United States Patent
Bayly et al.

(10) Patent No.: US 10,988,477 B2
(45) Date of Patent: Apr. 27, 2021

(54) GCN2 INHIBITORS AND USES THEREOF

(71) Applicants: Merck Patent GmbH, Darmstadt (DE); Vertex Pharmaceuticals Incorporated, Boston, MA (US)

(72) Inventors: Andrew Bayly, Abingdon (GB); Matthew Bleich, Brighton, MA (US); Jean-Damien Charrier, Wantage (GB); James Dodd, Abingdon (GB); Steven Durrant, Abingdon (GB); Meredith Suzanne Eno, Brighton, MA (US); Gorka Etxebarria I Jardi, Abingdon (GB); Simon Everitt, Abingdon (GB); Damien Fraysse, Abingdon (GB); Shazia Kelly, Abingdon (GB); Ronald Knegtel, Abingdon (GB); Igor Mochalkin, Westford, MA (US); Michael Mortimore, Burford (GB); Kiri North, Abingdon (GB); Filippos Porichis, Melrose, MA (US); Robert Pullin, Abingdon (GB); Alistair Rutherford, Abingdon (GB); Pierre-Henri Storck, Abingdon (GB); Heather Clare Twin, Wantage (GB); Yufang Xiao, Lexington, MA (US)

(73) Assignees: Merck Patent GmbH, Darmstardt (DE); Vertex Pharmaceuticals Incorporated, Boston, MA (US)

(*) Notice: Subject to any disclaimer, the term of this patent is extended or adjusted under 35 U.S.C. 154(b) by 13 days.

(21) Appl. No.: 16/259,979

(22) Filed: Jan. 28, 2019

(65) Prior Publication Data
US 2019/0233425 A1    Aug. 1, 2019

Related U.S. Application Data

(60) Provisional application No. 62/623,299, filed on Jan. 29, 2018.

(51) Int. Cl.
*C07D 487/04* (2006.01)
*A61K 31/5025* (2006.01)
*A61P 35/00* (2006.01)
*C07D 513/04* (2006.01)
*C07D 519/00* (2006.01)

(52) U.S. Cl.
CPC .......... *C07D 487/04* (2013.01); *A61P 35/00* (2018.01); *C07D 513/04* (2013.01); *C07D 519/00* (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese |
| 5,602,273 A | 2/1997 | Giese |
| 5,604,104 A | 2/1997 | Giese |
| 5,610,020 A | 3/1997 | Giese |
| 5,650,270 A | 7/1997 | Giese |
| 6,552,065 B2 | 4/2003 | Remiszewski |
| 7,226,926 B2 | 6/2007 | Blackaby |
| 7,390,799 B2 | 6/2008 | Bruncko |
| 8,138,347 B2 | 3/2012 | Knight |
| 8,513,276 B2 | 8/2013 | Berdini |
| 8,895,745 B2 | 11/2014 | Berdini |
| 8,906,682 B2 | 12/2014 | June |
| 2006/0247232 A1 | 11/2006 | Kawashima |
| 2010/0041662 A1 | 2/2010 | Ferrand |
| 2011/0176972 A1 | 7/2011 | Dien-Barataud |
| 2012/0071474 A1 | 3/2012 | Bo |
| 2015/0025058 A1 | 1/2015 | Deutsch |
| 2019/0233411 A1 | 8/2019 | Bleich et al. |

FOREIGN PATENT DOCUMENTS

| | | |
|---|---|---|
| WO | WO2000142246 | 6/2001 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | 2005037836 | 4/2005 |
| WO | WO2005113554 | 12/2005 |
| WO | WO2006029879 | 3/2006 |
| WO | WO2006078846 | 7/2006 |
| WO | WO2006105021 | 10/2006 |
| WO | WO2006122806 | 11/2006 |
| WO | WO2007005874 | 1/2007 |
| WO | WO2007016176 | 2/2007 |
| WO | WO2007044729 | 4/2007 |

(Continued)

OTHER PUBLICATIONS

Lind et al. PLOS One p. 1-20 downloaded at https://doi.org/10.1371/journal.pone.0219774 (Year: 2019).*
International Search Report for PCT/US2019/015469.
International Search Report for PCT/US2019/015473.
Adams et al., "Big opportunities for small molecules in immuno-oncology", Nature Reviews Drug Discovery, vol. 14, No. 9, 2015 (pp. 603-621).
Berge, S. M. et al., "Pharmaceutical Salts", J. Pharmaceutical Sciences, vol. 66, No. 1, Jan. 1977, (pp. 1-19).
Castilho et al., "Keeping the eIF2 alpha kinase Gcn2 in check", Biochimica et Biophysica Acta 1843, 2014, (pp. 1948-1968).
Corthay, "Does the immune system naturally protect against cancer?", Frontiers in Immunology, vol. 5, Article 197, May 2014, (pp. 1-8).

(Continued)

*Primary Examiner* — Emily A Bernhardt
(74) *Attorney, Agent, or Firm* — Andrea L.C. Reid; Dechert LLP

(57) ABSTRACT

The present invention provides compounds inhibiting General amino acid Control Non-derepressible 2 kinase ("GCN2"), compositions thereof, and methods of using the same for treating various disorders, such as cancer.

20 Claims, No Drawings

(56) References Cited

FOREIGN PATENT DOCUMENTS

| WO | WO2007053452 | 5/2007 |
|---|---|---|
| WO | WO2007070514 | 6/2007 |
| WO | WO2007084786 | 7/2007 |
| WO | WO2007129161 | 11/2007 |
| WO | WO2008039218 | 4/2008 |
| WO | 2008078091 | 7/2008 |
| WO | WO2008109943 | 9/2008 |
| WO | WO2008118802 | 10/2008 |
| WO | WO2008132601 | 11/2008 |
| WO | WO2009009116 | 1/2009 |
| WO | WO2009044273 | 4/2009 |
| WO | WO2009073620 | 6/2009 |
| WO | WO2009114512 | 9/2009 |
| WO | WO2010019570 | 2/2010 |
| WO | WO2010077634 | 7/2010 |
| WO | WO2011028683 | 3/2011 |
| WO | WO2011056652 | 5/2011 |
| WO | WO2011070024 | 6/2011 |
| WO | WO2011090760 | 7/2011 |
| WO | WO2011107553 | 9/2011 |
| WO | WO2011109400 | 9/2011 |
| WO | WO2011131407 | 10/2011 |
| WO | WO2011140249 | 11/2011 |
| WO | WO2012032433 | 3/2012 |
| WO | WO2012142237 | 10/2012 |
| WO | WO2012145493 | 10/2012 |
| WO | WO2013079174 | 6/2013 |
| WO | WO2013087699 | 6/2013 |
| WO | WO2013119716 | 8/2013 |
| WO | 2013131609 | 9/2013 |
| WO | WO2013132044 | 9/2013 |
| WO | WO2013169264 | 11/2013 |
| WO | WO2014008218 | 1/2014 |
| WO | WO2014036357 | 3/2014 |
| WO | 2016071293 | 5/2016 |
| WO | 2019148132 | 1/2019 |
| WO | 2019148136 | 1/2019 |

OTHER PUBLICATIONS

Dong et al., "Uncharged tRNA Activates GCN2 by Displacing the Protein Kinase Moiety from a Bipartite tRNA-Binding Domain", Molecular Cell, vol. 6, Aug. 2000, (pp. 269-279).

Fallarino et al., "The Combined Effects of Tryptophan Starvation and Tryptophan Catabolites Down-Regulate T Cell Receptor ζ-Chain and Induce a Regulatory Phenotype in Naive T Cells", J Immunol, 2006, 176, (pp. 6752-6761).

Fletcher et al., "∟-Arginine Depletion Blunts Antitumor T-cell Responses by Inducing Myeloid-Derived Suppressor Cells", Cancer Res, 2015, (pp. 275-283).

Holmgaard et al., "Indoleamine 2,3-dioxygenase is a critical resistance mechanism in antitumor T cell immunotherapy targeting CTLA-4", Journal of Exp Med., vol. 210, No. 7, 2013, (pp. 1389-1402).

Munn et al., "Expression of indoleamine 2,3-dioxygenase by plasmacytoid dendritic cells in tumor-draining lymph nodes", J. Clin. Invest. 114(2), Jul. 2004, (pp. 280-290).

Munn et al., "GCN2 Kinase in T Cells Mediates Proliferative Arrest and Anergy Induction in Response to Indoleamine 2,3-Dioxygenase", Immunity, vol. 22, May 2005, (pp. 633-642).

Okazaki, T et al., "A rheostat for immune responses—the unique properties of PD-1 and their advantage for clinical application", Nat. Immunol 14(12), Dec. 2013, (pp. 1212-1218).

Pilotte et al., "Reversal of tumoral immune resistance by inhibition of tryptophan 2,3-dioxygenase", Proc. Natl. Acad. Sci. U.S.A., vol. 109, No. 7, Feb. 2012, (pp. 2497-2502).

Ramirez et al., "Defining causative factors contributing in the activation of hedgehog signaling in diffuse large B-cell lymphoma", Leuk. Res., vol. 36(10), Oct. 2012 (pp. 1267-1273).

Ravishankar et al., "The amino acid sensor GCN2 inhibits inflammatory responses to apoptotic cells promoting tolerance and suppressing systemic autoimmunity", Proc. Natl. Acad. Sci. U.S.A., vol. 112(34), Aug. 2015, (pp. 10774-10779).

Rodriguez et al., "∟-arginine availability regulates T-lymphocyte cell-cycle progression", Blood, vol. 109, No. 4, Feb. 2007, (pp. 1568-1573).

Rodriguez et al., "∟-Arginine Deprivation Regulates Cyclin D3 mRNA Stability in Human T Cells by Controlling HuR Expression", J Immunol, vol. 185, 2010, (pp. 5198-5204).

Ross et al., "Bispecific T cell engager (BiTE®) antibody constructs can mediate bystander tumor cell killing", PLoS One vol. 12, No. 8, Aug. 2017, (pp. 1-24).

Rostovtsev et al., "A Stepwise Huisgen Cycloaddition Process: Copper(I)-Catalyzed Regioselective "Ligation" of Azides and Terminal Alkynes" Angew. Chem., vol. 41, 2002; (pp. 2708-2711).

Spranger et al., "Mechanism of tumor rejection with doublets of CTLA-4, PD-1/PD-L1, or IDO blockade involves restored IL-2 production and proliferation of $CD8^+$ T cells directly within the tumor microenvironment", Journal for ImmunoTherapy of Cancer, 2:3, 2014, (pp. 1-14).

Sun et al., "Carbohydrate and Protein Immobilization onto Solid Surfaces by Sequential Diels-Alder and Azide-Alkyne Cycloadditions", Bioconjugate Chem., vol. 17, 2006, (pp. 52-57).

Toogood, "Small molecule immuno-oncology therapeutic agents," Bioorganic & Medicinal Chemistry Letters, vol. 28, 2018, (pp. 319-329).

Uyttenhove et al., "Evidence for a tumoral immune resistance mechanism based on tryptophan degradation by indoleamine 2,3-dioxygenase", Nature Medicine, vol. 9, No. 10, Oct. 2003, (pp. 1269-1274).

Vattern and Wek, "Reinitiation involving upstream ORFs regulates ATF4 mRNA translation in mammalian cells", Proc. Natl. Acad. Sci USA, vol. 101(31), Aug. 2004, (pp. 11269-11274).

Wang et al., "Amino Acid Deprivation Promotes Tumor Angiogenesis through the GCN2/ATF4 Pathway", NeoPlasia, vol. 15, No. 8, Aug. 2013, (pp. 989-997).

Wek et al., "Juxtaposition of domains homologous to protein kinases and histidyl-tRNA synthetases in GCN2 protein suggest a mechanism for coupling GCN4 expression to amino acid availability", Proc. Nat. Acad. Sci, U.S.A., vol. 86, Jun. 1989, (pp. 4579-4583).

Whyte et al., "Suppressor of cytokine signaling (SOCS)1 is a key determinant of differential macrophage activation and function", Journal of Leukocyte Biology, vol. 90, Nov. 2011, (pp. 845-854).

Ye et al., "The GCN2-ATF4 pathway is critical for tumour cell survival and proliferation in response to nutrient deprivation", the EMBO Journal, vol. 29, 2010, (pp. 2082-2096).

Zea et al., "Arginase-Producing Myeloid Suppressor Cells in Renal Cell Carcinoma Patients: A Mechanism of Tumor Evasion", Cancer Res., vol. 65 (8), 2005, (pp. 3044-3048).

Zhang et al., "The GCN2 eIF2α Kinase is Required for Adaptation to Amino Acid Deprivation in Mice", Molecular and Cellular Biology, vol. 22, No. 19, Oct. 2002, (pp. 6681-6688).

Zou et al, "PD-L1 (B7-H1) and PD-01 pathway blockade for cancer therapy: Mechanisms, response biomarkers, and combinations", Sci. Transl. Med. vol. 8, Issue 328 (pp. 1-16).

Haning et al., "Comparison of different heterocyclic scaffolds as substrate analog PDE5 inhibitors", Bioorganic & Medicinal Chemistry Letters 15, vol. 15, 2005, pp. 3900-3907.

Popowycz, Inc., "Pyrazolo[1,5-a]=1,3,5-triazine as a Purine Bioisostere: Access to Potent Cyclin-Dependent Kinase Inhibitor (R)-Roscovitine Analogue", J. Med. Chem 2009, vol. 52, pp. 655-663.

Third Party Observation as submitted in PCT/US2019/015469 dated May 29, 2020.

* cited by examiner

GCN2 INHIBITORS AND USES THEREOF

CROSS-REFERENCE TO RELATED APPLICATIONS

This application claims the benefit under 35 U.S.C. § 119(e) of U.S. Provisional Application No. 62/623,299, filed Jan. 29, 2018, the content of which is incorporated herein in its entirety by reference.

TECHNICAL FIELD OF THE INVENTION

The present invention relates to compounds and methods useful for inhibiting General amino acid Control Non-derepressible 2 kinase ("GCN2"). The invention also provides pharmaceutically acceptable compositions comprising compounds of the present invention and methods of using said compositions in the treatment of various disorders.

BACKGROUND OF THE INVENTION

GCN2 (General amino acid Control Non-derepressible 2) is a ubiquitously expressed protein kinase involved in cellular responses to amino acid deficiency across eukaryotes (Castilho et al., 2014). Cellular deficiency in one or more amino acids causes the accumulation of uncharged cognate transfer RNAs (tRNAs), which are bound directly by GCN2, leading to kinase activation and phosphorylation of eukaryotic initiation factor 2α (eIF2α) on Serine 51 (Wek et al., 1989; Dong et al., 2000). Phosphorylation of eIF2α results in initiation of protein translation, which causes a reduction in the translation of most mRNAs leading to reduced global utilization of amino acids. Simultaneously, eIF2α phosphorylation increases the translation of a specific subset of mRNAs containing certain upstream open reading frames in their 5' untranslated regions (5'-UTRs), such as the transcription factor ATF4 in mammals (Vattem and Wek, 2004), which promotes restoration of protein homeostasis. GCN2 is therefore a critical determinant of cell fate in response to amino acid depletion.

Induction of cellular responses to amino acid deficiency is emerging as an important mechanism for regulation of the mammalian immune system, particularly in certain disease settings including cancer and autoimmunity. Various immunosuppressive cell types implicated in the control of immune responses in these settings, including tolerogenic dendritic cells, myeloid derived suppressor cells (MDSCs), tolerogenic/M2 macrophages and cancer cells themselves, have each been reported to use the depletion of amino acids to suppress T-cell responses (Munn et al., 2004; Munn et al., 2005; Rodriguez et al., 2010; Whyte et al., 2011; Uyttenhove et al., 2003). This is achieved by the intracellular transport of amino acids coupled with the overexpression of amino acid catabolizing enzymes in these cells, such as the tryptophan catabolizing enzymes indoleamine 2,3 dioxygenase (IDO) and tryptophan 2,3 dioxygenase (TDO), and the arginine catabolizing enzymes arginase 1 and 2 (ARG1, ARG2). As a result, these cells can reduce the local extracellular concentrations of specific amino acids wherever they reside, and therefore induce GCN2 activity in nearby T-cells in an antigen-specific manner (Munn et al., 2004). In the mouse system both in vitro and in vivo, the depletion of local tryptophan or arginine concentrations, for example by IDO- or ARG1-expressing dendritic cells, has been reported to induce proliferative arrest and anergy in T-cells in a GCN2-dependent manner (Munn et al., 2005; Rodriguez et al., 2007; Fletcher et al., 2015). In addition, the induction and/or maintenance of MDSCs and immunosuppressive regulatory T-cells (T-regs) may also be dependent on GCN2 activity under amino acid depleted conditions (Fletcher et al., 2015; Fallarino et al., 2006). Finally, other work implicates the activation of GCN2 by IDO within tolerogenic macrophages as a key mechanism for suppressing systemic autoimmune responses to apoptotic cells (Ravishankar et al., 2015). These findings identify GCN2 as a potentially key effector of the immunosuppressive effects of amino acid depletion associated with various disease states.

Incipient cancers need to evade host anti-cancer immunity in order to thrive (Corthay, 2014). This can be achieved by modulating tumor antigen presentation and/or by using tumor immune evasion mechanisms to actively suppress immune attack. High expression of amino acid catabolising enzymes such as IDO and ARG1 has been observed across a large proportion of cancer patients with various tumor types, both in the cancer cells themselves and in immunosuppressive host cell types that accumulate in tumors, tumor-draining lymph nodes and/or the peripheral circulation (Uyttenhove et al., 2003; Pilotte et al., 2012; Zea et al., 2005). Amino acid depletion may therefore be a powerful and widespread immune evasion mechanism whereby anti-cancer immunity is restrained. Consistently, amino acid depletion in both tumors and tumor-draining lymph nodes has been established as a resistance mechanism to existing immuno-oncology agents, including checkpoint receptor blocking antibodies, in several syngeneic mouse tumor models (Holmgaard et al., 2013; Spranger et al., 2014). On this basis, inhibitors of IDO and TDO are now being progressed in clinical trials for cancer and inhibitors of additional amino acid catabolases are in preclinical development. Accordingly, inhibitors of GCN2 may also be useful for cancer treatment by disrupting the nodal effector signal of amino acid depletion in the immune system and enabling an anti-cancer immune response. Genetic ablation of GCN2 is well tolerated in mice under standard growth conditions (Zhang et al., 2002), and inhibitors of GCN2 may have broader utility than inhibitors of individual amino acid catabolases because GCN2 responds to depletion of several different amino acids.

In addition, GCN2 activation and overexpression has been observed in various human tumors compared with normal tissues (Ye et al., 2010; Wang et al., 2013). Depletion of GCN2 reduced the growth of mouse embryonic fibroblasts and human cancer cells in vitro under severe amino acid or glucose depleted conditions, and blocked the growth of human tumor xenografts in mice (Ye et al., 2010). GCN2 inhibitors may therefore have direct anti-cancer effects due to the frequent disruption of nutrient supply in the tumor microenvironment.

For these reasons, there is a need for the development of potent and selective inhibitors of GCN2 for the treatment of cancer, either as single agents or in combination, for example with anti-CTLA4 and anti-PD1/PD-L1 checkpoint blocking antibodies.

SUMMARY OF THE INVENTION

It has now been found that compounds of this invention, and pharmaceutically acceptable compositions thereof, are effective as inhibitors of GCN2 kinase. Such compounds have the general formula I:

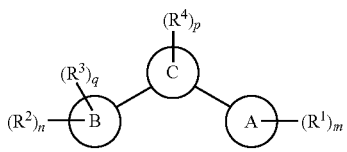

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating GCN2 kinase. Such diseases, disorders, or conditions include those described herein.

Compounds provided by this invention are also useful for the study of the GCN2 enzyme in biological and pathological phenomena; the study of intracellular signal transduction pathways occurring in bodily tissues; and the comparative evaluation of new GCN2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of GCN2 protein kinase. In some embodiments, a provided compound inhibits GCN2.

In certain embodiments, the present invention provides a compound of formula I:

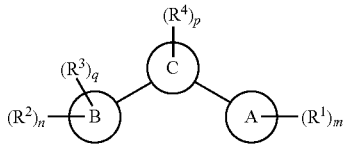

I or a pharmaceutically acceptable salt thereof, wherein:
Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bicyclic heteroaromatic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur, or Het, wherein Het is a 4-8 membered saturated monocyclic heterocyclic ring having 1-2 heteroatoms independently selected from nitrogen, oxygen, or sulfur, a 7-12 membered saturated spirocyclic heterocyclic ring having 1-4 heteroatoms independently selected from nitrogen, oxygen, or sulfur, a 7-12 membered saturated bicyclic heterocyclic ring having 1-3 heteroatoms independently selected from nitrogen, oxygen, or sulfur, or a 7-12 membered saturated bridged bicyclic heterocyclic ring having 1-2 heteroatoms independently selected from nitrogen, oxygen, or sulfur;

Ring B is

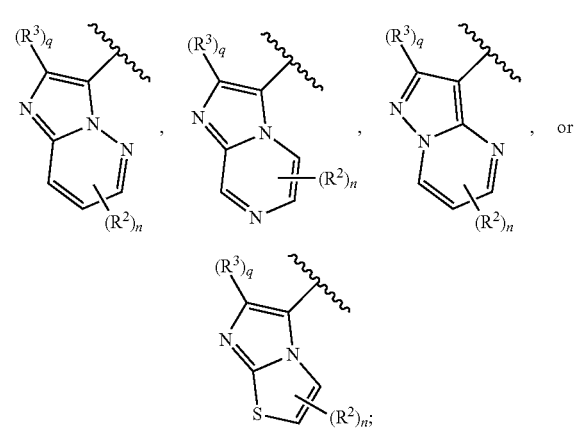

Ring C is

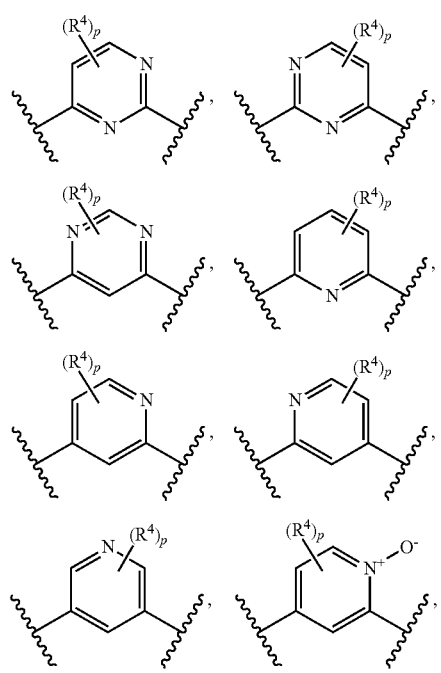

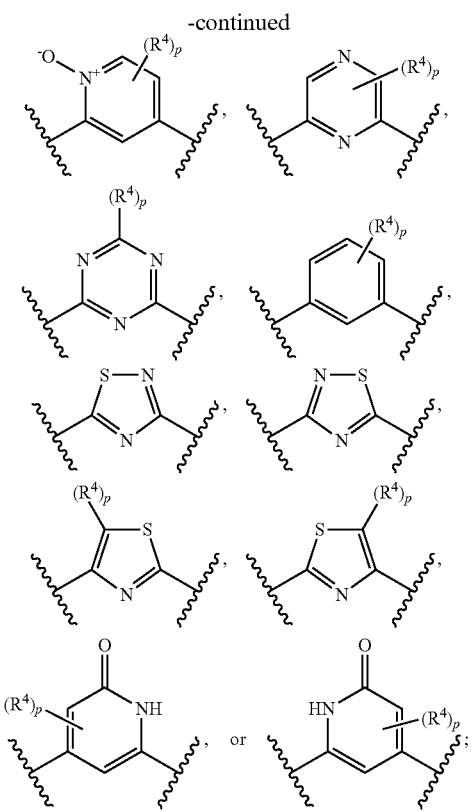

each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent C$_{2-4}$ alkylene chain; two R groups are optionally taken together with their intervening atoms to form an optionally substituted 3-7-membered saturated or partially unsaturated monocyclic ring having 0-4 heteroatoms independently selected from nitrogen, oxygen or sulfur;

each R' is independently hydrogen or a C$_{1-3}$ aliphatic group optionally substituted with halogen;

each of R$^1$ is independently hydrogen, halogen, —CN, —NO$_2$, —C(O)R, —C(O)OR, —C(O)N(R)$_2$, —C(O)N(R)S(O)$_2$R, —C(O)N=S(O)(R)$_2$, —N(R)$_2$, —N(R)C(O)R, —N(R)C(O)N(R)$_2$, —N(R)C(O)OR, —N(R)S(O)$_2$R, —N(R)S(O)$_2$N(R)$_2$, —OR, —ON(R)SO$_2$R, —P(O)(R)$_2$, —SR, —S(O)R, —S(O)$_2$R, —S(O)(NH)R, —S(O)$_2$N(R)$_2$, —S(NH$_2$)$_2$(O)OH, —N=S(O)(R)$_2$, —C(R)$_2$S(=O)(=NH)R, —C(R)$_2$NHSO$_2$CH$_3$, —CD$_3$, —CD$_2$N(R)S(O)$_2$R, or R; or:

two R$^1$ groups are optionally taken together to form =O, =NH or =NS(O)$_2$R; or two R$^1$ groups are optionally taken together to form a bivalent C$_{2-4}$ alkylene chain;

each of R$^2$ is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from C$_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur;

R$^3$ is hydrogen, halogen, —CN, —OR', —N(R')$_2$, or an optionally substituted group selected from C$_{1-3}$ aliphatic, phenyl, or a 5-6 membered monocyclic heteroaromatic ring having 1-4 heteroatoms independently selected from nitrogen, oxygen, or sulfur;

R$^4$ is hydrogen, halogen, —CN, —OR, —N=S(O)(R)$_2$, —N(R)$_2$, or an optionally substituted group selected from C$_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur;

m is 0, 1, 2, 3, 4 or 5;

n is 0, 1, or 2;

p is 0 or 1; and q is 0 or 1.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

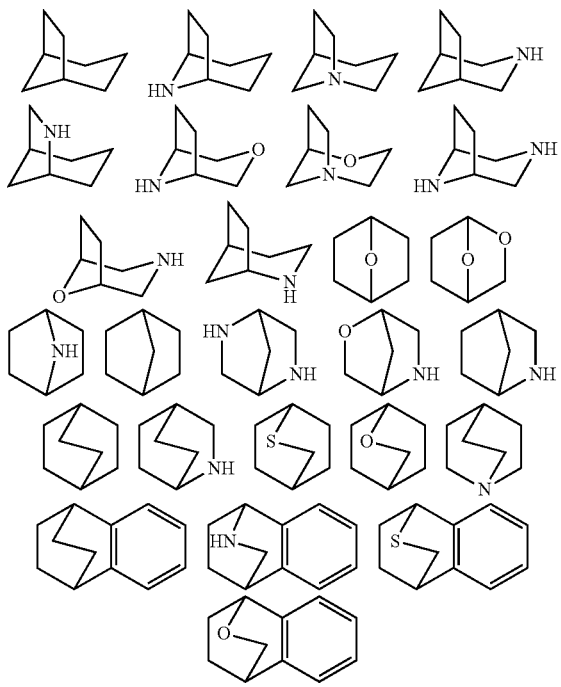

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

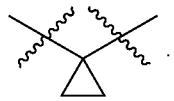 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 t electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroalkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)N(R°)$_2$; —N(R°)C(S)N(R°)$_2$; —(CH$_2$)$_{0-4}$N(R°)C(O)OR; —N(R°)N(R°)C(O)R°; —N(R°)N(R°)C(O)N(R°)$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSi(R°)$_3$; —(CH$_2$)$_{0-4}$OC(O)R°; —OC(O)(CH$_2$)$_{0-4}$SR, —SC(S)SRO; —(CH$_2$)$_{0-4}$SC(O)R; —(CH$_2$)$_{0-4}$C(O)N(R°)$_2$; —C(S)N(R°)$_2$; —C(S)SR°; —(CH$_2$)$_{0-4}$OC(O)N(R°)$_2$; —C(O)N(OR°)R°; —C(O)C(O)R°; —C(O)CH$_2$C(O)R; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$N(R°)$_2$; —(CH$_2$)$_{0-4}$S(O)R°; —(CH$_2$)$_{0-4}$S(O)(NR°)R; —N(R°)S(O)$_2$N(R°)$_2$; N(R°)S(O)$_2$R°; —N(R) S(O)(NR°)(R°)$_2$; —N(OR°)R°; —N=S(O)(R°)$_2$; —N(OR°)SO$_2$R°; —C(NH)N(R°)$_2$; —P(O)$_2$R°; —P(O)(R°)$_2$; —OP(O)(R°)$_2$; —OP(O)(OR°)$_2$; —Si(R°)$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR', —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$N(R')$_2$, —NO$_2$, —Si(R')$_3$, —OSi(R')$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, =NSO$_2$R*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —N(R$^\bullet$)$_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —N(R$^\dagger$)$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$N(R$^\dagger$)$_2$, —C(S)N(R$^\dagger$)$_2$, —C(NH)N(R)$_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —N(R$^\bullet$)$_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$-alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, R$^x$, of a provided compound comprises one or more deuterium atoms.

As used herein, the term "inhibitor" is defined as a compound that binds to and/or inhibits GCN2 with measurable affinity. In certain embodiments, an inhibitor has an IC$_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a GCN2 protein kinase activity between a sample comprising a compound of the present invention, or composition thereof, and a GCN2 protein kinase, and an equivalent sample comprising a GCN2 protein kinase, in the absence of said compound, or composition thereof.

3. Description of Exemplary Embodiments

As described above, in certain embodiments, the present invention provides a compound of formula I:

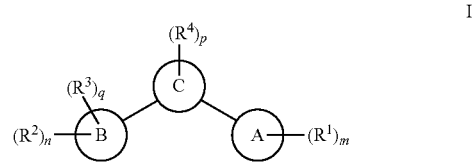

or a pharmaceutically acceptable salt thereof, wherein:

Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bicyclic heteroaromatic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur, or Het, wherein Het is a 4-8 membered saturated monocyclic heterocyclic ring having 1-2 heteroatoms independently selected from nitrogen, oxygen, or sulfur, a 7-12 membered saturated spirocyclic heterocyclic ring having 1-4 heteroatoms independently selected from nitrogen, oxygen, or sulfur, a 7-12 membered saturated bicyclic heterocyclic ring having 1-3 heteroatoms independently selected from nitrogen, oxygen, or sulfur, or a 7-12 membered saturated bridged bicyclic heterocyclic ring having 1-2 heteroatoms independently selected from nitrogen, oxygen, or sulfur;

Ring B is

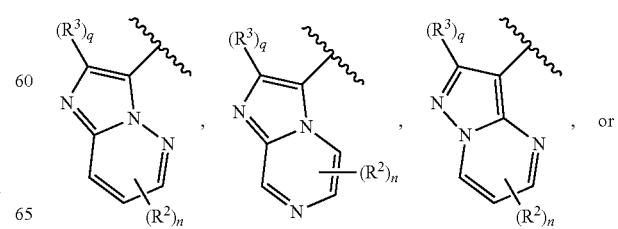

-continued

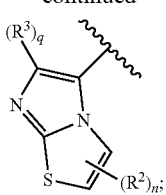

Ring C is

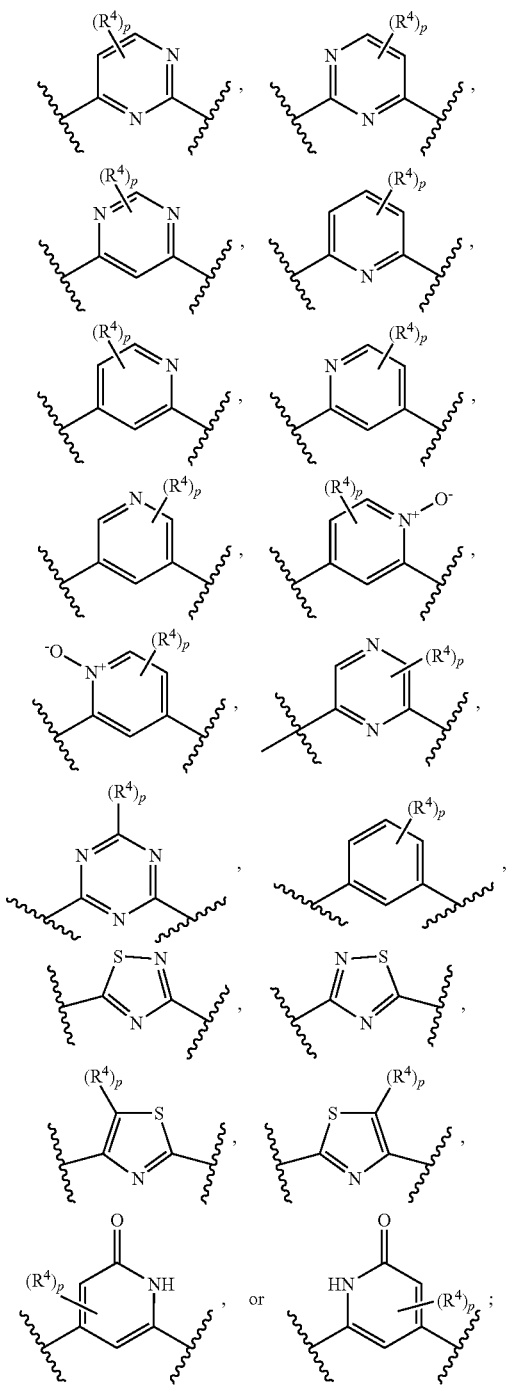

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or
two R groups are optionally taken together to form a bivalent $C_{2-4}$ alkylene chain; two R groups are optionally taken together with their intervening atoms to form an optionally substituted 3-7-membered saturated or partially unsaturated monocyclic ring having 0-4 heteroatoms independently selected from nitrogen, oxygen or sulfur;

each R' is independently hydrogen or a $C_{1-3}$ aliphatic group optionally substituted with halogen;

each of $R^1$ is independently hydrogen, halogen, —CN, —$NO_2$, —C(O)R, —C(O)OR, —C(O)N(R)$_2$, —C(O)N(R)S(O)$_2$R, —C(O)N=S(O)(R)$_2$, —N(R)$_2$, —N(R)C(O)R, —N(R)C(O)N(R)$_2$, —N(R)C(O)OR, —N(R)S(O)$_2$R, —N(R)S(O)$_2$N(R)$_2$, —OR, —ON(R)SO$_2$R, —P(O)(R)$_2$, —SR, —S(O)R, —S(O)$_2$R, —S(O)(NH)R, —S(O)$_2$N(R)$_2$, —S(NH$_2$)$_2$(O)OH, —N=S(O)(R)$_2$, —C(R)$_2$S(=O)(=NH)R, —C(R)$_2$NHSO$_2$CH$_3$, —CD$_3$, —CD$_2$N(R)S(O)$_2$R, or R; or:
two $R^1$ groups are optionally taken together to form =O, =NH or =NS(O)$_2$R; or
two $R^1$ groups are optionally taken together to form a bivalent $C_{2-4}$ alkylene chain;

each of $R^2$ is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from $C_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur;

$R^3$ is hydrogen, halogen, —CN, —OR', —N(R')$_2$, or an optionally substituted group selected from $C_{1-3}$ aliphatic, phenyl, or a 5-6 membered monocyclic heteroaromatic ring having 1-4 heteroatoms independently selected from nitrogen, oxygen, or sulfur;

$R^4$ is hydrogen, halogen, —CN, —OR, —N=S(O)(R)$_2$, —N(R)$_2$, or an optionally substituted group selected from $C_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur;

m is 0, 1, 2, 3, 4 or 5;
n is 0, 1, or 2;
p is 0 or 1; and
q is 0 or 1.

As defined above and described herein, Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bicyclic heteroaromatic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur.

In some embodiments, Ring A is 3-8 membered saturated or partially unsaturated monocyclic carbocyclic ring. In some embodiments, Ring A is phenyl. In some embodiments, Ring A is an 8-10 membered bicyclic aromatic carbocyclic ring. In some embodiments, Ring A is a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur. In some embodiments, Ring A is a 7-12 membered partially unsaturated spirocyclic heterocyclic ring having 1-2 heteroatoms independently selected from nitrogen, oxygen, or sulfur. In some embodiments, Ring A is a 7-12 membered partially unsaturated bicyclic heterocyclic ring having 1-4 heteroatoms independently selected from nitrogen, oxygen, or sulfur. In some embodiments, Ring A is a 7-12 membered partially unsaturated bicyclic heteroaromatic ring having 1-4 heteroatoms independently selected from nitrogen, oxygen, or sulfur. In some embodiments, Ring A is a 7-12 membered partially unsaturated bridged bicyclic heterocyclic ring having 1-2 heteroatoms independently selected from nitrogen, oxygen, or sulfur. In some embodiments, Ring A is a 5-6 membered monocyclic heteroaromatic ring having 1-4 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is Het. In some embodiments, Ring A is a 4-8 membered saturated monocyclic heterocyclic ring having 1-2 heteroatoms independently selected from nitrogen, oxygen, or sulfur. In some embodiments, Ring A is a 7-12 membered saturated spirocyclic heterocyclic ring having 1-4 heteroatoms independently selected from nitrogen, oxygen, or sulfur. In some embodiments, Ring A is a 7-12 membered saturated bicyclic heterocyclic ring having 1-3 heteroatoms independently selected from nitrogen, oxygen, or sulfur. In some embodiments, Ring A is a 7-12 membered saturated bridged bicyclic heterocyclic ring having 1-2 heteroatoms independently selected from nitrogen, oxygen, or sulfur.

In some embodiments, Ring A is

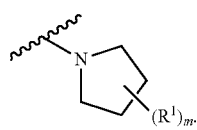

In some embodiments, Ring A is

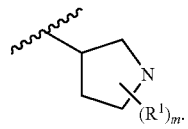

In some embodiments, Ring A is

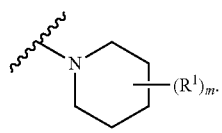

In some embodiments, Ring A is

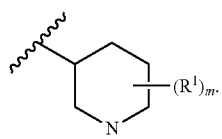

In some embodiments, Ring A is

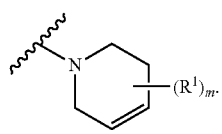

In some embodiments, Ring A is

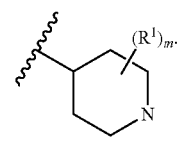

In some embodiments, Ring A is

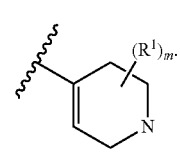

In some embodiments, Ring A is

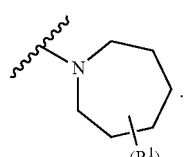

In some embodiments, Ring A is

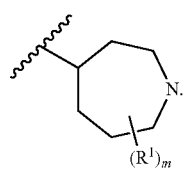

In some embodiments, Ring A is

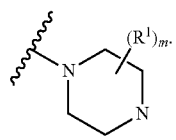

In some embodiments, Ring A is

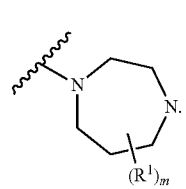

In some embodiments, Ring A is

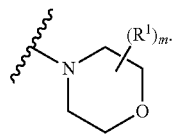

In some embodiments, Ring A is

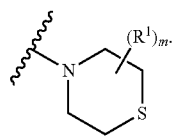

In some embodiments, Ring A is

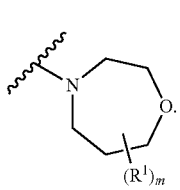

In some embodiments, Ring A is

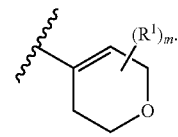

In some embodiments, Ring A is

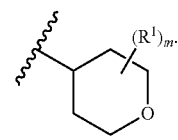

In some embodiments, Ring A is

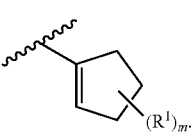

In some embodiments, Ring A is

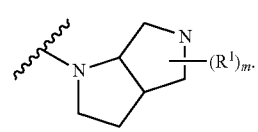

In some embodiments, Ring A is

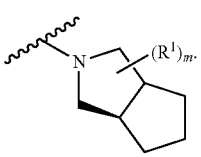

In some embodiments, Ring A is

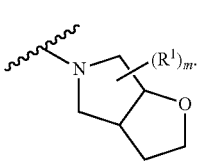

In some embodiments, Ring A is

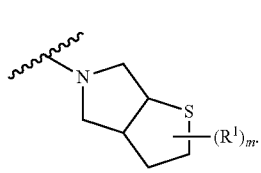

In some embodiments, Ring A is

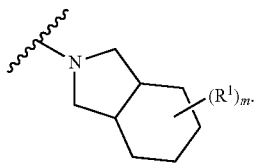

In some embodiments, Ring A is

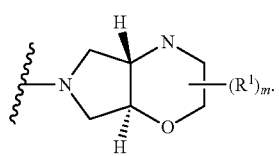

In some embodiments, Ring A is

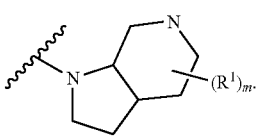

In some embodiments, Ring A is

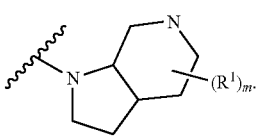

In some embodiments, Ring A is

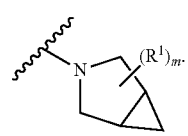

In some embodiments, Ring A is

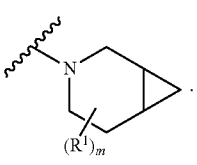

In some embodiments, Ring A is

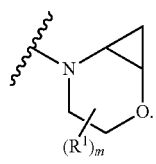

In some embodiments, Ring A is

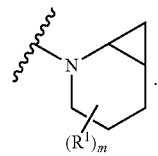

In some embodiments, Ring A is

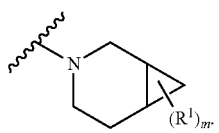

In some embodiments, Ring A is

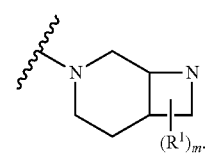

In some embodiments, Ring A is

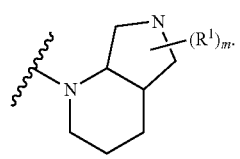

In some embodiments, Ring A is

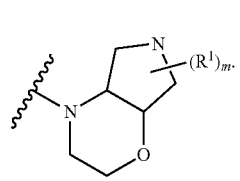

In some embodiments, Ring A is

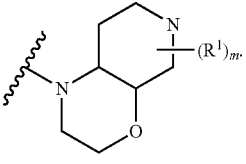

In some embodiments, Ring A is

In some embodiments, Ring A is

In some embodiments, Ring A is
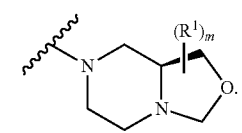
In some embodiments, Ring A is
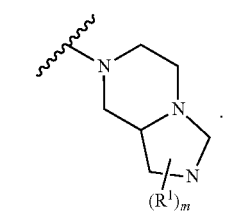
In some embodiments, Ring A is
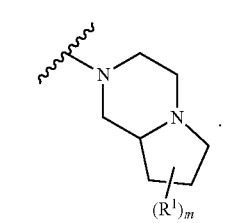
In some embodiments, Ring A is
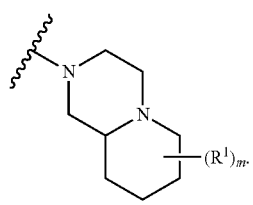
In some embodiments, Ring A is
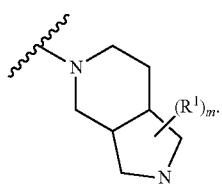
In some embodiments, Ring A is
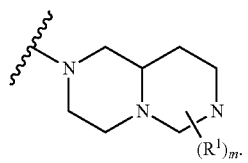
In some embodiments, Ring A is
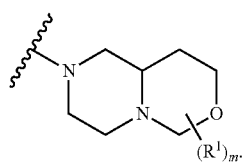
In some embodiments, Ring A is
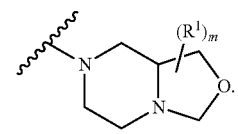
In some embodiments, Ring A is
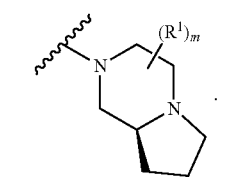

In some embodiments, Ring A is
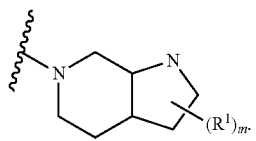
In some embodiments, Ring A is
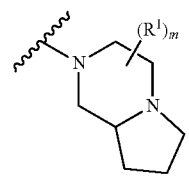
In some embodiments, Ring A is
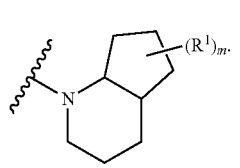
In some embodiments, Ring A is
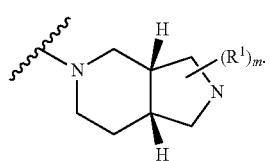
In some embodiments, Ring A is
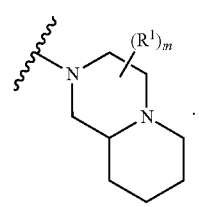
In some embodiments, Ring A is
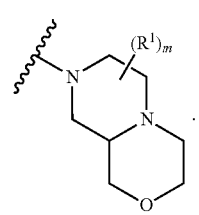
In some embodiments, Ring A is
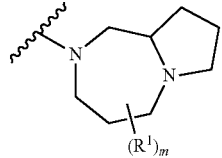
In some embodiments, Ring A is
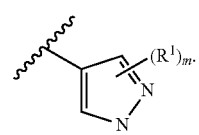
In some embodiments, Ring A is
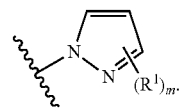
In some embodiments, Ring A is
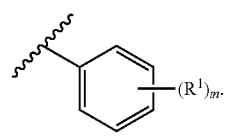
In some embodiments, Ring A is
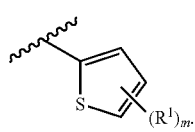
In some embodiments, Ring A is
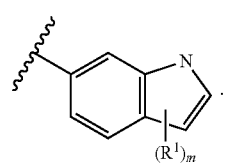

In some embodiments, Ring A is
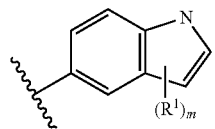
In some embodiments, Ring A is
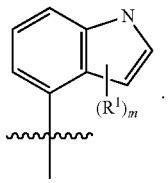
In some embodiments, Ring A is
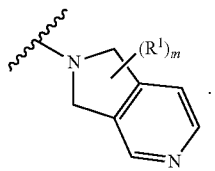
In some embodiments, Ring A is
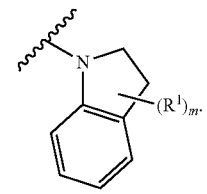
In some embodiments, Ring A is
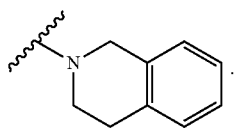
In some embodiments, Ring A is
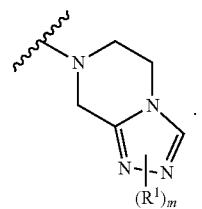
In some embodiments, Ring A is
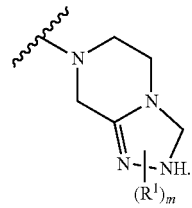
In some embodiments, Ring A is
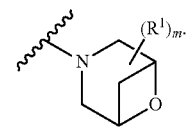
In some embodiments, Ring A is
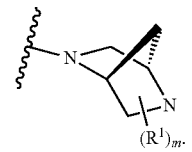
In some embodiments, Ring A is
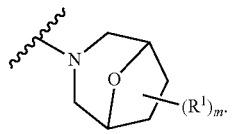
In some embodiments, Ring A is
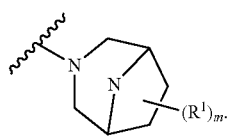
In some embodiments, Ring A is
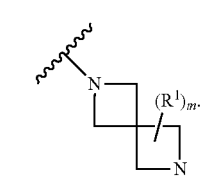

In some embodiments, Ring A is

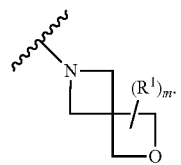

In some embodiments, Ring A is

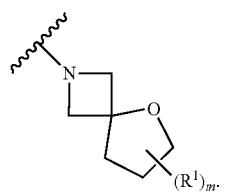

In some embodiments, Ring A is

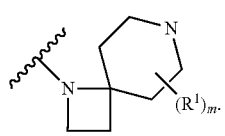

In some embodiments, Ring A is

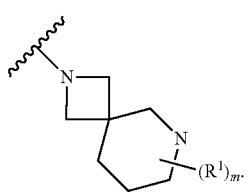

In some embodiments, Ring A is

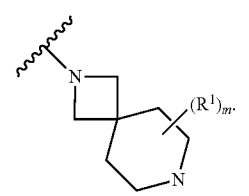

In some embodiments, Ring A is

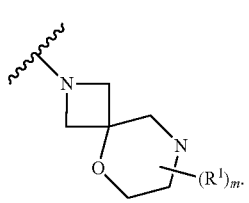

In some embodiments, Ring A is

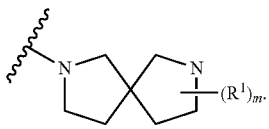

In some embodiments, Ring A is

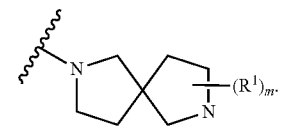

In some embodiments, Ring A is

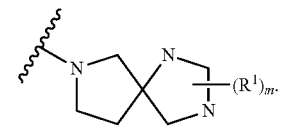

In some embodiments, Ring A is

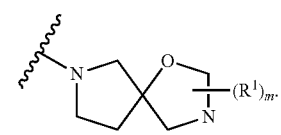

In some embodiments, Ring A is

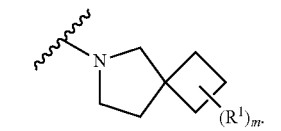

In some embodiments, Ring A is

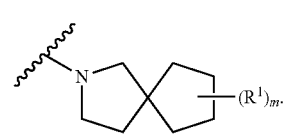

In some embodiments, Ring A is

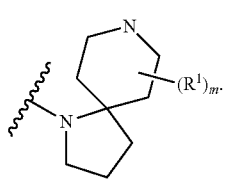

In some embodiments, Ring A is
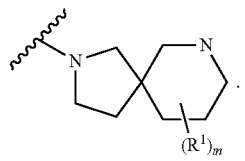
In some embodiments, Ring A is
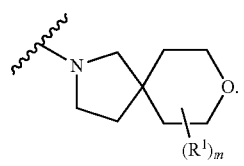
In some embodiments, Ring A is
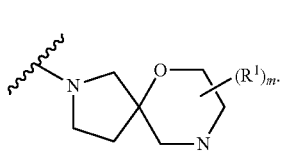
In some embodiments, Ring A is
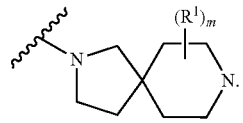
In some embodiments, Ring A is
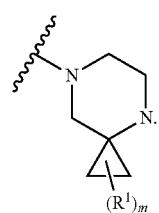
In some embodiments, Ring A is
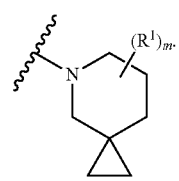
In some embodiments, Ring A is
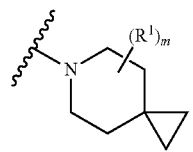
In some embodiments, Ring A is
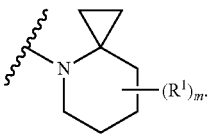
In some embodiments, Ring A is
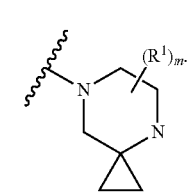
In some embodiments, Ring A is
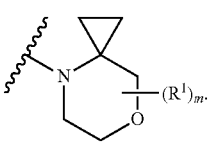
In some embodiments, Ring A is
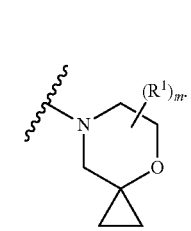
In some embodiments, Ring A is
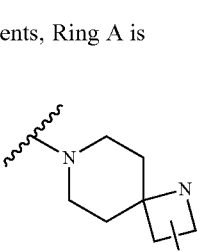

In some embodiments, Ring A is

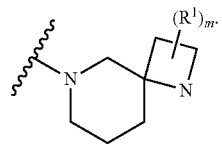

In some embodiments, Ring A is


In some embodiments, Ring A is


In some embodiments, Ring A is

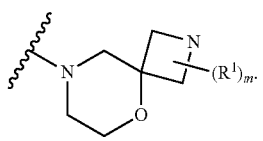

In some embodiments, Ring A is

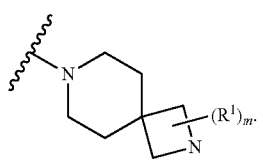

In some embodiments, Ring A is

In some embodiments, Ring A is

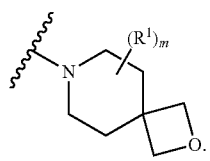

In some embodiments, Ring A is

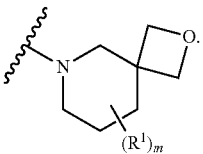

In some embodiments, Ring A is

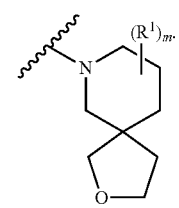

In some embodiments, Ring A is

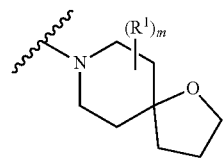

In some embodiments, Ring A is

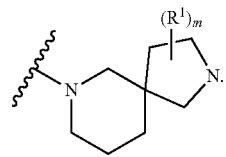

In some embodiments, Ring A is

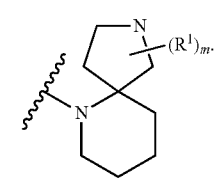

In some embodiments, Ring A is

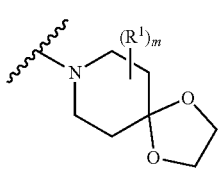

In some embodiments, Ring A is

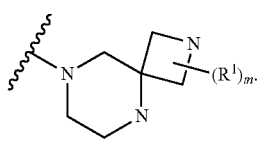

In some embodiments, Ring A is

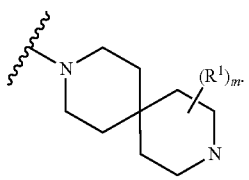

In some embodiments, Ring A is

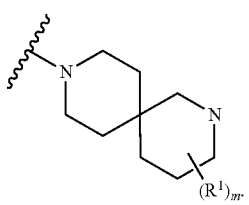

In some embodiments, Ring A is

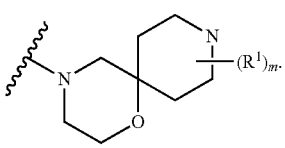

In some embodiments, Ring A is

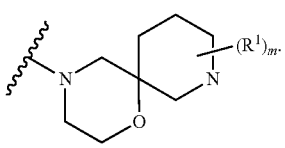

In some embodiments, Ring A is

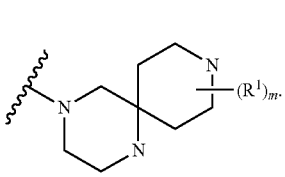

In some embodiments, Ring A is

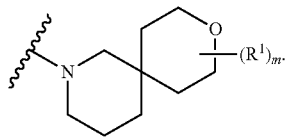

In some embodiments, Ring A is

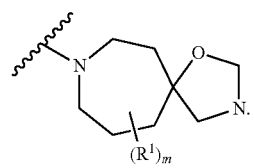

In some embodiments, Ring A is

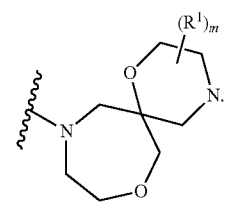

In some embodiments, Ring A is

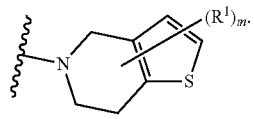

In some embodiments, Ring A is

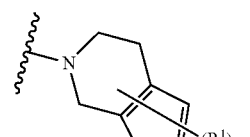

In some embodiments, Ring A is selected from those depicted in Tables 1-4, below.

As defined above and described herein, Ring B is

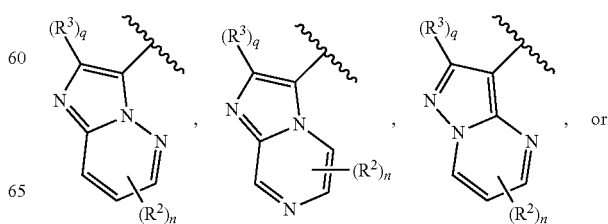

-continued
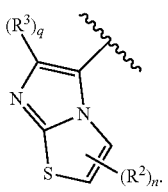
In some embodiments, Ring B is
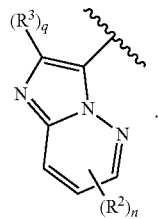
In some embodiments, Ring B is
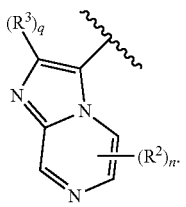
In some embodiments, Ring B is
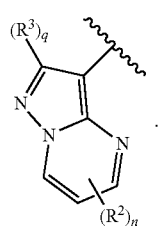
In some embodiments, Ring B is
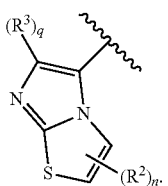
In some embodiments, Ring B is selected from those depicted in Tables 1-4, below.
As defined above and described herein, Ring C is
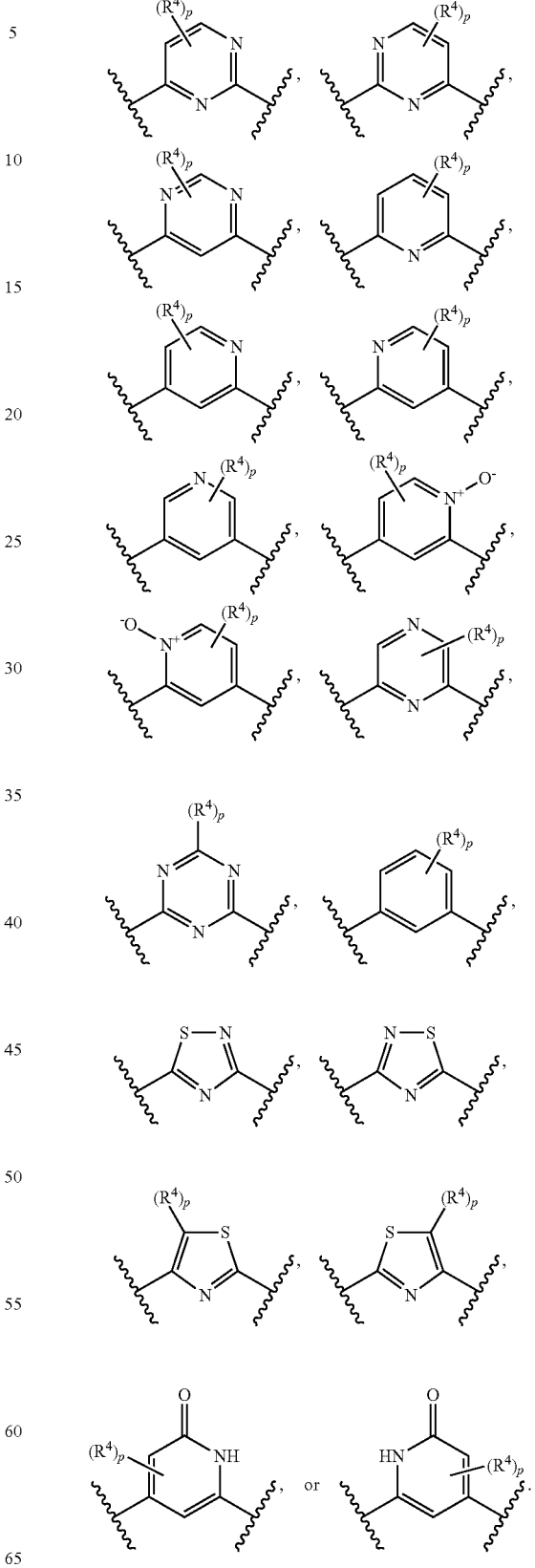

In some embodiments, Ring C is
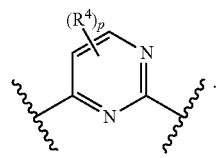
In some embodiments, Ring C is
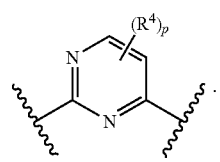
In some embodiments, Ring C is
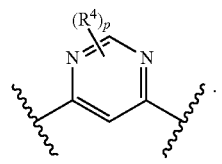
In some embodiments, Ring C is
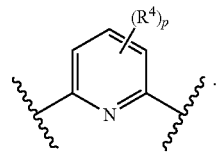
In some embodiments, Ring C is
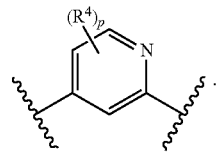
In some embodiments, Ring C is
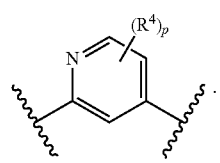
In some embodiments, Ring C is
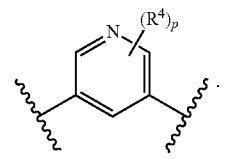
In some embodiments, Ring C is
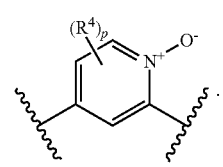
In some embodiments, Ring C is
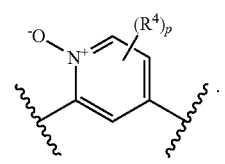
In some embodiments, Ring C is
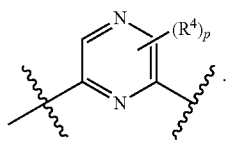
In some embodiments, Ring C is
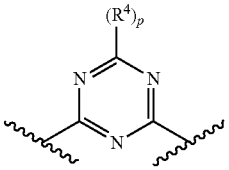
In some embodiments, Ring C is
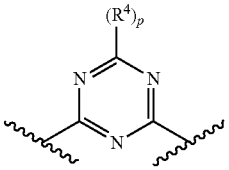

In some embodiments, Ring C is

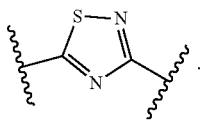 [SMILES: *c1nsc(*)n1]

In some embodiments, Ring C is

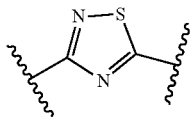

In some embodiments, Ring C is

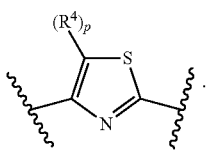

In some embodiments, Ring C is

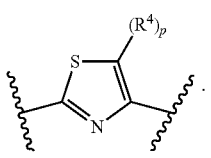

In some embodiments, Ring C is

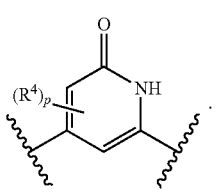

In some embodiments, Ring C is

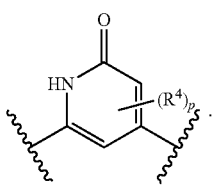

In some embodiments, Ring C is selected from those depicted in Tables 1-4, below.

As defined above and described herein, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent $C_{2-4}$ alkylene chain; or two R groups are optionally taken together with their intervening atoms to form an optionally substituted 3-7-membered saturated or partially unsaturated monocyclic ring having 0-4 heteroatoms independently selected from nitrogen, oxygen or sulfur.

In some embodiments R is hydrogen. In some embodiments R is an optionally substituted $C_{1-6}$ aliphatic group. In some embodiments R is an optionally substituted 3-8 membered saturated or partially unsaturated monocyclic carbocyclic ring. In some embodiments R is an optionally substituted phenyl. In some embodiments R is an optionally substituted 8-10 membered bicyclic aromatic carbocyclic ring. In some embodiments R is an optionally substituted 4-8 membered saturated or partially unsaturated monocyclic heterocyclic ring having 1-2 heteroatoms independently selected from nitrogen, oxygen, or sulfur. In some embodiments R is an optionally substituted 5-6 membered monocyclic heteroaromatic ring having 1-4 heteroatoms independently selected from nitrogen, oxygen, or sulfur. In some embodiments R is an optionally substituted 8-10 membered bicyclic heteroaromatic ring having 1-5 heteroatoms independently selected from nitrogen, oxygen, or sulfur. In some embodiments two R groups are optionally taken together to form a bivalent $C_{2-4}$ alkylene chain. In some embodiments two R groups are optionally taken together with their intervening atoms to form an optionally substituted 3-7-membered saturated or partially unsaturated monocyclic ring having 0-4 heteroatoms independently selected from nitrogen, oxygen or sulfur.

In some embodiments, R is selected from those depicted in Tables 1-4, below.

As defined above and described herein, each of R' is independently hydrogen or a $C_{1-3}$ aliphatic group optionally substituted with halogen.

In some embodiments, R' is hydrogen. In some embodiments, R' is a $C_{1-3}$ aliphatic group optionally substituted with halogen.

In some embodiments, R' is selected from those depicted in Tables 1-4, below.

As defined above and described herein, each of $R^1$ is independently hydrogen, halogen, —CN, —NO$_2$, —C(O)R, —C(O)OR, —C(O)N(R)$_2$, —C(O)N(R)S(O)$_2$R, —C(O)N=S(O)(R)$_2$, —N(R)$_2$, —N(R)C(O)R, —N(R)C(O)N(R)$_2$, —N(R)C(O)OR, —N(R)S(O)$_2$R, —N(R)S(O)$_2$N(R)$_2$, —OR, —ON(R)SO$_2$R, —P(O)(R)$_2$, —SR, —S(O)R, —S(O)$_2$R, —S(O)(NH)R, —S(O)$_2$N(R)$_2$, —S(NH$_2$)$_2$(O)OH, —N=S(O)(R)$_2$, —C(R)$_2$S(=O)(=NH)R, —C(R)$_2$NHSO$_2$CH$_3$, —CD$_3$, —CD$_2$N(R)S(O)$_2$R, or R; or: two $R^1$ groups are optionally taken together to form =O, =NH or =NS(O)$_2$R; or two $R^1$ groups are optionally taken together to form a bivalent $C_{2-4}$ alkylene chain.

In some embodiments, $R^1$ is hydrogen. In some embodiments, $R^1$ is halogen. In some embodiments, $R^1$ is —CN. In some embodiments, $R^1$ is —NO$_2$. In some embodiments, $R^1$ is —C(O)R. In some embodiments, $R^1$ is —C(O)OR. In some embodiments, $R^1$ is —C(O)N(R)$_2$. In some embodiments, $R^1$ is —C(O)N(R)S(O)$_2$R. In some embodiments, $R^1$ is —C(O)N=S(O)(R)$_2$. In some embodiments, $R^1$ is —N(R)₂. In some embodiments, R¹ is —N(R)C(O)R. In some embodiments, R¹ is —N(R)C(O)N(R)₂. In some embodiments, R¹ is —N(R)C(O)OR. In some embodiments, R¹ is —N(R)S(O)₂R. In some embodiments, R¹ is —N(R)S(O)₂N(R)₂. In some embodiments, R¹ is —OR. In some embodiments, R¹ is —ON(R)SO₂R. In some embodiments, R¹ is —P(O)(R)₂. In some embodiments, R¹ is —SR. In some embodiments, R¹ is —S(O)R. In some embodiments, R¹ is —S(O)₂R. In some embodiments, R¹ is —S(O)(NH)R. In some embodiments, R¹ is —S(O)₂N(R)₂. In some embodiments, R¹ is —S(NH₂)₂(O)OH. In some embodiments, R¹ is —N=S(O)(R)₂. In some embodiments, R¹ is —C(R)₂S(=O)(=NH)R. In some embodiments, R¹ is —C(R)₂NHSO₂CH₃. In some embodiments, R¹ is —CD₃. In some embodiments, R¹ is —CD₂N(R)S(O)₂R. In some embodiments, R¹ is R. In some embodiments, two R¹ groups are optionally taken together to form =O, =NH or =NS(O)₂R. In some embodiments, two R¹ groups are optionally taken together to form a bivalent C₂₋₄ alkylene chain.

In some embodiments, R¹ is fluoro. In some embodiments, R¹ is chloro. In some embodiments, R¹ is methyl. In some embodiments, R¹ is ethyl. In some embodiments, R¹ is —OH. In some embodiments, R¹ is —OCH₃. In some embodiments, R¹ is —CH₂OH. In some embodiments, R¹ is —CH₂CN. In some embodiments, R¹ is —CF₃. In some embodiments, R¹ is —CH₂NH₂. In some embodiments, R¹ is —COOH. In some embodiments, R¹ is —NH₂.

In some embodiments, two R¹ groups form =O. In some embodiments, two R¹ groups form =NH. In some embodiments, two R¹ groups form =NSO₂CH₃. In some embodiments, two R¹ groups form

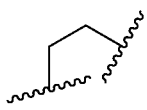

In some embodiments, R¹ is

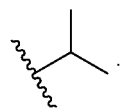

In some embodiments, R¹ is

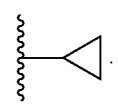

In some embodiments, R is

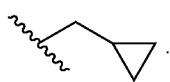

In some embodiments, R¹ is

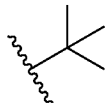

In some embodiments, R¹ is

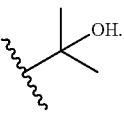 [SMILES: *C(C)(C)O]

In some embodiments, R¹ is

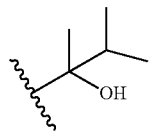

In some embodiments, R¹ is

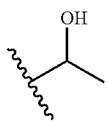

In some embodiments, R¹ is

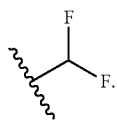

In some embodiments, R¹ is

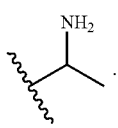

In some embodiments, R¹ is

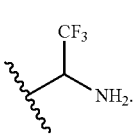

In some embodiments, R¹ is

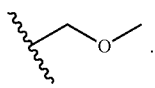

In some embodiments, R¹ is

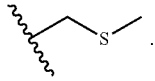

In some embodiments, R¹ is


In some embodiments, R¹ is

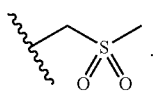

In some embodiments, R¹ is

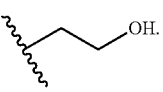 [SMILES: *CCO]

In some embodiments, R¹ is

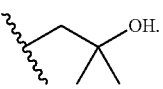 [SMILES: *CC(C)(C)O]

In some embodiments, R¹ is

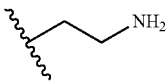

In some embodiments, R¹ is

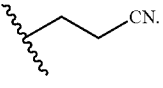 [SMILES: *CCC#N]

In some embodiments, R¹ is

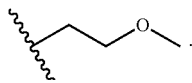 [SMILES: *CCOC ; "."]

In some embodiments, R¹ is

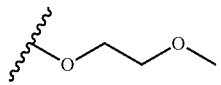

In some embodiments, R¹ is

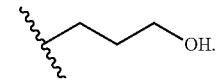 [SMILES: *CCCO]

In some embodiments, R¹ is


In some embodiments, R¹ is

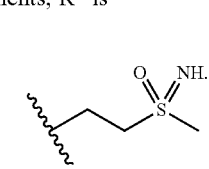

In some embodiments, R¹ is

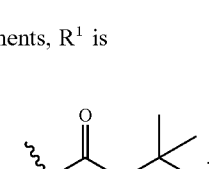

In some embodiments, R¹ is

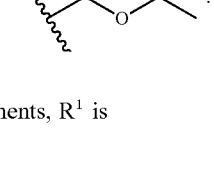

In some embodiments, R¹ is

In some embodiments R¹ is

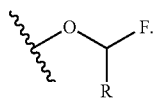

In some embodiments, R¹ is

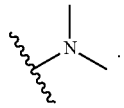 [SMILES: *N(C)C ; "."]

In some embodiments, R¹ is

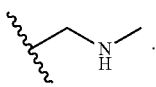

In some embodiments, R¹ is

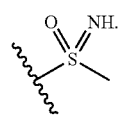

In some embodiments, R¹ is

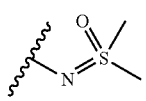

In some embodiments, R¹ is

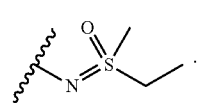 [SMILES: *N=S(C)(=O)CC ; "."]

In some embodiments, R¹ is

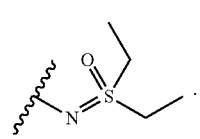 [SMILES: *N=S(=O)(CC)CC ; "."]

In some embodiments, R¹ is

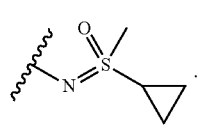 [SMILES: *N=S(C)(=O)C1CC1]

In some embodiments, R¹ is

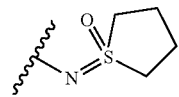

In some embodiments, R¹ is

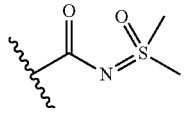

In some embodiments, R¹ is

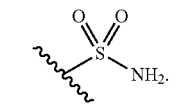

In some embodiments, R¹ is

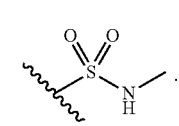 [SMILES: *S(=O)(=O)NC]

In some embodiments, R¹ is

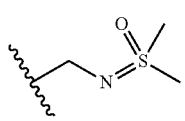

In some embodiments, R¹ is

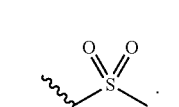

In some embodiments, R¹ is

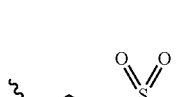

In some embodiments, R¹ is

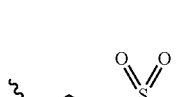

In some embodiments, R¹ is
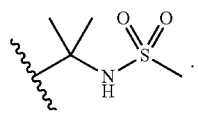
In some embodiments, R¹ is
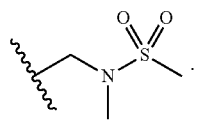
In some embodiments, R¹ is
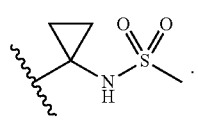
In some embodiments, R¹ is
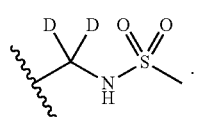
In some embodiments, R¹ is
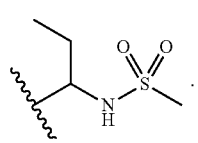 [SMILES: *C(CC)NS(C)(=O)=O]
In some embodiments, R¹ is
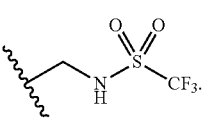 [SMILES: *CNS(=O)(=O)C(F)(F)F]
In some embodiments, R¹ is
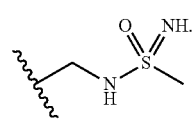
In some embodiments, R¹ is
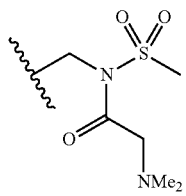
In some embodiments, R¹ is
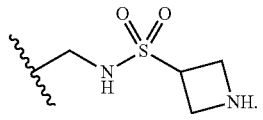 [SMILES: *CNS(=O)(=O)C1CNC1]
In some embodiments, R¹ is
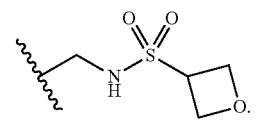 [SMILES: *CNS(=O)(=O)C1COC1]
In some embodiments, R¹ is
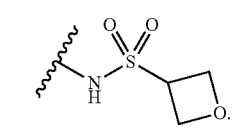 [SMILES: *NS(=O)(=O)C1COC1]
In some embodiments, R¹ is
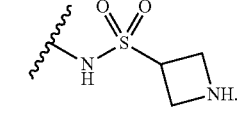
In some embodiments, R¹ is
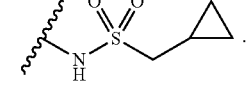
In some embodiments, R¹ is
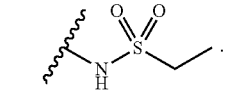 [SMILES: *NS(=O)(=O)CC]

In some embodiments, R¹ is

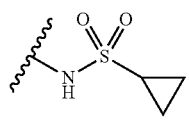

In some embodiments, R¹ is

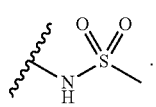

In some embodiments, R¹ is

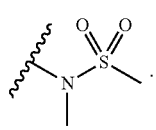

In some embodiments, R¹ is

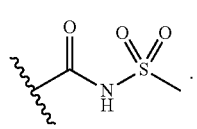

In some embodiments, R¹ is

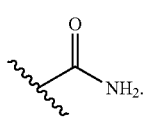 [SMILES: *C(N)=O]

In some embodiments, R¹ is

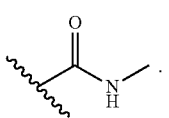 [SMILES: *C(=O)NC]

In some embodiments, R¹ is

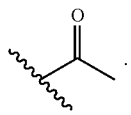

In some embodiments, R¹ is

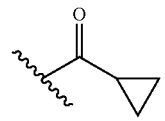

In some embodiments, R¹ is

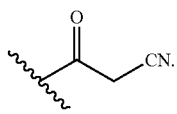 [SMILES: *C(=O)CC#N]

In some embodiments, R¹ is

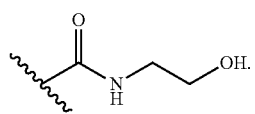 [SMILES: *C(=O)NCCO]

In some embodiments, R¹ is

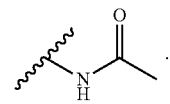

In some embodiments, R¹ is

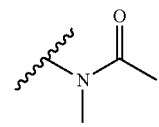

In some embodiments, R¹ is

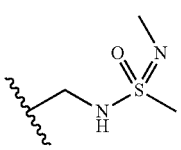

In some embodiments, R¹ is

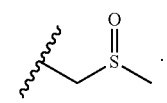 [SMILES: *CS(C)=O]

In some embodiments, R¹ is

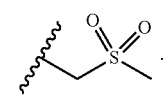 [SMILES: *CS(C)(=O)=O]

In some embodiments, R¹ is

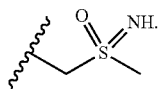

In some embodiments, R¹ is

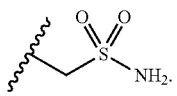

In some embodiments, R¹ is

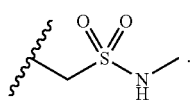 [SMILES: *CS(=O)(=O)NC]

In some embodiments, R¹ is

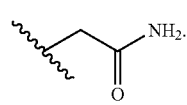 [SMILES: *CC(N)=O]

In some embodiments, R¹ is

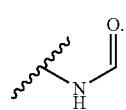 [SMILES: *NC=O]

In some embodiments, R¹ is

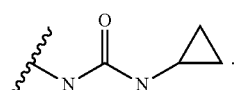

In some embodiments, R¹ is

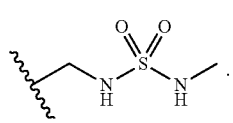 [SMILES: *CNS(=O)(=O)NC]

In some embodiments, R¹ is

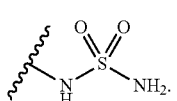

H In some embodiments, R¹ is

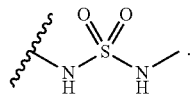

In some embodiments, R¹ is

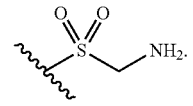

In some embodiments, R¹ is

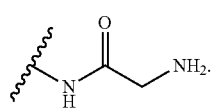

In some embodiments, R¹ is

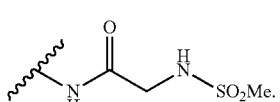

In some embodiments, R¹ is

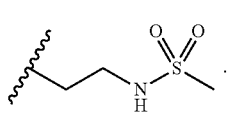 [SMILES: *CCNS(C)(=O)=O]

H In some embodiments, R¹ is

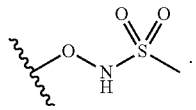

In some embodiments, R¹ is

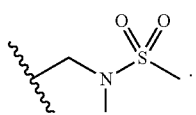

In some embodiments, R¹ is

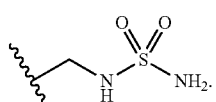

In some embodiments, R¹ is
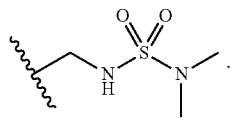 [SMILES: *CNS(=O)(=O)N(C)C]
In some embodiments, R¹ is
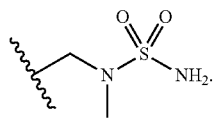 [SMILES: *CN(C)S(N)(=O)=O]
In some embodiments, R¹ is
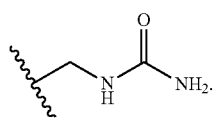 [SMILES: *CNC(N)=O]
In some embodiments, R¹ is
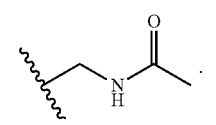 [SMILES: *CNC(C)=O]
In some embodiments, R¹ is
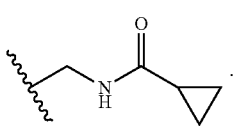 [SMILES: *CNC(=O)C1CC1]
In some embodiments, R¹ is
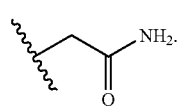
In some embodiments, R¹ is
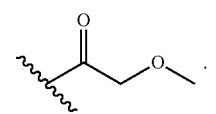 [SMILES: *C(=O)COC]
In some embodiments, R¹ is
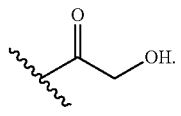 [SMILES: *C(=O)CO]
In some embodiments, R¹ is
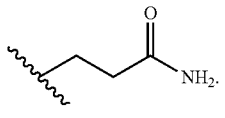 [SMILES: *CCC(N)=O]
In some embodiments, R¹ is
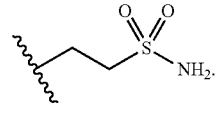 [SMILES: *CCS(N)(=O)=O]
In some embodiments, R¹ is
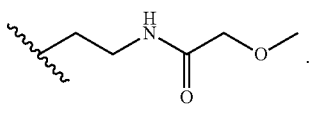 [SMILES: *CCNC(=O)COC]
In some embodiments, R¹ is
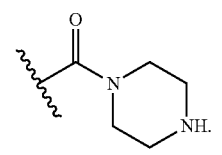
In some embodiments, R¹ is
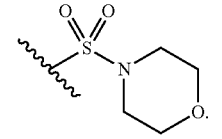 [SMILES: *S(=O)(=O)N1CCOCC1]
In some embodiments, R¹ is
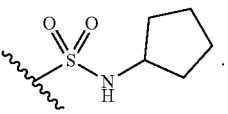

In some embodiments, R¹ is
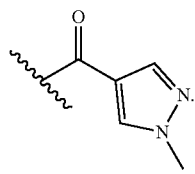 [SMILES: *C(=O)c1cnn(C)c1]
In some embodiments, R¹ is
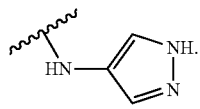
In some embodiments, R¹ is
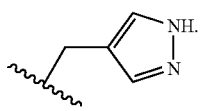 [SMILES: *Cc1cn[nH]c1]
In some embodiments, R¹ is
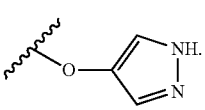
In some embodiments, R¹ is
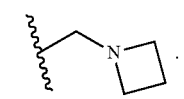 [SMILES: *CN1CCC1]
In some embodiments, R¹ is
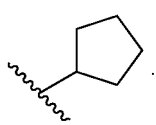 [SMILES: *C1CCCC1]
In some embodiments, R¹ is
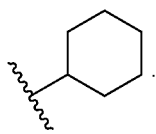
In some embodiments, R¹ is
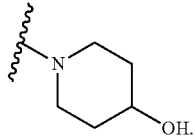 [SMILES: *N1CCC(O)CC1]
In some embodiments, R¹ is
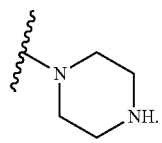 [SMILES: *N1CCNCC1]
In some embodiments, R¹ is
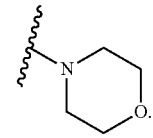
In some embodiments, R¹ is
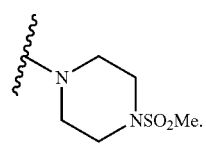
In some embodiments, R¹ is
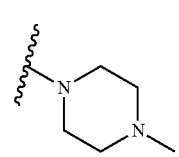
In some embodiments, R¹ is
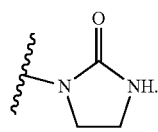 [SMILES: *N1CCNC1=O]
In some embodiments, R¹ is
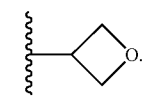

In some embodiments, R¹ is
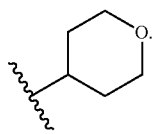 [SMILES: *C1CCOCC1]
In some embodiments, R¹ is

In some embodiments, R¹ is
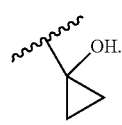
In some embodiments, R¹ is
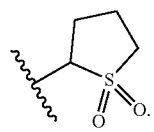
In some embodiments, R¹ is
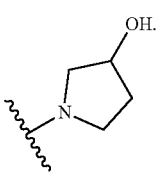 [SMILES: *N1CCC(O)C1]
In some embodiments, R¹ is
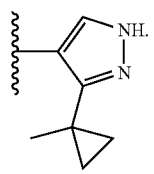 [SMILES: *c1c[nH]nc1C1(C)CC1]
In some embodiments, R¹ is
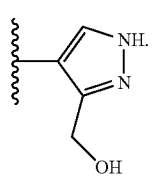 [SMILES: *c1c[nH]nc1CO]
In some embodiments, R¹ is
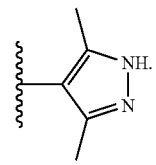
In some embodiments, R¹ is
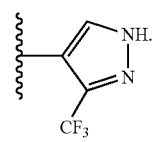
In some embodiments, R¹ is
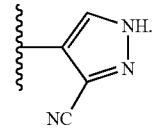 [SMILES: *c1c[nH]nc1C#N]
In some embodiments, R¹ is
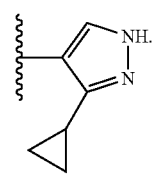 [SMILES: *c1c[nH]nc1C1CC1]
In some embodiments, R¹ is
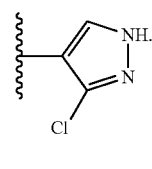
In some embodiments, R¹ is
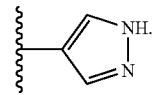
In some embodiments, R¹ is
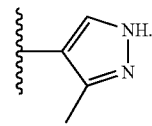

In some embodiments, R¹ is
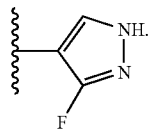
In some embodiments, R¹ is
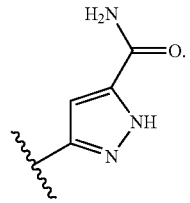 [SMILES: *c1cc(C(N)=O)[nH]n1]
In some embodiments, R¹ is
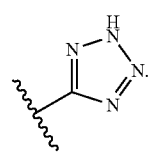 [SMILES: *c1nn[nH]n1]
In some embodiments, R¹ is
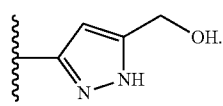 [SMILES: *c1cc(CO)[nH]n1]
In some embodiments, R¹ is
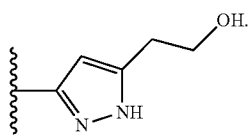 [SMILES: *c1cc(CCO)[nH]n1]
In some embodiments R¹ is
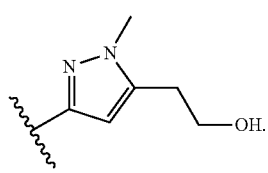 [SMILES: *c1cc(CCO)n(C)n1]
In some embodiments, R¹ is
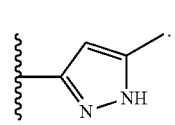
In some embodiments, R¹ is
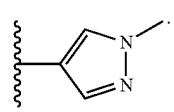
In some embodiments, R¹ is
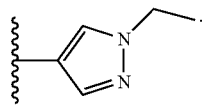 [SMILES: *c1cnn(CC)c1]
In some embodiments, R¹ is
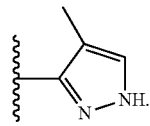 [SMILES: *c1n[nH]cc1C]
In some embodiments, R¹ is
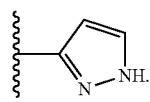
In some embodiments, R¹ is
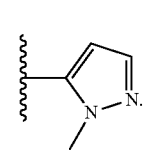
In some embodiments, R¹ is
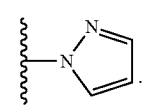
In some embodiments, R¹ is
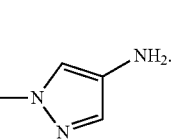

In some embodiments, R¹ is
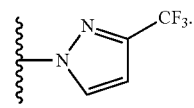
In some embodiments, R¹ is
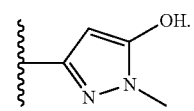 [SMILES: *c1cc(O)n(C)n1]
In some embodiments, R¹ is
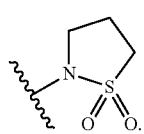
In some embodiments, R¹ is
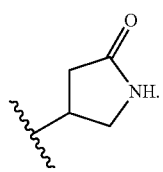 [SMILES: *C1CNC(=O)C1]
In some embodiments, R¹ is
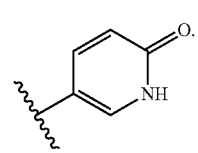 [SMILES: *c1ccc(=O)[nH]c1]
In some embodiments, R¹ is
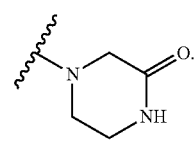
In some embodiments, R¹ is
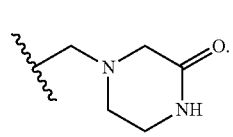 [SMILES: *CN1CCNC(=O)C1]
In some embodiments, R¹ is
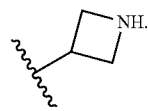 [SMILES: *C1CNC1]
In some embodiments, R¹ is
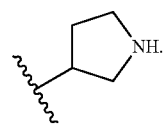 [SMILES: *C1CCNC1]
In some embodiments, R¹ is
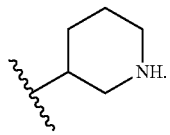 [SMILES: *C1CCCNC1]
In some embodiments, R¹ is
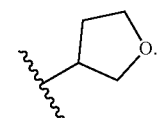
In some embodiments, R¹ is
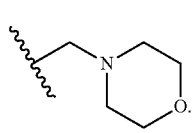
In some embodiments, R¹ is
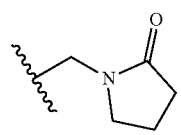
In some embodiments, R¹ is
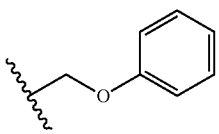

In some embodiments, R¹ is

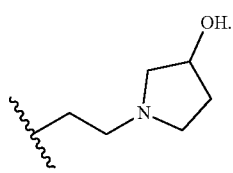 [SMILES: *CCN1CCC(O)C1]

In some embodiments, R¹ is

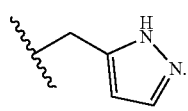

In some embodiments, R¹ is

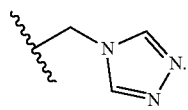

In some embodiments, R¹ is

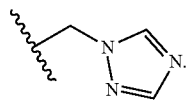

In some embodiments, R¹ is

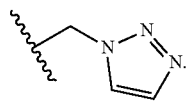

In some embodiments, R¹ is

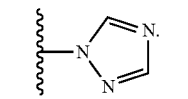

In some embodiments, R¹ is

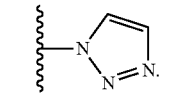

In some embodiments, R¹ is

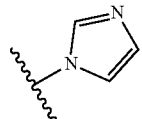

In some embodiments, R¹ is

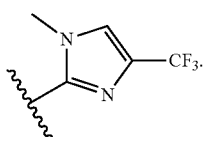 [SMILES: *c1nc(C(F)(F)F)cn1C]

In some embodiments, R¹ is

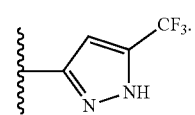

In some embodiments, R¹ is

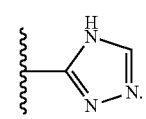

In some embodiments, R¹ is

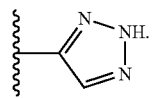

In some embodiments, R¹ is

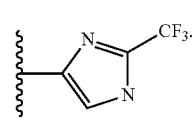

In some embodiments, R¹ is

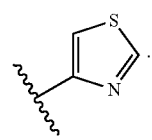

In some embodiments, R¹ is

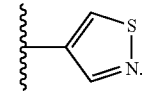

In some embodiments, R¹ is
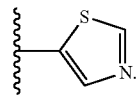
In some embodiments, R¹ is
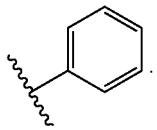
In some embodiments, R¹ is
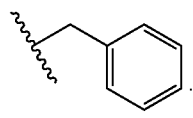
In some embodiments, R¹ is
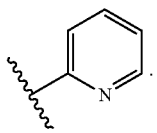 [SMILES: *c1ccccn1]
In some embodiments, R¹ is
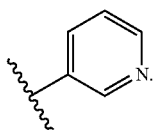 [SMILES: *c1cccnc1]
In some embodiments, R¹ is
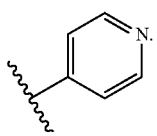 [SMILES: *c1ccncc1]
In some embodiments, R¹ is
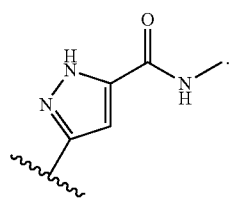 [SMILES: *c1cc(C(=O)NC)[nH]n1]
In some embodiments, R¹ is
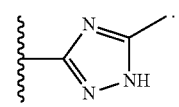
In some embodiments, R¹ is
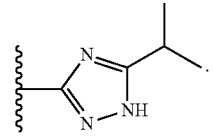 [SMILES: *c1n[nH]c(C(C)C)n1]
In some embodiments, R¹ is
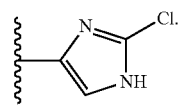 [SMILES: *c1c[nH]c(Cl)n1]
In some embodiments, R¹ is
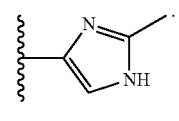
In some embodiments, R¹ is
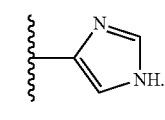
In some embodiments, R¹ is
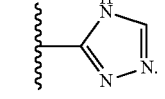
In some embodiments, R¹ is
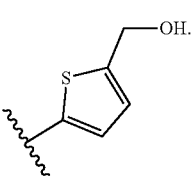 [SMILES: *c1ccc(CO)s1]

In some embodiments, R¹ is

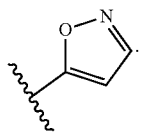 [SMILES: *c1ccno1]

In some embodiments, R¹ is

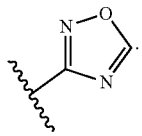

In some embodiments, R¹ is

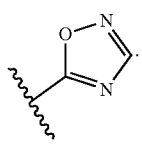 [SMILES: *c1ncno1]

In some embodiments, R¹ is

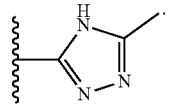

In some embodiments R¹ is

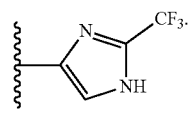 [SMILES: *c1c[nH]c(C(F)(F)F)n1]

In some embodiments, R¹ is

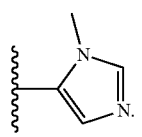

In some embodiments, R¹ is

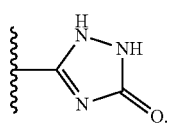 [SMILES: *c1nc(=O)[nH][nH]1]

In some embodiments, R¹ is

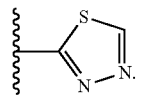

In some embodiments, R¹ is

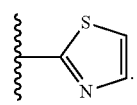

In some embodiments, R¹ is

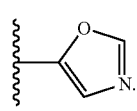

In some embodiments, R¹ is

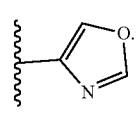

In some embodiments, R¹ is

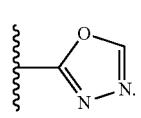

In some embodiments R¹ is

In some embodiments, R¹ is

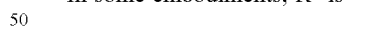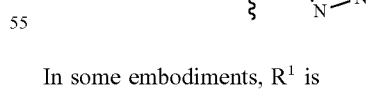

In some embodiments, R¹ is

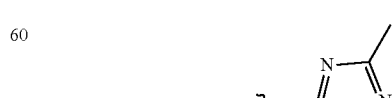

In some embodiments, R¹ is
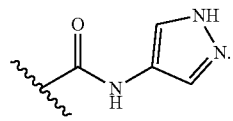 [SMILES: *C(=O)Nc1cn[nH]c1]
In some embodiments, R¹ is
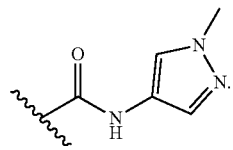 [SMILES: *C(=O)Nc1cnn(C)c1]
In some embodiments, R¹ is
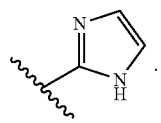
In some embodiments, R¹ is
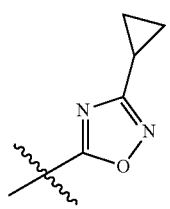
In some embodiments, R¹ is
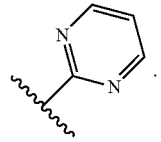 [SMILES: *c1ncccn1]
In some embodiments, R¹ is
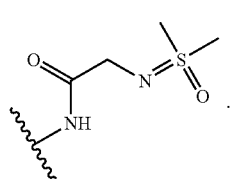 [SMILES: *NC(=O)CN=S(C)(C)=O]
In some embodiments, R¹ is
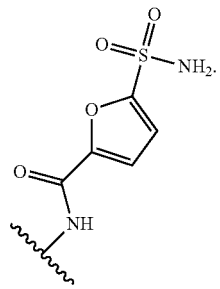 [SMILES: *NC(=O)c1ccc(S(N)(=O)=O)o1]
In some embodiments, R¹ is
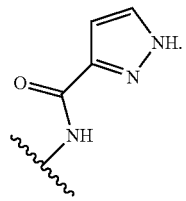 [SMILES: *NC(=O)c1cc[nH]n1]
In some embodiments, R¹ is
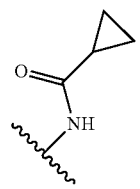
In some embodiments, R¹ is
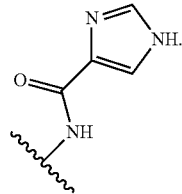 [SMILES: *NC(=O)c1c[nH]cn1]
In some embodiments, R¹ is
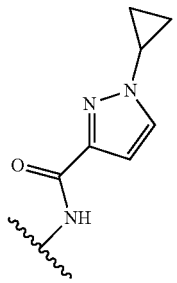

In some embodiments, R¹ is
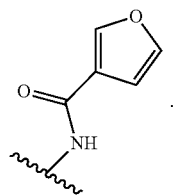
In some embodiments, R¹ is
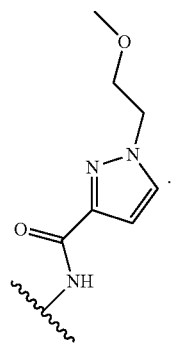 [SMILES: *NC(=O)c1ccn(CCOC)n1]
In some embodiments, R¹ is
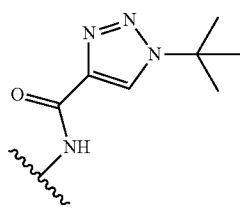
In some embodiments, R¹ is
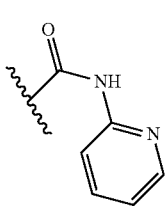
In some embodiments, R¹ is
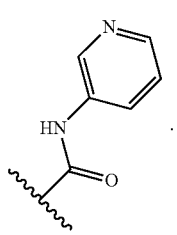 [SMILES: *C(=O)Nc1cccnc1]
In some embodiments, R¹ is
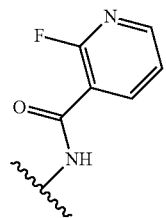
In some embodiments, R¹ is
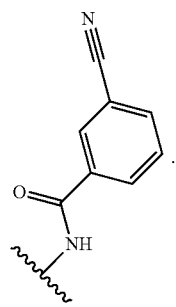 [SMILES: *NC(=O)c1cccc(C#N)c1]
In some embodiments, R¹ is
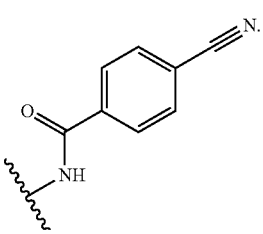 [SMILES: *NC(=O)c1ccc(C#N)cc1]
In some embodiments, R¹ is
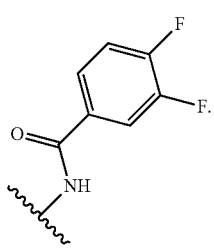 [SMILES: *NC(=O)c1ccc(F)c(F)c1]

In some embodiments, $R^1$ is

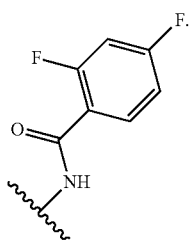 [SMILES: *NC(=O)c1ccc(F)cc1F]

In some embodiments, $R^1$ is

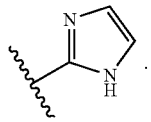

In some embodiments, $R^1$ is

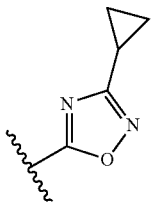

In some embodiments, $R^1$ is

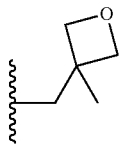

In some embodiments, $R^1$ is

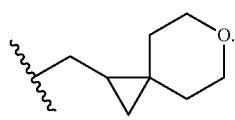 [SMILES: *CC1CC12CCOCC2]

In some embodiments, $R^1$ is

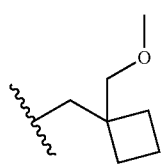

In some embodiments, $R^1$ is

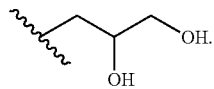 [SMILES: *CC(O)CO]

In some embodiments, $R^1$ is

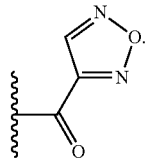 [SMILES: *C(=O)c1cnon1]

In some embodiments, $R^1$ is

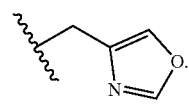 [SMILES: *Cc1cocn1]

In some embodiments, $R^1$ is

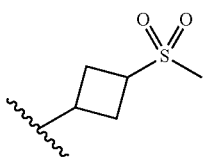

In some embodiments, $R^1$ is

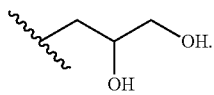

In some embodiments, $R^1$ is selected from those depicted in Tables 1-4, below.

As defined above and described herein, each of $R^2$ is each of $R^2$ is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from $C_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur.

In some embodiments, $R^2$ is hydrogen. In some embodiments, $R^2$ is halogen. In some embodiments, $R^2$ is —CN. In some embodiments, $R^2$ is —C(O)N(R')$_2$. In some embodiments, $R^2$ is —OR'. In some embodiments, $R^2$ is —N(R')$_2$. In some embodiments, $R^2$ is —S(O)$_2$R. In some embodiments, $R^2$ is —S(O)$_2$N(R)$_2$. In some embodiments, $R^2$ is —O-phenyl. In some embodiments, $R^2$ is an optionally substituted $C_{1-3}$ aliphatic group. In some embodiments, $R^2$ is an optionally substituted phenyl. In some embodiments, $R^2$ is an optionally substituted 5-6 membered monocyclic heteroaromatic ring having 1-4 heteroatoms independently selected from nitrogen, oxygen, or sulfur. In some embodiments, R² is an optionally substituted 4-8 membered saturated monocyclic heterocycle having 1-4 heteroatoms independently selected from nitrogen, oxygen, or sulfur.

In some embodiments, R² is fluoro. In some embodiments, R² is chloro. In some embodiments, R² is bromo. In some embodiments, R² is methyl. In some embodiments, R² is ethyl. In some embodiments, R² is —CF₃. In some embodiments, R² is

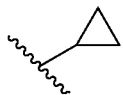

In some embodiments, R² is

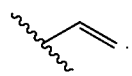 [SMILES: *C=C]

In some embodiments, R² is

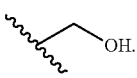

In some embodiments, R² is

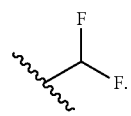

In some embodiments, R² is

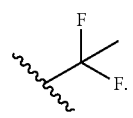 [SMILES: *C(C)(F)F]

In some embodiments, R² is

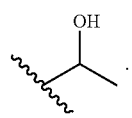 [SMILES: *C(C)O]

In some embodiments, R² is

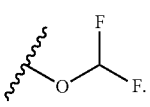

In some embodiments, R² is

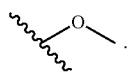

In some embodiments, R² is

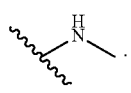

In some embodiments, R² is

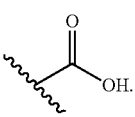 [SMILES: *C(=O)O]

In some embodiments, R² is

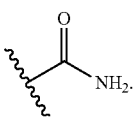

In some embodiments, R² is

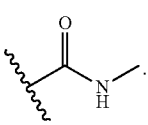

In some embodiments, R² is

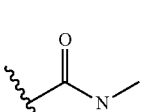

In some embodiments, R² is

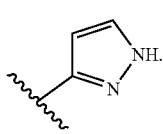

In some embodiments, R² is

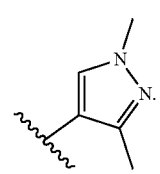 [SMILES: *c1cn(C)nc1C]

In some embodiments, R² is
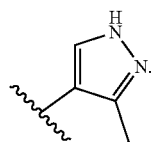 [SMILES: *c1c[nH]nc1C]
In some embodiments, R² is
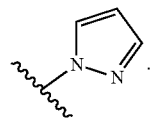
In some embodiments, R² is
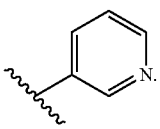 [SMILES: *c1cccnc1]
In some embodiments, R² is
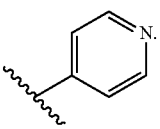 [SMILES: *c1ccncc1]
In some embodiments, R² is
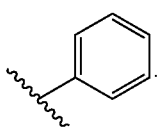
In some embodiments, R² is
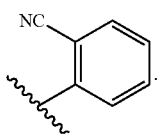
In some embodiments, R² is
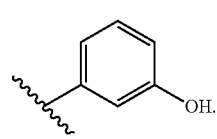 [SMILES: *c1cccc(O)c1]
In some embodiments, R² is
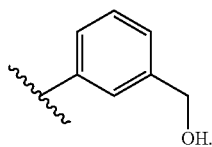 [SMILES: *c1cccc(CO)c1]
In some embodiments, R² is
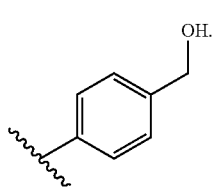 [SMILES: *c1ccc(CO)cc1]
In some embodiments, R² is
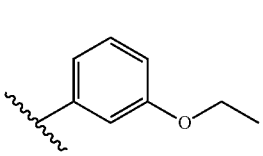
In some embodiments, R² is
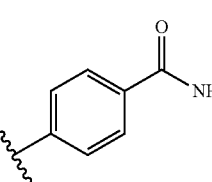
In some embodiments, R² is
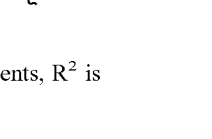
In some embodiments, R² is
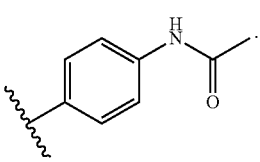 [SMILES: *c1ccc(NC(C)=O)cc1]
In some embodiments, R² is
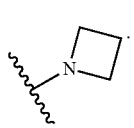

In some embodiments, $R^2$ is

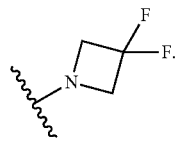 [SMILES: *N1CC(F)(F)C1]

In some embodiments, $R^2$ is selected from those depicted in Tables 1-4, below.

As defined above and described herein, $R^3$ is hydrogen, halogen, —CN, —OR', —N(R')$_2$, or an optionally substituted group selected from $C_{1-3}$ aliphatic, phenyl, or a 5-6 membered monocyclic heteroaromatic ring having 1-4 heteroatoms independently selected from nitrogen, oxygen, or sulfur.

In some embodiments, $R^3$ is hydrogen. In some embodiments, $R^3$ is halogen. In some embodiments, $R^3$ is —CN. In some embodiments, $R^3$ is —OR'. In some embodiments, $R^3$ is —N(R')$_2$. In some embodiments, $R^3$ is an optionally substituted $C_{1-3}$ aliphatic group. In some embodiments, $R^3$ is an optionally substituted phenyl. In some embodiments, $R^3$ is an optionally substituted 5-6 membered monocyclic heteroaromatic ring having 1-4 heteroatoms independently selected from nitrogen, oxygen, or sulfur.

In some embodiments, $R^3$ is selected from those depicted in Tables 1-4, below.

As defined above and described herein, $R^4$ is hydrogen, halogen, —CN, —OR, —N=S(O)(R)$_2$, —N(R)$_2$, or an optionally substituted group selected from $C_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur.

In some embodiments, $R^4$ is hydrogen. In some embodiments, $R^4$ is halogen. In some embodiments, $R^4$ is —CN. In some embodiments, $R^4$ is —OR. In some embodiments, $R^4$ is —N=S(O)(R)$_2$. In some embodiments, $R^4$ is —N(R)$_2$. In some embodiments, $R^4$ is an optionally substituted $C_{1-3}$ aliphatic group. In some embodiments, $R^4$ is an optionally substituted 4-8 membered saturated or partially unsaturated monocyclic heterocyclic ring having 1-2 heteroatoms independently selected from nitrogen, oxygen, or sulfur. In some embodiments, $R^4$ is an optionally substituted 7-12 membered saturated or partially unsaturated spirocyclic heterocyclic ring having 1-2 heteroatoms independently selected from nitrogen, oxygen, or sulfur.

In some embodiments, $R^4$ is fluoro. In some embodiments, $R^4$ is chloro. In some embodiments, $R^4$ is methyl. In some embodiments, $R^4$ is —CF$_3$. In some embodiments, $R^4$ is —OH. In some embodiments, $R^4$ is

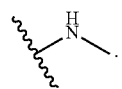

In some embodiments, $R^4$ is


In some embodiments, $R^4$ is

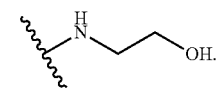 [SMILES: *NCCO]

In some embodiments, $R^4$ is

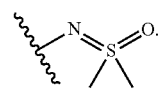

In some embodiments, $R^4$ is

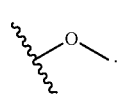

In some embodiments, $R^4$ is

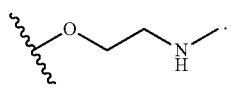 [SMILES: *OCCNC]

In some embodiments, $R^4$ is

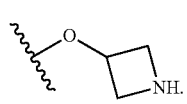 [SMILES: *OC1CNC1]

In some embodiments, $R^4$ is

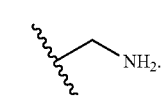

In some embodiments, $R^4$ is

In some embodiments, R⁴ is

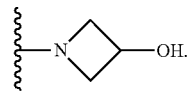 [SMILES: *N1CC(O)C1]

In some embodiments, R⁴ is

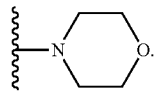 [SMILES: *N1CCOCC1]

In some embodiments, R¹ is

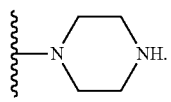

In some embodiments, R⁴ is

In some embodiments, R¹ is

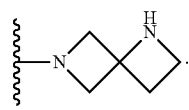 [SMILES: *N1CC2(CCN2)C1]

In some embodiments, R is

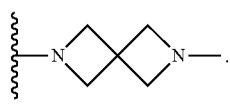 [SMILES: *N1CC2(C1)CN(C)C2]

In some embodiments, R⁴ is

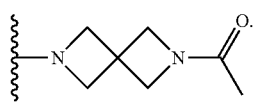

In some embodiments, R⁴ is

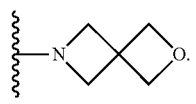 [SMILES: *N1CC2(COC2)C1]

In some embodiments, R⁴ is

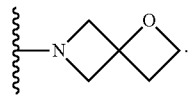 [SMILES: *N1CC2(CCO2)C1]

In some embodiments, R⁴ is selected from those depicted in Tables 1-4, below.

As defined above and described herein, m is 0, 1, 2, 3, 4 or 5.

In some embodiments, m is 0. In some embodiments, m is 1. In some embodiments, m is 2. In some embodiments, m is 3. In some embodiments, m is 4. In some embodiments, m is 5.

In some embodiments, m is 1, 2 or 3.

In some embodiments, m is selected from those depicted in Tables 1-4, below.

As defined above and described herein, n is 0, 1, or 2.

In some embodiments, n is 0. In some embodiments, n is 1. In some embodiments, n is 2.

In some embodiments, n is selected from those depicted in Tables 1-4, below.

As defined above and described herein, p is 0 or 1.

In some embodiments, p is 0. In some embodiments, p is 1.

In some embodiments, p is selected from those depicted in Tables 1-4, below.

As defined above and described herein, q is 0 or 1.

In some embodiments, q is 0. In some embodiments, q is 1.

In some embodiments, q is selected from those depicted in Tables 1-4, below.

In certain embodiments, the present invention provides a compound of Formula I, wherein Ring B is

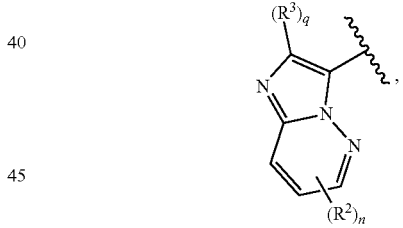

thereby forming a compound of formula II:

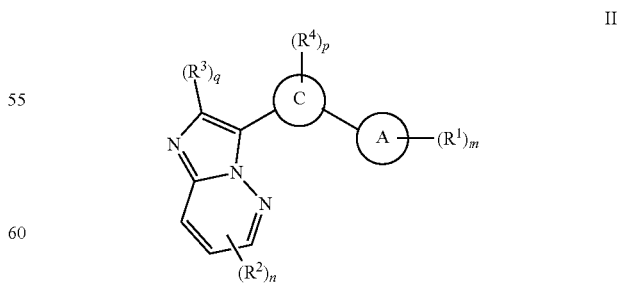

or a pharmaceutically acceptable salt thereof, wherein each of Ring A, Ring C, R¹, R², R³, R⁴, m, n, p, and q is as defined above and described in embodiments herein, both singly and in combination.

In certain embodiments, the present invention provides a compound of Formula I, wherein Ring B is

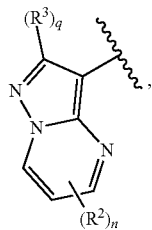

thereby forming a compound of formula III:

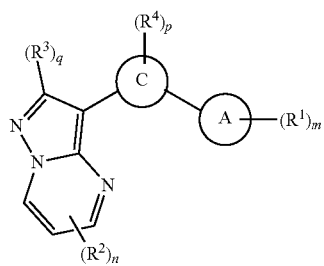

III or a pharmaceutically acceptable salt thereof, wherein each of Ring A, Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring B is

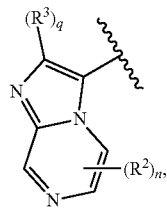

thereby forming a compound of formula IV:

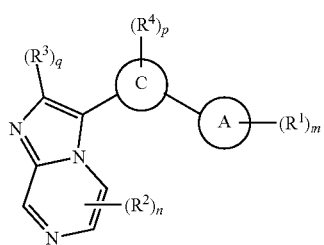

IV or a pharmaceutically acceptable salt thereof, wherein each of Ring A, Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring B is

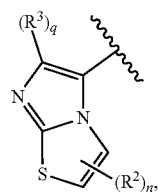

thereby forming a compound of formula V:

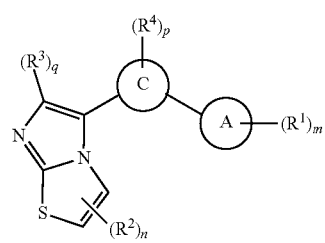

V or a pharmaceutically acceptable salt thereof, wherein each of Ring A, Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring B is

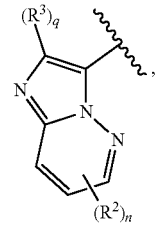

thereby forming a compound of formula VI:

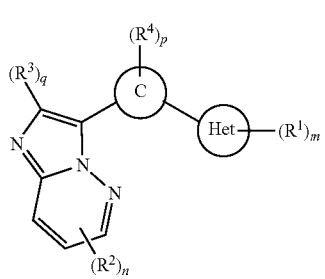

VI or a pharmaceutically acceptable salt thereof, wherein each of Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

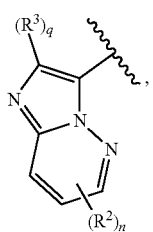

and Ring C is

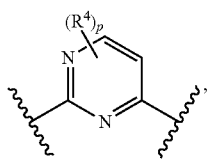

thereby forming a compound of formula VII:

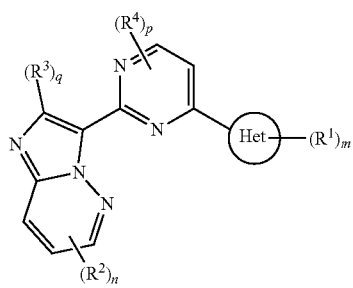
VII or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

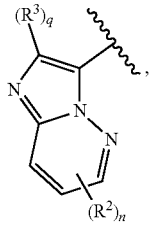

and Ring C is

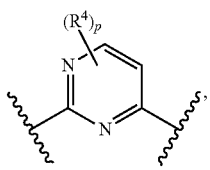

thereby forming a compound of formula VIII-a, VIII-b, or VIII-c, respectively:

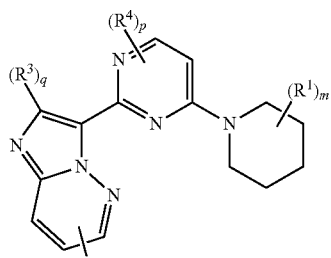
VIII-a

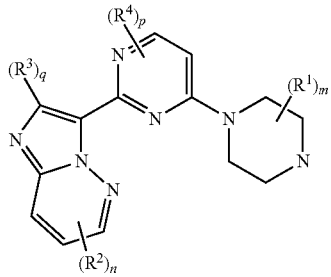
VIII-b

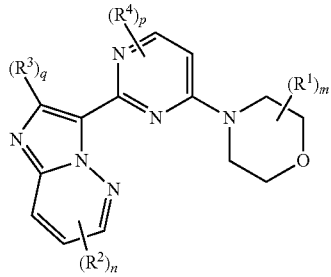
VIII-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

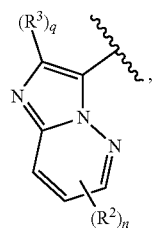

and Ring C is

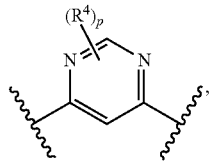

thereby forming a compound of formula IX:

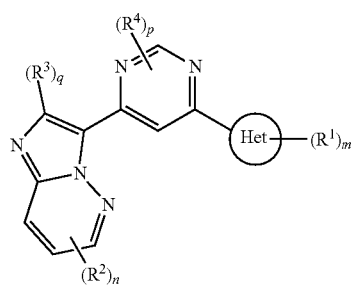

IX or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

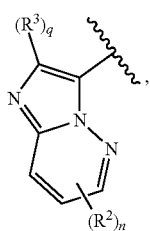

and Ring C is

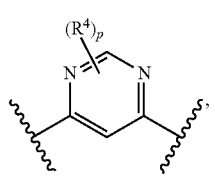

thereby forming a compound of formula X-a, X-b, or X-c, respectively:

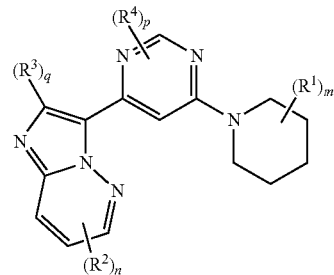

X-a

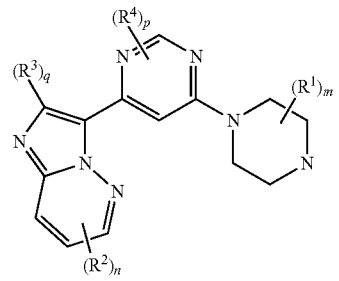

X-b

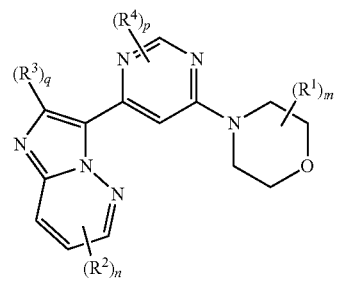

X-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

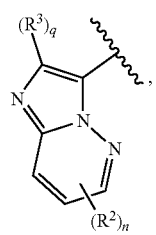

and Ring C is

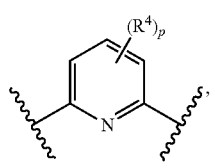

thereby forming a compound of formula XI:

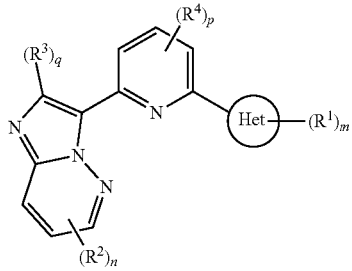

XI or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

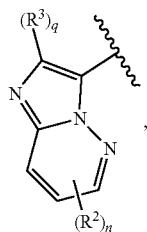

and Ring C is

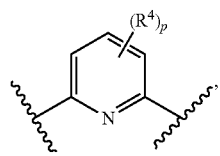

thereby forming a compound of formula XII-a, XII-b, or XII-c, respectively:

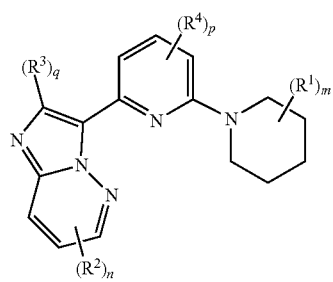

XII-a

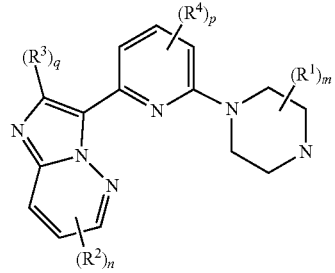

XII-b

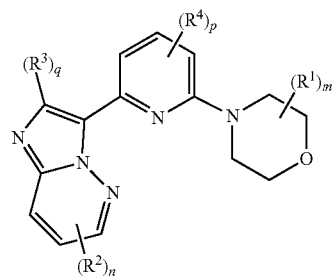

XII-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

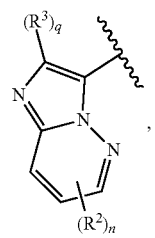

and Ring C is

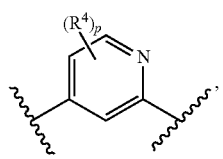

thereby forming a compound of formula XIII:

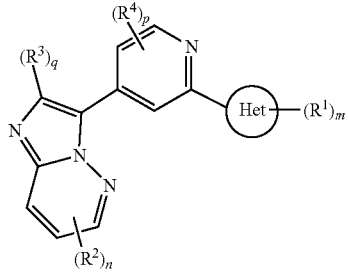

XIII or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

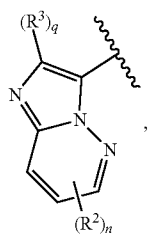

and Ring C is

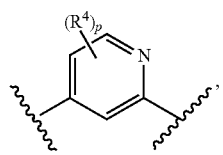

thereby forming a compound of formula XIV-a, XIV-b, or XIV-c, respectively:

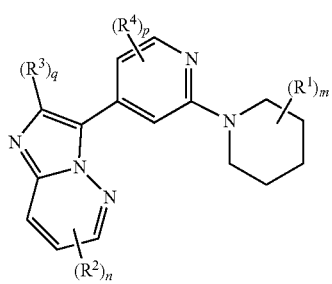

XIV-a

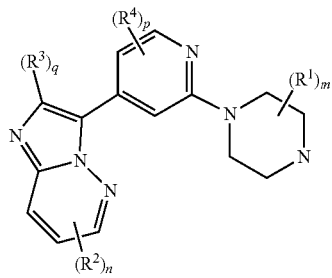

XIV-b

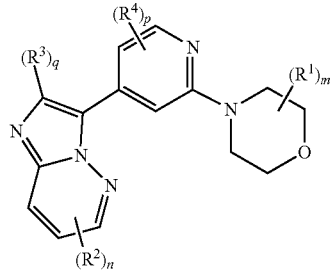

XIV-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring B is

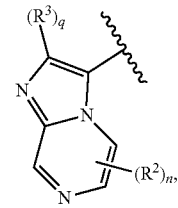

thereby forming a compound of formula XV:

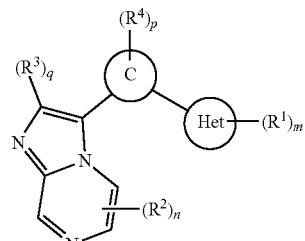

XV or a pharmaceutically acceptable salt thereof, wherein each of Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

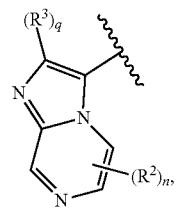

and Ring C is

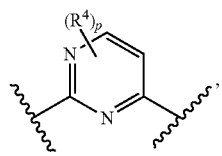

thereby forming a compound of formula XVI:

XVI

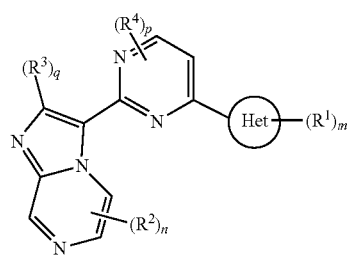

or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

and Ring C is

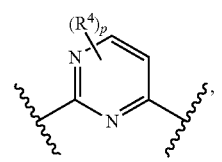

thereby forming a compound of formula XVII-a, XVII-b, or XVII-c, respectively:

XVII-a

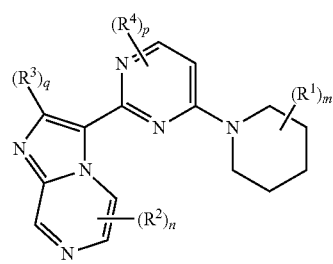

XVII-b

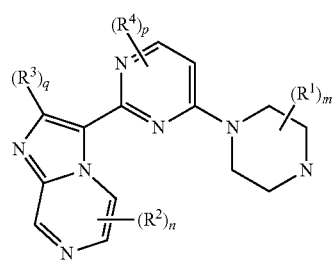

XVII-c

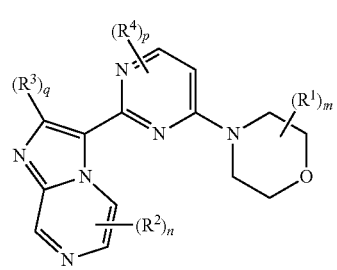

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

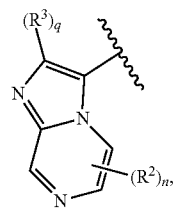

and Ring C is

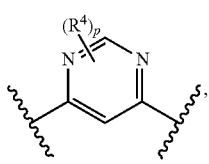

thereby forming a compound of formula XVIII:

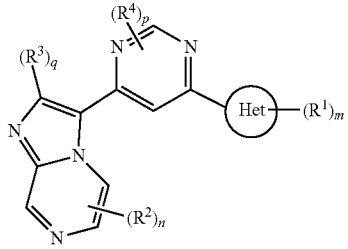

XVIII or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

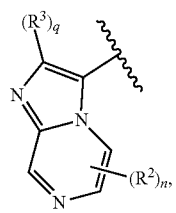

and Ring C is

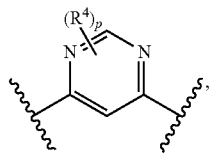

thereby forming a compound of formula XIX-a, XIX-b, or XIX-c, respectively:

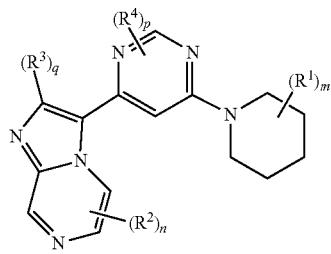

XIX-a

-continued

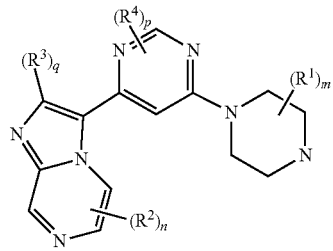

XIX-b

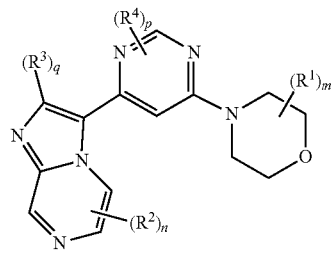

XIX-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, Ring B is

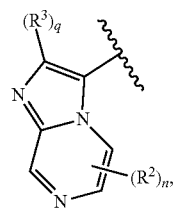

and Ring C is

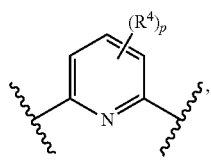

thereby forming a compound of formula XX:

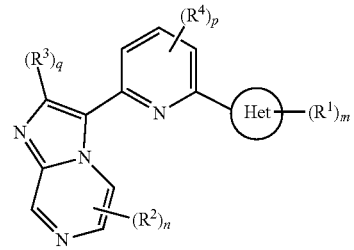

XX or a pharmaceutically acceptable salt thereof, wherein each of Het, R¹, R², R³, R⁴, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

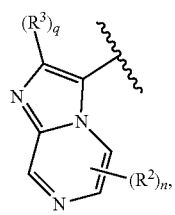

and Ring C is

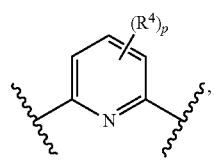

thereby forming a compound of formula XXI-a, XXI-b, or XXI-c, respectively:

XXI-a

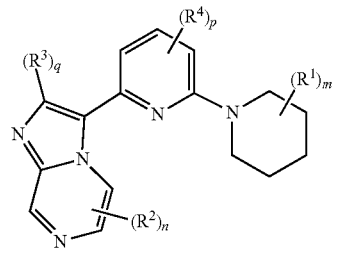

XXI-b

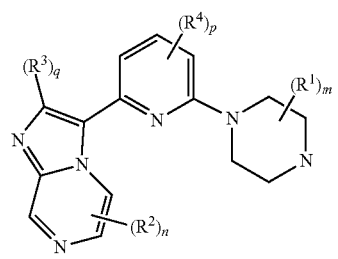

XXI-c

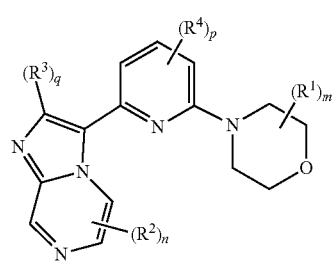

or a pharmaceutically acceptable salt thereof, wherein each of R¹, R², R³, R⁴, m, n, p, and q is as defined above and described in embodiments herein, both singly and in combination.

In certain embodiments, the present invention provides a compound of Formula I, wherein Ring A is Het, Ring B is

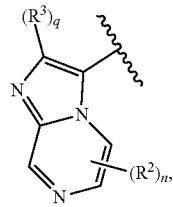

and Ring C is

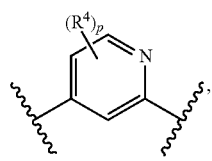

thereby forming a compound of formula XXII:

XXII

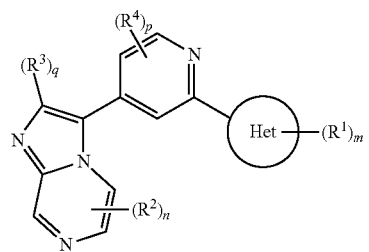

or a pharmaceutically acceptable salt thereof, wherein each of Het, R¹, R², R³, R⁴, m, n, p, and q is as defined above and described in embodiments herein, both singly and in combination.

In certain embodiments, the present invention provides a compound of Formula I, wherein Ring A is piperidinyl, piperazinyl, or morpholinyl, Ring B is

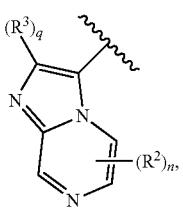

and Ring C is

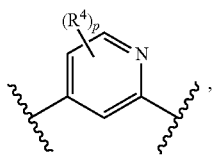

thereby forming a compound of formula XXIII-a, XXIII-b, or XXIII-c, respectively:

XXIII-a
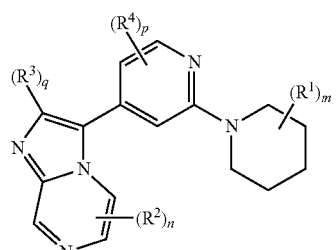

XXIII-b
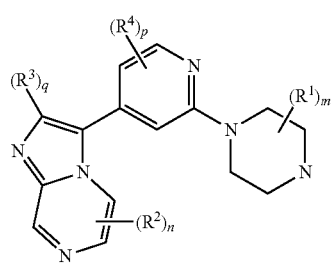

XXIII-c
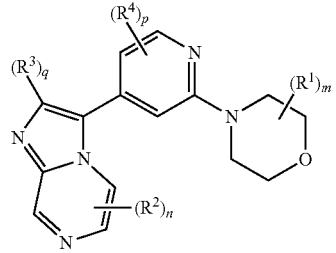

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of Formula I, wherein Ring A is Het, thereby forming a compound of formula XXIV:

XXIV
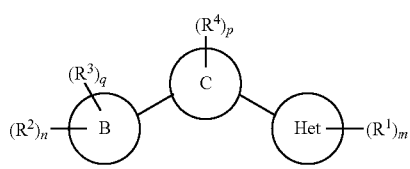

or a pharmaceutically acceptable salt thereof, wherein each of Het, Ring B, Ring C, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring C is

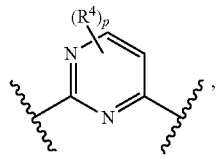

thereby forming a compound of formula XXV:

XXV
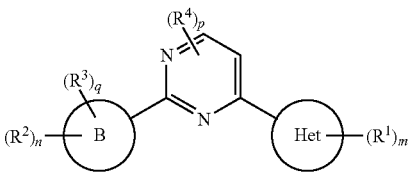

or a pharmaceutically acceptable salt thereof, wherein each of Het, Ring B, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring C is

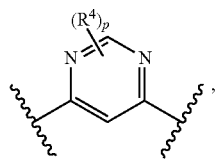

thereby forming a compound of formula XXVI:

XXVI
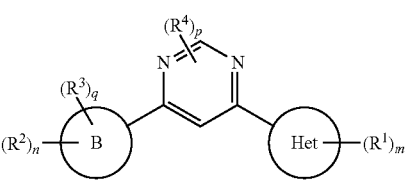

or a pharmaceutically acceptable salt thereof, wherein each of Het, Ring B, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring C is

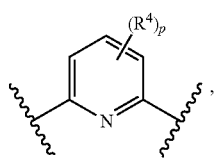

thereby forming a compound of formula XXVII:

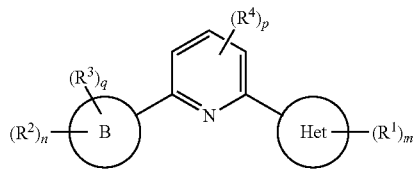

XXVII or a pharmaceutically acceptable salt thereof, wherein each of Het, Ring B, $R^1$, $R^2$, $R^3$, $R^4$, m, n, p, and q is as defined above and described in embodiments herein, both singly and in combination.

In certain embodiments, the present invention provides a compound of Formula I, wherein Ring A is Het and Ring C is

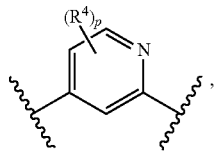

thereby forming a compound of formula XXVIII:

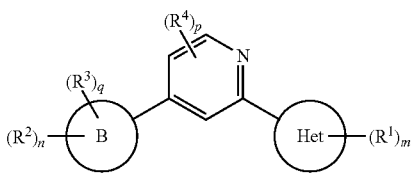

XXVIII or a pharmaceutically acceptable salt thereof, wherein each of Het, Ring B, $R^1$, $R^2$, $R^3$, $R^4$, m, n, p, and q is as defined above and described in embodiments herein, both singly and in combination.

In certain embodiments, the present invention provides a compound of Formula I, wherein n is 1, p is 1, q is 1, $R^2$ is —$CF_3$, $R^3$ is hydrogen, $R^4$ is hydrogen, Ring A is piperidinyl, piperazinyl, or morpholinyl, Ring B is

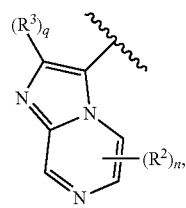

and Ring C is

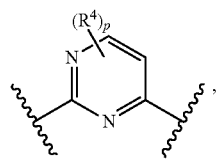

thereby forming a compound of formula XXIX-a, XXIX-b, or XXIX-c, respectively:

XXIX-a

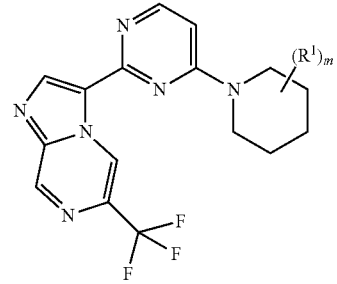

XXIX-b

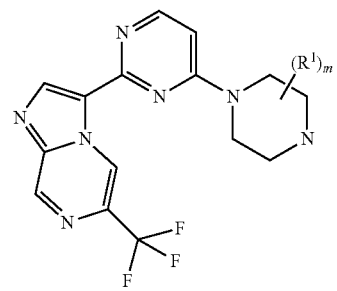

XXIX-c

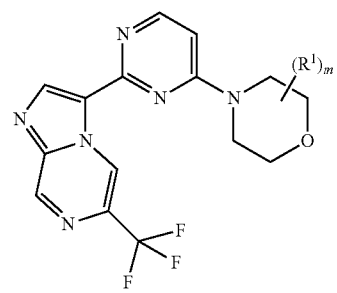

or a pharmaceutically acceptable salt thereof, wherein each of $R^1$ and m is as defined above and described in embodiments herein, both singly and in combination.

Exemplary compounds of the invention are set forth in Table 1, below.

TABLE 1
Exemplary compounds of formula II
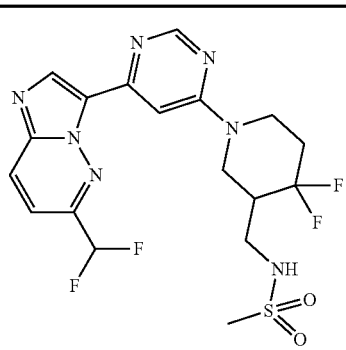
II-1
single stereoisomer
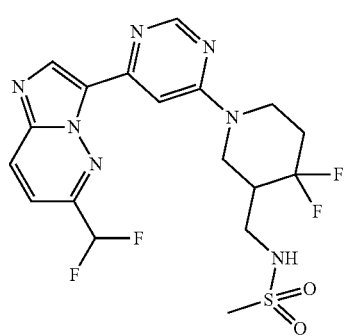
II-2
single stereoisomer
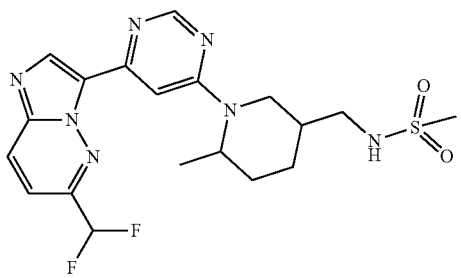 [SMILES: CC1CCC(CNS(C)(=O)=O)CN1c1cc(-c2cnc3ccc(C(F)F)nn23)ncn1]
II-3
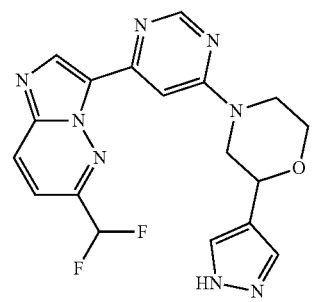 [SMILES: FC(F)c1ccc2ncc(-c3cc(N4CCOC(c5cn[nH]c5)C4)ncn3)n2n1]
II-4
TABLE 1-continued
Exemplary compounds of formula II
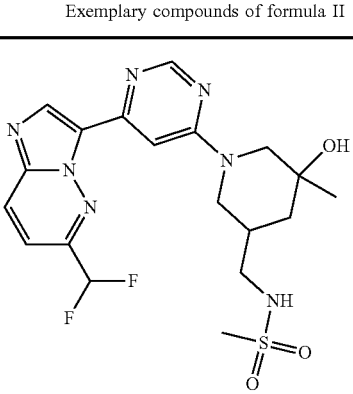
II-5
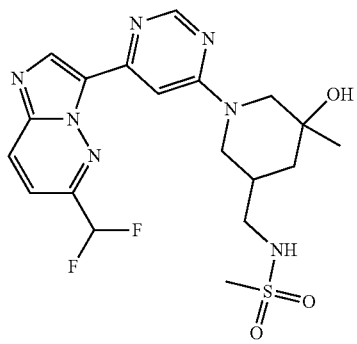 [SMILES: CC1(O)CC(CNS(C)(=O)=O)CN(c2cc(-c3cnc4ccc(C(F)F)nn34)ncn2)C1]
II-6
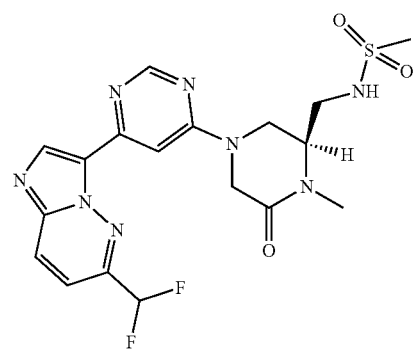 [SMILES: CN1C(=O)CN(c2cc(-c3cnc4ccc(C(F)F)nn34)ncn2)C[C@H]1CNS(C)(=O)=O]
II-7
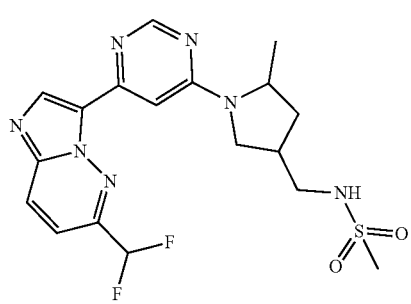 [SMILES: CC1CC(CNS(C)(=O)=O)CN1c1cc(-c2cnc3ccc(C(F)F)nn23)ncn1]
II-8

TABLE 1-continued
Exemplary compounds of formula II
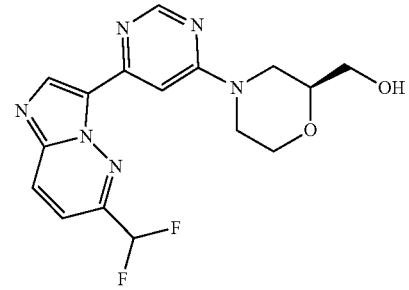 [SMILES: OC[C@@H]1CN(c2cc(-c3cnc4ccc(C(F)F)nn34)ncn2)CCO1] II-9
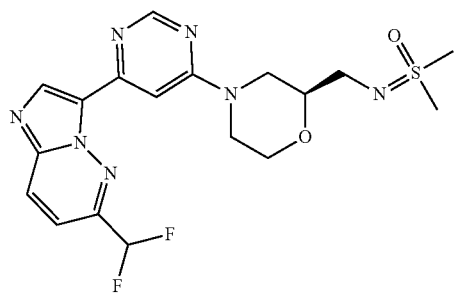 [SMILES: CS(C)(=O)=NC[C@@H]1CN(c2cc(-c3cnc4ccc(C(F)F)nn34)ncn2)CCO1] II-10
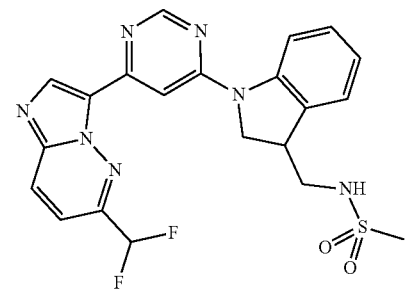 [SMILES: CS(=O)(=O)NCC1CN(c2cc(-c3cnc4ccc(C(F)F)nn34)ncn2)c2ccccc21] II-11
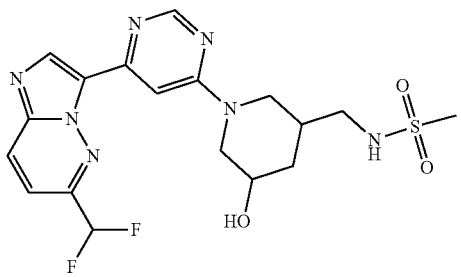 [SMILES: CS(=O)(=O)NCC1CC(O)CN(c2cc(-c3cnc4ccc(C(F)F)nn34)ncn2)C1] II-12
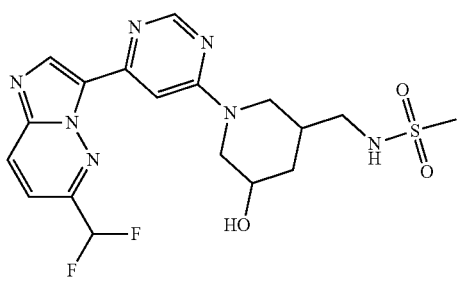 [SMILES: CS(=O)(=O)NCC1CC(O)CN(c2cc(-c3cnc4ccc(C(F)F)nn34)ncn2)C1] II-13
TABLE 1-continued
Exemplary compounds of formula II
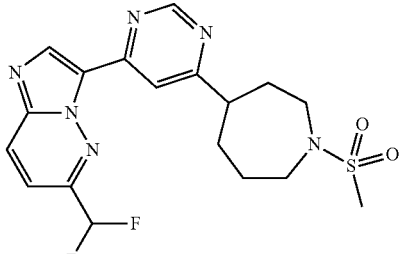 II-14
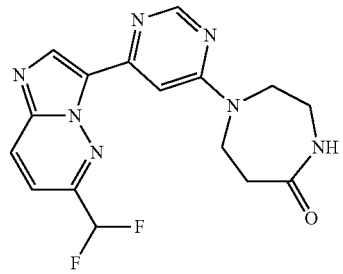 [SMILES: O=C1CCN(c2cc(-c3cnc4ccc(C(F)F)nn34)ncn2)CCN1] II-15
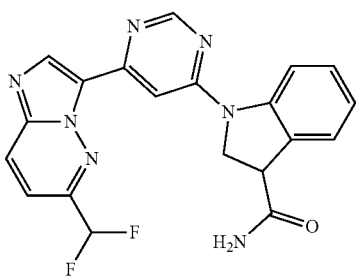 [SMILES: NC(=O)C1CN(c2cc(-c3cnc4ccc(C(F)F)nn34)ncn2)c2ccccc21] II-16
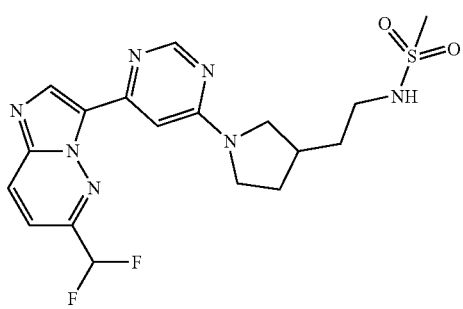 [SMILES: CS(=O)(=O)NCCC1CCN(c2cc(-c3cnc4ccc(C(F)F)nn34)ncn2)C1] II-17
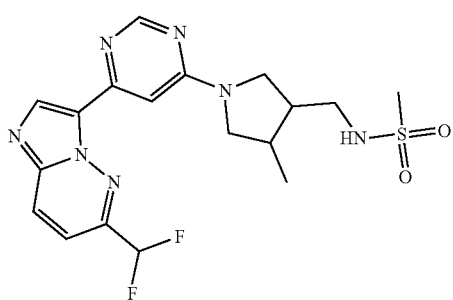 [SMILES: CC1CN(c2cc(-c3cnc4ccc(C(F)F)nn34)ncn2)CC1CNS(C)(=O)=O] II-18

TABLE 1-continued
Exemplary compounds of formula II
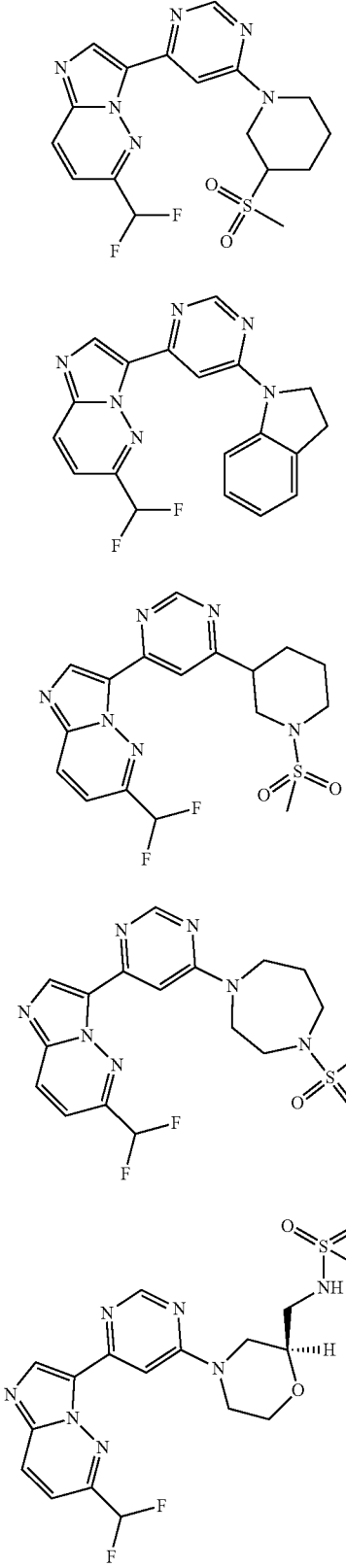
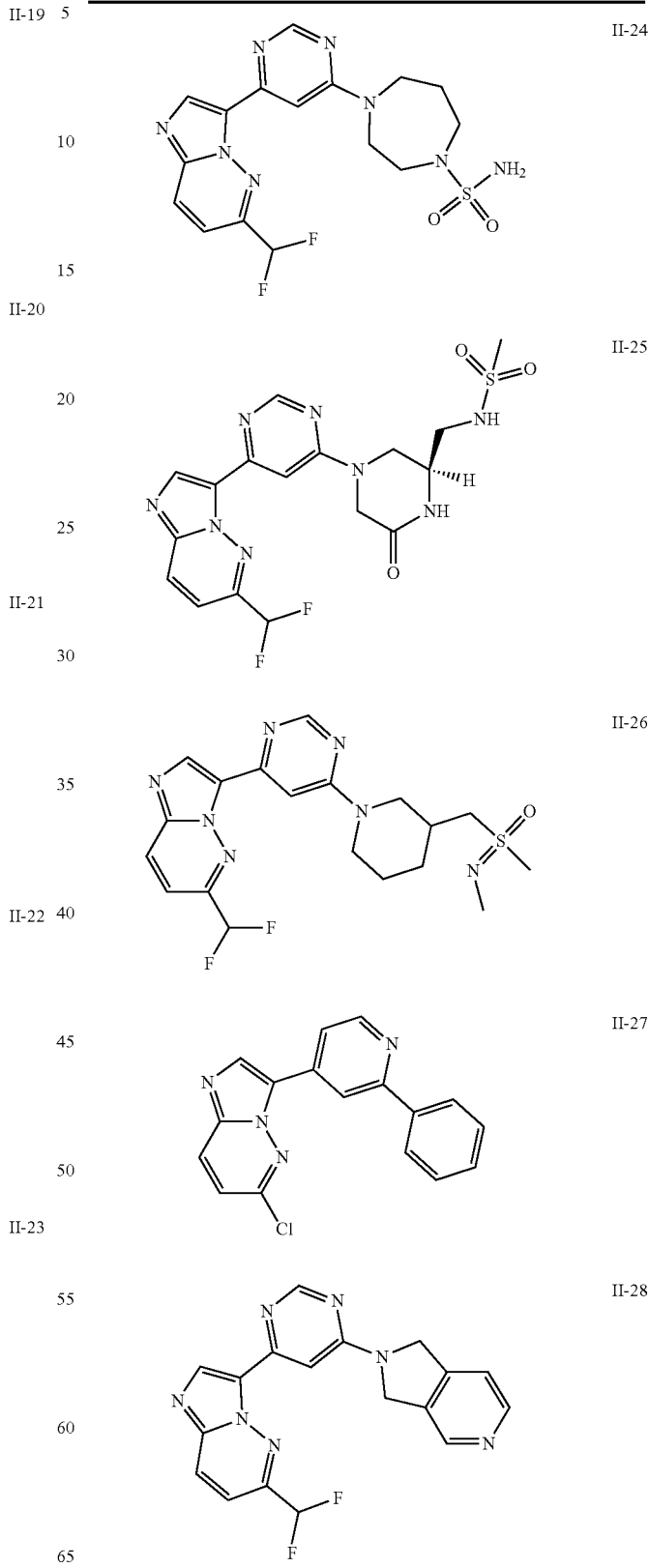

TABLE 1-continued
Exemplary compounds of formula II
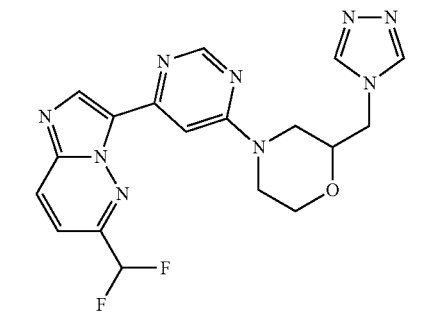 [SMILES: FC(F)c1ccc2ncc(-c3cc(N4CCOC(Cn5cnnc5)C4)ncn3)n2n1] II-29
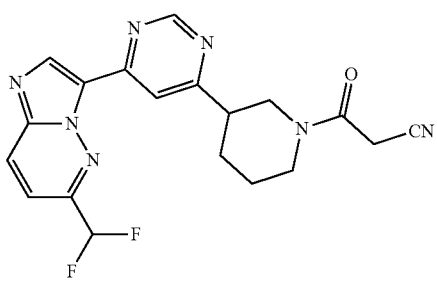 [SMILES: N#CCC(=O)N1CCCC(c2cc(-c3cnc4ccc(C(F)F)nn34)ncn2)C1] II-30
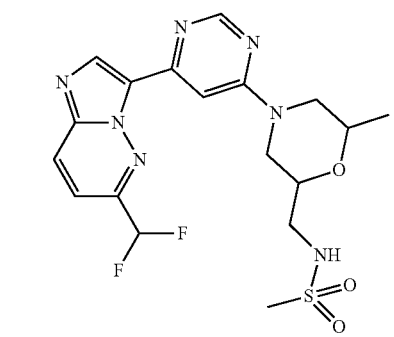 [SMILES: CC1CN(c2cc(-c3cnc4ccc(C(F)F)nn34)ncn2)CC(CNS(C)(=O)=O)O1] II-31
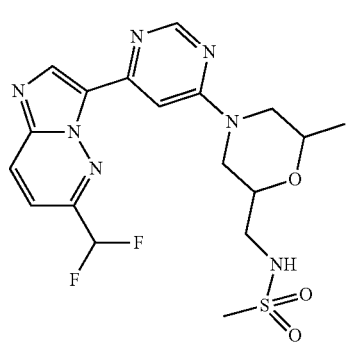 [SMILES: CC1CN(c2cc(-c3cnc4ccc(C(F)F)nn34)ncn2)CC(CNS(C)(=O)=O)O1] II-32
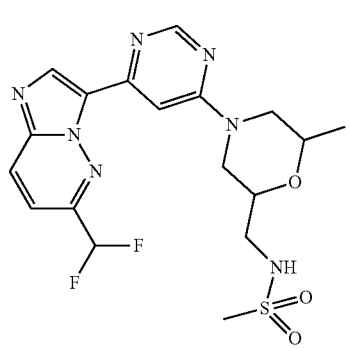 [SMILES: CC1CN(c2cc(-c3cnc4ccc(C(F)F)nn34)ncn2)CC(CNS(C)(=O)=O)O1] II-33
TABLE 1-continued
Exemplary compounds of formula II
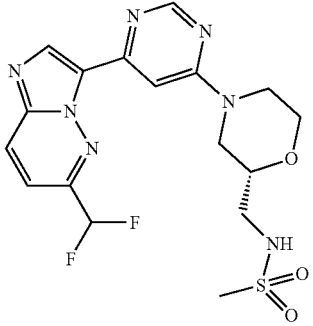 [SMILES: CS(=O)(=O)NC[C@@H]1CN(c2cc(-c3cnc4ccc(C(F)F)nn34)ncn2)CCO1] II-34
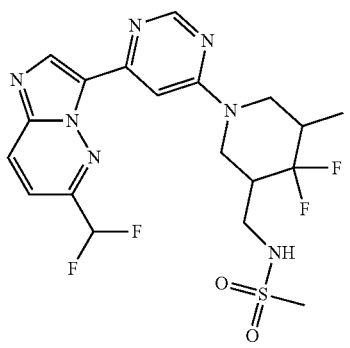 [SMILES: CC1CN(c2cc(-c3cnc4ccc(C(F)F)nn34)ncn2)CC(CNS(C)(=O)=O)C1(F)F] II-35
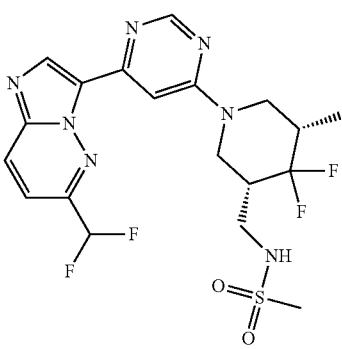 [SMILES: C[C@H]1CN(c2cc(-c3cnc4ccc(C(F)F)nn34)ncn2)C[C@@H](CNS(C)(=O)=O)C1(F)F] II-36
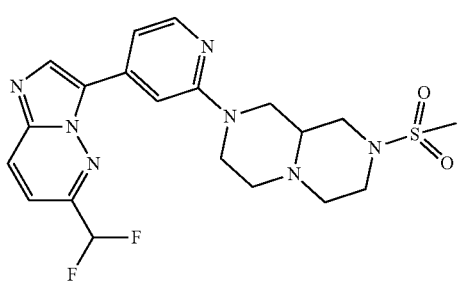 [SMILES: CS(=O)(=O)N1CCN2CCN(c3cc(-c4cnc5ccc(C(F)F)nn45)ccn3)CC2C1] II-37
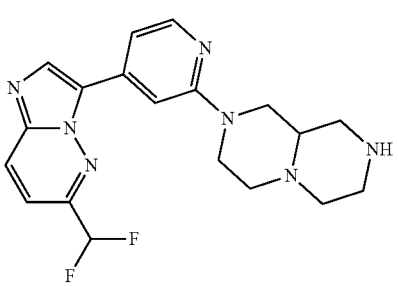 [SMILES: FC(F)c1ccc2ncc(-c3ccnc(N4CCN5CCNCC5C4)c3)n2n1] II-38

TABLE 1-continued
Exemplary compounds of formula II
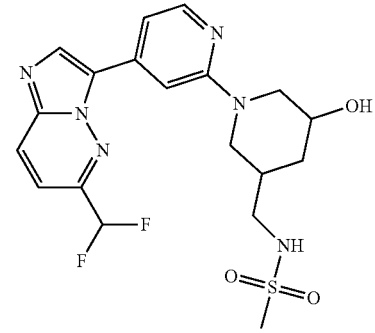 [SMILES: CS(=O)(=O)NCC1CC(O)CN(c2cc(-c3cnc4ccc(C(F)F)nn34)ccn2)C1] II-39
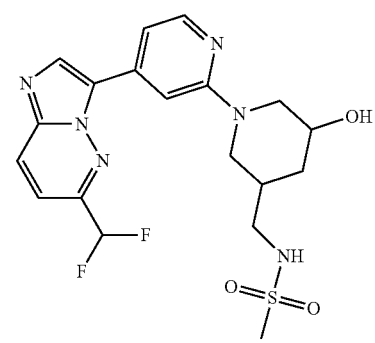 [SMILES: CS(=O)(=O)NCC1CC(O)CN(c2cc(-c3cnc4ccc(C(F)F)nn34)ccn2)C1] II-40
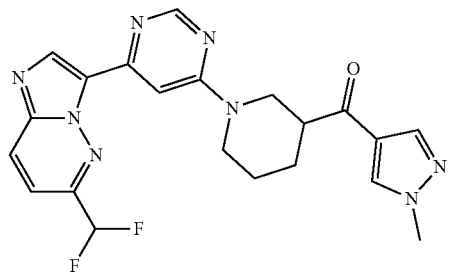 [SMILES: Cn1cc(C(=O)C2CCCN(c3cc(-c4cnc5ccc(C(F)F)nn45)ncn3)C2)cn1] II-41
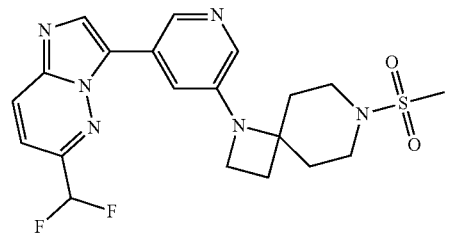 [SMILES: CS(=O)(=O)N1CCC2(CCN2c2cncc(-c3cnc4ccc(C(F)F)nn34)c2)CC1] II-42
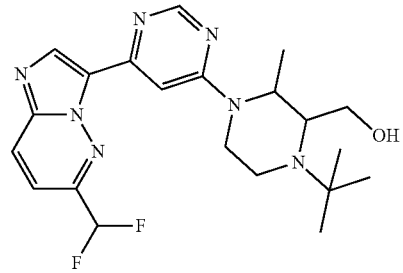 II-43
single diastereomer
(two enantiomers)
TABLE 1-continued
Exemplary compounds of formula II
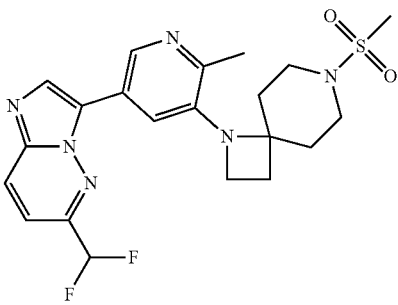 [SMILES: Cc1ncc(-c2cnc3ccc(C(F)F)nn23)cc1N1CCC12CCN(S(C)(=O)=O)CC2] II-44
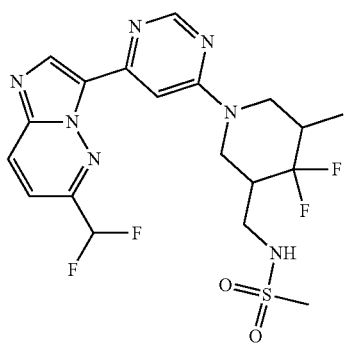 [SMILES: CC1CN(c2cc(-c3cnc4ccc(C(F)F)nn34)ncn2)CC(CNS(C)(=O)=O)C1(F)F] II-45
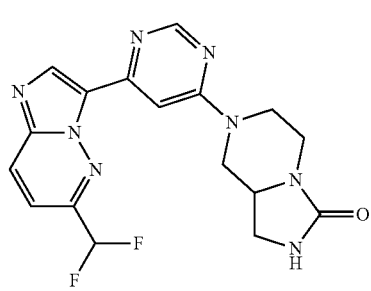 [SMILES: O=C1NCC2CN(c3cc(-c4cnc5ccc(C(F)F)nn45)ncn3)CCN12] II-46
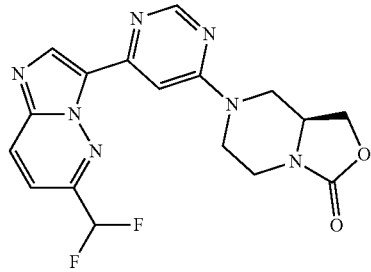 [SMILES: O=C1OC[C@@H]2CN(c3cc(-c4cnc5ccc(C(F)F)nn45)ncn3)CCN12] II-47
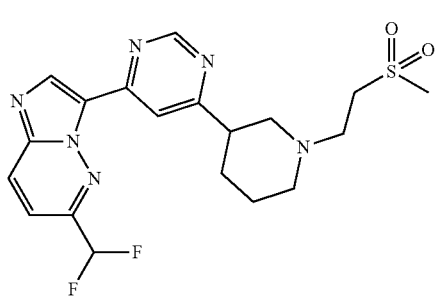 [SMILES: CS(=O)(=O)CCN1CCCC(c2cc(-c3cnc4ccc(C(F)F)nn34)ncn2)C1] II-48

TABLE 1-continued
Exemplary compounds of formula II
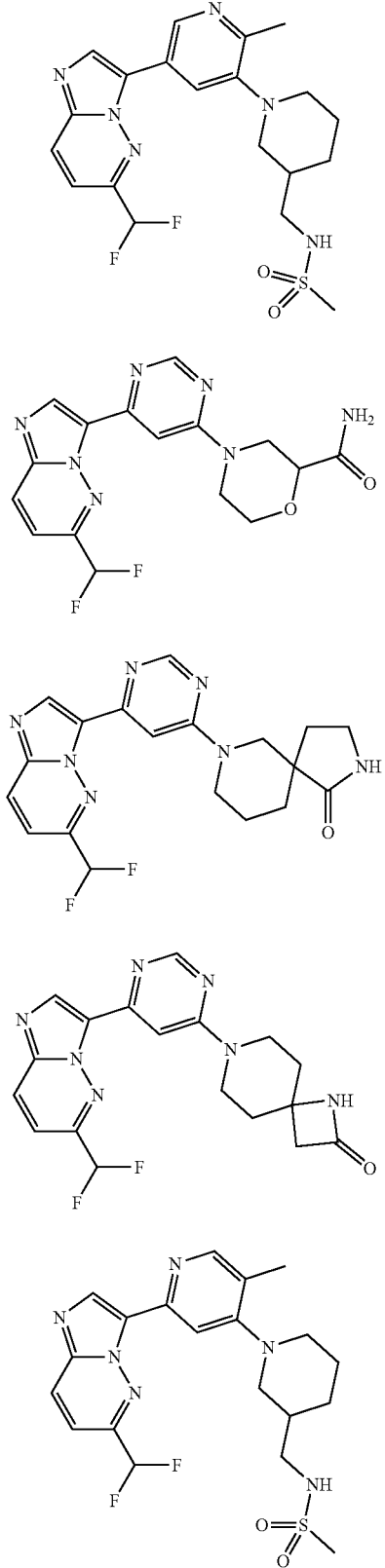
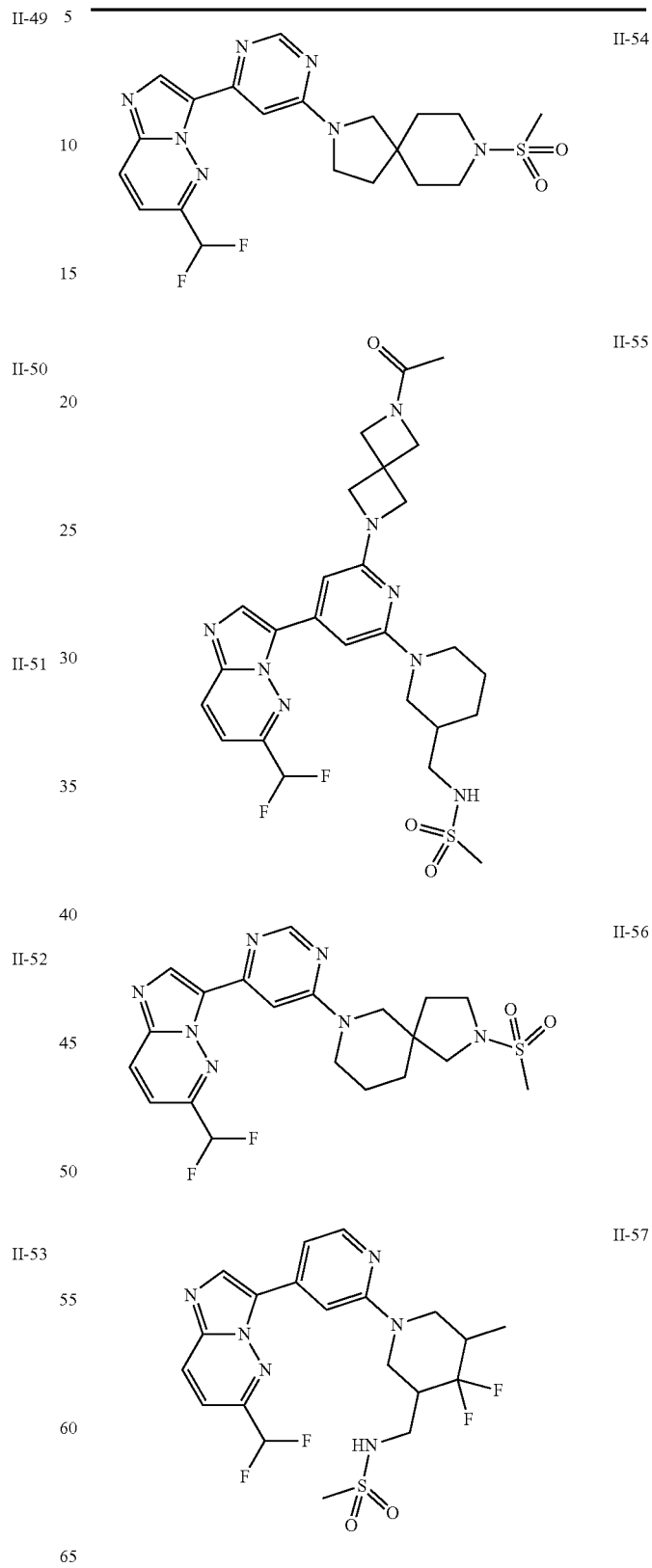

TABLE 1-continued
Exemplary compounds of formula II
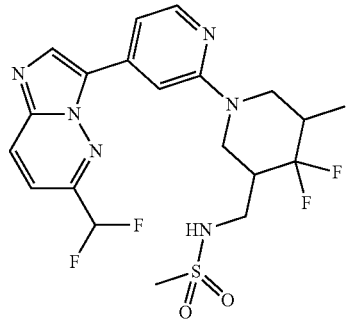 [SMILES: CC1CN(c2cc(-c3cnc4ccc(C(F)F)nn34)ccn2)CC(CNS(C)(=O)=O)C1(F)F]
II-58
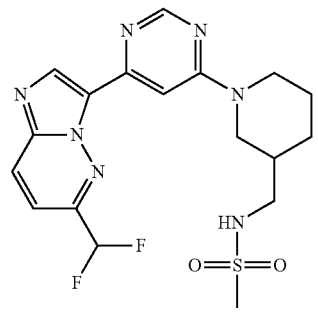 [SMILES: CS(=O)(=O)NCC1CCCN(c2cc(-c3cnc4ccc(C(F)F)nn34)ncn2)C1]
II-59
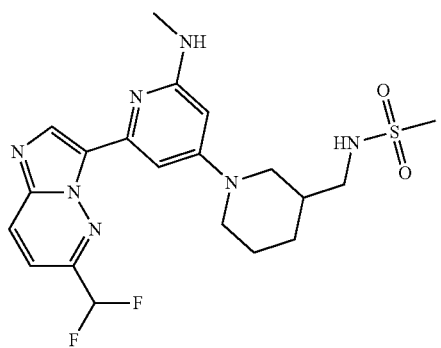 [SMILES: CNc1cc(N2CCCC(CNS(C)(=O)=O)C2)cc(-c2cnc3ccc(C(F)F)nn23)n1]
II-60
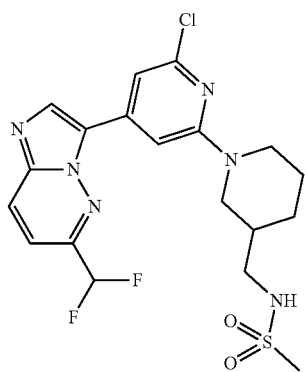 [SMILES: CS(=O)(=O)NCC1CCCN(c2cc(-c3cnc4ccc(C(F)F)nn34)cc(Cl)n2)C1]
II-61
TABLE 1-continued
Exemplary compounds of formula II
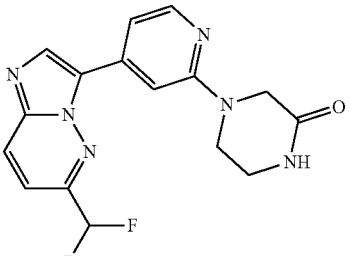
II-62
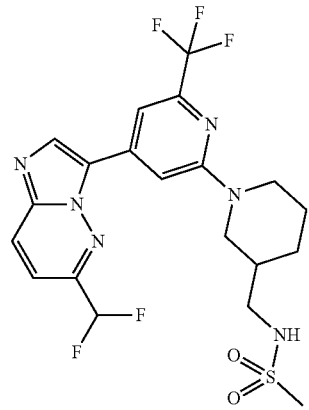 [SMILES: CS(=O)(=O)NCC1CCCN(c2cc(-c3cnc4ccc(C(F)F)nn34)cc(C(F)(F)F)n2)C1]
II-63
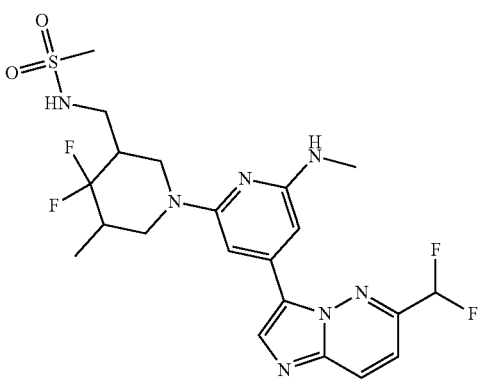 [SMILES: CNc1cc(-c2cnc3ccc(C(F)F)nn23)cc(N2CC(C)C(F)(F)C(CNS(C)(=O)=O)C2)n1]
II-64
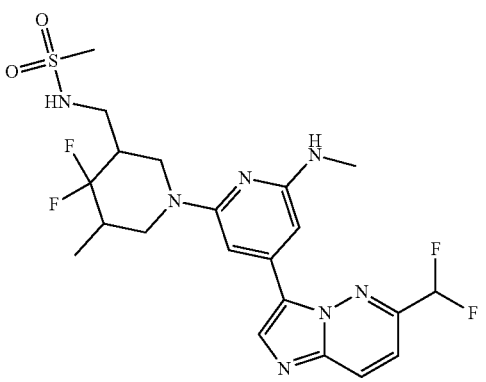 [SMILES: CNc1cc(-c2cnc3ccc(C(F)F)nn23)cc(N2CC(C)C(F)(F)C(CNS(C)(=O)=O)C2)n1]
II-65

TABLE 1-continued

Exemplary compounds of formula II

II-66, II-67, II-68, II-69, II-70, II-71, II-72, II-73

TABLE 1-continued
Exemplary compounds of formula II
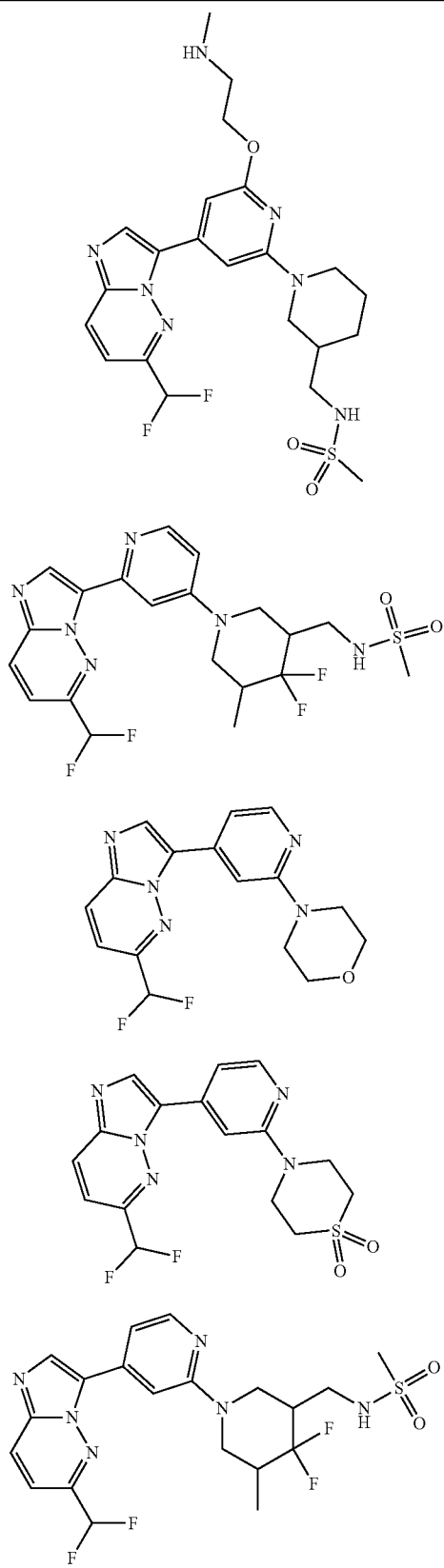
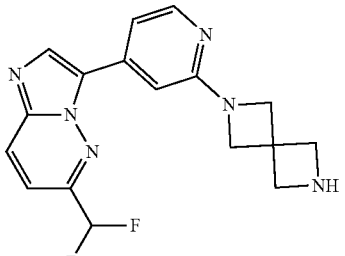

TABLE 1-continued
Exemplary compounds of formula II
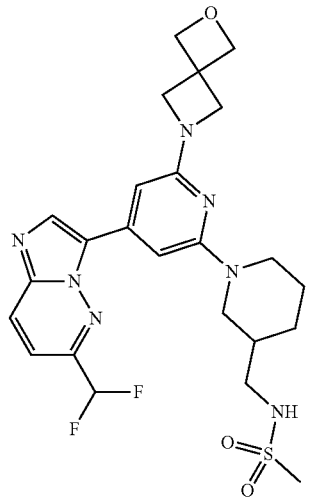 [SMILES: CS(=O)(=O)NCC1CCCN(c2cc(-c3cnc4ccc(C(F)F)nn34)cc(N3CC4(COC4)C3)n2)C1]
II-83
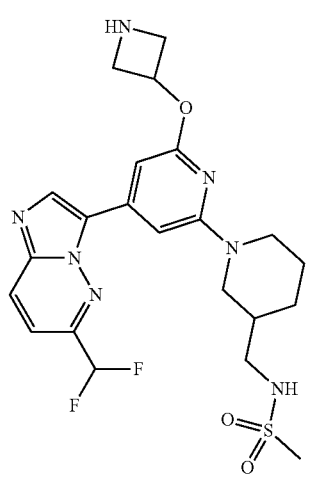 [SMILES: CS(=O)(=O)NCC1CCCN(c2cc(-c3cnc4ccc(C(F)F)nn34)cc(OC3CNC3)n2)C1]
II-84
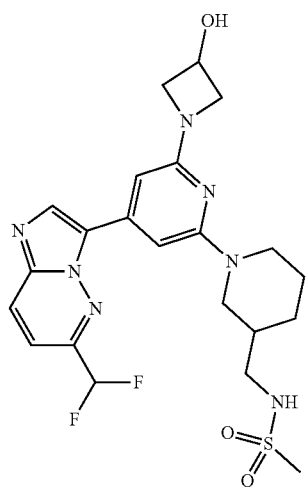 [SMILES: CS(=O)(=O)NCC1CCCN(c2cc(-c3cnc4ccc(C(F)F)nn34)cc(N3CC(O)C3)n2)C1]
II-85
TABLE 1-continued
Exemplary compounds of formula II
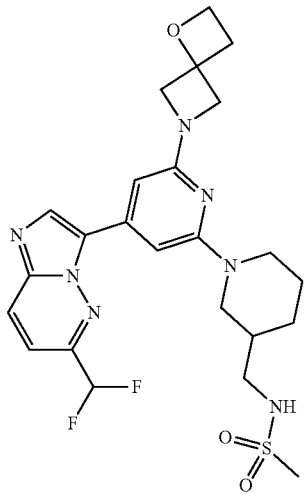 [SMILES: CS(=O)(=O)NCC1CCCN(c2cc(-c3cnc4ccc(C(F)F)nn34)cc(N3CC4(CCO4)C3)n2)C1]
II-86
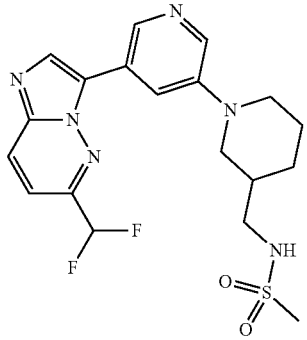 [SMILES: CS(=O)(=O)NCC1CCCN(c2cncc(-c3cnc4ccc(C(F)F)nn34)c2)C1]
II-87
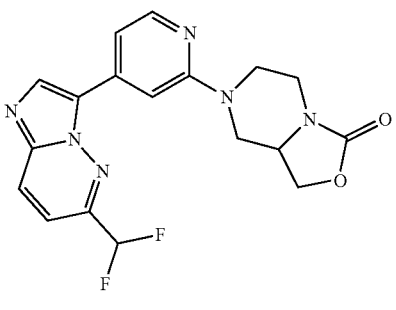 [SMILES: O=C1OCC2CN(c3cc(-c4cnc5ccc(C(F)F)nn45)ccn3)CCN12]
II-88

TABLE 1-continued
Exemplary compounds of formula II
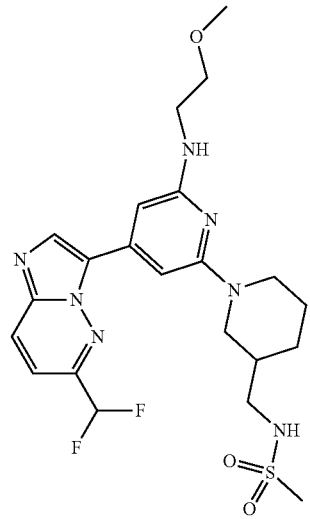 [SMILES: COCCNc1cc(-c2cnc3ccc(C(F)F)nn23)cc(N2CCCC(CNS(C)(=O)=O)C2)n1]
II-89
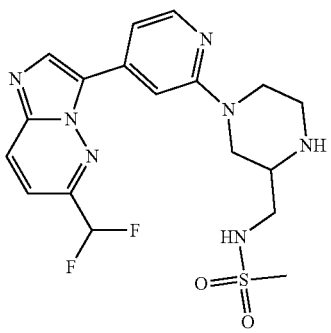 [SMILES: CS(=O)(=O)NCC1CN(c2cc(-c3cnc4ccc(C(F)F)nn34)ccn2)CCN1]
II-90
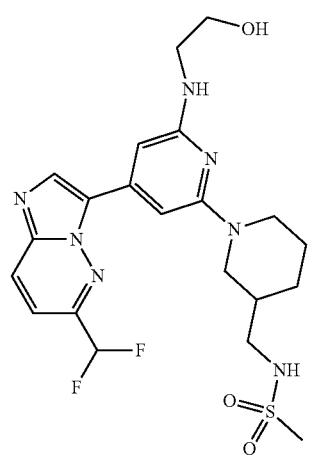 [SMILES: CS(=O)(=O)NCC1CCCN(c2cc(-c3cnc4ccc(C(F)F)nn34)cc(NCCO)n2)C1]
II-91
TABLE 1-continued
Exemplary compounds of formula II
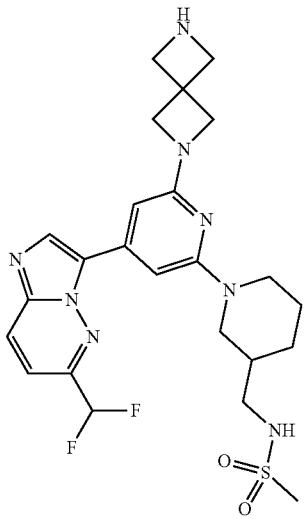 [SMILES: CS(=O)(=O)NCC1CCCN(c2cc(-c3cnc4ccc(C(F)F)nn34)cc(N3CC4(CNC4)C3)n2)C1]
II-92
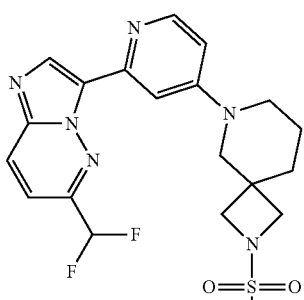
II-93
II-94
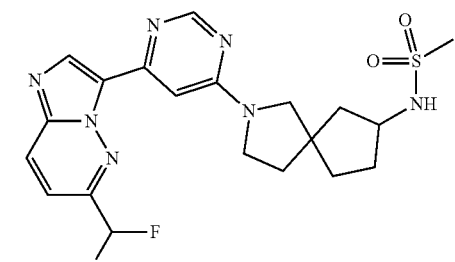
II-95
single diastereomer
(two enantiomers)

TABLE 1-continued
Exemplary compounds of formula II
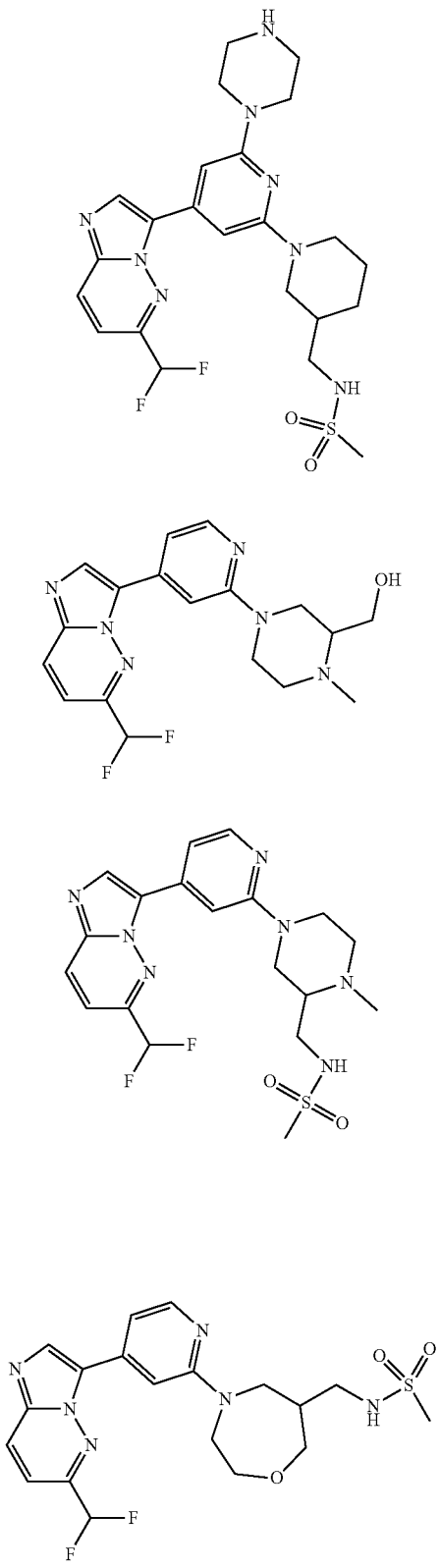
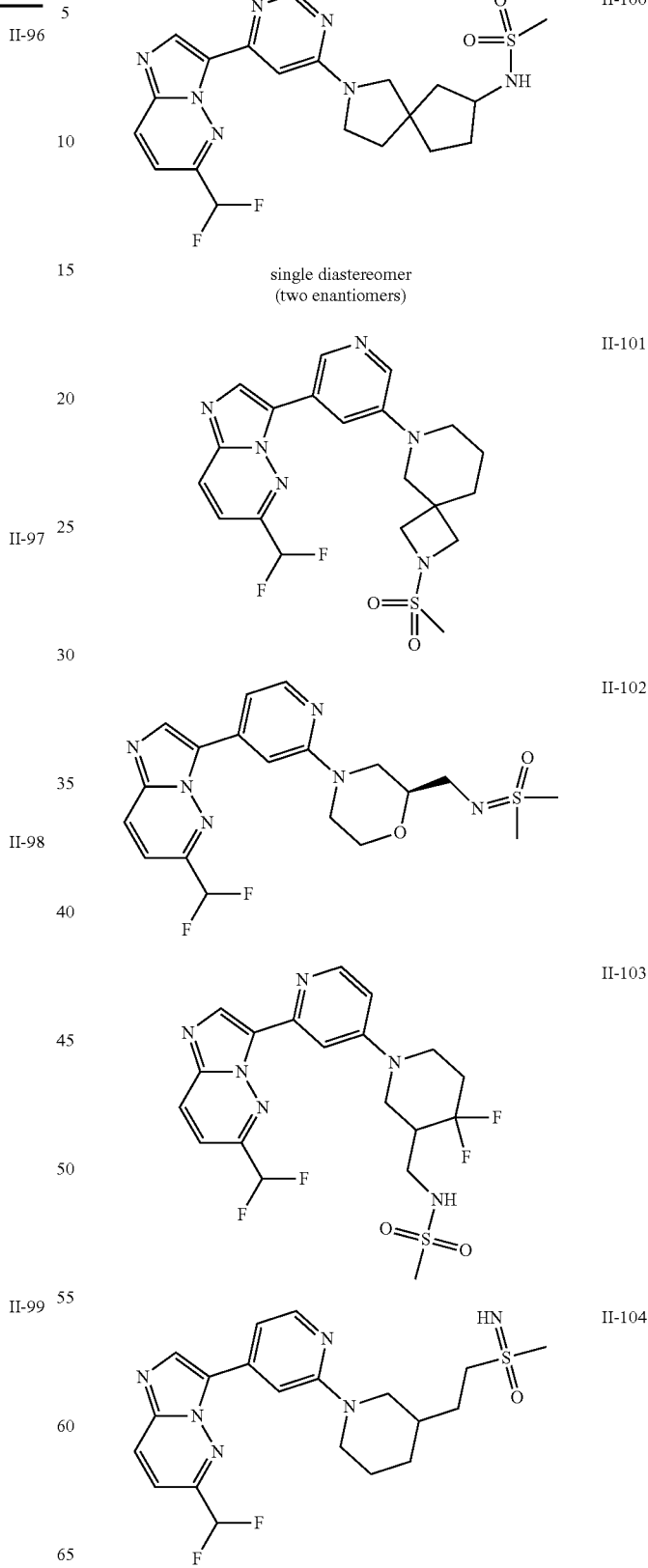
single diastereomer
(two enantiomers)

TABLE 1-continued

Exemplary compounds of formula II

| | |
|---|---|
| II-105 | II-110 |
| II-106 | II-111 |
| II-107 | II-112 |
| II-108 | II-113 |
| II-109 | II-114 |

TABLE 1-continued
Exemplary compounds of formula II
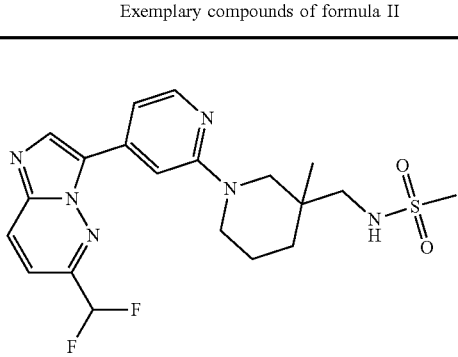
II-115
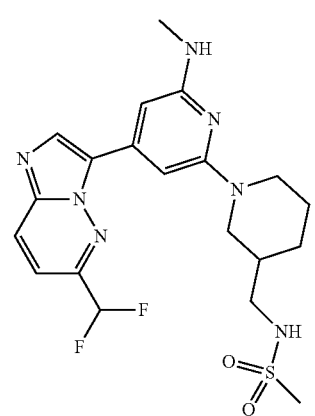 [SMILES: CNc1cc(-c2cnc3ccc(C(F)F)nn23)cc(N2CCCC(CNS(C)(=O)=O)C2)n1]
II-116
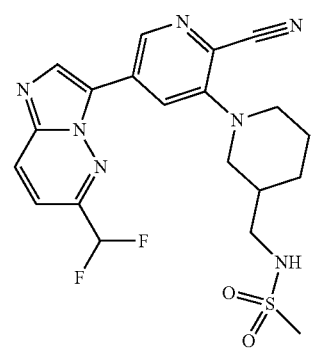 [SMILES: CS(=O)(=O)NCC1CCCN(c2cc(-c3cnc4ccc(C(F)F)nn34)cnc2C#N)C1]
II-117
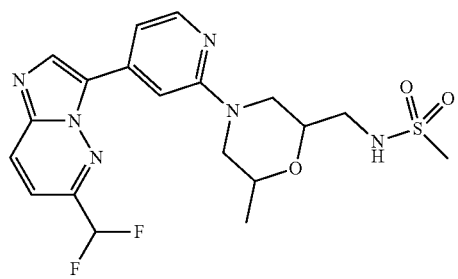 [SMILES: CC1CN(c2cc(-c3cnc4ccc(C(F)F)nn34)ccn2)CC(CNS(C)(=O)=O)O1]
II-118
TABLE 1-continued
Exemplary compounds of formula II
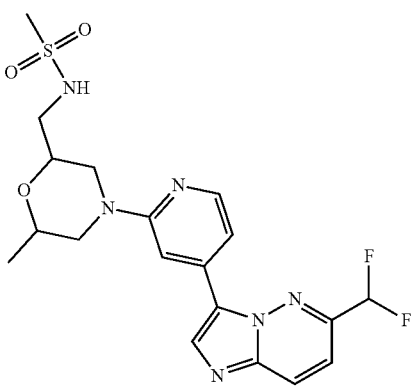 [SMILES: CC1CN(c2cc(-c3cnc4ccc(C(F)F)nn34)ccn2)CC(CNS(C)(=O)=O)O1]
II-119
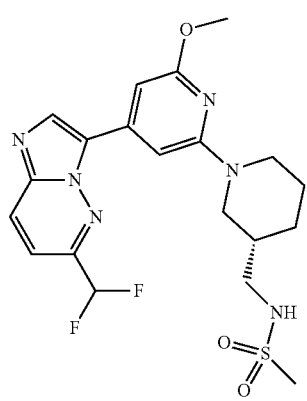 [SMILES: COc1cc(-c2cnc3ccc(C(F)F)nn23)cc(N2CCC[C@H](CNS(C)(=O)=O)C2)n1]
II-120
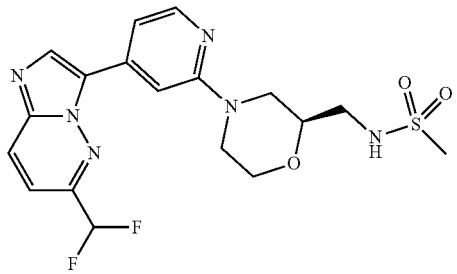 [SMILES: CS(=O)(=O)NC[C@@H]1CN(c2cc(-c3cnc4ccc(C(F)F)nn34)ccn2)CCO1]
II-121
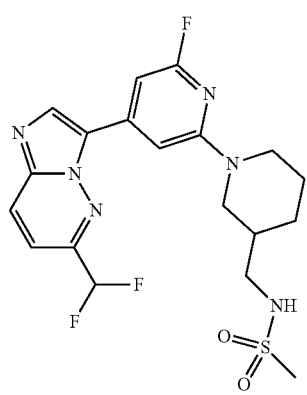 [SMILES: CS(=O)(=O)NCC1CCCN(c2cc(-c3cnc4ccc(C(F)F)nn34)cc(F)n2)C1]
II-122

TABLE 1-continued
Exemplary compounds of formula II
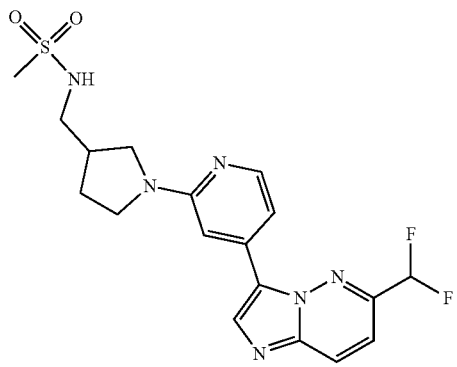 [SMILES: CS(=O)(=O)NCC1CCN(c2cc(-c3cnc4ccc(C(F)F)nn34)ccn2)C1] II-123
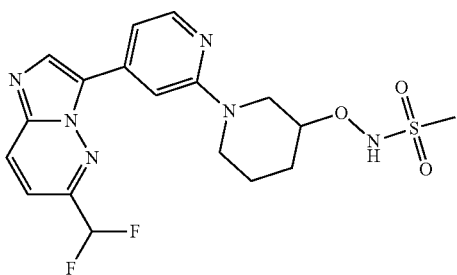 [SMILES: CS(=O)(=O)NOC1CCCN(c2cc(-c3cnc4ccc(C(F)F)nn34)ccn2)C1] II-124
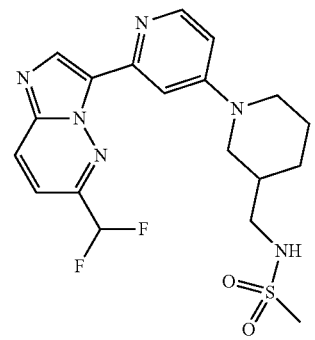 [SMILES: CS(=O)(=O)NCC1CCCN(c2ccnc(-c3cnc4ccc(C(F)F)nn34)c2)C1] II-125
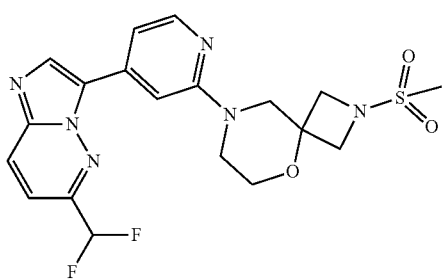 [SMILES: CS(=O)(=O)N1CC2(CN(c3cc(-c4cnc5ccc(C(F)F)nn45)ccn3)CCO2)C1] II-126
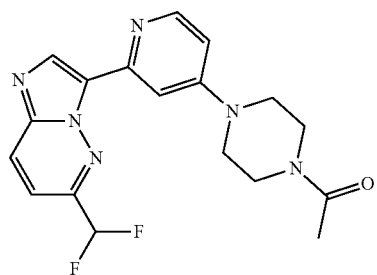 [SMILES: CC(=O)N1CCN(c2ccnc(-c3cnc4ccc(C(F)F)nn34)c2)CC1] II-127
TABLE 1-continued
Exemplary compounds of formula II
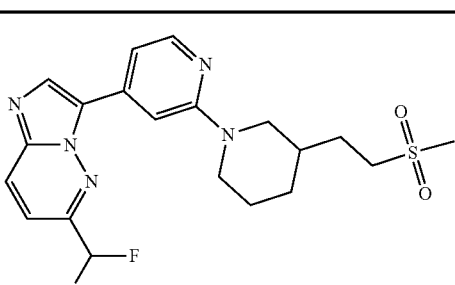 II-128
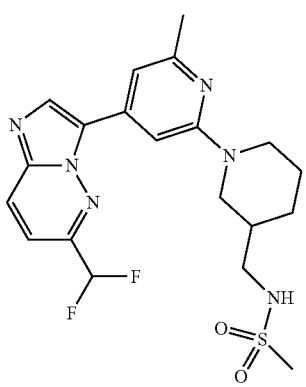 [SMILES: Cc1cc(-c2cnc3ccc(C(F)F)nn23)cc(N2CCCC(CNS(C)(=O)=O)C2)n1] II-129
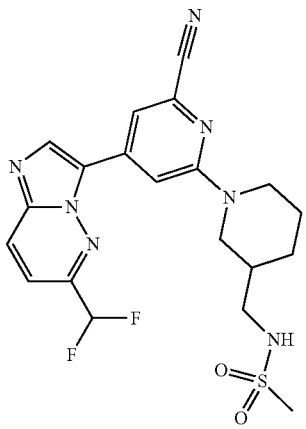 [SMILES: CS(=O)(=O)NCC1CCCN(c2cc(-c3cnc4ccc(C(F)F)nn34)cc(C#N)n2)C1] II-130
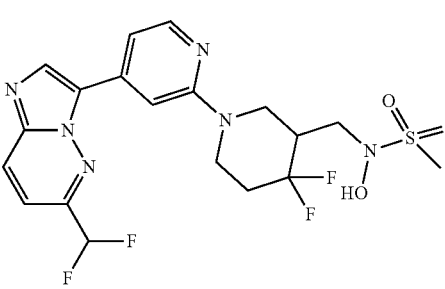 II-131

TABLE 1-continued

Exemplary compounds of formula II

| II-132 | II-137 |
| II-133 | II-138 |
| II-134 | II-139 |
| II-135 | II-140 (single diastereomer, two enantiomers) |
| II-136 | II-141 |

TABLE 1-continued
Exemplary compounds of formula II
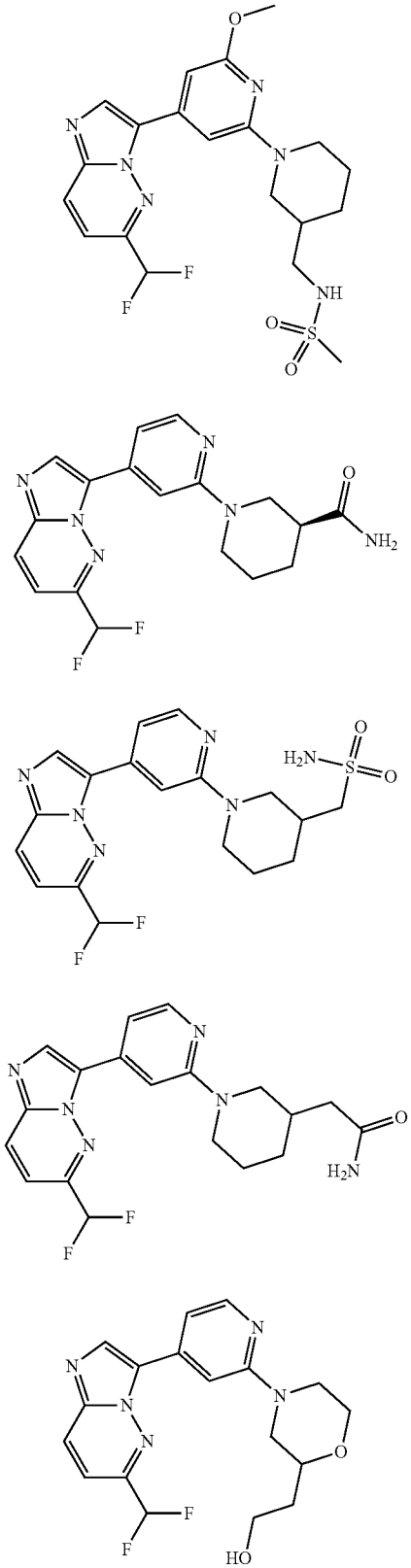
II-142
II-143
II-144
II-145
II-146
TABLE 1-continued
Exemplary compounds of formula II
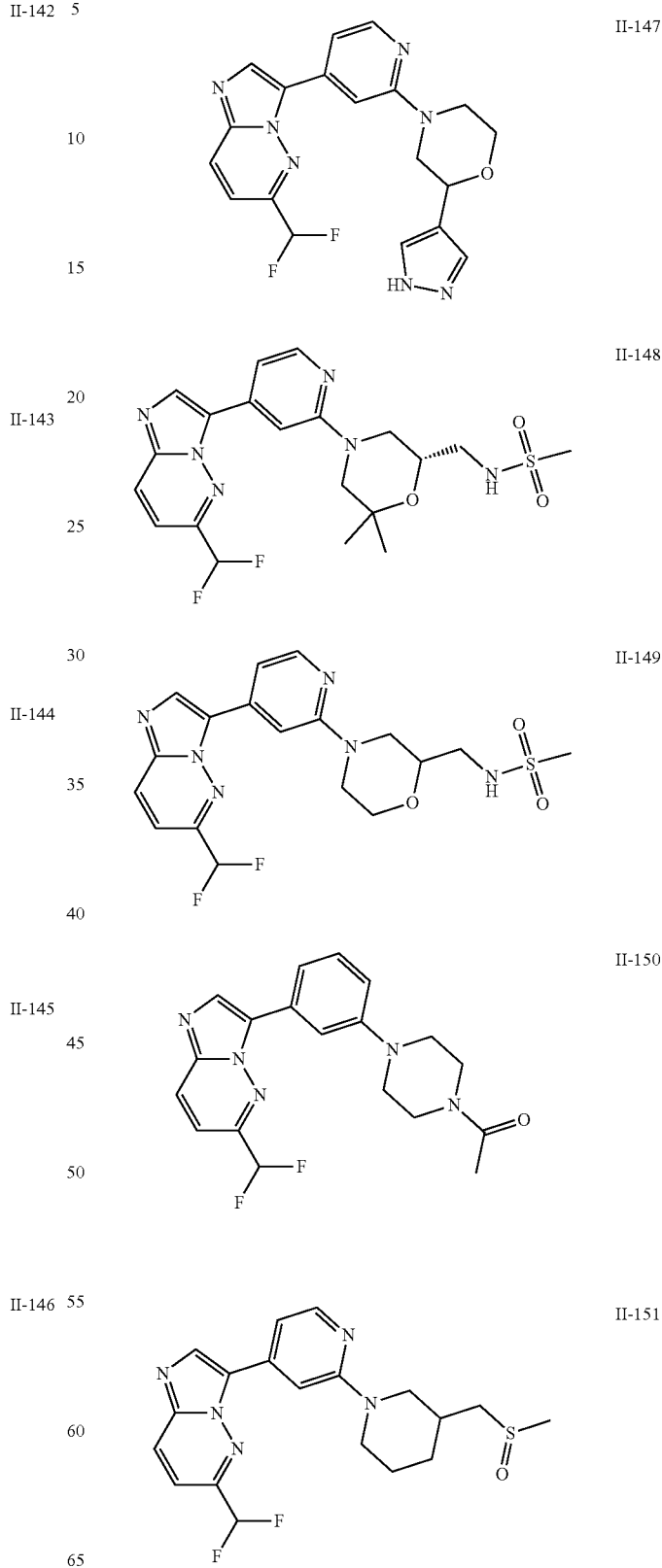
II-147
II-148
II-149
II-150
II-151

TABLE 1-continued
Exemplary compounds of formula II
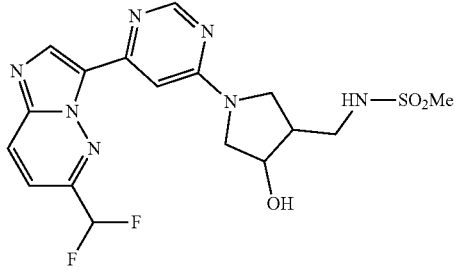
II-152
single diastereomer
(two enantiomers)
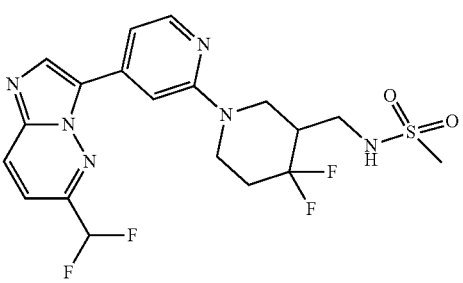 [SMILES: CS(=O)(=O)NCC1CN(c2cc(-c3cnc4ccc(C(F)F)nn34)ccn2)CCC1(F)F]
II-153
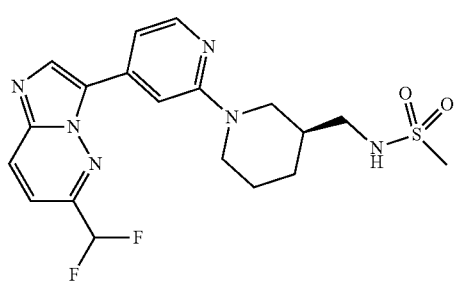 [SMILES: CS(=O)(=O)NC[C@H]1CCCN(c2cc(-c3cnc4ccc(C(F)F)nn34)ccn2)C1]
II-154
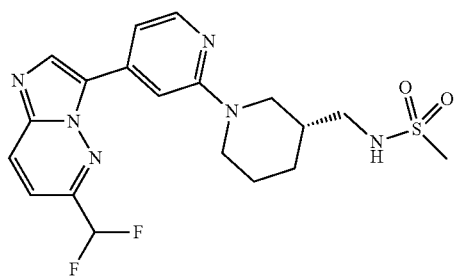 [SMILES: CS(=O)(=O)NC[C@@H]1CCCN(c2cc(-c3cnc4ccc(C(F)F)nn34)ccn2)C1]
II-155
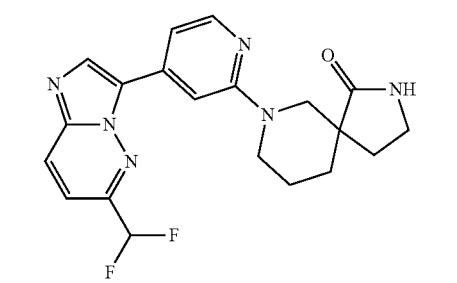 [SMILES: O=C1NCCC12CCCN(c1cc(-c3cnc4ccc(C(F)F)nn34)ccn1)C2]
II-156
TABLE 1-continued
Exemplary compounds of formula II
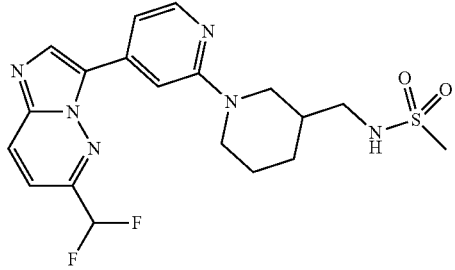 [SMILES: CS(=O)(=O)NCC1CCCN(c2cc(-c3cnc4ccc(C(F)F)nn34)ccn2)C1]
II-157
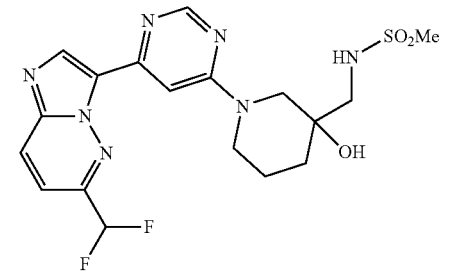 [SMILES: CS(=O)(=O)NCC1(O)CCCN(c2cc(-c3cnc4ccc(C(F)F)nn34)ncn2)C1]
II-158
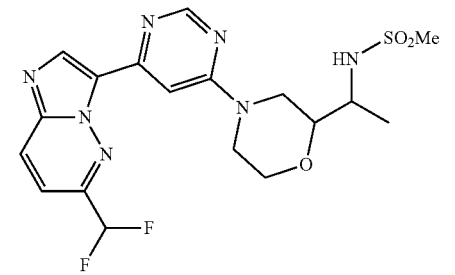
II-159
single diastereomer
(two enantiomers)
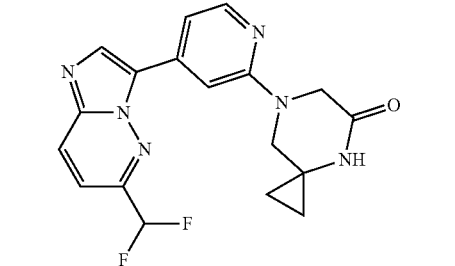 [SMILES: O=C1CN(c2cc(-c3cnc4ccc(C(F)F)nn34)ccn2)CC2(CC2)N1]
II-160
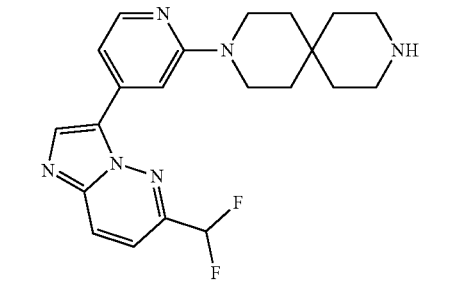 [SMILES: FC(F)c1ccc2ncc(-c3ccnc(N4CCC5(CCNCC5)CC4)c3)n2n1]
II-161

TABLE 1-continued
Exemplary compounds of formula II
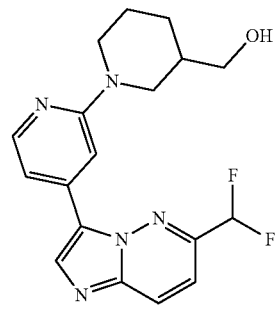 [SMILES: OCC1CCCN(c2cc(-c3cnc4ccc(C(F)F)nn34)ccn2)C1] II-162
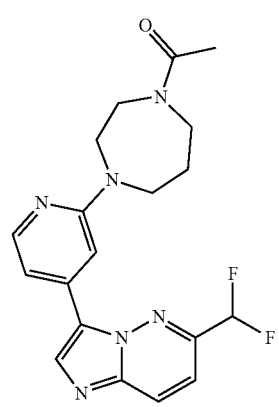 [SMILES: CC(=O)N1CCCN(c2cc(-c3cnc4ccc(C(F)F)nn34)ccn2)CC1] II-163
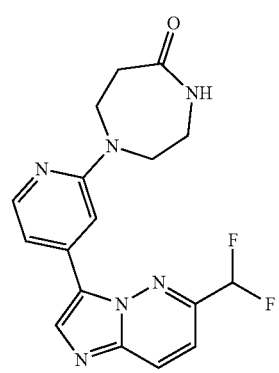 [SMILES: O=C1CCN(c2cc(-c3cnc4ccc(C(F)F)nn34)ccn2)CCN1] II-164
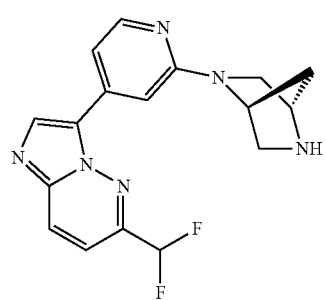 [SMILES: FC(F)c1ccc2ncc(-c3ccnc(N4C[C@@H]5C[C@H]4CN5)c3)n2n1] II-165
TABLE 1-continued
Exemplary compounds of formula II
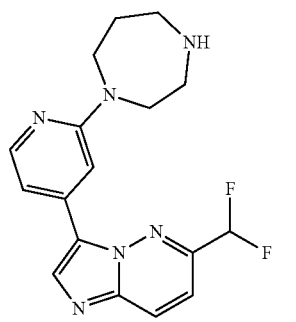 [SMILES: FC(F)c1ccc2ncc(-c3ccnc(N4CCCNCC4)c3)n2n1] II-166
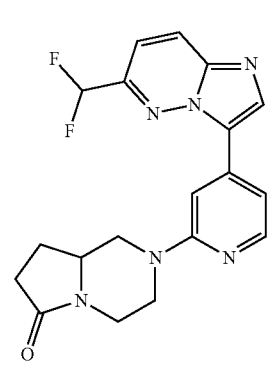 [SMILES: O=C1CCC2CN(c3cc(-c4cnc5ccc(C(F)F)nn45)ccn3)CCN12] II-167
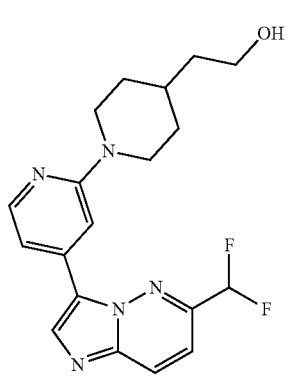 [SMILES: OCCC1CCN(c2cc(-c3cnc4ccc(C(F)F)nn34)ccn2)CC1] II-168
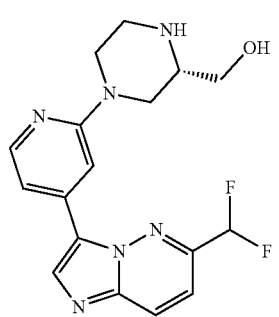 [SMILES: OC[C@@H]1CN(c2cc(-c3cnc4ccc(C(F)F)nn34)ccn2)CCN1] II-169

TABLE 1-continued
Exemplary compounds of formula II
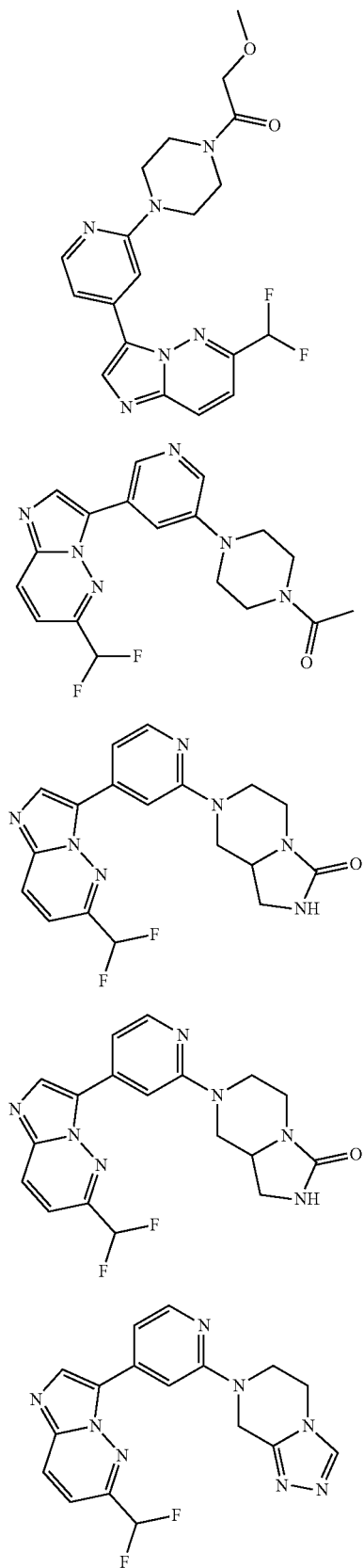
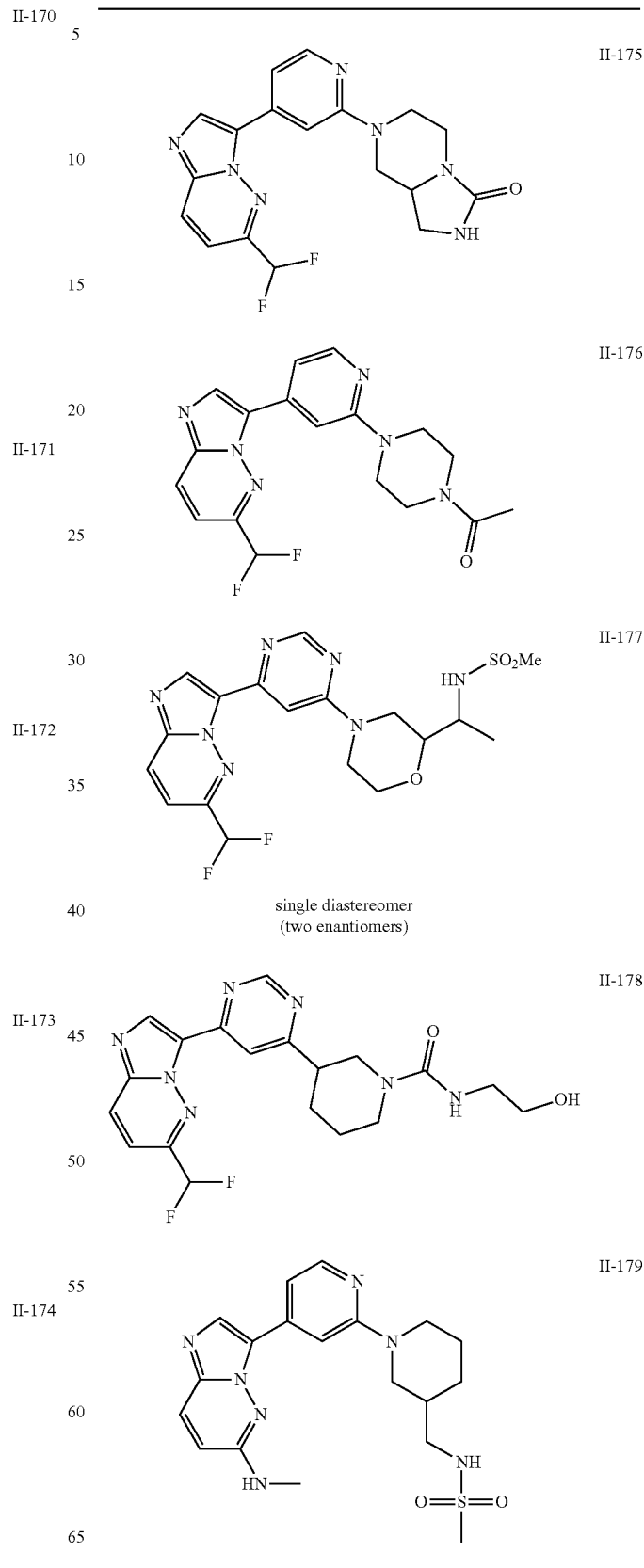

TABLE 1-continued
Exemplary compounds of formula II
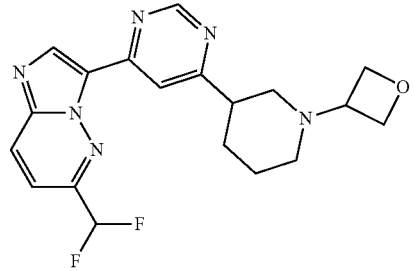 [SMILES: FC(F)c1ccc2ncc(-c3cc(C4CCCN(C5COC5)C4)ncn3)n2n1] II-180
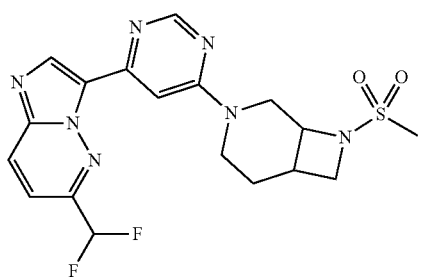 [SMILES: CS(=O)(=O)N1CC2CCN(c3cc(-c4cnc5ccc(C(F)F)nn45)ncn3)CC21] II-181
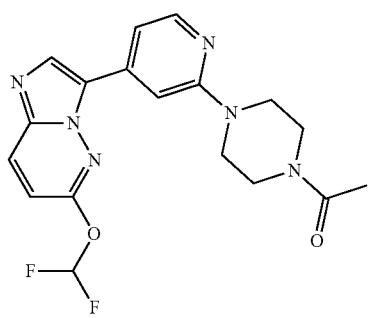 [SMILES: CC(=O)N1CCN(c2cc(-c3cnc4ccc(OC(F)F)nn34)ccn2)CC1] II-182
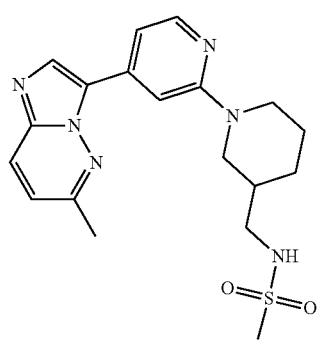 [SMILES: Cc1ccc2ncc(-c3ccnc(N4CCCC(CNS(C)(=O)=O)C4)c3)n2n1] II-183
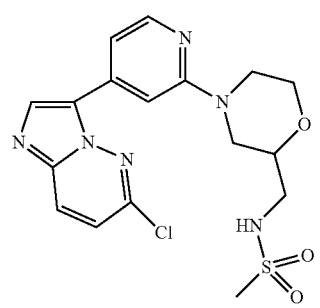 [SMILES: CS(=O)(=O)NCC1CN(c2cc(-c3cnc4ccc(Cl)nn34)ccn2)CCO1] II-184
TABLE 1-continued
Exemplary compounds of formula II
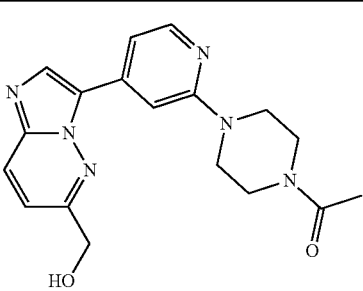 II-185
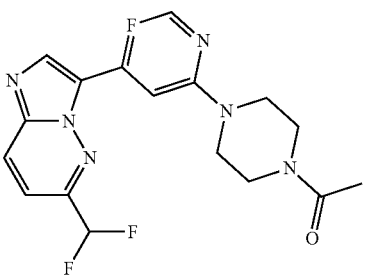 II-186
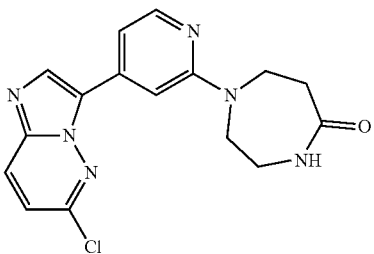 [SMILES: O=C1CCN(c2cc(-c3cnc4ccc(Cl)nn34)ccn2)CCN1] II-187
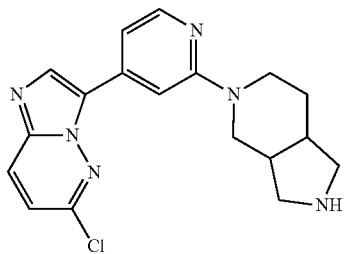 [SMILES: Clc1ccc2ncc(-c3ccnc(N4CCC5CNCC5C4)c3)n2n1] II-188
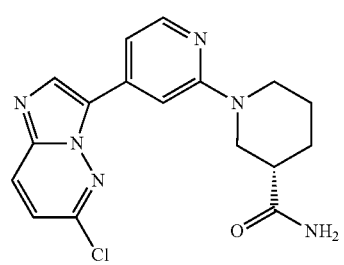 [SMILES: NC(=O)[C@H]1CCCN(c2cc(-c3cnc4ccc(Cl)nn34)ccn2)C1] II-189

TABLE 1-continued
Exemplary compounds of formula II
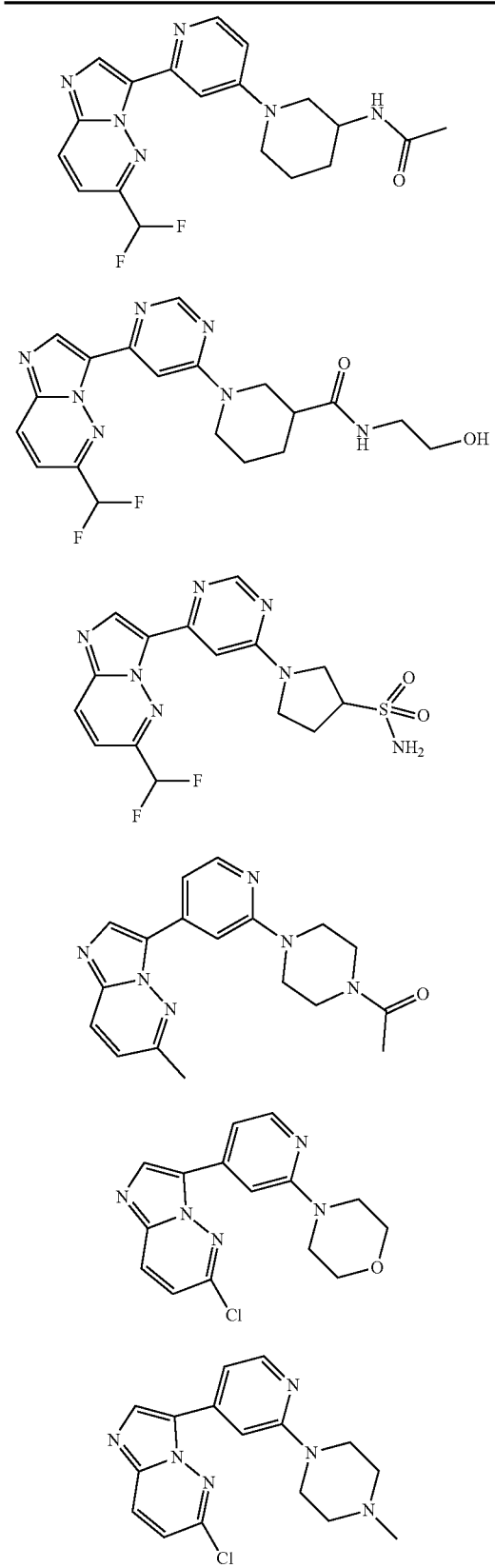
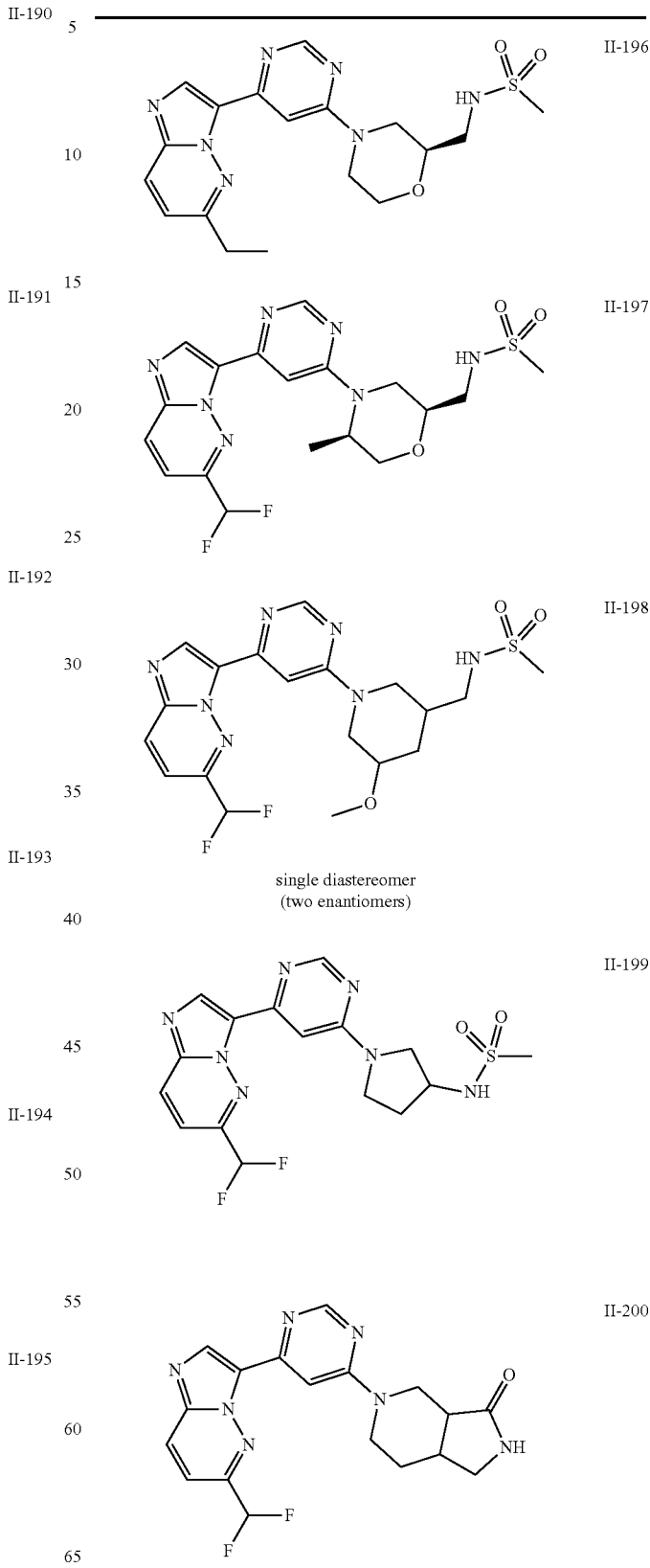

TABLE 1-continued
Exemplary compounds of formula II
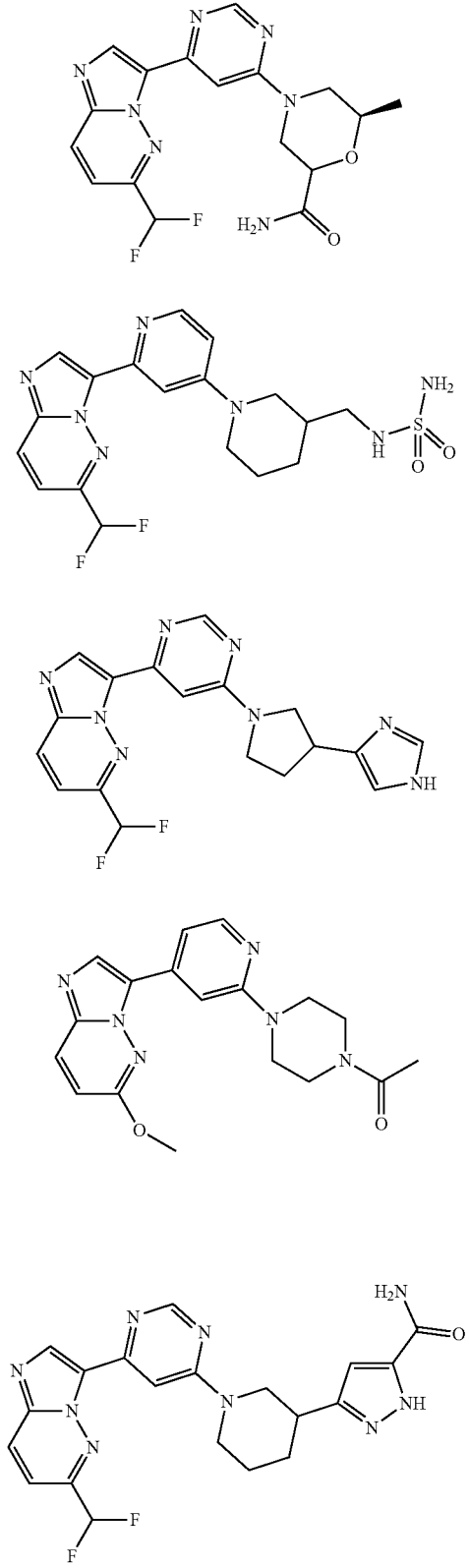
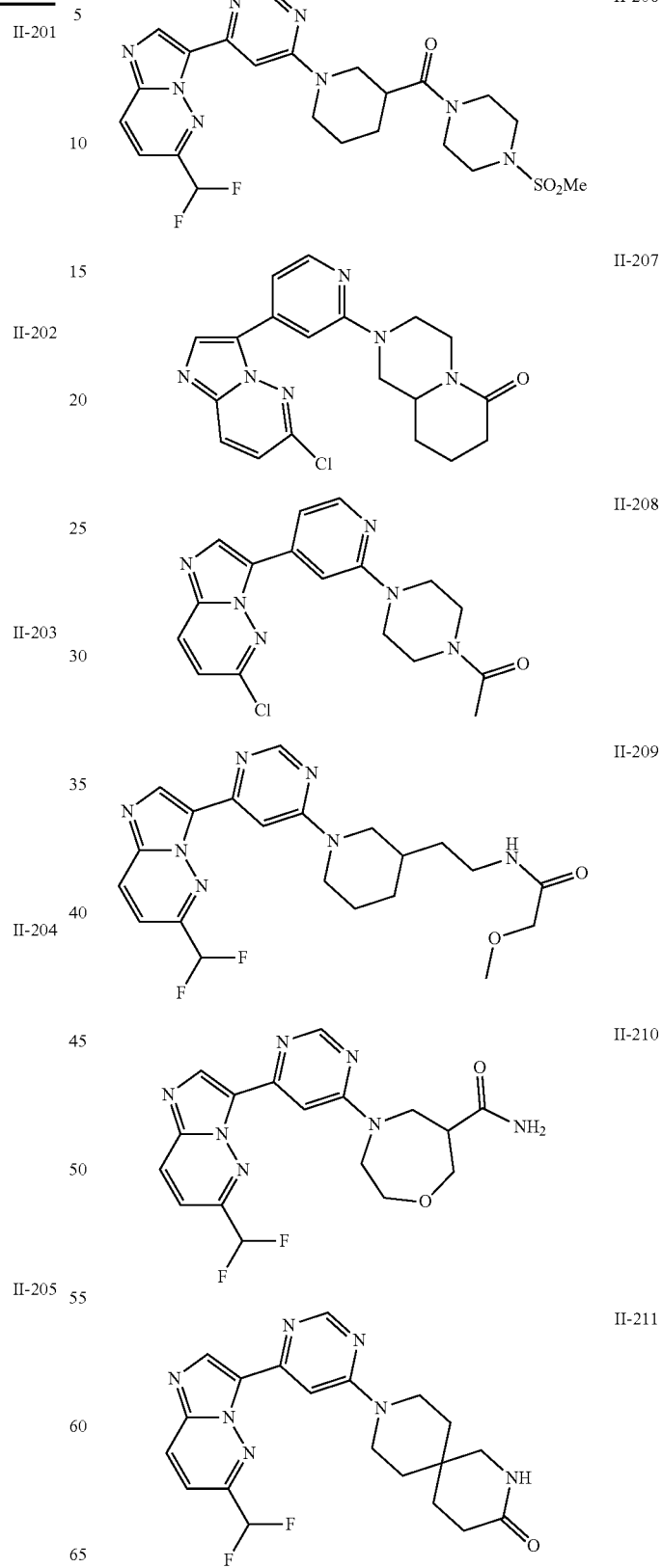

TABLE 1-continued
Exemplary compounds of formula II
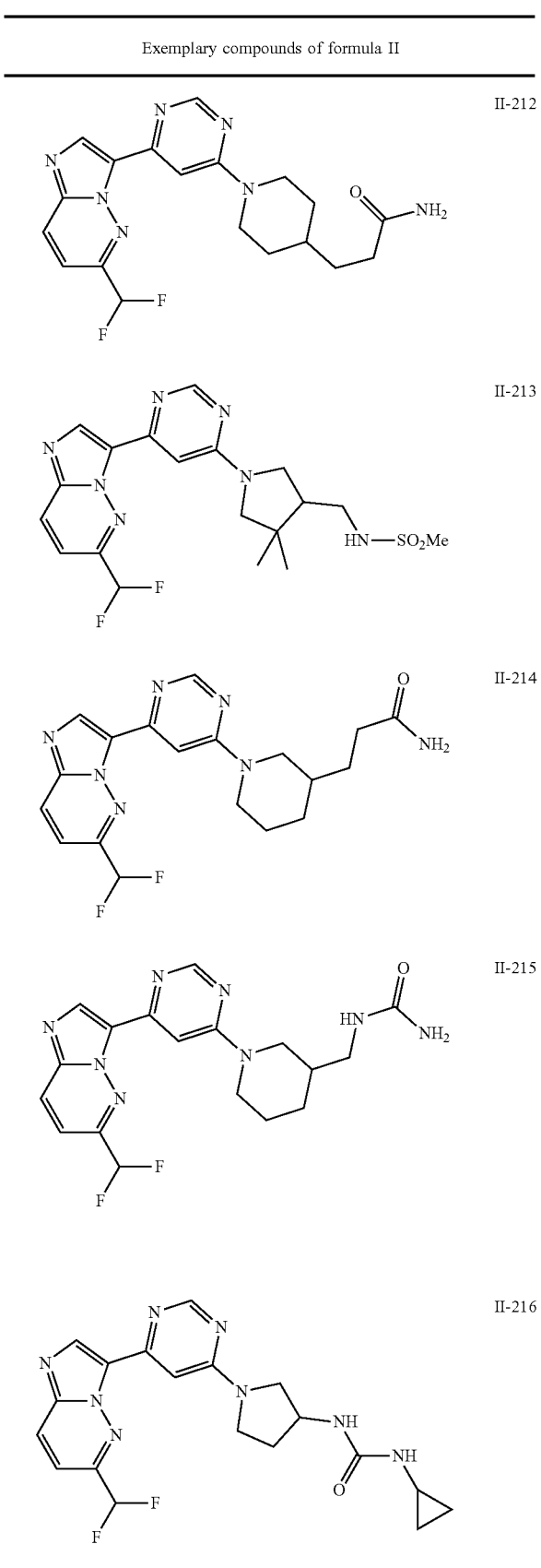
II-212
II-213
II-214
II-215
II-216
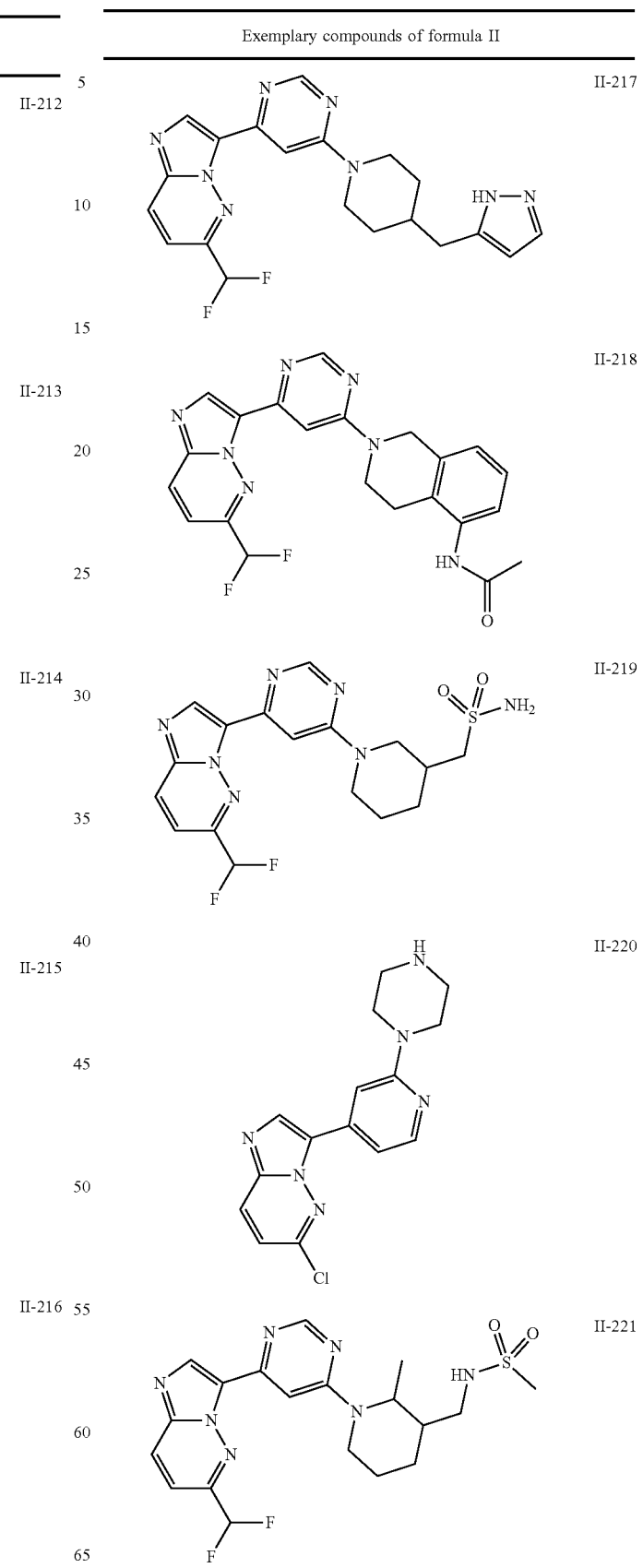
II-217
II-218
II-219
II-220
II-221

TABLE 1-continued
Exemplary compounds of formula II
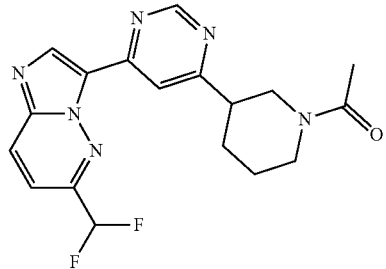 [SMILES: CC(=O)N1CCCC(c2cc(-c3cnc4ccc(C(F)F)nn34)ncn2)C1]
II-222
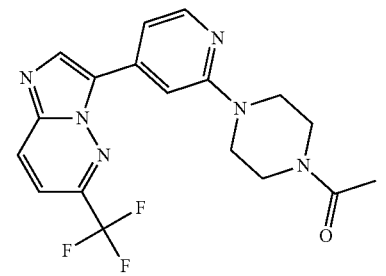 [SMILES: CC(=O)N1CCN(c2cc(-c3cnc4ccc(C(F)(F)F)nn34)ccn2)CC1]
II-223
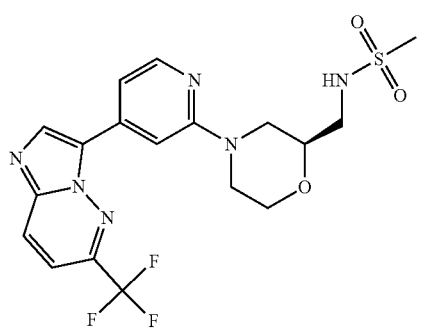 [SMILES: CS(=O)(=O)NC[C@@H]1CN(c2cc(-c3cnc4ccc(C(F)(F)F)nn34)ccn2)CCO1]
II-224
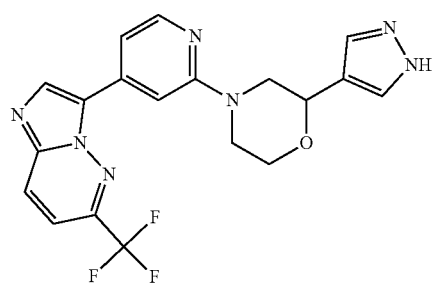 [SMILES: FC(F)(F)c1ccc2ncc(-c3ccnc(N4CCOC(c5cn[nH]c5)C4)c3)n2n1]
II-225
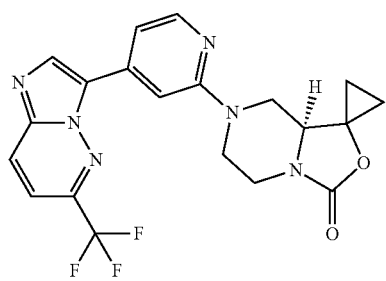 [SMILES: O=C1OC2(CC2)[C@@H]2CN(c3cc(-c4cnc5ccc(C(F)(F)F)nn45)ccn3)CCN12]
II-226
TABLE 1-continued
Exemplary compounds of formula II
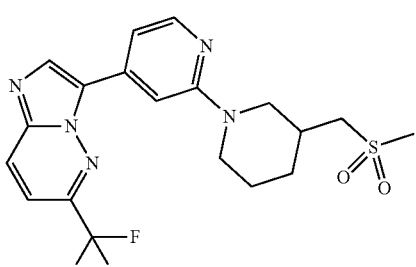
II-227
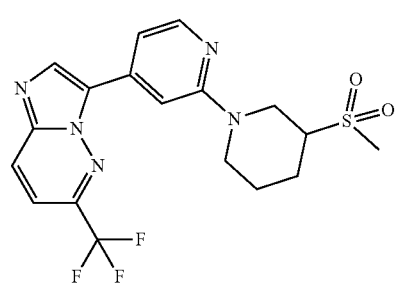 [SMILES: CS(=O)(=O)C1CCCN(c2cc(-c3cnc4ccc(C(F)(F)F)nn34)ccn2)C1]
II-228
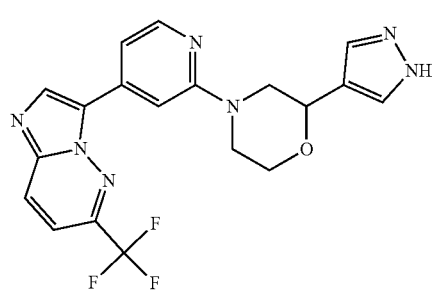
II-229
single stereoisomer
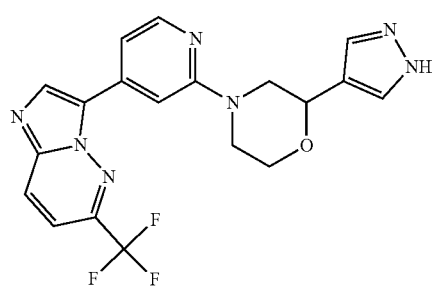
II-230
single stereoisomer
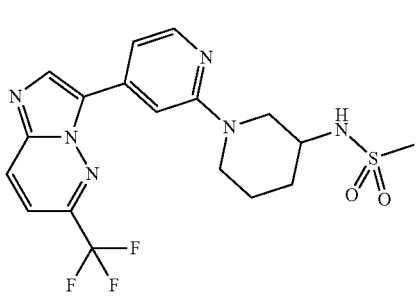 [SMILES: CS(=O)(=O)NC1CCCN(c2cc(-c3cnc4ccc(C(F)(F)F)nn34)ccn2)C1]
II-231

TABLE 1-continued
Exemplary compounds of formula II
II-232
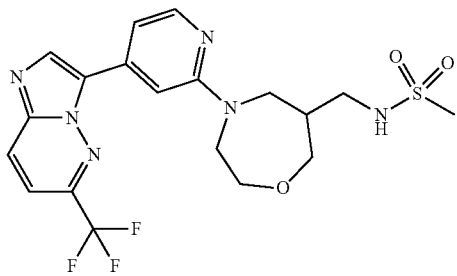 [SMILES: CS(=O)(=O)NCC1COCCN(c2cc(-c3cnc4ccc(C(F)(F)F)nn34)ccn2)C1]
II-233
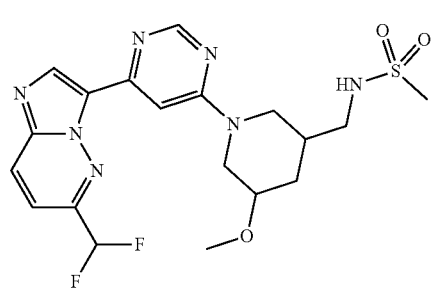
single diastereomer
(two enantiomers)
II-234
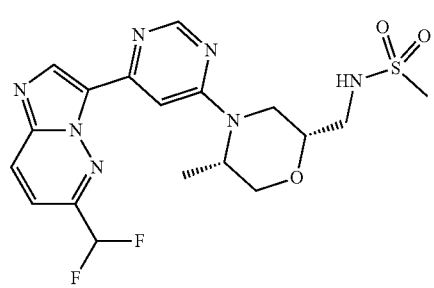 [SMILES: C[C@H]1CO[C@@H](CNS(C)(=O)=O)CN1c1cc(-c2cnc3ccc(C(F)F)nn23)ncn1]
II-235
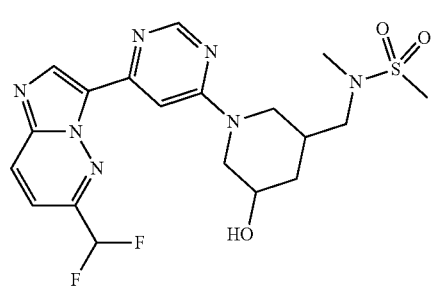 [SMILES: CN(CC1CC(O)CN(c2cc(-c3cnc4ccc(C(F)F)nn34)ncn2)C1)S(C)(=O)=O]
II-236
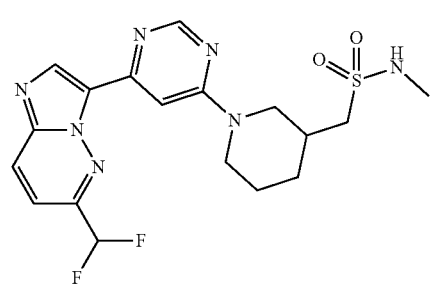 [SMILES: CNS(=O)(=O)CC1CCCN(c2cc(-c3cnc4ccc(C(F)F)nn34)ncn2)C1]
TABLE 1-continued
Exemplary compounds of formula II
II-237
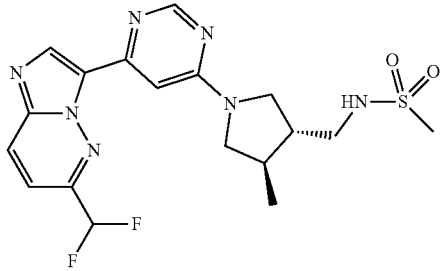 [SMILES: C[C@H]1CN(c2cc(-c3cnc4ccc(C(F)F)nn34)ncn2)C[C@@H]1CNS(C)(=O)=O]
II-238
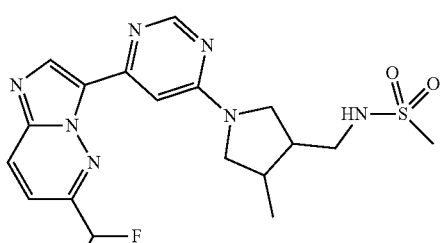
single stereoisomer
II-239
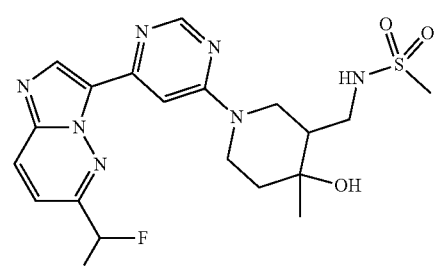
single diastereomer
(two enantiomers)
II-240
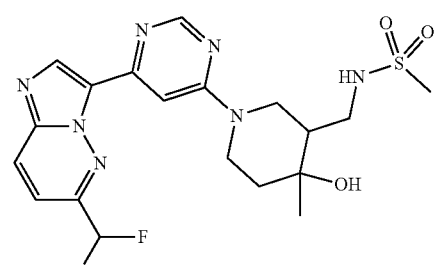
single diastereomer
(two enantiomers)
II-241
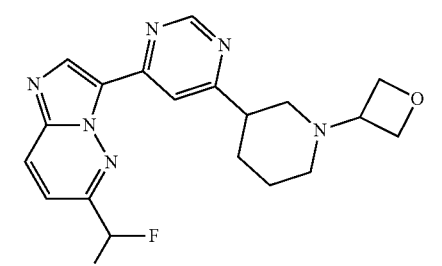
single stereoisomer TABLE 1-continued
Exemplary compounds of formula II
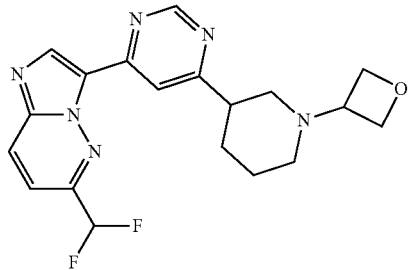
II-242
single stereoisomer
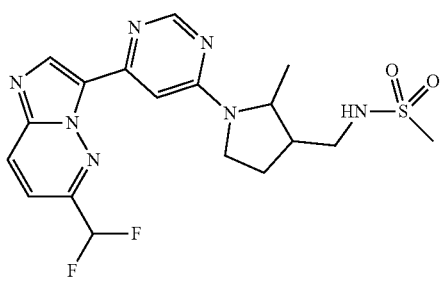
II-243
single diastereomer
(two enantiomers)
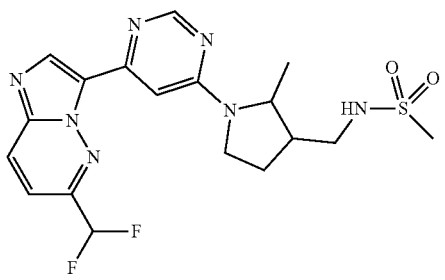
II-244
single diastereomer
(two enantiomers)
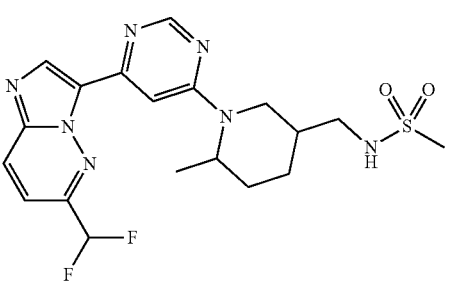
II-245
single stereoisomer
TABLE 1-continued
Exemplary compounds of formula II
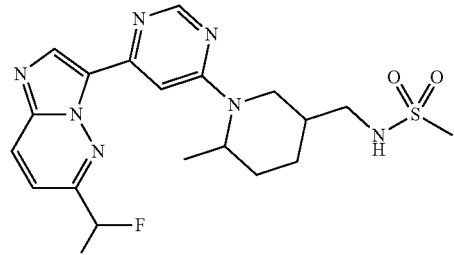
II-246
single stereoisomer
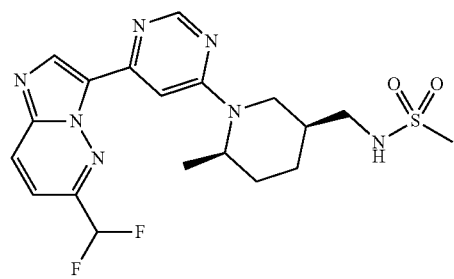 [SMILES: C[C@@H]1CC[C@H](CNS(C)(=O)=O)CN1c1cc(-c2cnc3ccc(C(F)F)nn23)ncn1]
II-247
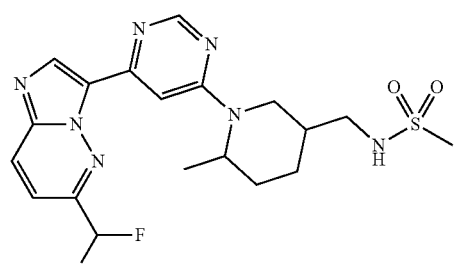
II-248
single stereoisomer
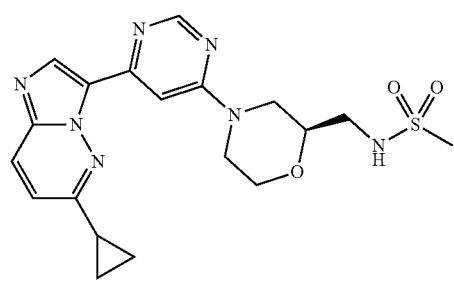 [SMILES: CS(=O)(=O)NC[C@@H]1CN(c2cc(-c3cnc4ccc(C5CC5)nn34)ncn2)CCO1]
II-249
II-250

TABLE 1-continued
Exemplary compounds of formula II
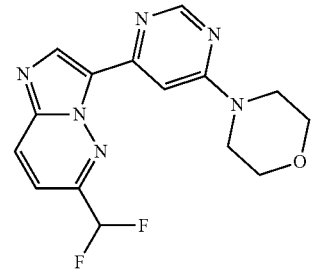 II-251
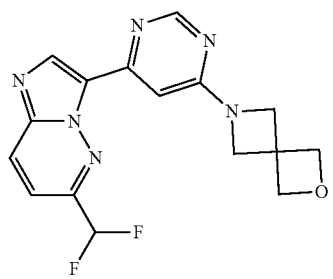 [SMILES: FC(F)c1ccc2ncc(-c3cc(N4CC5(COC5)C4)ncn3)n2n1] II-252
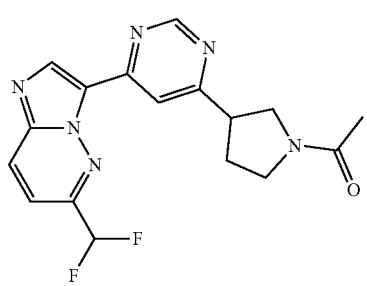 [SMILES: CC(=O)N1CCC(c2cc(-c3cnc4ccc(C(F)F)nn34)ncn2)C1] II-253
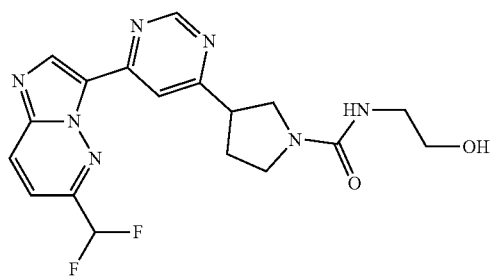 [SMILES: O=C(NCCO)N1CCC(c2cc(-c3cnc4ccc(C(F)F)nn34)ncn2)C1] II-254
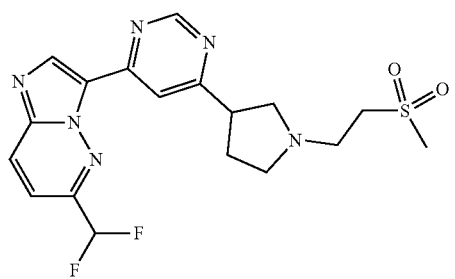 [SMILES: CS(=O)(=O)CCN1CCC(c2cc(-c3cnc4ccc(C(F)F)nn34)ncn2)C1] II-255
TABLE 1-continued
Exemplary compounds of formula II
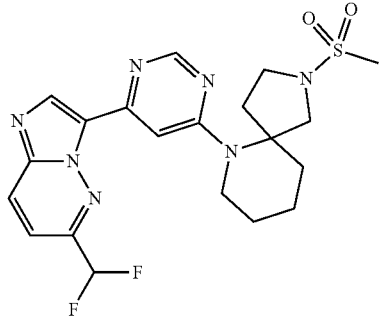 [SMILES: CS(=O)(=O)N1CCC2(CCCCN2c2cc(-c3cnc4ccc(C(F)F)nn34)ncn2)C1] II-256
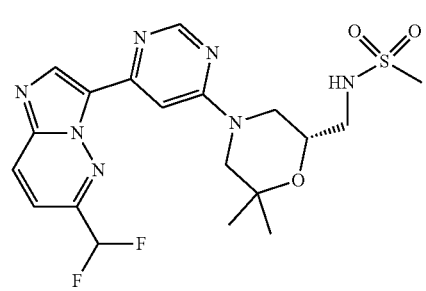 [SMILES: CC1(C)CN(c2cc(-c3cnc4ccc(C(F)F)nn34)ncn2)C[C@H](CNS(C)(=O)=O)O1] II-257
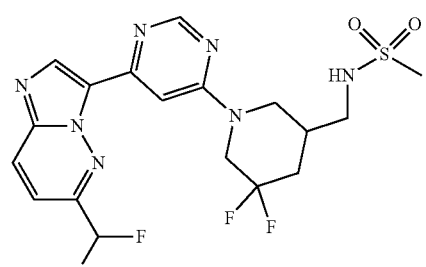 II-258
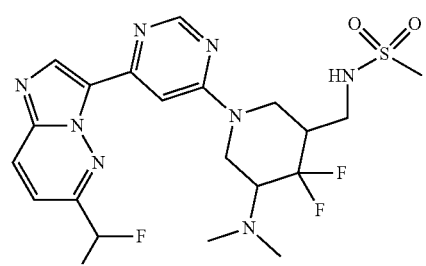 II-259
single diastereomer
(two enantiomers)
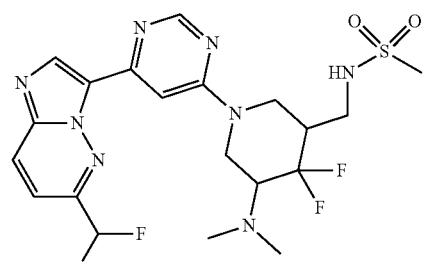 II-260
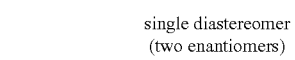
single diastereomer
(two enantiomers)

TABLE 1-continued
Exemplary compounds of formula II
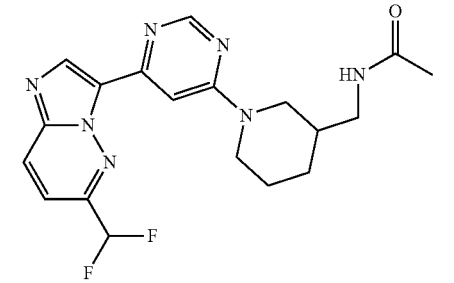 [SMILES: CC(=O)NCC1CCCN(c2cc(-c3cnc4ccc(C(F)F)nn34)ncn2)C1]
II-261
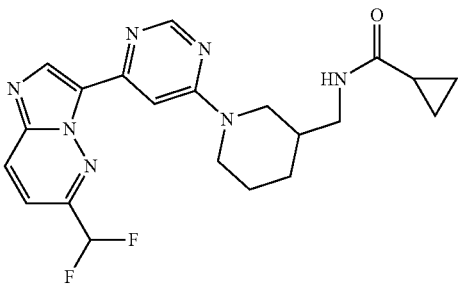 [SMILES: O=C(NCC1CCCN(c2cc(-c3cnc4ccc(C(F)F)nn34)ncn2)C1)C1CC1]
II-262
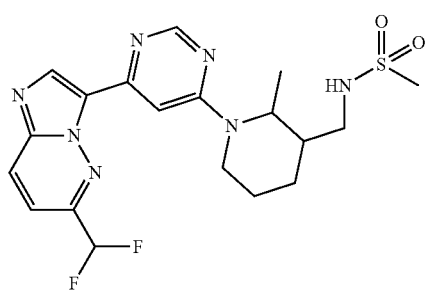
II-263
single stereoisomer
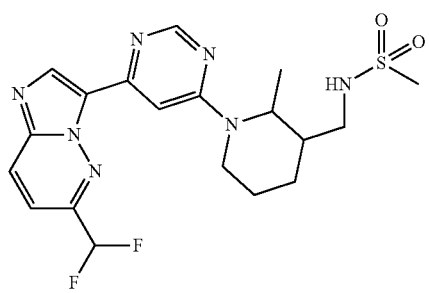
II-264
single stereoisomer
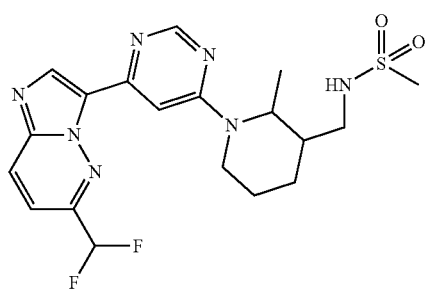
II-265
single stereoisomer
TABLE 1-continued
Exemplary compounds of formula II
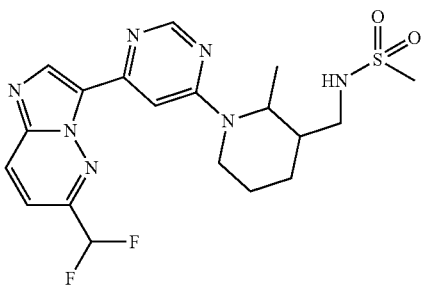 [SMILES: CC1CCC(CNS(C)(=O)=O)C(C)N1c1cc(-c2cnc3ccc(C(F)F)nn23)ncn1]
II-266
single stereoisomer
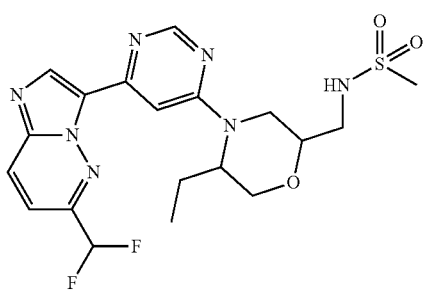
II-267
single diastereomer
(two enantiomers)
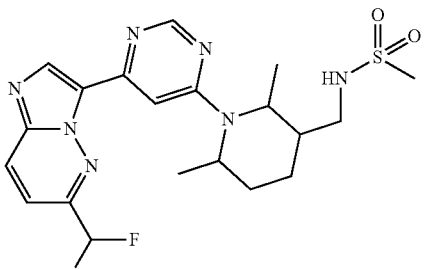
II-268
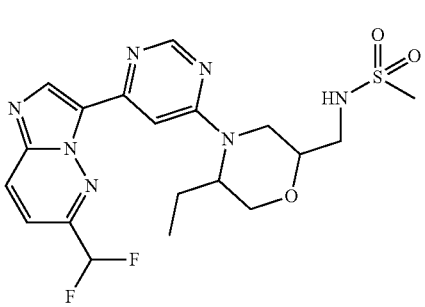
II-269
single diastereomer
(two enantiomers)
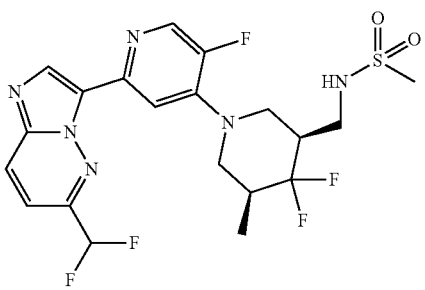 [SMILES: C[C@H]1CN(c2cc(-c3cnc4ccc(C(F)F)nn34)ncc2F)C[C@@H](CNS(C)(=O)=O)C1(F)F]
II-270

TABLE 1-continued
Exemplary compounds of formula II
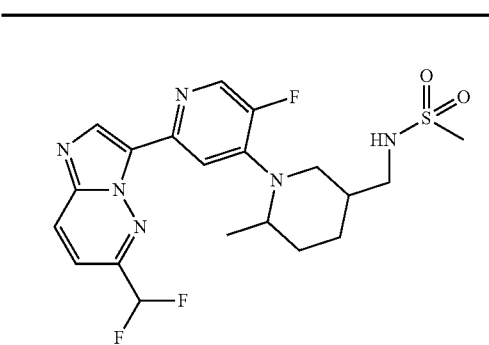 II-271
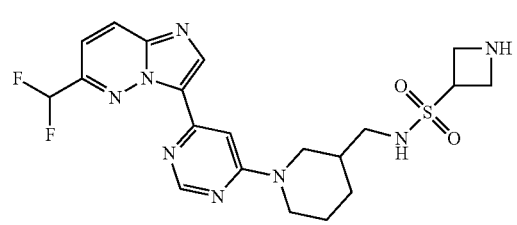 [SMILES: O=S(=O)(NCC1CCCN(c2cc(-c3cnc4ccc(C(F)F)nn34)ncn2)C1)C1CNC1] II-272
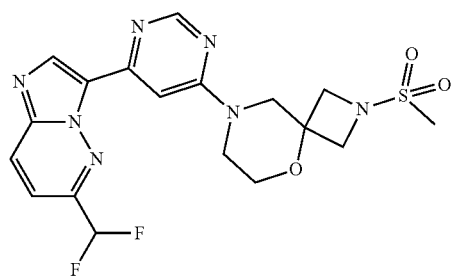 [SMILES: CS(=O)(=O)N1CC2(CN(c3cc(-c4cnc5ccc(C(F)F)nn45)ncn3)CCO2)C1] II-273
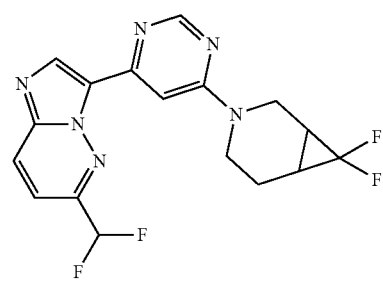 [SMILES: FC(F)c1ccc2ncc(-c3cc(N4CCC5C(C4)C5(F)F)ncn3)n2n1] II-274
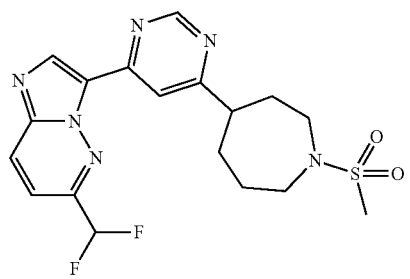 II-275
single stereoisomer
TABLE 1-continued
Exemplary compounds of formula II
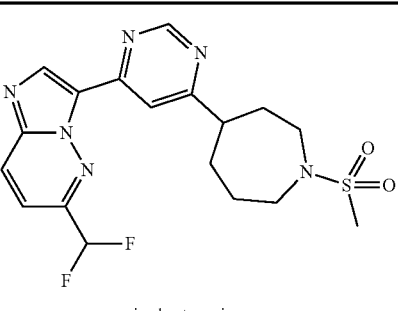 II-276
single stereoisomer
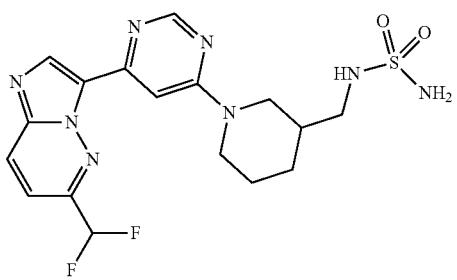 II-277
single stereoisomer
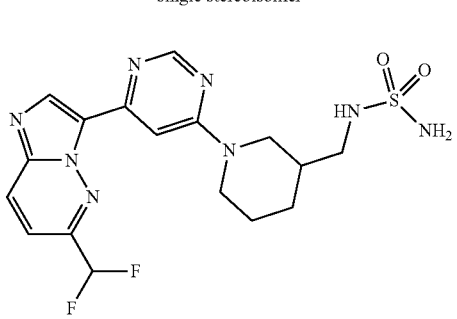 II-278
single stereoisomer
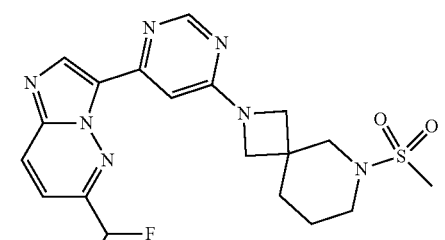 II-279
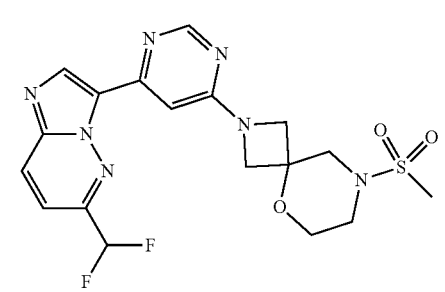 [SMILES: CS(=O)(=O)N1CCOC2(CN(c3cc(-c4cnc5ccc(C(F)F)nn45)ncn3)C2)C1] II-280

TABLE 1-continued
Exemplary compounds of formula II
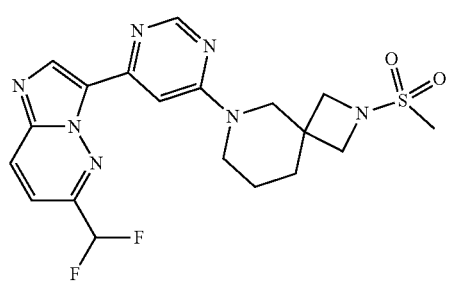 [SMILES: CS(=O)(=O)N1CC2(CCCN(c3cc(-c4cnc5ccc(C(F)F)nn45)ncn3)C2)C1] II-281
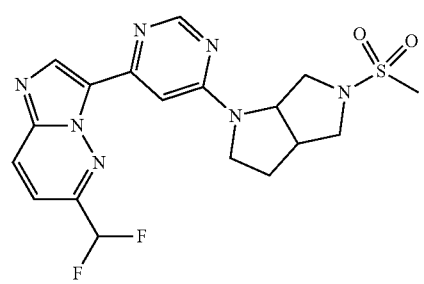 [SMILES: CS(=O)(=O)N1CC2CCN(c3cc(-c4cnc5ccc(C(F)F)nn45)ncn3)C2C1] II-282
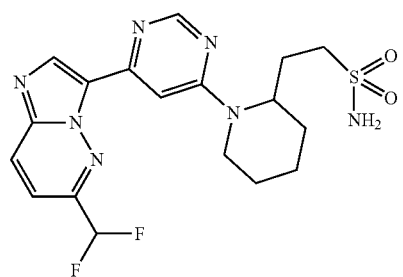 [SMILES: NS(=O)(=O)CCC1CCCCN1c1cc(-c2cnc3ccc(C(F)F)nn23)ncn1] II-283
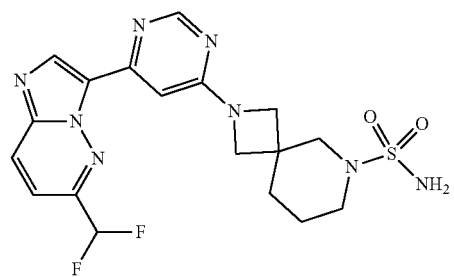 [SMILES: NS(=O)(=O)N1CCCC2(CN(c3cc(-c4cnc5ccc(C(F)F)nn45)ncn3)C2)C1] II-284
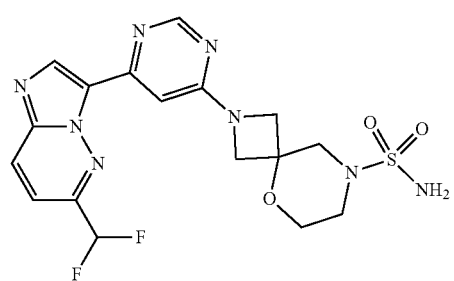 [SMILES: NS(=O)(=O)N1CCOC2(CN(c3cc(-c4cnc5ccc(C(F)F)nn45)ncn3)C2)C1] II-285
TABLE 1-continued
Exemplary compounds of formula II
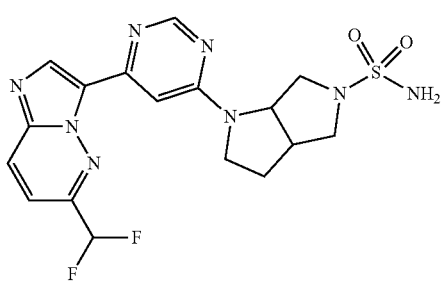 [SMILES: NS(=O)(=O)N1CC2CCN(c3cc(-c4cnc5ccc(C(F)F)nn45)ncn3)C2C1] II-286
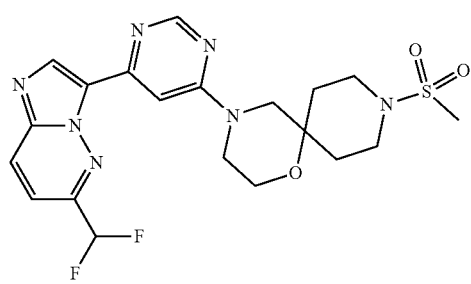 [SMILES: CS(=O)(=O)N1CCC2(CC1)CN(c1cc(-c3cnc4ccc(C(F)F)nn34)ncn1)CCO2] II-287
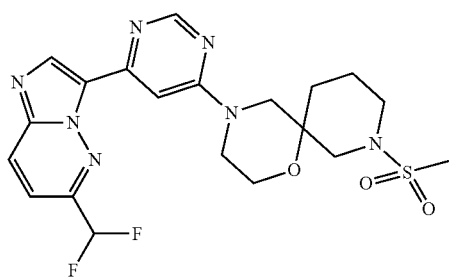 [SMILES: CS(=O)(=O)N1CCCC2(CN(c3cc(-c4cnc5ccc(C(F)F)nn45)ncn3)CCO2)C1] II-288
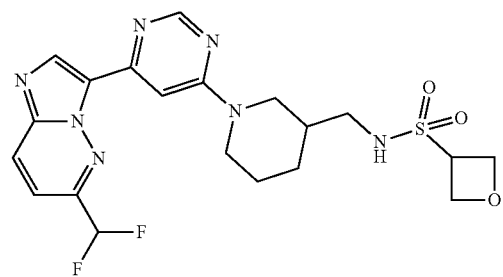 [SMILES: O=S(=O)(NCC1CCCN(c2cc(-c3cnc4ccc(C(F)F)nn34)ncn2)C1)C1COC1] II-289
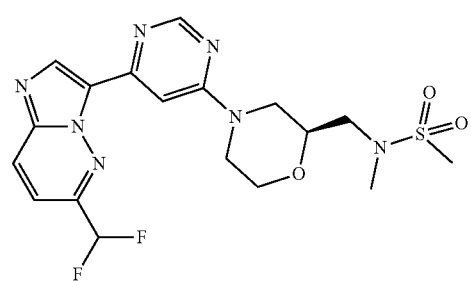 [SMILES: CN(C[C@@H]1CN(c2cc(-c3cnc4ccc(C(F)F)nn34)ncn2)CCO1)S(C)(=O)=O] II-290

TABLE 1-continued
Exemplary compounds of formula II
| | |
|---|---|
| II-291 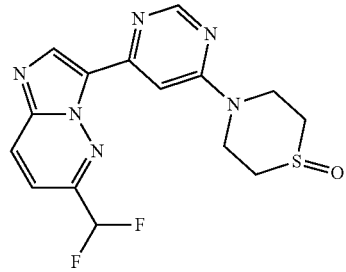 [SMILES: O=S1CCN(c2cc(-c3cnc4ccc(C(F)F)nn34)ncn2)CC1] | II-296 |
| II-292 | II-297 |
| II-293 single diastereomer (two enantiomers) | II-298 |
| II-294 single diastereomer (two enantiomers) | II-299 |
| II-295 | II-300 |

TABLE 1-continued
Exemplary compounds of formula II
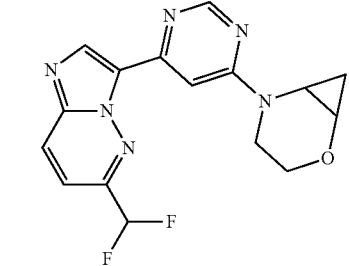 [SMILES: FC(F)c1ccc2ncc(-c3cc(N4CCOC5CC54)ncn3)n2n1] II-301
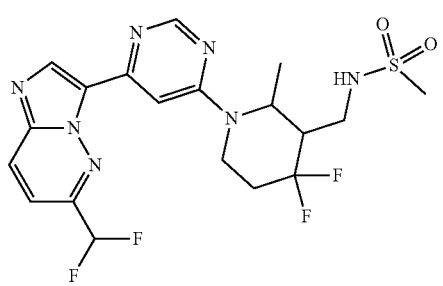 II-302
single diastereomer
(two enantiomers)
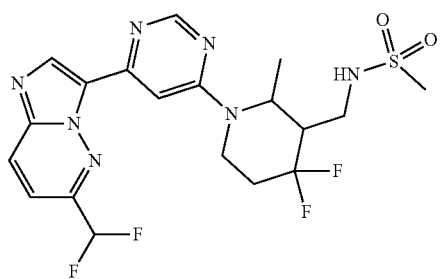 II-303
single diastereomer
(two enantiomers)
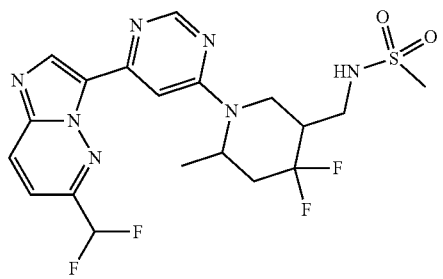 II-304
single diastereomer
(two enantiomers)
TABLE 1-continued
Exemplary compounds of formula II
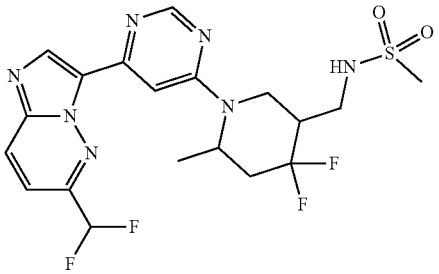 II-305
single diastereomer
(two enantiomers)
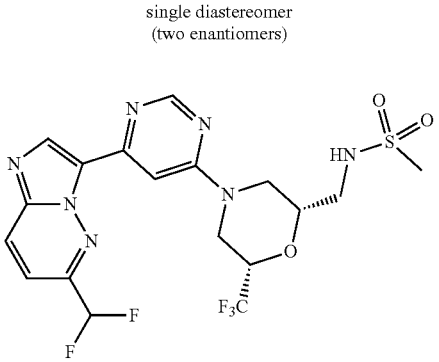 II-306
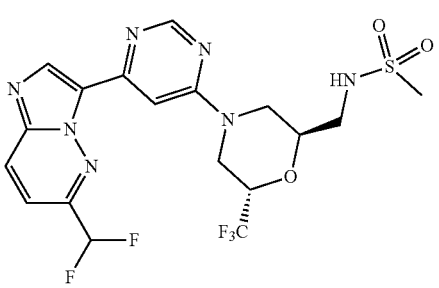 [SMILES: CS(=O)(=O)NC[C@@H]1CN(c2cc(-c3cnc4ccc(C(F)F)nn34)ncn2)C[C@@H](C(F)(F)F)O1] II-307
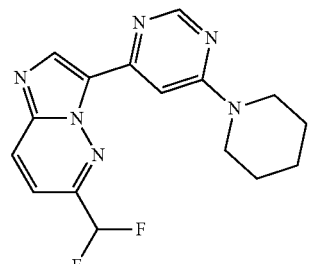 II-308
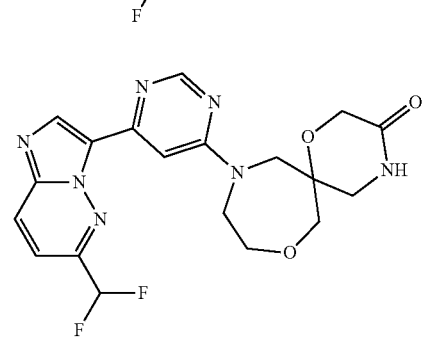 II-309

TABLE 1-continued
Exemplary compounds of formula II
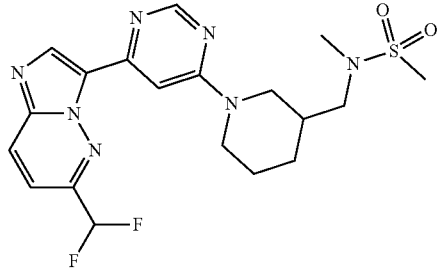 [SMILES: CN(CC1CCCN(c2cc(-c3cnc4ccc(C(F)F)nn34)ncn2)C1)S(C)(=O)=O]
II-310
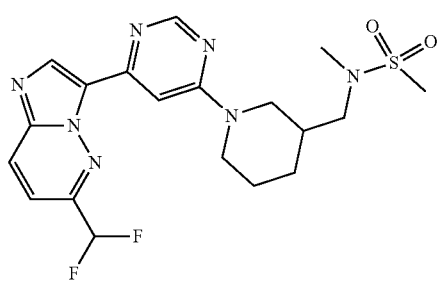 [SMILES: CN(CC1CCCN(c2cc(-c3cnc4ccc(C(F)F)nn34)ncn2)C1)S(C)(=O)=O]
II-311
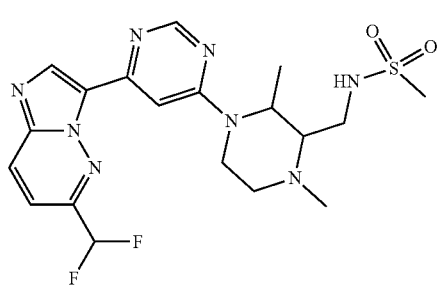 [SMILES: CC1C(CNS(C)(=O)=O)N(C)CCN1c1cc(-c2cnc3ccc(C(F)F)nn23)ncn1]
II-312
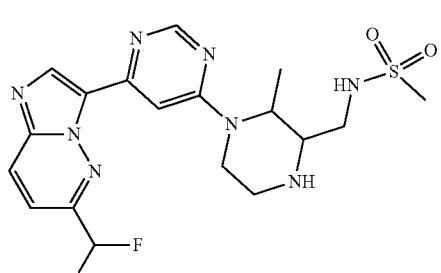
II-313
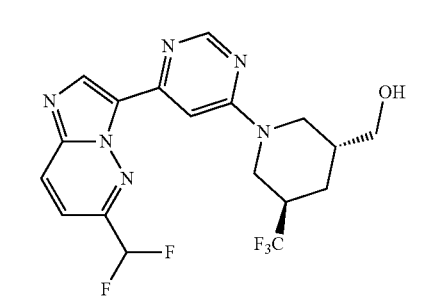 [SMILES: OC[C@@H]1C[C@@H](C(F)(F)F)CN(c2cc(-c3cnc4ccc(C(F)F)nn34)ncn2)C1]
II-314
TABLE 1-continued
Exemplary compounds of formula II
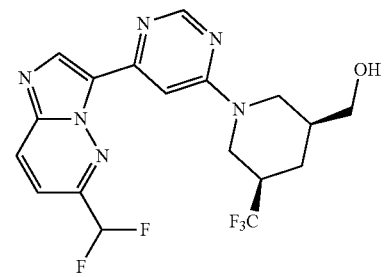 [SMILES: OC[C@H]1C[C@@H](C(F)(F)F)CN(c2cc(-c3cnc4ccc(C(F)F)nn34)ncn2)C1]
II-315
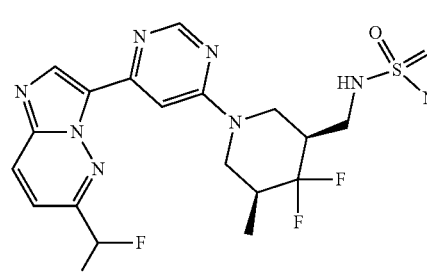
II-316
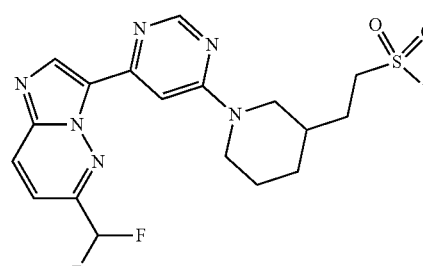
II-317
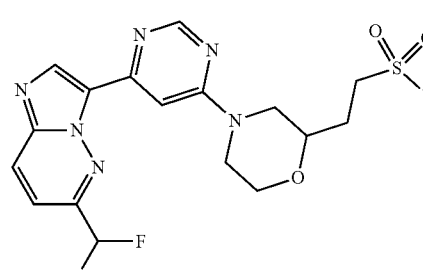
II-318
II-319

TABLE 1-continued
Exemplary compounds of formula II
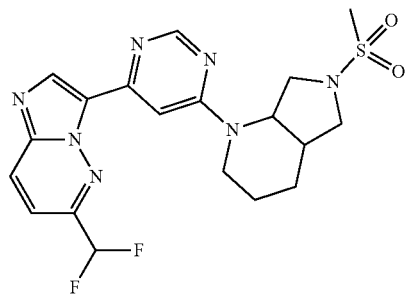 [SMILES: CS(=O)(=O)N1CC2CCCN(c3cc(-c4cnc5ccc(C(F)F)nn45)ncn3)C2C1] II-320
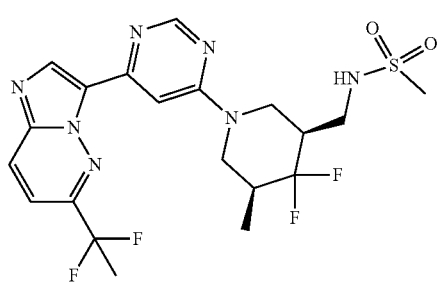 [SMILES: C[C@H]1CN(c2cc(-c3cnc4ccc(C(C)(F)F)nn34)ncn2)C[C@@H](CNS(C)(=O)=O)C1(F)F] II-321
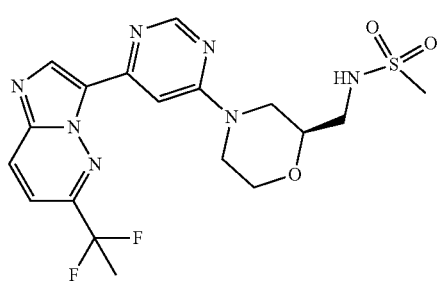 [SMILES: CC(F)(F)c1ccc2ncc(-c3cc(N4CCO[C@H](CNS(C)(=O)=O)C4)ncn3)n2n1] II-322
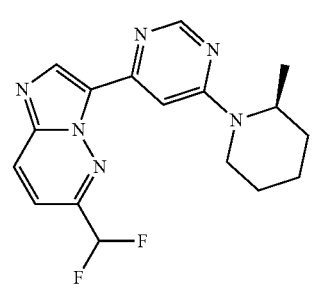 [SMILES: C[C@H]1CCCCN1c1cc(-c2cnc3ccc(C(F)F)nn23)ncn1] II-323
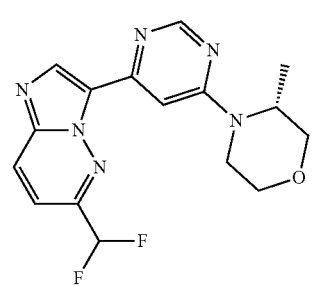 II-324
TABLE 1-continued
Exemplary compounds of formula II
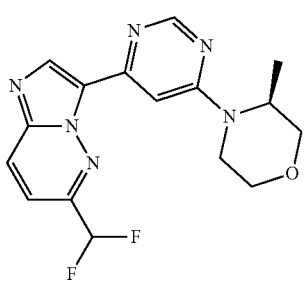 [SMILES: C[C@H]1COCCN1c1cc(-c2cnc3ccc(C(F)F)nn23)ncn1] II-325
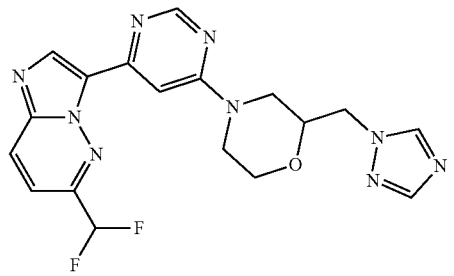 II-326
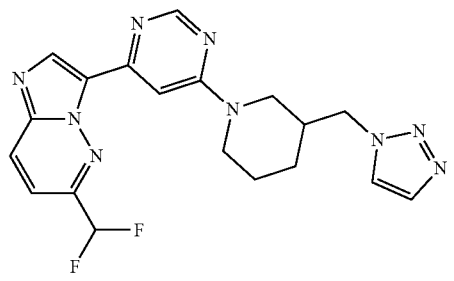 [SMILES: FC(F)c1ccc2ncc(-c3cc(N4CCCC(Cn5ccnn5)C4)ncn3)n2n1] II-327
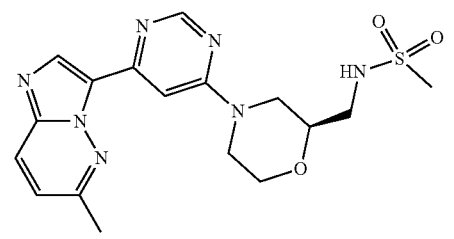 [SMILES: Cc1ccc2ncc(-c3cc(N4CCO[C@H](CNS(C)(=O)=O)C4)ncn3)n2n1] II-328
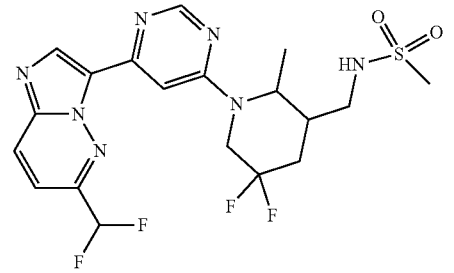 [SMILES: CC1C(CNS(C)(=O)=O)CC(F)(F)CN1c1cc(-c2cnc3ccc(C(F)F)nn23)ncn1] II-329

TABLE 1-continued
Exemplary compounds of formula II
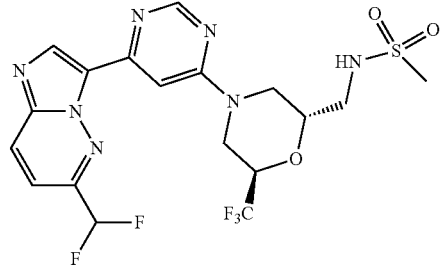 [SMILES: CS(=O)(=O)NC[C@H]1CN(c2cc(-c3cnc4ccc(C(F)F)nn34)ncn2)C[C@H](C(F)(F)F)O1]
II-330
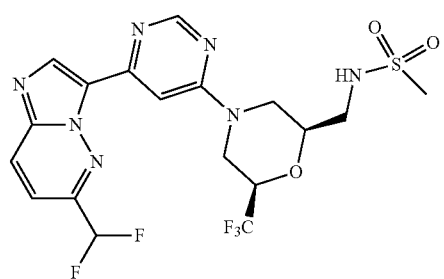 [SMILES: CS(=O)(=O)NC[C@@H]1CN(c2cc(-c3cnc4ccc(C(F)F)nn34)ncn2)C[C@H](C(F)(F)F)O1]
II-331
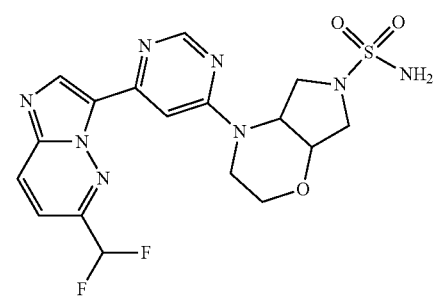 [SMILES: NS(=O)(=O)N1CC2OCCN(c3cc(-c4cnc5ccc(C(F)F)nn45)ncn3)C2C1]
II-332
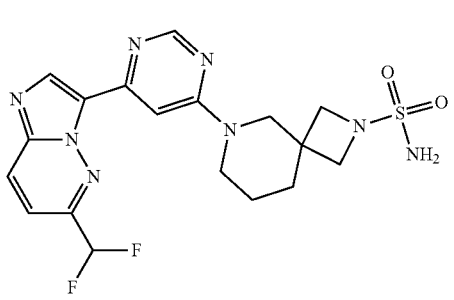 [SMILES: NS(=O)(=O)N1CC2(CCCN(c3cc(-c4cnc5ccc(C(F)F)nn45)ncn3)C2)C1]
II-333
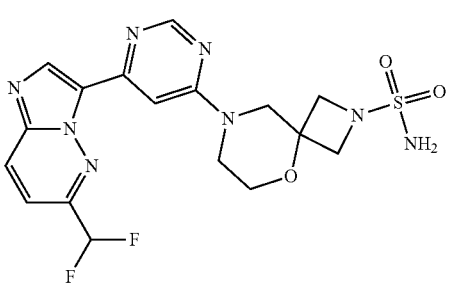 [SMILES: NS(=O)(=O)N1CC2(CN(c3cc(-c4cnc5ccc(C(F)F)nn45)ncn3)CCO2)C1]
II-334
TABLE 1-continued
Exemplary compounds of formula II
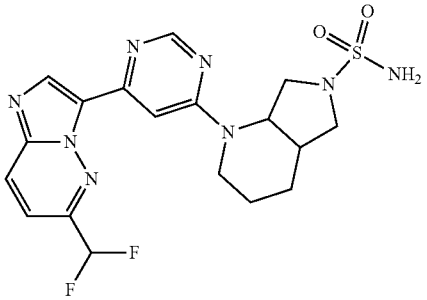 [SMILES: NS(=O)(=O)N1CC2CCCN(c3cc(-c4cnc5ccc(C(F)F)nn45)ncn3)C2C1]
II-335
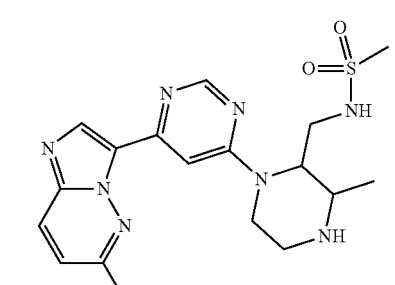
II-336
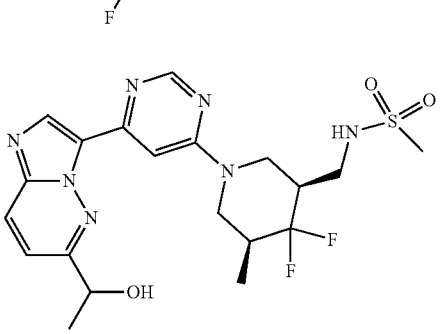
II-337
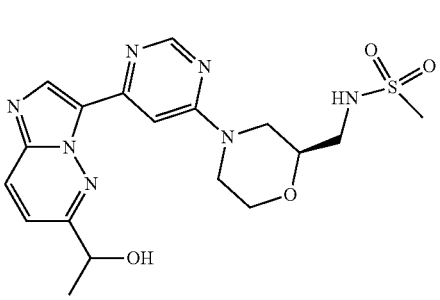 [SMILES: CC(O)c1ccc2ncc(-c3cc(N4CCO[C@H](CNS(C)(=O)=O)C4)ncn3)n2n1]
II-338
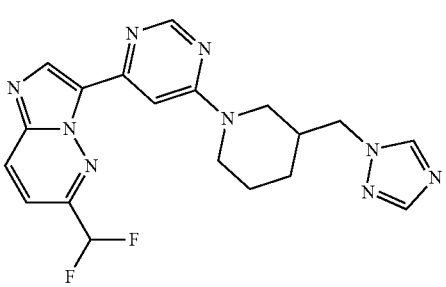 [SMILES: FC(F)c1ccc2ncc(-c3cc(N4CCCC(Cn5cncn5)C4)ncn3)n2n1]
II-339

TABLE 1-continued
Exemplary compounds of formula II
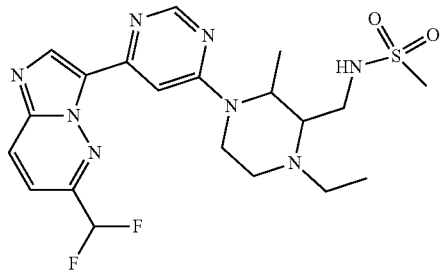 [SMILES: CCN1CCN(c2cc(-c3cnc4ccc(C(F)F)nn34)ncn2)C(C)C1CNS(C)(=O)=O] II-340
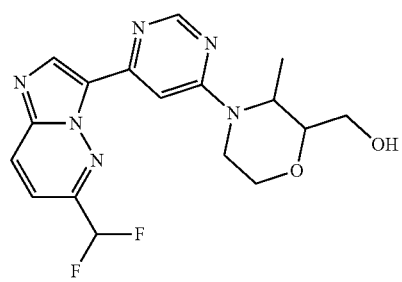 II-341
single stereoisomer
(trans diastereomer)
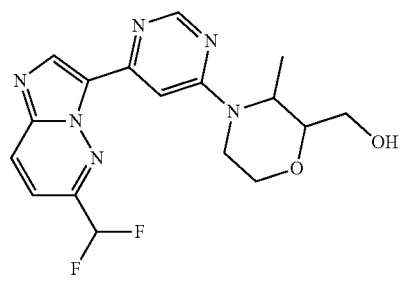 II-342
single stereoisomer
(trans diastereomer)
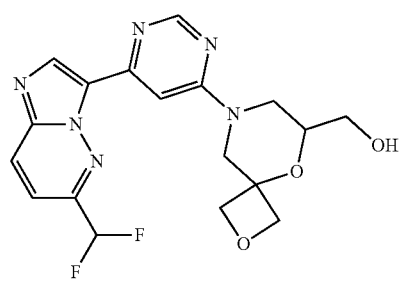 [SMILES: OCC1CN(c2cc(-c3cnc4ccc(C(F)F)nn34)ncn2)CC2(COC2)O1] II-343
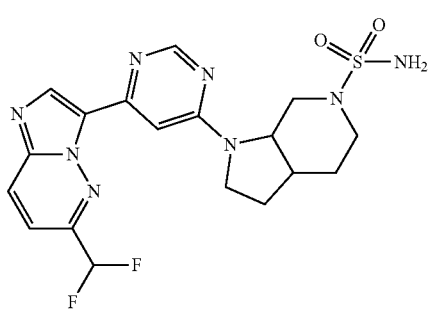 [SMILES: NS(=O)(=O)N1CCC2CCN(c3cc(-c4cnc5ccc(C(F)F)nn45)ncn3)C2C1] II-344
TABLE 1-continued
Exemplary compounds of formula II
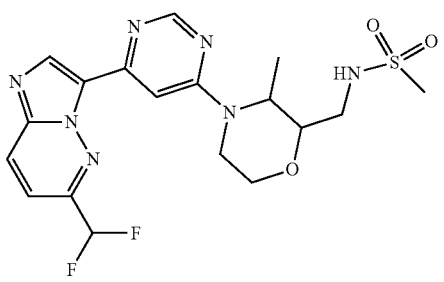 II-345
single diastereomer
(two cis- enantiomers)
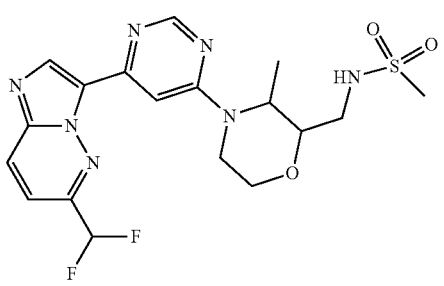 II-346
single diastereomer
(two trans- enantiomers)
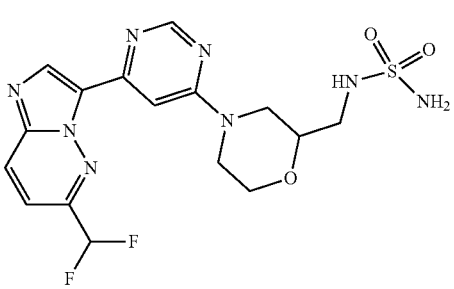 [SMILES: NS(=O)(=O)NCC1CN(c2cc(-c3cnc4ccc(C(F)F)nn34)ncn2)CCO1] II-347
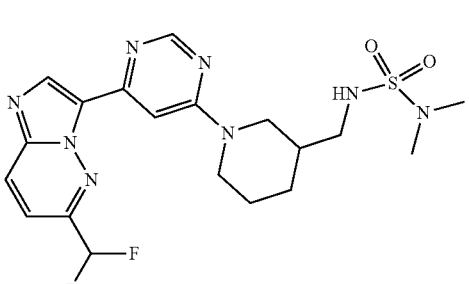 II-348
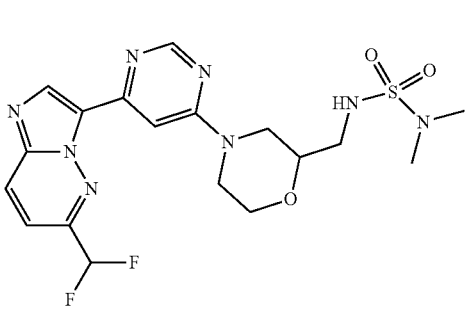 [SMILES: CN(C)S(=O)(=O)NCC1CN(c2cc(-c3cnc4ccc(C(F)F)nn34)ncn2)CCO1] II-349

TABLE 1-continued
Exemplary compounds of formula II
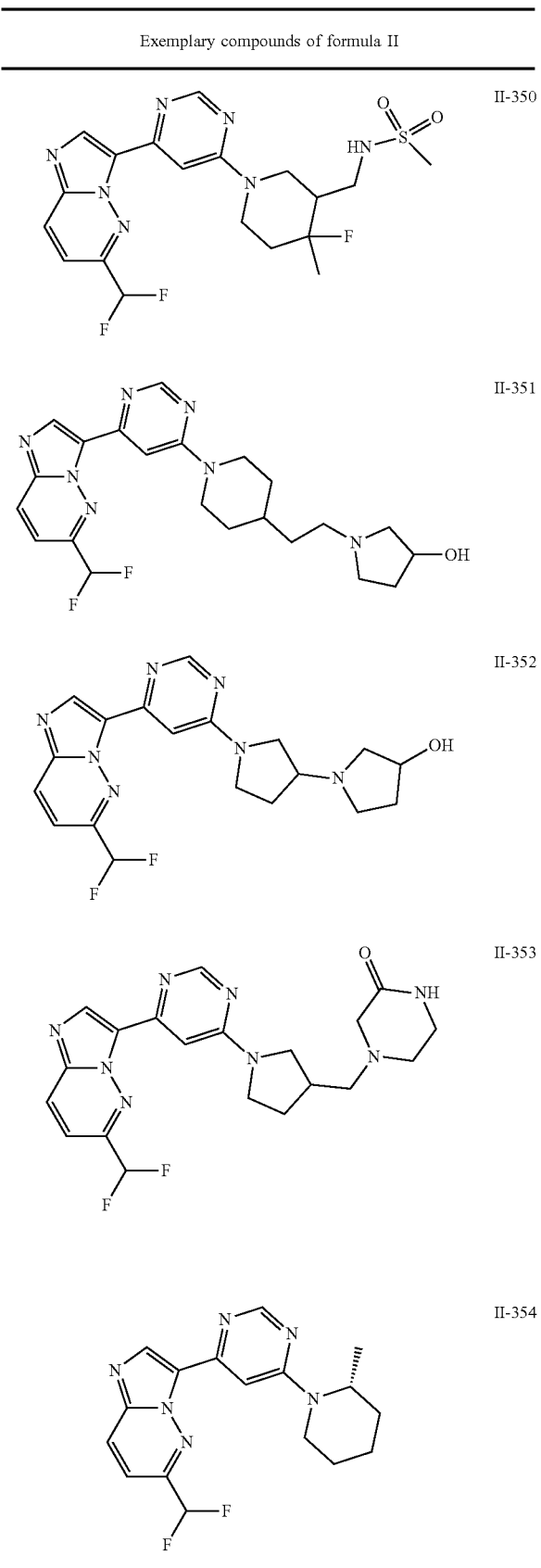
II-350
II-351
II-352
II-353
II-354
TABLE 1-continued
Exemplary compounds of formula II
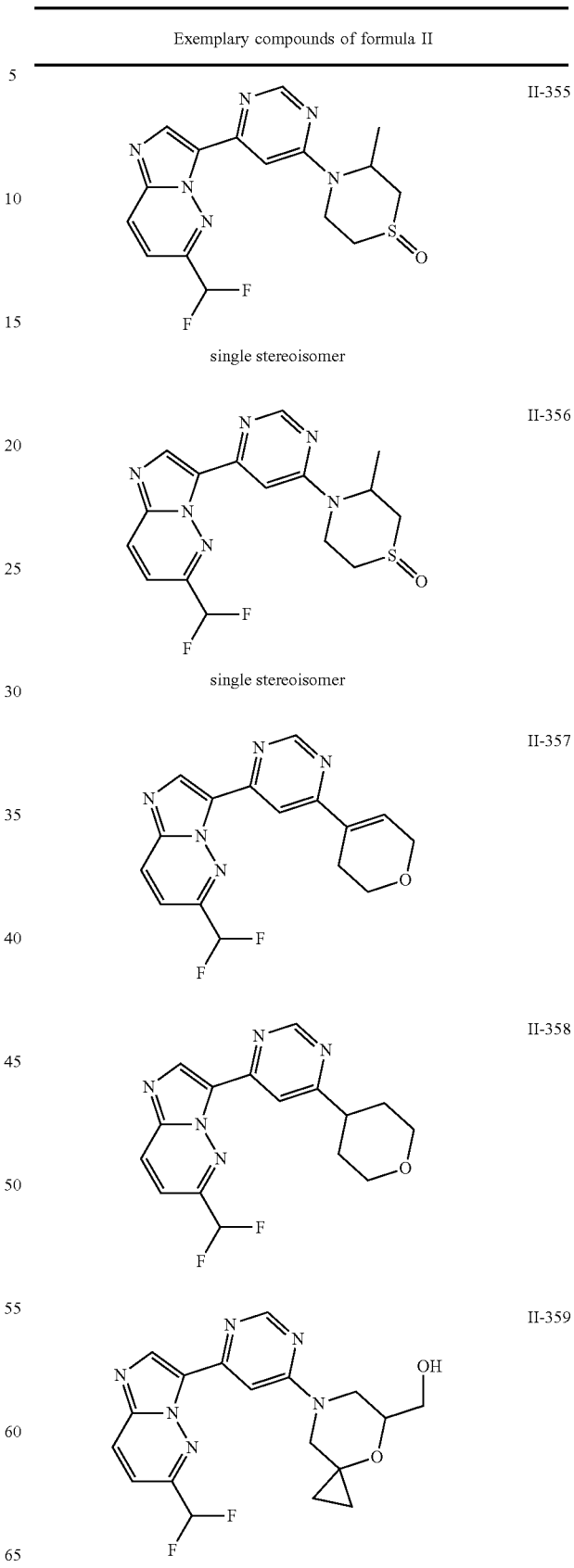
II-355
single stereoisomer
II-356
single stereoisomer
II-357
II-358
II-359

TABLE 1-continued
Exemplary compounds of formula II
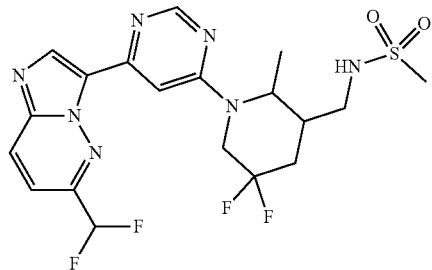
II-360
single stereoisomer
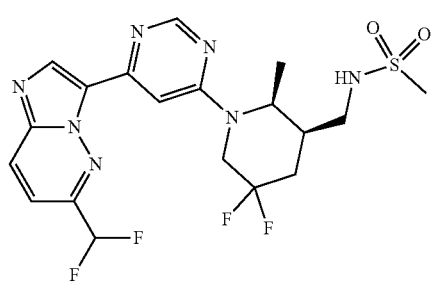 [SMILES: C[C@H]1[C@@H](CNS(C)(=O)=O)CC(F)(F)CN1c1cc(-c2cnc3ccc(C(F)F)nn23)ncn1]
II-361
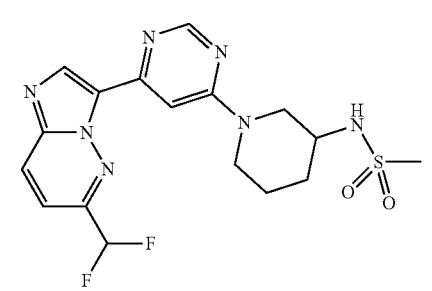 [SMILES: CS(=O)(=O)NC1CCCN(c2cc(-c3cnc4ccc(C(F)F)nn34)ncn2)C1]
II-362
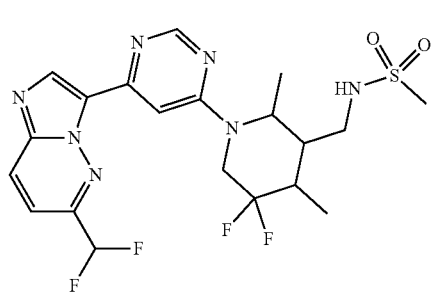 [SMILES: CC1C(CNS(C)(=O)=O)C(C)C(F)(F)CN1c1cc(-c2cnc3ccc(C(F)F)nn23)ncn1]
II-363
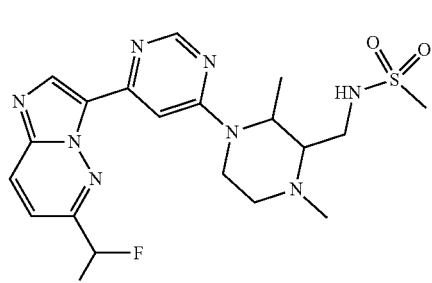
II-364
single stereoisomer
TABLE 1-continued
Exemplary compounds of formula II
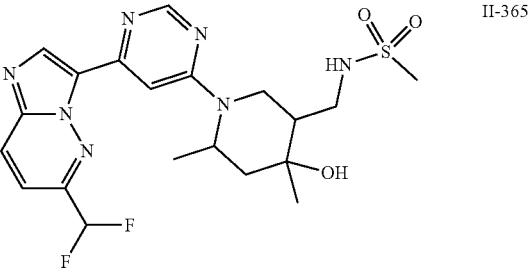
II-365
single diastereomer
(two enantiomers)
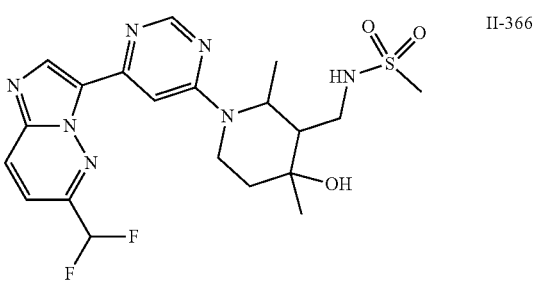
II-366
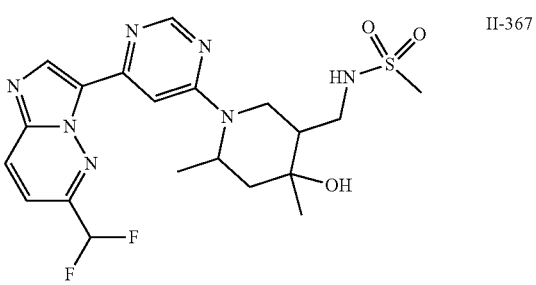
II-367
single diastereomer
(two enantiomers)
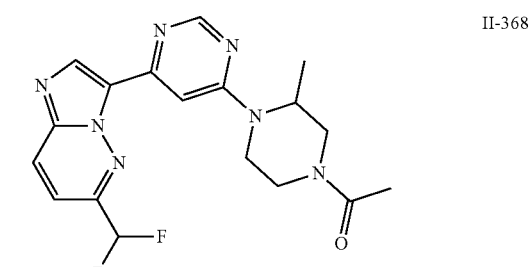
II-368
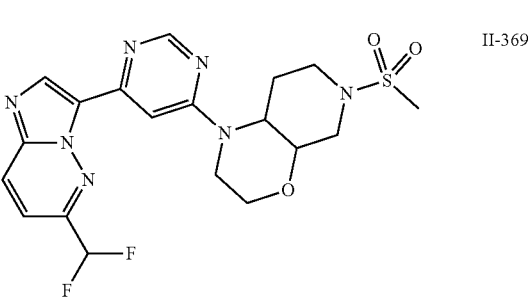
II-369

TABLE 1-continued
Exemplary compounds of formula II
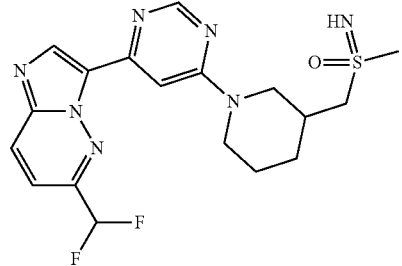 [SMILES: CS(=N)(=O)CC1CCCN(c2cc(-c3cnc4ccc(C(F)F)nn34)ncn2)C1]
II-370
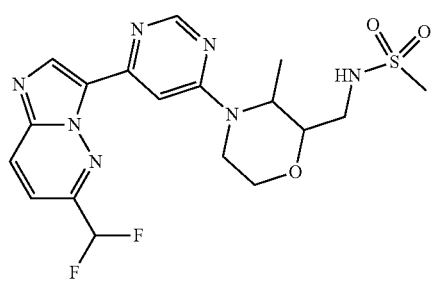
II-371
single stereoisomer
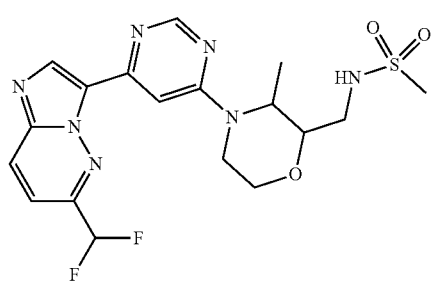
II-372
single stereoisomer
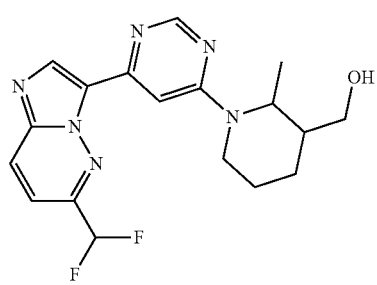 [SMILES: CC1C(CO)CCCN1c1cc(-c2cnc3ccc(C(F)F)nn23)ncn1]
II-373
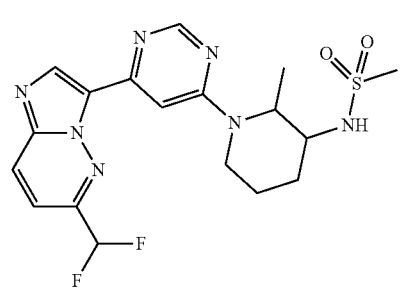 [SMILES: CC1C(NS(C)(=O)=O)CCCN1c1cc(-c2cnc3ccc(C(F)F)nn23)ncn1]
II-374
TABLE 1-continued
Exemplary compounds of formula II
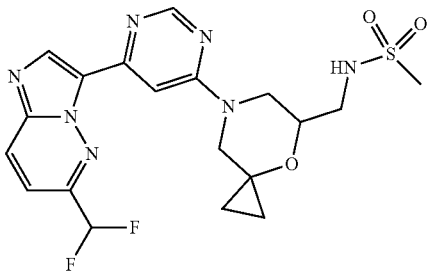 [SMILES: CS(=O)(=O)NCC1CN(c2cc(-c3cnc4ccc(C(F)F)nn34)ncn2)CC2(CC2)O1]
II-375
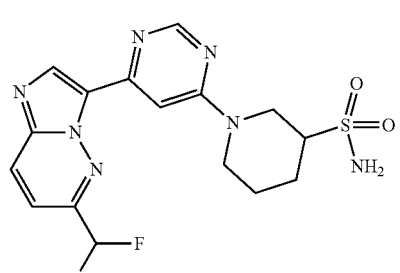
II-376
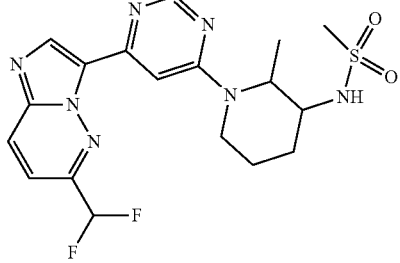
II-377
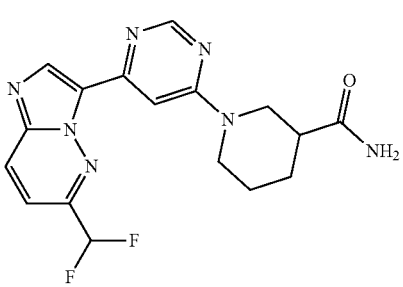 [SMILES: NC(=O)C1CCCN(c2cc(-c3cnc4ccc(C(F)F)nn34)ncn2)C1]
II-378
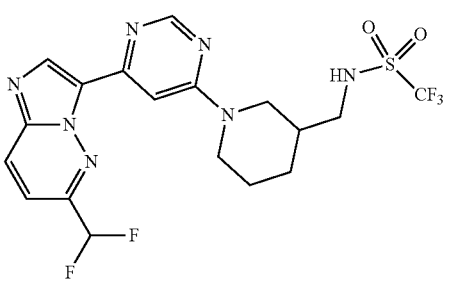 [SMILES: O=S(=O)(NCC1CCCN(c2cc(-c3cnc4ccc(C(F)F)nn34)ncn2)C1)C(F)(F)F]
II-379

TABLE 1-continued
Exemplary compounds of formula II
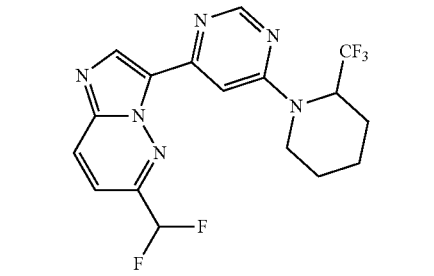 [SMILES: FC(F)c1ccc2ncc(-c3cc(N4CCCCC4C(F)(F)F)ncn3)n2n1]
II-380
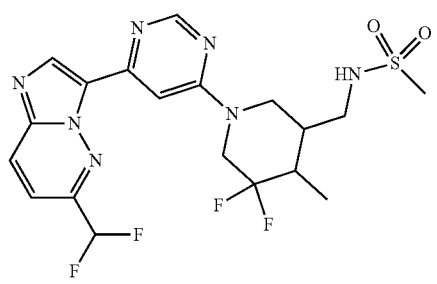
II-381
single diastereomer
(two enantiomers)
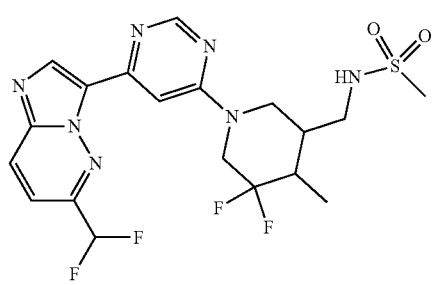
II-382
single diastereomer
(two enantiomers)
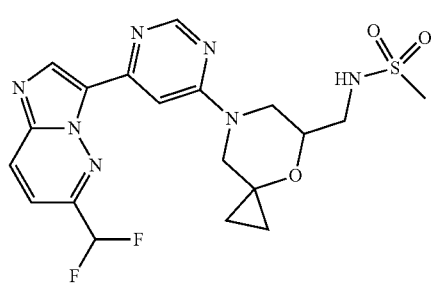
II-383
single stereoisomer
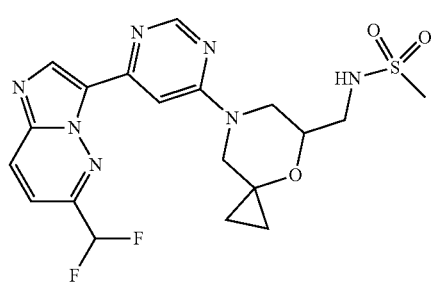
II-384
single stereoisomer
TABLE 1-continued
Exemplary compounds of formula II
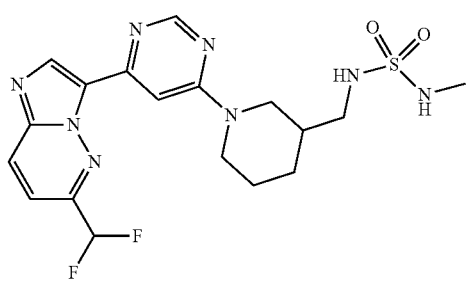 [SMILES: CNS(=O)(=O)NCC1CCCN(c2cc(-c3cnc4ccc(C(F)F)nn34)ncn2)C1]
II-385
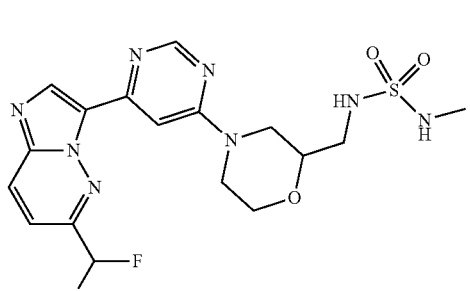
II-386
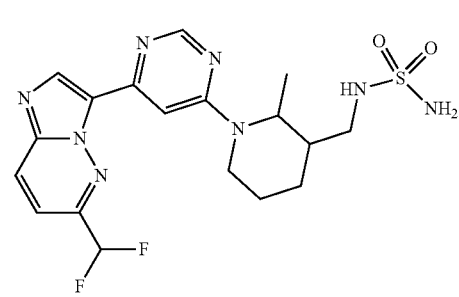 [SMILES: CC1C(CNS(N)(=O)=O)CCCN1c1cc(-c2cnc3ccc(C(F)F)nn23)ncn1]
II-387
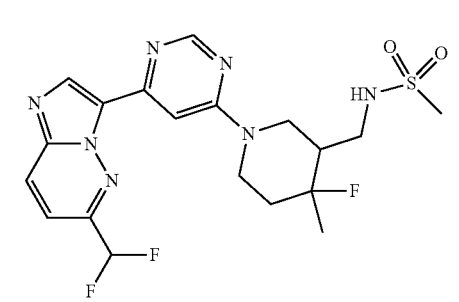
II-388
single stereoisomer
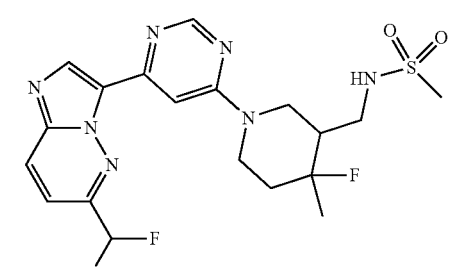
II-389
single stereoisomer TABLE 1-continued
Exemplary compounds of formula II
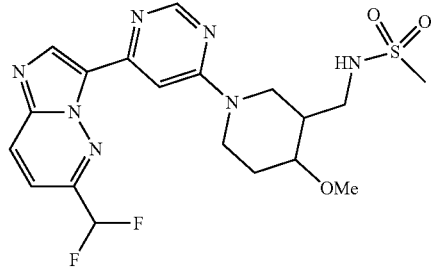 [SMILES: COC1CCN(c2cc(-c3cnc4ccc(C(F)F)nn34)ncn2)CC1CNS(C)(=O)=O]
II-390
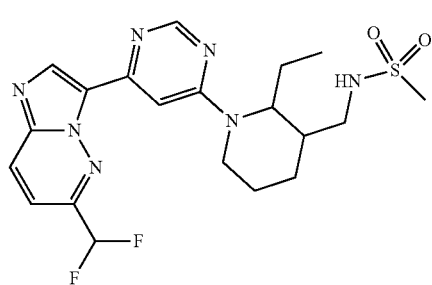 [SMILES: CCC1C(CNS(C)(=O)=O)CCCN1c1cc(-c2cnc3ccc(C(F)F)nn23)ncn1]
II-391
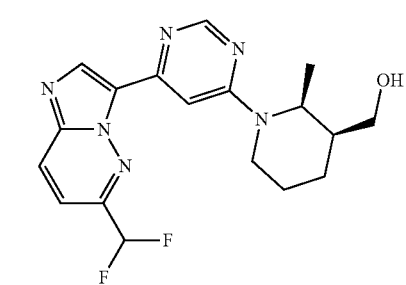 [SMILES: C[C@H]1[C@@H](CO)CCCN1c1cc(-c2cnc3ccc(C(F)F)nn23)ncn1]
II-392
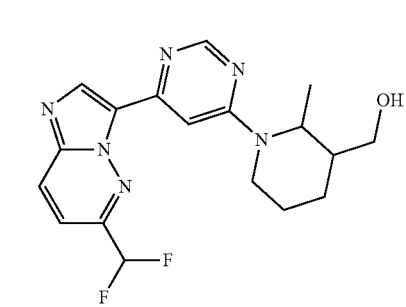
II-393
single stereoisomer

II-394
TABLE 1-continued
Exemplary compounds of formula II
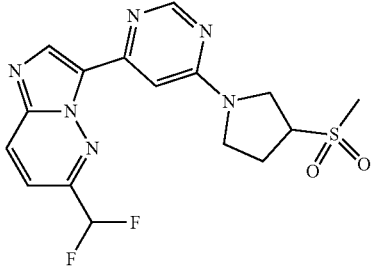 [SMILES: CS(=O)(=O)C1CCN(c2cc(-c3cnc4ccc(C(F)F)nn34)ncn2)C1]
II-395
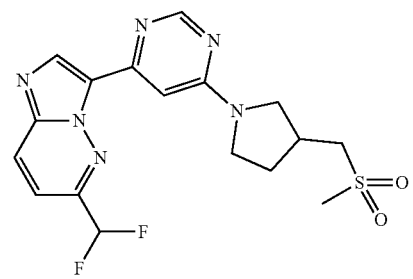 [SMILES: CS(=O)(=O)CC1CCN(c2cc(-c3cnc4ccc(C(F)F)nn34)ncn2)C1]
II-396
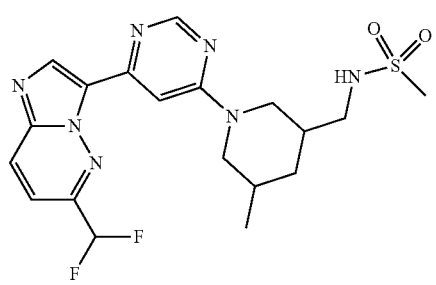
II-397
single diastereomer
(two enantiomers)
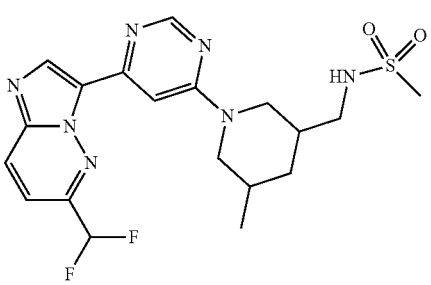
II-398
single diastereomer
(two enantiomers)
II-399

TABLE 1-continued
Exemplary compounds of formula II
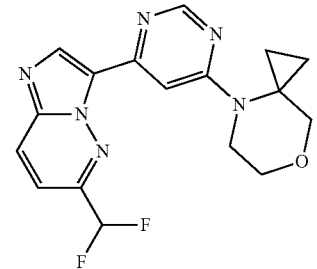 [SMILES: FC(F)c1ccc2ncc(-c3cc(N4CCOCC45CC5)ncn3)n2n1] II-400
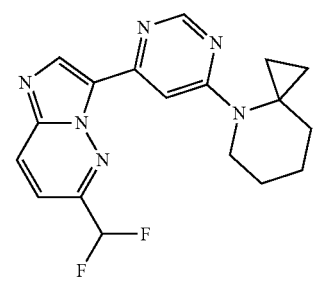 [SMILES: FC(F)c1ccc2ncc(-c3cc(N4CCCCC45CC5)ncn3)n2n1] II-401
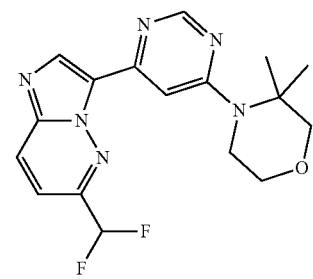 [SMILES: CC1(C)COCCN1c1cc(-c2cnc3ccc(C(F)F)nn23)ncn1] II-402
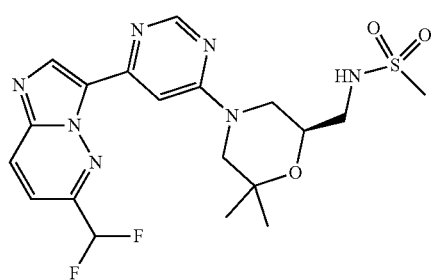 [SMILES: CC1(C)CN(c2cc(-c3cnc4ccc(C(F)F)nn34)ncn2)C[C@@H](CNS(C)(=O)=O)O1] II-403
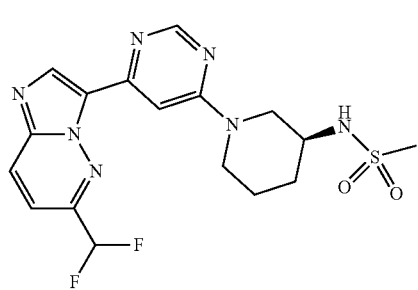 [SMILES: CS(=O)(=O)N[C@H]1CCCN(c2cc(-c3cnc4ccc(C(F)F)nn34)ncn2)C1] II-404
TABLE 1-continued
Exemplary compounds of formula II
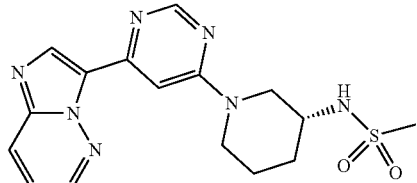 II-405
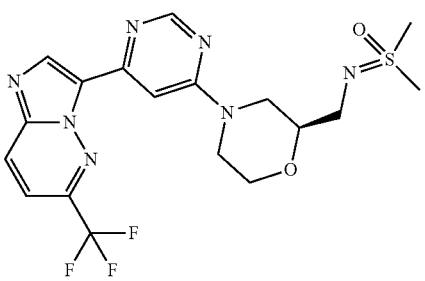 [SMILES: CS(C)(=O)=NC[C@@H]1CN(c2cc(-c3cnc4ccc(C(F)(F)F)nn34)ncn2)CCO1] II-406
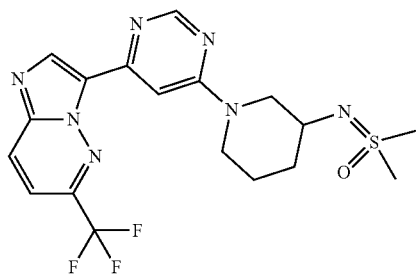 [SMILES: CS(C)(=O)=NC1CCCN(c2cc(-c3cnc4ccc(C(F)(F)F)nn34)ncn2)C1] II-407
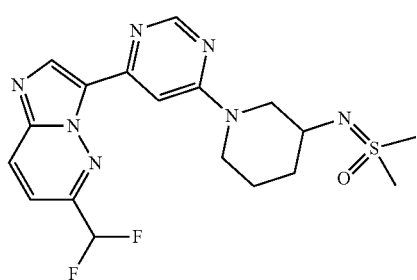 [SMILES: CS(C)(=O)=NC1CCCN(c2cc(-c3cnc4ccc(C(F)F)nn34)ncn2)C1] II-408
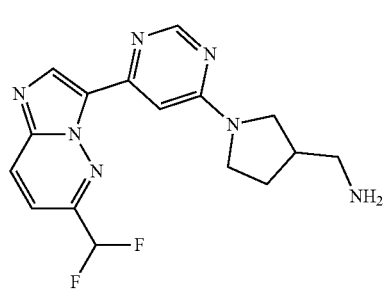 [SMILES: NCC1CCN(c2cc(-c3cnc4ccc(C(F)F)nn34)ncn2)C1] II-409

TABLE 1-continued
Exemplary compounds of formula II
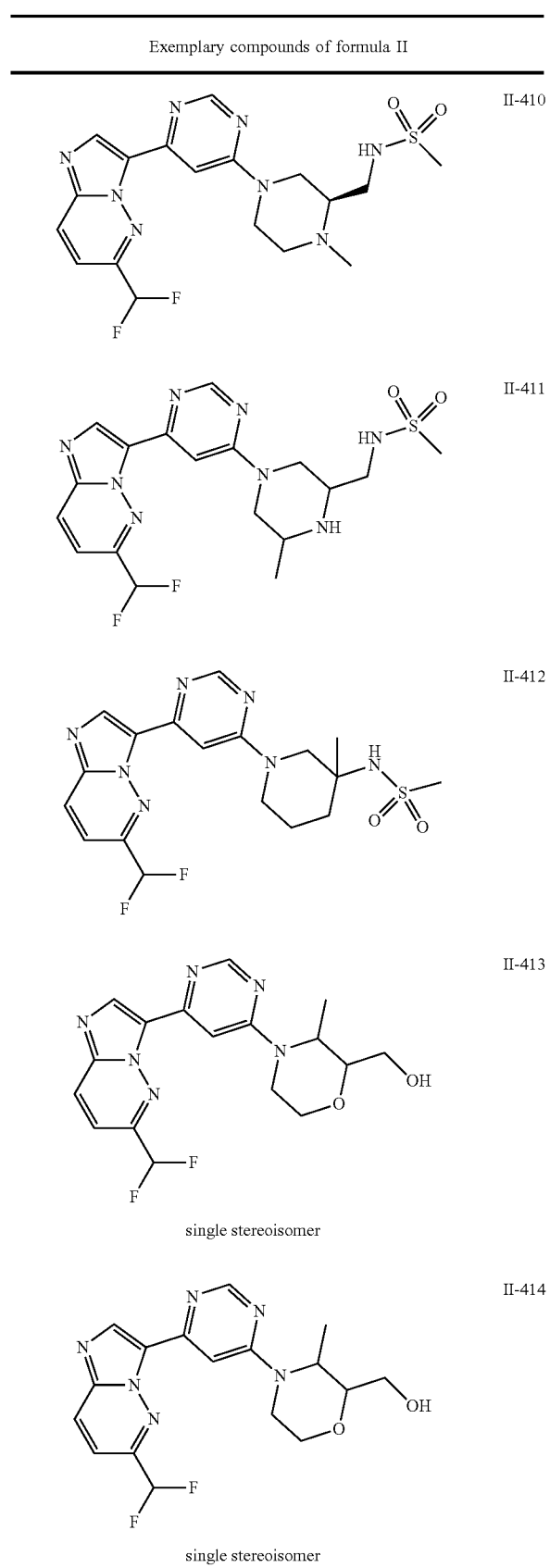
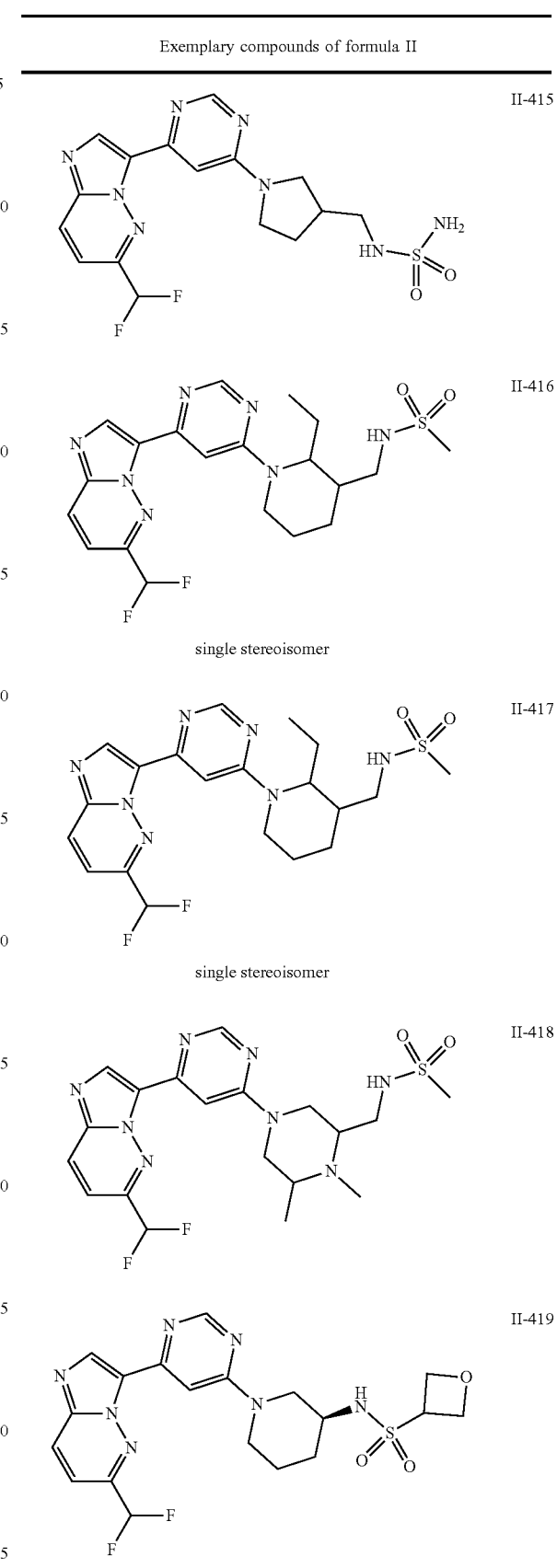

TABLE 1-continued
Exemplary compounds of formula II
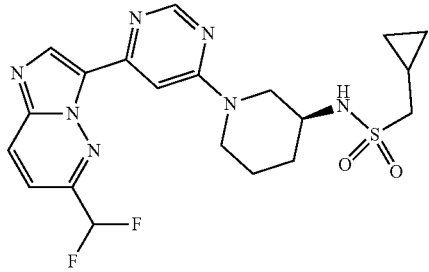 [SMILES: O=S(=O)(CC1CC1)N[C@H]1CCCN(c2cc(-c3cnc4ccc(C(F)F)nn34)ncn2)C1] II-420
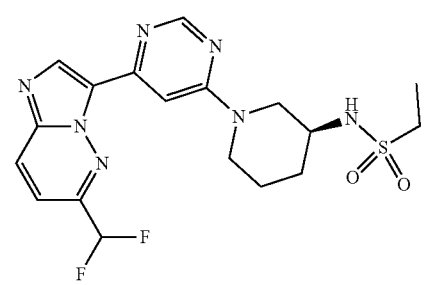 [SMILES: CCS(=O)(=O)N[C@H]1CCCN(c2cc(-c3cnc4ccc(C(F)F)nn34)ncn2)C1] II-421
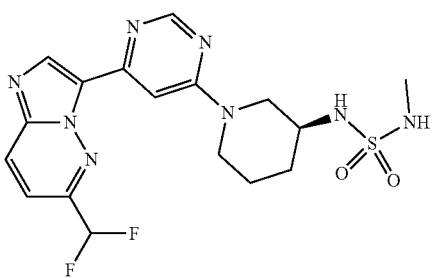 [SMILES: CNS(=O)(=O)N[C@H]1CCCN(c2cc(-c3cnc4ccc(C(F)F)nn34)ncn2)C1] II-422
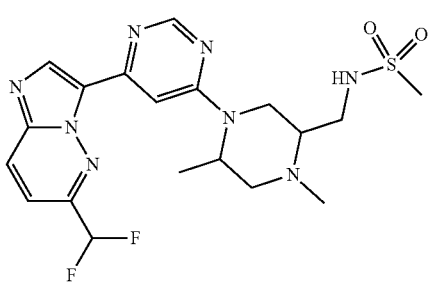 [SMILES: CC1CN(C)C(CNS(C)(=O)=O)CN1c1cc(-c2cnc3ccc(C(F)F)nn23)ncn1] II-423
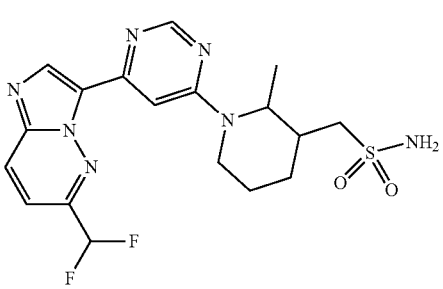 [SMILES: CC1C(CS(N)(=O)=O)CCCN1c1cc(-c2cnc3ccc(C(F)F)nn23)ncn1] II-424
TABLE 1-continued
Exemplary compounds of formula II
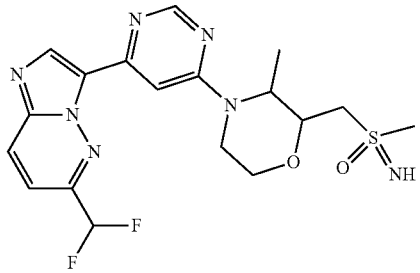 II-425
single stereoisomer
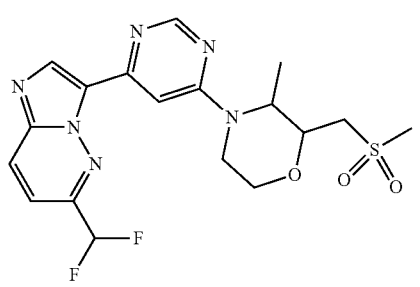 II-426
single stereoisomer
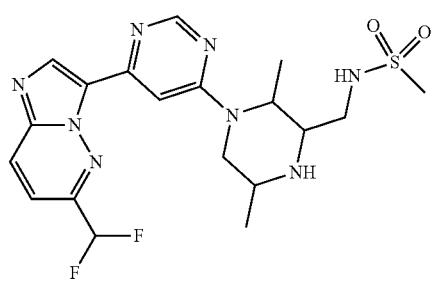 [SMILES: CC1CN(c2cc(-c3cnc4ccc(C(F)F)nn34)ncn2)C(C)C(CNS(C)(=O)=O)N1] II-427
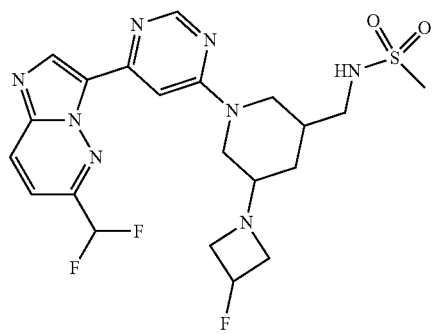 II-428
single diastereomer
(two enantiomers)

TABLE 1-continued
Exemplary compounds of formula II
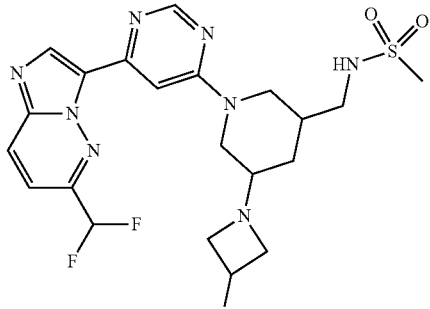
II-429
single diastereomer
(two enantiomers)
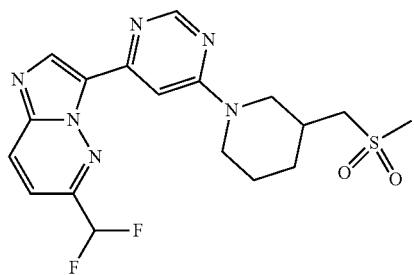 [SMILES: CS(=O)(=O)CC1CCCN(c2cc(-c3cnc4ccc(C(F)F)nn34)ncn2)C1]
II-430
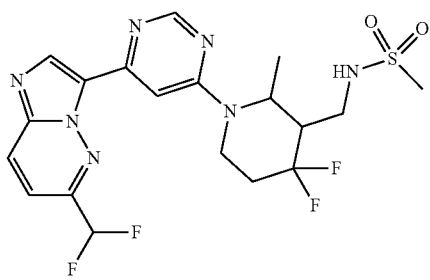
II-431
single stereoisomer
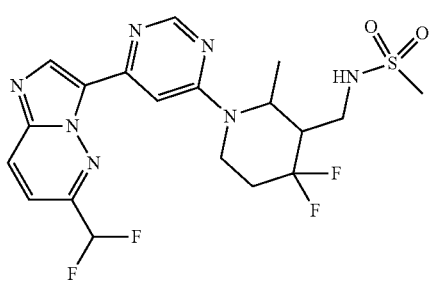
II-432
single stereoisomer
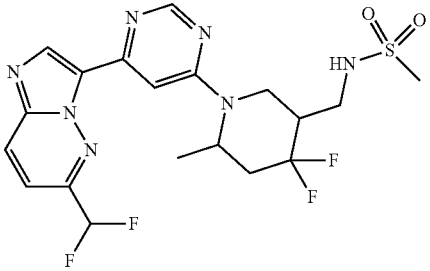
II-433
single stereoisomer
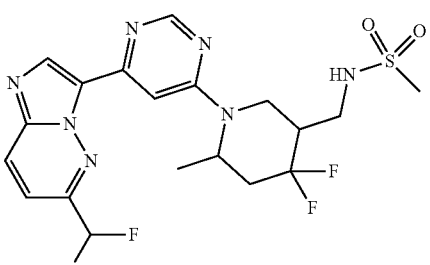
II-434
single stereoisomer
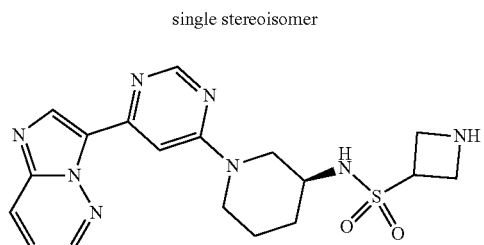
II-435
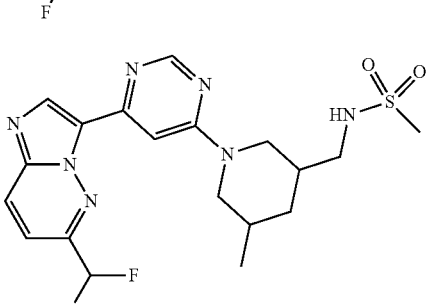
II-436
single stereoisomer
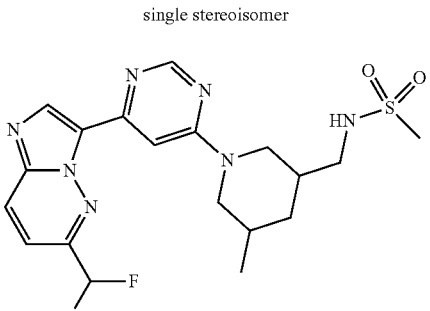
II-437
single stereoisomer TABLE 1-continued
Exemplary compounds of formula II
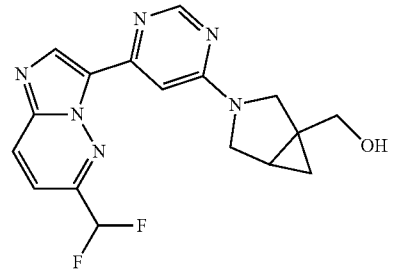 [SMILES: OCC12CC1CN(c1cc(-c3cnc4ccc(C(F)F)nn34)ncn1)C2]
II-438
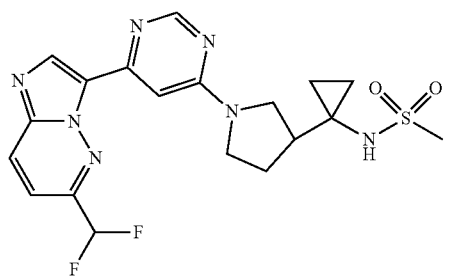 [SMILES: CS(=O)(=O)NC1(C2CCN(c3cc(-c4cnc5ccc(C(F)F)nn45)ncn3)C2)CC1]
II-439
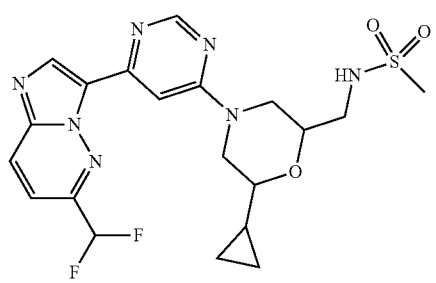
II-440
single stereoisomer
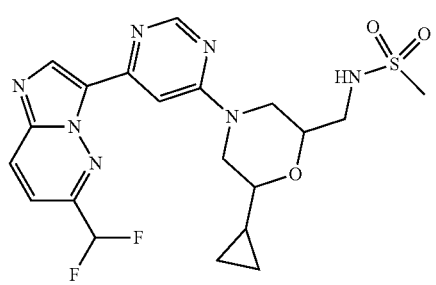
II-441
single stereoisomer
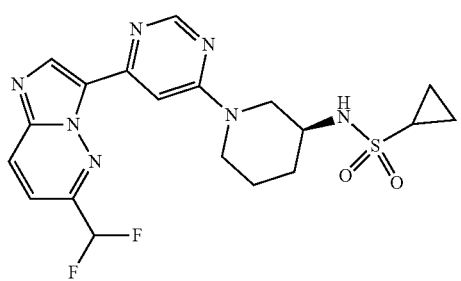 [SMILES: O=S(=O)(N[C@H]1CCCN(c2cc(-c3cnc4ccc(C(F)F)nn34)ncn2)C1)C1CC1]
II-442
TABLE 1-continued
Exemplary compounds of formula II
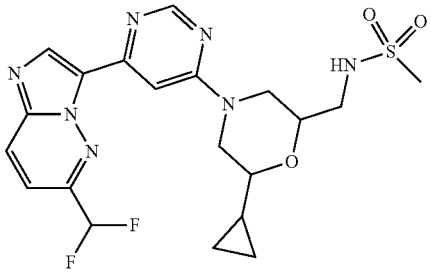
II-443
single stereoisomer
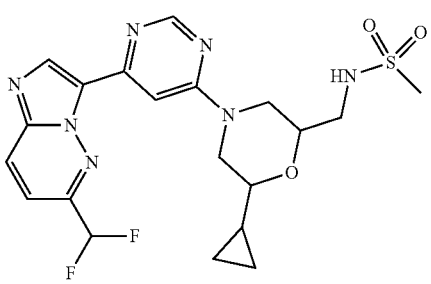
II-444
single stereoisomer
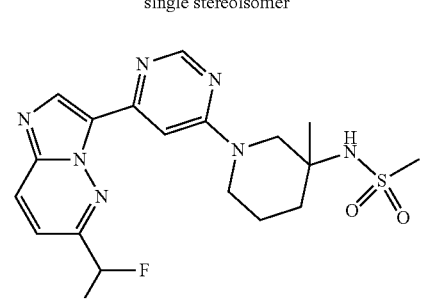
II-445
single stereoisomer
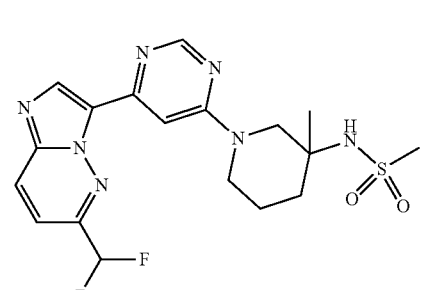
II-446
single stereoisomer
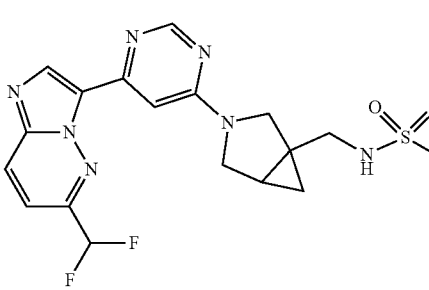
II-447

TABLE 1-continued
Exemplary compounds of formula II
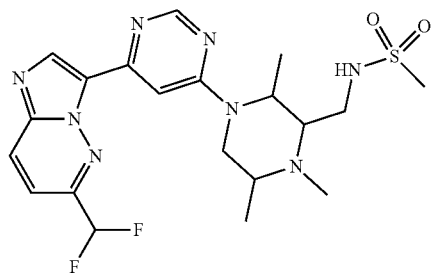 [SMILES: CC1C(CNS(C)(=O)=O)N(C)C(C)CN1c1cc(-c2cnc3ccc(C(F)F)nn23)ncn1] II-448
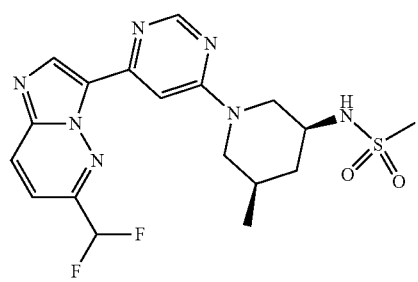 [SMILES: C[C@@H]1C[C@H](NS(C)(=O)=O)CN(c2cc(-c3cnc4ccc(C(F)F)nn34)ncn2)C1] II-449
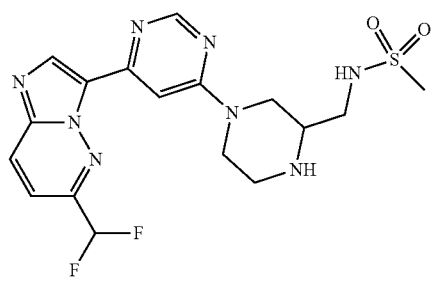 [SMILES: CS(=O)(=O)NCC1CN(c2cc(-c3cnc4ccc(C(F)F)nn34)ncn2)CCN1] II-450
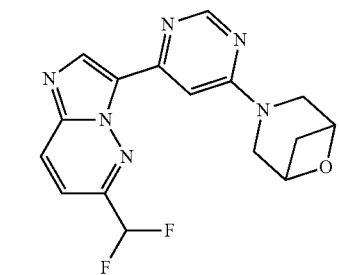 [SMILES: FC(F)c1ccc2ncc(-c3cc(N4CC5CC(C4)O5)ncn3)n2n1] II-451
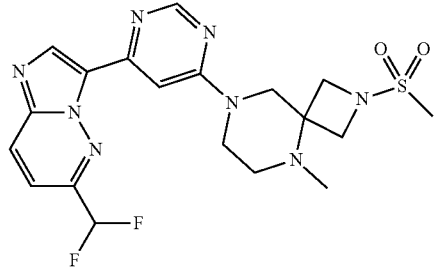 [SMILES: CN1CCN(c2cc(-c3cnc4ccc(C(F)F)nn34)ncn2)CC12CN(S(C)(=O)=O)C2] II-452
TABLE 1-continued
Exemplary compounds of formula II
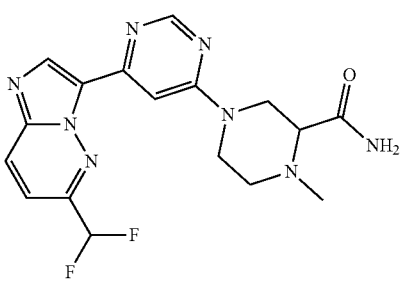 [SMILES: CN1CCN(c2cc(-c3cnc4ccc(C(F)F)nn34)ncn2)CC1C(N)=O] II-453
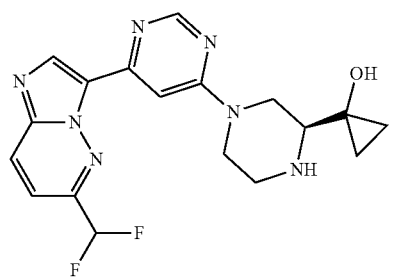 [SMILES: OC1([C@@H]2CN(c3cc(-c4cnc5ccc(C(F)F)nn45)ncn3)CCN2)CC1] II-454
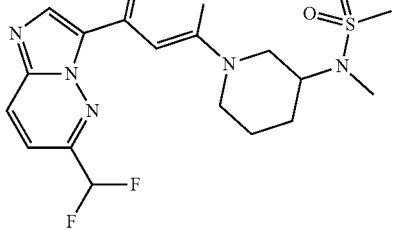 II-455
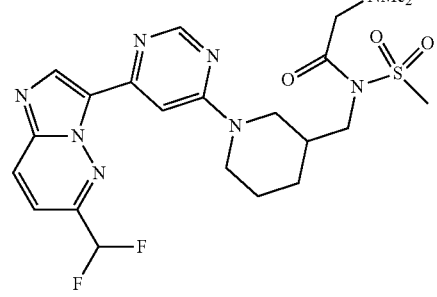 II-456
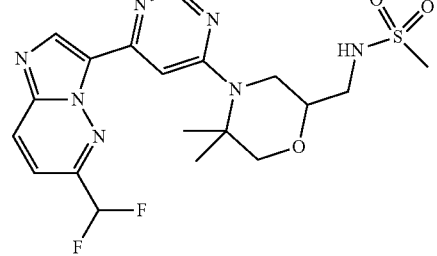 II-457

TABLE 1-continued
Exemplary compounds of formula II
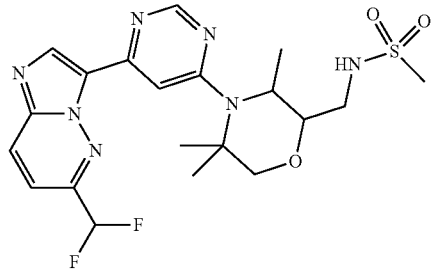 [SMILES: CC1C(CNS(C)(=O)=O)OCC(C)(C)N1c1cc(-c2cnc3ccc(C(F)F)nn23)ncn1] II-458
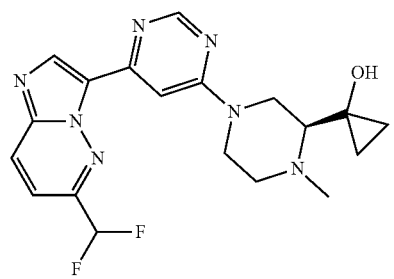 [SMILES: CN1CCN(c2cc(-c3cnc4ccc(C(F)F)nn34)ncn2)C[C@H]1C1(O)CC1] II-459
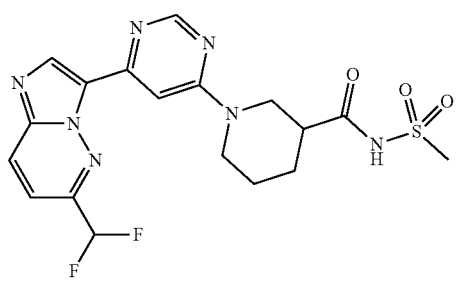 [SMILES: CS(=O)(=O)NC(=O)C1CCCN(c2cc(-c3cnc4ccc(C(F)F)nn34)ncn2)C1] II-460
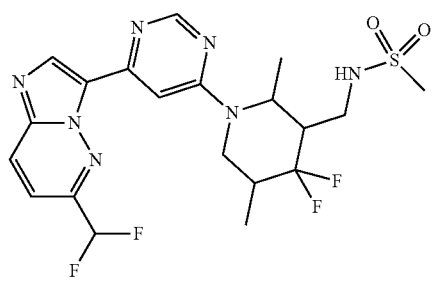 II-461
single diastereomer
(two enantiomers)
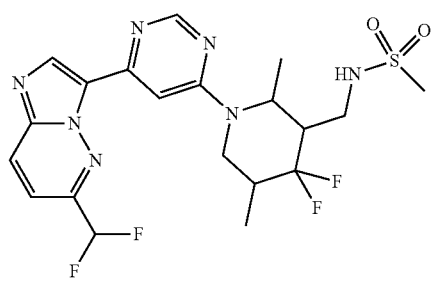 [SMILES: CC1C(CNS(C)(=O)=O)C(F)(F)C(C)CN1c1cc(-c2cnc3ccc(C(F)F)nn23)ncn1] II-462
TABLE 1-continued
Exemplary compounds of formula II
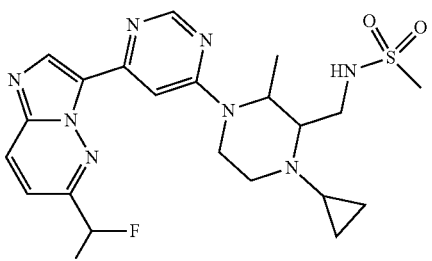 II-463
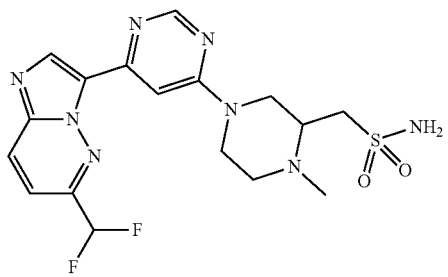 [SMILES: CN1CCN(c2cc(-c3cnc4ccc(C(F)F)nn34)ncn2)CC1CS(N)(=O)=O] II-464
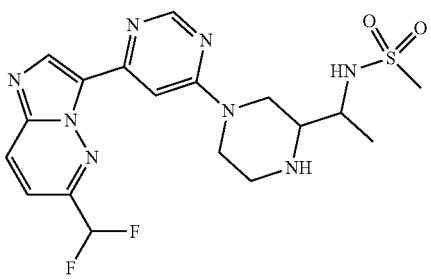 [SMILES: CC(NS(C)(=O)=O)C1CN(c2cc(-c3cnc4ccc(C(F)F)nn34)ncn2)CCN1] II-465
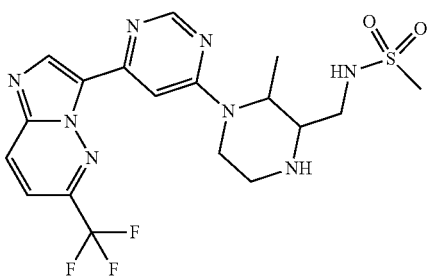 II-466
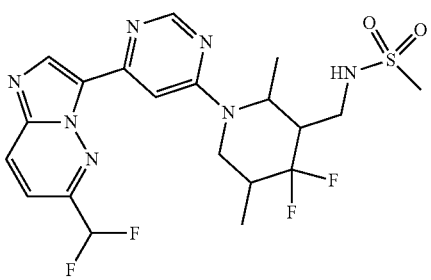 II-467
single stereoisomer TABLE 1-continued
Exemplary compounds of formula II
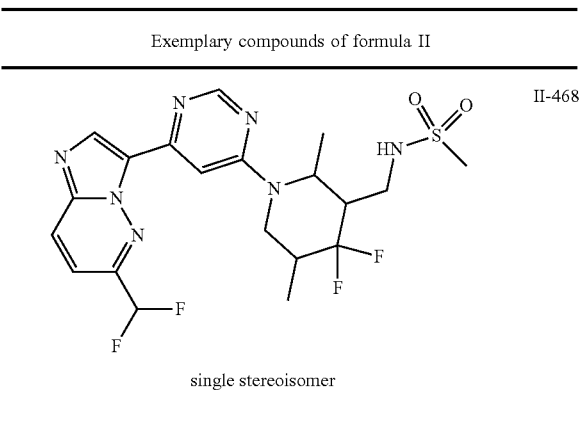
II-468
single stereoisomer
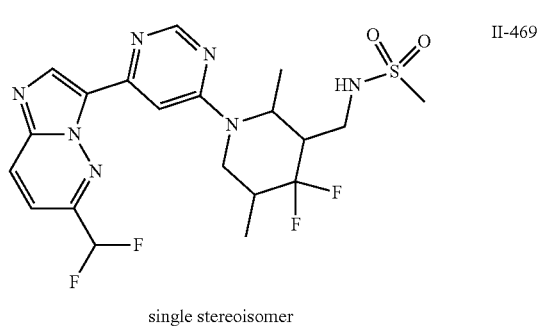
II-469
single stereoisomer
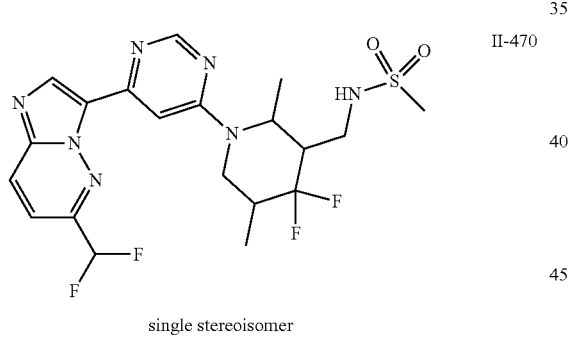
II-470
single stereoisomer
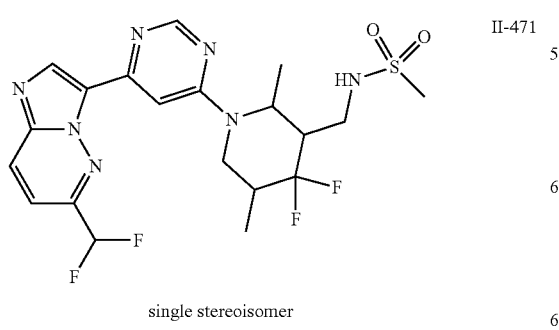
II-471
single stereoisomer
TABLE 1-continued
Exemplary compounds of formula II
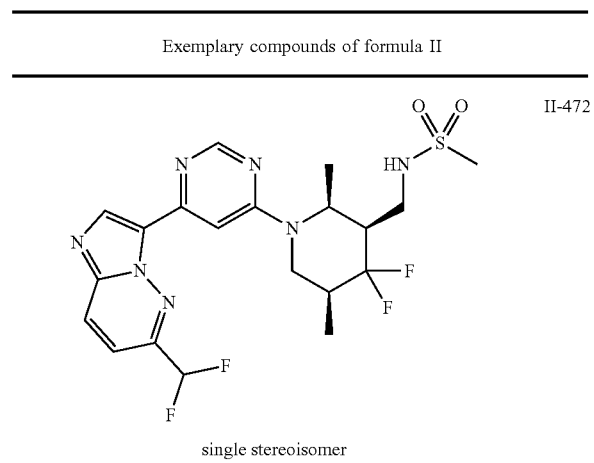
II-472
single stereoisomer
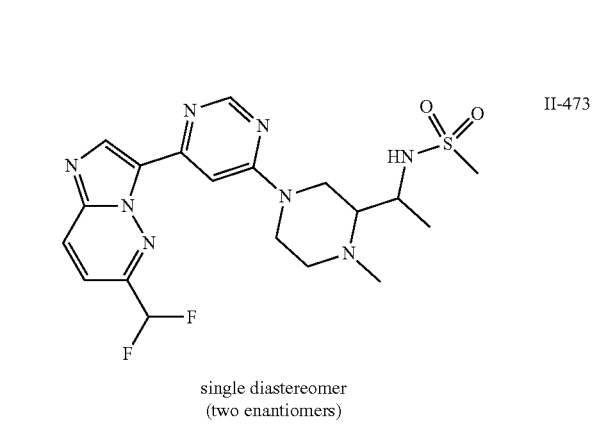
II-473
single diastereomer
(two enantiomers)
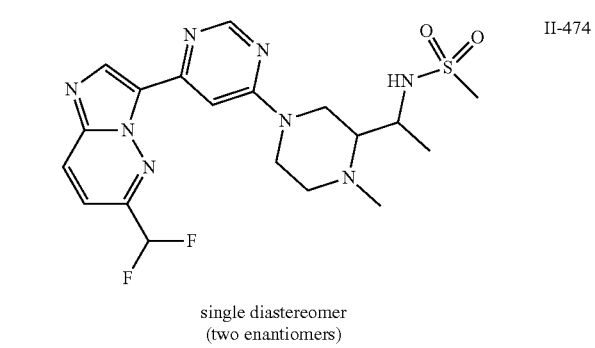
II-474
single diastereomer
(two enantiomers)
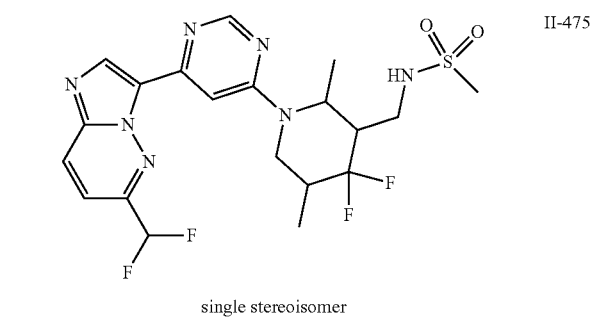
II-475
single stereoisomer TABLE 1-continued
Exemplary compounds of formula II
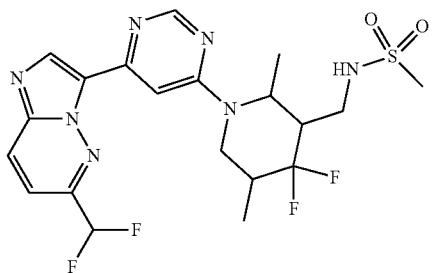
II-476
single stereoisomer
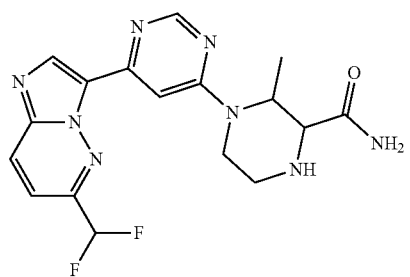 [SMILES: CC1C(C(N)=O)NCCN1c1cc(-c2cnc3ccc(C(F)F)nn23)ncn1]
II-477
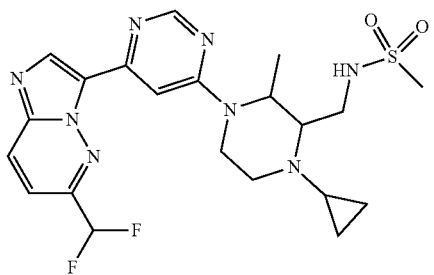
II-478
single stereoisomer
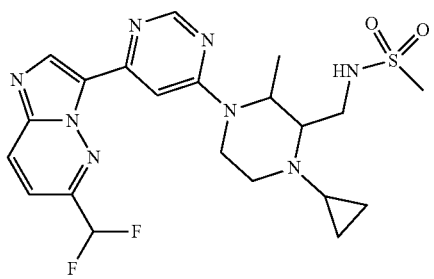
II-479
single stereoisomer
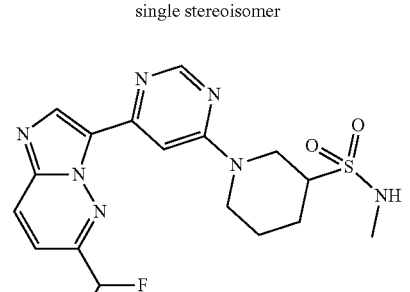
II-480
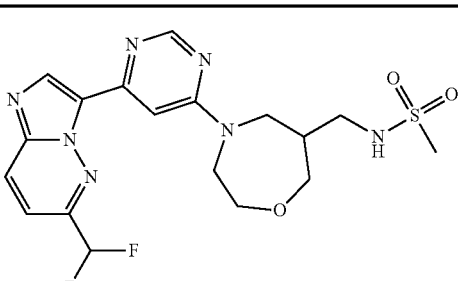
II-481
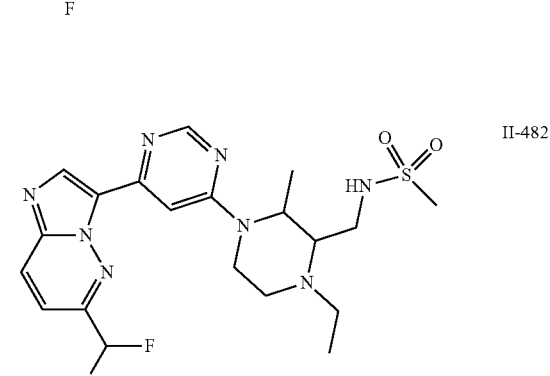
II-482
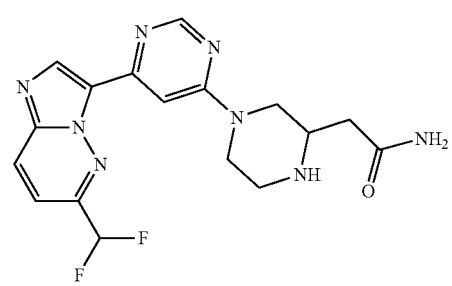 [SMILES: NC(=O)CC1CN(c2cc(-c3cnc4ccc(C(F)F)nn34)ncn2)CCN1]
II-483
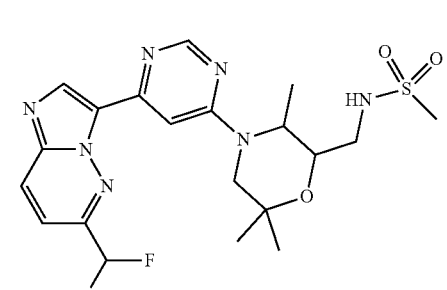
II-484
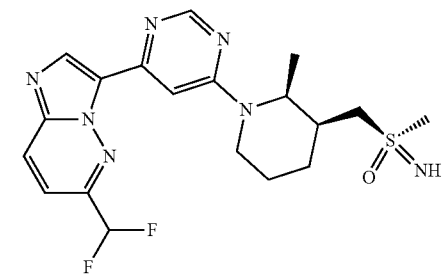
II-485

TABLE 1-continued
Exemplary compounds of formula II
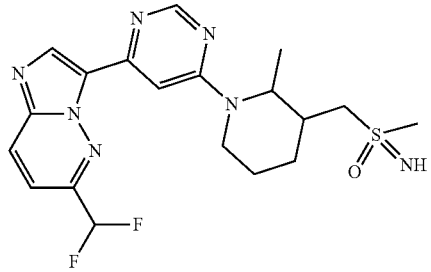 II-486
single stereoisomer
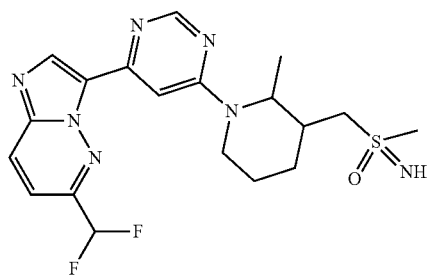 II-487
single stereoisomer
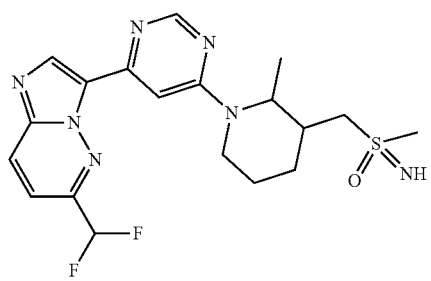 II-488
single stereoisomer
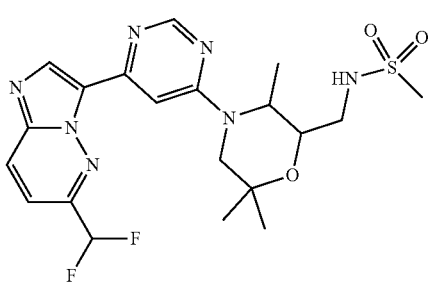 [SMILES: CC1C(CNS(C)(=O)=O)OC(C)(C)CN1c1cc(-c2cnc3ccc(C(F)F)nn23)ncn1] II-489
single stereoisomer
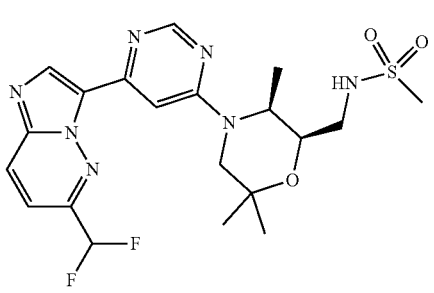 [SMILES: C[C@H]1[C@@H](CNS(C)(=O)=O)OC(C)(C)CN1c1cc(-c2cnc3ccc(C(F)F)nn23)ncn1] II-490
TABLE 1-continued
Exemplary compounds of formula II
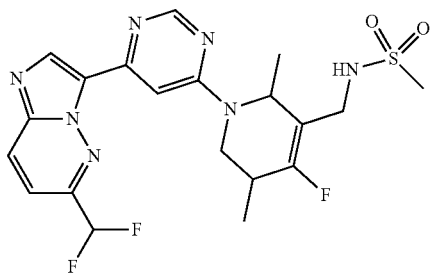 [SMILES: CC1CN(c2cc(-c3cnc4ccc(C(F)F)nn34)ncn2)C(C)C(CNS(C)(=O)=O)=C1F] II-491
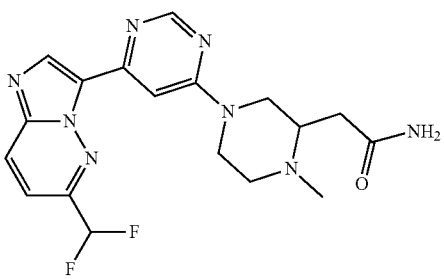 [SMILES: CN1CCN(c2cc(-c3cnc4ccc(C(F)F)nn34)ncn2)CC1CC(N)=O] II-492
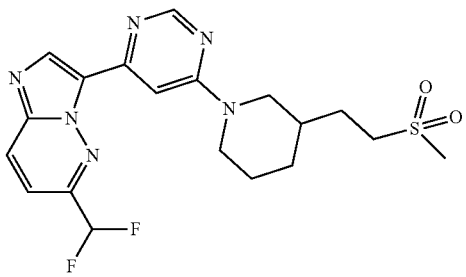 [SMILES: CS(=O)(=O)CCC1CCCN(c2cc(-c3cnc4ccc(C(F)F)nn34)ncn2)C1] II-493
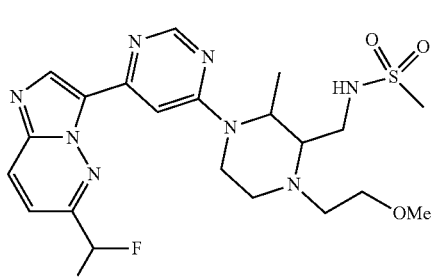 II-494
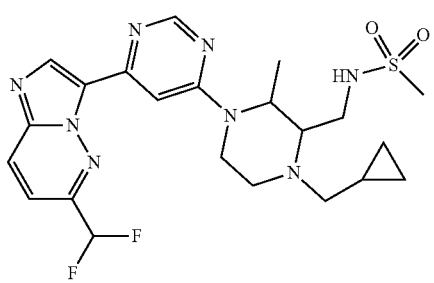 [SMILES: CC1C(CNS(C)(=O)=O)N(CC2CC2)CCN1c1cc(-c2cnc3ccc(C(F)F)nn23)ncn1] II-495

TABLE 1-continued

Exemplary compounds of formula II

| ID | |
|---|---|
| II-496 | (structure) |
| II-497 | (structure) |
| II-498 | (structure) |
| II-499 | (structure) |
| II-500 | (structure) |
| II-501 | (structure) |
| II-502 | (structure) |
| II-503 | (structure) single stereoisomer |
| II-504 | (structure) |
| II-505 | (structure) |

211
TABLE 1-continued
Exemplary compounds of formula II
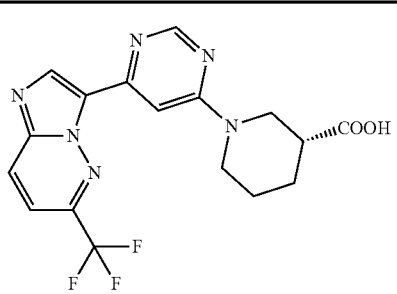
II-506
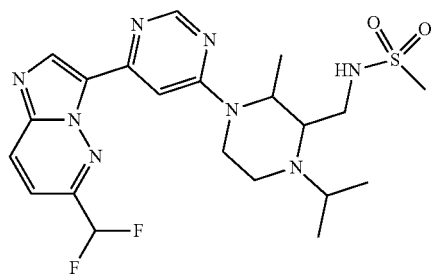 [SMILES: CC1C(CNS(C)(=O)=O)N(C(C)C)CCN1c1cc(-c2cnc3ccc(C(F)F)nn23)ncn1]
II-507
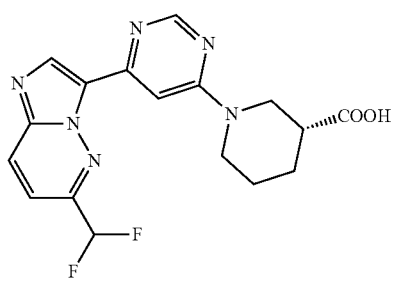 [SMILES: O=C(O)[C@@H]1CCCN(c2cc(-c3cnc4ccc(C(F)F)nn34)ncn2)C1]
II-508
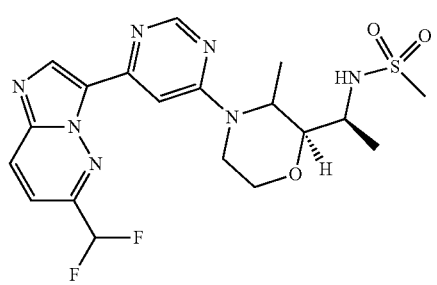 [SMILES: CC1[C@@H]([C@H](C)NS(C)(=O)=O)OCCN1c1cc(-c2cnc3ccc(C(F)F)nn23)ncn1]
II-509
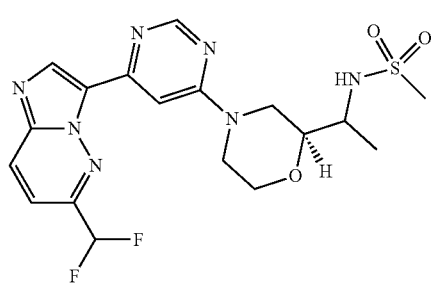
II-510
single stereoisomer
212
TABLE 1-continued
Exemplary compounds of formula II
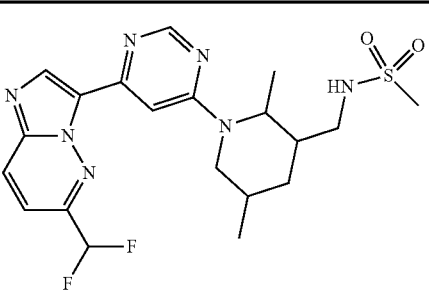
II-511
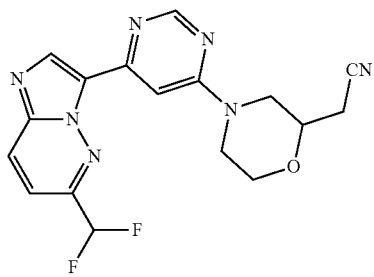 [SMILES: N#CCC1CN(c2cc(-c3cnc4ccc(C(F)F)nn34)ncn2)CCO1]
II-512
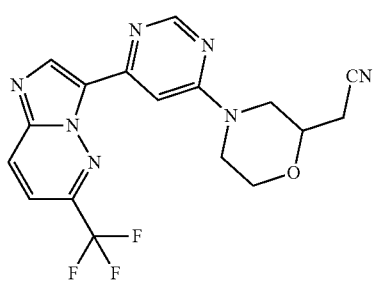 [SMILES: N#CCC1CN(c2cc(-c3cnc4ccc(C(F)(F)F)nn34)ncn2)CCO1]
II-513
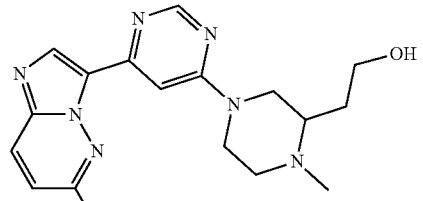
II-514
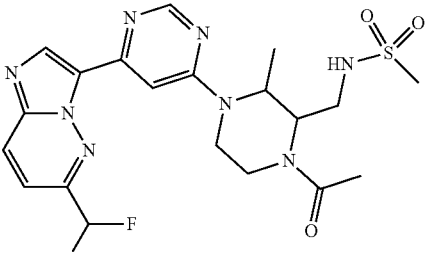
II-515

TABLE 1-continued
Exemplary compounds of formula II
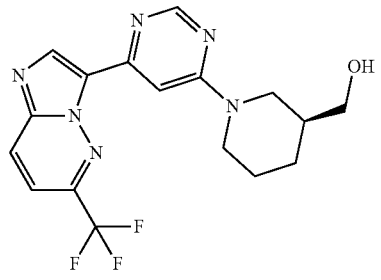 [SMILES: OC[C@H]1CCCN(c2cc(-c3cnc4ccc(C(F)(F)F)nn34)ncn2)C1] II-516
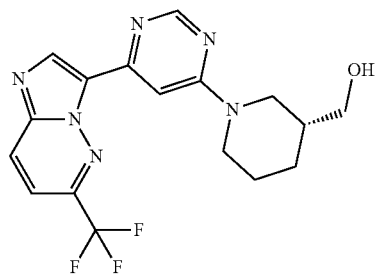 [SMILES: OC[C@@H]1CCCN(c2cc(-c3cnc4ccc(C(F)(F)F)nn34)ncn2)C1] II-517
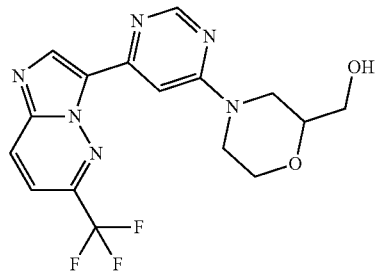 [SMILES: OCC1CN(c2cc(-c3cnc4ccc(C(F)(F)F)nn34)ncn2)CCO1] II-518
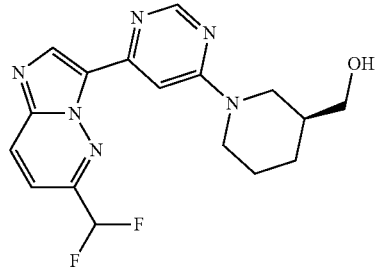 [SMILES: OC[C@H]1CCCN(c2cc(-c3cnc4ccc(C(F)F)nn34)ncn2)C1] II-519
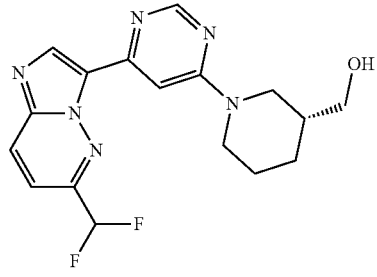 [SMILES: OC[C@@H]1CCCN(c2cc(-c3cnc4ccc(C(F)F)nn34)ncn2)C1] II-520
TABLE 1-continued
Exemplary compounds of formula II
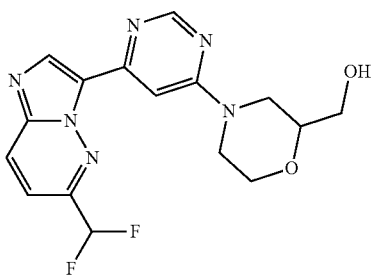 II-521
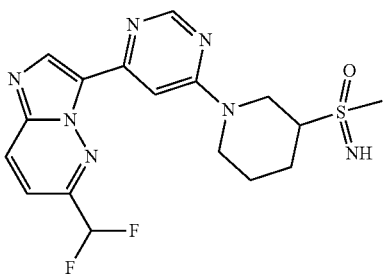 [SMILES: CS(=N)(=O)C1CCCN(c2cc(-c3cnc4ccc(C(F)F)nn34)ncn2)C1] II-522
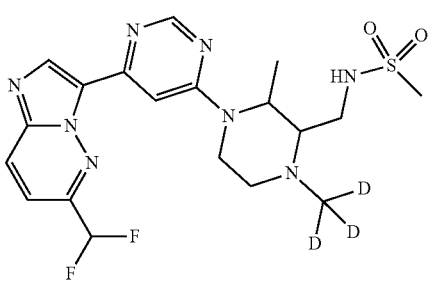 [SMILES: [2H]C([2H])([2H])N1CCN(c2cc(-c3cnc4ccc(C(F)F)nn34)ncn2)C(C)C1CNS(C)(=O)=O] II-523
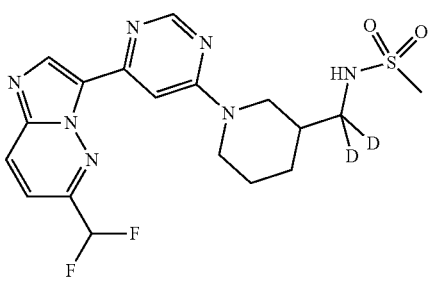 [SMILES: [2H]C([2H])(NS(C)(=O)=O)C1CCCN(c2cc(-c3cnc4ccc(C(F)F)nn34)ncn2)C1] II-524
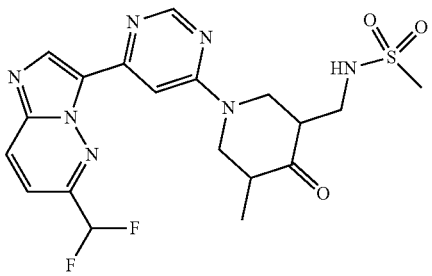 II-525
single diastereomer
(two enantiomers)

TABLE 1-continued
Exemplary compounds of formula II
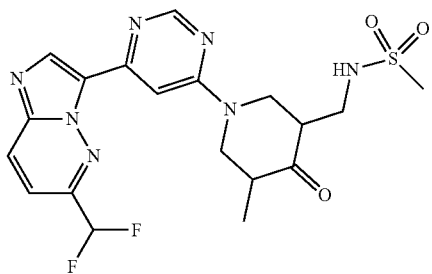 II-526
single diastereomer
(two enantiomers)
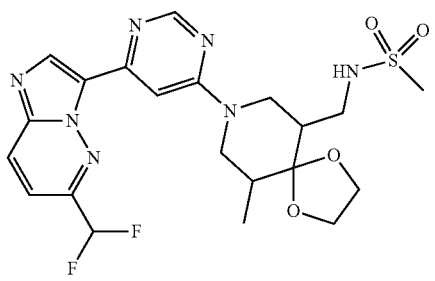 [SMILES: CC1CN(c2cc(-c3cnc4ccc(C(F)F)nn34)ncn2)CC(CNS(C)(=O)=O)C12OCCO2] II-527
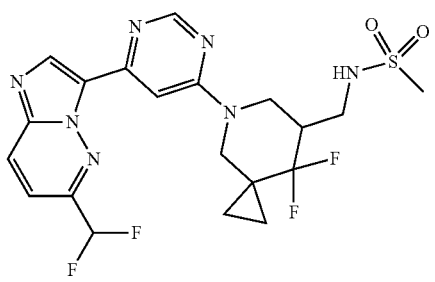 [SMILES: CS(=O)(=O)NCC1CN(c2cc(-c3cnc4ccc(C(F)F)nn34)ncn2)CC2(CC2)C1(F)F] II-528
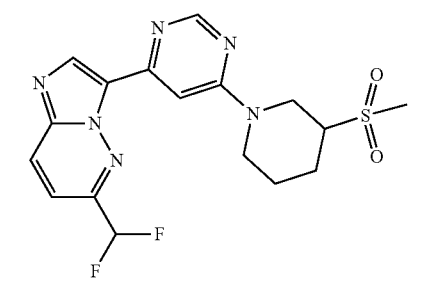 II-529
single stereoisomer
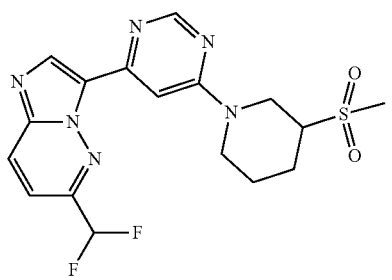 II-530
single stereoisomer
TABLE 1-continued
Exemplary compounds of formula II
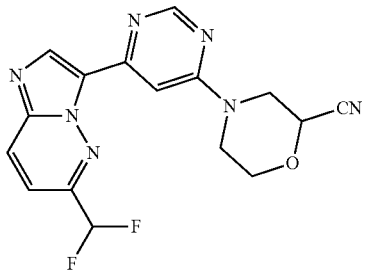 [SMILES: N#CC1CN(c2cc(-c3cnc4ccc(C(F)F)nn34)ncn2)CCO1] II-531
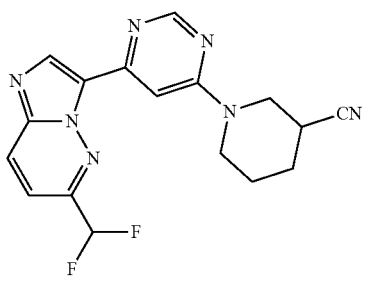 [SMILES: N#CC1CCCN(c2cc(-c3cnc4ccc(C(F)F)nn34)ncn2)C1] II-532
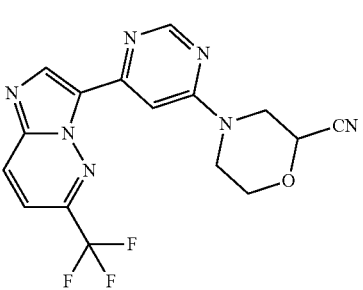 [SMILES: N#CC1CN(c2cc(-c3cnc4ccc(C(F)(F)F)nn34)ncn2)CCO1] II-533
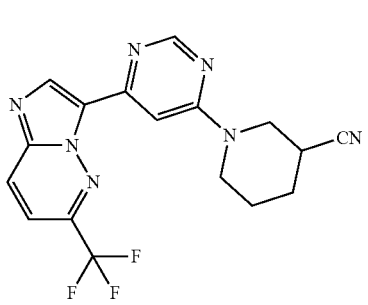 [SMILES: N#CC1CCCN(c2cc(-c3cnc4ccc(C(F)(F)F)nn34)ncn2)C1] II-534
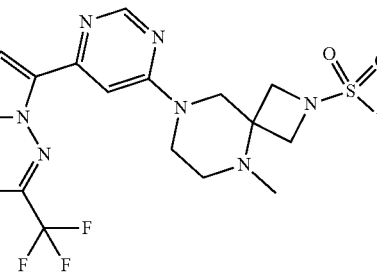 II-535

TABLE 1-continued
Exemplary compounds of formula II
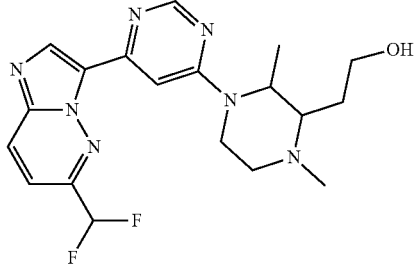 [SMILES: CC1C(CCO)N(C)CCN1c1cc(-c2cnc3ccc(C(F)F)nn23)ncn1] II-536
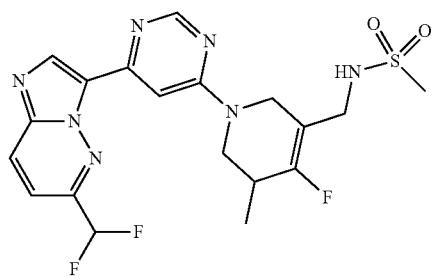 [SMILES: CC1CN(c2cc(-c3cnc4ccc(C(F)F)nn34)ncn2)CC(CNS(C)(=O)=O)=C1F] II-537
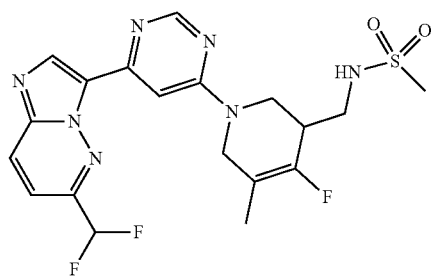 [SMILES: CC1=C(F)C(CNS(C)(=O)=O)CN(c2cc(-c3cnc4ccc(C(F)F)nn34)ncn2)C1] II-538
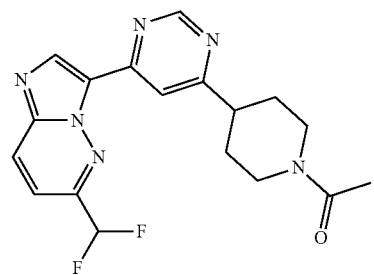 [SMILES: CC(=O)N1CCC(c2cc(-c3cnc4ccc(C(F)F)nn34)ncn2)CC1] II-539
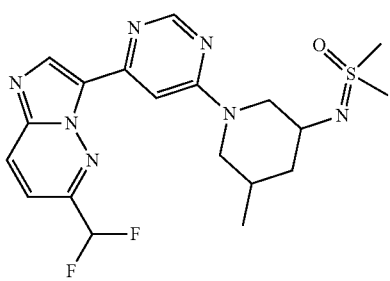 [SMILES: CC1CC(N=S(C)(C)=O)CN(c2cc(-c3cnc4ccc(C(F)F)nn34)ncn2)C1] II-540
TABLE 1-continued
Exemplary compounds of formula II
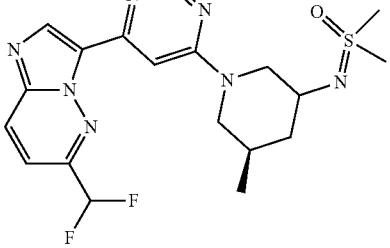 II-541
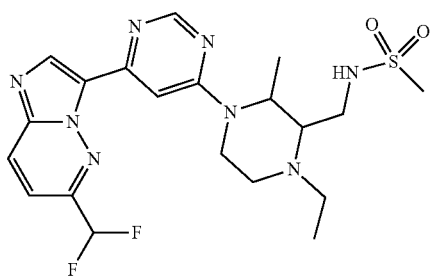 II-542
single stereoisomer
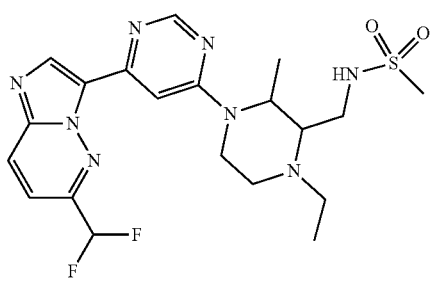 II-543
single stereoisomer
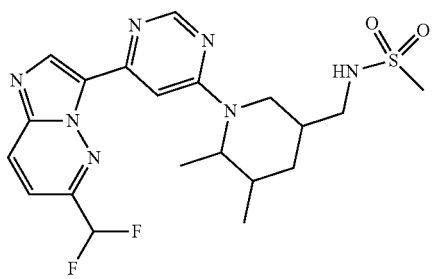 [SMILES: CC1CC(CNS(C)(=O)=O)CN(c2cc(-c3cnc4ccc(C(F)F)nn34)ncn2)C1C] II-544
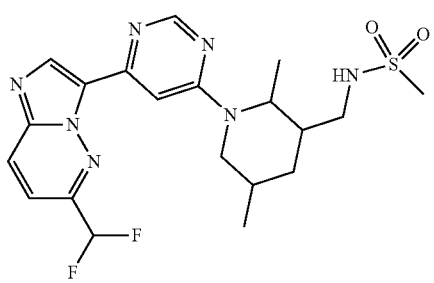 II-545
single stereoisomer TABLE 1-continued
Exemplary compounds of formula II
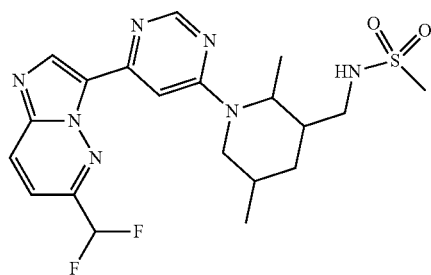
II-546
single stereoisomer
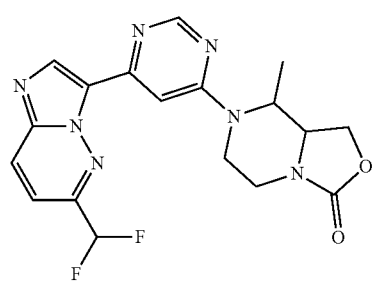 [SMILES: CC1C2COC(=O)N2CCN1c1cc(-c2cnc3ccc(C(F)F)nn23)ncn1]
II-547
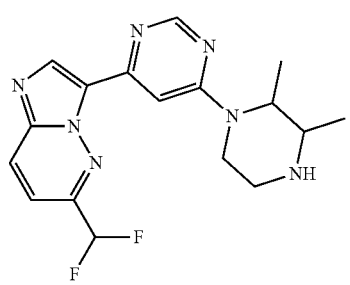 [SMILES: CC1NCCN(c2cc(-c3cnc4ccc(C(F)F)nn34)ncn2)C1C]
II-548
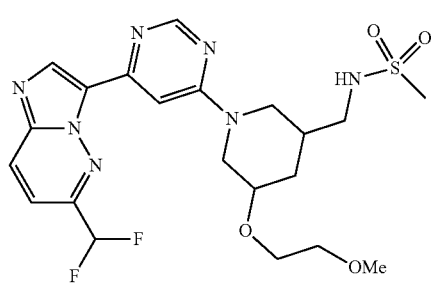
II-549
single diastereomer
(two enantiomers)
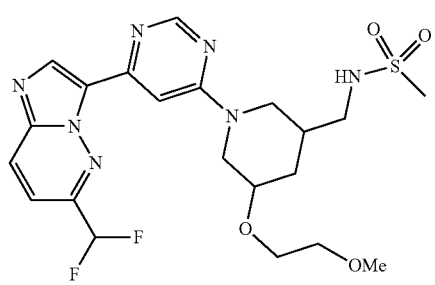
II-550
single diastereomer
(two enantiomers)
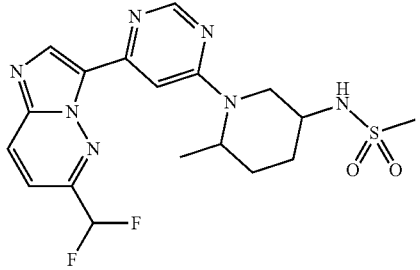
II-551
single diastereomer
(two enantiomers)
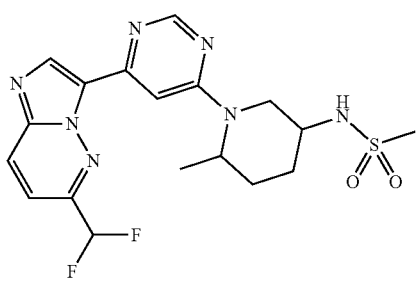
II-552
single diastereomer
(two enantiomers)
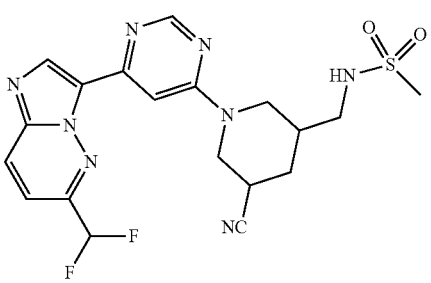 [SMILES: CS(=O)(=O)NCC1CC(C#N)CN(c2cc(-c3cnc4ccc(C(F)F)nn34)ncn2)C1]
II-553
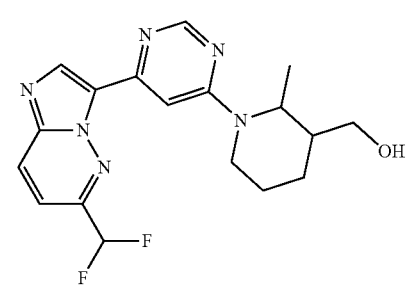
II-554
single stereoisomer
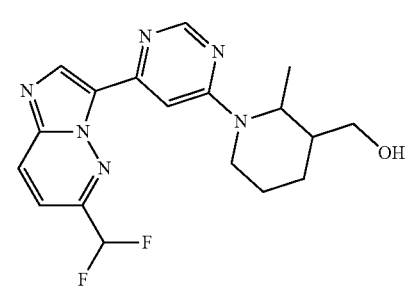
II-555
single stereoisomer TABLE 1-continued
Exemplary compounds of formula II
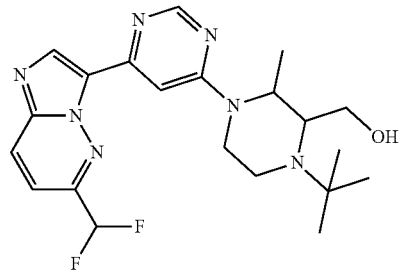 [SMILES: CC1C(CO)N(C(C)(C)C)CCN1c1cc(-c2cnc3ccc(C(F)F)nn23)ncn1] II-556
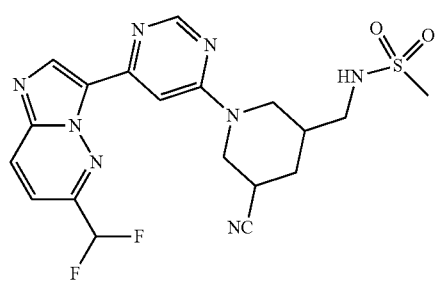 II-557
single stereoisomer
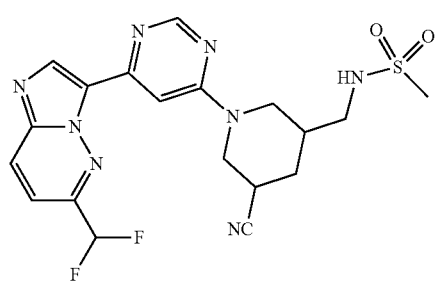 II-558
single stereoisomer
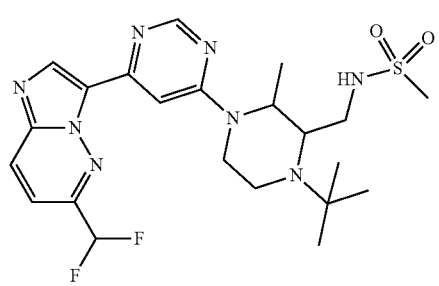 [SMILES: CC1C(CNS(C)(=O)=O)N(C(C)(C)C)CCN1c1cc(-c2cnc3ccc(C(F)F)nn23)ncn1] II-559
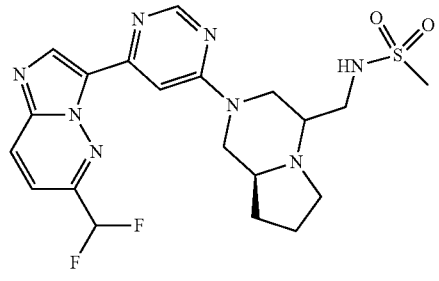 II-560
single stereoisomer
TABLE 1-continued
Exemplary compounds of formula II
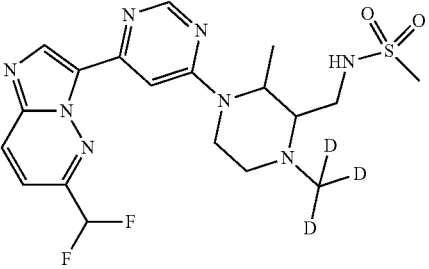 II-561
single stereoisomer
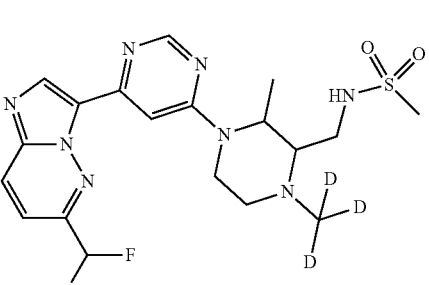 II-562
single stereoisomer
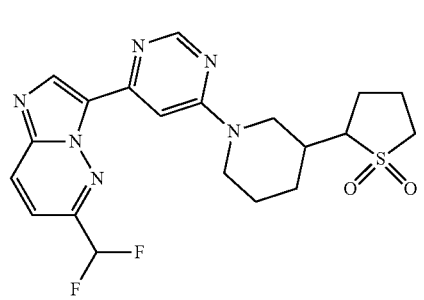 [SMILES: O=S1(=O)CCCC1C1CCCN(c2cc(-c3cnc4ccc(C(F)F)nn34)ncn2)C1] II-563
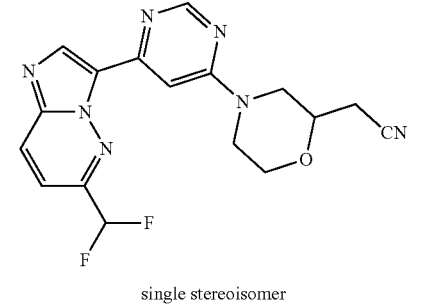 [SMILES: N#CCC1CN(c2cc(-c3cnc4ccc(C(F)F)nn34)ncn2)CCO1] II-564
single stereoisomer
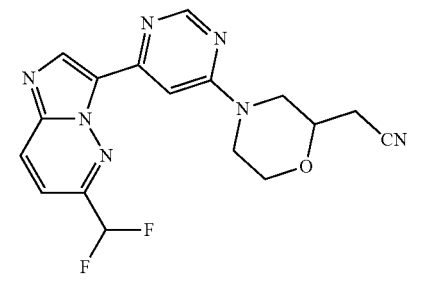 II-565
single stereoisomer TABLE 1-continued
Exemplary compounds of formula II
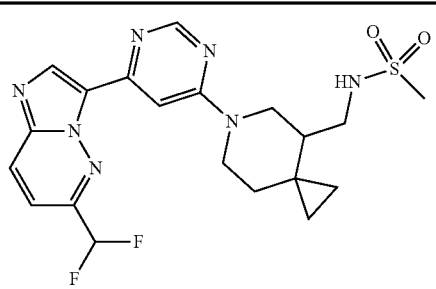 II-566
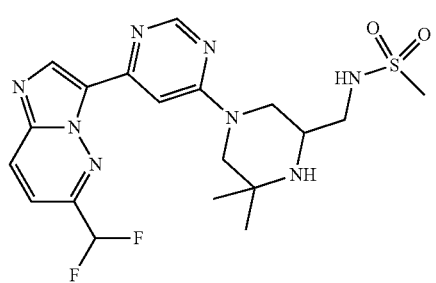 [SMILES: CC1(C)CN(c2cc(-c3cnc4ccc(C(F)F)nn34)ncn2)CC(CNS(C)(=O)=O)N1] II-567
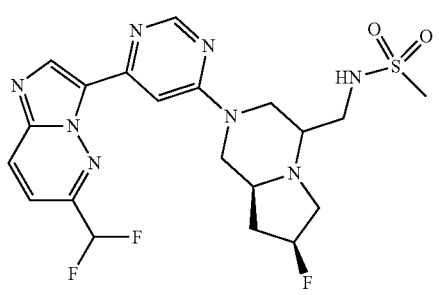 II-568
single stereoisomer
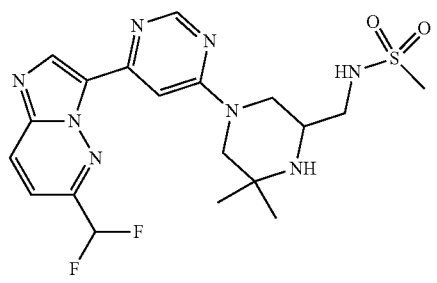 II-569
single stereoisomer
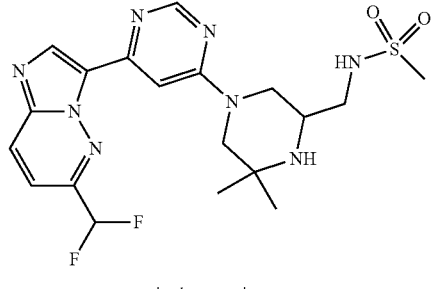 II-570
single stereoisomer
TABLE 1-continued
Exemplary compounds of formula II
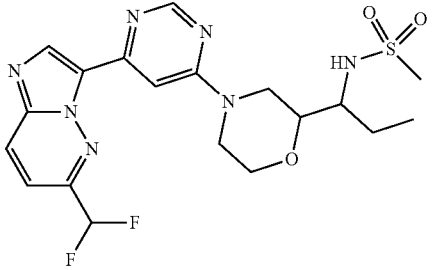 II-571
single diastereomer
(two enantiomers)
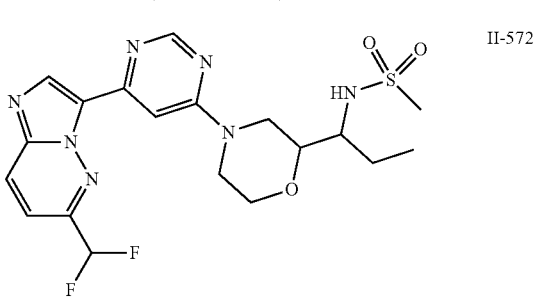 II-572
single diastereomer
(two enantiomers)
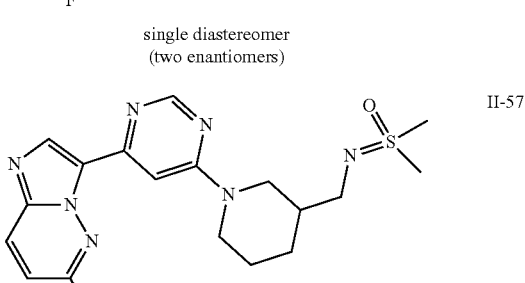 II-573
single stereoisomer
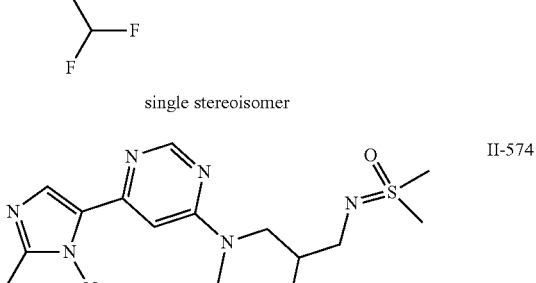 II-574
single stereoisomer
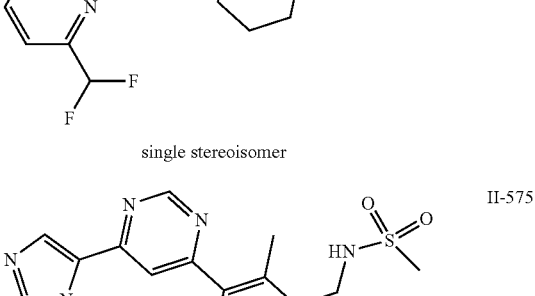 II-575

TABLE 1-continued
Exemplary compounds of formula II
II-576 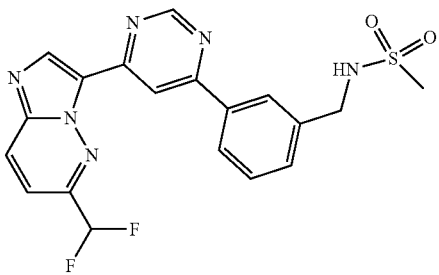 [SMILES: Cc1c(CNS(C)(=O)=O)cccc1-c1cc(-c2cnc3ccc(C(F)F)nn23)ncn1]
II-577 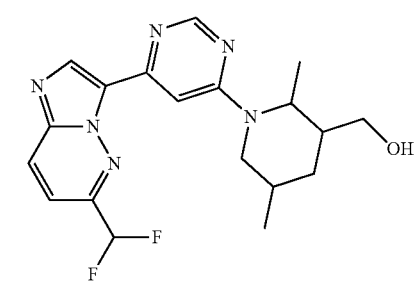 [SMILES: CC1CC(CO)C(C)N(c2cc(-c3cnc4ccc(C(F)F)nn34)ncn2)C1]
II-578 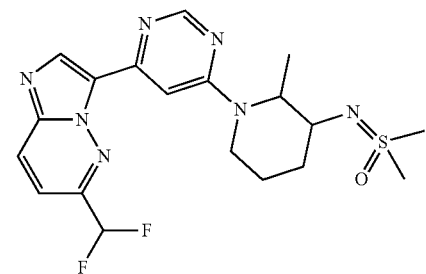 [SMILES: CC1C(N=S(C)(C)=O)CCCN1c1cc(-c2cnc3ccc(C(F)F)nn23)ncn1]
II-579 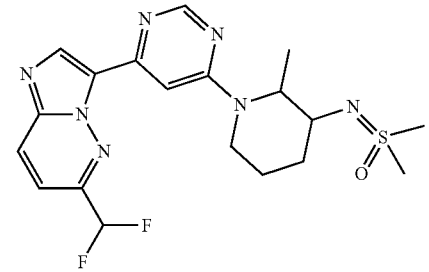 [SMILES: CC1C(N=S(C)(C)=O)CCCN1c1cc(-c2cnc3ccc(C(F)F)nn23)ncn1]
II-580 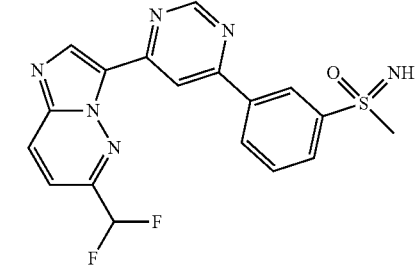 [SMILES: CS(=N)(=O)c1cccc(-c2cc(-c3cnc4ccc(C(F)F)nn34)ncn2)c1]
TABLE 1-continued
Exemplary compounds of formula II
II-581 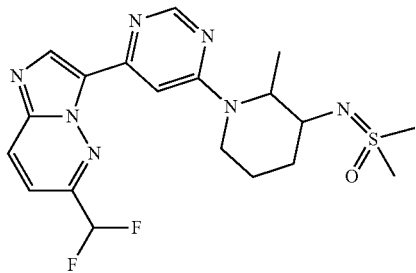
single stereoisomer
II-582 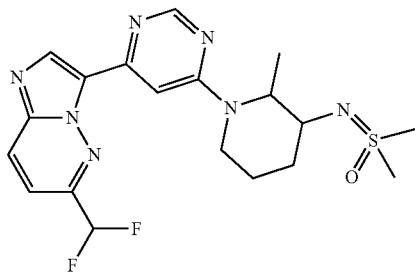
single stereoisomer
II-583 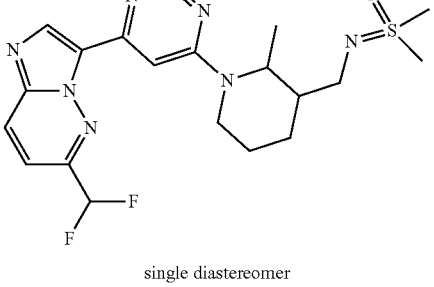
single diastereomer
(two enantiomers)
II-584 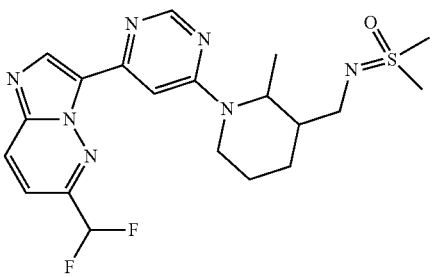
single diastereomer
(two enantiomers)
II-585 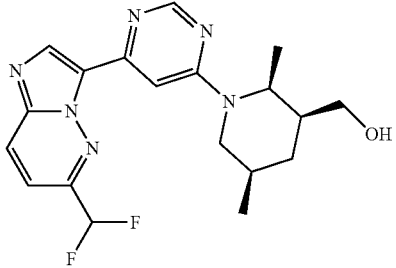 [SMILES: C[C@@H]1C[C@H](CO)[C@H](C)N(c2cc(-c3cnc4ccc(C(F)F)nn34)ncn2)C1]

TABLE 1-continued
Exemplary compounds of formula II
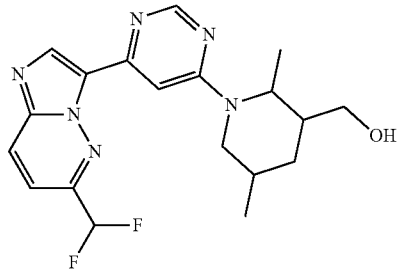
II-586
single stereoisomer
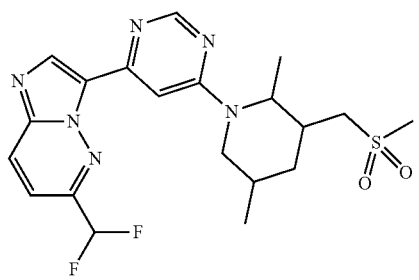
II-587
single diastereomer
(two enantiomers)
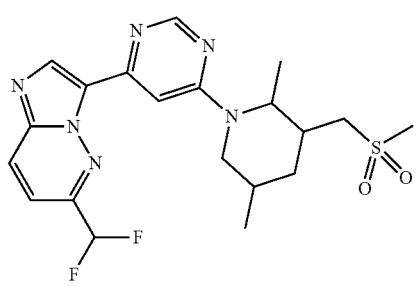
II-588
single diastereomer
(two enantiomers)
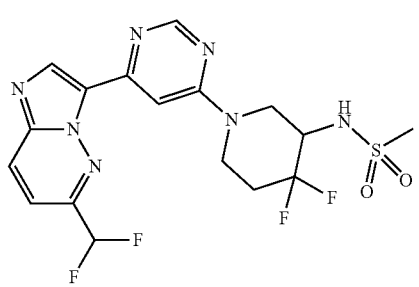 [SMILES: CS(=O)(=O)NC1CN(c2cc(-c3cnc4ccc(C(F)F)nn34)ncn2)CCC1(F)F]
II-589
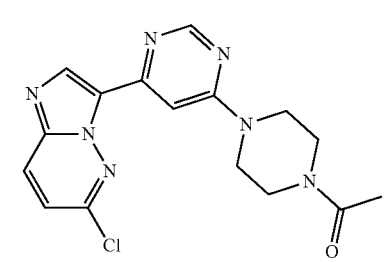 [SMILES: CC(=O)N1CCN(c2cc(-c3cnc4ccc(Cl)nn34)ncn2)CC1]
II-590
TABLE 1-continued
Exemplary compounds of formula II
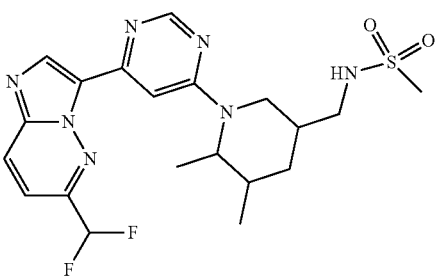
II-591
single stereoisomer
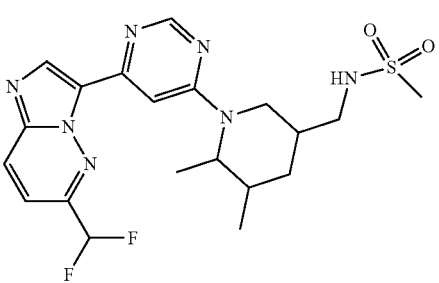
II-592
single stereoisomer
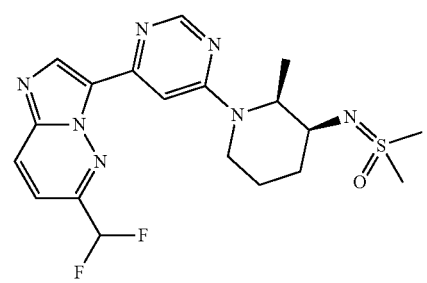 [SMILES: C[C@H]1[C@@H](N=S(C)(C)=O)CCCN1c1cc(-c2cnc3ccc(C(F)F)nn23)ncn1]
II-593
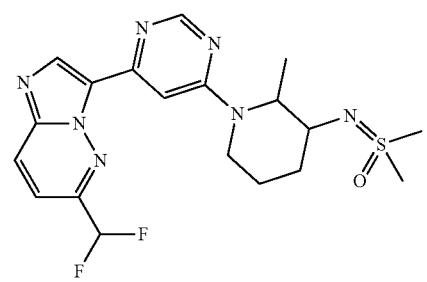
II-594
single stereoisomer
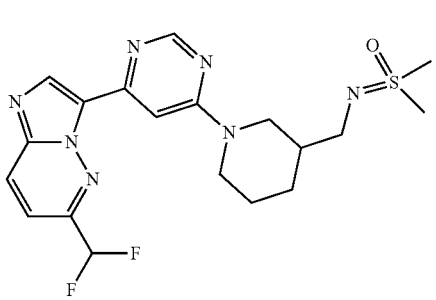 [SMILES: CS(C)(=O)=NCC1CCCN(c2cc(-c3cnc4ccc(C(F)F)nn34)ncn2)C1]
II-595

TABLE 1-continued
Exemplary compounds of formula II
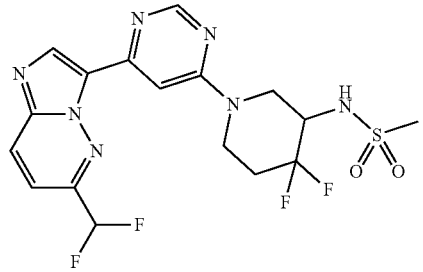
II-596
single stereoisomer
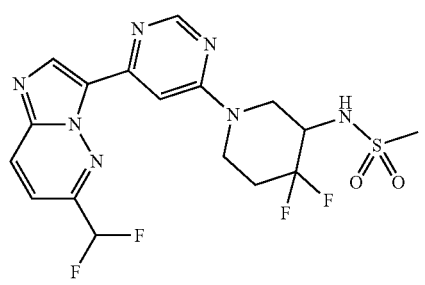
II-597
single stereoisomer
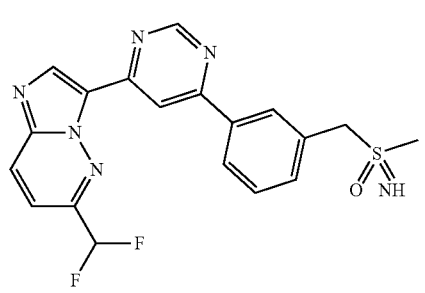 [SMILES: CS(=N)(=O)Cc1cccc(-c2cc(-c3cnc4ccc(C(F)F)nn34)ncn2)c1]
II-598
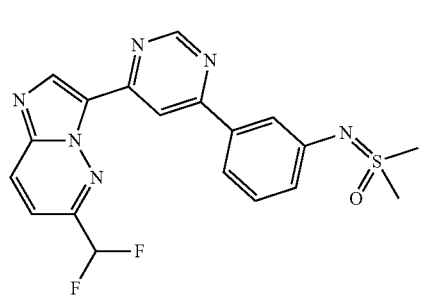 [SMILES: CS(C)(=O)=Nc1cccc(-c2cc(-c3cnc4ccc(C(F)F)nn34)ncn2)c1]
II-599
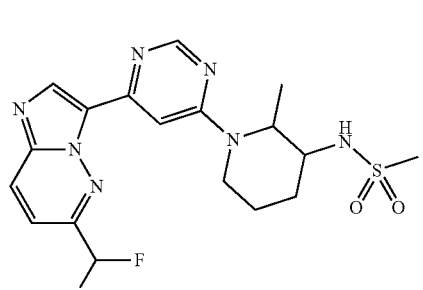
II-600
single stereoisomer
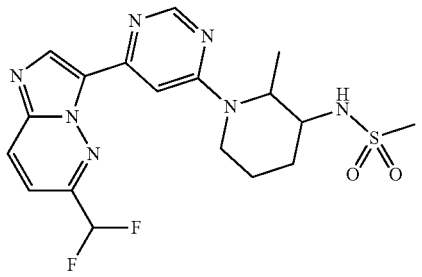
II-601
single stereoisomer
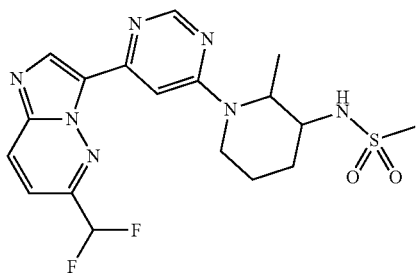
II-602
single stereoisomer
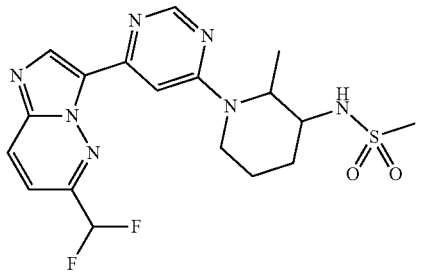
II-603
single stereoisomer
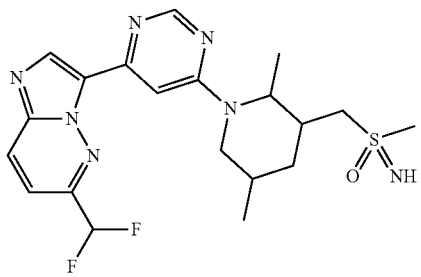
II-604
single stereoisomer
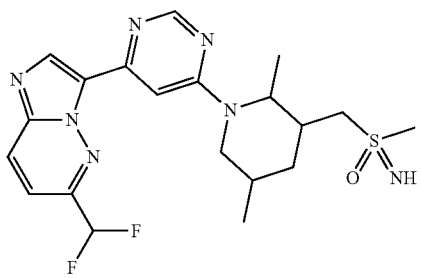
II-605
single stereoisomer TABLE 1-continued
Exemplary compounds of formula II
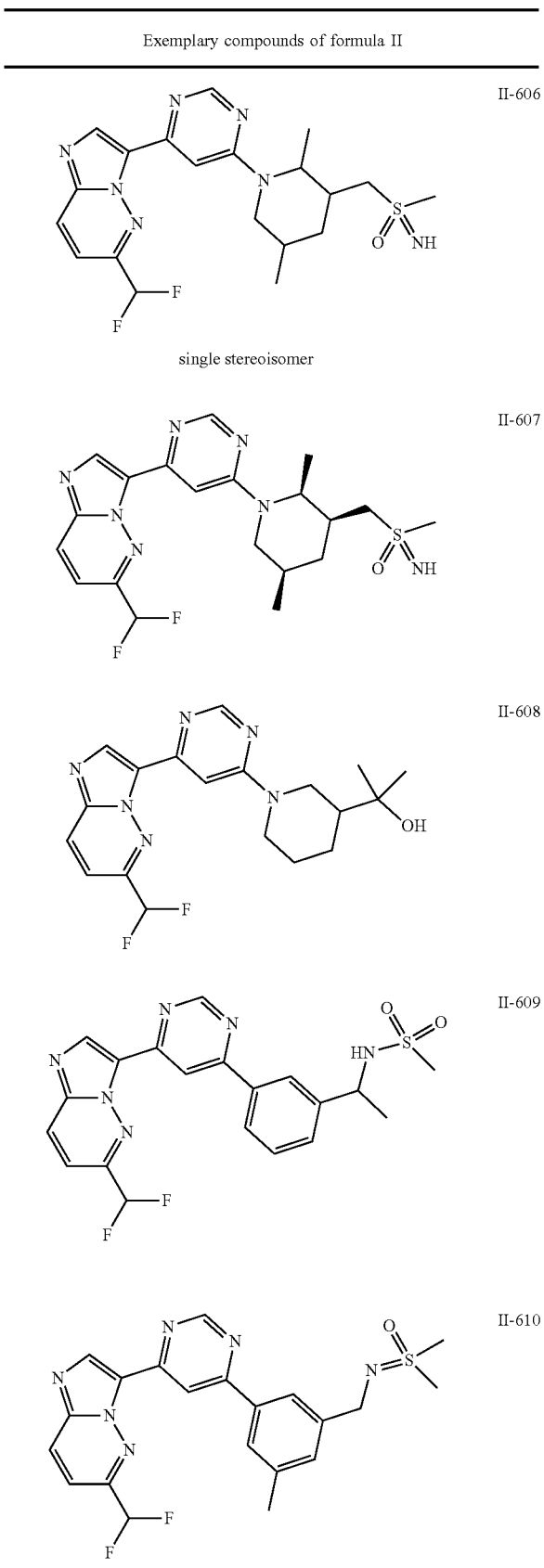
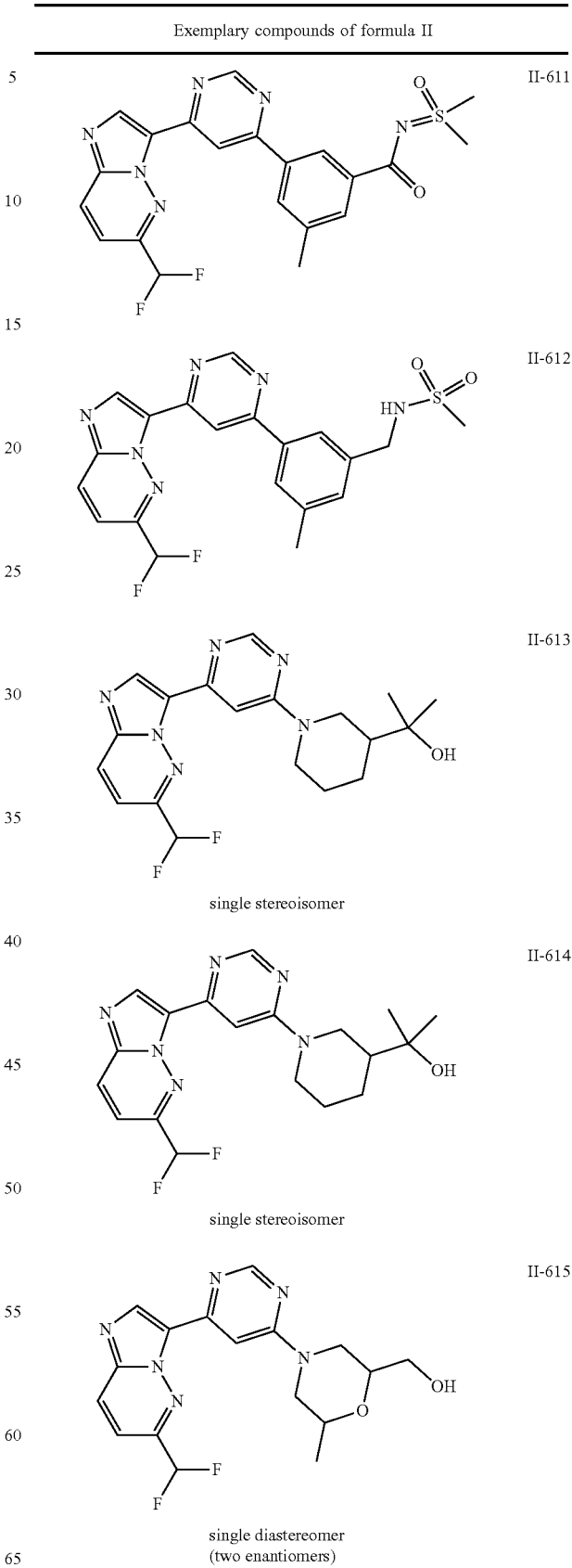

TABLE 1-continued

Exemplary compounds of formula II

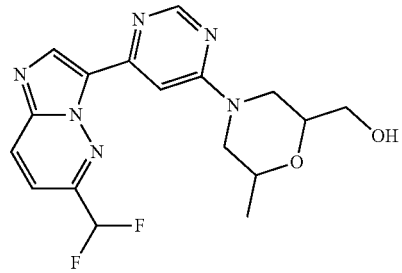
II-616 single diastereomer
(two enantiomers)

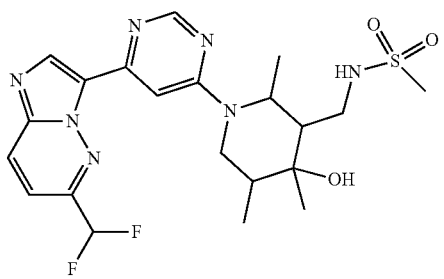
II-617 single stereoisomer

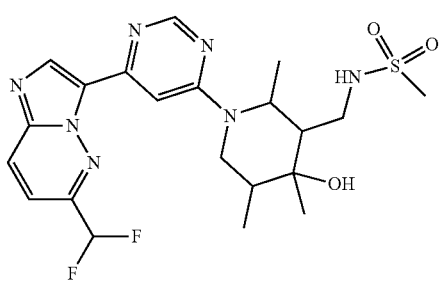
II-618 single stereoisomer

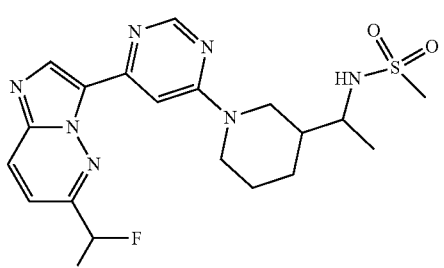
II-619 single stereoisomer
(two enantiomer)

TABLE 1-continued

Exemplary compounds of formula II

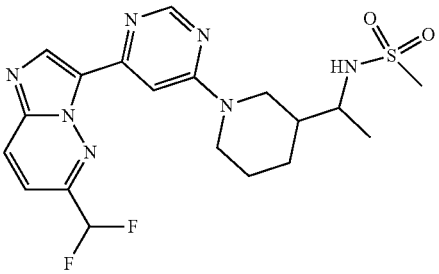 [SMILES: CC(NS(C)(=O)=O)c1cccc(-c2cc(-c3cnc4ccc(C(F)F)nn34)ncn2)c1]
II-620 single stereoisomer
(two enantiomers)

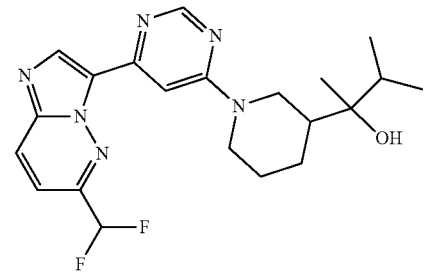
II-621 single stereoisomer

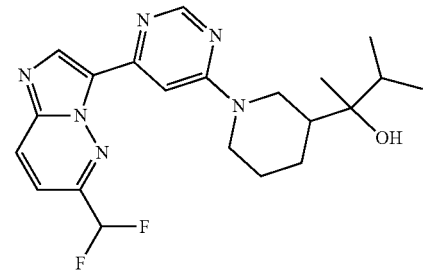
II-622 single stereoisomer

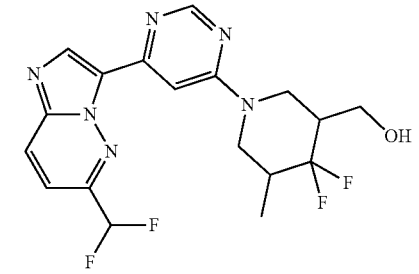
II-623 single stereoisomer

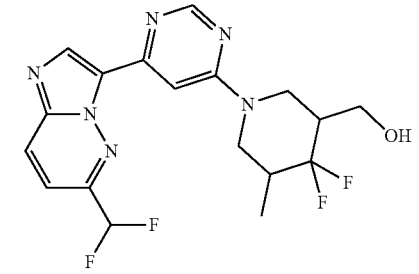
II-624 single stereoisomer

TABLE 1-continued
Exemplary compounds of formula II
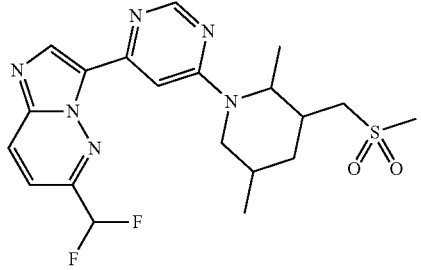
II-625
single stereoisomer
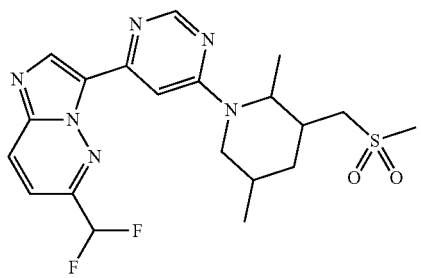
II-626
single stereoisomer
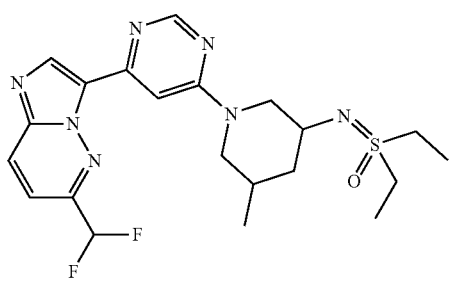 [SMILES: CCS(=O)(CC)=NC1CC(C)CN(c2cc(-c3cnc4ccc(C(F)F)nn34)ncn2)C1]
II-627
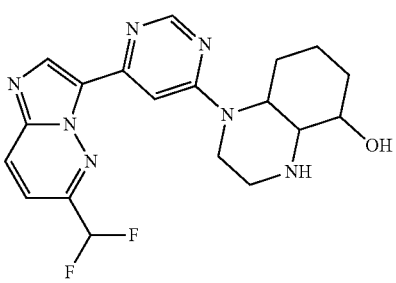 [SMILES: OC1CCCC2C1NCCN2c1cc(-c2cnc3ccc(C(F)F)nn23)ncn1]
II-628
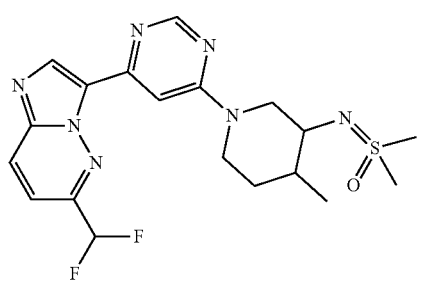 [SMILES: CC1CCN(c2cc(-c3cnc4ccc(C(F)F)nn34)ncn2)CC1N=S(C)(C)=O]
II-629
TABLE 1-continued
Exemplary compounds of formula II
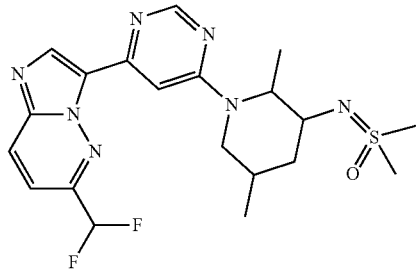
II-630
single stereoisomer
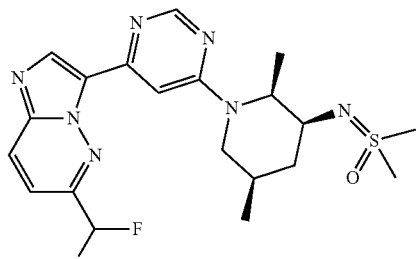
II-631
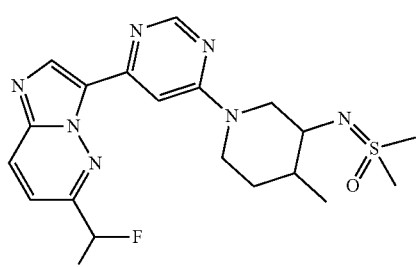
II-632
single stereoisomer
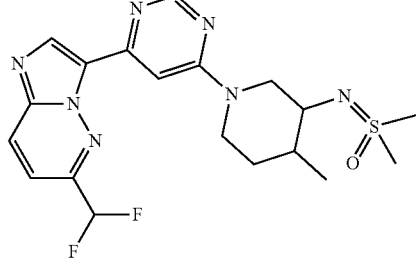
II-633
single stereoisomer
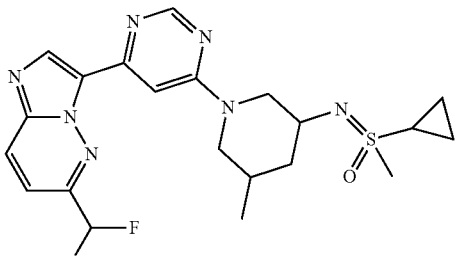
II-634

TABLE 1-continued
Exemplary compounds of formula II
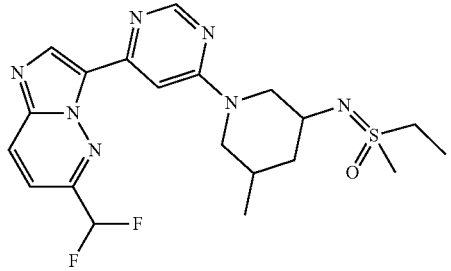
II-635
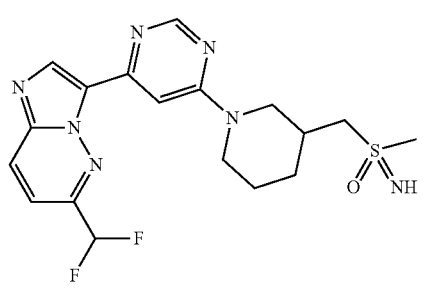
II-636
single stereoisomer
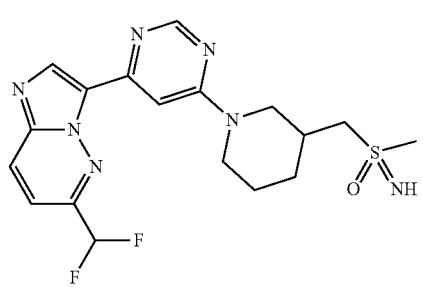
II-637
single stereoisomer
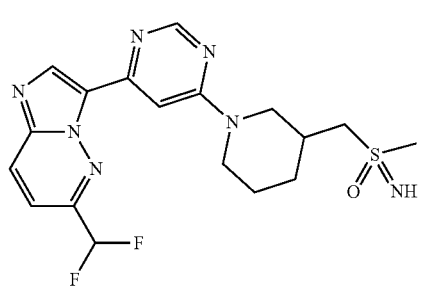
II-638
single stereoisomer
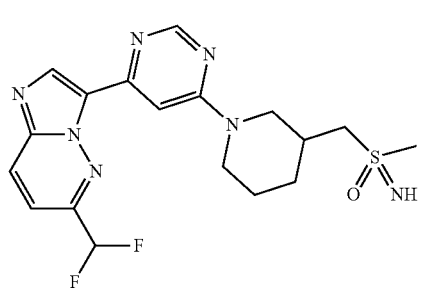
II-639
single stereoisomer
TABLE 1-continued
Exemplary compounds of formula II
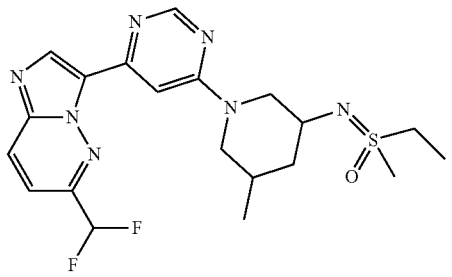
II-640
single stereoisomer
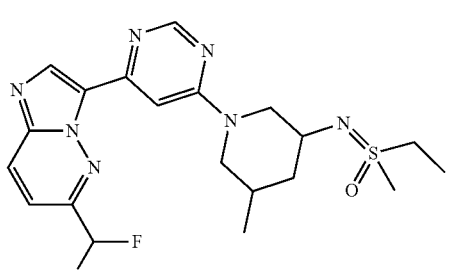
II-641
single stereoisomer
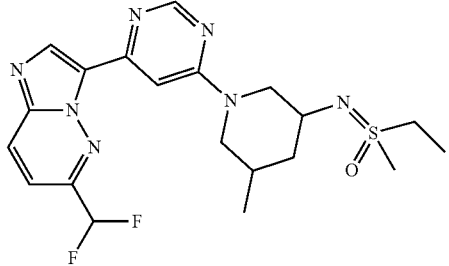
II-642
single stereoisomer
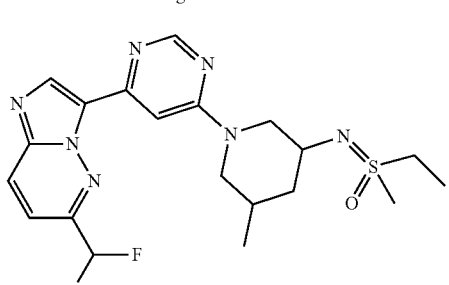
II-643
single stereoisomer
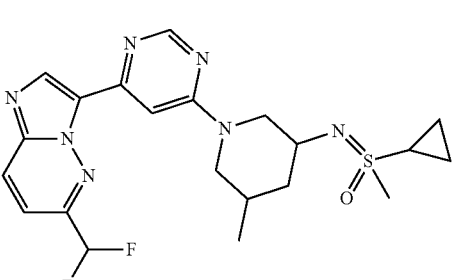
II-644
single stereoisomer TABLE 1-continued
Exemplary compounds of formula II
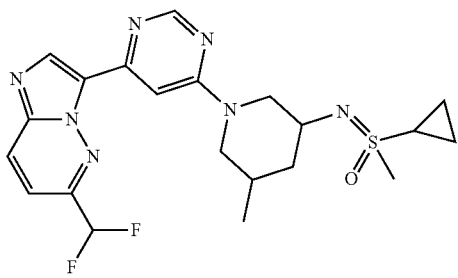 [SMILES: CC1CC(N=S(C)(=O)C2CC2)CN(c2cc(-c3cnc4ccc(C(F)F)nn34)ncn2)C1]
II-645
single stereoisomer
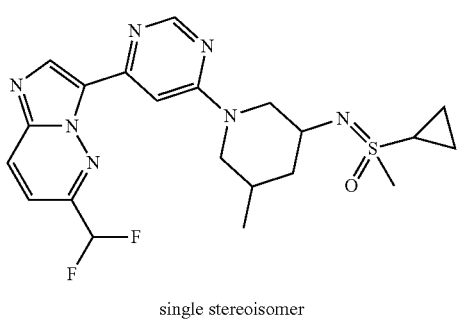 [SMILES: CC1CC(N=S(C)(=O)C2CC2)CN(c2cc(-c3cnc4ccc(C(F)F)nn34)ncn2)C1]
II-646
single stereoisomer
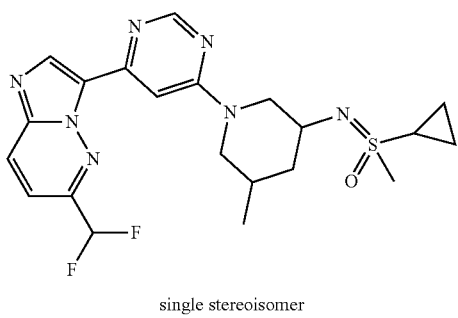 [SMILES: CC1CC(N=S(C)(=O)C2CC2)CN(c2cc(-c3cnc4ccc(C(F)F)nn34)ncn2)C1]
II-647
single stereoisomer
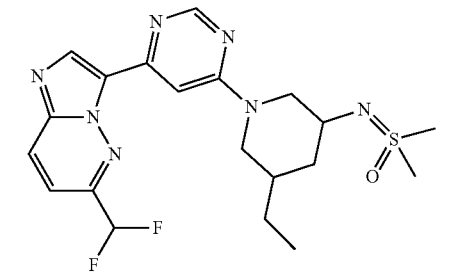 [SMILES: CCC1CC(N=S(C)(C)=O)CN(c2cc(-c3cnc4ccc(C(F)F)nn34)ncn2)C1]
II-648
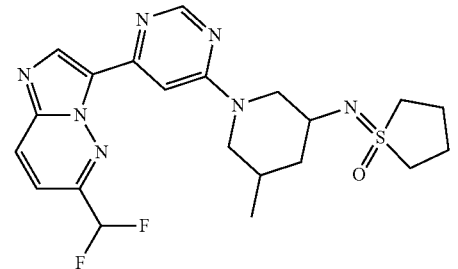 [SMILES: CC1CC(N=S2(=O)CCCC2)CN(c2cc(-c3cnc4ccc(C(F)F)nn34)ncn2)C1]
II-649
TABLE 1-continued
Exemplary compounds of formula II
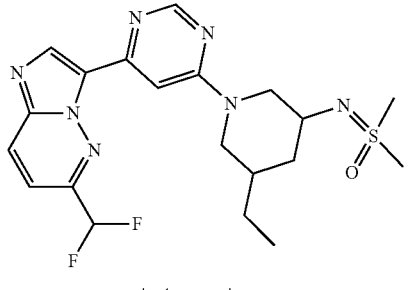
II-650
single stereoisomer
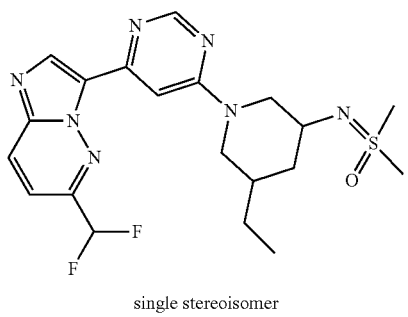 [SMILES: CCC1CC(N=S(C)(C)=O)CN(c2cc(-c3cnc4ccc(C(F)F)nn34)ncn2)C1]
II-651
single stereoisomer
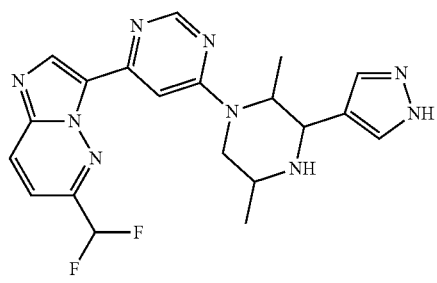
II-652
single stereoisomer
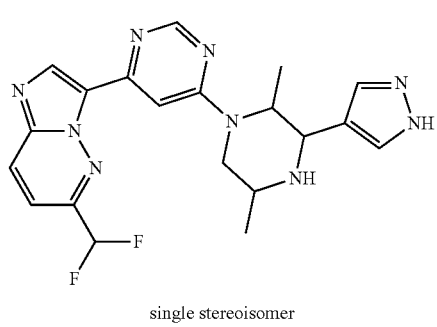 [SMILES: CC1CN(c2cc(-c3cnc4ccc(C(F)F)nn34)ncn2)C(C)C(c2cn[nH]c2)N1]
II-653
single stereoisomer
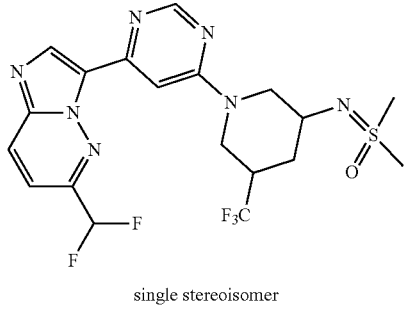 [SMILES: CS(C)(=O)=NC1CC(C(F)(F)F)CN(c2cc(-c3cnc4ccc(C(F)F)nn34)ncn2)C1]
II-654
single stereoisomer TABLE 1-continued
Exemplary compounds of formula II
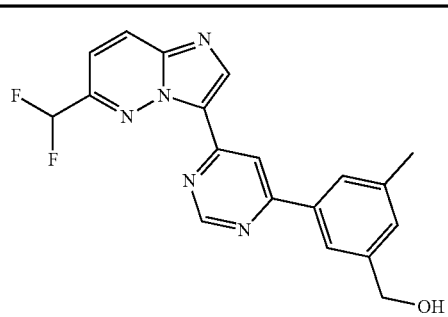
II-655
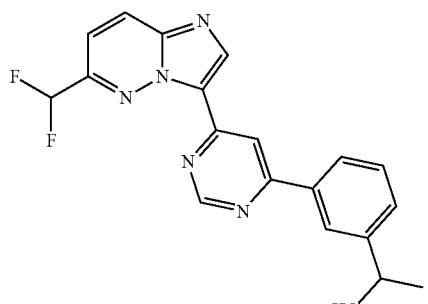
II-656
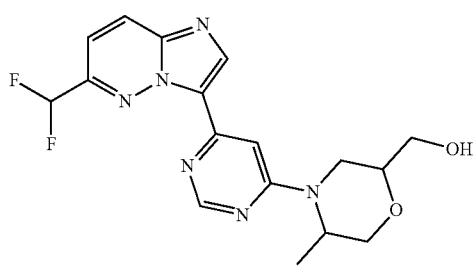 [SMILES: CC1COC(CO)CN1c1cc(-c2cnc3ccc(C(F)F)nn23)ncn1]
II-657
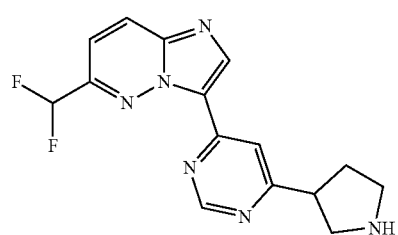 [SMILES: FC(F)c1ccc2ncc(-c3cc(C4CCNC4)ncn3)n2n1]
II-658
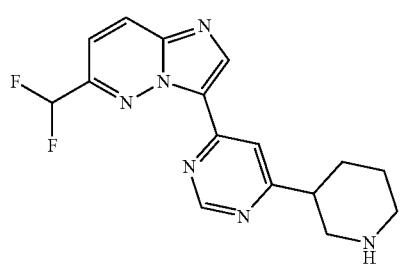 [SMILES: FC(F)c1ccc2ncc(-c3cc(C4CCCNC4)ncn3)n2n1]
II-659
TABLE 1-continued
Exemplary compounds of formula II
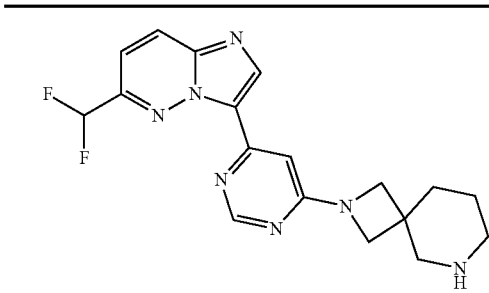
II-660
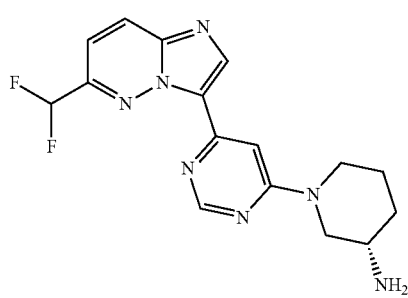 [SMILES: N[C@H]1CCCN(c2cc(-c3cnc4ccc(C(F)F)nn34)ncn2)C1]
II-661
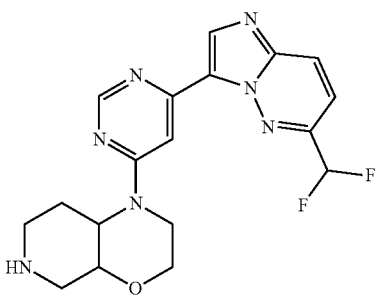 [SMILES: FC(F)c1ccc2ncc(-c3cc(N4CCOC5CNCCC54)ncn3)n2n1]
II-662
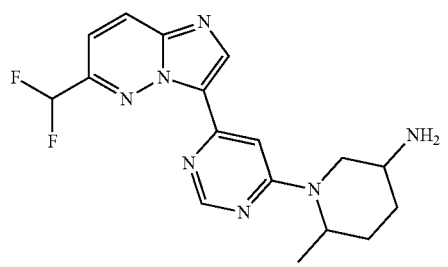 [SMILES: CC1CCC(N)CN1c1cc(-c2cnc3ccc(C(F)F)nn23)ncn1]
II-663
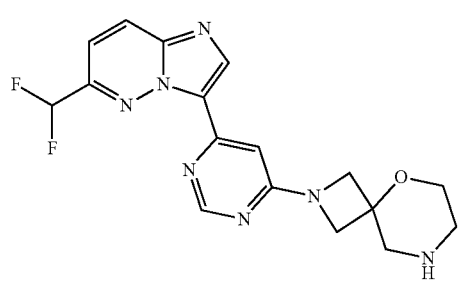 [SMILES: FC(F)c1ccc2ncc(-c3cc(N4CC5(CNCCO5)C4)ncn3)n2n1]
II-664

TABLE 1-continued
Exemplary compounds of formula II
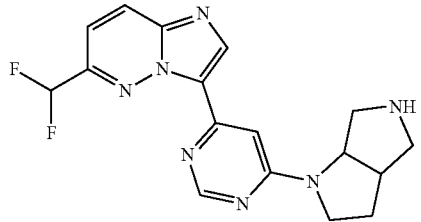 [SMILES: FC(F)c1ccc2ncc(-c3cc(N4CCC5CNCC54)ncn3)n2n1]
II-665
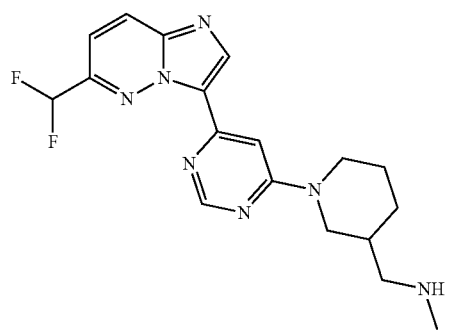 [SMILES: CNCC1CCCN(c2cc(-c3cnc4ccc(C(F)F)nn34)ncn2)C1]
II-666
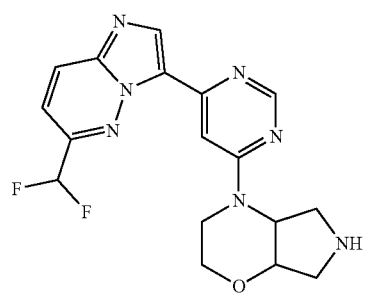 [SMILES: FC(F)c1ccc2ncc(-c3cc(N4CCOC5CNCC54)ncn3)n2n1]
II-667
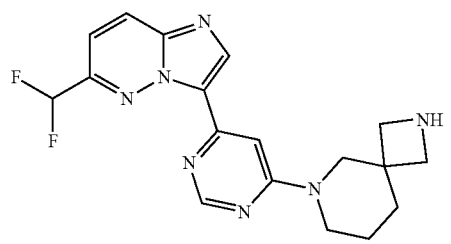 [SMILES: FC(F)c1ccc2ncc(-c3cc(N4CCCC5(CNC5)C4)ncn3)n2n1]
II-668
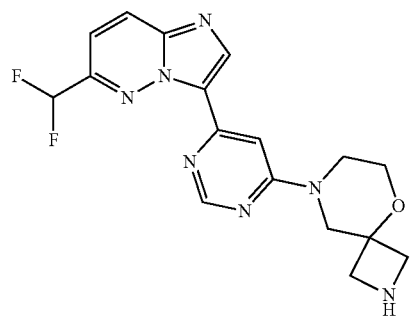 [SMILES: FC(F)c1ccc2ncc(-c3cc(N4CCOC5(CNC5)C4)ncn3)n2n1]
II-669
TABLE 1-continued
Exemplary compounds of formula II
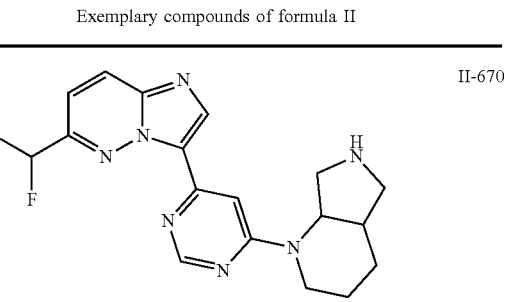
II-670
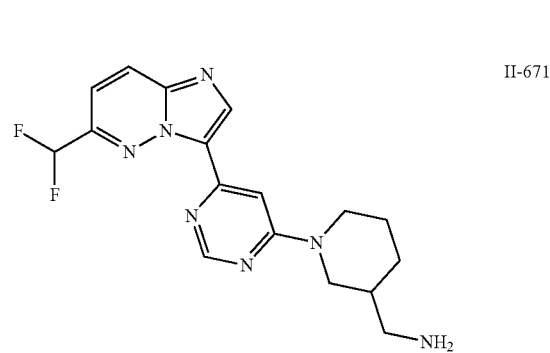
II-671
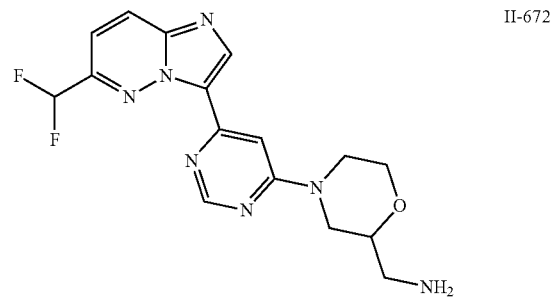
II-672
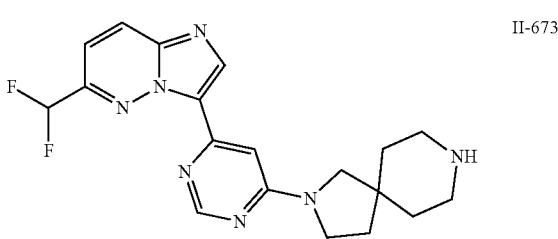
II-673
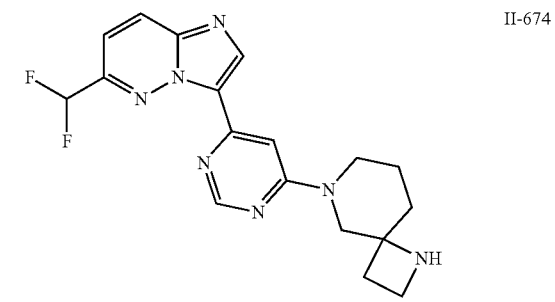
II-674

TABLE 1-continued
Exemplary compounds of formula II
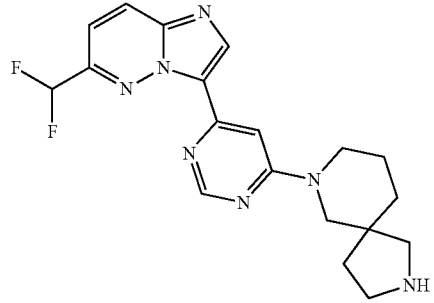 [SMILES: FC(F)c1ccc2ncc(-c3cc(N4CCCC5(CCNC5)C4)ncn3)n2n1] II-675
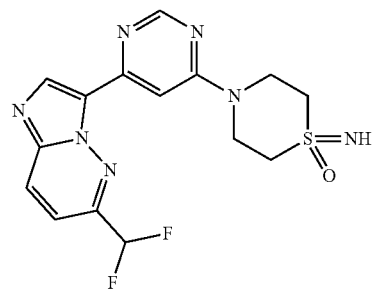 [SMILES: N=S1(=O)CCN(c2cc(-c3cnc4ccc(C(F)F)nn34)ncn2)CC1] II-676
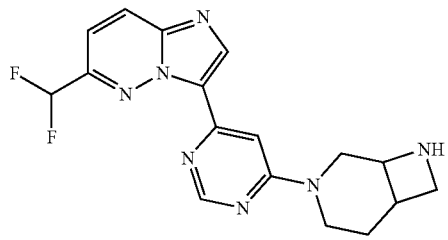 [SMILES: FC(F)c1ccc2ncc(-c3cc(N4CCC5CNC5C4)ncn3)n2n1] II-677
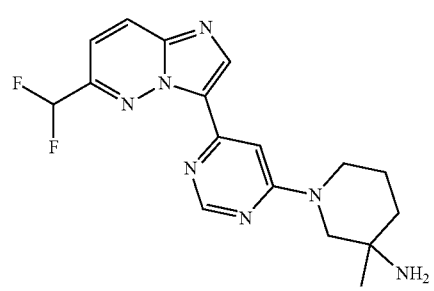 [SMILES: CC1(N)CCCN(c2cc(-c3cnc4ccc(C(F)F)nn34)ncn2)C1] II-678
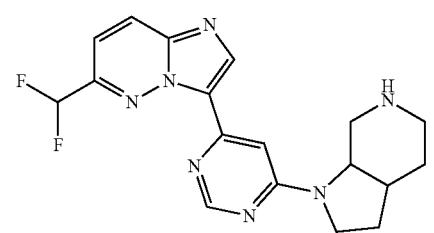 [SMILES: FC(F)c1ccc2ncc(-c3cc(N4CCC5CCNCC54)ncn3)n2n1] II-679
TABLE 1-continued
Exemplary compounds of formula II
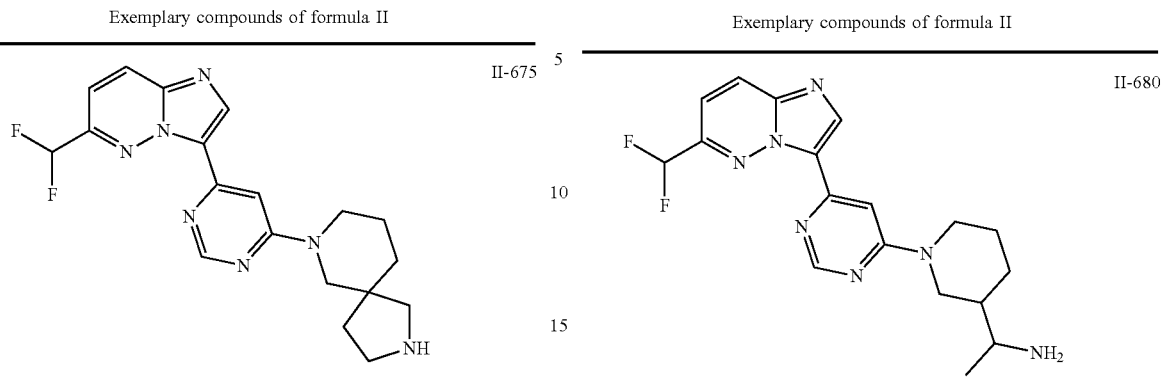 II-680
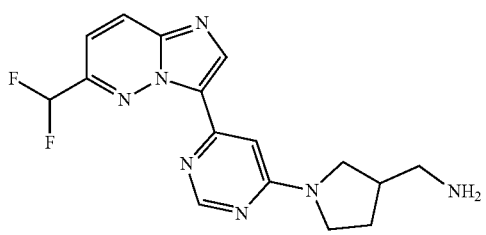 [SMILES: NCC1CCN(c2cc(-c3cnc4ccc(C(F)F)nn34)ncn2)C1] II-681
II-682
II-683
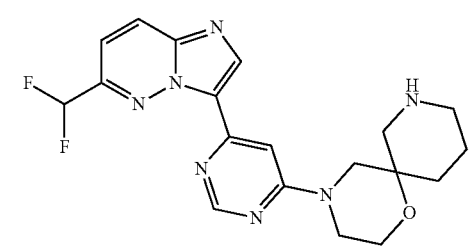 [SMILES: FC(F)c1ccc2ncc(-c3cc(N4CCOC5(CCCNC5)C4)ncn3)n2n1] II-683
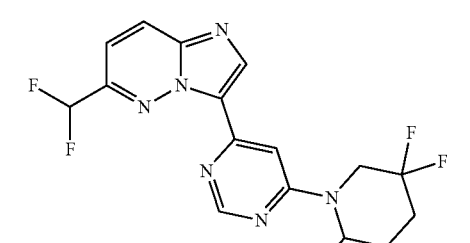 II-684

TABLE 1-continued
Exemplary compounds of formula II
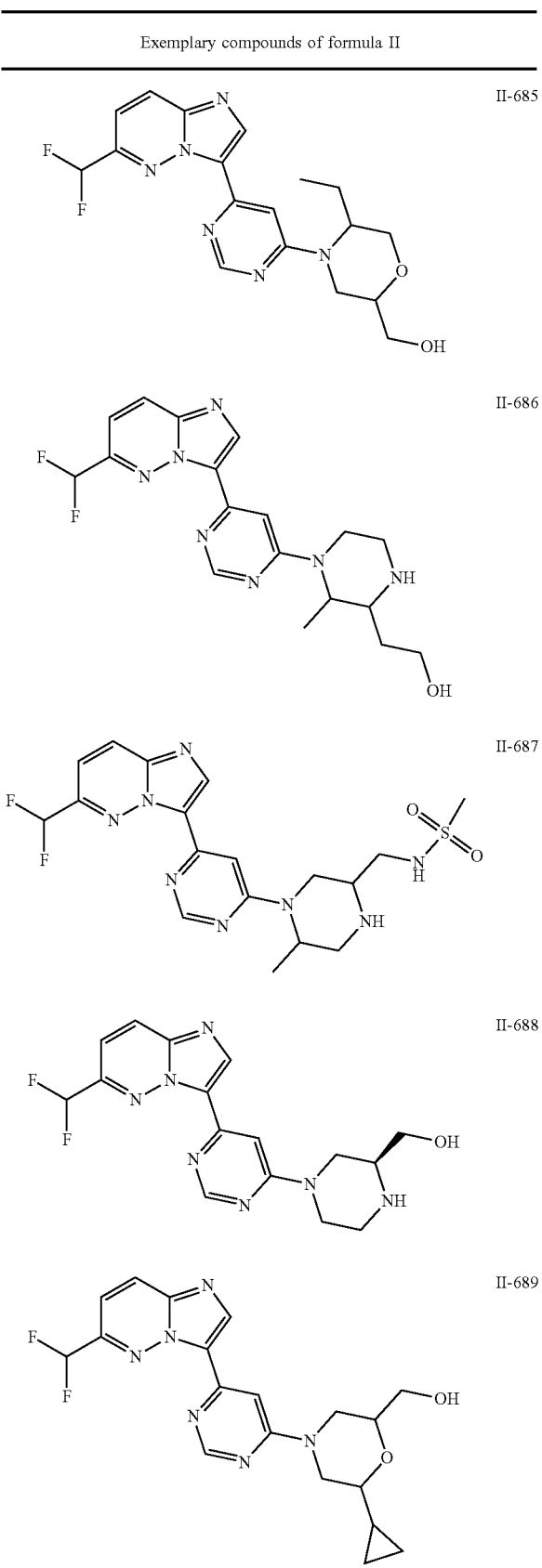
II-685
II-686
II-687
II-688
II-689
TABLE 1-continued
Exemplary compounds of formula II
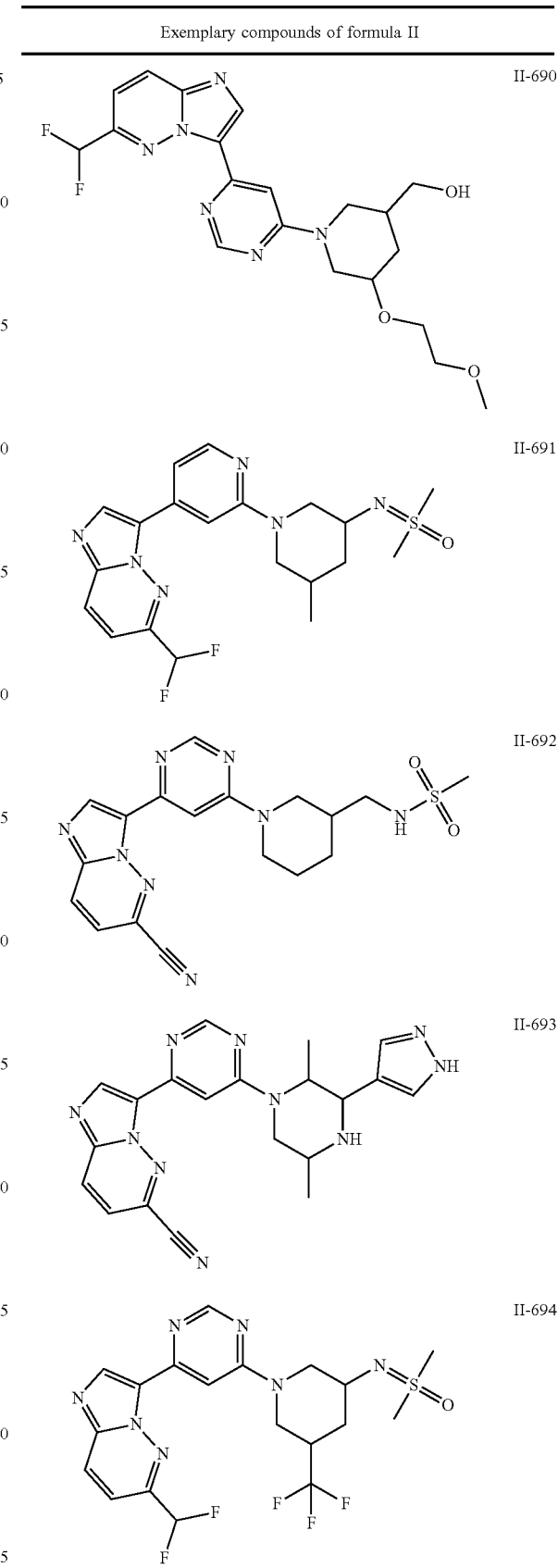
II-690
II-691
II-692
II-693
II-694

TABLE 1-continued
Exemplary compounds of formula II
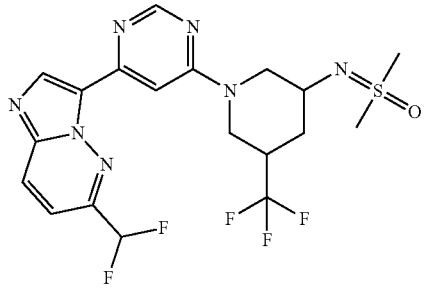 [SMILES: CS(C)(=O)=NC1CC(C(F)(F)F)CN(c2cc(-c3cnc4ccc(C(F)F)nn34)ncn2)C1] II-695
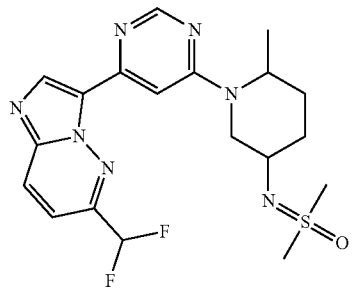 [SMILES: CC1CCC(N=S(C)(C)=O)CN1c1cc(-c2cnc3ccc(C(F)F)nn23)ncn1] II-696
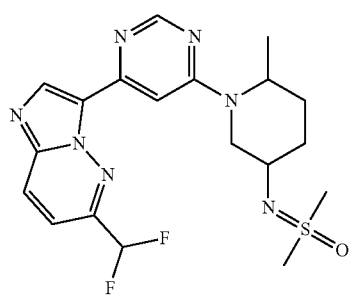 [SMILES: CC1CCC(N=S(C)(C)=O)CN1c1cc(-c2cnc3ccc(C(F)F)nn23)ncn1] II-697
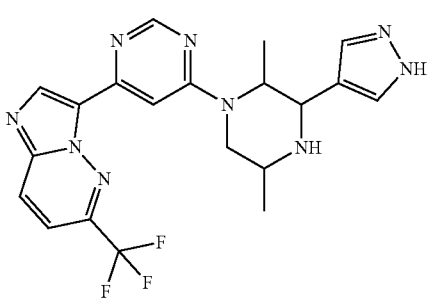 [SMILES: CC1CN(c2cc(-c3cnc4ccc(C(F)(F)F)nn34)ncn2)C(C)C(c2cn[nH]c2)N1] II-698
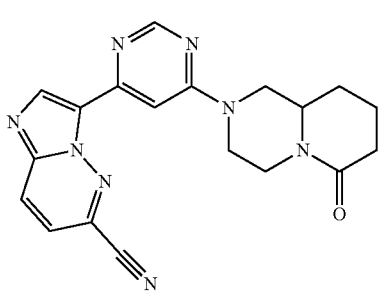 [SMILES: N#Cc1ccc2ncc(-c3cc(N4CCN5C(=O)CCCC5C4)ncn3)n2n1] II-699
TABLE 1-continued
Exemplary compounds of formula II
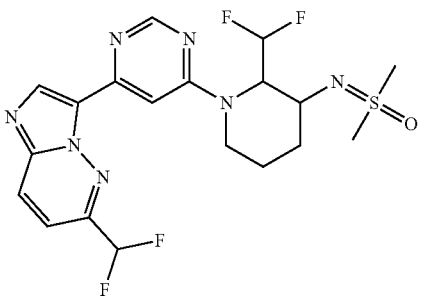 [SMILES: CS(C)(=O)=NC1CCCN(c2cc(-c3cnc4ccc(C(F)F)nn34)ncn2)C1C(F)F] II-700
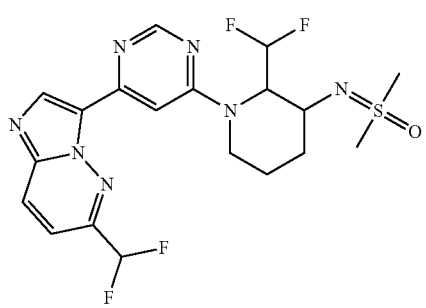 [SMILES: CS(C)(=O)=NC1CCCN(c2cc(-c3cnc4ccc(C(F)F)nn34)ncn2)C1C(F)F] II-701
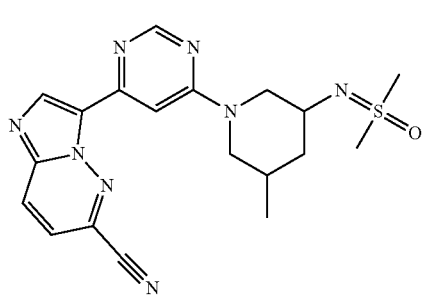 [SMILES: CC1CC(N=S(C)(C)=O)CN(c2cc(-c3cnc4ccc(C#N)nn34)ncn2)C1] II-702
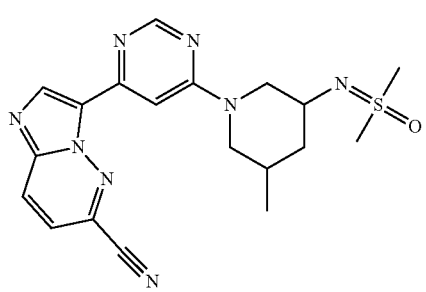 [SMILES: CC1CC(N=S(C)(C)=O)CN(c2cc(-c3cnc4ccc(C#N)nn34)ncn2)C1] II-703
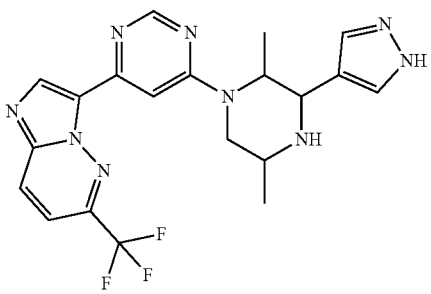 [SMILES: CC1CN(c2cc(-c3cnc4ccc(C(F)(F)F)nn34)ncn2)C(C)C(c2cn[nH]c2)N1] II-704

TABLE 1-continued
Exemplary compounds of formula II
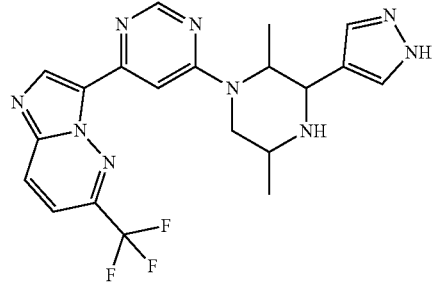 II-705
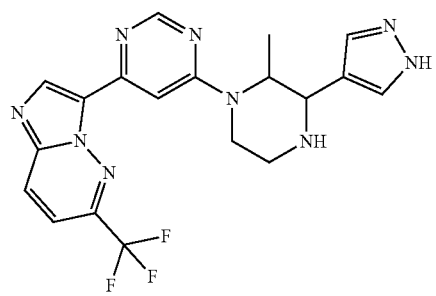 [SMILES: CC1C(c2cn[nH]c2)NCCN1c1cc(-c2cnc3ccc(C(F)(F)F)nn23)ncn1] II-706
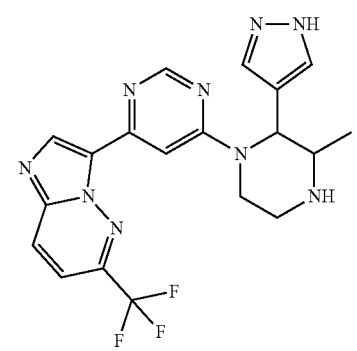 [SMILES: CC1NCCN(c2cc(-c3cnc4ccc(C(F)(F)F)nn34)ncn2)C1c1cn[nH]c1] II-707
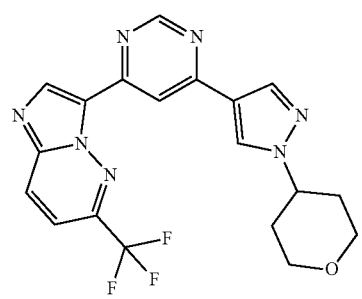 [SMILES: FC(F)(F)c1ccc2ncc(-c3cc(-c4cnn(C5CCOCC5)c4)ncn3)n2n1] II-708
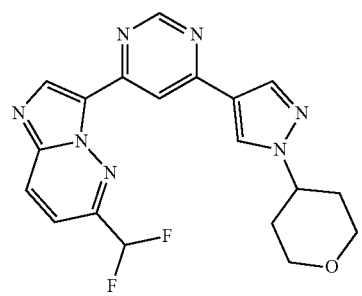 [SMILES: FC(F)c1ccc2ncc(-c3cc(-c4cnn(C5CCOCC5)c4)ncn3)n2n1] II-709
TABLE 1-continued
Exemplary compounds of formula II
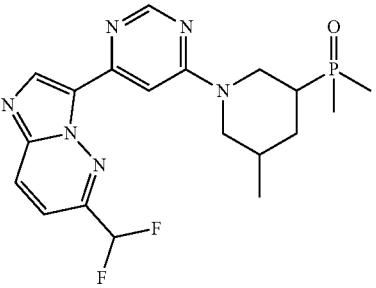 [SMILES: CC1CC(P(C)(C)=O)CN(c2cc(-c3cnc4ccc(C(F)F)nn34)ncn2)C1] II-710
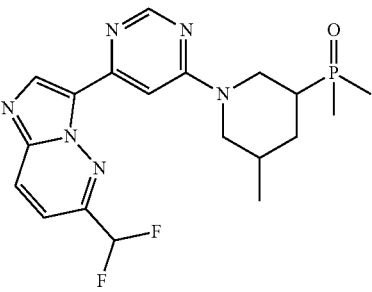 [SMILES: CC1CC(P(C)(C)=O)CN(c2cc(-c3cnc4ccc(C(F)F)nn34)ncn2)C1] II-711
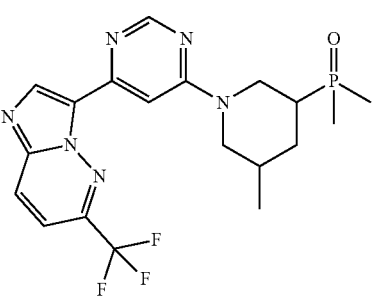 [SMILES: CC1CC(P(C)(C)=O)CN(c2cc(-c3cnc4ccc(C(F)(F)F)nn34)ncn2)C1] II-712
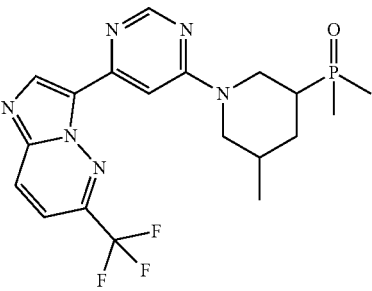 [SMILES: CC1CC(P(C)(C)=O)CN(c2cc(-c3cnc4ccc(C(F)(F)F)nn34)ncn2)C1] II-713
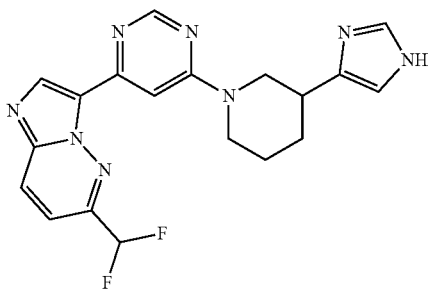 [SMILES: FC(F)c1ccc2ncc(-c3cc(N4CCCC(c5c[nH]cn5)C4)ncn3)n2n1] II-714

TABLE 1-continued
Exemplary compounds of formula II
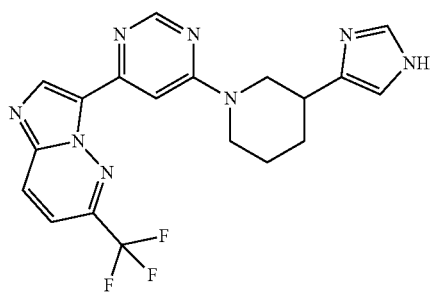 [SMILES: FC(F)(F)c1ccc2ncc(-c3cc(N4CCCC(c5c[nH]cn5)C4)ncn3)n2n1]
II-715
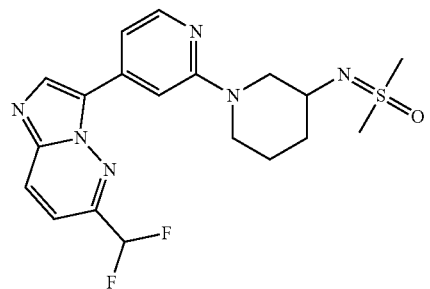 [SMILES: CS(C)(=O)=NC1CCCN(c2cc(-c3cnc4ccc(C(F)F)nn34)ccn2)C1]
II-716
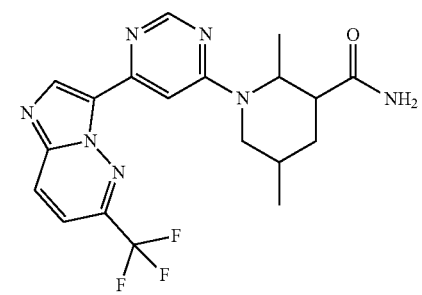 [SMILES: CC1CC(C(N)=O)C(C)N(c2cc(-c3cnc4ccc(C(F)(F)F)nn34)ncn2)C1]
II-717
single stereoisomer
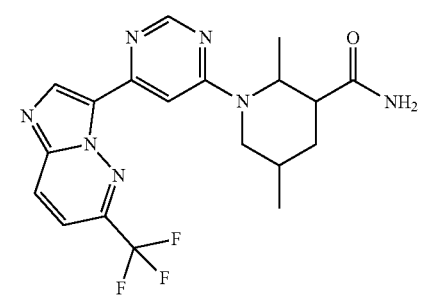
II-718
single stereoisomer
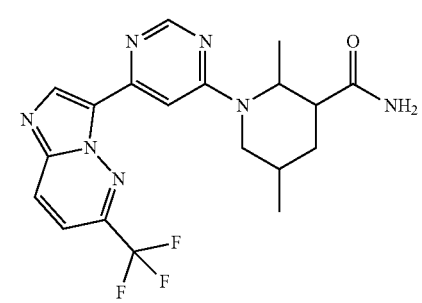 [SMILES: CC1CC(C(N)=O)C(C)N(c2cc(-c3cnc4ccc(C(F)(F)F)nn34)ncn2)C1]
II-719
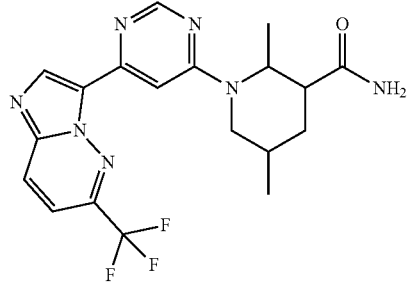
II-720
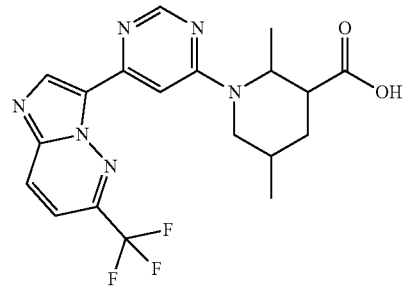 [SMILES: CC1CC(C(=O)O)C(C)N(c2cc(-c3cnc4ccc(C(F)(F)F)nn34)ncn2)C1]
II-721
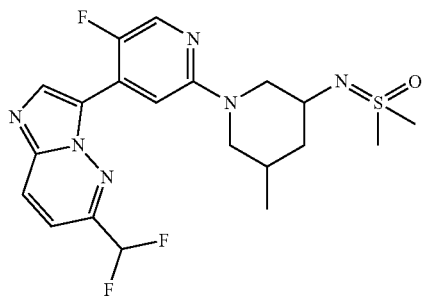
II-722
single stereoisomer
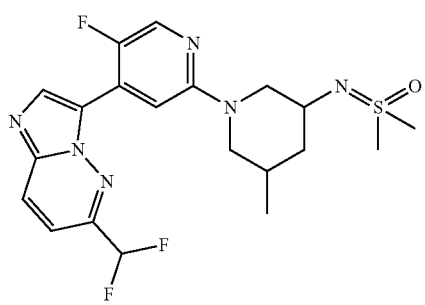
II-723
single stereoisomer
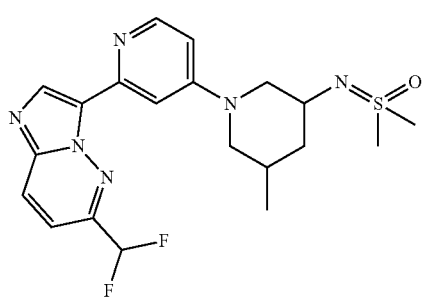
II-724
single stereoisomer TABLE 1-continued
Exemplary compounds of formula II
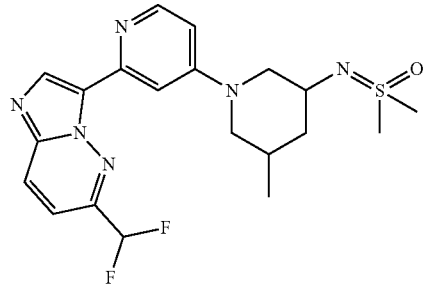
II-725
single stereoisomer
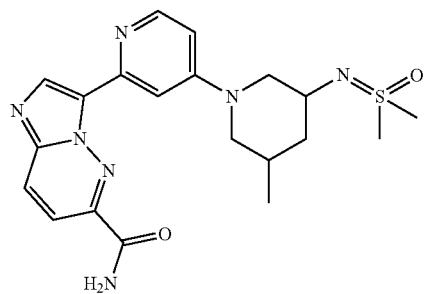 [SMILES: CC1CC(N=S(C)(C)=O)CN(c2ccnc(-c3cnc4ccc(C(N)=O)nn34)c2)C1]
II-726
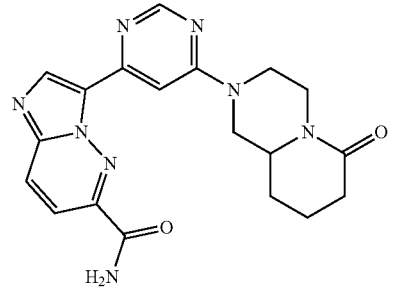 [SMILES: NC(=O)c1ccc2ncc(-c3cc(N4CCN5C(=O)CCCC5C4)ncn3)n2n1]
II-727
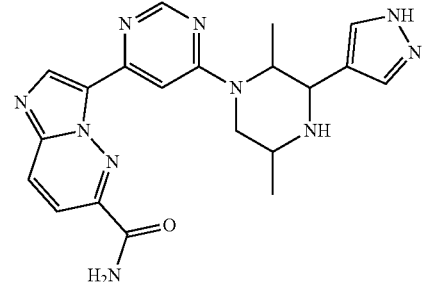 [SMILES: CC1CN(c2cc(-c3cnc4ccc(C(N)=O)nn34)ncn2)C(C)C(c2cn[nH]c2)N1]
II-728
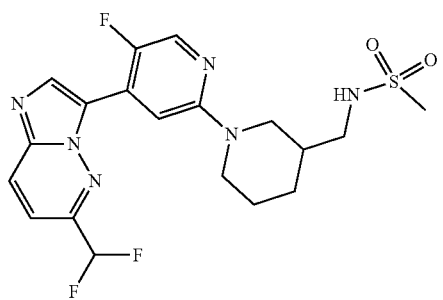 [SMILES: CS(=O)(=O)NCC1CCCN(c2cc(-c3cnc4ccc(C(F)F)nn34)c(F)cn2)C1]
II-729
TABLE 1-continued
Exemplary compounds of formula II
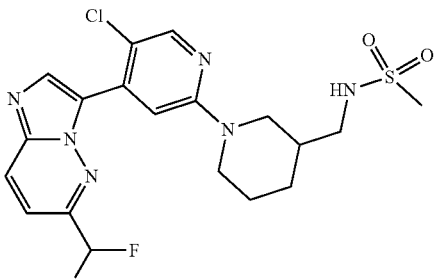
II-730
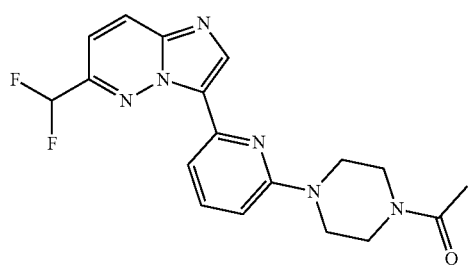 [SMILES: CC(=O)N1CCN(c2cccc(-c3cnc4ccc(C(F)F)nn34)n2)CC1]
II-731
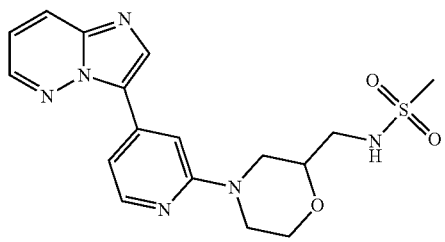 [SMILES: CS(=O)(=O)NCC1CN(c2cc(-c3cnc4cccnn34)ccn2)CCO1]
II-732
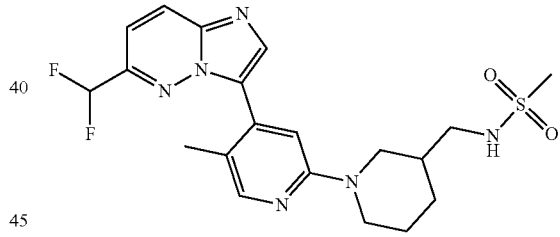
II-733
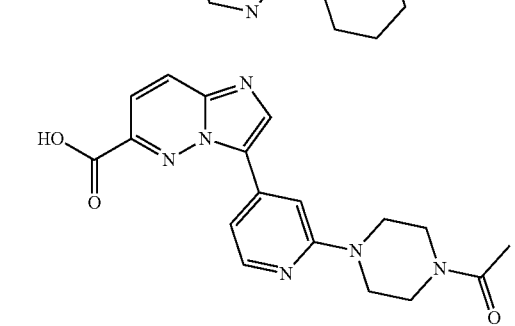
II-734
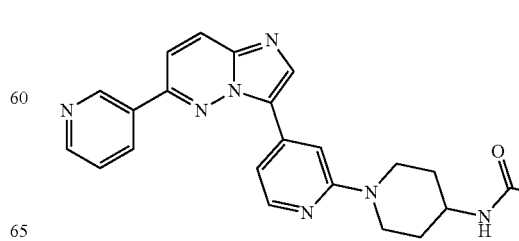
II-735

TABLE 1-continued
Exemplary compounds of formula II
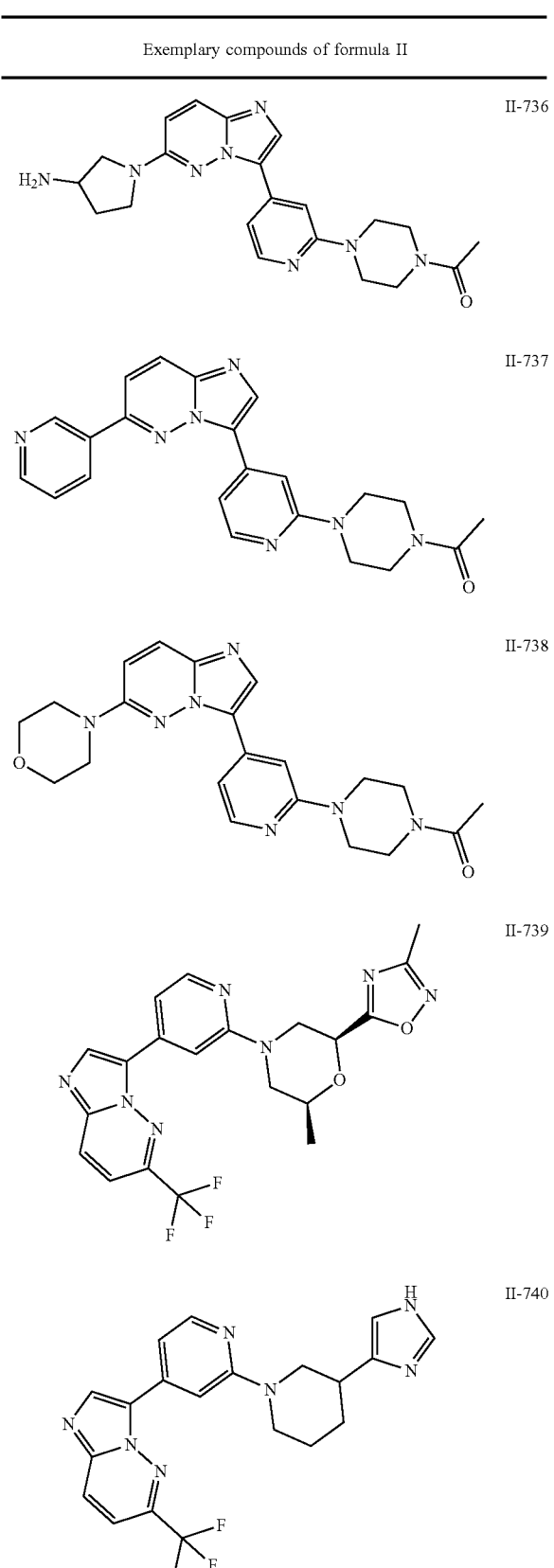
II-736
II-737
II-738
II-739
II-740
TABLE 1-continued
Exemplary compounds of formula II
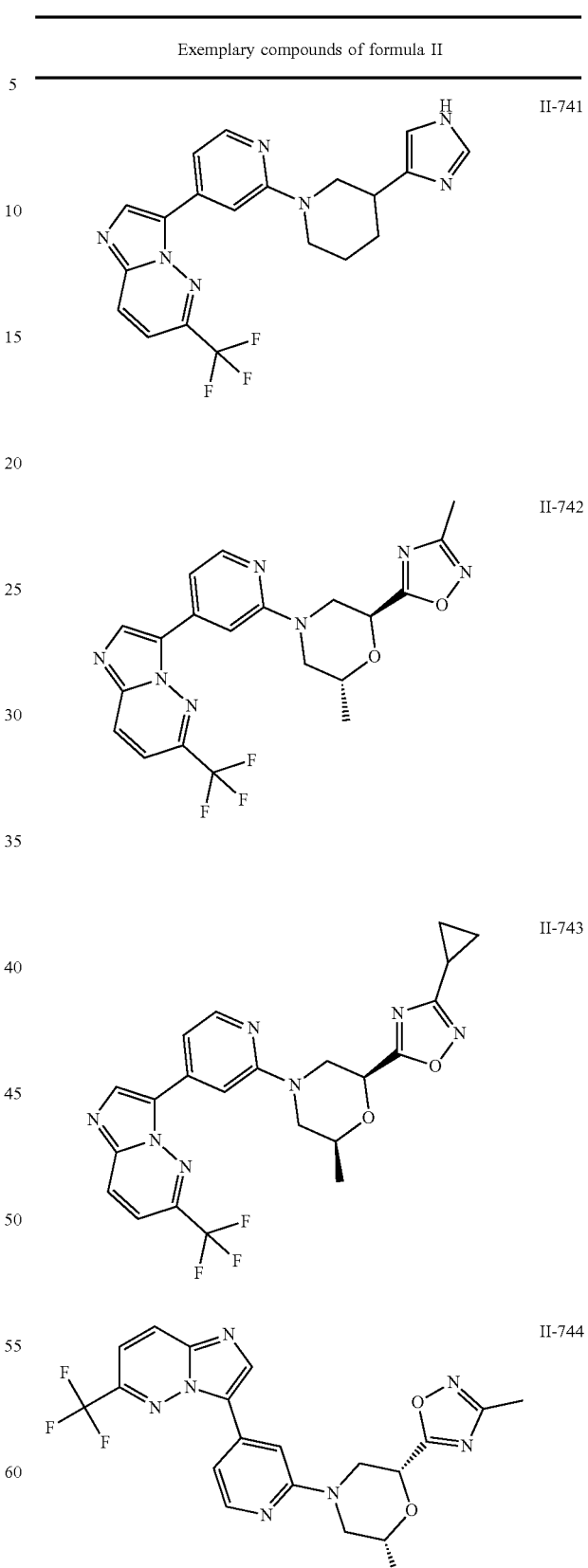
II-741
II-742
II-743
II-744

TABLE 1-continued
Exemplary compounds of formula II
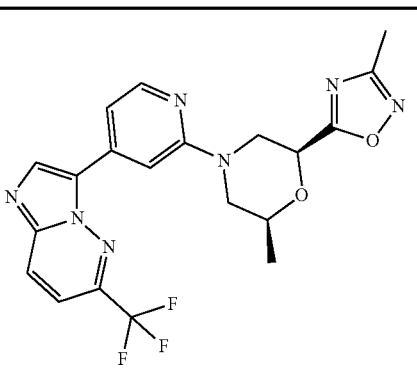 II-745
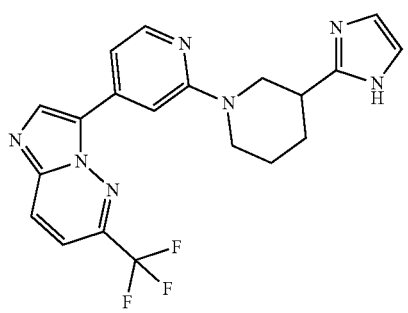 [SMILES: FC(F)(F)c1ccc2ncc(-c3ccnc(N4CCCC(c5ncc[nH]5)C4)c3)n2n1] II-746
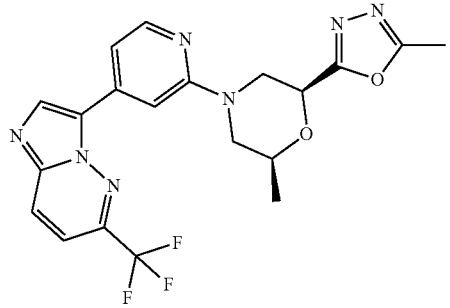 [SMILES: Cc1nnc([C@@H]2CN(c3cc(-c4cnc5ccc(C(F)(F)F)nn45)ccn3)C[C@H](C)O2)o1] II-747
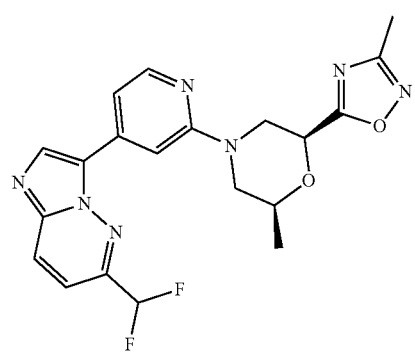 [SMILES: Cc1noc([C@@H]2CN(c3cc(-c4cnc5ccc(C(F)F)nn45)ccn3)C[C@H](C)O2)n1] II-748
TABLE 1-continued
Exemplary compounds of formula II
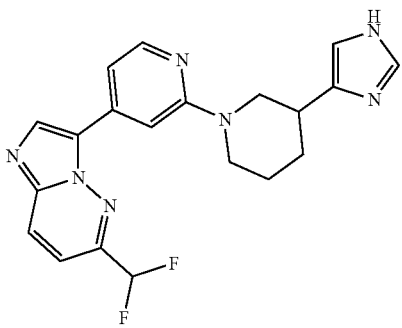 [SMILES: FC(F)c1ccc2ncc(-c3ccnc(N4CCCC(c5c[nH]cn5)C4)c3)n2n1] II-749
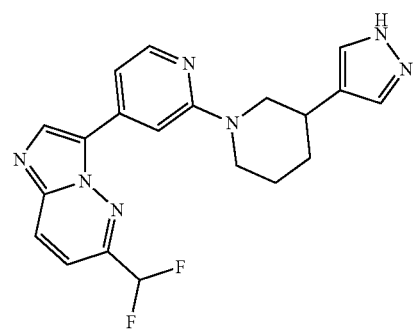 [SMILES: FC(F)c1ccc2ncc(-c3ccnc(N4CCCC(c5cn[nH]c5)C4)c3)n2n1] II-750
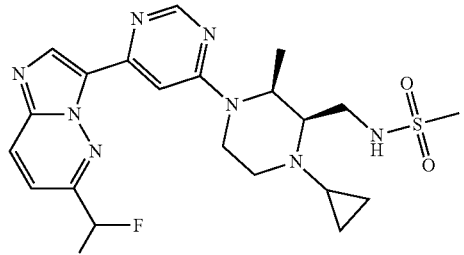 II-752
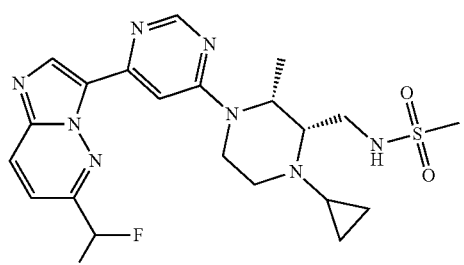 II-753
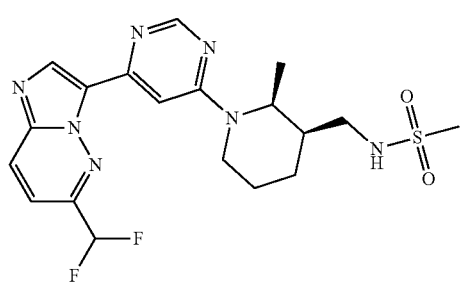 [SMILES: C[C@H]1[C@@H](CNS(C)(=O)=O)CCCN1c1cc(-c2cnc3ccc(C(F)F)nn23)ncn1] II-754

TABLE 1-continued
Exemplary compounds of formula II
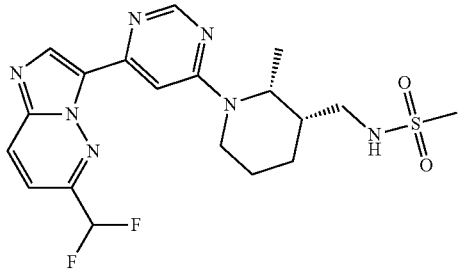 [SMILES: C[C@@H]1[C@H](CNS(C)(=O)=O)CCCN1c1cc(-c2cnc3ccc(C(F)F)nn23)ncn1] II-755
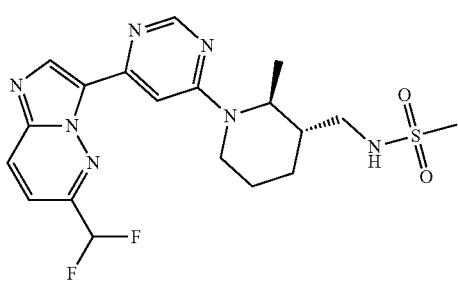 [SMILES: C[C@H]1[C@H](CNS(C)(=O)=O)CCCN1c1cc(-c2cnc3ccc(C(F)F)nn23)ncn1] II-756
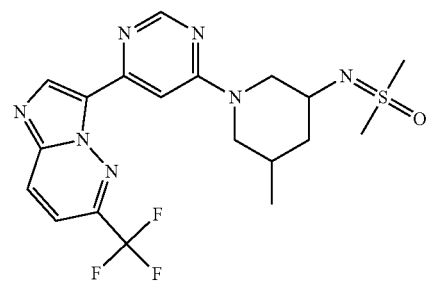 [SMILES: CC1CC(N=S(C)(C)=O)CN(c2cc(-c3cnc4ccc(C(F)(F)F)nn34)ncn2)C1] II-757
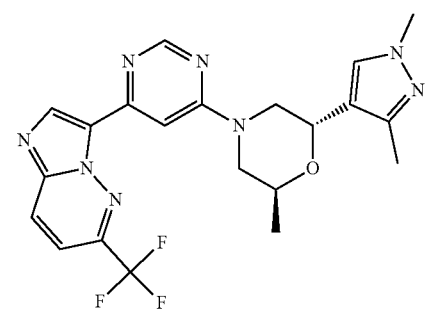 [SMILES: Cc1nn(C)cc1[C@H]1CN(c2cc(-c3cnc4ccc(C(F)(F)F)nn34)ncn2)C[C@H](C)O1] II-758
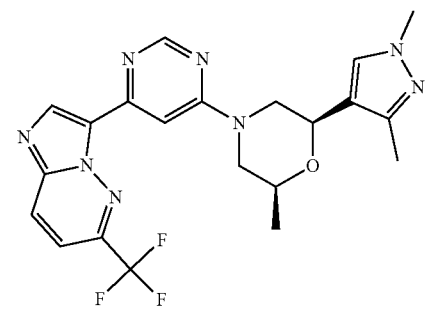 [SMILES: Cc1nn(C)cc1[C@@H]1CN(c2cc(-c3cnc4ccc(C(F)(F)F)nn34)ncn2)C[C@H](C)O1] II-759
TABLE 1-continued
Exemplary compounds of formula II
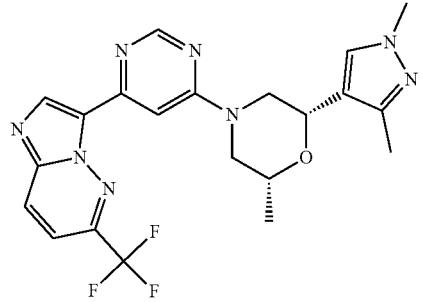 [SMILES: Cc1nn(C)cc1[C@H]1CN(c2cc(-c3cnc4ccc(C(F)(F)F)nn34)ncn2)C[C@@H](C)O1] II-760
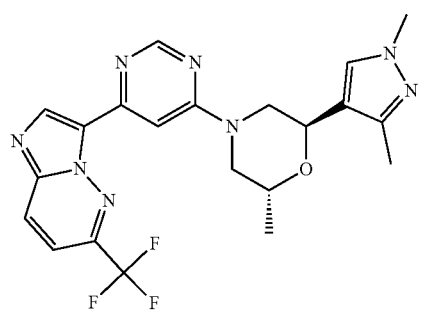 [SMILES: Cc1nn(C)cc1[C@@H]1CN(c2cc(-c3cnc4ccc(C(F)(F)F)nn34)ncn2)C[C@@H](C)O1] II-761
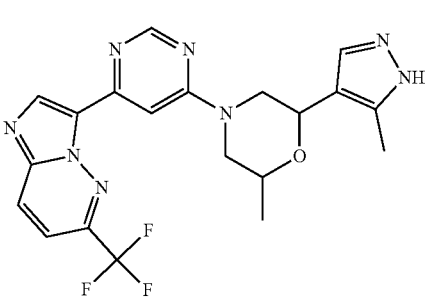 [SMILES: Cc1[nH]ncc1C1CN(c2cc(-c3cnc4ccc(C(F)(F)F)nn34)ncn2)CC(C)O1] II-762
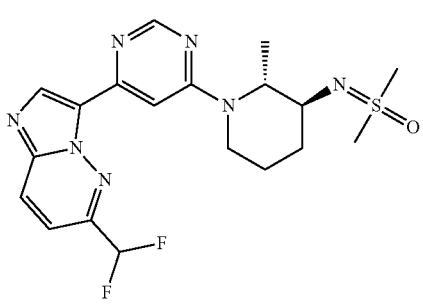 [SMILES: C[C@@H]1[C@@H](N=S(C)(C)=O)CCCN1c1cc(-c2cnc3ccc(C(F)F)nn23)ncn1] II-763
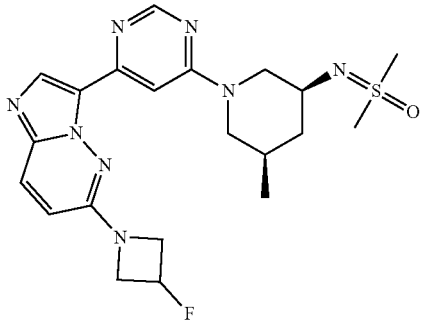 [SMILES: C[C@@H]1C[C@H](N=S(C)(C)=O)CN(c2cc(-c3cnc4ccc(N5CC(F)C5)nn34)ncn2)C1] II-764

TABLE 1-continued
Exemplary compounds of formula II
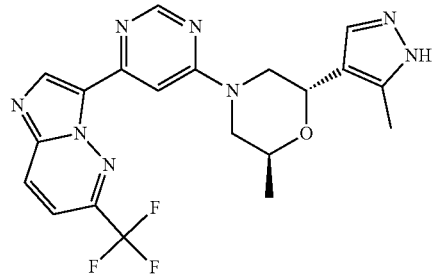 [SMILES: Cc1[nH]ncc1[C@H]1CN(c2cc(-c3cnc4ccc(C(F)(F)F)nn34)ncn2)C[C@H](C)O1] II-765
 II-766
 II-767
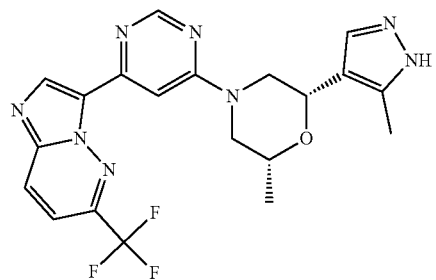 [SMILES: Cc1[nH]ncc1[C@H]1CN(c2cc(-c3cnc4ccc(C(F)(F)F)nn34)ncn2)C[C@@H](C)O1] II-768
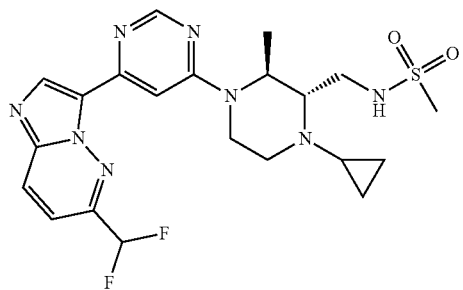 [SMILES: C[C@H]1[C@H](CNS(C)(=O)=O)N(C2CC2)CCN1c1cc(-c2cnc3ccc(C(F)F)nn23)ncn1] II-769
TABLE 1-continued
Exemplary compounds of formula II
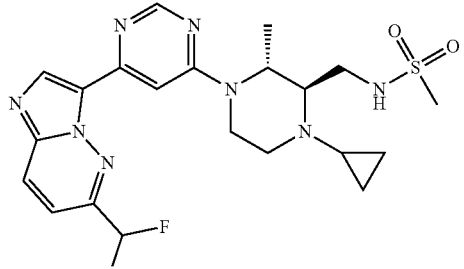 II-770
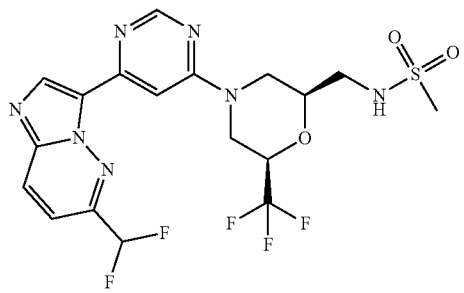 [SMILES: CS(=O)(=O)NC[C@@H]1CN(c2cc(-c3cnc4ccc(C(F)F)nn34)ncn2)C[C@H](C(F)(F)F)O1] II-771
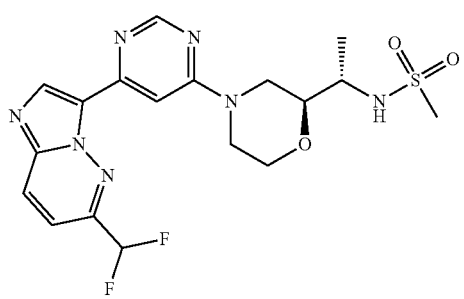 [SMILES: C[C@H](NS(C)(=O)=O)[C@@H]1CN(c2cc(-c3cnc4ccc(C(F)F)nn34)ncn2)CCO1] II-772
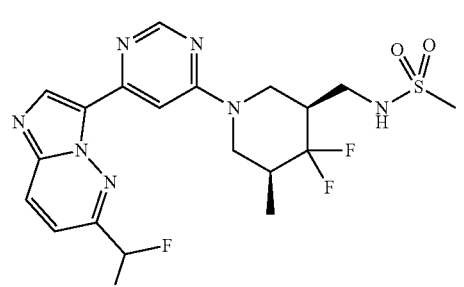 II-773
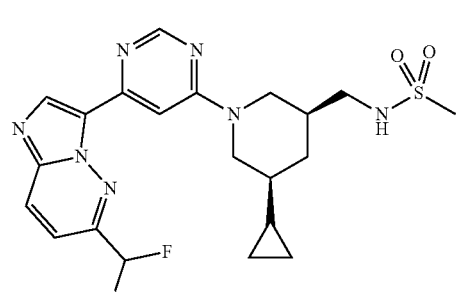 II-774

TABLE 1-continued

Exemplary compounds of formula II

II-775, II-776, II-777, II-778, II-779

TABLE 2

Exemplary compounds of Formula III

III-1, III-2, III-3, III-4, III-5

TABLE 2-continued
Exemplary compounds of Formula III
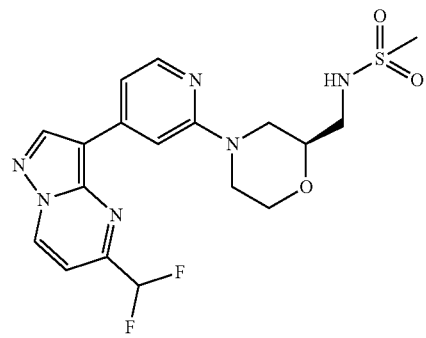 [SMILES: CS(=O)(=O)NC[C@@H]1CN(c2cc(-c3cnn4ccc(C(F)F)nc34)ccn2)CCO1]
III-6
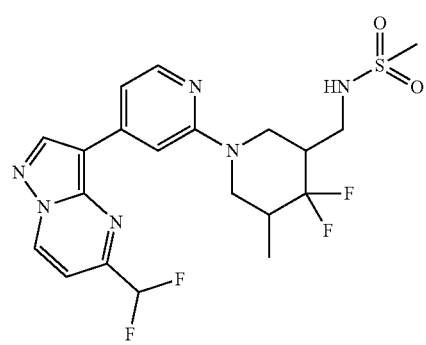 [SMILES: CC1CN(c2cc(-c3cnn4ccc(C(F)F)nc34)ccn2)CC(CNS(C)(=O)=O)C1(F)F]
III-7
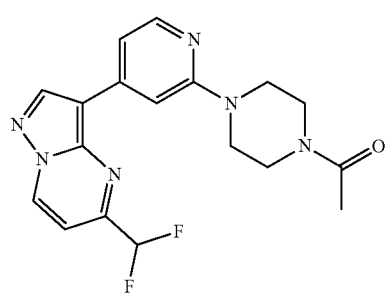 [SMILES: CC(=O)N1CCN(c2cc(-c3cnn4ccc(C(F)F)nc34)ccn2)CC1]
III-8
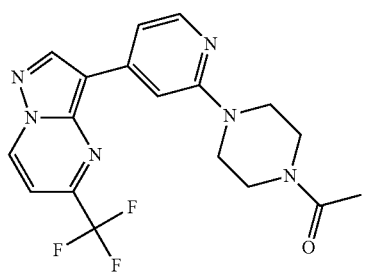 [SMILES: CC(=O)N1CCN(c2cc(-c3cnn4ccc(C(F)(F)F)nc34)ccn2)CC1]
III-9
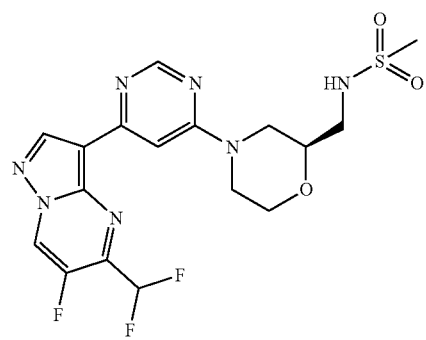 [SMILES: CS(=O)(=O)NC[C@@H]1CN(c2cc(-c3cnn4cc(F)c(C(F)F)nc34)ncn2)CCO1]
III-10
TABLE 2-continued
Exemplary compounds of Formula III
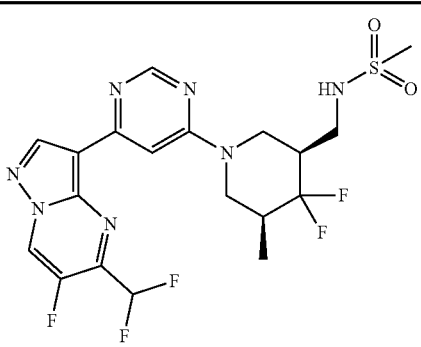
III-11
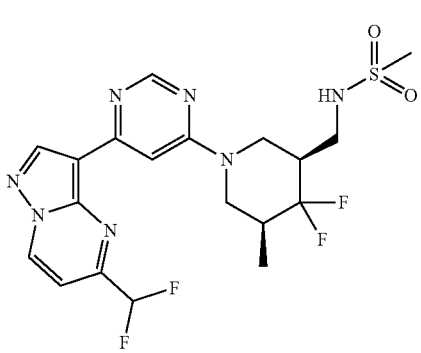 [SMILES: C[C@H]1CN(c2cc(-c3cnn4ccc(C(F)F)nc34)ncn2)C[C@@H](CNS(C)(=O)=O)C1(F)F]
III-12
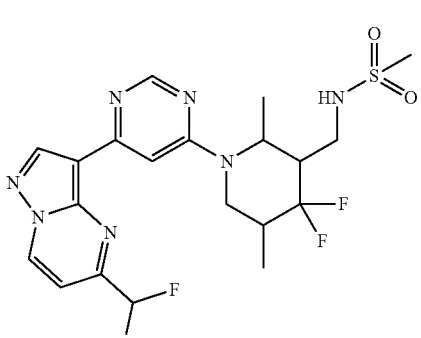
III-13
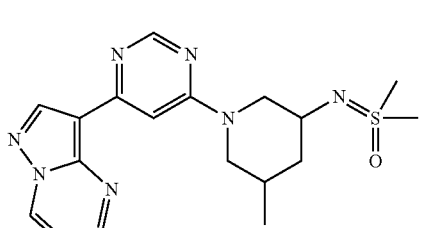
III-14
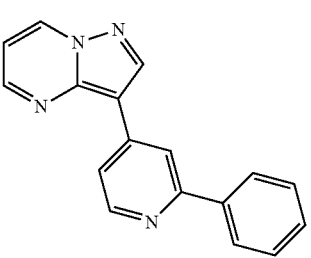 [SMILES: c1ccc(-c2cc(-c3cnn4cccnc34)ccn2)cc1]
III-15

TABLE 2-continued
Exemplary compounds of Formula III
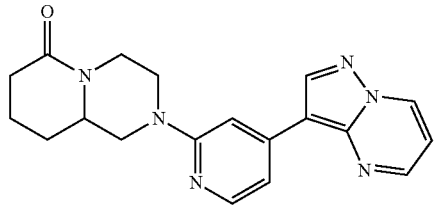 [SMILES: O=C1CCCC2CN(c3cc(-c4cnn5cccnc45)ccn3)CCN12]
III-16
TABLE 3
Exemplary compounds of formula IV
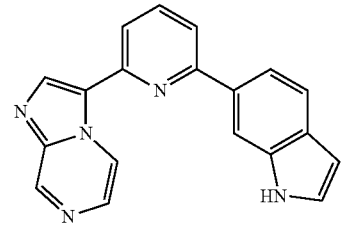 [SMILES: c1cc(-c2ccc3cc[nH]c3c2)nc(-c2cnc3cnccn23)c1]
IV-1
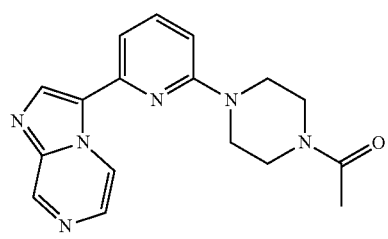 [SMILES: CC(=O)N1CCN(c2cccc(-c3cnc4cnccn34)n2)CC1]
IV-2
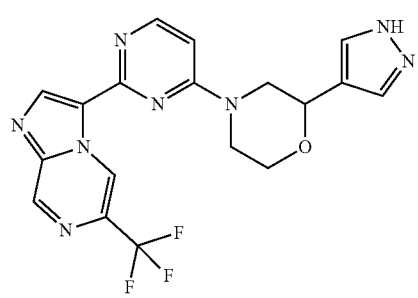 [SMILES: FC(F)(F)c1cn2c(-c3nccc(N4CCOC(c5cn[nH]c5)C4)n3)cnc2cn1]
IV-3
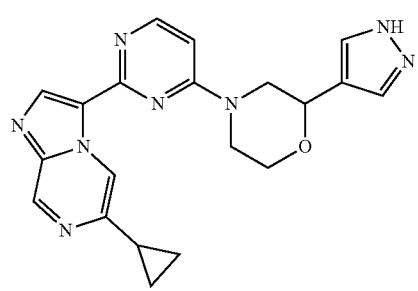 [SMILES: c1cc(N2CCOC(c3cn[nH]c3)C2)nc(-c2cnc3cnc(C4CC4)cn23)n1]
IV-4
TABLE 3-continued
Exemplary compounds of formula IV
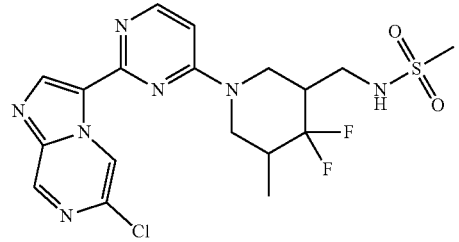 [SMILES: CC1CN(c2ccnc(-c3cnc4cnc(Cl)cn34)n2)CC(CNS(C)(=O)=O)C1(F)F]
IV-5
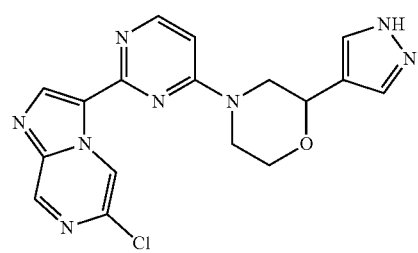 [SMILES: Clc1cn2c(-c3nccc(N4CCOC(c5cn[nH]c5)C4)n3)cnc2cn1]
IV-6
single stereoisomer
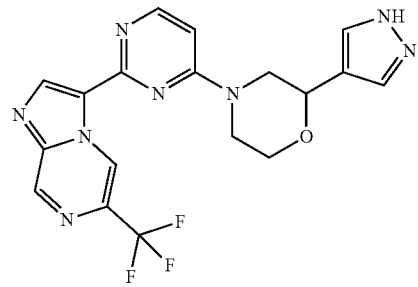 [SMILES: FC(F)(F)c1cn2c(-c3nccc(N4CCOC(c5cn[nH]c5)C4)n3)cnc2cn1]
IV-7
single stereoisomer
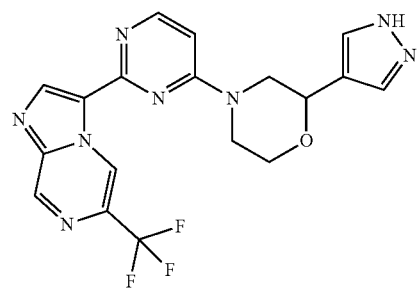
IV-8
single stereoisomer
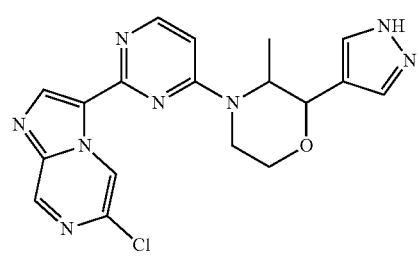 [SMILES: CC1C(c2cn[nH]c2)OCCN1c1ccnc(-c2cnc3cnc(Cl)cn23)n1]
IV-9

TABLE 3-continued
Exemplary compounds of formula IV
IV-10
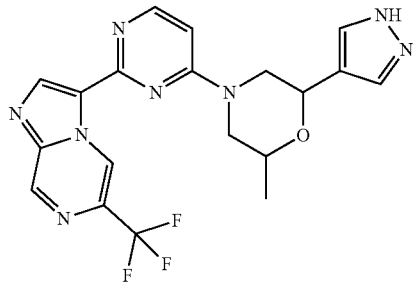 [SMILES: CC1CN(c2ccnc(-c3cnc4cnc(C(F)(F)F)cn34)n2)CC(c2cn[nH]c2)O1]
single diastereoisomer
(two enantiomers)
IV-11
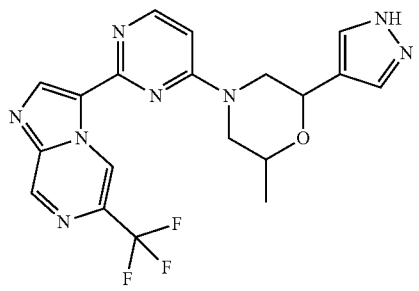 [SMILES: CC1CN(c2ccnc(-c3cnc4cnc(C(F)(F)F)cn34)n2)CC(c2cn[nH]c2)O1]
single diastereoisomer
(two enantiomers)
IV-12
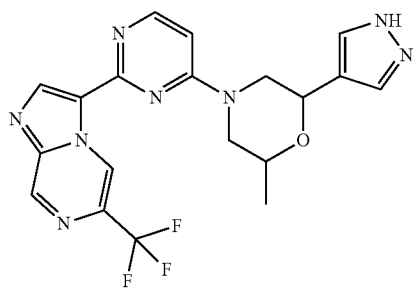 [SMILES: CC1CN(c2ccnc(-c3cnc4cnc(C(F)(F)F)cn34)n2)CC(c2cn[nH]c2)O1]
single stereoisomer
IV-13
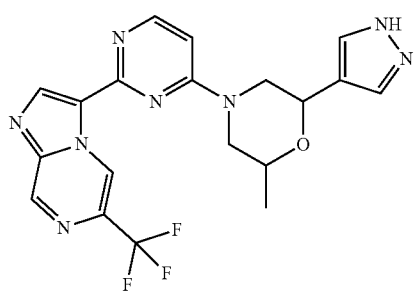 [SMILES: CC1CN(c2ccnc(-c3cnc4cnc(C(F)(F)F)cn34)n2)CC(c2cn[nH]c2)O1]
TABLE 3-continued
Exemplary compounds of formula IV
single stereoisomer
IV-14
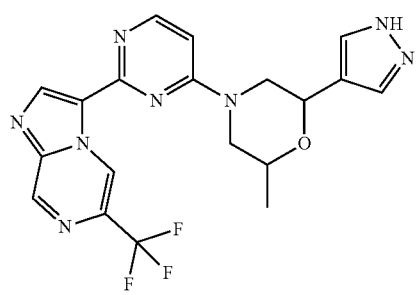 [SMILES: CC1CN(c2ccnc(-c3cnc4cnc(C(F)(F)F)cn34)n2)CC(c2cn[nH]c2)O1]
single stereoisomer
IV-15
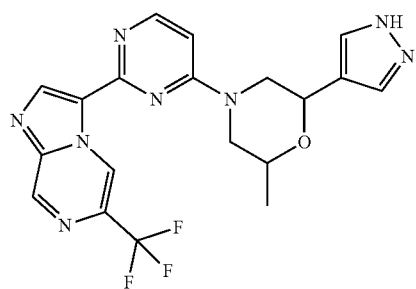
IV-16
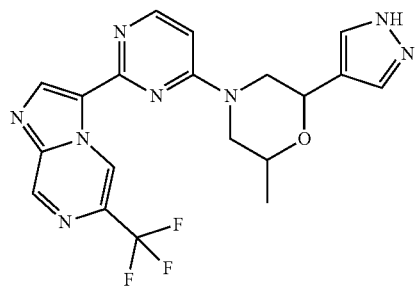 [SMILES: CC1CN(c2ccnc(-c3cnc4cnc(C(F)(F)F)cn34)n2)CC(c2cn[nH]c2)O1]
IV-17
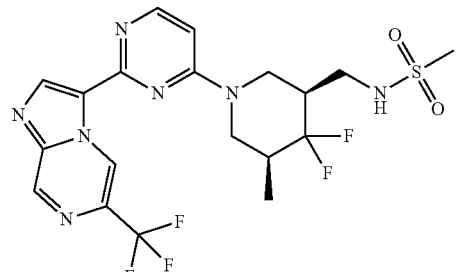
IV-18
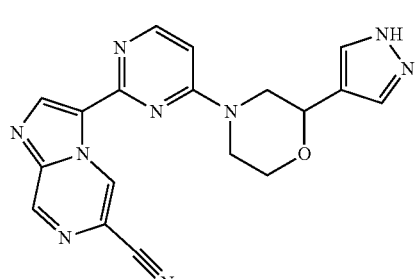

TABLE 3-continued
Exemplary compounds of formula IV
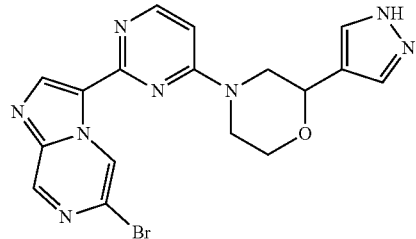 IV-19
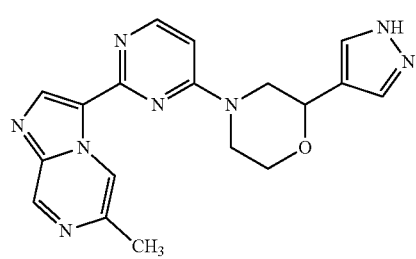 [SMILES: Cc1cn2c(-c3nccc(N4CCOC(c5cn[nH]c5)C4)n3)cnc2cn1] IV-20
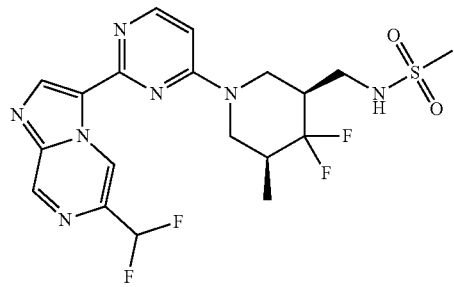 [SMILES: C[C@H]1CN(c2ccnc(-c3cnc4cnc(C(F)F)cn34)n2)C[C@@H](CNS(C)(=O)=O)C1(F)F] IV-21
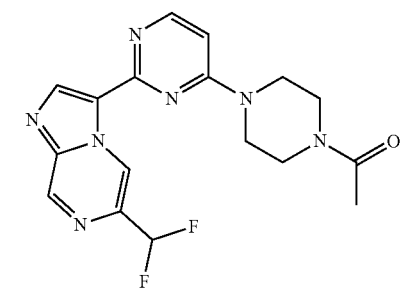 [SMILES: CC(=O)N1CCN(c2ccnc(-c3cnc4cnc(C(F)F)cn34)n2)CC1] IV-22
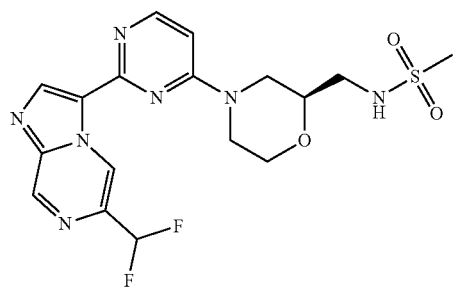 [SMILES: CS(=O)(=O)NC[C@@H]1CN(c2ccnc(-c3cnc4cnc(C(F)F)cn34)n2)CCO1] IV-23
TABLE 3-continued
Exemplary compounds of formula IV
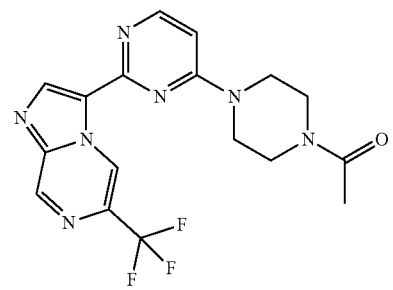 [SMILES: CC(=O)N1CCN(c2ccnc(-c3cnc4cnc(C(F)(F)F)cn34)n2)CC1] IV-24
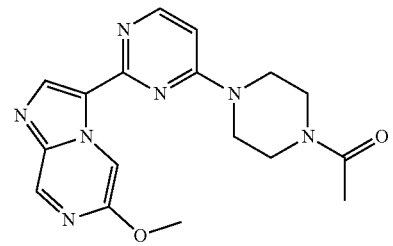 [SMILES: COc1cn2c(-c3nccc(N4CCN(C(C)=O)CC4)n3)cnc2cn1] IV-25
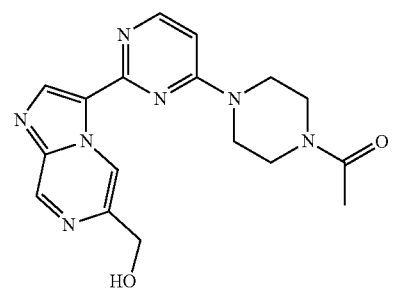 [SMILES: CC(=O)N1CCN(c2ccnc(-c3cnc4cnc(CO)cn34)n2)CC1] IV-26
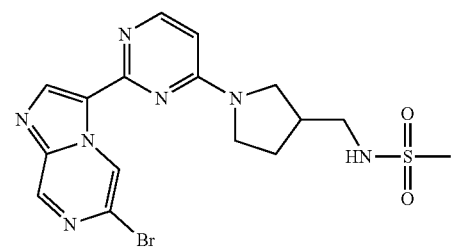 [SMILES: CS(=O)(=O)NCC1CCN(c2ccnc(-c3cnc4cnc(Br)cn34)n2)C1] IV-27
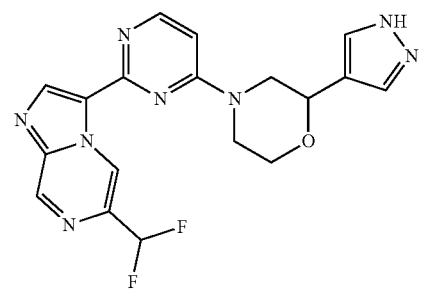 [SMILES: FC(F)c1cn2c(-c3nccc(N4CCOC(c5cn[nH]c5)C4)n3)cnc2cn1] IV-28

TABLE 3-continued
Exemplary compounds of formula IV
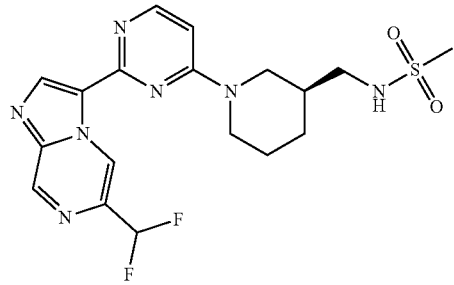 [SMILES: CS(=O)(=O)NC[C@H]1CCCN(c2ccnc(-c3cnc4cnc(C(F)F)cn34)n2)C1] IV-29
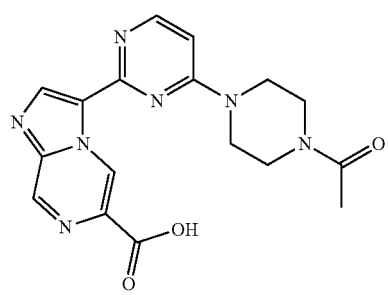 [SMILES: CC(=O)N1CCN(c2ccnc(-c3cnc4cnc(C(=O)O)cn34)n2)CC1] IV-30
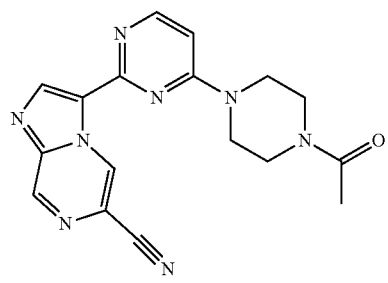 [SMILES: CC(=O)N1CCN(c2ccnc(-c3cnc4cnc(C#N)cn34)n2)CC1] IV-31
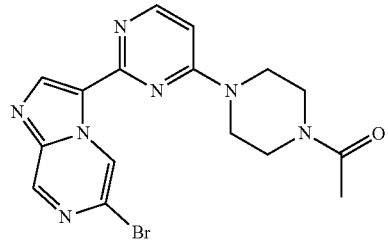 IV-32
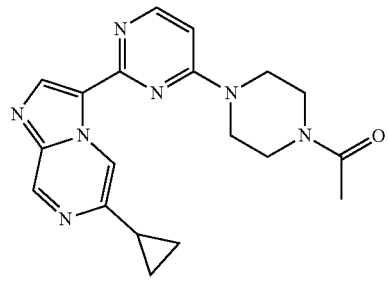 [SMILES: CC(=O)N1CCN(c2ccnc(-c3cnc4cnc(C5CC5)cn34)n2)CC1] IV-33
TABLE 3-continued
Exemplary compounds of formula IV
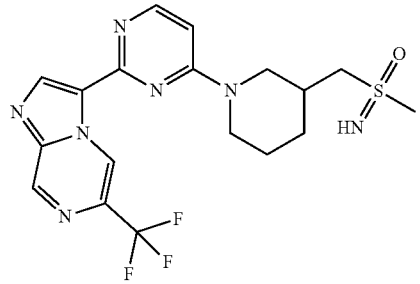 [SMILES: CS(=N)(=O)CC1CCCN(c2ccnc(-c3cnc4cnc(C(F)(F)F)cn34)n2)C1] IV-34
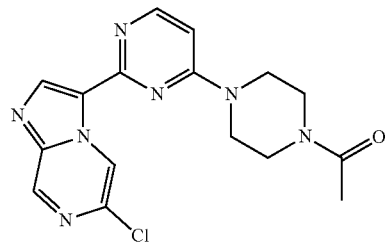 [SMILES: CC(=O)N1CCN(c2ccnc(-c3cnc4cnc(Cl)cn34)n2)CC1] IV-35
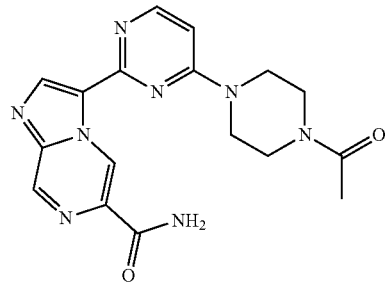 IV-36
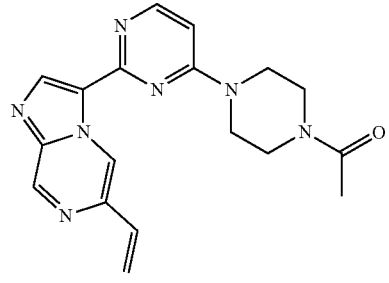 [SMILES: C=Cc1cn2c(-c3nccc(N4CCN(C(C)=O)CC4)n3)cnc2cn1] IV-37
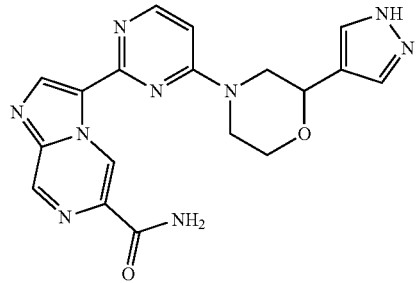 [SMILES: NC(=O)c1cn2c(-c3nccc(N4CCOC(c5cn[nH]c5)C4)n3)cnc2cn1] IV-38

TABLE 3-continued
Exemplary compounds of formula IV
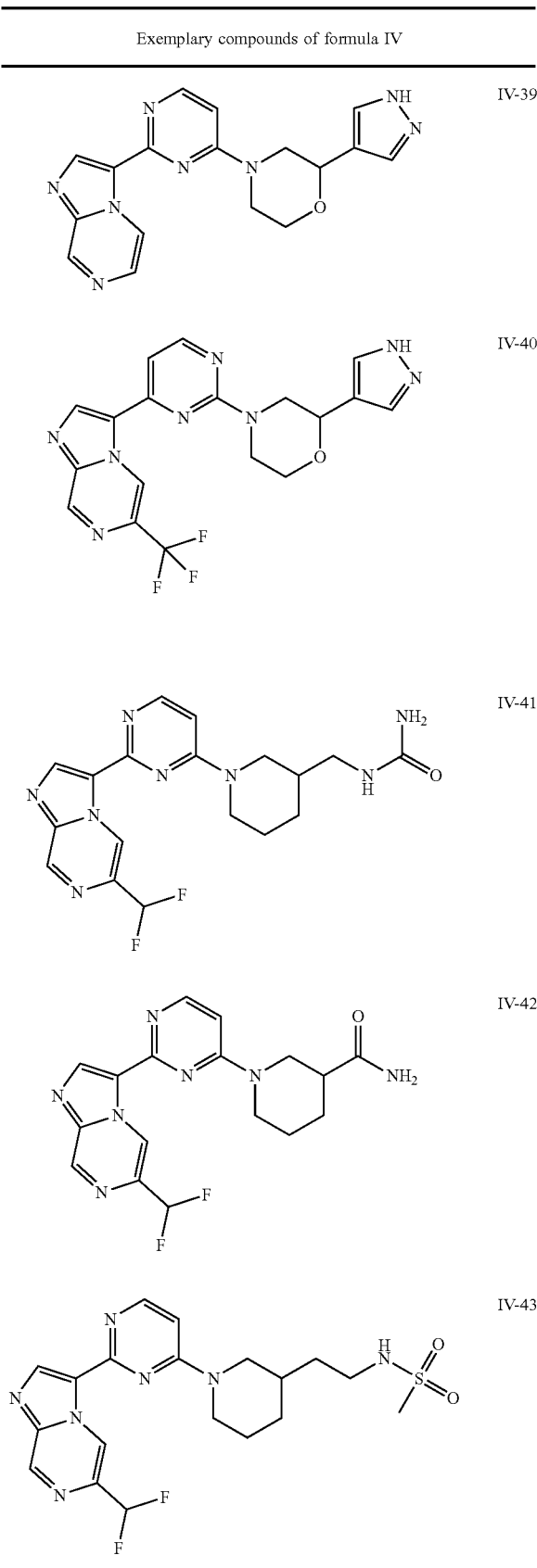
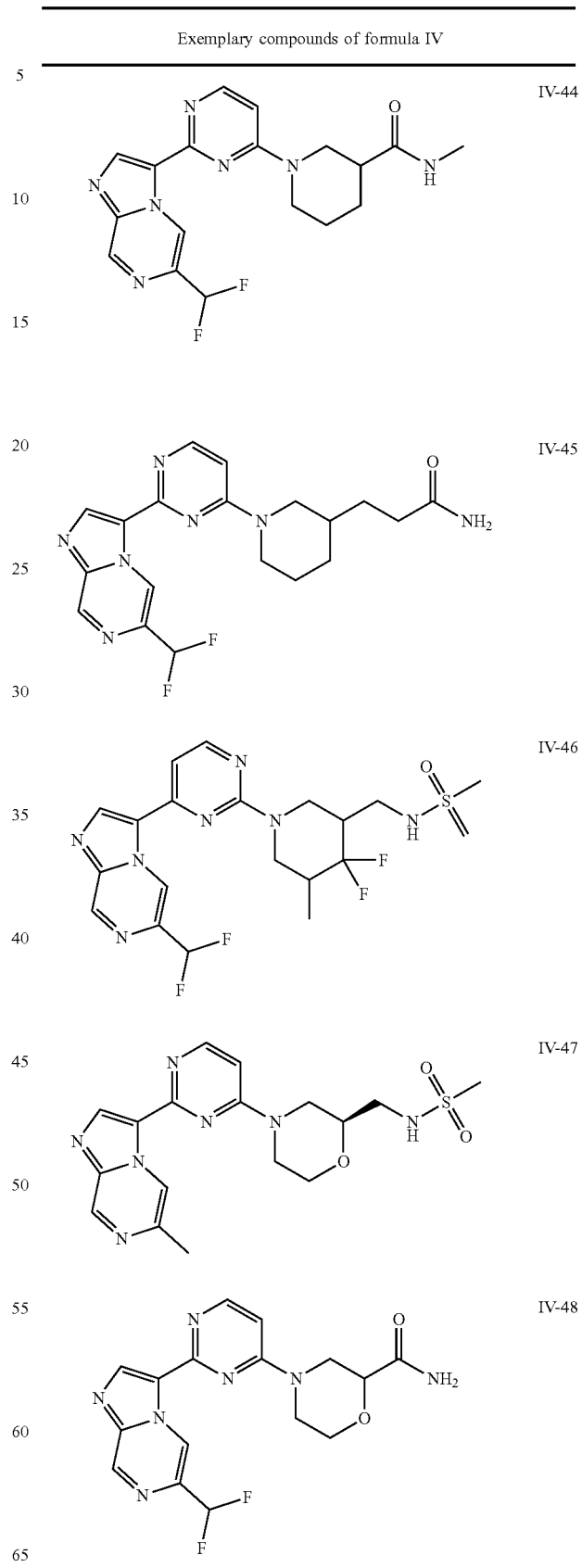

TABLE 3-continued
Exemplary compounds of formula IV
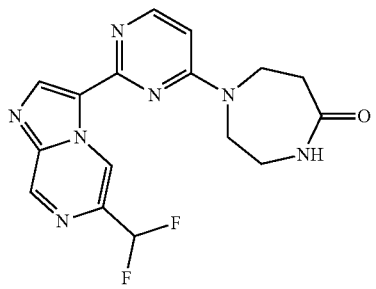 [SMILES: O=C1CCN(c2ccnc(-c3cnc4cnc(C(F)F)cn34)n2)CCN1] IV-49
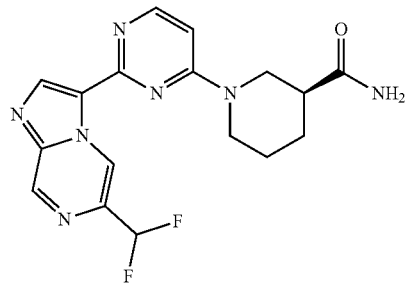 [SMILES: NC(=O)[C@H]1CCCN(c2ccnc(-c3cnc4cnc(C(F)F)cn34)n2)C1] IV-50
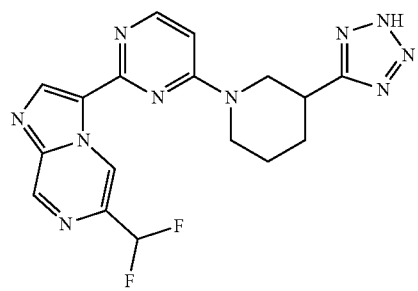 [SMILES: FC(F)c1cn2c(-c3nccc(N4CCCC(c5nn[nH]n5)C4)n3)cnc2cn1] IV-51
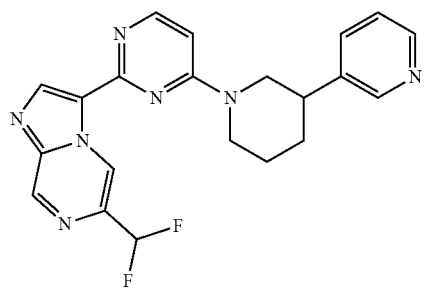 [SMILES: FC(F)c1cn2c(-c3nccc(N4CCCC(c5cccnc5)C4)n3)cnc2cn1] IV-52
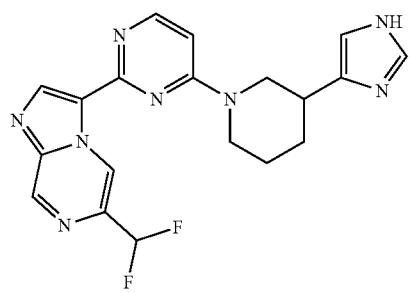 [SMILES: FC(F)c1cn2c(-c3nccc(N4CCCC(c5c[nH]cn5)C4)n3)cnc2cn1] IV-53
TABLE 3-continued
Exemplary compounds of formula IV
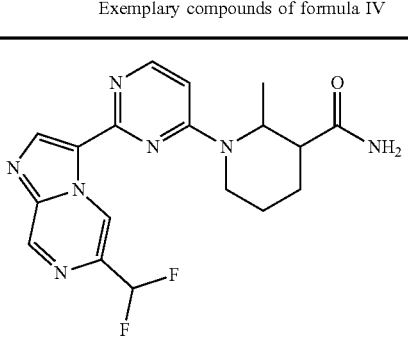 IV-54
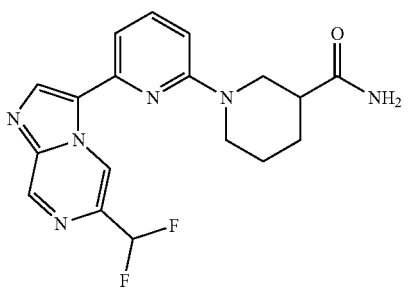 [SMILES: NC(=O)C1CCCN(c2cccc(-c3cnc4cnc(C(F)F)cn34)n2)C1] IV-55
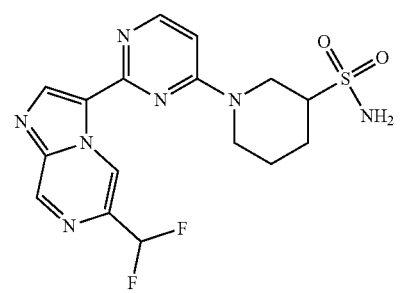 [SMILES: NS(=O)(=O)C1CCCN(c2ccnc(-c3cnc4cnc(C(F)F)cn34)n2)C1] IV-56
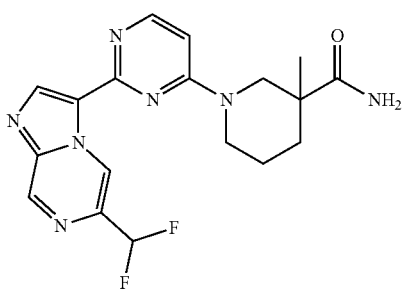 [SMILES: CC1(C(N)=O)CCCN(c2ccnc(-c3cnc4cnc(C(F)F)cn34)n2)C1] IV-57
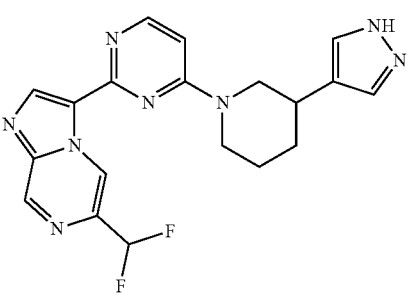 [SMILES: FC(F)c1cn2c(-c3nccc(N4CCCC(c5cn[nH]c5)C4)n3)cnc2cn1] IV-58

TABLE 3-continued
Exemplary compounds of formula IV
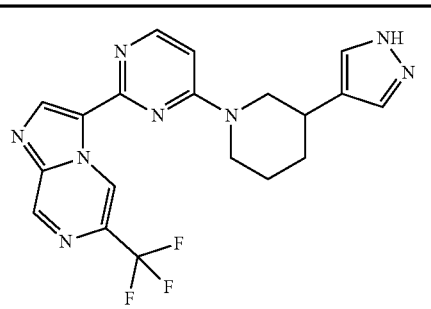 IV-59
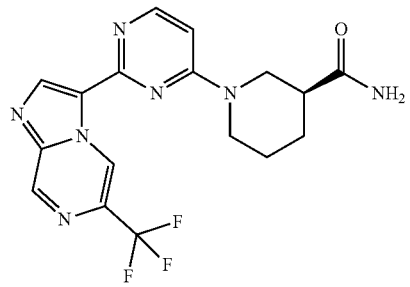 [SMILES: NC(=O)[C@H]1CCCN(c2ccnc(-c3cnc4cnc(C(F)(F)F)cn34)n2)C1] IV-60
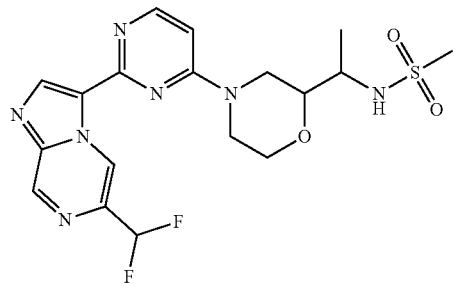 [SMILES: CC(NS(C)(=O)=O)C1CN(c2ccnc(-c3cnc4cnc(C(F)F)cn34)n2)CCO1] IV-61
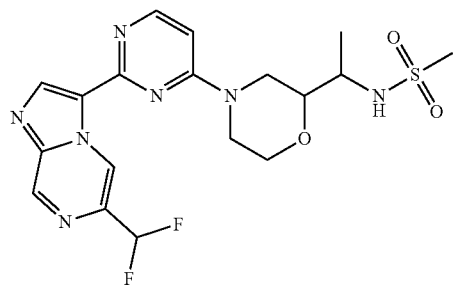 [SMILES: CC(NS(C)(=O)=O)C1CN(c2ccnc(-c3cnc4cnc(C(F)F)cn34)n2)CCO1] IV-62
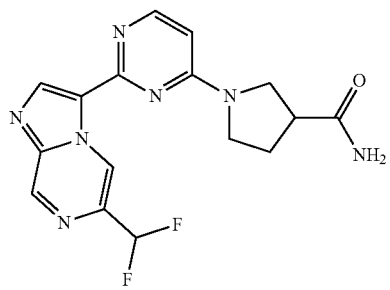 [SMILES: NC(=O)C1CCN(c2ccnc(-c3cnc4cnc(C(F)F)cn34)n2)C1] IV-63
TABLE 3-continued
Exemplary compounds of formula IV
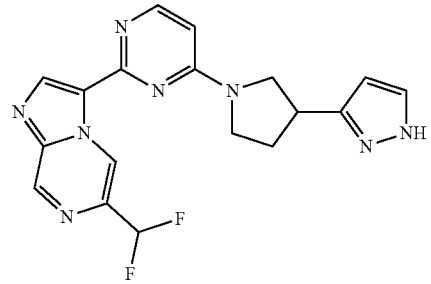 IV-64
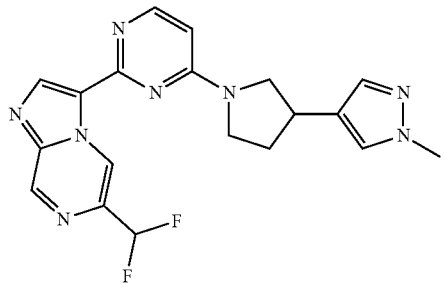 [SMILES: Cn1cc(C2CCN(c3ccnc(-c4cnc5cnc(C(F)F)cn45)n3)C2)cn1] IV-65
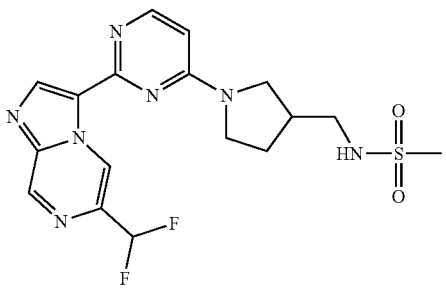 [SMILES: CS(=O)(=O)NCC1CCN(c2ccnc(-c3cnc4cnc(C(F)F)cn34)n2)C1] IV-66
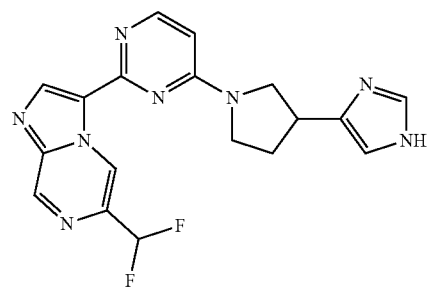 [SMILES: FC(F)c1cn2c(-c3nccc(N4CCC(c5c[nH]cn5)C4)n3)cnc2cn1] IV-67
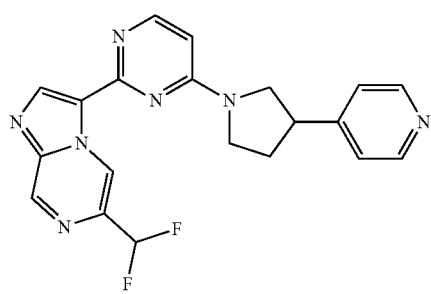 [SMILES: FC(F)c1cn2c(-c3nccc(N4CCC(c5ccncc5)C4)n3)cnc2cn1] IV-68

TABLE 3-continued
Exemplary compounds of formula IV
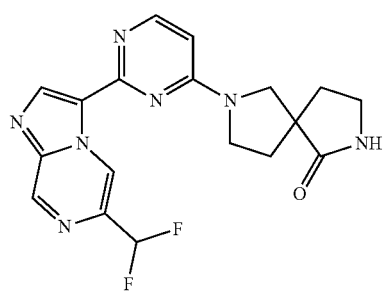 [SMILES: O=C1NCCC12CCN(c1ccnc(-c3cnc4cnc(C(F)F)cn34)n1)C2] IV-69
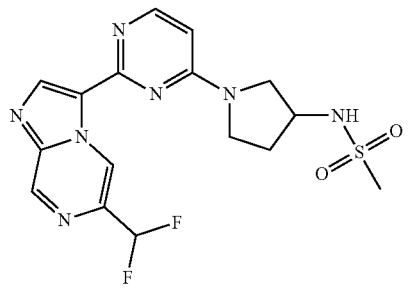 [SMILES: CS(=O)(=O)NC1CCN(c2ccnc(-c3cnc4cnc(C(F)F)cn34)n2)C1] IV-70
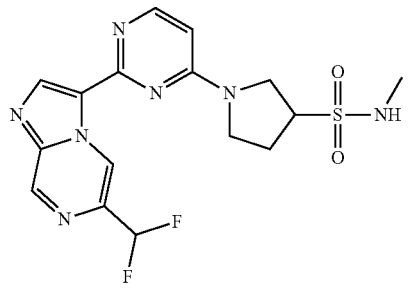 [SMILES: CNS(=O)(=O)C1CCN(c2ccnc(-c3cnc4cnc(C(F)F)cn34)n2)C1] IV-71
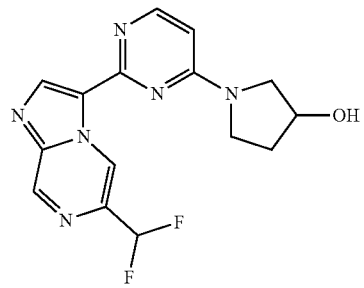 [SMILES: OC1CCN(c2ccnc(-c3cnc4cnc(C(F)F)cn34)n2)C1] IV-72
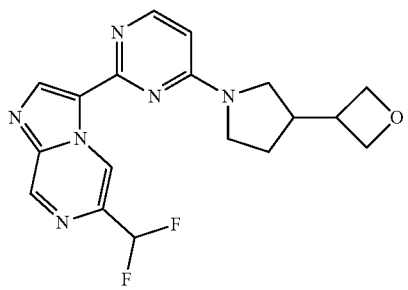 [SMILES: FC(F)c1cn2c(-c3nccc(N4CCC(C5COC5)C4)n3)cnc2cn1] IV-73
TABLE 3-continued
Exemplary compounds of formula IV
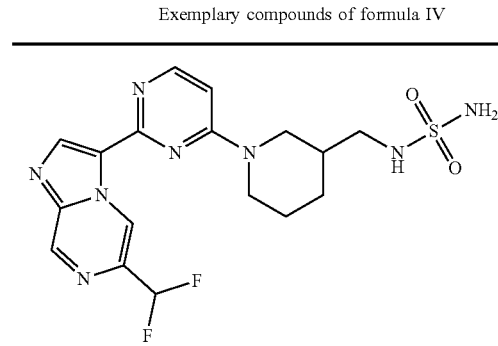 IV-74
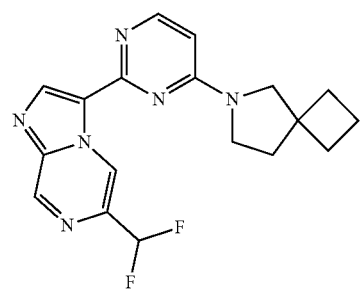 [SMILES: FC(F)c1cn2c(-c3nccc(N4CCC5(CCC5)C4)n3)cnc2cn1] IV-75
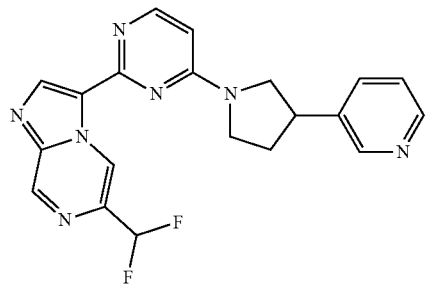 [SMILES: FC(F)c1cn2c(-c3nccc(N4CCC(c5cccnc5)C4)n3)cnc2cn1] IV-76
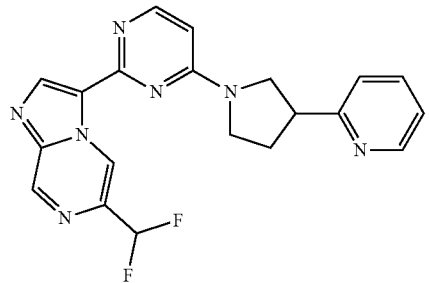 [SMILES: FC(F)c1cn2c(-c3nccc(N4CCC(c5ccccn5)C4)n3)cnc2cn1] IV-77
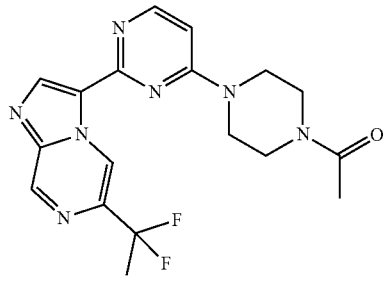 [SMILES: CC(=O)N1CCN(c2ccnc(-c3cnc4cnc(C(C)(F)F)cn34)n2)CC1] IV-78

TABLE 3-continued
Exemplary compounds of formula IV
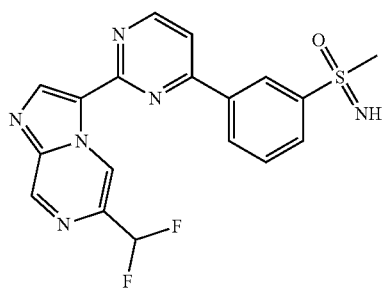 [SMILES: CS(=N)(=O)c1cccc(-c2ccnc(-c3cnc4cnc(C(F)F)cn34)n2)c1]  IV-79
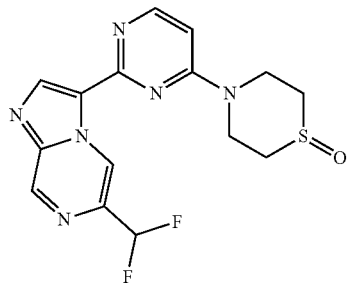 [SMILES: O=S1CCN(c2ccnc(-c3cnc4cnc(C(F)F)cn34)n2)CC1]  IV-80
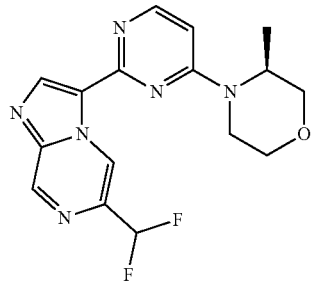 [SMILES: C[C@H]1COCCN1c1ccnc(-c2cnc3cnc(C(F)F)cn23)n1]  IV-81
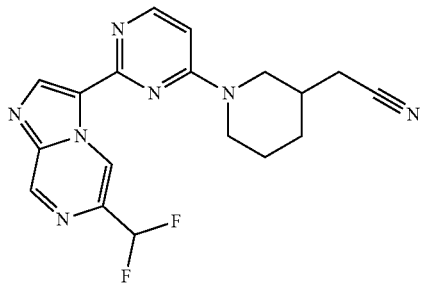 [SMILES: N#CCC1CCCN(c2ccnc(-c3cnc4cnc(C(F)F)cn34)n2)C1]  IV-82
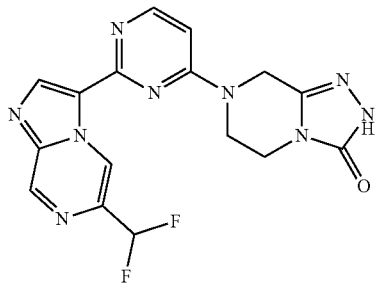 [SMILES: O=c1[nH]nc2n1CCN(c1ccnc(-c3cnc4cnc(C(F)F)cn34)n1)C2]  IV-83
TABLE 3-continued
Exemplary compounds of formula IV
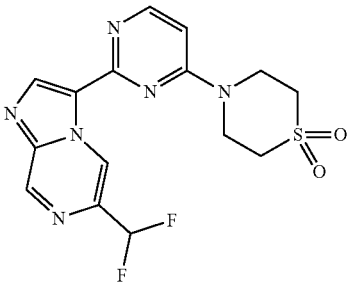 [SMILES: O=S1(=O)CCN(c2ccnc(-c3cnc4cnc(C(F)F)cn34)n2)CC1]  IV-84
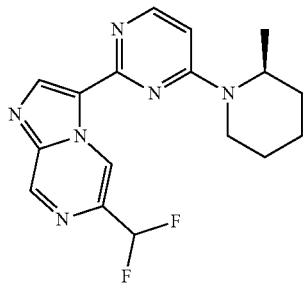 [SMILES: C[C@H]1CCCCN1c1ccnc(-c2cnc3cnc(C(F)F)cn23)n1]  IV-85
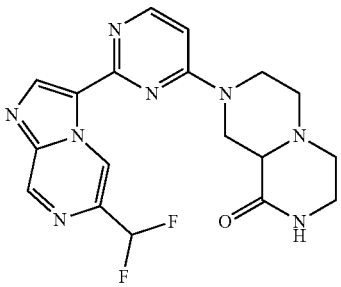 [SMILES: O=C1NCCN2CCN(c3ccnc(-c4cnc5cnc(C(F)F)cn45)n3)CC12]  IV-86
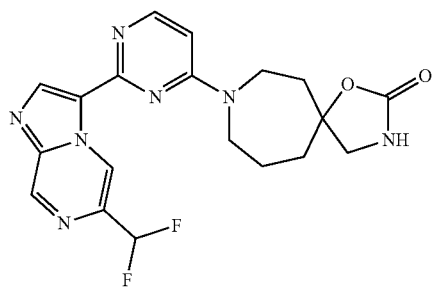 [SMILES: O=C1NCC2(CCCN(c3ccnc(-c4cnc5cnc(C(F)F)cn45)n3)CC2)O1]  IV-87
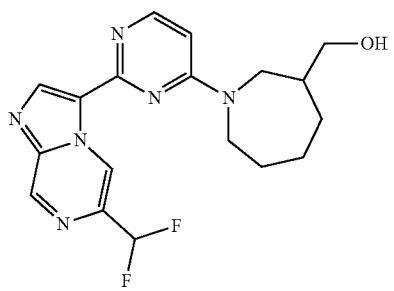 [SMILES: OCC1CCCCN(c2ccnc(-c3cnc4cnc(C(F)F)cn34)n2)C1]  IV-88

TABLE 3-continued

Exemplary compounds of formula IV

TABLE 3-continued
Exemplary compounds of formula IV
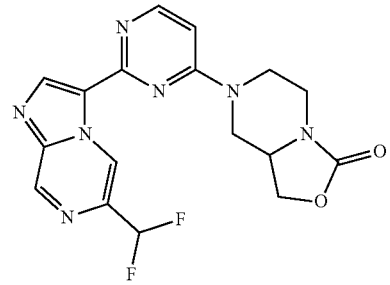 [SMILES: O=C1CCC2CN(c3ccnc(-c4cnc5cnc(C(F)F)cn45)n3)CCN12]
IV-100
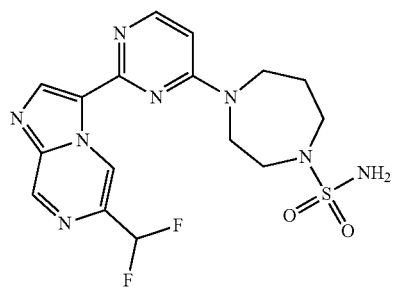 [SMILES: NS(=O)(=O)N1CCCN(c2ccnc(-c3cnc4cnc(C(F)F)cn34)n2)CC1]
IV-101
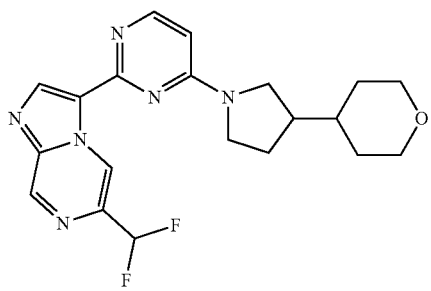 [SMILES: FC(F)c1cn2c(-c3nccc(N4CCC(C5CCOCC5)C4)n3)cnc2cn1]
IV-102
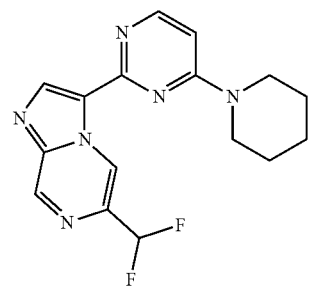 [SMILES: FC(F)c1cn2c(-c3nccc(N4CCCCC4)n3)cnc2cn1]
IV-103
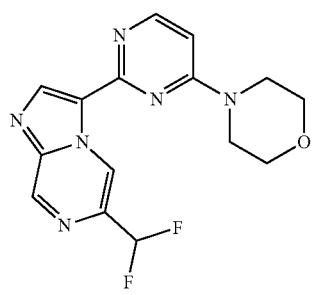 [SMILES: FC(F)c1cn2c(-c3nccc(N4CCOCC4)n3)cnc2cn1]
IV-104
TABLE 3-continued
Exemplary compounds of formula IV
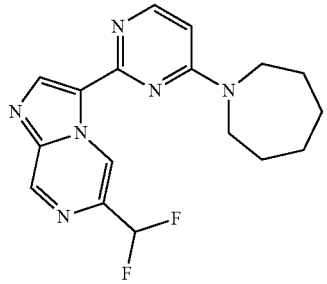 [SMILES: FC(F)c1cn2c(-c3nccc(N4CCCCCC4)n3)cnc2cn1]
IV-105
single diastereoisomer
(two enantiomers)
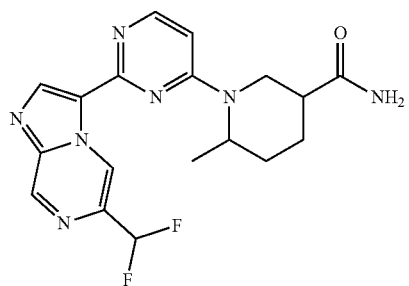 [SMILES: CC1CCC(C(N)=O)CN1c1ccnc(-c2cnc3cnc(C(F)F)cn23)n1]
IV-106
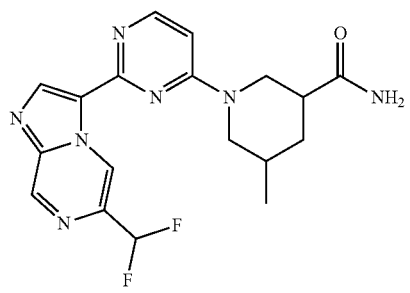 [SMILES: CC1CC(C(N)=O)CN(c2ccnc(-c3cnc4cnc(C(F)F)cn34)n2)C1]
IV-107
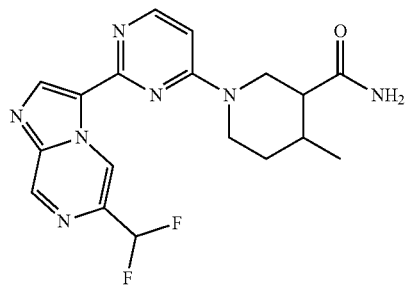 [SMILES: CC1CCN(c2ccnc(-c3cnc4cnc(C(F)F)cn34)n2)CC1C(N)=O]
IV-108
single diastereoisomer
(two enantiomers)
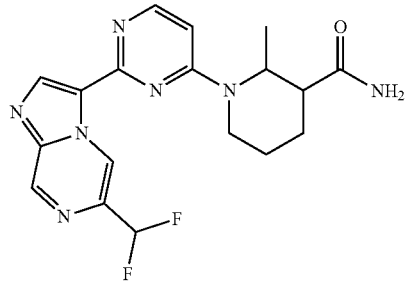 [SMILES: CC1C(C(N)=O)CCCN1c1ccnc(-c2cnc3cnc(C(F)F)cn23)n1]
IV-109

TABLE 3-continued

Exemplary compounds of formula IV

| | |
|---|---|
| single diastereoisomer (two enantiomers) | IV-110 |
| | IV-111 |
| | IV-112 |
| | IV-113 |
| | IV-114 |
| | IV-115 |
| | IV-116 |
| | IV-117 |
| | IV-118 |
| | IV-119 |

TABLE 3-continued

Exemplary compounds of formula IV

| | |
|---|---|
| IV-120 | IV-125 |
| IV-121 | IV-126 |
| IV-122 | IV-127 |
| IV-123 | IV-128 |
| IV-124 | IV-129 |

TABLE 3-continued
Exemplary compounds of formula IV
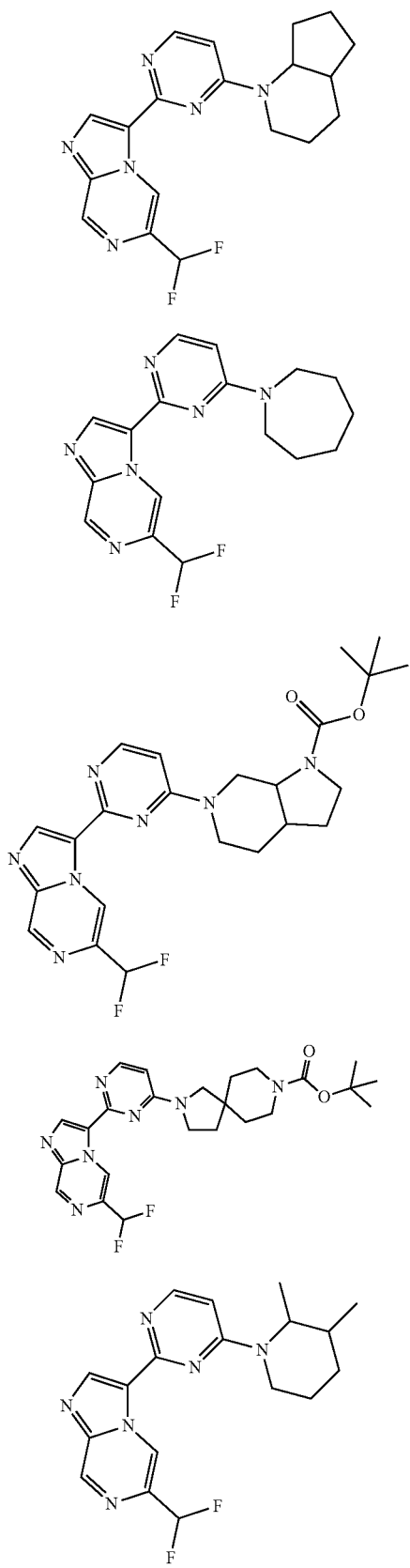
IV-130
IV-131
IV-132
IV-133
IV-134
TABLE 3-continued
Exemplary compounds of formula IV
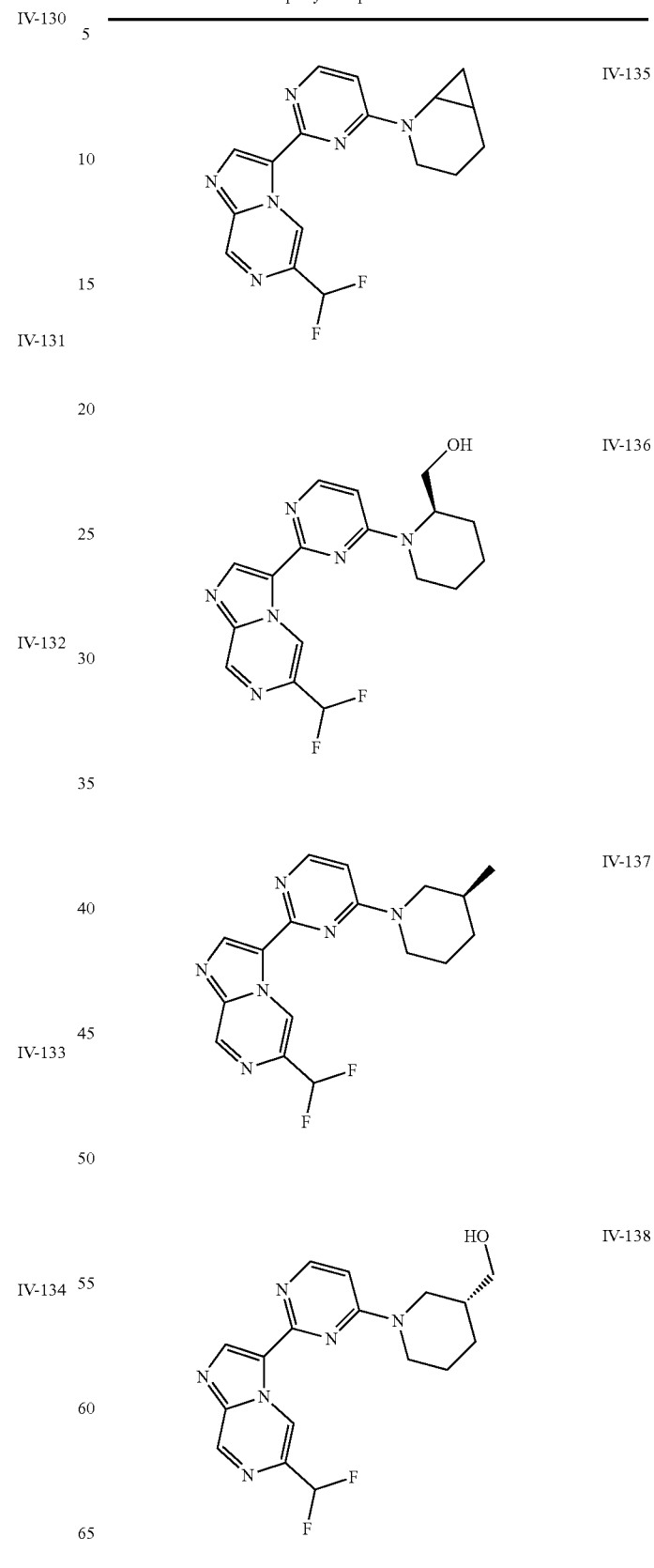
IV-135
IV-136
IV-137
IV-138

TABLE 3-continued

Exemplary compounds of formula IV

| | |
|---|---|
| IV-139 | IV-144 |
| IV-140 | IV-145 |
| IV-141 | IV-146 |
| IV-142 | IV-147 |
| IV-143 | IV-148 |

TABLE 3-continued
Exemplary compounds of formula IV
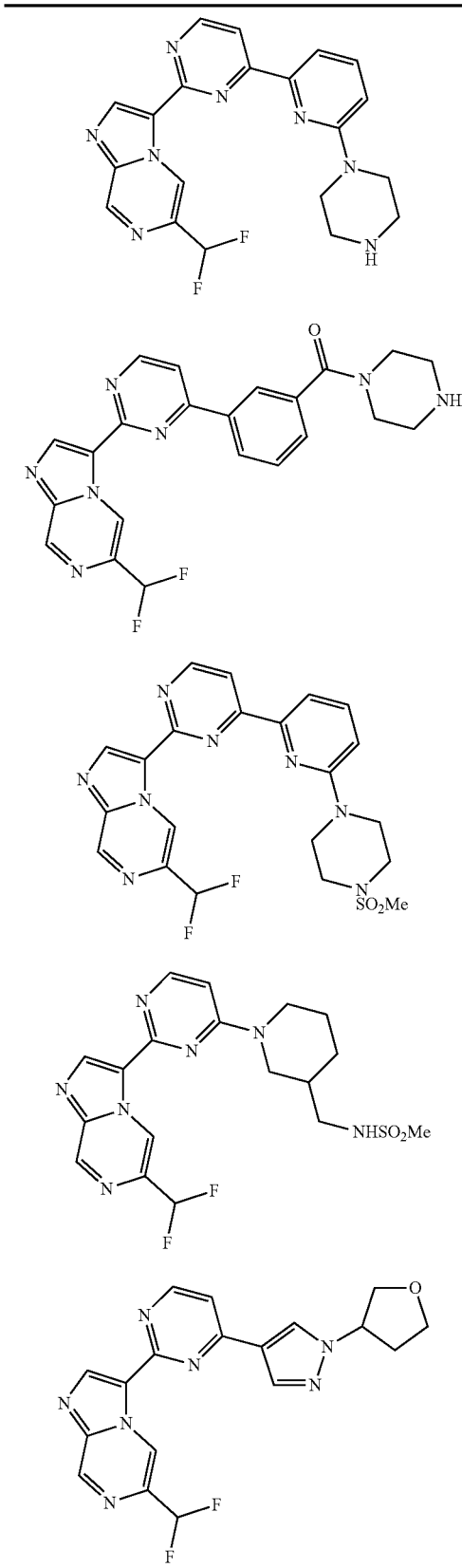
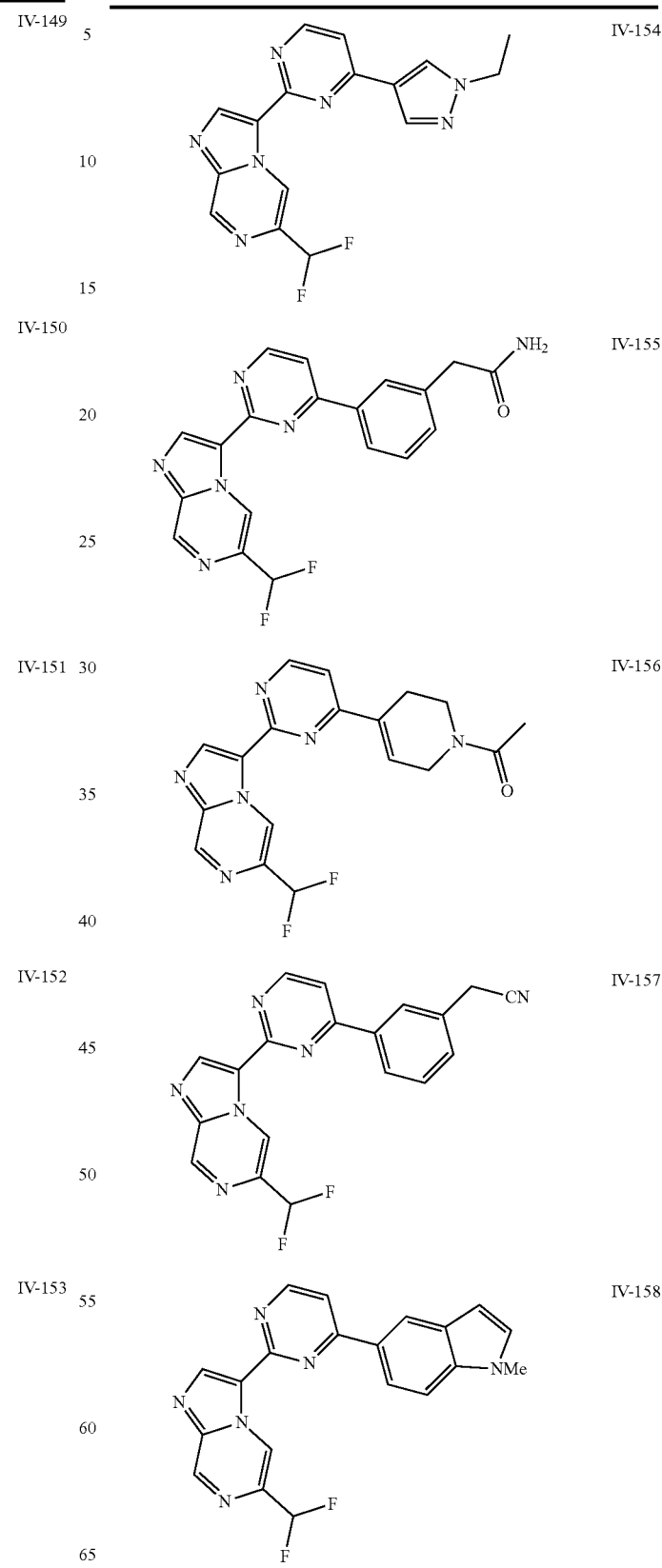

TABLE 3-continued
Exemplary compounds of formula IV
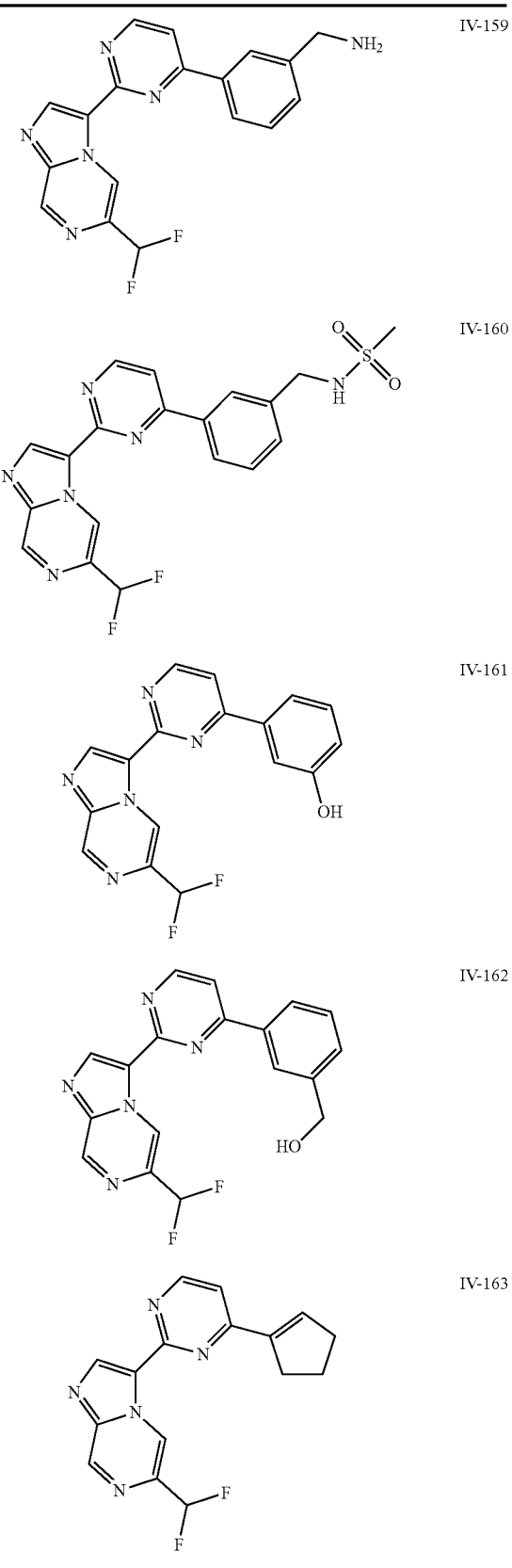
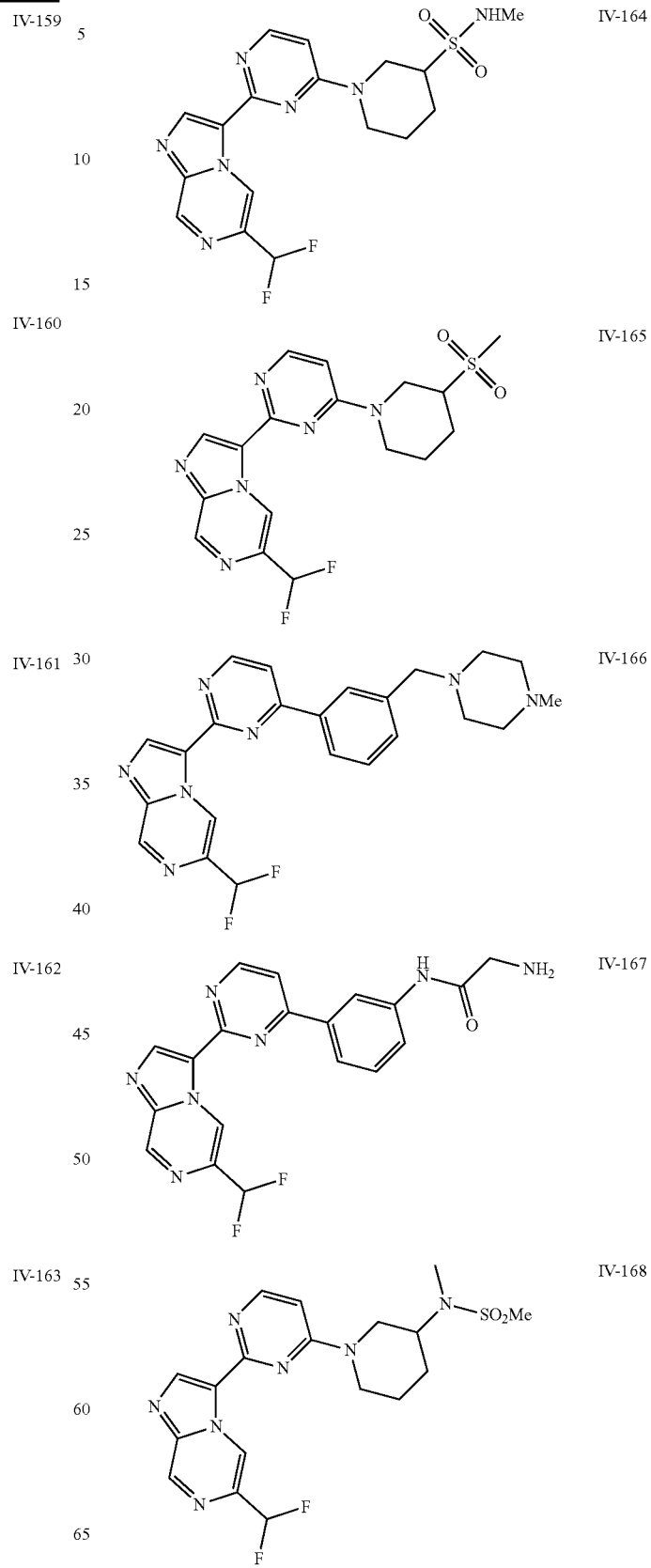

TABLE 3-continued

Exemplary compounds of formula IV

| | |
|---|---|
| IV-169 | IV-173 |
| IV-170 | IV-174 |
| IV-171 | IV-175 |
| IV-172 | IV-176 |
| | IV-177 single stereoisomer |

TABLE 3-continued
Exemplary compounds of formula IV
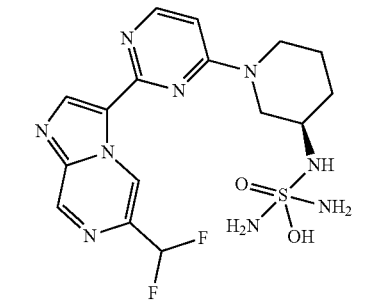 [SMILES: NS(N)(=O)(O)N[C@@H]1CCCN(c2ccnc(-c3cnc4cnc(C(F)F)cn34)n2)C1] IV-178
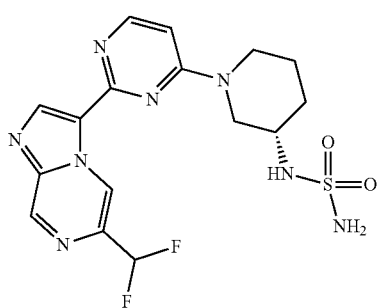 [SMILES: NS(=O)(=O)N[C@H]1CCCN(c2ccnc(-c3cnc4cnc(C(F)F)cn34)n2)C1] IV-179
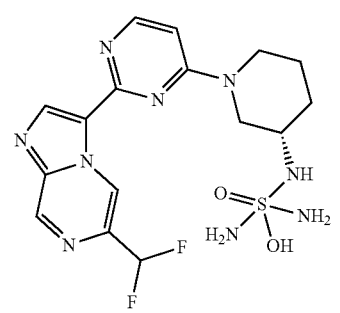 [SMILES: NS(N)(=O)(O)N[C@H]1CCCN(c2ccnc(-c3cnc4cnc(C(F)F)cn34)n2)C1] IV-180
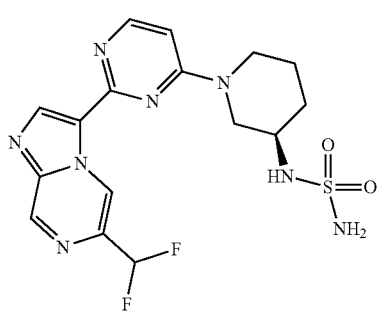 [SMILES: NS(=O)(=O)N[C@@H]1CCCN(c2ccnc(-c3cnc4cnc(C(F)F)cn34)n2)C1] IV-181
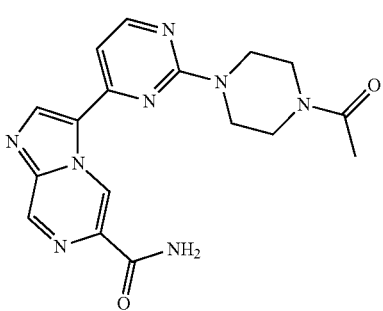 [SMILES: CC(=O)N1CCN(c2nccc(-c3cnc4cnc(C(N)=O)cn34)n2)CC1] IV-182
TABLE 3-continued
Exemplary compounds of formula IV
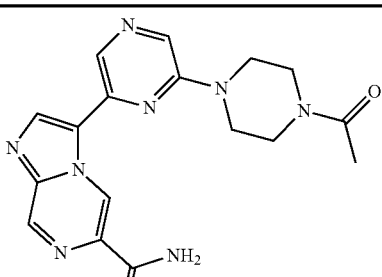 IV-183
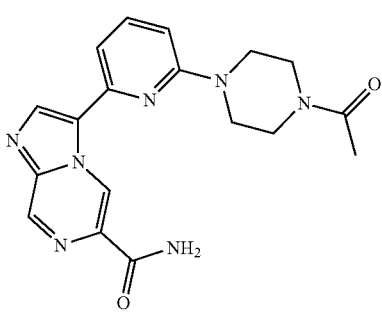 [SMILES: CC(=O)N1CCN(c2cccc(-c3cnc4cnc(C(N)=O)cn34)n2)CC1] IV-184
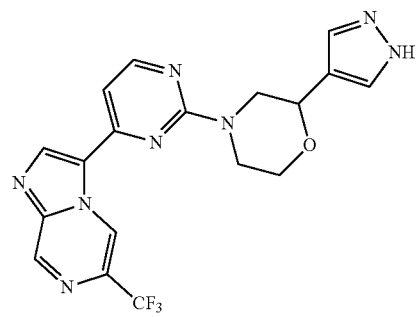 [SMILES: FC(F)(F)c1cn2c(-c3ccnc(N4CCOC(c5cn[nH]c5)C4)n3)cnc2cn1] IV-185
single stereoisomer
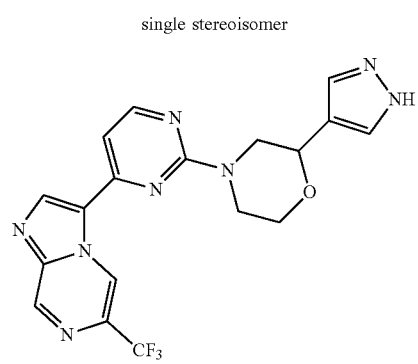 IV-186
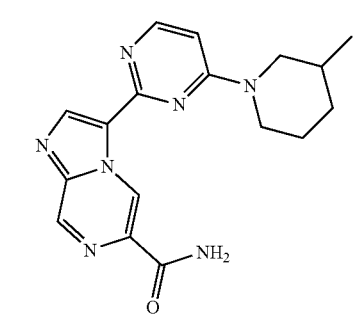 [SMILES: CC1CCCN(c2ccnc(-c3cnc4cnc(C(N)=O)cn34)n2)C1] IV-187

TABLE 3-continued
Exemplary compounds of formula IV
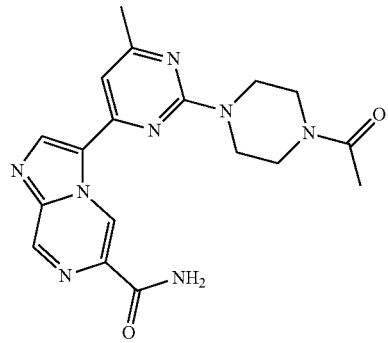 [SMILES: CC(=O)N1CCN(c2nc(C)cc(-c3cnc4cnc(C(N)=O)cn34)n2)CC1]
IV-188
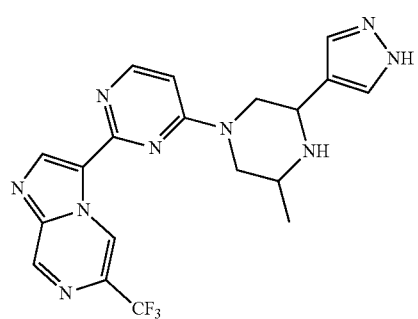 [SMILES: CC1CN(c2ccnc(-c3cnc4cnc(C(F)(F)F)cn34)n2)CC(c2cn[nH]c2)N1]
IV-189
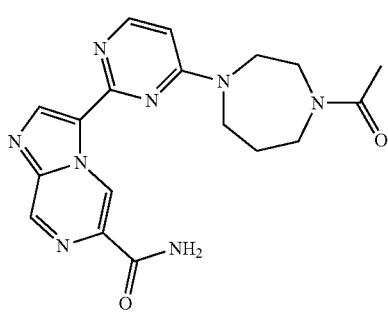 [SMILES: CC(=O)N1CCCN(c2ccnc(-c3cnc4cnc(C(N)=O)cn34)n2)CC1]
IV-190
single diastereomer
(two enantiomers)
IV-191
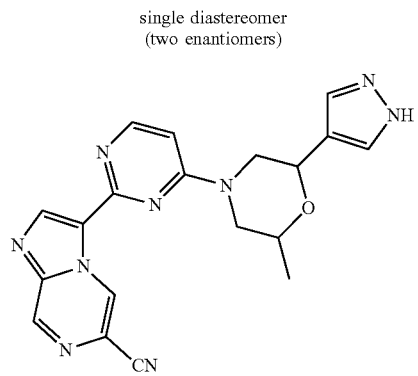
TABLE 3-continued
Exemplary compounds of formula IV
single diastereomer
(two enantiomers)
IV-192
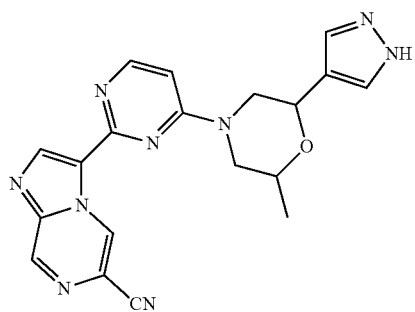
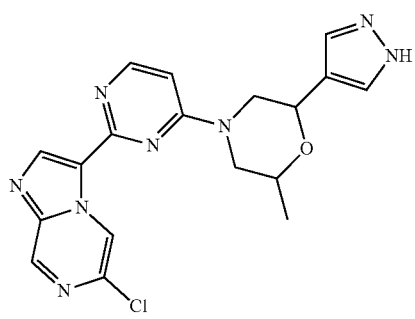 [SMILES: CC1CN(c2ccnc(-c3cnc4cnc(Cl)cn34)n2)CC(c2cn[nH]c2)O1]
IV-193
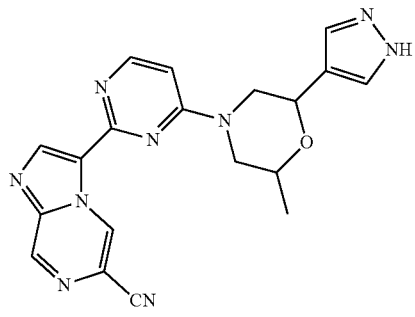
IV-194
single diastereoisomer
(two enantiomers)
IV-195
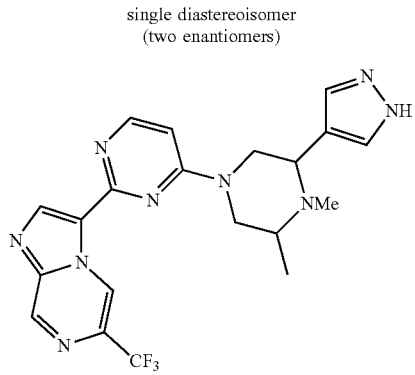

TABLE 3-continued
Exemplary compounds of formula IV
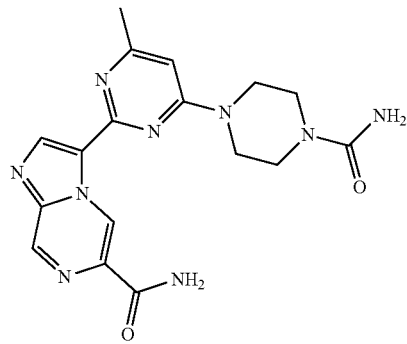 [SMILES: Cc1cc(N2CCN(C(N)=O)CC2)nc(-c2cnc3cnc(C(N)=O)cn23)n1]
IV-196
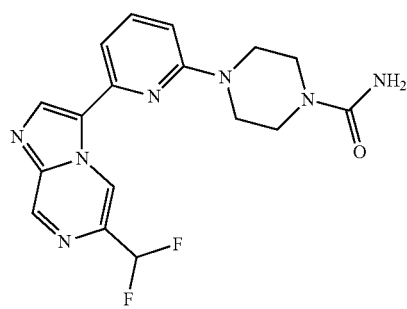 [SMILES: NC(=O)N1CCN(c2cccc(-c3cnc4cnc(C(F)F)cn34)n2)CC1]
IV-197
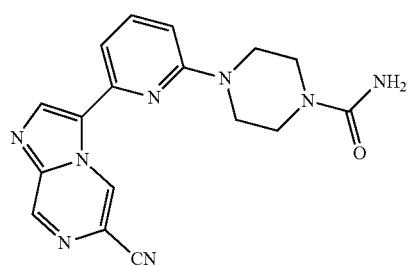 [SMILES: N#Cc1cn2c(-c3cccc(N4CCN(C(N)=O)CC4)n3)cnc2cn1]
IV-198
single stereoisomer
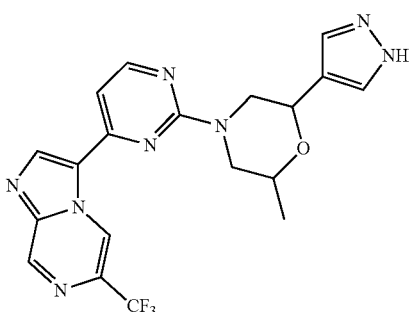
IV-199
TABLE 3-continued
Exemplary compounds of formula IV
single stereoisomer
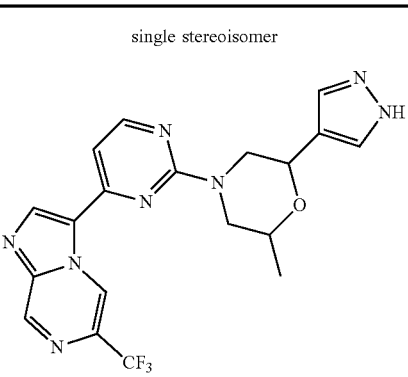
IV-200
single stereoisomer
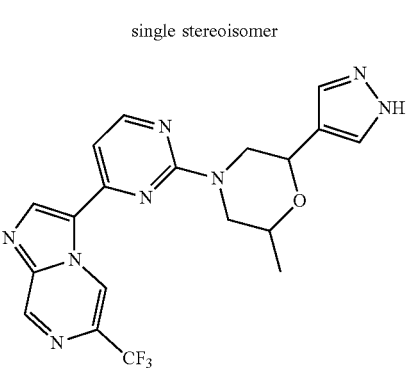
IV-201
single stereoisomer
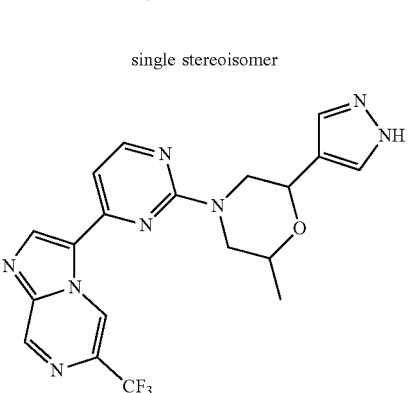
IV-202
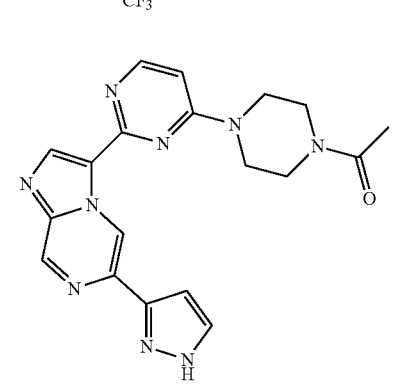
IV-203

TABLE 3-continued
Exemplary compounds of formula IV
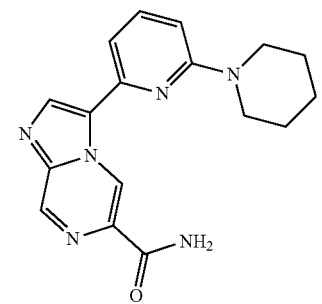 [SMILES: NC(=O)c1cn2c(-c3cccc(N4CCCCC4)n3)cnc2cn1]
IV-204
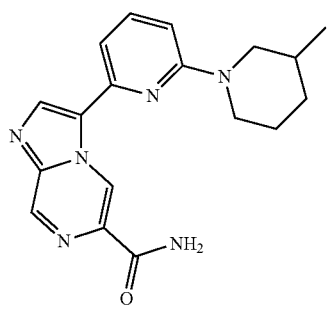 [SMILES: CC1CCCN(c2cccc(-c3cnc4cnc(C(N)=O)cn34)n2)C1]
IV-205
single diastereoisomer
(two enantiomers)
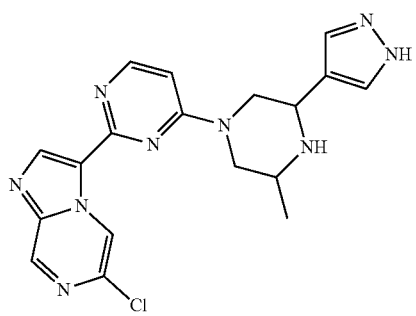 [SMILES: CC1CN(c2ccnc(-c3cnc4cnc(Cl)cn34)n2)CC(c2cn[nH]c2)N1]
IV-206
single diastereoisomer
(two enantiomers)
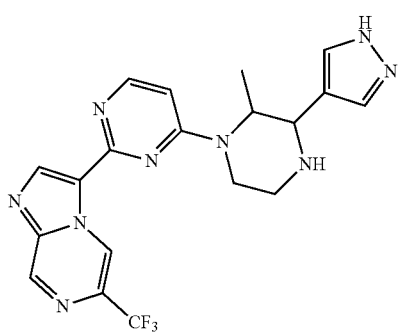 [SMILES: CC1C(c2cn[nH]c2)NCCN1c1ccnc(-c2cnc3cnc(C(F)(F)F)cn23)n1]
IV-207
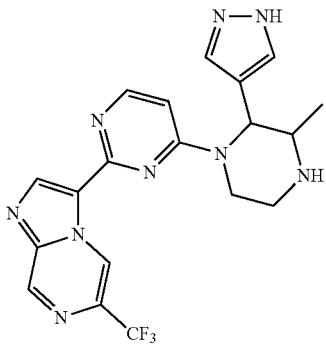 [SMILES: CC1NCCN(c2ccnc(-c3cnc4cnc(C(F)(F)F)cn34)n2)C1c1cn[nH]c1]
IV-208
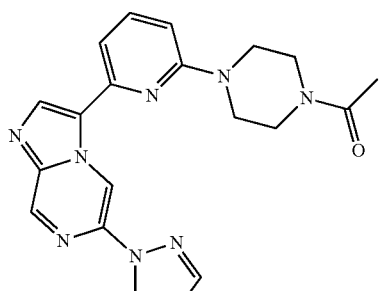
IV-209
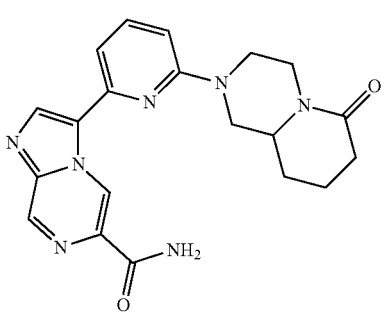 [SMILES: NC(=O)c1cn2c(-c3cccc(N4CCN5C(=O)CCCC5C4)n3)cnc2cn1]
IV-210
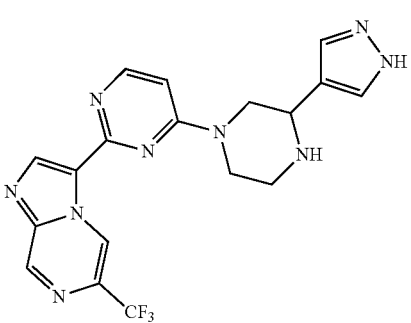 [SMILES: FC(F)(F)c1cn2c(-c3nccc(N4CCNC(c5cn[nH]c5)C4)n3)cnc2cn1]
IV-211
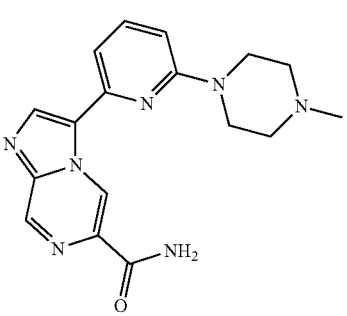 [SMILES: CN1CCN(c2cccc(-c3cnc4cnc(C(N)=O)cn34)n2)CC1]
IV-212

TABLE 3-continued
Exemplary compounds of formula IV
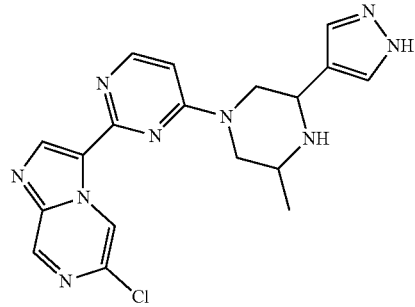
IV-213
single stereoisomer IV-214
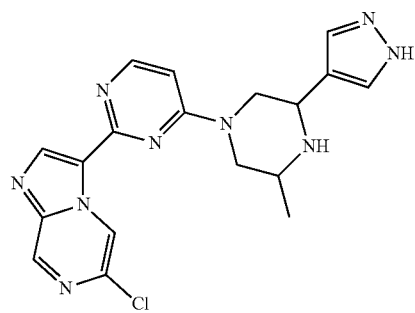 [SMILES: CC1CN(c2ccnc(-c3cnc4cnc(Cl)cn34)n2)CC(c2cn[nH]c2)N1]
single diastereoisomer IV-215
(two enantiomers)
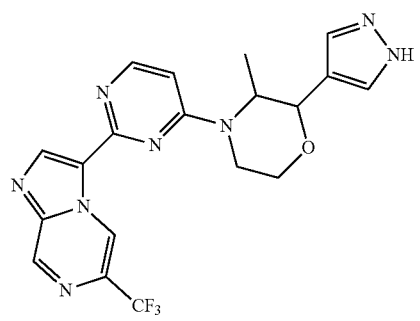
single stereoisomer IV-216
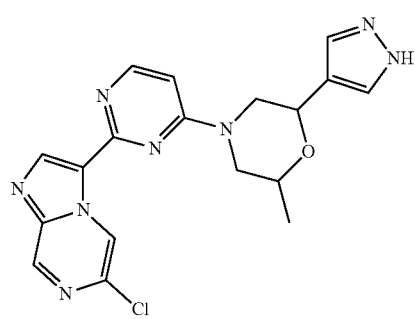 [SMILES: CC1CN(c2ccnc(-c3cnc4cnc(Cl)cn34)n2)CC(c2cn[nH]c2)O1]
TABLE 3-continued
Exemplary compounds of formula IV
single stereoisomer IV-217
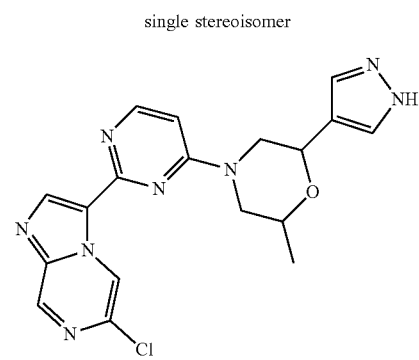
single diastereoisomer IV-218
(two enantiomers)
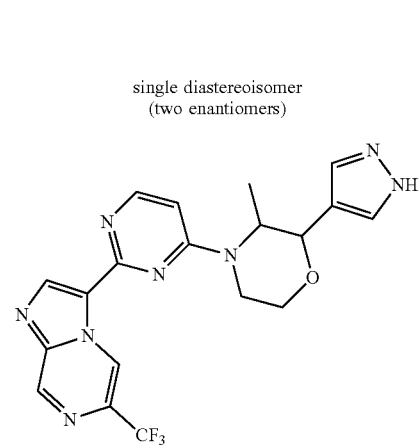
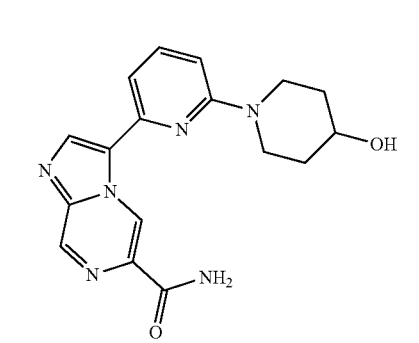
IV-219
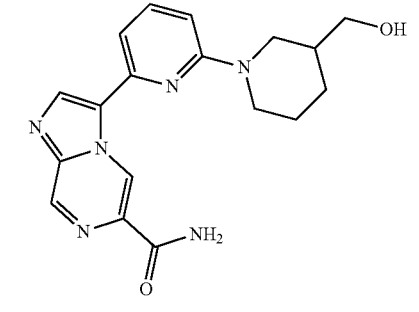 [SMILES: NC(=O)c1cn2c(-c3cccc(N4CCCC(CO)C4)n3)cnc2cn1]
IV-220

TABLE 3-continued
Exemplary compounds of formula IV
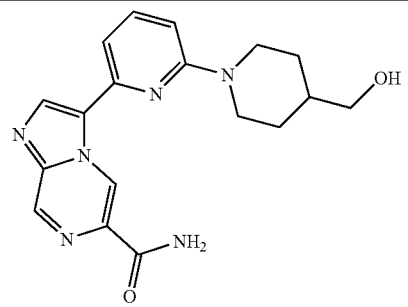
IV-221
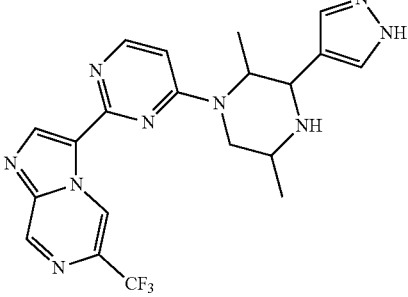
IV-222
single stereoisomer
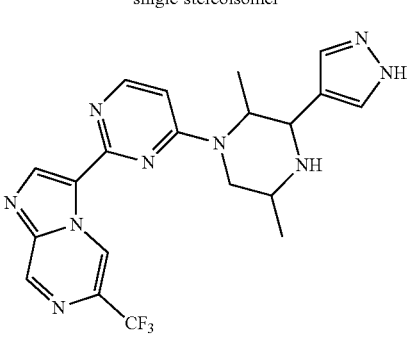
IV-223
single stereoisomer
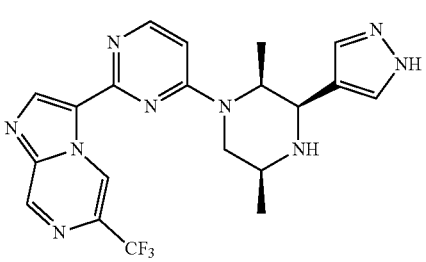 [SMILES: C[C@H]1CN(c2ccnc(-c3cnc4cnc(C(F)(F)F)cn34)n2)[C@@H](C)[C@@H](c2cn[nH]c2)N1]
IV-224
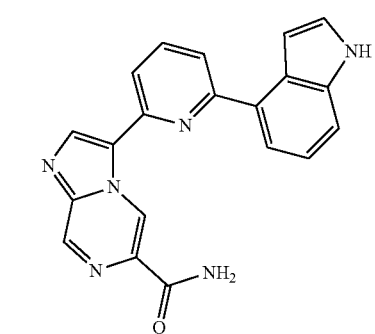 [SMILES: NC(=O)c1cn2c(-c3cccc(-c4cccc5[nH]ccc45)n3)cnc2cn1]
IV-225
TABLE 3-continued
Exemplary compounds of formula IV
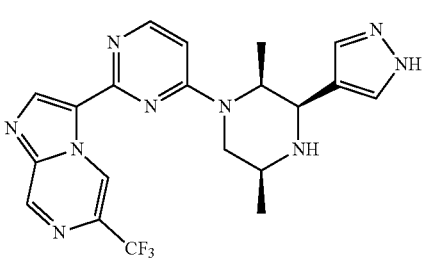
IV-226
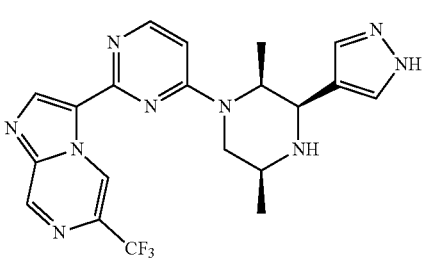
IV-227
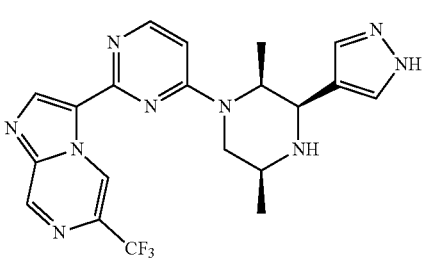
IV-228
single diastereoisomer
(two enantiomers)
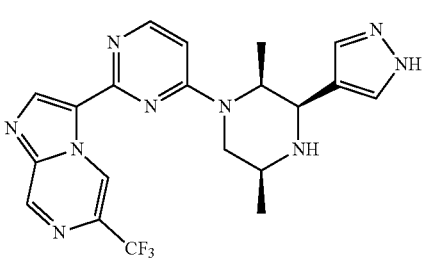
IV-229

TABLE 3-continued
Exemplary compounds of formula IV
single diastereoisomer (two enantiomers) IV-230
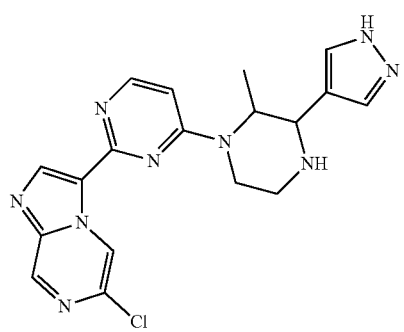 [SMILES: CC1C(c2cn[nH]c2)NCCN1c1ccnc(-c2cnc3cnc(Cl)cn23)n1]
single stereoisomer IV-231
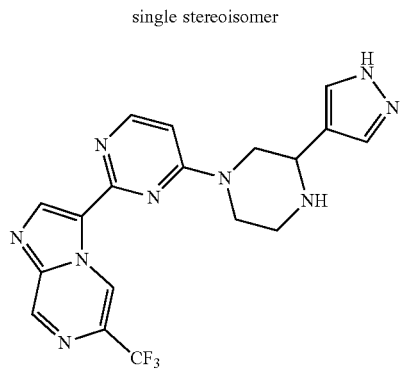
single stereoisomer IV-232
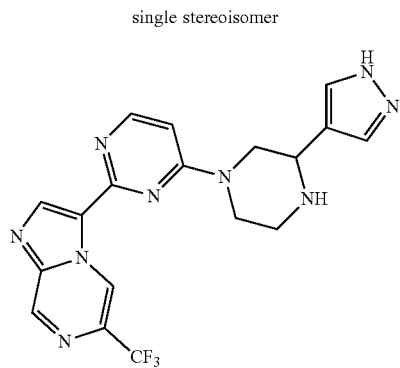
IV-233
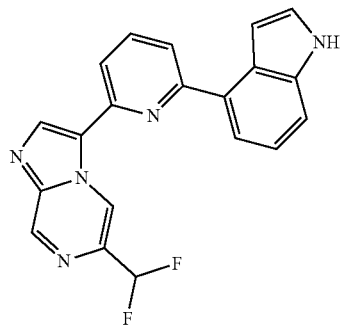 [SMILES: FC(F)c1cn2c(-c3cccc(-c4cccc5[nH]ccc45)n3)cnc2cn1]
TABLE 3-continued
Exemplary compounds of formula IV
IV-234
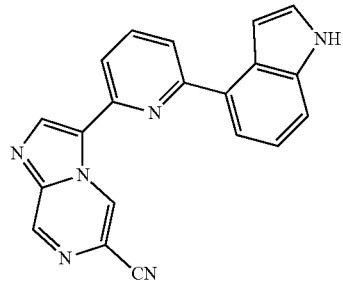 [SMILES: N#Cc1cn2c(-c3cccc(-c4cccc5[nH]ccc45)n3)cnc2cn1]
single diastereoisomer (two enantiomers) IV-235
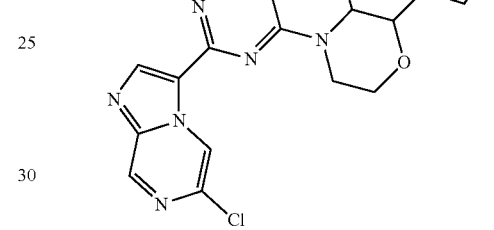
single diastereoisomer (two enantiomers) IV-236
single stereoisomer IV-237

TABLE 3-continued
Exemplary compounds of formula IV
single stereoisomer IV-238
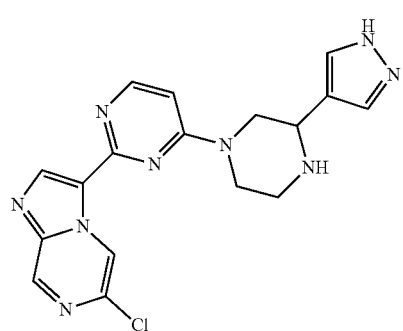 [SMILES: Clc1cn2c(-c3nccc(N4CCNC(c5cn[nH]c5)C4)n3)cnc2cn1]
IV-239
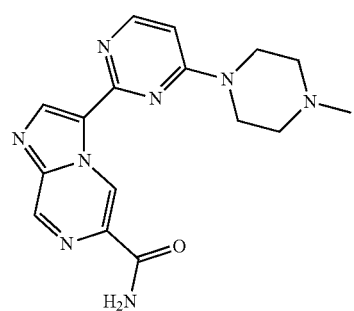 [SMILES: CN1CCN(c2ccnc(-c3cnc4cnc(C(N)=O)cn34)n2)CC1]
IV-240
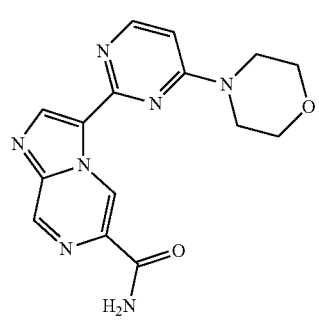 [SMILES: NC(=O)c1cn2c(-c3nccc(N4CCOCC4)n3)cnc2cn1]
IV-241
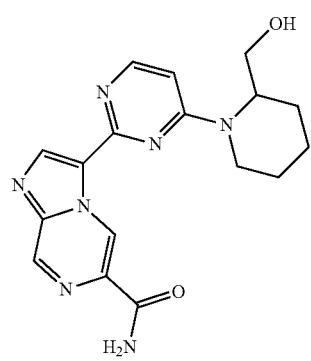 [SMILES: NC(=O)c1cn2c(-c3nccc(N4CCCCC4CO)n3)cnc2cn1]
TABLE 3-continued
Exemplary compounds of formula IV
IV-242
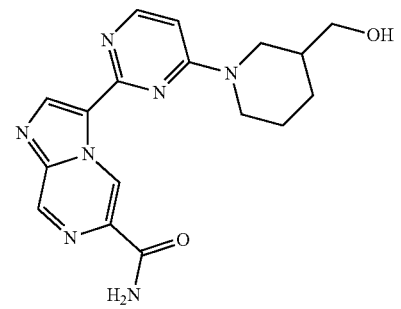 [SMILES: NC(=O)c1cn2c(-c3nccc(N4CCCC(CO)C4)n3)cnc2cn1]
IV-243
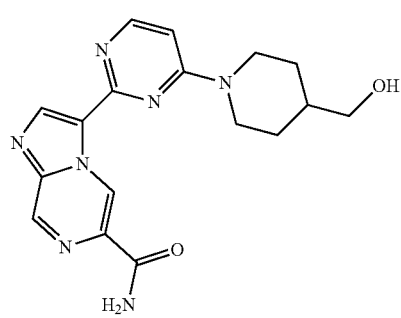 [SMILES: NC(=O)c1cn2c(-c3nccc(N4CCC(CO)CC4)n3)cnc2cn1]
single stereoisomer IV-244
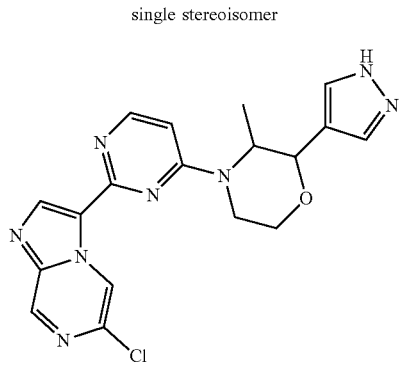
single stereoisomer IV-245
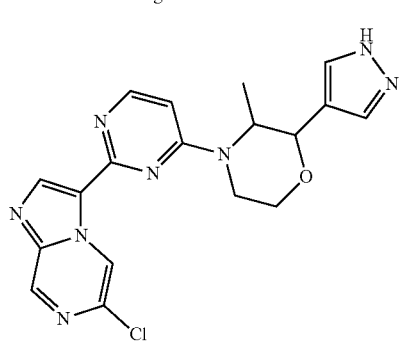

TABLE 3-continued
Exemplary compounds of formula IV
| | |
|---|---|
| single stereoisomer 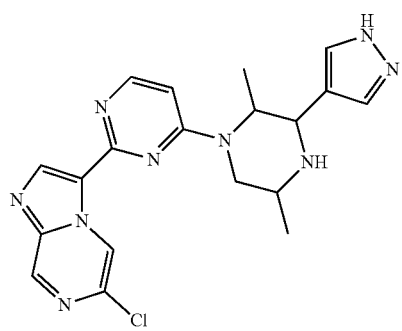 [SMILES: CC1CN(c2ccnc(-c3cnc4cnc(Cl)cn34)n2)C(C)C(c2cn[nH]c2)N1] | IV-246 |
| single stereoisomer 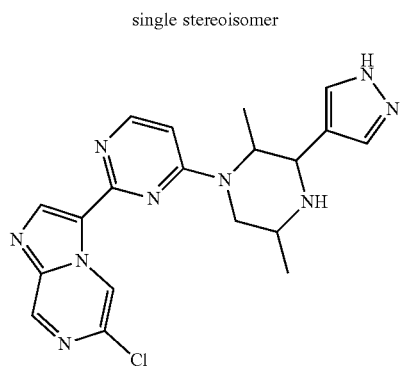 | IV-247 |
| 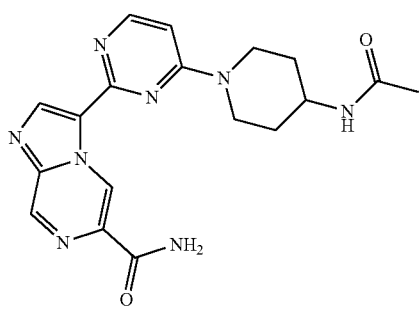 [SMILES: CC(=O)NC1CCN(c2ccnc(-c3cnc4cnc(C(N)=O)cn34)n2)CC1] | IV-248 |
| 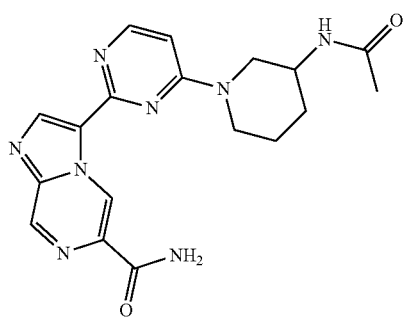 [SMILES: CC(=O)NC1CCCN(c2ccnc(-c3cnc4cnc(C(N)=O)cn34)n2)C1] | IV-249 |
| 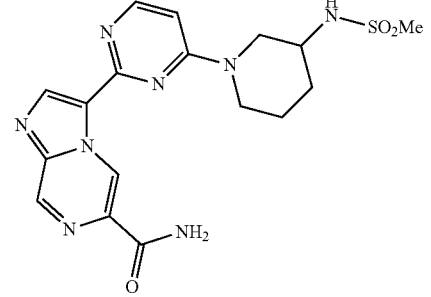 | IV-250 |
| 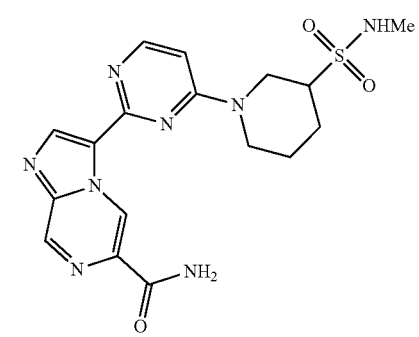 [SMILES: CNS(=O)(=O)C1CCCN(c2ccnc(-c3cnc4cnc(C(N)=O)cn34)n2)C1] | IV-251 |
| 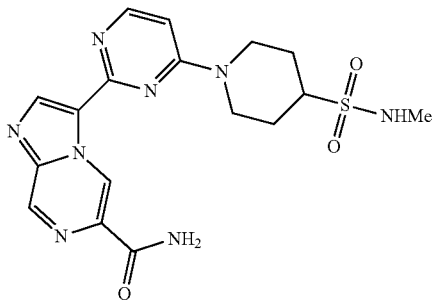 [SMILES: CNS(=O)(=O)C1CCN(c2ccnc(-c3cnc4cnc(C(N)=O)cn34)n2)CC1] | IV-252 |
| 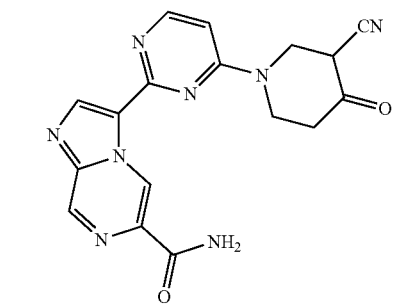 [SMILES: N#CC1CN(c2ccnc(-c3cnc4cnc(C(N)=O)cn34)n2)CCC1=O] | IV-253 |
| 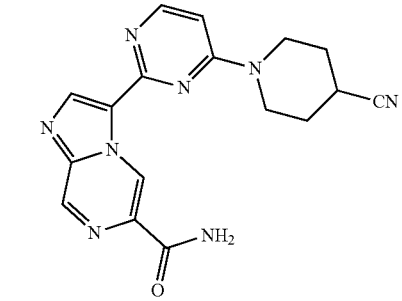 [SMILES: N#CC1CCN(c2ccnc(-c3cnc4cnc(C(N)=O)cn34)n2)CC1] | IV-254 |

TABLE 3-continued
Exemplary compounds of formula IV
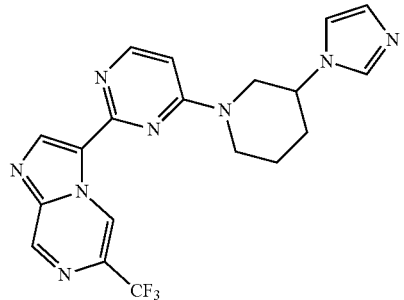 IV-255
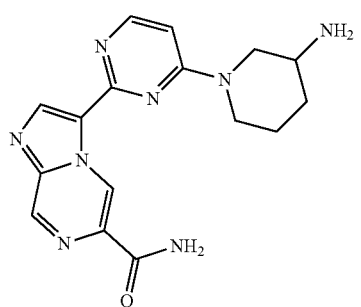 [SMILES: NC(=O)c1cn2c(-c3nccc(N4CCCC(N)C4)n3)cnc2cn1] IV-256
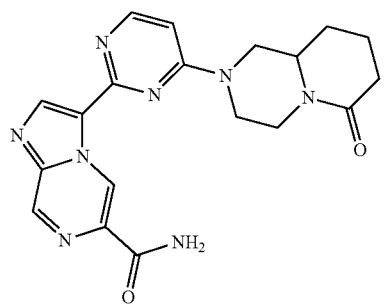 [SMILES: NC(=O)c1cn2c(-c3nccc(N4CCN5C(=O)CCCC5C4)n3)cnc2cn1] IV-257
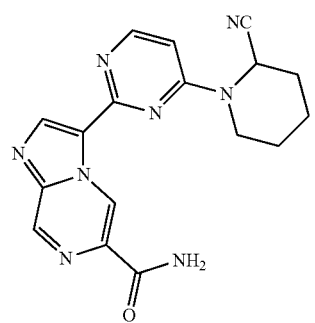 [SMILES: N#CC1CCCCN1c1ccnc(-c2cnc3cnc(C(N)=O)cn23)n1] IV-258
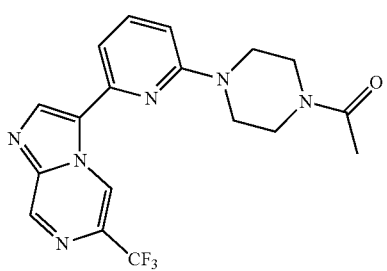 [SMILES: CC(=O)N1CCN(c2cccc(-c3cnc4cnc(C(F)(F)F)cn34)n2)CC1] IV-259
TABLE 3-continued
Exemplary compounds of formula IV
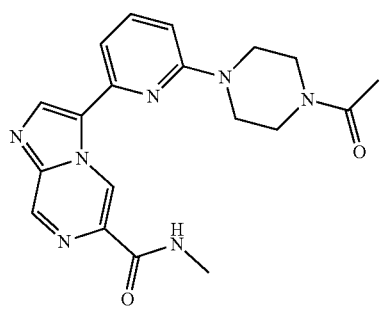 [SMILES: CNC(=O)c1cn2c(-c3cccc(N4CCN(C(C)=O)CC4)n3)cnc2cn1] IV-260
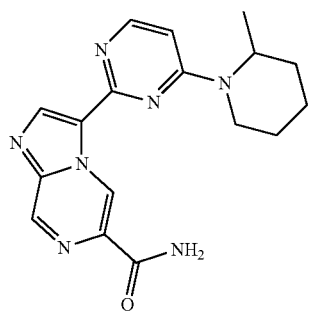 [SMILES: CC1CCCCN1c1ccnc(-c2cnc3cnc(C(N)=O)cn23)n1] IV-261
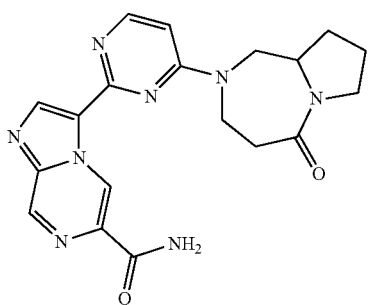 [SMILES: NC(=O)c1cn2c(-c3nccc(N4CCC(=O)N5CCCC5C4)n3)cnc2cn1] IV-262
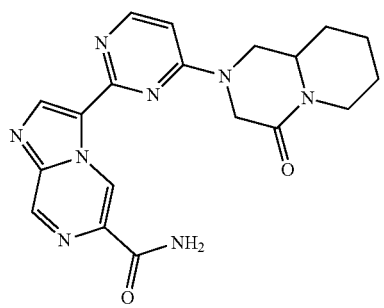 [SMILES: NC(=O)c1cn2c(-c3nccc(N4CC(=O)N5CCCCC5C4)n3)cnc2cn1] IV-263
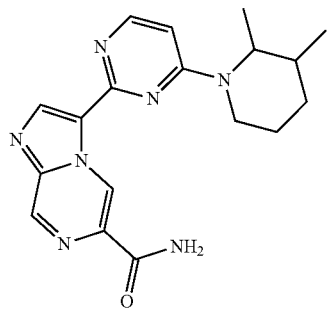 IV-264

TABLE 3-continued
Exemplary compounds of formula IV
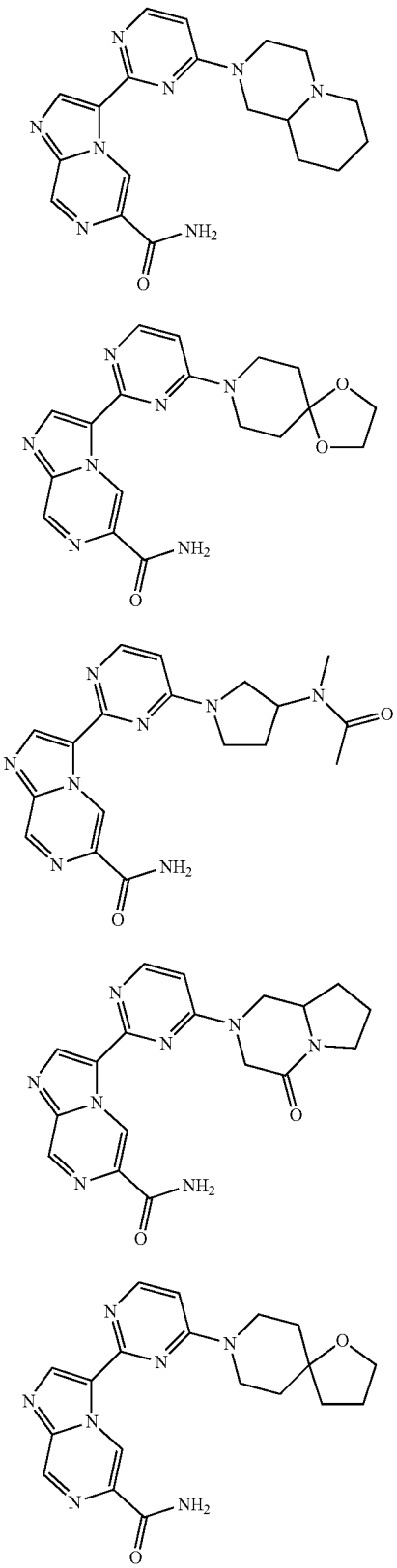
IV-265
IV-266
IV-267
IV-268
IV-269
TABLE 3-continued
Exemplary compounds of formula IV
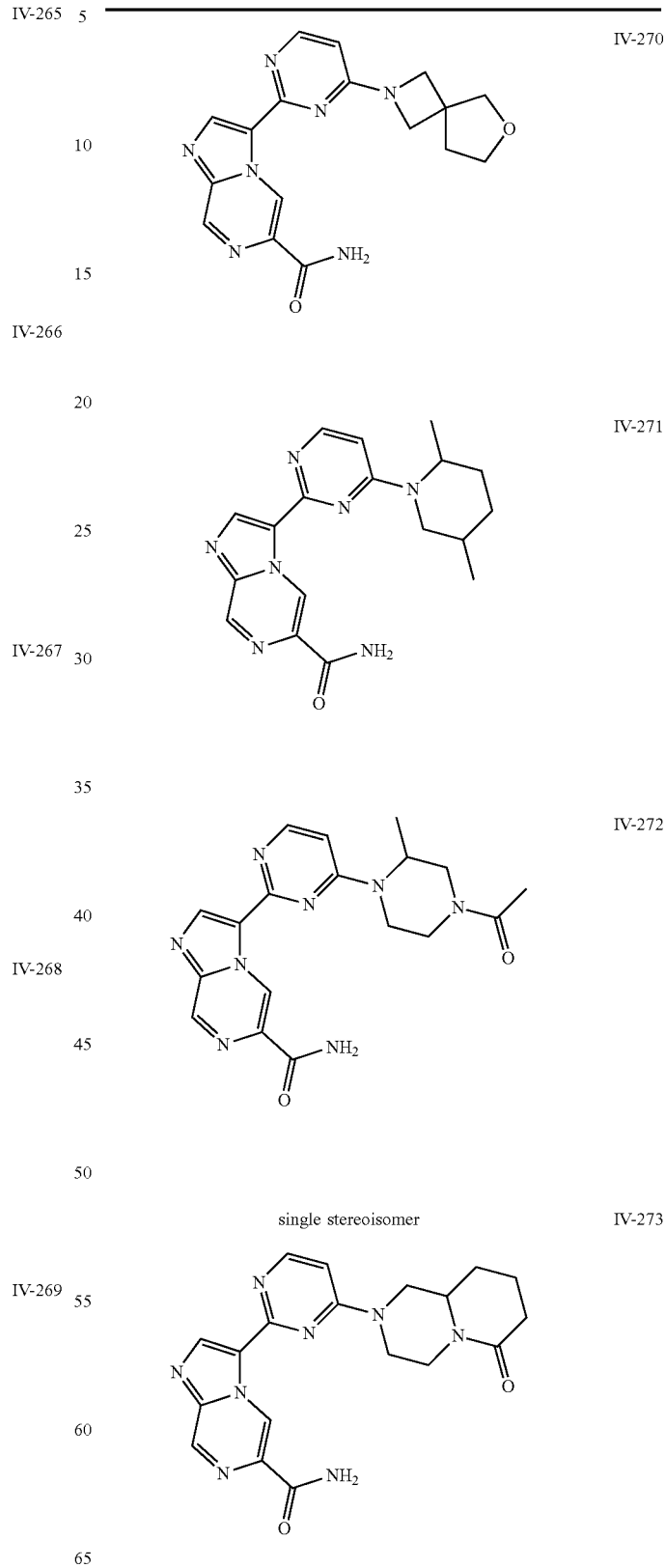
IV-270
IV-271
IV-272
single stereoisomer    IV-273

TABLE 3-continued
Exemplary compounds of formula IV
| | |
|---|---|
| single stereoisomer 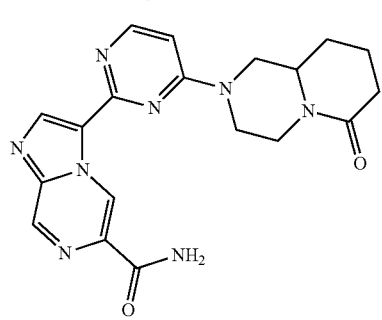 [SMILES: NC(=O)c1cn2c(-c3nccc(N4CCN5C(=O)CCCC5C4)n3)cnc2cn1] | IV-274 |
| single stereoisomer 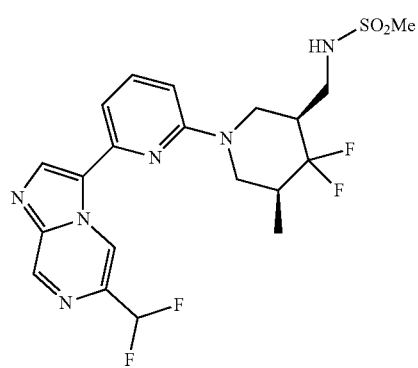 [SMILES: C[C@H]1CN(c2cccc(-c3cnc4cnc(C(F)F)cn34)n2)C[C@@H](CNS(C)(=O)=O)C1(F)F] | IV-275 |
| 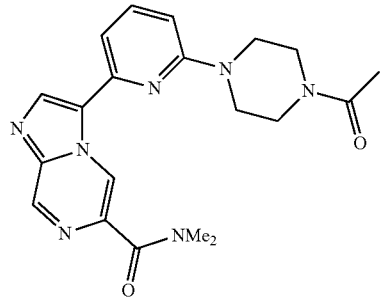 [SMILES: CC(=O)N1CCN(c2cccc(-c3cnc4cnc(C(=O)N(C)C)cn34)n2)CC1] | IV-276 |
| 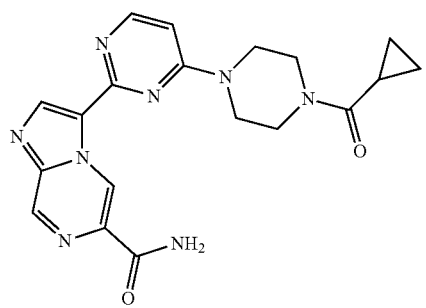 [SMILES: NC(=O)c1cn2c(-c3nccc(N4CCN(C(=O)C5CC5)CC4)n3)cnc2cn1] | IV-277 |
| single diastereoisomer (two enantiomers) 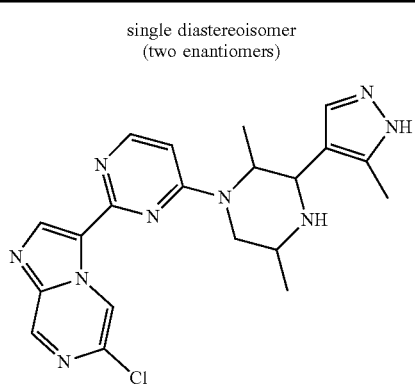 | IV-278 |
| single diastereoisomer (two enantiomers) 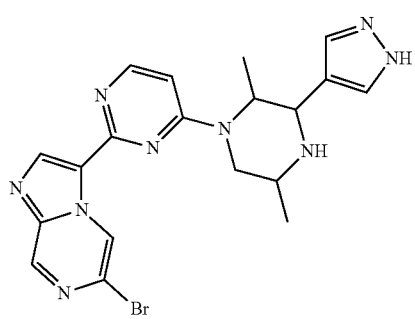 [SMILES: CC1CN(c2ccnc(-c3cnc4cnc(Br)cn34)n2)C(C)C(c2cn[nH]c2)N1] | IV-279 |
| single diastereoisomer (two enantiomers) 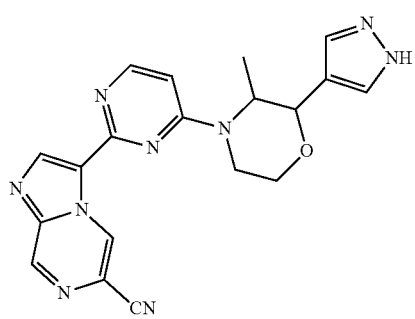 [SMILES: CC1C(c2cn[nH]c2)OCCN1c1ccnc(-c2cnc3cnc(C#N)cn23)n1] | IV-280 |
| single diastereoisomer (two enantiomers) 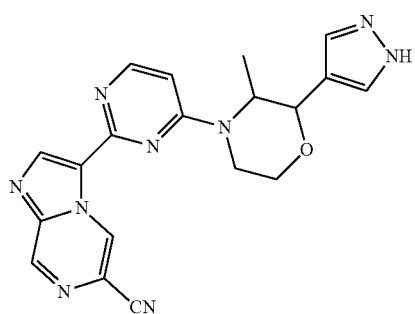 [SMILES: CC1C(c2cn[nH]c2)OCCN1c1ccnc(-c2cnc3cnc(C#N)cn23)n1] | IV-281 |

TABLE 3-continued

Exemplary compounds of formula IV

| single stereoisomer | IV-282 |
| single stereoisomer | IV-283 |
| | IV-284 |
| | IV-285 |
| | IV-286 |
| single stereoisomer | IV-287 |
| single stereoisomer | IV-288 |
| | IV-289 |
| single stereoisomer | IV-290 |

TABLE 3-continued
Exemplary compounds of formula IV
| | |
|---|---|
| single stereoisomer | IV-291 |
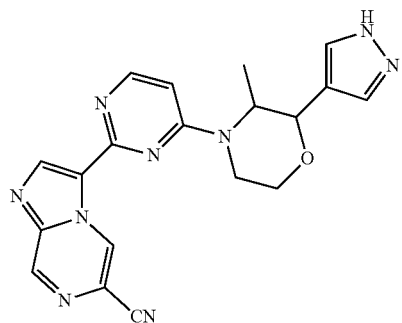
| | |
|---|---|
| single diastereoisomer (two enantiomers) | IV-292 |
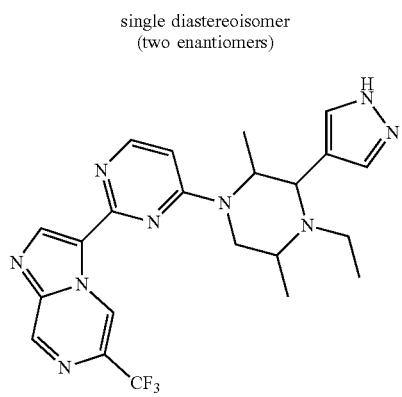
| | |
|---|---|
| single stereoisomer | IV-293 |
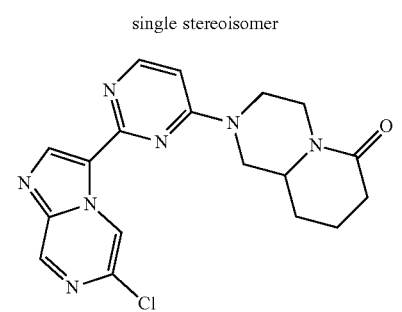
| | |
|---|---|
| single stereoisomer | IV-294 |
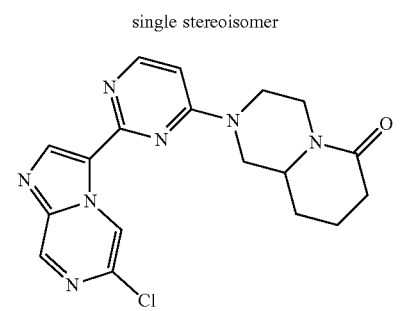
TABLE 3-continued
Exemplary compounds of formula IV
| | |
|---|---|
| single stereoisomer | IV-295 |
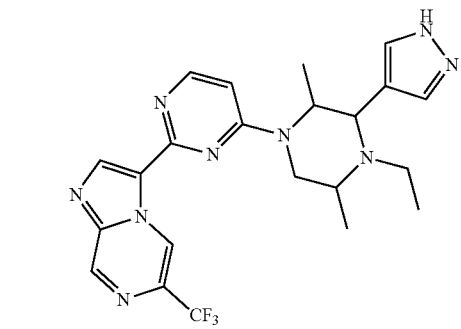
| | |
|---|---|
| single stereoisomer | IV-296 |
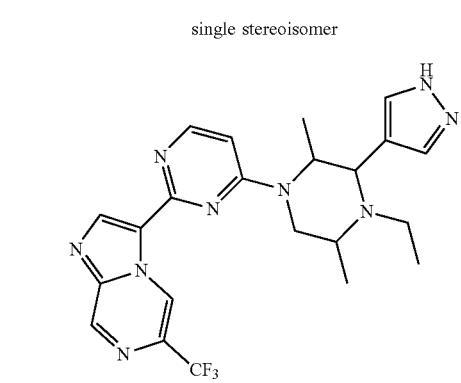
IV-297
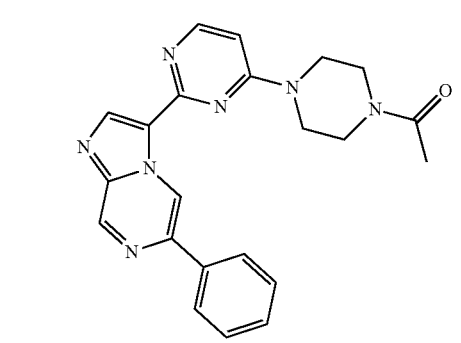 [SMILES: CC(=O)N1CCN(c2ccnc(-c3cnc4cnc(-c5ccccc5)cn34)n2)CC1]
IV-298
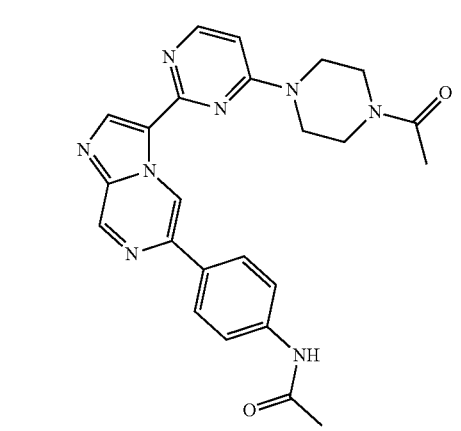 [SMILES: CC(=O)Nc1ccc(-c2cn3c(-c4nccc(N5CCN(C(C)=O)CC5)n4)cnc3cn2)cc1]

TABLE 3-continued
Exemplary compounds of formula IV
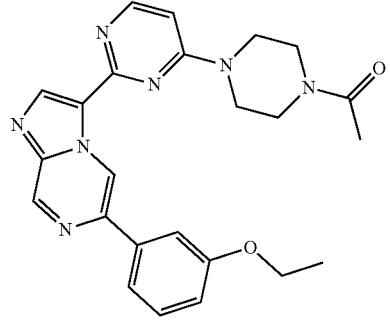 [SMILES: CCOc1cccc(-c2cn3c(-c4nccc(N5CCN(C(C)=O)CC5)n4)cnc3cn2)c1]
IV-299
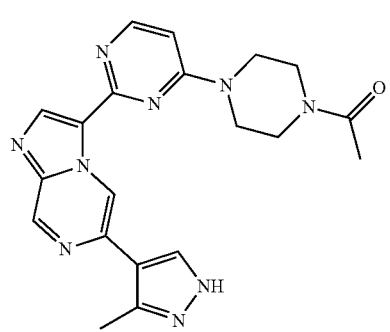 [SMILES: CC(=O)N1CCN(c2ccnc(-c3cnc4cnc(-c5c[nH]nc5C)cn34)n2)CC1]
IV-300
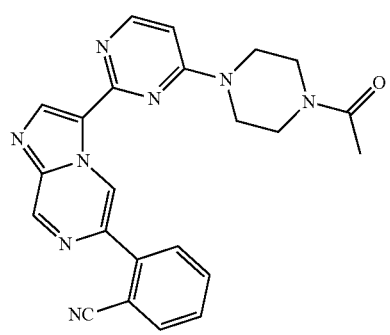 [SMILES: CC(=O)N1CCN(c2ccnc(-c3cnc4cnc(-c5ccccc5C#N)cn34)n2)CC1]
IV-301
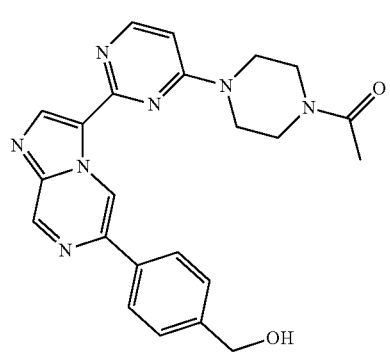 [SMILES: CC(=O)N1CCN(c2ccnc(-c3cnc4cnc(-c5ccc(CO)cc5)cn34)n2)CC1]
IV-302
TABLE 3-continued
Exemplary compounds of formula IV
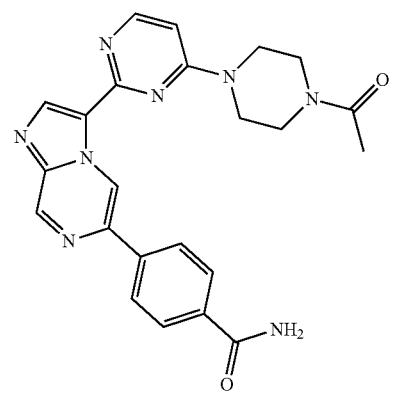 [SMILES: CC(=O)N1CCN(c2ccnc(-c3cnc4cnc(-c5ccc(C(N)=O)cc5)cn34)n2)CC1]
IV-303
single diastereoisomer (two enantiomers)
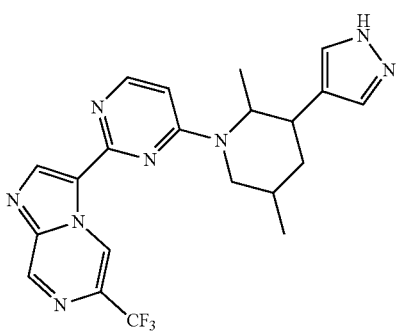
IV-304
single diastereoisomer (two enantiomers)
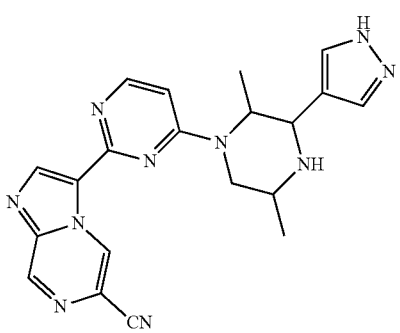 [SMILES: CC1CN(c2ccnc(-c3cnc4cnc(C#N)cn34)n2)C(C)C(c2cn[nH]c2)N1]
IV-305
single diastereoisomer (two enantiomers)
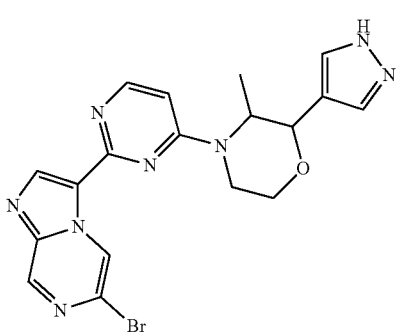
IV-306

TABLE 3-continued
Exemplary compounds of formula IV
IV-307
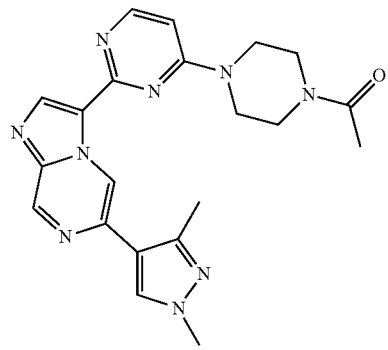 [SMILES: CC(=O)N1CCN(c2ccnc(-c3cnc4cnc(-c5cn(C)nc5C)cn34)n2)CC1]
IV-308
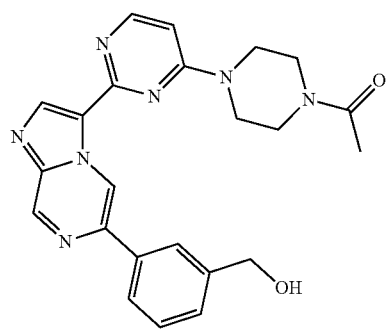 [SMILES: CC(=O)N1CCN(c2ccnc(-c3cnc4cnc(-c5cccc(CO)c5)cn34)n2)CC1]
IV-309
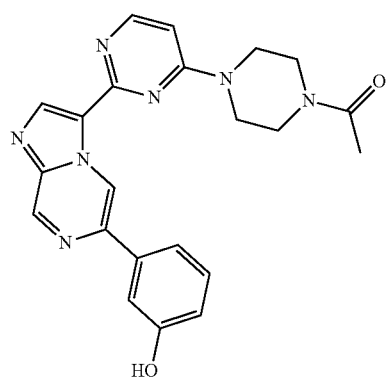 [SMILES: CC(=O)N1CCN(c2ccnc(-c3cnc4cnc(-c5cccc(O)c5)cn34)n2)CC1]
single stereoisomer  IV-310
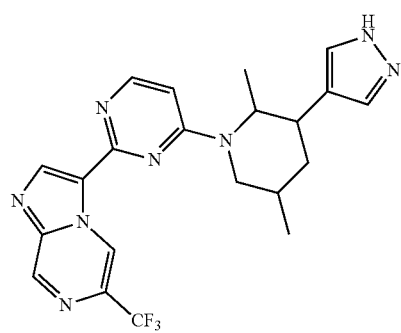
TABLE 3-continued
Exemplary compounds of formula IV
single stereoisomer  IV-311
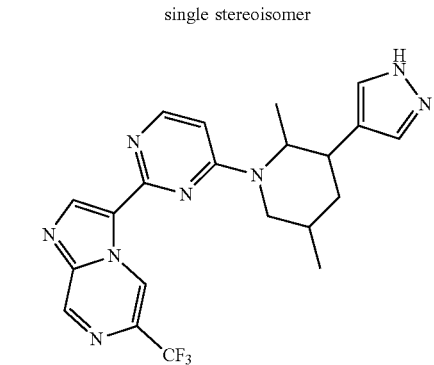
single diastereoisomer  IV-312
(two enantiomers)
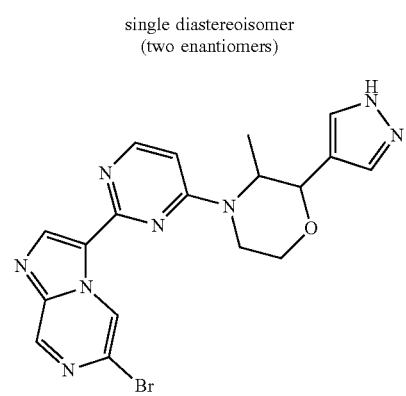
single stereoisomer  IV-313
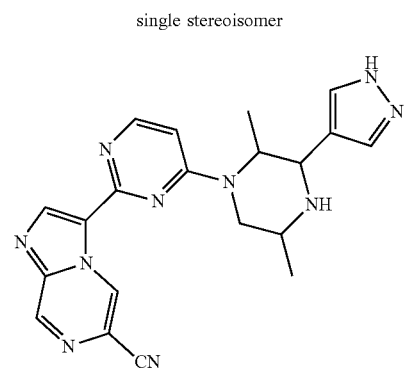
single stereoisomer  IV-314
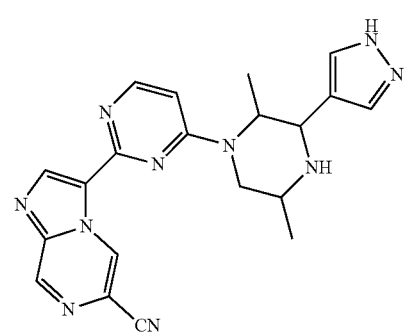

TABLE 3-continued
Exemplary compounds of formula IV
| single stereoisomer | IV-315 |
| single stereoisomer | IV-316 |
| | IV-317 |
| single stereoisomer | IV-318 |
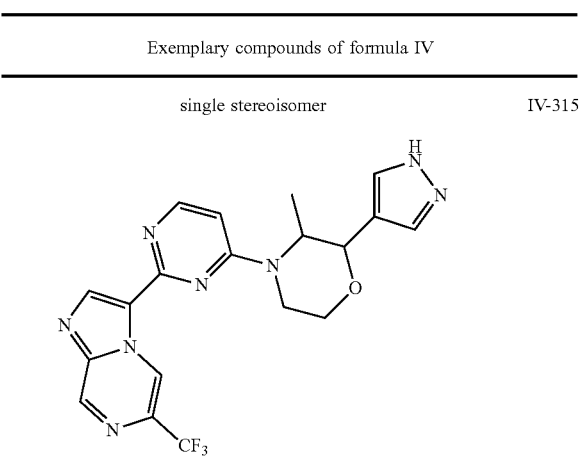
TABLE 3-continued
Exemplary compounds of formula IV
| | IV-319 |
| | IV-320 |
| | IV-321 |
| | IV-322 |
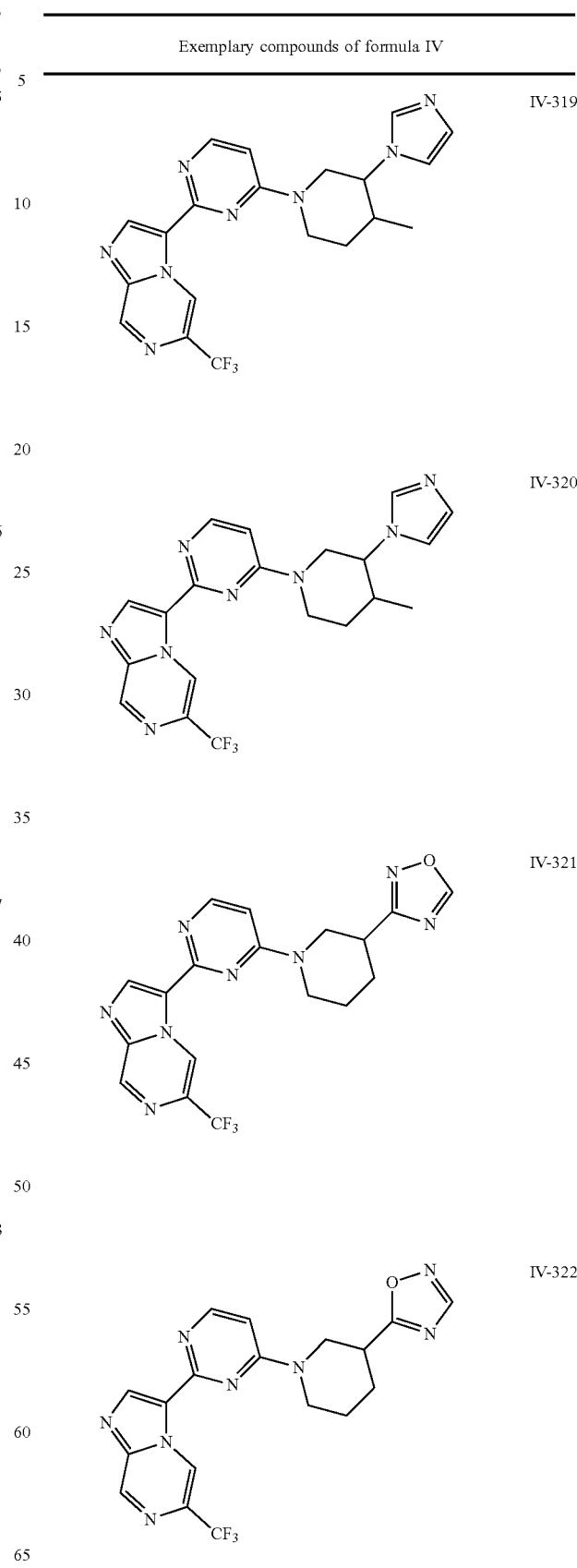

TABLE 3-continued

Exemplary compounds of formula IV

| | |
|---|---|
| single diastereoisomer (two enantiomers) | IV-323 |
| single diastereomer (two enantiomers) | IV-324 |
| | IV-325 |
| | IV-326 |
| | IV-327 |
| single stereoisomer | IV-328 |
| | IV-329 |
| single diastereoisomer (two enantiomers) | IV-330 |

TABLE 3-continued
Exemplary compounds of formula IV
| | |
|---|---|
| 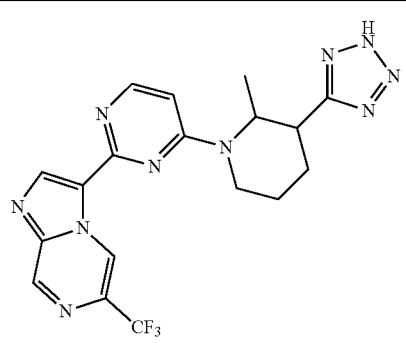 IV-331 | single diastereomer (two enantiomers) IV-335 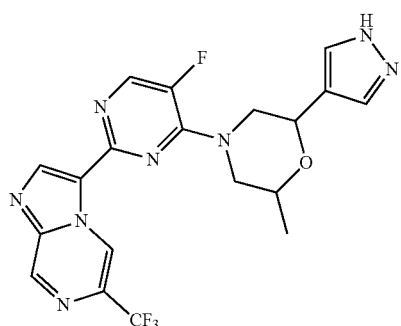 |
|  IV-332 | single stereoisomer IV-336 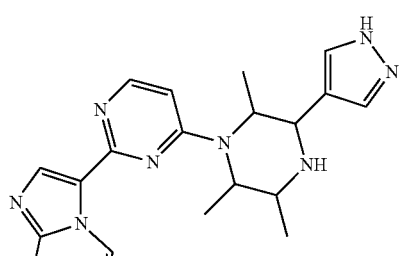 |
| single diastereomer (two enantiomers) IV-333  | single stereoisomer IV-337 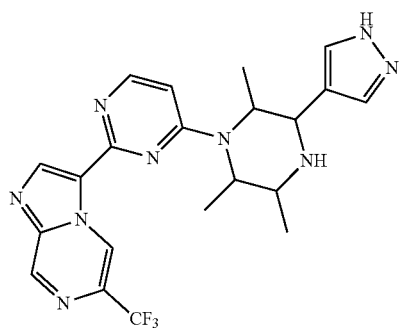 |
| single diastereomer (two enantiomers) IV-334 | single stereoisomer IV-338 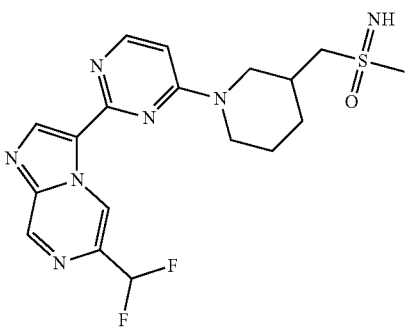 [SMILES: CS(=N)(=O)CC1CCCN(c2ccnc(-c3cnc4cnc(C(F)F)cn34)n2)C1] |

TABLE 3-continued
Exemplary compounds of formula IV
single stereoisomer IV-339
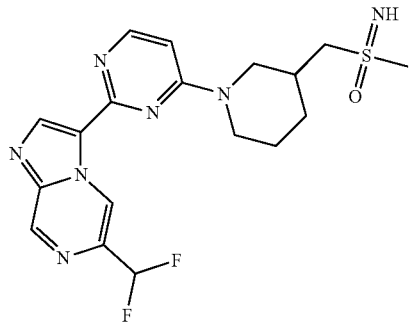 [SMILES: CS(=N)(=O)CC1CCCN(c2ccnc(-c3cnc4cnc(C(F)F)cn34)n2)C1]
IV-340
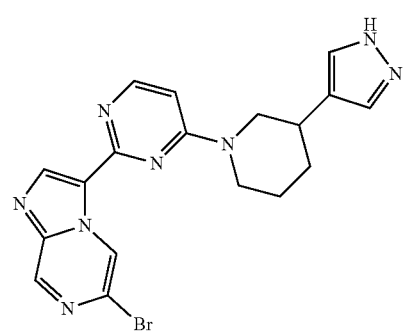 [SMILES: Brc1cn2c(-c3nccc(N4CCCC(c5cn[nH]c5)C4)n3)cnc2cn1]
IV-341
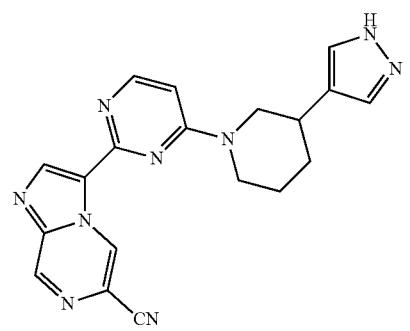 [SMILES: N#Cc1cn2c(-c3nccc(N4CCCC(c5cn[nH]c5)C4)n3)cnc2cn1]
single diastereoisomer IV-342
(two enantiomers)
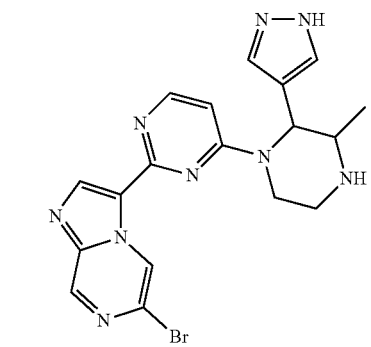 [SMILES: CC1NCCN(c2ccnc(-c3cnc4cnc(Br)cn34)n2)C1c1cn[nH]c1]
TABLE 3-continued
Exemplary compounds of formula IV
single diastereoisomer IV-343
(two enantiomers)
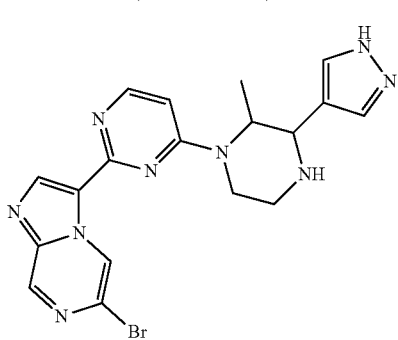
single diastereoisomer IV-344
(two enantiomers)
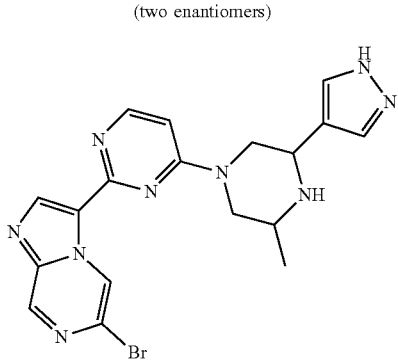
single diastereoisomer IV-345
(two enantiomers)
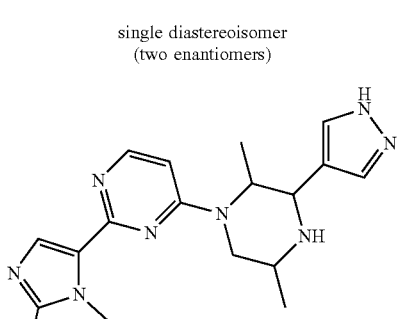
IV-346
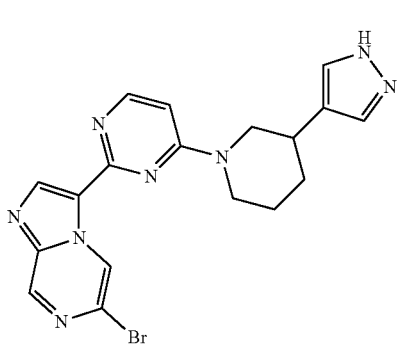 [SMILES: Brc1cn2c(-c3nccc(N4CCCC(c5cn[nH]c5)C4)n3)cnc2cn1]

TABLE 3-continued
Exemplary compounds of formula IV
IV-347
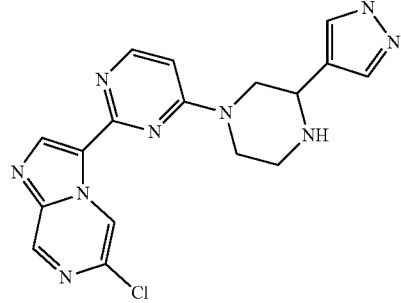
IV-348
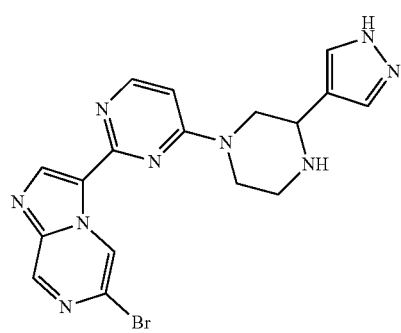 [SMILES: Clc1cn2c(-c3nccc(N4CCNC(c5cn[nH]c5)C4)n3)cnc2cn1]
IV-349
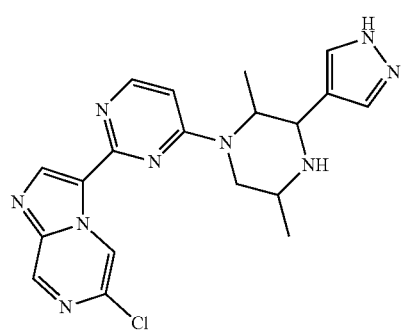 [SMILES: CC1CN(c2ccnc(-c3cnc4cnc(Cl)cn34)n2)C(C)C(c2cn[nH]c2)N1]
single stereoisomer IV-350
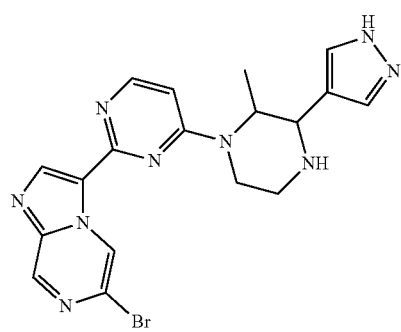
TABLE 3-continued
Exemplary compounds of formula IV
single stereoisomer IV-351
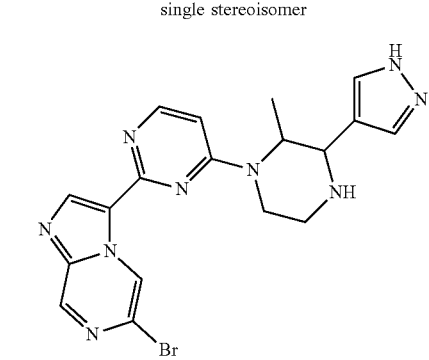
IV-352
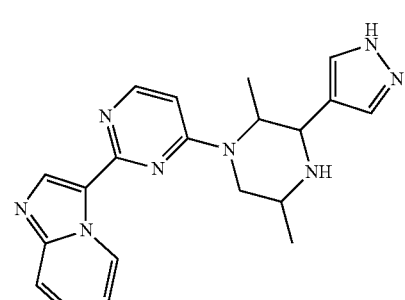
IV-353
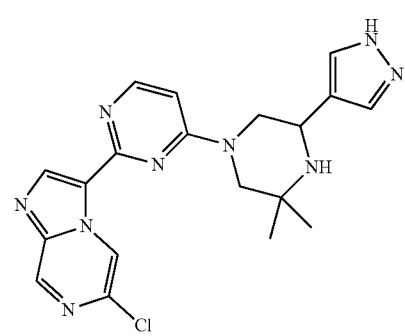 [SMILES: CC1(C)CN(c2ccnc(-c3cnc4cnc(Cl)cn34)n2)CC(c2cn[nH]c2)N1]
IV-354
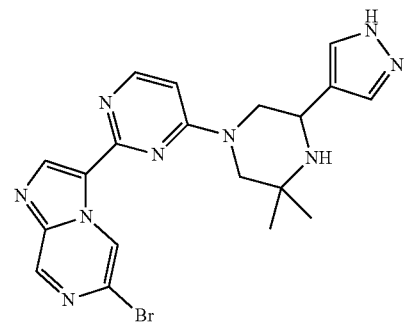

TABLE 3-continued
Exemplary compounds of formula IV
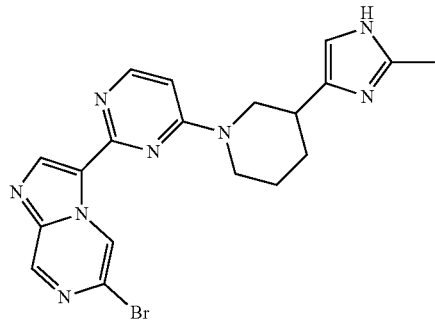 [SMILES: Cc1nc(C2CCCN(c3ccnc(-c4cnc5cnc(Br)cn45)n3)C2)c[nH]1]
IV-355
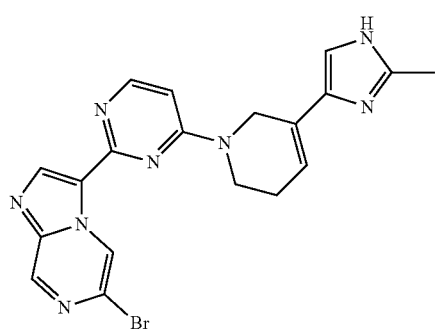 [SMILES: Cc1nc(C2=CCCN(c3ccnc(-c4cnc5cnc(Br)cn45)n3)C2)c[nH]1]
IV-356
single stereoisomer
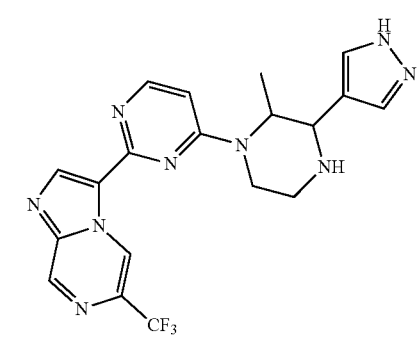
IV-357
single stereoisomer
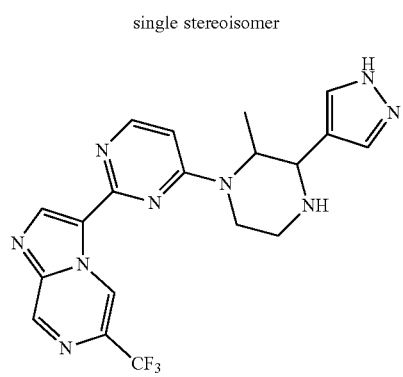
IV-358
TABLE 3-continued
Exemplary compounds of formula IV
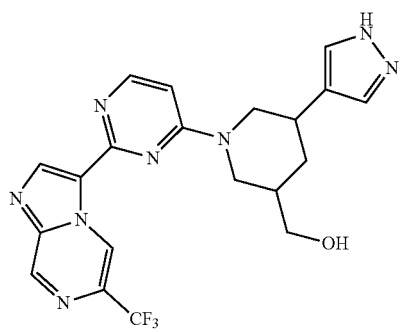
IV-359
single stereoisomer
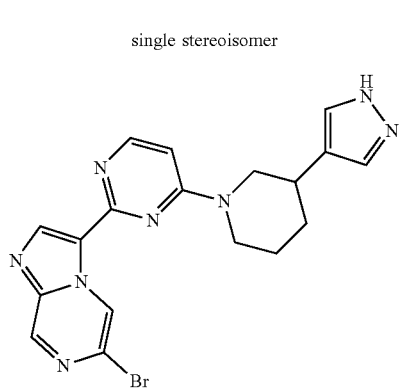
IV-360
single stereoisomer
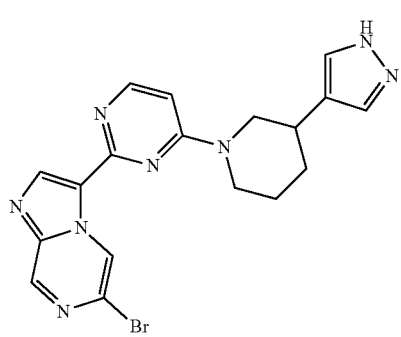 [SMILES: Brc1cn2c(-c3nccc(N4CCCC(c5cn[nH]c5)C4)n3)cnc2cn1]
IV-361
single stereoisomer
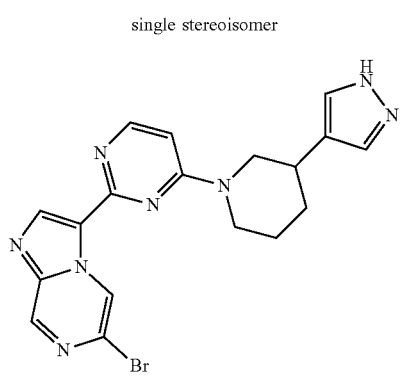
IV-362

TABLE 3-continued

Exemplary compounds of formula IV

| single stereoisomer | IV-363 |
| single stereoisomer | IV-364 |
| single stereoisomer | IV-365 |
| single stereoisomer | IV-366 |
| single stereoisomer | IV-367 |
| single stereoisomer | IV-368 |
| single stereoisomer | IV-369 |
| single stereoisomer | IV-370 |

TABLE 3-continued
Exemplary compounds of formula IV
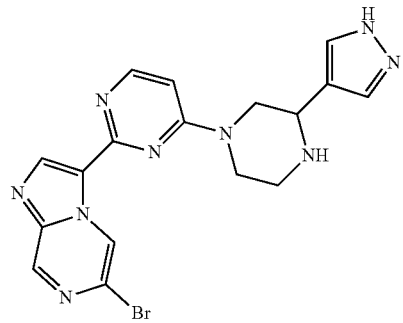 [SMILES: Brc1cn2c(-c3nccc(N4CCNC(c5cn[nH]c5)C4)n3)cnc2cn1]
IV-371
single diastereoisomer (two enantiomers)
IV-372
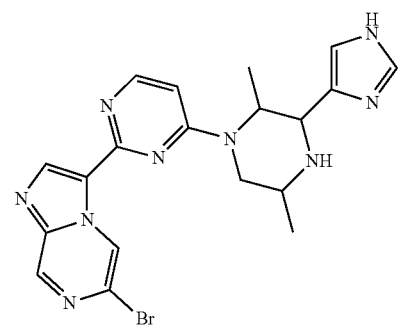 [SMILES: CC1CN(c2ccnc(-c3cnc4cnc(Br)cn34)n2)C(C)C(c2c[nH]cn2)N1]
single diastereoisomer (two enantiomers)
IV-373
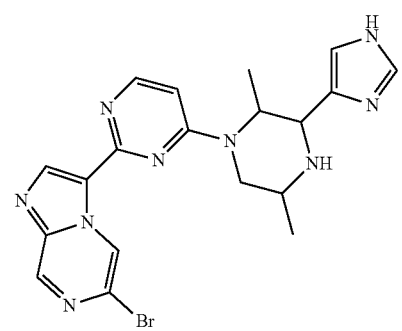 [SMILES: CC1CN(c2ccnc(-c3cnc4cnc(Br)cn34)n2)C(C)C(c2c[nH]cn2)N1]
single stereoisomer
IV-374
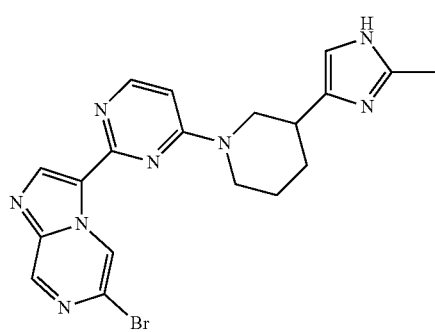 [SMILES: Cc1nc(C2CCCN(c3ccnc(-c4cnc5cnc(Br)cn45)n3)C2)c[nH]1]
TABLE 3-continued
Exemplary compounds of formula IV
single stereoisomer
IV-375
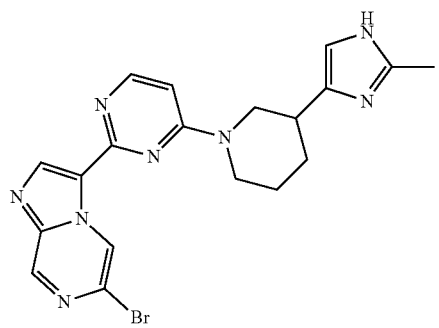 [SMILES: Cc1nc(C2CCCN(c3ccnc(-c4cnc5cnc(Br)cn45)n3)C2)c[nH]1]
single stereoisomer
IV-376
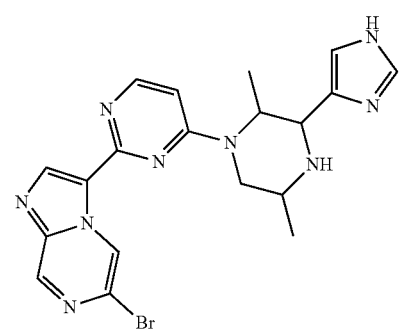 [SMILES: CC1CN(c2ccnc(-c3cnc4cnc(Br)cn34)n2)C(C)C(c2c[nH]cn2)N1]
single stereoisomer
IV-377
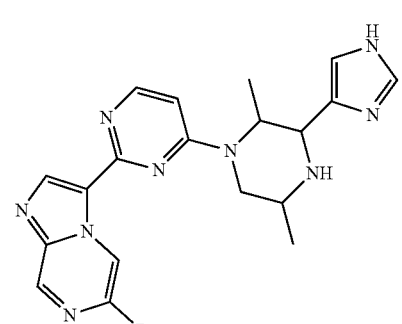
IV-378
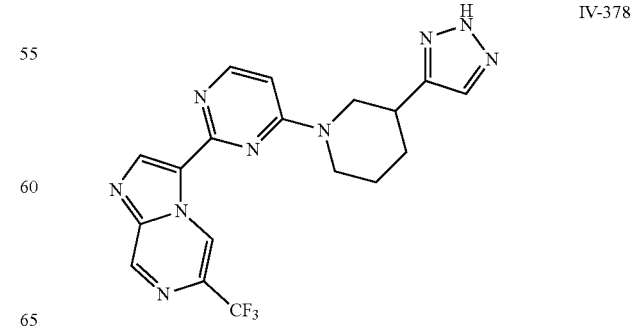

TABLE 3-continued
Exemplary compounds of formula IV
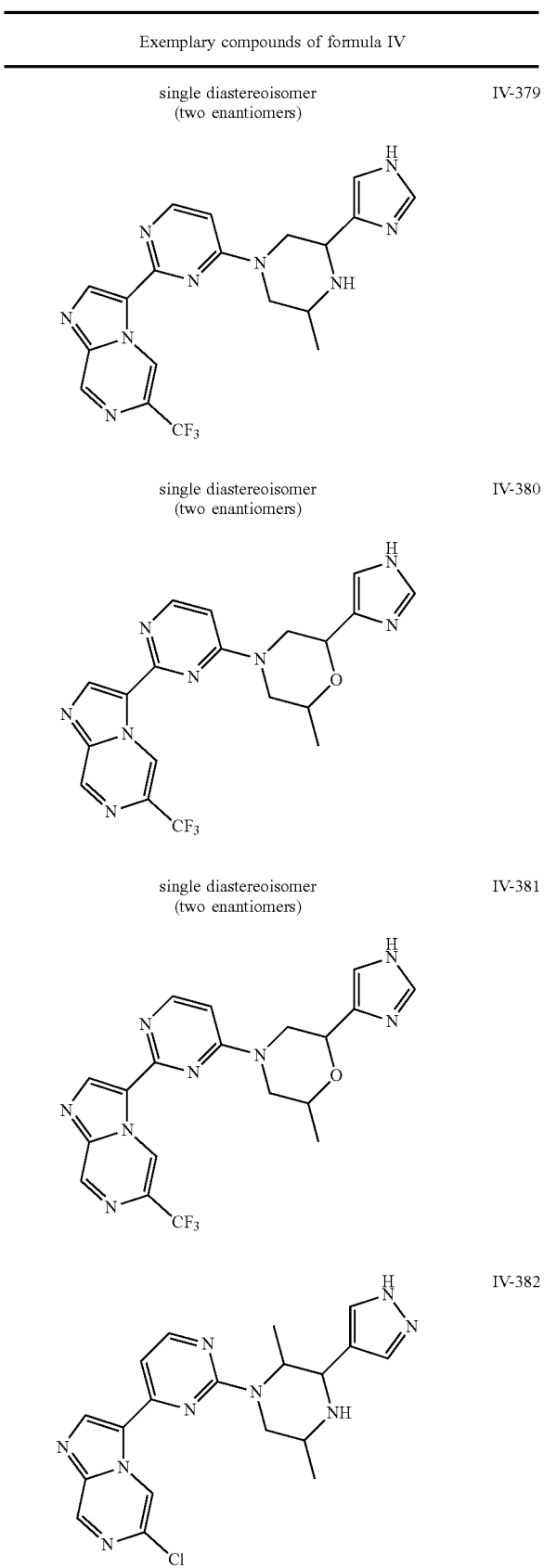
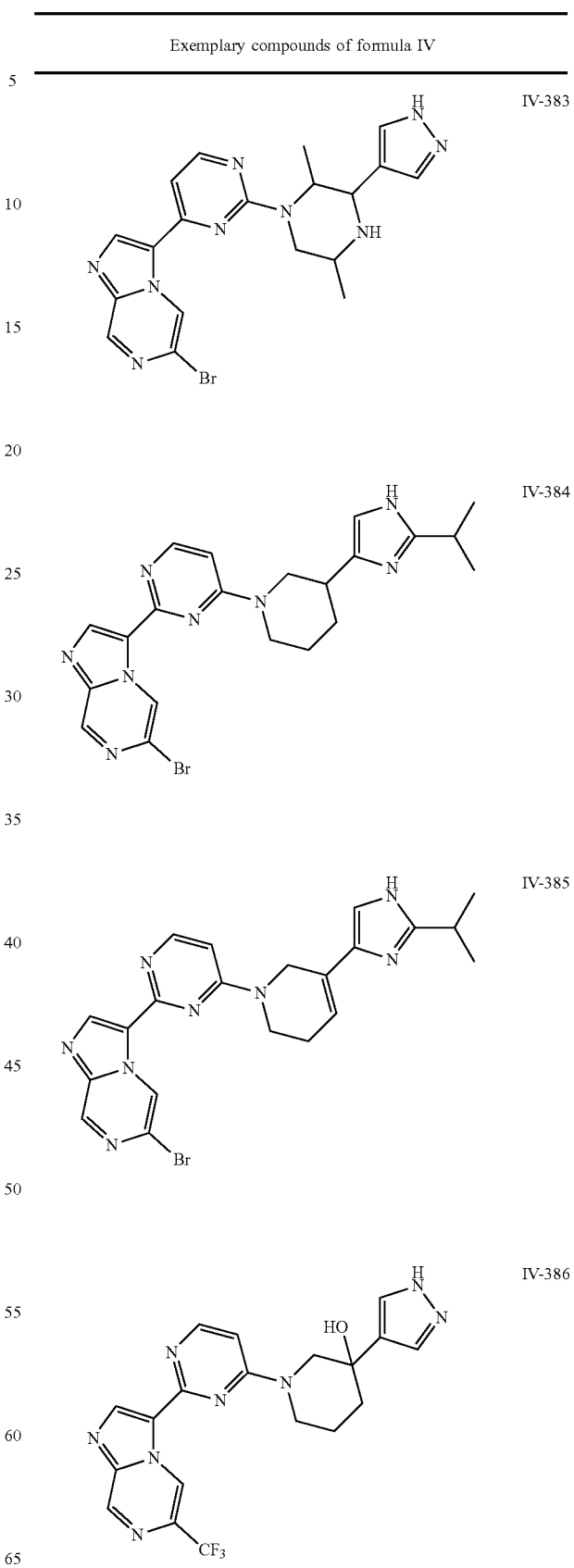

TABLE 3-continued
Exemplary compounds of formula IV
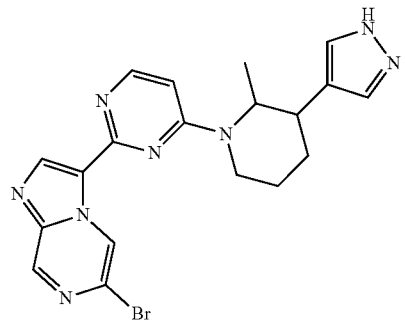
IV-387
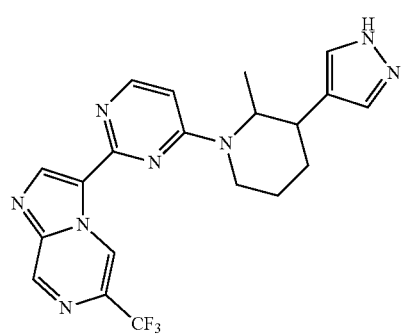
IV-388
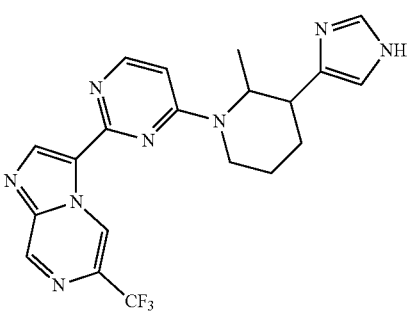 [SMILES: CC1C(c2c[nH]cn2)CCCN1c1ccnc(-c2cnc3cnc(C(F)(F)F)cn23)n1]
IV-389
single diastereoisomer
(two enantiomers)
IV-390
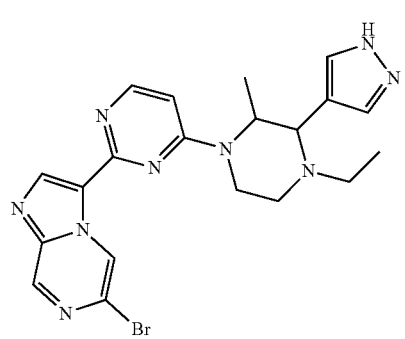 [SMILES: CCN1CCN(c2ccnc(-c3cnc4cnc(Br)cn34)n2)C(C)C1c1cn[nH]c1]
TABLE 3-continued
Exemplary compounds of formula IV
single diastereoisomer
(two enantiomers)
IV-391
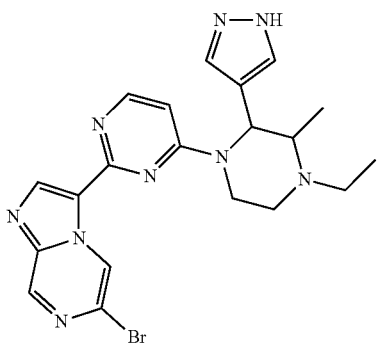 [SMILES: CCN1CCN(c2ccnc(-c3cnc4cnc(Br)cn34)n2)C(c2cn[nH]c2)C1C]
single diastereoisomer
(two enantiomers)
IV-392
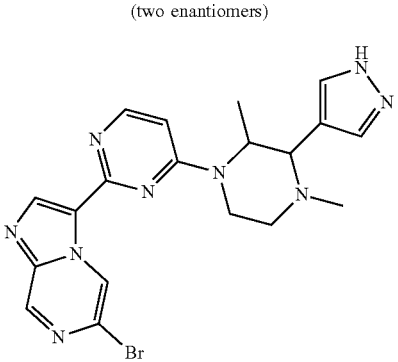
single diastereoisomer
(two enantiomers)
IV-393
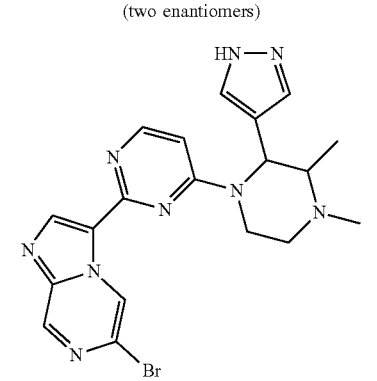
single diastereoisomer
(two enantiomers)
IV-394
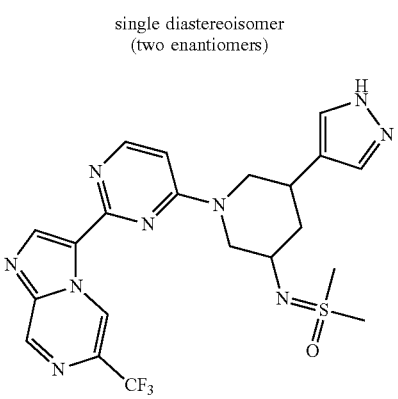

TABLE 3-continued
Exemplary compounds of formula IV
single diastereoisomer (two enantiomers)     IV-395
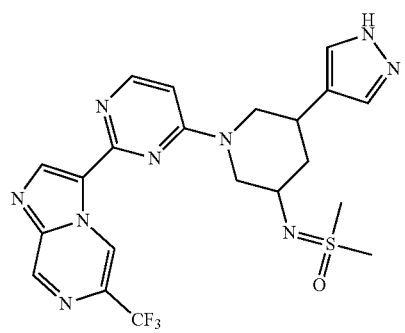 [SMILES: CS(C)(=O)=NC1CC(c2cn[nH]c2)CN(c2ccnc(-c3cnc4cnc(C(F)(F)F)cn34)n2)C1]
IV-396
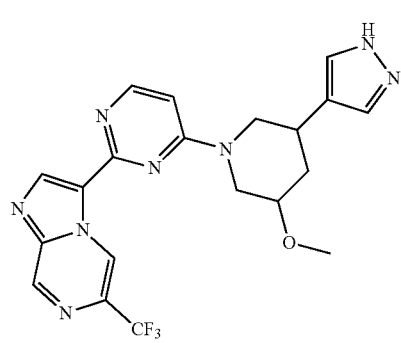 [SMILES: COC1CC(c2cn[nH]c2)CN(c2ccnc(-c3cnc4cnc(C(F)(F)F)cn34)n2)C1]
IV-397
single diastereoisomer (two enantiomers)     IV-398
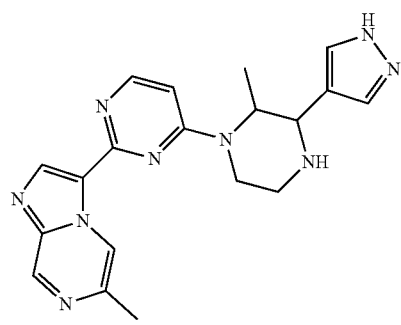 [SMILES: Cc1cn2c(-c3nccc(N4CCNC(c5cn[nH]c5)C4C)n3)cnc2cn1]
TABLE 3-continued
Exemplary compounds of formula IV
single stereoisomer     IV-399
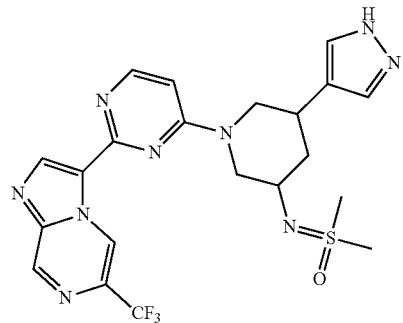
single stereoisomer     IV-400
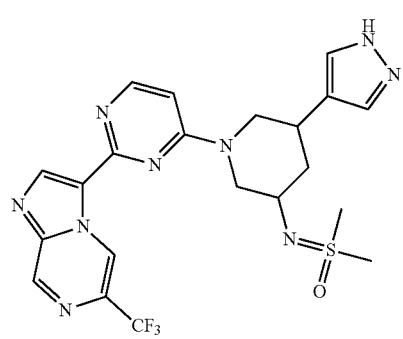
single stereoisomer     IV-401
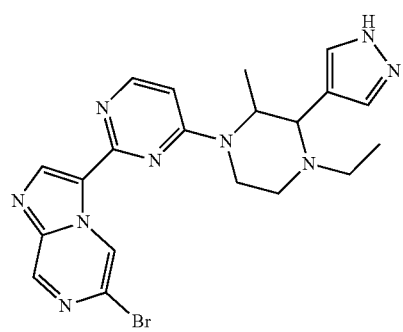 [SMILES: CCN1CCN(c2ccnc(-c3cnc4cnc(Br)cn34)n2)C(C)C1c1cn[nH]c1]
single stereoisomer     IV-402
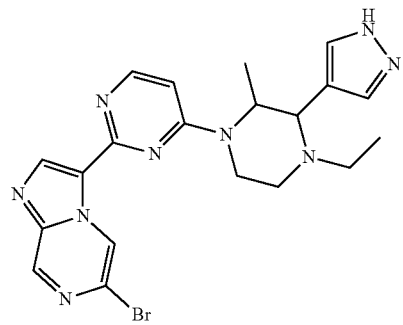 [SMILES: CCN1CCN(c2ccnc(-c3cnc4cnc(Br)cn34)n2)C(C)C1c1cn[nH]c1]

TABLE 3-continued
Exemplary compounds of formula IV
single stereoisomer IV-403
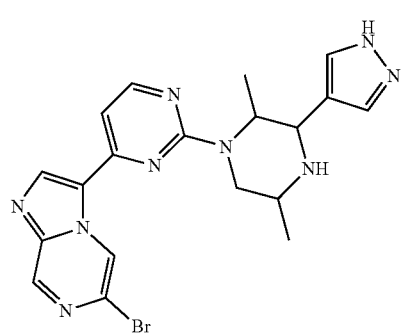 [SMILES: CC1CN(c2nccc(-c3cnc4cnc(Br)cn34)n2)C(C)C(c2cn[nH]c2)N1]
single stereoisomer IV-404
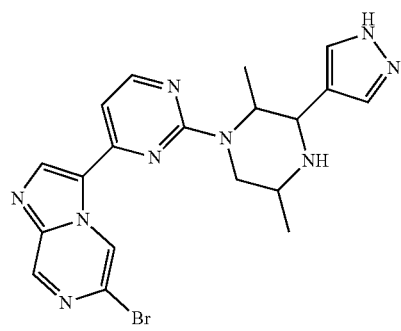 [SMILES: CC1CN(c2nccc(-c3cnc4cnc(Br)cn34)n2)C(C)C(c2cn[nH]c2)N1]
single stereoisomer IV-405
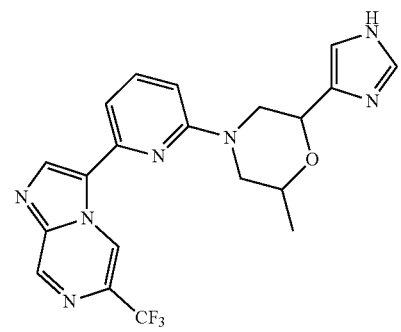 [SMILES: CC1CN(c2cccc(-c3cnc4cnc(C(F)(F)F)cn34)n2)CC(c2c[nH]cn2)O1]
single stereoisomer IV-406
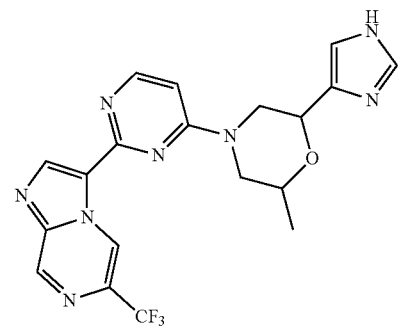
TABLE 3-continued
Exemplary compounds of formula IV
single stereoisomer IV-407
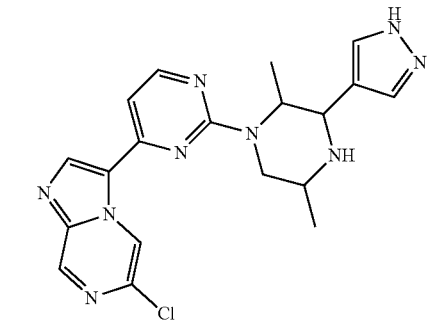 [SMILES: CC1CN(c2nccc(-c3cnc4cnc(Cl)cn34)n2)C(C)C(c2cn[nH]c2)N1]
single stereoisomer IV-408
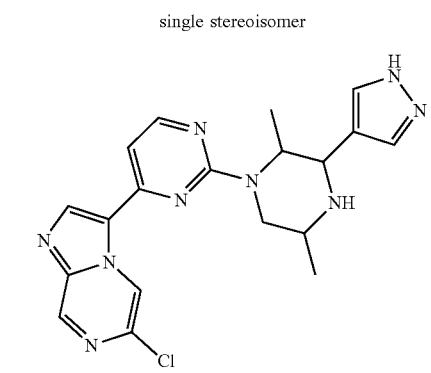
IV-409
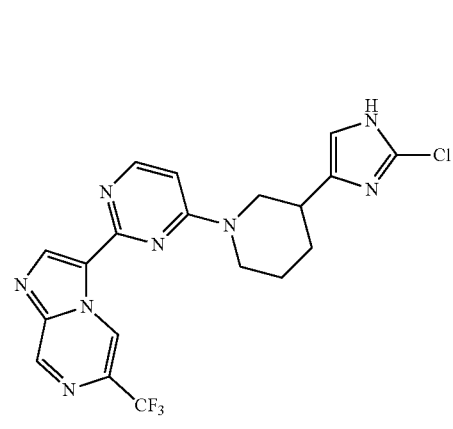 [SMILES: FC(F)(F)c1cn2c(-c3nccc(N4CCCC(c5c[nH]c(Cl)n5)C4)n3)cnc2cn1]
IV-410
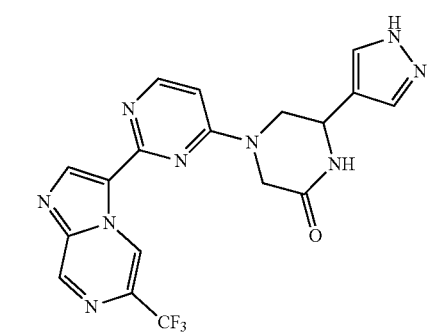 [SMILES: O=C1CN(c2ccnc(-c3cnc4cnc(C(F)(F)F)cn34)n2)CC(c2cn[nH]c2)N1]

TABLE 3-continued
Exemplary compounds of formula IV
single diastereoisomer (two enantiomers) IV-411
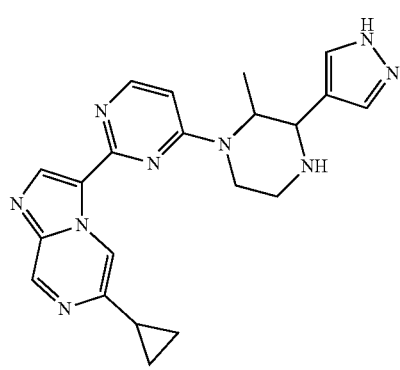 [SMILES: CC1C(c2cn[nH]c2)NCCN1c1ccnc(-c2cnc3cnc(C4CC4)cn23)n1]
IV-412
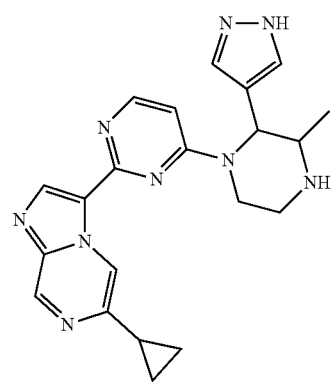 [SMILES: CC1NCCN(c2ccnc(-c3cnc4cnc(C5CC5)cn34)n2)C1c1cn[nH]c1]
single stereoisomer IV-413
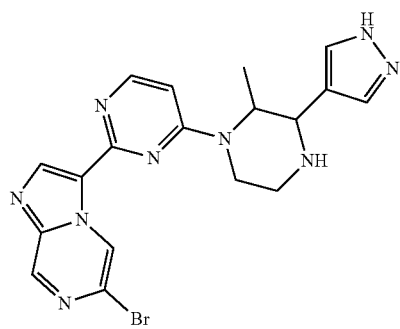 [SMILES: CC1C(c2cn[nH]c2)NCCN1c1ccnc(-c2cnc3cnc(Br)cn23)n1]
single stereoisomer IV-414
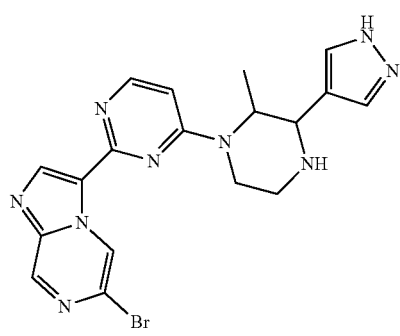 [SMILES: CC1C(c2cn[nH]c2)NCCN1c1ccnc(-c2cnc3cnc(Br)cn23)n1]
TABLE 3-continued
Exemplary compounds of formula IV
IV-415
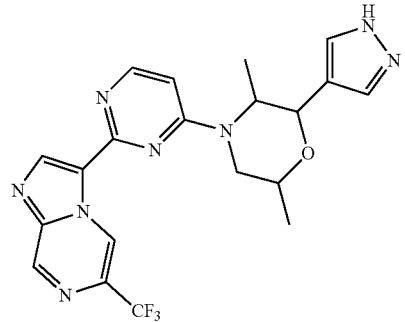 [SMILES: CC1CN(c2ccnc(-c3cnc4cnc(C(F)(F)F)cn34)n2)C(C)C(c2cn[nH]c2)O1]
IV-416
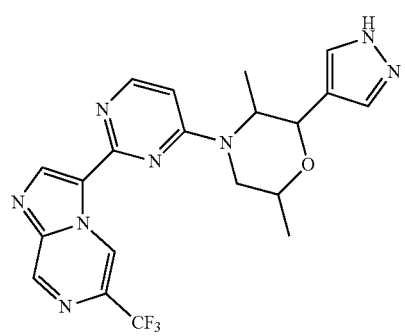
single diastereoisomer (two enantiomers) IV-417
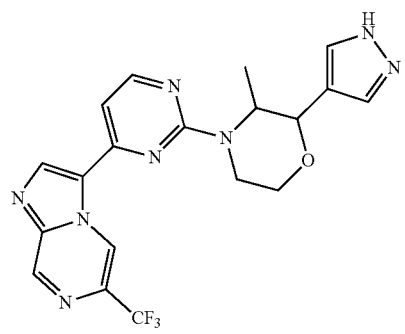 [SMILES: CC1C(c2cn[nH]c2)OCCN1c1nccc(-c2cnc3cnc(C(F)(F)F)cn23)n1]
single diastereoisomer (two enantiomers) IV-418
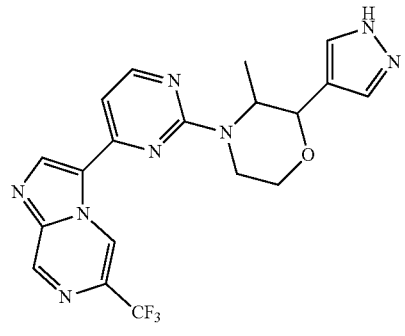 [SMILES: CC1C(c2cn[nH]c2)OCCN1c1nccc(-c2cnc3cnc(C(F)(F)F)cn23)n1]

TABLE 3-continued
Exemplary compounds of formula IV
| | |
|---|---|
| single stereoisomer 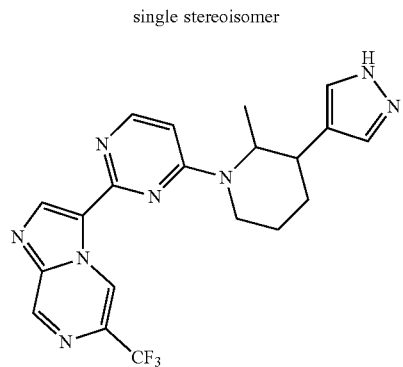 | IV-419 |
| single stereoisomer 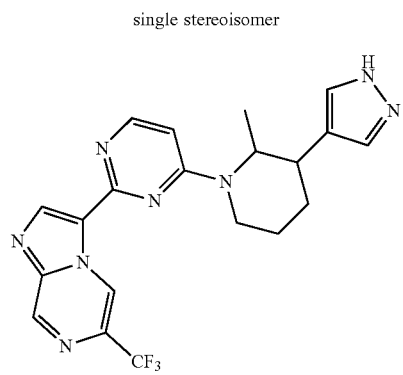 | IV-420 |
| single diastereoisomer (two enantiomers) 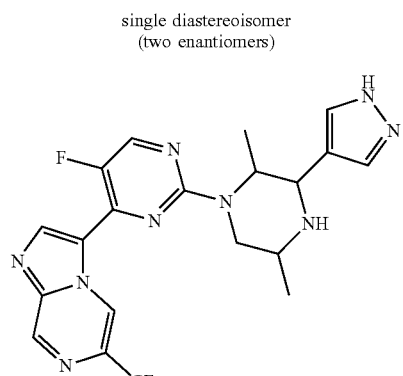 | IV-421 |
| single diastereoisomer (two enantiomers) 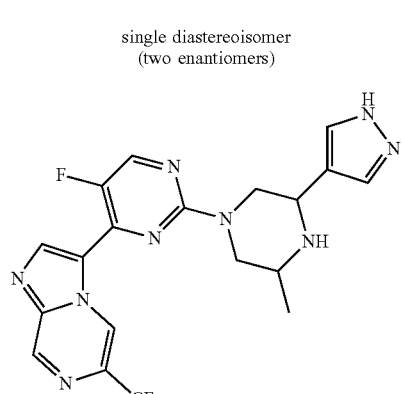 | IV-422 |
TABLE 3-continued
Exemplary compounds of formula IV
| | |
|---|---|
| 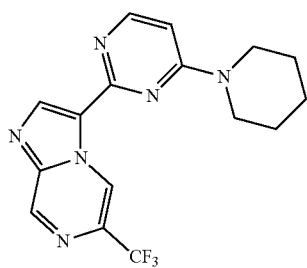 [SMILES: FC(F)(F)c1cn2c(-c3nccc(N4CCCCC4)n3)cnc2cn1] | IV-423 |
| 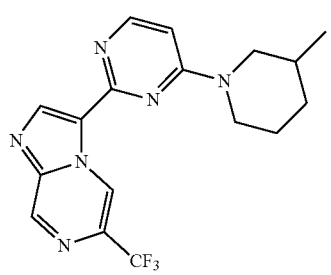 | IV-424 |
| 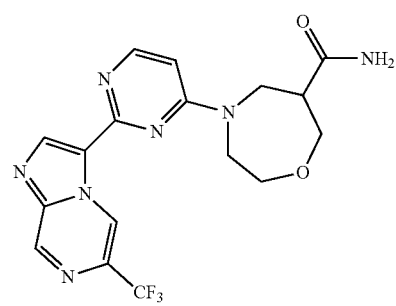 [SMILES: NC(=O)C1COCCN(c2ccnc(-c3cnc4cnc(C(F)(F)F)cn34)n2)C1] | IV-425 |
| 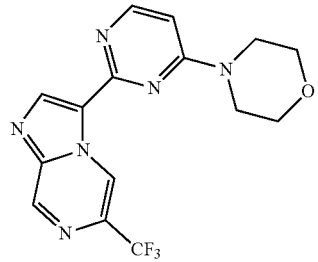 | IV-426 |
| 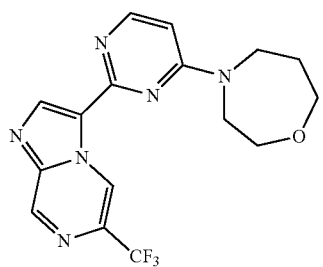 | IV-427 |

TABLE 3-continued
Exemplary compounds of formula IV
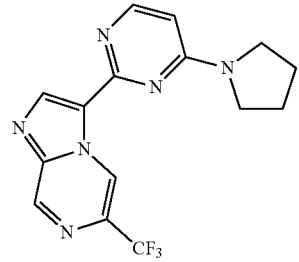 [SMILES: FC(F)(F)c1cn2c(-c3nccc(N4CCCC4)n3)cnc2cn1] IV-428
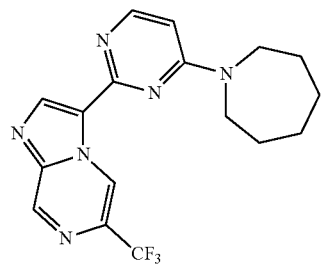 [SMILES: FC(F)(F)c1cn2c(-c3nccc(N4CCCCCC4)n3)cnc2cn1] IV-429
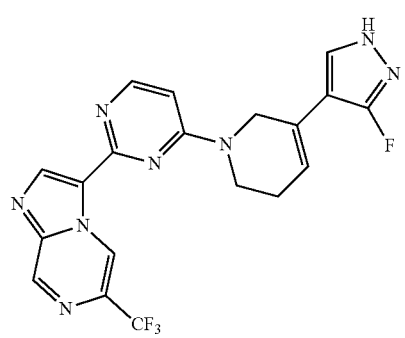 [SMILES: Fc1n[nH]cc1C1=CCCN(c2ccnc(-c3cnc4cnc(C(F)(F)F)cn34)n2)C1] IV-430
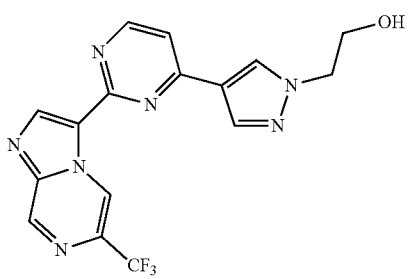 [SMILES: OCCn1cc(-c2ccnc(-c3cnc4cnc(C(F)(F)F)cn34)n2)cn1] IV-431
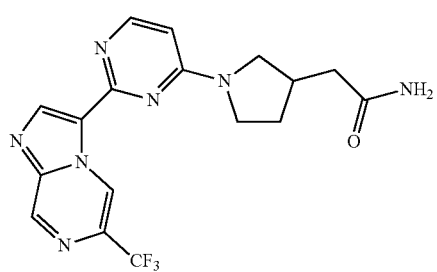 [SMILES: NC(=O)CC1CCN(c2ccnc(-c3cnc4cnc(C(F)(F)F)cn34)n2)C1] IV-432
TABLE 3-continued
Exemplary compounds of formula IV
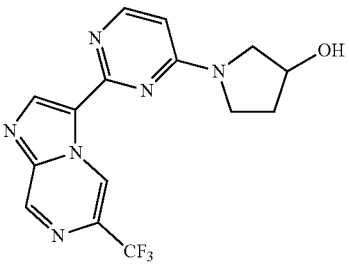 [SMILES: OC1CCN(c2ccnc(-c3cnc4cnc(C(F)(F)F)cn34)n2)C1] IV-433
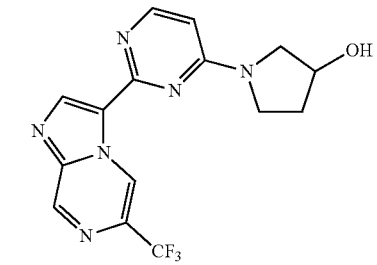 IV-434
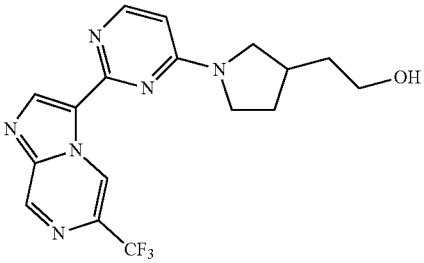 [SMILES: OCCC1CCN(c2ccnc(-c3cnc4cnc(C(F)(F)F)cn34)n2)C1] IV-435
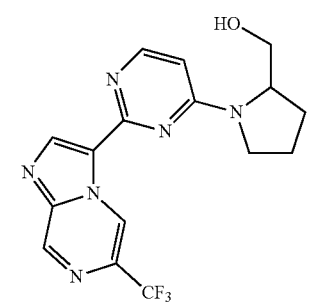 [SMILES: OCC1CCCN1c1ccnc(-c2cnc3cnc(C(F)(F)F)cn23)n1] IV-436
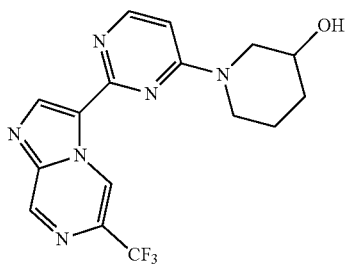 IV-437

TABLE 3-continued
Exemplary compounds of formula IV
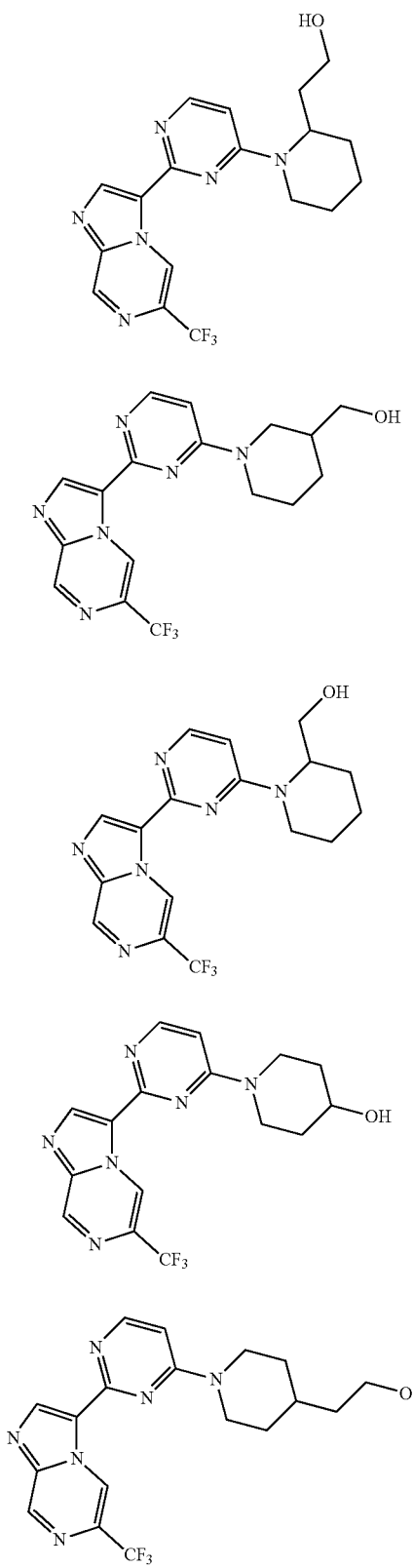
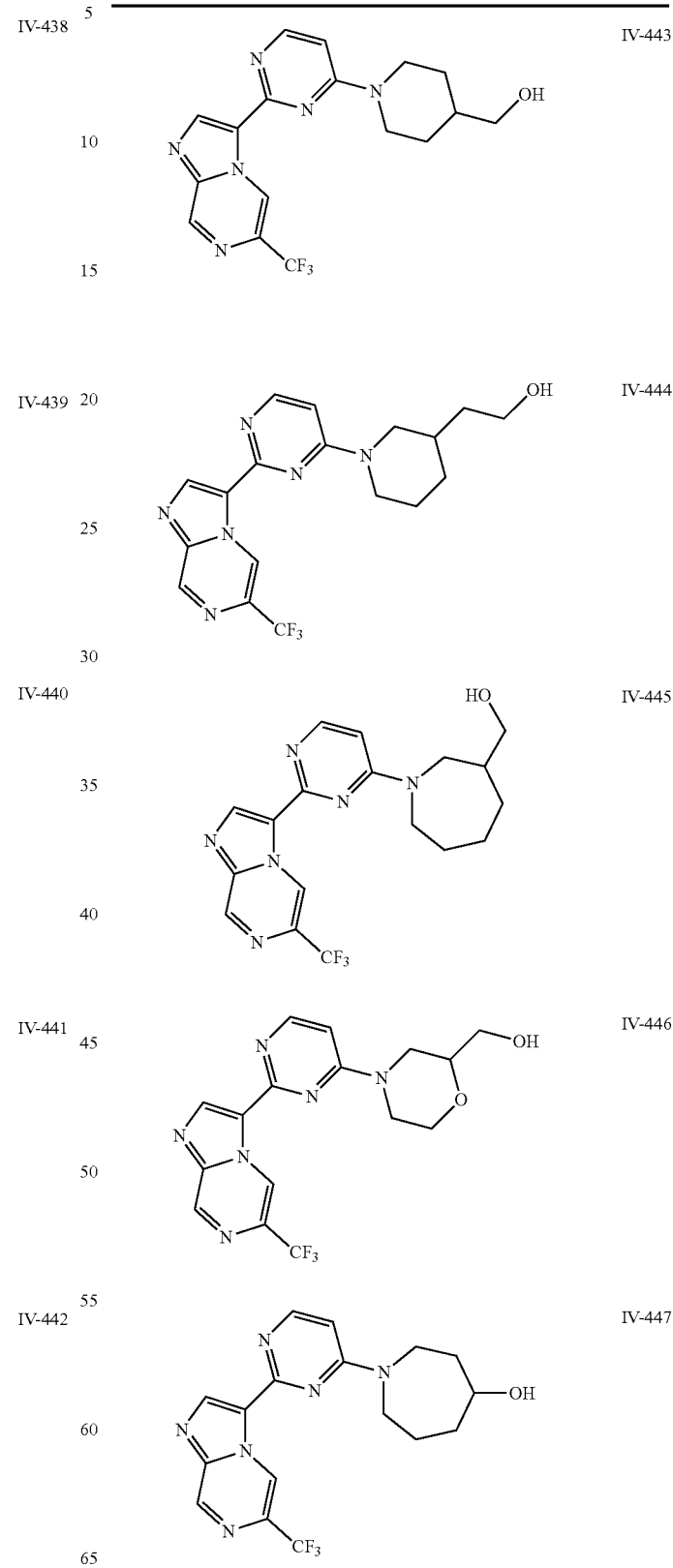

TABLE 3-continued

Exemplary compounds of formula IV

| Compound | Notes |
|---|---|
| IV-448 | |
| IV-449 | |
| IV-450 | single stereoisomer |
| IV-451 | single stereoisomer |
| IV-452 | |
| IV-453 | single diastereoisomer (two enantiomers) |
| IV-454 | single diastereoisomer (two enantiomers) |
| IV-455 | single diastereoisomer (two enantiomers) |
| IV-456 | |

TABLE 3-continued
Exemplary compounds of formula IV
IV-457
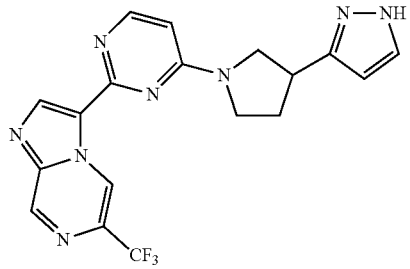 [SMILES: FC(F)(F)c1cn2c(-c3nccc(N4CCC(c5cc[nH]n5)C4)n3)cnc2cn1]
single stereoisomer    IV-458
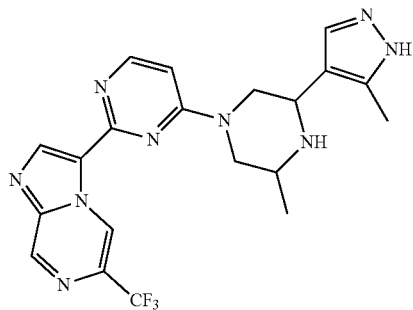 [SMILES: Cc1[nH]ncc1C1CN(c2ccnc(-c3cnc4cnc(C(F)(F)F)cn34)n2)CC(C)N1]
single stereoisomer    IV-459
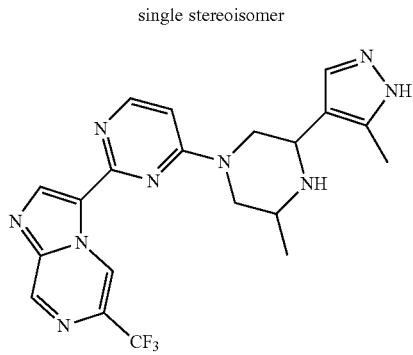
single stereoisomer    IV-460
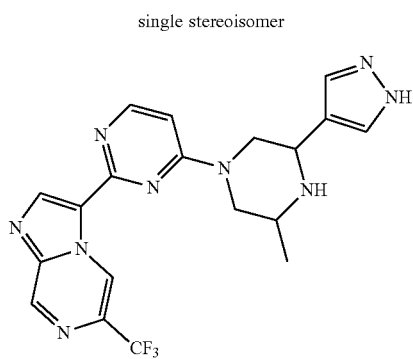
TABLE 3-continued
Exemplary compounds of formula IV
single stereoisomer    IV-461
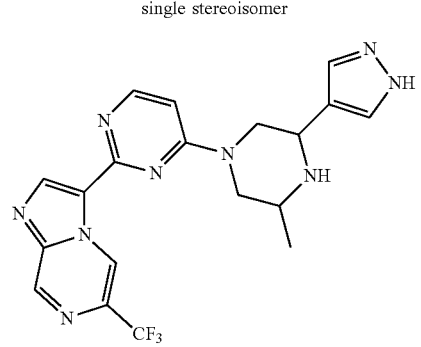
single stereoisomer    IV-462
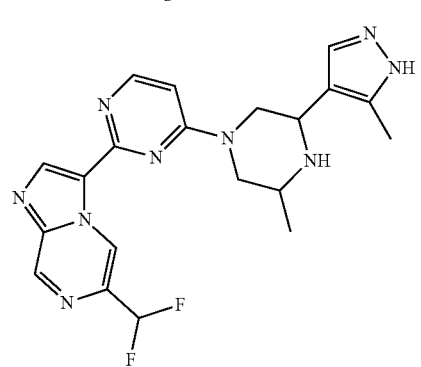
single stereoisomer    IV-463
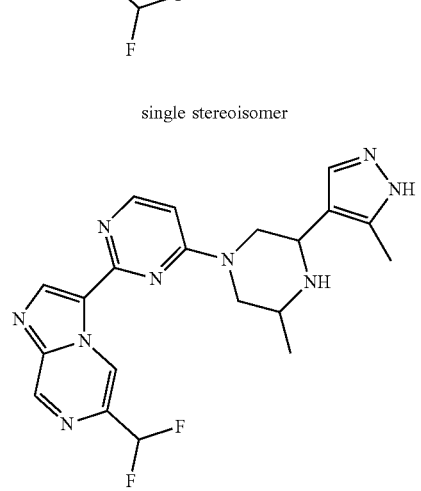
single diastereoisomer    IV-464
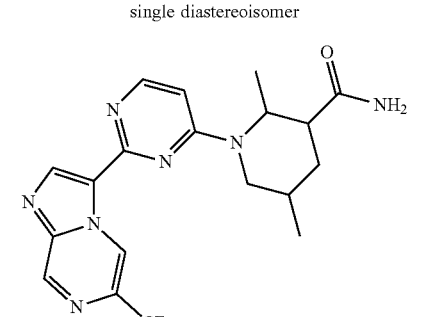

TABLE 3-continued
Exemplary compounds of formula IV
single stereoisomer IV-465
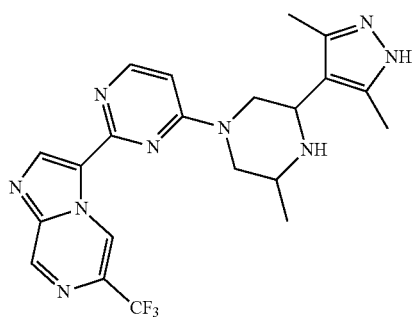 [SMILES: Cc1n[nH]c(C)c1C1CN(c2ccnc(-c3cnc4cnc(C(F)(F)F)cn34)n2)CC(C)N1]
single diastereoisomer IV-466
(two enantiomers)
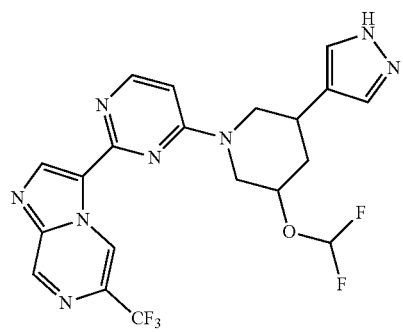 [SMILES: FC(F)OC1CC(c2cn[nH]c2)CN(c2ccnc(-c3cnc4cnc(C(F)(F)F)cn34)n2)C1]
single stereoisomer IV-467
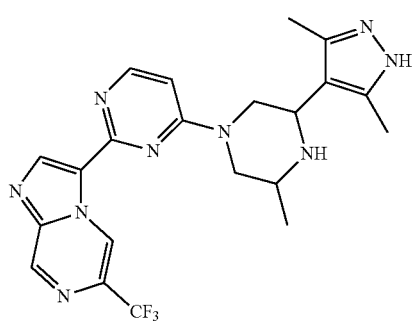 [SMILES: Cc1n[nH]c(C)c1C1CN(c2ccnc(-c3cnc4cnc(C(F)(F)F)cn34)n2)CC(C)N1]
single stereoisomer IV-468
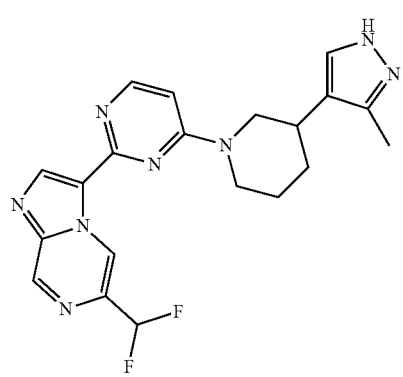 [SMILES: Cc1n[nH]cc1C1CCCN(c2ccnc(-c3cnc4cnc(C(F)F)cn34)n2)C1]
TABLE 3-continued
Exemplary compounds of formula IV
single stereoisomer IV-469
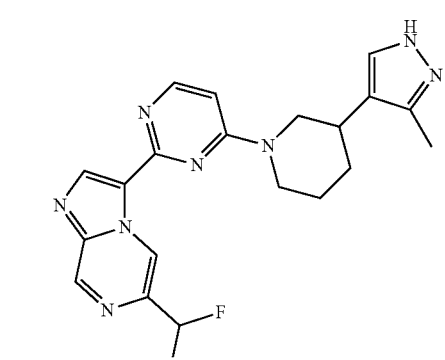
single stereoisomer IV-470
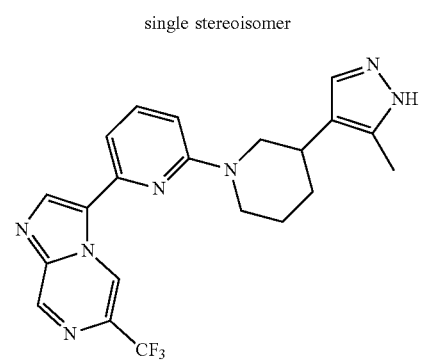
single stereoisomer IV-471
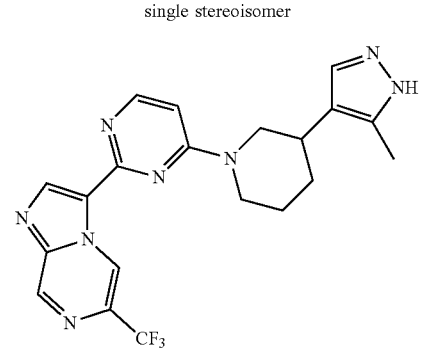
single diastereoisomer IV-472
(two enantiomers)
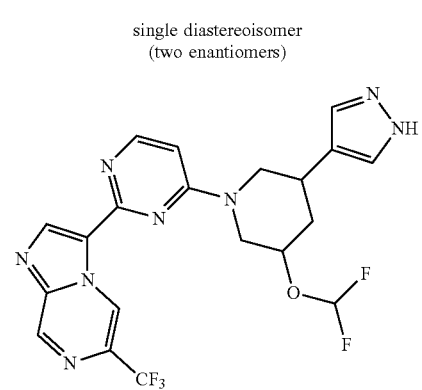

TABLE 3-continued
Exemplary compounds of formula IV
| | |
|---|---|
| 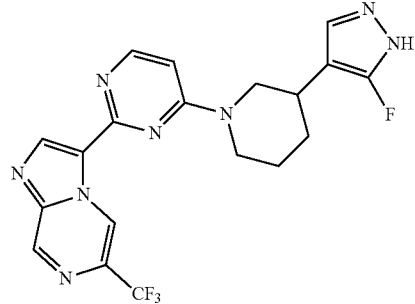 [SMILES: Cc1[nH]ncc1C1CCCN(c2cccc(-c3cnc4cnc(C(F)(F)F)cn34)n2)C1] | IV-473 |
| 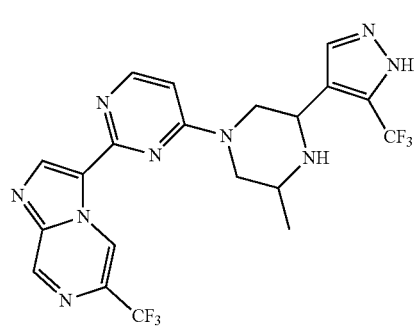 [SMILES: CC1CN(c2ccnc(-c3cnc4cnc(C(F)(F)F)cn34)n2)CC(c2cn[nH]c2C(F)(F)F)N1]<br>single stereoisomer | IV-474 |
| 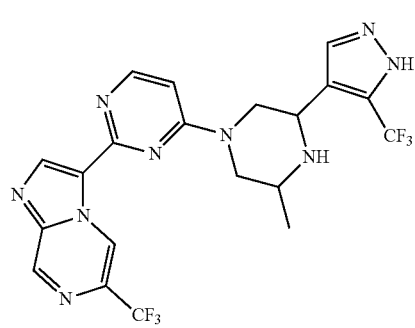 [SMILES: CC1CN(c2ccnc(-c3cnc4cnc(C(F)(F)F)cn34)n2)CC(c2cn[nH]c2C(F)(F)F)N1]<br>single stereoisomer | IV-475 |
| 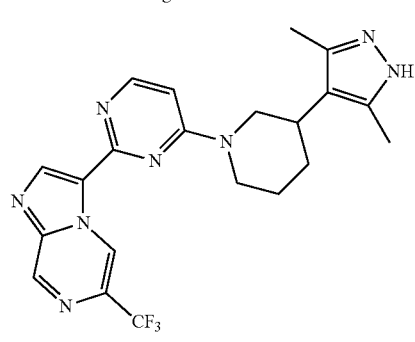<br>single stereoisomer | IV-476 |
| 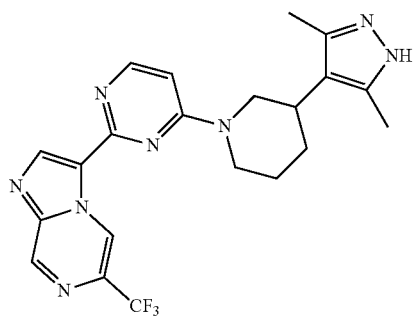 [SMILES: Cc1n[nH]c(C)c1C1CCCN(c2ccnc(-c3cnc4cnc(C(F)(F)F)cn34)n2)C1]<br>single stereoisomer | IV-477 |
| 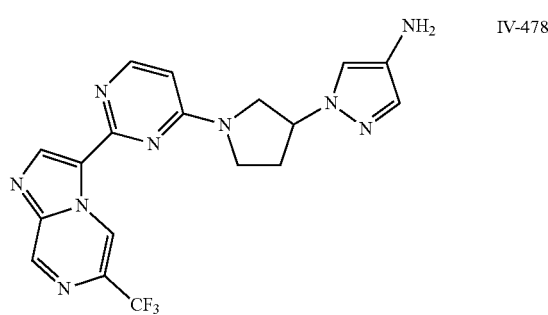 | IV-478 |
| 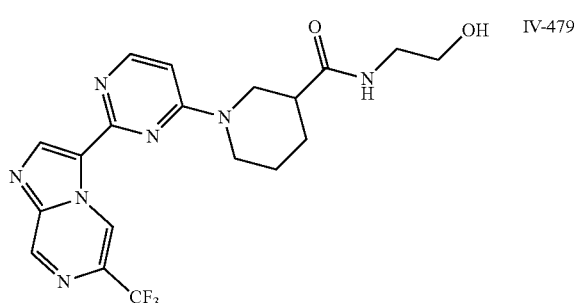 | IV-479 |
| 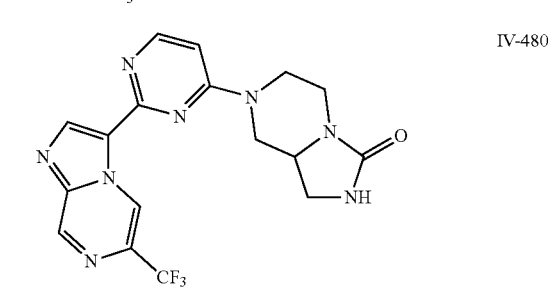 | IV-480 |
| 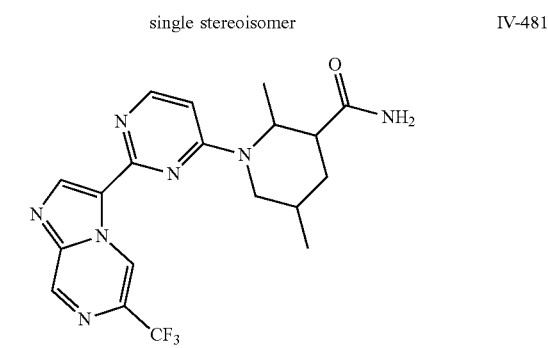<br>single stereoisomer | IV-481 |

TABLE 3-continued
Exemplary compounds of formula IV
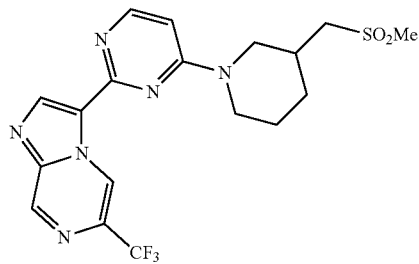 [SMILES: CS(=O)(=O)CC1CCCN(c2ccnc(-c3cnc4cnc(C(F)(F)F)cn34)n2)C1] IV-482
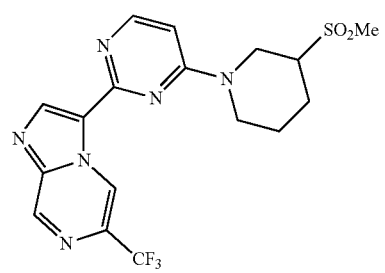 [SMILES: CS(=O)(=O)C1CCCN(c2ccnc(-c3cnc4cnc(C(F)(F)F)cn34)n2)C1] IV-483
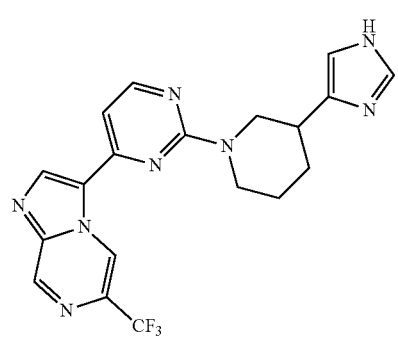 IV-484
single diastereoisomer (two enantiomers)
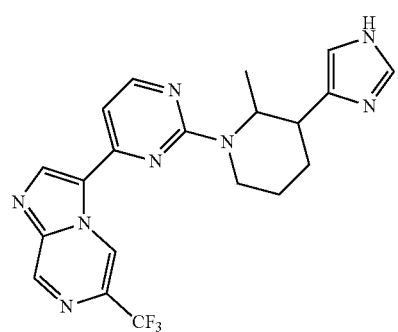 [SMILES: CC1C(c2c[nH]cn2)CCCN1c1nccc(-c2cnc3cnc(C(F)(F)F)cn23)n1] IV-485
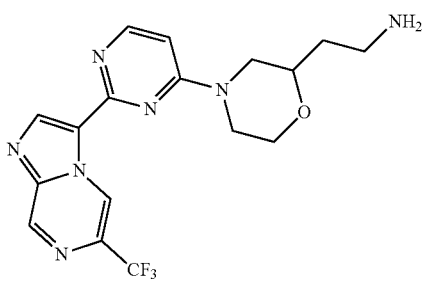 IV-486
TABLE 3-continued
Exemplary compounds of formula IV
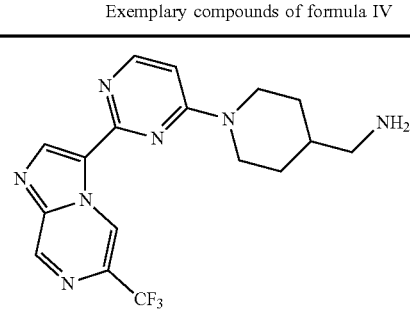 IV-487
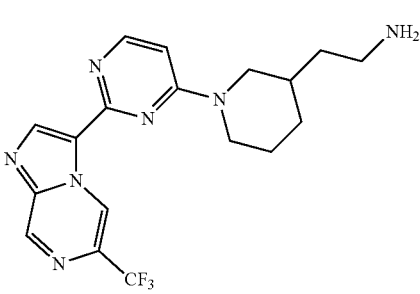 [SMILES: NCCC1CCCN(c2ccnc(-c3cnc4cnc(C(F)(F)F)cn34)n2)C1] IV-488
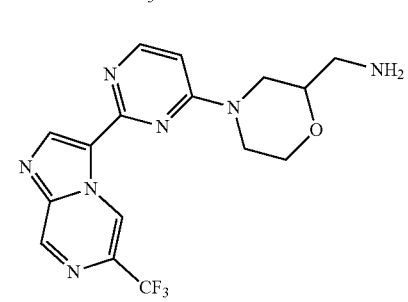 IV-489
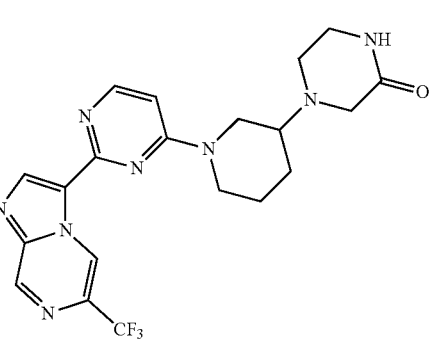 IV-490
single stereoisomer
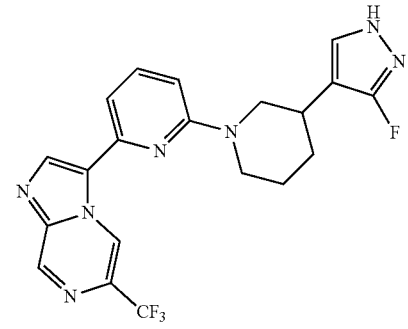 [SMILES: Fc1n[nH]cc1C1CCCN(c2cccc(-c3cnc4cnc(C(F)(F)F)cn34)n2)C1] IV-491

TABLE 3-continued
Exemplary compounds of formula IV
single stereoisomer  IV-492
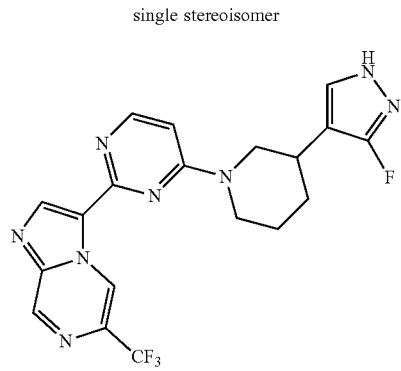
IV-493
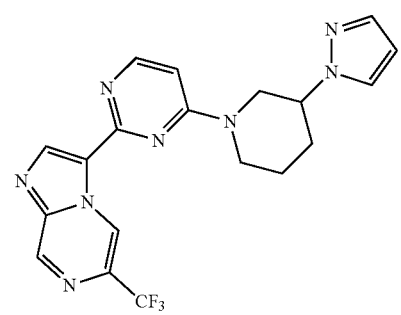 [SMILES: FC(F)(F)c1cn2c(-c3nccc(N4CCCC(n5cccn5)C4)n3)cnc2cn1]
IV-494
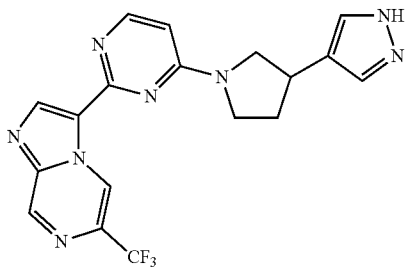 [SMILES: FC(F)(F)c1cn2c(-c3nccc(N4CCC(c5cn[nH]c5)C4)n3)cnc2cn1]
IV-495
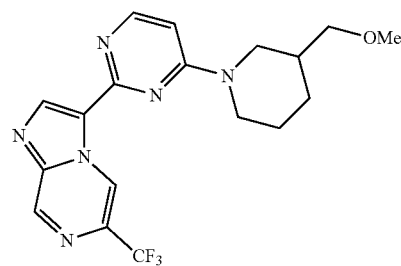 [SMILES: COCC1CCCN(c2ccnc(-c3cnc4cnc(C(F)(F)F)cn34)n2)C1]
IV-496
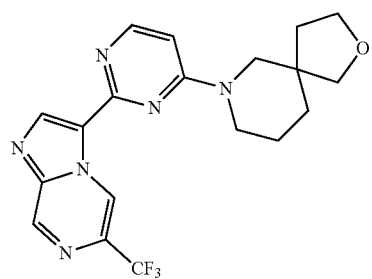
TABLE 3-continued
Exemplary compounds of formula IV
IV-497
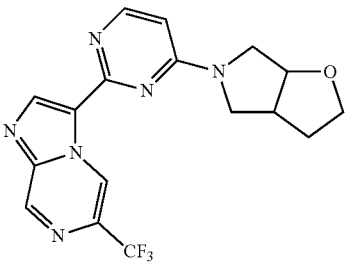 [SMILES: FC(F)(F)c1cn2c(-c3nccc(N4CC5CCOC5C4)n3)cnc2cn1]
single diastereoisomer  IV-498
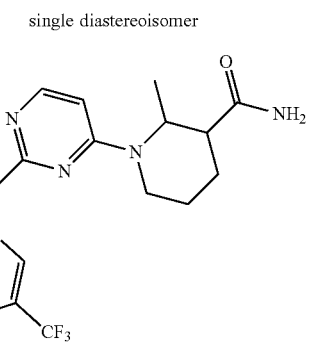
single diastereoisomer  IV-499
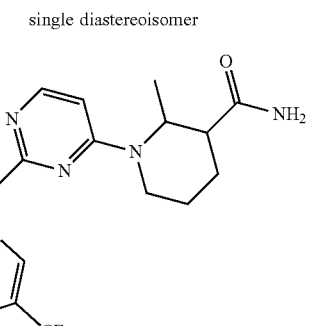
single diastereoisomer  IV-500
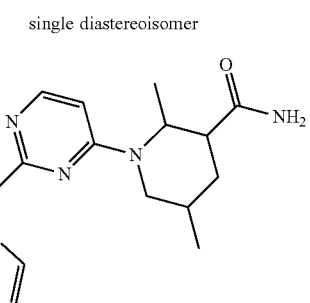

TABLE 3-continued
Exemplary compounds of formula IV
single diastereoisomer IV-501
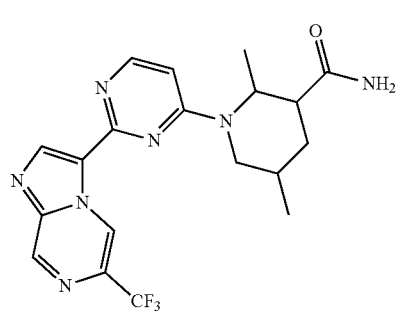 [SMILES: CC1CC(C(N)=O)C(C)N(c2ccnc(-c3cnc4cnc(C(F)(F)F)cn34)n2)C1]
single diastereoisomer
(two enantiomers) IV-502
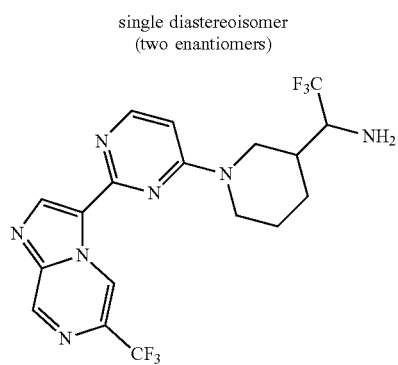
single diastereoisomer
(two enantiomers) IV-503
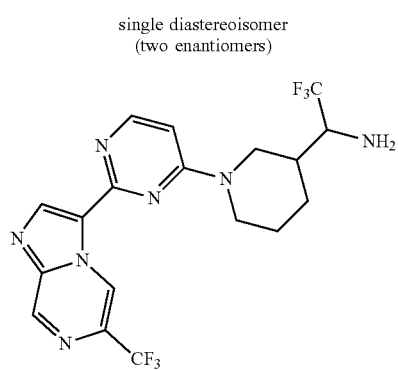
IV-504
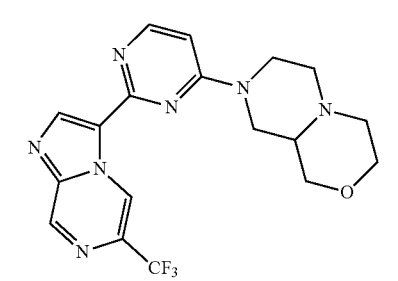 [SMILES: FC(F)(F)c1cn2c(-c3nccc(N4CCN5CCOCC5C4)n3)cnc2cn1]
TABLE 3-continued
Exemplary compounds of formula IV
IV-505
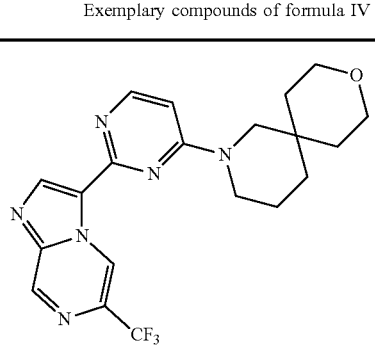
IV-506
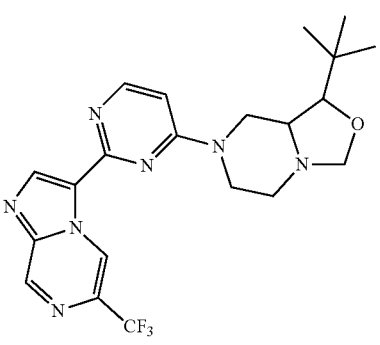 [SMILES: CC(C)(C)C1OCN2CCN(c3ccnc(-c4cnc5cnc(C(F)(F)F)cn45)n3)CC12]
IV-507
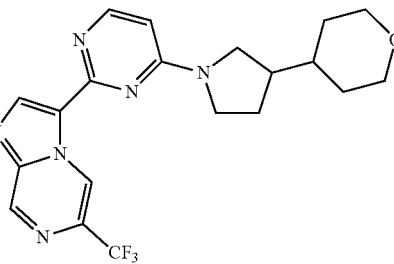
IV-508
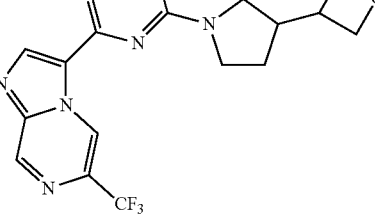
IV-509
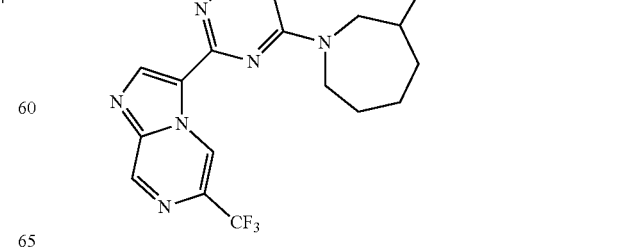

TABLE 3-continued
Exemplary compounds of formula IV
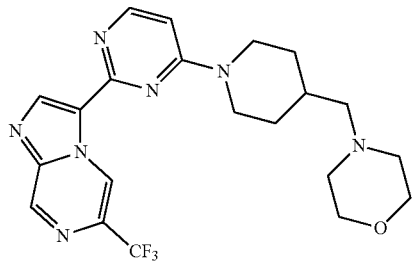 IV-510
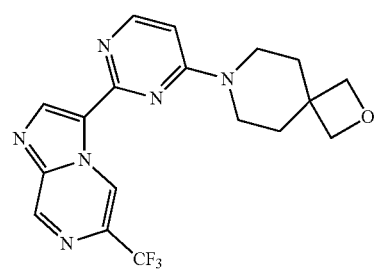 [SMILES: FC(F)(F)c1cn2c(-c3nccc(N4CCC5(CC4)COC5)n3)cnc2cn1] IV-511
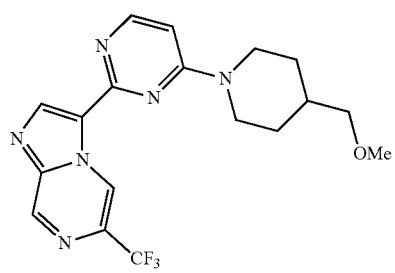 IV-512
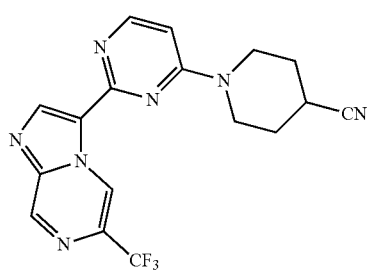 [SMILES: N#CC1CCN(c2ccnc(-c3cnc4cnc(C(F)(F)F)cn34)n2)CC1] IV-513
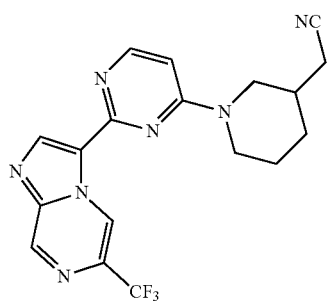 IV-514
TABLE 3-continued
Exemplary compounds of formula IV
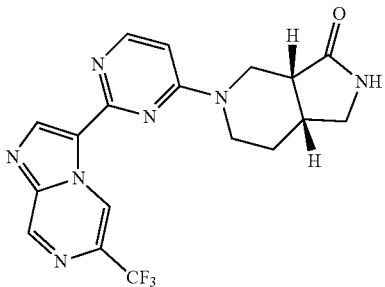 [SMILES: O=C1NC[C@@H]2CCN(c3ccnc(-c4cnc5cnc(C(F)(F)F)cn45)n3)C[C@H]12] IV-515
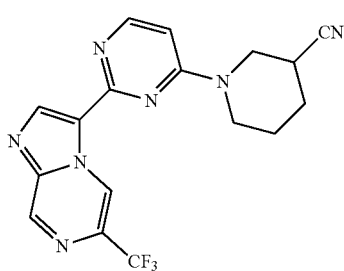 [SMILES: N#CC1CCCN(c2ccnc(-c3cnc4cnc(C(F)(F)F)cn34)n2)C1] IV-516
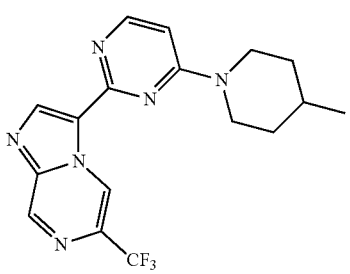 IV-517
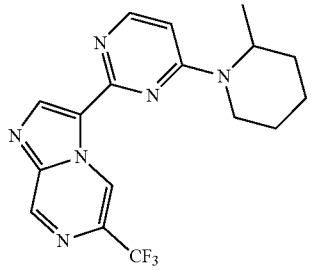 [SMILES: CC1CCCCN1c1ccnc(-c2cnc3cnc(C(F)(F)F)cn23)n1] IV-518
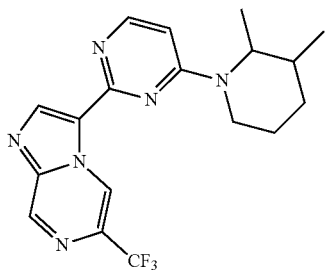 [SMILES: CC1CCCN(c2ccnc(-c3cnc4cnc(C(F)(F)F)cn34)n2)C1C] IV-519

TABLE 3-continued

Exemplary compounds of formula IV

| Compound | Notes |
|---|---|
| IV-520 | |
| IV-521 | single stereoisomer |
| IV-522 | |
| IV-523 | |
| IV-524 | |
| IV-525 | single diastereoisomer (two enantiomers) |
| IV-526 | |
| IV-527 | |
| IV-528 | |
| IV-529 | |

TABLE 3-continued
Exemplary compounds of formula IV
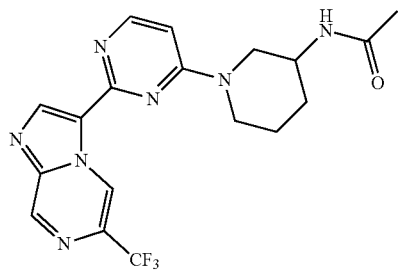 [SMILES: CC(=O)NC1CCCN(c2ccnc(-c3cnc4cnc(C(F)(F)F)cn34)n2)C1] IV-530
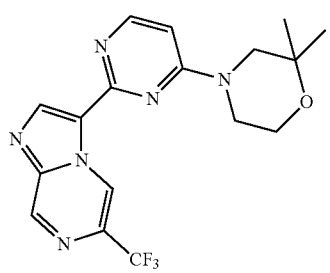 [SMILES: CC1(C)CN(c2ccnc(-c3cnc4cnc(C(F)(F)F)cn34)n2)CCO1] IV-531
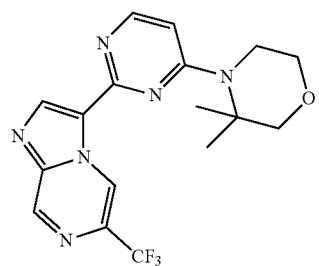 [SMILES: CC1(C)COCCN1c1ccnc(-c2cnc3cnc(C(F)(F)F)cn23)n1] IV-532
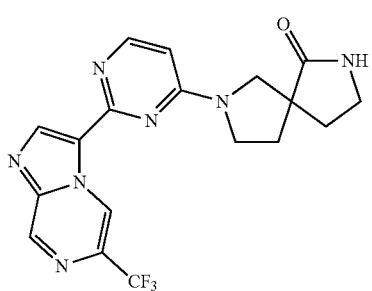 [SMILES: O=C1NCCC12CCN(c1ccnc(-c3cnc4cnc(C(F)(F)F)cn34)n1)C2] IV-533
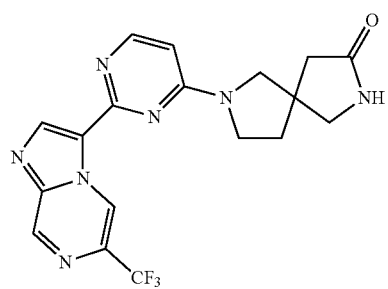 [SMILES: O=C1CC2(CCN(c3ccnc(-c4cnc5cnc(C(F)(F)F)cn45)n3)C2)CN1] IV-534
TABLE 3-continued
Exemplary compounds of formula IV
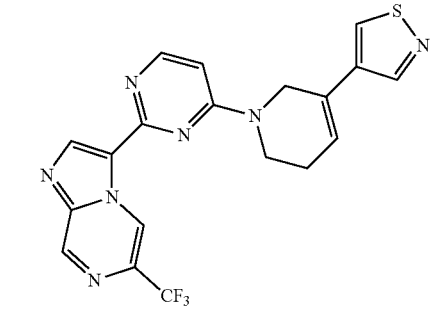 [SMILES: FC(F)(F)c1cn2c(-c3nccc(N4CCC=C(c5cnsc5)C4)n3)cnc2cn1] IV-535
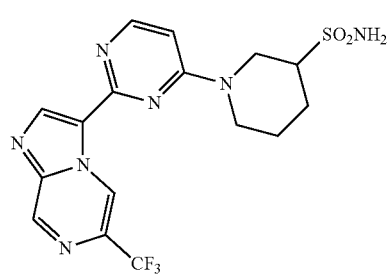 [SMILES: NS(=O)(=O)C1CCCN(c2ccnc(-c3cnc4cnc(C(F)(F)F)cn34)n2)C1] IV-536
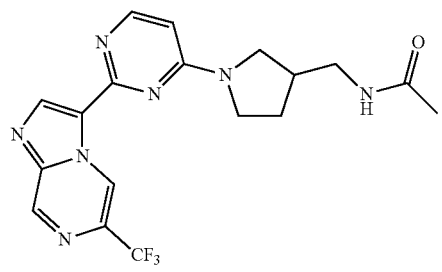 [SMILES: CC(=O)NCC1CCN(c2ccnc(-c3cnc4cnc(C(F)(F)F)cn34)n2)C1] IV-537
single stereoisomer
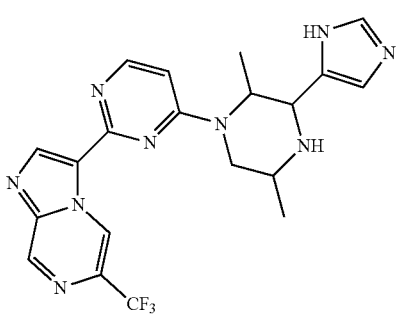 [SMILES: CC1CN(c2ccnc(-c3cnc4cnc(C(F)(F)F)cn34)n2)C(C)C(c2cnc[nH]2)N1] IV-538
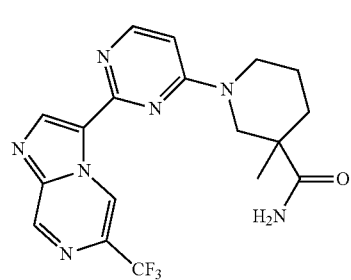 [SMILES: CC1(C(N)=O)CCCN(c2ccnc(-c3cnc4cnc(C(F)(F)F)cn34)n2)C1] IV-539

TABLE 3-continued
Exemplary compounds of formula IV
| | |
|---|---|
| single stereoisomer | IV-540 |
| single stereoisomer | IV-541 |
| | IV-542 |
| single diastereoisomer (two enantiomers) | IV-543 |
| single diastereoisomer (two enantiomers) | IV-544 |
| single stereoisomer | IV-545 |
| single stereoisomer | IV-546 |
| | IV-547 |
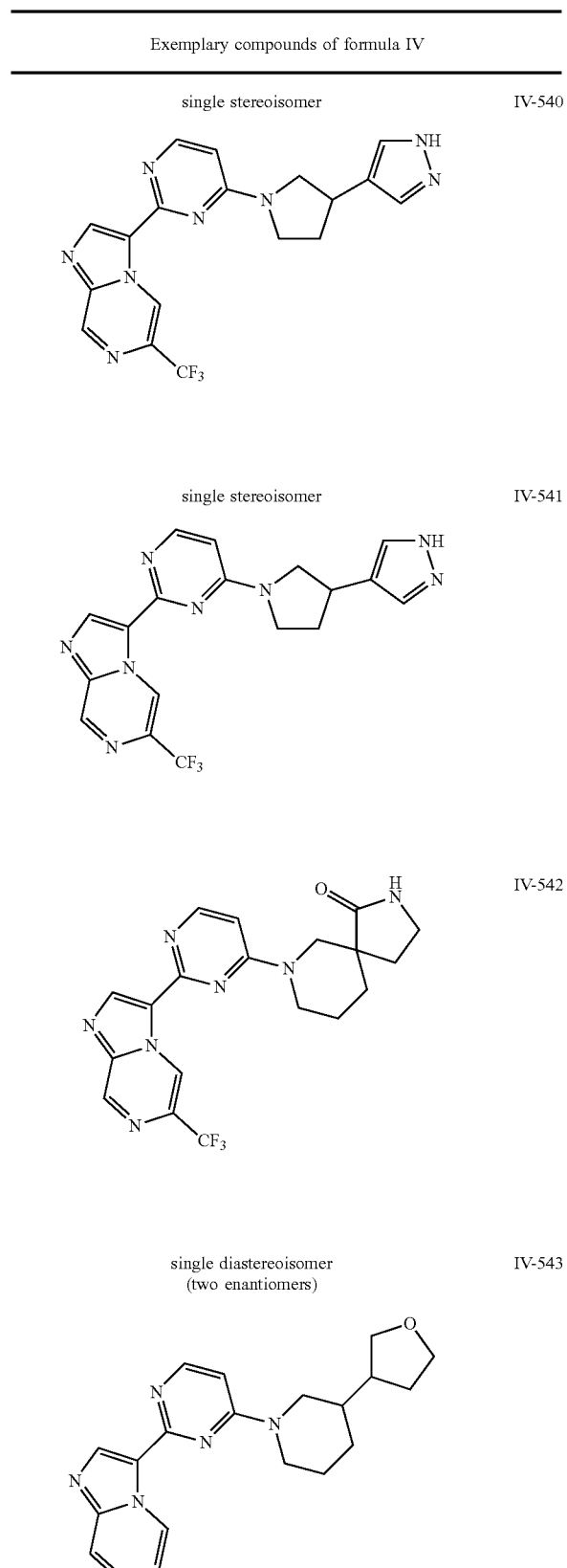
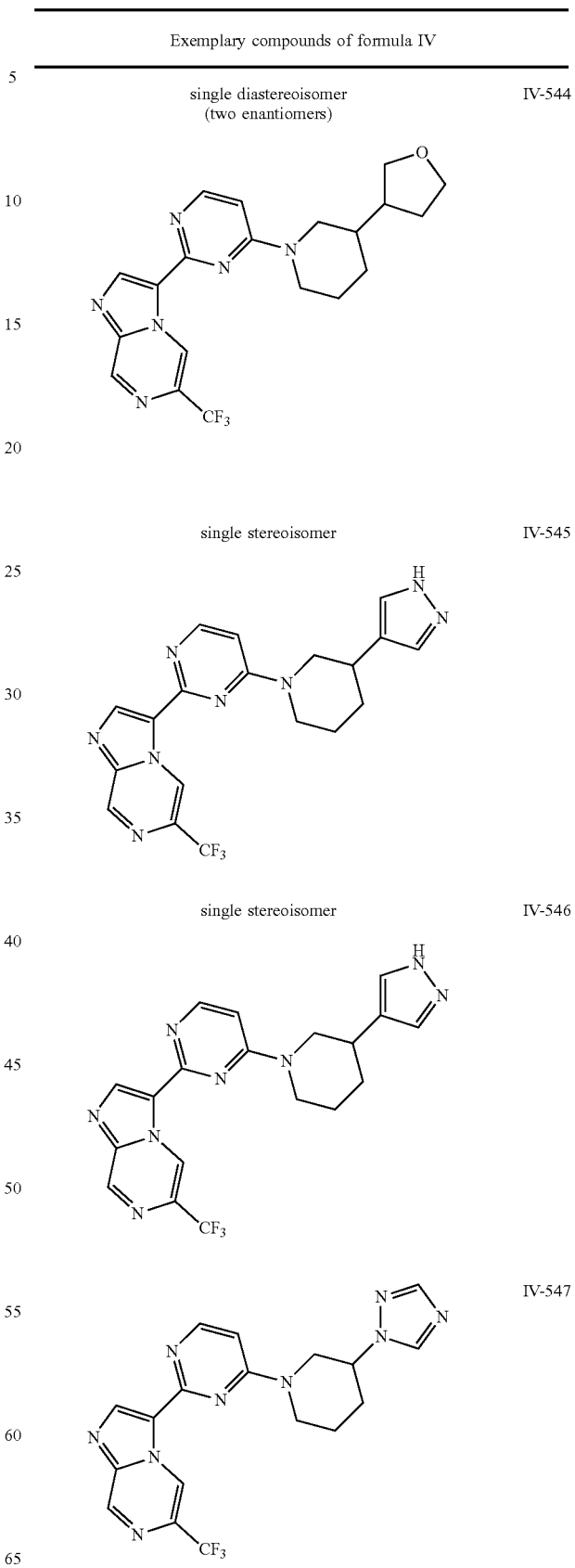

TABLE 3-continued
Exemplary compounds of formula IV
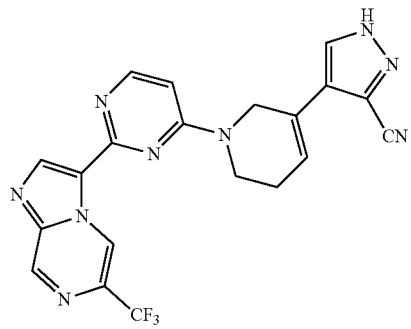 [SMILES: N#Cc1n[nH]cc1C1=CCCN(c2ccnc(-c3cnc4cnc(C(F)(F)F)cn34)n2)C1]
IV-548
single stereoisomer
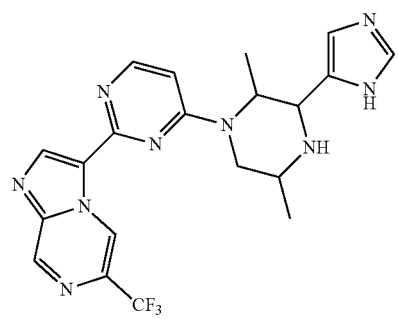 [SMILES: CC1CN(c2ccnc(-c3cnc4cnc(C(F)(F)F)cn34)n2)C(C)C(c2cnc[nH]2)N1]
IV-549
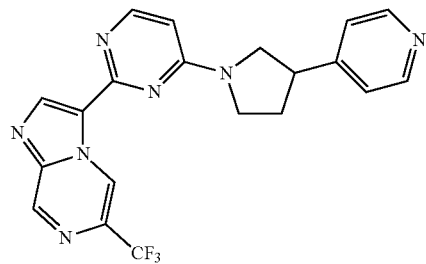 [SMILES: FC(F)(F)c1cn2c(-c3nccc(N4CCC(c5ccncc5)C4)n3)cnc2cn1]
IV-550
single stereoisomer
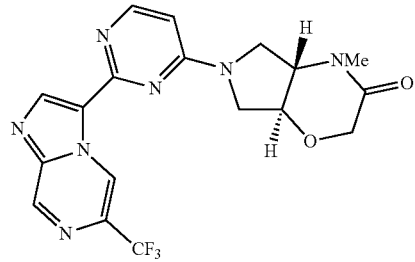 [SMILES: CN1C(=O)CO[C@H]2CN(c3ccnc(-c4cnc5cnc(C(F)(F)F)cn45)n3)C[C@@H]21]
IV-551
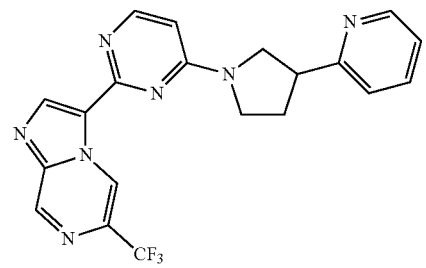
IV-552
TABLE 3-continued
Exemplary compounds of formula IV
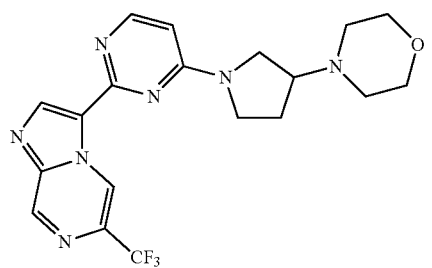
IV-553
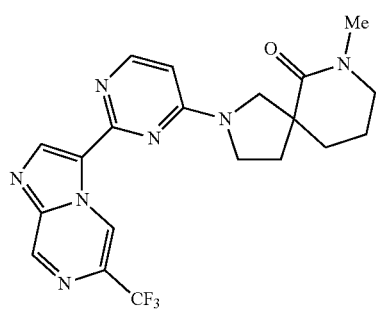 [SMILES: CN1CCCC2(CCN(c3ccnc(-c4cnc5cnc(C(F)(F)F)cn45)n3)C2)C1=O]
IV-554
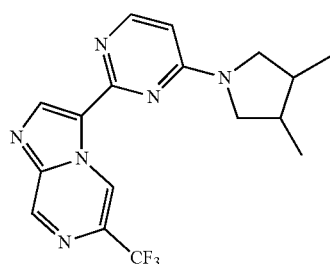
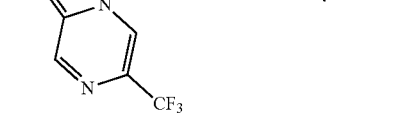
IV-555
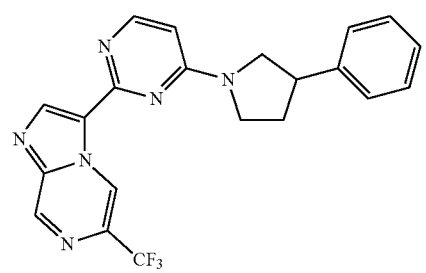 [SMILES: FC(F)(F)c1cn2c(-c3nccc(N4CCC(c5ccccc5)C4)n3)cnc2cn1]
IV-556
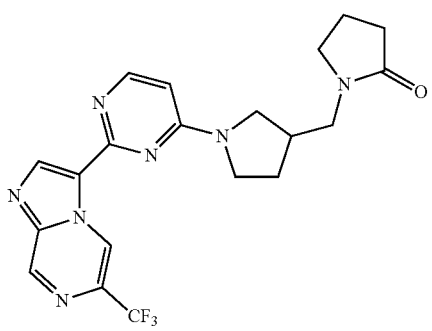 [SMILES: O=C1CCCN1CC1CCN(c2ccnc(-c3cnc4cnc(C(F)(F)F)cn34)n2)C1]
IV-557

TABLE 3-continued
Exemplary compounds of formula IV
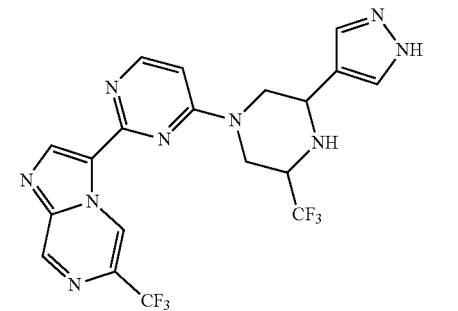
IV-558
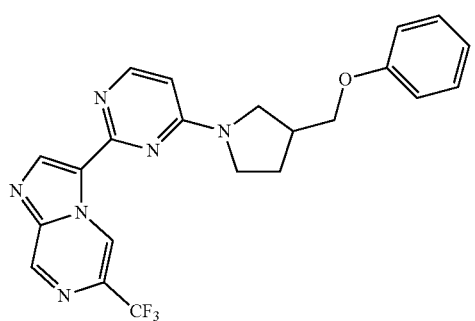 [SMILES: FC(F)(F)c1cn2c(-c3nccc(N4CCC(COc5ccccc5)C4)n3)cnc2cn1]
IV-559
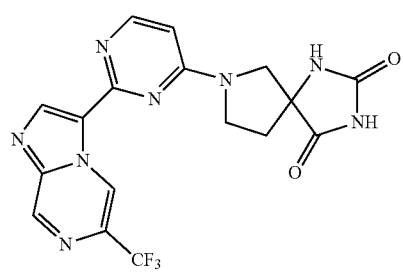 [SMILES: O=C1NC(=O)C2(CCN(c3ccnc(-c4cnc5cnc(C(F)(F)F)cn45)n3)C2)N1]
IV-560
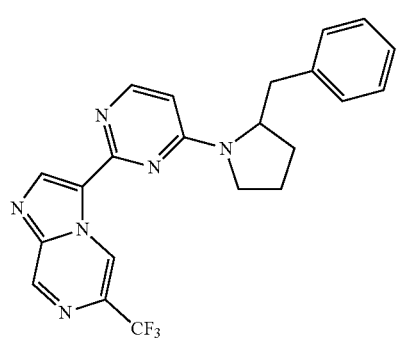 [SMILES: FC(F)(F)c1cn2c(-c3nccc(N4CCCC4Cc4ccccc4)n3)cnc2cn1]
IV-561
single stereoisomer   IV-562
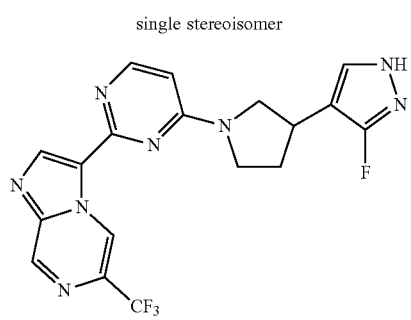
TABLE 3-continued
Exemplary compounds of formula IV
single stereoisomer   IV-563
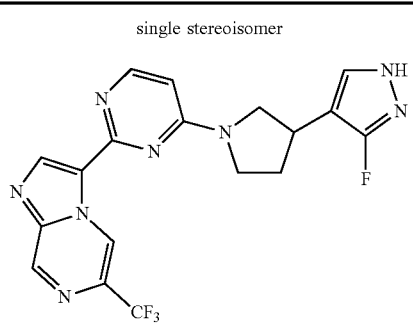
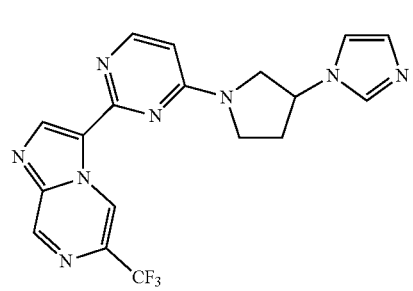 [SMILES: FC(F)(F)c1cn2c(-c3nccc(N4CCC(n5ccnc5)C4)n3)cnc2cn1]
IV-564
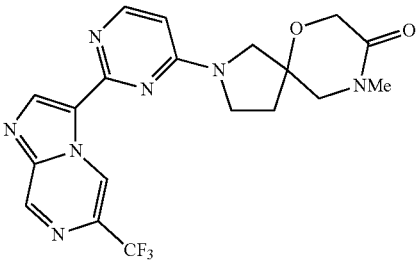 [SMILES: CN1CC2(CCN(c3ccnc(-c4cnc5cnc(C(F)(F)F)cn45)n3)C2)OCC1=O]
IV-565
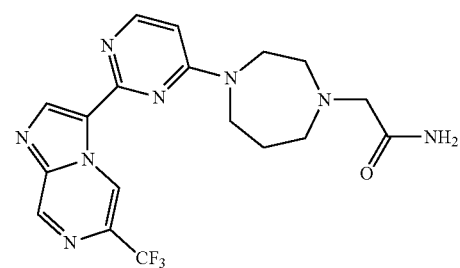 [SMILES: NC(=O)CN1CCCN(c2ccnc(-c3cnc4cnc(C(F)(F)F)cn34)n2)CC1]
IV-566
single diastereoisomer   IV-567
(two enantiomers)
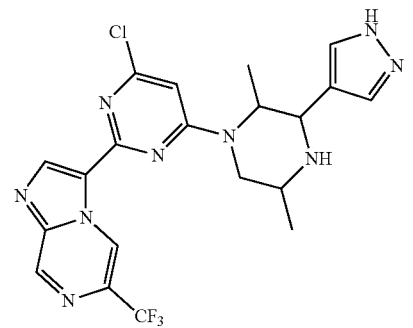 [SMILES: CC1CN(c2cc(Cl)nc(-c3cnc4cnc(C(F)(F)F)cn34)n2)C(C)C(c2cn[nH]c2)N1]

TABLE 3-continued
Exemplary compounds of formula IV
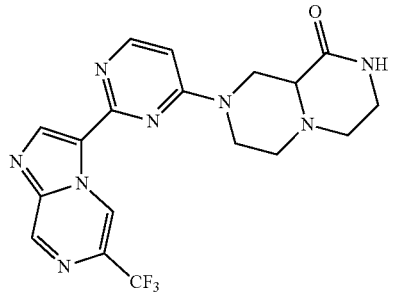
IV-568
single diastereoisomer
(two enantiomers)
IV-569
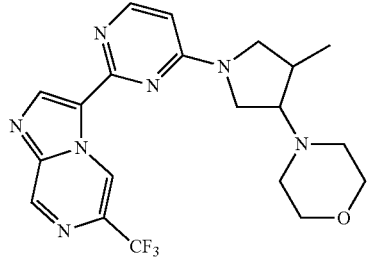 [SMILES: CC1CN(c2ccnc(-c3cnc4cnc(C(F)(F)F)cn34)n2)CC1N1CCOCC1]
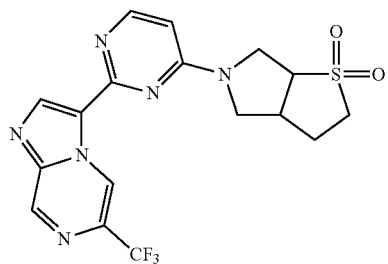 [SMILES: O=S1(=O)CCC2CN(c3ccnc(-c4cnc5cnc(C(F)(F)F)cn45)n3)CC21]
IV-570
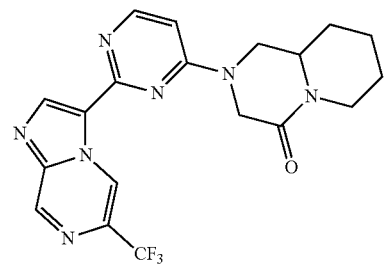 [SMILES: O=C1CN(c2ccnc(-c3cnc4cnc(C(F)(F)F)cn34)n2)CC2CCCCN12]
IV-571
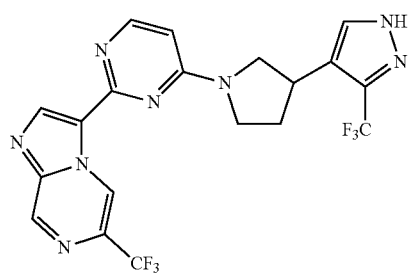 [SMILES: FC(F)(F)c1cn2c(-c3nccc(N4CCC(c5c[nH]nc5C(F)(F)F)C4)n3)cnc2cn1]
IV-572
TABLE 3-continued
Exemplary compounds of formula IV
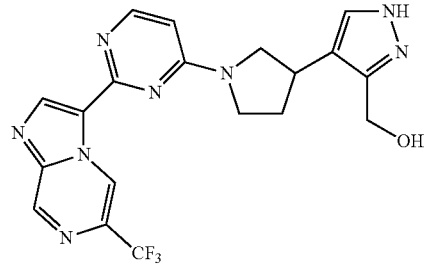 [SMILES: OCc1n[nH]cc1C1CCN(c2ccnc(-c3cnc4cnc(C(F)(F)F)cn34)n2)C1]
IV-573
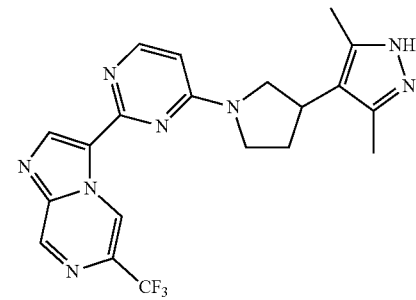 [SMILES: Cc1n[nH]c(C)c1C1CCN(c2ccnc(-c3cnc4cnc(C(F)(F)F)cn34)n2)C1]
IV-574
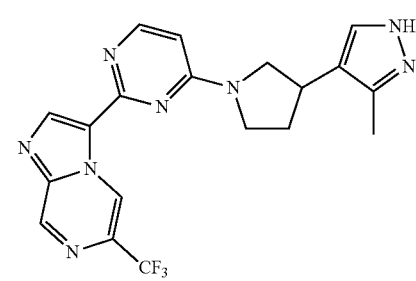 [SMILES: Cc1n[nH]cc1C1CCN(c2ccnc(-c3cnc4cnc(C(F)(F)F)cn34)n2)C1]
IV-575
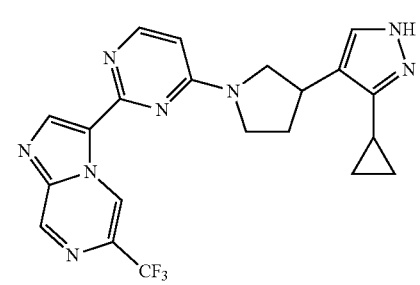 [SMILES: FC(F)(F)c1cn2c(-c3nccc(N4CCC(c5c[nH]nc5C5CC5)C4)n3)cnc2cn1]
IV-576
single diastereoisomer
(two enantiomers)
IV-577
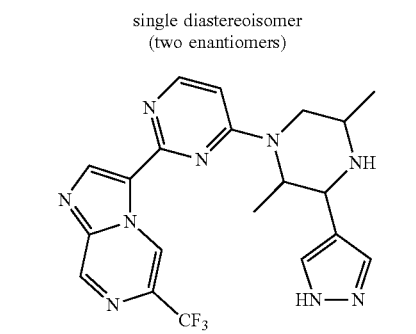

TABLE 3-continued
Exemplary compounds of formula IV
| single diastereoisomer (two enantiomers) | IV-578 |
| --- | --- |
| 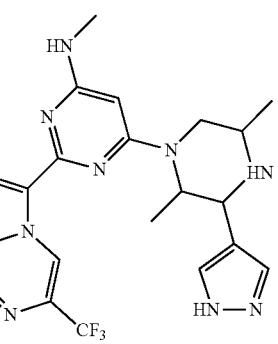 | |
| | IV-579 |
| 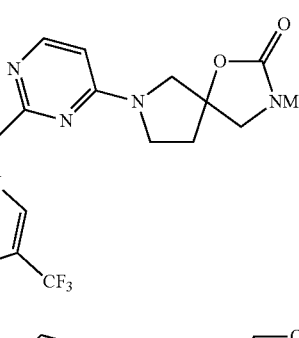 | |
| | IV-580 |
| 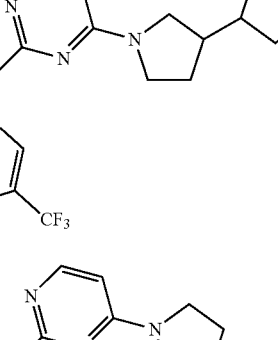 | |
| | IV-581 |
|  | |
| | IV-582 |
| 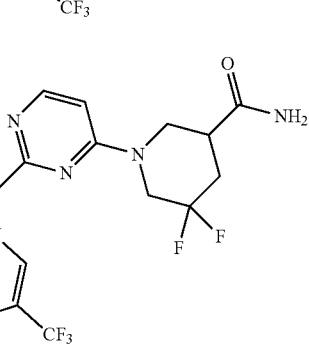 | |
TABLE 3-continued
Exemplary compounds of formula IV
| single diastereoisomer (two enantiomers) | IV-583 |
| --- | --- |
| 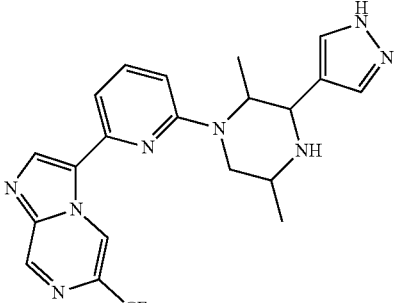 | |
| | IV-584 |
| 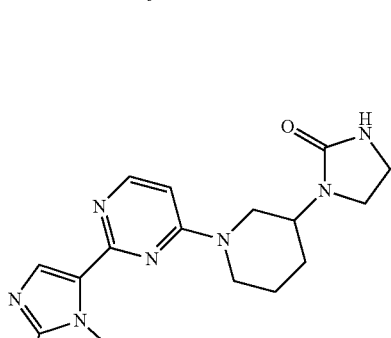 | |
| | IV-585 |
| 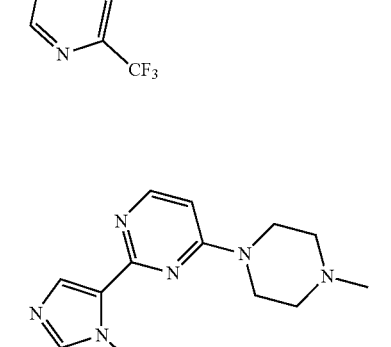 | |
| single diastereoisomer (two enantiomers) | IV-586 |
| 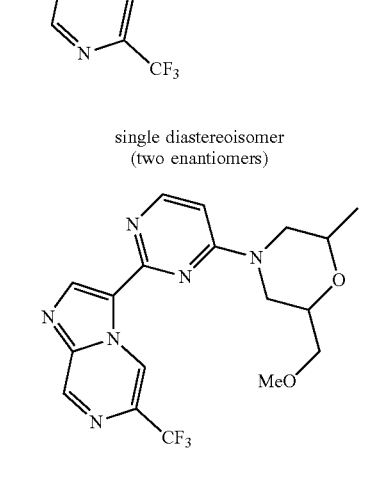 | |

TABLE 3-continued
Exemplary compounds of formula IV
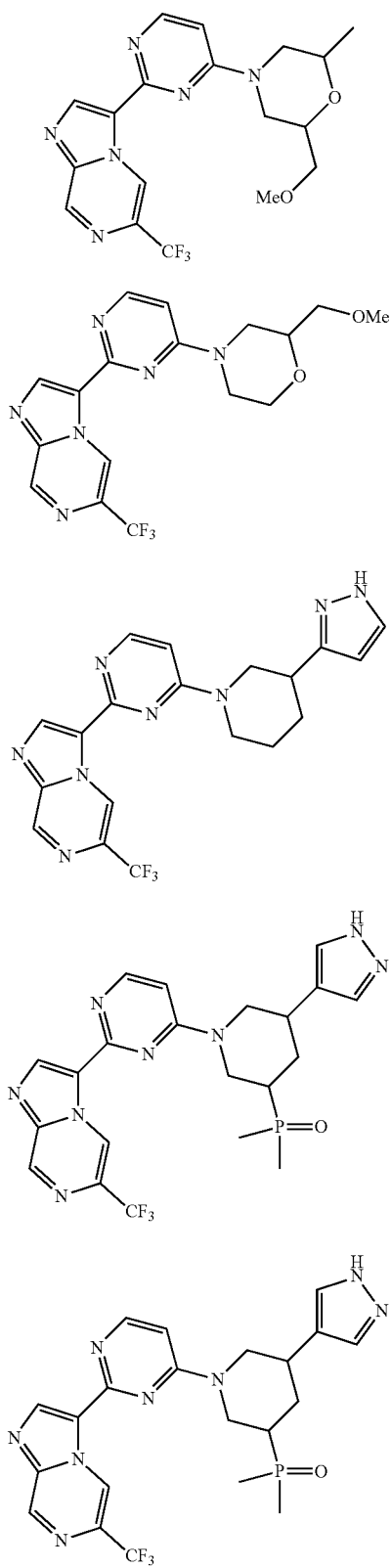
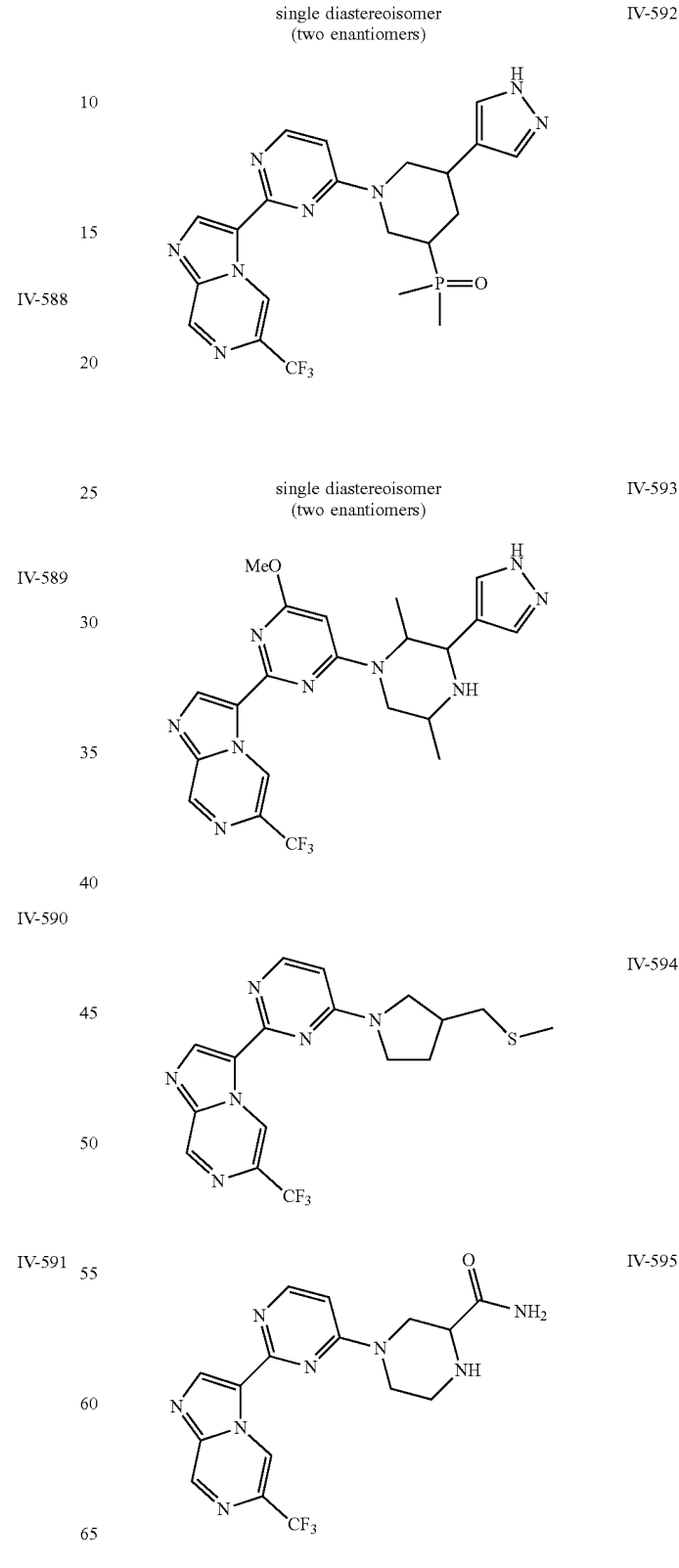

TABLE 3-continued
Exemplary compounds of formula IV
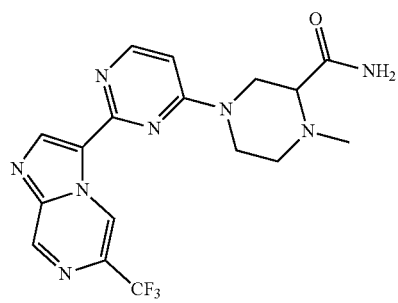
IV-596
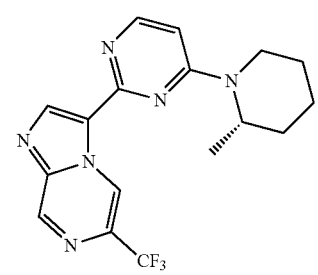
single stereoisomer IV-597
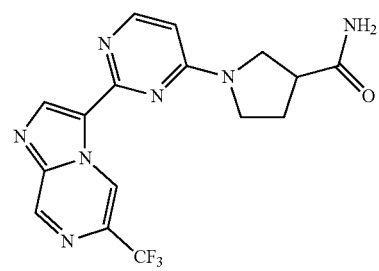 [SMILES: NC(=O)C1CCN(c2ccnc(-c3cnc4cnc(C(F)(F)F)cn34)n2)C1]
IV-598
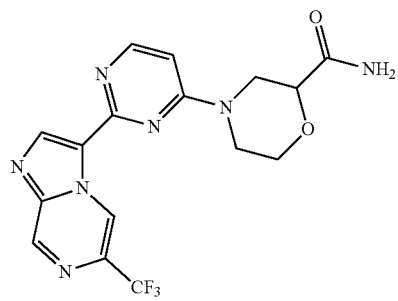 [SMILES: NC(=O)C1CN(c2ccnc(-c3cnc4cnc(C(F)(F)F)cn34)n2)CCO1]
IV-599
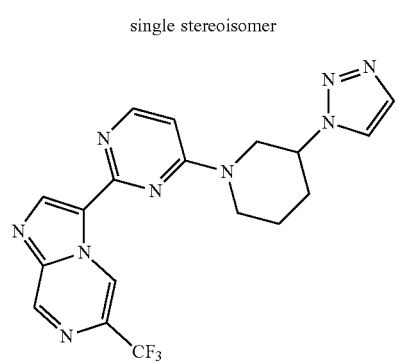
single stereoisomer IV-600
TABLE 3-continued
Exemplary compounds of formula IV
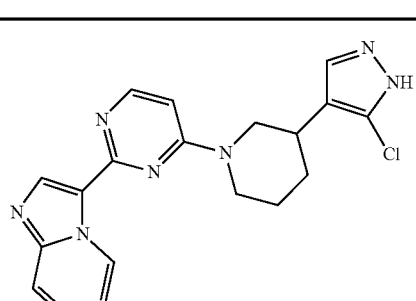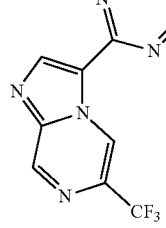
IV-601
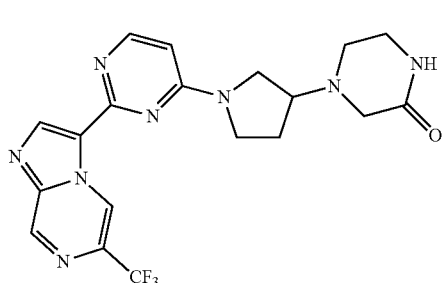
IV-602
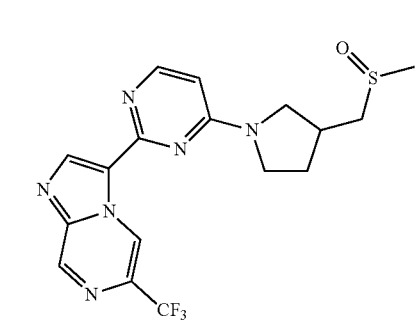 [SMILES: CS(=O)CC1CCN(c2ccnc(-c3cnc4cnc(C(F)(F)F)cn34)n2)C1]
IV-603
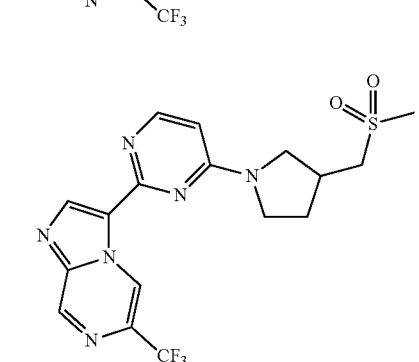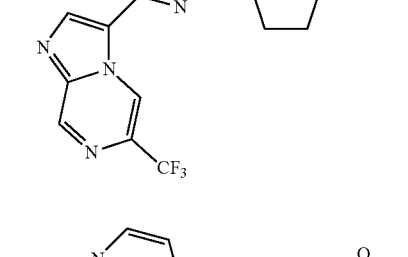
IV-604
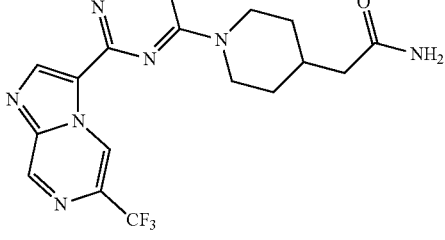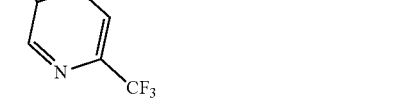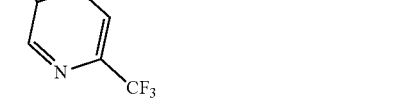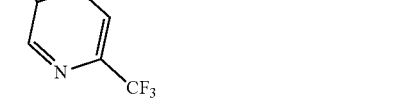
IV-605

TABLE 3-continued
Exemplary compounds of formula IV
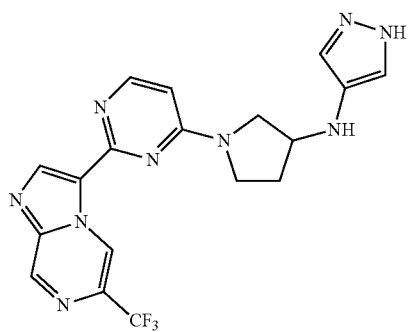 [SMILES: FC(F)(F)c1cn2c(-c3nccc(N4CCC(Nc5cn[nH]c5)C4)n3)cnc2cn1] IV-606
single diastereoisomer (two enantiomers) IV-607
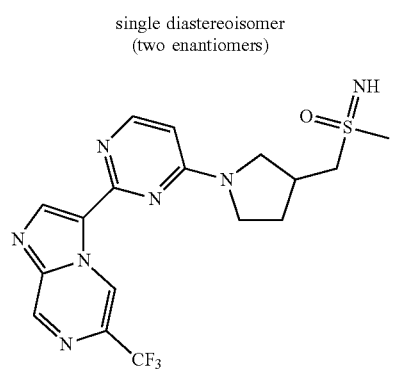
single diastereoisomer (two enantiomers) IV-608
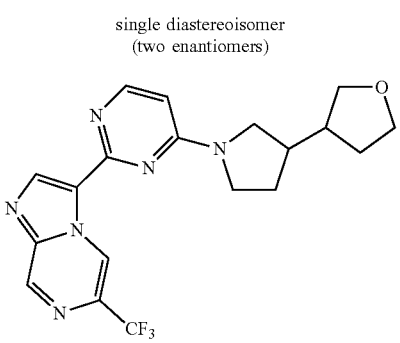
single diastereoisomer (two enantiomers) IV-609
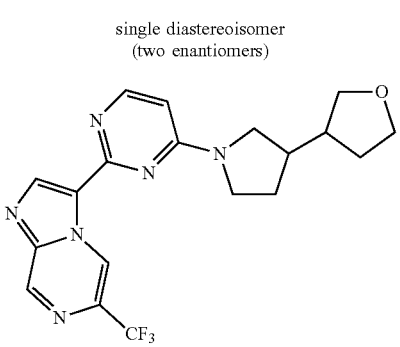
TABLE 3-continued
Exemplary compounds of formula IV
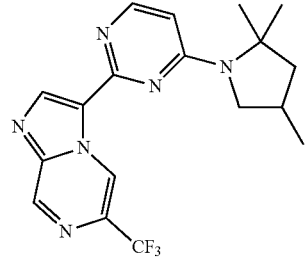 [SMILES: CC1CN(c2ccnc(-c3cnc4cnc(C(F)(F)F)cn34)n2)C(C)(C)C1] IV-610
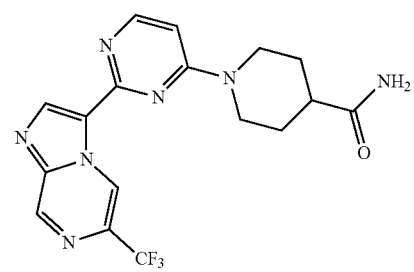 [SMILES: NC(=O)C1CCN(c2ccnc(-c3cnc4cnc(C(F)(F)F)cn34)n2)CC1] IV-611
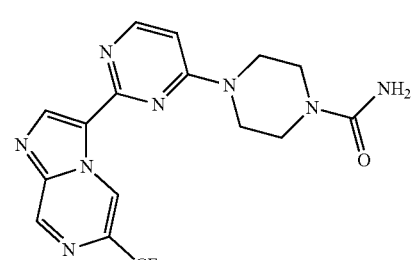 IV-612
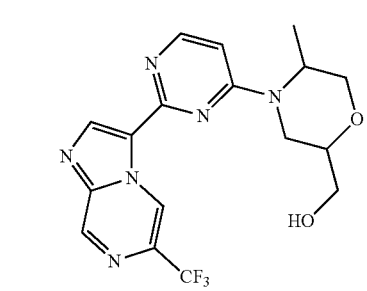 [SMILES: CC1COC(CO)CN1c1ccnc(-c2cnc3cnc(C(F)(F)F)cn23)n1] IV-613
single stereoisomer IV-614
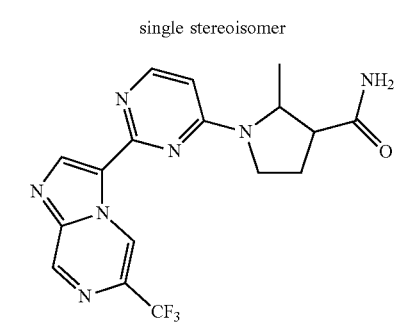

TABLE 3-continued

Exemplary compounds of formula IV

IV-615 single stereoisomer

IV-616

IV-617

IV-618

IV-619

TABLE 3-continued

Exemplary compounds of formula IV

IV-620

IV-621 single stereoisomer

IV-622 single stereoisomer

IV-623 single stereoisomer

TABLE 3-continued
Exemplary compounds of formula IV
| single stereoisomer | IV-624 |
| single stereoisomer | IV-625 |
| | IV-626 |
| single diastereoisomer (two enantiomers) | IV-627 |
| single stereoisomer | IV-628 |
| single stereoisomer | IV-629 |
| | IV-630 |
| | IV-631 |
| single stereoisomer | IV-632 |
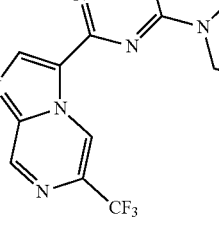
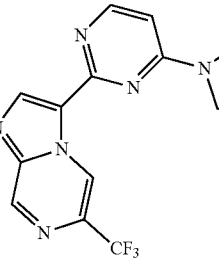
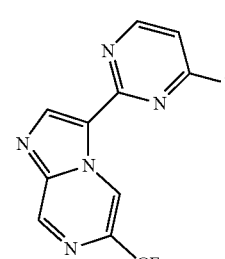
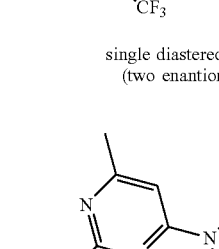
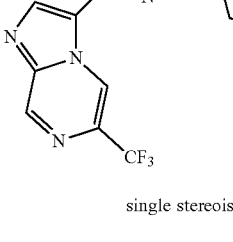

TABLE 3-continued
Exemplary compounds of formula IV
| single stereoisomer | IV-633 |
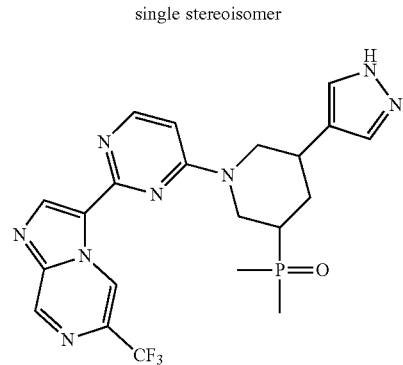
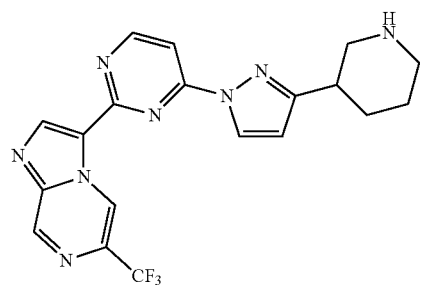 [SMILES: FC(F)(F)c1cn2c(-c3nccc(-n4ccc(C5CCCNC5)n4)n3)cnc2cn1]
IV-634
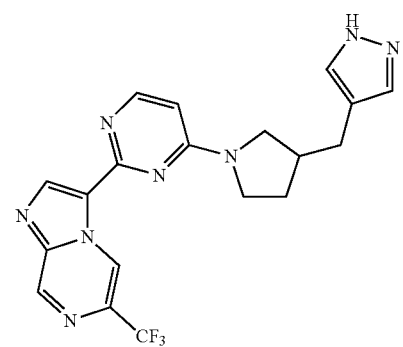 [SMILES: FC(F)(F)c1cn2c(-c3nccc(N4CCC(Cc5cn[nH]c5)C4)n3)cnc2cn1]
IV-635
| single stereoisomer | IV-636 |
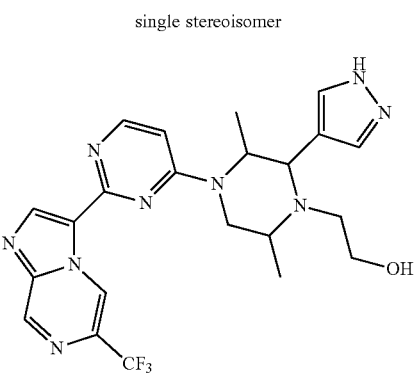
TABLE 3-continued
Exemplary compounds of formula IV
| single diastereoisomer (two enantiomers) | IV-637 |
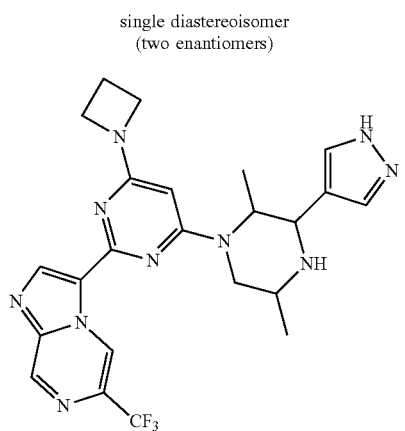
| single stereoisomer | IV-638 |
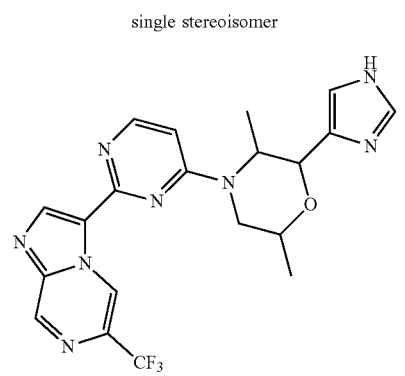
| single stereoisomer | IV-639 |
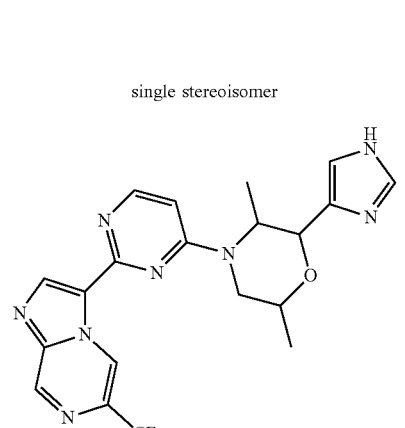

TABLE 3-continued
Exemplary compounds of formula IV
| | |
|---|---|
| single diastereoisomer (two enantiomers) 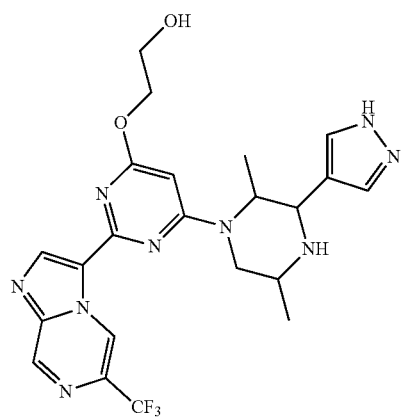 [SMILES: CC1CN(c2cc(OCCO)nc(-c3cnc4cnc(C(F)(F)F)cn34)n2)C(C)C(c2cn[nH]c2)N1] | IV-640 |
| 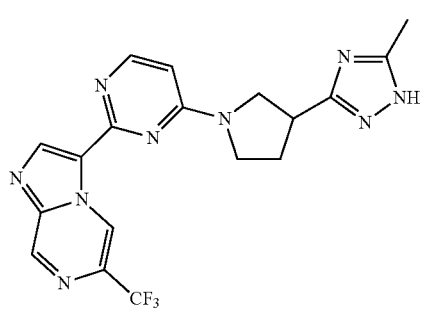 [SMILES: Cc1nc(C2CCN(c3ccnc(-c4cnc5cnc(C(F)(F)F)cn45)n3)C2)n[nH]1] | IV-641 |
| 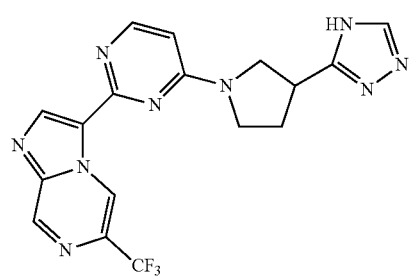 [SMILES: FC(F)(F)c1cn2c(-c3nccc(N4CCC(c5nnc[nH]5)C4)n3)cnc2cn1] | IV-642 |
| 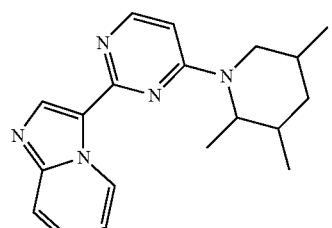 | IV-643 |
| 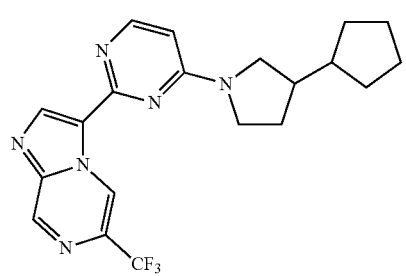 [SMILES: FC(F)(F)c1cn2c(-c3nccc(N4CCC(C5CCCC5)C4)n3)cnc2cn1] | IV-644 |
TABLE 3-continued
Exemplary compounds of formula IV
| | |
|---|---|
| 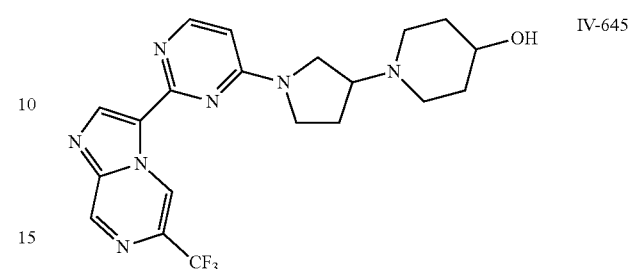 | IV-645 |
| 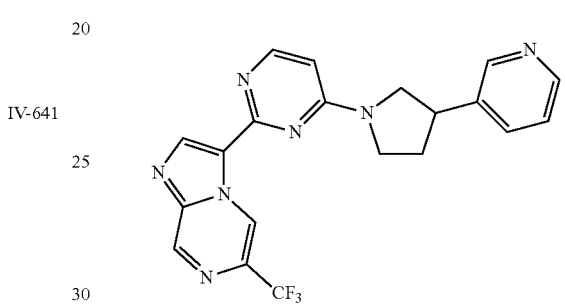 | IV-646 |
| 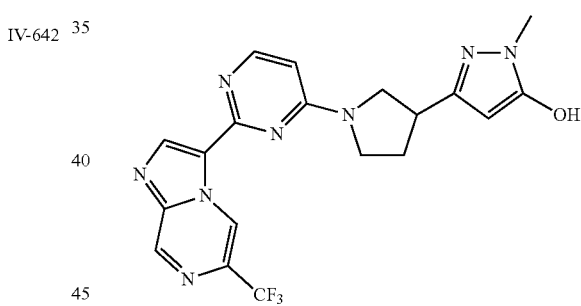 | IV-647 |
| single diastereoisomer (two enantiomers) 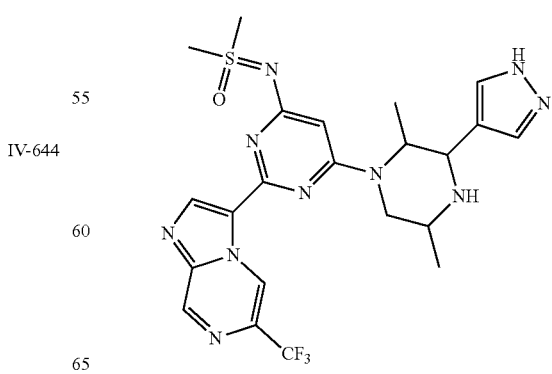 | IV-648 |

TABLE 3-continued
Exemplary compounds of formula IV
single stereoisomer  IV-649
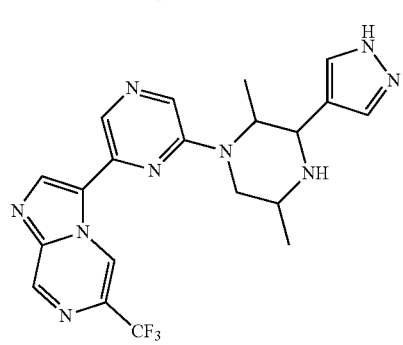 [SMILES: CC1CN(c2cncc(-c3cnc4cnc(C(F)(F)F)cn34)n2)C(C)C(c2cn[nH]c2)N1]
single stereoisomer  IV-650
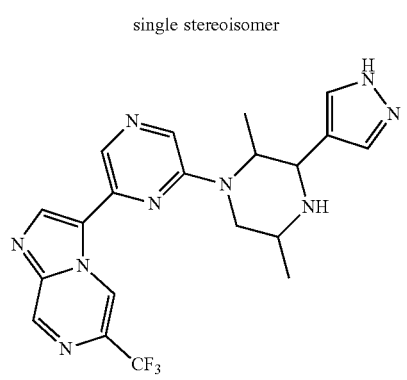
single stereoisomer  IV-651
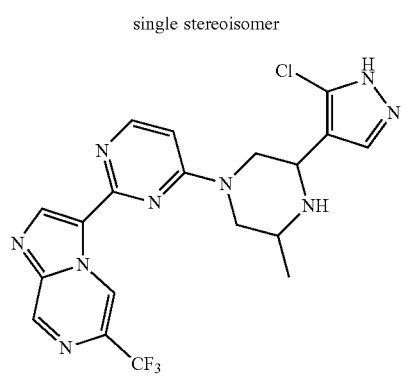
single stereoisomer  IV-652
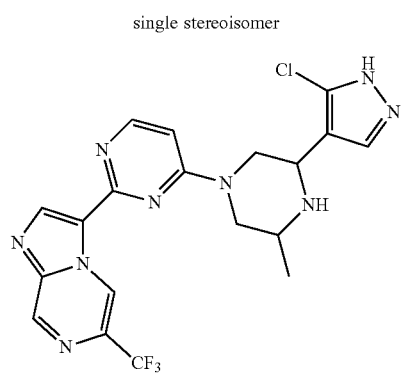
TABLE 3-continued
Exemplary compounds of formula IV
IV-653
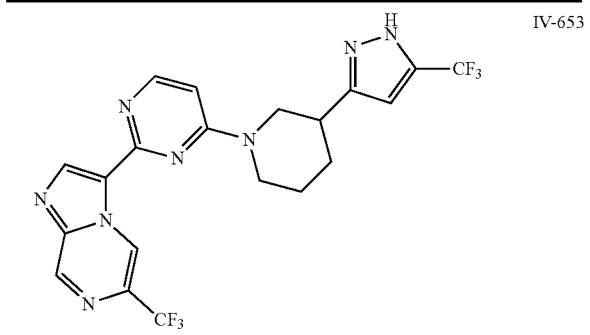
IV-654
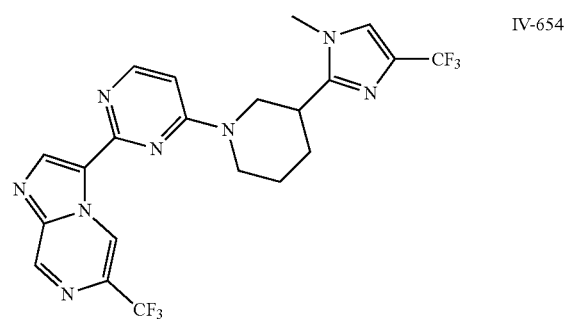
IV-655
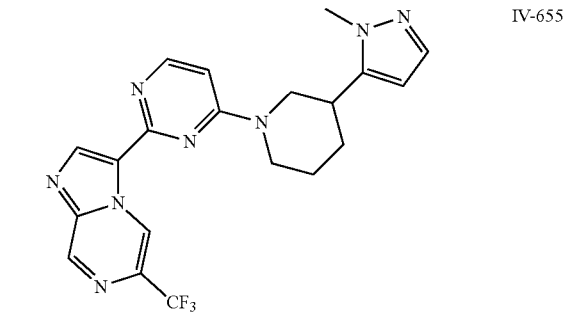
IV-656
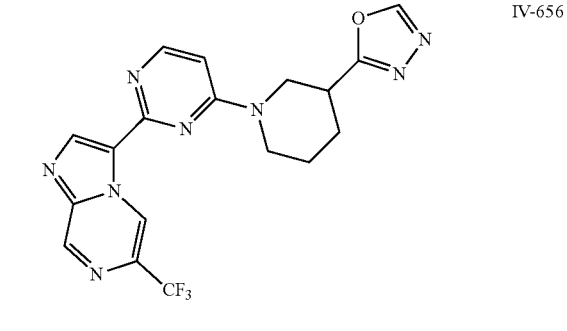
IV-657
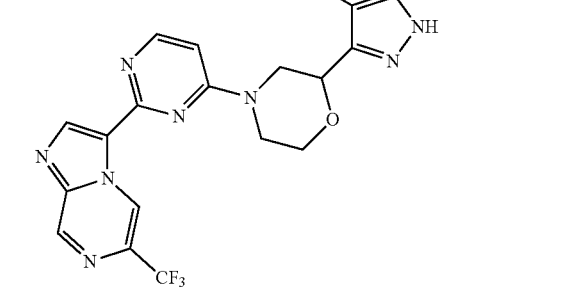

TABLE 3-continued
Exemplary compounds of formula IV
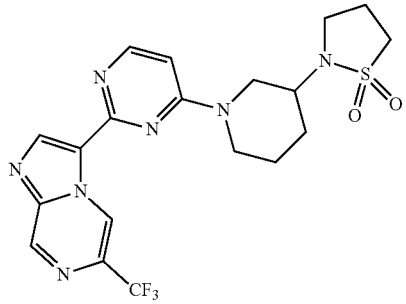 [SMILES: O=S1(=O)CCCN1C1CCCN(c2ccnc(-c3cnc4cnc(C(F)(F)F)cn34)n2)C1] IV-658
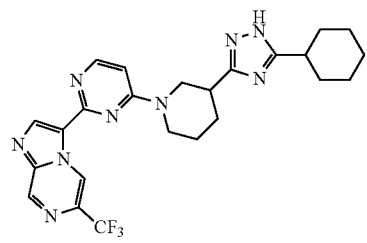 [SMILES: FC(F)(F)c1cn2c(-c3nccc(N4CCCC(c5n[nH]c(C6CCCCC6)n5)C4)n3)cnc2cn1] IV-659
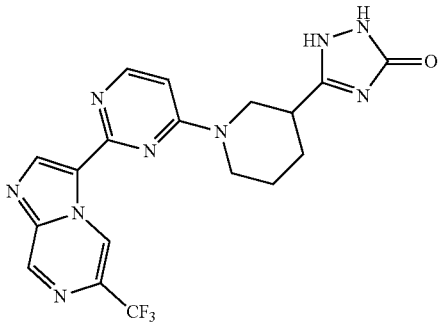 [SMILES: O=c1nc(C2CCCN(c3ccnc(-c4cnc5cnc(C(F)(F)F)cn45)n3)C2)[nH][nH]1] IV-660
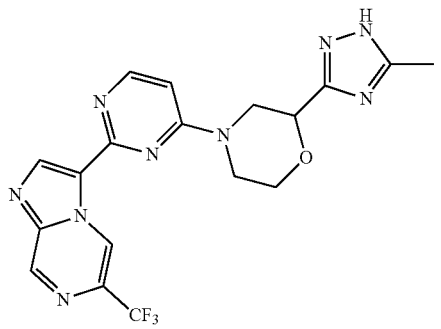 [SMILES: Cc1nc(C2CN(c3ccnc(-c4cnc5cnc(C(F)(F)F)cn45)n3)CCO2)n[nH]1] IV-661
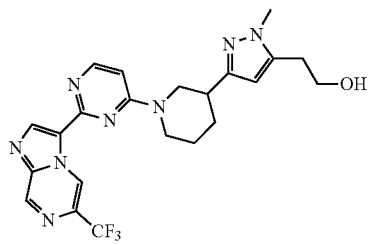 [SMILES: Cn1nc(C2CCCN(c3ccnc(-c4cnc5cnc(C(F)(F)F)cn45)n3)C2)cc1CCO] IV-662
TABLE 3-continued
Exemplary compounds of formula IV
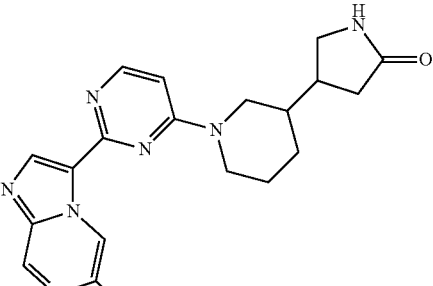 IV-663
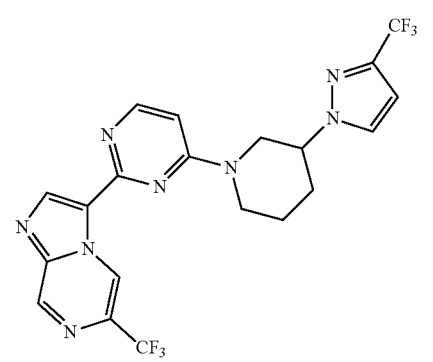 [SMILES: FC(F)(F)c1cn2c(-c3nccc(N4CCCC(n5ccc(C(F)(F)F)n5)C4)n3)cnc2cn1] IV-664
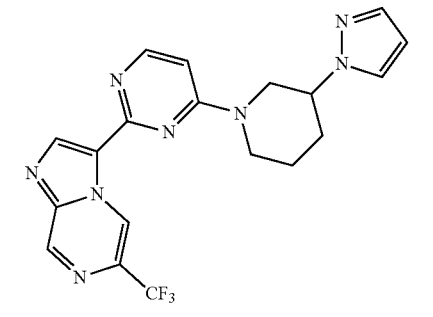 [SMILES: FC(F)(F)c1cn2c(-c3nccc(N4CCCC(n5cccn5)C4)n3)cnc2cn1] IV-665
single diastereoisomer (two enantiomers) IV-666
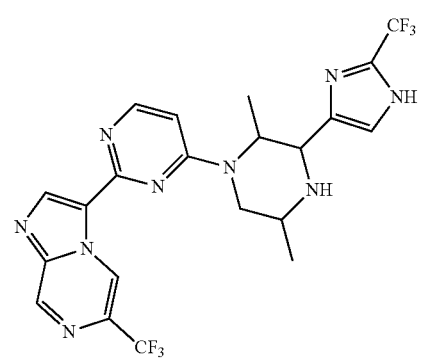 [SMILES: CC1CN(c2ccnc(-c3cnc4cnc(C(F)(F)F)cn34)n2)C(C)C(c2c[nH]c(C(F)(F)F)n2)N1]

TABLE 3-continued
Exemplary compounds of formula IV
IV-667 single diastereoisomer (two enantiomers)
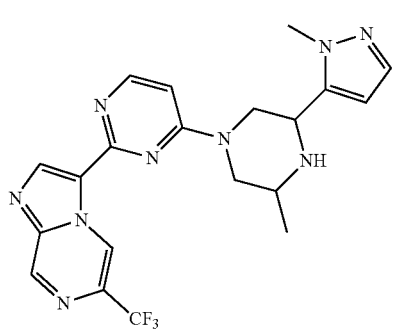 [SMILES: CC1CN(c2ccnc(-c3cnc4cnc(C(F)(F)F)cn34)n2)CC(c2ccnn2C)N1]
IV-668
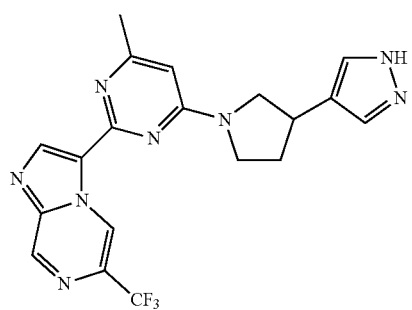 [SMILES: Cc1cc(N2CCC(c3cn[nH]c3)C2)nc(-c2cnc3cnc(C(F)(F)F)cn23)n1]
IV-669 single stereoisomer
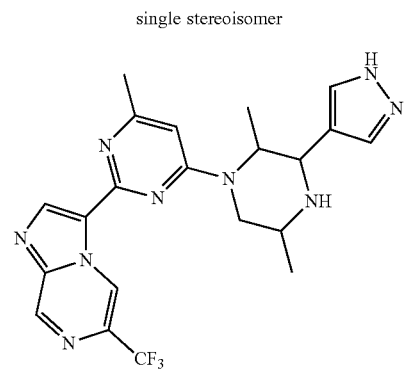
IV-670 single stereoisomer
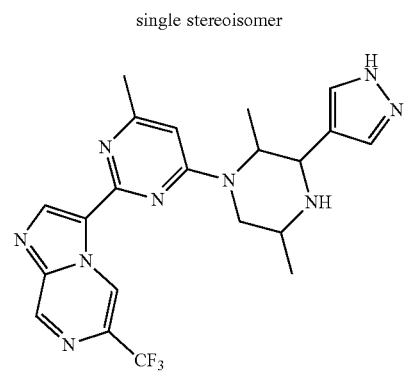
TABLE 3-continued
Exemplary compounds of formula IV
IV-671
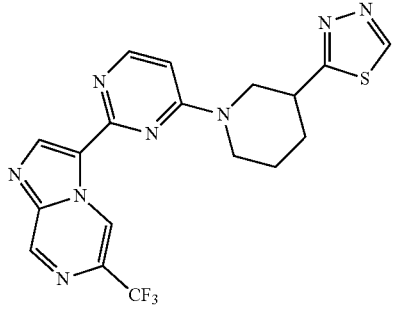
IV-672 single diastereoisomer (two enantiomers)
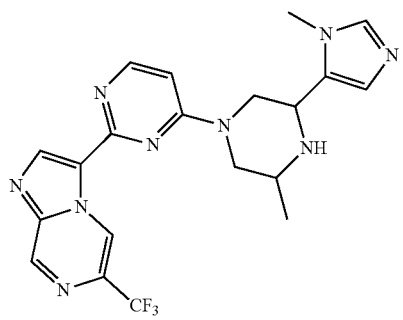 [SMILES: CC1CN(c2ccnc(-c3cnc4cnc(C(F)(F)F)cn34)n2)CC(c2cncn2C)N1]
IV-673 single stereoisomer
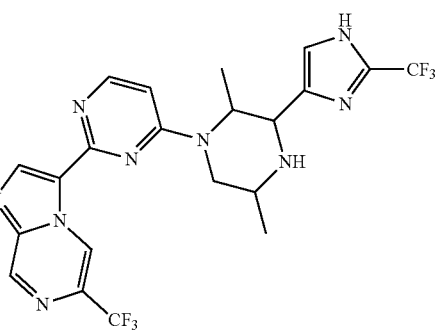
IV-674 single stereoisomer
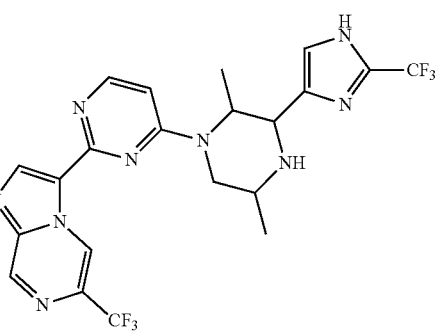

TABLE 3-continued
Exemplary compounds of formula IV
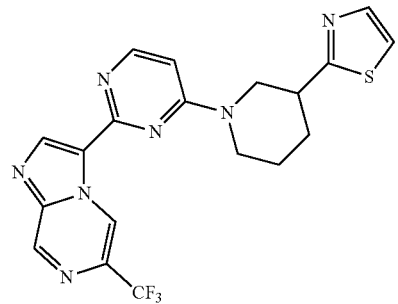 [SMILES: FC(F)(F)c1cn2c(-c3nccc(N4CCCC(c5nccs5)C4)n3)cnc2cn1]
IV-675
single diastereoisomer
(two enantiomers)
IV-676
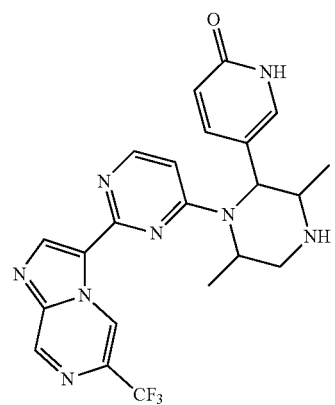 [SMILES: CC1NCC(C)N(c2ccnc(-c3cnc4cnc(C(F)(F)F)cn34)n2)C1c1ccc(=O)[nH]c1]
single diastereoisomer
(two enantiomers)
IV-677
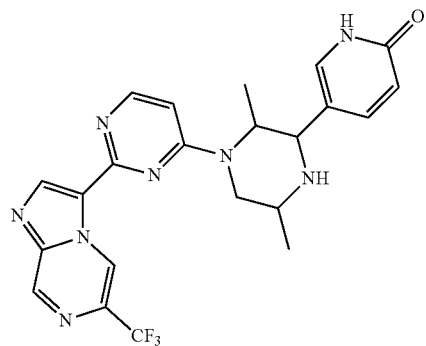 [SMILES: CC1CN(c2ccnc(-c3cnc4cnc(C(F)(F)F)cn34)n2)C(C)C(c2ccc(=O)[nH]c2)N1]
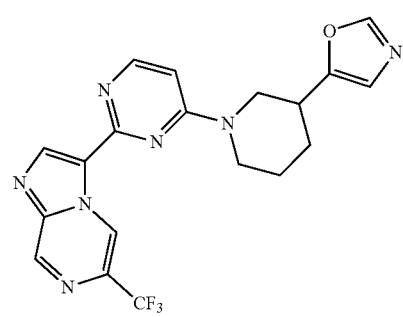 [SMILES: FC(F)(F)c1cn2c(-c3nccc(N4CCCC(c5cnco5)C4)n3)cnc2cn1]
IV-678
TABLE 3-continued
Exemplary compounds of formula IV
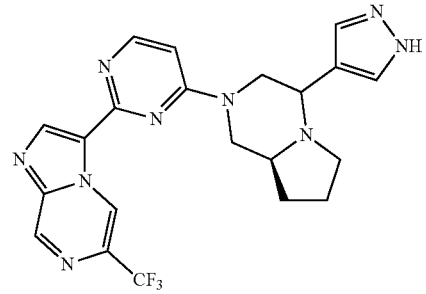 [SMILES: FC(F)(F)c1cn2c(-c3nccc(N4CC(c5cn[nH]c5)N5CCC[C@H]5C4)n3)cnc2cn1]
IV-679
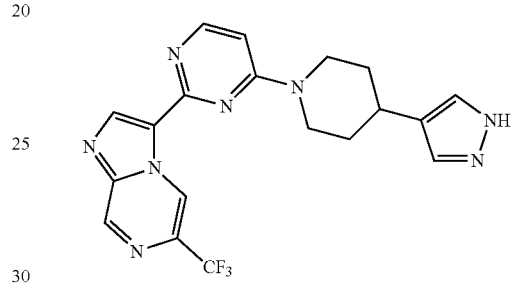
IV-680
IV-681
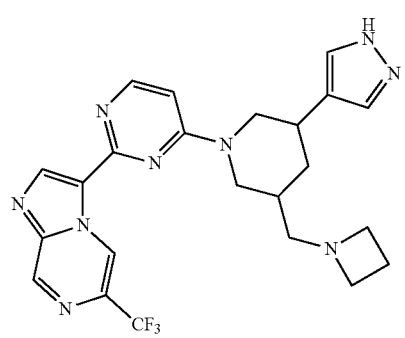 [SMILES: FC(F)(F)c1cn2c(-c3nccc(N4CC(CN5CCC5)CC(c5cn[nH]c5)C4)n3)cnc2cn1]
single stereoisomer
IV-682
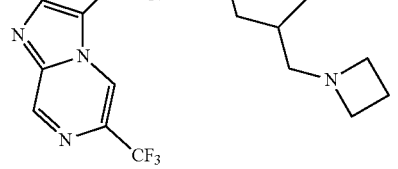

TABLE 3-continued

Exemplary compounds of formula IV

| single stereoisomer | IV-683 |
| single stereoisomer | IV-684 |
| single stereoisomer | IV-685 |
| | IV-686 |

TABLE 3-continued

Exemplary compounds of formula IV

| single diastereoisomer (two enantiomers) | IV-687 |
| single diastereoisomer (two enantiomers) | IV-688 |
| single diastereoisomer (two enantiomers) | IV-689 |
| single diastereoisomer (two enantiomers) | IV-690 |

TABLE 3-continued

Exemplary compounds of formula IV

| | |
|---|---|
| IV-691 | IV-696 |
| IV-692 | single diastereoisomer (two enantiomers) IV-697 |
| single diastereoisomer (two enantiomers) IV-693 | IV-698 |
| IV-694 | IV-699 |
| IV-695 | |

TABLE 3-continued
Exemplary compounds of formula IV
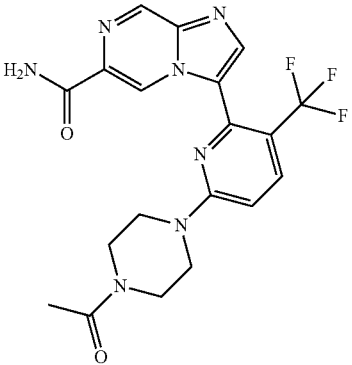 [SMILES: CC(=O)N1CCN(c2ccc(C(F)(F)F)c(-c3cnc4cnc(C(N)=O)cn34)n2)CC1] IV-700
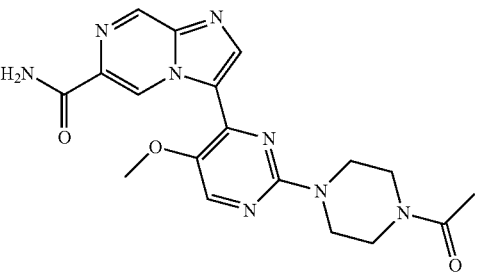 [SMILES: COc1cnc(N2CCN(C(C)=O)CC2)nc1-c1cnc2cnc(C(N)=O)cn12] IV-701
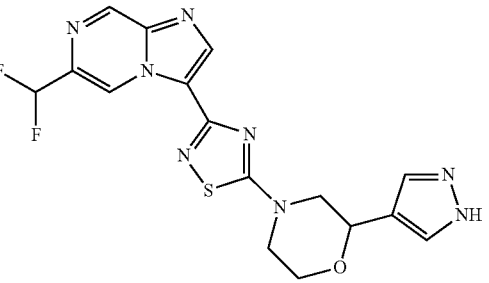 IV-702
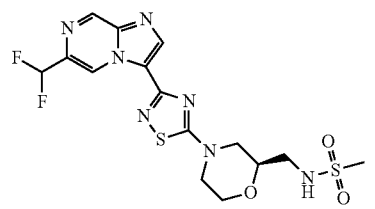 [SMILES: CS(=O)(=O)NC[C@@H]1CN(c2nc(-c3cnc4cnc(C(F)F)cn34)ns2)CCO1] IV-703
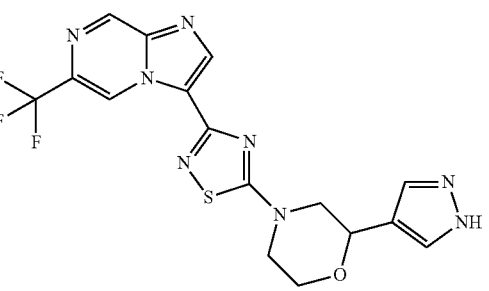 IV-704
TABLE 3-continued
Exemplary compounds of formula IV
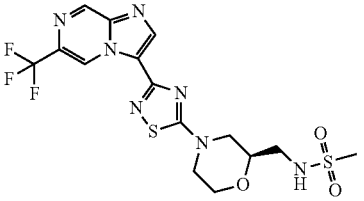 [SMILES: CS(=O)(=O)NC[C@@H]1CN(c2nc(-c3cnc4cnc(C(F)(F)F)cn34)ns2)CCO1] IV-705
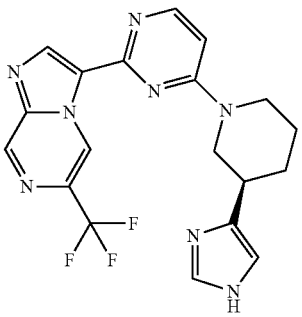 [SMILES: FC(F)(F)c1cn2c(-c3nccc(N4CCC[C@@H](c5c[nH]cn5)C4)n3)cnc2cn1] IV-706
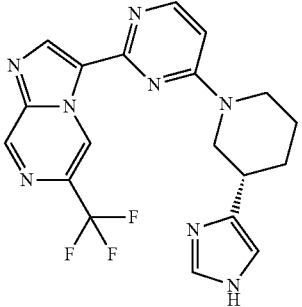 [SMILES: FC(F)(F)c1cn2c(-c3nccc(N4CCC[C@H](c5c[nH]cn5)C4)n3)cnc2cn1] IV-707
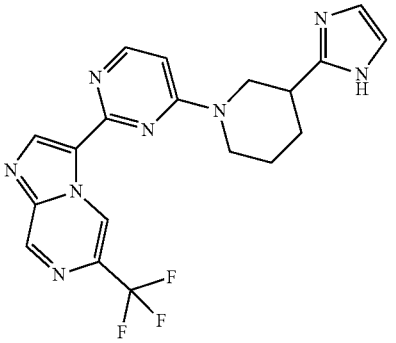 [SMILES: FC(F)(F)c1cn2c(-c3nccc(N4CCCC(c5ncc[nH]5)C4)n3)cnc2cn1] IV-708

TABLE 3-continued
Exemplary compounds of formula IV
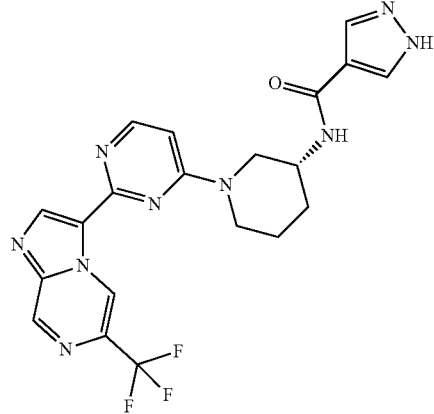 [SMILES: O=C(N[C@@H]1CCCN(c2ccnc(-c3cnc4cnc(C(F)(F)F)cn34)n2)C1)c1cn[nH]c1]
IV-709
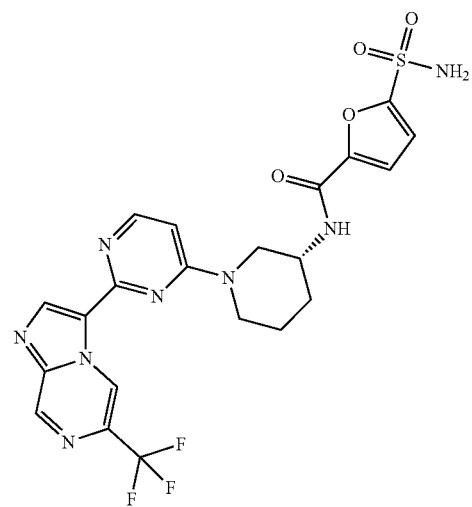 [SMILES: NS(=O)(=O)c1ccc(C(=O)N[C@@H]2CCCN(c3ccnc(-c4cnc5cnc(C(F)(F)F)cn45)n3)C2)o1]
IV-710
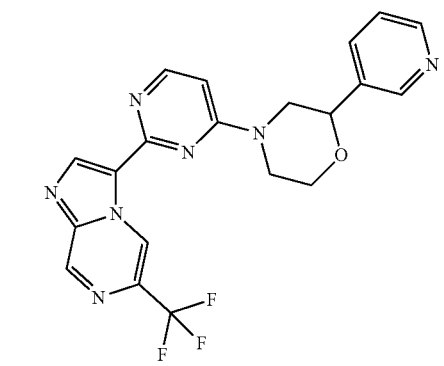 [SMILES: FC(F)(F)c1cn2c(-c3nccc(N4CCOC(c5cccnc5)C4)n3)cnc2cn1]
IV-711
TABLE 3-continued
Exemplary compounds of formula IV
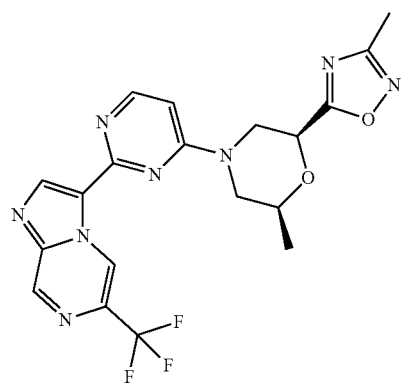 [SMILES: Cc1noc([C@@H]2CN(c3ccnc(-c4cnc5cnc(C(F)(F)F)cn45)n3)C[C@H](C)O2)n1]
IV-712
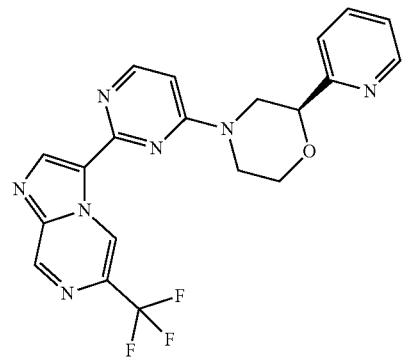 [SMILES: FC(F)(F)c1cn2c(-c3nccc(N4CCO[C@H](c5ccccn5)C4)n3)cnc2cn1]
IV-713
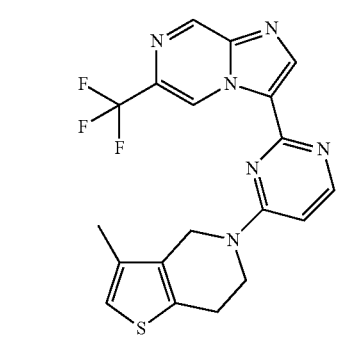 [SMILES: Cc1csc2c1CN(c1ccnc(-c3cnc4cnc(C(F)(F)F)cn34)n1)CC2]
IV-714
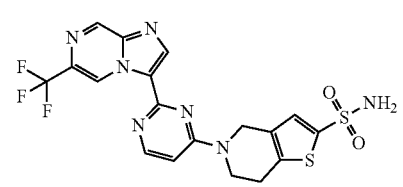 [SMILES: NS(=O)(=O)c1cc2c(s1)CCN(c1ccnc(-c3cnc4cnc(C(F)(F)F)cn34)n1)C2]
IV-715

TABLE 3-continued
Exemplary compounds of formula IV
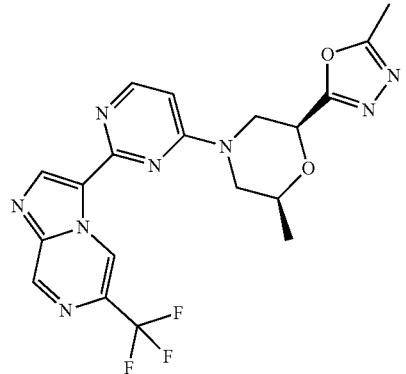 [SMILES: Cc1nnc([C@@H]2CN(c3ccnc(-c4cnc5cnc(C(F)(F)F)cn45)n3)C[C@H](C)O2)o1]
IV-716
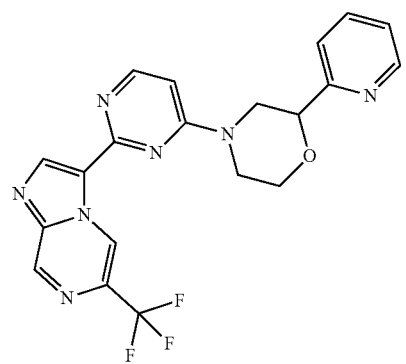 [SMILES: FC(F)(F)c1cn2c(-c3nccc(N4CCOC(c5ccccn5)C4)n3)cnc2cn1]
IV-717
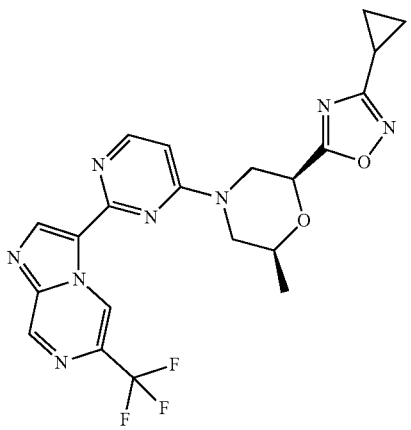 [SMILES: C[C@H]1CN(c2ccnc(-c3cnc4cnc(C(F)(F)F)cn34)n2)C[C@@H](c2nc(C3CC3)no2)O1]
IV-718
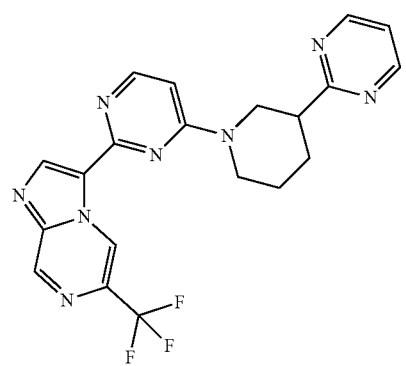 [SMILES: FC(F)(F)c1cn2c(-c3nccc(N4CCCC(c5ncccn5)C4)n3)cnc2cn1]
IV-719
TABLE 3-continued
Exemplary compounds of formula IV
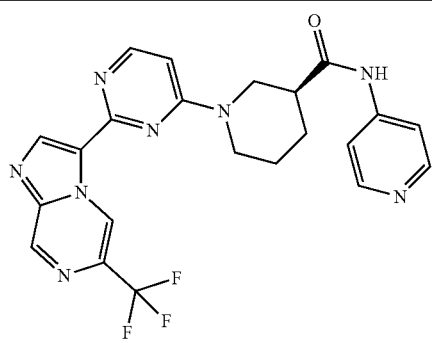
IV-720
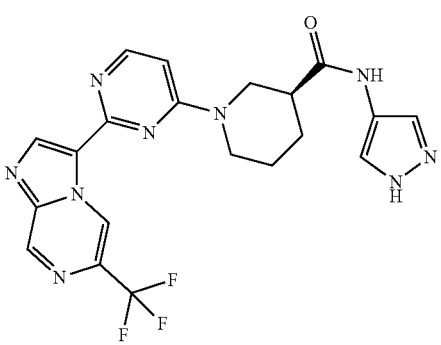 [SMILES: O=C(Nc1cn[nH]c1)[C@H]1CCCN(c2ccnc(-c3cnc4cnc(C(F)(F)F)cn34)n2)C1]
IV-721
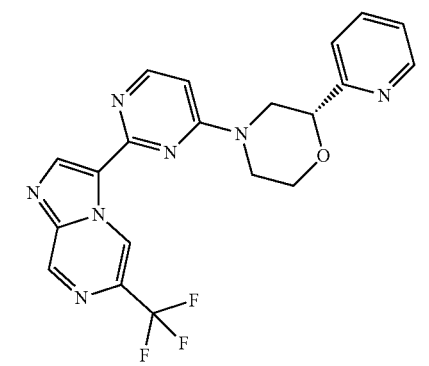
IV-722
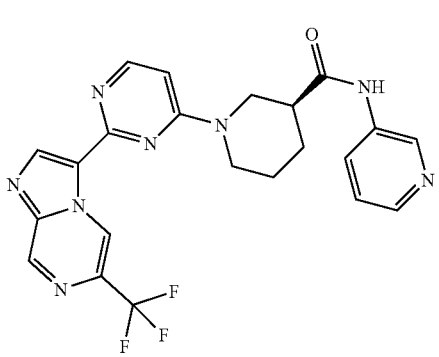 [SMILES: O=C(Nc1cccnc1)[C@H]1CCCN(c2ccnc(-c3cnc4cnc(C(F)(F)F)cn34)n2)C1]
IV-723

TABLE 3-continued
Exemplary compounds of formula IV
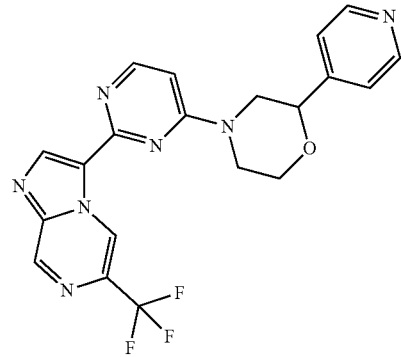 [SMILES: FC(F)(F)c1cn2c(-c3nccc(N4CCOC(c5ccncc5)C4)n3)cnc2cn1] IV-724
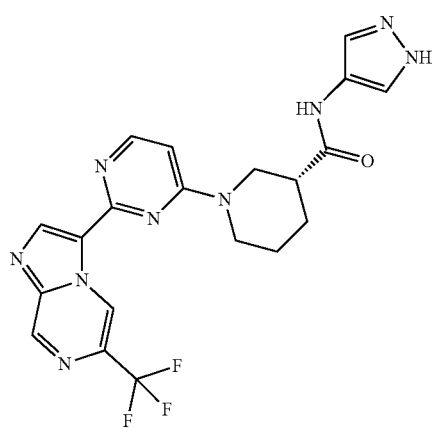 [SMILES: O=C(Nc1cn[nH]c1)[C@@H]1CCCN(c2ccnc(-c3cnc4cnc(C(F)(F)F)cn34)n2)C1] IV-725
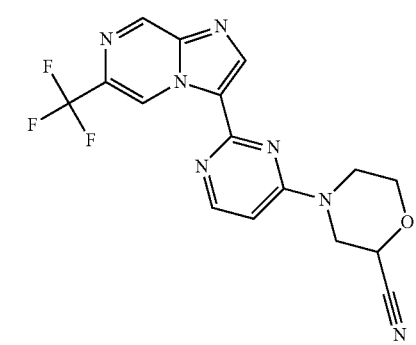 [SMILES: N#CC1CN(c2ccnc(-c3cnc4cnc(C(F)(F)F)cn34)n2)CCO1] IV-726
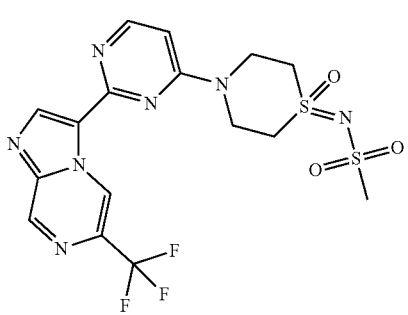 [SMILES: CS(=O)(=O)N=S1(=O)CCN(c2ccnc(-c3cnc4cnc(C(F)(F)F)cn34)n2)CC1] IV-727
TABLE 3-continued
Exemplary compounds of formula IV
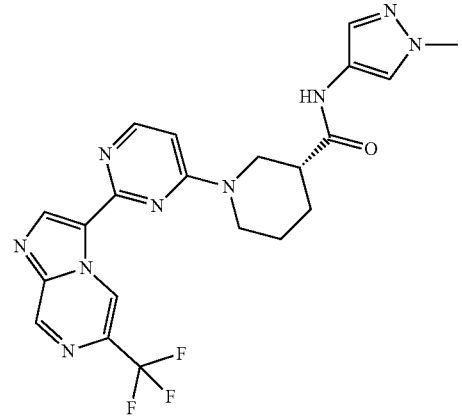 [SMILES: Cn1cc(NC(=O)[C@@H]2CCCN(c3ccnc(-c4cnc5cnc(C(F)(F)F)cn45)n3)C2)cn1] IV-728
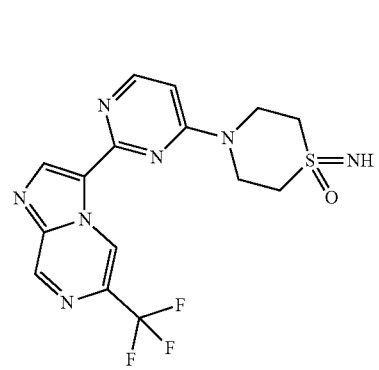 [SMILES: N=S1(=O)CCN(c2ccnc(-c3cnc4cnc(C(F)(F)F)cn34)n2)CC1] IV-729
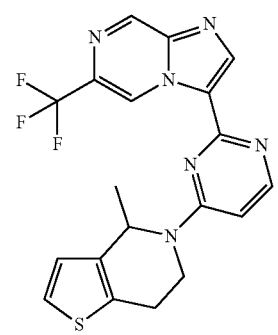 [SMILES: CC1c2ccsc2CCN1c1ccnc(-c2cnc3cnc(C(F)(F)F)cn23)n1] IV-730
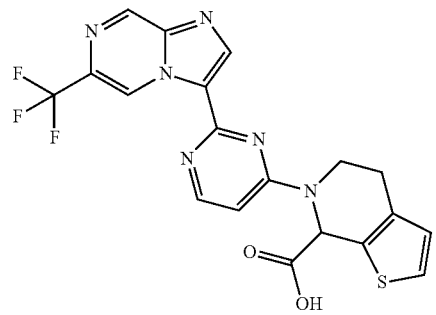 [SMILES: O=C(O)C1c2sccc2CCN1c1ccnc(-c2cnc3cnc(C(F)(F)F)cn23)n1] IV-731

TABLE 3-continued
Exemplary compounds of formula IV
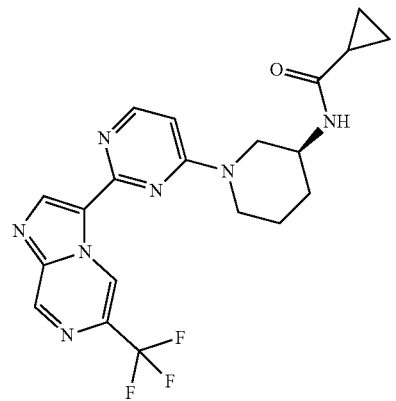 [SMILES: O=C(N[C@H]1CCCN(c2ccnc(-c3cnc4cnc(C(F)(F)F)cn34)n2)C1)C1CC1] IV-732
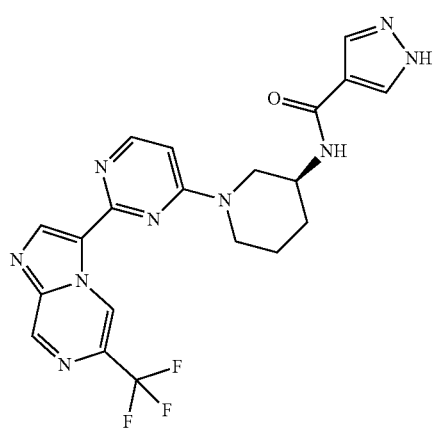 [SMILES: O=C(N[C@H]1CCCN(c2ccnc(-c3cnc4cnc(C(F)(F)F)cn34)n2)C1)c1cn[nH]c1] IV-733
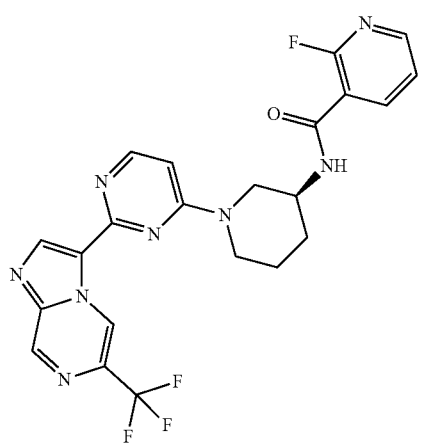 [SMILES: O=C(N[C@H]1CCCN(c2ccnc(-c3cnc4cnc(C(F)(F)F)cn34)n2)C1)c1cccnc1F] IV-734
TABLE 3-continued
Exemplary compounds of formula IV
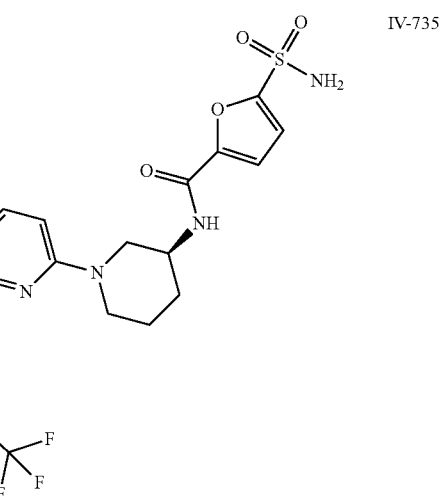 IV-735
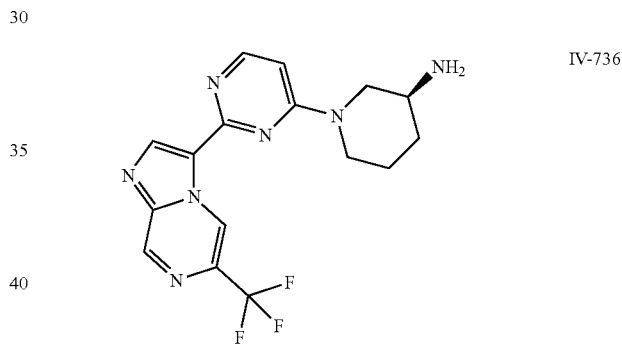 IV-736
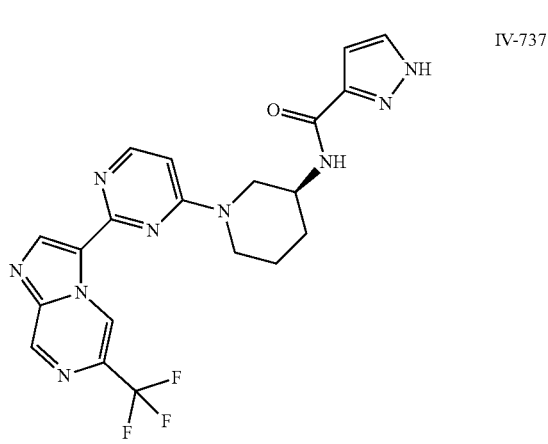 IV-737

TABLE 3-continued
Exemplary compounds of formula IV
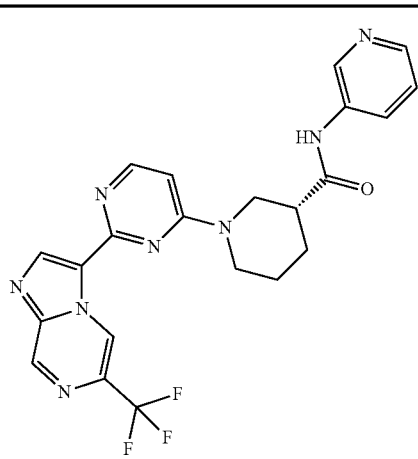
IV-738
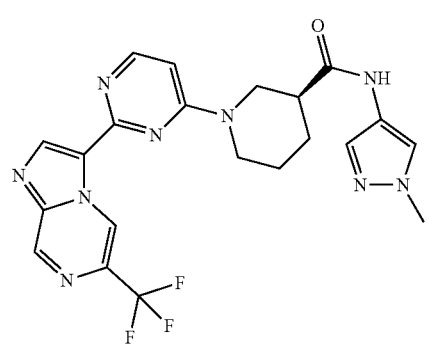 [SMILES: Cn1cc(NC(=O)[C@H]2CCCN(c3ccnc(-c4cnc5cnc(C(F)(F)F)cn45)n3)C2)cn1]
IV-739
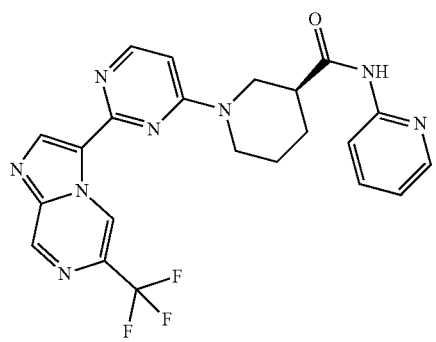 [SMILES: O=C(Nc1ccccn1)[C@H]1CCCN(c2ccnc(-c3cnc4cnc(C(F)(F)F)cn34)n2)C1]
IV-740
TABLE 3-continued
Exemplary compounds of formula IV
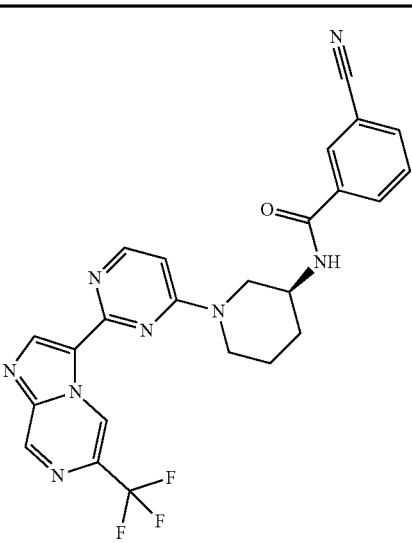
IV-741
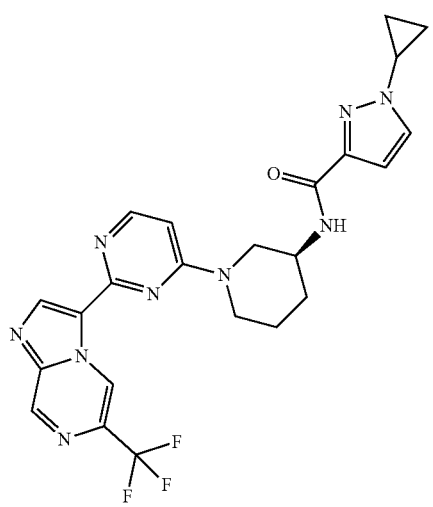 [SMILES: O=C(N[C@H]1CCCN(c2ccnc(-c3cnc4cnc(C(F)(F)F)cn34)n2)C1)c1ccn(C2CC2)n1]
IV-742
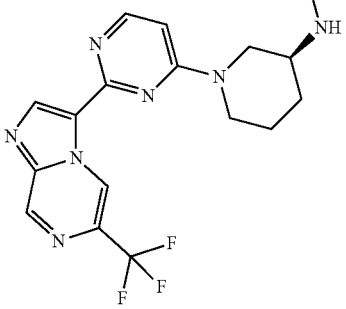
IV-743

TABLE 3-continued
Exemplary compounds of formula IV
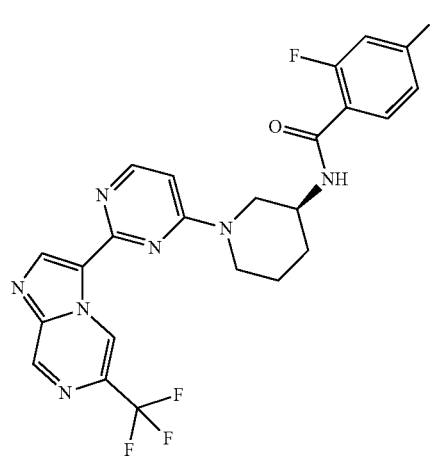
IV-744
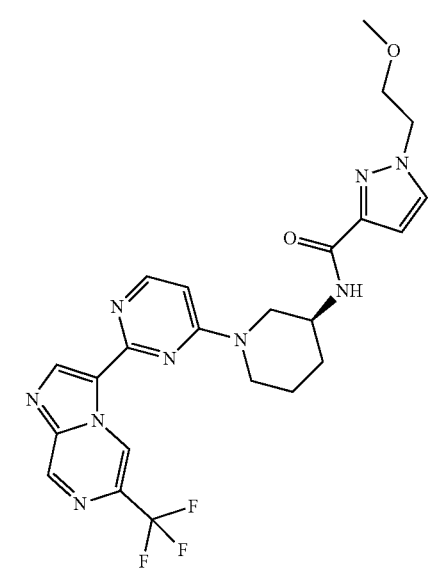 [SMILES: COCCn1ccc(C(=O)N[C@H]2CCCN(c3ccnc(-c4cnc5cnc(C(F)(F)F)cn45)n3)C2)n1]
IV-745
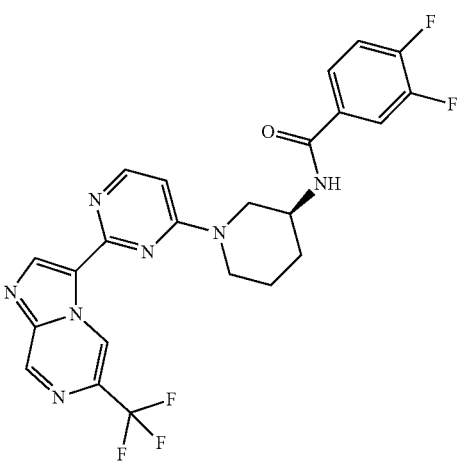 [SMILES: O=C(N[C@H]1CCCN(c2ccnc(-c3cnc4cnc(C(F)(F)F)cn34)n2)C1)c1ccc(F)c(F)c1]
IV-746
TABLE 3-continued
Exemplary compounds of formula IV
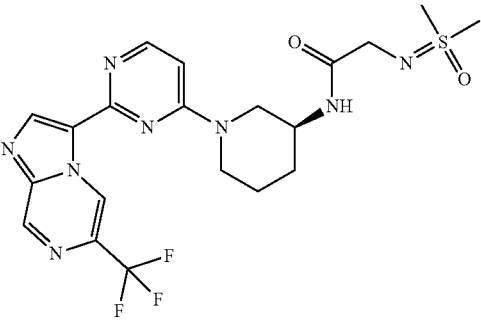 [SMILES: CS(C)(=O)=NCC(=O)N[C@H]1CCCN(c2ccnc(-c3cnc4cnc(C(F)(F)F)cn34)n2)C1]
IV-747
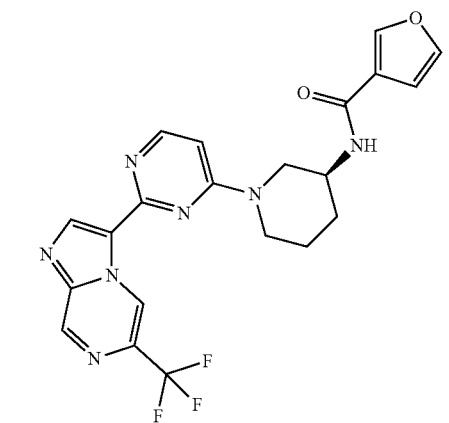 [SMILES: O=C(N[C@H]1CCCN(c2ccnc(-c3cnc4cnc(C(F)(F)F)cn34)n2)C1)c1ccoc1]
IV-748
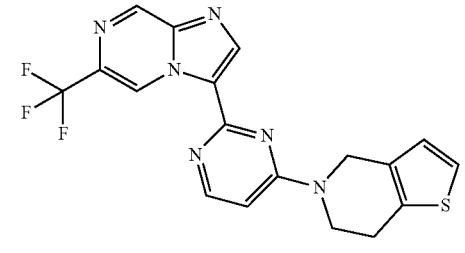 [SMILES: FC(F)(F)c1cn2c(-c3nccc(N4CCc5sccc5C4)n3)cnc2cn1]
IV-749
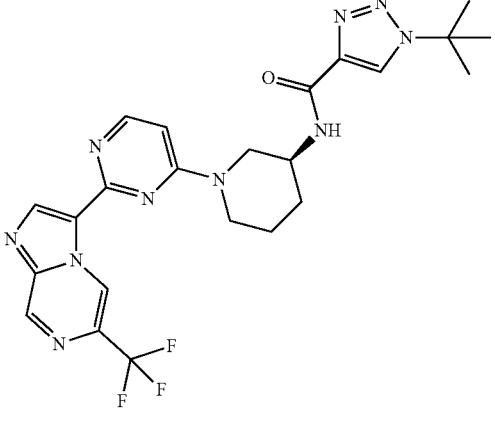 [SMILES: CC(C)(C)n1cc(C(=O)N[C@H]2CCCN(c3ccnc(-c4cnc5cnc(C(F)(F)F)cn45)n3)C2)nn1]
IV-750

TABLE 3-continued
Exemplary compounds of formula IV
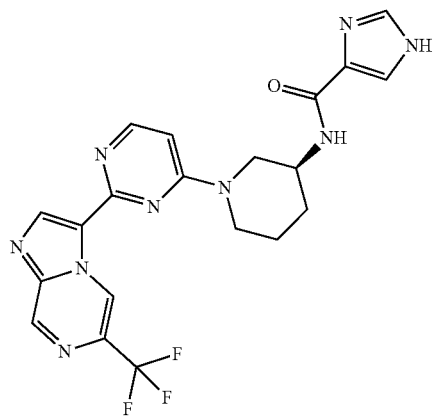 [SMILES: O=C(N[C@H]1CCCN(c2ccnc(-c3cnc4cnc(C(F)(F)F)cn34)n2)C1)c1c[nH]cn1]
IV-751
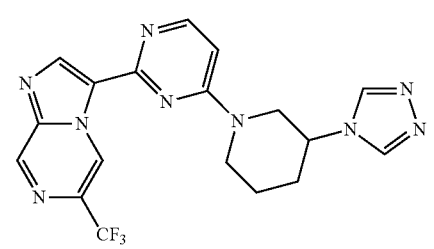 [SMILES: FC(F)(F)c1cn2c(-c3nccc(N4CCCC(n5cnnc5)C4)n3)cnc2cn1]
IV-752
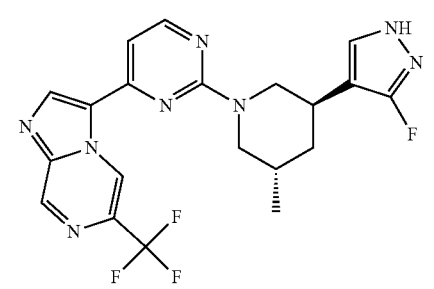 [SMILES: C[C@H]1C[C@H](c2c[nH]nc2F)CN(c2nccc(-c3cnc4cnc(C(F)(F)F)cn34)n2)C1]
IV-754
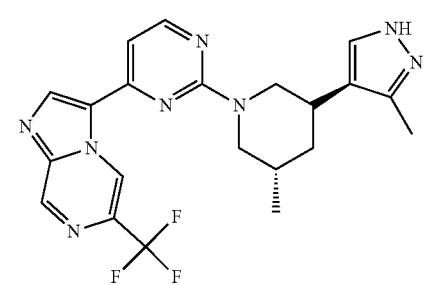
IV-755
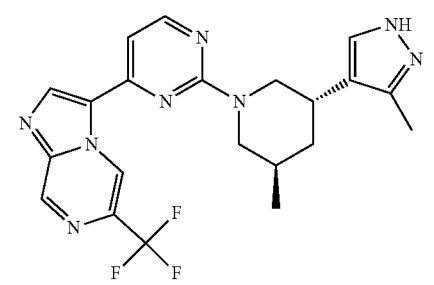 [SMILES: Cc1n[nH]cc1[C@@H]1C[C@@H](C)CN(c2nccc(-c3cnc4cnc(C(F)(F)F)cn34)n2)C1]
IV-756
TABLE 3-continued
Exemplary compounds of formula IV
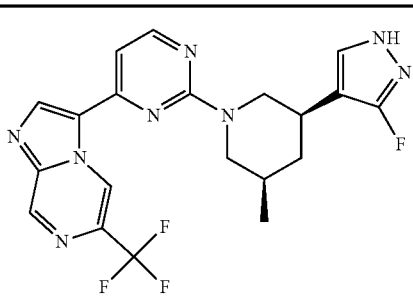
IV-757
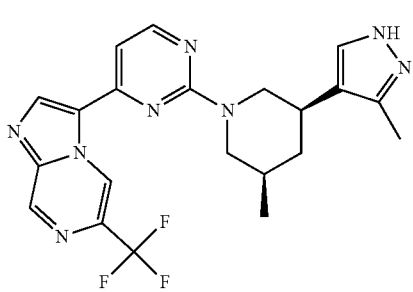 [SMILES: Cc1n[nH]cc1[C@H]1C[C@@H](C)CN(c2nccc(-c3cnc4cnc(C(F)(F)F)cn34)n2)C1]
IV-758
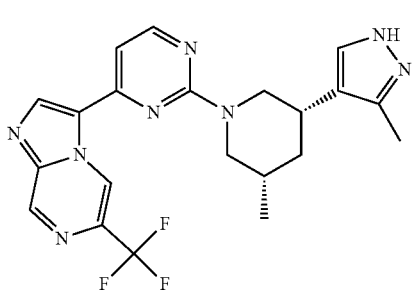 [SMILES: Cc1n[nH]cc1[C@@H]1C[C@H](C)CN(c2nccc(-c3cnc4cnc(C(F)(F)F)cn34)n2)C1]
IV-759
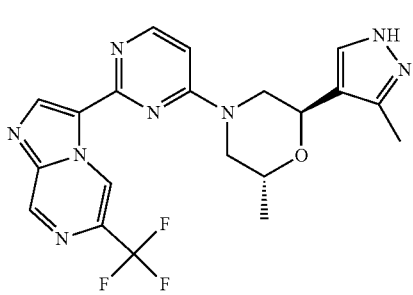 [SMILES: Cc1n[nH]cc1[C@@H]1CN(c2ccnc(-c3cnc4cnc(C(F)(F)F)cn34)n2)C[C@@H](C)O1]
IV-760
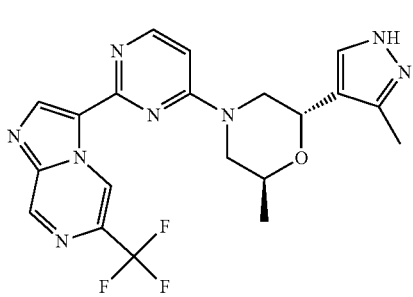
IV-761

TABLE 3-continued
Exemplary compounds of formula IV
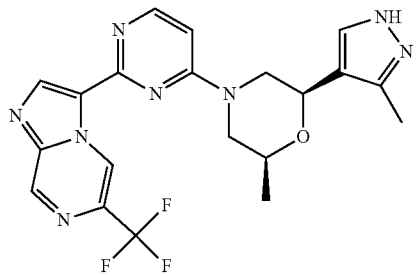 IV-762
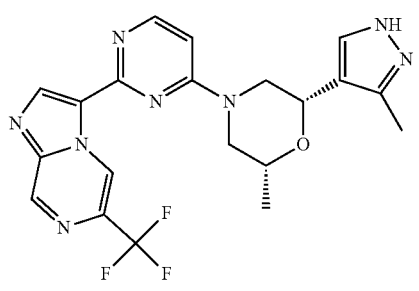 [SMILES: Cc1n[nH]cc1[C@H]1CN(c2ccnc(-c3cnc4cnc(C(F)(F)F)cn34)n2)C[C@@H](C)O1] IV-763
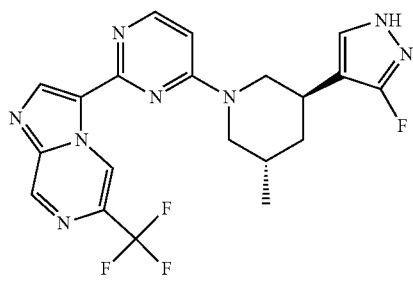 IV-764
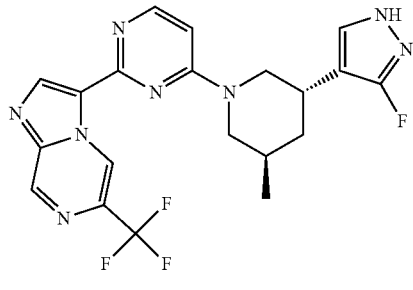 [SMILES: C[C@@H]1C[C@@H](c2c[nH]nc2F)CN(c2ccnc(-c3cnc4cnc(C(F)(F)F)cn34)n2)C1] IV-765
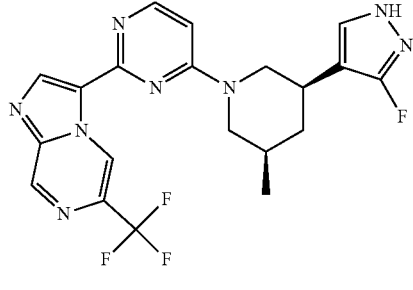 [SMILES: C[C@@H]1C[C@H](c2c[nH]nc2F)CN(c2ccnc(-c3cnc4cnc(C(F)(F)F)cn34)n2)C1] IV-766
TABLE 3-continued
Exemplary compounds of formula IV
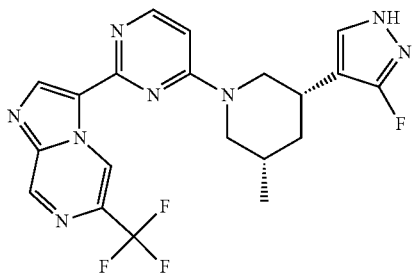 [SMILES: C[C@H]1C[C@@H](c2c[nH]nc2F)CN(c2ccnc(-c3cnc4cnc(C(F)(F)F)cn34)n2)C1] IV-767
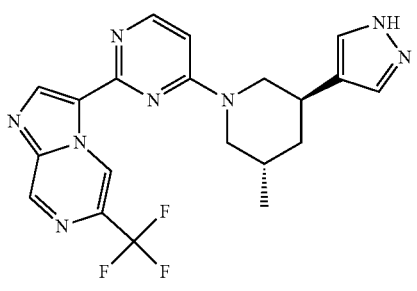 [SMILES: C[C@H]1C[C@H](c2cn[nH]c2)CN(c2ccnc(-c3cnc4cnc(C(F)(F)F)cn34)n2)C1] IV-768
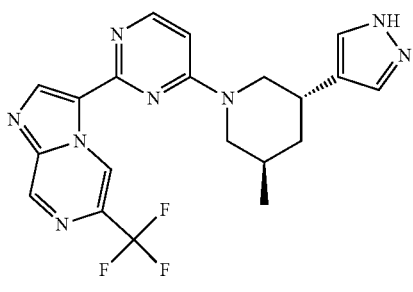 [SMILES: C[C@@H]1C[C@@H](c2cn[nH]c2)CN(c2ccnc(-c3cnc4cnc(C(F)(F)F)cn34)n2)C1] IV-769
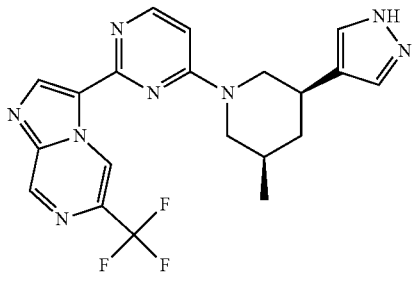 [SMILES: C[C@@H]1C[C@H](c2cn[nH]c2)CN(c2ccnc(-c3cnc4cnc(C(F)(F)F)cn34)n2)C1] IV-770
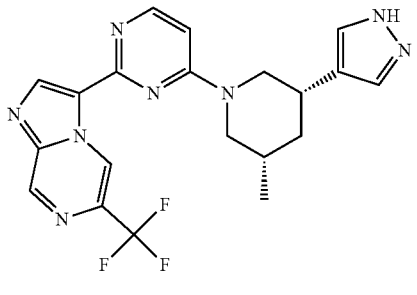 [SMILES: C[C@H]1C[C@@H](c2cn[nH]c2)CN(c2ccnc(-c3cnc4cnc(C(F)(F)F)cn34)n2)C1] IV-771

TABLE 3-continued
Exemplary compounds of formula IV
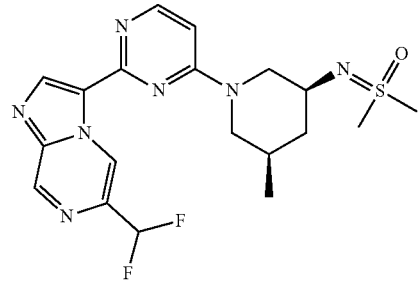 [SMILES: C[C@@H]1C[C@H](N=S(C)(C)=O)CN(c2ccnc(-c3cnc4cnc(C(F)F)cn34)n2)C1] IV-772
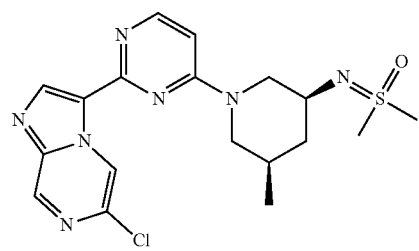 [SMILES: C[C@@H]1C[C@H](N=S(C)(C)=O)CN(c2ccnc(-c3cnc4cnc(Cl)cn34)n2)C1] IV-773
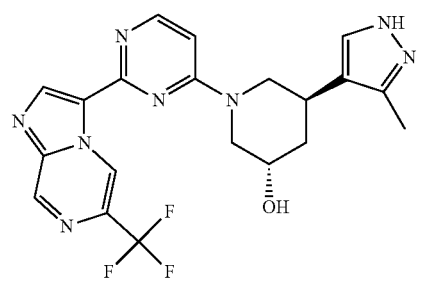 [SMILES: Cc1n[nH]cc1[C@H]1C[C@H](O)CN(c2ccnc(-c3cnc4cnc(C(F)(F)F)cn34)n2)C1] IV-774
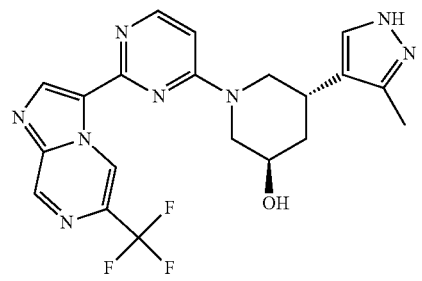 [SMILES: Cc1n[nH]cc1[C@@H]1C[C@@H](O)CN(c2ccnc(-c3cnc4cnc(C(F)(F)F)cn34)n2)C1] IV-775
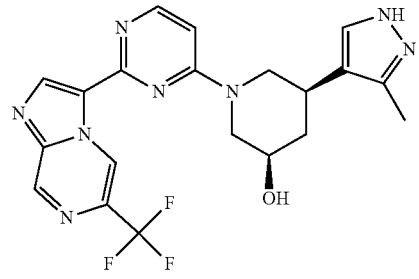 [SMILES: Cc1n[nH]cc1[C@H]1C[C@@H](O)CN(c2ccnc(-c3cnc4cnc(C(F)(F)F)cn34)n2)C1] IV-776
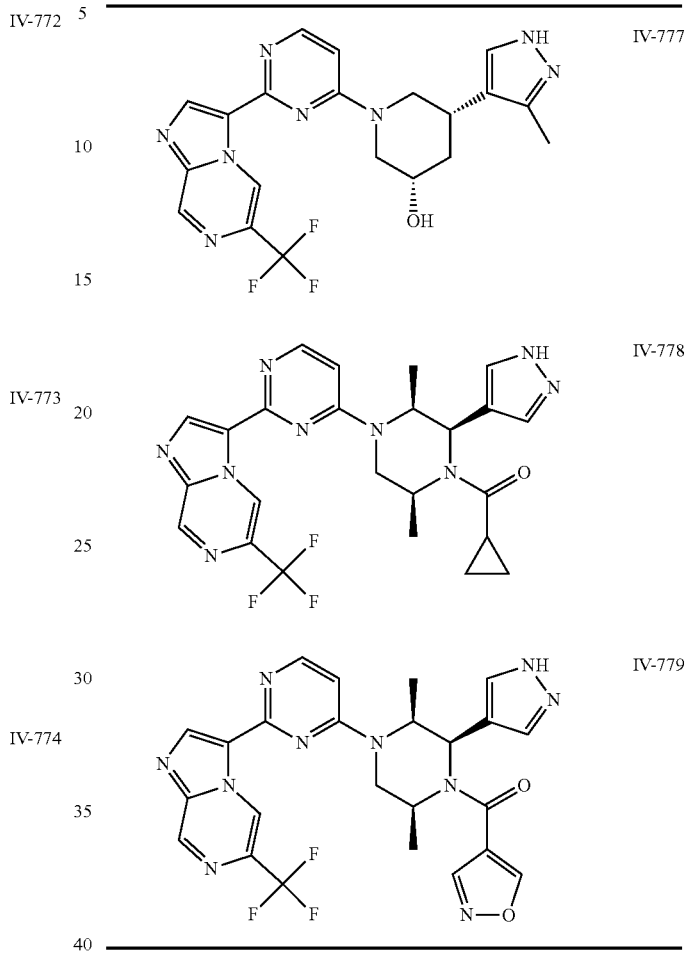
TABLE 4
Exemplary compounds of formula V
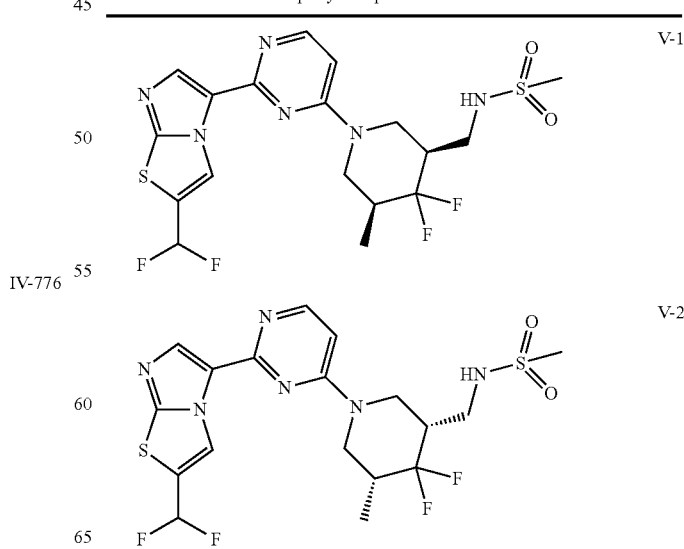

TABLE 4-continued

Exemplary compounds of formula V

V-3

V-4

V-5 single diastereomer
(pair of enantiomers)

V-6 single diastereomer
(pair of enantiomers)

V-7

TABLE 4-continued

Exemplary compounds of formula V

V-8

V-9

V-10

V-11 single stereoisomer

V-12 single stereoisomer

TABLE 4-continued

Exemplary compounds of formula V

V-13, V-14, V-15, V-16, V-17 (structures shown)

single diastereomer (pair of enantiomers) [noted for V-14, V-16, V-17]

V-18, V-19 (structures shown)
single diastereomer (pair of enantiomers)

V-20 (structure shown)

In some embodiments, the present invention provides a compound set forth in Tables 1-4, above, or a pharmaceutically acceptable salt thereof.

In certain embodiments, the present invention provides a complex comprising GCN2 and an inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention of formula II are generally prepared according to Schemes 1-17 set forth below:

Scheme 1: General scheme for the preparation of compounds of formula II where Ring C is a pyrimidine, $R^3$ is hydrogen, $R^4$ is hydrogen, n is 1, p is 1, and q is 1.

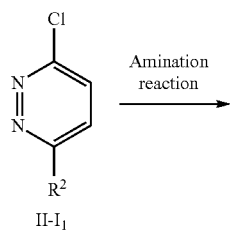

II-I$_1$

Amination reaction →

-continued

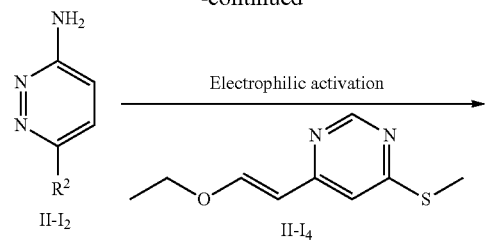

II-I$_2$

Electrophilic activation →

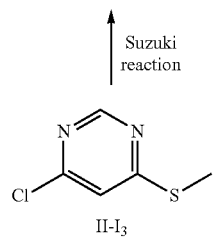

II-I$_3$

↑ Suzuki reaction

II-I$_4$

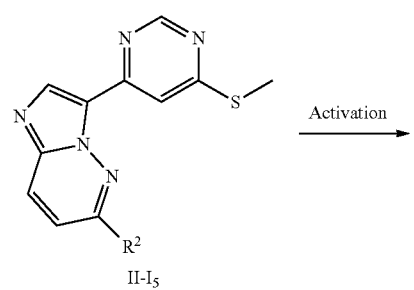

II-I$_5$

Activation →

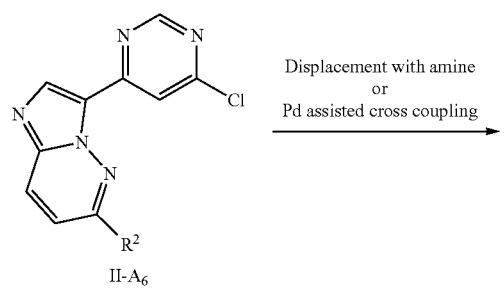

II-A$_6$

Displacement with amine or Pd assisted cross coupling →

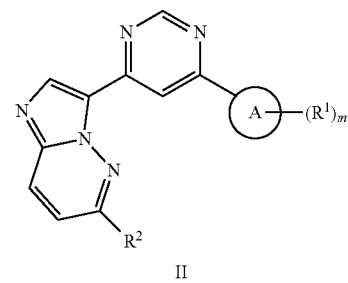

II

In Scheme 1 above, each of Ring A, $R^1$, $R^2$, and m is as defined above and below and in classes and subclasses as described herein.

Scheme 2: General scheme for the preparation of compounds of formula II where Ring C is a pyrimidine, $R^2$ is —CHF$_2$, $R^3$ is hydrogen, $R^4$ is hydrogen, n is 1, p is 1, and q is 1.

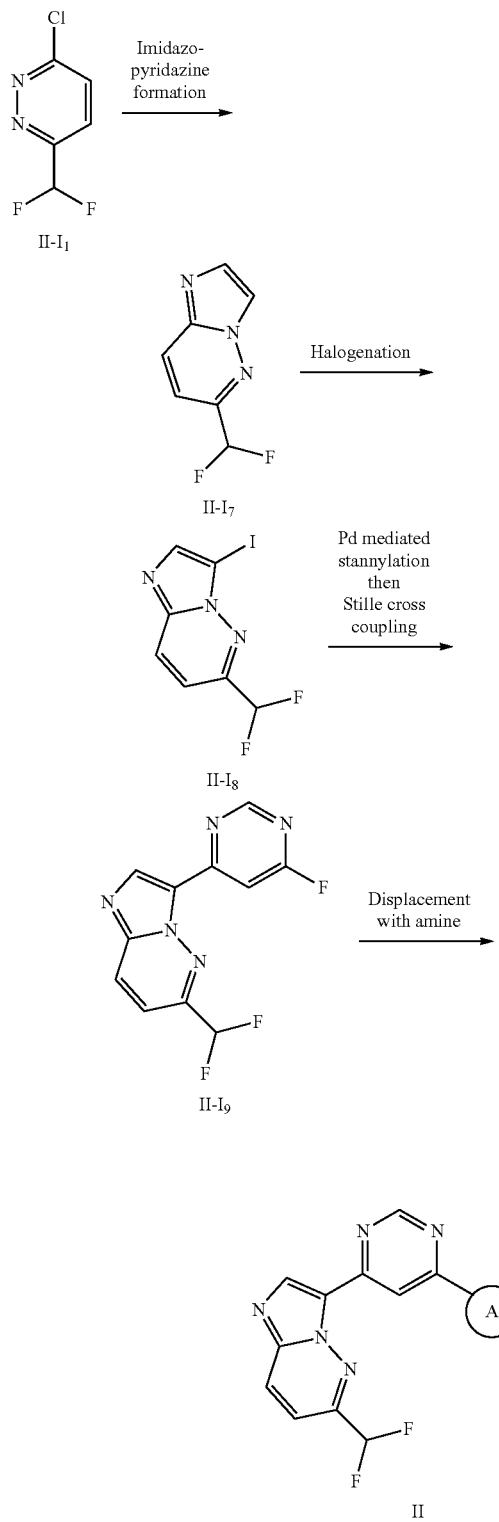

In Scheme 2 above, each of Ring A, $R^1$, and m is as defined above and below and in classes and subclasses as described herein.

Scheme 3: General scheme for the preparation of compounds of formula II where Ring C is a pyridine, $R^3$ is hydrogen, n is 1, and q is 1.

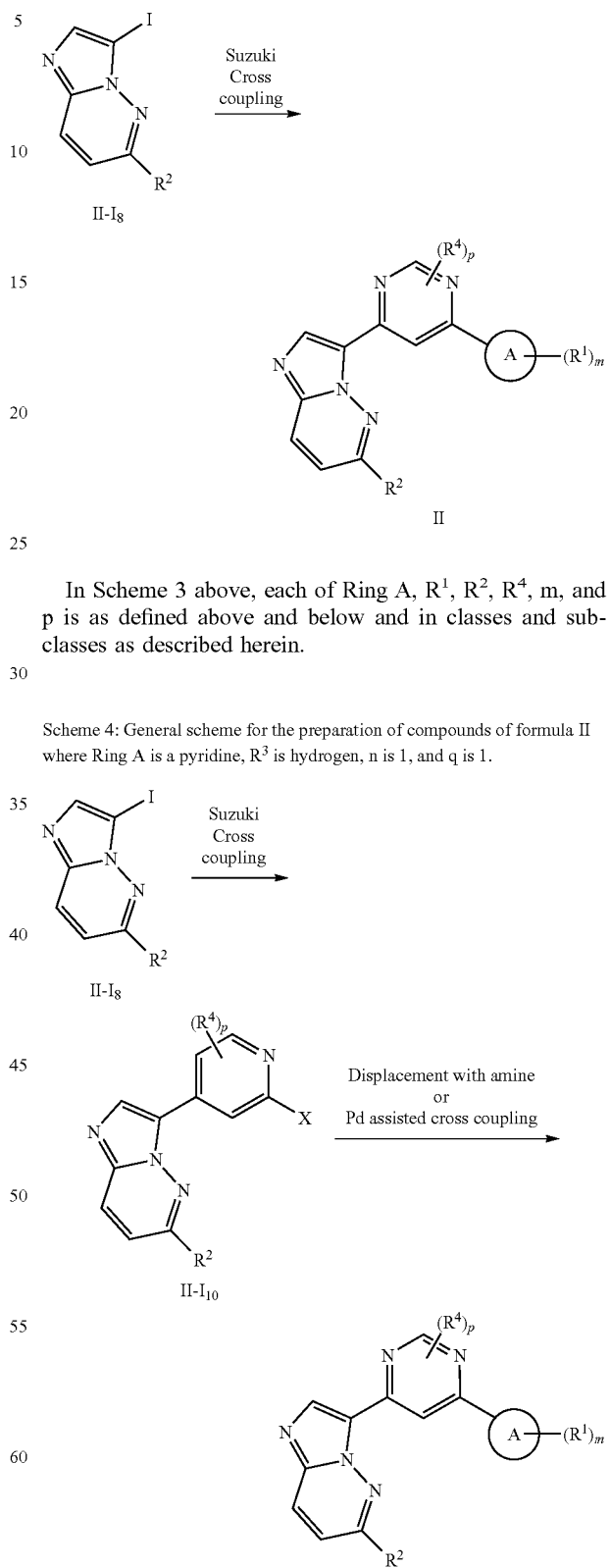

In Scheme 3 above, each of Ring A, $R^1$, $R^2$, $R^4$, m, and p is as defined above and below and in classes and subclasses as described herein.

Scheme 4: General scheme for the preparation of compounds of formula II where Ring A is a pyridine, $R^3$ is hydrogen, n is 1, and q is 1.

In Scheme 4 above, each of Ring A, $R^1$, $R^2$, $R^4$, m, and p is as defined above and below and in classes and subclasses as described herein.

Scheme 5: General scheme for the preparation of compounds of formula II where Ring C is a pyridine, $R^2$ is —CHF$_2$, $R^3$ is hydrogen, n is 1, and q is 1.

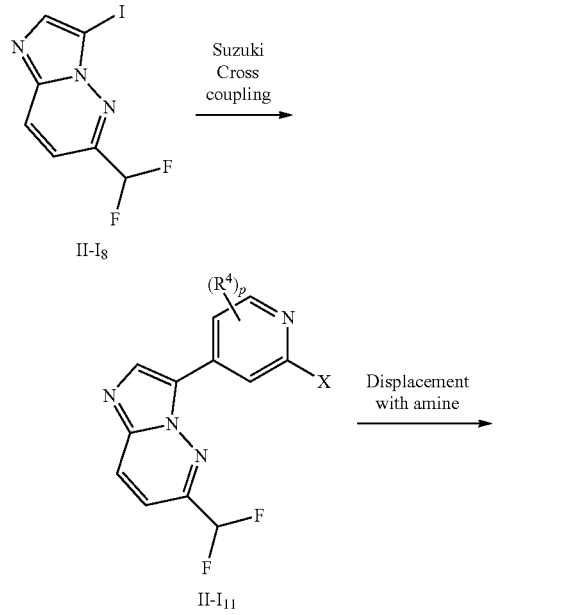

In Scheme 5 above, each of Ring A, $R^1$, $R^4$, m, and p is as defined above and below and in classes and subclasses as described herein.

Scheme 6: General scheme for the preparation of compounds of formula II where Ring C is a pyridine, $R^2$ is —CHF$_2$, $R^3$ is hydrogen, n is 1, and q is 1.

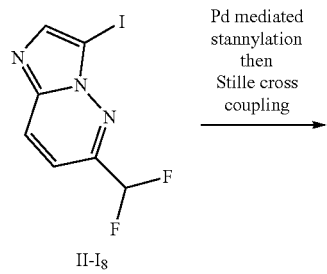

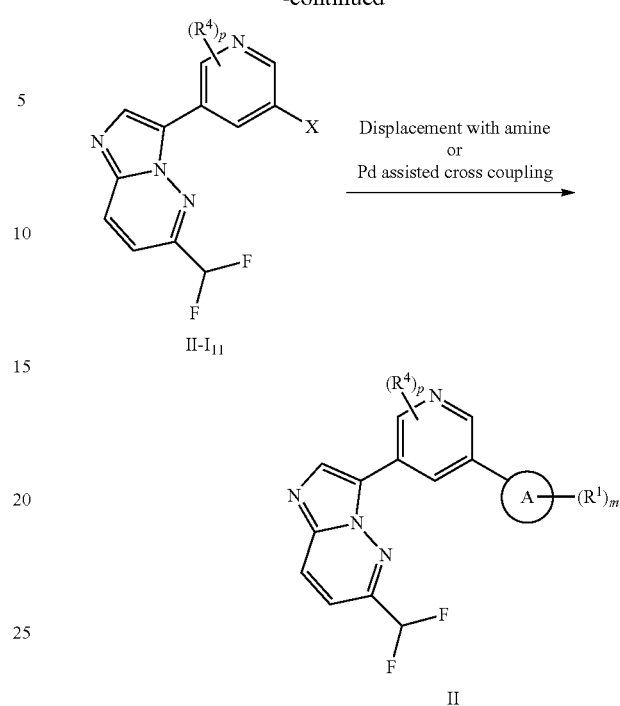

In Scheme 6 above, each of Ring A, $R^1$, $R^4$, m, and p is as defined above and below and in classes and subclasses as described herein.

Scheme 7: General scheme for the preparation of compounds of formula II where Ring C is a pyridine, $R^2$ is —CHF$_2$, $R^3$ is hydrogen, n is 1, and q is 1.

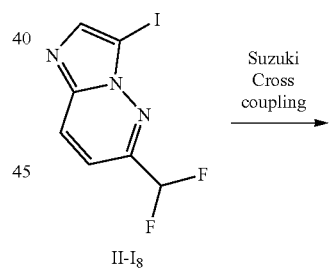

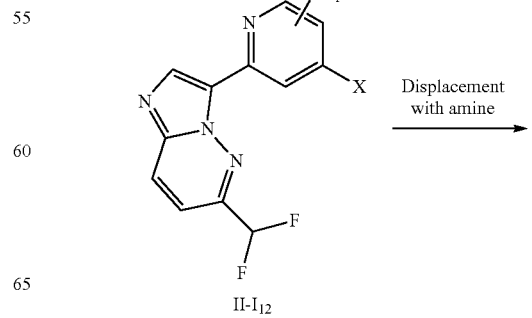

-continued

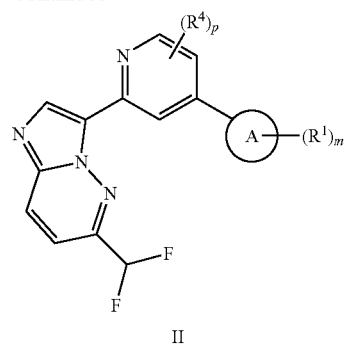

In Scheme 7 above, each of Ring A, R$^1$, R$^4$, m, and p is as defined above and below and in classes and subclasses as described herein.

Scheme 8: General scheme for the preparation of compounds of formula II where Ring C is a pyridine, R$^2$ is —CHF$_2$, R$^3$ is hydrogen, n is 1, and q is 1.

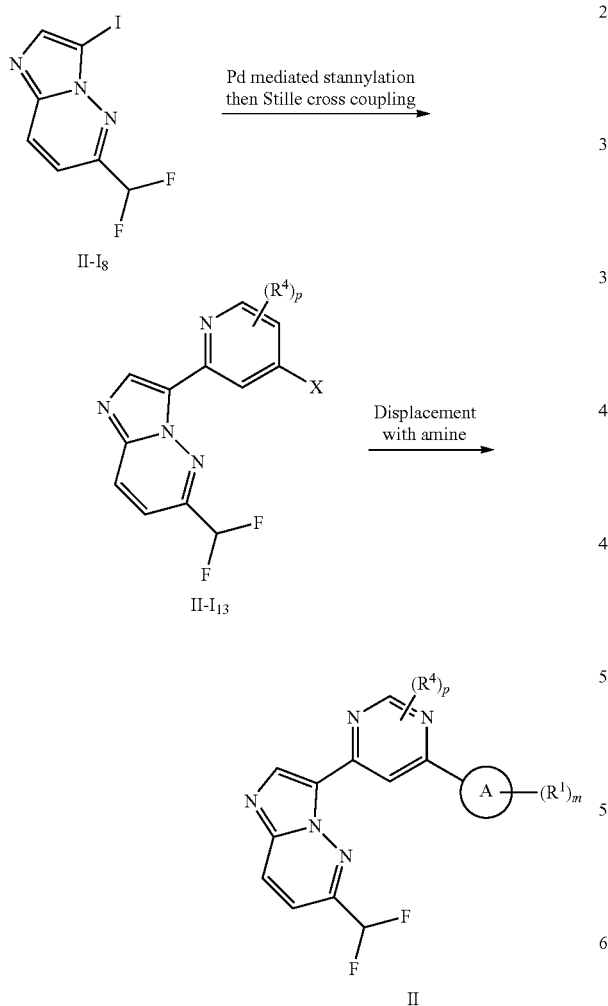

In Scheme 8 above, each of Ring A, R$^1$, R$^4$, m, and p is as defined above and below and in classes and subclasses as described herein.

Scheme 9: General scheme for the preparation of compounds of formula II where Ring C is a pyridine, R$^2$ is —CHF$_2$, R$^3$ is hydrogen, n is 1, p is 1 and q is 1.

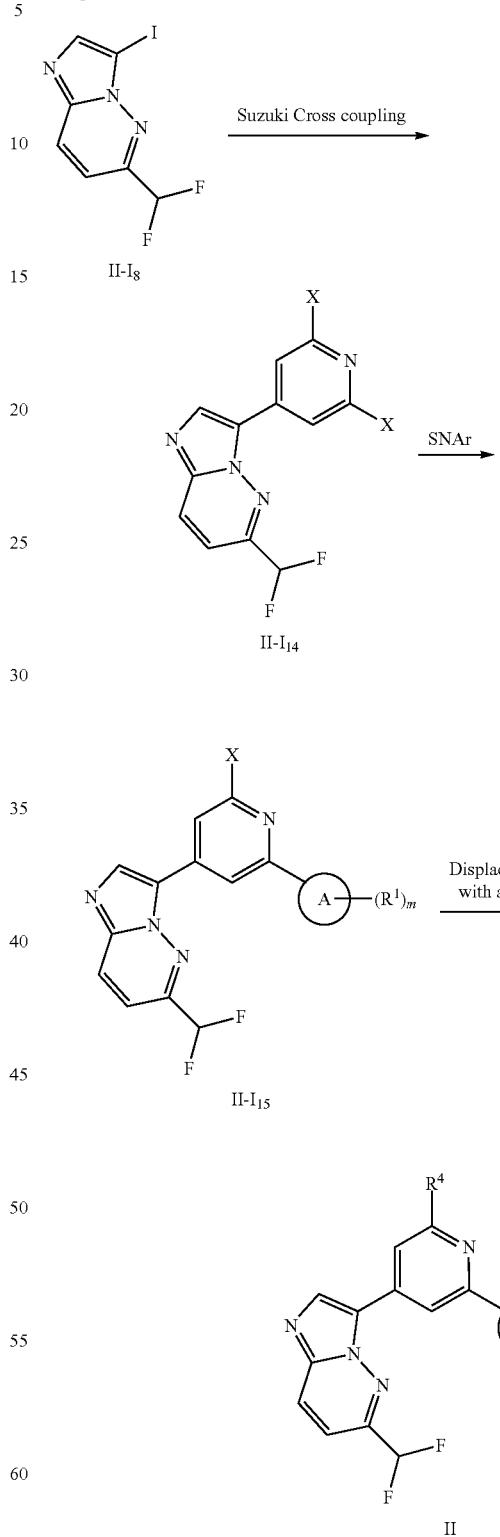

In Scheme 9 above, each of Ring A, R$^1$, R$^4$, and m is as defined above and below and in classes and subclasses as described herein.

Scheme 10: General scheme for the preparation of compounds of formula II where Ring C is a pyridine, R² is ——CHF₂, R³ is hydrogen, n is 1, and q is 1.

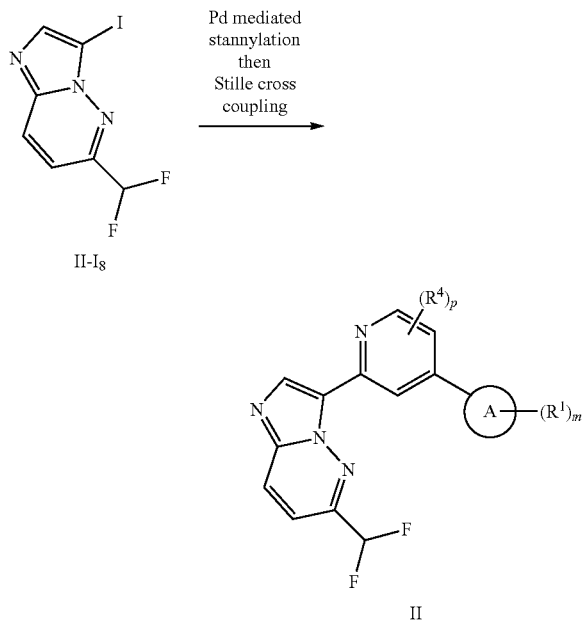

In Scheme 10 above, each of Ring A, $R^1$, $R^4$, m, and p is as defined above and below and in classes and subclasses as described herein.

Scheme 11: General scheme for the preparation of compounds of formula II where Ring C is a phenyl, R² is ——CHF₂, R³ is hydrogen, n is 1, and q is 1.

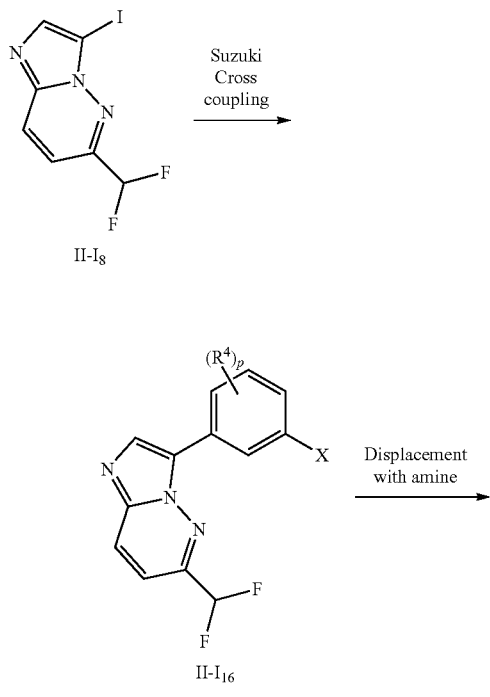

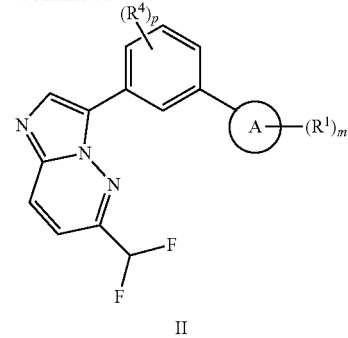

In Scheme 11 above, each of Ring A, $R^1$, $R^4$, m, and p is as defined above and below and in classes and subclasses as described herein.

Scheme 12: General scheme for the preparation of compounds of formula II where Ring C is a phenyl, R² is ——CHF₂, R³ is hydrogen, n is 1, and q is 1.

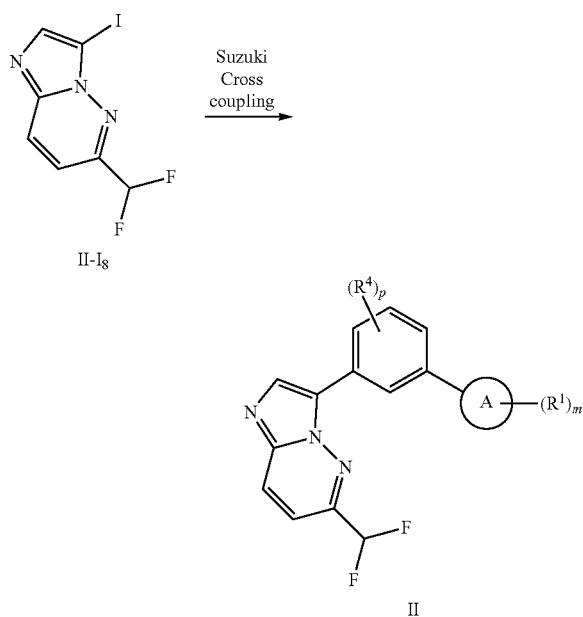

In Scheme 12 above, each of Ring A, $R^1$, $R^4$, m, and p is as defined above and below and in classes and subclasses as described herein.

Scheme 13: General scheme for the preparation of compounds of formula II where Ring C is a pyridine, R² is ——OCF₂H, R³ is hydrogen, n is 1, and q is 1.

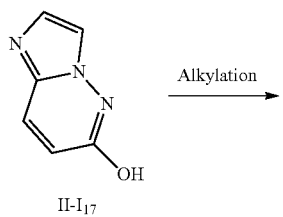

-continued

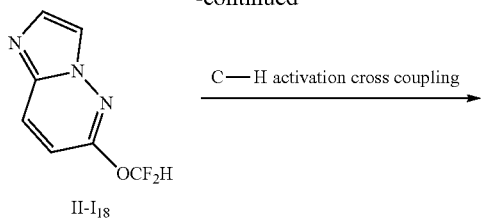

II-I<sub>18</sub>

C—H activation cross coupling →

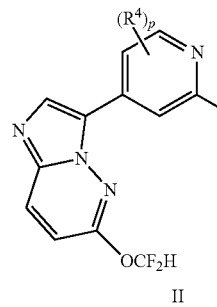

II

In Scheme 13 above, each of Ring A, $R^1$, $R^4$, m, and p is as defined above and below and in classes and subclasses as described herein.

Scheme 14: General scheme for the preparation of compounds of formula II where Ring C is a pyridine, $R^2$ is —$CF_3$, $R^3$ is hydrogen, n is 1, and q is 1.

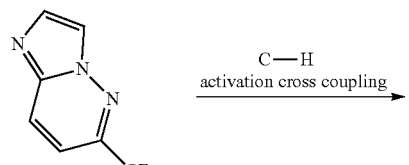

II-I<sub>19</sub>

C—H activation cross coupling →

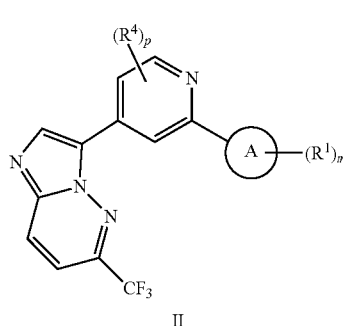

II-I<sub>20</sub>

Displacement with amine →

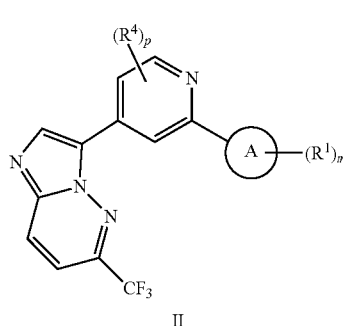

II

In Scheme 14 above, each of Ring A, $R^1$, $R^4$, m, and p is as defined above and below and in classes and subclasses as described herein.

Scheme 15: General scheme for the preparation of compounds of formula II where Ring C is a pyridine, $R^2$ is —$CHF_2$, $R^3$ is hydrogen, n is 1, and q is 1.

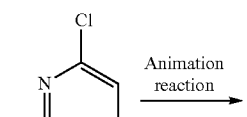

II-I<sub>21</sub>

Amination reaction →

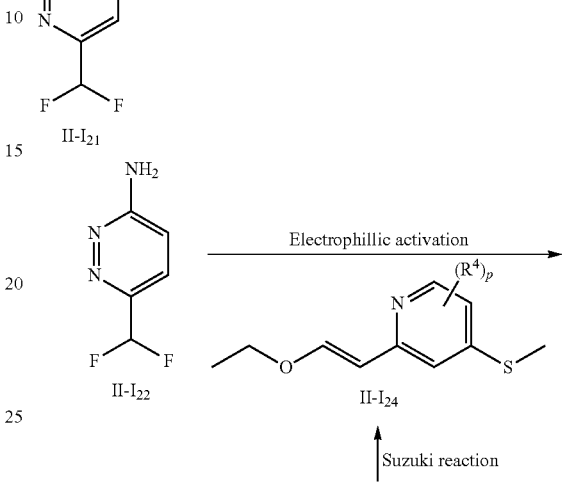

II-I<sub>22</sub>

Electrophillic activation →

II-I<sub>24</sub>

Suzuki reaction ↑

II-I<sub>23</sub>

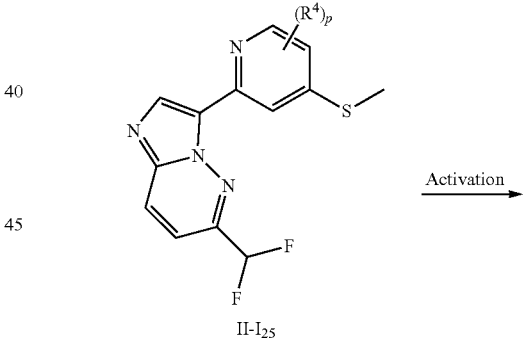

II-I<sub>25</sub>

Activation →

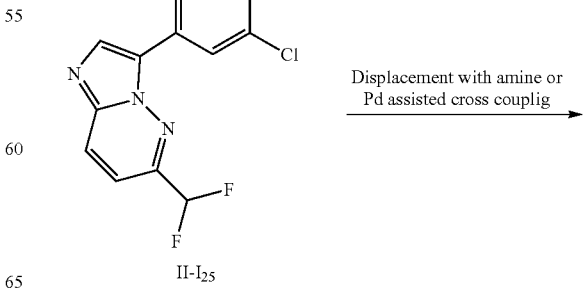

II-I<sub>25</sub>

Displacement with amine or Pd assisted cross couplig →

461

-continued

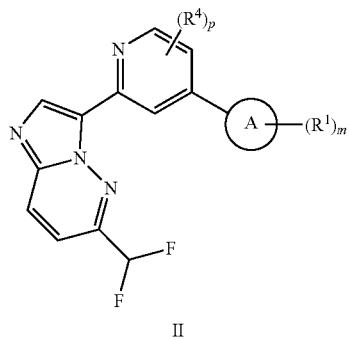

II

In Scheme 15 above, each of Ring A, $R^1$, $R^4$, m, and p is as defined above and below and in classes and subclasses as described herein.

Scheme 16: General scheme for the preparation of compounds of formula II where Ring C is a pyrimidine, $R^2$ is ——Cl, $R^3$ is hydrogen, n is 1, and q is 1.

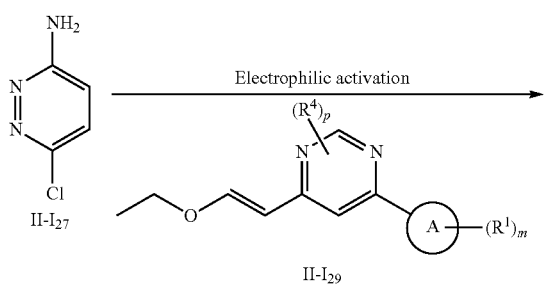

In Scheme 16 above, each of Ring A, $R^1$, $R^4$, m, and p is as defined above and below and in classes and subclasses as described herein.

462

Scheme 17: General scheme for the preparation of compounds of formula II where Ring C is a pyrimidine, $R^2$ is ——$CHF_2$, $R^3$ is hydrogen, $R^4$ is hydrogen, n is 1, p is 1, and q is 1.

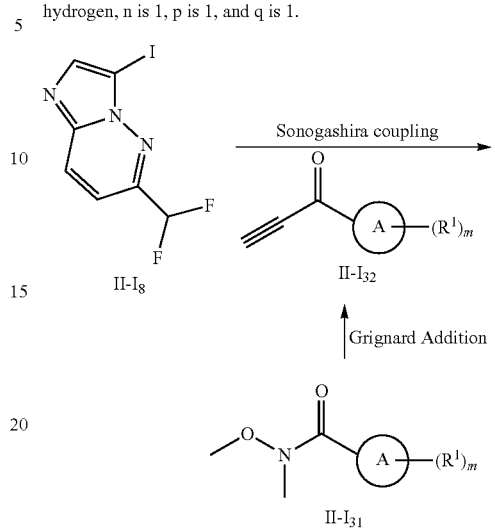

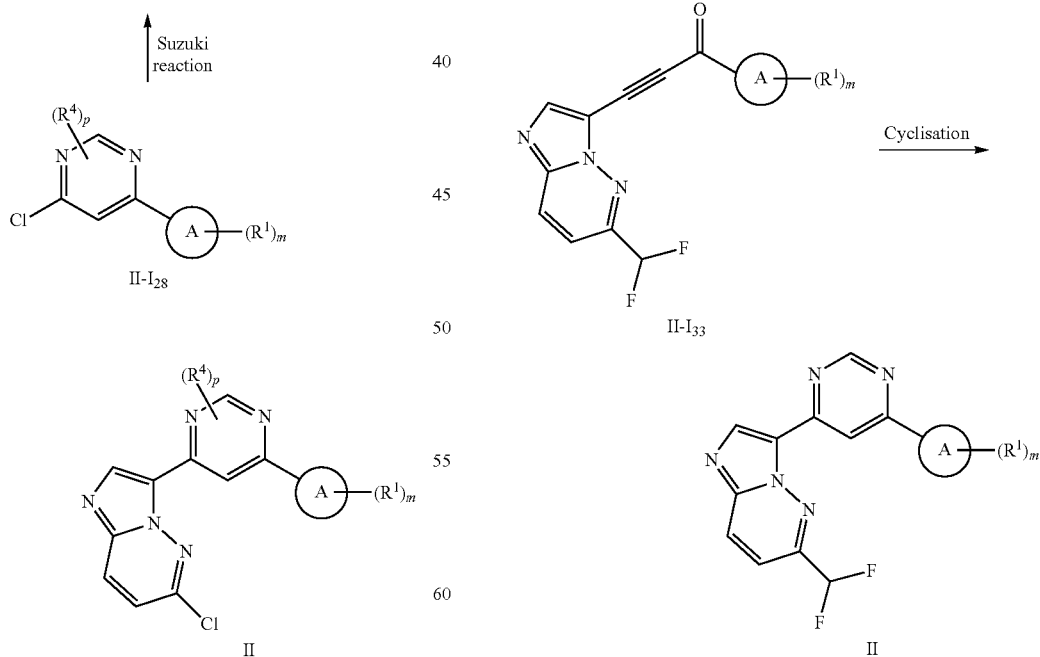

In Scheme 17 above, each of Ring A, $R^1$, and m is as defined above and below and in classes and subclasses as described herein.

Scheme 18: General scheme for the preparation of compounds of Formula III where Ring C is a pyrimidine linked to the bicyclic core from position 4, $R^3$ is hydrogen, $R^4$ is hydrogen, p is 1, and q is 1.

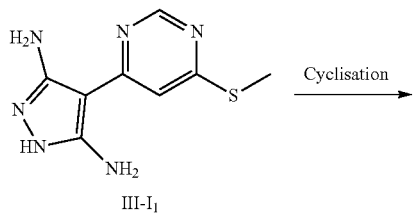

III-I$_1$ — Cyclisation →

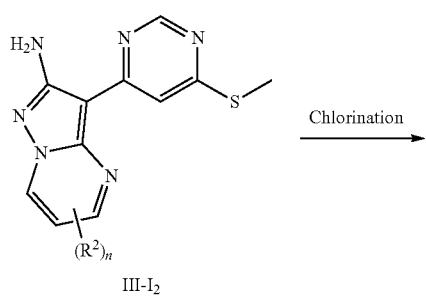

III-I$_2$ — Chlorination →

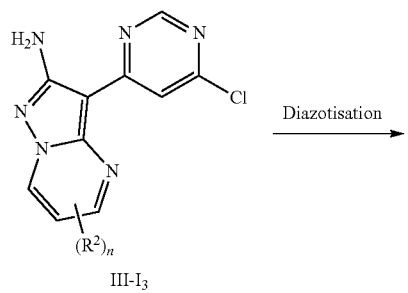

III-I$_3$ — Diazotisation →

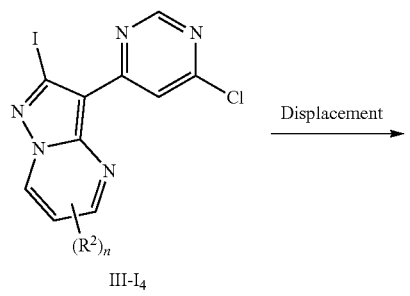

III-I$_4$ — Displacement →

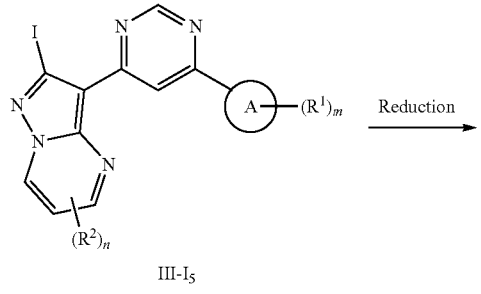

III-I$_5$ — Reduction →

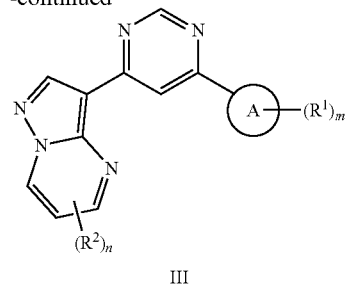

III

In Scheme 18 above, each of Ring A, $R^1$, $R^2$, m, and n is as defined above and below and in classes and subclasses as described herein.

Scheme 19: General scheme for the preparation of compounds of Formula III where Ring C is a pyrimidine linked to the bicyclic core from position 4, $R^3$ is hydrogen, $R^4$ is hydrogen, p is 1, and q is 1.

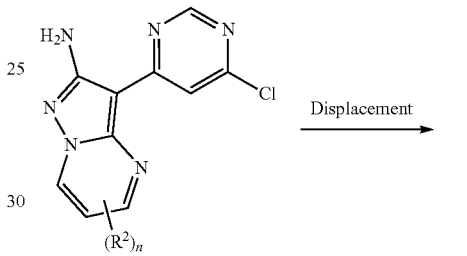

III-I$_3$ — Displacement →


III-I$_5$ — Diazotisation →

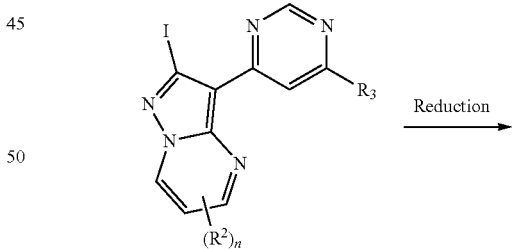

III-I$_6$ — Reduction →

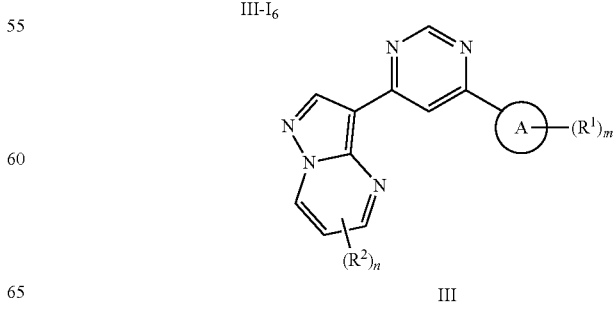

III

In Scheme 19 above, each of Ring A, $R^1$, $R^2$, m, and n is as defined above and below and in classes and subclasses as described herein.

Scheme 20: General scheme for the preparation of compounds of Formula III where Ring C is a pyrimidine linked to the bicyclic core from position 4, $R^3$ is hydrogen, $R^4$ is hydrogen, p is 1, and q is 1.

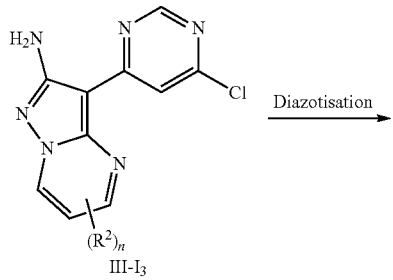

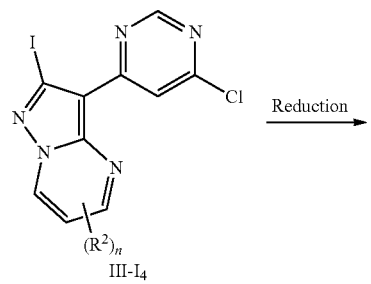

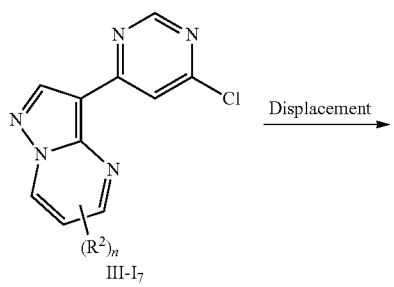

In Scheme 20 above, each of Ring A, $R^1$, $R^2$, m, and n is as defined above and below and in classes and subclasses as described herein.

Scheme 21: General scheme for the preparation of compounds of Formula III where Ring C is a pyridine linked to the bicyclic core from position 4, $R^3$ is hydrogen, $R^4$ is hydrogen, p is 1, and q is 1.

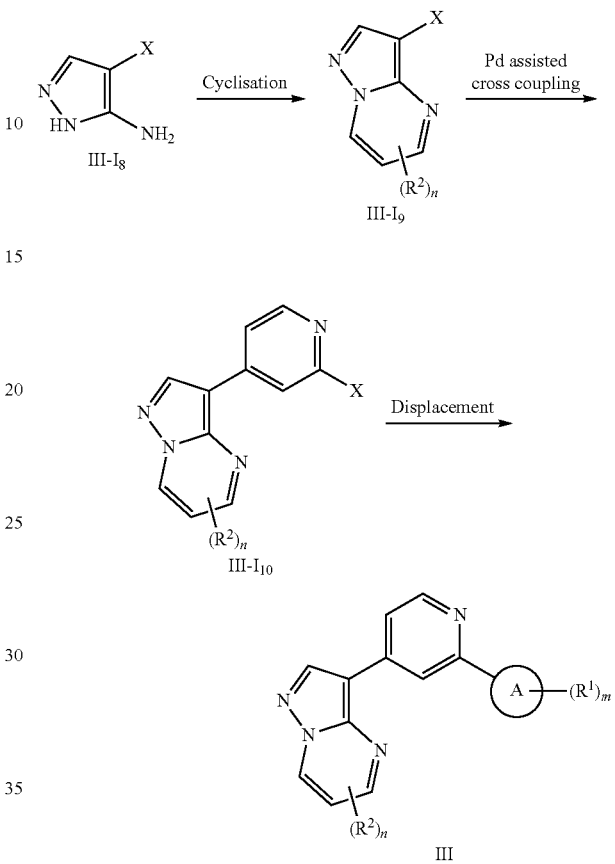

In Scheme 21 above, each of Ring A, $R^1$, $R^2$, m, and n is as defined above and below and in classes and subclasses as described herein.

Scheme 22: General scheme for the preparation of compounds of Formula III where Ring C is a pyrimidine, $R^3$ is hydrogen, and q is 1.

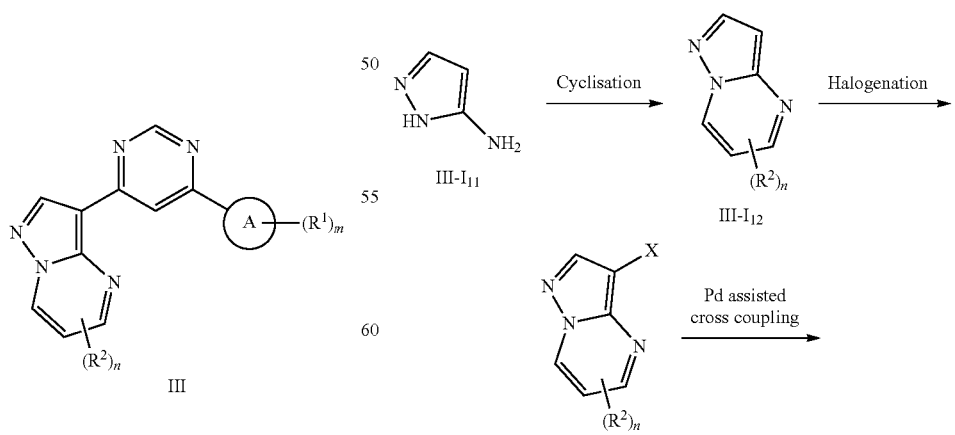

467

-continued

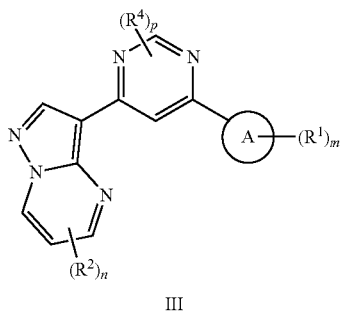

III

In Scheme 22 above, each of Ring A, $R^1$, $R^2$, $R^4$, m, n, and p is as defined above and below and in classes and subclasses as described herein.

Scheme 23: General scheme for the preparation of compounds of Formula III where Ring C is a pyridine-4-yl further substituted at position 2, $R^3$ is hydrogen, and q is 1.

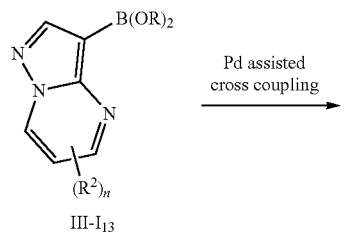

III-I$_{13}$

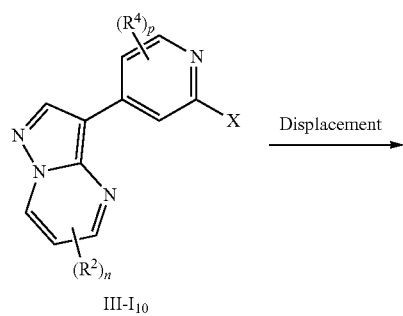

III-I$_{10}$

III

In Scheme 23 above, each of Ring A, $R^1$, $R^2$, $R^4$, m, n, and p is as defined above and below and in classes and subclasses as described herein.

468

Scheme 24: General scheme for the preparation of compounds of Formula III where Ring C is a pyridine introduced by a cross coupling reaction, $R^3$ is hydrogen, and q is 1.

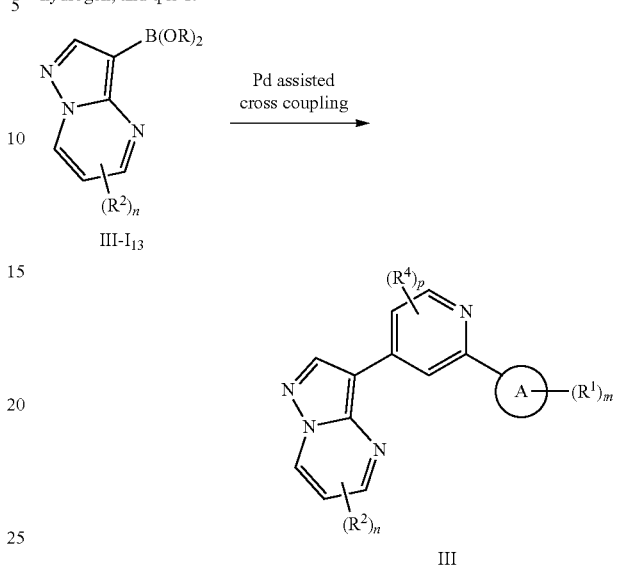

III

In Scheme 24 above, each of Ring A, $R^1$, $R^2$, $R^4$, m, n, and p is as defined above and below and in classes and subclasses as described herein.

Scheme 25: General scheme for the preparation of compounds of formula III where Ring C is a pyridine introduced by C—H activation, $R^3$ is hydrogen, and q is 1.

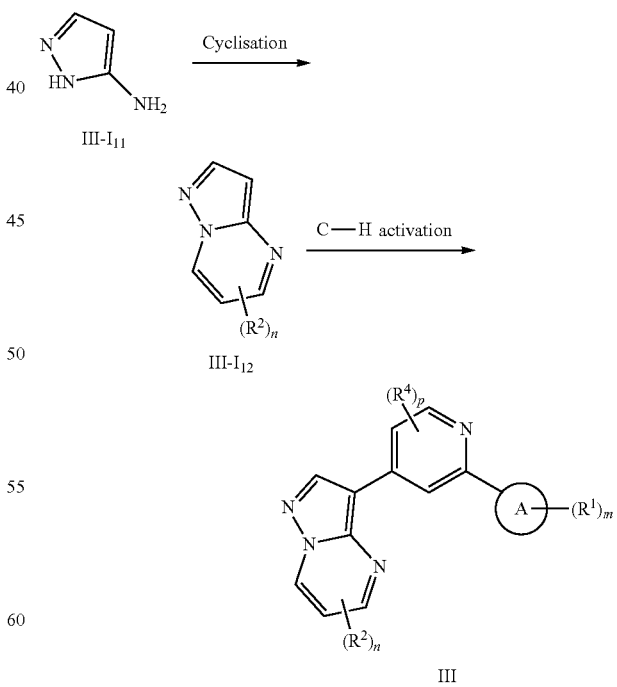

III

In Scheme 25 above, each of Ring A, $R^1$, $R^2$, $R^4$, m, n, and p is as defined above and below and in classes and subclasses as described herein.

Scheme 26: General scheme for the preparation of compounds of formula IV where Ring C is a pyrimidine, $R^3$ is hydrogen, $R^4$ is hydrogen, p is 1, and q is 1.

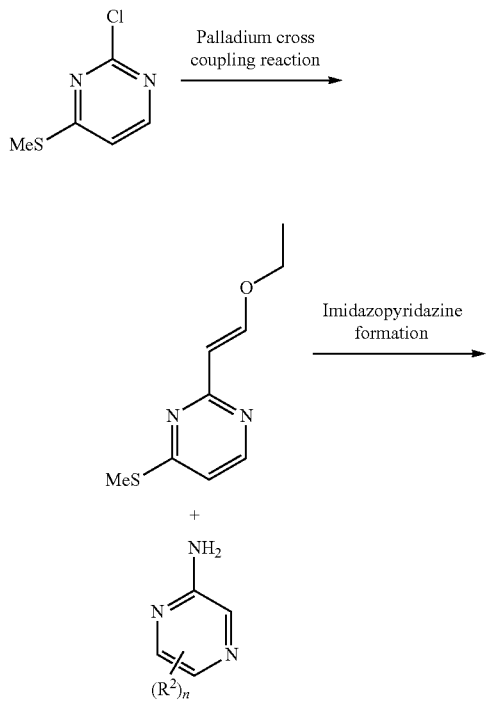

In Scheme 26 above, each of Ring A, $R^1$, $R^2$, m, and n is as defined above and below and in classes and subclasses as described herein.

Scheme 27: General scheme for the preparation of compounds of formula IV where Ring C is a pyridine, $R^3$ is hydrogen, $R^4$ is hydrogen, p is 1, and q is 1.

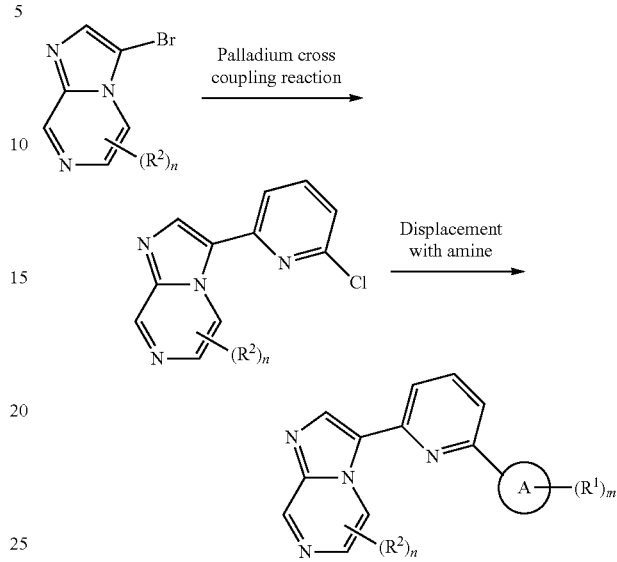

In Scheme 27 above, each of Ring A, $R^1$, $R^2$, m, and n is as defined above and below and in classes and subclasses as described herein.

Scheme 28: General scheme for the preparation of compounds of formula IV where Ring C is a pyrimidine, $R^3$ is hydrogen, $R^4$ is hydrogen, p is 1, and q is 1.

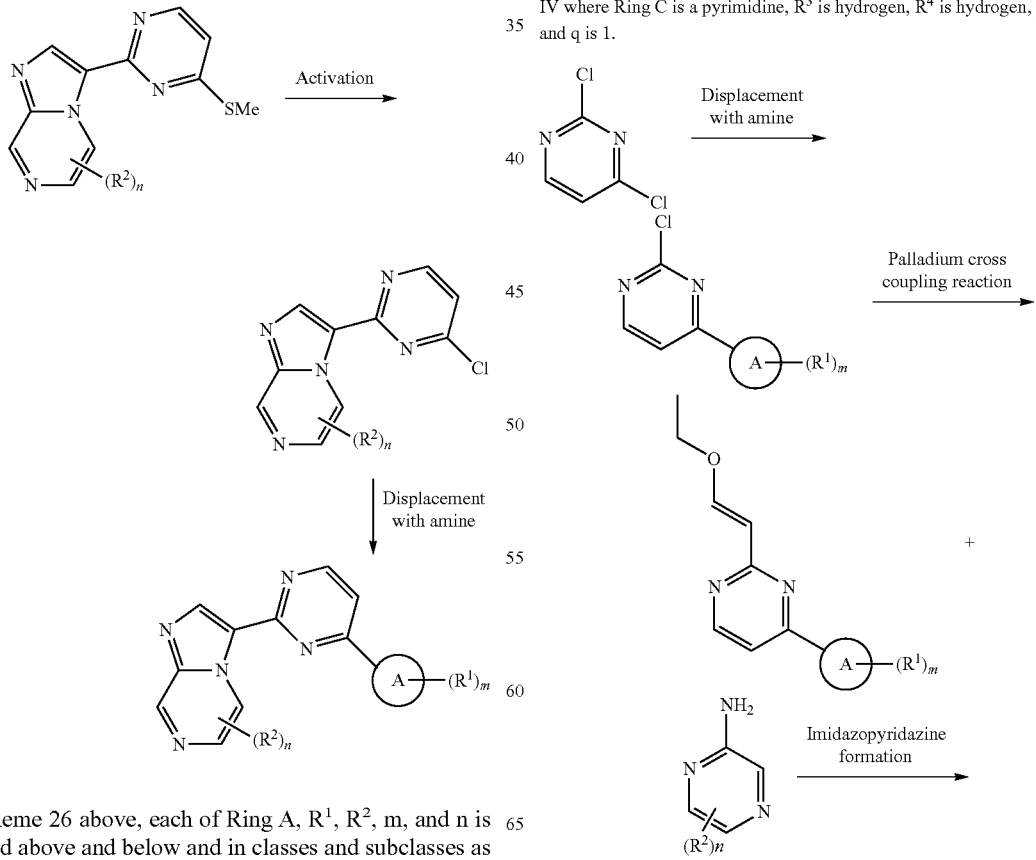

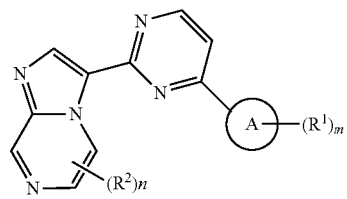

In Scheme 28 above, each of Ring A, $R^1$, $R^2$, m, and n is as defined above and below and in classes and subclasses as described herein.

Scheme 29: General scheme for the preparation of compounds of formula IV where Ring C is a pyrimidine, $R^3$ is hydrogen, $R^4$ is hydrogen, p is 1, and q is 1.

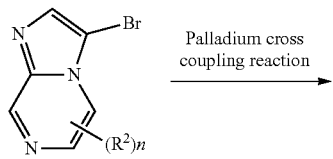

In Scheme 29 above, each of Ring A, $R^1$, $R^2$, m, and n is as defined above and below and in classes and subclasses as described herein.

Scheme 30: General scheme for the preparation of compounds of formula IV where Ring C is a pyrimidine, $R^3$ is hydrogen, $R^4$ is hydrogen, p is 1, and q is 1.

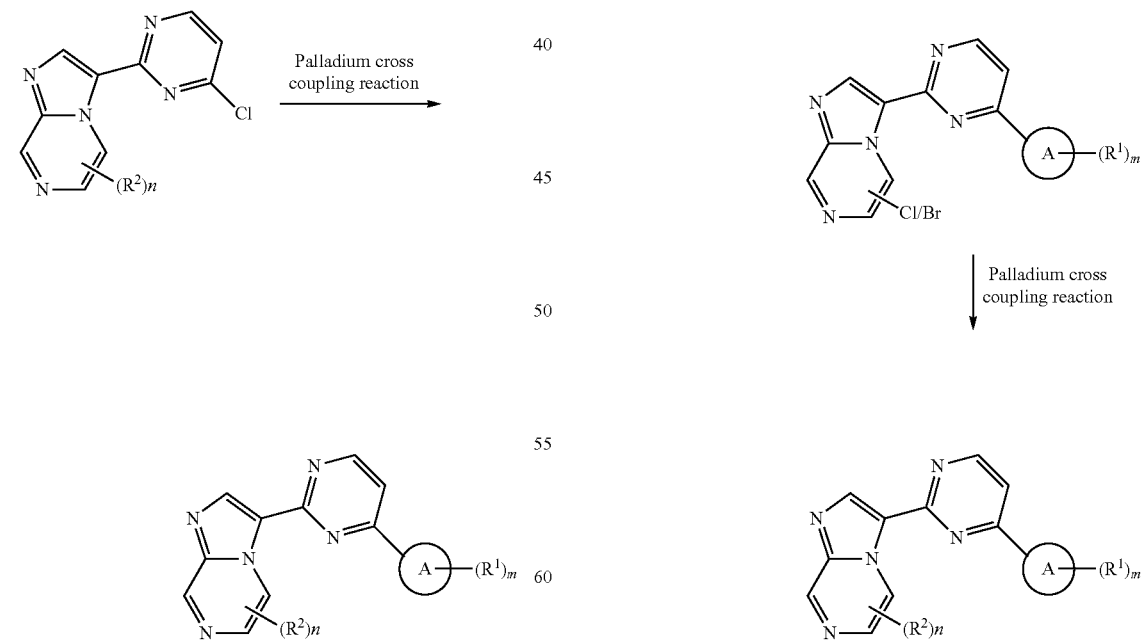

In Scheme 30 above, each of Ring A, $R^1$, $R^2$, m, and n is as defined above and below and in classes and subclasses as described herein.

Scheme 31: General scheme for the preparation of compounds of formula IV where Ring C is a pyrimidine, $R^3$ is hydrogen, $R^4$ is hydrogen, n is 1, p is 1, and q is 1.

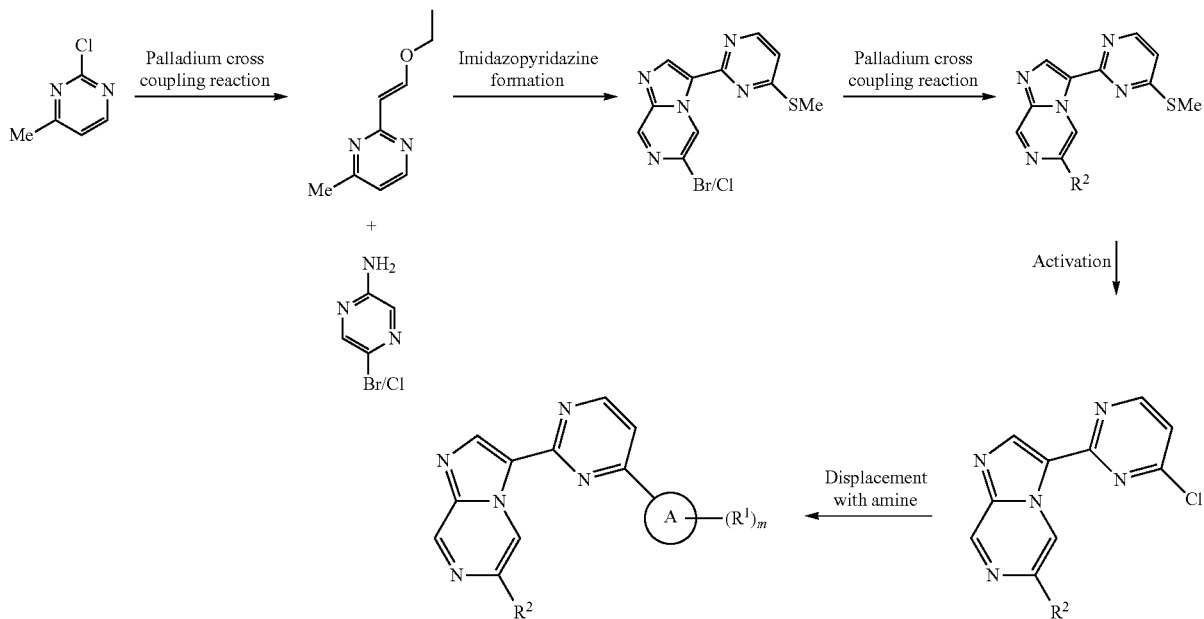

In scheme 31 above, each of Ring A, $R^1$, $R^2$, and m is as defined above and below and in classes and subclasses as described herein.

Scheme 32: General scheme for the preparation of compounds of formula IV where Ring C is a pyrimidine, $R^2$ is —C(O)NH$_2$, $R^3$ is hydrogen, $R^4$ is hydrogen, n is 1, p is 1, and q is 1.

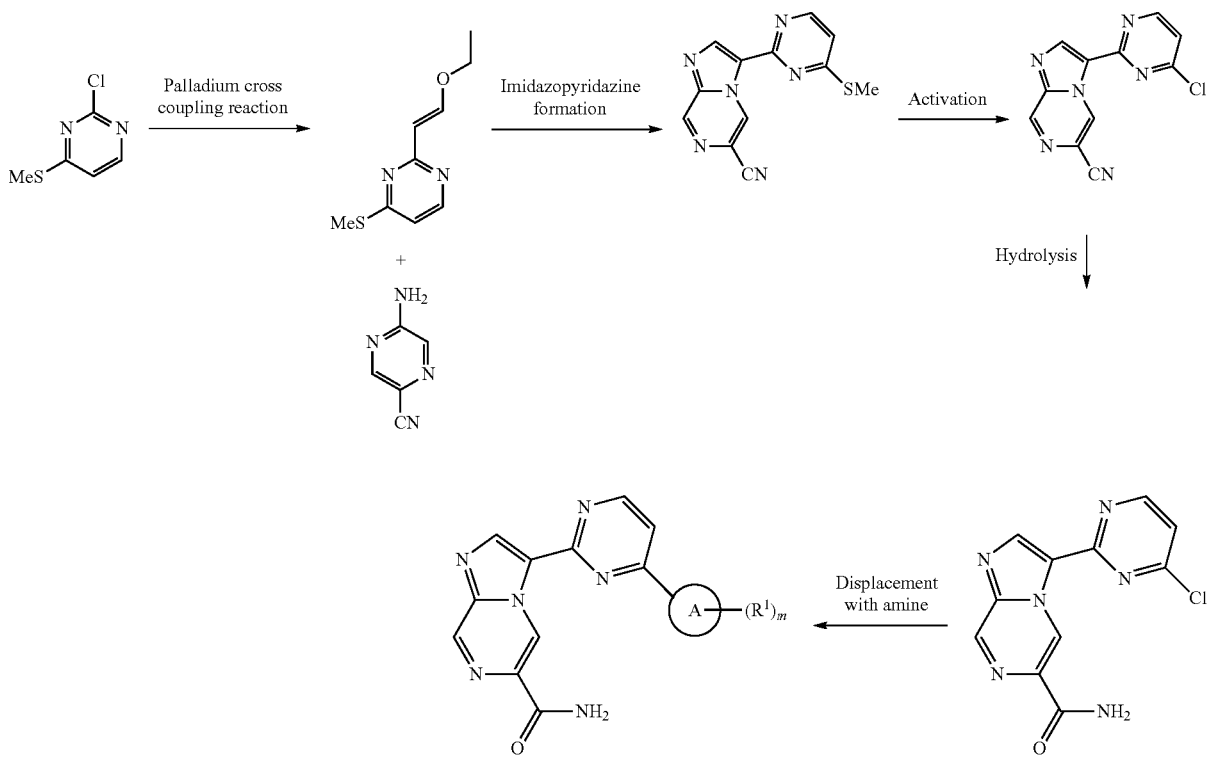

In Scheme 32 above, each of Ring A, $R^1$, and m is as defined above and below and in classes and subclasses as described herein.

Scheme 33: General scheme for the preparation of compounds of formula IV where Ring C is a 5-fluoropyrimidine, $R^3$ is hydrogen, $R^4$ is hydrogen, n is 1, p is 1, and q is 1.

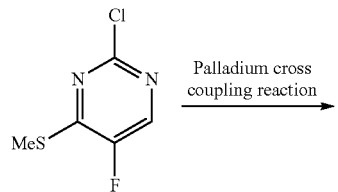

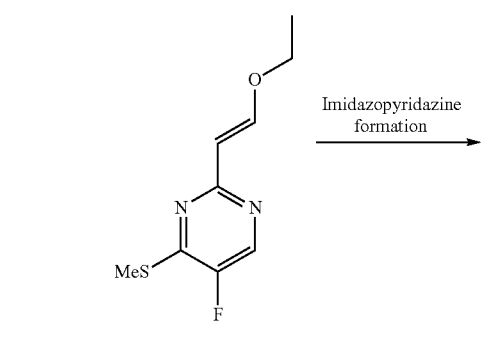

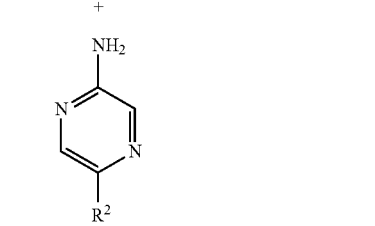

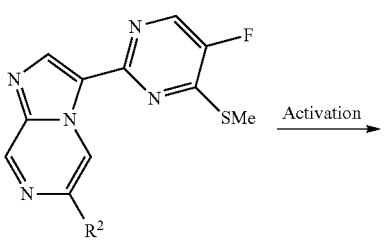

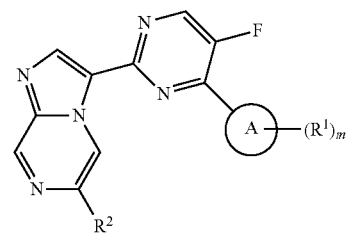

In Scheme 33 above, each of Ring A, $R^1$, $R^2$, and m is as defined above and below and in classes and subclasses as described herein.

Scheme 34: General scheme for the preparation of compounds of formula IV where Ring C is a 6-chloropyrimidine, $R^3$ is hydrogen, $R^4$ is hydrogen, n is 1, p is 1, and q is 1.

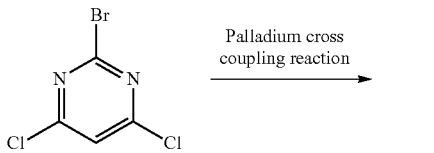

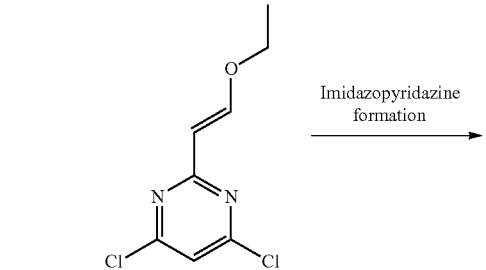

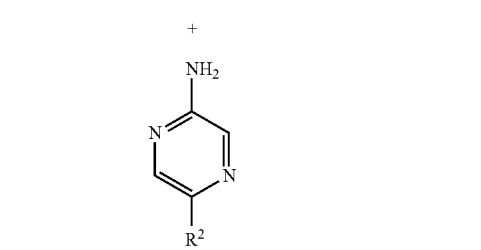

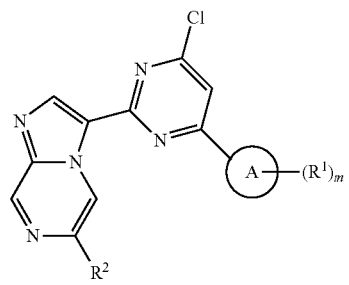

In Scheme 34 above, each of Ring A, $R^1$, $R^2$, and m is as defined above and below and in classes and subclasses as described herein.

Scheme 35: General scheme for the preparation of compounds of formula IV where Ring C is a 6-substituted pyrimidine, $R^3$ is hydrogen, n is 1, p is 1, and q is 1.

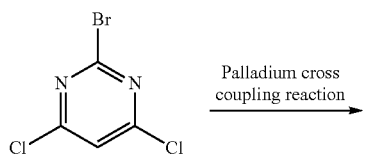

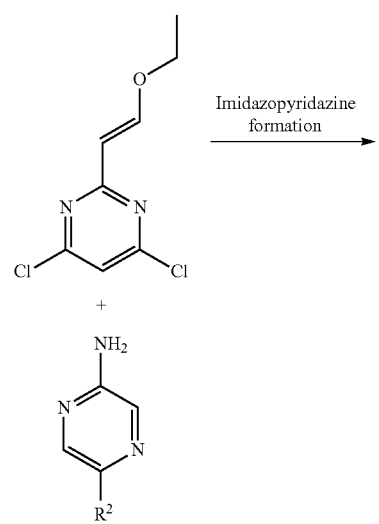

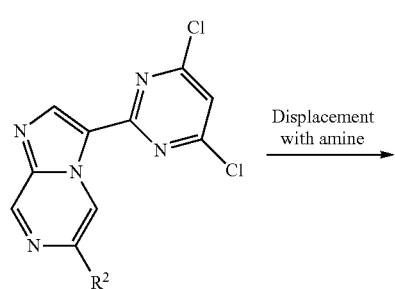

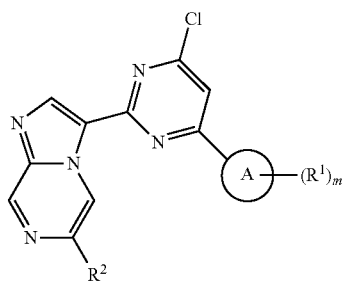

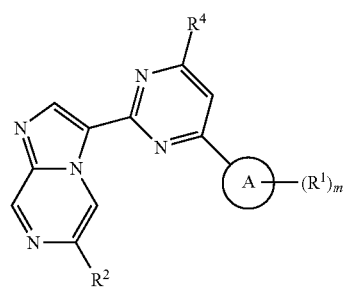

In Scheme 35 above, each of Ring A, $R^1$, $R^2$, $R^4$, and m is as defined above and below and in classes and subclasses as described herein.

Scheme 36: General scheme for the preparation of compounds of formula IV where Ring C is a 6-methylpyrimidine, $R^3$ is hydrogen, $R^4$ is methyl, n is 1, p is 1, and q is 1.

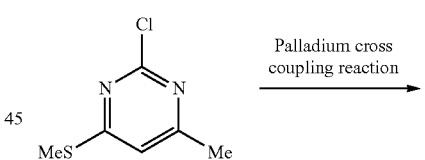

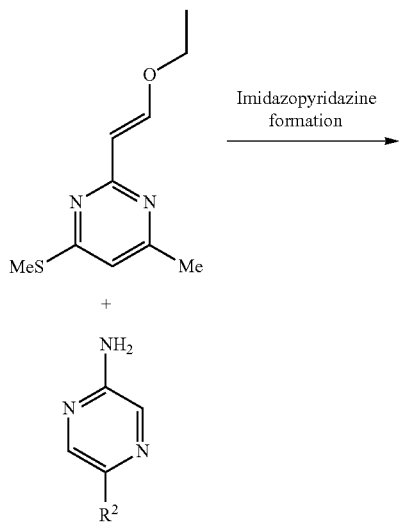

479

-continued

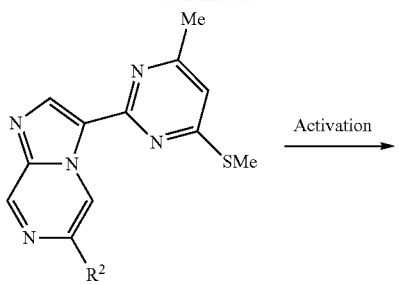

Activation →

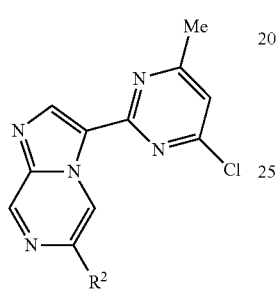

Displacement with amine ↓

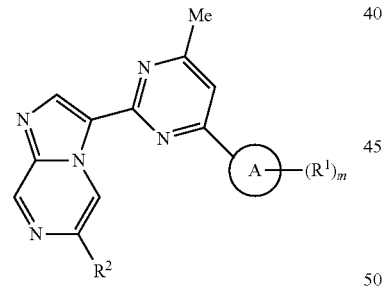

In Scheme 36 above, each of Ring A, R¹, R², and m is as defined above and below and in classes and subclasses as described herein.

Scheme 37: General scheme for the preparation of compounds of formula IV where Ring C is a pyrimidine, R³ is hydrogen, R⁴ is hydrogen, n is 1, p is 1, and q is 1.

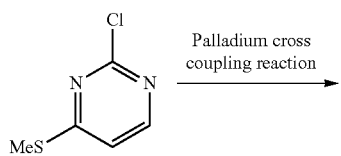

Palladium cross coupling reaction →

480

-continued

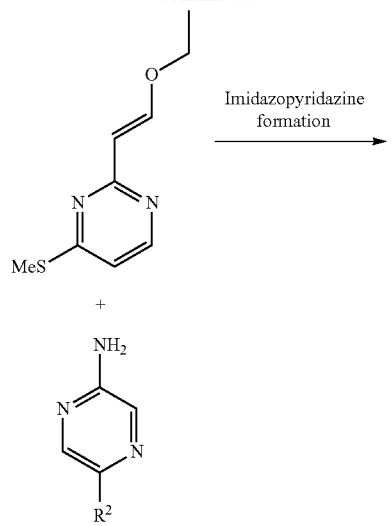

Imidazopyridazine formation →

+

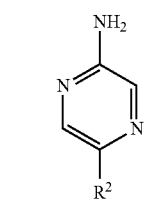

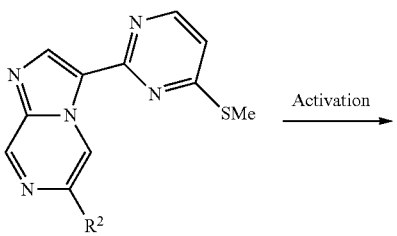

Activation →

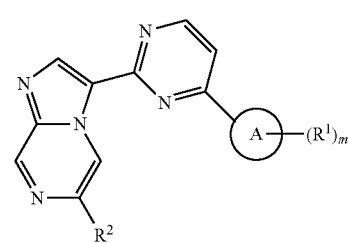

Palladium catalysed cross coupling ↓

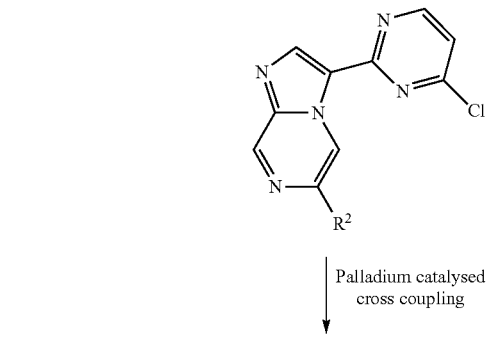

In Scheme 37 above, each of Ring A, R¹, R², and m is as defined above and below and in classes and subclasses as described herein.

481

Scheme 38: General scheme for the preparation of compounds of formula IV where Ring C is a pyridine, $R^3$ is hydrogen, $R^4$ is hydrogen, n is 1, p is 1, and q is 1.

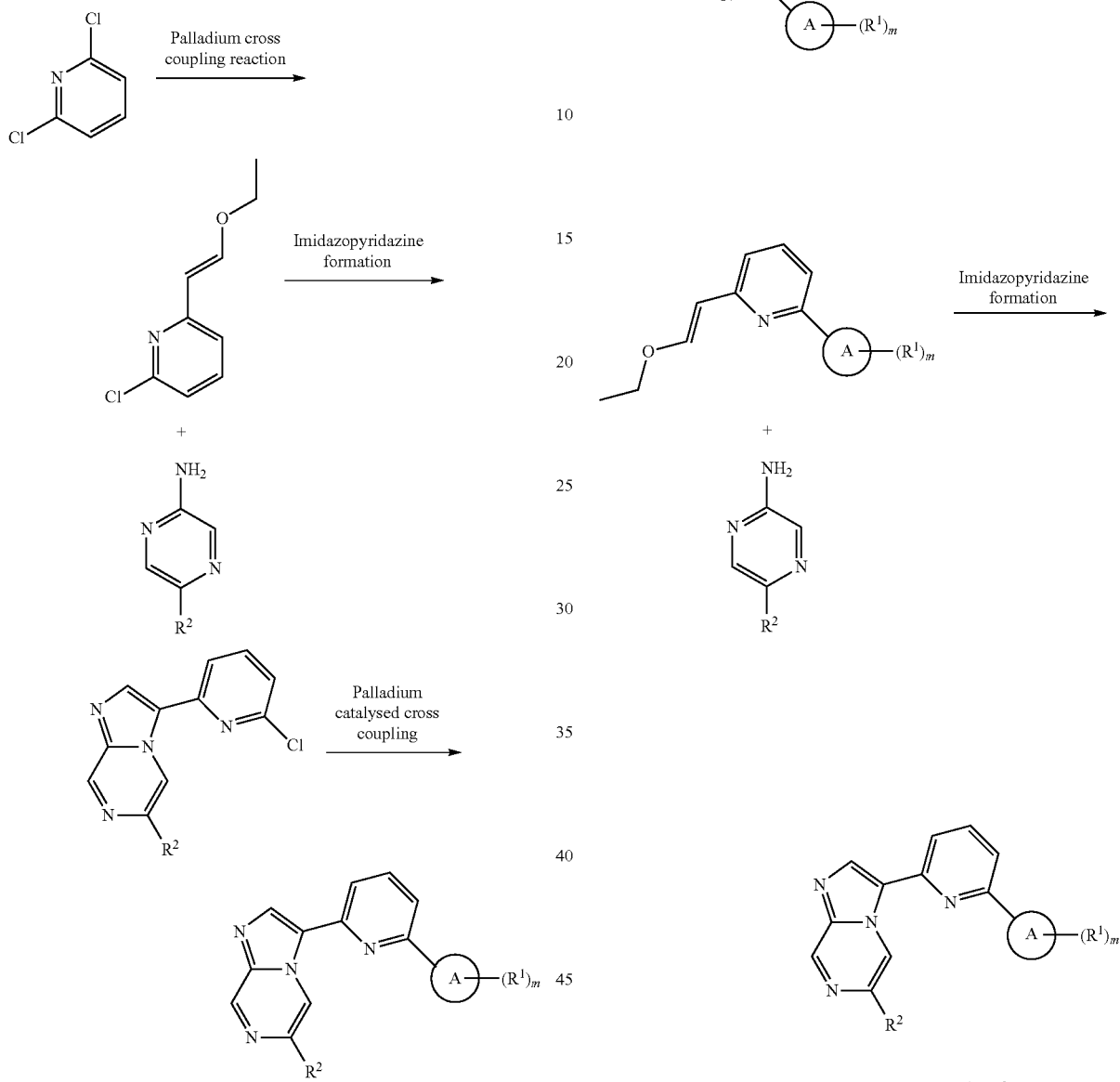

In Scheme 38 above, each of Ring A, $R^1$, $R^2$, and m is as defined above and below and in classes and subclasses as described herein.

In Scheme 39 above, each of Ring A, $R^1$, $R^2$, and m is as defined above and below and in classes and subclasses as described herein.

Scheme 39: General scheme for the preparation of compounds of formula IV where Ring C is a pyridine, $R^3$ is hydrogen, $R^4$ is hydrogen, n is 1, p is 1, and q is 1.

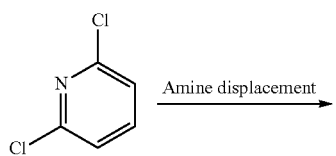

Scheme 40: General scheme for the preparation of compounds of formula IV where Ring C is a pyridine, $R^3$ is hydrogen, $R^4$ is hydrogen, n is 1, p is 1, and q is 1.

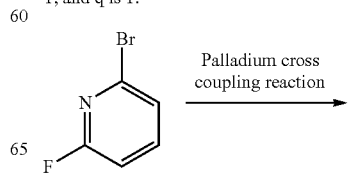

483
-continued

484
-continued

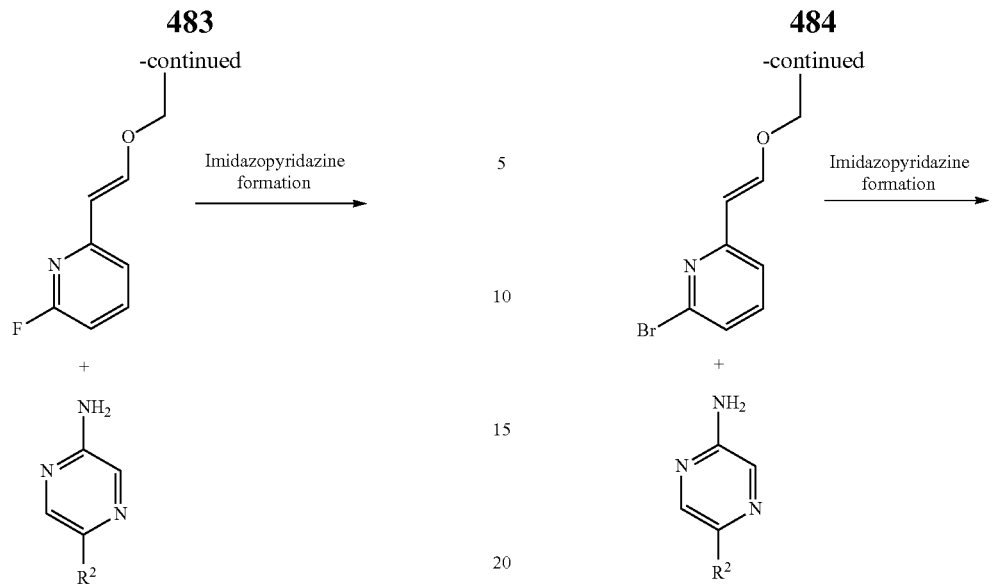

In Scheme 40 above, each of Ring A, $R^1$, $R^2$, and m is as defined above and below and in classes and subclasses as described herein.

In Scheme 41 above, each of Ring A, $R^1$, $R^2$, and m is as defined above and below and in classes and subclasses as described herein.

Scheme 41: General scheme for the preparation of compounds of formula IV where Ring C is a pyridine, $R^3$ is hydrogen, $R^4$ is hydrogen, n is 1, p is 1, and q is 1.

Scheme 42: General scheme for the preparation of compounds of formula IV where Ring C is a pyrimidine, $R^3$ is hydrogen, $R^4$ is hydrogen, n is 1, p is 1, and q is 1.

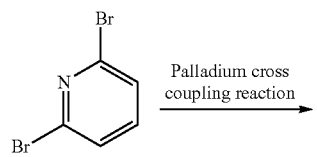

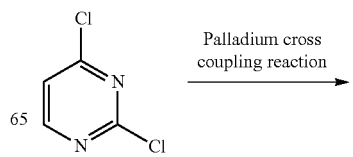

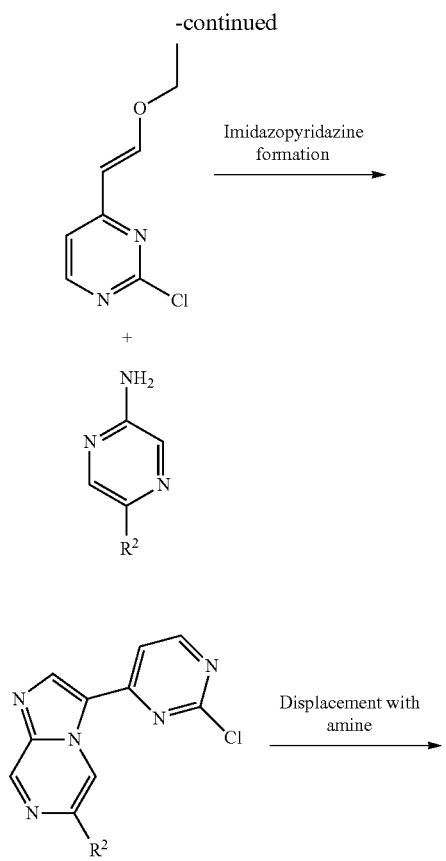

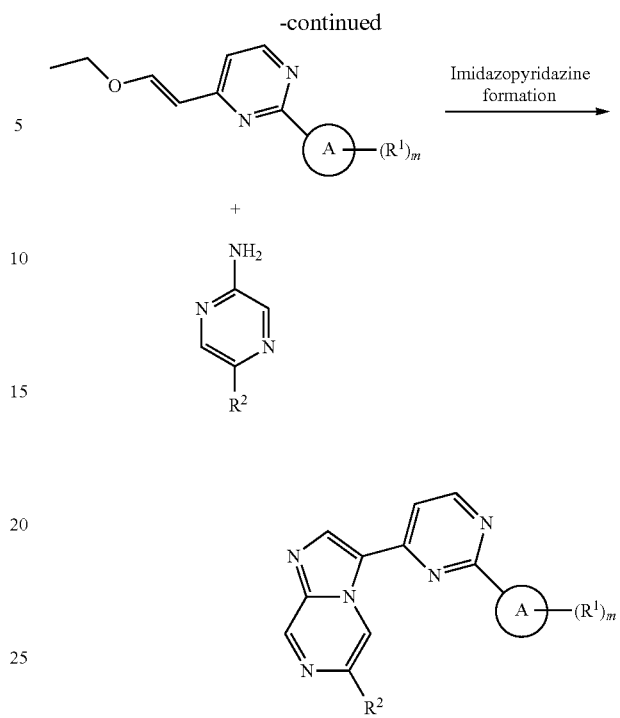

In Scheme 43 above, each of Ring A, R¹, R², and m is as defined above and below and in classes and subclasses as described herein.

Scheme 44: General scheme for the preparation of compounds of formula IV where Ring C is a pyridazine, R³ is hydrogen, R⁴ is hydrogen, n is 1, p is 1, and q is 1.

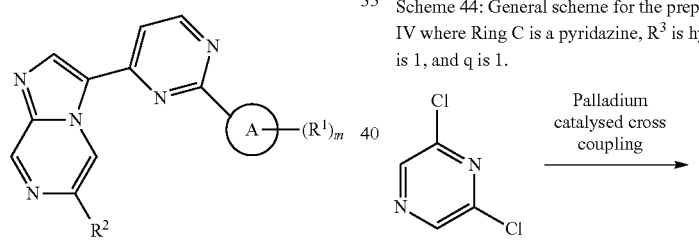

In Scheme 42 above, each of Ring A, R¹, R², and m is as defined above and below and in classes and subclasses as described herein.

Scheme 43: General scheme for the preparation of compounds of formula IV where Ring C is a pyrimidine, R³ is hydrogen, R⁴ is hydrogen, n is 1, p is 1, and q is 1.

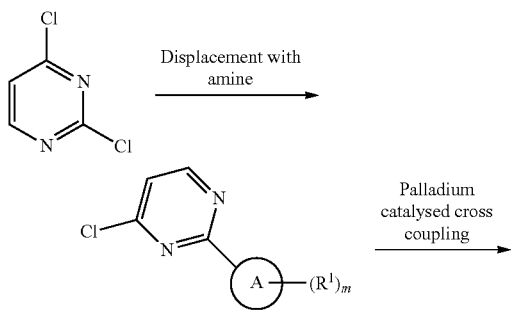

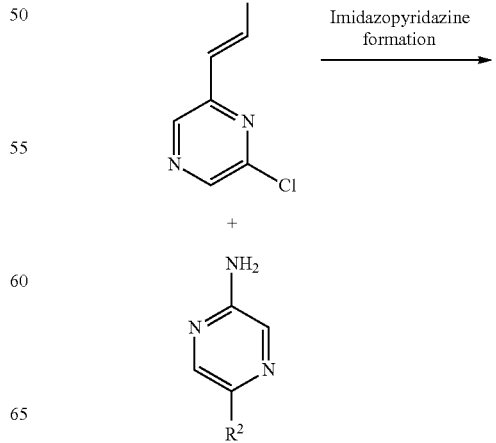

-continued

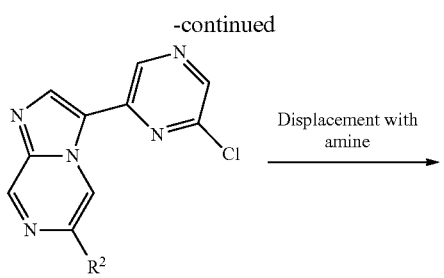

In Scheme 44 above, each of Ring A, $R^1$, $R^2$, and m is as defined above and below and in classes and subclasses as described herein.

Scheme 45: General scheme for the preparation of compounds of formula IV where Ring C is a pyridazine, $R^3$ is hydrogen, $R^4$ is hydrogen, n is 1, p is 1, and q is 1.

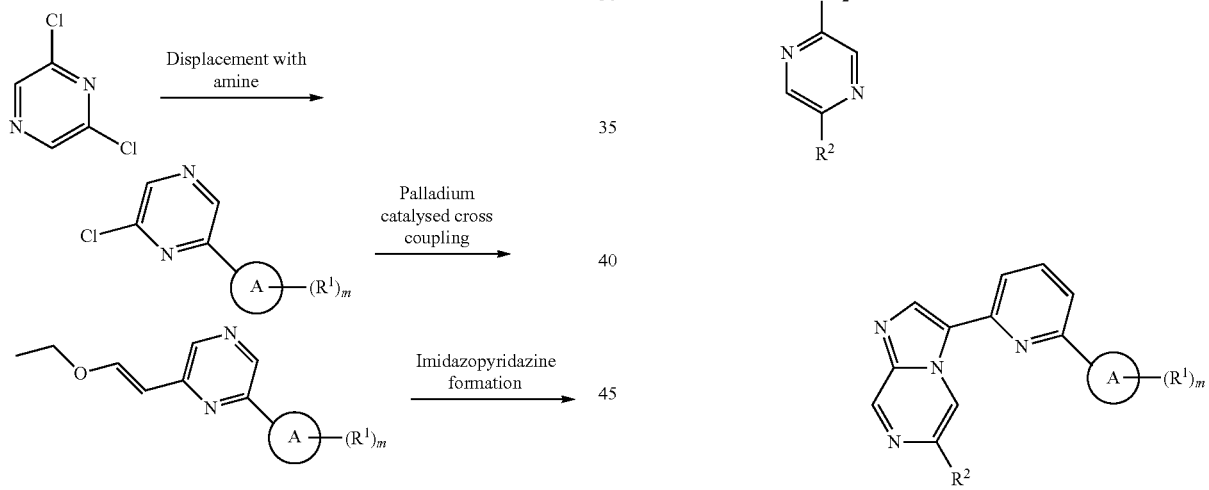

In Scheme 45 above, each of Ring A, $R^1$, $R^2$, and m is as defined above and below and in classes and subclasses as described herein.

Scheme 46: General scheme for the preparation of compounds of formula IV where Ring C is a pyridine, $R^3$ is hydrogen, $R^4$ is hydrogen, n is 1, p is 1, and q is 1.

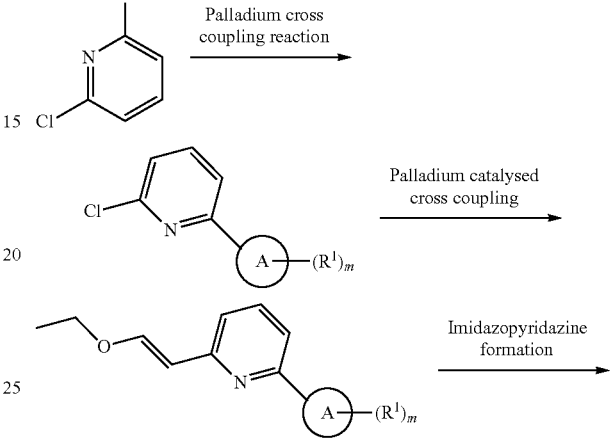

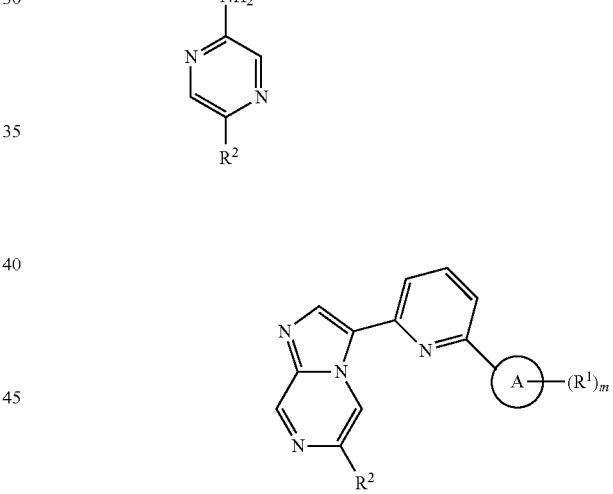

In Scheme 46 above, each of Ring A, $R^1$, $R^2$, and m is as defined above and below and in classes and subclasses as described herein.

Scheme 47: General scheme for the preparation of compounds of formula IV where Ring C is a pyridine, $R^3$ is hydrogen, $R^4$ is fluoro, n is 1, p is 1, and q is 1.

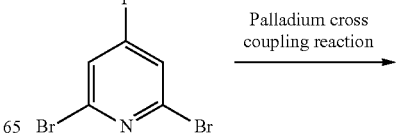

489
-continued

490
-continued

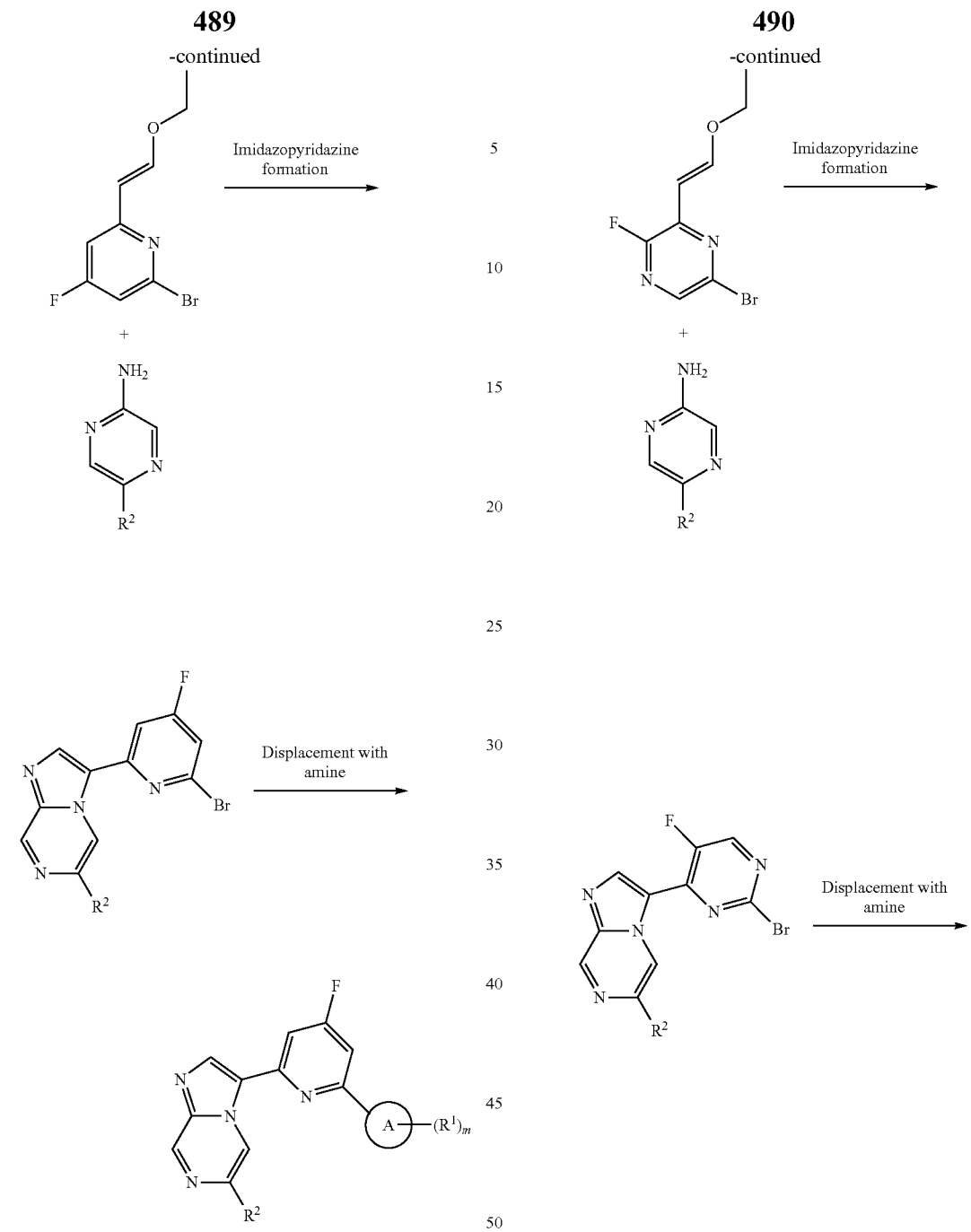

In Scheme 47 above, each of Ring A, $R^1$, $R^2$, and m is as defined above and below and in classes and subclasses as described herein.

Scheme 48: General scheme for the preparation of compounds of formula IV where Ring C is a pyrimidine, $R^3$ is hydrogen, $R^4$ is fluoro, n is 1, p is 1, and q is 1.

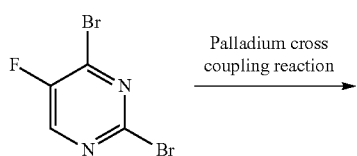

In Scheme 48 above, each of Ring A, $R^1$, $R^2$, and m is as defined above and below and in classes and subclasses as described herein.

Scheme 49: General scheme for the preparation of compounds of formula IV where Ring C is a pyrimidine, $R^2$ is ——$CF_2CH_3$, $R^3$ is hydrogen, $R^4$ is hydrogen, n is 1, p is 1, and q is 1.

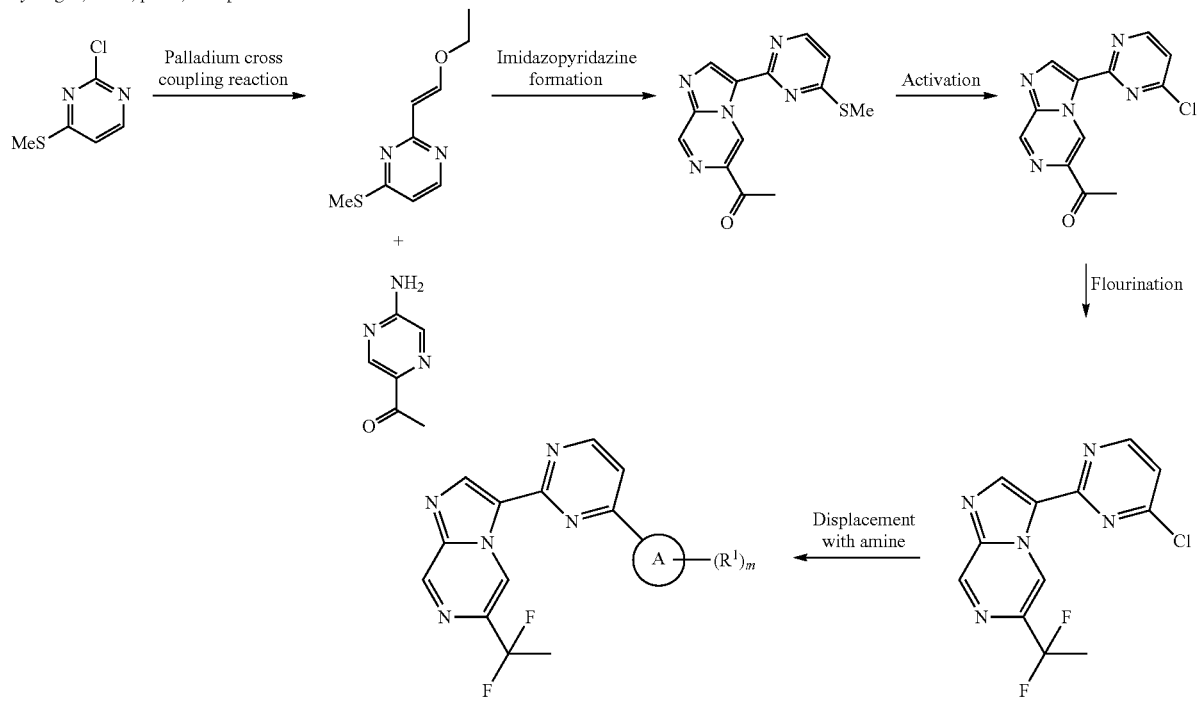

In Scheme 49 above, each of Ring A, $R^1$, and m is as defined above and below and in classes and subclasses as described herein.

Scheme 50: General scheme for the preparation of compounds of Formula V where Ring C is a pyrimidine linked to the bicyclic core from position 2, $R^3$ is hydrogen, $R^4$ is hydrogen, n is 1, p is 1, and q is 1.

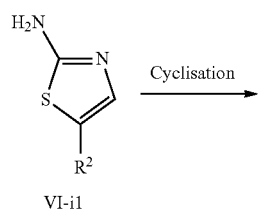

VI-i1

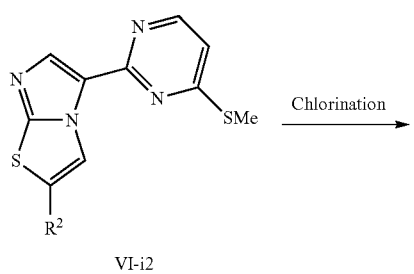

VI-i2

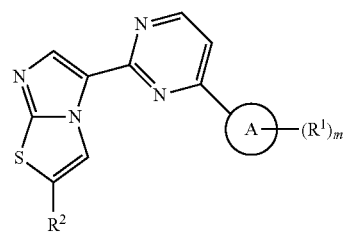

VI

In Scheme 50 above, each of Ring A, $R^1$, $R^2$, and m is as defined above and below and in classes and subclasses as described herein.

Scheme 51: General scheme for the preparation of compounds of Formula V where Ring C is a pyrimidine linked to the bicyclic core from position 2, R² is —CF₂H, R³ is hydrogen, R⁴ is hydrogen, n is 1, p is 1, and q is 1.

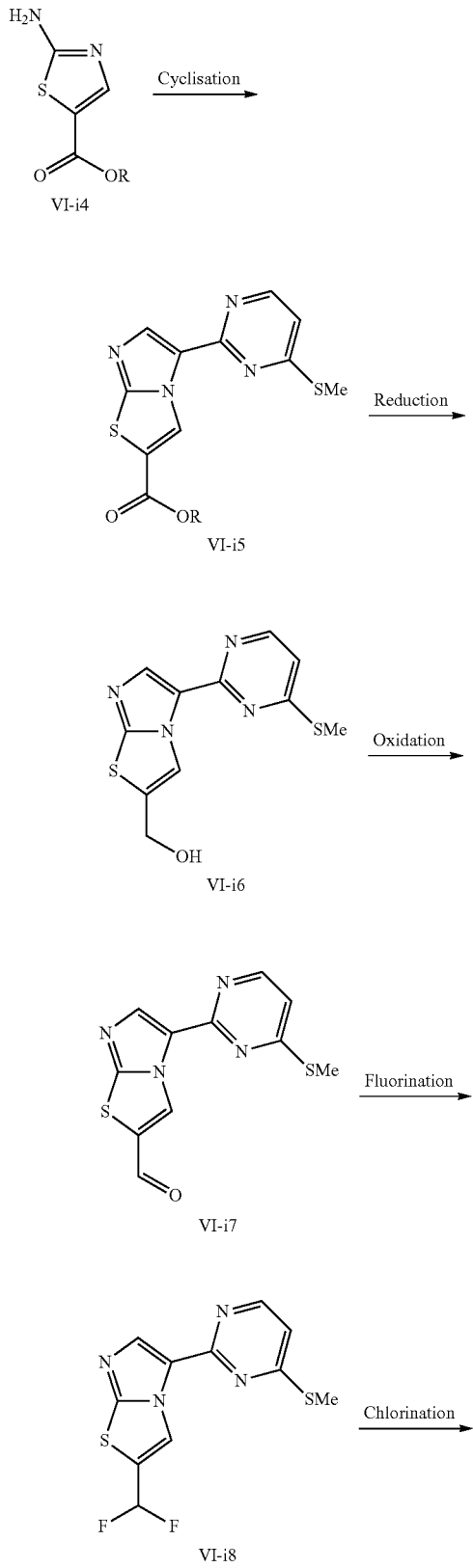

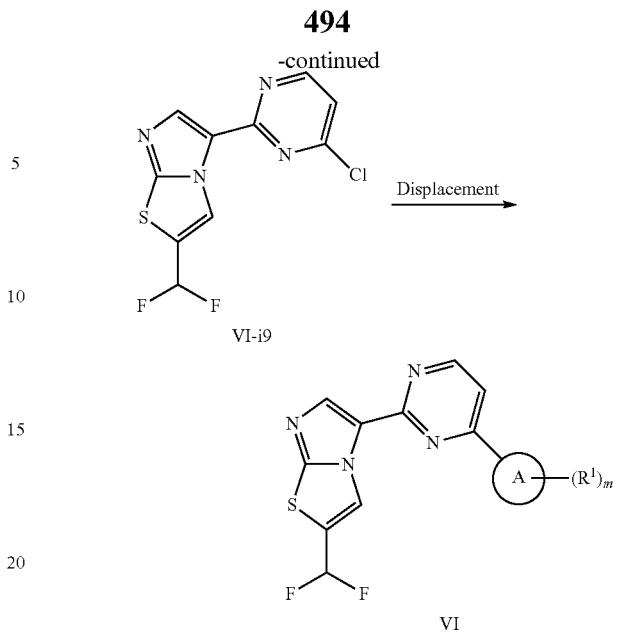

In Scheme 51 above, each of Ring A, R¹, and m is as defined above and in classes and subclasses as described herein.

One of skill in the art will appreciate that compounds of formula I-V may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5th Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration a. Pharmaceutically Acceptable Compositions According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit GCN2 protein kinase, or a mutant thereof, in a biological sample or in a patient. In certain embodiments, the amount of compound in compositions of this invention is such that is effective to measurably inhibit GCN2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of GCN2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

b. Uses of Compounds and Pharmaceutically Acceptable Compositions

Compounds and compositions described herein are generally useful for the inhibition of GCN2 kinase activity.

The activity of a compound utilized in this invention as an inhibitor of GCN2, or a mutant thereof, may be assayed in vitro, in vivo or in a cell line. In vitro assays include assays that determine inhibition of either the phosphorylation activity and/or the subsequent functional consequences, or ATPase activity of activated GCN2, or a mutant thereof. Alternate in vitro assays quantitate the ability of the inhibitor to bind to GCN2. Inhibitor binding may be measured by radiolabeling the inhibitor prior to binding, isolating the inhibitor/GCN2 complex and determining the amount of radiolabel bound. Alternatively, inhibitor binding may be determined by running a competition experiment where new inhibitors are incubated with GCN2 bound to known radioligands. Detailed conditions for assaying a compound utilized in this invention as an inhibitor of GCN2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of GCN2 and are therefore useful for treating one or more disorders associated with activity of GCN2. Thus, in certain embodiments, the present invention provides a method for treating a GCN2-mediated disorder comprising the step of administering to a patient in need thereof a compound of the present invention, or pharmaceutically acceptable composition thereof.

As used herein, the terms "GCN2-mediated" disorders, diseases, and/or conditions as used herein means any disease or other deleterious condition in which GCN2, or a mutant thereof, are known to play a role. Accordingly, another embodiment of the present invention relates to treating or lessening the severity of one or more diseases in which GCN2, or a mutant thereof, are known to play a role.

In some embodiments, the present invention provides a method for treating one or more disorders, diseases, and/or conditions wherein the disorder, disease, or condition is selected from the group consisting of inflammatory conditions, immunological conditions, autoimmune conditions, allergic conditions, rheumatic conditions, thrombotic conditions, cancer, infections, neurodegenerative diseases, degenerative diseases, neuroinflammatory diseases, cardiovascular diseases, and metabolic conditions.

In some embodiments, the cancer to be treated is a solid tumor or a tumor of the blood and immune system.

In some embodiments, the cancer is a solid tumor, wherein the solid tumor originates from the group of tumors of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondrosarcoma and Ewing sarcoma, germ cells, including embryonal tissue tumors, and/or the lung, from the group of monocytic leukemia, lung adenocarcinoma, small-cell lung carcinomas, pancreatic cancer, glioblastomas, neurofibroma, angiosarcoma, breast carcinoma and/or maligna melanoma.

In some embodiments, the autoimmune condition is rheumatoid arthritis, systemic lupus, multiple sclerosis, psoriasis, Sjögrens syndrome or transplant organ rejection.

In some embodiments, the metabolic condition is diabetes.

In some embodiments, the degenerative disease is osteoarthritis.

In some embodiments, the inflammatory condition is asthma, inflammatory bowel disease, or giant cell arteritis.

In some embodiments, the cardiovascular disease is an ischemic injury.

In some embodiments, the neurodegenerative disease is Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, or Parkinson's disease.

In some embodiments, the infection is caused by *leishmania*, mycobacteria, including *M. leprae, M. tuberculosis* and/or *M. avium, plasmodium*, human immunodeficiency virus, Epstein Barr virus, Herpes simplex virus, or hepatitis C virus.

Furthermore, the invention provides the use of a compound according to the definitions herein, or a pharmaceutically acceptable salt, or a hydrate or solvate thereof for the preparation of a medicament for the treatment of inflammatory conditions, immunological conditions, autoimmune conditions, allergic conditions, rheumatic conditions, thrombotic conditions, cancer, infections, neurodegenerative diseases, degenerative diseases, neuroinflammatory diseases, cardiovascular diseases, or metabolic conditions.

c. Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo- 24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a compound of formula I and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/

Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis *nodosa* (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting GCN2, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a GCN2 protein kinase, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting GCN2, or a mutant thereof, activity in a patient comprising the step of administering to said patient a compound of the present invention, or a composition comprising said compound. In other embodiments, the present invention provides a method for treating a disorder mediated by GCN2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™ Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-10}$33, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™.

Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof; 1-(4-chloroanilino)-4-(4-pyridylmethyl)phthalazine succinate; Angiostatin™;

Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YER-VOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO006/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti- PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MED14736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981).

REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI11873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors.

KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation 1: 2-(1H-Pyrazol-4-yl)morpholine A1

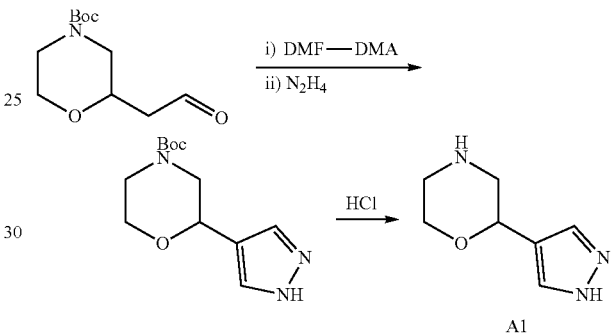

A mixture of tert-butyl 2-(2-oxoethyl)morpholine-4-carboxylate (5.77 g, 25 mmol) and DMF-DMA (6.7 mL, 50 mmol) in DMF (50 mL) was stirred at 80° C. for 17 hours. The reaction mixture was cooled to ambient temperature and the solvent removed in vacuo. The residue was taken up in EtOH (100 mL) and hydrazine hydrate (1.3 mL, 26.5 mmol) was added with stirring at ambient temperature. After 3 hours, the solvent was removed in vacuo and the residue purified by column chromatography (silica, PE/EtOAc gradient elution), to give tert-butyl 2-(1H-pyrazol-4-yl)morpholine-4-carboxylate (2.35 g, 37%) as a yellow solid; $^1$H NMR (500 MHz, Chloroform-d) δ 7.63 (s, 2H), 4.52 (dd, 1H), 4.12 (br s, 1H), 3.97-3.90 (m, 2H), 3.68 (td, 1H), 3.05 (d, 2H), 1.51 (s, 9H); MS m/z: 254.1 (M+H)$^+$.

3M HCl in MeOH (45 mL of 3 M, 135 mmol) was added to a stirred solution of tert-butyl 2-(1H-pyrazol-4-yl)morpholine-4-carboxylate (2.35 g, 9.3 mmol) in DCM (75 mL) and the reaction heated under reflux for 5 hours. The reaction was cooled to ambient temperature and the solvent removed in vacuo. The residue was dissolved in the minimum amount of DCM/MeOH and loaded on to an ion-exchange cartridge. The cartridge was washed with MeOH/DCM mixtures, which were discarded. The product was eluted by washing with 2 M NH$_3$ in MeOH/DCM. Solvent was removed in vacuo to give 2-(1H-pyrazol-4-yl)morpholine A1 (1.27 g, 89%) as an orange solid, which was taken on to the next reaction without further purification; $^1$H NMR (500 MHz, Chloroform-d) δ 7.60 (s, 2H), 4.56 (dd, 1H), 3.98 (ddd, 1H), 3.77 (td, 1H), 3.11 (dd, 1H), 3.00 (td, 1H), 2.93-2.88 (m, 2H); MS m/z: 154.2 (M+H)$^+$.

Preparation 2: N-((6-Methylmorpholin-2-yl)methyl)methanesulfonamide A2

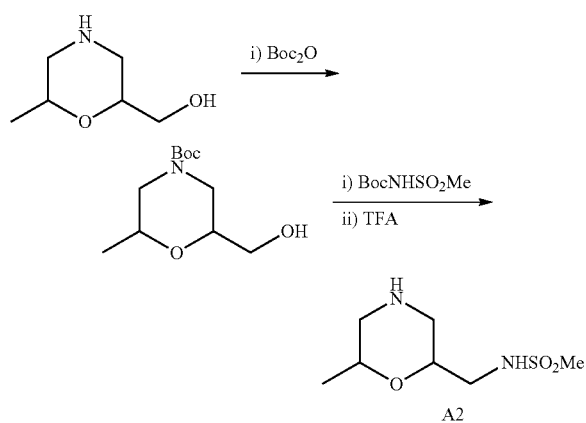

Di-tert-butyl dicarbonate (600 mg, 2.75 mmol) was added to a stirred solution of (6-methylmorpholin-2-yl)methanol (300 mg, 2.3 mmol) and Et$_3$N (835 µL, 6 mmol) in DCM (5 mL) at ambient temperature and the reaction stirred for 2 hours. The reaction mixture was washed with 0.5 M HCl (×1), water (×2) and brine (×1). The combined organics were dried (MgSO$_4$) and concentrated in vacuo. The residue was purified by column chromatography (silica, PE/EtOAc gradient elution) to give cis-tert-butyl 2-(hydroxymethyl)-6-methyl-morpholine-4-carboxylate (225 mg, 42%) as a colourless oil, $^1$H NMR (500 MHz, Chloroform-d) δ 3.90 (s, 2H), 3.73-3.68 (m, 1H), 3.64-3.55 (m, 3H), 2.67 (s, 1H), 2.49 (s, 1H), 1.94 (dd, 1H), 1.49 (s, 9H), 1.21 (d, 3H), and trans-tert-butyl 2-(hydroxymethyl)-6-methyl-morpholine-4-carboxylate (170 mg, 32%) as a colourless oil; $^1$H NMR (500 MHz, Chloroform-d) δ 4.00-3.96 (m, 1H), 3.90 (s, 1H), 3.72 (s, 1H), 3.66-3.49 (m, 3H), 3.38 (ddd, 1H), 3.15 (s, 1H), 1.98-1.82 (m, 1H), 1.49 (s, 9H), 1.23 (d, 3H).

To a solution of cis-tert-butyl 2-(hydroxymethyl)-6-methyl-morpholine-4-carboxylate (225 mg, 1 mmol), tert-butyl N-methylsulfonylcarbamate (280 mg, 1.4 mmol) and PPh$_3$ (760 mg, 3 mmol) in THF (10 mL) was added DEAD (330 µL, 2 mmol) dropwise and the reaction mixture stirred at ambient temperature under N$_2$ for 18 hours. The reaction mixture was concentrated in vacuo and purified by column chromatography to give cis-tert-butyl 2-[[tert-butoxycarbonyl (methylsulfonyl)amino]methyl]-6-methyl-morpholine-4-carboxylate as a colourless oil. This material was taken up in DCM (10 mL) and TFA (2 mL, 26 mmol) was added at ambient temperature. After 3 hours the solvent was removed in vacuo and the residue azeotroped with DCM (×2) and diethyl ether (×2). The residue was taken up in MeOH and passed through an ion-exchange cartridge, washing with MeOH/DCM mixtures. The product was eluted with 2 M NH$_3$ in MeOH/DCM. The solvent was removed in vacuo to give cis-N-[(6-methylmorpholin-2-yl)methyl]methanesulfonamide A2 (173 mg, 85%) as a white solid, which was taken on to the next reaction without further purification; $^1$H NMR (500 MHz, Chloroform-d) δ 4.66 (br s, 1H), 3.59-3.49 (m, 2H), 3.17 (dd, 1H), 2.99 (dd, 1H), 2.90 (s, 3H), 2.78 (dd, 2H), 2.47 (dd, 1H), 2.35 (dd, 1H), 1.05 (d, 3H); MS m/z: 209 (M+H)$^+$.

Preparation 3: N-((4,4-Difluoropiperidin-3-yl)methyl)methanesulfonamide A3

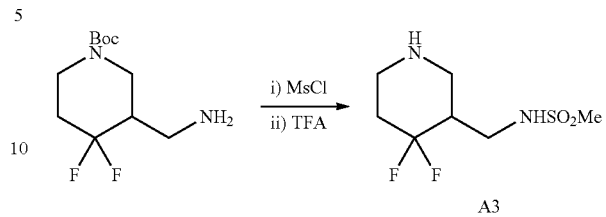

Methanesulfonyl chloride (200 µL, 2.6 mmol) was added to a solution of tert-butyl 3-(aminomethyl)-4,4-difluoropiperidine-1-carboxylate (500 mg, 1.8 mmol) and Et$_3$N (400 µL, 2.9 mmol) in THF (11 mL) under N$_2$. The reaction mixture was stirred at ambient temperature for 3 hours then diluted with DCM and saturated aqueous NaHCO$_3$ solution. The mixture was stirred for 10 minutes then passed through a phase separator cartridge. The organic phase was concentrated and the residue taken up in DCM/TFA (2 mL/2 mL), stirred for 2 hours then concentrated. The residue was taken up in MeOH and passed through an ion-exchange cartridge, washing with methanol and eluting the product with 2 M methanolic ammonia solution. The solution was concentrated in vacuo to give a white solid of N-((4,4-difluoropiperidin-3-yl)methyl) methanesulfonamide A3 (450 mg), which was taken on to the next reaction without further purification; $^1$H NMR (500 MHz, DMSO-d$_6$) δ 7.10 (t, 1H), 3.27 (ddd, 2H), 3.11-3.01 (m, 1H), 2.91-2.85 (m, 5H), 2.69-2.56 (m, 1H), 2.40 (dd, 1H), 2.08-1.86 (m, 2H), 1.84-1.66 (m, 1H).

Preparation 4: (S)—N-((6-Oxopiperazin-2-yl)methyl)methanesulfonamide A4

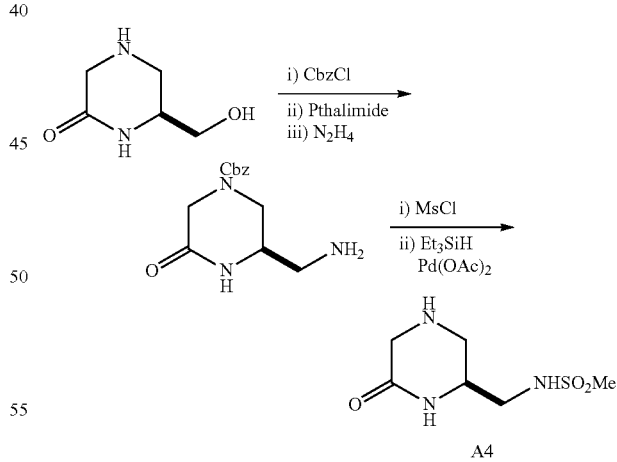

Benzyl chloroformate (1.2 mL, 8.5 mmol) was added to an ice cold solution of (6S)-6-(hydroxymethyl)piperazin-2-one (800 mg, 6.15 mmol) and K$_2$CO$_3$ (5.95 g, 43 mmol) in EtOAc (20 mL)/H$_2$O (20 mL). The reaction mixture was stirred for 18 hours at ambient temperature. The reaction mixture was diluted with EtOAc, washed with saturated aqueous sodium bicarbonate solution and brine. The organic phase was dried (Na$_2$SO$_4$), filtered and concentrated in vacuo. The residue was purified by column chromatography to give benzyl (3S)-3-(hydroxymethyl)-5-oxo-piperazine-1-carboxylate as a colourless oil (700 mg, 43%); MS m/z: 265 (M+H)$^+$.

DIAD (1.5 mL, 7.6 mmol) was added to an ice cold solution of phthalimide (1.11 g, 7.6 mmol) and PPh$_3$ (1.75 mL, 7.6 mmol) in DCM (10 mL) under N$_2$. The solution was stirred for 10 minutes, then benzyl (3S)-3-(hydroxymethyl)-5-oxo-piperazine-1-carboxylate (500 mg, 1.9 mmol) was added. The solution was stirred for 18 hours, gradually warming to ambient temperature. The solution was diluted with a saturated aqueous NaHCO$_3$ solution. After 5 minutes stirring, the layers were separated using a phase separator cartridge. The organic phase was concentrated in vacuo and the residue purified by column chromatography (silica, PE/EtOAc gradient elution to give benzyl (3R)-3-[(1,3-dioxoisoindolin-2-yl)methyl]-5-oxo-piperazine-1-carboxylate as an oil (700 mg, ~60% pure), which was taken directly on to the next step; MS m/z: 394 (M+H)$^+$.

A mixture of benzyl (3R)-3-[(1,3-dioxoisoindolin-2-yl)methyl]-5-oxo-piperazine-1-carboxylate (700 mg, 1.068 mmol) and hydrazine hydrate (100 µL, 2.04 mmol) in ethanol (5 mL) was heated under reflux for 5 hours. The resulting suspension was filtered and the white solid was washed thoroughly with ethanol. The ethanolic solution was added to an ion-exchange cartridge washing with methanol, then eluting the product with a 2 M methanolic NH$_3$ solution. The filtrate was concentrated to give (R)-benzyl 3-(aminomethyl)-5-oxopiperazine-1-carboxylate as a colourless oil which was taken directly on to the next step (240 mg, 85%); MS m/z: 264 (M+H)$^+$.

Methanesulfonyl chloride (100 µL, 1.3 mmol) was added to an ice cold solution of benzyl (3R)-3-(aminomethyl)-5-oxo-piperazine-1-carboxylate (240 mg, 1 mmol) and Et$_3$N (200 µL, 1.4 mmol) in DCM (5 mL) under N$_2$. The solution was stirred for 3 hours, gradually warming to ambient temperature. The reaction mixture was diluted with DCM and a saturated aqueous NaHCO$_3$ solution. After 5 minutes, the organic phase was isolated using a phase separator cartridge, then concentrated in vacuo. The residue was purified by column chromatography (silica, PE/EtOAc gradient elution) to give benzyl (3S)-3-(methanesulfonamidomethyl)-5-oxo-piperazine-1-carboxylate as a white foam (233 mg, 75%) that was taken directly on to the next step; MS m/z: 342 (M+H)$^+$.

A mixture of benzyl (3S)-3-(methanesulfonamidomethyl)-5-oxo-piperazine-1-carboxylate (230 mg, 0.7 mmol), Pd(OAc)$_2$ (60 mg, 0.3 mmol), Et$_3$SiH (500 µL, 3 mmol) and Et$_3$N (300 µL, 2 mmol) in DCM (5 mL) was stirred at ambient temperature for 2 hours under N$_2$. The residue was passed through an ion-exchange cartridge washing with MeOH/DCM mixtures and eluting the product with 2 M NH$_3$ in MeOH/DCM mixtures. The solvent was removed in vacuo to give (S)—N-((6-oxopiperazin-2-yl)methyl)methanesulfonamide, A4 as a white solid (130 mg, 93%), which was taken on to the next reaction without further purification; MS m/z: 208 (M+H)$^+$.

Preparation 5: (S)-Dimethyl((morpholin-2-ylmethyl)imino)-λ$^6$-sulfanone A5

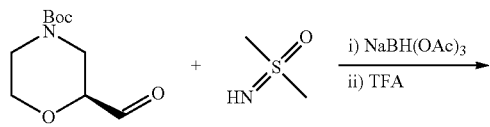

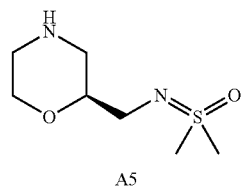

Sodium triacetoxyborohydride (1.26 g, 5.95 mmol) was added to a mixture of tert-butyl (2S)-2-formylmorpholine-4-carboxylate (320 mg, 1.5 mmol) and (methylsulfonimidoyl)methane (165 mg, 1.8 mmol) in DCE (20 mL) and the reaction stirred at ambient temperature for 60 hours. The mixture was diluted with DCM and saturated aqueous NaHCO$_3$ and stirred for 30 minutes. The layers were separated and the organic layer washed with saturated aqueous NaHCO$_3$ (×2), brine, dried (MgSO$_4$), filtered and concentrated in vacuo to give tert-butyl (S)-2-(((dimethyl(oxo)-λ$^6$-sulfanylidene)amino)methyl)morpholine-4-carboxylate (343 mg); MS m/z: 293 (M+H)$^+$.

The residue was taken up in DCM (10 mL) and TFA (5 mL) was added at ambient temperature. The mixture was stirred at ambient temperature for 17 hours. The solvent was removed in vacuo and the residue azeotroped with DCM (×2) and diethyl ether (×2). The residue was passed through an ion-exchange cartridge washing with MeOH/DCM mixtures and eluting the product with 2 M NH$_3$ in MeOH/DCM mixtures. The solvent was removed in vacuo to give (S)-dimethyl((morpholin-2-ylmethyl)imino)-λ$^6$-sulfanone A5 as a pale yellow oil (140 mg, 63%), which was taken on to the next reaction without further purification; $^1$H NMR (500 MHz, DMSO-d$_6$) δ 4.54 (s, 1H), 3.69 (ddd, 2H), 3.40 (td, 1H), 3.33-3.26 (m, 2H), 3.25-3.23 (m, 1H), 2.96 (s, 3H), 2.81-2.77 (m, 1H), 2.66-2.57 (m, 3H), 2.32 (dd, 1H); MS m/z: 193 (M+H)$^+$.

Preparation 6: N-((5-Ethyl-4,4-difluoropiperidin-3-yl)methyl)methanesulfonamide A6

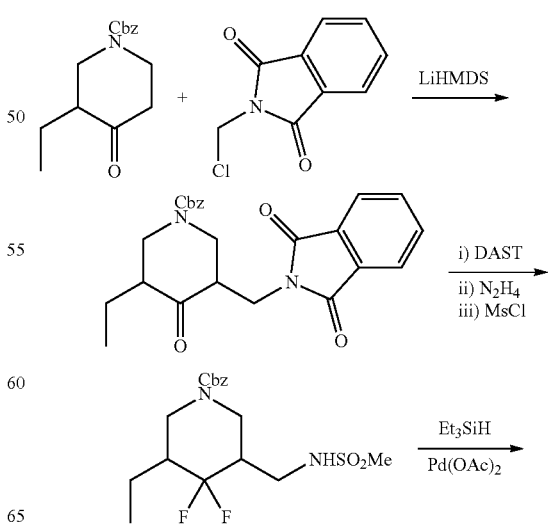

-continued

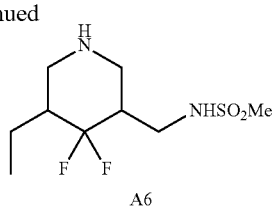

A6

LiHMDS (5 mL of 1M solution, 5.0 mmol) was added dropwise to a solution of benzyl 3-ethyl-4-oxo-piperidine-1-carboxylate (1 g, 3.8 mmol) in THF (14 mL) cooled to −78° C. under $N_2$. 90 minutes later, a solution of 2-(chloromethyl)isoindoline-1,3-dione (1.0 g, 5.1 mmol) in THF (2 mL) was added. The solution was stirred at −78° C. for 1 hour then at 0° C. for 1 hour, then quenched by adding saturated aqueous $NH_4Cl$ solution (~2 mL). The reaction mixture was diluted with EtOAc, washed with a saturated aqueous sodium bicarbonate solution and brine. The organic phase was dried ($Na_2SO_4$), filtered and concentrated in vacuo. The residue was purified by column chromatography (silica, PE/EtOAc gradient elution) to give benzyl 3-[(1,3-dioxoisoindolin-2-yl)methyl]-5-ethyl-4-oxo-piperidine-1-carboxylate as a colourless gum (1.1 g), which was taken directly on to the next step; MS m/z: 421 (M+H)$^+$.

A mixture of benzyl 3-[(1,3-dioxoisoindolin-2-yl)methyl]-5-ethyl-4-oxo-piperidine-1-carboxylate (1.1 g, 2.6 mmol) and DAST (6 mL, 45 mmol) was stirred at 0° C. for 3 hours, then at ambient temperature for 16 hours. The reaction mixture was diluted with DCM and carefully quenched with a saturated aqueous $NaHCO_3$ solution. The layers were separated and the organic phase was washed with brine, dried ($Na_2SO_4$) and concentrated in vacuo. The crude mixture was purified by column chromatography to give benzyl 3-((1,3-dioxoisoindolin-2-yl)methyl)-5-ethyl-4,4-difluoropiperidine-1-carboxylate as an off-white solid (200 mg, 17%); MS m/z: 423 (M+H)$^+$.

This material was dissolved in EtOH (3 mL) and hydrazine hydrate (60 μL, 1.2 mmol) was added. The mixture was stirred under reflux for 24 hours, then left standing at ambient temperature for 36 hours. The resulting suspension was diluted with methanol and passed through an ion-exchange cartridge. The cartridge was washed with MeOH and the product eluted with 2 M methanolic $NH_3$ solution. The filtrate was concentrated to give benzyl 3-(aminomethyl)-5-ethyl-4,4-difluoropiperidine-1-carboxylate as a gum (115 mg); MS m/z: 313 (M+H)$^+$.

This material was dissolved in DCM (3 mL) under $N_2$. $Et_3N$ (100 μL, 0.7 mmol) was added and the solution cooled in an ice bath. Methanesulfonyl chloride (50 μL, 0.6 mmol) was added dropwise and the mixture was stirred for 10 minutes. The cooling bath was removed and the mixture stirred at ambient temperature for 10 minutes. The reaction was quenched with a few drops of saturated $NaHCO_3$, and stirred for 5 minutes, then filtered through a phase separator cartridge and concentrated under reduced pressure to give benzyl 3-ethyl-4,4-difluoro-5-(methylsulfonamidomethyl)piperidine-1-carboxylate as a colourless oil (140 mg); MS m/z: 391 (M+H)$^+$.

This material was dissolved in DCM (3 mL) and Pd(OAc)$_2$ (35.23 mg, 0.2 mmol), $Et_3N$ (176.0 μL, 1.3 mmol) and $Et_3SiH$ (381.5 μL, 2.4 mmol) were added to the reaction mixture. The solution was stirred at ambient temperature for 1 hour. The solution was poured onto an ion-exchange cartridge, washing with methanol and eluting the product with a 2 M methanolic $NH_3$ solution. The filtrate was concentrated to give N-((5-Ethyl-4,4-difluoropiperidin-3-yl)methyl)methanesulfonamide, A6 as a colourless gum (70 mg), which was taken on to the next reaction without further purification; MS m/z: 257 (M+H)$^+$.

Preparation 7:
N-((1,4-Oxazepan-6-yl)methyl)methanesulfonamide
A7

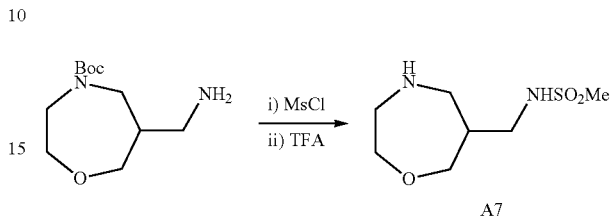

Methanesulfonyl chloride (150 μL, 1.9 mmol) was added to a solution of tert-butyl 6-(aminomethyl)-1,4-oxazepane-4-carboxylate (300 mg, 1.3 mmol) and $Et_3N$ (300 μL, 2.2 mmol) in DCM (5 mL) under $N_2$ with cooling in an ice bath. The solution was stirred at ambient temperature for 2 hours then diluted with DCM. A saturated aqueous $NaHCO_3$ solution was added, the mixture stirred for 10 minutes and the organic phase isolated with a phase separator cartridge. The filtrate was concentrated in vacuo and the residue taken up in DCM/TFA (1:1, 1 mL in total), and stirred at ambient temperature for 2 hours. The solution was concentrated in vacuo to give N-((1,4-oxazepan-6-yl)methyl)methanesulfonamide, A7 as a yellow oil (300 mg), which was taken on to the next reaction without purification, assuming the mono TFA salt was isolated; MS m/z: 209 (M+H)$^+$.

Preparation 8:
2-Methyl-6-(1H-pyrazol-4-yl)morpholine A8

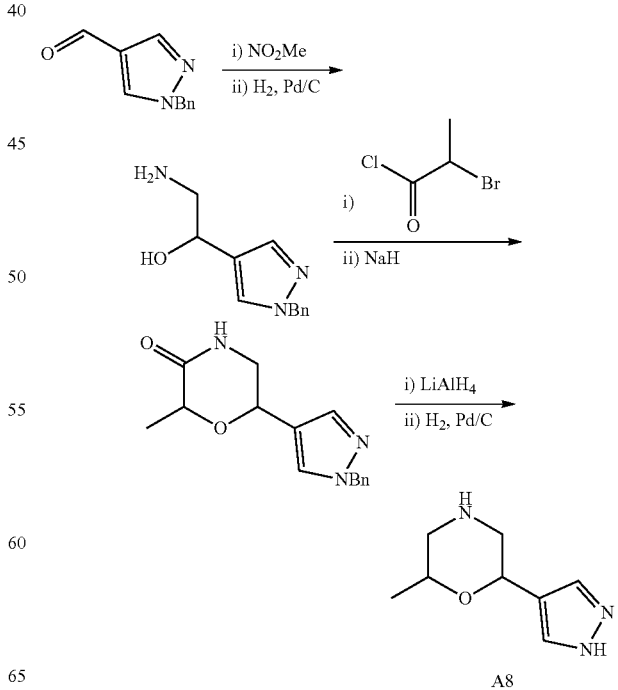

To a solution of 1-benzylpyrazole-4-carbaldehyde (2 g, 10.7 mmol) and nitromethane (7 mL, 129 mmol) cooled in an ice bath was added Et₃N (150 μL, 1.1 mmol). The mixture was stirred with cooling for 15 minutes, then at ambient temperature for 18 hours. The reaction mixture was concentrated in vacuo and the residue purified by column chromatography (silica, PE/EtOAc gradient elution) to give 1-(1-benzylpyrazol-4-yl)-2-nitro-ethanol as a colourless oil (Ig, 37%), which was taken directly on to next reaction; MS m/z: 248 (M+H)⁺

A mixture of 1-(1-benzylpyrazol-4-yl)-2-nitro-ethanol (100 mg, 0.4 mmol), Pd on C, wet, Degussa (20 mg, 0.2 mmol) in methanol (4 mL) was stirred at ambient temperature for 18 hours under a balloon of H₂. The reaction mixture was filtered and the filtrate concentrated in vacuo to give 2-amino-1-(1-benzylpyrazol-4-yl)ethanol as a colourless gum (90 mg), which was taken directly on to next reaction; MS m/z: 218 (M+H)⁺.

2-Bromopropanoyl bromide (114 mg, 0.5 mmol) was added to an ice-cold solution of 2-amino-1-(1-benzylpyrazol-4-yl)ethanol (100 mg, 0.5 mmol) and Et₃N (83 μL, 0.6 mmol) in DCM (4 mL) under N₂. The reaction mixture was stirred at ambient temperature for 1 hour. The reaction mixture was diluted with DCM, washed with a 2 M aqueous HCl solution, a saturated aqueous NaHCO₃ solution and brine. The organic phase was dried (Na₂SO₄), filtered and concentrated in vacuo to give a colourless oil. This material was taken up in THF (3 mL) and the solution cooled in an ice bath. Sodium hydride (37 mg of a 60% dispersion in mineral oil, 0.9 mmol) was added and the resulting suspension was stirred at ambient temperature for 2 hours. The reaction was quenched with MeOH then diluted with EtOAc, washed with a saturated aqueous sodium bicarbonate solution and brine. The organic phase was dried (MgSO₄), filtered and concentrated in vacuo to give a pale yellow gum (100 mg), MS m/z: 272 (M+H)⁺, that was taken directly on to next reaction without purification.

A mixture of 6-(1-benzylpyrazol-4-yl)-2-methyl-morpholin-3-one (100 mg, 0.4 mmol) and LiAlH₄ (184 μL of 2 M, 0.4 mmol) in THF (3 mL) was stirred at 60° C. for 1 hour. The resulting suspension was quenched with Na₂SO₄.10H₂O pellets and stirred for 30 minutes, then filtered. The filtrate was concentrated in vacuo and the residue taken up in MeOH (2 mL). Three drops of concentrated HCl and Pd on C, wet, Degussa (20 mg, 0.02 mmol) were added to the solution. The reaction mixture was stirred at ambient temperature under a balloon of H₂ for 18 hours. The reaction mixture was poured onto an ion-exchange cartridge, washing with methanol and eluting the product with a 2 M methanolic NH₃ solution. The filtrate was concentrated in vacuo to give 2-methyl-6-(1H-pyrazol-4-yl)morpholine A8 (23 mg), which was taken directly on to the next reaction; MS m/z: 168 (M+H)⁺.

Preparation 9: N-((5,5-Difluoropiperidin-3-yl)methyl)methanesulfonamide A9

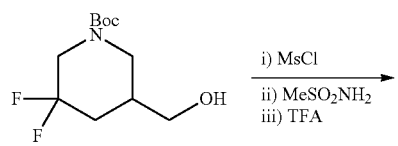

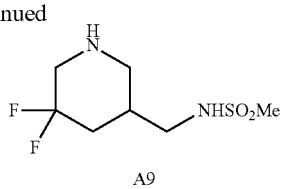

A9

Methanesulfonyl chloride (151 μL, 2 mmol) was added to an ice cold solution of tert-butyl 3,3-difluoro-5-(hydroxymethyl)piperidine-1-carboxylate (378 mg, 1.5 mmol) and Et₃N (314 μL, 2.3 mmol) in DCM (7 mL) under N₂. The solution was stirred for 18 hours, gradually warming to ambient temperature. The reaction mixture was diluted with DCM and quenched with a saturated aqueous NaHCO₃ solution. After stirring for 15 minutes, the mixture was poured onto a phase separator cartridge. The organic phase was concentrated in vacuo to give tert-butyl 3,3-difluoro-5-(((methylsulfonyl)oxy)methyl)piperidine-1-carboxylate as a colourless oil (400 mg).

A portion of this material (100 mg, 0.3 mmol) was taken up in DMF (3 mL) under N₂, and methanesulfonamide (100 mg, 1.1 mmol) and K₂CO₃ (150 mg, 1.1 mmol) added. The reaction mixture was stirred at ambient temperature for 18 hours. The resulting suspension was stirred at 80° C. for 24 hours, then diluted with water and extracted with EtOAc. The organic phase was washed with brine, dried (Na₂SO₄) and concentrated in vacuo to give tert-butyl 3,3-difluoro-5-(methylsulfonamidomethyl)piperidine-1-carboxylate as a colourless oil (150 mg).

This material was taken up in TFA (1.5 mL)/DCM (2 mL) and stirred for 2 hours at ambient temperature. The solution was concentrated in vacuo. The residue was taken up in MeOH and poured onto an ion-exchange cartridge, washing with methanol and eluting the product with a 2 M methanolic NH₃ solution. The filtrate was concentrated in vacuo to give N-((5,5-difluoropiperidin-3-yl)methyl)methanesulfonamide A9 as a colourless oil (20 mg), which was taken on to the next reaction without further purification; MS m/z: 229 (M+H)⁺.

Preparation 10: (R)—N-((6,6-Dimethylmorpholin-2-yl)methyl)methanesulfonamide A10

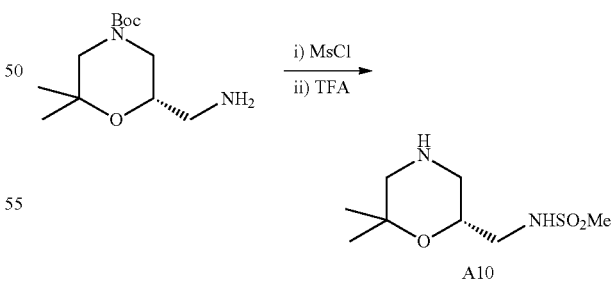

A10

Methanesulfonyl chloride (80 μL, 1 mmol) was added to a stirred suspension of tert-butyl (6S)-6-(aminomethyl)-2,2-dimethyl-morpholine-4-carboxylate (200 mg, 0.8 mmol) and Et₃N (175 μL, 1.3 mmol) in THF (10 mL) under an atmosphere of N₂ and the reaction was stirred at ambient temperature for 15 hours. DMF (2 mL) was added to aid solubility and the reaction stirred at ambient temperature for a further 3 hours. The reaction was diluted with DCM and saturated aqueous NaHCO₃ solution and the mixture was stirred for 10 minutes. The layers were separated and the aqueous layer extracted with DCM (×2). The combined organic extracts were washed with brine (×2), dried (MgSO₄), filtered and concentrated in vacuo to give a pale yellow oil (1 g); MS m/z: 323 (M+H)⁺.

This material was dissolved in DCM (5 mL) and TFA (0.5 mL) added. The reaction mixture was stirred at ambient temperature for 4 hours then concentrated in vacuo. The residue was azeotroped with DCM (×2) and diethyl ether (×2) then taken up in MeOH and passed through an ion-exchange cartridge. The cartridge was washed with MeOH/DCM mixtures and the product was eluted by washing the cartridge with 2 M NH₃ in MeOH/DCM. The filtrate was concentrated in vacuo to give N-[[(2R)-6,6-dimethylmorpholin-2-yl]methyl]methanesulfonamide A10 (122 mg, 67%) as a colourless oil, which was taken on to the next reaction without further purification; ¹H NMR (500 MHz, Chloroform-d) δ 4.65 (s, 1H), 3.87-3.82 (m, 1H), 3.22 (ddd, 1H), 3.03-2.99 (m, 1H), 2.99 (s, 3H), 2.87 (ddd, 1H), 2.67 (d, 1H), 2.59 (d, 1H), 2.51 (dd, 1H), 1.32 (s, 3H), 1.16 (s, 3H); MS m/z: 223 (M+H)⁺.

Preparation 11: N-((4-Fluoropiperidin-3-yl)methyl)methanesulfonamide A11

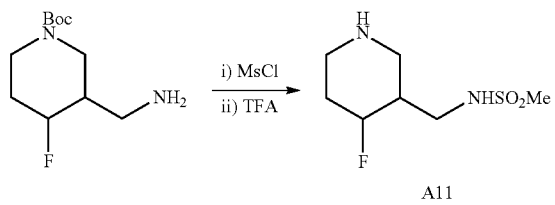

A11

Methanesulfonyl chloride (100 μL, 1.3 mmol) was added to a solution of tert-butyl 3-(aminomethyl)-4-fluoro-piperidine-1-carboxylate (250 mg, 1.1 mmol) and Et₃N (200 μL, 1.4 mmol) in DCM (3 mL) with cooling in an ice bath. The solution was stirred at ambient temperature for 2 hours then diluted with DCM. The mixture was washed with a 2 M aqueous HCl solution, a saturated aqueous NaHCO₃ solution and brine. The organic phase was dried (Na₂SO₄), filtered and concentrated in vacuo.

The residue was taken up in DCM (2 mL) and TFA (2 mL, 26 mmol), stirred at ambient temperature for 1 hour then concentrated in vacuo. The residue was diluted in MeOH and poured onto an ion-exchange cartridge, washing with methanol and eluting the product with a 2 M methanolic NH₃ solution. The filtrate was concentrated in vacuo to give N-((4-fluoropiperidin-3-yl)methyl)methanesulfonamide A11, which was used without further purification.

Preparation 12: 2-(Methylsulfonyl)-4,5,6,7-tetrahydro-2H-pyrazolo[3,4-c]pyridine A12

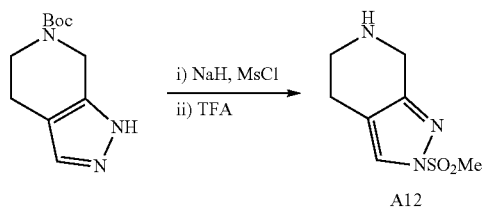

A12

NaH (79 mg of a 60% dispersion in mineral oil, 2 mmol) was added in one portion to a solution of tert-butyl 1,4,5,7-tetrahydropyrazolo[3,4-c]pyridine-6-carboxylate (400 mg, 1.8 mmol) in THF (7 mL) under N₂ with cooling in an ice bath. After fifteen minutes, methanesulfonyl chloride (166 μL, 2.2 mmol) was added to the solution. The reaction mixture was stirred for 18 hours, with the temperature rising to ambient, then diluted with EtOAc and washed with a 2 M aqueous NaOH solution and brine. The organic phase was dried (Na₂SO₄) and concentrated in vacuo.

The residue was taken up in DCM (3 mL) and TFA (2 mL) and the solution stirred for 2 hours at ambient temperature, then concentrated in vacuo. The residue was diluted in MeOH and poured onto an ion-exchange cartridge, washing with methanol and eluting the product with a 2 M methanolic NH₃ solution. The filtrate was concentrated in vacuo to give 2-(methylsulfonyl)-4,5,6,7-tetrahydro-2H-pyrazolo[3,4-c]pyridine A12 as a colourless oil (240 mg, 67%), which was taken on to the next reaction without further purification; MS m/z: 202 (M+H)⁺.

Preparation 13: Imino(methyl)(piperidin-3-ylmethyl)-λ⁶-sulfanone A13

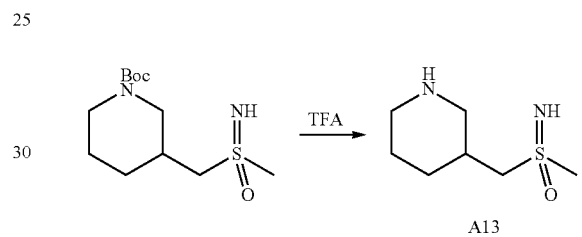

A13 tert-Butyl 3-[(methyl sulfonimidoyl)methyl]piperidine-1-carboxylate (600 mg, 2.2 mmol) [see preparation 35] was dissolved in DCM (3 mL) and TFA (1.7 mL, 22 mmol) added. The mixture was stirred overnight at ambient temperature then concentrated in vacuo. The residue was taken up in MeOH and loaded on to an ion-exchange cartridge, eluting the product with a 2 M methanolic ammonia solution. The filtrate was concentrated in vacuo to give imino(methyl)(piperidin-3-ylmethyl)-λ⁶-sulfanone A13 (250 mg, 65%); ¹H NMR (500 MHz, Methanol-d₄) δ 3.34-3.24 (m, 1H), 3.19-3.10 (m, 2H), 3.10-3.07 (m, 3H), 3.05-2.97 (m, 1H), 2.60 (ddd, 1H), 2.52-2.43 (m, 1H), 2.30-2.18 (m, 1H), 2.08 (ddtd, 1H), 1.75 (dq, 1H), 1.61 (dtq, 1H), 1.37 (dtd, 1H).

Preparation 14: 2-(1H-Pyrazol-4-yl)piperazine A14

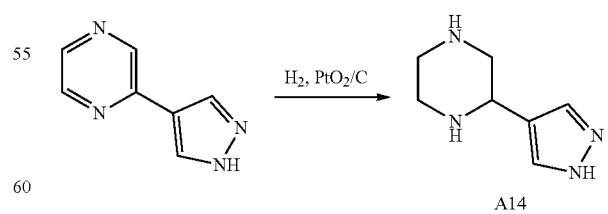

A14

A mixture of 2-(1H-pyrazol-4-yl)pyrazine (400 mg, 2.7 mmol) and PtO₂ (100 mg, 0.4 mmol) in MeOH (15 mL) was shaken at ambient temperature under a 60 psi H₂ pressure for 18 hours. The reaction mixture was filtered and the filtrate concentrated in vacuo to give 2-(1H-pyrazol-4-yl)piperazine A14 as a colourless oil, which was taken directly on to the next reaction without purification; MS m/z: 153 (M+H)+.

Preparation 15: N-((4,4-Difluoro-5,5-dimethylpiperidin-3-yl)methyl)methanesulfonamide A15

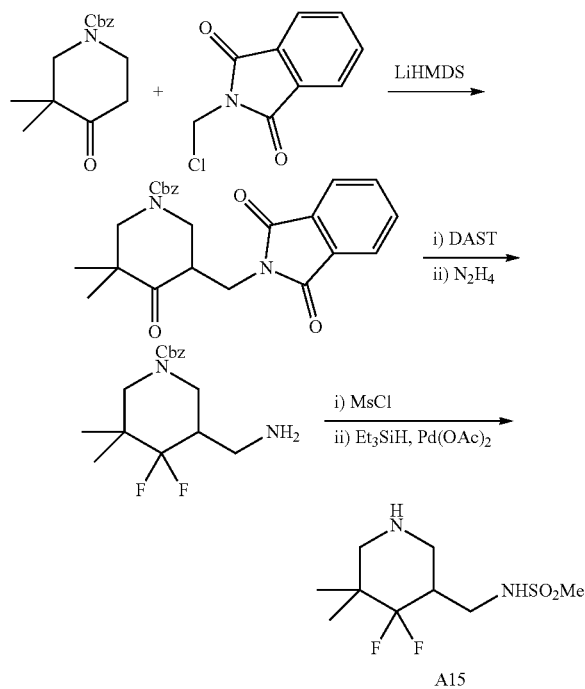

A15

(Bis(trimethylsilyl)amino)lithium (2.4 mL of a 1 M solution in THF, 2.4 mmol) was added dropwise to a solution of benzyl 3,3-dimethyl-4-oxo-piperidine-1-carboxylate (500 mg, 2 mmol) in THF (7 mL) at −78° C. under N₂. After 90 minutes, a solution of 2-(chloromethyl)isoindoline-1,3-dione (560 mg, 3 mmol) in THF (2 mL) was added. The reaction mixture was stirred for 1 hour then quenched by the addition of saturated aqueous NH₄Cl solution (~2 mL). The reaction mixture was diluted with EtOAc, washed with a saturated aqueous sodium bicarbonate solution and brine. The organic phase was dried (MgSO₄), filtered and concentrated in vacuo. The residue was purified by column chromatography (silica, PE/EtOAc gradient elution) and then by reverse phase chromatography (C18, MeCN/water—0.1% ammonium hydroxide as eluent) to give benzyl 5-[(1,3-dioxoisoindolin-2-yl)methyl]-3,3-dimethyl-4-oxo-piperidine-1-carboxylate as a colourless oil (180 mg, 21%); MS m/z: 421 (M+H)+.

DAST (450 μL, 3.4 mmol) was added dropwise to a solution of benzyl 5-[(1,3-dioxoisoindolin-2-yl)methyl]-3,3-dimethyl-4-oxo-piperidine-1-carboxylate (150 mg, 0.4 mmol) in DCM (3 mL) under N₂ with cooling in an ice bath. After 5 minutes, the ice bath was removed and the solution stirred at ambient temperature for 22 hours. A further 0.45 mL of DAST were added to the reaction mixture. After 16 hours the reaction was quenched by the careful addition of MeOH. The reaction mixture was concentrated in vacuo and the residue purified by column chromatography (silica, PE/EtOAc gradient elution) to give benzyl 5-((1,3-dioxoisoindolin-2-yl)methyl)-4,4-difluoro-3,3-dimethylpiperidine-1-carboxylate (60 mg, 34%); MS m/z: 443 (M+H)+.

The residue was taken up in EtOH (2.8 mL) and hydrazine hydrate (30 μL, 0.6 mmol) was added. The mixture was stirred under reflux for 16 hours. The resulting suspension was diluted with methanol and loaded onto an ion-exchange cartridge, washing with MeOH and eluting the product with 2 M methanolic NH₃ solution. The filtrate was concentrated in vacuo to give the product as a pale yellow gum; MS m/z: 313 (M+H)+.

This material was dissolved in DCM (5 mL) under N₂. Methanesulfonyl chloride (18 μL, 0.2 mmol) and Et₃N (40 μL, 0.3 mmol) were added with cooling in an ice bath. After stirring for 5 minutes, the ice bath was removed and the solution stirred at ambient temperature for 2 hours. The solution was diluted with DCM and washed with saturated aqueous NaHCO₃ solution. The organic phase was dried (Na₂SO₄), filtered and concentrated in vacuo. The residue was taken up in DCM (3 mL). Pd(OAc)₂ (20 mg, 0.1 mmol), Et₃N (100 μL, 0.7 mmol) and triethylsilane (250 μL, 1.6 mmol) were added and the reaction mixture stirred at ambient temperature for 1 hour. The solution was poured onto an ion-exchange cartridge, washing with MeOH then eluting the product with a 2 M methanolic NH₃ solution. The filtrate was concentrated in vacuo to give N-((4,4-difluoro-5,5-dimethylpiperidin-3-yl)methyl)methanesulfonamide A15 as a colourless gum (50 mg), which was taken on to the next reaction without further purification; MS m/z: 257 (M+H)+.

Preparation 16: (S)—N-((1-Methyl-6-oxopiperazin-2-yl)methyl)methanesulfonamide A16

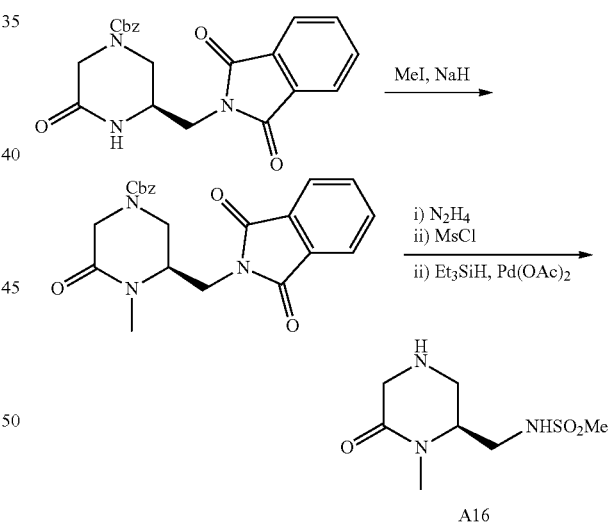

A16

NaH (30 mg of a 60% dispersion in mineral oil, 0.75 mmol) was added to a solution of benzyl (3R)-3-[(1,3-dioxoisoindolin-2-yl)methyl]-5-oxo-piperazine-1-carboxylate (200 mg, 0.5 mmol) in DMF (2 mL) under N₂ with cooling in an ice bath. After 20 minutes MeI (45 μL, 0.7 mmol) was added and the reaction mixture stirred for 18 hours, with the temperature rising to ambient. The reaction mixture was diluted with EtOAc and washed with a saturated aqueous sodium bicarbonate solution and brine. The organic phase was dried (Na₂SO₄), filtered and concentrated in vacuo. The residue was purified by column chromatography (silica, DCM/EtOAc elution) to give benzyl (R)-3-

((1,3-dioxoisoindolin-2-yl)methyl)-4-methyl-5-oxopiperazine-1-carboxylate as a colourless oil (13 mg, 6%); MS m/z: 408 (M+H)+.

This material was taken up in EtOH (3 mL) and hydrazine hydrate (1 drop) added. The reaction mixture was heated under reflux for 2 hours then cooled to ambient temperature. The solution was loaded onto an ion-exchange cartridge, washing with methanol and eluting the product with a 2 M methanolic $NH_3$ solution. The filtrate was concentrated in vacuo to give a yellow gum, which was taken up in DCM (2 mL). $Et_3N$ (45 µL, 0.3 mmol) then methanesulfonyl chloride (15 µL, 0.2 mmol) were added and the reaction mixture stirred at ambient temperature for 2 hours. The residue was diluted with DCM and a saturated aqueous $NaHCO_3$ solution. After 5 minutes stirring, the organic phase was isolated using a phase separation cartridge then concentrated in vacuo; MS m/z: 356 (M+H)+.

The residue was taken up in DCM (2 mL) and $Et_3SiH$ (50 µL, 0.3 mmol), $Et_3N$ (45 µL, 0.3 mmol) and $Pd(OAc)_2$ (4 mg, 0.02 mmol) were added. The resulting suspension was stirred at ambient temperature for 3 hours then diluted with methanol (3 mL) and loaded onto an ion-exchange cartridge. The cartridge was washed with methanol and the product eluted with a 2 M methanolic $NH_3$ solution. The filtrate was concentrated in vacuo to give a brown gum (~10 mg), containing (S)—N-((1-methyl-6-oxopiperazin-2-yl)methyl)methanesulfonamide A16; MS m/z: 222 (M+H)+. This material was taken directly on to the next reaction without further purification.

Preparation 17: N—((S)-Morpholin-2-ylmethyl)methanesulfonimidamide A17

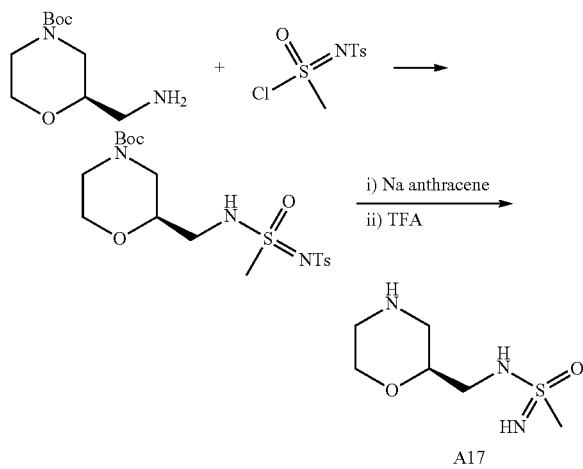

N-Tosylmethanesulfonimidoyl chloride (297 mg, 3.7 mmol) was added to a solution of tert-butyl (2R)-2-(aminomethyl)morpholine-4-carboxylate (637 mg, 3 mmol) and $Et_3N$ (868 µL, 6 mmol) in DCM (15 mL) under $N_2$ with cooling in an ice bath. The ice bath was removed and the reaction mixture was stirred at ambient temperature for 18 hours. The reaction mixture was diluted with DCM, washed with a saturated aqueous sodium bicarbonate solution and brine. The organic phase was dried ($MgSO_4$), filtered and concentrated in vacuo. The residue was purified by column chromatography (silica, PE/EtOAc elution) to give tert-butyl (2S)-2-[[[S-methyl-N-(p-tolyl sulfonyl)sulfonimidoyl] amino]methyl]morpholine-4-carboxylate as a colourless oil (400 mg, 30%); MS m/z: 446 (M−H)−.

This material was dissolved in THF (10 mL) under argon. A sodium anthracene solution was freshly prepared by the addition of sodium pellets (270 mg, 12 mmol) to a suspension of anthracene (2.14 g, 12 mmol) in THF (30 mL) under argon. The suspension was stirred at ambient temperature for 3 hours to give a dark blue/green solution. This solution was added dropwise to the tert-butyl (2S)-2-[[[S-methyl-N-(p-tolylsulfonyl)sulfonimidoyl]amino]methyl]morpholine-4-carboxylate solution until a blue colour persisted. After 15 minutes, the reaction mixture was quenched with a saturated aqueous $NH_4Cl$ solution and extracted with EtOAc (×2). The combined organics were washed with brine and dried ($Na_2SO_4$) then filtered and concentrated in vacuo. The residue was purified by column chromatography (silica, (EtOAc+10% MeOH)/PE, 5% to 100% gradient elution). Fractions containing product were combined and concentrated in vacuo. The residue was taken up in DCM (1 mL) and treated with TFA (0.5 mL). After stirring at ambient temperature for 3 hours, the reaction mixture was concentrated in vacuo to give N—((S)-morpholin-2-ylmethyl)methanesulfonimidamide A17 as a yellow oil (150 mg), which was taken on to the next reaction without further purification; $^1H$ NMR (500 MHz, DMSO-$d_6$) δ 4.03 (m, 1H), 3.82 (m, 1H), 3.72 (m, 1H), 3.42 (s, 3H), 3.33-3.17 (m, 4H), 2.99 (m, 1H), 2.83 (m, 1H).

Preparation 18: N-(2-(Piperidin-3-yl)propan-2-yl)methanesulfonamide A18

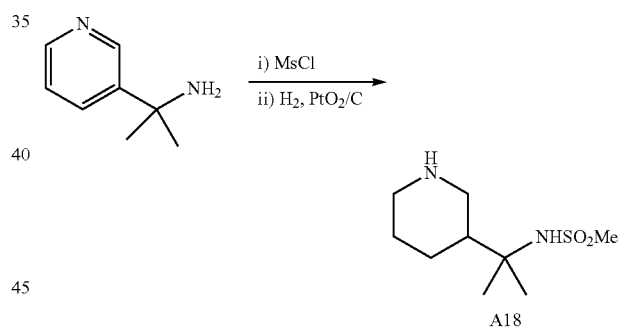

Methanesulfonyl chloride (200 µL, 2.6 mmol) was added to a solution of 2-(3-pyridyl)propan-2-amine (250 mg, 1.8 mmol) and $Et_3N$ (400 µL, 2.9 mmol) in DCM (4 mL) with cooling in an ice bath. After 5 minutes, the ice bath was removed and the solution stirred at ambient temperature for 2 hours. The solution was diluted with DCM and a saturated aqueous $NaHCO_3$ solution was added. The mixture was stirred at ambient temperature for 5 minutes. The organic phase was separated using a phase separation cartridge and concentrated in vacuo to give a pale yellow gum (350 mg, 90%), which was used directly in next reaction; MS m/z: 215 (M+H)+.

A mixture of N-[1-methyl-1-(3-pyridyl)ethyl]methanesulfonamide (350 mg, 1.6 mmol), $PtO_2$ (100 mg, 0.4 mmol) and HCl (5 mL of 3 M solution in MeOH, 15 mmol) was shaken for 18 hours under a 60 psi $H_2$ pressure. The reaction mixture was filtered and the filtrate concentrated in vacuo to give N-(2-(piperidin-3-yl)propan-2-yl)methanesulfonamide A18 as a colourless oil (400 mg, 98%), which was taken on

Preparation 19: N-((5-Methoxypiperidin-3-yl)methyl)methanesulfonamide A19

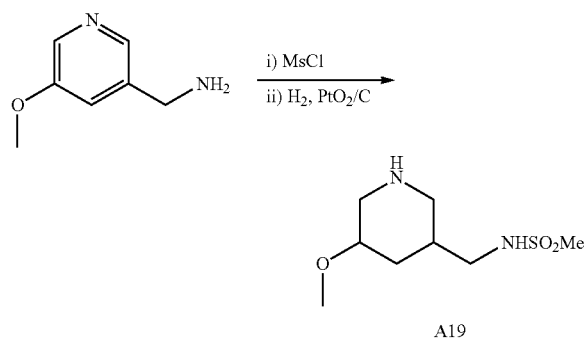

Methanesulfonyl chloride (400 µL, 5.2 mmol) was added dropwise to a solution of (5-methoxy-3-pyridyl)methanamine (500 mg, 3.6 mmol) in DCM (10 mL) under $N_2$ with cooling in an ice bath. The reaction mixture was stirred at ambient temperature for 2 hours. The resulting suspension was diluted with DCM and a saturated aqueous $NaHCO_3$ solution. After stirring for 5 minutes, the organic phase was isolated using a phase separation cartridge and concentrated in vacuo to give N-[(5-methoxy-3-pyridyl)methyl]methanesulfonamide as a brown oil (770 mg); MS m/z: 217 (M+H)$^+$ which was taken directly on to next reaction.

A mixture of N-[(5-methoxy-3-pyridyl)methyl]methanesulfonamide (300 mg, 1.4 mmol), $PtO_2$ (150 mg, 0.6 mmol) and HCl (15 mL of 3 M solution in MeOH, 45 mmol) was shaken for 18 hours under a 60 psi $H_2$ pressure. The reaction mixture was filtered and the filtrate concentrated in vacuo to give N-((5-methoxypiperidin-3-yl)methyl)methanesulfonamide A19 as a yellow oil, which was taken directly on to next reaction without purification (assuming the mono HCl salt); MS m/z: 223 (M+H)$^+$.

Preparation 20: N-((2-Methylpiperidin-3-yl)methyl)methanesulfonamide A20

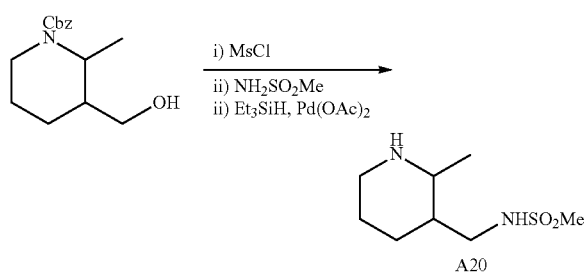

Et$_3$N (400 µL, 2.9 mmol) then methanesulfonyl chloride (200 µL, 2.6 mmol) were added to a solution of benzyl 3-(hydroxymethyl)-2-methyl-piperidine-1-carboxylate (500 mg, 1.9 mmol) in DCM (10 mL) and the mixture was stirred at ambient temperature for 18 hours. The solution was diluted with DCM and saturated aqueous NaHCO$_3$ solution. After stirring for 5 minutes, the organic phase was isolated using a phase separation cartridge and concentrated in vacuo; MS m/z: 342 (M+H)$^+$. The residue was taken up in DMF (5 mL). Methanesulfonamide (600 mg, 6.3 mmol) and K$_2$CO$_3$ (1.0 g, 7.2 mmol) were added to the solution which was stirred at 80° C. for 20 hours. The resulting suspension was diluted with DCM and water. After stirring for 5 minutes, the organic phase was isolated using a phase separation cartridge and concentrated in vacuo. The residue was purified by column chromatography (silica, PE/EtOAc elution) to give benzyl 3-(methanesulfonamidomethyl)-2-methyl-piperidine-1-carboxylate as a pale yellow oil (210 mg, 33% over two steps); MS m/z: 341 (M+H)$^+$.

A suspension of benzyl 3-(methanesulfonamidomethyl)-2-methyl-piperidine-1-carboxylate (210 mg, 0.6 mmol), Et$_3$SiH (300 µL, 1.9 mmol), Pd(OAc)$_2$ (80 mg, 0.36 mmol) and Et$_3$N (200 µL, 1.4 mmol) in DCM (4 mL) was stirred at ambient temperature for 2 hours. The resulting solution was diluted with MeOH and loaded on to an ion-exchange cartridge, washing with MeOH and eluting the product with a 2 M methanolic NH$_3$ solution. The filtrate was concentrated in vacuo to give N-((2-methylpiperidin-3-yl)methyl) methanesulfonamide A20 as a brown oil (120 mg, 97%), which was taken on to the next reaction without further purification; MS m/z: 207 (M+H)$^+$.

Preparation 21: N-(2-Azaspiro[4.4]nonan-7-yl)methanesulfonamide A21

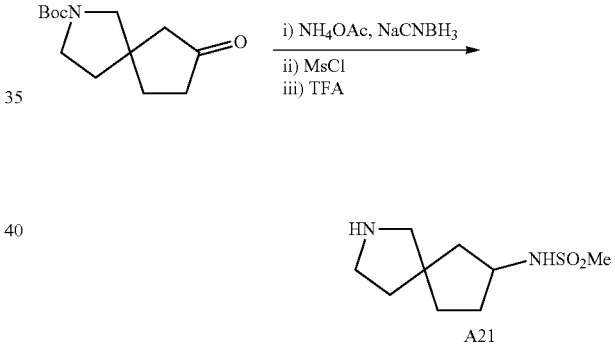

tert-Butyl 8-oxo-2-azaspiro[4.4]nonane-2-carboxylate (100 mg, 0.4 mmol) and ammonium acetate (300 mg, 3.9 mmol) were stirred in methanol (2 mL) at ambient temperature for 3 hours. Sodium cyanoborohydride (26 mg, 0.4 mmol) was added and the mixture stirred at ambient temperature for 18 hours. The solution was loaded onto an ion-exchange cartridge, washing with methanol and eluting the product with a methanolic ammonia solution. The filtrate was concentrated in vacuo to give a colourless oil (60 mg). This material was taken up in DCM (3 mL) and Et$_3$N (70 µL, 0.5 mmol) then methanesulfonyl chloride (30 µL, 0.4 mmol) were added. After 1 hour, the solution was diluted with DCM and a saturated aqueous NaHCO$_3$ solution. After 2 minutes stirring, the organic phase was isolated using a phase separation cartridge and concentrated in vacuo. The residue was taken up in TFA (500 µL, 6.5 mmol) and DCM (3 mL) and stirred at ambient temperature for 18 hours, then concentrated in vacuo to give N-(2-azaspiro[4.4]nonan-7-yl)methanesulfonamide A21 as a colourless oil, which was taken on to the next reaction (assuming mono TFA salt); MS m/z: 219 (M+H)$^+$.

Preparation 22: N-((3-Fluoropiperidin-3-yl)methyl)methanesulfonamide A22

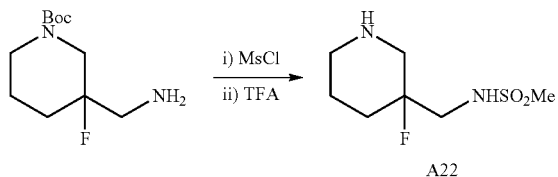

Methanesulfonyl chloride (82 μL, 1.1 mmol) was added to a solution of tert-butyl 3-(aminomethyl)-3-fluoro-piperidine-1-carboxylate (206 mg, 0.9 mmol) and Et₃N (185 μL, 1.3 mmol) in DCM (7 mL) under N₂. The reaction mixture was stirred at ambient temperature for 18 hours. The reaction mixture was diluted with DCM and a saturated aqueous NaHCO₃ solution. After 10 minutes the mixture was passed through a phase separator cartridge. The organic phase was concentrated in vacuo and the residue taken up in DCM (2 mL)/TFA (2 mL). After stirring for 2 hours at ambient temperature, the mixture was concentrated in vacuo to give N-((3-fluoropiperidin-3-yl)methyl)methanesulfonamide A22, which was taken directly on to the next reaction without purification (assuming the mono TFA salt); ¹H NMR (500 MHz, CDCl₃) δ 3.31-3.27 (m, 2H), 2.96 (m, 1H), 2.92 (s, 3H), 2.86 (m, 1H), 2.78-2.71 (m, 1H), 2.62 (m, 1H), 1.95 (m, 1H), 1.75-1.45 (masked, 3H).

Preparation 23: N-((5-(Trifluoromethyl)piperidin-3-yl)methyl)methanesulfonamide A23

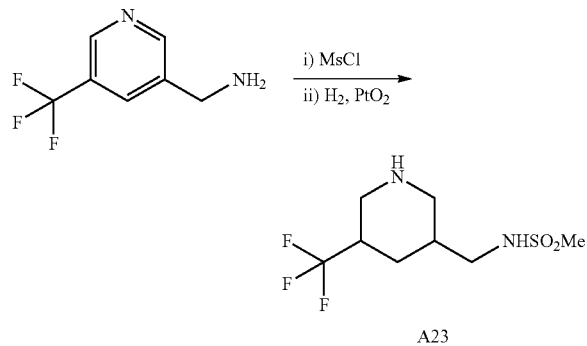

A round-bottomed flask was charged with [5-(trifluoromethyl)-3-pyridyl]methanamine (358 mg, 2 mmol), Et₃N (566 μL, 4 mmol) in DCM (7 mL) under N₂. The mixture was then cooled to 0° C. and methanesulfonyl chloride (315 μL, 4 mmol) added dropwise. The mixture was stirred at that temperature for 10 minutes then quenched with a few drops of sat NaHCO₃, and stirred for 5 minutes. The mixture was passed through a phase separator cartridge and the organic phase concentrated in vacuo. The residue was purified by reverse phase chromatography (C18, MeCN/water/0.05% TFA as eluent). The product fractions were concentrated in vacuo to give N-[[5-(trifluoromethyl)-3-pyridyl]methyl]methanesulfonamide as a white solid (32 mg, 6%); ¹H NMR (500 MHz, DMSO-d₆) δ 8.94-8.88 (m, 1H), 8.88-8.83 (m, 1H), 8.21-8.08 (m, 1H), 7.71 (t, 1H), 4.34 (d, 2H), 2.96 (s, 3H).

A suspension of N-[[5-(trifluoromethyl)-3-pyridyl]methyl]methanesulfonamide (32 mg, 0.14 mmol) and PtO₂ (50 mg, 0.2 mmol) in HCl (1 mL of 3 M, 3 mmol) and MeOH (761 L) was stirred at ambient temperature for 18 hours under a 60 psi H₂ pressure. The catalyst was filtered off and the solvent removed in vacuo. The residue was taken up in MeOH and passed through an ion-exchange cartridge, eluting the product with a methanolic ammonia solution. The filtrate was concentrated in vacuo to give N-((5-(trifluoromethyl)piperidin-3-yl)methyl)methanesulfonamide A23 as a white solid (23 mg, 64%); MS m/z: 261 (M+H)⁺.

Preparation 24: N-[Ethyl(oxo)[(3S)-piperidin-3-ylmethyl]-λ⁶-sulfanylidene]-2,2,2-trifluoroacetamide A24

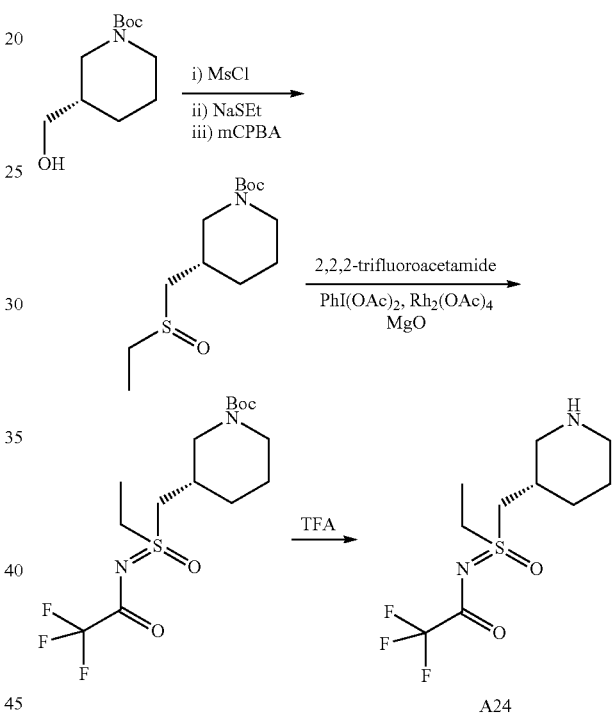

A round-bottomed flask was charged with tert-butyl (3S)-3-(hydroxymethyl)piperidine-1-carboxylate (1.1 g, 5 mmol) and Et₃N (1.4 mL, 10 mmol) in DCM (11 mL) under N₂. The mixture was then cooled to 0° C. and methanesulfonyl chloride (791 μL, 10 mmol) added dropwise. The mixture was stirred for 10 minutes then allowed to warm to ambient temperature and stirred for 1 hour. The reaction was quenched by the addition of saturated aqueous NaHCO₃ solution, and stirred for 5 minutes, then passed through a phase separator cartridge. The organic layer was concentrated in vacuo to give tert-Butyl (3S)-3-(methylsulfonyloxymethyl)piperidine-1-carboxylate (1.4 g), which was taken directly on to the next reaction.

tert-Butyl (3S)-3-(methylsulfonyloxymethyl)piperidine-1-carboxylate (500 mg, 1.7 mmol) was taken up in DMF (5 mL), and ethylsulfanylsodium (538 mg, 5 mmol) was added. The reaction was stirred at 130° C. in a sealed tube overnight. The reaction mixture was cooled to ambient temperature then filtered though a pad of Celite. The filtrate was concentrated in vacuo and the residue purified by column chromatography (silica, EtOAc/PE 0-50% gradient elution) to give tert-butyl (3S)-3-(ethylsulfanylmethyl)piperidine-1-carboxylate (150 mg, 35%).

mCPBA (130 mg, 0.6 mmol) was added portionwise to an ice/brine cold solution (−15° C.) of tert-butyl (3S)-3-(ethylsulfanylmethyl)piperidine-1-carboxylate (150 mg, 0.6 mmol) in DCM (3 mL). After the addition was complete, the reaction was quenched by the addition of saturated aqueous $Na_2S_2O_3$ solution. After stirring for 1 hour, the mixture was passed through a phase separator cartridge, and the organic phase was concentrated in vacuo to give tert-butyl (3S)-3-(ethyl sulfinylmethyl)piperidine-1-carboxylate (150 mg, 91%) that was used directly in the next reaction; MS m/z: 276 (M+H)$^+$.

Rhodium (II) acetate (12 mg, 0.03 mmol) was added to a solution of tert-butyl (3S)-3-(ethylsulfinylmethyl)piperidine-1-carboxylate (150 mg, 0.5 mmol), 2,2,2-trifluoroacetamide (123 mg, 1 mmol), diacetoxyiodobenzene (263 mg, 0.8 mmol) and MgO (88 mg, 2 mmol) in DCM (6 mL) and the mixture stirred at ambient temperature overnight. The reaction mixture was filtered through a pad of Celite and the filtrate concentrated in vacuo to a colourless oil (200 mg). This material was taken up in DCM (2.2 mL) and TFA (0.8 mL) was added. The mixture was stirred for 16 hours at ambient temperature then concentrated in vacuo. The residue, N-[ethyl(oxo)[(3S)-piperidin-3-ylmethyl]-$\lambda^6$-sulfanylidene]-2,2,2-trifluoroacetamide A24 (120 mg), was taken on to the next reaction without purification (assuming the mono TFA salt); MS m/z: 287 (M+H)$^+$.

Preparation 25: N-((4-Fluoro-4-methylpiperidin-3-yl)methyl)methanesulfonamide A25

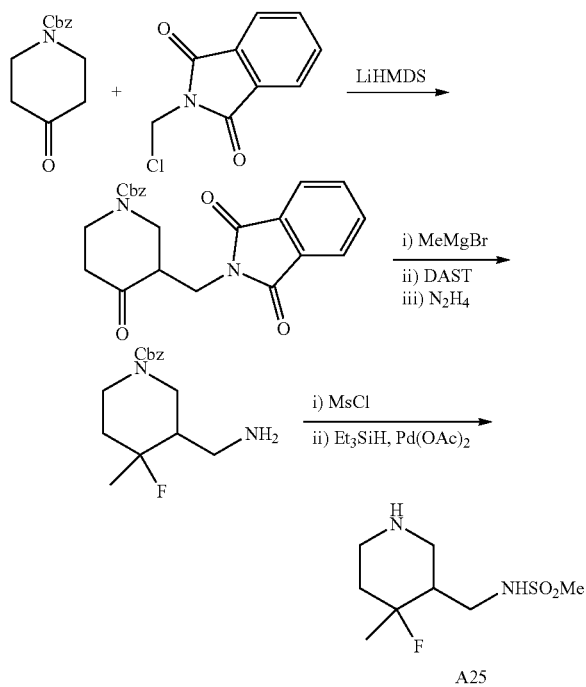

A round-bottomed flask was charged with benzyl 3-[(1,3-dioxoisoindolin-2-yl)methyl]-4-oxo-piperidine-1-carboxylate (2.58 g, 6 mmol) in THF (58 mL). The reaction was cooled to 0° C. and MeMgBr (2.4 mL of 3 M, 7 mmol) added dropwise. After 2 hours, an additional MeMgBr (1 mL of 3 M, 2.9 mmol) was added and the mixture stirred for 16 hours. The reaction was quenched by the addition of saturated aqueous $NH_4Cl$ (3 mL) and the mixture concentrated in vacuo. The residue was extracted with DCM (×3). The combined organic extracts were washed with brine, dried ($MgSO_4$), filtered and concentrated in vacuo. The residue was purified by column chromatography (silica, 0 to 100% EtOAc/PE gradient elution) to give benzyl 3-[(1,3-dioxoisoindolin-2-yl)methyl]-4-hydroxy-4-methyl-piperidine-1-carboxylate as a colourless foam (1.28 g, 52%), which was taken directly on to the next reaction; MS m/z: 409 (M+H)$^+$.

Benzyl 3-[(1,3-dioxoisoindolin-2-yl)methyl]-4-hydroxy-4-methyl-piperidine-1-carboxylate (1.28 g, 3 mmol) was dissolved in DCM (25 mL) under $N_2$. The solution was cooled to 0° C., and DAST (414 µL, 3 mmol) added dropwise. The reaction was stirred at 0° C. for 2 hours then quenched by the addition of MeOH (2 mL) and concentrated in vacuo. The residue was diluted with DCM and the organics were washed with brine, dried ($MgSO_4$), filtered and concentrated in vacuo. The residue was purified by column chromatography (silica, 0 to 100% EtOAc/PE gradient elution) to give 340 mg of a mixture of the desired product and the fluorine elimination by-product. This mixture was taken directly on to the next reaction.

A mixture of crude benzyl 3-[(1,3-dioxoisoindolin-2-yl)methyl]-4-fluoro-4-methyl-piperidine-1-carboxylate (340 mg, 0.8 mmol) and hydrazine hydrate (314 µL, 3 mmol) in EtOH (15 mL) was stirred under reflux for 16 hours. The resulting suspension was diluted with MeOH and loaded onto an ion-exchange cartridge washing with MeOH then eluting the product with 2 M methanolic $NH_3$ solution. The filtrate was concentrated in vacuo to give benzyl 3-(aminomethyl)-4-fluoro-4-methyl-piperidine-1-carboxylate as a pale yellow gum (100 mg), which was taken on directly to next reaction; MS m/z: 281 (M+H)$^+$.

A round-bottomed flask was charged with benzyl 3-(aminomethyl)-4-fluoro-4-methyl-piperidine-1-carboxylate (100 mg, 0.35 mmol), $Et_3N$ (96 µL, 0.7 mmol) in DCM (2 mL) under $N_2$. The mixture was cooled to 0° C. and methanesulfonyl chloride (54 µL, 0.7 mmol) added dropwise. The mixture was stirred for 10 minutes then allowed to warm to ambient temperature and stirred for a further 10 minutes. The reaction was quenched by the addition of saturated aqueous $NaHCO_3$ solution, stirred for 5 minutes then passed through a phase separator cartridge. The filtrate was concentrated in vacuo to give a brown oil that was taken directly on to next reaction (120 mg); MS m/z: 359 (M+H)$^+$.

Benzyl 4-fluoro-3-(methanesulfonamidomethyl)-4-methyl-piperidine-1-carboxylate (120 mg, 0.3 mmol) was taken up in DCM (2 mL). $Pd(OAc)_2$ (34 mg, 0.15 mmol), $Et_3N$ (170 µL, 1 mmol) and $Et_3SiH$ (390 µL, 2 mmol) were added and the reaction mixture stirred at ambient temperature for 1 hour. The reaction mixture was loaded onto an ion-exchange cartridge, washing with MeOH then eluting the product with 2 M methanolic $NH_3$ solution. The filtrate was concentrated in vacuo to give N-((4-fluoro-4-methylpiperidin-3-yl)methyl)methanesulfonamide A25 as a brown gum (60 mg), which was taken on to the next reaction without further purification; MS m/z: 225 (M+H)$^+$.

Preparation 26: 3-(3,3-Difluoroazetidin-1-yl)piperidine A26

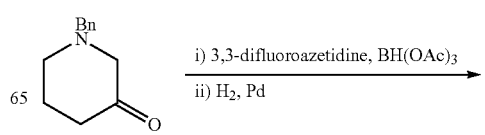

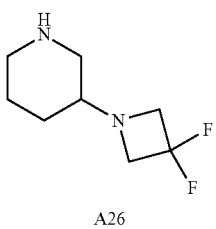

A26

A microwave vial was charged with 1-benzylpiperidin-3-one hydrate HCl salt (100 mg, 0.4 mmol), 3,3-difluoroazetidine hydrochloride (80 mg, 0.6 mmol) and AcOH (47 μL, 0.8 mmol) in THF (1 mL). The resulting suspension was stirred at 50° C. until a clear solution was obtained, then NaBH(OAc)$_3$ (261 mg, 1.2 mmol) was added. The reaction mixture was stirred at 50° C. for 30 minutes then allowed to cool to ambient temperature and quenched by the addition of saturated aqueous NaHCO$_3$ solution. The mixture was stirred for 10 minutes then extracted with DCM (×3). The combined organic extracts were dried (MgSO$_4$), filtered and concentrated in vacuo to give 1-benzyl-3-(3,3-difluoroazetidin-1-yl)piperidine, which was used directly in the next step.

The residue was dissolved in methanol (2 mL) and 2 drops of concentrated HCl (~15 mg, ~0.4 mmol) were added. The flask was degassed and filled with N$_2$ (×3 vacuum-N$_2$ cycles) and Pd on C, wet, Degussa 10% w/w (44 mg, 0.1 mmol) was added in one portion. The flask was equipped with a hydrogen balloon and filled (×3 vacuum-hydrogen cycles). The reaction was vigorously stirred overnight at ambient temperature. The mixture was filtered though a pad of Celite and the filtrate concentrated in vacuo to give 3-(3,3-difluoroazetidin-1-yl)piperidine A26, which was used directly in the next reaction (assuming quantitative conversion to the HCl salt); MS m/z: 177 (M+H)$^+$.

Preparation 27: 8a-Methyltetrahydro-1H-oxazolo[3,4-a]pyrazin-3(5H)-one A27

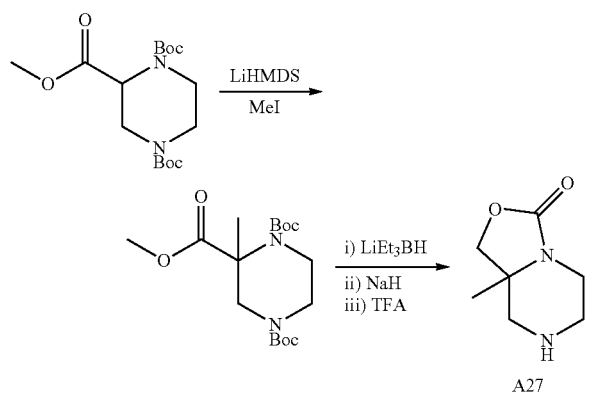

A27

LiHMDS (9.9 mL of 1 M, 9.9 mmol) was added to a solution of 1,4-di-tert-butyl 2-methyl piperazine-1,2,4-tricarboxylate (2.0 g, 5.8 mmol) in THF (30 mL) at −78° C. under N$_2$. After 45 minutes, iodomethane (615 μL, 9.9 mmol) in THF (5 mL) was added slowly. The mixture was allowed to warm slowly to ambient temperature and stirred overnight. The reaction mixture was partitioned between DCM and saturated aqueous NH$_4$Cl solution. The organic phase was dried, filtered and concentrated in vacuo. The residue was purified by column chromatography (silica, DCM/MeOH elution) to give 1,4-di-tert-butyl 2-methyl 2-methylpiperazine-1,2,4-tricarboxylate as a colourless oil (1.5 g, 72%); MS m/z: 359 (M+H)$^+$.

Lithium triethyl borohydride (10.5 mL of 1M, 10.5 mmol) was slowly added to a solution of 1,4-di-tert-butyl 2-methyl 2-methylpiperazine-1,2,4-tricarboxylate (1.5 g, 4.2 mmol) in THF (37.5 mL) at 0° C. with stirring. After 10 minutes the reaction was quenched by the addition of saturated aqueous NaHCO$_3$ solution and extracted with EtOAc. The organic phase was dried, filtered and concentrated in vacuo. The residue was purified by column chromatography (silica, DCM/MeOH gradient elution). The product was taken on to the next reaction; MS m/z: 330 (M+H)$^+$.

TFA (1 mL, 13 mmol) was added to a solution of tert-butyl 8a-methyl-3-oxo-1,5,6,8-tetrahydrooxazolo[3,4-a]pyrazine-7-carboxylate (50 mg, 0.2 mmol) in DCM (3 mL). After 20 minutes the reaction mixture was concentrated in vacuo to give 8a-methyltetrahydro-1H-oxazolo[3,4-a]pyrazin-3(5H)-one A27, which was used without further purification in the next step (assuming quantitative yield as the mono TFA salt); MS m/z: 157 (M+H)$^+$.

Preparation 28:
N-(1-(Morpholin-2-yl)ethyl)methanesulfonamide A28

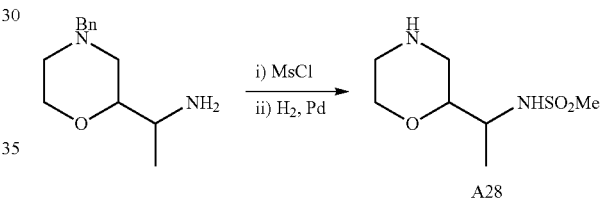

A28

A round-bottomed flask was charged with 1-(4-benzylmorpholin-2-yl)ethanamine (520 mg, 2.4 mmol) and Et$_3$N (658 μL, 4.7 mmol) in DCM (11 mL) under N$_2$. The mixture was cooled to −78° C. and methanesulfonyl chloride (164 μL, 2 mmol) added dropwise. The mixture was stirred for 10 minutes then allowed to warm to ambient temperature and stirred for a further 10 minutes. The reaction was quenched by the addition of saturated aqueous NaHCO$_3$ solution. After 5 minutes the reaction mixture was passed through a phase separator cartridge and concentrated in vacuo. The resulting brown oil (700 mg), was taken directly on to the next reaction; MS m/z: 299 (M+H)$^+$.

A round-bottomed flask was charged with N-[1-(4-benzylmorpholin-2-yl)ethyl]methanesulfonamide (700 mg, 2 mmol) in MeOH (10 mL) and concentrated HCl (196 μL, 2 mmol) was added. The flask was degassed and filled with N$_2$ (×3 vacuum-N$_2$ cycles) and Pd on C, wet, Degussa 10% w/w (249 mg, 0.2 mmol) was added in one portion. The flask was coupled with a hydrogen balloon and filled (vacuum-hydrogen×3 cycles). The reaction was vigorously stirred at ambient temperature for 16 hours. The mixture was filtered though a pad of Celite and the filtrate concentrated in vacuo. The residue was dissolved in methanol and loaded into an ion-exchange cartridge washing with MeOH then eluting the product with 2 M methanolic NH$_3$ solution. The filtrate was concentrated in vacuo to give N-(1-(morpholin-2-yl)ethyl)methanesulfonamide A28 (450 mg), which was taken directly on to the next reaction without further purification; MS m/z: 209 (M+H)$^+$.

Preparation 29: Dimethyl[(piperidin-3-ylmethyl)imino]-λ⁶-sulfanone A29

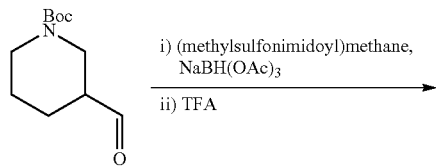

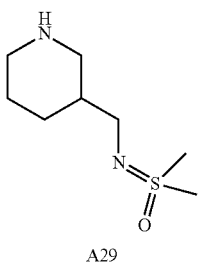

NaBH(OAc)₃ (455 mg, 2 mmol) was added to a mixture of tert-butyl 3-formylpiperidine-1-carboxylate (230 mg, 1 mmol) and (methylsulfonimidoyl)methane (50 mg, 0.5 mmol) in DCE (7 mL) and the reaction stirred at 35° C. for 15 hours. The reaction mixture was cooled to ambient temperature, filtered and the filtrate concentrated in vacuo. The residue was dissolved in water, the pH was adjusted to ~1 with 2 M aqueous HCl and the mixture was extracted with DCM (×3). The aqueous layer was taken to pH ~9 with 2 M NaOH and extracted with DCM (×3). The combined organic extracts were dried (MgSO₄), filtered and concentrated in vacuo to give a colourless oil (83 mg, 53%) which was taken on to the next reaction without further purification; ¹H NMR (500 MHz, Chloroform-d) δ 4.05-3.90 (m, 2H), 3.02 (2×s, 6H), 2.95 (dd, 2H), 2.82 (br s, 1H), 2.61 (dd, 1H), 1.91-1.86 (m, 1H), 1.69-1.64 (m, 1H), 1.60 (br s, 1H), 1.50-1.46 (m, 1H), 1.48 (s, 9H), 1.24-1.16 (m, 1H); MS m/z: 291 (M+H)⁺.

TFA (500 μL, 6.5 mmol) was added to a stirred solution of tert-butyl 3-({[dimethyl(oxo)-λ⁶-sulfanylidene]amino}methyl)piperidine-1-carboxylate (82 mg, 0.3 mmol) in DCM (5 mL) and the reaction stirred at ambient temperature for 18 hours. The solvent was removed in vacuo and the residue azeotroped with DCM (×2) and diethyl ether (×2). The residue was loaded onto an ion-exchange cartridge, washing with MeOH/DCM then eluting the product with 2 M NH₃ in MeOH/DCM. The filtrate was concentrated in vacuo to give dimethyl[(piperidin-3-ylmethyl)imino]-λ⁶-sulfanone A29 as a colourless oil (51 mg, 96%); ¹H NMR (500 MHz, Chloroform-d) δ 3.19 (dd, 1H), 3.03-3.00 (m, 2H), 3.02 (s, 6H), 2.92 (dd, 2H), 2.57 (td, 1H), 2.32 (dd, 1H), 1.93-1.88 (m, 1H), 1.71-1.60 (m, 1H), 1.51-1.42 (m, 1H), 1.16-1.08 (m, 1H); MS m/z: 191 (M+H).

Preparation 30: N-((3-Hydroxypiperidin-3-yl)methyl)methanesulfonamide A30

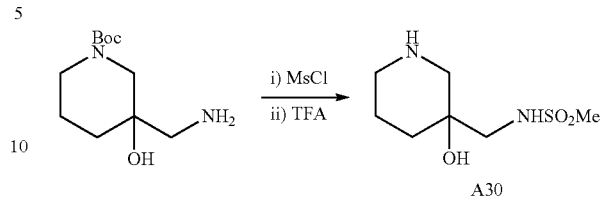

A solution of tert-butyl 3-(aminomethyl)-3-hydroxy-piperidine-1-carboxylate (333 mg, 1.4 mmol) and Et₃N (605 μL, 4.3 mmol) in DCM (10 mL) was treated with methanesulfonyl chloride (123 μL, 1.6 mmol) at ambient temperature. The mixture was stirred for 10 minutes, then washed with saturated aqueous sodium bicarbonate solution. The organic phase was dried (Na₂SO₄), filtered and concentrated in vacuo to give an oil. This material was dissolved in DCM (3 mL) and treated with TFA (1.67 mL, 22 mmol) at ambient temperature. After 1 hour the reaction mixture was concentrated in vacuo. The residue was taken up in MeOH and loaded onto an ion-exchange cartridge. The cartridge was washed with MeOH/DCM, then the product eluted with 2 M NH₃ in MeOH. The filtrate was concentrated in vacuo to give N-((3-hydroxypiperidin-3-yl)methyl)methanesulfonamide A30 as an oil (289 mg), which was taken directly on to the next reaction without further purification; MS m/z 209 (M+H)⁺.

Preparation 31: N-((4-Hydroxypiperidin-3-yl)methyl)methanesulfonamide A31

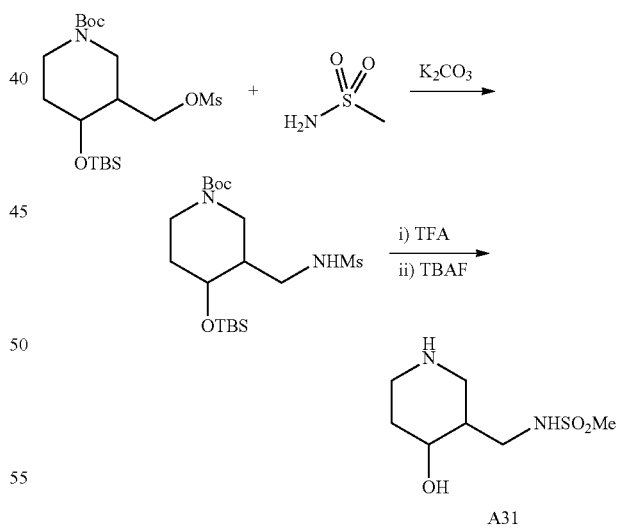

Methanesulfonamide (846 mg, 9 mmol), tert-butyl 4-[tert-butyl(dimethyl)silyl]oxy-3-(methylsulfonyloxymethyl)piperidine-1-carboxylate (1.08 g, 2.5 mmol) and K₂CO₃ (1.23 g, 9 mmol) were combined in DMF (12 mL) and heated at 120° C. under N₂ for 16 hours. The mixture was allowed to cool to ambient temperature, diluted with EtOAc then washed with saturated aqueous sodium bicarbonate solution and brine (×2). The organic layer was separated, dried (Na₂SO₄), filtered and concentrated in vacuo. The residue was treated with DCM (3 mL) and TFA (3 mL, 39 mmol) and the mixture stirred at 40° C. under N₂ for 18 hours. The reaction mixture was concentrated in vacuo and the residue treated with TBAF (12.7 mL of 1 M solution in THF, 12.7 mmol) and stirred at 65° C. for 16 hours. The reaction mixture was concentrated in vacuo to provide N-((4-hydroxypiperidin-3-yl)methyl)methanesulfonamide A31, which was taken on to the next reaction without purification assuming quantitative conversion; MS m/z 209 (M+H)⁺.

Preparation 32: N-((5-Hydroxypiperidin-3-yl)methyl)methanesulfonamide A32

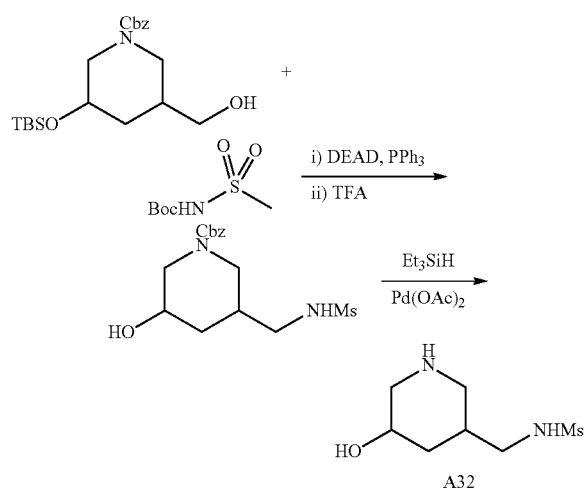

tert-Butyl N-methylsulfonylcarbamate (1.11 g, 5.7 mmol), benzyl 3-[tert-butyl(dimethyl)silyl]oxy-5-(hydroxymethyl)piperidine-1-carboxylate (1.43 g, 3.8 mmol) and Ph₃P (2.97 g, 11.33 mmol) were dissolved in THF (15 mL). DEAD (1.25 mL, 7.9 mmol) was added dropwise to the mixture at ambient temperature. After 3 hours the mixture was diluted with EtOAc and saturated aqueous sodium bicarbonate solution. The organic phase was washed with brine, dried (MgSO₄), filtered and concentrated in vacuo. The residue was purified by column chromatography (silica, PE eluent). The product fractions were combined and concentrated in vacuo. The residue was taken up in DCM (5 mL) and TFA (5 mL, 65 mmol) and stirred at ambient temperature for 3 hours, then warmed to 40° C. and stirred for 2 hours. The reaction mixture was concentrated in vacuo. The residue was purified by column chromatography (silica, EtOAc/PE gradient elution) to give benzyl 3-hydroxy-5-(methanesulfonamidomethyl)piperidine-1-carboxylate (313 mg, 24%); MS m/z 343 (M+H)⁺.

This material was dissolved in DCM (10 mL). The resulting solution was sequentially treated with N,N-diethylethanamine (127 µL, 0.9 mmol), Pd(OAc)₂ (103 mg, 0.46 mmol), and Et₃SiH (950 µL, 6 mmol). The mixture was stirred at ambient temperature for 1 hour then concentrated in vacuo. The residue was taken up in MeOH and loaded onto an ion-exchange cartridge, washing with MeOH/DCM then eluting the product with 2 M NH₃ in MeOH. The filtrate was concentrated in vacuo to give N-((5-hydroxypiperidin-3-yl)methyl)methanesulfonamide A32, which was taken directly on to the next reaction without further purification, assuming quantitative conversion; MS m/z: 209 (M+H)⁺.

Preparation 33: N-((5-Hydroxy-5-methylpiperidin-3-yl)methyl)methanesulfonamide, A33

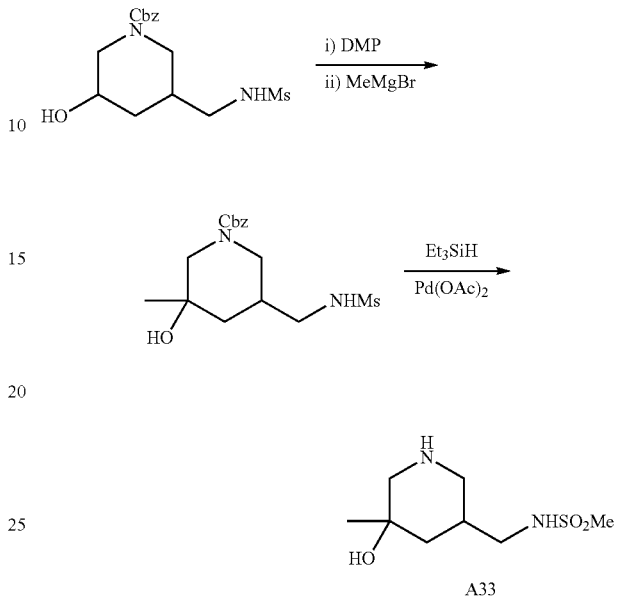

Benzyl 3-hydroxy-5-(methanesulfonamidomethyl)piperidine-1-carboxylate (200 mg, 0.58 mmol) was dissolved DCM (20 mL) under N₂. Dess-Martin periodinane (396 mg, 0.9 mmol) was added at ambient temperature. The reaction mixture was stirred for 16 hours then additional Dess-Martin periodinane (200 mg) was added and the reaction mixture stirred for a further 16 hours. The reaction was quenched by the addition of 1:1 saturated aqueous sodium bicarbonate solution: saturated aqueous sodium thiosulfate solution (15 mL). The organic layer was separated, dried (Na₂SO₄), filtered and concentrated in vacuo; MS m/z: 341 (M+H)⁺.

The residue was dissolved in THF (10 mL) under N₂. The solution was cooled to −78° C. and MeMgBr (388 µL of 3 M, 1.2 mmol) was added dropwise. The cooling bath was removed and the mixture allowed to warm to ambient temperature. After 2 hours additional MeMgBr (388 µL of 3 M, 1.2 mmol) was added and the mixture stirred for 16 hours. Additional MeMgBr (1.9 mL of 3 M) was added and after a further 5 hours the reaction was quenched by the addition of water (3 mL). Saturated aqueous ammonium chloride solution was added and the mixture extracted with EtOAc. The organic phase was dried (Na₂SO₄), filtered and concentrated in vacuo. The residue (200 mg) was dissolved in DCM (10 mL) and treated with Pd(OAc)₂ (42 mg, 0.19 mmol), Et₃N (235 µL, 1.7 mmol) and Et₃SiH (421 µL, 2.6 mmol). The mixture was stirred at ambient temperature under N₂ and after 7 hours additional Et₃SiH (421 µL, 2.6 mmol) and Pd(OAc)₂ (42 mg, 0.19 mmol) were added. After 90 minutes the reaction mixture was diluted with MeOH and loaded on to an ion-exchange cartridge. The product was eluted with 2 M methanolic ammonia solution and the filtrate concentrated in vacuo. The residue, which contained the desired product N-((5-hydroxy-5-methylpiperidin-3-yl)methyl)methanesulfonamide A33, was taken directly on to the next reaction without further purification; MS m/z: 223 (M+H)⁺.

Preparation 34: N-(Piperidin-3-yloxy)methanesulfonamide A34

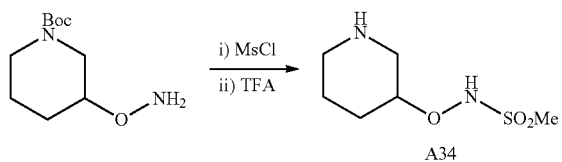

A solution of tert-butyl 3-aminooxypiperidine-1-carboxylate (2.1 g, 9.7 mmol) and Et₃N (2.71 mL, 19.4 mmol) in DCM (10 mL) was treated with methanesulfonyl chloride (751 µL, 9.7 mmol). The mixture was stirred at ambient temperature for 16 hours. The resulting suspension was filtered, washing with DCM. The filtrate was concentrated in vacuo and the residue purified by column chromatography (silica, PE/EtOAc gradient elution). The product fractions were concentrated in vacuo and the residue taken up in DCM (10 mL). TFA (7.48 mL, 97.10 mmol) was added and after 30 minutes stirring at ambient temperature the mixture was concentrated in vacuo. The residue was loaded onto an ion-exchange cartridge, washing with MeOH then eluting the product with 2 M methanolic NH₃ solution. The filtrate was concentrated in vacuo to give N-(piperidin-3-yloxy) methanesulfonamide A34 (876 mg, 46%), which was taken on to the next reaction without further purification; $^1$H NMR (500 MHz, DMSO-$d_6$) δ 3.73 (tt, 1H), 3.46 (s, 1H), 3.03-2.99 (m, 1H), 2.97 (s, 3H), 2.68 (dt, 1H), 2.45 (dt, 2H), 1.94-1.86 (m, 1H), 1.61 (dtt, 1H), 1.46-1.36 (m, 1H), 1.36-1.27 (m, 1H).

Preparation 35: Methyl(methylimino)(piperidin-3-ylmethyl)-$\lambda^6$-sulfanone, A35

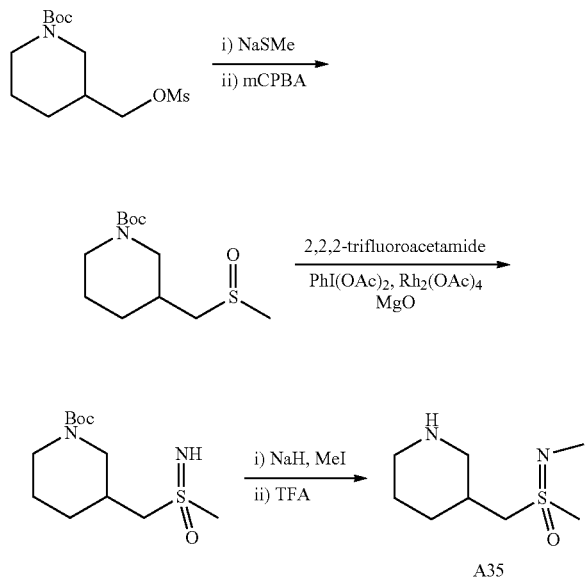

NaSMe (4.06 g, 58 mmol) was added to a solution of tert-butyl 3-(methylsulfonyloxymethyl)piperidine-1-carboxylate (8.5 g, 29 mmol) in EtOH (170 mL). The mixture was stirred at ambient temperature for 6 hours then concentrated in vacuo. The residue was partitioned between DCM and saturated aqueous NaHCO₃ solution, and the organic phase separated, dried and concentrated in vacuo. The residue was purified by column chromatography (silica, MeOH/DCM gradient elution) to give a pale yellow oil (6.9 g). This material was dissolved in DCM (100 mL), the solution cooled in an ice bath and mCPBA (6.93 g of 70% pure w/w, 28 mmol) was added portionwise. After the addition was complete, the reaction mixture was stirred for 10 minutes then partitioned between DCM, saturated aqueous sodium bicarbonate solution and saturated aqueous sodium thiosulfate solution. The organic phase was dried and concentrated in vacuo. The residue was purified by column chromatography (silica, DCM/MeOH gradient elution) to give tert-butyl 3-((methylsulfinyl)methyl)piperidine-1-carboxylate (5.5 g, 72% over two steps) as a colourless oil.

tert-Butyl 3-((methylsulfinyl)methyl)piperidine-1-carboxylate (5.5 g, 21.0 mmol), 2,2,2-trifluoroacetamide (5.23 g, 46.3 mmol), (diacetoxyiodo)benzene (10.17 g, 31.6 mmol) and magnesium oxide (3.39 g, 84.2 mmol) were dissolved in DCM (250 mL) and rhodium acetate (II) dimer (0.9 g, 2.04 mmol) was added. The mixture was stirred at ambient temperature overnight before being filtered through Celite and concentrated in vacuo. The residue was dissolved in methanol (50 mL) and water (10 mL), and K₂CO₃ (17.44 g, 126.2 mmol) was added. The mixture was stirred at ambient temperature for 3 hours before heating 50° C. for 3 days. The mixture was concentrated in vacuo and the residue dissolved in methanol (5 mL) and acetonitrile/water (3:1 mixture, 5 mL). After 1.5 hours at 90° C. the mixture was cooled, diluted in EtOAc and washed with brine and saturated aq. NaHCO₃ solution. The organic layer was dried (Na₂SO₄) and concentrated in vacuo to give tert-butyl 3-((S-methylsulfonimidoyl)methyl)piperidine-1-carboxylate (5.96 g) as an amber oil which was used without further purification.

tert-Butyl 3-[(methyl sulfonimidoyl)methyl]piperidine-1-carboxylate (2 g, 7.2 mmol) was dissolved in in THF (12 mL) under N₂. The solution was cooled in an ice bath and NaH (868 mg of a 60% dispersion in mineral oil, 22 mmol) then MeI (5.4 mL of a 2 M solution in TBME, 10.85 mmol) were added with stirring. The reaction mixture was allowed to warm to ambient temperature and stirred for 16 hours. Additional NaH (289 mg of a 60% dispersion in mineral oil, 1 equivalent) and MeI (5.4 mL of 2 M solution in TBME, 10.85 mmol) were added. After 5 hours, the reaction mixture was quenched by dropwise addition of water. The mixture was diluted with EtOAc and washed with saturated aqueous sodium bicarbonate solution. The organic layer was dried (Na₂SO₄), filtered and concentrated in vacuo. The residue was purified by column chromatography (silica, MeOH/DCM gradient elution) to give an oil (1.59 g). This material was dissolved in DCM (3 mL), treated with TFA (3 mL) and stirred at ambient temperature for 45 minutes before being concentrated in vacuo. The residue was loaded onto an ion-exchange cartridge, washing with MeOH then eluting the product with 2 M methanolic NH₃ solution. The filtrate was concentrated in vacuo to give methyl(methylimino) (piperidin-3-ylmethyl)-$\lambda^6$-sulfanone A35 (612 mg, 44%), which was taken on to the next reaction without further purification; $^1$H NMR (500 MHz, Methanol-$d_4$) δ 3.39 (s, 1H), 3.32-3.25 (m, 1H), 3.21-3.08 (m, 2H), 3.05 (d, 2H), 3.04-2.96 (m, 1H), 2.79 (s, 3H), 2.66-2.56 (m, 1H), 2.51-2.42 (m, 1H), 2.27-2.15 (m, 1H), 2.07 (m, 1H), 1.79-1.70 (m, 1H), 1.61 (m, 1H), 1.36 (m, 1H).

Preparation 36: 2-(3-Methyl-1H-pyrazol-4-yl)morpholine A36 and 2-((1H-pyrazol-4-yl)methyl)morpholine A37

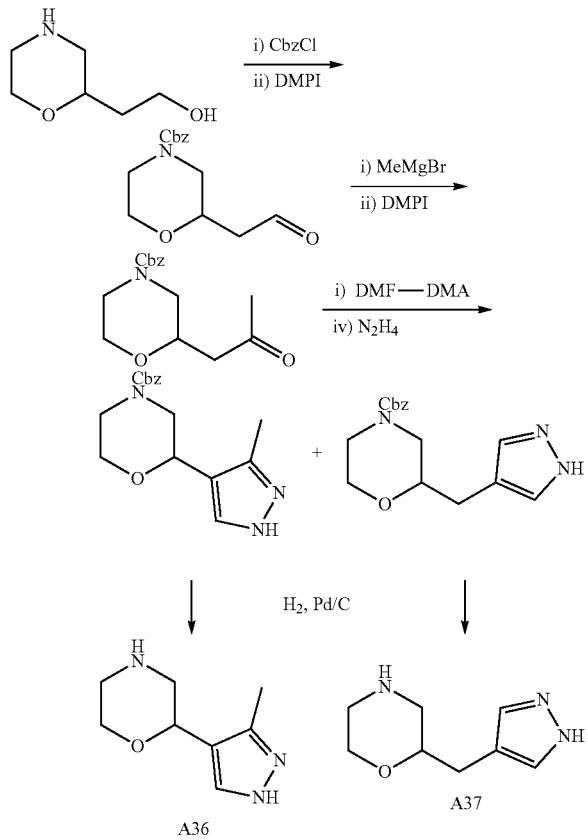

Benzyl chloroformate (5.9 mL, 41 mmol) was added dropwise to an ice-cold solution of 2-morpholin-2-ylethanol (4.5 g, 34 mmol) and DIPEA (9 mL, 52 mmol) in DCM (50 mL) under an atmosphere of $N_2$. The solution was allowed to warm to ambient temperature over 18 hours. The solution was diluted with 2 M aqueous HCl, stirred for 10 minutes and the layers separated. The aqueous layer was extracted with DCM (×3) and the combined organic extracts dried (MgSO$_4$), filtered and concentrated in vacuo. The residue was purified by column chromatography (silica, 0 to 100% EtOAc/PE gradient elution) to give benzyl 2-(2-hydroxyethyl)morpholine-4-carboxylate (7.18 g, 79%) as a colourless oil; $^1$H NMR (500 MHz, Chloroform-d) δ 7.41-7.33 (m, 5H), 5.17 (d, 2H), 4.04-3.91 (m, 3H), 3.81 (t, 2H), 3.66-3.55 (m, 2H), 3.04 (s, 1H), 2.77 (s, 1H), 2.28 (s, 1H), 1.73 (s, 2H); MS m/z: 266 (M+H)$^+$.

Dess-Martin periodinane (11.5 g, 27 mmol) was added to a stirred solution of benzyl 2-(2-hydroxyethyl)morpholine-4-carboxylate (7.18 g, 27 mmol) in DCM (100 mL) at 0° C. and the reaction allowed to warm to ambient temperature over 16 hours. The reaction mixture was quenched by the addition of 1:1 saturated aqueous NaHCO$_3$/sodium thiosulfate solution, stirred for 10 minutes and the layers separated. The aqueous layer was extracted with DCM (×2) and the combined organic extracts washed with 1:1 saturated aqueous NaHCO$_3$/sodium thiosulfate solution (×2) and brine, dried (MgSO$_4$), filtered and concentrated in vacuo to give benzyl 2-(2-oxoethyl)morpholine-4-carboxylate (6.91 g, 97%) as a colourless oil; $^1$H NMR (500 MHz, Chloroform-d) δ 9.79 (dd, 1H), 7.41-7.33 (m, 5H), 5.17 (d, 2H), 4.09-3.88 (m, 4H), 3.59 (br t, 1H), 3.04 (s, 1H), 2.78 (s, 1H), 2.63 (ddd, 1H), 2.51 (dd, 1H).

MeMgBr (1.8 mL of 3 M, 5.4 mmol) was added to a stirred solution of benzyl 2-(2-oxoethyl)morpholine-4-carboxylate (720 mg, 2.7 mmol) in THF (20 mL) at 0° C. and the reaction was allowed to warm to ambient temperature over 20 hours. The reaction was quenched by the addition of 2 M HCl and the mixture extracted with DCM (×3). The combined organic extracts were washed with brine, dried (MgSO$_4$), filtered and concentrated in vacuo. The residue was purified by column chromatography (silica, 0-100% EtOAc/PE gradient elution) to give benzyl 2-(2-hydroxypropyl)morpholine-4-carboxylate (563 mg, 74%) as a colourless oil; $^1$H NMR (500 MHz, Chloroform-d) δ 7.43-7.32 (m, 5H), 5.19-5.14 (m, 2H), 4.13-3.93 (m, 4H), 3.70-3.54 (m, 2H), 3.21-3.04 (m, 2H), 2.75 (br s, 1H), 1.65-1.57 (m, 2H), 1.22 (dd, 3H); MS m/z: 280 (M+1)$^+$.

Dess-Martin periodinane (855 mg, 2 mmol) was added to a stirred solution of benzyl 2-(2-hydroxypropyl)morpholine-4-carboxylate (563 mg, 2 mmol) in DCM (10 mL) at 0° C. and the reaction allowed to warm to ambient temperature over 24 hours. The reaction mixture was quenched by the addition of 1:1 saturated aqueous NaHCO$_3$/sodium thiosulfate solution, stirred for 10 minutes and the layers separated. The aqueous layer was extracted with DCM (×2) and the combined organic extracts washed with 1:1 saturated aqueous NaHCO$_3$/sodium thiosulfate solution (×2) and brine, dried (MgSO$_4$), filtered and concentrated in vacuo to give benzyl 2-acetonylmorpholine-4-carboxylate (558 mg, 100%) as a colourless oil; $^1$H NMR (500 MHz, Chloroform-d) δ 7.41-7.33 (m, 5H), 5.20-5.14 (m, 2H), 3.96 (br d, 4H), 3.57 (t, 1H), 3.02 (s, 1H), 2.72 (s, 1H), 2.68 (dd, 1H), 2.47 (dd, 1H), 2.21 (s, 3H); MS m/z: 278.2 (M+H)$^+$.

A mixture of benzyl 2-acetonylmorpholine-4-carboxylate (557 mg, 2 mmol) and DMF-DMA (270 μL, 2 mmol) in DMF (10 mL) was stirred at 80° C. for 21 hours. A further portion of DMF-DMA (140 μL, 1.1 mmol) was added and the reaction stirred at 80° C. for a further 6 hours. A further portion of DMF-DMA (100 μL, 0.75 mmol) was added and the reaction stirred at 80° C. for a further 18 hours. The reaction mixture was cooled to ambient temperature and the solvent removed in vacuo. The residue was used directly assuming 100% yield and purity.

Hydrazine hydrate (100 μL, 2 mmol) was added to a stirred solution of benzyl 2-(4-(dimethylamino)-2-oxobut-3-en-1-yl)morpholine-4-carboxylate (668 mg, 2 mmol) in EtOH (10 mL) and the reaction mixture stirred at 80° C. for 4 hours. A further portion of hydrazine hydrate (100 μL, 2 mmol) was added and the reaction stirred at 80° C. for 1.5 hours. The solvent was removed in vacuo and the residue purified by column chromatography (silica, 0-100% EtOAc/PE gradient elution), to give benzyl 2-(1H-pyrazol-3-ylmethyl)morpholine-4-carboxylate (215 mg, 36%) as a colourless oil; $^1$H NMR (500 MHz, Chloroform-d) δ 10.19 (s, 1H), 7.51 (d, 1H), 7.40-7.33 (m, 5H), 6.14 (fine d, 1H), 5.16 (s, 2H), 4.05-3.95 (m, 3H), 3.68 (s, 1H), 3.59-3.56 (m, 1H), 3.06 (s, 1H), 2.88 (s, 2H), 2.75 (s, 1H); MS m/z: 302 (M+H)$^+$; and benzyl 2-(3-methyl-1H-pyrazol-4-yl)morpholine-4-carboxylate (76 mg, 13%) as a colourless oil; $^1$H NMR (500 MHz, Chloroform-d) δ 7.42 (s, 1H), 7.32-7.24 (m, 5H), 5.10 (s, 2H), 4.41-4.34 (m, 1H), 4.03-3.89 (m, 2H), 3.61-3.55 (m, 2H), 3.08-3.01 (m, 2H), 2.24 (s, 3H); MS m/z: 302 (M+H)$^+$.

Pd on C, wet, Degussa 10% w/w (7 mg, 0.007 mmol) was added to a stirred solution of benzyl 2-(3-methyl-1H-pyrazol-4-yl)morpholine-4-carboxylate (76 mg, 0.25 mmol) in MeOH (1 mL) and EtOAc (1 mL) and the reaction placed under an atmosphere of hydrogen. The reaction was stirred at ambient temperature for 15 hours then further Pd on C, wet, Degussa 10% w/w (7 mg, 0.07 mmol) was added and the reaction placed under an atmosphere of hydrogen. The reaction was stirred at ambient temperature for 6 hours then the catalyst removed by filtration and the solvent removed in vacuo to give 2-(3-methyl-1H-pyrazol-4-yl)morpholine A36 (41 mg, 98%); MS m/z: 168 (M+H)$^+$.

Pd on C, wet, Degussa 10% w/w, (20 mg, 0.02 mmol) was added to a stirred solution of benzyl 2-(1H-pyrazol-3-ylmethyl)morpholine-4-carboxylate (215 mg, 0.7 mmol) in MeOH (1.5 mL)/EtOAc (1.5 mL) and the reaction placed under an atmosphere of hydrogen. The reaction was stirred at ambient temperature for 15 hours then the catalyst removed by filtration and the solvent removed in vacuo to give 2-(1H-pyrazol-4-ylmethyl)morpholine A37 (113 mg, 94%) as a colourless oil; MS m/z: 168 (M+H)$^+$.

Preparation 37: N-((4,4-Dimethylpyrrolidin-3-yl)methyl)methanesulfonamide A38

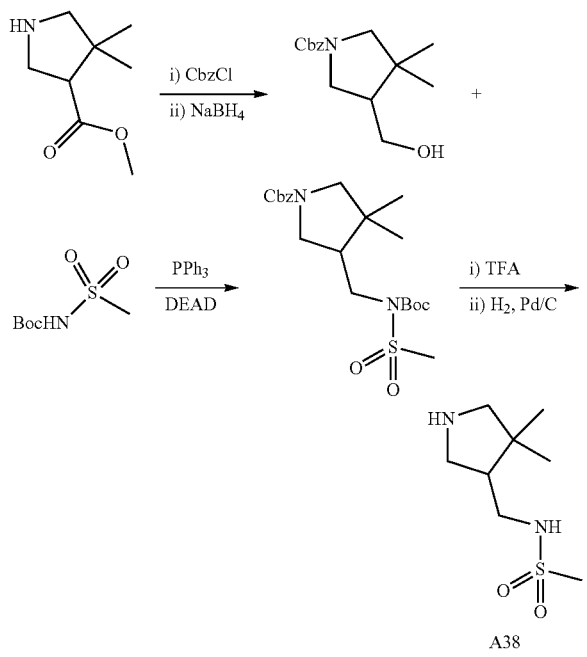

Benzyl chloroformate (1.4 mL, 9.807 mmol) was added dropwise to a stirred solution of methyl 4,4-dimethylpyrrolidine-3-carboxylate (1 g, 6.36 mmol) and DIPEA (2.4 mL, 13.78 mmol) in DCM (20 mL) at 0° C. and the reaction allowed to warm to ambient temperature over 48 hours. The reaction was diluted with saturated aqueous NH$_4$Cl and the layers separated. The organic layer was washed with brine, dried (MgSO$_4$), filtered and concentrated in vacuo. The residue was purified by column chromatography (silica, 0 to 30% EtOAc/Petroleum Ether gradient elution) to give O1-Benzyl O3-methyl 4,4-dimethylpyrrolidine-1,3-dicarboxylate (1.49 g, 81%) as a colourless oil; $^1$H NMR (500 MHz, Chloroform-d) δ 7.32-7.22 (m, 5H), 5.11-5.04 (m, 2H), 3.74-3.59 (m, 2H), 3.64 (s, 3H), 3.31 (dd, J=28.1, 10.5 Hz, 1H), 3.14 (t, J=10.6 Hz, 1H), 2.69 (dt, J=17.6, 8.1 Hz, 1H), 1.15 (d, J=12.7 Hz, 3H), 0.94 (s, 3H); MS m/z: 292.0 (M+H)$^+$.

O1-Benzyl O3-methyl 4,4-dimethylpyrrolidine-1,3-dicarboxylate (1.49 g, 5 mmol) in THF (10 mL) was cooled to 0° C. before the addition of NaBH$_4$ (580 mg, 15 mmol) and MeOH (1 mL). The mixture was allowed to warm to ambient temperature over 24 hours. A further portion of NaBH$_4$ (580 mg, 15 mmol) was added and the reaction stirred at ambient temperature for a further 4 hours. The mixture was diluted with H$_2$O and EtOAc and the layers separated. The organic layer was washed with saturated aqueous NaHCO$_3$ solution (×2), brine, dried (MgSO$_4$), filtered and concentrated in vacuo. The residue was purified by column chromatography (silica, 0 to 30% EtOAc/PE gradient elution) to give benzyl 4-(hydroxymethyl)-3,3-dimethyl-pyrrolidine-1-carboxylate (898 mg, 67%) as a colourless oil; MS m/z: 264 (M+H)$^+$.

To a solution of benzyl 4-(hydroxymethyl)-3,3-dimethyl-pyrrolidine-1-carboxylate (300 mg, 1.14 mmol), tert-butyl N-methylsulfonylcarbamate (330 mg, 1.7 mmol) and PPh$_3$ (890 mg, 3.4 mmol) in THF (20 mL) was added DEAD (390 µL, 2.5 mmol) dropwise and the reaction mixture stirred at ambient temperature under N$_2$ for 16 hours. The reaction mixture was concentrated in vacuo and the residue purified by column chromatography (silica, 0 to 50% EtOAc/PE gradient elution) to give benzyl 4-[[tert-butoxycarbonyl(methylsulfonyl)amino]methyl]-3,3-dimethyl-pyrrolidine-1-carboxylate as a colourless oil that was taken directly on to the next step; MS m/z: 441 (M+H)$^+$.

TFA (2 mL, 26 mmol) was added to a stirred solution of benzyl 4-[[tert-butoxycarbonyl(methylsulfonyl)amino]methyl]-3,3-dimethyl-pyrrolidine-1-carboxylate (502 mg, 1.1 mmol) in DCM (15 mL) and the reaction mixture stirred at ambient temperature for 15 hours. The solvent was removed in vacuo and the residue azeotroped with DCM (×2) and diethyl ether (×2). The residue was diluted with EtOAc and washed with saturated aqueous NaHCO$_3$ (×2) and brine, dried (MgSO$_4$), filtered and concentrated in vacuo. The residue was used directly in next step.

Pd on C, wet, Degussa 10% w/w (60 mg, 0.06 mmol) was added to a stirred solution of benzyl 4-(methanesulfonamidomethyl)-3,3-dimethyl-pyrrolidine-1-carboxylate (388 mg, 1.1 mmol) in MeOH (10 mL) and EtOAc (10 mL) and the reaction placed under an atmosphere of hydrogen. The reaction was stirred at ambient temperature for 4 hours then the catalyst removed by filtration and the solvent removed in vacuo. The residue was loaded onto an ion-exchange cartridge, washing with MeOH then eluting the product with 2 M methanolic NH$_3$ solution. The filtrate was concentrated in vacuo to give N-[(4,4-dimethylpyrrolidin-3-yl)methyl]methanesulfonamide A38 (188 mg, 80%) as a pale yellow oil; $^1$H NMR (500 MHz, DMSO-d$_6$) δ 6.88 (s, 1H), 3.17 (s, 2H), 3.05-3.01 (m, 2H), 2.88 (s, 3H), 2.73 (t, 1H), 2.55-2.51 (m, 1H), 1.74-1.67 (m, 1H), 1.01 (s, 3H), 0.85 (s, 3H); MS m/z: 207 (M+H)$^+$.

Preparation 38: N-((4-Hydroxypyrrolidin-3-yl)methyl)methanesulfonamide A39

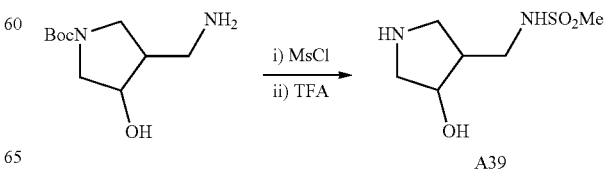

Methanesulfonyl chloride (115 μL, 1.5 mmol) was added to a stirred solution of tert-butyl 3-(aminomethyl)-4-hydroxy-pyrrolidine-1-carboxylate (250 mg, 1.2 mmol) and Et$_3$N (250 μL, 1.6 mmol) in THF (10 mL) under an atmosphere of N$_2$ and the reaction was stirred at ambient temperature for 2 hours. The reaction was diluted with DCM and saturated aqueous NaHCO$_3$ solution and the mixture was stirred for 10 minutes. The layers were separated and the aqueous layer extracted with DCM (×2). The combined organic extracts were dried (MgSO$_4$), filtered and concentrated in vacuo to give tert-butyl 3-hydroxy-4-(methanesulfonamidomethyl)pyrrolidine-1-carboxylate as a pale yellow oil.

TFA (0.5 mL) was added to a stirred solution of the crude tert-butyl 3-hydroxy-4-(methanesulfonamidomethyl)pyrrolidine-1-carboxylate (340 mg, 1.2 mmol) in DCM (5 mL) and the reaction mixture stirred at ambient temperature for 16 hours. The solvent was removed in vacuo and the residue azeotroped with DCM (×2) and diethyl ether (×2). The residue was loaded onto an ion-exchange cartridge, washed with MeOH and the product eluted with 2 M methanolic NH$_3$ solution. The filtrate was concentrated in vacuo to give N-((4-hydroxypyrrolidin-3-yl)methyl)methanesulfonamide A39 as a pale orange oil which was taken directly on to the next reaction without further purification; MS m/z: 195 (M+H)$^+$.

Preparation 39: N-((2-Methylpyrrolidin-3-yl)methyl)methanesulfonamide A40

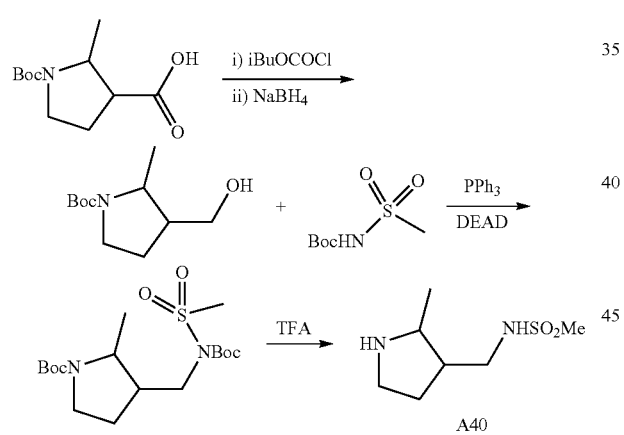

1-tert-Butoxycarbonyl-2-methyl-pyrrolidine-3-carboxylic acid (1 g, 4.4 mmol) was suspended in THF (20 mL) and cooled to −20° C. Et$_3$N (910 μL, 6.5 mmol) was added followed by isobutyl chloroformate (850 μL, 6.6 mmol). The reaction was allowed to warm to ambient temperature over 60 minutes before NaBH$_4$ (250 mg, 6.6 mmol) was added followed by methanol (7.5 mL). The reaction mixture was stirred for 2.5 hours at ambient temperature then quenched by the addition of saturated aqueous NaHCO$_3$ solution and stirred for 10 minutes. Water was added to dissolve salts and the mixture was extracted with EtOAc (×3). The combined organic extracts were washed with brine, dried (MgSO$_4$), filtered and concentrated in vacuo. The residue was purified by column chromatography (silica, 0 to 50% EtOAc/PE gradient elution) to give tert-butyl 3-(hydroxymethyl)-2-methyl-pyrrolidine-1-carboxylate (395 mg, 42%) as a mixture of diastereomers (~1:1) as a colourless oil, which was taken directly on to next reaction.

To a solution of tert-butyl 3-(hydroxymethyl)-2-methyl-pyrrolidine-1-carboxylate (394 mg, 1.8 mmol), tert-butyl N-methylsulfonylcarbamate (530 mg, 2.7 mmol) and PPh$_3$ (1.4 g, 5.3 mmol) in THF (25 mL) was added DEAD (625 μL, 4 mmol) dropwise and the reaction mixture stirred at ambient temperature under N$_2$ for 16 hours. The reaction mixture was then concentrated in vacuo and the residue used directly without further purification; MS m/z: 393 (M+H)$^+$.

TFA (2 mL, 26 mmol) was added to a stirred solution of tert-butyl 3-[[tert-butoxycarbonyl(methylsulfonyl)amino]methyl]-2-methyl-pyrrolidine-1-carboxylate (718 mg, 1.83 mmol) in DCM (10 mL) and the reaction mixture stirred at ambient temperature for 22 hours. A further portion of TFA (5 mL, 65 mmol) was added and the reaction stirred at ambient temperature for another 4 hours. The solvent was removed in vacuo and the residue azeotroped with DCM (×2) and diethyl ether (×2). The residue was loaded onto an ion-exchange cartridge and washed with MeOH/DCM mixtures. The product was eluted by washing the cartridge with 2 M NH$_3$ in MeOH/DCM mixtures. The solvent was removed in vacuo to give N-[(2-methylpyrrolidin-3-yl)methyl]methanesulfonamide A40, which was used directly in the next reaction; MS m/z: 193 (M+H)$^+$.

Preparation 40:
4-((3-Fluoroazetidin-1-yl)methyl)piperidine A41

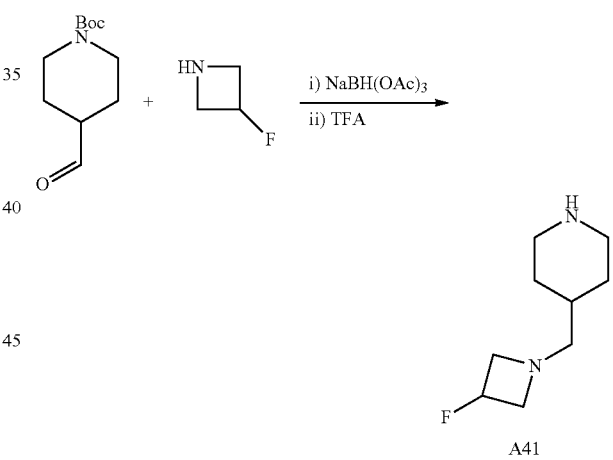

A mixture of 3-fluoroazetidine hydrochloride (1.0 g, 9 mmol), tert-butyl 4-formylpiperidine-1-carboxylate (2.3 g, 11 mmol), DIPEA (1.7 mL, 10 mmol) and crushed 4 Å molecular sieves (1 g) in DCE (30 mL) was stirred at ambient temperature for 5 hours. NaBH(OAc)$_3$ (3.8 g, 18 mmol) was added and the reaction stirred at ambient temperature for a further 16 hours. The mixture was filtered through Celite (washing with DCM) and the filtrate concentrated in vacuo. The residue was purified by column chromatography (silica, 0-10% MeOH/DCM gradient elution) to give tert-butyl 4-[(3-fluoroazetidin-1-yl)methyl]piperidine-1-carboxylate as a colourless oil (2.44 g); $^1$H NMR (500 MHz, DMSO-d$_6$) δ 5.20-5.04 (m, 1H), 3.90 (d, 2H), 3.61-3.47 (m, 2H), 3.07-3.00 (m, 2H), 2.65 (s, 1H), 2.31 (d, 2H), 1.62 (dd, 2H), 1.44-1.39 (m, 2H), 1.39 (s, 9H), 1.08-0.82 (m, 2H).

TFA (5 mL, 65 mmol) was added to a solution of tert-butyl 4-[(3-fluoroazetidin-1-yl)methyl]piperidine-1-carboxylate (2.44 g, 9 mmol) in DCM (15 mL) and the reaction stirred at ambient temperature for 15 hours. The solvent was removed in vacuo and the residue azeotroped with DCM (×2) and ether (×2). The residue was loaded onto an ion-exchange cartridge, washed with MeOH/DCM mixtures and then the product was eluted with 2 M $NH_3$ in MeOH/DCM mixtures. The filtrate was concentrated in vacuo to give 4-((3-fluoroazetidin-1-yl)methyl)piperidine A41 as a pale yellow oil (1.11 g, 72% over two steps); $^1$H NMR (500 MHz, DMSO-$d_6$) δ 5.11 (dtt, 1H), 3.59-3.48 (m, 2H), 3.04-2.97 (m, 2H), 2.87 (dt, 2H), 2.38 (td, 2H), 2.27 (d, 2H), 1.97 (s, 1H), 1.62-1.48 (m, 2H), 1.31 (ttt, 1H), 1.04-0.83 (m, 2H).

Preparation 41:
N-(Indolin-3-ylmethyl)methanesulfonamide A42

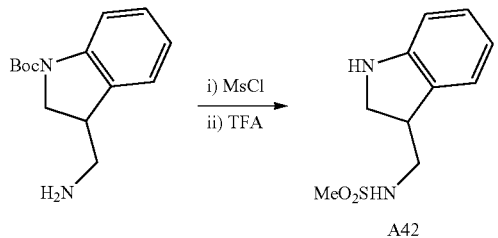

tert-Butyl 3-(aminomethyl)indoline-1-carboxylate (172 mg, 0.7 mmol) was dissolved in DCM (5 mL) and DIPEA (241 µL, 1.4 mmol) was added. The solution was cooled in an ice bath and methanesulfonyl chloride (59 µL, 0.8 mmol) was added slowly with stirring. After 5 minutes, water (~0.2 mL) was added and the reaction mixture was concentrated to dryness in vacuo. DCM (5 mL) and TFA (2 mL, 26 mmol) were added to the residue and the resulting solution stirred for 16 hours. The reaction mixture was concentrated in vacuo and the residue azeotroped with DCM (×2), then taken up in EtOAc and washed with saturated aqueous $NaHCO_3$ solution. The organic phase was dried ($Na_2SO_4$), filtered and concentrated in vacuo. The residue was purified by column chromatography (silica, 0-10% MeOH/DCM gradient elution) to give N-(indolin-3-ylmethyl)methanesulfonamide A42 as a pale yellow glass (115 mg, 73% over two steps); $^1$H NMR (500 MHz, DMSO-$d_6$) δ 7.16 (t, 1H), 7.09 (dt, 1H), 7.01-6.90 (m, 1H), 6.61-6.45 (m, 2H), 5.47 (s, 1H), 3.51 (dd, 1H), 3.30-3.24 (m, 2H), 3.20 (dt, J=12.6, 5.6 Hz, 1H), 2.98 (ddd, 1H), 2.89 (s, 3H); MS m/z: 227 (M+H)$^+$.

Preparation 42: 4-(Methylsulfonyl)octahydropyrrolo
[3,4-b][1,4]oxazine A43

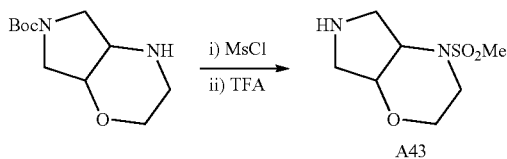

tert-Butyl 3,4,4a,5,7,7a-hexahydro-2H-pyrrolo[3,4-b][1,4]oxazine-6-carboxylate (107 mg, 0.5 mmol) was dissolved in DCM (2 mL) under $N_2$. DIPEA (163 µL, 1 mmol) was added and the mixture cooled in an ice bath. Methanesulfonyl chloride (54 µL, 0.7 mmol) was added with stirring. After 1 hour, water (~0.1 mL) was added and the mixture diluted with DCM (10 mL). Saturated aqueous $NaHCO_3$ was added and the layers separated. The aqueous phase was extracted with DCM. Combined organics were washed with brine, dried ($Na_2SO_4$), filtered and concentrated in vacuo. The residue was taken up in DCM and purified by column chromatography (silica, 0-10% MeOH/DCM gradient elution) to give a brown glass (116 mg). This material was dissolved in DCM (3 mL) and TFA (2 mL) added. After 30 minutes the mixture was concentrated in vacuo and residue azeotroped with DCM. The residue was taken up in MeOH and passed through an SPE bicarbonate cartridge. The filtrate was concentrated to give 4-(methylsulfonyl)octahydropyrrolo[3,4-b][1,4]oxazine A43 as a light brown oil (69 mg, 71% over two steps), which was taken on to the next reaction without further purification; MS m/z: 207 (M+H)$^+$.

Preparation 43: N-((1SR,6RS,8RS)-3-Azabicyclo
[4.2.0]octan-8-yl)methanesulfonamide A44

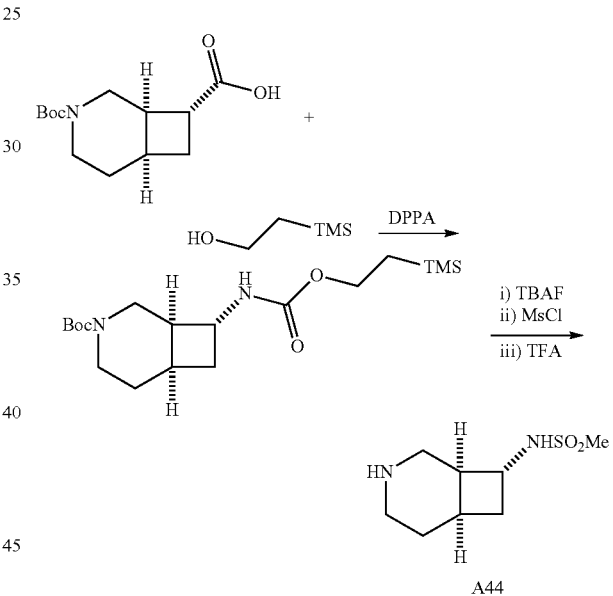

(1SR,6RS,7RS)-4-tert-Butoxycarbonyl-4-azabicyclo [4.2.0]octane-7-carboxylic acid (590 mg, 2.3 mmol), DIPEA (886 µL, 5 mmol) and 2-trimethylsilylethanol (2.65 mL, 18.5 mmol) were dissolved in toluene (20 mL) and heated under reflux. DPPA (1.1 mL, 5 mmol) was added slowly and the reaction was heated under reflux for 16 hours. The mixture was cooled to ambient temperature and concentrated in vacuo. The residue was taken up in DCM and purified by column chromatography (silica, 0-5% MeOH/DCM gradient elution) to give tert-butyl (1S,6R,8R)-8-(((2-(trimethylsilyl)ethoxy)carbonyl)amino)-3-azabicyclo[4.2.0] octane-3-carboxylate as a sticky brown solid (800 mg, 94%); MS m/z: 371 (M+H)$^+$.

This material was dissolved in THF (5 mL) under $N_2$ and TBAF (3.3 mL of 1 M, 3.2 mmol) was added. The reaction mixture was stirred overnight at ambient temperature. Further TBAF (3 mL of 1 M, 3 mmol) was added. After 2 hours, the reaction mixture was concentrated in vacuo. The residue was taken up in DCM and purified directly by column chromatography (silica, 0-10% MeOH/DCM gradient elution) to give a colourless oil. This material was dissolved in DCM (5 mL) and the solution cooled to −5° C. DIPEA (565 µL, 3.2 mmol) was added, followed by the dropwise addition of methanesulfonyl chloride (84 µL, 1.1 mmol). The reaction mixture was stirred for 2 hours, with the temperature rising to 5° C. The reaction mixture was quenched by addition of a small amount of water then concentrated to dryness in vacuo. The residue was taken up in DCM and purified by column chromatography (silica, 0-10% MeOH/DCM gradient elution) to give tert-butyl (1S,6R,8R)-8-(methylsulfonamido)-3-azabicyclo[4.2.0]octane-3-carboxylate as a glass (70 mg, 21% over two steps); MS m/z: 305 (M+H)⁺.

This material was dissolved in DCM (5 mL) and TFA (500 µL) added. The reaction mixture was stirred for 3 hours at ambient temperature then concentrated in vacuo. The residue was azeotroped with DCM (×3), then taken up in MeOH and filtered through an SPE bicarbonate cartridge. The filtrate was concentrated in vacuo to give N-((1SR,6RS,8RS)-3-azabicyclo[4.2.0]octan-8-yl)methanesulfonamide A44 as a pale yellow glass (39 mg, 83%), which was taken on to the next reaction without further purification; MS m/z: 205 (M+H)⁺.

Preparation 44: 3-(Piperidin-3-yl)oxetan-3-amine A45

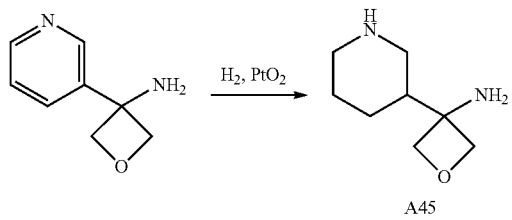

3-(3-Pyridyl)oxetan-3-amine hydrochloride (100 mg, 0.5 mmol) was dissolved in MeOH (10 mL). The solution was re-circulated for 8 hours through a PtO₂ catalyst cartridge at 2.5 mL min⁻¹, under 60 bar of H₂ pressure at 60° C. in an H-cube. The solution was then concentrated in vacuo to give 3-(piperidin-3-yl)oxetan-3-amine A45 as a pale yellow solid (84 mg, 80%), which was taken directly on to the next reaction; MS m/z: 157 (M+H)⁺.

Preparation 45: N-(((3S,5S)-4,4-Difluoro-5-methylpiperidin-3-yl)methyl)methanesulfonamide A46

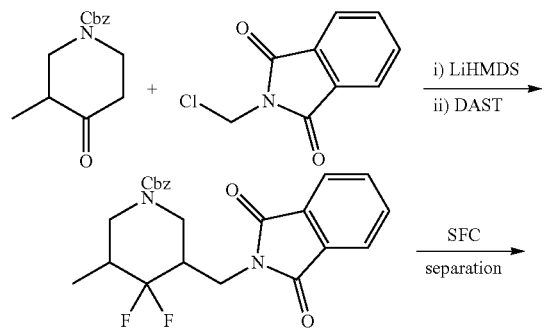

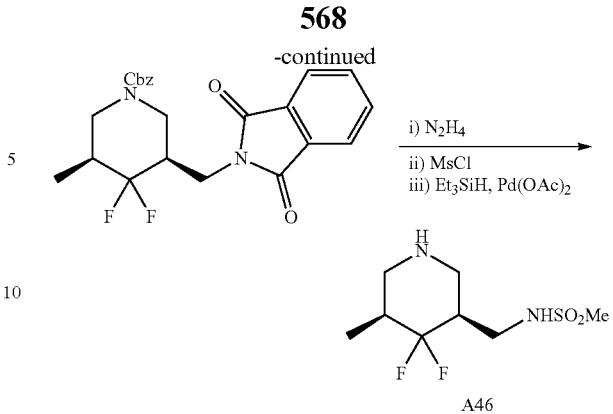

Benzyl 3-methyl-4-oxo-piperidine-1-carboxylate (20 g, 0.08 mol) was dissolved in THF (300 mL) under N₂. The solution was cooled to −78° C. and LiHMDS (1 M in THF, 101.1 mL, 0.1 mol) was added dropwise over 20 minutes, keeping the temperature below −70° C. After stirring at −78° C. for 90 minutes, a solution of 2-(chloromethyl)isoindoline-1,3-dione (23.7 g, 0.12 mol) in THF (200 mL) was added dropwise over 25 minutes, keeping the temperature below −70° C. The reaction was stirred at −78° C. for 1 hour then quenched at −78° C. by the addition of saturated aqueous ammonium chloride solution (65 mL) and the mixture allowed to warm to ambient temperature. The reaction was repeated and the two mixtures obtained were combined and extracted with EtOAc (300 mL). The organic phase was washed with saturated aqueous sodium bicarbonate solution (300 mL) and brine (300 mL), dried (Na₂SO₄), filtered and concentrated in vacuo. The residue was purified by column chromatography (silica, EtOAc/PE elution). The product fractions were combined and concentrated in vacuo and the residue recrystallized from EtOAc to give benzyl 3-((1,3-dioxoisoindolin-2-yl)methyl)-5-methyl-4-oxopiperidine-1-carboxylate as a white solid (7.56 g, 23%).

A flask was charged with benzyl 3-((1,3-dioxoisoindolin-2-yl)methyl)-5-methyl-4-oxopiperidine-1-carboxylate (60 g, 0.15 mol) and cooled in an ice/water bath. DAST (325 mL, 2.5 mol) was added in one portion and the mixture stirred at ambient temperature for 3 days. The resulting yellow solution was diluted with DCM (1 L) and slowly added to a mixture of ice/water and solid sodium bicarbonate with overhead stirring. The temperature remained below 0° C. and additional sodium bicarbonate was added to maintain a pH of 7-8. The mixture was warmed to ambient temperature and the layers separated. The aqueous phase was extracted with DCM (2 L). The combined organics were washed with brine, dried (Na₂SO₄), filtered and concentrated in vacuo. The residue was purified by column chromatography (silica, EtOAc/PE elution) to give benzyl 3-((1,3-dioxoisoindolin-2-yl)methyl)-4,4-difluoro-5-methylpiperidine-1-carboxylate as a glass (32.5 g, 51%); ¹H NMR (400 MHz, chloroform-d) δ 7.89-7.64 (4H, m), 7.42-7.11 (5H, m), 5.15-5.03 (2H, m), 4.39-4.07 (3H, m), 3.83-3.66 (1H, m), 2.97-2.60 (2H, m), 2.56-2.31 (1H, m), 2.08-1.89 (1H, m), 1.05 (3H, d) as a mixture of isomers.

Preparative chiral supercritical fluid chromatography (conditions: Chiralpak® IC 5 µm, CO₂/iPrOH 90/10, 230 nm) was used to isolate the single enantiomer benzyl (3R,5S)-3-[(1,3-dioxoisoindolin-2-yl)methyl]-4,4-difluoro-5-methyl-piperidine-1-carboxylate, (98.7% ee).

To a suspension of benzyl (3R,5S)-3-[(1,3-dioxoisoindolin-2-yl)methyl]-4,4-difluoro-5-methyl-piperidine-1-carboxylate (9.6 g, 22.4 mmol) in ethanol (144 mL) was added hydrazine hydrate (8.5 mL, 112 mmol). The reaction mixture was heated under reflux for 5 hours then allowed to cool to ambient temperature overnight. The resulting suspension was filtered and the precipitate washed with EtOH (×2). The filtrate was loaded onto ion-exchange cartridges (50 g×10). The cartridges were washed with MeOH/DCM mixtures, then the product eluted with 2 M methanolic ammonia solution. The filtrates were combined and concentrated in vacuo. The residue was taken up in MeOH and concentrated in vacuo (×2), then treated with heptane and concentrated in vacuo. The resulting yellow oil was dried under vacuum overnight to give benzyl (3R,5S)-3-(aminomethyl)-4,4-difluoro-5-methyl-piperidine-1-carboxylate as a solid (6.77 g), which was taken directly on to the next reaction; $^1$H NMR (400 MHz, DMSO-$d_6$) δ 7.48-7.17 (m, 5H), 5.11 (s, 2H), 4.41 (ddt, 1H), 4.02 (d, 1H), 2.98 (dd, 1H), 2.64 (s, 2H), 2.41 (dd, 1H), 2.15-1.78 (m, 2H), 1.50 (s, 2H), 0.93 (d, 3H); MS m/z: 299 (M+H)$^+$.

Benzyl (3R,5S)-3-(aminomethyl)-4,4-difluoro-5-methyl-piperidine-1-carboxylate (6.6 g, 22 mmol) was dissolved in DCM (66 mL) and cooled in an ice bath. The internal temperature reached 3° C. Et$_3$N (3.4 mL, 24 mmol) was added with stirring. Methanesulfonyl chloride (1.88 mL, 24 mmol) was added over 5 minutes, at such a rate to keep the internal temperature below 10° C. After 30 minutes, the ice bath was removed. The solution was warmed up to ambient temperature and quenched with a saturated aqueous NaHCO$_3$ solution (66 mL). The layers were separated and the aqueous phase extracted with DCM (33 mL). The combined organics were dried (MgSO$_4$), filtered and concentrated in vacuo. The residue was purified by column chromatography (silica, 0 to 100% EtOAc/PE gradient elution). The product fractions were combined and concentrated in vacuo and the residue dried overnight under vacuum to give benzyl (3S,5S)-4,4-difluoro-3-(methanesulfonamidomethyl)-5-methyl-piperidine-1-carboxylate as a white solid (7.92 g; 95%); $^1$H NMR (400 MHz, DMSO-$d_6$) δ 7.45-7.31 (m, 5H), 7.31-7.19 (m, 1H), 5.12 (s, 2H), 4.37 (d, 1H), 4.18-3.94 (m, 1H), 3.38 (ddd, 1H), 3.00-2.80 (m, 4H), 2.68 (s, 2H), 2.15 (s, 2H), 0.95 (d, 3H); MS m/z: 377 (M+H)$^+$.

To a solution of benzyl (3S,5S)-4,4-difluoro-3-(methanesulfonamidomethyl)-5-methyl-piperidine-1-carboxylate (7.54 g, 20 mmol) in DCM (113 mL) was added Et$_3$N (8.38 mL, 60 mmol), followed by Pd(OAc)$_2$ (1.80 g, 8 mmol). Et$_3$SiH (19.20 mL, 120 mmol) was added over 5 minutes. The solution was stirred at ambient temperature for 1 hour then separated into 6 equal portions and loaded onto ion-exchange cartridges (50 g×6). The cartridges were washed with DCM, 1:1 MeOH:DCM and MeOH and the product eluted with 2 M methanolic ammonia solution. The filtrates were combined and concentrated in vacuo. The residue was azeotroped with DCM then taken up in MeOH (45 mL) and stirred with SPM32 (3-mercaptopropyl ethyl sulfide silica) for 2 hours at ambient temperature, then at 50° C. for 1 hour. The mixture was cooled, filtered through celite and the filtrate concentrated in vacuo. The residue was taken up in DCM and concentrated in vacuo. The residue was dried overnight under vacuum to give N-(((3S,5S)-4,4-difluoro-5-methylpiperidin-3-yl)methyl)methanesulfonamide A46 as a white solid (4.40 g, 91%); $^1$H NMR (400 MHz, DMSO-d6) δ 7.10 (t, 1H), 3.43-3.33 (m, 1H), 3.26-3.10 (m, 1H), 2.93-2.88 (m, 4H), 2.79 (dtd, 1H), 2.38-2.20 (m, 2H), 2.13-1.78 (m, 2H), 0.89 (d, 3H); MS m/z: 243 (M+H)$^+$.

Preparation 46: N-[[(2S)-Morpholin-2-yl]methyl]methanesulfonamide A47

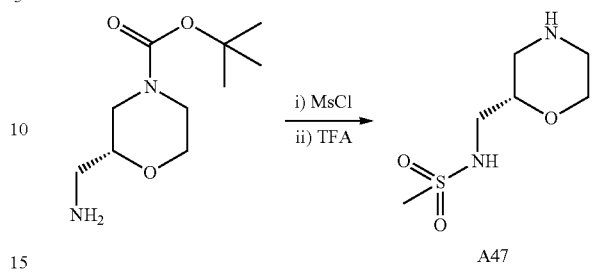

To a round bottom flask was added tert-butyl (2R)-2-(aminomethyl)morpholine-4-carboxylate (5 g, 23 mmol) and Et$_3$N (16.1 mL, 115 mmol) followed by THF (100 mL). DCM (50 mL) was added and the mixture was cooled to 0° C. Methanesulfonyl chloride (2.4 mL, 30.5 mmol) was added dropwise and the mixture stirred for 30 minutes, then left at ambient temperature for 16 hours under an atmosphere of N$_2$. The reaction was quenched with saturated aqueous NaHCO$_3$ solution (100 mL) and concentrated in vacuo. The aqueous layer was extracted with ethyl acetate (3×50 mL). The combined organics were dried (Na$_2$SO$_4$), filtered and concentrated in vacuo. The residue was purified by column chromatography (silica, 70 to 100% EtOAc/PE gradient elution). The product fractions were combined and concentrated in vacuo. The residue was dried overnight under vacuum to give tert-butyl (2S)-2-(methanesulfonamidomethyl)morpholine-4-carboxylate (3.61 g, 53%) as a white solid; $^1$H NMR (500 MHz, Chloroform-d) δ 4.71-4.59 (m, 1H), 3.98-3.82 (m, 2H), 3.63-3.49 (m, 2H), 3.38-3.24 (m, 1H), 3.20-3.11 (m, 1H), 3.04-2.90 (m, 4H), 2.73 (s, 1H), 1.49 (s, 9H).

TFA (9 mL, 115 mmol) was added to a stirred solution of tert-butyl (2S)-2-(methanesulfonamidomethyl)morpholine-4-carboxylate (3.6 g, 12 mmol) in DCM (60 mL) and the reaction stirred at ambient temperature for 6 hours. The solvent was removed in vacuo and the residue azeotroped with DCM (×2) and diethyl ether (×2). The residue was taken up in MeOH and passed through an ion-exchange cartridge, washing with methanol then eluting the product with a 2 M methanolic ammonia solution. The filtrate was concentrated in vacuo to give N-[[(2S)-morpholin-2-yl]methyl]methanesulfonamide A47 (2.3 g, 97%); $^1$H NMR (500 MHz, Chloroform-d) δ 4.73 (s, 1H), 3.90-3.87 (m, 1H), 3.65-3.60 (m, 2H), 3.26 (dd, 1H), 3.09 (dd, 1H), 2.99 (s, 3H), 2.92-2.84 (m, 3H), 2.66 (dd, 1H), MS m/z: 195 (M+H)$^+$.

Preparation 47: N-[(4-Hydroxy-4-methyl-3-piperidyl)methyl]methanesulfonamide A48

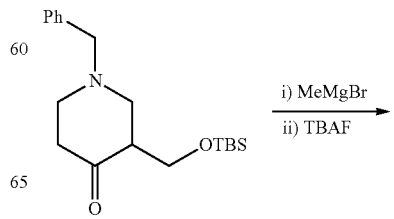

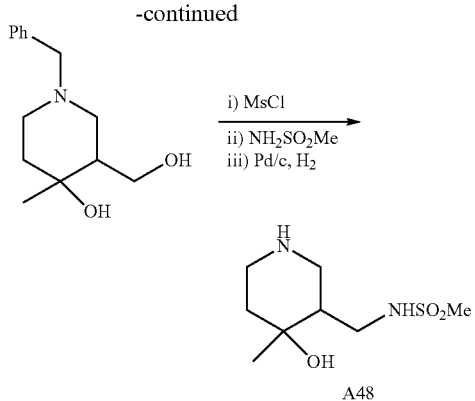

A solution of 1-benzyl-3-[[tert-butyl(dimethyl)silyl]oxymethyl]piperidin-4-one (2.5 g, 7.5 mmol) in diethyl ether (22 mL) under $N_2$ was cooled to 0° C. before the dropwise addition of MeMgBr (3 mL of a 3 M solution in ether, 9 mmol). The stirred mixture was then allowed to warm to ambient temperature over 20 minutes. The mixture was diluted with saturated aqueous $NH_4Cl$ solution and EtOAc. The organic layer was separated, dried ($MgSO_4$), filtered and concentrated in vacuo. The residue was dissolved in THF (3 mL) and treated with TBAF (2.5 mL of a 75% w/v solution in water, 7.2 mmol) and stirred at ambient temperature for 16 hours. The mixture was concentrated in vacuo and dissolved in DCM (8 mL). $Et_3N$ (2.7 mL, 19 mmol) was added under $N_2$ and the solution cooled in an ice bath. Methanesulfonyl chloride (789 μL, 10.2 mmol) was added and the mixture stirred for 3 hours, with the temperature rising to ambient. Methanesulfonyl chloride (789 μL, 10.2 mmol) was added and the reaction mixture stirred for 90 minutes. The reaction was diluted with DCM and washed with saturated aqueous $NaHCO_3$ solution and brine. The organic phase was dried ($Na_2SO_4$), filtered and concentrated in vacuo to give (1-benzyl-4-hydroxy-4-methyl-3-piperidyl)methyl methanesulfonate (2.0 g, 100%) as an oil; MS m/z: 314 (M+H)$^+$.

Methanesulfonamide (607 mg, 6.38 mmol), (1-benzyl-4-hydroxy-4-methyl-3-piperidyl)methyl methanesulfonate (2.00 g, 6.38 mmol) and $K_2CO_3$ (3.09 g, 22.3 mmol) were combined in dry DMF (24 mL) and stirred at 100° C. under nitrogen for 16 hours. The reaction mixture was cooled to ambient temperature, diluted with EtOAc and washed with saturated aqueous sodium bicarbonate solution (×2). The organic layer was dried ($Na_2SO_4$), filtered and concentrated in vacuo. The residue was purified by column chromatography (silica, 0-10% [10% $NH_4OH$ in MeOH]-DCM gradient elution) to give N-[(1-benzyl-4-hydroxy-4-methyl-3-piperidyl)methyl]methanesulfonamide (550 mg, 28%) as a yellow oil that was taken directly on to the next reaction; MS m/z: 313 (M+H)$^+$.

A round-bottomed flask was charged with N-[(1-benzyl-4-hydroxy-4-methyl-3-piperidyl)methyl]methanesulfonamide (550 mg, 1.76 mmol) in MeOH (8 mL) and concentrated HCl (147 μL of 37% w/v, 1.760 mmol) was added. The flask was degassed and filled with nitrogen (×3 vacuum-nitrogen cycles) and Pd/C (degussa) (187 mg of 10% w/w, 0.18 mmol) was added in one portion. The $N_2$ was replaced with $H_2$ (×3 vacuum-hydrogen cycles) and the reaction mixture stirred at ambient temperature. After 3 hours additional concentrated HCl (147 μL of 37% w/v, 1.760 mmol) and Pd/C (degussa) (187 mg of 10% w/w, 0.18 mmol) were added and the mixture degassed and refilled with $H_2$ as before. The mixture was stirred for 20 hours then filtered through Celite. The filtrate was concentrated in vacuo to give N-[(4-hydroxy-4-methyl-3-piperidyl)methyl]methanesulfonamide A48 (321 mg, 70%), which was taken on to the next reaction without further purification; MS m/z: 223 (M+H)$^+$.

Preparation 48: N-[(6-Methyl-3-piperidyl)methyl]methanesulfonamide A49

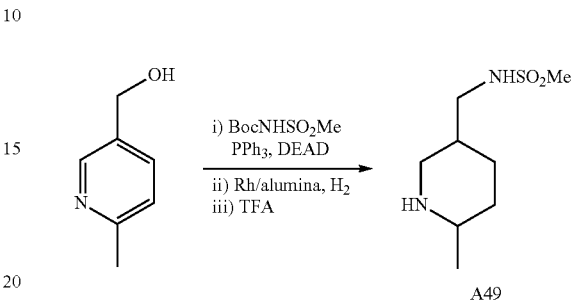

To a solution of (6-methyl-3-pyridyl)methanol (250 mg, 2.03 mmol), tert-butyl N-methylsulfonylcarbamate (590 mg, 3.02 mmol) and $PPh_3$ (1.6 g, 6.10 mmol) in THF (10 mL) was added DEAD (690 μL, 4.38 mmol) dropwise and the reaction mixture stirred at ambient temperature under nitrogen for 2 hours. The resulting precipitate was removed by filtration and the filtrate concentrated in vacuo. The residue was purified by column chromatography (silica, 0-50% EtOAc/PE gradient elution) to give tert-butyl ((6-methylpyridin-3-yl)methyl)(methylsulfonyl)carbamate (567 mg, 93%) as a white solid that was taken directly on to the next reaction; MS m/z: 301 (M+H)$^+$.

tert-Butyl ((6-methylpyridin-3-yl)methyl)(methylsulfonyl)carbamate (566 mg, 1.88 mmol) was dissolved in MeOH (30 mL). Rh on Alumina (56 mg of 5% w/w, Degussa) was added and the reaction placed under a hydrogen atmosphere and stirred at ambient temperature for 54 hours. The catalyst was removed by filtration and the filtrate concentrated in vacuo. The residue was dissolved in DCM (10 mL) and TFA (2 mL) added. The mixture was stirred at ambient temperature for 17 hours. The solvent was removed in vacuo and the residue azeotroped with DCM (×2) and diethyl ether (×2). The residue was passed through an ion-exchange cartridge, washing with MeOH/DCM mixtures then eluting the product with 2 M $NH_3$ in MeOH/DCM mixtures. The filtrates were concentrated in vacuo to give N-[(6-methyl-3-piperidyl)methyl]methanesulfonamide A49 (98 mg, 25%) as a brown solid that was taken on to the next reaction without further purification; MS m/z: 207 (M+H)$^+$.

Preparation 49: 2-Methylsulfonyl-2,6-diazaspiro[4.5]decane A50

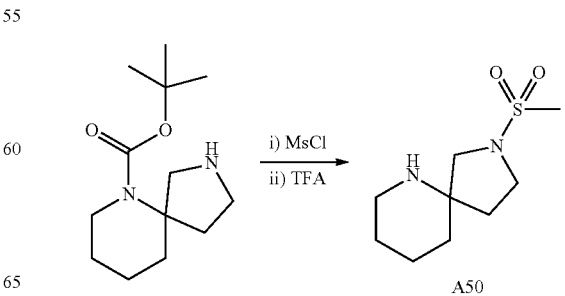

To a solution of tert-butyl 2,6-diazaspiro[4.5]decane-6-carboxylate (250 mg, 1.04 mmol) and Et₃N (200 μL, 1.44 mmol) in DCM (4 mL) was added methanesulfonyl chloride (100 μL, 1.3 mmol). The reaction mixture was stirred at ambient temperature for 3 hours then diluted with DCM and saturated aqueous NaHCO₃ solution. After 5 minutes stirring, the organic phase was isolated using a phase separation cartridge. The filtrate was concentrated in vacuo to give a colourless oil, MS m/z: 319 (M+H)⁺.

The residue was taken up in DCM (3 mL)/TFA (1 mL) and the reaction mixture stirred at ambient temperature for 2 hours. The mixture was concentrated in vacuo to give 2-methylsulfonyl-2, 6-diazaspiro[4.5]decane A50 (250 mg, 72%) as a yellow oil that was taken directly on to the next reaction.

Preparation 50: N-[[5-(Dimethylamino)-4,4-difluoro-3-piperidyl]methyl]methane Sulfonamide A51

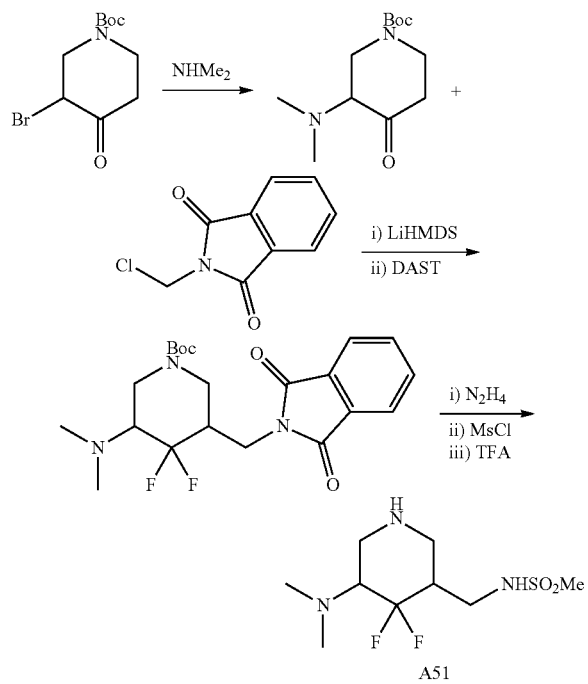

tert-Butyl 3-bromo-4-oxo-piperidine-1-carboxylate (2 g, 7.2 mmol) was suspended in THF (2 mL) and cooled in an ice bath before addition of dimethylamine (16 mL of 2 M, 32 mmol). Upon complete addition, the ice bath was removed and the mixture was stirred at ambient temperature for 16 hours. The mixture was partitioned between saturated aqueous sodium bicarbonate solution and EtOAc. The organic phase was dried (Na₂SO₄), filtered and concentrated in vacuo. The residue was dissolved in THF (28 mL) under N₂. The solution was cooled to −78° C. and LiHMDS (10 mL of 1 M, 10 mmol) was added dropwise. After 40 minutes, 2-(chloromethyl)isoindoline-1,3-dione (2.32 g, 11.8 mmol) was added in portions over 5 minutes. The solution was stirred for 1 hour then left to warm up to 0° C. before being quenched by addition of saturated aqueous NH₄Cl solution. The mixture was partitioned between saturated aqueous sodium bicarbonate solution and EtOAc. The organic layer was separated, dried (Na₂SO₄), filtered and concentrated in vacuo. The residue was purified by column chromatography (silica, 0-10% MeOH/DCM gradient elution) to give tert-butyl 3-(dimethylamino)-5-[(1,3-dioxoisoindolin-2-yl)methyl]-4-oxo-piperidine-1-carboxylate (1.58 g, 50%); MS m/z: 402 (M+H)⁺.

tert-Butyl 3-(dimethylamino)-5-[(1,3-dioxoisoindolin-2-yl)methyl]-4-oxo-piperidine-1-carboxylate (1.4 g, 3.5 mmol) in DCM (5 mL) was cooled in an ice bath before slowly adding DAST (3.7 mL, 28 mmol). The mixture was stirred under N₂ for 3.5 hours. The ice bath was removed and DAST (2 mL, 15 mmol) added and the mixture stirred for 18 hours. Additional DAST (3.7 mL, 28 mmol) was added and the mixture stirred for a further 18 hours. The mixture was quenched by slow addition to a mixture of ice/DCM with vigorous stirring. The aqueous phase was carefully basified by addition of NaHCO₃, the layers separated and the organic phase dried (Na₂SO₄), filtered and concentrated in vacuo. The residue was purified by column chromatography (silica, 0-15% MeOH/DCM gradient elution) to give tert-butyl 3-(dimethylamino)-5-[(1,3-dioxoisoindolin-2-yl)methyl]-4,4-difluoro-piperidine-1-carboxylate (500 mg, 34%); MS m/z: 424 (M+H)⁺.

tert-Butyl 3-(dimethylamino)-5-[(1,3-dioxoisoindolin-2-yl)methyl]-4,4-difluoro-piperidine-1-carboxylate (500 mg, 1.181 mmol) and hydrazine hydrate (240 μL of 50% w/v, 2.4 mmol) were combined in EtOH (5 mL) and the mixture heated under reflux for 1 hour. The mixture was allowed to cool to ambient temperature then loaded onto an ion-exchange cartridge. The product was eluted with methanolic ammonia solution and the filtrate concentrated in vacuo. The residue was dissolved in DCM (5 mL), the solution cooled in an ice bath and Et₃N (494 μL, 3.5 mmol) then methanesulfonyl chloride (114 μL, 1.5 mmol) were added. After 5 minutes the ice bath was removed and the mixture stirred at ambient temperature overnight. Methanesulfonyl chloride (25 μL, 0.3 mmol) was added. After 30 minutes saturated aqueous sodium bicarbonate solution was added. The mixture was stirred vigorously for 5 minutes then passed through a phase separation cartridge. The filtrate was concentrated in vacuo. The residue was dissolved in DCM (3 mL) and TFA (1.5 mL) was added. The mixture was stirred at ambient temperature for 45 minutes then concentrated in vacuo. The residue was loaded on to an ion-exchange cartridge, washing with DCM/MeOH mixtures then eluting the product with a methanolic ammonia solution. The filtrate was concentrated in vacuo to give N-[[5-(dimethylamino)-4,4-difluoro-3-piperidyl]methyl]methane sulfonamide A51 (219 mg, 68%) as an oil that was taken directly on to the next reaction without further purification; MS m/z: 272 (M+H)⁺.

Preparation 51: N-[(2,6-Dimethyl-3-piperidyl)methyl]methanesulfonamide A52

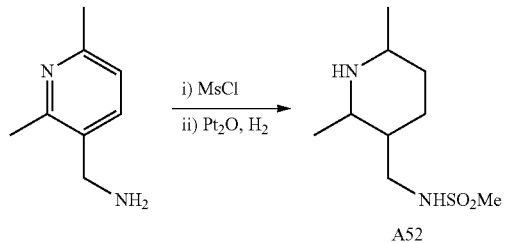

Et₃N (600 μL, 4.3 mmol) then methanesulfonyl chloride (300 μL, 4 mmol) were added to an ice cold solution of (2,6-dimethyl-3-pyridyl)methanamine (400 mg, 3 mmol) in DCM (10 mL) under N$_2$. After 5 minutes, the ice bath was removed and the solution stirred at ambient temperature for 1 hour. The solution was diluted with DCM and saturated aqueous NaHCO$_3$ solution. After 5 minutes stirring, the organic phase was isolated using a phase separation cartridge. The filtrate was concentrated in vacuo to give N-[(2,6-dimethyl-3-pyridyl)methyl]methanesulfonamide (700 mg), which was taken on to the next step without further purification; MS m/z: 215 (M+H)$^+$.

A suspension of N-[(2,6-dimethyl-3-pyridyl)methyl]methanesulfonamide (700 mg, 3.3 mmol), PtO$_2$ (200 mg, 0.9 mmol) and HCl (5 mL of a 3 M solution in MeOH, 15 mmol) in MeOH (2 mL) was shaken in a Parr hydrogenator under a 60 psi H$_2$ pressure for 72 hours. The reaction mixture was filtered and the filtrate concentrated in vacuo to give N-[(2,6-dimethyl-3piperidyl)methyl]methanesulfonamide A52 (500 mg, 69%) as a colourless oil that was taken on to the next reaction without further purification; MS m/z: 221 (M+H)$^+$.

Preparation 52: ((2S,6S)-6-(Trifluoromethyl)morpholin-2-yl)methanol A53 and ((2R,6S)-6-(trifluoromethyl)morpholin-2-yl)methanol A54

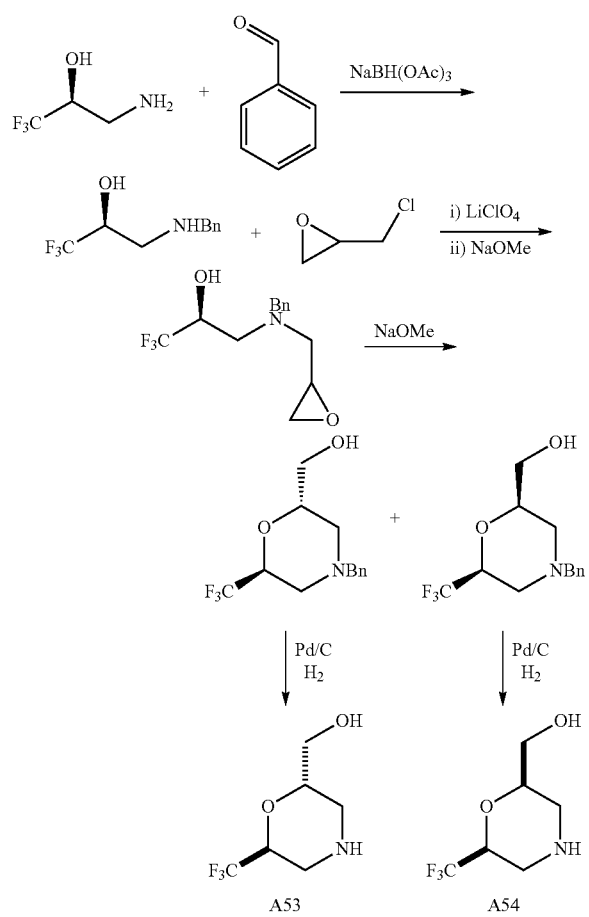

A mixture of (2S)-3-amino-1,1,1-trifluoro-propan-2-ol hydrochloride (1.0 g, 6.0 mmol), benzaldehyde (740 μL, 7.3 mmol), DIPEA (1.2 mL, 6.889 mmol) and crushed 4 Å MS (1 g) in DCE (30 mL) were stirred at ambient temperature for 1.5 hours. NaBH(OAc)$_3$ (2.56 g, 12.1 mmol) was added and the reaction stirred at ambient temperature for a further 18.5 hours. The mixture was filtered through Celite (washing with DCM) and the filtrate concentrated in vacuo. The residue was purified by column chromatography (silica, 0-10% (10% NH$_4$OH in MeOH)/DCM gradient elution) to give an off-white solid that was dissolved in DCM and passed through an ion-exchange cartridge. The cartridge was washed with MeOH/DCM mixtures and the product eluted by washing the cartridge with 2 M NH$_3$ in MeOH/DCM mixtures. The solvent was removed in vacuo to give (2S)-3-(benzylamino)-1,1,1-trifluoro-propan-2-ol (515 mg, 39%) as a white solid; $^1$H NMR (500 MHz, DMSO-d$_6$) δ 7.35-7.30 (m, 4H), 7.25-7.22 (m, 1H), 6.22 (d, 1H), 4.10-4.02 (m, 1H), 3.74 (d, 2H), 2.70 (dd, 1H), 2.65-2.61 (m, 1H), 2.18 (br s, 1H); $^{19}$F NMR (471 MHz, DMSO-d$_6$) δ −76.87; MS m/z: 220 (M+H)$^+$.

A solution of (2S)-3-(benzylamino)-1,1,1-trifluoro-propan-2-ol (515 mg, 2.35 mmol) in toluene (10 mL) was treated with 2-(chloromethyl)oxirane (240 μL, 3.1 mmol) and lithium perchlorate (325 mg, 3.06 mmol) and the mixture stirred at ambient temperature for 18 hours. MeOH (2.6 mL) and sodium methoxide (320 mg, 5.9 mmol) were added and the reaction stirred at ambient temperature for a further 25 hours. The reaction was quenched by the addition of saturated aqueous NH$_4$Cl and the aqueous layer extracted with EtOAc (×3). The combined organic extracts were washed with brine, dried (MgSO$_4$), filtered and concentrated in vacuo. The residue was purified by column chromatography (silica, 0-100% EtOAc-PE gradient elution) and the relevant fractions concentrated in vacuo. The residue was dissolved in MeOH (5 mL). Sodium methoxide (320 mg, 5.9 mmol) was added and the reaction heated under reflux for 21 hours. The reaction was cooled to ambient temperature and quenched by the addition of saturated aqueous NH$_4$Cl solution. The aqueous layer was diluted with water to dissolve salts and extracted with EtOAc (×3). The combined organic extracts were dried (MgSO$_4$), filtered and concentrated in vacuo. The residue was purified by column chromatography (silica, 0-30% EtOAc-PE gradient elution) to give [(2S,6S)-4-benzyl-6-(trifluoromethyl)morpholin-2-yl]methanol (221.9 mg, 34%) as a colourless oil; $^1$H NMR (500 MHz, DMSO-d$_6$) δ 7.47-7.11 (m, 5H), 4.70 (t, 1H), 4.34 (ddt, 1H), 3.87 (d, 1H), 3.59-3.45 (m, 4H), 2.56-2.49 (m, 3H), 2.30 (dd, 1H); and [(2R,6S)-4-benzyl-6-(trifluoromethyl)morpholin-2-yl]methanol (86.1 mg, 13%) as a colourless oil; $^1$H NMR (500 MHz, DMSO-d$_6$) δ 7.37-7.26 (m, 5H), 4.78 (t, 1H), 4.26-4.19 (m, 1H), 3.65-3.60 (m, 1H), 3.61 (d, 1H), 3.54 (d, 1H), 3.45 (dt, 1H), 3.35 (dt, 1H), 2.89 (dt, 1H), 2.81 (dt, 1H), 2.03 (t, 1H), 1.87-1.83 (m, 1H).

A mixture of [(2S,6S)-4-benzyl-6-(trifluoromethyl)morpholin-2-yl]methanol (220 mg, 0.8 mmol), Pd on C, wet, Degussa (30 mg, 0.3 mmol) and HCl in MeOH (5 mL of 3 M, 15.0 mmol) was placed under an atmosphere of hydrogen and stirred at ambient temperature for 24 hours. The catalyst was removed by filtration through Celite, washing with MeOH, and the filtrate concentrated in vacuo to give [(2S,6S)-6-(trifluoromethyl)morpholin-2-yl]methanol A53 (183 mg, 103%) as a yellow oil that was taken on to the next step without further purification (assuming the mono HCl salt); $^1$H NMR (500 MHz, DMSO-d$_6$) δ 9.40 (s, 2H), 4.78-4.71 (m, 1H), 4.07 (p, 1H), 3.70 (dd, 1H), 3.64 (dd, 1H), 3.40 (dd, 1H), 3.30-3.23 (m, 2H), 3.17 (dd, 1H); MS m/z: 186 (M+H)$^+$.

A mixture of [(2R,6S)-4-benzyl-6-(trifluoromethyl)morpholin-2-yl]methanol (86 mg, 0.312 mmol), Pd on C, wet, Degussa 10% w/w (15 mg, 0.14 mmol) and HCl in MeOH (3 mL of 3 M, 9.0 mmol) was placed under an atmosphere of hydrogen and stirred at ambient temperature for 24 hours. The catalyst was removed by filtration through Celite, washing with MeOH, and the filtrate concentrated in vacuo to give [(2R,6S)-6-(trifluoromethyl)morpholin-2-yl]methanol A54 (76.2 mg, quantitative yield) that was taken on to the next step without further purification (assuming the mono HCl salt); $^1$H NMR (500 MHz, DMSO-d$_6$) δ 9.79 (s, 2H), 4.66-4.60 (m, 1H), 4.02-3.98 (m, 1H), 3.54-3.48 (m, 3H), 3.32-3.29 (m, 1H), 3.00 (t, 1H), 2.90 (t, 1H); MS m/z: 186.0 (M+H)$^+$.

Preparation 53: ((2R,6R)-6-(Trifluoromethyl)morpholin-2-yl)methanol A55 and ((2S,6R)-6-(Trifluoromethyl)morpholin-2-yl)methanol A56

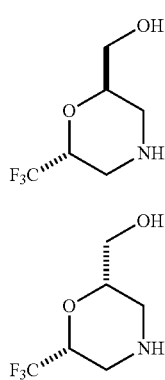

Using the method described in Preparation 52 for A53 and A54, A55 and A56 were prepared using (2R)-3-amino-1,1,1-trifluoro-propan-2-ol hydrochloride in place of (2S)-3-amino-1,1,1-trifluoro-propan-2-ol hydrochloride.

((2R,6R)-6-(Trifluoromethyl)morpholin-2-yl)methanol A55 was obtained as the free base; $^1$H NMR (500 MHz, DMSO-d$_6$) δ 4.68 (br s, 1H), 4.19-4.12 (m, 1H), 3.72-3.67 (m, 1H), 3.56-3.54 (m, 2H), 2.91 (dd, 1H), 2.80 (dd, 1H), 2.74 (dd, 1H), 2.65 (dd, 1H), 2.39 (br s, 1H); MS m/z: 186 (M+H)$^+$.

((2S,6R)-6-(Trifluoromethyl)morpholin-2-yl)methanol A56 was obtained as the free base; $^1$H NMR (500 MHz, DMSO-d$_6$) δ 4.72 (t, 1H), 4.06-4.00 (m, 1H), 3.53-3.48 (m, 1H), 3.41 (dt, 1H), 3.35-3.31 (m, 2H), 2.93-2.90 (m, 1H), 2.85-2.81 (m, 1H), 2.59 (br s, 1H), 2.33 (dd, 1H); MS m/z: 186 (M+H)$^+$.

Preparation 54: (S)—N-(Piperidin-3-ylmethyl)methanesulfonamide A57

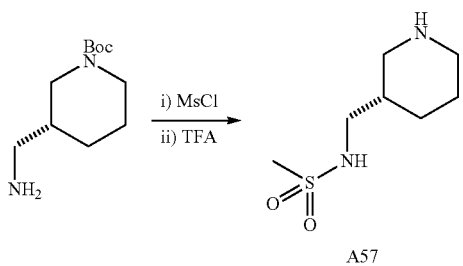

Methanesulfonyl chloride (465 μL, 6.0 mmol) was added to a stirred solution of tert-butyl (3R)-3-(aminomethyl)piperidine-1-carboxylate (1.0 g, 4.7 mmol) and Et$_3$N (1 mL, 7.2 mmol) in THF (20 mL) under an atmosphere of nitrogen and the reaction was stirred at ambient temperature for 16 hours. The reaction was diluted with DCM and saturated aqueous NaHCO$_3$ and the mixture was stirred for 10 minutes. The layers were separated and the aqueous layer extracted with DCM (×2). The combined organic extracts were dried (MgSO$_4$), filtered and concentrated in vacuo to give a pale yellow oil that was taken up in DCM (30 mL). TFA (7.5 mL, 97.4 mmol) was added and the reaction mixture was stirred at ambient temperature for 20 hours. The solvent was removed in vacuo and the residue azeotroped with DCM (×2) and diethyl ether (×2). The residue was passed through an ion-exchange cartridge and washed with MeOH/DCM mixtures. The product was eluted by washing the cartridge with 2 M NH$_3$ in MeOH/DCM mixtures. The solvent was removed in vacuo to give (S)—N-(piperidin-3-ylmethyl)methanesulfonamide A57 (846 mg, 94%) as a colourless oil; $^1$H NMR (500 MHz, Chloroform-d) δ 3.13 (dd, 1H), 3.06 (d, 2H), 3.02-2.98 (m, 1H), 2.97 (s, 3H), 2.64-2.58 (m, 1H), 2.41 (dd, 1H), 1.89-1.83 (m, 1H), 1.75-1.67 (m, 1H), 1.59 (br s, 1H), 1.54-1.45 (m, 1H), 1.22-1.14 (m, 1H); MS m/z: 193 (M+H)$^+$.

Preparation 55: Mixture of N-((4,4-Difluoro-2-methylpiperidin-3-yl)methyl)methanesulfonamide A58 and N-((4,4-difluoro-6-methylpiperidin-3-yl)methyl)methanesulfonamide, A59

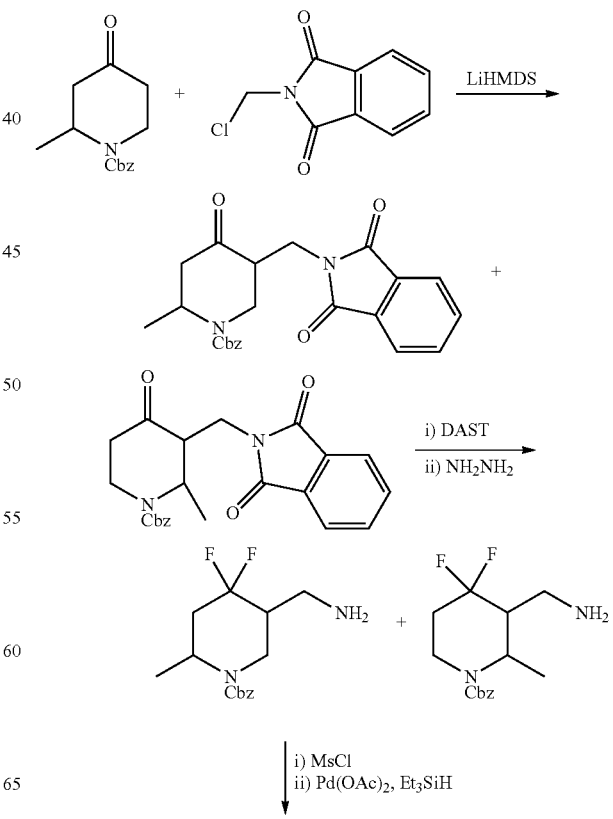

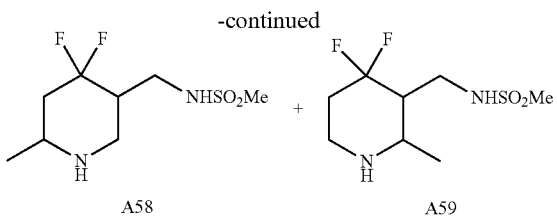

LiHMDS (37 mL of a 1 M solution in THF, 37.0 mmol) was added dropwise to a stirred solution of benzyl 2-methyl-4-oxo-piperidine-1-carboxylate (7.5 g, 30.3 mmol) in THF (150 mL) at −78° C. under $N_2$. After 50 minutes, a solution of 2-(chloromethyl)isoindoline-1,3-dione (8.0 g, 40.9 mmol) in THF (30 mL) was added to the reaction mixture over 5 minutes. The solution was stirred for 2 hours then quenched with a saturated aqueous $NH_4Cl$ solution. After warming to ambient temperature, the reaction mixture was diluted with EtOAc, washed with saturated aqueous sodium bicarbonate solution and brine. The organic phase was dried ($MgSO_4$), filtered and concentrated in vacuo. The residue was purified by column chromatography (silica, 0-100% EtAOc/PE gradient elution) to give a mixture of benzyl 5-((1,3-dioxoisoindolin-2-yl)methyl)-2-methyl-4-oxopiperidine-1-carboxylate and benzyl 3-((1,3-dioxoisoindolin-2-yl)methyl)-2-methyl-4-oxopiperidine-1-carboxylate (2.4 g). This material was treated with DAST (8 mL, 61 mmol), with cooling in an ice bath. The resulting solution was stirred at 0° C. for 15 minutes, then left to warm up to ambient temperature and stirred for 5 hours. The solution was poured carefully, dropwise, onto a stirred mixture of ice/water/$NaHCO_3$/DCM. After 30 minutes, the organic phase was isolated and washed with brine. The organic was dried ($Na_2SO_4$), filtered and concentrated in vacuo. The crude mixture was purified by column chromatography (silica, 0-100% EtOAc-PE gradient elution) give a colourless oil (1.5 g), of which 540 mg was dissolved in ethanol (15 mL) and hydrazine hydrate (100 µL, 2.0 mmol) added. The mixture was heated under reflux for 3 hours then cooled to ambient temperature. The resulting suspension was filtered and the filtrate poured directly onto a pre-wetted ion-exchange cartridge. The cartridge was washed with methanol and the product eluted with a 2 M methanolic ammonia solution. The filtrate was concentrated under reduced pressure to give a pale yellow oil (300 mg). This material was dissolved in DCM (3 mL) and $Et_3N$ (200 µL, 1.4 mmol) was added under $N_2$. The solution was cooled in an ice bath and methanesulfonyl chloride (100 µL, 1.3 mmol) added. After 5 minutes the cooling bath was removed and the mixture stirred at ambient temperature for 2 hours. The solution was diluted with DCM and saturated aqueous $NaHCO_3$ solution. After stirring for 5 minutes, the organic phase was isolated using a phase separation cartridge. After concentration in vacuo, the residue was purified by column chromatography (silica, 0-100% [10% MeOH in EtOAc]-PE gradient elution) to give a pale yellow oil (150 mg). This material was taken up in DCM (3 mL) and Pd(OAc)$_2$ (40 mg, 0.18 mmol), $Et_3SiH$ (150 µL, 0.94 mmol) and $Et_3N$ (100 µL, 0.72 mmol) were added. The reaction mixture was stirred at ambient temperature for 1 hour then diluted with MeOH. It was added onto a pre-wetted ion-exchange cartridge. The cartridge was washed with MeOH then the product eluted with a 2 M methanolic $NH_3$ solution. The filtrate was concentrated under reduced pressure to give a brown oil (70 mg) containing a mixture of N-((4,4-difluoro-2-methylpiperidin-3-yl)methyl)methanesulfonamide A58 and N-((4,4-difluoro-6-methylpiperidin-3-yl)methyl)methanesulfonamide A59, that was taken directly on to the next reaction; MS m/z: 234 $(M+H)^+$.

Preparation 56: tert-Butyl ((3-methylpiperazin-2-yl) methyl)(methylsulfonyl)carbamate A60

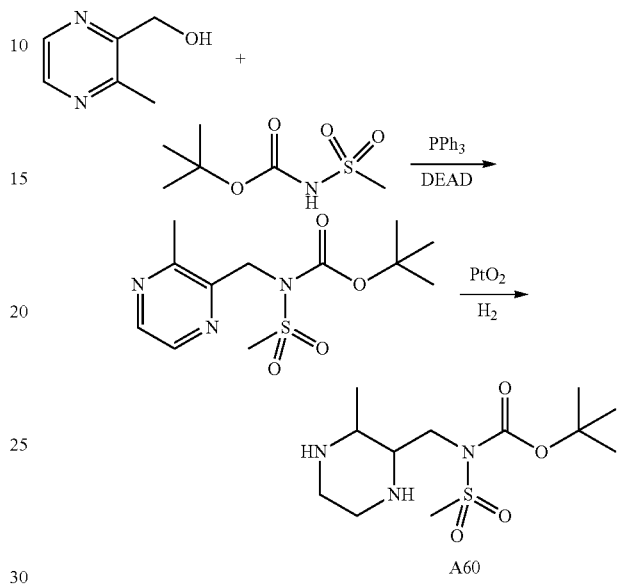

DEAD (810 µL, 5.1 mmol) was added dropwise to a solution of $PPh_3$ (2.0 g, 7.7 mmol), (3-methylpyrazin-2-yl) methanol (300 mg, 2.42 mmol) and tert-butyl N-methylsulfonylcarbamate (1.1 g, 5.6 mmol) in DCM (15 mL). The solution was stirred at ambient temperature for 36 hours. The resulting suspension was diluted with DCM and saturated aqueous $NaHCO_3$ solution. After stirring for 5 minutes, the organic phase was isolated using a phase separation cartridge, then concentrated in vacuo. The residue was purified by column chromatography (silica, 0-100% EtOAc-PE gradient elution) to give tert-butyl ((3-methylpyrazin-2-yl)methyl)(methylsulfonyl)carbamate as a white solid (1.0 g).

tert-butyl ((3-methylpyrazin-2-yl)methyl)(methylsulfonyl)carbamate (500 mg, 1.66 mmol) was dissolved in 3 M methanolic HCl solution (20 mL) and $PtO_2$ (200 mg, 0.9 mmol) added. The reaction mixture was shaken in a Parr hydrogenator for 18 hours under 60 psi $H_2$ pressure. The mixture was filtered and the catalyst washed with methanol. The filtrate was concentrated under reduced pressure to give tert-butyl ((3-methylpiperazin-2-yl)methyl)(methylsulfonyl)carbamate A60 as an off-white solid (500 mg, 79%) that was taken directly on to the next reaction without purification (assuming the bis-HCl salt); MS m/z: 308 $(M+H)^+$.

Preparation 57: (3S,5S)-4,4-Difluoro-3-methyl-5-[(sulfamoylamino)methyl]piperidine A61

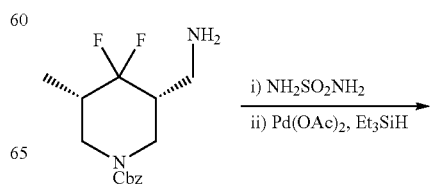

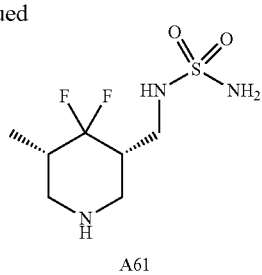

Benzyl (3R,5S)-3-(aminomethyl)-4,4-difluoro-5-methyl-piperidine-1-carboxylate (100 mg, 0.34 mmol) (see A46) and sulfamide (81 mg, 0.84 mmol) were dissolved in 1,4-dioxane (1 mL) under $N_2$. The reaction mixture was heated to 100° C. and stirred for 16 hours. The reaction was cooled and partitioned between EtOAc and water. The layers were separated and the aqueous phase extracted with EtOAc (×2). The combined organics were washed with brine, dried ($Na_2SO_4$), filtered and concentrated in vacuo to a yellow oil (147 mg); MS m/z: 378 (M+H)$^+$.

This material was dissolved in DCM (2 mL) and DIPEA (190 μL, 1.1 mmol) then $Et_3SiH$ (340 μL, 2.13 mmol) added. The mixture was degassed with $N_2$ and $Pd(OAc)_2$ (32 mg, 0.14 mmol) added under $N_2$. After 15 minutes the mixture was diluted with DCM and filtered through GF/C paper. The filtrate was loaded on to an ion-exchange cartridge, washing with DCM then DCM-MeOH (1:1) and eluting the product with 2 M methanolic ammonia solution. The filtrate was concentrated in vacuo to give (3S,5S)-4,4-difluoro-3-methyl-5-[(sulfamoylamino)methyl]piperidine A61 as a colourless glass (43 mg, 49%); $^1$H NMR (500 MHz, DMSO-$d_6$) δ 6.57 (d, 3H), 3.23 (d, 1H), 2.93-2.85 (m, 1H), 2.74-2.66 (m, 1H), 2.25 (q, 2H), 2.08-1.80 (m, 2H), 0.89 (d, 3H); MS m/z: 244 (M+H)$^+$.

Preparation 58:
2-(Piperidin-3-yl)ethane-1-sulfonamide A62

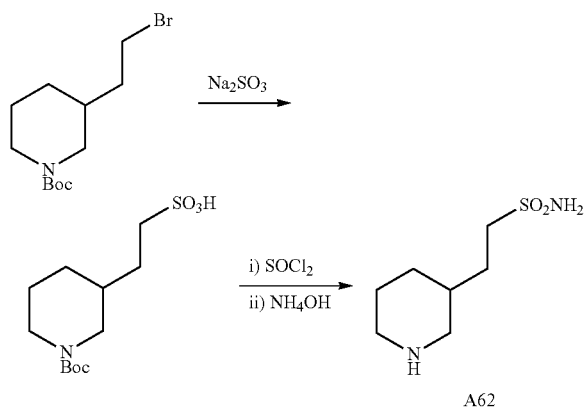

tert-Butyl 3-(2-bromoethyl)piperidine-1-carboxylate (270 mg, 0.92 mmol) was suspended in EtOH (2 mL) and water (2 mL), and $Na_2SO_3$ (233 mg, 1.85 mmol) added. The mixture was stirred under reflux for 16 hours. The reaction mixture was concentrated to dryness in vacuo. The residue was taken up in MeCN/water and freeze dried to give a white powder (406 mg). This material was suspended in $SOCl_2$ (2.0 mL, 27.4 mmol) in a reaction tube under $N_2$. The reaction mixture was heated to 80° C. and stirred for 16 hours. The mixture was cooled to ambient temperature and concentrated in vacuo. The residue was treated with aqueous $NH_4OH$ (3 mL of 30% w/v solution) at ambient temperature and NMP (2 mL) was added to solubilise the mixture. After 1 hour the mixture was concentrated in vacuo and the resulting suspension filtered to remove inorganic salts. The resulting clear NMP solution of 2-(piperidin-3-yl)ethane-1-sulfonamide A62 was used directly in next reaction; MS m/z: 193 (M+H)$^+$.

Preparation 59:
2-(Morpholin-2-yl)ethane-1-sulfonamide A63

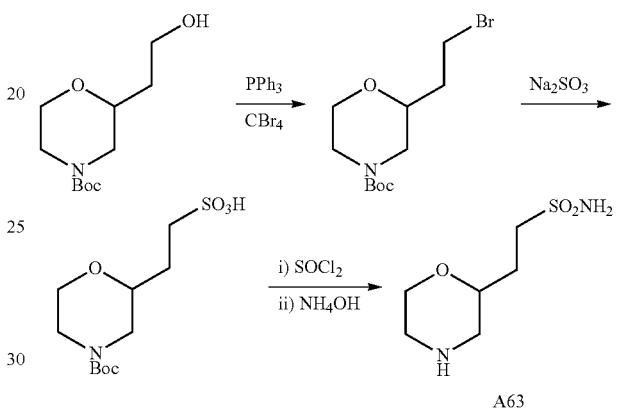

$CBr_4$ (3.05 g, 9.2 mmol) was added to a stirred solution of tert-butyl 2-(2-hydroxyethyl)morpholine-4-carboxylate (1.42 g, 6.14 mmol), $PPh_3$ (1.53 g, 5.83 mmol) and imidazole (835 mg, 12.3 mmol) in DCM (30 mL) at 0° C. under an atmosphere of nitrogen and the reaction mixture was allowed to warm to ambient temperature over 17 hours. The reaction mixture was diluted with DCM, washed with water (×2) and brine, dried ($MgSO_4$), filtered and concentrated in vacuo. The residue was purified by column chromatography (silica, 0-30% EtOAc-PE) to give tert-butyl 2-(2-bromoethyl)morpholine-4-carboxylate (951 mg, 55%) as a white solid; $^1$H NMR (500 MHz, Chloroform-d) δ 3.88 (d, 2H), 3.88 (br s, 1H), 3.60-3.50 (m, 4H), 2.94 (s, 1H), 2.64 (s, 1H), 2.09-2.02 (m, 1H), 1.98-1.92 (m, 1H), 1.49 (s, 9H); MS m/z: 194 (M-Boc)$^+$.

tert-Butyl 2-(2-bromoethyl)morpholine-4-carboxylate (250 mg, 0.85 mmol) was suspended in EtOH (2 mL) and water (2 mL), and $Na_2SO_3$ (214 mg, 1.70 mmol) was added. The mixture was stirred under reflux for 16 hours. The reaction mixture was concentrated to dryness and the residue taken up in MeCN/water and freeze dried to give a white powder (330 mg), which was taken on to next reaction without further purification. The material was suspended in $SOCl_2$ (2 mL, 27.4 mmol) under $N_2$. The mixture was heated to 80° C. and stirred for 16 hours. The mixture was cooled to ambient temperature, concentrated in vacuo and the residue treated with aqueous $NH_4OH$ (3 mL of 30% w/v) at ambient temperature. NMP (2 mL) was added to solubilise the mixture. After 1 hour the mixture was concentrated in vacuo to remove aqueous ammonia and the resulting suspension filtered to remove inorganic salts. The resulting clear NMP solution of 2-(morpholin-2-yl)ethane-1-sulfonamide A63 was used directly in the next reaction; MS m/z: 195 (M+H)$^+$.

Preparation 60: tert-Butyl ((5,5-difluoro-2-methylpiperidin-3-yl)methyl)(methylsulfonyl)carbamate A64

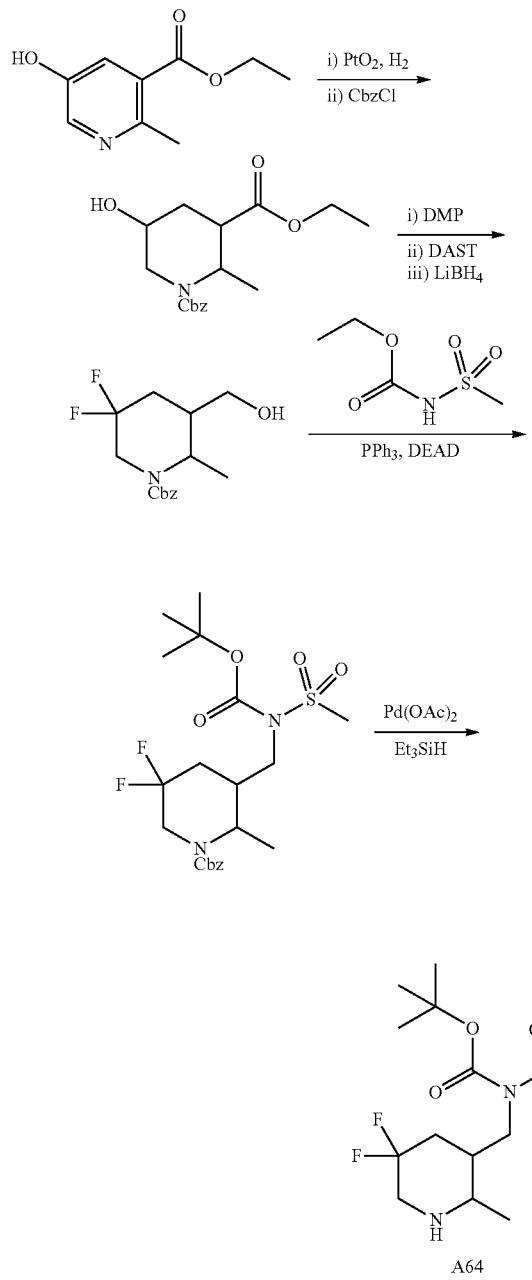

A mixture of ethyl 5-hydroxy-2-methyl-pyridine-3-carboxylate (500 mg, 2.8 mmol) and PtO$_2$ (300 mg, 1.3 mmol) in 3 M methanolic HCl (30 mL, 90 mmol) was shaken in a Parr hydrogenator for 18 hours at 60 psi H$_2$ pressure. The reaction mixture was filtered and the filtrate concentrated in vacuo to give ethyl 5-hydroxy-2-methyl-piperidine-3-carboxylate hydrochloride as a yellow oil (800 mg), which was taken directly on to the next step.

Benzyl chloroformate (1.9 mL, 13.1 mmol) was added to a suspension ethyl 5-hydroxy-2-methyl-piperidine-3-carboxylate hydrochloride (2.5 g, 11.2 mmol) and potassium carbonate (15 g, 109 mmol) in EtOAc (50 mL) and water (25 mL). The reaction was stirred vigorously for 18 hours at ambient temperature. The organic phase was separated and collected, and the aqueous phase extracted with ethyl acetate. The combined organic extracts were washed with water and brine, dried (Na$_2$SO$_4$) and concentrated in vacuo. The residue was purified by column chromatography (silica, 0-100% EtOAc-PE gradient elution) to give 1-benzyl 3-ethyl 5-hydroxy-2-methylpiperidine-1,3-dicarboxylate as a colourless oil (270 mg) that was taken directly on to the next step without further purification; MS m/z: 322 (M+H)$^+$.

Dess-Martin periodinane (360 mg, 0.85 mmol) was added to an ice cold solution of 1-benzyl 3-ethyl 5-hydroxy-2-methylpiperidine-1,3-dicarboxylate (270 mg, 0.84 mmol) in DCM (5 mL) under N$_2$. After 5 minutes, the cooling bath was removed and the mixture stirred at ambient temperature for 24 hours. The resulting suspension was diluted with DCM, saturated aqueous NaHCO$_3$ solution and saturated aqueous Na$_2$S$_2$O$_3$ solution. After stirring for 30 minutes, the organic phase was isolated using a phase separation cartridge and the filtrate concentrated under reduced pressure to give a yellow oil. This material was treated with DAST (1.2 mL, 9.1 mmol) and the resulting solution stirred at ambient temperature for 4 hours. The solution was poured carefully onto a stirred mixture of DCM, ice, water and NaHCO$_3$. After stirring for 10 minutes, the organic phase was isolated using a phase separation cartridge. The filtrate was concentrated in vacuo and the residue purified by column chromatography (silica, 0-60% EtOAc-PE gradient elution) to give a colourless oil (110 mg) that was taken on to the next step without further purification; MS m/z: 342 (M+H)$^+$.

Lithium borohydride (200 μL of 2 M, 0.40 mmol) was added to an ice cold solution of 1-benzyl 3-ethyl 5,5-difluoro-2-methyl-piperidine-1,3-dicarboxylate (110 mg, 0.32 mmol) in THF (4 mL) under N$_2$. The solution was stirred for 18 hours, with the temperature rising to ambient. The reaction mixture was quenched with saturated aqueous NaHCO$_3$ solution. DCM was added to the mixture and the organic phase was isolated using a phase separation cartridge. The filtrate was concentrated under reduced pressure to give a brown oil (100 mg) that was taken directly on to the next reaction without further purification; MS m/z: 300 (M+H)$^+$.

DEAD (100 μL, 0.6351 mmol) was added to an ice cold solution of benzyl 5,5-difluoro-3-(hydroxymethyl)-2-methyl-piperidine-1-carboxylate (100 mg, 0.33 mmol), PPh$_3$ (250 mg, 0.95 mmol) and tert-butyl N-methylsulfonylcarbamate (130 mg, 0.67 mmol) in DCM (4 mL) under N$_2$. The reaction mixture was stirred at ambient temperature for 20 hours. The resulting suspension was diluted with DCM and saturated aqueous NaHCO$_3$ solution. After stirring for 5 minutes, the organic phase was isolated using a phase separation cartridge. The filtrate was concentrated under reduced pressure and the residue purified by column chromatography (silica, 0-100% EtOAc-PE gradient elution) to give a colourless oil (120 mg). This material was taken up in DCM (5 mL) and Pd(OAc)$_2$ (25 mg, 0.11 mmol), Et$_3$SiH (100 μL, 0.63 mmol) and Et$_3$N (70 μL, 0.50 mmol) were added. The mixture was stirred at ambient temperature for 1 hour then diluted with MeOH. The solution was poured onto a pre-wetted ion-exchange cartridge washing with methanol then eluting the product with a 2 M methanolic NH$_3$ solution. The filtrate was concentrated to give tert-butyl ((5,5-difluoro-2-methylpiperidin-3-yl)methyl)(methylsulfonyl)carbamate A64 as a brown oil (70 mg) that was taken on to the next reaction without further purification; MS m/z: 343 (M+H)$^+$.

Preparation 61:
((2S)-3-Methylmorpholin-2-yl)methanol A65 and C-3 epimer A66

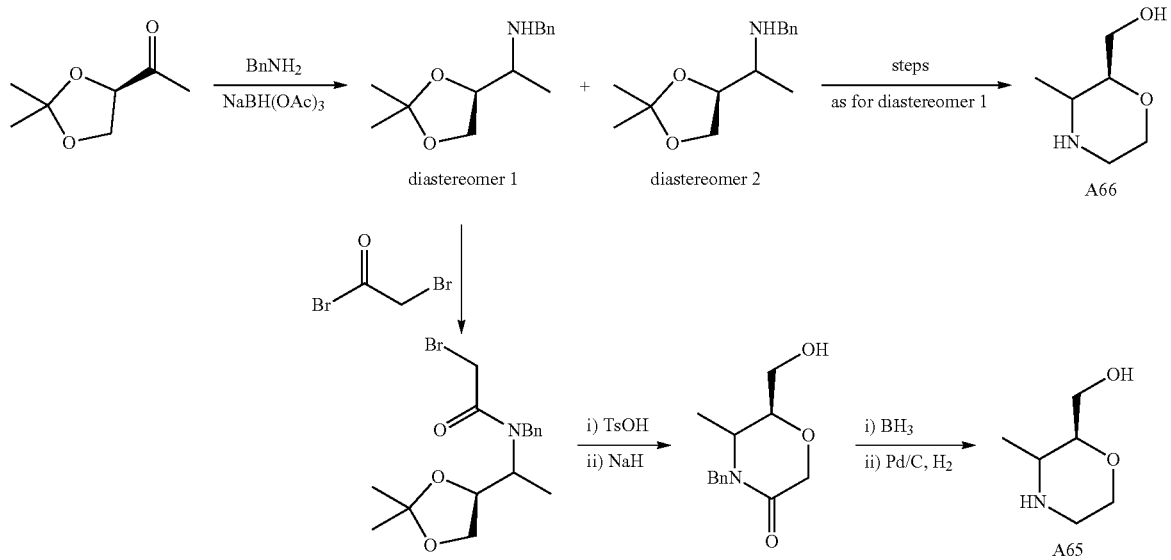

1-[(4R)-2,2-Dimethyl-1,3-dioxolan-4-yl]ethanone (2.4 g, 16.7 mmol) was dissolved in DCE (132 mL). Acetic acid (5.2 mL, 91.6 mmol) and benzyl amine (10.0 mL, 91.6 mmol) were added and the reaction mixture stirred for 30 minutes at ambient temperature, then cooled to 0° C. Sodium triacetoxy borohydride (14.1 g, 66.6 mmol) was added portionwise over 25 minutes. The reaction mixture was stirred for 16 hours with the temperature rising to ambient temperature. Saturated aqueous NaHCO$_3$ solution was added and the mixture extracted with DCM (×2). The combined organics were washed with NaHCO$_3$ solution, dried (MgSO$_4$) and concentrated in vacuo. The residue was purified by column chromatography (silica, 20-80% EtOAc-PE gradient elution). Two diastereomers were isolated in ~2:1 ratio: (Minor) diastereomer 1 (800 mg); $^1$H NMR (400 MHz, methanol-d$_4$) δ 7.41-7.21 (m, 5H), 4.85 (s, 2H), 4.05 (dd, 1H), 3.98-3.88 (m, 2H), 3.72 (d, 1H), 3.66 (dd, 1H), 2.71 (dq, 1H), 1.33 (d, 6H), 1.03 (d, 3H); (Major) diastereomer 2 (2.9 g, containing 1 equivalent of BnNH$_2$); $^1$H NMR (400 MHz, methanol-d$_4$) δ 7.44-7.20 (m, 10H, 5H from BnNH$_2$), 4.09-4.01 (m, 2H), 3.88 (d, 1H), 3.82-3.77 (m, 1H), 3.76-3.70 (m, 3H, 2H from BnNH$_2$), 2.89-2.70 (m, 1H), 1.38 (s, 3H), 1.33 (d, 3H), 1.12 (d, 3H).

Diastereomer 1 (100 mg, 0.42 mmol) was dissolved in DCM (4 mL) under N$_2$. Et$_3$N (150 μL, 1.1 mmol) was added and the mixture cooled in an ice bath. 2-Bromoacetyl bromide (75 μL, 0.85 mmol) was added and the reaction mixture allowed to warm to ambient temperature. After 45 minutes the reaction mixture was diluted with DCM and washed with water (×2). The organic phase was dried (MgSO$_4$), filtered and concentrated in vacuo to a brown oil (110 mg) that was taken on to the next step without further purification; MS m/z: 357 (M+H)$^+$.

4-Methylbenzenesulfonic acid hydrate (150 μL, 0.84 mmol) was added to a solution of N-benzyl-2-bromo-N-[1-[(4S)-2,2-dimethyl-1,3-dioxolan-4-yl]ethyl]acetamide (600 mg, 1.68 mmol) in MeOH (6 mL) and the mixture was stirred at ambient temperature for 16 hours. The reaction mixture was concentrated in vacuo, and the residue dissolved in EtOAc and washed with saturated aqueous NaHCO$_3$ (×2). The aqueous phase was extracted with EtOAc (×3). The combined organic phases were dried (MgSO$_4$), filtered and concentrated in vacuo to give an oil (530 mg) that was taken directly on to the next step; MS m/z: 317 (M+H)$^+$.

NaH (100 mg, 4.2 mmol) was added to a solution of N-benzyl-2-bromo-N-[(2S)-2,3-dihydroxy-1-methyl-propyl]acetamide (530 mg, 1.68 mmol) in THF (11 mL) and the reaction stirred at ambient temperature for 100 minutes. The reaction was quenched by slow addition of water, and the mixture extracted with ethyl acetate. The organic phase was dried and concentrated in vacuo. The residue (200 mg) was taken directly on to the next reaction; MS m/z: 236 (M+H)$^+$.

BH$_3$.THF (4.25 mL of 1 M, 4.25 mmol) was added to a solution of (6S)-4-benzyl-6-(hydroxymethyl)-5-methyl-morpholin-3-one (200 mg, 0.85 mmol) in THF (3 mL) with stirring at 0° C. under N$_2$. After addition was complete, the ice bath was removed and the reaction mixture stirred at ambient temperature for 40 minutes. The reaction mixture was cooled in an ice bath and MeOH added until no effervescence was observed. The reaction mixture was concentrated, and the residue taken up in MeOH and passed through an ion-exchange cartridge washing with MeOH and eluting the product with a methanolic ammonia solution. The filtrate was concentrated in vacuo to give an oil (140 mg) that was taken directly on to the next step; $^1$H NMR (400 MHz, MeOH-d$_4$) δ 7.45-7.17 (m, 5H), 4.15 (d, 1H), 3.80 (ddd, 1H), 3.74 (dd, 1H), 3.67 (dd, 1H), 3.65-3.57 (m, 1H), 3.33 (p, 1H), 3.25 (ddd, 1H), 3.20 (d, 1H), 2.61 (dt, 1H), 2.39 (dq, 1H), 2.25 (td, 1H), 1.24 (d, 3H).

A mixture of [(2S)-4-benzyl-3-methyl-morpholin-2-yl]methanol (140 mg, 0.63 mmol), Pd on C, wet, Degussa 10% w/w (30 mg, 0.29 mmol) and 3 M methanolic HCl (6 mL) was placed under an atmosphere of hydrogen and stirred at ambient temperature for 16 hours. The reaction mixture was filtered through Celite and the filtrate concentrated to dryness in vacuo. The residue, ((2S)-3-methylmorpholin-2-yl)methanol A65 (103 mg) was taken on to the next reaction without purification or characterisation assuming the HCl salt was isolated in quantitative yield.

The epimer A66 was prepared from the major product of the reductive amination reaction (diastereoisomer 2) in the same way as described above and taken on to the next reaction without purification assuming the HCl salt was isolated in quantitative yield; $^1$H NMR (400 MHz, MeOH-d$_4$) δ 4.14 (ddd, 1H), 3.91-3.77 (m, 2H), 3.70-3.61 (m, 2H), 3.53 (dd, 1H), 3.37 (s, 1H), 3.12 (dt, 1H), 1.39 (d, 3H).

Preparation 62: (2,5-Dioxa-8-azaspiro[3.5]nonan-6-yl)methanol A67

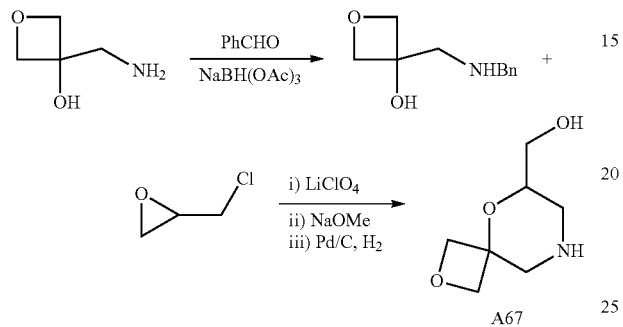

A mixture of 3-(aminomethyl)oxetan-3-ol (1.0 g, 9.7 mmol), benzaldehyde (1.2 mL, 11.8 mmol) and crushed 4 Å MS (1 g) in DCE (30 mL) were stirred at ambient temperature for 1.5 hours. NaBH(OAc)$_3$ (4.1 g, 19.4 mmol) was added and the reaction stirred at ambient temperature for a further 19 hours. The mixture was filtered through Celite (washing with DCM) and the filtrate concentrated in vacuo. The residue was passed through an ion-exchange cartridge and washed with MeOH/DCM mixtures. The product was eluted by washing the cartridge with 2 M NH$_3$ in MeOH/DCM mixtures. The filtrates were concentrated in vacuo and the residue purified by column chromatography (silica, 0-5% (10% NH$_4$OH in MeOH)/DCM gradient elution) to give 3-[(benzylamino)methyl]oxetan-3-ol (1.02 g, 55%) as a pale yellow oil; $^1$H NMR (500 MHz, Chloroform-d) δ 7.30-7.20 (m, 5H), 4.59-4.58 (m, 2H), 4.36-4.34 (m, 2H), 3.77 (s, 2H), 2.99 (s, 2H); MS m/z: 194 (M+H)$^+$.

A solution of 3-[(benzylamino)methyl]oxetan-3-ol (1.02 g, 5.28 mmol) in toluene (15 mL) was treated with 2-(chloromethyl)oxirane (540 μL, 6.90 mmol) and lithium perchlorate (730 mg, 6.86 mmol) and the mixture stirred at ambient temperature for 17 hours. The mixture was diluted with EtOAc and washed with water (×2). The combined aqueous layers were extracted with EtOAc (×2) and the combined organic extracts washed with brine, dried (MgSO$_4$), filtered and concentrated in vacuo. The residue was dissolved in MeOH (5 mL), sodium methoxide (715 mg, 13.2 mmol) was added and the reaction was heated under reflux for 23 hours. The reaction was cooled to ambient temperature and quenched by the addition of saturated aqueous NH$_4$Cl. The aqueous layer was diluted with water to dissolve salts and extracted with EtOAc (×3) and the combined organic extracts were dried (MgSO$_4$), filtered and concentrated in vacuo. The residue was purified by column chromatography (silica, 0-100% EtOAc-PE gradient elution) to give (8-benzyl-2,5-dioxa-8-azaspiro[3.5]nonan-6-yl)methanol (381 mg, 29%) as a colourless oil; $^1$H NMR (500 MHz, DMSO-d$_6$) δ 7.37-7.31 (m, 4H), 7.29-7.26 (m, 1H), 4.68 (t, 1H), 4.50 (dd, 1H), 4.37 (d, 1H), 4.33 (d, 1H), 4.23 (d, 1H), 3.53 (q, 1H), 3.48-3.41 (m, 1H), 3.35-3.28 (m, 2H), 3.05 (dd, 1H), 2.73 (dt, 1H), 2.02 (dd, 1H), 1.81 (dd, 1H); MS m/z: 251 (M+H)$^+$.

A mixture of (8-benzyl-2,5-dioxa-8-azaspiro[3.5]nonan-6-yl)methanol (380 mg, 1.52 mmol), Pd on C, wet, Degussa 10% w/w (60 mg, 0.56 mmol) and 3 M methanolic HCl (15 mL, 45 mmol) was placed under an atmosphere of hydrogen and stirred at ambient temperature for 3 hours. The catalyst was removed by filtration through Celite, washing with MeOH, and the filtrate concentrated in vacuo. The residue was passed through an ion-exchange cartridge and washed with MeOH/DCM mixtures. The product was eluted by washing the cartridge with 2 M NH$_3$ in MeOH/DCM mixtures and the solvent removed in vacuo to give 2,5-dioxa-8-azaspiro[3.5]nonan-6-ylmethanol A67 (243 mg, 100%) as a colourless oil; MS m/z: 160 (M+H)$^+$.

Preparation 63: (4-Oxa-7-azaspiro[2.5]octan-5-yl)methanol A68

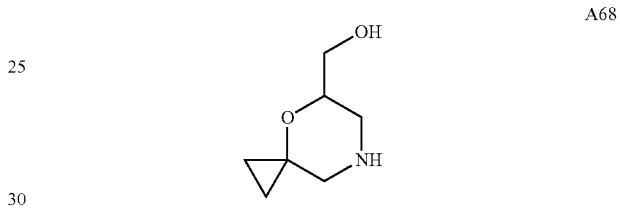

Using the same method as above for A67, (4-oxa-7-azaspiro[2.5]octan-5-yl)methanol A68 was prepared using 1-(aminomethyl)cyclopropanol in place of 3-(aminomethyl)oxetan-3-ol; $^1$H NMR (500 MHz, DMSO-d$_6$) δ 4.53-4.51 (m, 1H), 3.48-3.43 (m, 1H), 3.32-3.23 (m, 2H), 3.03 (dd, 1H), 2.86 (ddd, 1H), 2.39 (dd, 1H), 2.16 (d, 1H), 0.69-0.65 (m, 1H), 0.54-0.39 (m, 3H); MS m/z: 144 (M+H)$^+$.

Preparation 64: Mixture of N-((4-hydroxy-4,6-dimethylpiperidin-3-yl)methyl)methanesulfonamide A69 and N-((4-hydroxy-2,4-dimethylpiperidin-3-yl)methyl)methanesulfonamide A70

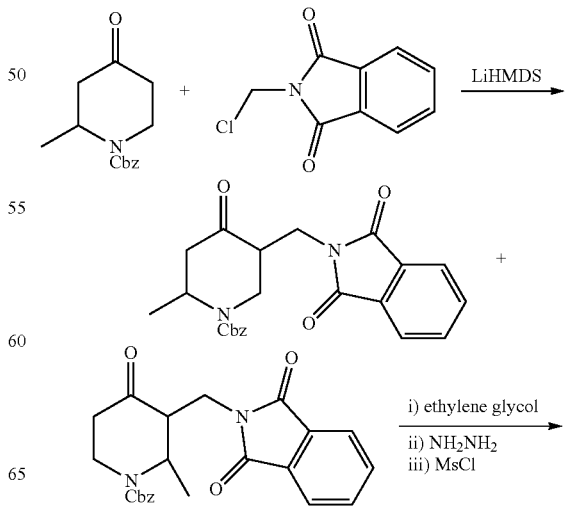

-continued

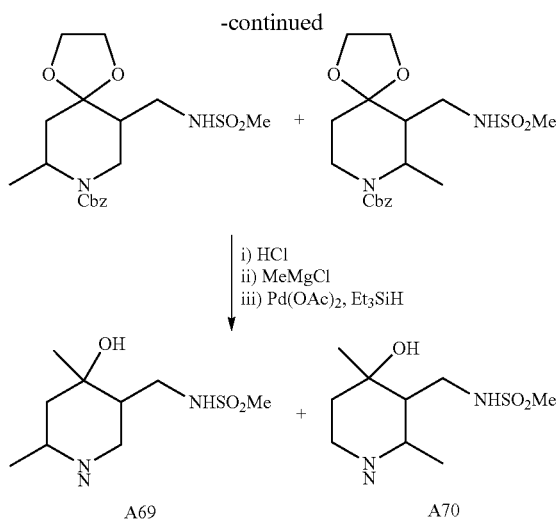

LiHMDS (10 mL of a 1 M solution, 10 mmol) was added dropwise to a solution of benzyl 2-methyl-4-oxo-piperidine-1-carboxylate (2.0 g, 8.1 mmol) in THF (40 mL) cooled to −78° C. under N$_2$. After 50 minutes, a solution of 2-(chloromethyl)isoindoline-1,3-dione (2.1 g, 10.7 mmol) in THF (~30 mL) was added to the reaction mixture over 5 minutes. The solution was stirred for 2 hours then quenched with a saturated aqueous NH$_4$Cl solution. The reaction mixture was warmed to ambient temperature, diluted with EtOAc and washed with saturated aqueous sodium bicarbonate solution and brine. The organic phase was dried (MgSO$_4$), filtered and concentrated in vacuo. The residue was purified by column chromatography (silica, 0-100% EtOAc-PE gradient elution) to give a mixture of regioisomers (as drawn) (1.7 g); MS m/z: 407 (M+H)$^+$. This material was dissolved in toluene (15 mL) and ethylene glycol (330 μL, 5.92 mmol) and 4-methylbenzenesulfonic acid hydrate (20 mg, 0.11 mmol) was added. The mixture was heated under reflux for 18 hours then cooled to ambient temperature. The reaction mixture was diluted with EtOAc, washed with saturated aqueous sodium bicarbonate solution and brine. The organic phase was dried (MgSO$_4$), filtered and concentrated in vacuo. The residue was purified by column chromatography (silica, 0-100% EtOAc-PE gradient elution) to give a colourless oil (480 mg); MS m/z: 451 (M+H)$^+$. This material was dissolved in ethanol (7 mL) and hydrazine hydrate (250 μL of 50% w/v, 2.5 mmol) was added. The mixture was heated under reflux for 2 hours then cooled to ambient temperature. The resulting suspension was filtered and the filtrate concentrated in vacuo to give a white solid. The residue was dissolved in DCM (5 mL) and Et$_3$N (200 μL, 1.44 mmol) added under N$_2$. The solution was cooled in an ice bath and methanesulfonyl chloride (100 μL, 1.29 mmol) added. After 5 minutes the cooling bath was removed and the reaction mixture stirred at ambient temperature for 18 hours. The resulting suspension was diluted with DCM and a saturated aqueous NaHCO$_3$ solution. After stirring for 5 minutes, the organic phase was isolated using a phase separation cartridge. The filtrate was concentrated in vacuo and the residue purified by column chromatography (silica, 0-100% EtOAc-PE gradient elution) to give a gum (240 mg); MS m/z: 399 (M+H)$^+$. This material was dissolved in THF (4 mL) and treated with aqueous HCl (1.5 mL of a 2 M solution, 3.0 mmol). The mixture was heated under reflux for 18 hours then cooled to ambient temperature. The reaction mixture was diluted with EtOAc then washed with saturated aqueous sodium bicarbonate solution and brine. The organic phase was dried (MgSO$_4$), filtered and concentrated in vacuo. The residue was purified by column chromatography (silica, 0-100% EtOAc-PE gradient elution) to give a colourless gum (120 mg); MS m/z: 355 (M+H)$^+$. This material was dissolved in THF (3 mL) under N$_2$ and the solution cooled in an ice bath. MeMgBr (300 μL of a 3 M solution in Et$_2$O, 0.90 mmol) was added and the reaction mixture stirred for 2 hours. The reaction mixture was quenched with saturated aqueous ammonium chloride solution then diluted with EtOAc. The organic phase was washed with brine, dried (Na$_2$SO$_4$), filtered and concentrated in vacuo to give a colourless oil. The residue was taken up in DCM (3 mL). Et$_3$N (100 μL, 0.72 mmol), Et$_3$SiH (100 μL, 0.63 mmol) and Pd(OAc)$_2$ (76 mg, 0.34 mmol) were successively added to the reaction mixture. After stirring at ambient temperature for 90 minutes the solution was loaded onto an SCX-2 cartridge. The cartridge was washed with MeOH/DCM mixtures then the product eluted with 2 M methanolic ammonia solution. The filtrate was concentrated in vacuo to give a mixture of N-((4-hydroxy-4,6-dimethylpiperidin-3-yl)methyl)methanesulfonamide A69 and N-((4-hydroxy-2,4-dimethylpiperidin-3-yl)methyl)methanesulfonamide A70 (70 mg); MS m/z: 237 (M+H)$^+$; that was taken on to the next reaction without further purification or characterisation.

Preparation 65: Imino(methyl)(piperidin-3-ylmethyl)-λ$^6$-sulfanone A71

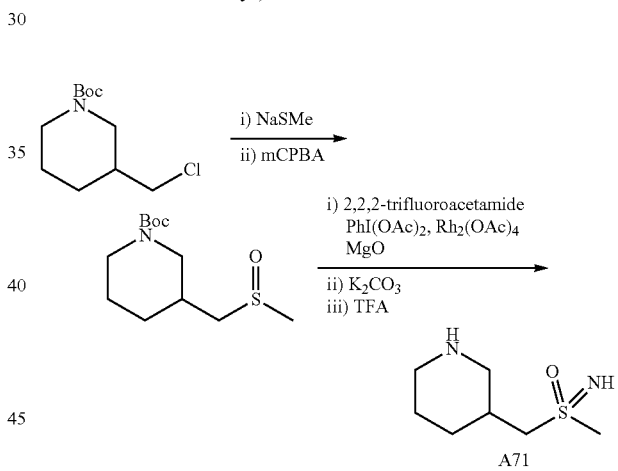

A mixture of tert-butyl 3-(chloromethyl)piperidine-1-carboxylate (500 mg, 2.14 mmol), NaSMe (3 mL of 20% w/v, 8.56 mmol) and KI (355 mg, 2.14 mmol) in ethanol (10 mL) was stirred at 80° C. for 22 hours. The reaction mixture was cooled to ambient temperature then concentrated in vacuo. The residue was partitioned between EtOAc and saturated aqueous sodium bicarbonate solution. The organic phase was washed with brine, dried (MgSO$_4$), filtered and concentrated in vacuo to give the product as a pale brown oil (460 mg, 88%) that was taken on to the next step without further purification or characterisation.

mCPBA (324 mg, 1.88 mmol) was added to an ice cold solution of tert-butyl 3-(methylsulfanylmethyl)piperidine-1-carboxylate (460 mg, 1.88 mmol) in DCM (7 mL) under N$_2$. The reaction mixture was stirred for 20 hours, with the temperature rising to ambient. The reaction mixture was diluted with DCM, washed with saturated aqueous sodium bicarbonate solution and brine. The organic phase was dried (MgSO$_4$), filtered and concentrated in vacuo to give a pale brown oil (460 mg) that was used in the next step without further purification or characterization; MS m/z: 262 (M+H)⁺.

tert-Butyl 3-(methylsulfinylmethyl)piperidine-1-carboxylate (5.5 g, 21.0 mmol), 2,2,2-trifluoroacetamide (5.2 g, 46.3 mmol), diacetoxyiodobenzene (10.2 g, 31.6 mmol) and MgO (3.39 g, 84.2 mmol) were combined in DCM (250 mL) under N₂. Rh₂(OAc)₄ (0.9 g, 2.0 mmol) was added and the reaction mixture mixture stirred at ambient temperature for 16 hours. The mixture was filtered through Celite, washing with MeOH and DCM. The filtrate was concentrated in vacuo and the residue taken up in MeOH (5 mL) and MeCN/water (3:1) (5 mL). K₂CO₃ (17.4 g, 126.0 mmol) was added and the mixture stirred at 90° C. for 2 hours. The mixture was diluted with EtOAc and washed with saturated aqueous sodium bicarbonate solution and brine. The organic phase was dried (Na₂SO₄), filtered and concentrated in vacuo to give tert-butyl 3-[(methylsulfonimidoyl)methyl]piperidine-1-carboxylate (5.96 g, 103%) as an amber oil that was taken directly on to the next reaction; MS m/z: 277 (M+H)⁺.

tert-Butyl 3-[(methylsulfonimidoyl)methyl]piperidine-1-carboxylate (600 mg, 2.17 mmol) in DCM (3 mL) was treated with TFA (1.7 mL, 21.7 mmol). The mixture was stirred at ambient temperature for 16 hours. The reaction mixture was concentrated in vacuo then dissolved in MeOH and loaded on to an ion-exchange cartridge. The cartridge was washed with MeOH/DCM then the product was with methanolic ammonia. The filtrate was concentrated in vacuo to give imino(methyl)(piperidin-3-ylmethyl)-$\lambda^6$-sulfanone A71, (250 mg, 65%); ¹H NMR (500 MHz, MeOH-d₄) δ 3.34-3.24 (m, 1H), 3.19-3.10 (m, 2H), 3.10-3.07 (m, 3H), 3.05-2.97 (m, 1H), 2.60 (ddd, 1H), 2.52-2.43 (m, 1H), 2.30-2.18 (m, 1H), 2.08 (ddtd, 1H), 1.75 (dq, 1H), 1.61 (dtq, 1H), 1.37 (dtd, 1H).

Preparation 66: 1,1,1-Trifluoro-N-(piperidin-3-ylmethyl)methanesulfonamide A72

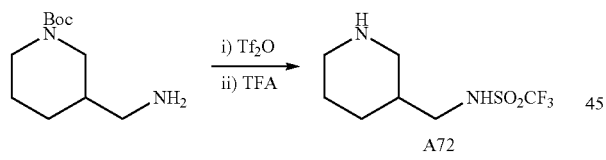

A72

Trifluoromethylsulfonyl trifluoromethanesulfonate (1.1 mL of 1 M in DCM, 1.1 mmol) was added to a solution of tert-butyl 3-(aminomethyl)piperidine-1-carboxylate (200 mg, 0.93 mmol) and DIPEA (490 µL, 2.80 mmol) in DCM (5 mL) chilled in an ice bath. The reaction mixture was stirred for 16 hours with the temperature rising to ambient, then concentrated in vacuo and the residue partitioned between DCM and saturated aqueous sodium bicarbonate solution. The organic phase was dried (MgSO₄), filtered and concentrated in vacuo. The residue was dissolved in DCM (5 mL) and TFA (1.4 mL, 18.7 mmol) was added. After stirring at ambient temperature for 1 hour the reaction mixture was concentrated in vacuo to give a yellow oil. The residue was taken up in MeOH and loaded onto an ion-exchange cartridge. The cartridge was washed with MeOH/DCM mixtures, then the product eluted with a 2 M methanolic ammonia solution. The filtrate was concentrated in vacuo to give 1,1,1-trifluoro-N-(piperidin-3-ylmethyl)methanesulfonamide A72 as a yellow oil that solidified on standing (230 mg, quantitative yield); ¹H NMR (500 MHz, Methanol-d₄) δ 3.48-3.37 (m, 1H), 3.33 (p, 2H), 3.30 (d, 1H), 3.15 (dd, 1H), 3.04 (dd, 1H), 2.86 (td, 1H), 2.64 (t, 1H), 2.00-1.82 (m, 3H), 1.79-1.62 (m, 1H), 1.38-1.21 (m, 1H).

Preparation 67: N-((5,5-Difluoro-4-methylpiperidin-3-yl)methyl)methanesulfonamide A73

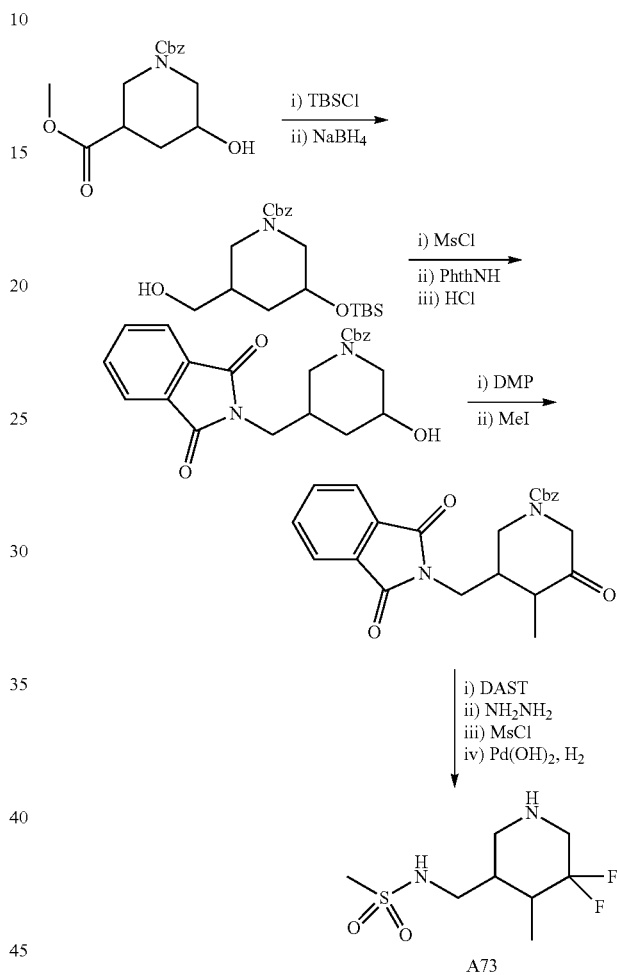

A73

To O1-benzyl O3-methyl 5-hydroxypiperidine-1,3-dicarboxylate (45.2 mL of 1 M, 45.2 mmol) was added tert-butyl-chloro-dimethyl-silane:imidazole (3.95 g, 18.1 mmol) in DMF (40 mL). The mixture was stirred at ambient temperature. After 2 hours TBSCl (2.72 g, 18.1 mmol) was added and the mixture stirred for a further 2 hours. The reaction mixture was partitioned between EtOAc and saturated aqueous sodium bicarbonate solution. The organic layer was separated, dried (Na₂SO₄), filtered and concentrated in vacuo to give O1-benzyl O3-methyl 5-[tert-butyl(dimethyl)silyl]oxypiperidine-1,3-dicarboxylate (7.36 g, quantitative yield) as an amber oil that was taken directly on to the next reaction; MS m/z: 408 (M+H)⁺.

A solution of O1-Benzyl O3-methyl 5-[tert-butyl(dimethyl)silyl]oxypiperidine-1,3-dicarboxylate (7.36 g, 18.1 mmol) in THF (50 mL) and MeOH (5 mL) was treated with NaBH₄ (2.05 g, 54.2 mmol) under N₂. After 2 hours, NaBH₄ (680 mg, 18.1 mmol) was added and after a further 2 hours the reaction mixture was quenched by addition of water (2 mL) and diluted with EtOAc. The mixture was washed with saturated aqueous sodium bicarbonate solution (×2) then brine. The organic phase was separated, dried (Na₂SO₄), filtered and concentrated to give benzyl 3-[tert-butyl(dimethyl)silyl]oxy-5-(hydroxymethyl)piperidine-1-carboxylate (6.86 g), which was taken directly on to the next reaction without further purification, assuming quantitative yield; MS m/z: 380 (M+H)⁺.

A solution of benzyl 3-[tert-butyl(dimethyl)silyl]oxy-5-(hydroxymethyl)piperidine-1-carboxylate (6.86 g, 18.1 mmol) and Et₃N (7.6 mL, 54.4 mmol) in DCM (15 mL) under N₂ was cooled to 0° C. in an ice bath. Methanesulfonyl chloride (1.5 mL, 20.0 mmol) was added dropwise. After 20 minutes the mixture was diluted with saturated aqueous sodium bicarbonate solution and extracted with EtOAc. The organic layer was separated, dried (Na₂SO₄), filtered and concentrated in vacuo to give an oil (9 g) that was taken directly on to the next reaction, assuming quantitative yield; MS m/z: 458 (M+H)⁺.

A mixture of potassium phthalimide (2.86 g, 15.5 mmol) and benzyl 3-[tert-butyl(dimethyl)silyl]oxy-5-(methylsulfonyloxymethyl)piperidine-1-carboxylate (7.86 g, 17.2 mmol) in DMF (63 mL) was heated at 110° C. After stirring for 3 hours, the reaction was allowed to cool to ambient temperature and partitioned between EtOAc and saturated aqueous sodium bicarbonate solution. The organic layer was separated and washed with brine (×2), then dried (Na₂SO₄), filtered and concentrated in vacuo to give a yellow solid which was dissolved in MeOH (20 mL) and treated with concentrated HCl (2.5 mL of 37% w/v, 25.8 mmol). The mixture was stirred for 2 hours then concentrated in vacuo. The residue was suspended in DCM and filtered. The filtrate was purified by column chromatography (silica, 15-90% EtOAc-PE gradient elution) to give benzyl 3-[(1,3-dioxoisoindolin-2-yl)methyl]-5-hydroxy-piperidine-1-carboxylate (1.86 g, 27%); MS m/z: 395 (M+H)⁺.

A solution of benzyl 3-[(1,3-dioxoisoindolin-2-yl)methyl]-5-hydroxy-piperidine-1-carboxylate (1.86 g, 4.71 mmol) in DCM (20 mL) under N₂ was treated with Dess-Martin periodinane (7.0 g, 16.5 mmol). The mixture was stirred at ambient temperature under nitrogen. After 2 hours, further Dess-Martin periodinane (2.0 g, 4.71 mmol) was added and the mixture stirred for 5 hours. The reaction mixture was quenched by the addition of 1:1 aqueous saturated sodium bicarbonate solution/saturated aqueous sodium thiosulfate solution (20 mL). The organic layer was separated, dried (Na₂SO₄), filtered and concentrated in vacuo. The residue was taken up in THF (20 mL) under N₂. The solution was cooled to −78° C. and LiHMDS (6.6 mL of a 1 M solution in THF, 6.6 mmol) added. After 15 minutes MeI (290 μL, 4.7 mmol) was added. After the addition was complete the cooling bath was removed and the reaction mixture stirred for 3 hours at ambient temperature. The reaction mixture was partitioned between EtOAc and saturated aqueous ammonium chloride solution. The organic phase was dried (Na₂SO₄), filtered and concentrated in vacuo. The residue was purified by column chromatography (silica, 0-50% EtOAc-PE gradient elution) to give benzyl 3-[(1,3-dioxoisoindolin-2-yl)methyl]-4-methyl-5-oxo-piperidine-1-carboxylate (300 mg, 16%); MS m/z: 407 (M+H)⁺.

Benzyl 3-[(1,3-dioxoisoindolin-2-yl)methyl]-4-methyl-5-oxo-piperidine-1-carboxylate (300 mg, 0.74 mmol) was dissolved in DCM (10 mL) under N₂. The solution was cooled to −78° C. and DAST (195 μL, 1.48 mmol) added. The mixture was allowed to warm to ambient temperature. After stirring for 1 hour, DAST (195 μL, 1.476 mmol) was added and after a further 2 hours another portion of DAST (195 μL, 1.48 mmol) was added. After another 2 hours, further DAST (293 μL, 2.22 mmol) was added, and another portion of DAST (586 μL, 4.44 mmol) was added after a further 3 hours. The mixture was stirred for 16 hours then slowly added to a mixture of ice and aqueous saturated sodium bicarbonate solution. The mixture was extracted with EtOAc. The organic phase was dried (Na₂SO₄), filtered and concentrated in vacuo. The residue was purified by column chromatography (silica, 0-50% EtOAc-petrol gradient elution) to give benzyl 5-[(1,3-dioxoisoindolin-2-yl)methyl]-3,3-difluoro-4-methyl-piperidine-1-carboxylate (259 mg); MS m/z: 429 (M+H)⁺.

Benzyl 5-[(1,3-dioxoisoindolin-2-yl)methyl]-3,3-difluoro-4-methyl-piperidine-1-carboxylate (259 mg, 0.60 mmol) in EtOH (10 mL) was treated with hydrazine hydrate (60 μL, 1.2 mmol) and the mixture heated under reflux for 16 hours. The reaction mixture was cooled to ambient temperature, diluted with EtOAc and washed with saturated aqueous sodium bicarbonate solution. The aqueous phase was extracted with EtOAc and the combined organic extracts dried (Na₂SO₄), filtered and concentrated in vacuo. The residue was dissolved in DCM (15 mL) and Et₃N (253 μL, 1.81 mmol) then methanesulfonyl chloride (70 μL, 0.91 mmol) added. The solution was stirred at ambient temperature for 1 hour then quenched by the addition of saturated aqueous sodium bicarbonate solution. The mixture was extracted with DCM (×2). The combined organics were dried (Na₂SO₄), filtered and concentrated in vacuo to give the desired product (206 mg); MS m/z: 377 (M+H)⁺. The residue was dissolved in MeOH (1.6 mL) and EtOAc (2.4 mL). Pd(OH)₂ (38 mg of 20% w/w, 0.05 mmol) was added and the mixture degassed (×3 vacuum-N₂ cycles). N₂ was replaced with H₂ (×3 cycles) and the mixture stirred at ambient temperature. After 72 hours the reaction mixture was filtered through Celite, eluting with MeOH. The filtrate was concentrated in vacuo to give N-((5,5-difluoro-4-methylpiperidin-3-yl)methyl)methanesulfonamide A73 (127 mg) that was taken on to the next step without further purification; MS m/z: 243 (M+H)⁺.

Preparation 68: N-((2-Ethylpiperidin-3-yl)methyl)methanesulfonamide A74

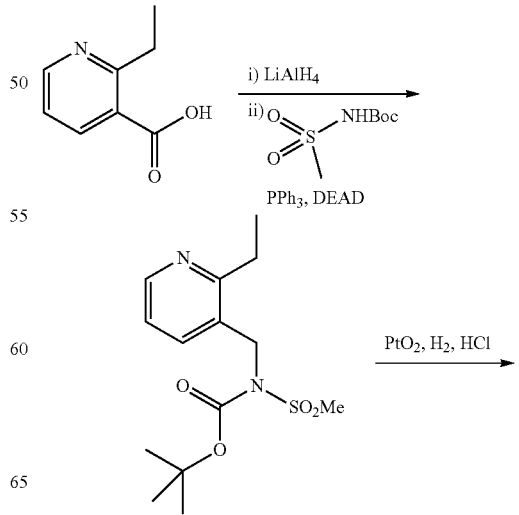

-continued

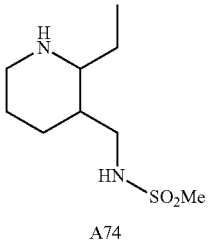

A74

LiAlH$_4$ (9.0 mL of a 1 M solution in THF, 9.0 mmol) was added dropwise to a suspension of 2-ethylpyridine-3-carboxylic acid (500 mg, 3.31 mmol) in THF (5 mL) under N$_2$ with cooling in an ice bath. The resulting solution was stirred for 1 hour, then quenched by the careful addition of water (0.35 mL) then aqueous NaOH (0.25 mL of a 15% w/v solution) then water (1 mL). After stirring for 10 minutes the mixture was filtered and the filtrate concentrated in vacuo to give a colourless oil (250 mg); MS m/z: 138 (M+H)$^+$. This material was dissolved in DCM (10 mL) and tert-butyl N-methylsulfonylcarbamate (630 mg, 3.23 mmol) and PPh$_3$ (950 mg, 3.62 mmol) were added followed by DEAD (500 µL, 3.04 mmol). The reaction mixture was stirred at ambient temperature for 18 hours, then partitioned between EtOAc and saturated aqueous sodium bicarbonate solution. After stirring for 5 minutes the organic phase was isolated using a phase separation cartridge. The solvent was removed in vacuo and the residue purified by column chromatography (silica, DCM-EtOAc elution) to give an oil that was taken up in HCl (10 mL of a 3 M solution in MeOH). PtO$_2$ (150 mg, 0.66 mmol) was added and the mixture shaken in a Parr hydrogenator for 18 hours under 60 psi of H$_2$ pressure. The reaction mixture was poured onto a pre-wetted ion-exchange cartridge, washing with MeOH then eluting the product with 2 M methanolic NH$_3$ solution. The filtrate was concentrated in vacuo to give N-((2-ethylpiperidin-3-yl)methyl)methanesulfonamide A74 as a colourless oil (70 mg) that was taken directly on to the next reaction without further purification; MS m/z: 221 (M+H)$^+$.

Preparation 69: N-((5-Methylpiperidin-3-yl)methyl)methanesulfonamide A75

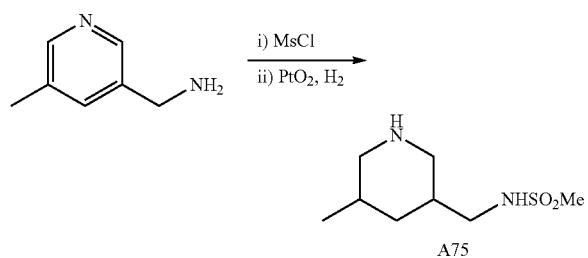

A75

Methanesulfonyl chloride (700 µL, 9.00 mmol) was added to a solution of (5-methyl-3-pyridyl)methanamine (1.0 g, 8.2 mmol) and triethylamine (1.25 mL, 9.0 mmol) in DCM (33 mL) at ambient temperature. After stirring for 1 hour, the reaction mixture was diluted in DCM (30 volumes) and washed with saturated aqueous NaHCO$_3$ solution (2×50 volumes). The organic layer was dried (MgSO$_4$), filtered and evaporated in vacuo to give N-((5-Methylpyridin-3-yl)methyl)methanesulfonamide as a white solid, (1.5 g, 92%);

$^1$H NMR (400 MHz, MeOH-d$_4$) δ 8.41-8.35 (m, 1H), 8.34-8.28 (m, 1H), 7.72 (d, 1H), 4.29 (s, 2H), 2.95 (s, 3H), 2.39 (s, 3H).

N-((5-Methylpyridin-3-yl)methyl)methanesulfonamide (1.5 g, 7.49 mmol) was dissolved in MeOH (74 mL). HCl (37.5 mL of a 3 M solution in MeOH, 112 mmol) and PtO$_2$ (225 mg, 0.99 mmol) were added and the reaction mixture shaken in a Parr hydrogenator under 60 psi hydrogen pressure for 16 hours. The reaction mixture was filtered through Celite and the filtrate concentrated. The residue was taken up in MeOH and loaded onto an ion-exchange cartridge, washing with DCM/MeOH mixtures then eluting the product with a 2 M methanolic ammonia solution. The filtrate was concentrated to give N-((5-methylpiperidin-3-yl)methyl)methanesulfonamide A75 as a white solid (200 mg, 13%) as a mixture of diastereomers that was taken on to the next reaction without further purification; MS m/z: 207 (M+H)$^+$.

Preparation 70: tert-Butyl ((6-methylpiperazin-2-yl)methyl)(methylsulfonyl)carbamate A76

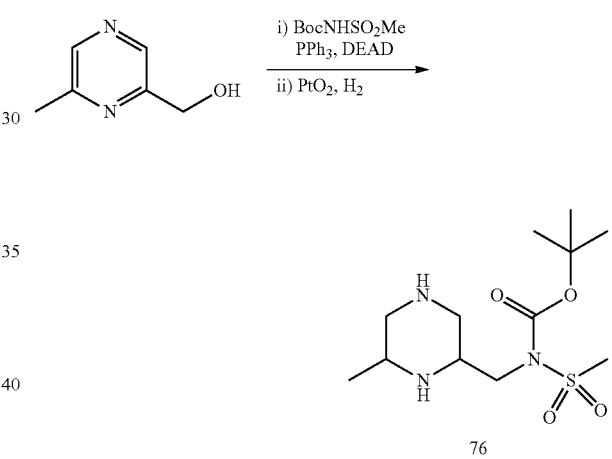

DEAD (1.7 mL, 10.8 mmol) was added dropwise to a solution of PPh$_3$ (4.0 g, 15.3 mmol), (6-methylpyrazin-2-yl)methanol (630 mg, 5.08 mmol) and tert-butyl N-methylsulfonylcarbamate (2.3 g, 11.8 mmol) in DCM (30 mL). The solution was stirred at ambient temperature for 18 hours. The resulting suspension was diluted with DCM and saturated aqueous NaHCO$_3$ solution. After stirring for 5 minutes, the organic phase was isolated using a phase separation cartridge. The filtrate was concentrated in vacuo and the residue purified by column chromatography (silica, 0-100% EtOAc-PE gradient elution) to give a white solid (2.2 g). This material was dissolved in methanolic HCl (40 mL of a 3 M solution, 120 mmol) and PtO$_2$ (200 mg, 0.88 mmol) added. The reaction mixture was stirred under an atmosphere of H$_2$ for 18 hours. The reaction mixture was loaded directly on to a pre-wetted ion-exchange cartridge, washing with methanol then eluting the product with a 2 M methanolic ammonia solution. The filtrate was concentrated in vacuo to give tert-butyl ((6-methylpiperazin-2-yl)methyl)(methylsulfonyl)carbamate A76 as a white solid (1.0 g, 45%) that was taken on to the next reaction without further purification; MS m/z: 308 (M+H)$^+$.

Preparation 71: (2-Methylpiperidin-3-yl)methanesulfonamide A77

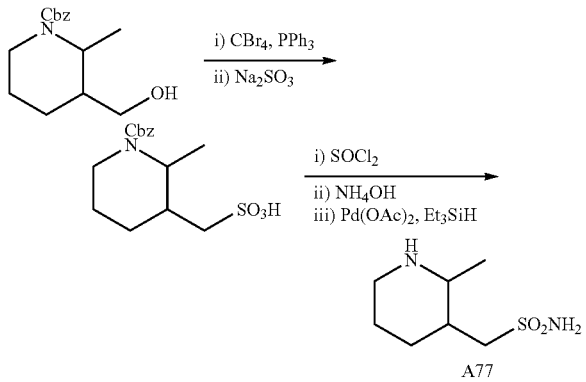

Benzyl 3-(hydroxymethyl)-2-methyl-piperidine-1-carboxylate (537 mg, 2.04 mmol) was dissolved in DCM (10 mL) under $N_2$, and $CBr_4$ (1.15 g, 3.47 mmol) was added. The solution was cooled in an ice bath and $PPh_3$ (910 mg, 3.47 mmol) was added in two portions. The reaction mixture was stirred overnight at ambient temperature then concentrated in vacuo. The residue was treated with EtOAc (~100 mL) and the resulting white solid filtered off. The filtrate was washed with brine, dried ($Na_2SO_4$), filtered and concentrated in vacuo. The residue was taken up in DCM and purified by column chromatography (silica, 0-5% MeOH-DCM gradient elution) to give the product as a colourless oil (412 mg, 62%); MS m/z: 326 (M+H)$^+$. The material was taken on without further characterisation.

Benzyl 3-(bromomethyl)-2-methyl-piperidine-1-carboxylate (412 mg, 1.26 mmol) was suspended in EtOH (5 mL) and water (5 mL), and $Na_2SO_3$ (478 mg, 3.79 mmol) was added. The reaction mixture was heated to 80° C. for 16 hours. Further $Na_2SO_3$ (500 mg) was added and the temperature increased to 100° C. After 2 hours a final portion of $Na_2SO_3$ (500 mg) was added, together with EtOH (5 mL) and water (5 mL). The reaction mixture was stirred overnight, then cooled to ambient temperature and concentrated in vacuo. The resulting cloudy solution was acidified to ~pH 1 by the addition of 2 M aqueous HCl solution, then concentrated to dryness in vacuo. The resulting white solid was triturated with MeOH, the fine precipitate filtered off through GF/C paper and the clear filtrate concentrated to dryness in vacuo. The resulting white solid was triturated with EtOH. The ethanolic suspension was filtered and concentrated as above to give a white solid (585 mg), taken directly on to the next reaction assuming quantitative yield; MS m/z: 328 (M+H)$^+$.

(1-Benzyloxycarbonyl-2-methyl-3-piperidyl)methanesulfonic acid (413 mg, 1.26 mmol) was dissolved in $SOCl_2$ (5 mL) and the mixture heated at 80° C. for 16 hours. The reaction mixture was cooled to ambient and concentrated in vacuo. The residue was cooled in an ice bath and aqueous $NH_4OH$ (10 mL of 30% w/v) added. The cooling bath was removed and the resulting cloudy solution stirred vigorously at ambient temperature for 3 hours. The reaction mixture was partitioned between EtOAc and water. The layers were separated and the aqueous phase extracted with EtOAc (×2). The combined organics were washed with brine, dried ($Na_2SO_4$), filtered and concentrated in vacuo. The product was obtained as a waxy solid (137 mg, 33% over two steps) that was taken directly on to the next reaction without further purification; MS m/z: 327 (M+H)$^+$.

Benzyl 2-methyl-3-(sulfamoylmethyl)piperidine-1-carboxylate (137 mg, 0.42 mmol) was dissolved in DCM (5 mL) and DIPEA (220 μL, 1.26 mmol) was added. The mixture was degassed (×2 vacuum-$N_2$ cycles) and Pd(OAc)$_2$ (38 mg, 0.17 mmol) was added. The mixture was degassed (×2 cycles) and Et$_3$SiH (400 μL, 2.52 mmol) was added at ambient temperature. After stirring for 20 minutes, the reaction mixture was diluted with DCM and filtered through GF/C paper. The filtrate was concentrated in vacuo and the residue taken up in MeOH and loaded on to an ion-exchange cartridge. The cartridge was washed sequentially with DCM, 1:1 DCM-MeOH and MeOH. The filtrates were discarded and the product eluted with a 2 M methanolic ammonia solution. The filtrate was concentrated in vacuo to give (2-methylpiperidin-3-yl)methanesulfonamide A77 as a gum (52 mg, 64%) that was taken on to the next step without further purification; MS m/z: 193 (M+H)$^+$.

Preparation 72: N-((3,6-Dimethylpiperazin-2-yl)methyl)methanesulfonamide A78

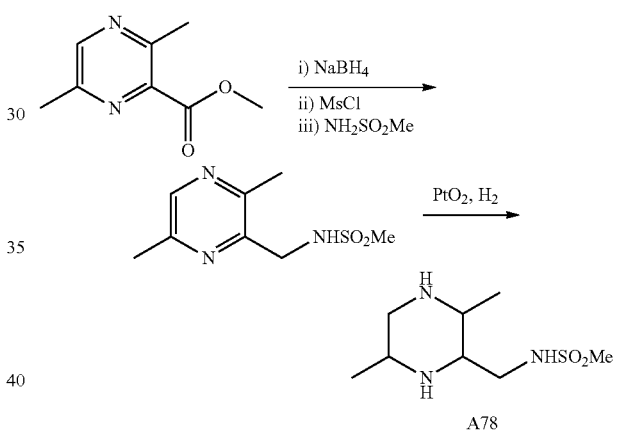

NaBH$_4$ (1.2 g, 31.5 mmol) was added to a solution of methyl 3,6-dimethylpyrazine-2-carboxylate (1.0 g, 6.0 mmol) in water (10 mL) with cooling in an ice bath. After 5 minutes the ice bath was removed and the solution stirred at ambient temperature for 1 hour. Saturated aqueous K$_2$CO$_3$ solution (20 mL) and ethanol (10 mL) were added and the mixture stirred for a further 2 hours, then extracted with EtOAc (×2). The combined organics were dried (Na$_2$SO$_4$), filtered and concentrated in vacuo to give an orange oil (470 mg, 56%) that was taken directly on to the next reaction; MS m/z: 139 (M+H)$^+$.

Methanesulfonyl chloride (350 μL, 4.52 mmol) was added to an ice cold solution of (3,6-dimethylpyrazin-2-yl)methanol (470 mg, 3.40 mmol) and Et$_3$N (700 μL, 5.02 mmol) in DCM (7 mL) under N$_2$. After five minutes, the ice bath was removed and the solution stirred at ambient temperature for 2 hours. The resulting suspension was diluted with DCM and saturated aqueous NaHCO$_3$ solution. After stirring for 5 minutes, the organic phase was isolated using a phase separation cartridge. The filtrate was concentrated under reduced pressure to give a yellow oil which was taken up in DMF (7 mL). Potassium carbonate (1.5 g, 10.9 mmol) and methanesulfonamide (800 mg, 8.41 mmol) were added and the reaction mixture stirred at 80° C. for 18 hours under N$_2$.

The reaction mixture was diluted with EtOAc, washed with saturated aqueous sodium bicarbonate solution and brine. The organic phase was dried (Na$_2$SO$_4$), filtered and concentrated in vacuo. The residue was purified by column chromatography (silica, 5-100% (EtOAc/MeOH/Et$_3$N 90-10-1)-petrol gradient elution) to give a yellow oil that was taken up in methanolic HCl (10 mL of a 3 M solution, 30 mmol). PtO$_2$ (150 mg, 0.66 mmol) was added and the reaction mixture stirred under H$_2$ for 18 hours. The reaction mixture was filtered through Celite and the filtrate concentrated in vacuo to give N-((3,6-dimethylpiperazin-2-yl)methyl)methanesulfonamide A78 as a yellow gum (460 mg) that was taken on to the next reaction without further purification, assuming the bis HCl salt was isolated in quantitative yield; MS m/z: 222 (M+H)$^+$.

Preparation 73: N-((5-(3-Fluoroazetidin-1-yl)piperidin-3-yl)methyl)methanesulfonamide A79

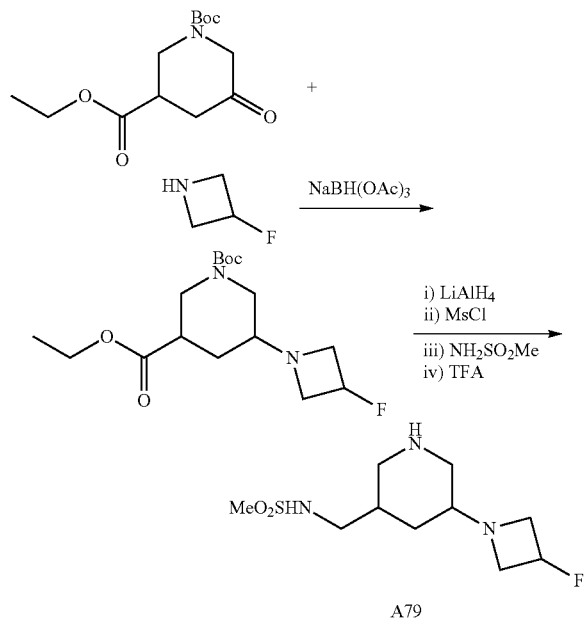

3-Fluoroazetidine hydrochloride (739 mg, 6.63 mmol) was dissolved in MeOH (10 mL) and DIPEA (1.21 mL, 6.96 mmol) added under N$_2$. The solution was stirred for 10 minutes then a solution of O1-tert-butyl O3-ethyl 5-oxopiperidine-1,3-dicarboxylate (899 mg, 3.31 mmol) in MeOH (10 mL) was added. The reaction mixture was cooled in an ice bath and NaBH(OAc)$_3$ (2.11 g, 9.94 mmol) was added portionwise. The reaction mixture was stirred for 16 hours, with the temperature rising to ambient. The reaction mixture was concentrated in vacuo and the residue partitioned between DCM and brine. The layers were separated and the aqueous phase extracted with EtOAc (×2). The combined organics were dried (Na$_2$SO$_4$), filtered and concentrated in vacuo. The residue was taken up in DCM and purified by column chromatography (silica, 0-100% EtOAc-PE gradient elution) to give the product as a pale yellow oil (654 mg, 60%); MS m/z: 331 (M+H)$^+$. The material was taken on to next step without further characterisation.

O1-tert-Butyl O3-ethyl 5-(3-fluoroazetidin-1-yl)piperidine-1,3-dicarboxylate (654 mg, 1.98 mmol) was dissolved in THF (10 mL) under N$_2$ and the solution cooled in an ice bath. LiAlH$_4$ (2.2 mL of a 1 M solution in THF, 2.2 mmol) was added slowly. After 1 hour the reaction was quenched by the dropwise addition of water (~5 mL). The reaction mixture was concentrated and the residue partitioned between EtOAc and water, then filtered through GF/C paper. The filtrate was separated and the aqueous phase extracted with EtOAc. The combined organics were washed with brine, dried (Na$_2$SO$_4$), filtered and concentrated in vacuo to give the product as a colourless oil (552 mg, 97%); MS m/z: 289 (M+H)$^+$. The product was taken directly on to the next reaction.

tert-Butyl 3-(3-fluoroazetidin-1-yl)-5-(hydroxymethyl)piperidine-1-carboxylate (552 mg, 1.91 mmol) was dissolved in DCM (6 mL) under N$_2$. The solution was cooled in an ice bath and DIPEA (500 μL, 2.87 mmol) then methanesulfonyl chloride (180 μL, 2.326 mmol) were added. The reaction mixture was stirred for 16 hours with the temperature rising to ambient. The reaction mixture was diluted with DCM and saturated aqueous NaHCO$_3$. The layers were separated and the aqueous phase extracted with DCM. The combined organics were washed with brine, dried (Na$_2$SO$_4$), filtered and concentrated in vacuo. The residue (a pale brown oil, 660 mg) was dissolved in DMF (8 mL) under N$_2$. Methanesulfonamide (550 mg, 5.78 mmol) and K$_2$CO$_3$ (794 mg, 5.75 mmol) were added and the mixture heated at 80° C. for 24 hours. The reaction mixture was partitioned between EtOAc and water and the layers separated. The aqueous phase was extracted with EtOAc (×2) and the combined organics were washed with brine, dried (Na$_2$SO$_4$), filtered and concentrated to a yellow oil. The residue (817 mg) was taken up in DCM (2 mL) and TFA (2 mL) was added at ambient temperature. After 30 minutes the reaction mixture was concentrated and the residue azeotroped with DCM (×2). The residue was taken up in MeOH and passed through SPE bicarbonate cartridges. The filtrate was concentrated in vacuo and the residue, N-((5-(3-fluoroazetidin-1-yl)piperidin-3-yl)methyl)methanesulfonamide A79, was obtained as a pale brown viscous oil (903 mg); MS m/z: 266 (M+H)$^+$. This material was taken directly on to the next reaction without further purification.

Preparation 74: N-(Piperazin-2-ylmethyl)methanesulfonamide A80

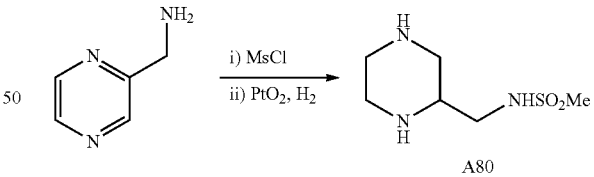

Methanesulfonyl chloride (1.0 mL, 12.9 mmol) was added to a solution of pyrazin-2-ylmethanamine (1.0 g, 9.2 mmol) and Et$_3$N (2.0 mL, 14.4 mmol) in DCM (15 mL) under N$_2$ with cooling in an ice bath. The reaction mixture was stirred at ambient temperature for 2 hours then diluted with DCM and washed with saturated aqueous sodium bicarbonate solution and brine. The organic phase was dried (MgSO$_4$), filtered and concentrated in vacuo. The residue was taken up in MeOH (20 mL) and PtO$_2$ (300 mg, 1.32 mmol) was added. The reaction mixture was shaken in a Parr hydrogenator for 20 hours under a 60 psi pressure of H$_2$. The reaction mixture was filtered and the filtrate concentrated in vacuo to give N-(piperazin-2-ylmethyl)methanesulfonamide A80 (1.0 g, 56%) that was taken on to the next reaction without further purification or characterization; MS m/z: 194 (M+H)⁺.

Preparation 75: N-((5,5-Dimethylmorpholin-2-yl)methyl)methanesulfonamide A81

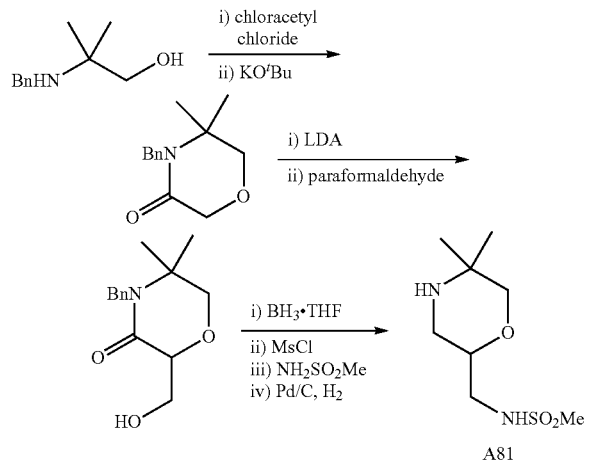

Chloroacetyl chloride (490 µL, 6.14 mmol) was added dropwise to a solution of 2-(benzylamino)-2-methyl-propan-1-ol (1.0 g, 5.58 mmol) and DIPEA (1.3 mL, 7.3 mmol) in DCM (56 mL) at 0° C. The reaction mixture was warmed to ambient temperature over 30 minutes then stirred at ambient temperature for 2 hours. Saturated aqueous NaHCO₃ was added and the aqueous layer extracted with DCM. The organics were washed sequentially with saturated aqueous NH₄Cl solution and brine, dried (MgSO₄), filtered and concentrated in vacuo to afford a brown oil (1.59 g) that was taken directly on to the next reaction without further purification; MS m/z: 256 (M+H)⁺.

N-Benzyl-2-chloro-N-(2-hydroxy-1,1-dimethyl-ethyl)acetamide (1.43 g, 5.58 mmol) and KO'Bu (751, 6.70 mmol) were stirred in THF (38 mL) at 0° C. After 15 minutes the reaction mixture was allowed to warm to ambient temperature and stirred for 2 hours. Saturated aqueous NH₄Cl solution was added and the organics were extracted with EtOAc, dried (MgSO₄), filtered and concentrated in vacuo to afford an orange oil. The residue was purified by column chromatography (silica, 0-100% EtOAc-PE gradient elution) to give the product as a white solid (879 mg, 72% over 2 steps); MS m/z: 220 (M+H)⁺.

Butyllithium (3.0 mL of a 1.6 M solution in hexanes, 4.81 mmol) was added dropwise to a solution of diisopropylamine (674 µL, 4.81 mmol) in THF (6 mL) at −78° C. The reaction was stirred at this temperature for 15 minutes and then at 0° C. for 15 minutes. The LDA solution was added dropwise to a stirred solution of 4-benzyl-5,5-dimethyl-morpholin-3-one (879 mg, 4.01 mmol) in THF (2 mL) at −78° C. and stirred at this temperature for 1 hour. Paraformaldehyde (151 mg, 5.01 mmol) was added and the mixture was warmed to ambient temperature over 3 hours. After stirring at ambient temperature for 2 further hours, water was added to the reaction. The aqueous layer was separated and extracted with EtOAc and the combined organics washed with brine solution, dried (MgSO₄), filtered and concentrated in vacuo to afford a pale yellow oil. The residue was purified by column chromatography (silica, 0 to 100% EtOAc-PE gradient elution) to give 4-benzyl-2-(hydroxymethyl)-5,5-dimethyl-morpholin-3-one as a colourless oil (494 mg, 49%); MS m/z: 250 (M+H)⁺.

BH₃.THF (9.9 mL of a 1 M solution in THF, 9.9 mmol) was added cautiously to a solution of 4-benzyl-2-(hydroxymethyl)-5,5-dimethyl-morpholin-3-one (494 mg, 1.98 mmol) in THF (3 mL) at 0° C. After 10 minutes the reaction was warmed to ambient temperature and stirred for 2 hours. The reaction mixture was cooled to 0° C. and quenched (very cautiously) with MeOH until effervescence had finished. The reaction mixture was passed through an ion-exchange cartridge, washing with MeCN/MeOH. The product was eluted with 2 M methanolic NH₃. The filtrate was concentrated in vacuo to afford a colourless oil (227 mg, 49%) that was taken directly on to the next reaction; MS m/z: 236 (M+H)⁺.

Methanesulfonyl chloride (112 µL, 1.45 mmol) was added to a solution of (4-benzyl-5,5-dimethyl-morpholin-2-yl)methanol (227 mg, 0.96 mmol) and Et₃N (270 µL, 1.93 mmol) in DCM (4 mL) at 0° C. The reaction mixture was allowed to warm to ambient temperature and stirred for 2 hours. Saturated aqueous NaHCO₃ solution was added and the organics were extracted with DCM, dried (MgSO₄), filtered and concentrated in vacuo to afford an orange oil (320 mg) that was taken directly on to the next reaction; MS m/z: 314 (M+H)⁺.

(4-Benzyl-5,5-dimethyl-morpholin-2-yl)methyl methanesulfonate (302 mg, 0.96 mmol), methanesulfonamide (275 mg, 2.90 mmol) and potassium carbonate (467 mg, 3.38 mmol) were mixed in DMF (5 mL) and heated at 120° C. for 16 hours. The mixture was cooled to ambient temperature and diluted with water. The organics were extracted with EtOAc and washed with brine (×3), dried (MgSO₄), filtered and concentrated in vacuo to afford an orange oil which was purified by column chromatography (silica, 0-100% EtOAc-PE gradient elution). The product was obtained as a colourless oil (143 mg, over 2 steps); MS m/z: 313 (M+H)⁺.

HCl (4 mL of a 3 M solution in MeOH, 12 mmol) was added to N-[(4-benzyl-5,5-dimethyl-morpholin-2-yl)methyl]methanesulfonamide (143 mg, 0.46 mmol) and palladium on carbon (30 mg, 0.28 mmol). The solution was stirred under a balloon of hydrogen for 16 hours. The reaction mixture was filtered through Celite and the filtrate concentrated in vacuo. The residue was passed through an ion-exchange cartridge, washing with MeCN/MeOH. The product was eluted with 2 M methanolic NH₃ solution and the filtrate concentrated in vacuo to afford N-((5,5-dimethylmorpholin-2-yl)methyl)methanesulfonamide A81 as a colourless oil (87 mg), which was taken on to the next reaction without further purification; MS m/z: 223 (M+H)⁺.

Preparation 76: (1-Methylpiperazin-2-yl)methanesulfonamide A82

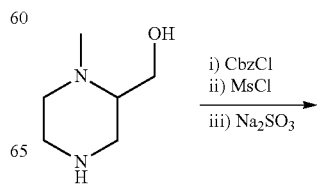

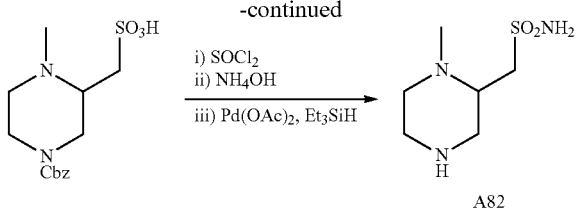

A82

(1-Methylpiperazin-2-yl)methanol dihydrochloride (993 mg, 4.89 mmol) was suspended in DCM (50 mL) under N₂ and DIPEA (3.0 mL, 17.2 mmol) added. The mixture was cooled in an ice bath and Cbz-Cl (730 µL, 5.11 mmol) added slowly. The reaction mixture was stirred for 16 hours, with the temperature rising to ambient. The reaction mixture was concentrated in vacuo and the residue partitioned between EtOAc and water. The layers were separated and the aqueous phase extracted with EtOAc. The combined organics were washed with brine, dried (Na₂SO₄), filtered and concentrated in vacuo. The residue was taken up in DCM and purified by column chromatography (silica, 5-10% MeOH-DCM gradient elution) to give benzyl 3-(hydroxymethyl)-4-methyl-piperazine-1-carboxylate as a colourless oil, (537 mg, 42%); MS m/z: 265 (M+H)⁺.

Benzyl 3-(hydroxymethyl)-4-methyl-piperazine-1-carboxylate (537 mg, 2.03 mmol) was dissolved in DCM (10 mL) under N₂. DIPEA (1 mL, 5.74 mmol) was added and the solution cooled in an ice bath. Methanesulfonyl chloride (170 µL, 2.20 mmol) was added slowly and the mixture stirred for 16 hours, with the temperature rising to ambient. The reaction mixture was concentrated in vacuo and the residue taken up in EtOH (10 mL). The solution was transferred to a 35 mL microwave vessel and water (10 mL) and Na₂SO₃ (770 mg, 6.11 mmol) added. The mixture was heated in the microwave at 130° C. for 20 minutes. The reaction mixture was concentrated to dryness in vacuo and the residue triturated with EtOH. The fine white precipitate was filtered off and the filtrate concentrated in vacuo to give a sticky white solid that was taken directly on to the next reaction without further purification or characterisation, assuming the sodium salt was isolated in quantitative yield (892 mg); MS m/z: 329 (M+H)⁺.

SOCl₂ (5.0 mL, 68.6 mmol) was added slowly to (4-benzyloxycarbonyl-1-methyl-piperazin-2-yl)methanesulfonic acid sodium salt (713 mg, 2.03 mmol) under N₂ at ambient temperature. The mixture was heated to 80° C. After 2 hours, the reaction mixture was cooled to ambient temperature and concentrated to dryness in vacuo. The residue was cooled in an ice bath and NH₄OH (5 mL of 28% w/w, 36.0 mmol) added carefully. The ice bath was removed and the mixture stirred at ambient temperature for 16 hours. The reaction mixture was extracted with EtOAc (×3). The combined organics were washed with brine, dried (Na₂SO₄), filtered and concentrated in vacuo to give the product as a yellow oil (107 mg, 16% over 4 steps); MS m/z: 328 (M+H)⁺. This material was taken on to the next step without further purification or characterisation.

Benzyl 4-methyl-3-(sulfamoylmethyl)piperazine-1-carboxylate (107 mg, 0.33 mmol) was dissolved in DCM (5 mL) under N₂. DIPEA (170 µL, 0.98 mmol) was added and the mixture degassed (×2 vacuum-N₂ cycles). Pd(OAc)₂ (30 mg, 0.13 mmol) was added and the mixture degassed (×3 cycles), then Et₃SiH (320 µL, 2.0 mmol) was added and the mixture degassed (×3 cycles). After stirring for 3 hours, the reaction mixture was loaded on to an ion-exchange cartridge. The cartridge was washed sequentially with DCM, 1:1 DCM-MeOH and MeOH. These filtrates were discarded and the product was eluted with 2 M methanolic ammonia solution. The filtrate was concentrated in vacuo to give (1-methylpiperazin-2-yl)methanesulfonamide A82 as a pale brown oil (65 mg) that was taken directly on to the next reaction without further purification or characterisation; MS m/z: 194 (M+H)⁺.

Preparation 77:
N-(1-(Piperazin-2-yl)ethyl)methanesulfonamide A83

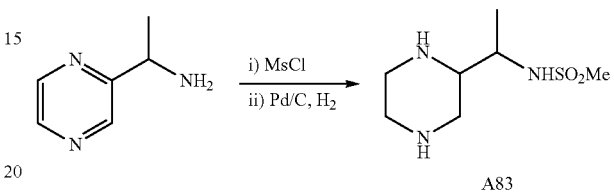

A83

1-Pyrazin-2-ylethanamine (252 mg, 2.05 mmol) was dissolved in DCM (3 mL) under N₂. DIPEA (700 µL, 4.02 mmol) was added and the solution cooled in an ice bath. Methanesulfonyl chloride (160 µL, 2.07 mmol) was added slowly. After 20 minutes, the reaction mixture was diluted with DCM and washed with water. The organic phase was dried (Na₂SO₄), filtered and concentrated in vacuo. The residue was purified by column chromatography (silica, 0-5% MeOH-DCM gradient elution) to give N-(1-pyrazin-2-ylethyl)methanesulfonamide as a colourless oil (236 mg, 57%); MS m/z: 202 (M+H)⁺.

N-(1-Pyrazin-2-ylethyl)methanesulfonamide (236 mg, 1.17 mmol) was dissolved in MeOH (5 mL) and the solution degassed (×3 vacuum-N₂ cycles). Pd on C, wet, Degussa (126 mg of 10% w/w, 0.12 mmol) was added and the mixture degassed (×3 cycles). The N₂ atmosphere was replaced with H₂ (×5 cycles) and the reaction mixture stirred for 16 hours at ambient temperature. The reaction mixture was diluted with MeOH and filtered through GF/C paper. The filtrate was concentrated in vacuo to give N-(1-(piperazin-2-yl)ethyl)methanesulfonamide A83 as a colourless oil (241 mg, 99%) that was taken directly on to the next reaction without further purification; MS m/z: 208 (M+H)⁺.

Preparation 78: 3-Methylpiperazine-2-carboxamide A84

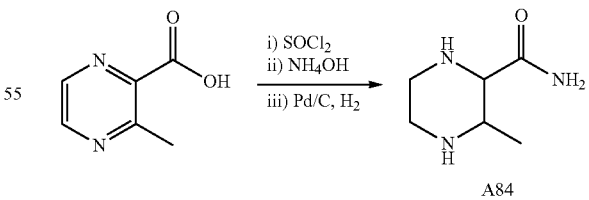

A84

3-Methylpyrazine-2-carboxylic acid (500 mg, 3.62 mmol) was suspended in SOCl₂ (2 mL, 27.4 mmol) and the mixture heated under N₂ at 80° C. for 30 minutes. The reaction mixture was concentrated in vacuo and the residue cooled in an ice bath. NH₄OH (10 mL of 28% w/w, 71.9 mmol) was added carefully and the mixture stirred for 16 hours. The reaction mixture was concentrated to dryness and the resulting dark brown solid (730 mg) was taken directly on to the next reaction without purification; MS m/z: 138 (M+H)$^+$.

3-Methylpyrazine-2-carboxamide (730 mg, 2.66 mmol) was suspended in MeOH (60 mL). 2 M Aqueous HCl (~10 mL) was added and the mixture degassed (×3 vacuum-N$_2$ cycles) and Pd on C, wet, Degussa (567 mg of 5% w/w, 0.27 mmol) added. The mixture was degassed (×3 cycles) then the N$_2$ atmosphere replaced with H$_2$ (×5 cycles). The reaction mixture was stirred for 16 hours at ambient temperature then filtered through GF/C paper. The filtrate was concentrated in vacuo to give a yellow solid containing 3-methylpiperazine-2-carboxamide A84 (698 mg), which was taken directly on to the next reaction without further purification; MS m/z: 144 (M+H)$^+$.

Preparation 79: 2-(Piperazin-2-yl)acetamide A85

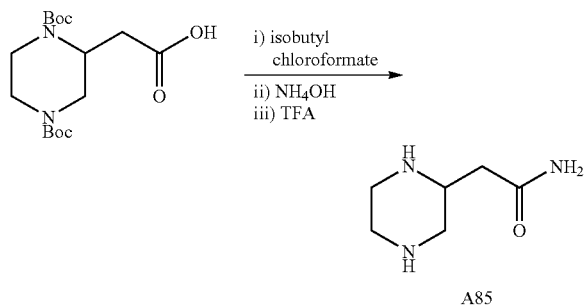

2-[1,4-Bis(tert-butoxycarbonyl)piperazin-2-yl]acetic acid (500 mg, 1.45 mmol) was dissolved in THF (10 mL) under N$_2$ and DIPEA (1.0 mL, 5.74 mmol) added. The solution was cooled in an ice bath and isobutylchloroformate (210 μL, 1.62 mmol) added slowly. After stirring for 1 hour, NH$_4$OH (1.5 mL of 28% w/w, 22.20 mmol) was added to the cloudy solution. The resulting clear solution was stirred for a further 1 hour. The reaction mixture was concentrated in vacuo and the residue partitioned between EtOAc and brine. The layers were separated and the aqueous phase extracted with EtOAc. The combined organics were dried (Na$_2$SO$_4$), filtered and concentrated in vacuo to give the product as a sticky foam (570 mg) that was taken directly on to the next reaction; MS m/z: 344 (M+H)$^+$.

Di-tert-butyl 2-(2-amino-2-oxo-ethyl)piperazine-1,4-dicarboxylate (570 mg, 1.50 mmol) was dissolved in DCM (10 mL) at ambient temperature and TFA (5 mL) was added. After 15 minutes the reaction mixture was concentrated in vacuo and the residue azeotroped with DCM (×2). The residue was taken up in MeOH and passed through SPE bicarbonate cartridges. The filtrate was concentrated to give 2-(piperazin-2-yl)acetamide A85 as a colourless oil (250 mg) that was taken directly on to the next reaction assuming quantitative yield over two steps; MS m/z: 144 (M+H)$^+$.

Preparation 80: N-((3,6,6-Trimethylmorpholin-2-yl)methyl)methanesulfonamide A86

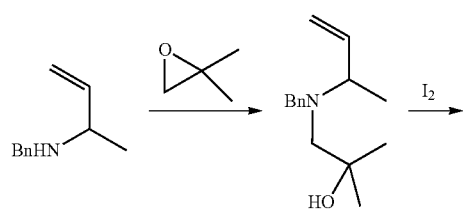

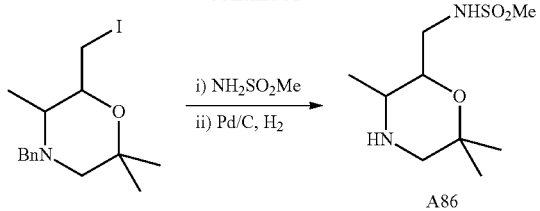

LiBr (275 mg, 3.17 mmol) was added to a stirred mixture of 2,2-dimethyloxirane (1.7 mL, 19.1 mmol) and N-benzyl-but-3-en-2-amine (2.56 g, 15.9 mmol) and the mixture stirred at ambient temperature for 15 hours. The mixture was diluted with DCM (50 mL) and washed with water (2×15 mL). The organic phase was dried (MgSO$_4$), filtered and concentrated in vacuo. The residue was purified by column chromatography (silica, 0-30% EtOAc-PE gradient elution) to give 1-[benzyl(1-methylallyl)amino]-2-methyl-propan-2-ol (2.46 g, 66%) as a colourless oil; $^1$H NMR (500 MHz, Chloroform-d) δ 7.39-7.33 (m, 4H), 7.28-7.25 (m, 1H), 5.90 (ddd, 1H), 5.20 (dt, 1H), 5.07 (dt, 1H), 3.81 (d, 1H), 3.76 (d, 1H), 3.30 (pt, 1H), 2.87 (s, 1H), 2.57 (d, 1H), 2.46 (d, 1H), 1.18-1.16 (m, 9H); MS m/z 234 (M+H)$^+$.

I$_2$ (2.94 g, 11.6 mmol) was added to a stirred biphasic mixture of 1-[benzyl(1-methylallyl)amino]-2-methyl-propan-2-ol (2.46 g, 10.5 mmol) in MTBE (35 mL) and 1 M NaHCO$_3$ (15 mL) and the mixture stirred at ambient temperature for 15 hours. The reaction was diluted with MTBE (35 mL) and a further portion of I$_2$ (2.94 g, 11.6 mmol) added. The reaction mixture was stirred at ambient temperature for a further 24 hours. The reaction was quenched by the addition of saturated aqueous Na$_2$S$_2$O$_3$ (30 mL), diluted with MTBE (30 mL) and the layers separated. The organic phase was washed with a 1:1 mixture of saturated aqueous Na$_2$S$_2$O$_3$/saturated aqueous NaHCO$_3$ (60 mL), dried (MgSO$_4$), filtered and concentrated in vacuo. The residue was purified by column chromatography (silica, 0-10% EtOAc-PE gradient elution) to give 4-benzyl-6-(iodomethyl)-2,2,5-trimethyl-morpholine (646 mg, 17%) as a purple oil; $^1$H NMR (500 MHz, Chloroform-d) δ 7.39-7.25 (m, 5H), 4.18 (td, 1H), 3.72 (d, 1H), 3.52 (d, 1H), 3.10 (d, 2H), 2.97 (dd, 1H), 2.37 (d, 1H), 2.07 (d, 1H), 1.33 (s, 3H), 1.16 (s, 3H), 0.90 (d, 3H); MS m/z: 360 (M+H)$^+$.

4-Benzyl-6-(iodomethyl)-2,2,5-trimethyl-morpholine (645 mg, 1.80 mmol), methanesulfonamide (510 mg, 5.36 mmol) and potassium carbonate (870 mg, 6.30 mmol) were heated at 120° C. in DMF (10 mL) for 20 hours. The mixture was cooled to ambient temperature and diluted with water. The mixture was extracted with EtOAc (×2) and the combined organic extracts washed with water (×3), brine (×2), dried (MgSO$_4$), filtered and concentrated in vacuo. The residue was purified by column chromatography (silica, 0-50% EtOAc-PE gradient elution) to give N-[(4-benzyl-3,6,6-trimethyl-morpholin-2-yl)methyl]methanesulfonamide (249 mg, 43%) as a colourless oil; $^1$H NMR (500 MHz, DMSO-d$_6$) δ 7.37-7.29 (m, 5H), 7.23 (tt, 1H), 6.98 (t, 1H), 3.94 (td, 1H), 3.66 (d, 1H), 3.47 (d, 1H), 2.89 (s, 3H), 2.87-2.83 (m, 2H), 2.82-2.77 (m, 1H), 2.32 (d, 1H), 2.09 (d, 1H), 1.27 (s, 3H), 1.07 (s, 3H), 0.84 (d, 3H); MS m/z: 327 (M+1)$^+$.

A mixture of N-[(4-benzyl-3,6,6-trimethyl-morpholin-2-yl)methyl]methanesulfonamide (249 mg, 0.76 mmol), Pd on C, wet, Degussa (30 mg of 10% w/w, 0.03 mmol) and HCl (3 M in methanol) (10 mL, 30 mmol) was placed under an atmosphere of H$_2$ and stirred at ambient temperature for 15 hours. The catalyst was removed by filtration through Celite, washing with MeOH, and the filtrate concentrated in vacuo. The residue was re-dissolved in HCl (3 M in methanol) (10 mL, 30 mmol) and re-charged with Pd on C, wet, Degussa (60 mg of 10% w/w, 0.06 mmol), placed under an atmosphere of $H_2$ and stirred at ambient temperature for 24 hours. The catalyst was removed by filtration through Celite, washing with MeOH, and the filtrate concentrated in vacuo. The residue was passed through an ion-exchange cartridge and washed with MeOH/DCM mixtures. The product was eluted with 2 M $NH_3$ in MeOH/DCM mixtures and the solvent removed in vacuo to give N-[(3,6,6-trimethylmorpholin-2-yl)methyl]methanesulfonamide A86 (73 mg, 41%) as a colourless oil; MS m/z: 237 $(M+H)^+$.

Preparation 81:
3-(2-(Methylsulfonyl)ethyl)piperidine A87

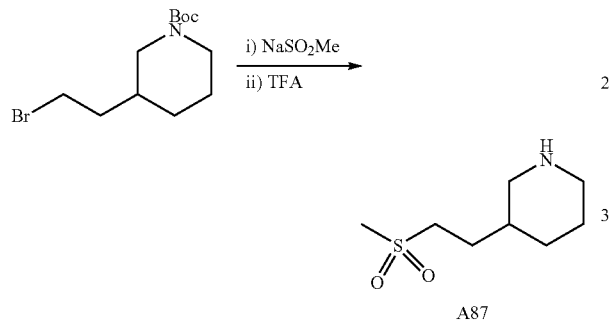

tert-Butyl 3-(2-bromoethyl)piperidine-1-carboxylate (338 mg, 1.16 mmol) and sodium methanesulfinate (209 mg, 1.74 mmol) were combined in EtOH under $N_2$ in a sealed tube and heated for 16 hours at 80° C. The reaction mixture was partitioned between EtOAc and water, the layers separated and the aqueous phase extracted with EtOAc. The combined organics were dried ($Na_2SO_4$), filtered and concentrated in vacuo to give a colourless oil which was taken up in DCM (10 mL). TFA (3 mL) was added and the mixture stirred at ambient temperature for 1.5 hours. The reaction mixture was concentrated in vacuo and the residue azeotroped with DCM (×2). The residue was taken up in MeOH and passed through SPE bicarbonate cartridges. The filtrates were combined and concentrated in vacuo to give 3-(2-(methylsulfonyl)ethyl) piperidine A87 as a colourless oil (301 mg, 87% over two steps) that was taken directly on to the next reaction without further purification or characterization; MS m/z: 192 $(M+H)^+$.

Preparation 82: tert-Butyl ((2,5-dimethylpiperidin-3-yl)methyl)(methylsulfonyl)carbamate A88

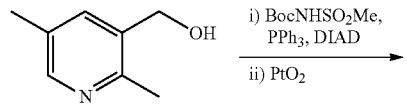

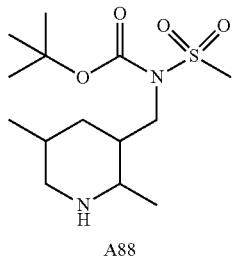

DIAD (1.6 g, 7.91 mmol) in DCM (0.5 mL) was slowly added to a solution of (2,5-dimethyl-3-pyridyl)methanol (690 mg, 5.03 mmol), tert-butyl N-methylsulfonylcarbamate (1.8 g, 9.2 mmol) and $PPh_3$ (1.9 g, 7.2 mmol) in DCM (40 mL) and the mixture was stirred at ambient temperature for 1 hour. The reaction mixture was partitioned between DCM and saturated aqueous $NaHCO_3$ solution. The combined organics were dried, filtered and concentrated in vacuo. The residue was purified by column chromatography (silica, 0-50% EtOAc-PE elution) to give the product as an oil (500 mg, 32%); $^1$H NMR (500 MHz, DMSO-$d_6$) δ 8.18 (dd, 1H), 7.40-7.17 (m, 1H), 4.76 (s, 2H), 3.45 (s, 3H), 2.42 (s, 3H), 2.26 (dd, 3H), 1.42 (s, 9H); MS m/z: 315 $(M+H)^+$.

A mixture of $PtO_2$ (45 mg, 0.20 mmol) and tert-butyl ((2,5-dimethylpyridin-3-yl)methyl)(methylsulfonyl)carbamate (500 mg, 1.59 mmol) in AcOH (15 mL) was shaken in a Parr hydrogenator under 60 psi of $H_2$ for 4 hours. The reaction mixture was filtered and the filtrate concentrated in vacuo to give tert-butyl ((2,5-dimethylpiperidin-3-yl) methyl)(methylsulfonyl)carbamate A88, which was used directly in the next step without further purification; MS m/z: 321 $(M+H)^+$.

Preparation 83: 2,2,2-Trifluoro-N-(methyl(oxo)(piperidin-3-yl)-$\lambda^6$-sulfanylidene)acetamide A89

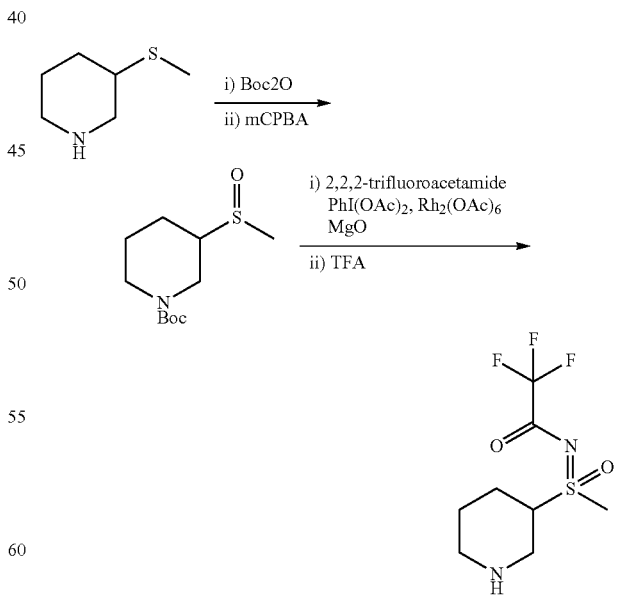

Di-tert-butyl dicarbonate (282 mg, 1.29 mmol) was added to a solution of 3-methylsulfanylpiperidine hydrochloride (199 mg, 1.19 mmol) and $Et_3N$ (330 µL, 2.37 mmol) in DCM (10 mL) and the mixture was stirred at ambient temperature for 16 hours. The reaction mixture was concentrated and the residue taken up in DCM (5 mL). mCPBA (288 mg, 1.17 mmol) was added and the mixture stirred at ambient temperature for 30 minutes. The reaction was quenched by addition of saturated aqueous NaHCO₃ solution and saturated aqueous Na₂S₂O₃ solution. After 30 minutes the phases were separated and the aqueous phase extracted with DCM. The combined organics were dried and concentrated in vacuo. The residue was taken up in DCE (12 mL) and Rh$_2$(OAc)$_6$ (47 mg, 0.11 mmol), 2,2,2-trifluoroacetamide (272 mg, 2.40 mmol) and MgO (176 mg, 4.37 mmol) were added. Iodobenzene diacetate (528 mg, 1.64 mmol) was then added and the mixture stirred at ambient temperature for 16 hours. The reaction mixture was filtered and the filtrate concentrated in vacuo. The residue was dissolved in DCM (5 mL) and TFA (1 mL) was added. The mixture was stirred for 1 hour at ambient temperature then concentrated in vacuo. The residue was azeotroped with toluene (×2) to give 2,2,2-trifluoro-N-(methyl(oxo)(piperidin-3-yl)-$\lambda^6$-sulfanylidene)acetamide A89 (260 mg); $^1$H NMR (500 MHz, DMSO-d$_6$) δ 8.97 (s, 2H), 4.04 (qt, 1H), 3.74 (d, 1H), 3.69 (d, 3H), 3.31 (m, 1H), 3.19 (dt, 1H), 2.93 (tt, 1H), 2.24 (d, 1H), 2.02 (dq, 1H), 1.88-1.62 (m, 2H). This material was taken directly on to the next reaction.

Preparation 84: (S)—N-(Piperidin-3-ylmethyl-d$_2$)methanesulfonamide A90

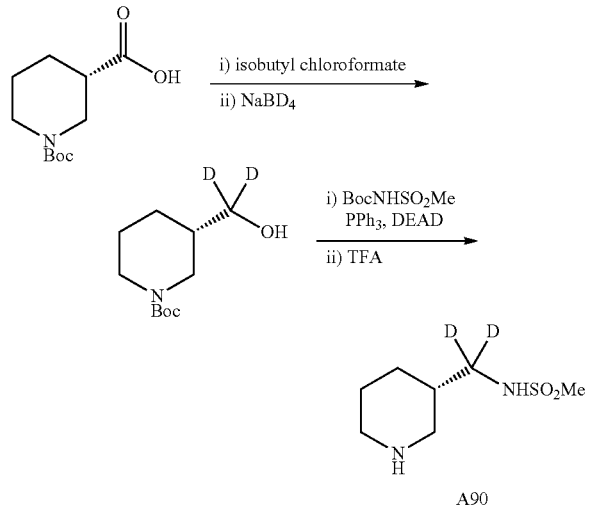

(3S)-1-tert-Butoxycarbonylpiperidine-3-carboxylic acid (500 mg, 2.18 mmol) was suspended in THF (10 mL) and cooled to −20° C. Et$_3$N (455 μL, 3.26 mmol) was added, followed by isobutyl chloroformate (425 μL, 3.28 mmol). The reaction was allowed to warm to ambient temperature over 1 hour, then sodium tetradeuterioboranuide (140 mg, 3.35 mmol) was added followed by trideuterio(deuteriooxy)methane (3.5 mL). The reaction mixture was stirred for 2.5 hours at ambient temperature then quenched by addition of saturated aqueous NaHCO₃ and stirred for 10 minutes. Water was added to dissolve salts and the mixture was extracted with EtOAc (×3). The combined organic extracts were washed with brine, dried (MgSO$_4$), filtered and concentrated in vacuo. The residue was purified by column chromatography (silica, 0-50% EtOAc-PE gradient elution) to give tert-butyl (3S)-3-[dideuterio(hydroxy)methyl]piperidine-1-carboxylate (281 mg, 59%) as a white solid; $^1$H NMR (500 MHz, DMSO-d$_6$) δ 4.44 (s, 1H), 3.93 (br s, 1H), 3.82-3.77 (m, 1H), 2.71 (t, 1H), 2.53-2.47 (m, 1H), 1.69-1.64 (m, 1H), 1.61-1.56 (m, 1H), 1.48-1.42 (m, 1H), 1.39 (s, 9H), 1.34-1.24 (m, 1H), 1.08 (qd, 1H); MS m/z: 218 (M+H)$^+$.

To a solution of tert-butyl (3S)-3-[dideuterio(hydroxy)methyl]piperidine-1-carboxylate (280 mg, 1.29 mmol), tert-butyl N-methylsulfonylcarbamate (375 mg, 1.92 mmol) and PPh$_3$ (990 mg, 3.78 mmol) in THF (15 mL) was added DEAD (440 μL, 2.79 mmol) dropwise and the reaction mixture stirred at ambient temperature under nitrogen for 16 hours. The reaction mixture was concentrated in vacuo. The residue was dissolved in DCM (10 mL) and TFA (2.5 mL, 32.5 mmol) was added. After stirring for 22 hours, TFA (1 mL, 13.0 mmol) was added and the reaction stirred at ambient temperature for a further 5 hours. The solvent was removed in vacuo and the residue azeotroped with DCM (×2) and diethyl ether (×2). The residue was passed through an ion-exchange cartridge, washing with MeOH/DCM and eluting the product with 2 M methanolic NH$_3$/DCM mixtures. The combined filtrates were concentrated in vacuo to give (S)—N-(piperidin-3-ylmethyl-d$_2$)methanesulfonamide A90, (508 mg) as a solid that was taken on to the next step without further purification; MS m/z: 195 (M+H)$^+$.

Preparation 85: N-((5-Methyl-4-oxopiperidin-3-yl)methyl)methanesulfonamide A91

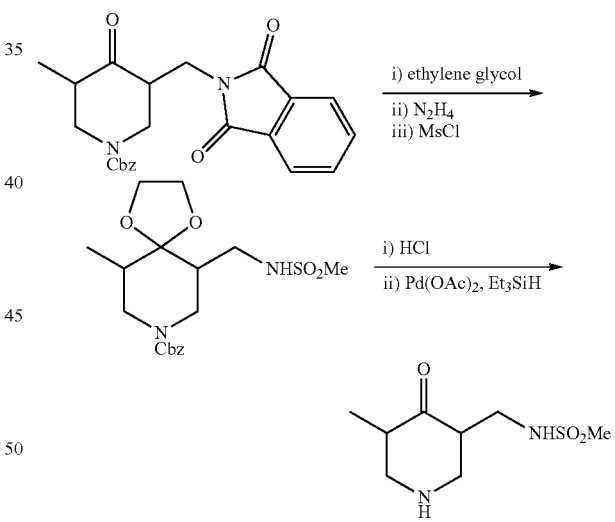

A mixture of benzyl 3-[(1,3-dioxoisoindolin-2-yl)methyl]-5-methyl-4-oxo-piperidine-1-carboxylate (550 mg, 1.35 mmol) (see A46), ethylene glycol (250 μL, 4.48 mmol) and 4-methylbenzenesulfonic acid hydrate (15 mg, 0.08 mmol) in toluene (10 mL) was heated under reflux for 24 hours. The reaction mixture was diluted with EtOAc and washed with saturated aqueous sodium bicarbonate solution and brine. The organic phase was dried (MgSO$_4$), filtered and concentrated in vacuo. The residue was purified by column chromatography (silica, 0-100% EtOAc-PE gradient elution) to give a colourless oil (370 mg) that was taken directly on to the next reaction; MS m/z: 451 (M+H)$^+$.

A mixture of benzyl 6-[(1,3-dioxoisoindolin-2-yl)methyl]-10-methyl-1,4-dioxa-8-azaspiro[4.5]decane-8-carboxylate (370 mg, 0.82 mmol) and hydrazine hydrate (180 µL of 50% w/v, 1.80 mmol) in ethanol (7 mL) was heated under reflux for 2 hours, then cooled to ambient temperature. The resulting suspension was filtered, washing with EtOH. The filtrate was concentrated under reduced pressure to give a white solid, which was taken up in DCM (4 mL). Et$_3$N (160 µL, 1.15 mmol) was added under N$_2$ and the solution cooled in an ice bath. Methanesulfonyl chloride (80 µL, 1.034 mmol) was added. After 5 minutes, the ice bath was removed and the reaction mixture stirred at ambient temperature for 18 hours. The resulting suspension was diluted with DCM and saturated aqueous NaHCO$_3$ solution. After stirring for 5 minutes, the organic phase was isolated using a phase separation cartridge. The filtrate was concentrated in vacuo and the residue purified by column chromatography (silica, 0-100% EtOAc-PE gradient elution) to give benzyl 6-(methanesulfonamidomethyl)-10-methyl-1,4-dioxa-8-azaspiro[4.5]decane-8-carboxylate as a white gum (250 mg) that was taken directly on to the next reaction; MS m/z: 399 (M+H)$^+$.

A mixture of HCl (1.8 mL of a 2 M aqueous solution, 3.6 mmol) and benzyl 6-(methanesulfonamidomethyl)-10-methyl-1,4-dioxa-8-azaspiro[4.5]decane-8-carboxylate (250 mg, 0.63 mmol) in THF (4 mL) was heated under reflux for 18 hours then cooled to ambient temperature. The solution was diluted with EtOAc and water. After stirring for 5 minutes, the organic phase was isolated, washed with saturated aqueous NaHCO$_3$ solution and brine. The organic phase was dried (Na$_2$SO$_4$), filtered and concentrated in vacuo. The residue was taken up in DCM (5 mL). Et$_3$SiH (150 µL, 0.94 mmol), Et$_3$N (150 µL, 1.08 mmol) and Pd(OAc)$_2$ (30 mg, 0.13 mmol) were added successively to the solution which was then stirred for 2 hours at ambient temperature. The resulting suspension was diluted with methanol (~5 mL) and loaded directly onto an ion-exchange cartridge. The cartridge was washed with methanol then the product eluted with a 2 M methanolic NH$_3$ solution. The filtrate was concentrated in vacuo to give N-((5-methyl-4-oxopiperidin-3-yl)methyl)methanesulfonamide A91 as a brown oil (100 mg, 72%) that was taken on to the next reaction without further purification; MS m/z: 221 (M+H)$^+$.

Preparation 86: N-((8,8-Difluoro-5-azaspiro[2.5]octan-7-yl)methyl)methanesulfonamide A92

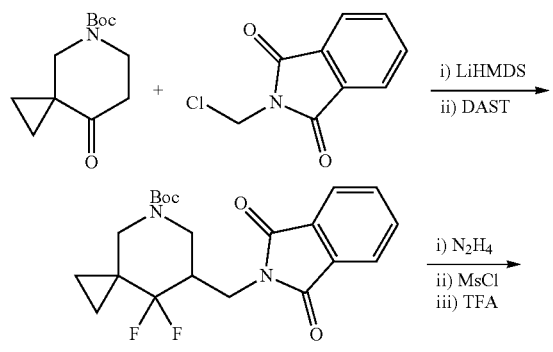

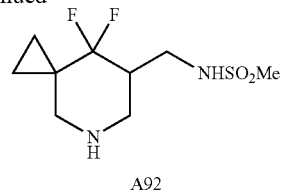

A92

LiHMDS (2.33 mL of 1 M, 2.33 mmol) was slowly added to a solution of tert-butyl 8-oxo-5-azaspiro[2.5]octane-5-carboxylate (500 mg, 2.22 mmol) in THF (10 mL) stirring at −78° C. under N$_2$. After 10 minutes, a solution of 2-(chloromethyl)isoindoline-1,3-dione (478 mg, 2.44 mmol) in THF (2 mL) was slowly added and the mixture was stirred at −78° C. for 10 minutes. Saturated aqueous NH$_4$Cl was added and the mixture allowed to warm to ambient temperature, then partitioned between water and DCM. The combined organics were dried and concentrated in vacuo. The residue was purified by column chromatography (silica, 0-30% EtOAc-PE gradient elution) to give tert-Butyl 7-[(1,3-dioxoisoindolin-2-yl)methyl]-8-oxo-5-azaspiro[2.5]octane-5-carboxylate as an oil that solidified on standing (285 mg, 33%); $^1$H NMR (500 MHz, DMSO-d$_6$) δ 7.94-7.82 (m, 4H), 4.12-4.02 (m, 1H), 3.89-3.78 (m, 1H), 3.60 (td, 2H), 3.46 (d, 2H), 3.07 (ddt, 1H), 1.37 (s, 9H), 1.16-1.04 (m, 2H), 0.91-0.83 (m, 2H).

tert-Butyl 7-[(1,3-dioxoisoindolin-2-yl)methyl]-8-oxo-5-azaspiro[2.5]octane-5-carboxylate (263 mg, 0.68 mmol) was treated with DAST (904 µL, 6.84 mmol) and the mixture stirred for 96 hours at ambient temperature. Further DAST (904 µL, 6.84 mmol) was added and the mixture stirred for 24 hours then poured carefully onto a mixture of ice and saturated aqueous NaHCO$_3$ solution. The mixture was stirred for 30 minutes then extracted with DCM. The combined organics were dried, filtered and concentrated in vacuo. The residue was purified by column chromatography (silica, 0-50% EtOAc-PE gradient elution) to give tert-Butyl 7-[(1,3-dioxoisoindolin-2-yl)methyl]-8,8-difluoro-5-azaspiro[2.5]octane-5-carboxylate (280 mg), which was used directly in the next reaction.

tert-Butyl 7-[(1,3-dioxoisoindolin-2-yl)methyl]-8,8-difluoro-5-azaspiro[2.5]octane-5-carboxylate (280 mg, 0.69 mmol), hydrazine (54 µL, 1.72 mmol) in EtOH (2.8 mL) was heated at 80° C. for 2 hours. The resulting suspension was filtered and the filtrate concentrated in vacuo. The residue was loaded on to an ion-exchange cartridge. The cartridge was washed with DCM-MeOH mixtures then the product eluted with 2 M methanolic NH$_3$. The basic eluant was concentrated in vacuo, and the residue was azeotroped with toluene then dissolved in DCM (2 mL). Et$_3$N (96 µL, 0.69 mmol) was added, followed by methanesulfonyl chloride (69 µL, 0.90 mmol) and the mixture was stirred at ambient temperature for 1 hour. The reaction mixture was concentrated in vacuo and the residue treated with TFA/DCM. After 1 hour at ambient temperature, the mixture was concentrated in vacuo and the residue purified by reverse phase chromatography (C18, MeCN/water/0.05% TFA as eluent) to give N-((8,8-difluoro-5-azaspiro[2.5]octan-7-yl)methyl)methanesulfonamide A92, (90 mg, 99%); $^1$H NMR (500 MHz, DMSO-d$_6$) δ 9.22 (s, 2H), 7.32 (t, 1H), 3.66-3.28 (m, 3H), 3.14-2.90 (m, 6H), 2.63-2.52 (m, 1H), 1.02 (ddd, 1H), 0.90-0.77 (m, 2H), 0.74 (ddd, 1H).

Preparation 87: N-((5,6-Dimethylpiperidin-3-yl)methyl)methanesulfonamide A93

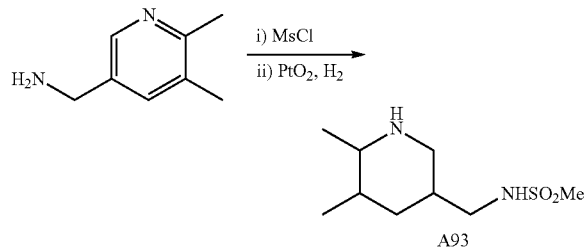

Methanesulfonyl chloride (200 µL, 2.58 mmol) was added to a solution of (5,6-dimethyl-3-pyridyl)methanamine dihydrochloride (400 mg, 1.91 mmol) and Et$_3$N (1.0 mL, 7.18 mmol) in DCM (6 mL). The solution was stirred at ambient temperature for 19 hours. The resulting suspension was diluted with DCM and saturated aqueous NaHCO$_3$ solution. After stirring for 5 minutes, the organic phase was isolated using a phase separation cartridge. The filtrate was concentrated in vacuo to give a brown oil (370 mg) that was taken on to the next step without further purification; MS m/z: 215 (M+H)$^+$.

A mixture of N-[(5,6-dimethyl-3-pyridyl)methyl]methanesulfonamide (370 mg, 1.73 mmol), PtO$_2$ (70 mg, 0.31 mmol) and HCl (10 mL of a 3 M solution in MeOH, 30 mmol) was shaken in a Parr hydrogenator for 3 hours under 60 psi H$_2$ pressure. The reaction mixture was filtered, washing with methanol. The filtrate was concentrated in vacuo to give N-((5,6-dimethylpiperidin-3-yl)methyl)methanesulfonamide A93 as a brown oil, (350 mg, 79%) that was taken on to the next reaction without further purification; MS m/z: 221 (M+H)$^+$.

Preparation 88: 8-Methylhexahydro-3H-oxazolo[3,4-a]pyrazin-3-one A94

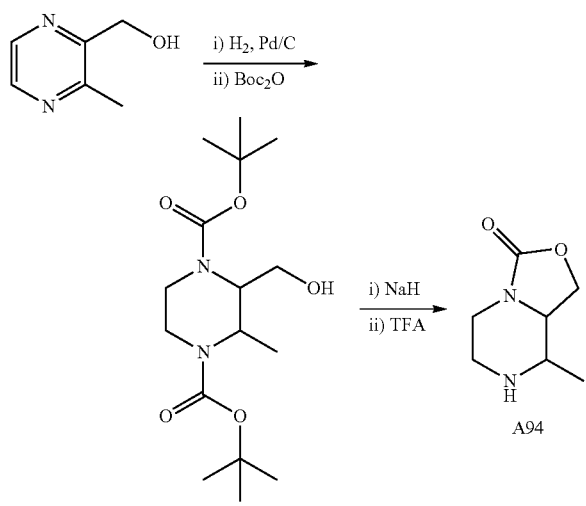

(3-Methylpyrazin-2-yl)methanol (4.92 g, 39.6 mmol) was dissolved in MeOH (200 mL) and HCl (20 mL of a 2 M aqueous solution, 40 mmol) added. The solution was degassed (×3 vacuum-N$_2$ cycles) and Pd on C, wet, Degussa (2.5 g of 10% w/w, 2.35 mmol) added. The mixture was degassed (×3 cycles) and the N$_2$ replaced with H$_2$ (×5 cycles). The mixture was stirred for 48 hours. The reaction mixture was degassed with N$_2$ then filtered through GF/F paper. The filtrate was concentrated in vacuo to give the product as a brown oil (6.7 g) that was taken directly on to the next reaction without purification, assuming the HCl salt was isolated; MS m/z: 131 (M+H)$^+$.

(3-Methylpiperazin-2-yl)methanol hydrochloride (6.7 g, 36.2 mmol) was dissolved in MeOH (50 mL) and DIPEA (19.0 mL, 109.1 mmol) added under N$_2$. The solution was cooled in an ice bath and a solution of di-tert-butyl dicarbonate (19.0 g, 87.06 mmol) in MeOH (50 mL) was added slowly over 10 minutes. The reaction mixture was stirred with cooling for 1 hour, then at ambient temperature for 1 hour. The reaction mixture was then warmed to 50° C. and stirred for 16 hours. The reaction mixture was cooled to ambient temperature and concentrated in vacuo. The residue was partitioned between EtOAc and water, the aqueous phase extracted with EtOAc and the combined organics dried (Na$_2$SO$_4$), filtered and concentrated in vacuo. The residue was purified by column chromatography (silica, 0-100% EtOAc-PE gradient elution) to give the product as a colourless oil (3.72 g, 31%) that was taken directly on to the next reaction; MS m/z: 331 (M+H)$^+$.

Di-tert-butyl 2-(hydroxymethyl)-3-methyl-piperazine-1,4-dicarboxylate (3.72 g, 11.3 mmol) was dissolved in THF (80 mL) under N$_2$. The solution was cooled in an ice bath and NaH (550 mg of a 60% w/w dispersion in mineral oil, 13.8 mmol) was added in one portion. The cooling bath was removed and the mixture allowed to warm to ambient temperature. After 1 hour the reaction mixture was cooled in an ice bath and quenched by the careful addition of water. The reaction mixture was concentrated in vacuo and the residue partitioned between EtOAc and brine. The aqueous phase was extracted with EtOAc and the combined organics dried (Na$_2$SO$_4$), filtered and concentrated in vacuo to give the product as a colourless oil (2.40 g, 83%) that was taken directly on to the next reaction without further purification; MS m/z: 201 (M-tBu)$^+$.

tert-Butyl 8-methyl-3-oxo-5,6,8,8a-tetrahydro-1H-oxazolo[3,4-a]pyrazine-7-carboxylate (156 mg, 0.61 mmol) was dissolved in DCM (2 mL) and TFA (0.5 mL) added. The reaction mixture was stirred for 16 hours at ambient temperature. The reaction mixture was concentrated in vacuo and the residue azeotroped with DCM (×2). The residue was taken up in MeOH and passed through SPE bicarbonate cartridges. The combined filtrates were concentrated in vacuo to give 8-methylhexahydro-3H-oxazolo[3,4-a]pyrazin-3-one A94 as a pale yellow glass (95 mg, quantitative yield) that was taken directly on to the next reaction; MS m/z: 157 (M+H)$^+$.

Preparation 89: N-((5-Cyanopiperidin-3-yl)methyl)methanesulfonamide A95

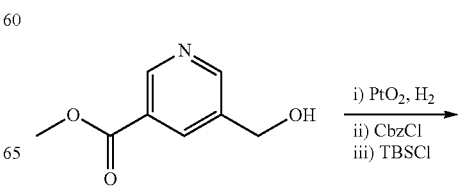

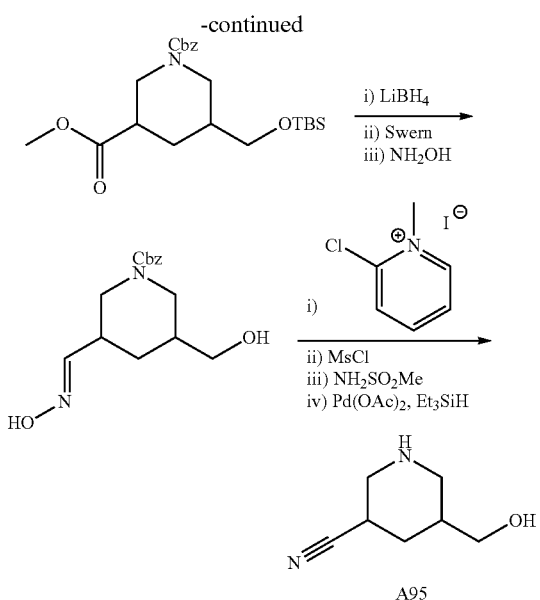

A95

Platinum oxide (2.72 g, 12.0 mmol), acetic acid (20 mL) and methyl 5-(hydroxymethyl)pyridine-3-carboxylate (2.0 g, 12.0 mmol) were combined and shaken in a Parr hydrogenator for 3 days under 60 psi $H_2$ pressure. The catalyst was filtered off, washing with acetic acid. The filtrate was concentrated under reduced pressure to give a pale yellow gum (2.8 g). This material was treated with EtOAc (100 mL) and water (50 mL), and benzyl chloroformate (1.7 mL, 11.9 mmol) and $K_2CO_3$ (10 g, 72.4 mmol) were added. The mixture was stirred at ambient temperature for 18 hours. The phases were separated and the aqueous phase diluted with water and extracted with EtOAc. The combined organics were washed with brine, dried ($Na_2SO_4$), filtered and concentrated in vacuo. The residue was purified by column chromatography (silica, 0-100% EtOAc-PE gradient elution) to give a pale yellow oil (1 g) that was dissolved in DCM (10 mL). Imidazole (440 mg, 6.46 mmol) and TBDMS chloride (600 mg, 3.98 mmol) were added, and the resulting suspension stirred at ambient temperature for 18 hours. The reaction mixture was diluted with DCM and saturated aqueous $NaHCO_3$ solution. After stirring for 5 minutes, the organic phase was isolated using a phase separation cartridge. The filtrate was concentrated under reduced pressure. The residue was purified by column chromatography (silica, 0-50% EtOAc-PE gradient elution) to give a colourless oil (800 mg, 58%); MS m/z: 422 $(M+H)^+$. This material was dissolved in THF (8 mL) under $N_2$ and the solution cooled in an ice bath. $LiBH_4$ (1.2 mL of a 2 M solution in THF, 2.4 mmol) was added and the reaction mixture stirred for 18 hours, with the temperature rising to ambient. Further $LiBH_4$ (0.4 mL of a 2 M solution in THF, 0.8 mmol) was added and the solution stirred for 2 hours at ambient temperature. The reaction mixture was quenched with 2 M aqueous NaOH solution and diluted with EtOAc. The organic phase was washed with brine, dried ($Na_2SO_4$), filtered and concentrated in vacuo to give benzyl 3-[[tert-butyl(dimethyl)silyl]oxymethyl]-5-(hydroxymethyl)piperidine-1-carboxylate as a colourless oil (710 mg, 95%); MS m/z: 394 $(M+H)^+$.

DMSO (200 µL, 2.82 mmol) was added dropwise to a solution of oxalyl chloride (160 µL, 1.83 mmol) in DCM (10 mL) cooled to −78° C. under $N_2$. After 10 minutes, a solution of benzyl 3-[[tert-butyl(dimethyl)silyl]oxymethyl]-5-(hydroxymethyl)piperidine-1-carboxylate (700 mg, 1.78 mmol) in DCM (5 mL) was added dropwise to the reaction mixture. After 50 minutes at −78° C., $Et_3N$ (750 µL, 5.38 mmol) was added. After 10 minutes, the reaction mixture was allowed to warm to ambient temperature then quenched with a 10% aqueous citric acid solution. The mixture was extracted with DCM and the organic layer washed with brine, dried ($Na_2SO_4$), filtered and concentrated in vacuo to afford the product as a light yellow oil (660 mg, 95%); MS m/z: 392 $(M+H)^+$.

A mixture of benzyl 3-[[tert-butyl(dimethyl)silyl]oxymethyl]-5-formyl-piperidine-1-carboxylate (660 mg, 1.69 mmol), hydroxylamine hydrochloride (140 mg, 2.02 mmol) and NaOAc (110 mg, 1.34 mmol) in ethanol (10 mL) and water (5 mL) was stirred at ambient temperature for 3 days. The solution was diluted with water and EtOAc. The organic phase was washed with saturated aqueous sodium bicarbonate solution and brine, dried ($MgSO_4$), filtered and concentrated in vacuo to a yellow gum (590 mg) that was taken directly on to the next reaction; MS m/z: 293 $(M+H)^+$.

2-Chloro-1-methyl-pyridin-1-ium iodide (470 mg, 1.84 mmol) was added to a solution of benzyl 3-[(E)-hydroxyiminomethyl]-5-(hydroxymethyl)piperidine-1-carboxylate (490 mg, 1.68 mmol) in DCM (5 mL) at ambient temperature. After 10 minutes, $Et_3N$ (350 µL, 2.51 mmol) was added and the suspension was stirred at ambient temperature for 18 hours. The reaction mixture was partitioned between EtOAc and a 10% aqueous citric acid solution. The organic phase was washed with brine, dried ($Na_2SO_4$), filtered and concentrated in vacuo. The residue was purified by column chromatography (silica, 0-100% EtOAc-PE gradient elution) to give a colourless oil (80 mg, 17%); MS m/z: 275 $(M+H)^+$.

Methanesulfonyl chloride (15 µL, 0.19 mmol) was added to a solution of benzyl 3-cyano-5-(hydroxymethyl)piperidine-1-carboxylate (40 mg, 0.15 mmol) and $Et_3N$ (30 µL, 0.22 mmol) in DCM (2 mL). The solution was stirred at ambient temperature for 1 hour. The resulting suspension was diluted with DCM and saturated aqueous $NaHCO_3$ solution. After stirring for 5 minutes, the organic phase was isolated using a phase separation cartridge. The filtrate was concentrated in vacuo to give a yellow oil that was taken up in DMF (2 mL). $K_2CO_3$ (60 mg, 0.43 mmol) and methanesulfonamide (40 mg, 0.42 mmol) were added to the solution which was stirred at 80° C. for 18 hours then cooled to ambient temperature. The reaction mixture was diluted with EtOAc. The organic phase was washed with saturated aqueous sodium bicarbonate solution and brine then dried ($MgSO_4$), filtered and concentrated in vacuo to give a pale yellow oil that was taken up in DCM (2 mL). $Et_3N$ (30 µL, 0.22 mmol), $Et_3SiH$ (30 µL, 0.188 mmol) then $Pd(OAc)_2$ (10 mg, 0.04 mmol) were added to the reaction mixture. After stirring for 2 hours at ambient temperature the reaction mixture was diluted with methanol and poured onto an ion-exchange cartridge. The cartridge was washed with methanol the the product eluted with a 2 M methanolic $NH_3$ solution. The filtrate was concentrated under reduced pressure to give N-((5-cyanopiperidin-3-yl)methyl)methanesulfonamide A95 as a pale yellow film (17 mg, 54%) that was taken directly on to the next reaction; MS m/z: 218 $(M+H)^+$.

Preparation 90:
(1-(tert-Butyl)-3-methylpiperazin-2-yl)methanol
A96

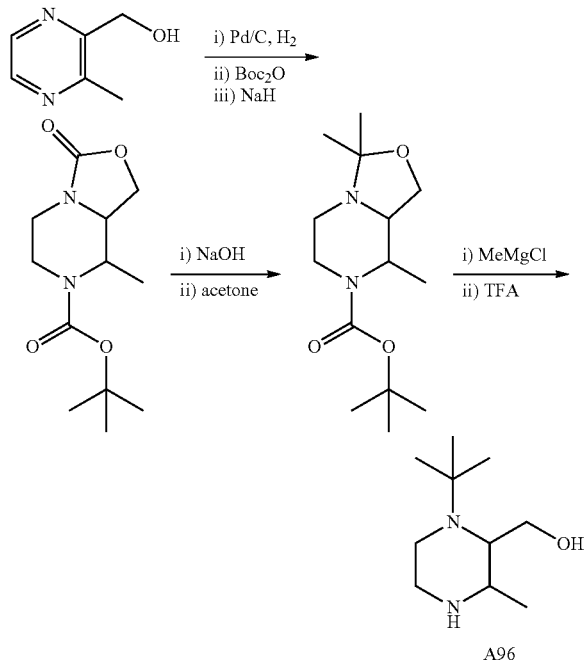

(3-Methylpyrazin-2-yl)methanol (4.92 g, 39.6 mmol), was dissolved in MeOH (200 mL) and HCl (20 mL of a 2 M aqueous solution, 40 mmol) was added. The solution was degassed (×3 vacuum-$N_2$ cycles) and Pd on C, wet, Degussa (2.5 g of 10% w/w, 2.35 mmol) was added. The mixture was degassed (×3 cycles) and the $N_2$ replaced with $H_2$ (×5 cycles). The mixture was stirred for 2 days. The reaction mixture was degassed with $N_2$, then filtered through GF/F paper. The filtrate was concentrated in vacuo to give the product as a brown oil (6.7 g), which was taken directly on to the next reaction without purification, assuming the HCl salt was isolated; MS m/z: 131 (M+H)$^+$.

(3-Methylpiperazin-2-yl)methanol hydrochloride (6.7 g, 36.2 mmol) was dissolved in MeOH (50 mL) and DIPEA (19.0 mL, 109 mmol) added under $N_2$. The solution was cooled in an ice bath and a solution of di-tert-butyl dicarbonate (19.0 g, 87.1 mmol) in MeOH (50 mL) added slowly over 10 minutes. The reaction mixture was stirred with cooling for 1 hour, then at ambient temperature for 1 hour. The reaction mixture was warmed to 50° C. overnight, then cooled to ambient and concentrated in vacuo. The residue was partitioned between EtOAc and water. The aqueous phase was extracted with EtOAc and the combined organics dried ($Na_2SO_4$), filtered and concentrated in vacuo. The residue was purified by column chromatography (silica, 0-100% EtOAc-PE gradient elution) to give the product as a colourless oil (3.72 g, 31%) that was taken on to the next reaction; MS m/z: 331 (M+H)$^+$.

Di-tert-butyl 2-(hydroxymethyl)-3-methyl-piperazine-1,4-dicarboxylate (3.72 g, 11.26 mmol) was dissolved in THF (80 mL) under $N_2$. The solution was cooled in an ice bath and NaH (550 mg of a 60% w/w dispersion in mineral oil, 13.8 mmol) added in one portion. The cooling bath was removed and the mixture allowed to warm to ambient temperature. After 1 hour the reaction mixture was cooled in an ice bath and quenched by the careful addition of water. The reaction mixture was concentrated in vacuo and the residue partitioned between EtOAc and brine. The aqueous phase was extracted with EtOAc. The combined organics were dried ($Na_2SO_4$), filtered and concentrated in vacuo to give the product as a colourless oil (2.40 g, 83%), which was taken directly on to the next reaction without further purification; MS m/z: 201 (M-tBu)$^+$.

tert-Butyl 8-methyl-3-oxo-5,6,8,8a-tetrahydro-1H-oxazolo[3,4-a]pyrazine-7-carboxylate (2.24 g, 8.76 mmol) was suspended in EtOH (30 mL) and a solution of NaOH (1.75 g, 43.8 mmol) in water (30 mL) added. The reaction mixture was stirred overnight at 100° C. The reaction mixture was cooled to ambient and the solution adjusted to ~pH 10 by the addition of 2 M aqueous HCl. The mixture was extracted with $CHCl_3$ (×2). The combined organics were dried ($Na_2SO_4$), filtered and concentrated in vacuo. The residue was taken up in MeOH and concentrated in vacuo to give the product as a yellow oil (1.91 g, 95%) that was taken directly on to the next reaction; MS m/z: 231 (M+H)$^+$.

tert-Butyl 3-(hydroxymethyl)-2-methyl-piperazine-1-carboxylate (1.9 g, 8.25 mmol) was dissolved in dry acetone (3.0 mL, 40.9 mmol) under $N_2$ and $BF_3.OEt_2$ (100 µL, 0.79 mmol) added. The mixture was heated at 100° C. for 20 minutes in a microwave reactor. The reaction mixture was concentrated in vacuo to a yellow oil, which was taken up in EtOAc and purified by column chromatography (neutral alumina, 0-100% EtOAc-PE gradient elution). The product fractions were combined and concentrated in vacuo to give the product as a colourless oil (540 mg, 24%); $^1$H NMR (500 MHz, DMSO-$d_6$) δ 4.25 (vbrs, 1H), 3.90-3.71 (m, 2H), 3.37 (dd, 1H), 3.07-2.69 (m, 3H), 2.14 (ddd, 1H), 1.41 (s, 9H), 1.22 (s, 3H), 1.04 (d, 3H), 1.00 (s, 3H); MS m/z: 271 (M+H)$^+$.

tert-Butyl 3,3,8-trimethyl-5,6,8,8a-tetrahydro-1H-oxazolo[3,4-a]pyrazine-7-carboxylate (540 mg, 2.0 mmol) was dissolved in THF (10 mL) under $N_2$. The solution was cooled to −10° C. and MeMgCl (1.5 mL of a 3 M solution in THF, 4.5 mmol) added. The reaction mixture was stirred for 16 hours, with the temperature rising to ambient. MeMgCl (1.5 mL of a 3 M solution in THF, 4.5 mmol) was added and the reaction mixture warmed to 40° C. After 3 hours the reaction mixture was cooled to ambient and quenched by the careful addition of water. The reaction mixture was extracted with EtOAc (×2). The combined organics were washed with brine, dried ($Na_2SO_4$), filtered and concentrated in vacuo to a yellow oil. The residue was taken up in EtOAc and purified by column chromatography (neutral alumina, 0-100% EtOAc-PE gradient elution). The product was obtained as a colourless oil (122 mg, 21%); $^1$H NMR (500 MHz, DMSO-$d_6$) δ 4.46 (t, 1H), 4.21 (p, 1H), 3.65-3.52 (m, 1H), 3.45 (ddd, 1H), 3.02-2.81 (m, 3H), 2.71 (ddd, 1H), 1.39 (s, 10H), 1.15 (d, J=6.9 Hz, 3H), 1.04 (s, 9H); MS m/z: 287 (M+H)$^+$. This material was taken on to the next reaction.

tert-Butyl 4-tert-butyl-3-(hydroxymethyl)-2-methyl-piperazine-1-carboxylate (122 mg, 0.426 mmol) was dissolved in DCM (5 mL) and TFA (1 mL) added under $N_2$. After 2 hours the reaction mixture was concentrated in vacuo and the residue azeotroped with DCM (×2). The residue was taken up in MeOH and passed through an SPE bicarbonate cartridge. The filtrate was concentrated in vacuo to give (1-(tert-butyl)-3-methylpiperazin-2-yl)methanol A96 (TFA salt) as a pale yellow glass (125 mg, 88%) that was taken directly on to the next reaction; MS m/z: 187 (M+H)⁺.

Preparation 91: N-(((8aS)-Octahydropyrrolo[1,2-a]pyrazin-4-yl)methyl)methanesulfonamide A97

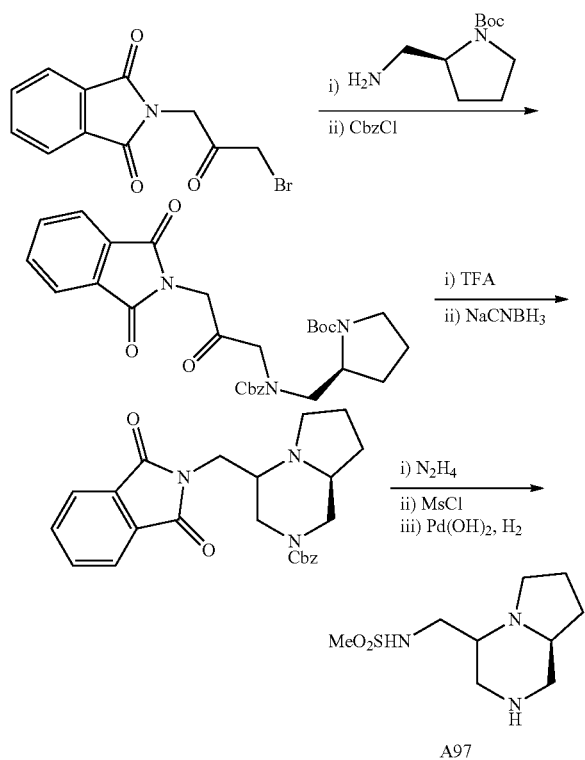

2-(3-Bromo-2-oxo-propyl)isoindoline-1,3-dione (550 mg, 1.95 mmol) was dissolved in DCM (20 mL) before addition of tert-butyl (2S)-2-(aminomethyl)pyrrolidine-1-carboxylate (391 mg, 1.95 mmol) and triethylamine (300 μL, 2.15 mmol). The colourless solution was stirred at ambient temperature for 1 hour. Cbz-Cl (334 μL, 2.34 mmol) followed by triethylamine (815 μL, 5.85 mmol) were then added to the yellow solution and stirring continued at ambient temperature. After 5 minutes the reaction was diluted with water (20 mL), the layers separated and the aqueous extracted with further DCM (2×30 mL). The combined organics were washed with 1 M aqueous HCl (20 mL), brine (20 mL), dried and filtered. The filtrate was concentrated in vacuo and the residue purified by column chromatography (silica, 30-80% EtOAc-PE gradient elution) to give tert-butyl (2S)-2-[[benzyloxycarbonyl-[3-(1,3-dioxoisoindolin-2-yl)-2-oxopropyl]amino]methyl]pyrrolidine-1-carboxylate (550 mg, 53%) as a colourless gum; MS m/z: 536 (M+H)⁺.

tert-Butyl (2S)-2-[[benzyloxycarbonyl-[3-(1,3-dioxoisoindolin-2-yl)-2-oxo-propyl]amino]methyl]pyrrolidine-1-carboxylate (550 mg, 1.03 mmol) was dissolved in DCM (6 mL) before cooling to 0° C. TFA (4 mL) was then added slowly, with stirring continued at 0° C. After 45 minutes the reaction was concentrated under reduced pressure and the residue dissolved in methanol (13 mL) before addition of NaCNBH₃ (226 mg, 3.60 mmol). The solution was stirred at ambient temperature. After 1 hour the reaction was quenched with saturated aqueous NaHCO₃ before extracting with EtOAc (3×40 mL). The combined organics were washed with water (30 mL) and brine (20 mL), then dried (Na₂SO₄), filtered and concentrated in vacuo to give benzyl (8aS)-4-[(1,3-dioxoisoindolin-2-yl)methyl]-3,4,6,7,8,8a-hexahydro-1H-pyrrolo[1,2-a]pyrazine-2-carboxylate (390 mg, 80%) as a colourless gum; MS m/z: 420 (M+H)⁺.

Benzyl (8aS)-4-[(1,3-dioxoisoindolin-2-yl)methyl]-3,4,6,7,8,8a-hexahydro-1H-pyrrolo[1,2-a]pyrazine-2-carboxylate (140 mg, 0.31 mmol) was dissolved in ethanol (3 mL) before the addition of hydrazine hydrate (46 μL, 0.94 mmol). The colourless solution was then heated to 80° C. After 3 hours the reaction mixture was cooled to ambient temperature then filtered through Celite. The filtrate was concentrated in vacuo to a colourless gum. This material was taken up in DCM (3 mL) before cooling to 0° C. Triethylamine (66 μL, 0.47 mmol) then methanesulfonyl chloride (29 μL, 0.38 mmol) were added and stirring continued for 45 minutes. The reaction was quenched by addition of saturated aqueous NaHCO₃ solution (10 mL) before separation of the layers and extraction of the aqueous with further DCM (2×30 mL). The combined organics were washed with water and passed through a hydrophobic frit. The filtrate was concentrated under reduced pressure and the residue purified by column chromatography (silica, 20-80% EtOAc-PE gradient elution) to give the product (35 mg, 27%) as a colourless oil; ¹H NMR (500 MHz, Chloroform-d) δ 7.43-7.30 (m, 5H), 5.15 (d, 2H), 4.88 (s, 1H), 4.18 (dd, 3H), 3.37-3.28 (m, 1H), 3.26-3.13 (m, 2H), 2.98 (s, 3H), 2.63-2.56 (m, 1H), 2.38 (s, 1H), 2.11 (q, 4H), 1.88-1.68 (m, 4H); MS m/z: 368 (M+H)⁺.

Benzyl (8aS)-4-(methanesulfonamidomethyl)-3,4,6,7,8,8a-hexahydro-1H-pyrrolo[1,2-a]pyrazine-2-carboxylate (35 mg, 0.09 mmol) was dissolved in EtOAc (724 μL) and MeOH (181 μL) and stirred under a balloon of H₂. Pd(OH)₂ (6.4 mg of 20% w/w, 0.009 mmol) was added and the black suspension stirred at ambient temperature for 45 minutes. The reaction was filtered through Celite before concentrating in vacuo to give N-(((8aS)-octahydropyrrolo[1,2-a]pyrazin-4-yl)methyl)methanesulfonamide A97 (20 mg, 95%) as a colourless gum that was taken on to the next reaction; MS m/z: 234 (M+H)⁺.

Preparation 92: N-(((7S,8aS)-7-Fluorooctahydropyrrolo[1,2-a]pyrazin-4-yl)methyl)methanesulfonamide A98

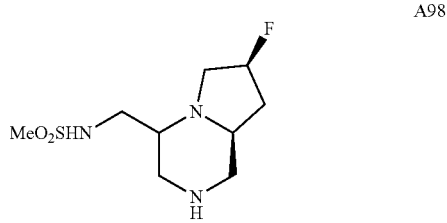

Using tert-butyl (2S,4S)-2-(aminomethyl)-4-fluoropyrrolidine-1-carboxylate in place of tert-butyl (2S)-2-(aminomethyl)pyrrolidine-1-carboxylate in the method above for A97, N-(((7S,8aS)-7-fluorooctahydropyrrolo[1,2-a]pyrazin-4-yl)methyl)methanesulfonamide A98 was obtained as a colourless gum that was taken on to the next reaction; MS m/z: 252 (M+H)⁺.

Preparation 93: tert-Butyl ((6-azaspiro[2.5]octan-4-yl)methyl)(methylsulfonyl)carbamate A99

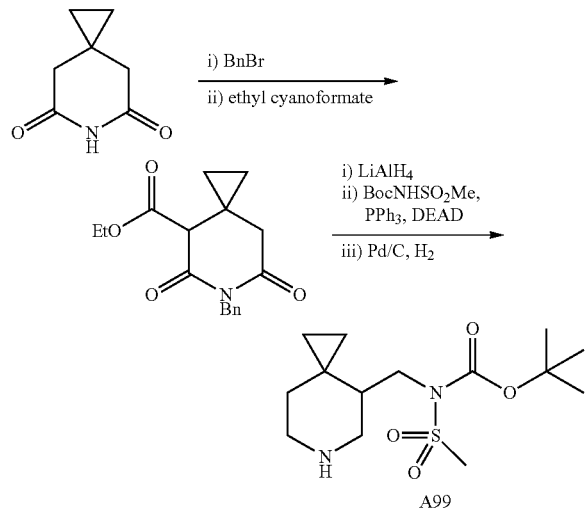

A mixture of $K_2CO_3$ (2.0 g, 14.4 mmol), BnBr (855 μL, 7.19 mmol) and 6-azaspiro[2.5]octane-5,7-dione (1 g, 7.19 mmol) in DMF (10 mL) was stirred at ambient temperature for 72 hours. The solvent was removed in vacuo and the residue was triturated with water. The solid was washed with water and dried in vacuo at 60° C. for 3 hours to give 6-benzyl-6-azaspiro[2.5]octane-5,7-dione (1.42 g, 84%); $^1$H NMR (500 MHz, DMSO-$d_6$) δ 7.31 (dd, 2H), 7.28-7.16 (m, 3H), 4.88 (s, 2H), 2.64 (s, 4H), 0.49 (s, 4H); MS m/z: 230 (M+H)$^+$.

LiHMDS (9.16 mL of 1 M, 9.16 mmol) was slowly added to a solution of 6-benzyl-6-azaspiro[2.5]octane-5,7-dione (1 g, 4.36 mmol) in THF (20 mL) at −78° C. under $N_2$. The mixture was stirred at that temperature for 30 minutes before ethyl cyanoformate (610 μL, 6.54 mmol) was added. After 30 minutes saturated aqueous $NH_4Cl$ solution was added and the mixture was brought to ambient temperature then concentrated in vacuo. The residue was partitioned between DCM and water. The organic phase was dried, filtered and concentrated in vacuo. The residue was purified by column chromatography (silica, 5-50% EtOAc-PE gradient elution) to give ethyl 6-benzyl-5,7-dioxo-6-azaspiro[2.5]octane-8-carboxylate as a colourless oil (950 mg, 68%); $^1$H NMR (500 MHz, DMSO-$d_6$) δ 7.34-7.28 (m, 2H), 7.27-7.20 (m, 3H), 5.00-4.84 (m, 2H), 4.18 (qd, 2H), 3.43 (d, 1H), 3.05 (dd, 1H), 2.30 (dd, 1H), 1.19 (t, 3H), 0.85-0.78 (m, 1H), 0.74-0.67 (m, 1H), 0.67-0.57 (m, 2H); MS m/z: 302 (M+H)$^+$.

LiAlH$_4$ (95 mg, 2.5 mmol) was added to a solution of ethyl 6-benzyl-5,7-dioxo-6-azaspiro[2.5]octane-8-carboxylate (203 mg, 0.67 mmol) in THF (10 mL) under $N_2$. After stirring at ambient temperature for 2 hours, the reaction mixture was quenched by sequential addition of $H_2O$ (100 μL), 15% aqueous NaOH solution (100 μL) and $H_2O$ (300 μL). The mixture was stirred at ambient temperature overnight, filtered through Celite and the filtrate concentrated in vacuo. The residue was taken up in DCM (5 mL) and tert-butyl N-methylsulfonylcarbamate (262 mg, 1.34 mmol) and PS—PPh$_3$ (476 mg of 2.11 mmol/g, 1.00 mmol) were added. DIAD (182 μL, 0.94 mmol) in DCM (1 mL) was slowly added with stirring at ambient temperature. After 4 hours the reaction mixture was filtered and the filtrate concentrated in vacuo. The residue was loaded on to an ion-exchange column. The column was washed with MeOH and the product eluted with 2 M methanolic ammonia. The filtrate was concentrated in vacuo and the residue was purified by reverse phase chromatography (C18, MeCN/water—0.1% ammonium hydroxide as eluent). The product fractions were lyophilised to give tert-butyl N-[(6-benzyl-6-azaspiro[2.5]octan-8-yl)methyl]-N-methylsulfonyl-carbamate (19 mg, 7%), which was taken directly on to the next reaction; MS m/z: 409 (M+H)$^+$.

Pd on C, wet, Degussa (5 mg of 10% w/w, 0.047 mmol) was transferred to a nitrogen-filled flask and the vessel evacuated and re-filled with nitrogen. A solution of tert-butyl N-[(6-benzyl-6-azaspiro[2.5]octan-8-yl)methyl]-N-methylsulfonyl-carbamate (19 mg, 0.047 mmol) in MeOH (5 mL) was added and the resulting solution degassed with vacuum/nitrogen cycles (×3). The atmosphere was exchanged with vacuum/hydrogen cycles (×3) and the reaction mixture stirred at ambient temperature for 30 minutes. The reaction mixture was filtered through Celite, washing with MeOH. The filtrate was concentrated in vacuo to give tert-butyl ((6-azaspiro[2.5]octan-4-yl)methyl)(methylsulfonyl)carbamate A99 (15 mg), which was used directly in the next step without any purification; MS m/z: 319 (M+H)$^+$.

Preparation 94: N-((6,6-Dimethylpiperazin-2-yl)methyl)methanesulfonamide A100

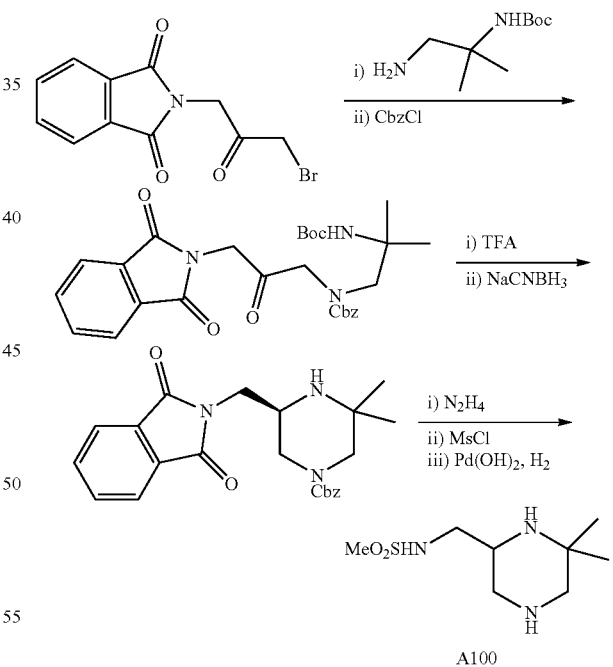

2-(3-Bromo-2-oxo-propyl)isoindoline-1,3-dione (250 mg, 0.89 mmol) was dissolved in DCM (9 mL) before the addition of tert-butyl N-(2-amino-1,1-dimethyl-ethyl)carbamate (167 mg, 0.89 mmol) and triethylamine (136 μL, 0.97 mmol). The colourless solution was stirred at ambient temperature for 1 hour. Cbz-Cl (152 μL, 1.06 mmol) and triethylamine (370 μL, 2.66 mmol) were added and stirring continued. After 50 minutes the reaction was diluted with water (20 mL). The layers were separated and the aqueous phase extracted with DCM (2×30 mL). The combined organics were washed with 1 M aqueous HCl solution (20 mL) and brine (20 mL) and filtered through a hydrophobic frit. The filtrate was concentrated in vacuo and the residue purified by column chromatography (silica, 30-80% EtOAc-PE gradient elution) to give benzyl N-[2-(tert-butoxycarbonylamino)-2-methyl-propyl]-N-[3-(1,3-dioxoisoindolin-2-yl)-2-oxo-propyl]carbamate (260 mg, 54%) as a colourless gum; MS m/z: 524 (M+H)$^+$.

Benzyl N-[2-(tert-butoxycarbonylamino)-2-methyl-propyl]-N-[3-(1,3-dioxoisoindolin-2-yl)-2-oxo-propyl]carbamate (260 mg, 0.48 mmol) was dissolved in DCM (3 mL) and the solution cooled to 0° C. TFA (1.8 mL) was slowly added. After 15 minutes the reaction mixture was concentrated in vacuo. The orange residue was dissolved in methanol before addition of sodium cyanoborohydride (75 mg, 1.19 mmol). The solution was stirred at ambient temperature for 1 hour. The reaction was quenched with saturated aqueous NaHCO$_3$ solution before extracting with EtOAc (3×40 mL). The combined organics were washed with water (30 mL) and brine (20 mL), then dried (Na$_2$SO$_4$), filtered and concentrated in vacuo to give benzyl 5-[(1,3-dioxoisoindolin-2-yl)methyl]-3,3-dimethyl-piperazine-1-carboxylate (190 mg, 95%) as a colourless gum; MS m/z: 408 (M+H)$^+$.

Benzyl 5-[(1,3-dioxoisoindolin-2-yl)methyl]-3,3-dimethyl-piperazine-1-carboxylate (190 mg, 0.44 mmol) was dissolved in ethanol (4 mL) before addition of hydrazine hydrate (64 µL, 1.32 mmol). The colourless solution was then heated to 80° C. for 90 minutes. The resulting white suspension was allowed to cool to ambient temperature then filtered through Celite. The filtrate was concentrated, the residue dissolved in DCM and filtered again. The filtrate was concentrated to give a colourless gum which was dissolved in DCM (4.5 mL) before cooling to 0° C. Triethylamine (90 µL, 0.66 mmol) then methanesulfonyl chloride (41 µL, 0.53 mmol) were added and stirring continued for 15 minutes. The reaction was quenched by addition of saturated aqueous NaHCO$_3$ solution (10 mL) before separation of the layers and extraction of the aqueous with further DCM (2×30 mL). The combined organics were washed with water and passed through a hydrophobic frit. The organic phase was concentrated and the residue purified by column chromatography (silica, 20-80% EtOAc-PE gradient elution) to give benzyl 5-(methanesulfonamidomethyl)-3,3-dimethyl-piperazine-1-carboxylate (119 mg, 76%) as a colourless oil; MS m/z: 356 (M+H)$^+$.

Benzyl 5-(methanesulfonamidomethyl)-3,3-dimethyl-piperazine-1-carboxylate (119 mg, 0.33 mmol) was dissolved in ethyl acetate (2.5 mL) and MeOH (600 µL) and submitted to an atmosphere of H$_2$. Pd(OH)$_2$ (24 mg of 20% w/w, 0.03 mmol) was added and the black suspension stirred at ambient temperature for 30 minutes. The reaction was filtered through Celite before concentrating to give N-((6,6-dimethylpiperazin-2-yl)methyl)methanesulfonamide A100 as a colourless gum, (71 mg, 96%); MS m/z: 222 (M+H)$^+$. This material was taken on to the next reaction without further purification.

Preparation 95:
N-(1-(Morpholin-2-yl)propyl)methanesulfonamide
A101

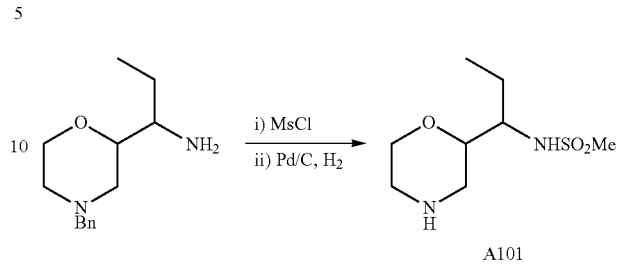

1-(4-Benzylmorpholin-2-yl)propan-1-amine (594 mg, 2.54 mmol) and Et$_3$N (707 µL, 5.07 mmol) in DCM (12 mL) were cooled to 0° C. in an ice bath before the dropwise addition of methanesulfonyl chloride (220 µL, 2.84 mmol). The reaction mixture was allowed to warm to ambient temperature and stirred for 4 hours. The reaction mixture was quenched with saturated aqueous NaHCO$_3$ solution. The layers were separated and the aqueous phase extracted once with DCM. The combined organics were dried (MgSO$_4$), filtered and concentrated in vacuo. The residue was purified by column chromatography (silica, 0-100% EtOAc-PE gradient elution) to give the product as a pale yellow solid (652 mg, 82%); $^1$H NMR (500 MHz, DMSO-d$_6$) δ7.39-7.17 (m, 5H), 3.86-3.73 (m, 1H), 3.55-3.34 (m, 4H), 3.31 (m, 2H), 3.23-3.04 (m, 1H), 2.87 (d, J=2.5 Hz, 3H), 2.08-1.97 (m, 1H), 1.97-1.83 (m, 1H), 1.64-1.47 (m, 1H), 1.42-1.23 (m, 1H), 0.87 (td, J=7.4, 1.3 Hz, 3H); MS m/z: 313 (M+H)$^+$.

Pd on C, wet, Degussa (88 mg of 10% w/w, 0.08 mmol) was transferred to a nitrogen-filled flask and the vessel evacuated and re-filled with nitrogen. A solution of N-[1-(4-benzylmorpholin-2-yl)propyl]methanesulfonamide (350 mg, 1.12 mmol) in HCl (14.7 mL of a 3 M solution in MeOH, 44.1 mmol) was added and the resulting solution degassed with vacuum/nitrogen cycles (×3). The atmosphere was exchanged with vacuum/hydrogen cycles (×3) and the reaction mixture stirred at ambient temperature for 6 hours. The reaction mixture was filtered through Celite, washing with MeOH. The filtrate was concentrated in vacuo to give N-(1-(morpholin-2-yl)propyl)methanesulfonamide A101 as a yellow oil (246 mg, 85%); $^1$H NMR (500 MHz, DMSO-d$_6$) δ 9.42 (s, NH), 3.99 (dt, J=12.5, 3.8 Hz, 1H), 3.74 (td, J=12.4, 2.3 Hz, 1H), 3.63 (ddd, J=11.3, 6.1, 2.1 Hz, 1H), 3.23 (ddt, J=14.9, 9.2, 3.1 Hz, 2H), 3.17 (m, 2H), 2.96 (s, 3H), 2.87-2.73 (m, 1H), 1.59 (dtd, J=15.0, 7.4, 4.7 Hz, 1H), 1.39 (dddd, J=16.7, 14.0, 9.0, 7.2 Hz, 1H), 0.91 (td, J=7.4, 4.6 Hz, 3H); MS m/z: 223 (M+H)$^+$. This material was taken on to the next step without further purification.

Preparation 96: Dimethyl((piperidin-3-ylmethyl)imino)-λ$^6$-sulfanone A102

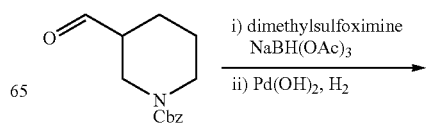

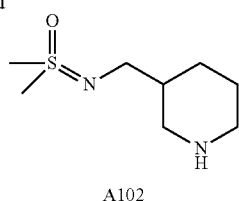

A102

Benzyl 3-formylpiperidine-1-carboxylate (100 mg, 0.40 mmol) was dissolved in DCE (2 mL). Dimethylsulfoximine (57 mg, 0.61 mmol), then NaBH(OAc)$_3$ (341 mg, 1.62 mmol) were added and the mixture stirred at ambient temperature for 30 minutes. The reaction was quenched by the addition of saturated aqueous NaHCO$_3$ solution. The mixture was stirred until effervescence stopped. The layers were separated and the aqueous phase extracted with DCM (2×20 mL). The combined organics were washed with brine, filtered through a hydrophobic frit and the filtrate concentrated in vacuo. The residue was purified by column chromatography (silica, 30-100% EtOAc-PE followed by 0-20% MeOH-DCM gradient elution) to give benzyl 3-[[[dimethyl(oxo)-$\lambda^6$-sulfanylidene]amino]methyl]piperidine-1-carboxylate as a colourless oil (55 mg, 42%); $^1$H NMR (500 MHz, Chloroform-d) δ 7.42-7.28 (m, 5H), 5.15 (d, J=2.8 Hz, 2H), 4.18-4.08 (m, 1H), 3.98 (s, 1H), 2.97 (d, J=8.4 Hz, 9H), 2.76-2.67 (m, 1H), 1.89 (dd, J=13.3, 4.3 Hz, 1H), 1.70 (s, 2H), 1.50 (s, 1H), 1.31-1.18 (m, 1H); MS m/z: 325 (M+H)$^+$.

Benzyl 3-[[[dimethyl(oxo)-$\lambda^6$-sulfanylidene]amino]methyl]piperidine-1-carboxylate (55 mg, 0.17 mmol) was dissolved in EtOAc (1.2 mL) and MeOH (310 μL) and submitted to an atmosphere of H$_2$. Pd(OH)$_2$ (12 mg of 20% w/w, 0.02 mmol) was added and the black suspension stirred at ambient temperature overnight. Pd(OH)$_2$ (12 mg of 20% w/w, 0.02 mmol) was added. After stirring for 30 minutes the reaction was filtered through Celite. The filtrate was concentrated in vacuo to give dimethyl((piperidin-3-ylmethyl)imino)-$\lambda^6$-sulfanone A102, (28 mg, 87%) as a colourless gum, which was taken on to the next reaction without further purification; MS m/z: 191 (M+H)$^+$.

Preparation 97:
(2,5-Dimethylpiperidin-3-yl)methanol A103

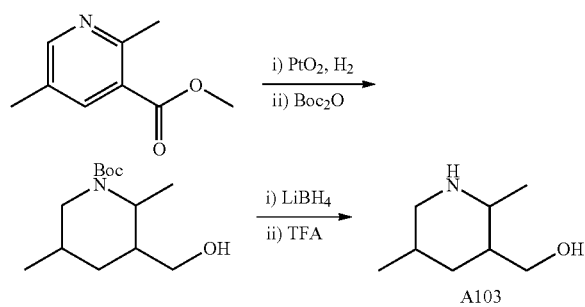

A103

A mixture of methyl 2,5-dimethylpyridine-3-carboxylate (2.6 g, 15.74 mmol) and PtO$_2$ (713 mg, 3.14 mmol) in HCl (57 mL of a 3 M solution in MeOH, 171.1 mmol) was stirred under a balloon of H$_2$ for 16 hours at ambient temperature. The reaction mixture was filtered through Celite and the filtrate concentrated in vacuo. The residue was dissolved in THF (27 mL) and triethylamine (6.6 mL, 47.3 mmol), DMAP (96 mg, 0.79 mmol) and di-tert-butyl dicarbonate (17.4 mL of a 1 M solution in THF, 17.4 mmol) were added sequentially. The reaction mixture was stirred overnight, then partitioned between EtOAc and water. The organic layer was separated and washed with NH$_4$Cl solution, water, brine, then dried (MgSO$_4$), filtered and concentrated in vacuo. The residue was purified by column chromatography (silica, 0-10% EtOAc-PE gradient elution). The product fractions were combined and concentrated in vacuo to give the product as a colourless oil containing a mixture of diastereomers (1.4 g, 33%); $^1$H NMR (400 MHz, MeOH-d$_4$) δ 4.80-4.62 (m, 1H), 3.95-3.78 (m, 1H), 3.71 (d, 3H), 2.71 (dq, 1H), 2.46 (dt, 1H), 1.89-1.77 (m, 1H), 1.48 (q, 10H), 1.10-0.92 (m, 7H).

O1-tert-Butyl O3-methyl 2,5-dimethylpiperidine-1,3-dicarboxylate (1.4 g, 5.16 mmol) was dissolved in THF (42 mL) and cooled to 0° C. Lithium borohydride (10.3 mL of a 2 M solution in THF, 20.6 mmol) was added and the reaction allowed to warm to ambient temperature. After 30 minutes the reaction mixture was warmed to 50° C. and stirred for 16 hours. The reaction was cooled to ambient temperature then quenched with water. The mixture was extracted with EtOAc (×3). The combined organics were dried and concentrated in vacuo to give tert-butyl 3-(hydroxymethyl)-2,5-dimethyl-piperidine-1-carboxylate (1.25 g, 100%) as a colourless oil that was taken directly on to the next reaction without further purification; $^1$H NMR (400 MHz, MeOH-d$_4$) δ 4.42-4.27 (m, 1H), 3.82-3.68 (m, 1H), 3.34-3.23 (m, 2H), 2.33 (dt, 1H), 1.91 (s, 1H), 1.82-1.68 (m, 1H), 1.54-1.37 (m, 2H), 1.35 (s, 9H), 0.95-0.87 (m, 3H), 0.86-0.76 (m, 4H).

tert-Butyl 3-(hydroxymethyl)-2,5-dimethyl-piperidine-1-carboxylate (1.25 g, 5.14 mmol) was dissolved in DCM (62.5 mL) and stirred at 0° C. TFA (6.0 mL, 77.1 mmol) was added and the reaction allowed to warm slowly to ambient temperature. After stirring for 16 hours, the reaction mixture was concentrated in vacuo. The residue was taken up in MeOH and passed through an ion-exchange cartridge, eluting the product with a 2 M methanolic ammonia solution. The filtrate was concentrated in vacuo to give (2,5-dimethylpiperidin-3-yl)methanol A103 as a colourless oil (510 mg, 69%); $^1$H NMR (400 MHz, MeOH-d$_4$) δ 3.76 (d, 1H), 3.38 (d, 2H), 2.72 (ddd, 1H), 2.45 (dd, 1H), 1.99 (dtdd, 1H), 1.61 (dddd, 2H), 1.10 (d, 3H), 1.02-0.95 (m, 1H), 0.92 (d, 3H).

Preparation 98: Dimethyl((2-methylpiperidin-3-yl)imino)-$\lambda^6$-sulfanone A104

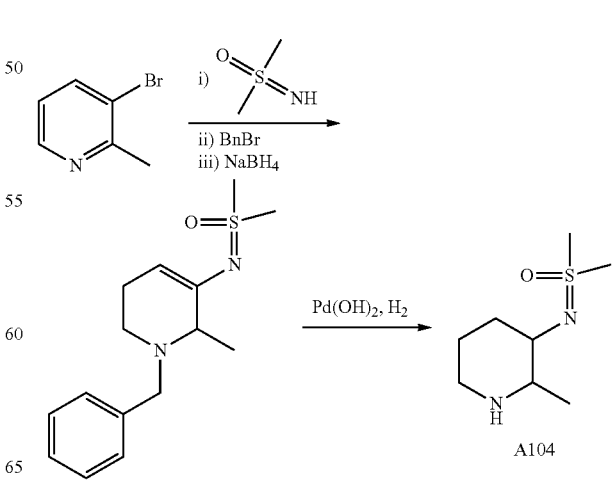

A104

3-Bromo-2-methylpyridine (5.17 g, 30.1 mmol), iminodimethyl-$\lambda^6$-sulfane (2.94 g, 31.6 mmol), Xantphos (1.74 g, 3.0 mmol) and cesium carbonate (14.7 g, 45.0 mmol) were dissolved in 1,4-dioxane (52 mL). The reaction mixture was degassed (vacuum/$N_2$ cycles) and $Pd_2(dba)_3$ (1.38 g, 1.50 mmol) was added. The reaction flask was purged under $N_2$ and the mixture heated under reflux for 7 hours then allowed to cool to ambient temperature. The reaction mixture was filtered, washing with EtOAc. The filtrate was concentrated in vacuo and the residue purified by column chromatography (silica, 0-10% MeOH-DCM gradient elution) to give the product as an orange oil (5.46 g, 97%); $^1$H NMR (500 MHz, DMSO-$d_6$) δ 7.96 (dd, 1H), 7.32 (ddd 1H), 7.03 (ddd, 1H), 3.24 (s, 6H), 2.35 (s, 3H); MS m/z: 185 (M+H)$^+$.

To a solution of dimethyl((2-methylpyridin-3-yl)imino)-$\lambda^6$-sulfanone (5.38 g, 28.6 mmol) in MeCN (53 mL) was added BnBr (3.44 mL, 28.9 mmol). The mixture was heated under reflux for 4 hours. The reaction mixture was allowed to cool to ambient temperature and the resulting precipitate collected by filtration, washing with cold MeCN. The product was obtained as an off-white solid (8.56 g, 84%); $^1$H NMR (500 MHz, DMSO-$d_6$) δ 8.58 (dd, J=6.1, 1.2 Hz, 1H), 8.11 (dd, J=8.5, 1.2 Hz, 1H), 7.81 (dd, J=8.4, 6.1 Hz, 1H), 7.51-7.36 (m, 3H), 7.28-7.14 (m, 2H), 5.87 (s, 2H), 3.37 (d, J=61.8 Hz, 6H), 2.57 (s, 3H).

NaBH$_4$ (1.28 g, 33.8 mmol) was added portionwise to a solution of 1-benzyl-3-((dimethyl(oxo)-$\lambda^6$-sulfanylidene)amino)-2-methylpyridin-1-ium bromide (4.0 g, 11.3 mmol) in MeOH (25 mL) at 0° C. under $N_2$. After 30 minutes, NaBH$_4$ (1.28 g, 33.8 mmol) was added and the reaction mixture stirred for 16 hours, with the temperature rising to ambient. The mixture was partitioned between DCM and water. The layers were separated and the aqueous phase extracted with DCM (×2). The combined organics were dried (MgSO$_4$), filtered and concentrated in vacuo to give the desired product (2.61 g, 83%); $^1$H NMR (500 MHz, DMSO-$d_6$) δ 7.39-7.15 (m, 5H), 3.77-3.51 (m, 2H), 3.11-2.98 (m, 6H), 2.83-2.68 (m, 2H), 2.42 (ddd, J=12.3, 5.6, 3.4 Hz, 2H), 2.27-2.05 (m, 1H), 1.95-1.77 (m, 1H), 1.12 (d, J=6.6 Hz, 3H); MS m/z: 279 (H+H)$^+$.

Pd(OH)$_2$, (1.36 g, 20% w/w, Degussa, 9.68 mmol) was transferred to a nitrogen-filled bottle and the vessel evacuated and re-filled with nitrogen. A solution of ((1-benzyl-2-methyl-1,2,5,6-tetrahydropyridin-3-yl)imino)dimethyl-$\lambda^6$-sulfanone (2.45 g, 8.80 mmol) in MeOH (120 mL) was then added and the resulting solution degassed by vacuum/nitrogen cycles (×3). The atmosphere was exchanged by vacuum/hydrogen cycles and the reaction mixture was shaken on a Parr hydrogenator for 4 days under a pressure of 60 psi H$_2$. The reaction mixture was filtered through Celite, washing with MeOH. The combined filtrates were concentrated in vacuo. The residue was resubmitted to the reaction conditions and shaken under a pressure of 60 psi H$_2$ for 1 day. The reaction mixture was filtered through Celite, washing with MeOH. The filtrate was concentrated in vacuo to give dimethyl((2-methylpiperidin-3-yl)imino)-$\lambda^6$-sulfanone A104 as an oil which solidified to a white solid on standing (1.46 g, 83%); $^1$H NMR (500 MHz, DMSO-$d_6$) δ 3.34-3.22 (m, 1H), 3.06-2.97 (m, 6H), 2.88 (d, J=13.0 Hz, 1H), 2.85-2.72 (m, 2H), 2.65-2.54 (m, 2H), 2.41 (td, J=12.0, 2.8 Hz, 1H), 2.23 (dq, J=8.8, 6.2 Hz, 1H), 1.82-1.70 (m, 2H), 1.69-1.61 (m, 1H), 1.63-1.47 (m, 2H), 1.40 (qt, J=12.7, 3.9 Hz, 1H), 1.31-1.14 (m, 2H), 0.99 (d, J=6.2 Hz, 3H), 0.93 (d, J=6.6 Hz, 3H), approximately 1:1 mixture of rotamers observed, hence doubling of all aliphatic peaks; MS m/z: 191 (M+H)$^+$.

Preparation 99: Dimethyl((4-methylpiperidin-3-yl)imino)-$\lambda^6$-sulfanone A105

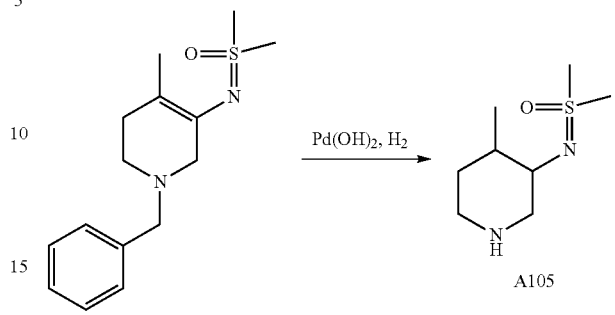

Using the same method as above for A104, ((1-benzyl-4-methyl-1,2,5,6-tetrahydropyridin-3-yl)imino)dimethyl-$\lambda^6$-sulfanone was prepared using 3-bromo-4-methylpyridine in place of 3-bromo-2-methyl-pyridine.

((1-benzyl-4-methyl-1,2,5,6-tetrahydropyridin-3-yl)imino)dimethyl-$\lambda^6$-sulfanone (860 mg, 3.03 mmol), Pd(OH)$_2$ (425 mg, 3.03 mmol), AcOH (258 μL, 4.54 mmol) in MeOH was shaken in a Parr hydrogenator at ambient temperature under 60 psi pressure of H$_2$ for 48 hours. The reaction mixture was filtered and the residue, containing dimethyl((4-methylpiperidin-3-yl)imino)-$\lambda^6$-sulfanone A105, was taken directly on to the next reaction without purification; MS m/z: 191 (M+H)$^+$.

Preparation 100: Dimethyl(((2-methylpiperidin-3-yl)methyl)imino)-$\lambda^6$-sulfanone A106

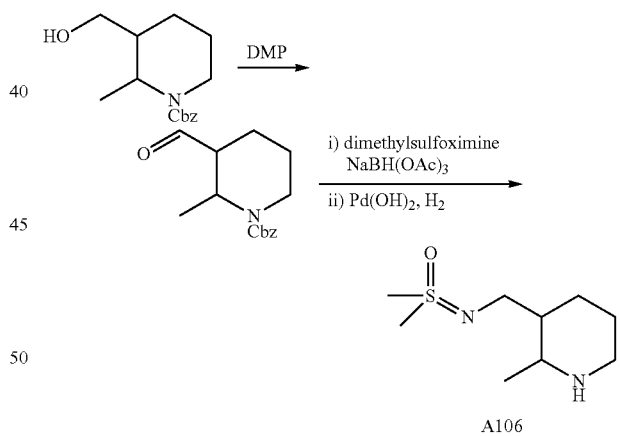

Benzyl 3-(hydroxymethyl)-2-methyl-piperidine-1-carboxylate (500 mg, 1.90 mmol) was dissolved in DCM (19 mL) before addition of Dess-Martin periodinane (967 mg, 2.28 mmol). The resulting suspension was stirred at ambient temperature for 50 minutes. The reaction was quenched by addition of saturated aqueous NaHCO$_3$ solution and stirred for 20 minutes. The layers were separated and the aqueous extracted with DCM (2×20 mL). The combined organics were dried (Na$_2$SO$_4$), filtered through a hydrophobic frit and purified by column chromatography (silica, 0-40% EtOAc-PE gradient elution) to give benzyl 3-formyl-2-methyl-piperidine-1-carboxylate (360 mg, 47%); MS m/z: 262 (M+H)$^+$.

Benzyl 3-formyl-2-methyl-piperidine-1-carboxylate (360 mg, 1.38 mmol) was dissolved in DCE (14 mL) before addition of dimethylsulfoximine (193 mg, 2.07 mmol) followed by NaBH(OAc)$_3$ (1.13 g, 5.51 mmol). After 80 minutes the reaction was quenched by addition of saturated aqueous NaHCO$_3$ solution and stirred until effervescence stopped. The layers were separated and the aqueous phase extracted with DCM (2×20 mL). The combined organics were washed with brine, filtered through a hydrophobic frit and purified by column chromatography (silica, 0-20% MeOH-DCM gradient elution) to give benzyl 3-(((dimethyl(oxo)-λ$^6$-sulfanylidene)amino)methyl)-2-methylpiperidine-1-carboxylate (260 mg, 56%) as a colourless oil; MS m/z: 261 (M-SOMe$_2$)$^+$.

Benzyl 3-(((dimethyl(oxo)-λ$^6$-sulfanylidene)amino) methyl)-2-methylpiperidine-1-carboxylate (260 mg, 0.768 mmol) was dissolved in EtOAc (6 mL) and MeOH (1.5 mL) and submitted to an atmosphere of H$_2$. Pd(OH)$_2$ (54 mg of 20% w/w, 0.08 mmol) was added and the black suspension stirred at ambient temperature for 15 minutes. The reaction was filtered through Celite before concentrating in vacuo to give dimethyl-[(2-methyl-3-piperidyl)methylimino]-oxo-λ$^6$-sulfane A106 (145 mg, 92%) as a colourless gum; MS m/z: 205 (M+H)$^+$.

Preparation 101: N-((4-Hydroxy-2,4,5-trimethylpiperidin-3-yl)methyl)methanesulfonamide, A107

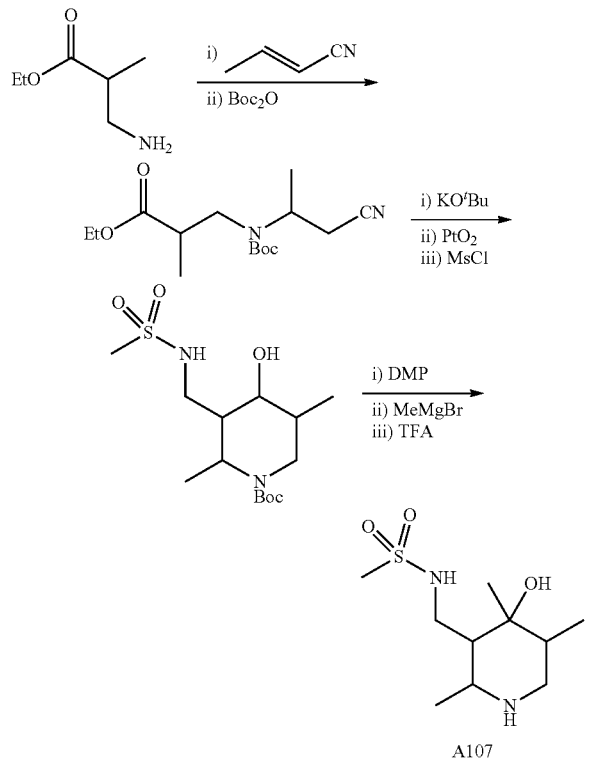

A107

A mixture of ethyl 3-amino-2-methyl-propanoate (6.0 g, 45.7 mmol) and (E)-but-2-enenitrile (4.0 mL, 49.1 mmol) in ethanol (60 mL) was heated under reflux for 18 hours. The reaction mixture was cooled to ambient temperature and concentrated under reduced pressure to give a colourless oil. The residue was purified by column chromatography (silica, 5-100% [EtOAc+1% Et$_3$N]-PE gradient elution) to give the product as an oil (2.5 g, 28%); MS m/z: 199 (M+H)$^+$.

Ethyl 3-[(2-cyano-1-methyl-ethyl)amino]-2-methyl-propanoate (1.46 g, 7.36 mmol) and K$_2$CO$_3$ (3.6 mL of a 4 M aqueous solution, 14.5 mmol) were combined in 1,4-dioxane (3.4 mL) and water (6.7 mL) and di-tert-butyl dicarbonate (2.67 g, 12.2 mmol) was added. The mixture was stirred at ambient temperature for 16 hours, then diluted with saturated aqueous sodium bicarbonate solution and extracted with EtOAc. The organic layer was dried (MgSO$_4$) and concentrated in vacuo. The residue was purified by column chromatography (silica, 0-65% EtOAc-PE gradient elution) to give ethyl 3-[tert-butoxycarbonyl-(2-cyano-1-methylethyl)amino]-2-methyl-propanoate (2.3 g, quantitative yield) as a colourless oil, that was taken on to the next step without further purification; $^1$H NMR (500 MHz, Chloroform-d) δ 4.17 (qtd, 2H), 3.87 (dt, 1H), 3.48-3.27 (m, 2H), 2.87 (d, 2H), 2.71-2.51 (m, 1H), 1.49 (d, 9H), 1.37 (dd, 3H), 1.28 (td, 3H), 1.22-1.12 (m, 3H).

Potassium tert-butoxide (958 mg, 8.54 mmol) in toluene (50 mL) was heated to 75° C. before the addition of ethyl 3-[tert-butoxycarbonyl-(2-cyano-1-methyl-ethyl)amino]-2-methyl-propanoate (2.39 g, 8.00 mmol). The mixture was heated under reflux. After 2 hours potassium tert-butoxide (200 mg, 1.78 mmol) was added. After 4 hours the reaction mixture was allowed to cool to ambient temperature then concentrated in vacuo. The residue was partitioned between DCM and water and the layers separated. The aqueous phase was acidified to pH 4 and extracted with EtOAc (×2). The combined extracts were dried (MgSO$_4$), filtered and concentrated to give tert-butyl 3-cyano-2,5-dimethyl-4-oxo-piperidine-1-carboxylate (1.14 g, 56%) as an orange oil that was taken directly on to the next reaction; $^1$H NMR (500 MHz, Chloroform-d) δ 5.11 (d, J=30.5 Hz, 1H), 4.13 (d, J=7.1 Hz, 1H), 4.00 (d, J=5.8 Hz, 1H), 3.53-3.47 (m, 1H), 2.70 (qdd, J=7.1, 3.9, 3.0 Hz, 1H), 1.53 (d, J=1.4 Hz, 9H), 1.34-1.28 (m, 3H), 1.25 (s, 3H).

tert-Butyl 3-cyano-2,5-dimethyl-4-oxo-piperidine-1-carboxylate (1.14 g, 4.52 mmol) in EtOH (23 mL) and CHCl$_3$ (500 μL) was purged (×3 N$_2$/vacuum cycles) before the addition of PtO$_2$ (180 mg, 0.79 mmol). The N$_2$ was replaced with H$_2$ (×3 vacuum/H$_2$ purges) and the reaction mixture stirred at ambient temperature for 16 hours. PtO$_2$ (56 mg, 0.25 mmol) was added and the reaction mixture stirred for 24 hours. The mixture was filtered through Celite, washing with MeOH. The filtrate was concentrated to give tert-butyl 3-(aminomethyl)-4-hydroxy-2,5-dimethyl-piperidine-1-carboxylate (1.18 g, 100%), which was taken directly on to the next reaction; MS m/z: 259 (M+H)$^+$.

tert-Butyl 3-(aminomethyl)-4-hydroxy-2,5-dimethyl-piperidine-1-carboxylate (1.18 g, 4.57 mmol) in DCM (20 mL) was cooled to 0° C., then treated with Et$_3$N (1.9 mL, 13.7 mmol) followed by the dropwise addition of methanesulfonyl chloride (354 μL, 4.57 mmol). The reaction mixture was allowed to warm to ambient temperature. After stirring for 3 hours, the reaction mixture was partitioned between saturated aqueous sodium bicarbonate solution and DCM. The layers were separated and the organic phase dried (MgSO$_4$), filtered and concentrated in vacuo. The residue was partially purified by column chromatography (silica, 0-10% MeOH-DCM gradient elution) to give a mixture of 0- and N-mesylated products (575 mg) as an orange oil. This material was dissolved in DCM (5 mL) under N$_2$ and the solution cooled in an ice bath. Dess-Martin periodinane (750 mg, 1.77 mmol) was added and the reaction mixture stirred for 18 hours, with the temperature rising to ambient. The resulting solution was diluted with DCM, saturated aqueous sodium thiosulfate solution and saturated aqueous NaHCO$_3$ solution. After stirring for 5 minutes, the organic phase was isolated using a phase separation cartridge. The organic phase was concentrated in vacuo and the residue taken up in THF (10 mL) under N$_2$. The solution was cooled to 0° C. and MeMgBr (3 mL of a 3 M solution in ether, 9 mmol) was added dropwise. The reaction mixture was stirred for 18 hours with the temperature rising to ambient. The reaction mixture was diluted with EtOAc. The organic phase was washed with a 10% aqueous citric acid solution, saturated aqueous sodium bicarbonate solution and brine, then dried (Na$_2$SO$_4$) filtered and concentrated. The residue was taken up in DCM (2 mL), TFA (2 mL) was added and the resultant mixture stirred for 2 hours at ambient temperature. The mixture was concentrated in vacuo to give a brown oil containing N-((4-hydroxy-2,4,5-trimethylpiperidin-3-yl)methyl)methanesulfonamide A107 (400 mg) that was used in the next reaction without further purification; MS m/z: 251 (M+H)$^+$.

Preparation 102: Diethyl((5-methylpiperidin-3-yl)imino)-λ$^6$-sulfanone A108

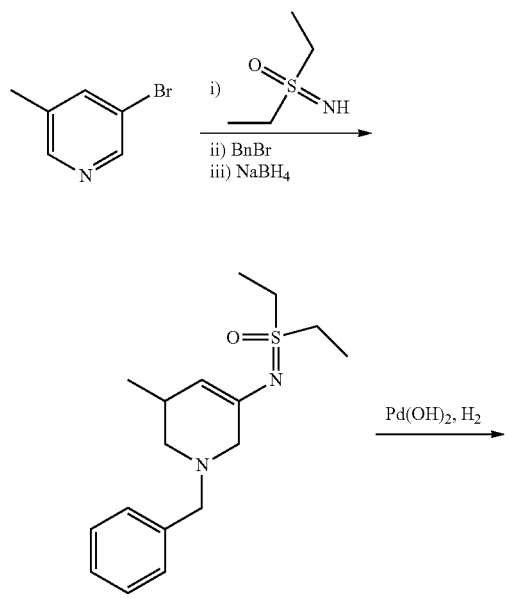

3-Bromo-5-methyl-pyridine (676 mg, 3.93 mmol), diethyl(imino)-λ$^6$-sulfanone (500 mg, 4.13 mmol), Xantphos (227 mg, 0.39 mmol) and cesium carbonate (1.92 g, 5.89 mmol) were dissolved in 1,4-dioxane (7 mL). The reaction mixture was degassed (vacuum/nitrogen cycles) and Pd$_2$(dba)$_3$ (180 mg, 0.20 mmol) added. The reaction flask was purged under N$_2$ and the mixture heated under reflux for 4 hours. The reaction mixture was cooled to ambient temperature and filtered, washing with EtOAc. The filtrate was concentrated in vacuo and residue purified by column chromatography (silica 40 g, 0-10% MeOH-DCM gradient elution) to give the product as a yellow solid (741 mg, 89%); $^1$H NMR (500 MHz, DMSO-d$_6$) δ8.00 (d, J=2.6 Hz, 1H), 7.90 (dd, J=1.9, 0.9 Hz, 1H), 7.15 (ddd, J=2.7, 1.9, 0.8 Hz, 1H), 3.37-3.26 (m, 4H), 2.21 (d, J=0.7 Hz, 3H), 1.26 (t, J=7.4 Hz, 6H); MS m/z: 213 (M+H)$^+$.

To a solution of diethyl-[(5-methyl-3-pyridyl)imino]-oxo-λ$^6$-sulfane (741 mg, 3.49 mmol) in MeCN (11 mL) was added BnBr (420 μL, 3.53 mmol). The mixture was heated under reflux for 3 hours then cooled to ambient temperature. The resulting precipitate was collected by filtration, washing with MeCN. The filtrate was concentrated and the residue triturated with MeCN. This was combined with the first crop to give (1-benzyl-5-methyl-3-pyridyl)imino-diethyl-oxo-λ$^6$-sulfane bromide as a white solid (855 mg, 64%); $^1$H NMR (500 MHz, DMSO-d$_6$) δ 8.64-8.38 (m, 2H), 7.88 (ddd, 1H), 7.66-7.23 (m, 5H), 5.67 (s, 2H), 3.53 (q, 4H), 2.40 (d, 3H), 1.28 (t, 6H).

To a solution of (1-benzyl-5-methyl-3-pyridyl)imino-diethyl-oxo-λ$^6$-sulfane bromide (855 mg, 2.23 mmol) in MeOH (11 mL) was added NaBH$_4$ (169 mg, 4.46 mmol) at 0° C. The reaction mixture was stirred for 30 minutes then NaBH$_4$ (84 mg, 2.23 mmol) was added. Two further additions of NaBH$_4$ (84 mg, 2.23 mmol) were made at 60 and 90 minutes. After 2 hours the reaction mixture was diluted with water and concentrated in vacuo. The residue was partitioned between DCM and water. The organic layer was separated, dried (MgSO$_4$), filtered and concentrated in vacuo to give the product as a yellow oil (585 mg) which was taken on to the next reaction; MS m/z: 307 (M+H)$^+$.

Pd(OH)$_2$ (206 mg, 1.47 mmol) was added to a solution of ((1-benzyl-5-methyl-1,2,5,6-tetrahydropyridin-3-yl)imino)diethyl-λ$^6$-sulfanone (585 mg, 1.34 mmol) and AcOH (150 μL, 2.64 mmol) in MeOH (15 mL). The mixture was shaken in a Parr hydrogenator under a pressure of 60 psi H$_2$ for 24 hours. The reaction mixture was filtered and the filtrate concentrated in vacuo. The residue, containing diethyl((5-methylpiperidin-3-yl)imino)-λ$^6$-sulfanone A108 was taken directly on to the next reaction; MS m/z: 219 (M+H)$^+$.

Preparation 103: Cyclopropyl(methyl)((5-methylpiperidin-3-yl)imino)-λ$^6$-sulfanone, A109

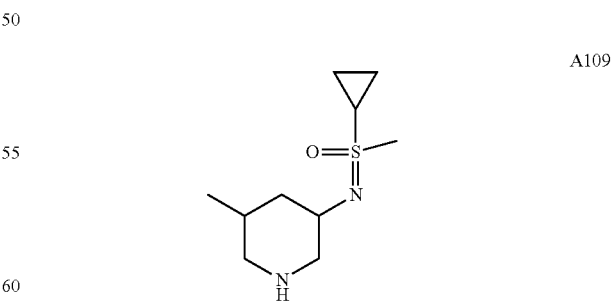

Using the method above for A108, cyclopropyl(methyl)((5-methylpiperidin-3-yl)imino)-λ$^6$-sulfanone, A109, [MS m/z: 217 (M+H)$^+$] was prepared by using cyclopropyl(imino)(methyl)-λ$^6$-sulfanone in place of diethyl(imino)-λ$^6$-sulfanone.

Preparation 104: Ethyl(methyl)((5-methylpiperidin-3-yl)imino)-$\lambda^6$-sulfanone A110

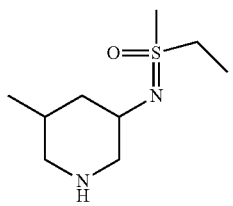

Similarly, ethyl(methyl)((5-methylpiperidin-3-yl)imino)-$\lambda^6$-sulfanone A110 was prepared using ethyl(imino)(methyl)-$\lambda^6$-sulfanone in place of diethyl(imino)-$\lambda^6$-sulfanone; $^1$H NMR (500 MHz, DMSO-d$_6$) δ 2.88-2.79 (m, 3H), 2.71-2.57 (m, 2H), 2.14-2.03 (m, 1H), 1.83-1.73 (m, 1H), 1.27-1.12 (m, 5H), 0.98-0.88 (m, 4H), 0.76 (d, J=6.6 Hz, 3H).

Preparation 105: ((2,5-Dimethylpiperidin-3-yl)imino)dimethyl-$\lambda^6$-sulfanone A111

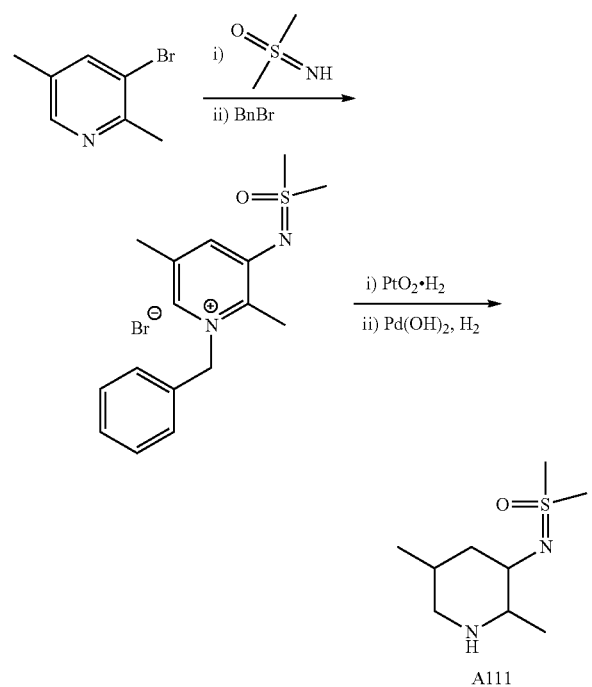

Xantphos (622 mg, 1.08 mmol), cesium carbonate (5.25 g, 16.1 mmol) and Pd$_2$(dba)$_3$ (492 mg, 0.54 mmol) were combined under N$_2$. The mixture was dissolved in 1,4-dioxane (22 mL) before addition of 3-bromo-2,5-dimethyl-pyridine (2.0 g, 10.8 mmol) and iminodimethyl-$\lambda^6$-sulfanone (1.05 g, 11.3 mmol). The reaction mixture was heated at 105° C. for 4 hours then cooled to ambient temperature. The reaction mixture was filtered, washing with EtOAc and the filtrate concentrated in vacuo. The residue was purified by column chromatography (silica, 0-20% MeOH-DCM gradient elution) to give the product as a pale yellow solid (1.85 g, 87%); $^1$H NMR (500 MHz, Chloroform-d) δ 7.99 (dd, 1H), 7.31-7.27 (m, 1H), 3.17 (s, 6H), 2.44 (s, 3H), 2.26 (q, 3H); MS m/z: 199 (M+H)$^+$.

To a solution of (2,5-dimethyl-3-pyridyl)imino-dimethyl-$\lambda^6$-sulfane (680 mg, 3.43 mmol) in MeCN (17 mL) was added BnBr (420 μL, 3.46 mmol). The resulting white suspension was heated to 85° C. After stirring for 3 hours the reaction mixture was cooled to ambient temperature and concentrated in vacuo. The residue was triturated with TBME (20 mL) and MeCN. The resulting solid was collected by filtration and dried overnight in vacuo to give 1-benzyl-3-((dimethyl(oxo)-$\lambda^6$-sulfanylidene)amino)-2,5-dimethylpyridin-1-ium bromide as a white solid (1.1 g, 87%); MS m/z: 289 (M$^+$).

Platinum oxide (25 mg, 0.11 mmol) was added to a flask under nitrogen before the addition of 1-benzyl-3-((dimethyl(oxo)-$\lambda^6$-sulfanylidene)amino)-2,5-dimethylpyridin-1-ium bromide (200 mg, 0.54 mmol), methanol (2.7 mL) and triethylamine (151 μL, 1.08 mmol). The flask was purged of air (evacuate/back-fill with N$_2$×3) before submitting to an atmosphere of H$_2$ and stirring at ambient temperature. After 90 minutes, platinum oxide (25 mg, 0.11 mmol) was added and stirring continued for 90 minutes. Platinum oxide (25 mg, 0.11 mmol) was added and stirring continued for 2 hours. Pd(OH)$_2$ (8 mg, 0.05 mmol) was added and stirring continued for 16 hours.

The reaction mixture was filtered through Celite and the filtrate concentrated in vacuo. The residue, which contained ((2,5-dimethylpiperidin-3-yl)imino)dimethyl-$\lambda^6$-sulfanone, A111 (190 mg, 17%) was taken directly on to the next reaction without further purification; MS m/z: 201 (M+H)$^+$.

Preparation 106: ((5-Ethylpiperidin-3-yl)imino)dimethyl-$\lambda^6$-sulfanone A112

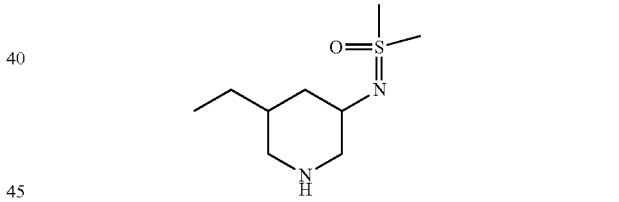

Using the method above for A111, ((5-ethylpiperidin-3-yl)imino)dimethyl-$\lambda^6$-sulfanone A112 [MS m/z: 205 (M+H)$^+$] was prepared using 3-bromo-5-ethylpyridine in place of 3-bromo-2,5-dimethyl-pyridine.

Preparation 107: 1-((5-Methylpiperidin-3-yl)imino)tetrahydro-1H-1$\lambda^6$-thiophene 1-oxide A113

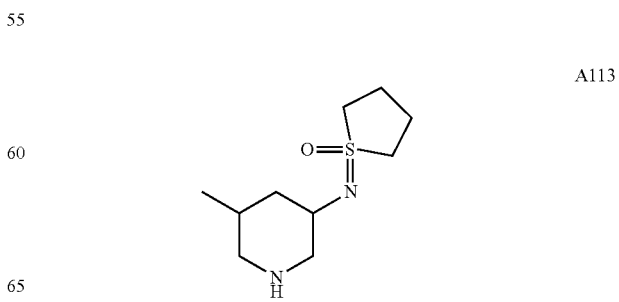

Using the same method as A108, 1-((5-methylpiperidin-3-yl)imino)tetrahydro-1H-1λ⁶-thiophene 1-oxide A113 [MS m/z: 217 (M+H)⁺] was prepared using 1-iminotetrahydro-1H-1λ⁶-thiophene 1-oxide in place of diethyl(imino)-λ⁶-sulfanone.

Preparation 108: Dimethyl((5-(trifluoromethyl)piperidin-3-yl)imino)-λ⁶-sulfanone A114

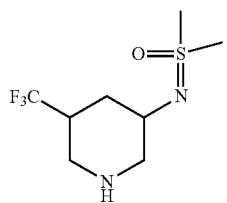

A114

Using the same method as A111, dimethyl((5-(trifluoromethyl)piperidin-3-yl)imino)-λ⁶-sulfanone A114 was prepared using 3-bromo-5-(trifluoromethyl)pyridine in place of 3-bromo-2,5-dimethyl-pyridine. The crude reaction mixture from the hydrogenation reaction was used directly in the next reaction.

Preparation 109: 2,5-Dimethyl-3-(1H-pyrazol-4-yl)piperazine A115

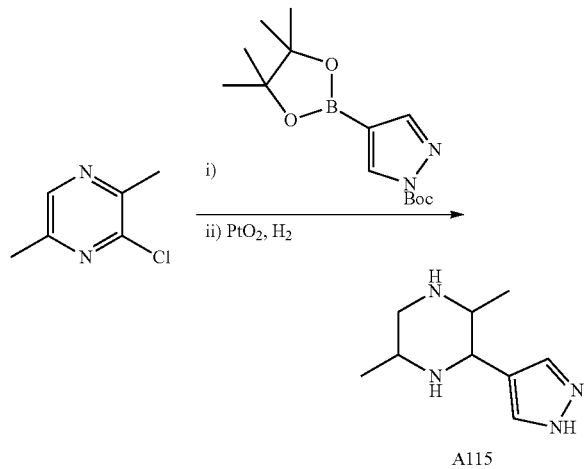

A115

A 3-necked flask equipped with reflux condenser and thermometer was charged with 3-chloro-2,5-dimethyl-pyrazine (5 mL, 40 mmol), tert-butyl 4-(4,4,5,5-tetramethyl-1,3,2-dioxaborolan-2-yl)pyrazole-1-carboxylate (10 g, 34 mmol) and 1,4-dioxane (100 mL). Pd(PPh₃)₄ (2 g, 2 mmol), and Na₂CO₃ (60 mL of 2 M, 100 mmol) were added and the solution was evacuated and backfilled with N₂ (×2). The solution was heated at 100° C. and stirred for 16 hours. The reaction mixture was cooled to ambient temperature and filtered, washing with diethyl ether. The filtrate was concentrated in vacuo and the residue purified by column chromatography (silica, 0-100% [EtOAc+2% 2 M methanolic ammonia]-PE gradient elution) to give 2,5-dimethyl-3-(1H-pyrazol-4-yl)pyrazine as a white solid (4.5 g, 64%); MS m/z: 175 (M+H)⁺.

A mixture of 2,5-dimethyl-3-(1H-pyrazol-4-yl)pyrazine (4.5 g, 26 mmol), PtO₂ (1 g, 4 mmol) and HCl (60 mL of a 3 M solution in MeOH, 200 mmol) was shaken in a Parr hydrogenator for 24 hours under a pressure of 60 psi H₂. The reaction mixture was filtered and the filtrate concentrated in vacuo to give the product 2,5-dimethyl-3-(1H-pyrazol-4-yl)piperazine A115 as an off-white solid (4.0 g, 61%) that was used in the next reaction assuming the dihydrochloride salt was isolated; MS m/z: 181 (M+H)⁺.

Preparation 110: Dimethyl((5-methylpiperidin-3-yl)imino)-λ⁶-sulfanone A116

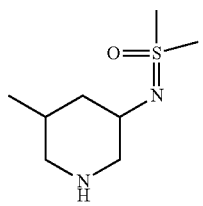

A116

Using the same method as for A104, dimethyl((5-methylpiperidin-3-yl)imino)-λ⁶-sulfanone A116 [MS m/z: 191 (M+H)⁺] was prepared using 3-bromo-5-methylpyridine in place of 3-bromo-2-methylpyridine.

Preparation 111: N-((4-Methoxypiperidin-2-yl)methyl)methanesulfonamide A117

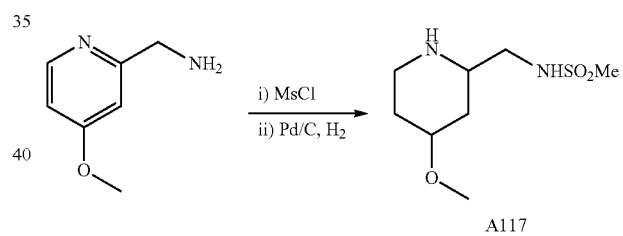

A117

Methanesulfonyl chloride (1.4 mL, 18.09 mmol) was added to a stirred solution of (4-methoxy-3-pyridyl)methanamine (2 g, 14.5 mmol) and Et₃N (3.0 mL, 21.5 mmol) in THF (50 mL) under an atmosphere of nitrogen and the reaction was stirred at ambient temperature for 16 hours. The reaction was diluted with DCM and saturated aqueous NaHCO₃ solution and the mixture was stirred for 10 minutes. The layers were separated and the aqueous layer extracted with DCM (×2). The combined organic extracts were dried (MgSO₄), filtered and concentrated in vacuo. The residue was triturated with DCM and the precipitate isolated by filtration to give N-[(4-methoxy-3-pyridyl)methyl]methanesulfonamide as a beige solid (1.82 g, 58%); ¹H NMR (500 MHz, DMSO-d₆) δ 8.41 (d, 1H), 8.36 (s, 1H), 7.38 (t, 1H), 7.05 (d, 1H), 4.14 (d, 2H), 3.88 (s, 3H), 2.90 (s, 3H).

A mixture of N-[(4-methoxy-3-pyridyl)methyl]methanesulfonamide (50 mg, 0.23 mmol), 10% Pd on C, wet, Degussa (100 mg of 10% w/w, 0.09 mmol) in acetic acid (2 mL)/methanol (5 mL) was stirred at ambient temperature for 18 hours under H₂. The reaction mixture was filtered through a Celite cartridge, washing with MeOH. The filtrate was concentrated under reduced pressure to give a colourless oil containing N-((4-methoxypiperidin-2-yl)methyl)

methanesulfonamide A117, which was taken directly on to the next reaction without further purification; MS m/z: 223 (M+H)+.

Preparation 112: (R)-Dimethyl((morpholin-2-ylmethyl)imino)-λ⁶-sulfanone A118

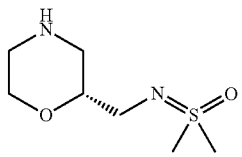

Using the method for preparation of A5, (R)-dimethyl ((morpholin-2-ylmethyl)imino)-λ⁶-sulfanone A118 [MS m/z: 193 (M+H)+] was prepared using tert-butyl (R)-2-formylmorpholine-4-carboxylate in place of tert-butyl (S)-2-formylmorpholine-4-carboxylate.

Preparation 113: N-((4-Fluoro-5-methyl-1,2,5,6-tetrahydropyridin-3-yl)methyl)methanesulfonamide A119

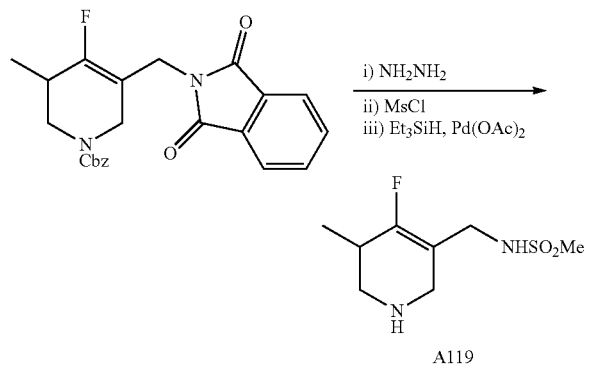

A mixture of benzyl 5-[(1,3-dioxoisoindolin-2-yl) methyl]-4-fluoro-3-methyl-3,6-dihydro-2H-pyridine-1-carboxylate (600 mg, 1.47 mmol) (formed as a side product in the fluorination reaction described in the preparation of A46), and hydrazine hydrate (290 μL, 2.9 mmol) in ethanol (15 mL) was heated under reflux for 2 hours. The reaction mixture was cooled to ambient temperature and filtered, washing with EtOH. The filtrate was concentrated under reduced pressure and the residue taken up in DCM (10 mL). Et₃N (300 μL, 2.2 mmol) and methanesulfonyl chloride (140 μL, 1.8 mmol) were added and the mixture stirred at ambient temperature for 2 hours. The solution was diluted with DCM and saturated aqueous NaHCO₃ solution. After stirring for 5 minutes, the organic phase was isolated using a phase separation cartridge. To this solution was added Et₃SiH (300 μL, 1.9 mmol) and Et₃N (300 μL, 2.2 mmol), then Pd(OAc)₂ (30 mg, 0.13 mmol). The solution was stirred at ambient temperature for 90 minutes then diluted with methanol. The solution was loaded on to an ion-exchange cartridge, washing with methanol then eluting the product with a 2 M methanolic ammonia solution. The filtrate was concentrated under reduced pressure to give a yellow gum containing N-((4-Fluoro-5-methyl-1,2,5,6-tetrahydropyridin-3-yl) methyl)methanesulfonamide A119 that was taken on to the next reaction without further purification; MS m/z: 223 (M+H)+.

Preparation 114: (4,4-Difluoro-5-methylpiperidin-3-yl)methanol A120

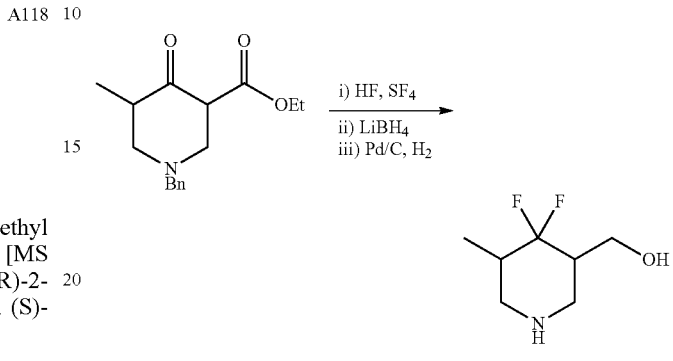

Ethyl 1-benzyl-5-methyl-4-oxopiperidine-3-carboxylate (10.0 g, 1 eq.) was placed in a 250 mL stainless steel autoclave. The vessel was cooled to −60° C. and anhydrous HF (7 eq.) was transferred under reduced pressure. The vessel was cooled to −90° C. using liquid N₂ and SF₄ (3 eq.) was added. An exotherm from −90° C. to −48° C. was observed. The vessel was cooled below −70° C., then allowed to warm to ambient temperature over 21 hours (4 bar pressure). The vessel was vented through a KOH scrubber. DCM (10 vols.) was added and the reaction quenched onto ice (5 weight vol.). The mixture was basified to pH 8 using KHCO₃ solution and the mixture stirred for 20 minutes. The layers were separated and the aqueous phase extracted with DCM (2×20 vol.). The combined organics were dried (Na₂SO₄), filtered and concentrated in vacuo. The residue contained a mixture of two diastereoisomers and was purified by column chromatography (silica, 0-1% EtOAc-PE to elute the one isomer, then 1-100% EtOAc-PE to elute the other). The product fractions were combined and concentrated in vacuo. The first eluting isomer was obtained as a solid (3.0 g) and the second eluting isomer as a yellow oil (5.8 g) (81% total yield); MS m/z: 298 (M+H)+. The major isomer was used in the next step.

To a solution of ethyl 1-benzyl-4,4-difluoro-5-methyl-piperidine-3-carboxylate (175 mg, 0.59 mmol) in THF (1.8 mL) was added LiBH₄ (618 μL of 2 M, 1.24 mmol) at ambient temperature. MeOH (50 μL, 1.2 mmol) was added to the clear yellow solution and the reaction mixture was heated to 50° C. After 45 minutes the reaction mixture was cooled to ambient temperature then cooled further in an ice bath. Saturated aqueous NH₄Cl solution was added and the mixture stirred until effervescence ceased. The mixture was diluted with water and EtOAc. The organic layer was separated, washed with brine (1x), dried (MgSO₄), filtered and concentrated in vacuo. The residue was taken up in MeOH (1.5 mL) and Pd/C (7 mg of 10% w/w, 0.06 mmol) was added. The mixture was degassed (×3 vacuum-N₂ cycles) and filled with an atmosphere of H₂ (×3 vacuum-H₂ cycles). The reaction mixture was stirred at ambient temperature. After 3 hours the reaction mixture was filtered through Celite. The filtrate was concentrated in vacuo and the residue containing (4,4-difluoro-5-methylpiperidin-3-yl)

methanol A120 (100 mg) that was used directly in the next reaction without further purification; MS m/z: 166 (M+H)$^+$.

Preparation 115: N-((4,4-Difluoro-2,5-dimethylpiperidin-3-yl)methyl)methanesulfonamide Diastereoisomers A121, A122 and A123

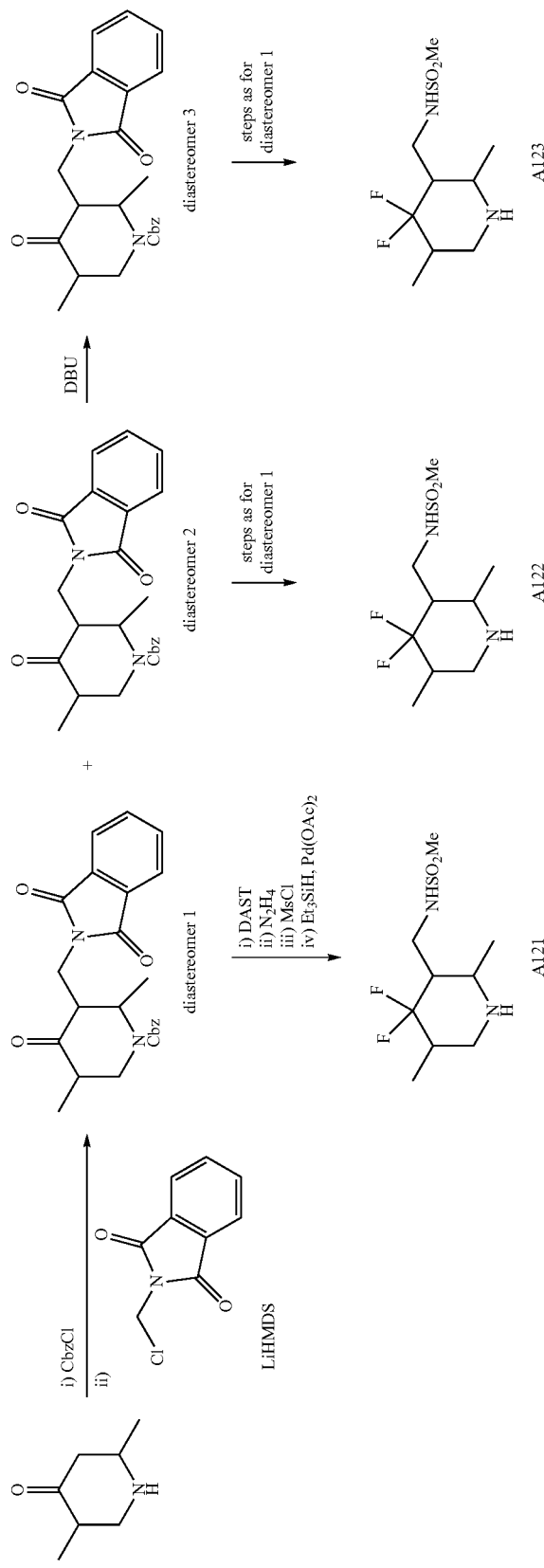

Cbz-Cl (10 mL, 70 mmol) was added to 2,5-dimethylpiperidin-4-one (10 g, 78.6 mmol) and $K_2CO_3$ (25 g, 180.9 mmol) in EtOAc (200 mL) and water (100 mL). The reaction was stirred vigorously at ambient temperature. After 18 hours the organic phase was isolated. The aqueous phase was extracted with ethyl acetate and the combined organics washed with water and brine then dried ($Na_2SO_4$), filtered and concentrated in vacuo. The residue was purified by column chromatography (silica, 0-100% EtOAc-PE gradient elution) to give the product as a colourless oil (6.5 g, 32%); MS m/z: 262 (M+H)$^+$.

LiHMDS (16 mL of 1 M, 16 mmol) was added dropwise to a solution of benzyl 2,5-dimethyl-4-oxo-piperidine-1-carboxylate (3.8 g, 14.5 mmol) in THF (70 mL) cooled to −78° C. under $N_2$. After 90 minutes, a solution of 2-(chloromethyl)isoindoline-1,3-dione (3.4 g, 17.4 mmol) in THF (2 mL) was added dropwise. After 1 hour the reaction mixture was allowed to warm to 0° C. then quenched by the addition of saturated aqueous $NH_4Cl$ solution (~10 mL). The reaction mixture was diluted with EtOAc, washed with saturated aqueous sodium bicarbonate solution and brine. The organic was dried ($Na_2SO_4$), filtered and concentrated in vacuo. The residue was purified by column chromatography (silica, 0-100% EtOAc-PE gradient elution). Two diastereomers were isolated as colourless oils: diastereomer 1 (700 mg) and diastereomer 2 (2.0 g).

Diastereomer 1 (600 mg, 1.43 mmol) and DAST (5 mL, 38 mmol) were stirred at ambient temperature for three days then poured dropwise onto a stirred mixture of DCM/ice/water/$NaHCO_3$. This mixture was stirred for 30 minutes. The organic phase was isolated using a phase separation cartridge. The filtrate was concentrated in vacuo and the residue purified by column chromatography (silica, 0-50% EtOAc-PE gradient elution) to give a colourless oil (450 mg) that was taken directly on to the next reaction; MS m/z: 443 (M+H)$^+$.

A mixture of benzyl 3-[(1,3-dioxoisoindolin-2-yl)methyl]-4,4-difluoro-2,5-dimethyl-piperidine-1-carboxylate (450 mg, 1.02 mmol) and hydrazine hydrate (150 µL, 3.06 mmol) in ethanol (4 mL) was heated under reflux for 2 hours then allowed to cool to ambient temperature. The reaction mixture was filtered, washing with MeOH, and the filtrate was poured onto a pre-wetted ion-exchange cartridge. The cartridge was washed with methanol then the product eluted with a 2 M methanolic ammonia solution. The filtrate was concentrated under reduced pressure to give a colourless oil. The residue was dissolved in DCM (3 mL). $Et_3N$ (200 µL, 1.44 mmol) and methanesulfonyl chloride (70 µL, 0.9 mmol) were added under $N_2$ and the solution stirred at ambient temperature. After 2 hours the reaction mixture was diluted with DCM and saturated aqueous $NaHCO_3$ solution. After stirring for 5 minutes the organic layer was isolated using a phase separation cartridge. The filtrate was concentrated under reduced pressure and the residue purified by column chromatography (silica, 0-100% EtOAc-PE gradient elution) to give a colourless oil (180 mg) that was used directly in the next reaction; MS m/z: 391 (M+H)$^+$.

A mixture of benzyl 4,4-difluoro-3-(methanesulfonamidomethyl)-2,5-dimethyl-piperidine-1-carboxylate (180 mg, 0.46 mmol), $Et_3SiH$ (150 µL, 0.939 mmol), $Et_3N$ (180 µL, 1.3 mmol) and Pd(OAc)$_2$ (50 mg, 0.2 mmol) in DCM (4 mL) was stirred at ambient temperature for 2 hours, then diluted with methanol (~5 mL). The mixture was poured onto a pre-wetted ion-exchange cartridge. The cartridge was washed with methanol then the product eluted with a 2 M methanolic ammonia solution. The filtrate was concentrated under reduced pressure to give a brown oil containing A121 (120 mg) that was taken directly on to the next reaction without further purification; MS m/z: 257 (M+H)$^+$.

A122 [MS m/z: 257 (M+H)$^+$] was prepared in a similar fashion starting from diastereomer 2, and was taken directly on to the next reaction.

Diastereomer 3 was prepared by stirring diastereomer 2 (600 mg, 1.43 mmol) in THF (7 mL) with DBU (150 µL, 1.00 mmol) in THF (7 mL) at ambient temperature for 20 hours. The reaction mixture was diluted with EtOAc, washed with 2 M aqueous HCl solution, saturated aqueous sodium bicarbonate solution and brine. The organic was dried ($Na_2SO_4$), filtered and concentrated in vacuo. Diastereomer 3 was obtained as a white foam (600 mg) that was treated as above to give A123 [MS m/z: 257 (M+H)$^+$], which was taken directly on to the next reaction.

Preparation 116: N-(((2S,3R,5S)-4,4-Difluoro-2,5-dimethylpiperidin-3-yl)methyl)methanesulfonamide A124

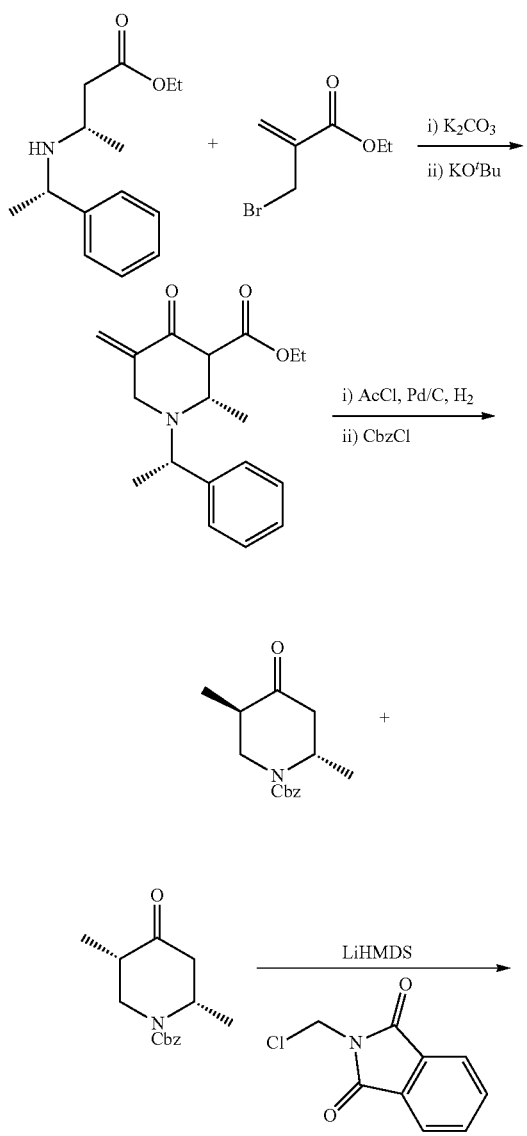

-continued

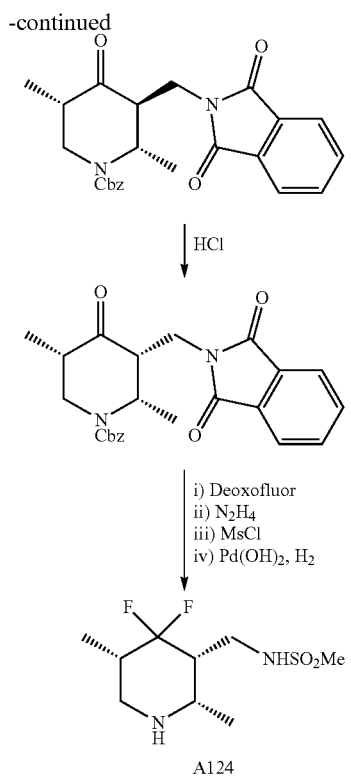

A124

Ethyl (S)-3-(((S)-1-phenylethyl)amino)butanoate (40 g, 170 mmol) was dissolved in MeCN (400 mL). Ethyl 2-(bromomethyl)acrylate was dissolved in MeCN (100 mL) and added to the amine solution. $K_2CO_3$ (47 g, 340 mmol) was added and the mixture stirred overnight at ambient temperature. The reaction mixture was filtered, washing with MeCN. The filtrate was evaporated in vacuo to afford an oily solid. The residue was taken up in DCM (~400 mL) and purified by column chromatography (silica, DCM elution). The product-containing fractions were combined and concentrated in vacuo to afford ethyl (3S)-3-[2-ethoxycarbonylallyl-[(1S)-1-phenylethyl]amino]butanoate as a colorless oil (38.8 g, 65%); MS m/z: 348 (M+H)$^+$.

Ethyl (3S)-3-[2-ethoxycarbonylallyl-[(1S)-1-phenylethyl]amino]butanoate (33.4 g, 96.0 mmol) was dissolved in anhydrous THF (500 mL) in a flame-dried 1000 mL three-necked round-bottomed flask equipped with a temperature thermocouple under $N_2$. The flask was cooled to 0° C. in an ice-bath. KO$^t$Bu (210 mL of a 1 M solution, 210 mmol) was added via syringe. After 30 minutes the reaction was poured into saturated aqueous $NH_4Cl$ and extracted with $Et_2O$. The extract was dried ($MgSO_4$), filtered and concentrated in vacuo. The residue was taken up in DCM and passed through a plug of silica gel, eluting with DCM. The filtrate was concentrated in vacuo to give the product as a light yellow oil (27.9 g, 96%); MS m/z: 302 (M+H)$^+$.

Acetyl chloride (200 mL, 2.8 mol) was dissolved in EtOH (2.6 L). The solution was stirred for 30 minutes and then added to ethyl (2S)-2-methyl-5-methylene-4-oxo-1-[(1S)-1-phenylethyl]piperidine-3-carboxylate (223 g, 740 mmol). Pd/C (50 g of 10% w/w, 47 mmol) was added. The atmosphere was evacuated in vacuo and replaced with hydrogen from a balloon. The reaction was stirred at ambient temperature for 9 days then filtered through a pad of Celite, washing with EtOH. The filtrate was concentrated in vacuo. The residue was dissolved in THF (1 L). To this solution was added NaOH (1 L of a 1 M aqueous solution). The mixture was cooled in an ice bath and CbzCl (110 mL, 771 mmol) was added dropwise. The mixture was stirred overnight at ambient temperature. MTBE was added and the layers separated. The organic layer was dried ($MgSO_4$), filtered, and concentrated in vacuo. This material was combined with the product of a separate reaction using ethyl (2S)-2-methyl-5-methylene-4-oxo-1-[(1S)-1-phenylethyl]piperidine-3-carboxylate (303 g, 1.0 mol). The combined material was purified by column chromatography (silica, 10-40% DCM-heptane gradient elution). Two isomers were isolated (32% combined yield): the major anti isomer benzyl (2S,5R)-2,5-dimethyl-4-oxo-piperidine-1-carboxylate (105 g); $^1$H NMR (400 MHz, DMSO-d$_6$) δ 7.43-7.27 (m, 5H), 5.11 (q, 2H), 4.36 (pd, 1H), 3.71 (dd, 1H), 3.62 (dd, 1H), 2.84 (dd, 1H), 2.51 (m, 1H), 2.28 (dd, 1H), 1.16 (d, 3H), 1.00 (d, 3H); and the minor syn isomer benzyl (2S,5S)-2,5-dimethyl-4-oxo-piperidine-1-carboxylate (43 g); $^1$H NMR (400 MHz, DMSO-d$_6$) δ 7.46-7.27 (m, 5H), 5.21-5.05 (m, 2H), 4.72 (q, 1H), 4.22 (d, 1H), 2.89 (d, 1H), 2.80-2.70 (m, 1H), 2.67-2.53 (m, 1H), 2.13 (dd, 1H), 1.06 (d, 3H), 0.90 (d, 3H).

A solution of benzyl (2S,5S)-2,5-dimethyl-4-oxo-piperidine-1-carboxylate (46.3 g, 177.2 mmol) in THF (280 mL) was cooled to −78° C. before LiHMDS (1 M in THF) (212 mL of 1 M, 212 mmol) was added at such a rate as to keep the temperature below −65° C. On complete addition, the mixture was stirred at −78° C. for a further 10 minutes before a solution of 2-(chloromethyl)isoindoline-1,3-dione (41.6 g, 213 mmol) in THF (230 mL) was added at such a rate as to keep the temperature below −65° C. On complete addition, the dry ice/acetone cooling bath was removed and the reaction flask was placed in an ice/water bath. The reaction mixture was allowed to warm to 0° C. over 30 minutes. The mixture was re-cooled to −78° C. before being quenched carefully with saturated aqueous $NH_4Cl$ solution (93 mL) at such a rate as to keep the internal temp below −65° C. On complete addition the cooling bath was removed and the mixture allowed to warm to ambient temperature. EtOAc (500 mL) was added and the organic phase separated. The organic phase was washed with water (×2), brine, dried ($MgSO_4$), filtered and concentrated in vacuo. IPA (500 mL) was added to the residue and the resulting solution left to stand over the weekend. The resulting crystallised solid was collected by filtration, washed with minimal IPA and dried under vacuum to give benzyl (2S,3S,5S)-3-[(1,3-dioxoisoindolin-2-yl)methyl]-2,5-dimethyl-4-oxo-piperidine-1-carboxylate (31 g, 42%) as a colourless solid; $^1$H NMR (400 MHz, DMSO-d$_6$) δ 7.95-7.78 (m, 5H), 7.49-7.24 (m, 6H), 5.25-5.07 (m, 2H), 4.73-4.53 (m, 1H), 4.33 (t, 1H), 3.95-3.75 (m, 2H), 3.01 (s, 2H), 2.70-2.57 (m, 1H), 1.11 (d, 3H), 0.88 (d, 3H); MS m/z: 421 (M+H)$^+$.

Benzyl (2S,3S,5S)-3-[(1,3-dioxoisoindolin-2-yl)methyl]-2,5-dimethyl-4-oxo-piperidine-1-carboxylate (77.1 g, 183.4 mmol) was suspended in hydrogen chloride (325 mL of a 4 M solution in 1,4-dioxane, 1.30 mol). The reaction mixture was stirred at ambient temperature. After 5.5 hours the resulting yellow solution was diluted with EtOAc (500 mL) and water (200 mL). The organic phase was washed with brine (200 mL), dried ($MgSO_4$), filtered and concentrated in vacuo to give a yellow oil (102.5 g). IPA (500 mL) was added and the mixture was stirred for 72 hours. The resulting white precipitate was collected by filtration, washing with IPA. The filtrate was concentrated in vacuo and the residue azeotroped with DCM (×3). The residue was purified by column chromatography (silica, 0-60% EtOAc-heptane gradient elution) to give benzyl (2S,3R,5S)-3-[(1,3-dioxoisoindolin-2-yl)methyl]-2,5-dimethyl-4-oxo-piperidine-1-carboxylate as a pale yellow, sticky gum (37.6 g, 49%); $^1$H NMR (400 MHz, DMSO-d$_6$) δ 7.92-7.83 (m, 4H), 7.48-7.08 (m, 5H), 5.22-4.94 (m, 2H), 4.64 (m, 1H), 4.32 (m, 1H), 3.87 (dd, 1H), 3.61-3.48 (m, 1H), 3.39-3.32 (m, 1H), 2.90 (m, 1H), 2.77 (br s, 1H), 1.07 (m, 3H), 0.90 (m, 3H); MS m/z: 421 (M+H)$^+$.

The white solid, benzyl (2S,3S,5S)-3-[(1,3-dioxoisoindolin-2-yl)methyl]-2,5-dimethyl-4-oxo-piperidine-1-carboxylate (33.4 g, 43%) was suspended in hydrogen chloride (160 mL of a 4 M solution in 1,4-dioxane, 640 mmol) and the reaction mixture stirred at ambient temperature. After 5.5 hours the reaction mixture was diluted with MTBE (220 mL) and water (85 mL). The organic phase was washed with brine (85 mL), dried (MgSO$_4$), filtered and concentrated in vacuo. The residue was stirred in IPA (220 mL) overnight. The resulting mixture was treated as before to give further benzyl (2S,3R,5S)-3-[(1,3-dioxoisoindolin-2-yl)methyl]-2,5-dimethyl-4-oxo-piperidine-1-carboxylate (14.7 g, 44%).

To a solution of benzyl (2S,3R,5S)-3-[(1,3-dioxoisoindolin-2-yl)methyl]-2,5-dimethyl-4-oxo-piperidine-1-carboxylate (51.2 g, 122 mmol) and Deoxofluor® (485 mL of a 50% w/v solution in toluene, 1.1 mol) was added BF$_3$.OEt$_2$ (7.4 mL, 60.0 mmol). The mixture was heated to 60° C. (internal) for 24 hours. The mixture was then cooled to ambient temperature and carefully quenched by slow addition into a stirred solution of saturated aqueous NaHCO$_3$ solution (30 mL). On complete addition, the mixture was stirred for 30 minutes. The mixture was then extracted with EtOAc (2×20 mL). The combined organics were and washed with water (2×20 mL), brine (20 mL), dried (MgSO$_4$), filtered and concentrated in vacuo. The residue was purified by column chromatography (silica, 0-20% EtOAc-PE gradient elution). The product-containing fractions were combined and concentrated in vacuo and the residue further purified by SFC (15% MeOH @ 5 mL/min on an CHIRALPAK IC, 4.6×100 mm, 100 bar, 35 C, 220 nm) to give benzyl (2S,3R,5S)-3-[(1,3-dioxoisoindolin-2-yl)methyl]-4,4-difluoro-2,5-dimethyl-piperidine-1-carboxylate as an orange gum (12.8 g, 24%); $^1$H NMR (400 MHz, DMSO-d$_6$) δ 7.97-7.78 (m, 4H), 7.44-7.14 (m, 5H), 5.21-4.95 (m, 2H), 4.46 (s, 1H), 4.03-3.85 (m, 2H), 3.74-3.53 (m, 1H), 2.96-2.59 (m, 2H), 2.25-1.96 (m, 1H), 1.18 (s, 3H), 1.03-0.85 (m, 3H); MS m/z: 443 (M+H)$^+$. The absolute configurations were confirmed at this stage using 2D NMR studies.

To a solution of benzyl (2S,3R,5S)-3-[(1,3-dioxoisoindolin-2-yl)methyl]-4,4-difluoro-2,5-dimethyl-piperidine-1-carboxylate (12.8 g, 28.8 mmol) in ethanol (190 mL) was added hydrazine hydrate (3.3 mL, 43 mmol) and the resulting solution heated under reflux for 2 hours. Further hydrazine hydrate (1.2 mL, 16 mmol) was added and the mixture heated under reflux for 16 hours. The mixture was diluted with ethanol (100 mL), cooled to ambient temperature and stirred rapidly for 1 hour. The resulting suspension was filtered, washing with minimal ethanol, and the filtrate concentrated in vacuo. The residue was partitioned between EtOAc and minimal water, mixed and the organic phase separated. The organics were washed with water (2×), brine, dried (Na$_2$SO$_4$), filtered and concentrated in vacuo to give benzyl (2S,3R,5S)-3-(aminomethyl)-4,4-difluoro-2,5-dimethyl-piperidine-1-carboxylate (8.3 g, 92%); $^1$H NMR (400 MHz, DMSO-d$_6$) δ 7.45-7.27 (m, 5H), 5.21-5.00 (m, 2H), 4.77-4.57 (m, 1H), 4.02-3.86 (m, 1H), 3.01 (dd, 1H), 2.77 (dt, 1H), 2.20-1.90 (m, 2H), 1.44 (s, 2H), 1.09-0.98 (m, 3H), 0.98-0.85 (m, 4H); MS m/z: 313 (M+H)$^+$.

A solution of benzyl (2S,3R,5S)-3-(aminomethyl)-4,4-difluoro-2,5-dimethyl-piperidine-1-carboxylate (8.27 g, 26.5 mmol) in DCM (100 mL) was cooled to 0° C. then Et$_3$N (4.1 mL, 29 mmol) was added followed by the slow addition of methanesulfonyl chloride (2.2 mL, 28 mmol) over 2 minutes. The mixture was stirred in an ice bath for 1 hour. The reaction mixture was washed with water (3×) and brine, dried (MgSO$_4$), filtered and concentrated in vacuo to give benzyl (2S,3R,5S)-4,4-difluoro-3-(methanesulfonamidomethyl)-2,5-dimethyl-piperidine-1-carboxylate (10.4 g, quantitative yield) as a yellow foam that was taken directly on to the next reaction without further purification; $^1$H NMR (400 MHz, DMSO-d$_6$) δ 7.47-7.27 (m, 5H), 7.23 (dd, 1H), 5.24-5.00 (m, 2H), 4.63 (s, 1H), 4.51 (s, 1H), 4.06-3.86 (m, 1H), 3.39 (dt, 1H), 3.07-2.92 (m, 4H), 2.92-2.63 (m, 1H), 2.35 (s, 1H), 2.10 (d, 1H), 1.08 (t, 3H), 0.94 (t, 3H); MS m/z: 391 (M+H)$^+$.

A mixture of benzyl (2S,3R,5S)-4,4-difluoro-3-(methanesulfonamidomethyl)-2,5-dimethyl-piperidine-1-carboxylate (10.6 g, 27.2 mmol) and Pd(OH)$_2$ (1.9 g of 20% w/w, 2.7 mmol) in IPA (100 mL) was heated at 45° C. and stirred for 3 days under a balloon of hydrogen. The mixture was flushed with nitrogen and then filtered through Celite, washing with IPA then EtOAc followed by methanol. The filtrate was concentrated in vacuo. To the residue was added Pd(OH)$_2$ (1.9 g of 20% w/w, 2.7 mmol) followed by IPA (160 mL) and the mixture was stirred under a hydrogen atmosphere for 16 hours. The mixture was filtered through Celite, washing with IPA and EtOAc and concentrated in vacuo. To the residue was added Pd(OH)$_2$ (1.9 g of 20% w/w, 2.7 mmol) followed by IPA (160 mL) and stirred under a hydrogen atmosphere for 16 hours. The mixture was filtered through Celite, washing with IPA. The filtrate was concentrated in vacuo, dissolved in methanol (280 mL) and SMP-32 (40.72 g of 0.8 mmol/g) was added. The mixture was heated at 50° C. and stirred for 3 hours before cooling to ambient temperature, then filtered through Celite, washing with methanol. The filtrate was concentrated in vacuo and dried overnight under vacuum, to give N-(((2S,3R,5S)-4,4-difluoro-2,5-dimethylpiperidin-3-yl)methyl)methanesulfonamide A124 (6.06 g, 87%); $^1$H NMR (400 MHz, Chloroform-d) δ 3.66 (dh, 1H), 3.50 (dd, 1H), 3.16 (dd, 1H), 3.04-2.89 (m, 4H), 2.85-2.70 (m, 1H), 2.54-2.34 (m, 1H), 2.20-1.97 (m, 1H), 1.20 (dd, 3H), 1.06-0.93 (m, 3H); MS m/z: 257 (M+H)$^+$.

Preparation 117: Dimethyl((6-methylpiperidin-3-yl)imino)-λ$^6$-sulfanone A125

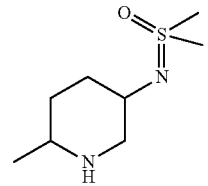

A125

Using the same method used for the preparation of A104, dimethyl((6-methylpiperidin-3-yl)imino)-λ$^6$-sulfanone A125 [MS m/z: 191 (M+H)$^+$] was prepared using 5-bromo-2-methyl-pyridine in place of 3-bromo-2-methylpyridine. The crude reaction mixture from the hydrogenation reaction was used directly in the next reaction.

Preparation 118: ((2-(Difluoromethyl)piperidin-3-yl)imino)dimethyl-λ⁶-sulfanone A126

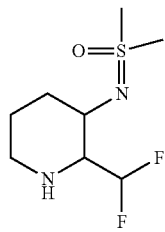

A126

Using the same method used for the preparation of A111, ((2-(difluoromethyl)piperidin-3-yl)imino)dimethyl-λ⁶-sulfanone A126 [MS m/z: 227 (M+H)⁺] was prepared using 3-bromo-2-(difluoromethyl)pyridine in place of 3-bromo-2,5-dimethyl-pyridine. The crude reaction mixture from the hydrogenation reaction was used directly in the next reaction.

Preparation 119: 2-Methyl-3-(1H-pyrazol-4-yl)piperazine A127

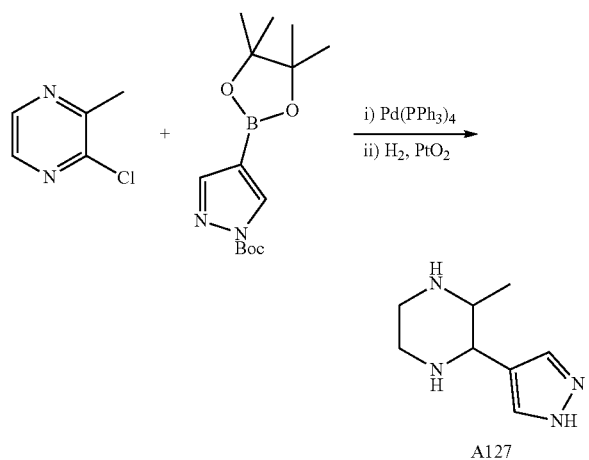

A127

To a suspension of 2-chloro-3-methyl-pyrazine (500 mg, 3.89 mmol) in 1,4-dioxane (10 mL) was added tert-butyl 4-(4,4,5,5-tetramethyl-1,3,2-dioxaborolan-2-yl)pyrazole-1-carboxylate (1.26 g, 4.28 mmol), Pd(Ph₃)₄ (225 mg, 0.19 mmol) and Na₂CO₃ (5.8 mL of a 2 M aqueous solution, 11.7 mmol). The reaction mixture was stirred in a sealed tube at 130° C. for 3 hours, then cooled and filtered through a pad of Celite. The filtrate was concentrated in vacuo to give 2-methyl-3-(1H-pyrazol-4-yl)pyrazine (750 mg, 94%) as a white solid; MS m/z: 161 (M+H)⁺.

A mixture of 2-methyl-3-(1H-pyrazol-4-yl)pyrazine (585 mg, 3.65 mmol), PtO₂ (84 mg, 0.37 mmol) and concentrated HCl (2 mL, 55 mmol) in methanol (60 mL) was shaken at ambient temperature in a Parr hydrogenator under a pressure of 60 psi H₂ for 6 hours. The reaction mixture was filtered and the filtrate concentrated in vacuo. The residue was dissolved in MeOH and loaded onto an ion-exchange cartridge. The cartridge was washed with MeOH then the product eluted with methanolic ammonia. The filtrate was concentrated under reduced pressure to give 2-methyl-3-(1H-pyrazol-4-yl)piperazine A127 (600 mg, 99%) as a brown solid; MS m/z: 167 (M+H)⁺. This material was taken on to the next reaction without further purification.

Preparation 120: Dimethyl(5-methylpiperidin-3-yl)phosphine Oxide A128

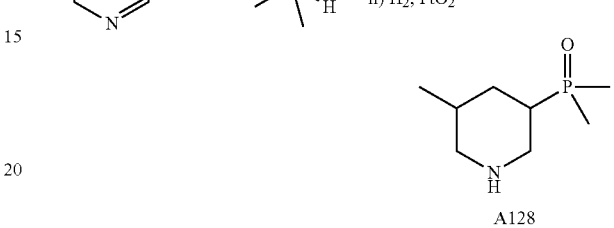

A128

Methylphosphonoylmethane (45 mg, 0.58 mmol), 3-bromo-5-methyl-pyridine (100 mg, 0.58 mmol), NEt₃ (324 µL, 2.32 mmol) and Pd(PPh₃)₄ (288 mg, 0.25 mmol) were combined in MeCN (580 µL) and the solution degassed before heating under reflux. The reaction was stirred under reflux for 18 hours then further methylphosphonoylmethane (45 mg, 0.58 mmol) was added. After 1 hour further methylphosphonoylmethane (45 mg, 0.58 mmol) was added. After 1 hour the reaction was cooled to ambient temperature, diluted in MeCN and purified by purified by reverse phase chromatography (C18, MeCN/water/0.05% TFA as eluent) to give 3-dimethylphosphoryl-5-methyl-pyridine (98 mg, 100%); ¹H NMR (500 MHz, MeOH-d₄) δ 8.84-8.70 (m, 1H), 8.62 (t, 1H), 8.08 (dt, 1H), 2.46 (s, 3H), 1.88 (s, 3H), 1.85 (s, 3H), MS m/z: 170 (M+H)⁺.

3-Dimethylphosphoryl-5-methyl-pyridine (100 mg, 0.59 mmol) and PtO₂ (27 mg, 0.12 mmol) were combined in methanol (3.3 mL) and HCl (985 µL of 3M, 2.96 mmol). The mixture was degassed and stirred under a balloon of H₂ for 2 hours before being passed through Celite. The filtrate was concentrated in vacuo to give 3-dimethyl(5-methylpiperidin-3-yl)phosphine oxide A128 as a 1:1 mixture of diastereomers (189 mg, 100%); MS m/z: 176 (M+H)⁺. This material was taken on to the next reaction without further purification.

Preparation 121: (5,5-Difluoro-2-methylpiperidin-3-yl)methanol A129

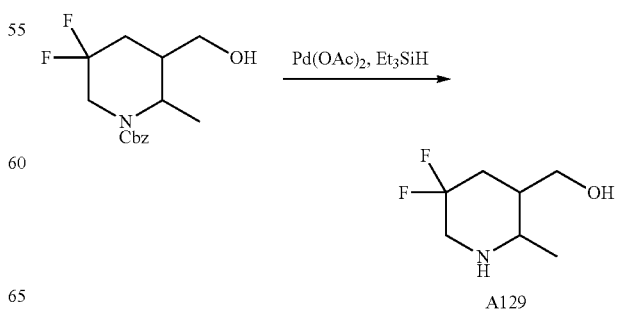

A129

A mixture of benzyl 5,5-difluoro-3-(hydroxymethyl)-2-methyl-piperidine-1-carboxylate, (see A64), (110 mg, 0.37 mmol), Pd(OAc)$_2$ (35 mg, 0.16 mmol), Et$_3$SiH (140 μL, 0.88 mmol) and Et$_3$N (100 μL, 0.717 mmol) in DCM (4 mL) was stirred at ambient temperature for 1 hour. The reaction mixture was diluted with methanol and the solution poured onto an ion-exchange cartridge. The cartridge was washed with methanol then the product eluted with a 2 M methanolic ammonia solution. The filtrate was concentrated in vacuo to give (5,5-difluoro-2-methylpiperidin-3-yl)methanol A129 (55 mg, 91%) as a brown oil; MS m/z: 166 (M+H)$^+$. This material was taken on to the next reaction without further purification.

Preparation 122:
2-(3-Methylpiperazin-2-yl)ethan-1-ol A130

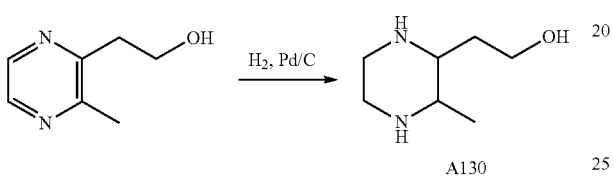

2-(3-Methylpyrazin-2-yl)ethanol (930 mg, 6.73 mmol) was dissolved in MeOH (20 mL). HCl (340 μL of 2 M, 0.68 mmol) was added and the mixture degassed (×3 vacuum-N$_2$ cycles). Pd on C, wet, Degussa (430 mg of 10% w/w, 0.40 mmol) was added and the mixture degassed (×3 cycles) then the N$_2$ atmosphere was replaced with H$_2$ (×5 cycles) and the reaction mixture stirred for 16 hours. Further Pd on C, wet, Degussa (430 mg of 10% w/w, 0.404 mmol) was added (degassing as above). After 5 hours, Pd on C, wet, Degussa (430 mg of 10% w/w, 0.404 mmol) and HCl (340 μL of 2 M, 0.680 mmol) were added, the mixture degassed as before and stirred for a further 16 hours. The reaction mixture was degassed with N$_2$ then filtered and concentrated in vacuo to give a colourless oil. The residue was taken up in MeOH (~5 mL) and passed through SPE biarbonate cartridges. The filtrate was concentrated in vacuo to give 2-(3-methylpiperazin-2-yl)ethan-1-ol A130 as a pale yellow oil (781 mg, 80%) that was taken directly on to the next reaction without further purification; MS m/z: 145 (M+H)$^+$.

Preparation 123: N-((5-Methylpiperazin-2-yl)methyl)methanesulfonamide A131

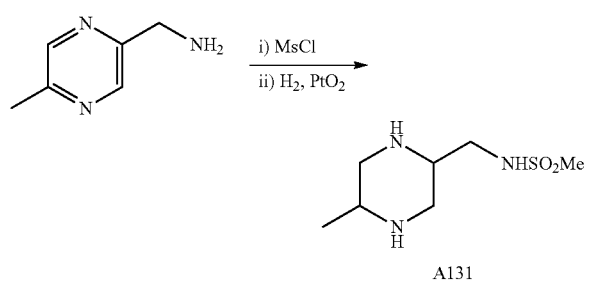

Methanesulfonyl chloride (240 μL, 3.10 mmol) was added to an ice cold solution of (5-methylpyrazin-2-yl)methanamine (300 mg, 2.44 mmol) and Et$_3$N (500 μL, 3.59 mmol) in DCM (4 mL) under N$_2$. After the addition, the ice bath was removed and the reaction mixture stirred at ambient temperature for 2 hours. The solution was diluted with DCM and saturated aqueous NaHCO$_3$ solution. The organic phase was isolated using a phase separation cartridge and the filtrate concentrated under reduced pressure to give a brown oil. This material was combined with PtO$_2$ (200 mg, 0.88 mmol) in 3 M methanolic HCl (15 mL, 45 mmol) and stirred vigorously at ambient temperature under a balloon of H$_2$ for 18 hours. The reaction mixture was poured directly onto an ion-exchange cartridge. The cartridge was washed with methanol then the product eluted with a 2 M methanolic ammonia solution. The filtrate was concentrated under reduced pressure to give N-((5-methylpiperazin-2-yl)methyl)methanesulfonamide A131 (271 mg, 56%) as a brown gum, which was taken on to the next reaction without further purification; MS m/z: 208 (M+H)$^+$.

Preparation 124: trans-(4-Benzyl-6-cyclopropylmorpholin-2-yl)methanol A132 and cis-(4-benzyl-6-cyclopropylmorpholin-2-yl)methanol A133

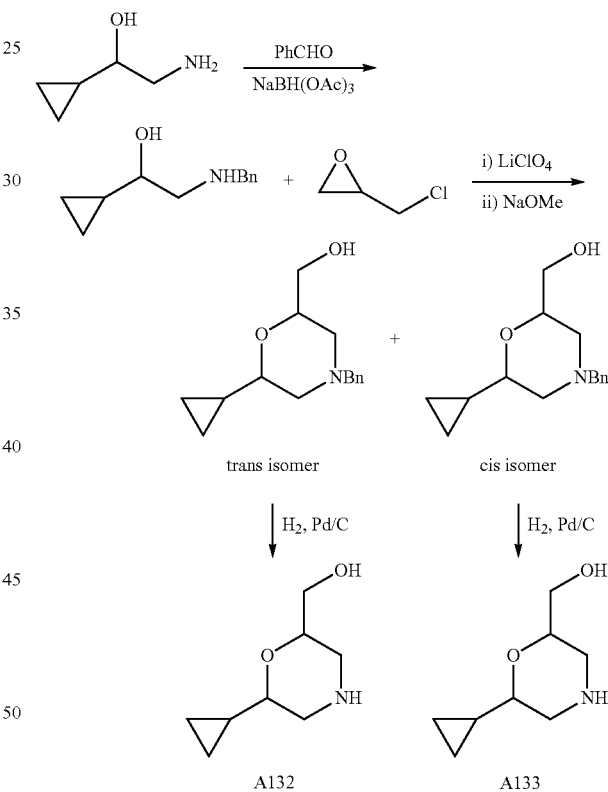

A mixture of 2-amino-1-cyclopropyl-ethanol (1.0 g, 9.9 mmol), benzaldehyde (1.2 mL, 11.8 mmol) and crushed 4 Å MS (1 g) in DCE (30 mL) were stirred at ambient temperature for 1 hour. NaBH(OAc)$_3$ (4.2 g, 19.9 mmol) was added and the reaction stirred at ambient temperature for a further 15 hours. The mixture was filtered through Celite (washing with DCM) and the filtrate concentrated in vacuo. The residue was passed through an ion-exchange cartridge, washing with MeOH/DCM and eluting the product with 2 M NH$_3$ in MeOH/DCM mixtures. The solvent was removed in vacuo and the residue purified by column chromatography (silica, 0-10% [10% NH$_4$OH in MeOH]-DCM gradient elution) to give 2-(benzylamino)-1-cyclopropyl-ethanol (1.04 g, 55%) as a colourless oil. ¹H NMR (500 MHz, DMSO-d₆) δ 7.19-7.14 (m, 4H), 7.09-7.06 (m, 1H), 4.33 (d, 1H), 3.56 (d, 2H), 2.87-2.82 (m, 1H), 2.43 (dd, 1H), 2.39-2.35 (m, 1H), 1.84 (br s, 1H), 0.68-0.61 (m, 1H), 0.22-0.15 (m, 2H), 0.13-0.07 (m, 1H), 0.02-0.03 (m, 1H); MS m/z: 192 (M+H)⁺.

A solution of 2-(benzylamino)-1-cyclopropyl-ethanol (1.03 g, 5.39 mmol) in toluene (15 mL) was treated with 2-(chloromethyl)oxirane (550 μL, 7.03 mmol) and lithium perchlorate (750 mg, 7.05 mmol) and the mixture stirred at ambient temperature for 22 hours. The mixture was diluted with EtOAc and washed with water (×2). The combined aqueous layers were extracted with EtOAc (×2) and the combined organic extracts washed with brine, dried (MgSO₄), filtered and concentrated in vacuo. The residue was dissolved in MeOH (5 mL) and NaOMe (730 mg, 13.5 mmol) added. The reaction was heated under reflux for 23 hours then cooled to ambient temperature and quenched by the addition of saturated aqueous NH₄Cl. The aqueous layer was diluted with water to dissolve salts, extracted with EtOAc (×3) and the combined organic extracts were dried (MgSO₄), filtered and concentrated in vacuo. The residue was purified by column chromatography (silica, 0-100% EtOAc-PE gradient elution) to give trans-(4-benzyl-6-cyclopropyl-morpholin-2-yl)methanol (229 mg, 17%) as a colourless oil and cis-(4-benzyl-6-cyclopropyl-morpholin-2-yl)methanol (293 mg, 22%) as a colourless oil.

A mixture of trans-(4-benzyl-6-cyclopropyl-morpholin-2-yl)methanol (228 mg, 0.92 mmol), Pd on C, wet, Degussa (50 mg, 0.47 mmol) and HCl (10 mL of 3 M in methanol, 30 mmol) was placed under an atmosphere of hydrogen and stirred at ambient temperature for 62 hours. The catalyst was removed by filtration through Celite, washing with MeOH, and the filtrate concentrated in vacuo. The residue was loaded on to an ion-exchange cartridge. The cartridge was washed with MeOH/DCM mixtures then the product eluted with 2 M NH₃ in MeOH/DCM mixtures. The filtrates were combined and concentrated in vacuo to give trans-(6-cyclopropylmorpholin-2-yl)methanol A132 (107 mg, 74%) as a colourless oil; ¹H NMR (500 MHz, DMSO-d₆) δ 4.52 (br s, 1H), 3.64 (qd, 1H), 3.44 (d, 2H), 2.81-2.75 (m, 3H), 2.57 (ddd, 1H), 1.21-1.14 (m, 1H), 0.46-0.38 (m, 2H), 0.26-0.11 (m, 2H), MS m/z: 158 (M+H)⁺.

A mixture of cis-(4-benzyl-6-cyclopropyl-morpholin-2-yl)methanol (293 mg, 1.19 mmol), Pd on C, wet, Degussa (50 mg, 0.47 mmol) and HCl (3M in methanol) (10 mL, 30 mmol) was placed under an atmosphere of hydrogen and stirred at ambient temperature for 62 hours. The catalyst was removed by filtration through Celite, washing with MeOH, and the filtrate concentrated in vacuo. The residue was loaded on to an ion-exchange cartridge. The cartridge was washed with MeOH/DCM mixtures, then the product eluted with 2 M NH₃ in MeOH/DCM mixtures. The filtrates were combined and concentrated in vacuo to give cis-(6-cyclopropylmorpholin-2-yl)methanol A133 (93 mg, 50%) as a colourless oil; ¹H NMR (500 MHz, DMSO-d₆) δ 4.55 (t, 1H), 3.38-3.23 (m, 3H), 2.82-2.78 (m, 2H), 2.68 (ddd, 1H), 2.38 (dd, 1H), 2.26 (dd, 1H), 0.76-0.69 (m, 1H), 0.43-0.35 (m, 2H), 0.27-0.15 (m, 2H); MS m/z: 158 (M+H)⁺.

Preparation 125: 2-[(E)-2-Ethoxyvinyl]-4-methyl sulfanyl-pyrimidine

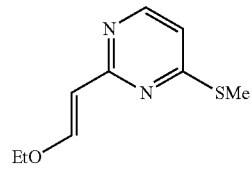 [SMILES: CCO/C=C/c1nccc(SC)n1]

A solution of 2-chloro-4-methylsulfanyl-pyrimidine (1 g, 6.23 mmol), Na₂CO₃ (9.3 mL of 2 M aq., 18.60 mmol) and 2-[(E)-2-ethoxyvinyl]-4,4,5,5-tetramethyl-1,3,2-dioxaborolane (1.35 g, 6.82 mmol) in 1,2-dimethoxyethane (15 mL) was degassed with nitrogen. Pd(PPh₃)₄ (600 mg, 0.519 mmol) was added and the mixture again degassed with nitrogen. The mixture was heated under reflux for 2 hours. The reaction mixture was cooled to ambient temperature, partitioned between EtOAc and water and the layers separated. The aqueous layer was extracted with EtOAc and the combined organic extracts washed with brine, dried (MgSO₄), filtered and concentrated in vacuo. The residue was purified by column chromatography (silica, EtOAc/petrol gradient) to afford 2-[(E)-2-ethoxyvinyl]-4-methylsulfanyl-pyrimidine (1.10 g, 90%); ¹H NMR (500 MHz, Chloroform-d) δ 8.19 (d, 1H), 7.94 (d, 1H), 6.85 (d, 1H), 5.90 (d, 1H), 4.02 (q, 2H), 2.56 (s, 3H), 1.40 (t, 3H); MS m/z 197.1 (M+H).

Preparation 126: 2-Chloro-4-(2-ethoxyvinyl)pyrimidine

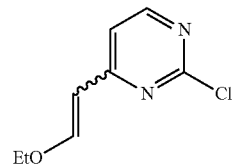 [SMILES: CCOC=Cc1ccnc(Cl)n1]

To a solution of 2,4-dichloropyrimidine (750 mg, 5.03 mmol) and Na₂CO₃ (7.4 mL of 2 M, 14.80 mmol) in 1,2-dimethoxyethane (15 mL) was added 2-(2-ethoxyvinyl)-4,4,5,5-tetramethyl-1,3,2-dioxaborolane (1.05 g, 5.30 mmol). The mixture was then degassed with nitrogen and Pd(PPh₃)₄ (295 mg, 0.255 mmol) was added and the mixture again degassed with nitrogen. The mixture was heated under reflux for 16 hours. The reaction mixture was cooled to ambient temperature, partitioned between EtOAc/water and the layers separated. The aqueous layer was extracted with EtOAc and the combined organic extracts washed with brine, dried (MgSO₄), filtered and concentrated in vacuo. The residue was purified by column chromatography (silica, EtOAc/petrol gradient) to afford (2-chloro-4-(2-ethoxyvinyl)pyrimidine (472.4 mg, 51%); MS m/z: 185.1 (M+H).

Preparation 127: 1-[4-[4-(4,4,5,5-Tetramethyl-1,3,2-dioxaborolan-2-yl)-2-pyridyl]piperazin-1-yl]ethanone

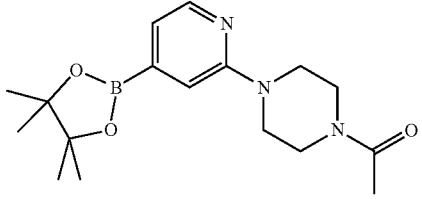 [SMILES: CC(=O)N1CCN(c2cc(B3OC(C)(C)C(C)(C)O3)ccn2)CC1]

Acetyl chloride (280 μL, 3.94 mmol) was added to a solution of 1-[4-(4,4,5,5-tetramethyl-1,3,2-dioxaborolan-2-yl)-2-pyridyl]piperazine (750 mg, 2.59 mmol) and Et$_3$N (900 μL, 6.46 mmol) in DCM (7.5 mL) and the reaction mixture allowed to stir at ambient temperature for 1 hour. The residue was purified directly passing through a Florisil cartridge (petroleum ether/EtOAc gradient elution) to give 1-[4-[4-(4,4,5,5-tetramethyl-1,3,2-dioxaborolan-2-yl)-2-pyridyl]piperazin-1-yl]ethanone as an off-white solid (693 mg, 81%); $^1$H NMR (500 MHz, DMSO-d$_6$) δ 8.16 (dd, 1H), 6.98 (s, 1H), 6.85 (dd, 1H), 3.55-3.52 (m, 6H), 3.48-3.46 (m, 2H), 2.04 (s, 3H), 1.31 (s, 12H); MS m/z: 332.2 (M+1)$^+$.

Preparation 128: 4-[(E)-2-ethoxyvinyl]-6-methylsulfanyl-pyrimidine

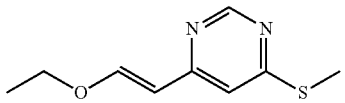

To a suspension of 4-chloro-6-methylsulfanyl-pyrimidine (30 g, 186.8 mmol) and Na$_2$CO$_3$ (280.2 mL of 2 M, 560.4 mmol) in 1,2-dimethoxyethane (400 mL) was added 2-[(E)-2-ethoxyvinyl]-4,4,5,5-tetramethyl-1,3,2-dioxaborolane (37.7 g, 190.3 mmol). The mixture was then degassed via vacuum/nitrogen cycles (×3), then Pd(PPh$_3$)$_4$ (12.95 g, 11.21 mmol) was added and the vessel was flushed with nitrogen via vacuum/nitrogen cycles (×3) and heated under reflux for 2 hours. The dark brown reaction mixture was cooled down to ambient temperature and the crude mixture was partitioned between EtOAc (600 mL) and water (300 mL). The combined organic extract was washed with water (300 mL), brine, dried (MgSO$_4$), filtered and concentrated in vacuo. The residue was purified by column chromatography (silica, 0 to 30% EtOAc/Petroleum Ether gradient elution) to give 4-[(E)-2-ethoxyvinyl]-6-methylsulfanyl-pyrimidine as an orange oil which crystallised on standing (27.39 g, 74%); $^1$H NMR (400 MHz, DMSO-d$_6$) δ 8.65 (d, J=1.2 Hz, 1H), 7.87 (d, J=12.5 Hz, 1H), 7.18 (d, J=1.3 Hz, 1H), 5.80 (d, J=12.5 Hz, 1H), 4.01 (q, J=7.0 Hz, 2H), 1.28 (t, J=7.0 Hz, 3H); MS m/z: 197.3 (M+H)$^+$ The following intermediate was prepared according to a procedure similar to Preparation 128:

(E)-2-(2-Ethoxyvinyl)-5-fluoro-4-(methylthio)pyridine;

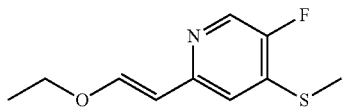

Preparation 129: 3-Chloro-6-(difluoromethyl)pyridazine

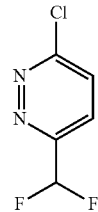

Deoxofluor® (485 μL, 2.631 mmol) was added to a solution of 6-chloropyridazine-3-carbaldehyde (250 mg, 1.754 mmol) in DCM (10 mL) at 0° C. and the mixture warmed to ambient temperature and stirred for 17 hours. Saturated aqueous sodium bicarbonate was added dropwise and the reaction stirred for 30 minutes. The layers were separated and the aqueous phase extracted with DCM (×2). The combined organic extracts were washed with brine and dried (MgSO$_4$), filtered and concentrated in vacuo. The residue was purified by column chromatography (silica, 0 to 100% EtOAc/Petroleum Ether gradient elution) to give 3-chloro-6-(difluoromethyl)pyridazine as a white solid (234.2 mg, 81%); $^1$H NMR (500 MHz, DMSO-d$_6$) δ 7.29 (t, J=54.0 Hz, 1H), 8.12 (d, J=9.0 Hz, 1H), 8.16 (d, J=9.0 Hz, 1H); MS m/z: 165.1 (M+H)$^+$.

Preparation 130: 6-(Difluoromethyl)pyridazin-3-amine

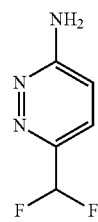

In a 1 L sealed tube, NH$_4$OH (265.8 g, 295.3 mL, 7.584 mol) was added to a stirred solution of 3-chloro-6-(difluoromethyl)pyridazine (20.8 g, 126.4 mmol) in THF (160 mL) and the biphasic solution was heated at 100° C. for 16 hours. The brown reaction mixture was cooled down to ambient temperature and the solvent was removed in vacuo. The residue was triturated with EtOAc (10 vol) and the insoluble material was filtered off. The filtrate was concentrated in vacuo to give the 6-(difluoromethyl)pyridazin-3-amine as a yellow solid (16 g, 87%); $^1$H NMR (500 MHz, DMSO-d$_6$) δ 7.53 (d, J=9.2 Hz, 1H), 7.07-6.85 (m, 4H); MS m/z: 146.1 (M+H)$^+$.

Preparation 131: 6-(Difluoromethyl)-3-(6-methyl-sulfanylpyrimidin-4-yl)imidazo[1,2-b]pyridazine

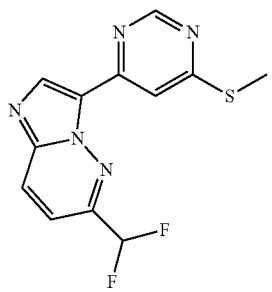 [SMILES: CSc1cc(-c2cnc3ccc(C(F)F)nn23)ncn1]

4-[(E)-2-Ethoxyvinyl]-6-methylsulfanyl-pyrimidine (19.4 g, 98.82 mmol) was dissolved in a mixture of 1,4-dioxane (390 mL) and water (145 mL) at ambient temperature. NBS (17.59 g, 98.82 mmol) was added and the bright yellow solution was stirred at ambient temperature for 15 minutes before 6-(difluoromethyl)pyridazin-3-amine (14.34 g, 98.82 mmol) was added. The orange reaction mixture was heated to 80° C. After 2 hours, the mixture was cooled down to ambient temperature and diluted with saturated aqueous NaHCO₃ (390 mL) and water (485 mL). A brown solid was filtered off, washed copiously with water and dried in vacuo to give 3-(6-methyl sulfanylpyrimidin-4-yl)-6-(trifluoromethyl)imidazo[1,2-b]pyridazine as a brown solid (16.4 g, 56%); $^1$H NMR (400 MHz, DMSO-$d_6$) δ 9.01 (d, J=1.3 Hz, 1H), 8.74 (s, 1H), 8.56 (d, J=9.4 Hz, 1H), 8.53 (d, J=1.3 Hz, 1H), 7.74 (d, J=9.4 Hz, 1H), 7.39 (t, J=53.7 Hz, 1H), 2.64 (s, 3H); MS m/z: 294.2 (M+H)$^+$.

The following compounds were prepared according to a procedure similar to Preparation 131:

3-(6-(Methylthio)pyrimidin-4-yl)-6-(trifluoromethyl)imidazo[1,2-b]pyridazine;

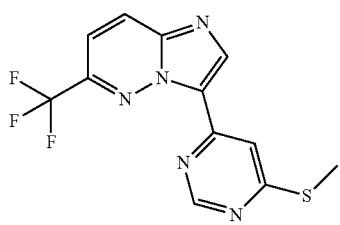 [SMILES: CSc1cc(-c2cnc3ccc(C(F)(F)F)nn23)ncn1]

6-Ethyl-3-(6-(methylthio)pyrimidin-4-yl)imidazo[1,2-b]pyridazine;

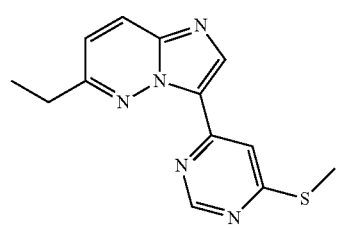 [SMILES: CCc1ccc2ncc(-c3cc(SC)ncn3)n2n1]

6-Methyl-3-(6-(methylthio)pyrimidin-4-yl)imidazo[1,2-b]pyridazine;

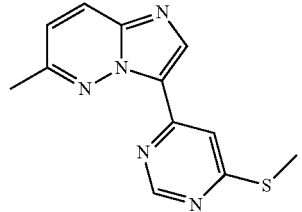

6-Cyclopropyl-3-(6-(methylthio)pyrimidin-4-yl)imidazo[1,2-b]pyridazine;

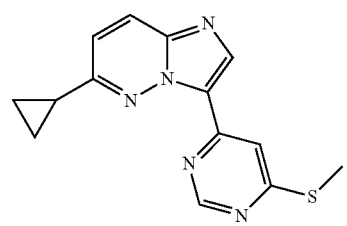 [SMILES: CSc1cc(-c2cnc3ccc(C4CC4)nn23)ncn1]

1-(3-(6-(Methylthio)pyrimidin-4-yl)imidazo[1,2-b]pyridazin-6-yl)ethan-1-one;

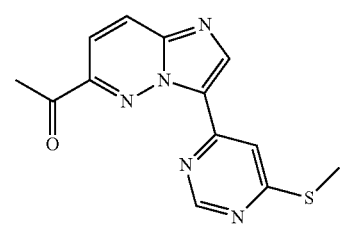 [SMILES: CSc1cc(-c2cnc3ccc(C(C)=O)nn23)ncn1]

3-(6-(Methylthio)pyrimidin-4-yl)imidazo[1,2-b]pyridazine-6-carbonitrile.

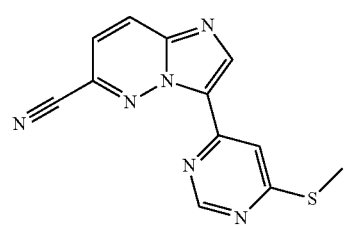 [SMILES: CSc1cc(-c2cnc3ccc(C#N)nn23)ncn1]

6-(Difluoromethyl)-3-(5-fluoro-4-(methylthio)pyridin-2-yl)imidazo[1,2-b]pyridazine

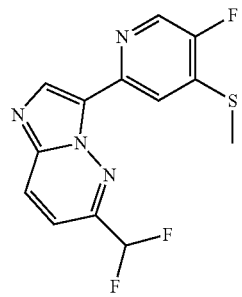 [SMILES: CSc1cc(-c2cnc3ccc(C(F)F)nn23)ncc1F]

Preparation 132: 3-(6-Chloropyrimidin-4-yl)-6-(difluoromethyl)imidazo[1,2-b]pyridazine

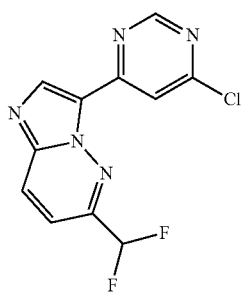 [SMILES: FC(F)c1ccc2ncc(-c3cc(Cl)ncn3)n2n1]

3-(6-Methylsulfanylpyrimidin-4-yl)-6-(trifluoromethyl)imidazo-[1,2-b]pyridazine (7.8 g, 25.06 mmol) was suspended in MeCN (133 mL) and concentrated HCl (2.2 mL of 37% w/w, 40.1 mmol) was added. To the ochre suspension, sulfuryl chloride (13.52 g, 8.11 mL, 100.2 mmol) was slowly added. 20 minutes after the end of addition of sulfuryl chloride, the reaction mixture was slowly added to an ice-water mixture (230 mL) at such a rate that the temperature was kept below 10° C. The suspension was aged for 1 hour before the precipitate was filtered off and washed with water. The solid was stirred for 1 hour in an aqueous saturated solution of NaHCO$_3$ (78 mL), then filtered off, washed with water and dried in the oven at 45° C. under reduced pressure overnight to give 3-(6-chloropyrimidin-4-yl)-6-(difluoromethyl)imidazo[1,2-b]pyridazine as a beige solid (7 g, 93%); 1H NMR (500 MHz, DMSO-d$_6$) δ 9.12 (d, J=1.1 Hz, 1H), 8.82 (s, 1H), 8.67 (d, J=1.1 Hz, 1H), 8.59 (d, J=9.5 Hz, 1H), 7.79 (d, J=9.5 Hz, 1H), 7.43 (t, J=53.6 Hz, 1H); MS m/z: 282.0 (M+H)$^+$.

The following compounds were prepared according to a procedure similar to Preparation 132:

3-(6-Chloropyrimidin-4-yl)-6-(trifluoromethyl)imidazo[1,2-b]pyridazine;

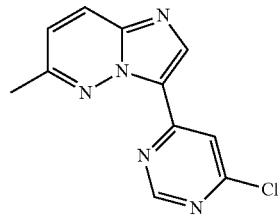 [SMILES: Cc1ccc2ncc(-c3cc(Cl)ncn3)n2n1]

3-(6-Chloropyrimidin-4-yl)-6-ethylimidazo[1,2-b]pyridazine;

3-(6-Chloropyrimidin-4-yl)-6-methylimidazo[1,2-b]pyridazine;

3-(6-Chloropyrimidin-4-yl)-6-cyclopropylimidazo[1,2-b]pyridazine;

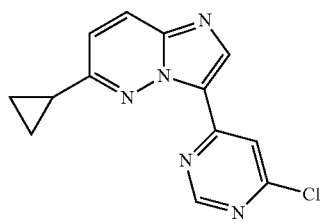 [SMILES: Clc1cc(-c2cnc3ccc(C4CC4)nn23)ncn1]

1-(3-(6-Chloropyrimidin-4-yl)imidazo[1,2-b]pyridazin-6-yl)ethan-1-one;

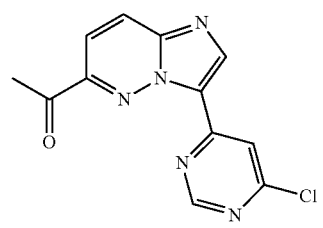 [SMILES: CC(=O)c1ccc2ncc(-c3cc(Cl)ncn3)n2n1]

3-(6-Chloropyrimidin-4-yl)imidazo[1,2b]pyridazine-6-carbonitrile

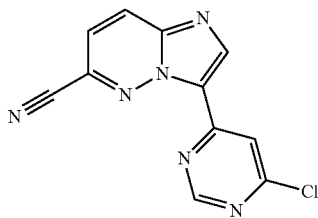 [SMILES: N#Cc1ccc2ncc(-c3cc(Cl)ncn3)n2n1]

3-(4-Chloro-5-fluoropyridin-2-yl)-6-(difluoromethyl)imidazo[1,2-b]pyridazine;

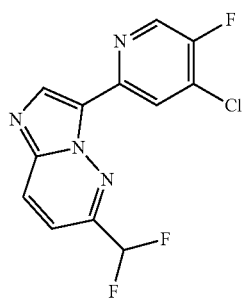 [SMILES: Fc1cnc(-c2cnc3ccc(C(F)F)nn23)cc1Cl]

3-(6-Chloropyrimidin-4-yl)imidazo[1,2-b]pyridazine-6-carboxamide.

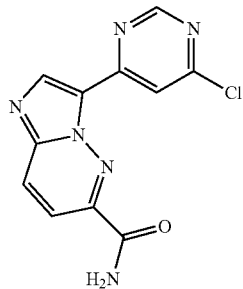 [SMILES: NC(=O)c1ccc2ncc(-c3cc(Cl)ncn3)n2n1]

4-Chloro-6-[6-(3-fluoroazetidin-1-yl)imidazo[1,2-b]pyridazin-3-yl]pyrimidine

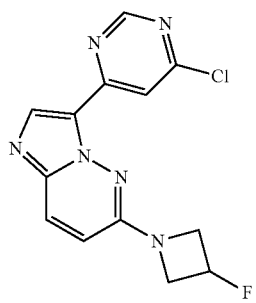 [SMILES: FC1CN(c2ccc3ncc(-c4cc(Cl)ncn4)n3n2)C1]

Preparation 133: Tributyl-[6-(difluoromethyl)imidazo[1,2-b]pyridazin-3-yl]stannane

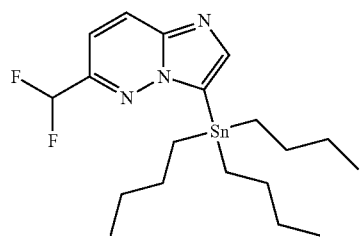 [SMILES: CCC[CH2][Sn]([CH2]CCC)([CH2]CCC)[c]1cnc2ccc(C(F)F)nn12]

A solution of 6-(difluoromethyl)-3-iodo-imidazo[1,2-b]pyridazine (2 g, 6.78 mmol) in dry THF (36 mL) was cooled to 0° C. before the dropwise addition of EtMgBr (6.78 mL of 3 M in Et$_2$O, 20.34 mmol). The mixture was stirred for 10 minutes at 0° C. before adding tributyl-chloro-stannane (2.76 g, 2.3 mL, 8.47 mmol). The mixture was allowed to warm to ambient temperature and stirred for 25 minutes. The mixture was then carefully quenched by addition of water (10 mL) and then partitioned between an aqueous saturated solution of NH$_4$Cl (20 mL) and EtOAc (50 mL). The organic layer was washed with brine, dried (MgSO$_4$) and concentrated in vacuo to give tributyl-[6-(difluoromethyl)imidazo[1,2-b]pyridazin-3-yl]stannane (3.45 g). The residue was used in the next step without further purification.

Preparation 134: 6-(Difluoromethyl)-3-(6-fluoropyrimidin-4-yl)imidazo[1,2-b]pyridazine

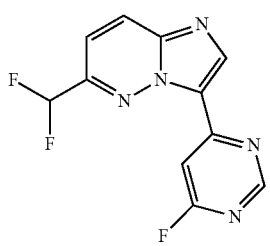 [SMILES: Fc1cc(-c2cnc3ccc(C(F)F)nn23)ncn1]

Tributyl-[6-(difluoromethyl)imidazo[1,2-b]pyridazin-3-yl]stannane (3.4 g, 7.421 mmol) was added to a degassed solution of 4-bromo-6-fluoro-pyrimidine (1.313 g, 7.421 mmol) and PdCl$_2$(PPh$_3$)$_2$ (520.9 mg, 0.742 mmol) in DMF (45 mL). The mixture was further degassed before heating at 70° C. for 16 h. The mixture was concentrated in vacuo and purified by chromatography (silica, 0-45% EtOAc in PE gradient elution) to yield 6-(difluoromethyl)-3-(6-fluoropyrimidin-4-yl)imidazo[1,2-b]pyridazine (500 mg, 25%); MS m/z: 266.1 (M+H)$^+$.

Preparation 135: 6-(Difluoromethyl)-N-(2,2-dimethoxyethyl)pyridazin-3-amine

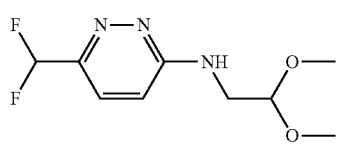 [SMILES: COC(CNc1ccc(C(F)F)nn1)OC]

To 3-difluoromethyl-6-chloropyridazine (7.3 g, 44.3 mmol) was added aminoacetaldehyde dimethylacetal (24.2 mL, 221.83 mmol) at ambient temperature. The mixture was heated at 95° C. for 20 hours then cooled to ambient temperature. The reaction mixture was diluted with dichloromethane (400 mL) and the solution was washed with 5% aq NaHCO₃ (3×100 mL) and brine. The aqueous phase was extracted with dichloromethane (3×150 mL). The combined organic extracts were dried (Na₂SO₄), filtered and the solvent was removed under reduced pressure then dried under vacuum. The solid obtained was triturated in heptane (2×100 mL), filtered and dried to give 6-(difluoromethyl)-N-(2,2-dimethoxyethyl) pyridazin-3-amine as beige solid (9.8 g, 94%); $^1$H NMR (500 MHz, DMSO-$d_6$) δ 3.32 (s, 6H), 3.52 (t, J=5.7 Hz, 2H), 4.56 (t, J=5.4 Hz, 1H), 6.75-7.16 (m, 2H), 7.41 (t, J=6.0 Hz, 1H), 7.52 (d, J=9.0 Hz, 1H); $^{19}$F NMR (282 MHz, DMSO-$d_6$) δ −112.8 (d, J=54.9 Hz, 2F); MS m/z: 234.1 (M+H)⁺.

Preparation 136: 6-(Difluoromethyl)imidazo[1,2-b]pyridazine

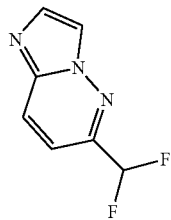 [SMILES: FC(F)c1ccc2nccn2n1]

In a three-necked flask equipped with a thermometer was added concentrated sulfuric acid (13.3 mL, 249.5 mmol, 95-98%) under nitrogen. The sulfuric acid was cooled to 15° C. (internal temperature) then 6-(difluoromethyl)-N-(2,2-dimethoxyethyl) pyridazin-3-amine (9.7 g, 41.6 mmol) was added portion-wise to maintain the internal temperature below 20° C. The cooling bath was removed and after 15 minutes at ambient temperature, the reaction mixture was heated at 70° C. for 5 hours. After being cooled to ambient temperature, the reaction mixture was added dropwise to a cooled (0° C.) aqueous solution of sodium hydroxide (19.96 g of NaOH, 499.1 mmol, in 400 mL of water). The internal temperature was maintained below 10° C. during the addition of the reaction mixture. At the end of the addition, the pH of the aqueous mixture was adjusted to 8 with NaHCO₃ and/or 3% HCl. The aqueous phase was extracted with dichloromethane. The combined organic extracts were dried (Na₂SO₄), filtered and the solvent was removed under reduced pressure. The residue was purified by column chromatography (silica, 0-60% EtOAc in DCM gradient elution) to give 6-(difluoromethyl)imidazo[1,2-b]pyridazine as beige solid (6.53 g, 86% (2 steps)); $^1$H NMR (500 MHz, DMSO-$d_6$) δ 7.07 (t, J=54.0 Hz, 1H), 7.48 (d, J=9.4 Hz, 1H, 7.92-7.98 (m, 1H), 8.35 (d, J=9.4 Hz, 1H), 8.46 (s, 1H); $^{19}$F NMR (282 MHz, DMSO-d6) δ −115.0 (d, J=53.4 Hz, 2F); MS m/z: 170.1 (M+H)⁺.

Preparation 137: 3-Iodo-6-(difluoromethyl)imidazo[1,2-b]pyridazine

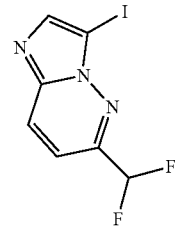 [SMILES: FC(F)c1ccc2ncc(I)n2n1]

In round bottom flask equipped with a refrigerant and an addition funnel was added 6-(difluoromethyl)imidazo[1,2-b]pyridazine (15.2 g, 89.87 mmol) followed by dichloroethane (200 mL) and anhydrous pyridine (130 mL, 1.617 mol). The solution was cooled to 0° C. and iodine monochloride (269.6 mL, 0.269 mol, 1M solution in dichloromethane) was added dropwise. The reaction mixture was stirred 20 minutes at 0° C. then for 30 h at 45° C. The reaction was chilled to 0° C. then 3 more equivalents of ICl (269.6 mL) were added. The reaction mixture was stirred at 0° C. for 20 minutes then at 45° C. overnight. The reaction mixture was diluted with dichloromethane then the organic phase was washed with saturated aqueous sodium thiosulfate and brine, dried (Na₂SO₄), filtered and the solvent was removed under reduced pressure. The residue was purified by column chromatography (silica, 0-50% EtOAc in DCM elution) to give 3-iodo-6-(difluoromethyl)imidazo[1,2-b]pyridazine as a yellow solid (26.75 g, 83%); $^1$H NMR (500 MHz, DMSO-$d_6$) δ 7.23 (t, J=54.0 Hz, 1H), 7.54 (d, J=9.5 Hz, 1H), 8.07 (s, 1H), 8.34 (d, J=9.4 Hz, 1H); $^{19}$F NMR (282 MHz, DMSO-$d_6$) δ −114.9 (d, J=54.9 Hz, 2F); MS m/z: 295.9 (M+H)⁺.

Preparation 138: 6-(Difluoromethyl)-3-(2-fluoro-4-pyridyl)imidazo[1,2-b]pyridazine

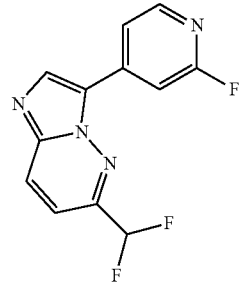 [SMILES: Fc1cc(-c2cnc3ccc(C(F)F)nn23)ccn1]

2-Fluoro-4-(4,4,5,5-tetramethyl-1,3,2-dioxaborolan-2-yl) pyridine (1.966 g, 8.813 mmol), 6-(difluoromethyl)-3-iodo-imidazo[1,2-b]pyridazine (2 g, 6.779 mmol) and Na₂CO₃ (10.2 mL of 2 M, 20.34 mmol) were combined in 1,4-dioxane (80 mL) and degassed with multiple N₂/vacuum cycles before the addition of dichloropalladium triphenylphosphane (476 mg, 0.678 mmol). The mixture was subjected to further degassing cycles before sealing and heating at 90° C. for 8 h. Additional dichloropalladium triphenylphosphane (119 mg, 0.025 eq.) and 2-fluoro-4-(4,4,5,5-tetramethyl-1,3,2-dioxaborolan-2-yl)pyridine (453 mg, 0.3 eq.) were added and the mixture heated at 95° C. for 4 h. The mixture was partitioned between DCM and water. The organic extract was dried (MgSO₄) and concentrated in vacuo to give 6-(difluoromethyl)-3-(2-fluoro-4-pyridyl)imidazo[1,2-b]pyridazine; ¹H NMR (500 MHz, DMSO-d₆) δ 8.82 (s, 1H), 8.53 (d, J=9.4 Hz, 1H), 8.39 (d, J=5.4 Hz, 1H), 8.23 (dt, J=5.4, 1.7 Hz, 1H), 8.09 (s, 1H), 7.71 (d, J=9.4 Hz, 1H), 7.35 (t, J=53.7 Hz, 1H); MS m/z: 265.1 (M+H)⁺.

Preparation 139: 6-(Difluoromethyl)-3-(2,6-difluoropyridin-4-yl)imidazo[1,2-b]pyridazine

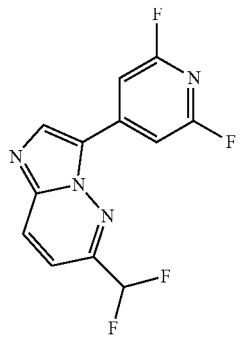 [SMILES: Fc1cc(-c2cnc3ccc(C(F)F)nn23)cc(F)n1]

A mixture of 6-(difluoromethyl)-3-iodo-imidazo[1,2-b]pyridazine (250 mg, 0.847 mmol), 2,6-difluoro-4-(4,4,5,5-tetramethyl-1,3,2-dioxaborolan-2-yl)pyridine (306 mg, 1.271 mmol), PdCl₂(dppf).CH₂Cl₂ (69.2 mg, 0.0847 mmol) and Na₂CO₃ (1.27 mL of 2 M, 2.542 mmol) in THF (4.2 mL) was degassed with N₂ and then heated at 80° C. for 16 hours. The reaction mixture was cooled to ambient temperature, partitioned between EtOAc and an aqueous saturated aqueous solution of sodium bicarbonate. The organic layer was dried (MgSO₄) and concentrated in vacuo to afford 6-(difluoromethyl)-3-(2,6-difluoropyridin-4-yl)imidazo[1,2-b]pyridazine as a light brown solid (350 mg, 89%); MS m/z: 283.1 (M+H)⁺.

The following intermediates were prepared according to a procedure similar to Preparation 139:

6-Chloro-4-(6-(difluoromethyl)imidazo[1,2-b]pyridazin-3-yl)picolinonitrile;

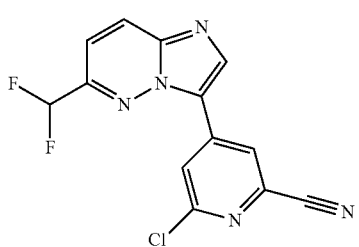 [SMILES: N#Cc1cc(-c2cnc3ccc(C(F)F)nn23)cc(Cl)n1]

3-(2-Chloro-6-(trifluoromethyl)pyridin-4-yl)-6-(difluoromethyl)imidazo[1,2-b]pyridazine;

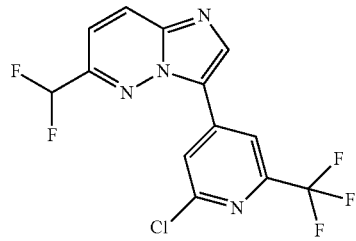 [SMILES: FC(F)c1ccc2ncc(-c3cc(Cl)nc(C(F)(F)F)c3)n2n1]

3-(2,6-Dichloropyridin-4-yl)-6-(difluoromethyl)imidazo[1,2-b]pyridazine;

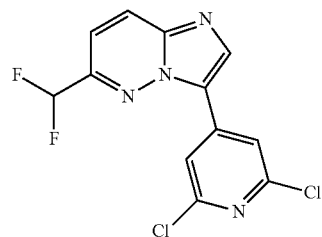 [SMILES: FC(F)c1ccc2ncc(-c3cc(Cl)nc(Cl)c3)n2n1]

4-(6-(Difluoromethyl)imidazo[1,2-b]pyridazin-3-yl)-2-fluorobenzonitrile;

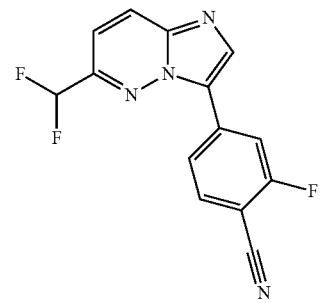 [SMILES: N#Cc1ccc(-c2cnc3ccc(C(F)F)nn23)cc1F]

5-(6-(Difluoromethyl)imidazo[1,2-b]pyridazin-3-yl)-3-fluoropicolinonitrile;

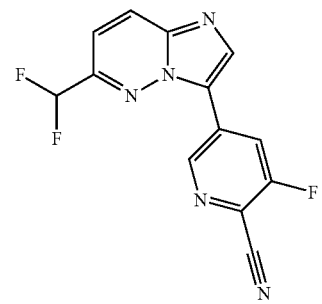 [SMILES: N#Cc1ncc(-c2cnc3ccc(C(F)F)nn23)cc1F]

667

3-(2-Chloro-6-methylpyridin-4-yl)-6-(difluoromethyl)imidazo[1,2-b]pyridazine;

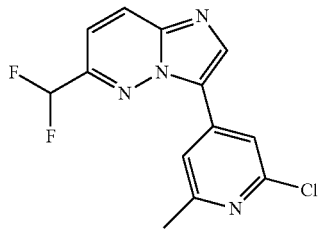 [SMILES: Cc1cc(-c2cnc3ccc(C(F)F)nn23)cc(Cl)n1]

6-(Difluoromethyl)-3-(2,5-difluoropyridin-4-yl)imidazo[1,2-b]pyridazine;

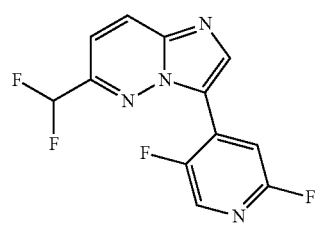 [SMILES: Fc1cc(-c2cnc3ccc(C(F)F)nn23)c(F)cn1]

3-(5-Chloro-2-fluoropyridin-4-yl)-6-(difluoromethyl)imidazo[1,2-b]pyridazine;

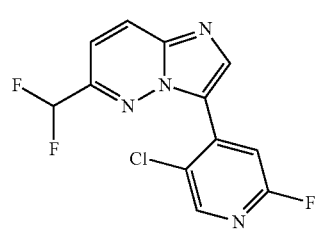 [SMILES: Fc1cc(-c2cnc3ccc(C(F)F)nn23)c(Cl)cn1]

3-(2-Chloro-6-methoxypyridin-4-yl)-6-(difluoromethyl)imidazo[1,2-b]pyridazine;

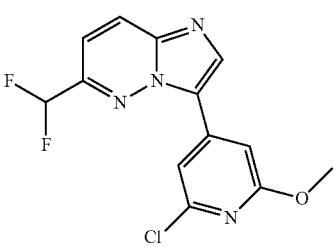 [SMILES: COc1cc(-c2cnc3ccc(C(F)F)nn23)cc(Cl)n1]

668

6-(Difluoromethyl)-3-(2-fluoro-5-methylpyridin-4-yl)imidazo[1,2-b]pyridazine;

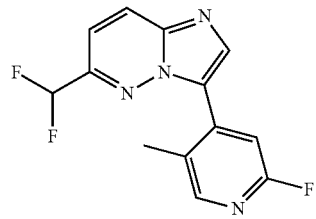 [SMILES: Cc1cnc(F)cc1-c1cnc2ccc(C(F)F)nn12]

8-(4-(6-(Difluoromethyl)imidazo[1,2-b]pyridazin-3-yl)pyridin-2-yl)-2-(methylsulfonyl)-5-oxa-2,8-diazaspiro[3.5]nonane II-126

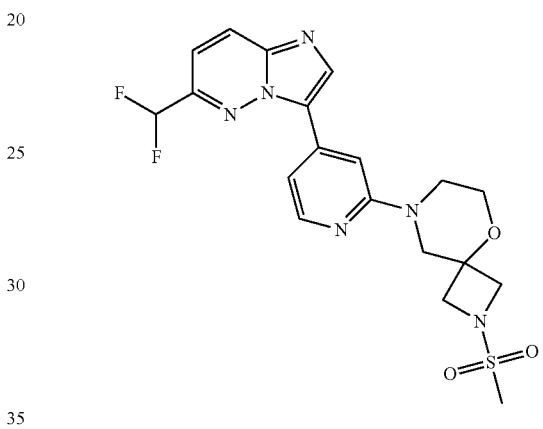

6-(Difluoromethyl)-3-(2,5-difluoropyridin-4-yl)imidazo[1,2-b]pyridazine;

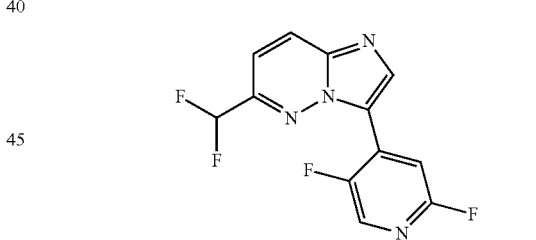

3-(5-Chloro-2-fluoropyridin-4-yl)-6-(difluoromethyl)imidazo[1,2-b]pyridazine

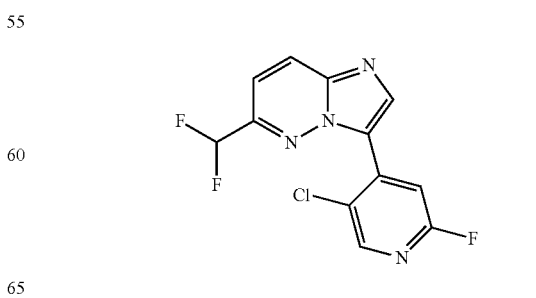

Preparation 140: 6-(Difluoromethyl)-3-(4-fluoro-2-pyridyl)imidazo[1,2-b]pyridazine

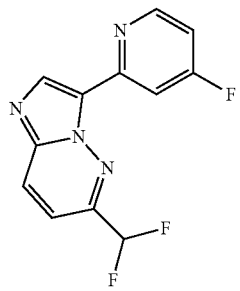 [SMILES: Fc1ccnc(-c2cnc3ccc(C(F)F)nn23)c1]

A mixture of 6-(difluoromethyl)-3-iodo-imidazo[1,2-b]pyridazine (480 mg, 1.63 mmol), 4-fluoro-2-(4,4,5,5-tetramethyl-1,3,2-dioxaborolan-2-yl)pyridine (725 mg, 3.25 mmol), $Cs_2CO_3$ (1.59 g, 4.88 mmol), $Pd(OAc)_2$ (18.3 mg, 0.081 mmol), dppf (90.2 mg, 0.163 mmol) and CuCl (161.1 mg, 1.627 mmol) in DMF (20 mL) was degassed with $N_2$ and then heated at 90° C. for 3 hours. The reaction mixture was partitioned between EtOAc and a saturated aqueous solution of sodium bicarbonate. The organic layer was dried ($Na_2SO_4$) and concentrated in vacuo to afford 6-(difluoromethyl)-3-(4-fluoro-2-pyridyl)imidazo[1,2-b]pyridazine as a dark solid (270 mg) that was used in next step without further purification; MS m/z: 265.1 (M+H)+.

Preparation 141: 2-(Methylsulfonyl)-8-(4-(4,4,5,5-tetramethyl-1,3,2-dioxaborolan-2-yl)pyridin-2-yl)-5-oxa-2,8-diazaspiro[3.5]nonane

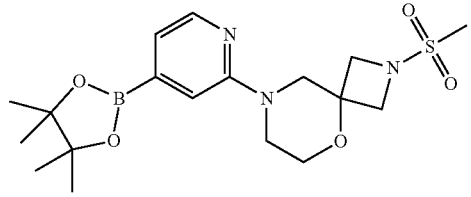

Step 1: tert-Butyl 8-(4-bromopyridin-2-yl)-5-oxa-2,8-diazaspiro[3.5]nonane-2-carboxylate A solution of 4-bromo-2-fluoro-pyridine (50 mg, 0.284 mmol), tert-butyl 5-oxa-2,8-diazaspiro[3.5]nonane-2-carboxylate (97.3 mg, 0.426 mmol) and $Et_3N$ (120 µL, 0.861 mmol) in NMP (1 mL) was heated at 110° C. in a sealed tube for 21 hours. The reaction mixture was cooled to ambient temperature and partitioned between EtOAc and brine. The layers were separated and the organic phase washed with brine (×3), dried ($MgSO_4$), filtered and concentrated in vacuo. The residue was purified by column chromatography (silica, 0 to 30% EtOAc/Petroleum Ether gradient elution) to give tert-butyl 8-(4-bromo-2-pyridyl)-5-oxa-2,8-diazaspiro[3.5]nonane-2-carboxylate (75.8 mg, 0.197 mmol, 69%) as a colourless oil; 1H NMR (500 MHz, Chloroform-d) δ 8.03 (d, J=5.3 Hz, 1H), 6.86 (d, J=5.2 Hz, 1H), 6.83 (s, 1H), 3.90 (d, J=9.3 Hz, 2H), 3.84 (d, J=9.2 Hz, 2H), 3.80 (t, J=5.0 Hz, 2H), 3.66 (s, 2H), 3.47 (dd, J=5.7, 4.6 Hz, 2H), 1.47 (s, 9H); MS m/z: 384.1 (M+H)+.

Step 2: 8-(4-Bromopyridin-2-yl)-5-oxa-2,8-diazaspiro[3.5]nonane

TFA (1 mL, 12.98 mmol) was added to a stirred solution of tert-butyl 8-(4-bromo-2-pyridyl)-5-oxa-2,8-diazaspiro[3.5]nonane-2-carboxylate (75 mg, 0.195 mmol) in DCM (5 mL) and the reaction was stirred at ambient temperature for 17 hours. The solvent was removed in vacuo and the residue azeotroped with DCM (×2) and diethyl ether (×2). The residue was passed through a 2 g SCX-2 cartridge and washed with MeOH/DCM mixtures. The product was eluted by washing the cartridge with 2 M $NH_3$ in MeOH/DCM mixtures. The solvent was removed in vacuo to give 8-(4-bromo-2-pyridyl)-5-oxa-2,8-diazaspiro[3.5]nonane (55.5 mg, 0.195 mmol, 100%) as a colourless oil; 1H NMR (500 MHz, Chloroform-d) δ 8.02 (d, J=5.3 Hz, 1H), 6.89 (d, J=1.4 Hz, 1H), 6.83 (dd, J=5.3, 1.5 Hz, 1H), 3.77-3.75 (m, 2H), 3.71-3.66 (m, 4H), 3.53-3.51 (m, 2H), 3.47-3.45 (m, 2H); MS m/z: 286.1 (M+H)+.

Step 3: 8-(4-Bromopyridin-2-yl)-2-(methylsulfonyl)-5-oxa-2,8-diazaspiro[3.5]nonane Methanesulfonyl chloride (20 µL, 0.258 mmol) was added to a stirred solution of 8-(4-bromo-2-pyridyl)-5-oxa-2,8-diazaspiro[3.5]nonane (55 mg, 0.194 mmol) and $Et_3N$ (50 µL, 0.359 mmol) in THF (2 mL) under an atmosphere of nitrogen. The reaction was stirred at ambient temperature for 16 hours, then diluted with DCM and saturated aqueous $NaHCO_3$ and the mixture was stirred for 10 minutes. The layers were separated and the aqueous layer extracted with DCM (×2). The combined organic extracts were dried ($MgSO_4$), filtered and concentrated in vacuo to give as a white solid that was used directly in the next step without further purification; 1H NMR (500 MHz, Chloroform-d) δ 8.04 (d, J=5.3 Hz, 1H), 6.88 (dd, J=5.3, 1.5 Hz, 1H), 6.86-6.84 (m, 1H), 3.95 (d, J=9.0 Hz, 2H), 3.85 (d, J=9.1 Hz, 2H), 3.81-3.79 (m, 2H), 3.73 (s, 2H), 3.49-3.47 (m, 2H), 2.95 (s, 3H); MS m/z: 364.0 (M+H)+.

Step 4: 2-(Methylsulfonyl)-8-(4-(4,4,5,5-tetramethyl-1,3,2-dioxaborolan-2-yl)pyridin-2-yl)-5-oxa-2,8-diazaspiro[3.5]nonane 8-(4-Bromo-2-pyridyl)-2-methylsulfonyl-5-oxa-2,8-diazaspiro[3.5]nonane (67 mg, 0.185 mmol) was dissolved in 1,4-dioxane (2.5 mL) and bis(pinacolato)diboron (70 mg, 0.276 mmol) and KOAc (55 mg, 0.560 mmol) were added. The reaction was degassed and filled with nitrogen five times, then $PdCl_2(PCy_3)_2$ (15 mg, 0.020 mmol) was added and the reaction heated to 90° C. for 2 hours. The reaction mixture was cooled to ambient temperature and the solution was used in next step without further purification.

Preparation 142: 3-(2-Fluoropyridin-4-yl)-6-(trifluoromethyl)imidazo[1,2-b]pyridazine

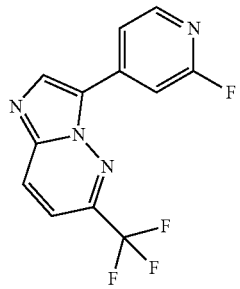 [SMILES: Fc1cc(-c2cnc3ccc(C(F)(F)F)nn23)ccn1]

Step 1: 6-(Trifluoromethyl)pyridazin-3-amine

A mixture of 3-chloro-6-(trifluoromethyl)pyridazine (0.5 g, 2.739 mmol) and NH$_4$OH (3 mL, 77.04 mmol) in THF (1 mL) was heated at 100° C. in a sealed tube for 2 hours. The reaction was cooled to ambient temperature and the solvent removed in vacuo. The residue was diluted with the minimum of water and extracted with DCM (×3). The combined organic extracts were dried (MgSO$_4$), filtered and concentrated in vacuo to give the title product as an orange solid; $^1$H NMR (500 MHz, DMSO-d$_6$) δ 7.66 (d, J=9.3 Hz, 1H), 7.15 (s, 2H), 6.90 (d, J=9.3 Hz, 1H); 19F NMR (471 MHz, DMSO-d$_6$) δ −64.58; MS m/z: 164.0 (M+H)$^+$.

Step 2: 6-(Trifluoromethyl)imidazo[1,2-b]pyridazine

To a solution of 6-(trifluoromethyl)pyridazin-3-amine (438 mg, 2.685 mmol) in n-BuOH (5 mL) was added 2-chloroacetaldehyde (562 μL of 45% w/v in water, 3.22 mmol) and the reaction heated under reflux for 20 hours. The reaction was cooled to ambient temperature and the solvent removed in vacuo. The residue was partitioned between DCM and saturated aqueous NaHCO$_3$ and the layers separated. The aqueous layer was extracted with DCM (×3) and the combined organic extracts dried (MgSO$_4$), filtered and concentrated in vacuo. The residue was purified by column chromatography (silica, 0 to 50% EtOAc/Petroleum Ether gradient elution) to give 6-(trifluoromethyl)imidazo[1,2-b]pyridazine (368.7 mg, 73%) as a beige solid; $^1$H NMR (500 MHz, DMSO-d$_6$) δ 8.59 (s, 1H), 8.47 (d, J=9.5 Hz, 1H), 8.06 (d, J=1.2 Hz, 1H), 7.67 (d, J=9.5 Hz, 1H); $^{19}$F NMR (471 MHz, DMSO-d$_6$) δ −65.14; MS m/z: 188.0 (M+H)$^+$.

Step 3: 3-Iodo-6-(trifluoromethyl)imidazo[1,2-b]pyridazine

To a stirred solution of 6-(trifluoromethyl)imidazo[1,2-b]pyridazine (268 mg, 1.432 mmol) in DCM (3 mL) and pyridine (1.5 mL) at 0° C. was added dropwise iodine monochloride (3.6 mL of 1 M, 3.6 mmol). The reaction mixture was heated at 50° C. in a sealed tube for 137 hours then cooled to ambient temperature. A further portion of iodine monochloride (1.5 mL of 1 M, 1.5 mmol) was added and the reaction mixture heated at 50° C. in a sealed tube for 45 hours. The reaction was cooled to ambient temperature and diluted with DCM. The mixture was washed with saturated aqueous sodium thiosulfate (×2) and brine, dried (MgSO$_4$), filtered and concentrated in vacuo. The residue was triturated with DCM and the resultant precipitate isolated by filtration and dried to give 3-iodo-6-(trifluoromethyl)imidazo[1,2-b]pyridazine (118 mg, 26%) as a pale yellow solid; $^1$H NMR (500 MHz, DMSO-d$_6$) δ 8.45 (d, J=9.4 Hz, 1H), 8.18 (s, 1H), 7.72 (d, J=9.4 Hz, 1H); $^{19}$F NMR (471 MHz, DMSO-d$_6$) δ −65.08; MS m/z: 313.9 (M+H)$^+$.

Step 4: 3-(2-Fluoro-4-pyridyl)-6-(trifluoromethyl)imidazo[1,2-b]pyridazine

A mixture of 6-(trifluoromethyl)imidazo[1,2-b]pyridazine (300 mg, 1.603 mmol), 4-bromo-2-fluoro-pyridine (396.3 mg, 2.252 mmol), K$_2$CO$_3$ (433.8 mg, 3.139 mmol), LiCl (70.5 mg, 1.662 mmol), PPh$_3$ (86.8 mg, 0.331 mmol) and Pd(OAc)$_2$ (38.0 mg, 0.169 mmol) in toluene (6 mL) was heated at 150° C. for 17 hours. The mixture was concentrated under reduced pressure and purified by column chromatography (silica, hexane/EtOAc gradient elution) to give 3-(2-fluoro-4-pyridyl)-6-(trifluoromethyl)imidazo[1,2-b]pyridazine (150 mg, 0.531 mmol, 33%); MS m/z: 283.1 (M+H)$^+$.

Preparation 143: 3-Iodo-N-methylimidazo[1,2-b]pyridazin-6-amine

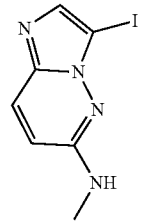

To a solution of 6-chloro-3-iodo-imidazo[1,2-b]pyridazine (612 mg, 2.19 mmol) in a mixture of isopropyl alcohol (6 mL) and DMF (3 mL) was added methylamine (1.7 mL of 40% w/v in water, 21.9 mmol). The mixture was heated at 80° C. for 10 hours then at 100° C. for 8 hours. The mixture was diluted with EtOAc and sequentially washed with a saturated aqueous solution of NH$_4$Cl, an aqueous saturated solution of NaHCO$_3$ and brine. The organic layer was dried (MgSO$_4$) and concentrated to give an orange solid, which was purified by column chromatography (silica, PE/EtOAc 9/1 to 6/4 gradient elution) to give 3-iodo-N-methylimidazo[1,2-b]pyridazin-6-amine (325 mg, 40%); MS m/z: 275.0 (M+H)$^+$.

Preparation 144: 6-Methylimidazo[1,2-b]pyridazine

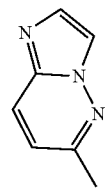

6-Chloroimidazo[1,2-b]pyridazine (1 g, 6.51 mmol), methylboronic acid (467.7 mg, 7.81 mmol) and K$_3$PO$_4$ (4.15 g, 19.5 mmol) were combined in toluene (15 mL). The mixture was degassed (×2 vacuum-N$_2$ cycles) and SPhos (267.3 mg, 0.651 mmol) followed by Pd(OAc)$_2$ (73.1 mg, 0.326 mmol) were added before the mixture was heated at 150° C. for 3 hours. The reaction mixture was partitioned between EtOAc (100 mL) and water (100 mL). The combined organic layers were dried and concentrated in vacuo. The residue was purified by column chromatography (silica, 0-3% MeOH/DCM gradient elution), to give 6-methylimidazo[1,2-b]pyridazine (323 mg, 37%); $^1$H NMR (500 MHz, DMSO-d$_6$) δ 8.17 (dd, J=1.2, 0.7 Hz, 1H), 8.01 (dd, J=9.3, 0.7 Hz, 1H), 7.69 (d, J=1.2 Hz, 1H), 7.13 (d, J=9.3 Hz, 1H), 2.52 (s, 3H); MS m/z: 134.4 (M+H)$^+$.

Preparation 145: 6-(Difluoromethoxy)imidazo[1,2-b]pyridazine

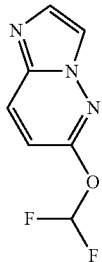 [SMILES: FC(F)Oc1ccc2nccn2n1]

A mixture of imidazo[1,2-b]pyridazin-6-ol (250 mg, 1.85 mmol), Cs$_2$CO$_3$ (845 mg, 2.593 mmol) and methyl 2-chloro-2,2-difluoro-acetate (390 µL, 3.697 mmol) in DMF (2.5 mL) was heated at 95° C. for 1 hour. The reaction was cooled to ambient temperature and quenched with water. The mixture was extracted with EtOAc (×3) and the combined organic extracts washed with brine (×3), dried (MgSO$_4$), filtered and concentrated in vacuo. The material was purified by reverse phase chromatography (C18, MeCN/Water/0.05% TFA as eluent) give 6-(difluoromethoxy)imidazo[1,2-b]pyridazine (23 mg, 4.2%) as an off-white solid; $^1$H NMR (500 MHz, DMSO-d$_6$) δ 8.32-8.30 (m, 2H), 7.86 (d, J=1.3 Hz, 1H), 7.69 (t, J=71.3 Hz, 1H), 7.20 (d, J=9.7 Hz, 1H); MS m/z: 186.1 (M+H)$^+$.

Preparation 146: 3-Bromo-6-(trifluoromethyl)imidazo[1,2-b]pyridazine

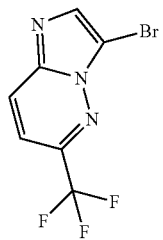 [SMILES: FC(F)(F)c1ccc2ncc(Br)n2n1]

A solution of 3-bromoimidazo[2,1-f]pyridazine (50 mg, 0.252 mmol) and zinc trifluoromethanesulfinate (168 mg, 0.507 mmol) in DCM (1 mL) and water (0.4 mL) was cooled to 0° C. followed by the slow addition of t-BuOOH (100 µL of 70% w/v, 0.777 mmol). The solution was warmed to ambient temperature over 15 hours. The reaction mixture was partitioned between DCM and saturated aqueous NaHCO$_3$ and the layers separated. The aqueous layer was extracted with DCM (×3) and the combined organic extracts dried (MgSO$_4$), filtered and concentrated in vacuo. The residue was purified by column chromatography (silica, 0 to 10% EtOAc/Petroleum Ether gradient elution) to give a mixture of two regioisomers (29.5 mg, 0.1109 mmol, 44%) that was used directly in the next reaction; MS m/z: (M+H)$^+$.

Preparation 147: 1-(4-(4-(7-Chloroimidazo[1,2-b]pyridazin-3-yl)pyridin-2-yl)piperazin-1-yl)ethanone

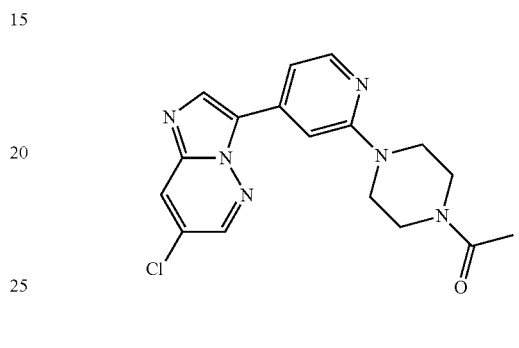

Step 1: 1-(4-(4-Bromopyridin-2-yl)piperazin-1-yl)ethanone

Acetyl chloride (335 µL, 4.71 mmol) was added to a solution of 1-(4-bromo-2-pyridyl)piperazine (750 mg, 3.10 mmol) and Et$_3$N (1 mL, 7.18 mmol) in DCM (7.5 mL) and the reaction mixture allowed to stir at ambient temperature for 48 hours. The mixture was washed with saturated aqueous NaHCO$_3$ (×2) and brine (×1), dried (MgSO$_4$), filtered and concentrated in vacuo. The residue was purified by column chromatography (silica, 0 to 100% EtOAc/Petroleum Ether gradient elution) to give 1-(4-(4-bromopyridin-2-yl)piperazin-1-yl)ethanone (715.7 mg, 81%) as a cream solid; $^1$H NMR (500 MHz, Chloroform-d) δ 8.02 (dd, J=5.1, 0.9 Hz, 1H), 6.84-6.82 (m, 2H), 3.77-3.75 (m, 2H), 3.67-3.65 (m, 2H), 3.61-3.59 (m, 2H), 3.55-3.53 (m, 2H), 1.57 (s, 3H); MS m/z: 286.1 (M+H)$^+$.

Step 2: 1-(4-(4-(7-Chloroimidazo[1,2-b]pyridazin-3-yl)pyridin-2-yl)piperazin-1-yl)ethanone A mixture of 7-chloroimidazo[1,2-b]pyridazine (30 mg, 0.195 mmol), 1-[4-(4-bromo-2-pyridyl)piperazin-1-yl]ethanone (75 mg, 0.264 mmol), K$_2$CO$_3$ (55 mg, 0.398 mmol), LiCl (9 mg, 0.212 mmol), PPh$_3$ (12 mg, 0.046 mmol) and Pd(OAc)$_2$ (5 mg, 0.022 mmol) in toluene (1 mL) was heated at 110° C. for 17 hours. The reaction was cooled to ambient temperature, diluted with DCM and the precipitate removed by filtration. The filtrate was concentrated in vacuo and purified by reverse phase chromatography (C18, MeCN/Water/0.05% TFA as eluent) to give 1-(4-(4-(7-chloroimidazo[1,2-b]pyridazin-3-yl)pyridin-2-yl)piperazin-1-yl)ethanone (24.4 mg, 26%) as an off-white solid.

The following compounds were prepared using a methodology similar to the one described in Preparation 147:

1-(4-(4-(6-(Difluoromethoxy)imidazo[1,2-b]pyridazin-3-yl)pyridin-2-yl)piperazin-1-yl)ethanone II-182.

Preparation 148:
2,5-Dimethylpiperidine-3-carboxamide A134 and
2,5-dimethylpiperidine-3-carboxylic Acid A135

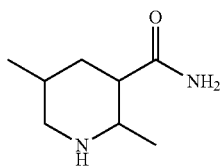

A134

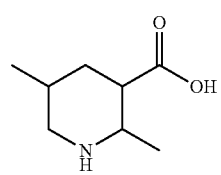

A135

Step 1: 2,5-Dimethylnicotinamide

Methyl 2,5-dimethylpyridine-3-carboxylate (100 mg, 0.61 mmol) was dissolved in ammonium hydroxide (480 µL, 12.3 mmol) and the mixture heated to 70° C. in a sealed tube. After 16 hours the reaction was diluted in water and the mixture concentrated in vacuo to give 2,5-dimethylpyridine-3-carboxamide (91 mg, 100%) as a white solid; MS m/z: 151.0 (M+H)$^+$.

Step 2: 2,5-Dimethylpiperidine-3-carboxamide 2,5-Dimethylnicotinamide (99 mg, 0.66 mmol) and PtO$_2$ (30.4 mg, 0.13 mmol) were dissolved in methanol (3 mL) and 3 M HCl (1.1 mL, 3.30 mmol). The mixture was degassed and stirred under a balloon of H$_2$ for 90 minutes before being passed through Celite and the filtrate concentrated in vacuo to give 2,5-dimethylpiperidine-3-carboxamide (dihydrochloride salt) (150 mg, 99%); MS m/z: 157.0 (M+H)$^+$. Some 2,5-dimethylpiperidine-3-carboxylic acid was also isolated but not characterized.

Preparation 149: cis-[6-Cyclopropyl-4-[6-[6-(difluoromethyl)imidazo[1,2-b]pyridazin-3-yl]pyrimidin-4-yl]morpholin-2-yl]methyl Methanesulfonate

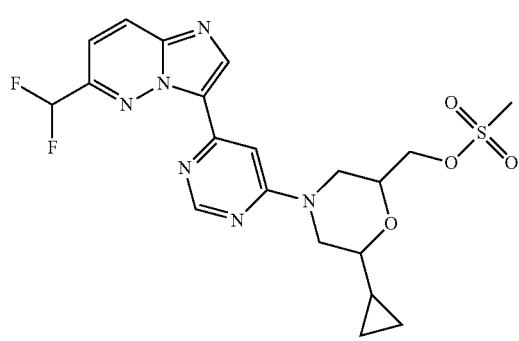 [SMILES: CS(=O)(=O)OCC1CN(c2cc(-c3cnc4ccc(C(F)F)nn34)ncn2)CC(C2CC2)O1]

Methanesulfonyl chloride (30 µL, 0.39 mmol) was added to a suspension of cis-[6-cyclopropyl-4-[6-[6-(difluoromethyl)imidazo[1,2-b]pyridazin-3-yl]pyrimidin-4-yl]morpholin-2-yl]methanol (106 mg, 0.26 mmol) and triethylamine (55 µL, 0.39 mmol) in DCM (15 mL) under N$_2$ and the reaction stirred at ambient temperature for 3 hours. The mixture was diluted with DCM and quenched by the addition of saturated aqueous NaHCO$_3$. After stirring for 10 minutes the layers were separated and the organic phase concentrated to give cis-[6-cyclopropyl-4-[6-[6-(difluoromethyl)imidazo[1,2-b]pyridazin-3-yl]pyrimidin-4-yl]morpholin-2-yl]methyl methanesulfonate (126.6 mg, 100%); MS m/z: 481.3 (M+H)$^+$.

The following compounds were prepared according to a procedure similar to the one described in Preparation 149:

(1-(6-(6-(Difluoromethyl)imidazo[1,2-b]pyridazin-3-yl)pyrimidin-4-yl)-5-(2-methoxyethoxy)piperidin-3-yl)methyl methanesulfonate;

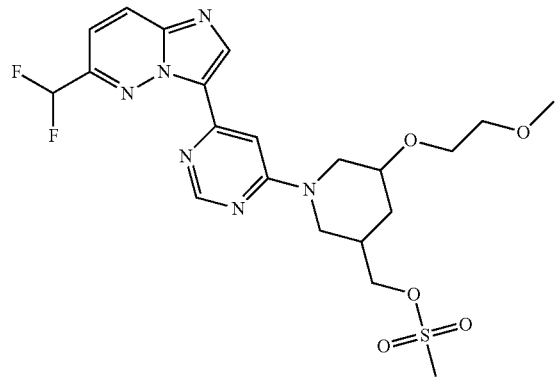 [SMILES: COCCOC1CC(COS(C)(=O)=O)CN(c2cc(-c3cnc4ccc(C(F)F)nn34)ncn2)C1]

(4-(6-(6-(Difluoromethyl)imidazo[1,2-b]pyridazin-3-yl)pyrimidin-4-yl)-3-methylmorpholin-2-yl)methyl methanesulfonate;

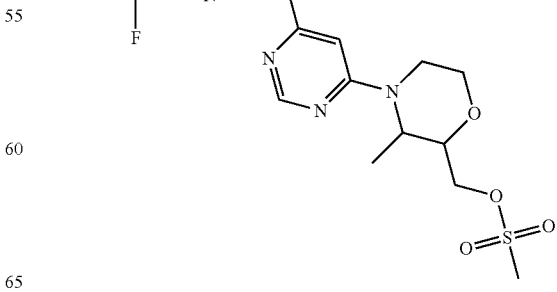

(1-(tert-Butyl)-4-(6-(6-(difluoromethyl)imidazo[1,2-b]pyridazin-3-yl)pyrimidin-4-yl)-3-methylpiperazin-2-yl)methyl methanesulfonate;

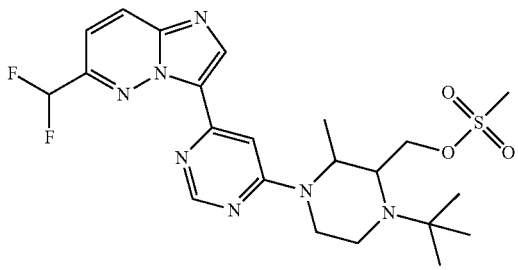 [SMILES: CC1C(COS(C)(=O)=O)N(C(C)(C)C)CCN1c1cc(-c2cnc3ccc(C(F)F)nn23)ncn1]

(S)-(4-(6-(6-(Difluoromethyl)imidazo[1,2-b]pyridazin-3-yl)pyrimidin-4-yl)-1-methylpiperazin-2-yl)methyl methanesulfonate.

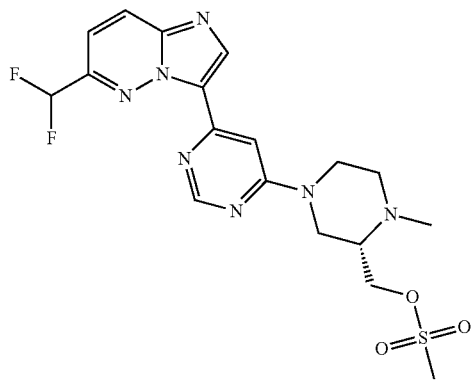 [SMILES: CN1CCN(c2cc(-c3cnc4ccc(C(F)F)nn34)ncn2)C[C@H]1COS(C)(=O)=O]

Preparation 150: 3-(6-Chloropyrimidin-4-yl)-5-(difluoromethyl)-2-iodopyrazolo[1,5-a]pyrimidine

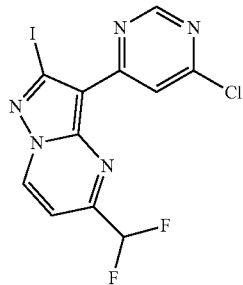 [SMILES: FC(F)c1ccn2nc(I)c(-c3cc(Cl)ncn3)c2n1]

Step 1: 5-(Difluoromethyl)-3-(6-methylsulfanylpyrimidin-4-yl)pyrazolo[1,5-a]pyrimidin-2-amine 4-(6-Methylsulfanylpyrimidin-4-yl)-1H-pyrazole-3,5-diamine (described in WO2009/085913) (25 g, 112.5 mmol) and 4-ethoxy-1,1-difluoro-but-3-en-2-one (21.1 g, 140.3 mmol) were suspended in 1,4-dioxane (150 mL). KOH (6.23 g, 111.1 mmol) was added and the reaction mixture stirred at 90° C. for 5 hours. The reaction mixture was cooled to ambient temperature and HCl (55.5 mL of 2 M, 111.0 mmol) was added slowly. The mixture was stirred at ambient temperature for 15 minutes before adding water (250 mL) and stirring for another 1 hour. The solid was isolated by filtration, washed with water and dried under vacuum at 40° C. to give 5-(difluoromethyl)-3-(6-methylsulfanylpyrimidin-4-yl)pyrazolo[1,5-a]pyrimidin-2-amine as a brown solid (27.0 g, 78%); $^1$H NMR (400 MHz, DMSO-$d_6$) δ 9.20 (d, 1H), 8.86 (d, 1H), 8.33 (d, 1H), 7.27 (br s, 2H), 7.24 (d, 1H), 7.10 (t, 1H), 2.59 (s, 3H); $^{19}$F NMR (376 MHz, DMSO-$d_6$) δ −117.1; MS m/z: 309.0 (M+H)$^+$.

Step 2: 3-(6-Chloropyrimidin-4-yl)-5-(difluoromethyl)pyrazolo[1,5-a]pyrimidin-2-amine 5-(Difluoromethyl)-3-(6-methylsulfanylpyrimidin-4-yl)pyrazolo[1,5-a]pyrimidin-2-amine (27.0 g, 87.58 mmol) was suspended in MeCN (459 mL) and concentrated HCl (13.8 g, 7.67 mL of 37% w/w, 140.1 mmol) was added. Sulfuryl chloride (47.3 g, 28.4 mL, 350.3 mmol) was added and the reaction stirred at ambient temperature for 25 minutes. The reaction mixture was added slowly to ice water (810 mL) at such a rate that the temperature was kept below 10° C. The suspension was aged for 1 hour and the solid was isolated by filtration, washing with water. The solid was added to saturated aqueous NaHCO$_3$ (270 mL) and stirred for 30 minutes. The solid was isolated by filtration, washed with water and dried under vacuum at 40° C. to give 3-(6-chloropyrimidin-4-yl)-5-(difluoromethyl)pyrazolo[1,5-a]pyrimidin-2-amine as a beige solid (21.4 g, 84% purity, 69%); $^1$H NMR (400 MHz, DMSO-$d_6$) δ 9.13 (d, 1H), 8.92 (d, 1H), 8.42 (d, 1H), 7.32 (br s, 2H), 7.30 (d, 1H), 7.13 (t, 1H); $^{19}$F NMR (376 MHz, DMSO-$d_6$) δ −117.1; MS m/z: 296.9 (M+H)$^+$, 294.9 (M−H)$^+$.

Step 3: 3-(6-Chloropyrimidin-4-yl)-5-(difluoromethyl)-2-iodo-pyrazolo[1,5-a]pyrimidine p-Toluenesulfonic acid hydrate (483 mg, 2.54 mmol) was added to a suspension of 3-(6-chloropyrimidin-4-yl)-5-(difluoromethyl)pyrazolo[1,5-a]pyrimidin-2-amine (250 mg, 0.843 mmol) in MeCN (5 mL) at ambient temperature. A solution of KI (350 mg, 2.11 mmol) and sodium nitrite (117 mg, 1.69 mmol) in H$_2$O (2.5 mL) was added dropwise and the reaction was allowed to stir at ambient temperature for 16 hours. The reaction was quenched by the addition of saturated aqueous NaHCO$_3$ and saturated aqueous Na$_2$S$_2$O$_3$ and the resultant precipitate was isolated by filtration. The solid was taken up in DCM/MeOH and filtered to remove insoluble residues. The filtrate was concentrated in vacuo to give 3-(6-chloropyrimidin-4-yl)-5-(difluoromethyl)-2-iodopyrazolo[1,5-a]pyrimidine as a red solid that was used directly in the next step; MS m/z: 407.9 (M+H)$^+$.

Preparation 151: 3-(6-Chloropyrimidin-4-yl)-5-(difluoromethyl)pyrazolo[1,5-a]pyrimidine

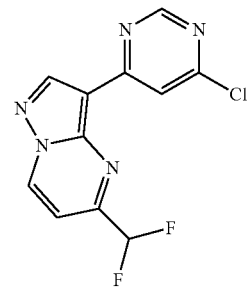 [SMILES: FC(F)c1ccn2ncc(-c3cc(Cl)ncn3)c2n1]

MeOH (34 mL) was added to 3-(6-chloropyrimidin-4-yl)-5-(difluoromethyl)-2-iodo-pyrazolo[1,5-a]pyrimidine (1.37 g, 3.37 mmol) and palladium on carbon (100 mg) under a nitrogen atmosphere. The vessel was then purged and the solution was stirred under a balloon of $H_2$ for 16 hours. The catalyst was removed by filtration through Celite, washing with MeOH, and the filtrate concentrated. Purification by column chromatography (silica, petrol/EtOAc, then MeOH/DCM gradients) gave 3-(6-chloropyrimidin-4-yl)-5-(difluoromethyl)pyrazolo[1,5-a]pyrimidine as a yellow solid (88 mg, 9%); MS m/z: 282.1 $(M+H)^+$.

Preparation 152: 3-(6-Chloropyrimidin-4-yl)-5-(difluoromethyl)-6-fluoro-2-iodo-pyrazolo[1,5-a]pyrimidine

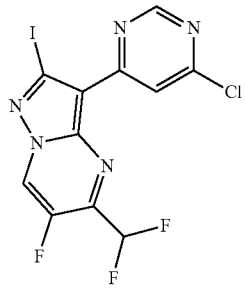 [SMILES: Fc1cn2nc(I)c(-c3cc(Cl)ncn3)c2nc1C(F)F]

Step 1: 7-(Difluoromethyl)-6-fluoro-3-(6-methylsulfanylpyrimidin-4-yl)pyrazolo[1,5-a]pyrimidin-2-amine A solution of 2,4,4-trifluoro-3,3-dihydroxy-butanal (0.907 g, 5.74 mmol), 4-(6-methylsulfanylpyrimidin-4-yl)-1H-pyrazole-3,5-diamine (described in WO2009/085913) (776 mg, 3.49 mmol) and KOH (399 mg, 7.10 mmol) in 1,4-dioxane (45 mL) was stirred at 85° C. for 16 hours. The reaction mixture was cooled to ambient temperature and concentrated in vacuo. The residue was partitioned between DCM and 0.5 M aqueous HCl and the layers separated. The organic phase was dried ($MgSO_4$), filtered and concentrated in vacuo. The residue was purified by column chromatography (silica, DCM/MeOH gradient as the eluent) to give 7-(difluoromethyl)-6-fluoro-3-(6-methylsulfanylpyrimidin-4-yl)pyrazolo[1,5-a]pyrimidin-2-amine as gold solid (500 mg, 44%); MS m/z: 327.1 $(M+H)^+$.

Step 2: 3-(6-Chloropyrimidin-4-yl)-5-(difluoromethyl)-6-fluoro-pyrazolo[1,5-a]pyrimidin-2-amine $SO_2Cl_2$ (608 mg, 365 μL, 4.51 mmol) was added to a suspension of 7-(difluoromethyl)-6-fluoro-3-(6-methylsulfanylpyrimidin-4-yl)pyrazolo[1,5-a]pyrimidin-2-amine (490 mg, 1.50 mmol) and concentrated HCl (142 μL, 1.65 mmol) in acetonitrile (20 mL) and the mixture was stirred at ambient temperature for 10 minutes. A further portion of $SO_2Cl_2$ (608 mg, 365 μL, 4.51 mmol) was added and the mixture was stirred for a further 5 minutes. The reaction was quenched by the addition of saturated aqueous $NaHCO_3$ and the acetonitrile was removed in vacuo. The precipitate was isolated by filtration, washed with water and dried in vacuo to give 3-(6-chloropyrimidin-4-yl)-5-(difluoromethyl)-6-fluoro-pyrazol[1,5-a]pyrimidin-2-amine as an off-white solid (405 mg, 86%); MS m/z: 315.1 $(M+H)^+$.

Step 3: 3-(6-Chloropyrimidin-4-yl)-5-(difluoromethyl)-6-fluoro-2-iodo-pyrazolo[1,5-a]pyrimidine 3-(6-Chloropyrimidin-4-yl)-5-(difluoromethyl)-6-fluoro-pyrazolo[1,5-a]pyrimidin-2-amine (300 mg, 0.953 mmol) was suspended in MeCN (12 mL) and p-toluenesulfonic acid hydrate (546 mg, 2.87 mmol) was added followed by the dropwise addition of a solution of KI (396 mg, 2.39 mmol) and sodium nitrite (132 mg, 1.91 mmol) in $H_2O$ (3 mL). The reaction was allowed to stir at ambient temperature for 16 hours. Further p-toluenesulfonic acid hydrate (546 mg, 2.87 mmol) and KI (396 mg, 2.39 mmol) in water (1 mL) was added and the mixture stirred at ambient temperature for 16 hours. The reaction was quenched by the addition of saturated aqueous $NaHCO_3$ and saturated aqueous $Na_2S_2O_3$ and the resultant precipitate was isolated by filtration to give 3-(6-chloropyrimidin-4-yl)-5-(difluoromethyl)-6-fluoro-2-iodo-pyrazolo[1,5-a]pyrimidine as a red solid (351 mg, 84% purity, 73%); MS m/z: 426.0 $(M+H)^+$.

Preparation 153: 5-(Difluoromethyl)-3-(2-fluoro-4-pyridyl)pyrazolo[1,5-a]pyrimidine

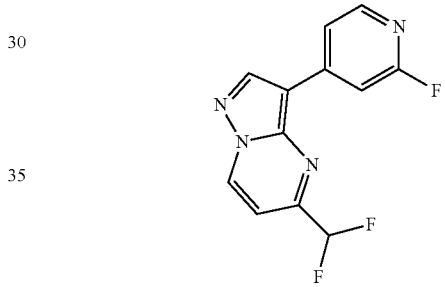

Step 1: 3-Bromo-5-(difluoromethyl)pyrazolo[1,5-a]pyrimidine

KOH (7.64 g, 136.2 mmol) was added to a solution of 3-(1,3-dioxolan-2-yl)-1,1-difluoro-propan-2-one (described in Tetrahedron, 63(30), 7246-7255, 2007) (27.4 g, 164.9 mmol) and 4-bromo-1H-pyrazol-5-amine (20.1 g, 123.8 mmol) in 1,4-dioxane (200 mL) and the mixture was stirred at 70° C. for 5.5 hours. The reaction mixture was cooled to ambient temperature and 2 M aqueous HCl (68.1 mL, 136.2 mmol) was added. The mixture was poured into water (800 mL) and aged for 30 minutes. The resultant precipitate was isolated by filtration and dried in vacuo. The solid was slurried in DCM and filtered through a pad of silica (1:1 EtOAc/Petroleum Ether elution). The solvent was removed in vacuo to give 3-bromo-5-(difluoromethyl)pyrazolo[1,5-a]pyrimidine as an orange solid (14.8 g, 48%); $^1$H NMR (400 MHz, DMSO-$d_6$) δ 9.38 (d, 1H), 8.54 (s, 1H), 7.36 (d, 1H), 7.08 (t, 1H); $^{19}$F NMR (376 MHz, DMSO-$d_6$) δ −117.0; MS m/z: 249.8 $(M+H)^+$.

Step 2: 5-(Difluoromethyl)-3-(2-fluoro-4-pyridyl)pyrazolo[1,5-a]pyrimidine

To a solution of 3-bromo-5-(difluoromethyl)pyrazolo[1,5-a]pyrimidine (400 mg, 1.61 mmol) in 1,4-dioxane (10 mL)

and water (3.3 mL) was added 2-fluoro-4-(4,4,5,5-tetramethyl-1,3,2-dioxaborolan-2-yl)pyridine (540 mg, 2.42 mmol), 2 M aqueous $Na_2CO_3$ (2.4 mL, 4.84 mmol) and $Pd(PPh_3)_4$ (93.2 mg, 0.08 mmol), and the reaction heated at 80° C. overnight. The reaction mixture was cooled to ambient temperature and diluted with EtOAc and water. The layers were separated and the aqueous layer extracted with EtOAc (×3). The combined organics were dried ($MgSO_4$), filtered and the solvent removed under reduced pressure. The crude mixture was purified by column chromatography (silica, petroleum ether/EtOAc gradient elution) to give 5-(difluoromethyl)-3-(2-fluoro-4-pyridyl)pyrazolo[1,5-a]pyrimidine as yellow solid (334 mg, 78%); $^1$H NMR (500 MHz, DMSO-$d_6$) δ 9.49 (d, 1H), 9.17 (s, 1H), 8.31 (d, 1H), 8.14 (ddd, 1H), 7.91 (s, 1H), 7.49 (d, 1H), 7.19 (t, 1H); $^{19}$F NMR (471 MHz, DMSO-d6) δ −68.69, −117.04, −117.16; MS m/z: 265.1 $(M+H)^+$.

Preparation 154: 3-Iodo-5-(trifluoromethyl)pyrazolo[1,5-a]pyrimidine

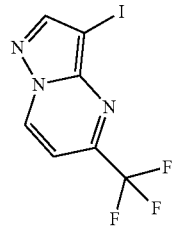 [SMILES: FC(F)(F)c1ccn2ncc(I)c2n1]

Step 1: 5-(Trifluoromethyl)pyrazolo[1,5-a]pyrimidine

To a solution of 3-(1,3-dioxolan-2-yl)-1,1,1-trifluoro-propan-2-one (described in WO2014/143242 and Journal of Fluorine Chemistry, 126, (2005), 543-550) (1.2 g, 6.52 mmol) and 4H-pyrazol-3-amine (500 mg, 6.02 mmol) in 1,4-dioxane (3 mL) was added KOH (35 mg, 0.624 mmol). The reaction mixture was stirred at ambient temperature for 2 hours then at 90° C. for 18 hours. The reaction was cooled to ambient temperature and the solvent removed in vacuo. The residue was purified by column chromatography (silica, petroleum ether/EtOAc gradient elution) to give 5-(trifluoromethyl)pyrazolo[1,5-a]pyrimidine as a white solid (246 mg, 22%); $^1$H NMR (500 MHz, DMSO-$d_6$) δ 9.47 (d, 1H), 8.48 (d, 1H), 7.48 (d, 1H), 7.05 (dd, 1H); $^{19}$F NMR (471 MHz, DMSO-$d_6$) δ −67.09.

Step 2: 3-Iodo-5-(trifluoromethyl)pyrazolo[1,5-a]pyrimidine

To a stirred solution of 5-(trifluoromethyl)pyrazolo[1,5-a]pyrimidine (246 mg, 1.32 mmol) in DCM (4 mL) and pyridine (2 mL) at 0° C. was added dropwise 1 M iodine monochloride in DCM (3.3 mL, 3.3 mmol). The reaction mixture was heated at 50° C. in a sealed tube for 3 days then cooled to ambient temperature. A further portion of 1 M iodine monochloride in DCM (1.5 mL, 1.5 mmol) was added and the reaction mixture heated at 50° C. in a sealed tube for a further 2 days. The reaction was cooled to ambient temperature and diluted with DCM. The mixture was washed with saturated aqueous sodium thiosulfate (×2) and brine, dried ($MgSO_4$), filtered and concentrated in vacuo.

The residue was purified by column chromatography (silica, petroleum ether/EtOAc gradient elution) to give 3-iodo-5-(trifluoromethyl)pyrazolo[1,5-a]pyrimidine as a yellow solid (249 mg, 60%); $^1$H NMR (500 MHz, DMSO-$d_6$) δ 9.50 (d, 1H), 8.58 (s, 1H), 7.53 (d, 1H); $^{19}$F NMR (471 MHz, DMSO-$d_6$) δ −67.03.

Preparation 155: (S)—N-((6,6-dimethylmorpholin-2-yl)methyl)methanesulfonamide

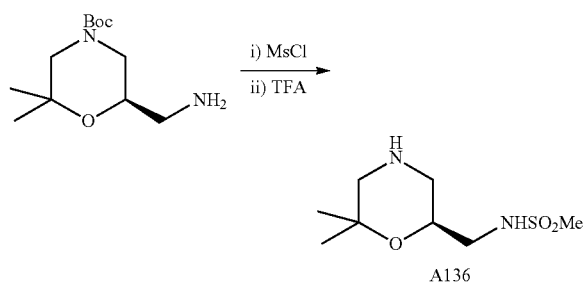

A136

Using the same method as above for A10, (4-oxa-7-azaspiro[2.5]octan-5-yl)methanol A136 was prepared using tert-butyl (6R)-6-(aminomethyl)-2,2-dimethylmorpholine-4-carboxylate in place of tert-butyl (6S)-6-(aminomethyl)-2,2-dimethylmorpholine-4-carboxylate.

Preparation 156: 3-(6-Chloropyrimidin-4-yl)-6-(1,1-difluoroethyl)imidazo[1,2-b]pyridazine

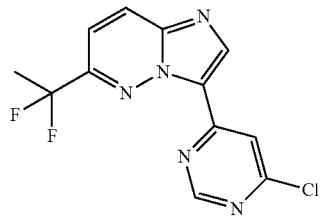 [SMILES: CC(F)(F)c1ccc2ncc(-c3cc(Cl)ncn3)n2n1]

Step 1: 1-(3-(6-(Methylthio)pyrimidin-4-yl)imidazo[1,2-b]pyridazin-6-yl)ethan-1-one 1-(3-(6-(Methylthio)pyrimidin-4-yl)imidazo[1,2-b]pyridazin-6-yl)ethan-1-one was prepared from 1-(6-aminopyridazin-3-yl)ethan-1-one using a procedure similar to Preparation 131.

Step 2: 6-(1,1-Difluoroethyl)-3-(6-(methylthio)pyrimidin-4-yl)imidazo[1,2-b]pyridazine To a suspension of 1-(3-(6-(methylthio)pyrimidin-4-yl)imidazo[1,2-b]pyridazin-6-yl)ethan-1-one (50 mg, 0.18 mmol) in DCM (2 mL) was added DAST (282 mg, 1.75 mmol). The reaction mixture was stirred at ambient temperature for 4 hours before further DAST (282 mg, 1.75 mmol) was added. DAST (282 mg, 1.75 mmol) was added at 24-hour intervals for 3 days, then again (282 mg, 1.75 mmol) after a further 3 days and a final portion (282 mg, 1.75 mmol) after a further 14 days. The reaction mixture was then poured slowly onto saturated aqueous $NaHCO_3$, the layers separated and the organic layer dried (MgSO$_4$) and concentrated in vacuo. The material was used in next step without further purification.

Step 3: 3-(6-Chloropyrimidin-4-yl)-6-(1,1-difluoro-ethyl)imidazo[1,2-b]pyridazine 3-(6-Chloropyrimidin-4-yl)-6-(1,1-difluoroethyl)imidazo[1,2-b]pyridazine was prepared using a procedure similar to Preparation 132.

Preparation 157: 2-(1H-Pyrazol-4-yl)morpholine

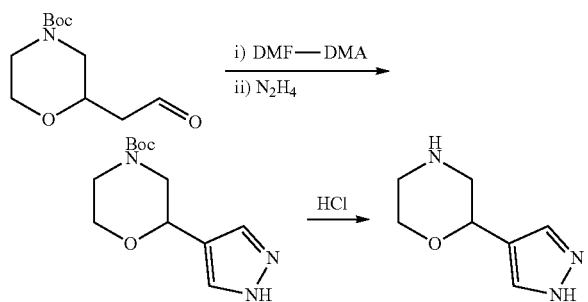

A mixture of tert-butyl 2-(2-oxoethyl)morpholine-4-carboxylate (5.77 g, 25 mmol) and DMF-DMA (6.7 mL, 50 mmol) in DMF (50 mL) was stirred at 80° C. for 17 hours. The reaction mixture was cooled to ambient temperature and the solvent removed in vacuo. The residue was taken up in EtOH (100 mL) and hydrazine hydrate (1.3 mL, 26.5 mmol) was added with stirring at ambient temperature. After 3 hours, the solvent was removed in vacuo and the residue purified by chromatography (silica, petroleum ether/EtOAc gradient elution), to give tert-butyl 2-(1H-pyrazol-4-yl)morpholine-4-carboxylate (2.35 g, 37%) as a yellow solid; $^1$H NMR (500 MHz, Chloroform-d) δ 7.63 (s, 2H), 4.52 (dd, 1H), 4.12 (br s, 1H), 3.97-3.90 (m, 2H), 3.68 (td, 1H), 3.05 (d, 2H), 1.51 (s, 9H); MS m/z: 254.1 (M+H)$^+$.

3 M HCl in MeOH (45 mL, 135 mmol) was added to a stirred solution of tert-butyl 2-(1H-pyrazol-4-yl)morpholine-4-carboxylate (2.35 g, 9.3 mmol) in DCM (75 mL) and the reaction heated at reflux for 5 hours. The reaction was cooled to ambient temperature and the solvent removed in vacuo. The residue was dissolved in the minimum amount of DCM/MeOH and loaded on to an ion-exchange cartridge. The cartridge was washed with MeOH/DCM mixtures, which were discarded. The product was eluted by washing with 2 M NH$_3$ in MeOH/DCM. Solvent was removed in vacuo to give 2-(1H-pyrazol-4-yl)morpholine (1.27 g, 89%) as an orange solid, which was taken on to the next reaction without further purification; $^1$H NMR (500 MHz, Chloroform-d) δ 7.60 (s, 2H), 4.56 (dd, 1H), 3.98 (ddd, 1H), 3.77 (td, 1H), 3.11 (dd, 1H), 3.00 (td, 1H), 2.93-2.88 (m, 2H); MS m/z: 154.2 [M+H]$^+$.

Preparation 158: 2-Methyl-6-(1H-pyrazol-4-yl)morpholine

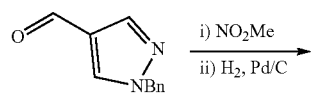

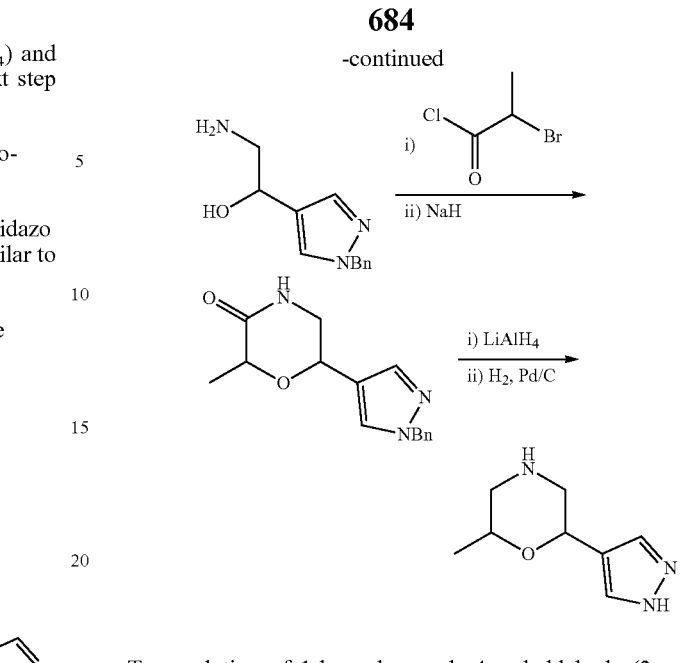

To a solution of 1-benzylpyrazole-4-carbaldehyde (2 g, 10.7 mmol) and nitromethane (7 mL, 129 mmol) cooled in an ice bath, was added Et$_3$N (150 μL, 1.1 mmol). The mixture was stirred with cooling for 15 minutes, then at ambient temperature for 18 hours. The reaction mixture was concentrated in vacuo and the residue purified by chromatography (silica, petroleum ether/EtOAc gradient elution). The relevant fractions were combined and concentrated in vacuo to give a colourless oil (1 g, 37%); MS m/z: 248 (M+H)$^+$, taken directly on to next reaction.

A mixture of 1-(1-benzylpyrazol-4-yl)-2-nitro-ethanol (100 mg, 0.4 mmol), Pd on C, wet, Degussa (20 mg, 0.2 mmol) in methanol (4 mL) was stirred at ambient temperature for 18 hours under H$_2$ at 1 atmosphere. The reaction mixture was filtered and the filtrate concentrated in vacuo to give a colourless gum (90 mg), MS m/z: 218 (M+H)$^+$, which was taken directly on to next reaction. 2-Bromopropanoyl bromide (114 mg, 0.5 mmol) was added to an ice-cold solution of 2-amino-1-(1-benzylpyrazol-4-yl)ethanol (100 mg, 0.5 mmol) and Et$_3$N (83 μL, 0.6 mmol) in DCM (4 mL) under N$_2$. The reaction mixture was stirred at ambient temperature for 1 hour. The reaction mixture was diluted with DCM, washed with a 2 M aqueous HCl solution, a saturated aqueous NaHCO$_3$ solution and brine. The organic phase was dried over sodium sulfate, filtered and concentrated in vacuo to give a colourless oil. This material was taken up in THF (3 mL) and the solution cooled in an ice bath. Sodium hydride (37 mg of a 60% dispersion in mineral oil, 0.9 mmol) was added and the resulting suspension was stirred at ambient temperature for 2 hours. The reaction was quenched with MeOH then diluted with EtOAc, washed with a saturated aqueous sodium bicarbonate solution and brine. The organic phase was dried over MgSO$_4$, filtered and concentrated in vacuo to give a pale yellow gum (100 mg), MS m/z: 272 (M+H)$^+$, that was taken directly on to next reaction without purification.

A mixture of 6-(1-benzylpyrazol-4-yl)-2-methyl-morpholin-3-one (100 mg, 0.4 mmol) and LiAlH$_4$ (184 μL of 2 M, 0.4 mmol) in THF (3 mL) was stirred at 60° C. for 1 hour. The resulting suspension was quenched with Na$_2$SO$_4$.10H$_2$O pellets and stirred for 30 minutes, then filtered. The filtrate was concentrated in vacuo and the residue taken up in MeOH (2 mL). Three drops of concentrated HCl and Pd on C, wet, Degussa (20 mg, 0.02 mmol) were added to the solution. The reaction mixture was stirred at ambient temperature under $H_2$ at 1 atmosphere pressure for 18 hours. The reaction mixture was poured onto an ion-exchange cartridge and eluted with methanol (filtrate discarded), then a 2 M methanolic $NH_3$ solution. The filtrate was concentrated in vacuo to give 2-methyl-6-(1H-pyrazol-4-yl)morpholine (23 mg), which was taken directly on to the next reaction; MS m/z: 168 (M+H)$^+$.

Preparation 159: Imino(methyl)(piperidin-3-ylmethyl)-$\lambda^6$-sulfanone

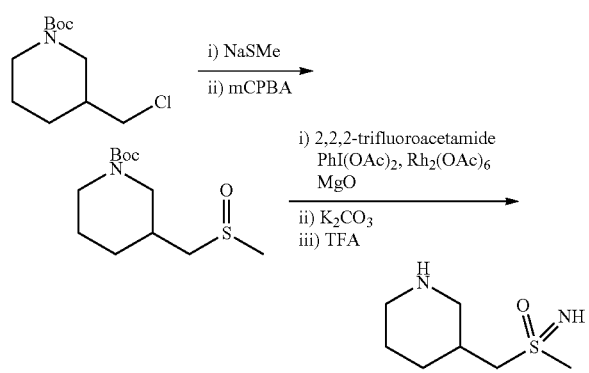

A mixture of tert-butyl 3-(chloromethyl)piperidine-1-carboxylate (500 mg, 2.14 mmol), NaSMe (3 mL of 20% w/v, 8.56 mmol), KI (355 mg, 2.14 mmol) in ethanol (10 mL) was stirred at 80° C. for 22 hours. The reaction mixture was cooled to ambient temperature, then concentrated in vacuo. The residue was partitioned between EtOAc and saturated aqueous sodium bicarbonate solution. The organic phase was washed with brine, dried (MgSO$_4$), filtered and concentrated in vacuo to give the product as a pale brown oil (460 mg, 88%), that was taken on to the next step without further purification or characterisation.

m-CPBA (324 mg, 1.88 mmol) was added to an ice cold solution of tert-butyl 3-(methylsulfanylmethyl)piperidine-1-carboxylate (460 mg, 1.88 mmol) in DCM (7 mL) under $N_2$. The reaction mixture was stirred for 20 hours, with the temperature rising to ambient. The reaction mixture was diluted with DCM, washed with saturated aqueous sodium bicarbonate solution and brine. The organic phase was dried over MgSO$_4$, filtered and concentrated in vacuo to give a pale brown oil (460 mg), MS m/z: 262 (M+H)$^+$, that was used in the next step without further purification or characterisation. tert-Butyl 3-(methylsulfinylmethyl)piperidine-1-carboxylate (5.5 g, 21.0 mmol), 2,2,2-trifluoroacetamide (5.2 g, 46.3 mmol), diacetoxyiodobenzene (10.2 g, 31.6 mmol) and MgO (3.39 g, 84.2 mmol) were combined in DCM (250 mL) under $N_2$. Rh$_2$(OAc)$_6$ (0.9 g, 2.0 mmol) was added and the reaction mixture mixture stirred at ambient temperature overnight. The mixture was filtered through Celite, washing with MeOH and DCM. The filtrate was concentrated in vacuo and the residue taken up in MeOH (5 mL) and MeCN/water (3:1) (5 mL). K$_2$CO$_3$ (17.4 g, 126.0 mmol) was added and the mixture stirred at 90° C. for 2 hours. The mixture was diluted with EtOAc and washed with saturated aqueous sodium bicarbonate solution and brine. The organic phase was dried (Na$_2$SO$_4$), filtered and concentrated in vacuo to give tert-butyl 3-[(methylsulfonimidoyl)methyl]piperidine-1-carboxylate (5.96 g, quantitative yield) as an amber oil, MS m/z: 277 (M+H)$^+$, that was taken directly on to the next reaction.

tert-Butyl 3-[(methylsulfonimidoyl)methyl]piperidine-1-carboxylate (600 mg, 2.17 mmol) in DCM (3 mL) was treated with TFA (1.7 mL, 21.7 mmol). The mixture was stirred at room temperature overnight. The reaction mixture was concentrated in vacuo. The residue was taken up in MeOH and loaded on to an ion-exchange cartridge. The cartridge was eluted MeOH/DCM (filtrate discarded) then with methanolic ammonia. The filtrate was concentrated in vacuo to give imino(methyl)(piperidin-3-ylmethyl)-$\lambda^6$-sulfanone (250 mg, 65%); $^1$H NMR (500 MHz, Methanol-d$_4$) δ 3.34-3.24 (m, 1H), 3.19-3.10 (m, 2H), 3.10-3.07 (m, 3H), 3.05-2.97 (m, 1H), 2.60 (ddd, 1H), 2.52-2.43 (m, 1H), 2.30-2.18 (m, 1H), 2.08 (ddtd, 1H), 1.75 (dq, 1H), 1.61 (dtq, 1H), 1.37 (dtd, 1H).

Preparation 160: 2-(1H-Pyrazol-4-yl)piperazine

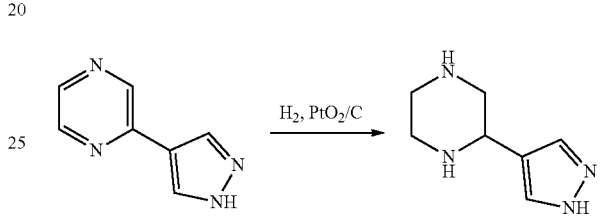

A mixture of 2-(1H-pyrazol-4-yl)pyrazine (400 mg, 2.7 mmol), PtO$_2$ (100 mg, 0.4 mmol) in MeOH (15 mL) was shaken at ambient temperature under a 60 psi H$_2$ pressure for 18 hours. The reaction mixture was filtered and the filtrate concentrated in vacuo to give 2-(1H-pyrazol-4-yl)piperazine as a colourless oil, which was taken directly on to the next reaction without purification; [MS m/z: 153 (M+H)$^+$].

Preparation 161: 2-Methyl-3-(1H-pyrazol-4-yl)piperazine

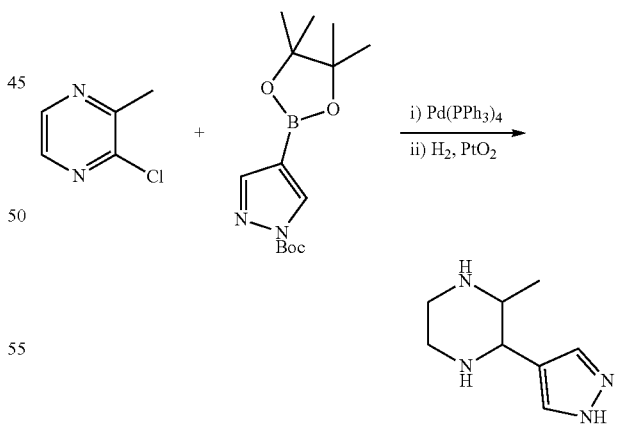

To a suspension of 2-chloro-3-methyl-pyrazine (500 mg, 3.89 mmol) in 1,4-dioxane (10 mL) was added tert-butyl 4-(4,4,5,5-tetramethyl-1,3,2-dioxaborolan-2-yl)pyrazole-1-carboxylate (1.26 g, 4.28 mmol), tetrakis(triphenylphosphine)palladium(0) (225 mg, 0.19 mmol) and Na$_2$CO$_3$ (5.8 mL of a 2 M aqueous solution, 11.7 mmol). The reaction mixture was stirred in a sealed tube at 130° C. for 3 hours, then cooled and filtered through a pad of Celite. The filtrate was concentrated in vacuo to give 2-methyl-3-(1H-pyrazol-4-yl)pyrazine (750 mg, 94%) as a white solid; MS m/z: 161 (M+H)+.

A mixture of 2-methyl-3-(1H-pyrazol-4-yl)pyrazine (585 mg, 3.65 mmol), PtO$_2$ (84 mg, 0.37 mmol) and concentrated HCl (2 mL, 55 mmol) in methanol (60 mL) was shaken at ambient temperature in a Parr hydrogenator under a pressure of 60 psi H$_2$ for 6 hours. The reaction mixture was filtered and the filtrate concentrated in vacuo. The residue was dissolved in methanol and loaded onto an ion-exchange cartridge. The cartridge was washed with methanol (filtrate discarded), then with methanolic ammonia. The filtrate was concentrated under reduced pressure to give 2-methyl-3-(1H-pyrazol-4-yl)piperazine (600 mg, 99%) as a brown solid; MS m/z: 167 (M+H)+. This material was taken on to the next reaction without further purification.

The following amines were made using methodology similar to Preparation 161:

3-(Difluoromethoxy)-5-(1H-pyrazol-4-yl)piperidine;

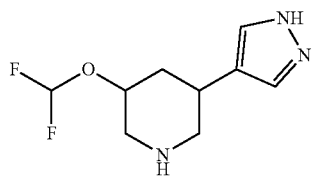 [SMILES: FC(F)OC1CNCC(c2cn[nH]c2)C1]

3-Methoxy-5-(1H-pyrazol-4-yl)piperidine;

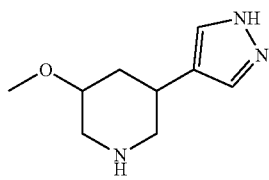

3-(2H-1,2,3-Triazol-4-yl)piperidine;

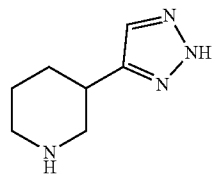 [SMILES: c1n[nH]nc1C1CCCNC1]

2-Methyl-5-(1H-pyrazol-4-yl)piperazine;

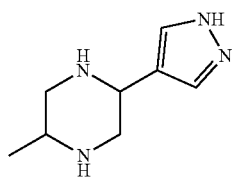

2-Methyl-6-(1H-pyrazol-4-yl)piperazine;

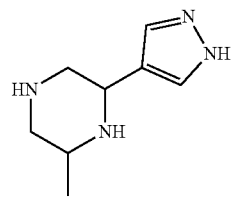

5-Isopropyl-2-methyl-3-(1H-pyrazol-4-yl)piperazine;

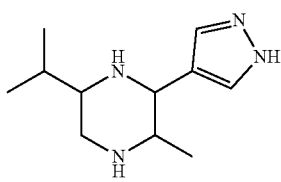

2,3,5-Trimethyl-6-(1H-pyrazol-4-yl)piperazine;

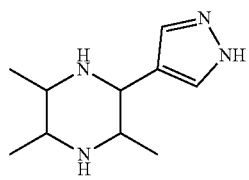

2,5-Dimethyl-3-(1H-pyrazol-4-yl)piperidine;

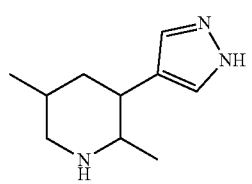

2-Methyl-3-(1H-pyrazol-4-yl)piperidine;

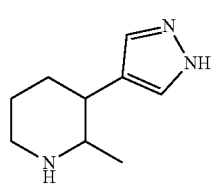

3-(1H-Imidazol-4-yl)-2-methylpiperidine;

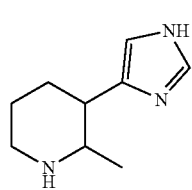

(5-(1H-Pyrazol-4-yl)piperidin-3-yl)methanol;

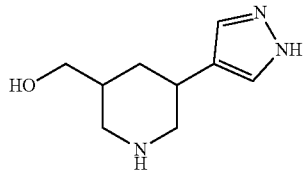 [SMILES: OCC1CNCC(c2cn[nH]c2)C1]

3-(1H-Imidazol-4-yl)-2-methylpiperidine;

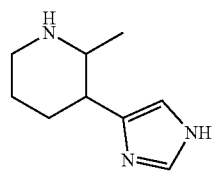

3-(3-Methyl-1H-pyrazol-4-yl)piperidine;

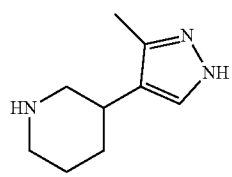

2-Methyl-6-(3-methyl-1H-pyrazol-4-yl)piperazine;

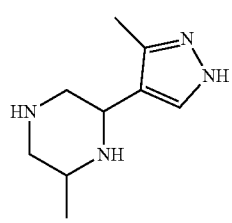

2-Methyl-6-(3-(trifluoromethyl)-1H-pyrazol-4-yl)piperazine;

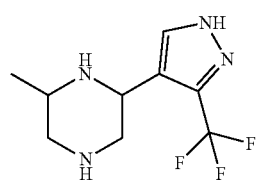 [SMILES: CC1CNCC(c2c[nH]nc2C(F)(F)F)N1]

2,5-Dimethyl-3-(5-methyl-1H-pyrazol-4-yl)piperazine;

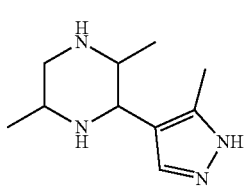

2-(1H-Imidazol-4-yl)piperazine;

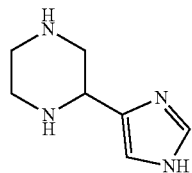 [SMILES: c1nc(C2CNCCN2)c[nH]1]

3-(1H-Imidazol-4-yl)-2,5-dimethylpiperazine;

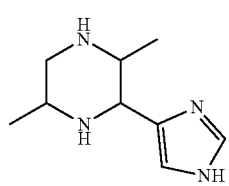

2-(3,5-Dimethyl-1H-pyrazol-4-yl)-6-methylpiperazine;

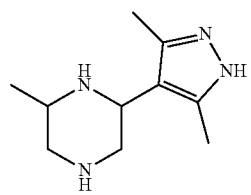

3-(3,5-Dimethyl-1H-pyrazol-4-yl)piperidine;

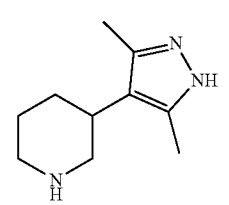

2-(1H-Pyrazol-4-yl)-6-(trifluoromethyl)piperazine;

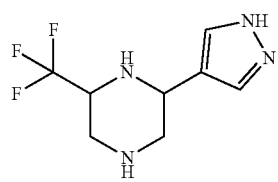 [SMILES: FC(F)(F)C1CNCC(c2cn[nH]c2)N1]

2,5-Dimethyl-3-(2-(trifluoromethyl)-1H-imidazol-4-yl)piperazine;

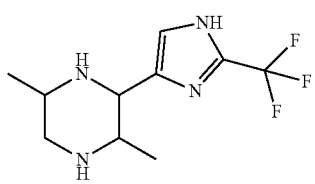 [SMILES: CC1CNC(C)C(c2c[nH]c(C(F)(F)F)n2)N1]

691

2-Methyl-6-(1-methyl-1H-pyrazol-5-yl)piperazine;

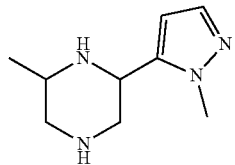

2-Methyl-6-(1-methyl-1H-imidazol-5-yl)piperazine;

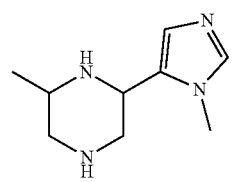

5-(3,6-Dimethylpiperazin-2-yl)pyridin-2(1H)-one;

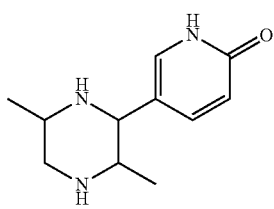

3-(Azetidin-1-ylmethyl)-5-(1H-pyrazol-4-yl)piperidine;

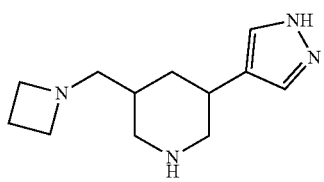 [SMILES: c1n[nH]cc1C1CNCC(CN2CCC2)C1]

2-(5-(1H-Pyrazol-4-yl)piperidin-3-yl)propan-2-ol;

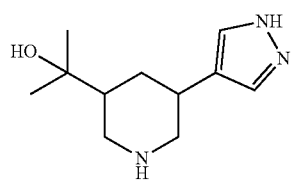

2,5-Dimethyl-3-(1-methyl-1H-pyrazol-4-yl)piperazine;

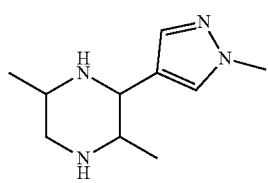

692

2,5-Dimethyl-3-(1H-pyrazol-4-yl)piperazine.

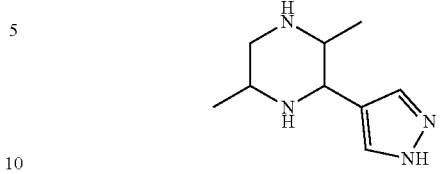

Preparation 162:
6-(1H-Pyrazol-4-yl)piperazin-2-one

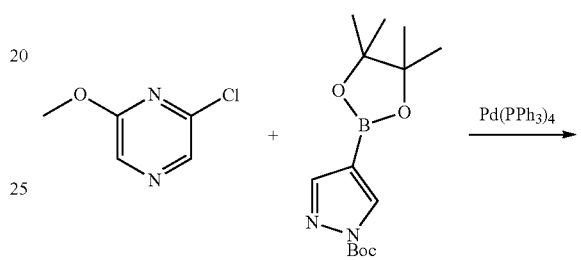

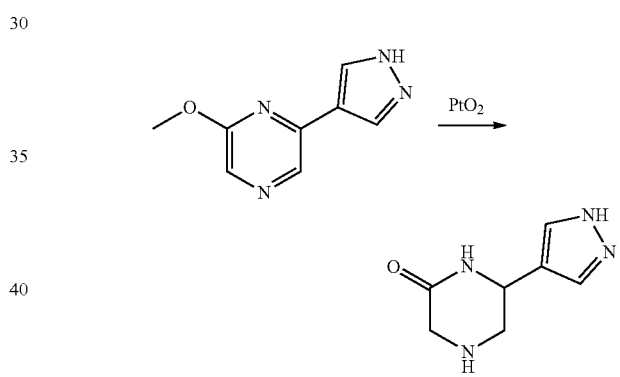

Step 1: 2-Methoxy-6-(1H-pyrazol-4-yl)pyrazine

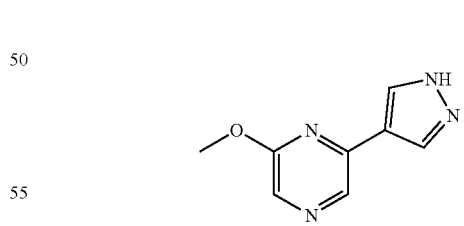

To a suspension of 2-chloro-6-methoxy-pyrazine (500 mg, 3.46 mmol) in 1,4-dioxane (10 mL) was added tetrakis(triphenylphosphine)palladium(0) (220 mg, 0.19 mmol), tert-butyl 4-(4,4,5,5-tetramethyl-1,3,2-dioxaborolan-2-yl)pyrazole-1-carboxylate (1.10 g, 3.70 mmol) and 2 M Na$_2$CO$_3$ (6 mL, 12 mmol). The reaction was stirred in a sealed tube at 100° C. for 2 hours before being filtered and concentrated in vacuo to give 2-methoxy-6-(1H-pyrazol-4-yl)pyrazine (800 mg, 72%); MS m/z: 177.1 (M+H)$^+$.

Step 2: 6-(1H-Pyrazol-4-yl)piperazin-2-one

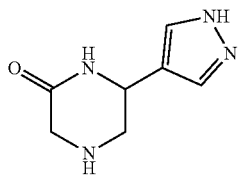 [SMILES: O=C1CNCC(c2cn[nH]c2)N1]

A mixture of 2-methoxy-6-(1H-pyrazol-4-yl)pyrazine (610 mg, 3.462 mmol), PtO$_2$ (120 mg, 0.528 mmol), HCl (3 M in methanol, 2.20 mL, 6.60 mmol) in methanol (40 mL) was shaken in the Parr hydrogenator at 60 psi pressure of H$_2$. The catalyst was filtered off and the filtrate concentrated to afford 6-(1H-pyrazol-4-yl)piperazin-2-one (450 mg, 78%); MS m/z: 167.0 (M+H)$^+$.

Preparation 163: ((5-(1H-Pyrazol-4-yl)piperidin-3-yl)imino)dimethyl-λ$^6$-sulfanone

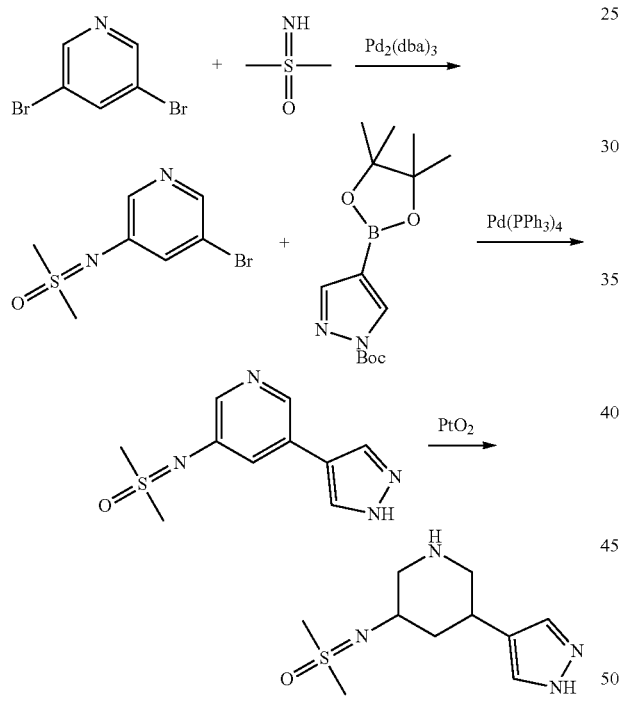

Step 1: ((5-Bromopyridin-3-yl)imino)dimethyl-λ$^6$-sulfanone

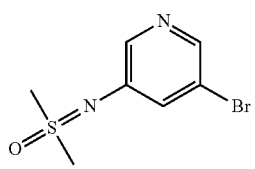

3,5-Dibromopyridine (3.0 g, 12.7 mmol), imino-dimethyl-oxo-λ$^6$-sulfane (800 mg, 8.59 mmol), Xantphos (470 mg, 0.81 mmol) and cesium carbonate (4.0 g, 10.0 mmol) were mixed in 1,4-dioxane (10 mL). The reaction mixture was degassed and treated with tris(benzylideneacetone)dipalladium(0) (370 mg, 0.40 mmol) and the mixture was stirred at 100° C. overnight. The reaction was cooled and filtered, and the solid washed with EtOAc. The combined washings were concentrated in vacuo and purified by column chromatography (40 g SiO$_2$, eluting with 0 to 100% ethyl acetate in petroleum ether gradient) to give ((5-bromopyridin-3-yl)imino)dimethyl-λ$^6$-sulfanone (1.8 g, 84%) as a brown oil; MS m/z: 251.1 (M+H)$^+$.

Step 2: ((5-(1H-Pyrazol-4-yl)pyridin-3-yl)imino)dimethyl-λ$^6$-sulfanone

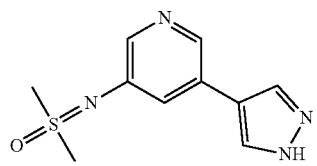 [SMILES: CS(C)(=O)=Nc1cncc(-c2cn[nH]c2)c1]

A mixture of ((5-bromopyridin-3-yl)imino)dimethyl-λ$^6$-sulfanone (770 mg, 3.09 mmol), tetrakis(triphenylphosphine)palladium(0) (200 mg, 0.17 mmol), 2 M Na$_2$CO$_3$ (3.50 mL, 7.0 mmol) and tert-butyl 4-(4,4,5,5-tetramethyl-1,3,2-dioxaborolan-2-yl)pyrazole-1-carboxylate (1.6 g, 5.4 mmol) in dioxane (15 mL) was stirred at 130° C. for 90 min. The reaction mixture was diluted with EtOAc, and washed with saturated aq. sodium bicarbonate and brine. The organic layer was dried (MgSO$_4$) and concentrated in vacuo. Purification by column chromatography (40 g SiO$_2$, eluting with a 90:10:1 petroleum ether/EtOAc/NH$_3$ in MeOH mixture) provided ((5-(1H-pyrazol-4-yl)pyridin-3-yl)imino)dimethyl-λ$^6$-sulfanone (100 mg, 14%) as a white solid; MS m/z: 237.2 (M+H)$^+$.

Step 3: ((5-(1H-Pyrazol-4-yl)piperidin-3-yl)imino)dimethyl-λ$^6$-sulfanone

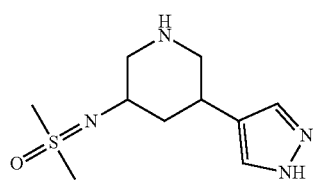 [SMILES: CS(C)(=O)=NC1CNCC(c2cn[nH]c2)C1]

A mixture of ((5-(1H-pyrazol-4-yl)pyridin-3-yl)imino)dimethyl-λ$^6$-sulfanone (100 mg, 0.42 mmol), PtO$_2$ (50 mg, 0.22 mmol), 3 M HCl in methanol (15.0 mL, 45.0 mmol) was shaken in the Parr hydrogenator under 60 psi pressure of H$_2$. After 18 hours, a further portion of PtO$_2$ (50 mg, 0.22 mmol) was added and the reaction was stirred for a further 24 hours under 60 psi pressure of H$_2$. The reaction mixture was filtered to give ((5-(1H-pyrazol-4-yl)piperidin-3-yl)imino)dimethyl-λ$^6$-sulfanone (100 mg, 97%) which was used without further purification; MS m/z: 243.0 (M+H)$^+$.

The following compounds were made using methodology similar to that described in Preparation 163:
(5-(1H-Pyrazol-4-yl)piperidin-3-yl)dimethylphosphine oxide;

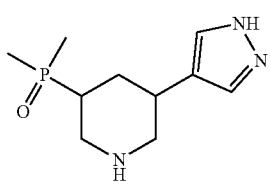

Dimethyl(6-methyl-5-(1H-pyrazol-4-yl)piperidin-3-yl)
phosphine oxide.

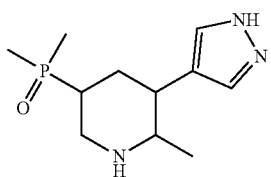 [SMILES: CC1NCC(P(C)(C)=O)CC1c1cn[nH]c1]

Preparation 164: tert-Butyl 5-(isothiazol-4-yl)-3,6-dihydropyridine-1 (2H)-carboxylate

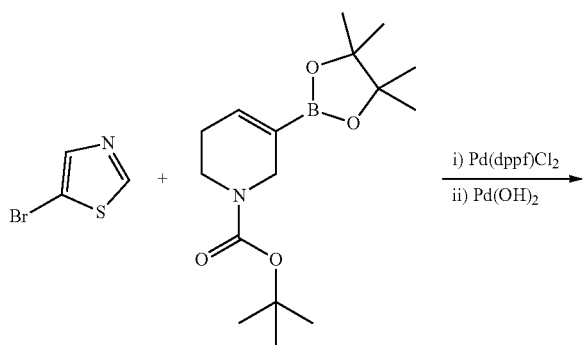

Step 1: tert-Butyl 5-(isothiazol-4-yl)-3,6-dihydropyridine-1 (2H)-carboxylate

4-Bromoisothiazole (668 mg, 4.08 mmol) and tert-butyl 5-(4,4,5,5-tetramethyl-1,3,2-dioxaborolan-2-yl)-3,6-dihydro-2H-pyridine-1-carboxylate (1.05 g, 3.40 mmol) were mixed in 1,4-dioxane (20 mL) and tetrakis(triphenylphosphine)palladium(0) (196 mg, 0.17 mmol) and $Na_2CO_3$ (5 mL of 2 M, 10 mmol) were added. The reaction mixture was degassed and purged with nitrogen and heated at 130° C. for 2 hours. The reaction was cooled and diluted with EtOAc and water, and the aqueous layer extracted 3 times with EtOAc. The combined organics were passed through a phase separator cartridge and concentrated in vacuo. Purification by column chromatography (24 g $SiO_2$, eluting with 0-100% EtOAc in petroleum ether gradient) gave tert-butyl 5-(isothiazol-4-yl)-3,6-dihydropyridine-1(2H)-carboxylate (741 mg, 80%) as a yellow oil; $^1$H NMR (500 MHz, DMSO-$d_6$) δ 8.92 (s, 1H), 8.83 (s, 1H), 6.50 (tt, J=4.1, 1.9 Hz, 1H), 4.20-15 (m, 2H), 3.47 (t, J=5.7 Hz, 2H), 2.29-2.21 (m, 2H), 1.43 (s, 9H); MS m/z: 267.0 (M+H)$^+$.

Step 2: 4-(1,2,5,6-Tetrahydropyridin-3-yl)isothiazole

tert-Butyl 5-(isothiazol-4-yl)-3,6-dihydropyridine-1(2H)-carboxylate (499 mg, 1.87 mmol) was dissolved in DCM (2.8 mL) and TFA (1.5 mL, 19.5 mmol) was added and the reaction stirred at ambient temperature overnight. The mixture was passed through an SCX-2 cartridge, rinsing with MeOH and eluting the product with methanolic ammonia. The ammonia extracts were concentrated in vacuo to give 4-(1,2,3,6-tetrahydropyridin-5-yl)isothiazole (288 mg, 92%) as a brown oil which was used without further purification; $^1$H NMR (500 MHz, DMSO-$d_6$) δ 8.78 (d, J=13.3 Hz, 2H), 6.40 (tt, J=4.0, 1.8 Hz, 1H), 3.50 (td, J=2.7, 1.7 Hz, 2H), 2.80 (t, J=5.6 Hz, 2H), 2.13 (ddq, J=6.9, 5.6, 2.8 Hz, 2H); MS m/z: 167.0 (M+H).

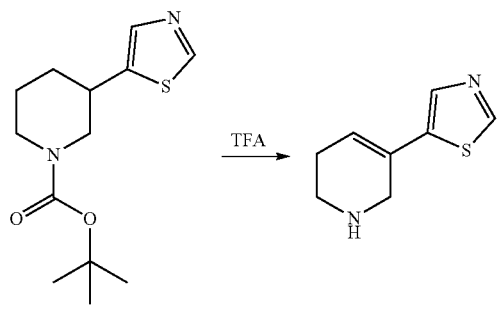

The following compounds were made using methodology similar to that described in Preparation 164:
4-(1,2,5,6-Tetrahydropyridin-3-yl)-1H-pyrazole-3-carbonitrile;

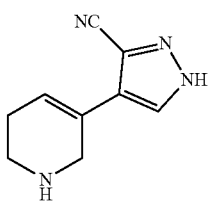 [SMILES: N#Cc1n[nH]cc1C1=CCCNC1]

5-(3-Fluoro-1H-pyrazol-4-yl)-1,2,3,6-tetrahydropyridine;

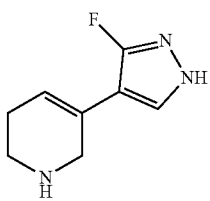 [SMILES: Fc1n[nH]cc1C1=CCCNC1]

5-(2-Isopropyl-1H-imidazol-4-yl)-1,2,3,6-tetrahydropyridine;

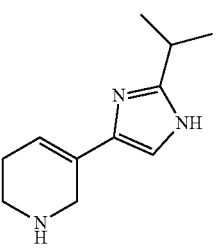

5-(3-Methyl-1H-pyrazol-4-yl)-1,2,3,6-tetrahydropyridine;

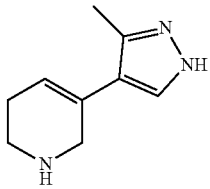

5-(2-Methyl-1H-imidazol-4-yl)-1,2,3,6-tetrahydropyridine.

Preparation 165: 5-(Piperidin-3-yl)thiazole

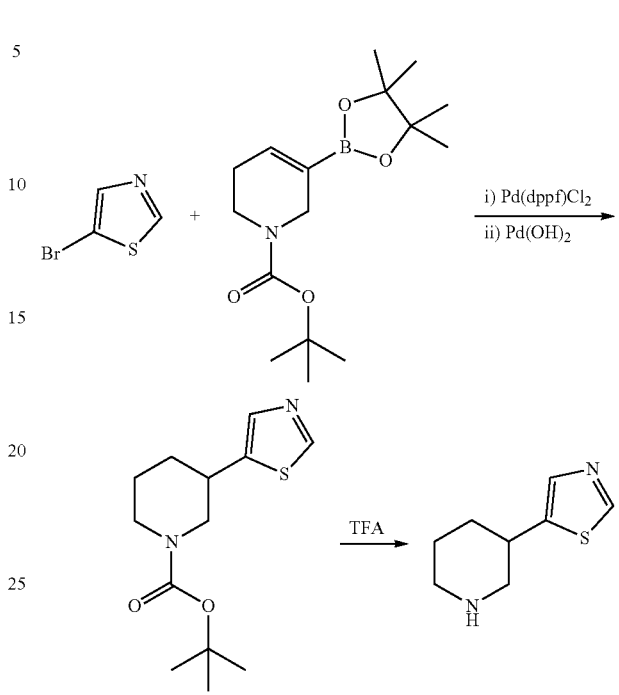

Step 1: tert-Butyl 5-(thiazol-5-yl)-3,6-dihydropyridine-(2H)-carboxylate

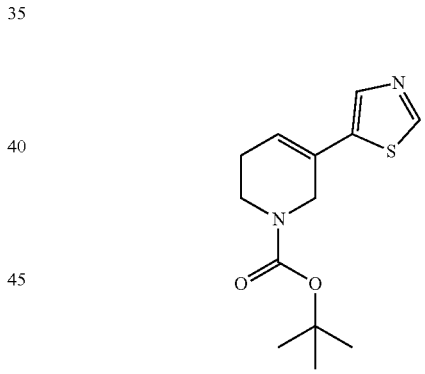

5-Bromothiazole (520 mg, 3.17 mmol), tert-butyl 5-(4,4,5,5-tetramethyl-1,3,2-dioxaborolan-2-yl)-3,6-dihydro-2H-pyridine-1-carboxylate (1.08 g, 3.49 mmol), (dppf)PdCl$_2$.DCM (259 mg, 0.31 mmol) and 2 M Na$_2$CO$_3$ (3.96 mL, 7.93 mmol) were mixed in 1,4-dioxane (18.3 mL). The mixture was degassed and stirred at 85° C. for 3 hours before being diluted in EtOAc. The layers were separated and the organic layer washed with brine, dried (MgSO$_4$) and concentrated in vacuo. Purification by column chromatography (40 g, SiO$_2$, eluting with a gradient of 0-80% EtOAc in petroleum ether) gave tert-butyl 5-(thiazol-5-yl)-3,6-dihydropyridine-1(2H)-carboxylate; $^1$H NMR (500 MHz, DMSO-d$_6$) δ 8.64 (s, 1H), 7.75 (s, 1H), 6.24 (s, 1H), 4.27 (s, 2H), 3.56 (s, 2H), 2.32 (s, 2H), 1.50 (s, 9H); MS m/z: 267.2 (M+H).

Step 2: tert-Butyl 3-(thiazol-5-yl)piperidine-1-carboxylate

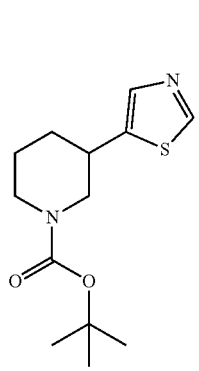 [SMILES: CC(C)(C)OC(=O)N1CCCC(c2cncs2)C1]

Methanol (8.6 mL) was added to tert-butyl 5-(thiazol-5-yl)-3,6-dihydropyridine-1(2H)-carboxylate (230 mg, 0.86 mmol), followed by Pd(OH)$_2$ (60.6 mg, 0.086 mmol). The mixture was degassed and stirred under a balloon of H$_2$ for 3 days before being filtered through Celite. The filtrate was evaporated in vacuo to give tert-butyl 3-(thiazol-5-yl)piperidine-1-carboxylate (230 mg, 100%) which was used without further purification; MS m/z: 269.2 (M+H).

Step 3: 5-(Piperidin-3-yl)thiazole

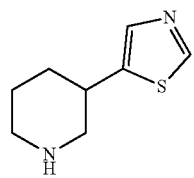 [SMILES: c1ncc(C2CCCNC2)s1]

TFA (4.89 g, 3.30 mL, 42.9 mmol) was added to a solution of tert-butyl 3-(thiazol-5-yl)piperidine-1-carboxylate (230 mg, 0.86 mmol) in DCM (2 mL). After 1 hour, the solution was concentrated in vacuo and the residue passed through an SCX-2 cartridge, washing with MeCN/MeOH and eluting the product with 2 M NH$_3$ in MeOH. The solution was concentrated in vacuo to afford 5-(piperidin-3-yl)thiazole (106 mg, 74% over two steps) as a yellow oil; MS m/z: 169.1 (M+H).

The following compounds were made using methodology similar to that described in Preparation 165:

2-(Piperidin-3-yl)oxazole;

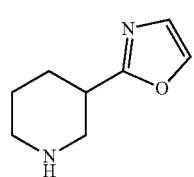 [SMILES: c1coc(C2CCCNC2)n1]

(4-(Pyrrolidin-3-yl)-1H-pyrazol-3-yl)methanol;

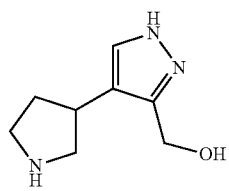 [SMILES: OCc1n[nH]cc1C1CCNC1]

4-(Pyrrolidin-3-yl)-1H-pyrazole;

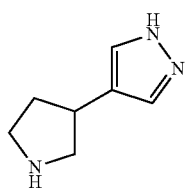

3-Fluoro-4-(pyrrolidin-3-yl)-1H-pyrazole;

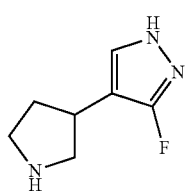 [SMILES: Fc1n[nH]cc1C1CCNC1]

3-Methyl-4-(pyrrolidin-3-yl)-1H-pyrazole;

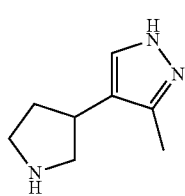

3,5-Dimethyl-4-(pyrrolidin-3-yl)-1H-pyrazole;

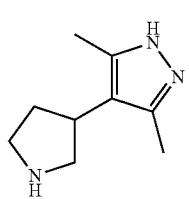

3-Cyclopropyl-4-(pyrrolidin-3-yl)-1H-pyrazole;

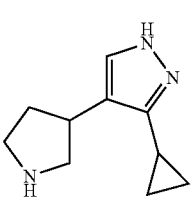 [SMILES: c1[nH]nc(C2CC2)c1C1CCNC1]

701
3-(1-Methylcyclopropyl)-4-(pyrrolidin-3-yl)-1H-pyrazole;
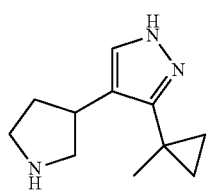
4-(Pyrrolidin-3-yl)-3-(trifluoromethyl)-1H-pyrazole;
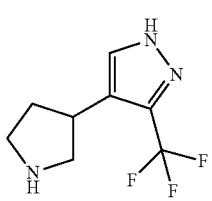 [SMILES: FC(F)(F)c1n[nH]cc1C1CCNC1]
3-(3-Fluoro-1H-pyrazol-4-yl)piperidine;
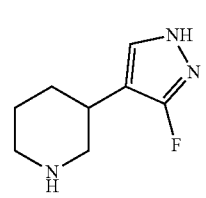 [SMILES: Fc1n[nH]cc1C1CCCNC1]
702
3-(2-Methyl-1H-imidazol-4-yl)piperidine;
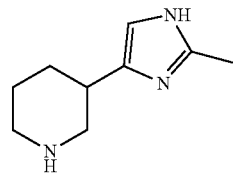
3-(2-Isopropyl-1H-imidazol-4-yl)piperidine;
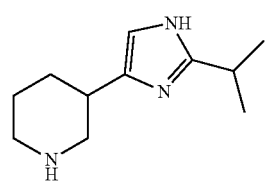
4-(Piperidin-3-yl)oxazole.
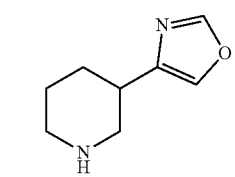 [SMILES: c1nc(C2CCCNC2)co1]
Preparation 166:
3-Methyl-2-(1-trityl-1H-imidazol-4-yl)morpholine
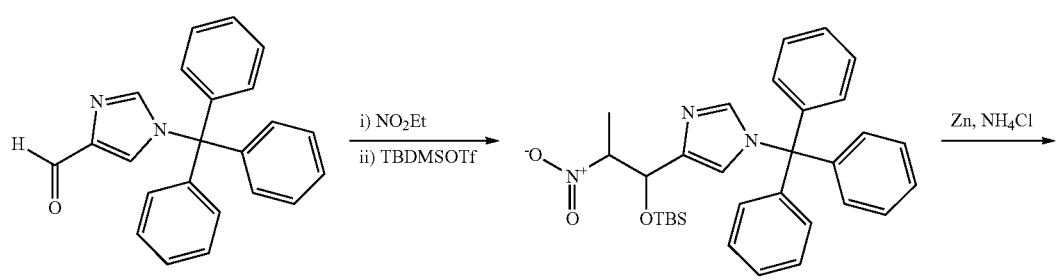
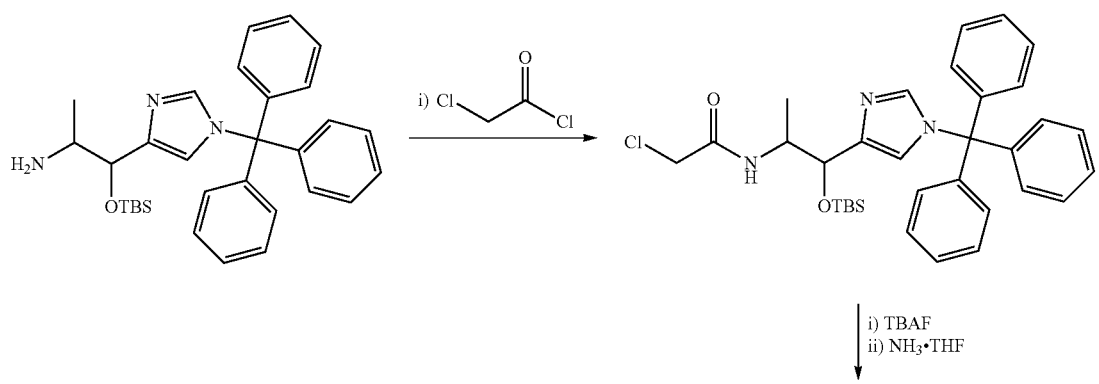

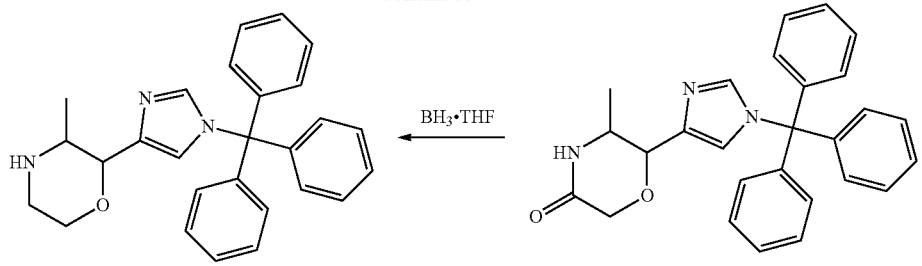

BH₃·THF

Step 1: 2-Nitro-1-(1-trityl-1H-imidazol-4-yl)propan-1-ol

Step 3: 1-((tert-Butyldimethylsilyl)oxy)-1-(1-trityl-1H-imidazol-4-yl)propan-2-amine

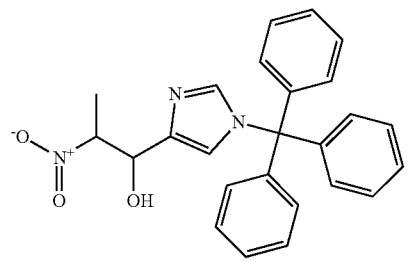

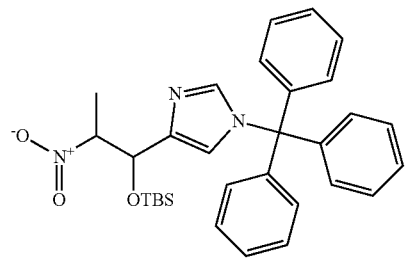

1-Tritylimidazole-4-carbaldehyde (5.0 g, 14.8 mmol) was added to a solution of 1-nitroethane (13 mL, 180 mmol) in DCM (6 mL). Et₃N (300 µL, 2.15 mmol) was added and the solution was stirred for 18 hours before being concentrated in vacuo to give 2-nitro-1-(1-trityl-1H-imidazol-4-yl)propan-1-ol (6.1 g, 100%), which was used without further purification; MS m/z: 414.3 (M+H)⁺.

Step 2: 4-(1-((tert-Butyldimethylsilyl)oxy)-2-nitropropyl)-1-trityl-1H-imidazole

[tert-Butyl(dimethyl)silyl]trifluoromethanesulfonate (60 µL, 0.26 mmol) was added to a solution of 2-nitro-1-(1-trityl-1H-imidazol-4-yl)propan-1-ol (100 mg, 0.24 mmol) and DIPEA (42 µL, 0.24 mmol) in DMF (1 mL). After stirring at ambient temperature for 1 hour, further [tert-butyl(dimethyl)silyl]trifluoromethanesulfonate (60 µL, 0.26 mmol) was added and the reaction stirred overnight. The reaction mixture was concentrated in vacuo and the residue partitioned between DCM and water. The organic layer was concentrated in vacuo to give 4-(1-((tert-butyldimethylsilyl)oxy)-2-nitropropyl)-1-trityl-1H-imidazole (128 mg, 100%) which was used without further purification; MS m/z: 528.5 (M+H)⁺.

Saturated aq. NH₄Cl (1 mL, 30 mmol) was added to a suspension of Zn (50 mg, 0.76 mmol) and 4-(1-((tert-butyldimethylsilyl)oxy)-2-nitropropyl)-1-trityl-1H-imidazole (128 mg, 0.24 mmol) stirring at ambient temperature in methanol (5 mL). After 1 hour the reaction was filtered and the filtrate concentrated in vacuo. The residue was passed through an SCX-2 cartridge, eluting the product with 2 M NH₃ in methanol. Concentration in vacuo gave 1-[tert-butyl(dimethyl)silyl]oxy-1-(1-tritylimidazol-4-yl)propan-2-amine (121 mg, 100%) which was used without further purification; MS m/z: 498.5 (M+H)⁺.

Step 4: N-(1-((tert-Butyldimethylsilyl)oxy)-1-(1-trityl-1H-imidazol-4-yl)propan-2-yl)-2-chloroacetamide

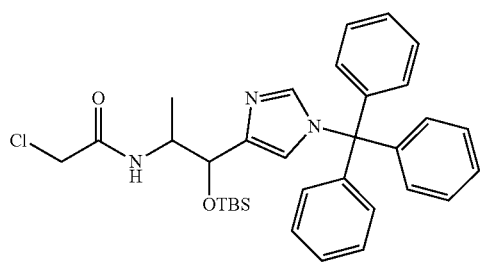 [SMILES: CC(NC(=O)CCl)C(O[Si](C)(C)C(C)(C)C)c1cn(C(c2ccccc2)(c2ccccc2)c2ccccc2)cn1]

2-Chloroacetyl chloride (16 µL, 0.20 mmol) was added to a solution of 1-((tert-butyldimethylsilyl)oxy)-1-(1-trityl-1H-imidazol-4-yl)propan-2-amine (90 mg, 0.18 mmol) and DIPEA (65 µL, 0.37 mmol) in DCM (3 mL) and the mixture stirred at ambient temperature. After 5 mins the reaction mixture was diluted in DCM and washed with saturated aq. NaHCO₃. The organic layer was dried (MgSO₄) and concentrated in vacuo to give N-(1-((tert-butyldimethylsilyl)

oxy)-1-(1-trityl-1H-imidazol-4-yl)propan-2-yl)-2-chloroacetamide (104 mg, 100%) which was used without further purification; MS m/z: 574.6 (M+H)⁺.

Step 5: 5-Methyl-6-(1-trityl-1H-imidazol-4-yl)morpholin-3-one

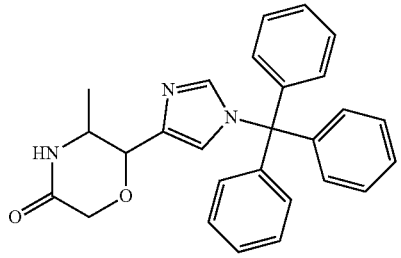 [SMILES: CC1NC(=O)COC1c1cn(C(c2ccccc2)(c2ccccc2)c2ccccc2)cn1]

TBAF (180 μL of 1 M, 0.18 mmol) was added to a solution of N-(1-(((tert-butyldimethylsilyl)oxy)-1-(1-trityl-1H-imidazol-4-yl)propan-2-yl)-2-chloroacetamide (104 mg, 0.18 mmol) in THF (4 mL). The mixture was stirred at ambient temperature for 2 hours before potassium 2-methylpropan-2-olate (180 μL of 1 M, 0.18 mmol) was added and the mixture was stirred overnight. The reaction mixture was diluted in DCM and washed with saturated aq. NH₄Cl, and the organic layer dried (MgSO₄) and evaporated in vacuo. Purification by column chromatography (SiO₂, eluting with 0-15% methanol in DCM gradient) gave 5-methyl-6-(1-trityl-1H-imidazol-4-yl)morpholin-3-one (77 mg, 100%) as a colourless glass; MS m/z: 424.4 (M+H)⁺.

Step 6: 2-(1H-Imidazol-4-yl)-3-methylmorpholine

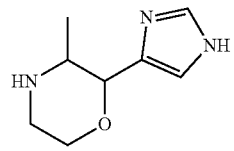

Borane tetrahydrofuran complex (1 mL of 1 M, 1.0 mmol) was added slowly to a solution of 5-methyl-6-(1-trityl-1H-imidazol-4-yl)morpholin-3-one (80 mg, 0.19 mmol) in THF (5 mL), stirring at ambient temperature. After 1 hour the reaction was quenched by addition of methanol and the mixture stirred for 15 mins before conc. HCl (1 mL) was added. The reaction mixture was stirred at ambient temperature for 2 hours before being concentrated in vacuo. The residue was passed through an SCX-2 cartridge, washing with methanol and eluting the product with 2 M NH₃ in methanol. The basic washings were concentrated in vacuo to give 2-(1H-imidazol-4-yl)-3-methylmorpholine (30 mg, 95%); MS m/z: 168.1 (M+H)⁺.

The following compound was made using methodology similar to that described in Preparation 166:

2-(1H-Imidazol-4-yl)-3,6-dimethylmorpholine.

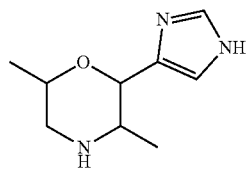

Preparation 167:
3,6-Dimethyl-2-(1H-pyrazol-4-yl)morpholine

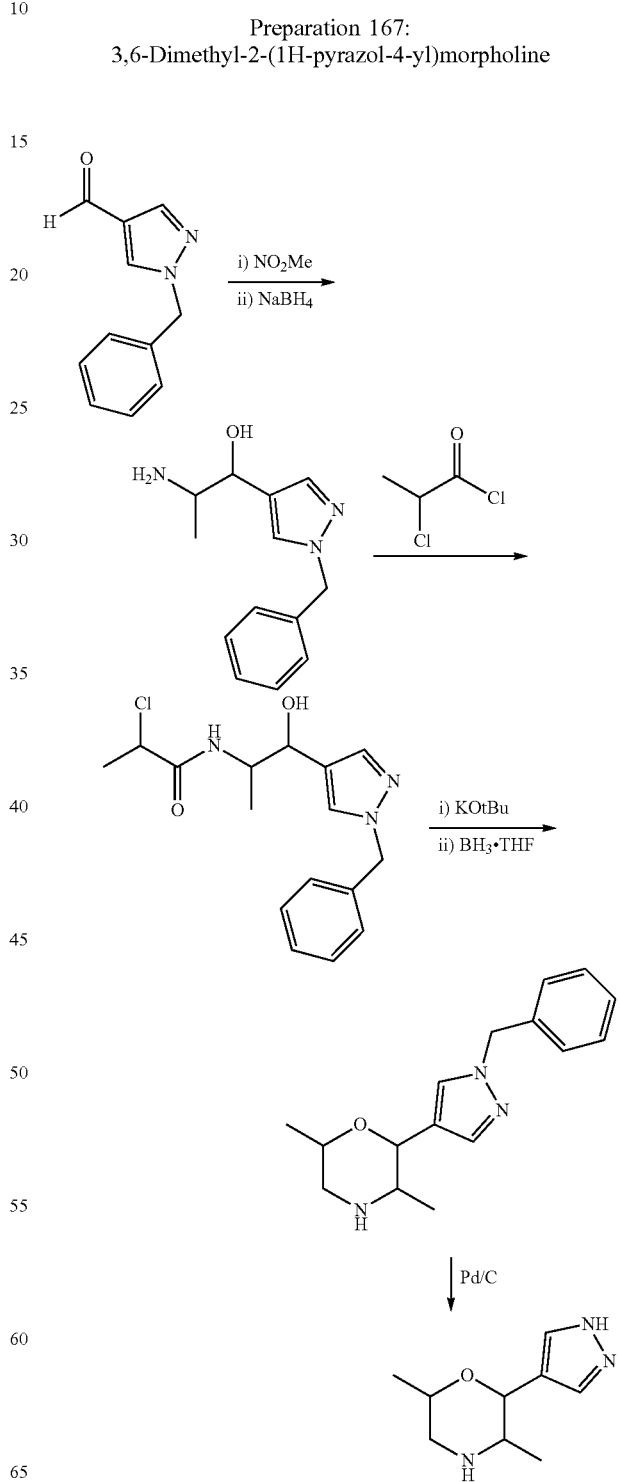

Step 1: 1-(1-Benzyl-H-pyrazol-4-yl)-2-nitropropan-1-ol

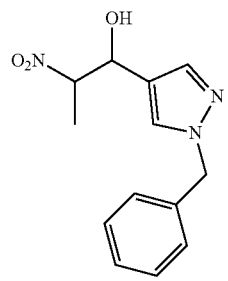 [SMILES: CC(C(O)c1cnn(Cc2ccccc2)c1)[N+](=O)[O-]]

1-Benzylpyrazole-4-carbaldehyde (10.5 g, 56.4 mmol) was dissolved in 1-nitroethane (49 mL, 681.8 mmol) and the solution cooled to 0° C. before addition of Et$_3$N (784 µL, 5.62 mmol). The solution was allowed to warm to ambient temperature and stirred overnight. The reaction was quenched with concentrated HCl (705 µL of 12 M, 8.46 mmol) and the mixture stirred for 10 minutes before being concentrated in vacuo. Purification by flash chromatography (330 g SiO$_2$, eluting with 50% EtOAc in petroleum ether) gave 1-(1-benzyl-1H-pyrazol-4-yl)-2-nitropropan-1-ol (10.5 g, 71%) as a crystalline white solid; MS m/z: 261.1 (M+H)$^+$.

Step 2: 2-Amino-1-(1-benzyl-1H-pyrazol-4-yl)propan-1-ol

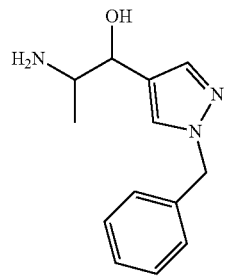

Sodium borohydride (6.82 g, 7.21 mL, 180.2 mmol) was added portionwise to a solution of 1-(1-benzyl-1H-pyrazol-4-yl)-2-nitropropan-1-ol (11.85 g, 45.35 mmol) and nickel (II) chloride hexahydrate (10.8 g, 45.3 mmol) in methanol (225 mL), stirring at 0° C. After addition, the solution was stirred at 0° C. for 20 min before being quenched by addition of water then 1 M HCl was added and the reaction stirred for 30 min. The suspension was filtered through Celite and the filtrate concentrated in vacuo. The residue was redissolved in methanol and acidified using HCl. This mixture was concentrated in vacuo to give 2-amino-1-(1-benzyl-1H-pyrazol-4-yl)propan-1-ol (Hydrochloride salt) (12.1 g) which was used without further purification; MS m/z: 232.1 (M+H)$^+$.

Step 3: N-(1-(1-Benzyl-1H-pyrazol-4-yl)-1-hydroxypropan-2-yl)-2-chloropropanamide

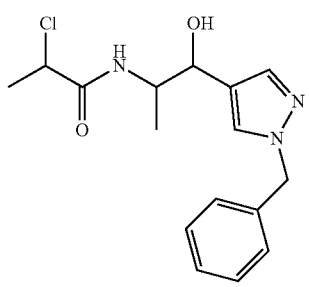 [SMILES: CC(Cl)C(=O)NC(C)C(O)c1cnn(Cc2ccccc2)c1]

2-Chloropropanoyl chloride (68.6 mg, 52.5 µL, 0.54 mmol) was added to a solution of 2-amino-1-(1-benzylpyrazol-4-yl)propan-1-ol (500 mg, 2.162 mmol) and Et$_3$N (904 µL, 6.49 mmol), stirring at 0° C. in DCM (27 mL). After 30 mins at this temperature the reaction mixture was quenched by addition of methanol (5 mL), and concentrated in vacuo. Purification by column chromatography (12 g SiO$_2$, eluting with 0-100% [90% EtOAc-10% 2 M methanolic NH$_3$] in petroleum ether) provided N-(1-(1-benzyl-1H-pyrazol-4-yl)-1-hydroxypropan-2-yl)-2-chloropropanamide (110 mg, 16% over two steps); MS m/z: 261.1 (M+H)$^+$.

Step 4: 6-(1-Benzyl-1H-pyrazol-4-yl)-2,5-dimethylmorpholin-3-one

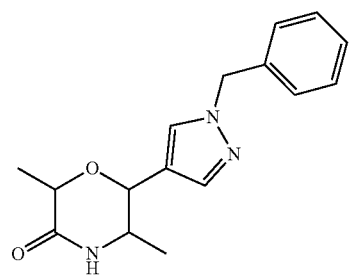 [SMILES: CC1OC(c2cnn(Cc3ccccc3)c2)C(C)NC1=O]

Potassium tert-butoxide (400 µL of 1 M, 0.40 mmol) was added to a solution of N-(1-(1-benzyl-1H-pyrazol-4-yl)-1-hydroxypropan-2-yl)-2-chloropropanamide (110 mg, 0.34 mmol) in THF (2 mL) and stirred at ambient temperature. After 3 days the reaction was diluted with DCM and washed with saturated aq. NH$_4$Cl. The organic layer was dried (MgSO$_4$) and concentrated in vacuo to 6-(1-benzyl-1H-pyrazol-4-yl)-2,5-dimethylmorpholin-3-one (49 mg, 100%) which was used without further purification; MS m/z: 286.3 (M+H)$^+$.

Step 5: 2-(1-Benzyl-1H-pyrazol-4-yl)-3,6-dimethyl-morpholine

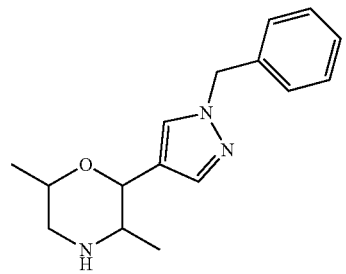 [SMILES: CC1CNC(C)C(c2cnn(Cc3ccccc3)c2)O1]

Borane THF complex (1.7 mL of 1 M, 1.70 mmol) was added to a solution of 6-(1-benzylpyrazol-4-yl)-2,5-dimethyl-morpholin-3-one (97 mg, 0.34 mmol) in THF (5 mL) stirring at 0° C. After 1 hour the reaction was quenched by addition of methanol and the mixture was concentrated in vacuo. Methanol (5 mL) was added followed by 1 M HCl (5 mL) and the mixture was stirred at ambient temperature for 1 hour before being concentrated in vacuo. The residue was passed through an SCX cartridge, washing with DCM/MeOH mixtures and eluting the product with 2 M NH$_3$ in MeOH. The ammonium extracts were concentrated in vacuo, and the residue was further dried by azeotroping from methanol and toluene (1:1 mixture) to give 2-(1-benzyl-1H-pyrazol-4-yl)-3,6-dimethylmorpholine (92 mg, 100%); MS m/z: 272.2 (M+H)$^+$.

Step 6: 3,6-Dimethyl-2-(1H-pyrazol-4-yl)morpholine

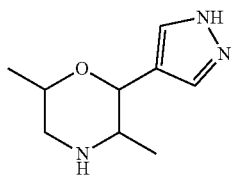

A solution of 2-(1-benzyl-1H-pyrazol-4-yl)-3,6-dimethylmorpholine (100 mg, 0.37 mmol), palladium on carbon (10% w/w wet, Degussa, 40 mg, 0.038 mmol) and concentrated HCl (200 µL of 12 M, 2.4 mmol) in methanol (5 mL) was stirred at ambient temperature under a balloon of H$_2$ overnight. The reaction mixture was filtered through Celite and the filtrate concentrated in vacuo. The residue was further dried by azeotroping from methanol and toluene (1:1 mixture) to give 3,6-dimethyl-2-(1H-pyrazol-4-yl)morpholine (80 mg, 100%); MS m/z: 182.2 (M+H)$^+$.

Preparation 168: 2,2-Dimethyl-6-(1H-pyrazol-4-yl)piperazine

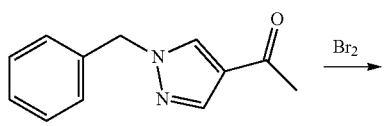

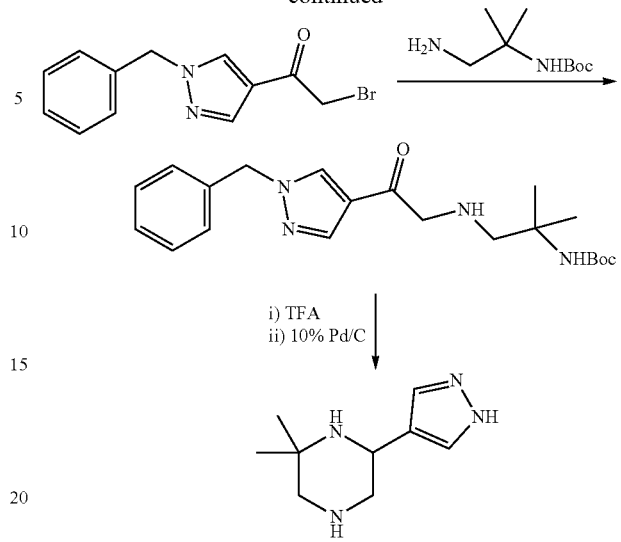

Step 1: 1-(1-Benzyl-1H-pyrazol-4-yl)-2-bromo-ethan-1-one

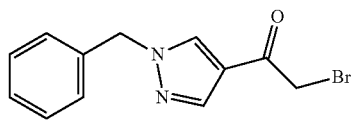 [SMILES: O=C(CBr)c1cnn(Cc2ccccc2)c1]

Bromine (390 µL, 7.57 mmol) was added dropwise to a solution of 1-(1-benzylpyrazol-4-yl)ethanone (1.5 g, 7.49 mmol) in chloroform (20 mL) stirring at 0° C. under a nitrogen atmosphere. After 5 min, the reaction was warmed to ambient temperature and stirred overnight. Further bromine (200 µL, 3.88 mmol) was added and the reaction stirred for a further 4 hours before being quenched by addition of saturated aq. NaHCO$_3$ (30 mL). The layers were separated, and the organic layer washed with brine, dried (MgSO$_4$) and concentrated in vacuo. Purification by column chromatography (40 g SiO$_2$, 0-100% ethyl acetate in hexanes) to give 1-(1-benzyl-1H-pyrazol-4-yl)-2-bromoethan-1-one as a yellow oil (1.34 g, 61%); MS m/z: 281.1 (M+H)$^+$.

Step 2: tert-Butyl (1-((2-(1-benzyl-1H-pyrazol-4-yl)-2-oxoethyl)amino)-2-methylpropan-2-yl) carbamate

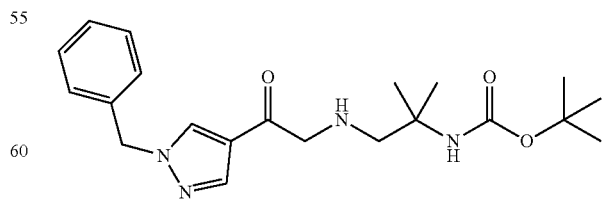

A solution of 1-(1-benzyl-1H-pyrazol-4-yl)-2-bromo-ethan-1-one (510 mg, 1.83 mmol), Et$_3$N (280 µL, 2.01 mmol) and tert-butyl (1-amino-2-methylpropan-2-yl)carbamate (344 mg, 1.83 mmol) in DCM (10.2 mL) was stirred at ambient temperature for 90 min before being diluted in DCM. The layers were separated and the organic layer washed with water and brine, dried (MgSO₄) and concentrated in vacuo. The material was used in the next step with no further purification.

Step 3: 6-(1-Benzyl-1H-pyrazol-4-yl)-2,2-dimethylpiperazine

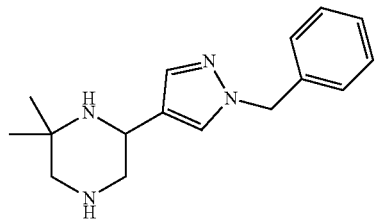 [SMILES: CC1(C)CNCC(c2cnn(Cc3ccccc3)c2)N1]

tert-Butyl (1-((2-(1-benzyl-1H-pyrazol-4-yl)-2-oxoethyl)amino)-2-methylpropan-2-yl)carbamate (700 mg, 1.81 mmol) was dissolved in DCM (10 mL) and the mixture stirred at 0° C. TFA (3 mL) was added and the reaction stirred for 3 hours before being concentrated in vacuo. The residue was dissolved in methanol (16.8 mL) and sodium triacetoxyborahydride (1.54 g, 7.24 mmol) was added. After stirring for 30 mins at ambient temperature the reaction was quenched by addition of saturated aq. NaHCO₃ and concentrated in vacuo. The residue was passed through an SCX cartridge and the ammonia extracts concentrated in vacuo to give 6-(1-benzyl-1H-pyrazol-4-yl)-2,2-dimethylpiperazine (400 mg, 82%); MS m/z: 271.3 (M+H)⁺.

Step 4: 2,2-Dimethyl-6-(1H-pyrazol-4-yl)piperazine

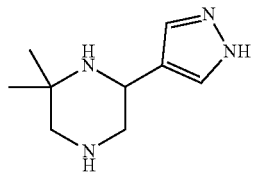

12 M HCl (616 µL, 7.40 mmol) was added to a solution of 6-(1-benzyl-1H-pyrazol-4-yl)-2,2-dimethylpiperazine (400 mg, 1.48 mmol) and palladium on carbon (wet, Degussa 10% w/w, 157 mg, 0.15 mmol) in methanol (6 mL). The reaction was stirred under a balloon of H₂ overnight before being filtered through Celite and concentrated in vacuo. The residue was passed through an SCX cartridge and the ammonia extracts concentrated in vacuo to give 2,2-dimethyl-6-(1H-pyrazol-4-yl)piperazine (133 mg, 50%); MS m/z: 181.0 (M+H)⁺.

Preparation 169: 3-(1H-Pyrazol-4-yl)piperidin-3-ol

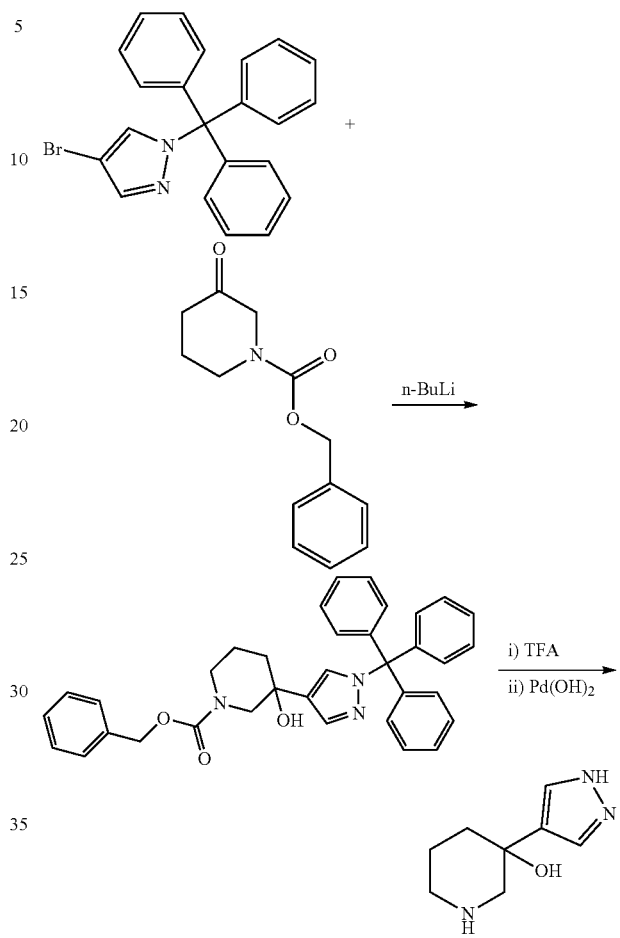

Step 1: Benzyl 3-hydroxy-3-(1-trityl-1H-pyrazol-4-yl)piperidine-1-carboxylate

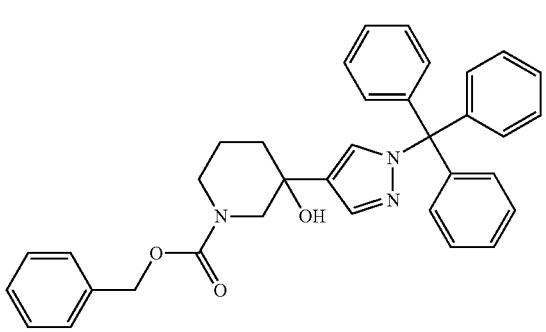 [SMILES: O=C(OCc1ccccc1)N1CCCC(O)(c2cnn(C(c3ccccc3)(c3ccccc3)c3ccccc3)c2)C1]

4-Bromo-1-trityl-pyrazole (3.03 g, 7.77 mmol) in THF (40 mL) was cooled to −78° C. before dropwise addition of n-BuLi (3.36 mL of 2.5 M in hexanes, 8.39 mmol). After 20 mins benzyl 3-oxopiperidine-1-carboxylate (1.903 g, 8.160 mmol) was added as a solution in THF (15 mL). After a further 20 mins, the mixture was quenched with saturated aq. NH₄Cl (15 mL) and allowed to warm to ambient temperature. The mixture was partitioned between water and EtOAc, the organic layer separated, dried (MgSO₄) and concentrated in vacuo. Purification by column chromatography (120 g SiO₂, 10-45% ethyl acetate in petroleum ether) to give benzyl 3-hydroxy-3-(1-trityl-1H-pyrazol-4-yl)piperidine-1-carboxylate (2.00 g, 47%); ¹H NMR (500 MHz, DMSO-d₆) δ 7.60 (d, J=0.8 Hz, 1H), 7.39-7.27 (m, 16H), 7.07-7.00 (m, 5H), 5.01 (t, J=13.6 Hz, 3H), 3.56 (s, 2H), 3.37 (d, J=12.9 Hz, 1H), 3.18 (d, J=54.4 Hz, 1H), 1.84 (s, 1H), 1.73 (s, 2H), 1.34 (s, 1H).

Step 2: Benzyl 3-hydroxy-3-(1H-pyrazol-4-yl)piperidine-1-carboxylate

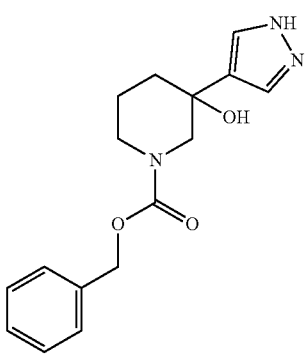 [SMILES: O=C(OCc1ccccc1)N1CCCC(O)(c2cn[nH]c2)C1]

TFA (5 mL, 60 mmol) was added to a solution of benzyl 3-hydroxy-3-(1-trityl-1H-pyrazol-4-yl)piperidine-1-carboxylate (1 g, 1.84 mmol) in DCM (10 mL), stirring at ambient temperature. After 40 minutes, the reaction was concentrated in vacuo and the residue partitioned between saturated aq. NaHCO₃ and DCM. The layers were separated and the aqueous layer extracted again with DCM. The combined organics were dried (MgSO₄), concentrated in vacuo and purified by column chromatography (24 g SiO₂, 20-100% ethyl acetate in petroleum ether) to give benzyl 3-hydroxy-3-(1H-pyrazol-4-yl)piperidine-1-carboxylate (440 mg, 79%); ¹H NMR (500 MHz, DMSO-d₆) δ 12.60 (s, 1H), 7.76-7.18 (m, 7H), 5.08 (s, 2H), 4.90 (s, 1H), 3.64 (d, J=16.0 Hz, 2H), 3.35 (d, J=13.0 Hz, 1H), 3.13 (d, J=61.2 Hz, 1H), 1.95-1.68 (m, 3H), 1.39 (s, 1H).

Step 3: 3-(1H-Pyrazol-4-yl)piperidin-3-ol

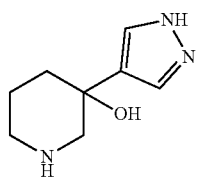 [SMILES: OC1(c2cn[nH]c2)CCCNC1]

Pd(OH)₂ (164 mg of 20% w/w, 0.234 mmol) was added to a solution of benzyl 3-hydroxy-3-(1H-pyrazol-4-yl)piperidine-1-carboxylate (440 mg, 1.46 mmol) in degassed methanol (15 mL). The mixture was degassed and stirred under a balloon of H₂. After 1.5 hours, the reaction mixture was filtered through Celite and concentrated to give 3-(1H-pyrazol-4-yl)piperidin-3-ol (244 mg, 100%); ¹H NMR (500 MHz, DMSO-d₆) δ 7.50 (s, 2H), 4.68 (s, 1H), 3.31 (s, 3H), 2.81 (dt, J=12.7, 3.8 Hz, 1H), 2.76-2.63 (m, 2H), 2.48 (dd, J=10.0, 3.2 Hz, 1H), 1.83-1.65 (m, 3H), 1.36 (dq, J=12.1, 4.3, 3.9 Hz, 1H)

Preparation 170:
3-(2-Chloro-1H-imidazol-4-yl)piperidine

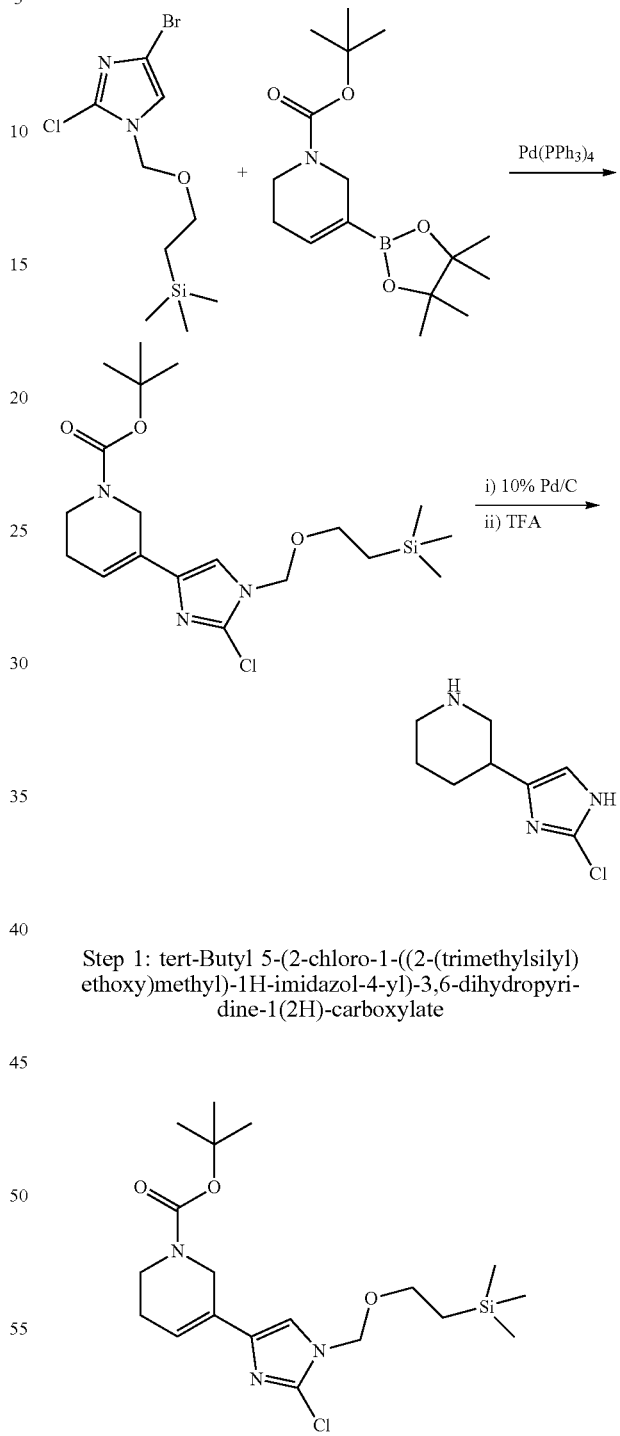

Step 1: tert-Butyl 5-(2-chloro-1-((2-(trimethylsilyl)ethoxy)methyl)-1H-imidazol-4-yl)-3,6-dihydropyridine-1(2H)-carboxylate To a suspension of 2-[(4-bromo-2-chloro-imidazol-1-yl)methoxy]ethyl-trimethyl-silane (400 mg, 1.28 mmol) and tert-butyl 5-(4,4,5,5-tetramethyl-1,3,2-dioxaborolan-2-yl)-3,6-dihydro-2H-pyridine-1-carboxylate (400 mg, 1.29 mmol) in 1,4-dioxane (8 mL) was added tetrakis(triphenylphosphine)palladium(0) (140 mg, 0.12 mmol) and Na₂CO₃ (2 mL of 2 M, 4.00 mmol). The reaction was stirred in a sealed tube at 130° C. for 2 hours before being filtered and concentrated in vacuo to give tert-butyl 5-(2-chloro-1-((2-(trimethylsilyl)ethoxy)methyl)-1H-imidazol-4-yl)-3,6-dihydropyridine-1(2H)-carboxylate (500 mg, 94%) as a yellow solid, which was used without further purification; MS m/z: 414.4 (M–H)⁻.

Step 2: 3-(2-Chloro-1H-imidazol-4-yl)piperidine

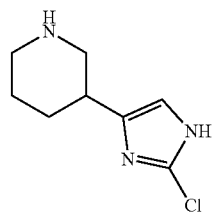 [SMILES: Clc1nc(C2CCCNC2)c[nH]1]

A mixture of tert-butyl 5-(2-chloro-1-((2-(trimethylsilyl)ethoxy)methyl)-1H-imidazol-4-yl)-3,6-dihydropyridine-1(2H)-carboxylate (530 mg, 1.28 mmol), palladium on carbon (wet, Degussa, 10% w/w, 280 mg, 2.63 mmol) in methanol (50 mL) was shaken at ambient temperature in the Parr hydrogenator under 60 psi H₂ pressure overnight. The mixture was filtered through Celite and concentrated in vacuo to give 3-(2-chloro-1H-imidazol-4-yl)piperidine. The crude material was redissolved in DCM (3 mL) and TFA (3 mL) and the mixture stirred for 1 hour before being concentrated in vacuo. The crude material was redissolved in methanol and passed through a SCX-2 cartridge, rinsing with methanol and eluting the product with methanolic ammonia. The ammonia extracts were concentrated in vacuo to give (200 mg, 84% over two steps) as a brown solid; MS m/z: 186.0 (M+H)⁺.

The following compound was made using methodology similar to that described in Preparation 170:
3-(3-Fluoro-1H-pyrazol-4-yl)piperidine.

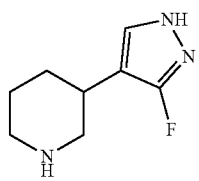 [SMILES: Fc1n[nH]cc1C1CCCNC1]

Preparation 171:
N-(Pyrrolidin-3-yl)-1H-pyrazol-4-amine

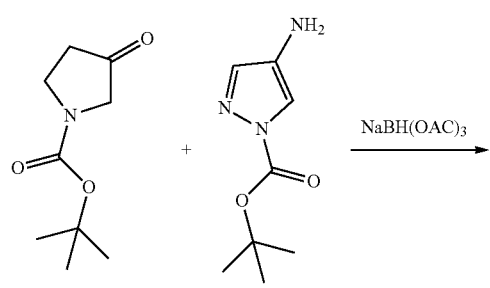

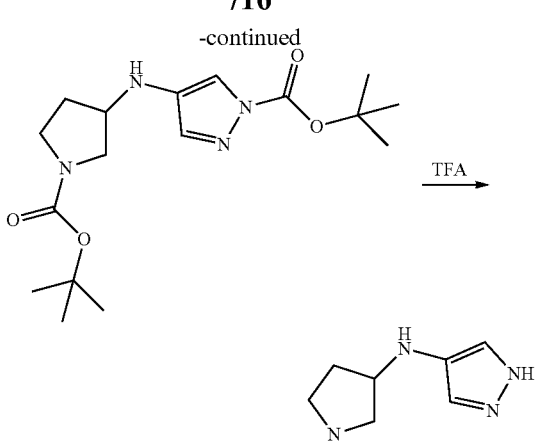

Step 1: tert-Butyl 4-((1-(tert-butoxycarbonyl)pyrrolidin-3-yl)amino)-1H-pyrazole-1-carboxylate

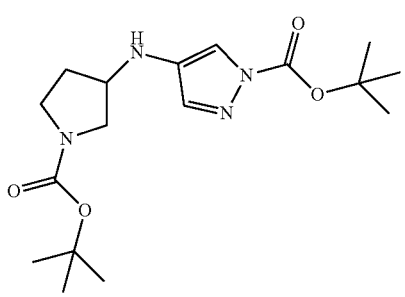 [SMILES: CC(C)(C)OC(=O)N1CCC(Nc2cnn(C(=O)OC(C)(C)C)c2)C1]

tert-Butyl 3-oxopyrrolidine-1-carboxylate (309 mg, 1.67 mmol) and tert-butyl 4-aminopyrazole-1-carboxylate (611 mg, 3.34 mmol) were combined in methanol (5 mL). After stirring for 10 mins at ambient temperature, the solution was cooled to 0° C. and NaBH(OAc)₃ (1.03 g, 4.88 mmol) was added. The reaction was allowed to warm to ambient temperature and stirred overnight before being heated at 50° C. for 6 hours. The reaction mixture was concentrated in vacuo and the residue partitioned between EtOAc and saturated aq. NaHCO₃ solution. The aqueous phase was extracted with EtOAc and the combined organics were washed with brine, dried (Na₂SO₄) and concentrated in vacuo. Purification by column chromatography (40 g SiO₂, eluting with a 0-100% EtOAc in petroleum ether) gave tert-butyl 4-((1-(tert-butoxycarbonyl)pyrrolidin-3-yl)amino)-1H-pyrazole-1-carboxylate, which was used without further purification.

Step 2: N-(Pyrrolidin-3-yl)-1H-pyrazol-4-amine

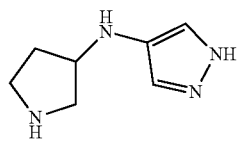 [SMILES: c1n[nH]cc1NC1CCNC1]

The material from step 1 was dissolved in DCM (2 mL) and TFA (1 mL) was added. After 3 hours at ambient temperature the reaction was evaporated in vacuo to give N-(pyrrolidin-3-yl)-1H-pyrazol-4-amine (50 mg, 8%) as the TFA salt; MS m/z: 153.0 (M+H)+.

Preparation 172:
N-(1-(Morpholin-2-yl)ethyl)methanesulfonamide

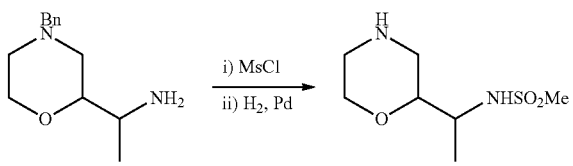

A round-bottomed flask was charged with 1-(4-benzylmorpholin-2-yl)ethanamine (520 mg, 2.4 mmol), Et$_3$N (658 μL, 4.7 mmol) in DCM (11 mL) under N$_2$. The mixture was then cooled to −78° C. and MsCl (164 μL, 2 mmol) added dropwise. The mixture was stirred for 10 minutes then allowed to warm to ambient temperature and stirred for a further 10 minutes. The reaction was quenched by the addition of saturated aqueous NaHCO$_3$ solution. After 5 minutes the reaction mixture was filtered through a phase separator cartridge and concentrated in vacuo. The resulting brown oil (700 mg), was taken directly on to the next reaction; MS m/z: 299 (M+H)+.

A round-bottomed flask was charged with N-[1-(4-benzylmorpholin-2-yl)ethyl]methanesulfonamide (700 mg, 2 mmol) in MeOH (10 mL) and concentrated HCl (196 μL, 2 mmol) was added. The flask was degassed and filled with N$_2$ (×3 vacuum-N$_2$ cycles) and Pd on C, wet, Degussa 10% w/w (249 mg, 0.2 mmol) was added in one portion. The flask was coupled with a hydrogen balloon and filled (vacuum-hydrogen×3 cycles). The reaction was vigorously stirred at ambient temperature overnight. The mixture was filtered though a pad of Celite and the filtrate concentrated in vacuo. The residue was dissolved in methanol and loaded into an ion-exchange cartridge. The cartridge was eluted with methanol (filtrate discarded) then with 2 M methanolic NH$_3$ solution. The filtrate was concentrated in vacuo to give N-(1-(morpholin-2-yl)ethyl)methanesulfonamide (450 mg), which was taken directly on to the next reaction without further purification; MS m/z: 209 (M+H)+.

Preparation 173: N-[[(2S)-Morpholin-2-yl]methyl]methanesulfonamide

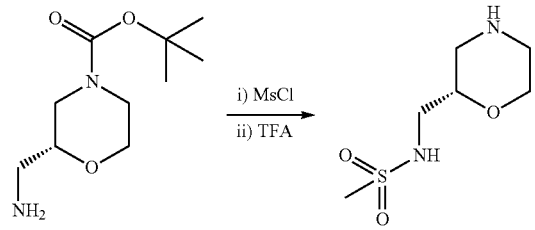

To a round bottom flask was added tert-butyl (2R)-2-(aminomethyl)morpholine-4-carboxylate (5 g, 23 mmol) and Et3N (16.1 mL, 115 mmol) followed by THF (100 mL). DCM (50 mL) was added and the mixture was cooled to 0° C. Methanesulfonyl chloride (2.4 mL, 30.5 mmol) was added dropwise and the mixture stirred for 0.5 hours, then left at ambient temperature for 16 hours under an atmosphere of N2. The reaction was quenched with saturated aqueous NaHCO3 solution (100 mL) and the majority of the volatiles were removed in vacuo. The aqueous layer was extracted with ethyl acetate (3×50 mL). The combined organics were dried over Na2SO4, filtered and concentrated in vacuo. The residue was purified by column chromatography (silica, eluting with 70 to 100% EtOAc/petroleum ether). The product fractions were combined and concentrated in vacuo. The residue was dried overnight under vacuum to give N-[[(2S)-morpholin-2-yl]methyl]methanesulfonamide (3.61 g, 53%) as a white solid; 1H NMR (500 MHz, Chloroform-d) δ 4.71-4.59 (m, 1H), 3.98-3.82 (m, 2H), 3.63-3.49 (m, 2H), 3.38-3.24 (m, 1H), 3.20-3.11 (m, 1H), 3.04-2.90 (m, 4H), 2.73 (s, 1H), 1.49 (s, 9H).

TFA (9 mL, 115 mmol) was added to a stirred solution of tert-butyl (2S)-2-(methanesulfonamidomethyl)morpholine-4-carboxylate (3.6 g, 12 mmol) in DCM (60 mL) and the reaction stirred at ambient temperature for 6 hours. The solvent was removed in vacuo and the residue azeotroped with DCM (×2) and diethyl ether (×2). The residue was taken up in methanol and passed through an ion-exchange cartridge, eluting with methanol (discarded) then a 2 M methanolic ammonia solution. The filtrate was concentrated in vacuo to give N-[[(2S)-morpholin-2-yl]methyl]methanesulfonamide (2.3 g, 97%); 1H NMR (500 MHz, Chloroform-d) δ 4.73 (s, 1H), 3.90-3.87 (m, 1H), 3.65-3.60 (m, 2H), 3.26 (dd, 1H), 3.09 (dd, 1H), 2.99 (s, 3H), 2.92-2.84 (m, 3H), 2.66 (dd, 1H); MS m/z: 195 (M+H)+.

Preparation 174: 2-Methylpiperidine-3-carboxamide

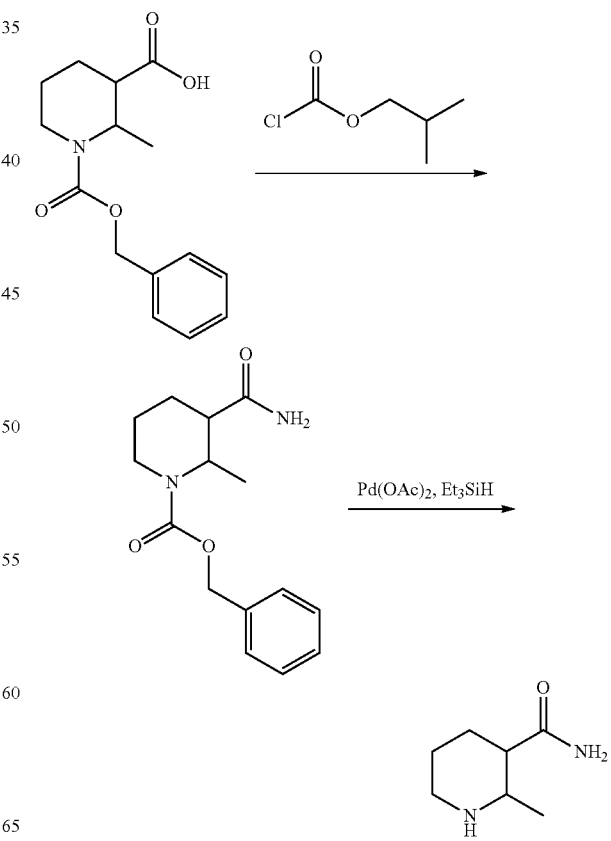

Step 1: Benzyl 3-carbamoyl-2-methylpiperidine-1-carboxylate

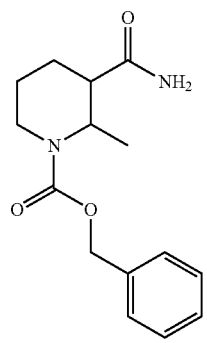 [SMILES: CC1C(C(N)=O)CCCN1C(=O)OCc1ccccc1]

Triethylamine (413 µL, 2.96 mmol) was added to a solution of 1-((benzyloxy)carbonyl)-2-methylpiperidine-3-carboxylic acid (685 mg, 2.47 mmol) in THF (5.5 mL). The reaction mixture was cooled to 10° C. before isobutyl carbonochloridate (388 mg, 368 µL, 2.84 mmol) was added dropwise. The mixture was stirred for 30 mins before NH$_4$OH (4 mL, 103 mmol) was added. The reaction was stirred for a further hour before water (5 mL) was added and the mixture extracted with DCM (×3). The combined organic extracts were dried (MgSO4) and concentrated in vacuo to give benzyl 3-carbamoyl-2-methylpiperidine-1-carboxylate (680 mg, 99%) which was used without further purification; MS m/z: 277.3 (M+H)$^+$.

Step 2: 2-Methylpiperidine-3-carboxamide

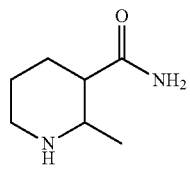

A mixture of benzyl 3-carbamoyl-2-methylpiperidine-1-carboxylate (680 mg, 2.46 mmol), Pd(OAc)$_2$ (247 mg, 1.10 mmol), Et$_3$SiH (927 µL, 5.80 mmol) and Et$_3$N (618 µL, 4.43 mmol) in DCM (13.6 mL) was stirred at ambient temperature for 1 hour before being diluted in methanol. The mixture was passed through an SCX-2 cartridge, washing with methanol and eluting the product with 2 M NH$_3$ in methanol. The ammonium extracts were concentrated in vacuo to give 2-methylpiperidine-3-carboxamide (200 mg, 57%) as a colourless oil; MS m/z: 141.0 (M−H)$^−$.

Preparation 175: 2,5-Dimethylpiperidine-3-carboxamide

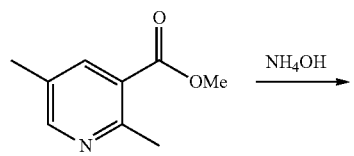

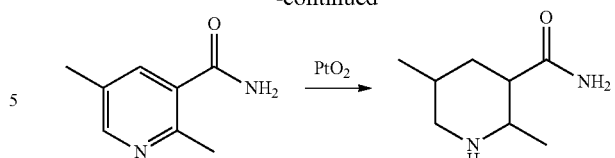

Step 1: 2,5-Dimethylnicotinamide

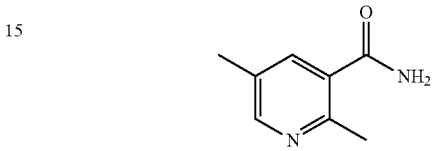

Methyl 2,5-dimethylpyridine-3-carboxylate (100 mg, 0.61 mmol) was dissolved in ammonium hydroxide (480 µL, 12.3 mmol) and the mixture heated to 70° C. in a sealed tube. After 16 hours the reaction was diluted in water and the mixture concentrated in vacuo to give 2,5-dimethylpyridine-3-carboxamide (91 mg, 100%) as a white solid; MS m/z: 151.0 (M+H)$^+$.

Step 2: 2,5-Dimethylpiperidine-3-carboxamide

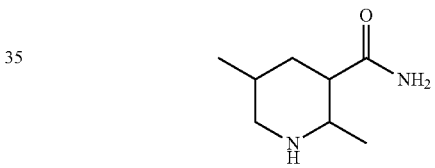

2,5-Dimethylnicotinamide (99 mg, 0.66 mmol) and PtO$_2$ (30.4 mg, 0.13 mmol) were dissolved in methanol (3 mL) and 3 M HCl (1.1 mL, 3.30 mmol). The mixture was degassed and stirred under a balloon of H$_2$ for 90 mins before being passed through Celite and the filtrate concentrated in vacuo to give 2,5-dimethylpiperidine-3-carboxamide (dihydrochloride salt) (150 mg, 99%); MS m/z: 157.0 (M+H)$^+$.

Preparation 176: (S)—N-(Piperidin-3-ylmethyl)methanesulfonamide

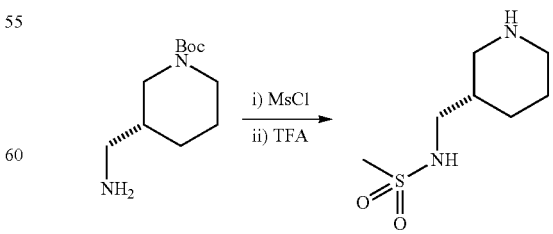

Methanesulfonyl chloride (465 µL, 6.0 mmol) was added to a stirred solution of tert-butyl (3R)-3-(aminomethyl)piperidine-1-carboxylate (1.0 g, 4.7 mmol) and Et$_3$N (1 mL, 7.2 mmol) in THF (20 mL) under an atmosphere of nitrogen and the reaction was stirred at ambient temperature for 16 hours. The reaction was diluted with DCM and saturated aqueous NaHCO$_3$ and the mixture was stirred for 10 minutes. The layers were separated and the aqueous layer extracted with DCM (×2). The combined organic extracts were dried (MgSO$_4$), filtered and concentrated in vacuo to give a pale yellow oil that was taken up in DCM (30 mL). TFA (7.5 mL, 97.4 mmol) was added and the reaction mixture was stirred at ambient temperature for 20 hours. The solvent was removed in vacuo and the residue azeotroped with DCM (×2) and diethyl ether (×2). The residue was passed through an ion-exchange cartridge and washed with MeOH/DCM mixtures (filtrates discarded). The product was eluted by washing the cartridge with 2 M NH$_3$ in MeOH/DCM mixtures. The solvent was removed in vacuo to give (S)—N-(piperidin-3-ylmethyl)methanesulfonamide (846 mg, 94%) as a colourless oil; $^1$H NMR (500 MHz, Chloroform-d) δ 3.13 (dd, 1H), 3.06 (d, 2H), 3.02-2.98 (m, 1H), 2.97 (s, 3H), 2.64-2.58 (m, 1H), 2.41 (dd, 1H), 1.89-1.83 (m, 1H), 1.75-1.67 (m, 1H), 1.59 (br s, 1H), 1.54-1.45 (m, 1H), 1.22-1.14 (m, 1H); MS m/z: 193 (M+H)$^+$.

Preparation 177: N-(((3S,5S)-4,4-Difluoro-5-methylpiperidin-3-yl)methyl)methanesulfonamide

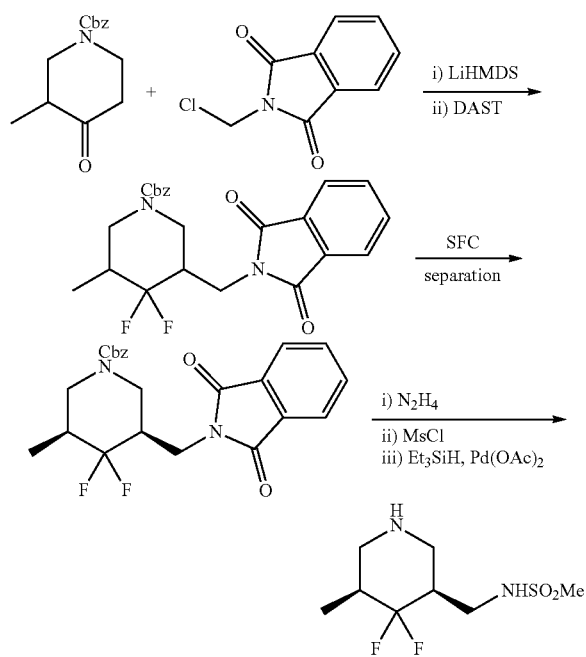

Benzyl 3-methyl-4-oxo-piperidine-1-carboxylate (20 g, 0.08 mol) was dissolved in THF (300 mL) under N$_2$. The solution was cooled to −78° C. and LiHMDS (1 M in THF, 101.1 mL, 0.1 mol) was added dropwise over 20 minutes, keeping the temperature below −70° C. After stirring at −78° C. for 90 minutes, a solution of 2-(chloromethyl)isoindoline-1,3-dione (23.7 g, 0.12 mol) in THF (200 mL) was added dropwise over 25 minutes, keeping the temperature below −70° C. The reaction was stirred at −78° C. for 1 hour then quenched at −78° C. by the addition of saturated aqueous ammonium chloride solution (65 mL) and the mixture allowed to warm to ambient temperature. The reaction was repeated and the two mixtures obtained were combined and extracted with EtOAc (300 mL). The organic phase was washed with saturated aqueous sodium bicarbonate solution (300 mL) and brine (300 mL), dried (Na$_2$SO$_4$), filtered and concentrated in vacuo. The residue was purified by chromatography (silica, EtOAc/petroleum ether elution). Product fractions were combined and concentrated in vacuo and the residue recrystallized from EtOAc to give the product as a white solid (7.56 g, 23%).

A flask was charged with benzyl 3-((1,3-dioxoisoindolin-2-yl)methyl)-5-methyl-4-oxopiperidine-1-carboxylate (60 g, 0.15 mol) and cooled in an ice/water bath. DAST (325 mL, 2.5 mol) was added in one portion and the mixture stirred at ambient temperature for 3 days. The resulting yellow solution was diluted with DCM (1 L) and slowly added to a mixture of ice/water and solid sodium bicarbonate with overhead stirring. The temperature remained below 0° C. and additional sodium bicarbonate was added to maintain a pH of 7-8. The mixture was warmed to ambient temperature and the layers separated. The aqueous phase was extracted with DCM (2 L). The combined organics were washed with brine, dried (Na$_2$SO$_4$), filtered and concentrated in vacuo. The residue was purified by chromatography (silica, EtOAc/petroleum ether elution). Product fractions were combined and concentrated in vacuo. The product benzyl 3-((1,3-dioxoisoindolin-2-yl)methyl)-4,4-difluoro-5-methylpiperidine-1-carboxylate, was obtained as a glass (32.5 g, 51%); $^1$H NMR (300 MHz, chloroform-d) δ 7.89-7.64 (4H, m), 7.42-7.11 (5H, m), 5.15-5.03 (2H, m), 4.39-4.07 (3H, m), 3.83-3.66 (1H, m), 2.97-2.60 (2H, m), 2.56-2.31 (1H, m), 2.08-1.89 (1H, m), 1.05 (3H, d) as a mixture of isomers.

Preparative chiral supercritical fluid chromatography (conditions: Chiralpak® IC 5 m, CO$_2$/iPrOH 90/10, 230 nm) was used to isolate the single enantiomer benzyl (3R,5S)-3-[(1,3-dioxoisoindolin-2-yl)methyl]-4,4-difluoro-5-methyl-piperidine-1-carboxylate, (98.7% ee).

To a suspension of benzyl (3R,5S)-3-[(1,3-dioxoisoindolin-2-yl)methyl]-4,4-difluoro-5-methyl-piperidine-1-carboxylate (9.6 g, 22.4 mmol) in ethanol (144 mL) was added hydrazine hydrate (8.5 mL, 112 mmol). The reaction mixture was heated at reflux for 5 hours then allowed to cool to ambient temperature overnight. The resulting suspension was filtered and the precipitate washed with EtOH (×2). The filtrate was loaded onto ion-exchange cartridges (50 g×10). The cartridges were washed with MeOH/DCM mixtures (filtrates discarded), then with 2 M methanolic ammonia solution. The filtrates were combined and concentrated in vacuo. The residue was taken up in MeOH and concentrated in vacuo (×2), then treated with heptane and concentrated in vacuo. The resulting yellow oil was dried under vacuum overnight to give the product as a solid (6.77 g), which was taken directly on to the next reaction; $^1$H NMR (400 MHz, DMSO-d$_6$) δ 7.48-7.17 (m, 5H), 5.11 (s, 2H), 4.41 (ddt, 1H), 4.02 (d, 1H), 2.98 (dd, 1H), 2.64 (s, 2H), 2.41 (dd, 1H), 2.15-1.78 (m, 2H), 1.50 (s, 2H), 0.93 (d, 3H); MS m/z: 299 (M+H)$^+$.

Benzyl (3R,5S)-3-(aminomethyl)-4,4-difluoro-5-methyl-piperidine-1-carboxylate (6.6 g, 22 mmol) was dissolved in DCM (66 mL) and cooled in an ice bath. The internal temperature reached 3° C. Et$_3$N (3.4 mL, 24 mmol) was added with stirring. Methanesulfonyl chloride (1.88 mL, 24 mmol) was added over 5 minutes, at such a rate to keep the internal temperature below 10° C. After 30 minutes, the ice bath was removed. The solution was warmed up to ambient temperature and quenched with a saturated aqueous NaHCO$_3$ solution (66 mL). The layers were separated and the aqueous phase extracted with DCM (33 mL). The combined organics were dried over MgSO$_4$, filtered and concentrated in vacuo. The residue was purified by chromatography (silica; 0 to 100% EtOAc/PE gradient elution). The product fractions were combined and concentrated in vacuo. The residue was dried overnight under vacuum to give a white solid (7.92 g, 95%); $^1$H NMR (400 MHz, DMSO-d$_6$) δ 7.45-7.31 (m, 5H), 7.31-7.19 (m, 1H), 5.12 (s, 2H), 4.37 (d, 1H), 4.18-3.94 (m, 1H), 3.38 (ddd, 1H), 3.00-2.80 (m, 4H), 2.68 (s, 2H), 2.15 (s, 2H), 0.95 (d, 3H); MS m/z: 377 (M+H)$^+$.

To a solution of benzyl (3S,5S)-4,4-difluoro-3-(methanesulfonamidomethyl)-5-methyl-piperidine-1-carboxylate (7.54 g, 20 mmol) in DCM (113 mL) was added Et$_3$N (8.38 mL, 60 mmol), followed by Pd(OAc)$_2$ (1.799 g, 8 mmol). Et$_3$SiH (19.20 mL, 120 mmol) was added over 5 minutes. The solution was stirred at ambient temperature for 1 hour then separated into 6 equal portions and loaded onto ion-exchange cartridges (50 g). The cartridges were washed with DCM, 1:1 MeOH:DCM and MeOH. The filtrates were discarded. The cartridges were washed with 2 M methanolic ammonia solution. The filtrates were combined and concentrated in vacuo. The residue was azeotroped with DCM then taken up in MeOH (45 mL) and stirred with SPM32 (3-mercaptopropyl ethyl sulfide silica) for 2 hours at ambient temperature, then at 50° C. for 1 hour. The mixture was cooled and filtered through celite and the filtrate concentrated in vacuo. The residue was taken up in DCM and concentrated in vacuo. The residue was dried overnight under vacuum to give N-(((3S,5S)-4,4-difluoro-5-methylpiperidin-3-yl)methyl)methanesulfonamide as a white solid (4.40 g, 91%); $^1$H NMR (400 MHz, DMSO-d$_6$) δ 7.10 (t, 1H), 3.43-3.33 (m, 1H), 3.26-3.10 (m, 1H), 2.93-2.88 (m, 4H), 2.79 (dtd, 1H), 2.38-2.20 (m, 2H), 2.13-1.78 (m, 2H), 0.89 (d, 3H); MS m/z: 243.0 (M+H)$^+$.

Preparation 178:
2,5-Dimethyl-3-((methylsulfinyl)methyl)piperidine

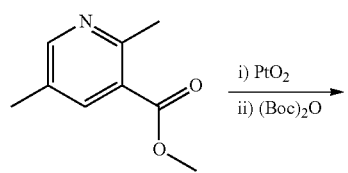

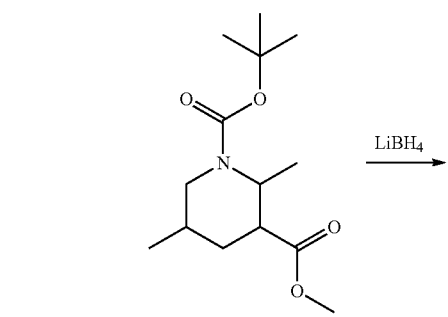

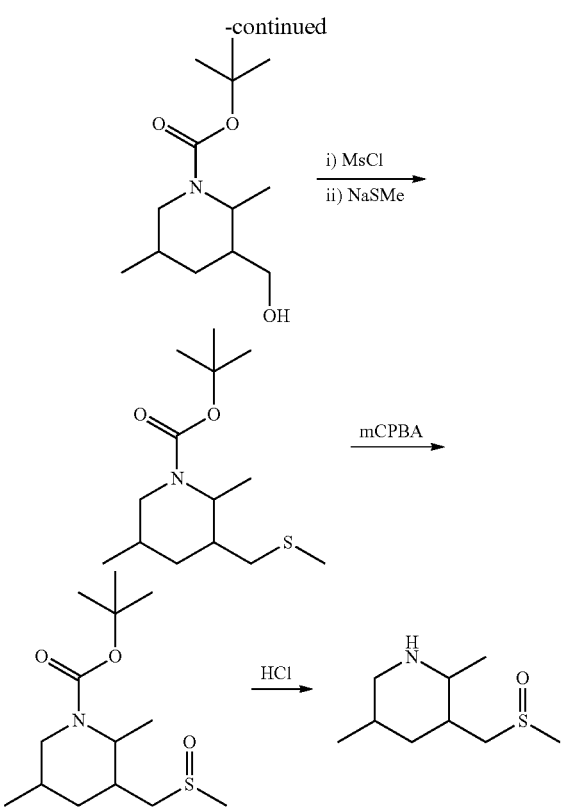

Step 1: 1-(tert-Butyl) 3-methyl 2,5-dimethylpiperidine-1,3-dicarboxylate

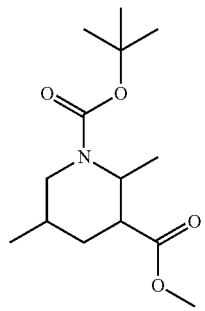

A mixture of methyl 2,5-dimethylpyridine-3-carboxylate (2.6 g, 15.74 mmol) and PtO$_2$ (713 mg, 3.14 mmol) in HCl (57 mL of a 3 M solution in MeOH, 171.1 mmol) was stirred under a balloon of H$_2$. The reaction mixture was stirred overnight before being filtered through Celite and the filtrate concentrated in vacuo. The residue was dissolved in THF (27 mL) and triethylamine (6.6 mL, 47.3 mmol), DMAP (96 mg, 0.79 mmol) and di-tert-butyl dicarbonate (17.4 mL of a 1 M solution in THF, 17.4 mmol) sequentially added. The reaction mixture was stirred overnight, then partitioned between EtOAc and water. The organic layer was separated and washed with NH$_4$Cl solution, water (1×), brine (1×), then dried (MgSO$_4$), filtered and concentrated in vacuo. The residue was purified by chromatography (silica, 0-10% EtOAc-/petroleum ether gradient elution) to give 1-(tert-butyl) 3-methyl 2,5-dimethylpiperidine-1,3-dicarboxylate (1.4 g, 33%) as a colourless oil containing a mixture of diastereomers; $^1$H NMR (400 MHz, d$_4$-methanol) δ 4.80-4.62 (m, 1H), 3.95-3.78 (m, 1H), 3.71 (d, 3H), 2.71 (dq, 1H), 2.46 (dt, 1H), 1.89-1.77 (m, 1H), 1.48 (q, 10H), 1.10-0.92 (m, 7H).

Step 2. tert-Butyl 3-(hydroxymethyl)-2,5-dimethylpiperidine-1-carboxylate

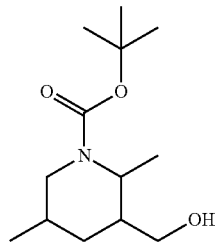 [SMILES: CC1CC(CO)C(C)N(C(=O)OC(C)(C)C)C1]

O1-tert-Butyl O3-methyl 2,5-dimethylpiperidine-1,3-dicarboxylate (1400 mg, 5.16 mmol) was dissolved in THF (42 mL) and cooled to 0° C. Lithium borohydride (10.3 mL of a 2 M solution in THF, 20.6 mmol) was added and the reaction allowed to warm to ambient temperature. After 30 minutes the reaction mixture was warmed to 50° C. and stirred overnight. The reaction was cooled to ambient temperature then quenched with water. The mixture was extracted with EtOAc (×3). The combined organics were dried and concentrated in vacuo to give tert-butyl 3-(hydroxymethyl)-2,5-dimethyl-piperidine-1-carboxylate (1.25 g, 100%) as a colourless oil that was taken directly on to the next reaction without further purification; $^1$H NMR (400 MHz, methanol-d$_4$) δ 4.42-4.27 (m, 1H), 3.82-3.68 (m, 1H), 3.34-3.23 (m, 2H), 2.33 (dt, 1H), 1.91 (s, 1H), 1.82-1.68 (m, 1H), 1.54-1.37 (m, 2H), 1.35 (s, 9H), 0.95-0.87 (m, 3H), 0.86-0.76 (m, 4H).

Step 3: tert-Butyl 2,5-dimethyl-3-(((methylsulfonyl)oxy)methyl)piperidine-1-carboxylate

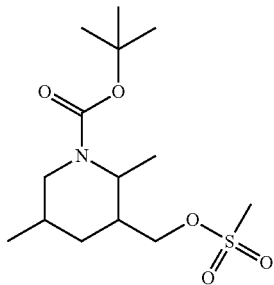 [SMILES: CC1CC(COS(C)(=O)=O)C(C)N(C(=O)OC(C)(C)C)C1]

Methanesulfonyl chloride (2.77 mL, 35.7 mmol) was added to a solution of tert-butyl 3-(hydroxymethyl)-2,5-dimethylpiperidine-1-carboxylate (5.80 g, 23.8 mmol) and triethylamine (6.64 mL, 47.7 mmol) in DCM (116 mL) stirring at 0° C. After 30 mins the reaction was quenched with saturated aq. NaHCO$_3$, stirred for 5 mins and then the layers separated using a phase separator cartridge. The organic phase was evaporated in vacuo to give tert-butyl 2,5-dimethyl-3-(((methylsulfonyl)oxy)methyl)piperidine-1-carboxylate (7.6 g) which was used directly in the next step without further purification.

Step 4: tert-Butyl 2,5-dimethyl-3-((methylthio)methyl)piperidine-1-carboxylate

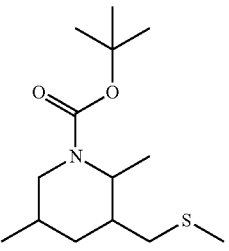

Sodium thiomethoxide (9.939 g, 141.8 mmol) was added to a solution of tert-butyl 2,5-dimethyl-3-(((methylsulfonyl)oxy)methyl)piperidine-1-carboxylate (7.6 g, 23.6 mmol) in EtOH (99 mL), stirring at 0° C. After addition, cooling was removed and the reaction heated at 60° C. overnight. The reaction was cooled to ambient temperature, concentrated in vacuo and purified by column chromatography (SiO$_2$, eluting with 0-12.5% MeOH in DCM gradient) to give tert-butyl 2,5-dimethyl-3-((methylthio)methyl)piperidine-1-carboxylate (3.4 g, 66%) as a colourless oil; $^1$H NMR (500 MHz, Methanol-d$_4$) δ 4.53-4.43 (m, 1H), 3.86 (td, J=13.3, 4.4 Hz, 1H), 2.53-2.31 (m, 3H), 2.10 (s, 3H), 1.91-1.81 (m, 1H), 1.74-1.63 (m, 1H), 1.61-1.50 (m, 1H), 1.48 (s, 9H), 1.10-0.99 (m, 4H), 0.93 (t, J=6.4 Hz, 3H).

Step 5. tert-Butyl 2,5-dimethyl-3-((methylsulfinyl)methyl)piperidine-1-carboxylate

tert-Butyl 2,5-dimethyl-3-((methylthio)methyl)piperidine-1-carboxylate (2 g, 7.31 mmol) was dissolved in DCM (73 mL) and the solution cooled to 0° C. m-CPBA (1.80 g, 7.31 mmol) was added portionwise over 5 mins and the reaction stirred for a further 5 mins before being quenched by addition of saturated aq. sodium thiosulphate (40 mL) and stirred for 5 min before extracting with DCM (3×50 mL). The combined organics were washed with with saturated aq. NaHCO$_3$ (2×40 mL), filtered through a phase separator cartridge and concentrated in vacuo to give tert-butyl 2,5-dimethyl-3-((methylsulfinyl)methyl)piperidine-1-carboxylate (2.1 g, 100%) as a colourless oil which was used without further purification.

Step 6:
2,5-Dimethyl-3-((methylsulfinyl)methyl)piperidine

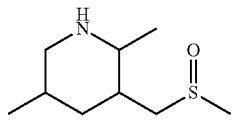

tert-Butyl 2,5-dimethyl-3-((methylsulfinyl)methyl)piperidine-1-carboxylate (2.1 g, 7.26 mmol) was dissolved in methanol (36 mL) and 4 M HCl in dioxane (9.1 mL, 36.3 mmol) was added. The reaction was stirred overnight before being concentrated in vacuo to give 2,5-dimethyl-3-((methylsulfinyl)methyl)piperidine (1.85 g, 97%) as a white solid; MS m/z: 190.1 (M+H)+.

Preparation 179: Imino(methyl)(piperidin-3-ylmethyl)-$\lambda^6$-sulfanone

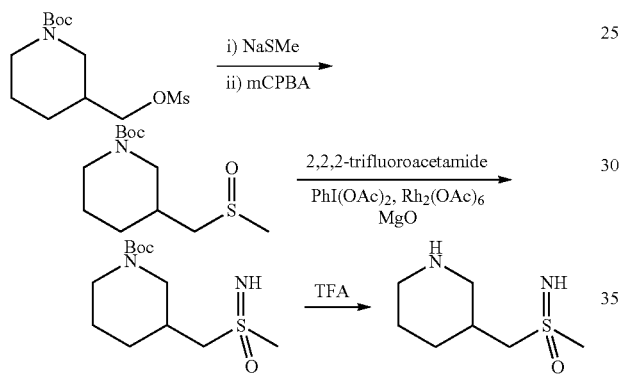

Sodium thiomethoxide (4.06 g, 58 mmol) was added to a solution of tert-butyl 3-(methylsulfonyloxymethyl)piperidine-1-carboxylate (8.5 g, 29 mmol) in EtOH (170 mL). The mixture was stirred at ambient temperature for 6 hours then concentrated in vacuo. The residue was partitioned between DCM and saturated aqueous NaHCO₃ solution. The organic phase was dried and concentrated in vacuo. The residue was purified by chromatography (silica, MeOH/DCM gradient elution) to give a pale yellow oil (6.9 g).

This material was dissolved in DCM (100 mL) and the solution cooled in an ice bath. m-CPBA (6.93 g of 70% pure w/w, 28 mmol) was added portionwise. After addition was complete the reaction mixture was stirred for 10 minutes then partitioned between DCM, saturated aqueous sodium bicarbonate solution and saturated aqueous sodium thiosulfate solution. The organic phase was dried and concentrated in vacuo. The residue was purified by chromatography (silica, DCM/MeOH gradient elution) to give the product as a colourless oil.

tert-Butyl 3-((methylsulfinyl)methyl)piperidine-1-carboxylate (5.5 g, 21.0 mmol), 2,2,2-trifluoroacetamide (5.23 g, 46.3 mmol), (diacetoxyiodo)benzene (10.17 g, 31.6 mmol) and magnesium oxide (3.39 g, 84.2 mmol) were dissolved in DCM (250 mL) and diacetoxy(diacetoxyrhodio)rhodium (0.9 g, 2.04 mmol) was added. The mixture was stirred at ambient temperature overnight before being filtered through Celite and concentrated in vacuo. The residue was dissolved in methanol (50 mL) and water (10 mL) and K₂CO₃ (17.44 g, 126.2 mmol) was added. The mixture was stirred at ambient temperature for 3 hours before heating 50° C. for 3 days. The mixture was concentrated in vacuo and the residue dissolved in methanol (5 mL) and acetonitrile/water (3:1 mixture, 5 mL). After 1.5 hours at 90° C. the mixture was cooled, diluted in EtOAc and washed with brine and saturated aq. NaHCO₃ solution. The organic layer was dried (Na₂SO₄) and concentrated in vacuo to give tert-butyl 3-((S-methylsulfonimidoyl)methyl)piperidine-1-carboxylate (5.96 g) as an amber oil which was used without further purification.

A solution of tert-butyl 3-[(methyl sulfonimidoyl)methyl]piperidine-1-carboxylate (600 mg, 2.17 mmol) and TFA (1.67 mL, 21.71 mmol) in DCM (3 mL) was stirred at ambient temperature overnight before being concentrated in vacuo and the residue passed through an SCX-2 cartridge. The product was eluted with ammonia in methanol to give imino(methyl)(piperidin-3-ylmethyl)-$\lambda^6$-sulfanone (250 mg, 65%); $^1$H NMR (500 MHz, Methanol-$d_4$) δ 3.34-3.24 (m, 1H), 3.19-3.10 (m, 2H), 3.10-3.07 (m, 3H), 3.05-2.97 (m, 1H), 2.60 (ddd, J=12.4, 11.5, 3.1 Hz, 1H), 2.52-2.43 (m, 1H), 2.30-2.18 (m, 1H), 2.08 (ddtd, J=30.1, 10.9, 3.8, 1.8 Hz, 1H), 1.75 (dq, J=13.8, 3.3 Hz, 1H), 1.61 (dtq, J=13.6, 11.5, 3.8 Hz, 1H), 1.37 (dtd, J=12.8, 11.3, 3.9 Hz, 1H).

Preparation 180:
2-Chloro-4-methyl-6-(methylthio)pyrimidine

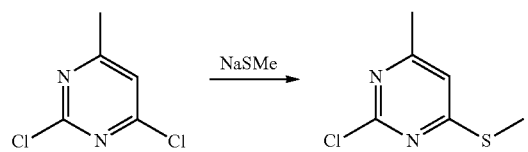

Sodium thiomethoxide (6.4 mL of 21% w/v, 19.2 mmol) was added to a solution of 2,4-dichloro-6-methyl-pyrimidine (3.0 g, 18.4 mmol) in THF (50 mL), stirring at 0° C. The reaction mixture was stirred for 18 h, gradually warming up to ambient temperature. The reaction was diluted in EtOAc and washed with saturated aq. NaHCO₃. The layers were separated and the aqueous phase extracted with EtOAc. The combined organic phases were washed with brine, dried (Na₂SO₄) and concentrated in vacuo. Purification by column chromatography (silica, eluting with 0 to 100% ethyl acetate in petroleum ether) to give 2-chloro-4-methyl-6-(methylthio)pyrimidine (2.40 g, 75%) as a yellow solid; MS m/z: 175.0 (M+H)+.

Preparation 181: 1-(4-(2-Chloropyrimidin-4-yl)piperazin-1-yl)ethan-1-one and 1-(4-(4-chloropyrimidin-2-yl)piperazin-1-yl)ethan-1-one

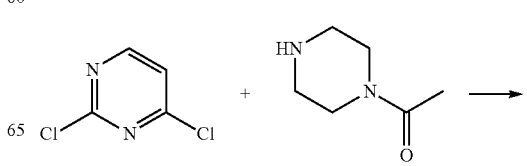

729

-continued

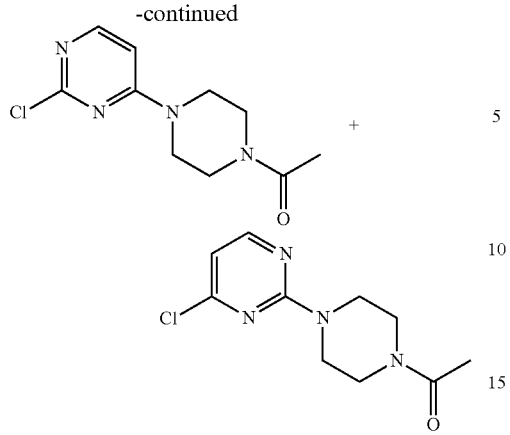

To a solution of 1-piperazin-1-ylethanone (1.72 g, 1.91 mL, 13.4 mmol) and triethylamine (1.43 g, 1.96 mL, 14.1 mmol) in 1,2-dimethoxyethane (30.0 mL) was added 2,4-dichloropyrimidine (2.0 g, 13.4 mmol) and the resultant suspension stirred at ambient temperature for 5 mins. The reaction mixture was filtered and the filtrate concentrated in vacuo. The residue was purified by column chromatography (silica, eluting with 5-100% EtOAC in hexanes) to give two products:

1-(4-(4-Chloropyrimidin-2-yl)piperazin-1-yl)ethan-1-one (0.33 g, 10%); $^1$H NMR (400 MHz, DMSO-d$_6$) δ 8.10 (d, J=5.1 Hz, 1H), 6.53 (d, J=5.1 Hz, 1H), 3.56-3.44 (m, 2H), 3.32-3.24 (m, 4H), 3.07 (s, 2H), 1.80 (s, 3H).

1-(4-(2-Chloropyrimidin-4-yl)piperazin-1-yl)ethan-1-one (1.23 g, 38%); $^1$H NMR (400 MHz, DMSO-d$_6$) δ 8.11 (d, J=6.2 Hz, 1H), 6.86 (d, J=6.2 Hz, 1H), 3.72-3.50 (m, 8H), 2.05 (s, 3H).

The following compounds were made using methodology similar to that described in Preparation 181:
1-(4-(2-Chloro-6-methylpyrimidin-4-yl)piperazin-1-yl)ethan-1-one;

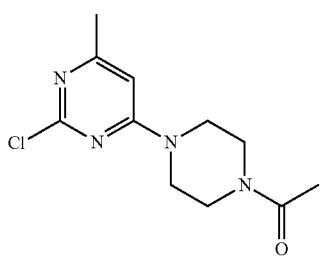 [SMILES: CC(=O)N1CCN(c2cc(C)nc(Cl)n2)CC1]

1-(4-(4-Chloro-6-methylpyrimidin-2-yl)piperazin-1-yl)ethan-1-one.

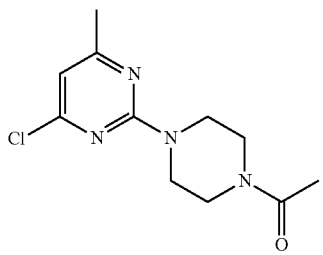 [SMILES: CC(=O)N1CCN(c2nc(C)cc(Cl)n2)CC1]

730

Preparation 182: 1-(4-(6-Chloropyrazin-2-yl)piperazin-1-yl)ethan-1-one

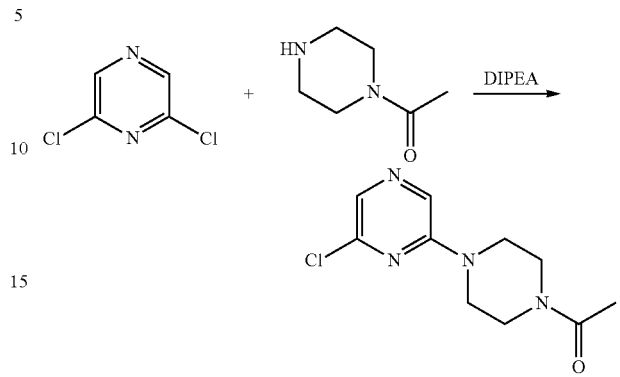

2,6-Dichloropyrazine (500 mg, 3.36 mmol), 1-piperazin-1-ylethanone (860 mg, 953 µL, 6.71 mmol) and DIPEA (1.75 mL, 10.1 mmol) were mixed and heated at 130° C. overnight in a sealed tube. The reaction mixture was allowed to cool to ambient temperature, then partitioned between EtOAc and water, the layers separated and the aqueous phase extracted with EtOAc. The combined organics were dried (MgSO$_4$) and concentrated in vacuo. Purification by column chromatography (silica, eluting with a gradient of 0-10% methanol in DCM) gave 1-(4-(6-chloropyrazin-2-yl)piperazin-1-yl)ethan-1-one (790 mg, 98%) as a white solid; $^1$H NMR (400 MHz, DMSO-d$_6$) δ 8.30 (s, 1H), 7.88 (s, 1H), 3.64 (td, J=4.7, 2.9 Hz, 2H), 3.57 (d, J=6.2 Hz, 2H), 3.35-3.27 (m, 1H), 2.70 (t, J=0.8 Hz, 1H), 2.18 (t, J=8.1 Hz, 1H), 2.05 (s, 3H), 1.97-1.84 (m, 1H).

The following compound was made using methodology similar to that described in Preparation 182:
1-(4-(6-Chloropyridin-2-yl)piperazin-1-yl)ethan-1-one.

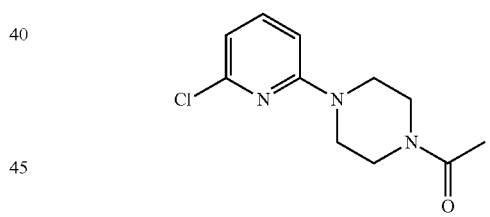

Preparation 183: (E)-2-(2-Ethoxyvinyl)-4-(methylthio)pyrimidine

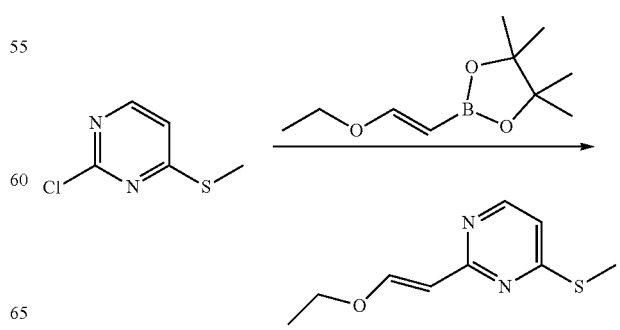

To a suspension of 2-chloro-4-(methylthio)pyrimidine (56.1 g, 349.3 mmol) and 2 M aq. $Na_2CO_3$ (524 mL, 1.05 mol) in 1,2-dimethoxyethane (730 mL) was added 2-[(E)-2-ethoxyvinyl]-4,4,5,5-tetramethyl-1,3,2-dioxaborolane (76.1 g, 384 mmol). $Pd(PPh_3)_4$ (20.2 g, 17.5 mmol) was added and the mixture degassed. The reaction was placed under a nitrogen atmosphere and heated at reflux for 4 hours. The mixture was cooled to ambient temperature and partitioned between EtOAc (1.1 L) and water (560 mL). The organic layer was washed with water (2×560 mL), the combined organic layers were re-extracted with EtOAc (280 mL) and the combined organic phases were washed with brine (×1), dried ($MgSO_4$), filtered and concentrated in vacuo. The residue was purified by column chromatography (silica, eluting with 0 to 25% EtOAc/petroleum ether) to give (E)-2-(2-ethoxyvinyl)-4-(methylthio)pyrimidine as a pale yellow, crystalline solid (62.4 g, 91%); $^1$H NMR (500 MHz, Chloroform-d) δ 8.18 (d, J=5.5 Hz, 1H), 7.95 (d, J=12.6 Hz, 1H), 6.85 (d, J=5.5 Hz, 1H), 5.91 (d, J=12.6 Hz, 1H), 4.02 (q, J=7.0 Hz, 2H), 2.56 (s, 3H), 1.40 (t, J=7.0 Hz, 3H); ES+ [M+H]=197.1.

The following compounds were made using methodology similar to that described in Preparation 183:

(E)-2-Chloro-4-(2-ethoxyvinyl)pyrimidine;

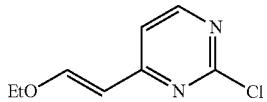 [SMILES: CCO/C=C/c1ccnc(Cl)n1]

(E)-1-(4-(2-(2-Ethoxyvinyl)pyrimidin-4-yl)piperazin-1-yl)ethan-1-one;

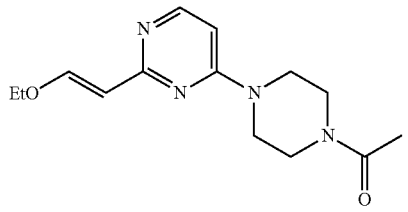 [SMILES: CCO/C=C/c1nccc(N2CCN(C(C)=O)CC2)n1]

(E)-1-(4-(4-(2-Ethoxyvinyl)pyrimidin-2-yl)piperazin-1-yl)ethan-1-one;

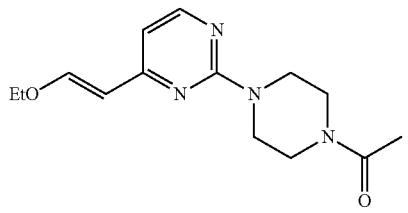 [SMILES: CCO/C=C/c1ccnc(N2CCN(C(C)=O)CC2)n1]

(E)-2-(2-Ethoxyvinyl)-5-fluoro-4-(methylthio)pyrimidine;

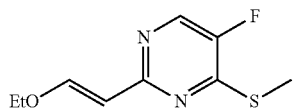

(E)-2-(2-Ethoxyvinyl)-4-methyl-6-(methylthio)pyrimidine;

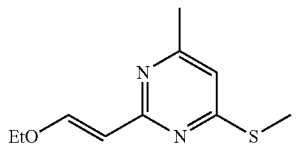

(E)-1-(4-(6-(2-Ethoxyvinyl)pyrazin-2-yl)piperazin-1-yl)ethan-1-one;

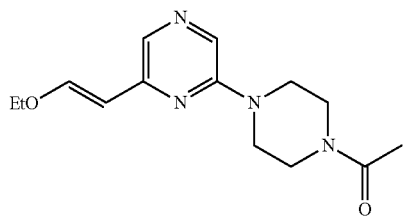 [SMILES: CCO/C=C/c1cncc(N2CCN(C(C)=O)CC2)n1]

(E)-1-(4-(2-(2-ethoxyvinyl)-6-methylpyrimidin-4-yl)piperazin-1-yl)ethan-1-one;

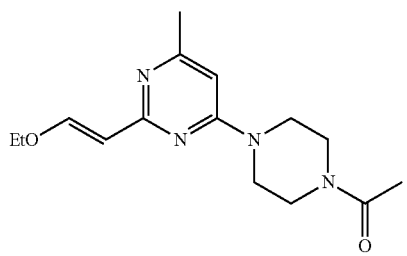 [SMILES: CCO/C=C/c1nc(C)cc(N2CCN(C(C)=O)CC2)n1]

(E)-1-(4-(4-(2-ethoxyvinyl)-6-methylpyrimidin-2-yl)piperazin-1-yl)ethan-1-one;

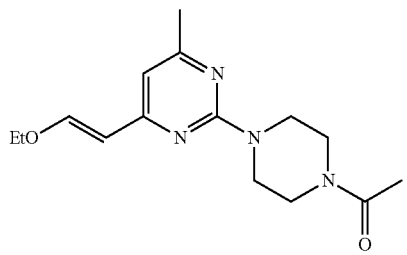 [SMILES: CCO/C=C/c1cc(C)nc(N2CCN(C(C)=O)CC2)n1]

(E)-1-(4-(6-(2-Ethoxyvinyl)pyridin-2-yl)piperazin-1-yl)ethan-1-one;

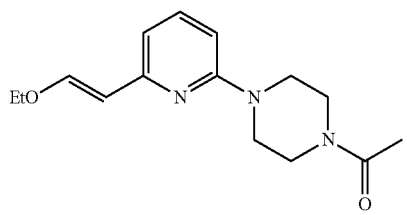 [SMILES: CCO/C=C/c1cccc(N2CCN(C(C)=O)CC2)n1]

733

(E)-2-Chloro-6-(2-ethoxyvinyl)pyridine;

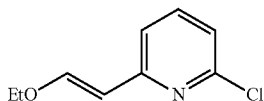 [SMILES: CCO/C=C/c1cccc(Cl)n1]

(E)-2-(2-ethoxyvinyl)-6-fluoropyridine;

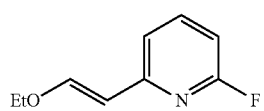

(E)-2-Bromo-6-(2-ethoxyvinyl)pyridine;

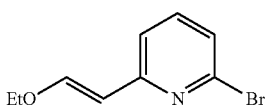

(E)-2-(2-Ethoxyvinyl)-4,6-difluoropyridine;

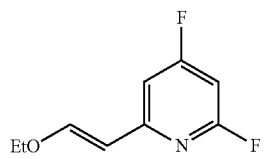 [SMILES: CCO/C=C/c1cc(F)cc(F)n1]

(E)-4,6-Dichloro-2-(2-ethoxyvinyl)pyrimidine;

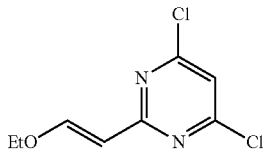 [SMILES: CCO/C=C/c1nc(Cl)cc(Cl)n1]

(E)-2-Bromo-4-(2-ethoxyvinyl)-5-fluoropyrimidine.

Preparation 184: 5-(Difluoromethyl)pyrazin-2-amine

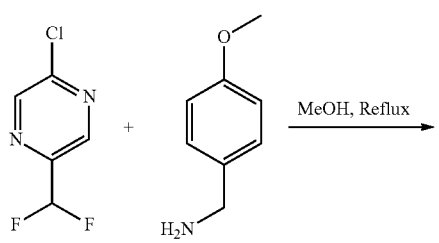

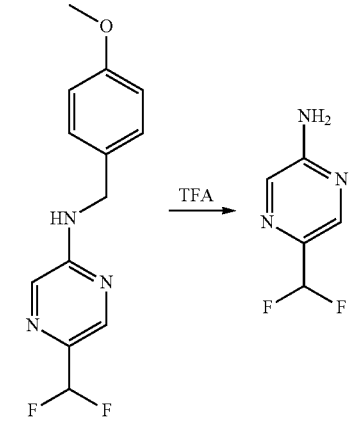

Step 1: 5-(Difluoromethyl)-N-(4-methoxybenzyl)pyrazin-2-amine

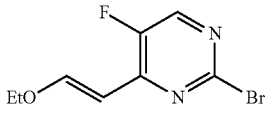

(4-methoxyphenyl)methanamine (35 mL, 267.9 mmol) was added to a stirred solution of 2-chloro-5-(difluoromethyl)pyrazine (17.4 g, 105.7 mmol) in THF (174 mL) and the reaction heated at reflux overnight. The resulting yellow suspension was cooled to ambient temperature then partitioned between EtOAc and water. The aqueous phase was removed and the organics further washed with water (2×), brine (1×), dried (MgSO$_4$), filtered and concentrated in vacuo. The crude product was purified by column chromatography (silica, eluting with 0 to 30% EtOAc/petroleum ether) to give 5-(difluoromethyl)-N-[(4-methoxyphenyl)methyl]pyrazin-2-amine as a white solid, (17.7 g, 63%); $^1$H NMR (500 MHz, DMSO-d$_6$) δ 8.20 (q, J=1.3 Hz, 1H), 8.04 (t, J=5.9 Hz, 1H), 8.01 (d, J=1.4 Hz, 1H), 7.28-7.25 (m, 2H), 6.91-6.88 (m, 2H), 6.84 (t, J=54.9 Hz, 1H), 4.46 (d, J=5.8 Hz, 2H), 3.73 (s, 3H); $^{19}$F NMR (471 MHz, DMSO-d$_6$) δ −113.02; ES+ [M+H]=266.2.

Step 2: 5-(Difluoromethyl)pyrazin-2-amine

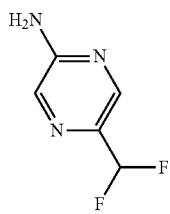

A solution of 5-(difluoromethyl)-N-[(4-methoxyphenyl)methyl]pyrazin-2-amine (17.7 g, 66.7 mmol) in TFA (130 mL) was stirred at 60° C. for 2 hours. The reaction mixture was cooled to ambient temperature and the solvent removed in vacuo. The residue was azeotroped with DCM (×2) and dried further. The resulting orange solid was dissolved in DCM and saturated aq. NaHCO$_3$ was added slowly until the solution was at pH 8. The layers were separated and the aqueous layer extracted with DCM (×2). The combined organic extracts were dried (MgSO$_4$), filtered and concentrated in vacuo. The residue was purified by column chromatography (silica, eluting with 0 to 50% EtOAc/petroleum ether) to give 5-(difluoromethyl)pyrazin-2-amine as a pale yellow solid (7.5 g, 77%); $^1$H NMR (500 MHz, DMSO-d$_6$) δ 8.14 (q, J=1.4 Hz, 1H), 7.90 (d, J=1.4 Hz, 1H), 6.96 (s, 2H), 6.82 (t, J=55.0 Hz, 1H); ES+ [M+H]=146.0.

Preparation 185: 1-(5-Aminopyrazin-2-yl)ethan-1-one

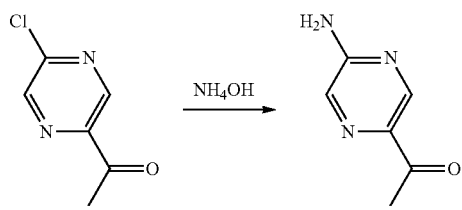

Ammonium hydroxide solution (224 mg, 249 μL, 6.39 mmol) was added to a solution of 1-(5-chloropyrazin-2-yl)ethanone (50 mg, 0.3193 mmol) in THF (1 mL) and the mixture heated in a microwave vial at 110° C. in the microwave for 1 hour. The reaction mixture was concentrated in vacuo, the residue triturated with a minimum of EtOAc and the solid dried in vacuo to yield 1-(5-aminopyrazin-2-yl)ethan-1-one (31 mg, 71%); ES+ [M+H]=138.1.

Preparation 186: 6-(Difluoromethyl)-3-(4-(methylthio)pyrimidin-2-yl)imidazo[1,2-a]pyrazine

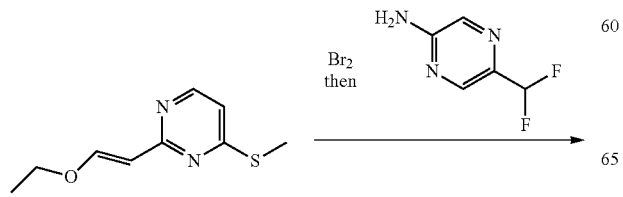

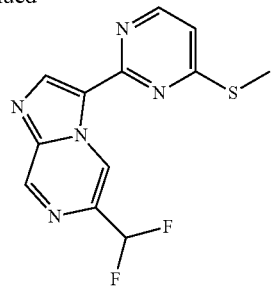

N-Bromosuccinimide (570 mg, 3.20 mmol) was added to a stirred solution of (E)-2-(2-ethoxyvinyl)-4-(methylthio)pyrimidine (630 mg, 3.21 mmol) in dioxane (10 mL) and water (3.75 mL) and the reaction mixture stirred at ambient temperature for 20 mins. 5-(Difluoromethyl)pyrazin-2-amine (460 mg, 3.170 mmol) in dioxane (0.5 mL) was added and the reaction mixture heated at 80° C. for 2 h. The mixture was cooled to ambient temperature before saturated aq. NaHCO$_3$ (10 mL) was added slowly, followed by water (40 mL). The reaction was stirred for 10 minutes and the resultant precipitate isolated by filtration, washing with water. The solid was taken up in DCM, passed through a phase separation cartridge to remove water and concentrated in vacuo to give 6-(difluoromethyl)-3-(4-(methylthio)pyrimidin-2-yl)imidazo[1,2-a]pyrazine as a brown solid (734 mg, 79%); $^1$H NMR (500 MHz, DMSO-d$_6$) δ 10.05-10.04 (m, 1H), 9.36 (d, J=1.4 Hz, 1H), 8.76 (s, 1H), 8.64 (d, J=5.5 Hz, 1H), 7.44 (d, J=5.5 Hz, 1H), 7.25 (t, J=54.5 Hz, 1H), 2.71 (s, 3H); $^{19}$F NMR (471 MHz, DMSO) δ −116.13.

The following compounds were made using methodology similar to that described in Preparation 186:

3-(4-(Methylthio)pyrimidin-2-yl)imidazo[1,2-a]pyrazine-6-carbonitrile;

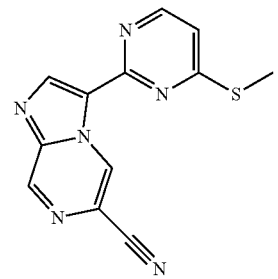 [SMILES: CSc1ccnc(-c2cnc3cnc(C#N)cn23)n1]

3-(4-(Methylthio)pyrimidin-2-yl)imidazo[1,2-a]pyrazine-6-carboxamide;

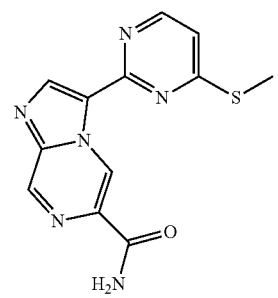 [SMILES: CSc1ccnc(-c2cnc3cnc(C(N)=O)cn23)n1]

737

3-(6-Chloropyridin-2-yl)imidazo[1,2-a]pyrazine-6-carboxamide;

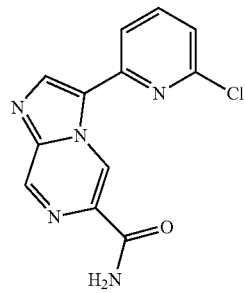 [SMILES: NC(=O)c1cn2c(-c3cccc(Cl)n3)cnc2cn1]

6-Methyl-3-(4-(methylthio)pyrimidin-2-yl)imidazo[1,2-a]pyrazine;

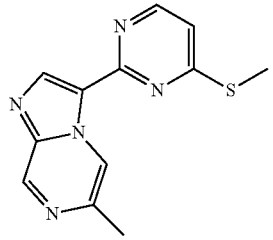 [SMILES: CSc1ccnc(-c2cnc3cnc(C)cn23)n1]

1-(3-(4-(Methylthio)pyrimidin-2-yl)imidazo[1,2-a]pyrazin-6-yl)ethan-1-one;

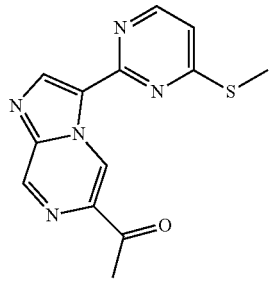 [SMILES: CSc1ccnc(-c2cnc3cnc(C(C)=O)cn23)n1]

3-(4-(Methylthio)pyrimidin-2-yl)-6-(trifluoromethyl)imidazo[1,2-a]pyrazine;

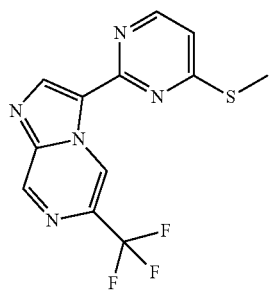 [SMILES: CSc1ccnc(-c2cnc3cnc(C(F)(F)F)cn23)n1]

738

6-Chloro-3-(4-(methylthio)pyrimidin-2-yl)imidazo[1,2-a]pyrazine;

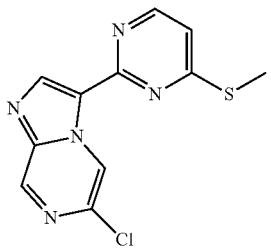 [SMILES: CSc1ccnc(-c2cnc3cnc(Cl)cn23)n1]

6-Bromo-3-(4-(methylthio)pyrimidin-2-yl)imidazo[1,2-a]pyrazine;

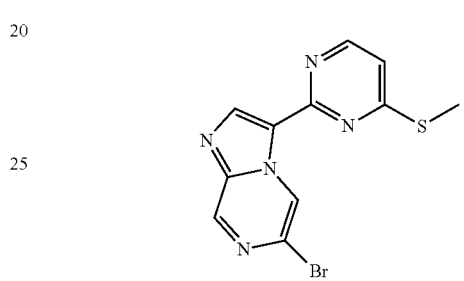

3-(2-Chloropyrimidin-4-yl)-6-(trifluoromethyl)imidazo[1,2-a]pyrazine;

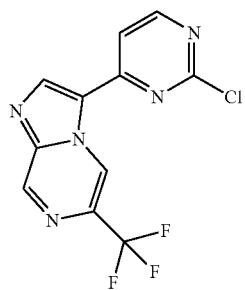 [SMILES: FC(F)(F)c1cn2c(-c3ccnc(Cl)n3)cnc2cn1]

3-(2-Chloropyrimidin-4-yl)-6-(difluoromethyl)imidazo[1,2-a]pyrazine;

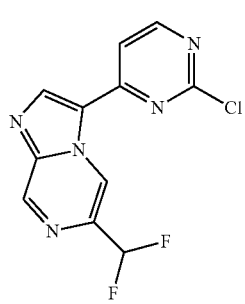 [SMILES: FC(F)c1cn2c(-c3ccnc(Cl)n3)cnc2cn1]

3-(5-Fluoro-4-(methylthio)pyrimidin-2-yl)-6-(trifluoromethyl)imidazo[1,2-a]pyrazine;

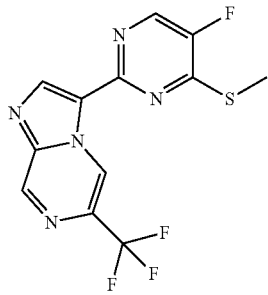 [SMILES: CSc1nc(-c2cnc3cnc(C(F)(F)F)cn23)ncc1F]

3-(4-Methyl-6-(methylthio)pyrimidin-2-yl)-6-(trifluoromethyl)imidazo[1,2-a]pyrazine;

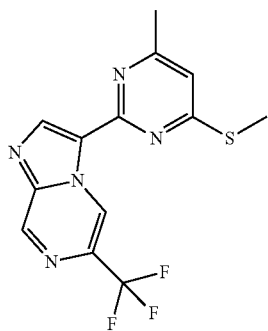 [SMILES: CSc1cc(C)nc(-c2cnc3cnc(C(F)(F)F)cn23)n1]

3-(6-Chloropyridin-2-yl)-6-(difluoromethyl)imidazo[1,2-a]pyrazine;

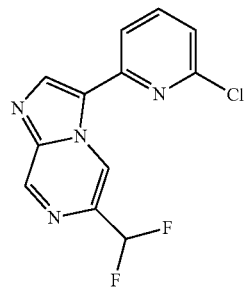 [SMILES: FC(F)c1cn2c(-c3cccc(Cl)n3)cnc2cn1]

3-(6-Chloropyridin-2-yl)-6-(trifluoromethyl)imidazo[1,2-a]pyrazine;

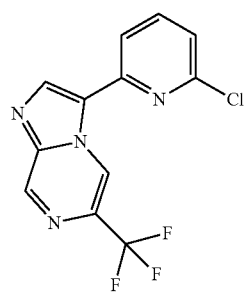 [SMILES: FC(F)(F)c1cn2c(-c3cccc(Cl)n3)cnc2cn1]

3-(6-Chloropyridin-2-yl)imidazo[1,2-a]pyrazine-6-carbonitrile;

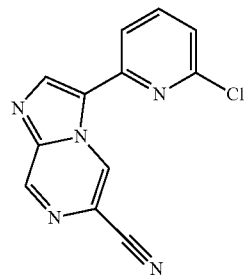 [SMILES: N#Cc1cn2c(-c3cccc(Cl)n3)cnc2cn1]

Methyl 3-(6-chloropyridin-2-yl)imidazo[1,2-a]pyrazine-6-carboxylate;

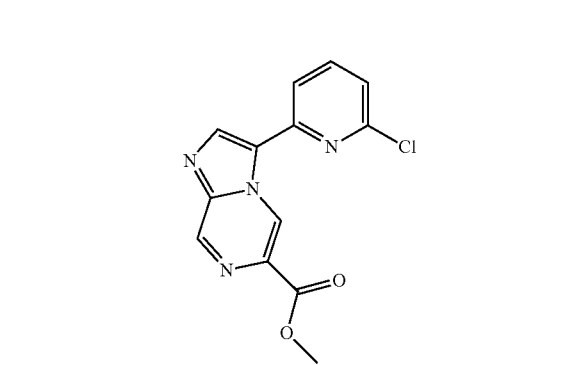 [SMILES: COC(=O)c1cn2c(-c3cccc(Cl)n3)cnc2cn1]

6-Bromo-3-(4-(methylthio)pyrimidin-2-yl)imidazo[1,2-a]pyrazine;

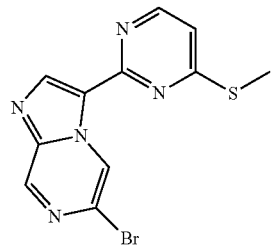 [SMILES: CSc1ccnc(-c2cnc3cnc(Br)cn23)n1]

6-Cyclopropyl-3-(4-(methylthio)pyrimidin-2-yl)imidazo[1,2-a]pyrazine;

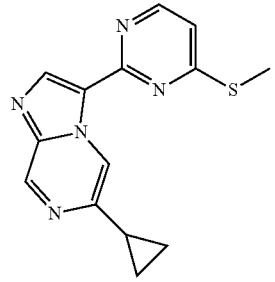 [SMILES: CSc1ccnc(-c2cnc3cnc(C4CC4)cn23)n1]

6-(Difluoromethyl)-3-(6-fluoropyridin-2-yl)imidazo[1,2-a]pyrazine;

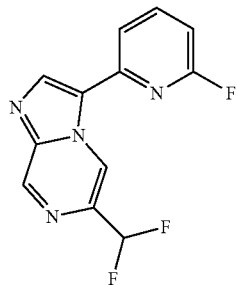 [SMILES: Fc1cccc(-c2cnc3cnc(C(F)F)cn23)n1]

3-(6-Bromopyridin-2-yl)-6-(trifluoromethyl)imidazo[1,2-a]pyrazine;

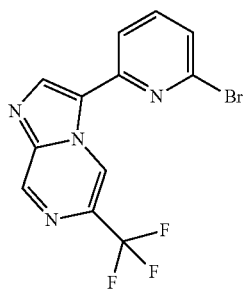 [SMILES: FC(F)(F)c1cn2c(-c3cccc(Br)n3)cnc2cn1]

3-(4,6-Difluoropyridin-2-yl)-6-(trifluoromethyl)imidazo[1,2-a]pyrazine;

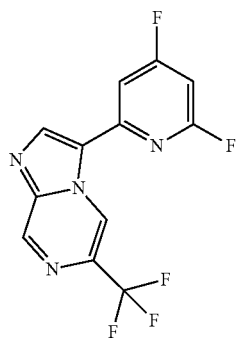 [SMILES: Fc1cc(F)nc(-c2cnc3cnc(C(F)(F)F)cn23)c1]

3-(4,6-Dichloropyrimidin-2-yl)-6-(trifluoromethyl)imidazo[1,2-a]pyrazine.

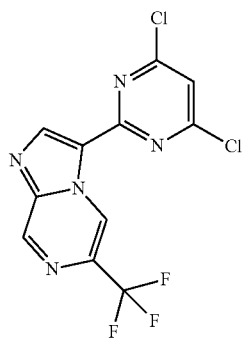 [SMILES: FC(F)(F)c1cn2c(-c3nc(Cl)cc(Cl)n3)cnc2cn1]

The following final compounds were also made using methodology similar to that described in Preparation 186:

1-(4-(2-(6-(Trifluoromethyl)imidazo[1,2-a]pyrazin-3-yl)pyrimidin-4-yl)piperazin-1-yl)ethan-1-one IV-24;

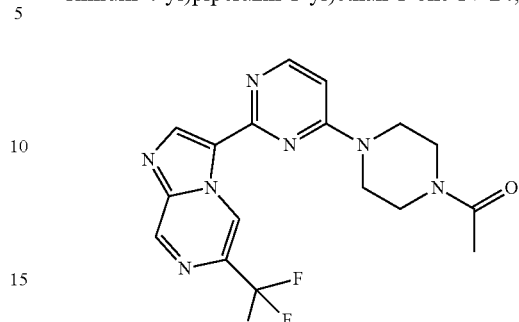

1-(4-(2-(6-Methoxyimidazo[1,2-a]pyrazin-3-yl)pyrimidin-4-yl)piperazin-1-yl)ethan-1-one IV-25;

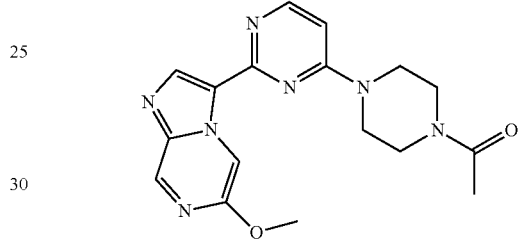

1-(4-(2-(6-(Hydroxymethyl)imidazo[1,2-a]pyrazin-3-yl)pyrimidin-4-yl)piperazin-1-yl)ethan-1-one IV-26;

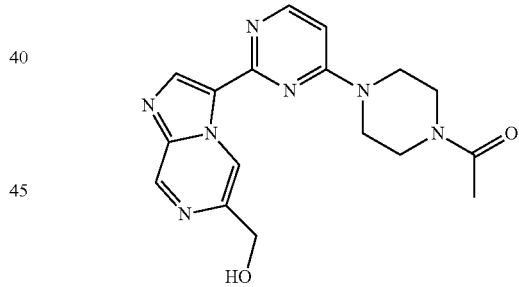

3-(4-(4-Acetylpiperazin-1-yl)pyrimidin-2-yl)imidazo[1,2-a]pyrazine-6-carboxylic acid IV-30;

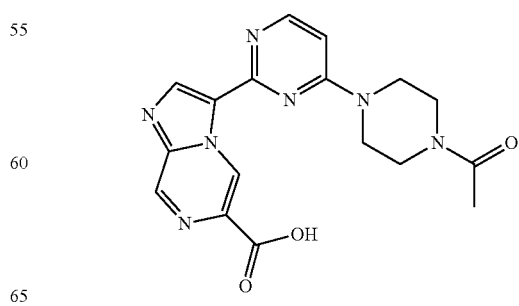

3-(4-(4-Acetylpiperazin-1-yl)pyrimidin-2-yl)imidazo[1,2-a]
pyrazine-6-carbonitrile IV-31;

1-(4-(2-(6-Bromoimidazo[1,2-a]pyrazin-3-yl)pyrimidin-4-
yl)piperazin-1-yl)ethan-1-one IV-32;

1-(4-(2-(6-Cyclopropylimidazo[1,2-a]pyrazin-3-yl)pyrimi-
din-4-yl)piperazin-1-yl)ethan-1-one IV-33;

3-(2-(4-Acetylpiperazin-1-yl)pyrimidin-4-yl)imidazo[1,2-a]
pyrazine-6-carboxamide IV-182;

3-(6-(4-Acetylpiperazin-1-yl)pyrazin-2-yl)imidazo[1,2-a]
pyrazine-6-carboxamide IV-183;

3-(2-(4-Acetylpiperazin-1-yl)-6-methylpyrimidin-4-yl)imi-
dazo[1,2-a]pyrazine-6-carboxamide IV-188;

3-(4-(4-Carbamoylpiperazin-1-yl)-6-methylpyrimidin-2-yl)
imidazo[1,2-a]pyrazine-6-carboxamide IV-196;

1-(4-(6-(6-(1H-Pyrazol-1-yl)imidazo[1,2-a]pyrazin-3-yl)
pyridin-2-yl)piperazin-1-yl)ethan-1-one IV-209.

Preparation 187: 6-(1,1-Difluoroethyl)-3-(4-(methylthio)pyrimidin-2-yl)imidazo[1,2-a]pyrazine

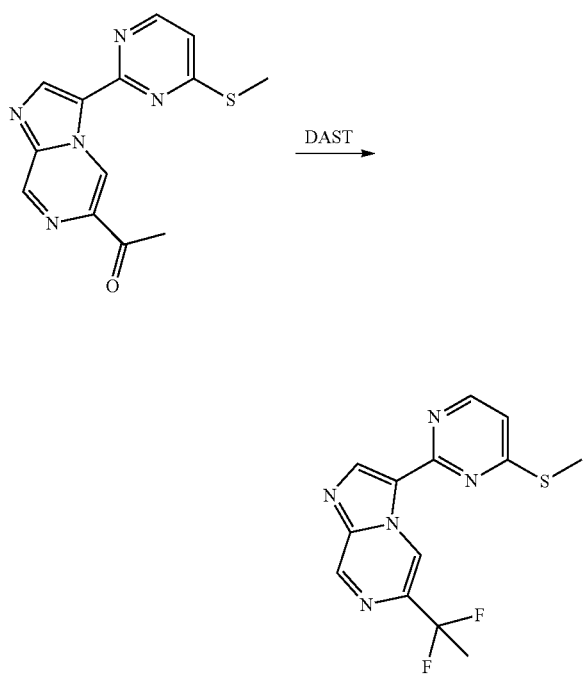

DAST (297 mg, 243 µL, 1.84 mmol) was added to a solution of 1-(3-(4-(methylthio)pyrimidin-2-yl)imidazo[1,2-a]pyrazin-6-yl)ethan-1-one (35 mg, 0.12 mmol) in DCM (1 mL) and the mixture stirred at room temperature overnight. A further three portions of DAST were added (297 mg each, 243 µL, 1.84 mmol) at 24 hours intervals and the reaction stirred for a further 7 days after addition was completed. The reaction was quenched by addition of a mixture of saturated aq. NaHCO₃ solution and ice and the product extracted with DCM. The organic layer was dried (MgSO₄) and concentrated in vacuo to give 6-(1,1-difluoroethyl)-3-(4-(methylthio)pyrimidin-2-yl)imidazo[1,2-a]pyrazine (37 mg, 98%) which was used without any further purification; ES+ [M+H]=308.2.

Preparation 188: 3-(6-Chloropyridin-2-yl)-N,N-dimethylimidazo[1,2-a]pyrazine-6-carboxamide

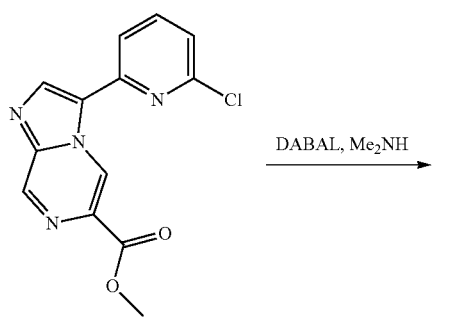

DABAL, Me₂NH →

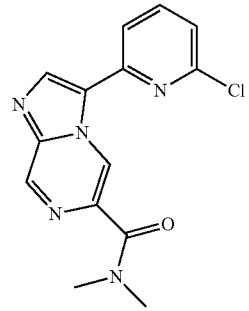 [SMILES: CNC(=O)c1cn2c(-c3cccc(Cl)n3)cnc2cn1]

N-Methylmethanamine (138 µL of 2 M, 0.28 mmol) and DABAL (56.5 mg, 0.22 mmol) were added to a solution of methyl 3-(6-chloropyridin-2-yl)imidazo[1,2-a]pyrazine-6-carboxylate (53 mg, 0.18 mmol) in THF (1 mL) and the reaction was heated at 130° C. in the microwave for 10 mins. The reaction mixture was quenched by dropwise addition of DMSO and water, then purified directly by reverse phase chromatography (C18; MeCN/water—0.05% TFA as eluent) to give 3-(6-chloropyridin-2-yl)-N,N-dimethylimidazo[1,2-a]pyrazine-6-carboxamide (15 mg, 27%) as a white solid; ¹H NMR (400 MHz, DMSO-d₆) δ 9.86 (d, J=1.4 Hz, 1H), 9.23 (d, J=1.4 Hz, 1H), 8.79 (s, 1H), 8.19 (dd, J=7.8, 0.7 Hz, 1H), 8.05 (t, J=7.9 Hz, 1H), 7.54 (dd, J=7.9, 0.7 Hz, 1H), 3.10 (d, J=19.8 Hz, 6H).

The following compound was made using methodology similar to that described in Preparation 188:

3-(6-Chloropyridin-2-yl)-N-methylimidazo[1,2-a]pyrazine-6-carboxamide;

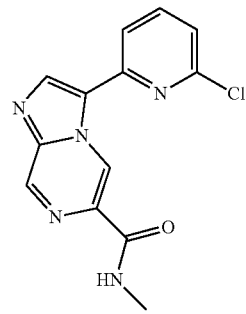

Preparation 189: 3-(4-Chloropyrimidin-2-yl)-6-(trifluoromethyl)imidazo[1,2-a]pyrazine

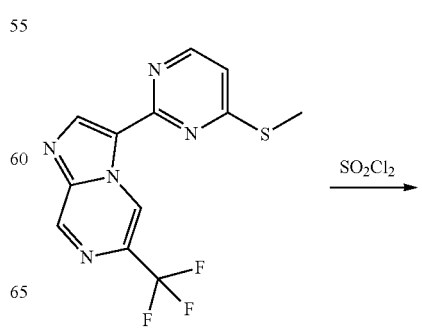

SO₂Cl₂ →

-continued

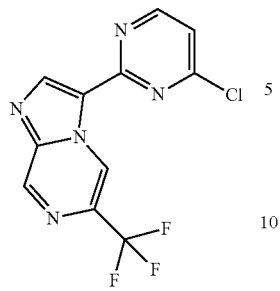

3-(4-(Methylthio)pyrimidin-2-yl)-6-(trifluoromethyl)imidazo[1,2-a]pyrazine (3 g, 9.6 mmol) was suspended in MeCN (51 mL) and concentrated HCl (1.52 g of 37% w/w, 844 μL of 37% w/w, 15.4 mmol) was added. Sulfuryl chloride (5.2 g, 3.12 mL, 38.6 mmol) was added to the suspension and the reaction mixture was stirred at ambient temperature for 15 mins. The reaction was quenched by addition of iced water (90 mL) and the resultant precipitate collected by filtration to give 3-(4-chloropyrimidin-2-yl)-6-(trifluoromethyl)imidazo[1,2-a]pyrazine as a pale yellow powder (2.85 g, 99%); $^1$H NMR (400 MHz, DMSO-$d_6$) δ 10.09 (s, 1H), 9.46 (d, J=1.4 Hz, 1H), 9.02 (d, J=5.4 Hz, 1H), 8.82 (s, 1H), 7.74 (d, J=5.4 Hz, 1H).

The following compounds were made using methodology similar to that described in Preparation 189:

3-(4-Chloropyrimidin-2-yl)imidazo[1,2-a]pyrazine-6-carboxamide;

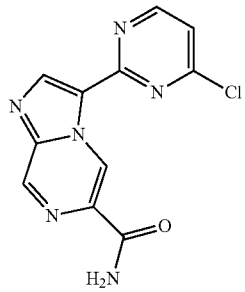 [SMILES: NC(=O)c1cn2c(-c3nccc(Cl)n3)cnc2cn1]

6-Bromo-3-(4-chloropyrimidin-2-yl)imidazo[1,2-a]pyrazine;

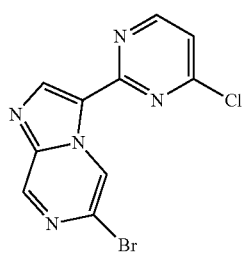 [SMILES: Clc1ccnc(-c2cnc3cnc(Br)cn23)n1]

3-(4-Chloropyrimidin-2-yl)-6-(1,1-difluoroethyl)imidazo[1,2-a]pyrazine.

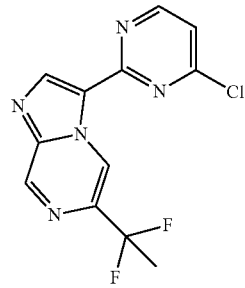 [SMILES: CC(F)(F)c1cn2c(-c3nccc(Cl)n3)cnc2cn1]

Preparation 190: 3-(4-Chloropyrimidin-2-yl)-6-(difluoromethyl)imidazo[1,2-a]pyrazine

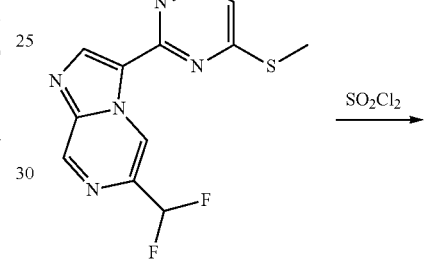

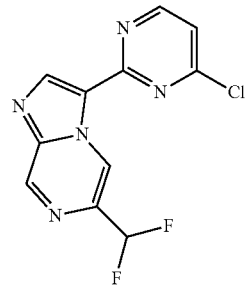

6-(Difluoromethyl)-3-(4-(methylthio)pyrimidin-2-yl)imidazo[1,2-a]pyrazine (5.7 g, 19.4 mmol) was suspended in MeCN (100 mL) and concentrated HCl (3.0 g of 37% w/w, 1.7 mL of 37% w/w, 31.1 mmol) was added. Sulfuryl chloride (6.3 mL, 77.8 mmol) was added slowly and the reaction mixture stirred at ambient temperature for 10 mins. The resulting solution was poured slowly into iced water (170 mL) kept cool with an external ice/water bath and the resulting cream suspension stirred at ambient temperature for 30 mins. The solid was collected by filtration, washed with water and dried under vacuum for 30 mins. The solid (still wet) was stirred as a suspension in saturated aq. NaHCO$_3$ solution (50 mL) for 30 mins then the solid collected by filtration, washed with copious amounts of water and dried under vacuum for 1 hour at ambient temperature and then in a vacuum oven at 40° C. overnight to furnish 3-(4-chloropyrimidin-2-yl)-6-(difluoromethyl)imidazo[1,2-a]pyrazine as a beige solid (4.7 g, 86%); $^1$H NMR (500 MHz, DMSO-$d_6$) δ 9.93 (q, J=1.4 Hz, 1H), 9.39 (d, J=1.4 Hz, 1H), 8.98 (d, J=5.4 Hz, 1H), 8.75 (s, 1H), 7.69 (d, J=5.4 Hz, 1H), 7.27 (t, J=54.4 Hz, 1H); 19F NMR (470 MHz, DMSO-$d_6$) −115.98; ES+ [M+H]=283.9.

The following compound was made using methodology similar to that described in Preparation 190:

3-(4-Chloro-5-fluoropyrimidin-2-yl)-6-(trifluoromethyl)imidazo[1,2-a]pyrazine.

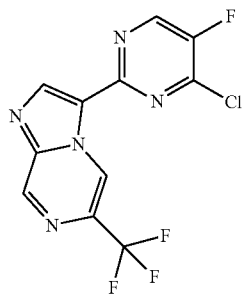 [SMILES: Fc1cnc(-c2cnc3cnc(C(F)(F)F)cn23)nc1Cl]

Preparation 191: 3-(4-Chloropyrimidin-2-yl)imidazo[1,2-a]pyrazine-6-carbonitrile

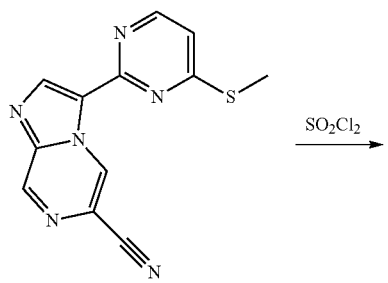

3-(4-(Methylthio)pyrimidin-2-yl)imidazo[1,2-a]pyrazine-6-carbonitrile (500 mg, 1.86 mmol) was suspended in MeCN (8.5 mL) and concentrated HCl (293 mg of 37% w/w, 163 μL of 37% w/w, 2.98 mmol) was added. Sulfuryl chloride (1.76 g, 1.06 mL, 13.1 mmol) was added and the reaction mixture was stirred vigorously at ambient temperature for 30 mins. Saturated aq. NaHCO$_3$ solution (19 mL) was added followed by water (28 mL), and the resultant brown precipitate collected by filtration and dried to give 3-(4-chloropyrimidin-2-yl)imidazo[1,2-a]pyrazine-6-carbonitrile as a brown powder (393 mg, 82%); $^1$H NMR (400 MHz, DMSO-d$_6$) δ 10.22 (d, J=1.4 Hz, 1H), 9.41 (d, J=1.4 Hz, 1H), 9.01 (d, J=5.4 Hz, 1H), 8.82 (s, 1H), 7.74 (d, J=5.4 Hz, 1H).

The following compounds were made using methodology similar to that described in Preparation 191:

6-Chloro-3-(4-chloropyrimidin-2-yl)imidazo[1,2-a]pyrazine;

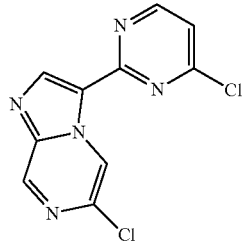 [SMILES: Clc1cn2c(-c3nccc(Cl)n3)cnc2cn1]

3-(4-Chloropyrimidin-2-yl)-6-methylimidazo[1,2-a]pyrazine;

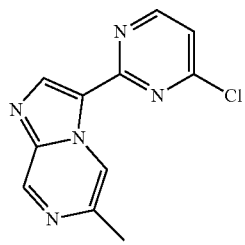 [SMILES: Cc1cn2c(-c3nccc(Cl)n3)cnc2cn1]

3-(4-Chloro-6-methylpyrimidin-2-yl)-6-(trifluoromethyl)imidazo[1,2-a]pyrazine;

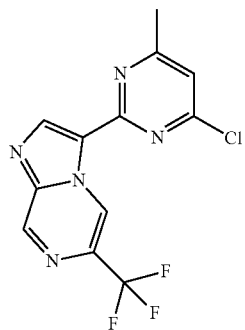 [SMILES: Cc1cc(Cl)nc(-c2cnc3cnc(C(F)(F)F)cn23)n1]

3-(4-Chloropyrimidin-2-yl)-6-(1H-pyrazol-3-yl)imidazo[1,2-a]pyrazine;

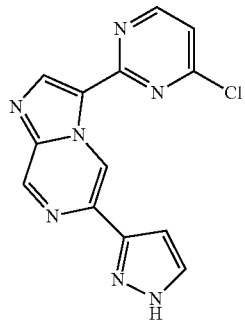 [SMILES: Clc1ccnc(-c2cnc3cnc(-c4cc[nH]n4)cn23)n1]

3-(4-Chloropyrimidin-2-yl)-6-(pyridin-4-yl)imidazo[1,2-a]pyrazine;

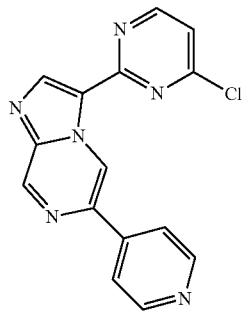 [SMILES: Clc1ccnc(-c2cnc3cnc(-c4ccncc4)cn23)n1]

3-(4-Chloropyrimidin-2-yl)-6-cyclopropylimidazo[1,2-a]pyrazine;

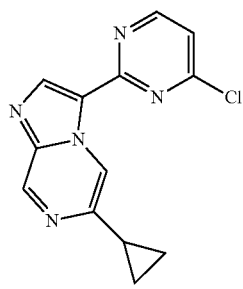 [SMILES: Clc1ccnc(-c2cnc3cnc(C4CC4)cn23)n1]

Preparation 192:
5,5-Difluoropiperidine-3-carboxamide

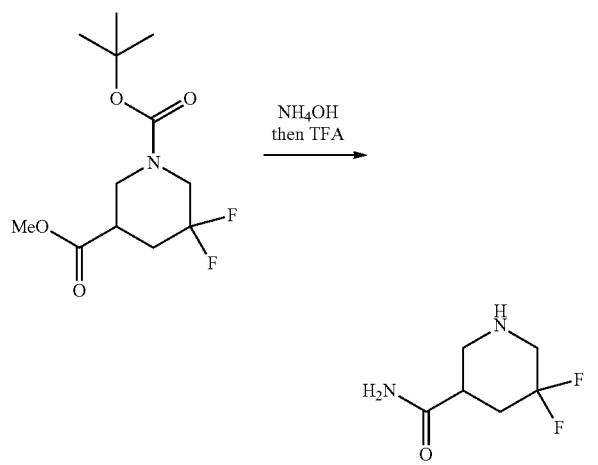

1-(tert-Butyl) 3-methyl 5,5-difluoropiperidine-1,3-dicarboxylate (100 mg, 0.358 mmol) was dissolved in ammonium hydroxide (255.6 mg, 284.0 µL, 7.294 mmol) and the reaction mixture heated to 70° C. in a sealed tube. The reaction was stirred 70° C. for 16 hours behind a blast shield. After this time, the reaction was cooled to ambient temperature, and the resulting mixture concentrated in vacuo and then dissolved in DCM (5 mL) and treated with TFA (200 µL, 2.596 mmol) and stirred for 3 hours. The crude material was then used directly in the next step without further purification.

Preparation 193: 4-Methylpiperidine-3-carboxamide

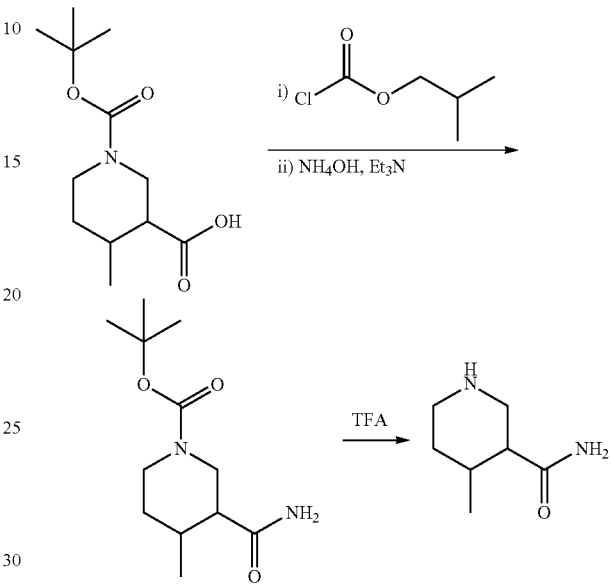

Step 1: tert-Butyl 3-carbamoyl-4-methylpiperidine-1-carboxylate

To a stirred solution of 1-tert-butoxycarbonyl-4-methylpiperidine-3-carboxylic acid (227 mg, 0.9330 mmol) in THF (1.8 mL) was added Et$_3$N (113.3 mg, 156 µL, 1.120 mmol) and the mixture then cooled to 0° C. Isobutyl chloroformate (146.5 mg, 139 µL, 1.073 mmol) was added dropwise and the resulting mixture stirred for 30 min. After this time, NH$_4$OH (2.616 g, 2.907 mL, 18.66 mmol) was added at the same temperature and the resulting mixture stirred for 1 hour. Water was then added (5 mL) and the mixture extracted three times with DCM, the combined organic extracts dried over MgSO$_4$, filtered and concentrated under reduced pressure to give tert-butyl 3-carbamoyl-4-methylpiperidine-1-carboxylate, which was used directly in the next step without further purification, assumed quantitative; MS m/z: 243 (M+H)$^+$.

Step 2: 4-Methylpiperidine-3-carboxamide

A round-bottomed flask was charged with tert-butyl 3-carbamoyl-4-methyl-piperidine-1-carboxylate (226 mg, 0.933 mmol) in DCM (1.9 mL). TFA (2.127 g, 1.437 mL, 18.65 mmol) was then added and the resulting mixture stirred at ambient temperature for 12 hours. The crude mixture was loaded into a methanol pre-washed SCX column, rinsed with methanol and released with methanolic ammonia. The combined ammonia extracts were then concentrated under reduced pressure to give 4-methylpiperidine-3-carboxamide which was used directly in the next step without further purification; MS m/z: 143 (M+H)$^+$

Preparation 194: 2,5-Dimethylpiperidine-3-carboxamide

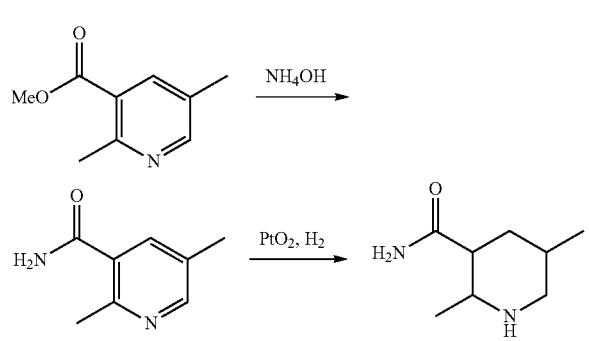

Step 1: 2,5-Dimethylnicotinamide

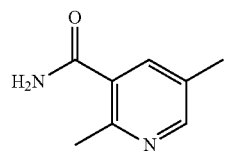

Methyl 2,5-dimethylpyridine-3-carboxylate (100 mg, 0.6054 mmol) was dissolved in ammonium hydroxide (480 µL, 12.33 mmol) and the reaction heated to 70° C. in a sealed tube. The reaction was stirred at this temperature for 16 hours behind a blast shield. After 16 hours, the reaction was cooled to ambient temperature, during which time the orange solution became a thick suspension of pale yellow solid. This precipitate was collected by filtration and washed with water. The filtrate was evaporated to dryness to leave 2,5-dimethylpyridine-3-carboxamide (99 mg, quantitative yield), which was used directly in the next step without further purification; MS m/z: 151.0 (M+H)$^+$.

Step 2: 2,5-Dimethylpiperidine-3-carboxamide

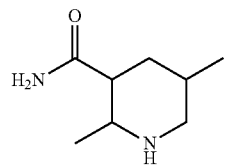

2,5-Dimethylpyridine-3-carboxamide (99 mg, 0.6592 mmol) and PtO$_2$ (30.4 mg, 0.134 mmol) were mixed and dissolved in methanol (3 mL) and HCl (1.1 mL of 3 M, 3.296 mmol) was added. The mixture was degassed and stirred under a balloon of H$_2$ for 1.5 hours before being passed through Celite and the filtrate evaporated to give 2,5-dimethylpiperidine-3-carboxamide (dihydrochloride salt) (150 mg, 99%) as a mixture of diastereomers (3:1 ratio); MS m/z 157.0 (M+H)$^+$.

Preparation 195: 2-(Pyrrolidin-3-yl)acetamide

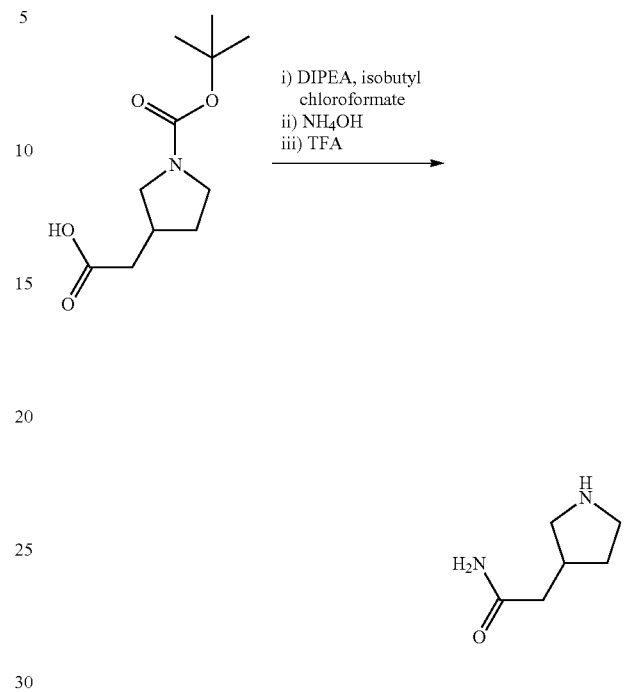

2-(1-tert-Butoxycarbonylpyrrolidin-3-yl)acetic acid (100 mg, 0.44 mmol) was dissolved in THF (2 mL) under N$_2$ and DIPEA (304 µL, 1.75 mmol) was added. The solution was cooled in an ice bath and isobutylchloroformate (62 µL, 0.48 mmol) added slowly. After stirring for 1 hour, NH$_4$OH (440 µL of 28% w/w, 6.51 mmol) was added to the cloudy solution. The resulting clear solution was stirred for a further 1 hour and concentrated in vacuo to leave crude product as a pale yellow oil (140 mg). This residue was dissolved in DCM (5 mL) and TFA (500 µL, 6.49 mmol) was added. The reaction mixture was stirred at ambient temperature overnight before being evaporated in vacuo to give 2-pyrrolidin-3-ylacetamide (60 mg, 57%) as a colourless oil that was used without further purification; MS m/z 129.0 (M+1)$^+$.

Preparation 196: 3-(1H-Pyrazol-4-yl)piperidin-4-ol

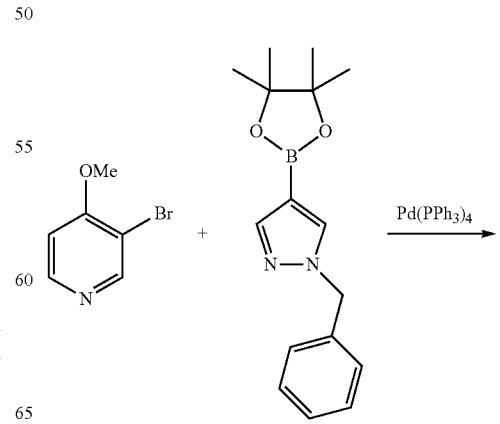

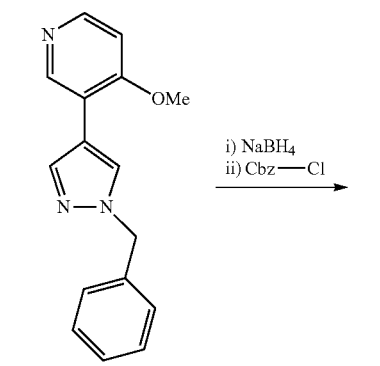

i) NaBH₄
ii) Cbz—Cl
→

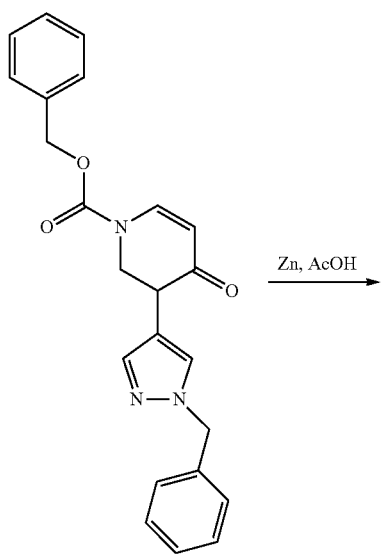

Zn, AcOH
→

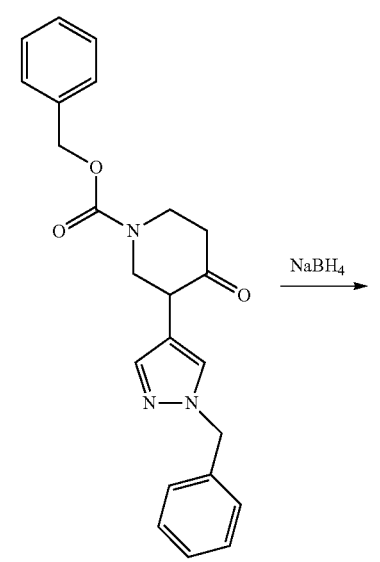

NaBH₄
→

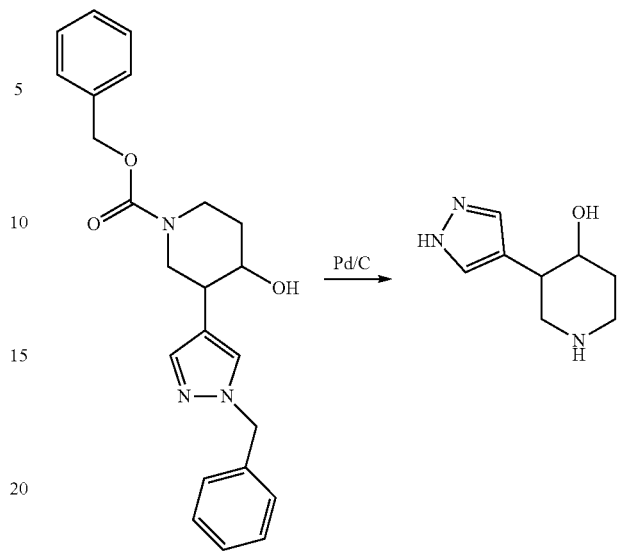

Pd/C
→

Step 1:
3-(1-Benzyl-1H-pyrazol-4-yl)-4-methoxypyridine

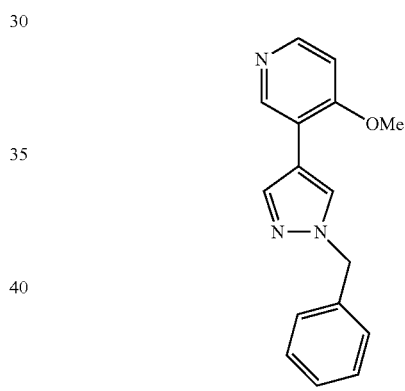

To a solution of 3-bromo-4-methoxy-pyridine (1.5 g, 7.98 mmol) in 1,4-dioxane (30 mL) was added 1-benzyl-4-(4,4,5,5-tetramethyl-1,3,2-dioxaborolan-2-yl)pyrazole (2.50 g, 8.80 mmol), Pd(PPh₃)₄ (480 mg, 0.42 mmol) and Na₂CO₃ (12 mL of 2 M, 24.00 mmol). The mixture was degassed (3× vacuum/nitrogen cycles) and was stirred at 120° C. for 4 hours. The reaction was cooled to ambient temperature and diluted with EtOAc/brine. The layers were separated and the aqueous layer extracted with EtOAc (×2). The combined organic extracts were washed with brine (×1), dried (MgSO₄), filtered and concentrated in vacuo. The residue was purified by column chromatography (silica, eluting with 0-100% EtOAc/Petroleum Ether, loaded in DCM) to give 3-(1-benzylpyrazol-4-yl)-4-methoxy-pyridine (1.85 g, 87%) as a cream semi-solid; ¹H NMR (500 MHz, DMSO-d₆) δ 8.73 (s, 1H), 8.34 (d, J=0.8 Hz, 1H), 8.31 (d, J=5.7 Hz, 1H), 8.03 (d, J=0.8 Hz, 1H), 7.38-7.34 (m, 2H), 7.32-7.25 (m, 3H), 7.10 (d, J=5.7 Hz, 1H), 5.38 (s, 2H), 3.94 (s, 3H); MS m/z 266.5 (M+H)⁺.

Step 2: Benzyl 3-(1-benzyl-1H-pyrazol-4-yl)-4-oxo-3,4-dihydropyridine-1(2H)-carboxylate

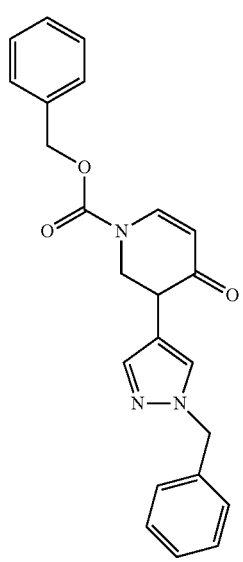 [SMILES: O=C1C=CN(C(=O)OCc2ccccc2)CC1c1cnn(Cc2ccccc2)c1]

To a suspension of 3-(1-benzylpyrazol-4-yl)-4-methoxypyridine (500 mg, 1.89 mmol) in MeOH (7 mL) was added sodium borohydride (80 mg, 2.12 mmol) at −78° C. After stirring for 15 minutes a solution of benzyl chloroformate (300 μL, 2.10 mmol) in Et$_2$O (0.3 mL) was added dropwise. After stirring at −78° C. for 1.5 hours, water was added (3 mL) and the reaction was warmed to ambient temperature. After stirring for 2.5 hours the mixture was diluted with water (plus brine to aid separation) and extracted with EtOAc (×3). The combined organic extracts were washed with brine (×3), dried (MgSO$_4$), filtered and concentrated in vacuo. The residue was purified by column chromatography (silica, eluting with 0 to 50% EtOAc/Petroleum Ether, loaded in DCM) to give:

Benzyl 5-(1-benzylpyrazol-4-yl)-4-oxo-2,3-dihydropyridine-1-carboxylate (115.3 mg, 16%) as a pale yellow oil; $^1$H NMR (500 MHz, DMSO-d$_6$) δ 8.11 (d, J=4.6 Hz, 2H), 7.71 (s, 1H), 7.48-7.46 (m, 2H), 7.43-7.27 (m, 6H), 7.24-7.21 (m, 2H), 5.32 (s, 2H), 5.29 (s, 2H), 4.04-4.01 (m, 2H), 2.65-2.62 (m, 2H); MS m/z 388.3 (M+H)$^+$.

and

Benzyl 3-(1-benzylpyrazol-4-yl)-4-oxo-2,3-dihydropyridine-1-carboxylate (264.2 mg, 36%) as a pale yellow oil; $^1$H NMR (500 MHz, DMSO-d$_6$) δ 7.92 (d, J=8.2 Hz, 1H), 7.65 (s, 1H), 7.44-7.26 (m, 9H), 7.21-7.18 (m, 2H), 5.32-5.24 (m, 5H), 4.12 (qd, J=13.3, 6.7 Hz, 2H), 3.71 (dd, J=7.9, 5.4 Hz, 1H); MS m/z 388.3 (M+H)$^+$.

These were combined with the mixed fractions to give a total isolated amount of 551.9 mg (74%) as a 65:35 mixture benzyl 3-(1-benzylpyrazol-4-yl)-4-oxo-2,3-dihydropyridine-1-carboxylate:benzyl 5-(1-benzylpyrazol-4-yl)-4-oxo-2,3-dihydropyridine-1-carboxylate.

Step 3: Benzyl 3-(1-benzyl-1H-pyrazol-4-yl)-4-oxopiperidine-1-carboxylate

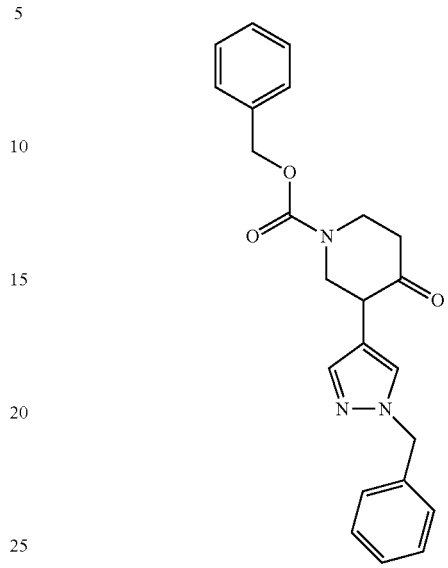

A solution of a 35:65 mixture of benzyl 5-(1-benzylpyrazol-4-yl)-4-oxo-2,3-dihydropyridine-1-carboxylate and benzyl 3-(1-benzylpyrazol-4-yl)-4-oxo-2,3-dihydropyridine-1-carboxylate (550 mg, 1.420 mmol) in acetic acid (15 mL) was stirred vigorously as zinc (1.4 g, 21.40 mmol) was added in one portion. The mixture was stirred at ambient temperature for 93 hours, filtered through Celite, washing with DCM, and concentrated in vacuo. The residue was purified by column chromatography (silica, eluting with 0 to 50% EtOAc/petroleum ether, loaded in DCM) to give benzyl 3-(1-benzylpyrazol-4-yl)-4-oxo-piperidine-1-carboxylate (230.1 mg, 42%) as a colourless oil; $^1$H NMR (500 MHz, DMSO-d$_6$) δ 7.44-7.27 (m, 10H), 7.23-7.18 (m, 2H), 5.28 (s, 2H), 5.13 (s, 2H), 4.18-4.03 (m, 2H), 3.80 (dd, J=10.1, 5.7 Hz, 1H), 3.59-3.47 (m, 2H), 2.64-2.40 (m, 2H); MS m/z 390.3 (M+H)$^+$.

Step 4: Benzyl 3-(1-benzyl-1H-pyrazol-4-yl)-4-hydroxypiperidine-1-carboxylate

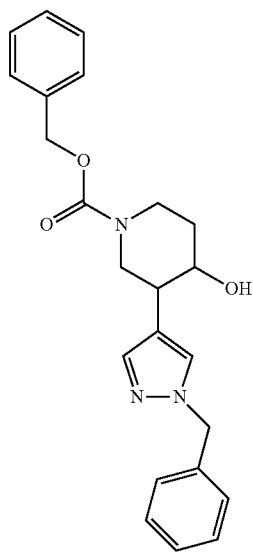 [SMILES: O=C(OCc1ccccc1)N1CCC(O)C(c2cnn(Cc3ccccc3)c2)C1]

To a solution of benzyl 3-(1-benzylpyrazol-4-yl)-4-oxo-piperidine-1-carboxylate (230 mg, 0.59 mmol) in methanol (10 mL) was added sodium borohydride (45 mg, 1.19 mmol) and the mixture stirred at ambient temperature for 4 hours. A further portion of sodium borohydride (25 mg, 0.66 mmol) was added and the reaction stirred at ambient temperature for 1 hour. The reaction was quenched by the addition of saturated aqueous NH$_4$Cl and the mixture extracted with diethyl ether (×3). The combined organic extracts were washed with water (×1), brine (×1), dried (MgSO$_4$), filtered and concentrated in vacuo. The residue was purified by column chromatography (silica, eluting with 0 to 100% EtOAc/petroleum ether, loaded in DCM) to give benzyl 3-(1-benzylpyrazol-4-yl)-4-hydroxy-piperidine-1-carboxylate (171.5 mg, 74%) as a colourless oil; MS m/z 392.4 (M+H)$^+$.

Step 5: 3-(1H-Pyrazol-4-yl)piperidin-4-ol

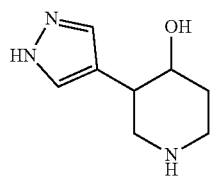 [SMILES: OC1CCNCC1c1cn[nH]c1]

A mixture of benzyl 3-(1-benzylpyrazol-4-yl)-4-hydroxy-piperidine-1-carboxylate (170 mg, 0.43 mmol), Pd on C, wet, Degussa (70 mg of 10% w/w, 0.066 mmol) and concentrated HCl (240 μL of 12 M, 2.88 mmol) in methanol (10 mL) and was placed under an atmosphere of H$_2$ and stirred at ambient temperature for 18 hours. The catalyst was removed by filtration through Celite, washing with methanol, and the filtrate concentrated in vacuo. The residue was azeotroped with methanol (×3) and diethyl ether (×3) to give 3-(1H-pyrazol-4-yl)piperidin-4-ol (hydrochloride salt) (88.45 mg, 100%) as a beige solid that was used directly assuming 100% yield and purity; MS m/z 168.1 (M+H)$^+$.

Preparation 197:
3-methyl-2-(1H-pyrazol-4-yl)morpholine

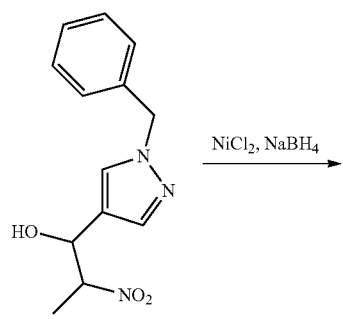

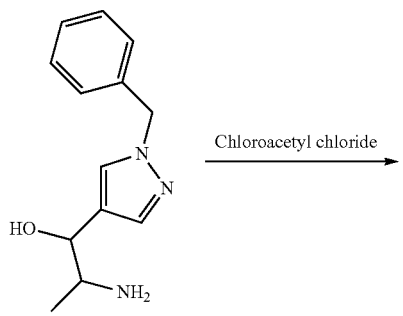

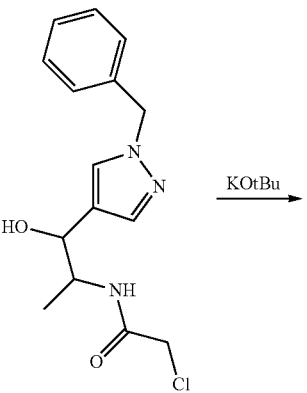

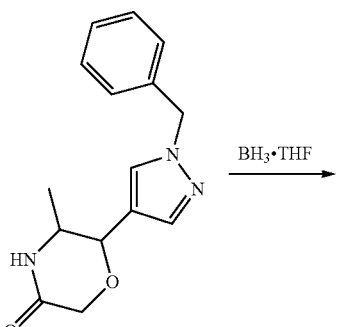 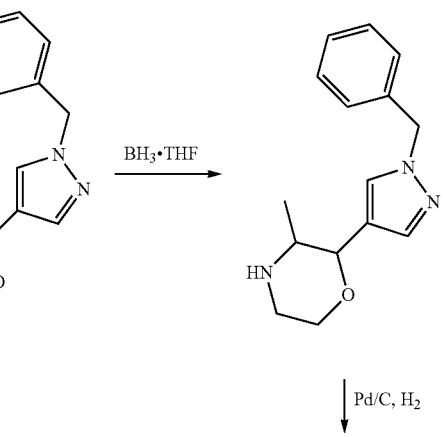

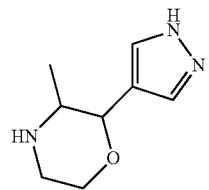

Step 1: 2-Amino-1-(1-benzyl-1H-pyrazol-4-yl)propan-1-ol

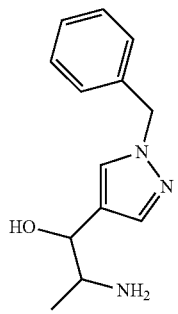 [SMILES: CC(N)C(O)c1cnn(Cc2ccccc2)c1]

Sodium borohydride (6.82 g, 7.22 mL, 180.2 mmol) was added over 15 mins to a solution of 1-(1-benzylpyrazol-4-yl)-2-nitro-propan-1-ol (11.85 g, 45.35 mmol) and dichloronickel hexahydrate (10.77 g, 45.33 mmol) in methanol (225 mL) at 0° C. The initial green solution turned dark green/black upon addition of sodium borohydride. After the addition, the solution was stirred at 0° C. for 20 mins. The reaction mixture was quenched by addition of water followed by 1 M HCl and stirred for 30 mins. The suspension was filtered over Celite and the filtrate concentrated in vacuo. The residue was redissolved in methanol, resulting in a green solution and white solid. The suspension was filtered and the filtrate passed through an SCX-2 cartridge (3×50 g), washing with MeCN/MeOH and released with 2 M $NH_3$/MeOH. The ammonia extracts were concentrated in vacuo to give 1.95 g of material. The aqueous layer was acidified and concentrated. The concentrated residue was then redissolved in MeCN/$H_2O$ and lyophilised. This afforded 2-amino-1-(1-benzylpyrazol-4-yl)propan-1-ol (hydrochloride salt) as an off-white solid (7.26 g). This was used directly in the next step without further purification.

Step 2: N-(1-(1-Benzyl-1H-pyrazol-4-yl)-1-hydroxypropan-2-yl)-2-chloroacetamide

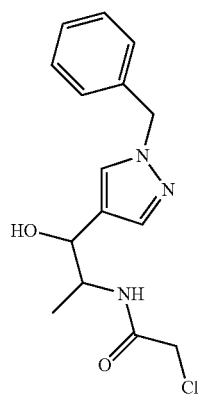 [SMILES: CC(NC(=O)CCl)C(O)c1cnn(Cc2ccccc2)c1]

2-Chloroacetyl chloride (approximately 952.2 mg, 670.6 µL, 8.431 mmol) was added dropwise to a solution of 2-amino-1-(1-benzylpyrazol-4-yl)propan-1-ol (1.95 g, 8.431 mmol) and N-ethyl-N-isopropyl-propan-2-amine (1.417 g, 1.910 mL, 10.96 mmol) in DCM (84 mL) at 0° C. An orange colour developed upon addition. The resulting solution was warmed to ambient temperature after 10 mins. After 1 hour the reaction mixture was quenched with saturated aqueous $NaHCO_3$. The aqueous layer was extracted with DCM, the combined organic layers were washed sequentially with saturated aqueous $NH_4Cl$ and brine solutions, dried ($MgSO_4$), filtered and concentrated in vacuo to afford N-(1-(1-benzyl-1H-pyrazol-4-yl)-1-hydroxypropan-2-yl)-2-chloroacetamide as a brown oil (2.25 g, 86%); MS m/z 308.1 $(M+H)^+$.

Step 3: 6-(1-Benzyl-1H-pyrazol-4-yl)-5-methylmorpholin-3-one

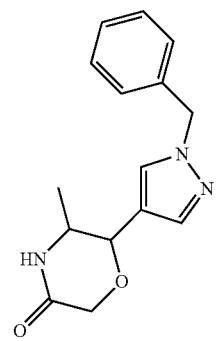 [SMILES: CC1NC(=O)COC1c1cnn(Cc2ccccc2)c1]

N-[2-(1-Benzylpyrazol-4-yl)-2-hydroxy-1-methyl-ethyl]-2-chloro-acetamide (2.25 g, 7.311 mmol) and KOtBu (984.4 mg, 8.773 mmol) were stirred at 0° C. in THF (48 mL). The reaction mixture was warmed to ambient temperature after 15 mins and then stirred for 2 hours. Saturated aqueous $NH_4Cl$ solution was added and the organics were extracted with EtOAc, dried ($MgSO_4$), filtered and concentrated in vacuo to give 6-(1-benzyl-1H-pyrazol-4-yl)-5-methylmorpholin-3-one as an orange oil. The material was purified by column chromatography (silica, 0-100% EtOAc/petroleum ether then 0-10% MeOH/DCM) to give 6-(1-benzylpyrazol-4-yl)-5-methyl-morpholin-3-one (1.55 g, 78%) as an orange foam; MS m/z 272.2 $(M+H)^+$.

Step 4: 2-(1-Benzyl-1H-pyrazol-4-yl)-3-methylmorpholine

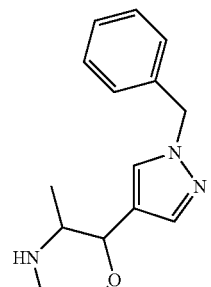

Borane-Tetrahydrofuran complex (28.56 mL of 1 M, 28.56 mmol) was added cautiously to a solution of 6-(1-benzylpyrazol-4-yl)-5-methyl-morpholin-3-one (1.55 g, 5.713 mmol) in THF (23 mL) at 0° C. After 10 mins, the reaction mixture was warmed to ambient temperature. After 2 hours, the reaction mixture was cooled to 0° C. and cautiously quenched with methanol until effervescence has subsided. Then conc. HCl (5 mL) was added and the resulting mixture stirred for 1 hour. The reaction mixture was passed through an SCX-2 cartridge (25 g), washing with MeCN/MeOH and the product released with 2 M $NH_3$/MeOH. The product fractions were concentrated in vacuo to afford 2-(1-benzylpyrazol-4-yl)-3-methyl-morpholine (0.98 g, 67%) as a pale yellow oil; MS m/z 258.2 $(M+H)^+$.

Step 5: 3-Methyl-2-(1H-pyrazol-4-yl)morpholine

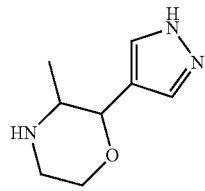

2-(1-Benzylpyrazol-4-yl)-3-methyl-morpholine (1.1 g, 4.275 mmol), Pd on C, wet, Degussa (439.9 mg of 10% w/w, 0.413 mmol) and concentrated HCl (2 mL of 12 M, 24.00 mmol) were taken up in methanol (16.5 mL) and stirred at ambient temperature for 22 hours under a $H_2$ atmosphere. The catalyst was filtered off through Celite and was partially concentrated. The crude mixture was loaded onto a methanol pre-washed SCX column, rinsed with methanol and released with methanolic ammonia. The ammonia extracts were concentrated under reduced pressure to give 3-methyl-2-(1H-pyrazol-4-yl)morpholine (720 mg, 76%) which was used directly in the next step.

Preparation 198:
2-Methylpyrrolidine-3-carboxamide

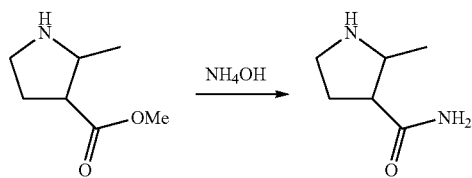

Methyl 2-methylpyrrolidine-3-carboxylate (100 mg, 0.698 mmol) was dissolved in ammonium hydroxide (500 µL, 12.84 mmol) and the reaction mixture heated to 70° C. in a sealed tube. The reaction mixture was stirred at this temperature for 16 hours behind a blast shield. After 16 hours the reaction mixture was cooled to ambient temperature and then concentrated to dryness to give 2-methylpyrrolidine-3-carboxamide as a yellow residue which was used directly without further purification; MS m/z 129.1 $(M+H)^+$.

Preparation 199: (S)-Octahydro-6H-pyrido[1,2-a]pyrazin-6-one

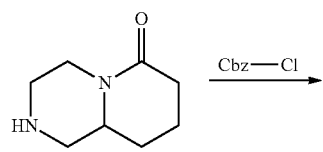

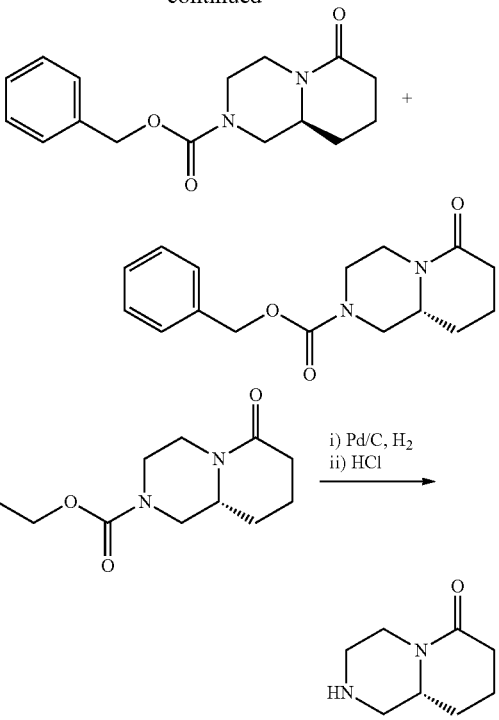

Step 1: Benzyl (S)-6-oxooctahydro-2H-pyrido[1,2-a]pyrazine-2-carboxylate and benzyl (R)-6-oxooctahydro-2H-pyrido[1,2-a]pyrazine-2-carboxylate

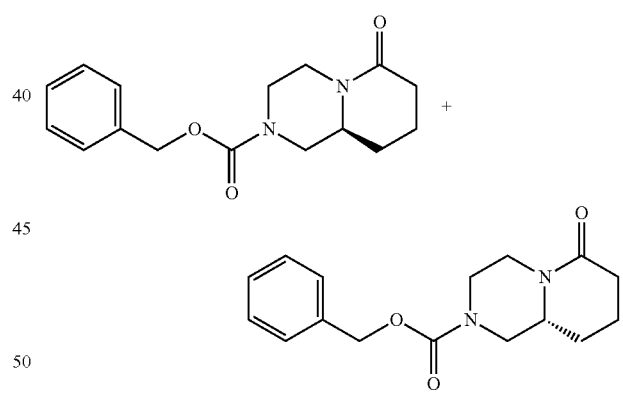

Benzyl chloroformate (2.4 mL, 16.81 mmol) was added dropwise to a stirred solution of 1,2,3,4,7,8,9,9a-octahydropyrido[1,2-a]pyrazin-6-one (hydrochloride salt) (2.1 g, 11.01 mmol) and DIPEA (4.2 mL, 24.11 mmol) in DCM (20 mL) at 0° C. and the reaction allowed to warm to ambient temperature over 16 hours. The reaction was diluted with saturated aqueous $NH_4Cl$, water was added to dissolve the resultant precipitate, and the layers separated. The aqueous layer was extracted further with DCM (×2) and the combined organic extracts washed with brine, dried ($MgSO_4$), filtered and concentrated in vacuo. The residue was purified by column chromatography (silica, eluting with 50-100% EtOAc/Petroleum ether, dry loaded) to give the racemic compound as a white solid (2.69 g, 84%). SFC separation (LuxCel2, 30% MeOH, 0.2% DMIPA) gave separation of the isomers benzyl (9aS)-6-oxo-3,4,7,8,9,9a-hexahydro-1H-pyrido[1,2-a]pyrazine-2-carboxylate (peak 1, 1.09 g, 34.3% yield, 98% ee) and benzyl (9aR)-6-oxo-3,4,7,8,9,9a-hexahydro-1H-pyrido[1,2-a]pyrazine-2-carboxylate (peak 2, 1.12 g, 35% yield, 98.4% ee) as colourless oils.

Step 2: (S)-Octahydro-6H-pyrido[1,2-a]pyrazin-6-one

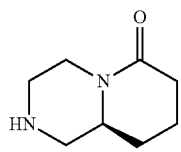 [SMILES: O=C1CCC[C@H]2CNCCN12]

Pd on C, wet, Degussa (110 mg of 10% w/w, 0.103 mmol) was added to a stirred solution of benzyl 6-oxo-3,4,7,8,9,9a-hexahydro-1H-pyrido[1,2-a]pyrazine-2-carboxylate (1.09 g, 3.780 mmol) in methanol (7.5 mL)/EtOAc (7.5 mL) and the reaction placed under an atmosphere of $H_2$. The reaction was stirred at ambient temperature for 15 hours then the catalyst removed by filtration and the solvent removed in vacuo. The residue was dissolved in DCM (15 mL) and hydrogen chloride (1.3 mL of 4 M, 5.20 mmol) was added. The solvent was removed in vacuo to give (9aS)-1,2,3,4,7,8,9,9a-octahydropyrido[1,2-a]pyrazin-6-one (hydrochloride salt) (660.4 mg, 92%) as a white solid; $^1$H NMR (500 MHz, DMSO-$d_6$) δ 9.28 (br s, 2H), 4.60-4.54 (m, 1H), 3.70-3.64 (m, 1H), 3.29-3.24 (m, 2H), 2.86-2.76 (m, 3H), 2.30-2.19 (m, 2H), 1.98-1.93 (m, 1H), 1.78-1.75 (m, 1H), 1.67-1.64 (m, 1H), 1.50-1.43 (m, 1H); MS m/z 155.1 (M+H)$^+$; $α_D$ (20)=−39.2°.

Preparation 200: N-((4,4-Difluoro-5-methylpiperidin-3-yl)methyl)methanesulfonamide

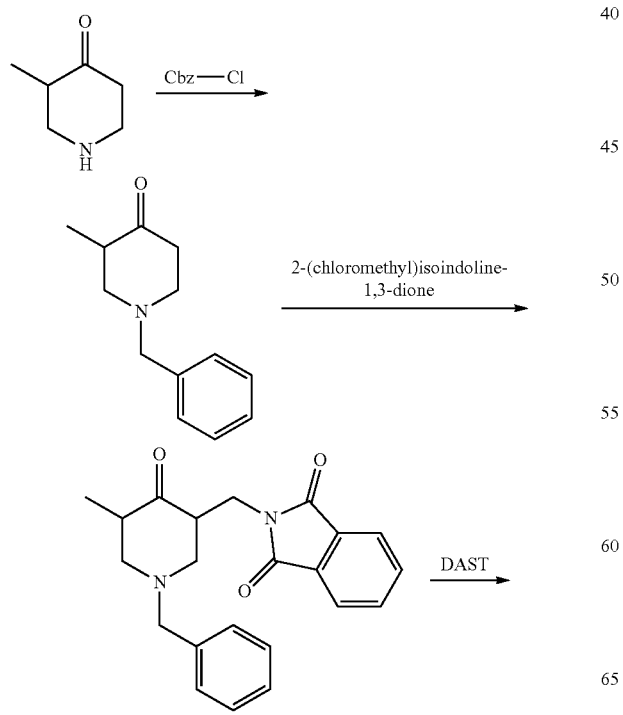

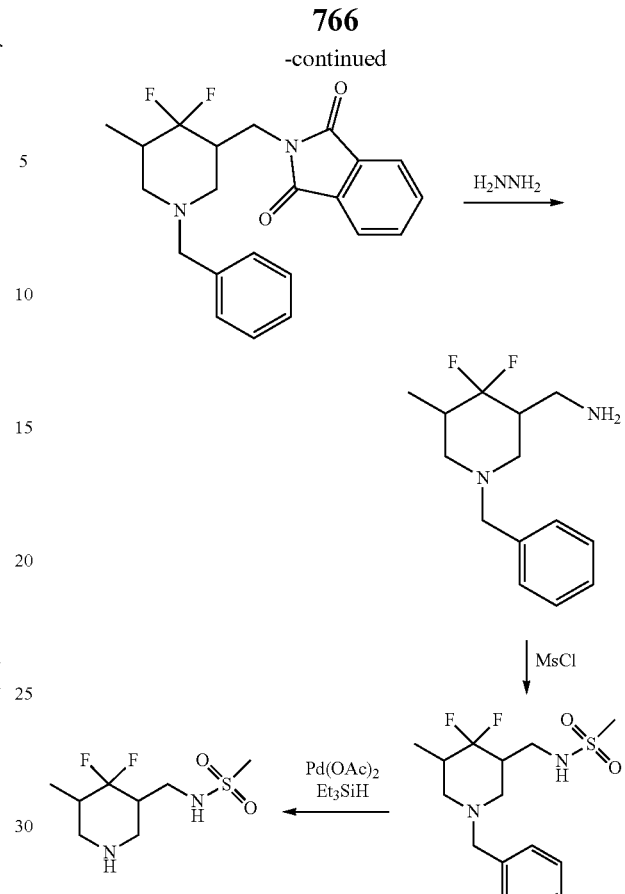

Step 1: 1-Benzyl-3-methylpiperidin-4-one

Benzyl chloroformate (6.841 g, 5.73 mL, 40.10 mmol) was added to 3-methylpiperidin-4-one (hydrochloride salt) (5 g, 33.42 mmol) and $K_2CO_3$ (37 g, 267.7 mmol) in EtOAc (100 mL) and water (50 mL). The resulting mixture was stirred vigorously for 16 hours at ambient temperature. The organic phase was separated and collected, and the aqueous phase extracted further with ethyl acetate (2×). The combined organic extracts were washed with water and brine, and dried over $MgSO_4$ and concentrated in vacuo. The crude material was purified by column chromatography (silica, 0-100% EtOAc/hexanes). The pure product fractions were combined and concentrated under reduced pressure to give 1-benzyl-3-methylpiperidin-4-one (6.7 g, 81%), which was used directly in the next step.

Step 2: 2-((1-Benzyl-5-methyl-4-oxopiperidin-3-yl)methyl)isoindoline-1,3-dione

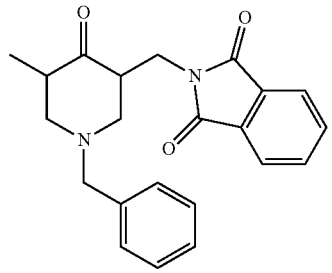 [SMILES: CC1CN(Cc2ccccc2)CC(CN2C(=O)c3ccccc3C2=O)C1=O]

(Bis(trimethylsilyl)amino)lithium (33.48 mL of 1 M, 33.48 mmol) was added dropwise to a solution of benzyl 3-methyl-4-oxo-piperidine-1-carboxylate (6.7 g, 27.09 mmol) in tetrahydrofuran (100 mL) cooled to −78° C. under N$_2$. After 90 mins, a solution of 2-(chloromethyl)isoindoline-1,3-dione (8.002 g, 40.91 mmol) in THF (30 mL) was added. The resulting solution was stirred at −78° C. for 1 hour. The reaction mixture was quenched by addition of saturated aqueous NH$_4$Cl (~20 ml) and warmed to ambient temperature. The reaction mixture was diluted with EtOAc, washed with a saturated bicarbonate aqueous solution and brine. The organic layer was dried over MgSO$_4$ and concentrated in vacuo. The crude material was purified by column chromatography (silica; 0-100% EtOAc/petroleum ether). The clean product fractions were combined and concentrated under reduced pressure to give 2-((1-benzyl-5-methyl-4-oxopiperidin-3-yl)methyl)isoindoline-1,3-dione (7.4 g, 67%) as a white gum; MS m/z 407.2 (M+H)$^+$.

Step 3: 2-((1-Benzyl-4,4-difluoro-5-methylpiperidin-3-yl)methyl)isoindoline-1,3-dione

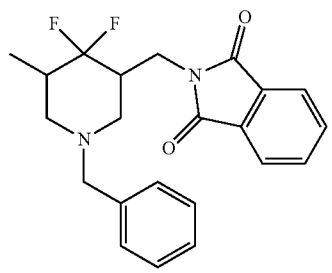 [SMILES: CC1CN(Cc2ccccc2)CC(CN2C(=O)c3ccccc3C2=O)C1(F)F]

A 250 mL round-bottomed flask equipped with a thermometer, nitrogen line and air condenser was charged with benzyl 3-[(1,3-dioxoisoindolin-2-yl)methyl]-5-methyl-4-oxo-piperidine-1-carboxylate (19.1 g, 46.99 mmol). The vessel was cooled in an ice/salt/water bath, then DAST (60 mL, 454.1 mmol) was added slowly (no exotherms were noted once all DAST was added) forming a thick white suspension. The mixture was stirred in an ice bath for a further 20 mins then removed from the ice bath and stirred at room temperature for 3 days. After this time, the mixture was an orange solution. The reaction mixture was diluted with DCM (200 mL) and then added slowly to a stirred mixture of ice/water (approx. 800 mL) and solid sodium bicarbonate, keeping the temperature around 0° C. and the pH at 7-8 by addition of more solid sodium bicarbonate. After complete addition, the mixture was allowed to warm to ambient temperature then transferred to a separating funnel and extracted with DCM (3×). The organics were combined, washed with water (1×), brine (1×), dried (Na$_2$SO$_4$), filtered and concentrated in vacuo to give the crude product as a viscous orange oil (23.5 g). The crude product was purified by column chromatography (silica, 0-16% EtOAc/petroleum ether), and the product fractions combined and concentrated in vacuo to give the product as a colourless oil (14 g). The oil was dissolved in ethanol (50 mL) and concentrated in vacuo and the resulting product oil was dried on the high vacuum line for 1 hour to give 2-((1-benzyl-4,4-difluoro-5-methylpiperidin-3-yl)methyl)isoindoline-1,3-dione (9.8 g, 49%) as a colourless foam; $^1$HNMR (500 MHz, DMSO-d$_6$) δ 7.92-7.85 (m, 4H), 7.25 (br m, 5H), 4.98 (m, 2H), 4.10-4.06 (m, 1H), 4.03-4.01 (m, 1H), 3.99-3.94 (m, 1H), 3.57 (dd, 1H), 2.64 (br m, 2H), 2.50 (m, 1H), 2.17 (m, 1H) and 0.93 (d, 3H); MS m/z 429.3 (M+H+)$^+$.

Step 4: (1-Benzyl-4,4-difluoro-5-methylpiperidin-3-yl)methanamine

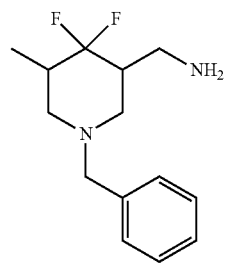 [SMILES: CC1CN(Cc2ccccc2)CC(CN)C1(F)F]

A mixture of benzyl 3-[(1,3-dioxoisoindolin-2-yl)methyl]-4,4-difluoro-5-methyl-piperidine-1-carboxylate (600 mg, 1.40 mmol) and hydrazine monohydrate (204.2 mg, 200 µL, 4.079 mmol) in ethanol (10 mL) was stirred under reflux conditions for 16 hours. The reaction mixture was cooled to ambient temperature and the crude suspension was diluted with methanol. The solution was passed through a pre-wetted 5 g SCX cartridge. The column was eluted with methanol and the product then eluted with 2 M ammonia in methanol and the product fractions concentrated in vacuo to give (1-benzyl-4,4-difluoro-5-methylpiperidin-3-yl)methanamine (370 mg, 89%) as a pale yellow gum which was used directly in the next step without further purification; MS m/z 299.2 (M+H)$^+$.

Step 5: N-((1-Benzyl-4,4-difluoro-5-methylpiperidin-3-yl)methyl)methanesulfonamide

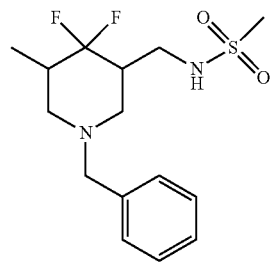 [SMILES: CC1CN(Cc2ccccc2)CC(CNS(C)(=O)=O)C1(F)F]

A round-bottomed flask was charged with benzyl 3-(aminomethyl)-4,4-difluoro-5-methyl-piperidine-1-carboxylate (1.4 g, 4.693 mmol) and Et$_3$N (961.6 mg, 1.325 mL, 9.503 mmol) in DCM (19 mL) under nitrogen. The mixture was then cooled to 0° C. and MsCl (1.009 g, 681.8 µL, 8.804 mmol) was then added dropwise. The resulting mixture was stirred at 0° C. for 10 mins and then stirred at ambient temperature for a further 10 mins. The reaction mixture was quenched by addition of saturated NaHCO$_3$ aqueous solution and stirred at ambient temperature for 5 mins. The solution was filtered through a phase separator cartridge and concentrated under reduced pressure. The crude mixture was purified by column chromatography (silica; EtOAc/Petroleum ether). The product fractions were combined and concentrated under reduced pressure to give N-((1-benzyl-4,4-difluoro-5-methylpiperidin-3-yl)methyl)methanesulfonamide (1.3 g, 74%) as a colourless oil which was used directly in the next step; MS m/z 377.1 (M+H)$^+$.

Step 6: N-((4,4-Difluoro-5-methylpiperidin-3-yl)methyl)methanesulfonamide

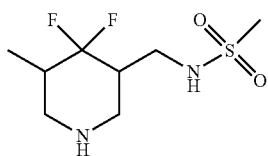

Benzyl 4,4-difluoro-3-(methanesulfonamidomethyl)-5-methyl-piperidine-1-carboxylate (1.3 g, 3.454 mmol) was dissolved in DCM (26 mL). Pd(OAc)$_2$ (340 mg, 1.514 mmol), Et$_3$N (1.7 mL, 12.20 mmol) and Et$_3$SiH (3.6 mL, 22.54 mmol) were added to the reaction mixture under nitrogen. Effervescence was observed therefore the reaction mixture was cooled in an ice bath for 10 mins and then stirred at ambient temperature for 1 hour. The reaction mixture was poured onto a 50 g SCX-2 column. The column was eluted with methanol, followed by 2 M ammonia in methanol. The product fractions were concentrated in vacuo to give N-((4,4-difluoro-5-methylpiperidin-3-yl)methyl)methanesulfonamide (1.5 g, 75%) as a colourless gum; MS m/z 243.1 (M+H)$^+$.

Preparation 201: 2-[(E)-2-Ethoxyvinyl]-4-methyl sulfanyl-pyrimidine

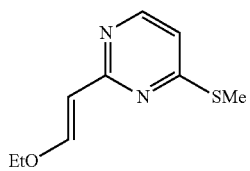 [SMILES: CCO/C=C/c1nccc(SC)n1]

A solution of 2-chloro-4-methylsulfanyl-pyrimidine (1 g, 6.226 mmol), Na$_2$CO$_3$ (9.3 mL of 2M aq., 18.60 mmol) and 2-[(E)-2-ethoxyvinyl]-4,4,5,5-tetramethyl-1,3,2-dioxaborolane (1.35 g, 6.816 mmol) in 1,2-dimethoxyethane (15 mL) was degassed with nitrogen. Pd(PPh$_3$)$_4$ (600 mg, 0.519 mmol) was added and the mixture again degassed with nitrogen. The mixture was heated under reflux for 2 hours. The reaction mixture was cooled to ambient temperature, partitioned between EtOAc/water and the layers separated. The aqueous layer was extracted with EtOAc and the combined organic extracts washed with brine, dried (MgSO$_4$), filtered and concentrated in vacuo. The residue was purified by flash column chromatography (silica, EtOAc/petroleum ether gradient) to afford 2-[(E)-2-ethoxyvinyl]-4-methylsulfanyl-pyrimidine (1.10 g, 90%); $^1$H NMR (500 MHz, chloroform-d) δ 8.19 (d, 1H), 7.94 (d, 1H), 6.85 (d, 1H), 5.90 (d, 1H), 4.02 (q, 2H), 2.56 (s, 3H), 1.40 (t, 3H); ESVI-MS m/z 197.1 (M+H).

Preparation 202: 5-(4-Chloropyrimidin-2-yl)-2-(difluoromethyl)imidazo[2,1-b]thiazole

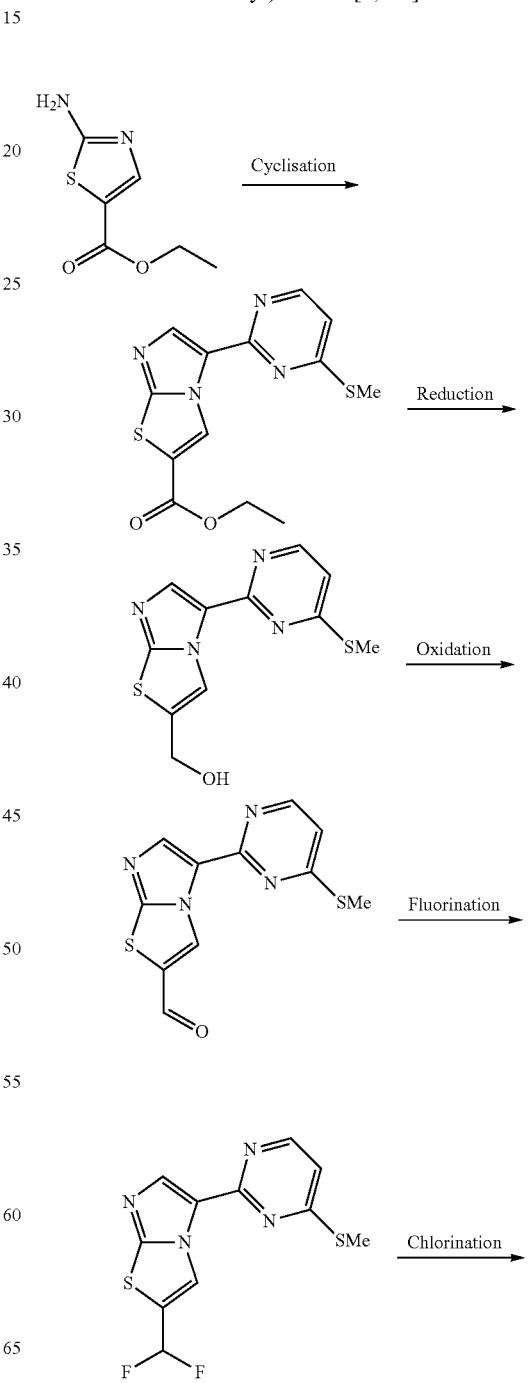

Step 1: Ethyl 5-(4-methylsulfanylpyrimidin-2-yl)imidazo[2,1-b]thiazole-2-carboxylate

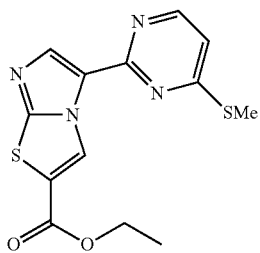 [SMILES: CCOC(=O)c1cn2c(-c3nccc(SC)n3)cnc2s1]

NBS (230 mg, 1.29 mmol) was added to a stirred solution of 2-[(E)-2-ethoxyvinyl]-4-methylsulfanyl-pyrimidine (250 mg, 1.27 mmol) in dioxane (8 mL)/water (3 mL) and the reaction mixture was stirred at ambient temperature for 15 minutes. Ethyl 2-aminothiazole-5-carboxylate (440 mg, 2.56 mmol) was added and the reaction mixture heated at 65° C. for 1 hour then at 100° C. for 19 hours. The mixture was cooled to ambient temperature and the resultant precipitate isolated by filtration washing with dioxane. The filtrate was concentrated in vacuo and purified by column chromatography (silica, EtOAc/Petroleum ether gradient). The desired fractions were combined with the initial precipitate and concentrated in vacuo to give the title compound as a yellow solid (175 mg, 43%); $^1$H NMR (500 MHz, chloroform-d) δ 9.30 (s, 1H), 8.38 (d, 1H), 8.26 (s, 1H), 7.01 (d, 1H), 4.45 (q, 2H), 2.69 (s, 3H), 1.45 (t, 3H); MS m/z: 321.1 (M+H)$^+$.

Step 2: [5-(4-Methylsulfanylpyrimidin-2-yl)imidazo[2,1-b]thiazol-2-yl]methanol

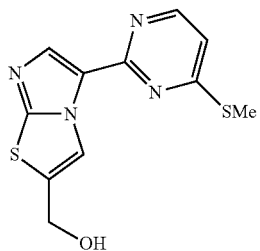 [SMILES: CSc1ccnc(-c2cnc3sc(CO)cn23)n1]

Ethyl 5-(4-methylsulfanylpyrimidin-2-yl)imidazo[2,1-b]thiazole-2-carboxylate (175 mg, 0.546 mmol) was dissolved in dry THF (20 mL) and cooled in an ice-bath. 2M LiAlH$_4$ in THF (185 µL, 0.370 mmol) was added dropwise and the reaction allowed to warm to ambient temperature over 30 minutes. The reaction was quenched by the sequential addition of 15 µL water, µL of 15% NaOH and 60 µL of water. The resultant solid was removed by filtration, washing with EtOAc and the filtrate concentrated in vacuo to give the title compound as a yellow solid (152 mg, 100%) that was used directly without further purification; $^1$H NMR (500 MHz, chloroform-d) δ 8.46 (s, 1H), 8.24 (d, 1H), 8.08 (s, 1H), 6.86 (d, 1H), 4.78 (s, 2H), 2.56 (s, 3H); MS m/z: 279.1 (M+H)$^+$.

Step 3: 5-(4-Methylsulfanylpyrimidin-2-yl)imidazo[2,1-b]thiazole-2-carbaldehyde

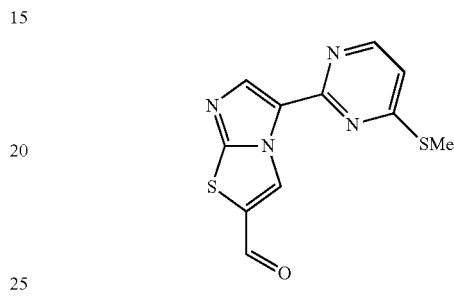

MnO$_2$ (485 mg, 5.58 mmol) was added to a stirred solution of [5-(4-methylsulfanylpyrimidin-2-yl)imidazo[2,1-b]thiazol-2-yl]methanol (152 mg, 0.546 mmol) in THF (30 mL) and the reaction stirred at ambient temperature for 16 hours. The reaction was filtered through a pad of Celite (washing with THF) and the filtrate concentrated in vacuo to give the title compound as a yellow solid (128 mg, 85%); $^1$H NMR (500 MHz, chloroform-d) δ 9.95 (s, 1H), 9.25 (s, 1H), 8.29 (d, 1H), 8.19 (s, 1H), 6.94 (d, 1H), 2.58 (s, 3H); MS m/z: 277.1 (M+H)$^+$.

Step 4: 2-(Difluoromethyl)-5-(4-methylsulfanylpyrimidin-2-yl)imidazo[2,1-b]thiazole

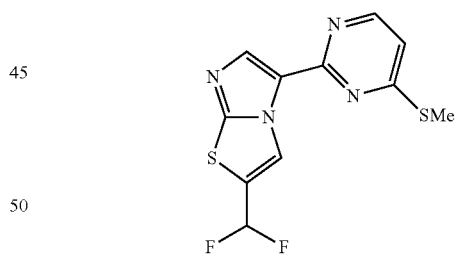

Deoxofluor (130 µL, 0.705 mmol) was added to a solution of 5-(4-methylsulfanylpyrimidin-2-yl)imidazo[2,1-b]thiazole-2-carbaldehyde (127 mg, 0.460 mmol) in DCM (10 mL) at 0° C. and the mixture warmed to ambient temperature over 20 hours. A further portion of Deoxofluor (130 µL, 0.705 mmol) was added and the reaction stirred at ambient temperature for a further 24 hours. Saturated aqueous NaHCO$_3$ was added dropwise and the reaction stirred for 30 minutes. The layers were separated and the aqueous phase extracted with DCM (×2). The combined organic extracts were washed with brine (×1) and dried (MgSO$_4$), filtered and concentrated in vacuo. The residue was purified by column chromatography (silica, EtOAc/Petroleum ether gradient) to give the title compound as a white solid (71 mg,

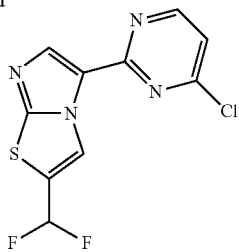

52%); ¹H NMR (500 MHz, chloroform-d) δ 8.89 (t, 1H), 8.36 (d, 1H), 8.23 (s, 1H), 7.01-6.77 (m, 1H), 7.00 (d, 1H), 2.67 (s, 3H); ¹⁹F NMR (471 MHz, Chloroform-d) 6-105.56; MS m/z: 299.1 (M+H)⁺.

Step 5: 5-(4-Chloropyrimidin-2-yl)-2-(difluoromethyl)imidazo[2,1-b]thiazole

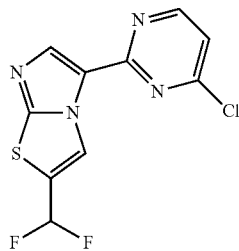 [SMILES: FC(F)c1cn2c(-c3nccc(Cl)n3)cnc2s1]

2-(Difluoromethyl)-5-(4-methylsulfanylpyrimidin-2-yl)imidazo[2,1-b]thiazole (70 mg, 0.235 mmol) was dissolved in MeCN (6 mL) and concentrated HCl (20 μL, 0.365 mmol) was added. Sulfuryl chloride (80 μL, 0.988 mmol) was added and the reaction mixture was stirred at ambient temperature for 5 minutes. Cold saturated aqueous NaHCO₃ was added dropwise and the mixture stirred at ambient temperature for 10 minutes. The resultant precipitate was isolated by filtration, washed with water and dried to give the title compound as a white solid (39 mg, 58%); ¹H NMR (500 MHz, DMSO-d₆) δ 9.05 (t, 1H), 8.85 (d, 1H), 8.21 (s, 1H), 7.57 (d, 1H), 7.56 (t, 1H); 19F NMR (471 MHz, DMSO-d₆) δ −104.83; MS m/z: 287.0 (M+H)⁺.

Preparation 203: 5-(4-Chloropyrimidin-2-yl)-2-(trifluoromethyl)imidazo[2,1-b]thiazole

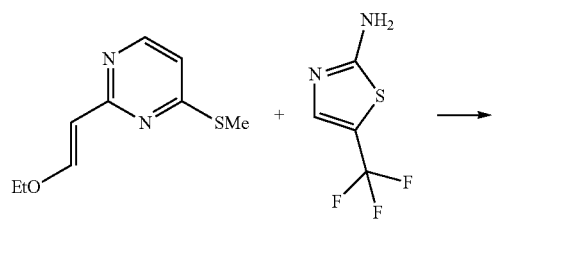

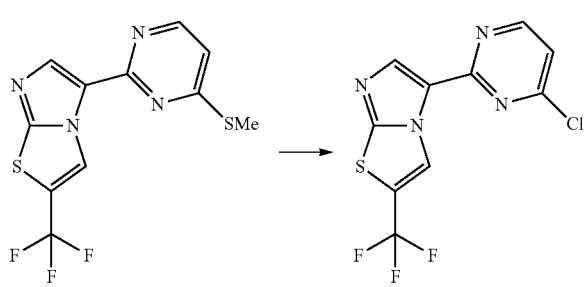

Step 1: 5-(4-Methylsulfanylpyrimidin-2-yl)-2-(trifluoromethyl)imidazo[2,1-b]thiazole

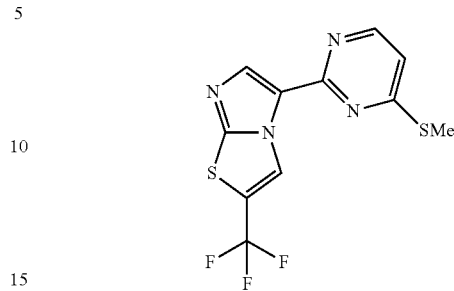

NBS (1.08 g, 6.07 mmol) was added to a stirred solution of 2-[(E)-2-ethoxyvinyl]-4-methylsulfanyl-pyrimidine (1.16 g, 5.91 mmol) in dioxane (20 mL)/water (7.5 mL) and the reaction mixture was stirred at ambient temperature for 15 minutes. 5-(Trifluoromethyl)thiazol-2-amine (564 mg, 3.35 mmol) in dioxane (1 mL) was added and the reaction mixture heated at 100° C. for 22 hours. The mixture was cooled to ambient temperature and the solvent removed in vacuo. The residue was partitioned between DCM and saturated aqueous NaHCO₃ and the layers separated. The aqueous layer was extracted with DCM (×2) and the combined organic extracts dried (MgSO₄), filtered and concentrated in vacuo. The residue was purified by column chromatography (silica, EtOAc/Petroleum ether gradient) to give the title compound as a white solid (137 mg, 13%); 1H NMR (500 MHz, Chloroform-d) δ 9.19 (s, 1H), 8.42 (d, J=5.6 Hz, 1H), 8.40 (s, 1H), 7.14 (d, J=5.6 Hz, 1H), 2.69 (s, 3H); NMR (471 MHz, CDCl3) δ −56.87; MS m/z: 317.0 (M+H)⁺.

Step 2: 5-(4-Chloropyrimidin-2-yl)-2-(trifluoromethyl)imidazo[2,1-b]thiazole

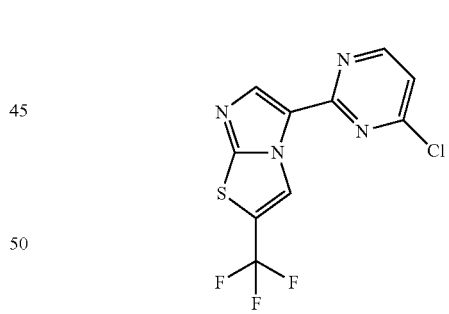

5-(4-Methylsulfanylpyrimidin-2-yl)-2-(trifluoromethyl)imidazo[2,1-b]thiazole (137 mg, 0.433 mmol) was dissolved in MeCN (15 mL) and concentrated HCl (40 μL, 0.731 mmol) was added. Sulfuryl chloride (150 μL, 1.85 mmol) was added and the reaction mixture was stirred at ambient temperature for 55 minutes. Cold saturated aqueous NaHCO₃ was added dropwise and the mixture stirred at ambient temperature for 10 minutes. The resultant precipitate was isolated by filtration, washed with water and dried to give the title compound as a beige solid (61 mg, 46%); ¹H NMR (500 MHz, DMSO-d₆) δ 9.11 (q, 1H), 8.88 (d, 1H), 8.25 (s, 1H), 7.59 (d, 1H); 19F NMR (471 MHz, DMSO-d₆) δ −55.63; MS m/z: 305.0 (M+H)⁺.

Preparation 204: 2-(1H-Pyrazol-4-yl)morpholine

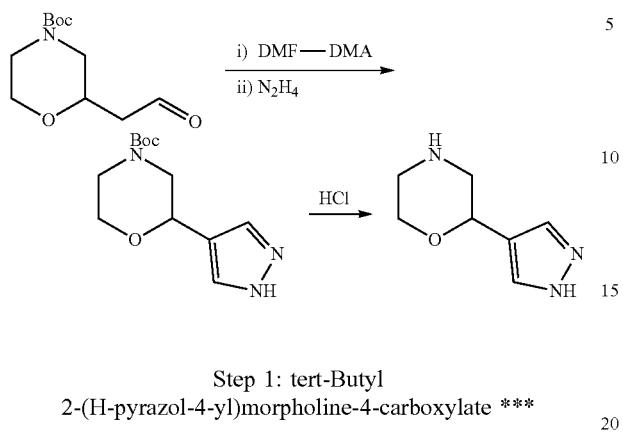

Step 1: tert-Butyl 2-(H-pyrazol-4-yl)morpholine-4-carboxylate ***

A mixture of tert-butyl 2-(2-oxoethyl)morpholine-4-carboxylate (5.77 g, 25.17 mmol) and DMF-DMA (6.7 mL, 50.06 mmol) in DMF (50 mL) was stirred at 80° C. for 17 hours. The reaction mixture was cooled to ambient temperature and the solvent removed in vacuo. The residue was taken up in ethanol (100 mL) and hydrazine hydrate (1.3 mL, 26.51 mmol) was added with stirring at ambient temperature. After 3 hours, the solvent was removed in vacuo and the residue purified by chromatography (silica, EtOAc/Petroleum ether gradient), to give tert-butyl 2-(1H-pyrazol-4-yl)morpholine-4-carboxylate (2.35 g, 9.29 mmol, 37%) as a yellow solid; $^1$H NMR (500 MHz, chloroform-d) δ 7.63 (s, 2H), 4.52 (dd, 1H), 4.12 (br s, 1H), 3.97-3.90 (m, 2H), 3.68 (td, 1H), 3.05 (d, 2H), 1.51 (s, 9H); MS m/z: 254.1 [M+H]$^+$.

Step 2: 2-(1H-pyrazol-4-yl)morpholine

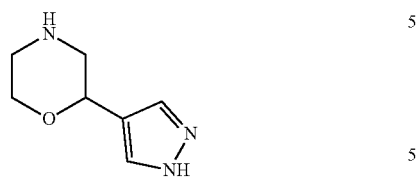

3M HCl in methanol (45 mL of 3M, 135.0 mmol) was added to a stirred solution of tert-butyl 2-(1H-pyrazol-4-yl)morpholine-4-carboxylate (2.35 g, 9.29 mmol) in DCM (75 mL) and the reaction heated at reflux for 5 hours. The reaction was cooled to ambient temperature and the solvent removed in vacuo. The residue was dissolved in the minimum amount of DCM/MeOH and loaded on to an ion-exchange cartridge. The cartridge was washed with MeOH/DCM mixtures, which were discarded. The product was eluted by washing with 2M NH$_3$ in MeOH/DCM. Solvent was removed in vacuo to give 2-(1H-pyrazol-4-yl)morpholine (1.27 g, 8.29 mmol, 89%) as an orange solid; $^1$H NMR (500 MHz, chloroform-d) δ 7.60 (s, 2H), 4.56 (dd, 1H), 3.98 (ddd, 1H), 3.77 (td, 1H), 3.11 (dd, 1H), 3.00 (td, 1H), 2.93-2.88 (m, 2H); MS m/z: 154.2 [M+H]$^+$. The product was taken on to the next reaction without further purification.

Preparation 205: 2,5-Dimethyl-3-((methylsulfinyl)methyl)piperidine

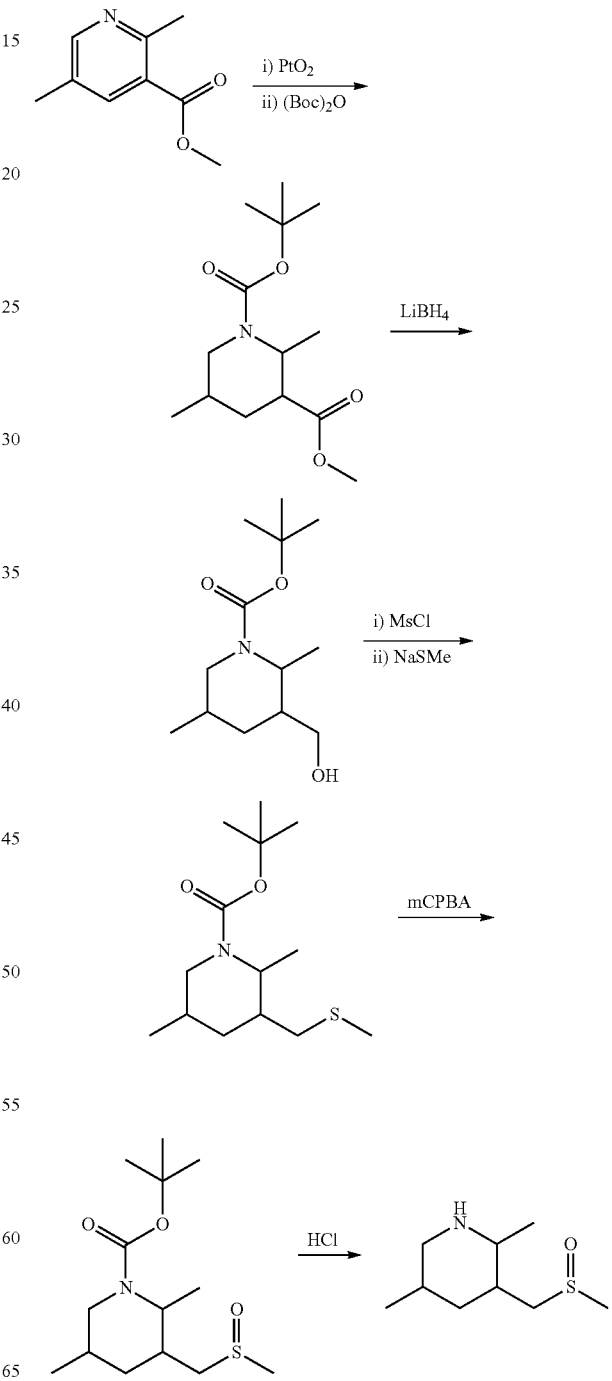

Step 1: 1-(tert-Butyl) 3-methyl 2,5-dimethylpiperidine-1,3-dicarboxylate

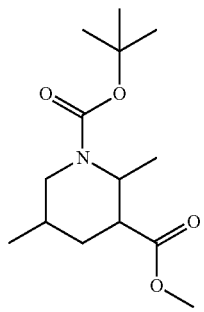

A mixture of methyl 2,5-dimethylpyridine-3-carboxylate (2.6 g, 15.74 mmol) and PtO₂ (713 mg, 3.14 mmol) in HCl (57 mL of a 3M solution in MeOH, 171.1 mmol) was stirred under a balloon of H₂. The reaction mixture was stirred overnight before being filtered through Celite and the filtrate concentrated in vacuo. The residue was dissolved in THF (27 mL) and triethylamine (6.6 mL, 47.3 mmol), DMAP (96 mg, 0.79 mmol) and di-tert-butyl dicarbonate (17.4 mL of a 1M solution in THF, 17.4 mmol) sequentially added. The reaction mixture was stirred overnight, then partitioned between EtOAc and water. The organic layer was separated and washed with NH₄Cl solution, water (1×), brine (1×), then dried (MgSO₄), filtered and concentrated in vacuo. The residue was purified by chromatography (silica, 0-10% EtOAc/Petroleum ether gradient) to give 1-(tert-butyl) 3-methyl 2,5-dimethylpiperidine-1,3-dicarboxylate (1.4 g, 33%) as a colourless oil containing a mixture of diastereomers; $^1$H NMR (400 MHz, methanol-$d_4$) δ 4.80-4.62 (m, 1H), 3.95-3.78 (m, 1H), 3.71 (d, 3H), 2.71 (dq, 1H), 2.46 (dt, 1H), 1.89-1.77 (m, 1H), 1.48 (q, 10H), 1.10-0.92 (m, 7H).

Step 2: tert-Butyl 3-(hydroxymethyl)-2,5-dimethylpiperidine-1-carboxylate

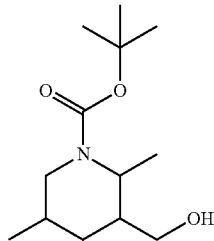 [SMILES: CC1CC(CO)C(C)N(C(=O)OC(C)(C)C)C1]

O1-tert-Butyl O3-methyl 2,5-dimethylpiperidine-1,3-dicarboxylate (1.4 g, 5.16 mmol) was dissolved in THF (42 mL) and cooled to 0° C. Lithium borohydride (10.3 mL of a 2M solution in THF, 20.6 mmol) was added and the reaction allowed to warm to ambient temperature. After 30 minutes the reaction mixture was warmed to 50° C. and stirred overnight. The reaction was cooled to ambient temperature then quenched with water. The mixture was extracted with EtOAc (×3). The combined organics were dried and concentrated in vacuo to give tert-butyl 3-(hydroxymethyl)-2,5-dimethyl-piperidine-1-carboxylate (1.25 g, 100%) as a colourless oil that was taken directly on to the next reaction without further purification; $^1$H NMR (400 MHz, methanol-$d_4$) δ 4.42-4.27 (m, 1H), 3.82-3.68 (m, 1H), 3.34-3.23 (m, 2H), 2.33 (dt, 1H), 1.91 (s, 1H), 1.82-1.68 (m, 1H), 1.54-1.37 (m, 2H), 1.35 (s, 9H), 0.95-0.87 (m, 3H), 0.86-0.76 (m, 4H).

Step 3: tert-Butyl 2,5-dimethyl-3-(((methylsulfonyl)oxy)methyl)piperidine-1-carboxylate

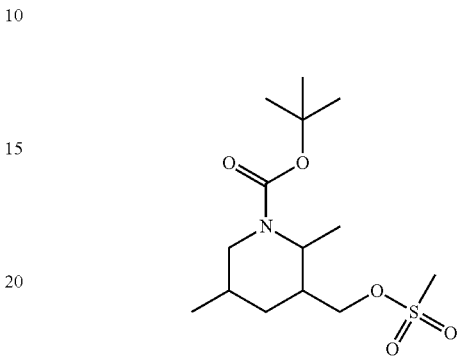

Methanesulfonyl chloride (2.77 mL, 35.7 mmol) was added to a solution of tert-butyl 3-(hydroxymethyl)-2,5-dimethylpiperidine-1-carboxylate (5.80 g, 23.8 mmol) and triethylamine (6.64 mL, 47.7 mmol) in DCM (116 mL) stirring at 0° C. After 30 mins the reaction was quenched with saturated aq. NaHCO₃, stirred for 5 mins and then the layers separated using a phase separator cartridge. The organic phase was evaporated in vacuo to give tert-butyl 2,5-dimethyl-3-(((methylsulfonyl)oxy)methyl)piperidine-1-carboxylate (7.6 g) which was used directly in the next step without further purification.

Step 4: tert-Butyl 2,5-dimethyl-3-((methylthio)methyl)piperidine-1-carboxylate

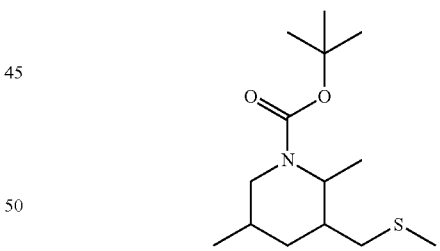

Sodium thiomethoxide (9.939 g, 141.8 mmol) was added to a solution of tert-butyl 2,5-dimethyl-3-(((methylsulfonyl)oxy)methyl)piperidine-1-carboxylate (7.6 g, 23.6 mmol) in EtOH (100 mL), stirring at 0° C. After addition, cooling was removed and the reaction heated at 60° C. for 16 hours. The reaction was cooled to ambient temperature, concentrated in vacuo and purified by column chromatography (silica, 0-12.5% MeOH/DCM gradient) to give tert-butyl 2,5-dimethyl-3-((methylthio)methyl)piperidine-1-carboxylate (3.4 g, 66%) as a colourless oil; $^1$H NMR (500 MHz, methanol-$d_4$) δ 4.53-4.43 (m, 1H), 3.86 (td, J=13.3, 4.4 Hz, 1H), 2.53-2.31 (m, 3H), 2.10 (s, 3H), 1.91-1.81 (m, 1H), 1.74-1.63 (m, 1H), 1.61-1.50 (m, 1H), 1.48 (s, 9H), 1.10-0.99 (m, 4H), 0.93 (t, J=6.4 Hz, 3H).

Step 5: tert-Butyl 2,5-dimethyl-3-((methylsulfinyl)methyl)piperidine-1-carboxylate

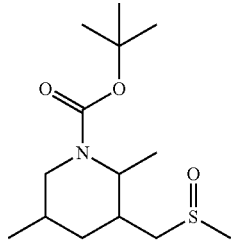

tert-Butyl 2,5-dimethyl-3-((methylthio)methyl)piperidine-1-carboxylate (2 g, 7.31 mmol) was dissolved in DCM (73 mL) and the solution cooled to 0° C. m-CPBA (1.80 g, 7.31 mmol) was added portionwise over 5 minutes and the reaction stirred for a further 5 minutes before being quenched by addition of saturated aq. sodium thiosulphate (40 mL) and stirred for 5 minutes before extracting with DCM (3×50 mL). The combined organics were washed with saturated aq. NaHCO$_3$ (2×40 mL), filtered through a phase separator cartridge and concentrated in vacuo to give tert-butyl 2,5-dimethyl-3-((methylsulfinyl)methyl)piperidine-1-carboxylate (2.1 g, 100%) as a colourless oil which was used without further purification.

Step 6: 2,5-Dimethyl-3-((methylsulfinyl)methyl)piperidine

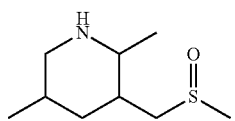

tert-Butyl 2,5-dimethyl-3-((methylsulfinyl)methyl)piperidine-1-carboxylate (2.1 g, 7.26 mmol) was dissolved in methanol (36 mL) and 4M HCl in dioxane (9.1 mL, 36.3 mmol) was added. The reaction was stirred for 16 hours at ambient temperature before being concentrated in vacuo to give 2,5-dimethyl-3-((methylsulfinyl)methyl)piperidine (1.85 g, 97%) as a white solid; MS m/z: 190.1 (M+H)$^+$.

The following compound was prepared in an analogous manner to that exemplified in preparation 205:

3-((Methylsulfinyl)methyl)piperidine

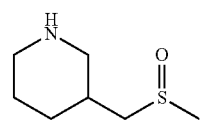

Preparation 206: N-(((3S,5S)-4,4-Difluoro-5-methylpiperidin-3-yl)methyl)methanesulfonamide

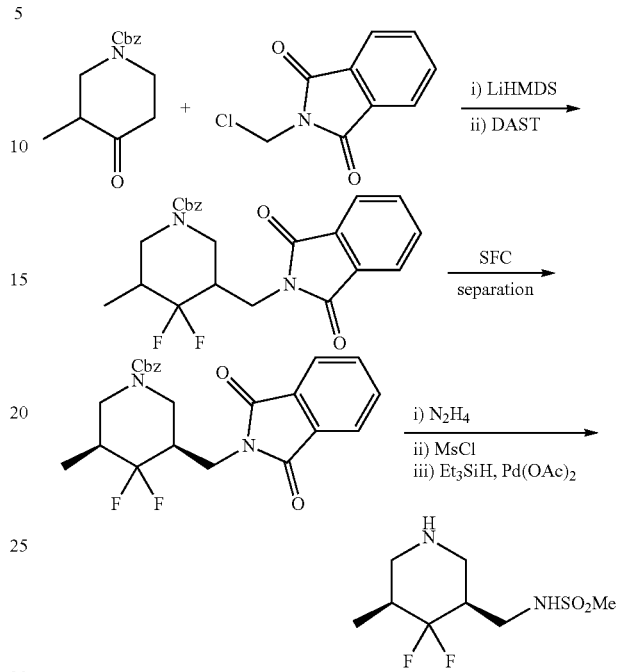

Step 1: Benzyl 3-((1,3-dioxoisoindolin-2-yl)methyl)-5-methyl-4-oxopiperidine-1-carboxylate

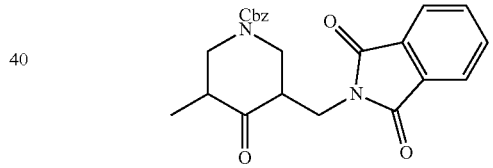

Benzyl 3-methyl-4-oxo-piperidine-1-carboxylate (20 g, 0.081 mol) was dissolved in THF (300 mL) under N$_2$. The solution was cooled to −78° C. and LiHMDS (1M in THF, 101.1 mL, 0.101 mol) was added dropwise over 20 minutes, keeping the temperature below −70° C. After stirring at −78° C. for 90 minutes, a solution of 2-(chloromethyl)isoindoline-1,3-dione (23.7 g, 0.121 mol) in THF (200 mL) was added dropwise over 25 minutes, keeping the temperature below −70° C. The reaction was stirred at −78° C. for 1 hour then quenched at −78° C. by the addition of saturated aqueous ammonium chloride solution (65 mL) and the mixture allowed to warm to ambient temperature. The reaction was repeated and the two mixtures obtained were combined and extracted with EtOAc (300 mL). The organic phase was washed with saturated aqueous sodium bicarbonate solution (300 mL) and brine (300 mL), dried (Na$_2$SO$_4$), filtered and concentrated in vacuo. The residue was purified by chromatography (silica, EtOAc/Pet.ether gradient). The product fractions were combined and concentrated in vacuo and the residue recrystallized from EtOAc to give the product as a white solid (7.56 g, 23%).

Step 2: Benzyl 3-((1,3-dioxoisoindolin-2-yl)methyl)-4,4-difluoro-5-methylpiperidine-1-carboxylate

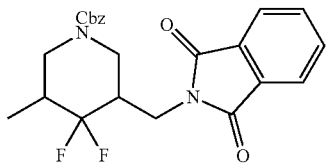 [SMILES: CC1CN(C(=O)OCc2ccccc2)CC(CN2C(=O)c3ccccc3C2=O)C1(F)F]

A flask was charged with benzyl 3-((1,3-dioxoisoindolin-2-yl)methyl)-5-methyl-4-oxopiperidine-1-carboxylate (60 g, 0.148 mol) and cooled in an ice/water bath. DAST (325 mL, 2.460 mol) was added in one portion and the mixture stirred at ambient temperature for 3 days. The resulting yellow solution was diluted with DCM (1 L) and slowly added to a mixture of ice/water and solid sodium bicarbonate with overhead stirring. The temperature remained below 0° C. and additional sodium bicarbonate was added to maintain a pH of 7-8. The mixture was warmed to room temperature and the layers separated. The aqueous phase was extracted with DCM (2 L). The combined organics were washed with brine, dried ($Na_2SO_4$), filtered and concentrated in vacuo. The residue was purified by chromatography (silica, EtOAc/PE elution). The product fractions were combined and concentrated in vacuo. The product, benzyl 3-((1,3-dioxoisoindolin-2-yl)methyl)-4,4-difluoro-5-methylpiperidine-1-carboxylate, was obtained as a glass (32.5 g, 0.08 mol, 51%); $^1$H NMR (300 MHz, chloroform-d) δ 7.89-7.64 (4H, m), 7.42-7.11 (5H, m), 5.15-5.03 (2H, m), 4.39-4.07 (3H, m), 3.83-3.66 (1H, m), 2.97-2.60 (2H, m), 2.56-2.31 (1H, m), 2.08-1.89 (1H, m), 1.05 (3H, d) as a mixture of isomers. Preparative chiral supercritical fluid chromatography (conditions: Chiralpak® IC 5 μm, $CO_2$/iPrOH 90/10, 230 nm) was used to isolate the single enantiomer benzyl (3R,5S)-3-[(1,3-dioxoisoindolin-2-yl)methyl]-4,4-difluoro-5-methyl-piperidine-1-carboxylate, (98.7% ee).

Step 3: Benzyl (3R,5S)-3-(aminomethyl)-4,4-difluoro-5-methyl-piperidine-1-carboxylate

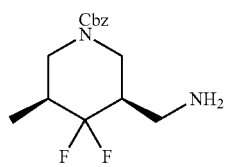 [SMILES: C[C@H]1CN(C(=O)OCc2ccccc2)C[C@@H](CN)C1(F)F]

To a suspension of benzyl (3R,5S)-3-[(1,3-dioxoisoindolin-2-yl)methyl]-4,4-difluoro-5-methyl-piperidine-1-carboxylate (9.6 g, 22.41 mmol) in ethanol (144 mL) was added hydrazine hydrate (8.5 mL, 112.0 mmol). The reaction mixture was heated to reflux for 5 hours then allowed to cool to ambient temperature overnight. The resulting suspension was filtered and the precipitate washed with EtOH (×2). The filtrate was loaded onto ion-exchange cartridges (50 g×10). The cartridges were washed with MeOH/DCM mixtures (filtrates discarded), then with 2M methanolic ammonia solution. The filtrates were combined and concentrated in vacuo. The residue was taken up in methanol and concentrated in vacuo (×2), then treated with heptane and concentrated in vacuo. The resulting yellow oil was dried under vacuum overnight to give the product as a solid (6.77 g); $^1$H NMR (400 MHz, DMSO-$d_6$) δ 7.48-7.17 (m, 5H), 5.11 (s, 2H), 4.41 (ddt, 1H), 4.02 (d, 1H), 2.98 (dd, 1H), 2.64 (s, 2H), 2.41 (dd, 1H), 2.15-1.78 (m, 2H), 1.50 (s, 2H), 0.93 (d, 3H); MS m/z: 299 [M+H]$^+$, that was taken directly on to the next reaction.

Step 4: Benzyl (3S,5S)-4,4-difluoro-3-(methanesulfonamidomethyl)-5-methyl-piperidine-1-carboxylate

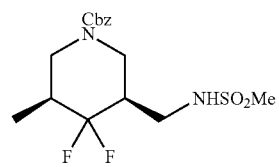

Benzyl (3R,5S)-3-(aminomethyl)-4,4-difluoro-5-methyl-piperidine-1-carboxylate (6.60 g, 22.12 mmol) was dissolved in DCM (66 mL) and cooled in an ice bath. The internal temperature reached 3° C. $Et_3N$ (3.39 mL, 24.33 mmol) was added with stirring. Methanesulfonyl chloride (1.88 mL, 24.33 mmol) was added over 5 minutes, at such a rate to keep the internal temperature below 10° C. After 30 minutes, the ice batch was removed. The solution was warmed up to ambient temperature and quenched with a saturated aqueous $NaHCO_3$ solution (66 mL). The layers were separated and the aqueous phase extracted with DCM (33 mL). The combined organics were dried over $MgSO_4$, filtered and concentrated in vacuo. The residue was purified by chromatography (silica, 0 to 100% EtOAc/Petroleum ether gradient). The product fractions were combined and concentrated in vacuo. The residue was dried overnight under vacuum to give a white solid (7.92 g; 95%); $^1$H NMR (400 MHz, DMSO-$d_6$) δ 7.45-7.31 (m, 5H), 7.31-7.19 (m, 1H), 5.12 (s, 2H), 4.37 (d, 1H), 4.18-3.94 (m, 1H), 3.38 (ddd, 1H), 3.00-2.80 (m, 4H), 2.68 (s, 2H), 2.15 (s, 2H), 0.95 (d, 3H); MS m/z: 377 [M+H]$^+$.

Step 5: N-(((3S,5S)-4,4-difluoro-5-methylpiperidin-3-yl)methyl)methanesulfonamide

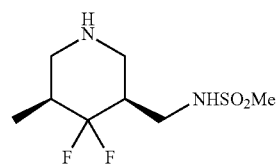

To a solution of benzyl (3S,5S)-4,4-difluoro-3-(methanesulfonamidomethyl)-5-methyl-piperidine-1-carboxylate (7.54 g, 20.03 mmol) in DCM (113 mL) was added $Et_3N$ (8.38 mL, 60.09 mmol), followed by Pd(OAc)$_2$ (1.799 g, 8.012 mmol). $Et_3SiH$ (19.20 mL, 120.2 mmol) was added over 5 minutes. The solution was stirred at ambient temperature for 1 hour then separated into 6 equal portions and loaded onto ion-exchange cartridges (50 g). The cartridges were washed with DCM, 1:1 MeOH:DCM and MeOH. The filtrates were discarded. The cartridges were washed with 2M methanolic ammonia solution. The filtrates were combined and concentrated in vacuo. The residue was azeotroped with DCM then taken up in methanol (45 mL) and stirred with SPM32 (3-mercaptopropyl ethyl sulfide silica) for 2 hours at ambient temperature, then at 50° C. for 1 hour. The mixture was cooled and filtered through Celite and the filtrate concentrated in vacuo. The residue was taken up in DCM and concentrated in vacuo. The residue was dried overnight under vacuum to give N-(((3S,5S)-4,4-difluoro-5-methylpiperidin-3-yl)methyl)methanesulfonamide as a white solid (4.40 g, 91%); $^1$H NMR (400 MHz, DMSO-$d_6$) δ 7.10 (t, 1H), 3.43-3.33 (m, 1H), 3.26-3.10 (m, 1H), 2.93-2.88 (m, 4H), 2.79 (dtd, 1H), 2.38-2.20 (m, 2H), 2.13-1.78 (m, 2H), 0.89 (d, 3H); MS m/z: 243 [M+H]$^+$.

Preparation 207: 4-Pyrrolidin-3-yl-1H-pyrazole

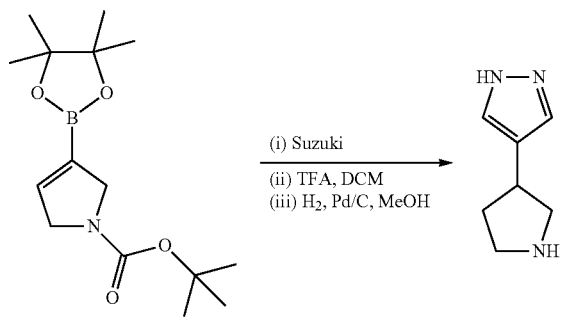 [SMILES: CC(C)(C)OC(=O)N1CC=C(B2OC(C)(C)C(C)(C)O2)C1 ; "(ii) TFA, DCM(iii) H2, Pd/C, MeOH" ; "(i) Suzuki" ; c1n[nH]cc1C1CCNC1]

Step 1: tert-Butyl 3-(1H-pyrazol-4-yl)-2,5-dihydropyrrole-1-carboxylate

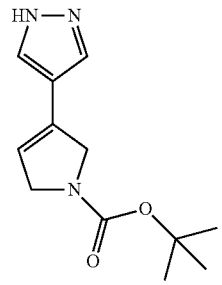 [SMILES: CC(C)(C)OC(=O)N1CC=C(c2cn[nH]c2)C1]

tert-Butyl 4-bromopyrazole-1-carboxylate (230 mg, 0.931 mmol), tert-butyl 3-(4,4,5,5-tetramethyl-1,3,2-dioxaborolan-2-yl)-2,5-dihydropyrrole-1-carboxylate (250 mg, 0.847 mmol) and potassium carbonate (1.3 mL of 2M, 2.6 mmol) were combined in dioxane (3 mL) and the mixture de-gassed (×2 vacuum cycles). Pd(dppf)Cl$_2$.DCM (70 mg, 0.086 mmol) was added and the mixture de-gassed (×2 vacuum cycles) then heated at 90° C. for 16 hours. The reaction mixture was partitioned between EtOAc and water. The organic phase was dried (Na$_2$SO$_4$), filtered and concentrated in vacuo. The residue was purified by chromatography (silica, 0-100% EtOAc/Petroleum ether gradient). The product fractions were combined and concentrated to give the product as a pale yellow film (65 mg, 33%) that was taken on to the next reaction. ESVI-MS m/z 236.0 (M+1)$^+$.

Steps 2 and 3: 4-Pyrrolidin-3-yl-1H-pyrazole

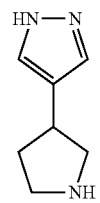

tert-Butyl 3-(1H-pyrazol-4-yl)-2,5-dihydropyrrole-1-carboxylate (550 mg, 2.338 mmol) was dissolved in DCM (10 mL) and TFA added. After 1 hour the reaction mixture was concentrated in vacuo and the residue azeotroped with DCM (×2). The residue was taken up in methanol (10 mL) and the solution degassed (×3 vacuum-N$_2$ cycles). Pd on C, wet, Degussa (200 mg of 10% w/w, 0.188 mmol) was added and the mixture degassed (×3 cycles). The N$_2$ atmosphere was replaced with hydrogen (×3 cycles) and the mixture stirred at ambient temperature. After 90 minutes the reaction mixture was filtered over Celite, washing with methanol. The filtrate was concentrated in vacuo (cold water bath) to give crude 4-pyrrolidin-3-yl-1H-pyrazole (trifluoroacetate salt) (600 mg, quantitative yield) ESVI-MS m/z 136.0 (M+1)$^+$.

Preparation 208:
2,5-Dimethyl-3-(1H-pyrazol-4-yl)piperazine

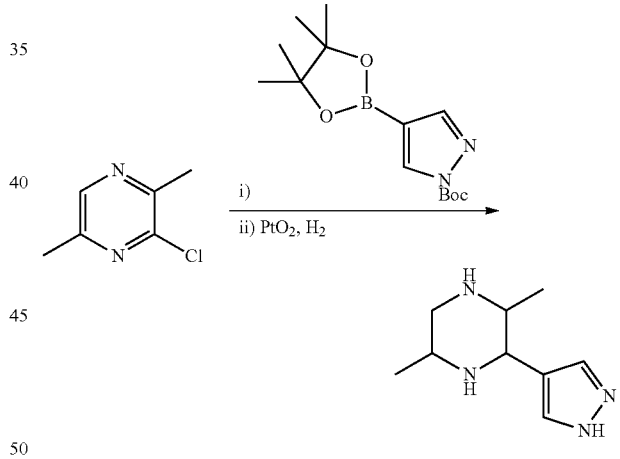

Step 1: 2,5-Dimethyl-3-(1H-pyrazol-4-yl)pyrazine

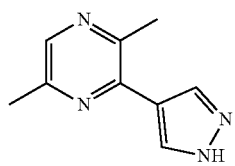

A 3-necked flask equipped with reflux condenser and thermometer was charged with 3-chloro-2,5-dimethyl-pyrazine (5 mL, 40 mmol), tert-butyl 4-(4,4,5,5-tetramethyl-1,3,2-dioxaborolan-2-yl)pyrazole-1-carboxylate (10 g, 34 mmol) in 1,4-dioxane (100 mL). Pd(PPh₃)₄ (2 g, 2 mmol), and Na₂CO₃ (60 mL of 2M, 100 mmol) were added and the solution was evacuated and backfilled with N₂ (×2). The solution was heated at 100° C. and stirred overnight. The reaction mixture was cooled to ambient temperature and filtered, washing with diethyl ether. The filtrate was concentrated in vacuo and the residue purified by chromatography (silica, 0-100% [EtOAc+2% 2M methanolic ammonia]-Petroleum ether gradient). The product fractions were combined and concentrated in vacuo to give 2,5-dimethyl-3-(1H-pyrazol-4-yl)pyrazine as a white solid (4.5 g, 64%); MS m/z: 175 (M+H)⁺.

Step 2: 2,5-Dimethyl-3-(1H-pyrazol-4-yl)piperazine

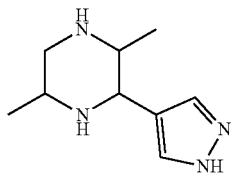

A mixture of 2,5-dimethyl-3-(1H-pyrazol-4-yl)pyrazine (4.5 g, 26 mmol), PtO₂ (1 g, 4 mmol) and HCl (60 mL of a 3M solution in MeOH, 200 mmol) was shaken in a Parr hydrogenator for 24 hours under a pressure of 60 psi H₂. The reaction mixture was filtered and the filtrate concentrated in vacuo to give the product 2,5-dimethyl-3-(1H-pyrazol-4-yl)piperazine as an off-white solid (4.0 g, 61%); MS m/z: 181 (M+H)⁺. This material was used in the next reaction assuming the dihydrochloride salt was isolated.

Preparation 209: (5-(1H-Pyrazol-4-yl)piperidin-3-yl) dimethylphosphine Oxide (Hydrochloride Salt)

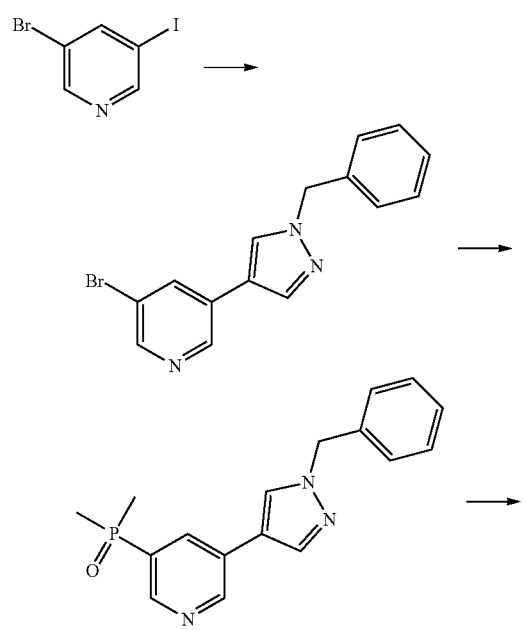

Step 1: 3-(1-Benzylpyrazol-4-yl)-5-bromo-pyridine

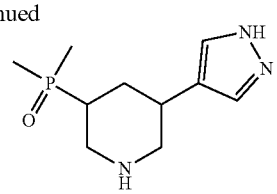

3-Bromo-5-iodo-pyridine (2.02 g, 7.115 mmol), ferrous; cyclopenta-1,4-dien-1-yl(diphenyl)phosphane; dichloromethane; dichloropalladium (290 mg, 0.355 mmol), 1-benzyl-4-(4,4,5,5-tetramethyl-1,3,2-dioxaborolan-2-yl) pyrazole (2.12 g, 7.461 mmol) and sodium carbonate (7.1 mL of 2M, 14.20 mmol) in 1,4-dioxane (70 mL) were degassed and then heated to 85° C. for 16 hours. The reaction vessel was cooled to ambient temperature, diluted with ethyl acetate, washed with brine, dried (MgSO₄), filtered and concentrated in vacuo to afford a brown residue. The crude product was purified by column chromatography (silica, 0-100% EtOAc/petroleum ether) to afford 3-(1-benzylpyrazol-4-yl)-5-bromo-pyridine (1.24 g, 55%); ¹H NMR (500 MHz, chloroform-d) δ 8.72 (s, 1H), 8.54 (s, 1H), 8.06 (s, 1H), 7.86 (s, 1H), 7.74 (s, 1H), 7.43-7.33 (m, 3H), 7.33-7.27 (m, 2H), 5.36 (s, 2H). MS m/z 316.1 (M+H)⁺.

Step 2: 3-(1-Benzylpyrazol-4-yl)-5-dimethylphosphoryl-pyridine 3-(1-Benzylpyrazol-4-yl)-5-bromo-pyridine (624 mg, 1.986 mmol), methylphosphonoylmethane (170.5 mg, 2.185 mmol), Xantphos (68.9 mg, 0.119 mmol), palladium (II) acetate (22.3 mg, 0.099 mmol) and K₃PO₄ (505.8 mg, 2.383 mmol) in DMF (10 mL) were degassed and heated to 100° C. for 16 hours. The reaction was cooled to ambient temperature, filtered and washed with methanol and then directly concentrated onto silica gel. Purification by column chromatography (silica, 0-15% MeOH/CH₂Cl₂ gradient)

afforded 3-(1-benzylpyrazol-4-yl)-5-dimethylphosphoryl-pyridine (200 mg, 32%); $^1$H NMR (500 MHz, methanol-$d_4$) δ 8.97 (t, J=2.2 Hz, 1H), 8.74 (dd, J=6.1, 1.9 Hz, 1H), 8.34 (dt, J=12.1, 2.1 Hz, 1H), 8.29 (d, J=0.8 Hz, 1H), 8.06 (d, J=0.8 Hz, 1H), 7.39-7.33 (m, 2H), 7.33-7.25 (m, 3H), 5.40 (s, 2H), 1.87 (d, J=13.6 Hz, 6H). MS m/z 312.2 (M+H)$^+$.

Step 3: (5-(1H-Pyrazol-4-yl)piperidin-3-yl)dimethylphosphine Oxide

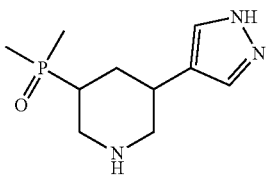

PtO$_2$ (30 mg, 0.132 mmol) was added to a high pressure vessel under nitrogen before adding a solution of 3-(1-benzylpyrazol-4-yl)-5-dimethylphosphoryl-pyridine (200 mg, 0.642 mmol) in methanol (12.9 mL). HCl in MeOH (3 mL of 3M, 9 mmol) was added before transferring the vessel to a Parr hydrogenation apparatus. The reaction was shaken under 60 psi of hydrogen gas for 16 hours. At this time further PtO$_2$ (30 mg, 0.132 mmol) was added and the reaction shaken under 60 psi of hydrogen gas for a further 24 hours. The reaction was filtered and concentrated to give 3-dimethylphosphoryl-5-(1H-pyrazol-4-yl)piperidine (Hydrochloride salt) (240 mg, 34%); MS m/z 147.1 (M+H)$^+$. This material was used without further purification.

Preparation 210: Dimethyl(piperidin-3-ylimino)-$\lambda^6$-sulfanone

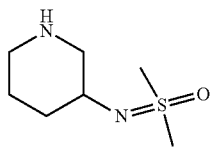

Compound prepared as in Tetrahedron, 2014, 70, 6613-6622.

Example 1: N-[[(3S,5S)-1-[6-[6-(Difluoromethyl)imidazo[1,2-b]pyridazin-3-yl]pyrimidin-4-yl]-4,4-difluoro-5-methyl-3-piperidyl]methyl]methanesulfonamide, II-36

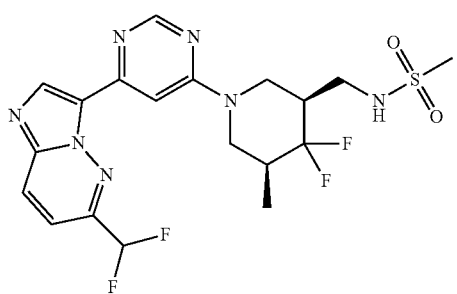 [SMILES: C[C@H]1CN(c2cc(-c3cnc4ccc(C(F)F)nn34)ncn2)C[C@@H](CNS(C)(=O)=O)C1(F)F]

3-(6-Chloropyrimidin-4-yl)-6-(difluoromethyl)imidazo[1,2-b]pyridazine (511.5 mg, 1.82 mmol), N-[[(3S,5S)-4,4-difluoro-5-methyl-3-piperidyl]methyl]methane sulfonamide (400 mg, 1.65 mmol) and DIPEA (426.8 mg, 575.2 μL, 3.30 mmol) were combined in NMP (5 mL) and stirred at 80° C. for 16 hours. The mixture was filtered through a Whatman filter, washing with DMSO (8 mL) and the resulting solution was purified by reverse phase chromatography (C18, MeCN/water/0.05% TFA as eluent). The clean fractions were then passed through bicarbonate resin cartridges, combined and the resulting solution lyophilised, to give N-[[(3S,5S)-1-[6-[6-(difluoromethyl)imidazo[1,2-b]pyridazin-3-yl]pyrimidin-4-yl]-4,4-difluoro-5-methyl-3-piperidyl]methyl]methanesulfonamide as an off-white solid (428 mg, 53%).

The following compounds were prepared using a methodology similar to the one described in Example 1:

N-((1-(6-(6-(Difluoromethyl)imidazo[1,2-b]pyridazin-3-yl)pyrimidin-4-yl)-4,4-difluoropiperidin-3-yl)methyl)methanesulfonamide II-1;

N-((1-(6-(6-(Difluoromethyl)imidazo[1,2-b]pyridazin-3-yl)pyrimidin-4-yl)-4,4-difluoropiperidin-3-yl)methyl)methanesulfonamide II-2;

N-((1-(6-(6-(Difluoromethyl)imidazo[1,2-b]pyridazin-3-yl)pyrimidin-4-yl)-6-methylpiperidin-3-yl)methyl)methanesulfonamide II-3;

4-(6-(6-(Difluoromethyl)imidazo[1,2-b]pyridazin-3-yl)pyrimidin-4-yl)-2-(1H-pyrazol-4-yl)morpholine II-4;

N-((1-(6-(6-(Difluoromethyl)imidazo[1,2-b]pyridazin-3-yl)pyrimidin-4-yl)-5-hydroxy-5-methylpiperidin-3-yl)methyl)methanesulfonamide II-5;

N-((1-(6-(6-(Difluoromethyl)imidazo[1,2-b]pyridazin-3-yl)pyrimidin-4-yl)-5-hydroxy-5-methylpiperidin-3-yl)methyl)methanesulfonamide II-6;

N-((1-(6-(6-(Difluoromethyl)imidazo[1,2-b]pyridazin-3-yl)pyrimidin-4-yl)indolin-3-yl)methyl)methanesulfonamide II-11;

1-(6-(6-(Difluoromethyl)imidazo[1,2-b]pyridazin-3-yl)pyrimidin-4-yl)-1,4-diazepan-5-one II-15;

1-(6-(6-(Difluoromethyl)imidazo[1,2-b]pyridazin-3-yl)pyrimidin-4-yl)indoline-3-carboxamide II-16;

6-(Difluoromethyl)-3-(6-(3-(methylsulfonyl)piperidin-1-yl)pyrimidin-4-yl)imidazo[1,2-b]pyridazine II-19;

6-(Difluoromethyl)-3-(6-(indolin-1-yl)pyrimidin-4-yl)imidazo[1,2-b]pyridazine II-20;

6-(Difluoromethyl)-3-(6-(4-(methylsulfonyl)-1,4-diazepan-1-yl)pyrimidin-4-yl)imidazo[1,2-b]pyridazine II-22;

4-(6-(6-(Difluoromethyl)imidazo[1,2-b]pyridazin-3-yl)pyrimidin-4-yl)-1,4-diazepane-1-sulfonamide II-24;

(1-(tert-Butyl)-4-(6-(6-(difluoromethyl)imidazo[1,2-b]pyridazin-3-yl)pyrimidin-4-yl)-3-methylpiperazin-2-yl)methanol II-43;

7-(6-(6-(Difluoromethyl)imidazo[1,2-b]pyridazin-3-yl)pyrimidin-4-yl)hexahydroimidazo[1,5-a]pyrazin-3(2H)-one II-46;

(S)-7-(6-(6-(Difluoromethyl)imidazo[1,2-b]pyridazin-3-yl)pyrimidin-4-yl)hexahydro-3H-oxazolo[3,4-a]pyrazin-3-one II-47;

4-(6-(6-(Difluoromethyl)imidazo[1,2-b]pyridazin-3-yl)pyrimidin-4-yl)morpholine-2-carboxamide II-50;

7-(6-(6-(Difluoromethyl)imidazo[1,2-b]pyridazin-3-yl)pyrimidin-4-yl)-2,7-diazaspiro[4.5]decan-1-one II-51;

7-(6-(6-(Difluoromethyl)imidazo[1,2-b]pyridazin-3-yl)pyrimidin-4-yl)-1,7-diazaspiro[3.5]nonan-2-one II-52;

N-((1-(6-(6-(Difluoromethyl)imidazo[1,2-b]pyridazin-3-yl)pyrimidin-4-yl)-4-hydroxypiperidin-3-yl)methyl)methanesulfonamide II-112;

N-((1-(6-(6-(Difluoromethyl)imidazo[1,2-b]pyridazin-3-yl)pyrimidin-4-yl)-3-hydroxypyrrolidin-3-yl)methyl)methanesulfonamide II-137;

N-((1-(6-(6-(Difluoromethyl)imidazo[1,2-b]pyridazin-3-yl)pyrimidin-4-yl)-4-hydroxypyrrolidin-3-yl)methyl)methanesulfonamide II-140;

N-((1-(6-(6-(Difluoromethyl)imidazo[1,2-b]pyridazin-3-yl)pyrimidin-4-yl)-4-hydroxypyrrolidin-3-yl)methyl)methanesulfonamide II-152;

N-((1-(6-(6-(Difluoromethyl)imidazo[1,2-b]pyridazin-3-yl)pyrimidin-4-yl)-3-hydroxypiperidin-3-yl)methyl)methanesulfonamide II-158;

N-(1-(4-(6-(6-(Difluoromethyl)imidazo[1,2-b]pyridazin-3-yl)pyrimidin-4-yl)morpholin-2-yl)ethyl)methanesulfonamide II-159;

N-(1-(4-(6-(6-(Difluoromethyl)imidazo[1,2-b]pyridazin-3-yl)pyrimidin-4-yl)morpholin-2-yl)ethyl)methanesulfonamide II-177;

1-(4-(6-(6-(Difluoromethyl)imidazo[1,2-b]pyridazin-3-yl)pyrimidin-4-yl)piperazin-1-yl)ethan-1-one II-186;

N-(1-(6-(6-(Difluoromethyl)imidazo[1,2-b]pyridazin-3-yl)pyrimidin-4-yl)piperidin-3-yl)acetamide II-190;

1-(6-(6-(Difluoromethyl)imidazo[1,2-b]pyridazin-3-yl)pyrimidin-4-yl)-N-(2-hydroxyethyl)piperidine-3-carboxamide II-191;

1-(6-(6-(Difluoromethyl)imidazo[1,2-b]pyridazin-3-yl)pyrimidin-4-yl)pyrrolidine-3-sulfonamide II-192;

(S)—N-((4-(6-(6-Ethylimidazo[1,2-b]pyridazin-3-yl)pyrimidin-4-yl)morpholin-2-yl)methyl)methanesulfonamide II-196;

N-((1-(6-(6-(Difluoromethyl)imidazo[1,2-b]pyridazin-3-yl)pyrimidin-4-yl)-5-methoxypiperidin-3-yl)methyl)methanesulfonamide II-198;

N-(1-(6-(6-(Difluoromethyl)imidazo[1,2-b]pyridazin-3-yl)pyrimidin-4-yl)pyrrolidin-3-yl)methanesulfonamide II-199;

5-(6-(6-(Difluoromethyl)imidazo[1,2-b]pyridazin-3-yl)pyrimidin-4-yl)octahydro-3H-pyrrolo[3,4-c]pyridin-3-one II-200;

(6R)-4-(6-(6-(Difluoromethyl)imidazo[1,2-b]pyridazin-3-yl)pyrimidin-4-yl)-6-methylmorpholine-2-carboxamide II-201;

1-((1-(6-(6-(Difluoromethyl)imidazo[1,2-b]pyridazin-3-yl)pyrimidin-4-yl)piperidin-3-yl)methyl)sulfuric diamide II-202;

3-(6-(3-(1H-imidazol-4-yl)pyrrolidin-1-yl)pyrimidin-4-yl)-6-(difluoromethyl)imidazo[1,2-b]pyridazine II-203;

3-(1-(6-(6-(Difluoromethyl)imidazo[12-b]pyridazin-3-yl)pyrimidin-4-yl)piperidin-3-yl)-1H-pyrazole-5-carboxamide II-205;

N-(2-(1-(6-(6-(Difluoromethyl)imidazo[1,2-b]pyridazin-3-yl)pyrimidin-4-yl)piperidin-3-yl)ethyl)-2-methoxyacetamide II-209;

4-(6-(6-(Difluoromethyl)imidazo[1,2-b]pyridazin-3-yl)pyrimidin-4-yl)-1,4-oxazepane-6-carboxamide II-210;

9-(6-(6-(Difluoromethyl)imidazo[1,2-b]pyridazin-3-yl)pyrimidin-4-yl)-2,9-diazaspiro[5.5]undecan-3-one II-211;

3-(1-(6-(6-(Difluoromethyl)imidazo[1,2-b]pyridazin-3-yl)pyrimidin-4-yl)piperidin-4-yl)propanamide II-212;

N-((1-(6-(6-(Difluoromethyl)imidazo[1,2-b]pyridazin-3-yl)pyrimidin-4-yl)-4,4-dimethylpyrrolidin-3-yl)methyl)methanesulfonamide II-213;

3-(1-(6-(6-(Difluoromethyl)imidazo[1,2-b]pyridazin-3-yl)pyrimidin-4-yl)piperidin-3-yl)propanamide II-214;

1-((1-(6-(6-(Difluoromethyl)imidazo[1,2-b]pyridazin-3-yl)pyrimidin-4-yl)piperidin-3-yl)methyl)urea II-215;

1-Cyclopropyl-3-(1-(6-(6-(difluoromethyl)imidazo[1,2-b]pyridazin-3-yl)pyrimidin-4-yl)pyrrolidin-3-yl)urea II-216;

3-(6-(4-((1H-Pyrazol-5-yl)methyl)piperidin-1-yl)pyrimidin-4-yl)-6-(difluoromethyl)imidazo[1,2-b]pyridazine II-217;

N-(2-(6-(6-(Difluoromethyl)imidazo[1,2-b]pyridazin-3-yl)pyrimidin-4-yl)-1,2,3,4-tetrahydroisoquinolin-5-yl)acetamide II-218;

(1-(6-(6-(Difluoromethyl)imidazo[1,2-b]pyridazin-3-yl)pyrimidin-4-yl)piperidin-3-yl)methanesulfonamide II-219;

N-((1-(6-(6-(Difluoromethyl)imidazo[1,2-b]pyridazin-3-yl)pyrimidin-4-yl)-2-methylpiperidin-3-yl)methyl)methanesulfonamide II-221;

N-((1-(6-(6-(Difluoromethyl)imidazo[1,2-b]pyridazin-3-yl)pyrimidin-4-yl)-4-hydroxy-4-methylpiperidin-3-yl)methyl)methanesulfonamide II-239;

N-((1-(6-(6-(Difluoromethyl)imidazo[1,2-b]pyridazin-3-yl)pyrimidin-4-yl)-4-hydroxy-4-methylpiperidin-3-yl)methyl)methanesulfonamide II-240;

N-((1-(6-(6-(Difluoromethyl)imidazo[1,2-b]pyridazin-3-yl)pyrimidin-4-yl)-2-methylpyrrolidin-3-yl)methyl)methanesulfonamide II-243;

N-((1-(6-(6-(Difluoromethyl)imidazo[1,2-b]pyridazin-3-yl)pyrimidin-4-yl)-2-methylpyrrolidin-3-yl)methyl)methanesulfonamide II-244;

N-((1-(6-(6-(Difluoromethyl)imidazo[1,2-b]pyridazin-3-yl)pyrimidin-4-yl)-6-methylpiperidin-3-yl)methyl)methanesulfonamide II-245;

N-((1-(6-(6-(Difluoromethyl)imidazo[1,2-b]pyridazin-3-yl)pyrimidin-4-yl)-6-methylpiperidin-3-yl)methyl)methanesulfonamide II-246;

N-(((3S,6R)-1-(6-(6-(Difluoromethyl)imidazo[1,2-b]pyridazin-3-yl)pyrimidin-4-yl)-6-methylpiperidin-3-yl)methyl)methanesulfonamide II-247;

N-((1-(6-(6-(Difluoromethyl)imidazo[1,2-b]pyridazin-3-yl)pyrimidin-4-yl)-6-methylpiperidin-3-yl)methyl)methanesulfonamide II-248;

(S)—N-((4-(6-(6-Cyclopropylimidazo[1,2-b]pyridazin-3-yl)pyrimidin-4-yl)morpholin-2-yl)methyl)methanesulfonamide II-249;

4-(6-(6-(Difluoromethyl)imidazo[1,2-b]pyridazin-3-yl)pyrimidin-4-yl)morpholine II-251;

6-(6-(6-(Difluoromethyl)imidazo[1,2-b]pyridazin-3-yl)pyrimidin-4-yl)-2-oxa-6-azaspiro[3.3]heptane II-252;

6-(6-(6-(Difluoromethyl)imidazo[1,2-b]pyridazin-3-yl)pyrimidin-4-yl)-2-(methylsulfonyl)-2,6-diazaspiro[4.5]decane II-256;

(R)—N-((4-(6-(6-(Difluoromethyl)imidazo[1,2-b]pyridazin-3-yl)pyrimidin-4-yl)-6,6-dimethylmorpholin-2-yl)methyl)methanesulfonamide II-257;

N-((1-(6-(6-(Difluoromethyl)imidazo[1,2-b]pyridazin-3-yl)pyrimidin-4-yl)-5,5-difluoropiperidin-3-yl)methyl)methanesulfonamide II-258;

N-((1-(6-(6-(Difluoromethyl)imidazo[1,2-b]pyridazin-3-yl)pyrimidin-4-yl)-5-(dimethylamino)-4,4-difluoropiperidin-3-yl)methyl)methanesulfonamide II-259;

N-((1-(6-(6-(Difluoromethyl)imidazo[1,2-b]pyridazin-3-yl)pyrimidin-4-yl)-5-(dimethylamino)-4,4-difluoropiperidin-3-yl)methyl)methanesulfonamide II-260;

N-((1-(6-(6-(Difluoromethyl)imidazo[1,2-b]pyridazin-3-yl)pyrimidin-4-yl)piperidin-3-yl)methyl)acetamide II-261;

N-((1-(6-(6-(Difluoromethyl)imidazo[1,2-b]pyridazin-3-yl)pyrimidin-4-yl)-2,6-dimethylpiperidin-3-yl)methyl)methanesulfonamide II-268;

N-[[(3S,5S)-1-[2-[6-(Difluoromethyl)imidazo[1,2-b]pyridazin-3-yl]-5-fluoro-4-pyridyl]-4,4-difluoro-5-methyl-3-piperidyl]methyl]methanesulfonamide II-270;

N-[[1-[2-[6-(Difluoromethyl)imidazo[1,2-b]pyridazin-3-yl]-5-fluoro-4-pyridyl]-6-methyl-3-piperidyl]methyl]methanesulfonamide II-271;

3-(6-(7,7-Difluoro-3-azabicyclo[4.1.0]heptan-3-yl)pyrimidin-4-yl)-6-(difluoromethyl)imidazo[1,2-b]pyridazine II-274;

2-(1-(6-(6-(Difluoromethyl)imidazo[1,2-b]pyridazin-3-yl)pyrimidin-4-yl)piperidin-2-yl)ethane-1-sulfonamide II-283;

(S)—N-((1-(6-(6-(Trifluoromethyl)imidazo[1,2-b]pyridazin-3-yl)pyrimidin-4-yl)piperidin-3-yl)methyl)methanesulfonamide II-291;

(S)—N-((4-(6-(6-(Trifluoromethyl)imidazo[1,2-b]pyridazin-3-yl)pyrimidin-4-yl)morpholin-2-yl)methyl)methanesulfonamide II-292;

N-((4,4-Difluoro-5-methyl-1-(6-(6-(trifluoromethyl)imidazo[1,2-b]pyridazin-3-yl)pyrimidin-4-yl)piperidin-3-yl)methyl)methanesulfonamide II-293;

N-((4,4-Difluoro-5-methyl-1-(6-(6-(trifluoromethyl)imidazo[1,2-b]pyridazin-3-yl)pyrimidin-4-yl)piperidin-3-yl)methyl)methanesulfonamide II-294;

4-(6-(6-(Difluoromethyl)imidazo[1,2-b]pyridazin-3-yl)pyrimidin-4-yl)thiomorpholine 1,1-dioxide II-295;

4-(6-(6-(Difluoromethyl)imidazo[1,2-b]pyridazin-3-yl)pyrimidin-4-yl)thiomorpholine 1-oxide II-296;

((2S,6S)-4-(6-(6-(Difluoromethyl)imidazo[1,2-b]pyridazin-3-yl)pyrimidin-4-yl)-6-(trifluoromethyl)morpholin-2-yl)methanol II-297;

((2R,6S)-4-(6-(6-(Difluoromethyl)imidazo[1,2-b]pyridazin-3-yl)pyrimidin-4-yl)-6-(trifluoromethyl)morpholin-2-yl)methanol II-298;

2-(1-(6-(6-(Difluoromethyl)imidazo[1,2-b]pyridazin-3-yl)pyrimidin-4-yl)piperidin-3-yl)acetonitrile II-299;

(S)—N-((1-(6-(6-(Difluoromethyl)imidazo[1,2-b]pyridazin-3-yl)pyrimidin-4-yl)piperidin-3-yl)methyl)methanesulfonamide II-300;

5-(6-(6-(Difluoromethyl)imidazo[1,2-b]pyridazin-3-yl)pyrimidin-4-yl)-2-oxa-5-azabicyclo[4.1.0]heptane II-301;

6-(Difluoromethyl)-3-(6-(piperidin-1-yl)pyrimidin-4-yl)imidazo[1,2-b]pyridazine II-308;

11-(6-(6-(Difluoromethyl)imidazo[1,2-b]pyridazin-3-yl)pyrimidin-4-yl)-1,8-dioxa-4,11-diazaspiro[5.6]dodecan-3-one II-309;

N-((4-(6-(6-(Difluoromethyl)imidazo[1,2-b]pyridazin-3-yl)pyrimidin-4-yl)-3-methylpiperazin-2-yl)methyl)methanesulfonamide II-313;

((3R,5R)-1-(6-(6-(Difluoromethyl)imidazo[1,2-b]pyridazin-3-yl)pyrimidin-4-yl)-5-(trifluoromethyl)piperidin-3-yl)methanol II-314;

((3S,5R)-1-(6-(6-(Difluoromethyl)imidazo[1,2-b]pyridazin-3-yl)pyrimidin-4-yl)-5-(trifluoromethyl)piperidin-3-yl)methanol II-315;

1-(((3S,5S)-1-(6-(6-(Difluoromethyl)imidazo[1,2-b]pyridazin-3-yl)pyrimidin-4-yl)-4,4-difluoro-5-methylpiperidin-3-yl)methyl)sulfuric diamide II-316;

2-(1-(6-(6-(Difluoromethyl)imidazo[12-b]pyridazin-3-yl)pyrimidin-4-yl)piperidin-3-yl)ethane-1-sulfonamide II-317;

2-(4-(6-(6-(Difluoromethyl)imidazo[1,2-b]pyridazin-3-yl)pyrimidin-4-yl)morpholin-2-yl)ethane-1-sulfonamide II-318;

N-(((3S,5S)-1-(6-(6-(1,1-Difluoroethyl)imidazo[1,2-b]pyridazin-3-yl)pyrimidin-4-yl)-4,4-difluoro-5-methylpiperidin-3-yl)methyl)methanesulfonamide II-321;

(S)—N-((4-(6-(6-(1,1-Difluoroethyl)imidazo[1,2-b]pyridazin-3-yl)pyrimidin-4-yl)morpholin-2-yl)methyl)methanesulfonamide II-322;

(S)-6-(Difluoromethyl)-3-(6-(2-methylpiperidin-1-yl)pyrimidin-4-yl)imidazo[1,2-b]pyridazine II-323;

(R)-4-(6-(6-(Difluoromethyl)imidazo[1,2-b]pyridazin-3-yl)pyrimidin-4-yl)-3-methylmorpholine II-324;

(S)-4-(6-(6-(Difluoromethyl)imidazo[1,2-b]pyridazin-3-yl)pyrimidin-4-yl)-3-methylmorpholine II-325;

2-((1H-1,2,4-Triazol-1-yl)methyl)-4-(6-(6-(difluoromethyl)imidazo[1,2-b]pyridazin-3-yl)pyrimidin-4-yl)morpholine II-326;

3-(6-(3-((1H-1,2,3-Triazol-1-yl)methyl)piperidin-1-yl)pyrimidin-4-yl)-6-(difluoromethyl)imidazo[1,2-b]pyridazine II-327;

(S)—N-((4-(6-(6-Methylimidazo[1,2-b]pyridazin-3-yl)pyrimidin-4-yl)morpholin-2-yl)methyl)methanesulfonamide II-328;

N-((1-(6-(6-(Difluoromethyl)imidazo[1,2-b]pyridazin-3-yl)pyrimidin-4-yl)-5,5-difluoro-2-methylpiperidin-3-yl)methyl)methanesulfonamide II-329;

N-((1-(6-(6-(Difluoromethyl)imidazo[1,2-b]pyridazin-3-yl)pyrimidin-4-yl)-3-methylpiperazin-2-yl)methyl)methanesulfonamide II-336;

3-(6-(3-((1H-1,2,4-Triazol-1-yl)methyl)piperidin-1-yl)pyrimidin-4-yl)-6-(difluoromethyl)imidazo[1,2-b]pyridazine II-339;

(4-(6-(6-(Difluoromethyl)imidazo[1,2-b]pyridazin-3-yl)pyrimidin-4-yl)-3-methylmorpholin-2-yl)methanol II-341;

(4-(6-(6-(Difluoromethyl)imidazo[1,2-b]pyridazin-3-yl)pyrimidin-4-yl)-3-methylmorpholin-2-yl)methanol II-342;

(8-(6-(6-(Difluoromethyl)imidazo[1,2-b]pyridazin-3-yl)pyrimidin-4-yl)-2,5-dioxa-8-azaspiro[3.5]nonan-6-yl)methanol II-343;

1-(2-(1-(6-(6-(Difluoromethyl)imidazo[1,2-b]pyridazin-3-yl)pyrimidin-4-yl)piperidin-4-yl)ethyl)pyrrolidin-3-ol II-351;

1'-(6-(6-(Difluoromethyl)imidazo[1,2-b]pyridazin-3-yl)pyrimidin-4-yl)-[1,3'-bipyrrolidin]-3-ol II-352;

4-((1-(6-(6-(Difluoromethyl)imidazo[1,2-b]pyridazin-3-yl)pyrimidin-4-yl)pyrrolidin-3-yl)methyl)piperazin-2-one II-353;

(R)-6-(Difluoromethyl)-3-(6-(2-methylpiperidin-1-yl)pyrimidin-4-yl)imidazo[1,2-b]pyridazine II-354;

(7-(6-(6-(Difluoromethyl)imidazo[1,2-b]pyridazin-3-yl)pyrimidin-4-yl)-4-oxa-7-azaspiro[2.5]octan-5-yl)methanol II-359;

N-(1-(6-(6-(Difluoromethyl)imidazo[1,2-b]pyridazin-3-yl)pyrimidin-4-yl)piperidin-3-yl)methanesulfonamide II-362;

N-((1-(6-(6-(Difluoromethyl)imidazo[1,2-b]pyridazin-3-yl)pyrimidin-4-yl)-4-hydroxy-4,6-dimethylpiperidin-3-yl)methyl)methanesulfonamide II-365;

N-((1-(6-(6-(Difluoromethyl)imidazo[1,2-b]pyridazin-3-yl)pyrimidin-4-yl)-4-hydroxy-2,4-dimethylpiperidin-3-yl)methyl)methanesulfonamide II-366;

N-((1-(6-(6-(Difluoromethyl)imidazo[1,2-b]pyridazin-3-yl)pyrimidin-4-yl)-4-hydroxy-4,6-dimethylpiperidin-3-yl)methyl)methanesulfonamide II-367;

1-(4-(6-(6-(Difluoromethyl)imidazo[1,2-b]pyridazin-3-yl)pyrimidin-4-yl)-3-methylpiperazin-1-yl)ethan-1-one II-368;

(1-(6-(6-(Difluoromethyl)imidazo[1,2-b]pyridazin-3-yl)pyrimidin-4-yl)-2-methylpiperidin-3-yl)methanol II-373;

1-(6-(6-(Difluoromethyl)imidazo[1,2-b]pyridazin-3-yl)pyrimidin-4-yl)piperidine-3-sulfonamide II-376;

1-(6-(6-(Difluoromethyl)imidazo[1,2-b]pyridazin-3-yl)pyrimidin-4-yl)piperidine-3-carboxamide II-378;

N-((1-(6-(6-(Difluoromethyl)imidazo[1,2-b]pyridazin-3-yl)pyrimidin-4-yl)piperidin-3-yl)methyl)-1,1,1-trifluoromethanesulfonamide II-379;

6-(Difluoromethyl)-3-(6-(2-(trifluoromethyl)piperidin-1-yl)pyrimidin-4-yl)imidazo[1,2-b]pyridazine II-380;

N-((1-(6-(6-(Difluoromethyl)imidazo[1,2-b]pyridazin-3-yl)pyrimidin-4-yl)-5,5-difluoro-4-methylpiperidin-3-yl)methyl)methanesulfonamide II-381;

N-((1-(6-(6-(Difluoromethyl)imidazo[1,2-b]pyridazin-3-yl)pyrimidin-4-yl)-5,5-difluoro-4-methylpiperidin-3-yl)methyl)methanesulfonamide II-382;

N-((1-(6-(6-(Difluoromethyl)imidazo[1,2-b]pyridazin-3-yl)pyrimidin-4-yl)-4-methoxypiperidin-3-yl)methyl)methanesulfonamide II-390;

N-((1-(6-(6-(Difluoromethyl)imidazo[1,2-b]pyridazin-3-yl)pyrimidin-4-yl)-2-ethylpiperidin-3-yl)methyl)methanesulfonamide II-391;

N-((1-(6-(6-(Difluoromethyl)imidazo[1,2-b]pyridazin-3-yl)pyrimidin-4-yl)pyrrolidin-3-yl)methyl)methanesulfonamide II-394;

6-(Difluoromethyl)-3-(6-(3-(methylsulfonyl)pyrrolidin-1-yl)pyrimidin-4-yl)imidazo[1,2-b]pyridazine II-395;

6-(Difluoromethyl)-3-(6-(3-((methylsulfonyl)methyl)pyrrolidin-1-yl)pyrimidin-4-yl)imidazo[1,2-b]pyridazine II-396;

N-((1-(6-(6-(Difluoromethyl)imidazo[1,2-b]pyridazin-3-yl)pyrimidin-4-yl)-5-methylpiperidin-3-yl)methyl)methanesulfonamide II-397;

N-((1-(6-(6-(Difluoromethyl)imidazo[1,2-b]pyridazin-3-yl)pyrimidin-4-yl)-5-methylpiperidin-3-yl)methyl)methanesulfonamide II-398;

1-(6-(6-(Difluoromethyl)imidazo[1,2-b]pyridazin-3-yl)pyrimidin-4-yl)pyrrolidine-3-carboxamide II-399;

4-(6-(6-(Difluoromethyl)imidazo[1,2-b]pyridazin-3-yl)pyrimidin-4-yl)-7-oxa-4-azaspiro[2.5]octane II-400;

3-(6-(4-Azaspiro[2.5]octan-4-yl)pyrimidin-4-yl)-6-(trifluoromethyl)imidazo[1,2-b]pyridazine II-401;

4-(6-(6-(Difluoromethyl)imidazo[1,2-b]pyridazin-3-yl)pyrimidin-4-yl)-3,3-dimethylmorpholine II-402;

(S)—N-((4-(6-(6-(Difluoromethyl)imidazo[1,2-b]pyridazin-3-yl)pyrimidin-4-yl)-6,6-dimethylmorpholin-2-yl)methyl)methanesulfonamide II-403;

(S)-Dimethyl(((4-(6-(6-(trifluoromethyl)imidazo[1,2-b]pyridazin-3-yl)pyrimidin-4-yl)morpholin-2-yl)methyl)imino)-$\lambda^6$-sulfanone II-406;

Dimethyl((1-(6-(6-(trifluoromethyl)imidazo[1,2-b]pyridazin-3-yl)pyrimidin-4-yl)piperidin-3-yl)imino)-$\lambda^6$-sulfanone II-407;

((1-(6-(6-(Difluoromethyl)imidazo[1,2-b]pyridazin-3-yl)pyrimidin-4-yl)piperidin-3-yl)imino)dimethyl-$\lambda^6$-sulfanone II-408;

(((4-(6-(6-(Difluoromethyl)imidazo[1,2-b]pyridazin-3-yl)pyrimidin-4-yl)-6-methylpiperazin-2-yl)methyl)imino)dimethyl-$\lambda^6$-sulfanone II-411;

(1-(6-(6-(Difluoromethyl)imidazo[1,2-b]pyridazin-3-yl)pyrimidin-4-yl)-2-methylpiperidin-3-yl)methanesulfonamide II-424;

N-((4-(6-(6-(Difluoromethyl)imidazo[1,2-b]pyridazin-3-yl)pyrimidin-4-yl)-3,6-dimethylpiperazin-2-yl)methyl)methanesulfonamide II-427;

N-((1-(6-(6-(Difluoromethyl)imidazo[1,2-b]pyridazin-3-yl)pyrimidin-4-yl)-5-(3-fluoroazetidin-1-yl)piperidin-3-yl)methyl)methanesulfonamide II-428;

N-((1-(6-(6-(Difluoromethyl)imidazo[1,2-b]pyridazin-3-yl)pyrimidin-4-yl)-5-(3-fluoroazetidin-1-yl)piperidin-3-yl)methyl)methanesulfonamide II-429;

6-(Difluoromethyl)-3-(6-(3-((methylsulfonyl)methyl)piperidin-1-yl)pyrimidin-4-yl)imidazo[1,2-b]pyridazine II-430;

N-((1-(6-(6-(Difluoromethyl)imidazo[1,2-b]pyridazin-3-yl)pyrimidin-4-yl)-4,4-difluoro-2-methylpiperidin-3-yl)methyl)methanesulfonamide II-431;

N-((1-(6-(6-(Difluoromethyl)imidazo[1,2-b]pyridazin-3-yl)pyrimidin-4-yl)-4,4-difluoro-2-methylpiperidin-3-yl)methyl)methanesulfonamide II-432;

N-((1-(6-(6-(Difluoromethyl)imidazo[1,2-b]pyridazin-3-yl)pyrimidin-4-yl)-4,4-difluoro-6-methylpiperidin-3-yl)methyl)methanesulfonamide II-433;

N-((1-(6-(6-(Difluoromethyl)imidazo[1,2-b]pyridazin-3-yl)pyrimidin-4-yl)-4,4-difluoro-6-methylpiperidin-3-yl)methyl)methanesulfonamide II-434;

(3-(6-(6-(Difluoromethyl)imidazo[1,2-b]pyridazin-3-yl)pyrimidin-4-yl)-3-azabicyclo[3.1.0]hexan-1-yl)methanol II-438;

N-((3S,5R)-1-(6-(6-(Difluoromethyl)imidazo[1,2-b]pyridazin-3-yl)pyrimidin-4-yl)-5-methylpiperidin-3-yl)methanesulfonamide II-449;

N-((4-(6-(6-(Difluoromethyl)imidazo[1,2-b]pyridazin-3-yl)pyrimidin-4-yl)piperazin-2-yl)methyl)methanesulfonamide II-450;

3-(6-(6-(Difluoromethyl)imidazo[1,2-b]pyridazin-3-yl)pyrimidin-4-yl)-6-oxa-3-azabicyclo[3.1.1]heptane II-451;

8-(6-(6-(Difluoromethyl)imidazo[1,2-b]pyridazin-3-yl)pyrimidin-4-yl)-5-methyl-2-(methylsulfonyl)-2,5,8-triazaspiro[3.5]nonane II-452;

4-(6-(6-(Difluoromethyl)imidazo[1,2-b]pyridazin-3-yl)pyrimidin-4-yl)-1-methylpiperazine-2-carboxamide II-453;

(S)-1-(4-(6-(6-(Difluoromethyl)imidazo[1,2-b]pyridazin-3-yl)pyrimidin-4-yl)piperazin-2-yl)cyclopropan-1-ol II-454;

N-(1-(6-(6-(Difluoromethyl)imidazo[1,2-b]pyridazin-3-yl)pyrimidin-4-yl)piperidin-3-yl)-N-methylmethanesulfonamide II-455;

N-((4-(6-(6-(Difluoromethyl)imidazo[1,2-b]pyridazin-3-yl)pyrimidin-4-yl)-5,5-dimethylmorpholin-2-yl)methyl)methanesulfonamide II-457;

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-461;

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-462;

(4-(6-(6-(Difluoromethyl)imidazo[1,2-b]pyridazin-3-yl)pyrimidin-4-yl)-1-methylpiperazin-2-yl)methanesulfonamide II-464;

N-(1-(4-(6-(6-(Difluoromethyl)imidazo[1,2-b]pyridazin-3-yl)pyrimidin-4-yl)piperazin-2-yl)ethyl)methanesulfonamide II-465;

N-((3-Methyl-4-(6-(6-(trifluoromethyl)imidazo[1,2-b]pyridazin-3-yl)pyrimidin-4-yl)piperazin-2-yl)methyl)methanesulfonamide II-466;

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-475;

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-476;

4-(6-(6-(Difluoromethyl)imidazo[1,2-b]pyridazin-3-yl)pyrimidin-4-yl)-3-methylpiperazine-2-carboxamide II-477;

1-(6-(6-(Difluoromethyl)imidazo[1,2-b]pyridazin-3-yl)pyrimidin-4-yl)-N-methylpiperidine-3-sulfonamide II-480;

N-((4-(6-(6-(Difluoromethyl)imidazo[1,2-b]pyridazin-3-yl)pyrimidin-4-yl)-1,4-oxazepan-6-yl)methyl)methanesulfonamide II-481;

2-(4-(6-(6-(Difluoromethyl)imidazo[1,2-b]pyridazin-3-yl)pyrimidin-4-yl)piperazin-2-yl)acetamide II-483;

N-((1-(6-(6-(Difluoromethyl)imidazo[1,2-b]pyridazin-3-yl)pyrimidin-4-yl)-4-fluoro-2,5-dimethyl-1,2,5,6-tetrahydropyridin-3-yl)methyl)methanesulfonamide II-491;

6-(Difluoromethyl)-3-(6-(3-(2-(methylsulfonyl)ethyl)piperidin-1-yl)pyrimidin-4-yl)imidazo[1,2-b]pyridazine II-493;

2-(4-(6-(6-(Difluoromethyl)imidazo[1,2-b]pyridazin-3-yl)pyrimidin-4-yl)piperazin-2-yl)ethan-1-ol II-496;

2-(1-(6-(6-(Difluoromethyl)imidazo[1,2-b]pyridazin-3-yl)pyrimidin-4-yl)piperidin-3-yl)ethan-1-ol II-497;

2-(4-(6-(6-(Difluoromethyl)imidazo[1,2-b]pyridazin-3-yl)pyrimidin-4-yl)morpholin-2-yl)ethan-1-ol II-498;

2-(1-(6-(6-(Trifluoromethyl)imidazo[1,2-b]pyridazin-3-yl)pyrimidin-4-yl)piperidin-3-yl)ethan-1-ol II-499;

2-(4-(6-(6-(Trifluoromethyl)imidazo[1,2-b]pyridazin-3-yl)pyrimidin-4-yl)morpholin-2-yl)ethan-1-ol II-500;

2-(1-(6-(6-(Trifluoromethyl)imidazo[1,2-b]pyridazin-3-yl)pyrimidin-4-yl)piperidin-3-yl)acetonitrile II-501;

(S)-1-(6-(6-(Trifluoromethyl)imidazo[1,2-b]pyridazin-3-yl)pyrimidin-4-yl)piperidine-3-carboxylic acid II-504;

(S)-1-(6-(6-(Difluoromethyl)imidazo[1,2-b]pyridazin-3-yl)pyrimidin-4-yl)piperidine-3-carboxylic acid II-505;

(R)-1-(6-(6-(Trifluoromethyl)imidazo[1,2-b]pyridazin-3-yl)pyrimidin-4-yl)piperidine-3-carboxylic acid II-506;

(R)-1-(6-(6-(Difluoromethyl)imidazo[1,2-b]pyridazin-3-yl)pyrimidin-4-yl)piperidine-3-carboxylic acid II-508;

N-((1-(6-(6-(Difluoromethyl)imidazo[1,2-b]pyridazin-3-yl)pyrimidin-4-yl)-2,5-dimethylpiperidin-3-yl)methyl)methanesulfonamide II-511;

2-(4-(6-(6-(Difluoromethyl)imidazo[1,2-b]pyridazin-3-yl)pyrimidin-4-yl)morpholin-2-yl)acetonitrile II-512;

2-(4-(6-(6-(Trifluoromethyl)imidazo[1,2-b]pyridazin-3-yl)pyrimidin-4-yl)morpholin-2-yl)acetonitrile II-513;

(S)-(1-(6-(6-(Trifluoromethyl)imidazo[1,2-b]pyridazin-3-yl)pyrimidin-4-yl)piperidin-3-yl)methanol II-516;

(R)-(1-(6-(6-(Trifluoromethyl)imidazo[1,2-b]pyridazin-3-yl)pyrimidin-4-yl)piperidin-3-yl)methanol II-517;

(4-(6-(6-(Trifluoromethyl)imidazo[1,2-b]pyridazin-3-yl)pyrimidin-4-yl)morpholin-2-yl)methanol II-518;

(S)-(1-(6-(6-(Difluoromethyl)imidazo[1,2-b]pyridazin-3-yl)pyrimidin-4-yl)piperidin-3-yl)methanol II-519;

(R)-(1-(6-(6-(Difluoromethyl)imidazo[1,2-b]pyridazin-3-yl)pyrimidin-4-yl)piperidin-3-yl)methanol II-520;

(4-(6-(6-(Difluoromethyl)imidazo[1,2-b]pyridazin-3-yl)pyrimidin-4-yl)morpholin-2-yl)methanol II-521;

(1-(6-(6-(Difluoromethyl)imidazo[1,2-b]pyridazin-3-yl)pyrimidin-4-yl)piperidin-3-yl)(imino)(methyl)-$\lambda^6$-sulfanone II-522;

N-((1-(6-(6-(Difluoromethyl)imidazo[1,2-b]pyridazin-3-yl)pyrimidin-4-yl)piperidin-3-yl)methyl-d2)methanesulfonamide II-524;

N-((1-(6-(6-(Difluoromethyl)imidazo[1,2-b]pyridazin-3-yl)pyrimidin-4-yl)-5-methyl-4-oxopiperidin-3-yl)methyl)methanesulfonamide II-525;

N-((1-(6-(6-(Difluoromethyl)imidazo[1,2-b]pyridazin-3-yl)pyrimidin-4-yl)-5-methyl-4-oxopiperidin-3-yl)methyl)methanesulfonamide II-526;

N-((8-(6-(6-(Difluoromethyl)imidazo[1,2-b]pyridazin-3-yl)pyrimidin-4-yl)-10-methyl-1,4-dioxa-8-azaspiro[4.5]decan-6-yl)methyl)methanesulfonamide II-527;

N-((5-(6-(6-(Difluoromethyl)imidazo[1,2-b]pyridazin-3-yl)pyrimidin-4-yl)-8,8-difluoro-5-azaspiro[2.5]octan-7-yl)methyl)methanesulfonamide II-528;

4-(6-(6-(Difluoromethyl)imidazo[1,2-b]pyridazin-3-yl)pyrimidin-4-yl)morpholine-2-carbonitrile II-531;

1-(6-(6-(Difluoromethyl)imidazo[1,2-b]pyridazin-3-yl)pyrimidin-4-yl)piperidine-3-carbonitrile II-532;

4-(6-(6-(Trifluoromethyl)imidazo[1,2-b]pyridazin-3-yl)pyrimidin-4-yl)morpholine-2-carbonitrile II-533;

1-(6-(6-(Trifluoromethyl)imidazo[1,2-b]pyridazin-3-yl)pyrimidin-4-yl)piperidine-3-carbonitrile II-534;

N-((1-(6-(6-(Difluoromethyl)imidazo[1,2-b]pyridazin-3-yl)pyrimidin-4-yl)-4-fluoro-5-methyl-1,2,5,6-tetrahydropyridin-3-yl)methyl)methanesulfonamide II-537;

N-((1-(6-(6-(Difluoromethyl)imidazo[1,2-b]pyridazin-3-yl)pyrimidin-4-yl)-4-fluoro-5-methyl-1,2,3,6-tetrahydropyridin-3-yl)methyl)methanesulfonamide II-538;

N-((1-(6-(6-(Difluoromethyl)imidazo[1,2-b]pyridazin-3-yl)pyrimidin-4-yl)-5,6-dimethylpiperidin-3-yl)methyl)methanesulfonamide II-544;

7-(6-(6-(Difluoromethyl)imidazo[1,2-b]pyridazin-3-yl)pyrimidin-4-yl)-8-methylhexahydro-3H-oxazolo[3,4-a]pyrazin-3-one II-547;

6-(Difluoromethyl)-3-(6-(2,3-dimethylpiperazin-1-yl)pyrimidin-4-yl)imidazo[1,2-b]pyridazine II-548;

N-((5-Cyano-1-(6-(6-(difluoromethyl)imidazo[1,2-b]pyridazin-3-yl)pyrimidin-4-yl)piperidin-3-yl)methyl)methanesulfonamide II-553;

(1-(6-(6-(Difluoromethyl)imidazo[1,2-b]pyridazin-3-yl)pyrimidin-4-yl)-2-methylpiperidin-3-yl)methanol II-554;

(1-(6-(6-(Difluoromethyl)imidazo[1,2-b]pyridazin-3-yl)pyrimidin-4-yl)-2-methylpiperidin-3-yl)methanol II-555;

(1-(tert-Butyl)-4-(6-(6-(difluoromethyl)imidazo[1,2-b]pyridazin-3-yl)pyrimidin-4-yl)-3-methylpiperazin-2-yl)methanol II-556;

(1-(tert-Butyl)-4-(6-(6-(difluoromethyl)imidazo[1,2-b]pyridazin-3-yl)pyrimidin-4-yl)-3-methylpiperazin-2-yl)methanol II-557;

(1-(tert-Butyl)-4-(6-(6-(difluoromethyl)imidazo[1,2-b]pyridazin-3-yl)pyrimidin-4-yl)-3-methylpiperazin-2-yl)methanol II-558;

N-(((8aS)-2-(6-(6-(Difluoromethyl)imidazo[1,2-b]pyridazin-3-yl)pyrimidin-4-yl)octahydropyrrolo[1,2-a]pyrazin-4-yl)methyl)methanesulfonamide II-560;

2-(1-(6-(6-(Difluoromethyl)imidazo[1,2-b]pyridazin-3-yl)pyrimidin-4-yl)piperidin-3-yl)tetrahydrothiophene 1,1-dioxide II-563;

N-((6-(6-(6-(Difluoromethyl)imidazo[1,2-b]pyridazin-3-yl)pyrimidin-4-yl)-6-azaspiro[2.5]octan-4-yl)methyl)methanesulfonamide II-566;

N-((4-(6-(6-(Difluoromethyl)imidazo[1,2-b]pyridazin-3-yl)pyrimidin-4-yl)-6,6-dimethylpiperazin-2-yl)methyl)methanesulfonamide II-567;

N-(((7S,8aS)-2-(6-(6-(Difluoromethyl)imidazo[1,2-b]pyridazin-3-yl)pyrimidin-4-yl)-7-fluorooctahydropyrrolo[1,2-a]pyrazin-4-yl)methyl)methanesulfonamide II-568;

N-((4-(6-(6-(Difluoromethyl)imidazo[1,2-b]pyridazin-3-yl)pyrimidin-4-yl)-6,6-dimethylpiperazin-2-yl)methyl)methanesulfonamide II-569;

N-((4-(6-(6-(Difluoromethyl)imidazo[1,2-b]pyridazin-3-yl)pyrimidin-4-yl)-6,6-dimethylpiperazin-2-yl)methyl)methanesulfonamide II-570;

N-(1-(4-(6-(6-(Difluoromethyl)imidazo[1,2-b]pyridazin-3-yl)pyrimidin-4-yl)morpholin-2-yl)propyl)methanesulfonamide II-571;

N-(1-(4-(6-(6-(Difluoromethyl)imidazo[1,2-b]pyridazin-3-yl)pyrimidin-4-yl)morpholin-2-yl)propyl)methanesulfonamide II-572;

(((1-(6-(6-(Difluoromethyl)imidazo[1,2-b]pyridazin-3-yl)pyrimidin-4-yl)piperidin-3-yl)methyl)imino)dimethyl-λ⁶-sulfanone II-573;

(((1-(6-(6-(Difluoromethyl)imidazo[1,2-b]pyridazin-3-yl)pyrimidin-4-yl)piperidin-3-yl)methyl)imino)dimethyl-λ⁶-sulfanone II-574;

(1-(6-(6-(Difluoromethyl)imidazo[1,2-b]pyridazin-3-yl)pyrimidin-4-yl)-2,5-dimethylpiperidin-3-yl)methanol II-577;

((1-(6-(6-(Difluoromethyl)imidazo[1,2-b]pyridazin-3-yl)pyrimidin-4-yl)-2-methylpiperidin-3-yl)imino)dimethyl-λ⁶-sulfanone II-578;

((1-(6-(6-(Difluoromethyl)imidazo[1,2-b]pyridazin-3-yl)pyrimidin-4-yl)-2-methylpiperidin-3-yl)imino)dimethyl-λ⁶-sulfanone II-579;

(((1-(6-(6-(Difluoromethyl)imidazo[1,2-b]pyridazin-3-yl)pyrimidin-4-yl)-2-methylpiperidin-3-yl)methyl)imino)dimethyl-λ⁶-sulfanone II-583;

(((1-(6-(6-(Difluoromethyl)imidazo[1,2-b]pyridazin-3-yl)pyrimidin-4-yl)-2-methylpiperidin-3-yl)methyl)imino)dimethyl-λ⁶-sulfanone II-584;

N-((1-(6-(6-(Difluoromethyl)imidazo[1,2-b]pyridazin-3-yl)pyrimidin-4-yl)-5,6-dimethylpiperidin-3-yl)methyl)methanesulfonamide II-591;

N-((1-(6-(6-(Difluoromethyl)imidazo[1,2-b]pyridazin-3-yl)pyrimidin-4-yl)-5,6-dimethylpiperidin-3-yl)methyl)methanesulfonamide II-592;

2-(1-(6-(6-(Difluoromethyl)imidazo[1,2-b]pyridazin-3-yl)pyrimidin-4-yl)piperidin-3-yl)propan-2-ol II-608;

(4-(6-(6-(Difluoromethyl)imidazo[1,2-b]pyridazin-3-yl)pyrimidin-4-yl)-6-methylmorpholin-2-yl)methanol II-615;

(4-(6-(6-(Difluoromethyl)imidazo[1,2-b]pyridazin-3-yl)pyrimidin-4-yl)-6-methylmorpholin-2-yl)methanol II-616;

N-((1-(6-(6-(Difluoromethyl)imidazo[1,2-b]pyridazin-3-yl)pyrimidin-4-yl)-4-hydroxy-2,4,5-trimethylpiperidin-3-yl)methyl)methanesulfonamide II-617;

N-((1-(6-(6-(Difluoromethyl)imidazo[1,2-b]pyridazin-3-yl)pyrimidin-4-yl)-4-hydroxy-2,4,5-trimethylpiperidin-3-yl)methyl)methanesulfonamide II-618;

2-(1-(6-(6-(Difluoromethyl)imidazo[1,2-b]pyridazin-3-yl)pyrimidin-4-yl)piperidin-3-yl)-3-methylbutan-2-ol II-621;

2-(1-(6-(6-(Difluoromethyl)imidazo[1,2-b]pyridazin-3-yl)pyrimidin-4-yl)piperidin-3-yl)-3-methylbutan-2-ol II-622;

(1-(6-(6-(Difluoromethyl)imidazo[1,2-b]pyridazin-3-yl)pyrimidin-4-yl)-4,4-difluoro-5-methylpiperidin-3-yl)methanol II-623;

(1-(6-(6-(Difluoromethyl)imidazo[1,2-b]pyridazin-3-yl)pyrimidin-4-yl)-4,4-difluoro-5-methylpiperidin-3-yl)methanol II-624;

((1-(6-(6-(Difluoromethyl)imidazo[1,2-b]pyridazin-3-yl)pyrimidin-4-yl)-5-methylpiperidin-3-yl)imino)diethyl-λ⁶-sulfanone II-627;

((1-(6-(6-(Difluoromethyl)imidazo[1,2-b]pyridazin-3-yl)pyrimidin-4-yl)-4-methylpiperidin-3-yl)imino)dimethyl-λ⁶-sulfanone II-629;

Cyclopropyl((1-(6-(6-(difluoromethyl)imidazo[1,2-b]pyridazin-3-yl)pyrimidin-4-yl)-5-methylpiperidin-3-yl)imino)(methyl)-λ⁶-sulfanone II-634;

((1-(6-(6-(Difluoromethyl)imidazo[1,2-b]pyridazin-3-yl)pyrimidin-4-yl)-5-methylpiperidin-3-yl)imino)(ethyl)(methyl)-λ⁶-sulfanone II-635;

((1-(6-(6-(Difluoromethyl)imidazo[1,2-b]pyridazin-3-yl)pyrimidin-4-yl)-5-ethylpiperidin-3-yl)imino)dimethyl-λ⁶-sulfanone II-648;

1-((1-(6-(6-(Difluoromethyl)imidazo[1,2-b]pyridazin-3-yl)pyrimidin-4-yl)-5-methylpiperidin-3-yl)imino)tetrahydro-1H-1-λ⁶-thiophene 1-oxide II-649;

((1-(6-(6-(Difluoromethyl)imidazo[1,2-b]pyridazin-3-yl)pyrimidin-4-yl)-5-(trifluoromethyl)piperidin-3-yl)imino)dimethyl-λ⁶-sulfanone II-654;

[1-[6-[6-(Difluoromethyl)imidazo[1,2-b]pyridazin-3-yl]pyrimidin-4-yl]-5,5-difluoro-2-methyl-3-piperidyl]methanol II-684;

(4-(6-(6-(Difluoromethyl)imidazo[1,2-b]pyridazin-3-yl)pyrimidin-4-yl)-5-ethylmorpholin-2-yl)methanol II-685;

2-[4-[6-[6-(Difluoromethyl)imidazo[1,2-b]pyridazin-3-yl]pyrimidin-4-yl]-3-methyl-piperazin-2-yl]ethanol II-686;

N-((4-(6-(6-(Difluoromethyl)imidazo[1,2-b]pyridazin-3-yl)pyrimidin-4-yl)-5-methylpiperazin-2-yl)methyl)methanesulfonamide II-687;

(S)-(4-(6-(6-(Difluoromethyl)imidazo[1,2-b]pyridazin-3-yl)pyrimidin-4-yl)piperazin-2-yl)methanol II-688;

cis-[6-Cyclopropyl-4-[6-[6-(difluoromethyl)imidazo[1,2-b]pyridazin-3-yl]pyrimidin-4-yl]morpholin-2-yl]methanol II-689;

[1-[6-[6-(Difluoromethyl)imidazo[1,2-b]pyridazin-3-yl]pyrimidin-4-yl]-5-(2-methoxyethoxy)-3-piperidyl]methanol II-690;

N-[[1-[6-[6-Cyanoimidazo[1,2-b]pyridazin-3-yl)pyrimidin-4-yl]-3-piperidyl]methyl]methanesulfonamide II-692;

3-[6-[2,5-Dimethyl-3-(1H-pyrazol-4-yl)piperazin-1-yl]pyrimidin-4-yl]imidazo[1,2-b]pyridazine-6-carbonitrile II-693;

((1-(6-(6-(Difluoromethyl)imidazo[1,2-b]pyridazin-3-yl)pyrimidin-4-yl)-5-(trifluoromethyl)piperidin-3-yl)imino)dimethyl-λ⁶-sulfanone II-694;

((1-(6-(6-(Difluoromethyl)imidazo[1,2-b]pyridazin-3-yl)pyrimidin-4-yl)-5-(trifluoromethyl)piperidin-3-yl)imino)dimethyl-λ⁶-sulfanone II-695;

[1-[6-[6-(Difluoromethyl)imidazo[1,2-b]pyridazin-3-yl]pyrimidin-4-yl]-6-methyl-3-piperidyl]imino-dimethyl-λ⁶-sulfanone II-696;

[1-[6-[6-(Difluoromethyl)imidazo[1,2-b]pyridazin-3-yl]pyrimidin-4-yl]-6-methyl-3-piperidyl]imino-dimethyl-λ⁶-sulfanone II-697;

3-[6-[2,5-Dimethyl-3-(1H-pyrazol-4-yl)piperazin-1-yl]pyrimidin-4-yl]-6-(trifluoromethyl)imidazo[1,2-b]pyridazine II-698;

3-(6-(6-Oxooctahydro-2H-pyrido[1,2-a]pyrazin-2-yl)pyrimidin-4-yl)imidazo[1,2-b]pyridazine-6-carbonitrile II-699;

[2-(Difluoromethyl)-1-[6-[6-(difluoromethyl)imidazo[1,2-b]pyridazin-3-yl]pyrimidin-4-yl]-3-piperidyl]imino-dimethyl-λ⁶-sulfanone II-700;

[2-(Difluoromethyl)-1-[6-[6-(difluoromethyl)imidazo[1,2-b]pyridazin-3-yl]pyrimidin-4-yl]-3-piperidyl]imino-dimethyl-λ⁶-sulfanone II-701;

3-(6-(3-((Dimethyl(oxo)-λ⁶-sulfanylidene)amino)-5-methylpiperidin-1-yl)pyrimidin-4-yl)imidazo[1,2-b]pyridazine-6-carbonitrile II-702;

3-(6-(3-((Dimethyl(oxo)-λ⁶-sulfanylidene)amino)-5-methylpiperidin-1-yl)pyrimidin-4-yl)imidazo[1,2-b]pyridazine-6-carbonitrile II-703;

3-(6-(2,5-Dimethyl-3-(1H-pyrazol-4-yl)piperazin-1-yl)pyrimidin-4-yl)-6-(trifluoromethyl)imidazo[1,2-b]pyridazine II-704;

3-(6-(2,5-Dimethyl-3-(1H-pyrazol-4-yl)piperazin-1-yl)pyrimidin-4-yl)-6-(trifluoromethyl)imidazo[1,2-b]pyridazine II-705;

3-(6-(2-Methyl-3-(1H-pyrazol-4-yl)piperazin-1-yl)pyrimidin-4-yl)-6-(trifluoromethyl)imidazo[1,2-b]pyridazine II-706;

3-(6-(3-Methyl-2-(1H-pyrazol-4-yl)piperazin-1-yl)pyrimidin-4-yl)-6-(trifluoromethyl)imidazo[1,2-b]pyridazine II-707;

6-(Difluoromethyl)-3-[6-(3-dimethylphosphoryl-5-methyl-1-piperidyl)pyrimidin-4-yl]imidazo[1,2-b]pyridazine II-710;

6-(Difluoromethyl)-3-[6-(3-dimethylphosphoryl-5-methyl-1-piperidyl)pyrimidin-4-yl]imidazo[1,2-b]pyridazine II-711;

3-[6-(3-Dimethylphosphoryl-5-methyl-1-piperidyl)pyrimidin-4-yl]-6-(trifluoromethyl)imidazo[1,2-b]pyridazine II-712;

3-[6-(3-Dimethylphosphoryl-5-methyl-1-piperidyl)pyrimidin-4-yl]-6-(trifluoromethyl)imidazo[1,2-b]pyridazine II-713;

3-(6-(3-(1H-Imidazol-4-yl)piperidin-1-yl)pyrimidin-4-yl)-6-(difluoromethyl)imidazo[1,2-b]pyridazine II-714;

3-(6-(3-(1H-Imidazol-4-yl)piperidin-1-yl)pyrimidin-4-yl)-6-(difluoromethyl)imidazo[1,2-b]pyridazine II-715;

2,5-Dimethyl-1-[6-[6-(trifluoromethyl)imidazo[1,2-b]pyridazin-3-yl]pyrimidin-4-yl]piperidine-3-carboxamide (racemic pair of diastereomers, 2 compounds) II-719;

2,5-Dimethyl-1-[6-[6-(trifluoromethyl)imidazo[1,2-b]pyridazin-3-yl]pyrimidin-4-yl]piperidine-3-carboxamide (racemic pair of diastereomers, 2 compounds) II-720;

2,5-Dimethyl-1-[6-[6-(trifluoromethyl)imidazo[1,2-b]pyridazin-3-yl]pyrimidin-4-yl]piperidine-3-carboxylic acid II-721;

3-(6-(3-((Dimethyl(oxo)-$\lambda^6$-sulfanylidene)amino)-5-methylpiperidin-1-yl)pyrimidin-4-yl)imidazo[1,2-b]pyridazine-6-carboxamide II-726;

3-[6-(6-Oxo-3,4,7,8,9,9a-hexahydro-1H-pyrido[1,2-a]pyrazin-2-yl)pyrimidin-4-yl]imidazo[1,2-b]pyridazine-6-carboxamide II-727;

3-[6-[2,5-Dimethyl-3-(1H-pyrazol-4-yl)piperazin-1-yl]pyrimidin-4-yl]imidazo[1,2-b]pyridazine-6-carboxamide II-728;

N-((1-(4-(6-(Difluoromethyl)imidazo[1,2-b]pyridazin-3-yl)-5-fluoropyridin-2-yl)piperidin-3-yl)methyl)methanesulfonamide II-729;

N-((1-(5-Chloro-4-(6-(difluoromethyl)imidazo[1,2-b]pyridazin-3-yl)pyridin-2-yl)piperidin-3-yl)methyl)methanesulfonamide II-730

The following compounds were prepared using a methodology similar to the one described in Example 1 and further purified by chiral SFC:

N-(2-(6-(6-(Difluoromethyl)imidazo[1,2-b]pyridazin-3-yl)pyrimidin-4-yl)-2-azaspiro[4.4]nonan-7-yl)methanesulfonamide II-95 (single stereoisomer, separated by chiral SFC);

N-(2-(6-(6-(Difluoromethyl)imidazo[1,2-b]pyridazin-3-yl)pyrimidin-4-yl)-2-azaspiro[4.4]nonan-7-yl)methanesulfonamide II-100 (single stereoisomer, separated by chiral SFC);

N-((1-(6-(6-(Difluoromethyl)imidazo[1,2-b]pyridazin-3-yl)pyrimidin-4-yl)-5-methoxypiperidin-3-yl)methyl)methanesulfonamide II-233 (single stereoisomer, separated by chiral SFC);

N-((1-(6-(6-(Difluoromethyl)imidazo[1,2-b]pyridazin-3-yl)pyrimidin-4-yl)-2-methylpiperidin-3-yl)methyl)methanesulfonamide II-263 (single stereoisomer, separated by chiral SFC);

N-((1-(6-(6-(Difluoromethyl)imidazo[1,2-b]pyridazin-3-yl)pyrimidin-4-yl)-2-methylpiperidin-3-yl)methyl)methanesulfonamide II-264 (single stereoisomer, separated by chiral SFC);

N-((1-(6-(6-(Difluoromethyl)imidazo[1,2-b]pyridazin-3-yl)pyrimidin-4-yl)-2-methylpiperidin-3-yl)methyl)methanesulfonamide II-265 (single stereoisomer, separated by chiral SFC);

N-((1-(6-(6-(Difluoromethyl)imidazo[1,2-b]pyridazin-3-yl)pyrimidin-4-yl)-2-methylpiperidin-3-yl)methyl)methanesulfonamide II-266 (single stereoisomer, separated by chiral SFC);

(S)-1-((1-(6-(6-(Difluoromethyl)imidazo[1,2-b]pyridazin-3-yl)pyrimidin-4-yl)piperidin-3-yl)methyl)sulfuric diamide (single stereoisomer, separated by chiral SFC) and (R)-1-((1-(6-(6-(difluoromethyl)imidazo[1,2-b]pyridazin-3-yl)pyrimidin-4-yl)piperidin-3-yl)methyl)sulfuric diamide (single stereoisomer, separated by chiral SFC); II-277 and II-278 (in no particular order)

N-((1-(6-(6-(Difluoromethyl)imidazo[1,2-b]pyridazin-3-yl)pyrimidin-4-yl)-4,4-difluoro-2-methylpiperidin-3-yl)methyl)methanesulfonamide II-302 (single stereoisomer, separated by chiral SFC);

N-((1-(6-(6-(Difluoromethyl)imidazo[1,2-b]pyridazin-3-yl)pyrimidin-4-yl)-4,4-difluoro-2-methylpiperidin-3-yl)methyl)methanesulfonamide II-303 (single stereoisomer, separated by chiral SFC);

N-((1-(6-(6-(Difluoromethyl)imidazo[1,2-b]pyridazin-3-yl)pyrimidin-4-yl)-4,4-difluoro-6-methylpiperidin-3-yl)methyl)methanesulfonamide II-304 (single stereoisomer, separated by chiral SFC);

N-((1-(6-(6-(Difluoromethyl)imidazo[1,2-b]pyridazin-3-yl)pyrimidin-4-yl)-4,4-difluoro-6-methylpiperidin-3-yl)methyl)methanesulfonamide II-305 (single stereoisomer, separated by chiral SFC);

4-(6-(6-(Difluoromethyl)imidazo[1,2-b]pyridazin-3-yl)pyrimidin-4-yl)-3-methylthiomorpholine 1-oxide II-355 (single stereoisomer, separated by chiral SFC);

4-(6-(6-(Difluoromethyl)imidazo[1,2-b]pyridazin-3-yl)pyrimidin-4-yl)-3-methylthiomorpholine 1-oxide II-356 (single stereoisomer, separated by chiral SFC);

N-((1-(6-(6-(Difluoromethyl)imidazo[1,2-b]pyridazin-3-yl)pyrimidin-4-yl)-5,5-difluoro-2-methylpiperidin-3-yl)methyl)methanesulfonamide II-360 (single stereoisomer, separated by chiral SFC);

N-(((2S,3R)-1-(6-(6-(Difluoromethyl)imidazo[1,2-b]pyridazin-3-yl)pyrimidin-4-yl)-5,5-difluoro-2-methylpiperidin-3-yl)methyl)methanesulfonamide II-361 (single stereoisomer, separated by chiral SFC);

N-((4-(6-(6-(Difluoromethyl)imidazo[1,2-b]pyridazin-3-yl)pyrimidin-4-yl)-3-methylmorpholin-2-yl)methyl)methanesulfonamide II-371 (single stereoisomer, separated by chiral SFC);

N-((4-(6-(6-(Difluoromethyl)imidazo[1,2-b]pyridazin-3-yl)pyrimidin-4-yl)-3-methylmorpholin-2-yl)methyl)methanesulfonamide II-372 (single stereoisomer, separated by chiral SFC);

((2S,3S)-1-(6-(6-(Difluoromethyl)imidazo[1,2-b]pyridazin-3-yl)pyrimidin-4-yl)-2-methylpiperidin-3-yl)methanol II-392 (single stereoisomer, separated by chiral SFC);

(1-(6-(6-(Difluoromethyl)imidazo[1,2-b]pyridazin-3-yl)pyrimidin-4-yl)-2-methylpiperidin-3-yl)methanol II-393 (single stereoisomer, separated by chiral SFC);

(S)—N-(1-(6-(6-(Difluoromethyl)imidazo[1,2-b]pyridazin-3-yl)pyrimidin-4-yl)piperidin-3-yl)methanesulfonamide II-404 (single stereoisomer, separated by chiral SFC);

(R)—N-(1-(6-(6-(Difluoromethyl)imidazo[1,2-b]pyridazin-3-yl)pyrimidin-4-yl)piperidin-3-yl)methanesulfonamide II-405 (single stereoisomer, separated by chiral SFC);

(4-(6-(6-(Difluoromethyl)imidazo[1,2-b]pyridazin-3-yl)pyrimidin-4-yl)-3-methylmorpholin-2-yl)methanol II-413 (single stereoisomer, separated by chiral SFC);

(4-(6-(6-(Difluoromethyl)imidazo[1,2-b]pyridazin-3-yl)pyrimidin-4-yl)-3-methylmorpholin-2-yl)methanol II-414 (single stereoisomer, separated by chiral SFC);

(((1-(6-(6-(Difluoromethyl)imidazo[1,2-b]pyridazin-3-yl)pyrimidin-4-yl)-2-ethylpiperidin-3-yl)methyl)imino)dimethyl-$\lambda^6$-sulfanone II-416 (single stereoisomer, separated by chiral SFC);

(((1-(6-(6-(Difluoromethyl)imidazo[1,2-b]pyridazin-3-yl)pyrimidin-4-yl)-2-ethylpiperidin-3-yl)methyl)imino)dimethyl-$\lambda^6$-sulfanone II-417 (single stereoisomer, separated by chiral SFC);

N-((1-(6-(6-(Difluoromethyl)imidazo[1,2-b]pyridazin-3-yl)pyrimidin-4-yl)-5-methylpiperidin-3-yl)methyl)methanesulfonamide II-436 (single stereoisomer, separated by chiral SFC);

N-((1-(6-(6-(Difluoromethyl)imidazo[1,2-b]pyridazin-3-yl)pyrimidin-4-yl)-5-methylpiperidin-3-yl)methyl)methanesulfonamide II-437 (single stereoisomer, separated by chiral SFC);

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-467 (single stereoisomer, separated by chiral SFC);

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-468 (single stereoisomer, separated by chiral SFC);

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-469 (single stereoisomer, separated by chiral SFC);

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-470 (single stereoisomer, separated by chiral SFC);

N-((1-(6-(6-(Difluoromethyl)imidazo[1,2-b]pyridazin-3-yl)pyrimidin-4-yl)-4,4-difluoro-2,5-dimethylpiperidin-3-yl)methyl)methanesulfonamide II-471 (single stereoisomer, separated by chiral SFC);

N-(((2S,3R,5S)-1-(6-(6-(difluoromethyl)imidazo[1,2-b]pyridazin-3-yl)pyrimidin-4-yl)-4,4-difluoro-2,5-dimethylpiperidin-3-yl)methyl)methanesulfonamide II-472 (single stereoisomer, separated by chiral SFC);

N-((4-(6-(6-(Difluoromethyl)imidazo[1,2-b]pyridazin-3-yl)pyrimidin-4-yl)-3,6,6-trimethylmorpholin-2-yl)methyl)methanesulfonamide II-484 (single stereoisomer, separated by chiral SFC);

N-((4-(6-(6-(Difluoromethyl)imidazo[1,2-b]pyridazin-3-yl)pyrimidin-4-yl)-3,6,6-trimethylmorpholin-2-yl)methyl)methanesulfonamide II-489 (single stereoisomer, separated by chiral SFC);

N-(((2R,3S)-4-(6-(6-(Difluoromethyl)imidazo[1,2-b]pyridazin-3-yl)pyrimidin-4-yl)-3,6,6-trimethylmorpholin-2-yl)methyl)methanesulfonamide II-490 (single stereoisomer, separated by chiral SFC);

(S)-((1-(6-(6-(Difluoromethyl)imidazo[1,2-b]pyridazin-3-yl)pyrimidin-4-yl)piperidin-3-yl)imino)dimethyl-$\lambda^6$-sulfanone II-502 (single stereoisomer, separated by chiral SFC);

((1-(6-(6-(Difluoromethyl)imidazo[1,2-b]pyridazin-3-yl)pyrimidin-4-yl)piperidin-3-yl)imino)dimethyl-$\lambda^6$-sulfanone II-503 (single stereoisomer, separated by chiral SFC);

N—((S)-1-((S)-4-(6-(6-(Difluoromethyl)imidazo[1,2-b]pyridazin-3-yl)pyrimidin-4-yl)morpholin-2-yl)ethyl)methanesulfonamide II-509 (single stereoisomer, separated by chiral SFC);

N-(-1-((R)-4-(6-(6-(Difluoromethyl)imidazo[1,2-b]pyridazin-3-yl)pyrimidin-4-yl)morpholin-2-yl)ethyl)methanesulfonamide II-510 (single stereoisomer, separated by chiral SFC);

6-(Difluoromethyl)-3-(6-(3-(methylsulfonyl)piperidin-1-yl)pyrimidin-4-yl)imidazo[1,2-b]pyridazine II-529 (single stereoisomer, separated by chiral SFC);

6-(Difluoromethyl)-3-(6-(3-(methylsulfonyl)piperidin-1-yl)pyrimidin-4-yl)imidazo[1,2-b]pyridazine II-530 (single stereoisomer, separated by chiral SFC);

((1-(6-(6-(Difluoromethyl)imidazo[1,2-b]pyridazin-3-yl)pyrimidin-4-yl)-5-methylpiperidin-3-yl)imino)dimethyl-$\lambda^6$-sulfanone II-540 (single stereoisomer, separated by chiral SFC);

(((3S,5R)-1-(6-(6-(Difluoromethyl)imidazo[1,2-b]pyridazin-3-yl)pyrimidin-4-yl)-5-methylpiperidin-3-yl)imino)dimethyl-$\lambda^6$-sulfanone II-541 (single stereoisomer, separated by chiral SFC);

N-((1-(6-(6-(Difluoromethyl)imidazo[1,2-b]pyridazin-3-yl)pyrimidin-4-yl)-2,5-dimethylpiperidin-3-yl)methyl)methanesulfonamide II-545 (single stereoisomer, separated by chiral SFC);

N-((1-(6-(6-(Difluoromethyl)imidazo[1,2-b]pyridazin-3-yl)pyrimidin-4-yl)-2,5-dimethylpiperidin-3-yl)methyl)methanesulfonamide II-546 (single stereoisomer, separated by chiral SFC);

2-(4-(6-(6-(Difluoromethyl)imidazo[1,2-b]pyridazin-3-yl)pyrimidin-4-yl)morpholin-2-yl)acetonitrile II-564 (single stereoisomer, separated by chiral SFC);

2-(4-(6-(6-(Difluoromethyl)imidazo[1,2-b]pyridazin-3-yl)pyrimidin-4-yl)morpholin-2-yl)acetonitrile II-565 (single stereoisomer, separated by chiral SFC);

((1-(6-(6-(Difluoromethyl)imidazo[1,2-b]pyridazin-3-yl)pyrimidin-4-yl)-2-methylpiperidin-3-yl)imino)dimethyl-$\lambda^6$-sulfanone II-581 (single stereoisomer, separated by chiral SFC);

((1-(6-(6-(Difluoromethyl)imidazo[1,2-b]pyridazin-3-yl)pyrimidin-4-yl)-2-methylpiperidin-3-yl)imino)dimethyl-$\lambda^6$-sulfanone II-582 (single stereoisomer, separated by chiral SFC);

((2S,3S,5R)-1-(6-(6-(Difluoromethyl)imidazo[1,2-b]pyridazin-3-yl)pyrimidin-4-yl)-2,5-dimethylpiperidin-3-yl)methanol II-585 (single stereoisomer, separated by chiral SFC);

(1-(6-(6-(Difluoromethyl)imidazo[1,2-b]pyridazin-3-yl)pyrimidin-4-yl)-2,5-dimethylpiperidin-3-yl)methanol II-586 (single stereoisomer, separated by chiral SFC);

(((2S,3S)-1-(6-(6-(Difluoromethyl)imidazo[1,2-b]pyridazin-3-yl)pyrimidin-4-yl)-2-methylpiperidin-3-yl)imino)dimethyl-$\lambda^6$-sulfanone II-593 (single stereoisomer, separated by chiral SFC);

((1-(6-(6-(Difluoromethyl)imidazo[1,2-b]pyridazin-3-yl)pyrimidin-4-yl)-2-methylpiperidin-3-yl)imino)dimethyl-$\lambda^6$-sulfanone II-594 (single stereoisomer, separated by chiral SFC);

2-(1-(6-(6-(Difluoromethyl)imidazo[1,2-b]pyridazin-3-yl)pyrimidin-4-yl)piperidin-3-yl)propan-2-ol II-613 (single stereoisomer, separated by chiral SFC);

2-(1-(6-(6-(Difluoromethyl)imidazo[1,2-b]pyridazin-3-yl)pyrimidin-4-yl)piperidin-3-yl)propan-2-ol II-614 (single stereoisomer, separated by chiral SFC);

((1-(6-(6-(Difluoromethyl)imidazo[1,2-b]pyridazin-3-yl)pyrimidin-4-yl)-2,5-dimethylpiperidin-3-yl)imino)dimethyl-$\lambda^6$-sulfanone II-630 (single stereoisomer, separated by chiral SFC);

(((2S,3S,5R)-1-(6-(6-(Difluoromethyl)imidazo[1,2-b]pyridazin-3-yl)pyrimidin-4-yl)-2,5-dimethylpiperidin-3-yl)imino)dimethyl-$\lambda^6$-sulfanone II-631 (single stereoisomer, separated by chiral SFC);

((1-(6-(6-(Difluoromethyl)imidazo[1,2-b]pyridazin-3-yl)pyrimidin-4-yl)-4-methylpiperidin-3-yl)imino)dimethyl-$\lambda^6$-sulfanone II-632 (single stereoisomer, separated by chiral SFC);

((1-(6-(6-(Difluoromethyl)imidazo[1,2-b]pyridazin-3-yl)pyrimidin-4-yl)-4-methylpiperidin-3-yl)imino)dimethyl-$\lambda^6$-sulfanone II-633 (single stereoisomer, separated by chiral SFC);

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-636 (single stereoisomer, separated by chiral SFC);

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-637 (single stereoisomer, separated by chiral SFC);

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-638 (single stereoisomer, separated by chiral SFC);

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-639 (single stereoisomer, separated by chiral SFC);

((1-(6-(6-(Difluoromethyl)imidazo[1,2-b]pyridazin-3-yl)pyrimidin-4-yl)-5-methylpiperidin-3-yl)imino)(ethyl)(methyl)-$\lambda^6$-sulfanone II-640 (single stereoisomer, separated by chiral SFC);

((1-(6-(6-(Difluoromethyl)imidazo[1,2-b]pyridazin-3-yl)pyrimidin-4-yl)-5-methylpiperidin-3-yl)imino)(ethyl)(methyl)-$\lambda^6$-sulfanone II-641 (single stereoisomer, separated by chiral SFC);

((1-(6-(6-(Difluoromethyl)imidazo[1,2-b]pyridazin-3-yl)pyrimidin-4-yl)-5-methylpiperidin-3-yl)imino)(ethyl)(methyl)-$\lambda^6$-sulfanone II-642 (single stereoisomer, separated by chiral SFC);

((1-(6-(6-(Difluoromethyl)imidazo[1,2-b]pyridazin-3-yl)pyrimidin-4-yl)-5-methylpiperidin-3-yl)imino)(ethyl)(methyl)-$\lambda^6$-sulfanone II-643 (single stereoisomer, separated by chiral SFC);

Cyclopropyl((1-(6-(6-(difluoromethyl)imidazo[1,2-b]pyridazin-3-yl)pyrimidin-4-yl)-5-methylpiperidin-3-yl)imino)(methyl)-$\lambda^6$-sulfanone II-644 (single stereoisomer, separated by chiral SFC);

Cyclopropyl((1-(6-(6-(difluoromethyl)imidazo[1,2-b]pyridazin-3-yl)pyrimidin-4-yl)-5-methylpiperidin-3-yl)imino)(methyl)-$\lambda^6$-sulfanone II-645 (single stereoisomer, separated by chiral SFC);

Cyclopropyl((1-(6-(6-(difluoromethyl)imidazo[1,2-b]pyridazin-3-yl)pyrimidin-4-yl)-5-methylpiperidin-3-yl)imino)(methyl)-$\lambda^6$-sulfanone II-646 (single stereoisomer, separated by chiral SFC);

Cyclopropyl((1-(6-(6-(difluoromethyl)imidazo[1,2-b]pyridazin-3-yl)pyrimidin-4-yl)-5-methylpiperidin-3-yl)imino)(methyl)-$\lambda^6$-sulfanone II-647 (single stereoisomer, separated by chiral SFC);

((1-(6-(6-(Difluoromethyl)imidazo[1,2-b]pyridazin-3-yl)pyrimidin-4-yl)-5-ethylpiperidin-3-yl)imino)dimethyl-$\lambda^6$-sulfanone II-650 (single stereoisomer, separated by chiral SFC);

((1-(6-(6-(Difluoromethyl)imidazo[1,2-b]pyridazin-3-yl)pyrimidin-4-yl)-5-ethylpiperidin-3-yl)imino)dimethyl-$\lambda^6$-sulfanone II-651 (single stereoisomer, separated by chiral SFC);

6-(Difluoromethyl)-3-(6-(2,5-dimethyl-3-(1H-pyrazol-4-yl)piperazin-1-yl)pyrimidin-4-yl)imidazo[1,2-b]pyridazine II-652 (single stereoisomer, separated by chiral SFC);

6-(Difluoromethyl)-3-(6-(2,5-dimethyl-3-(1H-pyrazol-4-yl)piperazin-1-yl)pyrimidin-4-yl)imidazo[1,2-b]pyridazine II-653 (single stereoisomer, separated by chiral SFC);

2,5-Dimethyl-1-[6-[6-(trifluoromethyl)imidazo[1,2-b]pyridazin-3-yl]pyrimidin-4-yl]piperidine-3-carboxamide II-717 (single stereoisomer, separated by chiral SFC);

2,5-Dimethyl-1-[6-[6-(trifluoromethyl)imidazo[1,2-b]pyridazin-3-yl]pyrimidin-4-yl]piperidine-3-carboxamide II-718 (single stereoisomer, separated by chiral SFC);

((1-(4-(6-(Difluoromethyl)imidazo[1,2-b]pyridazin-3-yl)-5-fluoropyridin-2-yl)-5-methylpiperidin-3-yl)imino)dimethyl-$\lambda^6$-sulfanone II-722 (single stereoisomer, separated by chiral SFC);

((1-(4-(6-(Difluoromethyl)imidazo[1,2-b]pyridazin-3-yl)-5-fluoropyridin-2-yl)-5-methylpiperidin-3-yl)imino)dimethyl-$\lambda^6$-sulfanone II-723 (single stereoisomer, separated by chiral SFC);

((1-(4-(6-(Difluoromethyl)imidazo[1,2-b]pyridazin-3-yl)pyridin-2-yl)-5-methylpiperidin-3-yl)imino)dimethyl-$\lambda^6$-sulfanone II-724 (single stereoisomer, separated by chiral SFC);

((1-(4-(6-(Difluoromethyl)imidazo[1,2-b]pyridazin-3-yl)pyridin-2-yl)-5-methylpiperidin-3-yl)imino)dimethyl-$\lambda^6$-sulfanone II-725 (single stereoisomer, separated by chiral SFC);

Example 2: 2-((4H-1,2,4-Triazol-4-yl)methyl)-4-(6-(6-(difluoromethyl)imidazo[1,2-b]pyridazin-3-yl)pyrimidin-4-yl)morpholine, II-29

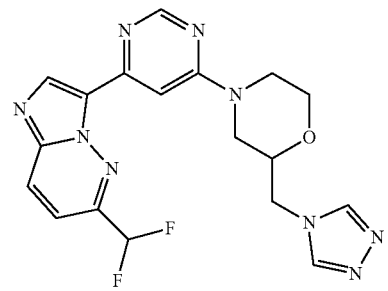 [SMILES: FC(F)c1ccc2ncc(-c3cc(N4CCOC(Cn5cnnc5)C4)ncn3)n2n1]

A mixture of 2-(1,2,4-triazol-4-ylmethyl)morpholine (trifluoroacetate salt) (15 mg, 0.053 mmol), 6-(difluoromethyl)-3-(6-fluoropyrimidin-4-yl)imidazo[1,2-b]pyridazine (14.1 mg, 0.053 mmol) and $K_2CO_3$ (40 mg, 0.289 mmol) in NMP (1 mL) was stirred at 90° C. in a sealed tube for 24 hours. The crude mixture was purified by reverse phase chromatography (C18, MeCN/water/0.05% TFA as eluent). The pure fractions were combined and lyophilised to yield 2-((4H-1,2,4-triazol-4-yl)methyl)-4-(6-(6-(difluoromethyl) imidazo[1,2-b]pyridazin-3-yl)pyrimidin-4-yl)morpholine as a pale yellow solid (10 mg, 45%).

The following compounds were prepared using a methodology similar to the one described in Example 2:

(S)—N-((4-(6-(6-(Difluoromethyl)imidazo[1,2-b] pyridazin-3-yl)pyrimidin-4-yl)-1-methyl-6-oxopiperazin-2-yl)methyl)methanesulfonamide II-7;

N-((1-(6-(6-(Difluoromethyl)imidazo[1,2-b]pyridazin-3-yl) pyrimidin-4-yl)-5-methylpyrrolidin-3-yl)methyl)methanesulfonamide II-8;

(S)-(4-(6-(6-(Difluoromethyl)imidazo[1,2-b]pyridazin-3-yl) pyrimidin-4-yl)morpholin-2-yl)methanol II-9;

[(2S)-4-[6-[6-(Difluoromethyl)imidazo[1,2-b]pyridazin-3-yl]pyrimidin-4-yl]morpholin-2-yl]methylimino-dim-ethyl-oxo-sulfane II-10;

N-((1-(6-(6-(Difluoromethyl)imidazo[1,2-b]pyridazin-3-yl) pyrimidin-4-yl)-5-hydroxypiperidin-3-yl)methyl)methanesulfonamide II-12;

N-((1-(6-(6-(Difluoromethyl)imidazo[1,2-b]pyridazin-3-yl) pyrimidin-4-yl)-5-hydroxypiperidin-3-yl)methyl)methanesulfonamide II-13;

N-(2-(1-(6-(6-(Difluoromethyl)imidazo[1,2-b]pyridazin-3-yl)pyrimidin-4-yl)pyrrolidin-3-yl)ethyl)methanesulfonamide II-17;

N-((1-(6-(6-(Difluoromethyl)imidazo[1,2-b]pyridazin-3-yl) pyrimidin-4-yl)-4-methylpyrrolidin-3-yl)methyl)methanesulfonamide II-18;

N—(((S)-4-(6-(6-(Difluoromethyl)imidazo[1,2-b] pyridazin-3-yl)pyrimidin-4-yl)morpholin-2-yl)methyl) methanesulfonimidamide II-23;

(S)—N-((4-(6-(6-(Difluoromethyl)imidazo[1,2-b] pyridazin-3-yl)pyrimidin-4-yl)-6-oxopiperazin-2-yl) methyl)methanesulfonamide II-25;

[1-[6-[6-(Difluoromethyl)imidazo[1,2-b]pyridazin-3-yl]pyrimidin-4-yl]-3-piperidyl]methyl-methyl-methylimino-oxo-sulfane II-26;

3-(6-(1H-Pyrrolo[3,4-c]pyridin-2(3H)-yl)pyrimidin-4-yl)-6-(difluoromethyl)imidazo[1,2-b]pyridazine II-28;

N-((4-(6-(6-(Difluoromethyl)imidazo[1,2-b]pyridazin-3-yl) pyrimidin-4-yl)-6-methylmorpholin-2-yl)methyl)methanesulfonamide II-31;

N-((4-(6-(6-(Difluoromethyl)imidazo[1,2-b]pyridazin-3-yl) pyrimidin-4-yl)-6-methylmorpholin-2-yl)methyl)methanesulfonamide II-32;

N-((1-(6-(6-(Difluoromethyl)imidazo[1,2-b]pyridazin-3-yl) pyrimidin-4-yl)-4,4-difluoro-5-methylpiperidin-3-yl) methyl)methanesulfonamide II-35;

N-((4-(6-(6-(Difluoromethyl)imidazo[1,2-b]pyridazin-3-yl) pyrimidin-4-yl)-6-methylmorpholin-2-yl)methyl)methanesulfonamide II-33;

(S)—N-((4-(6-(6-(Difluoromethyl)imidazo[1,2-b] pyridazin-3-yl)pyrimidin-4-yl)morpholin-2-yl)methyl) methanesulfonamide II-34;

N-((1-(6-(6-(Difluoromethyl)imidazo[1,2-b]pyridazin-3-yl) pyrimidin-4-yl)-4,4-difluoro-5-methylpiperidin-3-yl) methyl)methanesulfonamide II-45;

4-(4-(6-(Difluoromethyl)imidazo[1,2-b]pyridazin-3-yl) pyridin-2-yl)piperazin-2-one II-62.

Example 3: N-((1-(6-(6-(Difluoromethyl)imidazo[1, 2-b]pyridazin-3-yl)pyrimidin-4-yl)piperidin-3-yl) methyl)methanesulfonamide, II-59

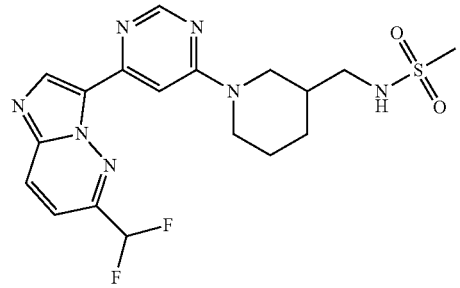 [SMILES: CS(=O)(=O)NCC1CCCN(c2cc(-c3cnc4ccc(C(F)F)nn34)ncn2)C1]

To 6-(difluoromethyl)-3-iodo-imidazo[1,2-b]pyridazine (65 mg, 0.22 mmol) in dry 1,4-dioxane (4 mL) was added tributyl(tributylstannyl)stannane (255.6 mg, 0.44 mmol), LiCl (46.72 mg, 1.1 mmol) and tetrakis(triphenylphosphine)palladium(0) (12.7 mg, 0.011 mmol). The mixture was heated at 105° C. under nitrogen for 15 hours. N-[[1-(6-Bromopyrimidin-4-yl)-3-piperidyl]methyl]methanesulfonamide (38 mg, 0.11 mmol) and Pd(PPh$_3$)$_2$Cl$_2$ (15.5 mg, 0.022 mmol) were added sequentially and the mixture was stirred at 140° C. in a sealed tube for 4 hours. Another portion of N-[[1-(6-bromopyrimidin-4-yl)-3-piperidyl]methyl]methanesulfonamide (76 mg, 0.22 mmol) was added and the mixture was stirred at 140° C. for a further 4 hours. The mixture was purified by reverse phase chromatography (C18, MeCN/Water 0.05% TFA as eluent) to afford N-((1-(6-(6-(Difluoromethyl)imidazo[1,2-b]pyridazin-3-yl)pyrimidin-4-yl)piperidin-3-yl)methyl)methanesulfonamide (6.6 mg, 5.4%).

Example 4: N-((1-(2-(6-(Difluoromethyl)imidazo[1, 2-b]pyridazin-3-yl)-6-(methylamino)pyridin-4-yl) piperidin-3-yl)methyl)methanesulfonamide, II-60

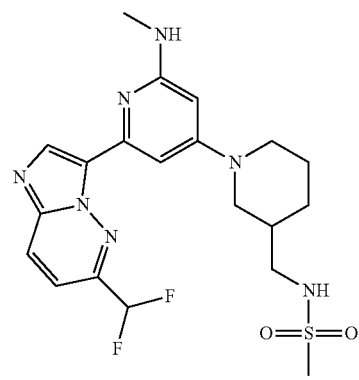 [SMILES: CNc1cc(N2CCCC(CNS(C)(=O)=O)C2)cc(-c2cnc3ccc(C(F)F)nn23)n1]

A solution of tributyl-[6-(difluoromethyl)imidazo[1,2-b] pyridazin-3-yl]stannane (82 mg, 0.179 mmol) in DMF (5 mL) was degassed with several vacuum/N$_2$ cycles before N-[[1-[2-bromo-6-(methylamino)-4-pyridyl]-3-piperidyl] methyl]methanesulfonamide (67.5 mg, 0.179 mmol) and Pd(PPh$_3$)$_2$Cl$_2$ (18.8 mg, 0.027 mmol) were added. The mixture was further degassed before heating at 90° C. under nitrogen for 2 hours. The mixture was loaded onto a 5 g SCX-2 cartridge and washed with DCM/MeOH mixtures. The product was eluted with a 2 M solution of NH₃ in MeOH and the filtrate concentrated in vacuo. The residue was purified by reverse phase chromatography (C18, MeCN/Water 0.05% TFA as eluent) to afford N-((1-(2-(6-(Difluoromethyl)imidazo[1,2-b]pyridazin-3-yl)-6-(methylamino)pyridin-4-yl)piperidin-3-yl)methyl)methanesulfonamide (5.3 mg, 4.6%).

Example 5: N-[[(2S)-4-[4-[6-(Difluoromethyl)imidazo[1,2-b]pyridazin-3-yl]-2-pyridyl]morpholin-2-yl]methyl]methanesulfonamide, II-121

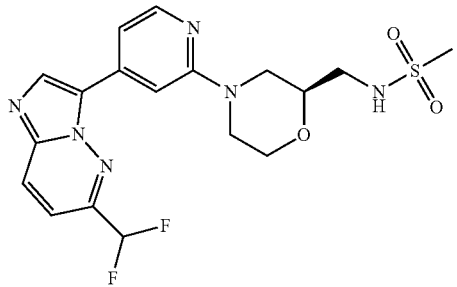 [SMILES: CS(=O)(=O)NC[C@@H]1CN(c2cc(-c3cnc4ccc(C(F)F)nn34)ccn2)CCO1]

A solution of 6-(Difluoromethyl)-3-(2-fluoro-4-pyridyl)imidazo[1,2-b]pyridazine (124 mg, 0.469 mmol), N-[[(2S)-morpholin-2-yl]methyl]methanesulfonamide (1.85 mL of 0.51 M, 0.943 mmol) and DIPEA (245 µL, 1.41 mmol) in NMP (0.15 mL) was heated at 160° C. for 16 hours. The reaction was cooled to ambient temperature and purified directly by reverse phase chromatography (C18, MeCN/water—0.1% ammonium hydroxide as eluent). The fractions were collected and freeze-dried to give N-[[(2S)-4-[4-[6-(difluoromethyl)imidazo[1,2-b]pyridazin-3-yl]-2-pyridyl]morpholin-2-yl]methyl]methanesulfonamide as beige solid (38 mg, 18%).

The following compounds were prepared using a methodology similar to the one described in Example 5:

N-((1-(4-(6-(Difluoromethyl)imidazo[1,2-b]pyridazin-3-yl)pyridin-2-yl)-5-hydroxypiperidin-3-yl)methyl)methanesulfonamide II-39;
N-((1-(4-(6-(Difluoromethyl)imidazo[1,2-b]pyridazin-3-yl)pyridin-2-yl)-5-hydroxypiperidin-3-yl)methyl)methanesulfonamide II-40;
N-((1-(4-(6-(Difluoromethyl)imidazo[1,2-b]pyridazin-3-yl)pyridin-2-yl)-4,4-difluoro-5-methylpiperidin-3-yl)methyl)methanesulfonamide II-57;
N-((1-(4-(6-(Difluoromethyl)imidazo[1,2-b]pyridazin-3-yl)pyridin-2-yl)-4,4-difluoro-5-methylpiperidin-3-yl)methyl)methanesulfonamide II-58;
4-(4-(6-(Difluoromethyl)imidazo[1,2-b]pyridazin-3-yl)pyridin-2-yl)morpholine II-76;
4-(4-(6-(Difluoromethyl)imidazo[1,2-b]pyridazin-3-yl)pyridin-2-yl)thiomorpholine 1,1-dioxide II-77;
N-((1-(4-(6-(Difluoromethyl)imidazo[1,2-b]pyridazin-3-yl)pyridin-2-yl)-4,4-difluoro-5-methylpiperidin-3-yl)methyl)methanesulfonamide II-78;
7-(4-(6-(Difluoromethyl)imidazo[1,2-b]pyridazin-3-yl)pyridin-2-yl)tetrahydro-1H-oxazolo[3,4-a]pyrazin-3(5H)-one II-88;
N-((4-(4-(6-(Difluoromethyl)imidazo[1,2-b]pyridazin-3-yl)pyridin-2-yl)piperazin-2-yl)methyl)methanesulfonamide II-90;
(4-(4-(6-(Difluoromethyl)imidazo[1,2-b]pyridazin-3-yl)pyridin-2-yl)-1-methylpiperazin-2-yl)methanol II-97;
N-((4-(4-(6-(Difluoromethyl)imidazo[1,2-b]pyridazin-3-yl)pyridin-2-yl)-1,4-oxazepan-6-yl)methyl)methanesulfonamide II-99;
[(2S)-4-[4-[6-(Difluoromethyl)imidazo[1,2-b]pyridazin-3-yl]-2-pyridyl]morpholin-2-yl]methylimino-dimethyl-oxo-sulfane II-102;
N-(1-(4-(4-(6-(Difluoromethyl)imidazo[1,2-b]pyridazin-3-yl)pyridin-2-yl)morpholin-2-yl)ethyl)methanesulfonamide II-106;
4-(4-(6-(Difluoromethyl)imidazo[1,2-b]pyridazin-3-yl)pyridin-2-yl)-2-(1H-pyrazol-4-yl)morpholine II-107;
4-(4-(6-(Difluoromethyl)imidazo[1,2-b]pyridazin-3-yl)pyridin-2-yl)-2-(1H-pyrazol-4-yl)morpholine II-108;
N-((1-(4-(6-(Difluoromethyl)imidazo[1,2-b]pyridazin-3-yl)pyridin-2-yl)piperidin-3-yl)methyl)-N-methylmethanesulfonamide II-109;
N-(2-(1-(4-(6-(Difluoromethyl)imidazo[1,2-b]pyridazin-3-yl)pyridin-2-yl)piperidin-3-yl)propan-2-yl)methanesulfonamide II-114;
N-((1-(4-(6-(Difluoromethyl)imidazo[1,2-b]pyridazin-3-yl)pyridin-2-yl)-3-methylpiperidin-3-yl)methyl)methanesulfonamide II-115;
N-((4-(4-(6-(Difluoromethyl)imidazo[1,2-b]pyridazin-3-yl)pyridin-2-yl)-6-methylmorpholin-2-yl)methyl)methanesulfonamide II-118;
N-((4-(4-(6-(Difluoromethyl)imidazo[1,2-b]pyridazin-3-yl)pyridin-2-yl)-6-methylmorpholin-2-yl)methyl)methanesulfonamide II-119;
N-((1-(4-(6-(Difluoromethyl)imidazo[1,2-b]pyridazin-3-yl)pyridin-2-yl)pyrrolidin-3-yl)methyl)methanesulfonamide II-123;
N-((1-(4-(6-(Difluoromethyl)imidazo[1,2-b]pyridazin-3-yl)pyridin-2-yl)piperidin-3-yl)oxy)methanesulfonamide II-124;
6-(Difluoromethyl)-3-(2-(3-(2-(methylsulfonyl)ethyl)piperidin-1-yl)pyridin-4-yl)imidazo[1,2-b]pyridazine II-128;
N-(1-(1-(4-(6-(Difluoromethyl)imidazo[1,2-b]pyridazin-3-yl)pyridin-2-yl)piperidin-3-yl)ethyl)methanesulfonamide II-133;
N-(1-(1-(4-(6-(Difluoromethyl)imidazo[1,2-b]pyridazin-3-yl)pyridin-2-yl)piperidin-3-yl)ethyl)methanesulfonamide II-134;
4-(4-(6-(Difluoromethyl)imidazo[1,2-b]pyridazin-3-yl)pyridin-2-yl)morpholine-2-carboxamide II-135;
6-(Difluoromethyl)-3-(2-(2-(methylsulfonyl)-2,6-diazaspiro[3.5]nonan-6-yl)pyridin-4-yl)imidazo[1,2-b]pyridazine II-136;
N-((1-(4-(6-(Difluoromethyl)imidazo[1,2-b]pyridazin-3-yl)pyridin-2-yl)-3-fluoropiperidin-3-yl)methyl)methanesulfonamide II-139;
(S')-1-(4-(6-(Difluoromethyl)imidazo[1,2-b]pyridazin-3-yl)pyridin-2-yl)piperidine-3-carboxamide II-143;
(1-(4-(6-(Difluoromethyl)imidazo[1,2-b]pyridazin-3-yl)pyridin-2-yl)piperidin-3-yl)methanesulfonamide II-144;
2-(1-(4-(6-(Difluoromethyl)imidazo[1,2-b]pyridazin-3-yl)pyridin-2-yl)piperidin-3-yl)acetamide II-145;
2-(4-(4-(6-(Difluoromethyl)imidazo[1,2-b]pyridazin-3-yl)pyridin-2-yl)morpholin-2-yl)ethanol II-146;
4-(4-(6-(Difluoromethyl)imidazo[1,2-b]pyridazin-3-yl)pyridin-2-yl)-2-(1H-pyrazol-4-yl)morpholine II-147;
(R)—N-((4-(4-(6-(Difluoromethyl)imidazo[1,2-b]pyridazin-3-yl)pyridin-2-yl)-6,6-dimethylmorpholin-2-yl)methyl)methanesulfonamide II-148;

N-((4-(4-(6-(Difluoromethyl)imidazo[1,2-b]pyridazin-3-yl)pyridin-2-yl)morpholin-2-yl)methyl)methanesulfonamide II-149;

6-(Difluoromethyl)-3-(2-(3-((methylsulfinyl)methyl)piperidin-1-yl)pyridin-4-yl)imidazo[1,2-b]pyridazine II-151;

N-((1-(4-(6-(Difluoromethyl)imidazo[1,2-b]pyridazin-3-yl)pyridin-2-yl)-4,4-difluoropiperidin-3-yl)methyl)methanesulfonamide II-153;

(S)—N-((1-(4-(6-(Difluoromethyl)imidazo[1,2-b]pyridazin-3-yl)pyridin-2-yl)piperidin-3-yl)methyl)methanesulfonamide II-154;

(R)—N-((1-(4-(6-(Difluoromethyl)imidazo[1,2-b]pyridazin-3-yl)pyridin-2-yl)piperidin-3-yl)methyl)methanesulfonamide II-155;

7-(4-(6-(Difluoromethyl)imidazo[1,2-b]pyridazin-3-yl)pyridin-2-yl)-2,7-diazaspiro[4.5]decan-1-one II-156;

N-((1-(4-(6-(Difluoromethyl)imidazo[1,2-b]pyridazin-3-yl)pyridin-2-yl)piperidin-3-yl)methyl)methanesulfonamide II-157;

7-(4-(6-(Difluoromethyl)imidazo[1,2-b]pyridazin-3-yl)pyridin-2-yl)-4,7-diazaspiro[2.5]octan-5-one II-160;

(1-(4-(6-(Difluoromethyl)imidazo[1,2-b]pyridazin-3-yl)pyridin-2-yl)piperidin-3-yl)methanol II-162;

1-(4-(4-(6-(Difluoromethyl)imidazo[1,2-b]pyridazin-3-yl)pyridin-2-yl)-1,4-diazepan-1-yl)ethanone II-163;

1-(4-(6-(Difluoromethyl)imidazo[1,2-b]pyridazin-3-yl)pyridin-2-yl)-1,4-diazepan-5-one II-164;

2-(4-(6-(Difluoromethyl)imidazo[1,2-b]pyridazin-3-yl)pyridin-2-yl)hexahydropyrrolo[1,2-a]pyrazin-6(2H)-one II-167;

2-(1-(4-(6-(Difluoromethyl)imidazo[1,2-b]pyridazin-3-yl)pyridin-2-yl)piperidin-4-yl)ethanol II-168;

1-(4-(4-(6-(Difluoromethyl)imidazo[12-b]pyridazin-3-yl)pyridin-2-yl)piperazin-1-yl)-2-methoxyethanone II-170;

7-(4-(6-(Difluoromethyl)imidazo[1,2-b]pyridazin-3-yl)pyridin-2-yl)hexahydroimidazo[1,5-a]pyrazin-3(2H)-one II-172;

7-(4-(6-(Difluoromethyl)imidazo[1,2-b]pyridazin-3-yl)pyridin-2-yl)hexahydroimidazo[1,5-a]pyrazin-3(2H)-one II-173;

7-(4-(6-(Difluoromethyl)imidazo[1,2-b]pyridazin-3-yl)pyridin-2-yl)-5,6,7,8-tetrahydro-[1,2,4]triazolo[4,3-a]pyrazine II-174;

7-(4-(6-(Difluoromethyl)imidazo[1,2-b]pyridazin-3-yl)pyridin-2-yl)hexahydroimidazo[1,5-a]pyrazin-3(2H)-one II-175;

1-(4-(4-(6-(Difluoromethyl)imidazo[1,2-b]pyridazin-3-yl)pyridin-2-yl)piperazin-1-yl)ethanone II-176;

(S)—N-((4-(4-(6-(Trifluoromethyl)imidazo[1,2-b]pyridazin-3-yl)pyridin-2-yl)morpholin-2-yl)methyl)methanesulfonamide II-224;

2-(1H-Pyrazol-4-yl)-4-(4-(6-(trifluoromethyl)imidazo[1,2-b]pyridazin-3-yl)pyridin-2-yl)morpholine II-225;

(S)-7'-(4-(6-(Trifluoromethyl)imidazo[1,2-b]pyridazin-3-yl)pyridin-2-yl)tetrahydrospiro[cyclopropane-1,1'-oxazolo[3,4-a]pyrazin]-3'(5'H)-one II-226;

3-(2-(3-((Methylsulfonyl)methyl)piperidin-1-yl)pyridin-4-yl)-6-(trifluoromethyl)imidazo[1,2-b]pyridazine II-227;

3-(2-(3-(Methylsulfonyl)piperidin-1-yl)pyridin-4-yl)-6-(trifluoromethyl)imidazo[1,2-b]pyridazine II-228;

2-(1H-Pyrazol-4-yl)-4-(4-(6-(trifluoromethyl)imidazo[1,2-b]pyridazin-3-yl)pyridin-2-yl)morpholine II-229 (single stereoisomer, separated by chiral SFC);

2-(1H-Pyrazol-4-yl)-4-(4-(6-(trifluoromethyl)imidazo[1,2-b]pyridazin-3-yl)pyridin-2-yl)morpholine II-230 (single stereoisomer, separated by chiral SFC);

N-(1-(4-(6-(Trifluoromethyl)imidazo[1,2-b]pyridazin-3-yl)pyridin-2-yl)piperidin-3-yl)methanesulfonamide II-231;

N-((4-(4-(6-(Trifluoromethyl)imidazo[1,2-b]pyridazin-3-yl)pyridin-2-yl)-1,4-oxazepan-6-yl)methyl)methanesulfonamide II-232;

((1-(4-(6-(Difluoromethyl)imidazo[1,2-b]pyridazin-3-yl)pyridin-2-yl)-5-methylpiperidin-3-yl)imino)dimethyl-λ$^6$-sulfanone II-716;

((1-(4-(6-(Difluoromethyl)imidazo[1,2-b]pyridazin-3-yl)pyridin-2-yl)-5-methylpiperidin-3-yl)imino)dimethyl-λ$^6$-sulfanone II-691.

Example 6: 2-(4-(6-(Difluoromethyl)imidazo[1,2-b]pyridazin-3-yl)pyridin-2-yl)octahydro-1H-pyrazino[1,2-a]pyrazine, II-38

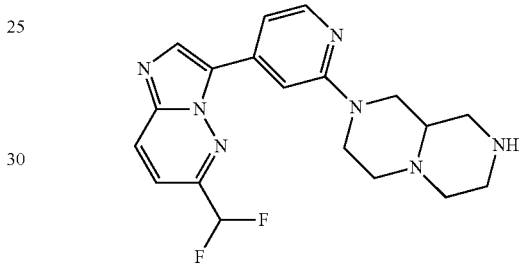

TFA (500 μL, 6.49 mmol) was added to a stirred solution of tert-butyl 8-[4-[6-(difluoromethyl)imidazo[1,2-b]pyridazin-3-yl]-2-pyridyl]-3,4,6,7,9,9a-hexahydro-1H-pyrazino[1,2-a]pyrazine-2-carboxylate (55.1 mg, 0.113 mmol, prepared according to a procedure similar to Example 5) in DCM (5 mL) and the reaction stirred at ambient temperature for 22 hours. The solvent was removed in vacuo and the residue azeotroped with DCM (×2) and diethyl ether (×2). The material was purified by reverse phase chromatography (C18, MeCN/water/0.05% TFA as eluent). The pure fractions were collected and freeze-dried to give 2-[4-[6-(difluoromethyl)imidazo[1,2-b]pyridazin-3-yl]-2-pyridyl]-1,3,4,6,7,8,9,9a-octahydropyrazino[1,2-a]pyrazine (28.1 mg, 39.5%) as a beige solid.

The following compounds were prepared using a methodology similar to the one described in Example 6:

3-(2-(2,6-Diazaspiro[3.3]heptan-2-yl)pyridin-4-yl)-6-(difluoromethyl)imidazo[1,2-b]pyridazine II-79;

3-(2-(3,9-Diazaspiro[5.5]undecan-3-yl)pyridin-4-yl)-6-(difluoromethyl)imidazo[1,2-b]pyridazine II-161;

3-(2-((1S,4S)-2,5-Diazabicyclo[2.2.1]heptan-2-yl)pyridin-4-yl)-6-(difluoromethyl)imidazo[1,2-b]pyridazine II-165;

3-(2-((1S,4S)-2,5-Diazabicyclo[2.2.1]heptan-2-yl)pyridin-4-yl)-6-(difluoromethyl)imidazo[1,2-b]pyridazine II-166;

(S)-(4-(4-(6-(Difluoromethyl)imidazo[1,2-b]pyridazin-3-yl)pyridin-2-yl)piperazin-2-yl)methanol II-169.

Example 7: 2-(4-(6-(Difluoromethyl)imidazo[1,2-b]pyridazin-3-yl)pyridin-2-yl)-8-(methylsulfonyl)octahydro-1H-pyrazino[1,2-a]pyrazine, II-37

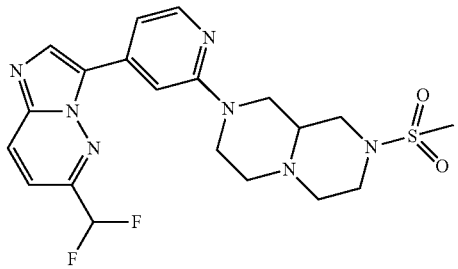 [SMILES: CS(=O)(=O)N1CCN2CCN(c3cc(-c4cnc5ccc(C(F)F)nn45)ccn3)CC2C1]

2-[4-[6-(Difluoromethyl)imidazo[1,2-b]pyridazin-3-yl]-2-pyridyl]-1,3,4,6,7,8,9,9a-octahydropyrazino[1,2-a]pyrazine (bis-trifluoroacetate salt) (28.1 mg, 0.045 mmol, prepared according to a procedure similar to Example 6) was dissolved in DMF (1 mL) and Et$_3$N (35 μL, 0.251 mmol) was added followed by methanesulfonyl chloride (6 μL, 0.077 mmol). The reaction mixture was stirred at ambient temperature for 1.5 hours. Water (200 μL) was added and the reaction mixture purified by reverse phase chromatography (C18, MeCN/water/0.05% TFA as eluent). The pure fractions were collected and freeze-dried to give 8-[4-[6-(difluoromethyl)imidazo[1,2-b]pyridazin-3-yl]-2-pyridyl]-2-methylsulfonyl-3,4,6,7,9,9a-hexahydro-1H-pyrazino[1,2-a]pyrazine) (10.1 mg, 38%) as a beige solid.

The following compounds were prepared using a methodology similar to the one described in Example 7:

6-(Difluoromethyl)-3-(6-(6-(methylsulfonyl)-2,6-diazaspiro[3.5]nonan-2-yl)pyrimidin-4-yl)imidazo[1,2-b]pyridazine II-279;

2-(6-(6-(Difluoromethyl)imidazo[1,2-b]pyridazin-3-yl)pyrimidin-4-yl)-8-(methylsulfonyl)-5-oxa-2,8-diazaspiro[3.5]nonane II-280;

6-(Difluoromethyl)-3-(6-(2-(methylsulfonyl)-2,6-diazaspiro[3.5]nonan-6-yl)pyrimidin-4-yl)imidazo[1,2-b]pyridazine II-281;

6-(Difluoromethyl)-3-(6-(5-(methylsulfonyl)hexahydropyrrolo[3,4-b]pyrrol-1 (2H)-yl)pyrimidin-4-yl)imidazo[1,2-b]pyridazine II-282;

N-((1-(6-(6-(Difluoromethyl)imidazo[1,2-b]pyridazin-3-yl)pyrimidin-4-yl)piperidin-3-yl)methyl)-N-methylmethanesulfonamide II-310;

4-(6-(6-(Difluoromethyl)imidazo[1,2-b]pyridazin-3-yl)pyrimidin-4-yl)-6-(methylsulfonyl)octahydropyrrolo[3,4-b][1,4]oxazine II-319;

6-(Difluoromethyl)-3-(6-(6-(methylsulfonyl)octahydro-1H-pyrrolo[3,4-b]pyridin-1-yl)pyrimidin-4-yl)imidazo[1,2-b]pyridazine II-320;

1-(6-(6-(Difluoromethyl)imidazo[1,2-b]pyridazin-3-yl)pyrimidin-4-yl)-6-(methylsulfonyl)octahydro-1H-pyrido[3,4-b][1,4]oxazine II-369;

N-(1-(6-(6-(Difluoromethyl)imidazo[1,2-b]pyridazin-3-yl)pyrimidin-4-yl)-4,4-difluoropiperidin-3-yl)methanesulfonamide II-589;

N-(1-(6-(6-(Difluoromethyl)imidazo[1,2-b]pyridazin-3-yl)pyrimidin-4-yl)-4,4-difluoropiperidin-3-yl)methanesulfonamide II-596;

N-(1-(6-(6-(Difluoromethyl)imidazo[1,2-b]pyridazin-3-yl)pyrimidin-4-yl)-4,4-difluoropiperidin-3-yl)methanesulfonamide II-597;

N-(1-(6-(6-(Difluoromethyl)imidazo[1,2-b]pyridazin-3-yl)pyrimidin-4-yl)-2-methylpiperidin-3-yl)methanesulfonamide II-600;

N-(1-(6-(6-(Difluoromethyl)imidazo[1,2-b]pyridazin-3-yl)pyrimidin-4-yl)-2-methylpiperidin-3-yl)methanesulfonamide II-601;

N-(1-(6-(6-(Difluoromethyl)imidazo[1,2-b]pyridazin-3-yl)pyrimidin-4-yl)-2-methylpiperidin-3-yl)methanesulfonamide II-602;

N-(1-(6-(6-(Difluoromethyl)imidazo[1,2-b]pyridazin-3-yl)pyrimidin-4-yl)-2-methylpiperidin-3-yl)methanesulfonamide II-603;

N-(1-(1-(6-(6-(Difluoromethyl)imidazo[1,2-b]pyridazin-3-yl)pyrimidin-4-yl)piperidin-3-yl)ethyl)methanesulfonamide II-619;

N-(1-(1-(6-(6-(Difluoromethyl)imidazo[1,2-b]pyridazin-3-yl)pyrimidin-4-yl)piperidin-3-yl)ethyl)methanesulfonamide II-620.

Example 8: N-((4-(4-(6-(Difluoromethyl)imidazo[1,2-b]pyridazin-3-yl)pyridin-2-yl)-1-(oxetan-3-yl)piperazin-2-yl)methyl)methanesulfonamide, II-81

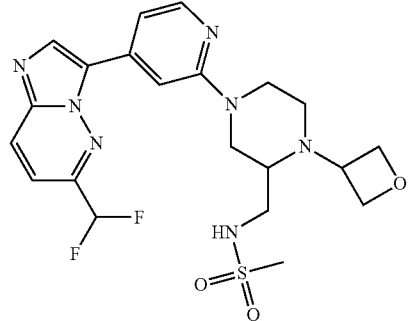 [SMILES: CS(=O)(=O)NCC1CN(c2cc(-c3cnc4ccc(C(F)F)nn34)ccn2)CCN1C1COC1]

A mixture of N-((4-(4-(6-(difluoromethyl)imidazo[1,2-b]pyridazin-3-yl)pyridin-2-yl)piperazin-2-yl)methyl)methanesulfonamide (trifluoroacetate salt) (80 mg, 0.135 mmol), acetic acid (15 μL, 0.264 mmol) and oxetan-3-one (25 mg, 0.347 mmol) in THF (3 mL) was stirred at ambient temperature for 90 minutes before sodium cyanoborohydride (15 mg, 0.239 mmol) was added and the reaction mixture was stirred at ambient temperature for 18 hours. The reaction mixture was concentrated in vacuo and the residue was purified by reverse phase chromatography (C18, MeCN/water/0.05% TFA as eluent). The pure fractions were collected and freeze-dried to afford the title compound (20 mg, 22%).

Example 9: N-((1-(4-(6-(Difluoromethyl)imidazo[1,2-b]pyridazin-3-yl)-6-fluoropyridin-2-yl)piperidin-3-yl)methyl)methanesulfonamide, II-122

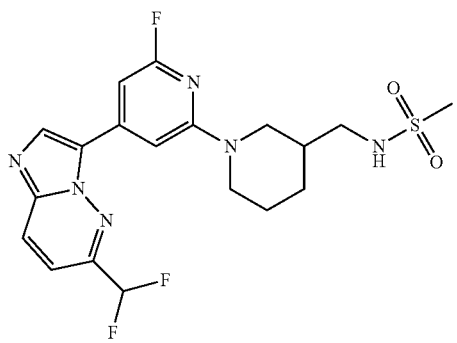 [SMILES: CS(=O)(=O)NCC1CCCN(c2cc(-c3cnc4ccc(C(F)F)nn34)cc(F)n2)C1]

6-(Difluoromethyl)-3-(2,6-difluoro-4-pyridyl)imidazo[1,2-b]pyridazine (478 mg, 1.694 mmol), N-(3-piperidylmethyl)methanesulfonamide (325.7 mg, 1.694 mmol) and DIPEA (875.8 mg, 1.18 mL, 6.776 mmol) were heated in NMP (10 mL) at 120° C. for 3 hours. The reaction mixture was cooled to ambient temperature and partitioned between EtOAc and brine. The organic extract was dried (MgSO₄) and concentrated in vacuo to afford N-((1-(4-(6-(difluoromethyl)imidazo[1,2-b]pyridazin-3-yl)-6-fluoropyridin-2-yl)piperidin-3-yl)methyl)methanesulfonamide as a brown solid (593 mg, 77%).

Example 10: N-((1-(4-(6-(Difluoromethyl)imidazo[1,2-b]pyridazin-3-yl)-6-morpholinopyridin-2-yl)piperidin-3-yl)methyl)methanesulfonamide, II-66

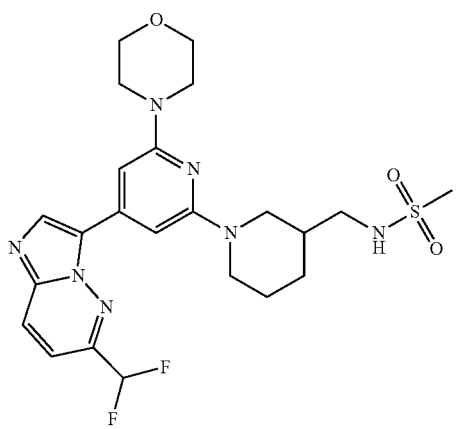 [SMILES: CS(=O)(=O)NCC1CCCN(c2cc(-c3cnc4ccc(C(F)F)nn34)cc(N3CCOCC3)n2)C1]

A mixture of N-[[1-[4-[6-(difluoromethyl)imidazo[1,2-b]pyridazin-3-yl]-6-fluoro-2-pyridyl]-3-piperidyl]methyl]methanesulfonamide (36 mg, 0.079 mmol), morpholine (100 µL, 1.147 mmol) and DIPEA (50 µL, 0.287 mmol) in NMP (0.5 mL) was heated at 170° C. for 16 hours. The reaction mixture was cooled to ambient temperature and was purified by reverse phase chromatography (C18, MeCN/Water/0.05% TFA as eluent). The pure fractions were freeze dried to afford N-((1-(4-(6-(difluoromethyl)imidazo[1,2-b]pyridazin-3-yl)-6-morpholinopyridin-2-yl)piperidin-3-yl)methyl)methanesulfonamide (24.1 mg, 35%).

The following compounds were prepared using a methodology similar to the one described in Example 10:

N-((1-(4-(6-(Difluoromethyl)imidazo[1,2-b]pyridazin-3-yl)-6-(6-methyl-2,6-diazaspiro[3.3]heptan-2-yl)pyridin-2-yl)piperidin-3-yl)methyl)methanesulfonamide II-72;

N-((1-(4-(6-(Difluoromethyl)imidazo[1,2-b]pyridazin-3-yl)-6-(2-oxa-6-azaspiro[3.3]heptan-6-yl)pyridin-2-yl)piperidin-3-yl)methyl)methanesulfonamide II-83;

N-((1-(4-(6-(Difluoromethyl)imidazo[1,2-b]pyridazin-3-yl)-6-(3-hydroxyazetidin-1-yl)pyridin-2-yl)piperidin-3-yl)methyl)methanesulfonamide II-85;

N-((1-(4-(6-(Difluoromethyl)imidazo[1,2-b]pyridazin-3-yl)-6-(1-oxa-6-azaspiro[3.3]heptan-6-yl)pyridin-2-yl)piperidin-3-yl)methyl)methanesulfonamide II-86;

N-((1-(4-(6-(Difluoromethyl)imidazo[1,2-b]pyridazin-3-yl)-6-((2-methoxyethyl)amino)pyridin-2-yl)piperidin-3-yl)methyl)methanesulfonamide II-89;

N-((1-(4-(6-(Difluoromethyl)imidazo[1,2-b]pyridazin-3-yl)-6-((2-hydroxyethyl)amino)pyridin-2-yl)piperidin-3-yl)methyl)methanesulfonamide II-91;

N-((1-(4-(6-(Difluoromethyl)imidazo[1,2-b]pyridazin-3-yl)-6-(piperazin-1-yl)pyridin-2-yl)piperidin-3-yl)methyl)methanesulfonamide II-96;

N-((1-(4-(6-(Difluoromethyl)imidazo[1,2-b]pyridazin-3-yl)-6-(methylamino)pyridin-2-yl)piperidin-3-yl)methyl)methanesulfonamide II-116.

Example 11: N-[[1-[6-(2,6-Diazaspiro[3.3]heptan-2-yl)-4-[6-(difluoromethyl)imidazo[1,2-b]pyridazin-3-yl]-2-pyridyl]-3-piperidyl]methyl]methanesulfonamide, II-92

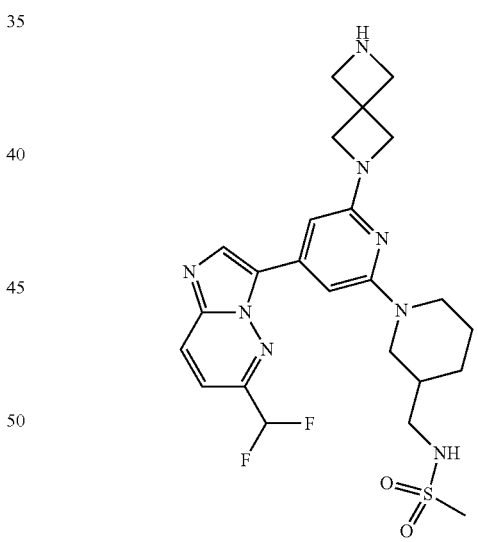

A suspension of N-[[1-[4-[6-(difluoromethyl)imidazo[1,2-b]pyridazin-3-yl]-6-fluoro-2-pyridyl]-3-piperidyl]methyl]methanesulfonamide (50 mg, 0.11 mmol), tert-butyl 2,6-diazaspiro[3.3]heptane-2-carboxylate (65.4 mg, 0.33 mmol) and Cs₂CO₃ (179.2 mg, 0.55 mmol) in 1,4-dioxane (730 µL) was heated at 120° C. for 16 hours. The reaction was concentrated in vacuo and the residue was suspended in DCM before TFA (1.254 g, 847 µL, 11 mmol) was added. The mixture was stirred at ambient temperature for 1 hour before the solution was concentrated in vacuo. The residue was purified by reverse phase chromatography (C18, MeCN/Water/0.05% TFA as eluent) to afford N-[[1-[6-(2,6-

Diazaspiro[3.3]heptan-2-yl)-4-[6-(difluoromethyl)imidazo[1,2-b]pyridazin-3-yl]-2-pyridyl]-3-piperidyl]methyl]methanesulfonamide (15.2 mg, 19%).

The following compounds were prepared using a methodology similar to the one described in Example 11:

N-((1-(4-(6-(Difluoromethyl)imidazo[1,2-b]pyridazin-3-yl)-6-(1,6-diazaspiro[3.3]heptan-6-yl)pyridin-2-yl)piperidin-3-yl)methyl)methanesulfonamide II-67;

N-((1-(4-(6-(Difluoromethyl)imidazo[1,2-b]pyridazin-3-yl)-6-(2-(methylamino)ethoxy)pyridin-2-yl)piperidin-3-yl)methyl)methanesulfonamide II-74;

N-((1-(6-(Azetidin-3-yloxy)-4-(6-(difluoromethyl)imidazo[1,2-b]pyridazin-3-yl)pyridin-2-yl)piperidin-3-yl)methyl)methanesulfonamide II-84.

Example 12: N-((1-(6-(6-Acetyl-2,6-diazaspiro[3.3]heptan-2-yl)-4-(6-(difluoromethyl)imidazo[1,2-b]pyridazin-3-yl)pyridin-2-yl)piperidin-3-yl)methyl)methanesulfonamide, II-55

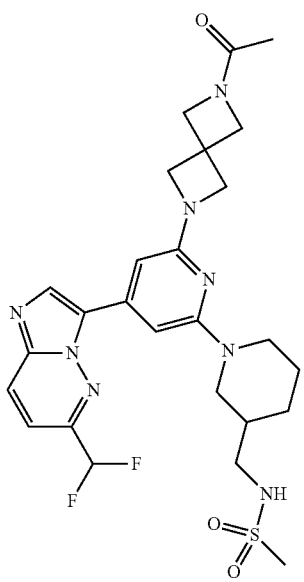 [SMILES: CC(=O)N1CC2(C1)CN(c1cc(-c3cnc4ccc(C(F)F)nn34)cc(N3CCCC(CNS(C)(=O)=O)C3)n1)C2]

Acetyl chloride (2.4 mg, 2.2 μL, 0.031 mmol) and DMAP (0.13 mg, 0.001 mmol) were added sequentially to a solution of N-[[1-[6-(2,6-diazaspiro[3.3]heptan-2-yl)-4-[6-(difluoromethyl)imidazo[1,2-b]pyridazin-3-yl]-2-pyridyl]-3-piperidyl]methyl]methanesulfonamide (13.3 mg, 0.021 mmol) and Et₃N (8.4 mg, 11.56 μL, 0.083 mmol) in DCM (300 μL). After 1 hour, MeOH was added to quench the reaction and the mixture was purified by reverse phase chromatography (C18, MeCN/Water/0.05% TFA as eluent) to give N-((1-(6-(6-acetyl-2,6-diazaspiro[3.3]heptan-2-yl)-4-(6-(difluoromethyl)imidazo[1,2-b]pyridazin-3-yl)pyridin-2-yl)piperidin-3-yl)methyl)methanesulfonamide (4.5 mg, 27%).

Example 13: (S)—N-((1-(4-(6-(Difluoromethyl)imidazo[1,2-b]pyridazin-3-yl)-6-(methylamino)pyridin-2-yl)piperidin-3-yl)methyl)methanesulfonamide, II-68

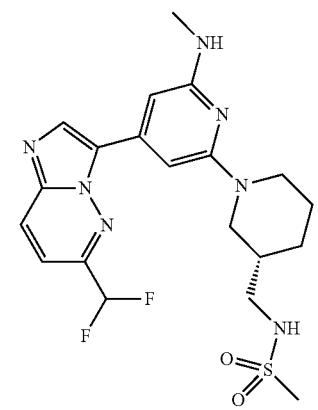 [SMILES: CNc1cc(-c2cnc3ccc(C(F)F)nn23)cc(N2CCC[C@H](CNS(C)(=O)=O)C2)n1]

A mixture of 6-(difluoromethyl)-3-(2,6-difluoro-4-pyridyl)imidazo[1,2-b]pyridazine (100 mg, 0.354 mmol), N-[[(3S)-3-piperidyl]methyl]methanesulfonamide (68.1 mg, 0.354 mmol) and DIPEA (183.3 mg, 247 μL, 1.418 mmol) was heated in NMP (1.8 mL) at 120° C. After 3 hours, methylamine (500 μL of 40% w/v, 6.44 mmol) was added and the reaction and was heated at 150° C. for 16 hours. An additional portion of methylamine (500 μL of 40% w/v, 6.44 mmol) was added, and the reaction mixture was heated at 170° C. for 6 hours. The crude reaction mixture was purified by reverse phase chromatography (C18, MeCN/Water/0.05% TFA as eluent) to give (S)—N-((1-(4-(6-(difluoromethyl)imidazo[1,2-b]pyridazin-3-yl)-6-(methylamino)pyridin-2-yl)piperidin-3-yl)methyl)methanesulfonamide (13.1 mg, 8%).

The following compounds were prepared using a methodology similar to the one described in Example 13:

N-((1-(4-(6-(Difluoromethyl)imidazo[1,2-b]pyridazin-3-yl)-6-(methylamino)pyridin-2-yl)-4,4-difluoro-5-methylpiperidin-3-yl)methyl)methanesulfonamide II-64;

N-((1-(4-(6-(Difluoromethyl)imidazo[1,2-b]pyridazin-3-yl)-6-(methylamino)pyridin-2-yl)-4,4-difluoro-5-methylpiperidin-3-yl)methyl)methanesulfonamide II-65;

(S)—N-((4-(4-(6-(Difluoromethyl)imidazo[1,2-b]pyridazin-3-yl)-6-(methylamino)pyridin-2-yl)morpholin-2-yl)methyl)methanesulfonamide II-69;

N-((1-(4-(6-(Difluoromethyl)imidazo[1,2-b]pyridazin-3-yl)-6-(methylamino)pyridin-2-yl)-4,4-difluoropiperidin-3-yl)methyl)methanesulfonamide II-71.

Example 14: N-((1-(6-Cyano-4-(6-(difluoromethyl) imidazo[1,2-b]pyridazin-3-yl)pyridin-2-yl)piperidin-3-yl)methyl)methanesulfonamide, II-130

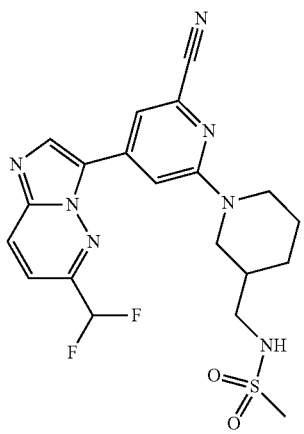 [SMILES: CS(=O)(=O)NCC1CCCN(c2cc(-c3cnc4ccc(C(F)F)nn34)cc(C#N)n2)C1]

A mixture of 6-chloro-4-[6-(difluoromethyl)imidazo[1,2-b]pyridazin-3-yl]pyridine-2-carbonitrile (40 mg, 0.073 mmol), N-(3-piperidylmethyl)methanesulfonamide (28.2 mg, 0.147 mmol) and DIPEA (37.9 mg, 51.0 μL, 0.293 mmol) was heated in NMP (375 μL) at 150° C. for 3 hours. The crude reaction mixture was purified by reverse phase chromatography (C18, MeCN/Water/0.05% TFA as eluent) to give N-((1-(6-cyano-4-(6-(difluoromethyl)imidazo[1,2-b]pyridazin-3-yl)pyridin-2-yl)piperidin-3-yl)methyl)methanesulfonamide as a beige solid (14.3 mg, 33%).

The following compounds were prepared using a methodology similar to the one described in Example 14:
N-((1-(4-(6-(Difluoromethyl)imidazo[1,2-b]pyridazin-3-yl)-6-methylpyridin-2-yl)piperidin-3-yl)methyl)methanesulfonamide II-129.

Example 15: N-((1-(6-(Aminomethyl)-4-(6-(difluoromethyl)imidazo[1,2-b]pyridazin-3-yl)pyridin-2-yl)piperidin-3-yl)methyl)methanesulfonamide, II-80

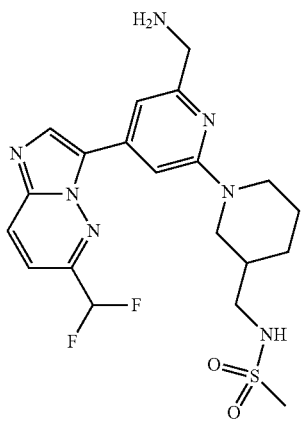 [SMILES: CS(=O)(=O)NCC1CCCN(c2cc(-c3cnc4ccc(C(F)F)nn34)cc(CN)n2)C1]

Methanol (16.9 mL), followed by HCl (100 μL of 12 M, 1.2 mmol) was added to N-[[1-[6-cyano-4-[6-(difluoromethyl)imidazo[1,2-b]pyridazin-3-yl]-2-pyridyl]-3-piperidyl]methyl]methanesulfonamide (35 mg, 0.076 mmol) and Pd(OH)$_2$ on carbon (10.6 mg, 0.076 mmol). The suspension was stirred under a balloon of H$_2$ for 5 hours then the catalyst was filtered off and the filtrate concentrated in vacuo. The residue was purified by reverse phase chromatography (C18, MeCN/Water/0.05% TFA as eluent) to give N-((1-(6-(aminomethyl)-4-(6-(difluoromethyl)imidazo[1,2-b]pyridazin-3-yl)pyridin-2-yl)piperidin-3-yl)methyl)methanesulfonamide (7.8 mg, 15%).

Example 16: N-((1-(4-(6-(Difluoromethyl)imidazo[1,2-b]pyridazin-3-yl)-6-(trifluoromethyl)pyridin-2-yl)piperidin-3-yl)methyl)methanesulfonamide, II-63

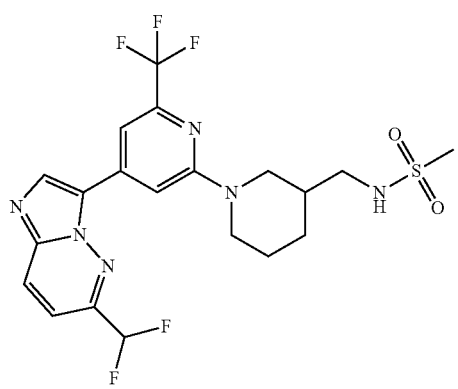 [SMILES: CS(=O)(=O)NCC1CCCN(c2cc(-c3cnc4ccc(C(F)F)nn34)cc(C(F)(F)F)n2)C1]

A mixture of 3-[2-chloro-6-(trifluoromethyl)-4-pyridyl]-6-(difluoromethyl)imidazo[1,2-b]pyridazine (40 mg, 0.115 mmol), N-(3-piperidylmethyl)methanesulfonamide (33.1 mg, 0.172 mmol) and DIPEA (59.3 mg, 79.9 μL, 0.459 mmol) in NMP (570 μL) was heated at 150° C. for 16 hours. After cooling, the reaction mixture was purified by reverse phase chromatography (C18, MeCN/Water/0.05% TFA as eluent) to give N-((1-(4-(6-(difluoromethyl)imidazo[1,2-b]pyridazin-3-yl)-6-(trifluoromethyl)pyridin-2-yl)piperidin-3-yl)methyl)methanesulfonamide (10.1 mg, 13%).

Example 17: N-((1-(6-Chloro-4-(6-(difluoromethyl) imidazo[1,2-b]pyridazin-3-yl)pyridin-2-yl)piperidin-3-yl)methyl)methanesulfonamide, II-61

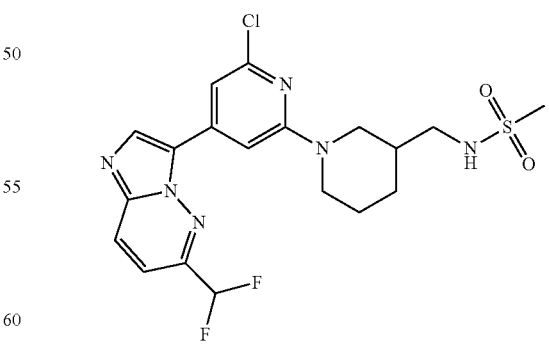

A mixture of 3-(2,6-dichloro-4-pyridyl)-6-(difluoromethyl)imidazo[1,2-b]pyridazine (40 mg, 0.127 mmol), N-(3-piperidylmethyl)methanesulfonamide (26.8 mg, 0.140 mmol) and DIPEA (65.6 mg, 88.4 μL, 0.508 mmol) in NMP (630 μL) was heated at 150° C. for 16 hours. After cooling,

819 the reaction mixture was purified by reverse phase chromatography (C18, MeCN/Water/0.05% TFA as eluent) to give N-((1-(6-chloro-4-(6-(difluoromethyl)imidazo[1,2-b]pyridazin-3-yl)pyridin-2-yl)piperidin-3-yl)methyl)methanesulfonamide (17.5 mg, 21%).

Example 18: N-((1-(2-(6-(Difluoromethyl)imidazo[1,2-b]pyridazin-3-yl)pyridin-4-yl)-4,4-difluoro-5-methylpiperidin-3-yl)methyl)methanesulfonamide, II-75

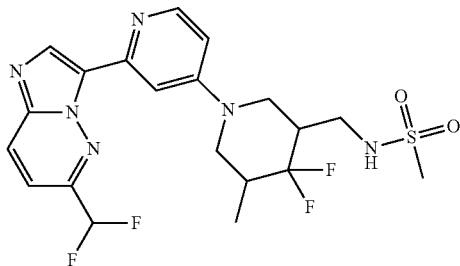 [SMILES: CC1CN(c2ccnc(-c3cnc4ccc(C(F)F)nn34)c2)CC(CNS(C)(=O)=O)C1(F)F]

6-(Difluoromethyl)-3-(4-fluoro-2-pyridyl)imidazo[1,2-b]pyridazine (18 mg, 0.068 mmol), DIPEA (26.4 mg, 35.6 μL, 0.204 mmol) and N-[(4,4-difluoro-5-methyl-3-piperidyl)methyl]methanesulfonamide (24.8 mg, 0.102 mmol) were added to NMP (225 μL) and heated at 150° C. for 13 hours. After cooling, the crude reaction mixture was filtered and purified by reverse phase chromatography (C18, MeCN/Water/0.05% TFA as eluent) to give N-[[1-[2-[6-(difluoromethyl)imidazo[1,2-b]pyridazin-3-yl]-4-pyridyl]-4,4-difluoro-5-methyl-3-piperidyl]methyl]methanesulfonamide (2.2 mg, 6.8%).

The following compounds were prepared using a methodology similar to the one described in Example 18:

N-((1-(2-(6-(Difluoromethyl)imidazo[1,2-b]pyridazin-3-yl)pyridin-4-yl)-4,4-difluoro-5-methylpiperidin-3-yl)methyl)methanesulfonamide II-93;

N-((4-(2-(6-(Difluoromethyl)imidazo[1,2-b]pyridazin-3-yl)pyridin-4-yl)-6-methylmorpholin-2-yl)methyl)methanesulfonamide II-94;

N-((1-(2-(6-(Difluoromethyl)imidazo[1,2-b]pyridazin-3-yl)pyridin-4-yl)-4,4-difluoropiperidin-3-yl)methyl)methanesulfonamide II-103;

N-(1-(4-(2-(6-(Difluoromethyl)imidazo[1,2-b]pyridazin-3-yl)pyridin-4-yl)morpholin-2-yl)ethyl)methanesulfonamide II-105;

(S)—N-((4-(2-(6-(Difluoromethyl)imidazo[1,2-b]pyridazin-3-yl)pyridin-4-yl)morpholin-2-yl)methyl)methanesulfonamide II-110;

N-((1-(2-(6-(Difluoromethyl)imidazo[1,2-b]pyridazin-3-yl)pyridin-4-yl)piperidin-3-yl)methyl)methanesulfonamide II-125;

1-(4-(2-(6-(Difluoromethyl)imidazo[1,2-b]pyridazin-3-yl)pyridin-4-yl)piperazin-1-yl)ethanone II-127.

Example 19: 6-(Difluoromethyl)-3-(6-(1-(methylsulfonyl)azepan-4-yl)pyrimidin-4-yl)imidazo[1,2-b]pyridazine, II-14

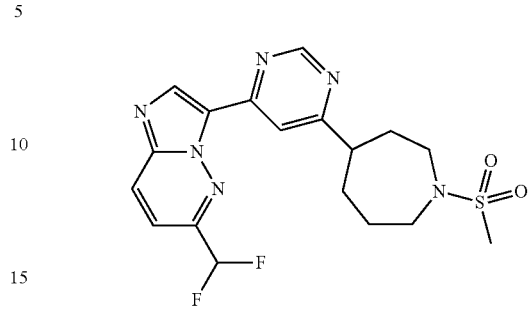

Step 1: 6-(Difluoromethyl)-3-[6-(2,3,6,7-tetrahydro-1H-azepin-4-yl)pyrimidin-4-yl]imidazo[1,2-b]pyridazine 3-(6-Chloropyrimidin-4-yl)-6-(difluoromethyl)imidazo[1,2-b]pyridazine (100 mg, 0.355 mmol), tert-butyl 4-(4,4,5,5-tetramethyl-1,3,2-dioxaborolan-2-yl)-2,3,6,7-tetrahydroazepine-1-carboxylate (172.2 mg, 0.533 mmol) and aqueous K₂CO₃ (888 μL of 2 M, 1.776 mmol) were combined in 1,4-dioxane (1.5 mL) and the mixture was degassed (×2 vacuum-N₂ cycles). Pd(dppf)Cl₂.DCM (14.5 mg, 0.018 mmol) was added and the mixture was degassed (×2 cycles) again then heated at 130° C. for 45 minutes in a microwave. The reaction mixture was partitioned between EtOAc and water. The organic extract was washed with brine, dried and concentrated in vacuo. The residue was purified by column chromatography (silica, 0-100% EtOAc/PE gradient elution). The pure fractions were concentrated to a yellow solid. The solid was taken up in DCM (2 mL) and TFA (1 mL) was added. After 1 hour at ambient temperature, the reaction mixture was concentrated in vacuo to yield 6-(difluoromethyl)-3-[6-(2,3,6,7-tetrahydro-1H-azepin-4-yl)pyrimidin-4-yl]imidazo[1,2-b]pyridazine (120 mg, 99%); MS m/z: 343.0 (M+H)⁺.

Step 2: 6-(Difluoromethyl)-3-(6-(1-(methylsulfonyl)-2,3,6,7-tetrahydro-1H-azepin-4-yl)pyrimidin-4-yl)imidazo[1,2-b]pyridazine DIPEA (170 mg, 229.1 μL, 1.315 mmol) was added to 6-(difluoromethyl)-3-[6-(2,3,6,7-tetrahydro-1H-azepin-4-yl)pyrimidin-4-yl]imidazo[1,2-b]pyridazine (90 mg, 0.263 mmol) in NMP (0.5 mL). The solution was cooled in an ice bath and methanesulfonyl chloride (30.1 mg, 20.35 μL, 0.263 mmol) was added. After 5 minutes, the reaction was quenched by the addition of water. The reaction mixture was purified by reverse phase chromatography (C18, MeCN/water/0.05% TFA as eluent) and the clean fractions were combined and concentrated to give 6-(difluoromethyl)-3-[6-(1-methylsulfonyl-2,3,6,7-tetrahydroazepin-4-yl)pyrimidin-4-yl]imidazo[1,2-b]pyridazine as a tan solid (39 mg, 35%); MS m/z: 421.0 (M+H)⁺.

Step 3: 6-(Difluoromethyl)-3-[6-(1-methylsulfonylazepan-4-yl)pyrimidin-4-yl]imidazo[1,2-b]pyridazine 6-(Difluoromethyl)-3-[6-(1-methylsulfonyl-2,3,6,7-tetrahydroazepin-4-yl)pyrimidin-4-yl]imidazo[1,2-b]pyridazine (39 mg, 0.093 mmol) was suspended in MeOH (5 mL). The mixture was degassed (×5 vacuum-$N_2$ cycles) before Pd on C, wet, Degussa (1.9 mg, 0.018 mmol) was added and the mixture degassed with $N_2$ (×5 cycles). The reaction mixture was hydrogenated for 16 hours at ambient temperature under a balloon of $H_2$. The catalyst was filtered off and the filtrate was concentrated in vacuo to afford 6-(difluoromethyl)-3-(6-(1-(methylsulfonyl)azepan-4-yl)pyrimidin-4-yl)imidazo[1,2-b]pyridazine as a pale yellow solid (17.6 mg, 43%).

The following enantiomers were prepared using a methodology similar to the one described in Example 19 and separated by chiral SFC:
(R)-6-(Difluoromethyl)-3-(6-(1-(methylsulfonyl)azepan-4-yl)pyrimidin-4-yl)imidazo[1,2-b]pyridazine and (S)-6-(Difluoromethyl)-3-(6-(1-(methylsulfonyl)azepan-4-yl)pyrimidin-4-yl)imidazo[1,2-b]pyridazine; II-275 and II-276 (in no particular order).

Example 20: 6-(Difluoromethyl)-3-(6-(1-(methylsulfonyl)piperidin-3-yl)pyrimidin-4-yl)imidazo[1,2-b]pyridazine, II-21

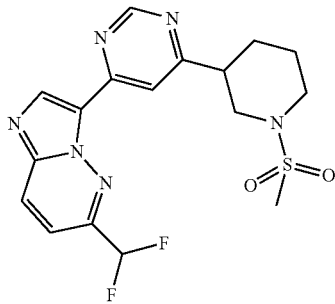 [SMILES: CS(=O)(=O)N1CCCC(c2cc(-c3cnc4ccc(C(F)F)nn34)ncn2)C1]

Step 1: 6-(Difluoromethyl)-3-(6-(1,2,5,6-tetrahydropyridin-3-yl)pyrimidin-4-yl)imidazo[1,2-b]pyridazine 3-(6-Chloropyrimidin-4-yl)-6-(difluoromethyl)imidazo[1,2-b]pyridazine (100 mg, 0.355 mmol), tert-butyl 5-(4,4,5,5-tetramethyl-1,3,2-dioxaborolan-2-yl)-3,6-dihydro-2H-pyridine-1-carboxylate (109.8 mg, 0.355 mmol) and aqueous $K_2CO_3$ (888 μL of 2 M, 1.776 mmol) were combined in 1,4-dioxane (1.5 mL). Pd(dppf)$Cl_2$.DCM (14.5 mg, 0.018 mmol) was added and the mixture was degassed (×2 vacuum-$N_2$ cycles) before the reaction was heated at 130° C. for 45 minutes in a microwave. The reaction mixture was partitioned between EtOAc and water. The organic extract was washed with brine, dried and concentrated in vacuo. The residue was purified by column chromatography (silica, 0-100% EtOAc/PE gradient elution). The pure fractions were concentrated in vacuo, the residue was taken up in DCM (2 mL) and TFA (607.4 mg, 410 μL, 5.326 mmol) was added. The reaction was stirred at ambient temperature for 16 hours and concentrated in vacuo. The residue was loaded on a SCX-2 cartridge and washed with DCM-MeOH mixtures. The product was eluted with 2 M $NH_3$ in MeOH. The filtrate was concentrated in vacuo to yield 6-(difluoromethyl)-3-(6-(1,2,5,6-tetrahydropyridin-3-yl)pyrimidin-4-yl)imidazo[1,2-b]pyridazine (55 mg, 47%); MS m/z: 329.2 $(M+H)^+$.

Step 2: 6-(Difluoromethyl)-3-(6-(piperidin-3-yl)pyrimidin-4-yl)imidazo[1,2-b]pyridazine Pd on C, wet, Degussa (45.4 mg, 0.426 mmol) was added to 6-(difluoromethyl)-3-[6-(1,2,3,6-tetrahydropyridin-5-yl)pyrimidin-4-yl]imidazo[1,2-b]pyridazine (200 mg, 0.61 mmol) and the mixture was dissolved in MeOH (26 mL). The mixture was degassed (×5 cycles), then hydrogenated for 16 hours ($H_2$ at balloon pressure). The catalyst was filtered off and the filtrate was evaporated in vacuo to afford 6-(difluoromethyl)-3-(6-(piperidin-3-yl)pyrimidin-4-yl)imidazo[1,2-b]pyridazine; MS m/z: 331.3 $(M+H)^+$.

Step 3: 6-(Difluoromethyl)-3-(6-(1-(methylsulfonyl)piperidin-3-yl)pyrimidin-4-yl)imidazo[1,2-b]pyridazine To a solution of 6-(difluoromethyl)-3-(6-(piperidin-3-yl)pyrimidin-4-yl)imidazo[1,2-b]pyridazine (7.7 mg, 0.023 mmol) and DIPEA (20.2 μL, 0.116 mmol) in acetonitrile (0.2 mL) was added methanesulfonyl chloride (2.7 mg, 2 μL, 0.023 mmol) and the mixture was stirred at ambient temperature for 1 hour. The reaction was quenched with water and purified by reverse phase chromatography (C18, MeCN/Water/0.05% TFA as eluent) to give 6-(difluoromethyl)-3-(6-(1-(methylsulfonyl)piperidin-3-yl)pyrimidin-4-yl)imidazo[1,2-b]pyridazine (6 mg, 58%).

The following compound was prepared using a methodology similar to the one described in Example 20:
6-(Difluoromethyl)-3-(6-(1-(methylsulfonyl)pyrrolidin-3-yl)pyrimidin-4-yl)imidazo[1,2-b]pyridazine II-250.
The following compounds were prepared according to Step 1 and Step 2 of Example 20:
6-(Difluoromethyl)-3-(6-(3,6-dihydro-2H-pyran-4-yl)pyrimidin-4-yl)imidazo[1,2-b]pyridazine II-357;
6-(Difluoromethyl)-3-(6-tetrahydropyran-4-ylpyrimidin-4-yl)imidazo[1,2-b]pyridazine II-358.

Example 21: 6-(Difluoromethyl)-3-(5-(7-(methylsulfonyl)-1,7-diazaspiro[3.5]nonan-1-yl)pyridin-3-yl)imidazo[1,2-b]pyridazine, II-42

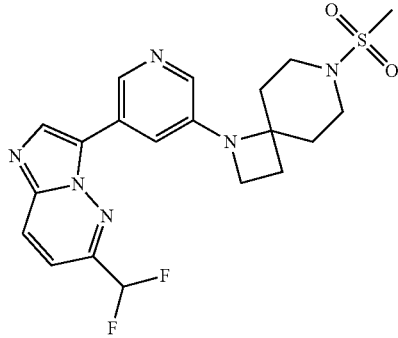 [SMILES: CS(=O)(=O)N1CCC2(CCN2c2cncc(-c3cnc4ccc(C(F)F)nn34)c2)CC1]

Step 1: 3-(5-Bromopyridin-3-yl)-6-(difluoromethyl)imidazo[1,2-b]pyridazine

A mixture of 6-(difluoromethyl)-3-iodo-imidazo[1,2-b]pyridazine (250 mg, 0.847 mmol), 3-bromo-5-(4,4,5,5-tetramethyl-1,3,2-dioxaborolan-2-yl)pyridine (200.5 mg, 0.706 mmol), Pd(dppf)$Cl_2$.$CH_2Cl_2$ (57.7 mg, 0.071 mmol) and $Na_2CO_3$ (706 μL of 2 M, 1.412 mmol) in THF (3.5 mL) was degassed with nitrogen for 10 minutes. The suspension was heated at 65° C. for 20 hours. The reaction mixture was cooled to ambient temperature and partitioned between EtOAc and a saturated aqueous sodium bicarbonate. The organic layer was dried ($MgSO_4$) and concentrated in vacuo to afford 3-(5-bromopyridin-3-yl)-6-(difluoromethyl)imidazo[1,2-b]pyridazine as a light brown solid that was used in next step without further purification; MS m/z: 325.0 (M+H)⁺.

Step 2: 6-(Difluoromethyl)-3-(5-(7-(methylsulfonyl)-1,7-diazaspiro[3.5]nonan-1-yl)pyridin-3-yl)imidazo[1,2-b]pyridazine A mixture of 3-(5-bromo-3-pyridyl)-6-(difluoromethyl)imidazo[1,2-b]pyridazine (50 mg, 0.154 mmol), 7-methylsulfonyl-1,7-diazaspiro[3.5]nonane (47.1 mg, 0.231 mmol), Cs₂CO₃ (100.2 mg, 0.308 mmol), Pd₂(dba)₃ (7.0 mg, 0.008 mmol) and Xantphos (8.9 mg, 0.015 mmol) in 1,4-dioxane (737 µL) was degassed with nitrogen. The suspension was then heated to 120° C. for 16 hours. After cooling to ambient temperature the reaction mixture was purified by reverse phase chromatography (C18, MeCN/Water/0.05% TFA as eluent) to give 6-(difluoromethyl)-3-(5-(7-(methylsulfonyl)-1,7-diazaspiro[3.5]nonan-1-yl)pyridin-3-yl)imidazo[1,2-b]pyridazine (3.41 mg, 3%).

The following compounds were prepared using a methodology similar to the one described in Example 21:
N-((1-(5-(6-(Difluoromethyl)imidazo[1,2-b]pyridazin-3-yl)pyridin-3-yl)piperidin-3-yl)methyl)methanesulfonamide II-87;
6-(Difluoromethyl)-3-(5-(2-(methylsulfonyl)-2,6-diazaspiro[3.5]nonan-6-yl)pyridin-3-yl)imidazo[1,2-b]pyridazine II-101;
1-(4-(5-(6-(Difluoromethyl)imidazo[12-b]pyridazin-3-yl)pyridin-3-yl)piperazin-1-yl)ethanone II-171.

Example 22: N-((1-(5-(6-(Difluoromethyl)imidazo[1,2-b]pyridazin-3-yl)-2-methylpyridin-3-yl)piperidin-3-yl)methyl)methanesulfonamide, II-49

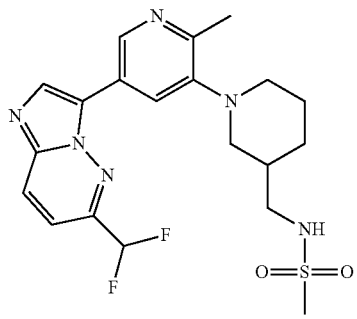 [SMILES: Cc1ncc(-c2cnc3ccc(C(F)F)nn23)cc1N1CCCC(CNS(C)(=O)=O)C1]

Step 1: 3-(5-Bromo-6-methylpyridin-3-yl)-6-(difluoromethyl)imidazo[1,2-b]pyridazine and 3-(5-bromo-2-methylpyridin-3-yl)-6-(difluoromethyl)imidazo[1,2-b]pyridazine A mixture of tributyl-[6-(difluoromethyl)imidazo[1,2-b]pyridazin-3-yl]stannane (104 mg, 0.227 mmol), 3,5-dibromo-2-methyl-pyridine (62.6 mg, 0.250 mmol) and PdCl₂(PPh₃)₂ (15.9 mg, 0.023 mmol) in DMF (1.5 mL) was degassed with nitrogen and then heated to 80° C. for 16 hours. The mixture was diluted with EtOAc and washed sequentially with saturated aqueous solutions of NH₄Cl, NaHCO₃ and brine. The organic extract was dried (MgSO₄) and concentrated in vacuo to give a mixture of 3-(5-bromo-6-methylpyridin-3-yl)-6-(difluoromethyl)imidazo[1,2-b]pyridazine and 3-(5-bromo-2-methylpyridin-3-yl)-6-(difluoromethyl)imidazo[1,2-b]pyridazine as a yellow solid that was used in next step without further purification.

Step 2: N-((1-(5-(6-(Difluoromethyl)imidazo[1,2-b]pyridazin-3-yl)-2-methylpyridin-3-yl)piperidin-3-yl)methyl)methanesulfonamide and N-((1-(5-(6-(difluoromethyl)imidazo[1,2-b]pyridazin-3-yl)-6-methylpyridin-3-yl)piperidin-3-yl)methyl)methanesulfonamide A mixture of 3-(5-bromo-6-methylpyridin-3-yl)-6-(difluoromethyl)imidazo[1,2-b]pyridazine and 3-(5-bromo-2-methylpyridin-3-yl)-6-(difluoromethyl)imidazo[1,2-b]pyridazine, N-(3-piperidylmethyl)methanesulfonamide (27.2 mg, 0.141 mmol), Pd₂(dba)₃ (3.4 mg, 0.006 mmol), Xantphos (6.8 mg, 0.012 mmol) and Cs₂CO₃ (76.8 mg, 0.236 mmol) in 1,4-dioxane (589 µL) was degassed with nitrogen. The suspension was then heated to 120° C. for 16 hours. The reaction mixture was purified by reverse phase chromatography (C18, MeCN/Water/0.05% TFA as eluent) affording 2 separable, regioisomeric products. The pure fractions were lyophilised to afford the N-((1-(5-(6-(difluoromethyl)imidazo[1,2-b]pyridazin-3-yl)-2-methylpyridin-3-yl)piperidin-3-yl)methyl)methanesulfonamide (4 mg, 3.8%) and N-((1-(5-(6-(difluoromethyl)imidazo[1,2-b]pyridazin-3-yl)-6-methylpyridin-3-yl)piperidin-3-yl)methyl)methanesulfonamide (2.3 mg, 2.0%).

The following compounds were prepared using a methodology similar to the one described in Example 22:
6-(Difluoromethyl)-3-(6-methyl-5-(7-(methylsulfonyl)-1,7-diazaspiro[3.5]nonan-1-yl)pyridin-3-yl)imidazo[1,2-b]pyridazine II-44;
N-((1-(2-(6-(Difluoromethyl)imidazo[1,2-b]pyridazin-3-yl)-5-methylpyridin-4-yl)piperidin-3-yl)methyl)methanesulfonamide II-53.

Example 23: 1-(4-(3-(6-(Difluoromethyl)imidazo[1,2-b]pyridazin-3-yl)phenyl)piperazin-1-yl)ethanone, II-150

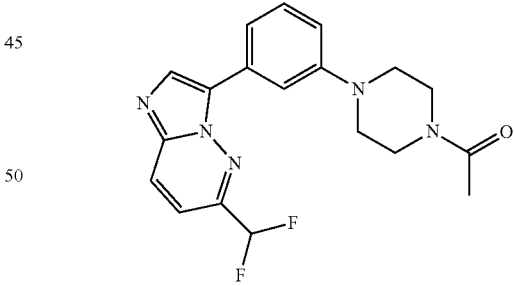

Step 1: 6-(Difluoromethyl)-3-(3-(piperazin-1-yl)phenyl)imidazo[1,2-b]pyridazine

A mixture of 6-(difluoromethyl)-3-iodo-imidazo[1,2-b]pyridazine (82 mg, 0.278 mmol), 1-(3-(4,4,5,5-tetramethyl-1,3,2-dioxaborolan-2-yl)phenyl)piperazine (80 mg, 0.278 mmol), Pd(PPh₃)₄ (16.1 mg, 0.014 mmol) and Na₂CO₃ (416.8 µL of 2 M, 0.834 mmol) in 1,4-dioxane (1.4 mL) was degassed with N₂ and then heated at 80° C. for 16 hours. The reaction mixture was partitioned between EtOAc and a saturated aqueous sodium bicarbonate. The organic layer was dried (MgSO$_4$) and concentrated in vacuo to afford 6-(difluoromethyl)-3-(3-piperazin-1-ylphenyl)imidazo[1,2-b]pyridazine as a yellow oil that was used in next step without further purification; MS m/z: 330.2 (M+H)$^+$.

Step 2: 1-(4-(3-(6-(Difluoromethyl)imidazo[1,2-b]pyridazin-3-yl)phenyl)piperazin-1-yl)ethanone Acetyl chloride (32.7 mg, 29.6 µL, 0.417 mmol) and DMAP (1.7 mg, 0.014 mmol) were added sequentially to a solution of 6-(difluoromethyl)-3-(3-piperazin-1-ylphenyl)imidazo[1,2-b]pyridazine (91.6 mg, 0.278 mmol) and Et$_3$N (112.5 mg, 155 µL, 1.112 mmol) in DCM (2 mL) and the mixture was stirred at ambient temperature for 1 hour. MeOH was added and the reaction mixture then concentrated in vacuo. The reaction mixture was purified by reverse phase chromatography (C18, MeCN/Water 0.05% TFA as eluent) to afford 1-(4-(3-(6-(difluoromethyl)imidazo[1,2-b]pyridazin-3-yl)phenyl)piperazin-1-yl)ethanone (20.3 mg, 13%).

The following compound was prepared using a methodology similar to the one described in Example 23:

6-Chloro-3-(2-phenylpyridin-4-yl)imidazo[1,2-b]pyridazine II-27.

Example 24: N-((1-(2-Cyano-5-(6-(difluoromethyl)imidazo[1,2-b]pyridazin-3-yl)phenyl)piperidin-3-yl)methyl)methanesulfonamide, II-82

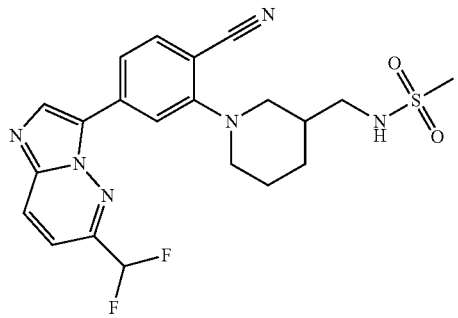 [SMILES: CS(=O)(=O)NCC1CCCN(c2cc(-c3cnc4ccc(C(F)F)nn34)ccc2C#N)C1]

N-(3-Piperidylmethyl)methanesulfonamide (150 mg, 0.78 mmol), 4-[6-(difluoromethyl)imidazo[1,2-b]pyridazin-3-yl]-2-fluoro-benzonitrile (75 mg, 0.26 mmol) and K$_2$CO$_3$ (71.9 mg, 0.52 mmol) were combined in DMF (5 mL) and heated at 90° C. for 16 hours. The solid was filtered off and the filtrate was purified by reverse phase chromatography (C18, MeCN/Water 0.05% TFA as eluent) to afford N-((1-(2-cyano-5-(6-(difluoromethyl)imidazo[1,2-b]pyridazin-3-yl)phenyl)piperidin-3-yl)methyl)methanesulfonamide (46 mg, 37%).

Example 25: N-((1-(2-Cyano-5-(6-(difluoromethyl)imidazo[1,2-b]pyridazin-3-yl)pyridin-3-yl)piperidin-3-yl)methyl)methanesulfonamide, II-117

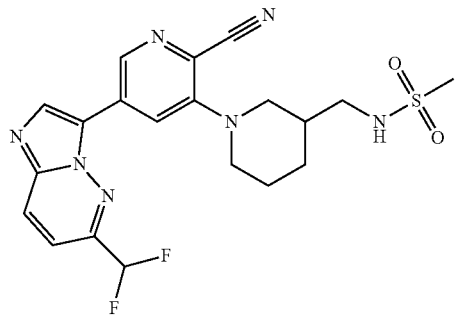 [SMILES: CS(=O)(=O)NCC1CCCN(c2cc(-c3cnc4ccc(C(F)F)nn34)cnc2C#N)C1]

5-[6-(Difluoromethyl)imidazo[1,2-b]pyridazin-3-yl]-3-fluoro-pyridine-2-carbonitrile (40 mg, 0.138 mmol), N-(3-piperidylmethyl)methanesulfonamide (53.2 mg, 0.277 mmol) and DIPEA (96.4 µL, 0.553 mmol) were heated in NMP (800 µL) at 120° C. for 4 hours. The reaction mixture was purified by reverse phase chromatography (C18, MeCN/Water 0.05% TFA as eluent) to afford N-((1-(2-cyano-5-(6-(difluoromethyl)imidazo[1,2-b]pyridazin-3-yl)pyridin-3-yl)piperidin-3-yl)methyl)methanesulfonamide (27.5 mg, 31%).

Example 26: N-((1-(2-(Aminomethyl)-5-(6-(difluoromethyl)imidazo[1,2-b]pyridazin-3-yl)pyridin-3-yl)piperidin-3-yl)methyl)methanesulfonamide, II-73

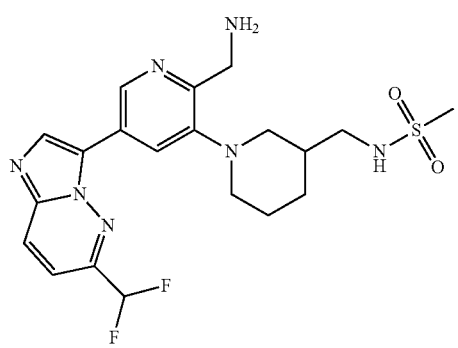 [SMILES: CS(=O)(=O)NCC1CCCN(c2cc(-c3cnc4ccc(C(F)F)nn34)cnc2CN)C1]

MeOH (0.8 mL) and HCl (114.2 µL of 12 M, 1.371 mmol) were added to N-[[1-[2-cyano-5-[6-(difluoromethyl)imidazo[1,2-b]pyridazin-3-yl]-3-pyridyl]-3-piperidyl]methyl]methanesulfonamide (40 mg, 0.087 mmol) and Pd(OH)$_2$ on carbon (12.2 mg, 0.087 mmol). The suspension was stirred under a positive pressure of hydrogen (balloon pressure) for 6 hours before the catalyst was filtered off. The filtrate was concentrated in vacuo and the residue was purified by reverse phase chromatography (C18, MeCN/Water 0.05% TFA as eluent) to afford N-((1-(2-(aminomethyl)-5-(6-(difluoromethyl)imidazo[1,2-b]pyridazin-3-yl)pyridin-3-yl)piperidin-3-yl)methyl)methanesulfonamide (15.2 mg, 24%).

Example 27: N-((1-(4-(6-(Difluoromethyl)imidazo[1,2-b]pyridazin-3-yl)-6-methoxypyridin-2-yl)piperidin-3-yl)methyl)methanesulfonamide, II-142 and N-((1-(4-(6-(difluoromethyl)imidazo[1,2-b]pyridazin-3-yl)-6-oxo-1,6-dihydropyridin-2-yl)piperidin-3-yl)methyl)methanesulfonamide, II-141

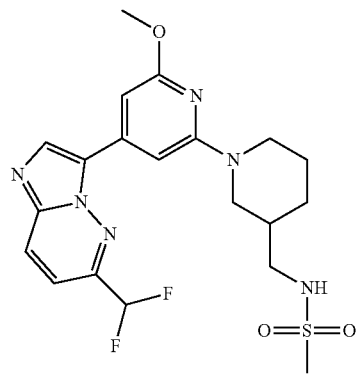

and

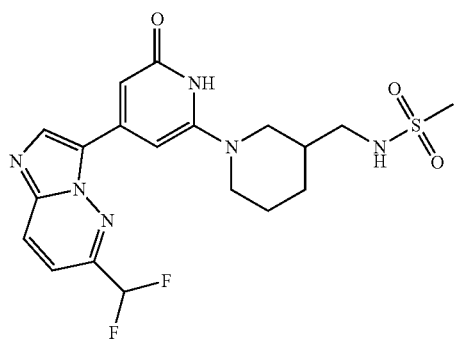

N-(3-Piperidylmethyl)methanesulfonamide (34.6 mg, 0.18 mmol), 3-(2-chloro-6-methoxy-4-pyridyl)-6-(difluoromethyl)imidazo[1,2-b]pyridazine (28.0 mg, 0.09 mmol and DIPEA (46.5 mg, 62.7 µL, 0.36 mmol) were heated in NMP (700 µL) to 190° C. for 16 hours. The mixture was purified by reverse phase chromatography (C18, MeCN/Water 0.05% TFA as eluent) to afford N-((1-(4-(6-(difluoromethyl)imidazo[1,2-b]pyridazin-3-yl)-6-methoxypyridin-2-yl)piperidin-3-yl)methyl)methanesulfonamide (16.5 mg, 28%) and N-((1-(4-(6-(difluoromethyl)imidazo[1,2-b]pyridazin-3-yl)-6-oxo-1,6-dihydropyridin-2-yl)piperidin-3-yl)methyl)methanesulfonamide (11.9 mg, 21%).

The following compounds were prepared using a methodology similar to the one described in Example 27:

(S)—N-((1-(4-(6-(Difluoromethyl)imidazo[1,2-b]pyridazin-3-yl)-6-oxo-1,6-dihydropyridin-2-yl)piperidin-3-yl)methyl)methanesulfonamide II-111;

(S)—N-((1-(4-(6-(Difluoromethyl)imidazo[1,2-b]pyridazin-3-yl)-6-methoxypyridin-2-yl)piperidin-3-yl)methyl)methanesulfonamide II-120.

Example 28: N-((1-(4-(6-(Difluoromethyl)imidazo[1,2-b]pyridazin-3-yl)pyridin-2-yl)-4,4-difluoropiperidin-3-yl)methyl)-N-hydroxymethanesulfonamide, II-131 and 2-(4,4-difluoro-3-(methylsulfonamidomethyl)piperidin-1-yl)-4-(6-(difluoromethyl)imidazo[1,2-b]pyridazin-3-yl)pyridine 1-oxide, II-132

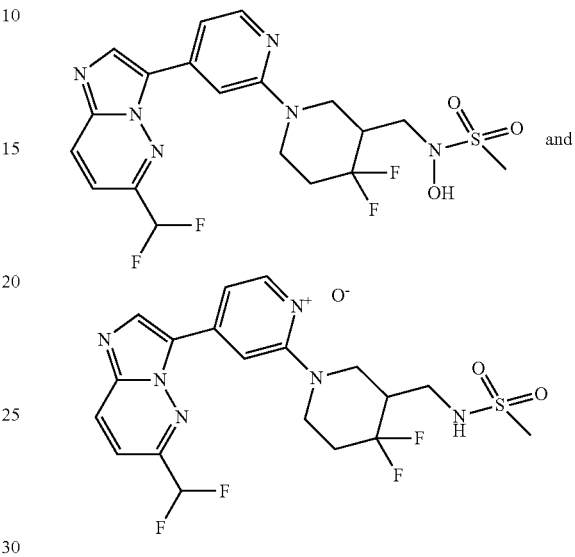

N-[[1-[4-[6-(Difluoromethyl)imidazo[1,2-b]pyridazin-3-yl]-2-pyridyl]-4,4-difluoro-3-piperidyl]methyl]methanesulfonamide (50 mg, 0.106 mmol) (II-153) and m-CPBA (20 mg, 0.106 mmol) were combined in DCM (15 mL) and stirred at ambient temperature for 2.5 hours. The solvent was removed in vacuo and the residue was purified by reverse phase chromatography (C18, MeCN/Water 0.05% TFA as eluent) to afford N-[[1-[4-[6-(difluoromethyl)imidazo[1,2-b]pyridazin-3-yl]-2-pyridyl]-4,4-difluoro-3-piperidyl]methyl]-N-hydroxy-methanesulfonamide (2.4 mg) and N-[[1-[4-[6-(difluoromethyl)imidazo[1,2-b]pyridazin-3-yl]-1-oxido-pyridin-1-ium-2-yl]-4,4-difluoro-3-piperidyl]methyl]methanesulfonamide (2.2 mg)

Example 29: N-((4-(4-(6-(Difluoromethyl)imidazo[1,2-b]pyridazin-3-yl)pyridin-2-yl)-1-methylpiperazin-2-yl)methyl)methanesulfonamide, II-98

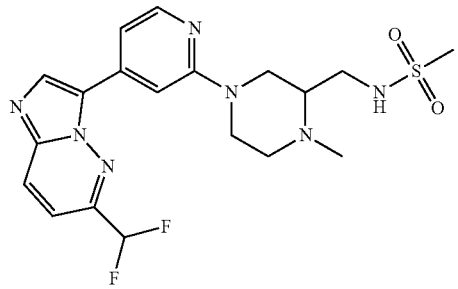 [SMILES: CN1CCN(c2cc(-c3cnc4ccc(C(F)F)nn34)ccn2)CC1CNS(C)(=O)=O]

To a solution of (4-(4-(6-(difluoromethyl)imidazo[1,2-b]pyridazin-3-yl)pyridin-2-yl)-1-methylpiperazin-2-yl)methanol (17 mg, 0.045 mmol, synthesised according to a procedure similar to Example 5), tert-butyl N-methylsulfonylcarbamate (16 mg, 0.082 mmol) and PPh₃ (37 mg, 0.141 mmol) in THF (1 mL) was added DEAD (15 µL, 0.095 mmol) dropwise and the reaction mixture stirred at ambient temperature under nitrogen for 18 hours. The solution was partitioned between DCM and saturated aqueous NaHCO₃. The organic layer was dried and concentrated in vacuo. The residue was taken up in DCM (1 mL) and TFA (1 mL) and stirred at ambient temperature for 3 hours before being concentrated in vacuo. The residue was purified by reverse phase chromatography (C18, MeCN/water/0.05% TFA as eluent) to give N-((4-(4-(6-(difluoromethyl)imidazo[1,2-b]pyridazin-3-yl)pyridin-2-yl)-1-methylpiperazin-2-yl)methyl)methanesulfonamide (10 mg, 49%).

Example 30: 2-(4-(4-(6-(Difluoromethyl)imidazo[1,2-b]pyridazin-3-yl)pyridin-2-yl)-1H-pyrazol-1-yl)ethanol, II-113

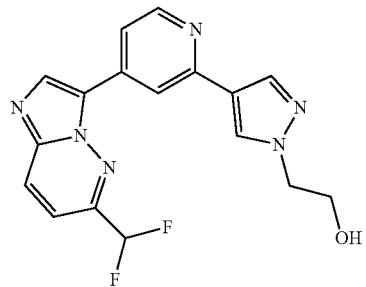 [SMILES: OCCn1cc(-c2cc(-c3cnc4ccc(C(F)F)nn34)ccn2)cn1]

(2-Chloro-4-pyridyl)boronic acid (64 mg, 0.407 mmol) was added to a solution of 6-(difluoromethyl)-3-iodo-imidazo[1,2-b]pyridazine (100 mg, 0.339 mmol), 1,1'-bis(diphenylphosphino)ferrocene palladium(II)chloride dichloromethane complex (27.7 mg, 0.034 mmol) and Na₂CO₃ (508.5 µL of 2 M, 1.017 mmol) in 1,4-dioxane (6 mL) and the mixture was heated at 70° C. for 16 hours. After cooling to ambient temperature, 2-[4-(4,4,5,5-tetramethyl-1,3,2-dioxaborolan-2-yl)pyrazol-1-yl]ethanol (40.4 mg, 0.169 mmol) was added to the mixture, followed by Pd(PPh₃)₄ (19.6 mg, 0.017 mmol). The mixture was heated in a microwave for 30 minutes at 140° C., then concentrated in vacuo and the residue purified by reverse phase chromatography (C18, MeCN/water/0.05% TFA as eluent) to give 2-(4-(4-(6-(difluoromethyl)imidazo[1,2-b]pyridazin-3-yl)pyridin-2-yl)-1H-pyrazol-1-yl)ethanol (4.5 mg, 3.7%).

Example 31: 1-(4-(4-(6-(Trifluoromethyl)imidazo[1,2-b]pyridazin-3-yl)pyridin-2-yl)piperazin-1-yl)ethanone, II-223

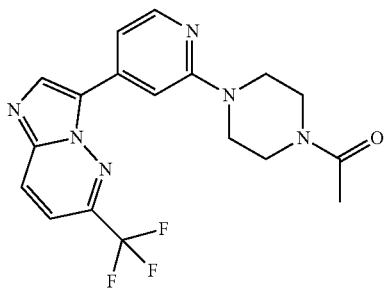 [SMILES: CC(=O)N1CCN(c2cc(-c3cnc4ccc(C(F)(F)F)nn34)ccn2)CC1]

Step 1: 1-(4-(4-(4,4,5,5-Tetramethyl-1,3,2-dioxaborolan-2-yl)pyridin-2-yl)piperazin-1-yl)ethanone Acetyl chloride (280 µL, 3.938 mmol) was added to a solution of 1-[4-(4,4,5,5-tetramethyl-1,3,2-dioxaborolan-2-yl)-2-pyridyl]piperazine (750 mg, 2.59 mmol) and Et₃N (900 µL, 6.46 mmol) in DCM (7.5 mL) and the reaction mixture allowed to stir at ambient temperature for 1 hour. The residue was purified directly by passing it through a 10 g Florisil cartridge, eluting with 0 to 50% EtOAc/petroleum ether. The pure fractions were combined and concentrated in vacuo to give 1-[4-[4-(4,4,5,5-tetramethyl-1,3,2-dioxaborolan-2-yl)-2-pyridyl]piperazin-1-yl]ethanone (693.3 mg, 81%) as an off-white solid; ¹H NMR (500 MHz, DMSO-d₆) δ 8.16 (dd, J=4.8, 0.9 Hz, 1H), 6.98 (s, 1H), 6.85 (dd, J=4.8, 0.7 Hz, 1H), 3.55-3.52 (m, 6H), 3.48-3.46 (m, 2H), 2.04 (s, 3H), 1.31 (s, 12H); MS m/z: 332.2 (M+H)⁺.

Step 2: 1-(4-(4-(6-(Trifluoromethyl)imidazo[1,2-b]pyridazin-3-yl)pyridin-2-yl)piperazin-1-yl)ethanone A mixture of 3-iodo-6-(trifluoromethyl)imidazo[1,2-b]pyridazine (45.4 mg, 0.145 mmol), 1-[4-[4-(4,4,5,5-tetramethyl-1,3,2-dioxaborolan-2-yl)-2-pyridyl]piperazin-1-yl]ethanone (40 mg, 0.121 mmol), Pd(PPh₃)₄ (7 mg, 0.006 mmol) and Na₂CO₃ (185 µL of 2 M) in 1,4-dioxane (1.2 mL) and H₂O (0.3 mL) was stirred at 80° C. for 18 hours. The reaction mixture was cooled to ambient temperature and the solvent removed under a stream of nitrogen. The residue was dissolved in DMSO and purified by reverse phase chromatography (C18, MeCN/water/0.05% TFA as eluent). The pure fractions were collected, passed through a sodium bicarbonate cartridge and freeze-dried to give 1-(4-(4-(6-(trifluoromethyl)imidazo[1,2-b]pyridazin-3-yl)pyridin-2-yl)piperazin-1-yl)ethanone (14.7 mg, 31%).

Example 32: N-((1-(4-(6-Methylimidazo[1,2-b]pyridazin-3-yl)pyridin-2-yl)piperidin-3-yl)methyl)methanesulfonamide, II-183

N-(3-Piperidylmethyl)methanesulfonamide (42.1 mg, 0.219 mmol), 3-(2-fluoro-4-pyridyl)-6-methyl-imidazo[1,2-b]pyridazine (25 mg, 0.109 mmol) and DIPEA (42.5 mg, 57.2 µL, 0.328 mmol) were combined in NMP (830 µL) and heated at 140° C. in a sealed tube for 16 hours. The crude mixture was purified by reverse phase chromatography (C18, MeCN/Water/0.05% TFA as eluent) to give N-((1-(4-(6-methylimidazo[1,2-b]pyridazin-3-yl)pyridin-2-yl)piperidin-3-yl)methyl)methanesulfonamide (15 mg, 17%).

The following compounds were prepared using a methodology similar to the one described in Example 32:

N-((1-(4-(6-(Methylamino)imidazo[1,2-b]pyridazin-3-yl)pyridin-2-yl)piperidin-3-yl)methyl)methanesulfonamide II-179;

N-((4-(4-(6-Chloroimidazo[1,2-b]pyridazin-3-yl)pyridin-2-yl)morpholin-2-yl)methyl)methanesulfonamide II-184;

1-(4-(4-(6-Methylimidazo[1,2-b]pyridazin-3-yl)pyridin-2-yl)piperazin-1-yl)ethanone II-193;

2-(4-(6-Chloroimidazo[1,2-b]pyridazin-3-yl)pyridin-2-yl)hexahydro-1H-pyrido[1,2-a]pyrazin-6(2H)-one II-207.

Example 33: 1-(4-(4-(6-(Hydroxymethyl)imidazo[1,2-b]pyridazin-3-yl)pyridin-2-yl)piperazin-1-yl)ethanone, II-185

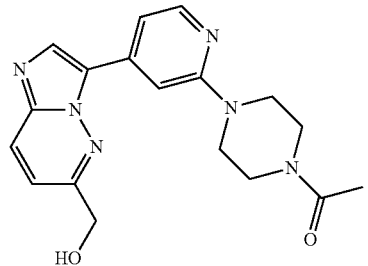 [SMILES: CC(=O)N1CCN(c2cc(-c3cnc4ccc(CO)nn34)ccn2)CC1]

Step 1: Ethyl imidazo[1,2-b]pyridazine-6-carboxylate

2-Bromo-1,1-diethoxy-ethane (16.55 g, 12.63 mL, 84 mmol) was dissolved in hydrogen bromide (3.52 mL of 48% w/v, 20.88 mmol) and stirred at 120° C. for 30 minutes. The reaction mixture was allowed to cool to ambient temperature and EtOH (100 mL) was added, followed by NaHCO$_3$ (3.196 g, 38.04 mmol) and ethyl 6-aminopyridazine-3-carboxylate (2 g, 12 mmol). The resulting mixture was stirred at 80° C. for 1.5 hours. The dark brown reaction mixture was allowed to cool to ambient temperature and concentrated under reduced pressure to give a dark brown gum. This material was partitioned between EtOAc and water, the aqueous layer was extracted with further EtOAc (3×20 mL) and the combined organic layers were dried (Na$_2$SO$_4$), filtered and concentrated under reduced pressure to give a brown oil which was purified by column chromatography (silica, 3% MeOH in EtOAc) to give a brown solid. This material was recrystallised from EtOAc/hexane mixtures to give ethyl imidazo[1,2-b]pyridazine-6-carboxylate as a light brown powder (1.1 g, 48%); $^1$H NMR (400 MHz, DMSO-d$_6$) δ 8.52 (s, 1H), 8.28 (d, J=9.5 Hz, 1H), 7.98 (d, J=1.2 Hz, 1H), 7.73 (d, J=9.5 Hz, 1H), 4.43 (q, J=7.1 Hz, 2H), 1.37 (t, J=7.1 Hz, 3H).

Step 2: Ethyl 3-iodoimidazo[1,2-b]pyridazine-6-carboxylate

Ethyl imidazo[1,2-b]pyridazine-6-carboxylate (500 mg, 2.615 mmol) was dissolved in 1 M iodine monochloride (9.153 mL of 1 M, 9.153 mmol) in a pressure tube and cooled in an ice bath. Pyridine (2.5 mL) was added slowly dropwise, and immediately after the end of the addition, a dark yellow solid began to precipitate out of the reaction mixture. This mixture was stirred at 50° C. for 48 hours then allowed to cool to ambient temperature, diluted with DCM and washed with saturated Na$_2$S$_2$O$_3$. The aqueous layer was extracted with further DCM (3×20 mL) and the combined organic layers were dried (Na$_2$SO$_4$), filtered and concentrated under reduced pressure to give a bright yellow solid. This material was triturated with ether and the suspended solid collected by filtration and washed with pentane (3×2 mL) to give ethyl 3-iodoimidazo[1,2-b]pyridazine-6-carboxylate as a bright yellow powder (689.8 mg, 83%); $^1$H NMR (400 MHz, DMSO-d$_6$) δ 8.27 (d, J=9.4 Hz, 1H), 8.10 (s, 1H), 7.76 (d, J=9.4 Hz, 1H), 4.46 (q, J=7.1 Hz, 2H), 1.39 (t, J=7.1 Hz, 3H).

Step 3: 3-(2-(4-Acetylpiperazin-1-yl)pyridin-4-yl)imidazo[1,2-b]pyridazine-6-carboxylic Acid A mixture of ethyl 3-iodoimidazo[1,2-b]pyridazine-6-carboxylate (114.9 mg, 0.362 mmol), 1-[4-[4-(4,4,5,5-tetramethyl-1,3,2-dioxaborolan-2-yl)-2-pyridyl]piperazin-1-yl]ethanone (100 mg, 0.302 mmol, see Example 31, Step 1), Pd(PPh$_3$)$_4$ (18 mg, 0.016 mmol) and Na$_2$CO$_3$ (454.8 µL of 2 M, 0.910 mmol) in 1,4-dioxane (1.5 mL) and H$_2$O (500 µL) was stirred at 80° C. for 22 hours. The reaction mixture was cooled to ambient temperature and the solvent removed under a stream of nitrogen. The residue was dissolved in DMSO and TFA and purified by reverse phase chromatography (C18, MeCN/Water/0.05% TFA as eluent). The pure fractions were collected and lyophilised to give 3-[2-(4-acetylpiperazin-1-yl)-4-pyridyl]imidazo[1,2-b]pyridazine-6-carboxylic acid as a yellow solid (72.9 mg, 49%).

Step 4: 1-(4-(4-(6-(Hydroxymethyl)imidazo[1,2-b]pyridazin-3-yl)pyridin-2-yl)piperazin-1-yl)ethanone, II-185

Et$_3$N (50 µL, 0.359 mmol) was added to a suspension of 3-[2-(4-acetylpiperazin-1-yl)-4-pyridyl]imidazo[1,2-b]pyridazine-6-carboxylic acid (TFA salt) (68 mg, 0.137 mmol) in THF (5 mL) and the mixture was cooled to −20° C. Isobutyl chloroformate (27 µL, 0.208 mmol) was added and the reaction was stirred at this temperature for 30 minutes. Sodium borohydride (8 mg, 0.211 mmol) was added followed by methanol (2 mL) and the reaction mixture stirred at −20° C. for a further 30 minutes. The reaction was quenched by the addition of saturated aqueous NaHCO$_3$ and allowed to warm to ambient temperature. Water was added to dissolve the solids and the mixture was extracted with EtOAc (×3). The combined organic extracts were washed with brine, dried (MgSO$_4$), filtered and concentrated in vacuo. The material was purified by reverse phase chromatography (C18, MeCN/Water/0.05% TFA as eluent) to give 1-(4-(4-(6-(hydroxymethyl)imidazo[1,2-b]pyridazin-3-yl)pyridin-2-yl)piperazin-1-yl)ethanone as a white solid (22.8 mg, 35%).

The following compounds were prepared using a methodology similar to Step 3 described in Example 33:

1-(4-(6-Chloroimidazo[1,2-b]pyridazin-3-yl)pyridin-2-yl)-1,4-diazepan-5-one II-187;

(S)-1-(4-(6-Chloroimidazo[1,2-b]pyridazin-3-yl)pyridin-2-yl)piperidine-3-carboxamide II-189;

4-(4-(6-Chloroimidazo[1,2-b]pyridazin-3-yl)pyridin-2-yl)morpholine II-194;

6-Chloro-3-(2-(4-methylpiperazin-1-yl)pyridin-4-yl)imidazo[1,2-b]pyridazine II-195;

1-(4-(4-(6-Chloroimidazo[1,2-b]pyridazin-3-yl)pyridin-2-yl)piperazin-1-yl)ethanone II-208;

6-Chloro-3-(2-(piperazin-1-yl)pyridin-4-yl)imidazo[1,2-b]pyridazine II-220.

Example 34: N-(((2S,5R)-4-(6-(6-(Difluoromethyl)
imidazo[1,2-b]pyridazin-3-yl)pyrimidin-4-yl)-5-
methylmorpholin-2-yl)methyl)methanesulfonamide,
II-197 and N-(((2R,5S)-4-(6-(6-(difluoromethyl)
imidazo[1,2-b]pyridazin-3-yl)pyrimidin-4-yl)-5-
methylmorpholin-2-yl)methyl)methanesulfonamide,
II-234

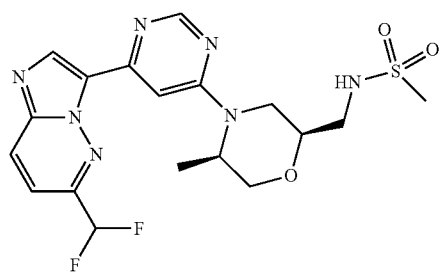

II-197

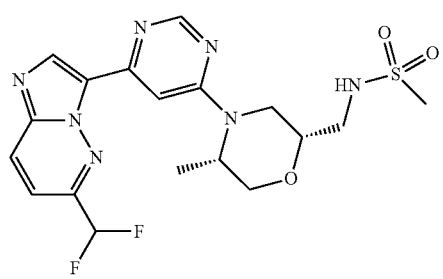

II-234

Step 1: (4-(6-(6-(Difluoromethyl)imidazo[1,2-b]
pyridazin-3-yl)pyrimidin-4-yl)-5-methylmorpholin-
2-yl)methyl methanesulfonate Under an atmosphere of $N_2$, $Et_3N$ (200 μL, 1.43 mmol) and methanesulfonyl chloride (80 μL, 1.03 mmol) were sequentially added to an ice-cold solution of [4-[6-[6-(difluoromethyl)imidazo[1,2-b]pyridazin-3-yl]pyrimidin-4-yl]-5-methyl-morpholin-2-yl]methanol (300 mg, 0.79 mmol, prepared according to a methodology similar to the one described in Example 1) in DCM (5 mL). The mixture was stirred for 5 minutes at 0° C. before the ice bath was removed and the suspension stirred at ambient temperature. After 18 hours, DMF (2 mL) was added followed by $Et_3N$ (200 μL, 1.43 mmol) and methanesulfonyl chloride (80 μL, 1.03 mmol) and the mixture was stirred at ambient temperature for 24 hours. The reaction mixture was partitioned between DCM and a saturated aqueous solution of $NaHCO_3$. The combined organics were dried ($MgSO_4$), filtered and concentrated in vacuo and taken directly on to the next step.

Step 2: N-((4-(6-(6-(Difluoromethyl)imidazo[1,2-b]
pyridazin-3-yl)pyrimidin-4-yl)-5-methylmorpholin-
2-yl)methyl)methanesulfonamide To the crude material prepared in Step 1 was added DMF (5 mL), methanesulfonamide (300 mg, 3.15 mmol) and solid $K_2CO_3$ (500 mg, 3.62 mmol) and the reaction mixture was stirred at 80° C. for 3 days under $N_2$. The crude mixture was first purified by reverse phase chromatography (C18, MeCN/Water/0.05% TFA as eluent) before the stereoisomers were separated by chiral SFC to afford N-(((2S,5R)-4-(6-(6-(difluoromethyl)imidazo[1,2-b]pyridazin-3-yl)pyrimidin-4-yl)-5-methylmorpholin-2-yl)methyl)methanesulfonamide II-197 (33 mg, 9.1%) and N-(((2R,5S)-4-(6-(6-(difluoromethyl)imidazo[1,2-b]pyridazin-3-yl)pyrimidin-4-yl)-5-methylmorpholin-2-yl)methyl)methanesulfonamide II-234 (27 mg, 7.4%).

The following compounds were prepared using a methodology similar to the one described in Example 34:

N-((4-(6-(6-(Difluoromethyl)imidazo[1,2-b]pyridazin-3-yl)
pyrimidin-4-yl)-3-methylmorpholin-2-yl)methyl)methanesulfonamide II-345;

N-((4-(6-(6-(Difluoromethyl)imidazo[1,2-b]pyridazin-3-yl)
pyrimidin-4-yl)-3-methylmorpholin-2-yl)methyl)methanesulfonamide II-346;

N-((7-(6-(6-(Difluoromethyl)imidazo[1,2-b]pyridazin-3-yl)
pyrimidin-4-yl)-4-oxa-7-azaspiro[2.5]octan-5-yl)methyl)
methanesulfonamide II-375;

N-((7-(6-(6-(Difluoromethyl)imidazo[1,2-b]pyridazin-3-yl)
pyrimidin-4-yl)-4-oxa-7-azaspiro[2.5]octan-5-yl)methyl)
methanesulfonamide II-383;

N-((7-(6-(6-(Difluoromethyl)imidazo[1,2-b]pyridazin-3-yl)
pyrimidin-4-yl)-4-oxa-7-azaspiro[2.5]octan-5-yl)methyl)
methanesulfonamide II-384;

(S)-(((4-(6-(6-(Difluoromethyl)imidazo[1,2-b]pyridazin-3-
yl)pyrimidin-4-yl)-1-methylpiperazin-2-yl)methyl)
imino)dimethyl-$\lambda^6$-sulfanone II-410;

N-((6-Cyclopropyl-4-(6-(6-(difluoromethyl)imidazo[1,2-b]
pyridazin-3-yl)pyrimidin-4-yl)morpholin-2-yl)methyl)
methanesulfonamide II-440;

N-((6-Cyclopropyl-4-(6-(6-(difluoromethyl)imidazo[1,2-b]
pyridazin-3-yl)pyrimidin-4-yl)morpholin-2-yl)methyl)
methanesulfonamide II-441;

N-((6-Cyclopropyl-4-(6-(6-(difluoromethyl)imidazo[1,2-b]
pyridazin-3-yl)pyrimidin-4-yl)morpholin-2-yl)methyl)
methanesulfonamide II-443;

N-((6-Cyclopropyl-4-(6-(6-(difluoromethyl)imidazo[1,2-b]
pyridazin-3-yl)pyrimidin-4-yl)morpholin-2-yl)methyl)
methanesulfonamide II-444;

N-((3-(6-(6-(Difluoromethyl)imidazo[1,2-b]pyridazin-3-yl)
pyrimidin-4-yl)-3-azabicyclo[3.1.0]hexan-1-yl)methyl)
methanesulfonamide II-447;

N-[[4-[6-[6-(Difluoromethyl)imidazo[1,2-b]pyridazin-3-yl]
pyrimidin-4-yl]-3,6,6-trimethyl-morpholin-2-yl]methyl]
methanesulfonamide II-458;

N-((1-(6-(6-(Difluoromethyl)imidazo[1,2-b]pyridazin-3-yl)
pyrimidin-4-yl)-5-(2-methoxyethoxy)piperidin-3-yl)
methyl)methanesulfonamide II-549;

N-((1-(6-(6-(Difluoromethyl)imidazo[1,2-b]pyridazin-3-yl)
pyrimidin-4-yl)-5-(2-methoxyethoxy)piperidin-3-yl)
methyl)methanesulfonamide II-550;

N-((1-(tert-Butyl)-4-(6-(6-(difluoromethyl)imidazo[1,2-b]
pyridazin-3-yl)pyrimidin-4-yl)-3-methylpiperazin-2-yl)
methyl)methanesulfonamide II-559.

Example 35: N-((4-(6-(6-(Difluoromethyl)imidazo[1,2-b]pyridazin-3-yl)pyrimidin-4-yl)-1,3-dimethylpiperazin-2-yl)methyl)methanesulfonamide, II-312 (Mixture of Stereoisomers), N-((4-(6-(6-(difluoromethyl)imidazo[1,2-b]pyridazin-3-yl)-1,3-dimethylpiperazin-2-yl)methyl)methanesulfonamide, II-363 (Single Stereoisomer) and N-((4-(6-(6-(difluoromethyl)imidazo[1,2-b]pyridazin-3-yl)pyrimidin-4-yl)-1,3-dimethylpiperazin-2-yl)methyl)methanesulfonamide, II-364 (Single Stereoisomer)

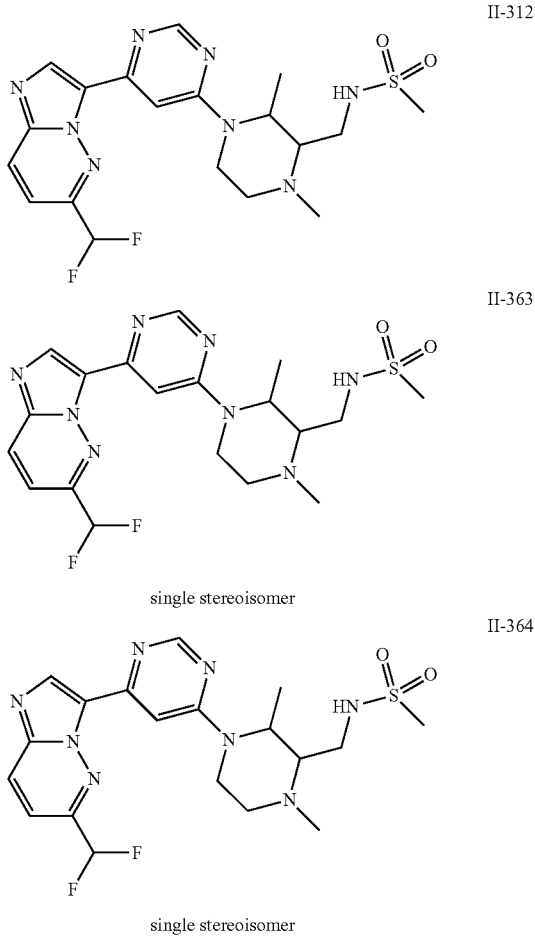

single stereoisomer single stereoisomer

A mixture of N-[[4-[6-[6-(difluoromethyl)imidazo[1,2-b]pyridazin-3-yl]pyrimidin-4-yl]-3-methyl-piperazin-2-yl]methyl]methanesulfonamide (500 mg, 1 mmol, prepared according to a methodology similar to the one described in Example 1), formic acid (2 mL of 50% w/w, 24.3 mmol) and formaldehyde (2 mL of 37% w/v, 24.65 mmol) in MeOH (2 mL) in a sealed vessel was stirred at 100° C. After 12 hours, the mixture was concentrated in vacuo and the residue was purified by reverse phase chromatography (C18, MeCN/Water/0.05% TFA as eluent). The clean fractions were freeze dried affording N-((4-(6-(6-(difluoromethyl)imidazo[1,2-b]pyridazin-3-yl)pyrimidin-4-yl)-1,3-dimethylpiperazin-2-yl)methyl)methanesulfonamide II-312.

The stereoisomers were separated by chiral SFC to afford N-((4-(6-(6-(difluoromethyl)imidazo[1,2-b]pyridazin-3-yl)pyrimidin-4-yl)-1,3-dimethylpiperazin-2-yl)methyl)methanesulfonamide II-363 (58.9 mg, 69%) and N-((4-(6-(6-(difluoromethyl)imidazo[1,2-b]pyridazin-3-yl)pyrimidin-4-yl)-1,3-dimethylpiperazin-2-yl)methyl)methanesulfonamide II-364 (63.3 mg, 74%).

The following compounds were prepared using a methodology similar to the one described in Example 35:

N-((4-(6-(6-(Difluoromethyl)imidazo[1,2-b]pyridazin-3-yl)pyrimidin-4-yl)-1-ethyl-3-methylpiperazin-2-yl)methyl)methanesulfonamide II-340;

N-((4-(6-(6-(Difluoromethyl)imidazo[1,2-b]pyridazin-3-yl)pyrimidin-4-yl)-1,6-dimethylpiperazin-2-yl)methyl)methanesulfonamide II-418;

N-((4-(6-(6-(Difluoromethyl)imidazo[1,2-b]pyridazin-3-yl)pyrimidin-4-yl)-1,5-dimethylpiperazin-2-yl)methyl)methanesulfonamide II-423;

N-((4-(6-(6-(Difluoromethyl)imidazo[1,2-b]pyridazin-3-yl)pyrimidin-4-yl)-1,3,6-trimethylpiperazin-2-yl)methyl)methanesulfonamide II-448;

(S)-1-(4-(6-(6-(Difluoromethyl)imidazo[1,2-b]pyridazin-3-yl)pyrimidin-4-yl)-1-methylpiperazin-2-yl)cyclopropan-1-ol II-459;

N-((1-Cyclopropyl-4-(6-(6-(difluoromethyl)imidazo[1,2-b]pyridazin-3-yl)pyrimidin-4-yl)-3-methylpiperazin-2-yl)methyl)methanesulfonamide II-463;

N-(1-(4-(6-(6-(Difluoromethyl)imidazo[1,2-b]pyridazin-3-yl)pyrimidin-4-yl)-1-methylpiperazin-2-yl)ethyl)methanesulfonamide II-473;

N-(1-(4-(6-(6-(Difluoromethyl)imidazo[1,2-b]pyridazin-3-yl)pyrimidin-4-yl)-1-methylpiperazin-2-yl)ethyl)methanesulfonamide II-474;

N-((1-Cyclopropyl-4-(6-(6-(difluoromethyl)imidazo[1,2-b]pyridazin-3-yl)pyrimidin-4-yl)-3-methylpiperazin-2-yl)methyl)methanesulfonamide II-478 (single stereoisomer, separated by chiral SFC);

N-((1-Cyclopropyl-4-(6-(6-(difluoromethyl)imidazo[1,2-b]pyridazin-3-yl)pyrimidin-4-yl)-3-methylpiperazin-2-yl)methyl)methanesulfonamide II-479 (single stereoisomer, separated by chiral SFC);

2-(4-(6-(6-(Difluoromethyl)imidazo[1,2-b]pyridazin-3-yl)pyrimidin-4-yl)-1-methylpiperazin-2-yl)acetamide II-492;

2-(4-(6-(6-(Difluoromethyl)imidazo[1,2-b]pyridazin-3-yl)pyrimidin-4-yl)-1-methylpiperazin-2-yl)ethan-1-ol II-514;

2-(4-(6-(6-(Difluoromethyl)imidazo[1,2-b]pyridazin-3-yl)pyrimidin-4-yl)-1,3-dimethylpiperazin-2-yl)ethan-1-ol II-536.

Example 36: 2-(6-(6-(Difluoromethyl)imidazo[1,2-b]pyridazin-3-yl)pyrimidin-4-yl)-2,6-diazaspiro[3.5]nonane-6-sulfonamide, II-284

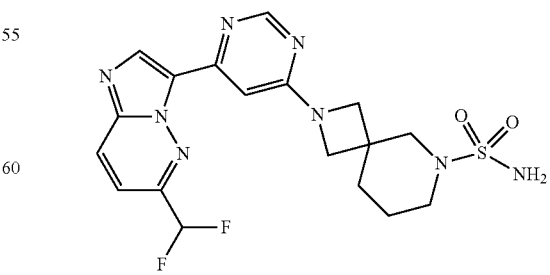

A mixture of 3-(6-(2,6-diazaspiro[3.5]nonan-2-yl)pyrimidin-4-yl)-6-(difluoromethyl)imidazo[1,2-b]pyridazine (50 mg, 0.13 mmol, prepared according to a procedure similar to the one described in Example 59) and sulfamide (129 mg, 1.34 mmol) in 1,4-dioxane (2 mL) was heated in an Anton-Paar microwave at 120° C. for 30 minutes. The reaction mixture was concentrated in vacuo and the residue purified by reverse phase chromatography (C18, MeCN/Water/0.05% TFA as eluent) to afford 2-(6-(6-(difluoromethyl)imidazo[1,2-b]pyridazin-3-yl)pyrimidin-4-yl)-2,6-diazaspiro[3.5]nonane-6-sulfonamide II-284 (4 mg, 6.6%).

The following compounds were prepared using a methodology similar to the one described in Example 36:

2-(6-(6-(Difluoromethyl)imidazo[1,2-b]pyridazin-3-yl)pyrimidin-4-yl)-5-oxa-2,8-diazaspiro[3.5]nonane-8-sulfonamide II-285;

1-(6-(6-(Difluoromethyl)imidazo[1,2-b]pyridazin-3-yl)pyrimidin-4-yl)hexahydropyrrolo[3,4-b]pyrrole-5(1H)-sulfonamide II-286;

1-((1-(6-(6-(Difluoromethyl)imidazo[1,2-b]pyridazin-3-yl)pyrimidin-4-yl)piperidin-3-yl)methyl)-1-methylsulfuric diamide II-311;

4-(6-(6-(Difluoromethyl)imidazo[1,2-b]pyridazin-3-yl)pyrimidin-4-yl)hexahydropyrrolo[3,4-b][1,4]oxazine-6(2H)-sulfonamide II-332;

6-(6-(6-(Difluoromethyl)imidazo[1,2-b]pyridazin-3-yl)pyrimidin-4-yl)-2,6-diazaspiro[3.5]nonane-2-sulfonamide II-333;

8-(6-(6-(Difluoromethyl)imidazo[1,2-b]pyridazin-3-yl)pyrimidin-4-yl)-5-oxa-2,8-diazaspiro[3.5]nonane-2-sulfonamide II-334;

1-(6-(6-(Difluoromethyl)imidazo[1,2-b]pyridazin-3-yl)pyrimidin-4-yl)octahydro-6H-pyrrolo[3,4-b]pyridine-6-sulfonamide II-335;

1-(6-(6-(Difluoromethyl)imidazo[1,2-b]pyridazin-3-yl)pyrimidin-4-yl)octahydro-6H-pyrrolo[2,3-c]pyridine-6-sulfonamide II-344;

N-((4-(6-(6-(Difluoromethyl)imidazo[1,2-b]pyridazin-3-yl)pyrimidin-4-yl)morpholin-2-yl)methyl)sulfuric diamide II-347;

6-(Difluoromethyl)-3-[6-[2-methyl-3-[(sulfamoylamino)methyl]-1-piperidyl]pyrimidin-4-yl]imidazo[1,2-b]pyridazine II-387.

Example 37: 3-((1-(6-(6-(Difluoromethyl)imidazo[1,2-b]pyridazin-3-yl)pyrimidin-4-yl)piperidin-3-yl)methyl)-1,1-dimethylsulfuric Diamide, II-348

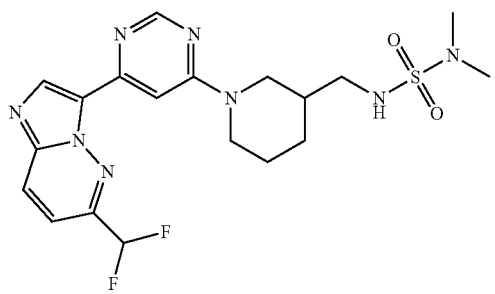 [SMILES: CN(C)S(=O)(=O)NCC1CCCN(c2cc(-c3cnc4ccc(C(F)F)nn34)ncn2)C1]

[1-[6-[6-(Difluoromethyl)imidazo[1,2-b]pyridazin-3-yl]pyrimidin-4-yl]-3-piperidyl]methanamine (7.5 mg, 0.02 mmol, prepared according to a procedure similar to Example 59) and DIPEA (8.1 mg, 11 µL, 0.062 mmol) were combined in NMP (1 mL) and N,N-dimethylsulfamoyl chloride (3 mg, 2.24 µL, 0.021 mmol) was added. The mixture was left to stand overnight at ambient temperature, then purified by reverse phase chromatography (C18, MeCN/water-0.1% ammonium hydroxide as eluent) to give 3-((1-(6-(6-(difluoromethyl)imidazo[1,2-b]pyridazin-3-yl)pyrimidin-4-yl)piperidin-3-yl)methyl)-1,1-dimethylsulfuric diamide II-348 as a white solid (3.67 mg, 37%).

The following compounds were prepared using a methodology similar to the one described in Example 37:

3-((4-(6-(6-(Difluoromethyl)imidazo[1,2-b]pyridazin-3-yl)pyrimidin-4-yl)morpholin-2-yl)methyl)-1,1-dimethyl sulfuric diamide II-349;

1-((1-(6-(6-(Difluoromethyl)imidazo[1,2-b]pyridazin-3-yl)pyrimidin-4-yl)piperidin-3-yl)methyl)-3-methylsulfuric diamide II-385;

1-((4-(6-(6-(Difluoromethyl)imidazo[1,2-b]pyridazin-3-yl)pyrimidin-4-yl)morpholin-2-yl)methyl)-3-methylsulfuric diamide II-386;

1-((1-(6-(6-(Difluoromethyl)imidazo[1,2-b]pyridazin-3-yl)pyrimidin-4-yl)pyrrolidin-3-yl)methyl)sulfuric diamide II-415.

Example 38: N-[1-[6-[6-(Difluoromethyl)imidazo[1,2-b]pyridazin-3-yl]pyrimidin-4-yl]-2-methyl-3-piperidyl]methanesulfonamide, II-377 and II-374

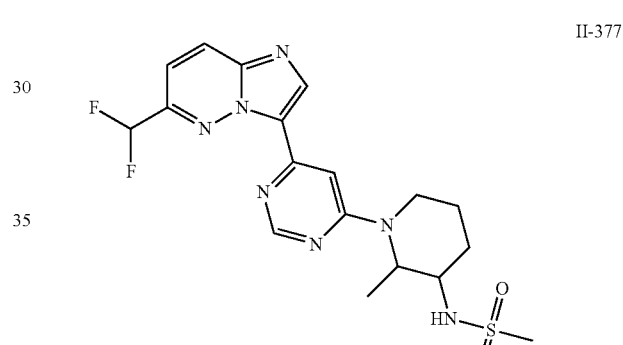

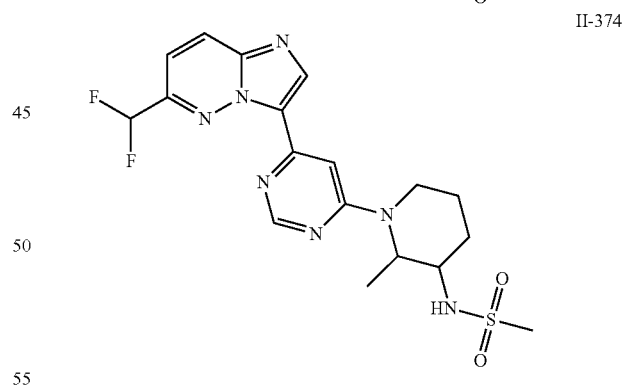

To a solution of 1-(6-(6-(difluoromethyl)imidazo[1,2-b]pyridazin-3-yl)pyrimidin-4-yl)-2-methylpiperidin-3-amine (prepared according to a procedure similar to Example 59) in DCM (2 mL) was added Et₃N (108 mg, 150 µL, 1.06 mmol) then methanesulfonyl chloride (57 mg, 39 µL, 0.50 mmol). The mixture was stirred at ambient temperature for 1 hour, then concentrated in vacuo. The residue was purified by reverse phase chromatography (C18, MeCN/Water/0.05% TFA as eluent) to give N-[1-[6-[6-(difluoromethyl)imidazo[1,2-b]pyridazin-3-yl]pyrimidin-4-yl]-2-methyl-3-piperidyl]methanesulfonamide II-377 and N-[1-[6-[6-

(difluoromethyl)imidazo[1,2-b]pyridazin-3-yl]pyrimidin-4-yl]-2-methyl-3-piperidyl]methanesulfonamide II-374.

The following compounds were prepared using a methodology similar to the one described in Example 38:

2-(6-(6-(Difluoromethyl)imidazo[1,2-b]pyridazin-3-yl)pyrimidin-4-yl)-8-(methylsulfonyl)-2,8-diazaspiro[4.5]decane II-54;

7-(6-(6-(Difluoromethyl)imidazo[1,2-b]pyridazin-3-yl)pyrimidin-4-yl)-2-(methylsulfonyl)-2,7-diazaspiro[4.5]decane II-56;

6-(Difluoromethyl)-3-(6-(1-(methylsulfonyl)-1,6-diazaspiro[3.5]nonan-6-yl)pyrimidin-4-yl)imidazo[1,2-b]pyridazine II-70;

6-(Difluoromethyl)-3-(6-(8-(methylsulfonyl)-3,8-diazabicyclo[4.2.0]octan-3-yl)pyrimidin-4-yl)imidazo[1,2-b]pyridazine II-181;

(1-(6-(6-(Difluoromethyl)imidazo[1,2-b]pyridazin-3-yl)pyrimidin-4-yl)piperidin-3-yl)(4-(methylsulfonyl)piperazin-1-yl)methanone II-206;

N-(((3R,4R)-1-(6-(6-(Difluoromethyl)imidazo[1,2-b]pyridazin-3-yl)pyrimidin-4-yl)-4-methylpyrrolidin-3-yl)methyl)methanesulfonamide II-237;

N-((1-(6-(6-(Difluoromethyl)imidazo[1,2-b]pyridazin-3-yl)pyrimidin-4-yl)-4-methylpyrrolidin-3-yl)methyl)methanesulfonamide II-238;

N-((1-(6-(6-(Difluoromethyl)imidazo[1,2-b]pyridazin-3-yl)pyrimidin-4-yl)piperidin-3-yl)methyl)cyclopropanesulfonamide II-262;

8-(6-(6-(Difluoromethyl)imidazo[1,2-b]pyridazin-3-yl)pyrimidin-4-yl)-2-(methylsulfonyl)-5-oxa-2,8-diazaspiro[3.5]nonane II-273;

4-(6-(6-(Difluoromethyl)imidazo[1,2-b]pyridazin-3-yl)pyrimidin-4-yl)-9-(methylsulfonyl)-1-oxa-4,9-diazaspiro[5.5]undecane II-287;

4-(6-(6-(Difluoromethyl)imidazo[1,2-b]pyridazin-3-yl)pyrimidin-4-yl)-8-(methylsulfonyl)-1-oxa-4,8-diazaspiro[5.5]undecane II-288;

N-((1-(6-(6-(Difluoromethyl)imidazo[1,2-b]pyridazin-3-yl)pyrimidin-4-yl)piperidin-3-yl)methyl)oxetane-3-sulfonamide II-289;

(1-(6-(6-(Difluoromethyl)imidazo[1,2-b]pyridazin-3-yl)pyrimidin-4-yl)pyrrolidin-3-yl)methanamine II-409 (Using only Step 1 of Example 38);

N-(1-(6-(6-(Difluoromethyl)imidazo[1,2-b]pyridazin-3-yl)pyrimidin-4-yl)-3-methylpiperidin-3-yl)methanesulfonamide II-412;

(S)—N-(1-(6-(6-(Difluoromethyl)imidazo[1,2-b]pyridazin-3-yl)pyrimidin-4-yl)piperidin-3-yl)oxetane-3-sulfonamide II-419;

(S)-1-Cyclopropyl-N-(1-(6-(6-(difluoromethyl)imidazo[1,2-b]pyridazin-3-yl)pyrimidin-4-yl)piperidin-3-yl)methanesulfonamide II-420;

(S)—N-(1-(6-(6-(Difluoromethyl)imidazo[1,2-b]pyridazin-3-yl)pyrimidin-4-yl)piperidin-3-yl)ethanesulfonamide II-421;

(S)-1-(1-(6-(6-(Difluoromethyl)imidazo[1,2-b]pyridazin-3-yl)pyrimidin-4-yl)piperidin-3-yl)-3-methylsulfuric diamide II-422;

N-(1-(1-(6-(6-(Difluoromethyl)imidazo[1,2-b]pyridazin-3-yl)pyrimidin-4-yl)pyrrolidin-3-yl)cyclopropyl)methanesulfonamide II-439;

(S)—N-(1-(6-(6-(Difluoromethyl)imidazo[1,2-b]pyridazin-3-yl)pyrimidin-4-yl)piperidin-3-yl)cyclopropanesulfonamide II-442;

N-(1-(6-(6-(Difluoromethyl)imidazo[1,2-b]pyridazin-3-yl)pyrimidin-4-yl)-3-methylpiperidin-3-yl)methanesulfonamide II-445;

N-(1-(6-(6-(Difluoromethyl)imidazo[1,2-b]pyridazin-3-yl)pyrimidin-4-yl)-3-methylpiperidin-3-yl)methanesulfonamide II-446;

8-(6-(6-(Difluoromethyl)imidazo[1,2-b]pyridazin-3-yl)pyrimidin-4-yl)-5-methyl-2,5,8-triazaspiro[3.5]nonane-2-sulfonamide II-535;

N-(1-(6-(6-(Difluoromethyl)imidazo[1,2-b]pyridazin-3-yl)pyrimidin-4-yl)-6-methylpiperidin-3-yl)methanesulfonamide II-551;

N-(1-(6-(6-(Difluoromethyl)imidazo[1,2-b]pyridazin-3-yl)pyrimidin-4-yl)-6-methylpiperidin-3-yl)methanesulfonamide II-552.

Example 39: 1-(1-(6-(6-(Difluoromethyl)imidazo[1,2-b]pyridazin-3-yl)pyrimidin-4-yl)piperidin-3-yl)-N-methylmethanesulfonamide II-236

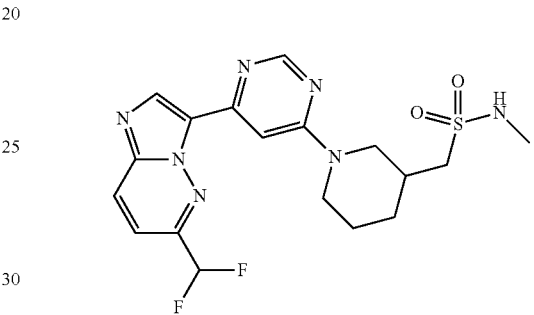

A mixture of [1-[6-[6-(difluoromethyl)imidazo[1,2-b]pyridazin-3-yl]pyrimidin-4-yl]-3-piperidyl]methanesulfonamide (8 mg, prepared according to a procedure similar to Example 1), K₂CO₃ (2.6 mg, 0.019 mmol) and iodomethane (2.7 mg, 1.2 μL, 0.019 mmol) in DMF (0.5 mL) was stirred at ambient temperature for 16 hours. K₂CO₃ (2.6 mg, 0.019 mmol) and iodomethane (2.7 mg, 1.2 μL, 0.019 mmol) were added and the mixture was stirred at ambient temperature for a further 6 hours. The insoluble material was filtered off and the filtrate was purified by reverse phase chromatography (C18, MeCN/Water/0.05% TFA as eluent) to give 1-(1-(6-(6-(difluoromethyl)imidazo[1,2-b]pyridazin-3-yl)pyrimidin-4-yl)piperidin-3-yl)-N-methylmethanesulfonamide II-236 (1.2 mg, 2.9%).

Example 40: N-((1-(6-(6-(Difluoromethyl)imidazo[1,2-b]pyridazin-3-yl)pyrimidin-4-yl)-4-fluoro-4-methylpiperidin-3-yl)methyl)methanesulfonamide, II-350, II-388, II-389

II-350

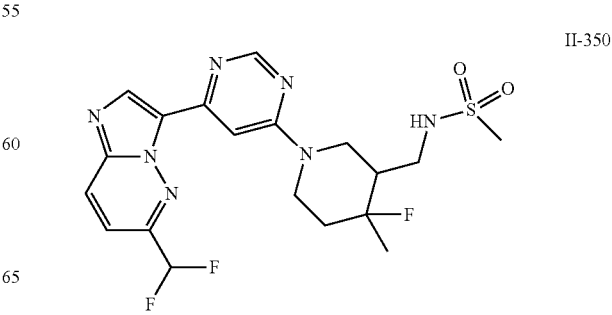

841

-continued

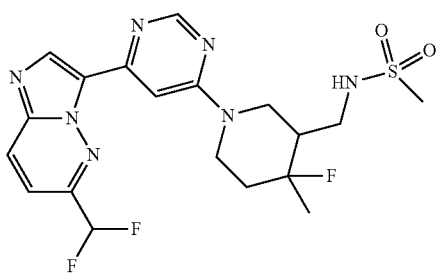

II-388 single stereoisomer

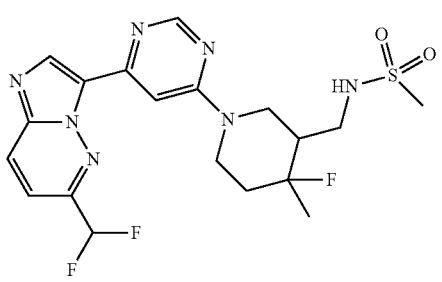

II-389 single stereoisomer

A solution of N-[[1-[6-[6-(difluoromethyl)imidazo[1,2-b]pyridazin-3-yl]pyrimidin-4-yl]-4-hydroxy-4-methyl-3-piperidyl]methyl]methanesulfonamide (200 mg, 0.43 mmol) in DCM (10 mL) was cooled to −78° C. under nitrogen before the dropwise addition of DAST (150 µL, 1.13 mmol). The mixture was stirred at this temperature for 10 minutes before removing the cold bath. The mixture was cautiously poured into a cold, saturated aqueous solution of NaHCO$_3$, then extracted with EtOAc (×2). The combined organic layers were dried (MgSO$_4$), filtered and evaporated. The residue was purified by reverse phase chromatography (C18, MeCN/water—0.1% ammonium hydroxide as eluent), affording the racemic mixture N-((1-(6-(6-(difluoromethyl)imidazo[1,2-b]pyridazin-3-yl)pyrimidin-4-yl)-4-fluoro-4-methylpiperidin-3-yl)methyl)methanesulfonamide II-350, which was further purified by chiral SFC to give enantiomerically pure N-((1-(6-(6-(difluoromethyl)imidazo[1,2-b]pyridazin-3-yl)pyrimidin-4-yl)-4-fluoro-4-methylpiperidin-3-yl)methyl)methanesulfonamide II-388 (19 mg, 9.5%) and N-((1-(6-(6-(difluoromethyl)imidazo[1,2-b]pyridazin-3-yl)pyrimidin-4-yl)-4-fluoro-4-methylpiperidin-3-yl)methyl)methanesulfonamide II-389 (6.6 mg, 3.3%).

842

Example 41: N-(((2S,6R)-4-(6-(6-(Difluoromethyl)imidazo[1,2-b]pyridazin-3-yl)pyrimidin-4-yl)-6-(trifluoromethyl)morpholin-2-yl)methyl)methanesulfonamide, II-331

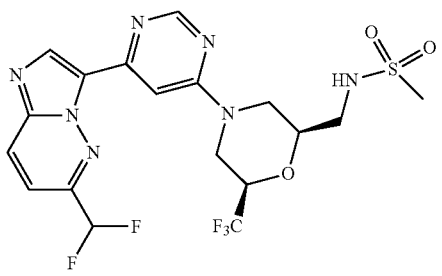 [SMILES: CS(=O)(=O)NC[C@@H]1CN(c2cc(-c3cnc4ccc(C(F)F)nn34)ncn2)C[C@H](C(F)(F)F)O1]

To a solution of [(2S,6S)-4-[6-[6-(difluoromethyl)imidazo[1,2-b]pyridazin-3-yl]pyrimidin-4-yl]-6-(trifluoromethyl)morpholin-2-yl]methanol (68.4 mg, 0.16 mmol, prepared according to a procedure similar to Example 1), tert-butyl N-methylsulfonylcarbamate (45 mg, 0.23 mmol) and PPh$_3$ (125 mg, 0.47 mmol) in THF (5 mL) was added DEAD (55 µL, 0.35 mmol) dropwise and the reaction mixture stirred at ambient temperature under nitrogen for 16 hours. The solvent was removed in vacuo and the residue redissolved in DCM (5 mL) and TFA (1 mL, 13 mmol). The reaction mixture was stirred at ambient temperature for 4.5 hours and the solvent removed in vacuo. The material was purified by reverse phase chromatography (C18, MeCN/Water/0.05% TFA as eluent). The product containing fractions were collected, passed through a sodium bicarbonate cartridge and freeze-dried to give N-[[(2S,6S)-4-[6-[6-(difluoromethyl)imidazo[1,2-b]pyridazin-3-yl]pyrimidin-4-yl]-6-(trifluoromethyl)morpholin-2-yl]methyl]methanesulfonamide II-331 (46.3 mg, 57%) as a white solid.

The following compounds were prepared using a methodology similar to the one described in Example 41:

N-((4-(6-(6-(Difluoromethyl)imidazo[1,2-b]pyridazin-3-yl)pyrimidin-4-yl)-5-ethylmorpholin-2-yl)methyl)methanesulfonamide II-267;

N-((4-(6-(6-(Difluoromethyl)imidazo[1,2-b]pyridazin-3-yl)pyrimidin-4-yl)-5-ethylmorpholin-2-yl)methyl)methanesulfonamide II-269;

N-(((2R,6S)-4-(6-(6-(Difluoromethyl)imidazo[1,2-b]pyridazin-3-yl)pyrimidin-4-yl)-6-(trifluoromethyl)morpholin-2-yl)methyl)methanesulfonamide II-306;

N-(((2S,6S)-4-(6-(6-(Difluoromethyl)imidazo[1,2-b]pyridazin-3-yl)pyrimidin-4-yl)-6-(trifluoromethyl)morpholin-2-yl)methyl)methanesulfonamide II-307;

N-(((2R,6R)-4-(6-(6-(Difluoromethyl)imidazo[1,2-b]pyridazin-3-yl)pyrimidin-4-yl)-6-(trifluoromethyl)morpholin-2-yl)methyl)methanesulfonamide II-330.

Example 42: 3-(3-(6-(6-(Difluoromethyl)imidazo[1,2-b]pyridazin-3-yl)pyrimidin-4-yl)piperidin-1-yl)-3-oxopropanenitrile, II-30

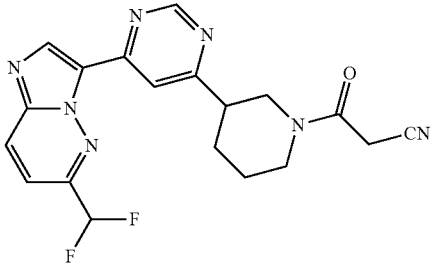 [SMILES: N#CCC(=O)N1CCCC(c2cc(-c3cnc4ccc(C(F)F)nn34)ncn2)C1]

A solution of 6-(difluoromethyl)-3-(6-(piperidin-3-yl)pyrimidin-4-yl)imidazo[1,2-b]pyridazine (20 mg, 0.06 mmol, prepared using Step 1 and Step 2 of Example 20) in MeCN (0.6 mL) was added to a solution of 2-cyanoacetic acid (5.2 mg, 0.06 mmol), (dimethylamino)-N,N-dimethyl(3H-[1,2,3]triazolo[4,5-b]pyridin-3-yloxy)methaniminium hexafluorophosphate (25.3 mg, 0.066 mmol) and DIPEA (42 uL, 0.24 mmol) in MeCN (0.4 mL) and the reaction stirred at ambient temperature for 16 hours. The reaction mixture was purified directly by reverse phase (C18, MeCN/Water/0.1% NH$_4$OH as eluent) to give 3-(3-(6-(6-(difluoromethyl)imidazo[1,2-b]pyridazin-3-yl)pyrimidin-4-yl)piperidin-1-yl)-3-oxopropanenitrile II-30 (11 mg, 44%).

The following compounds were prepared using a methodology similar to the one described in Example 42:
(3-(6-(6-(Difluoromethyl)imidazo[1,2-b]pyridazin-3-yl)pyrimidin-4-yl)piperidin-1-yl)(1-methyl-1H-pyrazol-4-yl)methanone II-41;
1-(3-(6-(6-(Difluoromethyl)imidazo[12-b]pyridazin-3-yl)pyrimidin-4-yl)piperidin-1-yl)ethan-1-one II-222;
1-(3-(6-(6-(Difluoromethyl)imidazo[1,2-b]pyridazin-3-yl)pyrimidin-4-yl)pyrrolidin-1-yl)ethan-1-one II-253.

Example 43: 6-(Difluoromethyl)-3-(6-(1-(oxetan-3-yl)piperidin-3-yl)pyrimidin-4-yl)imidazo[1,2-b]pyridazine, II-180

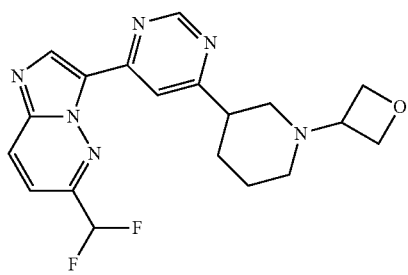 [SMILES: FC(F)c1ccc2ncc(-c3cc(C4CCCN(C5COC5)C4)ncn3)n2n1]

6-(Difluoromethyl)-3-(6-(piperidin-3-yl)pyrimidin-4-yl)imidazo[1,2-b]pyridazine (20 mg, 0.06 mmol, prepared using Step 1 and Step 2 of Example 20) was dissolved in THF (200 μL) and oxetan-3-one (6.5 mg, 0.091 mmol) was added. After 10 min, the reaction was cooled to approximately 10° C. then sodium triacetoxyborohydride (25.7 mg, 0.12 mmol) was added portionwise and the reaction was stirred at ambient temperature for 16 hours. The reaction mixture was partitioned between saturated aqueous NaHCO$_3$ and EtOAc. The layers were separated and the organic layer was washed with brine, dried (MgSO$_4$), filtered and concentrated under reduced pressure. The residue was purified directly by reverse phase (C18, MeCN/Water/0.1% NH$_4$OH as eluent) to give 6-(difluoromethyl)-3-(6-(1-(oxetan-3-yl)piperidin-3-yl)pyrimidin-4-yl)imidazo[1,2-b]pyridazine II-180 (11 mg, 38%).

The enantiomers were separated by chiral SFC to give:
(R)-6-(Difluoromethyl)-3-(6-(1-(oxetan-3-yl)piperidin-3-yl)pyrimidin-4-yl)imidazo[1,2-b]pyridazine and (S)-6-(Difluoromethyl)-3-(6-(1-(oxetan-3-yl)piperidin-3-yl)pyrimidin-4-yl)imidazo[1,2-b]pyridazine; II-241 and II-242 (in no particular order).

Example 44: 3-(6-(6-(Difluoromethyl)imidazo[1,2-b]pyridazin-3-yl)pyrimidin-4-yl)-N-(2-hydroxyethyl)piperidine-1-carboxamid, II-178

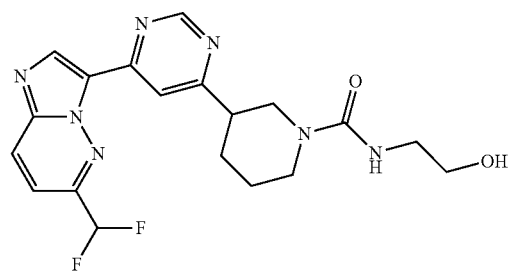

bis-(Trichloromethyl) carbonate (14.4 mg, 0.048 mmol) was added to a solution of 6-(difluoromethyl)-3-(6-(piperidin-3-yl)pyrimidin-4-yl)imidazo[1,2-b]pyridazine (20 mg, 0.06 mmol, prepared using Step 1 and Step 2 of Example 20) and DIPEA (39 mg, 53 μL, 0.30 mmol) in DCM (750 μL) and the reaction stirred at ambient temperature for 10 minutes. Ethanolamine (4.4 mg, 4.4 μL, 0.072 mmol) was added and the reaction was stirred at ambient temperature for a further 16 hours. The reaction mixture was partitioned between DCM and saturated aqueous NaHCO$_3$ and the organic layer dried and concentrated in vacuo. The residue was purified directly by reverse phase (C18, MeCN/Water/0.1% NH$_4$OH as eluent) to give 3-(6-(6-(difluoromethyl)imidazo[1,2-b]pyridazin-3-yl)pyrimidin-4-yl)-N-(2-hydroxyethyl)piperidine-1-carboxamide II-178 (10 mg, 38%).

The following compound was prepared using a methodology similar to the one described in Example 44:
3-(6-(6-(Difluoromethyl)imidazo[1,2-b]pyridazin-3-yl)pyrimidin-4-yl)-N-(2-hydroxyethyl)pyrrolidine-1-carboxamide II-254.

845

Example 45: 6-(Difluoromethyl)-3-(6-(1-(2-(methyl-sulfonyl)ethyl)piperidin-3-yl)pyrimidin-4-yl)imidazo[1,2-b]pyridazine, II-48

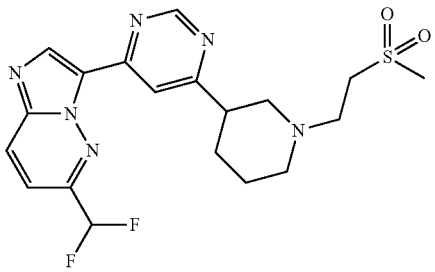 [SMILES: CS(=O)(=O)CCN1CCCC(c2cc(-c3cnc4ccc(C(F)F)nn34)ncn2)C1]

1-Methylsulfonylethylene (8.8 mg, 7.3 µL, 0.083 mmol) was added to a solution of 6-(difluoromethyl)-3-(6-(piperidin-3-yl)pyrimidin-4-yl)imidazo[1,2-b]pyridazine (25 mg, 0.075 mmol, prepared using Step 1 and Step 2 of Example 20) in ethanol (625 µL) and the reaction mixture was stirred at ambient temperature for 16 hours. The solvent was removed in vacuo and the residue purified by reverse phase chromatography (C18, MeCN/Water/0.05% TFA as eluent). The clean fractions were lyophilised to give 6-(difluoromethyl)-3-(6-(1-(2-(methylsulfonyl)ethyl)piperidin-3-yl)pyrimidin-4-yl)imidazo[1,2-b]pyridazine II-48 (6.9 mg, 16%).

The following compound was prepared using a methodology similar to the one described in Example 45:

6-(Difluoromethyl)-3-(6-(1-(2-(methylsulfonyl)ethyl)pyrrolidin-3-yl)pyrimidin-4-yl)imidazo[1,2-b]pyridazine II-255.

Example 46: N-((4-(6-(6-(Difluoromethyl)imidazo[1,2-b]pyridazin-3-yl)pyrimidin-4-yl)-1-ethyl-3-methylpiperazin-2-yl)methyl)methanesulfonamide, II-542, and N-((4-(6-(6-(difluoromethyl)imidazo[1,2-b]pyridazin-3-yl)pyrimidin-4-yl)-1-ethyl-3-methylpiperazin-2-yl)methyl)methanesulfonamide, II-543

II-542

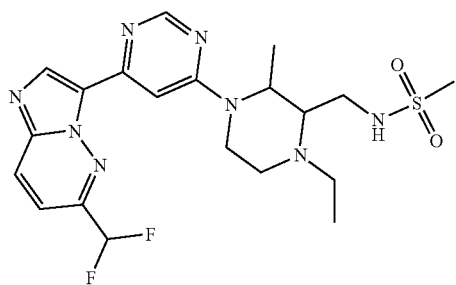

(single stereoisomer)

846

-continued

II-543

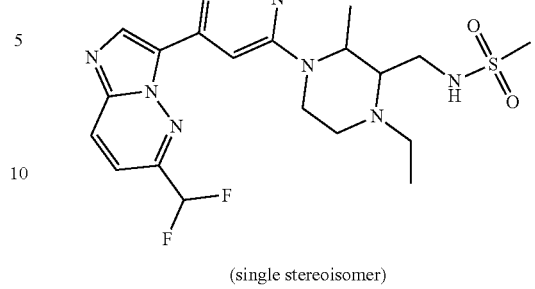

(single stereoisomer)

N-[[4-[6-[6-(Difluoromethyl)imidazo[1,2-b]pyridazin-3-yl]pyrimidin-4-yl]-3-methyl-piperazin-2-yl]methyl]methanesulfonamide II-313 (200 mg, 0.44 mmol) was dissolved in DMF (1.8 mL) before addition of ethyl iodide (138 mg, 71 µL, 0.88 mmol), followed by potassium carbonate (92 mg, 0.66 mmol). The solution was then heated at 60° C. for 7 hours. The reaction mixture was diluted with DMSO (3 mL) and the insoluble material was filtered off. The filtrate was purified directly by reverse phase (C18, MeCN/Water/0.1% NH₄OH as eluent) to give N-((4-(6-(6-(difluoromethyl)imidazo[12-b]pyridazin-3-yl)pyrimidin-4-yl)-1-ethyl-3-methylpiperazin-2-yl)methyl)methanesulfonamide II-482 (130 mg, 62%).

The enantiomers were separated by chiral SFC affording:

N-((4-(6-(6-(Difluoromethyl)imidazo[1,2-b]pyridazin-3-yl)pyrimidin-4-yl)-1-ethyl-3-methylpiperazin-2-yl)methyl)methanesulfonamide II-542 (50 mg, 47%), and N-((4-(6-(6-(difluoromethyl)imidazo[1,2-b]pyridazin-3-yl)pyrimidin-4-yl)-1-ethyl-3-methylpiperazin-2-yl)methyl)methanesulfonamide II-543 (45 mg, 41%).

The following compounds were prepared using a methodology similar to the one described in Example 46:

N-((4-(6-(6-(Difluoromethyl)imidazo[1,2-b]pyridazin-3-yl)pyrimidin-4-yl)-1-(2-methoxyethyl)-3-methylpiperazin-2-yl)methyl)methanesulfonamide II-494;

N-((1-(Cyclopropylmethyl)-4-(6-(6-(difluoromethyl)imidazo[1,2-b]pyridazin-3-yl)pyrimidin-4-yl)-3-methylpiperazin-2-yl)methyl)methanesulfonamide II-495;

N-((4-(6-(6-(Difluoromethyl)imidazo[1,2-b]pyridazin-3-yl)pyrimidin-4-yl)-1-isopropyl-3-methylpiperazin-2-yl)methyl)methanesulfonamide II-507;

N-((4-(6-(6-(Difluoromethyl)imidazo[1,2-b]pyridazin-3-yl)pyrimidin-4-yl)-3-methyl-1-(methyl-d3)piperazin-2-yl)methyl)methanesulfonamide II-523;

N-((4-(6-(6-(Difluoromethyl)imidazo[1,2-b]pyridazin-3-yl)pyrimidin-4-yl)-3-methyl-1-(methyl-d3)piperazin-2-yl)methyl)methanesulfonamide II-561;

N-((4-(6-(6-(Difluoromethyl)imidazo[1,2-b]pyridazin-3-yl)pyrimidin-4-yl)-3-methyl-1-(methyl-d3)piperazin-2-yl)methyl)methanesulfonamide II-562.

847

Example 47: N-[[3-[6-[6-(Difluoromethyl)imidazo[1,2-b]pyridazin-3-yl]pyrimidin-4-yl]phenyl]methyl]methanesulfonamide II-576

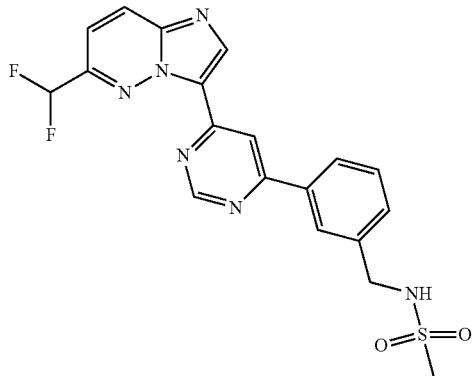 [SMILES: CS(=O)(=O)NCc1cccc(-c2cc(-c3cnc4ccc(C(F)F)nn34)ncn2)c1]

A mixture of Pd(PPh$_3$)$_4$ (8 mg, 0.007 mmol), Na$_2$CO$_3$ (213 µL of 2 M, 0.42 mmol), [3-(methanesulfonamidomethyl)phenyl]boronic acid (42.3 mg, 0.185 mmol) and 3-(6-chloropyrimidin-4-yl)-6-(difluoromethyl)imidazo[1,2-b]pyridazine (40 mg, 0.14 mmol) in 1,4-dioxane (2.4 mL) was stirred at 60° C. for 1 hour. The reaction mixture was partitioned between DCM and water, the layers separated and the organic layer dried and concentrated in vacuo. The residue was triturated in 2 mL MeOH. The insoluble material was filtered off and collected to give N-[[3-[6-[6-(difluoromethyl)imidazo[1,2-b]pyridazin-3-yl]pyrimidin-4-yl]phenyl]methyl]methanesulfonamide II-576 (9 mg, 14%).

The following compounds were prepared according to a procedure similar to Example 47:

3-[6-[6-(Difluoromethyl)imidazo[1,2-b]pyridazin-3-yl]pyrimidin-4-yl]-5-methyl-benzaldehyde;

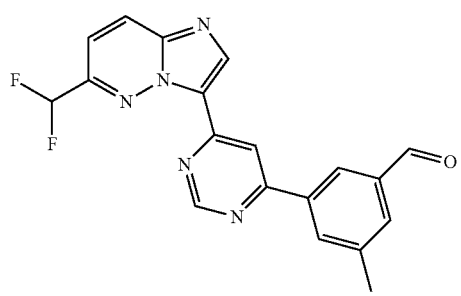 [SMILES: Cc1cc(C=O)cc(-c2cc(-c3cnc4ccc(C(F)F)nn34)ncn2)c1]

[3-[6-[6-(Difluoromethyl)imidazo[1,2-b]pyridazin-3-yl]pyrimidin-4-yl]-5-methyl-phenyl]methanol II-655;
1-(3-(6-(6-(Difluoromethyl)imidazo[1,2-b]pyridazin-3-yl)pyrimidin-4-yl)phenyl)ethan-1-ol II-656;
3-(6-(3-Bromophenyl)pyrimidin-4-yl)-6-(difluoromethyl)imidazo[1,2-b]pyridazine;

848

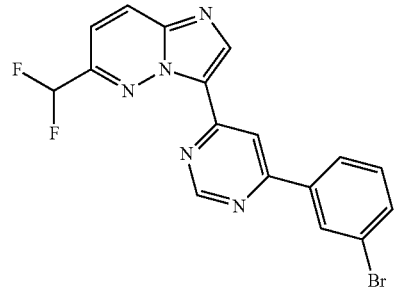 [SMILES: FC(F)c1ccc2ncc(-c3cc(-c4cccc(Br)c4)ncn3)n2n1]

6-(Difluoromethyl)-3-[6-[3-(methylsulfanylmethyl)phenyl]pyrimidin-4-yl]imidazo[1,2-b]pyridazine;

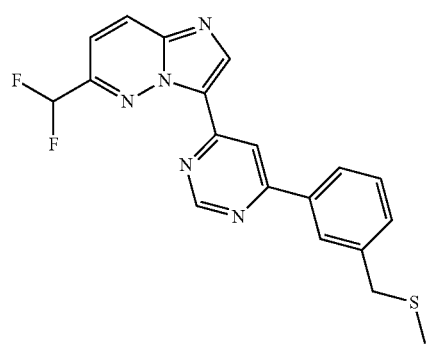 [SMILES: CSCc1cccc(-c2cc(-c3cnc4ccc(C(F)F)nn34)ncn2)c1]

3-(6-(6-(Difluoromethyl)imidazo[1,2-b]pyridazin-3-yl)pyrimidin-4-yl)-2-methylbenzaldehyde;

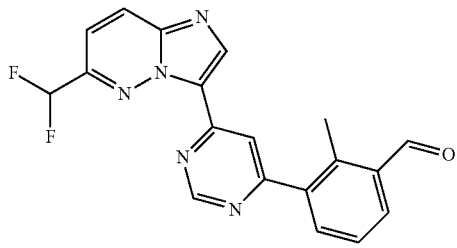 [SMILES: Cc1c(C=O)cccc1-c1cc(-c2cnc3ccc(C(F)F)nn23)ncn1]

3-[6-(1-Tetrahydropyran-4-ylpyrazol-4-yl)pyrimidin-4-yl]-6-(trifluoromethyl)imidazo[1,2-b]pyridazine II-708;
6-(Difluoromethyl)-3-[6-(1-tetrahydropyran-4-ylpyrazol-4-yl)pyrimidin-4-yl]imidazo[1,2-b]pyridazine II-709.

Example 48: N-[[3-[6-[6-(Difluoromethyl)imidazo[1,2-b]pyridazin-3-yl]pyrimidin-4-yl]-2-methyl-phenyl]methyl]methanesulfonamide, II-575

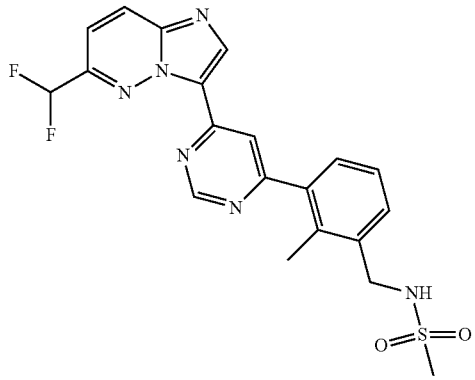 [SMILES: Cc1c(CNS(C)(=O)=O)cccc1-c1cc(-c2cnc3ccc(C(F)F)nn23)ncn1]

Step 1: [3-[6-[6-(Difluoromethyl)imidazo[1,2-b]pyridazin-3-yl]pyrimidin-4-yl]-2-methyl-phenyl]methanol Sodium borohydride (1.7 mg, 0.044 mmol) was added to a suspension of 3-[6-[6-(difluoromethyl)imidazo[1,2-b]pyridazin-3-yl]pyrimidin-4-yl]-2-methyl-benzaldehyde (32 mg, 0.09 mmol, prepared according to a procedure similar to Example 47) in MeOH (2 mL) and DCM (1 mL). After 1 minute, the mixture was quenched with 1 drop of 1 M HCl and the layers were separated. The aqueous layer was extracted with DCM and the combined organic layers were dried (MgSO$_4$) and concentrated in vacuo to give [3-[6-[6-(difluoromethyl) imidazo[1,2-b]pyridazin-3-yl]pyrimidin-4-yl]-2-methyl-phenyl]methanol (32 mg, 99%).

Step 2: N-[[3-[6-[6-(Difluoromethyl)imidazo[1,2-b]pyridazin-3-yl]pyrimidin-4-yl]-2-methyl-phenyl]methyl]methanesulfonamide, II-575

Isopropyl N-isopropoxycarbonyliminocarbamate (30 µL, 0.15 mmol) in DCM (0.5 mL) was slowly added to a suspension of [3-[6-[6-(difluoromethyl) imidazo[1,2-b]pyridazin-3-yl]pyrimidin-4-yl]-2-methyl-phenyl]methanol (31 mg, 0.08 mmol), tert-butyl N-methylsulfonylcarbamate (33 mg, 0.17 mmol) and PS—PPh$_3$ (80 mg of 2.11 mmol/g, 0.17 mmol) in DCM (3 mL) and the mixture was stirred at ambient temperature for 2 hours. Further PS—PPh$_3$ (80 mg of 2.11 mmol/g, 0.17 mmol) and tert-butyl N-methylsulfonylcarbamate (33 mg, 0.17 mmol) were added followed by a solution of isopropyl N-isopropoxycarbonyliminocarbamate (30 µL, 0.15 mmol) in DCM (0.5 mL), and the reaction mixture was left to stir at ambient temperature for 1 hour. The reaction mixture was filtered and the filtrate concentrated in vacuo. The residue was purified by reverse phase chromatography (C18, MeCN/Water/0.05% TFA as eluent). The pure fractions were combined and concentrated, and the residual solid was dried overnight at 60° C. in a drying piston to give N-[[3-[6-[6-(difluoromethyl)imidazo[1,2-b]pyridazin-3-yl]pyrimidin-4-yl]-2-methyl-phenyl]methyl]methanesulfonamide (13 mg, 35%).

Example 49: ((3-(6-(6-(Difluoromethyl)imidazo[1,2-b]pyridazin-3-yl)pyrimidin-4-yl)benzyl)imino)dimethyl-$\lambda^6$-sulfanone, II-595

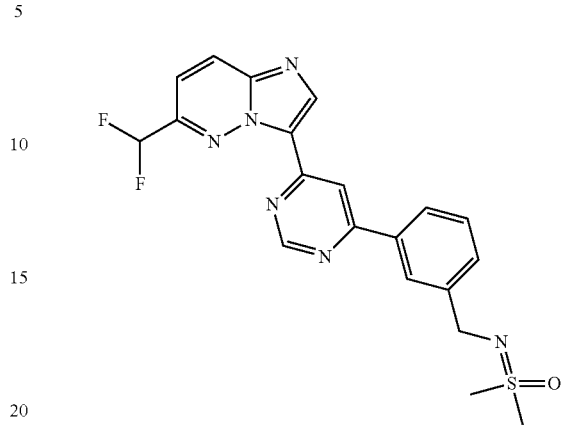

A mixture of (3-bromophenyl)methylimino-dimethyl-oxo-$\lambda^6$-sulfane (139 mg, 0.53 mmol, prepared according to a procedure similar to Example 47), potassium acetate (260 mg, 2.7 mmol), 4,4,5,5-tetramethyl-2-(4,4,5,5-tetramethyl-1,3,2-dioxaborolan-2-yl)-1,3,2-dioxaborolane (202 mg, 0.8 mmol) and Pd(dppf)Cl$_2$.DCM (44 mg, 0.05 mmol) in DMF (3 mL) was stirred at 100° C. for 1 hour. The mixture was concentrated in vacuo and the residue dissolved in 1,4-dioxane (4 mL). Na$_2$CO$_3$ (795 L of 2 M, 1.6 mmol), Pd(PPh$_3$)$_4$ (30.6 mg, 0.03 mmol) and 3-(6-chloropyrimidin-4-yl)-6-(difluoromethyl)imidazo[1,2-b]pyridazine (134 mg, 0.48 mmol) were added and the reaction was stirred at 100° C. for 4 hours. The mixture was concentrated in vacuo and the residue was purified by reverse phase chromatography (C18, MeCN/Water/0.05% TFA as eluent) to give ((3-(6-(6-(difluoromethyl)imidazo[1,2-b]pyridazin-3-yl)pyrimidin-4-yl)benzyl)imino)dimethyl-$\lambda^6$-sulfanone (14 mg, 5%).

Example 50: [3-[6-[6-(Difluoromethyl)imidazo[1,2-b]pyridazin-3-yl]pyrimidin-4-yl]phenyl]imino-dimethyl-oxo-$\lambda^6$-sulfane, II-599

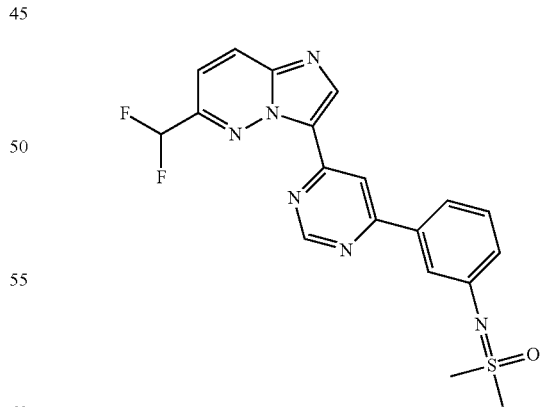

3-[6-(3-Bromophenyl)pyrimidin-4-yl]-6-(difluoromethyl)imidazo[1,2-b]pyridazine (110 mg, 0.27 mmol) (prepared according to a procedure similar to Example 47), imino-dimethyl-oxo-$\lambda^6$-sulfane (32 mg, 0.34 mmol), di-tert-butyl-(2-phenylphenyl)phosphane (23 mg, 0.078 mmol), tris(dibenzylideneacetone)dipalladium(0) (25 mg, 0.027 mmol), 2-methylpropan-2-olate (sodium salt) (39 mg, 0.4 mmol) in 1,4-dioxane (4 mL) was degassed (N$_2$) then heated at 90° C. for 15 minutes. The mixture was concentrated in vacuo and the residue was purified by reverse phase chromatography (C18, MeCN/Water/0.05% TFA as eluent). The pure fractions were combined and freeze dried to give [3-[6-[6-(difluoromethyl)imidazo[1,2-b]pyridazin-3-yl]pyrimidin-4-yl]phenyl]imino-dimethyl-oxo-λ6-sulfane (41 mg, 36%).

Example 51: N-[1-[3-[6-[6-(Difluoromethyl)imidazo[1,2-b]pyridazin-3-yl]pyrimidin-4-yl]phenyl]ethyl]methanesulfonamide, II-609

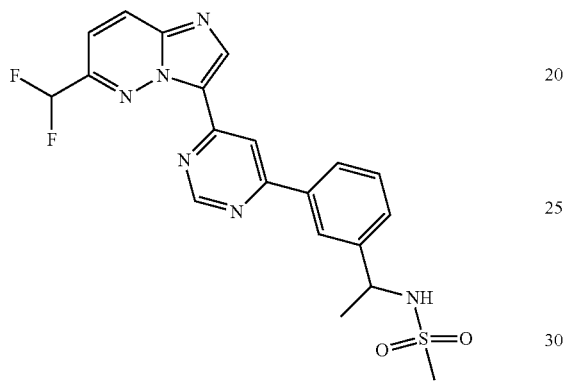

To a stirred solution of 1-[3-[6-[6-(difluoromethyl)imidazo[1,2-b]pyridazin-3-yl]pyrimidin-4-yl]phenyl]ethanol (130 mg, 0.35 mmol, prepared according to a procedure similar to Example 47), tert-butyl N-methylsulfonylcarbamate (138.2 mg, 0.7 mmol) and PS—PPh$_3$ (334 mg, 0.7 mmol) was added DIAD (103 µL, 0.5 mmol) and the mixture was stirred at ambient temperature for 16 hours. Further tert-butyl N-methylsulfonylcarbamate (138 mg, 0.7 mmol), PS—PPh$_3$ (334 mg of 2.12 mmol/g, 0.7 mmol) and DIAD (103 µL, 0.5 mmol) were sequentially added and the mixture was stirred at ambient temperature for 6 hours. The reaction mixture was filtered off and the filtrate concentrated in vacuo. The residue was dissolved in MeOH and DCM and loaded on a SCX-2 cartridge, washing with DCM/MeOH mixtures. The product was eluted with 2 M NH$_3$ in MeOH and the basic eluent was concentrated in vacuo. To the residue was added DCM (5 mL) followed by TFA (3 mL). The mixture was stirred at ambient temperature for 1 hour then concentrated in vacuo. The residue was purified by reverse phase chromatography (C18, MeCN/Water/0.05% TFA as eluent) to give N-[1-[3-[6-[6-(difluoromethyl)imidazo[1,2-b]pyridazin-3-yl]pyrimidin-4-yl]phenyl]ethyl]methanesulfonamide (12.9 mg, 7%)

The following compound was prepared according to a procedure similar to Example 51:

N-(3-(6-(6-(Difluoromethyl)imidazo[1,2-b]pyridazin-3-yl)pyrimidin-4-yl)-5-methylbenzyl)methanesulfonamide II-612.

Example 52: [3-[6-[6-(Difluoromethyl)imidazo[1,2-b]pyridazin-3-yl]pyrimidin-4-yl]-5-methyl-phenyl]methylimino-dimethyl-oxo-λ$^6$-sulfane, II-610 and 3-(6-(6-(difluoromethyl)imidazo[1,2-b]pyridazin-3-yl)pyrimidin-4-yl)-N-(dimethyl(oxo)-λ$^6$-sulfanylidene)-5-methylbenzamide, II-611

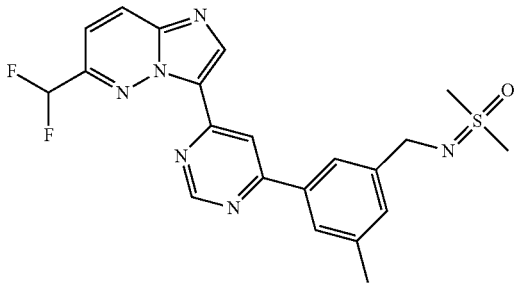

II-610

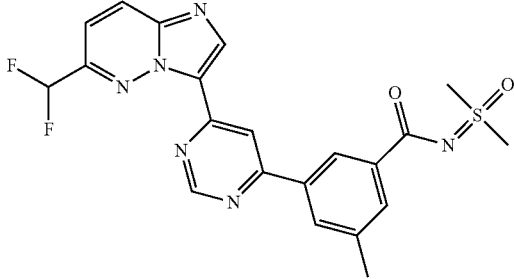

II-611

A solution of 3-[6-[6-(difluoromethyl)imidazo[1,2-b]pyridazin-3-yl]pyrimidin-4-yl]-5-methyl-benzaldehyde (130 mg, 0.36 mmol, prepared according to a procedure similar to Example 47), iminodimethyl-λ$^6$-sulfanone (100 mg, 1 mmol) and NaBH(OAc)$_3$ (150 mg, 0.7 mmol) in DCE (5 mL) was stirred at ambient temperature for 4 hours. Further iminodimethyl-λ$^6$-sulfanone (100 mg, 1 mmol) and NaBH(OAc)$_3$ (150 mg, 0.7 mmol) were added and the mixture was stirred at ambient temperature for 4 hours. Iminodimethyl-λ$^6$-sulfanone (99.4 mg, 1.1 mmol) and NaBH(OAc)$_3$ (150 mg, 0.7 mmol) were added and the mixture stirred at ambient temperature for a further 16 hours. The mixture was partitioned between DCM and saturated aqueous NaHCO$_3$. The layers were separated and the organic layer was dried and concentrated in vacuo. The residue was purified by reverse phase chromatography (C18, MeCN/Water/0.05% TFA as eluent) to give [3-[6-[6-(difluoromethyl)imidazo[1,2-b]pyridazin-3-yl]pyrimidin-4-yl]-5-methyl-phenyl]methylimino-dimethyl-oxo-λ$^6$-sulfane II-610 (30.8 mg, 14%) and 3-(6-(6-(difluoromethyl)imidazo[1,2-b]pyridazin-3-yl)pyrimidin-4-yl)-N-(dimethyl(oxo)-λ$^6$-sulfanylidene)-5-methylbenzamide II-611 (5 mg, 3%).

Example 53: 6-(Difluoromethyl)-3-[6-[2,5-dimethyl-3-(methylsulfonylmethyl)-1-piperidyl]pyrimidin-4-yl]imidazo[1,2-b]pyridazine, II-587 and 6-(difluoromethyl)-3-[6-[2,5-dimethyl-3-(methylsulfonylmethyl)-1-piperidyl]pyrimidin-4-yl]imidazo[1,2-b]pyridazine, II-588

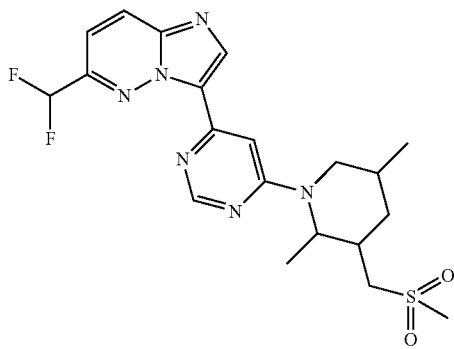

II-588

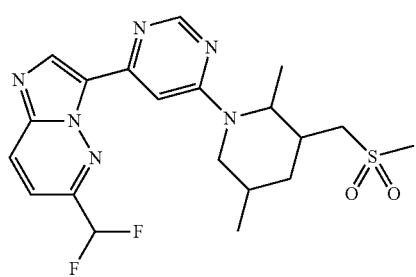

II-625 single stereoisomer

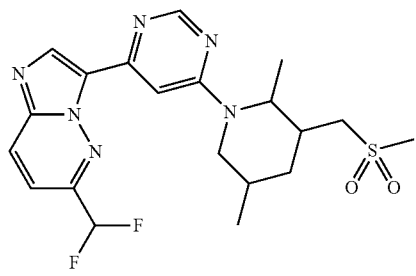

II-626 single stereoisomer

Step 1: 6-(Difluoromethyl)-3-[6-[2,5-dimethyl-3-(methylsulfanylmethyl)-1-piperidyl]pyrimidin-4-yl]imidazo[1,2-b]pyridazine Sodium methanethiolate (683 mg, 9.7 mmol) was added to a solution of [1-[6-[6-(difluoromethyl)imidazo[1,2-b]pyridazin-3-yl]pyrimidin-4-yl]-2,5-dimethyl-3-piperidyl]methyl methanesulfonate (757 mg, 1.6 mmol, prepared according to a procedure similar to Preparation 149) in EtOH (11 mL) stirring at 0° C. The cold bath was removed and the reaction was heated at 60° C. overnight. The reaction mixture was cooled to ambient temperature and concentrated in vacuo. The residue was purified by column chromatography (silica, 0 to 5% DCM/MeOH gradient elution) to give 6-(difluoromethyl)-3-[6-[2,5-dimethyl-3-(methylsulfanylmethyl)-1-piperidyl]pyrimidin-4-yl]imidazo[1,2-b]pyridazine (520 mg, 77%).

Step 2: 6-(Difluoromethyl)-3-[6-[2,5-dimethyl-3-(methylsulfonylmethyl)-1-piperidyl]pyrimidin-4-yl]imidazo[1,2-b]pyridazine mCPBA (44 mg, 0.18 mmol) was added portionwise to an ice-cold solution of 6-(difluoromethyl)-3-[6-[2,5-dimethyl-3-(methylsulfanylmethyl)-1-piperidyl]pyrimidin-4-yl]imidazo[1,2-b]pyridazine (30 mg, 0.07 mmol) in DCM (615 µL). The reaction mixture was stirred for 4 hours before it was quenched with a Na$_2$S$_2$O$_3$ aqueous solution (20 mL). The mixture was partitioned between DCM and water and the organic layer washed with NaHCO$_3$ (×2), dried (MgSO$_4$) and concentrated in vacuo. The residue was purified directly by reverse phase (C18, MeCN/Water/0.1% NH$_4$OH as eluent) to give 6-(difluoromethyl)-3-[6-[2,5-dimethyl-3-(methylsulfonylmethyl)-1-piperidyl]pyrimidin-4-yl]imidazo[1,2-b]pyridazine II-587 (5 mg, 15%) and 6-(difluoromethyl)-3-[6-[2,5-dimethyl-3-(methylsulfonylmethyl)-1-piperidyl]pyrimidin-4-yl]imidazo[1,2-b]pyridazine II-588 (1.9 mg, 5.9%).

The enantiomers of II-587 were separated by chiral SFC affording:
6-(Difluoromethyl)-3-[6-[2,5-dimethyl-3-(methylsulfonylmethyl)-1-piperidyl]pyrimidin-4-yl]imidazo[1,2-b]pyridazine II-625 and
6-(difluoromethyl)-3-[6-[2,5-dimethyl-3-(methylsulfonylmethyl)-1-piperidyl]pyrimidin-4-yl]imidazo[1,2-b]pyridazine II-626.

The following compound was prepared according to a procedure similar to Example 53:
4-(6-(6-(Difluoromethyl)imidazo[1,2-b]pyridazin-3-yl)pyrimidin-4-yl)-3-methyl-2-((methylsulfonyl)methyl)morpholine II-426.

Example 54: 1-(4-(4-(6-Methoxyimidazo[1,2-b]pyridazin-3-yl)pyridin-2-yl)piperazin-1-yl)ethan-1-one trifluoroacetate, II-204

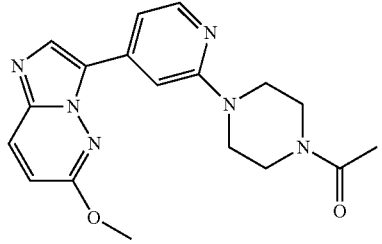 [SMILES: COc1ccc2ncc(-c3ccnc(N4CCN(C(C)=O)CC4)c3)n2n1]

Step 1: 6-Chloro-3-(2-(piperazin-1-yl)pyridin-4-yl)imidazo[1,2-b]pyridazine To a solution of 6-chloro-3-iodo-imidazo[1,2-b]pyridazine (440 mg, 1.57 mmol) in 1,4-dioxane (6 mL) and H$_2$O (2 mL) was added 1-[4-(4,4,5,5-tetramethyl-1,3,2-dioxaborolan-2-yl)-2-pyridyl]piperazine (350 mg, 1.21 mmol), Pd(PPh$_3$)$_4$ (98 mg, 0.084 mmol) and Na$_2$CO$_3$ (1.82 mL of 2 M, 3.63 mmol). The reaction mixture was stirred at 100° C. for 45 minutes. The mixture was diluted with EtOAc and sequentially washed with saturated aqueous NaHCO$_3$ and brine. The organic layer was dried (MgSO$_4$) and concentrated to give 6-chloro-3-(2-(piperazin-1-yl)pyridin-4-yl)imidazo[1,2-b]pyridazine, which was used directly in the next step.

Step 2: 1-(4-(4-(6-Chloroimidazo[1,2-b]pyridazin-3-yl)pyridin-2-yl)piperazin-1-yl)ethan-1-one To a solution of 6-chloro-3-(2-piperazin-1-yl-4-pyridyl)imidazo[1,2-b]pyridazine (700 mg, 2.22 mmol) in DCM (10 mL) was added N,N,N',N'-tetramethyl-O-(benzotriazol-1-yl)uronium tetrafluoroborate (714 mg, 2.22 mmol), acetic acid (200 mg, 190 µL, 3.34 mmol) and triethylamine (450 mg, 620 µL, 4.45 mmol). The reaction was stirred at ambient temperature for 3 hours and then at 100° C. for 45 minutes. The mixture was diluted with EtOAc and sequentially washed with a 10% aqueous solution of citric acid and brine. The organic layer was dried (Na$_2$SO$_4$) and concentrated to give a yellow oil that was purified by column chromatography (silica, 5 to 15% MeOH/NH$_3$ in DCM gradient elution) to give 1-[4-[4-(6-chloroimidazo[1,2-b]pyridazin-3-yl)-2-pyridyl]piperazin-1-yl]ethanone (760 mg, 96%) as a yellow solid; MS m/z: 357.2 (M+H)$^+$.

Step 3: 1-(4-(4-(6-Methoxyimidazo[1,2-b]pyridazin-3-yl)pyridin-2-yl)piperazin-1-yl)ethan-1-one trifluoroacetate, II-204

To a solution of 1-[4-[4-(6-chloroimidazo[1,2-b]pyridazin-3-yl)-2-pyridyl]piperazin-1-yl]ethanone (50 mg, 0.14 mmol) in MeOH (7 mL) was added NaOMe (22.7 mg, 0.42 mmol). The reaction was stirred at 120° C. for 90 minutes then directly purified by reverse phase chromatography (C18, MeCN/water/0.05% TFA as eluent) to give 1-(4-(4-(6-methoxyimidazo[1,2-b]pyridazin-3-yl)pyridin-2-yl)piperazin-1-yl)ethan-1-one trifluoroacetate (1 mg, 1.4%).

Example 55: N-(((3S,5S)-4,4-Difluoro-1-(6-(6-(1-hydroxyethyl)imidazo[1,2-b]pyridazin-3-yl)pyrimidin-4-yl)-5-methylpiperidin-3-yl)methylmethanesufonamide, II-337

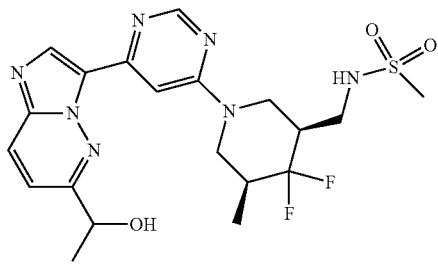 [SMILES: CC(O)c1ccc2ncc(-c3cc(N4C[C@@H](CNS(C)(=O)=O)C(F)(F)[C@@H](C)C4)ncn3)n2n1]

Step 1: N-(((3S,5S)-1-(6-(6-acetylimidazo[1,2-b]pyridazin-3-yl)pyrimidin-4-yl)-4,4-difluoro-5-methylpiperidin-3-yl)methyl)methanesulfonamide N-(((3S,5S)-1-(6-(6-acetylimidazo[1,2-b]pyridazin-3-yl)pyrimidin-4-yl)-4,4-difluoro-5-methylpiperidin-3-yl)methyl)methanesulfonamide was prepared from 1-(3-(6-chloropyrimidin-4-yl)imidazo[1,2-b]pyridazin-6-yl)ethan-1-one using a procedure similar to Example 1; MS m/z: 480.1 (M+H)$^+$.

Step 2: N-(((3S,5S)-4,4-Difluoro-1-(6-(6-(1-hydroxyethyl)imidazo[1,2-b]pyridazin-3-yl)pyrimidin-4-yl)-5-methylpiperidin-3-yl)methyl)methanesulfonamide, II-337

NaBH$_4$ (0.15 mg, 0.004 mmol) was added to a suspension of N-(((3S,5S)-1-(6-(6-acetylimidazo[1,2-b]pyridazin-3-yl)pyrimidin-4-yl)-4,4-difluoro-5-methylpiperidin-3-yl)methyl)methanesulfonamide (2 mg, 0.004 mmol) in MeOH (1 mL). The reaction was stirred at ambient temperature for 1 hour. The reaction mixture was directly purified by reverse phase chromatography (C18, MeCN/water/0.05% TFA as eluent) to afford N-(((3S,5S)-4,4-difluoro-1-(6-(6-(1-hydroxyethyl)imidazo[1,2-b]pyridazin-3-yl)pyrimidin-4-yl)-5-methylpiperidin-3-yl)methyl)methanesulfonamide (1.8 mg, 69%).

The following compound was prepared according to a procedure similar to Example 55:
N-(((2S)-4-(6-(6-(1-Hydroxyethyl)imidazo[1,2-b]pyridazin-3-yl)pyrimidin-4-yl)morpholin-2-yl)methyl)methanesulfonamide trifluoroacetate II-338.

Example 56: [4-[6-[6-(Difluoromethyl)imidazo[1,2-b]pyridazin-3-yl]pyrimidin-4-yl]-5-methyl-morpholin-2-yl]methanol, II-657

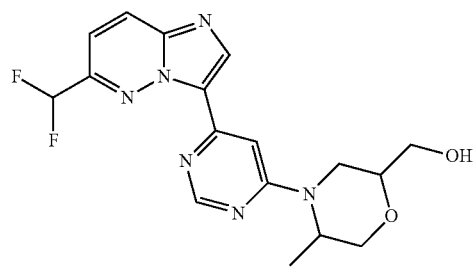 [SMILES: CC1COC(CO)CN1c1cc(-c2cnc3ccc(C(F)F)nn23)ncn1]

A mixture of (5-methylmorpholin-2-yl)methanol (250 mg, 1.906 mmol), 3-(6-chloropyrimidin-4-yl)-6-(difluoromethyl)imidazo[1,2-b]pyridazine (250 mg, 0.888 mmol) and DIPEA (300 µL, 1.722 mmol) in DMF (2 mL) was stirred at 90° C. for 18 hours. The solution was diluted with DCM and saturated aqueous NaHCO$_3$. After 5 minutes stirring, the organic layer was isolated using a phase separation cartridge and concentrated. Purification by column chromatography (silica, EtOAc/MeOH/petroleum ether elution) gave [4-[6-[6-(difluoromethyl)imidazo[1,2-b]pyridazin-3-yl]pyrimidin-4-yl]-5-methyl-morpholin-2-yl]methanol (305 mg, 91%); MS m/z: 377.3 (M+H)$^+$.

Example 57: 6-(Difluoromethyl)-3-[6-(2,5-dihydro-1H-pyrrol-3-yl)pyrimidin-4-yl]imidazo[1,2-b]pyridazine, II-658

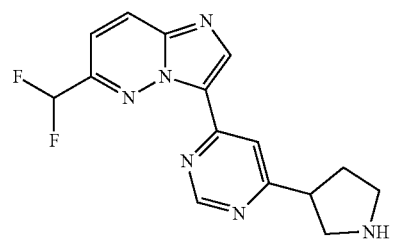 [SMILES: FC(F)c1ccc2ncc(-c3cc(C4CCNC4)ncn3)n2n1]

Step 1: tert-Butyl 3-(6-(6-(difluoromethyl)imidazo[1,2-b]pyridazin-3-yl)pyrimidin-4-yl)-2,5-dihydro-1H-pyrrole-1-carboxylate 3-(6-Chloropyrimidin-4-yl)-6-(difluoromethyl)imidazo[1,2-b]pyridazine (300 mg, 1.07 mmol), tert-butyl 3-(4,4,5, 5-tetramethyl-1,3,2-dioxaborolan-2-yl)-2,5-dihydropyrrole-1-carboxylate (314 mg, 1.07 mmol) and 2 M aqueous $K_2CO_3$ solution (2.66 mL of 2 M, 5.33 mmol) were combined in 1,4-dioxane (4.5 mL) and 1,1'-bis(diphenylphosphino)ferrocene-palladium(II)dichloride dichloromethane complex (43 mg, 0.05 mmol) was added. The mixture was degassed and the reaction heated in the microwave at 130° C. for 45 minutes. The reaction was diluted with EtOAc and water and filtered. The layers were separated and the aqueous phase extracted with EtOAc (×2). The combined organics were washed with brine, dried ($MgSO_4$) and concentrated. Purification by column chromatography (silica, 50-100% ethyl acetate in petroleum ether gradient elution) gave tert-butyl 3-(6-(6-(difluoromethyl)imidazo[1,2-b]pyridazin-3-yl)pyrimidin-4-yl)-2,5-dihydro-1H-pyrrole-1-carboxylate as a fine white powder (150 mg, 32%); 1H NMR (400 MHz, DMSO-$d_6$) δ 9.30-9.15 (m, 1H), 8.82-8.67 (m, 2H), 8.58 (d, J=9.4 Hz, 1H), 7.76 (d, J=9.5 Hz, 1H), 7.42 (t, J=53.7 Hz, 1H), 7.13 (s, 1H), 4.55 (s, 2H), 4.38 (s, 2H), 1.52-1.40 (m, 9H); MS m/z: 415.1 $(M+H)^+$.

Step 2: 6-(Difluoromethyl)-3-[6-(2,5-dihydro-1H-pyrrol-3-yl)pyrimidin-4-yl]imidazo[1,2-b]pyridazine tert-Butyl 3-(6-(6-(difluoromethyl)imidazo[1,2-b]pyridazin-3-yl)pyrimidin-4-yl)-2,5-dihydro-1H-pyrrole-1-carboxylate (150 mg, 0.32 mmol) was dissolved in DCM (6 mL) and TFA (1.2 mL, 16.0 mmol) was added. The reaction was stirred at ambient temperature for 1 hour before being concentrated in vacuo. The residue was passed through an SCX-2 cartridge eluting the product with 2 M ammonia in MeOH, and the basic wash concentrated to give 6-(difluoromethyl)-3-(6-(2,5-dihydro-1H-pyrrol-3-yl)pyrimidin-4-yl)imidazo[1,2-b]pyridazine as a pale yellow solid (100 mg, 100%); MS m/z: 315.0 $(M+H)^+$.

Step 3: 6-(Difluoromethyl)-3-(6-pyrrolidin-3-ylpyrimidin-4-yl)imidazo[1,2-b]pyridazine II-658

Palladium (10% on carbon, 23.7 mg, 0.22 mmol) was added to 6-(difluoromethyl)-3-(6-(2,5-dihydro-1H-pyrrol-3-yl)pyrimidin-4-yl)imidazo[1,2-b]pyridazine (100 mg, 0.32 mmol) and MeOH (12.8 mL) was added. The mixture was degassed and stirred under a balloon of hydrogen. After 16 hours, the reaction mixture was filtered through Celite and concentrated to give 6-(difluoromethyl)-3-[6-(2,5-dihydro-1H-pyrrol-3-yl)pyrimidin-4-yl]imidazo[1,2-b]pyridazine II-658 (100 mg, 85%).

The following compound was prepared according to a procedure similar to Example 57:
6-(Difluoromethyl)-3-(6-(piperidin-3-yl)pyrimidin-4-yl)imidazo[1,2-b]pyridazine II-659.

Example 58: 1-(4-(6-(6-(Difluoromethyl)imidazo[1,2-b]pyridazin-3-yl)pyrimidin-4-yl)-3,6-dihydropyridin-1 (2H)-yl)ethan-1-one, II-539

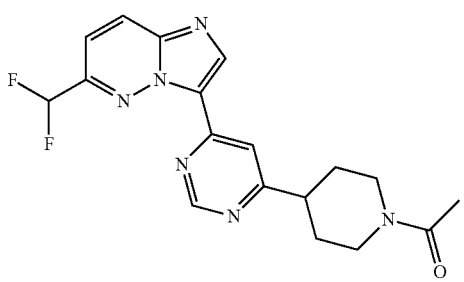 [SMILES: CC(=O)N1CCC(c2cc(-c3cnc4ccc(C(F)F)nn34)ncn2)CC1]

Step 1: 1-(4-(6-(6-(Difluoromethyl)imidazo[1,2-b]pyridazin-3-yl)pyrimidin-4-yl)-3,6-dihydropyridin-1 (2H)-yl)ethan-1-one 3-(6-Chloropyrimidin-4-yl)-6-(difluoromethyl)imidazo[1,2-b]pyridazine (101 mg, 0.36 mmol), 1-[4-(4,4,5,5-tetramethyl-1,3,2-dioxaborolan-2-yl)-3,6-dihydro-2H-pyridin-1-yl]ethanone (135 mg, 0.54 mmol) and 2 M saturated aqueous $K_2CO_3$ (900 μL of 2 M, 1.80 mmol) were combined in 1,4-dioxane (1.5 mL). The mixture was degassed, $Pd(dppf)Cl_2$.DCM (15 mg, 0.018 mmol) was added and the mixture degassed again before being heated at 130° C. for 45 minutes in a microwave. The reaction mixture was diluted with EtOAc and water and filtered through Celite. The layers were separated and the aqueous phase extracted with ethyl acetate (×2). The combined organics were washed with brine, dried ($MgSO_4$) and concentrated in vacuo. The residue was dissolved in DMSO, filtered and purified by reverse phase chromatography (C18, MeCN/Water/0.1% $NH_4OH$ as eluent) to give 1-[4-[6-[6-(difluoromethyl)imidazo[1,2-b]pyridazin-3-yl]pyrimidin-4-yl]-3,6-dihydro-2H-pyridin-1-yl]ethanone as a pale yellow solid (23 mg, 17%); MS m/z: 371.0 $(M+H)^+$.

Step 2: 1-(4-(6-(6-(Difluoromethyl)imidazo[1,2-b]pyridazin-3-yl)pyrimidin-4-yl)piperidin-1-yl)ethan-1-one A mixture of 1-[4-[6-[6-(difluoromethyl)imidazo[1,2-b]pyridazin-3-yl]pyrimidin-4-yl]-3,6-dihydro-2H-pyridin-1-yl]ethanone (23 mg, 0.062 mmol) [mixture of isomers] and Pd on C, wet, Degussa (28 mg of 10% w/w, 0.026 mmol) was stirred at ambient temperature under a balloon of $H_2$. After 3 hours, the catalyst was filtered off through Celite, the filtrate concentrated in vacuo and the residue purified by reverse phase chromatography (C18, MeCN/Water/0.1% $NH_4OH$ as eluent) to give 1-(4-(6-(6-(difluoromethyl)imidazo[1,2-b]pyridazin-3-yl)pyrimidin-4-yl)-3,6-dihydropyridin-1(2H)-yl)ethan-1-one II-539 as a white solid (8 mg, 32%)

Example 59: 3-[6-(2,8-Diazaspiro[3.5]nonan-2-yl)pyrimidin-4-yl]-6-(difluoromethyl)imidazo[1,2-b]pyridazine, II-660

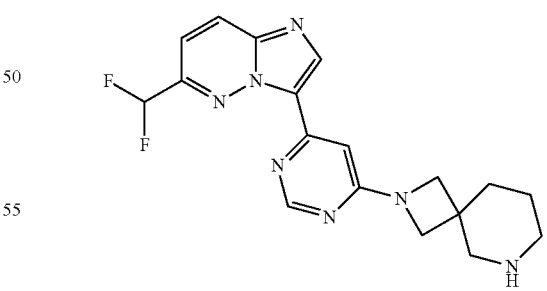

Step 1: tert-Butyl 2-(6-(6-(difluoromethyl)imidazo[1,2-b]pyridazin-3-yl)pyrimidin-4-yl)-2,6-diazaspiro[3.5]nonane-6-carboxylate 3-(6-Chloropyrimidin-4-yl)-6-(difluoromethyl)imidazo[1,2-b]pyridazine (60 mg, 0.21 mmol), tert-butyl 2,6-diazaspiro[3.5]nonane-6-carboxylate (96 mg, 0.43 mmol) and DIPEA (185 µL, 1.07 mmol) were combined in NMP (2 mL) and heated in the microwave for 35 minutes at 120° C. before being cooled to ambient temperature and purified by reverse phase chromatography (C18, MeCN/Water/0.1% NH₄OH as eluent) to give tert-butyl 2-(6-(6-(difluoromethyl)imidazo[1,2-b]pyridazin-3-yl)pyrimidin-4-yl)-2,6-diazaspiro[3.5]nonane-6-carboxylate, which was used directly in the next step.

Step 2: 3-[6-(2,8-diazaspiro[3.5]nonan-2-yl)pyrimidin-4-yl]-6-(difluoromethyl)imidazo[1,2-b]pyridazine, II-660 tert-Butyl 2-(6-(6-(difluoromethyl)imidazo[1,2-b]pyridazin-3-yl)pyrimidin-4-yl)-2,6-diazaspiro[3.5]nonane-6-carboxylate was dissolved in DCM (3 mL) and TFA (1 mL). After stirring for 2 hours at ambient temperature the mixture was concentrated. The residue was taken up in MeOH, passed through SPE bicarbonate cartridges and concentrated to give 3-[6-(2,8-Diazaspiro[3.5]nonan-2-yl)pyrimidin-4-yl]-6-(difluoromethyl)imidazo[1,2-b]pyridazine as a white solid (100 mg, 100%); MS m/z: 372.1 (M+H)⁺.

The following compounds were prepared according to a procedure similar to Example 59:
1-[6-[6-(Difluoromethyl)imidazo[1,2-b]pyridazin-3-yl]pyrimidin-4-yl]-3,4,4a,5,6,7,8,8a-octahydro-2H-quinoxalin-5-ol II-628;
(3S)-1-[6-[6-(Difluoromethyl)imidazo[1,2-b]pyridazin-3-yl]pyrimidin-4-yl]piperidin-3-amine II-661;
1-(6-(6-(Difluoromethyl)imidazo[1,2-b]pyridazin-3-yl)pyrimidin-4-yl)octahydro-1H-pyrido[3,4-b][1,4]oxazine II-662;
1-(6-(6-(Difluoromethyl)imidazo[1,2-b]pyridazin-3-yl)pyrimidin-4-yl)-6-methylpiperidin-3-amine II-663;
2-[6-[6-(Difluoromethyl)imidazo[1,2-b]pyridazin-3-yl]pyrimidin-4-yl]-5-oxa-2,8-diazaspiro[3.5]nonane II-664;
3-[6-(3,3a,4,5,6,6a-Hexahydro-2H-pyrrolo[2,3-c]pyrrol-1-yl)pyrimidin-4-yl]-6-(difluoromethyl)imidazo[1,2-b]pyridazine II-665;
1-[1-[6-[6-(Difluoromethyl)imidazo[1,2-b]pyridazin-3-yl]pyrimidin-4-yl]-3-piperidyl]-N-methyl-methanamine II-666;
4-[6-[6-(Difluoromethyl)imidazo[1,2-b]pyridazin-3-yl]pyrimidin-4-yl]-3,4a,5,6,7,7a-hexahydro-2H-pyrrolo[3,4-b][1,4]oxazine II-667;
3-[6-(2,6-Diazaspiro[3.5]nonan-6-yl)pyrimidin-4-yl]-6-(difluoromethyl)imidazo[1,2-b]pyridazine II-668;
8-[6-[6-(Difluoromethyl)imidazo[1,2-b]pyridazin-3-yl]pyrimidin-4-yl]-5-oxa-2,8-diazaspiro[3.5]nonane II-669;
3-[6-(2,3,4,4a, 5,6,7,7a-Octahydropyrrolo[3,4-b]pyridin-1-yl)pyrimidin-4-yl]-6-(difluoromethyl)imidazo[1,2-b]pyridazine II-670;
[1-[6-[6-(Difluoromethyl)imidazo[1,2-b]pyridazin-3-yl]pyrimidin-4-yl]-3-piperidyl]methanamine II-671;
[4-[6-[6-(Difluoromethyl)imidazo[1,2-b]pyridazin-3-yl]pyrimidin-4-yl]morpholin-2-yl]methanamine II-672;
2-(6-(6-(Difluoromethyl)imidazo[1,2-b]pyridazin-3-yl)pyrimidin-4-yl)-2,8-diazaspiro[4.5]decane II-673;
3-(6-(1,6-Diazaspiro[3.5]nonan-6-yl)pyrimidin-4-yl)-6-(difluoromethyl)imidazo[1,2-b]pyridazine II-674;
7-(6-(6-(Difluoromethyl)imidazo[1,2-b]pyridazin-3-yl)pyrimidin-4-yl)-2,7-diazaspiro[4.5]decane II-675;
3-(6-(3,8-Diazabicyclo[4.2.0]octan-3-yl)pyrimidin-4-yl)-6-(difluoromethyl)imidazo[1,2-b]pyridazine II-677;
1-(6-(6-(Difluoromethyl)imidazo[1,2-b]pyridazin-3-yl)pyrimidin-4-yl)-3-methylpiperidin-3-amine II-678;
3-[6-(2,3,3a,4,5,6,7,7a-Octahydropyrrolo[2,3-c]pyridin-1-yl)pyrimidin-4-yl]-6-(difluoromethyl)imidazo[1,2-b]pyridazine II-679;
1-(1-(6-(6-(Difluoromethyl)imidazo[1,2-b]pyridazin-3-yl)pyrimidin-4-yl)piperidin-3-yl)ethan-1-amine II-680;
(1-(6-(6-(Difluoromethyl)imidazo[1,2-b]pyridazin-3-yl)pyrimidin-4-yl)pyrrolidin-3-yl)methanamine II-681;
1-[6-[6-(Difluoromethyl)imidazo[1,2-b]pyridazin-3-yl]pyrimidin-4-yl]-4,4-difluoro-piperidin-3-amine II-682.
4-(6-(6-(Difluoromethyl)imidazo[1,2-b]pyridazin-3-yl)pyrimidin-4-yl)-1-oxa-4,8-diazaspiro[5.5]undecane II-683.

Example 60: ((((2S,3S,5R)-1-(6-(6-(Difluoromethyl)imidazo[1,2-b]pyridazin-3-yl)pyrimidin-4-yl)-2,5-dimethylpiperidin-3-yl)methyl)(imino)(methyl)-λ⁶-sulfanone, II-607

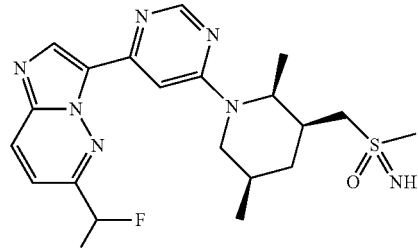

Step 1: [1-[6-[6-(difluoromethyl)imidazo[1,2-b]pyridazin-3-yl]pyrimidin-4-yl]-2,5-dimethyl-3-piperidyl]methyl Methanesulfonate Methanesulfonyl chloride (188 µL, 2.43 mmol) was added to a cooled solution of [1-[6-[6-(difluoromethyl)imidazo[1,2-b]pyridazin-3-yl]pyrimidin-4-yl]-2,5-dimethyl-3-piperidyl]methanol (630 mg, 1.62 mmol) and triethylamine (452 µL, 3.24 mmol) in DCM (12.6 mL) stirring under nitrogen. After 15 minutes at 0° C. the reaction was quenched with a saturated aqueous solution of NaHCO₃. After stirring for 10 minutes the layers were separated using a phase separator cartridge and the organic layer concentrated to give [1-[6-[6-(difluoromethyl)imidazo[1,2-b]pyridazin-3-yl]pyrimidin-4-yl]-2,5-dimethyl-3-piperidyl] methyl methanesulfonate as a colourless oil which was used directly in the next step; MS m/z: 467.1 (M+H)⁺.

Step 2: 6-(Difluoromethyl)-3-[6-[2,5-dimethyl-3-(methylsulfanylmethyl)-1-piperidyl]pyrimidin-4-yl] imidazo[1,2-b]pyridazine Sodium methanethiolate (683 mg, 9.74 mmol) was added to a solution of [1-[6-[6-(difluoromethyl)imidazo[1,2-b]pyridazin-3-yl]pyrimidin-4-yl]-2,5-dimethyl-3-piperidyl] methyl methanesulfonate (757 mg, 1.62 mmol) in EtOH (11.2 mL) stirring at 0° C. The cold bath was removed and the reaction heated to 60° C. for 16 hours before being cooled to ambient temperature and evaporated in vacuo. The residue was purified by column chromatography (silica, 0-5% MeOH in DCM gradient elution) to give 6-(difluoromethyl)-3-[6-[2,5-dimethyl-3-(methylsulfanylmethyl)-1-piperidyl]pyrimidin-4-yl]imidazo[1,2-b]pyridazine (520 mg, 77% over two steps); MS m/z: 419.3 (M+H)⁺.

Step 3: 6-(Difluoromethyl)-3-[6-[2,5-dimethyl-3-(methylsulfinylmethyl)-1-piperidyl]pyrimidin-4-yl]imidazo[1,2-b]pyridazine mCPBA (276 mg, 1.12 mmol) was added to an ice cold solution of 6-(difluoromethyl)-3-[6-[2,5-dimethyl-3-(methylsulfanylmethyl)-1-piperidyl]pyrimidin-4-yl]imidazo[1,2-b]pyridazine (520 mg, 1.24 mmol) in DCM (10.7 mL). After 5 minutes the reaction mixture was quenched with a saturated aqueous solution of $Na_2S_2O_3$ (20 mL) and stirred for 5 minutes before the layers were separated. The aqueous layer was extracted with DCM, then the combined organic layers were washed with saturated aqueous $NaHCO_3$ (2×20 mL), dried ($MgSO_4$) and concentrated to give 6-(difluoromethyl)-3-[6-[2,5-dimethyl-3-(methylsulfinylmethyl)-1-piperidyl]pyrimidin-4-yl]imidazo[1,2-b]pyridazine as a colourless gum (530 mg, 98%); MS m/z: 435.3 (M+H)$^+$.

Step 4: (((2S,3S,5R)-1-(6-(6-(Difluoromethyl)imidazo[1,2-b]pyridazin-3-yl)pyrimidin-4-yl)-2,5-dimethylpiperidin-3-yl)methyl)(imino)(methyl)-$\lambda^6$-sulfanone, II-607

6-(Difluoromethyl)-3-[6-[2,5-dimethyl-3-(methylsulfinylmethyl)-1-piperidyl]pyrimidin-4-yl]imidazo[1,2-b]pyridazine (340 mg, 0.78 mmol), ammonium carbamate (244 mg, 3.13 mmol) and iodobenzene diacetate (756 mg, 2.35 mmol) were dissolved in MeOH (1.6 mL) and stirred in an open flask. After 40 minutes, the reaction was concentrated under reduced pressure and the residue purified by column chromatography (silica, 0-10% MeOH in DCM gradient elution) to give a mixture of four stereoisomers as a pale yellow solid. This solid was dissolved in DMSO and purified by reverse phase chromatography (C18, MeCN/Water/0.1% $NH_4OH$ as eluent). The pure fractions were lyophilised to provide two sets of two isomers each.

Chiral separation using SFC provided:

(((2S,3S,5R)-1-(6-(6-(Difluoromethyl)imidazo[1,2-b]pyridazin-3-yl)pyrimidin-4-yl)-2,5-dimethylpiperidin-3-yl)methyl)(imino)(methyl)-$\lambda^6$-sulfanone II-607 as a yellow solid (25 mg, 23%); MS m/z: 450.1 (M+H)$^+$.

(((2R,3R,5S)-1-(6-(6-(Difluoromethyl)imidazo[1,2-b]pyridazin-3-yl)pyrimidin-4-yl)-2,5-dimethylpiperidin-3-yl)methyl)(imino)(methyl)-$\lambda^6$-sulfanone II-604; MS m/z: 450.1 (M+H)$^+$.

(((2R,3R,5S)-1-(6-(6-(Difluoromethyl)imidazo[1,2-b]pyridazin-3-yl)pyrimidin-4-yl)-2,5-dimethylpiperidin-3-yl)methyl)(imino)(methyl)-$\lambda^6$-sulfanone II-605; MS m/z: 450.1 (M+H)$^+$ and (((2S,3S,5R)-1-(6-(6-(Difluoromethyl)imidazo[1,2-b]pyridazin-3-yl)pyrimidin-4-yl)-2,5-dimethylpiperidin-3-yl)methyl)(imino)(methyl)-$\lambda^6$-sulfanone II-606; MS m/z: 450.1 (M+H)$^+$.

The following compounds were made using a similar method to Example 60:

((1-(4-(6-(Difluoromethyl)imidazo[1,2-b]pyridazin-3-yl)pyridin-2-yl)piperidin-3-yl)methyl)(imino)(methyl)-$\lambda^6$-sulfanone II-138;

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-370;

((4-(6-(6-(Difluoromethyl)imidazo[1,2-b]pyridazin-3-yl)pyrimidin-4-yl)-3-methylmorpholin-2-yl)methyl)(imino)(methyl)-$\lambda^6$-sulfanone II-425;

(S)-(((2S,3S)-1-(6-(6-(Difluoromethyl)imidazo[1,2-b]pyridazin-3-yl)pyrimidin-4-yl)-2-methylpiperidin-3-yl)methyl)(imino)(methyl)-$\lambda^6$-sulfanone II-485;

((1-(6-(6-(Difluoromethyl)imidazo[1,2-b]pyridazin-3-yl)pyrimidin-4-yl)-2-methylpiperidin-3-yl)methyl)(imino)(methyl)-$\lambda^6$-sulfanone II-486;

((1-(6-(6-(Difluoromethyl)imidazo[1,2-b]pyridazin-3-yl)pyrimidin-4-yl)-2-methylpiperidin-3-yl)methyl)(imino)(methyl)-$\lambda^6$-sulfanone II-487;

((1-(6-(6-(Difluoromethyl)imidazo[1,2-b]pyridazin-3-yl)pyrimidin-4-yl)-2-methylpiperidin-3-yl)methyl)(imino)(methyl)-$\lambda^6$-sulfanone II-488;

(1-(6-(6-(Difluoromethyl)imidazo[1,2-b]pyridazin-3-yl)pyrimidin-4-yl)piperidin-3-yl)(imino)(methyl)-$\lambda^6$-sulfanone II-522;

(2-(1-(4-(6-(Difluoromethyl)imidazo[1,2-b]pyridazin-3-yl)pyridin-2-yl)piperidin-3-yl)ethyl)(imino)(methyl)-$\lambda^6$-sulfanone II-104;

(3-(6-(6-(Difluoromethyl)imidazo[1,2-b]pyridazin-3-yl)pyrimidin-4-yl)phenyl)(imino)(methyl)-$\lambda^6$-sulfanone II-580;

(3-(6-(6-(Difluoromethyl)imidazo[1,2-b]pyridazin-3-yl)pyrimidin-4-yl)benzyl)(imino)(methyl)-$\lambda^6$-sulfanone II-598;

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-636;

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-637;

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-638;

((1-(6-(6-(Difluoromethyl)imidazo[1,2-b]pyridazin-3-yl)pyrimidin-4-yl)piperidin-3-yl)methyl)(imino)(methyl)-$\lambda^6$-sulfanone II-639.

Example 61: 1-[4-[6-(6-Chloroimidazo[1,2-b]pyridazin-3-yl)pyrimidin-4-yl]piperazin-1-yl]ethanone, II-590

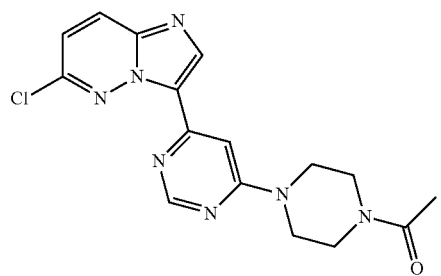 [SMILES: CC(=O)N1CCN(c2cc(-c3cnc4ccc(Cl)nn34)ncn2)CC1]

N-Bromosuccinimide (30.5 mg, 0.17 mmol) was added to a stirred solution of 1-[4-[6-[(E)-2-ethoxyvinyl]pyrimidin-4-yl]piperazin-1-yl]ethanone (45 mg, 0.16 mmol) in 1,4-dioxane (1 mL) and water (375 μL). The reaction mixture was stirred at ambient temperature for 1 hour before a solution of 6-chloropyridazin-3-amine (21 mg, 0.16 mmol) in 1,4-dioxane (63 μL) was added. The reaction mixture was heated at 80° C. for 16 hours before being cooled to ambient temperature and purified directly by reverse phase (C18, MeCN/Water/0.1% $NH_4OH$ as eluent) to give 1-[4-[6-(6-chloroimidazo[1,2-b]pyridazin-3-yl)pyrimidin-4-yl]piperazin-1-yl]ethanone (0.9 mg, 2%).

Example 62: N-((1-(6-(6-(Difluoromethyl)imidazo[1,2-b]pyridazin-3-yl)pyrimidin-4-yl)-5-hydroxypiperidin-3-yl)methyl)-N-methylmethanesulfonamide, II-235

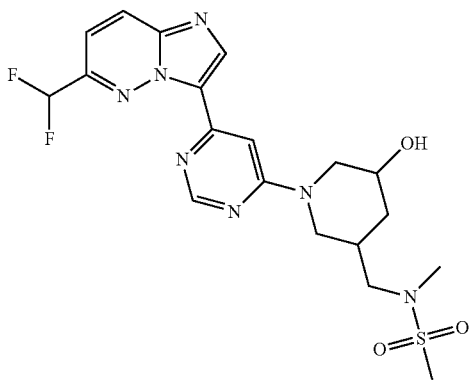 [SMILES: CN(CC1CC(O)CN(c2cc(-c3cnc4ccc(C(F)F)nn34)ncn2)C1)S(C)(=O)=O]

NaH (4 mg, 0.1 mmol) was added to an ice-cold suspension of N-[[1-[6-[6-(difluoromethyl)imidazo[1,2-b]pyridazin-3-yl]pyrimidin-4-yl]-5-hydroxy-3-piperidyl]methyl]methanesulfonamide (40 mg, 0.088 mmol, prepared according to a procedure similar to Example 1) in DMF (1 mL) stirring under nitrogen. After 10 min, MeI (6 μL, 0.096 mmol) was added and the reaction mixture was stirred at ambient temperature for 18 hours. The reaction was quenched by the addition of methanol (0.1 mL) and the crude mixture purified by reverse phase chromatography (C18, MeCN/water/0.05% TFA as eluent) to give N-((1-(6-(6-(difluoromethyl)imidazo[1,2-b]pyridazin-3-yl)pyrimidin-4-yl)-5-hydroxypiperidin-3-yl)methyl)-N-methylmethanesulfonamide (30 mg, 47%).

The following compound was prepared according to a procedure similar to Example 62:
(S)—N-((4-(6-(6-(Difluoromethyl)imidazo[1,2-b]pyridazin-3-yl)pyrimidin-4-yl)morpholin-2-yl)methyl)-N-methylmethanesulfonamide II-290.

Example 63: N-((1-(6-(6-(Difluoromethyl)imidazo[1,2-b]pyridazin-3-yl)pyrimidin-4-yl)piperidin-3-yl)methyl)azetidine-3-sulfonamide, II-272

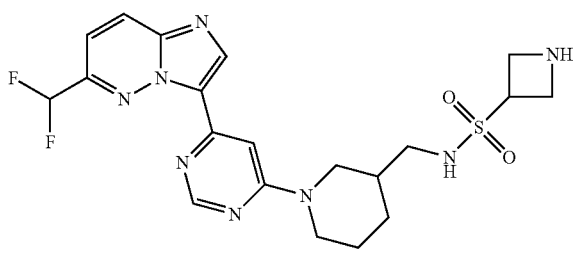 [SMILES: O=S(=O)(NCC1CCCN(c2cc(-c3cnc4ccc(C(F)F)nn34)ncn2)C1)C1CNC1]

Step 1: tert-Butyl 3-(N-((1-(6-(6-(difluoromethyl)imidazo[1,2-b]pyridazin-3-yl)pyrimidin-4-yl)piperidin-3-yl)methyl)sulfamoyl)azetidine-1-carboxylate DIPEA (65 μL, 0.38 mmol) and tert-butyl 3-chlorosulfonylazetidine-1-carboxylate (21 mg, 0.08 mmol) were added to a solution of [1-[6-[6-(difluoromethyl)imidazo[1,2-b]pyridazin-3-yl]pyrimidin-4-yl]-3-piperidyl]methanamine (30 mg, 0.08 mmol, prepared according to a procedure similar to Example 59) in acetonitrile (600 μL). The reaction was stirred at ambient temperature for 24 hours before being diluted in DMSO and purified by reverse phase chromatography (C18, MeCN/Water/0.1% NH$_4$OH as eluent) to give tert-butyl 3-(N-((1-(6-(6-(difluoromethyl)imidazo[1,2-b]pyridazin-3-yl)pyrimidin-4-yl)piperidin-3-yl)methyl)sulfamoyl)azetidine-1-carboxylate (50 mg, 100%); MS m/z: 579.1 (M+H)$^+$.

Step 2: N-((1-(6-(6-(Difluoromethyl)imidazo[1,2-b]pyridazin-3-yl)pyrimidin-4-yl)piperidin-3-yl)methyl)azetidine-3-sulfonamide TFA (148 mg, 100 μL, 1.3 mmol) was added to a solution of tert-butyl 3-(N-((1-(6-(6-(difluoromethyl)imidazo[1,2-b]pyridazin-3-yl)pyrimidin-4-yl)piperidin-3-yl)methyl)sulfamoyl)azetidine-1-carboxylate (50 mg, 0.086 mmol) in DCM (1 mL) and the reaction stirred at ambient temperature for 45 minutes. The reaction was concentrated in vacuo and the residue was loaded on a SCX-2 cartridge, washing with a DCM/MeOH mixture and eluting the product with 2 M NH$_3$ in MeOH. The basic washings were concentrated in vacuo and the residue purified by reverse phase chromatography (C18, MeCN/Water/0.1% NH$_4$OH as eluent) to give N-((1-(6-(6-(difluoromethyl)imidazo[1,2-b]pyridazin-3-yl)pyrimidin-4-yl)piperidin-3-yl)methyl)azetidine-3-sulfonamide (7.5 mg, 17%).

The following compound was prepared according to a procedure similar to Example 63:
(S)—N-(1-(6-(6-(Difluoromethyl)imidazo[1,2-b]pyridazin-3-yl)pyrimidin-4-yl)piperidin-3-yl)azetidine-3-sulfonamide II-435.

Example 64: 1-(6-(6-(Difluoromethyl)imidazo[1,2-b]pyridazin-3-yl)pyrimidin-4-yl)-N-(methylsulfonyl)piperidine-3-carboxamide, II-460

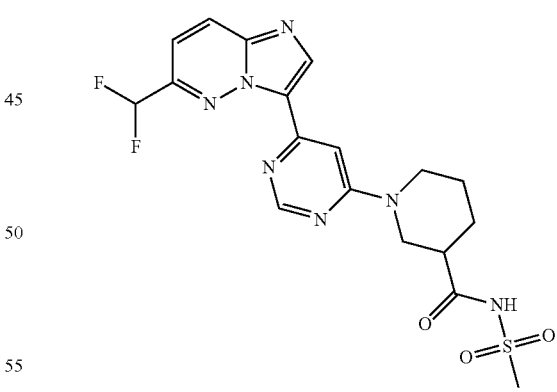

3-(Ethyliminomethyleneamino)-N,N-dimethyl-propan-1-amine hydrochloride (9 mg, 0.046 mmol) was added to a suspension of methanesulfonamide (6 mg, 0.066 mmol), DMAP (12 mg, 0.1 mmol) and 1-[6-[6-(difluoromethyl)imidazo[1,2-b]pyridazin-3-yl]pyrimidin-4-yl]piperidine-3-carboxylic acid (di-trifluoroacetate) (20 mg, 0.033 mmol, prepared according to a procedure similar to Example 1) in CH$_3$CN (2 mL) and the mixture was stirred at ambient temperature for 24 hours. The solvent was removed in vacuo and the residue purified by reverse phase chromatography (C18, MeCN/Water/0.05% TFA as eluent to give 1-(6-(6-(difluoromethyl)imidazo[1,2-b]pyridazin-3-yl)pyrimidin-4-yl)-N-(methylsulfonyl)piperidine-3-carboxamide II-460 (14 mg, 64%).

Example 65: N-((1-(6-(6-(Difluoromethyl)imidazo [1,2-b]pyridazin-3-yl)pyrimidin-4-yl)piperidin-3-yl) methyl)-2-(dimethylamino)-N-(methylsulfonyl)acetamide, II-456

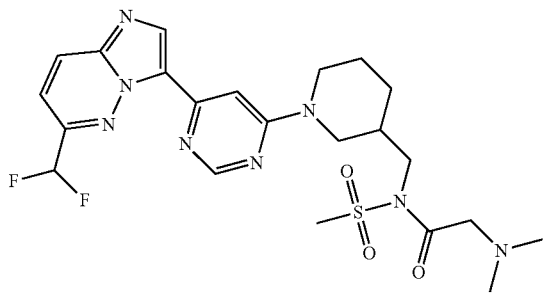 [SMILES: CN(C)CC(=O)N(CC1CCCN(c2cc(-c3cnc4ccc(C(F)F)nn34)ncn2)C1)S(C)(=O)=O]

N-[[1-[6-[6-(Difluoromethyl)imidazo[1,2-b]pyridazin-3-yl]pyrimidin-4-yl]-3-piperidyl]methyl]methanesulfonamide (50 mg, 0.114 mmol) was suspended in THF (2 mL) and NaH (9 mg, 0.23 mmol) was added. After 5 minutes, 2-bromoacetyl bromide (23 mg, 0.11 mmol) was added and the mixture was stirred at ambient temperature for 5 minutes. 2-Bromoacetyl bromide (23 mg, 0.11 mmol) was added and the reaction was stirred at ambient temperature for a further 5 minutes. The reaction was partitioned between an aqueous saturated solution of NH$_4$Cl and DCM. The organic layer was dried and concentrated in vacuo. The residue was dissolved in 2 M HNMe$_2$ in THF (4 mL) and the mixture was stirred at ambient temperature for 5 minutes before being concentrated in vacuo. Purification by reverse phase chromatography (C18, MeCN/Water/0.05% TFA as eluent) gave N-((1-(6-(6-(difluoromethyl)imidazo[1,2-b]pyridazin-3-yl) pyrimidin-4-yl)piperidin-3-yl)methyl)-2-(dimethylamino)-N-(methylsulfonyl)acetamide II-456 (15 mg, 14%).

Example 66: N-((1-Acetyl-4-(6-(6-(difluoromethyl) imidazo[1,2-b]pyridazin-3-yl)pyrimidin-4-yl)-3-methylpiperazin-2-yl)methyl)methanesulfonamide, II-515

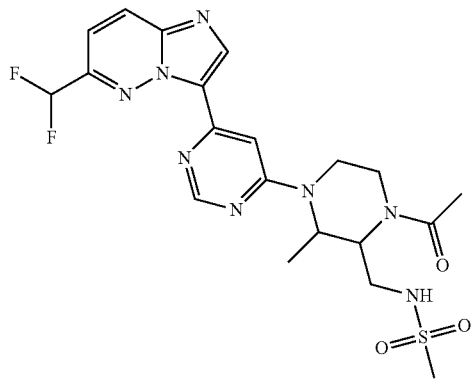 [SMILES: CC(=O)N1CCN(c2cc(-c3cnc4ccc(C(F)F)nn34)ncn2)C(C)C1CNS(C)(=O)=O]

N-[[4-[6-[6-(Difluoromethyl)imidazo[1,2-b]pyridazin-3-yl]pyrimidin-4-yl]-3-methyl-piperazin-2-yl]methyl]methanesulfonamide (25 mg, 0.055 mmol) was dissolved in DCM (550 μL) before addition of triethylamine (9 mg, 12 μL, 0.083 mmol) then acetyl chloride (5 mg, 5 μL, 0.072 mmol). The solution was stirred at ambient temperature for 30 minutes, then concentrated under reduced pressure. The residue was purified by reverse phase chromatography (C18, MeCN/Water/0.05% TFA as eluent) to give N-[[1-acetyl-4-[6-[6-(difluoromethyl)imidazo[1,2-b]pyridazin-3-yl]pyrimidin-4-yl]-3-methyl-piperazin-2-yl]methyl]methanesulfonamide II-515 as a white solid (17 mg, 62%).

Example 67: 4-[6-[6-(Difluoromethyl)imidazo[1,2-b]pyridazin-3-yl]pyrimidin-4-yl]-1-imino-1,4-thiazinane 1-oxide, II-676

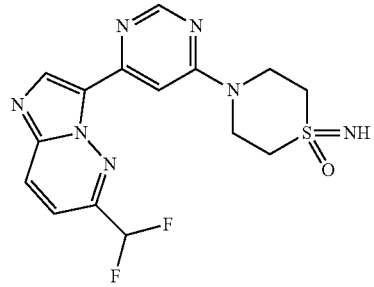 [SMILES: N=S1(=O)CCN(c2cc(-c3cnc4ccc(C(F)F)nn34)ncn2)CC1]

To a solution of 4-[6-[6-(difluoromethyl)imidazo[1,2-b] pyridazin-3-yl]pyrimidin-4-yl]-1,4-thiazinane 1-oxide (166 mg, 0.45 mmol, prepared according to a procedure similar to Example 1) in MeOH (1.5 mL) was added carbamic acid (144 mg, 1.8 mmol) and iodobenzene diacetate (450 mg, 1.4 mmol). The cloudy solution was stirred for 18 hours then 2 mL of MeOH was added. After 5 days, 2 mL of DCM was added followed by 2 mL of toluene, and the mixture was heated at 60° C. for 4 hours. The solution was filtered, the solvent was removed in vacuo and the residue purified by reverse phase chromatography (C18, MeCN/Water/0.1% NH$_4$OH as eluent) to give 4-[6-[6-(difluoromethyl)imidazo [1,2-b]pyridazin-3-yl]pyrimidin-4-yl]-1-imino-1,4-thiazinane 1-oxide (tri-trifluoroacetate salt) (6.2 mg, 2%).

Example 68: 1-[4-[6-[5-(Difluoromethyl)pyrazolo[1,5-a]pyrimidin-3-yl]pyrimidin-4-yl]piperazin-1-yl] ethanone, III-1

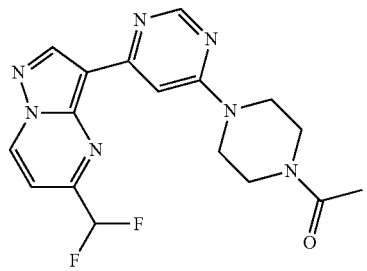 [SMILES: CC(=O)N1CCN(c2cc(-c3cnn4ccc(C(F)F)nc34)ncn2)CC1]

A mixture of 3-(6-chloropyrimidin-4-yl)-5-(difluoromethyl)-2-iodo-pyrazolo[1,5-a]pyrimidine (50 mg, 0.123 mmol), 1-piperazin-1-ylethanone (16 mg, 0.123 mmol) and DIPEA (32 mg, 43 µL, 0.245 mmol) in NMP (3 mL) was heated at 100° C. in the microwave for 1 hour. The mixture was purified directly by reverse phase chromatography (C18, MeCN/water/0.05% TFA as eluent). The desired fractions were combined in vacuo and the residue was dissolved in MeOH (10 mL). Pd on C, wet, Degussa (50 mg, 0.470 mmol) was added and the mixture was placed under a balloon of hydrogen and stirred at ambient temperature for 1 hour. The catalyst was removed by filtration and the filtrate concentrated in vacuo. The residue was purified by reverse phase chromatography (C18, MeCN/water/0.05% TFA as eluent) to give 1-[4-[6-[5-(Difluoromethyl)pyrazolo[1,5-a]pyrimidin-3-yl]pyrimidin-4-yl]piperazin-1-yl]ethanone (trifluoroacetate salt) as a white solid (1.7 mg, 3%); $^1$H NMR (500 MHz, DMSO-$d_6$) δ 9.54 (d, 1H), 9.02 (s, 1H), 8.70 (s, 1H), 7.80 (d, 1H), 7.55 (d, 1H), 7.35-7.07 (m, 1H), 3.90-3.61 (m, 8H), 2.08 (s, 3H); MS m/z: 374.1 (M+H)$^+$.

The following compounds were prepared using a methodology similar to the one described in Example 68:

N-[[1-[6-[5-(Difluoromethyl)pyrazolo[1,5-a]pyrimidin-3-yl]pyrimidin-4-yl]-3-piperidyl]methyl]methanesulfonamide III-2;

1-[6-[5-(Trifluoromethyl)pyrazolo[1,5-a]pyrimidin-3-yl]pyrimidin-4-yl]-1,4-diazepan-5-one III-3.

Example 69: N-[[(2R)-4-[6-[5-(Difluoromethyl)-6-fluoro-pyrazolo[1,5-a]pyrimidin-3-yl]pyrimidin-4-yl]morpholin-2-yl]methyl]methanesulfonamide, III-5

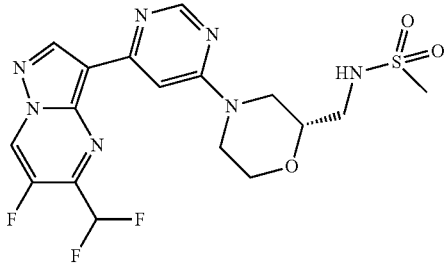 [SMILES: CS(=O)(=O)NC[C@H]1CN(c2cc(-c3cnn4cc(F)c(C(F)F)nc34)ncn2)CCO1]

Step 1: N-[[(2R)-4-[6-[5-(Difluoromethyl)-6-fluoro-2-iodo-pyrazolo[1,5-a]pyrimidin-3-yl]pyrimidin-4-yl]morpholin-2-yl]methyl]methanesulfonamide A mixture of 3-(6-chloropyrimidin-4-yl)-5-(difluoromethyl)-6-fluoro-2-iodo-pyrazolo[1,5-a]pyrimidine (55 mg, 0.129 mmol), DIPEA (84 mg, 113 µL, 0.646 mmol) and N-[[(2R)-morpholin-2-yl]methyl]methanesulfonamide (30 mg, 0.154 mmol) in NMP (2 mL) was stirred at 80° C. for 5 hours. The residue was purified directly by reverse phase chromatography (C18, MeCN/water—0.1% NH$_4$OH as eluent) to give N-[[(2R)-4-[6-[5-(difluoromethyl)-6-fluoro-2-iodo-pyrazolo[1,5-a]pyrimidin-3-yl]pyrimidin-4-yl]morpholin-2-yl]methyl]methanesulfonamide as an off-white solid that was used directly in the next step; MS m/z: 584.1 (M+H)$^+$.

Step 2: N-[[(2R)-4-[6-[5-(Difluoromethyl)-6-fluoro-pyrazolo[1,5-a]pyrimidin-3-yl]pyrimidin-4-yl]morpholin-2-yl]methyl]methanesulfonamide N-[[(2R)-4-[6-[5-(Difluoromethyl)-6-fluoro-2-iodo-pyrazolo[1,5-a]pyrimidin-3-yl]pyrimidin-4-yl]morpholin-2-yl]methyl]methanesulfonamide (75 mg, 0.129 mmol) was suspended in MeOH (5 mL) and Pd on C, wet, Degussa (14 mg, 0.129 mmol) was added. The mixture was placed under a balloon of hydrogen and stirred at ambient temperature for 1 hour. The catalyst was removed by filtration and the filtrate concentrated in vacuo. The residue was purified by reverse phase chromatography (C18, MeCN/water/0.05% TFA as eluent) to give N-[[(2R)-4-[6-[5-(difluoromethyl)-6-fluoro-pyrazolo[1,5-a]pyrimidin-3-yl]pyrimidin-4-yl]morpholin-2-yl]methyl]methanesulfonamide as a white solid (2.9 mg, 4%); $^1$H NMR (500 MHz, DMSO-$d_6$) δ 10.03 (d, 1H), 9.02 (s, 1H), 8.70 (s, 1H), 7.77 (d, 1H), 7.32 (t, 1H), 7.30 (t, 1H), 4.61-4.37 (m, 1H), 4.26 (s, 1H), 4.09-4.03 (m, 1H), 3.65-3.55 (m, 2H), 3.16 (m, 3H), 2.96 (s, 3H), 2.95-2.87 (m, 1H); MS m/z: 458.1 (M+H)$^+$.

The following compounds were prepared using a methodology similar to the one described in Example 69:

N-[[(2S)-4-[6-[5-(Difluoromethyl)-6-fluoro-pyrazolo[1,5-a]pyrimidin-3-yl]pyrimidin-4-yl]morpholin-2-yl]methyl]methanesulfonamide III-10;

N-[[(3S,5S)-1-[6-[5-(Difluoromethyl)-6-fluoro-pyrazolo[1,5-a]pyrimidin-3-yl]pyrimidin-4-yl]-4,4-difluoro-5-methyl-3-piperidyl]methyl]methanesulfonamide III-11.

Example 70: N-[[(2S)-4-[6-[5-(Difluoromethyl)pyrazolo[1,5-a]pyrimidin-3-yl]pyrimidin-4-yl]morpholin-2-yl]methyl]methanesulfonamide, III-4

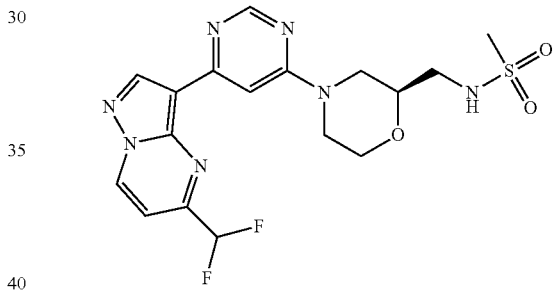

Step 1: N-[[(2S)-4-[6-[2-Amino-5-(difluoromethyl)pyrazolo[1,5-a]pyrimidin-3-yl]pyrimidin-4-yl]morpholin-2-yl]methyl]methanesulfonamide DIPEA (436 mg, 587 µL, 3.37 mmol) was added to a solution of 3-(6-chloropyrimidin-4-yl)-5-(difluoromethyl)pyrazolo[1,5-a]pyrimidin-2-amine (100 mg, 0.337 mmol) and N-[[(2S)-morpholin-2-yl]methyl]methanesulfonamide (72 mg, 0.371 mmol) in NMP (2 mL) and the mixture was stirred at 85° C. for 16 hours. The reaction was cooled to ambient temperature and loaded onto a pre-wetted SCX-2 column. The column was washed with MeOH and the product eluted with 2 M NH$_3$ in MeOH solution. The eluent was concentrated in vacuo to give N-[[(2S)-4-[6-[2-amino-5-(difluoromethyl)pyrazolo[1,5-a]pyrimidin-3-yl]pyrimidin-4-yl]morpholin-2-yl]methyl]methanesulfonamide as an off-white solid that was used directly in the next step; MS m/z: 455.2 (M+H)$^+$.

Step 2: N-[[(2S)-4-[6-[5-(Difluoromethyl)-2-iodo-pyrazolo[1,5-a]pyrimidin-3-yl]pyrimidin-4-yl]morpholin-2-yl]methyl]methanesulfonamide NaNO$_2$ (47 mg, 0.673 mmol) in water (0.5 mL) was slowly added to a solution of KI (140 mg, 0.842 mmol), p-toluenesulfonic acid (174 mg, 1.01 mmol) and N-[[(2S)-4-[6-[2-amino-5-(difluoromethyl)pyrazolo[1,5-a]pyrimidin-3-yl]pyrimidin-4-yl]morpholin-2-yl]methyl]methanesulfonamide (153 mg, 0.337 mmol) in acetonitrile (23 mL) and water (8 mL). The solution was stirred at ambient temperature for 4 hours before further KI (140 mg, 0.842 mmol) and p-toluenesulfonic acid (174 mg, 1.01 mmol) in water (1 mL) was added. After 5 minutes, $NaNO_2$ (47 mg, 0.673 mmol) in water (0.5 mL) was added and the mixture was stirred at ambient temperature for 16 hours. The reaction was quenched by the addition of saturated aqueous $NaHCO_3$ and saturated aqueous $Na_2S_2O_3$ and the mixture was concentrated in vacuo. The aqueous phase was extracted with DCM (×3) and the combined organic extracts dried ($MgSO_4$), filtered and concentrated in vacuo. The crude mixture was purified by column chromatography (silica, DCM/MeOH gradient as the eluent) to give N-[[(2S)-4-[6-[5-(difluoromethyl)-2-iodo-pyrazolo[1,5-a]pyrimidin-3-yl]pyrimidin-4-yl]morpholin-2-yl]methyl]methanesulfonamide as an off-white solid that was used directly in the next step; MS m/z: 566.1 $(M+H)^+$.

Step 3: N-[[(2S)-4-[6-[5-(Difluoromethyl)pyrazolo[1,5-a]pyrimidin-3-yl]pyrimidin-4-yl]morpholin-2-yl]methyl]methanesulfonamide, III-4

N-[[(2S)-4-[6-[5-(Difluoromethyl)-2-iodo-pyrazolo[1,5-a]pyrimidin-3-yl]pyrimidin-4-yl]morpholin-2-yl]methyl]methanesulfonamide (190 mg, 0.337 mmol) was dissolved in MeOH (10 mL) and Pd on C, wet, Degussa (36 mg, 0.337 mmol) was added. The mixture was stirred under a balloon of hydrogen at ambient temperature for 30 minutes. The catalyst was removed by filtration and the filtrate concentrated in vacuo. The residue was purified by reverse phase chromatography (C18, MeCN/water/0.05% TFA as eluent) to give N-[[(2S)-4-[6-[5-(Difluoromethyl)pyrazolo[1,5-a]pyrimidin-3-yl]pyrimidin-4-yl]morpholin-2-yl]methyl]methanesulfonamide (bis-trifluoroacetate salt) as a white solid (6.4 mg, 3%); $^1$H NMR (500 MHz, DMSO-$d_6$) δ 9.58 (d, 1H), 9.08 (s, 1H), 8.79 (d, 1H), 7.81 (d, 1H), 7.61 (d, 1H), 7.32 (t, 1H), 7.17 (t, 1H), 4.54 (s, 1H), 4.33 (s, 1H), 4.07 (ddd, 1H), 3.68-3.55 (m, 2H), 3.34-3.24 (m, 1H), 3.22-3.09 (m, 2H), 3.07-2.97 (m, 1H), 2.97 (s, 3H); MS m/z: 440.2 $(M+H)^+$.

Example 71: N-[[(3S,5S)-1-[6-[5-(Difluoromethyl)pyrazolo[1,5-a]pyrimidin-3-yl]pyrimidin-4-yl]-4,4-difluoro-5-methyl-3-piperidyl]methyl]methanesulfonamide, III-12

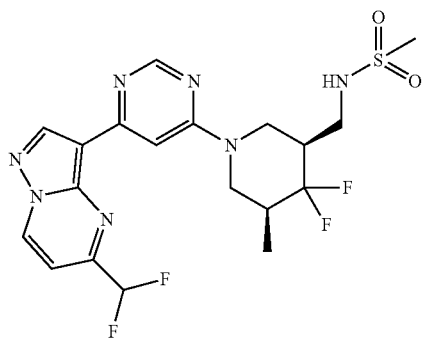 [SMILES: C[C@H]1CN(c2cc(-c3cnn4ccc(C(F)F)nc34)ncn2)C[C@@H](CNS(C)(=O)=O)C1(F)F]

3-(6-Chloropyrimidin-4-yl)-5-(difluoromethyl)pyrazolo[1,5-a]pyrimidine (13.2 mg, 0.047 mmol), N-[[(3S,5S)-4,4-difluoro-5-methyl-3-piperidyl]methyl]methanesulfonamide (11.4 mg, 0.047 mmol) and DIPEA (16.4 μL, 0.094 mmol) were heated in NMP (400 μL) at 90° C. Once the reaction was complete the mixture was cooled to ambient temperature, filtered and purified by reverse phase chromatography (C18, MeCN/water/0.05% TFA as eluent) to afford the trifluoroacetic acid salt of N-[[(3S,5S)-1-[6-[5-(difluoromethyl)pyrazolo[1,5-a]pyrimidin-3-yl]pyrimidin-4-yl]-4,4-difluoro-5-methyl-3-piperidyl]methyl]methanesulfonamide (14.7 mg, 47%).

The following compounds were prepared using a methodology similar to the one described in Example 71:

N-[[1-[6-[5-(Difluoromethyl)pyrazolo[1,5-a]pyrimidin-3-yl]pyrimidin-4-yl]-4,4-difluoro-2,5-dimethyl-3-piperidyl]methyl]methanesulfonamide III-13;

[1-[6-[5-(Difluoromethyl)pyrazolo[1,5-a]pyrimidin-3-yl]pyrimidin-4-yl]-5-methyl-3-piperidyl]imino-dimethyl-oxo-6-sulfane III-14.

Example 72: N-[[(2S)-4-[4-[5-(Difluoromethyl)pyrazolo[1,5-a]pyrimidin-3-yl]-2-pyridyl]morpholin-2-yl]methyl]methanesulfonamide, III-6

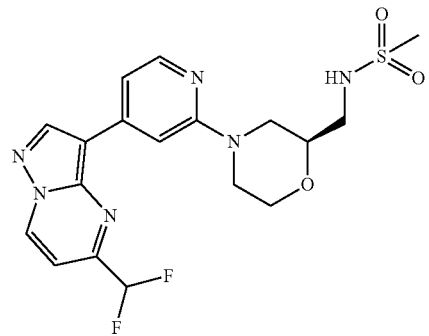 [SMILES: CS(=O)(=O)NC[C@@H]1CN(c2cc(-c3cnn4ccc(C(F)F)nc34)ccn2)CCO1]

N-[[(2S)-Morpholin-2-yl]methyl]methanesulfonamide (44 mg, 0.227 mmol), 5-(difluoromethyl)-3-(2-fluoro-4-pyridyl)pyrazolo[1,5-a]pyrimidine (40 mg, 0.151 mmol) and DIPEA (79 μL, 0.454 mmol) were heated in NMP (1 mL) at 170° C. under microwave conditions for 2 hours. The reaction mixture was cooled to ambient temperature and purified by reverse phase chromatography (C18, MeCN/water—0.1% $NH_4OH$ as eluent) to give N-[[(2S)-4-[4-[5-(difluoromethyl)pyrazolo[1,5-a]pyrimidin-3-yl]-2-pyridyl]morpholin-2-yl]methyl]methanesulfonamide as a white solid (3.5 mg, 5%); $^1$H NMR (500 MHz, DMSO-$d_6$) δ 9.43 (d, 1H), 9.09 (s, 1H), 8.23-8.18 (m, 1H), 7.61 (s, 1H), 7.56 (d, 1H), 7.42 (d, 1H), 7.26-7.01 (m, 2H), 4.38-4.26 (m, 1H), 4.18-4.07 (m, 1H), 4.02 (ddd, 1H), 3.69-3.55 (m, 2H), 3.14 (td, 2H), 3.02-2.88 (m, 4H), 2.72-2.59 (m, 1H); $^{19}$F NMR (471 MHz, DMSO-$d_6$) δ −116.51, −116.62; MS m/z: 439.1 $(M+H)^+$.

The following compound was prepared using a methodology similar to the one described in Example 72:

N-[[1-[4-[5-(Difluoromethyl)pyrazolo[1,5-a]pyrimidin-3-yl]-2-pyridyl]-4,4-difluoro-5-methyl-3-piperidyl]methyl]methanesulfonamide III-7.

Example 73: 1-[4-[6-[5-(Difluoromethyl)pyrazolo[1,5-a]pyrimidin-3-yl]pyrimidin-4-yl]piperazin-1-yl]ethanone, III-8

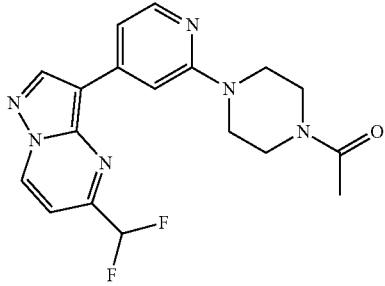 [SMILES: CC(=O)N1CCN(c2cc(-c3cnn4ccc(C(F)F)nc34)ccn2)CC1]

To a solution of 3-bromo-5-(difluoromethyl)pyrazolo[1,5-a]pyrimidine (30 mg, 0.121 mmol) in 1,4-dioxane (1 mL) and water (333 μL) was added 1-[4-[4-(4,4,5,5-tetramethyl-1,3,2-dioxaborolan-2-yl)-2-pyridyl]piperazin-1-yl]ethanone (48 mg, 0.145 mmol), 2 M aqueous $Na_2CO_3$ (182 μL, 0.363 mmol) and $Pd(PPh_3)_4$ (7 mg, 0.006 mmol) and the mixture was heated at 80° C. for 16 hours. The reaction mixture was cooled to ambient temperature and purified by reverse phase chromatography (C18, MeCN/water—0.1% $NH_4OH$ as eluent) to give 1-[4-[6-[5-(difluoromethyl)pyrazolo[1,5-a]pyrimidin-3-yl]pyrimidin-4-yl]piperazin-1-yl]ethanone as a yellow solid (22 mg, 49%); $^1H$ NMR (500 MHz, DMSO-$d_6$) δ 9.42 (d, 1H), 9.10 (s, 1H), 8.19 (dd, 1H), 7.61 (s, 1H), 7.58-7.51 (m, 1H), 7.41 (d, 1H), 7.15 (t, 1H), 3.69-3.63 (m, 2H), 3.63-3.52 (m, 6H), 2.07 (s, 3H); $^{19}F$ NMR (471 MHz, DMSO-$d_6$) δ −116.73, −116.85; MS m/z: 373.1 $(M+H)^+$.

Example 74: 1-[4-[6-[5-(Difluoromethyl)pyrazolo[1,5-a]pyrimidin-3-yl]pyrimidin-4-yl]piperazin-1-yl]ethanone, III-9

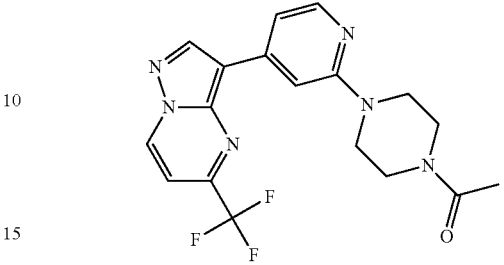

A mixture of 3-iodo-5-(trifluoromethyl)pyrazolo[1,5-a]pyrimidine (45 mg, 0.145 mmol), 1-[4-[4-(4,4,5,5-tetramethyl-1,3,2-dioxaborolan-2-yl)-2-pyridyl]piperazin-1-yl]ethanone (40 mg, 0.121 mmol), $Pd(PPh_3)_4$ (7 mg, 0.006 mmol), and 2 M aqueous $Na_2CO_3$ (185 μL, 0.370 mmol) in 1,4-dioxane (1.2 mL)/$H_2O$ (0.3 mL) was stirred at 80° C. for 18 hours. The reaction mixture was cooled to ambient temperature and the solvent removed under a stream of nitrogen. The residue was dissolved in DMSO and purified by reverse phase chromatography (C18, MeCN/water/ 0.05% TFA as eluent). The fractions were collected, passed through a sodium bicarbonate cartridge and lyophilised to give 1-[4-[6-[5-(difluoromethyl)pyrazolo[1,5-a]pyrimidin-3-yl]pyrimidin-4-yl]piperazin-1-yl]ethanone as a yellow solid (15.9 mg, 34%); $^1H$ NMR (500 MHz, DMSO-$d_6$) δ 9.55 (d, 1H), 9.18 (s, 1H), 8.22 (d, 1H), 7.61 (d, 1H), 7.58 (s, 1H), 7.51 (dd, 1H), 3.66-3.64 (m, 2H), 3.60-3.55 (m, 6H), 2.07 (s, 3H); $^{19}F$ NMR (471 MHz, DMSO-$d_6$) δ −67.26; MS m/z: 391.1 $(M+H)^+$.

TABLE 5

Analytical data for compounds of Formula II

| II- | LCMS_Plus | LCMS_RT | NMR |
|---|---|---|---|
| II-1 | 474 | 2.37 | 1H NMR (500 MHz, DMSO-d6) δ 8.66 (d, 1H), 8.65 (d, 1H), 8.06 (d, 1H), 7.72 (d, 1H), 7.40-7.10 (m, 2H), 4.65 (m, 1H), 4.50 (m, 1H), 3.40 (m, 1H), 3.15 (m, 1H), 2.96 (m, 4H), 2.30 (m, 2H), 2.06 (m, 1H), 1.20 (m, 1H). |
| II-2 | 474 | 2.37 | |
| II-3 | 452.2 | 2.38 | 1H NMR (500 MHz, DMSO-d6) δ 8.73 (d, 2H), 8.57 (d, 1H), 8.00 (s, 1H), 7.75 (d, 1H), 7.30 (t, 1H), 7.19 (m, 1H), 3.05 (m, 6H), 2.85 (m, 1H), 1.80-1.60 (m, 5H), 1.51 (m, 1H), 1.25 (d, 3H). |
| II-4 | 399.2 | 1.98 | 1H NMR (500 MHz, DMSO-d6) δ 8.73 (d, 2H), 8.57 (d, 1H), 8.04 (s, 1H), 7.75 (d, 1H), 7.69 (s, 2H), 7.45-7.23 (t, 1H), 4.63 (m, 1H), 4.54 (m, 1H), 4.34 (m, 1H), 4.07 (m, 1H), 3.75 (m, 1H), 3.33-3.25 (m, 2H). |
| II-5 | 468.2 | 1.96 | 1H NMR (500 MHz, DMSO-d6) δ 8.61 (s, 1H), 8.57-8.49 (m, 2H), 8.03 (s, 1H), 7.68 (d, J = 9.5 Hz, 1H), 7.42-7.09 (m, 2H), 4.39 (s, 1H), 2.93 (s, 5H), 1.73 (d, J = 12.8 Hz, 1H), 1.23 (d, J = 17.9 Hz, 6H). |
| II-6 | 468.2 | 1.87 | 1H NMR (500 MHz, DMSO-d6) δ 8.62 (s, 1H), 8.59-8.47 (m, 2H), 8.01 (d, J = 1.2 Hz, 1H), 7.69 (d, J = 9.4 Hz, 1H), 7.40-7.07 (m, 2H), 4.90 (s, 1H), 4.28 (d, J = 109.2 Hz, 1H), 2.99-2.85 (m, 6H), 2.79-2.62 (m, 1H), 1.79 (d, J = 11.3 Hz, 2H), 1.36 (t, J = 12.7 Hz, 1H), 1.10 (s, 3H). |
| II-7 | 467 | 1.7 | |
| II-8 | 438 | 2.16 | |
| II-9 | 363.1 | 1.84 | |
| II-10 | 437 | 1.81 | |

TABLE 5-continued

Analytical data for compounds of Formula II

| II- | LCMS_Plus | LCMS_RT | NMR |
|---|---|---|---|
| II-11 | 472 | 2.54 | 1H NMR (500 MHz, DMSO-d6) δ 8.84 (d, J = 1.1 Hz, 1H), 8.71 (s, 1H), 8.57 (d, J = 9.4 Hz, 1H), 8.42 (br d, J = 8.6 Hz, 1H), 8.18 (s, 1H), 7.74 (d, J = 9.4 Hz, 1H), 7.42-7.21 (m, 4H), 7.06 (td, J = 7.4, 1.0 Hz, 1H), 4.32 (dd, J = 10.9, 9.6 Hz, 1H), 4.14 (dd, J = 11.0, 5.0 Hz, 1H), 3.70 (tt, J = 9.6, 5.1 Hz, 1H), 3.46-3.32 (m, 1H), 3.22-3.17 (m, 1H), 2.91 (s, 3H). |
| II-12 | 454.2 | 1.81 | 1H NMR (500 MHz, Methanol-d4) δ 8.61 (s, 1H), 8.53 (d, J = 1.1 Hz, 1H), 8.37 (d, J = 9.4 Hz, 1H), 8.13 (d, J = 1.2 Hz, 1H), 7.69 (d, J = 9.5 Hz, 1H), 7.13 (t, J = 53.9 Hz, 1H), 4.42 (s, 1H), 4.29 (s, 1H), 4.10 (s, 1H), 3.51 (dd, J = 13.6, 2.5 Hz, 1H), 3.19-3.00 (m, 3H), 2.97 (s, 3H), 2.26 (td, J = 8.9, 4.3 Hz, 1H), 1.99-1.85 (m, 1H), 1.70 (ddd, J = 13.5, 10.4, 3.2 Hz, 1H). |
| II-13 | 454.2 | 1.79 | 1H NMR (500 MHz, Methanol-d4) δ 8.64 (s, 1H), 8.57 (d, J = 1.1 Hz, 1H), 8.38 (d, J = 9.5 Hz, 1H), 8.13 (d, J = 1.2 Hz, 1H), 7.70 (d, J = 9.5 Hz, 1H), 7.15 (t, J = 53.8 Hz, 1H), 4.57 (s, 1H), 3.69 (td, J = 10.2, 4.9 Hz, 1H), 3.19-3.04 (m, 2H), 2.99 (s, 3H), 2.80 (t, J = 12.5 Hz, 2H), 2.21 (d, J = 12.5 Hz, 1H), 1.89 (s, 1H), 1.41-1.19 (m, 1H). |
| II-14 | 423 | 2.21 | 1H NMR (500 MHz, DMSO-d6) δ 9.17 (d, J = 1.3 Hz, 1H), 8.75 (s, 1H), 8.56 (d, J = 9.4 Hz, 1H), 8.52 (d, J = 1.3 Hz, 1H), 7.74 (d, J = 9.4 Hz, 1H), 7.38 (t, J = 52.5 Hz, 1H), 3.57 (ddd, J = 14.0, 5.5, 3.9 Hz, 1H), 3.47 (dt, J = 13.3, 4.6 Hz, 1H), 3.40-3.33 (m, 1H), 3.28-3.26 (m, 1H), 3.13-2.99 (m, 1H), 2.93 (s, 3H), 2.12 (dq, J = 13.6, 4.3 Hz, 1H), 2.07-1.92 (m, 3H), 1.90-1.84 (m, 1H), 1.81-1.76 (m, 1H). |
| II-15 | 360 | 1.72 | 1H NMR (500 MHz, DMSO-d6) δ 8.68-8.59 (m, 2H), 8.53 (d, J = 9.4 Hz, 1H), 8.01 (d, J = 1.2 Hz, 1H), 7.76-7.63 (m, 2H), 7.37 (t, J = 53.7 Hz, 1H), 4.02-3.82 (m, 4H), 3.29-3.327 (m, 2H), 2.64-2.55 (m, 2H). |
| II-16 | 408 | 2.21 | 1H NMR (500 MHz, DMSO-d6) δ 8.86 (d, J = 1.1 Hz, 1H), 8.74 (s, 1H), 8.57 (d, J = 9.4 Hz, 1H), 8.46 (brs, 1H), 8.17 (s, 1H), 7.93 (d, J = 5.0 Hz, 1H), 7.74 (d, J = 9.4 Hz, 1H), 7.52-7.28 (m, 3H), 7.26 (brs, 1H), 7.07 (td, J = 7.4, 1.0 Hz, 1H), 4.51-4.41 (m, 1H), 4.39-4.27 (m, 2H). |
| II-17 | 438.2 | 2.11 | 1H NMR (500 MHz; dmso-d6) δ 8.71 (s, 1H), 8.67 (s, 1H), 8.57 (d, 1H), 7.75 (m, 2H), 7.32 (t, 1H), 7.06 (br s, 1H), 3.92 (m, 1H), 3.80 (m, 1H), 3.71 (m, 1H), 3.52 (m, 1H), 3.18 (m, 1H), 3.08 (m, 2H), 2.93 (s, 3H), 1.65 (m, 4H). |
| II-18 | 438.1 | 1.79 | |
| II-19 | 409.7 | 2.08 | 1H NMR (400 MHz, DMSO-d6) δ 8.80-8.68 (m, 2H), 8.57 (d, J = 9.4 Hz, 1H), 8.07 (d, J = 1.2 Hz, 1H), 7.75 (d, J = 9.4 Hz, 1H), 7.32 (t, J = 53.7 Hz, 1H), 4.86 (s, 1H), 4.35 (s, 1H), 3.50-3.32 (m, 2H), 3.26 (t, J = 12.6 Hz, 1H), 3.07 (s, 3H), 2.31-2.13 (m, 1H), 1.92 (tq, J = 19.0, 7.5, 5.7 Hz, 2H), 1.60 (t, J = 12.4 Hz, 1H). |
| II-20 | 365 | 2.98 | 1H NMR (500 MHz, DMSO-d6) δ 8.83 (d, J = 1.1 Hz, 1H), 8.71 (s, 1H), 8.56 (d, J = 9.4 Hz, 1H), 8.43 (brd, J = 8.1 Hz, 1H), 8.14 (s, 1H), 7.73 (d, J = 9.4 Hz, 1H), 7.49-7.22 (m, 3H), 7.01 (td, J = 7.4, 1.0 Hz, 1H), 4.23 (dd, J = 9.1, 8.0 Hz, 2H). (water peak obscures some signals) |
| II-21 | 409 | 2.24 | 1H NMR (400 MHz, DMSO-d6) δ 9.21 (d, J = 1.3 Hz, 1H), 8.76 (s, 1H), 8.62 (d, J = 1.4 Hz, 1H), 8.57 (d, J = 9.5 Hz, 1H), 7.75 (d, J = 9.4 Hz, 1H), 7.40 (t, J = 53.7 Hz, 1H), 3.81 (d, J = 10.6 Hz, 1H), 3.59 (d, J = 11.9 Hz, 1H), 3.21-2.99 (m, 2H), 2.92 (s, 3H), 2.88-2.76 (m, 1H), 2.09 (d, J = 12.3 Hz, 1H), 1.89 (d, J = 12.7 Hz, 1H), 1.83-1.60 (m, 2H). |
| II-22 | 424 | 2.07 | 1H NMR (500 MHz, DMSO-d6) δ 8.62 (s, 1H), 8.61 (d, J = 1.2 Hz, 1H), 8.53 (d, J = 9.4 Hz, 1H), 7.96 (s, 1H), 7.68 (d, J = 9.4 Hz, 1H), 7.32 (t, J = 55.0 Hz, 1H), 4.07-3.72 (m, 4H), 3.50 (brs, 2H), 2.87 (s, 3H), 1.96 (brs, 2H), water peak obscures some signals. |

TABLE 5-continued

Analytical data for compounds of Formula II

| II- | LCMS_Plus | LCMS_RT | NMR |
|---|---|---|---|
| II-23 | 438 | 1.75 | 1H NMR (500 MHz, DMSO-d6) 8.64 (s, 1H), 8.59 (s, 1H), 8.40 (m, 1H), 8.12 (s, 1H), 7.29-7.02 (t, 1H), 4.52-4.41 (m, 3H), 4.13 (m, 1H), 3.74 (m, 3H), 3.06-2.98 (m, 5H). |
| II-24 | 425 | 1.9 | 1H NMR (500 MHz, DMSO-d6) δ 8.62 (s, 1H), 8.60 (d, J = 1.1 Hz, 1H), 8.53 (d, J = 9.4 Hz, 1H), 7.95 (s, 1H), 7.68 (d, J = 9.4 Hz, 1H), 7.32 (t, J = 55.0 Hz, 1H), 6.76 (s, 2H), 4.08-3.71 (m, 4H), 3.51-3.33 (m, 2H), 3.22-3.11 (m, 2H), 1.96 (br s, 2H). |
| II-25 | 453.1 | 1.66 | 1 H NMR (500 MHz, DMSO-d6) δ 8.70 (m, 2H), 8.55 (d, 1H), 8.29 (s, 1H), 7.96 (s, 1H), 7.73 (d, 1H), 7.41-7.25 (m, 2H), 4.35-4.10 (br m, 2H), 4.06 (m, 1H), 3.91 (m, 1H), 3.60 (m, 1H), 3.15-3.12 (m, 1H), 3.07-3.04 (m, 1H), 2.92 (s, 3H). |
| II-26 | 436.2 | 2.07 | 1H NMR (500 MHz, DMSO-d6) δ 8.62 (d, J = 3.4 Hz, 1H), 8.58 (dd, J = 2.0, 1.1 Hz, 1H), 8.52 (dd, J = 9.4, 1.4 Hz, 1H), 7.99 (dd, J = 9.9, 1.2 Hz, 1H), 7.69 (dd, J = 9.4, 2.1 Hz, 1H), 7.43 (d, J = 24.2 Hz, 1H), 4.45 (dd, J = 72.8, 25.2 Hz, 2H), 3.25-3.00 (m, 4H), 2.97 (d, J = 6.9 Hz, 3H), 2.62 (d, J = 4.0 Hz, 3H), 2.20 (tqd, J = 10.9, 7.5, 4.3 Hz, 1H), 1.98 (ddd, J = 23.2, 9.7, 5.2 Hz, 1H), 1.81-1.71 (m, 1H), 1.50 (dddt, J = 22.1, 20.3, 11.7, 5.8 Hz, 2H). |
| II-27 | 307.1 | 0.88 | 1H NMR (500 MHz, DMSO) δ 8.85 (dd, J = 5.4, 0.6 Hz, 1H), 8.81 (s, 1H), 8.69 (d, J = 0.9 Hz, 1H), 8.42 (d, J = 9.5 Hz, 1H), 8.26 (dd, J = 5.3, 1.5 Hz, 1H), 8.17 (dt, J = 8.4, 1.8 Hz, 2H), 7.63-7.56 (m, 3H), 7.56-7.49 (m, 1H). |
| II-28 | 366.1 | 2.14 | |
| II-29 | 413 | 1.81 | 1H NMR (500 MHz, Chloroform-d) δ 8.80 (d, 1H), 8.72 (d, 1H), 8.29 (d, 2H), 8.26 (m, 1H), 7.97 (d, 1H), 7.49-7.47 (d, 1H), 6.97-6.69 (t, 1H), 4.67 (m, 1H), 4.28 (m, 1H), 4.22-4.04 (m, 3H), 3.83 (m, 1H), 3.71 (m, 1H), 3.25 (m, 1H), 2.80 (m, 1H). |
| II-30 | 398.3 | 2.11 | 1H NMR (400 MHz, DMSO-d6) δ 9.21 (dd, J = 3.8, 1.3 Hz, 1H), 8.76 (s, 1H), 8.66-8.48 (m, 2H), 7.75 (dd, J = 9.5, 5.4 Hz, 1H), 7.39 (td, J = 53.7, 15.3 Hz, 1H), 4.56 (d, J = 12.2 Hz) and 4.32 (d, J = 12.5 Hz, 1H), 4.23-4.02 (m, 2H), 3.91 (d, J = 13.3 Hz) and 3.73 (d, J = 13.2 Hz, 1H), 3.45 (dd, J = 13.6, 10.8 Hz, 1H), 3.22-2.59 (m, 2H), 2.12 (s, 1H), 2.00-1.75 (m, 2H), 1.75-1.43 (m, 1H). |
| II-31 | 454.7 | 2.18 | |
| II-32 | 455 | 2.17 | 1H NMR (400 MHz, Methanol-d4) δ 8.63 (s, 1H), 8.58 (s, 1H), 8.37 (d, 1H), 8.10 (s, 1H), 7.70 (d, 1H), 7.23-7.01 (t, 1H), 4.50 (m, 2H), 3.72 (m, 2H), 3.03 (s, 3H), 2.87 (m, 1H), 2.77 (m, 1H), 1.31 (d, 3H). |
| II-33 | 454.2 | 2.18 | 1H NMR (500 MHz, DMSO-d6) δ 8.76-8.63 (m, 2H), 8.56 (d, J = 9.4 Hz, 1H), 8.01 (d, J = 1.1 Hz, 1H), 7.73 (d, J = 9.4 Hz, 1H), 7.45-7.16 (m, 2H), 4.60-4.30 (m, 2H), 3.71-3.66 (m, 1H), 3.65-3.59 (m, 1H), 3.23-3.08 (m, 2H), 2.96 (s, 3H), 2.79 (q, J = 13.6 Hz, 2H), 1.23 (d, J = 6.2 Hz, 3H). |
| II-34 | 440.1 | 1.98 | 1H NMR (500 MHz, DMSO-d6) δ 8.73-8.65 (m, 2H), 8.56 (d, J = 9.4 Hz, 1H), 7.99 (d, J = 1.1 Hz, 1H), 7.73 (d, J = 9.4 Hz, 1H), 7.45-7.18 (m, 2H), 4.58-4.42 (m, 1H), 4.34-4.23 (m, 1H), 4.04 (ddd, J = 11.6, 3.6, 1.5 Hz, 1H), 3.66-3.53 (m, 2H), 3.25-3.10 (m, 3H), 3.00-2.85 (m, 4H). |
| II-35 | 488.1 | 2.55 | 1H NMR (500 MHz, DMSO-d6) δ 8.67 (d, J = 1.1 Hz, 1H), 8.65 (s, 1H), 8.54 (d, J = 9.4 Hz, 1H), 8.08 (s, 1H), 7.71 (d, J = 9.4 Hz, 1H), 7.30 (t, J = 53.6 Hz, 1H), 4.83 (s, 1H), 4.51 (s, 1H), 3.45 (dd, J = 13.4, 3.5 Hz, 1H), 2.99 (s, 4H), 2.89 (s, 2H), 2.29-2.13 (m, 2H), 1.07 (d, J = 6.7 Hz, 3H). |
| II-36 | 488.2 | 2.55 | 1H NMR (500 MHz, DMSO-d6) δ 8.70-8.60 (m, 2H), 8.53 (d, J = 9.4 Hz, 1H), 8.06 (d, J = 1.1 Hz, 1H), 7.70 (d, J = 9.4 Hz, 1H), 7.30 (d, J = 16.1 Hz, 2H), 4.82 (s, 1H), 4.52 (s, 1H), 3.44 (dd, J = 13.5, 3.5 Hz, 1H), 2.98 (s, 4H), 2.88 (q, J = 15.6, |

TABLE 5-continued

Analytical data for compounds of Formula II

| II- | LCMS_Plus | LCMS_RT | NMR |
|---|---|---|---|
| | | | 14.1 Hz, 2H), 2.30-2.09 (m, 2H), 1.06 (d, J = 6.7 Hz, 3H). |
| II-37 | 464.2 | 2.28 | 1H NMR (400 MHz, DMSO-d6) δ 8.70 (s, 1H), 8.49 (d, J = 9.4 Hz, 1H), 8.31 (d, J = 5.4 Hz, 1H), 7.76 (s, 1H), 7.68-7.64 (m, 2H), 7.29 (t, J = 53.8 Hz, 1H), 4.60 (s, 2H), 3.89-3.76 (m, 3H), 3.49 (s, 2H), 3.20-2.92 (m, 6H), 3.04 (s, 3H). |
| II-38 | 386.2 | 1.98 | 1H NMR (400 MHz, DMSO-d6) δ 8.69 (s, 1H), 8.49 (d, J = 9.4 Hz, 1H), 8.27 (d, J = 5.6 Hz, 1H), 7.73 (s, 1H), 7.65 (d, J = 9.4 Hz, 1H), 7.58 (d, J = 5.0 Hz, 1H), 7.29 (t, J = 53.9 Hz, 1H), 4.41-4.29 (m, 2H), 3.35 (d, J = 12.0 Hz, 2H), 3.09-2.96 (m, 5H), 2.83-2.76 (m, 1H), 2.56-2.33 (m, 3H). |
| II-39 | 453.1 | 2.02 | 1H NMR (500 MHz, DMSO-d6) δ 8.62 (s, 1H), 8.47 (d, J = 9.4 Hz, 1H), 8.20 (d, J = 5.3 Hz, 1H), 7.67-7.59 (m, 2H), 7.41-7.03 (m, 3H), 4.68 (d, J = 3.9 Hz, 1H), 4.15 (d, J = 10.7 Hz, 1H), 3.89 (d, J = 4.8 Hz, 1H), 3.77 (dd, J = 13.2, 4.8 Hz, 1H), 3.18 (d, J = 5.2 Hz, 2H), 3.01-2.86 (m, 7H), 1.72 (d, J = 12.9 Hz, 1H), 1.58-1.50 (m, 1H), 1.16 (s, 1H). |
| II-40 | 453.1 | 1.98 | 1H NMR (500 MHz, DMSO-d6) δ 8.63 (s, 1H), 8.47 (d, J = 9.4 Hz, 1H), 8.23 (dd, J = 5.3, 0.7 Hz, 1H), 7.67-7.65 (m, 1H), 7.62 (d, J = 9.4 Hz, 1H), 7.41 (dd, J = 5.3, 1.3 Hz, 1H), 7.37-7.13 (m, 1H), 7.12 (d, J = 6.2 Hz, 1H), 4.97 (d, J = 4.6 Hz, 1H), 4.48 (ddd, J = 30.4, 12.8, 4.2 Hz, 2H), 3.51 (tq, J = 9.6, 4.4 Hz, 1H), 2.99-2.88 (m, 5H), 2.12-2.00 (m, 1H), 1.74 (th, J = 10.8, 3.4 Hz, 1H), 1.09 (q, J = 11.9 Hz, 1H). |
| II-41 | 439.3 | 2.1 | 1H NMR (400 MHz, DMSO-d6) δ 9.20 (d, J = 1.3 Hz, 1H), 8.75 (s, 1H), 8.63-8.41 (m, 2H), 8.06 (s, 1H), 7.74 (d, J = 9.4 Hz, 1H), 7.69 (d, J = 0.8 Hz, 1H), 7.40 (t, J = 53.7 Hz, 1H), 4.40 (d, J = 93.6 Hz, 2H), 3.85 (s, 3H), 3.04 (s, 2H), 2.16 (d, J = 12.9 Hz, 1H), 2.04-1.77 (m, 2H), 1.70-1.51 (m, 1H), 1.27 (d, J = 6.7 Hz, 1H). |
| II-42 | 449.2 | 2.34 | |
| II-43 | 432 | 2.76 | 1H NMR (500 MHz, DMSO-d6) δ 8.62-8.53 (m, 2H), 8.46 (d, J = 9.4 Hz, 1H), 7.93 (d, J = 1.2 Hz, 1H), 7.63 (d, J = 9.3 Hz, 1H), 7.24 (t, J = 55.0 Hz, 1H), 4.80-3.72 (m, 4H), 3.47 (s, 1H), 3.12 (dd, J = 13.2, 8.3 Hz, 1H), 2.67 (d, J = 10.8 Hz, 1H), 2.27 (d, J = 13.2 Hz, 1H), 1.28 (d, J = 6.8 Hz, 3H), 1.08 (s, 9H). NB Spectrum acquired at 350K |
| II-44 | 463.2 | 2.41 | 1H NMR (500 MHz, Methanol-d4) δ 8.68 (d, J = 1.6 Hz, 1H), 8.60 (s, 1H), 8.40 (d, J = 9.5 Hz, 1H), 8.35 (d, J = 1.6 Hz, 1H), 7.70 (d, J = 9.5 Hz, 1H), 7.03 (t, J = 54.2 Hz, 1H), 5.61 (tt, J = 3.3, 1.5 Hz, 1H), 3.71 (tq, J = 2.6, 1.3 Hz, 2H), 3.60 (t, J = 7.0 Hz, 2H), 3.37 (d, J = 5.7 Hz, 2H), 2.84 (d, J = 5.1 Hz, 3H), 2.64 (s, 3H), 2.52 (t, J = 6.9 Hz, 2H), 2.34 (td, J = 5.6, 2.7 Hz, 2H). |
| II-45 | 488.1 | 2.55 | 1H NMR (500 MHz, DMSO-d6) δ 8.70 (d, J = 1.0 Hz, 1H), 8.68 (s, 1H), 8.56 (d, J = 9.4 Hz, 1H), 8.08 (s, 1H), 7.72 (d, J = 9.4 Hz, 1H), 7.42-7.17 (m, 2H), 3.45 (ddd, J = 13.6, 5.6, 3.7 Hz, 1H), 2.99 (s, 4H), 2.91 (s, 2H), 2.23 (d, J = 25.5 Hz, 2H), 1.07 (d, J = 6.7 Hz, 3H). |
| II-46 | 387 | 1.77 | 1H NMR (500 MHz, DMSO-d6) δ 8.68-8.59 (m, 2H), 8.53 (d, J = 9.4 Hz, 1H), 8.02 (d, J = 1.2 Hz, 1H), 7.70 (d, J = 9.4 Hz, 1H), 7.38 (t, J = 55.0 Hz, 1H), 6.59 (s, 1H), 4.55 (brs, 1H), 4.39 (brs, 1H), 3.81-3.64 (m, 2H), 3.44 (ddd, J = 9.3, 8.2, 1.1 Hz, 1H), 3.13-2.80 (m, 4H). |
| II-47 | 388 | 1.92 | 1H NMR (500 MHz, DMSO-d6) δ 8.71-8.64 (m, 2H), 8.55 (d, J = 9.4 Hz, 1H), 8.03 (d, J = 1.2 Hz, 1H), 7.73 (d, J = 9.4 Hz, 1H), 7.38 (t, J = 55.0 Hz, 1H), 4.71 (brs, 1H), 4.47-4.44 (m, 3H), 4.10 (dd, J = 8.9, 5.3 Hz, 1H), 3.99-3.90 (m, 1H), 3.76-3.71 (m, 1H), 3.18-2.98 (m, 3H). |
| II-48 | 437.3 | 2.09 | 1H NMR (400 MHz, DMSO-d6) δ 8.29 (t, J = 1.2 Hz, 1H), 7.92 (s, 1H), 7.83 (s, 1H), 7.55 (d, J = 9.5 Hz, 1H), 6.88 (d, J = 9.5 Hz, 1H), 6.26 (t, J = 54.0 Hz, 1H), 2.90 (dd, J = 7.6, 5.5 Hz, 5H), 2.48 |

TABLE 5-continued

Analytical data for compounds of Formula II

| II- | LCMS_Plus | LCMS_RT | NMR |
|---|---|---|---|
| | | | (s, 3H), 2.29 (d, J = 3.0 Hz, 4H), 1.51-1.29 (m, 1H), 1.15 (d, J = 8.8 Hz, 3H). |
| II-49 | 451.2 | 2.43 | 1H NMR (500 MHz, Methanol-d4) δ 9.08 (d, J = 1.8 Hz, 1H), 8.68 (d, J = 1.8 Hz, 1H), 8.57 (s, 1H), 8.38 (d, J = 9.5 Hz, 1H), 7.68 (d, J = 9.5 Hz, 1H), 7.03 (t, J = 54.0 Hz, 1H), 3.51-3.45 (m, 1H), 3.30-3.27 (m, 1H), 3.13 (dd, J = 13.2, 5.6 Hz, 1H), 3.07 (dd, J = 13.2, 8.3 Hz, 1H), 2.98-2.88 (m, 4H), 2.77-2.69 (m, 4H), 2.09-1.98 (m, 1H), 1.98-1.90 (m, 2H), 1.88-1.77 (m, 1H), 1.38-1.31 (m, 1H). |
| II-50 | 376 | 1.74 | 1H NMR (500 MHz, DMSO-d6) δ 8.73-8.66 (m, 2H), 8.55 (d, J = 9.4 Hz, 1H), 8.05 (d, J = 1.2 Hz, 1H), 7.73 (d, J = 9.4 Hz, 1H), 7.49-7.20 (m, 3H), 4.59 (brs, 1H), 4.17 (brs, 1H), 4.09-3.95 (m, 2H), 3.70 (td, J = 11.3, 2.9 Hz, 1H), 3.32 (ddd, J = 13.9, 10.8, 3.6 Hz, 1H), 3.17-3.14 (m, 1H). |
| II-51 | 400 | 2.03 | 1H NMR (500 MHz, DMSO-d6) δ 8.70 (d, J = 16.5 Hz, 2H), 8.57 (d, J = 9.4 Hz, 1H), 8.02 (d, J = 1.1 Hz, 1H), 7.79-7.68 (m, 2H), 7.34 (t, J = 52.5 Hz, 1H), 3.35-3.13 (m, 6H), 1.99-1.78 (m, 4H), 1.69-1.51 (m, 2H). |
| II-52 | 386 | 1.93 | 1H NMR (500 MHz, DMSO-d6) δ 8.68 (d, J = 1.7 Hz, 2H), 8.56 (d, J = 9.4 Hz, 1H), 8.38 (s, 1H), 8.03 (d, J = 1.1 Hz, 1H), 7.73 (d, J = 9.4 Hz, 1H), 7.42 (t, J = 52.5 Hz, 1H), 3.87-3.84 (m, 2H), 3.74-3.70 (m, 2H), 2.72 (s, 2H), 1.86 (ddd, J = 11.8, 7.4, 3.8 Hz, 2H), 1.76 (ddd, J = 12.6, 7.4, 3.7 Hz, 2H). |
| II-53 | 451.1 | 2.5 | |
| II-54 | 464 | 2.24 | 1H NMR (500 MHz, DMSO-d6) δ 8.68 (m, 2H), 8.58 (d, J = 9.4 Hz, 1H), 7.81-7.70 (m, 2H), 7.36 (t, J = 52.5 Hz, 1H), 3.22-3.20 (m, 4H), 3.14-3.10 (m, 2H), 2.91 (s, 3H), 2.07-1.91 (m, 2H), 1.77-1.70 (m, 4H), water peak obscures some signals. |
| II-55 | 575.3 | 2.41 | 1H NMR (500 MHz, DMSO-d6) δ 8.56 (s, 1H), 8.43 (d, J = 9.4 Hz, 1H), 7.58 (d, J = 9.4 Hz, 1H), 7.22 (t, J = 53.9 Hz, 1H), 7.06 (t, J = 6.2 Hz, 1H), 6.90 (s, 1H), 6.55 (s, 1H), 4.31 (s, 2H), 4.27-4.19 (m, 1H), 4.19-4.13 (m, 1H), 4.13-4.06 (m, 4H), 4.03 (s, 2H), 2.95-2.85 (m, 6H), 2.72-2.62 (m, 1H), 1.87-1.79 (m, 1H), 1.76 (s, 3H), 1.74-1.64 (m, 2H), 1.52-1.41 (m, 1H), 1.29-1.21 (m, 1H). |
| II-56 | 464 | 2.36 | 1H NMR (500 MHz, DMSO-d6) δ 8.62 (s, 1H), 8.57 (d, J = 1.1 Hz, 1H), 8.53 (d, J = 9.4 Hz, 1H), 8.03 (d, J = 1.2 Hz, 1H), 7.68 (d, J = 9.4 Hz, 1H), 7.32 (t, J = 52.5 Hz, 1H), 3.84-3.79 (m, 2H), 3.70-3.65 (m, 2H), 3.45-3.36 (m, 2H), 3.15 (d, J = 9.8 Hz, 1H), 2.98 (d, J = 9.8 Hz, 1H), 2.91 (s, 3H), 1.90-1.78 (m, 1H), 1.78-1.53 (m, 5H). |
| II-57 | 488.1 | 2.75 | |
| II-58 | 488.1 | 2.77 | 1H NMR (500 MHz, Methanol-d4) δ 8.49 (s, 1H), 8.33-8.32 (d, 1H), 8.26-8.25 (d, 1H), 7.86 (s, 1H), 7.64 (d, 1H), 7.45 (m, 1H), 7.23-6.95 (t, 1H), 4.70 (m, 1H), 4.62 (m, 1H), 3.62 (m, 1H), 3.15 (m, 1H), 3.00-2.90 (m, 4H), 2.96 (m, 1H), 2.30-2.05 (m, 2H), 1.13 (d, 3H). |
| II-59 | 438 | 2.17 | 1H NMR (500 MHz, DMSO-d6) δ 7.76 (s, 1H), 7.71 (s, 1H), 7.48 (d, J = 9.8 Hz, 1H), 7.06 (s, 1H), 6.83 (d, J = 9.8 Hz, 1H), 6.29-6.01 (m, 1H), 3.60 (d, J = 89.8 Hz, 1H), 2.57 (d, J = 11.7 Hz, 1H), 2.10 (qd, J = 13.2, 12.7, 6.5 Hz, 2H), 1.96 (d, J = 3.4 Hz, 3H), 1.04-0.88 (m, 3H), 0.70 (d, J = 12.6 Hz, 1H), 0.55 (d, J = 11.2 Hz, 1H), 0.31 (s, 1H), 0.13--0.23 (m, 1H). |
| II-60 | 466.2 | 2.42 | 1H NMR (500 MHz, DMSO-d6) δ 11.95 (s, 1H), 8.63 (s, 1H), 8.57 (d, J = 9.4 Hz, 1H), 7.75 (d, J = 9.5 Hz, 1H), 7.49 (s, 1H), 7.36 (d, J = 2.3 Hz, 1H), 7.28-6.93 (m, 2H), 5.94 (d, J = 2.3 Hz, 1H), 4.04 (dt, J = 13.8, 6.9 Hz, 2H), 3.23 (t, J = 12.3 Hz, 1H), 3.04 (dd, J = 13.3, 10.3 Hz, 1H), 2.98-2.62 (m, 8H), 1.87 (dt, J = 12.6, 4.2 Hz, 1H), 1.78 (dq, J = 12.9, 4.3 Hz, 2H), 1.58-1.47 (m, 1H), 1.43-1.29 (m, 1H). |

TABLE 5-continued

Analytical data for compounds of Formula II

| II- | LCMS_Plus | LCMS_RT | NMR |
|---|---|---|---|
| II-61 | 471.1 | 2.89 | 1H NMR (500 MHz, DMSO-d6) δ 8.71 (s, 1H), 8.48 (d, J = 9.4 Hz, 1H), 7.67-7.61 (m, 2H), 7.45 (s, 1H), 7.27 (t, J = 53.8 Hz, 1H), 7.11 (t, J = 6.1 Hz, 1H), 4.34-4.27 (m, 1H), 4.20-4.14 (m, 1H), 2.99 (ddd, J = 12.9, 11.5, 3.0 Hz, 1H), 2.95-2.86 (m, 5H), 2.74 (dd, J = 13.1, 10.3 Hz, 1H), 1.90-1.80 (m, 1H), 1.79-1.65 (m, 2H), 1.55-1.42 (m, 1H), 1.32-1.20 (m, 1H). |
| II-62 | 345.1 | 1.94 | |
| II-63 | 505.1 | 3.09 | 1H NMR (500 MHz, DMSO-d6) δ 8.80 (s, 1H), 8.50 (d, J = 9.4 Hz, 1H), 7.98 (s, 1H), 7.80 (d, J = 1.1 Hz, 1H), 7.66 (d, J = 9.4 Hz, 1H), 7.26 (t, J = 53.8 Hz, 1H), 7.11 (t, J = 6.1 Hz, 1H), 4.34 (dd, J = 13.1, 3.8 Hz, 1H), 4.30-4.21 (m, 1H), 3.12-3.01 (m, 1H), 2.98-2.86 (m, 5H), 2.82 (dd, 1H), 1.91-1.81 (m, 1H), 1.82-1.67 (m, 2H), 1.57-1.44 (m, 1H), 1.36-1.18 (m, 1H). |
| II-64 | 516 | 2.92 | 1H NMR (500 MHz, DMSO-d6) δ 8.47 (s, 1H), 8.42 (d, J = 9.4 Hz, 1H), 7.57 (d, J = 9.4 Hz, 1H), 7.31-7.06 (m, 2H), 6.76 (s, 1H), 6.67 (d, J = 1.0 Hz, 1H), 6.29 (q, J = 4.8 Hz, 1H), 3.83 (dd, J = 13.5, 3.9 Hz, 1H), 3.76 (dd, J = 13.3, 4.2 Hz, 1H), 3.62 (dd, J = 13.5, 6.7 Hz, 1H), 3.44 (dd, J = 13.3, 7.1 Hz, 1H), 3.26-3.20 (m, 1H), 3.01 (dd, J = 13.0, 9.8 Hz, 1H), 2.91 (s, 3H), 2.82 (d, J = 4.8 Hz, 3H), 2.35-2.18 (m, 2H), 1.02 (d, J = 6.8 Hz, 3H). |
| II-65 | 517 | 2.87 | 1H NMR (500 MHz, DMSO-d6) δ 8.47 (s, 1H), 8.43 (d, J = 9.4 Hz, 1H), 7.58 (d, J = 9.4 Hz, 1H), 7.31-7.04 (m, 2H), 6.76 (s, 1H), 6.70 (s, 1H), 6.32 (q, J = 4.7 Hz, 1H), 4.78-4.64 (m, 1H), 4.44-4.32 (m, 1H), 3.43 (ddd, J = 13.5, 5.5, 3.5 Hz, 1H), 2.99-2.90 (m, 4H), 2.83 (d, J = 4.8 Hz, 3H), 2.69 (dd, 2H), 2.23-2.00 (m, 2H), 1.03 (d, J = 6.7 Hz, 3H). |
| II-66 | 522.3 | 2.72 | 1H NMR (500 MHz, DMSO-d6) δ 8.58 (s, 1H), 8.43 (d, J = 9.4 Hz, 1H), 7.58 (d, J = 9.4 Hz, 1H), 7.23 (t, J = 53.8 Hz, 1H), 7.07 (t, J = 6.2 Hz, 1H), 7.00 (s, 1H), 6.87 (s, 1H), 4.30-4.24 (m, 1H), 4.19-4.13 (m, 1H), 3.75-3.70 (m, 4H), 3.52-3.43 (m, 4H), 2.96-2.83 (m, 6H), 2.65 (dd, J = 12.9, 10.1 Hz, 1H), 1.87-1.77 (m, 1H), 1.76-1.63 (m, 2H), 1.53-1.40 (m, 1H), 1.29-1.17 (m, 1H). |
| II-67 | 533.1 | 2.42 | |
| II-68 | 466.2 | 2.62 | 1H NMR (500 MHz, DMSO-d6) δ 8.53-8.36 (m, 2H), 7.56 (d, J = 9.4 Hz, 1H), 7.32-7.02 (m, 2H), 6.69 (s, 1H), 6.59 (s, 1H), 6.18 (s, 1H), 4.31-4.22 (m, 1H), 4.21-4.13 (m, 1H), 2.96-2.75 (m, 9H), 2.68-2.56 (m, 1H), 1.87-1.79 (m, 1H), 1.75-1.64 (m, 2H), 1.53-1.41 (m, 1H), 1.29-1.14 (m, 1H). |
| II-69 | 468.2 | 2.35 | 1H NMR (500 MHz, DMSO-d6) δ 8.48 (s, 1H), 8.43 (d, J = 9.4 Hz, 1H), 7.57 (d, J = 9.4 Hz, 1H), 7.33-6.96 (m, 3H), 6.76-6.67 (m, 2H), 4.27-4.18 (m, 1H), 4.13-4.03 (m, 1H), 4.01-3.93 (m, 1H), 3.66-3.53 (m, 2H), 3.12 (t, J = 6.0 Hz, 2H), 2.94 (s, 3H), 2.91-2.77 (m, 4H), 2.58 (dd, J = 12.8, 10.5 Hz, 1H). |
| II-70 | 450 | 2.26 | 1H NMR (500 MHz, DMSO-d6) δ 8.59-8.51 (m, 2H), 8.46 (d, J = 9.4 Hz, 1H), 7.99 (s, 1H), 7.62 (d, J = 9.4 Hz, 1H), 7.28 (t, J = 52.5 Hz, 1H), 4.82 (vbrs, 1H), 4.24 (vbrs, 1H), 3.79 (t, J = 7.9 Hz, 2H), 3.22-3.13 (m, 1H), 2.96 (s, 3H), 2.88-2.82 (m, 1H), 2.13 (d, J = 12.3 Hz, 1H), 2.10-1.94 (m, 3H), 1.79-1.74 (m, 1H), 1.50-1.39 (m, 1H). |
| II-71 | 502.1 | 2.73 | 1H NMR (500 MHz, DMSO-d6) δ 8.51 (s, 1H), 8.45 (d, J = 9.4 Hz, 1H), 7.60 (d, J = 9.4 Hz, 1H), 7.33-7.06 (m, 2H), 6.83-6.71 (m, 2H), 4.46-4.35 (m, 1H), 4.30-4.18 (m, 1H), 3.39-3.34 (m, 2H), 3.25-3.15 (m, 1H), 3.01-2.92 (m, 5H), 2.85 (s, 3H), 2.27-1.90 (m, 2H). |
| II-72 | 547.2 | 2.42 | 1H NMR (500 MHz, DMSO-d6) δ 9.79-9.53 (m, 1H), 8.56 (s, 1H), 8.44 (d, J = 9.4 Hz, 1H), 7.58 (d, J = 9.4 Hz, 1H), 7.21 (t, J = 54.0 Hz, 1H), |

TABLE 5-continued

Analytical data for compounds of Formula II

| II- | LCMS_Plus | LCMS_RT | NMR |
|---|---|---|---|
| | | | 7.06 (t, J = 6.1 Hz, 1H), 6.92 (s, 1H), 6.54 (d, J = 1.0 Hz, 1H), 4.48-4.38 (m, 2H), 4.29-4.13 (m, 6H), 4.11 (s, 2H), 2.93-2.87 (m, 6H), 2.84 (d, J = 5.0 Hz, 3H), 2.70-2.61 (m, 1H), 1.88-1.78 (m, 1H), 1.75-1.63 (m, 2H), 1.53-1.40 (m, 1H), 1.30-1.18 (m, 1H). |
| II-73 | 466.2 | 2.17 | 1H NMR (500 MHz, DMSO-d6) δ 9.13 (d, J = 1.8 Hz, 1H), 8.62 (s, 1H), 8.48 (d, J = 9.4 Hz, 1H), 8.34 (d, J = 1.9 Hz, 1H), 8.29-8.20 (m, 2H), 7.62 (d, J = 9.4 Hz, 1H), 7.23 (t, J = 53.8 Hz, 1H), 7.07 (t, J = 6.2 Hz, 1H), 4.31-4.21 (m, 2H), 3.22-3.14 (m, 1H), 3.10-2.88 (m, 6H), 2.83-2.74 (m, 1H), 2.58-2.52 (m, 1H), 1.95-1.78 (m, 3H), 1.74-1.60 (m, 1H), 1.30-1.13 (m, 1H). |
| II-74 | 336 | 0.88 | 1H NMR (500 MHz, DMSO-d6) δ 8.66-8.54 (m, 2H), 8.46 (d, J = 9.4 Hz, 1H), 7.61 (d, J = 9.4 Hz, 1H), 7.33-7.09 (m, 3H), 6.92 (d, J = 0.9 Hz, 1H), 4.61-4.45 (m, 2H), 4.35-4.24 (m, 1H), 4.24-4.14 (m, 1H), 3.03-2.95 (m, 1H), 2.95-2.88 (m, 5H), 2.74 (dd, J = 13.0, 10.2 Hz, 1H), 2.65 (t, J = 5.4 Hz, 2H), 2.07 (s, 3H), 1.89-1.80 (m, 1H), 1.78-1.65 (m, 2H), 1.54-1.43 (m, 1H), 1.32-1.22 (m, 1H). |
| II-75 | 487.2 | 2.57 | 1H NMR (500 MHz, DMSO-d6) δ 8.53 (s, 1H), 8.48 (d, J = 9.4 Hz, 1H), 8.37 (d, J = 5.9 Hz, 1H), 8.17 (d, J = 2.5 Hz, 1H), 7.61 (d, J = 9.4 Hz, 1H), 7.40-7.12 (m, 2H), 6.93 (dd, J = 6.0, 2.7 Hz, 1H), 4.30 (d, J = 14.0 Hz, 1H), 4.07 (d, J = 14.0 Hz, 1H), 3.44 (ddd, J = 13.4, 5.8, 3.5 Hz, 1H), 2.98 (s, 3H), 2.94-2.79 (m, 2H), 2.27-2.13 (m, 2H), 1.24 (s, 1H), 1.06 (d, J = 6.7 Hz, 3H). |
| II-76 | 332.1 | 2.34 | |
| II-77 | 380 | 2.2 | |
| II-78 | 487 | 2.76 | |
| II-79 | 343.1 | 1.94 | 1H NMR (500 MHz, DMSO-d6) δ 8.79 (s, 1H), 8.63 (s, 2H), 8.53 (d, J = 9.4 Hz, 1H), 8.17 (d, J = 6.6 Hz, 1H), 7.71 (d, J = 9.4 Hz, 1H), 7.66-7.49 (m, 2H), 7.29 (t, J = 53.9 Hz, 1H), 4.34 (s, 4H), 4.22 (t, J = 6.2 Hz, 4H). |
| II-80 | 466.2 | 2.24 | 1H NMR (500 MHz, DMSO-d6) δ 8.63 (s, 1H), 8.50 (d, J = 9.4 Hz, 1H), 8.16 (s, 2H), 7.70 (s, 1H), 7.66 (d, J = 9.4 Hz, 1H), 7.47 (s, 1H), 7.26 (t, J = 53.8 Hz, 1H), 7.09 (t, J = 6.1 Hz, 1H), 4.40-4.34 (m, 1H), 4.34-4.28 (m, 1H), 4.16-4.07 (m, 2H), 3.09-2.88 (m, 6H), 2.82 (dd, J = 13.0, 10.0 Hz, 1H), 1.94-1.84 (m, 1H), 1.82-1.67 (m, 2H), 1.57-1.44 (m, 1H), 1.38-1.22 (m, 1H). |
| II-81 | 494 | 2.33 | 1H NMR (500 MHz, DMSO-d6) δ 8.85 (s, 1H), 8.78-8.76 (d, 1H), 8.19-8.17 (d, 1H), 8.15-8.12 (m, 2H), 7.66 (d, 1H), 7.28-78.07 (t, 1H), 4.86-4.80 (m, 4H), 4.50 (m, 1H), 4.24 (d, 1H), 4.08 (m, 1H), 4.79 (d, 1H), 4.75-4.70 (m, 1H), 3.30-3.25 (masked, 3H), 3.20 (m, 1H), 3.11-3.7 (m, 1H), 2.95 (s, 3H). |
| II-82 | 461.1 | 2.72 | 1H NMR (500 MHz, DMSO-d6) δ 8.63 (s, 1H), 8.48 (d, J = 9.4 Hz, 1H), 8.06 (d, J = 1.6 Hz, 1H), 7.92-7.82 (m, 2H), 7.63 (d, J = 9.4 Hz, 1H), 7.24 (t, J = 53.8 Hz, 1H), 7.07 (t, J = 6.2 Hz, 1H), 3.57 (dd, J = 42.3, 11.8 Hz, 2H), 3.29 (s, 1H), 3.07-2.83 (m, 6H), 2.69 (dd, J = 11.8, 9.6 Hz, 1H), 1.85 (d, J = 11.6 Hz, 2H), 1.69 (d, J = 11.5 Hz, 1H), 1.21 (q, J = 11.1, 10.1 Hz, 1H). |
| II-83 | 534.2 | 2.61 | 1H NMR (500 MHz, DMSO-d6) δ 8.56 (s, 1H), 8.44 (d, J = 9.4 Hz, 1H), 7.59 (d, J = 9.5 Hz, 1H), 7.23 (t, J = 53.8 Hz, 1H), 7.06 (t, J = 6.1 Hz, 1H), 6.89 (s, 1H), 6.56 (s, 1H), 4.74 (s, 4H), 4.24-4.11 (m, 6H), 2.98-2.82 (m, 6H), 2.68 (dd, J = 12.9, 10.0 Hz, 1H), 1.88-1.78 (m, 1H), 1.76-1.63 (m, 2H), 1.54-1.40 (m, 1H), 1.30-1.17 (m, 1H). |
| II-84 | 508.2 | 2.43 | 1H NMR (500 MHz, DMSO-d6) δ 9.12-8.88 (m, 1H), 8.80-8.59 (m, 2H), 8.46 (d, J = 9.4 Hz, 1H), 7.61 (d, J = 9.4 Hz, 1H), 7.36-7.10 (m, 3H), 6.96 (d, J = 0.9 Hz, 1H), 5.39 (p, 1H), 4.52-4.37 (m, 2H), 4.30-4.19 (m, 1H), 4.18-4.03 (m, 3H), 3.04-2.87 (m, 6H), 2.72 (dd, J = 13.1, 10.2 Hz, 1H), |

TABLE 5-continued

Analytical data for compounds of Formula II

| II- | LCMS_Plus | LCMS_RT | NMR |
|---|---|---|---|
| | | | 1.90-1.79 (m, 1H), 1.78-1.63 (m, 2H), 1.56-1.41 (m, 1H), 1.35-1.21 (m, 1H). |
| II-85 | 508.2 | 2.39 | 1H NMR (500 MHz, DMSO-d6) δ 8.54 (s, 1H), 8.43 (d, J = 9.4 Hz, 1H), 7.57 (d, J = 9.4 Hz, 1H), 7.22 (t, J = 53.9 Hz, 1H), 7.06 (t, J = 6.1 Hz, 1H), 6.87 (s, 1H), 6.52 (s, 1H), 4.62-4.53 (m, 1H), 4.29-4.22 (m, 1H), 4.21-4.12 (m, 3H), 3.70 (dd, J = 8.4, 4.6 Hz, 3H), 2.92-2.85 (m, 6H), 2.68-2.61 (m, 1H), 1.88-1.79 (m, 1H), 1.76-1.64 (m, 2H), 1.52-1.40 (m, 1H), 1.28-1.17 (m, 1H). |
| II-86 | 534.2 | 2.7 | 1H NMR (500 MHz, DMSO-d6) δ 8.56 (s, 1H), 8.44 (d, J = 9.4 Hz, 1H), 7.59 (d, J = 9.4 Hz, 1H), 7.24 (t, J = 53.8 Hz, 1H), 7.07 (t, J = 6.2 Hz, 1H), 6.90 (s, 1H), 6.56 (s, 1H), 4.46 (t, J = 7.5 Hz, 2H), 4.26-4.20 (m, 3H), 4.18-4.12 (m, 1H), 4.07-4.03 (m, 2H), 2.97-2.82 (m, 8H), 2.71-2.61 (m, 1H), 1.88-1.77 (m, 1H), 1.76-1.63 (m, 2H), 1.54-1.41 (m, 1H), 1.30-1.16 (m, 1H). |
| II-87 | 437.1 | 2.28 | 1H NMR (500 MHz, DMSO-d6) δ 8.83 (d, J = 1.6 Hz, 1H), 8.65 (s, 1H), 8.49 (d, J = 9.4 Hz, 1H), 8.40 (d, J = 2.7 Hz, 1H), 8.37-8.29 (m, 1H), 7.64 (d, J = 9.4 Hz, 1H), 7.37-7.09 (m, 2H), 3.94-3.87 (m, 1H), 3.87-3.79 (m, 1H), 3.05-2.87 (m, 6H), 2.78 (dd, J = 12.7, 9.8 Hz, 1H), 1.90-1.73 (m, 3H), 1.65-1.53 (m, 1H), 1.34-1.19 (m, 1H). |
| II-88 | 387 | 2.22 | |
| II-89 | 510.2 | 2.65 | 1H NMR (500 MHz, DMSO-d6) δ 8.45-8.39 (m, 2H), 7.56 (d, J = 9.4 Hz, 1H), 7.29-7.02 (m, 2H), 6.69-6.61 (m, 2H), 6.25 (t, J = 5.5 Hz, 1H), 4.28-4.21 (m, 1H), 4.21-4.14 (m, 1H), 3.54-3.47 (m, 2H), 3.47-3.41 (m, 2H), 3.29 (s, 3H), 2.95-2.82 (m, 6H), 2.66-2.58 (m, 1H), 1.87-1.79 (m, 1H), 1.75-1.63 (m, 2H), 1.53-1.40 (m, 1H), 1.28-1.17 (m, 1H). |
| II-90 | 438.1 | 1.99 | |
| II-91 | 496.2 | 2.33 | |
| II-92 | 533.2 | 2.39 | 1H NMR (500 MHz, DMSO-d6) δ 8.58-8.49 (m, 2H), 8.44 (d, J = 9.4 Hz, 1H), 7.58 (d, J = 9.4 Hz, 1H), 7.22 (t, J = 54.0 Hz, 1H), 7.06 (t, J = 6.1 Hz, 1H), 6.92 (s, 1H), 6.55 (s, 1H), 4.27-4.22 (m, 1H), 4.21-4.14 (m, 5H), 4.12 (s, 4H), 2.95-2.84 (m, 6H), 2.71-2.61 (m, 1H), 1.88-1.78 (m, 1H), 1.74-1.62 (m, 2H), 1.53-1.40 (m, 1H), 1.30-1.18 (m, 1H). |
| II-93 | 449.2 | 2.4 | 1H NMR (400 MHz, DMSO-d6) δ 8.92 (s, 1H), 8.68 (d, J = 9.5 Hz, 1H), 8.42 (d, J = 7.2 Hz, 1H), 7.89 (d, J = 9.5 Hz, 1H), 7.56-7.19 (m, 2H), 7.10 (d, J = 7.2 Hz, 1H), 3.37 (t, J = 12.0 Hz, 1H), 3.20-3.11 (m, 1H), 3.04 (td, J = 6.5, 3.0 Hz, 2H), 2.98 (s, 3H), 1.91 (q, J = 18.7, 16.9 Hz, 1H), 1.73-1.36 (m, 2H). |
| II-94 | 453.1 | 2.25 | 1H NMR (500 MHz, DMSO-d6) δ 8.78 (s, 1H), 8.62 (d, J = 9.5 Hz, 1H), 8.40 (d, J = 7.4 Hz, 1H), 8.01 (d, J = 2.8 Hz, 1H), 7.81 (d, J = 9.5 Hz, 1H), 7.33 (t, J = 53.7 Hz, 1H), 7.25-7.15 (m, 2H), 4.26 (d, J = 13.9 Hz, 2H), 3.81-3.64 (m, 2H), 3.17 (td, J = 6.0, 3.9 Hz, 2H), 3.01 (dd, J = 13.3, 10.7 Hz, 1H), 2.97 (s, 3H), 2.92 (dd, J = 13.3, 10.7 Hz, 1H), 1.24 (d, J = 6.1 Hz, 3H). |
| II-95 | 464.1 | 2.18 | 1H NMR (500 MHz, DMSO-d6) δ 8.69 (d, J = 27.0 Hz, 2H), 8.58 (d, J = 9.4 Hz, 1H), 7.82-7.65 (m, 2H), 7.37 (t, J = 53.7 Hz, 1H), 7.20 (dd, J = 13.2, 7.4 Hz, 1H), 3.85-3.56 (m, 2H), 3.56-3.48 (m, 1H), 3.43 (q, J = 10.5 Hz, 1H), 2.16-1.90 (m, 4H), 1.80-1.69 (m, 1H), 1.69-1.51 (m, 2H), 1.39 (d, J = 2.2 Hz, 2H). |
| II-96 | 521.2 | 2.44 | 1H NMR (500 MHz, DMSO-d6) δ 8.56 (s, 1H), 8.42 (d, J = 9.4 Hz, 1H), 7.56 (d, J = 9.4 Hz, 1H), 7.22 (t, J = 53.9 Hz, 1H), 7.07 (t, J = 6.1 Hz, 1H), 6.93 (s, 1H), 6.84 (s, 1H), 4.29-4.22 (m, 1H), 4.19-4.12 (m, 1H), 3.45-3.41 (m, 4H), 2.93-2.85 (m, 6H), 2.84-2.77 (m, 4H), 2.63 (dd, J = 12.9, 10.2 Hz, 1H), 1.86-1.76 (m, 1H), 1.74-1.64 (m, 2H), 1.52-1.31 (m, 1H), 1.28-1.17 (m, 1H). |

TABLE 5-continued

Analytical data for compounds of Formula II

| II- | LCMS_Plus | LCMS_RT | NMR |
|---|---|---|---|
| II-97 | 375.2 | 2.02 | |
| II-98 | 452.2 | 2.15 | 1H NMR (500 MHz, Methanol-d4) δ 8.46 (s, 1H), 8.33-8.30 (d, 1H), 8.23 (m, 1H), 7.78 (d, 1H), 7.64-7.62 (d, 1H), 7.42 (m, 1H), 7.16-6.94 (t, 1H), 4.22-4.12 (m, 2H), 3.42 (d, 1H), 3.25-3.15 (m, 2H), 3.08-2.96 (m, 5H), 2.60-2.38 (m, 5H). |
| II-99 | 453.1 | 2.24 | |
| II-100 | 464 | 2.23 | |
| II-101 | 449.2 | 2.39 | 1H NMR (500 MHz, DMSO-d6) δ 8.89 (s, 1H), 8.67 (s, 1H), 8.57-8.45 (m, 2H), 8.39 (s, 1H), 7.64 (d, J = 9.4 Hz, 1H), 7.26 (t, J = 53.8 Hz, 1H), 3.72-3.63 (m, 4H), 3.47 (s, 2H), 3.35-3.22 (m, 2H), 3.05 (s, 3H), 1.85-1.74 (m, 2H), 1.74-1.63 (m, 2H). |
| II-102 | 437.2 | 2.02 | 1H NMR (500 MHz, Methanol-d4) δ 8.72 (s, 1H), 8.42 (d, J = 9.5 Hz, 1H), 8.31-8.27 (m, 1H), 8.11 (d, J = 6.5 Hz, 1H), 7.78 (dd, J = 6.6, 1.5 Hz, 1H), 7.75 (d, J = 9.5 Hz, 1H), 7.09 (t, J = 54.0 Hz, 1H), 4.27-4.15 (m, 2H), 4.08 (dt, J = 13.1, 1.5 Hz, 1H), 3.90-3.79 (m, 2H), 3.61 (s, 6H), 3.57-3.45 (m, 2H), 3.43-3.36 (m, 1H), 3.35 (s, 2H), 3.18 (dd, J = 12.9, 10.6 Hz, 1H). |
| II-103 | 473.1 | 2.38 | |
| II-104 | 435 | 2.21 | 1H NMR (500 MHz, DMSO-d6) δ 8.66 (s, 1H), 8.46 (d, J = 9.4 Hz, 1H), 8.23 (d, J = 5.3 Hz, 1H), 7.67 (d, J = 1.3 Hz, 1H), 7.61 (d, J = 9.4 Hz, 1H), 7.42 (dd, J = 5.3, 1.3 Hz, 1H), 7.38 (s, 1H), 4.36-4.24 (m, 2H), 3.63-3.55 (m, 1H), 3.20-3.07 (m, 2H), 2.97-2.91 (m, 1H), 2.90 (s, 3H), 2.69 (dd, J = 12.9, 9.9 Hz, 1H), 1.88 (dd, J = 13.1, 3.9 Hz, 1H), 1.80-1.56 (m, 4H), 1.49 (dtt, J = 15.8, 12.3, 4.0 Hz, 1H), 1.24 (tt, J = 15.3, 7.7 Hz, 1H). |
| II-105 | 453.1 | 2.22 | 1H NMR (500 MHz, DMSO-d6) δ 8.77 (s, 1H), 8.61 (d, J = 9.5 Hz, 1H), 8.40 (dd, J = 7.3, 4.9 Hz, 1H), 8.00 (dd, J = 13.5, 2.8 Hz, 1H), 7.80 (d, J = 9.5 Hz, 1H), 7.31-7.07 (m, 3H), 4.27-4.02 (m, 3H), 3.71-3.39 (m, 3H), 3.39-3.11 (m, 2H), 2.98 (d, J = 13.6 Hz, 3H), 1.28-1.18 (m, 3H). |
| II-106 | 453.1 | 2.37 | 1H NMR (500 MHz, DMSO-d6) δ 8.76 (d, J = 10.8 Hz, 1H), 8.51 (dd, J = 9.4, 2.5 Hz, 1H), 8.24 (t, J = 5.6 Hz, 1H), 7.88 (d, J = 24.0 Hz, 1H), 7.68 (dd, J = 9.4, 3.7 Hz, 1H), 7.63-7.55 (m, 1H), 7.33 (t, J = 53.7 Hz, 1H), 7.16 (dd, J = 48.0, 8.4 Hz, 1H), 4.36 (d, J = 12.8 Hz, 1H), 4.23-4.15 (m, 1H), 4.15-4.02 (m, 2H), 3.67-3.59 (m, 2H), 3.59-3.33 (m, 1H), 3.05 (t, J = 12.3 Hz, 1H), 2.97 (d, J = 14.6 Hz, 3H), 2.84 (dd, J = 13.1, 10.2 Hz, 1H), 1.23 (dd, J = 6.7, 2.6 Hz, 3H). |
| II-107 | 398.7 | 2.19 | 1H NMR (500 MHz, DMSO-d6) δ 8.70 (s, 1H), 8.47 (d, J = 9.4 Hz, 1H), 8.28 (d, J = 5.3 Hz, 1H), 7.79 (br s, 1H), 7.72 (s, 1H), 7.62 (d, J = 9.4 Hz, 1H), 7.57 (dd, J = 5.4, 1.3 Hz, 1H), 7.56 (br s, 1H), 7.28 (t, J = 53.9 Hz, 1H), 4.62-4.59 (m, 1H), 4.37 (d, J = 13.3 Hz, 1H), 4.20 (d, J = 12.3 Hz, 1H), 4.05 (d, J = 11.5 Hz, 1H), 3.74 (td, J = 11.7, 3.2 Hz, 1H), 3.05-2.95 (m, 2H) |
| II-108 | 398.6 | 2.19 | 1H NMR (500 MHz, DMSO-d6) δ 8.70 (s, 1H), 8.47 (d, J = 9.4 Hz, 1H), 8.28 (d, J = 5.3 Hz, 1H), 7.80 (br s, 1H), 7.72 (s, 1H), 7.62 (d, J = 9.5 Hz, 1H), 7.57 (dd, J = 5.5, 1.2 Hz, 1H), 7.56 (br s, 1H), 7.28 (t, J = 53.9 Hz, 1H), 4.60 (dd, J = 10.6, 2.5 Hz, 1H), 4.38 (d, J = 11.9 Hz, 1H), 4.20 (d, J = 12.5 Hz, 1H), 4.05 (d, J = 9.1 Hz, 1H), 3.77-3.72 (m, 1H), 3.05-2.95 (m, 2H). |
| II-109 | 451.1 | 2.65 | |
| II-110 | 439.1 | 2.07 | 1H NMR (500 MHz, DMSO-d6) δ 8.58 (s, 1H), 8.51 (d, J = 9.4 Hz, 1H), 8.36 (d, J = 6.1 Hz, 1H), 8.12 (d, J = 2.6 Hz, 1H), 7.65 (d, J = 9.3 Hz, 1H), 7.41-7.14 (m, 2H), 6.94 (d, J = 5.9 Hz, 1H), 4.05 (dd, J = 11.3, 3.2 Hz, 1H), 3.99 (d, J = 12.7 Hz, 1H), 3.86 (s, 1H), 3.71-3.61 (m, 2H), 3.17 (t, J = 6.0 Hz, 2H), 3.04 (s, 1H), 2.96 (s, 3H), 2.80 (s, 1H). |
| II-111 | 453.2 | 1.98 | 1H NMR (500 MHz, DMSO-d6) δ 10.31 (s, 1H), 8.55 (s, 1H), 8.44 (d, J = 9.4 Hz, 1H), 7.59 (d, J = 9.4 Hz, 1H), 7.22 (t, J = 53.8 Hz, 1H), 7.05 (t, J = |

TABLE 5-continued

Analytical data for compounds of Formula II

| II- | LCMS_Plus | LCMS_RT | NMR |
|---|---|---|---|
| | | | 6.1 Hz, 1H), 6.89 (s, 1H), 6.72 (d, J = 1.1 Hz, 1H), 4.29-3.93 (m, 2H), 2.98-2.82 (m, 6H), 2.70-2.60 (m, 1H), 1.89-1.79 (m, 1H), 1.78-1.66 (m, 2H), 1.57-1.42 (m, 1H), 1.27-1.17 (m, 1H). |
| II-112 | 454.3 | 1.85 | 1H NMR (500 MHz, DMSO-d6) δ 8.63 (d, J = 3.0 Hz, 1H), 8.59 (dd, J = 5.8, 1.1 Hz, 1H), 8.53 (dd, J = 9.4, 1.8 Hz, 1H), 8.01 (dd, J = 4.4, 1.2 Hz, 1H), 7.69 (dd, J = 9.4, 2.9 Hz, 1H), 7.31 (t, J = 53.6 Hz, 1H), 4.37 (s, 3H), 3.97 (s, 1H), 3.56-3.36 (m, 1H), 3.23-3.02 (m, 2H), 3.00-2.81 (m, 4H), 1.76 (d, J = 13.2 Hz, 1H), 1.55 (d, J = 11.4 Hz, 1H), 1.46-1.26 (m, 1H). |
| II-113 | 357.1 | 1.94 | 1H NMR (500 MHz, DMSO-d6) δ 8.80 (s, 1H), 8.65 (dd, J = 5.3, 0.8 Hz, 1H), 8.51 (d, J = 9.4 Hz, 1H), 8.49-8.45 (m, 1H), 8.38 (s, 1H), 8.13 (s, 1H), 8.10 (dd, J = 5.3, 1.7 Hz, 1H), 7.67 (d, J = 9.4 Hz, 1H), 7.36 (t, J = 53.8 Hz, 1H), 5.03-4.89 (m, 1H), 4.23 (t, J = 5.6 Hz, 2H), 3.81 (t, J = 5.6 Hz, 2H). |
| II-114 | 465.2 | 2.68 | |
| II-115 | 451.2 | 2.63 | |
| II-116 | 466.1 | 2.61 | 1H NMR (500 MHz, DMSO-d6) δ 8.64 (s, 1H), 8.47 (d, J = 9.6 Hz, 1H), 7.63 (d, J = 9.3 Hz, 1H), 7.37-7.05 (m, 2H), 6.99-6.60 (m, 2H), 4.20-3.99 (m, 2H), 3.03 (s, 1H), 2.98-2.81 (m, 9H), 1.90-1.81 (m, 1H), 1.81-1.69 (m, 2H), 1.60-1.46 (m, 1H), 1.34-1.20 (m, 1H). |
| II-117 | 462.1 | 2.5 | 1H NMR (500 MHz, DMSO-d6) δ 9.05 (d, J = 1.8 Hz, 1H), 8.75 (s, 1H), 8.51 (d, J = 9.4 Hz, 1H), 8.46 (d, J = 1.8 Hz, 1H), 7.67 (d, J = 9.4 Hz, 1H), 7.26 (t, J = 53.7 Hz, 1H), 7.08 (t, J = 6.2 Hz, 1H), 3.69-3.56 (m, 2H), 3.06-2.92 (m, 3H), 2.90 (s, 3H), 2.78 (dd, J = 12.0, 9.5 Hz, 1H), 1.96-1.81 (m, 3H), 1.77-1.64 (m, 1H), 1.32-1.16 (m, 1H). |
| II-118 | 453.1 | 2.33 | 1H NMR (500 MHz, DMSO-d6) δ 8.75 (s, 1H), 8.51 (d, J = 9.4 Hz, 1H), 8.23 (d, J = 5.7 Hz, 1H), 7.85 (s, 1H), 7.68 (d, J = 9.4 Hz, 1H), 7.60 (d, J = 5.9 Hz, 1H), 7.28 (t, J = 53.8 Hz, 1H), 7.15 (t, J = 6.2 Hz, 1H), 4.12-4.06 (m, 1H), 4.00 (p, J = 5.9 Hz, 1H), 3.87 (dd, J = 12.8, 3.2 Hz, 1H), 3.68-3.61 (m, 2H), 3.28-3.15 (m, 3H), 2.93 (s, 3H), 1.21 (d, J = 6.3 Hz, 3H). |
| II-119 | 453.1 | 2.41 | 1H NMR (500 MHz, DMSO-d6) δ 8.74 (s, 1H), 8.51 (d, J = 9.4 Hz, 1H), 8.25 (d, J = 5.6 Hz, 1H), 7.84 (s, 1H), 7.67 (d, J = 9.4 Hz, 1H), 7.60 (d, J = 5.6 Hz, 1H), 7.28 (t, J = 53.8 Hz, 1H), 7.22 (t, J = 6.3 Hz, 1H), 4.33 (d, J = 12.4 Hz, 1H), 4.21 (dt, J = 13.1, 1.9 Hz, 1H), 3.75-3.64 (m, 2H), 3.19-3.11 (m, 2H), 2.97 (s, 3H), 2.69-2.61 (m, 2H), 1.23 (d, J = 6.2 Hz, 3H). |
| II-120 | 467.8 | 2.8 | 1H NMR (500 MHz, DMSO-d6) δ 8.62 (s, 1H), 8.45 (d, J = 9.4 Hz, 1H), 7.60 (d, J = 9.4 Hz, 1H), 7.39-7.13 (m, 2H), 7.10 (t, J = 6.2 Hz, 1H), 6.92 (s, 1H), 4.32 (dd, J = 13.1, 3.9 Hz, 1H), 4.21 (dt, J = 13.1 Hz, 1H), 3.86 (s, 3H), 3.03-2.84 (m, 6H), 2.72 (dd, J = 13.0, 10.2 Hz, 1H), 1.91-1.81 (m, 1H), 1.80-1.65 (m, 2H), 1.58-1.44 (m, 1H), 1.32-1.18 (m, 1H). |
| II-121 | 439.1 | 2.22 | 1H NMR (500 MHz, DMSO-d6) δ 8.67 (s, 1H), 8.48 (d, J = 9.4 Hz, 1H), 8.28 (d, J = 5.3 Hz, 1H), 7.70 (s, 1H), 7.63 (d, J = 9.4 Hz, 1H), 7.54 (dd, J = 5.3, 1.3 Hz, 1H), 7.27 (t, J = 53.7 Hz, 1H), 7.22 (t, J = 6.3 Hz, 1H), 4.34 (d, J = 12.4 Hz, 1H), 4.12 (d, J = 12.2 Hz, 1H), 4.02 (dd, J = 11.4, 3.0 Hz, 1H), 3.65-3.58 (m, 2H), 3.15 (t, J = 6.1 Hz, 2H), 2.98-2.92 (m, 1H), 2.95 (s, 3H), 2.66-2.64 (m, 1H). |
| II-122 | 455.1 | 2.74 | 1H NMR (500 MHz, DMSO-d6) δ 8.72 (s, 1H), 8.49 (d, J = 9.4 Hz, 1H), 7.65 (d, J = 9.4 Hz, 1H), 7.56 (s, 1H), 7.29 (t, J = 53.7 Hz, 1H), 7.16-7.08 (m, 2H), 4.35-4.27 (m, 1H), 4.23-4.13 (m, 1H), 3.05-2.95 (m, 1H), 2.95-2.89 (m, 5H), 2.74 (dd, J = 13.1, 10.3 Hz, 1H), 1.90-1.81 (m, 1H), 1.80-1.65 (m, 2H), 1.57-1.43 (m, 1H), 1.32-1.21 (m, 1H). |

TABLE 5-continued

Analytical data for compounds of Formula II

| II- | LCMS_Plus | LCMS_RT | NMR |
|---|---|---|---|
| II-123 | 423.1 | 2.23 | 1H NMR (500 MHz, DMSO-d6) δ 8.62 (s, 1H), 8.47 (d, J = 9.4 Hz, 1H), 8.19 (dd, J = 5.3, 0.7 Hz, 1H), 7.62 (d, J = 9.4 Hz, 1H), 7.38 (s, 1H), 7.32 (dd, J = 5.3, 1.4 Hz, 1H), 7.27 (t, J = 54.0 Hz, 1H), 7.21-7.16 (m, 1H), 3.66 (dd, J = 10.5, 7.3 Hz, 1H), 3.60-3.55 (m, 1H), 3.46 (dt, J = 10.3, 7.4 Hz, 1H), 3.25 (dd, J = 10.5, 6.8 Hz, 1H), 3.07-3.05 (m, 2H), 2.93 (s, 3H), 2.53-2.47 (m, 1H), 2.17-2.10 (m, 1H), 1.81 (dq, J = 12.0, 7.9 Hz, 1H). |
| II-124 | 439.1 | 2.51 | 1H NMR (500 MHz, DMSO-d6) δ 9.84 (s, 1H), 8.77 (s, 1H), 8.52 (d, J = 9.4 Hz, 1H), 8.20 (d, J = 5.8 Hz, 1H), 7.68 (d, J = 9.4 Hz, 1H), 7.53 (s, 1H), 7.26 (t, J = 53.8 Hz, 1H), 4.07 (s, 2H), 3.67 (s, 4H), 2.97 (s, 3H), 1.98 (dt, J = 11.6, 5.5 Hz, 1H), 1.90-1.67 (m, 1H), 1.60 (s, 1H). |
| II-125 | 437.1 | 2.3 | 1H NMR (500 MHz, DMSO-d6) δ 8.50 (s, 1H), 8.46 (d, J = 9.4 Hz, 1H), 8.28 (d, J = 5.9 Hz, 1H), 8.11 (d, J = 2.6 Hz, 1H), 7.59 (d, J = 9.4 Hz, 1H), 7.25 (t, J = 53.9 Hz, 1H), 7.12 (t, J = 6.1 Hz, 1H), 6.83 (dd, J = 6.0, 2.6 Hz, 1H), 4.04-3.95 (m, 1H), 3.95-3.86 (m, 1H), 3.06-2.86 (m, 6H), 2.76 (dd, J = 13.1, 10.3 Hz, 1H), 1.90-1.80 (m, 1H), 1.80-1.67 (m, 2H), 1.60-1.47 (m, 1H), 1.35-1.21 (m, 1H). |
| II-126 | 451.1 | 2.39 | 1H NMR (500 MHz, DMSO-d6) δ 8.71 (s, 1H), 8.48 (d, J = 9.4 Hz, 1H), 8.30 (d, J = 5.3 Hz, 1H), 7.75 (s, 1H), 7.64 (d, J = 9.4 Hz, 1H), 7.61 (dd, J = 5.3, 1.3 Hz, 1H), 7.29 (t, J = 53.7 Hz, 1H), 3.89 (d, J = 9.1 Hz, 2H), 3.82 (d, J = 9.2 Hz, 2H), 3.83-3.77 (m, 2H), 3.77 (s, 2H), 3.54-3.52 (m, 2H), 3.07 (s, 3H). |
| II-127 | 373.1 | 1.97 | 1H NMR (500 MHz, DMSO-d6) δ 8.53 (s, 1H), 8.48 (d, J = 9.4 Hz, 1H), 8.33 (d, J = 5.9 Hz, 1H), 8.14 (d, J = 2.5 Hz, 1H), 7.61 (d, J = 9.4 Hz, 1H), 7.33 (t, J = 53.7 Hz, 1H), 6.88 (dd, J = 6.0, 2.6 Hz, 1H), 3.68-3.60 (m, 4H), 3.55-3.49 (m, 2H), 3.48-3.41 (m, 2H), 2.08 (s, 3H). |
| II-128 | 436.1 | 2.5 | 1H NMR (500 MHz, DMSO-d6) δ 8.65 (s, 1H), 8.46 (d, J = 9.4 Hz, 1H), 8.23 (dd, J = 5.3, 0.7 Hz, 1H), 7.70-7.65 (m, 1H), 7.61 (d, J = 9.4 Hz, 1H), 7.42 (dd, J = 5.3, 1.3 Hz, 1H), 7.38 (s, 1H), 4.29 (tt, J = 8.9, 3.6 Hz, 2H), 3.27-3.19 (m, 2H), 2.98 (s, 3H), 2.93 (ddd, J = 12.9, 11.5, 2.9 Hz, 1H), 2.71 (dd, J = 13.0, 9.6 Hz, 1H), 1.94-1.86 (m, 1H), 1.79-1.69 (m, 2H), 1.70-1.59 (m, 2H), 1.49 (tdd, J = 11.9, 7.9, 3.9 Hz, 1H), 1.31-1.15 (m, 1H). |
| II-129 | 451.1 | 2.69 | 1H NMR (500 MHz, DMSO-d6) δ 8.76 (s, 1H), 8.52 (d, J = 9.4 Hz, 1H), 7.86 (s, 1H), 7.70 (d, J = 9.4 Hz, 1H), 7.46 (s, 1H), 7.28 (t, J = 53.7 Hz, 1H), 7.12 (t, J = 6.2 Hz, 1H), 4.25-4.10 (m, 2H), 3.27-3.12 (m, 1H), 3.09-2.86 (m, 6H), 1.94-1.74 (m, 3H), 1.63-1.50 (m, 1H), 1.41-1.27 (m, 1H). |
| II-130 | 462.2 | 2.71 | 1H NMR (500 MHz, DMSO-d6) δ 8.77 (s, 1H), 8.50 (d, J = 9.4 Hz, 1H), 8.04 (d, J = 1.3 Hz, 1H), 7.96 (d, J = 1.1 Hz, 1H), 7.67 (d, J = 9.4 Hz, 1H), 7.29 (t, J = 53.7 Hz, 1H), 7.12 (t, J = 6.1 Hz, 1H), 4.39-4.32 (m, 1H), 4.26-4.16 (m, 1H), 3.05 (ddd, J = 13.5, 11.3, 3.0 Hz, 1H), 2.97-2.88 (m, 5H), 2.79 (dd, J = 13.1, 10.2 Hz, 1H), 1.90-1.81 (m, 1H), 1.81-1.66 (m, 2H), 1.56-1.43 (m, 1H), 1.34-1.20 (m, 1H). |
| II-131 | 489.2 | 1.9 | 1H NMR (500 MHz, DMSO-d6) δ 9.39 (s, 1H), 9.24-9.18 (m, 1H), 8.82 (s, 1H), 8.68 (d, J = 5.2 Hz, 1H), 8.54 (d, J = 9.4 Hz, 1H), 8.47 (dd, J = 5.2, 1.6 Hz, 1H), 7.71 (d, J = 9.4 Hz, 1H), 7.27 (s, 1H), 4.51 (dd, J = 13.3, 5.6 Hz, 1H), 4.37 (td, J = 11.8, 10.9, 2.9 Hz, 1H), 3.66 (dt, J = 13.2, 6.8 Hz, 1H), 3.51 (d, J = 13.7 Hz, 1H), 3.38 (td, J = 8.9, 4.7 Hz, 1H), 3.09-2.97 (m, 1H), 2.95 (s, 3H), 2.82 (d, J = 8.9 Hz, 1H), 2.40-2.27 (m, 1H). |
| II-132 | 489.9 | 1.96 | 1H NMR (500 MHz, DMSO-d6) δ 9.33 (d, J = 1.6 Hz, 1H), 8.80 (s, 1H), 8.66 (d, J = 5.2 Hz, 1H), 8.53 (d, J = 9.4 Hz, 1H), 8.43 (dd, J = 5.2, |

TABLE 5-continued

Analytical data for compounds of Formula II

| II- | LCMS_Plus | LCMS_RT | NMR |
|---|---|---|---|
| | | | 1.7 Hz, 1H), 7.71 (d, J = 9.4 Hz, 1H), 7.39-7.15 (m, 2H), 4.28-4.15 (m, 1H), 4.11-3.93 (m, 1H), 3.47 (ddd, J = 13.6, 5.9, 3.4 Hz, 1H), 3.25-3.18 (m, 1H), 3.10-2.96 (m, 2H), 2.92 (s, 3H), 2.31 (t, J = 12.6 Hz, 1H). |
| II-133 | 451.2 | 2.58 | 1H NMR (500 MHz, DMSO-d6) δ 8.62 (s, 1H), 8.47 (d, J = 9.4 Hz, 1H), 8.23 (dd, J = 5.4, 0.6 Hz, 1H), 7.65-7.63 (m, 1H), 7.62 (d, J = 9.4 Hz, 1H), 7.39 (dd, J = 5.3, 1.3 Hz, 1H), 7.37 (s, 1H), 7.07 (d, J = 8.7 Hz, 1H), 4.56-4.46 (m, 1H), 4.34 (d, J = 13.2 Hz, 1H), 3.27-3.20 (m, 1H), 2.94 (s, 3H), 2.80 (td, J = 12.5, 2.8 Hz, 1H), 2.63 (dd, J = 13.1, 11.0 Hz, 1H), 1.87-1.70 (m, 2H), 1.49 (tddd, J = 16.7, 12.7, 7.6, 3.7 Hz, 2H), 1.30 (qd, J = 12.3, 3.8 Hz, 1H), 1.19 (d, J = 6.7 Hz, 3H). |
| II-134 | 451.2 | 2.52 | 1H NMR (500 MHz, DMSO-d6) δ 8.64 (s, 1H), 8.47 (d, J = 9.4 Hz, 1H), 8.23 (d, J = 5.3 Hz, 1H), 7.68 (s, 1H), 7.62 (d, J = 9.4 Hz, 1H), 7.39 (dd, J = 5.3, 1.3 Hz, 1H), 7.36 (s, 1H), 7.02 (d, J = 8.6 Hz, 1H), 4.31 (t, J = 15.4 Hz, 2H), 2.93 (s, 3H), 2.91-2.74 (m, 2H), 1.90 (d, J = 11.5 Hz, 1H), 1.77 (ddd, J = 13.1, 5.5, 3.3 Hz, 1H), 1.57-1.40 (m, 2H), 1.34 (qd, J = 12.1, 3.7 Hz, 1H), 1.21 (d, J = 6.7 Hz, 3H). |
| II-135 | 375.1 | 2.05 | 1H NMR (500 MHz, DMSO-d6) δ 8.79 (s, 1H), 8.52 (d, J = 9.4 Hz, 1H), 8.25 (d, J = 5.7 Hz, 1H), 7.95 (s, 1H), 7.69 (d, J = 9.4 Hz, 1H), 7.64 (dd, J = 5.8, 1.4 Hz, 1H), 7.48-7.14 (m, 3H), 4.40 (dt, J = 13.1, 1.9 Hz, 1H), 4.06 (ddd, J = 10.3, 6.7, 2.8 Hz, 3H), 3.78-3.68 (m, 1H), 3.26-3.16 (m, 1H), 3.14-3.03 (m, 1H). |
| II-136 | 449.2 | 2.56 | 1H NMR (500 MHz, DMSO-d6) δ 8.73 (s, 1H), 8.50 (d, J = 9.5 Hz, 1H), 8.24 (d, J = 5.8 Hz, 1H), 7.84 (s, 1H), 7.65 (d, J = 10.0 Hz, 1H), 7.54 (s, 1H), 7.28 (t, J = 53.6 Hz, 1H), 3.81 (s, 2H), 3.67-3.61 (m, 4H), 3.55-3.52 (m, 2H), 3.04 (s, 3H), 1.84-1.82 (m, 2H), 1.64 (br s, 2H). |
| II-137 | 440.2 | 1.53 | 1H NMR (500 MHz, DMSO-d6) δ 8.62 (s, 1H), 8.56-8.52 (m, 2H), 7.74-7.67 (m, 2H), 7.47-7.14 (m, 2H), 5.24-5.15 (2 x s, 1H), 3.82-3.78 (m, 0.4H), 3.63-3.51 (m, 3.6H), 3.21-3.17 (m, 2H), 2.98-2.96 (2 x s, 3H), 2.15-2.11 (m, 0.2H), 1.98-1.92 (m, 1.8H). |
| II-138 | 421.2 | 2.12 | 1H NMR (500 MHz, DMSO-d6) δ 8.63 (d, J = 1.9 Hz, 1H), 8.47 (d, J = 9.4 Hz, 1H), 8.23 (d, J = 5.3 Hz, 1H), 7.73-7.69 (m, 1H), 7.62 (d, J = 9.4 Hz, 1H), 7.43 (dt, J = 5.3, 1.2 Hz, 2H), 4.46-4.33 (m, 1H), 4.31-4.14 (m, 1H), 3.78 (d, J = 16.6 Hz, 1H), 3.16-3.01 (m, 3H), 3.00-2.95 (m, 3H), 2.21 (d, J = 7.3 Hz, 1H), 2.04-1.91 (m, 1H), 1.71 (dq, J = 12.2, 4.0 Hz, 1H), 1.54 (dd, J = 16.9, 7.8 Hz, 1H), 1.44 (qd, J = 11.1, 5.5 Hz, 1H). |
| II-139 | 455.2 | 2.38 | 1H NMR (500 MHz, DMSO-d6) δ 8.68 (s, 1H), 8.48 (d, J = 9.4 Hz, 1H), 8.22 (d, J = 5.4 Hz, 1H), 7.74 (s, 1H), 7.63 (d, J = 9.4 Hz, 1H), 7.46 (d, J = 5.5 Hz, 1H), 7.43-7.35 (m, 1H), 7.27 (s, 1H), 4.37 (dd, J = 14.0, 9.4 Hz, 1H), 4.14 (dt, J = 13.1, 3.9 Hz, 1H), 3.28-3.13 (m, 4H), 1.98-1.61 (m, 4H). |
| II-140 | 440.1 | 1.52 | 1H NMR (500 MHz, DMSO-d6) δ 8.63 (s, 1H), 8.56-8.52 (m, 2H), 7.73-7.68 (m, 2H), 7.46-7.18 (m, 1H), 7.11 (br s, 1H), 4.42 (s, 0.5H), 4.34 (s, 0.5H), 3.91-3.87 (m, 0.4H), 3.75 (d, J = 12.4 Hz, 0.2H), 3.69-3.59 (m, 2H), 3.47 (d, J = 10.8 Hz, 0.4H), 3.29 (q, J = 11.7, 10.2 Hz, 1H), 3.20-3.10 (m, 1H), 2.96-2.94 (2 x s, 3H), 242-2.38 (m, 2H). |
| II-141 | 453.1 | 1.96 | 1H NMR (500 MHz, DMSO-d6) δ 8.56 (s, 1H), 8.44 (d, J = 9.4 Hz, 1H), 7.59 (d, J = 9.4 Hz, 1H), 7.22 (t, J = 53.8 Hz, 1H), 7.05 (t, J = 6.1 Hz, 1H), 6.92 (s, 1H), 6.73 (d, J = 1.1 Hz, 1H), 4.23-4.00 (m, 2H), 2.93-2.85 (m, 6H), 2.68-2.62 (m, 1H), 1.90-1.79 (m, 1H), 1.78-1.65 (m, 2H), 1.54-1.43 (m, 1H), 1.28-1.17 (m, 1H). |
| II-142 | 467.2 | 2.81 | 1H NMR (500 MHz, DMSO-d6) δ 8.61 (s, 1H), 8.45 (d, J = 9.4 Hz, 1H), 7.59 (d, J = 9.4 Hz, 1H), |

TABLE 5-continued

Analytical data for compounds of Formula II

| II- | LCMS_Plus | LCMS_RT | NMR |
|---|---|---|---|
| | | | 7.39-7.12 (m, 2H), 7.09 (t, J = 6.2 Hz, 1H), 6.91 (d, J = 0.9 Hz, 1H), 4.31 (dd, J = 13.0, 3.7 Hz, 1H), 4.25-4.18 (m, 1H), 3.85 (s, 3H), 3.02-2.87 (m, 6H), 2.71 (dd, J = 13.0, 10.1 Hz, 1H), 1.89-1.81 (m, 1H), 1.77-1.65 (m, 2H), 1.55-1.43 (m, 1H), 1.32-1.20 (m, 1H). |
| II-143 | 373.1 | 2.09 | 1H NMR (500 MHz, DMSO-d6) δ 8.66 (s, 1H), 8.47 (d, J = 9.4 Hz, 1H), 8.24 (d, J = 5.3 Hz, 1H), 7.71 (s, 1H), 7.62 (d, J = 9.4 Hz, 1H), 7.43 (d, J = 5.4 Hz, 1H), 7.34 (s, 1H), 7.26 (t, J = 53.9 Hz, 1H), 6.86 (s, 1H), 4.45 (d, J = 12.1 Hz, 1H), 4.34 (d, J = 12.4 Hz, 1H), 2.98-2.86 (m, 2H), 2.38-2.33 (m, 1H), 1.92 (d, J = 9.0 Hz, 1H), 1.75-1.62 (m, 2H), 1.52-1.47 (m, 1H). |
| II-144 | 423.1 | 2.28 | 1H NMR (500 MHz, DMSO-d6) δ 8.62 (s, 1H), 8.47 (d, J = 9.4 Hz, 1H), 8.23 (d, J = 5.3 Hz, 1H), 7.71 (s, 1H), 7.63 (d, J = 9.4 Hz, 1H), 7.42 (dd, J = 5.3, 1.3 Hz, 1H), 7.29 (t, J = 53.7 Hz, 1H), 6.89 (s, 2H), 4.38-4.34 (m, 1H), 4.22 (dt, J = 13.2, 4.1 Hz, 1H), 3.10-2.90 (m, 4H), 2.19-2.13 (m, 1H), 2.02-1.98 (m, 1H), 1.76-1.70 (m, 1H), 1.57-1.50 (m, 1H), 1.45-1.38 (m, 1H). |
| II-145 | 387.2 | 2.17 | 1H NMR (500 MHz, DMSO-d6) δ 8.64 (s, 1H), 8.47 (d, J = 9.4 Hz, 1H), 8.22 (d, J = 5.2 Hz, 1H), 7.70 (s, 1H), 7.62 (d, J = 9.4 Hz, 1H), 7.40 (d, J = 6.5 Hz, 1H), 7.33 (s, 1H), 7.31 (t, J = 53.8 Hz, 1H), 6.78 (s, 1H), 4.28 (d, J = 10.9 Hz, 2H), 2.93 (td, J = 13.0, 12.2, 2.9 Hz, 1H), 2.71-2.66 (m, 1H), 2.12-2.02 (m, 2H), 1.96-1.92 (m, 1H), 1.83-1.80 (m, 1H), 1.71 (dt, J = 13.3, 3.6 Hz, 1H), 1.54-1.45 (m, 1H), 1.24 (qd, J = 12.0, 3.9 Hz, 1H). |
| II-146 | 376.2 | 2.13 | 1H NMR (500 MHz, DMSO-d6) δ 8.68 (s, 1H), 8.47 (d, J = 9.4 Hz, 1H), 8.27 (d, J = 5.3 Hz, 1H), 7.71 (s, 1H), 7.63 (d, J = 9.4 Hz, 1H), 7.52 (dd, J = 5.3, 1.3 Hz, 1H), 7.28 (t, J = 53.9 Hz, 1H), 4.50 (t, J = 5.2 Hz, 1H), 4.24 (d, J = 12.4 Hz, 1H), 4.14 (d, J = 13.3 Hz, 1H), 3.97 (dd, J = 11.1, 2.6 Hz, 1H), 3.65-3.55 (m, 4H), 2.90 (td, J = 12.5, 3.5 Hz, 1H), 2.62 (dd, J = 12.7, 10.6 Hz, 1H), 1.69-1.65 (m, 2H). |
| II-147 | 398.1 | 2.18 | 1H NMR (500 MHz, DMSO-d6) δ 8.79 (s, 1H), 8.51 (d, J = 9.4 Hz, 1H), 8.26 (d, J = 5.7 Hz, 1H), 7.89 (s, 1H), 7.67 (dd, J = 13.3, 4.0 Hz, 4H), 7.29 (t, J = 53.9 Hz, 1H), 4.64 (dd, J = 10.4, 2.7 Hz, 1H), 4.35 (d, J = 13.5 Hz, 1H), 4.18 (d, J = 13.8 Hz, 1H), 4.09-4.06 (m, 1H), 3.77 (td, J = 11.7, 2.8 Hz, 1H), 3.12 (dt, J = 24.2, 11.1 Hz, 2H). |
| II-148 | 467.1 | 2.52 | 1H NMR (500 MHz, DMSO-d6) δ 8.67 (s, 1H), 8.48 (d, J = 9.4 Hz, 1H), 8.24 (d, J = 5.4 Hz, 1H), 7.69 (s, 1H), 7.63 (d, J = 9.4 Hz, 1H), 7.49 (dd, J = 5.3, 1.3 Hz, 1H), 7.26 (t, J = 53.9 Hz, 1H), 7.14 (s, 1H), 4.45 (d, J = 12.3 Hz, 1H), 4.14 (d, J = 12.0 Hz, 1H), 3.87-3.82 (m, 1H), 3.08 (d, J = 5.7 Hz, 2H), 2.96 (s, 3H), 2.75 (d, J = 12.8 Hz, 1H), 2.57-2.53 (m, 1H), 1.25 (s, 3H), 1.23 (s, 3H). |
| II-149 | 439.1 | 2.2 | 1H NMR (500 MHz, DMSO-d6) δ 8.67 (s, 1H), 8.48 (d, J = 9.4 Hz, 1H), 8.28 (d, J = 5.3 Hz, 1H), 7.70 (s, 1H), 7.63 (d, J = 9.4 Hz, 1H), 7.54 (dd, J = 5.3, 1.3 Hz, 1H), 7.27 (t, J = 53.7 Hz, 1H), 7.22 (t, J = 6.3 Hz, 1H), 4.34 (d, J = 12.2 Hz, 1H), 4.12 (d, J = 12.7 Hz, 1H), 4.03-4.00 (m, 1H), 3.65-3.58 (m, 2H), 3.14 (t, J = 6.1 Hz, 2H), 2.98-2.92 (m, 1H), 2.95 (s, 3H), 2.68-2.64 (m, 1H). |
| II-150 | 372.2 | 2.38 | 1H NMR (500 MHz, DMSO-d6) δ 8.46 (s, 1H), 8.43 (d, J = 9.4 Hz, 1H), 7.76 (t, J = 2.0 Hz, 1H), 7.64-7.59 (m, 1H), 7.57 (d, J = 9.4 Hz, 1H), 7.40 (t, J = 8.0 Hz, 1H), 7.24 (t, J = 53.8 Hz, 1H), 7.05 (dd, J = 8.3, 2.5 Hz, 1H), 3.68-3.57 (m, 4H), 3.24 (dt, J = 33.2, 5.2 Hz, 4H), 2.06 (s, 3H). |
| II-151 | 406.1 | 2.19 | 1H NMR (500 MHz, DMSO-d6) δ 8.84 (d, J = 6.0 Hz, 1H), 8.54 (d, J = 9.4 Hz, 1H), 8.17 (dd, J = 6.1, 4.5 Hz, 1H), 8.06 (d, J = 16.1 Hz, 1H), 7.72 (dd, J = 9.4, 2.1 Hz, 1H), 7.60 (s, 1H), 7.36 (td, J = 53.7, 21.8 Hz, 1H), 4.29 (dd, J = 32.8, 13.2 Hz, 1H), 4.14 (t, J = 14.2 Hz, 1H), 3.20 (dd, J = 45.0, |

TABLE 5-continued

Analytical data for compounds of Formula II

| II- | LCMS_Plus | LCMS_RT | NMR |
|---|---|---|---|
| | | | 31.8 Hz, 1H), 2.90-2.65 (m, 2H), 2.61 (d, J = 6.9 Hz, 3H), 2.18 (s, 1H), 2.05-1.90 (m, 1H), 1.82 (d, J = 13.4 Hz, 1H), 1.64 (t, J = 12.1 Hz, 1H), 1.52 (q, J = 11.3, 10.9 Hz, 1H). |
| II-152 | 440.2 | 1.49 | 1H NMR (500 MHz, DMSO-d6) δ 8.63 (s, 1H), 8.56 (d, J = 1.2 Hz, 1H), 8.53 (d, J = 9.4 Hz, 1H), 7.74-7.68 (m, 2H), 7.47-7.15 (m, 2H), 4.22 (d, J = 35.8 Hz, 1H), 3.74 (s, 2H), 3.50 (d, J = 13.2 Hz, 1H), 3.07 (s, 1H), 2.95-2.90 (m, 2H), 2.91 (s, 3H), 2.47-2.40 (m, 1H). |
| II-153 | 473.1 | 2.58 | 1H NMR (500 MHz, Methanol-d4) δ 8.49 (s, 1H), 8.33 (d, J = 9.4 Hz, 1H), 8.27 (d, J = 5.4 Hz, 1H), 7.86 (d, J = 1.2 Hz, 1H), 7.64 (d, J = 9.4 Hz, 1H), 7.48 (dd, J = 5.5, 1.4 Hz, 1H), 7.06 (t, J = 54.1 Hz, 1H), 4.40 (d, J = 13.9 Hz, 1H), 4.33 (d, J = 13.7 Hz, 1H), 3.53 (dd, J = 13.6, 3.9 Hz, 1H), 3.48-3.36 (m, 2H), 3.36-3.34 (m, 1H), 3.22-3.12 (m, 2H), 2.99 (s, 3H), 2.31 (ddd, J = 21.0, 9.5, 4.8 Hz, 1H). |
| II-154 | 437.2 | 2.43 | 1H NMR (500 MHz, DMSO-d6) δ 8.64 (s, 1H), 8.47 (d, J = 9.4 Hz, 1H), 8.23 (d, J = 5.3 Hz, 1H), 7.68 (s, 1H), 7.62 (d, J = 9.4 Hz, 1H), 7.41 (dd, J = 5.3, 1.3 Hz, 1H), 7.26 (t, J = 53.8 Hz, 1H), 7.11-7.08 (m, 1H), 4.39 (dd, J = 12.2, 2.9 Hz, 1H), 4.24-4.20 (m, 1H), 2.98-2.91 (m, 3H), 2.91 (s, 3H), 2.69 (dd, J = 13.1, 10.3 Hz, 1H), 1.88-1.84 (m, 1H), 1.77-1.68 (m, 2H), 1.53-1.46 (m, 1H), 1.29-1.22 (m, 1H). |
| II-155 | 437.2 | 2.44 | 1H NMR (500 MHz, DMSO-d6) δ 8.64 (s, 1H), 8.47 (d, J = 9.5 Hz, 1H), 8.24 (d, J = 5.4 Hz, 1H), 7.68 (s, 1H), 7.62 (d, J = 9.4 Hz, 1H), 7.41 (dd, J = 5.3, 1.2 Hz, 1H), 7.26 (t, J = 53.8 Hz, 1H), 7.10 (t, J = 6.2 Hz, 1H), 4.39 (dd, J = 13.4, 3.2 Hz, 1H), 4.25-4.20 (m, 1H), 2.98-2.91 (m, 3H), 2.91 (s, 3H), 2.69 (dd, J = 13.0, 10.3 Hz, 1H), 1.85 (dd, J = 13.2, 4.1 Hz, 1H), 1.77-1.68 (m, 2H), 1.54-1.46 (m, 1H), 1.30-1.22 (m, 1H). |
| II-156 | 399.1 | 2.06 | 1H NMR (300 MHz, DMSO-d6) 1.49-1.64 (m, 2H), 1.69-1.87 (m, 3H), 1.93-2.03 (m, 1H), 2.77-2.94 (m, 2H), 3.11-3.28 (m, 2H), 4.29 (d, J = 12.6 Hz, 1H), 4.42 (d, J = 12.3 Hz, 1H), 7.06-7.48 (m, 2H), 7.62 (d, J = 9.0 Hz, 1H), 7.66-7.76 (m, 2H), 8.20 (d, J = 5.0 Hz, 1H), 8.47 (d, J = 9.5 Hz, 1H), 8.68 (s, 1H). |
| II-157 | 437.1 | 2.16 | 1H NMR (300 MHz, DMSO-d6) 1.14-1.33 (m, 1H), 1.40-1.58 (m, 1H), 1.63-1.90 (m, 3H), 2.66 (dd, J = 12.8, 10.6 Hz, 1H), 2.84-3.00 (m, 6H), 4.22 (br. d, J = 12.8 Hz, 1H), 4.40 (br. d, J = 10.9 Hz, 1H), 7.05-7.47 (m, 3H), 7.61 (d, J = 9.0 Hz, 1H), 7.67 (s, 1H), 8.22 (d, J = 5.1 Hz, 1H), 8.47 (d, J = 9.0 Hz, 1H), 8.64 (s, 1H). |
| II-158 | 454.3 | 1.91 | 1H NMR (500 MHz, DMSO-d6) δ 8.62 (s, 1H), 8.58-8.50 (m, 2H), 8.00 (d, J = 1.2 Hz, 1H), 7.70 (d, J = 9.4 Hz, 1H), 7.30 (t, J = 53.6 Hz, 1H), 7.02 (t, J = 6.7 Hz, 1H), 4.71 (s, 1H), 3.91 (s, 1H), 3.30 (d, J = 18.1 Hz, 3H), 3.00 (d, J = 6.6 Hz, 2H), 2.92 (s, 3H), 1.85-1.68 (m, 2H), 1.60 (dd, J = 19.0, 9.2 Hz, 2H). |
| II-159 | 454.3 | 2.15 | 1H NMR (500 MHz, DMSO-d6) δ 8.67-8.61 (m, 2H), 8.54 (d, J = 9.4 Hz, 1H), 8.01 (d, J = 1.2 Hz, 1H), 7.71 (d, J = 9.4 Hz, 1H), 7.46-7.01 (m, 2H), 4.28 (s, 3H), 4.09-4.04 (m, 1H), 3.62-3.49 (m, 2H), 3.43 (ddd, J = 10.7, 5.0, 2.5 Hz, 1H), 3.11 (d, J = 12.3 Hz, 1H), 2.96 (s, 3H), 1.22 (d, J = 6.9 Hz, 3H). |
| II-160 | 371.2 | 2.18 | 1H NMR (500 MHz, DMSO-d6) δ 8.72 (s, 1H), 8.48 (d, J = 9.4 Hz, 1H), 8.28 (s, 1H), 8.25 (dd, J = 5.4, 0.7 Hz, 1H), 7.66 (s, 1H), 7.64 (d, J = 9.4 Hz, 1H), 7.57 (d, J = 5.5 Hz, 1H), 7.28 (t, J = 53.9 Hz, 1H), 4.22 (s, 2H), 3.75 (s, 2H), 0.85 n-0.83 (m, 2H), 0.80-0.78 (m, 2H). |
| II-161 | 399.3 | 2.29 | 1H NMR (500 MHz, DMSO-d6) δ 8.72 (s, 1H), 8.50 (d, J = 9.4 Hz, 1H), 8.31 (s, 2H), 8.21 (d, J = 5.6 Hz, 1H), 7.83 (s, 1H), 7.66 (d, J = 9.5 Hz, 1H), 7.49 (s, 1H), 7.28 (t, J = 53.8 Hz, 1H), 3.66- |

TABLE 5-continued

Analytical data for compounds of Formula II

| II- | LCMS_Plus | LCMS_RT | NMR |
|---|---|---|---|
| | | | 3.63 (m, 4H), 3.10 (s, 4H), 1.67 (t, J = 5.9 Hz, 4H), 1.61 (t, J = 5.7 Hz, 4H). |
| II-162 | 360.2 | 2.36 | 1H NMR (500 MHz, DMSO-d6) δ 8.63 (s, 1H), 8.47 (d, J = 9.4 Hz, 1H), 8.21 (d, J = 5.0 Hz, 1H), 7.73 (s, 1H), 7.62 (d, J = 9.4 Hz, 1H), 7.36 (dd, J = 5.3, 1.3 Hz, 1H), 7.20 (t, J = 53.9 Hz, 1H), 4.58 (t, J = 5.2 Hz, 1H), 4.41-4.37 (m, 1H), 4.31-4.27 (m, 1H), 3.44-3.33 (m, 2H), 2.94-2.89 (m, 1H), 2.68 (dd, J = 13.0, 10.4 Hz, 1H), 1.80-1.77 (m, 1H), 1.74-1.62 (m, 2H), 1.53-1.44 (m, 1H), 1.23 (qd, J = 12.1, 3.9 Hz, 1H). |
| II-163 | 387.3 | 2.16 | 1H NMR (400 MHz, 380 K, DMSO-d6) δ 8.51 (s, 1H), 8.39 (d, J = 9.6 Hz, 1H), 8.21 (d, J = 6.0 Hz, 1H), 7.59 (s, 1H), 7.55 (d, J = 9.4 Hz, 1H), 7.27 (dd, J = 5.3, 1.4 Hz, 1H), 7.17 (t, J = 54.1 Hz, 1H), 3.88-3.76 (m, 4H), 3.71-3.68 (m, 2H), 3.48-3.45 (m, 2H), 2.00-1.88 (m, 5H). |
| II-164 | 359.2 | 1.97 | 1H NMR (500 MHz, DMSO-d6) δ 8.66 (s, 1H), 8.47 (d, J = 9.4 Hz, 1H), 8.26 (dd, J = 5.3, 0.7 Hz, 1H), 7.69 (s, 1H), 7.64-7.61 (m, 2H), 7.43 (dd, J = 5.3, 1.3 Hz, 1H), 7.29 (t, J = 53.9 Hz, 1H), 3.89-3.85 (m, 4H), 3.25-3.23 (m, 2H), 2.57-2.55 (m, 2H). |
| II-165 | 343.2 | 2.01 | 1H NMR (500 MHz, DMSO-d6) δ 8.62 (s, 1H), 8.46 (d, J = 9.3 Hz, 1H), 8.17 (d, J = 5.3 Hz, 1H), 7.61 (d, J = 9.4 Hz, 1H), 7.38-7.16 (m, 3H), 4.73 (s, 1H), 3.68 (s, 1H), 3.53 (dd, J = 9.3, 2.1 Hz, 1H), 3.26 (d, J = 8.4 Hz, 1H), 2.93 (dd, J = 9.5, 1.9 Hz, 1H), 2.84 (d, J = 9.5 Hz, 1H), 1.80 (d, J = 8.5 Hz, 1H), 1.69 (d, J = 9.3 Hz, 1H). |
| II-166 | 345.2 | 2.11 | 1H NMR (500 MHz, DMSO-d6) δ 8.62 (s, 1H), 8.46 (d, J = 9.4 Hz, 1H), 8.18 (d, J = 5.3 Hz, 1H), 7.60 (d, J = 9.4 Hz, 1H), 7.58 (s, 1H), 7.35-7.14 (m, 2H), 3.76 (t, J = 6.2 Hz, 2H), 3.71 (t, J = 5.3 Hz, 2H), 2.89 (d, J = 5.2 Hz, 2H), 2.68 (t, J = 5.9 Hz, 2H), 1.85-1.81 (m, 2H). |
| II-167 | 385.2 | 2.19 | 1H NMR (500 MHz, DMSO-d6) δ 8.69 (s, 1H), 8.48 (d, J = 9.4 Hz, 1H), 8.27 (d, J = 5.3 Hz, 1H), 7.75 (s, 1H), 7.63 (d, J = 9.4 Hz, 1H), 7.54-7.53 (m, 1H), 7.30 (t, J = 53.8 Hz, 1H), 4.63-4.59 (m, 1H), 4.49-4.45 (m, 1H), 3.90 (d, J = 10.9 Hz, 2H), 3.66-3.60 (m, 1H), 2.90-2.80 (m, 1H), 2.69-2.66 (m, 1H), 2.31-2.28 (m, 1H), 2.21-2.15 (m, 1H), 1.69-1.63 (m, 1H), 1.21 (d, J = 7.1 Hz, 1H). |
| II-168 | 374.2 | 2.38 | 1H NMR (500 MHz, DMSO-d6) δ 8.65 (s, 1H), 8.46 (d, J = 9.7 Hz, 1H), 8.22 (d, J = 5.3 Hz, 1H), 7.68 (s, 1H), 7.61 (d, J = 9.6 Hz, 1H), 7.41 (d, J = 5.2 Hz, 1H), 7.28 (t, J = 53.8 Hz, −1H), 4.39-4.37 (m, 3H), 3.50-3.47 (m, 2H), 2.86 (t, J = 12.0 Hz, 2H), 1.76 (d, J = 13.0 Hz, 2H), 1.72-1.65 (m, 1H), 1.40 (q, J = 6.6 Hz, 2H), 1.21-1.12 (m, 2H). |
| II-169 | 361.2 | 1.88 | 1H NMR (500 MHz, DMSO-d6) δ 8.65 (s, 1H), 8.47 (d, J = 9.4 Hz, 1H), 8.24 (d, J = 5.3 Hz, 1H), 7.69 (s, 1H), 7.62 (d, J = 9.4 Hz, 1H), 7.45 (dd, J = 5.4, 1.3 Hz, 1H), 7.26 (t, J = 53.9 Hz, 1H), 4.77-4.75 (m, 1H), 4.31 (d, J = 12.1 Hz, 1H), 4.19 (d, J = 12.4 Hz, 1H), 3.45-3.41 (m, 2H), 3.05 (d, J = 11.5 Hz, 1H), 2.90-2.85 (m, 1H), 2.79-2.75 (m, 2H), 2.56-2.52 (m, 1H). |
| II-170 | 403.2 | 2.16 | 1H NMR (500 MHz, DMSO-d6) δ 8.68 (s, 1H), 8.48 (d, J = 9.4 Hz, 1H), 8.27 (d, J = 5.4 Hz, 1H), 7.72 (s, 1H), 7.63 (d, J = 9.4 Hz, 1H), 7.52 (dd, J = 5.3, 1.3 Hz, 1H), 7.30 (t, J = 53.7 Hz, 1H), 4.16 (s, 2H), 3.65-3.56 (m, 8H), 3.32 (s, 3H). |
| II-171 | 373.2 | 1.96 | 1H NMR (500 MHz, DMSO-d6) δ 8.83 (d, J = 1.7 Hz, 1H), 8.56 (s, 1H), 8.46 (d, J = 9.4 Hz, 1H), 8.39 (d, J = 2.8 Hz, 1H), 8.09 (t, J = 2.3 Hz, 1H), 7.59 (d, J = 9.4 Hz, 1H), 7.27 (t, J = 53.7 Hz, 1H), 3.64 (dt, J = 6.4, 2.8 Hz, 4H), 3.37 (t, J = 5.4 Hz, 2H), 3.30 (m, 2H - hidden under DMSO), 2.07 (s, 3H). |
| II-172 | 386.2 | 2.06 | 1H NMR (500 MHz, DMSO-d6) δ 8.67 (s, 1H), 8.47 (d, J = 9.4 Hz, 1H), 8.26 (d, J = 5.3 Hz, 1H), 7.72 (s, 1H), 7.63 (d, J = 9.4 Hz, 1H), 7.52 (dd, J = 5.3, 1.3 Hz, 1H), 7.29 (t, J = 53.9 Hz, 1H), 6.51 |

TABLE 5-continued

Analytical data for compounds of Formula II

| II- | LCMS_Plus | LCMS_RT | NMR |
|---|---|---|---|
| | | | (s, 1H), 4.48 (dd, J = 13.0, 4.3 Hz, 1H), 4.35 (d, J = 11.4 Hz, 1H), 3.74-3.67 (m, 2H), 3.44 (t, J = 8.8 Hz, 1H), 3.01 (dd, J = 9.2, 4.6 Hz, 1H), 2.91 (td, J = 12.4, 3.3 Hz, 1H), 2.85-2.76 (m, 2H). |
| II-173 | 386.2 | 2.07 | 1H NMR (500 MHz, DMSO-d6) δ 8.67 (s, 1H), 8.47 (d, J = 9.4 Hz, 1H), 8.26 (d, J = 5.3 Hz, 1H), 7.71 (s, 1H), 7.63 (d, J = 9.4 Hz, 1H), 7.52 (dd, J = 5.4, 1.2 Hz, 1H), 7.29 (t, J = 53.9 Hz, 1H), 6.51 (s, 1H), 4.49-4.46 (m, 1H), 4.35 (d, J = 11.4 Hz, 1H), 3.74-3.67 (m, 2H), 3.44 (t, J = 8.8 Hz, 1H), 3.01 (dd, J = 9.2, 4.8 Hz, 1H), 2.91 (td, J = 12.4, 3.2 Hz, 1H), 2.85-2.76 (m, 2H). |
| II-174 | 369.2 | 1.94 | 1H NMR (500 MHz, DMSO-d6) δ 8.74 (s, 1H), 8.50-8.48 (m, 2H), 8.33 (d, J = 5.3 Hz, 1H), 7.81 (s, 1H), 7.66-7.63 (m, 2H), 7.31 (t, J = 53.8 Hz, 1H), 4.99 (s, 2H), 4.22-4.20 (m, 2H), 4.16-4.14 (m, 2H). |
| II-175 | 386.2 | 2.06 | 1H NMR (500 MHz, DMSO-d6) δ 8.67 (s, 1H), 8.47 (d, J = 9.4 Hz, 1H), 8.26 (d, J = 5.5 Hz, 1H), 7.72 (s, 1H), 7.63 (d, J = 9.4 Hz, 1H), 7.52 (dd, J = 5.3, 1.3 Hz, 1H), 7.29 (t, J = 53.8 Hz, 1H), 6.51 (s, 1H), 4.48 (dd, J = 12.8, 3.7 Hz, 1H), 4.35 (d, J = 13.0 Hz, 1H), 3.75-3.67 (m, 2H), 3.44 (t, J = 8.8 Hz, 1H), 3.01 (dd, J = 9.2, 4.8 Hz, 1H), 2.91 (td, J = 12.6, 3.4 Hz, 1H), 2.85-2.76 (m, 2H). |
| II-176 | 373.1 | 2.16 | 1H NMR (500 MHz, DMSO) δ 8.68 (s, 1H), 8.48 (d, J = 9.4 Hz, 1H), 8.27 (d, J = 5.1 Hz, 1H), 7.72 (s, 1H), 7.63 (d, J = 9.4 Hz, 1H), 7.51 (dd, J = 5.3, 1.3 Hz, 1H), 7.30 (t, J = 53.8 Hz, 1H), 3.68-3.66 (m, 2H), 3.61-3.58 (m, 6H), 2.07 (s, 3H). |
| II-177 | 454.3 | 2.18 | 1H NMR (500 MHz, DMSO-d6) δ 8.69-8.61 (m, 2H), 8.55 (d, J = 9.4 Hz, 1H), 7.98 (d, J = 1.2 Hz, 1H), 7.71 (d, J = 9.4 Hz, 1H), 7.31 (t, J = 53.4 Hz, 1H), 4.42 (d, J = 117.6 Hz, 2H), 4.06 (dd, J = 11.4, 3.4 Hz, 1H), 3.57 (td, J = 11.7, 2.8 Hz, 1H), 3.40 (dd, J = 12.8, 5.6 Hz, 1H), 3.28 (ddd, J = 10.2, 7.4, 2.6 Hz, 1H), 3.09 (d, J = 13.1 Hz, 1H), 3.01 (s, 3H), 2.87 (d, J = 11.9 Hz, 1H), 1.24 (d, J = 6.6 Hz, 3H). |
| II-178 | 418.8 | 1.85 | 1H NMR (400 MHz, DMSO-d6) δ 9.19 (d, J = 1.3 Hz, 1H), 8.75 (s, 1H), 8.56 (dd, J = 5.4, 4.0 Hz, 2H), 7.74 (d, J = 9.5 Hz, 1H), 7.41 (t, J = 53.6 Hz, 1H), 6.53 (t, J = 5.5 Hz, 1H), 4.59 (t, J = 5.5 Hz, 1H), 4.25-4.14 (m, 1H), 3.99 (d, J = 14.7 Hz, 1H), 3.39 (q, J = 6.1 Hz, 2H), 3.16-3.07 (m, 2H), 3.06-3.00 (m, 1H), 2.99-2.85 (m, 1H), 2.79 (td, J = 12.6, 2.8 Hz, 1H), 2.04 (d, J = 3.7 Hz, 1H), 1.90-1.65 (m, 2H), 1.62-1.43 (m, 1H). |
| II-179 | 416.2 | 2.14 | 1H NMR (500 MHz, DMSO-d6) δ 8.51 (s, 1H), 8.35 (s, 1H), 8.06 (d, J = 6.6 Hz, 1H), 7.93 (d, J = 9.7 Hz, 1H), 7.67-7.53 (m, 2H), 7.09 (t, J = 6.1 Hz, 1H), 4.13 (d, J = 13.3 Hz, 1H), 4.05 (d, J = 13.3 Hz, 1H), 3.26 (t, J = 12.0 Hz, 1H), 3.08 (t, J = 11.7 Hz, 1H), 2.99-2.85 (m, 8H), 1.94-1.76 (m, 3H), 1.59 (q, J = 12.3 Hz, 1H), 1.38 (t, J = 10.7 Hz, 1H). |
| II-180 | 387.1 | 2.07 | 1H NMR (400 MHz, Methanol-d4) δ 9.13 (d, J = 1.3 Hz, 1H), 8.78 (s, 1H), 8.68 (d, J = 1.3 Hz, 1H), 8.42 (d, J = 9.5 Hz, 1H), 7.74 (d, J = 9.5 Hz, 1H), 7.14 (t, J = 54.1 Hz, 1H), 4.82-4.65 (m, 4H), 4.01-3.53 (m, 1H), 3.20 (s, 2H), 2.99 (s, 1H), 2.59-2.33 (m, 1H), 2.26-2.08 (m, 2H), 2.06-1.68 (m, 3H). |
| II-181 | 436 | 2.02 | |
| II-182 | 389.1 | 2.21 | 1H NMR (500 MHz, DMSO-d6) δ 8.57 (s, 1H), 8.41 (d, J = 9.7 Hz, 1H), 8.22 (d, J = 5.7 Hz, 1H), 7.82 (t, J = 71.3 Hz, 1H), 7.77 (s, 1H), 7.47 (d, J = 5.6 Hz, 1H), 7.31 (d, J = 9.6 Hz, 1H), 3.72-3.70 (m, 2H), 3.62 (s, 6H), 2.08 (s, 3H). |
| II-183 | 401.1 | 2.33 | 1H NMR (500 MHz, DMSO-d6) δ 8.39 (s, 1H), 8.19 (d, J = 5.3 Hz, 1H), 8.14 (d, J = 9.3 Hz, 1H), 7.74 (s, 1H), 7.39 (dd, J = 5.3, 1.3 Hz, 1H), 7.27 (d, J = 9.3 Hz, 1H), 7.09 (t, J = 6.2 Hz, 1H), 4.37 (d, J = 13.5 Hz, 1H), 4.24 (d, J = 13.0 Hz, 1H), 2.98-2.84 (m, 6H), 2.64 (s, 4H), 1.91-1.80 (m, |

TABLE 5-continued

Analytical data for compounds of Formula II

| II- | LCMS_Plus | LCMS_RT | NMR |
|---|---|---|---|
| | | | 1H), 1.73 (ddd, J = 18.1, 8.9, 4.9 Hz, 2H), 1.58-1.37 (m, 1H), 1.25 (tt, J = 11.9, 5.8 Hz, 1H). |
| II-184 | 422.9 | 2.2 | |
| II-185 | 353.2 | 1.65 | 1H NMR (500 MHz, DMSO-d6) δ 8.65 (s, 1H), 8.30 (d, J = 9.4 Hz, 1H), 8.19 (d, J = 5.9 Hz, 1H), 8.05 (s, 1H), 7.64 (d, J = 5.9 Hz, 1H), 7.49 (d, J = 9.4 Hz, 1H), 4.76 (s, 2H), 3.74-3.72 (m, 2H), 3.67-3.65 (m, 6H), 2.08 (s, 3H). |
| II-186 | 374 | 1.85 | |
| II-187 | 343.1 | 1.95 | 1H NMR (500 MHz, DMSO) δ 8.62 (s, 1H), 8.38 (d, J = 9.5 Hz, 1H), 8.25 (d, J = 5.6 Hz, 1H), 7.67-7.65 (m, 2H), 7.55 (d, J = 9.5 Hz, 1H), 7.47 (d, J = 5.2 Hz, 1H), 3.90-3.85 (m, 4H), 3.28 (t, J = 6.6 Hz, 2H), 2.61-2.59 (m, 2H). |
| II-188 | 355.1 | 2.02 | 1H NMR (500 MHz, DMSO) δ 8.68 (s, 2H), 8.56 (s, 1H), 8.37 (d, J = 9.4 Hz, 1H), 8.23 (d, J = 5.6 Hz, 1H), 7.56-7.52 (m, 2H), 7.41 (s, 1H), 3.94-3.90 (m, 2H), 3.69-3.66 (m, 2H), 3.36-3.28 (m, 2H), 3.11-3.07 (m, 2H), 2.92-2.85 (m, 2H), 1.86-1.81 (m, 1H), 1.62-1.55 (m, 1H). |
| II-189 | 357.1 | 2.09 | 1H NMR (500 MHz, DMSO) δ 8.55 (s, 1H), 8.34 (d, J = 9.5 Hz, 1H), 8.24 (d, J = 5.5 Hz, 1H), 7.57 (s, 1H), 7.49 (d, J = 9.5 Hz, 1H), 7.36 (dd, J = 5.2, 1.2 Hz, 2H), 6.84 (s, 1H), 4.45-4.42 (m, 1H), 4.33 (d, J = 13.4 Hz, 1H), 2.94 (dd, J = 13.1, 11.1 Hz, 1H), 2.87 (td, J = 12.9, 3.2 Hz, 1H), 2.37-2.32 (m, 1H), 1.91 (d, J = 11.4 Hz, 1H), 1.76-1.70 (m, 1H), 1.69-1.60 (m, 1H), 1.53-1.44 (m, 1H). |
| II-190 | 388 | 1.97 | |
| II-191 | 418 | 1.81 | |
| II-192 | 396 | 1.71 | |
| II-193 | 337 | 2.03 | 1H NMR (500 MHz, DMSO-d6) δ 8.45 (s, 1H), 8.23 (dd, J = 5.4, 0.7 Hz, 1H), 8.15 (d, J = 9.3 Hz, 1H), 7.75 (brs, 1H), 7.53 (dd, J = 5.3, 1.3 Hz, 1H), 7.29 (d, J = 9.3 Hz, 1H), 3.75-3.52 (m, 8H), 2.65 (s, 3H), 2.07 (s, 3H). |
| II-194 | 316.1 | 2.29 | |
| II-195 | 329.1 | 2.23 | |
| II-196 | 418.4 | 2.04 | 1H NMR (500 MHz, DMSO-d6) δ 8.72 (d, J = 1.0 Hz, 1H), 8.56 (s, 1H), 8.27 (d, J = 9.4 Hz, 1H), 8.11 (d, J = 1.1 Hz, 1H), 7.46 (d, J = 9.4 Hz, 1H), 7.25 (t, J = 6.2 Hz, 1H), 4.47 (s, 1H), 4.28 (s, 1H), 4.05 (ddd, J = 11.6, 3.7, 1.5 Hz, 1H), 3.62 (tt, J = 7.7, 2.7 Hz, 2H), 3.28-3.19 (m, 1H), 3.14 (q, J = 6.1 Hz, 2H), 3.05 (q, J = 7.5 Hz, 2H), 3.01-2.96 (m, 1H), 2.95 (s, 3H), 1.39 (t, J = 7.5 Hz, 3H). |
| II-197 | 454.1 | 2.11 | 1H NMR (500 MHz, DMSO-d6) δ 8.65 (s, 2H), 8.54 (d, J = 1H), 7.99 (s, 1H), 7.71 (d, 1H), 7.29 (m, 2H), 3.87 (d, 1H), 3.75-3.73 (m, 1H), 3.55 (m, 1H), 3.35 (masked, 3H), 3.22 (m, 2H), 3.00 (s, 3H), 1.26 (m, 3H). |
| II-198 | 467 | 2.05 | 1H NMR (500 MHz, Methanol-d4) δ 8.75 (s, 1H), 8.71 (s, 1H), 8.48 (d, 1H), 8.14 (s, 1H), 7.80 (d, 1H), 7.15 (t, 1H), 4.43 (s, 1H), 3.85 (s, 1H), 3.65-3.50 (m, 3H), 3.45 (s, 3H), 3.20-3.10 (m, 2H), 2.94 (s, 3H), 2.30 (m, 1H), 2.03 (m, 1H), 1.51 (m, 1H). |
| II-199 | 410 | 1.85 | |
| II-200 | 386 | 1.86 | |
| II-201 | 390 | 2.01 | |
| II-202 | 439 | 2 | |
| II-203 | 383 | 1.83 | |
| II-204 | 353 | 2.09 | 1H NMR (500 MHz, Methanol-d4) δ 8.49 (s, 1H), 8.33 (d, 1H), 8.06-8.11 (m, 2H), 7.83 (dd, 1H), 7.17-7.19 (d, 1H), 4.20 (s, 3H), 3.86-3.89 (m, 8H), 2.20 (s, 3H). |
| II-205 | 440 | 1.95 | |
| II-206 | 521 | 2.12 | |
| II-207 | 383 | 2.31 | 1H NMR (500 MHz, Methanol-d4) δ 8.63 (s, 1H), 8.25-8.27 (d, 1H), 8.19 (s, 1H), 8.11-8.13 (m, 1H), 7.63 (d, 1H), 7.56-7.58 (d, 1H), 4.55 (d, 1H), 4.22-4.25 (d, 2H), 3.78-3.82 (m, 1H), 3.40-3.50 (m, 1H), 3.12-3.22 (m, 2H), 2.45-2.50 (m, 2H), 2.13- |

TABLE 5-continued

Analytical data for compounds of Formula II

| II- | LCMS_Plus | LCMS_RT | NMR |
|---|---|---|---|
| | | | 2.15 (m, 1H), 1.95-1.99 (m, 1H), 1.80-1.88 (m, 1H), 1.73-1.78 (m, 1H). |
| II-208 | 357 | 2.12 | 1H NMR (500 MHz, DMSO-d6) δ 8.66 (s, 1H), 8.38-8.40 (d, 1H), 8.25-8.26 (d, 1H), 7.72 (s, 1H), 7.55-7.57 (m, 2H), 3.70-3.71 (m, 2H), 3.64 (m, 6H), 2.08 (s, 3H). |
| II-209 | 446 | 2.27 | |
| II-210 | 390 | 1.67 | |
| II-211 | 414 | 1.99 | 1H NMR (500 MHz, DMSO-d6) δ 8.62 (s, 1H), 8.58 (d, J = 1.1 Hz, 1H), 8.53 (d, J = 9.4 Hz, 1H), 8.01 (d, J = 1.2 Hz, 1H), 7.69 (d, J = 9.4 Hz, 1H), 7.47-7.26 (m, 2H), 3.74 (br s, 4H), 3.11-2.96 (m, 2H), 2.19 (t, J = 7.0 Hz, 2H), 1.79-1.64 (m, 2H), 1.56 (t, J = 5.6 Hz, 4H). |
| II-212 | 402 | 1.98 | 1H NMR (500 MHz, DMSO-d6) δ 8.61 (s, 1H), 8.57 (d, J = 1.1 Hz, 1H), 8.53 (d, J = 9.4 Hz, 1H), 8.00 (d, J = 1.2 Hz, 1H), 7.68 (d, J = 9.5 Hz, 1H), 7.47-7.26 (m, 2H), 6.74 (s, 1H), 4.47 (br s, 2H), 2.98 (t, J = 12.6 Hz, 2H), 2.16-2.03 (m, 2H), 1.86-1.75 (m, 2H), 1.58 (ddp, J = 10.8, 7.0, 4.2, 3.3 Hz, 1H), 1.47 (q, J = 7.3 Hz, 2H), 1.11 (qd, J = 12.6, 4.3 Hz, 2H). |
| II-213 | 452.3 | 2.3 | 1H NMR (500 MHz, DMSO-d6) δ 8.74 (s, 1H), 8.71 (d, J = 11.9 Hz, 1H), 8.59 (d, J = 9.4 Hz, 1H), 7.78 (d, J = 9.3 Hz, 1H), 7.72 (d, J = 31.8 Hz, 1H), 7.48-7.26 (m, 1H), 7.16-7.11 (m, 1H), 4.04-3.99(m, 1H), 3.87-3.83 (m, 1H), 3.70 (d, J = 12.3 Hz, 1H), 3.49-3.45 (m, 1H), 3.40-3.36 (m, 1H), 3.24-3.19 (m, 1H), 2.96 (d, J = 11.8 Hz, 3H), 2.23 (d, J = 40.9 Hz, 1H), 1.21 (d, J = 18.1 Hz, 3H), 1.01 (d, J = 14.2 Hz, 3H). |
| II-214 | 402 | 2.06 | 1H NMR (500 MHz, DMSO-d6) δ 8.61 (s, 1H), 8.57 (d, J = 1.1 Hz, 1H), 8.52 (d, J = 9.4 Hz, 1H), 8.00 (d, J = 1.2 Hz, 1H), 7.68 (d, J = 9.4 Hz, 1H), 7.46-7.25 (m, 2H), 6.71 (s, 1H), 4.32 (br s, 2H), 3.09 (t, J = 12.5 Hz, 1H), 2.81 (t, J = 11.2 Hz, 1H), 2.24-2.08 (m, 2H), 1.96-1.83 (m, 1H), 1.83-1.70 (m, 1H), 1.62-1.34 (m, 4H), 1.33-1.15 (m, 1H). |
| II-215 | 403 | 1.9 | 1H NMR (500 MHz, DMSO-d6) δ 8.61 (s, 1H), 8.58 (d, J = 1.1 Hz, 1H), 8.52 (d, J = 9.4 Hz, 1H), 7.99 (d, J = 1.2 Hz, 1H), 7.68 (d, J = 9.4 Hz, 1H), 7.35 (t, J = 55.0 Hz, 1H), 6.10 (t, J = 5.9 Hz, 1H), 5.41 (d, J = 4.1 Hz, 2H), 4.68-4.07 (m, 2H), 3.10 (td, J = 12.3, 11.1, 2.8 Hz, 1H), 2.97 (t, J = 6.3 Hz, 2H), 2.81 (t, J = 11.7 Hz, 1H), 1.88-1.74 (m, 2H), 1.63 (ddd, J = 11.3, 7.2, 4.1 Hz, 1H), 1.46 (q, J = 12.4, 11.8 Hz, 1H), 1.37-1.20 (m, 1H). |
| II-216 | 415 | 1.91 | 1H NMR (500 MHz, DMSO-d6) δ 8.62 (s, 1H), 8.56 (d, J = 1.1 Hz, 1H), 8.52 (d, J = 9.4 Hz, 1H), 7.74-7.67 (m, 2H), 7.34 (t, J = 55.0 Hz, 1H), 6.17 (br s, 1H), 6.05 (s, 1H), 4.38-4.25 (m, 1H), 3.73-3.45 (m, 4H), 2.46-2.41 (m, 1H), 2.25-2.09 (m, 1H), 2.01-1.87 (m, 1H), 0.56 (td, J = 6.8, 4.7 Hz, 2H), 0.38-0.26 (m, 2H). |
| II-217 | 411 | 2.36 | 1H NMR (500 MHz, DMSO-d6) δ 12.49-12.42 (m, 1H), 8.61 (s, 1H), 8.57 (d, J = 1.1 Hz, 1H), 8.52 (d, J = 9.4 Hz, 1H), 7.99 (d, J = 1.2 Hz, 1H), 7.67 (d, J = 9.4 Hz, 1H), 7.61-7.24 (m, 2H), 6.05 (s, 1H), 4.46 (s, 2H), 2.99 (t, J = 12.7 Hz, 2H), 2.56 (s, 2H), 2.06-1.86 (m, 1H), 1.80-1.73 (m, 2H), 1.18 (qd, J = 12.5, 4.2 Hz, 2H). |
| II-218 | 436 | 2.2 | 1H NMR (500 MHz, DMSO-d6) δ 9.43 (s, 1H), 8.72-8.62 (m, 2H), 8.54 (d, J = 9.4 Hz, 1H), 8.06 (d, J = 1.3 Hz, 1H), 7.70 (d, J = 9.4 Hz, 1H), 7.52-7.29 (m, 2H), 7.22 (t, J = 7.7 Hz, 1H), 7.16 (d, J = 7.6 Hz, 1H), 4.89 (s, 2H), 3.92 (s, 2H), 2.86 (t, J = 6.0 Hz, 2H), 2.07 (s, 3H). |
| II-219 | 424 | 2.04 | 1H NMR (500 MHz, DMSO-d6) δ 8.63 (s, 1H), 8.58 (d, J = 1.1 Hz, 1H), 8.53 (d, J = 9.4 Hz, 1H), 8.02 (d, J = 1.2 Hz, 1H), 7.70 (d, J = 9.4 Hz, 1H), 7.36 (t, J = 55.0 Hz, 1H), 6.93 (s, 1H), 4.52-4.42 (m, 2H), 3.15-2.95 (m, 4H), 2.17-2.15 (m, 1H), 1.97 (br d, J = 11.4 Hz, 1H), 1.79-1.76 (m, 1H), 1.49 (tdd, J = 21.4, 11.4, 7.9 Hz, 2H). |

TABLE 5-continued

Analytical data for compounds of Formula II

| II- | LCMS_Plus | LCMS_RT | NMR |
|---|---|---|---|
| II-220 | 317.1 | 0.62 | |
| II-221 | 452.3 | 2.36 | 1H NMR (500 MHz, CD3OD) δ 8.75 (s, 1H), 8.72 (s, 1H), 8.50 (d, 1H), 8.08 (m, 1H), 7.85 (d, 1H), 7.28-7.04 (t, 1H), 5.30 (br m, 1H), 4.80-4.30 (br m, 2H), 2.95 (m, 5H), 1.90 (m, 2H), 1.70 (m, 1H), 1.47 (m, 2H), 1.35 (m, 3H). |
| 11-222 | 373.1 | 2.05 | 1H NMR (400 MHz, DMSO-d6) δ 9.20 (dd, J = 5.6, 1.3 Hz, 1H), 8.76 (d, J = 0.8 Hz, 1H), 8.61-8.53 (m, 2H), 7.75 (dd, J = 9.5, 3.1 Hz, 1H), 7.40 (d, J = 8.0 Hz, 1H), 4.57 (d, J = 11.2 Hz) and 4.35 (d, J = 13.0 Hz, 1H), 4.15-3.98 (m) and 3.86 (d, J = 13.5 Hz, 1H), 3.42 (dd, J = 13.3, 10.7 Hz, 1H), 3.23-2.62 (m, 2H), 2.06 (s, 4H), 2.01-1.73 (m, 2H), 1.55 (dd, J = 46.2, 12.7 Hz, 1H). NB 2 rotamers, approx 1:1 ratio. |
| 11-223 | 391.1 | 2.34 | 1H NMR (500 MHz, DMSO) δ 8.77 (s, 1H), 8.58 (d, J = 9.2 Hz, 1H), 8.30 (d, J = 5.5 Hz, 1H), 7.81 (d, J = 9.5 Hz, 1H), 7.71 (s, 1H), 7.48 (dd, J = 5.3, 1.3 Hz, 1H), 3.67-3.65 (m, 2H), 3.60-3.59 (m, 6H), 2.07 (s, 3H). |
| II-224 | 457.1 | 2.39 | |
| II-225 | 416.1 | 2.36 | |
| II-226 | 431.1 | 2.67 | 1H NMR (500 MHz, DMSO-d6) δ 8.77 (s, 1H), 8.61-8.56 (m, 1H), 8.30 (dd, J = 5.3, 0.7 Hz, 1H), 7.82 (d, J = 9.5 Hz, 1H), 7.76-7.72 (m, 1H), 7.50 (dd, J = 5.3, 1.3 Hz, 1H), 4.57-4.47 (m, 1H), 4.43-4.32 (m, 1H), 3.86 (dd, J = 11.1, 3.9 Hz, 1H), 3.83-3.73 (m, 1H), 3.23-3.11 (m, 1H), 3.00-2.87 (m, 2H), 1.19-0.96 (m, 3H), 0.89 (ddd, J = 10.2, 7.1, 4.8 Hz, 1H). |
| II-227 | 440.1 | 1.95 | 1H NMR (300 MHz, DMSO-d6) δ 1.36-1.62 (m, 2H), 1.65-1.77 (m, 1H), 2.00 (d, J = 11.7 Hz, 1H), 2.10-2.24 (m, 1H), 2.86-2.97 (m, 1H), 2.99-3.23 (m, 6H), 4.09 (d, J = 13.2 Hz, 1H), 4.43 (d, J = 13.2 Hz, 1H), 7.41 (d, J = 5.6 Hz, 1H), 7.66 (s, 1H), 7.80 (d, J = 9.4 Hz, 1H), 8.26 (d, J = 4.6 Hz, 1H), 8.58 (d, J = 9.4 Hz, 1H), 8.71 (s, 1H). |
| II-228 | 426.1 | 2.04 | 1H NMR (300 MHz, DMSO-d6) δ 1.51-1.68 (m, 1H), 1.69-1.93 (m, 2H), 2.15-2.26 (m, 1H), 2.93-3.14 (m, 5H), 3.21-3.31 (m, 1H), 4.25 (d, J = 13.8 Hz, 1H), 4.91 (d, J = 12.3 Hz, 1H), 7.42-7.50 (m, 1H), 7.76 (s, 1H), 7.82 (d, J = 9.4 Hz, 1H), 8.30 (d, J = 5.0 Hz, 1H), 8.59 (d, J = 9.4 Hz, 1H), 8.77 (s, 1H). |
| II-229 | 416.1 | 2.34 | 1H NMR (500 MHz, DMSO-d6) δ 12.80 (s, 1H), 8.78 (s, 1H), 8.57 (d, J = 9.5 Hz, 1H), 8.30 (d, J = 5.3 Hz, 1H), 7.80 (d, J = 9.5 Hz, 1H), 7.77 (d, J = 4.2 Hz, 1H), 7.75 (s, 1H), 7.54 (s, 1H), 7.50 (dd, J = 5.4, 1.3 Hz, 1H), 4.60 (dd, J = 10.5, 2.7 Hz, 1H), 4.36-4.28 (m, 1H), 4.21 (d, J = 12.8 Hz, 1H), 4.09-4.00 (m, 1H), 3.73 (td, J = 11.7, 2.8 Hz, 1H), 3.07-2.93 (m, 2H). |
| II-230 | 416.3 | 2.34 | 1H NMR (500 MHz, DMSO-d6) δ 12.80 (s, 1H), 8.78 (s, 1H), 8.57 (d, J = 9.5 Hz, 1H), 8.30 (d, J = 5.3 Hz, 1H), 7.80 (d, J = 9.5 Hz, 1H), 7.77 (d, J = 4.2 Hz, 1H), 7.75 (s, 1H), 7.54 (s, 1H), 7.50 (dd, J = 5.4, 1.3 Hz, 1H), 4.60 (dd, J = 10.5, 2.7 Hz, 1H), 4.36-4.28 (m, 1H), 4.21 (d, J = 12.8 Hz, 1H), 4.09-4.00 (m, 1H), 3.73 (td, J = 11.7, 2.8 Hz, 1H), 3.07-2.93 (m, 2H). |
| II-231 | 441.1 | 1.9 | 1H NMR (300 MHz, DMSO-d6) δ 1.39-1.63 (m, 2H), 1.70-1.84 (m, 1H), 1.92-2.05 (m, 1H), 2.77-2.88 (m, 1H), 2.95 (s, 4H), 3.19-3.31 (m, 1H), 4.10 (d, J = 13.2 Hz, 1H), 4.41 (d, J = 9.7 Hz, 1H), 7.26 (d, J = 7.6 Hz, 1H), 7.40 (d, J = 4.7 Hz, 1H), 7.70 (s, 1H), 7.80 (d, J = 9.5 Hz, 1H), 8.25 (d, J = 4.7 Hz, 1H), 8.57 (d, J = 9.5 Hz, 1H), 8.72 (s, 1H). |
| II-232 | 471.1 | 1.85 | 1H NMR (300 MHz, DMSO-d6) δ 2.20-2.34 (m, 1H), 2.86-3.02 (m, 4H), 3.29-3.39 (m, 2H), 3.41-3.59 (m, 2H), 3.60-3.90 (m, 3H), 4.02-4.24 (m, 2H), 7.11 (t, J = 5.6 Hz, 1H), 7.34 (dd, J = 5.3, 1.2 Hz, 1H), 7.59 (s, 1H), 7.81 (d, J = 9.4 Hz, 1H), 8.23 (d, J = 5.3 Hz, 1H), 8.58 (d, J = 9.4 Hz, 1H), 8.73 (s, 1H). |
| II-233 | 467 | 2.08 | 1H NMR (500 MHz, Methanol-d4) δ 8.75 (s, 1H), 8.71 (s, 1H), 8.48 (d, 1H), 8.14 (s, 1H), 7.80 (d, |

TABLE 5-continued

Analytical data for compounds of Formula II

| II- | LCMS_Plus | LCMS_RT | NMR |
|---|---|---|---|
| | | | 1H), 7.15 (t, 1H), 4.43 (s, 1H), 3.85 (s, 1H), 3.65-3.50 (m, 3H), 3.45 (s, 3H), 3.20-3.10 (m, 2H), 2.94 (s, 3H), 2.30 (m, 1H), 2.03 (m, 1H), 1.51 (m, 1H). |
| II-234 | 454.1 | 2.11 | 1H NMR (500 MHz, DMSO-d6) δ 8.65 (s, 2H), 8.54 (d, 1H), 7.99 (s, 1H), 7.71 (d, 1H), 7.29 (m, 2H), 3.87 (d, 1H), 3.75-3.73 (m, 1H), 3.55 (m, 1H), 3.35 (masked, 3H), 3.22 (m, 2H), 3.00 (s, 3H), 1.26 (m, 3H). |
| II-235 | 468.1 | 1.94 | 1H NMR (500 MHz, DMSO-d6) δ 8.72 (m, 2H), 8.55 (d, 1H), 7.99 (s, 1H), 7.76 (d, 1H), 7.36-7.15 (t, 1H), 3.51 (m, 1H), 4.40-4.10 (br s, 3H), 3.15 (m, 1H), 2.98-2.91 (m, 4H), 2.82-2.73 (m, 4H), 2.08-1.92 (m, 2H), 1.20-1.15 (m, 1H). |
| II-236 | 438.3 | 2.31 | 1H NMR (500 MHz, DMSO-d6) δ 8.67 (s, 1H), 8.64 (d, J = 1.0 Hz, 1H), 8.55 (d, J = 9.4 Hz, 1H), 8.09-8.01 (m, 1H), 7.73 (d, J = 9.5 Hz, 1H), 7.48-7.23 (m, 1H), 7.03 (d, J = 5.3 Hz, 1H), 4.54 (t, J = 52.6 Hz, 4H), 3.16-3.00 (m, 4H), 2.61 (d, J = 4.9 Hz, 2H), 2.12-2.04 (m, 1H), 1.96 (dd, J = 34.3, 12.7 Hz, 1H), 1.83-1.72 (m, 1H), 1.50 (q, J = 12.8 Hz, 1H). |
| II-237 | 438.1 | 2.14 | 1H NMR (500 MHz, DMSO-d6) δ 8.62 (s, 1H), 8.55 (d, J = 1.1 Hz, 1H), 8.53 (d, J = 9.4 Hz, 1H), 7.71 (s, 1H), 7.69 (d, J = 9.5 Hz, 1H), 7.46-7.25 (m, 1H), 7.19 (s, 1H), 3.91 (br s, 1H), 3.72 (br s, 1H), 3.35-3.33 (m, 1H), 3.23-3.18 (m, 1H), 3.10 (br s, 1H), 2.99 (br s, 1H), 2.94 (s, 3H), 2.22-2.03 (m, 2H), 1.13 (s, 3H). |
| II-238 | 438.1 | 2.14 | 1H NMR (500 MHz, DMSO-d6) δ 8.62 (s, 1H), 8.55 (d, J = 1.1 Hz, 1H), 8.53 (d, J = 9.4 Hz, 1H), 7.71 (s, 1H), 7.69 (d, J = 9.5 Hz, 1H), 7.46-7.24 (m, 1H), 7.20 (s, 1H), 3.90 (br s, 1H), 3.74 (br s, 1H), 3.35-3.33 (m, 1H), 3.21-3.17(m, 1H), 3.11 (br s, 1H), 3.01 (br s, 1H), 2.94 (s, 3H), 2.20-2.04 (m, 2H), 1.13 (s, 3H). |
| II-239 | 468.3 | 1.95 | 1H NMR (500 MHz, DMSO-d6) δ 8.77-8.68 (m, 2H), 8.57 (d, J = 9.4 Hz, 1H), 8.01 (d, J = 1.1 Hz, 1H), 7.76 (d, J = 9.4 Hz, 1H), 7.44-7.15 (m, 1H), 7.03 (dd, J = 7.8, 4.5 Hz, 1H), 4.11 (s, 3H), 3.53 (s, 2H), 3.30 (dt, J = 12.6, 4.0 Hz, 2H), 2.90 (s, 3H), 2.71 (ddd, J = 12.5, 10.8, 7.7 Hz, 1H), 1.80-1.64 (m, 1H), 1.60 (ddd, J = 13.5, 9.6, 4.2 Hz, 1H), 1.18 (s, 3H). |
| II-240 | 468.3 | 1.97 | 1H NMR (500 MHz, DMSO-d6) δ 8.69 (d, J = 6.4 Hz, 2H), 8.57 (d, J = 9.4 Hz, 1H), 7.98 (d, J = 1.1 Hz, 1H), 7.75 (d, J = 9.5 Hz, 1H), 7.30 (t, J = 53.5 Hz, 1H), 7.04 (dd, J = 7.5, 5.0 Hz, 1H), 3.42-3.29 (m, 2H), 3.07 (s, 1H), 2.94 (s, 4H), 1.63 (dt, J = 33.4, 12.4 Hz, 3H), 1.23 (s, 3H). |
| II-241 | 387.1 | 2.07 | |
| II-242 | 387.2 | 2.07 | |
| II-243 | 438.3 | 2.13 | 1H NMR (500 MHz, DMSO-d6) δ 8.61 (s, 1H), 8.56 (d, J = 1.1 Hz, 1H), 8.52 (d, J = 9.4 Hz, 1H), 7.82 (s, 0.3H), 7.68 (d, J = 9.4 Hz, 1H), 7.66 (br s, 0.7H), 7.46-7.18 (m, 1H), 7.14 (t, J = 5.5 Hz, 1H), 4.52 (br s, 0.7H), 4.16 (br s, 0.3H), 3.62 (br s, 1H), 3.42 (br s, 1H), 3.14-3.09 (m, 2H), 2.95 (s, 3H), 2.42 (br s, 1H), 2.16 (br s, 1H), 1.87 (br s, 1H), 1.13 (s, 3H). |
| II-244 | 438.3 | 2.16 | 1H NMR (500 MHz, DMSO-d6) δ 8.61 (s, 1H), 8.56 (d, J = 1.1 Hz, 1H), 8.52 (d, J = 9.4 Hz, 1H), 7.74 (br s, 1H), 7.68 (d, J = 9.4 Hz, 1H), 7.36 (br d, 1H), 7.21 (s, 1H), 4.09 (br d, 1H), 3.61-3.56 (m, 1H), 3.60 (br s, 1H), 2.99-2.95 (m, 1H), 2.92-2.87 (m, 1H), 2.89 (s, 3H), 2.16 (br s, 2H), 1.90 (br s, 1H), 1.29 (s, 3H). |
| II-245 | 452.1 | 2.37 | 1H NMR (500 MHz, DMSO-d6) δ 8.60 (s, 1H), 8.56 (d, 1H), 8.51 (d, 1H), 8.00 (d, 1H), 7.66 (d, 1H), 7.32 (t, 1H), 7.05 (s, 1H), 4.60 (s, 1H), 4.27 (s, 1H), 3.02-2.89 (m, 2H), 2.85 (s, 3H), 2.65 (masked, 1H), 2.05 (m, 2H), 1.87 (m, 2H), 1.60-1.50 (m, 1H), 1.24 (d, 3H). |
| II-246 | 452.3 | 2.37 | 1H NMR (500 MHz, DMSO-d6) δ 8.60 (s, 1H), 8.56 (d, 1H), 8.51 (d, 1H), 8.00 (d, 1H), 7.66 (d, 1H), 7.32 (t, 1H), 7.05 (s, 1H), 4.60 (s, 1H), 4.27 |

TABLE 5-continued

Analytical data for compounds of Formula II

| II- | LCMS_Plus | LCMS_RT | NMR |
|---|---|---|---|
| | | | (s, 1H), 3.02-2.89 (m, 2H), 2.85 (s, 3H), 2.65 (masked, 1H), 2.05 (m, 2H), 1.87 (m, 2H), 1.60-1.50 (m, 1H), 1.24 (d, 3H). |
| II-247 | 452.1 | 2.35 | 1H NMR (500 MHz, DMSO-d6) δ 8.60 (s, 1H), 8.59 (s, 1H), 8.51 (d, 1H), 8.00 (d, 1H), 7.69-7.67 (d, 1H), 7.39-7.21 (t, 1H), 7.18 (s, 1H), 4.60-4.27 (broad s, 2H), 3.02-2.89 (m, 5H), 2.70 (m, 1H), 1.75-1.62 (m, 4H), 1.40-1.35 (m, 1H), 1.24 (d, 3H). |
| II-248 | 452.3 | 2.35 | 1H NMR (500 MHz, DMSO-d6) δ 8.60 (s, 1H), 8.59 (s, 1H), 8.51 (d, 1H), 8.00 (d, 1H), 7.69-7.67 (d, 1H), 7.39-7.21 (t, 1H), 7.18 (s, 1H), 4.60-4.27 (broad s, 2H), 3.02-2.89 (m, 5H), 2.70 (m, 1H), 1.75-1.62 (m, 4H), 1.40-1.35 (m, 1H), 1.24 (d, 3H). |
| II-249 | 430.3 | 2.1 | 1H NMR (500 MHz, DMSO-d6) δ 8.72 (d, J = 0.9 Hz, 1H), 8.53 (s, 1H), 8.23 (d, J = 9.4 Hz, 1H), 8.03 (s, 1H), 7.37 (d, J = 9.5 Hz, 1H), 7.27 (t, J = 6.3 Hz, 1H), 4.48 (s, 1H), 4.30 (s, 1H), 4.06 (ddd, J = 11.6, 3.7, 1.5 Hz, 1H), 3.63 (ddd, J = 11.4, 8.9, 3.0 Hz, 2H), 3.26 (d, J = 12.6 Hz, 1H), 3.19-3.14 (m, 2H), 3.01 (d, J = 11.9 Hz, 1H), 2.95 (s, 3H), 2.41 (tt, J = 8.2, 4.9 Hz, 1H), 1.22 (ddd, J = 8.5, 5.0, 2.1 Hz, 2H), 1.13 (tt, J = 4.5, 2.3 Hz, 2H). |
| II-250 | 395 | 2.06 | 1H NMR (400 MHz, DMSO-d6) δ 9.22 (d, J = 1.3 Hz, 1H), 8.77 (s, 1H), 8.61 (d, J = 1.3 Hz, 1H), 8.57 (d, J = 9.4 Hz, 1H), 7.76 (d, J = 9.5 Hz, 1H), 7.38 (s, 1H), 3.81-3.73 (m, 2H), 3.59-3.37 (m, 3H), 2.99 (s, 3H), 2.49-2.39 (m, 1H), 2.28-2.14 (m, 1H). |
| II-251 | 333.3 | 2.14 | 1H NMR (500 MHz, DMSO-d6) δ 8.63 (s, 1H), 8.63 (d, J = 1.1 Hz, 1H), 8.53 (d, J = 9.4 Hz, 1H), 7.98 (d, J = 1.2 Hz, 1H), 7.70 (d, J = 9.4 Hz, 1H), 7.37 (t, J = 53.6 Hz, 1H), 3.79-3.64 (m, 8H). |
| II-252 | 345.3 | 1.92 | 1H NMR (500 MHz, DMSO-d6) δ 8.61 (s, 1H), 8.55 (d, J = 1.2 Hz, 1H), 8.52 (d, J = 9.4 Hz, 1H), 7.69 (d, J = 9.4 Hz, 1H), 7.56 (d, J = 1.2 Hz, 1H), 7.35 (t, J = 53.7 Hz, 1H), 4.77 (s, 4H), 4.32 (s, 4H). |
| II-253 | 359.3 | 1.88 | 1H NMR (400 MHz, DMSO-d6) δ 9.21 (dd, J = 2.8, 1.3 Hz, 1H), 8.77 (s, 1H), 8.62-8.51 (m, 2H), 7.75 (dd, J = 9.4, 1.3 Hz, 1H), 7.38 (td, J = 53.7, 2.3 Hz, 1H), 4.02-3.37 (m, 5H), 2.47-2.04 (m, 2H), 2.00 (d, J = 4.8 Hz, 3H). |
| II-254 | 404.1 | 1.65 | 1H NMR (400 MHz, DMSO-d6) δ 9.20 (d, J = 1.3 Hz, 1H), 8.76 (s, 1H), 8.57 (dd, J = 5.4, 4.0 Hz, 2H), 7.75 (d, J = 9.5 Hz, 1H), 7.38 (t, J = 53.6 Hz, 1H), 6.17 (t, J = 5.6 Hz, 1H), 4.63 (t, J = 5.5 Hz, 1H), 3.77 (dd, J = 9.7, 7.4 Hz, 1H), 3.68 (t, J = 7.3 Hz, 1H), 3.58-3.44 (m, 2H), 3.40 (d, J = 5.8 Hz, 3H), 3.12 (qd, J = 6.3, 1.9 Hz, 2H), 2.36 (ddd, J = 13.7, 7.0, 3.3 Hz, 1H), 2.26-2.10 (m, 1H). |
| II-255 | 423.2 | 1.98 | 1H NMR (400 MHz, DMSO-d6) δ 9.17 (d, J = 1.3 Hz, 1H), 8.75 (s, 1H), 8.62-8.47 (m, 2H), 7.74 (d, J = 9.4 Hz, 1H), 7.37 (t, J = 53.7 Hz, 1H), 3.62 (s, 1H), 3.29 (d, J = 3.5 Hz, 2H), 3.11 (t, J = 8.5 Hz, 1H), 3.02 (s, 3H), 2.95-2.62 (m, 4H), 2.60-2.51 (m, 1H), 2.39-2.21 (m, 1H), 2.12 (d, J = 7.8 Hz, 1H). |
| II-256 | 464.3 | 2.37 | |
| II-257 | 468.3 | 2.31 | 1H NMR (500 MHz, Methanol-d4) δ 8.80 (s, 1H), 8.77 (s, 1H), 8.51 (d, 1H), 8.05 (s, 1H), 7.85 (d, 1H), 7.27-7.05 (t, 1H), 4.03 (m, 1H), 3.35-3.10 (6H), 3.02 (s, 3H), 1.38 (s, 3H), 1.30 (s, 3H). |
| II-258 | 474.3 | 2.3 | 1H NMR (500 MHz, DMSO-d6) δ 8.68-8.63 (m, 2H), 8.54 (d, J = 9.4 Hz, 1H), 8.07 (d, J = 1.2 Hz, 1H), 7.70 (d, J = 9.4 Hz, 1H), 7.44-7.17 (m, 2H), 4.71 (s, 1H), 4.55-4.31 (m, 1H), 3.57 (dd, J = 29.9, 13.8 Hz, 1H), 3.09-2.99 (m, 3H), 2.94 (s, 3H), 2.30 (d, J = 10.8 Hz, 1H), 1.96 (dtd, J = 43.6, 12.3, 11.7, 5.1 Hz, 2H). |
| II-259 | 517.4 | 2.31 | 1H NMR (500 MHz, DMSO-d6) δ 8.70-8.62 (m, 2H), 8.54 (d, J = 9.4 Hz, 1H), 8.11-8.04 (m, 1H), 7.71 (d, J = 9.4 Hz, 1H), 7.40-7.08 (m, 2H), 4.68 |

TABLE 5-continued

Analytical data for compounds of Formula II

| II- | LCMS_Plus | LCMS_RT | NMR |
|---|---|---|---|
| | | | (s, 2H), 3.41 (ddd, J = 13.5, 5.5, 3.5 Hz, 1H), 3.03-2.87 (m, 6H), 2.48 (s, 6H), 2.17 (s, 1H), 1.24-1.17 (m, 1H). |
| II-260 | 517.3 | 2.36 | 1H NMR (500 MHz, DMSO-d6) δ 8.65 (d, J = 1.4 Hz, 2H), 8.54 (d, J = 9.4 Hz, 1H), 8.12 (d, J = 1.2 Hz, 1H), 7.70 (d, J = 9.4 Hz, 1H), 7.43-7.10 (m, 2H), 4.00 (s, 2H), 3.74 (dd, J = 13.7, 6.9 Hz, 1H), 3.27 (d, J = 12.9 Hz, 1H), 2.91 (s, 5H), 2.42 (s, 6H). |
| II-261 | 402.3 | 2.09 | 1H NMR (400 MHz, DMSO-d6) δ 8.61 (s, 1H), 8.57 (d, J = 1.0 Hz, 1H), 8.52 (d, J = 9.4 Hz, 1H), 8.07-7.85 (m, 2H), 7.68 (d, J = 9.4 Hz, 1H), 7.37 (t, J = 53.7 Hz, 1H), 4.30 (s, 2H), 3.17-2.99 (m, 3H), 2.88-2.76 (m, 1H), 1.83 (s, 5H), 1.67 (ddd, J = 10.7, 6.9, 3.9 Hz, 1H), 1.46 (d, J = 12.4 Hz, 1H), 1.29 (qd, J = 13.8, 4.2 Hz, 1H). |
| II-262 | 463.9 | 2.41 | 1H NMR (400 MHz, DMSO-d6) δ 8.62 (s, 1H), 8.58 (d, J = 1.0 Hz, 1H), 8.52 (d, J = 9.4 Hz, 1H), 7.99 (d, J = 1.2 Hz, 1H), 7.68 (d, J = 9.4 Hz, 1H), 7.47-7.12 (m, 2H), 4.67-4.13 (m, 2H), 3.15-3.04 (m, 1H), 2.98 (p, J = 6.7 Hz, 2H), 2.84 (t, J = 11.8 Hz, 1H), 2.65-2.52 (m, 1H), 1.94-1.63 (m, 3H), 1.48 (q, J = 12.0 Hz, 1H), 1.33 (dd, J = 11.9, 3.5 Hz, 1H), 1.02-0.83 (m, 4H). |
| II-263 | 452.1 | 2.34 | |
| II-264 | 452.1 | 2.34 | |
| II-265 | 452.1 | 2.33 | |
| II-266 | 452.1 | 2.33 | 1H NMR (500 MHz, DMSO-d6) δ 8.62 (s, 1H), 8.60 (d, 1H), 8.00 (s, 1H), 7.69 (d, 1H), 7.25 (t, 1H), 7.13 (m, 1H), 4.70-4.20 (br m, 2H), 2.94 (m, 5H), 1.90 (m, 2H), 1.77 (m, 1H), 1.41 (m, 2H), 1.22 (m, 1H), 1.10 (m, 3H). |
| II-267 | 468 | 2.29 | 1H NMR (500 MHz, Methanol-d4) δ 8.75 (m, 2H), 8.45 (dd, 1H), 8.09 (s, 1H), 7.79 (s, 1H), 7.27 (t, 1H), 4.84 (masked 3H), 4.12 (m, 2H), 3.79 (m, 1H), 3.70 (m, 1H), 3.02 (s, 3H), 1.97 (m, 2H), 1.01 (m, 4H). |
| II-268 | 466 | 2.46 | |
| II-269 | 468 | 2.25 | |
| II-270 | 505.3 | 2.77 | 1H NMR (500 MHz, DMSO-d6) δ 8.50 (m, 3H), 8.26 (d, J = 7.8 Hz, 1H), 7.63 (d, J = 9.4 Hz, 1H), 7.28 (t, J = 53.7 Hz, 1H), 4.17 (d, J = 11.6 Hz, 1H), 3.82 (d, J = 12.6 Hz, 1H), 3.43 (dd, J = 13.5, 3.4 Hz, 1H), 2.95 (m, 4H), 2.93 (s, 3H), 2.37 (m, 2H) 1.05 (d, J = 6.7 Hz, 3H). |
| II-271 | 469.3 | 2.67 | 1H NMR (500 MHz, Methanol-d4) δ 8.46 (s, 1H), 8.33 (d, J = 9.4 Hz, 1H), 8.24 (m, 2H), 7.63 (d, J = 9.5 Hz, 1H), 7.07 (t, J = 54.0 Hz, 1H), 4.41-4.31 (m, 1H), 3.77 (dd, J = 12.9, 4.3 Hz, 1H), 3.14-3.02 (m, 3H), 2.98 (s, 3H), 2.08-1.88 (m, 3H), 1.80-1.73 (m, 2H), 1.59-1.52 (m, 1H) 1.27 (d, J = 6.8 Hz, 3H). |
| II-272 | 479.3 | 2.11 | 1H NMR (400 MHz, DMSO-d6) δ 8.62 (s, 1H), 8.63-8.55 (m, 2H), 8.53 (d, J = 9.4 Hz, 1H), 7.99 (d, J = 1.2 Hz, 1H), 7.69 (d, J = 9.4 Hz, 1H), 7.52-7.12 (m, 2H), 4.64-4.37 (m, 1H), 4.40-4.16 (m, 1H), 4.09 (d, J = 15.5 Hz, 1H), 3.88-3.59 (m, 4H), 3.07 (d, J = 11.6 Hz, 1H), 2.96 (dq, J = 11.3, 6.8, 6.3 Hz, 2H), 2.82 (t, J = 11.9 Hz, 1H), 1.79 (d, J = 17.7 Hz, 2H), 1.66 (s, 1H), 1.47 (d, J = 12.3 Hz, 1H), 1.39-1.20 (m, 1H). |
| II-273 | 452.3 | 2.17 | 1H NMR (500 MHz, DMSO-d6) δ 8.67 (d, J = 1.1 Hz, 1H), 8.65 (s, 1H), 8.54 (d, J = 9.4 Hz, 1H), 8.04 (d, J = 1.2 Hz, 1H), 7.71 (d, J = 9.4 Hz, 1H), 7.34 (t, J = 53.6 Hz, 1H), 3.95 (s, 2H), 3.91-3.76 (m, 6H), 3.68 (t, J = 4.8 Hz, 2H), 3.07 (s, 3H). |
| II-274 | 379 | 2.66 | 1H NMR (500 MHz, DMSO-d6) δ 8.62 (s, 1H), 8.59 (d, J = 1.1 Hz, 1H), 8.53 (d, J = 9.4 Hz, 1H), 7.93 (d, J = 1.2 Hz, 1H), 7.69 (d, J = 9.4 Hz, 1H), 7.37 (t, J = 55.0 Hz, 1H), 4.12 (s, 1H), 3.93 (d, J = 14.2 Hz, 1H), 3.75 (s, 1H), 2.12-2.04 (m, 3H), 1.75 (s, 1H), water peak obscures one signal. |
| II-275 | 423 | 2.21 | 1H NMR (500 MHz, DMSO-d6) δ 9.17 (d, J = 1.3 Hz, 1H), 8.75 (s, 1H), 8.66-8.45 (m, 2H), 7.74 (d, J = 9.5 Hz, 1H), 7.38 (t, J = 55.0 Hz, |

TABLE 5-continued

Analytical data for compounds of Formula II

| II- | LCMS_Plus | LCMS_RT | NMR |
|---|---|---|---|
| | | | 1H), 3.64-3.53 (m, 1H), 3.47 (dt, J = 13.3, 4.5 Hz, 1H), 3.41-3.34 (m, 1H), 3.07 (tt, J = 10.7, 3.3 Hz, 1H), 2.93 (s, 3H), 2.12 (dq, J = 13.6, 4.3 Hz, 1H), 2.03-1.96 (m, 3H), 1.93-1.85 (dq, J = 10.9, 5.9, 5.3 Hz, 1H), 1.83-1.69 (m, 1H), water peak obscures some signals. |
| II-276 | 423 | 2.21 | 1H NMR (500 MHz, DMSO-d6) δ 9.17 (d, J = 1.3 Hz, 1H), 8.75 (s, 1H), 8.66-8.45 (m, 2H), 7.74 (d, J = 9.5 Hz, 1H), 7.38 (t, J = 55.0 Hz, 1H), 3.64-3.53 (m, 1H), 3.47 (dt, J = 13.3, 4.5 Hz, 1H), 3.41-3.34 (m, 1H), 3.07 (tt, J = 10.7, 3.3 Hz, 1H), 2.93 (s, 3H), 2.12 (dq, J = 13.6, 4.3 Hz, 1H), 2.03-1.96 (m, 3H), 1.93-1.85 (dq, J = 10.9, 5.9, 5.3 Hz, 1H), 1.83-1.69 (m, 1H), water peak obscures some signals. |
| II-277 | 439 | 2.04 | 1H NMR (500 MHz, DMSO-d6) δ 8.62 (s, 1H), 8.58 (d, J = 1.1 Hz, 1H), 8.53 (d, J = 9.4 Hz, 1H), 8.00 (d, J = 1.3 Hz, 1H), 7.69 (d, J = 9.4 Hz, 1H), 7.30 (t, J = 55.0 Hz, 1H), 6.66 (t, J = 6.3 Hz, 1H), 6.52 (s, 2H), 4.45 (brs, 1H), 4.32 (brs, 1H), 3.17-3.03 (m, 1H), 2.91-2.80 (m, 3H), 1.96-1.63 (m, 3H), 1.58-1.41 (m, 1H), 1.40-1.25 (m, 1H). |
| II-278 | 439 | 2.03 | 1H NMR (500 MHz, DMSO-d6) δ 8.62 (s, 1H), 8.58 (d, J = 1.1 Hz, 1H), 8.52 (d, J = 9.4 Hz, 1H), 8.00 (d, J = 1.2 Hz, 1H), 7.68 (d, J = 9.4 Hz, 1H), 7.30 (t, J = 55.0 Hz, 1H), 6.66 (s, 1H), 6.52 (s, 2H), 4.44 (brs, 1H), 4.31 (brs, 1H), 3.09 (t, J = 12.4 Hz, 1H), 2.86-2.82 (m, 3H), 1.92-1.67 (m, 3H), 1.46 (t, J = 12.9 Hz, 1H), 1.39-1.25 (m, 1H). |
| II-279 | 450 | 2.2 | 1H NMR (500 MHz, DMSO-d6) δ 8.62 (s, 1H), 8.56 (d, J = 1.2 Hz, 1H), 8.52 (d, J = 9.4 Hz, 1H), 7.69 (d, J = 9.4 Hz, 1H), 7.58 (d, J = 1.2 Hz, 1H), 7.35 (t, J = 55.0 Hz, 1H), 3.86 (s, 4H), 3.20-3.04 (m, 4H), 2.90 (s, 3H), 1.82-1.79 (m, 2H), 1.67-1.64 (m, 2H). |
| II-280 | 452 | 2.05 | 1H NMR (500 MHz, DMSO-d6) δ 8.63 (s, 1H), 8.59 (d, J = 1.2 Hz, 1H), 8.53 (d, J = 9.4 Hz, 1H), 7.70 (d, J = 9.4 Hz, 1H), 7.63 (d, J = 1.2 Hz, 1H), 7.37 (t, J = 55.0 Hz, 1H), 4.10 (d, J = 9.6 Hz, 2H), 4.05 (d, J = 9.6 Hz, 2H), 3.80 (t, J = 4.8 Hz, 2H), 3.37 (s, 2H), 3.21-3.11 (m, 2H), 2.96 (s, 3H). |
| II-281 | 450 | 2.27 | 1H NMR (500 MHz, DMSO-d6) δ 8.62 (s, 1H), 8.61 (d, J = 1.1 Hz, 1H), 8.53 (d, J = 9.4 Hz, 1H), 8.05 (d, J = 1.2 Hz, 1H), 7.69 (d, J = 9.4 Hz, 1H), 7.39 (d, J = 55.0 Hz, 1H), 3.95 (s, 2H), 3.71-3.58 (m, 6H), 3.03 (s, 3H), 1.87 (dd, J = 7.4, 4.6 Hz, 2H), 1.73-1.53 (m, 2H). |
| II-282 | 436 | 2.1 | 1H NMR (500 MHz, DMSO-d6) δ 8.64-8.61 (m, 2H), 8.53 (d, J = 9.4 Hz, 1H), 7.80-7.69 (m, 2H), 7.34 (t, J = 55.0 Hz, 1H), 4.62 (brs, 1H), 3.78-3.71 (m, 2H), 3.62 (brs, 1H), 3.47 (brs, 1H), 3.25-3.01 (m, 3H), 2.93 (s, 3H), 2.23 (brs, 1H), 1.98 (brs, 1H). |
| II-283 | 438 | 2.24 | 1H NMR (500 MHz, DMSO-d6) δ 8.61 (s, 1H), 8.58 (d, J = 1.1 Hz, 1H), 8.52 (d, J = 9.4 Hz, 1H), 7.99 (d, J = 1.2 Hz, 1H), 7.68 (d, J = 9.4 Hz, 1H), 7.35 (t, J = 55.0 Hz, 1H), 6.78 (s, 2H), 4.90 (vbrs, 1H), 4.37 (vbrs, 1H), 3.04 (ddd, J = 13.8, 11.5, 5.1 Hz, 2H), 2.86 (ddd, J = 13.7, 11.5, 4.4 Hz, 1H), 2.36-2.19 (m, 1H), 2.15-1.96 (m, 1H), 1.88-1.57 (m, 5H), 1.56-1.35 (m, 1H). |
| II-284 | 451 | 2.03 | |
| II-285 | 453 | 1.9 | 1H NMR (500 MHz, DMSO-d6) δ 8.68 (s, 1H), 8.66 (d, J = 1.1 Hz, 1H), 8.56 (d, J = 9.4 Hz, 1H), 7.74 (d, J = 9.4 Hz, 1H), 7.63 (d, J = 1.1 Hz, 1H), 7.32 (d, J = 55.0 Hz, 1H), 6.99 (s, 2H), 4.24-4.04 (m, 4H), 3.80 (t, J = 4.9 Hz, 2H), 3.20 (s, 2H), 2.99 (s, 2H). |
| II-286 | 437 | 1.93 | |
| II-287 | 480.3 | 2.23 | 1H NMR (500 MHz, DMSO-d6) δ 8.63 (s, 1H), 8.61 (d, J = 1.1 Hz, 1H), 8.53 (d, J = 9.4 Hz, 1H), 8.00 (d, J = 1.2 Hz, 1H), 7.69 (d, J = 9.4 Hz, 1H), 7.36 (t, J = 53.8 Hz, 1H), 3.84-3.77 (m, 2H), 3.78-3.71 (m, 2H), 3.68 (s, 2H), 3.38-3.27 (m, |

TABLE 5-continued

Analytical data for compounds of Formula II

| II- | LCMS_Plus | LCMS_RT | NMR |
|---|---|---|---|
| | | | 2H), 2.97 (dd, J = 11.8, 2.7 Hz, 2H), 2.88 (s, 3H), 1.94 (d, J = 13.9 Hz, 2H), 1.62 (ddd, J = 13.8, 11.6, 4.5 Hz, 2H). |
| II-288 | 480.3 | 2.23 | 1H NMR (500 MHz, DMSO-d6) δ 8.63 (s, 1H), 8.61 (d, J = 1.1 Hz, 1H), 8.53 (d, J = 9.4 Hz, 1H), 8.02 (d, J = 1.2 Hz, 1H), 7.69 (d, J = 9.4 Hz, 1H), 7.32 (t, J = 53.8 Hz, 1H), 3.93 (d, J = 13.5 Hz, 2H), 3.86-3.75 (m, 2H), 3.54 (ddd, J = 13.6, 8.1, 5.2 Hz, 2H), 3.28-3.18 (m, 1H), 3.16-3.04 (m, 3H), 2.85 (s, 3H), 1.87-1.74 (m, 1H), 1.74-1.56 (m, 3H). |
| II-289 | 480.1 | 2.21 | 1H NMR (400 MHz, DMSO-d6) δ 8.62 (s, 1H), 8.59 (d, J = 1.1 Hz, 1H), 8.53 (d, J = 9.4 Hz, 1H), 7.99 (d, J = 1.2 Hz, 1H), 7.69 (d, J = 9.4 Hz, 1H), 7.53 (s, 1H), 7.32 (t, J = 53.7 Hz, 1H), 4.87-4.75 (m, 2H), 4.73-4.58 (m, 3H), 4.56-4.16 (m, 2H), 3.08 (t, J = 11.5 Hz, 1H), 2.95 (d, J = 6.3 Hz, 2H), 2.82 (t, J = 11.7 Hz, 1H), 1.81 (t, J = 16.5 Hz, 2H), 1.66 (s, 1H), 1.48 (d, J = 12.5 Hz, 1H), 1.32 (t, J = 12.4 Hz, 1H). |
| II-290 | 454.3 | 2.2 | 1H NMR (500 MHz, DMSO-d6) δ 8.68-8.62 (m, 2H), 8.54 (d, J = 9.4 Hz, 1H), 8.01 (d, J = 1.2 Hz, 1H), 7.70 (d, J = 9.4 Hz, 1H), 7.30 (t, J = 53.5 Hz, 1H), 4.47-4.32 (m, 1H), 4.32-4.16 (m, 1H), 4.05 (ddd, J = 11.7, 3.6, 1.5 Hz, 1H), 3.75 (dtd, J = 10.9, 5.8, 2.6 Hz, 1H), 3.62 (td, J = 11.6, 2.8 Hz, 1H), 3.39-3.33 (m, 2H), 3.28 (dd, J = 5.9, 2.8 Hz, 1H), 3.21-3.09 (m, 1H), 2.95 (s, 3H), 2.88 (s, 3H). |
| II-291 | 456 | 2.37 | 1H NMR (500 MHz, Methanol-d4) δ 8.69 (s, 1H), 8.57 (s, 1H), 8.46 (d, J = 9.4 Hz, 1H), 8.14 (s, 1H), 7.78 (d, J = 9.5 Hz, 1H), 4.54 (s, 1H), 4.25 (s, 1H), 3.31-3.27 (m, 1H), 3.07 (s, 2H), 2.96 (s, 3H), 2.02 (s, 1H), 1.86 (s, 2H), 1.64 (s, 1H), 1.50 (d, J = 12.1 Hz, 1H), 1.35 (d, J = 5.8 Hz, 2H). |
| II-292 | 458 | 2.1 | 1H NMR (500 MHz, Methanol-d4) δ 8.72 (s, 1H), 8.62 (d, J = 1.2 Hz, 1H), 8.47 (d, J = 9.5 Hz, 1H), 8.13 (d, J = 1.1 Hz, 1H), 7.79 (d, J = 9.5 Hz, 1H), 4.52 (s, 1H), 4.27 (s, 1H), 4.12 (d, J = 11.5 Hz, 1H), 3.70 m, 2H), 3.26 (m, 4H), 3.01 (m, 4H). |
| II-293 | 506 | 2.71 | 1H NMR (500 MHz, Methanol-d4) δ 8.75 (s, 1H), 8.74 (d, J = 0.9 Hz, 1H), 8.53 (d, J = 9.4 Hz, 1H), 8.21 (s, 1H), 7.87 (d, J = 9.5 Hz, 1H), 5.19 (s, 1H), 4.45 (s, 1H), 3.61 (dd, J = 13.9, 3.9 Hz, 1H), 3.20 (m, 1H) 3.15 (m, 3H), 3.00 (s, 3H), 2.30 (s, 2H), 1.18 (d, J = 6.7 Hz, 3H). |
| II-294 | 506 | 2.71 | 1H NMR (500 MHz, Methanol-d4) δ 8.70 (s, 1H), 8.63 (d, J = 1.1 Hz, 1H), 8.46 (d, J = 9.5 Hz, 1H), 8.26 (d, J = 1.1 Hz, 1H), 7.79 (d, J = 9.5 Hz, 1H), 4.20-4.02 (m, 3H), 3.51 (d, J = 8.2 Hz, 1H), 3.38 (d, J = 4.2 Hz, 2H), 3.07 (dd, J = 13.3, 10.2 Hz, 1H), 2.92 (s, 3H), 2.35 (s, 2H), 1.14 (d, J = 6.9 Hz, 3H). |
| II-295 | 381.2 | 1.91 | 1H NMR (500 MHz, DMSO-d6) δ 8.70 (d, J = 1.1 Hz, 1H), 8.65 (s, 1H), 8.54 (d, J = 9.4 Hz, 1H), 8.09 (d, J = 1.2 Hz, 1H), 7.71 (d, J = 9.4 Hz, 1H), 7.35 (t, J = 53.6 Hz, 1H), 4.25-4.18 (m, 4H), 3.29-3.24 (m, 4H). |
| II-296 | 365.2 | 1.65 | 1H NMR (500 MHz, DMSO-d6) δ 8.67 (d, J = 1.1 Hz, 1H), 8.64 (s, 1H), 8.54 (d, J = 9.4 Hz, 1H), 8.08 (d, J = 1.2 Hz, 1H), 7.70 (d, J = 9.4 Hz, 1H), 7.36 (t, J = 53.6 Hz, 1H), 4.45-4.30 (m, 2H), 4.01 (ddd, J = 13.5, 11.3, 1.9 Hz, 2H), 2.97 (ddd, J = 14.4, 11.5, 3.4 Hz, 2H), 2.82 (ddd, J = 12.1, 4.3, 2.3 Hz, 2H). |
| II-297 | 431.2 | 2.27 | 1H NMR (500 MHz, DMSO-d6) δ 8.65-8.64 (m, 2H), 8.53 (d, J = 9.4 Hz, 1H), 8.05 (s, 1H), 7.70 (d, J = 9.4 Hz, 1H), 7.26 (t, J = 53.9 Hz, 1H), 4.96 (t, J = 5.6 Hz, 1H), 4.66-4.59 (m, 1H), 4.09-4.01 (m, 4H), 3.61-3.52 (m, 3H). |
| II-298 | 431.2 | 2.38 | 1H NMR (500 MHz, DMSO-d6) δ 8.68 (d, J = 1.1 Hz, 1H), 8.65 (s, 1H), 8.54 (d, J = 9.4 Hz, 1H), 8.10 (d, J = 1.2 Hz, 1H), 7.70 (d, J = 9.4 Hz, 1H), 7.28 (t, J = 54.0 Hz, 1H), 5.03 (t, J = 5.7 Hz, 1H), 4.59 (br s, 1H), 4.49-4.43 (m, 2H), 3.79-eb;normal |

TABLE 5-continued

Analytical data for compounds of Formula II

| II- | LCMS_Plus | LCMS_RT | NMR |
|---|---|---|---|
| | | | 3.74 (m, 1H), 3.64-3.54 (m, 2H), 3.13 (t, J = 11.9 Hz, 1H), 2.97 (t, J = 12.1 Hz, 1H). |
| II-299 | 370.3 | 2.42 | 1H NMR (500 MHz, DMSO-d6) δ 8.63 (s, 1H), 8.60 (d, J = 1.1 Hz, 1H), 8.53 (d, J = 9.4 Hz, 1H), 8.01 (d, J = 1.2 Hz, 1H), 7.69 (d, J = 9.4 Hz, 1H), 7.33 (t, J = 53.7 Hz, 1H), 4.56-4.39 (m, 1H), 4.39-4.22 (m, 1H), 3.15-3.03 (m, 1H), 2.94 (dd, J = 13.2, 10.3 Hz, 1H), 2.62 (dd, J = 6.8, 1.4 Hz, 2H), 1.99-1.86 (m, 2H), 1.80 (dp, J = 10.3, 3.3 Hz, 1H), 1.62-1.35 (m, 2H). |
| II-300 | 438.3 | 2.19 | 1H NMR (500 MHz, DMSO-d6) δ 8.62 (s, 1H), 8.58 (d, J = 1.1 Hz, 1H), 8.53 (d, J = 9.4 Hz, 1H), 7.99 (d, J = 1.2 Hz, 1H), 7.68 (d, J = 9.4 Hz, 1H), 7.30 (t, J = 53.7 Hz, 1H), 7.18-7.13 (m, 1H), 4.69-4.19 (m, 2H), 3.14-3.04 (m, 1H), 3.00-2.89 (m, 5H), 2.89-2.80 (m, 1H), 1.91-1.83 (m, 1H), 1.78 (dt, J = 13.5, 3.6 Hz, 1H), 1.75-1.65 (m, 1H), 1.54-1.42 (m, 1H), 1.33 (qd, J = 11.7, 3.8 Hz, 1H). |
| II-301 | | | 1H NMR (500 MHz, DMSO-d6) δ 8.67 (s, 1H), 8.65 (s, 1H), 8.54 (d, J = 9.4 Hz, 1H), 8.27 (s, 1H), 7.69 (d, J = 9.4 Hz, 1H), 7.41-7.16 (m, 1H), 3.99-3.91 (m, 1H), 3.91-3.83 (m, 1H), 3.80 (td, J = 11.4, 10.6, 3.6 Hz, 1H), 3.76-3.60 (m, 1H), 3.43-3.33 (m, 1H), 2.94-2.74 (m, 1H), 1.21-1.07 (m, 1H), 0.70-0.58 (m, 1H). |
| II-302 | 488 | 2.52 | 1H NMR (500 MHz, Methanol-d4) δ 8.52-8.50 (m, 2H), 8.26 (d, 1H), 8.11 (s, 1H), 7.58 (d, 1H), 7.12-6.91 (t. 1H), 5.02 (m, 1H), 3.22 (masked, 3H), 2.95 (m, 1H), 2.79 (s, 3H), 2.25 (m, 1H), 2.12-1.94 (m, 2H), 1.31 (s, 3H). 1 CH proton not observed. |
| II-303 | 488 | 2.5 | |
| II-304 | 488 | 2.51 | |
| II-305 | 488.1 | 2.55 | 1H NMR (500 MHz, Methanol-d4) δ 8.52-8.50 (m, 2H), 8.26 (d, 1H), 8.11 (s, 1H), 7.58 (d, 1H), 7.12-6.91 (t. 1H), 5.02 (m, 1H), 4.59 (m, 1H), 3.44 (m, 1H), 3.22 (m, 1H), 3.02 (m, 1H), 2.79 (s, 3H), 2.40 (m, 1H), 2.32-2.18 (m, 1H), 2.04 (m, 1H), 1.24 (s, 3H). |
| II-306 | 508.3 | 2.51 | 1H NMR (500 MHz, DMSO-d6) δ 8.70 (s, 1H), 8.67 (s, 1H), 8.55 (d, J = 9.4 Hz, 1H), 8.10 (s, 1H), 7.71 (d, J = 9.4 Hz, 1H), 7.40 (s, 1H), 7.28 (t, J = 53.8 Hz, 1H), 4.62-4.45 (m, 4H), 3.85-3.80 (m, 1H), 3.29-3.12 (m, 2H), 2.99-2.94 (m, 1H), 2.97 (s, 3H). |
| II-307 | 508.3 | 2.4 | 1H NMR (500 MHz, DMSO-d6) δ 8.67 (s, 1H), 8.66 (d, J = 4.6 Hz, 1H), 8.54 (d, J = 9.4 Hz, 1H), 8.05 (s, 1H), 7.71 (d, J = 9.4 Hz, 1H), 7.31 (t, J = 6.2 Hz, 1H), 7.27 (t, J = 53.8 Hz, 1H), 4.71-4.65 (m, 1H), 4.12-4.00 (m, 5H), 3.55 (dd, J = 13.4, 7.8 Hz, 1H), 3.30-3.19 (m, 1H), 2.95 (s, 3H). |
| II-308 | 331 | 2.68 | 1H NMR (500 MHz, DMSO-d6) δ 8.61 (s, 1H), 8.57 (d, J = 1.0 Hz, 1H), 8.52 (d, J = 9.4 Hz, 1H), 7.99 (d, J = 1.2 Hz, 1H), 7.67 (d, J = 9.4 Hz, 1H), 7.35 (t, J = 55.0 Hz, 1H), 3.74-3.72 (m, 4H), 1.72-1.67 (m, 2H), 1.64-1.55 (m, 4H). |
| II-309 | 432 | 1.78 | 1H NMR (500 MHz, DMSO-d6) δ 8.63 (s, 1H), 8.60 (d, J = 1.1 Hz, 1H), 8.53 (d, J = 9.4 Hz, 1H), 8.20-8.02 (m, 2H), 7.69 (d, J = 9.4 Hz, 1H), 7.30 (t, J = 55.0 Hz, 1H), 4.12 (br d, J = 15.0 Hz, 1H), 3.96 (d, J = 16.3 Hz, 2H), 3.86-3.83 (m, 4H), 3.71-3.66 (m, 2H), 3.29-3.27 (m, 2H), 3.16 (d, J = 13.0 Hz, 1H). |
| II-310 | 452 | 2.43 | 1H NMR (500 MHz, DMSO-d6) δ 8.63 (d, J = 1.1 Hz, 1H), 8.59 (d, J = 1.2 Hz, 1H), 8.53 (d, J = 9.4 Hz, 1H), 7.99 (d, J = 1.3 Hz, 1H), 7.69 (dd, J = 9.4, 1.1 Hz, 1H), 7.28 (t, J = 55.0 Hz, 1H), 4.54-4.22 (m, 2H), 3.17-3.05 (m, 2H), 2.94 (dd, J = 13.4, 6.2 Hz, 1H), 2.91-2.82 (m, 4H), 2.80 (s, 3H), 1.96-1.70 (m, 3H), 1.51 (d, J = 12.4 Hz, 1H), 1.32 (d, J = 11.3 Hz, 1H). |
| II-311 | 453 | 2.24 | 1H NMR (500 MHz, DMSO-d6) δ 8.61 (s, 1H), 8.58 (s, 1H), 8.48 (d, J = 9.4 Hz, 1H), 7.93 (d, J = 1.1 Hz, 1H), 7.65 (d, J = 9.4 Hz, 1H), 7.20 (t, J - 55.0 Hz, 1H), 6.66 (s, 2H), 4.58-4.07 (m, 2H), |

TABLE 5-continued

Analytical data for compounds of Formula II

| II- | LCMS_Plus | LCMS_RT | NMR |
|---|---|---|---|
| | | | 3.15 (t, J = 11.7 Hz, 1H), 2.90-2.84 (m, 2H), 2.73 (dd, J = 13.3, 6.0 Hz, 1H), 2.60 (s, 3H), 1.90-1.65 (m, 3H), 1.46-1.41 (m, 1H), 1.34-1.18 (m, 1H). |
| II-312 | 467.4 | 2.01 | 1H NMR (500 MHz, DMSO-d6) δ 8.63 (m, 2H), 8.54 (d, 1H), 7.97 (s, 1H), 7.70 (d, 1H), 7.20 (m, 2H), 4.80 (broad m, 1H), 4.30 (broad m, 1H), 3.35 (m, 1H), 2.99 (s, 3H), 2.80-2.65 (m, 2H), 2.25 (m, 6H), 1.15 (m, 3H). |
| II-313 | 453.4 | 1.83 | |
| II-314 | 431.3 | 2.28 | 1H NMR (500 MHz, DMSO-d6) δ 8.65 (d, J = 1.1 Hz, 1H), 8.65 (s, 1H), 8.54 (d, J = 9.4 Hz, 1H), 8.06 (d, J = 1.2 Hz, 1H), 7.70 (d, J = 9.4 Hz, 1H), 7.27 (t, J = 53.9 Hz, 1H), 4.96 (t, J = 5.6 Hz, 1H), 4.67-4.60 (m, 1H), 4.10-4.01 (m, 4H), 3.61-3.52 (m, 3H). |
| II-315 | 431.3 | 2.38 | 1H NMR (500 MHz, DMSO-d6) δ 8.69 (d, J = 1.1 Hz, 1H), 8.66 (s, 1H), 8.54 (d, J = 9.4 Hz, 1H), 8.11 (d, J = 1.2 Hz, 1H), 7.70 (d, J = 9.4 Hz, 1H), 7.28 (t, J = 54.0 Hz, 1H), 5.03 (t, J = 5.7 Hz, 1H), 4.60 (br s, 1H), 4.50-4.43 (m, 2H), 3.79-3.74 (m, 1H), 3.64-3.54 (m, 2H), 3.13 (t, J = 11.9 Hz, 1H), 2.97 (t, J = 12.1 Hz, 1H). |
| II-316 | 489 | 2.37 | 1H NMR (500 MHz, DMSO-d6) δ 8.76-8.62 (m, 2H), 8.54 (d, J = 9.4 Hz, 1H), 8.08 (d, J = 1.2 Hz, 1H), 7.71 (d, J = 9.4 Hz, 1H), 7.29 (t, J = 55.0 Hz, 1H), 6.82 (dd, J = 8.0, 5.1 Hz, 1H), 6.68 (s, 2H), 4.84 (br s, 1H), 4.55 (brs, 1H), 3.48-3.36 (m, 1H), 2.99-2.73 (m, 3H), 2.32-2.12 (m, 2H), 1.07 (d, J = 6.7 Hz, 3H). |
| II-317 | 438 | 2.12 | 1H NMR (500 MHz, DMSO-d6) δ 8.61 (s, 1H), 8.58 (d, J = 1.1 Hz, 1H), 8.52 (d, J = 9.4 Hz, 1H), 8.00 (d, J = 1.2 Hz, 1H), 7.68 (d, J = 9.4 Hz, 1H), 7.32 (t, J = 55.0 Hz, 1H), 6.77 (s, 2H), 4.32 (vbrs, 2H), 3.20-2.99 (m, 3H), 2.91 (dd, J = 13.2, 9.2 Hz, 1H), 1.96-1.82 (m, 1H), 1.83-1.59 (m, 4H), 1.48 (d, J = 12.9 Hz, 1H), 1.31 (d, J = 11.6 Hz, 1H). |
| II-318 | 440 | 1.89 | 1H NMR (500 MHz, DMSO-d6) δ 8.65 (d, J = 1.3 Hz, 2H), 8.54 (d, J = 9.4 Hz, 1H), 8.01 (d, J = 1.2 Hz, 1H), 7.71 (d, J = 9.4 Hz, 1H), 7.36 (t, J = 55.0 Hz, 1H), 6.85 (s, 2H), 4.40 (brs, 1H), 4.25 (brs, 1H), 4.07-3.96 (m, 1H), 3.66-3.55 (m, 2H), 3.21-3.01 (m, 3H), 2.87 (t, J = 11.8 Hz, 1H), 2.10-1.85 (m, 2H). |
| II-319 | 452 | 2.13 | |
| II-320 | 450 | 2.36 | 1H NMR (500 MHz, DMSO-d6) δ 8.72-8.62 (m, 2H), 8.54 (d, J = 9.4 Hz, 1H), 8.04 (d, J = 1.2 Hz, 1H), 7.71 (d, J = 9.4 Hz, 1H), 7.33 (t, J = 55.0 Hz, 1H), 5.17 (brs, 1H), 4.28 (brs, 1H), 3.27 (t, J = 9.8 Hz, 2H), 3.19 (d, J = 12.3 Hz, 2H), 3.09 (q, J = 12.2, 10.0 Hz, 1H), 2.99 (s, 3H), 2.37 (d, J = 17.6 Hz, 1H), 1.98-1.73 (m, 2H), 1.53 (dd, J = 11.0, 7.7 Hz, 2H). |
| II-321 | 502 | 2.67 | 1H NMR (500 MHz, DMSO-d6) δ 8.70 (d, J = 1.1 Hz, 1H), 8.64 (s, 1H), 8.53 (d, J = 9.4 Hz, 1H), 8.08 (s, 1H), 7.75 (d, J = 9.5 Hz, 1H), 7.25 (s, 1H), 5.04 (s, 1H), 4.27 (s, 1H), 3.44 (ddd, J = 13.4, 5.2, 3.6 Hz, 1H), 3.06-2.92 (m, 5H), 2.92-2.76 (m, 1H), 2.35-2.12 (m, 5H), 1.05 (d, J = 6.7 Hz, 3H). |
| 11-322 | 454.1 | 2.1 | 1H NMR (500 MHz, DMSO-d6) δ 8.71 (d, J = 1.0 Hz, 1H), 8.65 (s, 1H), 8.54 (d, J = 9.5 Hz, 1H), 7.98 (d, J = 1.1 Hz, 1H), 7.76 (d, J = 9.5 Hz, 1H), 7.22 (t, J = 6.2 Hz, 1H), 4.45 (bs, 1H), 4.23 (bs, 1H), 4.04 (ddd, J = 11.6, 3.6, 1.5 Hz, 1H), 3.61 (ddq, J = 11.0, 8.4, 2.8 Hz, 2H), 3.25-3.16 (m, 1H), 3.16-3.07 (m, 2H), 2.95 (s, 4H), 2.26 (t, J = 19.3 Hz, 3H). |
| II-323 | 345.3 | 2.85 | 1H NMR (500 MHz, DMSO-d6) δ 8.61 (s, 1H), 8.58 (d, J = 1.1 Hz, 1H), 8.52 (d, J = 9.4 Hz, 1H), 7.98 (d, J = 1.2 Hz, 1H), 7.67 (d, J = 9.4 Hz, 1H), 7.33 (t, J = 53.9 Hz, 1H), 4.86-4.68 (m, 1H), 4.45-4.27 (m, 1H), 3.03 (td, J = 13.2, 3.1 Hz, 1H), 1.84-1.76 (m, 1H), 1.76-1.56 (m, 4H), 1.45 |

TABLE 5-continued

Analytical data for compounds of Formula II

| II- | LCMS_Plus | LCMS_RT | NMR |
|---|---|---|---|
| | | | (tq, J = 11.9, 7.0, 5.9 Hz, 1H), 1.22 (d, J = 6.8 Hz, 3H). |
| II-324 | 347.3 | 2.26 | 1H NMR (500 MHz, DMSO-d6) δ 8.65-8.62 (m, 2H), 8.53 (d, J = 9.4 Hz, 1H), 7.97 (d, J = 1.2 Hz, 1H), 7.69 (d, J = 9.4 Hz, 1H), 7.34 (t, J = 53.7 Hz, 1H), 4.51-4.42 (m, 1H), 4.11 (d, J = 13.3 Hz, 1H), 4.00 (dd, J = 11.5, 3.9 Hz, 1H), 3.79 (dt, J = 11.4, 1.1 Hz, 1H), 3.71-3.64 (m, 1H), 3.56-3.48 (m, 1H), 3.28-3.19 (m, 1H), 1.26 (d, J = 6.7 Hz, 3H). |
| II-325 | 347.3 | 2.26 | 1H NMR (500 MHz, DMSO-d6) δ 8.65-8.62 (m, 2H), 8.53 (d, J = 9.4 Hz, 1H), 7.97 (d, J = 1.2 Hz, 1H), 7.69 (d, J = 9.4 Hz, 1H), 7.34 (t, J = 53.7 Hz, 1H), 4.54-4.42 (m, 1H), 4.11 (d, J = 13.1 Hz, 1H), 4.00 (dd, J = 11.5, 3.9 Hz, 1H), 3.79 (dt, J = 11.5, 1.1 Hz, 1H), 3.71-3.63 (m, 1H), 3.52 (ddd, J = 12.2, 11.4, 3.1 Hz, 1H), 3.29-3.20 (m, 1H), 1.26 (d, J = 6.7 Hz, 3H). |
| II-326 | 414.3 | 1.94 | 1H NMR (500 MHz, DMSO-d6) δ 8.67-8.62 (m, 2H), 8.57-8.51 (m, 2H), 8.04-7.98 (m, 2H), 7.71 (d, J = 9.4 Hz, 1H), 7.35 (t, J = 53.6 Hz, 1H), 4.55-4.37 (m, 3H), 4.27-4.09 (m, 1H), 4.01 (ddd, J = 11.6, 3.6, 1.7 Hz, 1H), 3.94 (ddq, J = 10.8, 7.1, 4.2, 3.5 Hz, 1H), 3.58 (td, J = 11.6, 2.9 Hz, 1H), 3.14 (td, J = 12.3, 3.6 Hz, 1H), 2.93 (dd, J = 13.2, 10.4 Hz, 1H). |
| II-327 | 412.4 | 2.18 | 1H NMR (500 MHz, DMSO-d6) δ 8.60 (s, 1H), 8.55 (d, J = 1.1 Hz, 1H), 8.51 (d, J = 9.4 Hz, 1H), 8.18 (d, J = 1.0 Hz, 1H), 7.92 (d, J = 1.2 Hz, 1H), 7.75 (d, J = 1.0 Hz, 1H), 7.68 (d, J = 9.4 Hz, 1H), 7.32 (t, J = 53.7 Hz, 1H), 4.45 (dd, J = 13.8, 7.2 Hz, 1H), 4.38 (dd, J = 13.8, 7.0 Hz, 1H), 4.35-4.10 (m, 2H), 3.23-3.11 (m, 1H), 3.01 (dd, J = 13.1, 10.1 Hz, 1H), 2.15 (ddq, J = 10.2, 7.0, 3.5 Hz, 1H), 1.80 (dq, J = 11.7, 3.8 Hz, 1H), 1.71 (dq, J = 12.5, 4.1 Hz, 1H), 1.57-1.42 (m, 1H), 1.41-1.28 (m, 1H). |
| II-328 | 404.3 | 1.8 | 1H NMR (500 MHz, DMSO-d6) δ 8.60 (d, J = 1.1 Hz, 1H), 8.44 (s, 1H), 8.20 (d, J = 9.3 Hz, 1H), 8.10 (d, J = 1.2 Hz, 1H), 7.34 (d, J = 9.3 Hz, 1H), 7.26 (t, J = 6.3 Hz, 1H), 4.49-4.34 (m, 1H), 4.31-4.15 (m, 1H), 4.03 (ddd, J = 11.6, 3.8, 1.5 Hz, 1H), 3.65-3.53 (m, 2H), 3.21-3.07 (m, 3H), 2.96 (s, 3H), 2.86 (dd, J = 13.3, 10.3 Hz, 1H), 2.68 (s, 3H). |
| II-329 | 488.1 | 2.4 | 1H NMR (500 MHz, Methanol-d4) δ 8.76 (s, 2H), 8.48 (d, 1H), 8.18 (s, 1H0, 7.81 (dd, 1H), 7.25-7.04 (t, 1H), 5.40 (br m, 1H), 3.50 (br s, 1H), 3.13 (m, 2H), 3.02 (s, 3H), 2.38 (m, 1H), 2.27 (m, 1H), 2.18-2.02 (m, 1H), 1.37 (d, 3H). |
| II-330 | 508.3 | 2.42 | 1H NMR (500 MHz, DMSO-d6) δ 8.67 (d, J = 1.1 Hz, 1H), 8.66 (s, 1H), 8.54 (d, J = 9.4 Hz, 1H), 8.05 (s, 1H), 7.71 (d, J = 9.4 Hz, 1H), 7.31 (s, 1H), 7.27 (t, J = 53.8 Hz, 1H), 4.72-4.65 (m, 1H), 4.15-4.00 (m, 4H), 3.55 (dd, J = 13.5, 7.9 Hz, 1H), 3.24-3.21 (m, 2H), 2.95 (s, 3H). |
| II-331 | 508.3 | 2.52 | 1H NMR (500 MHz, DMSO-d6) δ 8.70 (d, J = 1.1 Hz, 1H), 8.67 (s, 1H), 8.55 (d, J = 9.4 Hz, 1H), 8.10 (d, J = 1.2 Hz, 1H), 7.71 (d, J = 9.4 Hz, 1H), 7.40 (br s, 1H), 7.28 (t, J = 53.8 Hz, 1H), 4.64-4.49 (m, 4H), 3.85-3.80 (m, 1H), 3.26-3.13 (m, 2H), 2.99-2.94 (m, 1H), 2.98 (s, 3H) |
| 11-332 | 453 | 1.92 | 1H NMR (500 MHz, DMSO-d6) δ 8.61 (d, J = 1.1 Hz, 1H), 8.57 (s, 1H), 8.47 (d, J = 9.4 Hz, 1H), 7.93 (d, J = 1.2 Hz, 1H), 7.63 (d, J = 9.4 Hz, 1H), 7.22 (t, J = 55.0 Hz, 1H), 6.81 (s, 2H), 4.82 (vbrs, 1H), 4.13 (t, J = 4.1 Hz, 1H), 3.99 (dd, J = 11.8, 3.7 Hz, 1H), 3.89 (vbrs, 1H), 3.57 (td, J = 12.0, 2.9 Hz, 1H), 3.52-3.40 (m, 2H), 3.08 (t, J = 9.8 Hz, 1H), water peak obscures some signals. |
| 11-333 | 451 | 2.1 | 1H NMR (500 MHz, DMSO-d6) δ 8.62 (s, 1H), 8.60 (d, J = 1.1 Hz, 1H), 8.53 (d, J = 9.4 Hz, 1H), 8.04 (d, J = 1.2 Hz, 1H), 7.69 (d, J = 9.4 Hz, 1H), 7.32 (t, J = 55.0 Hz, 1H), 6.92 (s, 2H), 3.92 (s, 2H), 3.63 (s, 2H), 3.48 (d, J = 1.3 Hz, 4H), 1.84 (t, J = 5.8 Hz, 2H), 1.61 (s, 2H). |

TABLE 5-continued

Analytical data for compounds of Formula II

| II- | LCMS_Plus | LCMS_RT | NMR |
|---|---|---|---|
| II-334 | 453 | 1.93 | 1H NMR (500 MHz, DMSO-d6) δ 8.61 (d, J = 1.0 Hz, 1H), 8.59 (s, 1H), 8.47 (d, J = 9.4 Hz, 1H), 7.95 (d, J = 1.2 Hz, 1H), 7.65 (d, J = 9.4 Hz, 1H), 7.25 (t, J = 55.0 Hz, 1H), 6.98 (s, 2H), 3.89 (s, 2H), 3.69 (dd, J = 6.1, 3.8 Hz, 2H), 3.62 (t, J = 8.6 Hz, 4H), 3.59-3.53 (m, 2H). |
| II-335 | 451 | 2.19 | 1H NMR (500 MHz, DMSO-d6) δ 8.56 (d, J = 1.1 Hz, 1H), 8.55 (s, 1H), 8.46 (d, J = 9.4 Hz, 1H), 7.95 (d, J = 1.2 Hz, 1H), 7.62 (d, J = 9.4 Hz, 1H), 7.22 (t, J = 55.0 Hz, 1H), 6.78 (s, 2H), 5.05 (vbrs, 1H), 4.14 (vbrs, 1H), 3.43 (t, J = 9.2 Hz, 1H), 3.30 (dt, J = 8.8, 4.4 Hz, 1H), 3.09-2.86 (m, 3H), 2.25 (dd, J = 11.5, 5.8 Hz, 1H), 1.86-1.68 (m, 2H), 1.52-1.41 (m, 2H). |
| II-336 | 453.1 | 1.78 | 1H NMR (500 MHz, DMSO-d6) δ 8.61 (m, 2H), 8.52 (d, 1H), 8.02 (s, 1H), 7.70 (d, 1H), 7.45-7.25 (t, 1H), 7.05 (br s, 1H), 4.80 (br s, 1H), 3.60 (m, 1H), 3.30-3.12 (masked, 5H), 2.87 (m, 5H), 1.21 (m, 3H). |
| II-337 | 482.1 | 2.16 | 1H NMR (500 MHz, DMSO-d6) δ 8.69 (d, J = 1.0 Hz, 1H), 8.52 (d, J = 1.9 Hz, 1H), 8.31 (d, J = 9.4 Hz, 1H), 8.21 (d, J = 8.9 Hz, 1H), 7.57 (dd, J = 9.4, 3.3 Hz, 1H), 7.27 (t, J = 6.4 Hz, 1H), 5.02 (dq, J = 11.1, 6.5 Hz, 1H), 4.35 (s, 1H), 3.44 (ddd, J = 13.4, 5.4, 3.6 Hz, 1H), 3.03-2.94 (m, 5H), 2.91-2.81 (m, 1H), 2.24 (s, 2H), 1.58 (dd, J = 6.5, 2.7 Hz, 3H), 1.07 (dd, J = 6.8, 2.4 Hz, 3H). 1x CH not observed |
| II-338 | 434.1 | 1.65 | 1H NMR (500 MHz, DMSO-d6) δ 8.71 (d, J = 0.9 Hz, 1H), 8.58 (s, 1H), 8.34 (d, J = 9.5 Hz, 1H), 8.09 (d, J = 1.0 Hz, 1H), 7.61 (dd, J = 9.5, 0.7 Hz, 1H), 7.25 (t, J = 6.3 Hz, 1H), 5.06-4.97 (m, 1H), 4.50 (s, 3H), 4.23 (s, 15H), 4.06 (ddd, J = 11.6, 3.7, 1.5 Hz, 1H), 3.61 (dddd, J = 15.9, 8.5, 5.2, 3.0 Hz, 2H), 3.29-3.18 (m, 1H), 3.15 (tt, J = 6.4, 1.8 Hz, 2H), 2.96 (s, 4H), 1.56 (d, J = 6.5 Hz, 3H). |
| II-339 | 412.4 | 2.13 | 1H NMR (500 MHz, DMSO-d6) δ 8.60 (s, 1H), 8.57-8.54 (m, 2H), 8.51 (d, J = 9.4 Hz, 1H), 7.98 (s, 1H), 7.93 (d, J = 1.3 Hz, 1H), 7.68 (d, J = 9.4 Hz, 1H), 7.30 (t, J = 53.8 Hz, 1H), 4.37-4.21 (m, 2H), 4.22-4.07 (m, 2H), 3.20 (ddd, J = 13.6, 10.8, 3.1 Hz, 1H), 3.02 (dd, J = 13.2, 9.8 Hz, 1H), 2.20-2.09 (m, 1H), 1.79 (dq, J = 12.2, 4.1 Hz, 1H), 1.70 (dq, J = 12.8, 4.2 Hz, 1H), 1.57-1.43 (m, 1H), 1.32 (dtd, J = 12.8, 10.6, 3.8 Hz, 1H). |
| II-340 | 481.4 | 2.49 | |
| II-341 | 377.3 | 1.88 | 1H NMR (400 MHz, DMSO-d6) δ 8.72-8.57 (m, 2H), 8.53 (d, J = 9.4 Hz, 1H), 7.98 (d, J = 1.2 Hz, 1H), 7.69 (d, J = 9.5 Hz, 1H), 7.30 (t, J = 53.8 Hz, 1H), 4.79 (t, J = 3.5 Hz, 1H), 4.48 (d, J = 7.1 Hz, 1H), 4.15 (d, J = 13.3 Hz, 1H), 3.77 (dd, J = 10.1, 4.0 Hz, 2H), 3.67-3.53 (m, 3H), 1.30 (d, J = 6.7 Hz, 3H). |
| II-342 | 377.1 | 1.94 | 1H NMR (400 MHz, DMSO-d6) δ 8.63 (s, 2H), 8.54 (d, J = 9.4 Hz, 1H), 8.00 (s, 1H), 7.69 (d, J = 9.4 Hz, 1H), 7.52-7.06 (m, 1H), 4.86 (t, J = 5.5 Hz, 1H), 4.09 (q, J = 5.2 Hz, 1H), 4.06-3.99 (m, 1H), 3.68-3.46 (m, 3H), 3.40 (d, J = 10.4 Hz, 1H), 3.30 (s, 1H), 1.12 (d, J = 25.8 Hz, 3H). |
| II-343 | 405.3 | 1.73 | 1H NMR (500 MHz, Methanol-d4) δ 8.62 (s, 1H), 8.57 (d, J = 1.1 Hz, 1H), 8.39 (d, J = 9.5 Hz, 1H), 8.12 (s, 1H), 7.69 (d, J = 9.5 Hz, 1H), 7.09 (t, J = 54.1 Hz, 1H), 4.00-3.98 (m, 2H), 3.91 (s, 2H), 3.73 (dd, J = 11.6, 2.7 Hz, 1H), 3.55 (br s, 1H), 3.49 (s, 2H). One x CH2 and one x CH not observed. |
| II-344 | 451 | 2.14 | |
| II-345 | 454.1 | 2.11 | |
| II-346 | 454.4 | 2.04 | 1H NMR (400 MHz, methanol-d4) δ 8.66-8.53 (m, 2H), 8.38 (d, J = 9.4 Hz, 1H), 8.11 (d, J = 1.2 Hz, 1H), 7.69 (d, J = 9.5 Hz, 1H), 7.12 (t, J = 54.1 Hz, 1H), 4.70-4.53 (m, 1H), 4.33 (dd, J = 14.0, 3.9 Hz, 1H), 3.96 (td, J = 11.8, 4.0 Hz, 1H), 3.91-3.78 (m, 2H), 3.53-3.35 (m, 3H), 2.97 (s, 3H), 1.43 (d, J = 6.7 Hz, 3H). |

TABLE 5-continued

Analytical data for compounds of Formula II

| II- | LCMS_Plus | LCMS_RT | NMR |
|---|---|---|---|
| II-347 | 441 | 1.82 | 1H NMR (500 MHz, DMSO-d6) δ 8.57 (s, 1H), 8.56 (d, J = 1.1 Hz, 1H), 8.46 (d, J = 9.4 Hz, 1H), 7.92 (d, J = 1.2 Hz, 1H), 7.63 (d, J = 9.4 Hz, 1H), 7.24 (t, J = 55.0 Hz, 1H), 6.66 (t, J = 6.4 Hz, 1H), 6.54 (s, 2H), 4.43 (brs, 1H), 4.16 (brs, 1H), 3.99-3.88 (m, 1H), 3.55-3.48 (m, 2H), 3.07-3.01 (m, 2H), 2.93 (dt, J = 13.6, 7.0 Hz, 1H), 2.74 (t, J = 11.8 Hz, 1H). |
| II-348 | 467 | 2.47 | 1H NMR (500 MHz, DMSO-d6) δ 8.62 (s, 1H), 8.58 (d, J = 1.1 Hz, 1H), 8.53 (d, J = 9.4 Hz, 1H), 8.00 (d, J = 1.2 Hz, 1H), 7.69 (d, J = 9.4 Hz, 1H), 7.45-7.19 (m, 2H), 4.60-4.21 (m, 2H), 3.12-3.03 (m, 1H), 2.95-2.80 (m, 3H), 2.68 (s, 6H), 1.90-1.74 (m, 2H), 1.73-1.65 (m, 1H), 1.52-1.41 (m, 1H), 1.38-1.29 (m, 1H). |
| II-349 | 469 | 2.23 | 1H NMR (500 MHz, DMSO-d6) δ 8.69-8.60 (m, 2H), 8.54 (d, J = 9.4 Hz, 1H), 8.00 (d, J = 1.2 Hz, 1H), 7.70 (d, J = 9.4 Hz, 1H), 7.45-7.02 (m, 2H), 4.47 (brs, 1H), 4.24 (brs, 1H), 4.08-3.95 (m, 1H), 3.67-3.45 (m, 2H), 3.18-3.02 (m, 3H), 2.84 (dd, J = 13.2, 10.3 Hz, 1H), 2.70 (s, 6H). |
| II-350 | 471.5 | 2.34 | 1H NMR (500 MHz, DMSO-d6) δ 8.65-8.60 (m, 2H), 8.53 (dd, J = 9.4, 1.7 Hz, 1H), 8.06-7.95 (m, 1H), 7.70 (dt, J = 9.4, 1.8 Hz, 1H), 7.44-7.12 (m, 2H), 4.14 (s, 1H), 3.83 (s, 1H), 3.71(d, J = 6.1 Hz, 1H), 3.38-3.32 (m, 2H), 2.99-2.80 (m, 4H), 2.21 (d, J = 8.1 Hz, 1H), 1.79 (s, 1H), 1.44 (d, J = 21.3 Hz, 1H). |
| II-351 | 444 | 2.14 | |
| II-352 | 402 | 1.85 | |
| II-353 | 429 | 1.87 | |
| II-354 | 345.3 | 2.84 | 1H NMR (500 MHz, DMSO-d6) δ 8.61 (s, 1H), 8.57 (d, J = 1.1 Hz, 1H), 8.52 (d, J = 9.4 Hz, 1H), 7.98 (d, J = 1.2 Hz, 1H), 7.67 (d, J = 9.4 Hz, 1H), 7.33 (t, J = 53.9 Hz, 1H), 4.84-4.71 (m, 1H), 4.43-4.30 (m, 1H), 3.03 (td, J = 13.2, 3.1 Hz, 1H), 1.84-1.76 (m, 1H), 1.76-1.58 (m, 4H), 1.53-1.38 (m, 1H), 1.22 (d, J = 6.8 Hz, 3H). |
| II-355 | 379.3 | 1.77 | 1H NMR (500 MHz, DMSO-d6) δ 8.66 (d, J = 1.1 Hz, 1H), 8.64 (s, 1H), 8.54 (d, J = 9.4 Hz, 1H), 8.06 (d, J = 1.2 Hz, 1H), 7.70 (d, J = 9.4 Hz, 1H), 7.35 (t, J = 53.7 Hz, 1H), 5.16-5.02 (m, 1H), 4.67-4.54 (m, 1H), 4.03 (t, J = 13.3 Hz, 1H), 3.10 (dt, J = 14.6, 2.5 Hz, 1H), 3.07-2.91 (m, 2H), 2.81 (dd, J = 14.7, 5.7 Hz, 1H), 1.63 (d, J = 7.1 Hz, 3H). |
| II-356 | 379.3 | 1.82 | 1H NMR (500 MHz, DMSO-d6) δ 8.66 (d, J = 1.0 Hz, 1H), 8.64 (s, 1H), 8.54 (d, J = 9.4 Hz, 1H), 8.05 (d, J = 1.2 Hz, 1H), 7.70 (dd, J = 9.4, 0.7 Hz, 1H), 7.35 (t, J = 53.8 Hz, 1H), 5.11-4.97 (m, 1H), 4.84-4.69 (m, 1H), 3.56-3.37 (m, 3H), 2.94 (dd, J = 12.8, 4.6 Hz, 1H), 2.71-2.59 (m, 1H), 1.38 (d, J = 6.9 Hz, 3H). |
| II-357 | 330.3 | 2.24 | 1H NMR (500 MHz, DMSO-d6) δ 9.20 (d, J = 1.3 Hz, 1H), 8.77 (s, 1H), 8.72 (d, J = 1.4 Hz, 1H), 8.57 (d, J = 9.4 Hz, 1H), 7.75 (d, J = 9.4 Hz, 1H), 7.53-7.27 (m, 1H), 7.23-7.18 (m, 1H), 4.38 (q, J = 2.9 Hz, 2H), 3.90 (t, J = 5.4 Hz, 2H), 2.69-2.59 (m, 2H). |
| II-358 | 332.3 | 2.1 | 1H NMR (500 MHz, DMSO-d6) δ 9.19 (d, J = 1.3 Hz, 1H), 8.75 (s, 1H), 8.58-8.53 (m, 2H), 7.74 (d, J = 9.4 Hz, 1H), 7.39 (t, J = 53.7 Hz, 1H), 4.01 (ddd, J = 11.4, 4.3, 1.9 Hz, 2H), 3.52 (td, J = 11.6, 2.4 Hz, 2H), 3.08 (tt, J = 11.5, 4.1 Hz, 1H), 1.96-1.76 (m, 4H). |
| II-359 | 389.3 | 2.05 | 1H NMR (500 MHz, DMSO-d6) δ 8.62 (s, 1H), 8.61 (d, J = 1.1 Hz, 1H), 8.53 (d, J = 9.4 Hz, 1H), 7.99 (s, 1H), 7.69 (d, J = 9.4 Hz, 1H), 7.28 (t, J = 53.9 Hz, 1H), 4.86 (br s, 1H), 4.49 (br s, 1H), 3.83 (br s, 1H), 3.69-3.64 (m, 1H), 3.59 (d, J = 13.1 Hz, 1H), 3.52-3.44 (m, 2H), 3.04-2.99 (m, 1H), 0.91-0.86 (m, 1H), 0.83-0.78 (m, 1H), 0.66-0.62 (m, 1H), 0.57-0.53 (m, 1H). |
| II-360 | 488.4 | 2.39 | 1H NMR (500 MHz, Methanol-d4) δ 8.64 (m, 2H), 8.39 (d, 1H), 8.18 (s, 1H), 7.71 (dd, 1H), 7.22-7.01 (t, 1H), 3.35 (masked, 2H), 3.13 (m, |

TABLE 5-continued

Analytical data for compounds of Formula II

| II- | LCMS_Plus | LCMS_RT | NMR |
|---|---|---|---|
| | | | 2H), 3.02 (s, 3H), 2.38 (m, 1H), 2.27 (m, 1H), 2.18-2.02 (m, 2H), 1.32 (d, 3H). |
| II-361 | 488 | 2.39 | |
| II-362 | 424.1 | 2.09 | 1H NMR (400 MHz, DMSO-d6) δ 8.62 (s, 1H), 8.58 (d, J = 1.0 Hz, 1H), 8.52 (d, J = 9.5 Hz, 1H), 8.01 (d, J = 1.2 Hz, 1H), 7.69 (d, J = 9.4 Hz, 1H), 7.46-7.13 (m, 2H), 4.51-4.06 (m, 2H), 3.39 (d, J = 5.9 Hz, 1H), 3.11 (ddt, J = 22.5, 13.0, 6.5 Hz, 2H), 2.99 (s, 3H), 2.00 (dd, J = 8.7, 4.9 Hz, 1H), 1.86-1.75 (m, 1H), 1.55 (tt, J = 11.6, 6.2 Hz, 2H). |
| II-363 | 467.1 | 2.01 | |
| II-364 | 467.1 | 2.01 | 1H NMR (500 MHz, Methanol-d4) δ 8.58 (s, 1H), 8.53 (d, J = 1.1 Hz, 1H), 8.34 (d, J = 9.4 Hz, 1H), 8.03-7.99 (m, 1H), 7.66 (d, J = 9.4 Hz, 1H), 7.09 (t, J = 53.7 Hz, 1H), 3.53 (dd, J = 13.0, 5.0 Hz, 1H), 3.35 (s, 1H), 3.27 (m, 2H), 3.03 (m, 4H), 2.97 (m, 1H), 2.36 (s, 4H), 2.30 (td, J = 12.1, 3.6 Hz, 1H), 1.28 (d, J = 6.7 Hz, 3H). |
| II-365 | 482.4 | 1.99 | |
| II-366 | 480.3 | 2.01 | |
| II-367 | 482.3 | 2.07 | |
| II-368 | 388.3 | 2 | 1H NMR (500 MHz, DMSO-d6) δ 8.75 (m, 2H), 8.55 (d, 1H), 7.96 (s, 1H), 7.77 (d, 1H), 7.46-7.24 (t, 1H), 4.80 (br s, 1H), 4.32-4.18 (m, 2H), 3.91-3.83 (m, 1H), 3.45 (m, 1H), 3.37 (m, 1H), 3.16-2.99 (m, 1H), 2.11 (m, 3H), 1.26-1.18 (dd, 3H). |
| II-369 | 466.3 | 2.2 | 1H NMR (500 MHz, DMSO-d6) δ 8.67 (d, J = 1.1 Hz, 1H), 8.64 (s, 1H), 8.54 (d, J = 9.4 Hz, 1H), 7.94 (d, J = 1.2 Hz, 1H), 7.70 (d, J = 9.4 Hz, 1H), 7.34 (t, J = 53.9 Hz, 1H), 4.34-4.25 (m, 1H), 4.11 (td, J = 10.1, 4.3 Hz, 1H), 4.08-4.02 (m, 1H), 4.01-3.88 (m, 2H), 3.80-3.65 (m, 3H), 3.06-2.93 (m, 4H), 2.84 (dd, J = 11.2, 10.2 Hz, 1H), 2.61-2.53 (m, 1H), 1.70-1.58 (m, 1H). |
| II-370 | 422.3 | 1.89 | 1H NMR (500 MHz, DMSO-d6) δ 8.62 (s, 1H), 8.58 (d, J = 1.1 Hz, 1H), 8.52 (d, J = 9.4 Hz, 1H), 8.01 (d, J = 1.2 Hz, 1H), 7.69 (d, J = 9.4 Hz, 1H), 7.42 (t, J = 53.7 Hz, 1H), 4.52 (s, 1H), 4.37 (s, 1H), 3.80 (s, 1H), 3.16-3.02 (m, 4H), 2.97 (s, 3H), 2.22 (d, J = 9.9 Hz, 1H), 2.00 (d, J = 11.9 Hz, 1H), 1.76 (d, J = 12.1 Hz, 1H), 1.50 (tt, J = 20.7, 10.3 Hz, 2H). |
| II-371 | 454.3 | 2.11 | |
| II-372 | 454.1 | 2.12 | |
| II-373 | 375 | 2.27 | 1H NMR (500 MHz, DMSO-d6) δ 8.64-8.54 (m, 2H), 8.52 (d, J = 9.4 Hz, 1H), 8.04 (br s, 1H), 7.27 (t, J = 55.0 Hz, 1H), 4.63 (br s, 2H), 3.35 (ddd, J = 12.0, 7.6, 3.9 Hz, 2H), 3.02 (v br s, 1H), 1.90-1.75 (m, 2H), 1.58 (d, J = 11.2 Hz, 1H), 1.53-1.14 (m, 3H), 1.09 (br s, 3H). |
| II-374 | 438.3 | 2.26 | 1H NMR (500 MHz, DMSO-d6) δ 8.68 (s, 2H), 8.56 (d, J = 9.5 Hz, 1H), 8.02 (d, J = 1.1 Hz, 1H), 7.74 (d, J = 9.5 Hz, 1H), 7.46-7.16 (m, 2H), 3.10 (s, 1H), 2.97 (s, 3H), 2.03 (ddt, J = 13.3, 7.7, 4.2 Hz, 1H), 1.87 (s, 1H), 1.66 (dd, J = 33.7, 13.8 Hz, 2H), 1.28 (dd, J = 7.0, 1.7 Hz, 3H). |
| II-375 | 466.3 | 2.23 | 1H NMR (500 MHz, DMSO-d6) δ 8.63 (s, 1H), 8.62 (d, J = 1.1 Hz, 1H), 8.53 (d, J = 9.4 Hz, 1H), 7.98 (s, 1H), 7.70 (d, J = 9.4 Hz, 1H), 7.29 (t, J = 53.6 Hz, 1H), 7.21 (t, J = 6.2 Hz, 1H), 4.50 (br s, 2H), 3.76-3.70 (m, 1H), 3.61-3.57 (m, 1H), 3.14 (t, J = 6.3 Hz, 2H), 3.01-2.95 (m, 1H), 2.94 (s, 3H), 0.94-0.90 (m, 1H), 0.88-0.81 (m, 1H), 0.71-0.66 (m, 1H), 0.60-0.55 (m, 1H). |
| II-376 | 410.3 | 1.94 | 1H NMR (500 MHz, DMSO-d6) δ 8.74-8.66 (m, 2H), 8.57 (d, J = 9.4 Hz, 1H), 8.12-7.96 (m, 1H), 7.75 (d, J = 9.5 Hz, 1H), 7.30 (t, J = 53.7 Hz, 1H), 7.03 (s, 2H), 4.93 (d, J = 27.3 Hz, 1H), 4.38 (s, 1H), 3.32-3.01 (m, 3H), 2.23 (dt, J = 13.5, 4.0 Hz, 1H), 2.00-1.89 (m, 1H), 1.89-1.74 (m, 1H), 1.66-1.49 (m, 1H). |
| II-377 | 438.3 | 2.19 | 1H NMR (500 MHz, DMSO-d6) δ 8.61 (d, J = 9.1 Hz, 2H), 8.53 (d, J = 9.4 Hz, 1H), 8.02 (s, 1H), 7.69 (d, J = 9.4 Hz, 1H), 7.36 (d, J = 19.2 Hz, 2H), 3.47 (d, J = 9.9 Hz, 2H), 3.29 (s, 2H), |

TABLE 5-continued

Analytical data for compounds of Formula II

| II- | LCMS_Plus | LCMS_RT | NMR |
|---|---|---|---|
| | | | 2.99 (s, 4H), 1.87-1.66 (m, 3H), 1.69-1.48 (m, 1H), 1.22-1.12 (m, 3H). |
| II-378 | 374.1 | 1.85 | 1H NMR (400 MHz, DMSO-d6) δ 8.68-8.57 (m, 2H), 8.53 (d, J = 9.4 Hz, 1H), 8.03 (d, J = 1.2 Hz, 1H), 7.68 (d, J = 9.4 Hz, 1H), 7.49-7.14 (m, 2H), 6.94 (s, 1H), 4.82-4.08 (m, 2H), 3.07 (t, J = 11.9 Hz, 2H), 2.42-2.26 (m, 1H), 1.94 (d, J = 14.0 Hz, 1H), 1.84-1.61 (m, 2H), 1.53-1.36 (m, 1H). |
| II-379 | 492.1 | 2.45 | 1H NMR (500 MHz, DMSO-d6) δ 9.54 (t, J = 5.6 Hz, 1H), 8.72 (s, 2H), 8.58 (d, J = 9.4 Hz, 1H), 7.99 (d, J = 1.0 Hz, 1H), 7.76 (d, J = 9.5 Hz, 1H), 7.31 (t, J = 53.7 Hz, 1H), 4.40-4.25 (m, 1H), 3.19 (qd, J = 13.9, 5.1 Hz, 3H), 3.12-2.93 (m, 1H), 1.98-1.73 (m, 3H), 1.60-1.45 (m, 1H), 1.45-1.32 (m, 1H). 1 C-H missing |
| II-380 | 399.3 | 2.63 | |
| II-381 | 488.4 | 2.43 | 1H NMR (500 MHz, DMSO-d6) δ 8.72-8.65 (m, 2H), 8.55 (d, J = 9.4 Hz, 1H), 8.06 (d, J = 1.2 Hz, 1H), 7.72 (d, J = 9.5 Hz, 1H), 7.41-7.15 (m, 2H), 3.10 (t, J = 6.1 Hz, 2H), 2.96 (s, 4H), 2.22-2.12 (m, 1H), 2.06-1.99 (m, 1H), 1.33 (d, J = 6.9 Hz, 3H). |
| II-382 | 488.3 | 2.41 | 1H NMR (500 MHz, Methanol-d4) δ 8.67-8.59 (m, 2H), 8.37 (d, J = 9.5 Hz, 1H), 8.27 (d, J = 1.1 Hz, 1H), 7.68 (d, J = 9.5 Hz, 1H), 7.15 (t, J = 54.3 Hz, 1H), 5.36-5.22 (m, 1H), 4.57 (s, 1H), 4.41 (d, J = 14.4 Hz, 1H), 3.55-3.45 (m, 1H), 3.18 (ddd, J = 13.1, 10.1, 3.1 Hz, 1H), 3.09-3.02 (m, 1H), 2.88 (s, 3H), 2.42-2.33 (m, 1H), 2.17 (s, 1H), 1.40 (dd, J = 7.0, 1.9 Hz, 3H). |
| II-383 | 466.1 | 2.24 | 1H NMR (500 MHz, Methanol-d4) δ 8.63 (s, 1H), 8.57 (d, J = 1.1 Hz, 1H), 8.38 (d, J = 9.4 Hz, 1H), 8.09 (d, J = 1.2 Hz, 1H), 7.69 (d, J = 9.5 Hz, 1H), 7.11 (t, J = 54.0 Hz, 1H), 4.52 (br s, 1H), 4.02 (br s, 1H), 3.86 (dtd, J = 10.9, 5.7, 2.7 Hz, 1H), 3.63 (d, J = 13.4 Hz, 1H), 3.28 (dd, J = 5.7, 2.1 Hz, 2H), 3.11 (dd, J = 13.0, 10.9 Hz, 1H), 3.00 (s, 3H), 1.03-0.99 (m, 1H), 0.86-0.75 (m, 2H), 0.70-0.65 (m, 1H). |
| II-384 | 466.1 | 2.23 | 1H NMR (500 MHz, Methanol-d4) δ 8.63 (s, 1H), 8.57 (d, J = 1.1 Hz, 1H), 8.38 (d, J = 9.4 Hz, 1H), 8.10-8.00 (m, 1H), 7.69 (d, J = 9.5 Hz, 1H), 7.11 (t, J = 53.9 Hz, 1H), 4.51 (br s, 1H), 4.01 (br s, 1H), 3.88-3.83 (m, 1H), 3.63 (d, J = 13.3 Hz, 1H), 3.28 (dd, J = 5.7, 2.1 Hz, 2H), 3.11 (dd, J = 13.3, 10.7 Hz, 1H), 3.00 (s, 3H), 1.03-0.99 (m, 1H), 0.86-0.75 (m, 2H), 0.69-0.65 (m, 1H). |
| II-385 | 453 | 2.2 | 1H NMR (500 MHz, DMSO-d6) δ 8.62 (s, 1H), 8.58 (d, J = 1.1 Hz, 1H), 8.53 (d, J = 9.4 Hz, 1H), 8.00 (d, J = 1.2 Hz, 1H), 7.69 (d, J = 9.4 Hz, 1H), 7.30 (t, J = 55.0 Hz, 1H), 6.99 (t, J = 6.2 Hz, 1H), 6.70 (q, J = 5.1 Hz, 1H), 4.47 (v brs, 1H), 4.31 (v brs, 1H), 3.16-3.06 (m, 1H), 2.92-2.70 (m, 3H), 2.46 (d, J = 5.2 Hz, 3H), 1.88-1.82 (m, 1H), 1.81-1.69 (m, 2H), 1.52-1.343 (m, 1H), 1.36-1.28 (m, 1H). |
| II-386 | 455 | 1.98 | 1H NMR (500 MHz, DMSO-d6) δ 8.61-8.51 (m, 2H), 8.46 (d, J = 9.4 Hz, 1H), 7.92 (d, J = 1.2 Hz, 1H), 7.63 (d, J = 9.4 Hz, 1H), 7.24 (t, J = 55.0 Hz, 1H), 7.04 (t, J = 6.2 Hz, 1H), 6.69 (q, J = 5.1 Hz, 1H), 4.42 (br s, 1H), 4.15 (br s, 1H), 3.99-3.89 (m, 1H), 3.51 (tt, J = 11.6, 3.2 Hz, 2H), 3.06 (br t, J = 12.1 Hz, 1H), 2.96 (dt, J = 13.5, 5.8 Hz, 1H), 2.88 (dt, J = 13.4, 6.6 Hz, 1H), 2.74 (t, J = 11.7 Hz, 1H), 2.41 (d, J = 5.2 Hz, 3H). |
| II-387 | 453 | 2.08 | 1H NMR (500 MHz, DMSO-d6) δ 8.59 (s, 1H), 8.56-8.45 (m, 2H), 7.77 (d, J = 1.2 Hz, 2H), 7.68 (d, J = 9.4 Hz, 1H), 7.20 (t, J = 55.0 Hz, 1H), 6.63 (s, 2H), 4.03 (dt, J = 11.5, 5.7 Hz, 1H), 3.46-3.37 (m, 1H), 2.82 (td, J = 12.8, 2.9 Hz, 1H), 2.15-2.05 (m, 1H), 1.71-1.64 (m, 1H), 1.62-1.53 (m, 1H), 1.50-1.40 (m, 1H), 1.39-1.21 (m, 2H), 1.12 (d, J = 6.8 Hz, 3H), water peak obscures some signals. |
| II-388 | 470.1 | 2.36 | 1H NMR (500 MHz, Methanol-d4) δ 8.63 (s, 1H), 8.58 (d, J = 1.1 Hz, 1H), 8.37 (d, J = 9.4 Hz, 1H), |

TABLE 5-continued

Analytical data for compounds of Formula II

| II- | LCMS_Plus | LCMS_RT | NMR |
|---|---|---|---|
| | | | 8.19 (d, J = 1.2 Hz, 1H), 7.69 (d, J = 9.5 Hz, 1H), 7.16 (t, J = 54.0 Hz, 1H), 4.05 (d, J = 13.8 Hz, 1H), 3.95 (s, 2H), 3.85 (dd, J = 13.7, 6.4 Hz, 1H), 3.28 (dd, J = 12.9, 3.7 Hz, 1H), 2.97 (dd, J = 13.0, 11.0 Hz, 1H), 2.94 (s, 3H), 2.13 (s, 1H), 1.95-1.86 (m, 2H), 1.49 (d, J = 22.8 Hz, 3H). |
| II-389 | 470.1 | 2.38 | 1H NMR (500 MHz, Methanol-d4) δ 8.63 (s, 1H), 8.57 (d, J = 1.1 Hz, 1H), 8.37 (d, J = 9.4 Hz, 1H), 8.19 (d, J = 1.2 Hz, 1H), 7.69 (d, J = 9.5 Hz, 1H), 7.15 (t, J = 54.0 Hz, 1H), 4.05 (d, J = 14.2 Hz, 1H), 3.95 (d, J = 5.8 Hz, 2H), 3.84 (dd, J = 13.8, 6.5 Hz, 1H), 3.31-3.26 (m, 1H), 2.94 (s, 4H), 2.14 (dtd, J = 10.7, 6.8, 3.3 Hz, 1H), 2.00-1.87 (m, 2H), 1.49 (d, J = 22.8 Hz, 3H). |
| II-390 | 468.3 | 2.21 | |
| II-391 | 466.3 | 2.48 | 1H NMR (500 MHz, Methanol-d4) δ 8.69-8.62 (m, 2H0, 3.38 (d, 1H), 8.10-7.90 (m, 1H), 7.73 (d, 1H), 7.20-6.90 (dt, 1H), 3.25 (m, 3H), 3.10-2.90 (m, 2H), 2.86 (m, 2H), 2.10-1.85 (m, 4H), 1.72-1.50 (m, 4H), 0.80-0.70 (m, 3H). |
| II-392 | 377.3 | 1.96 | 1H NMR (400 MHz, DMSO-d6) δ 8.62 (d, J = 1.3 Hz, 2H), 8.52 (d, J = 9.4 Hz, 1H), 7.97 (s, 1H), 7.68 (d, J = 9.4 Hz, 1H), 7.29 (t, J = 56.1 Hz, 1H), 4.89 (s, 2H), 4.02 (dd, J = 11.4, 3.8 Hz, 1H), 3.69-3.43 (m, 3H), 3.45-3.37 (m, 1H), 3.32 (s, 1H), 1.09 (d, J = 6.5 Hz, 3H). |
| II-393 | 377.3 | 1.94 | 1H NMR (400 MHz, DMSO-d6) δ 8.63 (d, J = 1.2 Hz, 2H), 8.53 (dd, J = 9.4, 1.2 Hz, 1H), 8.00 (s, 1H), 7.69 (dd, J = 9.5, 1.1 Hz, 1H), 7.20-7.50 (m, 1H), 4.78-5.05 (m, 2H), 4.03 (d, J = 10.7 Hz, 1H), 3.72-3.45 (m, 3H), 3.45-3.35 (m, 1H), 3.30 (s, 1H), 1.12 (d, J = 25.0 Hz, 3H). |
| II-394 | 424 | 1.97 | 1H NMR (500 MHz, DMSO-d6) δ 8.62 (s, 1H), 8.55 (d, J = 1.1 Hz, 1H), 8.52 (d, J = 9.4 Hz, 1H), 7.72 (d, J = 1.2 Hz, 1H), 7.68 (d, J = 9.4 Hz, 1H), 7.44-7.19 (m, 2H), 3.86-3.42 (m, 4H), 3.07 (s, 2H), 2.93 (s, 3H), 2.53-2.45 (m, 1H) 2.28-2.05 (m, 1H), 1.92-1.75 (m, 1H). |
| II-395 | 395 | 1.85 | 1H NMR (500 MHz, DMSO-d6) δ 8.64 (s, 1H), 8.61 (d, J = 1.1 Hz, 1H), 8.53 (d, J = 9.4 Hz, 1H), 7.77 (d, J = 0.9 Hz, 1H), 7.69 (d, J = 9.4 Hz, 1H), 7.35 (t, J = 53.8 Hz, 1H), 4.15 (br s, 1H), 4.08-3.87 (m, 2H), 3.69 (br d, J = 24.6 Hz, 2H), 3.12 (s, 3H), 2.49-2.46 (m, 2H). |
| II-396 | 409 | 1.92 | 1H NMR (500 MHz, DMSO-d6) δ 8.63 (s, 1H), 8.57 (s, 1H), 8.53 (d, J = 9.3 Hz, 1H), 7.74 (s, 1H), 7.69 (d, J = 9.4 Hz, 1H), 7.51-7.17(m, 1H), 4.00 (br s, 1H), 3.81 (br s, 1H), 3.63 (br s, 1H), 3.53-3.37 (m, 3H), 3.06 (s, 3H), 2.82 (s, 1H), 2.43-2.18 (m, 1H), 2.01-1.76 (m, 1H). |
| II-397 | 452.3 | 2.4 | 1H NMR (500 MHz, DMSO-d6) δ 8.70 (d, J = 5.5 Hz, 2H), 8.57 (d, J = 9.3 Hz, 1H), 8.04 (s, 1H), 7.75 (dd, J = 9.6, 2.4 Hz, 1H), 7.43-7.11 (m, 2H), 2.93 (s, 5H), 2.68 (s, 2H), 1.93-1.85 (m, 1H), 1.68 (d, J = 37.4 Hz, 2H), 0.99 (d, J = 6.5 Hz, 4H). |
| II-398 | 452.3 | 2.38 | 1H NMR (500 MHz, DMSO-d6) δ 8.67 (d, J = 17.1 Hz, 2H), 8.56 (d, J = 9.4 Hz, 1H), 8.04 (d, J = 1.1 Hz, 1H), 7.73 (d, J = 9.4 Hz, 1H), 7.32 (s, 1H), 7.08 (t, J = 6.0 Hz, 1H), 3.65 (s, 2H), 3.40 (d, J = 7.5 Hz, 1H), 2.91 (td, J = 6.7, 3.8 Hz, 2H), 2.86 (s, 3H), 2.01 (s, 2H), 1.73-1.60 (m, 1H), 1.52 (ddd, J = 12.8, 8.0, 4.6 Hz, 1H), 0.95 (d, J = 6.7 Hz, 3H). |
| II-399 | 360 | 1.67 | 1H NMR (500 MHz, DMSO-d6) δ 8.62 (s, 1H), 8.56 (d, J = 1.2 Hz, 1H), 8.52 (d, J = 9.4 Hz, 1H), 7.72 (s, 1H), 7.68 (d, J = 9.4 Hz, 1H), 7.53 (br s, 1H), 7.34 (t, J = 53.6 Hz, 1H), 7.00 (br s, 1H), 3.87-3.46 (m, 4H), 3.09 (s, 1H), 2.46 (s, 1H), 2.30-2.16 (m, 1H). |
| II-400 | 357 | 2.89 | |
| II-401 | 359 | 2.27 | |
| II-402 | 361 | 2.49 | 1H NMR (500 MHz, DMSO-d6) δ 8.68 (d, J = 1.1 Hz, 1H), 8.64 (s, 1H), 8.53 (d, J = 9.4 Hz, 1H), 8.19 (d, J = 1.2 Hz, 1H), 7.69 (d, J = 9.4 Hz, 1H), 7.30 (t, J = 55.0 Hz, 1H), 3.88 (dd, J = 6.0, |

TABLE 5-continued

Analytical data for compounds of Formula II

| II- | LCMS_Plus | LCMS_RT | NMR |
|---|---|---|---|
| | | | 4.8 Hz, 2H), 3.74 (dd, J = 6.0, 4.8 Hz, 2H), 3.51 (s, 2H), 1.53 (s, 6H). |
| II-403 | 468.3 | 2.27 | 1H NMR (500 MHz, DMSO-d6) δ 8.63 (s, 1H), 8.61 (d, J = 1.1 Hz, 1H), 8.54 (d, J = 9.4 Hz, 1H), 8.01 (d, J = 1.2 Hz, 1H), 7.70 (d, J = 9.4 Hz, 1H), 7.41-7.22 (m, 1H), 7.20 (d, J = 5.5 Hz, 1H), 4.48 (br s, 1H), 4.20 (br s, 1H), 3.84-3.78 (m, 1H), 3.12-3.08 (m, 2H), 2.98-2.95 (m, 1H), 2.97 (s, 3H), 2.81-2.74 (m, 1H), 1.27 (s, 3H), 1.18 (s, 3H). |
| II-404 | 424.3 | 2.1 | |
| II-405 | 424.3 | 2.1 | |
| II-406 | 456.3 | 1.93 | 1H NMR (500 MHz, DMSO-d6) δ 8.72 (s, 1H), 8.65-8.63 (m, 2H), 7.96 (d, J = 1.2 Hz, 1H), 7.88 (d, J = 9.5 Hz, 1H), 4.43 (br s, 1H), 4.20 (br s, 1H), 4.01 (dd, J = 11.6, 3.4 Hz, 1H), 3.58 (td, J = 11.6, 2.9 Hz, 1H), 3.53-3.48 (m, 1H), 3.20 (dd, J = 12.3, 5.0 Hz, 1H), 3.12-2.99 (m, 2H), 2.06 (s, 6H), 2.84 (t, J = 11.7 Hz, 1H). |
| II-407 | 440 | 2.08 | 1H NMR (500 MHz, DMSO-d6) δ 8.69 (s, 1H), 8.63 (d, J = 9.5 Hz, 1H), 8.59 (d, J = 1.0 Hz, 1H), 7.97 (s, 1H), 7.86 (d, J = 9.5 Hz, 1H), 4.16 (br s, 1H), 3.30-3.21 (m, 2H), 3.13-3.04 (m, 1H), 3.01 (s, 3H), 3.00 (s, 3H), 2.94-2.77 (m, 1H), 1.95-1.89 (m, 1H), 1.83-1.71 (m, 1H), 1.58-1.43 (m, 2H). |
| II-408 | 422 | 1.94 | |
| II-409 | 346 | 1.77 | 1H NMR (500 MHz, DMSO-d6) δ 8.61 (s, 1H), 8.54 (d, J = 1.1 Hz, 1H), 8.52 (d, J = 9.4 Hz, 1H), 7.71 (s, 1H), 7.68 (d, J = 9.4 Hz, 1H), 7.34 (t, J = 53.7 Hz, 1H), 3.84-3.42 (m, 3H), 3.23-3.15 (m, 1H), 2.72-2.57 (m, 2H), 2.47-2.23 (m, 1H), 2.23-1.99 (m, 1H), 1.92-1.67 (m, 1H). |
| II-410 | 453.3 | 1.93 | |
| II-411 | 453.3 | 1.9 | 1H NMR (500 MHz, DMSO-d6) δ 8.63 (s, 1H), 8.60 (s, 1H), 8.54-8.52 (d, 1H), 8.01 (s, 1H), 7.70-7.68 (d, 1H), 7.30 (t, 1H), 7.20 (s, 1H), 4.40 (br s, 2H), 3.30 (masked, 2H), 3.04 (m, 2H), 2.96 (s, 3H), 2.75 (m, 2H), 1.08 (d, 3H). |
| II-412 | 438.1 | 2.26 | 1H NMR (400 MHz, DMSO-d6) δ 8.62 (s, 1H), 8.57 (d, J = 1.0 Hz, 1H), 8.53 (d, J = 9.4 Hz, 1H), 8.05 (d, J = 1.2 Hz, 1H), 7.70 (d, J = 9.4 Hz, 1H), 7.32 (t, J = 53.8 Hz, 1H), 7.05 (s, 1H), 3.98 (d, J = 13.9 Hz, 2H), 3.66 (d, J = 13.3 Hz, 1H), 3.49 (t, J = 10.7 Hz, 1H), 3.00 (s, 3H), 2.00-1.49 (m, 4H), 1.36 (s, 3H). |
| II-413 | 377.1 | 1.91 | |
| II-414 | 377.1 | 1.91 | |
| II-415 | 425 | 1.84 | 1H NMR (500 MHz, DMSO-d6) δ 8.62 (s, 1H), 8.55 (d, J = 1.1 Hz, 1H), 8.53 (d, J = 9.4 Hz, 1H), 7.71 (s, 1H), 7.68 (d, J = 9.4 Hz, 1H), 7.48-7.17 (t, J = 50 Hz, 1H), 6.76 (br s, 1H), 6.55 (s, 2H), 3.88-3.41 (m, 4H), 2.99 (br s, 2H), 2.26-2.00 (m, 2H), 1.96-1.73 (m, 1H). |
| II-416 | 466.1 | 2.48 | |
| II-417 | 466.1 | 2.48 | |
| II-418 | 467.1 | 2.09 | 1H NMR (500 MHz, DMSO-d6) δ 8.72 (d, 1H), 8.67 (s, 1H), 8.57-8.55 (d, 1H), 8.08 (s, 1H), 7.74-7.72 (d, 1H), 7.43 (s, 1H), 7.43-7.22 (t, 1H), 4.80-4.50 (br d, 1H), 3.50 (masked, 4H), 3.30 (m, 2H), 3.07 (s, 3H), 2.90 (s, 3H), 2.80 (m, 1H), 1.50-1.25 (m, 4H). |
| II-419 | 466.1 | 2.11 | |
| II-420 | 464.1 | 2.47 | |
| II-421 | 438.3 | 2.25 | |
| II-422 | 439.3 | 2.12 | |
| II-423 | 467.3 | 2.18 | 1H NMR (500 MHz, DMSO-d6) δ 8.72 (s, 1H), 8.67 (s, 1H), 8.57-8.54 (d, 1H), 8.04 (s, 1H), 7.74-7.72 (d, 1H), 7.55 (m, 1H), 7.30 (t, 1H), 4.90 (br s, 2H), 3.30 (masked, 6H), 2.98-2.90 (m, 6H), 1.08 (d, 3H). |
| II-424 | 438 | 2.2 | |
| II-425 | 438.1 | 1.88 | 1H NMR (500 MHz, DMSO-d6) δ 8.69-8.59 (m, 2H), 8.57-8.47 (m, 1H), 8.00 (s, 1H), 7.76-7.67 (m, 1H), 7.35 (t, J = 53.7 Hz, 1H), 4.08 (s, 2H), |

TABLE 5-continued

Analytical data for compounds of Formula II

| II- | LCMS_Plus | LCMS_RT | NMR |
|---|---|---|---|
| | | | 3.70 (d, J = 59.8 Hz, 2H), 3.31 (m, 2H hidden), 2.99 (s, 3H), 1.16 (m, 3H + 2H). |
| II-426 | 439.1 | 2.16 | 1H NMR (500 MHz, DMSO-d6) δ 8.74-8.59 (m, 2H), 8.55 (d, J = 9.4 Hz, 1H), 8.00 (s, 1H), 7.73 (d, J = 9.4 Hz, 1H), 7.34 (t, J = 53.5 Hz, 1H), 4.19-4.01 (m, 2H), 3.67 (m, J = 11.7 Hz, 6H, partially hidden), 3.05 (s, 3H), 1.25-1.05 (m, 3H). |
| II-427 | 467.3 | 2.02 | 1H NMR (500 MHz, Methanol-d4) δ 8.74 (d, 1H), 8.71 (s, 1H), 8.44 (d, 1H), 8.18 (s, 1H), 7.76-7.74 (d, 1H), 7.24-7.03 (t, 1H), 5.20 (brs, 2H), 3.69 (m, 1H), 3.52-3.40 (m, 3H), 3.23 (m, 1H), 3.09 (s, 3H), 1.54-1.53 (d, 3H), 1.41-1.40 (m, 3H). |
| II-428 | 511 | 2.14 | 1H NMR (500 MHz, DMSO-d6) δ 8.62-8.50 (m, 2H), 8.45 (d, J = 9.4 Hz, 1H), 7.86 (s, 1H), 7.61 (d, J = 9.4 Hz, 1H), 7.36-7.13 (m, 2H), 4.57-4.41 (m, 1H), 4.00 (v brs s, 2H), 3.20-2.96 (m, 4H), 2.94-2.75 (m, 5H), 2.68 (ddd, J = 24.1, 13.8, 3.7 Hz, 1H), 2.48 (br s, 1H), 1.86 (dt, J = 10.4, 5.2 Hz, 1H), 1.69 (d, J = 10.8 Hz, 1H), water peak obscures some signals. |
| II-429 | 511 | 2.11 | 1H NMR (500 MHz, DMSO-d6) δ 8.63 (d, J = 1.9 Hz, 1H), 8.57-8.41 (m, 2H), 7.97 (s, 1H), 7.68 (dd, J = 9.4, 1.8 Hz, 1H), 7.42 (br t, J = 55.0 Hz, 1H), 7.10 (br t, J = 7.2 Hz, 1H), 5.04 (br d, J = 58.1 Hz, 1H), 4.30 (v br s, 2H), 3.62-5.52 (m, 2H), 3.25-2.99 (m, 3H), 2.99-2.68 (m, 6H), 1.95 (br s, 1H), 1.72 (br d, J = 13.6 Hz, 1H), 1.42 (br t, J = 12.0 Hz, 1H), water peak obscures some signals. |
| II-430 | 423.3 | 2.2 | 1H NMR (500 MHz, DMSO-d6) δ 8.63 (s, 1H), 8.59 (d, J = 1.1 Hz, 1H), 8.53 (d, J = 9.5 Hz, 1H), 8.01 (d, J = 1.0 Hz, 1H), 7.70 (d, J = 9.4 Hz, 1H), 7.34 (t, J = 53.6 Hz, 1H), 4.53 (br s, 1H), 4.39 (br s, 1H), 3.23-3.22 (m, 2H), 3.11-3.03 (m, 2H), 3.05 (s, 3H), 2.20 (br s, 1H), 1.96 (d, J = 10.0 Hz, 1H), 1.79-1.76 (m, 1H), 1.58-1.45 (m, 2H). |
| II-431 | 488.1 | 2.5 | 1H NMR (500 MHz, DMSO-d6) δ 8.67 (d, J = 12.2 Hz, 2H), 8.55 (d, J = 9.4 Hz, 1H), 8.06 (s, 1H), 7.71 (d, J = 9.4 Hz, 1H), 7.29 (s, 1H), 3.47 (dd, J = 13.1, 4.1 Hz, 1H), 3.29 (s, 1H), 3.22 (s, 1H), 3.10 (t, J = 12.1 Hz, 1H), 3.01 (s, 3H), 2.46 (s, 1H), 2.40 (s, 1H), 2.25 (d, J = 14.0 Hz, 1H), 2.16 (s, 1H), 2.09 (s, 1H), 1.26-1.14 (m, 3H). |
| II-432 | 488.1 | 2.51 | 1H NMR (500 MHz, DMSO-d6) δ 8.70-8.62 (m, 2H), 8.54 (d, J = 9.4 Hz, 1H), 8.06 (d, J = 1.2 Hz, 1H), 7.71 (d, J = 9.5 Hz, 1H), 7.29 (s, 1H), 3.51-3.43 (m, 1H), 3.29 (s, 4H), 3.10 (t, J = 12.2 Hz, 1H), 3.01 (s, 3H), 2.41 (s, 1H), 2.32-2.22 (m, 2H), 2.17 (s, 1H), 2.09 (s, 1H), 1.21 (d, J = 6.9 Hz, 4H). |
| II-433 | 488.1 | 2.51 | 1H NMR (500 MHz, DMSO-d6) δ 8.70-8.62 (m, 2H), 8.54 (d, J = 9.4 Hz, 1H), 8.04 (d, J = 1.2 Hz, 1H), 7.70 (d, J = 9.4 Hz, 1H), 7.31 (t, J = 53.5 Hz, 1H), 5.00 (d, J = 19.8 Hz, 1H), 4.85 (s, 1H), 3.48-3.41 (m, 1H), 3.27 (s, 1H), 3.05-2.92 (m, 5H), 2.37-2.14 (m, 3H), 1.29-1.23 (m, 3H). |
| II-434 | 488.1 | 2.51 | 1H NMR (500 MHz, DMSO-d6) δ 8.70-8.62 (m, 2H), 8.54 (d, J = 9.4 Hz, 1H), 8.03 (d, J = 1.3 Hz, 1H), 7.71 (d, J = 9.4 Hz, 1H), 7.28 (t, J = 53.5 Hz, 1H), 5.02-4.95 (m, 1H), 4.83 (s, 1H), 3.45 (dd, J = 13.4, 3.5 Hz, 1H), 2.99 (s, 5H), 2.38-2.14 (m, 3H), 1.29-1.22 (m, 3H). |
| II-435 | 465.1 | 1.95 | 1H NMR (400 MHz, DMSO-d6) δ 9.12 (s, 2H), 8.69-8.58 (m, 2H), 8.54 (d, J = 9.4 Hz, 1H), 8.03 (d, J = 1.2 Hz, 1H), 7.96 (dd, J = 7.4, 4.5 Hz, 1H), 7.70 (d, J = 9.5 Hz, 1H), 7.30 (t, J = 53.7 Hz, 1H), 4.50 (t, J = 7.8 Hz, 1H), 4.28 (m, 2H), 4.09 (m, 2H), 3.20 (m, some protons obscured, should be 4H), 1.96 (s, 1H), 1.83 (s, 1H), 1.55 (d, J = 8.8 Hz, 2H), 1.33-1.08 (m, 1H). |
| II-436 | 452.1 | 2.14 | 1H NMR (500 MHz, Methanol-d4) δ 8.48 (s, 1H), 8.40 (s, 1H), 8.24 (d, J = 9.4 Hz, 1H), 7.91 (s, 1H), 7.57 (d, J = 9.5 Hz, 1H), 7.00 (t, J = 53.9 Hz, 1H), 4.53 (s, 2H), 2.99 (dd, J = 13.1, 5.3 Hz, 1H), 2.96-2.89 (m, 1H), 2.56 (t, J = 12.4 Hz, |

TABLE 5-continued

Analytical data for compounds of Formula II

| II- | LCMS_Plus | LCMS_RT | NMR |
|---|---|---|---|
| | | | 1H), 2.43 (t, J = 12.4 Hz, 1H), 1.85 (d, J = 13.4 Hz, 1H), 1.78-1.64 (m, 1H), 1.59 (dq, J = 10.3, 6.0, 5.0 Hz, 1H), 0.97-0.81 (m, 4H). |
| II-437 | 452.1 | 2.41 | 1H NMR (500 MHz, Methanol-d4) δ 8.56 (s, 1H), 8.47 (d, J = 1.1 Hz, 1H), 8.33 (d, J = 9.4 Hz, 1H), 8.00 (d, J = 1.3 Hz, 1H), 7.65 (d, J = 9.4 Hz, 1H), 7.10 (t, J = 54.0 Hz, 1H), 4.61 (s, 2H), 3.10 (dd, J = 13.1, 5.4 Hz, 1H), 3.05-3.01 (m, 1H), 2.63 (t, J = 12.4 Hz, 1H), 2.54-2.45 (m, 1H), 2.00-1.91 (m, 1H), 1.80 (dh, J = 11.9, 3.9 Hz, 1H), 1.69 (td, J = 11.4, 9.6, 5.6 Hz, 1H), 1.07-0.96 (m, 4H). |
| II-438 | 359 | 1.99 | 1H NMR (500 MHz, DMSO-d6) δ 8.61 (s, 1H), 8.58-8.47 (m, 2H), 7.68 (d, J = 9.4 Hz, 2H), 7.35 (t, J = 52.5 Hz, 1H), 4.76 (br s, 1H), 4.01-3.52 (m, 6H), 1.66-1.62 (m, 1H), 0.89 (dd, J = 8.0, 4.7 Hz, 1H), 0.43 (t, J = 4.5 Hz, 1H). |
| II-439 | 450 | 2.17 | 1H NMR (500 MHz, DMSO-d6) δ 8.62 (s, 1H), 8.58-8.46 (m, 2H), 7.69-7.65 (m, 3H), 7.48-7.08 (m, 1H), 3.84 (br s, 1H), 3.62 (br s, 1H), 3.43 (td, J = 10.2, 6.9 Hz, 1H), 3.19 (br t, J = 10.7 Hz, 1H), 2.93 (s, 3H), 2.76-2.54 (m, 1H), 2.05 (br s, 1H), 1.91-1.61 (m, 1H), 1.02-0.66 (m, 4H). |
| II-440 | 480.3 | 2.29 | 1H NMR (500 MHz, DMSO-d6) δ 8.64 (s, 1H), 8.62 (d, J = 1.1 Hz, 1H), 8.54 (d, J = 9.4 Hz, 1H), 8.05 (s, 1H), 7.70 (d, J = 9.5 Hz, 1H), 7.31 (t, J = 53.8 Hz, 1H), 7.18 (s, 1H), 4.04-4.01 (m, 2H), 3.85 (brs, 1H), 3.70 (dd, J = 13.0, 6.1 Hz, 1H), 3.49 (dd, J = 13.3, 7.1 Hz, 1H), 3.18-3.08 (m, 3H), 2.93 (s, 3H), 1.15-1.03 (m, 1H), 0.52-0.48 (m, 2H), 0.41-0.32 (m, 2H). |
| II-441 | 480.3 | 2.29 | 1H NMR (500 MHz, DMSO-d6) δ 8.64 (s, 1H), 8.62 (d, J = 1.1 Hz, 1H), 8.54 (d, J = 9.4 Hz, 1H), 8.05 (s, 1H), 7.70 (d, J = 9.4 Hz, 1H), 7.31 (t, J = 53.8 Hz, 1H), 7.18 (s, 1H), 4.05-4.00 (m, 2H), 3.85 (brs, 1H), 3.70 (dd, J = 13.6, 6.0 Hz, 1H), 3.49 (dd, J = 13.4, 7.1 Hz, 1H), 3.18-3.08 (m, 3H), 2.93 (s, 3H), 1.11-1.04 (m, 1H), 0.52-0.47 (m, 2H), 0.41-0.32 (m, 2H). |
| II-442 | 450.3 | 2.32 | 1H NMR (400 MHz, DMSO-d6) δ 8.69 (d, J = 3.8 Hz, 2H), 8.57 (d, J = 9.4 Hz, 1H), 8.02 (d, J = 1.1 Hz, 1H), 7.75 (d, J = 9.4 Hz, 1H), 7.52-7.13 (m, 2H), 4.34 (d, J = 100.4 Hz, 2H), 3.48-3.08 (m, 3H), 2.72-2.59 (m, 1H), 2.05 (dd, J = 12.8, 6.2 Hz, 1H), 1.92-1.77 (m, 1H), 1.72-1.44 (m, 2H), 1.03-0.83 (m, 4H). |
| II-443 | 480.1 | 2.39 | 1H NMR (500 MHz, DMSO-d6) δ 8.64 (s, 1H), 8.63 (d, J = 0.9 Hz, 1H), 8.54 (d, J = 9.5 Hz, 1H), 8.05 (s, 1H), 7.70 (d, J = 9.4 Hz, 1H), 7.30 (t, J = 54.0 Hz, 1H), 7.27 (br s, 1H), 4.44 (br s, 2H), 3.57-3.51 (m, 1H), 3.22-3.11 (m, 2H), 2.97 (s, 3H), 2.94-2.89 (m, 2H), 2.80-2.74 (m, 1H), 0.98-0.93 (m, 1H), 0.56-0.51 (m, 2H), 0.41-0.35 (m, 2H). |
| II-444 | 480.1 | 2.38 | 1H NMR (500 MHz, DMSO-d6) δ 8.65 (s, 1H), 8.63 (d, J = 1.1 Hz, 1H), 8.54 (d, J = 9.4 Hz, 1H), 8.05 (s, 1H), 7.70 (d, J = 9.4 Hz, 1H), 7.30 (t, J = 53.9 Hz, 1H), 7.28 (br s, 1H), 4.42 (br s, 2H), 3.57-3.51 (m, 1H), 3.22-3.12 (m, 2H), 2.98 (s, 3H), 2.96-2.89 (m, 2H), 2.77 (br s, 1H), 0.99-0.92 (m, 1H), 0.56-0.51 (m, 2H), 0.40-0.38 (m, 2H). |
| II-445 | 438.1 | 2.26 | 1H NMR (400 MHz, DMSO-d6) δ 8.62 (s, 1H), 8.58 (d, J = 1.1 Hz, 1H), 8.53 (d, J = 9.4 Hz, 1H), 8.05 (d, J = 1.2 Hz, 1H), 7.70 (d, J = 9.4 Hz, 1H), 7.33 (t, J = 53.7 Hz, 1H), 7.05 (s, 1H), 4.03 (d, J = 47.3 Hz, 2H), 3.66 (d, J = 13.2 Hz, 1H), 3.49 (dd, J = 12.7, 8.5 Hz, 1H), 3.00 (s, 3H), 1.94-1.53 (m, 4H), 1.36 (s, 3H). |
| II-446 | 438.1 | 2.26 | 1H NMR (400 MHz, DMSO-d6) δ 8.62 (s, 1H), 8.57 (d, J = 1.0 Hz, 1H), 8.53 (d, J = 9.5 Hz, 1H), 8.05 (d, J = 1.2 Hz, 1H), 7.70 (d, J = 9.4 Hz, 1H), 7.33 (t, J = 53.7 Hz, 1H), 7.06 (s, 1H), 4.15-3.88 (m, 2H), 3.65 (d, J = 13.3 Hz, 1H), 3.48 (td, J = 9.8, 8.8, 5.0 Hz, 1H), 2.99 (s, 3H), 1.97-1.54 (m, 4H), 1.36 (s, 3H). |

TABLE 5-continued

Analytical data for compounds of Formula II

| II- | LCMS_Plus | LCMS_RT | NMR |
|---|---|---|---|
| II-447 | 436 | 2.1 | 1H NMR (500 MHz, DMSO-d6) δ 8.62 (s, 1H), 8.58-8.48 (m, 2H), 7.70-7.68 (m, 2H), 7.47-7.18 (m, 2H), 4.01-3.50 (m, 4H), 3.24 (br s, 2H), 2.95 (brs, 3H), 1.78-1.65 (m, 1H), 0.95 (dd, J = 7.9, 4.9 Hz, 1H), 0.50 (t, J = 4.6 Hz, 1H). |
| II-448 | 481.4 | 2.19 | 1H NMR (500 MHz, Methanol-d4) δ 8.65 (s, 1H), 8.58 (s, 1H), 8.39-8.37 (d, 1H), 8.11 (s, 1H), 7.70-7.68 (d, 1H), 7.28-7.04 (t, 1H), 4.80-4.60 (m, 2H), 3.56 (m, 1H), 3.08-3.04 (m, 4H), 2.85 (m, 1H), 2.52 (m, 1H), 2.36 (s, 3H), 2.28 (m, 1H), 1.31-1.25 (m, 6H). |
| II-449 | 438.1 | 2.3 | 1H NMR (400 MHz, DMSO-d6) δ 8.62 (s, 1H), 8.59 (d, J = 1.1 Hz, 1H), 8.53 (d, J = 9.4 Hz, 1H), 8.05 (d, J = 1.2 Hz, 1H), 7.69 (d, J = 9.5 Hz, 1H), 7.47-7.10 (m, 2H), 4.95-3.98 (m, 2H), 3.34-3.20 (m, 2H), 2.99 (s, 3H), 2.80-2.64 (m, 1H), 2.04 (d, J = 12.3 Hz, 1H), 1.69 (s, 1H), 1.20 (q, J = 12.2 Hz, 1H), 0.97 (d, J = 6.5 Hz, 3H). |
| II-450 | 439.3 | 1.75 | 1H NMR (500 MHz, DMSO-d6) δ 8.62-8.59 (m, 2H), 8.53-8.51 (d, 1H0, 7.97 (s, 1H), 7.70-7.68 (d, 1H), 7.42-7.20 (m, 2H), 4.40 (br s, 1H), 4.20 (br s, 1H), 3.07 (m, 4H), 2.95 (s, 3H), 2.70 (m, 3H). |
| II-451 | 345 | 1.96 | 1H NMR (400 MHz, DMSO-d6) δ 8.72-8.61 (m, 2H), 8.54 (d, J = 9.4 Hz, 1H), 7.91 (d, J = 1.2 Hz, 1H), 7.70 (d, J = 9.4 Hz, 1H), 7.35 (t, J = 53.6 Hz, 1H), 4.78 (s, 2H), 4.05-3.60 (m, 4H), 3.20 (dt, J = 8.9, 6.6 Hz, 1H), 1.93 (d, J = 9.0 Hz, 1H). |
| II-452 | 465 | 2.02 | 1H NMR (500 MHz, DMSO-d6) δ 8.64 (d, J = 1.1 Hz, 2H), 8.54 (d, J = 9.4 Hz, 1H), 8.04 (d, J = 1.2 Hz, 1H), 7.70 (d, J = 9.4 Hz, 1H), 7.34 (t, J = 52.5 Hz, 1H), 4.12 (d, J = 8.9 Hz, 2H), 3.94 (s, 2H), 3.67 (s, 2H), 3.51 (d, J = 8.8 Hz, 2H), 3.07 (s, 3H), 2.59 (dd, J = 6.2, 4.4 Hz, 2H), 2.44 (s, 3H). |
| II-453 | 389 | 1.75 | 1H NMR (500 MHz, DMSO-d6) δ 8.68-8.57 (m, 2H), 8.53 (d, J = 9.4 Hz, 1H), 8.03 (d, J = 1.2 Hz, 1H), 7.69 (d, J = 9.4 Hz, 1H), 7.50-7.17 (m, 3H), 4.40 (brs, 1H), 4.24 (brs, 1H), 3.21 (t, J = 11.6 Hz, 1H), 2.98 (d, J = 11.6 Hz, 1H), 2.65-2.60 (m, 1H), 2.23-2.28 (m, 4H), water peak obscures some signals. |
| II-454 | 388 | 1.82 | 1H NMR (500 MHz, DMSO-d6) δ 8.62 (s, 1H), 8.58 (d, J = 1.1 Hz, 1H), 8.52 (d, J = 9.4 Hz, 1H), 8.01 (d, J = 1.1 Hz, 1H), 7.68 (d, J = 9.4 Hz, 1H), 7.30 (t, J = 52.5 Hz, 1H), 5.29 (s, 1H), 4.53 (brs, 1H), 4.35 (br s, 1H), 3.10-3.00 (m, 1H), 2.91-2.87 (m, 2H), 2.74-2.59 (m, 1H), 2.39 (dd, J = 10.8, 3.1 Hz, 1H), 2.22 (s, 1H), 0.68-0.45 (m, 4H). |
| II-455 | 438.05 | 2.29 | 1H NMR (400 MHz, Chloroform-d) δ 9.00 (s, 1H), 8.85 (s, 1H), 8.44 (d, J = 9.4 Hz, 1H), 8.10 (s, 1H), 7.70 (d, J = 9.4 Hz, 1H), 7.08 (s, 1H), 5.19 (s, 1H), 4.41 (s, 1H), 3.83 (ddt, J = 11.7, 8.1, 3.8 Hz, 1H), 3.33 (s, 1H), 3.02 (s, 1H), 2.96 (d, J = 16.0 Hz, 6H), 2.17-2.11 (m, 1H), 2.11 (s, 1H), 1.97 (qd, J = 11.7, 3.6 Hz, 1H), 1.77 (t, J = 13.6 Hz, 1H). |
| II-456 | 523.4 | 2.52 | 1H NMR (500 MHz, DMSO-d6) δ 9.74 (s, 1H), 8.71-8.61 (m, 2H), 8.55 (d, J = 9.4 Hz, 1H), 8.00 (d, J = 1.1 Hz, 1H), 7.72 (d, J = 9.4 Hz, 1H), 7.38 (d, J = 53.8 Hz, 1H), 4.59 (s, 2H), 3.76-3.64 (m, 2H), 3.56 (s, 3H), 3.17 (t, J = 11.2 Hz, 1H), 2.91 (s, 1H), 2.87 (s, 6H), 1.97 (ddp, J = 10.4, 6.8, 3.4 Hz, 1H), 1.93-1.80 (m, 2H), 1.55-1.44 (m, 1H), 1.39 (ddt, J = 13.8, 11.3, 5.7 Hz, 1H). 2 CH not observed. |
| II-457 | 468.3 | 2.3 | 1H NMR (500 MHz, DMSO-d6) δ 8.70 (s, 1H), 8.66 (s, 1H), 8.55 (d, J = 9.4 Hz, 1H), 8.19 (d, J = 1.2 Hz, 1H), 7.71 (d, J = 9.4 Hz, 1H), 7.38-7.12 (m, 2H), 4.31 (dd, J = 13.8, 3.7 Hz, 1H), 3.92-3.86 (m, 1H), 3.76 (d, J = 11.8 Hz, 1H), 3.50 (d, J = 11.9 Hz, 1H), 3.32 (dd, J = 13.8, 10.0 Hz, 1H), 3.20-3.10 (m, 2H), 2.95 (s, 3H), 1.61 (s, 3H), 1.47 (s, 3H). |
| II-458 | 482.1 | 2.41 | 1H NMR (400 MHz, DMSO-d6) δ 8.62 (d, J = 2.7 Hz, 2H), 8.53 (d, J = 9.4 Hz, 1H), 8.01 (s, |

TABLE 5-continued

Analytical data for compounds of Formula II

| II- | LCMS_Plus | LCMS_RT | NMR |
|---|---|---|---|
| | | | 1H), 7.69 (d, J = 9.5 Hz, 1H), 7.54-7.04 (m, 2H), 5.05 (s, 1H), 4.51 (s, 1H), 4.19 (s, 1H), 3.95 (s, 1H), 3.02 (d, J = 6.4 Hz, 2H), 2.96 (s, 3H), 1.30 (s, 3H), 1.22 (s, 3H), 1.17-1.07 (m, 3H). |
| II-459 | 402 | 2.11 | 1H NMR (500 MHz, DMSO-d6) δ 8.63 (s, 1H), 8.60 (s, 1H), 8.53 (d, J = 9.4 Hz, 1H), 8.03 (s, 1H), 7.69 (d, J = 9.4 Hz, 1H), 7.33 (t, J = 55.0 Hz, 1H), 5.02 (s, 1H), 4.37 (vbrs, 2H), 3.27-3.20 (m, 1H), 3.08 (br t, J = 15.0 Hz, 1H), 2.94 (br d, J = 11.6 Hz, 1H), 2.39 (s, 3H), 2.16 (br t, J = 15.0 Hz, 1H), 1.28 (d, J = 10.7 Hz, 1H), 0.85-0.79 (m, 1H), 0.69-0.48 (m, 2H), 0.38 (br s, 1H). |
| II-460 | 452.3 | 1.53 | 1H NMR (500 MHz, DMSO-d6) δ 11.85 (s, 1H), 8.68 (d, J = 2.5 Hz, 2H), 8.56 (d, J = 9.4 Hz, 1H), 8.04 (d, J = 1.2 Hz, 1H), 7.73 (d, J = 9.4 Hz, 1H), 7.32 (t, J = 53.8 Hz, 1H), 4.47 (s, 1H), 4.23 (d, J = 16.2 Hz, 1H), 3.40 (t, J = 11.6 Hz, 1H), 3.36-3.27 (m, 1H), 3.25 (s, 3H), 2.64-2.54 (m, 1H), 2.07-1.97 (m, 1H), 1.81 (dddd, J = 37.9, 14.2, 9.7, 4.0 Hz, 2H), 1.50 (q, J = 11.7, 11.3 Hz, 1H). |
| II-461 | 502.3 | 2.72 | |
| II-462 | 502.4 | 2.7 | 1H NMR (500 MHz, DMSO-d6) δ 8.67-8.63 (m, 2H), 8.55-8.52 (m, 1H), 8.09 (s, 1H), 7.71-7.68 (m, 1H), 7.29 m, 2H), 4.80 (brs, 1H), 3.62 (m, 1H), 3.30 (masked, 1H), 3.01 (s, 3H), 2.97 (s, 2H), 2.60-2.30 (m, 1H), 2.15 (m, 1H), 1.30-1.22 (m, 3H), 1.07 (m, 3H). |
| II-463 | 493.4 | 2.54 | 1H NMR (500 MHz, DMSO-d6) δ 8.63 (s, 1H), 8.62 (s, 1H), 8.53 (d, J = 9.4 Hz, 1H), 7.96 (s, 1H), 7.69 (d, J = 9.5 Hz, 1H), 7.49-7.02 (m, 2H), 3.83-3.66 (m, 1H), 3.10 (d, J = 11.2 Hz, 1H), 2.98 (s, 3H), 2.94-2.80 (m, 1H), 2.66-2.57 (m, 1H), 2.54 (s, 3H), 2.41-2.25 (m, 1H), 1.66-1.54 (m, 1H), 1.14-1.01 (m, 2H), 0.74-0.61 (m, 1H), 0.57-0.42 (m, 1H), 0.34 (d, J = 4.1 Hz, 1H). |
| II-464 | 439 | 1.82 | |
| II-465 | 453 | 1.83 | 1H NMR (500 MHz, DMSO-d6) δ 8.63 (d, J = 3.2 Hz, 1H), 8.59 (t, J = 1.3 Hz, 1H), 8.56-8.49 (m, 1H), 7.97 (dd, J = 19.0, 1.2 Hz, 1H), 7.69 (dd, J = 9.4, 2.2 Hz, 1H), 7.42-7.04 (m, 2H), 4.68-4.06 (vbr s, 2H), 3.51-3.33 (m, 1H), 3.18-2.87 (m, 5H), 2.87-2.53 (m, 3H), 1.24 (dd, J = 6.8, 1.4 Hz, 3H). |
| II-466 | 471.3 | 1.98 | 1H NMR (400 MHz, DMSO-d6) δ 9.32 (s, 1H), 9.15 (s, 1H), 8.80-8.70 (m, 2H), 8.67 (d, J = 9.5 Hz, 1H), 7.99 (d, J = 1.2 Hz, 1H), 7.91 (d, J = 9.5 Hz, 1H), 7.61-7.46 (m, 1H), 3.51 (d, J = 11.3 Hz, 2H), 3.23 (dt, J = 14.3, 6.7 Hz, 5H), 3.04 (s, 3H), 2.50 (s, 2H), 1.28 (d, J = 7.0 Hz, 3H). Some peaks obscured by solvent peaks. |
| II-467 | 502.4 | 2.62 | |
| II-468 | 502.4 | 2.62 | |
| II-469 | 502.1 | 2.71 | |
| II-470 | 502.1 | 2.7 | |
| II-471 | 502.1 | 2.68 | 1H NMR (500 MHz, Chloroform-d) δ 8.89-8.64 (m, 2H), 8.26 (d, 1H), 7.49 (d, 1H), 7.01 (d, 1H), 4.53 (s, 1H), 3.68 (d, 1H), 3.38 (d, 1H), 3.05 (s, 3H), 2.95 (m, 1H), 2.45 (d, 1H), 2.27-1.97 (m, 2H), 1.42-1.10 (m, 6H). |
| II-472 | 502.1 | 2.68 | 1H NMR (400 MHz, DMSO-d6) δ 8.67-8.64 (m, 2H), 8.54 (d, J = 9.4 Hz, 1H), 8.08 (s, 1H), 7.70 (d, J = 9.4 Hz, 1H), 7.38-7.11 (m, 2H), 5.75-3.98 (m, 2H), 3.49-3.45 (m, 1H), 3.14-3.06 (m, 1H), 3.00 (s, 3H), 2.54-2.49 (masked signal, 1H), 2.29-2.19 (m, 1H), 1.26-1.11 (m, 3H), 1.07 (d, J = 6.6 Hz, 3H). |
| II-473 | 467 | 2.05 | 1H NMR (500 MHz, DMSO-d6) δ 8.65-8.34 (m, 3H), 7.87 (s, 1H), 7.62 (d, J = 9.3 Hz, 1H), 7.36-7.04 (m, 2H), 4.42 (vbrs, 1H), 4.22 (vbrs, 1H), 3.77-3.69 (m, 1H), 3.10-2.70 (m, 6H), 2.19 (s, 3H), 2.06-2.01 (m, 1H), 1.35-1.02 (m, 4H). |
| II-474 | 467 | 2.13 | 1H NMR (500 MHz, DMSO-d6) δ 8.64 (s, 1H), 8.61 (s, 1H), 8.54 (d, J = 9.4 Hz, 1H), 7.99 (s, 1H), 7.70 (d, J = 9.4 Hz, 1H), 7.32 (t, J = 52.5 Hz, 1H), 6.96 (d, J = 7.9 Hz, 1H), 4.24 (vbrs, 2H), 3.88-3.70 (m, 1H), 3.16 (t, J = 13.1 Hz, 1H), |

TABLE 5-continued

Analytical data for compounds of Formula II

| II- | LCMS_Plus | LCMS_RT | NMR |
|---|---|---|---|
| | | | 3.12-3.02 (m, 4H), 2.97 (d, J = 12.1 Hz, 1H), 2.36-2.28 (m, 4H), 2.07 (dt, J = 10.5, 3.6 Hz, 1H), 1.27 (d, J = 6.8 Hz, 3H). |
| II-475 | 502.1 | 2.54 | |
| II-476 | 502.1 | 2.54 | |
| II-477 | 389 | 1.72 | 1H NMR (500 MHz, Methanol-d4) δ 8.61 (d, J = 1.1 Hz, 1H), 8.56 (s, 1H), 8.29 (d, J = 9.4 Hz, 1H), 8.10 (d, J = 1.3 Hz, 1H), 7.60 (d, J = 9.4 Hz, 1H), 6.99 (t, J = 55.0 Hz, 1H), 5.37 (vbrs, 1H), 4.49 (vbrs, 2H), 4.13 (d, J = 4.5 Hz, 1H), 3.47 (ddd, J = 12.6, 3.1, 1.6 Hz, 1H), 3.39-3.31 (m, 1H), 3.19-3.16 (m, 1H), 1.25 (d, J = 7.0 Hz, 3H), solvent peak obscures some signals. |
| II-478 | 493.1 | 2.54 | 1H NMR (500 MHz, Methanol-d4) δ 8.62 (s, 1H), 8.55 (d, J = 1.0 Hz, 1H), 8.36 (d, J = 9.4 Hz, 1H), 8.06 (s, 1H), 7.68 (d, J = 9.5 Hz, 1H), 7.11 (t, J = 53.6 Hz, 1H), 4.68-4.26 (m, 2H), 3.92 (dd, J = 12.9, 4.7 Hz, 1H), 3.18 (d, J = 10.4 Hz, 1H), 3.10-3.04 (m, 1H), 3.02 (s, 3H), 2.71 (dt, J = 11.0, 4.1 Hz, 1H), 2.46-2.35 (m, 1H), 1.72-1.58 (m, 1H), 1.23 (d, J = 6.7 Hz, 3H), 0.72 (dd, J = 7.2, 4.7 Hz, 1H), 0.62-0.51 (m, 2H), 0.48-0.39 (m, 1H). |
| II-479 | 493.1 | 2.54 | 1H NMR (500 MHz, Methanol-d4) δ 8.62 (s, 1H), 8.55 (d, J = 1.0 Hz, 1H), 8.36 (d, J = 9.4 Hz, 1H), 8.06 (s, 1H), 7.68 (d, J = 9.5 Hz, 1H), 7.11 (t, J = 53.6 Hz, 1H), 4.68-4.26 (m, 2H), 3.92 (dd, J = 12.9, 4.7 Hz, 1H), 3.18 (d, J = 10.4 Hz, 1H), 3.10-3.04 (m, 1H), 3.02 (s, 3H), 2.71 (dt, J = 11.0, 4.1 Hz, 1H), 2.46-2.35 (m, 1H), 1.72-1.58 (m, 1H), 1.23 (d, J = 6.7 Hz, 3H), 0.72 (dd, J = 7.2, 4.7 Hz, 1H), 0.62-0.51 (m, 2H), 0.48-0.39 (m, 1H). |
| II-480 | 424.1 | 2.17 | 1H NMR (400 MHz, DMSO-d6) δ 8.62 (d, J = 1.7 Hz, 2H), 8.53 (d, J = 9.4 Hz, 1H), 8.03 (s, 1H), 7.70 (d, J = 9.4 Hz, 1H), 7.52-7.11 (m, 2H), 4.88 (s, 1H), 4.50-4.15 (m, 1H), 3.31-3.21 (m, 1H), 3.17-3.00 (m, 2H), 2.64 (d, J = 4.8 Hz, 3H), 2.15 (d, J = 12.8 Hz, 1H), 1.94-1.73 (m, 2H), 1.65-1.47 (m, 1H). |
| II-481 | 454.1 | 1.95 | 1H NMR (500 MHz, DMSO-d6) δ 8.58 (d, J = 9.7 Hz, 2H), 8.50 (d, J = 9.4 Hz, 1H), 7.88 (s, 1H), 7.66 (d, J = 9.5 Hz, 1H), 7.45-6.94 (m, 2H), 4.31 (s, 1H), 4.06-3.35 (m, 7H), 2.91 (s, 5H), 2.25 (q, J = 19.4, 17.4 Hz, 1H). |
| II-482 | 481.4 | 2.25 | |
| II-483 | 389 | 1.54 | 1H NMR (500 MHz, DMSO-d6) δ 8.62 (s, 1H), 8.58 (d, J = 1.1 Hz, 1H), 8.52 (d, J = 9.4 Hz, 1H), 8.00 (d, J = 1.2 Hz, 1H), 7.69 (d, J = 9.4 Hz, 1H), 7.45 (brs, 1H), 7.40 (t, J = 55.0 Hz, 1H), 6.85 (brs, 1H), 4.40 (vbrs, 1H), 4.28 (vbrs, 1H), 3.10-2.88 (m, 3H), 2.82-2.54 (m, 3H), 2.24 (d, J = 6.7 Hz, 2H). |
| II-484 | 482.3 | 2.49 | 1H NMR (500 MHz, DMSO-d6) δ 8.63 (s, 1H), 8.61 (s, 1H), 8.53 (d, J = 9.3 Hz, 1H), 8.02 (s, 1H), 7.69 (d, J = 9.4 Hz, 1H), 7.41-7.20 (m, 1H), 3.70-3.66 (m, 1H), 3.46-3.43 (m, 1H), 3.00-2.93 (m, 5H), 1.27 (s, 3H), 1.20-1.16 (m, 6H). One x CH2 not observed. |
| II-485 | 436.1 | 2.04 | 1H NMR (400 MHz, Methanol-d4) δ 8.50 (s, 1H), 8.43 (d, J = 1.1 Hz, 1H), 8.25 (d, J = 9.5 Hz, 1H), 8.01 (s, 1H), 7.57 (d, J = 9.4 Hz, 1H), 7.13 (t, J = 53.7 Hz, 1H), 4.75 (s, 2H), 3.32 (dd, J = 13.9, 9.1 Hz, 1H), 3.02 (s, 5H), 2.51 (s, 1H), 1.86-1.47 (m, 4H), 1.21 (d, J = 6.9 Hz, 3H). |
| II-486 | 436.1 | 2.04 | 1H NMR (400 MHz, Methanol-d4) δ 8.50 (s, 1H), 8.42 (d, J = 1.1 Hz, 1H), 8.25 (d, J = 9.4 Hz, 1H), 8.10-7.93 (m, 1H), 7.57 (d, J = 9.5 Hz, 1H), 7.13 (t, J = 53.6 Hz, 1H), 5.27-4.30 (m, 2H), 3.32 (dd, J = 13.9, 9.1 Hz, 1H), 3.02 (s, 6H), 2.51 (s, 1H), 1.90-1.44 (m, 4H), 1.21 (d, J = 6.8 Hz, 3H). |
| II-487 | 436.3 | 2.04 | 1H NMR (400 MHz, Methanol-d4) δ 8.51 (s, 1H), 8.44 (d, J = 1.1 Hz, 1H), 8.26 (d, J = 9.5 Hz, 1H), 8.06-7.95 (m, 1H), 7.57 (d, J = 9.5 Hz, 1H), 7.10 (t, J = 53.8 Hz, 1H), 5.22-4.17 (m, 2H), 3.15 (td, J = 14.8, 6.8 Hz, 2H), 3.00 (s, 4H), 2.40 (s, 1H), 1.89-1.49 (m, 4H), 1.20 (d, J = 6.7 Hz, 3H). |

TABLE 5-continued

Analytical data for compounds of Formula II

| II- | LCMS_Plus | LCMS_RT | NMR |
|---|---|---|---|
| II-488 | 436.3 | 2.04 | 1H NMR (400 MHz, Methanol-d4) δ 8.50 (s, 1H), 8.43 (d, J = 1.1 Hz, 1H), 8.25 (d, J = 9.5 Hz, 1H), 7.99 (d, J = 1.2 Hz, 1H), 7.57 (d, J = 9.5 Hz, 1H), 7.10 (t, J = 53.9 Hz, 1H), 5.01 (s, 1H), 4.72-4.29 (m, 1H), 3.19-3.10 (m, 2H), 3.00 (s, 4H), 2.39 (d, J = 10.6 Hz, 1H), 1.93-1.47 (m, 4H), 1.20 (d, J = 6.8 Hz, 3H). |
| II-489 | 482.3 | 2.42 | 1H NMR (500 MHz, DMSO-d6) δ 8.63-8.62 (m, 2H), 8.53 (d, J = 9.4 Hz, 1H), 8.01 (s, 1H), 7.69 (d, J = 9.4 Hz, 1H), 7.39-7.16 (m, 2H), 5.08 (br s, 1H), 4.53 (br s, 1H), 4.15 (br s, 1H), 3.95 (s, 1H), 3.58 (br s, 1H), 3.06-3.00 (m, 1H), 2.96 (s, 3H), 1.30 (s, 3H), 1.22 (s, 3H), 1.17-1.11 (m, 3H). |
| II-490 | 482.3 | 2.42 | 1H NMR (500 MHz, DMSO-d6) δ 8.55-8.54 (m, 2H), 8.46 (d, J = 9.4 Hz, 1H), 7.94 (s, 1H), 7.62 (d, J = 9.4 Hz, 1H), 7.32-7.11 (m, 2H), 4.98 (br s, 1H), 4.44 (br s, 1H), 4.08 (br s, 1H), 3.87 (s, 1H), 3.51 (br s, 1H), 2.99-2.93 (m, 1H), 2.89 (s, 3H), 1.22 (s, 3H), 1.14 (s, 3H), 1.078-1.02 (m, 3H). |
| II-491 | 482 | 2.62 | 1H NMR (500 MHz, DMSO-d6) δ 8.66 (m, 2 H), 8.54-8.51 (d, 1H), 8.01 (m, 1H), 7.70-7.67 (m, 1H), 7.39 (m, 1H), 7.37-7.16 (m. 1H), 5.10-4.70 (m, 2H), 4.08-4.05 (m, 1H), 3.53 (m, 1H), 3.05-2.95 (m, 4H), 2.80 (m, 1H), 1.37 (d, 3H), 1.12 (d, 3H). |
| II-492 | 403 | 1.71 | 1H NMR (500 MHz, DMSO-d6) δ 8.62 (s, 1H), 8.59 (d, J = 1.1 Hz, 1H), 8.53 (d, J = 9.4 Hz, 1H), 8.01 (d, J = 1.2 Hz, 1H), 7.70 (d, J = 9.4 Hz, 1H), 7.54-7.32 (m, 2H), 6.84 (s, 1H), 4.22 (brs, 1H), 4.21 (brs, 1H), 3.36 (ddd, J = 12.9, 10.0, 3.2 Hz, 1H), 3.18-2.97 (m, 1H), 2.82 (d, J = 11.9 Hz, 1H), 2.60-2.52 (m, 1H), 2.31-2.24 (m, 4H), 2.14-2.06 (m, 1H), water and solvent peaks obscure some signals. |
| II-493 | 437 | 2.26 | 1H NMR (500 MHz, DMSO-d6) δ 8.61 (s, 1H), 8.60-8.55 (m, 1H), 8.52 (d, J = 9.4 Hz, 1H), 8.00 (d, J = 1.2 Hz, 1H), 7.68 (d, J = 9.4 Hz, 1H), 7.34 (t, J = 55.0 Hz, 1H), 4.33 (br s, 2H), 3.29-3.15 (m, 2H), 3.11 (t, J = 12.8 Hz, 1H), 2.97 (s, 3H), 2.95-2.77 (m, 1H), 1.99-1.84 (m, 1H), 1.84-1.59 (m, 4H), 1.55-1.21 (m, 2H). |
| II-494 | 511.3 | 2.26 | 1H NMR (500 MHz, Methanol-d4) δ 8.76 (d, J = 1.0 Hz, 2H), 8.74 (s, 1H), 8.46 (d, J = 9.5 Hz, 1H), 8.11 (d, J = 1.1 Hz, 1H), 7.78 (d, J = 9.5 Hz, 1H), 7.16 (t, J = 53.8 Hz, 1H), 5.22 (s, 1H), 4.71 (d, J = 14.7 Hz, 1H), 3.82 (td, J = 4.7, 4.2, 2.0 Hz, 2H), 3.81-3.75 (m, 1H), 3.75 (d, J = 5.0 Hz, 1H), 3.66 (m, 2H), 3.50-3.35 (m, 6H), 3.09 (s, 3H), 2.68 (s, 3H), 1.48 (d, J = 7.1 Hz, 3H). |
| II-495 | 507.4 | 2.52 | 1H NMR (500 MHz, Methanol-d4) δ 8.62 (s, 1H), 8.54 (d, J = 1.1 Hz, 1H), 8.31 (d, J = 9.4 Hz, 1H), 8.04 (d, J = 1.2 Hz, 1H), 7.63 (d, J = 9.4 Hz, 1H), 7.06 (t, J = 53.7 Hz, 1H), 4.51-4.35 (m, 2H), 3.53 (dd, J = 13.0, 4.9 Hz, 1H), 3.30-3.22 (m, 2H), 3.02 (dd, J = 13.0, 9.7 Hz, 1H), 3.01 (s, 3H), 2.74-2.70 (m, 1H), 2.70-2.60 (m, 1H), 2.50 (td, J = 12.9, 12.4, 3.5 Hz, 1H), 2.35 (dd, J = 13.3, 6.4 Hz, 1H), 1.30 (d, J = 6.7 Hz, 3H), 0.92 (dddd, J = 12.9, 6.5, 4.1, 1.5 Hz, 1H), 0.63-0.49 (m, 2H), 0.24-0.10 (m, 2H). |
| II-496 | 376 | 1.64 | 1H NMR (500 MHz, DMSO-d6) δ 8.62 (s, 1H), 8.58 (d, J = 1.1 Hz, 1H), 8.52 (d, J = 9.4 Hz, 1H), 7.99 (d, J = 1.2 Hz, 1H), 7.68 (d, J = 9.4 Hz, 1H), 7.34 (t, J = 52.5 Hz, 1H), 4.55 (brs, 1H), 4.31 (vbrs, 2H), 3.58 (s, 2H), 3.09-2.87 (m, 2H), 2.81-2.61 (m, 3H), 2.40 (brs, 1H), 1.64-1.47 (m, 2H). |
| II-497 | 375.2 | 2.28 | 1H NMR (400 MHz, DMSO-d6) δ 8.60 (s, 1H), 8.56 (d, J = 1.1 Hz, 1H), 8.51 (d, J = 9.4 Hz, 1H), 7.99 (d, J = 1.2 Hz, 1H), 7.67 (d, J = 9.4 Hz, 1H), 7.33 (t, J = 53.9 Hz, 1H), 4.47 (t, J = 5.2 Hz, 1H), 4.34 (s, 2H), 3.52 (tq, J = 9.8, 4.6 Hz, 2H), 3.06 (td, J = 12.3, 11.5, 2.9 Hz, 1H), 2.82 (dd, J = 13.2, 10.3 Hz, 1H), 1.92-1.83 (m, 1H), 1.80-1.58 (m, 2H), 1.52-1.17 (m, 4H). |

TABLE 5-continued

Analytical data for compounds of Formula II

| II- | LCMS_Plus | LCMS_RT | NMR |
|---|---|---|---|
| II-498 | 377.2 | 1.94 | 1H NMR (400 MHz, DMSO-d6) δ 8.66-8.58 (m, 2H), 8.53 (d, J = 9.4 Hz, 1H), 8.00 (d, J = 1.2 Hz, 1H), 7.69 (d, J = 9.4 Hz, 1H), 7.34 (t, J = 53.7 Hz, 1H), 4.55 (t, J = 5.2 Hz, 1H), 4.29 (d, J = 40.6 Hz, 2H), 4.04-3.94 (m, 1H), 3.67-3.49 (m, 4H), 3.16-3.00 (m, 1H), 2.81 (t, J = 11.8 Hz, 1H), 1.68 (q, J = 6.4 Hz, 2H). |
| II-499 | 393.3 | 2.45 | 1H NMR (400 MHz, DMSO-d6) δ 8.68 (s, 1H), 8.62 (d, J = 9.5 Hz, 1H), 8.57 (d, J = 1.0 Hz, 1H), 7.96 (d, J = 1.2 Hz, 1H), 7.86 (d, J = 9.5 Hz, 1H), 4.42 (t, J = 5.1 Hz, 1H), 4.27 (s, 2H), 3.50 (td, J = 6.6, 5.1 Hz, 2H), 3.06 (t, J = 12.1 Hz, 1H), 2.83 (dd, J = 13.1, 10.4 Hz, 1H), 1.94-1.82 (m, 1H), 1.75 (dt, J = 13.2, 3.7 Hz, 1H), 1.65 (ddd, J = 10.6, 7.0, 3.8 Hz, 1H), 1.54-1.19 (m, 4H). |
| II-500 | 395 | 2.05 | 1H NMR (400 MHz, DMSO-d6) δ 8.70 (s, 1H), 8.66-8.58 (m, 2H), 7.95 (d, J = 1.2 Hz, 1H), 7.88 (d, J = 9.5 Hz, 1H), 4.52 (t, J = 5.2 Hz, 1H), 4.20 (s, 2H), 4.07-3.94 (m, 1H), 3.67-3.47 (m, 4H), 3.15-3.02 (m, 1H), 2.84 (dd, J = 13.0, 10.5 Hz, 1H), 1.75-1.50 (m, 2H). |
| II-501 | 388.3 | 2.61 | 1H NMR (400 MHz, DMSO-d6) δ 8.69 (s, 1H), 8.67-8.62 (m, 1H), 8.62 (t, J = 1.2 Hz, 1H), 7.99 (d, J = 1.3 Hz, 1H), 7.88 (d, J = 9.5 Hz, 1H), 4.50 (s, 1H), 4.16 (s, 1H), 3.20-3.04 (m, 1H), 3.01-2.84 (m, 1H), 2.59 (dd, J = 6.6, 2.0 Hz, 2H), 1.99-1.71 (m, 2H), 1.66-1.33 (m, 2H), 1.26 (q, J = 7.3, 6.7 Hz, 1H). |
| II-502 | 422 | 1.95 | 1H NMR (500 MHz, Methanol-d4) δ 8.47 (s, 1H), 8.38 (s, 1H), 8.23 (d, J = 9.4 Hz, 1H), 7.94 (s, 1H), 7.55 (d, J = 9.4 Hz, 1H), 7.06 (t, J = 53.5 Hz, 1H), 4.35 (d, J = 71.4 Hz, 2H), 3.28 (s, 1H), 3.05 (s, 6H), 2.99-2.80 (m, 2H), 1.95 (s, 1H), 1.77 (s, 1H), 1.52 (s, 2H). |
| II-503 | 422 | 1.95 | 1H NMR (500 MHz, Methanol-d4) δ 8.47 (s, 1H), 8.38 (s, 1H), 8.23 (d, J = 9.4 Hz, 1H), 7.94 (s, 1H), 7.55 (d, J = 9.4 Hz, 1H), 7.06 (t, J = 53.5 Hz, 1H), 4.35 (d, J = 71.4 Hz, 2H), 3.28 (s, 1H), 3.05 (s, 6H), 2.99-2.80 (m, 2H), 1.95 (s, 1H), 1.77 (s, 1H), 1.52 (s, 2H). |
| II-504 | 393.2 | 1.54 | 1H NMR (400 MHz, DMSO-d6) δ 8.77-8.62 (m, 3H), 8.14-8.00 (m, 1H), 7.92 (d, J = 9.5 Hz, 1H), 4.30 (d, J = 96.9 Hz, 2H), 3.53-3.28 (m, 2H), 2.62-2.54 (m, 1H), 2.15-1.91 (m, 1H), 1.89-1.66 (m, 2H), 1.56 (t, J = 12.6 Hz, 1H). |
| II-505 | 375 | 1.45 | 1H NMR (400 MHz, DMSO-d6) δ 8.77-8.66 (m, 2H), 8.57 (d, J = 9.4 Hz, 1H), 8.06 (s, 1H), 7.75 (d, J = 9.4 Hz, 1H), 7.30 (t, J = 53.8 Hz, 1H), 4.47 (s, 1H), 4.15 (s, 1H), 3.58-3.35 (m, 2H), 2.66-2.54 (m, 1H), 2.13-1.91 (m, 1H), 1.80 (dq, J = 13.7, 8.6, 7.5 Hz, 2H), 1.65-1.45 (m, 1H). |
| II-506 | 393.2 | 1.54 | 1H NMR (400 MHz, DMSO-d6) δ 8.79-8.61 (m, 3H), 8.05 (d, J = 1.1 Hz, 1H), 7.92 (d, J = 9.5 Hz, 1H), 4.35 (d, J = 139.8 Hz, 2H), 3.36 (dd, J = 26.7, 13.4 Hz, 2H), 2.61-2.53 (m, 1H), 2.04 (d, J = 13.1 Hz, 1H), 1.90-1.66 (m, 2H), 1.55 (s, 1H). |
| II-507 | 495.3 | 2.6 | 1H NMR (500 MHz, Methanol-d4) δ 8.73 (d, J = 1.0 Hz, 1H), 8.71 (s, 1H), 8.43 (d, J = 9.5 Hz, 1H), 8.15 (d, J = 1.1 Hz, 1H), 7.75 (d, J = 9.4 Hz, 1H), 7.15 (t, J = 53.8 Hz, 1H), 5.28 (s, 1H), 4.82-4.72 (m, 1H), 4.13 (p, J = 6.8 Hz, 1H), 3.86-3.77 (m, 2H), 3.74-3.67 (m, 1H), 3.56 (t, J = 13.7 Hz, 1H), 3.39 (dd, J = 11.6, 4.7 Hz, 1H), 3.26 (d, J = 12.9 Hz, 1H), 3.12 (s, 3H), 1.52 (d, J = 6.5 Hz, 3H), 1.47 (d, J = 7.0 Hz, 3H), 1.40 (d, J = 6.6 Hz, 3H). |
| II-508 | 375.2 | 1.41 | 1H NMR (400 MHz, DMSO-d6) δ 8.72-8.63 (m, 2H), 8.56 (d, J = 9.5 Hz, 1H), 8.06 (s, 1H), 7.74 (d, J = 9.5 Hz, 1H), 7.30 (t, J = 53.8 Hz, 1H), 4.46 (s, 1H), 4.13 (s, 1H), 3.58-3.28 (m, 2H), 2.63-2.53 (m, 1H), 2.02 (dd, J = 9.9, 5.8 Hz, 1H), 1.79 (q, J = 9.4, 8.7 Hz, 2H), 1.55 (d, J = 12.5 Hz, 1H). |
| II-509 | 454.1 | 2.13 | 1H NMR (500 MHz, DMSO-d6) δ 8.70-8.58 (m, 2H), 8.54 (d, J = 9.4 Hz, 1H), 7.98 (d, J = 1.3 Hz, 1H), 7.71 (d, J = 9.4 Hz, 1H), 7.45-7.17 (m, 2H), |

TABLE 5-continued

Analytical data for compounds of Formula II

| II- | LCMS_Plus | LCMS_RT | NMR |
|---|---|---|---|
| | | | 4.52 (s, 1H), 4.30 (s, 1H), 4.06 (dd, J = 11.6, 3.2 Hz, 1H), 3.58 (td, J = 11.6, 2.8 Hz, 1H), 3.41 (dt, J = 14.3, 7.1 Hz, 1H), 3.29 (s, 3H), 3.09 (t, J = 12.3 Hz, 1H), 2.87 (t, J = 11.8 Hz, 1H), 1.24 (d, J = 6.6 Hz, 3H). |
| II-510 | 454 | 2.13 | |
| II-511 | 466.3 | 2.56 | 1H NMR (500 MHz, DMSO-d6) δ 8.64 (t, J = 3.3 Hz, 2H), 8.46 (dd, J = 9.6, 3.5 Hz, 1H), 8.01 (d, J = 3.9 Hz, 1H), 7.64 (dd, J = 9.6, 3.1 Hz, 1H), 7.35-7.08 (t, 1H), 7.07-6.37 (bs, 2H), 4.95 (s, 1H), 4.32 (d, J = 12.5 Hz, 1H), 2.98 (dd, J = 17.5, 10.0 Hz, 2H), 2.94 (d, J = 3.4 Hz, 3H), 2.78-2.67 (m, 1H), 1.98 (dq, J = 13.3, 7.6, 6.0 Hz, 1H), 1.79-1.62 (m, 2H), 1.21 (d, J = 12.4 Hz, 1H), 1.15 (t, J = 6.4 Hz, 3H), 1.04 (d, J = 6.3 Hz, 3H). |
| II-512 | 372.2 | 2.2 | 1H NMR (400 MHz, DMSO-d6) δ 8.64 (s, 2H), 8.54 (d, J = 9.4 Hz, 1H), 8.00 (d, J = 1.2 Hz, 1H), 7.71 (d, J = 9.4 Hz, 1H), 7.56-7.16 (m, 1H), 4.48 (s, 1H), 4.20 (s, 1H), 4.12-3.95 (m, 1H), 3.92-3.77 (m, 1H), 3.67 (td, J = 11.7, 2.8 Hz, 1H), 3.14 (td, J = 12.3, 3.6 Hz, 1H), 2.99 (dd, J = 17.0, 4.5 Hz, 1H), 2.93-2.82 (m, 2H). |
| II-513 | 390.2 | 2.36 | 1H NMR (400 MHz, DMSO-d6) δ 8.76-8.58 (m, 3H), 7.96 (d, J = 1.2 Hz, 1H), 7.89 (d, J = 9.5 Hz, 1H), 4.49 (s, 1H), 4.08 (dt, J = 11.7, 5.9 Hz, 2H), 3.89-3.73 (m, 1H), 3.67 (td, J = 11.7, 2.8 Hz, 1H), 3.19 (td, J = 12.4, 11.7, 3.8 Hz, 1H), 3.01-2.79 (m, 3H). |
| II-514 | 390 | 1.89 | 1H NMR (500 MHz, DMSO-d6) δ 8.62 (s, 1H), 8.58 (d, J = 1.1 Hz, 1H), 8.52 (d, J = 9.4 Hz, 1H), 7.99 (d, J = 1.2 Hz, 1H), 7.68 (d, J = 9.4 Hz, 1H), 7.33 (t, J = 55.0 Hz, 1H), 4.55 (brs, 1H), 4.18 (vbrs, 2H), 3.57 (t, J = 6.5 Hz, 2H), 3.29-3.24 (m, 1H), 3.07 (dd, J = 13.1, 9.4 Hz, 1H), 2.85 (dt, J = 11.9, 3.4 Hz, 1H), 2.25-2.21 (m, 5H), 1.84 (dtd, J = 14.0, 6.9, 3.2 Hz, 1H), 1.50 (ddt, J = 14.3, 8.2, 6.2 Hz, 1H). |
| II-515 | 495.3 | 1.95 | 1H NMR (500 MHz, DMSO-d6) δ 8.63 (d, J = 1.7 Hz, 2H), 8.54 (d, J = 9.4 Hz, 1H), 7.90 (d, J = 1.2 Hz, 1H), 7.70 (d, J = 9.4 Hz, 1H), 7.31 (t, J = 53.7 Hz, 1H), 5.02-4.94 (m, 1H), 4.29 (q, J = 7.3 Hz, 1H), 4.18 (s, 1H), 3.90-3.69 (m, 2H), 3.48-3.33 (m, 3H), 2.97 (s, 3H), 2.10 (s, 3H), 1.33 (d, J = 6.9 Hz, 3H). |
| II-516 | 379.2 | 2.32 | 1H NMR (400 MHz, DMSO-d6) δ 8.69 (s, 1H), 8.63 (d, J = 9.5 Hz, 1H), 8.58 (d, J = 1.1 Hz, 1H), 7.98 (d, J = 1.2 Hz, 1H), 7.87 (d, J = 9.5 Hz, 1H), 4.59 (t, J = 5.1 Hz, 1H), 4.31 (s, 2H), 3.43-3.34 (m, 1H), 3.30 (d, J = 2.8 Hz, 1H), 3.08 (t, J = 11.5 Hz, 1H), 2.86 (t, J = 11.8 Hz, 1H), 1.86-1.70 (m, 2H), 1.70-1.54 (m, 1H), 1.56-1.21 (m, 2H). |
| II-517 | 379.2 | 2.32 | 1H NMR (400 MHz, DMSO-d6) δ 8.69 (s, 1H), 8.63 (d, J = 9.5 Hz, 1H), 8.59 (d, J = 1.0 Hz, 1H), 7.99 (d, J = 1.2 Hz, 1H), 7.87 (d, J = 9.5 Hz, 1H), 4.46 (d, J = 100.1 Hz, 3H), 3.44-3.36 (m, 2H), 3.16-3.02 (m, 1H), 2.86 (t, J = 11.8 Hz, 1H), 1.86-1.71 (m, 2H), 1.64 (s, 1H), 1.56-1.29 (m, 2H). |
| II-518 | 381.2 | 1.97 | 1H NMR (400 MHz, DMSO-d6) δ 8.71 (s, 1H), 8.67-8.59 (m, 2H), 7.97 (d, J = 1.2 Hz, 1H), 7.88 (d, J = 9.5 Hz, 1H), 4.87 (t, J = 5.5 Hz, 1H), 4.27 (d, J = 69.2 Hz, 2H), 4.01 (dd, J = 12.1, 3.3 Hz, 1H), 3.60-3.38 (m, 4H), 3.19-3.05 (m, 1H), 2.96-2.76 (m, 1H). |
| II-519 | 361.3 | 2.15 | 1H NMR (400 MHz, DMSO-d6) δ 8.61 (s, 1H), 8.56 (d, J = 1.1 Hz, 1H), 8.53 (d, J = 9.4 Hz, 1H), 8.04 (d, J = 1.2 Hz, 1H), 7.68 (d, J = 9.4 Hz, 1H), 7.28 (t, J = 53.8 Hz, 1H), 4.69 (t, J = 5.1 Hz, 1H), 4.39 (s, 2H), 3.40 (dt, J = 10.3, 5.0 Hz, 1H), 3.30-3.24 (m, 1H), 3.18-3.03 (m, 1H), 2.85 (t, J = 11.8 Hz, 1H), 1.83-1.54 (m, 3H), 1.53-1.18 (m, 2H). |
| II-520 | 361.3 | 2.14 | 1H NMR (400 MHz, DMSO-d6) δ 8.61 (s, 1H), 8.57 (d, J = 1.1 Hz, 1H), 8.53 (d, J = 9.4 Hz, 1H), 8.04 (d, J = 1.2 Hz, 1H), 7.68 (d, J = 9.4 Hz, 1H), 7.28 (t, J = 53.8 Hz, 1H), 4.69 (t, J = 5.1 Hz, 1H), |

TABLE 5-continued

Analytical data for compounds of Formula II

| II- | LCMS_Plus | LCMS_RT | NMR |
|---|---|---|---|
| | | | 4.54-4.17 (m, 2H), 3.40 (dt, J = 10.3, 5.1 Hz, 1H), 3.32-3.27 (m, 1H), 3.08 (td, J = 12.3, 11.4, 2.8 Hz, 1H), 2.85 (t, J = 11.8 Hz, 1H), 1.86-1.57 (m, 3H), 1.54-1.20 (m, 2H). |
| II-521 | 363.2 | 1.82 | 1H NMR (400 MHz, DMSO-d6) δ 8.65-8.57 (m, 2H), 8.53 (d, J = 9.4 Hz, 1H), 8.00 (d, J = 1.2 Hz, 1H), 7.69 (d, J = 9.4 Hz, 1H), 7.32 (t, J = 53.7 Hz, 1H), 4.88 (t, J = 5.5 Hz, 1H), 4.44 (s, 1H), 4.22 (s, 1H), 4.05-3.93 (m, 1H), 3.65-3.40 (m, 4H), 3.12 (td, J = 12.5, 3.6 Hz, 1H), 2.92-2.74 (m, 1H). |
| II-522 | 408.2 | 1.8 | 1H NMR (500 MHz, DMSO-d6) δ 8.63 (dd, J = 1.9, 0.9 Hz, 2H), 8.53 (d, J = 9.4 Hz, 1H), 8.08 (dd, J = 6.0, 1.2 Hz, 1H), 7.70 (d, J = 9.4 Hz, 1H), 7.34 (td, J = 53.7, 11.3 Hz, 1H), 4.87 (s, 1H), 4.47 (s, 1H), 3.31-3.15(m, 2H), 3.03 (t, J = 12.9 Hz, 1H), 2.97 (d, J = 1.7 Hz, 3H), 2.32-2.17 (m, 1H), 1.87 (dtt, J = 36.5, 12.4, 5.7 Hz, 2H), 1.54 (qd, J = 10.2, 7.7, 5.0 Hz, 1H). |
| II-523 | 470.4 | 2.03 | 1H NMR (500 MHz, Methanol-d4) δ 8.64 (s, 1H), 8.59 (d, J = 1.1 Hz, 1H), 8.38 (d, J = 9.5 Hz, 1H), 8.08 (s, 1H), 7.70 (d, J = 9.5 Hz, 1H), 7.13 (t, J = 53.7 Hz, 1H), 4.52 (br s, 1H), 3.56 (dd, J = 13.2, 5.1 Hz, 1H), 3.34-3.32 (m, 2H), 3.12-3.05 (m, 2H), 3.05 (s, 3H), 2.47 (d, J = 43.5 Hz, 2H), 1.32 (d, J = 6.7 Hz, 3H). |
| II-524 | 440.3 | 2.21 | 1H NMR (500 MHz, DMSO-d6) δ 8.62 (s, 1H), 8.58 (d, J = 1.1 Hz, 1H), 8.53 (d, J = 9.4 Hz, 1H), 8.00 (d, J = 1.2 Hz, 1H), 7.69 (d, J = 9.4 Hz, 1H), 7.31 (t, J = 53.7 Hz, 1H), 7.12 (s, 1H), 4.39 (br d, J = 65.8 Hz, 2H), 3.12-3.06 (m, 1H), 2.92 (s, 3H), 2.87-2.82 (m, 1H), 1.87-1.84 (m, 1H), 1.80-1.76 (m, 1H), 1.72-1.66 (m, 1H), 1.52-1.44 (m, 1H), 1.37-1.29 (m, 1H) |
| II-525 | 466.3 | 2.13 | 1H NMR (500 MHz, DMSO-d6) δ 8.72 (m, 2H), 8.56-8.54 (d, 1H), 8.02 (s, 1H), 7.73-7.71 (d, 1H), 7.30-7.20 (t, 1H), 7.18 (m, 1H), 4.30 (br s, 2H), 3.78 (m, 1H), 3.65 (m, 1H), 3.38 (m, 1H), 3.15 (m, 1H), 2.90 (m, 5H), 1.08 (d, 3H). |
| II-526 | 466.3 | 2.18 | 1H NMR (500 MHz, DMSO-d6) δ 8.74 (d, 1H), 8.70 (s, 1H), 8.57-8.55 (d, 1H), 8.17 (s, 1H), 7.74-7.72 (d, 1H), 7.42-7.20 (t, 1H), 7.10 (m, 1H), 4.80 (br s, 1H), 4.60 (br s, 1H), 3.40 (m, 1H), 3.30-3.05 (m, 2H), 3.05 (m, 1H), 2.99 (s, 3H), 2.82-2.72 (m, 2H), 1.02 (d, 3H). |
| II-527 | 510.3 | 2.39 | |
| II-528 | 500.3 | 2.59 | 1H NMR (500 MHz, DMSO-d6, 380K) δ 8.68-8.56 (m, 2H), 8.46 (dd, J = 9.5, 2.4 Hz, 1H), 8.03 (d, J = 2.0 Hz, 1H), 7.64 (dt, J = 9.5, 2.0 Hz, 1H), 7.23 (td, J = 53.9, 2.3 Hz, 1H), 6.95 (d, J = 9.3 Hz, 1H), 4.58 (d, J = 13.9 Hz, 1H), 3.94-3.86 (m, 1H), 3.70 (d, J = 14.2 Hz, 1H), 3.55-3.45 (m, 1H), 3.40 (dd, J = 13.7, 5.3 Hz, 1H), 3.11 (ddt, J = 20.9, 13.8, 6.3 Hz, 1H), 2.95 (t, J = 1.7 Hz, 3H), 2.41 (d, J = 36.9 Hz, 1H), 1.10-0.97 (m, 1H), 0.78 (q, J = 11.5, 10.7 Hz, 3H). |
| II-529 | 409 | 2.06 | 1H NMR (500 MHz, DMSO-d6) δ 8.67-8.62 (m, 2H), 8.54 (d, J = 9.4 Hz, 1H), 8.08 (s, 1H), 7.71 (d, J = 9.4 Hz, 1H), 7.32 (t, J = 53.7 Hz, 1H), 4.85 (s, 1H), 4.36 (s, 1H), 3.38 (d, J = 5.1 Hz, 1H), 3.29 (s, 1H), 3.20-3.10 (m, 1H), 3.05 (s, 3H), 2.23 (d, J = 11.8 Hz, 1H), 1.97-1.76 (m, 2H), 1.62-1.48 (m, 1H). |
| II-530 | 409 | 2.06 | 1H NMR (500 MHz, DMSO-d6) δ 8.67-8.61 (m, 2H), 8.54 (d, J = 9.4 Hz, 1H), 8.08 (s, 1H), 7.71 (d, J = 9.4 Hz, 1H), 7.32 (t, J = 53.7 Hz, 1H), 4.85 (s, 1H), 4.36 (s, 1H), 3.40-3.32 (m, 1H), 3.19-3.10 (m, 1H), 3.05 (s, 3H), 2.23 (d, J = 12.7 Hz, 1H), 1.97-1.81 (m, 2H), 1.56 (d, J = 15.5 Hz, 1H). |
| II-531 | 358 | 2.2 | 1H NMR (400 MHz, DMSO-d6) δ 8.69 (d, J = 1.1 Hz, 1H), 8.66 (s, 1H), 8.55 (d, J = 9.5 Hz, 1H), 8.06 (d, J = 1.2 Hz, 1H), 7.72 (d, J = 9.4 Hz, 1H), 7.37 (t, J = 53.6 Hz, 1H), 5.20 (t, J = 3.5 Hz, 1H), 4.42 (d, J = 14.0 Hz, 1H), 4.11 (d, J = 13.5 Hz, 1H), 3.98 (dt, J = 12.0, 3.5 Hz, 1H), 3.94- |

TABLE 5-continued

Analytical data for compounds of Formula II

| II- | LCMS_Plus | LCMS_RT | NMR |
|---|---|---|---|
| | | | 3.84 (m, 1H), 3.69 (dd, J = 13.9, 3.7 Hz, 1H), 3.46 (ddd, J = 13.4, 9.5, 3.7 Hz, 1H). |
| II-532 | 356 | 2.24 | 1H NMR (400 MHz, DMSO-d6) δ 8.63 (d, J = 1.7 Hz, 2H), 8.53 (d, J = 9.4 Hz, 1H), 8.05 (d, J = 1.2 Hz, 1H), 7.69 (d, J = 9.4 Hz, 1H), 7.37 (t, J = 53.8 Hz, 1H), 4.19 (dd, J = 13.5, 6.2 Hz, 1H), 3.87 (dd, J = 13.5, 3.5 Hz, 2H), 3.58 (ddd, J = 12.9, 8.0, 3.8 Hz, 1H), 3.18 (tt, J = 6.3, 3.7 Hz, 1H), 2.07-1.89 (m, 2H), 1.71 (ddddd, J = 16.4, 13.6, 10.4, 7.1, 3.8 Hz, 2H). |
| II-533 | 376.2 | 2.4 | 1H NMR (400 MHz, DMSO-d6) δ 8.74-8.70 (m, 2H), 8.65 (d, J = 9.5 Hz, 1H), 8.01 (d, J = 1.2 Hz, 1H), 7.90 (d, J = 9.5 Hz, 1H), 5.23 (t, J = 3.6 Hz, 1H), 4.34 (d, J = 13.7 Hz, 1H), 4.09-3.94 (m, 2H), 3.94-3.84 (m, 1H), 3.73 (dd, J = 13.9, 3.7 Hz, 1H), 3.49 (ddd, J = 13.8, 9.3, 3.8 Hz, 1H). |
| II-534 | 374.2 | 2.48 | 1H NMR (400 MHz, DMSO-d6) δ 8.71 (s, 1H), 8.69-8.55 (m, 2H), 8.04 (d, J = 1.2 Hz, 1H), 7.89 (d, J = 9.5 Hz, 1H), 4.13 (dd, J = 13.5, 6.6 Hz, 1H), 3.90 (dd, J = 13.4, 3.5 Hz, 1H), 3.79 (dd, J = 16.7, 3.6 Hz, 1H), 3.70-3.57 (m, 1H), 3.19 (tt, J = 7.0, 3.8 Hz, 1H), 2.00 (dqd, J = 20.5, 7.7, 6.7, 4.3 Hz, 2H), 1.72 (dddd, J = 23.9, 14.7, 9.5, 5.5 Hz, 2H). |
| II-535 | 466 | 1.81 | 1H NMR (500 MHz, DMSO-d6) δ 8.63 (d, J = 1.0 Hz, 2H), 8.53 (d, J = 9.4 Hz, 1H), 8.03 (d, J = 1.2 Hz, 1H), 7.70 (d, J = 9.4 Hz, 1H), 7.32 (t, J = 55.0 Hz, 1H), 7.03 (s, 2H), 4.03-3.84 (m, 4H), 3.66 (br s, 2H), 3.36 (d, J = 8.6 Hz, 2H), 2.57 (br t, J = 5.0 Hz, 2H), 2.42 (s, 3H). |
| II-536 | 404 | 1.89 | 1H NMR (500 MHz, DMSO-d6) δ 8.62 (s, 1H), 8.60 (d, J = 1.1 Hz, 1H), 8.52 (d, J = 9.4 Hz, 1H), 7.98 (s, 1H), 7.68 (d, J = 9.4 Hz, 1H), 7.31 (t, J = 55.0 Hz, 1H), 5.30-3.60 (v brs, 3H), 3.57 (br s, 2H), 3.19 (br s, 1H), 2.91 (d, J = 11.1 Hz, 1H), 2.21-2.13 (m, 5H), 1.92 (dq, J = 12.7, 6.6 Hz, 1H), 1.43 (ddd, J = 13.7, 9.3, 6.6 Hz, 1H), 1.15 (br s, 3H). |
| II-537 | 468.3 | 2.44 | 1H NMR (500 MHz, Methanol-d4) δ 8.64 (m, 2H), 8.39-8.37 (d, 1H), 8.00 (s, 1H), 7.73-7.71 (d, 1H), 7.09 (t, 1H), 4.45 (m, 1H), 4.32 (m, 1H), 4.05 (m, 2H), 3.82 (m, 2H), 2.90 (s, 3H), 2.72 (m, 1H), 1.12 (d, 3H). |
| II-538 | 468.3 | 2.47 | 1H NMR (500 MHz, Methanol-d4) δ 8.62 (s, 1H), 8.60 (d, 1H), 8.37-8.35 (d, 1H), 8.22 (s, 1H), 7.69-7.67 (d, 1H), 7.24-7.03 (t, 1H), 4.45 (m, 2H), 3.95 (m, 1H), 3.70 (m, 1H), 3.35 (masked, 1H), 3.06 (m, 1H), 2.93 (s, 3H), 2.78 (m, 1H), 1.79 (d, 3H). |
| II-539 | 373 | 1.92 | 1H NMR (500 MHz, DMSO-d6) δ 9.18 (d, J = 1.3 Hz, 1H), 8.75 (s, 1H), 8.56 (d, J = 9.4 Hz, 1H), 8.54 (d, J = 1.3 Hz, 1H), 7.74 (d, J = 9.4 Hz, 1H), 7.39 (t, J = 52.5 Hz, 1H), 4.54 (ddt, J = 13.1, 4.4, 2.2 Hz, 1H), 4.04-3.92 (m, 1H), 3.22 (ddd, J = 13.6, 12.4, 2.7 Hz, 1H), 3.09 (tt, J = 11.7, 3.7 Hz, 1H), 2.71 (td, J = 12.8, 2.8 Hz, 1H), 2.06 (s, 3H), 2.04-1.93 (m, 2H), 1.76 (qd, J = 12.4, 4.2 Hz, 1H), 1.61 (qd, J = 12.4, 4.3 Hz, 1H). |
| II-540 | 436 | 2.13 | |
| II-541 | 436 | 2.13 | 1H NMR (500 MHz, Methanol-d4) δ 8.59 (s, 1H), 8.50 (s, 1H), 8.35 (d, J = 9.4 Hz, 1H), 8.07 (s, 1H), 7.67 (d, J = 9.4 Hz, 1H), 7.17 (t, J = 53.8 Hz, 1H), 4.64-4.49 (br m, 1H), 3.41-3.31 (m, 2H), 3.18 (d, J = 7.3 Hz, 6H), 2.82-2.71 (m, 1H), 2.48 (t, J = 12.6 Hz, 1H), 2.09-2.05 (m, 1H), 1.82-1.72 (m, 1H), 1.29 (q, J = 12.0 Hz, 1H), 1.04 (d, J = 6.6 Hz, 3H). |
| II-542 | 481.1 | 2.21 | 1H NMR (500 MHz, DMSO-d6) δ 8.64 (s, 1H), 8.62 (d, J = 1.1 Hz, 1H), 8.53 (d, J = 9.4 Hz, 1H), 7.97 (d, J = 1.2 Hz, 1H), 7.70 (d, J = 9.5 Hz, 1H), 7.24 (d, J = 26.4 Hz, 2H), 3.39 (dd, J = 12.8, 4.3 Hz, 2H), 3.30 (d, J = 7.8 Hz, 1H), 3.16 (s, 2H), 2.99 (s, 3H), 2.97 (d, J = 12.1 Hz, 1H), 2.90-2.79 (m, 2H), 2.48 (d, J = 7.0 Hz, 1H), 2.35-2.26 (m, 1H), 1.18-1.12 (m, 3H), 1.00 (t, J = 7.0 Hz, 3H). |
| II-543 | 481.1 | 2.21 | 1H NMR (500 MHz, DMSO-d6) δ 8.64 (s, 1H), 8.62 (s, 1H), 8.53 (d, J = 9.4 Hz, 1H), 7.97 (s, |

TABLE 5-continued

Analytical data for compounds of Formula II

| II- | LCMS_Plus | LCMS_RT | NMR |
|---|---|---|---|
| | | | 1H), 7.70 (d, J = 9.4 Hz, 1H), 7.25 (d, J = 26.1 Hz, 2H), 3.39 (dd, J = 12.8, 4.8 Hz, 1H), 3.28 (d, J = 14.9 Hz, 1H), 3.14 (d, J = 18.7 Hz, 1H), 2.99 (s, 3H), 2.96 (s, 1H), 2.90-2.76 (m, 2H), 2.35-2.26 (m, 1H), 1.15 (d, J = 6.6 Hz, 3H), 1.00 (t, J = 7.0 Hz, 3H). |
| II-544 | 466.3 | 2.59 | 1H NMR (500 MHz, DMSO-d6) δ 8.73 (m, 2H), 8.58 (d, 1H), 8.15-7.98 (m, 1H), 7.76 (d, 1H), 7.43-7.15 (m, 2H), 5.30-5.00 (m, 1H), 4.30 (masked, 2H), 3.05-2.90 (m, 5H), 1.95 (m, 1H), 1.72 (m, 1H), 1.60 (m, 1H), 1.28 (m, 1H), 1.15 (m, 3H), 0.98 (m, 3H). |
| II-545 | 466.1 | 2.59 | 1H NMR (500 MHz, DMSO-d6) δ 8.61 (d, J = 12.2 Hz, 2H), 8.53 (d, J = 9.4 Hz, 1H), 8.05 (s, 1H), 7.68 (d, J = 9.4 Hz, 1H), 7.52-7.19 (m, 1H), 7.19-7.03 (m, 1H), 5.08 (d, J = 269.3 Hz, 1H), 4.51-3.70 (m, 1H), 2.92 (d, J = 23.7 Hz, 6H), 1.92 (s, 1H), 1.70-1.51 (m, 2H), 1.36-0.90 (m, 7H). |
| II-546 | 466.1 | 2.59 | 1H NMR (500 MHz, DMSO-d6) δ 8.61 (d, J = 12.6 Hz, 2H), 8.53 (d, J = 9.4 Hz, 1H), 8.05 (s, 1H), 7.68 (d, J = 9.5 Hz, 1H), 7.46-7.18 (m, 1H), 7.14 (s, 1H), 5.47-4.69 (m, 1H), 4.55-3.66 (m, 1H), 3.08-2.69 (m, 6H), 1.89 (s, 1H), 1.74-1.54 (m, 2H), 1.29-0.90 (m, 7H). |
| II-547 | 402 | 2.11 | 1H NMR (500 MHz, DMSO-d6) δ 8.66 (d, J = 1.1 Hz, 1H), 8.64 (s, 1H), 8.54 (d, J = 9.4 Hz, 1H), 8.02 (d, J = 1.2 Hz, 1H), 7.71 (d, J = 9.4 Hz, 1H), 7.36 (t, J = 52.5 Hz, 1H), 5.00 (vbrs, 1H), 4.44-4.31 (m, 1H), 4.22 (dd, J = 9.4, 5.1 Hz, 1H), 4.08 (dt, J = 9.0, 4.7 Hz, 1H), 3.84-3.65 (m, 1H), 3.30-3.21 (m, 2H), 3.16 (td, J = 12.3, 4.1 Hz, 1H), 1.20 (d, J = 6.8 Hz, 3H). |
| II-548 | 360.3 | 2.15 | 1H NMR (500 MHz, DMSO-d6) δ 8.61 (s, 1H), 8.57 (d, J = 1.1 Hz, 1H), 8.52 (d, J = 9.4 Hz, 1H), 7.96 (d, J = 1.2 Hz, 1H), 7.67 (d, J = 9.4 Hz, 1H), 7.33 (t, J = 53.8 Hz, 1H), 4.24-4.18 (m, 1H), 3.12-3.06 (m, 1H), 3.01-2.91 (m, 3H), 2.76 (dd, J = 13.1, 3.3 Hz, 1H), 1.28 (d, J = 6.7 Hz, 3H), 1.15 (d, J = 6.7 Hz, 3H). |
| II-549 | 512.1 | 2.07 | |
| II-550 | 512.1 | 2.1 | |
| II-551 | 438.1 | 2.22 | 1H NMR (400 MHz, DMSO-d6) δ 8.70-8.59 (m, 2H), 8.53 (d, J = 9.4 Hz, 1H), 8.03 (s, 1H), 7.70 (d, J = 9.5 Hz, 1H), 7.46-7.04 (m, 2H), 4.68 (d, J = 58.5 Hz, 2H), 3.32-3.23 (m, 1H), 3.02 (s, 3H), 2.85 (m, 1H), 1.93-1.59 (m, 4H), 1.20 (d, J = 6.8 Hz, 3H). |
| II-552 | 438 | 2.27 | 1H NMR (400 MHz, DMSO-d6) δ 8.62 (s, 1H), 8.58 (d, J = 1.0 Hz, 1H), 8.53 (d, J = 9.4 Hz, 1H), 8.03 (s, 1H), 7.69 (d, J = 9.4 Hz, 1H), 7.46-7.14 (m, 2H), 4.78 (s, 1H), 4.43 (d, J = 14.1 Hz, 1H), 3.73 (s, 1H), 3.45-3.35 (m, 1H), 2.97 (s, 3H), 2.19-1.93 (m, 2H), 1.63 (d, J = 12.1 Hz, 1H), 1.44 (s, 1H), 1.23-1.15 (m, 3H). |
| II-553 | 463.3 | 2.22 | 1H NMR (500 MHz, DMSO-d6) δ 8.71 (d, 1H), 8.67 (s, 1H), 8.56 (d, 1H), 8.04 (d, 1H), 7.74 (d, 1H), 7.29-7.19 (m, 2H), 4.70-4.30 (m, 1H), 4.10 (masked, 1H), 3.27 (m, 1H), 3.03 (m, 1H), 2.98 (m, 2H), 2.95 (s, 3H), 2.87 (m, 1H), 2.21 (m, 1H), 1.76 (m, 1H), 1.65 (m, 1H). |
| II-554 | 375.1 | 2.36 | 1H NMR (400 MHz, Methanol-d4) δ 8.58 (s, 1H), 8.52 (d, J = 1.1 Hz, 1H), 8.36 (d, J = 9.5 Hz, 1H), 8.10 (s, 1H), 7.67 (d, J = 9.4 Hz, 1H), 7.03 (t, J = 54.2 Hz, 1H), 4.80 (d, J = 5.8 Hz, 2H), 3.53 (qd, J = 10.9, 7.6 Hz, 2H), 3.10 (s, 1H), 2.08-1.94 (m, 1H), 1.94-1.83 (m, 1H), 1.72-1.41 (m, 3H), 1.22 (d, J = 6.9 Hz, 3H). |
| II-555 | 375.1 | 2.36 | 1H NMR (400 MHz,) δ 8.58 (s, 1H), 8.52 (d, J = 1.1 Hz, 1H), 8.36 (d, J = 9.5 Hz, 1H), 8.10 (s, 1H), 7.67 (d, J = 9.5 Hz, 1H), 7.03 (t, J = 54.2 Hz, 1H), 4.95 (br s, 2H), 3.53 (qd, J = 10.9, 7.6 Hz, 2H), 3.10 (s, 1H), 1.99 (s, 1H), 1.89 (d, J = 12.6 Hz, 1H), 1.74-1.41 (m, 3H), 1.22 (d, J = 6.9 Hz, 3H). Peak at 4.95 quite broadened. |

TABLE 5-continued

Analytical data for compounds of Formula II

| II- | LCMS_Plus | LCMS_RT | NMR |
|---|---|---|---|
| II-556 | 432 | 2.54 | 1H NMR (500 MHz, DMSO-d6) δ 8.85 (brs, 1H), 8.72 (d, J = 1.1 Hz, 1H), 8.67 (s, 1H), 8.57 (d, J = 9.4 Hz, 1H), 8.00 (d, J = 1.2 Hz, 1H), 7.73 (d, J = 9.4 Hz, 1H), 7.30 (t, J = 55.0 Hz, 1H), 4.88-4.86 (m, 1H), 4.30-4.22 (m, 1H), 3.89 (dt, J = 12.9, 6.3 Hz, 3H), 3.66-3.55 (m, 3H), 1.48-1.45 (m, 12H), water peak obscures some signals. |
| II-557 | 463.3 | 2.17 | |
| II-558 | 463.3 | 2.17 | |
| II-559 | 509 | 2.58 | 1H NMR (500 MHz, DMSO-d6) δ 8.62 (s, 1H), 8.60 (d, J = 1.1 Hz, 1H), 8.53 (d, J = 9.4 Hz, 1H), 7.85 (d, J = 1.2 Hz, 1H), 7.69 (d, J = 9.4 Hz, 1H), 7.30 (t, J = 52.5 Hz, 1H), 7.04 (dd, J = 7.5, 4.2 Hz, 1H), 5.10-5.06 (m, 1H), 3.90-3.86 (m, 1H), 3.43-3.37 (m, 1H), 3.26-2.99 (m, 5H), 2.96 (s, 3H), 1.30 (d, J = 7.0 Hz, 3H), 1.06 (s, 9H). |
| II-560 | 479.1 | 2.21 | 1H NMR (500 MHz, DMSO-d6) δ 8.63 (s, 1H), 8.61 (s, 1H), 8.53 (d, J = 9.4 Hz, 1H), 8.01 (s, 1H), 7.69 (d, J = 9.4 Hz, 1H), 7.28 (t, J = 53.5 Hz, 1H), 7.20 (s, 1H), 4.58 (m, 2H), 3.28 (m, 2H), 2.98-3.01 (m, 4H), 2.74 (dt, J = 25.4, 11.6 Hz, 2H), 2.28 (dd, J = 11.4, 6.5 Hz, 1H), 2.12-2.00 (m, 2H), 1.85-1.90 (m, 1H), 1.79-1.68 (m, 2H), 1.48-1.35 (m, 1H). |
| II-561 | 470.1 | 2.04 | 1H NMR (500 MHz, DMSO-d6) δ 8.63 (d, J = 5.9 Hz, 2H), 8.53 (d, J = 9.4 Hz, 1H), 7.97 (s, 1H), 7.70 (d, J = 9.4 Hz, 1H), 7.35 (d, J = 57.9 Hz, 1H), 7.20 (s, 1H), 3.46-3.34 (m, 1H), 2.99 (s, 3H), 2.87 (dt, J = 30.2, 11.3 Hz, 2H), 2.20 (d, J = 28.2 Hz, 2H), 1.34-1.04 (m, 3H). 3 CH missing/not observed. |
| II-562 | 470.1 | 2.04 | 1H NMR (500 MHz, DMSO-d6) δ 8.67-8.58 (m, 2H), 8.53 (d, J = 9.5 Hz, 1H), 7.97 (s, 1H), 7.70 (d, J = 9.4 Hz, 1H), 7.27 (m, 1H), 7.20 (t, J = 6.4 Hz, 1H), 3.44-3.33 (m, 1H), 2.99 (s, 3H), 2.95-2.76 (m, 2H), 2.28-2.08 (m, 2H), 1.23-1.13 (m, 3H). 3 CH not observed. |
| II-563 | 449.3 | 2.37 | 1H NMR (500 MHz, DMSO-d6) δ 8.73-8.65 (m, 2H), 8.57 (d, J = 9.4 Hz, 1H), 8.01 (d, J = 1.1 Hz, 1H), 7.74 (d, J = 9.4 Hz, 1H), 7.35 (t, J = 53.8 Hz, 1H), 4.43-4.15 (m, 2H), 3.30 (dd, J = 13.2, 9.5 Hz, 2H), 3.26-3.13 (m, 1H), 3.08-2.95 (m, 2H), 2.49-2.41 (m, 1H), 2.11 (tp, J = 8.7, 2.9 Hz, 2H), 2.05-1.89 (m, 2H), 1.89-1.75 (m, 2H), 1.65 (dtd, J = 13.3, 10.1, 3.7 Hz, 1H), 1.61-1.49 (m, 1H). |
| II-564 | 372.2 | 2.29 | |
| II-565 | 372 | 2.25 | |
| II-566 | 464.3 | 2.52 | 1H NMR (500 MHz, DMSO-d6) δ 8.62 (s, 1H), 8.57 (d, J = 1.1 Hz, 1H), 8.52 (d, J = 9.5 Hz, 1H), 8.07 (d, J = 1.3 Hz, 1H), 7.67 (d, J = 9.4 Hz, 1H), 7.29 (t, J = 53.9 Hz, 1H), 6.91 (t, J = 5.9 Hz, 1H), 4.55-4.20 (m, 2H), 3.40 (dd, J = 13.3, 3.3 Hz, 1H), 3.20 (t, J = 12.0 Hz, 1H), 3.02-2.90 (m, 2H), 2.82 (s, 3H), 1.93-1.74 (m, 1H), 1.40-1.21 (m, 1H), 0.99 (d, J = 13.6 Hz, 1H), 0.63-0.46 (m, 2H), 0.46-0.37 (m, 2H). |
| II-567 | 467 | 1.97 | 1H NMR (500 MHz, DMSO-d6) δ 8.62 (s, 1H), 8.57 (d, J = 1.1 Hz, 1H), 8.53 (d, J = 9.4 Hz, 1H), 8.02 (d, J = 1.2 Hz, 1H), 7.68 (d, J = 9.4 Hz, 1H), 7.30 (t, J = 53.8 Hz, 1H), 7.16 (t, J = 5.7 Hz, 1H), 3.29 (s, 1H), 2.97-3.00 (m, 3H), 2.95 (s, 6H), 2.76 (s, 1H), 2.55 (s, 1H), 2.12 (s, 1H), 1.14 (s, 3H), 1.04 (s, 3H). |
| II-568 | 497 | 2.11 | 1H NMR (500 MHz, DMSO-d6) δ 8.63 (s, 1H), 8.62 (d, J = 1.1 Hz, 1H), 8.53 (d, J = 9.4 Hz, 1H), 8.01 (d, J = 1.2 Hz, 1H), 7.70 (d, J = 9.4 Hz, 1H), 7.29 (t, J = 53.5 Hz, 1H), 7.25 (s, 1H), 5.36-5.16 (m, 1H), 4.62-4.58 (m, 2H), 3.48 (dd, J = 22.7, 11.3 Hz, 1H), 3.32-3.27 (m, 1H), 3.04-2.97 (m, 1H), 2.99 (s, 3H), 2.88-2.81 (m, 2H), 2.50-2.41 (m, 1H), 2.28 (dtd, J = 24.6, 11.4, 5.2 Hz, 2H), 2.17-2.09 (m, 1H), 1.61 (dddd, J = 36.9, 13.6, 10.7, 3.0 Hz, 1H). |
| II-569 | 467.1 | 1.97 | |
| II-570 | 467.1 | 1.96 | |

TABLE 5-continued

Analytical data for compounds of Formula II

| II- | LCMS_Plus | LCMS_RT | NMR |
|---|---|---|---|
| II-571 | 468 | 2.31 | 1H NMR (500 MHz, DMSO-d6) δ 8.69 (s, 2H), 8.56 (d, J = 9.5 Hz, 1H), 8.01 (NH), 7.74 (d, J = 9.4 Hz, 1H), 7.31 (t, J = 53.6 Hz, 1H), 7.17 (d, J = 8.3 Hz, 1H), 4.08 (dd, J = 11.2, 3.5 Hz, 2H), 3.6 (m, 2H not observed), 3.34 (t, J = 4.6 Hz, 2H), 3.11 (dd, J = 51.5, 12.4 Hz, 1H), 2.97 (s, 3H), 2.53 (m, 1H) not observed, 1.76-1.63 (m, 1H), 1.50 (ddd, J = 13.6, 8.5, 6.9 Hz, 1H), 0.96 (t, J = 7.3 Hz, 3H). |
| II-572 | 468.1 | 2.35 | 1H NMR (500 MHz, DMSO-d6) δ 8.70 (s, 2H), 8.56 (d, J = 9.4 Hz, 1H), 7.97 (s, NH), 7.74 (d, J = 9.4 Hz, 1H), 7.48-7.15 (m, 2H), 4.06 (dd, J = 11.7, 3.4 Hz, 3H), 3.66-3.52 (m, 1H), 3.49-3.29 (m, 2H), 3.16 (d, J = 12.7 Hz, 1H), 3.02 (s, 3H), 1.71 (dq, J = 11.4, 3.8 Hz, 1H), 1.49 (td, J = 19.1, 17.0, 9.6 Hz, 1H), 1.19 (d, J = 6.3 Hz, 1H), 0.96 (t, J = 7.3 Hz, 3H). |
| II-573 | 436 | 2.05 | 1H NMR (500 MHz, DMSO-d6) δ 8.61 (s, 1H), 8.57 (d, J = 1.1 Hz, 1H), 8.52 (d, J = 9.4 Hz, 1H), 7.99 (d, J = 1.2 Hz, 1H), 7.68 (d, J = 9.5 Hz, 1H), 7.32 (t, J = 53.8 Hz, 1H), 4.45 (s, 1H), 4.34 (s, 1H), 3.10-3.02 (m, 1H), 3.01-2.97 (m, 6H), 2.97-2.85 (m, 2H), 2.87-2.79 (m, 1H), 1.87 (dd, J = 12.8, 3.9 Hz, 1H), 1.81-1.73 (m, 1H), 1.66-1.60 (m, 1H), 1.46 (t, J = 12.6 Hz, 1H), 1.40-1.28 (m, 1H). |
| II-574 | 436 | 2.05 | 1H NMR (500 MHz, DMSO-d6) δ 8.61 (s, 1H), 8.57 (d, J = 1.1 Hz, 1H), 8.52 (d, J = 9.4 Hz, 1H), 7.99 (d, J = 1.2 Hz, 1H), 7.68 (d, J = 9.5 Hz, 1H), 7.32 (t, J = 53.8 Hz, 1H), 4.45 (s, 1H), 4.34 (s, 1H), 3.10-3.02 (m, 1H), 3.01-2.97 (m, 6H), 2.97-2.85 (m, 2H), 2.87-2.79 (m, 1H), 1.87 (dd, J = 12.8, 3.9 Hz, 1H), 1.81-1.73 (m, 1H), 1.66-1.60 (m, 1H), 1.46 (t, J = 12.6 Hz, 1H), 1.40-1.28 (m, 1H). |
| II-575 | 445.3 | 2.26 | 1H NMR (500 MHz, DMSO-d6) δ 9.35 (d, J = 1.4 Hz, 1H), 8.83 (s, 1H), 8.70 (d, J = 1.4 Hz, 1H), 8.58 (d, J = 9.4 Hz, 1H), 7.73 (d, J = 9.5 Hz, 1H), 7.55 (dd, J = 7.7, 1.4 Hz, 1H), 7.53-7.46 (m, 2H), 7.43-7.40 (m, 1H), 7.39-7.18 (m, 1H), 4.29 (d, J = 6.1 Hz, 2H), 2.97 (s, 3H), 2.41 (s, 3H). |
| II-576 | 431.2 | 2.3 | 1H NMR (500 MHz, DMSO-d6) δ 9.34 (d, J = 1.3 Hz, 1H), 9.13 (d, J = 1.4 Hz, 1H), 8.82 (s, 1H), 8.59 (d, J = 9.4 Hz, 1H), 8.29 (q, J = 1.4, 1.0 Hz, 1H), 8.18 (dt, J = 7.3, 1.8 Hz, 1H), 7.78 (d, J = 9.4 Hz, 1H), 7.72 (t, J = 6.3 Hz, 1H), 7.66-7.56 (m, 2H), 7.43 (t, J = 53.6 Hz, 1H), 4.33 (d, J = 6.3 Hz, 2H), 2.95 (s, 3H). |
| II-577 | 389.1 | 2.49 | |
| II-578 | 436 | 2.02 | 1H NMR (500 MHz, DMSO-d6) δ 8.61 (s, 1H), 8.57 (s, 1H), 8.52 (d, J = 9.4 Hz, 1H), 8.00 (s, 1H), 7.68 (d, J = 9.5 Hz, 1H), 7.28 (1H, hidden), 3.40 (2H hidden), 3.06 (d, J = 3.7 Hz, 6H), 2.55 (2H, hidden), 1.78-1.52 (m, 4H), 1.17 (d, J = 18.7 Hz, 3H). |
| II-579 | 436 | 2.08 | 1H NMR (500 MHz, DMSO-d6) δ 8.59 (s, 1H), 8.53 (d, J = 1.1 Hz, 1H), 8.51 (d, J = 9.4 Hz, 1H), 7.97 (d, J = 1.2 Hz, 1H), 7.66 (d, J = 9.4 Hz, 1H), 7.30 (t, J = 53.8 Hz, 1H), 4.42 (s, 2H), 3.52 (d, J = 3.0 Hz, 2H), 2.98 (s, 6H), 2.08-1.87 (m, 2H), 1.52 (d, J = 10.0 Hz, 2H), 1.23 (d, J = 6.9 Hz, 3H). |
| II-580 | 401 | 1.89 | 1H NMR (500 MHz, DMSO-d6) δ 9.40 (d, J = 1.3 Hz, 1H), 9.22 (d, J = 1.4 Hz, 1H), 8.85 (s, 2H), 8.61 (d, J = 9.4 Hz, 1H), 8.55 (ddd, J = 7.9, 1.8, 1.0 Hz, 1H), 8.21 (ddd, J = 7.8, 1.9, 1.0 Hz, 1H), 7.91 (t, J = 7.8 Hz, 1H), 7.79 (d, J = 9.4 Hz, 1H), 7.42 (t, J = 53.7 Hz, 1H), 3.30 (s, 3H). |
| II-581 | 436 | 2.01 | 1H NMR (500 MHz, DMSO-d6) δ 8.59 (s, 1H), 8.53 (d, J = 1.1 Hz, 1H), 8.51 (d, J = 9.4 Hz, 1H), 7.97 (d, J = 1.1 Hz, 1H), 7.67 (d, J = 9.4 Hz, 1H), 7.30 (t, J = 53.8 Hz, 1H), 4.42 (s, 2H), 2.98 (s, 6H), 2.53 (d, J = 1.9 Hz, 2H, not observed), 2.07-1.83 (m, 2H), 1.52 (d, J = 10.2 Hz, 2H), 1.23 (d, J = 7.0 Hz, 3H). |

TABLE 5-continued

Analytical data for compounds of Formula II

| II- | LCMS_Plus | LCMS_RT | NMR |
|---|---|---|---|
| II-582 | 436 | 2.01 | 1H NMR (500 MHz, DMSO-d6) δ 8.59 (s, 1H), 8.57-8.46 (m, 2H), 7.97 (d, J = 1.2 Hz, 1H), 7.67 (d, J = 9.4 Hz, 1H), 7.30 (t, J = 53.8 Hz, 1H), 4.52-4.33 (m, 2H), 3.52 (d, J = 3.0 Hz, 2H), 2.98 (s, 6H), 2.08-1.87 (m, 2H), 1.52 (d, J = 10.1 Hz, 2H), 1.23 (d, J = 7.0 Hz, 3H). |
| II-583 | 450 | 2.04 | 1H NMR (500 MHz, Methanol-d4) δ 8.60 (s, 1H), 8.52 (d, J = 1.1 Hz, 1H), 8.37 (d, J = 9.4 Hz, 1H), 8.10 (d, J = 1.2 Hz, 1H), 7.68 (d, J = 9.4 Hz, 1H), 7.11 (t, J = 54.1 Hz, 1H), 4.81 (s, 1H), 4.51 (s, 1H), 3.21 (dd, J = 12.2, 8.5 Hz, 1H), 3.18-3.09 (m, 2H), 3.07-3.03 (m, 1H), 3.04-3.02 (m, 3H), 2.98 (d, J = 1.0 Hz, 7H), 2.09-1.97 (m, 1H), 1.93-1.85 (m, 1H), 1.84-1.71 (m, 2H), 1.72-1.63 (m, 1H), 1.39 (d, J = 6.9 Hz, 3H). |
| II-584 | 450.1 | 2.07 | 1H NMR (500 MHz, Methanol-d4) δ 8.57 (s, 1H), 8.52 (dd, J = 5.7, 1.5 Hz, 1H), 8.39-8.32 (m, 1H), 8.07-8.01 (m, 1H), 7.70-7.63 (m, 1H), 7.10 (dd, J = 55.0, 53.1 Hz, 1H), 4.73 (br s, 2H), 3.14 (s, 6H), 3.04 (d, J = 7.6 Hz, 3H), 2.01-1.87 (m, 2H), 1.77 (dd, J = 12.9, 3.8 Hz, 1H), 1.56 (dqd, J = 41.1, 12.9, 4.1 Hz, 2H), 1.21 (d, J = 7.0 Hz, 3H). |
| II-585 | 389.1 | 2.38 | 1H NMR (400 MHz, Methanol-d4) δ 8.61 (s, 1H), 8.54 (d, J = 1.1 Hz, 1H), 8.37 (d, J = 9.4 Hz, 1H), 8.12 (s, 1H), 7.69 (d, J = 9.4 Hz, 1H), 7.05 (t, J = 54.2 Hz, 1H), 5.70-5.34 (m, 1H), 4.59 (s, 1H), 3.90 (s, 1H), 3.50 (t, J = 9.7 Hz, 2H), 2.75 (d, J = 111.4 Hz, 1H), 2.00 (d, J = 33.9 Hz, 1H), 1.68 (s, 2H), 1.42-0.83 (m, 6H). |
| II-586 | 389.1 | 2.38 | 1H NMR (400 MHz, Methanol-d4) δ 8.46 (s, 1H), 8.39 (d, J = 1.1 Hz, 1H), 8.23 (d, J = 9.5 Hz, 1H), 8.00 (s, 1H), 7.55 (d, J = 9.5 Hz, 1H), 6.91 (t, J = 54.3 Hz, 1H), 5.33 (s, 1H), 4.44 (s, 1H), 3.74 (s, 1H), 3.38 (t, J = 9.6 Hz, 2H), 2.60 (d, J = 104.0 Hz, 1H), 1.88 (d, J = 30.9 Hz, 1H), 1.55 (s, 2H), 1.24-0.71 (m, 6H). |
| II-587 | 451 | 2.42 | |
| II-588 | 451 | 2.32 | 1H NMR (400 MHz, Methanol-d4) δ 8.64 (s, 1H), 8.55 (d, J = 1.1 Hz, 1H), 8.38 (d, J = 9.4 Hz, 1H), 8.16 (d, J = 1.1 Hz, 1H), 7.70 (d, J = 9.5 Hz, 1H), 7.23 (t, J = 53.7 Hz, 1H), 4.96 (s, 1H), 4.65-4.05 (m, 1H), 3.31-3.26 (m, 1H), 3.16 (dd, J = 14.1, 4.8 Hz, 1H), 3.08 (s, 3H), 2.83 (s, 1H), 2.22 (s, 1H), 2.13-1.88 (m, 1H), 1.61 (d, J = 11.3 Hz, 1H), 1.39-1.29 (m, 4H), 1.12 (d, J = 7.1 Hz, 3H). |
| II-589 | 460 | 2.09 | 1H NMR (400 MHz, DMSO-d6) δ 8.74-8.62 (m, 2H), 8.54 (d, J = 9.4 Hz, 1H), 8.10 (d, J = 1.2 Hz, 1H), 7.97 (d, J = 8.0 Hz, 1H), 7.71 (d, J = 9.4 Hz, 1H), 7.31 (t, J = 53.7 Hz, 1H), 4.39-4.02 (m, 2H), 3.88 (s, 1H), 3.59-3.39 (m, 2H), 3.02 (s, 3H), 2.43-1.97 (m, 2H). |
| II-590 | 358.1 | 1.79 | 1H NMR (500 MHz, Methanol-d4) δ 8.60 (d, J = 1.1 Hz, 1H), 8.54 (s, 1H), 8.22 (d, J = 9.5 Hz, 1H), 8.01 (d, J = 1.2 Hz, 1H), 7.51 (d, J = 9.5 Hz, 1H), 3.97-3.89 (m, 2H), 3.89-3.82 (m, 2H), 3.82-3.72 (m, 4H), 2.20 (s, 3H). |
| II-591 | 466 | 2.41 | |
| II-592 | 466 | 2.41 | |
| II-593 | 436 | 1.92 | 1H NMR (500 MHz, DMSO-d6) δ 8.61 (s, 1H), 8.57 (d, J = 1.1 Hz, 1H), 8.52 (d, J = 9.4 Hz, 1H), 8.00 (s, 1H), 7.68 (d, J = 9.4 Hz, 1H), 7.28 (t, J = 53.6 Hz, 1H), 3.43 (d, J = 5.3 Hz, 2H), 3.06 (d, J = 3.7 Hz, 6H), 1.82-1.59 (m, 4H), 1.55 (m, 2H), 1.19 (s, 3H). |
| II-594 | 436 | 1.91 | 1H NMR (500 MHz, DMSO-d6) δ 8.61 (s, 1H), 8.57 (d, J = 1.2 Hz, 1H), 8.52 (d, J = 9.4 Hz, 1H), 8.00 (s, 1H), 7.68 (d, J = 9.4 Hz, 1H), 7.28 (t, J = 53.5 Hz, 1H), 3.42 (m, 2H), 3.06 (d, J = 3.7 Hz, 6H), 2.51 (m, 2H) partially hidden, 1.75 (t, J = 9.9 Hz, 1H), 1.72-1.49 (m, 3H), 1.17 (d, J = 18.5 Hz, 3H). |
| II-595 | 429.2 | 2.1 | 1H NMR (500 MHz, DMSO-d6) δ 9.35 (d, J = 1.3 Hz, 1H), 9.12 (d, J = 1.3 Hz, 1H), 8.83 (s, 1H), 8.60 (d, J = 9.4 Hz, 1H), 8.32 (d, J = 1.9 Hz, 1H), 8.20 (dt, J = 7.0, 1.9 Hz, 1H), 7.78 (d, J = |

TABLE 5-continued

Analytical data for compounds of Formula II

| II- | LCMS_Plus | LCMS_RT | NMR |
|---|---|---|---|
| | | | 9.4 Hz, 1H), 7.69-7.61 (m, 2H), 7.44 (t, J = 53.7 Hz, 1H), 4.58 (s, 2H), 3.63 (s, 6H). |
| II-596 | 460 | 2.14 | 1H NMR (400 MHz, DMSO-d6) δ 8.69-8.62 (m, 2H), 8.54 (d, J = 9.4 Hz, 1H), 8.10 (d, J = 1.2 Hz, 1H), 7.97 (s, 1H), 7.71 (d, J = 9.5 Hz, 1H), 7.32 (t, J = 53.7 Hz, 1H), 4.25 (s, 2H), 3.88 (d, J = 19.1 Hz, 1H), 3.62-3.40 (m, 2H), 3.02 (s, 3H), 2.42-2.00 (m, 2H). |
| II-597 | 460 | 2.13 | 1H NMR (400 MHz, DMSO-d6) δ 8.76-8.61 (m, 2H), 8.54 (d, J = 9.4 Hz, 1H), 8.10 (d, J = 1.2 Hz, 1H), 7.97 (s, 1H), 7.71 (d, J = 9.5 Hz, 1H), 7.32 (t, J = 53.7 Hz, 1H), 4.25 (s, 2H), 3.88 (s, 1H), 3.48 (td, J = 15.6, 14.4, 9.9 Hz, 2H), 3.02 (s, 3H), 2.40-1.96 (m, 2H). |
| II-598 | 415.2 | 1.94 | 1H NMR (500 MHz, DMSO-d6) δ 9.34 (d, J = 1.3 Hz, 1H), 9.13 (d, J = 1.4 Hz, 1H), 8.83 (s, 1H), 8.60 (d, J = 9.4 Hz, 1H), 8.34 (d, J = 1.8 Hz, 1H), 8.23 (dt, J = 7.6, 1.6 Hz, 1H), 7.78 (d, J = 9.4 Hz, 1H), 7.73-7.61 (m, 2H), 7.43 (t, J = 53.5 Hz, 1H), 4.63-4.50 (m, 2H), 3.78-3.71 (m, 1H), 2.85 (d, J = 0.9 Hz, 3H). |
| II-599 | 415.2 | 2.17 | 1H NMR (500 MHz, DMSO-d6) δ 9.30 (d, J = 1.3 Hz, 1H), 9.08 (d, J = 1.3 Hz, 1H), 8.81 (s, 1H), 8.59 (d, J = 9.4 Hz, 1H), 7.90 (t, J = 2.0 Hz, 1H), 7.83-7.72 (m, 2H), 7.44 (t, J = 7.8 Hz, 1H), 7.38 (t, J = 53.6 Hz, 1H), 7.13 (ddd, J = 8.0, 2.3, 1.0 Hz, 1H), 3.30 (s, 6H). |
| II-600 | 438.2 | 2.26 | 1H NMR (400 MHz, Methanol-d4) δ 8.48 (s, 1H), 8.42 (d, J = 1.1 Hz, 1H), 8.25 (d, J = 9.4 Hz, 1H), 8.03 (d, J = 1.2 Hz, 1H), 7.56 (d, J = 9.5 Hz, 1H), 7.02 (t, J = 54.0 Hz, 1H), 4.92-4.70 (m, 1H), 4.49 (s, 1H), 3.59-3.50 (m, 1H), 3.01 (td, J = 13.5, 3.7 Hz, 1H), 2.90 (s, 3H), 2.07 (tt, J = 13.6, 4.5 Hz, 1H), 1.88-1.52 (m, 3H), 1.24 (d, J = 7.0 Hz, 3H). |
| II-601 | 438.2 | 2.26 | 1H NMR (400 MHz, Methanol-d4) δ 8.48 (s, 1H), 8.42 (d, J = 1.1 Hz, 1H), 8.25 (d, J = 9.4 Hz, 1H), 8.03 (d, J = 1.1 Hz, 1H), 7.56 (d, J = 9.5 Hz, 1H), 7.02 (t, J = 54.0 Hz, 1H), 4.78 (s, 1H), 4.49 (s, 1H), 3.56 (dd, J = 3.8, 2.3 Hz, 1H), 3.11-2.94 (m, 1H), 2.90 (s, 3H), 2.17-1.98 (m, 1H), 1.91-1.52 (m, 3H), 1.24 (d, J = 7.0 Hz, 3H). |
| II-602 | 438 | 2.14 | 1H NMR (400 MHz, Methanol-d4) δ 8.64 (s, 1H), 8.57 (d, J = 1.0 Hz, 1H), 8.39 (d, J = 9.5 Hz, 1H), 8.17 (d, J = 1.1 Hz, 1H), 7.71 (d, J = 9.5 Hz, 1H), 7.17 (t, J = 53.8 Hz, 1H), 4.96 (s, 1H), 4.63 (s, 1H), 3.58 (dt, J = 10.7, 5.2 Hz, 1H), 3.04 (s, 4H), 2.10-1.57 (m, 4H), 1.33 (d, J = 6.9 Hz, 3H). |
| II-603 | 438 | 2.13 | 1H NMR (400 MHz, Methanol-d4) δ 8.63 (s, 1H), 8.56 (d, J = 1.1 Hz, 1H), 8.38 (d, J = 9.5 Hz, 1H), 8.16 (d, J = 1.2 Hz, 1H), 7.70 (d, J = 9.5 Hz, 1H), 7.16 (t, J = 53.8 Hz, 1H), 4.96 (s, 1H), 4.63 (s, 1H), 3.57 (dt, J = 10.7, 5.3 Hz, 1H), 3.04 (s, 4H), 1.99-1.57 (m, 4H), 1.33 (d, J = 6.9 Hz, 3H). |
| II-604 | 450 | 2.16 | |
| II-605 | 450 | 2.18 | |
| II-606 | 450 | 2.16 | |
| II-607 | 450.1 | 2.17 | 1H NMR (500 MHz, Methanol-d4) δ 8.49 (s, 1H), 8.42 (s, 1H), 8.24 (d, J = 9.5 Hz, 1H), 8.01 (s, 1H), 7.56 (d, J = 9.4 Hz, 1H), 7.36-6.94 (m, 1H), 3.32 (s, 1H), 3.06-2.98 (m, 4H), 2.57 (s, 1H), 2.50-2.40 (m, 1H), 1.70-1.66 (m, 2H), 1.33 (q, J = 12.6 Hz, 1H), 1.21-1.17 (m, 5H), 0.96 (d, J = 6.3 Hz, 3H). |
| II-608 | 389 | 2.42 | 1H NMR (400 MHz, DMSO-d6) δ 8.60 (s, 1H), 8.54 (d, J = 1.0 Hz, 1H), 8.51 (d, J = 9.4 Hz, 1H), 7.98 (d, J = 1.3 Hz, 1H), 7.68 (d, J = 9.4 Hz, 1H), 7.24 (t, J = 53.8 Hz, 1H), 4.57 (s, 2H), 3.03-2.67 (m, 2H), 1.98-1.71 (m, 2H), 1.40 (h, J = 8.6 Hz, 3H), 1.14 (d, J = 6.9 Hz, 6H). |
| II-609 | 445.2 | 2.47 | |
| II-610 | 443.2 | 2.34 | 1H NMR (500 MHz, DMSO-d6) δ 9.33 (d, J = 1.3 Hz, 1H), 9.12 (d, J = 1.3 Hz, 1H), 8.82 (s, 1H), 8.60 (d, J = 9.4 Hz, 1H), 8.10 (d, J = 1.6 Hz, 1H), 8.00 (d, J = 2.1 Hz, 1H), 7.79 (s, 1H), 7.48 |

TABLE 5-continued

Analytical data for compounds of Formula II

| II- | LCMS_Plus | LCMS_RT | NMR |
|---|---|---|---|
| | | | (d, J = 2.0 Hz, 1H), 7.37 (t, J = 53.7 Hz, 1H), 4.54 (s, 2H), 3.65 (s, 6H), 2.48 (s, 3H). |
| II-611 | 457.2 | 2.48 | 1H NMR (500 MHz, DMSO-d6) δ 9.35 (d, J = 1.3 Hz, 1H), 9.16 (d, J = 1.4 Hz, 1H), 8.83 (s, 1H), 8.72 (dq, J = 1.7, 0.8 Hz, 1H), 8.59 (d, J = 9.4 Hz, 1H), 8.22 (dq, J = 1.8, 1.0 Hz, 1H), 8.03 (td, J = 1.6, 0.8 Hz, 1H), 7.77 (d, J = 9.4 Hz, 1H), 7.40 (t, J = 53.9 Hz, 1H), 3.52 (s, 6H), 2.52 (s, 3H). |
| II-612 | 445.2 | 2.53 | 1H NMR (500 MHz, DMSO-d6) δ 9.37 (d, J = 1.3 Hz, 1H), 9.17 (d, J = 1.3 Hz, 1H), 8.86 (s, 1H), 8.64 (d, J = 9.4 Hz, 1H), 8.12 (d, J = 1.8 Hz, 1H), 8.03 (q, J = 1.4 Hz, 1H), 7.82 (d, J = 9.4 Hz, 1H), 7.78-7.68 (m, 1H), 7.60-7.33 (m, 2H), 4.33 (d, J = 6.2 Hz, 2H), 3.00 (s, 3H), 2.52 (s, 3H). |
| II-613 | 389.1 | 2.42 | 1H NMR (400 MHz, DMSO-d6) δ 8.62 (s, 1H), 8.58-8.48 (m, 2H), 8.01 (d, J = 1.2 Hz, 1H), 7.69 (d, J = 9.4 Hz, 1H), 7.26 (t, J = 53.8 Hz, 1H), 4.58 (s, 2H), 4.43 (s, 1H), 2.82 (s, 2H), 1.89 (s, 1H), 1.79 (s, 1H), 1.51-1.28 (m, 3H), 1.14 (d, J = 6.7 Hz, 6H). |
| II-614 | 389 | 2.42 | 1H NMR (400 MHz, DMSO-d6) δ 8.62 (s, 1H), 8.58-8.41 (m, 2H), 8.02 (d, J = 1.2 Hz, 1H), 7.69 (d, J = 9.4 Hz, 1H), 7.26 (t, J = 53.8 Hz, 1H), 4.58 (s, 2H), 4.43 (s, 1H), 2.82 (s, 2H), 1.89 (s, 1H), 1.79 (s, 1H), 1.53-1.30 (m, 3H), 1.14 (d, J = 6.7 Hz, 6H). |
| II-615 | 377.2 | 1.95 | 1H NMR (400 MHz, DMSO-d6) δ 8.71-8.58 (m, 2H), 8.53 (d, J = 9.4 Hz, 1H), 7.99 (d, J = 1.2 Hz, 1H), 7.69 (d, J = 9.5 Hz, 1H), 7.30 (t, J = 53.8 Hz, 1H), 4.82 (dd, J = 6.1, 5.0 Hz, 1H), 4.04 (s, 1H), 3.96-3.73 (m, 3H), 3.63-3.37 (m, 4H), 1.17 (d, J = 6.3 Hz, 3H). |
| II-616 | 377.2 | 2.02 | 1H NMR (400 MHz, DMSO-d6) δ 8.69-8.56 (m, 2H), 8.53 (d, J = 9.4 Hz, 1H), 8.00 (d, J = 1.2 Hz, 1H), 7.69 (d, J = 9.4 Hz, 1H), 7.31 (t, J = 53.8 Hz, 1H), 4.71-4.09 (m, 2H), 3.72-3.40 (m, 4H), 2.72 (dt, J = 22.7, 12.0 Hz, 2H), 1.21 (d, J = 6.2 Hz, 3H). |
| II-617 | 496 | 2.21 | |
| II-618 | 496 | 2.21 | 1H NMR (500 MHz, DMSO-d6) δ 8.62 (m, 1H), 8.58 (m, 1H), 8.54-8.52 (m, 1H), 8.12-7.98 (m, 1H), 7.78 (m, 1H), 7.32-7.15 (m, 1H), 7.04 (m, 1H), 5.30-4.60 (m, 1H), 4.38 (s, 1H), 3.65-3.3 (masked, 2H), 3.21-3.12 (m, 1H), 2.99-2.85 (m, 4H), 1.85-1.65 (m, 1H), 1.54 (m, 1H), 1.37-1.17 (m, 3H), 1.17 (s, 3H), 0.97 (m, 3H). |
| II-619 | 452.3 | 2.33 | 1H NMR (500 MHz, DMSO-d6) δ 8.65-8.56 (m, 2H), 8.53 (d, J = 9.4 Hz, 1H), 8.00 (d, J = 1.3 Hz, 1H), 7.68 (d, J = 9.4 Hz, 1H), 7.31 (t, J = 53.8 Hz, 1H), 7.04 (d, J = 8.6 Hz, 1H), 4.61-4.18 (m, 1H), 3.41-3.25 (m, 2H), 3.11-2.96 (m, 1H), 2.98-2.87 (m, 4H), 1.97-1.88 (m, 1H), 1.88-1.77 (m, 1H), 1.50 (tq, J = 8.8, 5.7, 4.6 Hz, 1H), 1.41 (qd, J = 12.2, 11.5, 3.6 Hz, 2H), 1.23 (d, J = 6.7 Hz, 3H). |
| II-620 | 452.2 | 2.37 | 1H NMR (500 MHz, DMSO-d6) δ 8.63 (s, 1H), 8.58 (d, J = 1.1 Hz, 1H), 8.53 (d, J = 9.4 Hz, 1H), 7.96 (d, J = 1.2 Hz, 1H), 7.69 (d, J = 9.4 Hz, 1H), 7.31 (t, J = 53.6 Hz, 1H), 7.10 (s, 1H), 4.83-4.35 (m, 1H), 3.29-3.16 (m, 1H), 3.01-2.83 (m, 4H), 2.80-2.68 (m, 1H), 1.89-1.76 (m, 2H), 1.55-1.29 (m, 4H), 1.21 (d, J = 6.7 Hz, 3H). |
| II-621 | 417.1 | 2.7 | 1H NMR (400 MHz, DMSO-d6) δ 8.62 (s, 1H), 8.58-8.44 (m, 2H), 7.98 (d, J = 1.3 Hz, 1H), 7.68 (d, J = 9.4 Hz, 1H), 7.29 (t, J = 53.9 Hz, 1H), 4.54 (s, 2H), 2.84 (s, 2H), 2.04-1.69 (m, 3H), 1.66-1.26 (m, 3H), 1.05 (s, 3H), 0.88 (d, J = 6.7 Hz, 3H), 0.80 (d, J = 6.7 Hz, 3H). |
| II-622 | 417.1 | 2.87 | 1H NMR (400 MHz, DMSO-d6) δ 8.62 (s, 1H), 8.58-8.47 (m, 2H), 8.01 (d, J = 1.2 Hz, 1H), 7.70 (d, J = 9.4 Hz, 1H), 7.30 (t, J = 53.7 Hz, 1H), 4.59 (s, 2H), 2.86 (s, 2H), 1.96-1.69 (m, 3H), 1.59 (s, 1H), 1.45 (d, J = 10.2 Hz, 2H), 0.98 (s, 3H), 0.87 (dd, J = 6.7, 3.9 Hz, 6H). |

TABLE 5-continued

Analytical data for compounds of Formula II

| II- | LCMS_Plus | LCMS_RT | NMR |
|---|---|---|---|
| II-623 | 411 | 2.48 | 1H NMR (400 MHz, Methanol-d4) δ 8.59 (s, 1H), 8.55 (d, J = 1.1 Hz, 1H), 8.36 (d, J = 9.4 Hz, 1H), 8.16 (d, J = 1.3 Hz, 1H), 7.68 (d, J = 9.5 Hz, 1H), 7.07 (t, J = 54.0 Hz, 1H), 4.73 (d, J = 35.2 Hz, 2H), 4.07 (dd, J = 11.0, 3.7 Hz, 1H), 3.63 (dd, J = 11.0, 9.5 Hz, 1H), 3.40-3.25 (m, 1H), 3.12-2.97 (m, 1H), 2.89 (t, J = 12.8 Hz, 1H), 2.33-1.95 (m, 2H), 1.12 (d, J = 6.7 Hz, 3H). |
| II-624 | 411 | 2.47 | 1H NMR (400 MHz, Methanol-d4) δ 8.63-8.51 (m, 2H), 8.32 (d, J = 9.5 Hz, 1H), 8.08 (d, J = 1.0 Hz, 1H), 7.65 (d, J = 9.5 Hz, 1H), 6.99 (t, J = 54.0 Hz, 1H), 4.78-4.39 (m, 2H), 3.96 (dd, J = 11.0, 3.7 Hz, 1H), 3.53 (dd, J = 11.0, 9.4 Hz, 1H), 3.21 (p, J = 1.6 Hz, 1H), 3.04 (t, J = 13.0 Hz, 1H), 2.90 (t, J = 12.9 Hz, 1H), 2.26-1.94 (m, 2H), 1.03 (d, J = 6.7 Hz, 3H). |
| II-625 | 451 | 2.5 | |
| II-626 | 451 | 2.5 | |
| II-627 | 464.3 | 2.44 | 1H NMR (500 MHz, Chloroform-d) δ 8.72 (s, 1H), 8.61 (d, J = 1.1 Hz, 1H), 8.16 (d, J = 9.4 Hz, 1H), 7.98 (d, J = 1.2 Hz, 1H), 7.41 (d, J = 9.4 Hz, 1H), 7.18-6.93 (m, 1H), 4.69 (s, 1H), 4.34 (s, 1H), 3.23 (tt, J = 10.9, 4.5 Hz, 1H), 3.04 (ddddd, J = 21.6, 19.7, 12.5, 8.8, 6.2 Hz, 4H), 2.75 (dd, J = 13.2, 10.7 Hz, 1H), 2.36 (t, J = 12.3 Hz, 1H), 1.98 (ddq, J = 10.0, 3.8, 2.1, 1.6 Hz, 1H), 1.67 (qt, J = 10.4, 3.4 Hz, 1H), 1.36 (t, J = 7.5 Hz, 3H), 1.33-1.23 (m, 4H), 0.95 (d, J = 6.6 Hz, 3H). |
| II-628 | 402.3 | 1.96 | 1H NMR (500 MHz, DMSO-d6) δ 8.70 (d, J = 1.1 Hz, 1H), 8.66 (s, 1H), 8.53 (d, J = 9.4 Hz, 1H), 8.03 (s, 1H), 7.72 (d, J = 9.5 Hz, 1H), 7.32 (t, J = 53.9 Hz, 1H), 5.25-4.00 (m, 2H), 4.02-3.88 (m, 1H), 3.68-3.56 (m, 1H), 3.48-3.00 (m, 3H), 1.87-1.68 (m, 3H), 1.68-1.53 (m, 1H), 1.43 (q, J = 13.9, 12.8 Hz, 2H). |
| II-629 | 436.3 | 2.24 | 1H NMR (500 MHz, DMSO-d6) δ 8.60 (s, 1H), 8.54-8.49 (m, 2H), 8.05-7.98 (m, 1H), 7.67 (d, J = 9.4 Hz, 1H), 7.33 (t, J = 53.7 Hz, 1H), 4.58-4.26 (m, 1H), 4.04-3.85 (m, 1H), 3.52-3.33 (m, 2H), 3.28-3.11 (m, 1H), 2.92 (s, 6H), 1.88 (ddt, J = 10.1, 6.9, 3.6 Hz, 1H), 1.67-1.53 (m, 1H), 1.53-1.40 (m, 1H), 0.92 (d, J = 6.7 Hz, 3H). |
| II-630 | 450.1 | 2.25 | 1H NMR (500 MHz, Chloroform-d) δ 8.65 (s, 1H), 8.58 (s, 1H), 8.14 (d, J = 9.4 Hz, 1H), 7.97 (s, 1H), 7.39 (d, J = 9.4 Hz, 1H), 6.98 (d, J = 51.6 Hz, 1H), 4.74 (s, 1H), 4.32 (s, 1H), 3.48-3.39 (m, 1H), 3.03 (d, J = 1.0 Hz, 3H), 2.98 (d, J = 1.0 Hz, 3H), 2.45 (s, 1H), 1.75-1.65 (m, 1H), 1.46 (q, J = 12.5 Hz, 1H), 1.22 (d, J = 6.8 Hz, 3H), 1.14 (d, J = 6.1 Hz, 1H), 0.96 (d, J = 6.4 Hz, 3H). |
| II-631 | 450.1 | 2.25 | 1H NMR (500 MHz, Chloroform-d) δ 8.65 (s, 1H), 8.58 (s, 1H), 8.14 (d, J = 9.4 Hz, 1H), 7.97 (s, 1H), 7.39 (d, J = 9.4 Hz, 1H), 6.98 (d, J = 51.6 Hz, 1H), 4.74 (s, 1H), 4.32 (s, 1H), 3.48-3.39 (m, 1H), 3.03 (d, J = 1.0 Hz, 3H), 2.98 (d, J = 1.0 Hz, 3H), 2.45 (s, 1H), 1.75-1.65 (m, 1H), 1.46 (q, J = 12.5 Hz, 1H), 1.22 (d, J = 6.8 Hz, 3H), 1.14 (d, J = 6.1 Hz, 1H), 0.96 (d, J = 6.4 Hz, 3H). |
| II-632 | 436.1 | 2.22 | 1H NMR (500 MHz, Chloroform-d) δ 8.85-8.72 (m, 1H), 8.65 (d, J = 1.1 Hz, 1H), 8.23 (d, J = 9.4 Hz, 1H), 8.07 (s, 1H), 7.48 (d, J = 9.4 Hz, 1H), 7.07 (t, 1H), 4.44 (s, 1H), 4.13 (s, 1H), 3.54 (dt, J = 5.4, 3.0 Hz, 1H), 3.43 (dd, J = 13.2, 2.5 Hz, 1H), 3.27 (ddd, J = 13.6, 10.3, 3.4 Hz, 1H), 2.95 (s, 6H), 2.04-1.87 (m, 1H), 1.82-1.70 (m, 1H), 1.62-1.50 (m, 1H), 1.02 (d, J = 6.8 Hz, 3H). |
| II-633 | 436.1 | 2.22 | 1H NMR (500 MHz, Chloroform-d) δ 8.85-8.72 (m, 1H), 8.65 (d, J = 1.1 Hz, 1H), 8.23 (d, J = 9.4 Hz, 1H), 8.07 (s, 1H), 7.48 (d, J = 9.4 Hz, 1H), 7.07 (t, 1H), 4.44 (s, 1H), 4.13 (s, 1H), 3.54 (dt, J = 5.4, 3.0 Hz, 1H), 3.43 (dd, J = 13.2, 2.5 Hz, 1H), 3.27 (ddd, J = 13.6, 10.3, 3.4 Hz, 1H), 2.95 (s, 6H), 2.04-1.87 (m, 1H), 1.82-1.70 (m, 1H), 1.62-1.50 (m, 1H), 1.02 (d, J = 6.8 Hz, 3H). |
| II-634 | | | 1H NMR (500 MHz, DMSO-d6) δ 8.63 (d, J = 5.9 Hz, 1H), 8.57 (d, J = 1.0 Hz, 1H), 8.53 (dd, J = |

TABLE 5-continued

Analytical data for compounds of Formula II

| II- | LCMS_Plus | LCMS_RT | NMR |
|---|---|---|---|
| | | | 9.4, 4.3 Hz, 1H), 8.07-7.76 (m, 1H), 7.68 (dd, J = 9.4, 5.9 Hz, 1H), 7.30 (td, J = 53.8, 6.6 Hz, 1H), 3.31-3.23 (m, 3H, partially hidden), 3.02 (d, J = 12.4 Hz, 3H), 2.76-2.56 (m, 2H), 1.95 (dd, J = 28.1, 12.7 Hz, 1H), 1.65 (d, J = 3.7 Hz, 1H), 1.28-1.13 (m, 2H), 1.12-0.96 (m, 2H), 0.95 (dd, J = 6.6, 1.2 Hz, 3H), 0.93-0.80 (m, 2H). |
| II-635 | | | 1H NMR (500 MHz, DMSO-d6) δ 8.62 (d, J = 0.8 Hz, 1H), 8.57 (d, J = 1.1 Hz, 1H), 8.55-8.48 (m, 1H), 8.03 (dd, J = 5.0, 1.2 Hz, 1H), 7.68 (dd, J = 9.4, 1.1 Hz, 1H), 7.33 (td, J = 53.8, 4.4 Hz, 1H), 3.31 (s, 3H) not observed, 3.26-3.10 (m, 2H), 2.94 (d, J = 3.5 Hz, 3H), 2.52 (d, J = 1.8 Hz, 2H), 1.98-1.87 (m, 1H), 1.72-1.60 (m, 1H), 1.32-1.11 (m, 4H), 0.95 (d, J = 6.6 Hz, 3H). |
| II-636 | 422 | 1.9 | |
| II-637 | 422 | 1.9 | |
| II-638 | 422 | 1.91 | |
| II-639 | 422 | 1.91 | |
| II-640 | 450.1 | 2.27 | 1H NMR (500 MHz, DMSO-d6) δ 8.62 (s, 1H), 8.57 (d, J = 1.1 Hz, 1H), 8.53 (d, J = 9.4 Hz, 1H), 8.04 (d, J = 1.2 Hz, 1H), 7.69 (d, J = 9.4 Hz, 1H), 7.33 (t, J = 53.8 Hz, 1H), 3.27 (d, J = 13.3 Hz, 2H), 3.15 (d, J = 7.4 Hz, 2H), 2.94 (s, 3H), 2.51 (d, J = 1.9 Hz, 2H), 1.94 (d, J = 12.6 Hz, 2H), 1.70-1.61 (m, 2H), 1.27 (t, J = 7.4 Hz, 3H), 0.95 (d, J = 6.6 Hz, 3H). |
| II-641 | 450.1 | 2.26 | 1H NMR (500 MHz, DMSO-d6) δ 8.62 (s, 1H), 8.57 (d, J = 1.1 Hz, 1H), 8.52 (d, J = 9.3 Hz, 1H), 8.03 (d, J = 1.3 Hz, 1H), 7.68 (d, J = 9.4 Hz, 1H), 7.34 (t, J = 53.8 Hz, 1H), 3.17 (ddd, J = 32.8, 14.5, 7.1 Hz, 2H), 2.95 (s, 3H), 2.68 (s, 2H), 2.55-2.51 (m, 2H), 1.94 (d, J = 12.8 Hz, 2H), 1.67-1.63 (m, 2H), 1.27-1.13 (m, 3H), 0.95 (d, J = 6.6 Hz, 3H). |
| II-642 | 450.1 | 2.26 | 1H NMR (500 MHz, DMSO-d6) δ 8.62 (s, 1H), 8.57 (d, J = 1.1 Hz, 1H), 8.53 (d, J = 9.4 Hz, 1H), 8.03 (d, J = 1.2 Hz, 1H), 7.68 (d, J = 9.4 Hz, 1H), 7.34 (t, J = 53.8 Hz, 1H), 3.17 (ddd, J = 32.9, 14.4, 7.1 Hz, 2H), 2.95 (s, 3H), 2.70-2.66 (m, 2H), 2.51 (p, J = 1.8 Hz, 2H), 1.94 (d, J = 12.7 Hz, 2H), 1.67-1.63 (m, 2H), 1.26-1.13 (m, 3H), 0.95 (d, J = 6.6 Hz, 3H). |
| II-643 | 450.1 | 2.27 | 1H NMR (500 MHz, DMSO-d6) δ 8.62 (s, 1H), 8.57 (d, J = 1.1 Hz, 1H), 8.53 (d, J = 9.5 Hz, 1H), 8.04 (d, J = 1.3 Hz, 1H), 7.69 (d, J = 9.4 Hz, 1H), 7.33 (t, J = 53.7 Hz, 1H), 3.26 (s, 2H), 3.15 (q, J = 7.4 Hz, 2H), 2.94 (s, 3H), 2.51 (d, J = 1.9 Hz, 2H), 1.94 (d, J = 12.9 Hz, 2H), 1.66 (s, 2H), 1.27 (t, J = 7.4 Hz, 3H), 0.95 (d, J = 6.5 Hz, 3H). |
| II-644 | | | 1H NMR (500 MHz, DMSO-d6) δ 8.63 (s, 1H), 8.57 (d, J = 1.1 Hz, 1H), 8.53 (d, J = 9.4 Hz, 1H), 8.01 (s, 1H), 7.69 (d, J = 9.4 Hz, 1H), 7.29 (t, J = 53.7 Hz, 1H), 3.03 (s, 3H), 2.65 (s, 2H), 2.53 (d, J = 1.9 Hz, 1H), 1.98 (d, J = 12.7 Hz, 2H), 1.64 (s, 2H), 1.26-1.14 (m, 2H), 1.13-1.05 (m, 1H), 0.99 (dq, J = 7.9, 3.6 Hz, 1H), 0.95 (d, J = 6.6 Hz, 3H), 0.87 (dtd, J = 17.4, 10.2, 8.7, 5.6 Hz, 2H). |
| II-645 | | | 1H NMR (500 MHz, DMSO-d6) δ 8.62 (s, 1H), 8.57 (d, J = 1.1 Hz, 1H), 8.52 (d, J = 9.4 Hz, 1H), 8.03 (s, 1H), 7.68 (d, J = 9.4 Hz, 1H), 7.31 (t, J = 53.8 Hz, 1H), 3.29-3.20 (m, 2H), 3.01 (s, 3H), 2.50-2.42 (m, 3H), 1.92 (d, J = 12.6 Hz, 1H), 1.71-1.57 (m, 1H), 1.32-1.15 (m, 3H), 1.10-0.99 (m, 1H), 1.02-0.79 (m, 5H). |
| II-646 | | | 1H NMR (500 MHz, DMSO-d6) δ 8.62 (s, 1H), 8.57 (d, J = 1.1 Hz, 1H), 8.52 (d, J = 9.4 Hz, 1H), 8.03 (d, J = 1.2 Hz, 1H), 7.68 (d, J = 9.4 Hz, 1H), 7.31 (t, J = 53.8 Hz, 1H), 3.27 (dd, J = 7.0, 5.2 Hz, 3H), 3.01 (s, 3H), 2.73-2.62 (m, 2H), 1.92 (d, J = 12.8 Hz, 1H), 1.69-1.58 (m, 1H), 1.29-1.10 (m, 2H), 1.10-0.97 (m, 2H), 0.94 (dd, J = 8.2, 5.7 Hz, 5H). |
| II-647 | | | 1H NMR (500 MHz, DMSO-d6) δ 8.63 (s, 1H), 8.57 (d, J = 1.1 Hz, 1H), 8.53 (d, J = 9.4 Hz, 1H), 8.01 (s, 1H), 7.69 (d, J = 9.4 Hz, 1H), 7.29 (t, J = |

TABLE 5-continued

Analytical data for compounds of Formula II

| II- | LCMS_Plus | LCMS_RT | NMR |
|---|---|---|---|
| | | | 53.7 Hz, 1H), 3.31-3.25 (m, 3H), 3.03 (s, 3H), 2.64 (p, J = 1.9 Hz, 2H), 1.97 (d, J = 12.9 Hz, 1H), 1.73-1.56 (m, 1H), 1.30-1.13 (m, 2H), 1.08 (dd, J = 10.6, 5.1 Hz, 1H), 1.04-0.96 (m, 1H), 0.95 (d, J = 6.5 Hz, 3H), 0.87 (dddd, J = 21.0, 14.9, 9.3, 4.8 Hz, 2H). |
| II-648 | | | 1H NMR (500 MHz, DMSO-d6) δ 8.63 (s, 1H), 8.58 (d, J = 1.1 Hz, 1H), 8.53 (d, J = 9.4 Hz, 1H), 8.02 (d, J = 1.2 Hz, 1H), 7.68 (d, J = 9.5 Hz, 1H), 7.30 (t, J = 53.8 Hz, 1H), 3.27-3.20 (m, 2H), 3.05 (d, J = 6.6 Hz, 6H), 1.98 (d, J = 13.0 Hz, 2H), 1.50-1.41 (m, 2H), 1.38-1.31 (m, 1H), 1.29-1.23 (m, 1H), 1.19-1.09 (m, 2H), 0.95 (t, J = 7.5 Hz, 3H). |
| II-649 | 462.2 | 2.26 | 1H NMR (500 MHz, DMSO-d6) δ 8.62 (s, 1H), 8.58 (d, J = 1.1 Hz, 1H), 8.53 (d, J = 9.4 Hz, 1H), 8.03 (d, J = 1.2 Hz, 1H), 7.68 (d, J = 9.4 Hz, 1H), 7.32 (t, J = 53.9 Hz, 1H), 3.25-3.08 (m, 4H), 2.98 (ddt, J = 41.4, 13.1, 7.0 Hz, 4H), 2.19-2.00 (m, 4H), 1.97 (d, J = 13.0 Hz, 1H), 1.66 (m, 2H), 1.20 (dt, J = 23.8, 12.0 Hz, 1H), 0.95 (d, J = 6.6 Hz, 3H). |
| II-650 | 450.1 | 2.24 | 1H NMR (500 MHz, DMSO-d6) δ 8.63 (s, 1H), 8.58 (d, J = 1.1 Hz, 1H), 8.53 (d, J = 9.4 Hz, 1H), 8.02 (d, J = 1.1 Hz, 1H), 7.68 (d, J = 9.4 Hz, 1H), 7.30 (t, J = 53.8 Hz, 1H), 3.23 (d, J = 11.8 Hz, 2H), 3.13-3.01 (m, 6H), 2.68 (m, 2H), 1.98 (d, J = 12.7 Hz, 2H), 1.46 (d, J = 3.5 Hz, 1H), 1.31 (dtd, J = 37.8, 13.6, 6.7 Hz, 2H), 1.15 (q, J = 11.9 Hz, 1H), 0.95 (t, J = 7.4 Hz, 3H). |
| II-651 | 450.2 | 2.24 | 1H NMR (500 MHz, DMSO-d6) δ 8.63 (s, 1H), 8.58 (d, J = 1.1 Hz, 1H), 8.53 (d, J = 9.4 Hz, 1H), 8.02 (d, J = 1.2 Hz, 1H), 7.68 (d, J = 9.4 Hz, 1H), 7.30 (t, J = 53.8 Hz, 1H), 3.26 (m, 2H), 3.06 (d, J = 6.7 Hz, 6H), 2.53 (m, 2H), 1.99 (d, J = 12.8 Hz, 2H), 1.47 (t, J = 3.9 Hz, 1H), 1.45-1.21 (m, 2H), 1.16 (dd, J = 13.3, 10.4 Hz, 1H), 0.95 (t, J = 7.5 Hz, 3H). |
| II-652 | 426.4 | 2.01 | 1H NMR (500 MHz, DMSO-d6) δ 12.70 (s, 1H), 8.61 (d, J = 5.8 Hz, 2H), 8.52 (d, J = 9.4 Hz, 1H), 8.07 (s, 1H), 7.74-7.08 (m, 4H), 4.86 (d, J = 187.6 Hz, 1H), 4.30-3.61 (m, 2H), 2.77 (d, J = 101.3 Hz, 2H), 1.17 (d, J = 6.0 Hz, 3H), 0.98 (s, 3H). |
| II-653 | 426.4 | 2.01 | 1H NMR (500 MHz, DMSO-d6) δ 12.95-12.36 (m, 1H), 8.61 (d, J = 5.6 Hz, 2H), 8.52 (d, J = 9.4 Hz, 1H), 8.07 (s, 1H), 7.77-7.10 (m, 4H), 4.87 (d, J = 185.9 Hz, 1H), 4.26-3.60 (m, 2H), 2.96-2.57 (m, 2H), 1.17 (d, J = 5.8 Hz, 3H), 0.98 (d, J = 6.2 Hz, 3H). |
| II-654 | 490.1 | 2.35 | 1H NMR (500 MHz, Methanol-d4) δ 8.72 (s, 1H), 8.65 (d, J = 1.0 Hz, 1H), 8.32 (d, J = 9.4 Hz, 1H), 8.14 (s, 1H), 7.63 (d, J = 9.4 Hz, 1H), 7.04 (t, J = 53.7 Hz, 1H), 5.04 (s, 1H), 3.45-3.35 (m, 1H), 3.17 (s, 3H), 3.13 (s, 3H), 3.00-2.88 (m, 2H), 2.51 (dtt, J = 12.0, 8.2, 4.5 Hz, 1H), 2.32-2.21 (m, 1H), 1.71 (q, J = 12.4 Hz, 1H). |
| II-655 | 368.2 | 0.75* | — |
| II-656 | 368.2 | 0.75* | — |
| II-657 | 377.3 | | — |
| II-658 | 317.3 | | 1H NMR (400 MHz, DMSO-d6) δ 9.16 (d, J = 1.3 Hz, 1H), 8.75 (s, 1H), 8.61-8.51 (m, 3H), 7.81-7.70 (m, 1H), 7.37 (t, J = 53.8 Hz, 1H), 3.48-3.37 (m, 1H), 3.30-3.23 (m, 1H), 3.09-2.85 (m, 3H), 2.25-2.10 (m, 1H), 1.99 (dq, J = 12.6, 7.3 Hz, 1H) |
| II-659 | 331.0 | 0.64* | 1H NMR (400 MHz,) δ 9.18 (dd, J = 3.6, 1.3 Hz, 1H), 8.80 (d, J = 1.5 Hz, 1H), 8.69 (dd, J = 4.8, 1.3 Hz, 1H), 8.44 (d, J = 9.5 Hz, 1H), 7.76 (d, J = 9.5 Hz, 1H), 7.38-6.92 (m, 1H), 3.65 (dd, J = 12.5, 4.0 Hz, 1H), 3.59-3.48 (m, 1H), 3.48-3.36 (m, 2H), 3.29-3.02 (m, 1H), 2.41-1.69 (m, 4H) |
| II-660 | 372.1 | 0.62* | — |
| II-661 | 346.1 | 0.63* | 1H NMR (400 MHz, DMSO-d6) δ 8.61 (s, 1H), 8.57 (d, J = 1.1 Hz, 1H), 8.52 (d, J = 9.4 Hz, 1H), |

TABLE 5-continued

Analytical data for compounds of Formula II

| II- | LCMS_Plus | LCMS_RT | NMR |
|---|---|---|---|
| | | | 7.98 (d, J = 1.2 Hz, 1H), 7.68 (d, J = 9.5 Hz, 1H), 7.35 (t, J = 53.7 Hz, 1H), 4.27 (d, J = 51.8 Hz, 2H), 3.16-2.98 (m, 1H), 2.90-2.60 (m, 2H), 2.00-1.85 (m, 1H), 1.79 (dt, J = 12.8, 3.9 Hz, 1H), 1.60-1.24 (m, 2H). |
| II-662 | 388.3 | 0.60* | — |
| II-663 | 360.1 | 0.62* | — |
| II-664 | 374.1 | 0.58* | — |
| II-665 | 358.1 | 0.59* | — |
| II-666 | 374.1 | 0.66* | — |
| II-667 | 374.1 | 0.59* | — |
| II-668 | 372.1 | 0.63* | — |
| II-669 | 374.3 | 0.61* | — |
| II-670 | 372.1 | 0.65* | — |
| II-671 | 360.2 | 0.66* | — |
| II-672 | 362.1 | 0.58* | — |
| II-673 | 386.1 | 0.64* | — |
| II-674 | 372.1 | 0.67* | — |
| II-675 | 386.1 | 0.71* | — |
| II-676 | 380.2 | 1.63 | 1H NMR (500 MHz, Methanol-d4) δ 8.75 (d, J = 21.2 Hz, 2H), 8.45 (d, J = 9.4 Hz, 1H), 8.21 (s, 1H), 7.78 (dd, J = 10.9, 3.6 Hz, 1H), 7.16 (t, J = 54.0 Hz, 1H), 4.72 (dd, J = 12.4, 8.0 Hz, 2H), 4.30-4.10 (m, 2H), 3.60 (dd, J = 8.2, 3.9 Hz, 4H). |
| II-677 | 358.1 | 0.62* | — |
| II-678 | 360.3 | 0.65* | — |
| II-679 | 372.1 | 0.66* | — |
| II-680 | 374.2 | 0.63* | — |
| II-681 | 346.3 | 0.56* | — |
| II-682 | 382.0 | 0.65* | — |
| II-683 | 402.1 | 0.62* | — |
| II-684 | 411.3 | 0.74* | — |
| II-685 | 391.3 | 0.58* | — |
| II-686 | 390.1 | 0.59* | — |
| II-687 | 453.3 | 0.65* | — |
| II-688 | 362.3 | 0.52* | — |
| II-689 | 403.3 | 0.70* | — |
| II-690 | 435.1 | 0.64* | — |
| II-691 | 433.3 | 2.31 | 1H NMR (500 MHz, Chloroform-d) δ 8.35 (s, 1H), 8.24-8.13 (m, 2H), 8.03 (s, 1H), 7.46 (d, J = 9.4 Hz, 1H), 7.13 (dd, J = 6.1, 1.5 Hz, 1H), 6.89 (t, J = 54.1 Hz, 1H), 4.51 (s, 1H), 4.42 (d, J = 13.5 Hz, 1H), 3.35 (ddd, J = 10.9, 6.5, 4.6 Hz, 1H), 3.12 (s, 3H), 3.03 (d, J = 5.4 Hz, 1H), 3.00-2.99 (m, 3H), 2.91-2.80 (m, 1H), 2.61 (ddd, J = 12.6, 9.8, 6.8 Hz, 1H), 2.06-1.99 (m, 1H), 1.34-1.22 (m, 1H), 1.01 (d, J = 6.5 Hz, 3H). |
| II-692 | 413.2 | 2.03 | 1H NMR (500 MHz, DMSO-d6) δ 8.69 (s, 1H), 8.65-8.53 (m, 2H), 7.92 (d, J = 9.4 Hz, 1H), 7.80 (d, J = 1.2 Hz, 1H), 7.10 (t, J = 6.2 Hz, 1H), 4.13 (s, 1H), 3.19 (ddd, J = 13.8, 11.3, 3.0 Hz, 1H), 2.91 (d, J = 9.0 Hz, 7H), 1.96-1.84 (m, 1H), 1.85-1.76 (m, 1H), 1.70 (dd, J = 7.1, 3.5 Hz, 1H), 1.56-1.42 (m, 1H), 1.43-1.29 (m, 1H). |
| II-693 | 401.3 | 1.88 | 1H NMR (500 MHz, DMSO-d6) δ 8.83-8.53 (m, 3H), 8.03-7.82 (m, 2H), 7.73-7.49 (m, 2H), 5.26-4.55 (m, 1H), 4.13 (m, 1H), 3.03-2.75 (m, 1H), 1.24 (s, 1H), 1.17 (d, J = 6.0 Hz, 3H), 0.93 (m, 4H). |
| II-694 | 490.1 | 2.34 | 1H NMR (500 MHz, Methanol-d4) δ 8.65 (s, 1H), 8.61 (d, J = 1.3 Hz, 1H), 8.38 (d, J = 9.4 Hz, 1H), 8.19 (d, J = 1.1 Hz, 1H), 7.70 (d, J = 9.5 Hz, 1H), 7.17 (t, J = 53.8 Hz, 1H), 5.08 (s, 1H), 4.50 (s, 1H), 3.53-3.43 (m, 1H), 3.22-3.16 (m, 6H), 2.97-2.86 (m, 2H), 2.63 (dtd, J = 12.1, 8.2, 4.0 Hz, 1H), 2.27 (d, J = 12.7 Hz, 1H), 1.67 (td, J = 12.6, 11.1 Hz, 1H). |
| II-695 | 490.1 | 2.34 | 1H NMR (500 MHz, Methanol-d4) δ 8.65 (s, 1H), 8.61 (d, J = 1.1 Hz, 1H), 8.38 (d, J = 9.4 Hz, 1H), 8.19 (d, J = 1.3 Hz, 1H), 7.70 (d, J = 9.4 Hz, 1H), 7.17 (t, J = 53.8 Hz, 1H), 5.08 (s, 1H), 4.50 (s, 1H), 3.53-3.43 (m, 1H), 3.19 (dd, J = 7.1, 0.8 Hz, 6H), 2.91 (q, J = 13.1 Hz, 2H), 2.63 (dtd, J = 11.9, 8.1, 3.8 Hz, 1H), 2.27 (d, J = 12.5 Hz, 1H), 1.67 (td, J = 12.6, 11.1 Hz, 1H). |

TABLE 5-continued

Analytical data for compounds of Formula II

| II- | LCMS_Plus | LCMS_RT | NMR |
|---|---|---|---|
| II-696 | 436.1 | 2.03 | 1H NMR (500 MHz, DMSO-d6) δ 8.62 (s, 1H), 8.58 (d, J = 1.1 Hz, 1H), 8.52 (d, J = 9.4 Hz, 1H), 8.00 (d, J = 1.3 Hz, 1H), 7.68 (d, J = 9.4 Hz, 1H), 7.30 (t, J = 53.7 Hz, 1H), 3.31 (m, 4H) partially hidden, 3.07 (s, 6H), 1.86-1.51 (m, 4H), 1.20 (s, 3H). |
| II-697 | 436.1 | 2.13 | 1H NMR (500 MHz, DMSO-d6) δ 8.60 (s, 1H), 8.53 (d, J = 1.1 Hz, 1H), 8.51 (d, J = 9.4 Hz, 1H), 8.00 (d, J = 1.2 Hz, 1H), 7.67 (d, J = 9.4 Hz, 1H), 7.32 (t, J = 53.8 Hz, 1H), 4.84 (s, 1H), 4.11 (d, J = 13.9 Hz, 1H), 3.73 (m, 1H), 3.29 (m, 1H), 3.05-2.91 (m, 8H), 2.28-2.15 (m, 1H), 2.04-1.86 (m, 1H), 1.49 (d, J = 13.0 Hz, 1H), 1.42-1.33 (m, 1H), 1.20 (d, J = 6.8 Hz, 3H). |
| II-698 | 444.4 | 2.15 | 1H NMR (500 MHz, DMSO-d6) δ 8.71 (s, 1H), 8.63 (d, J = 10.3 Hz, 2H), 8.06 (d, J = 1.2 Hz, 1H), 7.87 (d, J = 9.5 Hz, 1H), 7.54 (d, J = 26.5 Hz, 2H), 4.10 (s, 1H), 2.89 (d, J = 19.9 Hz, 1H), 2.67-2.55 (m, 2H), 1.16 (d, J = 5.9 Hz, 3H), 0.99 (s, 3H). |
| II-699 | 375.3 | 1.89 | 1H NMR (500 MHz, DMSO-d6) δ 8.71 (s, 1H), 8.65 (d, J = 1.1 Hz, 1H), 8.59 (d, J = 9.4 Hz, 1H), 7.93 (d, J = 9.4 Hz, 1H), 7.83 (d, J = 1.2 Hz, 1H), 4.50 (dt, J = 13.2, 3.1 Hz, 1H), 4.40 (d, J = 11.5 Hz, 2H), 3.52 (dtd, J = 12.3, 7.2, 5.3, 3.1 Hz, 1H), 3.15-3.05 (m, 1H), 2.97-2.87 (m, 1H), 2.82-2.72 (m, 1H), 2.29 (dd, J = 8.1, 4.8 Hz, 2H), 2.03 (dtd, J = 10.8, 5.2, 2.9 Hz, 1H), 1.90-1.77 (m, 1H), 1.68 (dddd, J = 15.9, 11.1, 8.1, 2.9 Hz, 1H), 1.55 (tdd, J = 12.4, 9.4, 3.2 Hz, 1H). |
| II-700 | 472.1 | 2.2 | 1H NMR (500 MHz, Methanol-d4) δ 8.64 (s, 1H), 8.59 (d, J = 1.1 Hz, 1H), 8.38 (d, J = 9.5 Hz, 1H), 8.19 (s, 1H), 7.69 (d, J = 9.5 Hz, 1H), 7.13 (t, J = 53.9 Hz, 1H), 6.80-6.45 (m, 1H), 3.74 (s, 1H), 3.24-3.19 (m, 6H), 2.04-1.86 (m, 4H), 1.80-1.65 (m, 2H), 1.33-1.29 (m, 1H). |
| II-701 | 472 | 2.2 | 1H NMR (500 MHz, Methanol-d4) δ 8.52 (s, 1H), 8.47 (d, J = 1.1 Hz, 1H), 8.26 (d, J = 9.5 Hz, 1H), 8.07 (s, 1H), 7.57 (d, J = 9.5 Hz, 1H), 7.01 (t, J = 53.8 Hz, 1H), 6.68-6.34 (m, 1H), 3.63 (s, 2H), 3.12-3.07 (m, 6H), 1.93-1.74 (m, 3H), 1.61 (d, J = 13.9 Hz, 2H), 1.22-1.17 (m, 1H). |
| II-702 | 411.4 | 1.94 | 1H NMR (500 MHz, DMSO-d6) δ 8.70 (s, 1H), 8.61-8.55 (m, 2H), 7.91 (d, J = 9.4 Hz, 1H), 7.85 (d, J = 1.2 Hz, 1H), 4.10 (q, J = 5.2 Hz, 1H), 3.24 (ddt, J = 15.3, 9.3, 6.0 Hz, 1H), 3.18 (d, J = 4.7 Hz, 2H), 3.06 (d, J = 1.0 Hz, 3H), 3.02 (m, J = 1.0 Hz, 4H), 2.00-1.91 (m, 1H), 1.73-1.62 (m, 1H), 1.25-1.13 (m, 1H), 0.96 (d, J = 6.6 Hz, 3H). |
| II-703 | 411.4 | 1.94 | 1H NMR (500 MHz, DMSO-d6) δ 8.70 (s, 1H), 8.61-8.55 (m, 2H), 7.91 (d, J = 9.4 Hz, 1H), 7.85 (d, J = 1.2 Hz, 1H), 4.10 (q, J = 5.2 Hz, 1H), 3.24 (ddt, J = 15.3, 9.3, 6.0 Hz, 1H), 3.18 (d, J = 4.7 Hz, 2H), 3.06 (d, J = 1.0 Hz, 3H), 3.02 (m, J = 1.0 Hz, 4H), 2.00-1.91 (m, 1H), 1.73-1.62 (m, 1H), 1.25-1.13 (m, 1H), 0.96 (d, J = 6.6 Hz, 3H). |
| II-704 | 444.4 | 2.17 | 1H NMR (500 MHz, Methanol-d4) δ 8.60 (s, 1H), 8.48 (d, J = 1.1 Hz, 1H), 8.35 (d, J = 9.5 Hz, 1H), 8.09 (d, J = 1.2 Hz, 1H), 7.68 (d, J = 9.5 Hz, 1H), 7.57 (s, 2H), 5.10 (s, 1H), 4.16 (s, 1H), 3.73 (s, 1H), 3.05-2.78 (m, 1H), 2.60 (s, 1H), 1.19 (d, J = 6.0 Hz, 3H), 1.00 (d, J = 6.9 Hz, 3H). |
| II-705 | 444.4 | 2.16 | 1H NMR (500 MHz, Methanol-d4) δ 8.58 (s, 1H), 8.47 (d, J = 6.5 Hz, 1H), 8.33 (d, J = 9.4 Hz, 1H), 8.05 (s, 1H), 7.66 (d, J = 9.5 Hz, 1H), 7.57 (s, 2H), 5.08 (s, 1H), 4.15 (s, 1H), 3.71 (d, J = 19.1 Hz, 1H), 2.90 (s, 1H), 2.57 (d, J = 14.1 Hz, 1H), 1.18 (d, J = 5.9 Hz, 3H), 1.07-0.89 (m, 3H). |
| II-706 | 430.4 | 1.97 | 1H NMR (500 MHz, DMSO-d6) δ 12.72 (s, 1H), 8.71 (s, 1H), 8.65-8.59 (m, 2H), 8.03 (s, 1H), 7.87 (d, J = 9.5 Hz, 1H), 7.61 (s, 1H), 7.46 (s, 1H), 4.03-3.96 (m, 1H), 3.17-3.09 (m, 1H), 2.88-2.75 (m, 1H), 2.73 (s, 1H), 2.64 (p, J = 1.9 Hz, 1H), 2.37 (p, J = 1.9 Hz, 1H), 0.99 (d, J = 6.7 Hz, 3H). |

TABLE 5-continued

Analytical data for compounds of Formula II

| II- | LCMS_Plus | LCMS_RT | NMR |
|---|---|---|---|
| II-707 | 430.4 | 2.05 | 1H NMR (500 MHz, DMSO-d6) δ 12.68 (s, 1H), 8.76-8.50 (m, 4H), 8.23 (s, 1H), 7.85 (m, 2H), 3.24-3.15 (m, 1H), 2.97 (s, 1H), 2.90-2.77 (m, 1H), 2.69-2.63 (m, 1H), 2.37 (p, J = 1.9 Hz, 1H), 1.24 (s, 1H), 1.04 (d, J = 6.1 Hz, 1H), 0.86 (d, J = 6.4 Hz, 3H). |
| II-708 | 416.1 | 2.36 | 1H NMR (400 MHz, DMSO-d6) δ 9.17 (s, 1H), 8.83 (s, 1H), 8.74 (s, 1H), 8.68 (d, J = 9.3 Hz, 1H), 8.52 (s, 1H), 8.10 (s, 1H), 7.94 (d, J = 9.4 Hz, 1H), 4.57 (d, J = 8.8 Hz, 1H), 4.00 (d, J = 11.3 Hz, 2H), 3.51 (t, J = 10.9 Hz, 2H), 2.16-1.88 (m, 4H). |
| II-709 | 398.1 | 2.2 | 1H NMR (400 MHz, DMSO-d6) δ 9.14 (d, J = 1.4 Hz, 1H), 8.82-8.71 (m, 2H), 8.66-8.53 (m, 2H), 8.30 (s, 1H), 7.76 (d, J = 9.5 Hz, 1H), 7.51 (t, J = 53.5 Hz, 1H), 4.56 (ddd, J = 15.7, 9.2, 7.1 Hz, 1H), 4.01 (dt, J = 11.5, 3.4 Hz, 2H), 3.51 (ddd, J = 11.6, 7.7, 5.3 Hz, 2H), 2.05 (h, J = 4.4 Hz, 4H). |
| II-710 | 421.4 | 1.97 | 1H NMR (500 MHz, Methanol-d4) δ 8.60 (s, 1H), 8.55 (d, J = 1.1 Hz, 1H), 8.37 (d, J = 9.4 Hz, 1H), 8.11 (d, J = 1.2 Hz, 1H), 7.68 (d, J = 9.4 Hz, 1H), 7.12 (t, J = 54.2 Hz, 1H), 4.67-4.49 (m, 1H), 3.92 (s, 1H), 3.66-3.53 (m, 2H), 2.40-2.25 (m, 2H), 2.19-2.04 (m, 1H), 1.90-1.78 (m, 1H), 1.65 (d, J = 12.8 Hz, 3H), 1.60 (d, J = 12.8 Hz, 3H), 1.07 (d, J = 7.0 Hz, 3H). |
| II-711 | 421.4 | 2.01 | 1H NMR (500 MHz, Methanol-d4) δ 8.59 (s, 1H), 8.55 (d, J = 1.1 Hz, 1H), 8.35 (d, J = 9.4 Hz, 1H), 8.09 (d, J = 1.2 Hz, 1H), 7.67 (d, J = 9.4 Hz, 1H), 7.12 (t, J = 54.2 Hz, 1H), 4.91 (d, J = 21.7 Hz, 1H), 4.48 (s, 1H), 3.04 (td, J = 12.5, 3.4 Hz, 1H), 2.78-2.57 (m, 1H), 2.21-2.08 (m, 2H), 1.77 (dtd, J = 11.2, 7.0, 3.3 Hz, 1H), 1.65 (d, J = 12.8 Hz, 3H), 1.61 (d, J = 12.9 Hz, 3H), 1.53-1.36 (m, 1H), 1.10 (d, J = 6.5 Hz, 3H). |
| II-712 | 439.1 | 2.05 | 1H NMR (500 MHz, Methanol-d4) δ 8.68 (d, J = 3.2 Hz, 1H), 8.56 (t, J = 2.1 Hz, 1H), 8.45 (ddd, J = 9.8, 1.6, 0.9 Hz, 1H), 8.12-8.04 (m, 1H), 7.78 (dd, J = 9.5, 0.8 Hz, 1H), 4.58 (s, 1H), 3.76 (s, 1H), 3.73-3.56 (m, 2H), 2.41-2.22 (m, 2H), 2.16 (dddd, J = 13.3, 9.9, 8.5, 4.5 Hz, 1H), 1.85 (tt, J = 12.5, 4.9 Hz, 1H), 1.68-1.62 (m, 3H), 1.60 (dd, J = 12.8, 0.7 Hz, 3H), 1.08 (d, J = 6.9 Hz, 3H). |
| II-713 | 439.1 | 2.09 | 1H NMR (500 MHz, Methanol-d4) δ 8.60-8.52 (m, 1H), 8.49-8.40 (m, 1H), 8.33 (dd, J = 9.7, 3.8 Hz, 1H), 8.05-7.91 (m, 1H), 7.67 (dd, J = 9.5, 2.3 Hz, 1H), 4.93 (d, J = 16.8 Hz, 1H), 4.18 (s, 1H), 2.88 (t, J = 12.4 Hz, 1H), 2.63 (t, J = 12.7 Hz, 1H), 2.00 (ddt, J = 26.1, 10.7, 4.0 Hz, 2H), 1.67 (ddt, J = 18.5, 11.4, 5.7 Hz, 1H), 1.53 (d, J = 12.8 Hz, 3H), 1.49 (d, J = 12.8 Hz, 3H), 1.44-1.26 (m, 1H), 0.99 (d, J = 6.6 Hz, 3H). |
| II-714 | 397.3 | 2.14 | 1H NMR (400 MHz, DMSO-d6) δ 11.89 (s, 1H), 8.61 (s, 1H), 8.59 (d, J = 1.0 Hz, 1H), 8.52 (d, J = 9.4 Hz, 1H), 8.10 (s, 1H), 7.69 (d, J = 9.4 Hz, 1H), 7.62-7.22 (m, 2H), 6.90 (s, 1H), 4.54 (d, J = 73.6 Hz, 2H), 3.08 (dt, J = 22.6, 12.4 Hz, 2H), 2.90-2.63 (m, 1H), 2.19-2.03 (m, 1H), 1.79 (ddd, J = 24.0, 12.8, 8.8 Hz, 2H), 1.69-1.47 (m, 1H). |
| II-715 | 415.3 | 2.29 | |
| II-716 | 433.3 | 2.31 | 1H NMR (500 MHz, Chloroform-d) δ 8.32 (s, 1H), 8.17 (dd, J = 9.4, 7.8 Hz, 2H), 7.98-7.91 (m, 1H), 7.45 (d, J = 9.4 Hz, 1H), 7.11 (dd, J = 6.2, 1.5 Hz, 1H), 6.87 (t, J = 54.0 Hz, 1H), 4.49 (d, J = 13.5 Hz, 1H), 4.40 (d, J = 13.4 Hz, 1H), 3.39-3.30 (m, 1H), 3.10 (s, 3H), 3.03-3.01 (m, 1H), 2.99 (d, J = 1.0 Hz, 3H), 2.86-2.77 (m, 1H), 2.60-2.52 (m, 1H), 2.01 (dt, J = 13.0, 4.1 Hz, 1H), 1.32-1.21 (m, 1H), 0.99 (d, J = 6.5 Hz, 3H). |
| II-717 | 420.2 | 2.32 | 1H NMR (500 MHz, Methanol-d4) δ 8.69 (s, 1H), 8.58 (s, 1H), 8.46 (d, J = 9.5 Hz, 1H), 8.19 (s, 1H), 7.79 (d, J = 9.5 Hz, 1H), 5.74 (s, 1H), 3.97-3.65 (m, 1H), 2.97-2.82 (m, 1H), 2.76 (d, J = 12.0 Hz, 1H), 1.90-1.78 (m, 1H), 1.72 (h, J = |

TABLE 5-continued

Analytical data for compounds of Formula II

| II- | LCMS_Plus | LCMS_RT | NMR |
|---|---|---|---|
| | | | 11.5, 10.5 Hz, 2H), 1.36-1.16 (m, 4H), 1.11 (d, J = 5.5 Hz, 3H). |
| II-718 | 420.2 | 2.32 | 1H NMR (500 MHz, Methanol-d4) δ 8.58 (s, 1H), 8.46 (s, 1H), 8.34 (d, J = 9.4 Hz, 1H), 8.07 (s, 1H), 7.67 (d, J = 9.5 Hz, 1H), 5.49 (s, 1H), 3.94-3.61 (m, 1H), 2.62 (dd, J = 16.7, 9.4 Hz, 1H), 1.75-1.66 (m, 1H), 1.60 (t, J = 9.4 Hz, 2H), 1.24-1.14 (m, 1H), 1.14-1.05 (m, 3H), 0.99 (d, J = 5.4 Hz, 3H). |
| II-719 | 420.1 | 2.26 | 1H NMR (400 MHz,) δ 5.10 (s, 1H), 3.99 (s, 1H), 3.30 (dd, J = 13.8, 3.2 Hz, 1H), 2.87 (dt, J = 13.1, 4.6 Hz, 1H), 2.24-2.08 (m, 2H), 1.52-1.39 (m, 1H), 1.15 (d, J = 6.9 Hz, 3H), 0.98 (d, J = 6.7 Hz, 3H). |
| II-720 | 420.2 | 2.33 | |
| II-721 | 421.2 | 1.79 | 1H NMR (400 MHz, Chloroform-d) δ 8.66 (s, 1H), 8.38 (d, J = 9.1 Hz, 1H), 7.55 (d, J = 9.2 Hz, 1H), 5.31 (s, 1H), 4.28 (d, J = 13.6 Hz, 1H), 2.88 (d, J = 12.8 Hz, 2H), 1.97 (t, J = 14.8 Hz, 1H), 1.81 (s, 1H), 1.61 (q, J = 12.8 Hz, 1H), 1.48 (dd, J = 12.5, 7.0 Hz, 1H), 1.37 (dd, J = 6.6, 3.7 Hz, 2H), 1.33 (d, J = 6.6 Hz, 3H), 1.28-1.14 (m, 1H), 1.03 (d, J = 6.2 Hz, 3H), 0.77 (d, J = 7.6 Hz, 1H). |
| II-722 | 453.3 | 2.54 | |
| II-723 | 453.3 | 2.54 | |
| II-724 | 435.1 | 2.12 | 1H NMR (500 MHz, DMSO-d6) δ 8.52 (s, 1H), 8.47 (d, J = 9.4 Hz, 1H), 8.27 (d, J = 5.9 Hz, 1H), 8.15 (d, J = 2.6 Hz, 1H), 7.60 (d, J = 9.4 Hz, 1H), 7.28 (t, J = 53.9 Hz, 1H), 6.79 (dd, J = 6.0, 2.6 Hz, 1H), 3.96 (dddd, J = 23.7, 14.7, 4.2, 2.0 Hz, 2H), 3.05 (d, J = 0.9 Hz, 3H), 3.03 (d, J = 0.9 Hz, 3H), 2.65 (dd, J = 12.9, 10.7 Hz, 1H), 2.49-2.45 (m, 1H), 2.02-1.89 (m, 1H), 1.78-1.66 (m, 1H), 1.21-1.09 (m, 1H), 0.95 (d, J = 6.5 Hz, 3H). |
| II-725 | 435.2 | 2.12 | 1H NMR (500 MHz, DMSO-d6) δ 8.52 (s, 1H), 8.47 (d, J = 9.4 Hz, 1H), 8.27 (d, J = 5.9 Hz, 1H), 8.15 (d, J = 2.6 Hz, 1H), 7.60 (d, J = 9.4 Hz, 1H), 7.28 (t, J = 53.9 Hz, 1H), 6.79 (dd, J = 6.0, 2.6 Hz, 1H), 3.96 (dd, J = 20.9, 13.7 Hz, 2H), 3.05 (s, 3H), 3.03 (s, 3H), 2.70-2.59 (m, 2H), 2.37 (p, J = 1.9 Hz, 1H), 1.93 (d, J = 12.7 Hz, 1H), 1.80-1.67 (m, 1H), 1.14 (q, J = 11.8 Hz, 1H), 0.95 (d, J = 6.6 Hz, 3H). |
| II-726 | 429.4 | 1.64 | 1H NMR (500 MHz, DMSO-d6) δ 8.63-8.54 (m, 2H), 8.41 (d, J = 9.4 Hz, 1H), 8.26 (s, 1H), 8.09 (s, 2H), 7.79 (d, J = 9.4 Hz, 1H), 3.21 (tt, J = 11.3, 4.7 Hz, 1H), 3.07-3.01 (m, 6H), 3.07-2.91 (m, 1H), 1.94 (d, J = 12.9 Hz, 1H), 1.69 (s, 1H), 1.16 (q, J = 12.0 Hz, 1H), 0.94 (d, J = 6.6 Hz, 3H). |
| II-727 | 393.3 | 1.6 | 1H NMR (500 MHz, DMSO-d6) δ 8.61 (d, J = 3.1 Hz, 2H), 8.42 (d, J = 9.4 Hz, 1H), 8.40 (s, 1H), 8.17 (d, J = 1.3 Hz, 1H), 8.07 (s, 1H), 7.81 (d, J = 9.4 Hz, 1H), 4.52 (s, 1H), 4.49 (dt, J = 13.5, 3.0 Hz, 1H), 3.52 (q, J = 8.4, 7.5 Hz, 1H), 3.03 (td, J = 12.8, 12.4, 3.4 Hz, 1H), 2.88 (t, J = 12.0 Hz, 1H), 2.76 (td, J = 12.9, 12.3, 3.2 Hz, 1H), 2.29 (dd, J = 8.1, 4.8 Hz, 2H), 2.05 (dq, J = 13.2, 4.1 Hz, 1H), 1.87-1.77 (m, 1H), 1.68 (ddd, J = 16.0, 7.6, 3.4 Hz, 1H), 1.61-1.44 (m, 1H). |
| II-728 | 419.4 | 1.6 | |
| II-729 | 455.1 | 2.6 | 1H NMR (500 MHz, DMSO-d6) δ 8.51 (d, J = 9.4 Hz, 1H), 8.37 (d, J = 2.7 Hz, 1H), 8.28 (d, J = 2.2 Hz, 1H), 7.77 (d, J = 4.7 Hz, 1H), 7.67 (d, J = 9.4 Hz, 1H), 7.21 (t, J = 53.8 Hz, 1H), 7.06 (t, J = 6.2 Hz, 1H), 4.32-4.24 (m, 1H), 4.13-4.05 (m, 1H), 3.00-2.84 (m, 6H), 2.67 (dd, J = 12.9, 10.3 Hz, 1H), 1.88-1.78 (m, 1H), 1.79-1.65 (m, 2H), 1.58-1.44 (m, 1H), 1.29-1.18 (m, 1H). |
| II-730 | 471.2 | 2.72 | 1H NMR (500 MHz, DMSO-d6) δ 8.47 (d, J = 9.4 Hz, 1H), 8.29 (s, 1H), 8.26 (s, 1H), 7.62 (d, J = 9.4 Hz, 1H), 7.29-7.01 (m, 3H), 4.36-4.27 (m, 1H), 4.18-4.09 (m, 1H), 2.97-2.85 (m, 6H), 2.71-2.62 (m, 1H), 1.87-1.79 (m, 1H), 1.75-1.60 (m, 2H), 1.51-1.40 (m, 1H), 1.28-1.19 (m, 1H). |

TABLE 5-continued

Analytical data for compounds of Formula II

| II- | LCMS_Plus | LCMS_RT | NMR |
|---|---|---|---|
| II-764 | 458.90 | 1.477 | 1H NMR (400 MHz, Chloroform-d) d 8.65 (d, J = 1.1 Hz, 1H), 8.47 (s, 1H), 8.19 (s, 1H), 7.86 (d, J = 9.6 Hz, 1H), 6.52 (d, J = 9.6 Hz, 1H), 5.53 (dddd, J = 56.7, 9.4, 6.1, 3.4 Hz, 1H), 4.64-4.27 (m, 4H), 3.43-3.29 (m, 1H), 3.11-3.04 (m, 6H), 2.76 (t, J = 11.7 Hz, 2H), 2.44 (t, J = 12.3 Hz, 2H), 2.08 (d, J = 12.9 Hz, 2H), 1.31 (q, J = 12.0 Hz, 1H), 1.03 (d, J = 6.6 Hz, 3H). Spectra |

Purity and retention time of the compounds from this invention were measured by HPLC. Several methods have been used and are reported below.

Retention times (RT) marked with * have been recorded with Method 1;

Retention times with no * have been recorded with Method 2;

Method 1: analytical reverse phase UPLC-MS was carried out on a waters Acquity UPLC-MS system equipped with a waters BEH 1.7 mm C-18 reverse phase column (2.1 mm×50 mm, 1.7 µm). The mobile phases were acetonitrile and water/acetonitrile (95:5 with 10 mM ammonium formate, pH 9). Run time 1.5 min.

Method 2: analytical reverse phase UPLC-MS was carried out on a waters Acquity UPLC-MS system equipped with a waters BEH 1.7 mm C-18 reverse phase column (2.1 mm×50 mm, 1.7 µm). The mobile phases were acetonitrile and water/acetonitrile (95:5 with 10 mM ammonium formate, pH 9). Run time 5 min.

TABLE 6

Analytical data for compounds of Formula III

| III- | LCMS_Plus | LCMS_RT | NMR |
|---|---|---|---|
| III-1 | 374.1 | 1.96 | 1H NMR (500 MHz, DMSO-d6) δ 9.54 (d, J = 7.2 Hz, 1H), 9.02 (s, 1H), 8.70 (s, 1H), 7.80 (d, J = 1.1 Hz, 1H), 7.55 (d, J = 7.2 Hz, 1H), 7.35-7.07 (m, 1H), 3.90-3.61 (m, 8H), 2.08 (s, 3H). |
| III-2 | 438.2 | 2.28 | 1H NMR (500 MHz, DMSO-d6) δ 9.56 (d, J = 7.2 Hz, 1H), 9.05 (s, 1H), 8.71 (s, 1H), 7.80 (d, J = 1.1 Hz, 1H), 7.58 (d, J = 7.2 Hz, 1H), 7.35-7.00 (m, 2H), 4.67-4.25 (m, 2H), 3.21 (t, J = 12.3 Hz, 1H), 3.06-2.81 (m, 6H), 1.96-1.79 (m, 2H), 1.75 (dh, J = 10.1, 5.8, 5.3 Hz, 1H), 1.61-1.44 (m, 1H), 1.43-1.28 (m, 1H). |
| III-3 | 378.1 | 1.91 | 1H NMR (500 MHz, DMSO) δ 9.62 (d, J = 7.1 Hz, 1H), 9.01 (s, 1H), 8.60 (d, J = 1.0 Hz, 1H), 7.75 (d, J = 1.0 Hz, 1H), 7.68-7.66 (m, 2H), 3.88-3.85 (m, 4H), 3.31-3.27 (m, 2H), 2.60-2.58 (m, 2H). |
| III-4 | 440.2 | 2.06 | 1H NMR (500 MHz, DMSO-d6) δ 9.58 (d, J = 7.2 Hz, 1H), 9.08 (s, 1H), 8.79 (d, J = 0.9 Hz, 1H), 7.81 (d, J = 1.0 Hz, 1H), 7.61 (d, J = 7.2 Hz, 1H), 7.32 (t, J = 6.3 Hz, 1H), 7.17 (t, J = 54.0 Hz, 1H), 4.54 (s, 1H), 4.33 (s, 2H), 4.07 (ddd, J = 11.6, 3.5, 1.5 Hz, 1H), 3.68-3.55 (m, 2H), 3.34-3.24 (m, 1H), 3.22-3.09 (m, 2H), 3.07-2.97 (m, 1H), 2.97 (s, 3H). |
| III-5 | 458.1 | 2.14 | 1H NMR (500 MHz, DMSO-d6) δ 10.03 (d, J = 5.8 Hz, 1H), 9.02 (s, 1H), 8.70 (s, 1H), 7.77 (d, J = 1.1 Hz, 1H), 7.32 (t, J = 52.5 Hz, 1H), 7.30 (t, J = 6.3 Hz, 1H), 4.61-4.37 (m, 1H), 4.26 (s, 1H), 4.09-4.03 (m, 1H), 3.65-3.55 (m, 2H), 3.16 (m, 3H), 2.96 (s, 3H), 2.95-2.87 (m, 1H). |
| III-6 | 439.1 | 2.29 | 1H NMR (500 MHz, DMSO-d6) δ 9.43 (d, J = 7.2 Hz, 1H), 9.09 (s, 1H), 8.23-8.18 (m, 1H), 7.61 (s, 1H), 7.56 (d, J = 5.3 Hz, 1H), 7.42 (d, J = 7.2 Hz, 1H), 7.26-7.01 (m, 2H), 4.38-4.26 (m, 1H), 4.18-4.07 (m, 1H), 4.02 (ddd, J = 11.5, 3.5, 1.6 Hz, 1H), 3.69-3.55 (m, 2H), 3.14 (td, J = 6.1, 2.2 Hz, 2H), 3.02-2.88 (m, 4H), 2.72-2.59 (m, 1H). |
| III-7 | 487.2 | 2.86 | 1H NMR (500 MHz, DMSO-d6) δ 9.43 (d, J = 7.2 Hz, 1H), 9.07 (s, 1H), 8.25-8.19 (m, 1H), 7.67 (s, 1H), 7.52 (dd, J = 5.3, 1.2 Hz, 1H), 7.42 (d, J = 7.2 Hz, 1H), 7.28 (t, J = 6.3 |

TABLE 6-continued

Analytical data for compounds of Formula III

| III- | LCMS_Plus | LCMS_RT | NMR |
|---|---|---|---|
| | | | Hz, 1H), 7.13 (t, J = 54.2 Hz, 1H), 4.79 (d, J = 13.8 Hz, 1H), 4.43 (d, J = 13.5 Hz, 1H), 3.52-3.40 (m, 1H), 2.98 (s, 3H), 2.75 (td, J = 12.8, 5.4 Hz, 2H), 2.26-2.04 (m, 3H), 1.19-0.92 (m, 3H). |
| III-8 | 373.1 | 2.24 | 1H NMR (500 MHz, DMSO-d6) δ 9.42 (d, J = 7.1 Hz, 1H), 9.10 (s, 1H), 8.19 (dd, J = 5.3, 0.7 Hz, 1H), 7.61 (s, 1H), 7.58-7.51 (m, 1H), 7.41 (d, J = 7.2 Hz, 1H), 7.15 (t, J = 54.2 Hz, 1H), 3.69-3.63 (m, 2H), 3.63-3.52 (m, 6H), 2.07 (s, 3H). |
| III-9 | 391.1 | 2.45 | 1H NMR (500 MHz, DMSO) δ 9.55 (d, J = 7.2 Hz, 1H), 9.18 (s, 1H), 8.22 (d, J = 5.5 Hz, 1H), 7.61 (d, J = 7.3 Hz, 1H), 7.58 (s, 1H), 7.51 (dd, J = 5.2, 1.3 Hz, 1H), 3.66-3.64 (m, 2H), 3.60-3.55 (m, 6H), 2.07 (s, 3H). |
| III-10 | 458 | 2.14 | 1H NMR (500 MHz, DMSO-d6) δ 10.01 (d, J = 5.9 Hz, 1H), 9.00 (s, 1H), 8.71-8.62 (m, 1H), 7.77 (d, J = 1.1 Hz, 1H), 7.37 (d, J = 52.5 Hz, 1H), 7.29 (t, J = 6.3 Hz, 1H), 4.46 (s, 1H), 4.24 (s, 1H), 4.08-4.00 (m, 1H), 3.59 (dtt, J = 15.2, 5.9, 2.7 Hz, 2H), 3.22-3.08 (m, 3H), 2.96 (s, 3H), 2.95-2.84 (m, 1H). |
| III-11 | 506.3 | 2.73 | 1H NMR (500 MHz, Methanol-d4) δ 9.65 (d, J = 5.3 Hz, 1H), 8.98 (s, 1H), 8.72 (d, J = 0.9 Hz, 1H), 7.97 (d, J = 1.0 Hz, 1H), 7.17 (t, J = 52.5 Hz, 1H), 3.62 (dd, J = 14.0, 3.8 Hz, 1H), 3.36-3.30 (m, 1H), 3.26-3.19 (m, 2H), 3.18-3.05 (m, 1H), 3.03 (s, 3H), 2.45-2.17 (m, 2H), 1.18 (d, J = 6.7 Hz, 3H). |
| III-12 | 488.3 | 2.62 | 1H NMR (500 MHz, DMSO-d6) δ 9.54 (d, J = 7.2 Hz, 1H), 9.02 (s, 1H), 8.73 (s, 1H), 7.87 (s, 1H), 7.55 (d, J = 7.2 Hz, 1H), 7.34 (dd, J = 7.5, 5.4 Hz, 1H), 7.16 (t, J = 54.0 Hz, 1H), 5.03-4.69 (m, 1H), 4.69-4.38 (m, 1H), 3.05-2.87 (m, 7H), 2.34-2.15 (m, 2H), 1.06 (d, J = 6.7 Hz, 3H). |
| III-13 | 502.4 | 2.78 | 1H NMR (500 MHz, DMSO-d6) δ 9.49 (d, J = 7.2 Hz, 1H), 8.94 (s, 1H), 8.62 (d, J = 1.1 Hz, 1H), 7.87 (d, J = 1.2 Hz, 1H), 7.48 (d, J = 7.2 Hz, 1H), 7.30 (dd, J = 8.4, 4.2 Hz, 1H), 7.12 (s, 0H), 3.63 (dd, J = 10.3, 6.2 Hz, 1H), 3.48 (d, J = 13.2 Hz, 1H), 3.20-3.06 (m, 1H), 3.01 (s, 3H), 2.64 (p, J = 1.8 Hz, 1H), 2.37 (p, J = 1.8 Hz, 1H), 1.27 (t, J = 6.9 Hz, 4H), 1.19 (d, J = 6.9 Hz, 3H), 1.08 (d, J = 6.7 Hz, 3H). |
| III-14 | 436.4 | 1.68 | 1H NMR (500 MHz, Methanol-d4) δ 9.40 (d, J = 7.2 Hz, 1H), 9.02 (s, 1H), 8.70 (d, J = 0.8 Hz, 1H), 7.93 (s, 1H), 7.61 (d, J = 7.2 Hz, 1H), 7.03 (t, J = 54.3 Hz, 1H), 3.56 (tt, J = 10.1, 4.5 Hz, 1H), 3.30 (s, 3H), 3.00 (s, 1H), 2.78 (s, 1H), 2.15 (dd, J = 12.9, 4.2 Hz, 1H), 1.88 (d, J = 7.9 Hz, 1H), 1.46-1.34 (m, 1H), 1.31 (s, 1H), 1.10 (d, J = 6.6 Hz, 3H). |

Purity and retention time of the compounds from this invention were measured by HPLC.

HPLC method: analytical reverse phase UPLC-MS was carried out on a waters Acquity UPLC-MS system equipped with a waters BEH 1.7 mm C-18 reverse phase column (2.1 mm×50 mm, 1.7 μm). The mobile phases were acetonitrile and water/acetonitrile (95:5 with 10 mM ammonium formate, pH9). Run time 5 min.

Example 75: N-(2-Hydroxyethyl)-1-(2-(6-(trifluoromethyl)imidazo[1,2-a]pyrazin-3-yl)pyrimidin-4-yl)piperidine-3-carboxamide, IV-479

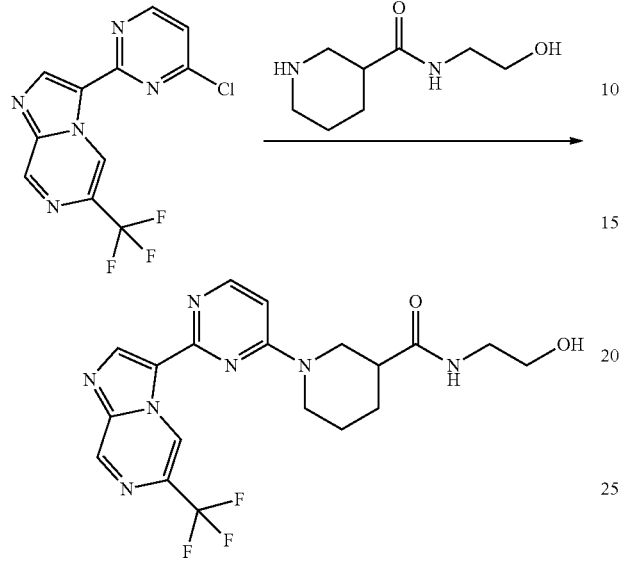

3-(4-Chloropyrimidin-2-yl)-6-(trifluoromethyl)imidazo[1,2-a]pyrazine (20 mg, 0.07 mmol), N-(2-hydroxyethyl)piperidine-3-carboxamide (11.5 mg, 0.07 mmol) and DIPEA (58 µL, 0.33 mmol) were mixed in NMP (1 mL). The reaction was stirred at 85° C. overnight before being diluted in DMSO and purified directly by reverse phase chromatography (C18; MeCN/water—0.1% ammonium hydroxide as eluent) to give N-(2-hydroxyethyl)-1-(2-(6-(trifluoromethyl)imidazo[1,2-a]pyrazin-3-yl)pyrimidin-4-yl)piperidine-3-carboxamide (28 mg, 95%); $^1$H NMR (400 MHz, DMSO-$d_6$) δ 10.34-10.14 (m, 1H), 9.36 (d, J=1.3 Hz, 1H), 8.69 (s, 1H), 8.37 (d, J=6.3 Hz, 1H), 7.94 (t, J=5.6 Hz, 1H), 6.89 (d, J=6.4 Hz, 1H), 4.65 (t, J=5.5 Hz, 1H), 4.42 (s, 2H), 3.40 (p, J=5.9 Hz, 2H), 3.23-2.97 (m, 4H), 2.45-2.31 (m, 1H), 1.90 (d, J=12.3 Hz, 1H), 1.76 (dtd, J=24.0, 12.2, 10.9, 3.9 Hz, 2H), 1.48 (d, J=12.9 Hz, 1H); ES+ [M+H]=436.4.

The following intermediates were made using methodology similar to that described in Example 75:
Methyl 1-(2-(6-(difluoromethyl)imidazo[1,2-a]pyrazin-3-yl)pyrimidin-4-yl)-5-methylpiperidine-3-carboxylate;

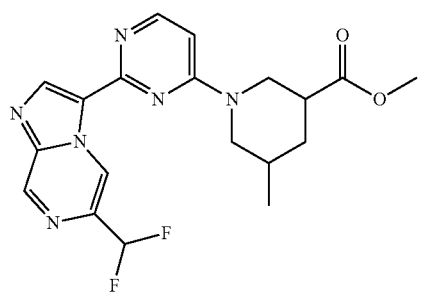 [SMILES: COC(=O)C1CC(C)CN(c2ccnc(-c3cnc4cnc(C(F)F)cn34)n2)C1]

6-(Difluoromethyl)-3-(4-(2,5-dimethyl-3-((methylsulfinyl)methyl)piperidin-1-yl)pyrimidin-2-yl)imidazo[1,2-a]pyrazine;

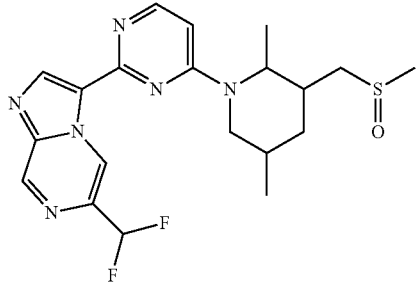 [SMILES: CC1CC(CS(C)=O)C(C)N(c2ccnc(-c3cnc4cnc(C(F)F)cn34)n2)C1]

3-(4-Chloro-6-(2,5-dimethyl-3-(1H-pyrazol-4-yl)piperazin-1-yl)pyrimidin-2-yl)-6-(trifluoromethyl)imidazo[1,2-a]pyrazine;

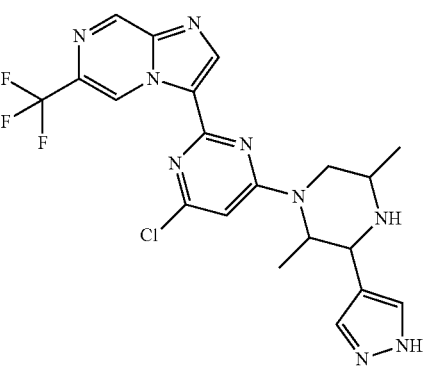 [SMILES: CC1CN(c2cc(Cl)nc(-c3cnc4cnc(C(F)(F)F)cn34)n2)C(C)C(c2cn[nH]c2)N1]

The following compounds were made using methodology similar to that described in Example 75:
1-(4-(6-(Imidazo[1,2-a]pyrazin-3-yl)pyridin-2-yl)piperazin-1-yl)ethan-1-one IV-2;

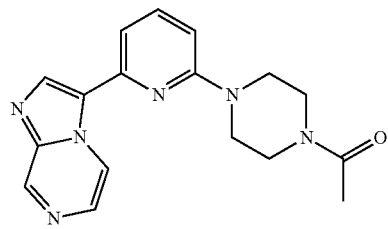 [SMILES: CC(=O)N1CCN(c2cccc(-c3cnc4cnccn34)n2)CC1]

2-(1H-Pyrazol-4-yl)-4-(2-(6-(trifluoromethyl)imidazo[1,2-a]pyrazin-3-yl)pyrimidin-4-yl)morpholine IV-3;

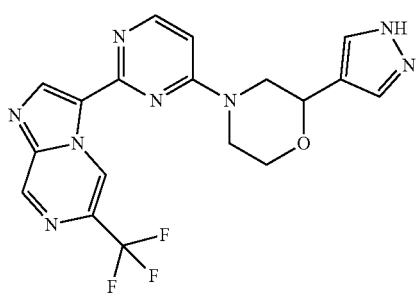

4-(2-(6-Cyclopropylimidazo[1,2-a]pyrazin-3-yl)pyrimidin-4-yl)-2-(1H-pyrazol-4-yl)morpholine IV-4;

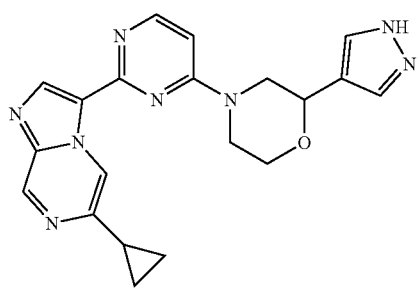 [SMILES: c1cc(N2CCOC(c3cn[nH]c3)C2)nc(-c2cnc3cnc(C4CC4)cn23)n1]

N-((1-(2-(6-Chloroimidazo[1,2-a]pyrazin-3-yl)pyrimidin-4-yl)-4,4-difluoro-5-methylpiperidin-3-yl)methyl)methanesulfonamide IV-5;

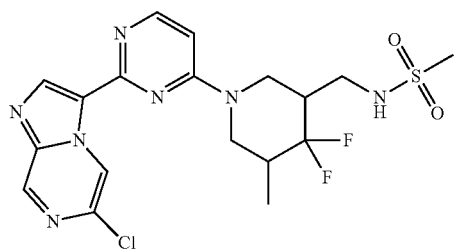 [SMILES: CC1CN(c2ccnc(-c3cnc4cnc(Cl)cn34)n2)CC(CNS(C)(=O)=O)C1(F)F]

4-(2-(6-Chloroimidazo[1,2-a]pyrazin-3-yl)pyrimidin-4-yl)-2-(1H-pyrazol-4-yl)morpholine IV-6;

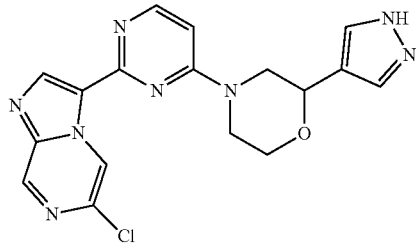

2-Methyl-6-(1H-pyrazol-4-yl)-4-(2-(6-(trifluoromethyl)imidazo[1,2-a]pyrazin-3-yl)pyrimidin-4-yl)morpholine IV-10;

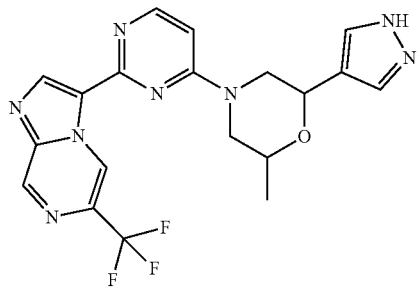

Trans-2-Methyl-6-(1H-pyrazol-4-yl)-4-(2-(6-(trifluoromethyl)imidazo[1,2-a]pyrazin-3-yl)pyrimidin-4-yl)morpholine IV-11;

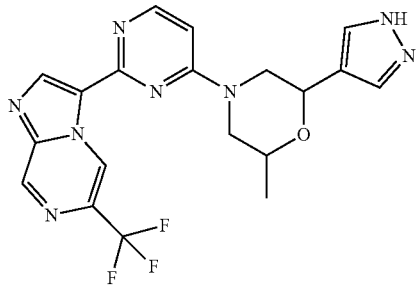 [SMILES: CC1CN(c2ccnc(-c3cnc4cnc(C(F)(F)F)cn34)n2)CC(c2cn[nH]c2)O1]

Cis-2-Methyl-6-(1H-pyrazol-4-yl)-4-(2-(6-(trifluoromethyl)imidazo[1,2-a]pyrazin-3-yl)pyrimidin-4-yl)morpholine IV-12;

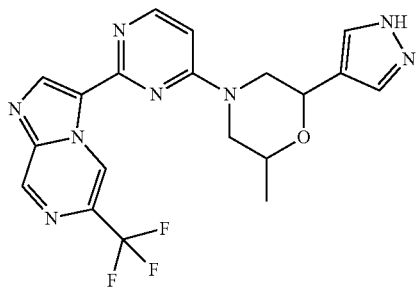

N-(((3S,5S)-4,4-Difluoro-5-methyl-1-(2-(6-(trifluoromethyl)imidazo[1,2-a]pyrazin-3-yl)pyrimidin-4-yl)piperidin-3-yl)methyl)methanesulfonamide IV-17;

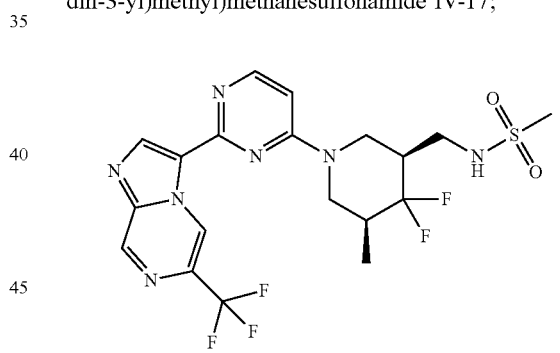

3-(4-(2-(1H-Pyrazol-4-yl)morpholino)pyrimidin-2-yl)imidazo[1,2-a]pyrazine-6-carbonitrile IV-18;

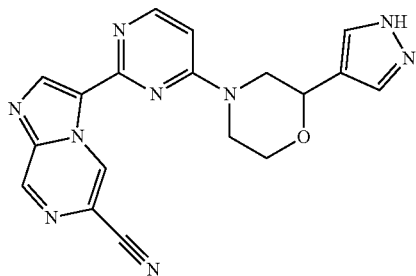 [SMILES: N#Cc1cn2c(-c3nccc(N4CCOC(c5cn[nH]c5)C4)n3)cnc2cn1]

4-(2-(6-Bromoimidazo[1,2-a]pyrazin-3-yl)pyrimidin-4-yl)-2-(1H-pyrazol-4-yl)morpholine IV-19;

991

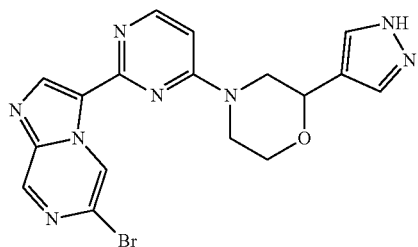 [SMILES: Brc1cn2c(-c3nccc(N4CCOC(c5cn[nH]c5)C4)n3)cnc2cn1]

4-(2-(6-Methylimidazo[1,2-a]pyrazin-3-yl)pyrimidin-4-yl)-2-(1H-pyrazol-4-yl)morpholine IV-20;

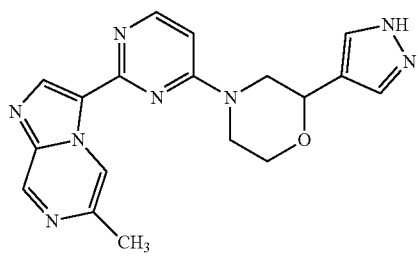 [SMILES: Cc1cn2c(-c3nccc(N4CCOC(c5cn[nH]c5)C4)n3)cnc2cn1]

N-(((3S,5S)-1-(2-(6-(Difluoromethyl)imidazo[1,2-a]pyrazin-3-yl)pyrimidin-4-yl)-4,4-difluoro-5-methylpiperidin-3-yl)methyl)methanesulfonamide IV-21;

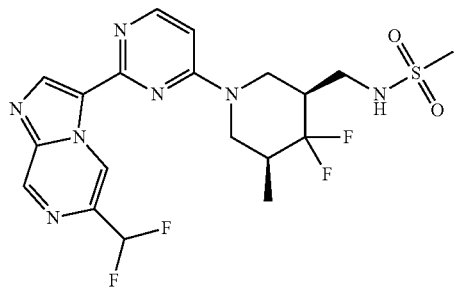 [SMILES: C[C@H]1CN(c2ccnc(-c3cnc4cnc(C(F)F)cn34)n2)C[C@@H](CNS(C)(=O)=O)C1(F)F]

1-(4-(2-(6-(Difluoromethyl)imidazo[1,2-a]pyrazin-3-yl)pyrimidin-4-yl)piperazin-1-yl)ethan-1-one IV-22;

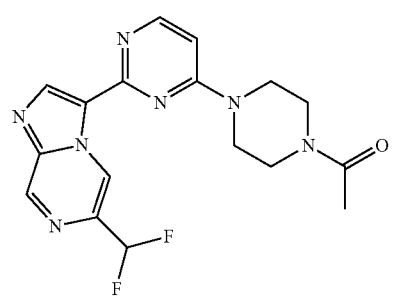 [SMILES: CC(=O)N1CCN(c2ccnc(-c3cnc4cnc(C(F)F)cn34)n2)CC1]

(S)—N-((4-(2-(6-(Difluoromethyl)imidazo[1,2-a]pyrazin-3-yl)pyrimidin-4-yl)morpholin-2-yl)methyl)methanesulfonamide IV-23;

992

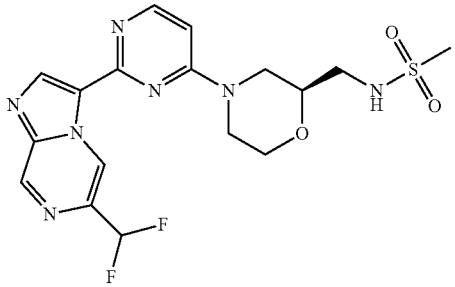 [SMILES: CS(=O)(=O)NC[C@@H]1CN(c2ccnc(-c3cnc4cnc(C(F)F)cn34)n2)CCO1]

N-((1-(2-(6-Bromoimidazo[1,2-a]pyrazin-3-yl)pyrimidin-4-yl)pyrrolidin-3-yl)methyl)methanesulfonamide IV-27;

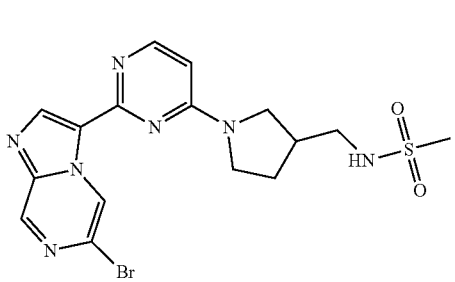 [SMILES: CS(=O)(=O)NCC1CCN(c2ccnc(-c3cnc4cnc(Br)cn34)n2)C1]

4-(2-(6-(Difluoromethyl)imidazo[1,2-a]pyrazin-3-yl)pyrimidin-4-yl)-2-(1H-pyrazol-4-yl)morpholine IV-28;

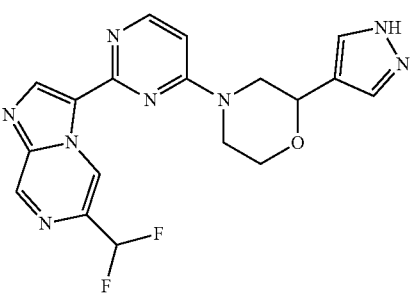 [SMILES: FC(F)c1cn2c(-c3nccc(N4CCOC(c5cn[nH]c5)C4)n3)cnc2cn1]

(S)—N-((1-(2-(6-(Difluoromethyl)imidazo[1,2-a]pyrazin-3-yl)pyrimidin-4-yl)piperidin-3-yl)methyl)methanesulfonamide IV-29;

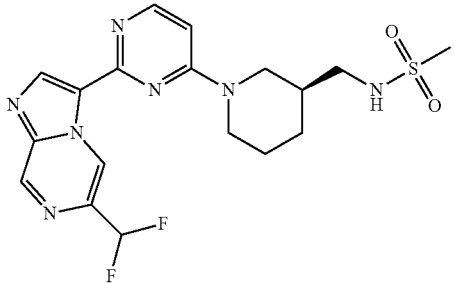 [SMILES: CS(=O)(=O)NC[C@H]1CCCN(c2ccnc(-c3cnc4cnc(C(F)F)cn34)n2)C1]

Imino(methyl)((1-(2-(6-(trifluoromethyl)imidazo[1,2-a]pyrazin-3-yl)pyrimidin-4-yl)piperidin-3-yl)methyl)-$\lambda^6$-sulfanone IV-34;

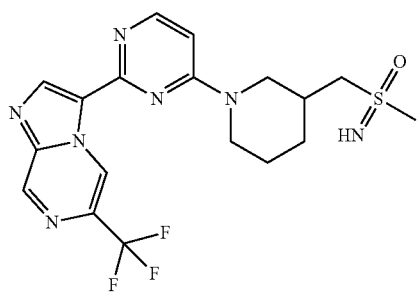 [SMILES: CS(=N)(=O)CC1CCCN(c2ccnc(-c3cnc4cnc(C(F)(F)F)cn34)n2)C1]

1-(4-(2-(6-Chloroimidazo[1,2-a]pyrazin-3-yl)pyrimidin-4-yl)piperazin-1-yl)ethan-1-one IV-35;

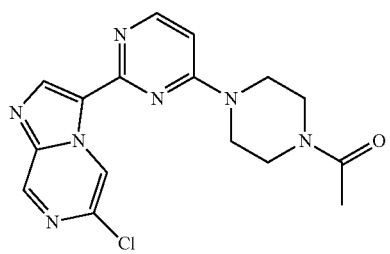 [SMILES: CC(=O)N1CCN(c2ccnc(-c3cnc4cnc(Cl)cn34)n2)CC1]

3-(4-(4-Acetylpiperazin-1-yl)pyrimidin-2-yl)imidazo[1,2-a]pyrazine-6-carboxamide IV-36;

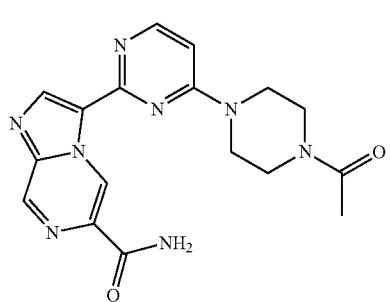

3-(4-(2-(1H-Pyrazol-4-yl)morpholino)pyrimidin-2-yl)imidazo[1,2-a]pyrazine-6-carboxamide IV-38;

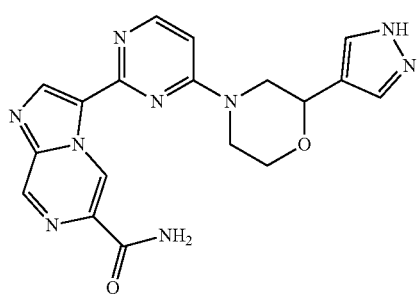 [SMILES: NC(=O)c1cn2c(-c3nccc(N4CCOC(c5cn[nH]c5)C4)n3)cnc2cn1]

4-(2-(Imidazo[1,2-a]pyrazin-3-yl)pyrimidin-4-yl)-2-(1H-pyrazol-4-yl)morpholine IV-39;

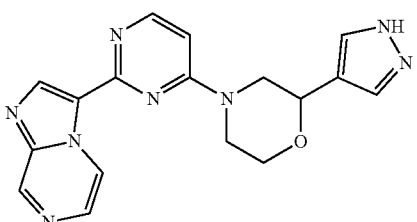

2-(1H-Pyrazol-4-yl)-4-(4-(6-(trifluoromethyl)imidazo[1,2-a]pyrazin-3-yl)pyrimidin-2-yl)morpholine IV-40;

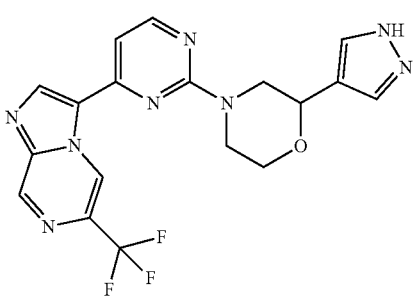 [SMILES: FC(F)(F)c1cn2c(-c3ccnc(N4CCOC(c5cn[nH]c5)C4)n3)cnc2cn1]

1-((1-(2-(6-(Difluoromethyl)imidazo[1,2-a]pyrazin-3-yl)pyrimidin-4-yl)piperidin-3-yl)methyl)urea IV-41;

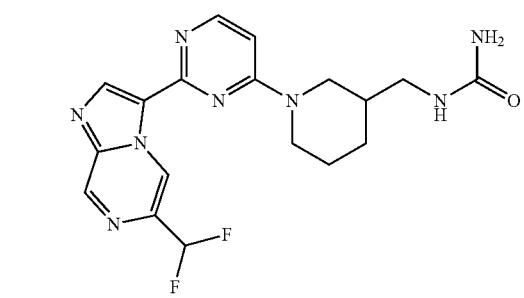 [SMILES: NC(=O)NCC1CCCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)piperidine-3-carboxamide IV-42;

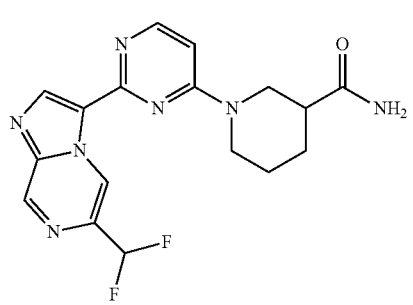 [SMILES: NC(=O)C1CCCN(c2ccnc(-c3cnc4cnc(C(F)F)cn34)n2)C1]

N-(2-(1-(2-(6-(Difluoromethyl)imidazo[1,2-a]pyrazin-3-yl)pyrimidin-4-yl)piperidin-3-yl)ethyl)methanesulfonamide IV-43;

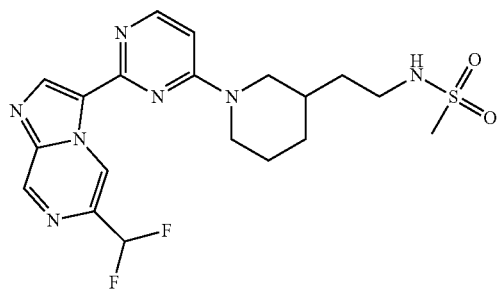 [SMILES: CS(=O)(=O)NCCC1CCCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)-N-methylpiperidine-3-carboxamide IV-44;

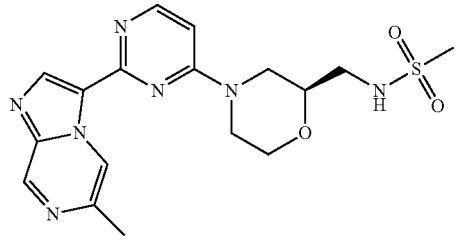

4-(2-(6-(Difluoromethyl)imidazo[1,2-a]pyrazin-3-yl)pyrimidin-4-yl)morpholine-2-carboxamide IV-48;

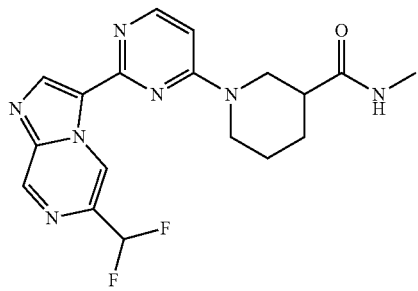 [SMILES: CNC(=O)C1CCCN(c2ccnc(-c3cnc4cnc(C(F)F)cn34)n2)C1]

3-(1-(2-(6-(Difluoromethyl)imidazo[1,2-a]pyrazin-3-yl)pyrimidin-4-yl)piperidin-3-yl)propanamide IV-45;

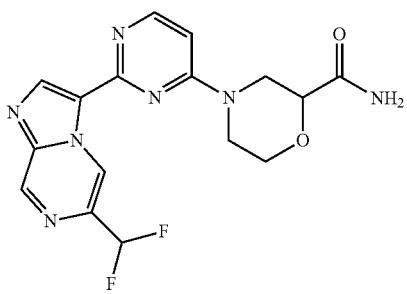

1-(2-(6-(Difluoromethyl)imidazo[1,2-a]pyrazin-3-yl)pyrimidin-4-yl)-1,4-diazepan-5-one IV-49;

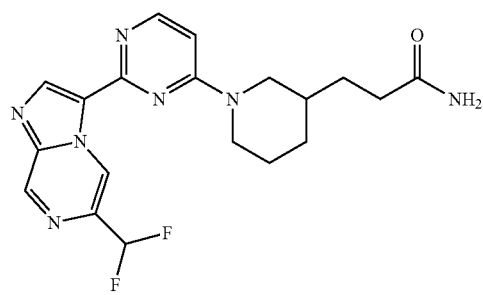 [SMILES: NC(=O)CCC1CCCN(c2ccnc(-c3cnc4cnc(C(F)F)cn34)n2)C1]

N-((1-(4-(6-(Difluoromethyl)imidazo[1,2-a]pyrazin-3-yl)pyrimidin-2-yl)-4,4-difluoro-5-methylpiperidin-3-yl)methyl)methanesulfonamide IV-46;

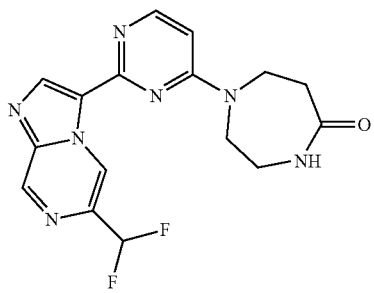

(S)-1-(2-(6-(Difluoromethyl)imidazo[1,2-a]pyrazin-3-yl)pyrimidin-4-yl)piperidine-3-carboxamide IV-50;

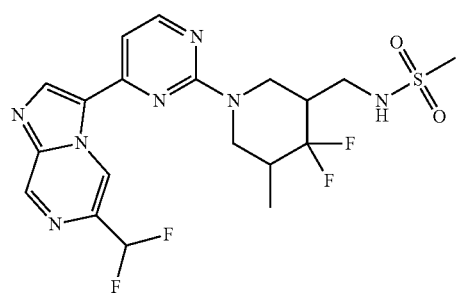 [SMILES: CC1CN(c2nccc(-c3cnc4cnc(C(F)F)cn34)n2)CC(CNS(C)(=O)=O)C1(F)F]

(S)—N-((4-(2-(6-Methylimidazo[1,2-a]pyrazin-3-yl)pyrimidin-4-yl)morpholin-2-yl)methyl)methanesulfonamide IV-47;

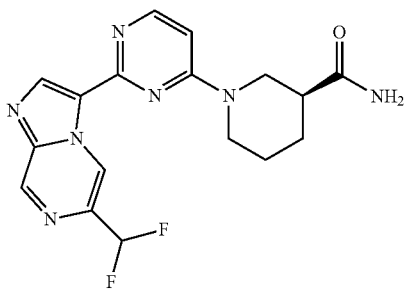 [SMILES: NC(=O)[C@H]1CCCN(c2ccnc(-c3cnc4cnc(C(F)F)cn34)n2)C1]

3-(4-(3-(2H-Tetrazol-5-yl)piperidin-1-yl)pyrimidin-2-yl)-6-(difluoromethyl)imidazo[1,2-a]pyrazine IV-51;

997

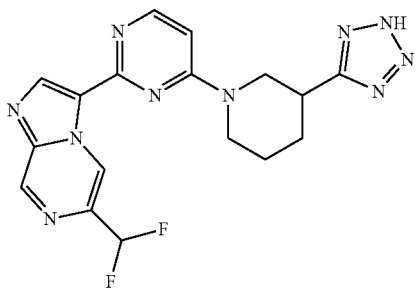 [SMILES: FC(F)c1cn2c(-c3nccc(N4CCCC(c5nn[nH]n5)C4)n3)cnc2cn1]

6-(Difluoromethyl)-3-(4-(3-(pyridin-3-yl)piperidin-1-yl)pyrimidin-2-yl)imidazo[1,2-a]pyrazine IV-52;

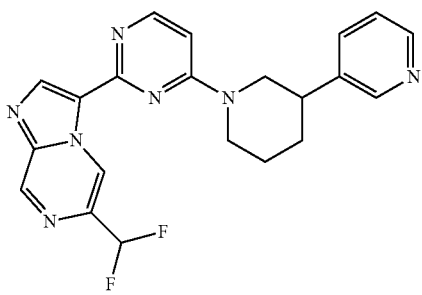 [SMILES: FC(F)c1cn2c(-c3nccc(N4CCCC(c5cccnc5)C4)n3)cnc2cn1]

3-(4-(3-(1H-Imidazol-4-yl)piperidin-1-yl)pyrimidin-2-yl)-6-(difluoromethyl)imidazo[1,2-a]pyrazine IV-53;

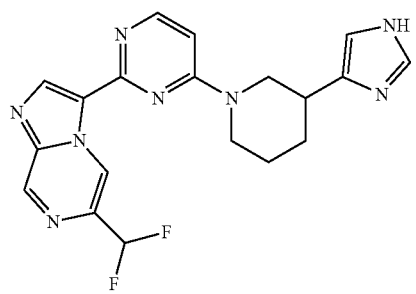 [SMILES: FC(F)c1cn2c(-c3nccc(N4CCCC(c5c[nH]cn5)C4)n3)cnc2cn1]

1-(2-(6-(Difluoromethyl)imidazo[1,2-a]pyrazin-3-yl)pyrimidin-4-yl)-2-methylpiperidine-3-carboxamide IV-54;

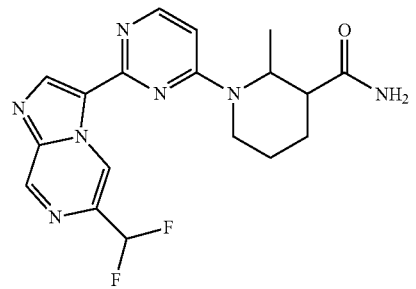 [SMILES: CC1C(C(N)=O)CCCN1c1ccnc(-c2cnc3cnc(C(F)F)cn23)n1]

1-(6-(6-(Difluoromethyl)imidazo[1,2-a]pyrazin-3-yl)pyridin-2-yl)piperidine-3-carboxamide IV-55;

998

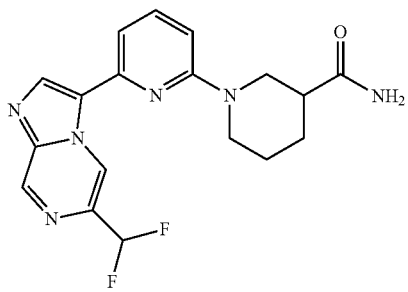 [SMILES: NC(=O)C1CCCN(c2cccc(-c3cnc4cnc(C(F)F)cn34)n2)C1]

1-(2-(6-(Difluoromethyl)imidazo[1,2-a]pyrazin-3-yl)pyrimidin-4-yl)piperidine-3-sulfonamide IV-56;

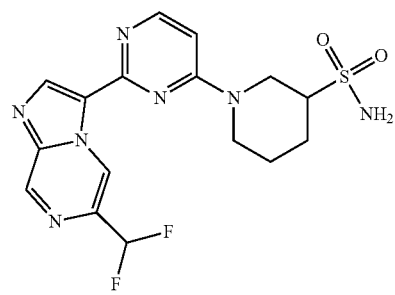 [SMILES: NS(=O)(=O)C1CCCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)-3-methylpiperidine-3-carboxamide IV-57;

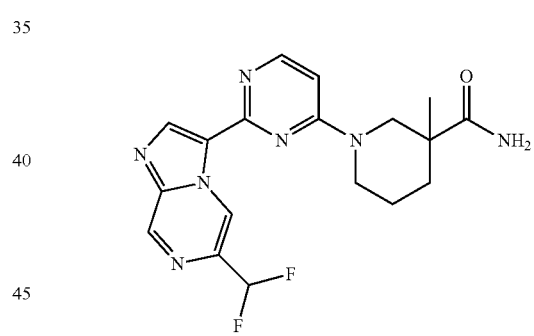

3-(4-(3-(1H-Pyrazol-4-yl)piperidin-1-yl)pyrimidin-2-yl)-6-(difluoromethyl)imidazo[1,2-a]pyrazine IV-58;

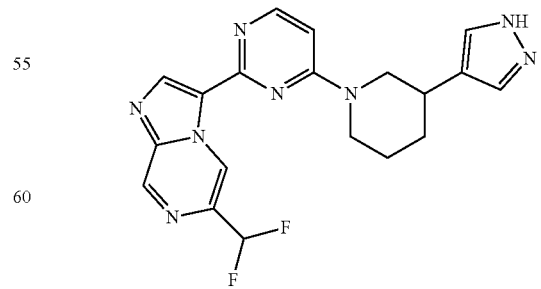

3-(4-(3-(1H-Pyrazol-4-yl)piperidin-1-yl)pyrimidin-2-yl)-6-(trifluoromethyl)imidazo[1,2-a]pyrazine IV-59;

999

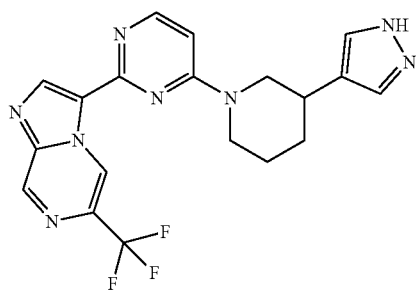

(S)-1-(2-(6-(Trifluoromethyl)imidazo[1,2-a]pyrazin-3-yl)pyrimidin-4-yl)piperidine-3-carboxamide IV-60;

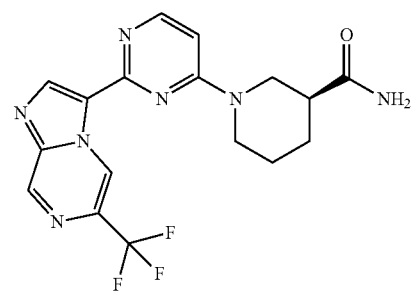 [SMILES: NC(=O)[C@H]1CCCN(c2ccnc(-c3cnc4cnc(C(F)(F)F)cn34)n2)C1]

N-(1-(4-(2-(6-(Difluoromethyl)imidazo[1,2-a]pyrazin-3-yl)pyrimidin-4-yl)morpholin-2-yl)ethyl)methanesulfonamide IV-61;

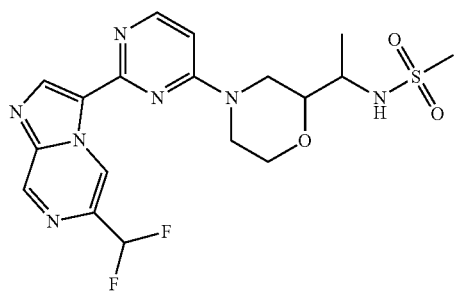 [SMILES: CC(NS(C)(=O)=O)C1CN(c2ccnc(-c3cnc4cnc(C(F)F)cn34)n2)CCO1]

N-(1-(4-(2-(6-(Difluoromethyl)imidazo[1,2-a]pyrazin-3-yl)pyrimidin-4-yl)morpholin-2-yl)ethyl)methanesulfonamide IV-62;

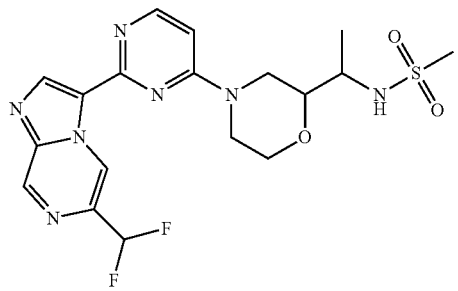 [SMILES: CC(NS(C)(=O)=O)C1CN(c2ccnc(-c3cnc4cnc(C(F)F)cn34)n2)CCO1]

1-(2-(6-(Difluoromethyl)imidazo[1,2-a]pyrazin-3-yl)pyrimidin-4-yl)pyrrolidine-3-carboxamide IV-63;

1000

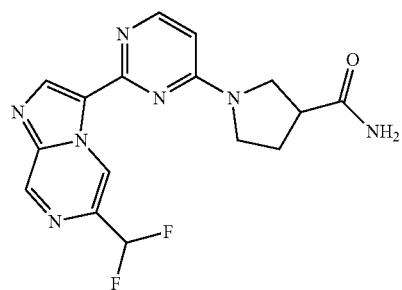 [SMILES: NC(=O)C1CCN(c2ccnc(-c3cnc4cnc(C(F)F)cn34)n2)C1]

3-(4-(3-(1H-Pyrazol-3-yl)pyrrolidin-1-yl)pyrimidin-2-yl)-6-(difluoromethyl)imidazo[1,2-a]pyrazine IV-64;

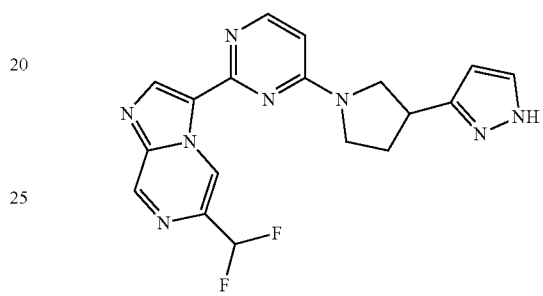

6-(Difluoromethyl)-3-(4-(3-(1-methyl-1H-pyrazol-4-yl)pyrrolidin-1-yl)pyrimidin-2-yl)imidazo[1,2-a]pyrazine IV-65;

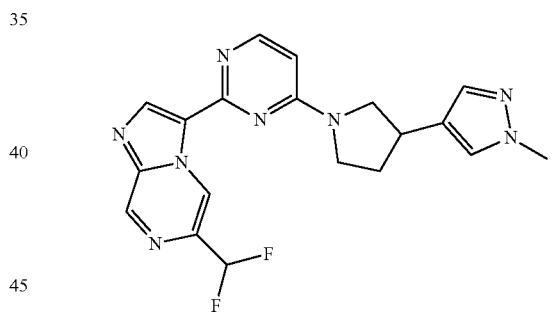

N-((1-(2-(6-(Difluoromethyl)imidazo[1,2-a]pyrazin-3-yl)pyrimidin-4-yl)pyrrolidin-3-yl)methyl)methanesulfonamide IV-66;

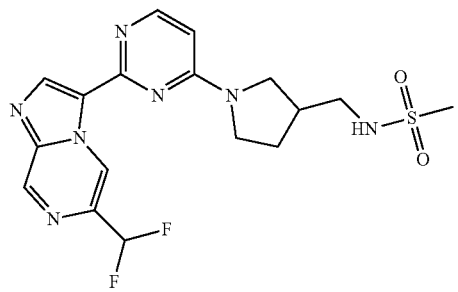 [SMILES: CS(=O)(=O)NCC1CCN(c2ccnc(-c3cnc4cnc(C(F)F)cn34)n2)C1]

3-(4-(3-(1H-Imidazol-4-yl)pyrrolidin-1-yl)pyrimidin-2-yl)-6-(difluoromethyl)imidazo[1,2-a]pyrazine IV-67;

1001

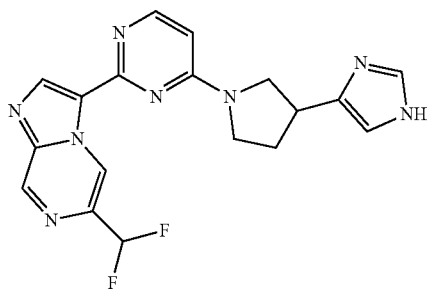 [SMILES: FC(F)c1cn2c(-c3nccc(N4CCC(c5c[nH]cn5)C4)n3)cnc2cn1]

6-(Difluoromethyl)-3-(4-(3-(pyridin-4-yl)pyrrolidin-1-yl) pyrimidin-2-yl)imidazo[1,2-a]pyrazine IV-68;

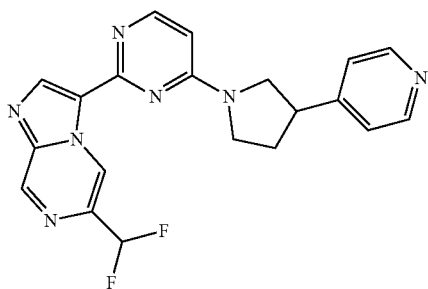 [SMILES: FC(F)c1cn2c(-c3nccc(N4CCC(c5ccncc5)C4)n3)cnc2cn1]

7-(2-(6-(Difluoromethyl)imidazo[1,2-a]pyrazin-3-yl)pyrimidin-4-yl)-2,7-di azaspiro[4.4]nonan-1-one IV-69;

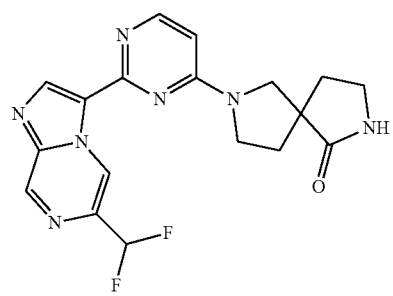 [SMILES: O=C1NCCC12CCN(c1ccnc(-c3cnc4cnc(C(F)F)cn34)n1)C2]

N-(1-(2-(6-(Difluoromethyl)imidazo[1,2-a]pyrazin-3-yl)pyrimidin-4-yl)pyrrolidin-3-yl)methanesulfonamide IV-70;

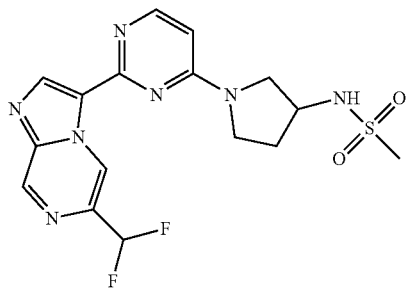 [SMILES: CS(=O)(=O)NC1CCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)-N-methylpyrrolidine-3-sulfonamide IV-71;

1002

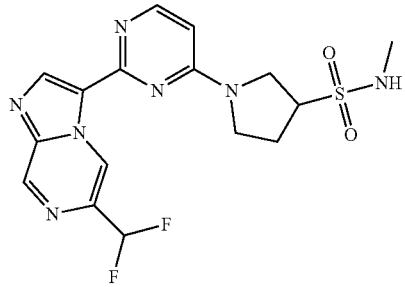 [SMILES: CNS(=O)(=O)C1CCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)pyrrolidin-3-ol IV-72;

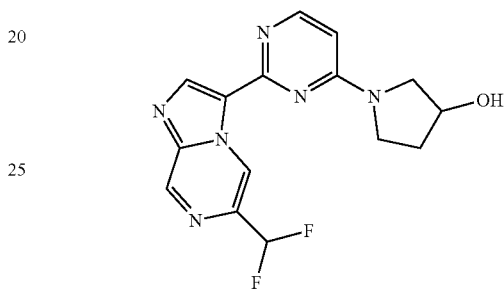

6-(Difluoromethyl)-3-(4-(3-(oxetan-3-yl)pyrrolidin-1-yl) pyrimidin-2-yl)imidazo[1,2-a]pyrazine IV-73;

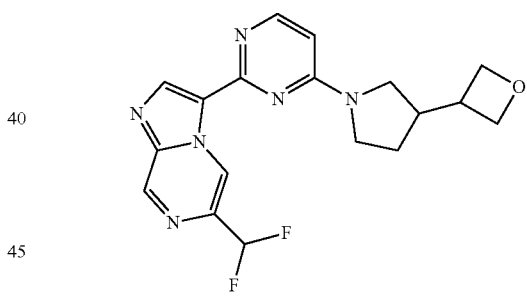

6-(Difluoromethyl)-3-[4-[3-[(sulfamoylamino)methyl]-1-piperidyl]pyrimidin-2-yl]imidazo[1,2-a]pyrazine IV-74;

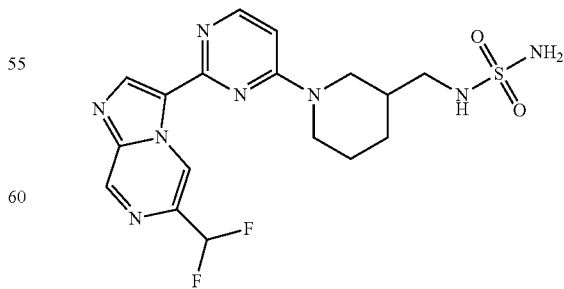

3-[4-(6-Azaspiro[3.4]octan-6-yl)pyrimidin-2-yl]-6-(difluoromethyl)imidazo[1,2-a]pyrazine IV-75;

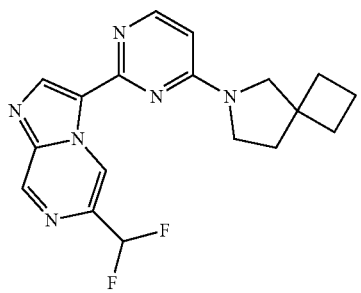 [SMILES: FC(F)c1cn2c(-c3nccc(N4CCC5(CCC5)C4)n3)cnc2cn1]

6-(Difluoromethyl)-3-(4-(3-(pyridin-3-yl)pyrrolidin-1-yl)
pyrimidin-2-yl)imidazo[1,2-a]pyrazine IV-76;

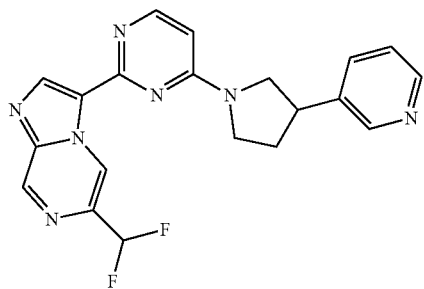 [SMILES: FC(F)c1cn2c(-c3nccc(N4CCC(c5cccnc5)C4)n3)cnc2cn1]

6-(Difluoromethyl)-3-(4-(3-(pyridin-2-yl)pyrrolidin-1-yl)
pyrimidin-2-yl)imidazo[1,2-a]pyrazine IV-77;

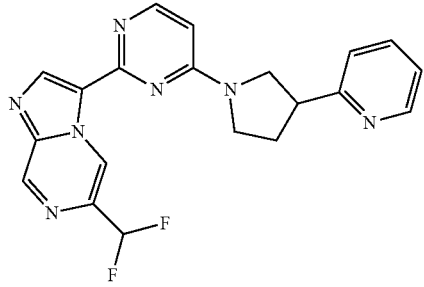 [SMILES: FC(F)c1cn2c(-c3nccc(N4CCC(c5ccccn5)C4)n3)cnc2cn1]

1-(4-(2-(6-(1,1-Difluoroethyl)imidazo[1,2-a]pyrazin-3-yl)
pyrimidin-4-yl)piperazin-1-yl)ethan-1-one IV-78;

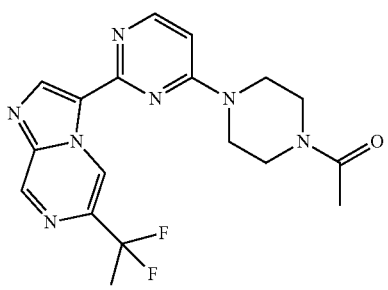 [SMILES: CC(=O)N1CCN(c2ccnc(-c3cnc4cnc(C(C)(F)F)cn34)n2)CC1]

4-(2-(6-(Difluoromethyl)imidazo[1,2-a]pyrazin-3-yl)py-
rimidin-4-yl)thiomorpholine 1-oxide IV-80;

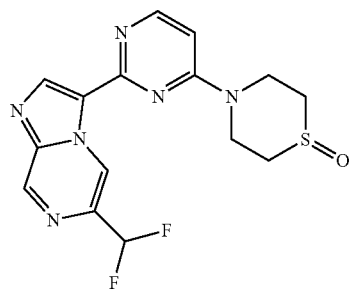 [SMILES: O=S1CCN(c2ccnc(-c3cnc4cnc(C(F)F)cn34)n2)CC1]

(S)-4-(2-(6-(Difluoromethyl)imidazo[1,2-a]pyrazin-3-yl)
pyrimidin-4-yl)-3-methylmorpholine IV-81;

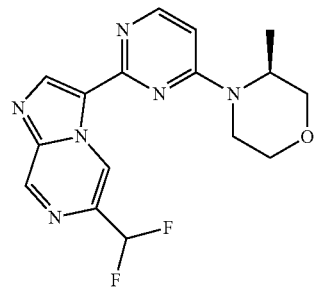 [SMILES: C[C@H]1COCCN1c1ccnc(-c2cnc3cnc(C(F)F)cn23)n1]

2-(1-(2-(6-(Difluoromethyl)imidazo[1,2-a]pyrazin-3-yl)py-
rimidin-4-yl)piperidin-3-yl)acetonitrile IV-82;

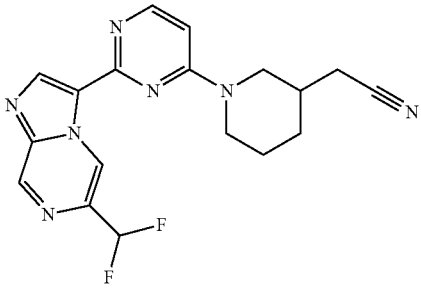 [SMILES: N#CCC1CCCN(c2ccnc(-c3cnc4cnc(C(F)F)cn34)n2)C1]

7-(2-(6-(Difluoromethyl)imidazo[1,2-a]pyrazin-3-yl)py-
rimidin-4-yl)-5,6,7,8-tetrahydro-[1,2,4]triazolo[4,3-a]
pyrazin-3 (2H)-one IV-83;

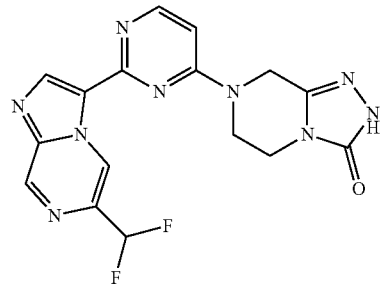 [SMILES: O=c1[nH]nc2n1CCN(c1ccnc(-c3cnc4cnc(C(F)F)cn34)n1)C2]

4-(2-(6-(Difluoromethyl)imidazo[1,2-a]pyrazin-3-yl)py-
rimidin-4-yl)thiomorpholine 1,1-dioxide IV-84;

1005

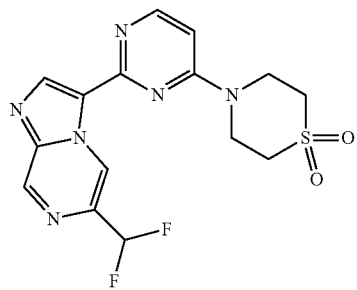 [SMILES: O=S1(=O)CCN(c2ccnc(-c3cnc4cnc(C(F)F)cn34)n2)CC1]

(S)-6-(Difluoromethyl)-3-(4-(2-methylpiperidin-1-yl)pyrimidin-2-yl)imidazo[1,2-a]pyrazine IV-85;

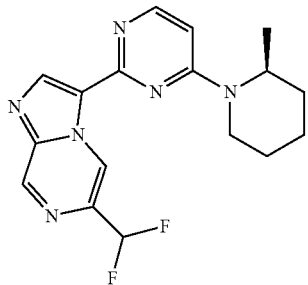 [SMILES: C[C@H]1CCCCN1c1ccnc(-c2cnc3cnc(C(F)F)cn23)n1]

8-(2-(6-(Difluoromethyl)imidazo[1,2-a]pyrazin-3-yl)pyrimidin-4-yl)hexahydro-2H-pyrazino[1,2-a]pyrazin-1(6H)-one IV-86;

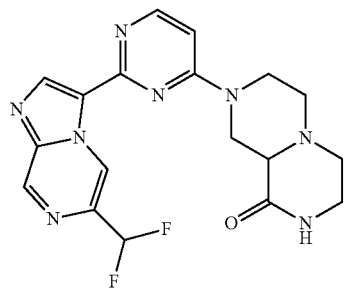 [SMILES: O=C1NCCN2CCN(c3ccnc(-c4cnc5cnc(C(F)F)cn45)n3)CC12]

8-(2-(6-(Difluoromethyl)imidazo[1,2-a]pyrazin-3-yl)pyrimidin-4-yl)-1-oxa-3,8-diazaspiro[4.6]undecan-2-one IV-87;

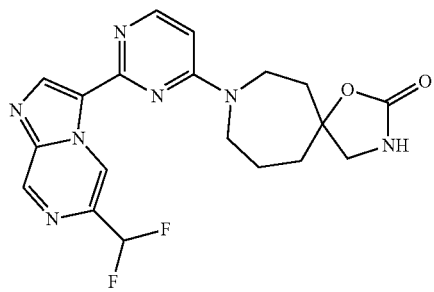 [SMILES: O=C1NCC2(CCCN(c3ccnc(-c4cnc5cnc(C(F)F)cn45)n3)CC2)O1]

(1-(2-(6-(Difluoromethyl)imidazo[1,2-a]pyrazin-3-yl)pyrimidin-4-yl)azepan-3-yl)methanol IV-88;

1006

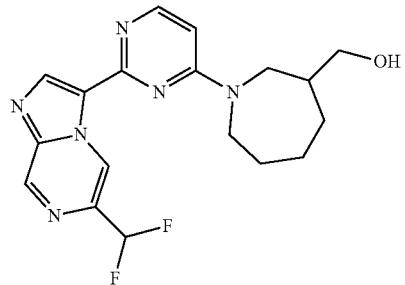 [SMILES: OCC1CCCCN(c2ccnc(-c3cnc4cnc(C(F)F)cn34)n2)C1]

4-(2-(6-(Difluoromethyl)imidazo[1,2-a]pyrazin-3-yl)pyrimidin-4-yl)-1-methylpiperazine-2-carboxamide IV-89;

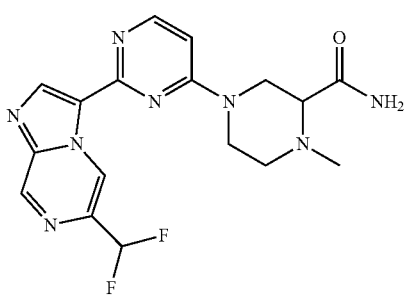

1-(2-(6-(Difluoromethyl)imidazo[1,2-a]pyrazin-3-yl)pyrimidin-4-yl)-4-methylazepan-4-ol IV-90;

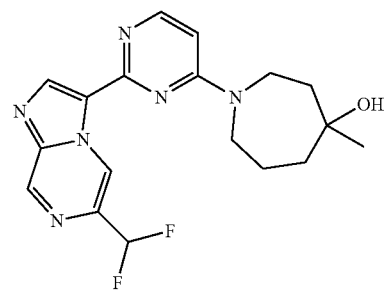 [SMILES: CC1(O)CCCN(c2ccnc(-c3cnc4cnc(C(F)F)cn34)n2)CC1]

3-(2-(6-(Difluoromethyl)imidazo[1,2-a]pyrazin-3-yl)pyrimidin-4-yl)-8-oxa-3-azabicyclo[3.2.1]octane IV-91;

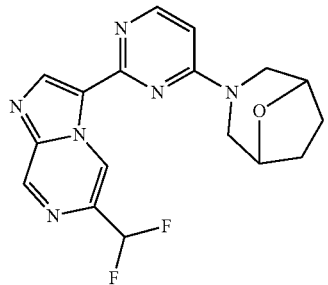 [SMILES: FC(F)c1cn2c(-c3nccc(N4CC5CCC(C4)O5)n3)cnc2cn1]

2-(3-(1-(2-(6-(Difluoromethyl)imidazo[1,2-a]pyrazin-3-yl)pyrimidin-4-yl)piperidin-3-yl)-1H-pyrazol-5-yl)ethan-1-ol IV-92;

1007

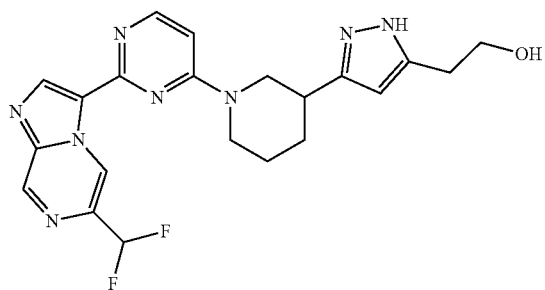 [SMILES: OCCc1cc(C2CCCN(c3ccnc(-c4cnc5cnc(C(F)F)cn45)n3)C2)n[nH]1]

(3-(1-(2-(6-(Difluoromethyl)imidazo[1,2-a]pyrazin-3-yl)
pyrimidin-4-yl)piperidin-3-yl)-1H-pyrazol-5-yl)methanol
IV-93;

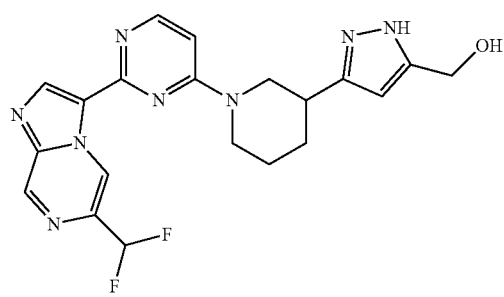 [SMILES: OCc1cc(C2CCCN(c3ccnc(-c4cnc5cnc(C(F)F)cn45)n3)C2)n[nH]1]

3-(1-(2-(6-(Difluoromethyl)imidazo[1,2-a]pyrazin-3-yl)py-
rimidin-4-yl)piperidin-3-yl)-1H-pyrazole-5-carboxamide
IV-94;

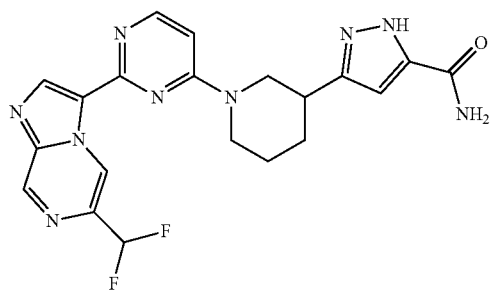 [SMILES: NC(=O)c1cc(C2CCCN(c3ccnc(-c4cnc5cnc(C(F)F)cn45)n3)C2)n[nH]1]

3-(1-(2-(6-(Difluoromethyl)imidazo[1,2-a]pyrazin-3-yl)py-
rimidin-4-yl)piperidin-3-yl)-N-methyl-1H-pyrazole-5-
carboxamide IV-95;

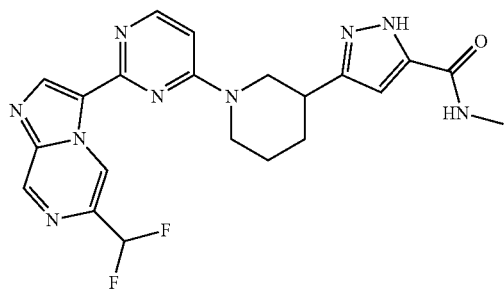 [SMILES: CNC(=O)c1cc(C2CCCN(c3ccnc(-c4cnc5cnc(C(F)F)cn45)n3)C2)n[nH]1]

6-(Difluoromethyl)-3-(4-(5-(3-methyl-1H-pyrazol-4-yl)-3,
6-dihydropyridin-1 (2H)-yl)pyrimidin-2-yl)imidazo[1,2-
a]pyrazine IV-96;

1008

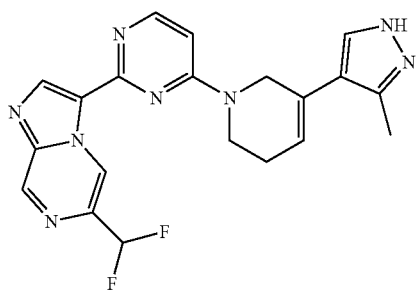 [SMILES: Cc1n[nH]cc1C1=CCCN(c2ccnc(-c3cnc4cnc(C(F)F)cn34)n2)C1]

6-(Difluoromethyl)-3-(4-(3-(3-methyl-1H-pyrazol-4-yl)pip-
eridin-1-yl)pyrimidin-2-yl)imidazo[1,2-a]pyrazine IV-97;

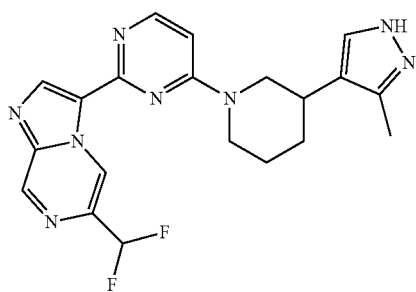 [SMILES: Cc1n[nH]cc1C1CCCN(c2ccnc(-c3cnc4cnc(C(F)F)cn34)n2)C1]

2-(2-(6-(Difluoromethyl)imidazo[1,2-a]py-
rimidin-4-yl)hexahydropyrrolo[1,2-a]pyrazin-6(2H)-one
IV-98;

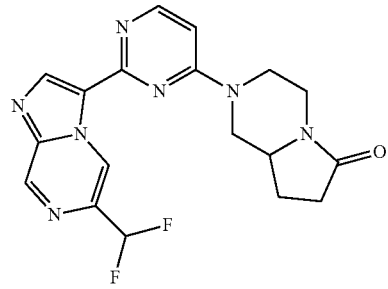 [SMILES: O=C1CCC2CN(c3ccnc(-c4cnc5cnc(C(F)F)cn45)n3)CCN12]

2-(2-(6-(Difluoromethyl)imidazo[1,2-a]pyrazin-3-yl)py-
rimidin-4-yl)octahydro-6H-pyrido[1,2-a]pyrazin-6-one
IV-99;

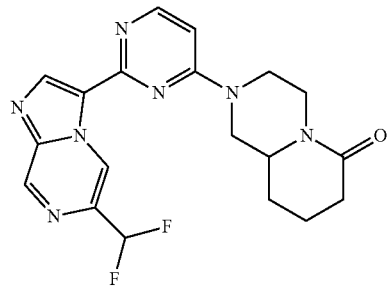 [SMILES: O=C1CCCC2CN(c3ccnc(-c4cnc5cnc(C(F)F)cn45)n3)CCN12]

7-(2-(6-(Difluoromethyl)imidazo[1,2-a]pyrazin-3-yl)py-
rimidin-4-yl)hexahydro-3H-oxazolo[3,4-a]pyrazin-3-one
IV-100;

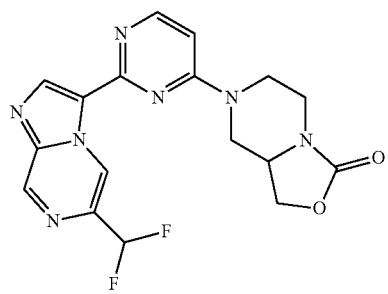 [SMILES: O=C1OCC2CN(c3ccnc(-c4cnc5cnc(C(F)F)cn45)n3)CCN12]

4-(2-(6-(Difluoromethyl)imidazo[1,2-a]pyrazin-3-yl)pyrimidin-4-yl)-1,4-diazepane-1-sulfonamide IV-101;

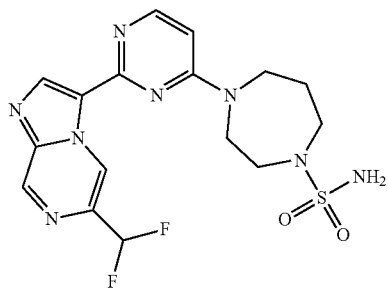 [SMILES: NS(=O)(=O)N1CCCN(c2ccnc(-c3cnc4cnc(C(F)F)cn34)n2)CC1]

6-(Difluoromethyl)-3-(4-(3-(tetrahydro-2H-pyran-4-yl)pyrrolidin-1-yl)pyrimidin-2-yl)imidazo[1,2-a]pyrazine IV-102;

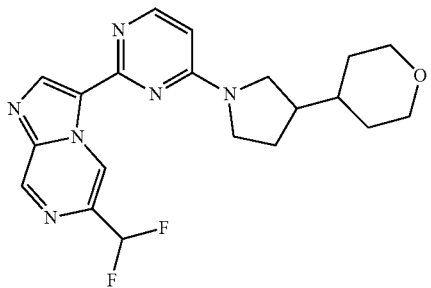 [SMILES: FC(F)c1cn2c(-c3nccc(N4CCC(C5CCOCC5)C4)n3)cnc2cn1]

6-(Difluoromethyl)-3-(4-(piperidin-1-yl)pyrimidin-2-yl)imidazo[1,2-a]pyrazine IV-103;

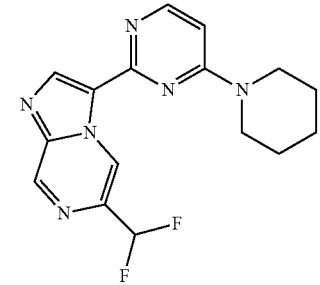 [SMILES: FC(F)c1cn2c(-c3nccc(N4CCCCC4)n3)cnc2cn1]

4-(2-(6-(Difluoromethyl)imidazo[1,2-a]pyrazin-3-yl)pyrimidin-4-yl)morpholine IV-104;

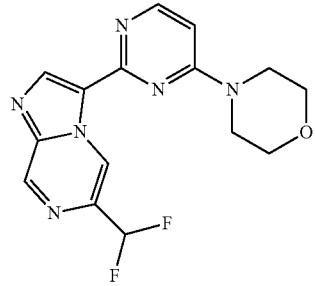 [SMILES: FC(F)c1cn2c(-c3nccc(N4CCOCC4)n3)cnc2cn1]

3-(4-(Azepan-1-yl)pyrimidin-2-yl)-6-(difluoromethyl)imidazo[1,2-a]pyrazine IV-105;

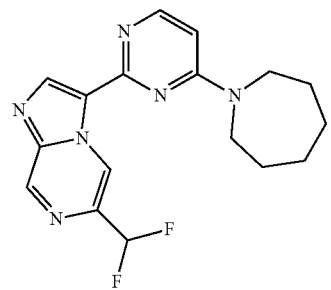 [SMILES: FC(F)c1cn2c(-c3nccc(N4CCCCCC4)n3)cnc2cn1]

Cis-1-(2-(6-(Difluoromethyl)imidazo[1,2-a]pyrazin-3-yl)pyrimidin-4-yl)-6-methylpiperidine-3 carboxamide IV-106;

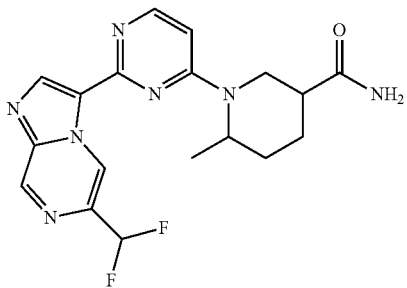 [SMILES: CC1CCC(C(N)=O)CN1c1ccnc(-c2cnc3cnc(C(F)F)cn23)n1]

1-(2-(6-(Difluoromethyl)imidazo[1,2-a]pyrazin-3-yl)pyrimidin-4-yl)-4-methylpiperidine-3-carboxamide IV-108;

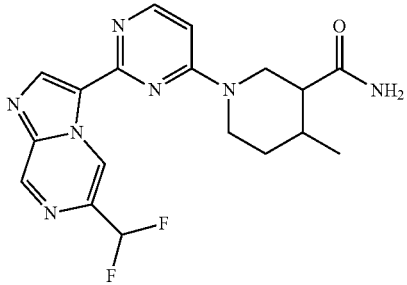 [SMILES: CC1CCN(c2ccnc(-c3cnc4cnc(C(F)F)cn34)n2)CC1C(N)=O]

1-(2-(6-(Difluoromethyl)imidazo[1,2-a]pyrazin-3-yl)pyrimidin-4-yl)-2-methylpiperidine-3-carboxamide IV-109;

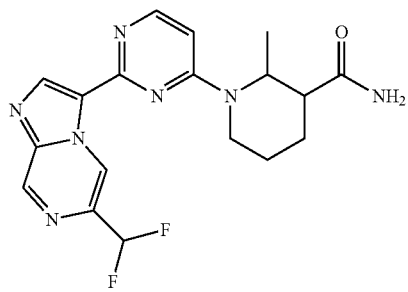 [SMILES: CC1C(C(N)=O)CCCN1c1ccnc(-c2cnc3cnc(C(F)F)cn23)n1]

Cis-1-(2-(6-(Difluoromethyl)imidazo[1,2-a]pyrazin-3-yl)pyrimidin-4-yl)-2-methylpiperidine-3-carboxylic acid IV-110;

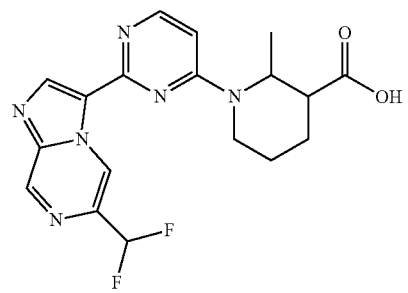 [SMILES: CC1C(C(=O)O)CCCN1c1ccnc(-c2cnc3cnc(C(F)F)cn23)n1]

(3-(2-(6-(Difluoromethyl)imidazo[1,2-a]pyrazin-3-yl)pyrimidin-4-yl)-3-azabicyclo[3.1.0]hexan-1-yl)methanol IV-111;

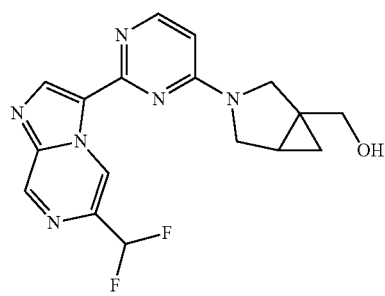 [SMILES: OCC12CC1CN(c1ccnc(-c3cnc4cnc(C(F)F)cn34)n1)C2]

6-(Difluoromethyl)-3-(4-(3-(5-methyl-1H-pyrazol-3-yl)piperidin-1-yl)pyrimidin-2-yl)imidazo[1,2-a]pyrazine IV-112;

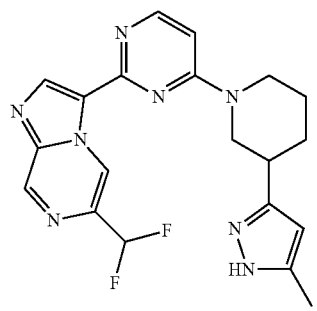 [SMILES: Cc1cc(C2CCCN(c3ccnc(-c4cnc5cnc(C(F)F)cn45)n3)C2)n[nH]1]

3-(1-(2-(6-(Difluoromethyl)imidazo[1,2-a]pyrazin-3-yl)pyrimidin-4-yl)piperidin-3-yl)-1-methyl-1H-pyrazol-5-ol IV-113;

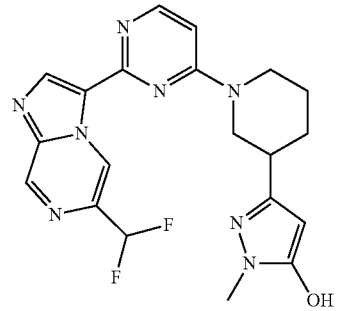 [SMILES: Cn1nc(C2CCCN(c3ccnc(-c4cnc5cnc(C(F)F)cn45)n3)C2)cc1O]

(1-(2-(6-(Difluoromethyl)imidazo[1,2-a]pyrazin-3-yl)pyrimidin-4-yl)piperidin-3-yl)methanesulfonamide IV-114;

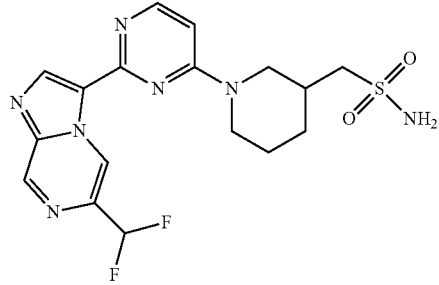 [SMILES: NS(=O)(=O)CC1CCCN(c2ccnc(-c3cnc4cnc(C(F)F)cn34)n2)C1]

2-(2-(6-(Difluoromethyl)imidazo[1,2-a]pyrazin-3-yl)pyrimidin-4-yl)-1,2,3,4-tetrahydroisoquinoline IV-115;

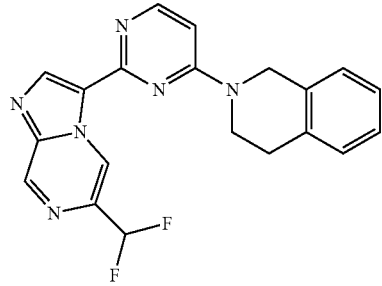 [SMILES: FC(F)c1cn2c(-c3nccc(N4CCc5ccccc5C4)n3)cnc2cn1]

2-(2-(6-(Difluoromethyl)imidazo[1,2-a]pyrazin-3-yl)pyrimidin-4-yl)octahydro-1H-isoindol-5-ol IV-116;

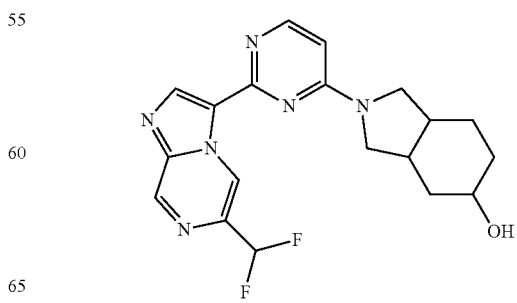

4-(2-(6-(Difluoromethyl)imidazo[1,2-a]pyrazin-3-yl)pyrimidin-4-yl)-1,4-oxazepane-6-carboxamide IV-117;

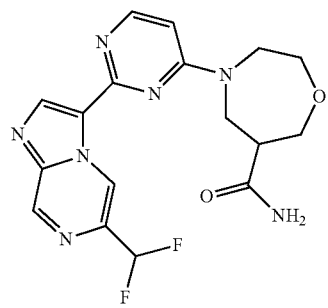 [SMILES: NC(=O)C1COCCN(c2ccnc(-c3cnc4cnc(C(F)F)cn34)n2)C1]

4-(2-(6-(Difluoromethyl)imidazo[1,2-a]pyrazin-3-yl)pyrimidin-4-yl)-2,6-dimethylmorpholine IV-119;

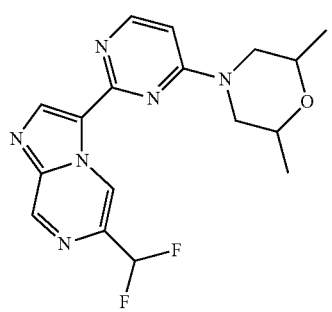 [SMILES: CC1CN(c2ccnc(-c3cnc4cnc(C(F)F)cn34)n2)CC(C)O1]

1-(2-(6-(Difluoromethyl)imidazo[1,2-a]pyrazin-3-yl)pyrimidin-4-yl)piperidin-3-ol IV-120;

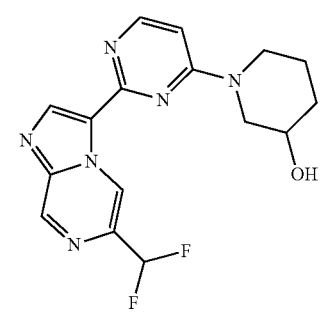 [SMILES: OC1CCCN(c2ccnc(-c3cnc4cnc(C(F)F)cn34)n2)C1]

(1-(2-(6-(Difluoromethyl)imidazo[1,2-a]pyrazin-3-yl)pyrimidin-4-yl)piperidin-3-yl)methanol IV-121;

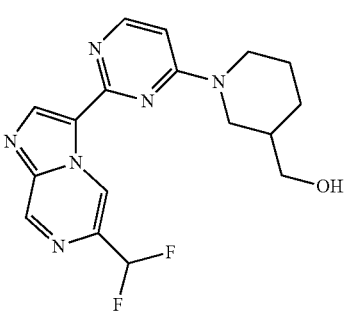 [SMILES: OCC1CCCN(c2ccnc(-c3cnc4cnc(C(F)F)cn34)n2)C1]

6-(Difluoromethyl)-3-(4-((2S,6R)-2,6-dimethylpiperidin-1-yl)pyrimidin-2-yl)imidazo[1,2-a]pyrazine IV-122;

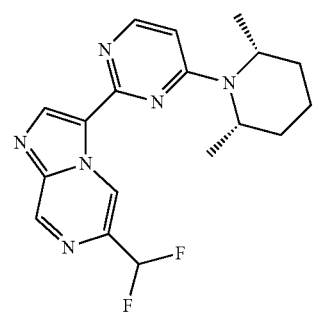 [SMILES: C[C@@H]1CCC[C@H](C)N1c1ccnc(-c2cnc3cnc(C(F)F)cn23)n1]

(R)-6-(Difluoromethyl)-3-(4-(3-methylpiperidin-1-yl)pyrimidin-2-yl)imidazo[1,2-a]pyrazine IV-129;

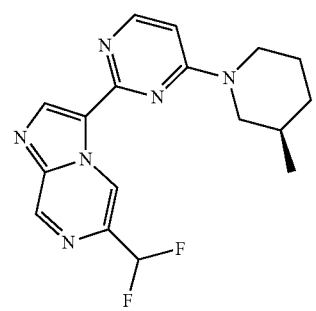 [SMILES: C[C@@H]1CCCN(c2ccnc(-c3cnc4cnc(C(F)F)cn34)n2)C1]

6-(Difluoromethyl)-3-(4-(octahydro-1H-cyclopenta[b]pyridin-1-yl)pyrimidin-2-yl)imidazo[1,2-a]pyrazine IV-130;

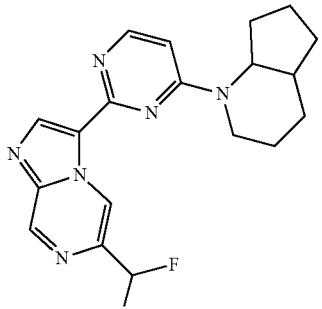

3-(4-(Azepan-1-yl)pyrimidin-2-yl)-6-(difluoromethyl)imidazo[1,2-a]pyrazine IV-131;

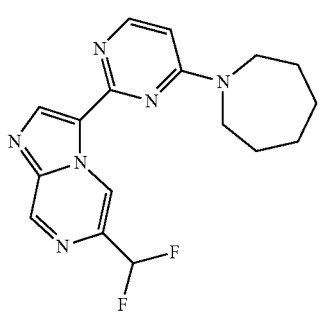 [SMILES: FC(F)c1cn2c(-c3nccc(N4CCCCCC4)n3)cnc2cn1]

tert-Butyl 6-(2-(6-(difluoromethyl)imidazo[1,2-a]pyrazin-3-
yl)pyrimidin-4-yl)octahydro-1H-pyrrolo[2,3-c]pyridine-
1-carboxylate IV-132;

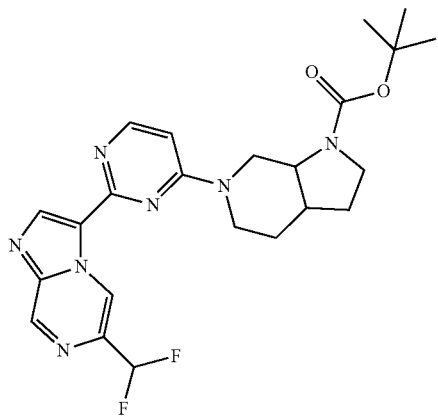 [SMILES: CC(C)(C)OC(=O)N1CCC2CCN(c3ccnc(-c4cnc5cnc(C(F)F)cn45)n3)CC21]

tert-Butyl 2-(2-(6-(difluoromethyl)imidazo[1,2-a]pyrazin-3-
yl)pyrimidin-4-yl)-2,8-diazaspiro[4.5]decane-8-carboxy-
late IV-133;

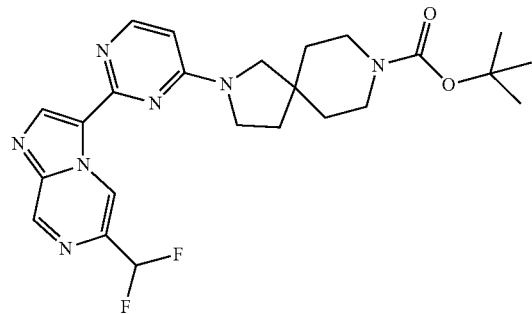 [SMILES: CC(C)(C)OC(=O)N1CCC2(CC1)CCN(c1ccnc(-c3cnc4cnc(C(F)F)cn34)n1)C2]

6-(Difluoromethyl)-3-(4-(2,3-dimethylpiperidin-1-yl)py-
rimidin-2-yl)imidazo[1,2-a]pyrazine IV-134;

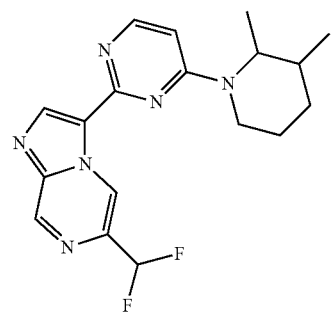 [SMILES: CC1CCCN(c2ccnc(-c3cnc4cnc(C(F)F)cn34)n2)C1C]

3-(4-(2-Azabicyclo[4.1.0]heptan-2-yl)pyrimidin-2-yl)-6-
(difluoromethyl)imidazo[1,2-a]pyrazine IV-135;

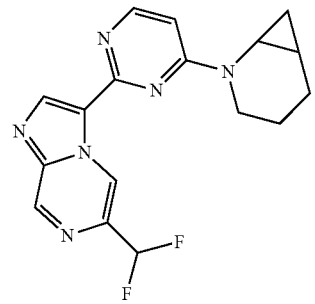 [SMILES: FC(F)c1cn2c(-c3nccc(N4CCCC5CC54)n3)cnc2cn1]

(R)-(1-(2-(6-(Difluoromethyl)imidazo[1,2-a]pyrazin-3-yl)
pyrimidin-4-yl)piperidin-2-yl)methanol IV-136;

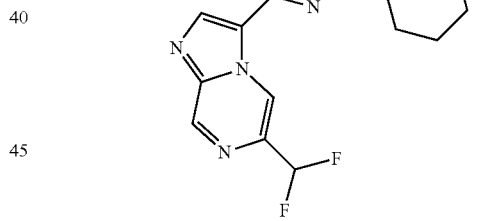

(S)-6-(Difluoromethyl)-3-(4-(3-methylpiperidin-1-yl)py-
rimidin-2-yl)imidazo[1,2-a]pyrazine IV-137;

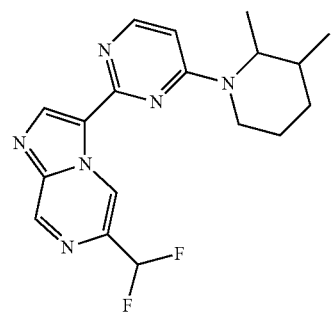

(R)-(1-(2-(6-(Difluoromethyl)imidazo[1,2-a]pyrazin-3-yl)
pyrimidin-4-yl)piperidin-3-yl)methanol IV-138;

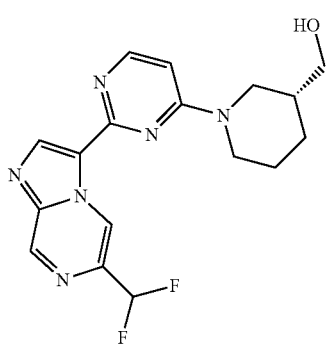 [SMILES: OC[C@@H]1CCCN(c2ccnc(-c3cnc4cnc(C(F)F)cn34)n2)C1]

((1-(2-(6-(Difluoromethyl)imidazo[1,2-a]pyrazin-3-yl)py-
rimidin-4-yl)piperidin-3-yl)imino)dimethyl-$\lambda^6$-sulfanone
IV-141;

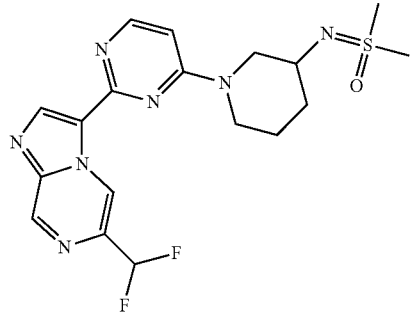 [SMILES: CS(C)(=O)=NC1CCCN(c2ccnc(-c3cnc4cnc(C(F)F)cn34)n2)C1]

(S)-(1-(2-(6-(Difluoromethyl)imidazo[1,2-a]pyrazin-3-yl)
pyrimidin-4-yl)piperidin-3-yl)methanol IV-142;

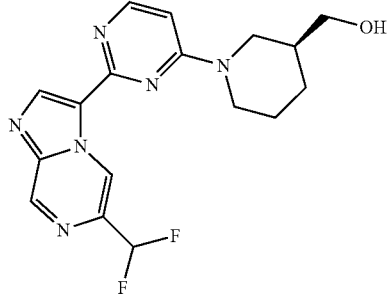 [SMILES: OC[C@H]1CCCN(c2ccnc(-c3cnc4cnc(C(F)F)cn34)n2)C1]

N-((1-(2-(6-(Difluoromethyl)imidazo[1,2-a]pyrazin-3-yl)
pyrimidin-4-yl)piperidin-3-yl)methyl)methanesulfona-
mide IV-152;

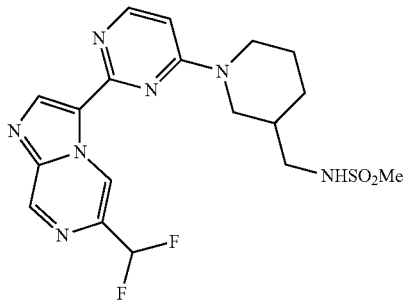

1-(2-(6-(Difluoromethyl)imidazo[1,2-a]pyrazin-3-yl)py-
rimidin-4-yl)-N-methylpiperidine-3-sulfonamide IV-164;

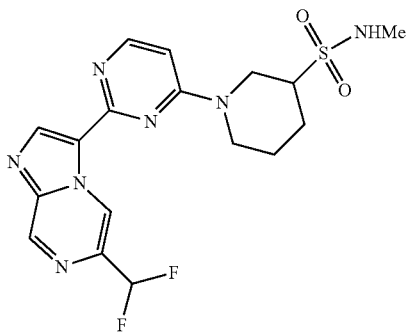 [SMILES: CNS(=O)(=O)C1CCCN(c2ccnc(-c3cnc4cnc(C(F)F)cn34)n2)C1]

6-(Difluoromethyl)-3-(4-(3-(methylsulfonyl)piperidin-1-yl)
pyrimidin-2-yl)imidazo[1,2-a]pyrazine IV-165;

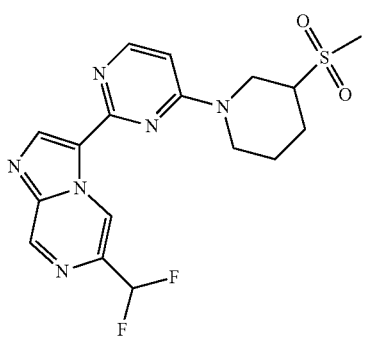 [SMILES: CS(=O)(=O)C1CCCN(c2ccnc(-c3cnc4cnc(C(F)F)cn34)n2)C1]

N-(1-(2-(6-(Difluoromethyl)imidazo[1,2-a]pyrazin-3-yl)py-
rimidin-4-yl)piperidin-3-yl)-N-methylmethanesulfona-
mide IV-168;

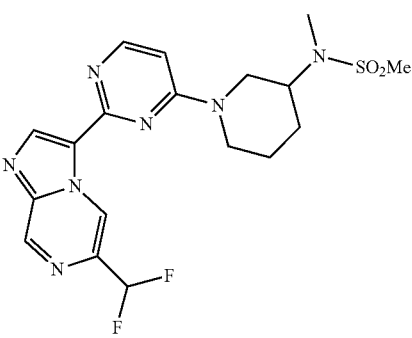 [SMILES: CN(C1CCCN(c2ccnc(-c3cnc4cnc(C(F)F)cn34)n2)C1)S(C)(=O)=O]

N-(1-(2-(6-(Difluoromethyl)imidazo[1,2-a]pyrazin-3-yl)py-
rimidin-4-yl)piperidin-3-yl)methanesulfonamide IV-169;

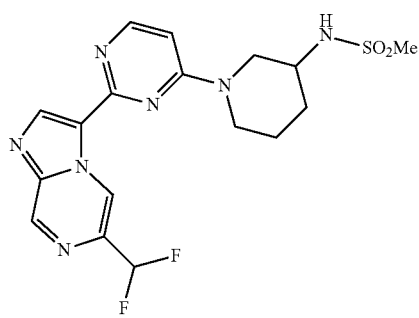 [SMILES: CS(=O)(=O)NC1CCCN(c2ccnc(-c3cnc4cnc(C(F)F)cn34)n2)C1]

1-(2-(6-(Difluoromethyl)imidazo[1,2-a]pyrazin-3-yl)pyrimidin-4-yl)-N,N-dimethylpiperidine-3-sulfonamide IV-170;

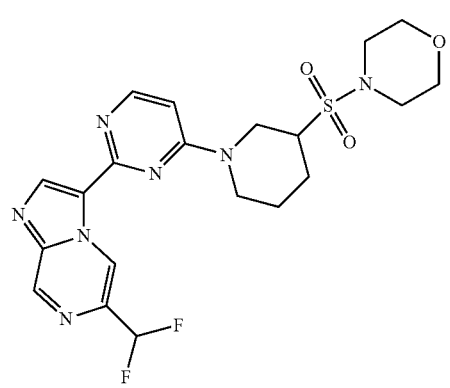

4-(1-(2-(6-(Difluoromethyl)imidazo[1,2-a]pyrimidin-4-yl)piperidin-3-yl)thiazole IV-174;

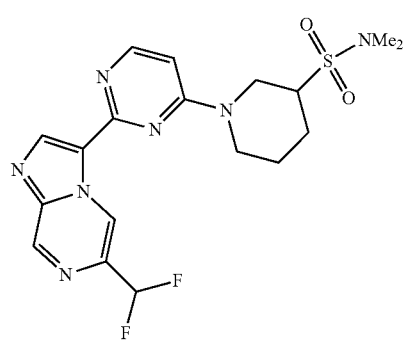 [SMILES: CN(C)S(=O)(=O)C1CCCN(c2ccnc(-c3cnc4cnc(C(F)F)cn34)n2)C1]

N-Cyclopentyl-1-(2-(6-(difluoromethyl)imidazo[1,2-a]pyrazin-3-yl)pyrimidin-4-yl)piperidine-3-sulfonamide IV-171;

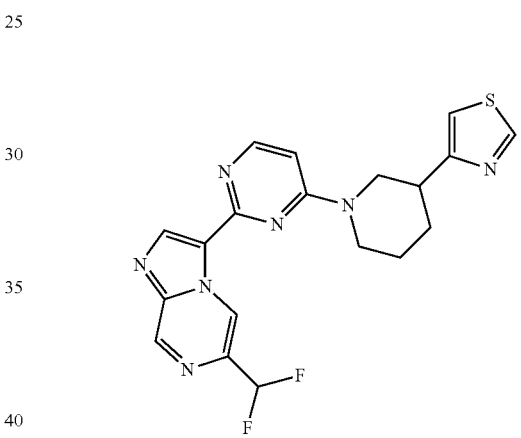

3-(6-(4-Acetylpiperazin-1-yl)pyridin-2-yl)imidazo[1,2-a]pyrazine-6-carboxamide IV-184;

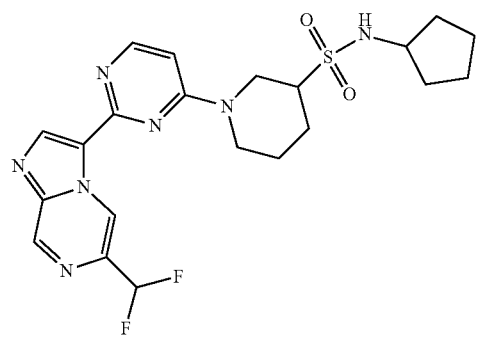 [SMILES: O=S(=O)(NC1CCCC1)C1CCCN(c2ccnc(-c3cnc4cnc(C(F)F)cn34)n2)C1]

4-((1-(2-(6-(Difluoromethyl)imidazo[1,2-a]pyrazin-3-yl)pyrimidin-4-yl)piperidin-3-yl)sulfonyl)morpholine IV-172;

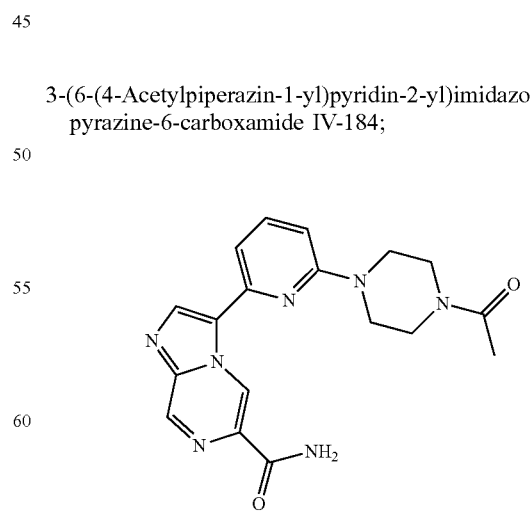

3-(4-(3-Methylpiperidin-1-yl)pyrimidin-2-yl)imidazo[1,2-a]pyrazine-6-carboxamide IV-187;

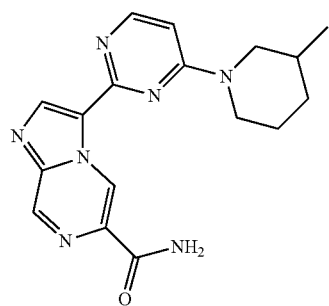 [SMILES: CC1CCCN(c2ccnc(-c3cnc4cnc(C(N)=O)cn34)n2)C1]

3-(4-(3-Methyl-5-(1H-pyrazol-4-yl)piperazin-1-yl)pyrimidin-2-yl)-6-(trifluoromethyl)imidazo[1,2-a]pyrazine IV-189;

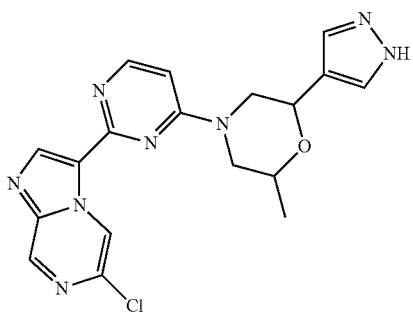

4-(2-(6-Chloroimidazo[1,2-a]pyrazin-3-yl)pyrimidin-4-yl)-2-methyl-6-(1H-pyrazol-4-yl)morpholine IV-193;

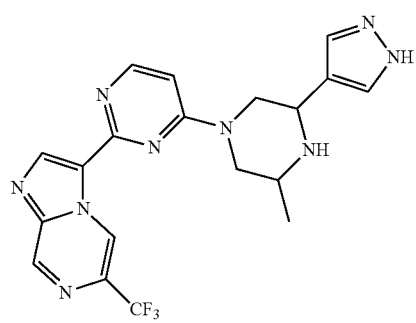

3-(4-(4-Acetyl-1,4-diazepan-1-yl)pyrimidin-2-yl)imidazo[1,2-a]pyrazine-6-carboxamide IV-190;

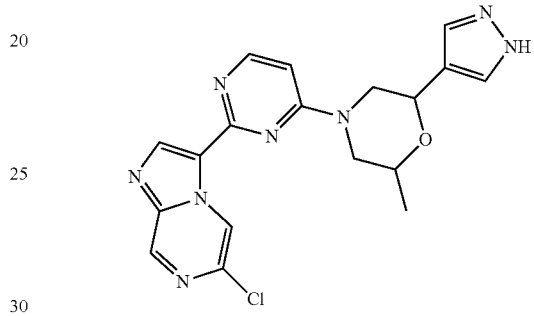

3-(4-(2-Methyl-6-(1H-pyrazol-4-yl)morpholino)pyrimidin-2-yl)imidazo[1,2-a]pyrazine-6-carbonitrile IV-194;

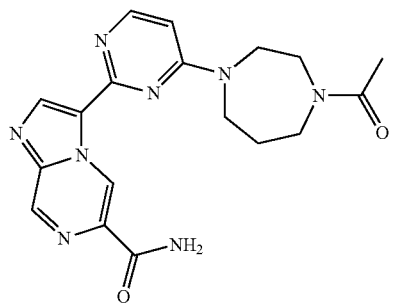 [SMILES: CC(=O)N1CCCN(c2ccnc(-c3cnc4cnc(C(N)=O)cn34)n2)CC1]

3-(4-(2-Methyl-6-(1H-pyrazol-4-yl)morpholino)pyrimidin-2-yl)imidazo[1,2-a]pyrazine-6-carbonitrile IV-191;

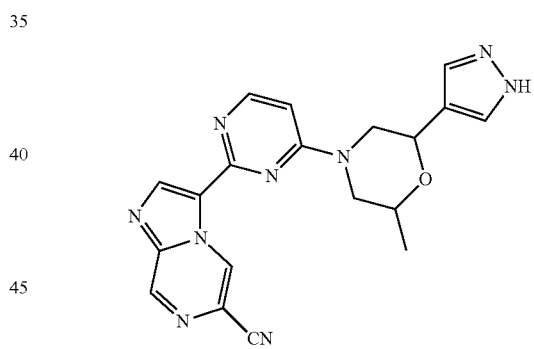

1-(4-(2-(6-(1H-Pyrazol-3-yl)imidazo[1,2-a]pyrazin-3-yl)pyrimidin-4-yl)piperazin-1-yl)ethan-1-one IV-203;

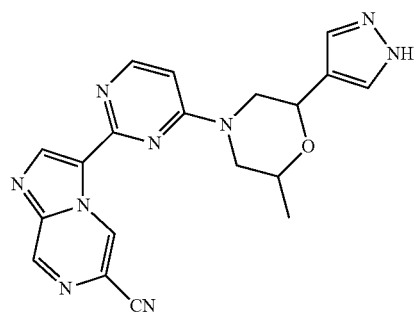 [SMILES: CC1CN(c2ccnc(-c3cnc4cnc(C#N)cn34)n2)CC(c2cn[nH]c2)O1]

4-(2-(6-Chloroimidazo[1,2-a]pyrazin-3-yl)pyrimidin-4-yl)-2-methyl-6-(1H-pyrazol-4-yl)morpholine IV-192;

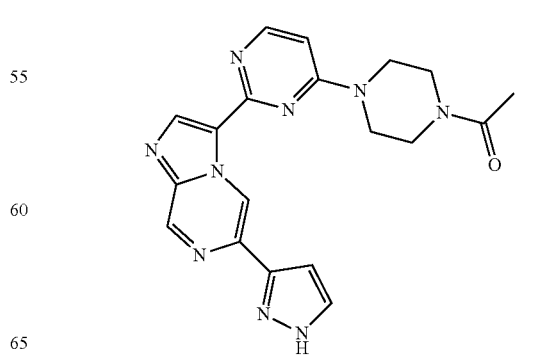

3-(6-(Piperidin-1-yl)pyridin-2-yl)imidazo[1,2-a]pyrazine-6-carboxamide IV-204;

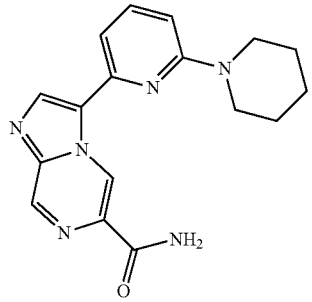 [SMILES: NC(=O)c1cn2c(-c3cccc(N4CCCCC4)n3)cnc2cn1]

3-(6-(3-Methylpiperidin-1-yl)pyridin-2-yl)imidazo[1,2-a]pyrazine-6-carboxamide IV-205;

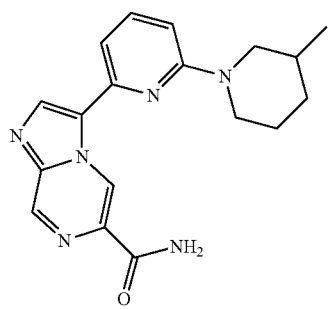 [SMILES: CC1CCCN(c2cccc(-c3cnc4cnc(C(N)=O)cn34)n2)C1]

Cis-6-Chloro-3-(4-(3-methyl-5-(H-pyrazol-4-yl)piperazin-1-yl)pyrimidin-2-yl)imidazo[1,2-a]pyrazine IV-206;

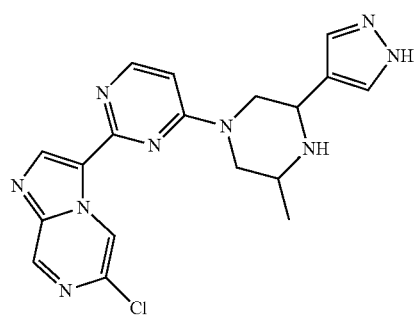 [SMILES: CC1CN(c2ccnc(-c3cnc4cnc(Cl)cn34)n2)CC(c2cn[nH]c2)N1]

Cis-3-(4-(2-Methyl-3-(1H-pyrazol-3-yl)piperazin-1-yl)pyrimidin-2-yl)-6-(trifluoromethyl)imidazo[1,2-a]pyrazine IV-207;

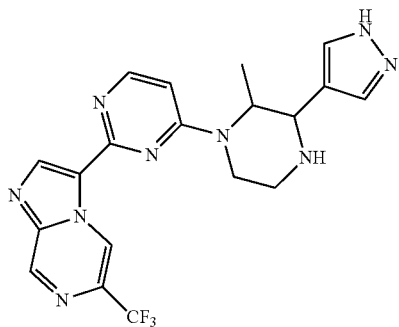

Cis-3-(4-(3-Methyl-2-(1H-pyrazol-4-yl)piperazin-1-yl)pyrimidin-2-yl)-6-(trifluoromethyl)imidazo[1,2-a]pyrazine IV-208;

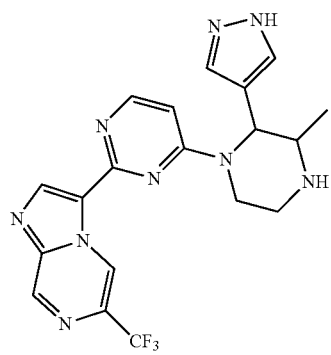 [SMILES: CC1NCCN(c2ccnc(-c3cnc4cnc(C(F)(F)F)cn34)n2)C1c1cn[nH]c1]

3-(6-(6-Oxooctahydro-2H-pyrido[1,2-a]pyrazin-2-yl)pyridin-2-yl)imidazo[1,2-a]pyrazine-6-carboxamide IV-210;

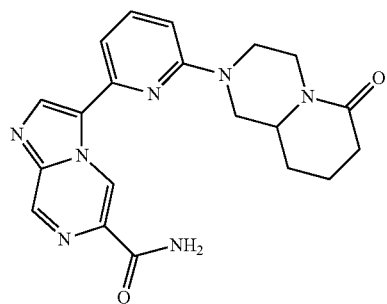 [SMILES: NC(=O)c1cn2c(-c3cccc(N4CCN5C(=O)CCCC5C4)n3)cnc2cn1]

3-(4-(3-(1H-Pyrazol-4-yl)piperazin-1-yl)pyrimidin-2-yl)-6-(trifluoromethyl)imidazo[1,2-a]pyrazine IV-211;

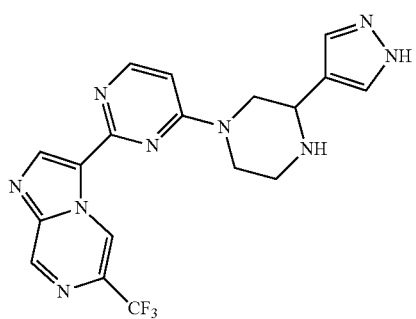 [SMILES: FC(F)(F)c1cn2c(-c3nccc(N4CCNC(c5cn[nH]c5)C4)n3)cnc2cn1]

3-(6-(4-Methylpiperazin-1-yl)pyridin-2-yl)imidazo[1,2-a]pyrazine-6-carboxamide IV-212;

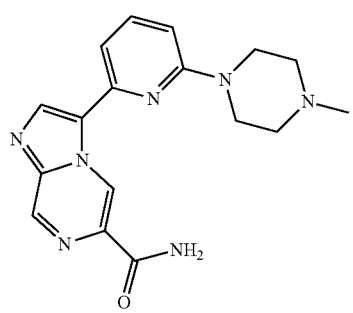 [SMILES: CN1CCN(c2cccc(-c3cnc4cnc(C(N)=O)cn34)n2)CC1]

Cis-3-Methyl-2-(1H-pyrazol-4-yl)-4-(2-(6-(trifluoromethyl)imidazo[1,2-a]pyrazin-3-yl)pyrimidin-4-yl)morpholine IV-215;

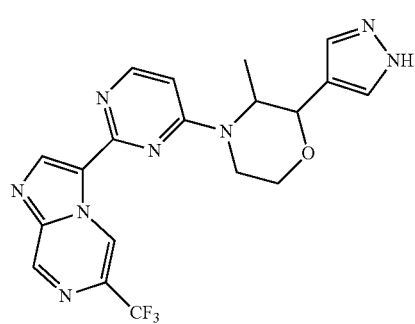 [SMILES: CC1C(c2cn[nH]c2)OCCN1c1ccnc(-c2cnc3cnc(C(F)(F)F)cn23)n1]

Trans-3-Methyl-2-(1H-pyrazol-4-yl)-4-(2-(6-(trifluoromethyl)imidazo[1,2-a]pyrazin-3-yl)pyrimidin-4-yl)morpholine IV-218;

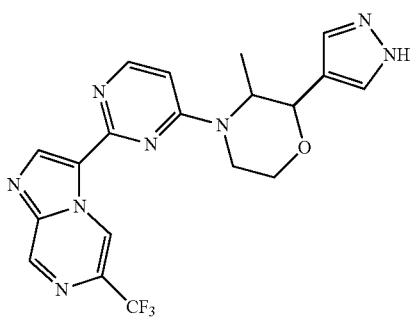 [SMILES: CC1C(c2cn[nH]c2)OCCN1c1ccnc(-c2cnc3cnc(C(F)(F)F)cn23)n1]

3-(6-(4-Hydroxypiperidin-1-yl)pyridin-2-yl)imidazo[1,2-a]pyrazine-6-carboxamide IV-219;

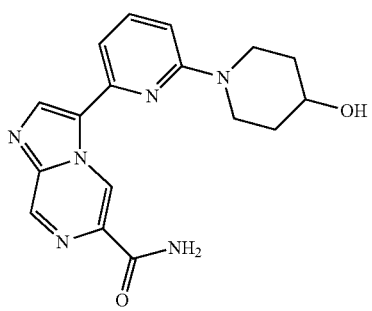 [SMILES: NC(=O)c1cn2c(-c3cccc(N4CCC(O)CC4)n3)cnc2cn1]

3-(6-(3-(Hydroxymethyl)piperidin-1-yl)pyridin-2-yl)imidazo[1,2-a]pyrazine-6-carboxamide IV-220;

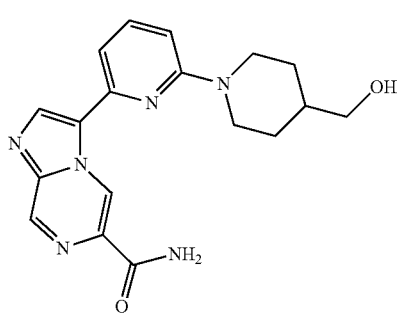 [SMILES: NC(=O)c1cn2c(-c3cccc(N4CCC(CO)CC4)n3)cnc2cn1]

3-(6-(4-(Hydroxymethyl)piperidin-1-yl)pyridin-2-yl)imidazo[1,2-a]pyrazine-6-carboxamide IV-221;

3-(4-(2,5-Dimethyl-3-(1H-pyrazol-4-yl)piperazin-1-yl)pyrimidin-2-yl)-6-(trifluoromethyl)imidazo[1,2-a]pyrazine IV-222;

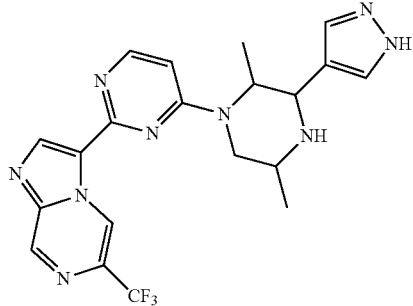

3-(6-(4-(2-Hydroxypropan-2-yl)piperidin-1-yl)pyridin-2-yl)
imidazo[1,2-a]pyrazine-6-carboxamide IV-226;

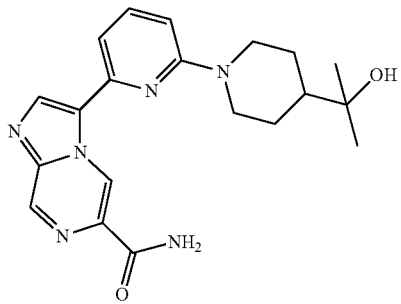 [SMILES: CC(C)(O)C1CCN(c2cccc(-c3cnc4cnc(C(N)=O)cn34)n2)CC1]

3-(6-(3-Oxohexahydroimidazo[1,5-a]pyrazin-7(1H)-yl)
pyridin-2-yl)imidazo[1,2-a]pyrazine-6-carboxamide
IV-227;

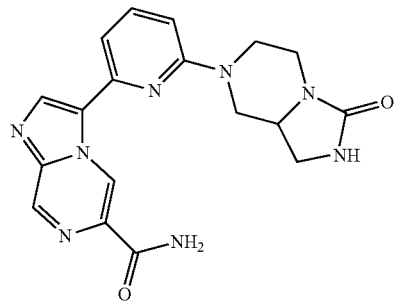 [SMILES: NC(=O)c1cn2c(-c3cccc(N4CCN5C(=O)NCC5C4)n3)cnc2cn1]

(S)-3-(6-(6-Oxooctahydro-2H-pyrido[1,2-a]pyrazin-2-yl)
pyridin-2-yl)imidazo[1,2-a]pyrazine-6-carboxamide
IV-228;

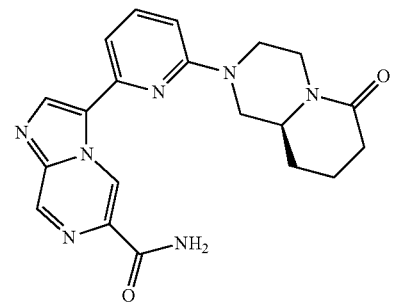 [SMILES: NC(=O)c1cn2c(-c3cccc(N4CCN5C(=O)CCC[C@H]5C4)n3)cnc2cn1]

Cis-4-(2-(6-Chloroimidazo[1,2-a]pyrazin-3-yl)pyrimidin-4-
yl)-3-methyl-2-(1H-pyrazol-4-yl)morpholine IV-235;

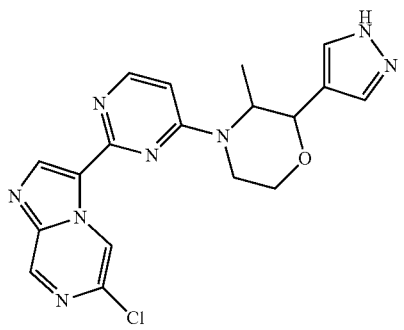 [SMILES: CC1C(c2cn[nH]c2)OCCN1c1ccnc(-c2cnc3cnc(Cl)cn23)n1]

Trans-4-(2-(6-Chloroimidazo[1,2-a]pyrazin-3-yl)pyrimidin-
4-yl)-3-methyl-2-(1H-pyrazol-4-yl)morpholine IV-236;

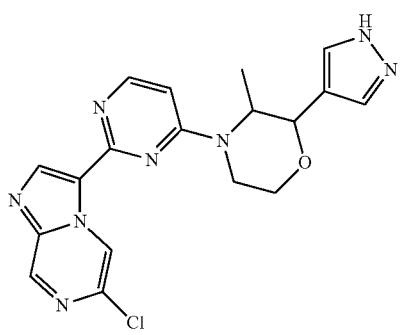 [SMILES: CC1C(c2cn[nH]c2)OCCN1c1ccnc(-c2cnc3cnc(Cl)cn23)n1]

3-(4-(4-Methylpiperazin-1-yl)pyrimidin-2-yl)imidazo[1,2-
a]pyrazine-6-carboxamide IV-239;


3-(4-(2-(Hydroxymethyl)piperidin-1-yl)pyrimidin-2-yl)imi-
dazo[1,2-a]pyrazine-6-carboxamide IV-241;

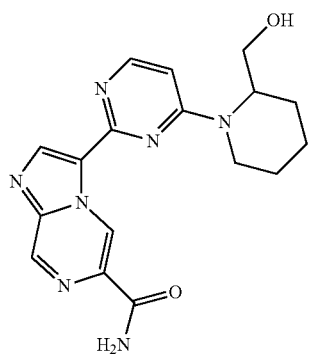

3-(4-(3-(Hydroxymethyl)piperidin-1-yl)pyrimidin-2-yl)imidazo[1,2-a]pyrazine-6-carboxamide IV-242;

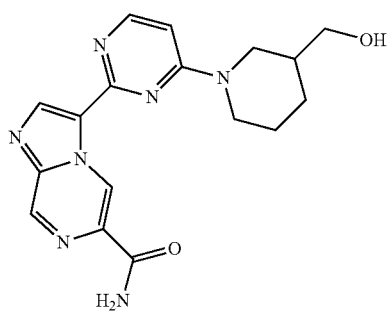 [SMILES: NC(=O)c1cn2c(-c3nccc(N4CCCC(CO)C4)n3)cnc2cn1]

3-(4-(4-(Hydroxymethyl)piperidin-1-yl)pyrimidin-2-yl)imidazo[1,2-a]pyrazine-6-carboxamide IV-243;

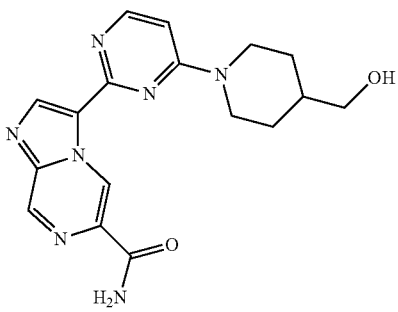 [SMILES: NC(=O)c1cn2c(-c3nccc(N4CCC(CO)CC4)n3)cnc2cn1]

3-(4-(4-Acetamidopiperidin-1-yl)pyrimidin-2-yl)imidazo[1,2-a]pyrazine-6-carboxamide IV-248;

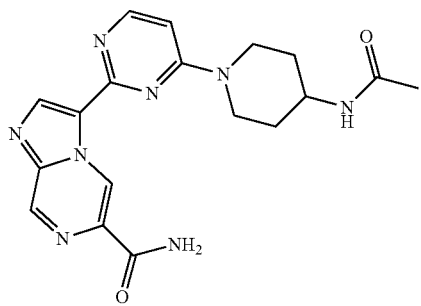 [SMILES: CC(=O)NC1CCN(c2ccnc(-c3cnc4cnc(C(N)=O)cn34)n2)CC1]

3-(4-(3-Acetamidopiperidin-1-yl)pyrimidin-2-yl)imidazo[1,2-a]pyrazine-6-carboxamide IV-249;

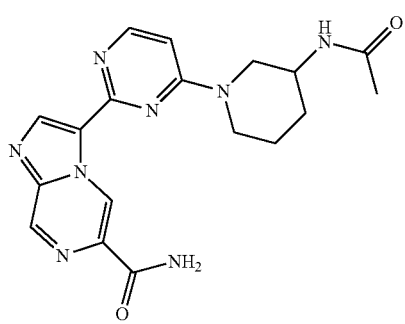 [SMILES: CC(=O)NC1CCCN(c2ccnc(-c3cnc4cnc(C(N)=O)cn34)n2)C1]

3-(4-(3-(Methylsulfonamido)piperidin-1-yl)pyrimidin-2-yl)imidazo[1,2-a]pyrazine-6-carboxamide IV-250;

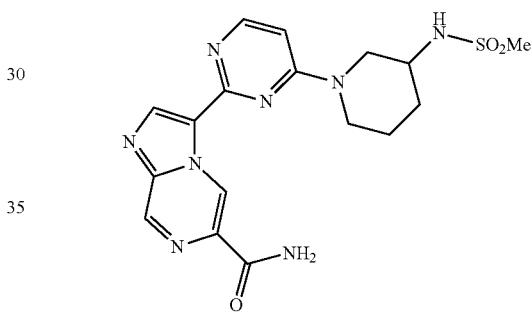

3-(4-(3-(N-Methylsulfamoyl)piperidin-1-yl)pyrimidin-2-yl)imidazo[1,2-a]pyrazine-6-carboxamide IV-251;

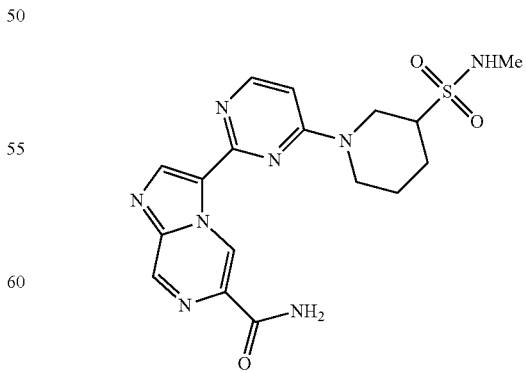

3-(4-(4-(N-Methylsulfamoyl)piperidin-1-yl)pyrimidin-2-yl)imidazo[1,2-a]pyrazine-6-carboxamide IV-252;

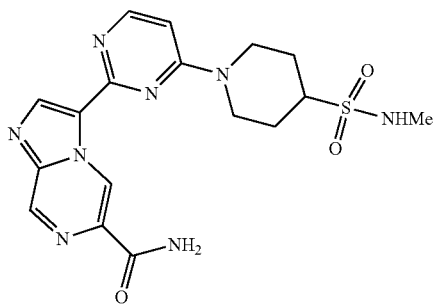 [SMILES: CNS(=O)(=O)C1CCN(c2ccnc(-c3cnc4cnc(C(N)=O)cn34)n2)CC1]

3-(4-(3-Cyano-4-oxopiperidin-1-yl)pyrimidin-2-yl)imidazo[1,2-a]pyrazine-6-carboxamide IV-253;

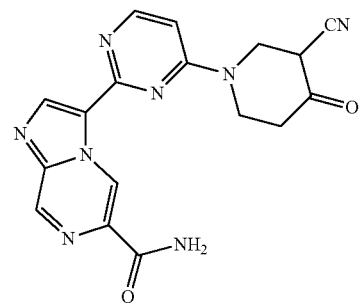 [SMILES: N#CC1CN(c2ccnc(-c3cnc4cnc(C(N)=O)cn34)n2)CCC1=O]

3-(4-(4-Cyanopiperidin-1-yl)pyrimidin-2-yl)imidazo[1,2-a]pyrazine-6-carboxamide IV-254;

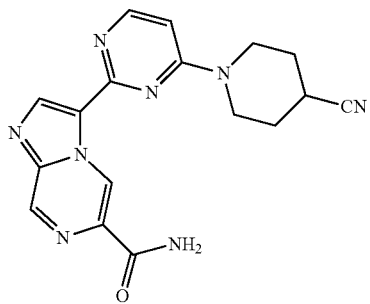 [SMILES: N#CC1CCN(c2ccnc(-c3cnc4cnc(C(N)=O)cn34)n2)CC1]

3-(4-(3-(1H-Imidazol-1-yl)piperidin-1-yl)pyrimidin-2-yl)-6-(trifluoromethyl)imidazo[1,2-a]pyrazine IV-255;

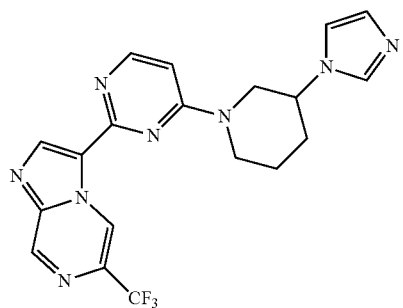 [SMILES: FC(F)(F)c1cn2c(-c3nccc(N4CCCC(n5ccnc5)C4)n3)cnc2cn1]

3-(4-(6-Oxooctahydro-2H-pyrido[1,2-a]pyrazin-2-yl)pyrimidin-2-yl)imidazo[1,2-a]pyrazine-6-carboxamide IV-257;

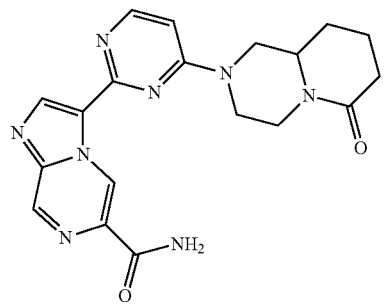 [SMILES: NC(=O)c1cn2c(-c3nccc(N4CCN5C(=O)CCCC5C4)n3)cnc2cn1]

3-(4-(2-Cyanopiperidin-1-yl)pyrimidin-2-yl)imidazo[1,2-a]pyrazine-6-carboxamide IV-258;

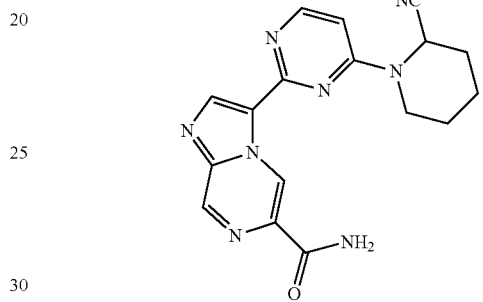

1-(4-(6-(6-(Trifluoromethyl)imidazo[1,2-a]pyrazin-3-yl)pyridin-2-yl)piperazin-1-yl)ethan-1-one IV-259;

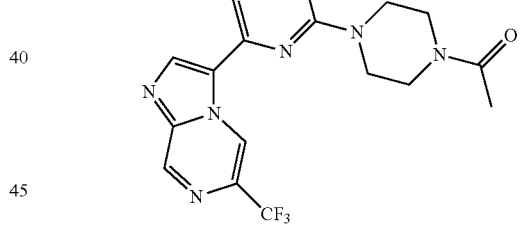

3-(6-(4-Acetylpiperazin-1-yl)pyridin-2-yl)-N-methylimidazo[1,2-a]pyrazine-6-carboxamide IV-260;

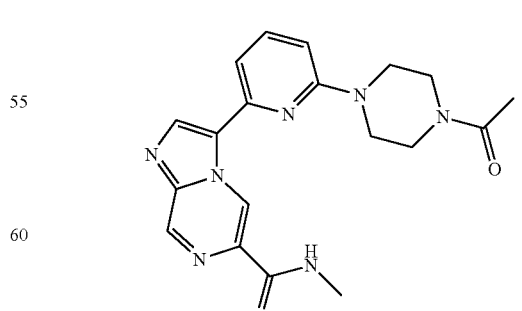

3-(4-(2-Methylpiperidin-1-yl)pyrimidin-2-yl)imidazo[1,2-a]pyrazine-6-carboxamide IV-261;

1033

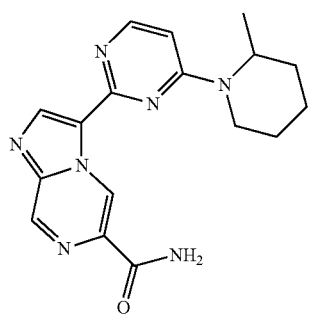 [SMILES: CC1CCCCN1c1ccnc(-c2cnc3cnc(C(N)=O)cn23)n1]

3-(4-(5-Oxohexahydro-1H-pyrrolo[1,2-a][1,4]diazepin-2(3H)-yl)pyrimidin-2-yl)imidazo[1,2-a]pyrazine-6-carboxamide IV-262;

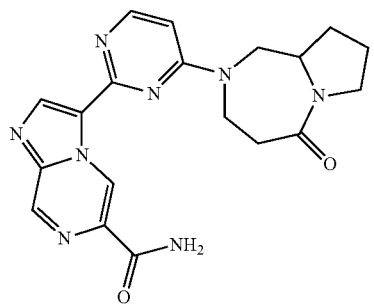 [SMILES: NC(=O)c1cn2c(-c3nccc(N4CCC(=O)N5CCCC5C4)n3)cnc2cn1]

3-(4-(4-Oxooctahydro-2H-pyrido[1,2-a]pyrazin-2-yl)pyrimidin-2-yl)imidazo[1,2-a]pyrazine-6-carboxamide IV-263;

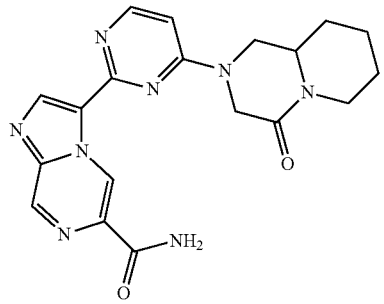 [SMILES: NC(=O)c1cn2c(-c3nccc(N4CC(=O)N5CCCCC5C4)n3)cnc2cn1]

3-(4-(2,3-Dimethylpiperidin-1-yl)pyrimidin-2-yl)imidazo[1,2-a]pyrazine-6-carboxamide IV-264;

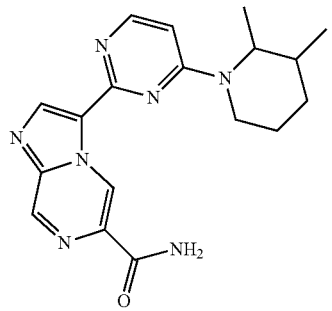 [SMILES: CC1CCCN(c2ccnc(-c3cnc4cnc(C(N)=O)cn34)n2)C1C]

1034

3-(4-(Octahydro-2H-pyrido[1,2-a]pyrazin-2-yl)pyrimidin-2-yl)imidazo[1,2-a]pyrazine-6-carboxamide IV-265;

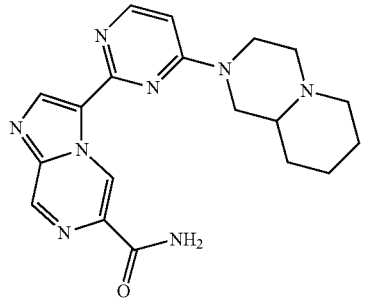 [SMILES: NC(=O)c1cn2c(-c3nccc(N4CCN5CCCCC5C4)n3)cnc2cn1]

3-(4-(1,4-Dioxa-8-azaspiro[4.5]decan-8-yl)pyrimidin-2-yl)imidazo[1,2-a]pyrazine-6-carboxamide IV-266;

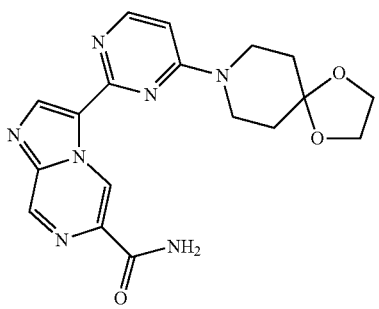 [SMILES: NC(=O)c1cn2c(-c3nccc(N4CCC5(CC4)OCCO5)n3)cnc2cn1]

3-(4-(3-(N-Methylacetamido)pyrrolidin-1-yl)pyrimidin-2-yl)imidazo[1,2-a]pyrazine-6-carboxamide IV-267;

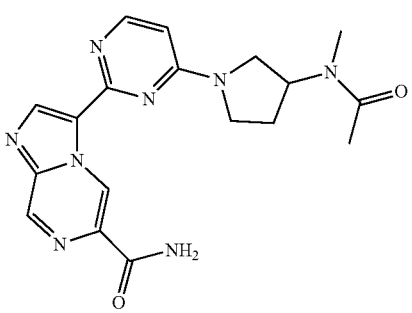 [SMILES: CC(=O)N(C)C1CCN(c2ccnc(-c3cnc4cnc(C(N)=O)cn34)n2)C1]

3-(4-(4-Oxohexahydropyrrolo[1,2-a]pyrazin-2(1H)-yl)pyrimidin-2-yl)imidazo[1,2-a]pyrazine-6-carboxamide IV-268;

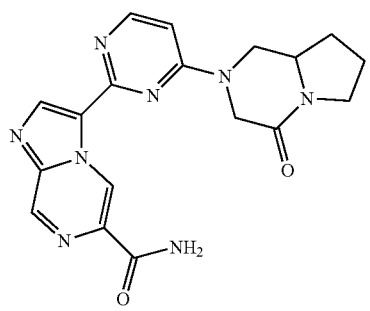 [SMILES: NC(=O)c1cn2c(-c3nccc(N4CC(=O)N5CCCC5C4)n3)cnc2cn1]

3-(4-(1-Oxa-8-azaspiro[4.5]decan-8-yl)pyrimidin-2-yl)imi-dazo[1,2-a]pyrazine-6-carboxamide IV-269;

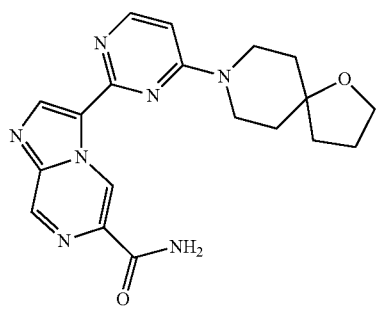 [SMILES: NC(=O)c1cn2c(-c3nccc(N4CCC5(CCCO5)CC4)n3)cnc2cn1]

3-(4-(6-Oxa-2-azaspiro[3.4]octan-2-yl)pyrimidin-2-yl)imi-dazo[1,2-a]pyrazine-6-carboxamide IV-270;

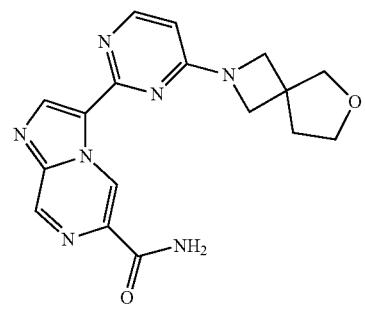 [SMILES: NC(=O)c1cn2c(-c3nccc(N4CC5(CCOC5)C4)n3)cnc2cn1]

3-(4-(2,5-Dimethylpiperidin-1-yl)pyrimidin-2-yl)imidazo[1,2-a]pyrazine-6-carboxamide IV-271;

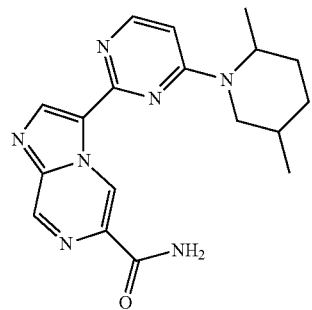 [SMILES: CC1CCC(C)N(c2ccnc(-c3cnc4cnc(C(N)=O)cn34)n2)C1]

3-(4-(4-Acetyl-2-methylpiperazin-1-yl)pyrimidin-2-yl)imi-dazo[1,2-a]pyrazine-6-carboxamide IV-272;

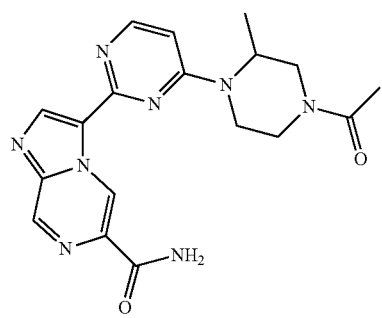 [SMILES: CC(=O)N1CCN(c2ccnc(-c3cnc4cnc(C(N)=O)cn34)n2)C(C)C1]

3-(6-(4-Acetylpiperazin-1-yl)pyridin-2-yl)-N,N-dimethyl-imidazo[1,2-a]pyrazine-6-carboxamide IV-276;

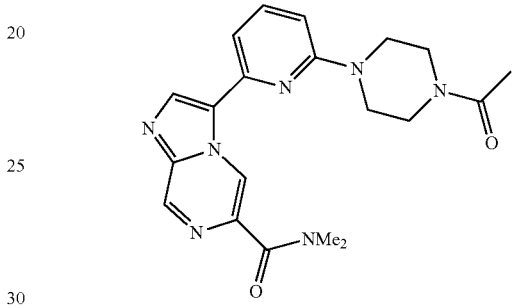

3-(4-(4-(Cyclopropanecarbonyl)piperazin-1-yl)pyrimidin-2-yl)imidazo[1,2-a]pyrazine-6-carboxamide IV-277;

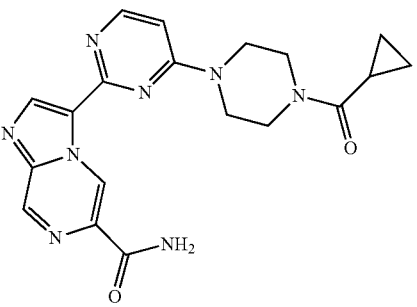

6-Chloro-3-(4-(2,5-dimethyl-3-(5-methyl-1H-pyrazol-4-yl)piperazin-1-yl)pyrimidin-2-yl)imidazo[1,2-a]pyrazine (all syn diastereomer) IV-278;

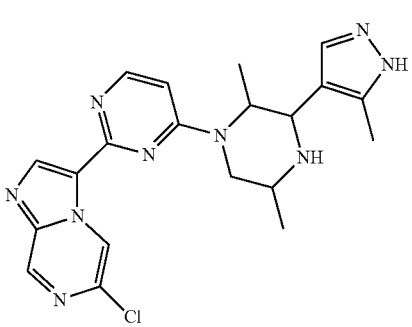 [SMILES: Cc1[nH]ncc1C1NC(C)CN(c2ccnc(-c3cnc4cnc(Cl)cn34)n2)C1C]

6-Bromo-3-(4-(2,5-dimethyl-3-(1H-pyrazol-4-yl)piperazin-1-yl)pyrimidin-2-yl)imidazo[1,2-a]pyrazine (all syn diastereomer) IV-279;

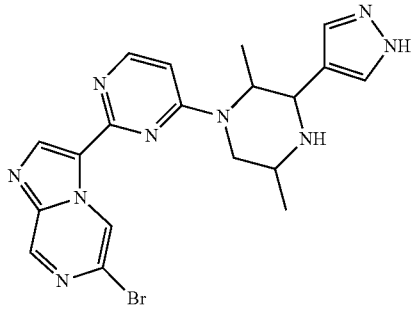 [SMILES: CC1CN(c2ccnc(-c3cnc4cnc(Br)cn34)n2)C(C)C(c2cn[nH]c2)N1]

Cis-3-(4-(3-Methyl-2-(1H-pyrazol-4-yl)morpholino)pyrimidin-2-yl)imidazo[1,2-a]pyrazine-6-carbonitrile IV-280;

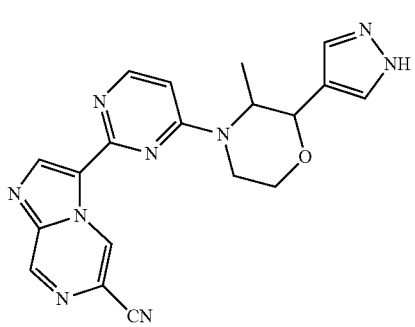 [SMILES: CC1C(c2cn[nH]c2)OCCN1c1ccnc(-c2cnc3cnc(C#N)cn23)n1]

Trans-3-(4-(3-Methyl-2-(1H-pyrazol-4-yl)morpholino)pyrimidin-2-yl)imidazo[1,2-a]pyrazine-6-carbonitrile IV-281;

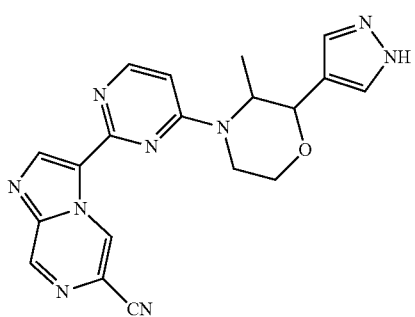 [SMILES: CC1C(c2cn[nH]c2)OCCN1c1ccnc(-c2cnc3cnc(C#N)cn23)n1]

3-(6-(4-(Cyclopropanecarbonyl)piperazin-1-yl)pyridin-2-yl)imidazo[1,2-a]pyrazine-6-carboxamide IV-284;

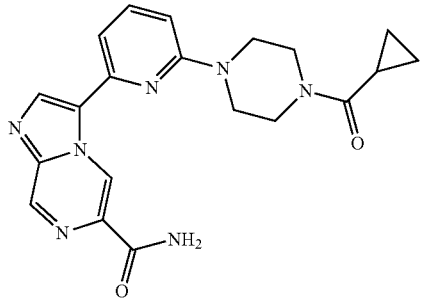 [SMILES: NC(=O)c1cn2c(-c3cccc(N4CCN(C(=O)C5CC5)CC4)n3)cnc2cn1]

1-(4-(2-(6-(Pyridin-4-yl)imidazo[1,2-a]pyrazin-3-yl)pyrimidin-4-yl)piperazin-1-yl)ethan-1-one IV-285;

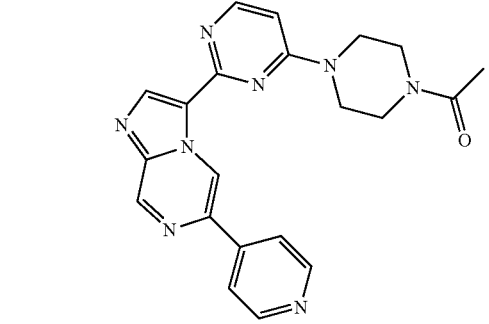 [SMILES: CC(=O)N1CCN(c2ccnc(-c3cnc4cnc(-c5ccncc5)cn34)n2)CC1]

2-(2-(6-Chloroimidazo[1,2-a]pyrazin-3-yl)pyrimidin-4-yl)octahydro-6H-pyrido[1,2-c]pyrazin-6-one IV-286;

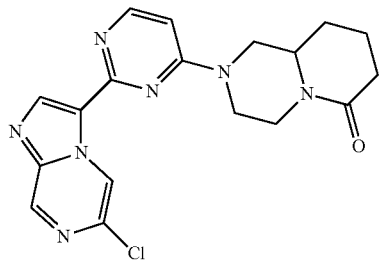 [SMILES: O=C1CCCC2CN(c3ccnc(-c4cnc5cnc(Cl)cn45)n3)CCN12]

3-(4-(2,5-Dimethyl-3-(1H-pyrazol-4-yl)piperidin-1-yl)pyrimidin-2-yl)-6-(trifluoromethyl)imidazo[1,2-a]pyrazine (all syn diastereoisomer) IV-304;

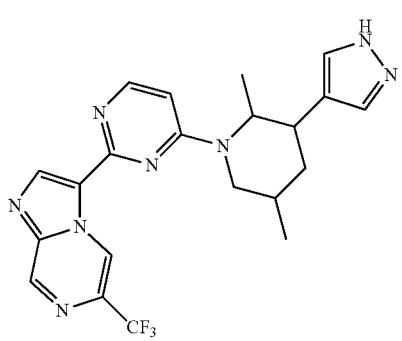

1039

3-(4-(2,5-Dimethyl-3-(1H-pyrazol-4-yl)piperazin-1-yl)pyrimidin-2-yl)imidazo[1,2-a]pyrazine-6-carbonitrile (all syn diastereoisomer) IV-305;

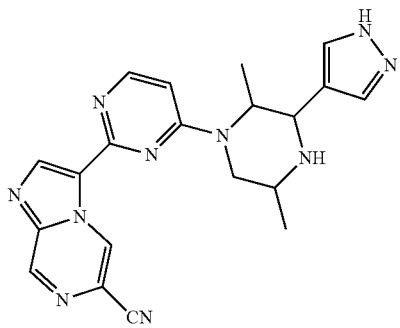 [SMILES: CC1CN(c2ccnc(-c3cnc4cnc(C#N)cn34)n2)C(C)C(c2cn[nH]c2)N1]

Cis-4-(2-(6-Bromoimidazo[1,2-a]pyrazin-3-yl)pyrimidin-4-yl)-3-methyl-2-(1H-pyrazol-4-yl)morpholine IV-306;

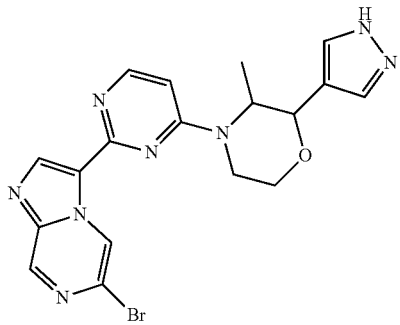 [SMILES: CC1C(c2cn[nH]c2)OCCN1c1ccnc(-c2cnc3cnc(Br)cn23)n1]

Trans-4-(2-(6-Bromoimidazo[1,2-a]pyrazin-3-yl)pyrimidin-4-yl)-3-methyl-2-(1H-pyrazol-4-yl)morpholine IV-312;

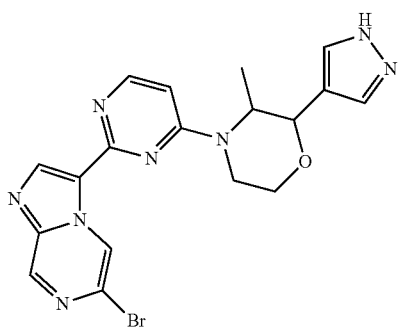 [SMILES: CC1C(c2cn[nH]c2)OCCN1c1ccnc(-c2cnc3cnc(Br)cn23)n1]

5-(1-(2-(6-(Trifluoromethyl)imidazo[1,2-a]pyrazin-3-yl)pyrimidin-4-yl)piperidin-3-yl)isoxazole IV-317;

1040

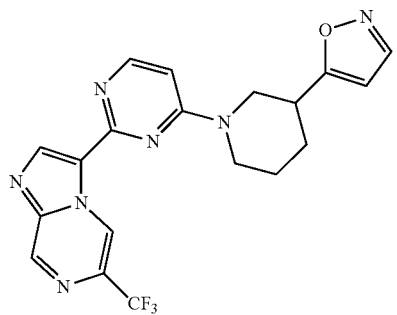

3-(4-(3-(1H-Imidazol-1-yl)-4-methylpiperidin-1-yl)pyrimidin-2-yl)-6-(trifluoromethyl)imidazo[1,2-a]pyrazine IV-319;

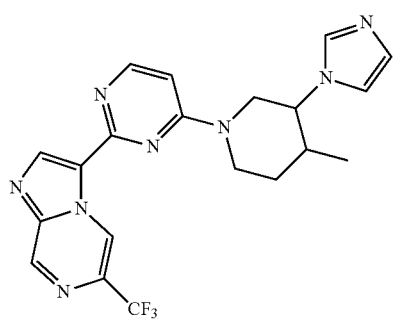

3-(4-(3-(1H-Imidazol-1-yl)-4-methylpiperidin-1-yl)pyrimidin-2-yl)-6-(trifluoromethyl)imidazo[1,2-a]pyrazine IV-320;

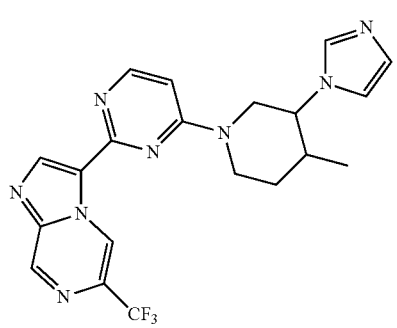 [SMILES: CC1CCN(c2ccnc(-c3cnc4cnc(C(F)(F)F)cn34)n2)CC1n1ccnc1]

3-(1-(2-(6-(Trifluoromethyl)imidazo[1,2-a]pyrazin-3-yl)pyrimidin-4-yl)piperidin-3-yl)-1,2,4-oxadiazole IV-321;

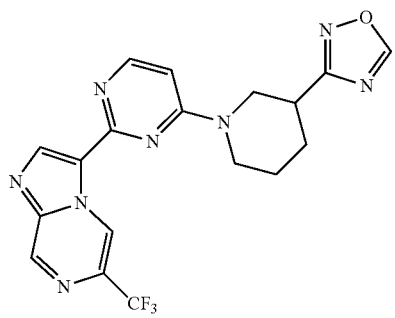 [SMILES: FC(F)(F)c1cn2c(-c3nccc(N4CCCC(c5ncon5)C4)n3)cnc2cn1]

5-(1-(2-(6-(Trifluoromethyl)imidazo[1,2-a]pyrazin-3-yl)pyrimidin-4-yl)piperidin-3-yl)-1,2,4-oxadiazole IV-322;

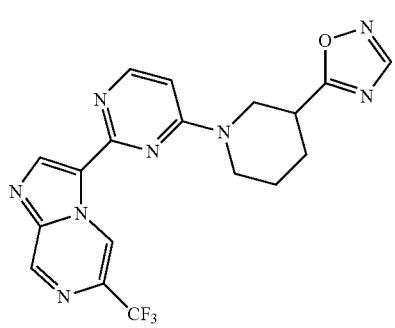

6-(Trifluoromethyl)-3-(4-(2,3,6-trimethyl-5-(1H-pyrazol-4-yl)piperazin-1-yl)pyrimidin-2-yl)imidazo[1,2-a]pyrazine IV-323;

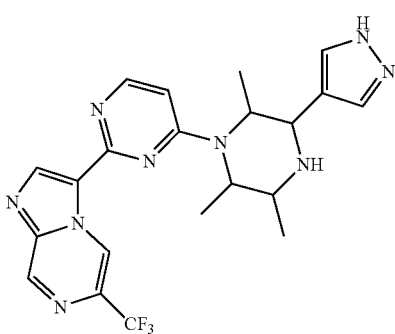 [SMILES: CC1NC(c2cn[nH]c2)C(C)N(c2ccnc(-c3cnc4cnc(C(F)(F)F)cn34)n2)C1C]

3-(4-(2,5-Dimethyl-3-(1H-pyrazol-4-yl)piperazin-1-yl)-5-fluoropyrimidin-2-yl)-6-(trifluoromethyl)imidazo[1,2-a]pyrazine IV-324;

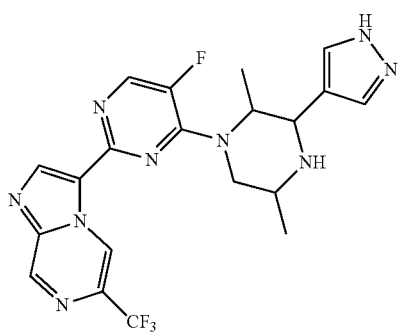 [SMILES: CC1CN(c2nc(-c3cnc4cnc(C(F)(F)F)cn34)ncc2F)C(C)C(c2cn[nH]c2)N1]

3-(4-(3-(1H-Imidazol-4-yl)piperidin-1-yl)pyrimidin-2-yl)-6-(trifluoromethyl)imidazo[1,2-a]pyrazine IV-325;

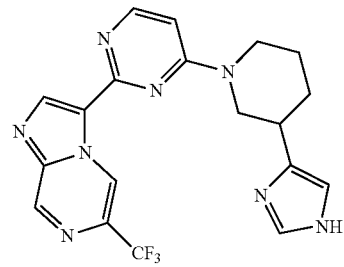 [SMILES: FC(F)(F)c1cn2c(-c3nccc(N4CCCC(c5c[nH]cn5)C4)n3)cnc2cn1]

3-(4-(3-(4H-1,2,4-Triazol-3-yl)piperidin-1-yl)pyrimidin-2-yl)-6-(trifluoromethyl)imidazo[1,2-a]pyrazine IV-326;

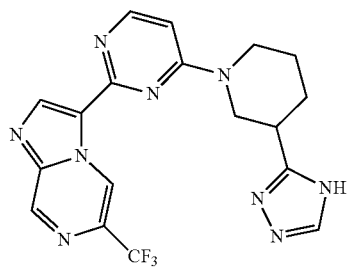 [SMILES: FC(F)(F)c1cn2c(-c3nccc(N4CCCC(c5nnc[nH]5)C4)n3)cnc2cn1]

3-(4-(3,3-Dimethyl-5-(1H-pyrazol-4-yl)piperazin-1-yl)pyrimidin-2-yl)-6-(trifluoromethyl)imidazo[1,2-a]pyrazine IV-327;

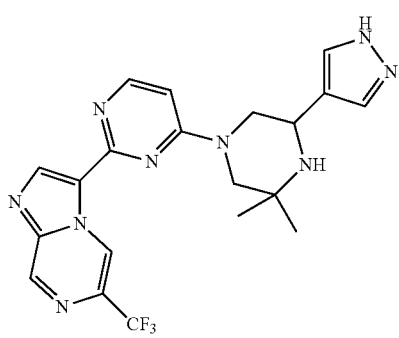 [SMILES: CC1(C)CN(c2ccnc(-c3cnc4cnc(C(F)(F)F)cn34)n2)CC(c2cn[nH]c2)N1]

3-(4-(5-Isopropyl-2-methyl-3-(1H-pyrazol-4-yl)piperazin-1-yl)pyrimidin-2-yl)-6-(trifluoromethyl)imidazo[1,2-a]pyrazine (all syn diastereoisomer) IV-330;

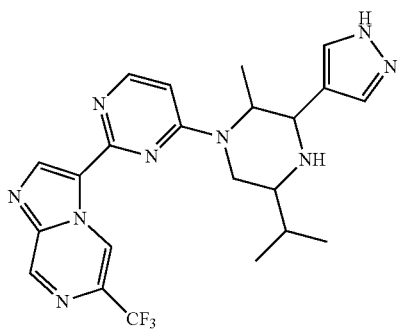 [SMILES: CC(C)C1CN(c2ccnc(-c3cnc4cnc(C(F)(F)F)cn34)n2)C(C)C(c2cn[nH]c2)N1]

3-(4-(3-(2H-Tetrazol-5-yl)piperidin-1-yl)pyrimidin-2-yl)-6-(trifluoromethyl)imidazo[1,2-a]pyrazine IV-331;


4-(5-Fluoro-2-(6-(trifluoromethyl)imidazo[1,2-a]pyrazin-3-yl)pyrimidin-4-yl)-2-methyl-6-(1H-pyrazol-4-yl)morpholine IV-334;

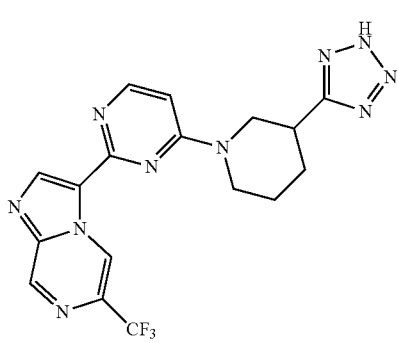 [SMILES: FC(F)(F)c1cn2c(-c3nccc(N4CCCC(c5nn[nH]n5)C4)n3)cnc2cn1]

N-(1-(2-(6-(Trifluoromethyl)imidazo[1,2-a]pyrazin-3-yl)pyrimidin-4-yl)piperidin-3-yl)formamide IV-332;

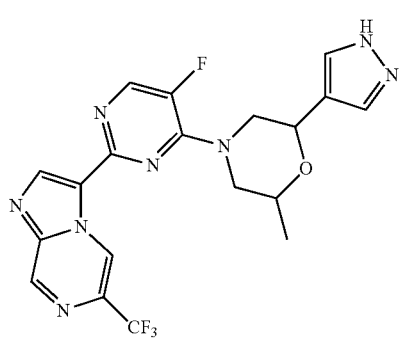

4-(5-Fluoro-2-(6-(trifluoromethyl)imidazo[1,2-a]pyrazin-3-yl)pyrimidin-4-yl)-2-methyl-6-(1H-pyrazol-4-yl)morpholine IV-335;

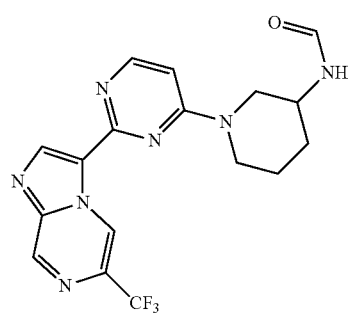 [SMILES: O=CNC1CCCN(c2ccnc(-c3cnc4cnc(C(F)(F)F)cn34)n2)C1]

3-(4-(2-Methyl-5-(1H-pyrazol-4-yl)piperazin-1-yl)pyrimidin-2-yl)-6-(trifluoromethyl)imidazo[1,2-a]pyrazine IV-333;

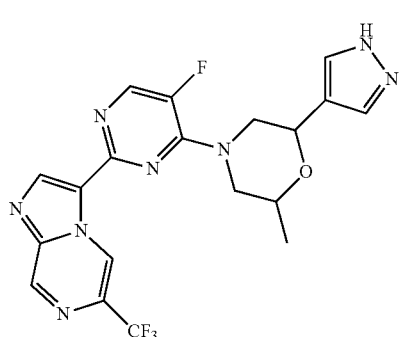

3-(4-(3-(1H-Imidazol-4-yl)piperidin-1-yl)pyrimidin-2-yl)-6-bromoimidazo[1,2-a]pyrazine IV-340;

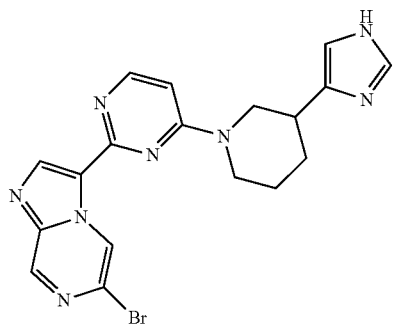 [SMILES: Brc1cn2c(-c3nccc(N4CCCC(c5c[nH]cn5)C4)n3)cnc2cn1]

3-(4-(3-(1H-Imidazol-4-yl)piperidin-1-yl)pyrimidin-2-yl)
imidazo[1,2-a]pyrazine-6-carbonitrile IV-341;

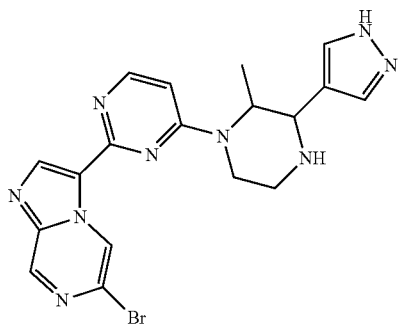

Cis-6-Bromo-3-(4-(3-methyl-5-(1H-pyrazol-4-yl)piperazin-
1-yl)pyrimidin-2-yl)imidazo[1,2-a]pyrazine IV-344;

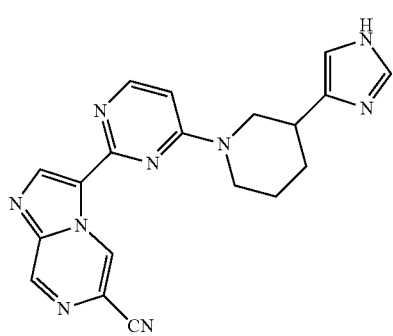 [SMILES: N#Cc1cn2c(-c3nccc(N4CCCC(c5c[nH]cn5)C4)n3)cnc2cn1]

Cis-6-Bromo-3-(4-(3-methyl-2-(1H-pyrazol-4-yl)piperazin-
1-yl)pyrimidin-2-yl)imidazo[1,2-a]pyrazine IV-342;

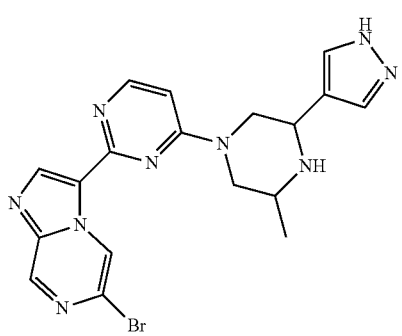

3-(4-(2,5-Dimethyl-3-(1H-pyrazol-4-yl)piperazin-1-yl)py-
rimidin-2-yl)-6-(trifluoromethyl)imidazo[1,2-a]pyrazine
IV-345;

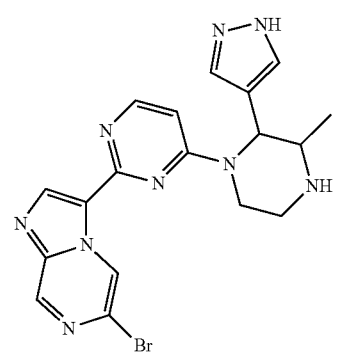 [SMILES: CC1NCCN(c2ccnc(-c3cnc4cnc(Br)cn34)n2)C1c1cn[nH]c1]

Cis-6-Bromo-3-(4-(2-methyl-3-(1H-pyrazol-4-yl)piperazin-
1-yl)pyrimidin-2-yl)imidazo[1,2-a]pyrazine IV-343;

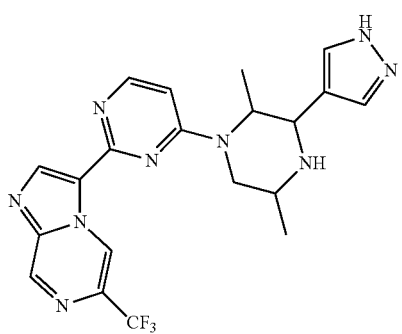

3-(4-(3-(1H-Pyrazol-4-yl)piperidin-1-yl)pyrimidin-2-yl)-6-
bromoimidazo[1,2-a]pyrazine IV-346;

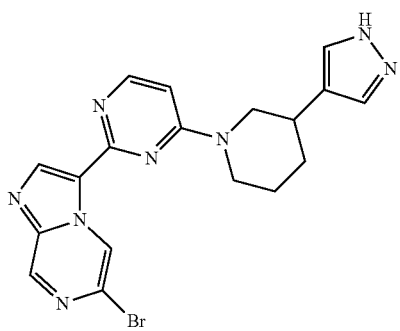 [SMILES: Brc1cn2c(-c3nccc(N4CCCC(c5cn[nH]c5)C4)n3)cnc2cn1]

3-(4-(3-(1H-Imidazol-4-yl)piperazin-1-yl)pyrimidin-2-yl)-
6-chloroimidazo[1,2-a]pyrazine IV-347;

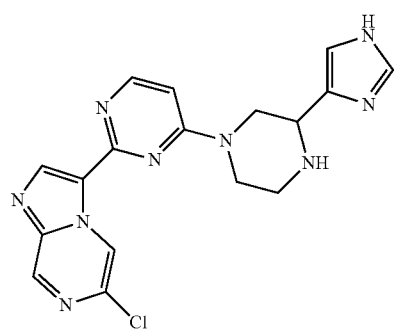 [SMILES: Clc1cn2c(-c3nccc(N4CCNC(c5c[nH]cn5)C4)n3)cnc2cn1]

3-(4-(3-(1H-Imidazol-4-yl)piperazin-1-yl)pyrimidin-2-yl)-
6-bromoimidazo[1,2-a]pyrazine IV-348;

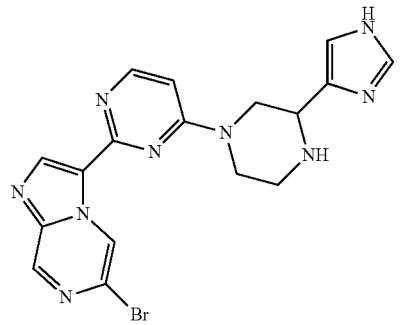 [SMILES: Brc1cn2c(-c3nccc(N4CCNC(c5c[nH]cn5)C4)n3)cnc2cn1]

3-(4-(3-(1H-Imidazol-4-yl)-2,5-dimethylpiperazin-1-yl)pyrimidin-2-yl)-6-chloroimidazo[1,2-a]pyrazine IV-349;

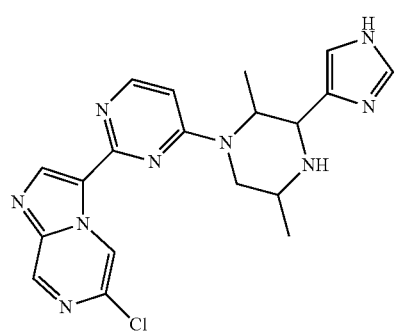 [SMILES: CC1CN(c2ccnc(-c3cnc4cnc(Cl)cn34)n2)C(C)C(c2c[nH]cn2)N1]

3-(4-(3-(1H-Imidazol-4-yl)-2,5-dimethylpiperazin-1-yl)pyrimidin-2-yl)-6-(trifluoromethyl)imidazo[1,2-a]pyrazine IV-352;

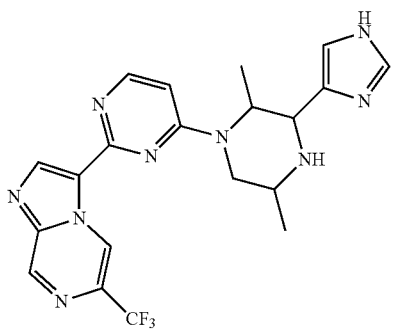

6-Chloro-3-(4-(3,3-dimethyl-5-(1H-pyrazol-4-yl)piperazin-1-yl)pyrimidin-2-yl)imidazo[1,2-a]pyrazine IV-353;

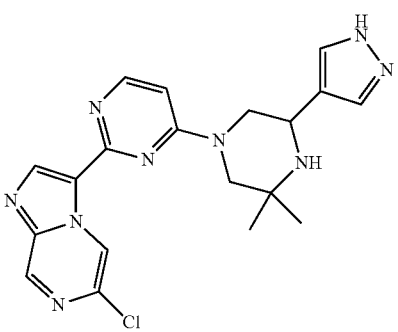 [SMILES: CC1(C)CN(c2ccnc(-c3cnc4cnc(Cl)cn34)n2)CC(c2cn[nH]c2)N1]

6-Bromo-3-(4-(3,3-dimethyl-5-(1H-pyrazol-4-yl)piperazin-1-yl)pyrimidin-2-yl)imidazo[1,2-a]pyrazine IV-354;

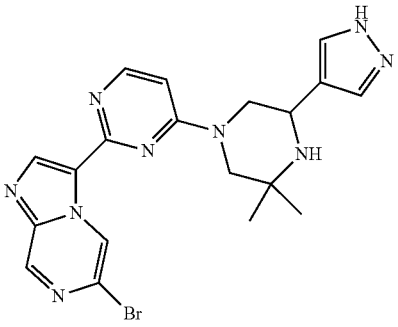 [SMILES: CC1(C)CN(c2ccnc(-c3cnc4cnc(Br)cn34)n2)CC(c2cn[nH]c2)N1]

6-Bromo-3-(4-(3-(2-methyl-1H-imidazol-4-yl)piperidin-1-yl)pyrimidin-2-yl)imidazo[1,2-a]pyrazine IV-355;

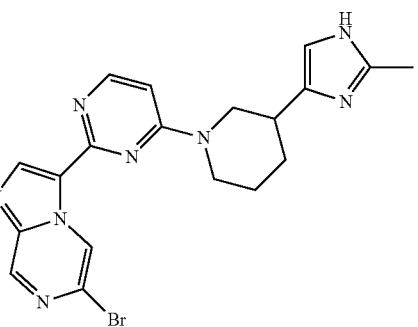

6-Bromo-3-(4-(5-(2-methyl-1H-imidazol-4-yl)-3,6-dihydropyridin-1(2H)-yl)pyrimidin-2-yl)imidazo[1,2-a]pyrazine IV-356;

1049

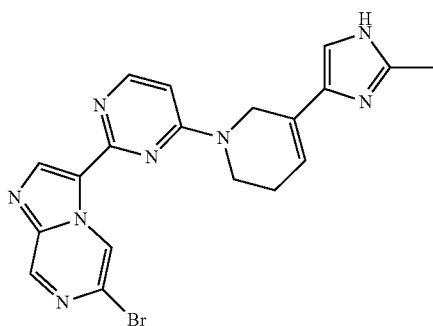 [SMILES: Cc1nc(C2=CCCN(c3ccnc(-c4cnc5cnc(Br)cn45)n3)C2)c[nH]1]

(5-(1H-Pyrazol-4-yl)-1-(2-(6-(trifluoromethyl)imidazo[1,2-a]pyrazin-3-yl)pyrimidin-4-yl)piperidin-3-yl)methanol IV-359;

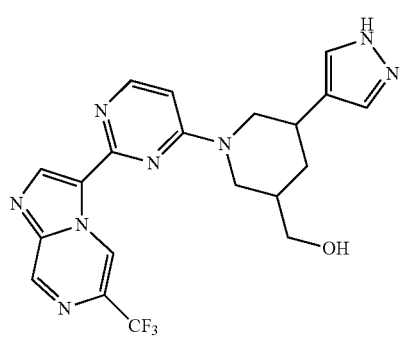 [SMILES: OCC1CC(c2cn[nH]c2)CN(c2ccnc(-c3cnc4cnc(C(F)(F)F)cn34)n2)C1]

3-(4-(3-(1H-Pyrazol-4-yl)piperazin-1-yl)pyrimidin-2-yl)-6-bromoimidazo[1,2-a]pyrazine IV-371;

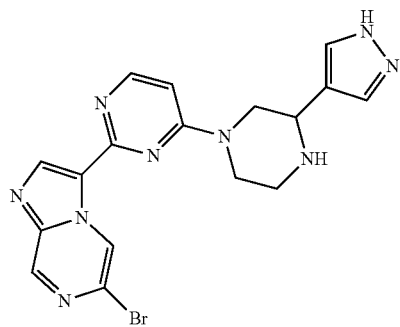 [SMILES: Brc1cn2c(-c3nccc(N4CCNC(c5cn[nH]c5)C4)n3)cnc2cn1]

3-(4-(2-(1H-Imidazol-4-yl)-3,6-dimethylpiperazin-1-yl)pyrimidin-2-yl)-6-bromoimidazo[1,2-a]pyrazine (all syn diastereomer) IV-372;

1050

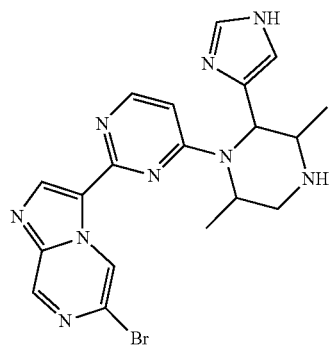 [SMILES: CC1NCC(C)N(c2ccnc(-c3cnc4cnc(Br)cn34)n2)C1c1c[nH]cn1]

3-(4-(3-(1H-Imidazol-4-yl)-2,5-dimethylpiperazin-1-yl)pyrimidin-2-yl)-6-bromoimidazo[1,2-a]pyrazine (all syn diastereomer) IV-373;

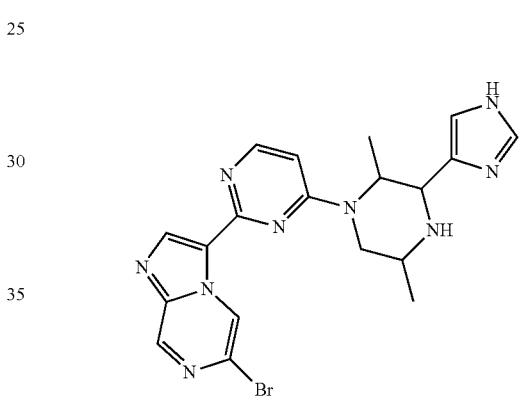

3-(4-(3-(2H-1,2,3-Triazol-4-yl)piperidin-1-yl)pyrimidin-2-yl)-6-(trifluoromethyl)imidazo[1,2-a]pyrazine IV-378;

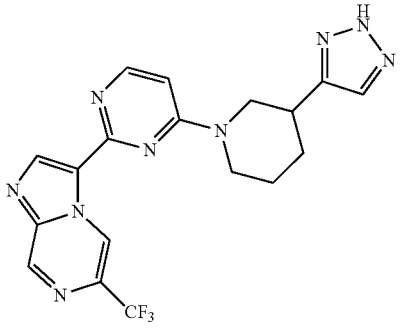

Cis-3-(4-(3-(1H-Imidazol-4-yl)-5-methylpiperazin-1-yl)pyrimidin-2-yl)-6-(trifluoromethyl)imidazo[1,2-a]pyrazine IV-379;

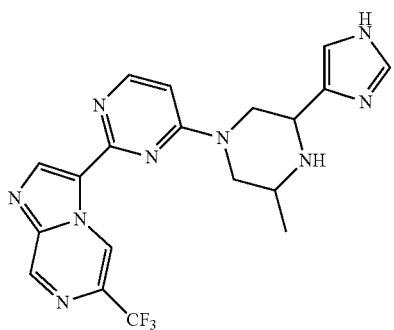

Cis-2-(1H-Imidazol-4-yl)-6-methyl-4-(2-(6-(trifluoromethyl)imidazo[1,2-a]pyrazin-3-yl)pyrimidin-4-yl)morpholine IV-380;

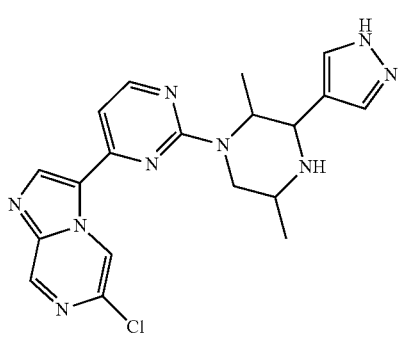

6-Bromo-3-(2-(2,5-dimethyl-3-(1H-pyrazol-4-yl)piperazin-1-yl)pyrimidin-4-yl)imidazo[1,2-a]pyrazine IV-383;

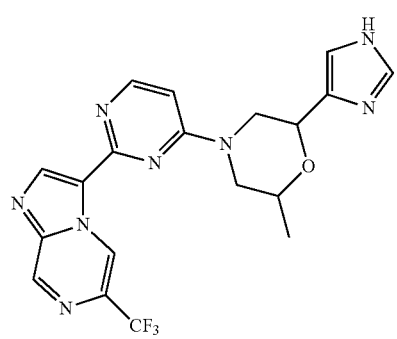

Trans-2-(1H-Imidazol-4-yl)-6-methyl-4-(2-(6-(trifluoromethyl)imidazo[1,2-a]pyrazin-3-yl)pyrimidin-4-yl)morpholine IV-381;

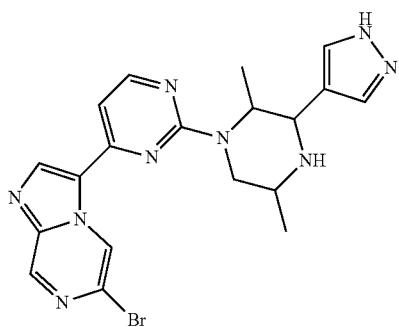

6-Bromo-3-(4-(3-(2-isopropyl-1H-imidazol-4-yl)piperidin-1-yl)pyrimidin-2-yl)imidazo[1,2-a]pyrazine IV-384;

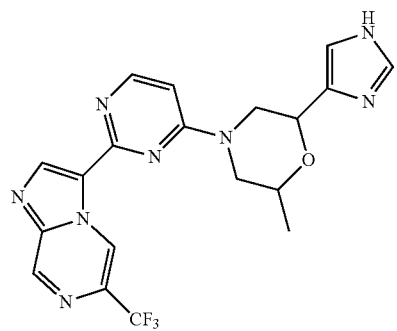

6-Chloro-3-(2-(2,5-dimethyl-3-(1H-pyrazol-4-yl)piperazin-1-yl)pyrimidin-4-yl)imidazo[1,2-a]pyrazine IV-382;

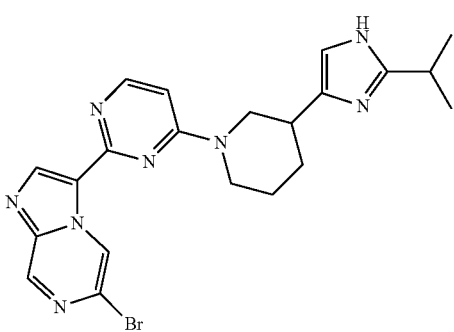 [SMILES: CC(C)c1nc(C2CCCN(c3ccnc(-c4cnc5cnc(Br)cn45)n3)C2)c[nH]1]

6-Bromo-3-(4-(5-(2-isopropyl-1H-imidazol-4-yl)-3,6-dihydropyridin-1(2H)-yl)pyrimidin-2-yl)imidazo[1,2-a]pyrazine IV-385;

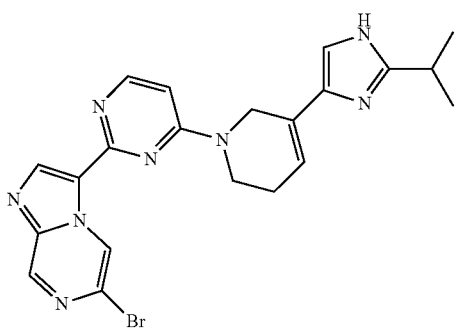 [SMILES: CC(C)c1nc(C2=CCCN(c3ccnc(-c4cnc5cnc(Br)cn45)n3)C2)c[nH]1]

3-(1H-Pyrazol-4-yl)-1-(2-(6-(trifluoromethyl)imidazo[1,2-a]pyrazin-3-yl)pyrimidin-4-yl)piperidin-3-ol IV-386;

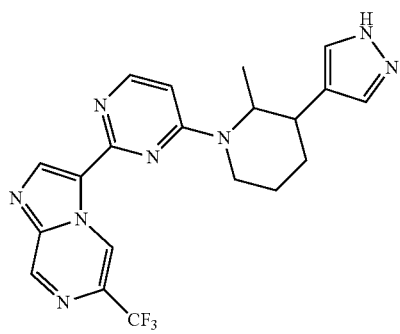

3-(4-(3-(1H-Imidazol-4-yl)-2-methylpiperidin-1-yl)pyrimidin-2-yl)-6-(trifluoromethyl)imidazo[1,2-a]pyrazine IV-389;

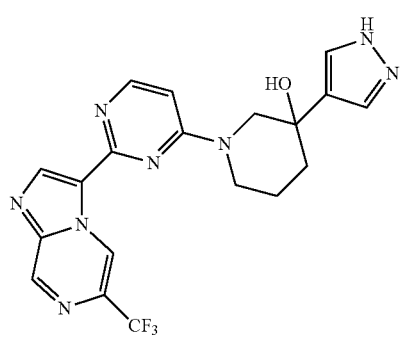

Cis-6-Bromo-3-(4-(2-methyl-3-(1H-pyrazol-4-yl)piperidin-1-yl)pyrimidin-2-yl)imidazo[1,2-a]pyrazine IV-387;

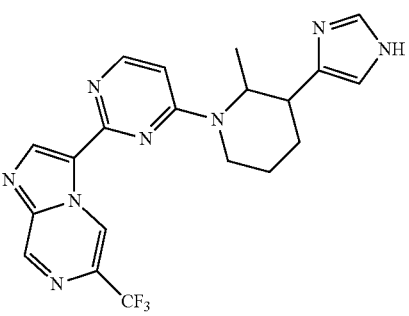 [SMILES: CC1C(c2c[nH]cn2)CCCN1c1ccnc(-c2cnc3cnc(C(F)(F)F)cn23)n1]

Trans-(5-(1H-Pyrazol-4-yl)-1-(2-(6-(trifluoromethyl)imidazo[1,2-a]pyrazin-3-yl)pyrimidin-4-yl)piperidin-3-yl)imino)dimethyl-$\lambda^6$-sulfanone IV-394;

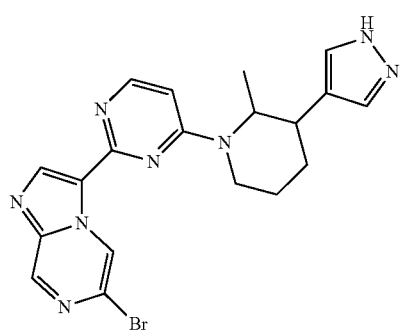

3-(4-(2-Methyl-3-(1H-pyrazol-4-yl)piperidin-1-yl)pyrimidin-2-yl)-6-(trifluoromethyl)imidazo[1,2-a]pyrazine IV-388;

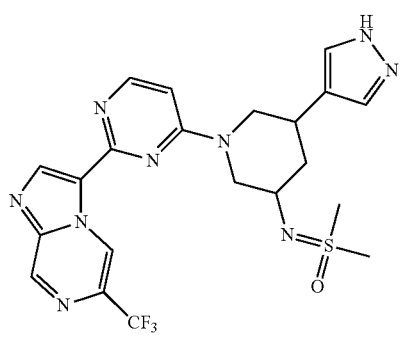 [SMILES: CS(C)(=O)=NC1CC(c2cn[nH]c2)CN(c2ccnc(-c3cnc4cnc(C(F)(F)F)cn34)n2)C1]

Cis-(5-(1H-Pyrazol-4-yl)-1-(2-(6-(trifluoromethyl)imidazo[1,2-a]pyrazin-3-yl)pyrimidin-4-yl)piperidin-3-yl)imino)dimethyl-$\lambda^6$-sulfanone IV-395;

1055

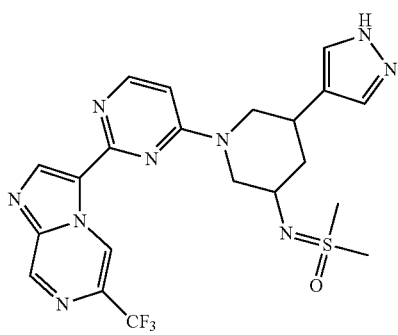 [SMILES: CS(C)(=O)=NC1CC(c2cn[nH]c2)CN(c2ccnc(-c3cnc4cnc(C(F)(F)F)cn34)n2)C1]

3-(4-(3-Methoxy-5-(1H-pyrazol-4-yl)piperidin-1-yl)pyrimidin-2-yl)-6-(trifluoromethyl)imidazo[1,2-a]pyrazine IV-396;

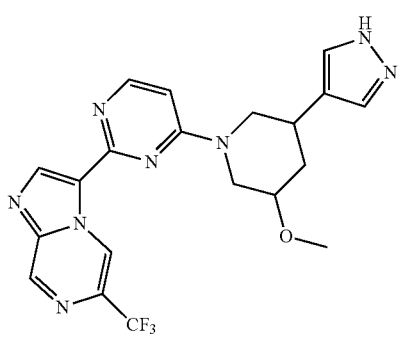

3-(4-(2-Methyl-3-(1H-pyrazol-4-yl)piperazin-1-yl)pyrimidin-2-yl)imidazo[1,2-a]pyrazine IV-397;

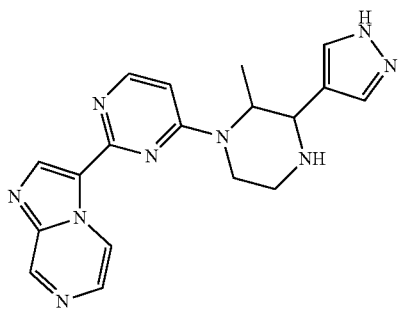 [SMILES: CC1C(c2cn[nH]c2)NCCN1c1ccnc(-c2cnc3cnccn23)n1]

6-Methyl-3-(4-(2-methyl-3-(1H-pyrazol-4-yl)piperazin-1-yl)pyrimidin-2-yl)imidazo[1,2-a]pyrazine IV-398;

1056

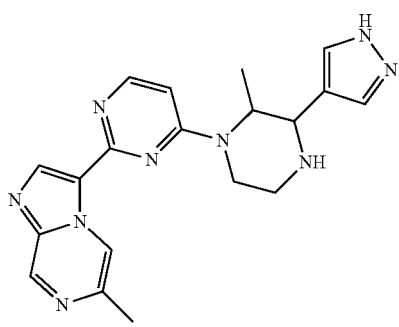 [SMILES: Cc1cn2c(-c3nccc(N4CCNC(c5cn[nH]c5)C4C)n3)cnc2cn1]

3-(4-(3-(2-Chloro-1H-imidazol-4-yl)piperidin-1-yl)pyrimidin-2-yl)-6-(trifluoromethyl)imidazo[1,2-a]pyrazine IV-409;

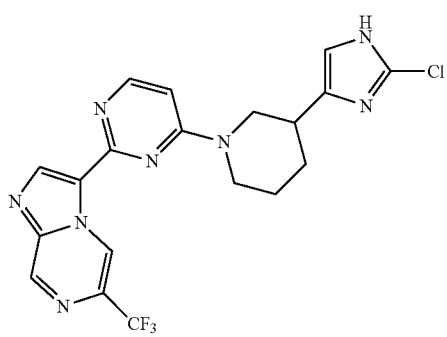 [SMILES: FC(F)(F)c1cn2c(-c3nccc(N4CCCC(c5c[nH]c(Cl)n5)C4)n3)cnc2cn1]

6-(1H-Pyrazol-4-yl)-4-(2-(6-(trifluoromethyl)imidazo[1,2-a]pyrazin-3-yl)pyrimidin-4-yl)piperazin-2-one IV-410;

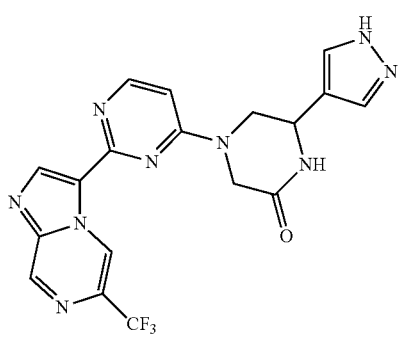 [SMILES: O=C1CN(c2ccnc(-c3cnc4cnc(C(F)(F)F)cn34)n2)CC(c2cn[nH]c2)N1]

Cis-6-Cyclopropyl-3-(4-(2-methyl-3-(1H-pyrazol-4-yl)piperazin-1-yl)pyrimidin-2-yl)imidazo[1,2-a]pyrazine IV-411;

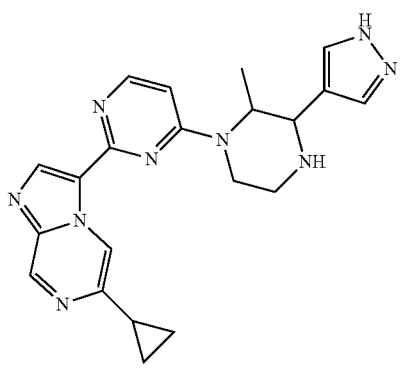 [SMILES: CC1C(c2cn[nH]c2)NCCN1c1ccnc(-c2cnc3cnc(C4CC4)cn23)n1]

Cis-6-Cyclopropyl-3-(4-(3-methyl-2-(1H-pyrazol-4-yl)piperazin-1-yl)pyrimidin-2-yl)imidazo[1,2-a]pyrazine IV-412;

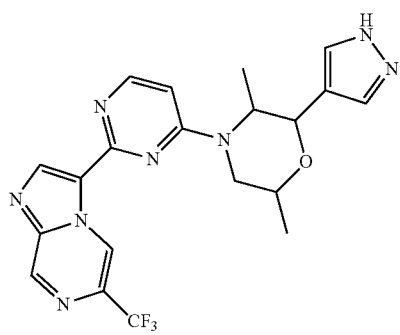

3-Methyl-2-(1H-pyrazol-4-yl)-4-(4-(6-(trifluoromethyl)imidazo[1,2-a]pyrazin-3-yl)pyrimidin-2-yl)morpholine IV-417;

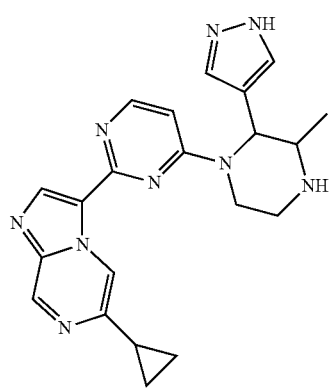 [SMILES: CC1NCCN(c2ccnc(-c3cnc4cnc(C5CC5)cn34)n2)C1c1cn[nH]c1]

3,6-Dimethyl-2-(1H-pyrazol-4-yl)-4-(2-(6-(trifluoromethyl)imidazo[1,2-a]pyrazin-3-yl)pyrimidin-4-yl)morpholine IV-415;

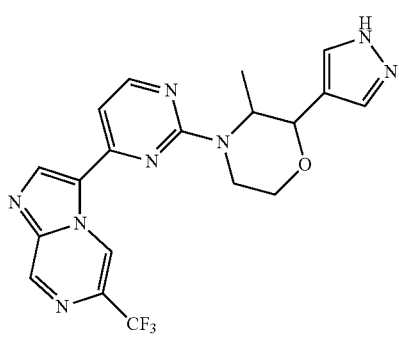

3-Methyl-2-(1H-pyrazol-4-yl)-4-(4-(6-(trifluoromethyl)imidazo[1,2-a]pyrazin-3-yl)pyrimidin-2-yl)morpholine IV-418;

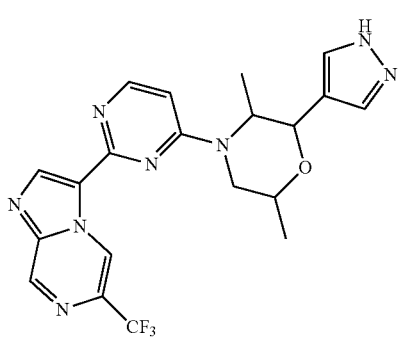

3,6-Dimethyl-2-(1H-pyrazol-4-yl)-4-(2-(6-(trifluoromethyl)imidazo[1,2-a]pyrazin-3-yl)pyrimidin-4-yl)morpholine IV-416;

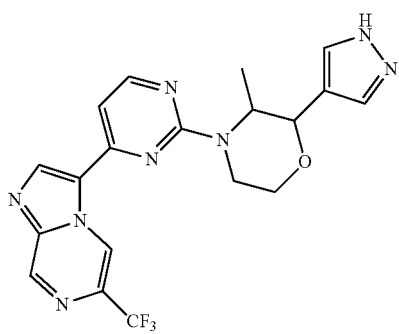

3-(2-(2,5-Dimethyl-3-(1H-pyrazol-4-yl)piperazin-1-yl)-5-fluoropyrimidin-4-yl)-6-(trifluoromethyl)imidazo[1,2-a]pyrazine (all syn diastereoisomer) IV-421;

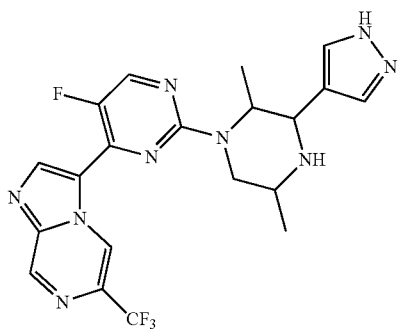

3-(5-Fluoro-2-(3-methyl-5-(1H-pyrazol-4-yl)piperazin-1-yl)pyrimidin-4-yl)-6-(trifluoromethyl)imidazo[1,2-a]pyrazine (all syn diastereoisomer) IV-422;

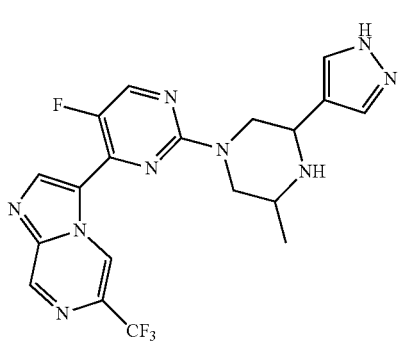 [SMILES: CC1CN(c2ncc(F)c(-c3cnc4cnc(C(F)(F)F)cn34)n2)CC(c2cn[nH]c2)N1]

3-(4-(Piperidin-1-yl)pyrimidin-2-yl)-6-(trifluoromethyl)imidazo[1,2-a]pyrazine IV-423;

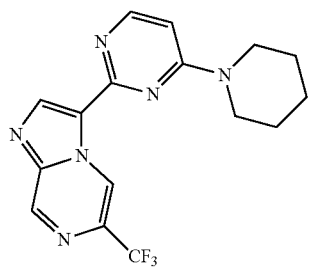

3-(4-(3-Methylpiperidin-1-yl)pyrimidin-2-yl)-6-(trifluoromethyl)imidazo[1,2-a]pyrazine IV-424;

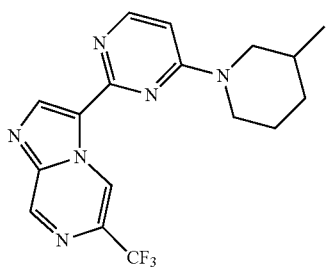

4-(2-(6-(Trifluoromethyl)imidazo[1,2-a]pyrazin-3-yl)pyrimidin-4-yl)-1,4-oxazepane-6-carboxamide IV-425;

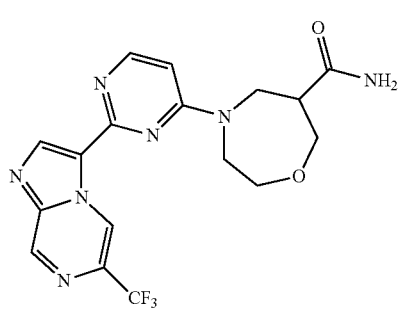 [SMILES: NC(=O)C1COCCN(c2ccnc(-c3cnc4cnc(C(F)(F)F)cn34)n2)C1]

4-(2-(6-(Trifluoromethyl)imidazo[1,2-a]pyrazin-3-yl)pyrimidin-4-yl)morpholine IV-426;

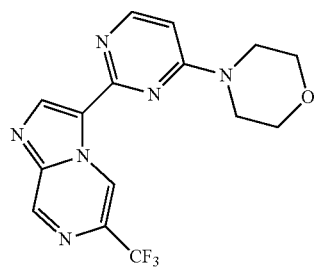 [SMILES: FC(F)(F)c1cn2c(-c3nccc(N4CCOCC4)n3)cnc2cn1]

4-(2-(6-(Trifluoromethyl)imidazo[1,2-a]pyrazin-3-yl)pyrimidin-4-yl)-1,4-oxazepane IV-427;

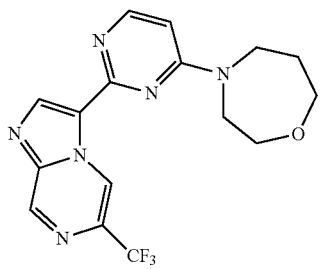

3-(4-(Pyrrolidin-1-yl)pyrimidin-2-yl)-6-(trifluoromethyl)imidazo[1,2-a]pyrazine IV-428;

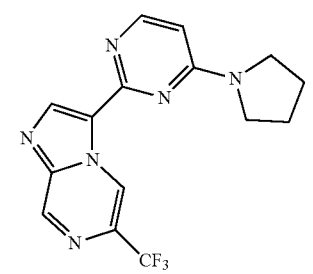 [SMILES: FC(F)(F)c1cn2c(-c3nccc(N4CCCC4)n3)cnc2cn1]

3-(4-(Azepan-1-yl)pyrimidin-2-yl)-6-(trifluoromethyl)imidazo[1,2-a]pyrazine IV-429;

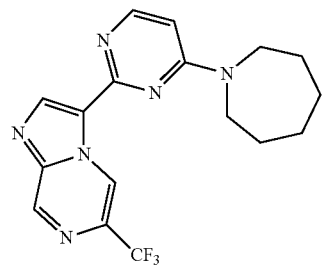 [SMILES: FC(F)(F)c1cn2c(-c3nccc(N4CCCCCC4)n3)cnc2cn1]

3-(4-(5-(3-Fluoro-1H-pyrazol-4-yl)-3,6-dihydropyridin-1(2H)-yl)pyrimidin-2-yl)-6-(trifluoromethyl)imidazo[1,2-a]pyrazine IV-430;

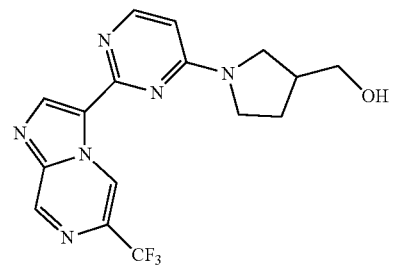

2-(1-(2-(6-(Trifluoromethyl)imidazo[1,2-a]pyrazin-3-yl)pyrimidin-4-yl)pyrrolidin-3-yl)ethan-1-ol IV-435;

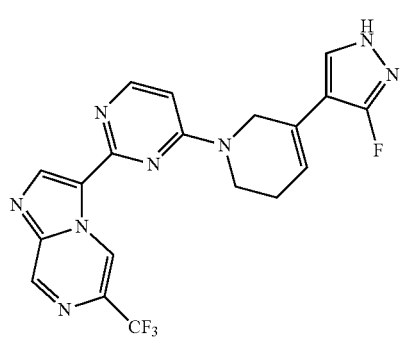 [SMILES: Fc1n[nH]cc1C1=CCCN(c2ccnc(-c3cnc4cnc(C(F)(F)F)cn34)n2)C1]

2-(1-(2-(6-(Trifluoromethyl)imidazo[1,2-a]pyrazin-3-yl)pyrimidin-4-yl)pyrrolidin-3-yl)acetamide IV-432;

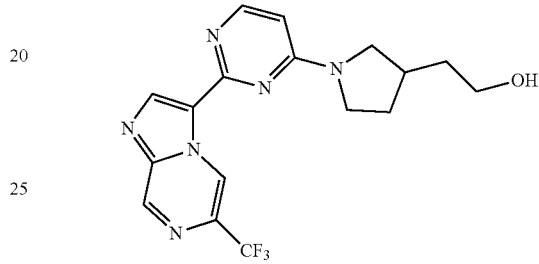

(1-(2-(6-(Trifluoromethyl)imidazo[1,2-a]pyrazin-3-yl)pyrimidin-4-yl)pyrrolidin-2-yl)methanol IV-436;

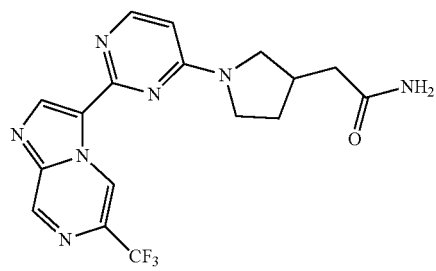 [SMILES: NC(=O)CC1CCN(c2ccnc(-c3cnc4cnc(C(F)(F)F)cn34)n2)C1]

1-(2-(6-(Trifluoromethyl)imidazo[1,2-a]pyrazin-3-yl)pyrimidin-4-yl)pyrrolidin-3-ol IV-433;

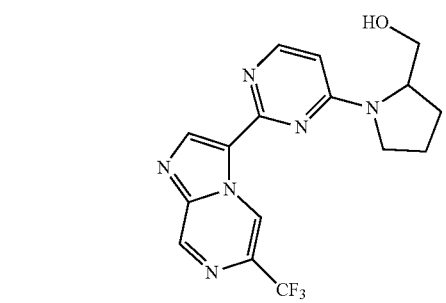

1-(2-(6-(Trifluoromethyl)imidazo[1,2-a]pyrazin-3-yl)pyrimidin-4-yl)piperidin-3-ol IV-437;

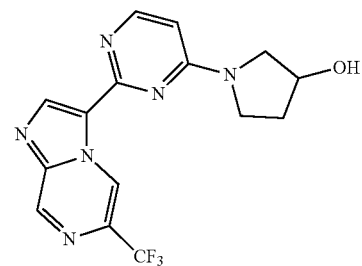 [SMILES: OC1CCN(c2ccnc(-c3cnc4cnc(C(F)(F)F)cn34)n2)C1]

(1-(2-(6-(Trifluoromethyl)imidazo[1,2-a]pyrazin-3-yl)pyrimidin-4-yl)pyrrolidin-3-yl)methanol IV-434;

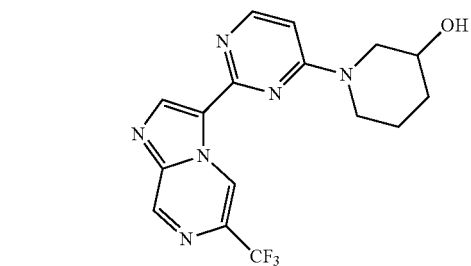

2-(1-(2-(6-(Trifluoromethyl)imidazo[1,2-a]pyrazin-3-yl)pyrimidin-4-yl)piperidin-2-yl)ethan-1-ol IV-438;

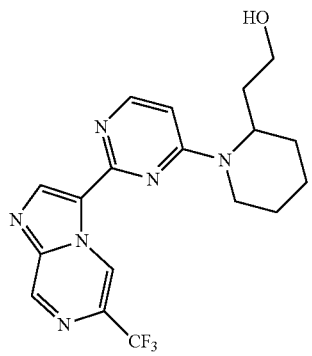 [SMILES: OCCC1CCCCN1c1ccnc(-c2cnc3cnc(C(F)(F)F)cn23)n1]

(1-(2-(6-(Trifluoromethyl)imidazo[1,2-a]pyrazin-3-yl)py-
rimidin-4-yl)piperidin-3-yl)methanol IV-439;

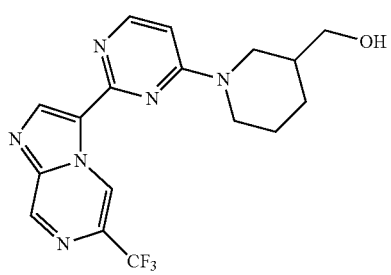

(1-(2-(6-(Trifluoromethyl)imidazo[1,2-a]pyrazin-3-yl)py-
rimidin-4-yl)piperidin-2-yl)methanol IV-440;

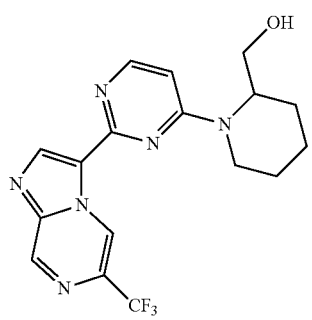 [SMILES: OCC1CCCCN1c1ccnc(-c2cnc3cnc(C(F)(F)F)cn23)n1]

1-(2-(6-(Trifluoromethyl)imidazo[1,2-a]pyrazin-3-yl)py-
rimidin-4-yl)piperidin-4-ol IV-441;

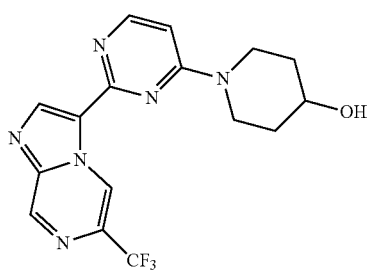

2-(1-(2-(6-(Trifluoromethyl)imidazo[1,2-a]pyrazin-3-yl)py-
rimidin-4-yl)piperidin-4-yl)ethan-1-ol IV-442;

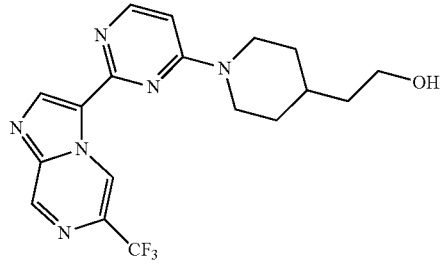

(1-(2-(6-(Trifluoromethyl)imidazo[1,2-a]pyrazin-3-yl)py-
rimidin-4-yl)piperidin-4-yl)methanol IV-443;

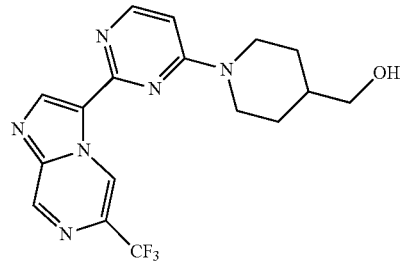 [SMILES: OCC1CCN(c2ccnc(-c3cnc4cnc(C(F)(F)F)cn34)n2)CC1]

2-(1-(2-(6-(Trifluoromethyl)imidazo[1,2-a]pyrazin-3-yl)py-
rimidin-4-yl)piperidin-3-yl)ethan-1-ol IV-444;

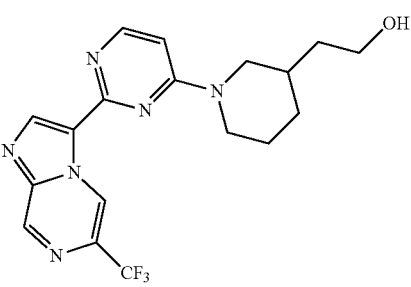 [SMILES: OCCC1CCCN(c2ccnc(-c3cnc4cnc(C(F)(F)F)cn34)n2)C1]

(1-(2-(6-(Trifluoromethyl)imidazo[1,2-a]pyrazin-3-yl)py-
rimidin-4-yl)azepan-3-yl)methanol IV-445;

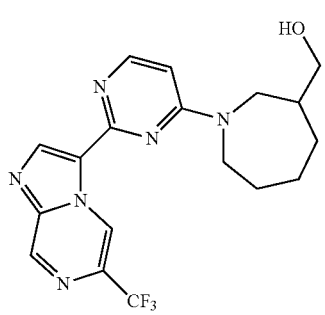 [SMILES: OCC1CCCCN(c2ccnc(-c3cnc4cnc(C(F)(F)F)cn34)n2)C1]

(4-(2-(6-(Trifluoromethyl)imidazo[1,2-a]pyrazin-3-yl)py-
rimidin-4-yl)morpholin-2-yl)methanol IV-446;

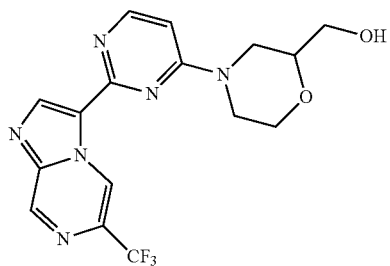 [SMILES: OCC1CN(c2ccnc(-c3cnc4cnc(C(F)(F)F)cn34)n2)CCO1]

1-(2-(6-(Trifluoromethyl)imidazo[1,2-a]pyrazin-3-yl)pyrimidin-4-yl)azepan-4-ol IV-447;

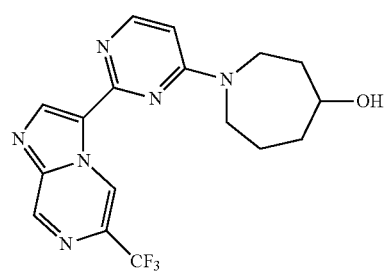 [SMILES: OC1CCCN(c2ccnc(-c3cnc4cnc(C(F)(F)F)cn34)n2)CC1]

3-(4-(3-(5-Methyl-1H-pyrazol-4-yl)piperidin-1-yl)pyrimidin-2-yl)-6-(trifluoromethyl)imidazo[1,2-a]pyrazine IV-452;

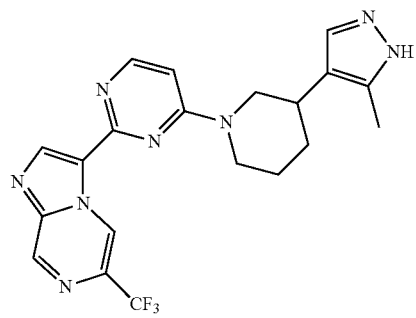

Cis-2-Methyl-1-(2-(6-(trifluoromethyl)imidazo[1,2-a]pyrazin-3-yl)pyrimidin-4-yl)piperidine-3-carboxamide IV-453;

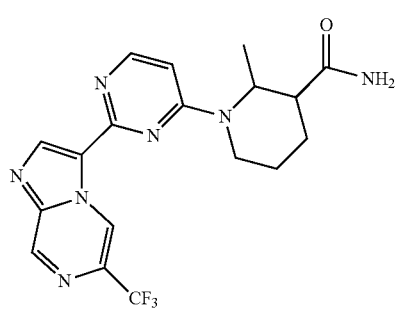 [SMILES: CC1C(C(N)=O)CCCN1c1ccnc(-c2cnc3cnc(C(F)(F)F)cn23)n1]

6-(Difluoromethyl)-3-(4-(2-methyl-3-(1H-pyrazol-4-yl)piperazin-1-yl)pyrimidin-2-yl)imidazo[1,2-a]pyrazine IV-454;

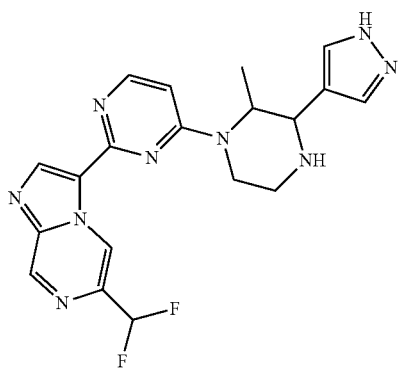 [SMILES: CC1C(c2cn[nH]c2)NCCN1c1ccnc(-c2cnc3cnc(C(F)F)cn23)n1]

6-(Difluoromethyl)-3-(4-(3-methyl-2-(1H-pyrazol-4-yl)piperazin-1-yl)pyrimidin-2-yl)imidazo[1,2-a]pyrazine IV-455;

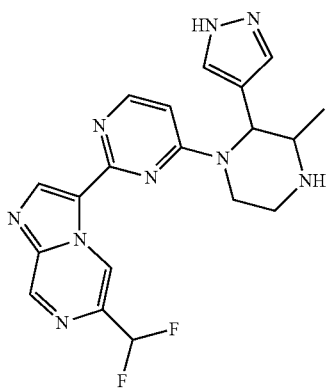 [SMILES: CC1NCCN(c2ccnc(-c3cnc4cnc(C(F)F)cn34)n2)C1c1cn[nH]c1]

3-(4-(3-(1H-Imidazol-4-yl)pyrrolidin-1-yl)pyrimidin-2-yl)-6-(trifluoromethyl)imidazo[1,2-a]pyrazine IV-456;

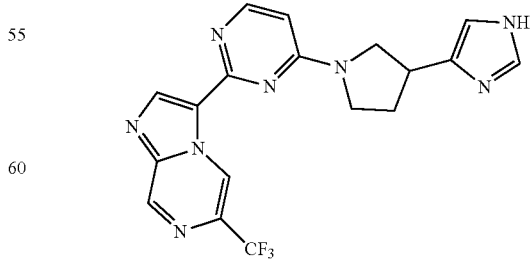

3-(4-(3-(1H-Pyrazol-3-yl)pyrrolidin-1-yl)pyrimidin-2-yl)-6-(trifluoromethyl)imidazo[1,2-a]pyrazine IV-457;

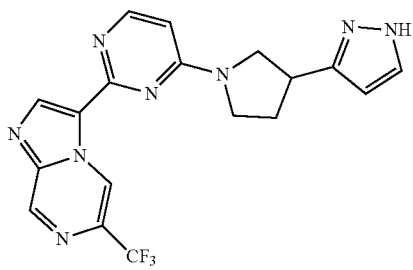 [SMILES: FC(F)(F)c1cn2c(-c3nccc(N4CCC(c5cc[nH]n5)C4)n3)cnc2cn1]

2,5-Dimethyl-1-(2-(6-(trifluoromethyl)imidazo[1,2-a]pyrazin-3-yl)pyrimidin-4-yl)piperidine-3-carboxamide IV-464;

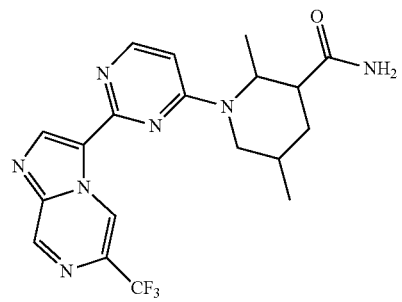 [SMILES: CC1CC(C(N)=O)C(C)N(c2ccnc(-c3cnc4cnc(C(F)(F)F)cn34)n2)C1]

3-(4-(3-(Difluoromethoxy)-5-(1H-pyrazol-4-yl)piperidin-1-yl)pyrimidin-2-yl)-6-(trifluoromethyl)imidazo[1,2-a]pyrazine IV-466;

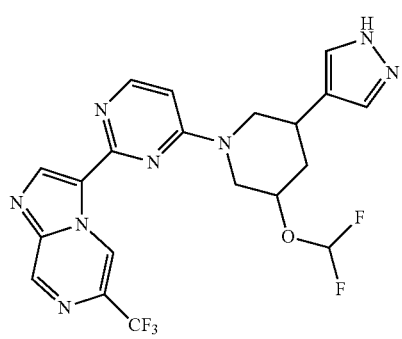 [SMILES: FC(F)OC1CC(c2cn[nH]c2)CN(c2ccnc(-c3cnc4cnc(C(F)(F)F)cn34)n2)C1]

3-(4-(3-(Difluoromethoxy)-5-(1H-pyrazol-4-yl)piperidin-1-yl)pyrimidin-2-yl)-6-(trifluoromethyl)imidazo[1,2-a]pyrazine IV-472;

3-(4-(3-(5-Fluoro-1H-pyrazol-4-yl)piperidin-1-yl)pyrimidin-2-yl)-6-(trifluoromethyl)imidazo[1,2-a]pyrazine IV-473;

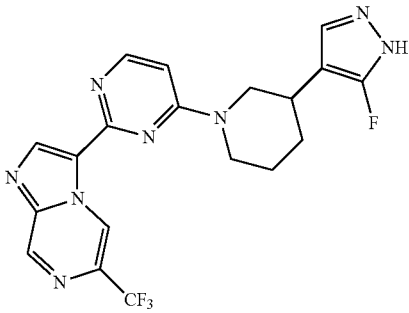

1-(1-(2-(6-(Trifluoromethyl)imidazo[1,2-a]pyrazin-3-yl)pyrimidin-4-yl)pyrrolidin-3-yl)-1H-pyrazol-4-amine IV-478;

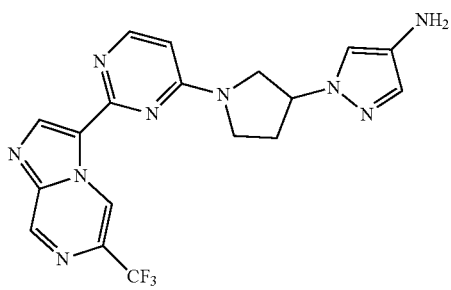 [SMILES: Nc1cnn(C2CCN(c3ccnc(-c4cnc5cnc(C(F)(F)F)cn45)n3)C2)c1]

7-(2-(6-(Trifluoromethyl)imidazo[1,2-a]pyrazin-3-yl)pyrimidin-4-yl)hexahydroimidazo[1,5-a]pyrazin-3(2H)-one IV-480;

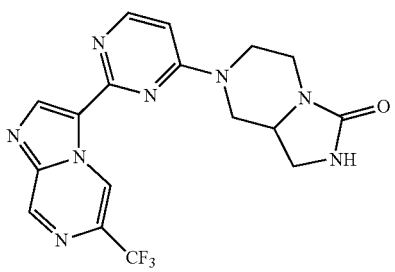 [SMILES: O=C1NCC2CN(c3ccnc(-c4cnc5cnc(C(F)(F)F)cn45)n3)CCN12]

2,5-Dimethyl-1-(2-(6-(trifluoromethyl)imidazo[1,2-a]pyrazin-3-yl)pyrimidin-4-yl)piperidine-3-carboxamide IV-481;

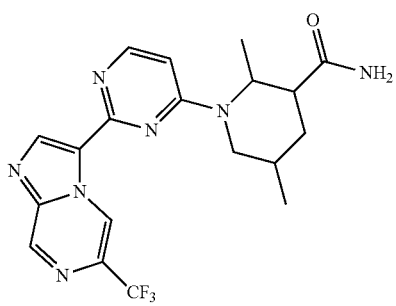

3-(4-(3-((Methylsulfonyl)methyl)piperidin-1-yl)pyrimidin-2-yl)-6-(trifluoromethyl)imidazo[1,2-a]pyrazine IV-482;

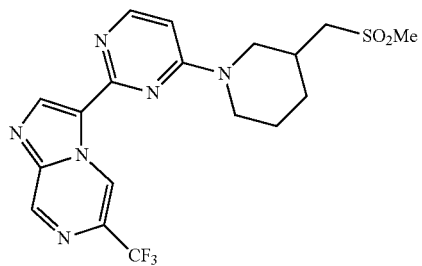 [SMILES: CS(=O)(=O)CC1CCCN(c2ccnc(-c3cnc4cnc(C(F)(F)F)cn34)n2)C1]

3-(4-(3-(Methylsulfonyl)piperidin-1-yl)pyrimidin-2-yl)-6-(trifluoromethyl)imidazo[1,2-a]pyrazine IV-483;

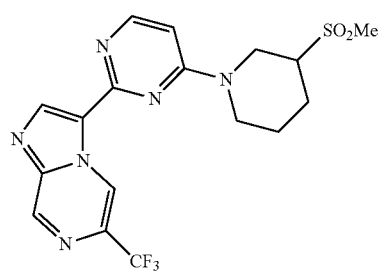 [SMILES: CS(=O)(=O)C1CCCN(c2ccnc(-c3cnc4cnc(C(F)(F)F)cn34)n2)C1]

3-(2-(3-(1H-Imidazol-4-yl)piperidin-1-yl)pyrimidin-4-yl)-6-(trifluoromethyl)imidazo[1,2-a]pyrazine IV-484;

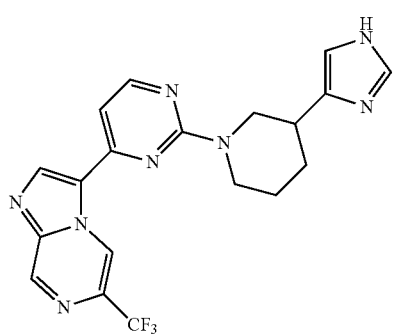

3-(2-(2-Methyl-3-(1H-pyrazol-4-yl)piperidin-1-yl)pyrimidin-4-yl)-6-(trifluoromethyl)imidazo[1,2-a]pyrazine IV-485;

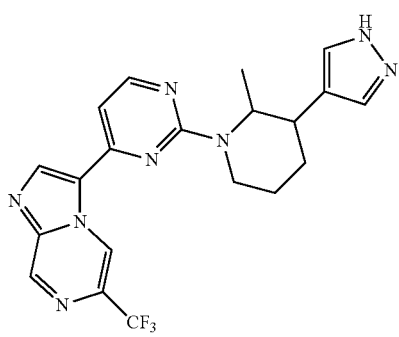

4-(1-(2-(6-(Trifluoromethyl)imidazo[1,2-a]pyrazin-3-yl)pyrimidin-4-yl)piperidin-3-yl)piperazin-2-one IV-490;

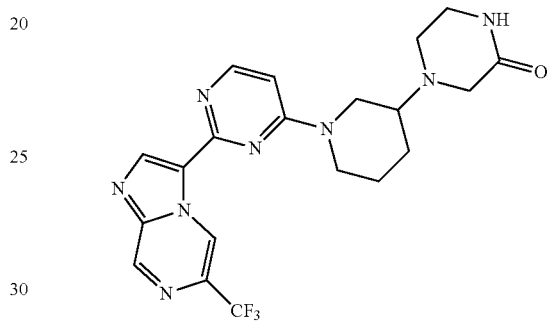

3-(4-(3-(1H-1,2,3-Triazol-1-yl)piperidin-1-yl)pyrimidin-2-yl)-6-(trifluoromethyl)imidazo[1,2-a]pyrazine IV-493;

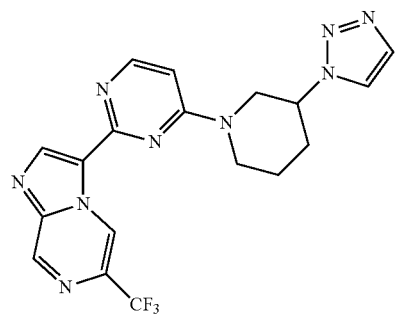 [SMILES: FC(F)(F)c1cn2c(-c3nccc(N4CCCC(n5ccnn5)C4)n3)cnc2cn1]

3-(4-(3-(1H-Pyrazol-4-yl)pyrrolidin-1-yl)pyrimidin-2-yl)-6-(trifluoromethyl)imidazo[1,2-a]pyrazine IV-494;

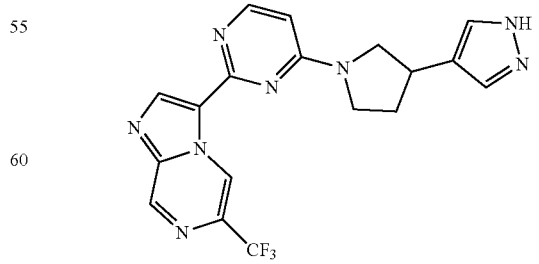

3-(4-(3-(Methoxymethyl)piperidin-1-yl)pyrimidin-2-yl)-6-(trifluoromethyl)imidazo[1,2-a]pyrazine IV-495;

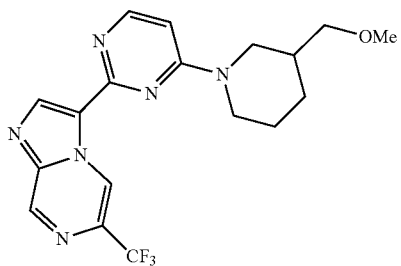

7-(2-(6-(Trifluoromethyl)imidazo[1,2-a]pyrazin-3-yl)py-rimidin-4-yl)-2-oxa-7-azaspiro[4.5]decane IV-496;

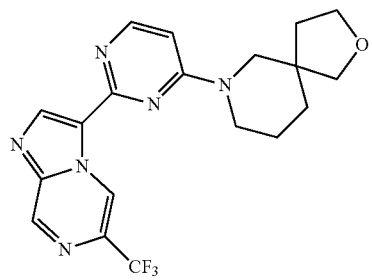 [SMILES: FC(F)(F)c1cn2c(-c3nccc(N4CCCC5(CCOC5)C4)n3)cnc2cn1]

5-(2-(6-(Trifluoromethyl)imidazo[1,2-a]pyrazin-3-yl)py-rimidin-4-yl)hexahydro-2H-furo[2,3-a]pyrrole IV-497;

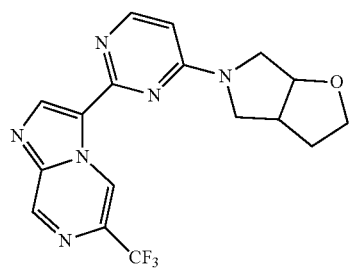 [SMILES: FC(F)(F)c1cn2c(-c3nccc(N4CC5CCOC5C4)n3)cnc2cn1]

2,2,2-Trifluoro-1-(1-(2-(6-(trifluoromethyl)imidazo[1,2-a]pyrazin-3-yl)pyrimidin-4-yl)piperidin-3-yl)ethan-1-amine IV-502;

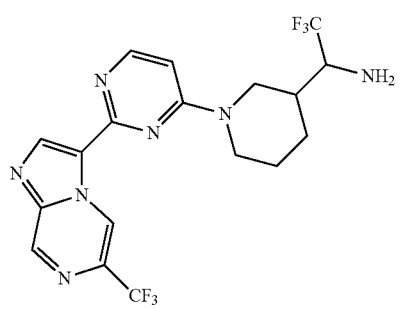

2,2,2-Trifluoro-1-(1-(2-(6-(trifluoromethyl)imidazo[1,2-a]pyrazin-3-yl)pyrimidin-4-yl)piperidin-3-yl)ethan-1-amine IV-503;

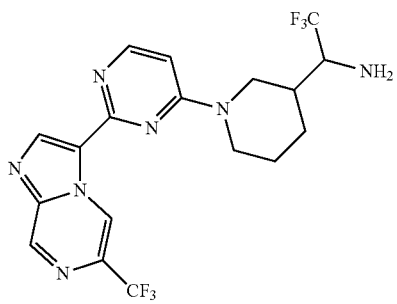 [SMILES: NC(C1CCCN(c2ccnc(-c3cnc4cnc(C(F)(F)F)cn34)n2)C1)C(F)(F)F]

8-(2-(6-(Trifluoromethyl)imidazo[1,2-a]pyrazin-3-yl)py-rimidin-4-yl)octahydropyrazino[2,1-a][1,4]oxazine IV-504;

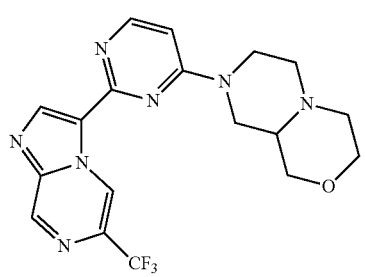 [SMILES: FC(F)(F)c1cn2c(-c3nccc(N4CCN5CCOCC5C4)n3)cnc2cn1]

2-(2-(6-(Trifluoromethyl)imidazo[1,2-a]pyrazin-3-yl)py-rimidin-4-yl)-9-oxa-2-azaspiro[5.5]undecane IV-505;

1-(tert-Butyl)-7-(2-(6-(trifluoromethyl)imidazo[1,2-a]pyrazin-3-yl)pyrimidin-4-yl)hexahydro-3H-oxazolo[3,4-a]pyrazine IV-506;

3-(4-(3-(Tetrahydro-2H-pyran-4-yl)pyrrolidin-1-yl)pyrimidin-2-yl)-6-(trifluoromethyl)imidazo[1,2-a]pyrazine IV-507;

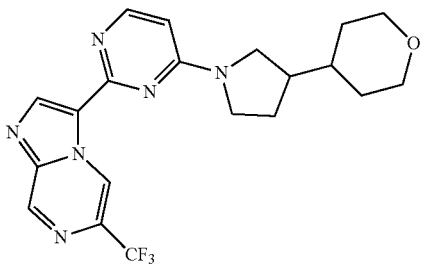 [SMILES: FC(F)(F)c1cn2c(-c3nccc(N4CCC(C5CCOCC5)C4)n3)cnc2cn1]

3-(4-(3-(Oxetan-3-yl)pyrrolidin-1-yl)pyrimidin-2-yl)-6-(trifluoromethyl)imidazo[1,2-a]pyrazine IV-508;

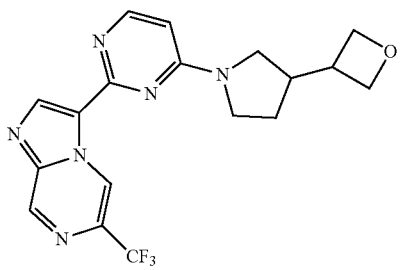 [SMILES: FC(F)(F)c1cn2c(-c3nccc(N4CCC(C5COC5)C4)n3)cnc2cn1]

3-(4-(3-(Methoxymethyl)azepan-1-yl)pyrimidin-2-yl)-6-(trifluoromethyl)imidazo[1,2-a]pyrazine IV-509;

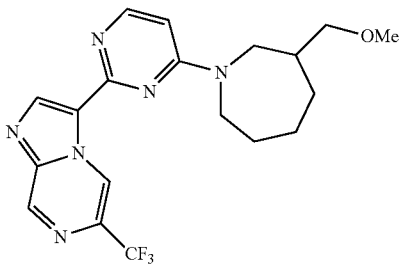 [SMILES: COCC1CCCCN(c2ccnc(-c3cnc4cnc(C(F)(F)F)cn34)n2)C1]

4-((1-(2-(6-(Trifluoromethyl)imidazo[1,2-a]pyrazin-3-yl)pyrimidin-4-yl)piperidin-4-yl)methyl)morpholine IV-510;

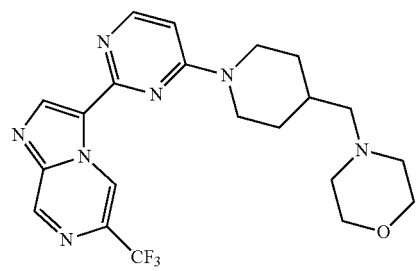 [SMILES: FC(F)(F)c1cn2c(-c3nccc(N4CCC(CN5CCOCC5)CC4)n3)cnc2cn1]

7-(2-(6-(Trifluoromethyl)imidazo[1,2-a]pyrazin-3-yl)pyrimidin-4-yl)-2-oxa-7-azaspiro[3.5]nonane IV-511;

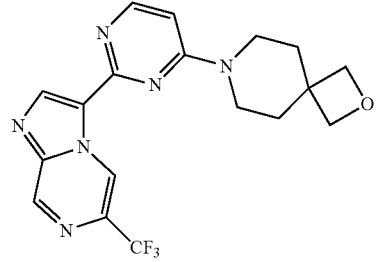

3-(4-(4-(Methoxymethyl)piperidin-1-yl)pyrimidin-2-yl)-6-(trifluoromethyl)imidazo[1,2-a]pyrazine IV-512;

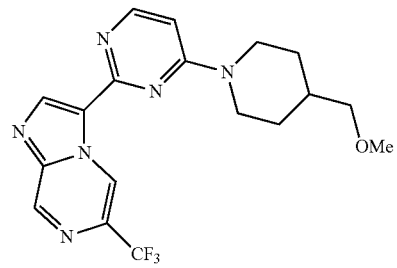 [SMILES: COCC1CCN(c2ccnc(-c3cnc4cnc(C(F)(F)F)cn34)n2)CC1]

1-(2-(6-(Trifluoromethyl)imidazo[1,2-a]pyrazin-3-yl)pyrimidin-4-yl)piperidine-4-carbonitrile IV-513;

2-(1-(2-(6-(Trifluoromethyl)imidazo[1,2-a]pyrazin-3-yl)pyrimidin-4-yl)piperidin-3-yl)acetonitrile IV-514;

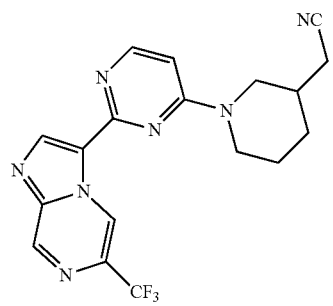 [SMILES: N#CCC1CCCN(c2ccnc(-c3cnc4cnc(C(F)(F)F)cn34)n2)C1]

(3aR,7aR)-5-(2-(6-(Trifluoromethyl)imidazo[1,2-a]pyrazin-3-yl)pyrimidin-4-yl)octahydro-3H-pyrrolo[3,4-a]pyridin-3-one IV-515;

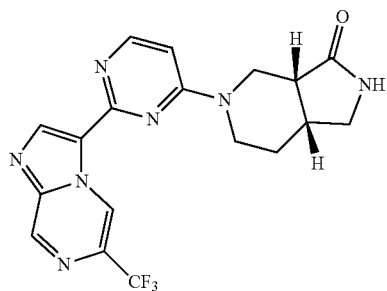 [SMILES: O=C1NC[C@@H]2CCN(c3ccnc(-c4cnc5cnc(C(F)(F)F)cn45)n3)C[C@H]12]

1-(2-(6-(Trifluoromethyl)imidazo[1,2-a]pyrazin-3-yl)py-
rimidin-4-yl)piperidine-3-carbonitrile IV-516;

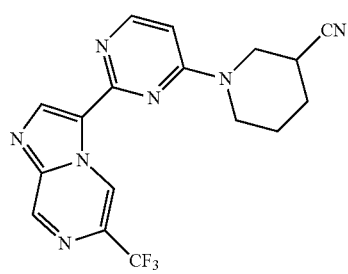

3-(4-(4-Methylpiperidin-1-yl)pyrimidin-2-yl)-6-(trifluo-
romethyl)imidazo[1,2-a]pyrazine IV-517;

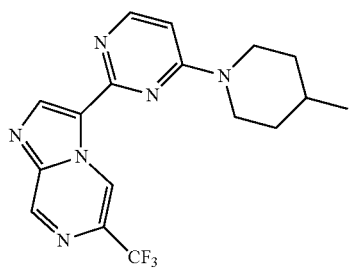

3-(4-(2-Methylpiperidin-1-yl)pyrimidin-2-yl)-6-(trifluo-
romethyl)imidazo[1,2-a]pyrazine IV-518;

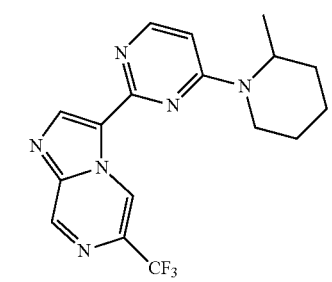 [SMILES: CC1CCCCN1c1ccnc(-c2cnc3cnc(C(F)(F)F)cn23)n1]

3-(4-(2,3-Dimethylpiperidin-1-yl)pyrimidin-2-yl)-6-(trif-
luoromethyl)imidazo[1,2-a]pyrazine IV-519;

2-(1-(2-(6-(Trifluoromethyl)imidazo[1,2-a]pyrazin-3-yl)py-
rimidin-4-yl)pyrrolidin-3-yl)propan-2-ol IV-520;

(R)-1-(2-(6-(Trifluoromethyl)imidazo[1,2-a]pyrazin-3-yl)
pyrimidin-4-yl)pyrrolidine-3-carbonitrile IV-521;

2-(2-(6-(Trifluoromethyl)imidazo[1,2-a]pyrazin-3-yl)py-
rimidin-4-yl)-8-oxa-2-azaspiro[4.5]decane IV-522;

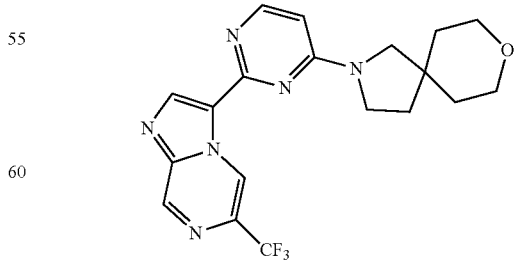

6-(2-(6-(Trifluoromethyl)imidazo[1,2-a]pyrazin-3-yl)py-
rimidin-4-yl)-2-oxa-6-azaspiro[3.5]nonane IV-523;

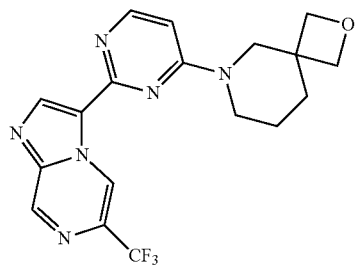 [SMILES: FC(F)(F)c1cn2c(-c3nccc(N4CCCC5(COC5)C4)n3)cnc2cn1]

3-(4-(3-(3-Fluoro-1H-pyrazol-4-yl)pyrrolidin-1-yl)pyrimidin-2-yl)-6-(trifluoromethyl)imidazo[1,2-a]pyrazine IV-524;

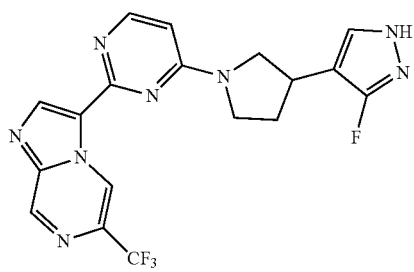

2-(1H-Imidazol-4-yl)-3,6-dimethyl-4-(2-(6-(trifluoromethyl)imidazo[1,2-a]pyrazin-3-yl)pyrimidin-4-yl)morpholine (all syn diastereoisomer) IV-525;

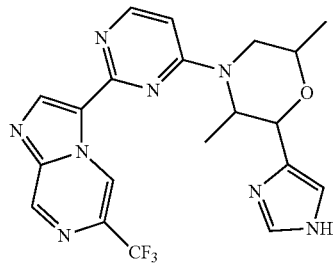 [SMILES: CC1CN(c2ccnc(-c3cnc4cnc(C(F)(F)F)cn34)n2)C(C)C(c2c[nH]cn2)O1]

N-((1-(2-(6-(Trifluoromethyl)imidazo[1,2-a]pyrazin-3-yl)pyrimidin-4-yl)piperidin-3-yl)methyl)acetamide IV-526;

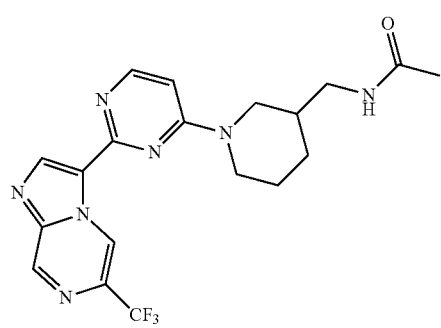 [SMILES: CC(=O)NCC1CCCN(c2ccnc(-c3cnc4cnc(C(F)(F)F)cn34)n2)C1]

1-((1-(2-(6-(Trifluoromethyl)imidazo[1,2-a]pyrazin-3-yl)pyrimidin-4-yl)piperidin-3-yl)methyl)urea IV-527;

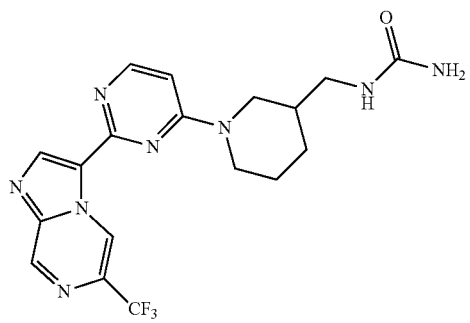 [SMILES: NC(=O)NCC1CCCN(c2ccnc(-c3cnc4cnc(C(F)(F)F)cn34)n2)C1]

N-(1-(2-(6-(Trifluoromethyl)imidazo[1,2-a]pyrazin-3-yl)pyrimidin-4-yl)pyrrolidin-3-yl)acetamide IV-528;

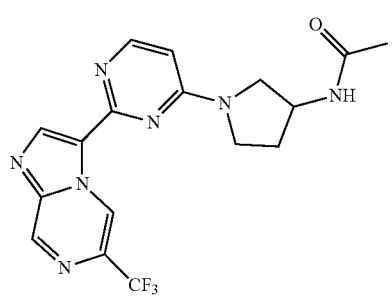 [SMILES: CC(=O)NC1CCN(c2ccnc(-c3cnc4cnc(C(F)(F)F)cn34)n2)C1]

2-(1-(2-(6-(Trifluoromethyl)imidazo[1,2-a]pyrazin-3-yl)pyrimidin-4-yl)piperidin-3-yl)acetamide IV-529;

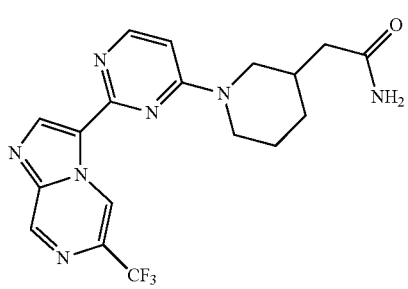 [SMILES: NC(=O)CC1CCCN(c2ccnc(-c3cnc4cnc(C(F)(F)F)cn34)n2)C1]

N-(1-(2-(6-(Trifluoromethyl)imidazo[1,2-a]pyrazin-3-yl)pyrimidin-4-yl)piperidin-3-yl)acetamide IV-530;

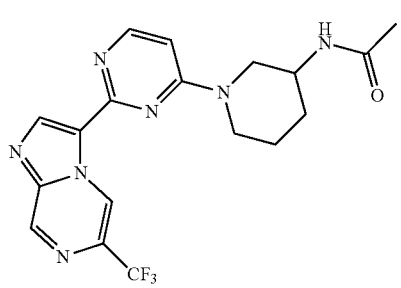 [SMILES: CC(=O)NC1CCCN(c2ccnc(-c3cnc4cnc(C(F)(F)F)cn34)n2)C1]

2,2-Dimethyl-4-(2-(6-(trifluoromethyl)imidazo[1,2-a]pyrazin-3-yl)pyrimidin-4-yl)morpholine IV-531;

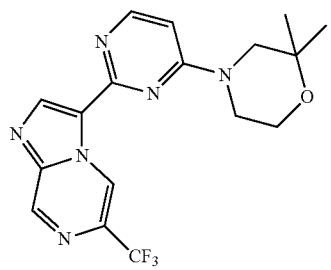 [SMILES: CC1(C)CN(c2ccnc(-c3cnc4cnc(C(F)(F)F)cn34)n2)CCO1]

3,3-Dimethyl-4-(2-(6-(trifluoromethyl)imidazo[1,2-a]
pyrazin-3-yl)pyrimidin-4-yl)morpholine IV-532;

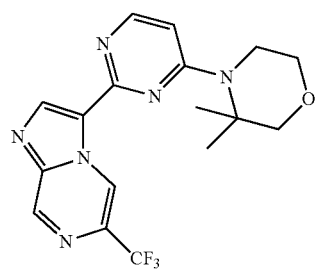 [SMILES: CC1(C)COCCN1c1ccnc(-c2cnc3cnc(C(F)(F)F)cn23)n1]

7-(2-(6-(Trifluoromethyl)imidazo[1,2-a]pyrazin-3-yl)py-
rimidin-4-yl)-2,7-diazaspiro[4.4]nonan-1-one IV-533;

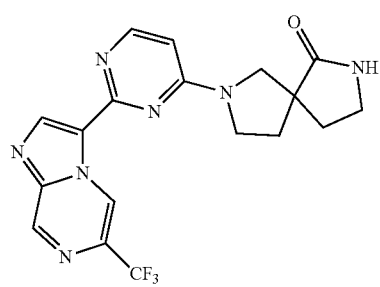 [SMILES: O=C1NCCC12CCN(c1ccnc(-c3cnc4cnc(C(F)(F)F)cn34)n1)C2]

7-(2-(6-(Trifluoromethyl)imidazo[1,2-a]pyrazin-3-yl)py-
rimidin-4-yl)-2,7-diazaspiro[4.4]nonan-3-one IV-534;

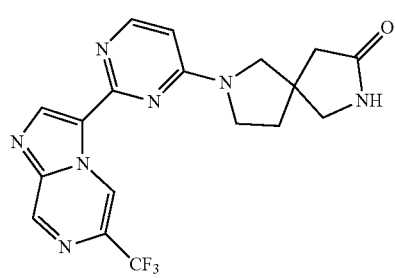 [SMILES: O=C1CC2(CCN(c3ccnc(-c4cnc5cnc(C(F)(F)F)cn45)n3)C2)CN1]

4-(1-(2-(6-(Trifluoromethyl)imidazo[1,2-a]pyrazin-3-yl)py-
rimidin-4-yl)-1,2,5,6-tetrahydropyridin-3-yl)isothiazole
IV-535;

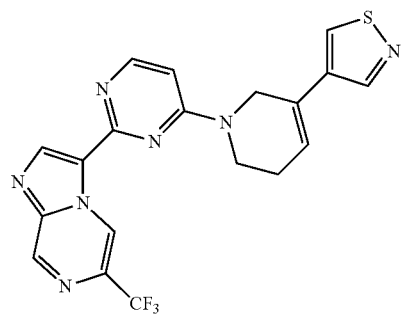 [SMILES: FC(F)(F)c1cn2c(-c3nccc(N4CCC=C(c5cnsc5)C4)n3)cnc2cn1]

1-(2-(6-(Trifluoromethyl)imidazo[1,2-a]pyrazin-3-yl)py-
rimidin-4-yl)piperidine-3-sulfonamide IV-536;

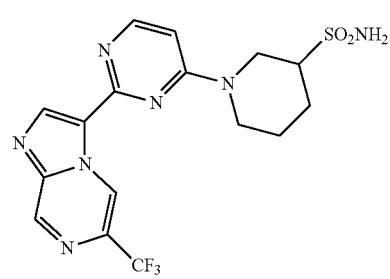 [SMILES: NS(=O)(=O)C1CCCN(c2ccnc(-c3cnc4cnc(C(F)(F)F)cn34)n2)C1]

N-((1-(2-(6-(Trifluoromethyl)imidazo[1,2-a]pyrazin-3-yl)
pyrimidin-4-yl)pyrrolidin-3-yl)methyl)acetamide IV-537;

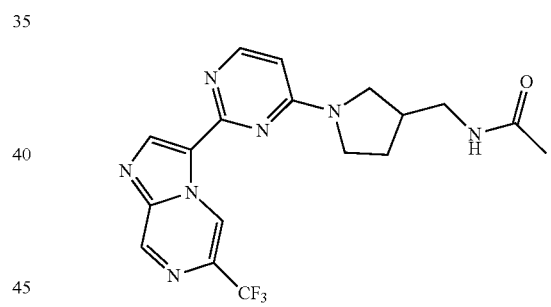

3-Methyl-1-(2-(6-(trifluoromethyl)imidazo[1,2-a]pyrazin-
3-yl)pyrimidin-4-yl)piperidine-3-carboxamide IV-539;

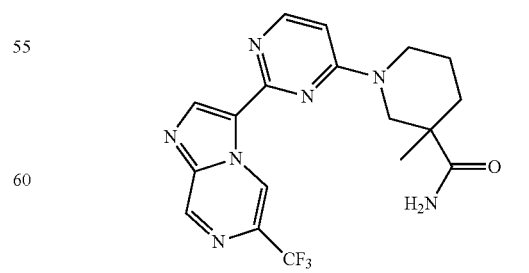

7-(2-(6-(Trifluoromethyl)imidazo[1,2-a]pyrazin-3-yl)py-
rimidin-4-yl)-2,7-diazaspiro[4.5]decan-1-one IV-542;

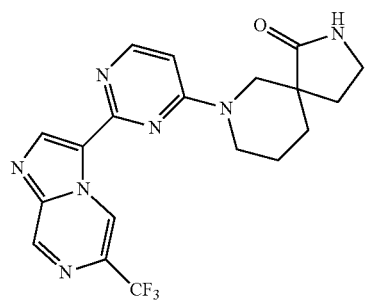 [SMILES: O=C1NCCC12CCCN(c1ccnc(-c3cnc4cnc(C(F)(F)F)cn34)n1)C2]

3-(4-(3-(1H-1,2,4-Triazol-1-yl)piperidin-1-yl)pyrimidin-2-yl)-6-(trifluoromethyl)imidazo[1,2-a]pyrazine IV-547;

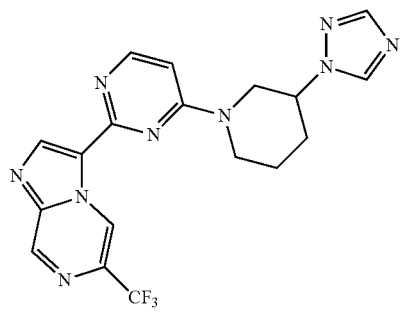 [SMILES: FC(F)(F)c1cn2c(-c3nccc(N4CCCC(n5cncn5)C4)n3)cnc2cn1]

4-(1-(2-(6-(Trifluoromethyl)imidazo[1,2-a]pyrazin-3-yl)pyrimidin-4-yl)-1,2,5,6-tetrahydropyridin-3-yl)-1H-pyrazole-3-carbonitrile IV-548;

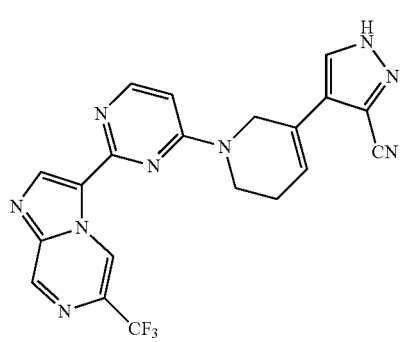 [SMILES: N#Cc1n[nH]cc1C1=CCCN(c2ccnc(-c3cnc4cnc(C(F)(F)F)cn34)n2)C1]

3-(4-(3-(Pyridin-4-yl)pyrrolidin-1-yl)pyrimidin-2-yl)-6-(trifluoromethyl)imidazo[1,2-a]pyrazine IV-550;

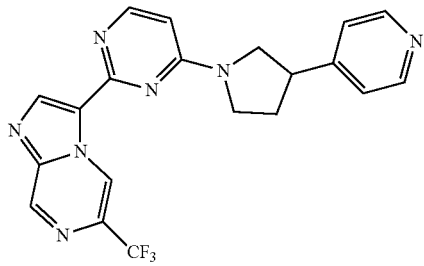 [SMILES: FC(F)(F)c1cn2c(-c3nccc(N4CCC(c5ccncc5)C4)n3)cnc2cn1]

(4aS,7aS)-4-Methyl-6-(2-(6-(trifluoromethyl)imidazo[1,2-a]pyrazin-3-yl)pyrimidin-4-yl)hexahydropyrrolo[3,4-b][1,4]oxazin-3(2H)-one IV-551;

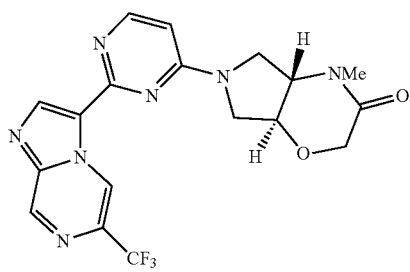 [SMILES: CN1C(=O)CO[C@H]2CN(c3ccnc(-c4cnc5cnc(C(F)(F)F)cn45)n3)C[C@@H]21]

3-(4-(3-(Pyridin-2-yl)pyrrolidin-1-yl)pyrimidin-2-yl)-6-(trifluoromethyl)imidazo[1,2-a]pyrazine IV-552;

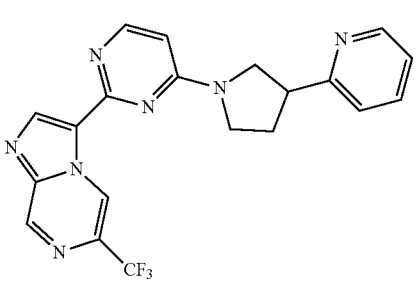

4-(1-(2-(6-(Trifluoromethyl)imidazo[1,2-a]pyrazin-3-yl)pyrimidin-4-yl)pyrrolidin-3-yl)morpholine IV-553;

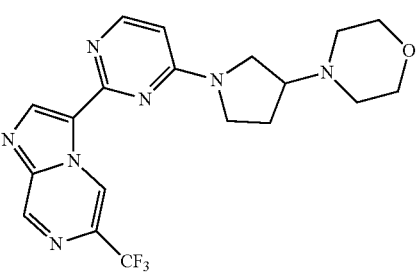 [SMILES: FC(F)(F)c1cn2c(-c3nccc(N4CCC(N5CCOCC5)C4)n3)cnc2cn1]

7-Methyl-2-(2-(6-(trifluoromethyl)imidazo[1,2-a]pyrazin-3-yl)pyrimidin-4-yl)-2,7-diazaspiro[4.5]decan-6-one IV-554;

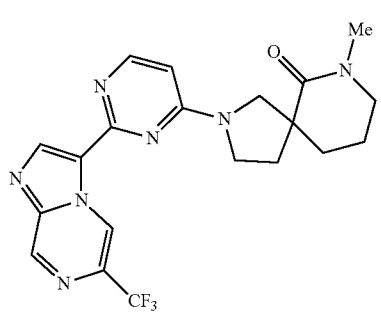 [SMILES: CN1CCCC2(CCN(c3ccnc(-c4cnc5cnc(C(F)(F)F)cn45)n3)C2)C1=O]

3-(4-(3,4-Dimethylpyrrolidin-1-yl)pyrimidin-2-yl)-6-(trifluoromethyl)imidazo[1,2-a]pyrazine IV-555;

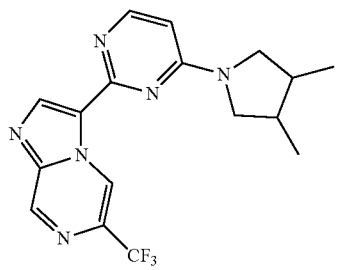 [SMILES: CC1CN(c2ccnc(-c3cnc4cnc(C(F)(F)F)cn34)n2)CC1C]

3-(4-(3-Phenylpyrrolidin-1-yl)pyrimidin-2-yl)-6-(trifluoromethyl)imidazo[1,2-a]pyrazine IV-556;

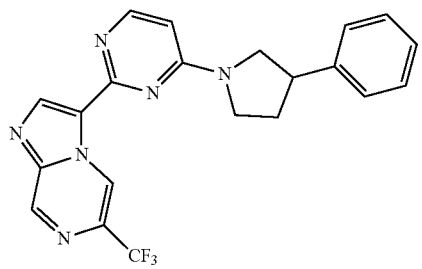 [SMILES: FC(F)(F)c1cn2c(-c3nccc(N4CCC(c5ccccc5)C4)n3)cnc2cn1]

1-((1-(2-(6-(Trifluoromethyl)imidazo[1,2-a]pyrazin-3-yl)pyrimidin-4-yl)pyrrolidin-3-yl)methyl)pyrrolidin-2-one IV-557;

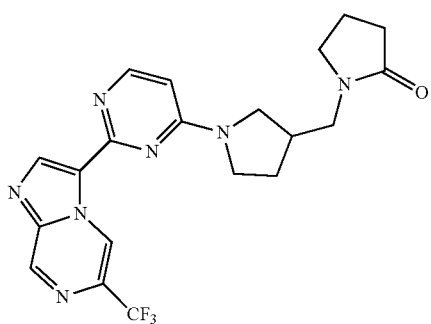 [SMILES: O=C1CCCN1CC1CCN(c2ccnc(-c3cnc4cnc(C(F)(F)F)cn34)n2)C1]

3-(4-(3-(1H-Pyrazol-4-yl)-5-(trifluoromethyl)piperazin-1-yl)pyrimidin-2-yl)-6-(trifluoromethyl)imidazo[1,2-a]pyrazine IV-558;

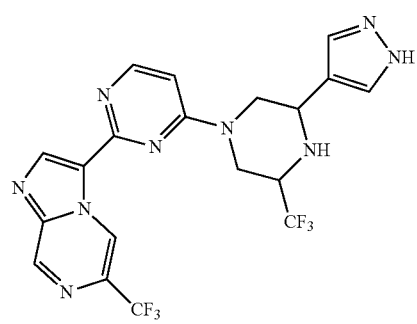

3-(4-(3-(Phenoxymethyl)pyrrolidin-1-yl)pyrimidin-2-yl)-6-(trifluoromethyl)imidazo[1,2-a]pyrazine IV-559;

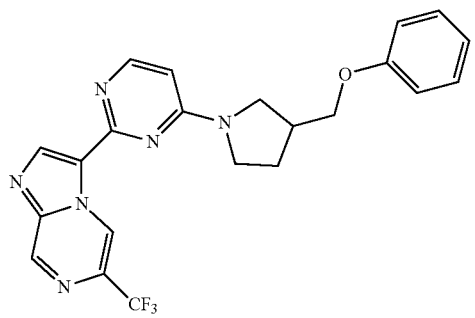 [SMILES: FC(F)(F)c1cn2c(-c3nccc(N4CCC(COc5ccccc5)C4)n3)cnc2cn1]

7-(2-(6-(Trifluoromethyl)imidazo[1,2-a]pyrazin-3-yl)pyrimidin-4-yl)-1,3,7-triazaspiro[4.4]nonane-2,4-dione IV-560;

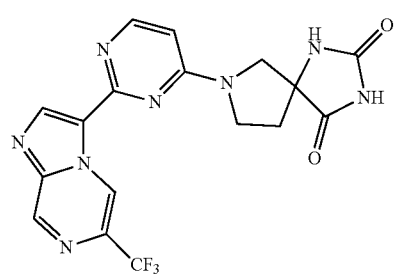 [SMILES: O=C1NC(=O)C2(CCN(c3ccnc(-c4cnc5cnc(C(F)(F)F)cn45)n3)C2)N1]

3-(4-(2-Benzylpyrrolidin-1-yl)pyrimidin-2-yl)-6-(trifluoromethyl)imidazo[1,2-a]pyrazine IV-561;

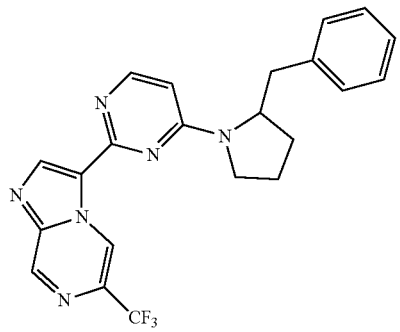 [SMILES: FC(F)(F)c1cn2c(-c3nccc(N4CCCC4Cc4ccccc4)n3)cnc2cn1]

3-(4-(3-(1H-Imidazol-1-yl)pyrrolidin-1-yl)pyrimidin-2-yl)-6-(trifluoromethyl)imidazo[1,2-a]pyrazine IV-564;

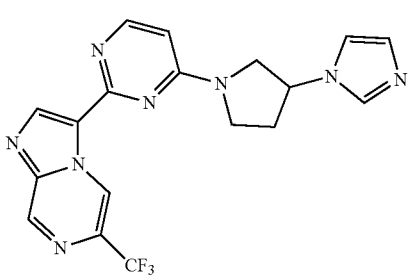 [SMILES: FC(F)(F)c1cn2c(-c3nccc(N4CCC(n5ccnc5)C4)n3)cnc2cn1]

9-Methyl-2-(2-(6-(trifluoromethyl)imidazo[1,2-a]pyrazin-3-yl)pyrimidin-4-yl)-6-oxa-2,9-diazaspiro[4.5]decan-8-one IV-565;

1085

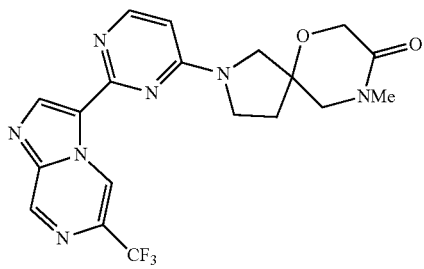 [SMILES: CN1CC2(CCN(c3ccnc(-c4cnc5cnc(C(F)(F)F)cn45)n3)C2)OCC1=O]

2-(4-(2-(6-(Trifluoromethyl)imidazo[1,2-a]pyrazin-3-yl)pyrimidin-4-yl)-1,4-diazepan-1-yl)acetamide IV-566;

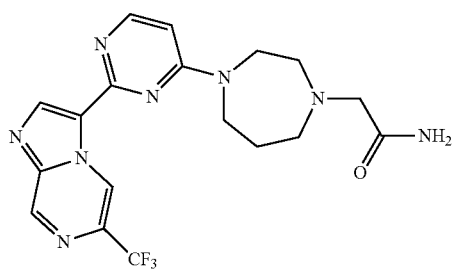 [SMILES: NC(=O)CN1CCCN(c2ccnc(-c3cnc4cnc(C(F)(F)F)cn34)n2)CC1]

3-(4-Chloro-6-(2,5-dimethyl-3-(1H-pyrazol-4-yl)piperazin-1-yl)pyrimidin-2-yl)-6-(trifluoromethyl)imidazo[1,2-a]pyrazine (all syn diastereoisomer) IV-567;

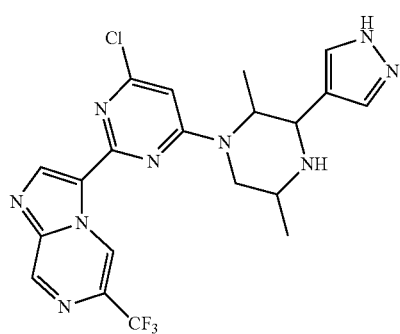

8-(2-(6-(Trifluoromethyl)imidazo[1,2-a]pyrazin-3-yl)pyrimidin-4-yl)hexahydro-2H-pyrazino[1,2-a]pyrazin-1(6H)-one IV-568;

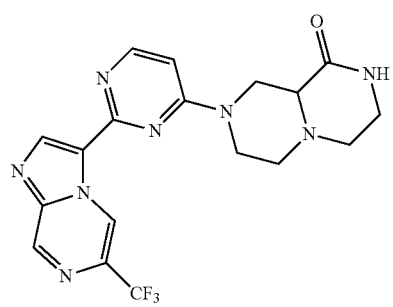 [SMILES: O=C1NCCN2CCN(c3ccnc(-c4cnc5cnc(C(F)(F)F)cn45)n3)CC12]

5-(2-(6-(Trifluoromethyl)imidazo[1,2-a]pyrazin-3-yl)pyrimidin-4-yl)hexahydro-2H-thieno[2,3-a]pyrrole 1,1-dioxide IV-570;

1086

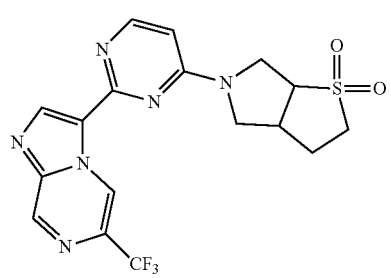 [SMILES: O=S1(=O)CCC2CN(c3ccnc(-c4cnc5cnc(C(F)(F)F)cn45)n3)CC21]

2-(2-(6-(Trifluoromethyl)imidazo[1,2-a]pyrazin-3-yl)pyrimidin-4-yl)octahydro-4H-pyrido[1,2-a]pyrazin-4-one IV-571;

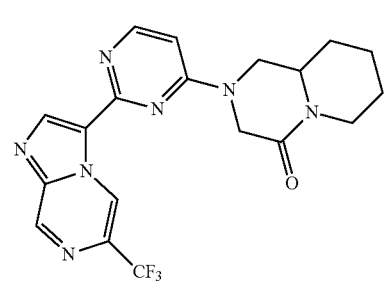 [SMILES: O=C1CN(c2ccnc(-c3cnc4cnc(C(F)(F)F)cn34)n2)CC2CCCCN12]

6-(Trifluoromethyl)-3-(4-(3-(3-(trifluoromethyl)-1H-pyrazol-4-yl)pyrrolidin-1-yl)pyrimidin-2-yl)imidazo[1,2-a]pyrazine IV-572;

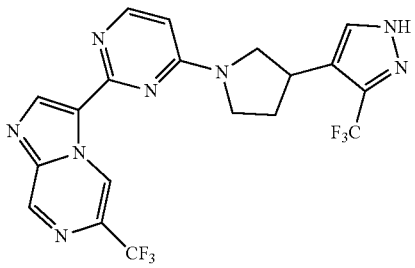 [SMILES: FC(F)(F)c1cn2c(-c3nccc(N4CCC(c5c[nH]nc5C(F)(F)F)C4)n3)cnc2cn1]

(4-(1-(2-(6-(Trifluoromethyl)imidazo[1,2-a]pyrazin-3-yl)pyrimidin-4-yl)pyrrolidin-3-yl)-1H-pyrazol-3-yl)methanol IV-573;

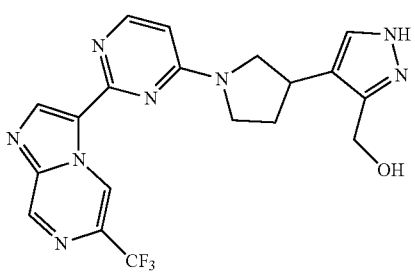 [SMILES: OCc1n[nH]cc1C1CCN(c2ccnc(-c3cnc4cnc(C(F)(F)F)cn34)n2)C1]

3-(4-(3-(3,5-Dimethyl-1H-pyrazol-4-yl)pyrrolidin-1-yl)pyrimidin-2-yl)-6-(trifluoromethyl)imidazo[1,2-a]pyrazine IV-574;

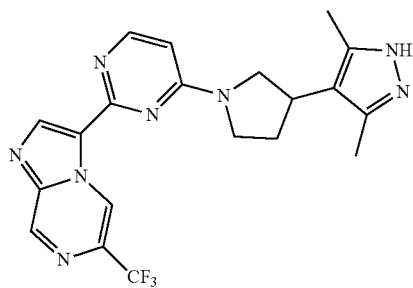 [SMILES: Cc1n[nH]c(C)c1C1CCN(c2ccnc(-c3cnc4cnc(C(F)(F)F)cn34)n2)C1]

3-(4-(3-(3-Methyl-1H-pyrazol-4-yl)pyrrolidin-1-yl)pyrimidin-2-yl)-6-(trifluoromethyl)imidazo[1,2-a]pyrazine IV-575;

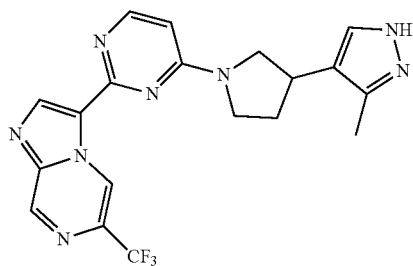 [SMILES: Cc1n[nH]cc1C1CCN(c2ccnc(-c3cnc4cnc(C(F)(F)F)cn34)n2)C1]

3-(4-(3-(3-Cyclopropyl-1H-pyrazol-4-yl)pyrrolidin-1-yl)pyrimidin-2-yl)-6-(trifluoromethyl)imidazo[1,2-a]pyrazine IV-576;

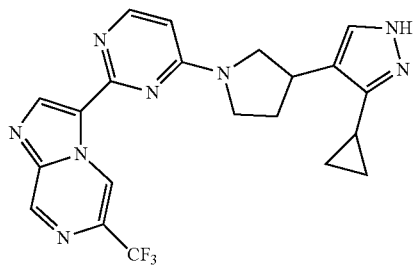 [SMILES: FC(F)(F)c1cn2c(-c3nccc(N4CCC(c5c[nH]nc5C5CC5)C4)n3)cnc2cn1]

3-(6-(2,5-Dimethyl-3-(1H-pyrazol-4-yl)piperazin-1-yl)pyrazin-2-yl)-6-(trifluoromethyl)imidazo[1,2-a]pyrazine (all syn diastereoisomer) IV-577;

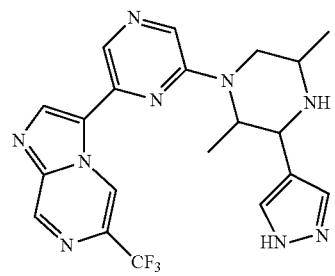 [SMILES: CC1CN(c2cncc(-c3cnc4cnc(C(F)(F)F)cn34)n2)C(C)C(c2cn[nH]c2)N1]

6-(2,5-Dimethyl-3-(1H-pyrazol-4-yl)piperazin-1-yl)-N-methyl-2-(6-(trifluoromethyl)imidazo[1,2-a]pyrazin-3-yl)pyrimidin-4-amine IV-578;

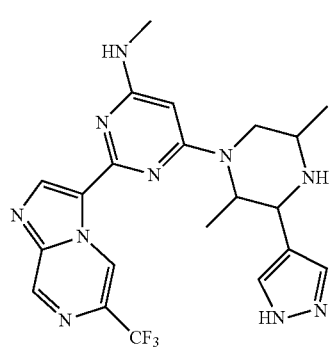 [SMILES: CNc1cc(N2CC(C)NC(c3cn[nH]c3)C2C)nc(-c2cnc3cnc(C(F)(F)F)cn23)n1]

3-Methyl-7-(2-(6-(trifluoromethyl)imidazo[1,2-a]pyrazin-3-yl)pyrimidin-4-yl)-1-oxa-3,7-diazaspiro[4.4]nonan-2-one IV-579;

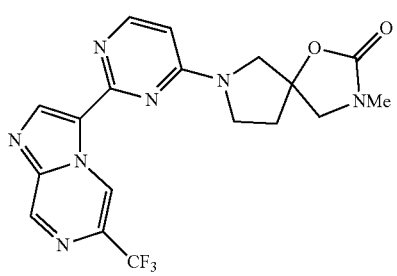 [SMILES: CN1CC2(CCN(c3ccnc(-c4cnc5cnc(C(F)(F)F)cn45)n3)C2)OC1=O]

3-(4-(3-(Tetrahydrofuran-3-yl)pyrrolidin-1-yl)pyrimidin-2-yl)-6-(trifluoromethyl)imidazo[1,2-a]pyrazine IV-580;

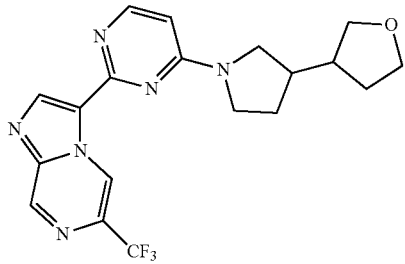

3-Methyl-1-(2-(6-(trifluoromethyl)imidazo[1,2-a]pyrazin-3-yl)pyrimidin-4-yl)pyrrolidine-3-carboxamide IV-581;

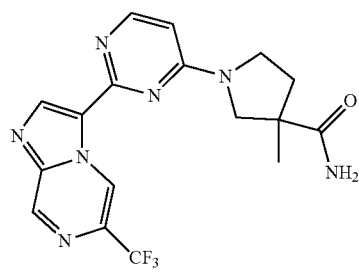 [SMILES: CC1(C(N)=O)CCN(c2ccnc(-c3cnc4cnc(C(F)(F)F)cn34)n2)C1]

5,5-Difluoro-1-(2-(6-(trifluoromethyl)imidazo[1,2-a]pyrazin-3-yl)pyrimidin-4-yl)piperidine-3-carboxamide IV-582;

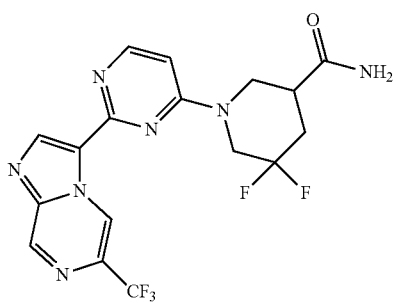 [SMILES: NC(=O)C1CN(c2ccnc(-c3cnc4cnc(C(F)(F)F)cn34)n2)CC(F)(F)C1]

3-(6-(2,5-Dimethyl-3-(1H-pyrazol-4-yl)piperazin-1-yl)pyridin-2-yl)-6-(trifluoromethyl)imidazo[1,2-a]pyrazine (all syn diastereoisomer) IV-583;

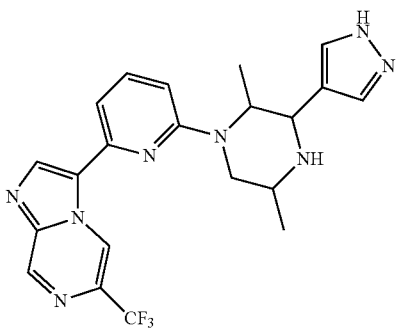 [SMILES: CC1CN(c2cccc(-c3cnc4cnc(C(F)(F)F)cn34)n2)C(C)C(c2cn[nH]c2)N1]

1-(1-(2-(6-(Trifluoromethyl)imidazo[1,2-a]pyrazin-3-yl)pyrimidin-4-yl)piperidin-3-yl)imidazolidin-2-one IV-584;

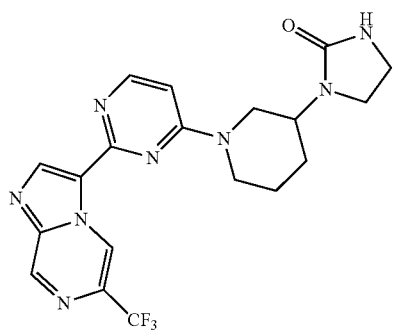 [SMILES: O=C1NCCN1C1CCCN(c2ccnc(-c3cnc4cnc(C(F)(F)F)cn34)n2)C1]

3-(4-(4-Methylpiperazin-1-yl)pyrimidin-2-yl)-6-(trifluoromethyl)imidazo[1,2-a]pyrazine IV-585;

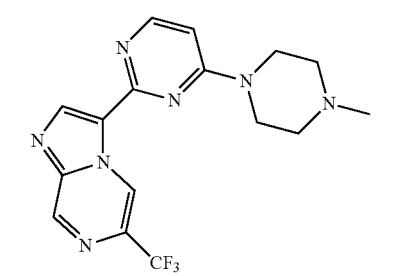

2-(Methoxymethyl)-6-methyl-4-(2-(6-(trifluoromethyl)imidazo[1,2-a]pyrazin-3-yl)pyrimidin-4-yl)morpholine IV-586;

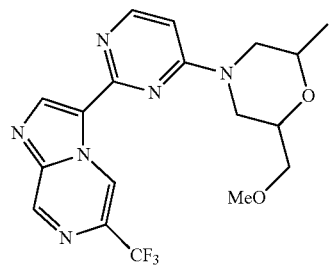 [SMILES: COCC1CN(c2ccnc(-c3cnc4cnc(C(F)(F)F)cn34)n2)CC(C)O1]

2-(Methoxymethyl)-6-methyl-4-(2-(6-(trifluoromethyl)imidazo[1,2-a]pyrazin-3-yl)pyrimidin-4-yl)morpholine IV-587;

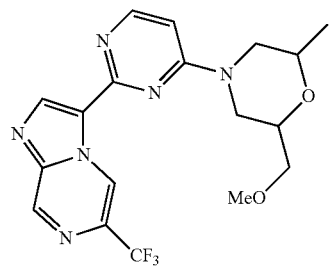 [SMILES: COCC1CN(c2ccnc(-c3cnc4cnc(C(F)(F)F)cn34)n2)CC(C)O1]

2-(Methoxymethyl)-4-(2-(6-(trifluoromethyl)imidazo[1,2-a]pyrazin-3-yl)pyrimidin-4-yl)morpholine IV-588;

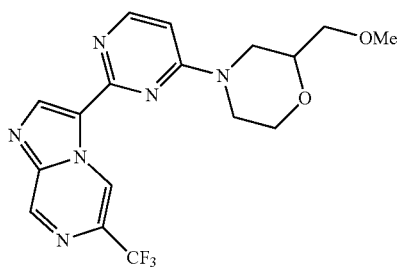

3-(4-(3-(1H-Pyrazol-3-yl)piperidin-1-yl)pyrimidin-2-yl)-6-(trifluoromethyl)imidazo[1,2-a]pyrazine IV-589;

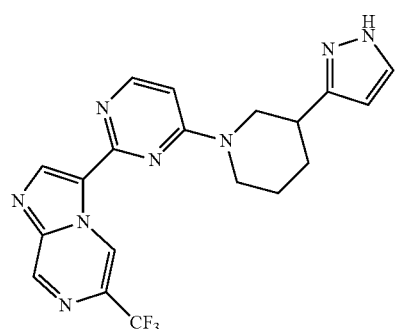

1091

(5-(1H-Pyrazol-4-yl)-1-(2-(6-(trifluoromethyl)imidazo[1,2-a]pyrazin-3-yl)pyrimidin-4-yl)piperidin-3-yl)dimethylphosphine oxide IV-590;

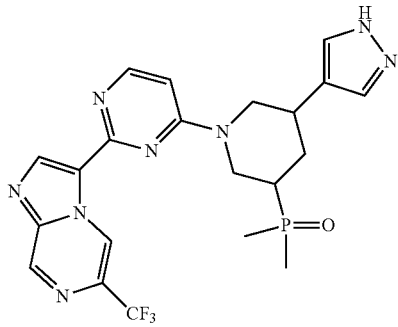 [SMILES: CP(C)(=O)C1CC(c2cn[nH]c2)CN(c2ccnc(-c3cnc4cnc(C(F)(F)F)cn34)n2)C1]

(5-(1H-Pyrazol-4-yl)-1-(2-(6-(trifluoromethyl)imidazo[1,2-a]pyrazin-3-yl)pyrimidin-4-yl)piperidin-3-yl)dimethylphosphine oxide IV-591;

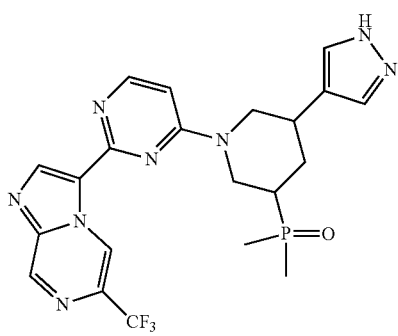 [SMILES: CP(C)(=O)C1CC(c2cn[nH]c2)CN(c2ccnc(-c3cnc4cnc(C(F)(F)F)cn34)n2)C1]

(5-(1H-Pyrazol-4-yl)-1-(2-(6-(trifluoromethyl)imidazo[1,2-a]pyrazin-3-yl)pyrimidin-4-yl)piperidin-3-yl)dimethylphosphine oxide IV-592;

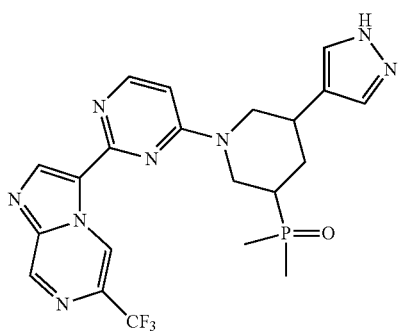 [SMILES: CP(C)(=O)C1CC(c2cn[nH]c2)CN(c2ccnc(-c3cnc4cnc(C(F)(F)F)cn34)n2)C1]

3-(4-(3-((Methylthio)methyl)pyrrolidin-1-yl)pyrimidin-2-yl)-6-(trifluoromethyl)imidazo[1,2-a]pyrazine IV-594;

1092

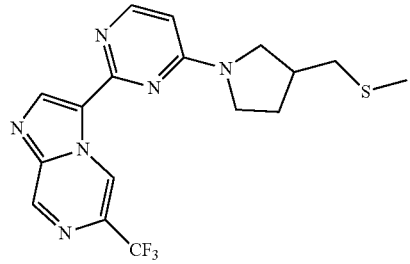 [SMILES: CSCC1CCN(c2ccnc(-c3cnc4cnc(C(F)(F)F)cn34)n2)C1]

4-(2-(6-(Trifluoromethyl)imidazo[1,2-a]pyrazin-3-yl)pyrimidin-4-yl)piperazine-2-carboxamide IV-595;

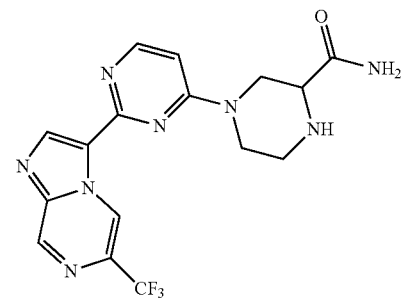

1-Methyl-4-(2-(6-(trifluoromethyl)imidazo[1,2-a]pyrazin-3-yl)pyrimidin-4-yl)piperazine-2-carboxamide IV-596;

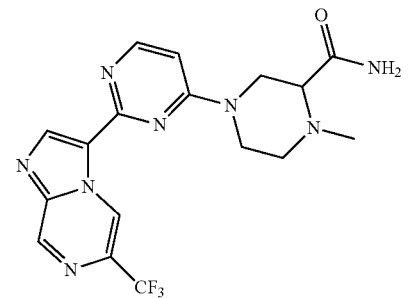

(S)-3-(4-(2-Methylpiperidin-1-yl)pyrimidin-2-yl)-6-(trifluoromethyl)imidazo[1,2-a]pyrazine IV-597;

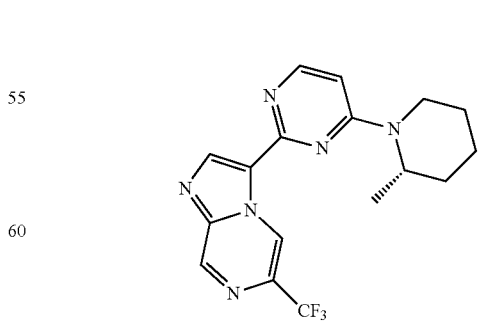

1-(2-(6-(Trifluoromethyl)imidazo[1,2-a]pyrazin-3-yl)pyrimidin-4-yl)pyrrolidine-3-carboxamide IV-598;

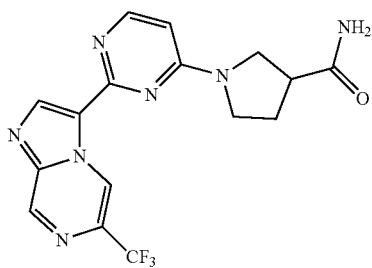 [SMILES: NC(=O)C1CCN(c2ccnc(-c3cnc4cnc(C(F)(F)F)cn34)n2)C1]

4-(2-(6-(Trifluoromethyl)imidazo[1,2-a]pyrazin-3-yl)pyrimidin-4-yl)morpholine-2-carboxamide IV-599;

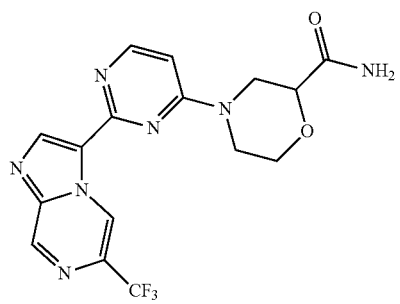

4-(1-(2-(6-(Trifluoromethyl)imidazo[1,2-a]pyrazin-3-yl)pyrimidin-4-yl)pyrrolidin-3-yl)piperazin-2-one IV-602;

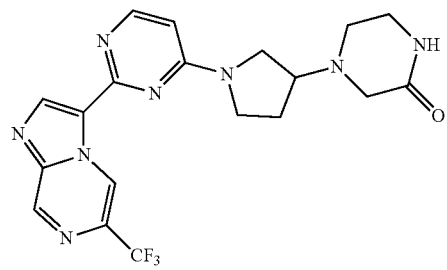 [SMILES: O=C1CN(C2CCN(c3ccnc(-c4cnc5cnc(C(F)(F)F)cn45)n3)C2)CCN1]

2-(1-(2-(6-(Trifluoromethyl)imidazo[1,2-a]pyrazin-3-yl)pyrimidin-4-yl)piperidin-4-yl)acetamide IV-605;

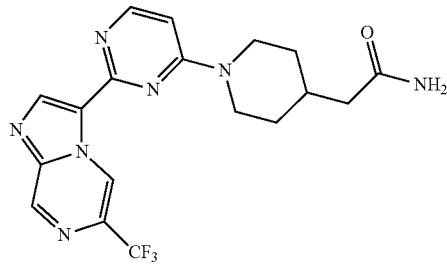 [SMILES: NC(=O)CC1CCN(c2ccnc(-c3cnc4cnc(C(F)(F)F)cn34)n2)CC1]

N-(1-(2-(6-(Trifluoromethyl)imidazo[1,2-a]pyrazin-3-yl)pyrimidin-4-yl)pyrrolidin-3-yl)-1H-pyrazol-4-amine IV-606;

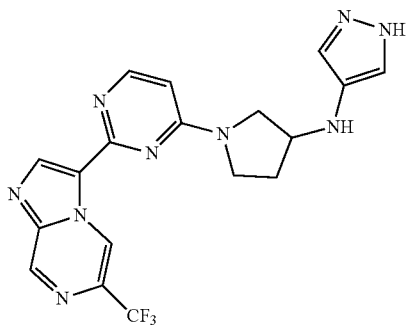 [SMILES: FC(F)(F)c1cn2c(-c3nccc(N4CCC(Nc5cn[nH]c5)C4)n3)cnc2cn1]

3-(4-(3-(Tetrahydrofuran-3-yl)pyrrolidin-1-yl)pyrimidin-2-yl)-6-(trifluoromethyl)imidazo[1,2-a]pyrazine IV-608;

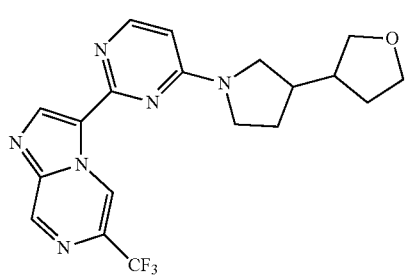 [SMILES: FC(F)(F)c1cn2c(-c3nccc(N4CCC(C5CCOC5)C4)n3)cnc2cn1]

3-(4-(3-(Tetrahydrofuran-3-yl)pyrrolidin-1-yl)pyrimidin-2-yl)-6-(trifluoromethyl)imidazo[1,2-a]pyrazine IV-609;

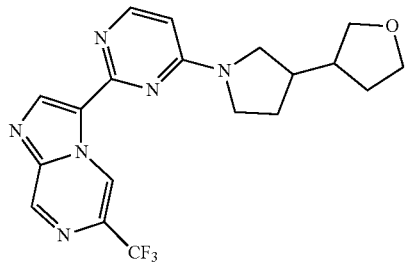 [SMILES: FC(F)(F)c1cn2c(-c3nccc(N4CCC(C5CCOC5)C4)n3)cnc2cn1]

6-(Trifluoromethyl)-3-(4-(2,2,4-trimethylpyrrolidin-1-yl)pyrimidin-2-yl)imidazo[1,2-a]pyrazine IV-610;

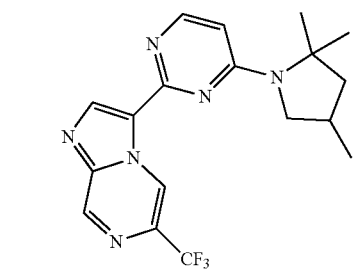 [SMILES: CC1CN(c2ccnc(-c3cnc4cnc(C(F)(F)F)cn34)n2)C(C)(C)C1]

1-(2-(6-(Trifluoromethyl)imidazo[1,2-a]pyrazin-3-yl)pyrimidin-4-yl)piperidine-4-carboxamide IV-611;

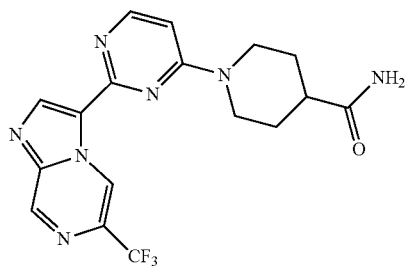

4-(2-(6-(Trifluoromethyl)imidazo[1,2-a]pyrazin-3-yl)pyrimidin-4-yl)piperazine-1-carboxamide IV-612;

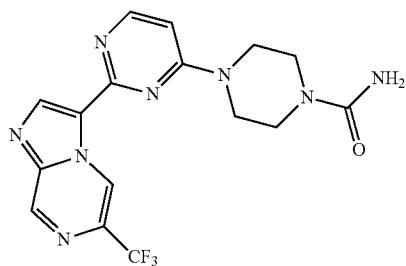

(5-Methyl-4-(2-(6-(trifluoromethyl)imidazo[1,2-a]pyrazin-3-yl)pyrimidin-4-yl)morpholin-2-yl)methanol IV-613;

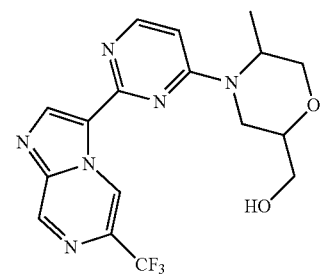 [SMILES: CC1COC(CO)CN1c1ccnc(-c2cnc3cnc(C(F)(F)F)cn23)n1]

3-(1-(2-(6-(Trifluoromethyl)imidazo[1,2-a]pyrazin-3-yl)pyrimidin-4-yl)pyrrolidin-3-yl)propan-1-ol IV-616;

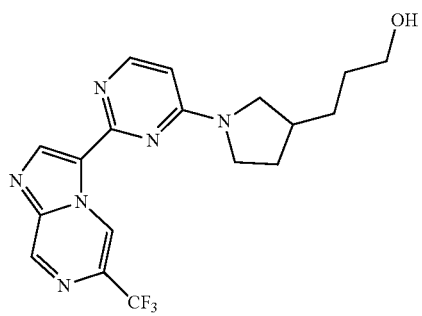 [SMILES: OCCCC1CCN(c2ccnc(-c3cnc4cnc(C(F)(F)F)cn34)n2)C1]

2-(4-(2-(6-(Trifluoromethyl)imidazo[1,2-a]pyrazin-3-yl)pyrimidin-4-yl)piperazin-1-yl)ethan-1-ol IV-617;

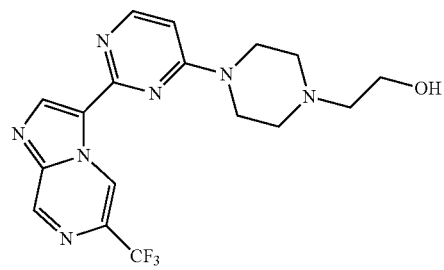

2-Hydroxy-1-(4-(2-(6-(trifluoromethyl)imidazo[1,2-a]pyrazin-3-yl)pyrimidin-4-yl)piperazin-1-yl)ethan-1-one IV-618;

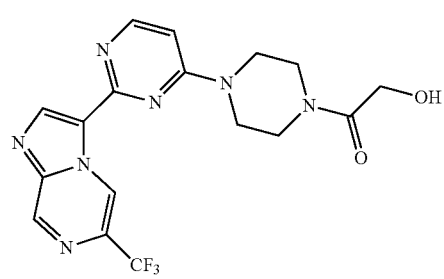 [SMILES: O=C(CO)N1CCN(c2ccnc(-c3cnc4cnc(C(F)(F)F)cn34)n2)CC1]

2-Methyl-1-(4-(2-(6-(trifluoromethyl)imidazo[1,2-a]pyrazin-3-yl)pyrimidin-4-yl)piperazin-1-yl)propan-2-ol IV-619;

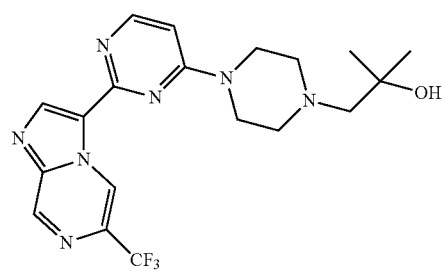 [SMILES: CC(C)(O)CN1CCN(c2ccnc(-c3cnc4cnc(C(F)(F)F)cn34)n2)CC1]

3-(4-(2-(6-(Trifluoromethyl)imidazo[1,2-a]pyrazin-3-yl)pyrimidin-4-yl)piperazin-1-yl)propanenitrile IV-620;

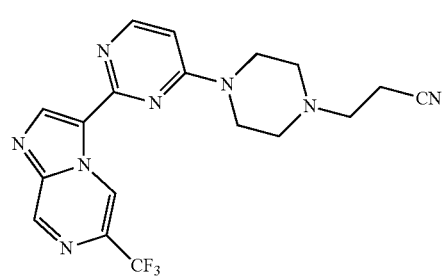

N-Methyl-1-(2-(6-(trifluoromethyl)imidazo[1,2-a]pyrazin-3-yl)pyrimidin-4-yl)pyrrolidine-3-carboxamide IV-625;

1097

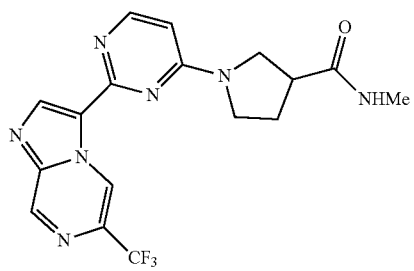 [SMILES: CNC(=O)C1CCN(c2ccnc(-c3cnc4cnc(C(F)(F)F)cn34)n2)C1]

1-(2-(6-(Trifluoromethyl)imidazo[1,2-a]pyrazin-3-yl)py-
rimidin-4-yl)piperidine-3-carboxamide IV-626;

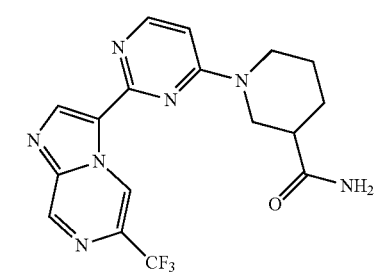 [SMILES: NC(=O)C1CCCN(c2ccnc(-c3cnc4cnc(C(F)(F)F)cn34)n2)C1]

3-(4-(2,5-Dimethyl-3-(1H-pyrazol-4-yl)piperazin-1-yl)-6-
methylpyrimidin-2-yl)-6-(trifluoromethyl)imidazo[1,2-a]
pyrazine IV-627;

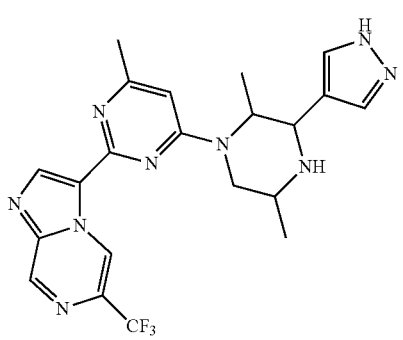

3-(4-(3-(3-(1-Methylcyclopropyl)-1H-pyrazol-4-yl)pyrroli-
din-1-yl)pyrimidin-2-yl)-6-(trifluoromethyl)imidazo[1,2-
a]pyrazine IV-630;

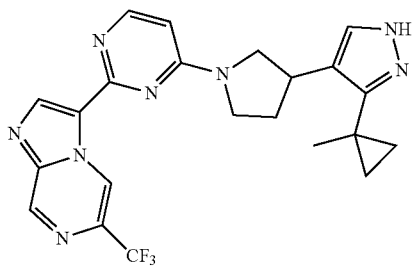 [SMILES: CC1(c2n[nH]cc2C2CCN(c3ccnc(-c4cnc5cnc(C(F)(F)F)cn45)n3)C2)CC1]

6-Methyl-1-(2-(6-(trifluoromethyl)imidazo[1,2-a]pyrazin-
3-yl)pyrimidin-4-yl)piperidine-3-carboxamide IV-631;

1098

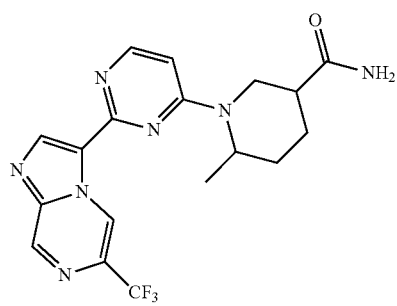

3-(4-(Azetidin-1-yl)-6-(2,5-dimethyl-3-(1H-pyrazol-4-yl)
piperazin-1-yl)pyrimidin-2-yl)-6-(trifluoromethyl)imi-
dazo[1,2-a]pyrazine (all syn diastereoisomer) IV-637;

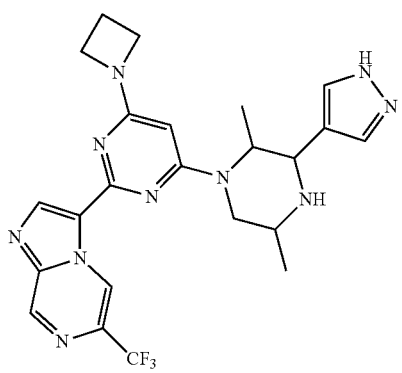 [SMILES: CC1CN(c2cc(N3CCC3)nc(-c3cnc4cnc(C(F)(F)F)cn34)n2)C(C)C(c2cn[nH]c2)N1]

3-(4-(3-(5-Methyl-1H-1,2,4-triazol-3-yl)pyrrolidin-1-yl)py-
rimidin-2-yl)-6-(trifluoromethyl)imidazo[1,2-a]pyrazine
IV-641;

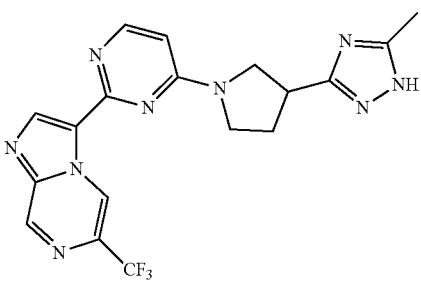 [SMILES: Cc1nc(C2CCN(c3ccnc(-c4cnc5cnc(C(F)(F)F)cn45)n3)C2)n[nH]1]

3-(4-(3-(4H-1,2,4-Triazol-3-yl)pyrrolidin-1-yl)pyrimidin-2-
yl)-6-(trifluoromethyl)imidazo[1,2-a]pyrazine IV-642;

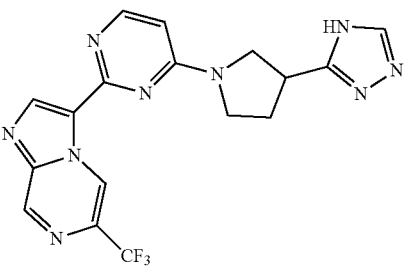 [SMILES: FC(F)(F)c1cn2c(-c3nccc(N4CCC(c5nnc[nH]5)C4)n3)cnc2cn1]

6-(Trifluoromethyl)-3-(4-(2,3,5-trimethylpiperidin-1-yl)pyrimidin-2-yl)imidazo[1,2-a]pyrazine IV-643;

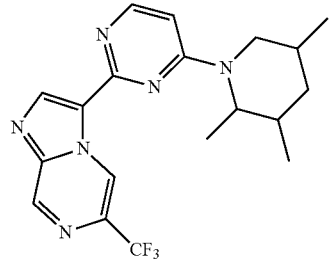 [SMILES: CC1CC(C)C(C)N(c2ccnc(-c3cnc4cnc(C(F)(F)F)cn34)n2)C1]

3-(4-(3-Cyclopentylpyrrolidin-1-yl)pyrimidin-2-yl)-6-(trifluoromethyl)imidazo[1,2-a]pyrazine IV-644;

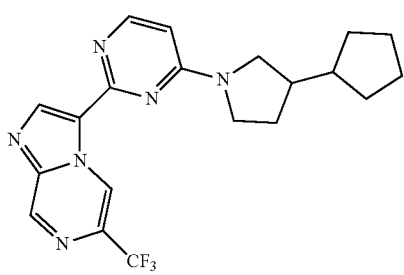 [SMILES: FC(F)(F)c1cn2c(-c3nccc(N4CCC(C5CCCC5)C4)n3)cnc2cn1]

1-(1-(2-(6-(Trifluoromethyl)imidazo[1,2-a]pyrazin-3-yl)pyrimidin-4-yl)pyrrolidin-3-yl)piperidin-4-ol IV-645;

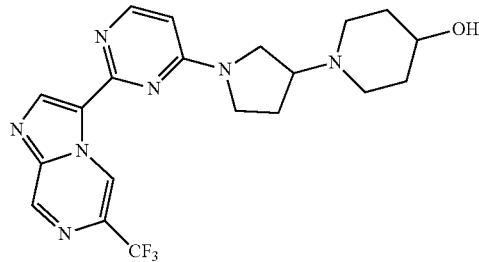 [SMILES: OC1CCN(C2CCN(c3ccnc(-c4cnc5cnc(C(F)(F)F)cn45)n3)C2)CC1]

3-(4-(3-(Pyridin-3-yl)pyrrolidin-1-yl)pyrimidin-2-yl)-6-(trifluoromethyl)imidazo[1,2-a]pyrazine IV-646;

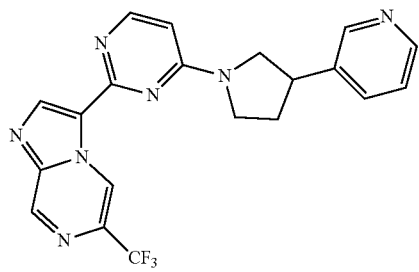 [SMILES: FC(F)(F)c1cn2c(-c3nccc(N4CCC(c5cccnc5)C4)n3)cnc2cn1]

1-Methyl-3-(1-(2-(6-(trifluoromethyl)imidazo[1,2-a]pyrazin-3-yl)pyrimidin-4-yl)pyrrolidin-3-yl)-1H-pyrazol-5-ol IV-647;

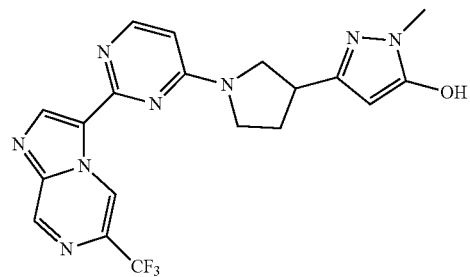 [SMILES: Cn1nc(C2CCN(c3ccnc(-c4cnc5cnc(C(F)(F)F)cn45)n3)C2)cc1O]

6-(Trifluoromethyl)-3-(4-(3-(5-(trifluoromethyl)-1H-pyrazol-3-yl)piperidin-1-yl)pyrimidin-2-yl)imidazo[1,2-a]pyrazine IV-653;

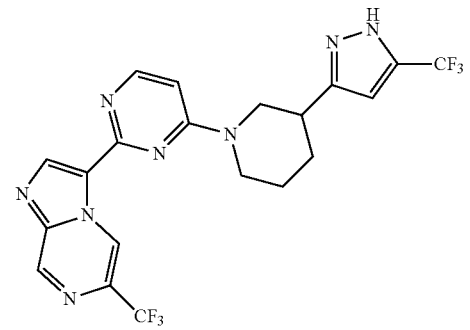 [SMILES: FC(F)(F)c1cn2c(-c3nccc(N4CCCC(c5cc(C(F)(F)F)[nH]n5)C4)n3)cnc2cn1]

3-(4-(3-(1-Methyl-4-(trifluoromethyl)-1H-imidazol-2-yl)piperidin-1-yl)pyrimidin-2-yl)-6-(trifluoromethyl)imidazo[1,2-a]pyrazine IV-654;

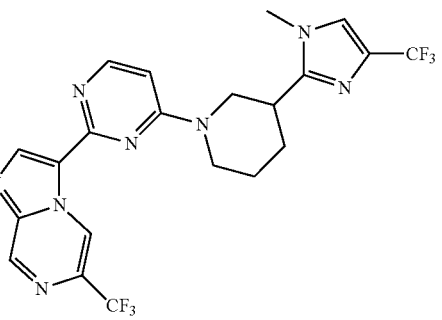

3-(4-(3-(1-Methyl-1H-pyrazol-5-yl)piperidin-1-yl)pyrimidin-2-yl)-6-(trifluoromethyl)imidazo[1,2-a]pyrazine IV-655;

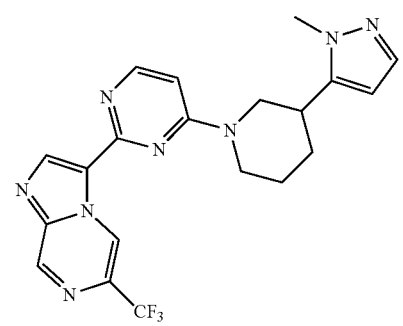 [SMILES: Cn1nccc1C1CCCN(c2ccnc(-c3cnc4cnc(C(F)(F)F)cn34)n2)C1]

2-(1-(2-(6-(Trifluoromethyl)imidazo[1,2-a]pyrazin-3-yl)pyrimidin-4-yl)piperidin-3-yl)-1,3,4-oxadiazole IV-656;

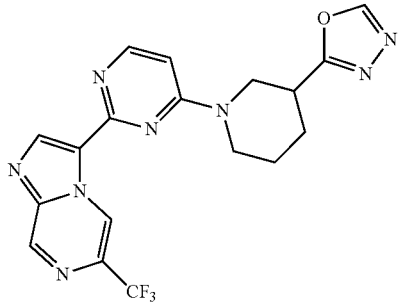

2-(4-Methyl-1H-pyrazol-3-yl)-4-(2-(6-(trifluoromethyl)imidazo[1,2-a]pyrazin-3-yl)pyrimidin-4-yl)morpholine IV-657;

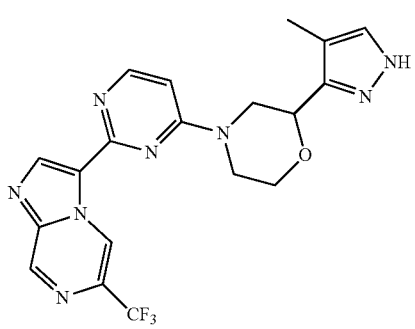 [SMILES: Cc1c[nH]nc1C1CN(c2ccnc(-c3cnc4cnc(C(F)(F)F)cn34)n2)CCO1]

2-(1-(2-(6-(Trifluoromethyl)imidazo[1,2-a]pyrimidin-4-yl)piperidin-3-yl)isothiazolidine 1,1-dioxide IV-658;

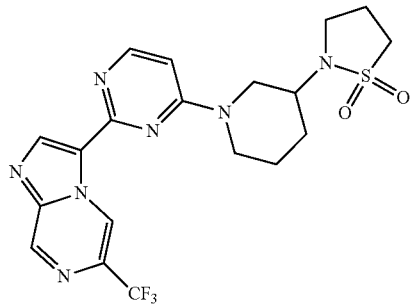 [SMILES: O=S1(=O)CCCN1C1CCCN(c2ccnc(-c3cnc4cnc(C(F)(F)F)cn34)n2)C1]

3-(4-(3-(5-Cyclohexyl-1H-1,2,4-triazol-3-yl)piperidin-1-yl)pyrimidin-2-yl)-6-(trifluoromethyl)imidazo[1,2-a]pyrazine IV-659;

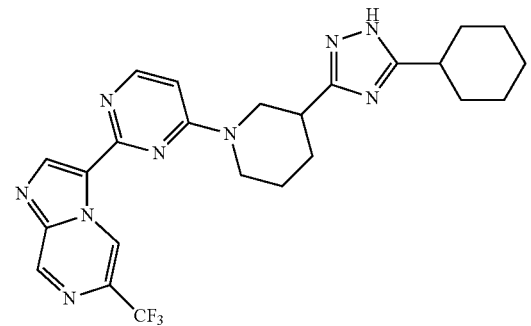 [SMILES: FC(F)(F)c1cn2c(-c3nccc(N4CCCC(c5n[nH]c(C6CCCCC6)n5)C4)n3)cnc2cn1]

5-(1-(2-(6-(Trifluoromethyl)imidazo[1,2-a]pyrazin-3-yl)pyrimidin-4-yl)piperidin-3-yl)-1,2-dihydro-3H-1,2,4-triazol-3-one IV-660;

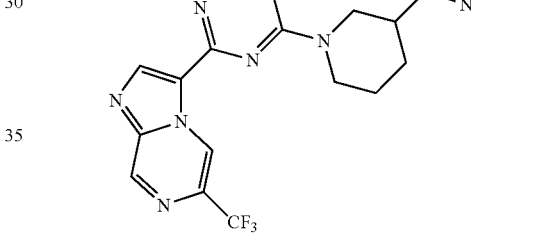

2-(5-Methyl-1H-1,2,4-triazol-3-yl)-4-(2-(6-(trifluoromethyl)imidazo[1,2-a]pyrazin-3-yl)pyrimidin-4-yl)morpholine IV-661;

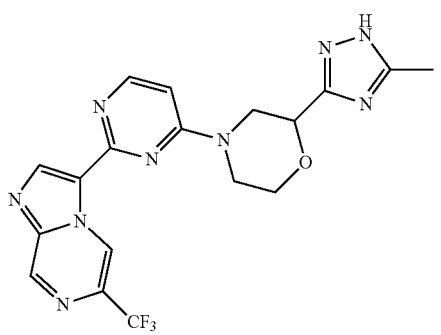 [SMILES: Cc1nc(C2CN(c3ccnc(-c4cnc5cnc(C(F)(F)F)cn45)n3)CCO2)n[nH]1]

2-(1-Methyl-3-(1-(2-(6-(trifluoromethyl)imidazo[1,2-a]pyrazin-3-yl)pyrimidin-4-yl)piperidin-3-yl)-1H-pyrazol-5-yl)ethan-1-ol IV-662;

1103

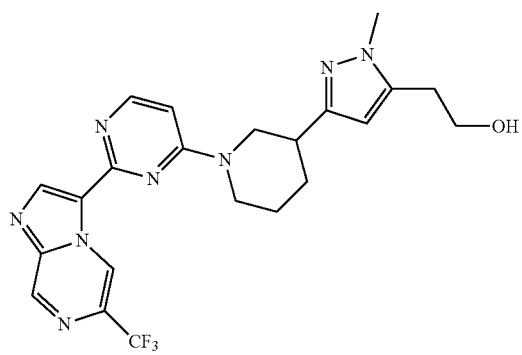 [SMILES: Cn1nc(C2CCCN(c3ccnc(-c4cnc5cnc(C(F)(F)F)cn45)n3)C2)cc1CCO]

4-(1-(2-(6-(Trifluoromethyl)imidazo[1,2-a]pyrazin-3-yl)pyrimidin-4-yl)piperidin-3-yl)pyrrolidin-2-one IV-663;

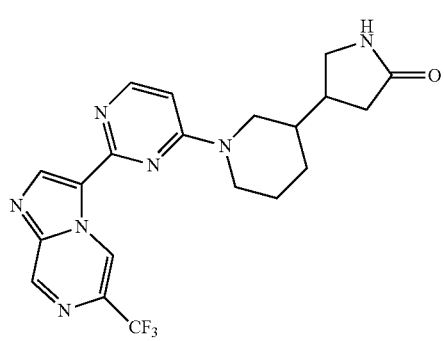 [SMILES: O=C1CC(C2CCCN(c3ccnc(-c4cnc5cnc(C(F)(F)F)cn45)n3)C2)CN1]

6-(Trifluoromethyl)-3-(4-(3-(3-(trifluoromethyl)-1H-pyrazol-1-yl)piperidin-1-yl)pyrimidin-2-yl)imidazo[1,2-a]pyrazine IV-664;

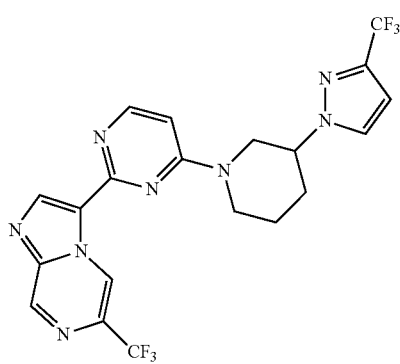 [SMILES: FC(F)(F)c1cn2c(-c3nccc(N4CCCC(n5ccc(C(F)(F)F)n5)C4)n3)cnc2cn1]

3-(4-(3-(1H-Pyrazol-1-yl)piperidin-1-yl)pyrimidin-2-yl)-6-(trifluoromethyl)imidazo[1,2-a]pyrazine IV-665;

1104

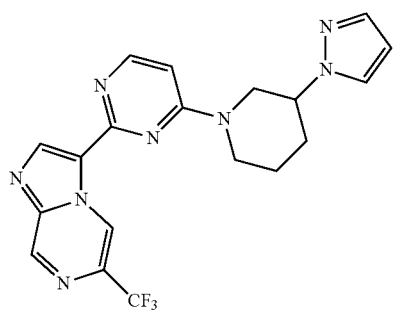 [SMILES: FC(F)(F)c1cn2c(-c3nccc(N4CCCC(n5cccn5)C4)n3)cnc2cn1]

3-(4-(2,5-Dimethyl-3-(2-(trifluoromethyl)-1H-imidazol-4-yl)piperazin-1-yl)pyrimidin-2-yl)-6-(trifluoromethyl)imidazo[1,2-a]pyrazine (all syn diastereoisomer) IV-666;

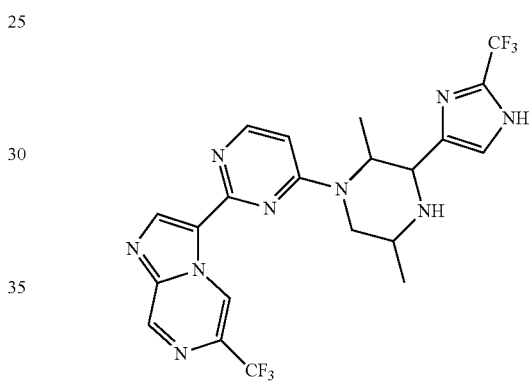

Cis-3-(4-(3-Methyl-5-(1-methyl-1H-pyrazol-5-yl)piperazin-1-yl)pyrimidin-2-yl)-6-(trifluoromethyl)imidazo[1,2-a]pyrazine IV-667;

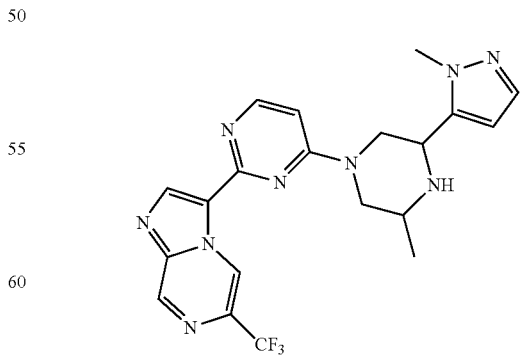

3-(4-(3-(1H-Pyrazol-4-yl)pyrrolidin-1-yl)-6-methylpyrimidin-2-yl)-6-(trifluoromethyl)imidazo[1,2-a]pyrazine IV-668;

1105

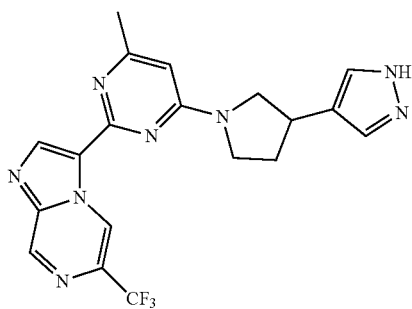 [SMILES: Cc1cc(N2CCC(c3cn[nH]c3)C2)nc(-c2cnc3cnc(C(F)(F)F)cn23)n1]

Cis-3-(4-(3-Methyl-5-(1-methyl-1H-imidazol-5-yl)piperazin-1-yl)pyrimidin-2-yl)-6-(trifluoromethyl)imidazo[1,2-a]pyrazine IV-672;

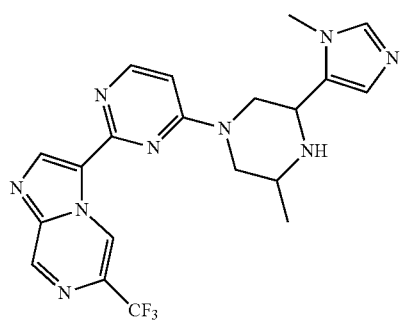 [SMILES: CC1CN(c2ccnc(-c3cnc4cnc(C(F)(F)F)cn34)n2)CC(c2cncn2C)N1]

2-(1-(2-(6-(Trifluoromethyl)imidazo[1,2-a]pyrazin-3-yl)pyrimidin-4-yl)piperidin-3-yl)thiazole IV-675;

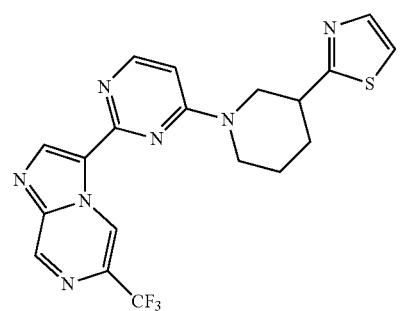

5-(3,6-Dimethyl-1-(2-(6-(trifluoromethyl)imidazo[1,2-a]pyrazin-3-yl)pyrimidin-4-yl)piperazin-2-yl)pyridin-2(1H)-one (all syn diastereoisomer) IV-676;

1106

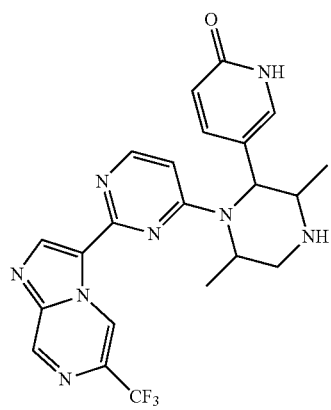 [SMILES: CC1NCC(C)N(c2ccnc(-c3cnc4cnc(C(F)(F)F)cn34)n2)C1c1ccc(=O)[nH]c1]

5-(3,6-Dimethyl-4-(2-(6-(trifluoromethyl)imidazo[1,2-a]pyrazin-3-yl)pyrimidin-4-yl)piperazin-2-yl)pyridin-2(1H)-one (all syn diastereoisomer) IV-677;

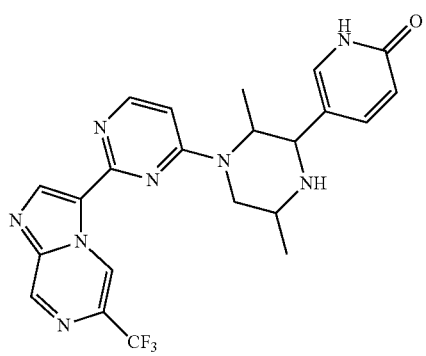 [SMILES: CC1CN(c2ccnc(-c3cnc4cnc(C(F)(F)F)cn34)n2)C(C)C(c2ccc(=O)[nH]c2)N1]

5-(1-(2-(6-(Trifluoromethyl)imidazo[1,2-a]pyrazin-3-yl)pyrimidin-4-yl)piperidin-3-yl)oxazole IV-678;

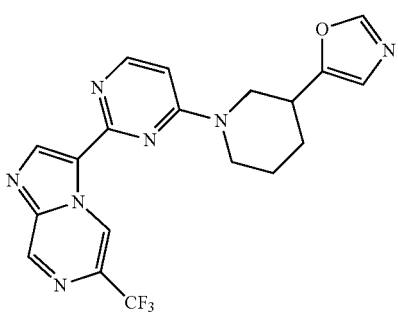 [SMILES: FC(F)(F)c1cn2c(-c3nccc(N4CCCC(c5cnco5)C4)n3)cnc2cn1]

3-(4-((8aS)-4-(1H-Pyrazol-4-yl)hexahydropyrrolo[1,2-a]pyrazin-2(1H)-yl)pyrimidin-2-yl)-6-(trifluoromethyl)imidazo[1,2-a]pyrazine IV-679;

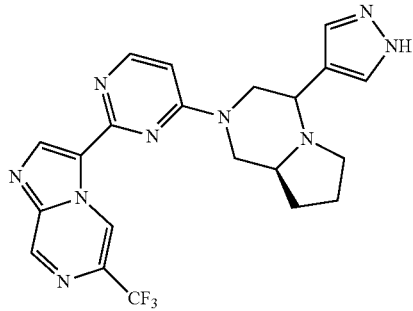 [SMILES: FC(F)(F)c1cn2c(-c3nccc(N4CC(c5cn[nH]c5)N5CCC[C@H]5C4)n3)cnc2cn1]

3-(4-(4-(1H-Pyrazol-4-yl)piperidin-1-yl)pyrimidin-2-yl)-6-(trifluoromethyl)imidazo[1,2-a]pyrazine IV-680;

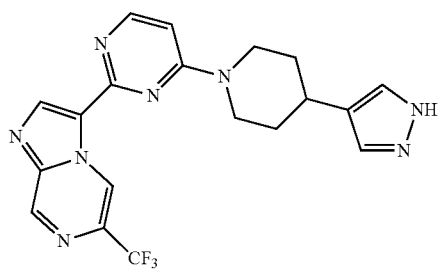 [SMILES: FC(F)(F)c1cn2c(-c3nccc(N4CCC(c5cn[nH]c5)CC4)n3)cnc2cn1]

3-(4-(3-(Azetidin-1-ylmethyl)-5-(1H-pyrazol-4-yl)piperidin-1-yl)pyrimidin-2-yl)-6-(trifluoromethyl)imidazo[1,2-a]pyrazine IV-681;

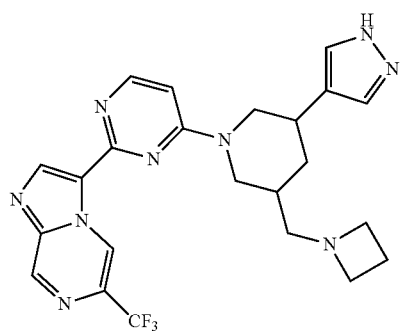

2-(1-(2-(6-(Trifluoromethyl)imidazo[1,2-a]pyrazin-3-yl)pyrimidin-4-yl)piperidin-3-yl)oxazole IV-686;

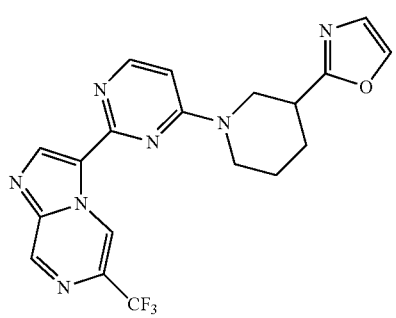

3-(4-(2,5-Dimethyl-3-(1-methyl-1H-pyrazol-4-yl)piperazin-1-yl)pyrimidin-2-yl)-6-(trifluoromethyl)imidazo[1,2-a]pyrazine (all syn diastereoisomer) IV-687;

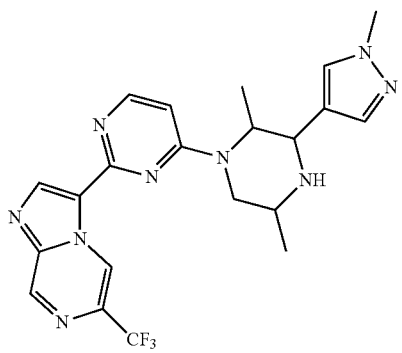 [SMILES: CC1CN(c2ccnc(-c3cnc4cnc(C(F)(F)F)cn34)n2)C(C)C(c2cnn(C)c2)N1]

3-(6-(2,5-Dimethyl-3-(1H-pyrazol-4-yl)piperazin-1-yl)-4-fluoropyridin-2-yl)-6-(trifluoromethyl)imidazo[1,2-a]pyrazine (all syn diastereoisomer) IV-690;

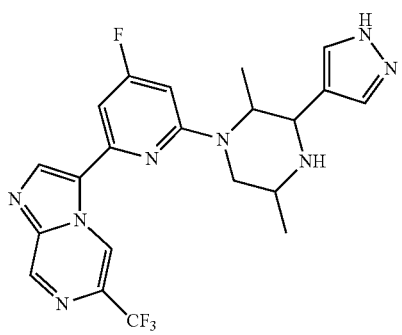

5-(1-(2-(6-(Trifluoromethyl)imidazo[1,2-a]pyrazin-3-yl)pyrimidin-4-yl)piperidin-3-yl)thiazole IV-691;

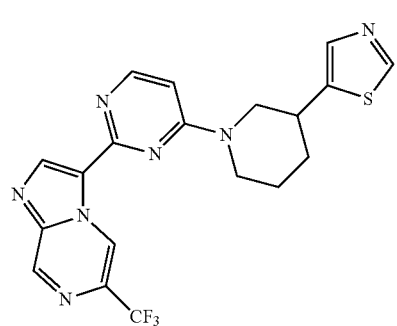

Dimethyl(6-methyl-5-(1H-pyrazol-4-yl)-1-(2-(6-(trifluoromethyl)imidazo[1,2-a]pyrazin-3-yl)pyrimidin-4-yl)piperidin-3-yl)phosphine oxide IV-693:

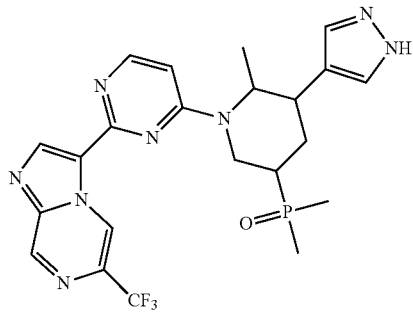 [SMILES: CC1C(c2cn[nH]c2)CC(P(C)(C)=O)CN1c1ccnc(-c2cnc3cnc(C(F)(F)F)cn23)n1]

4-(1-(2-(6-(Trifluoromethyl)imidazo[1,2-a]pyrazin-3-yl)pyrimidin-4-yl)piperidin-3-yl)oxazole IV-694;

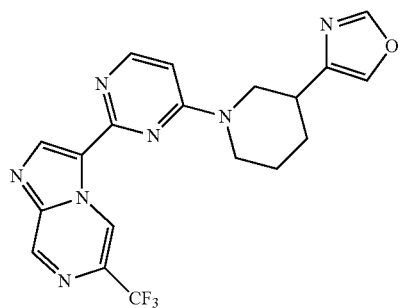 [SMILES: FC(F)(F)c1cn2c(-c3nccc(N4CCCC(c5cocn5)C4)n3)cnc2cn1]

Dimethyl(6-methyl-5-(1H-pyrazol-4-yl)-1-(2-(6-(trifluoromethyl)imidazo[1,2-a]pyrazin-3-yl)pyrimidin-4-yl)piperidin-3-yl)phosphine oxide IV-697;

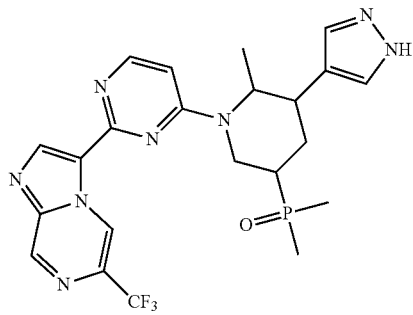 [SMILES: CC1C(c2cn[nH]c2)CC(P(C)(C)=O)CN1c1ccnc(-c2cnc3cnc(C(F)(F)F)cn23)n1]

3-(4-(4-Acetyl-3,3-dimethylpiperazin-1-yl)pyrimidin-2-yl)imidazo[1,2-a]pyrazine-6-carboxamide IV-699

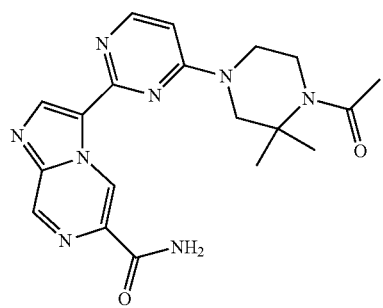 [SMILES: CC(=O)N1CCN(c2ccnc(-c3cnc4cnc(C(N)=O)cn34)n2)CC1(C)C]

The following compounds were made using methodology similar to that described in Example 1 and further purified by chiral SFC:

2-(1H-Pyrazol-4-yl)-4-(2-(6-(trifluoromethyl)imidazo[1,2-a]pyrazin-3-yl)pyrimidin-4-yl)morpholine IV-7;

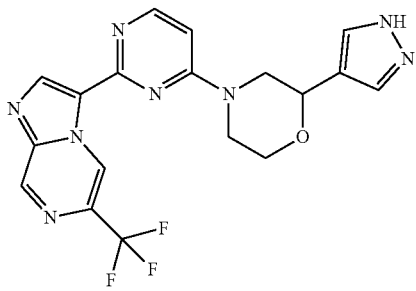 [SMILES: FC(F)(F)c1cn2c(-c3nccc(N4CCOC(c5cn[nH]c5)C4)n3)cnc2cn1]

2-(1H-Pyrazol-4-yl)-4-(2-(6-(trifluoromethyl)imidazo[1,2-a]pyrazin-3-yl)pyrimidin-4-yl)morpholine IV-8;

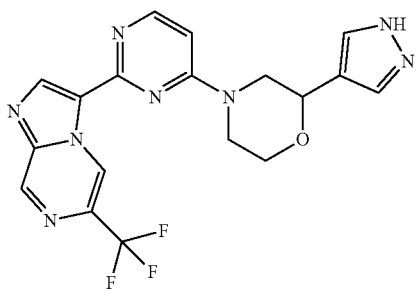

4-(2-(6-Chloroimidazo[1,2-a]pyrazin-3-yl)pyrimidin-4-yl)-3-methyl-2-(1H-pyrazol-4-yl)morpholine IV-9;

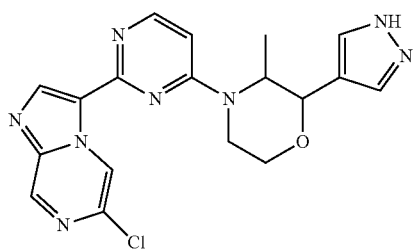 [SMILES: CC1C(c2cn[nH]c2)OCCN1c1ccnc(-c2cnc3cnc(Cl)cn23)n1]

2-Methyl-6-(1H-pyrazol-4-yl)-4-(2-(6-(trifluoromethyl)imidazo[1,2-a]pyrazin-3-yl)pyrimidin-4-yl)morpholine IV-13;

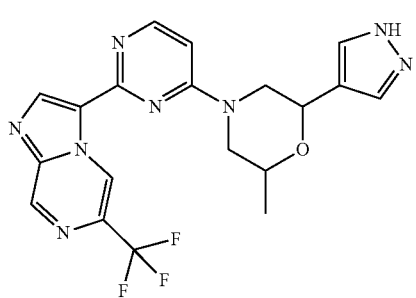 [SMILES: CC1CN(c2ccnc(-c3cnc4cnc(C(F)(F)F)cn34)n2)CC(c2cn[nH]c2)O1]

2-Methyl-6-(1H-pyrazol-4-yl)-4-(2-(6-(trifluoromethyl)imi-
dazo[1,2-a]pyrazin-3-yl)pyrimidin-4-yl)morpholine
IV-14;

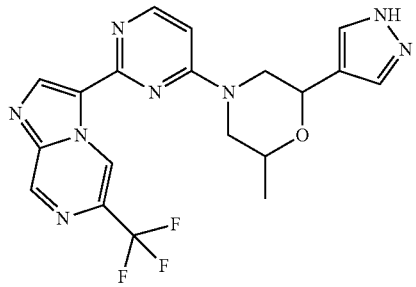 [SMILES: CC1CN(c2ccnc(-c3cnc4cnc(C(F)(F)F)cn34)n2)CC(c2cn[nH]c2)O1]

2-Methyl-6-(1H-pyrazol-4-yl)-4-(2-(6-(trifluoromethyl)imi-
dazo[1,2-a]pyrazin-3-yl)pyrimidin-4-yl)morpholine
IV-15;

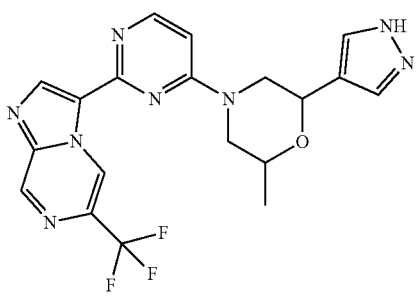

2-Methyl-6-(1H-pyrazol-4-yl)-4-(2-(6-(trifluoromethyl)imi-
dazo[1,2-a]pyrazin-3-yl)pyrimidin-4-yl)morpholine
IV-16;

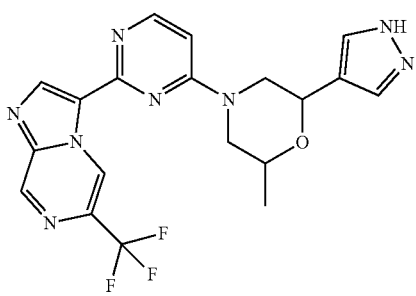

4-(2-(6-(Difluoromethyl)imidazo[1,2-a]pyrazin-3-yl)py-
rimidin-4-yl)-1,4-oxazepane-6-carboxamide IV-128;

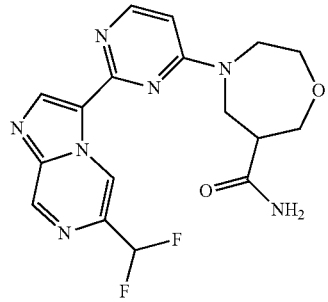

1-(2-(6-(Difluoromethyl)imidazo[1,2-a]pyrazin-3-yl)py-
rimidin-4-yl)piperidine-3-sulfonamide IV-177;

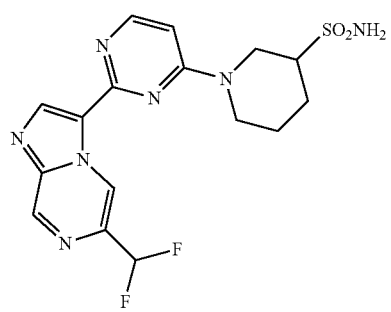 [SMILES: NS(=O)(=O)C1CCCN(c2ccnc(-c3cnc4cnc(C(F)F)cn34)n2)C1]

2-(1H-Pyrazol-4-yl)-4-(4-(6-(trifluoromethyl)imidazo[1,2-
a]pyrazin-3-yl)pyrimidin-2-yl)morpholine IV-185;

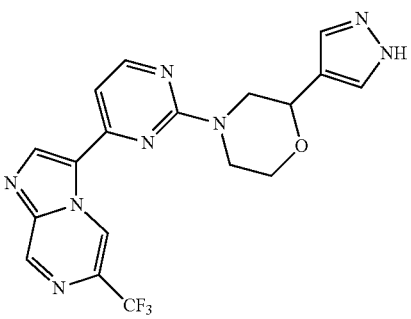 [SMILES: FC(F)(F)c1cn2c(-c3ccnc(N4CCOC(c5cn[nH]c5)C4)n3)cnc2cn1]

2-(1H-Pyrazol-4-yl)-4-(4-(6-(trifluoromethyl)imidazo[1,2-
a]pyrazin-3-yl)pyrimidin-2-yl)morpholine IV-186;

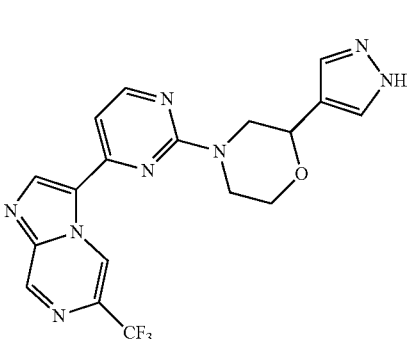

2-Methyl-6-(1H-pyrazol-4-yl)-4-(4-(6-(trifluoromethyl)imi-
dazo[1,2-a]pyrazin-3-yl)pyrimidin-2-yl)morpholine
IV-199;

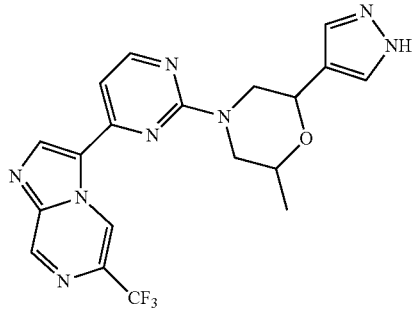

2-Methyl-6-(1H-pyrazol-4-yl)-4-(4-(6-(trifluoromethyl)imi-
dazo[1,2-a]pyrazin-3-yl)pyrimidin-2-yl)morpholine
IV-200;

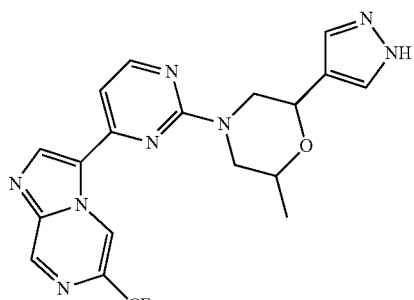

2-Methyl-6-(1H-pyrazol-4-yl)-4-(4-(6-(trifluoromethyl)imi-
dazo[1,2-a]pyrazin-3-yl)pyrimidin-2-yl)morpholine
IV-201;

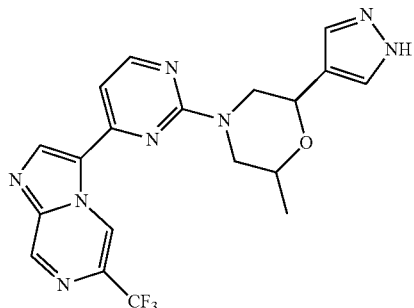

2-Methyl-6-(1H-pyrazol-4-yl)-4-(4-(6-(trifluoromethyl)imi-
dazo[1,2-a]pyrazin-3-yl)pyrimidin-2-yl)morpholine
IV-202;

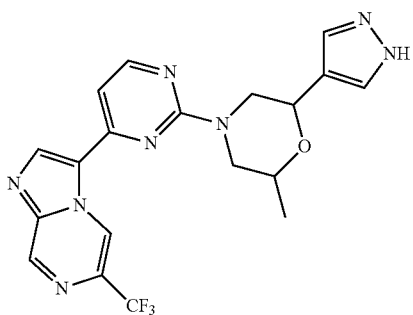 [SMILES: CC1CN(c2nccc(-c3cnc4cnc(C(F)(F)F)cn34)n2)CC(c2cn[nH]c2)O1]

6-Chloro-3-(4-(3-methyl-5-(1H-pyrazol-4-yl)piperazin-1-
yl)pyrimidin-2-yl)imidazo[1,2-a]pyrazine IV-213;

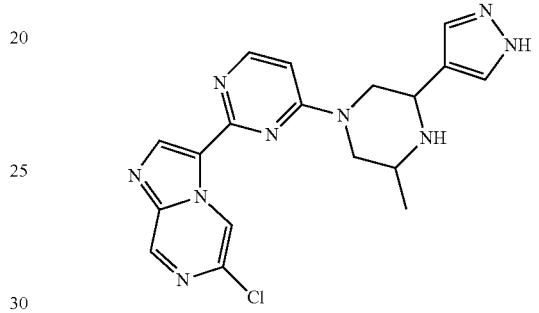

6-Chloro-3-(4-(3-methyl-5-(1H-pyrazol-4-yl)piperazin-1-
yl)pyrimidin-2-yl)imidazo[1,2-a]pyrazine IV-214;

4-(2-(6-Chloroimidazo[1,2-a]pyrazin-3-yl)pyrimidin-4-yl)-
2-methyl-6-(1H-pyrazol-4-yl)morpholine IV-216;

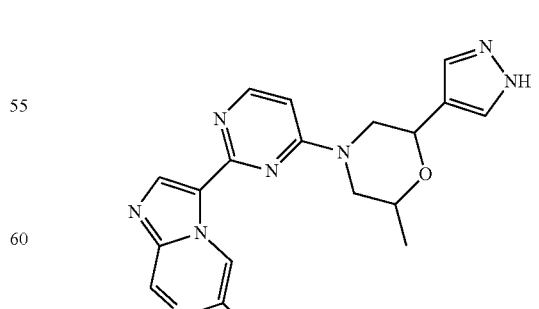

4-(2-(6-Chloroimidazo[1,2-a]pyrazin-3-yl)pyrimidin-4-yl)-
2-methyl-6-(1H-pyrazol-4-yl)morpholine IV-217;

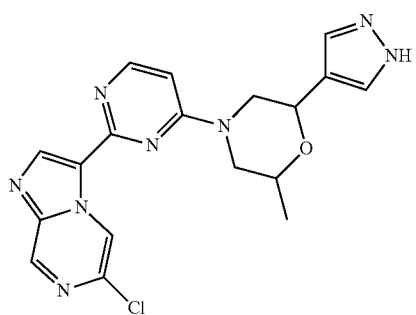 [SMILES: CC1CN(c2ccnc(-c3cnc4cnc(Cl)cn34)n2)CC(c2cn[nH]c2)O1]

3-(4-(2,5-Dimethyl-3-(1H-pyrazol-4-yl)piperazin-1-yl)pyrimidin-2-yl)-6-(trifluoromethyl)imidazo[1,2-a]pyrazine IV-223;

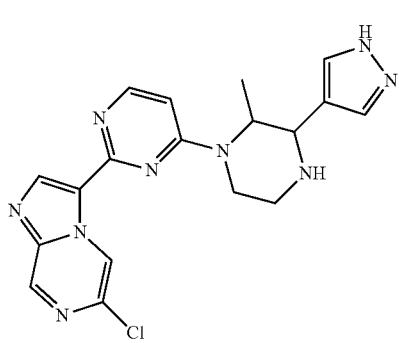

3-(4-(3-(1H-Pyrazol-4-yl)piperazin-1-yl)pyrimidin-2-yl)-6-(trifluoromethyl)imidazo[1,2-a]pyrazine IV-231;

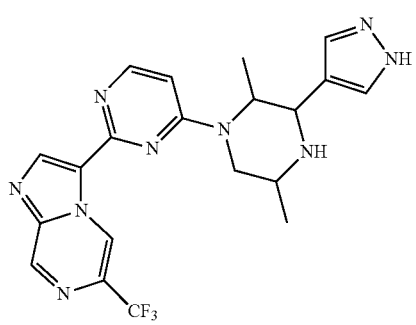

3-(4-((2S,3R,5S)-2,5-dimethyl-3-(1H-pyrazol-4-yl)piperazin-1-yl)pyrimidin-2-yl)-6-(trifluoromethyl)imidazo[1,2-a]pyrazine IV-224;

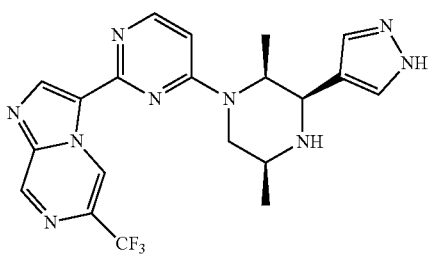 [SMILES: C[C@H]1CN(c2ccnc(-c3cnc4cnc(C(F)(F)F)cn34)n2)[C@@H](C)[C@@H](c2cn[nH]c2)N1]

6-Chloro-3-(4-(2-methyl-3-(1H-pyrazol-4-yl)piperazin-1-yl)pyrimidin-2-yl)imidazo[1,2-a]pyrazine IV-229;

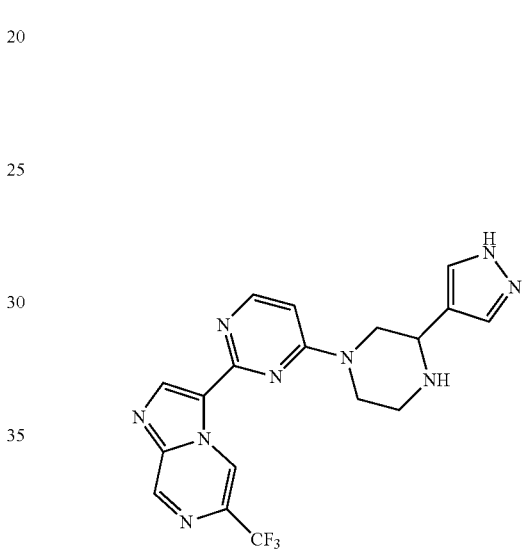

3-(4-(3-(1H-Pyrazol-4-yl)piperazin-1-yl)pyrimidin-2-yl)-6-(trifluoromethyl)imidazo[1,2-a]pyrazine IV-232;

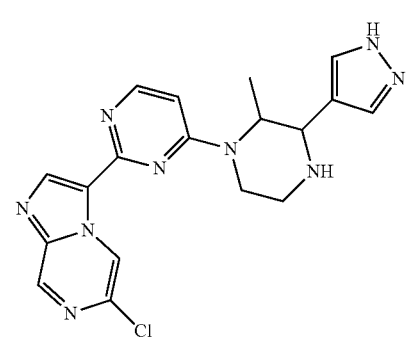 [SMILES: CC1C(c2cn[nH]c2)NCCN1c1ccnc(-c2cnc3cnc(Cl)cn23)n1]

6-Chloro-3-(4-(2-methyl-3-(1H-pyrazol-4-yl)piperazin-1-yl)pyrimidin-2-yl)imidazo[1,2-a]pyrazine IV-230;

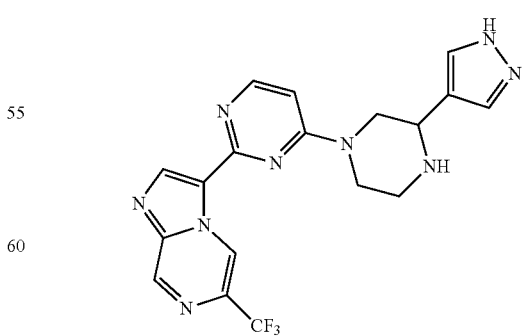

3-(4-(3-(1H-Pyrazol-4-yl)piperazin-1-yl)pyrimidin-2-yl)-6-chloroimidazo[1,2-a]pyrazine IV-237;

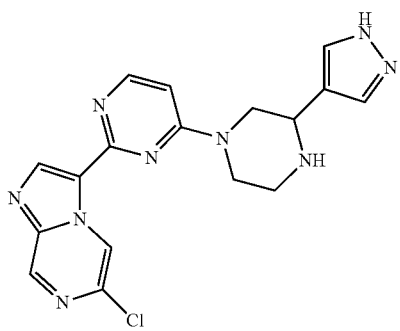 [SMILES: Clc1cn2c(-c3nccc(N4CCNC(c5cn[nH]c5)C4)n3)cnc2cn1]

3-(4-(3-(1H-Pyrazol-4-yl)piperazin-1-yl)pyrimidin-2-yl)-6-chloroimidazo[1,2-a]pyrazine IV-238;

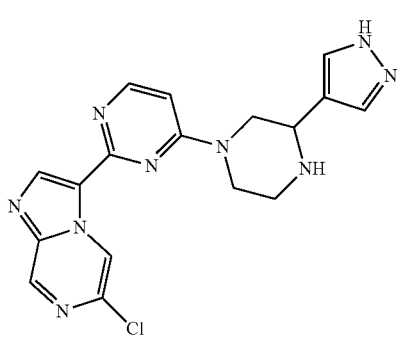 [SMILES: Clc1cn2c(-c3nccc(N4CCNC(c5cn[nH]c5)C4)n3)cnc2cn1]

4-(2-(6-Chloroimidazo[1,2-a]pyrazin-3-yl)pyrimidin-4-yl)-3-methyl-2-(1H-pyrazol-4-yl)morpholine IV-244;

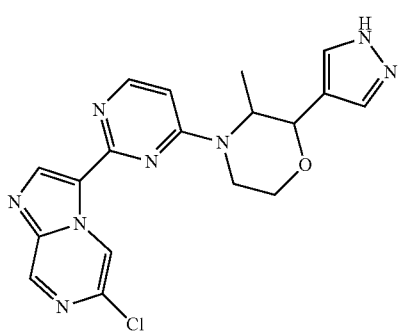 [SMILES: CC1C(c2cn[nH]c2)OCCN1c1ccnc(-c2cnc3cnc(Cl)cn23)n1]

4-(2-(6-Chloroimidazo[1,2-a]pyrazin-3-yl)pyrimidin-4-yl)-3-methyl-2-(1H-pyrazol-4-yl)morpholine IV-245;

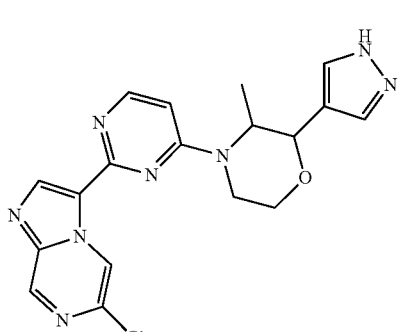

6-Chloro-3-(4-(2,5-dimethyl-3-(1H-pyrazol-4-yl)piperazin-1-yl)pyrimidin-2-yl)imidazo[1,2-a]pyrazine IV-246;

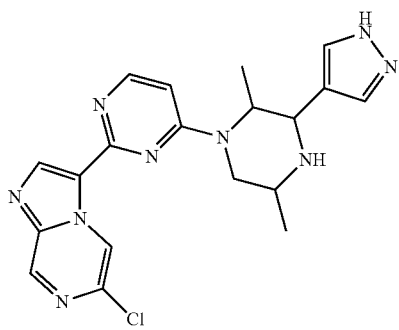 [SMILES: CC1CN(c2ccnc(-c3cnc4cnc(Cl)cn34)n2)C(C)C(c2cn[nH]c2)N1]

6-Chloro-3-(4-(2,5-dimethyl-3-(1H-pyrazol-4-yl)piperazin-1-yl)pyrimidin-2-yl)imidazo[1,2-a]pyrazine IV-247;

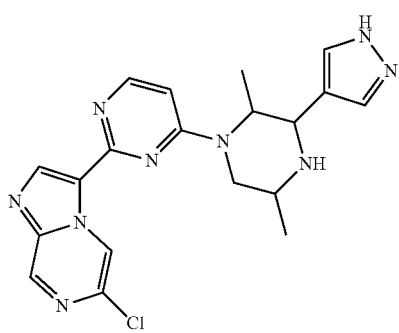 [SMILES: CC1CN(c2ccnc(-c3cnc4cnc(Cl)cn34)n2)C(C)C(c2cn[nH]c2)N1]

3-(4-(6-Oxooctahydro-2H-pyrido[1,2-a]pyrazin-2-yl)pyrimidin-2-yl)imidazo[1,2-a]pyrazine-6-carboxamide IV-273;

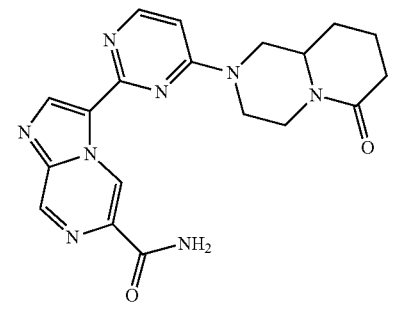

3-(4-(6-Oxooctahydro-2H-pyrido[1,2-a]pyrazin-2-yl)pyrimidin-2-yl)imidazo[1,2-a]pyrazine-6-carboxamide IV-274;

1119

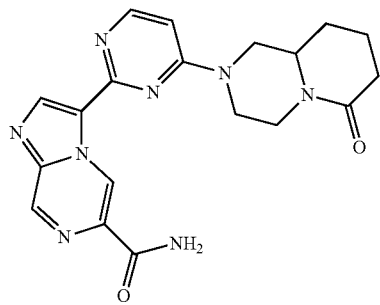 [SMILES: NC(=O)c1cn2c(-c3nccc(N4CCN5C(=O)CCCC5C4)n3)cnc2cn1]

6-Chloro-3-(4-(2,5-dimethyl-3-(5-methyl-1H-pyrazol-4-yl) piperazin-1-yl)pyrimidin-2-yl)imidazo[1,2-a]pyrazine IV-282;

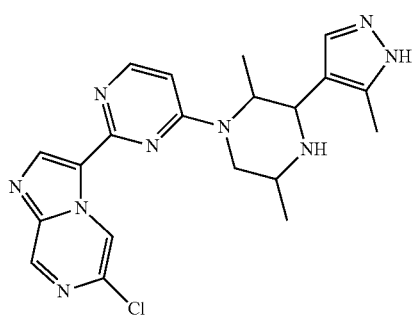 [SMILES: Cc1[nH]ncc1C1NC(C)CN(c2ccnc(-c3cnc4cnc(Cl)cn34)n2)C1C]

6-Chloro-3-(4-(2,5-dimethyl-3-(5-methyl-1H-pyrazol-4-yl) piperazin-1-yl)pyrimidin-2-yl)imidazo[1,2-a]pyrazine IV-283;

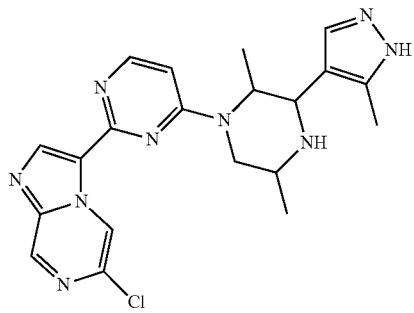 [SMILES: Cc1[nH]ncc1C1NC(C)CN(c2ccnc(-c3cnc4cnc(Cl)cn34)n2)C1C]

6-Bromo-3-(4-(2,5-dimethyl-3-(1H-pyrazol-4-yl)piperazin-1-yl)pyrimidin-2-yl)imidazo[1,2-a]pyrazine IV-287;

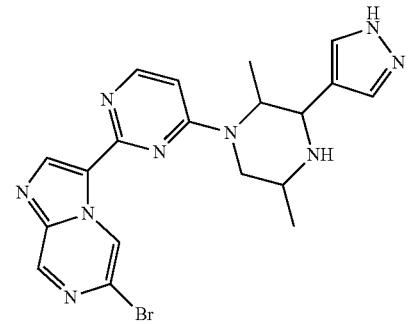

1120

6-Bromo-3-(4-(2,5-dimethyl-3-(1H-pyrazol-4-yl)piperazin-1-yl)pyrimidin-2-yl)imidazo[1,2-a]pyrazine IV-288;

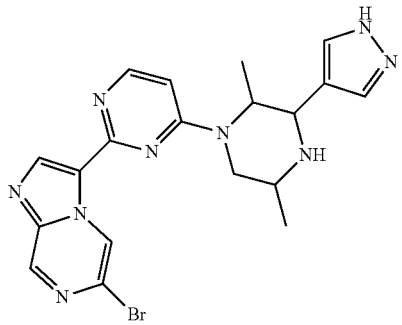 [SMILES: CC1CN(c2ccnc(-c3cnc4cnc(Br)cn34)n2)C(C)C(c2cn[nH]c2)N1]

3-(4-(3-Methyl-2-(1H-pyrazol-4-yl)morpholino)pyrimidin-2-yl)imidazo[1,2-a]pyrazine-6-carbonitrile IV-290;

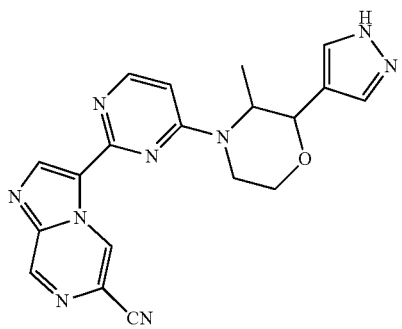 [SMILES: CC1C(c2cn[nH]c2)OCCN1c1ccnc(-c2cnc3cnc(C#N)cn23)n1]

3-(4-(3-Methyl-2-(1H-pyrazol-4-yl)morpholino)pyrimidin-2-yl)imidazo[1,2-a]pyrazine-6-carbonitrile IV-291;

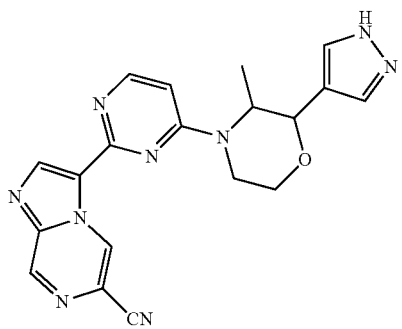 [SMILES: CC1C(c2cn[nH]c2)OCCN1c1ccnc(-c2cnc3cnc(C#N)cn23)n1]

2-(2-(6-Chloroimidazo[1,2-a]pyrazin-3-yl)pyrimidin-4-yl) octahydro-6H-pyrido[1,2-a]pyrazin-6-one IV-293;

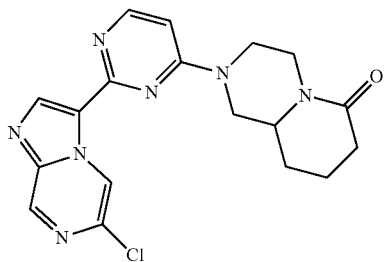 [SMILES: O=C1CCCC2CN(c3ccnc(-c4cnc5cnc(Cl)cn45)n3)CCN12]

2-(2-(6-Chloroimidazo[1,2-a]pyrazin-3-yl)pyrimidin-4-yl) octahydro-6H-pyrido[1,2-a]pyrazin-6-one IV-294;

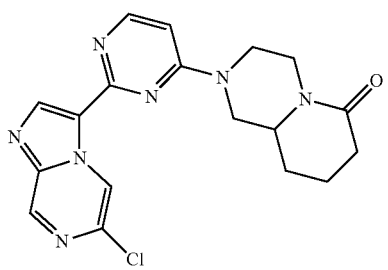 [SMILES: O=C1CCCC2CN(c3ccnc(-c4cnc5cnc(Cl)cn45)n3)CCN12]

3-(4-(4-Ethyl-2,5-dimethyl-3-(1H-pyrazol-4-yl)piperazin-1-yl)pyrimidin-2-yl)-6-(trifluoromethyl)imidazo[1,2-a]pyrazine IV-295;

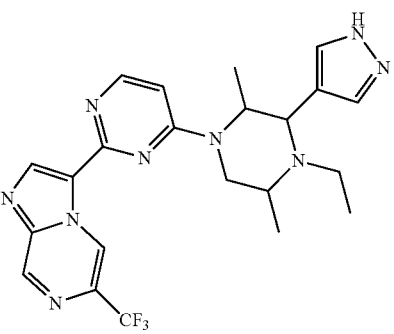

3-(4-(4-Ethyl-2,5-dimethyl-3-(1H-pyrazol-4-yl)piperazin-1-yl)pyrimidin-2-yl)-6-(trifluoromethyl)imidazo[1,2-a]pyrazine IV-296;

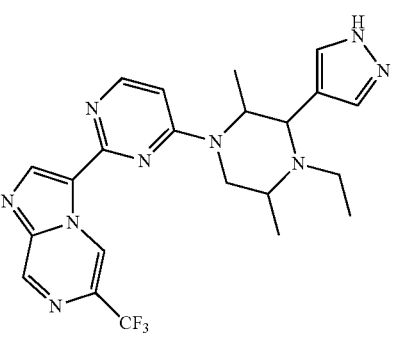

3-(4-(2,5-Dimethyl-3-(1H-pyrazol-4-yl)piperazin-1-yl)pyrimidin-2-yl)imidazo[1,2-a]pyrazine-6-carbonitrile IV-313;

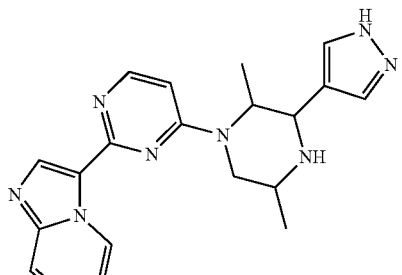

3-(4-(2,5-Dimethyl-3-(1H-pyrazol-4-yl)piperazin-1-yl)pyrimidin-2-yl)imidazo[1,2-a]pyrazine-6-carbonitrile IV-314;

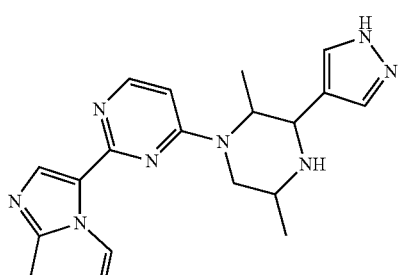

3-Methyl-2-(1H-pyrazol-4-yl)-4-(2-(6-(trifluoromethyl)imidazo[1,2-a]pyrazin-3-yl)pyrimidin-4-yl)morpholine IV-315;

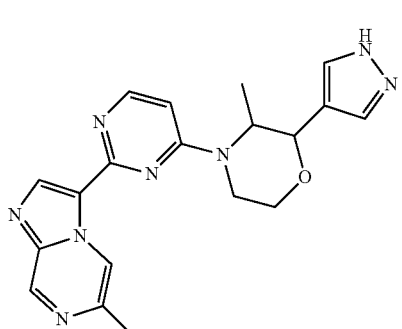

4-(2-(6-Chloroimidazo[1,2-a]pyrazin-3-yl)pyrimidin-4-yl)-3-methyl-2-(1H-pyrazol-4-yl)morpholine IV-316;

1123

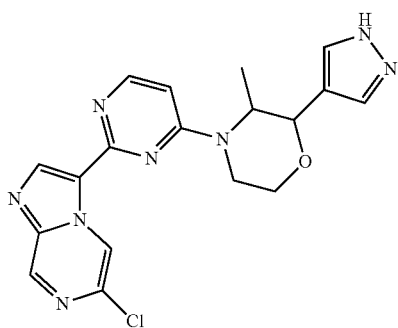 [SMILES: CC1C(c2cn[nH]c2)OCCN1c1ccnc(-c2cnc3cnc(Cl)cn23)n1]

3-Methyl-2-(1H-pyrazol-4-yl)-4-(2-(6-(trifluoromethyl)imidazo[1,2-a]pyrazin-3-yl)pyrimidin-4-yl)morpholine IV-318;

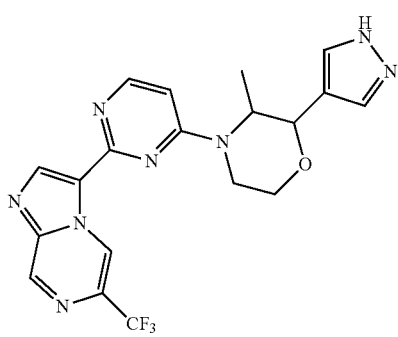

4-(2-(6-Bromoimidazo[1,2-a]pyrazin-3-yl)pyrimidin-4-yl)-3-methyl-2-(1H-pyrazol-4-yl)morpholine IV-328;

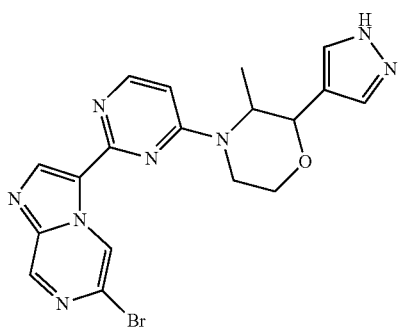 [SMILES: CC1C(c2cn[nH]c2)OCCN1c1ccnc(-c2cnc3cnc(Br)cn23)n1]

4-(2-(6-Bromoimidazo[1,2-a]pyrazin-3-yl)pyrimidin-4-yl)-3-methyl-2-(1H-pyrazol-4-yl)morpholine IV-329;

1124

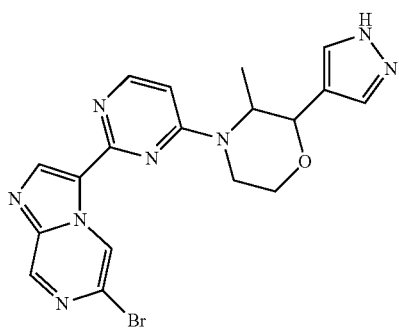 [SMILES: CC1C(c2cn[nH]c2)OCCN1c1ccnc(-c2cnc3cnc(Br)cn23)n1]

6-(Trifluoromethyl)-3-(4-(2,3,6-trimethyl-5-(1H-pyrazol-4-yl)piperazin-1-yl)pyrimidin-2-yl)imidazo[1,2-a]pyrazine IV-336;

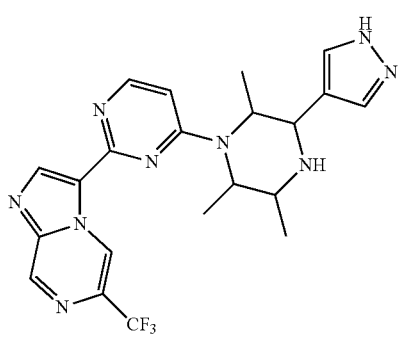 [SMILES: CC1NC(c2cn[nH]c2)C(C)N(c2ccnc(-c3cnc4cnc(C(F)(F)F)cn34)n2)C1C]

6-(Trifluoromethyl)-3-(4-(2,3,6-trimethyl-5-(1H-pyrazol-4-yl)piperazin-1-yl)pyrimidin-2-yl)imidazo[1,2-a]pyrazine IV-337;

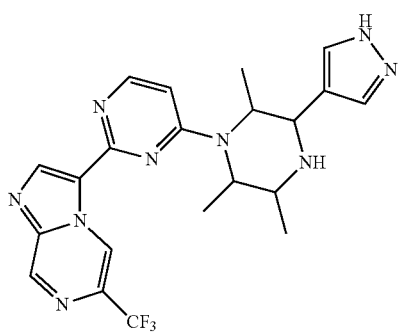 [SMILES: CC1NC(c2cn[nH]c2)C(C)N(c2ccnc(-c3cnc4cnc(C(F)(F)F)cn34)n2)C1C]

((1-(2-(6-(Difluoromethyl)imidazo[1,2-a]pyrazin-3-yl)pyrimidin-4-yl)piperidin-3-yl)methyl)(imino)(methyl)-$\lambda^6$-sulfanone IV-338;

1125

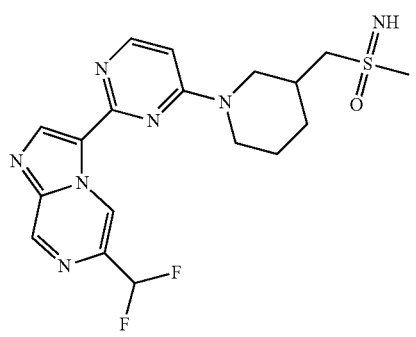 [SMILES: CS(=N)(=O)CC1CCCN(c2ccnc(-c3cnc4cnc(C(F)F)cn34)n2)C1]

((1-(2-(6-(Difluoromethyl)imidazo[1,2-a]pyrazin-3-yl)py-rimidin-4-yl)piperidin-3-yl)methyl)(imino)(methyl)-$\lambda^6$-sulfanone IV-339;

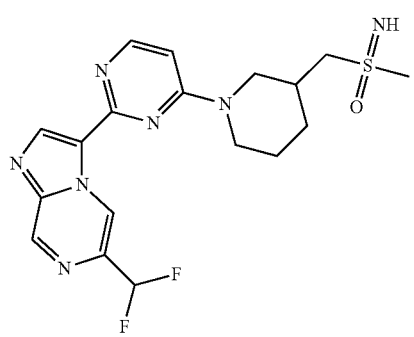 [SMILES: CS(=N)(=O)CC1CCCN(c2ccnc(-c3cnc4cnc(C(F)F)cn34)n2)C1]

6-Bromo-3-(4-(2-methyl-3-(1H-pyrazol-4-yl)piperazin-1-yl)pyrimidin-2-yl)imidazo[1,2-a]pyrazine IV-350;

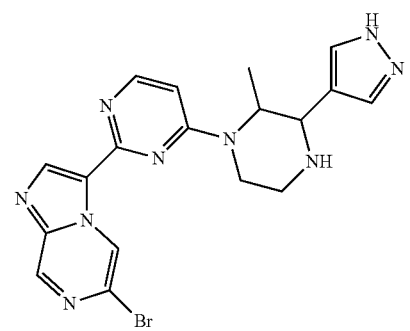 [SMILES: CC1C(c2cn[nH]c2)NCCN1c1ccnc(-c2cnc3cnc(Br)cn23)n1]

6-Bromo-3-(4-(2-methyl-3-(1H-pyrazol-4-yl)piperazin-1-yl)pyrimidin-2-yl)imidazo[1,2-a]pyrazine IV-351;

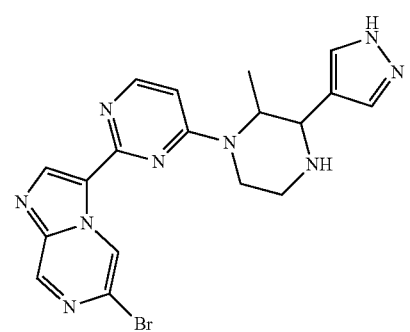 [SMILES: CC1C(c2cn[nH]c2)NCCN1c1ccnc(-c2cnc3cnc(Br)cn23)n1]

1126

3-(4-(2-Methyl-3-(1H-pyrazol-4-yl)piperazin-1-yl)pyrimidin-2-yl)-6-(trifluoromethyl)imidazo[1,2-a]pyrazine IV-357;

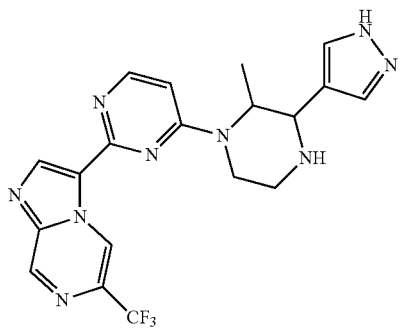 [SMILES: CC1C(c2cn[nH]c2)NCCN1c1ccnc(-c2cnc3cnc(C(F)(F)F)cn23)n1]

3-(4-(2-Methyl-3-(1H-pyrazol-4-yl)piperazin-1-yl)pyrimidin-2-yl)-6-(trifluoromethyl)imidazo[1,2-a]pyrazine IV-358;

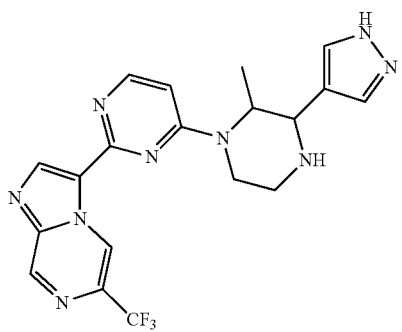

3-(4-(3-(1H-Pyrazol-4-yl)piperidin-1-yl)pyrimidin-2-yl)-6-bromoimidazo[1,2-a]pyrazine IV-360;

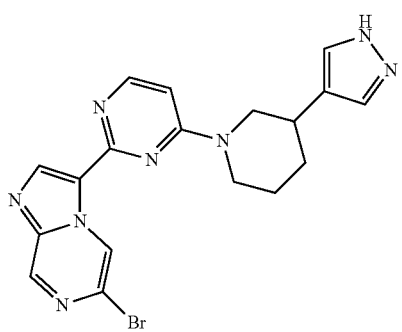 [SMILES: Brc1cn2c(-c3nccc(N4CCCC(c5cn[nH]c5)C4)n3)cnc2cn1]

3-(4-(3-(1H-Pyrazol-4-yl)piperidin-1-yl)pyrimidin-2-yl)-6-bromoimidazo[1,2-a]pyrazine IV-361;

| 1127 | 1128 |
|---|---|
| 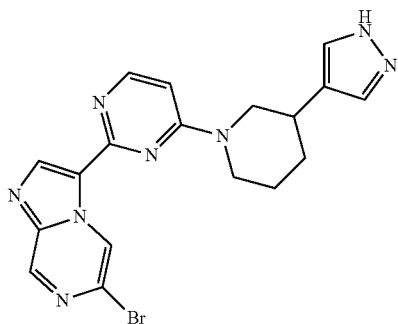 | 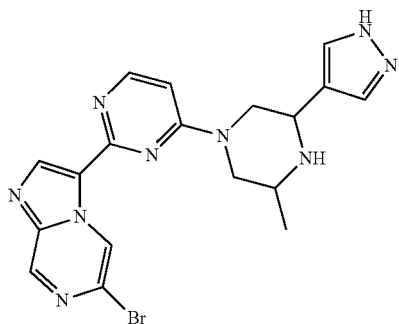 |
| 3-(4-(3-(1H-Imidazol-4-yl)piperidin-1-yl)pyrimidin-2-yl)-6-bromoimidazo[1,2-a]pyrazine IV-362; | 3-(2-(2,5-Dimethyl-3-(1H-pyrazol-4-yl)piperazin-1-yl)pyrimidin-4-yl)-6-(trifluoromethyl)imidazo[1,2-a]pyrazine (all syn diastereoisomer) IV-369; |
| 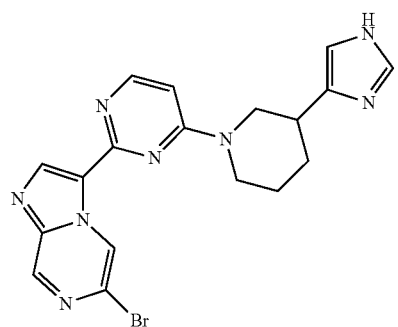 [SMILES: Brc1cn2c(-c3nccc(N4CCCC(c5c[nH]cn5)C4)n3)cnc2cn1] | 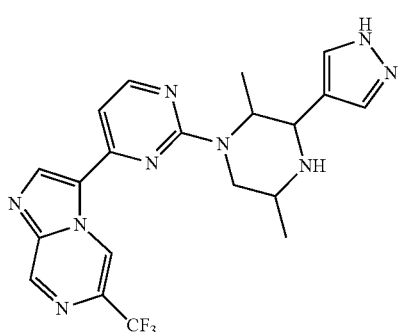 |
| 3-(4-(3-(1H-Imidazol-4-yl)piperidin-1-yl)pyrimidin-2-yl)-6-bromoimidazo[1,2-a]pyrazine IV-363; | 3-(2-(2,5-Dimethyl-3-(1H-pyrazol-4-yl)piperazin-1-yl)pyrimidin-4-yl)-6-(trifluoromethyl)imidazo[1,2-a]pyrazine (all syn diastereoisomer) IV-370; |
| 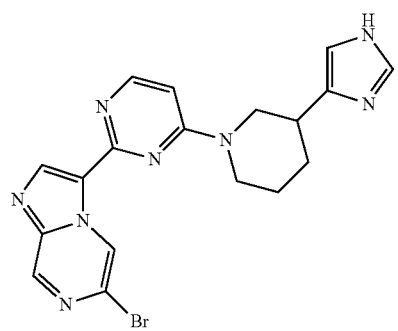 [SMILES: Brc1cn2c(-c3nccc(N4CCCC(c5c[nH]cn5)C4)n3)cnc2cn1] | 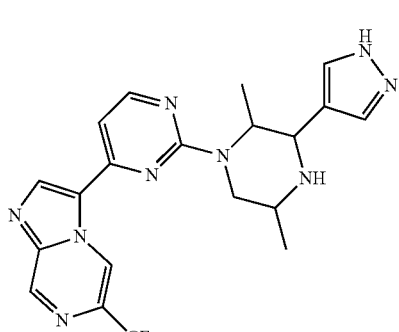 |
| 6-Bromo-3-(4-(3-methyl-5-(1H-pyrazol-4-yl)piperazin-1-yl)pyrimidin-2-yl)imidazo[1,2-a]pyrazine IV-364; | 6-Bromo-3-(4-(3-(2-methyl-1H-imidazol-4-yl)piperidin-1-yl)pyrimidin-2-yl)imidazo[1,2-a]pyrazine IV-374; |
| 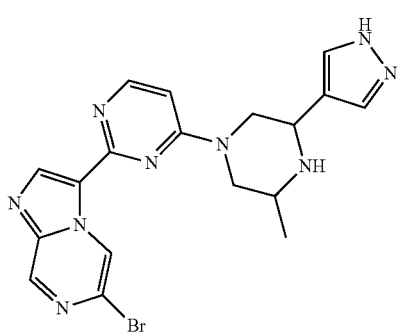 [SMILES: CC1CN(c2ccnc(-c3cnc4cnc(Br)cn34)n2)CC(c2cn[nH]c2)N1] | 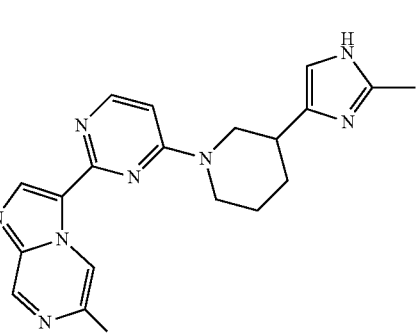 |
| 6-Bromo-3-(4-(3-methyl-5-(1H-pyrazol-4-yl)piperazin-1-yl)pyrimidin-2-yl)imidazo[1,2-a]pyrazine IV-365; | |

6-Bromo-3-(4-(3-(2-methyl-1H-imidazol-4-yl)piperidin-1-yl)pyrimidin-2-yl)imidazo[1,2-a]pyrazine IV-375;

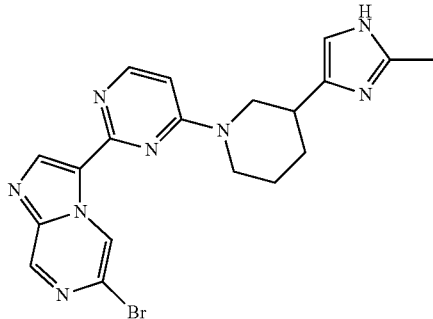 [SMILES: Cc1nc(C2CCCN(c3ccnc(-c4cnc5cnc(Br)cn45)n3)C2)c[nH]1]

3-(4-(3-(1H-Imidazol-4-yl)-2,5-dimethylpiperazin-1-yl)pyrimidin-2-yl)-6-bromoimidazo[1,2-a]pyrazine IV-376;

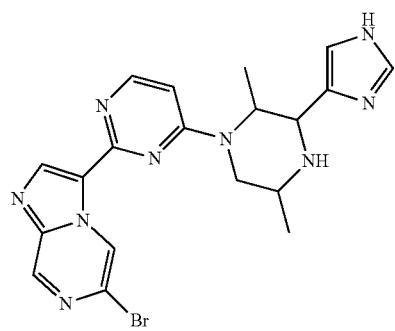 [SMILES: CC1CN(c2ccnc(-c3cnc4cnc(Br)cn34)n2)C(C)C(c2c[nH]cn2)N1]

3-(4-(3-(1H-Imidazol-4-yl)-2,5-dimethylpiperazin-1-yl)pyrimidin-2-yl)-6-bromoimidazo[1,2-a]pyrazine IV-377;

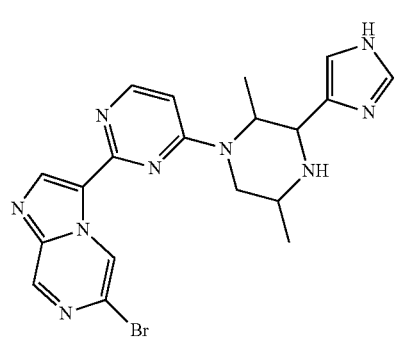 [SMILES: CC1CN(c2ccnc(-c3cnc4cnc(Br)cn34)n2)C(C)C(c2c[nH]cn2)N1]

((5-(1H-Pyrazol-4-yl)-1-(2-(6-(trifluoromethyl)imidazo[1,2-a]pyrazin-3-yl)pyrimidin-4-yl)piperidin-3-yl)imino)dimethyl-λ$^6$-sulfanone IV-399;

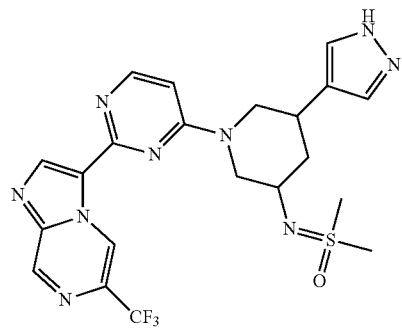 [SMILES: CS(C)(=O)=NC1CC(c2cn[nH]c2)CN(c2ccnc(-c3cnc4cnc(C(F)(F)F)cn34)n2)C1]

((5-(1H-Pyrazol-4-yl)-1-(2-(6-(trifluoromethyl)imidazo[1,2-a]pyrazin-3-yl)pyrimidin-4-yl)piperidin-3-yl)imino)dimethyl-λ$^6$-sulfanone IV-400;

6-Bromo-3-(2-(2,5-dimethyl-3-(1H-pyrazol-4-yl)piperazin-1-yl)pyrimidin-4-yl)imidazo[1,2-a]pyrazine IV-403;

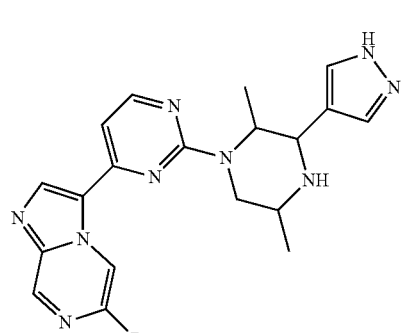

6-Bromo-3-(2-(2,5-dimethyl-3-(1H-pyrazol-4-yl)piperazin-1-yl)pyrimidin-4-yl)imidazo[1,2-a]pyrazine IV-404;

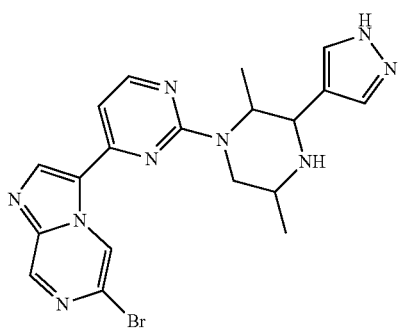

2-(1H-Imidazol-4-yl)-6-methyl-4-(2-(6-(trifluoromethyl)
imidazo[1,2-a]pyrazin-3-yl)pyrimidin-4-yl)morpholine
IV-405;

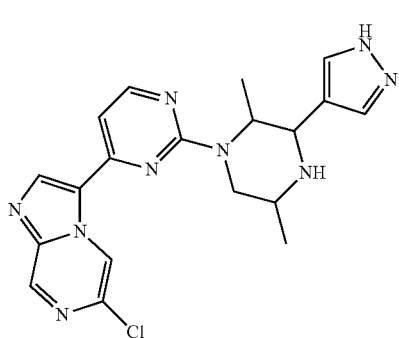

6-Chloro-3-(2-(2,5-dimethyl-3-(1H-pyrazol-4-yl)piperazin-
1-yl)pyrimidin-4-yl)imidazo[1,2-a]pyrazine IV-408;

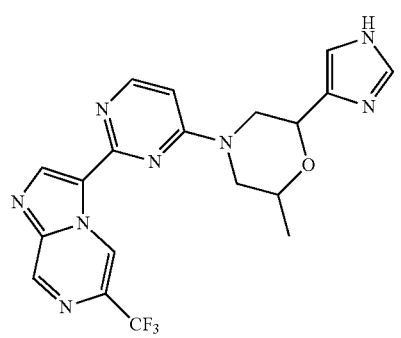 [SMILES: CC1CN(c2ccnc(-c3cnc4cnc(C(F)(F)F)cn34)n2)CC(c2c[nH]cn2)O1]

2-(1H-Imidazol-4-yl)-6-methyl-4-(2-(6-(trifluoromethyl)
imidazo[1,2-a]pyrazin-3-yl)pyrimidin-4-yl)morpholine
IV-406;

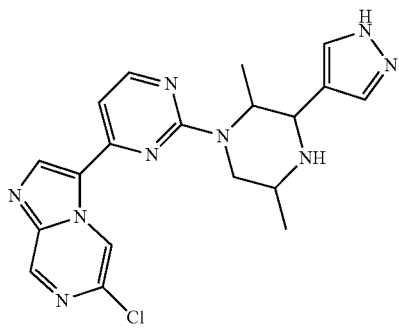

6-Bromo-3-(4-(2-methyl-3-(1H-pyrazol-4-yl)piperazin-1-
yl)pyrimidin-2-yl)imidazo[1,2-a]pyrazine IV-413;

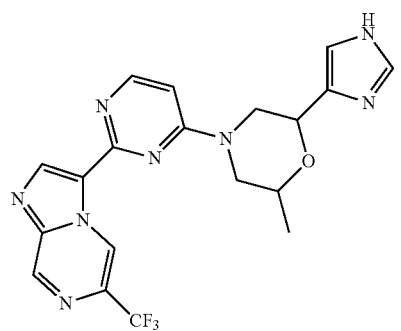 [SMILES: CC1CN(c2ccnc(-c3cnc4cnc(C(F)(F)F)cn34)n2)CC(c2c[nH]cn2)O1]

6-Chloro-3-(2-(2,5-dimethyl-3-(1H-pyrazol-4-yl)piperazin-
1-yl)pyrimidin-4-yl)imidazo[1,2-a]pyrazine IV-407;

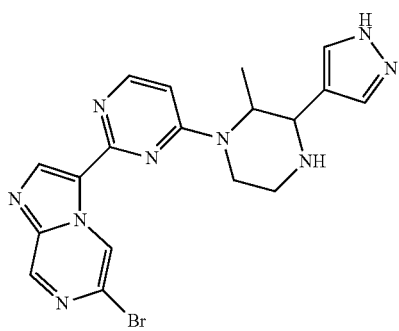

6-Bromo-3-(4-(2-methyl-3-(1H-pyrazol-4-yl)piperazin-1-
yl)pyrimidin-2-yl)imidazo[1,2-a]pyrazine IV-414;

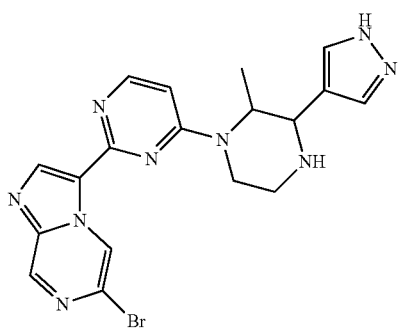

3-(4-(2-Methyl-3-(1H-pyrazol-4-yl)piperidin-1-yl)pyrimidin-2-yl)-6-(trifluoromethyl)imidazo[1,2-a]pyrazine IV-419;

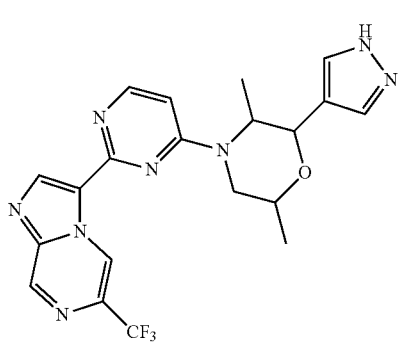

3,6-Dimethyl-2-(1H-pyrazol-4-yl)-4-(2-(6-(trifluoromethyl)imidazo[1,2-a]pyrazin-3-yl)pyrimidin-4-yl)morpholine IV-451;

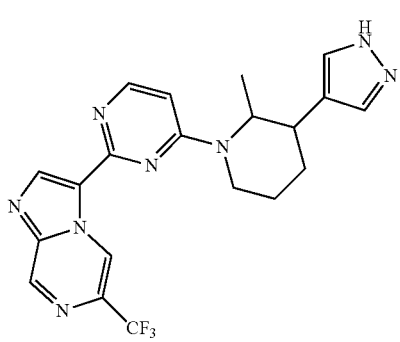 [SMILES: CC1C(c2cn[nH]c2)CCCN1c1ccnc(-c2cnc3cnc(C(F)(F)F)cn23)n1]

3-(4-(2-Methyl-3-(1H-pyrazol-4-yl)piperidin-1-yl)pyrimidin-2-yl)-6-(trifluoromethyl)imidazo[1,2-a]pyrazine IV-420;

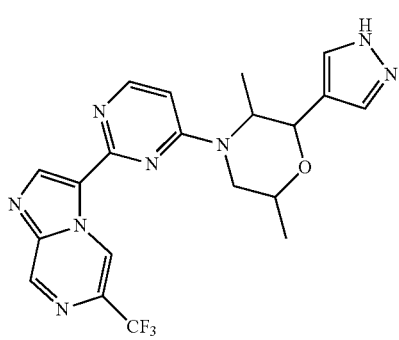

3-(4-(3-Methyl-5-(5-methyl-1H-pyrazol-4-yl)piperazin-1-yl)pyrimidin-2-yl)-6-(trifluoromethyl)imidazo[1,2-a]pyrazine IV-458;

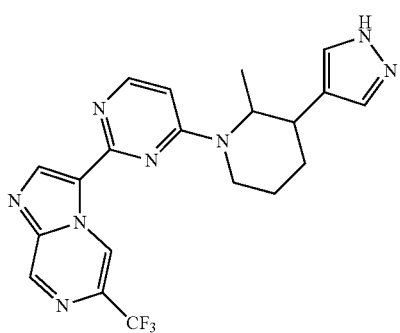

3,6-Dimethyl-2-(1H-pyrazol-4-yl)-4-(2-(6-(trifluoromethyl)imidazo[1,2-a]pyrazin-3-yl)pyrimidin-4-yl)morpholine IV-450;

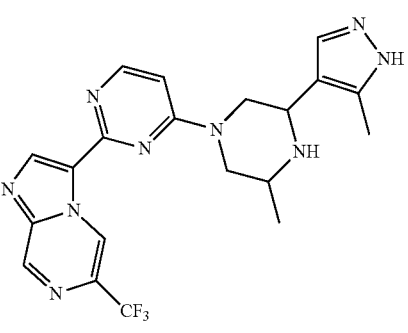

3-(4-(3-Methyl-5-(5-methyl-1H-pyrazol-4-yl)piperazin-1-yl)pyrimidin-2-yl)-6-(trifluoromethyl)imidazo[1,2-a]pyrazine IV-459;

1135

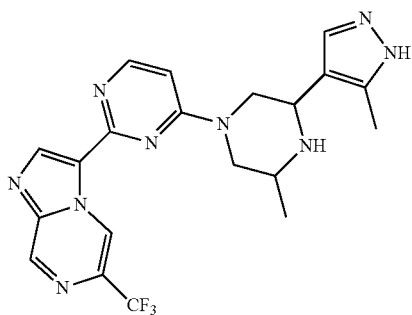 [SMILES: Cc1[nH]ncc1C1CN(c2ccnc(-c3cnc4cnc(C(F)(F)F)cn34)n2)CC(C)N1]

3-(4-(3-Methyl-5-(1H-pyrazol-4-yl)piperazin-1-yl)pyrimidin-2-yl)-6-(trifluoromethyl)imidazo[1,2-a]pyrazine IV-460;

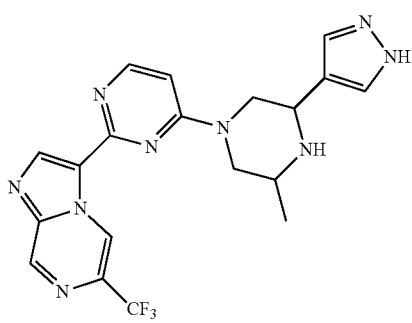

3-(4-(3-Methyl-5-(1H-pyrazol-4-yl)piperazin-1-yl)pyrimidin-2-yl)-6-(trifluoromethyl)imidazo[1,2-a]pyrazine IV-461;

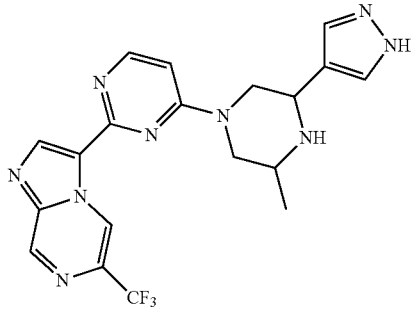 [SMILES: CC1CN(c2ccnc(-c3cnc4cnc(C(F)(F)F)cn34)n2)CC(c2cn[nH]c2)N1]

6-(Difluoromethyl)-3-(4-(3-methyl-5-(5-methyl-1H-pyrazol-4-yl)piperazin-1-yl)pyrimidin-2-yl)imidazo[1,2-a]pyrazine IV-462;

1136

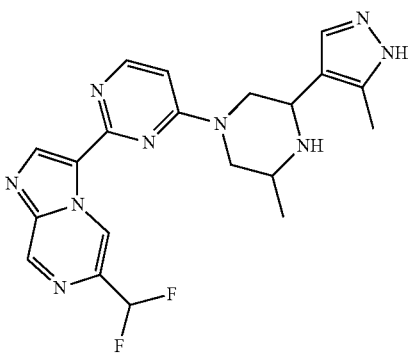 [SMILES: Cc1[nH]ncc1C1CN(c2ccnc(-c3cnc4cnc(C(F)F)cn34)n2)CC(C)N1]

6-(Difluoromethyl)-3-(4-(3-methyl-5-(5-methyl-1H-pyrazol-4-yl)piperazin-1-yl)pyrimidin-2-yl)imidazo[1,2-a]pyrazine IV-463;

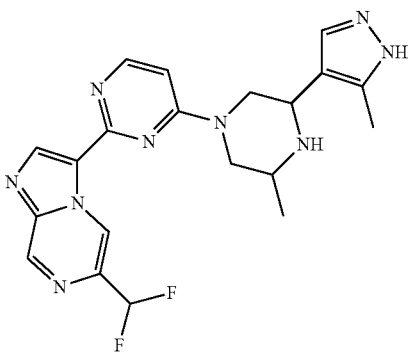 [SMILES: Cc1[nH]ncc1C1CN(c2ccnc(-c3cnc4cnc(C(F)F)cn34)n2)CC(C)N1]

3-(4-(3-(3,5-Dimethyl-1H-pyrazol-4-yl)-5-methylpiperazin-1-yl)pyrimidin-2-yl)-6-(trifluoromethyl)imidazo[1,2-a]pyrazine IV-465;

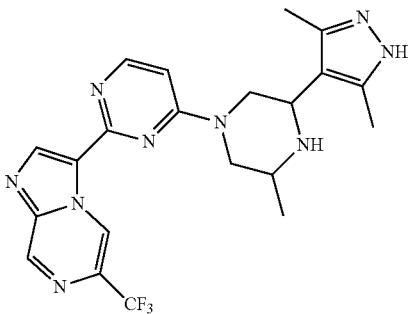 [SMILES: Cc1n[nH]c(C)c1C1CN(c2ccnc(-c3cnc4cnc(C(F)(F)F)cn34)n2)CC(C)N1]

3-(4-(3-(3,5-Dimethyl-1H-pyrazol-4-yl)-5-methylpiperazin-1-yl)pyrimidin-2-yl)-6-(trifluoromethyl)imidazo[1,2-a]pyrazine IV-467;

1137

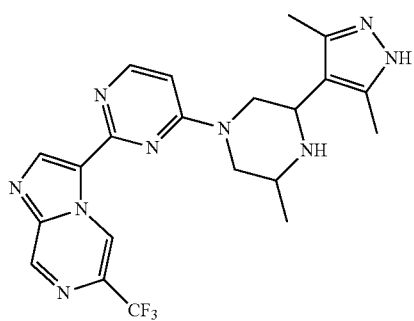 [SMILES: Cc1n[nH]c(C)c1C1CN(c2ccnc(-c3cnc4cnc(C(F)(F)F)cn34)n2)CC(C)N1]

6-(Difluoromethyl)-3-(4-(3-(3-methyl-1H-pyrazol-4-yl)piperidin-1-yl)pyrimidin-2-yl)imidazo[1,2-a]pyrazine IV-468;

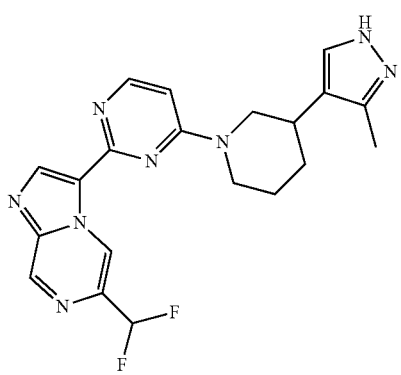 [SMILES: Cc1n[nH]cc1C1CCCN(c2ccnc(-c3cnc4cnc(C(F)F)cn34)n2)C1]

6-(Difluoromethyl)-3-(4-(3-(3-methyl-1H-pyrazol-4-yl)piperidin-1-yl)pyrimidin-2-yl)imidazo[1,2-a]pyrazine IV-469;

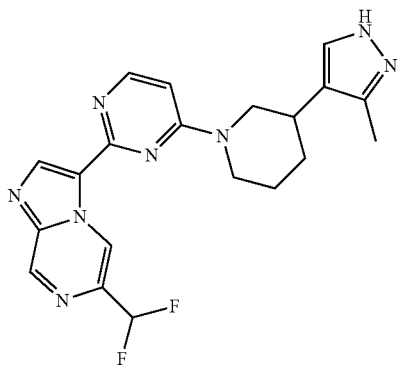 [SMILES: Cc1n[nH]cc1C1CCCN(c2ccnc(-c3cnc4cnc(C(F)F)cn34)n2)C1]

3-(4-(3-(5-Methyl-1H-pyrazol-4-yl)piperidin-1-yl)pyrimidin-2-yl)-6-(trifluoromethyl)imidazo[1,2-a]pyrazine IV-470;

1138

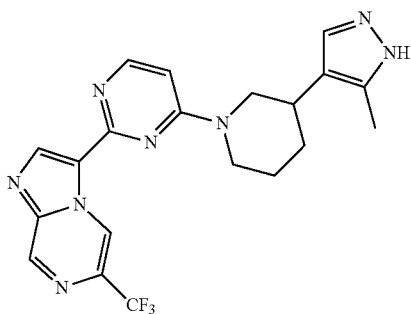

3-(4-(3-(5-Methyl-1H-pyrazol-4-yl)piperidin-1-yl)pyrimidin-2-yl)-6-(trifluoromethyl)imidazo[1,2-a]pyrazine IV-471;

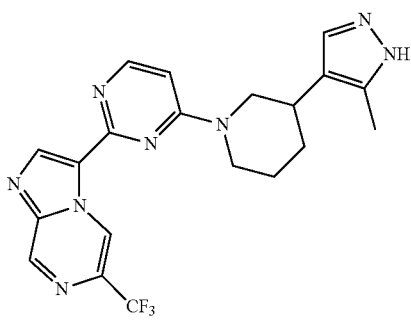 [SMILES: Cc1[nH]ncc1C1CCCN(c2ccnc(-c3cnc4cnc(C(F)(F)F)cn34)n2)C1]

3-(4-(3-Methyl-5-(5-(trifluoromethyl)-1H-pyrazol-4-yl)piperazin-1-yl)pyrimidin-2-yl)-6-(trifluoromethyl)imidazo[1,2-a]pyrazine IV-474;

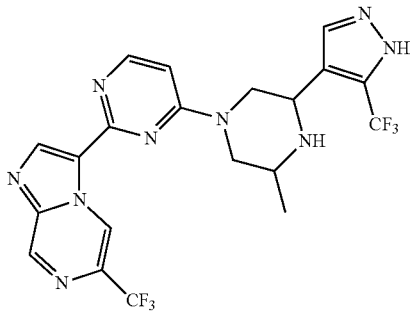 [SMILES: CC1CN(c2ccnc(-c3cnc4cnc(C(F)(F)F)cn34)n2)CC(c2cn[nH]c2C(F)(F)F)N1]

3-(4-(3-Methyl-5-(5-(trifluoromethyl)-1H-pyrazol-4-yl)piperazin-1-yl)pyrimidin-2-yl)-6-(trifluoromethyl)imidazo[1,2-a]pyrazine IV-475;

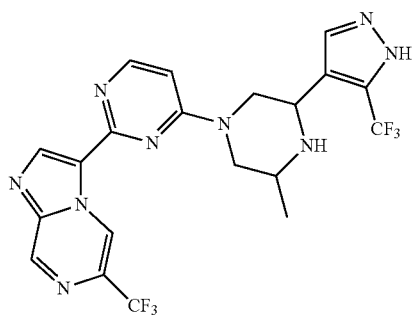 [SMILES: CC1CN(c2ccnc(-c3cnc4cnc(C(F)(F)F)cn34)n2)CC(c2cn[nH]c2C(F)(F)F)N1]

3-(4-(3-(3,5-Dimethyl-1H-pyrazol-4-yl)piperidin-1-yl)py-
rimidin-2-yl)-6-(trifluoromethyl)imidazo[1,2-a]pyrazine
IV-476;

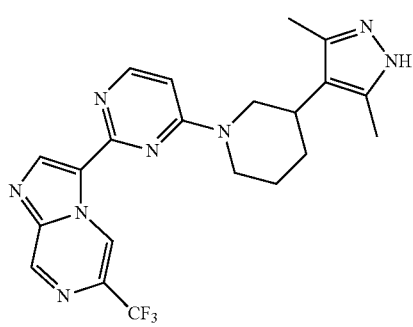 [SMILES: Cc1n[nH]c(C)c1C1CCCN(c2ccnc(-c3cnc4cnc(C(F)(F)F)cn34)n2)C1]

3-(4-(3-(3,5-Dimethyl-1H-pyrazol-4-yl)piperidin-1-yl)py-
rimidin-2-yl)-6-(trifluoromethyl)imidazo[1,2-a]pyrazine
IV-477;

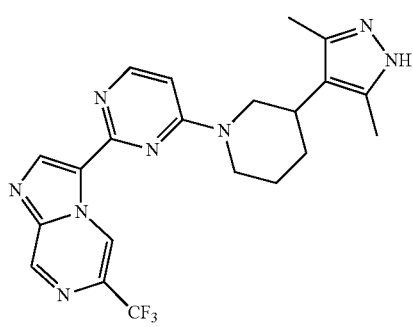 [SMILES: Cc1n[nH]c(C)c1C1CCCN(c2ccnc(-c3cnc4cnc(C(F)(F)F)cn34)n2)C1]

3-(4-(3-(3-Fluoro-1H-pyrazol-4-yl)piperidin-1-yl)pyrimi-
din-2-yl)-6-(trifluoromethyl)imidazo[1,2-a]pyrazine
IV-491;

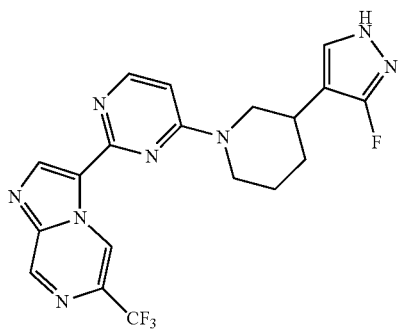 [SMILES: Fc1n[nH]cc1C1CCCN(c2ccnc(-c3cnc4cnc(C(F)(F)F)cn34)n2)C1]

3-(4-(3-(3-Fluoro-1H-pyrazol-4-yl)piperidin-1-yl)pyrimi-
din-2-yl)-6-(trifluoromethyl)imidazo[1,2-a]pyrazine
IV-492;

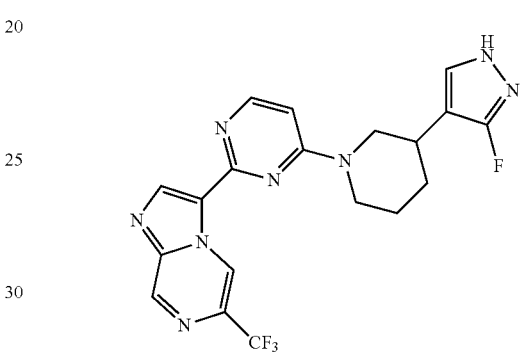

2-Methyl-1-(2-(6-(trifluoromethyl)imidazo[1,2-a]pyrazin-
3-yl)pyrimidin-4-yl)piperidine-3-carboxamide IV-498;

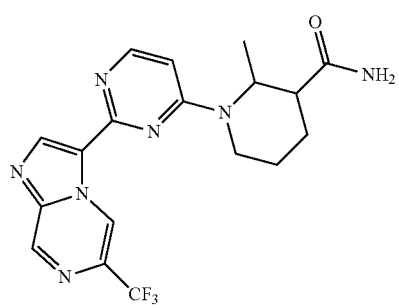

2-Methyl-1-(2-(6-(trifluoromethyl)imidazo[1,2-a]pyrazin-
3-yl)pyrimidin-4-yl)piperidine-3-carboxamide IV-499;

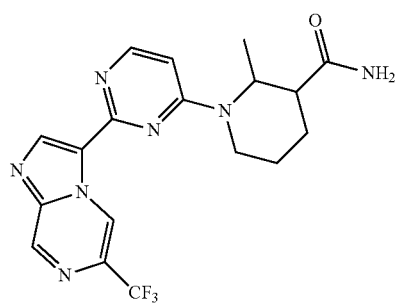 [SMILES: CC1C(C(N)=O)CCCN1c1ccnc(-c2cnc3cnc(C(F)(F)F)cn23)n1]

2,5-Dimethyl-1-(2-(6-(trifluoromethyl)imidazo[1,2-a]
pyrazin-3-yl)pyrimidin-4-yl)piperidine-3-carboxamide
IV-500;

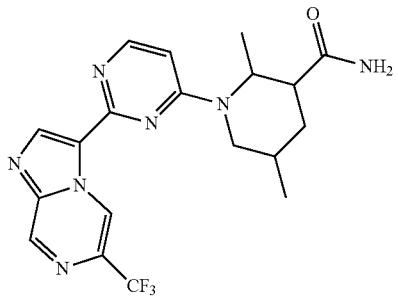

2,5-Dimethyl-1-(2-(6-(trifluoromethyl)imidazo[1,2-a]
pyrazin-3-yl)pyrimidin-4-yl)piperidine-3-carboxamide
IV-501;

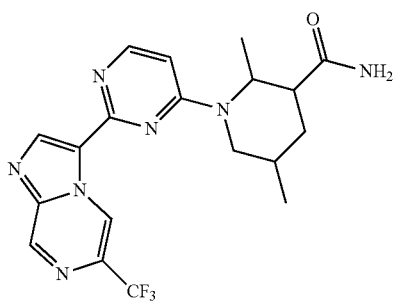 [SMILES: CC1CC(C(N)=O)C(C)N(c2ccnc(-c3cnc4cnc(C(F)(F)F)cn34)n2)C1]

3-(4-(3-(1H-Imidazol-5-yl)-2,5-dimethylpiperazin-1-yl)py-
rimidin-2-yl)-6-(trifluoromethyl)imidazo[1,2-a]pyrazine
IV-538;

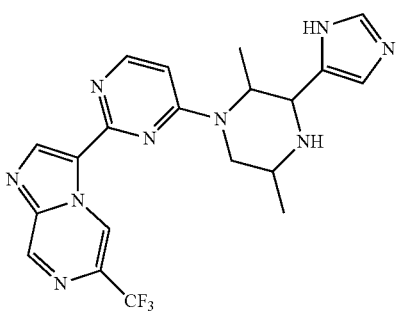 [SMILES: CC1CN(c2ccnc(-c3cnc4cnc(C(F)(F)F)cn34)n2)C(C)C(c2cnc[nH]2)N1]

3-(4-(3-(1H-Pyrazol-4-yl)pyrrolidin-1-yl)pyrimidin-2-yl)-
6-(trifluoromethyl)imidazo[1,2-a]pyrazine I-540;

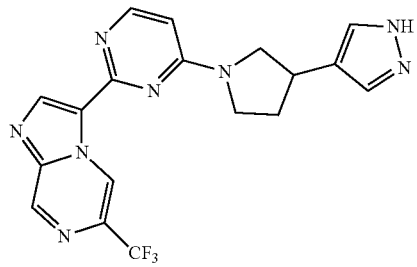

3-(4-(3-(1H-Pyrazol-4-yl)pyrrolidin-1-yl)pyrimidin-2-yl)-
6-(trifluoromethyl)imidazo[1,2-a]pyrazine IV-541;

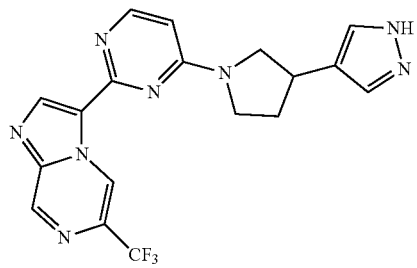 [SMILES: FC(F)(F)c1cn2c(-c3nccc(N4CCC(c5cn[nH]c5)C4)n3)cnc2cn1]

3-(4-(3-(Tetrahydrofuran-3-yl)piperidin-1-yl)pyrimidin-2-
yl)-6-(trifluoromethyl)imidazo[1,2-a]pyrazine IV-543;

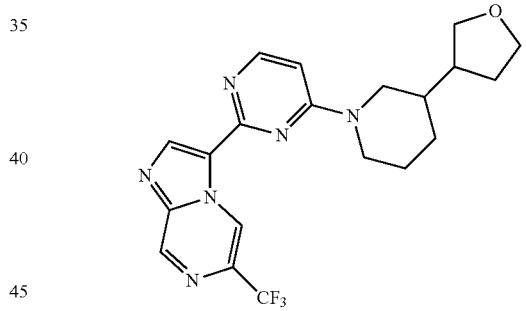

3-(4-(3-(Tetrahydrofuran-3-yl)piperidin-1-yl)pyrimidin-2-
yl)-6-(trifluoromethyl)imidazo[1,2-a]pyrazine IV-544;

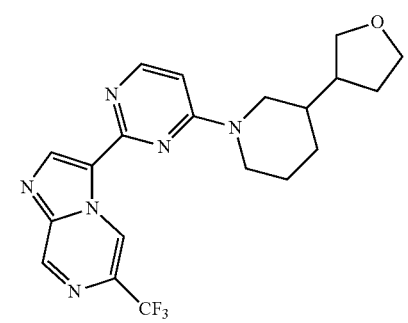 [SMILES: FC(F)(F)c1cn2c(-c3nccc(N4CCCC(C5CCOC5)C4)n3)cnc2cn1]

3-(4-(3-(1H-Pyrazol-4-yl)piperidin-1-yl)pyrimidin-2-yl)-6-
(trifluoromethyl)imidazo[1,2-a]pyrazine IV-545;

1143

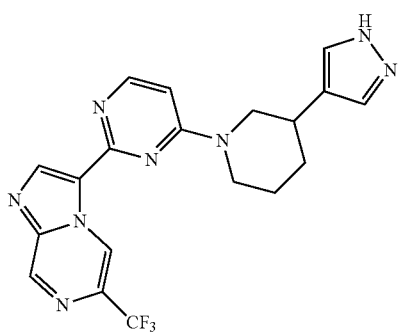 [SMILES: FC(F)(F)c1cn2c(-c3nccc(N4CCCC(c5cn[nH]c5)C4)n3)cnc2cn1]

3-(4-(3-(1H-Pyrazol-4-yl)piperidin-1-yl)pyrimidin-2-yl)-6-(trifluoromethyl)imidazo[1,2-a]pyrazine IV-546;

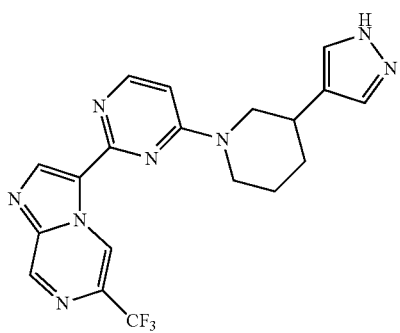 [SMILES: FC(F)(F)c1cn2c(-c3nccc(N4CCCC(c5cn[nH]c5)C4)n3)cnc2cn1]

3-(4-(3-(1H-Imidazol-5-yl)-2,5-dimethylpiperazin-1-yl)pyrimidin-2-yl)-6-(trifluoromethyl)imidazo[1,2-a]pyrazine IV-549;

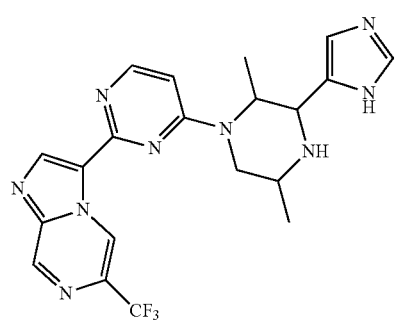

3-(4-(3-(3-Fluoro-1H-pyrazol-4-yl)pyrrolidin-1-yl)pyrimidin-2-yl)-6-(trifluoromethyl)imidazo[1,2-a]pyrazine IV-562;

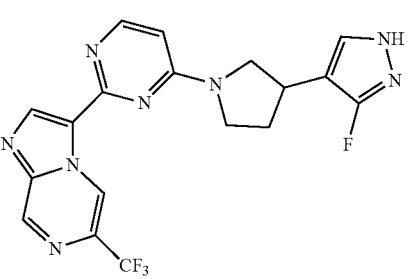 [SMILES: Fc1n[nH]cc1C1CCN(c2ccnc(-c3cnc4cnc(C(F)(F)F)cn34)n2)C1]

1144

3-(4-(3-(3-Fluoro-1H-pyrazol-4-yl)pyrrolidin-1-yl)pyrimidin-2-yl)-6-(trifluoromethyl)imidazo[1,2-a]pyrazine IV-563;

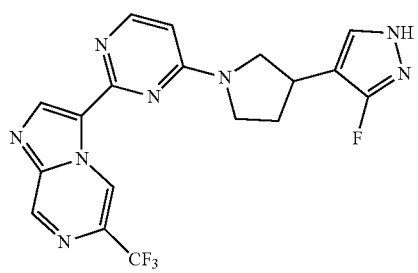

4-(4-Methyl-1-(2-(6-(trifluoromethyl)imidazo[1,2-a]pyrazin-3-yl)pyrimidin-4-yl)pyrrolidin-3-yl)morpholine IV-569;

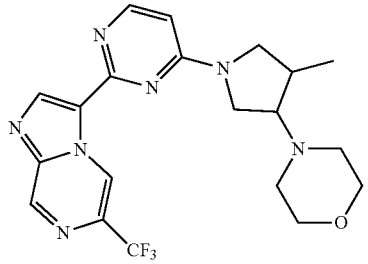 [SMILES: CC1CN(c2ccnc(-c3cnc4cnc(C(F)(F)F)cn34)n2)CC1N1CCOCC1]

3-(4-(3-(1H-1,2,3-Triazol-1-yl)piperidin-1-yl)pyrimidin-2-yl)-6-(trifluoromethyl)imidazo[1,2-a]pyrazine IV-600;

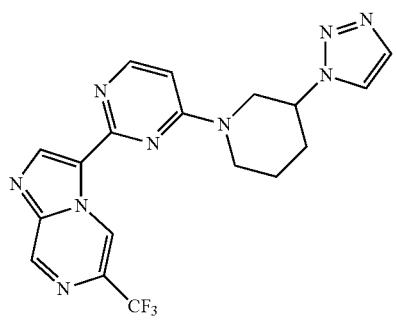 [SMILES: FC(F)(F)c1cn2c(-c3nccc(N4CCCC(n5ccnn5)C4)n3)cnc2cn1]

2-Methyl-1-(2-(6-(trifluoromethyl)imidazo[1,2-a]pyrazin-3-yl)pyrimidin-4-yl)pyrrolidine-3-carboxamide IV-614;

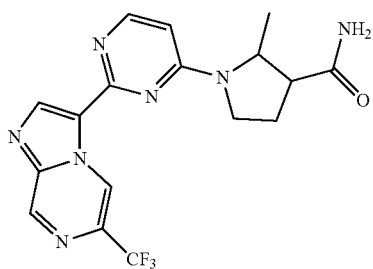 [SMILES: CC1C(C(N)=O)CCN1c1ccnc(-c2cnc3cnc(C(F)(F)F)cn23)n1]

2-Methyl-1-(2-(6-(trifluoromethyl)imidazo[1,2-a]pyrazin-3-yl)pyrimidin-4-yl)pyrrolidine-3-carboxamide IV-615;

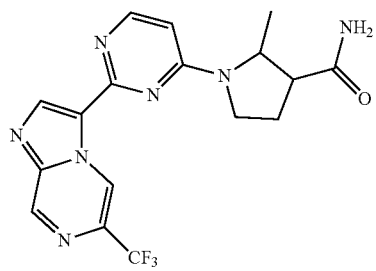

3-(1H-Pyrazol-4-yl)-1-(2-(6-(trifluoromethyl)imidazo[1,2-a]pyrazin-3-yl)pyrimidin-4-yl)piperidin-4-ol IV-621;

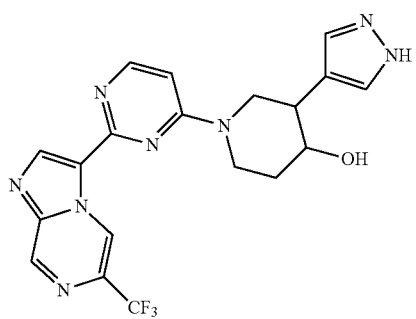 [SMILES: OC1CCN(c2ccnc(-c3cnc4cnc(C(F)(F)F)cn34)n2)CC1c1cn[nH]c1]

3-(1H-Pyrazol-4-yl)-1-(2-(6-(trifluoromethyl)imidazo[1,2-a]pyrazin-3-yl)pyrimidin-4-yl)piperidin-4-ol IV-622;

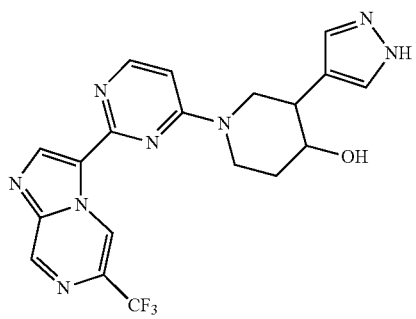 [SMILES: OC1CCN(c2ccnc(-c3cnc4cnc(C(F)(F)F)cn34)n2)CC1c1cn[nH]c1]

3-(1H-Pyrazol-4-yl)-1-(2-(6-(trifluoromethyl)imidazo[1,2-a]pyrazin-3-yl)pyrimidin-4-yl)piperidin-4-ol IV-623;

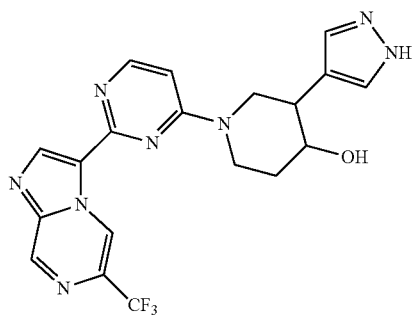 [SMILES: OC1CCN(c2ccnc(-c3cnc4cnc(C(F)(F)F)cn34)n2)CC1c1cn[nH]c1]

3-(1H-Pyrazol-4-yl)-1-(2-(6-(trifluoromethyl)imidazo[1,2-a]pyrazin-3-yl)pyrimidin-4-yl)piperidin-4-ol IV-624;

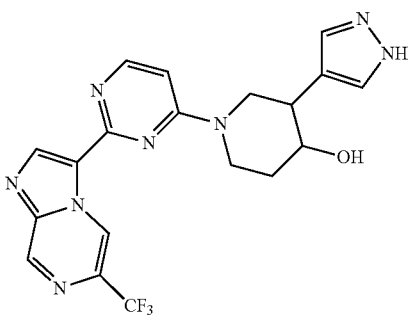

6-(Trifluoromethyl)-3-(4-(3-(3-(trifluoromethyl)-1H-pyrazol-4-yl)pyrrolidin-1-yl)pyrimidin-2-yl)imidazo[1,2-a]pyrazine IV-628;

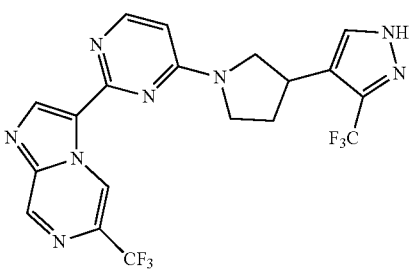

6-(Trifluoromethyl)-3-(4-(3-(3-(trifluoromethyl)-1H-pyrazol-4-yl)pyrrolidin-1-yl)pyrimidin-2-yl)imidazo[1,2-a]pyrazine IV-629;

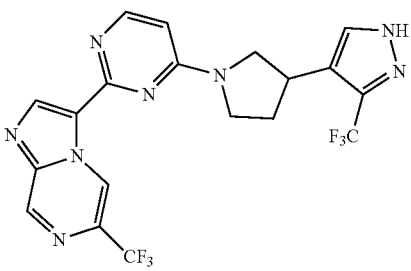 [SMILES: FC(F)(F)c1cn2c(-c3nccc(N4CCC(c5c[nH]nc5C(F)(F)F)C4)n3)cnc2cn1]

(5-(1H-Pyrazol-4-yl)-1-(2-(6-(trifluoromethyl)imidazo[1,2-a]pyrazin-3-yl)pyrimidin-4-yl)piperidin-3-yl)dimethylphosphine oxide IV-632;

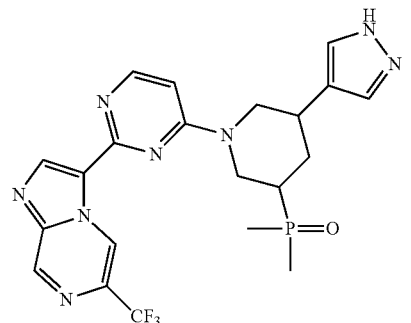

(5-(1H-Pyrazol-4-yl)-1-(2-(6-(trifluoromethyl)imidazo[1,2-a]pyrazin-3-yl)pyrimidin-4-yl)piperidin-3-yl)dimethylphosphine oxide IV-633;

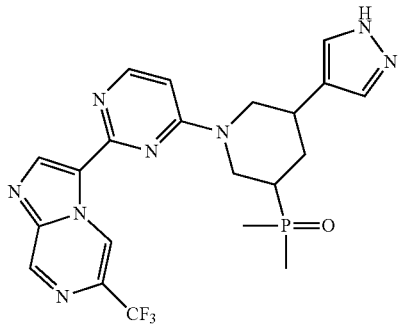 [SMILES: CP(C)(=O)C1CC(c2cn[nH]c2)CN(c2ccnc(-c3cnc4cnc(C(F)(F)F)cn34)n2)C1]

2-(1H-Imidazol-4-yl)-3,6-dimethyl-4-(2-(6-(trifluoromethyl)imidazo[1,2-a]pyrazin-3-yl)pyrimidin-4-yl)morpholine IV-638;

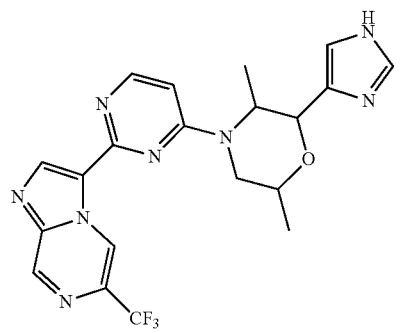 [SMILES: CC1CN(c2ccnc(-c3cnc4cnc(C(F)(F)F)cn34)n2)C(C)C(c2c[nH]cn2)O1]

2-(1H-Imidazol-4-yl)-3,6-dimethyl-4-(2-(6-(trifluoromethyl)imidazo[1,2-a]pyrazin-3-yl)pyrimidin-4-yl)morpholine IV-639;

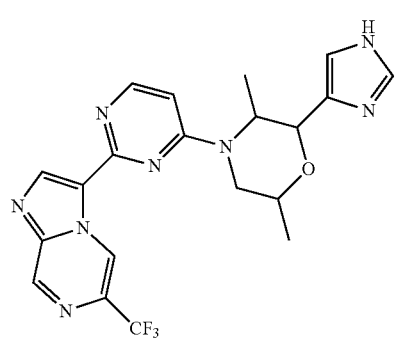 [SMILES: CC1CN(c2ccnc(-c3cnc4cnc(C(F)(F)F)cn34)n2)C(C)C(c2c[nH]cn2)O1]

3-(6-(2,5-Dimethyl-3-(1H-pyrazol-4-yl)piperazin-1-yl)pyrazin-2-yl)-6-(trifluoromethyl)imidazo[1,2-a]pyrazine IV-649;

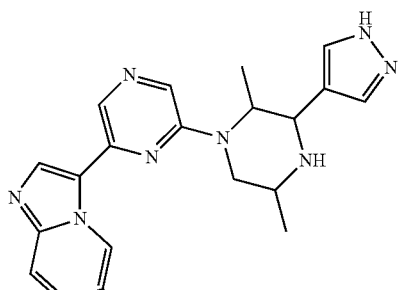

3-(6-(2,5-Dimethyl-3-(1H-pyrazol-4-yl)piperazin-1-yl)pyrazin-2-yl)-6-(trifluoromethyl)imidazo[1,2-a]pyrazine IV-650;

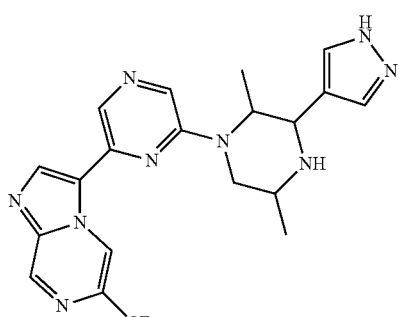

3-(4-(2,5-Dimethyl-3-(1H-pyrazol-4-yl)piperazin-1-yl)-6-methylpyrimidin-2-yl)-6-(trifluoromethyl)imidazo[1,2-a]pyrazine IV-669;

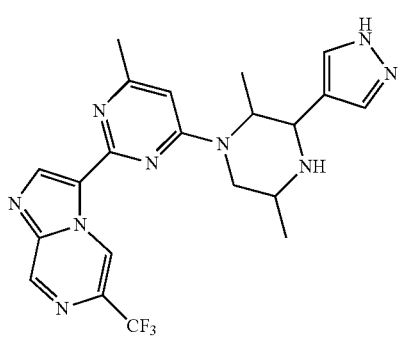 [SMILES: Cc1cc(N2CC(C)NC(c3cn[nH]c3)C2C)nc(-c2cnc3cnc(C(F)(F)F)cn23)n1]

3-(4-(2,5-Dimethyl-3-(1H-pyrazol-4-yl)piperazin-1-yl)-6-methylpyrimidin-2-yl)-6-(trifluoromethyl)imidazo[1,2-a]pyrazine IV-670;

1149

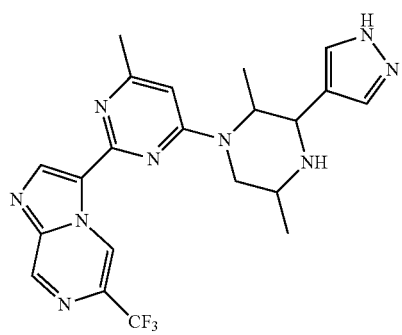 [SMILES: Cc1cc(N2CC(C)NC(c3cn[nH]c3)C2C)nc(-c2cnc3cnc(C(F)(F)F)cn23)n1]

3-(4-(2,5-Dimethyl-3-(2-(trifluoromethyl)-1H-imidazol-4-yl)piperazin-1-yl)pyrimidin-2-yl)-6-(trifluoromethyl)imidazo[1,2-a]pyrazine IV-673;

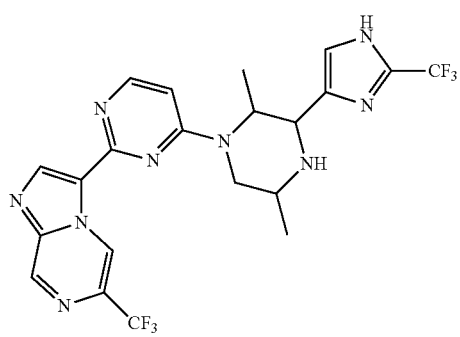 [SMILES: CC1CN(c2ccnc(-c3cnc4cnc(C(F)(F)F)cn34)n2)C(C)C(c2c[nH]c(C(F)(F)F)n2)N1]

3-(4-(2,5-Dimethyl-3-(2-(trifluoromethyl)-1H-imidazol-4-yl)piperazin-1-yl)pyrimidin-2-yl)-6-(trifluoromethyl)imidazo[1,2-a]pyrazine IV-674;

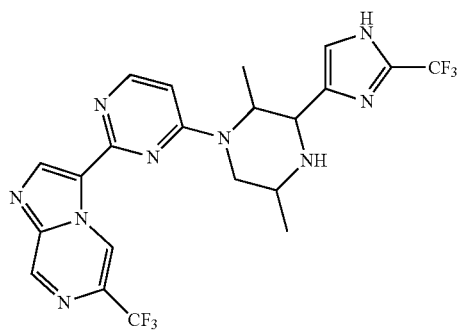 [SMILES: CC1CN(c2ccnc(-c3cnc4cnc(C(F)(F)F)cn34)n2)C(C)C(c2c[nH]c(C(F)(F)F)n2)N1]

2-(5-(1H-Pyrazol-4-yl)-1-(2-(6-(trifluoromethyl)imidazo[1,2-a]pyrazin-3-yl)pyrimidin-4-yl)piperidin-3-yl)propan-2-ol IV-682;

1150

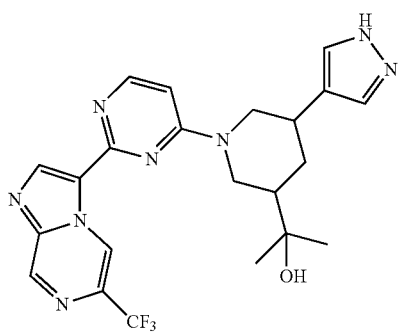 [SMILES: CC(C)(O)C1CC(c2cn[nH]c2)CN(c2ccnc(-c3cnc4cnc(C(F)(F)F)cn34)n2)C1]

2-(5-(1H-Pyrazol-4-yl)-1-(2-(6-(trifluoromethyl)imidazo[1,2-a]pyrazin-3-yl)pyrimidin-4-yl)piperidin-3-yl)propan-2-ol IV-683;

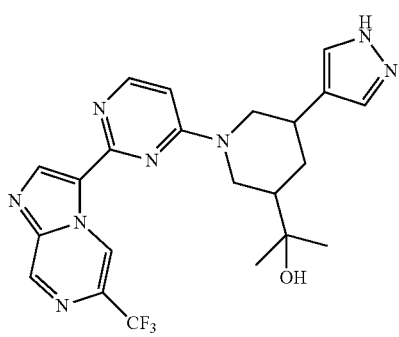 [SMILES: CC(C)(O)C1CC(c2cn[nH]c2)CN(c2ccnc(-c3cnc4cnc(C(F)(F)F)cn34)n2)C1]

2-(5-(1H-Pyrazol-4-yl)-1-(2-(6-(trifluoromethyl)imidazo[1,2-a]pyrazin-3-yl)pyrimidin-4-yl)piperidin-3-yl)propan-2-ol IV-684;

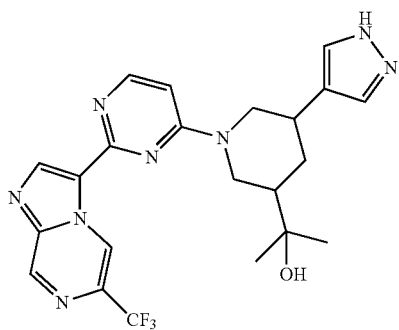 [SMILES: CC(C)(O)C1CC(c2cn[nH]c2)CN(c2ccnc(-c3cnc4cnc(C(F)(F)F)cn34)n2)C1]

2-(5-(1H-Pyrazol-4-yl)-1-(2-(6-(trifluoromethyl)imidazo[1,2-a]pyrazin-3-yl)pyrimidin-4-yl)piperidin-3-yl)propan-2-ol IV-685;

1151

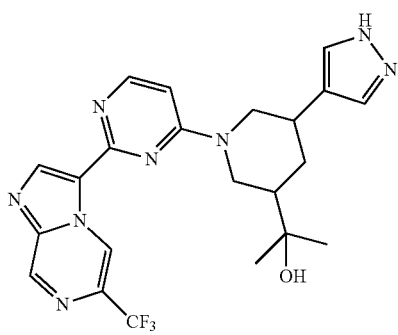 [SMILES: CC(C)(O)C1CC(c2cn[nH]c2)CN(c2ccnc(-c3cnc4cnc(C(F)(F)F)cn34)n2)C1]

Example 76: 3-(4-(2,7-Diazaspiro[3.5]nonan-7-yl)pyrimidin-2-yl)-6-(trifluoromethyl)imidazo[1,2-a]pyrazine, IV-692

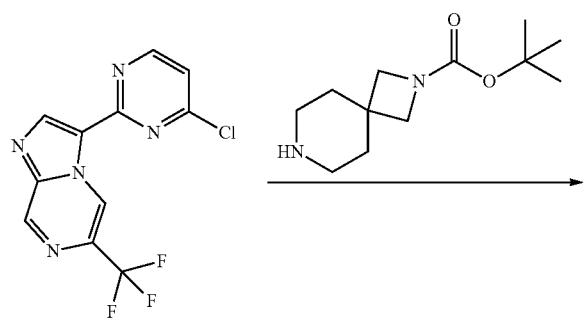

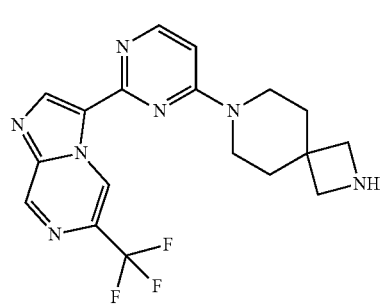 [SMILES: FC(F)(F)c1cn2c(-c3nccc(N4CCC5(CC4)CNC5)n3)cnc2cn1]

1152

Step 1: tert-Butyl 7-(2-(6-(trifluoromethyl)imidazo[1,2-a]pyrazin-3-yl)pyrimidin-4-yl)-2,7-diazaspiro[3.5]nonane-2-carboxylate

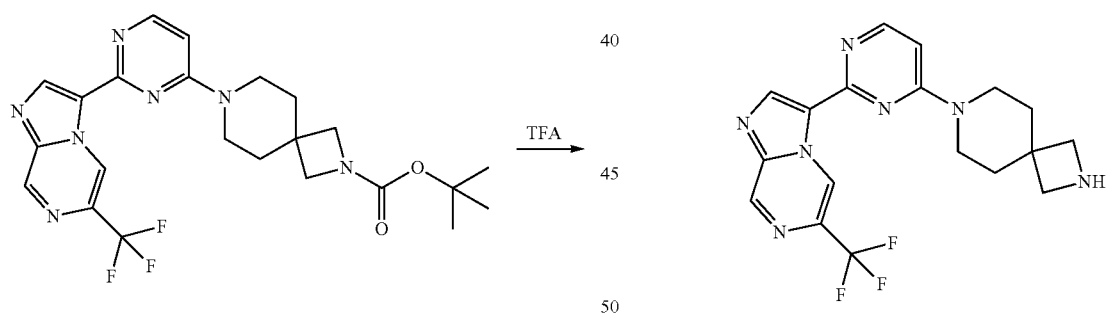

3-(4-Chloropyrimidin-2-yl)-6-(trifluoromethyl)imidazo[1,2-a]pyrazine (125 mg, 0.41 mmol) was dissolved in DMF (3 mL) and tert-butyl 2,7-diazaspiro[3.5]nonane-2-carboxylate (190 mg, 0.84 mmol) and DIPEA (450 μL, 2.58 mmol) were added. The reaction mixture was heated to 80° C. for 1 hour before the reaction was cooled, water added and the reaction stirred for mins. The resultant precipitate was filtered off to give tert-butyl 7-(2-(6-(trifluoromethyl)imidazo[1,2-a]pyrazin-3-yl)pyrimidin-4-yl)-2,7-diazaspiro[3.5]nonane-2-carboxylate (181 mg, 89%) as a pale yellow solid; $^1$H NMR (500 MHz, DMSO-$d_6$) δ 10.25 (s, 1H), 9.36 (d, J=1.2 Hz, 1H), 8.70 (d, J=0.8 Hz, 1H), 8.38 (d, J=6.3 Hz, 1H), 6.90 (d, J=6.4 Hz, 1H), 3.65 (br s, 8H), 1.78 (t, J=5.6 Hz, 4H), 1.40 (s, 9H); ES+ [M+H]=490.0.

Step 2: 3-(4-(2,7-Diazaspiro[3.5]nonan-7-yl)pyrimidin-2-yl)-6-(trifluoromethyl)imidazo[1,2-a]pyrazine tert-Butyl 7-(2-(6-(trifluoromethyl)imidazo[1,2-a]pyrazin-3-yl)pyrimidin-4-yl)-2,7-diazaspiro[3.5]nonane-2-carboxylate (181 mg, 0.37 mmol) was dissolved in DCM (5 mL) and TFA (1 mL, 13.0 mmol) was added. The reaction was stirred at ambient temperature overnight. The mixture was passed through an SCX-2 cartridge, washing with methanol and then eluting product with 2 M ammonia in methanol to give, after drying, 3-(4-(2,7-diazaspiro[3.5]nonan-7-yl)pyrimidin-2-yl)-6-(trifluoromethyl)imidazo[1,2-a]pyrazine (143 mg, 99%); 1H NMR (500 MHz, DMSO-$d_6$) δ 10.25 (s, 1H), 9.36 (s, 1H), 8.69 (s, 1H), 8.37 (d, J=6.4 Hz, 1H), 6.88 (d, J=6.3 Hz, 1H), 3.31 (br s, 4H) 3.68 (d, J=18.7 Hz, 4H), 1.80 (t, J=5.7 Hz, 4H); $^{19}$F NMR (471 MHz, DMSO-$d_6$) −65.84 (d, J=7.1 Hz); ES+ [M+H]=390.1.

The following compounds were made using methodology similar to that described in Example 76:

1-(2-(6-(Difluoromethyl)imidazo[1,2-a]pyrazin-3-yl)py-
rimidin-4-yl)azepan-4-amine IV-118;

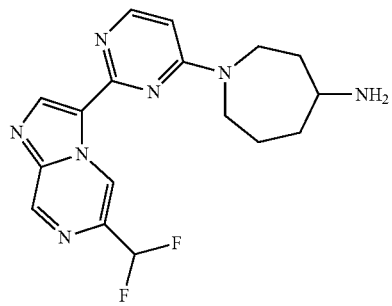 [SMILES: NC1CCCN(c2ccnc(-c3cnc4cnc(C(F)F)cn34)n2)CC1]

4-(2-(6-(Difluoromethyl)imidazo[1,2-a]pyrazin-3-yl)py-
rimidin-4-yl)-1-methyl-1,4,9-triazaspiro[5.5]undecane
IV-123;

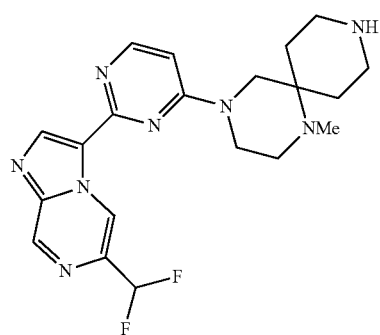 [SMILES: CN1CCN(c2ccnc(-c3cnc4cnc(C(F)F)cn34)n2)CC12CCNCC2]

(1-(2-(6-(Difluoromethyl)imidazo[1,2-a]pyrazin-3-yl)py-
rimidin-4-yl)piperidin-3-yl)(piperazin-1-yl)methanone
IV-139;

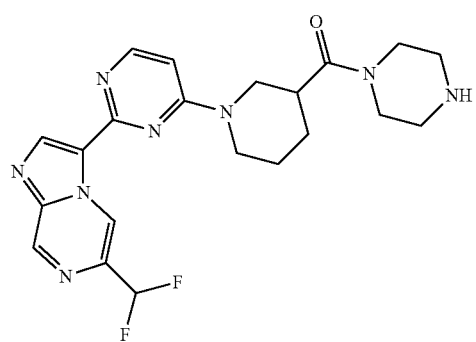 [SMILES: O=C(C1CCCN(c2ccnc(-c3cnc4cnc(C(F)F)cn34)n2)C1)N1CCNCC1]

2-(2-(6-(Difluoromethyl)imidazo[1,2-a]pyrazin-3-yl)py-
rimidin-4-yl)-2,8-diazaspiro[4.5]decane IV-140;

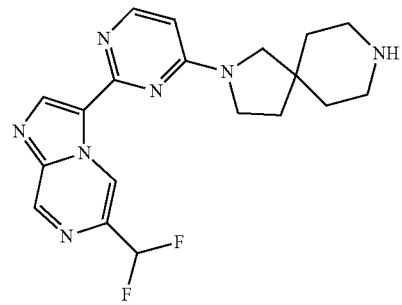 [SMILES: FC(F)c1cn2c(-c3nccc(N4CCC5(CCNCC5)C4)n3)cnc2cn1]

(1-(2-(6-(Difluoromethyl)imidazo[1,2-a]pyrazin-3-yl)py-
rimidin-4-yl)piperidin-3-yl)methanamine IV-143;

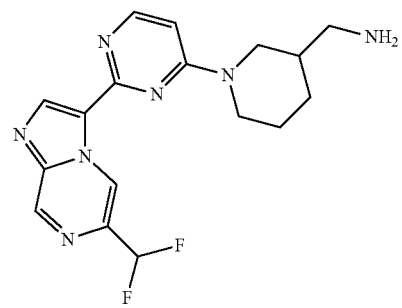 [SMILES: NCC1CCCN(c2ccnc(-c3cnc4cnc(C(F)F)cn34)n2)C1]

2-Amino-N-(3-(2-(6-(difluoromethyl)imidazo[1,2-a]
pyrazin-3-yl)pyrimidin-4-yl)phenyl)acetamide IV-167:

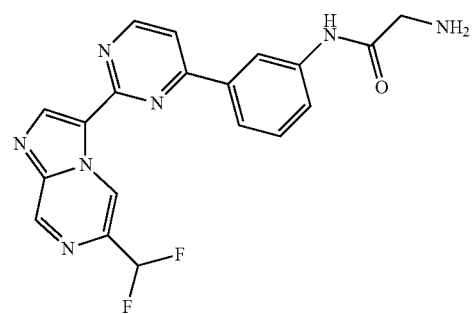 [SMILES: NCC(=O)Nc1cccc(-c2ccnc(-c3cnc4cnc(C(F)F)cn34)n2)c1]

3-(6-(4-Methylpiperazin-1-yl)pyridin-2-yl)imidazo[1,2-a]
pyrazine-6-carboxamide IV-212;

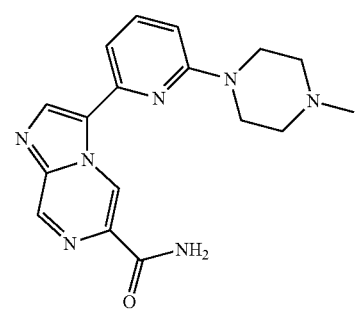 [SMILES: CN1CCN(c2cccc(-c3cnc4cnc(C(N)=O)cn34)n2)CC1]

6-Chloro-3-(4-(3-methyl-5-(1H-pyrazol-4-yl)piperazin-1-
yl)pyrimidin-2-yl)imidazo[1,2-a]pyrazine IV-213;

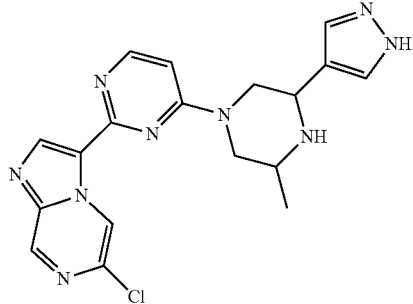 [SMILES: CC1CN(c2ccnc(-c3cnc4cnc(Cl)cn34)n2)CC(c2cn[nH]c2)N1]

6-Chloro-3-(4-(3-methyl-5-(1H-pyrazol-4-yl)piperazin-1-yl)pyrimidin-2-yl)imidazo[1,2-a]pyrazine IV-214;

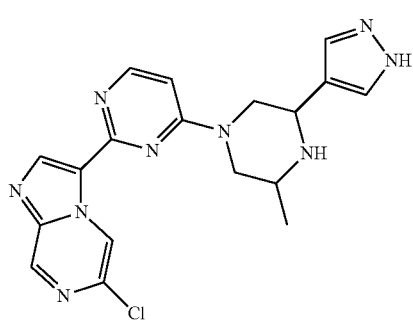 [SMILES: CC1CN(c2ccnc(-c3cnc4cnc(Cl)cn34)n2)CC(c2cn[nH]c2)N1]

3-Methyl-2-(1H-pyrazol-4-yl)-4-(2-(6-(trifluoromethyl)imidazo[1,2-a]pyrazin-3-yl)pyrimidin-4-yl)morpholine IV-218;

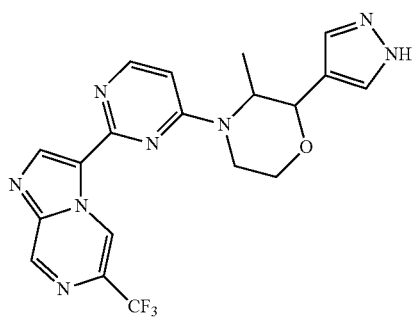 [SMILES: CC1C(c2cn[nH]c2)OCCN1c1ccnc(-c2cnc3cnc(C(F)(F)F)cn23)n1]

3-(4-(3-Aminopiperidin-1-yl)pyrimidin-2-yl)imidazo[1,2-a]pyrazine-6-carboxamide IV-256;

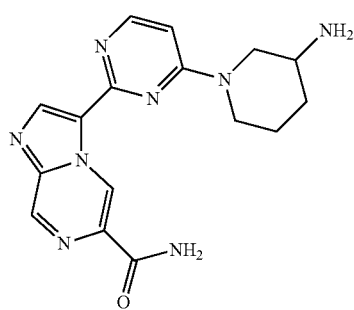 [SMILES: NC(=O)c1cn2c(-c3nccc(N4CCCC(N)C4)n3)cnc2cn1]

3-(4-(3-(Azetidin-3-yl)piperidin-1-yl)pyrimidin-2-yl)-6-(trifluoromethyl)imidazo[1,2-a]pyrazine IV-696;

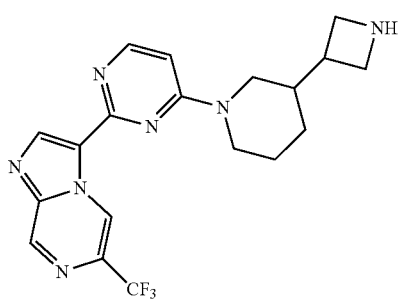 [SMILES: FC(F)(F)c1cn2c(-c3nccc(N4CCCC(C5CNC5)C4)n3)cnc2cn1]

Example 77: 3-(4-(7-(Methylsulfonyl)-2,7-diazaspiro[3.5]nonan-2-yl)pyrimidin-2-yl)-6-(trifluoromethyl)imidazo[1,2-a]pyrazine, IV-698

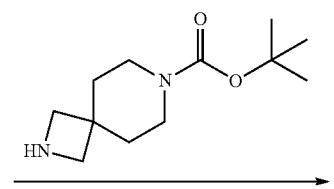

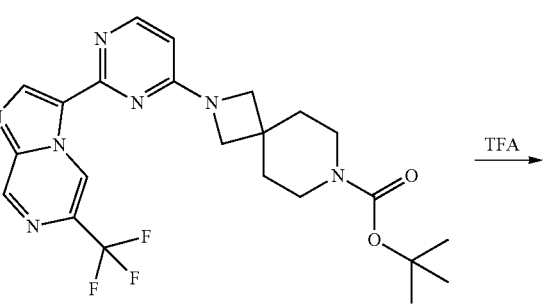

TFA

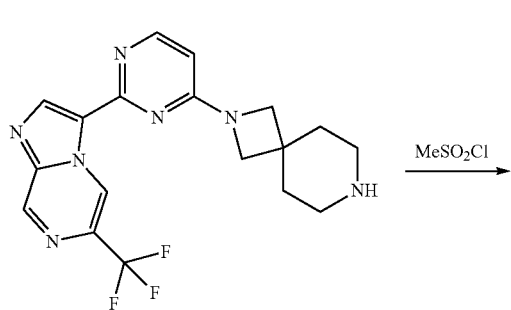

MeSO₂Cl

-continued

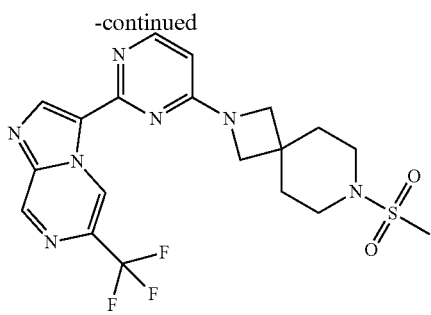

Step 1: tert-Butyl 2-(2-(6-(trifluoromethyl)imidazo[1,2-a]pyrazin-3-yl)pyrimidin-4-yl)-2,7-diazaspiro[3.5]nonane-7-carboxylate

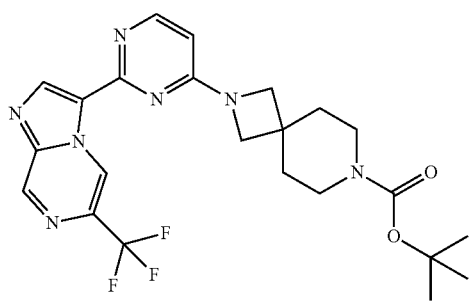 [SMILES: CC(C)(C)OC(=O)N1CCC2(CC1)CN(c1ccnc(-c3cnc4cnc(C(F)(F)F)cn34)n1)C2]

DIPEA (450 µL, 2.58 mmol) was added to a solution of 3-(4-chloropyrimidin-2-yl)-6-(trifluoromethyl)imidazo[1,2-a]pyrazine (125 mg, 0.417 mmol) and tert-butyl 2,7-diazaspiro[3.5]nonane-7-carboxylate (hydrochloride salt) (160 mg, 0.609 mmol) in DMF (3 mL). The reaction mixture was heated at 80° C. for 1 hour before being cooled, water added and the resultant precipitate filtered and dried to give tert-butyl 2-(2-(6-(trifluoromethyl)imidazo[1,2-a]pyrazin-3-yl)pyrimidin-4-yl)-2,7-diazaspiro[3.5]nonane-7-carboxylate (187 mg, 91%); ¹H NMR (500 MHz, DMSO-d₆) δ 10.36 (d, J=1.2 Hz, 1H), 9.36 (d, J=1.3 Hz, 1H), 8.64 (s, 1H), 8.36 (d, J=6.0 Hz, 1H), 6.41 (d, J=6.0 Hz, 1H), 3.91 (s, 2H), 3.34 (s, 2H), 1.76 (t, J=5.5 Hz, 4H), 1.42 (s, 9H), 1.41-1.37 (m, 2H), 1.26 (q, J=7.2 Hz, 2H); ES+ [M+H]=490.1.

Step 2: 3-(4-(2,7-Diazaspiro[3.5]nonan-2-yl)pyrimidin-2-yl)-6-(trifluoromethyl)imidazo[1,2-a]pyrazine

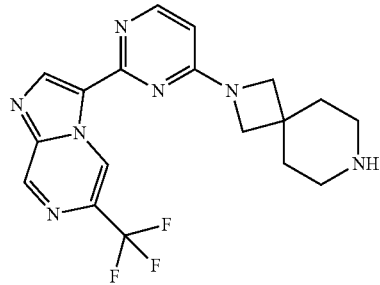 [SMILES: FC(F)(F)c1cn2c(-c3nccc(N4CC5(CCNCC5)C4)n3)cnc2cn1]

To a solution of tert-butyl 2-[2-[6-(trifluoromethyl)imidazo[1,2-a]pyrazin-3-yl]pyrimidin-4-yl]-2,7-diazaspiro[3.5]nonane-7-carboxylate (187 mg, 0.38 mmol) in DCM (5 mL) was added TFA (1 mL, 13.0 mmol). The mixture was stirred at ambient temperature overnight before being passed through an SCX-2 cartridge, eluting the product with 2 M ammonia in methanol. The ammonium washings were concentrated in vacuo to give 3-(4-(2,7-diazaspiro[3.5]nonan-2-yl)pyrimidin-2-yl)-6-(trifluoromethyl)imidazo[1,2-a]pyrazine (73.4 mg, 47%); ES+ [M+H]=390.0

Step 3: 3-(4-(7-(Methylsulfonyl)-2,7-diazaspiro[3.5]nonan-2-yl)pyrimidin-2-yl)-6-(trifluoromethyl)imidazo[1,2-a]pyrazine

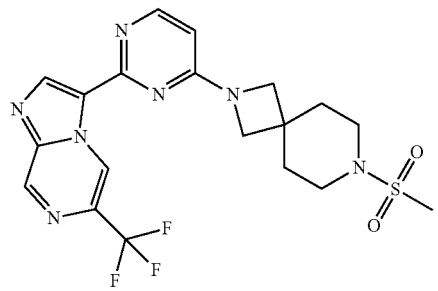 [SMILES: CS(=O)(=O)N1CCC2(CC1)CN(c1ccnc(-c3cnc4cnc(C(F)(F)F)cn34)n1)C2]

3-[4-(2,7-Diazaspiro[3.5]nonan-2-yl)pyrimidin-2-yl]-6-(trifluoromethyl)imidazo[1,2-a]pyrazine (20 mg, 0.048 mmol) and DIPEA (26 µL, 0.15 mmol) were mixed in DCM (1 mL) and methanesulfonyl chloride (4 µL, 0.052 mmol) was added. The reaction was stirred at ambient temperature overnight before being quenched with saturated aq. NaHCO₃, diluted with DCM and the layers separated. The aqueous layer was extracted with DCM (×3) and the combined organics passed through a phase separator cartridge and concentrated in vacuo. Purification by column chromatography (silica, eluting with a 0-15% MeOH in DCM gradient) gave 3-(4-(7-(methylsulfonyl)-2,7-diazaspiro[3.5]nonan-2-yl)pyrimidin-2-yl)-6-(trifluoromethyl)imidazo[1,2-a]pyrazine (12.4 mg, 54%); ¹H NMR (500 MHz, DMSO-d₆) δ 10.35 (dt, J=1.5, 0.8 Hz, 1H), 9.37 (d, J=1.3 Hz, 1H), 8.64 (s, 1H), 8.38 (d, J=5.9 Hz, 1H), 6.41 (d, J=6.0 Hz, 1H), 3.93 (s, 4H), 3.15 (s, 4H), 2.89 (s, 3H), 1.92 (t, J=5.5 Hz, 4H); ES+ [M+H]=468.0.

The following compounds were made using methodology similar to that described in Example 77:

(S)—N-(1-(2-(6-(Difluoromethyl)imidazo[1,2-a]pyrazin-3-yl)pyrimidin-4-yl)pyrrolidin-3-yl)-N-methylmethanesulfonamide IV-125;

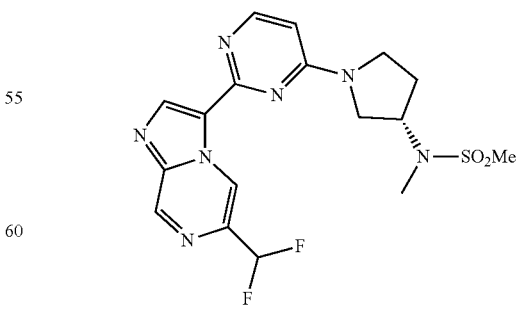

6-(Difluoromethyl)-3-(4-(8-(methylsulfonyl)-3,8-diazabicyclo[3.2.1]octan-3-yl)pyrimidin-2-yl)imidazo[1,2-a]pyrazine IV-126;

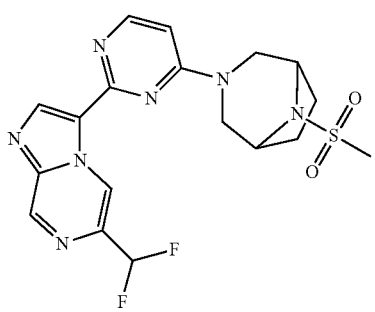 [SMILES: CS(=O)(=O)N1C2CCC1CN(c1ccnc(-c3cnc4cnc(C(F)F)cn34)n1)C2]

N-(1-(2-(6-(Difluoromethyl)imidazo[1,2-a]pyrazin-3-yl)pyrimidin-4-yl)-2-methylpiperidin-3-yl)methanesulfonamide IV-127;

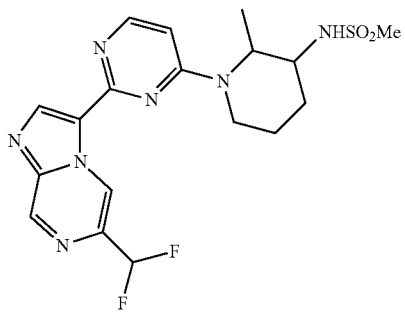

6-(Difluoromethyl)-3-(4-(1-(methylsulfonyl)octahydro-6H-pyrrolo[2,3-a]pyridin-6-yl)pyrimidin-2-yl)imidazo[1,2-a]pyrazine IV-144.

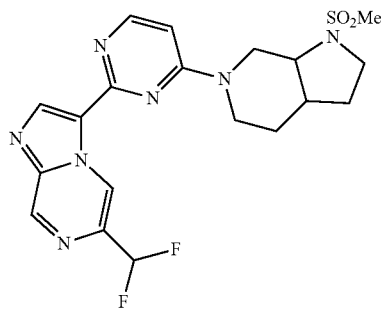

Example 78: N-(1-(2-(6-(Trifluoromethyl)imidazo[1,2-a]pyrazin-3-yl)pyrimidin-4-yl)azepan-4-yl)methanesulfonamide, IV-124

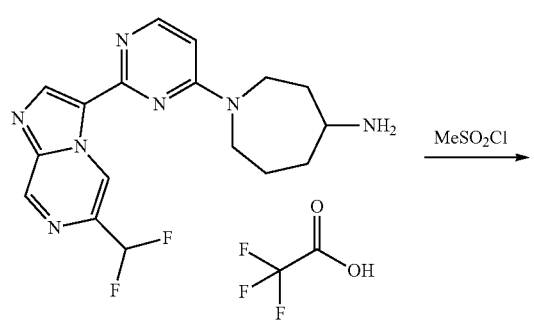

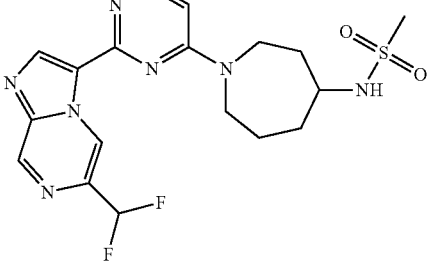

1-[2-[6-(Difluoromethyl)imidazo[1,2-a]pyrazin-3-yl]pyrimidin-4-yl]azepan-4-amine trifluoroacetate (20 mg, 0.0312 mmol) was dissolved in DCM (1 mL). DIPEA (20.3 mg, 27 μL, 0.16 mmol) was added, followed by dropwise addition of methanesulfonyl chloride (5 μL, 0.0628 mmol). The reaction was stirred at ambient temperature for 2 hours before the solvents were removed and the residue purified directly by reverse phase chromatography (C18; MeCN/water—0.05% TFA as eluent) to give N-(1-(2-(6-(trifluoromethyl)imidazo[1,2-a]pyrazin-3-yl)pyrimidin-4-yl)azepan-4-yl)methanesulfonamide (4.4 mg, 32%); $^1$H NMR (400 MHz, Methanol-$d_4$) δ 9.94 (d, J=7.5 Hz, 1H), 9.37-9.32 (m, 1H), 8.81 (s, 1H), 8.30 (d, J=7.4 Hz, 1H), 7.07-6.96 (m, 2H), 4.16 (s, 1H), 3.97 (s, 1H), 3.84 (s, 2H), 3.63 (s, 1H), 2.98 (s, 3H), 2.68 (s, 1H), 2.40 (s, 1H), 2.18 (s, 1H), 2.07 (s, 2H), 2.04 (s, 1H), 1.86-1.75 (m, 1H); ES+ [M+H]=438.6.

The following compounds were made using methodology similar to that described in Example 78:

2-(2-(6-(Difluoromethyl)imidazo[1,2-a]pyrazin-3-yl)pyrimidin-4-yl)-8-(methylsulfonyl)-2,8-diazaspiro[4.5]decane IV-145;

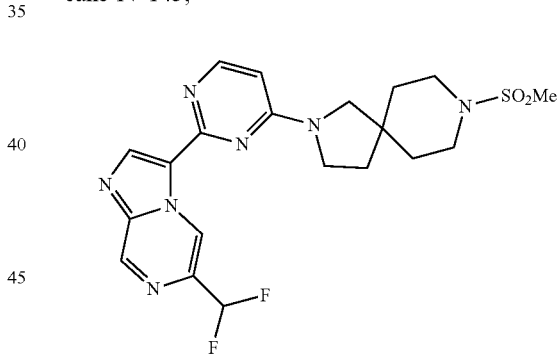

6-(Difluoromethyl)-3-(4-(6-(4-(methylsulfonyl)piperazin-1-yl)pyridin-2-yl)pyrimidin-2-yl)imidazo[1,2-a]pyrazine IV-151;

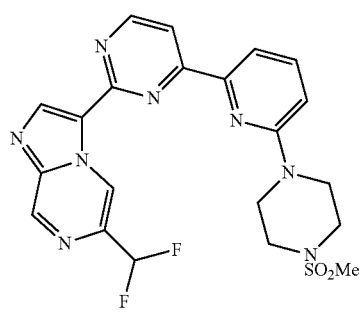

1161

N-((1-(2-(6-(Difluoromethyl)imidazo[1,2-a]pyrazin-3-yl)pyrimidin-4-yl)piperidin-3-yl)methyl)methanesulfonamide IV-152;

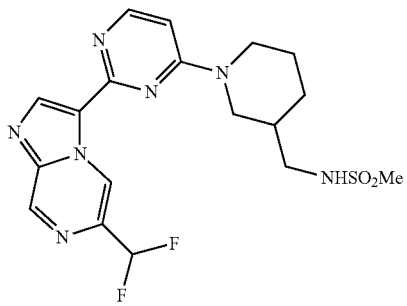

N-(3-(2-(6-(Difluoromethyl)imidazo[1,2-a]pyrazin-3-yl)pyrimidin-4-yl)phenyl)-2-(methylsulfonamido)acetamide IV-173.

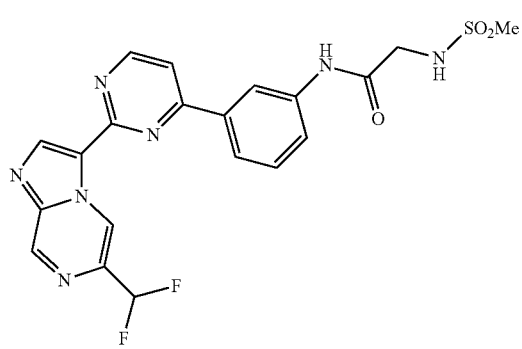 [SMILES: CS(=O)(=O)NCC(=O)Nc1cccc(-c2ccnc(-c3cnc4cnc(C(F)F)cn34)n2)c1]

Example 79: 1-(2-(6-(Difluoromethyl)imidazo[1,2-a]pyrazin-3-yl)pyrimidin-4-yl)-5-methylpiperidine-3-carboxamide, IV-107

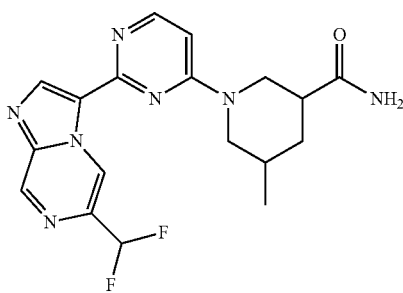 [SMILES: CC1CC(C(N)=O)CN(c2ccnc(-c3cnc4cnc(C(F)F)cn34)n2)C1]

A solution of methyl 1-(2-(6-(difluoromethyl)imidazo[1,2-a]pyrazin-3-yl)pyrimidin-4-yl)-5-methylpiperidine-3-carboxylate (42 mg, 0.10 mmol) and ammonium hydroxide (610 mg, 678 μL, 5.22 mmol) in NMP (0.2 mL) was stirred in a sealed tube at 100° C. for 3 days. The mixture was filtered, diluted with DMSO and purified directly by reverse phase chromatography (C18; MeCN/water—0.05% TFA as eluent) to give 1-(2-(6-(difluoromethyl)imidazo[1,2-a]pyrazin-3-yl)pyrimidin-4-yl)-5-methylpiperidine-3-carboxamide (0.6 mg, 1%); ES+ [M+H]=388.3.

1162

Example 80: 3-(4-(3-((Methylsulfinyl)methyl)pyrrolidin-1-yl)pyrimidin-2-yl)-6-(trifluoromethyl)imidazo[1,2-a]pyrazine and 3-(4-(3-((methylsulfonyl)methyl)pyrrolidin-1-yl)pyrimidin-2-yl)-6-(trifluoromethyl)imidazo[1,2-a]pyrazine, IV-603 and IV-604

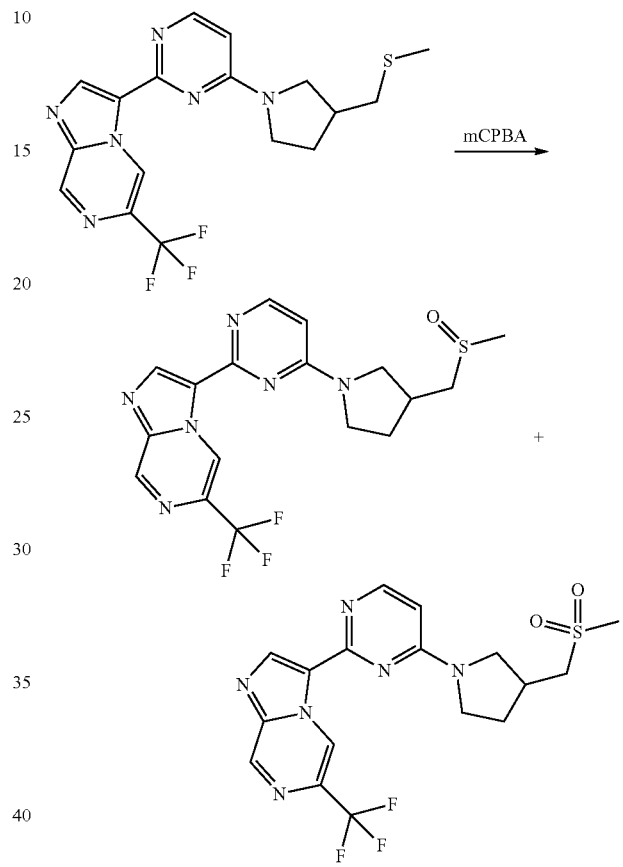

3-(4-(3-((Methylthio)methyl)pyrrolidin-1-yl)pyrimidin-2-yl)-6-(trifluoromethyl)imidazo[1,2-a]pyrazine (40 mg, 0.10 mmol) was dissolved in DCM (3 mL) and the solution cooled to 0° C. m-CPBA (28 mg, 0.11 mmol) was added portionwise over 5 mins and immediately after final addition the reaction was quenched with sodium thiosulphate (2 mL). After stirring for 5 mins the mixture was diluted with DCM (20 mL), the layers separated and the aqueous layer extracted further with DCM (2×20 mL). The combined organics were filtered through a hydrophobic frit and concentrated in vacuo. Purification by reverse phase chromatography (C18; MeCN/water—0.1% ammonium hydroxide as eluent) gave: 3-(4-(3-((methylsulfinyl)methyl)pyrrolidin-1-yl)pyrimidin-2-yl)-6-(trifluoromethyl)imidazo[1,2-a]pyrazine (24 mg, 58%) as a white solid; $^1$H NMR (500 MHz, Methanol-$d_4$) δ 10.40 (s, 1H), 9.10 (dd, J=1.4, 0.8 Hz, 1H), 8.56 (d, J=1.7 Hz, 1H), 8.19 (d, J=6.2 Hz, 1H), 6.38 (dd, J=6.2, 4.5 Hz, 1H), 3.98 (d, J=91.0 Hz, 1H), 3.71 (s, 1H), 3.45 (s, 2H), 2.95 (d, J=6.4 Hz, 2H), 2.82 (s, 1H), 2.63 (s, 3H), 2.35 (s, 1H), 1.92 (s, 1H); ES+ [M+H]=411.0; and 3-(4-(3-((methylsulfonyl)methyl)pyrrolidin-1-yl)pyrimidin-2-yl)-6-(trifluoromethyl)imidazo[1,2-a]pyrazine (4 mg, 9%) as a white solid; $^1$H NMR (500 MHz, DMSO-$d_6$) δ 10.36 (d, J=30.4 Hz, 1H), 9.36 (d, J=1.3 Hz, 1H), 8.66 (d, J=12.8 Hz, 1H), 8.36 (d, J=6.0 Hz, 1H), 6.50 (d, J=7.9 Hz, 1H), 3.96 (d, J=82.8 Hz, 1H), 3.79-3.60 (m, 1H), 3.57 (s, 1H), 3.51-3.36 (m, 2H), 3.32-3.24 (m, 1H), 3.06 (s, 3H), 2.87 (s, 1H), 2.33 (s, 1H), 1.92 (d, J=12.3 Hz, 1H); ES+ [M+H]=427.1.

Example 81: Imino(methyl)((1-(2-(6-(trifluoromethyl)imidazo[1,2-a]pyrazin-3-yl)pyrimidin-4-yl)pyrrolidin-3-yl)methyl)-λ⁶-sulfanone, IV-607

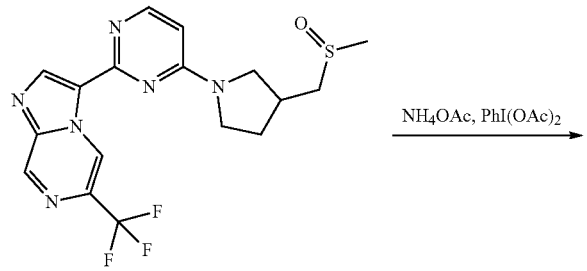

Example 82: ((1-(2-(6-(Difluoromethyl)imidazo[1,2-a]pyrazin-3-yl)pyrimidin-4-yl)-2,5-dimethylpiperidin-3-yl)methyl)(imino)(methyl)-λ⁶-sulfanone, IV-366, IV-367 and IV-368

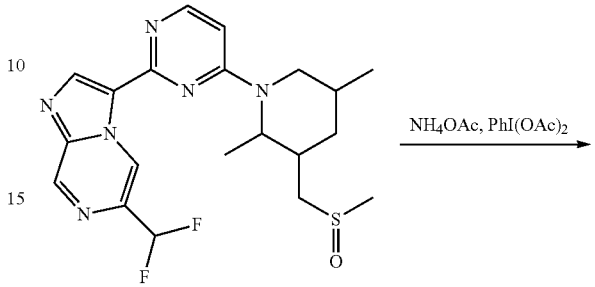

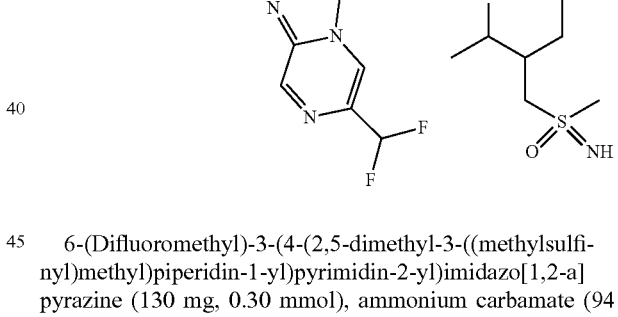

3-(4-(3-((Methylsulfinyl)methyl)pyrrolidin-1-yl)pyrimidin-2-yl)-6-(trifluoromethyl)imidazo[1,2-a]pyrazine (16 mg, 0.039 mmol), ammonium carbamate (13 mg, 0.17 mmol) and (diacetoxyiodo)benzene (38 mg, 0.12 mmol) were dissolved in methanol (400 µL) and DCM (100 µL). The reaction was stirred at ambient temperature in an open flask for 1 hour. The crude mixture was purified by reverse phase chromatography (C18; MeCN/water—0.1% ammonium hydroxide as eluent) to give imino(methyl)((1-(2-(6-(trifluoromethyl)imidazo[1,2-a]pyrazin-3-yl)pyrimidin-4-yl)pyrrolidin-3-yl)methyl)-λ⁶-sulfanone (9 mg, 52%) as a white solid; ¹H NMR (500 MHz, Methanol-d₄) δ 10.47 (s, 1H), 9.20 (d, J=1.3 Hz, 1H), 8.68-8.63 (m, 1H), 8.29 (d, J=6.1 Hz, 1H), 6.50-6.44 (m, 1H), 4.88-4.79 (m, 1H), 4.10 (d, J=111.6 Hz, 1H), 3.88 (s, 1H), 3.70 (s, 1H), 3.65 (s, 1H), 3.54 (s, 2H), 3.14 (s, 3H), 3.02 (s, 1H), 2.48 (s, 1H), 2.04 (dd, J=17.6, 9.7 Hz, 1H); ES+ [M+H]=426.1.

6-(Difluoromethyl)-3-(4-(2,5-dimethyl-3-((methylsulfinyl)methyl)piperidin-1-yl)pyrimidin-2-yl)imidazo[1,2-a]pyrazine (130 mg, 0.30 mmol), ammonium carbamate (94 mg, 1.20 mmol) and (diacetoxyiodo)benzene (293 mg, 0.91 mmol) were dissolved in MeOH (600 µL). The reaction was stirred at ambient temperature in an open flask for 1 hour. The crude mixture was diluted with DMSO and purified by reverse phase chromatography (C18; MeCN/water—0.1% ammonium hydroxide as eluent). Further purification by SFC gave:

((1-(2-(6-(difluoromethyl)imidazo[1,2-a]pyrazin-3-yl)pyrimidin-4-yl)-2,5-dimethylpiperidin-3-yl)methyl)(imino)(methyl)-λ⁶-sulfanone IV-366 (7.5 mg, 5%); ES+ [M+H]= 450.1.

[((1-(2-(6-(difluoromethyl)imidazo[1,2-a]pyrazin-3-yl)pyrimidin-4-yl)-2,5-dimethylpiperidin-3-yl)methyl)(imino)(methyl)-λ⁶-sulfanone IV-367 (8.5 mg, 6%); ES+ [M+H]= 450.1.

((1-(2-(6-(difluoromethyl)imidazo[1,2-a]pyrazin-3-yl)pyrimidin-4-yl)-2,5-dimethylpiperidin-3-yl)methyl)(imino)(methyl)-λ⁶-sulfanone IV-368 (11.9 mg, 8%); ES+ [M+H]= 450.1.

Example 83: (3-(2-(6-(difluoromethyl)imidazo[1,2-a]pyrazin-3-yl)pyrimidin-4-yl)benzyl)(imino)(methyl)-λ⁶-sulfanone, IV-79

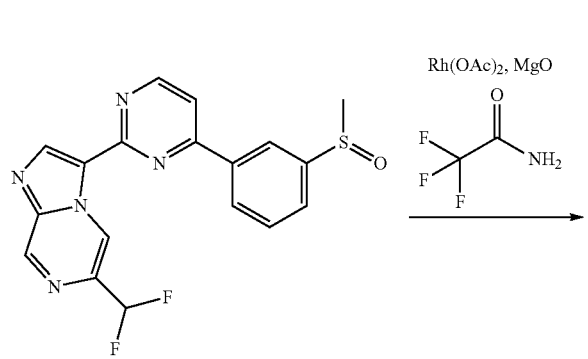

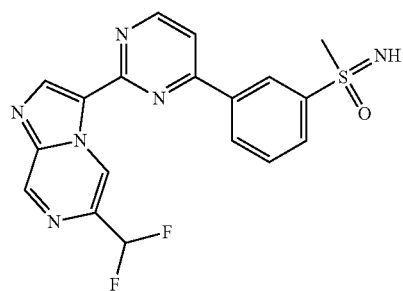

(Diacetoxyiodo)benzene (51.4 mg, 0.16 mmol) was added to a solution of 6-(difluoromethyl)-3-(4-(3-((methylsulfinyl)methyl)phenyl)pyrimidin-2-yl)imidazo[1,2-a]pyrazine (41 mg, 0.11 mmol), MgO (17.2 mg, 0.43 mmol), diacetoxyrhodium (1.2 mg, 0.005 mmol) in DCM (3 mL). 2,2,2-Trifluoroacetamide (24.1 mg, 0.21 mmol) was added and the reaction was stirred at ambient temperature overnight. After addition of further MgO (17.2 mg, 0.43 mmol), diacetoxyrhodium (1.2 mg, 0.005 mmol), (diacetoxyiodo)benzene (51.4 mg, 0.16 mmol) and 2,2,2-trifluoroacetamide (24.1 mg, 0.21 mmol), the reaction was left at ambient temperature for a further 18 hours before being filtered and concentrated in vacuo. The mixture was purified by reverse phase chromatography (C18; MeCN/water—0.1% ammonium hydroxide as eluent), and the trifluoroacetamide protecting group was removed upon standing in the basic solvent, giving (3-(2-(6-(difluoromethyl)imidazo[1,2-a]pyrazin-3-yl)pyrimidin-4-yl)benzyl)(imino)(methyl)-λ⁶-sulfanone (0.6 mg, 1%); ¹H NMR (500 MHz, DMSO-d₆) δ 10.15 (d, J=1.5 Hz, 1H), 9.41 (d, J=1.3 Hz, 1H), 9.14 (d, J=5.3 Hz, 1H), 8.90 (s, 1H), 8.86 (t, J=1.8 Hz, 1H), 8.61 (dt, J=7.9, 1.4 Hz, 1H), 8.22-8.15 (m, 2H), 7.88 (t, J=7.8 Hz, 1H), 7.29 (t, J=54.2 Hz, 1H), 6.32 (s, 2H), 3.22 (d, J=1.1 Hz, 3H); ES+ [M+H]=401.3.

Example 84: 1-(4-(2-(6-(3-(Hydroxymethyl)phenyl)imidazo[1,2-a]pyrazin-3-yl)pyrimidin-4-yl)piperazin-1-yl)ethan-1-one, IV-308

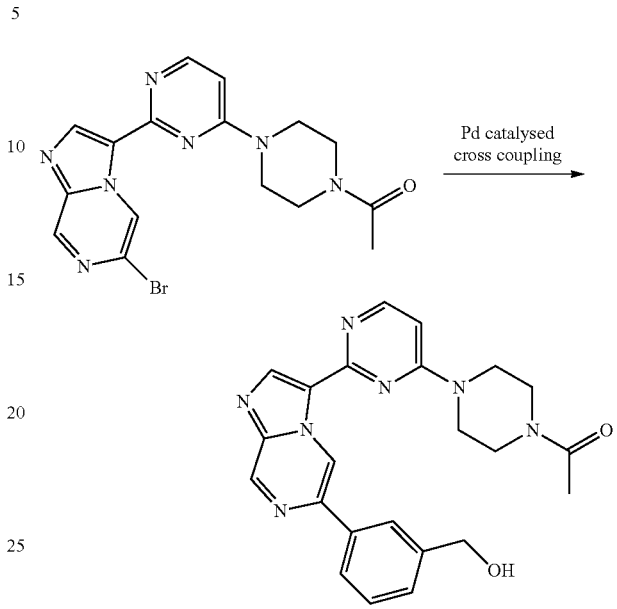

1-(4-(2-(6-Bromoimidazo[1,2-a]pyrazin-3-yl)pyrimidin-4-yl)piperazin-1-yl)ethan-1-one (15 mg, 0.04 mmol), tetrakis(triphenylphosphine)palladium(0) (2.2 mg, 0.002 mmol), aq. Na₂CO₃ (28 µL of 2 M, 0.06 mmol) and [3-(hydroxymethyl)phenyl]boronic acid (6.8 mg, 0.04 mmol) were combined in NMP (1 mL) and heated to 140° C. for 2 hours in the microwave. The mixture was diluted with DMSO (2 mL) and purified directly by reverse phase chromatography (C18; MeCN/water—0.05% TFA as eluent) to give 1-(4-(2-(6-(1-methyl-1H-imidazol-5-yl)imidazo[1,2-a]pyrazin-3-yl)pyrimidin-4-yl)piperazin-1-yl)ethan-1-one as an off-white solid (4.7 mg, 29%); ¹H NMR (400 MHz, methanol-d₄) δ 10.15 (d, J=1.4 Hz, 1H), 9.16 (d, J=1.4 Hz, 1H), 8.54 (s, 1H), 8.34 (d, J=6.2 Hz, 1H), 7.97 (s, 1H), 7.89 (dt, J=7.7, 1.5 Hz, 1H), 7.50 (t, J=7.6 Hz, 1H), 7.43 (dt, J=7.7, 1.4 Hz, 1H), 6.63 (d, J=6.3 Hz, 1H), 3.91 (t, J=5.2 Hz, 2H), 3.83-3.71 (m, 7H), 3.33 (p, J=1.6 Hz, 2H), 2.20 (s, 3H); ES+ [M+H]=430.0

The following intermediates were made using methodology similar to that described in Example 84:

3-(4-(Methylthio)pyrimidin-2-yl)-6-(pyridin-4-yl)imidazo[1,2-a]pyrazine;

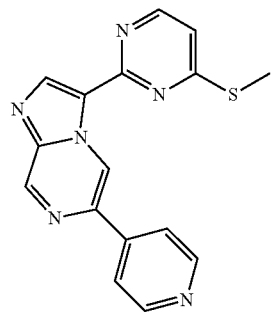 [SMILES: CSc1ccnc(-c2cnc3cnc(-c4ccncc4)cn23)n1]

3-(4-(Methylthio)pyrimidin-2-yl)-6-(1H-pyrazol-3-yl)imidazo[1,2-a]pyrazine;

1167

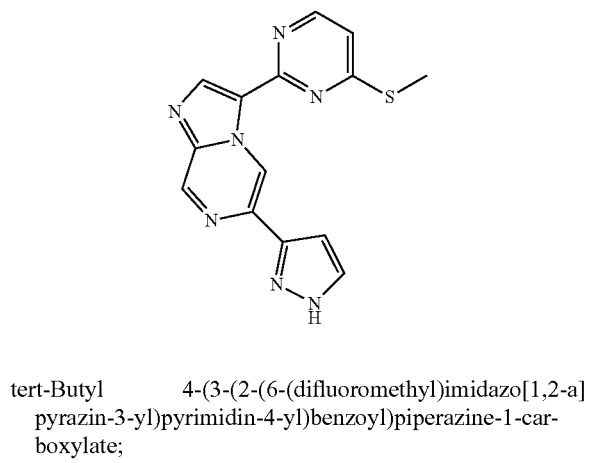

tert-Butyl 4-(3-(2-(6-(difluoromethyl)imidazo[1,2-a]pyrazin-3-yl)pyrimidin-4-yl)benzoyl)piperazine-1-carboxylate;

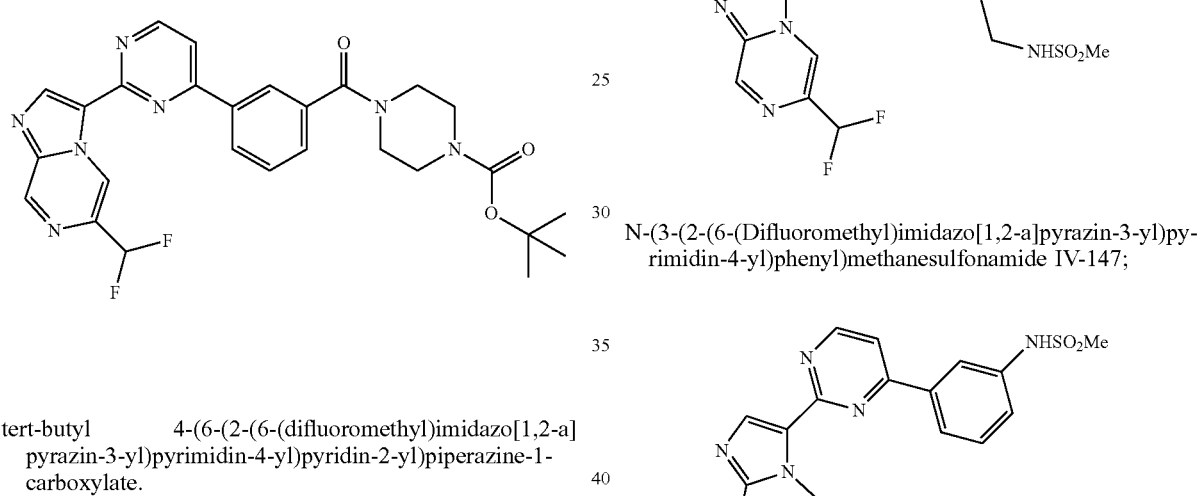

tert-butyl 4-(6-(2-(6-(difluoromethyl)imidazo[1,2-a]pyrazin-3-yl)pyrimidin-4-yl)pyridin-2-yl)piperazine-1-carboxylate.

The following compounds were made using methodology similar to that described in Example 84:

1-(4-(2-(6-Vinylimidazo[1,2-a]pyrazin-3-yl)pyrimidin-4-yl)piperazin-1-yl)ethan-1-one IV-37;

1168

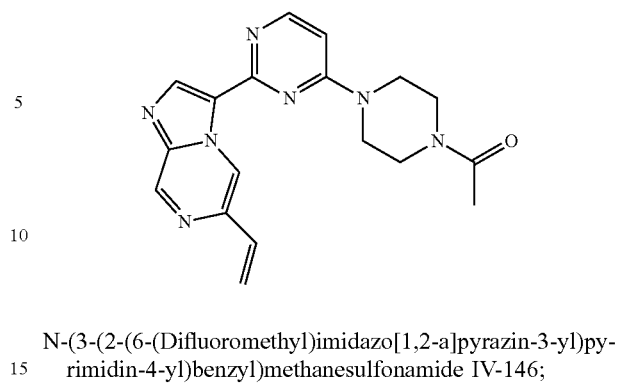

N-(3-(2-(6-(Difluoromethyl)imidazo[1,2-a]pyrazin-3-yl)pyrimidin-4-yl)benzyl)methanesulfonamide IV-146;

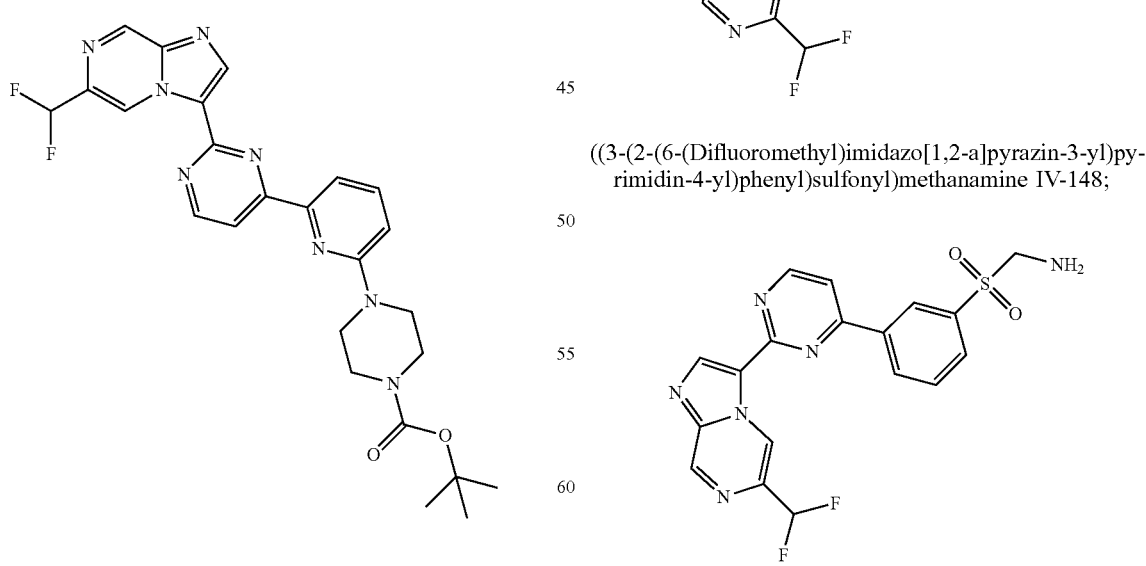

N-(3-(2-(6-(Difluoromethyl)imidazo[1,2-a]pyrazin-3-yl)pyrimidin-4-yl)phenyl)methanesulfonamide IV-147;

((3-(2-(6-(Difluoromethyl)imidazo[1,2-a]pyrazin-3-yl)pyrimidin-4-yl)phenyl)sulfonyl)methanamine IV-148;

6-(Difluoromethyl)-3-(4-(3-((4-methylpiperazin-1-yl)methyl)phenyl)pyrimidin-2-yl)imidazo[1,2-a]pyrazine IV-166;

1169

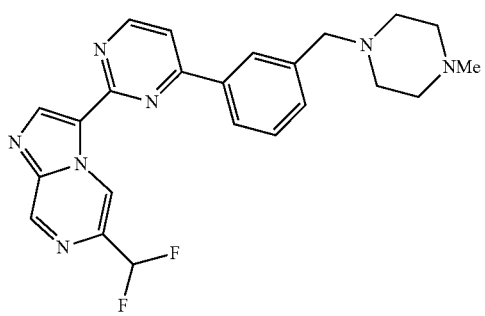 [SMILES: CN1CCN(Cc2cccc(-c3ccnc(-c4cnc5cnc(C(F)F)cn45)n3)c2)CC1]

1-(4-(2-(6-(Pyridin-3-yl)imidazo[1,2-a]pyrazin-3-yl)pyrimidin-4-yl)piperazin-1-yl)ethan-1-one IV-289;

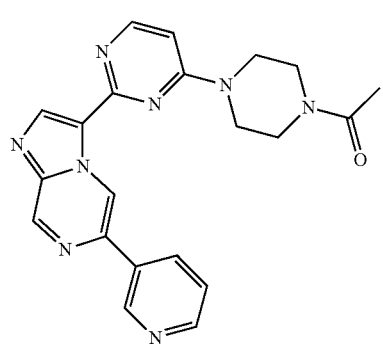 [SMILES: CC(=O)N1CCN(c2ccnc(-c3cnc4cnc(-c5cccnc5)cn34)n2)CC1]

1-(4-(2-(6-Phenylimidazo[1,2-a]pyrazin-3-yl)pyrimidin-4-yl)piperazin-1-yl)ethan-1-one IV-297;

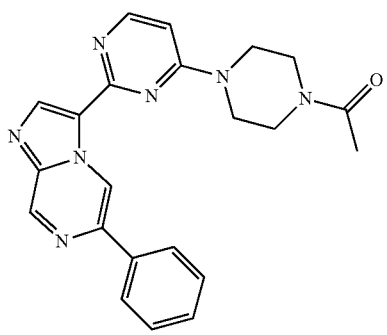 [SMILES: CC(=O)N1CCN(c2ccnc(-c3cnc4cnc(-c5ccccc5)cn34)n2)CC1]

N-(4-(3-(4-(4-Acetylpiperazin-1-yl)pyrimidin-2-yl)imidazo[1,2-a]pyrazin-6-yl)phenyl)acetamide IV-298;

1170

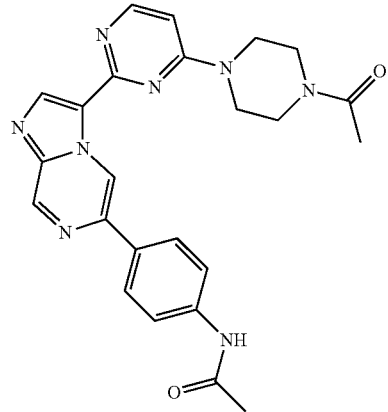 [SMILES: CC(=O)Nc1ccc(-c2cn3c(-c4nccc(N5CCN(C(C)=O)CC5)n4)cnc3cn2)cc1]

1-(4-(2-(6-(3-Ethoxyphenyl)imidazo[1,2-a]pyrazin-3-yl)pyrimidin-4-yl)piperazin-1-yl)ethan-1-one IV-299;

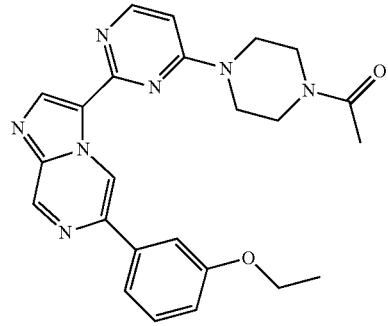 [SMILES: CCOc1cccc(-c2cn3c(-c4nccc(N5CCN(C(C)=O)CC5)n4)cnc3cn2)c1]

1-(4-(2-(6-(3-Methyl-1H-pyrazol-4-yl)imidazo[1,2-a]pyrazin-3-yl)pyrimidin-4-yl)piperazin-1-yl)ethan-1-one IV-300;

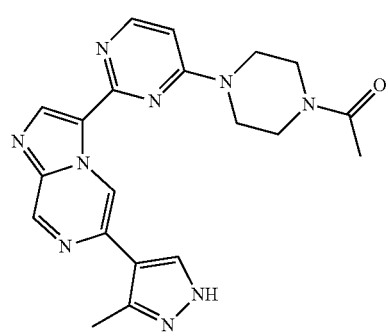 [SMILES: CC(=O)N1CCN(c2ccnc(-c3cnc4cnc(-c5c[nH]nc5C)cn34)n2)CC1]

2-(3-(4-(4-Acetylpiperazin-1-yl)pyrimidin-2-yl)imidazo[1,2-a]pyrazin-6-yl)benzonitrile IV-301;

1171

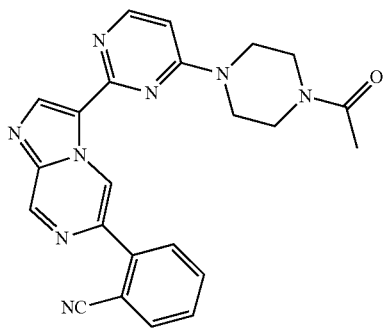 [SMILES: CC(=O)N1CCN(c2ccnc(-c3cnc4cnc(-c5ccccc5C#N)cn34)n2)CC1]

1-(4-(2-(6-(4-(Hydroxymethyl)phenyl)imidazo[1,2-a]
pyrazin-3-yl)pyrimidin-4-yl)piperazin-1-yl)ethan-1-one
IV-302;

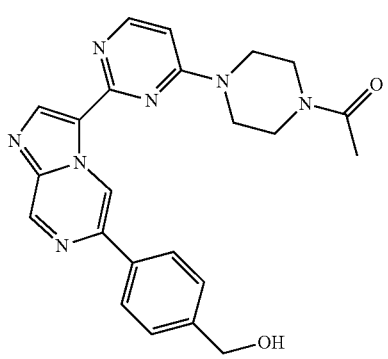 [SMILES: CC(=O)N1CCN(c2ccnc(-c3cnc4cnc(-c5ccc(CO)cc5)cn34)n2)CC1]

4-(3-(4-(4-Acetylpiperazin-1-yl)pyrimidin-2-yl)imidazo[1,
2-a]pyrazin-6-yl)benzamide IV-303;

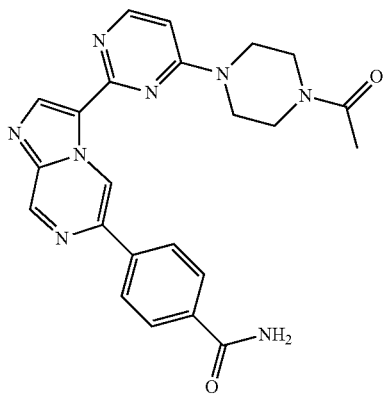 [SMILES: CC(=O)N1CCN(c2ccnc(-c3cnc4cnc(-c5ccc(C(N)=O)cc5)cn34)n2)CC1]

1-(4-(2-(6-(1,3-Dimethyl-1H-pyrazol-4-yl)imidazo[1,2-a]
pyrazin-3-yl)pyrimidin-4-yl)piperazin-1-yl)ethan-1-one
IV-307;

1172

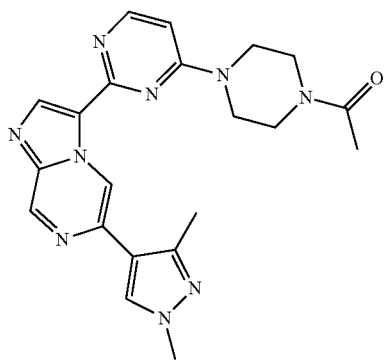 [SMILES: CC(=O)N1CCN(c2ccnc(-c3cnc4cnc(-c5cn(C)nc5C)cn34)n2)CC1]

1-(4-(2-(6-(3-Hydroxyphenyl)imidazo[1,2-a]pyrazin-3-yl)
pyrimidin-4-yl)piperazin-1-yl)ethan-1-one IV-309;

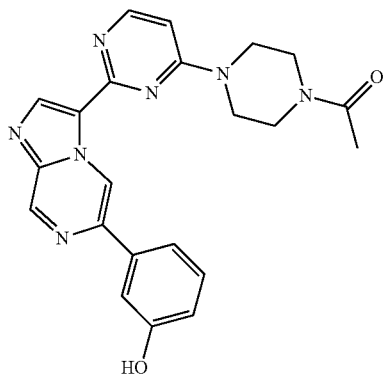 [SMILES: CC(=O)N1CCN(c2ccnc(-c3cnc4cnc(-c5cccc(O)c5)cn34)n2)CC1]

2-(4-(2-(6-(Trifluoromethyl)imidazo[1,2-a]pyrazin-3-yl)py-
rimidin-4-yl)-1H-pyrazol-1-yl)ethan-1-ol IV-431;

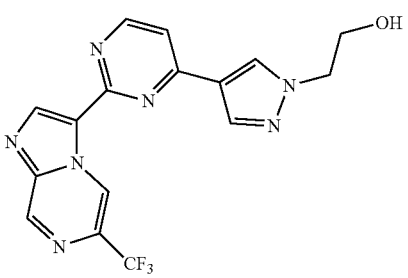 [SMILES: OCCn1cc(-c2ccnc(-c3cnc4cnc(C(F)(F)F)cn34)n2)cn1]

3-(4-(1-(Tetrahydro-2H-pyran-4-yl)-1H-pyrazol-4-yl)py-
rimidin-2-yl)-6-(trifluoromethyl)imidazo[1,2-a]pyrazine
IV-448;

1173

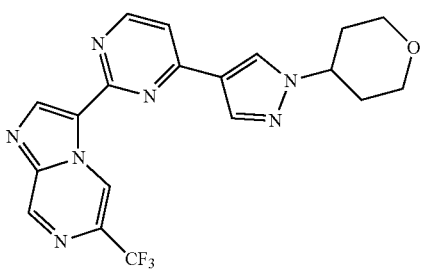 [SMILES: FC(F)(F)c1cn2c(-c3nccc(-c4cnn(C5CCOCC5)c4)n3)cnc2cn1]

3-(4-(1-(Tetrahydrofuran-3-yl)-1H-pyrazol-4-yl)pyrimidin-2-yl)-6-(trifluoromethyl)imidazo[1,2-a]pyrazine IV-449.

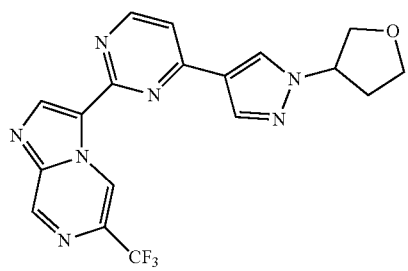 [SMILES: FC(F)(F)c1cn2c(-c3nccc(-c4cnn(C5CCOC5)c4)n3)cnc2cn1]

Example 85: (3-(2-(6-(Difluoromethyl)imidazo[1,2-a]pyrazin-3-yl)pyrimidin-4-yl)phenyl)(piperazin-1-yl)methanone, IV-150

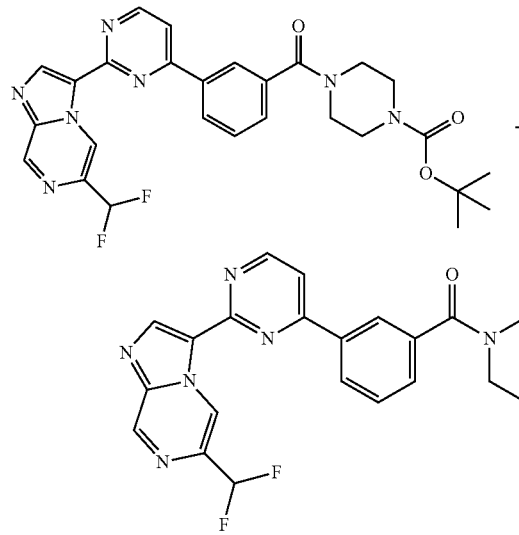

tert-Butyl 4-(3-(2-(6-(difluoromethyl)imidazo[1,2-a]pyrazin-3-yl)pyrimidin-4-yl)benzoyl)piperazine-1-carboxylate (20 mg, 0.037 mmol) was dissolved in DCM (1 mL) and TFA (0.1 mL) was added. After stirring at ambient temperature for 3 hours, the reaction mixture was concentrated in vacuo to give (3-(2-(6-(difluoromethyl)imidazo[1,2-a]pyrazin-3-yl)pyrimidin-4-yl)phenyl)(piperazin-1-yl)methanone trifluoroacetate (2.2 mg, 11%); ES+ [M+H]=436.3.

The following compound was made using methodology similar to that described in Example 85:

1174

6-(Difluoromethyl)-3-(4-(6-(piperazin-1-yl)pyridin-2-yl)pyrimidin-2-yl)imidazo[1,2-a]pyrazine IV-149.

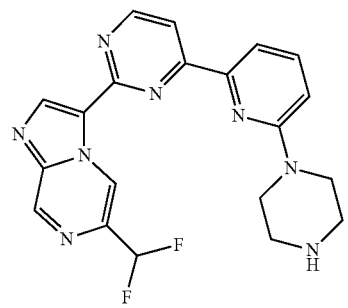 [SMILES: FC(F)c1cn2c(-c3nccc(-c4cccc(N5CCNCC5)n4)n3)cnc2cn1]

Example 86: Cis-6-Bromo-3-(4-(4-ethyl-2-methyl-3-(1H-pyrazol-4-yl)piperazin-1-yl)pyrimidin-2-yl)imidazo[1,2-a]pyrazine, IV-390

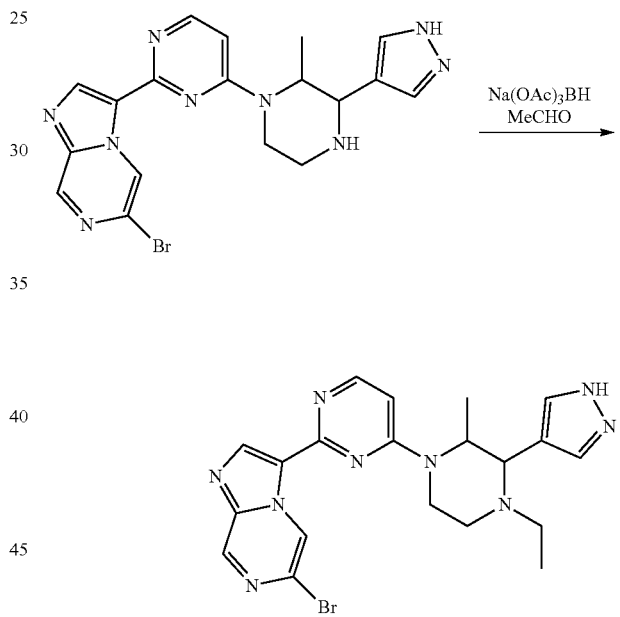

A microwave vial was charged with 6-bromo-3-(4-(2-methyl-3-(1H-pyrazol-4-yl)piperazin-1-yl)pyrimidin-2-yl)imidazo[1,2-a]pyrazine (20 mg, 0.045 mmol), acetaldehyde (20 μL, 0.36 mmol) and AcOH (5 μL, 0.09 mmol) in THF (0.5 mL). The reaction was stirred at ambient temperature for 10 mins before Na(OAc)$_3$BH (238 mg, 1.12 mmol) was added. After 1 hour the reaction mixture was filtered, diluted with DMSO and purified directly by reverse phase chromatography (C18; MeCN/water—0.1% ammonium hydroxide as eluent) to give 6-bromo-3-[4-[4-ethyl-2-methyl-3-(1H-pyrazol-4-yl)piperazin-1-yl]pyrimidin-2-yl]imidazo[1,2-a]pyrazine (7.9 mg, 37%); ES+ [M+H]=470.3.

The following compounds were made using methodology similar to that described in Example 86:

Cis-6-Bromo-3-(4-(4-ethyl-3-methyl-2-(1H-pyrazol-4-yl)piperazin-1-yl)pyrimidin-2-yl)imidazo[1,2-a]pyrazine IV-391;

1175

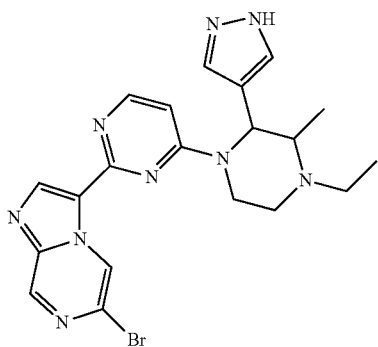 [SMILES: CCN1CCN(c2ccnc(-c3cnc4cnc(Br)cn34)n2)C(c2cn[nH]c2)C1C]

Cis-6-Bromo-3-(4-(2,4-dimethyl-3-(1H-pyrazol-4-yl)piperazin-1-yl)pyrimidin-2-yl)imidazo[1,2-a]pyrazine IV-392;

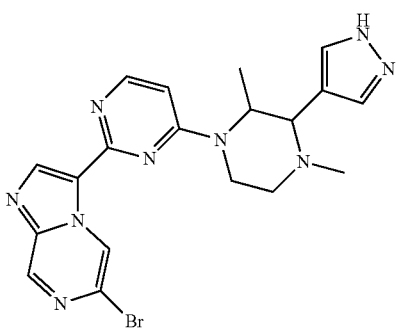 [SMILES: CC1C(c2cn[nH]c2)N(C)CCN1c1ccnc(-c2cnc3cnc(Br)cn23)n1]

Cis-6-Bromo-3-(4-(3,4-dimethyl-2-(1H-pyrazol-4-yl)piperazin-1-yl)pyrimidin-2-yl)imidazo[1,2-a]pyrazine IV-393.

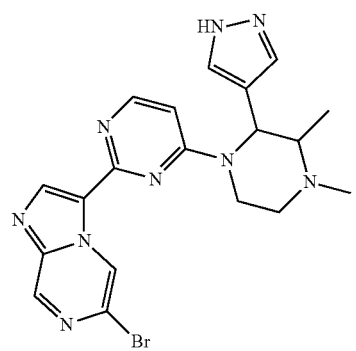 [SMILES: CC1C(c2cn[nH]c2)N(c2ccnc(-c3cnc4cnc(Br)cn34)n2)CCN1C]

The following compounds were made using methodology similar to that described in Example 86 and further purified by chiral SFC:

Cis-6-Bromo-3-(4-(4-ethyl-2-methyl-3-(1H-pyrazol-4-yl) piperazin-1-yl)pyrimidin-2-yl)imidazo[1,2-a]pyrazine IV-401;

1176

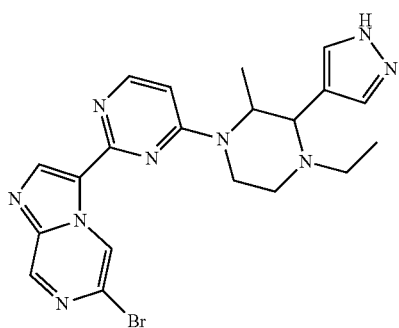 [SMILES: CCN1CCN(c2ccnc(-c3cnc4cnc(Br)cn34)n2)C(C)C1c1cn[nH]c1]

Cis-6-Bromo-3-(4-(4-ethyl-2-methyl-3-(1H-pyrazol-4-yl) piperazin-1-yl)pyrimidin-2-yl)imidazo[1,2-a]pyrazine IV-402;

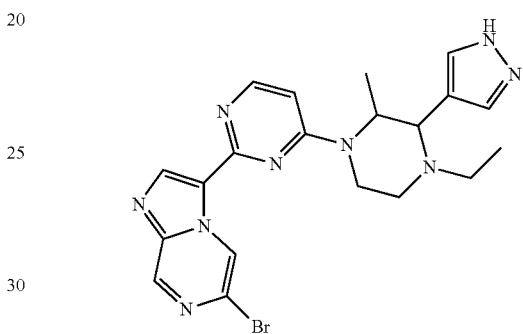

Example 87: 3-(6-(1H-Indol-6-yl)pyridin-2-yl)imidazo[1,2-a]pyrazine, IV-1

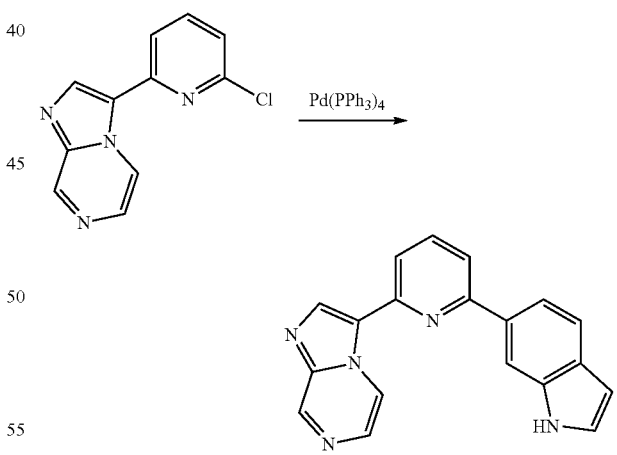

3-(6-Chloropyridin-2-yl)imidazo[1,2-a]pyrazine (35 mg, 0.152 mmol), 1H-indol-4-ylboronic acid (29.3 mg, 0.18 mmol), tetrakis(triphenylphosphine)palladium(0) (8.8 mg, 0.008 mmol), 2 M aq. $Na_2CO_3$ (228 μL, 0.46 mmol) and dioxane (1 mL) were mixed together and heated for 16 hours at 90° C. The mixture was diluted with EtOAc and washed with water and brine. The organic layer was dried ($MgSO_4$) and concentrated in vacuo. Purification by reverse phase chromatography (C18; MeCN/water/0.05% TFA as eluent) gave 3-(6-(1H-indol-6-yl)pyridin-2-yl)imidazo[1,2-a]pyrazine as a pale yellow solid (11 mg, 22%); $^1$H NMR (400 MHz, DMSO-d$_6$) δ 11.40 (s, 1H), 9.92 (dd, J=4.7, 1.4 Hz, 1H), 9.23 (d, J=1.4 Hz, 1H), 8.74 (s, 1H), 8.21-7.96 (m, 3H), 7.86 (d, J=6.7 Hz, 1H), 7.66-7.54 (m, 2H), 7.51 (t, J=2.7 Hz, 1H), 7.30 (t, J=7.7 Hz, 1H), 6.87 (s, 1H).

The following intermediate was made using methodology similar to that described in Example 87:

6-(Difluoromethyl)-3-(4-(3-(methylsulfinyl)phenyl)pyrimidin-2-yl)imidazo[1,2-a]pyrazine.

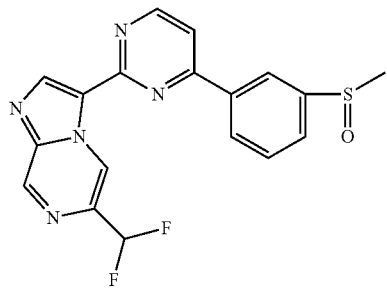 [SMILES: CS(=O)c1cccc(-c2ccnc(-c3cnc4cnc(C(F)F)cn34)n2)c1]

The following compounds were made using methodology similar to that described in Example 87:

6-(Difluoromethyl)-3-(4-(1-(tetrahydrofuran-3-yl)-1H-pyrazol-4-yl)pyrimidin-2-yl)imidazo[1,2-a]pyrazine IV-153;

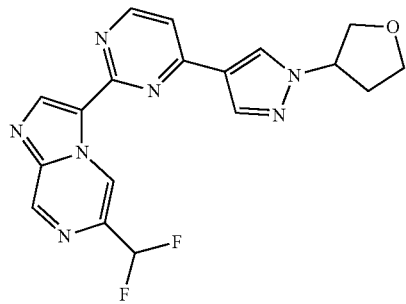 [SMILES: FC(F)c1cn2c(-c3nccc(-c4cnn(C5CCOC5)c4)n3)cnc2cn1]

6-(Difluoromethyl)-3-(4-(1-ethyl-1H-pyrazol-4-yl)pyrimidin-2-yl)imidazo[1,2-a]pyrazine IV-154;

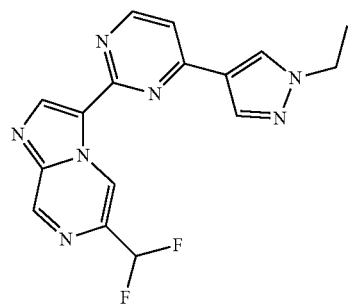 [SMILES: CCn1cc(-c2ccnc(-c3cnc4cnc(C(F)F)cn34)n2)cn1]

2-(3-(2-(6-(Difluoromethyl)imidazo[1,2-a]pyrazin-3-yl)pyrimidin-4-yl)phenyl)acetamide IV-155;

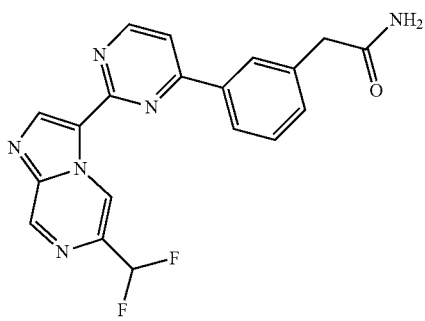 [SMILES: NC(=O)Cc1cccc(-c2ccnc(-c3cnc4cnc(C(F)F)cn34)n2)c1]

1-(4-(2-(6-(Difluoromethyl)imidazo[1,2-a]pyrazin-3-yl)pyrimidin-4-yl)-3,6-dihydropyridin-1(2H)-yl)ethan-1-one IV-156;

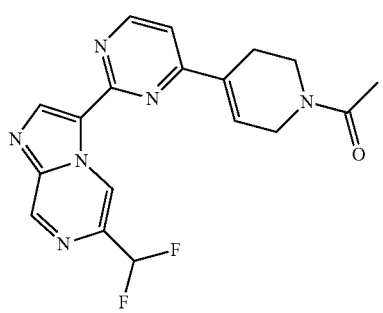 [SMILES: CC(=O)N1CC=C(c2ccnc(-c3cnc4cnc(C(F)F)cn34)n2)CC1]

2-(3-(2-(6-(Difluoromethyl)imidazo[1,2-a]pyrazin-3-yl)pyrimidin-4-yl)phenyl)acetonitrile IV-157;

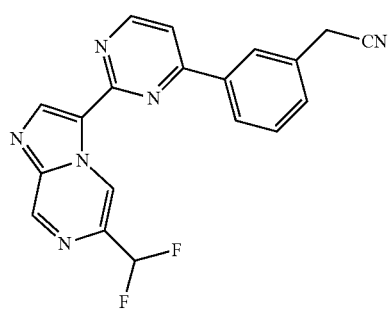 [SMILES: N#CCc1cccc(-c2ccnc(-c3cnc4cnc(C(F)F)cn34)n2)c1]

6-(Difluoromethyl)-3-(4-(1-methyl-1H-indol-5-yl)pyrimidin-2-yl)imidazo[1,2-a]pyrazine IV-158;

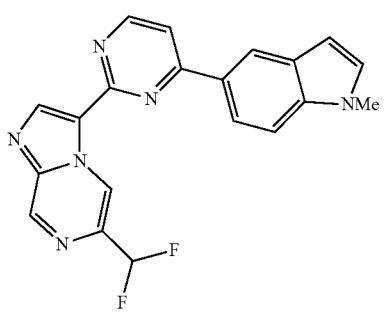 [SMILES: Cn1ccc2cc(-c3ccnc(-c4cnc5cnc(C(F)F)cn45)n3)ccc21]

(3-(2-(6-(Difluoromethyl)imidazo[1,2-a]pyrazin-3-yl)pyrimidin-4-yl)phenyl)methanamine IV-159;

| 1179 | 1180 |
|---|---|
| 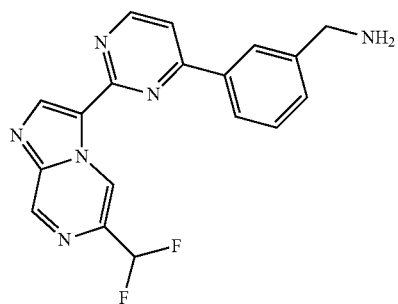 [SMILES: NCc1cccc(-c2ccnc(-c3cnc4cnc(C(F)F)cn34)n2)c1] N-(3-(2-(6-(Difluoromethyl)imidazo[1,2-a]pyrazin-3-yl)pyrimidin-4-yl)benzyl)methanesulfonamide IV-160; | 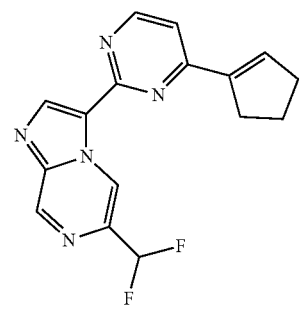 (5-(2-(6-(Difluoromethyl)imidazo[1,2-a]pyrazin-3-yl)pyrimidin-4-yl)thiophen-2-yl)methanol IV-175; |

3-(2-(6-(Difluoromethyl)imidazo[1,2-a]pyrazin-3-yl)pyrimidin-4-yl)phenol IV-161;

3-(2-(6-(Difluoromethyl)imidazo[1,2-a]pyrazin-3-yl)pyrimidin-4-yl)-4-fluorobenzamide IV-176;

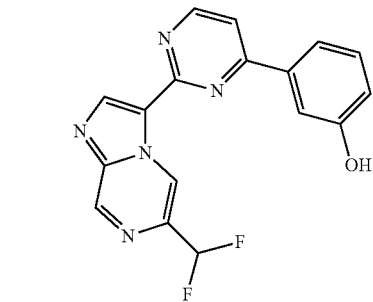 [SMILES: Oc1cccc(-c2ccnc(-c3cnc4cnc(C(F)F)cn34)n2)c1]

(3-(2-(6-(Difluoromethyl)imidazo[1,2-a]pyrazin-3-yl)pyrimidin-4-yl)phenyl)methanol IV-162;

3-(6-(1H-Indol-4-yl)pyridin-2-yl)imidazo[1,2-a]pyrazine-6-carboxamide IV-225;

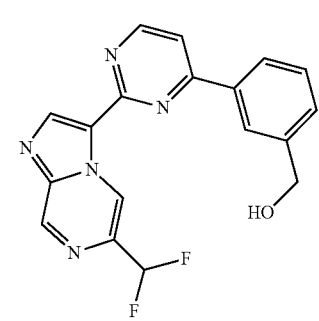 [SMILES: OCc1cccc(-c2ccnc(-c3cnc4cnc(C(F)F)cn34)n2)c1] 3-(4-(Cyclopent-1-en-1-yl)pyrimidin-2-yl)-6-(difluoromethyl)imidazo[1,2-a]pyrazine IV-163;

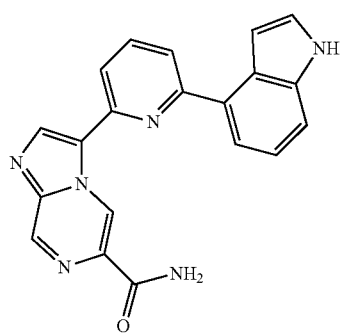 [SMILES: NC(=O)c1cn2c(-c3cccc(-c4cccc5[nH]ccc45)n3)cnc2cn1] 3-(6-(1H-Indol-4-yl)pyridin-2-yl)-6-(difluoromethyl)imidazo[1,2-a]pyrazine IV-233;

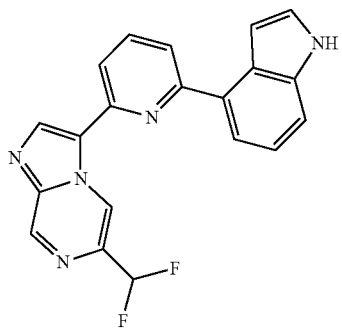 [SMILES: FC(F)c1cn2c(-c3cccc(-c4cccc5[nH]ccc45)n3)cnc2cn1]

3-(6-(1H-Indol-4-yl)pyridin-2-yl)imidazo[1,2-a]pyrazine-6-carbonitrile IV-234.

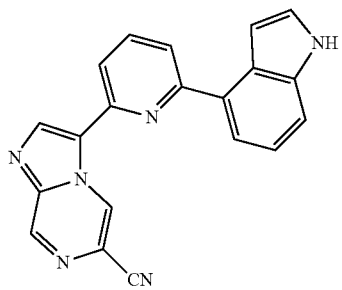 [SMILES: N#Cc1cn2c(-c3cccc(-c4cccc5[nH]ccc45)n3)cnc2cn1]

Example 88: (3-(2-(6-(difluoromethyl)imidazo[1,2-a]pyrazin-3-yl)pyrimidin-4-yl)phenyl)(imino)(methyl)-$\lambda^6$-sulfanone, IV-79

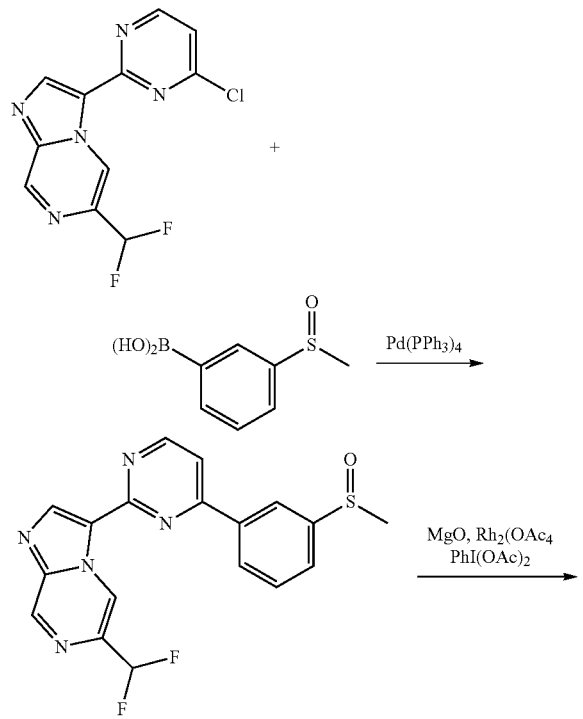

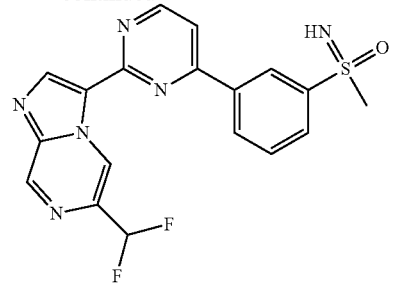 [SMILES: CS(=N)(=O)c1cccc(-c2ccnc(-c3cnc4cnc(C(F)F)cn34)n2)c1]

Step 1: 6-(Difluoromethyl)-3-(4-(3-(methylsulfinyl)phenyl)pyrimidin-2-yl)imidazo[1,2-a]pyrazine

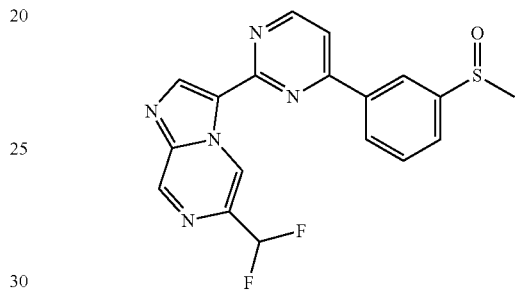

A mixture of 3-(4-chloropyrimidin-2-yl)-6-(difluoromethyl)imidazo[1,2-a]pyrazine (30 mg, 0.107 mmol), (3-methylsulfinylphenyl)boronic acid (19.6 mg, 0.11 mmol), 2 M NaHCO₃ (266 μL, 0.53 mmol) and tetrakis(triphenylphosphine)palladium(0) (12.3 mg, 0.011 mmol) in dioxane (3 mL) was heated at 60° C. for 3 hours before being concentrated in vacuo. The residue was partitioned between DCM and water and the organic extract was dried (MgSO₄) and concentrated in vacuo to give 6-(difluoromethyl)-3-(4-(3-(methylsulfinyl)phenyl)pyrimidin-2-yl)imidazo[1,2-a]pyrazine, which was used without further purification.

Step 2: (3-(2-(6-(Difluoromethyl)imidazo[1,2-a]pyrazin-3-yl)pyrimidin-4-yl)phenyl)(imino)(methyl)-$\lambda^6$-sulfanone

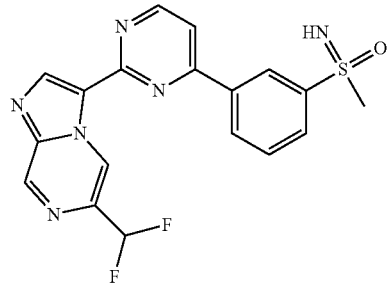

To a mixture of 6-(difluoromethyl)-3-(4-(3-(methylsulfinyl)phenyl)pyrimidin-2-yl)imidazo[1,2-a]pyrazine (41 mg, 0.11 mmol), magnesium oxide (17.2 mg, 0.43 mmol), diacetoxyrhodium (1.2 mg, 0.0053 mmol) in DCM (3 mL) was added (diacetoxyiodo)benzene (51.4 mg, 0.16 mmol) and 2,2,2-trifluoroacetamide (24.1 mg, 0.21 mmol). The mixture was stirred for 16 hours before addition of additional magnesium oxide (17.2 mg, 0.43 mmol), diacetoxyrhodium (1.2 mg, 0.0053 mmol), (diacetoxyiodo)benzene (51.4 mg, 0.16 mmol), 2,2,2-trifluoroacetamide (24.1 mg, 0.21 mmol). The reaction was stirred for a further 24 hours before being filtered and concentrated in vacuo. The residue was purified directly by reverse phase chromatography (C18; MeCN/water—0.1% ammonium hydroxide as eluent). The fractions were left standing in the basic media, causing deprotection of the trifluoroacetamide group, giving (3-(2-(6-(difluoromethyl)imidazo[1,2-a]pyrazin-3-yl)pyrimidin-4-yl)phenyl)(imino)(methyl)-λ⁶-sulfanone (0.6 mg, 1.1% over two steps); ¹H NMR (500 MHz, DMSO-d₆) δ 10.15 (d, J=1.5 Hz, 1H), 9.41 (d, J=1.3 Hz, 1H), 9.14 (d, J=5.3 Hz, 1H), 8.90 (s, 1H), 8.86 (t, J=1.8 Hz, 1H), 8.61 (dt, J=7.9, 1.4 Hz, 1H), 8.22-8.15 (m, 2H), 7.88 (t, J=7.8 Hz, 1H), 7.29 (t, J=54.2 Hz, 1H), 6.32 (s, 2H), 3.22 (d, J=1.1 Hz, 3H); ES+ [M+H]=401.3.

Example 89: 3-(4-(3-((1H-Pyrazol-4-yl)methyl)pyrrolidin-1-yl)pyrimidin-2-yl)-6-(trifluoromethyl)imidazo[1,2-a]pyrazine, IV-635

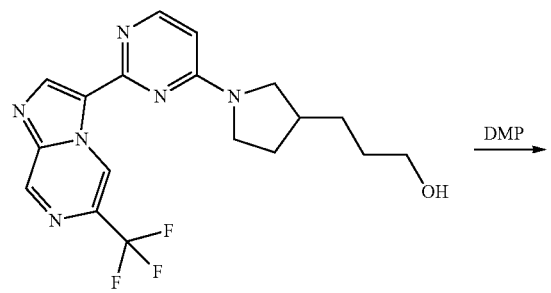

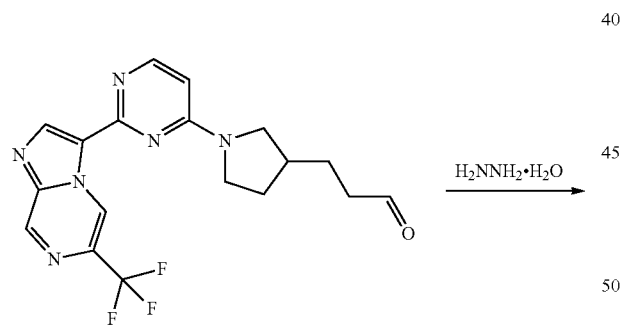

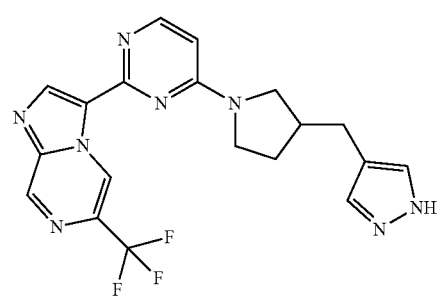

Step 1: 3-(1-(2-(6-(Trifluoromethyl)imidazo[1,2-a]pyrazin-3-yl)pyrimidin-4-yl)pyrrolidin-3-yl)propanal

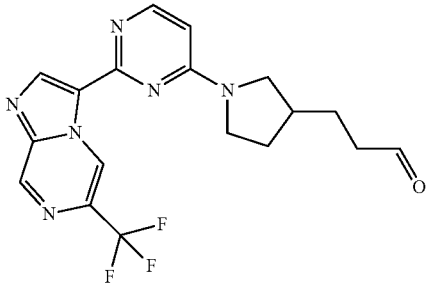 [SMILES: O=CCCC1CCN(c2ccnc(-c3cnc4cnc(C(F)(F)F)cn34)n2)C1]

3-[1-[2-[6-(Trifluoromethyl)imidazo[1,2-a]pyrazin-3-yl]pyrimidin-4-yl]pyrrolidin-3-yl]propan-1-ol (552 mg, 1.41 mmol) was suspended in DCM (50 mL) and the mixture cooled to 0° C. Dess-Martin periodinane (660 mg, 1.56 mmol) was added and the reaction mixture allowed to warm to ambient temperature overnight. The reaction was quenched by addition of a 1:1 mixture of saturated aq. NaHCO₃ and saturated aq. Na₂S₂O₃ (100 mL total) and stirred vigorously for 10 minutes. The layers were separated and the aqueous phase extracted with DCM. The combined organics were washed with brine, dried (Na₂SO₄), filtered and concentrated in vacuo to give 3-(1-(2-(6-(trifluoromethyl)imidazo[1,2-a]pyrazin-3-yl)pyrimidin-4-yl)pyrrolidin-3-yl) (517 mg, 91%) as an off-white solid; ES+ [M+H]= 391.0.

Step 2: 3-(4-(3-((1H-Pyrazol-4-yl)methyl)pyrrolidin-1-yl)pyrimidin-2-yl)-6-(trifluoromethyl)imidazo[1,2-a]pyrazine 3-(1-(2-(6-(Trifluoromethyl)imidazo[1,2-a]pyrazin-3-yl)pyrimidin-4-yl)pyrrolidin-3-yl) (517 mg, 1.29 mmol) was suspended in DMF (10 mL) and warmed to 40° C. DMF-DMA (400 μL, 3.01 mmol) was added and the resulting brown solution stirred overnight at 80° C. before being cooled to ambient temperature and concentrated in vacuo. The residue was suspended in EtOH (10 mL) and hydrazine hydrate (130 μL, 2.65 mmol) was added, and the mixture heated to 45° C. After 3 hours the reaction mixture was cooled to ambient temperature and the solvent removed in vacuo. The residue was taken up in DMSO and purified directly by reverse phase chromatography (C18; MeCN/water—0.05% TFA as eluent) to give 3-(4-(3-((1H-pyrazol-4-yl)methyl)pyrrolidin-1-yl)pyrimidin-2-yl)-6-(trifluoromethyl)imidazo[1,2-a]pyrazine, (17.4 mg, 3%) as a pale yellow solid; ¹H NMR (500 MHz, DMSO-d₆) δ 12.58 (s, 1H), 10.38 (d, J=13.3 Hz, 1H), 9.36 (d, J=1.3 Hz, 1H), 8.66 (s, 1H), 8.32 (d, J=5.6 Hz, 1H), 7.58 (br s, 1H), 7.40 (br s, 1H), 6.50 (d, J=6.0 Hz, 1H), 3.92-3.81 (m, 1H), 3.67-3.50 (m, 2H), 3.49-3.34 (m, 1H), 2.63-2.55 (m, 3H), 2.15 (br s, 1H), 1.82-1.70 (m, 1H). ES+ [M+H]=415.0.

Example 90: 2-((6-(2,5-Dimethyl-3-(1H-pyrazol-4-yl)piperazin-1-yl)-2-(6-(trifluoromethyl)imidazo[1,2-a]pyrazin-3-yl)pyrimidin-4-yl)oxy)ethan-1-ol, IV-640

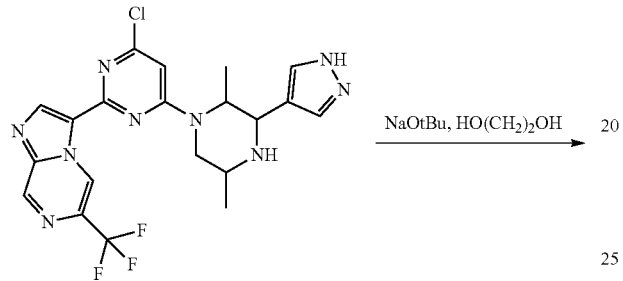

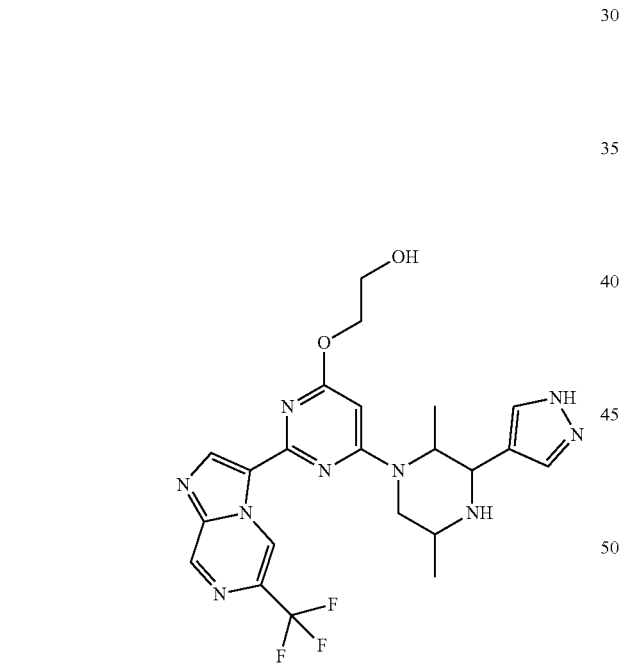

A mixture of 3-[4-chloro-6-[2,5-dimethyl-3-(1H-pyrazol-4-yl)piperazin-1-yl]pyrimidin-2-yl]-6-(trifluoromethyl)imidazo[1,2-a]pyrazine (40 mg, 0.084 mmol), ethylene glycol (15 μL, 0.27 mmol) and sodium tert-butoxide (30 mg, 0.31 mmol) in DME (2 mL) was stirred at 80° C. for 18 hours. The reaction mixture was purified directly by reverse phase chromatography (C18; MeCN/water—0.1% ammonium hydroxide as eluent) to give 2-((6-(2,5-dimethyl-3-(1H-pyrazol-4-yl)piperazin-1-yl)-2-(6-(trifluoromethyl)imidazo[1,2-a]pyrazin-3-yl)pyrimidin-4-yl)oxy)ethan-1-ol (2 mg, 4%); ES+ [M+H]=502.4.

Example 91: 3-(4-(2,5-Dimethyl-3-(1H-pyrazol-4-yl)piperazin-1-yl)-6-methoxypyrimidin-2-yl)-6-(trifluoromethyl)imidazo[1,2-a]pyrazine, IV-593

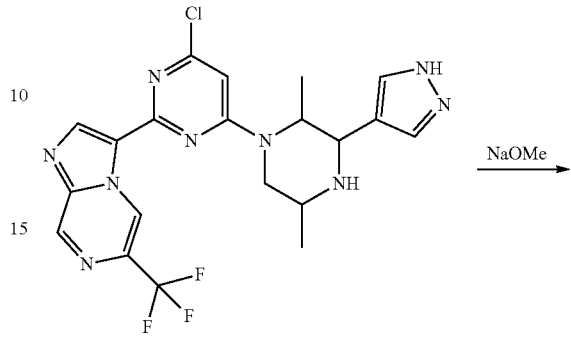

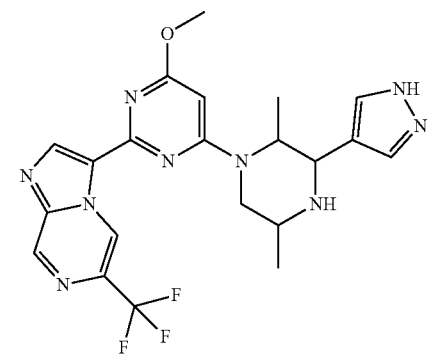

A mixture of 3-[4-chloro-6-[2,5-dimethyl-3-(1H-pyrazol-4-yl)piperazin-1-yl]pyrimidin-2-yl]-6-(trifluoromethyl)imidazo[1,2-a]pyrazine (20 mg, 0.042 mmol) and NaOMe (15 mg, 0.28 mmol) in methanol (500 μL) was stirred at 100° C. for 18 hours. The reaction mixture was allowed to cool to ambient temperature and was purified directly by reverse phase chromatography (C18; MeCN/water—0.1% ammonium hydroxide as eluent) to give 3-[4-[2,5-dimethyl-3-(1H-pyrazol-4-yl)piperazin-1-yl]-6-methoxy-pyrimidin-2-yl]-6-(trifluoromethyl)imidazo[1,2-a]pyrazine (3 mg, 15%); ¹H NMR (500 MHz, Methanol-d₄) δ 10.30 (s, 1H), 9.20 (s, 1H), 8.67 (s, 1H), 7.74 (s, 2H), 6.08 (s, 1H), 5.00-4.80 (masked, 2H), 4.39 (m, 1H), 4.06 (s, 3H), 3.15 (m, 1H), 2.90 (m, 1H), 1.35 (d, 3H), 1.14 (d, 3H); ES+ [M+H]=474.3.

Example 92: ((6-(2,5-Dimethyl-3-(1H-pyrazol-4-yl)piperazin-1-yl)-2-(6-(trifluoromethyl)imidazo[1,2-a]pyrazin-3-yl)pyrimidin-4-yl)imino)dimethyl-λ⁶-sulfanone, IV-648

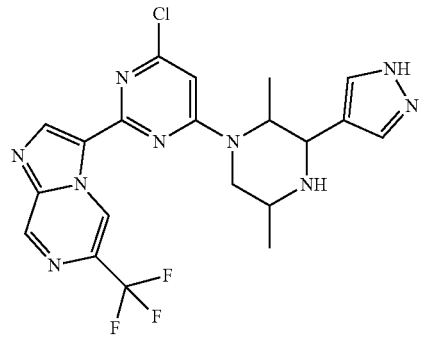

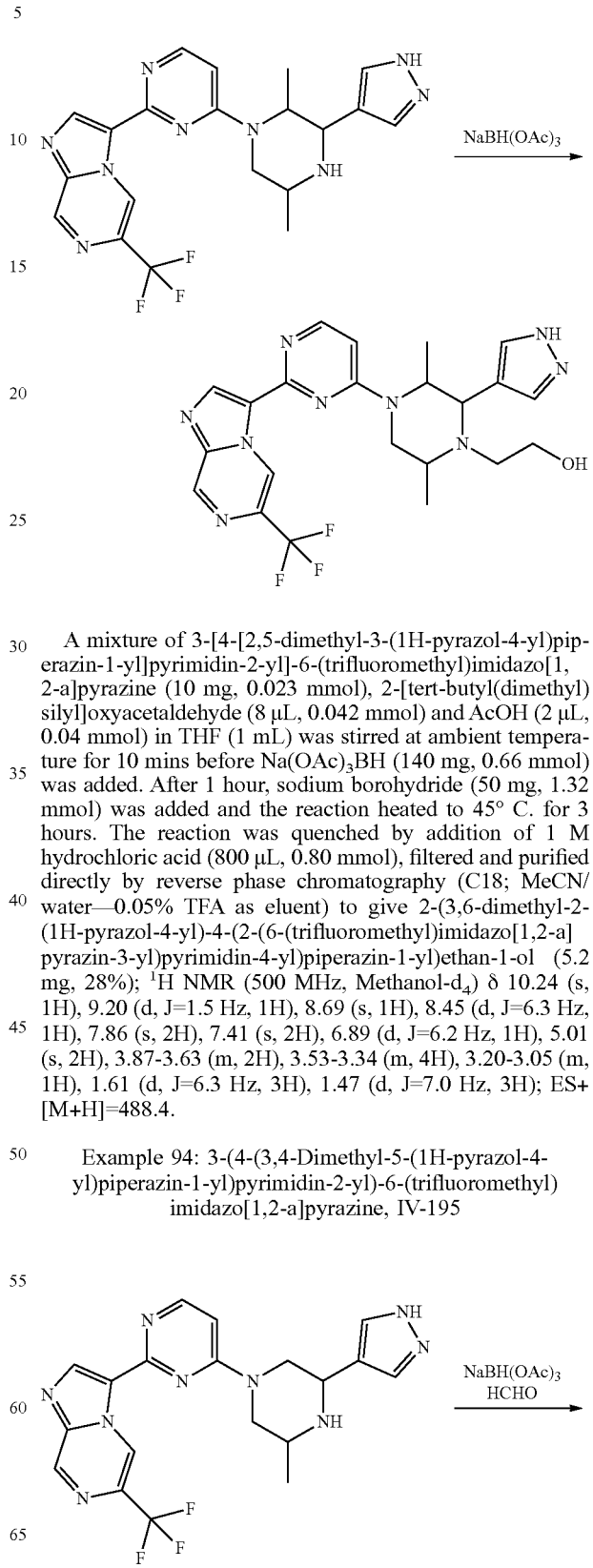

3-[4-Chloro-6-[2,5-dimethyl-3-(1H-pyrazol-4-yl)piperazin-1-yl]pyrimidin-2-yl]-6-(trifluoromethyl)imidazo[1,2-a]pyrazine (50 mg, 0.10 mmol), iminodimethyl-λ⁶-sulfanone (10 mg, 0.10 mmol), Xantphos (6 mg, 0.010 mmol) and cesium carbonate (40 mg, 0.12 mmol) were dissolved in 1,4-dioxane (1 mL), and tris(benzylideneacetone)dipalladium(0) (5 mg, 0.0055 mmol) was added. The reaction mixture was degassed and stirred at reflux for 18 hours before being concentrated in vacuo. Purification by reverse phase chromatography (C18; MeCN/water—0.1% ammonium hydroxide as eluent) gave ((6-(2,5-dimethyl-3-(1H-pyrazol-4-yl)piperazin-1-yl)-2-(6-(trifluoromethyl)imidazo[1,2-a]pyrazin-3-yl)pyrimidin-4-yl)imino)dimethyl-λ⁶-sulfanone (10 mg, 17%); ¹H NMR (400 MHz, DMSO-d₆) δ 12.68 (s, 1H), 10.32 (m, 1H), 9.34 (m, 1H), 8.66 (m, 1H), 7.70-7.48 (m, 2H), 5.97 (m, 1H), 5.01-4.71 (m, 1H), 4.05 (m, 2H), 3.45 (m, 6H), 2.85 (m, 1H), 2.50 (masked, 2H), 1.16 (m, 3H), 0.91 (m, 3H); ES+ [M+H]=535.3.

Example 93: 2-(3,6-Dimethyl-2-(1H-pyrazol-4-yl)-4-(2-(6-(trifluoromethyl)imidazo[1,2-a]pyrazin-3-yl)pyrimidin-4-yl)piperazin-1-yl)ethan-1-ol, IV-636

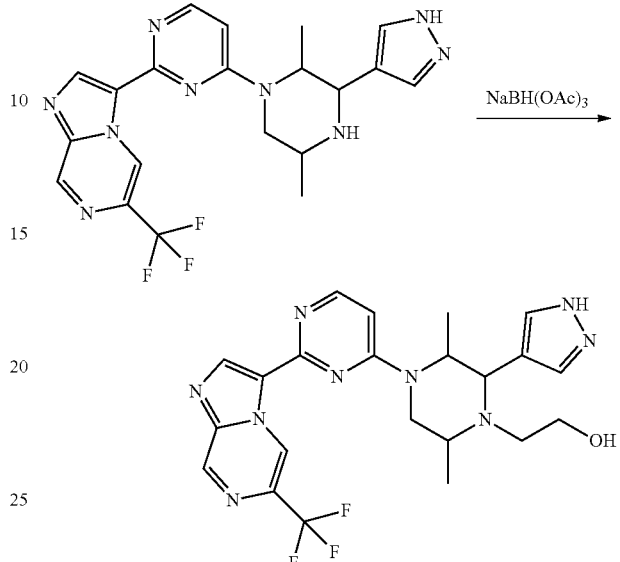

A mixture of 3-[4-[2,5-dimethyl-3-(1H-pyrazol-4-yl)piperazin-1-yl]pyrimidin-2-yl]-6-(trifluoromethyl)imidazo[1,2-a]pyrazine (10 mg, 0.023 mmol), 2-[tert-butyl(dimethyl)silyl]oxyacetaldehyde (8 μL, 0.042 mmol) and AcOH (2 μL, 0.04 mmol) in THF (1 mL) was stirred at ambient temperature for 10 mins before Na(OAc)₃BH (140 mg, 0.66 mmol) was added. After 1 hour, sodium borohydride (50 mg, 1.32 mmol) was added and the reaction heated to 45° C. for 3 hours. The reaction was quenched by addition of 1 M hydrochloric acid (800 μL, 0.80 mmol), filtered and purified directly by reverse phase chromatography (C18; MeCN/water—0.05% TFA as eluent) to give 2-(3,6-dimethyl-2-(1H-pyrazol-4-yl)-4-(2-(6-(trifluoromethyl)imidazo[1,2-a]pyrazin-3-yl)pyrimidin-4-yl)piperazin-1-yl)ethan-1-ol (5.2 mg, 28%); ¹H NMR (500 MHz, Methanol-d₄) δ 10.24 (s, 1H), 9.20 (d, J=1.5 Hz, 1H), 8.69 (s, 1H), 8.45 (d, J=6.3 Hz, 1H), 7.86 (s, 2H), 7.41 (s, 2H), 6.89 (d, J=6.2 Hz, 1H), 5.01 (s, 2H), 3.87-3.63 (m, 2H), 3.53-3.34 (m, 4H), 3.20-3.05 (m, 1H), 1.61 (d, J=6.3 Hz, 3H), 1.47 (d, J=7.0 Hz, 3H); ES+ [M+H]=488.4.

Example 94: 3-(4-(3,4-Dimethyl-5-(1H-pyrazol-4-yl)piperazin-1-yl)pyrimidin-2-yl)-6-(trifluoromethyl)imidazo[1,2-a]pyrazine, IV-195

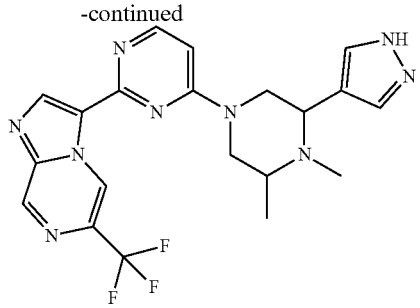

A solution of 3-[4-[3-methyl-5-(1H-pyrazol-4-yl)piperazin-1-yl]pyrimidin-2-yl]-6-(trifluoromethyl)imidazo[1,2-a]pyrazine (9.6 mg, 0.017 mmol), formaldehyde (2.8 mg, 2.6 µL, 0.035 mmol) and AcOH (1.0 mg, 1 µL, 0.017 mmol) in THF (376 µL) was stirred at ambient temperature for 10 mins before Na(OAc)₃BH (7.3 mg, 0.035 mmol) was added. The reaction was stirred at ambient temperature for 10 mins before additional Na(OAc)₃BH (7.3 mg, 0.035 mmol) was added, followed by a further two portions of Na(OAc)₃BH (7.3 mg, 0.035 mmol each) at 10 minute intervals. The reaction mixture was filtered, diluted with DMSO and purified by reverse phase chromatography (C18; MeCN/water—0.05% TFA as eluent) to give 3-(4-(3,4-dimethyl-5-(1H-pyrazol-4-yl)piperazin-1-yl)pyrimidin-2-yl)-6-(trifluoromethyl)imidazo[1,2-a]pyrazine (7.5 mg, 68%); ¹H NMR (500 MHz, Methanol-d₄) δ 10.34-10.23 (m, 1H), 9.21 (dd, J=1.3, 0.7 Hz, 1H), 8.71 (s, 1H), 8.51 (d, J=6.3 Hz, 1H), 7.92 (s, 2H), 6.96 (d, J=6.3 Hz, 1H), 4.88 (s, 2H), 4.62-4.44 (m, 1H), 3.71 (t, J=13.1 Hz, 1H), 3.62-3.47 (m, 1H), 3.36-3.32 (m, 1H), 2.80 (s, 3H), 1.60 (d, J=6.4 Hz, 3H); ES+ [M+H]= 444.3.

The following compound was made using methodology similar to that described in Example 94:

3-(4-(4-Ethyl-2,5-dimethyl-3-(1H-pyrazol-4-yl)piperazin-1-yl)pyrimidin-2-yl)-6-(trifluoromethyl)imidazo[1,2-a]pyrazine IV-292.

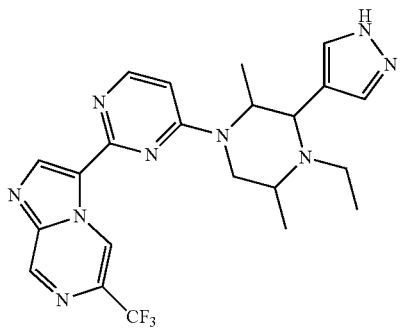 [SMILES: CCN1C(C)CN(c2ccnc(-c3cnc4cnc(C(F)(F)F)cn34)n2)C(C)C1c1cn[nH]c1]

The following compounds were made using methodology similar to that described in Example 94 and further purification by chrial SFC:

3-(4-(4-Ethyl-2,5-dimethyl-3-(1H-pyrazol-4-yl)piperazin-1-yl)pyrimidin-2-yl)-6-(trifluoromethyl)imidazo[1,2-a]pyrazine (all syn diastereoisomer) IV-295;

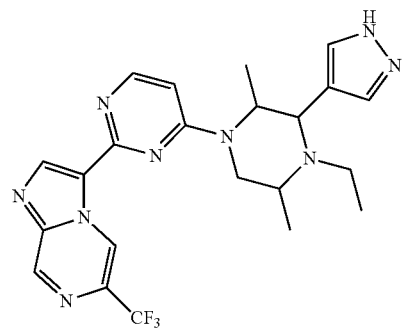 [SMILES: CCN1C(C)CN(c2ccnc(-c3cnc4cnc(C(F)(F)F)cn34)n2)C(C)C1c1cn[nH]c1]

3-(4-(4-Ethyl-2,5-dimethyl-3-(1H-pyrazol-4-yl)piperazin-1-yl)pyrimidin-2-yl)-6-(trifluoromethyl)imidazo[1,2-a]pyrazine (all syn diastereoisomer) IV-296;

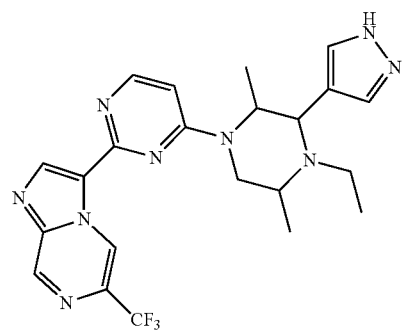 [SMILES: CCN1C(C)CN(c2ccnc(-c3cnc4cnc(C(F)(F)F)cn34)n2)C(C)C1c1cn[nH]c1]

Example 95: 3-(4-(3-(5-Chloro-1H-pyrazol-4-yl)piperidin-1-yl)pyrimidin-2-yl)-6-(trifluoromethyl)imidazo[1,2-a]pyrazine, IV-601

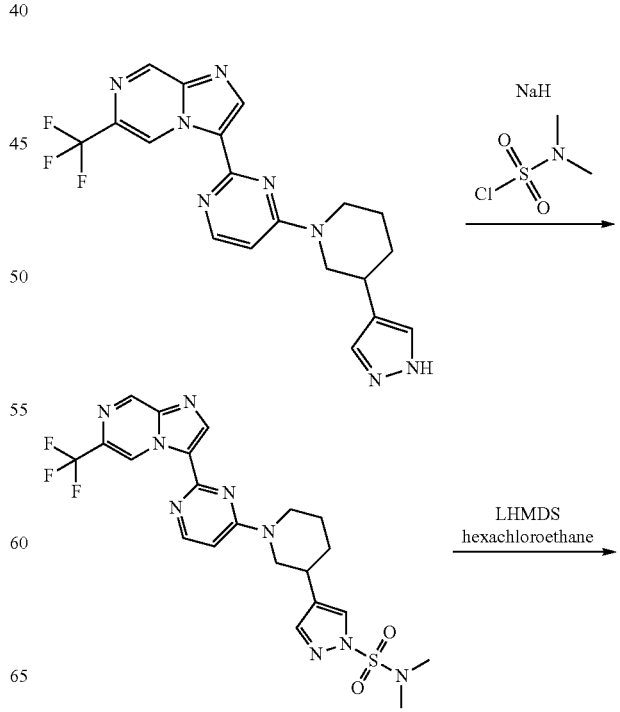

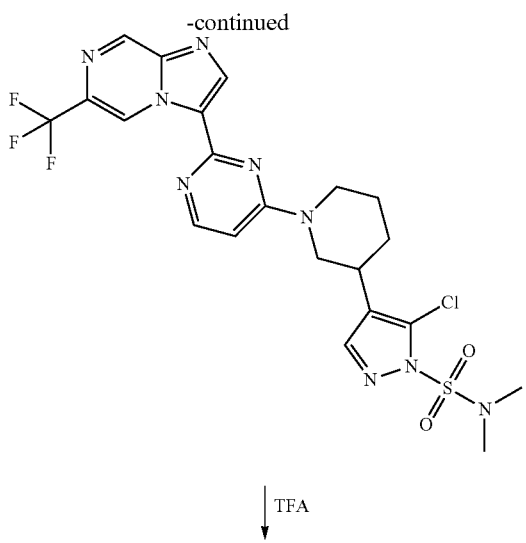

↓ TFA

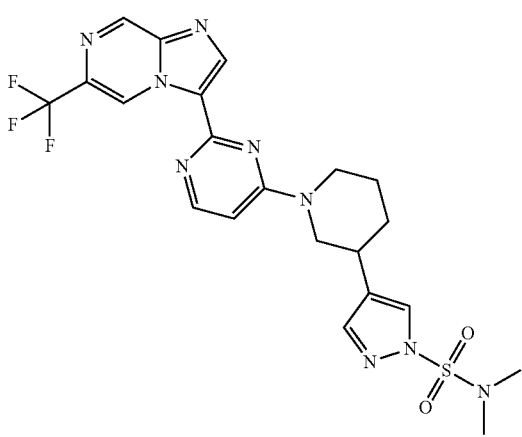 [SMILES: CN(C)S(=O)(=O)n1cc(C2CCCN(c3ccnc(-c4cnc5cnc(C(F)(F)F)cn45)n3)C2)cn1]

Step 1: N,N-Dimethyl-4-(1-(2-(6-(trifluoromethyl) imidazo[1,2-a]pyrazin-3-yl)pyrimidin-4-yl)piperidin-3-yl)-1H-pyrazole-1-sulfonamide To an oven dried flask was added 3-(4-(3-(1H-pyrazol-4-yl)piperidin-1-yl)pyrimidin-2-yl)-6-(trifluoromethyl)imidazo[1,2-a]pyrazine (76 mg, 0.18 mmol) and THF (1 mL) and the solution was stirred under nitrogen at −5° C. Sodium hydride (8.8 mg of 60% w/w, 0.22 mmol) was added and the reaction stirred for 30 mins at 0° C. before N,N-dimethylsulfamoyl chloride (25 μL, 0.23 mmol) was added dropwise. The reaction was stirred at 0° C. for 30 mins before being quenched with isopropanol and saturated aq. NaHCO₃ solution. The mixture was extracted with DCM and the organic layer passed through a phase separator cartridge and concentrated in vacuo. The residue was purified by column chromatography (silica, eluting with 0-15% DCM/MeOH gradient) to give N,N-dimethyl-4-(1-(2-(6-(trifluoromethyl) imidazo[1,2-a]pyrazin-3-yl)pyrimidin-4-yl)piperidin-3-yl)-1H-pyrazole-1-sulfonamide (19.9 mg, 10%); ES+ [M+H]= 522.1.

Step 2: 5-Chloro-N,N-dimethyl-4-(1-(2-(6-(trifluoromethyl)imidazo[1,2-a]pyrazin-3-yl)pyrimidin-4-yl)piperidin-3-yl)-1H-pyrazole-1-sulfonamide

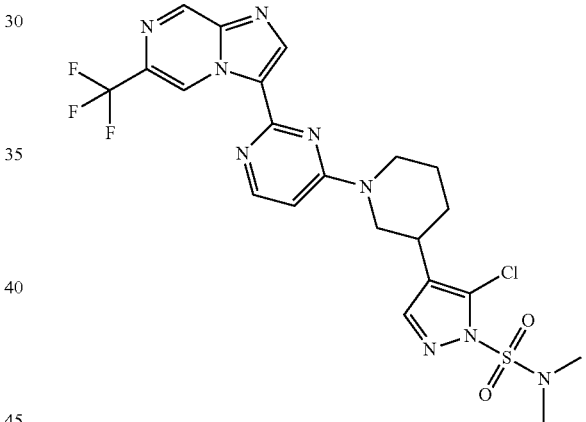

N,N-Dimethyl-4-(1-(2-(6-(trifluoromethyl)imidazo[1,2-a]pyrazin-3-yl)pyrimidin-4-yl)piperidin-3-yl)-1H-pyrazole-1-sulfonamide (19.9 mg, 0.018 mmol) was dissolved in THF (1 mL) and cooled to −78° C. LiHMDS (26 μL of 1 M, 0.026 mmol) was added and the reaction was stirred at −78° C. for 30 mins before a solution of hexachloroethane (8 mg, 0.034 mmol) in THE (1 mL) was added. After 1 hour the reaction was warmed to ambient temperature and stirred overnight before being quenched with saturated aq. NH₄Cl and diluted with EtOAc. The layers were separated, the aqueous layer extracted with EtOAc (×3) and the combined organic layers passed through a phase separator cartridge and concentrated in vacuo. The residue was purified by column (silica, eluting with 0-100% EtOAc/petroleum ether) to give 5-chloro-N, N-dimethyl-4-(1-(2-(6-(trifluoromethyl)imidazo[1,2-a] pyrazin-3-yl)pyrimidin-4-yl)piperidin-3-yl)-1H-pyrazole-1-sulfonamide (4 mg, 36%); ES+ [M+H]=556.3.

Step 3: 3-(4-(3-(5-Chloro-1H-pyrazol-4-yl)piperidin-1-yl)pyrimidin-2-yl)-6-(trifluoromethyl)imidazo[1,2-a]pyrazine

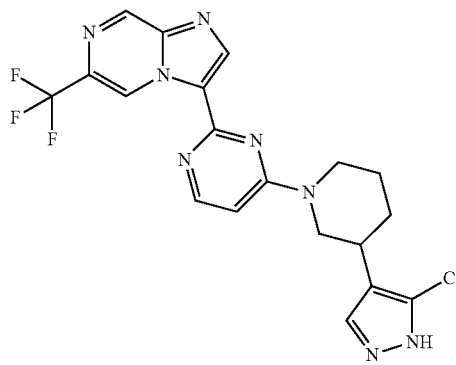 [SMILES: FC(F)(F)c1cn2c(-c3nccc(N4CCCC(c5cn[nH]c5Cl)C4)n3)cnc2cn1]

TFA (0.1 mL, 1.30 mmol) was added to a solution of 5-chloro-N,N-dimethyl-4-(1-(2-(6-(trifluoromethyl)imidazo[1,2-a]pyrazin-3-yl)pyrimidin-4-yl)piperidin-3-yl)-1H-pyrazole-1-sulfonamide (4 mg, 0.006 mmol) in DCM (2 mL). The reaction was stirred at ambient temperature for 30 minutes before being concentrated in vacuo, diluted with DMSO and purified directly by reverse phase chromatography (C18; MeCN/water—0.1% ammonium hydroxide as eluent) to give 3-(4-(3-(5-chloro-1H-pyrazol-4-yl)piperidin-1-yl)pyrimidin-2-yl)-6-(trifluoromethyl)imidazo[1,2-a]pyrazine (1.2 mg, 34%); $^1$H NMR (500 MHz, Methanol-$d_4$) δ 10.35-10.31 (m, 1H), 9.18 (dd, J=1.4, 0.7 Hz, 1H), 8.64 (s, 1H), 8.33 (d, J=6.4 Hz, 1H), 7.66-7.61 (m, 1H), 6.77 (d, J=6.4 Hz, 1H), 4.62 (s, 2H), 3.26-3.09 (m, 2H), 2.81 (tt, J=11.0, 3.8 Hz, 1H), 2.18-2.11 (m, 1H), 1.97-1.66 (m, 3H), 1.28 (s, 1H); ES+ [M+H]=449.0.

Example 96: 3-(4-(3-(5-Chloro-1H-pyrazol-4-yl)-5-methylpiperazin-1-yl)pyrimidin-2-yl)-6-(trifluoromethyl)imidazo[1,2-a]pyrazine, IV-651 and IV-652

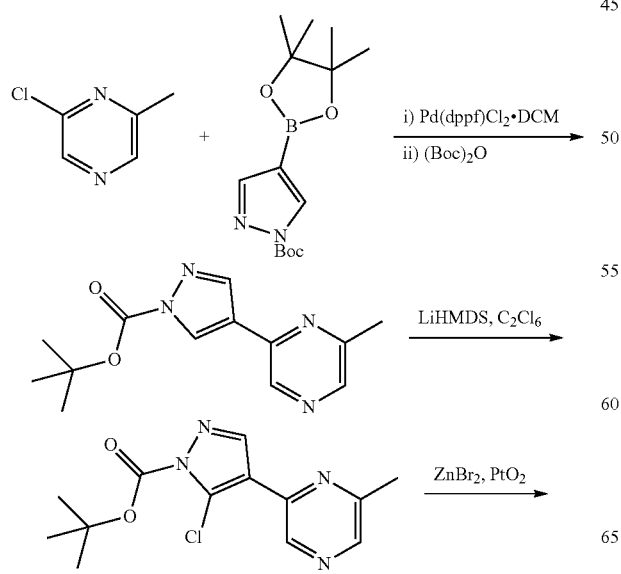

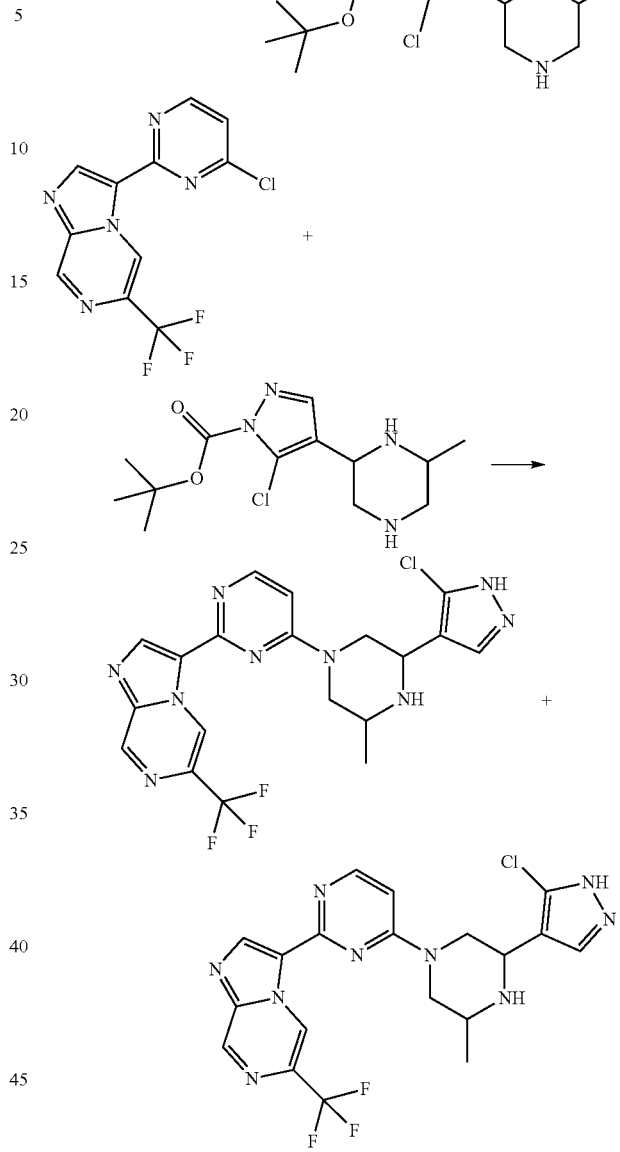

Step 1: 2-Methyl-6-(1H-pyrazol-4-yl)pyrazine

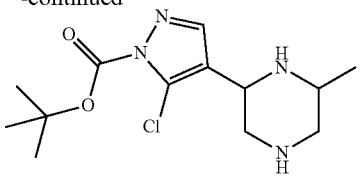

2-Chloro-6-methyl-pyrazine (2.06 g, 16.02 mmol), tert-butyl 4-(4,4,5,5-tetramethyl-1,3,2-dioxaborolan-2-yl)-1H-pyrazole-1-carboxylate (5.18 g, 17.6 mmol), Pd(dppf)Cl$_2$.DCM (654 mg, 0.80 mmol) and aq. Na$_2$CO$_3$ (20 mL of 2 M, 40.1 mmol) in 1,4-dioxane (80 mL) were heated at 90° C. for 16 hours. The reaction was cooled to ambient temperature, diluted with EtOAc, washed with brine, dried (MgSO₄) and concentrated in vacuo. Purification by column chromatography (silica, eluting with 0-100% EtOAc/petroleum ether) gave 2-methyl-6-(1H-pyrazol-4-yl)pyrazine as a white solid (1.97 g, 77%); ¹H NMR (500 MHz, DMSO-d₆) δ 13.19 (s, 1H), 8.79 (s, 1H), 8.41 (s, 1H), 8.29 (s, 1H), 8.25-7.98 (m, 1H), 2.49 (s, 3H).

Step 2: tert-Butyl 4-(6-methylpyrazin-2-yl)-1H-pyrazole-1-carboxylate

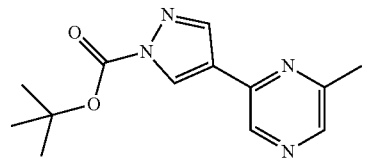 [SMILES: Cc1cncc(-c2cnn(C(=O)OC(C)(C)C)c2)n1]

Et₃N (1.37 g, 1.89 mL, 13.5 mmol), Boc₂O (3.22 g, 14.8 mmol) and DMAP (150 mg, 1.23 mmol) were added to a solution of 2-methyl-6-(1H-pyrazol-4-yl)pyrazine (1.97 g, 12.3 mmol) in THF (60 mL). The reaction was stirred at ambient temperature for 3 hours before being diluted with EtOAc and washed with 1 M HCl. The organics were dried (MgSO₄) and concentrated in vacuo, and the residue purified by column chromatography (silica, eluting with 0-100% EtOAc/petroleum ether) to afford tert-butyl 4-(6-methylpyrazin-2-yl)-1H-pyrazole-1-carboxylate as a white solid (2.84 g, 89%); ¹H NMR (500 MHz, DMSO-d₆) δ 8.98 (s, 1H), 8.93 (d, J=0.7 Hz, 1H), 8.43 (s, 1H), 8.40 (d, J=0.7 Hz, 1H), 2.53 (s, 3H), 1.62 (s, 9H).

Step 3: tert-Butyl 5-chloro-4-(6-methylpyrazin-2-yl)-1H-pyrazole-1-carboxylate

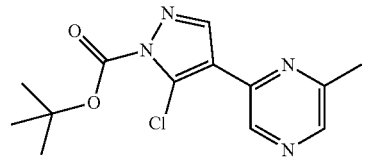 [SMILES: Cc1cncc(-c2cnn(C(=O)OC(C)(C)C)c2Cl)n1]

LiHMDS (1.56 mL of 1 M, 1.56 mmol) was added dropwise to a solution of 4-(6-methylpyrazin-2-yl)-1H-pyrazole-1-carboxylate (270 mg, 1.04 mmol) in THF (5.1 mL) stirring at −78° C. After 30 mins 1,1,1,2,2,2-hexachloroethane (491 mg, 2.07 mmol) in THF (2.5 mL) was added and the reaction stirred at −78° C. for 1 hour and then at ambient temperature for 1 hour. The reaction was quenched with saturated aq. NH₄Cl, extracted with EtOAc, dried (MgSO₄), filtered and concentrated in vacuo. Purification by column chromatography (silica, eluting with 0-100% EtOAc/petroleum ether) gave tert-butyl 5-chloro-4-(6-methylpyrazin-2-yl)-1H-pyrazole-1-carboxylate as a white solid (223 mg, 73%); ¹H NMR (500 MHz, Chloroform-d) δ 8.98 (s, 1H), 8.62 (s, 1H), 8.40 (s, 1H), 2.60 (s, 3H), 1.68 (s, 9H).

Step 4: tert-Butyl 5-chloro-4-(6-methylpiperazin-2-yl)-1H-pyrazole-1-carboxylate

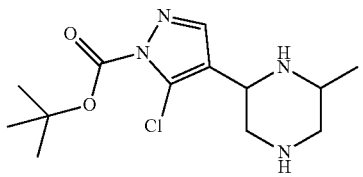 [SMILES: CC1CNCC(c2cnn(C(=O)OC(C)(C)C)c2Cl)N1]

tert-Butyl 5-chloro-4-(6-methylpyrazin-2-yl)-1H-pyrazole-1-carboxylate (220 mg, 0.75 mmol), dibromozinc (67.3 mg, 16.0 μL, 0.30 mmol) and PtO₂ (34.4 mg, 0.15 mmol) were suspended in methanol (15 mL) and HCl (1.24 mL of 3 M, 3.73 mmol) was added. The mixture was degassed and stirred under a balloon of H₂. After 2 hours the reaction was filtered through Celite and concentrated to afford tert-butyl 5-chloro-4-(6-methylpiperazin-2-yl)-1H-pyrazole-1-carboxylate as the hydrochloride salt and as a single diastereomer (250 mg, 100%); ES+ [M+H]=301.2.

Step 5: 3-(4-(3-(5-Chloro-1H-pyrazol-4-yl)-5-methylpiperazin-1-yl)pyrimidin-2-yl)-6-(trifluoromethyl)imidazo[1,2-a]pyrazine

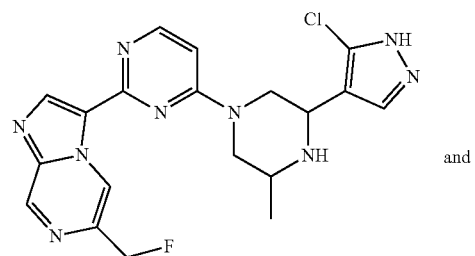

and

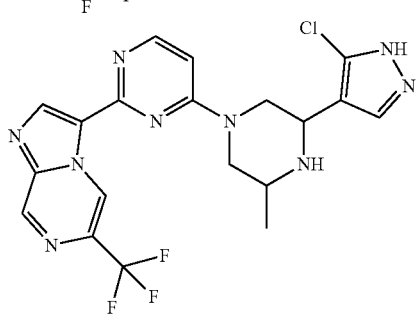

3-(4-Chloropyrimidin-2-yl)-6-(trifluoromethyl)imidazo[1,2-a]pyrazine (100 mg, 0.33 mmol), tert-butyl 5-chloro-4-(6-methylpiperazin-2-yl)-1H-pyrazole-1-carboxylate (hydrochloride salt) (169 mg, 0.50 mmol) and DIPEA (300 μL, 1.72 mmol) were combined in DMF (1.7 mL) and heated to 80° C. After 2 hours, 2 M aq. KOH (850 μL, 1.70 mmol) was added and the heating continued for 1 hour. The reaction was filtered and purified directly by reverse phase chromatography (C18; MeCN/water—0.05% TFA as eluent). Further purification by chiral SFC gave:

IV-651: 3-[4-[3-(5-Chloro-1H-pyrazol-4-yl)-5-methyl-piperazin-1-yl]pyrimidin-2-yl]-6-(trifluoromethyl)imidazo[1,2-a]pyrazine (4.0 mg, 18%) as the trifluoroacetate salt; ¹H NMR (400 MHz, DMSO-d$_6$) δ 13.40 (s, 1H), 10.19 (s, 1H), 9.68-9.43 (m, 1H), 9.38 (s, 1H), 9.18-8.94 (m, 1H), 8.80 (s, 1H), 8.54 (d, J=6.2 Hz, 1H), 8.12 (s, 1H), 7.08 (d, J=6.3 Hz, 1H), 5.21-4.51 (m, 2H), 4.50-4.36 (m, 1H), 3.75-3.63 (m, 2H), 3.20-3.06 (m, 1H), 1.36 (d, J=6.4 Hz, 3H); ES+[M+H]=464.2.

and

IV-652: 3-[4-[3-(5-Chloro-1H-pyrazol-4-yl)-5-methyl-piperazin-1-yl]pyrimidin-2-yl]-6-(trifluoromethyl)imidazo[1,2-a]pyrazine (3.9 mg, 17%); ES+ [M+H]=464.2.

Example 97: N-(((3S,5S)-1-(6-(6-(Difluoromethyl)imidazo[1,2-a]pyrazin-3-yl)pyridin-2-yl)-4,4-difluoro-5-methylpiperidin-3-yl)methyl)methanesulfonamide, IV-275

Example 98: 2-(1-(2-(6-(Trifluoromethyl)imidazo[1,2-a]pyrazin-3-yl)pyrimidin-4-yl)piperidin-3-yl)-1,3,4-thiadiazole, IV-671

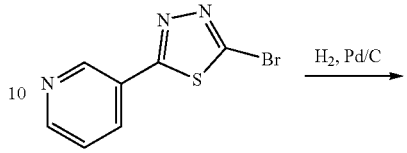

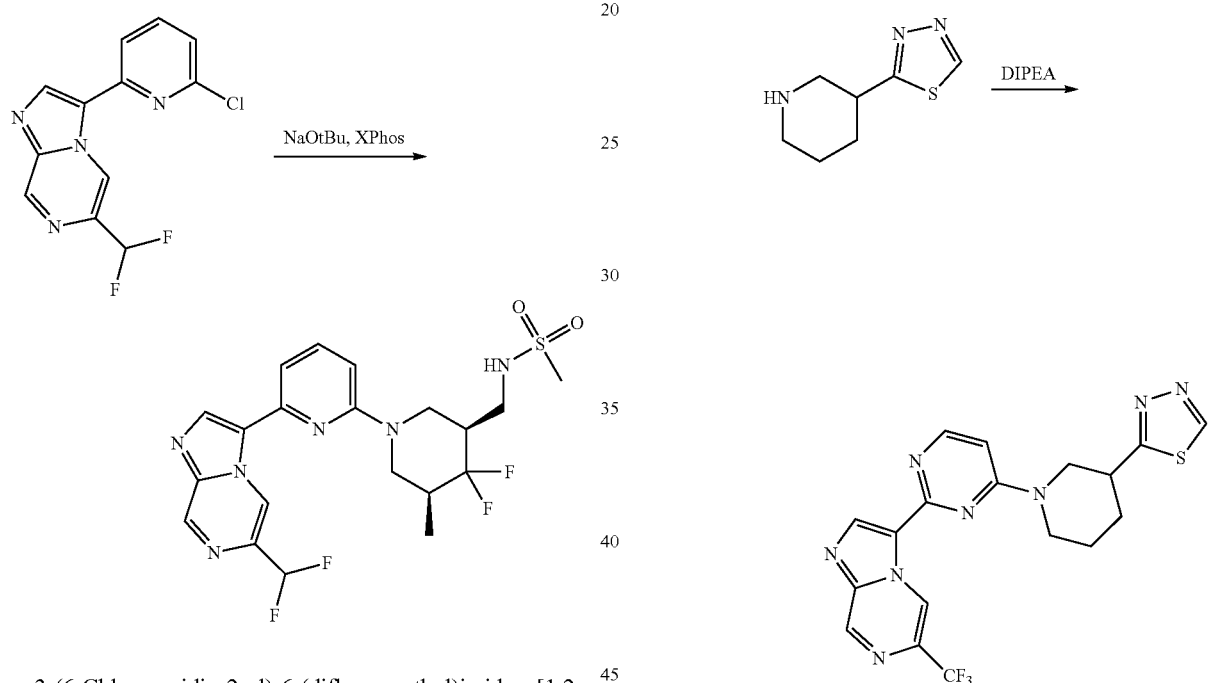

3-(6-Chloropyridin-2-yl)-6-(difluoromethyl)imidazo[1,2-a]pyrazine (23.0 mg, 0.08 mmol), N-(((3S,5S)-4,4-difluoro-5-methylpiperidin-3-yl)methyl)methanesulfonamide (10.0 mg, 0.04 mmol) and sodium tert-butoxide (8.0 mg, 0.08 mmol) were suspended in dioxane (400 μL) and purged with nitrogen gas for several minutes. (2-Dicyclohexylphosphino-2',4',6'-triisopropyl-1,1'-biphenyl)[2-(2-aminoethyl)phenyl)]palladium(II) chloride (2.5 mg, 0.004 mmol) was added and the mixture was heated at 125° C. for 70 minutes in the microwave and then 160° C. for 3 days in a heating block. After this time the mixture was filtered, diluted with DMSO and purified directly by reverse phase chromatography (C18; MeCN/water—0.05% TFA as eluent) to give N-(((3S,5S)-1-(6-(6-(difluoromethyl)imidazo[1,2-a]pyrazin-3-yl)pyridin-2-yl)-4,4-difluoro-5-methylpiperidin-3-yl)methyl)methanesulfonamide (0.8 mg, 4%); $^1$H NMR (500 MHz, Methanol-d$_4$) δ 10.06 (s, 1H), 9.12 (d, J=1.3 Hz, 1H), 8.43 (s, 1H), 7.74 (dd, J=8.6, 7.5 Hz, 1H), 7.38-7.34 (m, 1H), 7.10-6.83 (m, 2H), 4.64-4.50 (m, 2H), 3.56 (dd, J=13.7, 3.9 Hz, 1H), 3.14 (dd, J=13.7, 9.3 Hz, 1H), 3.03-2.97 (m, 1H), 2.96 (s, 3H), 2.94-2.86 (m, 1H), 2.38-2.07 (m, 2H), 1.13 (d, J=6.7 Hz, 3H).

A solution of 2-bromo-5-(3-pyridyl)-1,3,4-thiadiazole (100 mg, 0.41 mmol) in EtOH (10 mL) and TFA (200 μL, 2.60 mmol) was run through an H-cube (5% palladium on carbon cartridge, 100° C., 100 atm H$_2$, 0.5 mL/min) and the mixture recirculated for 2 hours. The residue was redissolved in NMP (1 mL) and DIPEA (100 μL, 0.57 mmol) and 3-(4-chloropyrimidin-2-yl)-6-(trifluoromethyl)imidazo[1,2-a]pyrazine (10 mg, 0.033 mmol) were added. The mixture was stirred at 80° C. for 2 hours before being filtered, diluted in acetonitrile/water (3:1) and purified by reverse phase chromatography (C18; MeCN/water—0.1% ammonium hydroxide as eluent) to give 2-(1-(2-(6-(trifluoromethyl)imidazo[1,2-a]pyrazin-3-yl)pyrimidin-4-yl)piperidin-3-yl)-1,3,4-thiadiazole (0.7 mg, 0.4%); $^1$H NMR (500 MHz, Methanol-d$_4$) δ 10.33 (s, 1H), 9.40 (s, 1H), 9.20 (d, J=1.4 Hz, 1H), 8.67 (s, 1H), 8.37 (d, J=6.3 Hz, 1H), 6.85 (d, J=6.4 Hz, 1H), 4.74 (s, 1H), 4.33 (s, 1H), 3.72 (dd, J=13.3, 9.5 Hz, 1H), 3.61 (dd, J=8.9, 5.1 Hz, 1H), 3.52-3.42 (m, 1H), 2.38 (dd, J=13.1, 4.4 Hz, 1H), 2.16-2.05 (m, 1H), 1.98 (dt, J=8.6, 4.4 Hz, 1H), 1.89-1.75 (m, 1H); ES+ [M+H]=433.1.

Example 99: 3-(4-(2-Methyl-3-(1H-pyrazol-4-yl)pyrrolidin-1-yl)pyrimidin-2-yl)-6-(trifluoromethyl)imidazo[1,2-a]pyrazine, IV-688 and IV-689

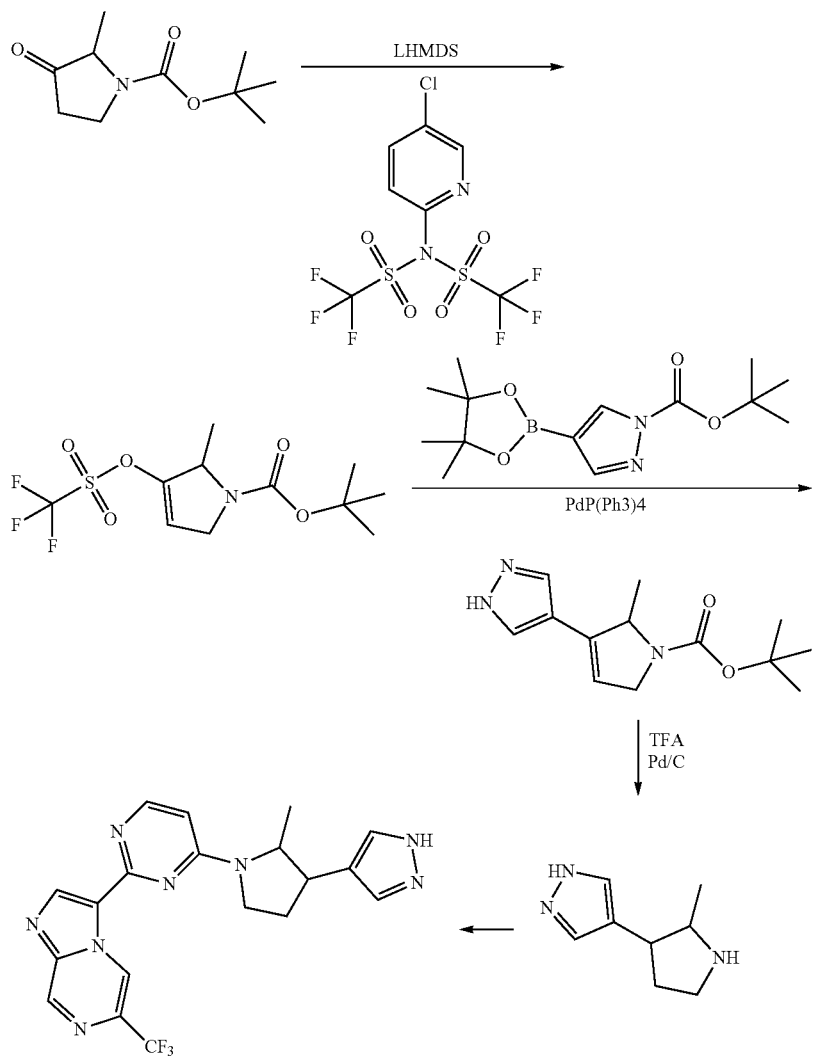

Step 1: tert-Butyl 2-methyl-3-(((trifluoromethyl)sulfonyl)oxy)-2,5-dihydro-1H-pyrrole-1-carboxylate

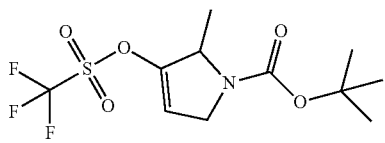 [SMILES: CC1C(OS(=O)(=O)C(F)(F)F)=CCN1C(=O)OC(C)(C)C]

A solution of tert-butyl 2-methyl-3-oxopyrrolidine-1-carboxylate (580 mg, 2.91 mmol) in THF (3 mL) was cooled to −78° C. and [bis(trimethylsilyl)amino]lithium (3.78 mL of 1 M, 3.78 mmol) was added dropwise. After 30 mins at this temperature, a solution of N-(5-chloro-2-pyridyl)-1,1,1-trifluoro-N-(trifluoromethylsulfonyl)methanesulfonamide (1.49 g, 3.78 mmol) in THF (3 mL) was added. The mixture was stirred at −78° C. for 1 hour before being quenched by addition of 2 M aq. $Na_2CO_3$ (2 mL) and stored at 4° C. overnight. The mixture was partitioned between EtOAc and saturated $NaHCO_3$ solution, the layers separated and the organic layer dried ($MgSO_4$) and concentrated in vacuo to give tert-butyl 2-methyl-3-(((trifluoromethyl)sulfonyl)oxy)-2,5-dihydro-1H-pyrrole-1-carboxylate as an amber oil, which was used without further purification.

Step 2: tert-Butyl 2-methyl-3-(1H-pyrazol-4-yl)-2,5-dihydro-1H-pyrrole-1-carboxylate

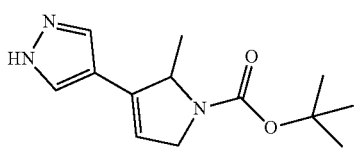 [SMILES: CC1C(c2cn[nH]c2)=CCN1C(=O)OC(C)(C)C]

tert-Butyl 2-methyl-3-(((trifluoromethyl)sulfonyl)oxy)-2,5-dihydro-1H-pyrrole-1-carboxylate (964 mg, 2.91 mmol), 2 M aq. Na$_2$CO$_3$ (3.20 mL, 6.40 mmol) and tert-butyl 4-(4,4,5,5-tetramethyl-1,3,2-dioxaborolan-2-yl)pyrazole-1-carboxylate (1.07 g, 3.64 mmol) were combined in dioxane (15 mL) and the mixture degassed. Tetrakis(triphenylphosphine)palladium(0) (336 mg, 0.291 mmol) was added and the mixture was heated to 80° C. under nitrogen. After 1.5 hours, 2 M aq. LiOH (2.91 mL, 5.82 mmol) was added and the temperature was increased to 100° C. After 1.5 hours the reaction was cooled and diluted in saturated aq. NaHCO$_3$ and ethyl acetate. The layers were separated and the organic layer dried (MgSO$_4$) and concentrated in vacuo. Purification by column chromatography (silica, eluting with 0-70% ethyl acetate/petroleum ether) gave tert-butyl 2-methyl-3-(11H-pyrazol-4-yl)-2,5-di H-pyrrole-1-carboxylate (498 mg, 69% over two steps); ES+ [M+H]=250.2.

Step 3: 4-(2-Methylpyrrolidin-3-yl)-1H-pyrazole

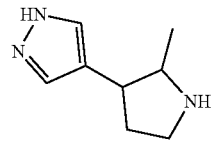

To a solution of tert-butyl 2-methyl-3-(1H-pyrazol-4-yl)-2,5-dihydro-1H-pyrrole-1-carboxylate (250 mg, 1.003 mmol) in DCM (3 mL) was added TFA (1 mL, 13.0 mmol). The reaction mixture was stirred at ambient temperature for 40 mins before concentrating in vacuo. Palladium on carbon (106.7 mg of 10% w/w, 0.100 mmol) and methanol were added to the residue and the mixture shaken on the Parr hydrogenator under a 60 psi pressure of hydrogen, at ambient temperature, for 2 hours. Filtration through Celite gave 4-(2-methylpyrrolidin-3-yl)-1H-pyrazole, which was used in the next step without further purification.

Step 4: 3-(4-(2-Methyl-3-(1H-pyrazol-4-yl)pyrrolidin-1-yl)pyrimidin-2-yl)-6-(trifluoromethyl)imidazo[1,2-a]pyrazine

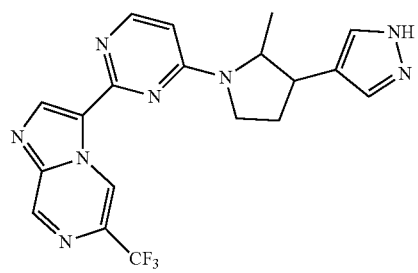 [SMILES: CC1C(c2cn[nH]c2)CCN1c1ccnc(-c2cnc3cnc(C(F)(F)F)cn23)n1]

A solution of 4-(2-methylpyrrolidin-3-yl)-1H-pyrazole (53.8 mg, 0.20 mmol), DIPEA (88 µL, 0.51 mmol) and 3-(4-chloropyrimidin-2-yl)-6-(trifluoromethyl)imidazo[1,2-a]pyrazine (50.7 mg, 0.17 mmol) in NMP (1 mL) was heated at 90° C. for 3 hours in a sealed tube. The reaction was cooled to ambient temperature, diluted with DMSO and purified by reverse phase chromatography (C18; MeCN/water—0.1% ammonium hydroxide as eluent) to give:

IV-688: 3-(4-(2-Methyl-3-(1H-pyrazol-4-yl)pyrrolidin-1-yl)pyrimidin-2-yl)-6-(trifluoromethyl)imidazo[1,2-a]pyrazine (19 mg, 26%); $^1$H NMR (500 MHz, DMSO-d$_6$) δ 12.71 (s, 1H), 10.34 (s, 1H), 9.36 (s, 1H), 8.68 (s, 1H), 8.35 (d, J=6.4 Hz, 1H), 7.68 (s, 1H), 7.46 (s, 1H), 6.67-6.42 (m, 1H), 4.44 (d, J=205.3 Hz, 1H), 3.78 (d, J=89.4 Hz, 1H), 3.59-3.39 (m, 1H), 2.36 (d, J=47.5 Hz, 2H), 1.26 (d, J=11.7 Hz, 1H), 1.03-0.84 (m, 3H); ES+ [M+H]=415.3.
and IV-689: 3-(4-(2-Methyl-3-(1H-pyrazol-4-yl)pyrrolidin-1-yl)pyrimidin-2-yl)-6-(trifluoromethyl)imidazo[1,2-a]pyrazine (4 mg, 6%); $^1$H NMR (500 MHz, DMSO-d$_6$) δ 12.63 (s, 1H), 10.34 (s, 1H), 9.35 (d, J=1.4 Hz, 1H), 8.67 (s, 1H), 8.35 (d, J=6.0 Hz, 1H), 7.49 (d, J=95.5 Hz, 2H), 6.53 (s, 1H), 4.22 (d, 1H) 3.59 (s, 2H), 2.16-1.92 (m, 1H), 1.34 (d, J=95.4 Hz, 5H); ES+ [M+H]=415.3.

Example 100: 1-(2-(6-(Difluoromethyl)imidazo[1,2-a]pyrazin-3-yl)pyrimidin-4-yl)-5-methylpiperidine-3-carboxamide, IV-107

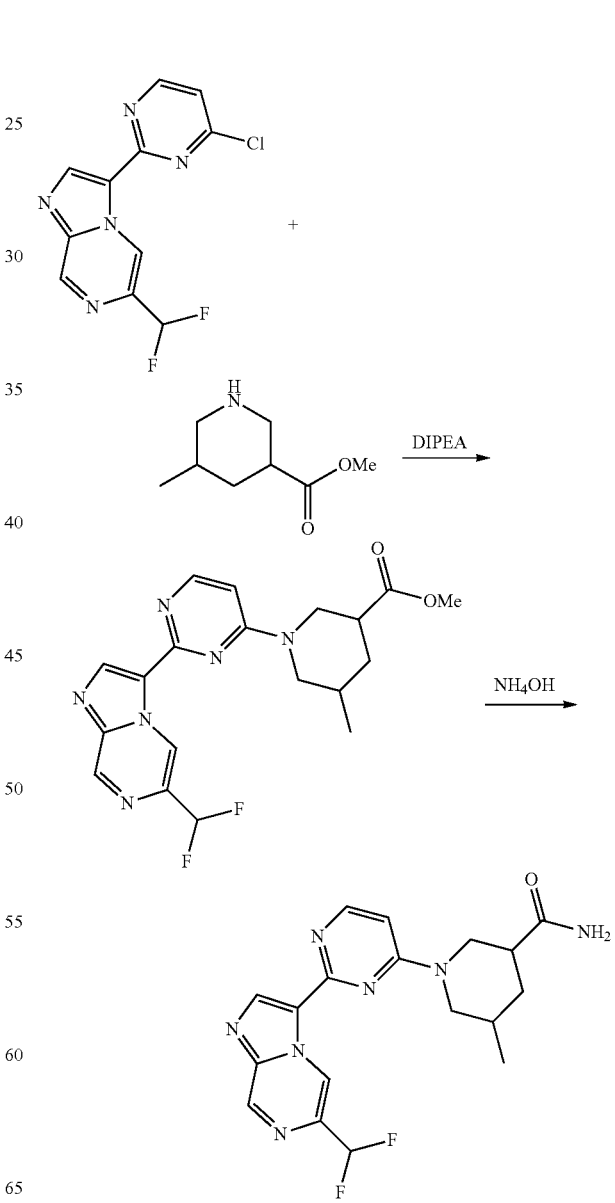

Step 1: Methyl 1-(2-(6-(difluoromethyl)imidazo[1,2-a]pyrazin-3-yl)pyrimidin-4-yl)-5-methylpiperidine-3-carboxylate

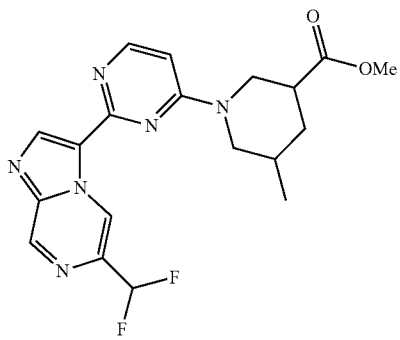 [SMILES: COC(=O)C1CC(C)CN(c2ccnc(-c3cnc4cnc(C(F)F)cn34)n2)C1]

A round-bottomed flask was charged with 3-(4-chloropyrimidin-2-yl)-6-(difluoromethyl)imidazo[1,2-a]pyrazine (30 mg, 0.1044 mmol), 1-piperazin-1-yl-ethanone (20.2 mg, 0.104 mmol) and DIPEA (54.5 μL, 0.3132 mmol) in NMP (0.2 mL). The vessel was sealed and then stirred at 80° C. for 20 minutes. The reaction mixture was cooled to ambient temperature and the mixture was filtered through a Whatman 0.45 μM syringe filter and diluted with DMSO. The solution was purified by reverse phase chromatography (C18; MeCN/water—0.05% TFA as eluent). The product fractions were then combined and lyophilised to give methyl 1-(2-(6-(difluoromethyl)imidazo[1,2-a]pyrazin-3-yl)pyrimidin-4-yl)-5-methylpiperidine-3-carboxylate

Step 2: 1-(2-(6-(Difluoromethyl)imidazo[1,2-a]pyrazin-3-yl)pyrimidin-4-yl)-5-methylpiperidine-3-carboxamide

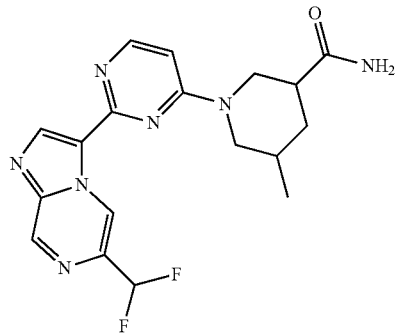 [SMILES: CC1CC(C(N)=O)CN(c2ccnc(-c3cnc4cnc(C(F)F)cn34)n2)C1]

A microwave vial was charged with methyl 1-[2-[6-(difluoromethyl)imidazo[1,2-a]pyrazin-3-yl]pyrimidin-4-yl]-5-methyl-piperidine-3-carboxylate (42 mg, 0.1044 mmol) in NMP (0.2 mL) and NH$_4$OH (approximately 610 mg, 677.6 μL, 5.220 mmol). The vessel was sealed and then heated at 100° C. for 3 days. The reaction mixture was cooled to ambient temperature and was then filtered and diluted with DMSO. The resulting solution was purified by reverse phase chromatography (C18; MeCN/water—0.05% TFA as eluent). Product fractions were combined and lyophilised to give 1-(2-(6-(difluoromethyl)imidazo[1,2-a]pyrazin-3-yl)pyrimidin-4-yl)-5-methylpiperidine-3-carboxamide (0.6 mg, 0.88%) as a 2:1 mixture of diastereomers; MS m/z: 388.3 (M+H)$^+$.

Example 101: 3-(4-((8aS)-4-(1H-pyrazol-4-yl)hexahydropyrrolo[1,2-a]pyrazin-2(1H)-yl)pyrimidin-2-yl)-6-(trifluoromethyl)imidazo[1,2-a]pyrazine, IV-679

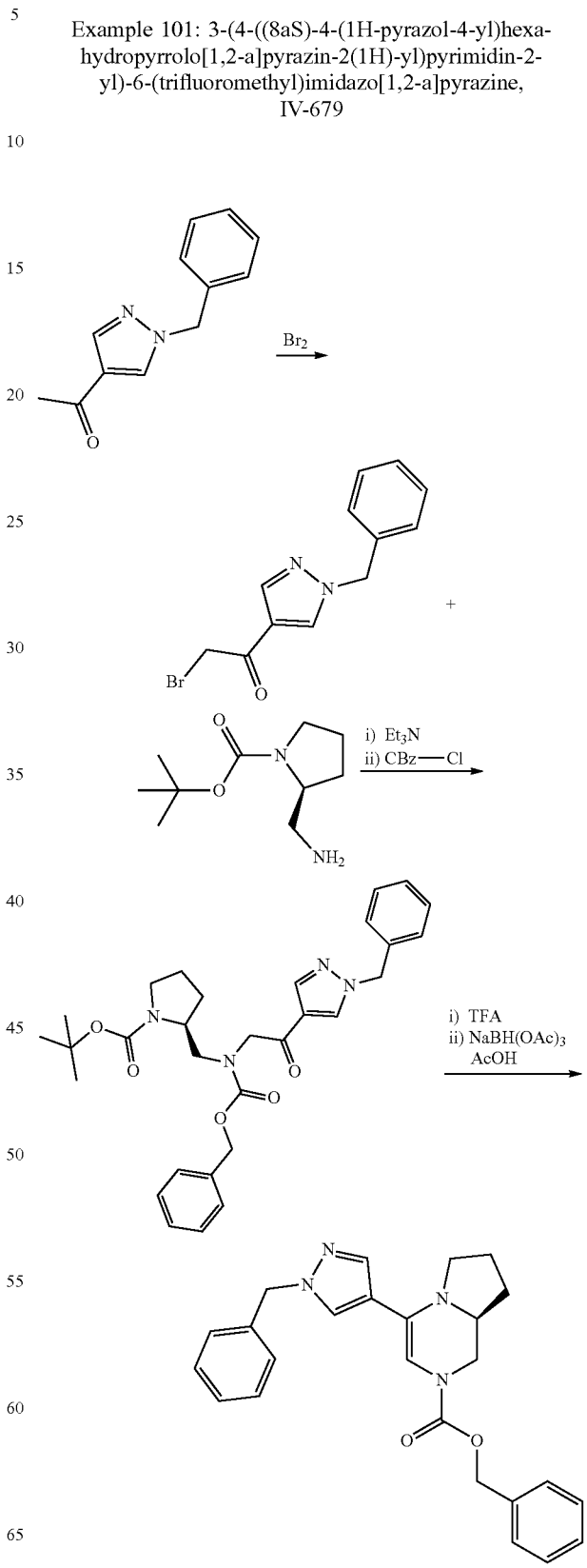

-continued

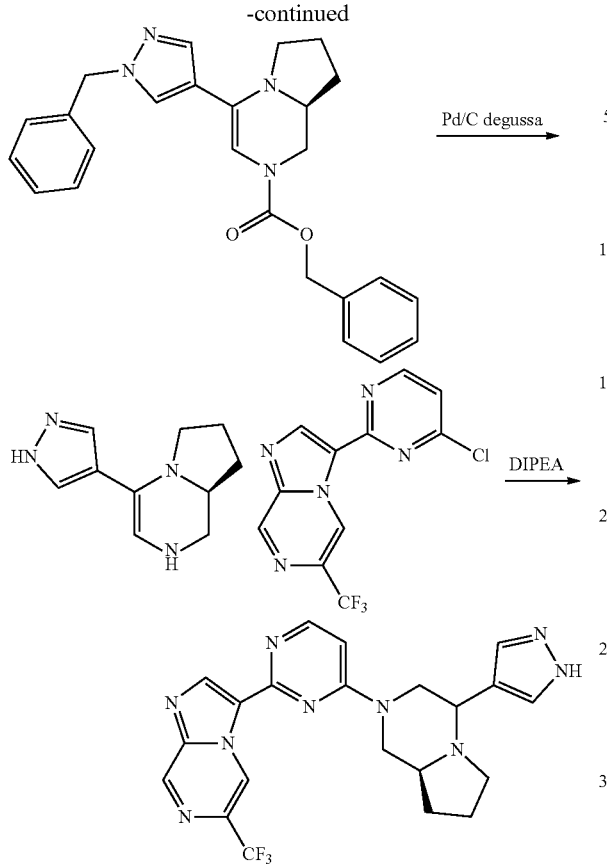

Step 1: 1-(1-Benzyl-1H-pyrazol-4-yl)-2-bromo-ethan-1-one

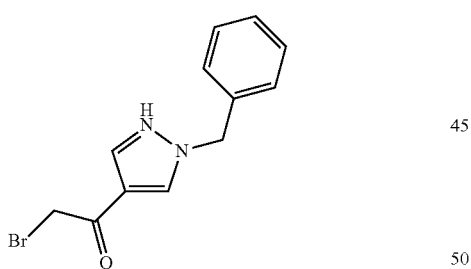

Bromine (390 µL, 7.570 mmol) was added dropwise to an ice cold solution of 1-(1-benzylpyrazol-4-yl)ethanone (1.5 g, 7.491 mmol) in chloroform (20 mL) under $N_2$. After 5 minutes, the ice bath was removed and the reaction mixture stirred at ambient temperature for 20 hours. After this time, additional bromine was added (0.2 mL, 0.39 mmol) and the reaction mixture stirred at ambient temperature for a further 24 hours. The reaction mixture was quenched by addition of 30 mL of saturated $NaHCO_3$ solution. The organic layer was further washed with saturated aqueous $NaHCO_3$, brine, dried over $MgSO_4$ and concentrated under reduced pressure. The crude material was purified by column chromatography (silica, 0-100% EtOAc/hexanes) to give 1-(1-benzylpyrazol-4-yl)-2-bromo-ethanone (1.34 g, 61%) as a yellow oil; MS m/z 281.1 $(M+H)^+$.

Step 2: tert-Butyl (S)-2-(((2-(1-benzyl-1H-pyrazol-4-yl)-2-oxoethyl)((benzyloxy)carbonyl)amino)methyl)pyrrolidine-1-carboxylate

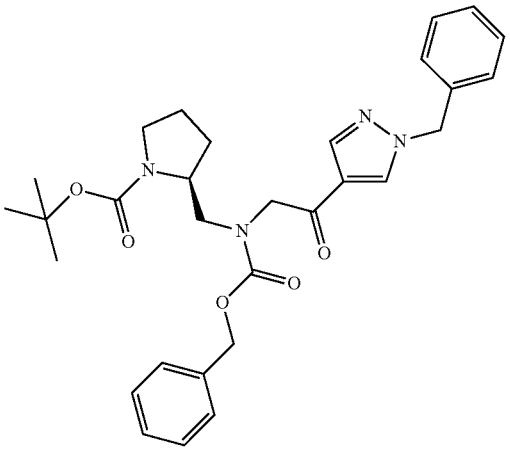 [SMILES: CC(C)(C)OC(=O)N1CCC[C@H]1CN(CC(=O)c1cnn(Cc2ccccc2)c1)C(=O)OCc1ccccc1]

1-(1-Benzylpyrazol-4-yl)-2-bromo-ethanone (280 mg, 0.95 mmol) was dissolved in DCM (10 mL) before addition of tert-butyl (2S)-2-(aminomethyl)pyrrolidine-1-carboxylate (200 mg, 1.00 mmol) and triethylamine (150 µL, 1.08 mmol). The resulting solution was stirred at ambient temperature for 1 hour. CBz-Cl (130 µL, 0.91 mmol) and $Et_3N$ (400 µL, 2.87 mmol) were added and the resulting mixture stirred for 90 mins and then concentrated in vacuo. The crude mixture was purified by column chromatography (silica, 0-100% EtOAc/petroleum ether, loaded in DCM). The product fractions were combined and concentrated under reduced pressure to give tert-butyl (2S)-2-[[benzyloxycarbonyl-[2-(1-benzylpyrazol-4-yl)-2-oxo-ethyl]amino]methyl]pyrrolidine-1-carboxylate (240 mg, 47%); MS m/z 533.2 $(M+H)^+$.

Step 3: Benzyl (S)-4-(1-benzyl-1H-pyrazol-4-yl)-6,7,8,8a-tetrahydropyrrolo[1,2-a]pyrazine-2(1H)-carboxylate

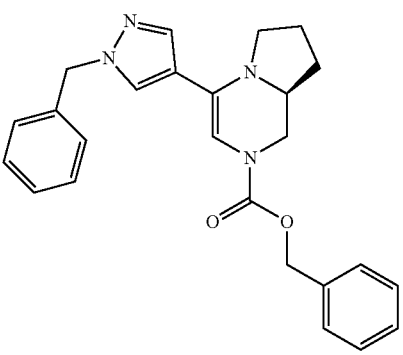 [SMILES: O=C(OCc1ccccc1)N1C=C(c2cnn(Cc3ccccc3)c2)N2CCC[C@H]2C1]

tert-Butyl (2S)-2-[[benzyloxycarbonyl-[2-(1-benzylpyrazol-4-yl)-2-oxo-ethyl]amino]methyl]pyrrolidine-1-carboxylate (240 mg, 0.45 mmol) was dissolved in DCM (3 mL) and then cooled to 0° C. TFA (2 mL) was then slowly added and the reaction mixture was warmed to ambient temperature. After 3 hours the reaction mixture was concentrated under reduced pressure with DCM to co-evaporate residual TFA (×5). The crude orange residue was dissolved in DCE (5 mL) and then acetic acid (20 μL, 0.35 mmol) was added followed by Na(OAc)₃BH (300 mg, 1.42 mmol). The resulting mixture was stirred at ambient temperature for 30 mins. The reaction mixture was then quenched with saturated aqueous NaHCO₃ before separating and extracting with DCM (2×40 mL). The combined organic extracts were washed with brine (20 mL), passed through a hydrophobic frit and concentrated to give benzyl (8aS)-4-(1-benzylpyrazol-4-yl)-6,7,8,8a-tetrahydro-1H-pyrrolo[1,2-a]pyrazine-2-carboxylate (150 mg, 80%) as a colourless gum; MS m/z 415.3 (M+H)⁺.

Step 4: 3-(4-((8aS)-4-(1H-pyrazol-4-yl)hexahydropyrrolo[1,2-a]pyrazin-2(1H)-yl)pyrimidin-2-yl)-6-(trifluoromethyl)imidazo[1,2-a]pyrazine

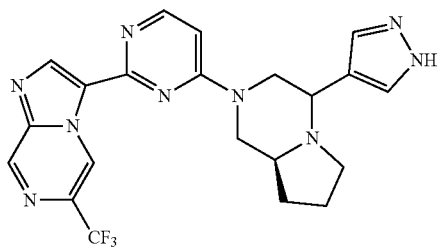 [SMILES: FC(F)(F)c1cn2c(-c3nccc(N4CC(c5cn[nH]c5)N5CCC[C@H]5C4)n3)cnc2cn1]

Benzyl (8aS)-4-(1-benzylpyrazol-4-yl)-6,7,8,8a-tetrahydro-1H-pyrrolo[1,2-a]pyrazine-2-carboxylate (40 mg, 0.097 mmol), Pd on C, wet Degussa (15 mg of 10% w/w, 0.014 mmol) and concentrated HCl (40 μL of 12 M, 0.480 mmol) were taken up in methanol (2 mL) and was stirred at ambient temperature for 22 hours under stirred under a balloon of H₂ for 24 hours. The catalyst was filtered off through Celite and the filtrate was partially concentrated to give crude (8aS)-4-(1H-pyrazol-4-yl)-1,2,3,4,6,7,8,8a-octahydropyrrolo[1,2-a]pyrazine. The crude (8a,S)-4-(1H-pyrazol-4-yl)-1,2,3,4,6,7,8,8a-octahydropyrrolo[1,2-a]pyrazine was dissolved in NMP (1 mL) and DIPEA (100 μL, 0.5741 mmol) and 3-(4-chloropyrimidin-2-yl)-6-(trifluoromethyl)imidazo[1,2-a]pyrazine (30 mg, 0.1001 mmol) was added and stirred at 90° C. for 3 hours. The material was purified by reverse phase chromatography (C18; MeCN/water—0.1% ammonium hydroxide as eluent) to give: 3-(4-((8aS)-4-(1H-pyrazol-4-yl)hexahydropyrrolo[1,2-a]pyrazin-2(1H)-yl)pyrimidin-2-yl)-6-(trifluoromethyl)imidazo[1,2-a]pyrazine (trifluoroacetate salt) (2.4 mg, 4%); MS m/z 456.3 (M+H)⁺.

Example 102: 3-(4-(3-((1H-Pyrazol-4-yl)oxy)pyrrolidin-1-yl)pyrimidin-2-yl)-6-(trifluoromethyl)imidazo[1,2-a]pyrazine, IV-695

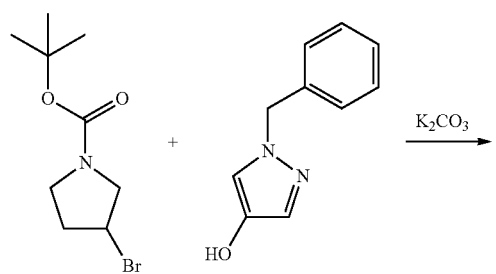

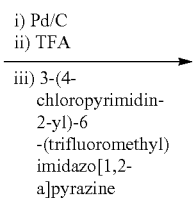

i) Pd/C
ii) TFA
iii) 3-(4-chloropyrimidin-2-yl)-6-(trifluoromethyl)imidazo[1,2-a]pyrazine

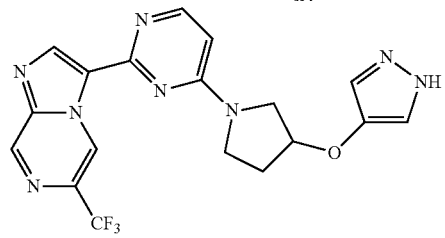

Step 1: tert-Butyl 3-((1-benzyl-1H-pyrazol-4-yl)oxy)pyrrolidine-1-carboxylate

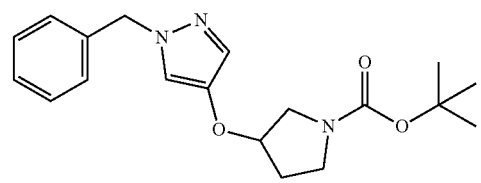 [SMILES: CC(C)(C)OC(=O)N1CCC(Oc2cnn(Cc3ccccc3)c2)C1]

A sealed vial was charged with tert-butyl 3-bromopyrrolidine-1-carboxylate (480 mg, 1.92 mmol), 1-benzylpyrazol-4-ol (330 mg, 1.89 mmol), and K₂CO₃ (850 mg, 6.15 mmol) in DMF (3 mL) and the reaction stirred at 110° C. for 4 hours. The crude mixture was purified directly by column chromatography (silica, eluting with a 0-100% EtOAc/Petroleum ether) to give tert-butyl 3-((1-benzyl-1H-pyrazol-4-yl)oxy)pyrrolidine-1-carboxylate (260 mg, 40%) as a pale brown solid; ES+ [M+H]=344.3.

Step 2: 4-(Pyrrolidin-3-yloxy)-1H-pyrazole

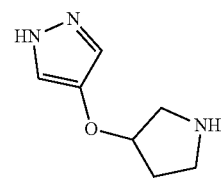

tert-Butyl 3-((1-benzyl-1H-pyrazol-4-yl)oxy)pyrrolidine-1-carboxylate (68 mg, 0.20 mmol), palladium on carbon (10% w/w wet, Degussa, 35 mg, 0.033 mmol) and concentrated HCl (100 μL of 12 M, 1.20 mmol) were dissolved in methanol (2 mL) and the mixture stirred at ambient temperature under a balloon of hydrogen for 22 hours. The reaction was filtered through Celite and concentrated in vacuo. The residue was dissolved in DCM (2 mL) and TFA (1.5 mL, 19.5 mmol) was added. After stirring for 4 hours at ambient temperature the reaction was concentrated in vacuo to give 4-(pyrrolidin-3-yloxy)-1H-pyrazole, which was used directly in the next step.

Step 3: 3-(4-(3-((1H-Pyrazol-4-yl)oxy)pyrrolidin-1-yl)pyrimidin-2-yl)-6-(trifluoromethyl)imidazo[1,2-a]pyrazine

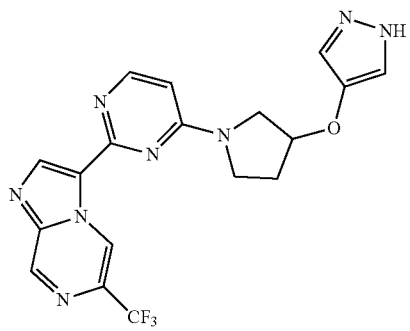 [SMILES: FC(F)(F)c1cn2c(-c3nccc(N4CCC(Oc5cn[nH]c5)C4)n3)cnc2cn1]

The crude 4-(pyrrolidin-3-yloxy)-1H-pyrazole was dissolved in DMSO (1 mL), and DIPEA (200 µL, 1.15 mmol) and 3-(4-chloropyrimidin-2-yl)-6-(trifluoromethyl)imidazo[1,2-a]pyrazine (30.0 mg, 0.099 mmol) were added. The reaction was stirred at 90° C. for 3 hours. The mixture was purified reverse phase chromatography (C18; MeCN/water—0.1% ammonium hydroxide as eluent) to give 3-(4-(3-((1H-pyrazol-4-yl)oxy)pyrrolidin-1-yl)pyrimidin-2-yl)-6-(trifluoromethyl)imidazo[1,2-a]pyrazine (23.5 mg, 57% over three steps); $^1$H NMR (500 MHz, Methanol-$d_4$) δ 10.44 (d, J=5.2 Hz, 1H), 9.18 (s, 1H), 8.64 (d, J=3.8 Hz, 1H), 8.34-8.21 (m, 1H), 7.40 (s, 2H), 6.50 (s, 1H), 4.93 (s, 1H), 4.56 (s, 1H), 3.91 (d, J=9.2 Hz, 1H), 3.77-3.58 (m, 1H), 2.43 (s, 1H), 2.32 (d, J=16.0 Hz, 1H), 1.30 (d, J=6.7 Hz, 1H); ES+ [M+H]=417.3.

Example 103: 6-(Difluoromethyl)-3-[4-[(3S)-3-(sulfamoylamino)-1-piperidyl]pyrimidin-2-yl]imidazo[1,2-a]pyrazine, IV-179

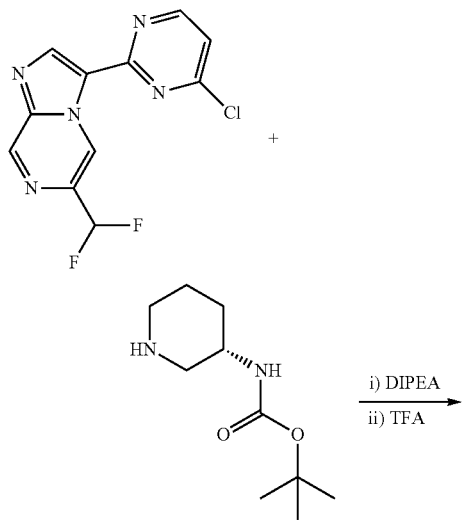

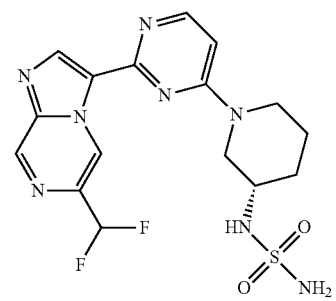

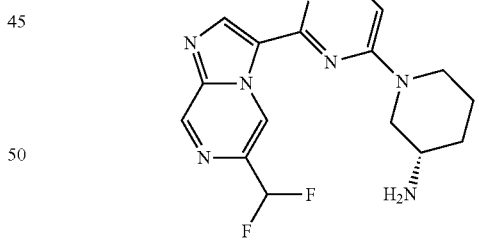

Step 1: (S)-1-(2-(6-(Difluoromethyl)imidazo[1,2-a]pyrazin-3-yl)pyrimidin-4-yl)piperidin-3-amine 3-(4-Chloropyrimidin-2-yl)-6-(difluoromethyl)imidazo[1,2-a]pyrazine (30 mg, 0.11 mmol), tert-butyl N-[(3S)-3-piperidyl]carbamate (42.66 mg, 0.21 mmol) and DIPEA (68.82 mg, 92.75 µL, 0.53 mmol) were dissolved in NMP and heated to 120° C. in the microwave for 30 mins. TFA (0.2 mL) was added and the resulting mixture stirred at ambient temperature for 1 hour and then the mixture was heated in the microwave for 30 mins at 100° C. The reaction mixture was then diluted with DMSO (2 mL) and purified by reverse phase chromatography (C18; MeCN/water—0.05% TFA as eluent). The residual oily solid was then reacted on directly (20.0 mg, 34%); MS m/z 446.1 (M+H)$^+$.

1211

Step 2: 6-(Difluoromethyl)-3-[4-[(3S)-3-(sulfamoylamino)-1-piperidyl]pyrimidin-2-yl]imidazo[1,2-a]pyrazine

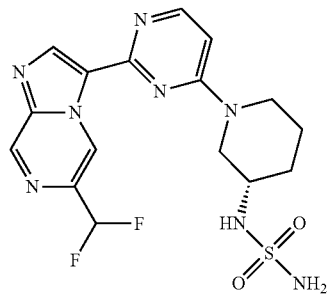 [SMILES: NS(=O)(=O)N[C@H]1CCCN(c2ccnc(-c3cnc4cnc(C(F)F)cn34)n2)C1]

(3S)-1-[2-[6-(Difluoromethyl)imidazo[1,2-a]pyrazin-3-yl]pyrimidin-4-yl]piperidin-3-amine (10 mg, 0.029 mmol) and sulfamide (27.83 mg, 17.27 µL, 0.290 mmol) were combined in dioxane (1 mL) and heated to 100° C. for 1 hour in a sealed tube. The reaction mixture was cooled to ambient temperature, DMSO (1 mL) was added and the mixture purified directly by reverse phase chromatography (C18; MeCN/water—0.05% TFA as eluent) to give 6-(difluoromethyl)-3-[4-[(3S)-3-(sulfamoylamino)-1-piperidyl]pyrimidin-2-yl]imidazo[1,2-a]pyrazine (3.6 mg, 23%); $^1$H NMR (400 MHz, Methanol-$d_4$) δ 9.96 (d, J=1.4 Hz, 1H), 9.26 (d, J=1.4 Hz, 1H), 8.71 (s, 1H), 8.29 (d, J=7.0 Hz, 1H), 6.97-6.87 (m, 2H), 4.45 (s, 1H), 4.18 (s, 1H), 3.63 (d, J=19.7 Hz, 1H), 3.61-3.52 (m, 3H), 2.18 (s, 1H), 1.77 (s, 2H); MS m/z 425.1 (M+H)$^+$.

The following compound was made using methodology similar to Example 103:

6-(Difluoromethyl)-3-[4-[(3R)-3-(sulfamoylamino)-1-piperidyl]pyrimidin-2-yl]imidazo[1,2-a]pyrazine IV-181.

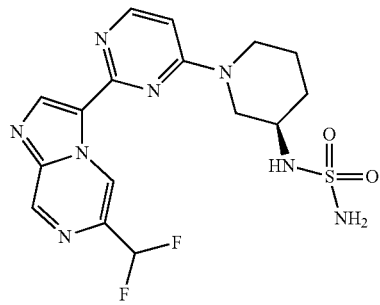 [SMILES: NS(=O)(=O)N[C@@H]1CCCN(c2ccnc(-c3cnc4cnc(C(F)F)cn34)n2)C1]

1212

Example 104: (3S)—N-(Diamino-hydroxy-oxo-$\lambda^6$-sulfanyl)-1-[2-[6-(difluoromethyl)imidazo[1,2-a]pyrazin-3-yl]pyrimidin-4-yl]piperidin-3-amine, IV-180

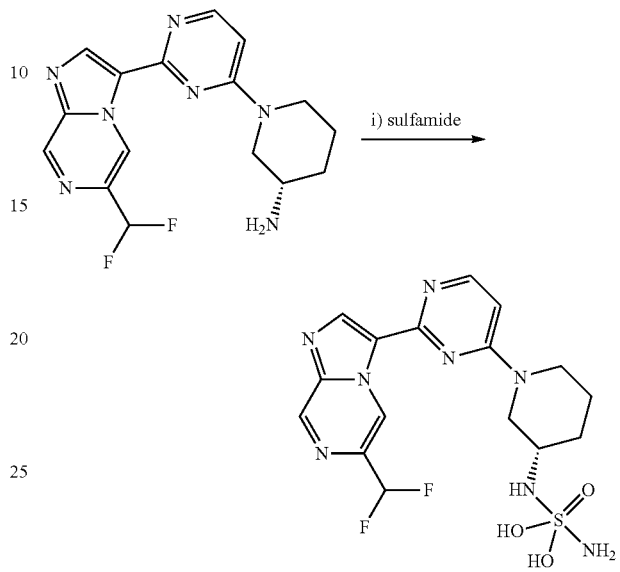

(3S)-1-[2-[6-(Difluoromethyl)imidazo[1,2-a]pyrazin-3-yl]pyrimidin-4-yl]piperidin-3-amine (10 mg, 0.029 mmol) and sulfamide (27.83 mg, 17.27 µL, 0.290 mmol) were combined in dioxane (1 mL) and heated to 100° C. for 16 hours in a sealed tube. The mixture was diluted with DMSO (1 mL) and purified directly by reverse phase chromatography (C18; MeCN/water—0.05% TFA as eluent) to give (3S)—N-(diamino-hydroxy-oxo-$\lambda^6$-sulfanyl)-1-[2-[6-(difluoromethyl)imidazo[1,2-a]pyrazin-3-yl]pyrimidin-4-yl]piperidin-3-amine (10.4 mg, 53%) as a TFA salt; $^1$H NMR (400 MHz, Methanol-$d_4$) δ 9.82 (s, 1H), 9.33 (dd, J=1.6, 0.8 Hz, 1H), 8.78 (d, J=0.9 Hz, 1H), 8.32 (dd, J=7.4, 0.9 Hz, 1H), 7.12-7.00 (m, 2H), 4.85 (s, 1H), 4.41 (s, 1H), 4.02 (td, J=9.9, 4.8 Hz, 1H), 3.55-3.39 (m, 2H), 2.23-2.13 (m, 1H), 2.07 (dq, J=11.8, 4.1, 3.6 Hz, 1H), 1.95-1.76 (m, 2H); MS m/z 442.2 (M+H)$^+$.

The following compound was made using methodology similar to Example 104:

(R)-3-(4-(3-((Di amino-(hydroxy)sulfinyl)amino)piperidin-1-yl)pyrimidin-2-yl)-6-(difluoromethyl)imidazo[1,2-a]pyrazine IV-178.

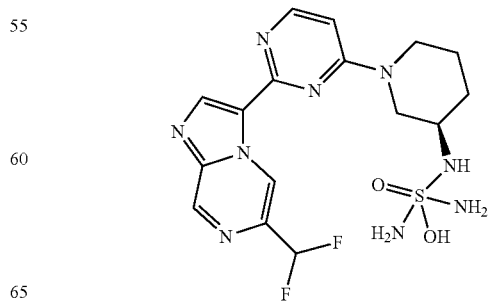

Example 105: 3-(4-(3-(4H-1,2,4-Triazol-4-yl)piperi-din-1-yl)pyrimidin-2-yl)-6-(trifluoromethyl)imidazo[1,2-a]pyrazine and N-(1-(2-(6-(trifluoromethyl)imidazo[1,2-a]pyrazin-3-yl)pyrimidin-4-yl)piperidin-3-yl)formamide, IV-752 and IV-332

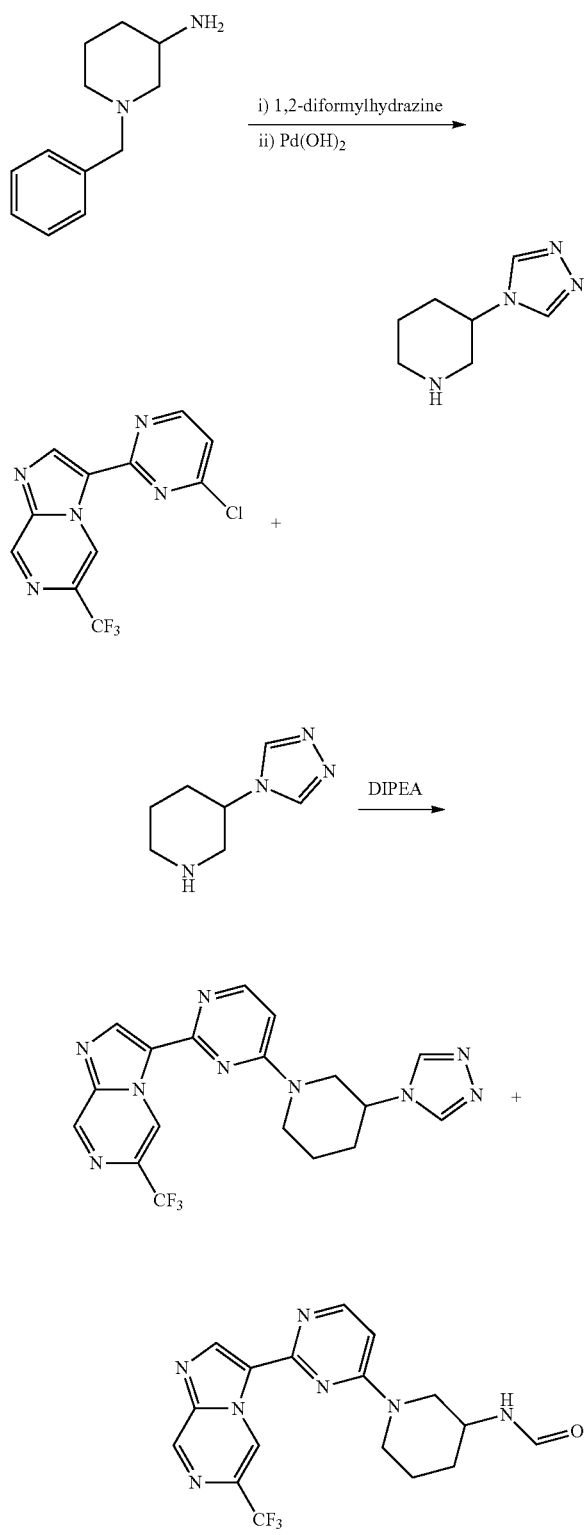

Step 1: 3-(4H-1,2,4-Triazol-4-yl)piperidine

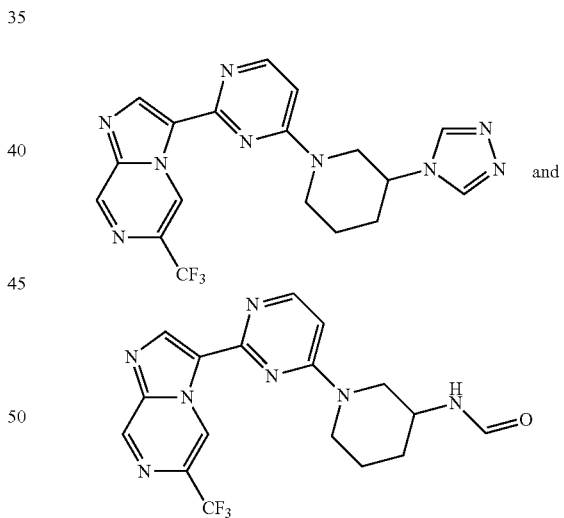

To a solution of 1-benzylpiperidin-3-amine (dihydrochloride salt) (101 mg, 0.384 mmol), N-formamidoformamide (112 mg, 1.272 mmol), Et$_3$N (550 μL, 3.946 mmol) in pyridine (5 mL) was added TMSCl (750 μL, 5.909 mmol) and the mixture was heated at 100° C. for 16 hours. The reaction mixture was cooled to ambient temperature and partitioned between DCM and saturated aqueous NaHCO$_3$ solution. The organic layers were separate, dried over MgSO$_4$ and concentrated in vacuo. The material was dissolved in methanol (10 mL), Pd(OH)$_2$ (53.88 mg, 0.384 mmol) was added and the mixture was stirred for 16 hours under an atmosphere of H$_2$. The catalyst was filtered off and the filtrate was concentrated in vacuo to give 3-(4H-1,2,4-triazol-4-yl)piperidine which was used in next step without further purification, assumed quantitative yield.

Step 2: 3-(4-(3-(4H-1,2,4-Triazol-4-yl)piperidin-1-yl)pyrimidin-2-yl)-6-(trifluoromethyl)imidazo[1,2-a]pyrazine and N-(1-(2-(6-(trifluoromethyl)imidazo[1,2-a]pyrazin-3-yl)pyrimidin-4-yl)piperidin-3-yl)formamide A mixture of 3-(1,2,4-triazol-4-yl)piperidine (60 mg, 0.394 mmol), 3-(4-chloropyrimidin-2-yl)-6-(trifluoromethyl)imidazo[1,2-a]pyrazine (62.1 mg, 0.197 mmol) and DIPEA (152.8 mg, 205.9 μL, 1.182 mmol) in NMP (3 mL) was heated at 75° C. for 16 hours. The crude mixture was purified directly by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. Product fractions were combined and lyophilised to give:

N-[1-[2-[6-(Trifluoromethyl)imidazo[1,2-a]pyrazin-3-yl]pyrimidin-4-yl]-3-piperidyl]formamide (trifluoroacetate salt) (4.03 mg, 1%); ¹H NMR (500 MHz, DMSO-d₆) δ 10.19 (s, 1H), 9.42-9.30 (m, 1H), 8.71 (s, 1H), 8.39 (d, J=6.3 Hz, 1H), 8.26-8.18 (m, 1H), 8.00 (dd, J=1.7, 0.9 Hz, 1H), 6.85 (d, J=6.4 Hz, 1H), 4.09 (d, J=83.8 Hz, 2H), 3.92-3.77 (m, 1H), 3.51 (dt, J=20.2, 7.0 Hz, 1H), 3.42-3.31 (m, 1H), 2.00-1.74 (m, 2H), 1.61 (tt, J=12.0, 9.4 Hz, 2H); MS m/z 392.2 (M+H)⁺.
and 3-[4-[3-(1,2,4-TriazolTriazol-4-yl)-1-piperidyl]pyrimidin-2-yl]-6-(trifluoromethyl)imidazo[1,2-a]pyrazine (trifluoroacetate salt (0.5)), (4.75 mg, 1.3%); ¹H NMR (500 MHz, DMSO-d₆) δ 10.21 (d, J=1.5 Hz, 1H), 9.37 (d, J=1.3 Hz, 1H), 9.15-9.01 (m, 2H), 8.79 (s, 1H), 8.46 (d, J=6.3 Hz, 1H), 7.00 (d, J=6.3 Hz, 1H), 4.67 (d, J=23.8 Hz, 1H), 4.58-4.46 (m, 1H), 4.41 (d, J=40.7 Hz, 1H), 3.62 (dd, J=13.1, 9.8 Hz, 1H), 3.24 (ddd, J=13.9, 11.3, 3.1 Hz, 1H), 2.28 (dq, J=12.9, 4.2 Hz, 1H), 2.23-2.08 (m, 1H), 1.99-1.86 (m, 1H), 1.67 (dtt, J=13.5, 11.3, 4.0 Hz, 1H); MS m/z 416.2 (M+H)⁺.

Example 106: 3-(4-(3-(Piperidin-3-yl)-1H-pyrazol-1-yl)pyrimidin-2-yl)-6-(trifluoromethyl)imidazo[1,2-a]pyrazine, IV-634

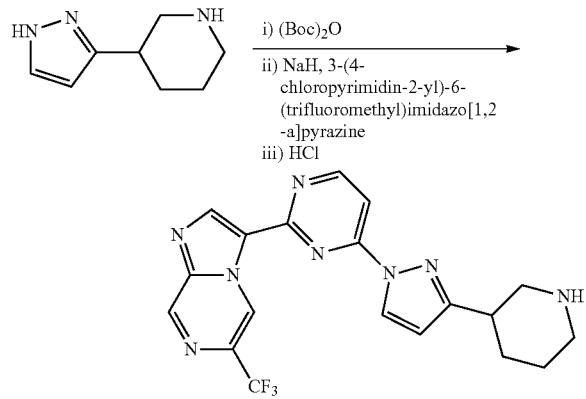

3-(1H-Pyrazol-3-yl)piperidine (50 mg, 0.33 mmol) was dissolved in dioxane (2.6 mL) and water (0.6 2.1 mm×50 mm, 1.7 µL) before addition of sodium carbonate (52.5 mg, 0.50 mmol), followed by tert-butoxycarbonyl tert-butyl carbonate (144.3 mg, 0.66 mmol). The suspension was stirred at ambient temperature for 2 hours. The reaction was quenched with K₂CO₃ (2 M, 0.5 mL) before extracting with DCM (2×2 mL). The organic layer was then filtered through a hydrophobic frit and concentrated in vacuo. The crude oil was dissolved in DMF and cooled to 0° C. before addition of NaH (15.8 mg, 0.40 mmol). The suspension was stirred for 15 minutes before addition of 3-(4-chloropyrimidin-2-yl)-6-(trifluoromethyl)imidazo[1,2-a]pyrazine (69.4 mg, 0.23 mmol) and the resulting mixture was heated to 80° C. for 45 mins and then at 100° C. for a further 5 hours. The reaction mixture was purified by (C18; MeCN/water—0.1% ammonium hydroxide as eluent). The purified material was dissolved in HCl in MeOH (110 µL, 0.33 mmol, 3 M solution) and the resulting mixture stirred at ambient temperature for 3 hours and then additional HCl in MeOH (110 µL, 0.33 mmol, 3 M solution) was added and the resulting mixture stirred at ambient temperature for 24 hours. The resulting suspension was diluted with DCM and purified by (C18; MeCN/water—0.1% ammonium hydroxide as eluent) to give 3-(4-(3-(piperidin-3-yl)-1H-pyrazol-1-yl)pyrimidin-2-yl)-6-(trifluoromethyl)imidazo[1,2-a]pyrazine (18 mg, 12%); ¹H NMR (500 MHz, Methanol-d₄) δ 10.31 (dd, J=1.5, 0.8 Hz, 1H), 9.30-9.21 (m, 1H), 8.97 (d, J=5.6 Hz, 1H), 8.87 (s, 1H), 8.77 (d, J=2.8 Hz, 1H), 7.87 (d, J=5.6 Hz, 1H), 6.67 (d, J=2.8 Hz, 1H), 3.72-3.61 (m, 1H), 3.47-3.33 (m, 2H), 3.33-3.21 (m, 1H), 3.11 (ddd, J=12.8, 11.0, 3.6 Hz, 1H), 2.33-2.24 (m, 1H), 2.10-1.99 (m, 1H), 2.00-1.84 (m, 2H); MS m/z 415.1 (M+H)⁺.

TABLE 7

Analytical data for compounds of Formula IV

| IV- | LCMS_Plus | LCMS_RT | NMR |
|---|---|---|---|
| IV-1 | 312.1 | 0.76 | 1H NMR (400 MHz, DMSO) δ 11.40 (s, 1H), 9.92 (dd, J = 4.7, 1.4 Hz, 1H), 9.23 (d, J = 1.4 Hz, 1H), 8.74 (s, 1H), 8.21-7.96 (m, 3H), 7.86 (d, J = 6.7 Hz, 1H), 7.66-7.54 (m, 2H), 7.51 (t, J = 2.7 Hz, 1H), 7.30 (t, J = 7.7 Hz, 1H), 6.87 (s, 1H). |
| IV-2 | 323.2 | 1.83 | 1H NMR (500 MHz, DMSO) δ 9.54 (dd, J = 4.5, 1.6 Hz, 1H), 9.17 (t, J = 1.9 Hz, 1H), 8.49 (s, 1H), 8.08 (d, J = 4.5 Hz, 1H), 7.72 (dd, J = 8.6, 7.4 Hz, 1H), 7.37 (d, J = 7.4 Hz, 1H), 6.88 (d, J = 8.6 Hz, 1H), 3.72-3.62 (m, 6H), 3.62-3.54 (m, 2H), 2.09 (d, J = 2.8 Hz, 3H). |
| IV-3 | 417.1 | 2.23 | |
| IV-4 | 389.2 | 2.09 | 1H NMR (500 MHz, Methanol-d4) δ 9.49-9.41 (m, 1H), 9.12 (d, J = 1.4 Hz, 1H), 8.65 (s, 1H), 8.32 (d, J = 7.2 Hz, 1H), 7.78 (s, 2H), 7.04 (d, J = 7.2 Hz, 1H), 4.79 (dd, J = 10.8, 2.5 Hz, 1H), 4.25-4.18 (m, 1H), 3.89 (td, J = 11.8, 2.8 Hz, 1H), 3.61-3.47 (m, 2H), 2.03 (s, 2H), 1.30 (s, 2H). |
| IV-5 | 472.1 | 2.65 | 1H NMR (500 MHz, DMSO-d6) δ 9.85 (d, J = 1.4 Hz, 1H), 9.15 (d, J = 1.4 Hz, 1H), |

TABLE 7-continued

Analytical data for compounds of Formula IV

| IV- | LCMS_Plus | LCMS_RT | NMR |
|---|---|---|---|
| | | | 8.72 (s, 1H), 8.48 (d, J = 6.3 Hz, 1H), 7.46-7.30 (m, 1H), 6.95 (d, J = 6.3 Hz, 1H), 5.23-4.33 (m, 2H), 3.52-3.41 (m, 1H), 3.06-2.99 (m, 1H), 2.98 (s, 3H), 2.94-2.82 (m, 2H), 2.20 (d, J = 27.3 Hz, 2H), 1.08 (d, J = 6.7 Hz, 3H). |
| IV-6 | 383.1 | 2.05 | 1H NMR (500 MHz, DMSO-d6) δ 9.80 (d, J = 1.5 Hz, 1H), 9.14 (d, J = 1.3 Hz, 1H), 8.67 (s, 1H), 8.44 (d, J = 6.3 Hz, 1H), 7.72 (s, 2H), 6.95 (d, J = 6.4 Hz, 1H), 4.61 (dd, J = 10.4, 2.7 Hz, 1H), 4.57-4.20 (m, 2H), 4.06 (ddd, J = 11.6, 3.6, 1.7 Hz, 1H), 3.72 (td, J = 11.6, 2.8 Hz, 1H), 3.28-3.14 (m, 2H). |
| IV-7 | 417.1 | 2.23 | 1H NMR (500 MHz, DMSO-d6) δ 12.83 (s, 1H), 10.23 (s, 1H), 9.36 (d, J = 1.4 Hz, 1H), 8.75 (s, 1H), 8.45 (d, J = 6.3 Hz, 1H), 7.82 (s, 1H), 7.58 (s, 1H), 6.96 (d, J = 6.4 Hz, 1H), 4.60 (dd, J = 10.5, 2.7 Hz, 1H), 4.47 (s, 2H), 4.09-4.01 (m, 1H), 3.72 (td, J = 11.6, 2.8 Hz, 1H), 3.27-3.15 (m, 2H). |
| IV-8 | 417.1 | 2.23 | 1H NMR (500 MHz, DMSO-d6) δ 12.83 (s, 1H), 10.23 (s, 1H), 9.36 (d, J = 1.4 Hz, 1H), 8.75 (s, 1H), 8.45 (d, J = 6.3 Hz, 1H), 7.82 (s, 1H), 7.58 (s, 1H), 6.96 (d, J = 6.4 Hz, 1H), 4.60 (dd, J = 10.5, 2.7 Hz, 1H), 4.47 (s, 2H), 4.09-4.01 (m, 1H), 3.72 (td, J = 11.6, 2.8 Hz, 1H), 3.27-3.15 (m, 2H). |
| IV-9 | 397.2 | 2.24 | 1H NMR (500 MHz, Methanol-d4) δ 9.95 (d, J = 1.3 Hz, 1H), 8.98 (d, J = 1.3 Hz, 1H), 8.62 (s, 1H), 8.38 (d, J = 6.3 Hz, 1H), 7.66 (s, 2H), 6.79 (d, J = 6.4 Hz, 1H), 4.90 (d, J = 3.0 Hz, 1H), 4.56 (s, 2H), 4.22 (dd, J = 11.5, 4.2 Hz, 1H), 3.87 (td, J = 11.8, 3.1 Hz, 1H), 3.49-3.36 (m, 1H), 1.14 (d, J = 6.8 Hz, 3H). |
| IV-10 | 431.2 | 2.39 | |
| IV-11 | 431.2 | 2.4 | 1H NMR (500 MHz, DMSO-d6) δ 12.71 (s, 1H), 10.24 (dd, J = 1.5, 0.8 Hz, 1H), 9.36 (dd, J = 1.5, 0.6 Hz, 1H), 8.76 (s, 1H), 8.42 (d, J = 6.3 Hz, 1H), 7.57 (s, 2H), 6.94 (s, 1H), 5.08 (t, J = 4.1 Hz, 1H), 3.93 (s, 1H), 3.77 (s, 1H), 3.25 (d, J = 7.9 Hz, 1H), 1.20 (d, J = 6.3 Hz, 3H), 2H not observed. |
| IV-12 | 431.2 | 2.42 | 1H NMR (500 MHz, DMSO-d6) δ 12.81 (s, 1H), 10.23 (s, 1H), 9.36 (d, J = 1.3 Hz, 1H), 8.75 (s, 1H), 8.43 (d, J = 6.3 Hz, 1H), 7.69 (s, 2H), 6.97 (d, J = 6.3 Hz, 1H), 4.62 (dd, J = 10.8, 2.6 Hz, 1H), 3.85-3.73 (m, 1H), 3.07 (t, J = 12.0 Hz, 1H), 2.78 (t, J = 11.9 Hz, 1H), 1.25 (d, J = 6.2 Hz, 3H), 2H not observed. |
| IV-13 | 430.9 | 2.4 | 1H NMR (500 MHz, DMSO-d6) δ 12.82 (s, 1H), 10.22 (s, 1H), 9.43-9.25 (m, 1H), 8.74 (s, 1H), 8.43 (d, J = 6.2 Hz, 1H), 7.80 (s, 1H), 7.59 (s, 1H), 6.96 (d, J = 6.3 Hz, 1H), 4.62 (dd, J = 11.0, 2.7 Hz, 1H), 4.46 (s, 2H), 3.79 (ddd, J = 10.8, 6.2, 2.7 Hz, 1H), 3.07 (dd, J = 13.1, 11.0 Hz, 1H), 2.85-2.69 (m, 1H), 1.25 (d, J = 6.2 Hz, 3H). |
| IV-14 | 431.1 | 2.41 | 1H NMR (500 MHz, DMSO-d6) δ 12.82 (s, 1H), 10.22 (s, 1H), 9.43-9.25 (m, 1H), 8.74 (s, 1H), 8.43 (d, J = 6.2 Hz, 1H), 7.80 (s, 1H), 7.59 (s, 1H), 6.96 (d, J = 6.3 Hz, 1H), 4.62 (dd, J = 11.0, 2.7 Hz, 1H), 4.46 (s, 2H), 3.79 (ddd, J = 10.8, 6.2, 2.7 Hz, 1H), 3.07 (dd, J = 13.1, 11.0 Hz, 1H), 2.85-2.69 (m, 1H), 1.25 (d, J = 6.2 Hz, 3H). |
| IV-15 | 431.3 | 2.37 | |
| IV-16 | 431.1 | 2.37 | |
| IV-17 | 506.1 | 2.85 | 1H NMR (500 MHz, DMSO-d6) δ 10.25 (s, 1H), 9.37 (d, J = 1.3 Hz, 1H), 8.79 (s, 1H), 8.50 (d, J = 6.3 Hz, 1H), 7.37 (s, 1H), 7.00-6.91 (m, 1H), 5.13-4.34 (m, 2H), 3.46 (ddd, J = 13.5, 6.3, 3.4 Hz, 1H), 3.05-2.95 (m, |

TABLE 7-continued

Analytical data for compounds of Formula IV

| IV- | LCMS_Plus | LCMS_RT | NMR |
|---|---|---|---|
| | | | 4H), 2.93-2.80 (m, 2H), 2.29-2.11 (m, 2H), 1.06 (d, J = 6.7 Hz, 3H). |
| IV-18 | 374.2 | 1.92 | 1H NMR (500 MHz, DMSO-d6) δ 10.29 (d, J = 1.4 Hz, 1H), 9.31 (d, J = 1.4 Hz, 1H), 8.75 (s, 1H), 8.44 (d, J = 6.3 Hz, 1H), 7.70 (s, 2H), 6.96 (d, J = 6.3 Hz, 1H), 4.59 (dd, J = 10.4, 2.7 Hz, 1H), 4.05 (ddd, J = 11.7, 3.6, 1.7 Hz, 1H), 3.70 (td, J = 11.6, 2.8 Hz, 1H), 3.26-3.11 (m, 2H), 3H not observed. |
| IV-19 | 429.1 | 2.08 | 1H NMR (500 MHz, DMSO-d6) δ 9.90 (d, J = 1.4 Hz, 1H), 9.10 (d, J = 1.3 Hz, 1H), 8.64 (s, 1H), 8.43 (d, J = 6.3 Hz, 1H), 7.71 (s, 2H), 6.93 (d, J = 6.4 Hz, 1H), 4.59 (dd, J = 10.5, 2.7 Hz, 1H), 4.05 (ddd, J = 11.7, 3.6, 1.7 Hz, 1H), 3.75-3.67 (m, 1H), 3.19 (td, J = 13.5, 9.9 Hz, 2H), 3H not observed. |
| IV-20 | 363.2 | 1.86 | 1H NMR (500 MHz, DMSO-d6) δ 9.49 (s, 1H), 9.15 (d, J = 1.4 Hz, 1H), 8.58 (s, 1H), 8.41 (d, J = 6.3 Hz, 1H), 7.71 (s, 2H), 6.93 (d, J = 6.4 Hz, 1H), 4.61 (dd, J = 10.6, 2.7 Hz, 1H), 4.10-4.00 (m, 1H), 3.73 (dd, J = 11.6, 2.8 Hz, 1H), 3.21 (dd, J = 13.3, 10.4 Hz, 2H), 2.48 (s, 3H), 3H not observed. |
| IV-21 | 488.1 | 2.57 | 1H NMR (500 MHz, DMSO-d6) δ 10.07 (s, 1H), 9.33 (d, J = 1.3 Hz, 1H), 8.75 (s, 1H), 8.49 (d, J = 6.3 Hz, 1H), 7.38 (s, 1H), 7.23 (t, J = 54.6 Hz, 1H), 6.95 (d, J = 8.1 Hz, 1H), 3.48-3.45 (m, 1H), 3.03-2.98 (m, 4H), 2.90-2.85 (m, 2H), 2.21 (br d, J = 28.0 Hz, 2H), 1.07 (d, J = 6.7 Hz, 3H). One × CH2 not observed. |
| IV-22 | 374.1 | 1.94 | 1H NMR (500 MHz, DMSO-d6) δ 10.06 (d, J = 1.5 Hz, 1H), 9.32 (d, J = 1.3 Hz, 1H), 8.68 (s, 1H), 8.43 (d, J = 6.3 Hz, 1H), 7.24 (t, J = 54.5 Hz, 1H), 6.87 (d, J = 6.3 Hz, 1H), 3.80 (br d, J = 30.3 Hz, 4H), 3.63-3.61 (m, 4H), 2.08 (s, 3H). |
| IV-23 | 440.1 | 2.01 | 1H NMR (500 MHz, DMSO-d6) δ 10.06 (d, J = 1.1 Hz, 1H), 9.32 (d, J = 1.3 Hz, 1H), 8.71 (s, 1H), 8.45 (d, J = 6.3 Hz, 1H), 7.37-7.03 (m, 2H), 6.85 (d, J = 6.3 Hz, 1H), 4.04-4.01 (m, 1H), 3.63-3.56 (m, 3H), 3.21-3.11 (m, 4H), 2.96 (s, 3H), 2.89-2.84 (m, 1H). |
| IV-24 | 392.2 | 2.22 | 1H NMR (500 MHz, Methanol-d4) δ 10.35 (dd, J = 1.5, 0.8 Hz, 1H), 9.23 (dd, J = 1.3, 0.7 Hz, 1H), 8.68 (s, 1H), 8.49 (d, J = 5.2 Hz, 1H), 7.29 (d, J = 5.2 Hz, 1H), 4.05-3.98 (m, 2H), 3.98-3.91 (m, 2H), 3.80-3.74 (m, 2H), 3.74-3.69 (m, 2H), 2.19 (s, 3H). |
| IV-25 | 354.2 | 1.9 | 1H NMR (500 MHz, Methanol-d4) δ 9.39 (d, J = 1.4 Hz, 1H), 8.90 (d, J = 1.4 Hz, 1H), 8.55 (s, 1H), 8.42 (d, J = 5.3 Hz, 1H), 7.23 (d, J = 5.3 Hz, 1H), 4.05 (s, 3H), 4.04-3.98 (m, 2H), 3.98-3.91 (m, 2H), 3.75 (ddd, J = 13.2, 6.6, 4.3 Hz, 4H), 2.19 (s, 3H). |
| IV-26 | 354.2 | 1.61 | 1H NMR (500 MHz, DMSO-d6) δ 9.82 (q, J = 1.4 Hz, 1H), 9.18 (d, J = 1.4 Hz, 1H), 8.73 (s, 1H), 8.49 (d, J = 5.2 Hz, 1H), 7.34 (d, J = 5.2 Hz, 1H), 4.74 (d, J = 1.4 Hz, 2H), 3.93-3.90 (m, 2H), 3.86-3.84 (m, 2H), 3.63-3.59 (m, 4H), 2.08 (s, 3H). |
| IV-27 | 454.1 | 2.2 | 1H NMR (500 MHz, DMSO-d6) δ 10.01 (s, 1H), 9.12 (s, 1H), 8.58 (s, 1H), 8.34 (d, J = 6.2 Hz, 1H), 7.22 (t, J = 6.3 Hz, 1H), 6.50 (s, 1H), 3.91-3.66 (m, 4H), 3.24 (s, 3H), 3.08-3.05 (m, 2H), 2.94 (s, 3H), 2.16 (s, 1H), 1.85 (s, 1H). |
| IV-28 | 399 | 1.94 | 1H NMR (500 MHz, DMSO-d6) δ 10.04 (q, J = 1.3 Hz, 1H), 9.31 (d, J = 1.4 Hz, 1H), 8.70 (s, 1H), 8.44 (d, J = 6.3 Hz, 1H), 7.70 (s, 2H), 7.19 (t, J = 54.6 Hz, 1H), 6.95 (d, J = 6.3 Hz, 1H), 4.60 (dd, J = 10.4, 2.7 Hz, 2H), 4.07-4.04 (m, 1H), 3.72 (td, J = 11.6, 2.8 Hz, 1H), 3.25-3.17 (m, 3H). |

TABLE 7-continued

Analytical data for compounds of Formula IV

| IV- | LCMS_Plus | LCMS_RT | NMR |
|---|---|---|---|
| IV-29 | 438.1 | 2.25 | 1H NMR (500 MHz, DMSO-d6) δ 10.08-10.07 (m, 1H), 9.31 (d, J = 1.4 Hz, 1H), 8.67 (s, 1H), 8.38 (d, J = 6.3 Hz, 1H), 7.22 (t, J = 54.5 Hz, 1H), 7.15 (t, J = 6.0 Hz, 1H), 6.83 (d, J = 6.4 Hz, 1H), 4.36 (br s, 2H), 3.12 (ddd, J = 13.8, 11.3, 3.1 Hz, 1H), 2.97-2.86 (m, 3H), 2.92 (s, 3H), 1.90-1.85 (m, 1H), 1.80-1.77 (m, 1H), 1.73-1.70 (m, 1H), 1.53-1.45 (m, 1H), 1.38-1.30 (m, 1H). |
| IV-30 | 368.2 | 1.23 | 1H NMR (500 MHz, Methanol-d4) δ 10.77 (d, J = 1.4 Hz, 1H), 9.17 (d, J = 1.3 Hz, 1H), 8.68 (s, 1H), 8.48 (d, J = 5.2 Hz, 1H), 7.29 (d, J = 5.2 Hz, 1H), 4.02 (ddd, J = 26.6, 6.5, 4.0 Hz, 4H), 3.75 (dt, J = 21.9, 5.3 Hz, 4H), 2.20 (s, 3H). |
| IV-31 | 349.3 | 1.88 | 1H NMR (500 MHz, Methanol-d4) δ 10.25 (d, J = 1.4 Hz, 1H), 9.19 (d, J = 1.4 Hz, 1H), 8.68 (s, 1H), 8.50 (d, J = 5.2 Hz, 1H), 7.28 (d, J = 5.2 Hz, 1H), 4.08-3.99 (m, 2H), 3.99-3.92 (m, 2H), 3.82-3.71 (m, 4H), 2.20 (s, 3H). |
| IV-32 | 404.2 | 2.05 | 1H NMR (500 MHz, Methanol-d4) δ 10.00 (d, J = 1.3 Hz, 1H), 9.00 (d, J = 1.3 Hz, 1H), 8.60 (s, 1H), 8.46 (d, J = 5.2 Hz, 1H), 7.26 (d, J = 5.3 Hz, 1H), 4.05-3.97 (m, 2H), 3.97-3.90 (m, 2H), 3.82-3.69 (m, 4H), 2.20 (s, 3H). |
| IV-33 | 364.1 | 2.04 | 1H NMR (500 MHz, Methanol-d4) δ 9.57 (d, J = 1.5 Hz, 1H), 9.08 (d, J = 1.4 Hz, 1H), 8.59 (s, 1H), 8.34 (d, J = 6.8 Hz, 1H), 6.89 (d, J = 6.9 Hz, 1H), 4.06-3.98 (m, 2H), 3.98-3.91 (m, 2H), 3.86-3.76 (m, 4H), 2.26-2.21 (m, 1H), 2.20 (s, 3H), 1.12-1.01 (m, 4H). |
| IV-34 | 440.3 | 2.26 | 1H NMR (500 MHz, DMSO-d6) δ 10.25 (d, J = 3.9 Hz, 1H), 9.37 (d, J = 1.3 Hz, 1H), 8.73 (d, J = 8.5 Hz, 1H), 8.43 (dd, J = 6.3, 1.5 Hz, 1H), 6.84 (d, J = 6.3 Hz, 1H), 4.74-3.03 (m, 10H), 2.43-2.29 (m, 1H), 2.07 (s, 2H), 2.05-1.95 (m, 1H), 1.82-1.74 (m, 1H), 1.66-1.50 (m, 2H). |
| IV-35 | 358.3 | 2.03 | 1H NMR (500 MHz, DMSO-d6) δ 9.83 (d, J = 1.3 Hz, 1H), 9.13 (d, J = 1.3 Hz, 1H), 8.65 (s, 1H), 8.42 (d, J = 6.3 Hz, 1H), 6.85 (d, J = 6.3 Hz, 1H), 3.88-3.78 (m, 2H), 3.78-3.69 (m, 2H), 3.65-3.55 (m, 4H), 2.07 (s, 3H). |
| IV-36 | 367.3 | 1.6 | 1H NMR (500 MHz, DMSO-d6) δ 10.40 (d, J = 1.4 Hz, 1H), 9.27 (s, 1H), 9.21 (d, J = 1.4 Hz, 1H), 8.66 (s, 1H), 8.44 (d, J = 6.2 Hz, 1H), 8.19 (d, J = 16.6 Hz, 1H), 7.81 (s, 1H), 6.86 (d, J = 6.3 Hz, 1H), 3.89-3.80 (m, 2H), 3.80-3.72 (m, 2H), 3.64-3.58 (m, 4H), 2.08 (s, 3H). |
| IV-37 | 350.3 | 2.03 | 1H NMR (500 MHz, DMSO-d6) δ 9.63 (d, J = 1.4 Hz, 1H), 9.21 (d, J = 1.3 Hz, 1H), 8.55 (s, 1H), 8.40 (d, J = 6.3 Hz, 1H), 6.95 (dd, J = 17.0, 10.6 Hz, 1H), 6.84 (d, J = 6.4 Hz, 1H), 6.29 (dd, J = 17.0, 1.9 Hz, 1H), 5.49 (dd, J = 10.6, 1.9 Hz, 1H), 3.87-3.79 (m, 2H), 3.79-3.70 (m, 2H), 3.65-3.60 (m, 4H), 2.08 (s, 3H). |
| IV-38 | 392.4 | 1.46 | |
| IV-39 | 349.3 | 1.68 | 1H NMR (500 MHz, Methanol-d4) δ 9.67 (dd, J = 4.7, 1.5 Hz, 1H), 9.25 (d, J = 1.4 Hz, 1H), 8.68 (s, 1H), 8.36 (d, J = 6.9 Hz, 1H), 8.20 (d, J = 4.7 Hz, 1H), 7.78 (s, 2H), 6.98 (d, J = 6.9 Hz, 1H), 4.77 (dd, J = 10.4, 2.8 Hz, 1H), 4.67-4.46 (m, 2H), 4.24-4.17 (m, 1H), 3.88 (td, J = 11.7, 2.8 Hz, 1H), 3.51-3.38 (m, 2H). |
| IV-40 | 417.3 | 2.19 | 1H NMR (500 MHz, DMSO-d6) δ 10.18 (s, 1H), 9.37 (d, J = 1.4 Hz, 1H), 8.90 (s, 1H), 8.56 (d, J = 5.2 Hz, 1H), 7.66 (s, 2H), 7.42 (d, J = 5.2 Hz, 1H), 4.63-4.54 (m, 2H), |

TABLE 7-continued

Analytical data for compounds of Formula IV

| IV- | LCMS_Plus | LCMS_RT | NMR |
|---|---|---|---|
| | | | 4.52-4.42 (m, 1H), 4.05 (ddd, J = 11.6, 3.5, 1.6 Hz, 1H), 3.76-3.67 (m, 1H), 3.26-3.17 (m, 1H), 2H not observed. |
| IV-41 | 403.15 | 1.96 | |
| IV-42 | 374.15 | 1.86 | |
| IV-43 | 452.05 | 2.38 | |
| IV-44 | 387.95 | 1.95 | |
| IV-45 | 402 | 2.12 | |
| IV-46 | 488.01 | 2.61 | 1H NMR (400 MHz, Chloroform-d) δ 10.07 (s, 1H), 9.37-9.31 (m, 1H), 8.53-8.43 (m, 2H), 7.07 (d, J = 5.5 Hz, 1H), 6.93 (s, 1H), 5.02 (d, J = 13.8 Hz, 1H), 4.78 (d, J = 14.1 Hz, 2H), 3.48 (ddd, J = 112.4, 13.9, 6.1 Hz, 2H), 3.08 (t, J = 12.9 Hz, 1H), 3.00 (s, 3H), 3.00-2.90 (m, 1H), 2.42-2.02 (m, 2H), 1.17 (d, J = 6.8 Hz, 3H). |
| IV-47 | 404.3 | 1.83 | 1H NMR (500 MHz, DMSO-d6) δ 9.56-9.48 (m, 1H), 9.14 (d, J = 1.4 Hz, 1H), 8.57 (s, 1H), 8.41 (d, J = 6.3 Hz, 1H), 7.23 (t, J = 6.2 Hz, 1H), 6.81 (d, J = 6.4 Hz, 1H), 4.50 (s, 1H), 4.26 (s, 1H), 4.07-3.97 (m, 1H), 3.65-3.54 (m, 2H), 3.22-3.09 (m, 3H), 2.95 (s, 3H), 2.87 (dd, J = 13.2, 10.5 Hz, 1H), 2.55 (d, J = 0.9 Hz, 3H). |
| IV-48 | 376.2 | 1.79 | 1H NMR (500 MHz, DMSO-d6) δ 10.03 (d, J = 1.5 Hz, 1H), 9.32 (d, J = 1.3 Hz, 1H), 8.63 (s, 1H), 8.43 (d, J = 6.2 Hz, 1H), 7.47 (s, 1H), 7.40 (s, 1H), 7.24 (t, J = 54.2 Hz, 1H), 6.88 (d, J = 6.3 Hz, 1H), 4.48 (s, 1H), 4.20 (s, 1H), 4.10-3.98 (m, 2H), 3.69 (td, J = 11.2, 2.9 Hz, 1H), 3.34-3.17 (m, 2H). |
| IV-49 | 360.2 | 1.72 | 1H NMR (500 MHz, DMSO-d6) δ 10.00 (d, J = 1.5 Hz, 1H), 9.31 (d, J = 1.3 Hz, 1H), 8.68 (s, 1H), 8.41 (d, J = 6.3 Hz, 1H), 7.69 (t, J = 5.5 Hz, 1H), 7.23 (t, J = 54.6 Hz, 1H), 6.88 (d, J = 6.3 Hz, 1H), 3.92 (d, J = 15.5 Hz, 4H), 3.33-3.27 (m, 2H), 2.66-2.57 (m, 2H). |
| IV-50 | 374.3 | 1.88 | 1H NMR (500 MHz, DMSO-d6) δ 10.00 (d, J = 1.6 Hz, 1H), 9.32 (d, J = 1.3 Hz, 1H), 8.66 (s, 1H), 8.37 (d, J = 6.4 Hz, 1H), 7.40 (s, 1H), 7.21 (t, J = 54.5 Hz, 1H), 6.98-6.93 (m, 1H), 6.91 (d, J = 6.5 Hz, 1H), 4.69-4.11 (m, 2H), 3.22 (dd, J = 13.4, 10.6 Hz, 1H), 3.13 (ddd, J = 13.9, 11.7, 2.9 Hz, 1H), 2.43-2.32 (m, 1H), 2.00-1.90 (m, 1H), 1.86-1.66 (m, 2H), 1.56-1.41 (m, 1H). |
| IV-51 | 399.3 | 1.58 | 1H NMR (500 MHz, DMSO-d6) δ 10.02 (t, J = 1.5 Hz, 1H), 9.31 (d, J = 1.4 Hz, 1H), 8.70 (s, 1H), 8.40 (d, J = 6.3 Hz, 1H), 7.20 (t, J = 54.5 Hz, 1H), 6.93 (d, J = 6.4 Hz, 1H), 4.71 (s, 1H), 4.34 (s, 1H), 3.38-3.21 (m, 3H), 2.28-2.16 (m, 1H), 2.03-1.82 (m, 2H), 1.75-1.59 (m, 1H). |
| IV-52 | 408.3 | 2.51 | 1H NMR (500 MHz, Methanol-d4) δ 9.88 (s, 1H), 9.23-9.17 (m, 1H), 8.94 (dd, J = 2.1, 0.9 Hz, 1H), 8.83 (ddd, J = 5.6, 1.4, 0.7 Hz, 1H), 8.69 (t, J = 1.8 Hz, 1H), 8.67 (s, 1H), 8.32 (d, J = 6.8 Hz, 1H), 8.09 (ddd, J = 8.2, 5.7, 0.7 Hz, 1H), 6.97 (d, J = 6.9 Hz, 1H), 6.80 (t, J = 55.1 Hz, 1H), 4.87-4.74 (m, 1H), 4.72-4.44 (m, 1H), 3.47 (dd, J = 13.1, 11.5 Hz, 1H), 3.39-3.34 (m, 1H), 3.25 (ddd, J = 11.5, 7.7, 3.9 Hz, 1H), 2.31-2.18 (m, 1H), 2.15-2.00 (m, 2H), 1.95-1.77 (m, 1H). |
| IV-53 | 397.3 | 2.12 | 1H NMR (500 MHz, Methanol-d4) δ 9.98 (d, J = 1.6 Hz, 1H), 9.18 (d, J = 1.4 Hz, 1H), 8.90 (d, J = 1.4 Hz, 1H), 8.64 (s, 1H), 8.32 (d, J = 6.6 Hz, 1H), 7.49 (t, J = 1.0 Hz, 1H), 7.02-6.78 (m, 2H), 4.56-4.32 (m, 1H), 3.41 (dd, J = 13.2, 10.7 Hz, 1H), 3.21-3.10 (m, 1H), 2.33-2.22 (m, 1H), 2.05-1.86 (m, 2H), 1.86-1.70 (m, 1H). |
| IV-54 | 388.3 | 1.99 | 1H NMR (400 MHz, DMSO-d6) δ 10.01 (s, 1H), 9.32 (d, J = 1.4 Hz, 1H), 8.67 (s, 1H), |

TABLE 7-continued

Analytical data for compounds of Formula IV

| IV- | LCMS_Plus | LCMS_RT | NMR |
|---|---|---|---|
| | | | 8.43-8.33 (m, 1H), 7.45 (s, 1H), 7.22 (t, J = 54.5 Hz, 1H), 7.04 (s, 1H), 6.88 (d, J = 6.5 Hz, 1H), 3.13-2.89 (m, 1H), 1.94-1.76 (m, 2H), 1.76-1.61 (m, 1H), 1.56-1.35 (m, 1H), 1.12 (d, J = 6.8 Hz, 3H). |
| IV-55 | 373.3 | 2.09 | 1H NMR (500 MHz, DMSO-d6) δ 10.02 (d, J = 1.3 Hz, 1H), 9.25 (d, J = 1.3 Hz, 1H), 8.61 (s, 1H), 7.70 (dd, J = 8.6, 7.5 Hz, 1H), 7.40-7.29 (m, 2H), 7.14 (t, J = 54.5 Hz, 1H), 6.98-6.86 (m, 2H), 4.35-4.24 (m, 2H), 3.09 (dd, J = 13.1, 10.9 Hz, 1H), 2.98 (td, 1H), 2.43-2.34 (m, 1H), 1.99-1.91 (m, 1H), 1.81-1.63 (m, 2H), 1.60-1.48 (m, 1H). |
| IV-56 | 410.1 | 1.96 | 1H NMR (500 MHz, DMSO-d6) δ 10.03 (s, 1H), 9.31 (d, J = 1.3 Hz, 1H), 8.68 (s, 1H), 8.42 (d, J = 6.2 Hz, 1H), 7.21 (t, J = 54.2 Hz, 1H), 7.04 (s, 2H), 6.87 (d, J = 6.3 Hz, 1H), 4.33 (s, 1H), 3.18-2.98 (m, 3H), 2.28-2.17 (m, 1H), 1.95-1.85 (m, 1H), 1.85-1.72 (m, 1H), 1.63-1.43 (m, 1H). |
| IV-57 | 388.2 | 2.08 | 1H NMR (500 MHz, DMSO-d6) δ 10.10 (s, 1H), 9.32 (d, J = 1.3 Hz, 1H), 8.68 (s, 1H), 8.33 (d, J = 6.5 Hz, 1H), 7.27 (s, 1H), 7.15 (t, J = 54.5 Hz, 1H), 6.95 (s, 1H), 6.91 (d, J = 6.4 Hz, 1H), 4.30 (s, 1H), 3.96 (s, 1H), 2.18-2.09 (m, 1H), 1.74-1.65 (m, 1H), 1.65-1.47 (m, 2H), 1.13 (s, 4H). |
| IV-58 | 397.1 | 2.32 | 1H NMR (500 MHz, DMSO-d6) δ 10.00 (d, J = 1.7 Hz, 1H), 9.32 (d, J = 1.3 Hz, 1H), 8.66 (s, 1H), 8.37 (d, J = 6.4 Hz, 1H), 7.60 (s, 2H), 7.15 (t, J = 54.6 Hz, 1H), 6.96 (d, J = 6.5 Hz, 1H), 3.22-3.08 (m, 2H), 2.82-2.69 (m, 1H), 2.15-2.02 (m, 1H), 1.89-1.78 (m, 1H), 1.71 (qd, J = 11.8, 3.2 Hz, 1H), 1.66-1.52 (m, 1H). |
| IV-59 | 415.1 | 2.59 | 1H NMR (500 MHz, DMSO-d6) δ 10.19 (s, 1H), 9.36 (d, J = 1.3 Hz, 1H), 8.71 (s, 1H), 8.38 (d, J = 6.4 Hz, 1H), 7.59 (s, 2H), 6.96 (d, J = 6.5 Hz, 1H), 3.20-3.08 (m, 2H), 2.80-2.70 (m, 1H), 2.13-2.04 (m, 1H), 1.83 (dt, J = 13.2, 3.5 Hz, 1H), 1.71 (qd, J = 11.9, 3.5 Hz, 1H), 1.66-1.52 (m, 1H). |
| IV-60 | 392.1 | 2.14 | 1H NMR (500 MHz, DMSO-d6) δ 10.27-10.20 (m, 1H), 9.36 (d, J = 1.3 Hz, 1H), 8.69 (s, 1H), 8.37 (d, J = 6.3 Hz, 1H), 7.39 (s, 1H), 6.95-6.86 (m, 2H), 4.41 (s, 1H), 3.17 (dd, J = 13.3, 10.8 Hz, 1H), 3.08 (td, J = 13.0, 12.5, 2.8 Hz, 1H), 2.41-2.30 (m, 1H), 1.99-1.88 (m, 1H), 1.84-1.66 (m, 2H), 1.57-1.39 (m, 1H). |
| IV-61 | 454.3 | 2.13 | 1H NMR (500 MHz, DMSO-d6) δ 10.04 (s, 1H), 9.32 (d, J = 1.4 Hz, 1H), 8.70 (s, 1H), 8.44 (d, J = 6.3 Hz, 1H), 7.28 (d, J = 54.4 Hz, 1H), 7.15 (d, J = 8.4 Hz, 1H), 6.86 (d, J = 6.4 Hz, 1H), 4.12-4.00 (m, 1H), 3.61-3.51 (m, 1H), 3.46-3.40 (m, 1H), 3.11 (d, J = 13.1 Hz, 1H), 3.02-2.98 (m, 1H), 2.97 (s, 3H), 1.23 (d, J = 6.8 Hz, 3H). 2 C—H missing |
| IV-62 | 454.3 | 2.15 | 1H NMR (500 MHz, DMSO-d6) δ 10.05 (d, J = 1.7 Hz, 1H), 9.32 (d, J = 1.3 Hz, 1H), 8.66 (s, 1H), 8.45 (d, J = 6.3 Hz, 1H), 7.29 (d, J = 47.9 Hz, 1H), 7.23 (d, J = 1.9 Hz, 1H), 6.84 (d, J = 6.3 Hz, 1H), 4.78-4.18 (m, 2H), 4.09-4.02 (m, 1H), 3.58 (td, J = 11.7, 2.8 Hz, 1H), 3.47 (dp, J = 9.0, 6.6 Hz, 1H), 3.34 (ddd, J = 10.6, 6.5, 2.5 Hz, 1H), 3.18-3.07 (m, 1H), 3.00 (s, 3H), 2.89 (t, J = 12.1 Hz, 1H), 1.23 (d, J = 6.7 Hz, 3H). |
| IV-63 | 360.1 | 1.7 | 1H NMR (400 MHz, DMSO-d6) δ 10.09 (s, 1H), 9.34 (d, J = 1.3 Hz, 1H), 8.67 (s, 1H), 8.35 (d, J = 6.3 Hz, 1H), 7.58 (s, 1H), 7.30 (d, J = 55.0 Hz, 1H), 7.07 (s, 1H), 6.57 (s, 1H), 4.00-3.46 (m, 2H), 2.36-2.13 (m, 2H), 1.31-1.21 (m, 3H). |

TABLE 7-continued

Analytical data for compounds of Formula IV

| IV- | LCMS_Plus | LCMS_RT | NMR |
|---|---|---|---|
| IV-64 | 383.2 | 2.17 | |
| IV-65 | 397 | 2.3 | |
| IV-66 | 424.15 | 2.04 | |
| IV-67 | 383.1 | 1.95 | |
| IV-68 | 393.85 | 2.33 | |
| IV-69 | 385.8 | 1.9 | |
| IV-70 | 410.05 | 1.93 | |
| IV-71 | 410.1 | 1.97 | |
| IV-72 | 333.14 | 1.84 | 1H NMR (400 MHz, DMSO-d6) δ 10.08 (d, J = 4.3 Hz, 1H), 9.36 (d, J = 1.3 Hz, 1H), 8.69 (s, 1H), 8.35 (s, 1H), 7.25 (s, 1H), 6.59 (s, 1H), 4.49 (s, 1H), 3.93-3.67 (m, 2H), 3.58 (s, 2H), 3.38 (d, J = 11.4 Hz, 1H), 2.17-2.06 (m, 1H), 2.02 (s, 1H). |
| IV-73 | 373.2 | 2.23 | |
| IV-74 | 439.3 | 2.1 | 1H NMR (500 MHz, DMSO-d6) δ 10.01 (s, 1H), 9.33 (d, J = 1.3 Hz, 1H), 8.69 (s, 1H), 8.38 (d, J = 6.4 Hz, 1H), 7.22 (t, J = 54.6 Hz, 1H), 6.88 (d, J = 6.5 Hz, 1H), 6.80-6.41 (m, 3H), 3.18 (ddd, J = 13.8, 11.2, 3.1 Hz, 1H), 2.93 (dd, J = 13.3, 10.1 Hz, 1H), 2.88 (d, J = 6.9 Hz, 2H), 1.87 (dt, J = 12.9, 4.0 Hz, 1H), 1.78 (th, J = 10.4, 3.5 Hz, 2H), 1.57-1.43 (m, 1H), 1.43-1.29 (m, 1H). 2C—H missing |
| IV-75 | 357.05 | 3.04 | |
| IV-76 | 394.05 | 2.34 | |
| IV-77 | 394 | 2.49 | |
| IV-78 | 388.3 | 2.09 | 1H NMR (500 MHz, DMSO-d6) δ 10.07 (d, J = 1.4 Hz, 1H), 9.31 (d, J = 1.3 Hz, 1H), 8.68 (s, 1H), 8.43 (d, J = 6.3 Hz, 1H), 6.87 (d, J = 6.4 Hz, 1H), 3.80 (d, J = 31.0 Hz, 4H), 3.66-3.60 (m, 4H), 2.11 (t, J = 19.1 Hz, 2H), 2.08 (s, 3H). |
| IV-79 | 401.3 | 1.98 | 1H NMR (500 MHz, DMSO-d6) δ 10.15 (q, J = 1.5 Hz, 1H), 9.41 (d, J = 1.4 Hz, 1H), 9.14 (d, J = 5.3 Hz, 1H), 8.90 (s, 1H), 8.86 (t, J = 1.8 Hz, 1H), 8.61 (dt, J = 7.9, 1.4 Hz, 1H), 8.24-8.04 (m, 2H), 7.88 (t, J = 7.8 Hz, 1H), 7.29 (t, J = 54.2 Hz, 1H), 6.32 (s, 2H), 3.22 (d, J = 1.2 Hz, 3H). |
| IV-80 | 365.05 | 1.62 | |
| IV-81 | 347.04 | 2.28 | |
| IV-82 | 370.15 | 2.43 | |
| IV-83 | 386.25 | 1.63 | |
| IV-84 | 381.1 | 1.85 | |
| IV-85 | 345.19 | 2.92 | |
| IV-86 | 401.3 | 1.8 | 1H NMR (500 MHz, DMSO-d6) δ 10.01 (s, 1H), 9.33 (d, J = 1.3 Hz, 1H), 8.64 (s, 1H), 8.45 (d, J = 6.2 Hz, 1H), 8.23 (s, 1H), 7.26 (t, J = 54.0 Hz, 1H), 6.92 (d, J = 6.3 Hz, 1H), 4.59-4.30 (m, 1H), 3.49-3.13 (m, 8H), 2.96-2.62 (m, 2H). |
| IV-87 | 415.95 | 1.97 | |
| IV-88 | 375.05 | 2.3 | |
| IV-89 | 389 | 1.73 | |
| IV-90 | 375.05 | 2.18 | |
| IV-91 | 359.1 | 2.25 | |
| IV-92 | 441.05 | 2.11 | |
| IV-93 | 427 | 2.04 | |
| IV-94 | 440.3 | 1.96 | |
| IV-95 | 454.1 | 2.05 | |
| IV-96 | 409.3 | 2.4 | 1H NMR (500 MHz, Methanol-d4) δ 10.14 (s, 1H), 9.21 (d, J = 1.3 Hz, 1H), 8.67 (s, 1H), 8.35 (d, J = 6.6 Hz, 1H), 7.68 (s, 1H), 7.00 (t, J = 55.1 Hz, 1H), 6.91 (d, J = 6.6 Hz, 1H), 6.08 (p, J = 2.4 Hz, 1H), 4.50 (s, 2H), 4.04 (s, 2H), 2.59-2.46 (m, 2H), 2.39 (s, 3H). |
| IV-97 | 411.4 | 2.4 | 1H NMR (500 MHz, Methanol-d4) δ 9.92-9.85 (m, 1H), 9.29-9.25 (m, 1H), 8.71 (s, 1H), 8.28 (d, J = 7.2 Hz, 1H), 7.76 (s, 1H), 7.01 (d, J = 7.2 Hz, 1H), 6.87 (t, J = 55.2 Hz, 1H), 4.79-4.37 (m, 2H), 3.43-3.33 (m, 2H), 2.91 (tt, J = 11.3, 3.9 Hz, 1H), 2.32 (s, |

TABLE 7-continued

Analytical data for compounds of Formula IV

| IV- | LCMS_Plus | LCMS_RT | NMR |
|---|---|---|---|
| | | | 3H), 2.19-2.10 (m, 1H), 2.10-1.98 (m, 1H), 1.98-1.69 (m, 2H). |
| IV-98 | 386.1 | 1.91 | |
| IV-99 | 400.15 | 2.04 | |
| IV-100 | 388.1 | 1.91 | |
| IV-101 | 424.85 | 1.92 | |
| IV-102 | 401.05 | 2.61 | 1H NMR (400 MHz, DMSO-d6) δ 10.04 (d, J = 6.9 Hz, 1H), 9.34 (d, J = 1.3 Hz, 1H), 8.69 (d, J = 6.2 Hz, 1H), 8.32 (d, J = 6.4 Hz, 1H), 7.22 (td, J = 54.3, 4.6 Hz, 1H), 6.57 (dd, J = 18.4, 6.5 Hz, 1H), 4.04-3.84 (m, 3H), 3.74-3.53 (m, 1H), 3.38-3.01 (m, 3H), 2.22-2.06 (m, 3H), 1.75-1.63 (m, 3H), 1.53 (d, J = 11.0 Hz, 1H), 1.30 (qd, J = 12.2, 11.8, 5.1 Hz, 2H). |
| IV-103 | 330.92 | 2.74 | 1H NMR (400 MHz, DMSO-d6) δ 9.98 (d, J = 1.4 Hz, 1H), 9.34 (d, J = 1.3 Hz, 1H), 8.67 (s, 1H), 8.36 (d, J = 6.5 Hz, 1H), 7.30 (d, J = 54.6 Hz, 1H), 6.89 (d, J = 6.6 Hz, 1H), 3.79 (d, J = 6.4 Hz, 4H), 1.71 (q, J = 6.2, 5.4 Hz, 2H), 1.68-1.57 (m, 4H). |
| IV-104 | 333.04 | 2.11 | |
| IV-105 | 344.99 | 2.88 | 1H NMR (400 MHz, DMSO-d6) δ 10.00 (d, J = 1.4 Hz, 1H), 9.35 (d, J = 1.3 Hz, 1H), 8.69 (s, 1H), 8.34 (d, J = 6.5 Hz, 1H), 7.23 (t, J = 54.7 Hz, 1H), 6.77 (d, J = 6.6 Hz, 1H), 3.93 (s, 2H), 3.65 (s, 2H), 1.82 (d, J = 21.9 Hz, 4H), 1.54 (p, J = 2.6 Hz, 4H). |
| IV-106 | 388.3 | 2.02 | 1H NMR (500 MHz, DMSO-d6) δ 10.03 (q, J = 1.3 Hz, 1H), 9.30 (d, J = 1.3 Hz, 1H), 8.62 (s, 1H), 8.36 (d, J = 6.3 Hz, 1H), 7.45 (d, J = 3.2 Hz, 1H), 7.20 (t, J = 54.5 Hz, 1H), 7.02-6.93 (m, 1H), 6.85 (d, J = 6.4 Hz, 1H), 3.14-2.99 (m, 1H), 2.41-2.26 (m, 1H), 1.89-1.74 (m, 2H), 1.74-1.67 (m, 2H), 1.22 (d, J = 6.8 Hz, 3H), 2H not observed. |
| IV-107 | 388.3 | 2.07 | |
| IV-108 | 388.3 | 2.04 | 1H NMR (500 MHz, DMSO-d6) δ 10.03 (s, 1H), 9.29 (s, 1H), 8.60 (s, 1H), 8.31 (d, J = 6.3 Hz, 1H), 7.30 (s, 1H), 7.14 (t, J = 54.4 Hz, 1H), 6.89-6.83 (m, 1H), 6.80 (d, J = 6.3 Hz, 1H), 3.87 (s, 2H), 3.78-3.66 (m, 1H), 3.66-3.53 (m, 1H), 2.30-2.15 (m, 1H), 1.84-1.70 (m, 1H), 1.70-1.58 (m, 1H), 1.01 (d, J = 7.0 Hz, 3H), 1H not observed. |
| IV-109 | 388.3 | 2.01 | 1H NMR (500 MHz, Methanol-d4) δ 9.92 (s, 1H), 9.31-9.24 (m, 1H), 8.73 (s, 1H), 8.30 (d, J = 7.1 Hz, 1H), 7.15-6.85 (m, 2H), 2.79-2.67 (m, 1H), 2.14-2.05 (m, 1H), 2.05-1.97 (m, 1H), 1.92-1.83 (m, 1H), 1.73-1.59 (m, 1H), 1.36 (d, J = 6.9 Hz, 3H), 3H not observed. |
| IV-110 | 389.3 | 1.57 | |
| IV-111 | 359.05 | 2.05 | |
| IV-112 | 411.15 | 2.46 | |
| IV-113 | 427.35 | 1.63 | |
| IV-114 | 424.15 | 2.07 | |
| IV-115 | 379.15 | 2.96 | |
| IV-116 | 387.1 | 2.22 | |
| IV-117 | 390 | 1.69 | |
| IV-118 | 359.85 | 1.88 | |
| IV-119 | 361.05 | 2.52 | |
| IV-120 | 347.09 | 2.02 | |
| IV-121 | 361.1 | 2.16 | |
| IV-122 | 359.45 | 3.08 | |
| IV-123 | 415.1 | 1.94 | 1H NMR (400 MHz, Methanol-d4) δ 10.18 (d, J = 1.6 Hz, 1H), 9.18 (d, J = 1.4 Hz, 1H), 8.65 (s, 1H), 8.53-8.44 (m, 1H), 7.45 (d, J = 1.5 Hz, 1H), 7.14-6.54 (m, 2H), 4.38 (s, 1H), 4.08 (d, J = 6.7 Hz, 2H), 3.47 (d, J = 5.1 Hz, 3H), 3.37 (d, J = 2.8 Hz, 1H), 3.33 (p, J = 1.6 Hz, 2H), 2.93 (d, J = 1.5 Hz, 2H), 2.43 (td, J = 13.6, 4.9 Hz, 2H), 2.17 (d, J = 14.0 Hz, 2H), 1.25 (s, 2H). |

TABLE 7-continued

Analytical data for compounds of Formula IV

| IV- | LCMS_Plus | LCMS_RT | NMR |
|---|---|---|---|
| IV-124 | 438.56 | 2.12 | 1H NMR (400 MHz, Methanol-d4) δ 10.18 (d, J = 1.6 Hz, 1H), 9.18 (d, J = 1.4 Hz, 1H), 8.65 (s, 1H), 8.53-8.44 (m, 1H), 7.45 (d, J = 1.5 Hz, 1H), 7.14-6.54 (m, 2H), 4.38 (s, 1H), 4.08 (d, J = 6.7 Hz, 2H), 3.47 (d, J = 5.1 Hz, 3H), 3.37 (d, J = 2.8 Hz, 1H), 3.33 (p, J = 1.6 Hz, 2H), 2.93 (d, J = 1.5 Hz, 2H), 2.43 (td, J = 13.6, 4.9 Hz, 2H), 2.17 (d, J = 14.0 Hz, 2H), 1.25 (s, 2H). |
| IV-125 | 424.41 | 2.16 | 1H NMR (400 MHz, Methanol-d4) δ 10.20 (s, 1H), 9.25 (s, 1H), 8.74 (s, 1H), 8.29 (d, J = 6.6 Hz, 1H), 6.96 (t, J = 55.0 Hz, 1H), 6.61 (d, J = 6.7 Hz, 1H), 4.16 (s, 1H), 3.83 (s, 2H), 3.58 (d, J = 61.8 Hz, 1H), 2.97 (d, J = 15.0 Hz, 6H), 2.67 (s, 1H), 2.41 (s, 2H). |
| IV-126 | 436.3 | 2.25 | 1H NMR (400 MHz, Methanol-d4) δ 10.12 (s, 1H), 9.21 (s, 1H), 8.67 (s, 1H), 8.38 (d, J = 6.4 Hz, 1H), 6.95 (t, J = 55.1 Hz, 1H), 6.74 (d, J = 6.5 Hz, 1H), 4.47 (s, 2H), 3.46-3.37 (m, 2H), 3.08 (s, 3H), 2.13 (d, J = 9.5 Hz, 2H), 2.04 (s, 2H), 1.87 (t, J = 7.1 Hz, 2H). |
| IV-127 | 438.3 | 2.2 | 1H NMR (400 MHz, Methanol-d4) δ 9.84 (s, 1H), 8.96 (d, J = 0.9 Hz, 1H), 8.44 (s, 1H), 8.08 (d, J = 6.5 Hz, 1H), 6.72 (t, J = 54.9 Hz, 1H), 6.48 (d, J = 6.6 Hz, 1H), 3.38-3.21 (m, 1H), 2.92 (t, J = 12.9 Hz, 1H), 2.76 (s, 3H), 2.43 (s, 3H), 1.78-1.44 (m, 4H), 1.12 (d, J = 6.9 Hz, 3H). |
| IV-128 | 390.3 | 1.72 | 1H NMR (400 MHz, DMSO-d6) δ 10.03 (s, 1H), 9.32 (d, J = 1.1 Hz, 1H), 8.66 (s, 1H), 8.40 (d, J = 6.2 Hz, 1H), 7.48 (s, 1H), 7.22 (t, J = 54.5 Hz, 1H), 7.05 (s, 1H), 6.89 (s, 1H), 4.45 (s, 1H), 4.10-3.51 (m, 6H), 2.95 (s, 2H). |
| IV-129 | 344.87 | 2.96 | 1H NMR (400 MHz, DMSO-d6) δ 9.75 (d, J = 1.4 Hz, 1H), 9.09 (d, J = 1.3 Hz, 1H), 8.43 (s, 1H), 8.11 (d, J = 6.5 Hz, 1H), 6.99 (t, J = 54.7 Hz, 1H), 6.66 (d, J = 6.6 Hz, 1H), 2.84 (ddd, J = 13.3, 11.7, 2.9 Hz, 1H), 2.54 (dd, J = 13.1, 10.6 Hz, 1H), 1.70-1.31 (m, 2H), 1.32-0.93 (m, 2H), 0.73 (d, J = 6.6 Hz, 3H). Water peak obscures some signals. |
| IV-130 | 370.88 | 3.17 | 1H NMR (400 MHz, DMSO-d6) δ 10.01 (d, J = 1.6 Hz, 1H), 9.33 (d, J = 1.4 Hz, 1H), 8.67 (s, 1H), 8.36 (d, J = 6.4 Hz, 1H), 7.23 (t, J = 54.7 Hz, 1H), 6.90-6.80 (m, 1H), 2.99 (td, J = 12.8, 3.0 Hz, 1H), 2.06 (dq, J = 11.7, 5.8 Hz, 1H), 1.99-1.58 (m, 8H), 1.57-1.27 (m, 3H). Water peak obscures some signals. |
| IV-131 | 359.43 | 3.04 | |
| IV-132 | 472.38 | 3.07 | |
| IV-133 | 486.23 | 3.13 | |
| IV-134 | 359.58 | 3.1 | |
| IV-135 | 343.27 | 2.83 | 1H NMR (400 MHz, DMSO-d6) δ 9.79 (s, 1H), 9.08 (s, 1H), 8.41 (s, 1H), 8.18 (d, J = 6.3 Hz, 1H), 6.98 (t, J = 54.6 Hz, 1H), 6.62 (d, J = 6.4 Hz, 1H), 2.58 (t, J = 7.5 Hz, 1H), 1.76 (tt, J = 11.9, 5.7 Hz, 1H), 1.61-1.43 (m, 3H), 1.29-1.08 (m, 3H), 0.80 (dt, J = 10.5, 5.8 Hz, 1H), 0.07 (d, J = 4.2 Hz, 1H). |
| IV-136 | 361.43 | 2.26 | |
| IV-137 | 345.12 | 2.95 | |
| IV-138 | 361.3 | 2.16 | |
| IV-139 | 443.1 | 0.64 | |
| IV-140 | 386.1 | 0.69 | |
| IV-141 | 422 | 1.99 | 1H NMR (500 MHz, DMSO-d6) δ 10.06 (s, 1H), 9.30 (s, 1H), 8.62 (s, 1H), 8.35 (d, J = 6.3 Hz, 1H), 7.22 (t, J = 54.5 Hz, 1H), 6.78 (d, J = 6.2 Hz, 1H), 4.25 (br s, 1H), 3.29-3.24 (m, 2H), 3.18-3.07 (m, 1H), 3.05 (s, 3H), 3.02 (s, 3H), 2.95-2.85 (m, 1H), 1.95-1.84 (m, 1H), 1.83-1.69 (m, 1H), 1.57-1.44 (m, 2H). |

TABLE 7-continued

Analytical data for compounds of Formula IV

| IV- | LCMS_Plus | LCMS_RT | NMR |
|---|---|---|---|
| IV-142 | 361.15 | 2.15 | |
| IV-143 | 357.45 | 2.06 | 1H NMR (400 MHz, Methanol-d4) δ 9.93 (s, 1H), 9.33-9.28 (m, 1H), 8.77 (d, J = 0.8 Hz, 1H), 8.33 (dd, J = 7.2, 0.8 Hz, 1H), 7.08-7.01 (m, 2H), 4.62 (s, 2H), 3.33 (pd, J = 1.7, 0.7 Hz, 4H), 3.19 (dd, J = 13.3, 10.7 Hz, 1H), 3.13-2.90 (m, 2H), 2.16-1.99 (m, 2H), 1.81-1.67 (m, 1H), 1.64-1.50 (m, 1H). |
| IV-144 | 450.1 | 2.29 | 1H NMR (400 MHz, Methanol-d4) δ 9.86 (s, 1H), 9.35 (d, J = 1.3 Hz, 1H), 8.80 (s, 1H), 8.29 (d, J = 7.5 Hz, 1H), 7.26-6.89 (m, 2H), 3.99 (dt, J = 7.5, 4.9 Hz, 1H), 3.81-3.61 (m, 1H), 3.50 (s, 1H), 2.83-2.69 (m, 1H), 2.68 (s, 3H), 2.24-2.07 (m, 1H), 1.69-1.13 (m, 7H). |
| IV-145 | 464.15 | 2.38 | 1H NMR (400 MHz, Methanol-d4) δ 10.14 (s, 1H), 9.36 (s, 1H), 8.84 (d, J = 4.6 Hz, 1H), 8.28 (d, J = 7.4 Hz, 1H), 7.20-7.03 (m, 1H), 6.94-6.80 (m, 1H), 4.12 (t, J = 7.3 Hz, 1H), 3.94 (s, 1H), 3.87 (t, J = 7.3 Hz, 1H), 3.68 (s, 1H), 3.52 (dt, J = 10.5, 5.3 Hz, 1H), 3.18 (td, J = 14.1, 12.4, 6.9 Hz, 1H), 2.90 (d, J = 4.9 Hz, 3H), 2.68 (s, 1H), 1.91-1.83 (m, 4H), 1.68-1.51 (m, 1H), 1.43-1.30 (m, 2H). |
| IV-146 | 431.1 | 2.34 | 1H NMR (400 MHz, DMSO-d6) δ 10.16 (q, J = 1.3 Hz, 1H), 9.39 (d, J = 1.3 Hz, 1H), 9.07 (d, J = 5.3 Hz, 1H), 8.89 (s, 1H), 8.36 (d, J = 2.0 Hz, 1H), 8.29-8.21 (m, 1H), 8.04 (d, J = 5.4 Hz, 1H), 7.71 (q, J = 6.4 Hz, 1H), 7.67-7.53 (m, 2H), 7.28 (t, J = 54.5 Hz, 1H), 4.34 (d, J = 6.2 Hz, 2H), 2.93 (s, 3H). |
| IV-147 | 416.7 | 2.25 | 1H NMR (400 MHz, DMSO-d6) δ 10.09 (d, J = 1.4 Hz, 1H), 10.02 (s, 1H), 9.39 (d, J = 1.3 Hz, 1H), 9.07 (d, J = 5.4 Hz, 1H), 8.83 (s, 1H), 8.23 (s, 1H), 8.08-7.95 (m, 2H), 7.60 (t, J = 7.9 Hz, 1H), 7.51-7.38 (m, 1H), 7.20 (d, J = 54.2 Hz, 1H), 3.10 (s, 3H). |
| IV-148 | 417 | 2.37 | 1H NMR (400 MHz, DMSO-d6) δ 10.12 (q, J = 1.4 Hz, 1H), 9.40 (d, J = 1.3 Hz, 1H), 9.14 (d, J = 5.4 Hz, 1H), 8.90 (s, 1H), 8.72 (t, J = 1.8 Hz, 1H), 8.60 (dt, J = 7.8, 1.4 Hz, 1H), 8.14 (d, J = 5.4 Hz, 1H), 8.03 (dt, J = 7.9, 1.3 Hz, 1H), 7.88 (t, J = 7.8 Hz, 1H), 7.68 (q, J = 5.0 Hz, 1H), 7.26 (t, J = 54.3 Hz, 1H). Some peaks obscured by solvent peaks |
| IV-149 | 409.2 | 2.49 | |
| IV-150 | 436.25 | 1.99 | |
| IV-151 | 487.26 | 2.68 | |
| IV-152 | 438.4 | 2.23 | 1H NMR (400 MHz, Methanol-d4) δ 9.86 (s, 1H), 9.34 (d, J = 1.3 Hz, 1H), 8.77 (s, 1H), 8.26 (d, J = 7.5 Hz, 1H), 7.12-7.03 (m, 2H), 3.68-3.58 (m, 2H), 3.11 (d, J = 7.0 Hz, 2H), 2.93 (s, 3H), 2.68 (s, 2H), 2.12-1.96 (m, 3H), 1.65-1.53 (m, 2H), 1.40 (dd, J = 6.7, 3.8 Hz, 1H). |
| IV-153 | 384 | 2.17 | |
| IV-154 | 342.19 | 2.27 | 1H NMR (400 MHz, DMSO-d6) δ 10.13 (q, J = 1.4 Hz, 1H), 9.36 (dd, J = 4.8, 1.3 Hz, 1H), 8.91-8.78 (m, 2H), 8.69 (d, J = 5.3 Hz, 1H), 8.32 (s, 1H), 7.72-7.64 (m, 1H), 7.30 (t, J = 54.4 Hz, 1H), 4.26 (q, J = 7.3 Hz, 2H), 1.48 (t, J = 7.3 Hz, 3H). |
| IV-155 | 381 | 2.06 | |
| IV-156 | 371.1 | 2.06 | |
| IV-157 | 363 | 2.56 | 1H NMR (400 MHz, DMSO-d6) δ 10.14 (q, J = 1.4 Hz, 1H), 9.39 (d, J = 1.3 Hz, 1H), 9.08 (d, J = 5.3 Hz, 1H), 8.89 (s, 1H), 8.38 (s, 1H), 8.30 (dt, J = 7.4, 1.8 Hz, 1H), 8.06 (d, J = 5.4 Hz, 1H), 7.71-7.60 (m, 2H), 7.29 (t, J = 54.4 Hz, 1H), 4.21 (s, 2H). |
| IV-158 | 377 | 2.96 | |
| IV-159 | 353 | 2.6 | |

TABLE 7-continued

Analytical data for compounds of Formula IV

| IV- | LCMS_Plus | LCMS_RT | NMR |
|---|---|---|---|
| IV-160 | 430.75 | 2.3 | |
| IV-161 | 340.04 | 2.35 | |
| IV-162 | 354.05 | 2.25 | 1H NMR (400 MHz, DMSO-d6) δ 10.18-10.05 (m, 1H), 9.35 (d, J = 1.3 Hz, 1H), 9.10-8.98 (m, 1H), 8.82 (s, 1H), 8.26 (d, J = 1.8 Hz, 1H), 8.23-8.06 (m, 1H), 8.00 (d, J = 5.4 Hz, 1H), 7.63-7.52 (m, 2H), 7.26 (t, J = 54.5 Hz, 1H), 5.32 (s, 1H), 4.66 (s, 2H). |
| IV-163 | 313.84 | 2.88 | |
| IV-164 | 424.1 | 2.15 | |
| IV-165 | 409.05 | 2.06 | |
| IV-166 | 436.15 | 2.53 | |
| IV-167 | 396 | 2.12 | |
| IV-168 | 438.05 | 2.3 | 1H NMR (400 MHz, Methanol-d4) δ 9.80 (d, J = 1.8 Hz, 1H), 9.31 (d, J = 1.4 Hz, 1H), 8.76 (d, J = 1.2 Hz, 1H), 8.29 (dd, J = 7.4, 1.2 Hz, 1H), 7.29-6.75 (m, 2H), 3.96-3.83 (m, 1H), 3.53-3.40 (m, 1H), 3.36-3.19 (m, 3H), 2.96 (dd, J = 11.5, 1.3 Hz, 6H), 2.08 (dq, J = 8.1, 4.6 Hz, 3H), 1.82 (dp, J = 18.9, 6.3, 5.0 Hz, 1H). |
| IV-169 | 424.55 | 2.09 | 1H NMR (400 MHz, Methanol-d4) δ 9.82 (s, 1H), 9.34 (d, J = 1.4 Hz, 1H), 8.78 (d, J = 6.8 Hz, 1H), 8.29 (dd, J = 7.3, 1.5 Hz, 1H), 7.13-7.04 (m, 2H), 4.13 (s, 1H), 3.82 (dd, J = 13.3, 7.6 Hz, 1H), 3.65 (dq, J = 8.0, 3.9 Hz, 1H), 3.00 (s, 3H), 2.18 (d, J = 10.0 Hz, 2H), 2.04 (ddd, J = 12.6, 7.7, 4.2 Hz, 2H), 1.91-1.78 (m, 3H). |
| IV-170 | 438.05 | 2.39 | |
| IV-171 | 478.16 | 2.7 | |
| IV-172 | 480.11 | 2.34 | |
| IV-173 | 474 | 2.19 | |
| IV-174 | 414.3 | 2.65 | 1H NMR (500 MHz, DMSO-d6) δ 10.01 (d, J = 1.8 Hz, 1H), 9.31 (d, J = 1.4 Hz, 1H), 9.09 (d, J = 1.9 Hz, 1H), 8.64 (s, 1H), 8.37 (d, J = 6.4 Hz, 1H), 7.52 (d, J = 1.9 Hz, 1H), 7.17 (t, J = 54.5 Hz, 1H), 6.92 (d, J = 6.4 Hz, 1H), 3.30 (t, J = 12.3 Hz, 1H), 3.20 (td, J = 12.6, 11.7, 2.8 Hz, 1H), 3.12-3.01 (m, 1H), 2.24-2.10 (m, 1H), 1.98-1.79 (m, 2H), 1.65 (d, J = 12.2 Hz, 1H), 2H not observed. |
| IV-175 | 359.8 | 2.16 | |
| IV-176 | 385.1 | 2.16 | |
| IV-177 | 410 | 1.97 | |
| IV-178 | 442.1 | 2.52 | 1H NMR (400 MHz, Methanol-d4) δ 9.98 (s, 1H), 9.56-9.02 (m, 1H), 8.73 (s, 1H), 8.30 (d, J = 6.8 Hz, 1H), 7.56 (s, 1H), 7.14-6.59 (m, 2H), 3.96 (tt, J = 9.8, 4.2 Hz, 1H), 3.43-3.13 (m, 7H), 2.26-1.66 (m, 5H). 1 exchangeable proton not observed. |
| IV-179 | 425.1 | 1.97 | 1H NMR (400 MHz, Methanol-d4) δ 10.08-9.84 (m, 1H), 9.35-9.20 (m, 1H), 8.71 (s, 1H), 8.29 (d, J = 6.9 Hz, 1H), 7.22-6.84 (m, 2H), 4.45 (s, 1H), 4.18 (s, 1H), 3.73-3.46 (m, 3H), 2.18 (d, J = 4.9 Hz, 1H), 2.00 (td, J = 8.3, 6.7, 4.8 Hz, 1H), 1.77 (ddt, J = 8.8, 5.7, 3.5 Hz, 2H). exchangeable protons not observed |
| IV-180 | 442.2 | 2.48 | 1H NMR (400 MHz, Methanol-d4) δ 9.98 (s, 1H), 9.56-9.02 (m, 1H), 8.73 (s, 1H), 8.30 (d, J = 6.8 Hz, 1H), 7.56 (s, 1H), 7.14-6.59 (m, 2H), 3.96 (tt, J = 9.8, 4.2 Hz, 1H), 3.43-3.13 (m, 7H), 2.26-1.66 (m, 5H). 1 exchangeable proton not observed. |
| IV-181 | 424.7 | 1.96 | 1H NMR (400 MHz, Methanol-d4) δ 9.82 (s, 1H), 9.36-9.30 (m, 1H), 8.78 (d, J = 0.8 Hz, 1H), 8.32 (dd, J = 7.4, 0.8 Hz, 1H), 7.19-6.88 (m, 2H), 4.80 (s, 1H), 4.41 (s, 1H), 4.02 (dq, J = 9.6, 4.8, 4.1 Hz, 1H), 3.47 (ddd, J = 19.8, 13.4, 10.5 Hz, 2H), 2.17 (dd, J = 10.3, 5.8 Hz, 1H), 2.12-2.02 (m, 1H), 1.93-1.77 (m, 2H). The exchangeable protons are not observed. |

TABLE 7-continued

Analytical data for compounds of Formula IV

| IV- | LCMS_Plus | LCMS_RT | NMR |
|---|---|---|---|
| IV-182 | 367.1 | 1.67 | 1H NMR (400 MHz, Methanol-d4) δ 10.60 (s, 1H), 9.12 (s, 1H), 8.50 (s, 1H), 8.44 (dd, J = 5.3, 0.6 Hz, 1H), 7.53 (d, J = 0.6 Hz, 2H), 7.13 (d, J = 5.2 Hz, 1H), 4.05 (dd, J = 6.5, 4.2 Hz, 2H), 4.01-3.93 (m, 2H), 3.76 (ddd, J = 11.1, 6.7, 4.2 Hz, 4H), 2.20 (s, 3H). |
| IV-183 | 367.05 | 1.56 | 1H NMR (400 MHz, Methanol-d4) δ 10.51 (d, J = 1.4 Hz, 1H), 9.15 (d, J = 1.4 Hz, 1H), 8.69-8.49 (m, 2H), 8.27 (d, J = 7.1 Hz, 2H), 6.74 (d, J = 74.5 Hz, 1H), 3.90-3.73 (m, 9H), 2.24-2.11 (m, 2H). |
| IV-184 | 366.15 | 1.83 | 1H NMR (400 MHz, Methanol-d4) δ 10.51 (d, J = 1.4 Hz, 1H), 9.15 (d, J = 1.4 Hz, 1H), 8.69-8.49 (m, 2H), 8.27 (d, J = 7.1 Hz, 2H), 6.74 (d, J = 74.5 Hz, 1H), 3.90-3.73 (m, 9H), 2.24-2.11 (m, 2H). |
| IV-185 | 417.1 | 2.21 | |
| IV-186 | 417 | 2.21 | |
| IV-187 | 337.94 | 2.35 | 1H NMR (400 MHz, DMSO-d6) δ 10.37 (d, J = 1.4 Hz, 1H), 9.23 (d, J = 1.4 Hz, 1H), 8.65 (s, 1H), 8.36 (d, J = 6.4 Hz, 1H), 8.19 (s, 1H), 7.83 (s, 1H), 6.88 (d, J = 6.5 Hz, 1H), 3.07 (t, J = 12.1 Hz, 1H), 2.82-2.68 (m, 1H), 1.85-1.74 (m, 2H), 1.66 (s, 1H), 1.51 (d, J = 12.4 Hz, 1H), 1.27 (d, J = 12.3 Hz, 1H), 1.16 (s, 1H), 1.01 (d, J = 6.6 Hz, 3H). 1 proton obscured by solvent peaks |
| IV-188 | 381.1 | 1.86 | 1H NMR (400 MHz, DMSO-d6) δ 10.46 (s, 1H), 9.23 (s, 1H), 8.77 (s, 1H), 8.17 (s, 1H), 7.80 (s, 1H), 7.30 (s, 1H), 3.90 (dt, J = 29.0, 5.2 Hz, 4H), 3.61 (q, J = 6.0 Hz, 4H), 2.39 (s, 3H), 2.09 (s, 3H). |
| IV-189 | 430.3 | 2.19 | 1H NMR (500 MHz, Methanol-d4) δ 10.30 (dd, J = 1.5, 0.7 Hz, 1H), 9.24-9.18 (m, 1H), 8.72 (s, 1H), 8.51 (d, J = 6.3 Hz, 1H), 7.92 (s, 2H), 6.98 (d, J = 6.3 Hz, 1H), 5.04-4.85 (m, 2H), 4.64 (dd, J = 11.9, 3.5 Hz, 1H), 3.63 (ddd, J = 11.6, 6.6, 3.6 Hz, 1H), 3.55 (dd, J = 14.4, 11.9 Hz, 1H), 3.15 (dd, J = 14.5, 11.5 Hz, 1H), 1.50 (d, J = 6.6 Hz, 3H). |
| IV-190 | 381.24 | 1.58 | 1H NMR (400 MHz, Methanol-d4) δ 10.51-10.42 (m, 1H), 9.21 (dd, J = 5.3, 1.4 Hz, 1H), 8.71 (d, J = 1.5 Hz, 1H), 8.32 (dd, J = 11.9, 6.8 Hz, 1H), 6.89 (d, J = 7.1 Hz, 1H), 4.25 (s, 2H), 3.94 (s, 5H), 3.65 (dt, J = 22.5, 6.0 Hz, 2H), 2.21 (s, 1H), 2.10 (d, J = 7.3 Hz, 3H), 1.39 (dd, J = 6.7, 3.3 Hz, 1H). one proton masked by solvent peaks |
| IV-191 | 388.3 | 2.05 | |
| IV-192 | 397.2 | 2.19 | |
| IV-193 | 397.3 | 2.24 | |
| IV-194 | 388.3 | 2.1 | |
| IV-195 | 444.3 | 2.35 | 1H NMR (500 MHz, Methanol-d4) δ 10.34-10.23 (m, 1H), 9.21 (dd, J = 1.3, 0.7 Hz, 1H), 8.71 (s, 1H), 8.51 (d, J = 6.3 Hz, 1H), 7.92 (s, 2H), 6.96 (d, J = 6.3 Hz, 1H), 4.88 (s, 2H), 4.62-4.44 (m, 1H), 3.71 (t, J = 13.1 Hz, 1H), 3.62-3.47 (m, 1H), 3.36-3.32 (m, 1H), 2.80 (s, 3H), 1.60 (d, J = 6.4 Hz, 3H). |
| IV-196 | 381.09 | 1.72 | 1H NMR (400 MHz, Methanol-d4) δ 10.45 (d, J = 1.3 Hz, 1H), 8.93 (d, J = 1.4 Hz, 1H), 8.46 (s, 1H), 7.61 (d, J = 0.6 Hz, 2H), 6.44 (s, 1H), 3.78 (t, J = 5.2 Hz, 2H), 3.60 (dt, J = 10.8, 4.0 Hz, 6H), 2.31 (s, 3H), 2.02 (s, 3H). |
| IV-197 | 373.05 | 2.1 | 1H NMR (400 MHz, Methanol-d4) δ 10.21 (d, J = 1.8 Hz, 1H), 9.19-9.13 (m, 1H), 8.49 (s, 1H), 7.75 (dd, J = 8.6, 7.5 Hz, 1H), 7.38 (d, J = 7.5 Hz, 1H), 7.14-6.82 (m, 2H), 3.84-3.68 (m, 8H), 2.20 (s, 3H). |
| IV-198 | 347.54 | 1.99 | 1H NMR (400 MHz, Methanol-d4) δ 10.32 (d, J = 1.4 Hz, 1H), 9.18 (d, J = 1.4 Hz, 1H), 8.53 (s, 1H), 7.80 (dd, J = 8.6, 7.5 Hz, |

TABLE 7-continued

Analytical data for compounds of Formula IV

| IV- | LCMS_Plus | LCMS_RT | NMR |
|---|---|---|---|
| | | | 1H), 7.42 (d, J = 7.5 Hz, 1H), 6.98 (d, J = 8.6 Hz, 1H), 3.97-3.68 (m, 8H), 2.24 (s, 3H). |
| IV-199 | 431.1429 | 2.41 | |
| IV-200 | 431.1 | 2.39 | |
| IV-201 | 431 | 2.39 | |
| IV-202 | 431.1 | 2.41 | |
| IV-203 | 390.3 | 1.81 | |
| IV-204 | 322.79 | 2.42 | 1H NMR (400 MHz, Methanol-d4) δ 10.65 (s, 1H), 9.10 (s, 1H), 8.45 (s, 1H), 7.80-7.55 (m, 1H), 7.28 (d, J = 7.4 Hz, 1H), 6.86 (d, J = 8.8 Hz, 1H), 3.74 (s, 5H), 3.60-3.37 (m, 1H), 3.24-3.01 (m, 4H), 2.27-1.95 (m, 2H). |
| IV-205 | 337.09 | 2.67 | 1H NMR (400 MHz, DMSO-d6) δ 10.44 (d, J = 1.4 Hz, 1H), 9.16 (d, J = 1.3 Hz, 1H), 8.60 (s, 1H), 8.12 (s, 1H), 7.76 (s, 1H), 7.67 (dd, J = 8.6, 7.5 Hz, 1H), 7.34 (d, J = 7.4 Hz, 1H), 6.87 (d, J = 8.6 Hz, 1H), 4.42-4.21 (m, 2H), 2.92 (td, J = 12.4, 2.8 Hz, 1H), 2.71-2.57 (m, 1H), 1.91-1.46 (m, 4H), 1.32-1.10 (m, 1H), 1.01 (d, J = 6.5 Hz, 3H). |
| IV-206 | 396.3 | 2.01 | 1H NMR (500 MHz, Methanol-d4) δ 9.92 (d, J = 1.4 Hz, 1H), 8.99 (d, J = 1.3 Hz, 1H), 8.64 (s, 1H), 8.50 (d, J = 6.2 Hz, 1H), 7.93 (s, 2H), 6.95 (d, J = 6.3 Hz, 1H), 5.08-4.95 (m, 1H), 4.93-4.86 (m, 1H), 4.64 (dd, J = 11.9, 3.5 Hz, 1H), 3.70-3.58 (m, 1H), 3.54 (dd, J = 14.4, 11.9 Hz, 1H), 3.34-3.32 (m, 1H), 3.21-3.04 (m, 1H), 1.50 (d, J = 6.6 Hz, 3H). |
| IV-207 | 430.4 | 2.13 | |
| IV-208 | 430.3 | 2.19 | |
| IV-209 | 389.05 | 2.4 | 1H NMR (400 MHz, Chloroform-d) δ 10.59 (d, J = 1.4 Hz, 1H), 9.29 (d, J = 1.4 Hz, 1H), 8.57 (dd, J = 2.5, 0.7 Hz, 1H), 8.37 (s, 1H), 7.79-7.66 (m, 2H), 7.21 (d, J = 7.5 Hz, 1H), 6.74 (d, J = 8.6 Hz, 1H), 6.56 (dd, J = 2.6, 1.7 Hz, 1H), 4.36 (s, 7H), 3.91 (dt, J = 7.2, 2.5 Hz, 4H), 3.77 (ddd, J = 11.0, 6.7, 4.0 Hz, 4H), 2.27 (s, 3H). |
| IV-210 | 392.1 | 1.58 | 1H NMR (400 MHz, Chloroform-d) δ 10.46 (d, J = 1.4 Hz, 1H), 9.11 (d, J = 1.4 Hz, 1H), 8.18 (s, 1H), 7.86 (d, J = 4.5 Hz, 1H), 7.50 (dd, J = 8.6, 7.5 Hz, 1H), 7.25 (s, 1H), 7.02 (d, J = 7.5 Hz, 1H), 6.55 (d, J = 8.6 Hz, 1H), 4.59 (dt, J = 13.3, 3.0 Hz, 1H), 4.46-4.38 (m, 1H), 3.87 (d, J = 12.7 Hz, 1H), 3.48 (d, J = 11.1 Hz, 1H), 3.02-2.78 (m, 2H), 2.71 (dd, J = 13.0, 10.9 Hz, 1H), 2.45 (d, J = 17.8 Hz, 1H), 2.31 (ddd, J = 17.5, 10.9, 5.8 Hz, 1H), 2.07-1.98 (m, 1H), 1.76 (dd, J = 12.3, 3.1 Hz, 1H), 1.68-1.54 (m, 1H), 1.55-1.42 (m, 1H). |
| IV-211 | 416.3 | 2.08 | 1H NMR (500 MHz, Methanol-d4) δ 10.32 (s, 1H), 9.26-9.13 (m, 1H), 8.68 (s, 1H), 8.44 (d, J = 6.3 Hz, 1H), 7.80 (s, 2H), 6.88 (d, J = 6.3 Hz, 1H), 4.71 (s, 1H), 4.55 (s, 2H), 4.28 (d, J = 10.4 Hz, 1H), 3.51-3.34 (m, 2H), 3.25-3.12 (m, 1H). |
| IV-212 | 339.34 | 1.96 | 1H NMR (400 MHz, DMSO-d6) δ 10.41 (s, 1H), 10.14-9.91 (m, 1H), 9.21 (s, 1H), 8.68 (s, 1H), 8.19 (s, 1H), 7.88-7.73 (m, 2H), 7.51 (d, J = 7.5 Hz, 1H), 7.02 (d, J = 8.5 Hz, 1H), 4.53 (d, J = 14.3 Hz, 2H), 3.59 (d, J = 12.0 Hz, 2H), 3.37 (t, J = 13.1 Hz, 2H), 3.19 (dt, J = 26.6, 13.0 Hz, 3H), 2.95-2.83 (m, 3H). exchangeable protons not observed |
| IV-213 | 396.3 | 2.1 | 1H NMR (500 MHz, Methanol-d4) δ 9.92 (d, J = 1.4 Hz, 1H), 8.99 (d, J = 1.3 Hz, 1H), 8.64 (s, 1H), 8.50 (d, J = 6.2 Hz, 1H), 7.93 (s, 2H), 6.95 (d, J = 6.3 Hz, 1H), 5.08-4.95 (m, 1H), 4.93-4.86 (m, 1H), 4.64 (dd, J = 11.9, 3.5 Hz, 1H), 3.70-3.58 (m, 1H), 3.54 (dd, J = 14.4, 11.9 Hz, 1H), 3.34-3.32 |

TABLE 7-continued

Analytical data for compounds of Formula IV

| IV- | LCMS_Plus | LCMS_RT | NMR |
|---|---|---|---|
| | | | (m, 1H), 3.21-3.04 (m, 1H), 1.50 (d, J = 6.6 Hz, 3H). |
| IV-214 | 396.3 | 2.09 | 1H NMR (500 MHz, Methanol-d4) δ 9.92 (d, J = 1.4 Hz, 1H), 8.99 (d, J = 1.3 Hz, 1H), 8.64 (s, 1H), 8.50 (d, J = 6.2 Hz, 1H), 7.93 (s, 2H), 6.95 (d, J = 6.3 Hz, 1H), 5.08-4.95 (m, 1H), 4.93-4.86 (m, 1H), 4.64 (dd, J = 11.9, 3.5 Hz, 1H), 3.70-3.58 (m, 1H), 3.54 (dd, J = 14.4, 11.9 Hz, 1H), 3.34-3.32 (m, 1H), 3.21-3.04 (m, 1H), 1.50 (d, J = 6.6 Hz, 3H). |
| IV-215 | 431.3 | 2.45 | 1H NMR (500 MHz, Methanol-d4) δ 10.19 (s, 1H), 9.25 (d, J = 1.3 Hz, 1H), 8.71 (s, 1H), 8.37 (d, J = 6.6 Hz, 1H), 7.65 (s, 2H), 6.91 (d, J = 6.7 Hz, 1H), 4.90 (d, J = 3.0 Hz, 1H), 4.27-4.18 (m, 1H), 3.88 (td, J = 12.0, 3.2 Hz, 1H), 3.61-3.46 (m, 1H), 1.18 (d, J = 6.8 Hz, 3H). |
| IV-216 | 397.2 | 2.29 | 1H NMR (500 MHz, Methanol-d4) δ 9.88 (d, J = 1.3 Hz, 1H), 8.95 (d, J = 1.3 Hz, 1H), 8.56 (s, 1H), 8.34 (d, J = 6.3 Hz, 1H), 7.75 (s, 2H), 6.78 (d, J = 6.3 Hz, 1H), 4.73 (dd, J = 10.9, 2.7 Hz, 1H), 4.66-4.48 (m, 1H), 4.48-4.31 (m, 1H), 3.88 (ddd, J = 10.8, 6.3, 2.7 Hz, 1H), 3.10 (dd, J = 13.1, 11.0 Hz, 1H), 2.85 (dd, J = 13.1, 10.7 Hz, 1H), 1.35 (d, J = 6.2 Hz, 3H). |
| IV-217 | 397.2 | 2.29 | 1H NMR (500 MHz, Methanol-d4) δ 9.88 (d, J = 1.3 Hz, 1H), 8.95 (d, J = 1.3 Hz, 1H), 8.56 (s, 1H), 8.34 (d, J = 6.3 Hz, 1H), 7.75 (s, 2H), 6.78 (d, J = 6.3 Hz, 1H), 4.73 (dd, J = 10.9, 2.7 Hz, 1H), 4.66-4.48 (m, 1H), 4.48-4.31 (m, 1H), 3.88 (ddd, J = 10.8, 6.3, 2.7 Hz, 1H), 3.10 (dd, J = 13.1, 11.0 Hz, 1H), 2.85 (dd, J = 13.1, 10.7 Hz, 1H), 1.35 (d, J = 6.2 Hz, 3H). |
| IV-218 | 431.3 | 2.47 | |
| IV-219 | 339.19 | 1.9 | 1H NMR (400 MHz, Methanol-d4) δ 10.64 (s, 1H), 9.11 (s, 1H), 8.45 (d, J = 26.0 Hz, 1H), 7.68 (dd, J = 8.6, 7.4 Hz, 1H), 7.29 (d, J = 7.4 Hz, 1H), 6.88 (d, J = 8.6 Hz, 1H), 4.45-3.78 (m, 2H), 3.72-3.42 (m, 1H), 2.43-1.82 (m, 3H), 1.63 (d, J = 9.6 Hz, 1H). 3 protons obscured by solvent peaks |
| IV-220 | 352.89 | 2.13 | 1H NMR (400 MHz, DMSO-d6) δ 10.44 (d, J = 1.4 Hz, 1H), 9.16 (s, 1H), 8.61 (s, 1H), 8.11 (s, 1H), 7.78-7.61 (m, 2H), 7.38 (d, J = 7.4 Hz, 1H), 6.88 (d, J = 8.6 Hz, 1H), 4.62-4.04 (m, 2H), 3.42 (dd, J = 15.3, 6.2 Hz, 1H), 3.15-2.91 (m, 2H), 2.09 (dd, J = 9.7, 4.5 Hz, 1H), 1.97-1.71 (m, 3H), 1.65-1.50 (m, 1H), 1.42 (dd, J = 11.9, 3.4 Hz, 1H). 1 exchangable proton not observed |
| IV-221 | 353.45 | 2.06 | 1H NMR (400 MHz, DMSO-d6) δ 10.47 (dd, J = 3.0, 1.4 Hz, 1H), 9.16 (s, 1H), 8.61 (s, 1H), 8.12 (s, 1H), 7.83-7.56 (m, 2H), 7.35 (dd, J = 11.1, 7.4 Hz, 1H), 7.00-6.75 (m, 1H), 4.43 (s, 1H), 4.33 (d, J = 6.6 Hz, 1H), 3.30 (d, J = 6.2 Hz, 1H), 2.99 (dtd, J = 18.3, 12.8, 2.7 Hz, 2H), 2.21-2.01 (m, 1H), 1.91-1.60 (m, 2H), 1.49-1.10 (m, 3H). 1 proton not observed - obscured by solvent peak |
| IV-222 | 444.4 | 2.41 | 1H NMR (500 MHz, Methanol-d4) δ 10.20 (d, J = 44.8 Hz, 1H), 9.15 (d, J = 1.4 Hz, 1H), 8.59 (s, 1H), 8.28 (d, J = 6.3 Hz, 1H), 7.69 (s, 2H), 6.75 (d, J = 6.4 Hz, 1H), 5.15-4.53 (m, 1H), 4.25 (d, J = 3.6 Hz, 1H), 3.93-3.71 (m, 1H), 3.09-2.97 (m, 1H), 2.97-2.71 (m, 1H), 1.30 (d, J = 6.3 Hz, 3H), 1.11 (d, J = 6.7 Hz, 3H). |
| IV-223 | 444.4 | 2.41 | 1H NMR (500 MHz, Methanol-d4) δ 10.35-9.99 (m, 1H), 9.18-9.13 (m, 1H), 8.59 (s, 1H), 8.28 (d, J = 6.3 Hz, 1H), 7.69 (s, 2H), 6.76 (d, J = 6.4 Hz, 1H), 5.17-4.97 (m, 1H), 4.76-4.59 (m, 1H), 4.25 (d, J = 3.6 |

TABLE 7-continued

Analytical data for compounds of Formula IV

| IV- | LCMS_Plus | LCMS_RT | NMR |
|---|---|---|---|
| | | | Hz, 2H), 3.92-3.74 (m, 1H), 3.08-2.97 (m, 1H), 2.97-2.70 (m, 1H), 1.30 (d, J = 6.2 Hz, 3H), 1.11 (d, J = 6.6 Hz, 3H). |
| IV-224 | 444.3 | 2.38 | 1H NMR (500 MHz, Methanol-d4) δ 10.35-9.99 (m, 1H), 9.18-9.13 (m, 1H), 8.59 (s, 1H), 8.28 (d, J = 6.3 Hz, 1H), 7.69 (s, 2H), 6.76 (d, J = 6.4 Hz, 1H), 5.17-4.97 (m, 1H), 4.76-4.59 (m, 1H), 4.25 (d, J = 3.6 Hz, 2H), 3.92-3.74 (m, 1H), 3.08-2.97 (m, 1H), 2.97-2.70 (m, 1H), 1.30 (d, J = 6.2 Hz, 3H), 1.11 (d, J = 6.6 Hz, 3H). |
| IV-225 | 354.7 | 2.3 | 1H NMR (400 MHz, DMSO-d6) δ 11.37 (s, 1H), 10.61 (d, J = 1.4 Hz, 1H), 9.23 (d, J = 1.4 Hz, 1H), 8.79 (s, 1H), 8.17-8.06 (m, 3H), 7.95 (dd, J = 6.8, 1.9 Hz, 1H), 7.78 (dd, J = 7.4, 1.0 Hz, 1H), 7.73-7.67 (m, 1H), 7.57 (dt, J = 8.1, 1.0 Hz, 1H), 7.48 (t, J = 2.8 Hz, 1H), 7.34-7.25 (m, 1H), 6.86 (ddd, J = 3.2, 2.0, 1.0 Hz, 1H). |
| IV-226 | 381.15 | 2.28 | 1H NMR (400 MHz, DMSO-d6) δ 10.49 (d, J = 1.4 Hz, 1H), 9.16 (d, J = 1.3 Hz, 1H), 8.59 (s, 1H), 8.11 (d, J = 2.4 Hz, 1H), 7.76-7.63 (m, 2H), 7.34 (d, J = 7.4 Hz, 1H), 6.87 (d, J = 8.6 Hz, 1H), 4.49 (d, J = 12.8 Hz, 2H), 4.13 (s, 1H), 2.87 (td, J = 12.8, 2.5 Hz, 2H), 1.91-1.82 (m, 2H), 1.50 (tt, J = 12.1, 3.2 Hz, 1H), 1.39-1.23 (m, 2H), 1.07 (s, 6H). |
| IV-227 | 379 | 1.84 | |
| IV-228 | 392.1 | 2.02 | 1H NMR (400 MHz, Methanol-d4) δ 10.57-10.51 (m, 1H), 9.05 (t, J = 1.0 Hz, 1H), 8.32 (s, 1H), 7.74-7.60 (m, 2H), 7.27 (d, J = 7.4 Hz, 1H), 6.80 (d, J = 8.6 Hz, 1H), 4.71 (t, J = 3.0 Hz, 1H), 4.68 (d, J = 2.9 Hz, 1H), 4.63-4.53 (m, 1H), 4.28-4.18 (m, 1H), 3.68 (dq, J = 11.3, 4.1, 3.6 Hz, 1H), 3.17-3.05 (m, 1H), 3.04-2.84 (m, 2H), 2.49-2.36 (m, 2H), 2.26 (dt, J = 13.2, 4.7 Hz, 1H), 1.95 (dt, J = 8.3, 4.0 Hz, 1H), 1.80 (dd, J = 10.2, 4.9 Hz, 1H), 1.79-1.64 (m, 1H). |
| IV-229 | 396 | 1.95 | 1H NMR (500 MHz, Methanol-d4) δ 9.89 (d, J = 1.4 Hz, 1H), 8.96 (d, J = 1.3 Hz, 1H), 8.57 (s, 1H), 8.33 (d, J = 6.3 Hz, 1H), 7.69 (s, 2H), 6.75 (d, J = 6.4 Hz, 1H), 4.21 (d, J = 3.8 Hz, 1H), 3.29-3.22 (m, 1H), 3.06-2.94 (m, 1H), 1.13 (d, J = 6.8 Hz, 3H), 3H not observed. |
| IV-230 | 396 | 1.95 | |
| IV-231 | 416 | 2.03 | 1H NMR (500 MHz, Methanol-d4) δ 10.31 (s, 1H), 9.19 (dd, J = 1.3, 0.6 Hz, 1H), 8.64 (s, 1H), 8.36 (d, J = 6.3 Hz, 1H), 7.72 (s, 2H), 6.80 (d, J = 6.4 Hz, 1H), 4.66-4.31 (m, 2H), 3.95 (dd, J = 10.6, 3.3 Hz, 1H), 3.27-3.13 (m, 3H), 3.03-2.93 (m, 1H). |
| IV-232 | 416 | 2.03 | 1H NMR (500 MHz, Methanol-d4) δ 10.31 (s, 1H), 9.19 (dd, J = 1.3, 0.6 Hz, 1H), 8.64 (s, 1H), 8.36 (d, J = 6.3 Hz, 1H), 7.72 (s, 2H), 6.80 (d, J = 6.4 Hz, 1H), 4.66-4.31 (m, 2H), 3.95 (dd, J = 10.6, 3.3 Hz, 1H), 3.27-3.13 (m, 3H), 3.03-2.93 (m, 1H). |
| IV-233 | 362.1 | 2.72 | 1H NMR (400 MHz, DMSO-d6) δ 11.42 (s, 1H), 10.41 (d, J = 1.5 Hz, 1H), 9.35 (s, 1H), 8.88 (s, 1H), 8.24-8.10 (m, 2H), 7.95 (dd, J = 7.7, 1.0 Hz, 1H), 7.70-7.49 (m, 4H), 7.40-7.28 (m, 1H), 6.97-6.89 (m, 1H). |
| IV-234 | 337.09 | 2.65 | 1H NMR (400 MHz, DMSO-d6) δ 11.41 (s, 1H), 10.62 (d, J = 1.4 Hz, 1H), 9.32 (d, J = 1.4 Hz, 1H), 8.93 (s, 1H), 8.21 (dd, J = 7.8, 1.0 Hz, 1H), 8.13 (t, J = 7.9 Hz, 1H), 7.92 (dd, J = 7.8, 0.9 Hz, 1H), 7.66-7.45 (m, 3H), 7.30 (dd, J = 8.1, 7.4 Hz, 1H), 6.96 (ddd, J = 3.1, 2.0, 0.9 Hz, 1H). |
| IV-235 | 397.1 | 1.79 | |
| IV-236 | 397.3 | 1.81 | |
| IV-237 | 382 | 1.84 | |
| IV-238 | 382 | 1.84 | |

TABLE 7-continued

Analytical data for compounds of Formula IV

| IV- | LCMS_Plus | LCMS_RT | NMR |
|---|---|---|---|
| IV-239 | 338.64 | 1.68 | 1H NMR (400 MHz, DMSO-d6) δ 10.37 (d, J = 1.4 Hz, 1H), 10.00 (s, 1H), 9.24 (d, J = 1.4 Hz, 1H), 8.74 (s, 1H), 8.55 (d, J = 6.2 Hz, 1H), 8.21 (s, 1H), 7.83 (d, J = 2.4 Hz, 1H), 6.97 (d, J = 6.3 Hz, 1H), 4.71 (s, 2H), 3.58 (s, 2H), 3.33 (s, 6H). |
| IV-240 | 325.84 | 1.64 | 1H NMR (400 MHz, Chloroform/Methanol-d4) δ 10.54 (s, 1H), 9.09 (s, 1H), 8.65 (s, 1H), 8.34 (d, J = 6.3 Hz, 1H), 7.44 (s, 2H), 6.59 (d, J = 6.4 Hz, 1H), 4.30 (s, 11H), 3.92-3.77 (m, 10H), 3.42 (t, J = 7.1 Hz, 2H), 3.33 (p, J = 1.6 Hz, 4H), 3.21-3.14 (m, 2H), 2.83 (d, J = 1.1 Hz, 3H), 2.37 (t, J = 8.2 Hz, 2H), 2.10-1.98 (m, 2H). |
| IV-241 | 353.85 | 1.83 | 1H NMR (400 MHz, DMSO-d6) δ 10.32 (s, 1H), 9.26 (s, 1H), 8.78-8.68 (m, 1H), 8.36 (d, J = 6.7 Hz, 1H), 7.90 (s, 1H), 6.91 (d, J = 6.8 Hz, 1H), 3.81-3.54 (m, 2H), 3.34-3.25 (m, 1H), 3.14 (qt, J = 8.7, 4.4 Hz, 1H), 2.74-2.67 (m, 2H), 1.99-1.77 (m, 3H), 1.75-1.43 (m, 4H). |
| IV-242 | 353.9 | 1.74 | 1H NMR (400 MHz, DMSO-d6) δ 10.14 (d, J = 1.5 Hz, 1H), 9.04 (d, J = 1.4 Hz, 1H), 8.46 (s, 1H), 8.17 (d, J = 6.5 Hz, 1H), 8.01 (s, 1H), 7.65 (s, 1H), 6.66 (d, J = 6.6 Hz, 1H), 3.28-3.15 (m, 2H), 3.03-2.63 (m, 2H), 1.71-1.39 (m, 4H), 1.38-1.01 (m, 3H). 1 proton obscured by solvent peak |
| IV-243 | 354 | 1.69 | 1H NMR (400 MHz, Methanol-d4) δ 10.50 (d, J = 1.4 Hz, 1H), 9.15-9.07 (m, 1H), 8.68 (s, 1H), 8.27 (dd, J = 17.3, 6.7 Hz, 1H), 7.40 (d, J = 0.6 Hz, 3H), 6.64 (dd, J = 15.8, 6.7 Hz, 1H), 4.28 (d, J = 6.5 Hz, 2H), 3.33 (dtd, J = 3.2, 1.6, 0.6 Hz, 5H), 3.15 (s, 1H), 2.21 (dt, J = 11.6, 6.2 Hz, 1H), 2.01 (d, J = 0.6 Hz, 1H), 1.51-1.34 (m, 1H). |
| IV-244 | 397.2 | 2.24 | 1H NMR (500 MHz, Methanol-d4) δ 9.95 (d, J = 1.3 Hz, 1H), 8.98 (d, J = 1.3 Hz, 1H), 8.62 (s, 1H), 8.38 (d, J = 6.3 Hz, 1H), 7.66 (s, 2H), 6.79 (d, J = 6.4 Hz, 1H), 4.90 (d, J = 3.0 Hz, 1H), 4.56 (s, 2H), 4.22 (dd, J = 11.5, 4.2 Hz, 1H), 3.87 (td, J = 11.8, 3.1 Hz, 1H), 3.49-3.36 (m, 1H), 1.14 (d, J = 6.8 Hz, 3H). |
| IV-245 | 397.2 | 2.2 | 1H NMR (500 MHz, Methanol-d4) δ 9.94 (d, J = 1.3 Hz, 1H), 8.96 (d, J = 1.3 Hz, 1H), 8.61 (s, 1H), 8.40 (d, J = 6.3 Hz, 1H), 7.59 (s, 2H), 6.77 (d, J = 6.3 Hz, 1H), 5.07-4.99 (m, 1H), 4.94 (d, J = 1.6 Hz, 1H), 4.12-4.04 (m, 1H), 3.84-3.69 (m, 2H), 3.55-3.45 (m, 1H), 1.52 (d, J = 6.7 Hz, 3H). |
| IV-246 | 410.1 | 2.1 | 1H NMR (500 MHz, Methanol-d4) δ 9.81 (s, 1H), 8.93 (d, J = 1.3 Hz, 1H), 8.52 (s, 1H), 8.27 (d, J = 6.3 Hz, 1H), 7.72 (s, 2H), 6.73 (d, J = 6.4 Hz, 1H), 5.19-4.95 (m, 1H), 4.27 (d, J = 3.7 Hz, 1H), 3.92-3.70 (m, 1H), 3.10-2.96 (m, 1H), 2.96-2.67 (m, 1H), 1.31 (d, J = 6.1 Hz, 3H), 1.10 (d, J = 6.8 Hz, 3H). |
| IV-247 | 410 | 2.1 | 1H NMR (500 MHz, DMSO-d6) δ 9.87-9.77 (m, 1H), 9.10-8.98 (m, 1H), 8.57 (s, 1H), 8.36 (d, J = 6.2 Hz, 1H), 7.59 (s, 2H), 6.79 (d, J = 6.2 Hz, 1H), 4.79-4.58 (m, 1H), 4.34-4.16 (m, 1H), 4.13 (d, J = 3.6 Hz, 1H), 2.80-2.74 (m, 2H), 1.22 (d, J = 6.2 Hz, 3H), 1.06 (d, J = 6.7 Hz, 3H). |
| IV-248 | 381.25 | 1.57 | 1H NMR (400 MHz, DMSO-d6) δ 9.45-9.40 (m, 1H), 8.15 (d, J = 1.3 Hz, 1H), 7.67 (s, 1H), 6.62 (d, J = 0.5 Hz, 1H), 5.79 (d, J = 6.9 Hz, 1H), 3.05 (td, J = 10.3, 5.2 Hz, 1H), 2.51-2.35 (m, 3H), 1.83 (t, J = 0.8 Hz, 2H), 1.37 (t, J = 8.1 Hz, 1H), 1.17-0.98 (m, 3H), 0.96 (s, 3H), 0.66-0.51 (m, 2H). |
| IV-249 | 380.9 | 1.57 | 1H NMR (400 MHz, DMSO-d6) δ 9.48 (d, J = 1.3 Hz, 1H), 8.43 (d, J = 1.4 Hz, 1H), 7.96 (s, 1H), 7.40 (d, J = 7.4 Hz, 1H), 6.84 |

TABLE 7-continued

Analytical data for compounds of Formula IV

| IV- | LCMS_Plus | LCMS_RT | NMR |
|---|---|---|---|
| | | | (s, 2H), 6.12 (d, J = 7.4 Hz, 1H), 3.63 (s, 1H), 3.07 (dd, J = 9.4, 4.5 Hz, 1H), 2.88-2.53 (m, 3H), 1.32-1.23 (m, 2H), 1.15 (s, 3H), 0.95 (t, J = 9.6 Hz, 2H). 1 exchangeable proton not observed |
| IV-250 | 417.1 | 1.68 | 1H NMR (400 MHz, DMSO-d6) δ 9.48 (d, J = 1.3 Hz, 1H), 8.43 (d, J = 1.4 Hz, 1H), 7.96 (s, 1H), 7.40 (d, J = 7.4 Hz, 1H), 6.84 (s, 2H), 6.12 (d, J = 7.4 Hz, 1H), 3.63 (s, 1H), 3.07 (dd, J = 9.4, 4.5 Hz, 1H), 2.88-2.53 (m, 3H), 1.32-1.23 (m, 2H), 1.15 (s, 3H), 0.95 (t, J = 9.6 Hz, 2H). 1 exchangeable proton not observed |
| IV-251 | 417.05 | 1.76 | 1H NMR (400 MHz, DMSO-d6) δ 10.38 (d, J = 1.4 Hz, 1H), 9.23 (d, J = 1.4 Hz, 1H), 8.69 (s, 1H), 8.45 (d, J = 6.3 Hz, 1H), 8.23 (d, J = 2.4 Hz, 1H), 7.91-7.86 (m, 1H), 7.20 (q, J = 4.9 Hz, 1H), 6.88 (d, J = 6.3 Hz, 1H), 5.00 (s, 1H), 4.36 (s, 1H), 3.32-3.21 (m, 1H), 3.19-3.05 (m, 2H), 2.62 (d, J = 4.7 Hz, 3H), 2.16 (d, J = 12.8 Hz, 1H), 1.94-1.74 (m, 2H), 1.65-1.51 (m, 1H). |
| IV-252 | 417.05 | 1.67 | 1H NMR (400 MHz, DMSO-d6) δ 10.40 (d, J = 1.4 Hz, 1H), 9.22 (d, J = 1.3 Hz, 1H), 8.65 (s, 1H), 8.42 (d, J = 6.2 Hz, 1H), 8.18 (d, J = 2.3 Hz, 1H), 7.83-7.78 (m, 1H), 7.03 (q, J = 4.8 Hz, 1H), 6.90 (d, J = 6.3 Hz, 1H), 4.66 (s, 2H), 3.49 (tt, J = 11.9, 3.8 Hz, 1H), 3.13 (td, J = 13.0, 2.6 Hz, 2H), 2.63 (d, J = 4.6 Hz, 3H), 2.15-2.06 (m, 2H), 1.61 (qd, J = 12.5, 4.3 Hz, 2H). |
| IV-253 | 362.85 | 1.73 | 1H NMR (400 MHz, DMSO-d6) δ 10.40 (d, J = 1.4 Hz, 1H), 9.22 (d, J = 1.4 Hz, 1H), 8.68 (s, 1H), 8.45 (d, J = 6.2 Hz, 1H), 8.18 (s, 1H), 7.81 (s, 1H), 6.87 (d, J = 6.3 Hz, 1H), 6.38 (s, 2H), 4.24 (s, 2H), 3.90 (s, 2H), 2.41 (t, J = 5.9 Hz, 1H). |
| IV-254 | 349.14 | 1.78 | 1H NMR (400 MHz, DMSO-d6) δ 10.37 (d, J = 1.4 Hz, 1H), 9.21 (d, J = 1.4 Hz, 1H), 8.64 (s, 1H), 8.42 (d, J = 6.2 Hz, 1H), 8.20-8.15 (m, 1H), 7.81 (d, J = 2.5 Hz, 1H), 6.88 (d, J = 6.3 Hz, 1H), 4.07 (s, 2H), 3.59 (ddd, J = 13.2, 9.0, 3.3 Hz, 2H), 3.27-3.18 (m, 1H), 2.02 (ddt, J = 13.5, 6.8, 3.6 Hz, 2H), 1.81 (dtd, J = 12.8, 8.8, 3.6 Hz, 2H). |
| IV-255 | 415.3 | 2.48 | 1H NMR (500 MHz, DMSO-d6) δ 10.20 (s, 1H), 9.40-9.34 (m, 1H), 9.25 (t, J = 1.4 Hz, 1H), 8.79 (s, 1H), 8.50-8.43 (m, 1H), 8.00 (t, J = 1.8 Hz, 1H), 7.78 (t, J = 1.7 Hz, 1H), 6.99 (d, J = 6.4 Hz, 1H), 4.89-4.66 (m, 1H), 4.57 (ddd, J = 10.5, 6.3, 4.0 Hz, 1H), 4.48-4.21 (m, 1H), 3.62 (dd, J = 13.0, 10.1 Hz, 1H), 3.21 (ddd, J = 13.9, 11.5, 3.1 Hz, 1H), 2.33-2.24 (m, 1H), 2.24-2.12 (m, 1H), 2.00-1.89 (m, 1H), 1.74-1.61 (m, 1H). |
| IV-256 | 339.14 | 1.61 | 1H NMR (400 MHz, DMSO-d6) δ 10.39 (d, J = 1.4 Hz, 1H), 9.25 (d, J = 1.4 Hz, 1H), 8.72 (s, 1H), 8.47 (d, J = 6.3 Hz, 1H), 8.30 (s, 1H), 8.03 (s, 3H), 7.94 (s, 1H), 6.88 (d, J = 6.3 Hz, 1H), 4.58 (s, 1H), 4.04 (s, 1H), 3.39 (dd, J = 12.7, 8.9 Hz, 1H), 2.07 (s, 1H), 1.91-1.81 (m, 1H), 1.74-1.55 (m, 2H).. 1 proton obscured by solvent peaks |
| IV-257 | 392.95 | 1.69 | 1H NMR (400 MHz, DMSO-d6) δ 10.37 (d, J = 1.4 Hz, 1H), 9.25 (d, J = 1.4 Hz, 1H), 8.71 (s, 1H), 8.44 (d, J = 6.4 Hz, 1H), 8.21 (d, J = 2.2 Hz, 1H), 7.89 (s, 1H), 6.94 (d, J = 6.5 Hz, 1H), 4.53 (dt, J = 13.4, 3.0 Hz, 1H), 3.55 (dt, J = 8.3, 4.4 Hz, 1H), 3.35-3.27 (m, 1H), 3.11 (td, J = 12.6, 3.4 Hz, 1H), 2.94 (dd, J = 13.2, 11.0 Hz, 1H), 2.85-2.52 (m, 1H), 2.30 (dd, J = 7.7, 5.0 Hz, 2H), 2.18 (dd, J = 10.1, 6.1 Hz, 1H), 1.97-1.78 (m, 2H), 1.76-1.53 (m, 2H). |

TABLE 7-continued

Analytical data for compounds of Formula IV

| IV- | LCMS_Plus | LCMS_RT | NMR |
|---|---|---|---|
| IV-258 | 349.29 | 1.98 | |
| IV-259 | 391.1 | 2.3 | 1H NMR (400 MHz, DMSO-d6) δ 10.28 (d, J = 1.2 Hz, 1H), 9.32 (d, J = 1.2 Hz, 1H), 8.71 (s, 1H), 7.77 (dd, J = 8.6, 7.5 Hz, 1H), 7.47 (d, J = 7.4 Hz, 1H), 6.95 (d, J = 8.5 Hz, 1H), 3.74-3.58 (m, 8H), 2.08 (d, J = 1.1 Hz, 3H). |
| IV-260 | 380 | 1.52 | 1H NMR (400 MHz, Methanol-d4) δ 10.68-10.49 (m, 1H), 9.14-9.00 (m, 1H), 8.52-8.34 (m, 1H), 7.78-7.69 (m, 1H), 7.45-7.27 (m, 1H), 6.94-6.82 (m, 1H), 3.96-3.66 (m, 8H), 3.11-2.97 (m, 3H), 2.32-2.13 (m, 3H). exchangeable proton not observed |
| IV-261 | 337.99 | 2.17 | 1H NMR (400 MHz, DMSO-d6) δ 10.40 (d, J = 1.4 Hz, 1H), 9.21 (d, J = 1.4 Hz, 1H), 8.61 (s, 1H), 8.36 (d, J = 6.3 Hz, 1H), 8.17 (d, J = 2.2 Hz, 1H), 7.80 (d, J = 2.5 Hz, 1H), 6.79 (d, J = 6.4 Hz, 1H), 4.86 (s, 1H), 4.39 (s, 1H), 3.05 (td, J = 13.2, 3.0 Hz, 1H), 1.84-1.65 (m, 5H), 1.46 (d, J = 12.8 Hz, 1H), 1.25 (d, J = 6.8 Hz, 3H). |
| IV-262 | 392.85 | 1.51 | 1H NMR (400 MHz, DMSO-d6) δ 10.34 (d, J = 1.4 Hz, 1H), 9.22 (d, J = 1.3 Hz, 1H), 8.64 (d, J = 1.0 Hz, 1H), 8.41 (d, J = 6.2 Hz, 1H), 8.19 (d, J = 2.6 Hz, 1H), 7.84 (d, J = 2.6 Hz, 1H), 6.90 (d, J = 6.3 Hz, 1H), 3.95 (q, J = 7.6 Hz, 1H), 3.60-3.35 (m, 2H), 3.26-3.17 (m, 4H), 2.78-2.63 (m, 2H), 2.26 (dt, J = 11.6, 5.9 Hz, 1H), 1.84 (dh, J = 10.1, 6.3, 4.1 Hz, 2H), 1.67 (dtt, J = 14.4, 6.4, 3.6 Hz, 1H). |
| IV-263 | 393.1 | 1.67 | 1H NMR (400 MHz, DMSO-d6) δ 10.38 (d, J = 1.4 Hz, 1H), 9.22 (d, J = 1.3 Hz, 1H), 8.68 (s, 1H), 8.44 (d, J = 6.2 Hz, 1H), 8.19 (d, J = 2.2 Hz, 1H), 7.86 (d, J = 2.4 Hz, 1H), 6.91 (d, J = 6.2 Hz, 1H), 4.55-4.39 (m, 3H), 4.19 (d, J = 17.5 Hz, 1H), 3.69-3.49 (m, 2H), 2.60-2.51 (m, 1H), 2.03 (d, J = 12.5 Hz, 1H), 1.81 (d, J = 13.0 Hz, 1H), 1.68 (d, J = 13.0 Hz, 1H), 1.50 (qt, J = 13.2, 3.5 Hz, 1H), 1.37-1.19 (m, 2H). |
| IV-264 | 352.09 | 2.39 | 1H NMR (400 MHz, DMSO-d6) δ 10.39 (d, J = 1.4 Hz, 1H), 9.21 (d, J = 1.3 Hz, 1H), 8.61 (s, 1H), 8.34 (d, J = 6.2 Hz, 1H), 8.17 (d, J = 2.5 Hz, 1H), 7.82 (d, J = 2.9 Hz, 1H), 6.80 (d, J = 6.4 Hz, 1H), 2.97 (dq, J = 10.6, 8.0, 6.6 Hz, 1H), 1.87-1.71 (m, 2H), 1.60-1.39 (m, 3H), 1.11 (d, J = 6.8 Hz, 3H), 1.03-0.90 (m, 5H). |
| IV-265 | 379.1 | 1.89 | 1H NMR (400 MHz, DMSO-d6) δ 10.39 (d, J = 1.4 Hz, 1H), 9.20 (d, J = 1.3 Hz, 1H), 8.63 (s, 1H), 8.37 (d, J = 6.3 Hz, 1H), 8.17 (d, J = 2.6 Hz, 1H), 7.85 (d, J = 2.7 Hz, 1H), 6.83 (d, J = 6.3 Hz, 1H), 4.39 (s, 2H), 3.09 (td, J = 12.5, 3.1 Hz, 1H), 2.82 (dq, J = 13.9, 3.6, 3.1 Hz, 2H), 2.70 (dd, J = 13.0, 10.7 Hz, 1H), 2.14 (td, J = 11.9, 3.2 Hz, 1H), 2.02-1.84 (m, 3H), 1.79-1.70 (m, 1H), 1.65-1.43 (m, 2H), 1.35-1.12 (m, 2H). |
| IV-266 | 382 | 1.74 | 1H NMR (400 MHz, DMSO-d6) δ 10.38 (d, J = 1.4 Hz, 1H), 9.21 (d, J = 1.4 Hz, 1H), 8.63 (s, 1H), 8.40 (d, J = 6.3 Hz, 1H), 8.18 (d, J = 2.6 Hz, 1H), 7.80 (d, J = 2.4 Hz, 1H), 6.89 (d, J = 6.4 Hz, 1H), 3.96 (s, 4H), 3.85 (s, 4H), 1.79-1.70 (m, 4H). |
| IV-267 | 381 | 1.49 | 1H NMR (400 MHz, DMSO-d6) δ 10.53-10.45 (m, 1H), 9.20 (d, J = 1.3 Hz, 1H), 8.60 (d, J = 4.0 Hz, 1H), 8.36 (d, J = 5.9 Hz, 1H), 8.16 (s, 1H), 7.80 (s, 1H), 6.52 (d, J = 5.9 Hz, 1H), 5.28-5.19 (m, 1H), 4.75 (s, 1H), 4.02 (s, 1H), 2.95 (s, 2H), 2.81 (s, 2H), 2.25 (s, 1H), 2.15 (d, J = 9.8 Hz, 3H), 2.06 (s, 2H). |

TABLE 7-continued

Analytical data for compounds of Formula IV

| IV- | LCMS_Plus | LCMS_RT | NMR |
|---|---|---|---|
| IV-268 | 379 | 1.45 | 1H NMR (400 MHz, DMSO-d6) δ 10.32 (d, J = 1.4 Hz, 1H), 9.13 (d, J = 1.4 Hz, 1H), 8.60 (s, 1H), 8.36 (d, J = 6.2 Hz, 1H), 8.10 (s, 1H), 7.75 (d, J = 2.3 Hz, 1H), 6.73 (d, J = 6.2 Hz, 1H), 3.80 (d, J = 17.3 Hz, 1H), 3.66 (tt, J = 10.2, 4.7 Hz, 1H), 3.49-3.36 (m, 1H), 3.35-3.25 (m, 1H), 3.20-3.10 (m, 1H), 2.91 (t, J = 11.8 Hz, 1H), 2.15 (s, 2H), 1.95-1.83 (m, 1H), 1.81-1.64 (m, 1H), 1.52 (qd, J = 11.3, 7.2 Hz, 1H). |
| IV-269 | 380 | 1.9 | 1H NMR (400 MHz, DMSO-d6) δ 10.40 (d, J = 1.4 Hz, 1H), 9.21 (d, J = 1.4 Hz, 1H), 8.62 (s, 1H), 8.37 (d, J = 6.3 Hz, 1H), 8.17 (d, J = 2.4 Hz, 1H), 7.80 (d, J = 2.0 Hz, 1H), 6.86 (d, J = 6.4 Hz, 1H), 4.02 (s, 2H), 3.80 (t, J = 6.7 Hz, 2H), 3.60 (tt, J = 8.8, 2.5 Hz, 2H), 1.92 (dq, J = 8.1, 6.8 Hz, 2H), 1.77-1.57 (m, 6H). |
| IV-270 | 352.04 | 1.58 | 1H NMR (400 MHz, DMSO-d6) δ 10.46 (d, J = 1.4 Hz, 1H), 9.21 (d, J = 1.4 Hz, 1H), 8.58 (s, 1H), 8.38 (d, J = 5.9 Hz, 1H), 8.20-8.14 (m, 1H), 7.79 (d, J = 2.3 Hz, 1H), 6.41 (d, J = 6.0 Hz, 1H), 4.17 (s, 4H), 3.88 (s, 2H), 3.78 (t, J = 7.0 Hz, 2H), 2.23 (t, J = 7.0 Hz, 2H). |
| IV-271 | 352.09 | 2.38 | 1H NMR (400 MHz, DMSO-d6) δ 10.27 (d, J = 1.4 Hz, 1H), 9.07 (d, J = 1.4 Hz, 1H), 8.46 (s, 1H), 8.19 (d, J = 6.3 Hz, 1H), 8.03 (s, 1H), 7.66 (s, 1H), 6.63 (d, J = 6.4 Hz, 1H), 4.63 (s, 1H), 4.01 (d, J = 13.4 Hz, 1H), 3.15 (d, J = 3.6 Hz, 1H), 1.95 (s, 1H), 1.84 (qd, J = 6.9, 2.9 Hz, 2H), 1.32 (d, J = 11.2 Hz, 1H), 1.12 (d, J = 6.7 Hz, 4H), 0.87 (d, J = 6.9 Hz, 3H). |
| IV-272 | 381 | 1.55 | 1H NMR (400 MHz, DMSO-d6) δ 10.40 (d, J = 1.4 Hz, 1H), 9.22 (d, J = 1.4 Hz, 1H), 8.65 (s, 1H), 8.44 (dd, J = 6.3, 1.7 Hz, 1H), 8.19 (s, 1H), 7.82 (d, J = 2.4 Hz, 1H), 6.83 (dd, J = 6.4, 2.1 Hz, 1H), 4.75 (s, 1H), 4.28 (dd, J = 31.7, 13.3 Hz, 2H), 3.84 (dd, J = 58.1, 12.1 Hz, 1H), 3.46 (d, J = 68.3 Hz, 1H), 3.13-2.87 (m, 1H), 2.09 (d, J = 17.0 Hz, 3H), 1.25 (d, J = 6.6 Hz, 2H), 1.17 (d, J = 6.6 Hz, 2H). NB Rotamers evident. |
| IV-273 | 393 | 1.59 | |
| IV-274 | 393 | 1.59 | |
| IV-275 | 487.2 | 2.72 | 1H NMR (500 MHz, Methanol-d4) δ 10.06 (s, 1H), 9.12 (d, J = 1.3 Hz, 1H), 8.43 (s, 1H), 7.74 (dd, J = 8.6, 7.5 Hz, 1H), 7.38-7.34 (m, 1H), 7.10-6.83 (m, 2H), 4.64-4.50 (m, 2H), 3.56 (dd, J = 13.7, 3.9 Hz, 1H), 3.14 (dd, J = 13.7, 9.3 Hz, 1H), 3.03-2.97 (m, 1H), 2.96 (s, 3H), 2.94-2.86 (m, 1H), 2.38-2.07 (m, 2H), 1.13 (d, J = 6.7 Hz, 3H). |
| IV-276 | 394 | 1.81 | 1H NMR (400 MHz, Methanol-d4) δ 10.26 (d, J = 1.4 Hz, 1H), 9.09 (d, J = 1.4 Hz, 1H), 8.44 (s, 1H), 7.74 (dd, J = 8.6, 7.5 Hz, 1H), 7.37 (d, J = 7.4 Hz, 1H), 6.89 (d, J = 8.6 Hz, 1H), 3.79 (tt, J = 6.3, 3.8 Hz, 6H), 3.70 (dd, J = 6.6, 3.9 Hz, 2H), 3.29 (s, 3H), 3.21 (s, 3H), 2.21 (s, 3H). |
| IV-277 | 393 | 1.75 | 1H NMR (400 MHz, DMSO-d6) δ 10.41 (d, J = 1.4 Hz, 1H), 9.22 (d, J = 1.4 Hz, 1H), 8.66 (s, 1H), 8.45 (d, J = 6.2 Hz, 1H), 8.19 (d, J = 2.4 Hz, 1H), 7.82 (d, J = 2.7 Hz, 1H), 6.87 (d, J = 6.3 Hz, 1H), 3.87 (s, 4H), 3.79 (s, 2H), 3.66 (s, 2H), 2.04 (tt, J = 7.7, 4.9 Hz, 1H), 0.78 (tt, J = 7.9, 2.9 Hz, 4H). |
| IV-278 | 424.3 | 2.25 | 1H NMR (500 MHz, Methanol-d4) δ 9.91 (s, 1H), 9.02 (d, J = 1.4 Hz, 1H), 8.66 (s, 1H), 8.51 (d, J = 6.3 Hz, 1H), 7.77 (s, 1H), 6.96 (d, J = 6.5 Hz, 1H), 4.80 (d, J = 4.2 Hz, 1H), 3.70 (ddd, J = 11.7, 6.6, 3.7 Hz, 1H), 3.29 (s, 1H), 2.41 (s, 3H), 1.58 (d, J = 6.6 Hz, 3H), 1.38 (d, J = 7.2 Hz, 3H). |

TABLE 7-continued

Analytical data for compounds of Formula IV

| IV- | LCMS_Plus | LCMS_RT | NMR |
|---|---|---|---|
| IV-279 | 456.1 | 2.17 | 1H NMR (500 MHz, Methanol-d4) δ 9.87 (s, 1H), 8.96 (d, J = 1.3 Hz, 1H), 8.59 (s, 1H), 8.44 (d, J = 6.4 Hz, 1H), 7.90 (s, 2H), 6.94 (d, J = 6.4 Hz, 1H), 4.93 (d, J = 4.1 Hz, 1H), 3.68 (dtd, J = 13.1, 6.5, 3.7 Hz, 1H), 3.30-3.24 (m, 1H), 1.58 (d, J = 6.5 Hz, 3H), 1.36 (d, J = 7.1 Hz, 3H), 2H not observed. |
| IV-280 | 388.2 | 2.08 | 1H NMR (500 MHz, Methanol-d4) δ 10.07 (s, 1H), 9.26 (s, 1H), 8.81 (s, 1H), 8.37 (d, J = 6.7 Hz, 1H), 7.86 (s, 2H), 7.09 (s, 1H), 5.39-5.08 (m, 1H), 5.08-4.95 (m, 1H), 4.28 (dd, J = 11.8, 3.9 Hz, 1H), 4.12-3.87 (m, 2H), 3.75-3.56 (m, 1H), 1.23 (d, J = 6.2 Hz, 3H). |
| IV-281 | 388.2 | 2.07 | |
| IV-282 | 424 | 2.21 | 1H NMR (500 MHz, Methanol-d4) δ 10.06-9.73 (m, 1H), 8.97 (s, 1H), 8.56 (s, 1H), 8.32 (d, J = 6.3 Hz, 1H), 7.62 (s, 1H), 6.75 (d, J = 6.4 Hz, 1H), 5.34-4.98 (m, 1H), 4.63-4.44 (m, 1H), 4.15 (d, J = 3.6 Hz, 1H), 3.97-3.74 (m, 1H), 3.13-2.98 (m, 1H), 2.98-2.68 (m, 1H), 2.33 (s, 3H), 1.30 (d, J = 6.5 Hz, 3H), 1.14 (d, J = 6.9 Hz, 3H). |
| IV-283 | 424 | 2.2 | 1H NMR (500 MHz, Methanol-d4) δ 10.06-9.73 (m, 1H), 8.97 (s, 1H), 8.56 (s, 1H), 8.32 (d, J = 6.3 Hz, 1H), 7.62 (s, 1H), 6.75 (d, J = 6.4 Hz, 1H), 5.34-4.98 (m, 1H), 4.63-4.44 (m, 1H), 4.15 (d, J = 3.6 Hz, 1H), 3.97-3.74 (m, 1H), 3.13-2.98 (m, 1H), 2.98-2.68 (m, 1H), 2.33 (s, 3H), 1.30 (d, J = 6.5 Hz, 3H), 1.14 (d, J = 6.9 Hz, 3H). |
| IV-284 | 392.15 | 2.02 | 1H NMR (400 MHz, Methanol-d4) δ 10.62 (d, J = 1.4 Hz, 1H), 9.06 (d, J = 1.3 Hz, 1H), 8.32 (s, 1H), 7.69 (d, J = 8.0 Hz, 1H), 7.27 (d, J = 7.5 Hz, 1H), 6.78 (d, J = 8.5 Hz, 1H), 4.10-3.56 (m, 8H), 2.00 (d, J = 4.5 Hz, 1H), 1.01-0.80 (m, 4H). |
| IV-285 | 401.05 | 1.91 | 1H NMR (400 MHz, DMSO-d6) δ 10.38-10.29 (m, 1H), 9.37 (d, J = 1.4 Hz, 1H), 8.78-8.70 (m, 2H), 8.61 (d, J = 10.7 Hz, 1H), 8.45 (d, J = 6.2 Hz, 1H), 8.04-7.95 (m, 2H), 6.86 (d, J = 6.3 Hz, 1H), 3.94-3.71 (m, 4H), 3.67-3.59 (m, 4H), 2.10 (s, 3H). |
| IV-286 | 384 | 2.13 | 1H NMR (400 MHz, DMSO-d6) δ 9.83-9.78 (m, 1H), 9.13 (d, J = 1.3 Hz, 1H), 8.67 (s, 1H), 8.40 (d, J = 6.2 Hz, 1H), 6.88 (d, J = 6.3 Hz, 1H), 4.50 (dt, J = 13.3, 3.0 Hz, 2H), 3.56-3.44 (m, 1H), 3.03 (td, J = 13.2, 12.7, 3.4 Hz, 1H), 2.90-2.68 (m, 2H), 2.29 (dd, J = 8.0, 4.8 Hz, 2H), 2.08 (ddd, J = 12.3, 6.3, 3.4 Hz, 1H), 1.89-1.76 (m, 1H), 1.75-1.48 (m, 2H), 0.97 (s, 1H). |
| IV-287 | 454.2 | 2.17 | |
| IV-288 | 456.2 | 2.17 | 1H NMR (500 MHz, DMSO-d6) δ 13.10 (s, 1H), 9.89 (s, 1H), 9.81-9.66 (m, 1H), 9.28 (s, 1H), 9.19-9.07 (m, 1H), 8.71 (s, 1H), 8.51 (d, J = 6.2 Hz, 1H), 8.14-7.60 (m, 1H), 7.02 (d, J = 6.3 Hz, 1H), 5.47-4.90 (m, 1H), 4.84-4.72 (m, 1H), 4.72-4.12 (m, 1H), 3.59-3.47 (m, 1H), 3.15-2.95 (m, 1H), 1.46 (s, 3H), 1.28-1.19 (m, 3H). |
| IV-289 | 401.1 | 1.89 | 1H NMR (400 MHz, DMSO-d6) δ 10.26 (d, J = 1.5 Hz, 1H), 9.36 (d, J = 1.4 Hz, 1H), 9.21 (dd, J = 2.4, 0.9 Hz, 1H), 8.68 (dd, J = 4.8, 1.6 Hz, 1H), 8.62 (s, 1H), 8.48-8.35 (m, 2H), 7.60 (ddd, J = 8.0, 4.8, 0.9 Hz, 1H), 6.86 (d, J = 6.3 Hz, 1H), 3.81 (d, J = 21.4 Hz, 4H), 3.63 (dd, J = 6.6, 3.9 Hz, 4H), 2.09 (s, 3H). |
| IV-290 | 388 | 2.05 | 1H NMR (500 MHz, Methanol-d4) δ 10.37 (d, J = 1.4 Hz, 1H), 9.16 (d, J = 1.4 Hz, 1H), 8.66 (s, 1H), 8.40 (d, J = 6.3 Hz, 1H), 7.73-7.59 (m, 2H), 6.81 (d, J = 6.3 Hz, 1H), 4.90 (d, J = 3.0 Hz, 1H), 4.25-4.17 |

TABLE 7-continued

Analytical data for compounds of Formula IV

| IV- | LCMS_Plus | LCMS_RT | NMR |
|---|---|---|---|
| | | | (m, 1H), 3.86 (td, J = 12.0, 3.2 Hz, 1H), 3.65 (d, J = 5.4 Hz, 1H), 3.59 (dd, J = 11.2, 4.9 Hz, 1H), 3.51 (dd, J = 11.2, 6.0 Hz, 1H), 1.13 (d, J = 6.8 Hz, 3H). |
| IV-291 | 388 | 2.05 | 1H NMR (500 MHz, Methanol-d4) δ 10.37 (d, J = 1.4 Hz, 1H), 9.16 (d, J = 1.4 Hz, 1H), 8.66 (s, 1H), 8.40 (d, J = 6.3 Hz, 1H), 7.73-7.59 (m, 2H), 6.81 (d, J = 6.3 Hz, 1H), 4.90 (d, J = 3.0 Hz, 1H), 4.25-4.17 (m, 1H), 3.86 (td, J = 12.0, 3.2 Hz, 1H), 3.65 (d, J = 5.4 Hz, 1H), 3.59 (dd, J = 11.2, 4.9 Hz, 1H), 3.51 (dd, J = 11.2, 6.0 Hz, 1H), 1.13 (d, J = 6.8 Hz, 3H). |
| IV-292 | 472 | 2.6 | |
| IV-293 | 384 | 2.16 | |
| IV-294 | 384 | 2.15 | |
| IV-295 | 472 | 2.59 | |
| IV-296 | 472 | 2.59 | 1H NMR (500 MHz, DMSO-d6) δ 12.57 (s, 1H), 10.16 (s, 1H), 9.30 (s, 1H), 8.65 (s, 1H), 8.37 (d, J = 6.3 Hz, 1H), 7.70-7.45 (m, 2H), 6.82 (d, J = 6.3 Hz, 1H), 4.26 (vbrs, 2H), 3.92 (d, J = 3.6 Hz, 1H), 3.00-2.98 (m, 1H), 2.83 (dt, J = 14.5, 7.3 Hz, 1H), 2.73-2.66 (m, 2H), 1.24 (s, 3H), 1.23 (s, 3H), 0.74 (t, J = 7.1 Hz, 3H). (NB T = 350 K) |
| IV-297 | 399.95 | 2.32 | 1H NMR (400 MHz, Methanol-d4) δ 9.97 (d, J = 1.5 Hz, 1H), 9.03 (d, J = 1.4 Hz, 1H), 8.39 (s, 1H), 8.20 (d, J = 6.2 Hz, 1H), 7.93-7.85 (m, 2H), 7.54-7.39 (m, 3H), 6.57 (d, J = 6.2 Hz, 1H), 3.80-3.65 (m, 8H), 2.20 (s, 3H). |
| IV-298 | 456.9 | 1.96 | 1H NMR (400 MHz, Methanol-d4) δ 10.16 (d, J = 1.5 Hz, 1H), 9.16 (d, J = 1.4 Hz, 1H), 8.55 (s, 1H), 8.38 (d, J = 6.2 Hz, 1H), 7.96-7.88 (m, 2H), 7.77-7.70 (m, 2H), 6.64 (d, J = 6.3 Hz, 1H), 3.92 (t, J = 5.2 Hz, 2H), 3.84-3.70 (m, 7H), 2.20 (s, 3H), 2.18 (s, 3H). |
| IV-299 | 444.15 | 2.52 | 1H NMR (400 MHz, Methanol-d4) δ 9.91-9.85 (m, 1H), 8.99 (d, J = 1.3 Hz, 1H), 8.37 (s, 1H), 8.18 (d, J = 6.1 Hz, 1H), 7.71-7.61 (m, 1H), 7.42-7.28 (m, 3H), 6.98-6.90 (m, 1H), 6.55 (d, J = 6.3 Hz, 1H), 4.10 (q, J = 7.0 Hz, 2H), 3.78-3.67 (m, 8H), 2.20 (s, 3H), 1.45 (t, J = 6.9 Hz, 3H). |
| IV-300 | 404.65 | 1.77 | 1H NMR (400 MHz, Methanol-d4) δ 9.70 (s, 1H), 8.97 (d, J = 1.4 Hz, 1H), 8.35 (s, 1H), 8.15 (d, J = 6.2 Hz, 1H), 7.88 (s, 1H), 6.54 (d, J = 6.3 Hz, 1H), 3.81-3.65 (m, 8H), 2.54 (s, 3H), 2.20 (s, 3H). exchangeable proton not observed |
| IV-301 | 424.95 | 2.11 | 1H NMR (400 MHz, Methanol-d4) δ 10.35 (d, J = 1.6 Hz, 1H), 9.26 (d, J = 1.4 Hz, 1H), 8.64 (d, J = 1.3 Hz, 1H), 8.38 (dd, J = 6.2, 1.2 Hz, 1H), 7.96 (dd, J = 16.5, 7.9 Hz, 2H), 7.85 (t, J = 7.7 Hz, 1H), 7.66 (t, J = 7.7 Hz, 1H), 6.74-6.66 (m, 1H), 3.95-3.69 (m, 8H), 2.19 (d, J = 1.3 Hz, 3H). |
| IV-302 | 432.85 | 1.91 | 1H NMR (400 MHz, DMSO-d6) δ 10.19 (d, J = 1.6 Hz, 1H), 9.31 (d, J = 1.5 Hz, 1H), 8.59 (s, 1H), 8.44 (d, J = 6.2 Hz, 1H), 8.04-7.96 (m, 2H), 7.66-7.58 (m, 1H), 7.50 (d, J = 8.1 Hz, 2H), 7.43-7.36 (m, 1H), 6.84 (d, J = 6.3 Hz, 1H), 5.30 (t, J = 5.7 Hz, 1H), 5.20 (t, J = 5.7 Hz, 1H), 4.57 (dd, J = 22.5, 5.7 Hz, 3H), 3.64 (t, J = 5.2 Hz, 4H), 2.10 (s, 3H). |
| IV-303 | 443 | 1.84 | 1H NMR (400 MHz, DMSO-d6) δ 10.23 (d, J = 1.5 Hz, 1H), 9.34 (d, J = 1.4 Hz, 1H), 8.60 (s, 1H), 8.53 (t, J = 1.8 Hz, 1H), 8.42 (d, J = 6.2 Hz, 1H), 8.25-8.14 (m, 2H), 7.97 (dt, J = 7.9, 1.3 Hz, 1H), 7.65 (t, J = 7.7 Hz, 1H), 7.48 (s, 1H), 6.84 (d, J = 6.3 Hz, 1H), 3.90 (s, 2H), 3.75 (s, 2H), 3.70-3.59 (m, 4H), 2.11 (s, 3H). |

TABLE 7-continued

Analytical data for compounds of Formula IV

| IV- | LCMS_Plus | LCMS_RT | NMR |
|---|---|---|---|
| IV-304 | 443 | 2.88 | 1H NMR (500 MHz, DMSO-d6) δ 12.45 (brs, 1H), 10.22 (s, 1H), 9.31 (d, J = 1.2 Hz, 1H), 8.68 (s, 1H), 8.38 (d, J = 6.4 Hz, 1H), 7.53 (s, 2H), 6.91 (d, J = 6.3 Hz, 1H), 4.86 (vbrs, 1H), 4.38 (vbrs, 1H), 2.75 (t, J = 12.5 Hz, 1H), 1.88 (dd, J = 12.7, 4.0 Hz, 1H), 1.79 (td, J = 11.2, 6.0 Hz, 1H), 1.70 (q, J = 12.3 Hz, 1H), 1.09 (d, J = 6.4 Hz, 3H), 1.01 (d, J = 6.8 Hz, 3H). NB Acquired at 350 K |
| IV-305 | 401.3 | 2.03 | 1H NMR (500 MHz, DMSO-d6) δ 10.28 (d, J = 9.4 Hz, 1H), 9.71 (s, 1H), 9.34 (d, J = 1.3 Hz, 1H), 9.03 (s, 1H), 8.81 (d, J = 29.4 Hz, 1H), 8.53 (dd, J = 6.3, 1.6 Hz, 1H), 7.92-7.70 (m, 2H), 7.06 (d, J = 6.3 Hz, 1H), 5.39 (s, 1H), 5.14 (s, 1H), 4.90-4.74 (m, 1H), 4.63 (s, 1H), 4.31 (s, 1H), 3.54 (d, J = 11.0 Hz, 1H), 3.07 (s, 1H), 1.44 (t, J = 5.9 Hz, 3H), 1.21 (d, J = 7.0 Hz, 3H). |
| IV-306 | 443.1 | 1.83 | 1H NMR (500 MHz, Methanol-d4) δ 9.84 (s, 1H), 9.02 (d, J = 1.3 Hz, 1H), 8.64 (d, J = 3.9 Hz, 1H), 8.34 (d, J = 6.7 Hz, 1H), 7.70 (s, 2H), 6.91 (d, J = 6.8 Hz, 1H), 4.93 (d, J = 3.0 Hz, 1H), 4.25 (dd, J = 11.6, 4.0 Hz, 1H), 3.90 (td, J = 12.0, 3.2 Hz, 1H), 3.63-3.48 (m, 1H), 1.20 (d, J = 6.8 Hz, 3H). |
| IV-307 | 418.15 | 1.92 | 1H NMR (400 MHz, Methanol-d4) δ 9.98 (d, J = 1.5 Hz, 1H), 9.11 (d, J = 1.5 Hz, 1H), 8.54 (s, 1H), 8.38 (d, J = 6.2 Hz, 1H), 7.95 (s, 1H), 7.66 (s, 1H), 6.66 (d, J = 6.3 Hz, 1H), 3.92 (s, 3H), 3.90 (dd, J = 6.9, 3.6 Hz, 2H), 3.86-3.68 (m, 6H), 2.54 (s, 3H), 2.19 (s, 3H). |
| IV-308 | 430.05 | 2.01 | 1H NMR (400 MHz, Methanol-d4) δ 10.15 (d, J = 1.4 Hz, 1H), 9.16 (d, J = 1.4 Hz, 1H), 8.54 (s, 1H), 8.34 (d, J = 6.2 Hz, 1H), 7.97 (s, 1H), 7.89 (dt, J = 7.7, 1.5 Hz, 1H), 7.50 (t, J = 7.6 Hz, 1H), 7.43 (dt, J = 7.7, 1.4 Hz, 1H), 6.63 (d, J = 6.3 Hz, 1H), 3.91 (t, J = 5.2 Hz, 2H), 3.83-3.71 (m, 6H), 3.33 (p, J = 1.6 Hz, 2H), 2.20 (s, 3H). |
| IV-309 | 416 | 2.03 | 1H NMR (400 MHz, Methanol-d4) δ 10.18 (d, J = 1.5 Hz, 1H), 9.16 (d, J = 1.4 Hz, 1H), 8.56 (s, 1H), 8.35 (d, J = 6.2 Hz, 1H), 7.46 (ddd, J = 7.7, 1.7, 1.0 Hz, 1H), 7.39 (t, J = 2.0 Hz, 1H), 7.36 (d, J = 7.9 Hz, 1H), 7.22-7.18 (m, 1H), 6.91 (dtd, J = 7.9, 2.9, 1.1 Hz, 1H), 6.64 (d, J = 6.3 Hz, 1H), 3.80 (s, 3H), 3.81-3.75 (m, 1H), 3.42-3.16 (m, 4H), 1.34 (s, 3H). |
| IV-310 | 443 | 2.84 | |
| IV-311 | 443 | 2.84 | |
| IV-312 | 441 | 1.84 | 1H NMR (500 MHz, Methanol-d4) δ 9.94 (d, J = 1.4 Hz, 1H), 8.99 (d, J = 1.4 Hz, 1H), 8.61 (s, 1H), 8.38 (d, J = 6.6 Hz, 1H), 7.61 (d, J = 2.3 Hz, 2H), 6.85 (d, J = 6.6 Hz, 1H), 5.04 (d, J = 6.9 Hz, 1H), 4.96 (d, J = 1.8 Hz, 1H), 4.18-4.03 (m, 1H), 3.87-3.71 (m, 2H), 3.58 (ddd, J = 13.3, 12.1, 4.7 Hz, 1H), 1.55 (d, J = 6.8 Hz, 3H). |
| IV-313 | 401 | 2 | 1H NMR (500 MHz, Methanol-d4) δ 10.37 (s, 1H), 9.17 (s, 1H), 8.72 (s, 1H), 8.51 (d, J = 6.2 Hz, 1H), 7.88 (s, 2H), 6.96 (d, J = 6.4 Hz, 1H), 3.65 (d, J = 6.3 Hz, 1H), 3.57-3.47 (m, 2H), 2.66 (d, J = 4.0 Hz, 1H), 2.20 (d, J = 11.0 Hz, 1H), 1.57 (d, J = 6.4 Hz, 3H), 1.26 (d, J = 6.7 Hz, 3H). |
| IV-314 | 401 | 2 | 1H NMR (500 MHz, Methanol-d4) δ 10.34 (s, 1H), 9.15 (d, J = 1.4 Hz, 1H), 8.63 (s, 1H), 8.34 (dd, J = 6.3, 1.2 Hz, 1H), 7.72 (s, 2H), 6.80 (d, J = 6.3 Hz, 1H), 5.15 (s, 1H), 4.27 (d, J = 3.6 Hz, 1H), 3.84 (s, 1H), 3.03 (dd, J = 5.3, 2.1 Hz, 1H), 2.85 (s, 1H), 1.36-1.27 (m, 3H), 1.11 (d, J = 6.7 Hz, 3H). |
| IV-315 | 431 | 2.36 | 1H NMR (500 MHz, Methanol-d4) δ 10.30 (s, 1H), 9.20 (d, J = 1.3 Hz, 1H), 8.68 (s, |

TABLE 7-continued

Analytical data for compounds of Formula IV

| IV- | LCMS_Plus | LCMS_RT | NMR |
|---|---|---|---|
| | | | 1H), 8.39 (d, J = 6.3 Hz, 1H), 7.64 (s, 2H), 6.81 (d, J = 6.4 Hz, 1H), 4.89 (d, J = 3.0 Hz, 1H), 4.21 (dd, J = 11.6, 3.9 Hz, 1H), 3.86 (td, J = 12.0, 3.3 Hz, 1H), 3.48-3.39 (m, 1H), 1.14 (d, J = 6.8 Hz, 3H), 2H not observed. |
| IV-316 | 397.2 | 2.2 | 1H NMR (500 MHz, Methanol-d4) δ 9.93-9.81 (m, 1H), 8.97-8.87 (m, 1H), 8.60-8.50 (m, 1H), 8.36 (ddd, J = 7.5, 4.6, 1.6 Hz, 1H), 7.65-7.52 (m, 2H), 6.80-6.69 (m, 1H), 5.05-4.96 (m, 1H), 4.93 (s, 1H), 4.13-4.00 (m, 1H), 3.86-3.67 (m, 2H), 3.55-3.42 (m, 1H), 1.51 (d, J = 6.8 Hz, 3H). |
| IV-317 | 416.2 | 2.83 | 1H NMR (500 MHz, DMSO-d6) δ 10.20 (s, 1H), 9.43-9.25 (m, 1H), 8.68 (s, 1H), 8.49 (d, J = 1.8 Hz, 1H), 8.39 (d, J = 6.3 Hz, 1H), 6.94 (d, J = 6.3 Hz, 1H), 6.40 (dd, J = 1.9, 0.8 Hz, 1H), 4.54 (s, 1H), 4.39-4.05 (m, 1H), 3.50 (dd, J = 13.2, 9.8 Hz, 1H), 3.25-3.08 (m, 1H), 2.22-2.10 (m, 1H), 1.95-1.72 (m, 2H), 1.72-1.58 (m, 1H), 1H not observed. |
| IV-318 | 431.2 | 2.38 | 1H NMR (500 MHz, Methanol-d4) δ 10.30 (s, 1H), 9.23-9.15 (m, 1H), 8.67 (s, 1H), 8.38 (d, J = 6.3 Hz, 1H), 7.98-7.88 (m, 1H), 7.64 (s, 2H), 6.80 (d, J = 6.4 Hz, 1H), 4.88 (d, J = 3.0 Hz, 1H), 4.21 (dd, J = 11.6, 3.9 Hz, 1H), 3.86 (td, J = 12.0, 3.2 Hz, 1H), 3.44 (s, 1H), 1.14 (d, J = 6.7 Hz, 3H), 2H not observed. |
| IV-319 | 429.1 | 2.52 | 1H NMR (500 MHz, Methanol-d4) δ 10.27 (s, 1H), 9.18 (dd, J = 1.4, 0.7 Hz, 1H), 8.61 (s, 1H), 8.38 (d, J = 6.3 Hz, 1H), 7.75 (d, J = 1.5 Hz, 1H), 7.17 (t, J = 1.4 Hz, 1H), 6.92 (d, J = 1.3 Hz, 1H), 6.79 (d, J = 6.3 Hz, 1H), 4.75 (d, J = 14.2 Hz, 1H), 4.60 (q, J = 3.8 Hz, 1H), 4.54 (d, J = 8.9 Hz, 1H), 3.72 (dd, J = 14.1, 3.5 Hz, 1H), 3.38 (ddd, J = 13.4, 11.3, 3.6 Hz, 1H), 2.42-2.28 (m, 1H), 1.92-1.80 (m, 1H), 1.80-1.62 (m, 1H), 0.84 (d, J = 6.9 Hz, 3H). |
| IV-320 | 429.1 | 2.59 | 1H NMR (500 MHz, Methanol-d4) δ 10.31 (d, J = 1.5 Hz, 1H), 9.19 (dd, J = 1.3, 0.7 Hz, 1H), 8.64 (s, 1H), 8.38 (d, J = 6.3 Hz, 1H), 7.82 (t, J = 1.2 Hz, 1H), 7.31 (t, J = 1.4 Hz, 1H), 7.07 (t, J = 1.1 Hz, 1H), 6.85 (d, J = 6.3 Hz, 1H), 4.73-4.45 (m, 1H), 3.94 (td, J = 11.2, 4.5 Hz, 1H), 3.47-3.34 (m, 1H), 3.27-3.13 (m, 1H), 2.33-2.13 (m, 1H), 2.11-1.97 (m, 1H), 1.50 (qd, J = 12.9, 4.4 Hz, 1H), 1.35-1.18 (m, 2H), 0.83 (d, J = 6.5 Hz, 3H). |
| IV-321 | 417 | 2.73 | 1H NMR (500 MHz, DMSO-d6) δ 10.21 (s, 1H), 9.57 (s, 1H), 9.36 (d, J = 1.3 Hz, 1H), 8.67 (s, 1H), 8.40 (d, J = 6.3 Hz, 1H), 6.92 (d, J = 6.3 Hz, 1H), 4.59 (s, 1H), 4.24 (s, 1H), 3.58 (dd, J = 13.3, 9.7 Hz, 1H), 3.40 (t, J = 12.0 Hz, 1H), 3.19 (tt, J = 9.9, 4.0 Hz, 1H), 2.16 (dt, J = 13.0, 4.3 Hz, 1H), 1.94 (dtd, J = 13.8, 10.5, 3.9 Hz, 1H), 1.86 (dt, J = 13.0, 4.1 Hz, 1H), 1.77-1.60 (m, 1H). |
| IV-322 | 417.2 | 1.85 | 1H NMR (500 MHz, DMSO-d6) δ 10.24 (s, 1H), 9.35 (d, J = 1.3 Hz, 1H), 8.68 (s, 1H), 8.35 (d, J = 6.3 Hz, 1H), 6.84 (d, J = 6.3 Hz, 1H), 4.56-4.11 (m, 2H), 3.22 (dd, J = 13.3, 10.4 Hz, 1H), 3.14 (ddd, J = 13.6, 11.3, 3.0 Hz, 1H), 2.30-2.19 (m, 1H), 2.02-1.90 (m, 1H), 1.83-1.73 (m, 1H), 1.73-1.63 (m, 1H), 1.55-1.41 (m, 1H). |
| IV-323 | 458.1 | 2.43 | 1H NMR (500 MHz, Methanol-d4) δ 10.24 (s, 1H), 9.22 (d, J = 1.4 Hz, 1H), 8.72 (s, 1H), 8.51 (d, J = 6.3 Hz, 1H), 7.89 (s, 2H), 6.91 (d, J = 6.3 Hz, 1H), 4.94 (d, J = 4.6 Hz, 1H), 3.96-3.79 (m, 1H), 1.55 (d, J = 6.8 Hz, 3H), 1.46 (d, J = 7.2 Hz, 3H), 1.36 (d, J = 7.1 Hz, 3H). |

TABLE 7-continued

Analytical data for compounds of Formula IV

| IV- | LCMS_Plus | LCMS_RT | NMR |
|---|---|---|---|
| IV-324 | 462.1 | 2.53 | 1H NMR (500 MHz, Methanol-d4) δ 10.21 (s, 1H), 9.21 (s, 1H), 8.62 (s, 1H), 8.35 (d, 1H), 7.68 (s, 2H), 4.85 (masked, 1H), 4.45 (m, 1H), 4.35 (d, 1H), 3.15-3.00 (m, 2H, 1.30 (d, 3H), 1.24 (d, 3H). |
| IV-325 | 415.3 | 2.39 | 1H NMR (500 MHz, DMSO-d6) δ 14.35 (d, J = 93.1 Hz, 2H), 10.22 (s, 1H), 9.38 (d, J = 1.3 Hz, 1H), 9.09 (d, J = 1.4 Hz, 1H), 8.77 (s, 1H), 8.44 (d, J = 6.3 Hz, 1H), 7.59 (t, J = 1.1 Hz, 1H), 6.96 (d, J = 6.4 Hz, 1H), 4.95-4.16 (m, 2H), 3.27 (dd, J = 13.1, 10.6 Hz, 1H), 3.19 (td, J = 13.3, 12.3, 2.8 Hz, 1H), 3.06-2.95 (m, 1H), 2.23-2.11 (m, 1H), 1.95-1.78 (m, 2H), 1.70-1.56 (m, 1H). |
| IV-326 | 416.2 | 2.2 | 1H NMR (500 MHz, DMSO-d6) δ 10.19 (d, J = 2.9 Hz, 1H), 9.37 (d, J = 1.2 Hz, 1H), 8.72 (s, 1H), 8.40 (d, J = 6.4 Hz, 1H), 8.33 (s, 1H), 6.95 (dd, J = 6.6, 2.1 Hz, 1H), 4.84-4.20 (m, 2H), 3.45 (t, J = 11.8 Hz, 1H), 3.30 (t, J = 12.2 Hz, 1H), 3.13-2.99 (m, 1H), 2.22-2.09 (m, 1H), 2.01-1.83 (m, 2H), 1.72-1.57 (m, 1H). |
| IV-327 | 444.2 | 2.27 | 1H NMR (500 MHz, DMSO-d6) δ 12.69 (s, 1H), 10.22 (s, 1H), 9.35 (s, 1H), 8.71 (s, 1H), 8.37 (d, J = 6.2 Hz, 1H), 7.74 (s, 1H), 7.57 (s, 1H), 6.94 (s, 1H), 4.07 (s, 1H), 2.83 (s, 2H), 2.23 (s, 1H), 1.19 (s, 3H), 1.16-1.03 (m, 3H). |
| IV-328 | 442.9 | 2.21 | 1H NMR (500 MHz, Methanol-d4) δ 10.07-10.01 (m, 1H), 8.98 (d, J = 1.3 Hz, 1H), 8.60 (s, 1H), 8.39 (d, J = 6.3 Hz, 1H), 7.69 (s, 2H), 6.80 (d, J = 6.3 Hz, 1H), 4.92 (d, J = 3.0 Hz, 1H), 4.24 (dd, J = 11.7, 3.8 Hz, 1H), 3.89 (td, J = 12.0, 3.3 Hz, 2H), 3.53-3.40 (m, 2H), 1.16 (d, J = 6.7 Hz, 3H). |
| IV-329 | 442.9 | 2.21 | 1H NMR (500 MHz, Methanol-d4) δ 10.07-10.01 (m, 1H), 8.98 (d, J = 1.3 Hz, 1H), 8.60 (s, 1H), 8.39 (d, J = 6.3 Hz, 1H), 7.69 (s, 2H), 6.80 (d, J = 6.3 Hz, 1H), 4.92 (d, J = 3.0 Hz, 1H), 4.24 (dd, J = 11.7, 3.8 Hz, 1H), 3.89 (td, J = 12.0, 3.3 Hz, 2H), 3.53-3.40 (m, 2H), 1.16 (d, J = 6.7 Hz, 3H). |
| IV-330 | 472.3 | 2.76 | 1H NMR (500 MHz, DMSO-d6) δ 10.24-10.04 (m, 1H), 9.39 (s, 1H), 9.02-8.91 (m, 1H), 8.74 (s, 1H), 8.55 (d, J = 6.3 Hz, 1H), 7.86 (s, 2H), 7.12 (dd, J = 6.3, 3.1 Hz, 1H), 5.42-5.04 (m, 1H), 4.76 (s, 1H), 3.20 (d, J = 24.8 Hz, 1H), 2.16 (d, 1H), 1.25 (d, J = 7.0 Hz, 3H), 1.17 (d, J = 6.8 Hz, 3H), 1.15-1.11 (m, 3H). 2 C—H missing |
| IV-331 | 417.3 | 1.83 | 1H NMR (500 MHz, DMSO-d6) δ 10.20 (s, 1H), 9.37 (d, J = 1.3 Hz, 1H), 8.75 (s, 1H), 8.42 (d, J = 6.4 Hz, 1H), 4.85-4.52 (m, 1H), 4.52-4.19 (m, 1H), 3.51 (dd, J = 13.2, 10.1 Hz, 1H), 3.44-3.26 (m, 2H), 2.28-2.15 (m, 1H), 2.05-1.93 (m, 1H), 1.93-1.84 (m, 1H), 1.75-1.59 (m, 1H). |
| IV-332 | 392.2 | 2.24 | 1H NMR (500 MHz, DMSO-d6) δ 10.21 (s, 1H), 9.37 (d, J = 1.3 Hz, 1H), 9.14-9.00 (m, 2H), 8.79 (s, 1H), 8.46 (d, J = 6.3 Hz, 1H), 7.00 (d, J = 6.3 Hz, 1H), 4.76-4.59 (m, 1H), 4.58-4.47 (m, 1H), 4.46-4.27 (m, 1H), 3.72-3.58 (m, 1H), 3.30-3.22 (m, 1H), 2.33-2.23 (m, 1H), 2.14 (dtd, J = 12.6, 11.1, 4.1 Hz, 1H), 1.99-1.85 (m, 1H), 1.76-1.61 (m, 1H). |
| IV-333 | 430.3 | 2.16 | 1H NMR (500 MHz, Methanol-d4) δ 10.27 (s, 1H), 9.19 (s, 1H), 8.63 (s, 1H), 8.34 (d, 1H), 7.78 (s, 2H), 6.78 (d, 1H), 4.70 (broad s, 1H), 3.94 (m, 1H), 3.23-3.18 (m, 3H), 3.10 (m, 1H), 1.44 (d, 3H). |
| IV-334 | 449.3 | 2.59 | 1H NMR (500 MHz, DMSO-d6) δ 12.78 (s, 1H), 10.11 (m, 1H), 9.36 (s, 1H), 8.72 (s, 1H), 8.52 (d, 1H), 7.65 (m, 2H), 5.10 (m, 1H), 4.27 (m, 1H), 4.16 (m, 1H), 4.05 (m, |

TABLE 7-continued

Analytical data for compounds of Formula IV

| IV- | LCMS_Plus | LCMS_RT | NMR |
|---|---|---|---|
| | | | 1H), 3.93 (m, 1H), 3.70 (m, 1H), 1.20 (d, 3H). |
| IV-335 | 449 | 2.65 | 1H NMR (500 MHz, DMSO-d6) δ 12.85 (s, 1H), 10.11 (m, 1H), 9.37 (s, 1H), 8.72 (s, 1H), 8.54 (d, 1H), 7.80-7.60 (m, 2H), 4.72 (m, 1H), 4.48 (m, 2H), 3.90 (m, 1H), 3.60 (masked, 1H), 2.96 (m, 1H), 1.25 (d, 3H). |
| IV-336 | 458.3 | 2.41 | 1H NMR (500 MHz, Methanol-d4) δ 10.25 (d, J = 71.8 Hz, 1H), 9.21 (d, J = 10.7 Hz, 1H), 8.78-8.60 (m, 1H), 8.46-8.26 (m, 1H), 7.73 (s, 2H), 6.77 (d, J = 6.3 Hz, 1H), 4.98 (d, J = 57.6 Hz, 1H), 4.30 (t, J = 6.7 Hz, 1H), 4.12 (d, J = 71.1 Hz, 1H), 3.26 (qd, J = 6.7, 4.2 Hz, 1H), 1.30 (t, J = 13.3 Hz, 6H), 1.21-1.04 (m, 3H). |
| IV-337 | 458.3 | 2.42 | 1H NMR (500 MHz, Methanol-d4) δ 10.13 (s, 1H), 9.11 (s, 1H), 8.60 (s, 1H), 8.38 (dd, J = 6.2, 1.3 Hz, 1H), 7.78 (d, J = 3.2 Hz, 2H), 6.79 (d, J = 6.3 Hz, 1H), 5.58-5.08 (m, 1H), 4.45 (d, J = 56.4 Hz, 1H), 3.71 (h, J = 5.1, 3.7 Hz, 1H), 1.42 (dd, J = 6.7, 2.4 Hz, 3H), 1.34 (d, J = 7.3 Hz, 3H), 1.29-1.14 (m, 3H). |
| IV-338 | 422.3 | 1.97 | |
| IV-339 | 422.3 | 1.96 | |
| IV-340 | 427.2 | 2.23 | 1H NMR (500 MHz, DMSO-d6) δ 14.34 (s, 1H), 9.88 (d, J = 1.3 Hz, 1H), 9.11 (d, J = 1.3 Hz, 1H), 9.07 (d, J = 1.4 Hz, 1H), 8.66 (s, 1H), 8.41 (d, J = 6.3 Hz, 1H), 7.59 (t, J = 1.1 Hz, 1H), 6.92 (d, J = 6.4 Hz, 1H), 4.93-4.53 (m, 1H), 4.53-4.12 (m, 1H), 3.26 (dd, J = 13.1, 10.5 Hz, 1H), 3.17 (ddd, J = 14.0, 11.4, 2.9 Hz, 1H), 3.00 (s, 1H), 2.21-2.11 (m, 1H), 1.92-1.75 (m, 2H), 1.69-1.54 (m, 1H). |
| IV-341 | 372.3 | 2.09 | 1H NMR (500 MHz, DMSO-d6) δ 14.34 (s, 1H), 10.26 (d, J = 1.5 Hz, 1H), 9.32 (d, J = 1.4 Hz, 1H), 9.07 (d, J = 1.3 Hz, 1H), 8.76 (s, 1H), 8.42 (d, J = 6.3 Hz, 1H), 7.59 (t, J = 1.1 Hz, 1H), 6.95 (d, J = 6.4 Hz, 1H), 4.71 (s, 1H), 4.54-4.19 (m, 1H), 3.26 (dd, J = 13.1, 10.5 Hz, 1H), 3.21-3.11 (m, 1H), 3.01 (d, J = 3.9 Hz, 1H), 2.16 (dd, J = 12.7, 3.6 Hz, 1H), 1.93-1.75 (m, 2H), 1.69-1.54 (m, 1H). |
| IV-342 | 442.2 | 2 | 1H NMR (500 MHz, DMSO-d6) δ 9.89 (d, J = 1.3 Hz, 1H), 9.58 (s, 1H), 9.12 (d, J = 1.3 Hz, 1H), 8.73 (s, 1H), 8.49 (d, J = 6.3 Hz, 1H), 8.24 (s, 1H), 7.84 (s, 1H), 6.89 (d, J = 6.3 Hz, 1H), 6.51 (s, 1H), 4.63 (s, 1H), 3.80 (s, 1H), 3.61-3.44 (m, 1H), 1.20 (d, J = 6.7 Hz, 3H). |
| IV-343 | 440.2 | 1.94 | 1H NMR (500 MHz, DMSO-d6) δ 9.89 (d, J = 1.4 Hz, 1H), 9.68 (s, 1H), 9.37 (s, 1H), 9.13 (d, J = 1.3 Hz, 1H), 8.68 (s, 1H), 8.53 (d, J = 6.3 Hz, 1H), 7.82 (s, 2H), 7.01 (d, J = 6.3 Hz, 1H), 5.01 (s, 1H), 4.78 (d, J = 9.4 Hz, 1H), 3.54 (d, J = 11.9 Hz, 1H), 1.21 (d, J = 7.0 Hz, 3H). |
| IV-344 | 442.3 | 2.02 | 1H NMR (500 MHz, Methanol-d4) δ 9.98 (d, J = 1.4 Hz, 1H), 8.94 (d, J = 1.3 Hz, 1H), 8.54 (s, 1H), 8.32 (d, J = 6.3 Hz, 1H), 7.77 (s, 2H), 6.78 (d, J = 6.4 Hz, 1H), 4.00 (dd, J = 11.2, 3.2 Hz, 1H), 3.11-2.95 (m, 2H), 2.74 (dd, J = 12.8, 11.1 Hz, 1H), 1.28 (d, J = 6.3 Hz, 3H). |
| IV-345 | 444.4 | 2.29 | 1H NMR (500 MHz, Methanol-d4) δ 10.44 (s, 1H), 10.28 (s, 1H), 9.24 (s, 1H), 8.71 (s, 1H), 8.49 (d, J = 5.2 Hz, 1H), 7.69 (s, 2H), 7.28 (d, J = 5.2 Hz, 1H), 5.11-4.88 (m, 1H), 4.75-4.43 (m, 1H), 4.29 (s, 1H), 3.15-2.75 (m, 2H), 1.31 (s, 3H), 1.25-1.01 (m, 3H). |
| IV-346 | 427.3 | 2.42 | 1H NMR (500 MHz, Methanol-d4) δ 9.90 (d, J = 1.4 Hz, 1H), 8.91 (d, J = 1.3 Hz, 1H), 8.48 (s, 1H), 8.24 (d, J = 6.3 Hz, 1H), |

TABLE 7-continued

Analytical data for compounds of Formula IV

| IV- | LCMS_Plus | LCMS_RT | NMR |
|---|---|---|---|
| | | | 7.61 (s, 2H), 6.71 (d, J = 6.4 Hz, 1H), 4.59 (s, 1H), 3.26-3.02 (m, 2H), 2.90-2.81 (m, 1H), 2.18 (dd, J = 12.9, 4.0 Hz, 1H), 2.00-1.85 (m, 1H), 1.87-1.63 (m, 2H), 1.37 (d, J = 6.6 Hz, 1H). |
| IV-347 | 382.3 | 1.77 | 1H NMR (500 MHz, Methanol-d4) δ 9.91 (s, 1H), 8.97 (s, 1H), 8.62 (s, 1H), 8.48-8.33 (m, 1H), 7.77 (s, 1H), 7.25 (s, 1H), 6.83 (d, J = 6.5 Hz, 1H), 4.61-4.46 (m, 2H), 4.27-4.14 (m, 1H), 3.70-3.47 (m, 1H), 3.21-3.09 (m, 2H), 2.10-1.85 (m, 1H). |
| IV-348 | 427.9 | 1.78 | 1H NMR (500 MHz, Methanol-d4) δ 10.03 (s, 1H), 8.94 (s, 1H), 8.60 (s, 1H), 8.36 (d, J = 6.3 Hz, 1H), 7.71 (s, 1H), 7.15 (s, 1H), 6.79 (d, J = 6.3 Hz, 1H), 4.42 (s, 1H), 4.00-3.89 (m, 1H), 3.26-3.11 (m, 2H), 3.07-2.94 (m, 1H). |
| IV-349 | 410.1 | 2.02 | 1H NMR (500 MHz, Methanol-d4) δ 9.95 (s, 1H), 8.97 (d, J = 1.3 Hz, 1H), 8.64 (s, 1H), 8.35 (d, J = 6.3 Hz, 1H), 7.72 (d, J = 1.2 Hz, 1H), 7.10 (s, 1H), 6.77 (d, J = 6.5 Hz, 1H), 5.38 (s, 1H), 4.55 (s, 1H), 4.29-4.15 (m, 1H), 3.86 (s, 1H), 3.12-2.97 (m, 1H), 2.86 (s, 1H), 1.32 (d, J = 6.3 Hz, 3H), 1.12-0.94 (m, 3H). |
| IV-350 | 442.1 | 1.94 | 1H NMR (500 MHz, Methanol-d4) δ 9.99 (s, 1H), 8.95 (d, J = 1.3 Hz, 1H), 8.56 (s, 1H), 8.33 (d, J = 6.3 Hz, 1H), 7.70 (s, 2H), 6.76 (d, J = 6.4 Hz, 1H), 4.56 (s, 2H), 4.21 (d, J = 3.8 Hz, 1H), 3.29-3.24 (m, 1H), 3.01 (td, J = 12.6, 3.7 Hz, 1H), 1.14 (d, J = 6.8 Hz, 3H). |
| IV-351 | 442.1 | 1.94 | 1H NMR (500 MHz, Methanol-d4) δ 10.03-9.93 (m, 1H), 8.95 (d, J = 1.3 Hz, 1H), 8.55 (s, 1H), 8.34 (d, J = 6.3 Hz, 1H), 7.72 (s, 2H), 6.77 (d, J = 6.4 Hz, 1H), 4.55 (s, 4H), 4.28 (d, J = 3.8 Hz, 1H), 3.06 (dd, J = 13.2, 3.9 Hz, 1H), 1.16 (d, J = 6.9 Hz, 3H). |
| IV-352 | 444.4 | 2.21 | 1H NMR (500 MHz, Methanol-d4) δ 10.36 (s, 1H), 9.22 (s, 1H), 8.75 (s, 1H), 8.38 (d, J = 6.3 Hz, 1H), 7.77-7.70 (m, 1H), 7.33 (d, J = 4.4 Hz, 1H), 7.11 (s, 1H), 6.83 (d, J = 6.3 Hz, 1H), 4.56 (s, 1H), 4.24 (s, 1H), 3.56 (d, J = 2.6 Hz, 1H), 3.00-2.85 (m, 1H), 1.33 (q, J = 8.6 Hz, 3H), 1.26 (d, J = 6.4 Hz, 3H). |
| IV-353 | 410.3 | 2.1 | 1H NMR (500 MHz, Methanol-d4) δ 9.85 (d, J = 1.4 Hz, 1H), 8.94 (d, J = 1.3 Hz, 1H), 8.53 (s, 1H), 8.29 (d, J = 6.3 Hz, 1H), 7.78 (s, 1H), 6.76 (d, J = 6.4 Hz, 1H), 4.55 (s, 1H), 4.29 (dd, J = 11.3, 3.4 Hz, 1H), 3.05-2.94 (m, 2H), 1.32 (s, 3H), 1.27 (s, 3H). |
| IV-354 | 456.3 | 2.12 | 1H NMR (500 MHz, Methanol-d4) δ 9.94 (s, 1H), 8.92 (s, 1H), 8.51 (s, 1H), 8.27 (d, J = 6.3 Hz, 1H), 7.78 (s, 2H), 6.75 (d, J = 6.4 Hz, 1H), 4.65-4.46 (m, 3H), 4.25 (dd, J = 11.3, 3.4 Hz, 1H), 3.05-2.88 (m, 2H), 1.31 (s, 3H), 1.27 (s, 3H). |
| IV-355 | 441.3 | 2.29 | 1H NMR (500 MHz, Methanol-d4) δ 9.94 (d, J = 1.3 Hz, 1H), 8.97 (d, J = 1.2 Hz, 1H), 8.58 (s, 1H), 8.34 (dd, J = 6.5, 0.8 Hz, 1H), 7.33 (d, J = 0.9 Hz, 1H), 6.88-6.81 (m, 1H), 4.38 (s, 1H), 3.41-3.33 (m, 1H), 3.12-2.98 (m, 1H), 2.63 (s, 3H), 2.26 (dd, J = 13.0, 4.1 Hz, 1H), 1.98 (dt, J = 13.5, 3.7 Hz, 1H), 1.94-1.84 (m, 1H), 1.78 (ddt, J = 13.1, 7.9, 3.9 Hz, 1H), 2H not observed. |
| IV-356 | 437.3 | 2.25 | 1H NMR (500 MHz, Methanol-d4) δ 10.02 (d, J = 1.3 Hz, 1H), 8.96 (d, J = 1.3 Hz, 1H), 8.61 (s, 1H), 8.38 (d, J = 6.3 Hz, 1H), 7.62 (s, 1H), 6.86 (d, J = 6.4 Hz, 1H), 6.56 (t, J = 2.1 Hz, 1H), 4.56 (s, 2H), 3.96 (s, 2H), 2.67 (s, 3H), 2.63-2.45 (m, 2H). |
| IV-357 | 430.1 | 2.1 | 1H NMR (500 MHz, Methanol-d4) δ 10.30-10.11 (m, 1H), 9.15 (d, J = 1.3 Hz, 1H), 8.59 (s, 1H), 8.29 (d, J = 6.3 Hz, 1H), 7.67 |

TABLE 7-continued

Analytical data for compounds of Formula IV

| IV- | LCMS_Plus | LCMS_RT | NMR |
|---|---|---|---|
| | | | (s, 2H), 6.74 (d, J = 6.4 Hz, 1H), 4.19 (d, J = 3.7 Hz, 1H), 3.29-3.21 (m, 1H), 3.00 (td, J = 12.7, 3.7 Hz, 1H), 1.13 (d, J = 6.8 Hz, 3H), 3H not observed. |
| IV-358 | 430.1 | 2.1 | 1H NMR (500 MHz, Methanol-d4) δ 10.30-10.11 (m, 1H), 9.15 (d, J = 1.3 Hz, 1H), 8.59 (s, 1H), 8.29 (d, J = 6.3 Hz, 1H), 7.67 (s, 2H), 6.74 (d, J = 6.4 Hz, 1H), 4.19 (d, J = 3.7 Hz, 1H), 3.29-3.21 (m, 1H), 3.00 (td, J = 12.7, 3.7 Hz, 1H), 1.13 (d, J = 6.8 Hz, 3H), 3H not observed. |
| IV-359 | 445.3 | 2.16 | 1H NMR (500 MHz, Methanol-d4) δ 9.40 (d, 1H), 8.46 (s, 1H), 7.93 (s, 1H), 7.59-7.49 (m, 1H), 6.85 (s, 1H), 6.80 (s, 1H), 6.16-6.12 (m, 1H), 3.07 (m, 2H), 2.83 (m, 2H), 2.39 (m, 1H), 2.27 (m, 1H), 2.11 (m, 1H), 1.37-1.19 (m, 3H). |
| IV-360 | 428 | 2.42 | 1H NMR (500 MHz, Methanol-d4) δ 9.91 (d, J = 1.3 Hz, 1H), 8.91 (d, J = 1.3 Hz, 1H), 8.49 (s, 1H), 8.24 (d, J = 6.3 Hz, 1H), 7.61 (s, 2H), 6.71 (d, J = 6.4 Hz, 1H), 4.59 (s, 1H), 4.38 (s, 1H), 3.22-3.06 (m, 2H), 2.86 (tt, J = 10.9, 3.9 Hz, 1H), 2.23-2.15 (m, 1H), 1.92 (dp, J = 13.4, 3.3 Hz, 1H), 1.85-1.64 (m, 2H). |
| IV-361 | 427 | 2.42 | 1H NMR (500 MHz, Methanol-d4) δ 9.92 (d, J = 1.5 Hz, 1H), 8.91 (d, J = 1.3 Hz, 1H), 8.49 (s, 1H), 8.25 (d, J = 6.3 Hz, 1H), 7.61 (s, 2H), 6.72 (d, J = 6.4 Hz, 1H), 4.59 (s, 1H), 4.38 (s, 1H), 3.22-3.06 (m, 2H), 2.86 (tt, J = 10.9, 4.0 Hz, 1H), 2.23-2.15 (m, 1H), 1.97-1.88 (m, 1H), 1.84-1.64 (m, 2H). |
| IV-362 | 425 | 2.23 | 1H NMR (500 MHz, Methanol-d4) δ 9.96 (d, J = 1.3 Hz, 1H), 8.92 (d, J = 1.3 Hz, 1H), 8.54 (s, 1H), 8.27 (d, J = 6.3 Hz, 1H), 7.65 (d, J = 1.1 Hz, 1H), 6.96 (s, 1H), 6.75 (d, J = 6.4 Hz, 1H), 4.74-4.61 (m, 1H), 4.56-4.36 (m, 1H), 3.24-3.13 (m, 2H), 2.98-2.83 (m, 1H), 2.25-2.13 (m, 1H), 1.99-1.80 (m, 2H), 1.80-1.67 (m, 1H). |
| IV-363 | 425 | 2.23 | 1H NMR (500 MHz, Methanol-d4) δ 9.96 (d, J = 1.3 Hz, 1H), 8.92 (d, J = 1.3 Hz, 1H), 8.54 (s, 1H), 8.27 (d, J = 6.3 Hz, 1H), 7.65 (d, J = 1.1 Hz, 1H), 6.96 (s, 1H), 6.75 (d, J = 6.4 Hz, 1H), 4.74-4.61 (m, 1H), 4.56-4.36 (m, 1H), 3.24-3.13 (m, 2H), 2.98-2.83 (m, 1H), 2.25-2.13 (m, 1H), 1.99-1.80 (m, 2H), 1.80-1.67 (m, 1H). |
| IV-364 | 442 | 2.01 | 1H NMR (500 MHz, Methanol-d4) δ 9.85 (s, 1H), 8.89 (s, 1H), 8.47 (s, 1H), 8.25 (d, J = 6.3 Hz, 1H), 7.77 (s, 2H), 6.72 (d, J = 6.3 Hz, 1H), 4.56 (s, 1H), 4.35 (s, 1H), 3.99 (dd, J = 11.1, 3.2 Hz, 1H), 3.10-2.89 (m, 2H), 2.71 (t, J = 11.9 Hz, 1H), 1.27 (d, J = 6.3 Hz, 3H). |
| IV-365 | 440 | 2 | 1H NMR (500 MHz, Methanol-d4) δ 9.85 (s, 1H), 8.89 (s, 1H), 8.47 (s, 1H), 8.25 (d, J = 6.3 Hz, 1H), 7.77 (s, 2H), 6.72 (d, J = 6.3 Hz, 1H), 4.56 (s, 1H), 4.35 (s, 1H), 3.99 (dd, J = 11.1, 3.2 Hz, 1H), 3.10-2.89 (m, 2H), 2.71 (t, J = 11.9 Hz, 1H), 1.27 (d, J = 6.3 Hz, 3H). |
| IV-366 | 450.1 | 2.24 | |
| IV-367 | 450.1 | 2.25 | |
| IV-368 | 450.1 | 2.25 | |
| IV-369 | 444.1 | 2.28 | 1H NMR (500 MHz, Methanol-d4) δ 10.33 (d, J = 74.1 Hz, 1H), 9.24 (s, 1H), 8.71 (s, 1H), 8.51 (d, J = 5.2 Hz, 1H), 7.72 (s, 2H), 7.30 (d, J = 5.2 Hz, 1H), 5.02 (d, J = 46.1 Hz, 1H), 4.59 (s, 1H), 4.40 (s, 1H), 3.23-3.09 (m, 1H), 3.00 (s, 1H), 1.36 (d, J = 6.3 Hz, 3H), 1.28-1.02 (m, 3H). |
| IV-370 | 444.1 | 2.28 | 1H NMR (500 MHz, Methanol-d4) δ 10.33 (d, J = 74.1 Hz, 1H), 9.24 (s, 1H), 8.71 (s, 1H), 8.51 (d, J = 5.2 Hz, 1H), 7.72 (s, 2H), |

TABLE 7-continued

Analytical data for compounds of Formula IV

| IV- | LCMS_Plus | LCMS_RT | NMR |
|---|---|---|---|
| | | | 7.30 (d, J = 5.2 Hz, 1H), 5.02 (d, J = 46.1 Hz, 1H), 4.59 (s, 1H), 4.40 (s, 1H), 3.23-3.09 (m, 1H), 3.00 (s, 1H), 1.36 (d, J = 6.3 Hz, 3H), 1.28-1.02 (m, 3H). |
| IV-371 | 428.2 | 1.67 | 1H NMR (500 MHz, DMSO-d6) δ 12.8 (m, 1H), 9.91 (s, 1H), 9.1 (s, 1H), 8.60 (s, 1H), 8.39 (d, 1H), 7.70 (s, 2H), 6.90 (d, 1H), 4.30 (br s, 2H), 3.81 (m, 1H), 3.10 (m, 2H), 3.02 (m, 1H), 2.85 (m, 1H). |
| IV-372 | 456.2 | 1.99 | |
| IV-373 | 456.3 | 2.06 | 1H NMR (500 MHz, Methanol-d4) δ 10.05 (s, 1H), 8.96 (d, J = 1.3 Hz, 1H), 8.62 (s, 1H), 8.35 (d, J = 6.4 Hz, 1H), 7.73 (d, J = 1.2 Hz, 1H), 7.10 (s, 1H), 6.78 (d, J = 6.4 Hz, 1H), 5.36 (s, 1H), 4.50 (s, 1H), 4.23 (d, J = 3.7 Hz, 1H), 3.87 (s, 1H), 3.11-2.99 (m, 1H), 2.87 (s, 1H), 1.33 (s, 3H), 1.05 (s, 3H). |
| IV-374 | 441 | 2.28 | 1H NMR (500 MHz, Methanol-d4) δ 9.98 (s, 1H), 8.92 (s, 1H), 8.54 (s, 1H), 8.28 (d, J = 6.3 Hz, 1H), 6.84-6.70 (m, 2H), 4.72-4.58 (m, 1H), 4.51-4.39 (m, 1H), 3.22-3.09 (m, 2H), 2.88-2.70 (m, 1H), 2.35 (s, 3H), 2.22-2.11 (m, 1H), 1.99-1.89 (m, 1H), 1.89-1.77 (m, 1H), 1.77-1.63 (m, 1H). |
| IV-375 | 441 | 2.28 | 1H NMR (500 MHz, Methanol-d4) δ 9.98 (s, 1H), 8.92 (s, 1H), 8.54 (s, 1H), 8.28 (d, J = 6.3 Hz, 1H), 6.84-6.70 (m, 2H), 4.72-4.58 (m, 1H), 4.51-4.39 (m, 1H), 3.22-3.09 (m, 2H), 2.88-2.70 (m, 1H), 2.35 (s, 3H), 2.22-2.11 (m, 1H), 1.99-1.89 (m, 1H), 1.89-1.77 (m, 1H), 1.77-1.63 (m, 1H). |
| IV-376 | 456 | 2.04 | 1H NMR (500 MHz, Methanol-d4) δ 10.04 (s, 1H), 8.95 (d, J = 1.3 Hz, 1H), 8.71-8.53 (m, 1H), 8.34 (d, J = 6.3 Hz, 1H), 7.73 (s, 1H), 7.11 (s, 1H), 6.78 (d, J = 6.3 Hz, 1H), 5.37 (s, 1H), 4.24 (dd, J = 4.0, 1.1 Hz, 1H), 3.87 (s, 1H), 3.06 (ddd, J = 10.2, 6.2, 3.6 Hz, 1H), 2.87 (s, 1H), 1.43-1.18 (m, 3H), 1.05 (s, 3H). |
| IV-377 | 454 | 2.03 | 1H NMR (500 MHz, Methanol-d4) δ 9.98 (s, 1H), 8.93 (d, J = 1.3 Hz, 1H), 8.57 (d, J = 16.6 Hz, 1H), 8.31 (d, J = 6.3 Hz, 1H), 7.73 (d, J = 1.2 Hz, 1H), 7.10 (s, 1H), 6.75 (d, J = 6.4 Hz, 1H), 5.34 (s, 1H), 4.55 (s, 1H), 4.23 (d, J = 4.0 Hz, 1H), 3.85 (s, 1H), 3.05 (ddt, J = 9.1, 6.4, 3.2 Hz, 1H), 2.86 (s, 1H), 1.33 (d, J = 6.5 Hz, 3H), 1.04 (s, 3H). |
| IV-378 | 416.3 | 2.41 | 1H NMR (500 MHz, DMSO-d6) δ 10.22 (s, 1H), 9.36 (s, 1H), 8.70 (s, 1H), 8.40 (d, 1H), 7.76 (s, 1H), 6.93 (d, 1H), 4.80-4.40 (m, 2H), 3.30 (masked, 2H), 3.00 (m, 1H), 2.18 (m, 1H), 1.86 (m, 2H), 1.66 (m, 1H). |
| IV-379 | 429.4 | 2.61 | |
| IV-380 | 431.4 | 2.26 | 1H NMR (500 MHz, Methanol-d4) δ 10.24 (s, 1H), 9.20 (d, J = 1.4 Hz, 1H), 8.98 (d, J = 1.4 Hz, 1H), 8.67 (s, 1H), 8.40 (d, J = 6.3 Hz, 1H), 7.70 (d, J = 1.4 Hz, 1H), 6.87 (d, J = 6.4 Hz, 1H), 4.94 (dd, J = 11.1, 2.8 Hz, 1H), 4.46 (s, 1H), 4.04-3.88 (m, 1H), 3.21 (dd, J = 13.0, 11.0 Hz, 1H), 2.92 (dd, J = 13.2, 10.7 Hz, 1H), 1.39 (d, J = 6.2 Hz, 3H). |
| IV-381 | 431.4 | 2.22 | 1H NMR (500 MHz, Methanol-d4) δ 10.34 (s, 1H), 9.21 (d, J = 1.4 Hz, 1H), 8.93 (d, J = 1.3 Hz, 1H), 8.73 (s, 1H), 8.44 (d, J = 6.3 Hz, 1H), 7.48 (d, J = 1.2 Hz, 1H), 6.85 (d, J = 6.3 Hz, 1H), 5.34-5.25 (m, 1H), 4.64 (d, J = 12.2 Hz, 1H), 4.20-4.02 (m, 1H), 3.88 (dd, J = 13.9, 4.2 Hz, 2H), 3.27 (dd, J = 13.1, 8.8 Hz, 1H), 1.33 (d, J = 6.2 Hz, 3H). |
| IV-382 | 410.3 | 2.12 | |
| IV-383 | 456.3 | 2.14 | |

TABLE 7-continued

Analytical data for compounds of Formula IV

| IV- | LCMS_Plus | LCMS_RT | NMR |
|---|---|---|---|
| IV-384 | 469.3 | 2.52 | 1H NMR (500 MHz, Methanol-d4) δ 9.83 (d, J = 1.4 Hz, 1H), 8.99 (d, J = 1.3 Hz, 1H), 8.59 (s, 1H), 8.32 (d, J = 6.7 Hz, 1H), 7.37 (d, J = 0.9 Hz, 1H), 6.91 (d, J = 6.7 Hz, 1H), 4.78 (s, 1H), 4.44 (s, 1H), 3.44 (dd, J = 13.2, 10.7 Hz, 1H), 3.38-3.32 (m, 2H), 3.10 (tt, J = 11.3, 10.5, 3.9 Hz, 1H), 2.33-2.23 (m, 1H), 2.07-1.97 (m, 1H), 1.97-1.86 (m, 1H), 1.86-1.73 (m, 1H), 1.43 (d, J = 7.0 Hz, 6H). |
| IV-385 | 467.3 | 2.52 | 1H NMR (500 MHz, Methanol-d4) δ 10.05 (d, J = 1.3 Hz, 1H), 8.97 (d, J = 1.3 Hz, 1H), 8.62 (s, 1H), 8.39 (d, J = 6.3 Hz, 1H), 7.66 (s, 1H), 6.87 (d, J = 6.3 Hz, 1H), 6.68-6.56 (m, 1H), 4.57 (s, 2H), 4.03-3.89 (m, 2H), 3.38 (p, J = 7.0 Hz, 1H), 2.61-2.52 (m, 2H), 1.47 (d, J = 7.1 Hz, 6H). |
| IV-386 | 431.4 | 2.18 | 1H NMR (400 MHz, DMSO-d6) δ 12.63 (s, 1H), 10.26 (s, 1H), 9.36 (d, J = 1.2 Hz, 1H), 8.69 (s, 1H), 8.32 (d, J = 6.3 Hz, 1H), 7.62 (s, 2H), 6.87 (d, J = 6.4 Hz, 1H), 4.91 (s, 1H), 3.54 (s, 1H), 2.09-1.83 (m, 3H), 1.59 (s, 1H). |
| IV-387 | 439.3 | 2.52 | 1H NMR (500 MHz, DMSO-d6) δ 12.66 (s, 1H), 9.93 (s, 1H), 9.10 (d, 1H), 8.60 (s, 1H), 8.37 (d, 1H), 7.66 (m, 1H), 7.51 (m, 1H), 6.87 (s, 1H), 5.00-4.00 (br m, 2H), 3.09 (m, 1H), 3.07 (m, 1H), 1.88-1.64 (m, 3H), 1.57 (m, 1H), 0.99 (m, 3H). |
| IV-388 | 429.4 | 2.67 | 1H NMR (500 MHz, DMSO-d6) δ 12.66 (s, 1H), 10.24 (s, 1H), 9.36 (d, 1H), 8.70 (s, 1H), 8.39 (d, 1H), 7.57 (m, 2H), 6.93 (s, 1H), 5.30-4.00 (br m, 2H), 3.15 (m, 1H), 2.95 (m, 1H), 2.00-1.84 (m, 3H), 1.64 (m, 1H), 0.99 (m, 3H). |
| IV-389 | 430.3 | 2.55 | |
| IV-390 | 470.3 | 2.34 | |
| IV-391 | 468.4 | 2.78 | |
| IV-392 | 454.3 | 2.13 | 1H NMR (500 MHz, DMSO-d6) δ 12.76 (s, 1H), 9.85 (s, 1H), 9.09 (d, J = 1.3 Hz, 1H), 8.57 (s, 1H), 8.39 (s, 1H), 7.66 (s, 2H), 6.84 (s, 1H), 6.50 (s, 1H), 2.26-2.12 (m, 1H), 2.07 (s, 6H), 1.36-1.21 (m, 1H), 1.21-1.07 (m, 2H). |
| IV-393 | 454.3 | 2.48 | |
| IV-394 | 506.4 | 2.03 | 1H NMR (500 MHz, Methanol-d4) δ 10.34 (s, 1H), 9.18 (d, J = 1.4 Hz, 1H), 8.65 (s, 1H), 8.29 (d, J = 6.4 Hz, 1H), 7.56 (s, 1H), 6.80 (d, J = 6.4 Hz, 1H), 4.59 (s, 1H), 3.95 (s, 1H), 3.80 (td, J = 5.5, 2.8 Hz, 1H), 3.72 (s, 1H), 3.61 (dd, J = 13.2, 8.7 Hz, 1H), 3.40 (dd, J = 8.7, 4.4 Hz, 1H), 3.07 (d, J = 2.4 Hz, 6H), 2.17-2.04 (m, 2H). |
| IV-395 | 506.3 | 2.05 | 1H NMR (500 MHz, Methanol-d4) δ 10.31 (s, 1H), 9.18 (d, J = 1.4 Hz, 1H), 8.66 (s, 1H), 8.34 (dd, J = 6.3, 1.0 Hz, 1H), 7.61 (d, J = 2.5 Hz, 2H), 6.80 (d, J = 6.2 Hz, 1H), 4.61 (s, 1H), 3.53-3.42 (m, 1H), 3.17 (s, 3H), 3.15 (s, 3H), 2.95 (dd, J = 9.2, 3.2 Hz, 3H), 2.39-2.25 (m, 1H), 1.75 (q, J = 11.3 Hz, 1H). |
| IV-396 | 445.3 | 2.46 | 1H NMR (500 MHz, DMSO-d6) δ 12.70 (s, 1H), 10.21 (s, 1H), 9.36 (dd, J = 5.0, 1.3 Hz, 1H), 8.93 (d, J = 76.8 Hz, 1H), 8.70 (s, 1H), 8.38 (dd, J = 27.7, 6.3 Hz, 1H), 7.62 (d, J = 1.0 Hz, 1H), 6.98 (dd, J = 42.7, 6.4 Hz, 1H), 3.61 (dtd, J = 13.2, 6.6, 3.9 Hz, 1H), 3.40 (s, 3H), 3.13 (qd, J = 7.3, 4.2 Hz, 1H), 2.95-2.87 (m, 1H), 2.77 (tt, J = 12.0, 3.9 Hz, 2H), 2.44 (d, J = 12.2 Hz, 1H), 1.90-1.77 (m, 1H), 1.59-1.48 (m, 1H). |
| IV-397 | 362.3 | 1.69 | 1H NMR (500 MHz, DMSO-d6) δ 12.7 (s, 1H), 9.69 (m, 1H), 9.22 (d, 1H), 8.58 (s, 1H), 8.39-8.34 (m, 1H), 8.14 (m, 1H), 7.90-7.60 (m, 2H), 6.88 (m, 1H), 4.80 (br s, 1H), |

TABLE 7-continued

Analytical data for compounds of Formula IV

| IV- | LCMS_Plus | LCMS_RT | NMR |
|---|---|---|---|
| | | | 4.1 (m, 1H), 3.25-3.10 (m, 3H), 2.94 (m, 1H), 1.02 (d, 3H) |
| IV-398 | 376.3 | 1.78 | |
| IV-399 | 506.1 | 2.03 | 1H NMR (500 MHz, Methanol-d4) δ 10.30 (s, 1H), 9.17 (d, J = 1.4 Hz, 1H), 8.65 (s, 1H), 8.33 (d, J = 6.3 Hz, 1H), 7.60 (s, 2H), 6.79 (d, J = 6.3 Hz, 1H), 3.53-3.41 (m, 1H), 3.17 (d, J = 1.0 Hz, 3H), 3.15 (d, J = 1.0 Hz, 3H), 3.00-2.92 (m, 1H), 2.84 (d, J = 11.7 Hz, 1H), 2.35-2.27 (m, 1H), 1.74 (q, J = 11.9 Hz, 1H), 1.29 (s, 1H), 1.26 (d, J = 6.5 Hz, 1H), 1H not observed. |
| IV-400 | 506.2 | 2.03 | |
| IV-401 | 470 | 2.33 | 1H NMR (500 MHz, Methanol-d4) δ 9.95 (d, J = 1.3 Hz, 1H), 8.94 (d, J = 1.3 Hz, 1H), 8.53 (s, 1H), 8.31 (d, J = 6.3 Hz, 1H), 7.65 (s, 2H), 6.72 (d, J = 6.4 Hz, 1H), 4.73-4.59 (m, 1H), 4.39-4.19 (m, 1H), 3.70 (d, J = 3.9 Hz, 1H), 3.48-3.37 (m, 1H), 2.84 (dd, J = 13.0, 7.5 Hz, 1H), 2.34 (td, J = 12.2, 3.6 Hz, 1H), 1.28 (d, J = 6.8 Hz, 3H), 1.26 (d, J = 6.5 Hz, 2H), 1.03 (t, J = 7.2 Hz, 3H). |
| IV-402 | 468 | 2.33 | |
| IV-403 | 456.3 | 2.16 | |
| IV-404 | 456.3 | 2.16 | 1H NMR (500 MHz, Methanol-d4) δ 10.04 (s, 1H), 9.00-8.94 (m, 1H), 8.58 (s, 1H), 8.44 (d, J = 5.2 Hz, 1H), 7.74 (s, 2H), 7.21 (d, J = 5.2 Hz, 1H), 4.90 (s, 1H), 4.69-4.44 (m, 1H), 4.30 (s, 1H), 3.02 (s, 1H), 2.78 (s, 1H), 1.29 (s, 3H), 1.14 (s, 3H). |
| IV-405 | 431.1 | 2.25 | 1H NMR (500 MHz, Methanol-d4) δ 10.32 (d, 1H), 9.22-9.14 (m, 1H), 8.68 (s, 1H), 8.37 (d, 1H), 7.71 (d, 1H), 7.18 (d, 1H), 6.81 (d, 1H), 4.71 (dd, 1H), 4.58 (s, 1H), 4.46 (s, 1H), 3.89 (m, 1H), 3.27-3.12 (m, 1H), 2.87 (dd, 1H), 1.35 (d, 3H). |
| IV-406 | 431.1 | 2.25 | |
| IV-407 | 410.1 | 2.11 | 1H NMR (500 MHz, Methanol-d4) δ 9.95 (s, 1H), 9.00 (d, J = 1.3 Hz, 1H), 8.61 (s, 1H), 8.44 (d, J = 5.2 Hz, 1H), 7.71 (s, 2H), 7.21 (d, J = 5.2 Hz, 1H), 4.95 (s, 1H), 4.58 (s, 1H), 4.30 (s, 1H), 3.02 (s, 1H), 2.79 (s, 1H), 1.30 (s, 3H), 1.12 (s, 3H). |
| IV-408 | 410.1 | 2.1 | |
| IV-409 | 449.3 | 2.61 | 1H NMR (500 MHz, Methanol-d4) δ 10.33 (s, 1H), 9.19 (d, J = 1.4 Hz, 1H), 8.67 (s, 1H), 8.32 (d, J = 6.3 Hz, 1H), 6.94 (s, 1H), 6.81 (d, J = 6.4 Hz, 1H), 4.71-4.35 (m, 2H), 2.82 (s, 1H), 2.16 (d, J = 12.9 Hz, 1H), 1.98-1.78 (m, 2H), 1.71 (d, J = 12.5 Hz, 1H), 2H not observed. |
| IV-410 | 430.3 | 1.88 | 1H NMR (500 MHz, Methanol-d4) δ 10.33 (s, 1H), 9.23-9.17 (m, 1H), 8.68 (s, 1H), 8.40 (d, J = 6.2 Hz, 1H), 7.71 (s, 1H), 7.64 (s, 1H), 6.74 (d, J = 6.3 Hz, 1H), 4.90 (dd, J = 6.6, 3.8 Hz, 1H), 4.43 (s, 2H), 4.24 (s, 1H), 4.14-4.02 (m, 1H). |
| IV-411 | 402.4 | 2.03 | |
| IV-412 | 402.4 | 2.06 | |
| IV-413 | 441 | 2.51 | |
| IV-414 | 441 | 2.51 | |
| IV-415 | 445.4 | 2.57 | 1H NMR (500 MHz, Methanol-d4) δ 10.33 (s, 1H), 9.23-9.17 (m, 1H), 8.68 (s, 1H), 8.40 (d, J = 6.2 Hz, 1H), 7.71 (s, 1H), 7.64 (s, 1H), 6.74 (d, J = 6.3 Hz, 1H), 4.90 (dd, J = 6.6, 3.8 Hz, 1H), 4.43 (s, 2H), 4.24 (s, 1H), 4.14-4.02 (m, 1H). |
| IV-416 | 445.4 | 2.57 | 1H NMR (500 MHz, Methanol-d4) δ 10.15 (s, 1H), 9.26 (d, J = 1.3 Hz, 1H), 8.74 (s, 1H), 8.39 (d, J = 6.8 Hz, 1H), 7.60 (s, 2H), 6.99 (s, 1H), 5.01 (d, J = 1.6 Hz, 1H), 3.98-3.83 (m, 1H), 3.26-3.13 (m, 1H), 1.55 (d, J = 6.7 Hz, 3H), 1.26 (d, J = 6.1 Hz, 3H). |
| IV-417 | 431.4 | 2.39 | 1H NMR (500 MHz, Methanol-d4) δ 10.30 (s, 1H), 9.25-9.20 (m, 1H), 8.70 (s, 1H), 8.50 (d, J = 5.2 Hz, 1H), 7.63 (s, 2H), 7.31 |

TABLE 7-continued

Analytical data for compounds of Formula IV

| IV- | LCMS_Plus | LCMS_RT | NMR |
|---|---|---|---|
| | | | (d, J = 5.2 Hz, 1H), 4.95-4.86 (m, 2H), 4.48 (d, J = 13.6 Hz, 1H), 4.25-4.14 (m, 1H), 3.92-3.78 (m, 1H), 3.45 (s, 1H), 1.15 (d, J = 6.6 Hz, 3H). |
| IV-418 | 431.4 | 2.45 | 1H NMR (500 MHz, DMSO-d6) δ 10.31 (s, 1H), 9.22 (s, 1H), 8.72-8.66 (m, 1H), 8.56-8.48 (m, 1H), 7.63-7.53 (m, 1H), 7.35-7.24 (m, 1H), 5.21-5.08 (m, 1H), 4.92 (s, 1H), 4.45-4.30 (m, 1H), 3.74 (ddd, J = 31.0, 11.4, 3.7 Hz, 2H), 3.53 (dt, J = 14.7, 7.3 Hz, 1H), 1.57-1.43 (m, 3H). |
| IV-419 | 429.2 | 2.61 | |
| IV-420 | 429.2 | 2.61 | 1H NMR (500 MHz, Methanol-d4) δ 10.27 (s, 1H), 9.18 (d, J = 1.3 Hz, 1H), 8.61 (s, 1H), 8.29 (d, J = 6.3 Hz, 1H), 7.57 (s, 2H), 6.77 (d, J = 6.4 Hz, 1H), 3.26-3.14 (m, 1H), 3.13-3.05 (m, 1H), 2.22-2.06 (m, 1H), 2.04-1.90 (m, 4H), 1.73 (qt, J = 13.0, 4.4 Hz, 1H), 1.10 (d, J = 6.9 Hz, 3H). |
| IV-421 | 462.5 | 2.5 | |
| IV-422 | 448.5 | 2.36 | |
| IV-423 | 349 | 3.08 | 1H NMR (400 MHz, DMSO-d6) δ 10.26 (dd, J = 1.5, 0.8 Hz, 1H), 9.36 (d, J = 1.3 Hz, 1H), 8.68 (s, 1H), 8.36 (d, J = 6.3 Hz, 1H), 6.85 (d, J = 6.4 Hz, 1H), 3.75 (s, 4H), 1.75-1.67 (m, 2H), 1.67-1.54 (m, 4H). |
| IV-424 | 363.1 | 3.29 | 1H NMR (400 MHz, DMSO-d6) δ 10.25 (dt, J = 1.7, 0.8 Hz, 1H), 9.42-9.22 (m, 1H), 8.69 (s, 1H), 8.35 (d, J = 6.3 Hz, 1H), 6.86 (d, J = 6.4 Hz, 1H), 4.36 (s, 2H), 3.11-2.98 (m, 1H), 2.81-2.61 (m, 1H), 1.92-1.70 (m, 2H), 1.63 (ddd, J = 10.6, 8.6, 5.1 Hz, 1H), 1.56-1.40 (m, 1H), 1.26 (qd, J = 12.0, 3.9 Hz, 1H), 0.96 (d, J = 6.6 Hz, 3H). |
| IV-425 | 408.1 | 1.97 | 1H NMR (400 MHz, DMSO-d6) δ 10.22 (s, 1H), 9.37 (d, J = 1.3 Hz, 1H), 8.71 (s, 1H), 8.41 (d, J = 6.2 Hz, 1H), 7.64-7.33 (m, 1H), 6.96 (d, J = 53.3 Hz, 2H), 4.50 (d, J = 53.8 Hz, 1H), 4.02 (s, 1H), 3.93-3.46 (m, 6H), 2.95 (s, 1H). |
| IV-426 | 351.1 | 2.45 | 1H NMR (400 MHz, DMSO-d6) δ 10.25 (d, J = 1.4 Hz, 1H), 9.37 (d, J = 1.3 Hz, 1H), 8.72 (s, 1H), 8.44 (d, J = 6.3 Hz, 1H), 6.87 (d, J = 6.3 Hz, 1H), 3.74 (s, 8H). |
| IV-427 | 365 | 2.48 | 1H NMR (400 MHz, DMSO-d6) δ 10.24 (s, 1H), 9.41-9.29 (m, 1H), 8.69 (s, 1H), 8.37 (d, J = 6.2 Hz, 1H), 6.78 (d, J = 6.3 Hz, 1H), 4.20-3.70 (m, 6H), 3.70-3.62 (m, 2H), 1.94 (p, J = 6.1 Hz, 2H). |
| IV-428 | 335 | 2.86 | 1H NMR (400 MHz, DMSO-d6) δ 10.41 (d, J = 1.4 Hz, 1H), 9.42-9.30 (m, 1H), 8.67 (s, 1H), 8.33 (d, J = 6.1 Hz, 1H), 6.51 (d, J = 6.1 Hz, 1H), 3.69 (s, 2H), 3.47-3.36 (m, 2H), 2.03 (s, 4H). |
| IV-429 | 363.1 | 3.2 | 1H NMR (400 MHz, DMSO-d6) δ 10.28 (s, 1H), 9.40-9.25 (m, 1H), 8.66 (s, 1H), 8.33 (d, J = 6.3 Hz, 1H), 6.69 (d, J = 6.3 Hz, 1H), 3.89 (s, 2H), 3.61 (s, 2H), 1.88-1.72 (m, 4H), 1.53 (dt, J = 5.9, 2.8 Hz, 4H). |
| IV-430 | 431.4 | 2.84 | 1H NMR (500 MHz, Methanol-d4) δ 10.27 (s, 1H), 9.27-9.18 (m, 1H), 8.70 (s, 1H), 8.33 (d, J = 6.6 Hz, 1H), 7.78 (s, 1H), 7.66 (d, J = 2.1 Hz, 1H), 6.87 (d, J = 6.6 Hz, 1H), 6.33-6.24 (m, 1H), 4.49 (s, 1H), 4.08-3.88 (m, 2H), 3.63-3.40 (m, 1H), 2.56-2.43 (m, 1H), 2.42-2.19 (m, 1H). |
| IV-431 | 376.3 | 2.14 | 1H NMR (400 MHz, DMSO-d6) δ 10.38-10.27 (m, 1H), 9.48-9.40 (m, 1H), 8.91 (d, J = 5.4 Hz, 1H), 8.88 (s, 1H), 8.64 (s, 1H), 8.30 (d, J = 0.7 Hz, 1H), 7.73 (d, J = 5.4 Hz, 1H), 5.00 (t, J = 5.3 Hz, 1H), 4.26 (t, J = 5.4 Hz, 2H), 3.81 (dq, J = 11.0, 5.4 Hz, 2H). |
| IV-432 | 392 | 2.03 | 1H NMR (400 MHz, DMSO-d6) δ 10.37 (s, 1H), 9.35 (d, J = 1.3 Hz, 1H), 8.64 (d, J = 3.3 Hz, 1H), 8.31 (d, J = 6.1 Hz, 1H), 7.36 |

TABLE 7-continued

Analytical data for compounds of Formula IV

| IV- | LCMS_Plus | LCMS_RT | NMR |
|---|---|---|---|
| | | | (s, 1H), 6.85 (s, 1H), 6.48 (d, J = 6.1 Hz, 1H), 3.99-3.74 (m, 1H), 3.61 (s, 1H), 3.57-3.35 (m, 1H), 3.29-3.03 (m, 1H), 2.80-2.58 (m, 1H), 2.37-2.07 (m, 3H), 1.74 (d, J = 11.7 Hz, 1H). |
| IV-433 | 351.04 | 2.1 | 1H NMR (400 MHz, DMSO-d6) δ 10.39 (d, J = 7.2 Hz, 1H), 9.36 (d, J = 1.3 Hz, 1H), 8.66 (s, 1H), 8.36-8.30 (m, 1H), 6.50 (dt, J = 6.7, 3.7 Hz, 1H), 5.12 (s, 1H), 4.48 (d, J = 5.7 Hz, 1H), 3.68 (q, J = 13.8, 11.5 Hz, 2H), 3.54 (d, J = 16.7 Hz, 2H), 2.10 (s, 1H), 1.99 (d, J = 10.4 Hz, 1H). |
| IV-434 | 365.05 | 2.22 | 1H NMR (400 MHz, DMSO-d6) δ 10.34 (s, 1H), 9.33 (d, J = 1.3 Hz, 1H), 8.62 (s, 1H), 8.28 (d, J = 6.1 Hz, 1H), 6.45 (d, J = 6.1 Hz, 1H), 4.78 (s, 1H), 3.69 (d, J = 53.0 Hz, 1H), 3.46 (ddd, J = 16.9, 11.3, 5.9 Hz, 4H), 3.20 (s, 1H), 2.10 (s, 1H), 1.84 (s, 1H). exchangeable proton not observed |
| IV-435 | 379 | 2.32 | 1H NMR (400 MHz, DMSO-d6) δ 10.38 (s, 1H), 9.35 (d, J = 1.3 Hz, 1H), 8.65 (s, 1H), 8.30 (d, J = 6.0 Hz, 1H), 6.47 (d, J = 6.1 Hz, 1H), 4.52 (t, J = 5.1 Hz, 1H), 3.83 (s, 1H), 3.53 (q, J = 6.2 Hz, 3H), 3.38 (s, 1H), 3.10 (dt, J = 63.4, 9.4 Hz, 1H), 2.41 (s, 1H), 2.19 (s, 1H), 1.66 (dq, J = 13.5, 8.3, 6.7 Hz, 3H). |
| IV-436 | 365.2 | 2.37 | 1H NMR (400 MHz, DMSO-d6) δ 10.32 (d, J = 34.3 Hz, 1H), 9.35 (d, J = 1.3 Hz, 1H), 8.69 (s, 1H), 8.33 (s, 1H), 6.57 (d, J = 62.8 Hz, 1H), 4.87 (d, J = 39.1 Hz, 1H), 4.38 (s, 1H), 3.97 (s, 1H), 3.70 (s, 1H), 3.51 (s, 3H), 2.17-1.92 (m, 3H). |
| IV-437 | 364.9 | 2.3 | 1H NMR (400 MHz, DMSO-d6) δ 10.24 (dd, J = 1.5, 0.8 Hz, 1H), 9.35 (d, J = 1.2 Hz, 1H), 8.66 (s, 1H), 8.34 (d, J = 6.3 Hz, 1H), 6.81 (d, J = 6.4 Hz, 1H), 4.92 (d, J = 4.3 Hz, 1H), 4.03 (d, J = 52.5 Hz, 2H), 3.60 (dq, J = 8.0, 4.0 Hz, 1H), 3.41 (s, 1H), 3.21 (dd, J = 12.9, 8.0 Hz, 1H), 2.02-1.75 (m, 1H), 1.60-1.42 (m, 2H). 1 proton obscured by solvent peak |
| IV-438 | 393.15 | 2.66 | |
| IV-439 | 379.35 | 2.44 | 1H NMR (400 MHz, DMSO-d6) δ 10.29 (dd, J = 1.5, 0.8 Hz, 1H), 9.40 (d, J = 1.4 Hz, 1H), 8.72 (s, 1H), 8.40 (d, J = 6.4 Hz, 1H), 6.85 (d, J = 6.4 Hz, 1H), 4.64 (t, J = 5.2 Hz, 1H), 4.38 (s, 1H), 3.41 (t, J = 5.7 Hz, 2H), 3.33 (s, 1H), 3.17 (s, 1H), 2.96 (dd, J = 13.1, 10.3 Hz, 1H), 1.92-1.63 (m, 3H), 1.60-1.33 (m, 2H). |
| IV-440 | 379 | 2.55 | 1H NMR (400 MHz, DMSO-d6) δ 10.27 (dd, J = 1.4, 0.7 Hz, 1H), 9.35 (d, J = 1.4 Hz, 1H), 8.68 (s, 1H), 8.33 (d, J = 6.4 Hz, 1H), 6.81 (d, J = 6.5 Hz, 1H), 4.78 (t, J = 5.7 Hz, 1H), 4.52 (s, 1H), 3.72-3.57 (m, 2H), 3.10-2.99 (m, 1H), 1.91 (d, J = 12.5 Hz, 1H), 1.77 (d, J = 13.2 Hz, 1H), 1.63 (s, 3H), 1.62 (s, 1H), 1.73-1.41 (m, 1H). |
| IV-441 | 365.4 | 2.19 | |
| IV-442 | 393.2 | 2.46 | 1H NMR (400 MHz, DMSO-d6) δ 10.25 (dd, J = 1.5, 0.8 Hz, 1H), 9.36 (d, J = 1.3 Hz, 1H), 8.67 (s, 1H), 8.35 (d, J = 6.3 Hz, 1H), 6.85 (d, J = 6.4 Hz, 1H), 4.47 (s, 2H), 4.39 (t, J = 5.1 Hz, 1H), 3.49 (td, J = 6.6, 5.1 Hz, 2H), 3.08-2.96 (m, 2H), 1.80 (d, J = 11.9 Hz, 3H), 1.41 (q, J = 6.5 Hz, 2H), 1.24-1.09 (m, 2H). |
| IV-443 | 378.7 | 2.32 | 1H NMR (400 MHz, DMSO-d6) δ 10.26 (dd, J = 1.4, 0.8 Hz, 1H), 9.36 (d, J = 1.2 Hz, 1H), 8.68 (s, 1H), 8.36 (d, J = 6.3 Hz, 1H), 6.85 (d, J = 6.4 Hz, 1H), 4.52 (t, J = 5.3 Hz, 1H), 3.30 (d, J = 5.3 Hz, 3H), 3.09-2.98 (m, 2H), 1.84-1.71 (m, 4H), 1.26-1.12 (m, 2H). |

TABLE 7-continued

Analytical data for compounds of Formula IV

| IV- | LCMS_Plus | LCMS_RT | NMR |
|---|---|---|---|
| IV-444 | 392.55 | 2.56 | 1H NMR (400 MHz, DMSO-d6) δ 10.25 (dt, J = 1.5, 0.8 Hz, 1H), 9.36 (dd, J = 1.4, 0.6 Hz, 1H), 8.67 (s, 1H), 8.35 (d, J = 6.3 Hz, 1H), 6.84 (d, J = 6.4 Hz, 1H), 4.48-4.08 (m, 2H), 3.53 (qt, J = 6.4, 4.4 Hz, 2H), 3.12 (ddd, J = 13.8, 11.4, 3.0 Hz, 1H), 2.86 (dd, J = 13.1, 10.3 Hz, 1H), 1.95-1.59 (m, 3H), 1.57-1.21 (m, 4H), 0.99-0.90 (m, 1H). |
| IV-445 | 393.1 | 2.58 | 1H NMR (400 MHz, DMSO-d6) δ 10.26 (s, 1H), 9.35 (q, J = 0.6 Hz, 1H), 8.67 (d, J = 17.1 Hz, 1H), 8.33 (d, J = 6.2 Hz, 1H), 6.69 (d, J = 6.3 Hz, 1H), 4.70 (d, J = 51.9 Hz, 1H), 4.30-4.07 (m, 1H), 3.86-3.64 (m, 1H), 3.61-3.45 (m, 1H), 3.44-3.36 (m, 1H), 3.30 (d, J = 6.3 Hz, 1H), 3.20 (d, J = 13.6 Hz, 1H), 2.06-1.54 (m, 5H), 1.39-1.17 (m, 2H). |
| IV-446 | 381.1 | 2.08 | 1H NMR (400 MHz, DMSO-d6) δ 10.25 (dd, J = 1.6, 0.8 Hz, 1H), 9.37 (d, J = 1.4 Hz, 1H), 8.72 (s, 1H), 8.44 (d, J = 6.3 Hz, 1H), 6.86 (d, J = 6.4 Hz, 1H), 4.88-4.80 (m, 1H), 4.41 (s, 1H), 4.30 (s, 1H), 4.00 (dd, J = 11.7, 2.8 Hz, 1H), 3.59 (td, J = 11.2, 2.4 Hz, 1H), 3.57-3.47 (m, 3H), 3.18-3.06 (m, 1H), 2.88 (d, J = 13.0 Hz, 1H). |
| IV-447 | 379.05 | 2.29 | 1H NMR (400 MHz, DMSO-d6) δ 10.26 (s, 1H), 9.35 (d, J = 1.3 Hz, 1H), 8.66 (s, 1H), 8.32 (d, J = 6.3 Hz, 1H), 6.67 (s, 1H), 4.61 (d, J = 3.8 Hz, 1H), 3.83 (d, J = 59.4 Hz, 3H), 3.56 (d, J = 30.1 Hz, 3H), 1.99 (dt, J = 8.3, 5.7 Hz, 1H), 1.84-1.38 (m, 4H). |
| IV-448 | 416.2 | 2.53 | |
| IV-449 | 402.1 | 2.46 | |
| IV-450 | 445.1 | 2.53 | 1H NMR (500 MHz, Methanol-d4) δ 10.30 (s, 1H), 9.19 (d, J = 1.3 Hz, 1H), 8.66 (s, 1H), 8.36 (d, J = 6.3 Hz, 1H), 7.63 (s, 2H), 6.81 (s, 1H), 5.18-4.46 (m, 2H), 4.40-3.70 (m, 2H), 3.11-2.83 (m, 1H), 1.39 (d, J = 6.1 Hz, 3H), 1.10 (d, J = 6.7 Hz, 3H) |
| IV-451 | 445.1 | 2.53 | 1H NMR (500 MHz, Methanol-d4) δ 10.46-10.08 (m, 1H), 9.19 (d, J = 2.5 Hz, 1H), 8.74-8.59 (m, 1H), 8.36 (dd, J = 6.9, 3.2 Hz, 1H), 7.63 (s, 2H), 6.81 (s, 1H), 5.17-4.58 (m, 2H), 4.48-3.72 (m, 2H), 3.12-2.79 (m, 1H), 1.39 (d, J = 6.1 Hz, 3H), 1.10 (d, J = 6.8 Hz, 3H). |
| IV-452 | 429.4 | 2.68 | 1H NMR (500 MHz, DMSO-d6) δ 12.19 (s, 1H), 10.23 (s, 1H), 9.35 (s, 1H), 8.65 (s, 1H), 8.38 (d, 1H), 7.43 (s, 1H), 6.90 (d, 1H), 4.56 (s, 2H), 3.12 (m, 1H), 2.97 (m, 1H), 2.62 (m, 1H), 2.19 (s, 3H), 1.98 (m, 1H), 1.86 (m, 1H), 1.72 (m, 1H), 1.62 (m, 1H). |
| IV-453 | 406.4 | 2.27 | 1H NMR (400 MHz, DMSO-d6) δ 10.23 (s, 1H), 9.37 (s, 1H), 8.71 (s, 1H), 8.40 (d, J = 6.3 Hz, 1H), 7.45 (s, 1H), 6.99 (s, 1H), 6.89 (d, J = 6.1 Hz, 1H), 5.63-5.21 (m, 1H), 5.01-4.33 (m, 2H), 4.18-3.76 (m, 1H), 1.94-1.75 (m, 2H), 1.67 (d, J = 13.2 Hz, 1H), 1.47 (d, J = 13.5 Hz, 1H), 1.13 (d, J = 6.8 Hz, 3H). |
| IV-454 | 412.4 | 1.9 | 1H NMR (500 MHz, DMSO-d6) δ 12.66 (s, 1H), 10.07 (m, 1H), 9.30 (d, 1H), 8.65 (s, 1H), 8.39 (d, 1H), 7.62 (m, 2H), 7.06 (t, 1H), 6.91 (s, 1H), 5.07-4.39 (m, 1H), 3.90 (m, 1H), 3.11 (m, 3H), 2.82-2.74 (m, 1H), 1.01 (d, 3H). |
| IV-455 | 412.4 | 1.93 | 1H NMR (500 MHz, DMSO-d6) δ 12.66 (s, 1H), 10.19-9.99 (m, 1H), 9.32 (d, 1H), 8.84-8.67 (m, 1H), 8.37 (s, 1H), 7.91-7.72 (m, 2H), 7.06 (t, 1H), 6.71-6.51 (m, 1H), 5.93-4.64 (m, 1H), 3.78 (m, 0.5H), 3.12 (m, 3.5H), 2.83 (m, 1H), 0.90 (m, 3H). |
| IV-456 | 401 | 2.18 | 1H NMR (500 MHz, DMSO-d6) δ 11.99 (s, 1H), 10.40 (s, 1H), 9.35 (s, 1H), 8.67 (s, 1H), 8.33 (s, 1H), 7.62 (s, 1H), 6.97 (d, J = |

TABLE 7-continued

Analytical data for compounds of Formula IV

| IV- | LCMS_Plus | LCMS_RT | NMR |
|---|---|---|---|
| | | | 14.6 Hz, 1H), 6.52 (q, J = 5.7, 4.4 Hz, 1H), 4.14-3.47 (m, 5H), 2.43-2.30 (m, 1H), 2.22-2.08 (m, 1H). |
| IV-457 | 401 | 2.42 | 1H NMR (500 MHz, DMSO-d6) δ 12.62 (br s, 1H), 10.39 (s, 1H), 9.35 (s, 1H), 8.67 (s, 1H), 8.34 (s, 1H), 7.61 (s, 1H), 6.54 (s, 1H), 6.21 (d, J = 9.8 Hz, 1H), 4.36-3.43 (m, 5H), 2.47-2.37 (m, 1H), 2.25-2.12 (m, 1H). |
| IV-458 | 444.2 | 2.26 | 1H NMR (500 MHz, Methanol-d4) δ 10.19 (s, 1H), 9.08 (s, 1H), 8.52 (m, 1H), 8.22 (m, 1H), 7.55 (s, 1H), 6.69 (m, 1H), 4.40 (s, 2H), 3.80 (dd, 1H), 2.90 (m, 1H), 2.66 (m, 1H), 2.23 (s, 3H), 1.16 (d, 3H). |
| IV-459 | 444.2 | 2.26 | 1H NMR (500 MHz, Methanol-d4) δ 10.19 (s, 1H), 9.08 (s, 1H), 8.52 (m, 1H), 8.22 (m, 1H), 7.55 (s, 1H), 6.69 (m, 1H), 4.40 (s, 2H), 3.80 (dd, 2H), 2.90 (m, 1H), 2.66 (m, 1H), 2.23 (s, 3H), 1.16 (d, 3H). |
| IV-460 | 430.2 | 2.14 | 1H NMR (500 MHz, Methanol-d4) δ 10.27 (s, 1H), 9.20 (d, 1H), 8.63 (m, 1H), 8.36 (d, 1H), 7.79 (s, 2H), 6.83 (d, 1H), 4.60 (s, 2H), 4.11-4.08 (m, 1H), 3.11 (m, 2H), 2.81 (m, 1H), 1.32 (d, 3H). |
| IV-461 | 430.1 | 2.14 | 1H NMR (500 MHz, Methanol-d4) δ 10.27 (s, 1H), 9.20 (d, 1H), 8.63 (m, 1H), 8.36 (d, 1H), 7.79 (s, 2H), 6.83 (d, 1H), 4.60 (s, 2H), 4.11-4.08 (m, 1H), 3.11 (m, 2H), 2.81 (m, 1H), 1.32 (d, 3H). |
| IV-462 | 426.2 | 2.01 | 1H NMR (500 MHz, DMSO-d6) δ 12.44-12.32 (m, 1H), 10.05 (s, 1H), 9.30 (s, 1H), 8.62 (s, 1H), 8.37 (d, 1H), 7.62-7.44 (m, 1H), 7.06 (t, 1H), 6.89 (d, 1H), 3.72 (m, 1H), 2.87 (m, 3H), 2.64 (m, 2H), 2.25 (s, 3H), 1.13 (d, 3H). |
| IV-463 | 426.2 | 2.01 | 1H NMR (500 MHz, DMSO-d6) δ 12.44-12.32 (m, 1H), 10.05 (s, 1H), 9.30 (s, 1H), 8.62 (s, 1H), 8.37 (d, 1H), 7.62-7.44 (m, 1H), 7.06 (t, 1H), 6.89 (d, 1H), 3.72 (m, 1H), 2.87 (m, 3H), 2.64 (m, 2H), 2.25 (s, 3H), 1.13 (d, 3H). |
| IV-464 | 420.2 | 2.44 | 1H NMR (400 MHz, DMSO-d6) δ 9.26 (dd, J = 1.6, 0.8 Hz, 1H), 8.15 (d, J = 1.3 Hz, 1H), 7.62 (s, 1H), 7.29 (d, J = 6.4 Hz, 1H), 5.76 (d, J = 6.4 Hz, 1H), 1.85-1.57 (m, 2H), 0.89-0.52 (m, 3H), 0.20 (d, J = 6.9 Hz, 3H), 0.07 (d, J = 5.6 Hz, 3H). 3 peaks not well resolved: 4.45, 3.74, 2.84 all broad singlets, likely coming from NH or CH next to N in piperidine ring. |
| IV-465 | 458.2 | 2.47 | 1H NMR (500 MHz, DMSO-d6) δ 12.01 (s, 1H), 10.22 (s, 1H), 9.35 (s, 1H), 8.69 (s, 1H), 8.38 (d, 1H), 6.90 (d, 1H), 4.67 (br s, 2H), 3.76 (m, 1H), 2.97 (m, 1H), 2.64 (m, 1H), 2.53 (masked, 1H), 2.24 (s, 6H), 1.12 (d, 3H). |
| IV-466 | 481.4 | 2.73 | 1H NMR (500 MHz, Methanol-d4) δ 10.31 (s, 1H), 9.27-9.20 (m, 1H), 8.68 (s, 1H), 8.41 (d, J = 6.4 Hz, 1H), 7.67 (s, 2H), 6.92 (d, J = 6.4 Hz, 1H), 6.57 (t, J = 75.1 Hz, 1H), 5.05-4.86 (m, 1H), 4.71-4.46 (m, 1H), 4.35 (tt, J = 10.4, 4.7 Hz, 1H), 3.16-2.98 (m, 3H), 2.57-2.46 (m, 1H), 1.99-1.88 (m, 1H). |
| IV-467 | 458.2 | 2.47 | 1H NMR (500 MHz, DMSO-d6) δ 12.01 (s, 1H), 10.22 (s, 1H), 9.35 (s, 1H), 8.69 (s, 1H), 8.38 (d, 1H), 6.90 (d, 1H), 4.67 (br s, 2H), 3.76 (m, 1H), 2.97 (m, 1H), 2.64 (m, 1H), 2.53 (masked, 1H), 2.24 (s, 6H), 1.12 (d, 3H). |
| IV-468 | 411.1 | 2.38 | 1H NMR (500 MHz, DMSO-d6) δ 12.30 (s, 1H), 10.04 (s, 1H), 9.29 (s, 1H), 8.60 (s, 1H), 8.38 (d, 1H), 7.43 (s, 1H), 7.30-7.05 (t, 1H), 6.87 (d, 1H), 4.47 (s, 2H), 3.31 (m, 1H), 3.09 (m, 1H), 2.97 (m, 1H), 2.20 (s, |

TABLE 7-continued

Analytical data for compounds of Formula IV

| IV- | LCMS_Plus | LCMS_RT | NMR |
|---|---|---|---|
| | | | 3H), 1.98 (m, 1H), 1.86 (m, 1H), 1.72 (m, 1H), 1.62 (m, 1H). |
| IV-469 | 411.1 | 2.38 | 1H NMR (500 MHz, DMSO-d6) δ 12.30 (s, 1H), 10.04 (s, 1H), 9.29 (s, 1H), 8.60 (s, 1H), 8.38 (d, 1H), 7.43 (s, 1H), 7.30-7.05 (t, 1H), 6.87 (d, 1H), 4.47 (s, 2H), 3.31 (m, 1H), 3.09 (m, 1H), 2.97 (m, 1H), 2.20 (s, 3H), 1.98 (m, 1H), 1.86 (m, 1H), 1.72 (m, 1H), 1.62 (m, 1H). |
| IV-470 | 429.1 | 2.64 | 1H NMR (500 MHz, DMSO-d6) δ 12.19 (s, 1H), 10.23 (s, 1H), 9.35 (s, 1H), 8.65 (s, 1H), 8.38 (d, 1H), 7.43 (s, 1H), 6.90 (d, 1H), 4.56 (s, 2H), 3.12 (m, 1H), 2.97 (m, 1H), 2.62 (m, 1H), 2.19 (s, 3H), 1.98 (m, 1H), 1.86 (m, 1H), 1.72 (m, 1H), 1.62 (m, 1H). |
| IV-471 | 429.1 | 2.64 | 1H NMR (500 MHz, DMSO-d6) δ 12.19 (s, 1H), 10.23 (s, 1H), 9.35 (s, 1H), 8.65 (s, 1H), 8.38 (d, 1H), 7.43 (s, 1H), 6.90 (d, 1H), 4.56 (s, 2H), 3.12 (m, 1H), 2.97 (m, 1H), 2.62 (m, 1H), 2.19 (s, 3H), 1.98 (m, 1H), 1.86 (m, 1H), 1.72 (m, 1H), 1.62 (m, 1H). |
| IV-472 | 481.4 | 2.63 | 1H NMR (500 MHz, Methanol-d4) δ 10.29 (s, 1H), 9.24 (d, J = 1.3 Hz, 1H), 8.69 (s, 1H), 8.36 (d, J = 6.5 Hz, 1H), 7.65 (s, 2H), 6.89 (d, J = 6.6 Hz, 1H), 6.50 (t, J = 75.3 Hz, 1H), 5.13-4.26 (m, 3H), 3.52 (d, J = 1.7 Hz, 1H), 3.32-3.22 (m, 2H), 2.40-2.30 (m, 1H), 2.16-2.07 (m, 1H). |
| IV-473 | 433.1 | 2.77 | 1H NMR (500 MHz, Methanol-d4) δ 10.23-10.06 (m, 1H), 9.08 (dd, J = 1.4, 0.7 Hz, 1H), 8.51 (s, 1H), 8.20 (d, J = 6.3 Hz, 1H), 7.41-7.30 (m, 1H), 6.65 (d, J = 6.4 Hz, 1H), 4.41 (d, J = 86.5 Hz, 2H), 3.15-3.00 (m, 2H), 2.71 (tt, J = 11.0, 3.9 Hz, 1H), 2.04 (dt, J = 12.2, 3.7 Hz, 1H), 1.82 (dp, J = 13.5, 3.4 Hz, 1H), 1.79-1.67 (m, 1H), 1.61 (dddt, J = 11.8, 9.3, 7.8, 3.9 Hz, 1H). |
| IV-474 | 498.1 | 2.66 | 1H NMR (500 MHz, DMSO-d6) δ 13.61 (s, 1H), 10.18 (s, 1H), 9.34 (s, 1H), 8.65 (s, 1H), 8.40 (d, 1H), 8.01 (s, 1H), 6.85 (s, 1H), 5.07-4.14 (br m, 2H), 3.88 (m, 1H), 2.90 (m, 2H), 2.79-2.65 (m, 1H), 1.13 (d, 3H). |
| IV-475 | 498.1 | 2.66 | 1H NMR (500 MHz, DMSO-d6) δ 13.61 (s, 1H), 10.18 (s, 1H), 9.34 (s, 1H), 8.65 (s, 1H), 8.40 (d, 1H), 8.01 (s, 1H), 6.85 (s, 1H), 5.07-4.14 (br m, 2H), 3.88 (m, 1H), 2.90 (m, 2H), 2.79-2.65 (m, 1H), 1.13 (d, 3H). |
| IV-476 | 443.1 | 2.7 | 1H NMR (500 MHz, DMSO-d6) δ 12.0 (s, 1H), 10.22 (s, 1H), 9.35 (s, 1H), 8.64 (s, 1H), 8.34 (d, 1H), 6.89 (d, 1H), 5.07-4.14 (br m, 2H), 3.17-3.02 (m, 2H), 2.61 (m, 1H), 2.18 (s, 6H), 1.95 (m, 1H), 1.84 (m, 2H), 1.58 (m, 1H). |
| IV-477 | 443.2 | 2.7 | 1H NMR (500 MHz, DMSO-d6) δ 12.0 (s, 1H), 10.22 (s, 1H), 9.35 (s, 1H), 8.64 (s, 1H), 8.34 (d, 1H), 6.89 (d, 1H), 5.07-4.14 (br m, 2H), 3.17-3.02 (m, 2H), 2.61 (m, 1H), 2.18 (s, 6H), 1.95 (m, 1H), 1.84 (m, 2H), 1.58 (m, 1H). |
| IV-478 | 416 | 2.07 | 1H NMR (500 MHz, DMSO-d6) δ 10.37 (br d, J = 20.3 Hz, 1H), 9.36 (s, 1H), 8.69 (s, 1H), 8.37 (br s, 1H), 7.15 (s, 1H), 6.97 (d, J = 0.9 Hz, 1H), 6.58 (d, J = 6.1 Hz, 1H), 5.02 (br s, 1H), 4.18-3.51 (m, 6H), 2.42 (br s, 2H). |
| IV-479 | 436.4 | 2.12 | 1H NMR (400 MHz, DMSO-d6) δ 10.34-10.14 (m, 1H), 9.36 (d, J = 1.3 Hz, 1H), 8.69 (s, 1H), 8.37 (d, J = 6.3 Hz, 1H), 7.94 (t, J = 5.6 Hz, 1H), 6.89 (d, J = 6.4 Hz, 1H), 4.65 (t, J = 5.5 Hz, 1H), 4.42 (s, 2H), 3.40 (p, J = 5.9 Hz, 2H), 3.23-2.97 (m, 4H), 2.45-2.31 (m, 1H), 1.90 (d, J = 12.3 Hz, 1H), 1.76 (dtd, J = 24.0, 12.2, 10.9, 3.9 Hz, 2H), 1.48 (d, J = 12.9 Hz, 1H). |
| IV-480 | 405.3 | 2.12 | 1H NMR (400 MHz, DMSO-d6) δ 10.23 (d, J = 1.4 Hz, 1H), 9.37 (d, J = 1.3 Hz, 1H), |

TABLE 7-continued

Analytical data for compounds of Formula IV

| IV- | LCMS_Plus | LCMS_RT | NMR |
|---|---|---|---|
| | | | 8.75 (s, 1H), 8.43 (d, J = 6.3 Hz, 1H), 6.91 (d, J = 6.3 Hz, 1H), 6.61 (s, 1H), 4.54 (d, J = 55.7 Hz, 2H), 3.72 (tt, J = 12.9, 3.7 Hz, 2H), 3.46 (ddd, J = 9.4, 8.3, 1.2 Hz, 1H), 3.07-2.86 (m, 4H). |
| IV-481 | 420.1 | 2.37 | 1H NMR (400 MHz, DMSO-d6) δ 10.24 (s, 1H), 9.37 (s, 1H), 8.71 (s, 1H), 8.38 (d, J = 6.4 Hz, 1H), 7.44 (s, 1H), 6.99 (d, J = 6.3 Hz, 1H), 6.87 (d, J = 6.4 Hz, 1H), 2.89-2.68 (m, 1H), 2.22-2.01 (m, 2H), 1.41 (d, J = 13.4 Hz, 1H), 1.14 (d, J = 6.9 Hz, 3H), 0.98 (d, J = 6.7 Hz, 3H); 3 protons missing signals, those corresponding to CH next to N of piperidine - these are often significantly broadened. |
| IV-482 | 441.3 | 2.54 | 1H NMR (400 MHz, DMSO-d6) δ 10.26 (d, J = 1.4 Hz, 1H), 9.36 (d, J = 1.3 Hz, 1H), 8.74 (s, 1H), 8.41 (d, J = 6.3 Hz, 1H), 6.81 (d, J = 6.3 Hz, 1H), 4.61 (s, 1H), 4.22 (s, 1H), 3.29-3.16 (m, 3H), 3.15-3.04 (m, 1H), 3.04 (s, 3H), 2.19 (s, 1H), 2.01 (s, 1H), 1.76 (s, 1H), 1.64-1.44 (m, 2H). |
| IV-483 | 427.3 | 2.42 | 1H NMR (400 MHz, DMSO-d6) δ 10.24 (dd, J = 1.5, 0.8 Hz, 1H), 9.38 (d, J = 1.3 Hz, 1H), 8.71 (s, 1H), 8.46 (d, J = 6.3 Hz, 1H), 6.96 (d, J = 6.3 Hz, 1H), 4.84 (s, 1H), 4.36 (s, 1H), 3.39-3.33 (m, 2H), 3.27-3.13 (m, 1H), 3.09 (s, 3H), 2.22 (d, J = 13.9 Hz, 1H), 2.04-1.75 (m, 2H), 1.56 (d, J = 12.8 Hz, 1H). |
| IV-484 | 415.3 | 2.44 | 1H NMR (500 MHz, Methanol-d4) δ 10.32 (s, 1H), 9.21 (s, 1H), 8.67 (s, 1H), 8.45 (d, 1H), 7.62 (s, 1H), 7.21 (d, 1H), 6.92 (s, 1H), 4.90 (masked, 1H), 4.73 (m, 1H), 3.18 (m, 2H), 2.89 (m, 1H), 2.19 (m, 1H), 1.93-1.88 (m, 2H), 1.75 (m, 1H). |
| IV-485 | 429.4 | 2.71 | 1H NMR (500 MHz, Methanol-d4) δ 10.34 (s, 1H), 9.23 (s, 1H), 8.68 (s, 1H), 8.48 (d, 1H), 7.54 (s, 2H), 7.21 (d, 1H), 5.20 (m, 1H), 4.73 (m, 1H), 3.18 (m, 1H), 3.09 (m, 1H), 2.15 (m, 1H), 1.97 (m, 2H), 1.176 (m, 1H), 1.22 (m, 1H), 1.10 (d, 3H). |
| IV-486 | 394.1 | 2.04 | |
| IV-487 | 378.2 | 2.15 | |
| IV-488 | 392.1 | 2.39 | |
| IV-489 | 380.2 | 2.05 | 1H NMR (400 MHz, DMSO-d6) δ 10.23 (d, J = 5.7 Hz, 1H), 9.36 (s, 1H), 8.74 (s, 1H), 8.43 (d, J = 6.2 Hz, 1H), 6.85 (dd, J = 9.4, 6.3 Hz, 1H), 4.46-4.17 (m, 4H), 4.05-3.97 (m, 1H), 3.58 (td, J = 11.6, 2.8 Hz, 1H), 3.41 (dtd, J = 10.8, 5.7, 2.6 Hz, 1H), 3.18-3.04 (m, 1H), 2.83 (dd, J = 13.1, 10.4 Hz, 1H), 2.70 (d, J = 5.7 Hz, 2H). |
| IV-490 | 447.1 | 2.22 | 1H NMR (400 MHz, DMSO-d6) δ 10.24 (dd, J = 1.5, 0.8 Hz, 1H), 9.36 (d, J = 1.3 Hz, 1H), 8.68 (s, 1H), 8.36 (d, J = 6.3 Hz, 1H), 7.72 (s, 1H), 6.89 (d, J = 6.4 Hz, 1H), 4.88-3.69 (m, 2H), 3.28-3.05 (m, 6H), 2.84 (dt, J = 10.7, 5.1 Hz, 1H), 2.75-2.63 (m, 1H), 2.43 (tt, J = 9.8, 3.6 Hz, 1H), 2.01-1.88 (m, 1H), 1.82 (dt, J = 13.1, 3.9 Hz, 1H), 1.70-1.57 (m, 1H), 1.48 (q, J = 11.9 Hz, 1H). |
| IV-491 | 433.1 | 2.73 | 1H NMR (500 MHz, Methanol-d4) δ 10.21-10.13 (m, 1H), 9.07 (dd, J = 1.3, 0.7 Hz, 1H), 8.50 (s, 1H), 8.19 (d, J = 6.4 Hz, 1H), 7.38 (dd, J = 2.4, 0.6 Hz, 1H), 6.64 (d, J = 6.4 Hz, 1H), 4.63-4.16 (m, 2H), 3.15-2.97 (m, 2H), 2.70 (tt, J = 11.0, 3.9 Hz, 1H), 2.09-1.99 (m, 1H), 1.82 (dp, J = 13.3, 3.3 Hz, 1H), 1.78-1.67 (m, 1H), 1.61 (dtt, J = 13.2, 11.7, 3.9 Hz, 1H). |
| IV-492 | 433.1 | 2.73 | 1H NMR (500 MHz, Methanol-d4) δ 10.35-10.28 (m, 1H), 9.19 (t, J = 1.8 Hz, 1H), 8.67-8.59 (m, 1H), 8.37-8.24 (m, 1H), 7.50 (d, J = 2.3 Hz, 1H), 6.82-6.69 (m, 1H), 4.75- |

TABLE 7-continued

Analytical data for compounds of Formula IV

| IV- | LCMS_Plus | LCMS_RT | NMR |
|---|---|---|---|
| | | | 4.29 (m, 2H), 3.27-3.12 (m, 2H), 2.82 (tq, J = 10.6, 3.3 Hz, 1H), 2.16 (ddd, J = 12.3, 4.4, 2.4 Hz, 1H), 2.00-1.90 (m, 1H), 1.90-1.79 (m, 1H), 1.79-1.65 (m, 1H). |
| IV-493 | 416 | 2.32 | 1H NMR (500 MHz, DMSO-d6) δ 10.21 (s, 1H), 9.42-9.33 (m, 1H), 8.71 (s, 1H), 8.43 (d, J = 6.3 Hz, 1H), 8.28 (d, J = 1.0 Hz, 1H), 7.77 (d, J = 1.0 Hz, 1H), 6.97 (d, J = 6.3 Hz, 1H), 4.75 (tt, J = 9.3, 4.4 Hz, 1H), 3.75 (dd, J = 13.1, 9.7 Hz, 1H), 3.41-3.34 (m, 1H), 3.29 (d, J = 6.2 Hz, 1H), 2.27 (qdt, J = 13.0, 9.9, 4.5 Hz, 2H), 1.93 (dq, J = 12.4, 4.1 Hz, 1H), 1.72 (dtt, J = 14.9, 9.9, 4.5 Hz, 1H). |
| IV-494 | 401 | 2.37 | 1H NMR (500 MHz, DMSO-d6) δ 12.68 (s, 1H), 10.41 (s, 1H), 9.36 (s, 1H), 8.68 (s, 1H), 8.35 (d, J = 5.7 Hz, 1H), 7.68 (s, 1H), 7.48 (s, 1H), 6.55 (s, 1H), 3.95-3.80 (m, 1H), 3.76-3.43 (m, 3H), 2.42 (br s, 1H), 2.07 (br s, 1H). |
| IV-495 | 393.1 | 3.01 | 1H NMR (500 MHz, DMSO-d6) δ 10.23 (dd, J = 1.4, 0.8 Hz, 1H), 9.35 (dd, J = 1.4, 0.6 Hz, 1H), 8.66 (s, 1H), 8.35 (d, J = 6.3 Hz, 1H), 6.81 (d, J = 6.4 Hz, 1H), 4.26 (s, 2H), 3.29 (d, J = 6.0 Hz, 2H), 3.25 (s, 3H), 3.22-3.15 (m, 1H), 3.01 (dd, J = 13.1, 9.7 Hz, 1H), 1.95-1.66 (m, 3H), 1.61-1.27 (m, 2H). |
| IV-496 | 405.1 | 2.82 | 1H NMR (500 MHz, DMSO-d6) δ 10.23 (d, J = 1.2 Hz, 1H), 9.35 (d, J = 1.3 Hz, 1H), 8.66 (s, 1H), 8.35 (d, J = 6.3 Hz, 1H), 6.87 (d, J = 6.3 Hz, 1H), 3.92-3.81 (m, 1H), 3.77-3.58 (m, 3H), 3.30 (m, 2H, not observed), 3.45 (dd, J = 992, 8.6 Hz, 2H), 1.86-1.52 (m, 6H). |
| IV-497 | 377.1 | 2.55 | 1H NMR (500 MHz, DMSO-d6) δ 10.36 (s, 1H), 9.36 (d, J = 1.2 Hz, 1H), 8.67 (s, 1H), 8.36 (d, J = 6.0 Hz, 1H), 6.54 (d, J = 6.1 Hz, 1H), 4.61 (t, J = 5.2 Hz, 1H), 4.01-3.87 (m, 1H), 3.80 (td, J = 8.3, 4.7 Hz, 4H), 3.36 (d, J = 5.2 Hz, 1H), 3.12 (s, 1H), 2.16 (dq, J = 12.4, 7.8 Hz, 1H), 1.88 (t, J = 7.3 Hz, 1H). |
| IV-498 | 406.3 | 2.29 | |
| IV-499 | 406.3 | 2.28 | |
| IV-500 | 420.1 | 2.44 | |
| IV-501 | 420.1 | 2.43 | |
| IV-502 | 446.1 | 2.9 | 1H NMR (400 MHz, Methanol-d4) δ 10.26-10.16 (m, 1H), 9.30-9.21 (m, 1H), 8.67 (d, J = 1.0 Hz, 1H), 8.37 (dd, J = 6.6, 1.2 Hz, 1H), 6.87 (d, J = 6.6 Hz, 1H), 4.86-4.70 (m, 1H), 4.51 (s, 1H), 4.32-4.19 (m, 1H), 3.19 (q, J = 11.4, 10.5 Hz, 2H), 2.31 (dtt, J = 20.4, 10.2, 5.6 Hz, 1H), 2.20-1.93 (m, 2H), 1.83-1.59 (m, 2H). |
| IV-503 | 446.1 | 2.96 | 1H NMR (400 MHz, Methanol-d4) δ 10.32 (dd, J = 1.5, 0.8 Hz, 1H), 9.30-9.18 (m, 1H), 8.70 (s, 1H), 8.40 (d, J = 6.5 Hz, 1H), 6.85 (d, J = 6.5 Hz, 1H), 4.87 (s, 1H), 4.49 (s, 1H), 4.24 (qd, J = 8.0, 5.0 Hz, 1H), 3.22-3.07 (m, 2H), 2.23 (dt, J = 11.3, 4.1 Hz, 1H), 2.10 (t, J = 10.9 Hz, 1H), 2.06-1.93 (m, 1H), 1.90-1.56 (m, 2H). |
| IV-504 | 406.1 | 2.31 | 1H NMR (500 MHz, DMSO-d6) δ 10.24 (d, J = 1.3 Hz, 1H), 9.37 (d, J = 1.3 Hz, 1H), 8.74 (s, 1H), 8.42 (d, J = 6.3 Hz, 1H), 6.88 (d, J = 6.3 Hz, 1H), 3.87-3.75 (m, 2H), 3.58 (td, J = 11.1, 2.2 Hz, 1H), 3.22 (t, J = 10.5 Hz, 1H), 3.13 (t, J = 11.7 Hz, 1H), 2.80 (dd, J = 78.4, 11.5 Hz, 2H), 2.69-2.58 (m, 2H), 2.30-2.13 (m, 3H). |
| IV-505 | 419.1 | 2.92 | 1H NMR (500 MHz, DMSO-d6) δ 10.27 (s, 1H), 9.37 (d, J = 1.3 Hz, 1H), 8.71 (s, 1H), 8.35 (d, J = 6.3 Hz, 1H), 6.92 (s, 1H), 3.73 (s, 4H), 3.60 (dddd, J = 45.4, 11.3, 7.0, 3.8 |

TABLE 7-continued

Analytical data for compounds of Formula IV

| IV- | LCMS_Plus | LCMS_RT | NMR |
|---|---|---|---|
| | | | Hz, 4H), 1.63 (d, J = 2.8 Hz, 4H), 1.52-1.30 (m, 4H). |
| IV-506 | 448.2 | 3.22 | 1H NMR (500 MHz, DMSO-d6) δ 10.19 (s, 1H), 9.37 (d, J = 1.3 Hz, 1H), 8.67 (s, 1H), 8.43 (d, J = 6.3 Hz, 1H), 6.96 (d, J = 6.4 Hz, 1H), 4.70 (d, J = 1.6 Hz, 1H), 3.82-3.60 (m, 2H), 3.23-3.00 (m, 2H), 2.51 (p, J = 1.8 Hz, 3H), 2.19 (td, J = 11.4, 3.3 Hz, 1H), 0.99 (s, 9H). |
| IV-507 | 419.1 | 2.89 | 1H NMR (500 MHz, DMSO-d6) δ 10.39 (s, 1H), 9.36 (d, J = 1.3 Hz, 1H), 8.74-8.57 (m, 1H), 8.33 (d, J = 6.0 Hz, 1H), 6.65-6.37 (m, 1H), 4.07-3.79 (m, 4H), 3.72-3.46 (m, 2H), 3.31 (s, 2H), 2.15 (d, J = 46.4 Hz, 2H), 1.66 (dd, J = 22.4, 12.8 Hz, 3H), 1.54 (s, 1H), 1.43-1.23 (m, 2H). |
| IV-508 | 391.4 | 2.61 | 1H NMR (500 MHz, DMSO-d6) δ 10.40 (s, 1H), 9.36 (s, 1H), 8.67 (s, 1H), 8.34 (d, J = 6.0 Hz, 1H), 6.51 (s, 1H), 4.72 (d, J = 7.6 Hz, 2H), 4.47-4.34 (m, 2H), 3.67-3.62 (m, 1H), 3.58-3.52 (m, 1H), 3.49-3.40 (m, 1H), 3.25 (d, J = 10.2 Hz, 1H), 3.14-2.99 (m, 1H), 2.87-2.71 (m, 1H), 2.26-2.13 (m, 1H), 1.77-1.60 (m, 1H). |
| IV-509 | 407.4 | 3.25 | 1H NMR (500 MHz, DMSO-d6) δ 10.29 (s, 1H), 9.36 (d, J = 1.3 Hz, 1H), 8.67 (s, 1H), 8.36 (d, J = 6.3 Hz, 1H), 6.69 (s, 1H), 4.29-4.17 (m, 1H), 3.86-3.64 (m, 1H), 3.65-3.37 (m, 1H), 3.29 (s, 3H + m, 3H), 3.26 (s, 2H), 1.83-1.69 (m, 2H), 1.67-1.56 (m, 1H), 1.37-1.24 (m, 2H). |
| IV-510 | 448.4 | 2.89 | 1H NMR (500 MHz, DMSO-d6) δ 10.26 (s, 1H), 9.36 (d, J = 1.3 Hz, 1H), 8.68 (s, 1H), 8.36 (d, J = 6.3 Hz, 1H), 6.85 (d, J = 6.4 Hz, 1H), 4.47 (m, 4H, broad), 3.59 (t, J = 4.6 Hz, 4H), 3.29 (s, 1H), 3.05 (d, J = 2.2 Hz, 1H), 2.42-2.28 (m, 4H), 2.17 (d, J = 7.3 Hz, 2H), 1.85 (d, J = 13.2 Hz, 2H), 1.14 (q, J = 12.2, 10.2 Hz, 2H). |
| IV-511 | 391.3 | 2.61 | 1H NMR (500 MHz, DMSO-d6) δ 10.24 (d, J = 0.7 Hz, 1H), 9.36 (d, J = 1.3 Hz, 1H), 8.69 (s, 1H), 8.37 (d, J = 6.2 Hz, 1H), 6.89 (d, J = 6.3 Hz, 1H), 4.40 (s, 4H), 3.70 (s, 4H), 2.01-1.79 (m, 4H). |
| IV-512 | 393.3 | 3 | 1H NMR (500 MHz, DMSO-d6) δ 10.25 (d, J = 1.3 Hz, 1H), 9.35 (d, J = 1.3 Hz, 1H), 8.68 (s, 1H), 8.36 (d, J = 6.3 Hz, 1H), 6.85 (d, J = 6.4 Hz, 1H), 4.49 (s, 2H), 3.25 (s, 3H), 3.23 (d, J = 6.3 Hz, 2H), 3.05 (td, J = 12.7, 2.8 Hz, 2H), 2.00-1.90 (m, 1H), 1.79 (dd, J = 13.3, 3.5 Hz, 2H), 1.31-1.13 (m, 2H). |
| IV-513 | 374.05 | 2.58 | 1H NMR (400 MHz, DMSO-d6) δ 10.24 (t, J = 1.1 Hz, 1H), 9.37 (d, J = 1.4 Hz, 1H), 8.72 (s, 1H), 8.42 (d, J = 6.3 Hz, 1H), 6.91 (d, J = 6.4 Hz, 1H), 4.06 (s, 2H), 3.58 (s, 1H), 3.32-3.19 (m, 2H), 2.11-1.97 (m, 2H), 1.81 (ddt, J = 13.7, 9.1, 4.4 Hz, 2H). |
| IV-514 | 388.05 | 2.75 | 1H NMR (400 MHz, DMSO-d6) δ 10.38 (s, 1H), 9.35 (s, 1H), 8.65 (s, 1H), 8.32 (d, J = 6.0 Hz, 1H), 6.47 (s, 1H), 3.80 (s, 1H), 3.53 (s, 1H), 3.06 (s, 1H), 2.68 (s, 2H), 2.38 (s, 2H), 2.14 (s, 2H), 1.80 (s, 1H). 1 proton obscured by solvent peaks |
| IV-515 | 404.1 | 2.19 | 1H NMR (400 MHz, DMSO-d6) δ 10.11 (s, 1H), 9.15-9.10 (m, 1H), 8.43 (s, 1H), 8.12 (d, J = 6.3 Hz, 1H), 7.39 (s, 1H), 6.58 (d, J = 6.3 Hz, 1H), 4.16 (s, 1H), 3.25-3.11 (m, 2H), 2.93 (s, 1H), 2.67 (d, J = 9.9 Hz, 1H), 2.52-2.38 (m, 2H), 1.78-1.69 (m, 1H), 1.27 (d, J = 10.3 Hz, 1H), 0.75 (s, 1H). |
| IV-516 | 373.9 | 2.57 | 1H NMR (400 MHz, DMSO-d6) δ 10.34 (dd, J = 1.5, 0.8 Hz, 1H), 9.48 (q, J = 0.6 Hz, 1H), 8.85 (s, 1H), 8.55 (d, J = 6.3 Hz, 1H), 7.09 (d, J = 6.3 Hz, 1H), 4.33-4.24 (m, 1H), 4.05 (d, J = 13.6 Hz, 2H), 3.82- |

TABLE 7-continued

Analytical data for compounds of Formula IV

| IV- | LCMS_Plus | LCMS_RT | NMR |
|---|---|---|---|
| | | | 3.68 (m, 1H), 3.29 (dq, J = 6.6, 3.4 Hz, 1H), 2.19 (s, 1H), 2.23-2.01 (m, 2H), 1.92-1.73 (m, 1H). |
| IV-517 | 363.25 | 3.29 | 1H NMR (400 MHz, DMSO-d6) δ 10.25 (t, J = 1.1 Hz, 1H), 9.36 (d, J = 1.2 Hz, 1H), 8.68 (s, 1H), 8.35 (d, J = 6.3 Hz, 1H), 6.85 (d, J = 6.4 Hz, 1H), 4.47 (s, 2H), 3.03 (td, J = 12.8, 2.5 Hz, 2H), 1.81-1.71 (m, 1H), 1.74 (s, 2H), 1.14 (dddd, J = 16.3, 14.0, 11.4, 3.9 Hz, 2H), 0.95 (d, J = 6.2 Hz, 3H). |
| IV-518 | 363.33 | 3.27 | 1H NMR (400 MHz, DMSO-d6) δ 10.25 (d, J = 1.2 Hz, 1H), 9.36 (d, J = 1.2 Hz, 1H), 8.68 (s, 1H), 8.36 (d, J = 6.3 Hz, 1H), 6.82 (d, J = 6.5 Hz, 1H), 4.81 (s, 1H), 4.34 (s, 1H), 3.13-3.01 (m, 1H), 1.79 (d, J = 13.8 Hz, 1H), 1.77-1.60 (m, 4H), 1.51-1.43 (m, 1H), 1.24 (d, J = 6.8 Hz, 3H). |
| IV-519 | 377.34 | 3.43 | 1H NMR (400 MHz, DMSO-d6) δ 10.15 (s, 1H), 9.28 (d, J = 1.3 Hz, 1H), 8.60 (s, 1H), 8.26 (d, J = 6.3 Hz, 1H), 6.75 (d, J = 6.4 Hz, 1H), 4.33 (s, 2H), 2.93 (t, J = 11.3 Hz, 1H), 1.71 (s, 2H), 1.48 (d, J = 7.4 Hz, 1H), 1.47-1.34 (m, 2H), 1.02 (d, J = 6.9 Hz, 3H), 0.97-0.84 (m, 3H). |
| IV-520 | 393.19 | 2.62 | 1H NMR (400 MHz, DMSO-d6) δ 10.40 (s, 1H), 9.36 (d, J = 1.2 Hz, 1H), 8.66 (s, 1H), 8.31 (d, J = 5.9 Hz, 1H), 6.50 (dd, J = 15.2, 6.3 Hz, 1H), 4.45 (s, 1H), 4.00-3.76 (m, 1H), 3.55 (dt, J = 39.5, 10.1 Hz, 2H), 2.37 (s, 1H), 1.97 (d, J = 35.9 Hz, 3H), 1.20 (d, J = 3.8 Hz, 6H). |
| IV-521 | 360.2 | 2.44 | 1H NMR (400 MHz, DMSO-d6) δ 10.34 (s, 1H), 9.37 (d, J = 1.3 Hz, 1H), 8.71 (s, 1H), 8.42 (d, J = 6.1 Hz, 1H), 6.60 (d, J = 6.1 Hz, 1H), 3.68 (t, J = 6.7 Hz, 5H), 2.45 (d, J = 6.6 Hz, 1H), 2.37 (d, J = 7.2 Hz, 1H). |
| IV-522 | 405.3 | 2.81 | 1H NMR (500 MHz, DMSO-d6) δ 10.42 (s, 1H), 9.36 (s, 1H), 8.69 (s, 1H), 8.33 (d, J = 6.0 Hz, 1H), 6.66-6.32 (m, 1H), 3.64 (dt, J = 57.6, 36.9 Hz, 6H), 1.98 (s, 2H), 1.60 (d, J = 5.1 Hz, 4H), 0.95 (d, J = 6.5 Hz, 2H). |
| IV-523 | | | 1H NMR (500 MHz, DMSO-d6) δ 10.26 (s, 1H), 9.36 (d, J = 1.5 Hz, 1H), 8.71 (d, J = 2.1 Hz, 1H), 8.37 (dd, J = 6.2, 1.5 Hz, 1H), 6.96 (d, J = 6.3 Hz, 1H), 4.37-4.16 (m, 4H), 4.00 (s, 2H), 3.65 (s, 2H), 2.08-1.87 (m, 2H), 1.58 (tt, J = 4.3, 1.8 Hz, 2H). |
| IV-524 | 419 | 2.62 | 1H NMR (500 MHz, DMSO-d6) δ 12.29 (br s, 1H), 10.40 (s, 1H), 9.36 (s, 1H), 8.68 (s, 1H), 8.36 (d, J = 6.0 Hz, 1H), 7.66 (s, 1H), 6.55 (d, J = 6.0 Hz, 1H), 4.19-3.32 (m, 5H), 2.41 (br s, 1H), 2.08 (brs, 1H). |
| IV-525 | 445.3 | 2.5 | 1H NMR (500 MHz, DMSO-d6) δ 14.51 (s, 2H), 10.20 (s, 1H), 9.39 (d, J = 1.3 Hz, 1H), 9.15 (d, J = 3.5 Hz, 1H), 8.81 (s, 1H), 8.51 (s, 1H), 7.66 (s, 1H), 6.92 (s, 1H), 5.09-5.02 (m, 1H), 5.38-4.65 (m, 1H), 4.60-3.99 (m, 1H), 3.99-3.85 (m, 1H), 3.08-2.92 (m, 1H), 1.36 (d, J = 6.1 Hz, 3H), 1.02 (d, J = 6.7 Hz, 3H). |
| IV-526 | 420.45 | 2.45 | 1H NMR (400 MHz, DMSO-d6) δ 10.27-10.21 (m, 1H), 9.35 (d, J = 1.2 Hz, 1H), 8.68 (s, 1H), 8.36 (d, J = 6.3 Hz, 1H), 7.94 (t, J = 5.8 Hz, 1H), 6.82 (d, J = 6.3 Hz, 1H), 4.30 (s, 2H), 3.13 (ddd, J = 13.8, 11.2, 2.9 Hz, 1H), 3.04 (t, J = 6.5 Hz, 2H), 2.87 (dd, J = 13.2, 10.2 Hz, 1H), 1.85 (s, 3H), 1.78 (dq, J = 17.2, 4.0 Hz, 1H), 1.66 (ddd, J = 10.3, 6.7, 3.6 Hz, 1H), 1.53-1.39 (m, 1H), 1.37-1.24 (m, 1H), 0.97 (d, J = 6.3 Hz, 1H). |
| IV-527 | 421.45 | 2.32 | 1H NMR (400 MHz, DMSO-d6) δ 10.03 (d, J = 1.6 Hz, 1H), 9.12 (d, J = 1.4 Hz, 1H), 8.47 (s, 1H), 8.14 (dd, J = 6.3, 1.3 Hz, 1H), 6.58 (d, J = 6.4 Hz, 1H), 5.87 (t, J = 5.9 Hz, 1H), 5.20 (s, 2H), 2.89 (t, J = 11.7 Hz, 1H), 2.81-2.68 (m, 2H), 2.61 (t, J = 11.8 Hz, |

TABLE 7-continued

Analytical data for compounds of Formula IV

| IV- | LCMS_Plus | LCMS_RT | NMR |
|---|---|---|---|
| | | | 2H), 1.62-1.50 (m, 2H), 1.22 (t, J = 12.3 Hz, 2H), 1.14-0.76 (m, 2H). |
| IV-528 | 392.09 | 2.17 | |
| IV-529 | 406.35 | 2.35 | 1H NMR (400 MHz, DMSO-d6) δ 10.25 (d, J = 1.3 Hz, 1H), 9.36 (d, J = 1.3 Hz, 1H), 8.69 (s, 1H), 8.37 (d, J = 6.3 Hz, 1H), 7.32 (s, 1H), 6.84-6.77 (m, 2H), 3.17 (t, J = 11.3 Hz, 1H), 2.92 (dd, J = 13.0, 10.0 Hz, 1H), 2.19-1.99 (m, 3H), 1.99-1.70 (m, 3H), 1.53-1.22 (m, 3H). |
| IV-530 | 406.3 | 2.32 | 1H NMR (400 MHz, DMSO-d6) δ 10.23 (t, J = 1.1 Hz, 1H), 9.37 (d, J = 1.3 Hz, 1H), 8.70 (s, 1H), 8.38 (d, J = 6.3 Hz, 1H), 7.93 (d, J = 7.2 Hz, 1H), 6.81 (d, J = 6.4 Hz, 1H), 3.74-3.69 (m, 1H), 3.17 (dd, J = 12.9, 8.9 Hz, 1H), 1.93-1.81 (m, 1H), 1.85 (s, 2H), 1.80 (s, 3H), 1.57 (d, J = 11.0 Hz, 2H), 0.96 (d, J = 6.2 Hz, 1H). 1 proton obscured by solvent peaks |
| IV-531 | 379.1 | 2.76 | 1H NMR (400 MHz, DMSO-d6) δ 10.24 (dd, J = 1.5, 0.8 Hz, 1H), 9.37 (d, J = 1.2 Hz, 1H), 8.74 (s, 1H), 8.41 (d, J = 6.3 Hz, 1H), 6.88 (d, J = 6.3 Hz, 1H), 3.79-3.70 (m, 4H), 3.64 (s, 2H), 1.21 (s, 6H). |
| IV-532 | 365 | 2.65 | 1H NMR (400 MHz, DMSO-d6) δ 9.99 (dt, J = 1.5, 0.9 Hz, 1H), 9.12 (d, J = 1.3 Hz, 1H), 8.46 (s, 1H), 8.19 (d, J = 6.3 Hz, 1H), 6.59 (d, J = 6.3 Hz, 1H), 4.28 (s, 1H), 3.90 (d, J = 13.6 Hz, 1H), 3.76 (dd, J = 11.5, 3.8 Hz, 1H), 3.55 (d, J = 11.5 Hz, 1H), 3.43 (dd, J = 11.6, 3.2 Hz, 1H), 3.29 (td, J = 11.9, 3.1 Hz, 1H), 3.09-2.97 (m, 1H), 1.04 (d, J = 6.8 Hz, 3H). |
| IV-533 | 404.1 | 2.23 | 1H NMR (400 MHz, DMSO-d6) δ 10.37 (s, 1H), 9.35 (s, 1H), 8.67 (s, 1H), 8.35 (d, J = 6.0 Hz, 1H), 7.88 (s, 1H), 6.53 (s, 1H), 4.04-3.33 (m, 6H), 2.35-1.82 (m, 4H). |
| IV-534 | 404.1 | 2.11 | 1H NMR (400 MHz, DMSO-d6) δ 10.46-10.33 (m, 1H), 9.36 (d, J = 1.3 Hz, 1H), 8.66 (d, J = 11.0 Hz, 1H), 8.36 (s, 1H), 7.70 (s, 1H), 6.53 (s, 1H), 3.76 (d, J = 30.5 Hz, 2H), 3.51 (d, J = 27.2 Hz, 2H), 2.40-2.23 (m, 2H), 2.09 (d, J = 6.2 Hz, 2H), 1.14-0.90 (m, 2H). |
| IV-535 | 430.1 | 3.02 | 1H NMR (500 MHz, DMSO-d6) δ 10.28 (s, 1H), 9.36 (d, J = 1.3 Hz, 1H), 9.15 (s, 1H), 8.94 (s, 1H), 8.79 (s, 1H), 8.46 (d, J = 6.3 Hz, 1H), 7.04 (d, J = 6.3 Hz, 1H), 6.63 (s, 1H), 4.55 (s, 1H), 3.95 (s, 1H), 3.27 (d, J = 0.8 Hz, 4H). |
| IV-536 | 428.05 | 2.31 | 1H NMR (400 MHz, DMSO-d6) δ 10.25 (t, J = 1.1 Hz, 1H), 9.37 (d, J = 1.4 Hz, 1H), 8.75 (s, 1H), 8.45 (d, J = 6.3 Hz, 1H), 7.03 (s, 2H), 6.88 (d, J = 6.4 Hz, 1H), 5.02 (s, 1H), 4.38 (s, 1H), 3.19-3.09 (m, 1H), 3.04 (ddd, J = 18.4, 10.8, 5.3 Hz, 2H), 2.23 (d, J = 11.7 Hz, 1H), 1.88 (s, 1H), 1.80 (qd, J = 12.1, 4.1 Hz, 1H), 1.57 (s, 1H). |
| IV-537 | 406.1 | 2.2 | |
| IV-538 | 444.4 | 2.31 | 1H NMR (500 MHz, Methanol-d4) δ 10.35 (s, 1H), 9.21 (s, 1H), 8.73 (s, 1H), 8.37 (d, J = 6.3 Hz, 1H), 7.74 (s, 1H), 7.11 (s, 1H), 6.81 (d, J = 6.1 Hz, 1H), 5.41 (s, 1H), 4.24 (d, J = 3.7 Hz, 1H), 3.06 (s, 1H), 2.88 (s, 1H), 1.33 (d, J = 6.2 Hz, 3H), 1.05 (s, 3H). |
| IV-539 | 406.1 | 2.4 | 1H NMR (500 MHz, DMSO-d6) δ 10.28 (s, 1H), 9.34 (d, J = 1.2 Hz, 1H), 8.70 (s, 1H), 8.42-8.10 (m, 1H), 7.24 (s, 1H), 6.99-6.73 (m, NH2), 4.08 (d, J = 130.3 Hz, 2H), 3.51 (d, J = 22.7 Hz, 1H), 3.35-3.31 (m, 2H), 2.13 (ddd, J = 13.3, 6.7, 3.7 Hz, 2H), 1.81-1.44 (m, 2H), 1.13 (s, 3H). |
| IV-540 | 401 | 2.49 | |
| IV-541 | 401 | 2.5 | |
| IV-542 | 418.1 | 2.37 | 1H NMR (500 MHz, DMSO-d6) δ 10.23 (d, J = 1.3 Hz, 1H), 9.35 (d, J = 1.3 Hz, 1H), |

TABLE 7-continued

Analytical data for compounds of Formula IV

| IV- | LCMS_Plus | LCMS_RT | NMR |
|---|---|---|---|
| | | | 8.69 (s, 1H), 8.34 (d, J = 6.4 Hz, 1H), 7.74 (s, 1H), 6.93 (d, J = 6.4 Hz, NH), 4.36 (s, 2H), 3.29-3.04 (m, 4H), 1.99-1.74 (m, 4H), 1.59 (td, J = 11.4, 3.9 Hz, 2H). |
| IV-543 | 419.2 | 2.98 | 1H NMR (500 MHz, DMSO-d6) δ 10.25 (d, J = 1.2 Hz, 1H), 9.37 (d, J = 1.3 Hz, 1H), 8.66 (s, 1H), 8.38 (d, J = 6.4 Hz, 1H), 6.87 (d, J = 6.4 Hz, 1H), 3.84 (t, J = 7.8 Hz, 1H), 3.75 (dd, J = 8.4, 3.9 Hz, 1H), 3.69-3.58 (m, 1H), 3.15 (d, J = 11.2 Hz, 1H), 2.99 (dd, J = 13.2, 9.9 Hz, 1H), 2.51, 3H not observed), 2.18-1.95 (m, 2H), 1.84-1.70 (m, 2H), 1.70-1.56 (m, 1H), 1.54-1.32 (m, 3H). |
| IV-544 | 419.2 | 3.02 | 1H NMR (500 MHz, DMSO-d6) δ 10.24 (s, 1H), 9.37 (s, 1H), 8.67 (s, 1H), 8.37 (d, J = 6.3 Hz, 1H), 6.86 (d, J = 6.4 Hz, 1H), 3.94 (t, J = 7.8 Hz, 1H), 3.74 (td, J = 8.3, 3.4 Hz, 1H), 3.62 (dd, J = 8.4, 6.8 Hz, 1H), 3.43 (t, J = 8.1 Hz, 1H), 3.19 (t, J = 12.0 Hz, 1H), 3.06-2.96 (m, 1H), 2.51 (2H not observed), 2.12-1.95 (m, 2H), 1.94-1.71 (m, 2H), 1.62-1.35 (m, 3H), 1.22 (d, J = 6.5 Hz, 1H). |
| IV-545 | 415.3 | 2.68 | 1H NMR (500 MHz, DMSO-d6) δ 12.63 (s, 1H), 10.24 (s, 1H), 9.51-9.25 (m, 1H), 8.69 (s, 1H), 8.38 (d, J = 6.3 Hz, 1H), 7.58 (d, J = 69.0 Hz, 2H), 6.94 (d, J = 6.3 Hz, 1H), 4.89-4.04 (m, 2H), 3.23-3.03 (m, 2H), 2.74 (tt, J = 10.9, 3.9 Hz, 1H), 2.15-2.02 (m, 1H), 1.83 (dt, J = 13.2, 3.5 Hz, 1H), 1.78-1.53 (m, 2H). |
| IV-546 | 415.3 | 2.67 | 1H NMR (500 MHz, DMSO-d6) δ 12.63 (s, 1H), 10.24 (s, 1H), 9.53-9.28 (m, 1H), 8.69 (s, 1H), 8.38 (d, J = 6.3 Hz, 1H), 7.66 (s, 1H), 7.49 (s, 1H), 6.94 (d, J = 6.4 Hz, 1H), 5.08-4.06 (m, 2H), 3.12 (ddd, J = 17.8, 12.3, 9.7 Hz, 2H), 2.74 (tt, J = 10.8, 3.9 Hz, 1H), 2.14-2.03 (m, 1H), 1.89-1.78 (m, 1H), 1.78-1.54 (m, 2H). |
| IV-547 | 416.1 | 2.4 | 1H NMR (500 MHz, DMSO-d6) δ 10.21 (s, 1H), 9.36 (d, J = 1.2 Hz, 1H), 8.72 (s, 1H), 8.63 (s, 1H), 8.42 (d, J = 6.3 Hz, 1H), 8.01 (s, 1H), 6.95 (d, J = 6.3 Hz, 1H), 4.64 (s, 1H), 4.54 (tt, J = 9.5, 4.7 Hz, 1H), 4.31 (s, 1H), 3.65 (dd, J = 13.1, 9.7 Hz, 1H), 3.28 (d, J = 0.9 Hz, 1H), 2.21 (td, J = 9.7, 4.5 Hz, 2H), 1.91 (dt, J = 13.6, 3.9 Hz, 1H), 1.68 (dh, J = 15.1, 4.7 Hz, 1H). |
| IV-548 | 438.3 | 2.88 | 1H NMR (500 MHz, Methanol-d4) δ 10.2 (s, 1H), 9.36 (s, 1H), 8.80 (s, 1H), 8.40 (d, 1H), 8.04 (s, 1H), 7.08 (d, 1H), 6.62 (s, 1H), 4.73 (m, 1H), 4.12 (m, 2H), 2.63 (m, 1H), 2.01 (m, 1H), 1.45-1.30 (m, 1H). |
| IV-549 | 444.4 | 2.31 | |
| IV-550 | 412.25 | 2.73 | 1H NMR (400 MHz, DMSO-d6) δ 10.34 (s, 1H), 9.32 (s, 1H), 8.65 (s, 1H), 8.56-8.49 (m, 2H), 8.34 (d, J = 6.0 Hz, 1H), 7.42-7.35 (m, 2H), 6.54 (d, J = 6.0 Hz, 1H), 4.24 (s, 1H), 3.93 (s, 1H), 3.52 (d, J = 66.1 Hz, 3H), 2.15 (s, 1H), 0.92 (d, J = 6.6 Hz, 1H). |
| IV-551 | 420.2 | 2.32 | 1H NMR (400 MHz, DMSO-d6) δ 10.36 (d, J = 8.3 Hz, 1H), 9.38 (s, 1H), 8.77-8.64 (m, 1H), 8.42 (d, J = 5.9 Hz, 1H), 6.62 (dd, J = 9.1, 6.0 Hz, 1H), 4.36 (s, 3H), 4.10-3.98 (m, 1H), 4.01-3.86 (m, 1H), 3.45 (dq, J = 35.9, 10.5 Hz, 2H), 2.93 (d, J = 12.3 Hz, 3H), 0.96 (d, J = 6.2 Hz, 1H). |
| IV-552 | 412.25 | 2.9 | 1H NMR (400 MHz, DMSO-d6) δ 10.40 (d, J = 7.5 Hz, 1H), 9.36 (s, 1H), 8.68 (s, 1H), 8.56 (ddd, J = 4.8, 1.8, 0.9 Hz, 1H), 8.35 (s, 1H), 7.80 (td, J = 7.7, 1.9 Hz, 1H), 7.44 (d, J = 7.9 Hz, 1H), 7.30 (ddd, J = 7.6, 4.8, 1.2 Hz, 1H), 6.57 (d, J = 5.8 Hz, 1H), 4.21 (s, 1H), 4.00-3.55 (m, 2H), 2.48-2.41 (m, 2H), 2.29 (s, 1H), 0.99-0.90 (m, 1H). |

TABLE 7-continued

Analytical data for compounds of Formula IV

| IV- | LCMS_Plus | LCMS_RT | NMR |
|---|---|---|---|
| IV-553 | 420.25 | 2.5 | 1H NMR (400 MHz, DMSO-d6) δ 10.37 (s, 2H), 9.36 (d, J = 1.3 Hz, 2H), 8.68 (d, J = 10.5 Hz, 2H), 8.34 (d, J = 6.1 Hz, 2H), 6.57-6.48 (m, 2H), 4.04 (s, 1H), 3.72 (s, 1H), 3.23 (d, J = 7.2 Hz, 1H), 2.99 (s, 3H), 2.27 (s, 2H), 1.90 (d, J = 10.3 Hz, 2H). |
| IV-554 | 432.26 | 2.65 | 1H NMR (400 MHz, DMSO-d6) δ 10.36 (d, J = 9.1 Hz, 1H), 9.34 (s, 1H), 8.66 (d, J = 2.0 Hz, 1H), 8.32 (t, J = 5.0 Hz, 1H), 6.49 (s, 1H), 3.94 (d, J = 11.2 Hz, 1H), 3.84 (d, J = 9.2 Hz, 1H), 3.61 (ddd, J = 35.2, 21.6, 9.1 Hz, 2H), 3.35 (d, J = 11.8 Hz, 2H), 2.85 (s, 3H), 2.43 (dd, J = 13.5, 7.1 Hz, 1H), 1.98 (dt, J = 12.6, 7.1 Hz, 1H), 1.94-1.79 (m, 4H). |
| IV-555 | 363.23 | 3.35 | 1H NMR (400 MHz, DMSO-d6) δ 10.42 (s, 1H), 9.36 (s, 1H), 8.66 (s, 1H), 8.32 (d, J = 6.1 Hz, 1H), 6.54-6.45 (m, 1H), 3.86-3.77 (m, 1H), 3.55 (d, J = 9.0 Hz, 1H), 3.40 (dd, J = 18.7, 8.9 Hz, 1H), 3.16 (d, J = 10.0 Hz, 1H), 2.44 (s, 2H), 1.00 (d, J = 6.4 Hz, 6H). |
| IV-556 | 411.25 | 3.42 | 1H NMR (400 MHz, DMSO-d6) δ 10.32 (d, J = 7.2 Hz, 1H), 9.27 (s, 1H), 8.60 (s, 1H), 8.27 (s, 1H), 7.35-7.24 (m, 4H), 7.19 (s, 1H), 6.47 (d, J = 19.0 Hz, 1H), 4.19 (s, 1H), 3.89 (d, J = 24.4 Hz, 1H), 3.61 (s, 1H), 3.51 (s, 2H), 3.35 (d, J = 11.1 Hz, 1H), 2.08 (d, J = 10.1 Hz, 1H). |
| IV-557 | 432.26 | 2.53 | 1H NMR (400 MHz, DMSO-d6) δ 10.32 (s, 1H), 9.34 (d, J = 1.3 Hz, 1H), 8.63 (s, 1H), 8.30 (d, J = 6.1 Hz, 1H), 6.47 (s, 1H), 3.79 (s, 1H), 3.53 (d, J = 7.5 Hz, 1H), 3.49-3.36 (m, 2H), 3.29 (dd, J = 7.5, 2.1 Hz, 2H), 3.12 (s, 1H), 2.68 (s, 1H), 2.26 (t, J = 8.4 Hz, 2H), 2.13 (s, 1H), 1.97 (tt, J = 8.3, 4.3 Hz, 2H), 1.77 (d, J = 5.4 Hz, 1H). 1 proton obscured by solvent peak |
| IV-558 | 484.1 | 2.57 | 1H NMR (500 MHz, DMSO-d6) δ 12.76 (s, 1H), 10.17 (t, J = 1.1 Hz, 1H), 9.47-9.21 (m, 1H), 8.69 (s, 1H), 8.46 (d, J = 6.2 Hz, 1H), 7.79 (s, 1H), 7.60 (s, 1H), 7.06 (d, J = 6.3 Hz, 1H), 4.76 (s, 1H), 3.95 (dt, J = 11.2, 3.9 Hz, 1H), 3.70 (s, 1H), 3.11 (dt, J = 10.5, 7.9 Hz, 2H), 3.02 (t, J = 12.0 Hz, 1H). |
| IV-559 | 441.26 | 3.46 | 1H NMR (400 MHz, DMSO-d6) δ 10.41 (s, 1H), 9.36 (s, 1H), 8.67 (s, 1H), 8.35 (d, J = 6.1 Hz, 1H), 7.36-7.25 (m, 2H), 7.02-6.90 (m, 3H), 6.54 (d, J = 6.1 Hz, 1H), 4.12 (s, 1H), 4.02 (d, J = 11.5 Hz, 1H), 3.89 (s, 1H), 3.70 (s, 1H), 3.60 (s, 1H), 3.50 (s, 1H), 2.88 (s, 1H), 2.26 (s, 1H), 1.97 (s, 1H). |
| IV-560 | 419.3 | 2.02 | 1H NMR (400 MHz, DMSO-d6) δ 10.55 (s, 1H), 10.34 (d, J = 19.5 Hz, 1H), 9.37 (s, 1H), 8.71 (s, 1H), 8.54 (s, 1H), 8.41 (s, 1H), 6.61 (s, 1H), 3.99-3.87 (m, 2H), 3.75 (s, 2H), 3.65 (d, J = 14.0 Hz, 1H), 2.25 (s, 1H). |
| IV-561 | 425.31 | 3.58 | 1H NMR (400 MHz, DMSO-d6) δ 10.34 (d, J = 36.2 Hz, 1H), 9.37 (s, 1H), 8.67 (s, 1H), 8.36 (d, J = 25.9 Hz, 1H), 7.35-7.23 (m, 5H), 6.59 (d, J = 41.0 Hz, 1H), 4.65 (s, 1H), 3.71 (d, J = 33.3 Hz, 1H), 3.44 (s, 1H), 3.13 (d, J = 13.0 Hz, 1H), 2.83 (s, 1H), 2.71 (s, 1H), 1.96-1.83 (m, 4H). |
| IV-562 | 419 | 2.73 | 1H NMR (500 MHz, DMSO-d6) δ 12.29 (br s, 1H), 10.40 (s, 1H), 9.36 (s, 1H), 8.68 (s, 1H), 8.36 (d, J = 6.0 Hz, 1H), 7.66 (s, 1H), 6.55 (d, J = 6.0 Hz, 1H), 4.19-3.32 (m, 5H), 2.41 (br s, 1H), 2.08 (brs, 1H). |
| IV-563 | 419 | 2.74 | 1H NMR (500 MHz, DMSO-d6) δ 12.29 (br s, 1H), 10.40 (s, 1H), 9.36 (s, 1H), 8.68 (s, 1H), 8.36 (d, J = 6.0 Hz, 1H), 7.66 (s, 1H), 6.55 (d, J = 6.0 Hz, 1H), 4.19-3.32 (m, 5H), 2.41 (br s, 1H), 2.08 (brs, 1H). |
| IV-564 | 401.25 | 2.38 | 1H NMR (400 MHz, DMSO-d6) δ 10.34 (s, 1H), 9.36 (s, 1H), 8.70 (s, 1H), 8.40 (d, J = |

TABLE 7-continued

Analytical data for compounds of Formula IV

| IV- | LCMS_Plus | LCMS_RT | NMR |
|---|---|---|---|
|  |  |  | 6.0 Hz, 1H), 7.80 (t, J = 1.2 Hz, 1H), 7.33 (s, 1H), 6.96 (s, 1H), 6.60 (d, J = 6.1 Hz, 1H), 5.11 (s, 1H), 4.24 (s, 1H), 4.02-3.75 (m, 2H), 3.65 (d, J = 37.0 Hz, 2H), 2.59 (s, 1H). |
| IV-565 | 434.26 | 2.31 | 1H NMR (400 MHz, DMSO-d6) δ 10.33 (s, 1H), 9.35 (d, J = 1.2 Hz, 1H), 8.67 (s, 1H), 8.35 (d, J = 6.0 Hz, 1H), 6.55 (d, J = 6.1 Hz, 1H), 5.76 (s, 1H), 4.21 (d, J = 17.0 Hz, 1H), 4.14 (d, J = 17.0 Hz, 1H), 3.99 (d, J = 12.0 Hz, 1H), 3.88 (s, 1H), 3.77-3.61 (m, 1H), 3.57 (s, 2H), 2.93 (s, 3H), 2.38 (s, 1H), 2.17 (s, 1H). |
| IV-566 | 421.3 | 2.31 | 1H NMR (400 MHz, DMSO-d6) δ 10.25 (d, J = 12.8 Hz, 1H), 9.35 (d, J = 1.4 Hz, 1H), 8.67 (s, 1H), 8.35 (d, J = 6.2 Hz, 1H), 7.19 (s, 1H), 7.09 (s, 1H), 6.72 (s, 1H), 5.76 (s, 1H), 3.98 (d, J = 20.8 Hz, 2H), 3.67 (s, 2H), 3.04 (s, 2H), 2.85 (s, 2H), 2.66 (s, 1H), 1.94 (dd, J = 8.4, 3.3 Hz, 2H). |
| IV-567 | 478.3 | 2.83 | 1H NMR (500 MHz, DMSO-d6) δ 12.67 (s, 1H), 10.12-10.00 (m, 1H), 9.40 (m, 1H), 8.73 (m, 1H), 7.72-7.56 (m, 2H), 7.11-7.03 (m, 1H), 4.94-4.60 (m, 1H), 4.30-4.03 (m, 2H), 2.94 (m, 1H), 2.80-2.71 (m, 1H), 2.62 (m, 1H), 1.15 (m, 3H), 0.97-0.90 (m, 3H). |
| IV-568 | 419.1 | 2.15 | 1H NMR (500 MHz, DMSO-d6) δ 10.22 (s, 1H), 9.37 (d, J = 1.3 Hz, 1H), 8.66 (s, 1H), 8.44 (d, J = 6.3 Hz, 1H), 7.88 (s, NH), 6.88 (d, J = 6.4 Hz, 1H), 3.36 (td, J = 13.3, 12.5, 5.6 Hz, 2H), 3.22-3.08 (m, 2H), 3.06-2.88 (m, 3H), 2.69 (d, J = 9.3 Hz, 1H), 2.50 (d, J = 1.9 Hz, 2H), 2.34-2.24 (m, 1H). |
| IV-569 | 434.3 | 2.87 | 1H NMR (500 MHz, DMSO-d6) δ 10.38 (s, 1H), 9.36 (s, 1H), 8.69 (d, J = 22.1 Hz, 1H), 8.35 (t, J = 5.8 Hz, 1H), 6.54 (dd, J = 24.7, 6.2 Hz, 1H), 3.99 (d, J = 9.8 Hz, 1H), 3.79-3.55 (m, 5H), 3.26 (t, J = 11.1 Hz, 3H), 2.91-2.77 (m, 1H), 2.61-2.56 (m, 1H), 2.50-2.39 (m, 3H), 0.96 (t, J = 6.6 Hz, 3H). |
| IV-570 | 425.21 | 2.36 | 1H NMR (400 MHz, DMSO-d6) δ 10.34 (d, J = 1.2 Hz, 1H), 9.37 (d, J = 1.3 Hz, 1H), 8.70 (s, 1H), 8.42 (d, J = 6.1 Hz, 1H), 6.63 (s, 1H), 3.92 (d, J = 5.7 Hz, 3H), 3.60 (s, 2H), 3.52 (s, 1H), 3.29-3.20 (m, 2H), 2.42-2.28 (m, 1H), 2.03 (ddd, J = 19.7, 12.6, 6.3 Hz, 1H). |
| IV-571 | 418.3 | 2.66 | 1H NMR (400 MHz, DMSO-d6) δ 10.23 (t, J = 1.0 Hz, 1H), 9.37 (d, J = 1.3 Hz, 1H), 8.76 (s, 1H), 8.45 (d, J = 6.2 Hz, 1H), 6.96 (d, J = 6.3 Hz, 1H), 4.51-4.42 (m, 2H), 4.34 (s, 1H), 4.23 (d, J = 17.5 Hz, 1H), 3.63 (dd, J = 13.6, 7.6 Hz, 1H), 3.58-3.50 (m, 1H), 1.83 (t, J = 12.5 Hz, 2H), 1.68 (d, J = 13.3 Hz, 1H), 1.50 (tdd, J = 12.9, 9.5, 3.7 Hz, 1H), 1.36-1.21 (m, 1H), 1.26 (s, 1H), 0.99-0.90 (m, 1H). |
| IV-572 | 469 | 3.03 |  |
| IV-573 | 431 | 2.32 |  |
| IV-574 | 429 | 2.72 |  |
| IV-575 | 415 | 2.66 |  |
| IV-576 | 441 | 2.86 |  |
| IV-577 | 444.3 | 2.33 | 1H NMR (500 MHz, Methanol-d4) δ 10.17 (s, 1H), 9.21 (s, 1H), 8.65 (s, 1H), 8.52 (s, 1H), 8.28 (s, 1H), 7.71 (s, 2H), 4.67 (m, 1H), 4.38 (m, 1H), 4.24 (m, 1H), 3.16 (m, 1H), 2.93 (m, 1H), 1.34 (d, 3H), 1.14 (d, 3H). |
| IV-578 | 473.3 | 2.59 | 1H NMR (500 MHz, DMSO-d6) δ 12.80 (s, 1H), 10.31 (s, 1H), 9.32 (s, 1H), 8.63 (s, 1H), 7.60 (s, 2H), 7.02 (s, 1H), 5.66 (s, 1H), 4.80-4.20 (br m, 2H), 3.30 (masked, 3H), 2.89 (m, 3H), 2.52 (s, 1H), 1.34 (d, 3H), 1.14 (d, 3H). |

TABLE 7-continued

Analytical data for compounds of Formula IV

| IV- | LCMS_Plus | LCMS_RT | NMR |
|---|---|---|---|
| IV-579 | 420.3 | 2.37 | |
| IV-580 | 405.35 | 2.83 | 1H NMR (400 MHz, DMSO-d6) δ 10.42 (d, J = 5.3 Hz, 1H), 9.40 (s, 1H), 8.70 (s, 1H), 8.35 (dd, J = 6.1, 1.4 Hz, 1H), 6.52 (d, J = 6.3 Hz, 1H), 4.02 (s, 1H), 3.93-3.69 (m, 4H), 3.64-3.43 (m, 3H), 2.26 (s, 4H), 2.07 (dd, J = 11.9, 4.8 Hz, 1H), 1.78-1.64 (m, 1H). |
| IV-581 | 392.1 | 2.25 | 1H NMR (500 MHz, DMSO-d6) δ 10.39 (s, 1H), 9.36 (d, J = 1.2 Hz, 1H), 8.67 (s, 1H), 8.34 (d, J = 6.1 Hz, 1H), 7.42 (s, NH), 7.07 (s, NH), 6.50 (d, J = 6.1 Hz, 1H), 3.99 (dd, J = 131.5, 10.7 Hz, 1H), 3.74 (d, J = 35.5 Hz, 1H), 3.61-3.39 (m, 1H), 3.23 (d, J = 10.3 Hz, 1H), 2.48-2.37 (m, 1H), 1.97 (d, J = 8.7 Hz, 1H), 1.35 (s, 3H). |
| IV-582 | 428.1 | 2.39 | 1H NMR (500 MHz, DMSO-d6) δ 10.20 (d, J = 1.2 Hz, 1H), 9.38 (d, J = 1.3 Hz, 1H), 8.76 (s, 1H), 8.49 (d, J = 6.3 Hz, 1H), 7.64 (s, NH), 7.16 (s, NH), 7.08 (d, J = 6.3 Hz, 1H), 3.55 (dd, J = 32.3, 13.9 Hz, 1H), 3.21 (t, J = 12.6 Hz, 1H), 2.77-2.61 (m, 1H), 2.45-2.16 (m, 3H). |
| IV-583 | 443.3 | 2.63 | 1H NMR (500 MHz, DMSO-d6) δ 12.63 (s, 1H), 10.20 (m, 1H), 9.31 (m, 1H), 8.70 (m, 1H), 7.77-7.44 (m, 3H), 6.97 (m, 1H), 4.80-4.45 (m, 1H), 4.45-4.10 (m, 2H), 2.98 (m, 1H), 2.71 (m, 1H), 2.51 (masked, 1H), 1.19 (m, 3H), 0.99 (m, 3H). |
| IV-584 | 433.1 | 2.42 | 1H NMR (500 MHz, DMSO-d6) δ 10.24 (s, 1H), 9.36 (d, J = 1.3 Hz, 1H), 8.71 (s, 1H), 8.40 (d, J = 6.3 Hz, 1H), 6.87 (d, J = 6.3 Hz, 1H), 6.37 (s, NH), 3.64-3.51 (m, 1H), 3.48-3.38 (m, 2H), 3.26 (t, J = 8.3 Hz, 3H), 3.14 (d, J = 12.2 Hz, 1H), 3.01 (t, J = 12.3 Hz, 1H), 2.50 (2H not observed), 1.90-1.76 (m, 4H), 1.56 (s, 1H). |
| IV-585 | 364.1 | 2.51 | 1H NMR (500 MHz, DMSO-d6) δ 10.26 (s, 1H), 9.36 (d, J = 1.2 Hz, 1H), 8.71 (s, 1H), 8.41 (d, J = 6.3 Hz, 1H), 6.87 (d, J = 6.3 Hz, 1H), 3.75 (s, 4H), 2.46-2.40 (m, 4H), 2.25 (s, 3H). |
| IV-586 | 409.2 | 2.74 | 1H NMR (500 MHz, DMSO-d6) δ 10.25 (dd, J = 1.5, 0.7 Hz, 1H), 9.37 (d, J = 1.2 Hz, 1H), 8.73 (s, 1H), 8.41 (d, J = 6.3 Hz, 1H), 6.84 (d, J = 6.3 Hz, 1H), 4.05 (t, J = 5.1 Hz, 2H), 3.88-3.65 (m, 2H), 3.57-3.40 (m, 2H), 3.37 (dd, J = 13.2, 7.5 Hz, 2H), 3.26 (s, 3H), 1.18 (d, J = 6.3 Hz, 3H). |
| IV-587 | 409.1 | 2.81 | 1H NMR (500 MHz, DMSO-d6) δ 10.24 (s, 1H), 9.37 (d, J = 1.3 Hz, 1H), 8.74 (s, 1H), 8.43 (d, J = 6.2 Hz, 1H), 6.89 (d, J = 6.3 Hz, 1H), 3.80-3.61 (m, 2H), 3.48 (dd, J = 4.8, 3.8 Hz, 2H), 3.32 (s, 3H), 3.31-3.26 (m, 2H), 2.76 (dt, J = 65.6, 11.9 Hz, 2H), 1.22 (d, J = 6.2 Hz, 3H). |
| IV-588 | 395.1 | 2.61 | 1H NMR (500 MHz, DMSO-d6) δ 10.24 (s, 1H), 9.37 (d, J = 1.3 Hz, 1H), 8.73 (s, 1H), 8.44 (d, J = 6.2 Hz, 1H), 6.88 (d, J = 6.3 Hz, 1H), 4.28 (s, 2H), 4.07-3.92 (m, 1H), 3.68 (ddd, J = 10.5, 7.7, 4.8 Hz, 1H), 3.59 (td, J = 11.6, 2.9 Hz, 1H), 3.52-3.44 (m, 2H), 3.32 (s, 3H), 3.21-3.06 (m, 1H), 2.93 (dd, J = 13.1, 10.7 Hz, 1H). |
| IV-589 | 415.1 | 2.71 | |
| IV-590 | 491.1 | 2.01 | |
| IV-591 | 491.1 | 2.01 | |
| IV-592 | 491.1 | 2.05 | |
| IV-593 | 474.3 | 2.72 | 1H NMR (500 MHz, Methanol-d4) δ 10.30 (s, 1H), 9.20 (s, 1H), 8.67 (s, 1H), 7.74 (s, 2H), 6.08 (s, 1H), 5.00-4.80 (masked, 2H), 4.39 (m, 1H), 4.06 (s, 3H), 3.15 (m, 1H), 2.90 (m, 1H), 1.35 (d, 3H), 1.14 (d, 3H). |
| IV-594 | 395.1 | 3.13 | 1H NMR (500 MHz, DMSO-d6) δ 10.37 (s, 1H), 9.35 (d, J = 1.3 Hz, 1H), 8.65 (s, 1H), 8.32 (d, J = 6.1 Hz, 1H), 6.50 (d, J = 5.9 |

TABLE 7-continued

Analytical data for compounds of Formula IV

| IV- | LCMS_Plus | LCMS_RT | NMR |
|---|---|---|---|
| | | | Hz, 1H), 3.88 (d, J = 43.5 Hz, 1H), 3.64 (s, 1H), 3.55 (s, 1H), 3.42 (s, 1H), 2.72-2.60 (m, 3H), 2.22 (s, 1H), 2.13 (s, 3H), 1.83 (s, 1H). |
| IV-595 | 393.1 | 1.98 | 1H NMR (500 MHz, DMSO-d6) δ 10.22 (s, 1H), 9.35 (d, J = 1.3 Hz, 1H), 8.67 (s, 1H), 8.38 (d, J = 6.3 Hz, 1H), 7.49-7.33 (NH), 7.29-7.14 (NH), 6.84 (d, J = 6.4 Hz, 1H), 4.09 (d, J = 77.0 Hz, 2H), 3.42-3.31 (m, 2H), 2.99 (dt, J = 12.7, 3.8 Hz, 1H), 2.82-2.65 (m, 2H). |
| IV-596 | 407.1 | 2.11 | 1H NMR (500 MHz, DMSO-d6) δ 10.21 (d, J = 1.4 Hz, 1H), 9.36 (d, J = 1.3 Hz, 1H), 8.68 (d, J = 0.9 Hz, 1H), 8.41 (dd, J = 6.3, 0.7 Hz, 1H), 7.59-7.39 (NH), 7.27-7.16 (NH), 6.90 (d, J = 6.3 Hz, 1H), 4.32 (s, 2H), 3.30-3.21 (m, 2H), 2.98 (dt, J = 11.7, 3.2 Hz, 1H), 2.62 (dd, J = 9.9, 3.5 Hz, 1H), 2.24 (s, 3H), 2.21 (dd, J = 11.4, 3.3 Hz, 1H). |
| IV-597 | 362.9 | 3.29 | 1H NMR (400 MHz, DMSO-d6) δ 10.24 (t, J = 1.1 Hz, 1H), 9.36 (d, J = 1.3 Hz, 1H), 8.67 (s, 1H), 8.35 (d, J = 6.3 Hz, 1H), 6.81 (d, J = 6.4 Hz, 1H), 4.81 (s, 1H), 4.34 (d, J = 13.4 Hz, 1H), 3.07 (td, J = 13.1, 2.9 Hz, 1H), 1.83-1.62 (m, 3H), 1.62 (s, 1H), 1.46 (dd, J = 12.5, 4.6 Hz, 1H), 1.24 (d, J = 6.8 Hz, 3H). 1 proton obscured by solvent peaks |
| IV-598 | 378.1 | 2.06 | 1H NMR (500 MHz, DMSO-d6) δ 10.39 (d, J = 1.3 Hz, 1H), 9.36 (d, J = 1.3 Hz, 1H), 8.68 (s, 1H), 8.35 (d, J = 6.0 Hz, 1H), 7.55 (s, 1H), 7.04 (s, NH), 6.53 (s, NH), 3.97-3.37 (m, 4H), 3.19-3.06 (m, 1H), 2.27 (dt, J = 13.1, 6.2 Hz, 1H), 2.14 (s, 1H). |
| IV-599 | | | 1H NMR (500 MHz, DMSO-d6) δ 10.23 (d, J = 1.3 Hz, 1H), 9.37 (d, J = 1.3 Hz, 1H), 8.70 (s, 1H), 8.46 (d, J = 6.3 Hz, 1H), 7.40 (d, J = 18.8 Hz, NH2), 6.91 (d, J = 6.4 Hz, 1H), 4.34 (d, J = 95.6 Hz, 2H), 4.11-3.98 (m, 2H), 3.70 (td, J = 11.2, 2.9 Hz, 1H), 3.32-3.31 (m, 1H), 3.27-3.15 (m, 1H). |
| IV-600 | 416.1 | 2.46 | 1H NMR (500 MHz, DMSO-d6) δ 10.19 (s, 1H), 9.35 (d, J = 1.2 Hz, 1H), 8.70 (s, 1H), 8.42 (d, J = 6.3 Hz, 1H), 8.26 (d, J = 1.1 Hz, 1H), 7.75 (d, J = 1.0 Hz, 1H), 6.96 (d, J = 6.4 Hz, 1H), 4.73 (dq, J = 9.2, 4.7, 4.3 Hz, 1H), 4.32 (s, 1H), 3.74 (dd, J = 13.0, 9.7 Hz, 1H), 3.40-3.32 (m, 1H), 2.33-2.18 (m, 3H), 1.97-1.87 (m, 1H), 1.70 (s, 1H). |
| IV-601 | 449 | 2.87 | 1H NMR (500 MHz, DMSO-d6) δ 10.19 (s, 1H), 9.35 (d, J = 1.3 Hz, 1H), 8.70 (s, 1H), 8.42 (d, J = 6.3 Hz, 1H), 8.26 (d, J = 1.1 Hz, 1H), 7.75 (d, J = 1.0 Hz, 1H), 6.96 (d, J = 6.4 Hz, 1H), 4.73 (tt, J = 9.3, 4.5 Hz, 1H), 3.74 (dd, J = 13.1, 9.7 Hz, 1H), 3.40-3.30 (m, 4H), 3.27 (s, 6H), 2.29-2.19 (m, 2H), 1.92 (dt, J = 13.5, 4.1 Hz, 1H), 1.72 (td, J = 10.2, 5.2 Hz, 1H). |
| IV-602 | 433.1 | 2.07 | 1H NMR (500 MHz, DMSO-d6) δ 10.38 (dd, J = 1.3, 0.7 Hz, 1H), 9.36 (d, J = 1.3 Hz, 1H), 8.75-8.61 (m, 1H), 8.35 (d, J = 6.1 Hz, 1H), 7.80 (d, J = 2.1 Hz, 1H), 6.64-6.51 (m, 1H), 4.00 (d, J = 73.3 Hz, 1H), 3.78-3.58 (m, 2H), 3.41 (d, J = 10.0 Hz, 2H), 3.21 (s, 2H), 3.08 (s, 2H), 2.77-2.66 (m, 2H), 2.30 (s, 1H), 1.92 (d, J = 17.4 Hz, 1H). |
| IV-603 | 411 | 2.13 | 1H NMR (500 MHz, Methanol-d4) δ 10.40 (s, 1H), 9.10 (dd, J = 1.4, 0.8 Hz, 1H), 8.56 (d, J = 1.7 Hz, 1H), 8.19 (d, J = 6.2 Hz, 1H), 6.38 (dd, J = 6.2, 4.5 Hz, 1H), 3.98 (d, J = 91.0 Hz, 1H), 3.71 (s, 1H), 3.45 (s, 2H), 2.95 (d, J = 6.4 Hz, 2H), 2.82 (s, 1H), 2.63 (s, 3H), 2.35 (s, 1H), 1.92 (s, 1H). |
| IV-604 | 427.1 | 2.33 | 1H NMR (500 MHz, Methanol-d4) δ 10.40 (s, 1H), 9.10 (dd, J = 1.4, 0.8 Hz, 1H), 8.56 |

TABLE 7-continued

Analytical data for compounds of Formula IV

| IV- | LCMS_Plus | LCMS_RT | NMR |
|---|---|---|---|
| | | | (d, J = 1.7 Hz, 1H), 8.19 (d, J = 6.2 Hz, 1H), 6.38 (dd, J = 6.2, 4.5 Hz, 1H), 3.98 (d, J = 91.0 Hz, 1H), 3.71 (s, 1H), 3.45 (s, 2H), 2.95 (d, J = 6.4 Hz, 2H), 2.82 (s, 1H), 2.63 (s, 3H), 2.35 (s, 1H), 1.92 (s, 1H). |
| IV-605 | 406.1 | 2.23 | 1H NMR (500 MHz, DMSO-d6) δ 10.26 (dt, J = 1.6, 0.8 Hz, 1H), 9.36 (dd, J = 1.4, 0.7 Hz, 1H), 8.69 (s, 1H), 8.36 (d, J = 6.3 Hz, 1H), 7.29-7.25 (m, 1H), 6.85 (d, J = 6.4 Hz, 1H), 6.77 (s, 1H), 4.46 (s, 2H), 3.10-3.01 (m, 2H), 2.04 (d, J = 2.9 Hz, 3H), 1.83-1.76 (m, 2H), 1.25-1.13 (m, 2H). |
| IV-606 | 416 | 2.16 | |
| IV-607 | 426.1 | 2.01 | 1H NMR (500 MHz, Methanol-d4) δ 10.47 (s, 1H), 9.20 (d, J = 1.3 Hz, 1H), 8.68-8.63 (m, 1H), 8.29 (d, J = 6.1 Hz, 1H), 6.50-6.44 (m, 1H), 4.88-4.79 (m, 1H), 4.10 (d, J = 111.6 Hz, 1H), 3.88 (s, 1H), 3.70 (s, 1H), 3.65 (s, 1H), 3.54 (s, 2H), 3.14 (s, 3H), 3.02 (s, 1H), 2.48 (s, 1H), 2.04 (dd, J = 17.6, 9.7 Hz, 1H). |
| IV-608 | 405.2 | 2.79 | 1H NMR (500 MHz, DMSO-d6) δ 10.43 (s, 1H), 9.37 (d, J = 1.2 Hz, 1H), 8.69 (s, 1H), 8.34 (d, J = 6.1 Hz, 1H), 6.52 (s, 1H), 3.83 (d, J = 32.9 Hz, 2H), 3.63 (d, J = 47.1 Hz, 2H), 3.43 (t, J = 7.6 Hz, 2H), 2.51 (4H not observed), 2.25-2.00 (m, 2H), 1.65 (s, 2H). |
| IV-609 | 405.2 | 2.83 | 1H NMR (500 MHz, DMSO-d6) δ 10.41 (s, 1H), 9.37 (d, J = 1.2 Hz, 1H), 8.68 (s, 1H), 8.33 (s, 1H), 6.51 (d, J = 6.1 Hz, 1H), 3.98-3.75 (m, 3H), 3.63 (d, J = 40.6 Hz, 2H), 3.45-3.38 (m, 1H), 2.26-2.14 (m, 4H), 1.90-1.72 (m, 2H), 1.71-1.57 (m, 2H). |
| IV-610 | 377.1 | 3.53 | 1H NMR (500 MHz, DMSO-d6) δ 10.30 (s, 1H), 9.36 (d, J = 1.4 Hz, 1H), 8.61 (s, 1H), 8.32 (s, 1H), 6.47 (d, J = 40.3 Hz, 1H), 3.70-3.58 (m, 1H), 3.08-2.94 (m, 1H), 2.46-2.36 (m, 2H), 2.16-2.00 (m, 1H), 1.65 (d, J = 52.4 Hz, 6H), 1.11 (d, J = 6.4 Hz, 3H). |
| IV-611 | 392.1 | 2.13 | 1H NMR (500 MHz, DMSO-d6) δ 10.26 (d, J = 1.2 Hz, 1H), 9.36 (d, J = 1.3 Hz, 1H), 8.70 (s, 1H), 8.39 (d, J = 6.3 Hz, 1H), 7.33 (NH), 6.88 (d, J = 6.4 Hz, 1H), 6.82 (NH), 4.62-4.39 (m, 2H), 3.11 (t, J = 12.2 Hz, 2H), 2.53-2.52 (m, 1H), 1.85 (d, J = 13.3 Hz, 2H), 1.65-1.51 (m, 2H). |
| IV-612 | 393.1 | 2.07 | 1H NMR (500 MHz, DMSO-d6) δ 10.38 (s, 1H), 9.36 (d, J = 1.2 Hz, 1H), 8.69 (d, J = 22.1 Hz, 1H), 8.35 (t, J = 5.8 Hz, 1H), 6.54 (dd, J = 24.7, 6.1 Hz, 1H), 3.75-3.56 (m, 4H), 0.96 (t, J = 6.6 Hz, 4H). |
| IV-613 | 395.1 | 2.32 | 1H NMR (500 MHz, DMSO-d6) δ 10.23 (d, J = 1.2 Hz, 1H), 9.37 (d, J = 1.6 Hz, 1H), 8.72 (s, 1H), 8.43 (d, J = 6.3 Hz, 1H), 6.94-6.74 (m, 1H), 4.86 (t, J = 5.6 Hz, 1H), 3.88-3.69 (m, 2H), 3.61-3.47 (m, 4H), 3.18 (d, J = 5.2 Hz, 1H), 1.28 (dd, J = 20.6, 6.7 Hz, 3H). |
| IV-614 | 392.3 | 2.22 | 1H NMR (500 MHz, DMSO-d6) δ 10.34 (s, 1H), 9.36 (d, J = 1.2 Hz, 1H), 8.67 (s, 1H), 8.34 (d, J = 6.0 Hz, 1H), 7.52 (s, 1H), 6.94 (s, 1H), 3.59-3.49 (m, 1H), 2.86-2.77 (m, 1H), 2.51 (2H, not observed), 2.33 (dd, J = 12.9, 7.7 Hz, 1H), 2.19-2.08 (m, 1H), 1.32 (d, J = 71.8 Hz, 3H). |
| IV-615 | 392.3 | 2.13 | 1H NMR (500 MHz, DMSO-d6) δ 10.40 (s, 1H), 9.35 (d, J = 1.4 Hz, 1H), 8.66 (s, 1H), 8.31 (d, J = 6.1 Hz, 1H), 6.48 (d, J = 7.5 Hz, 1H), 4.43 (t, J = 5.1 Hz, 1H), 4.04-3.76 (m, 1H), 3.74-3.33 (m, 4H), 3.09 (t, J = 9.4 Hz, 0.5H), 3.00 (t, J = 9.4 Hz, 0.5H), 2.32 (br s, 1H), 2.19 (br s, 1H), 1.66 (br s, 1H), 1.51, (br s, 4H). NB Rotameric signals evident. |
| IV-616 | 393 | 2.54 | 1H NMR (500 MHz, DMSO-d6) δ 10.40 (s, 1H), 9.35 (d, J = 1.4 Hz, 1H), 8.66 (s, 1H), |

TABLE 7-continued

Analytical data for compounds of Formula IV

| IV- | LCMS_Plus | LCMS_RT | NMR |
|---|---|---|---|
| | | | 8.31 (d, J = 6.1 Hz, 1H), 6.48 (d, J = 7.5 Hz, 1H), 4.43 (t, J = 5.1 Hz, 1H), 4.04-3.76 (m, 1H), 3.74-3.33 (m, 4H), 3.09 (t, J = 9.4 Hz, 0.5H), 3.00 (t, J = 9.4 Hz, 0.5H), 2.32 (br s, 1H), 2.19 (br s, 1H), 1.66 (br s, 1H), 1.51, (br s, 4H). NB Rotameric signals evident. |
| IV-617 | 394.1 | 2.17 | |
| IV-618 | 408.1 | 2.08 | 1H NMR (500 MHz, DMSO-d6) δ 10.24 (dd, J = 1.4, 0.8 Hz, 1H), 9.36 (dd, J = 1.2, 0.6 Hz, 1H), 8.72 (s, 1H), 8.44 (d, J = 6.2 Hz, 1H), 6.88 (d, J = 6.3 Hz, 1H), 4.70 (t, J = 5.5 Hz, 1H), 4.18 (d, J = 5.6 Hz, 2H), 3.80 (s, 4H), 3.64 (s, 2H), 3.55 (d, J = 5.7 Hz, 2H). |
| IV-619 | 422.2 | 2.71 | |
| IV-620 | 403.1 | 2.51 | 1H NMR (500 MHz, DMSO-d6) δ 10.25 (dt, J = 1.6, 0.8 Hz, 1H), 9.38-9.34 (m, 1H), 8.71 (s, 1H), 8.41 (d, J = 6.3 Hz, 1H), 6.88 (d, J = 6.3 Hz, 1H), 3.83-3.71 (m, 4H), 2.75 (td, J = 6.6, 1.0 Hz, 2H), 2.67 (td, J = 6.5, 1.0 Hz, 2H), 2.58 (t, J = 5.2 Hz, 4H). |
| IV-621 | 431.3 | 2.11 | 1H NMR (500 MHz, DMSO-d6) δ 12.58 (s, 1H), 10.22 (s, 1H), 9.35 (s, 1H), 8.69 (s, 1H), 8.38 (d, J = 6.3 Hz, 1H), 7.56 (s, 2H), 6.94 (d, J = 6.4 Hz, 1H), 4.80 (d, J = 5.5 Hz, 1H), 4.40 (br s, 2H), 3.73 (tt, J = 9.4, 4.4 Hz, 1H), 3.30-3.27 (m, 2H), 2.58 (td, J = 9.9, 4.4 Hz, 1H), 1.99 (dd, J = 13.0, 4.0 Hz, 1H), 1.52-1.45 (m, 1H). |
| IV-622 | 431.3 | 2.1 | 1H NMR (500 MHz, DMSO-d6) δ 12.58 (s, 1H), 10.22 (s, 1H), 9.36 (s, 1H), 8.69 (s, 1H), 8.38 (d, J = 6.3 Hz, 1H), 7.56 (br d, J = 67.6 Hz, 2H), 6.94 (d, J = 6.3 Hz, 1H), 4.80 (d, J = 5.6 Hz, 1H), 4.42 (br s, 2H), 3.76-3.70 (m, 1H), 3.28-3.25 (m, 2H), 2.58 (td, J = 9.3, 4.2 Hz, 1H), 1.99 (dd, J = 13.1, 3.9 Hz, 1H), 1.53-1.45 (m, 1H). |
| IV-623 | 431.3 | 2.15 | 1H NMR (500 MHz, DMSO-d6) δ 10.24 (s, 1H), 9.36 (d, J = 1.3 Hz, 1H), 8.70 (s, 1H), 8.38 (d, J = 6.3 Hz, 1H), 7.40 (NH) 6.90 (d, J = 6.5 Hz, 1H + NH), 4.42 (s, 2H), 3.24-2.99 (m, 2H), 2.37 (td, J = 3.6, 1.4 Hz, 1H), 1.94 (d, J = 11.7 Hz, 1H), 1.86-1.63 (m, 2H), 1.50 (t, J = 12.3 Hz, 1H). |
| IV-624 | 431.3 | 2.15 | 1H NMR (500 MHz, DMSO-d6) δ 10.24 (s, 1H), 9.36 (d, J = 1.3 Hz, 1H), 8.70 (s, 1H), 8.38 (d, J = 6.3 Hz, 1H), 7.40 (NH) 6.90 (d, J = 6.5 Hz, 1H + NH), 4.42 (s, 2H), 3.24-2.99 (m, 2H), 2.37 (td, J = 3.6, 1.4 Hz, 1H), 1.94 (d, J = 11.7 Hz, 1H), 1.86-1.63 (m, 2H), 1.50 (t, J = 12.3 Hz, 1H). |
| IV-625 | 392.1 | 2.2 | |
| IV-626 | 392.1 | 2.2 | 1H NMR (500 MHz, DMSO-d6) δ 10.24 (s, 1H), 9.36 (d, J = 1.3 Hz, 1H), 8.70 (s, 1H), 8.38 (d, J = 6.3 Hz, 1H), 7.40 (NH) 6.90 (d, J = 6.5 Hz, 1H + NH), 4.42 (s, 2H), 3.24-2.99 (m, 2H), 2.37 (td, J = 3.6, 1.4 Hz, 1H), 1.94 (d, J = 11.7 Hz, 1H), 1.86-1.63 (m, 2H), 1.50 (t, J = 12.3 Hz, 1H). |
| IV-627 | 458.2 | 2.48 | |
| IV-628 | 469 | 2.91 | 1H NMR (500 MHz, DMSO-d6) δ 13.54 (br s, 1H), 10.37 (m, 1H), 9.35 (s, 1H), 8.67 (s, 1H), 8.36 (d, J = 6.0 Hz, 1H), 8.01 (s, 1H), 6.55 (d, J = 6.1 Hz, 1H), 4.34-3.43 (m, 5H), 2.43 (br s, 1H), 2.22-2.03 (m, 1H). |
| IV-629 | 469 | 2.91 | 1H NMR (500 MHz, DMSO-d6) δ 13.54 (br s, 1H), 10.37 (m, 1H), 9.35 (s, 1H), 8.67 (s, 1H), 8.36 (d, J = 6.0 Hz, 1H), 8.01 (s, 1H), 6.55 (d, J = 6.1 Hz, 1H), 4.34-3.43 (m, 5H), 2.43 (br s, 1H), 2.22-2.03 (m, 1H). |
| IV-630 | 455 | 2.85 | 1H NMR (500 MHz, DMSO-d6) δ 10.39-10.33 (m, 1H), 9.38 (d, J = 9.5 Hz, 1H), 8.72 (d, J = 8.5 Hz, 1H), 8.38 (s, 1H), 7.48 (s, 1H), 6.61 (d, J = 6.3 Hz, 1H), 3.85-3.26 |

TABLE 7-continued

Analytical data for compounds of Formula IV

| IV- | LCMS_Plus | LCMS_RT | NMR |
|---|---|---|---|
| | | | (m, 4H), 2.44 (brs, 1H), 2.17-2.03 (m, 1H), 1.35 (s, 3H), 0.84 (s, 2H), 0.70 (s, 2H), water peak obscures some signals. |
| IV-631 | | | 1H NMR (500 MHz, DMSO-d6) δ 10.22 (s, 1H), 9.36 (d, J = 1.3 Hz, 1H), 8.69 (s, 1H), 8.38 (d, J = 6.3 Hz, 1H), 7.44 (s, NH), 6.96 (s, NH), 6.88 (d, J = 6.4 Hz, 1H), 3.09 (s, 1H), 2.55-2.52 (m, 2H), 2.41-2.31 (m, 1H), 1.92-1.65 (m, 4H), 1.23 (d, J = 6.8 Hz, 3H). |
| IV-632 | 491.1 | 1.98 | |
| IV-633 | 491.2 | 1.98 | 1H NMR (500 MHz, Methanol-d4) δ 10.33 (s, 1H), 9.20 (s, 1H), 8.68 (s, 1H), 8.41 (d, J = 6.3 Hz, 1H), 7.65 (s, 2H), 6.90 (d, J = 6.4 Hz, 1H), 5.09-4.92 (m, 1H), 3.25-3.14 (m, 1H), 3.14-3.04 (m, 1H), 2.99-2.88 (m, 1H), 2.41-2.31 (m, 1H), 2.30-2.16 (m, 2H), 1.96-1.82 (m, 1H), 1.67 (d, J = 12.8 Hz, 3H), 1.63 (d, J = 12.9 Hz, 3H). |
| IV-634 | 415.1 | 2.54 | 1H NMR (500 MHz, Methanol-d4) δ 10.31 (dd, J = 1.5, 0.8 Hz, 1H), 9.30-9.21 (m, 1H), 8.97 (d, J = 5.6 Hz, 1H), 8.87 (s, 1H), 8.77 (d, J = 2.8 Hz, 1H), 7.87 (d, J = 5.6 Hz, 1H), 6.67 (d, J = 2.8 Hz, 1H), 3.72-3.61 (m, 1H), 3.47-3.33 (m, 2H), 3.33-3.21 (m, 1H), 3.11 (ddd, J = 12.8, 11.0, 3.6 Hz, 1H), 2.33-2.24 (m, 1H), 2.10-1.99 (m, 1H), 2.00-1.84 (m, 2H). |
| IV-635 | 415 | 2.54 | 1H NMR (500 MHz, DMSO-d6) δ 12.58 (s, 1H), 10.38 (d, J = 13.3 Hz, 1H), 9.36 (d, J = 1.3 Hz, 1H), 8.66 (s, 1H), 8.32 (d, J = 5.6 Hz, 1H), 7.58 (brs, 1H), 7.40 (brs, 1H), 6.50 (d, J = 6.0 Hz, 1H), 3.92-3.81 (m, 1H), 3.67-3.50 (m, 2H), 3.49-3.34 (m, 1H), 2.63-2.55 (m, 3H), 2.15 (brs, 1H), 1.82-1.70 (m, 1H). |
| IV-636 | 488.4 | 2.27 | 1H NMR (500 MHz, Methanol-d4) δ 10.24 (s, 1H), 9.20 (d, J = 1.5 Hz, 1H), 8.69 (s, 1H), 8.45 (d, J = 6.3 Hz, 1H), 7.86 (s, 2H), 7.41 (s, 2H), 6.89 (d, J = 6.2 Hz, 1H), 5.01 (s, 2H), 3.87-3.63 (m, 2H), 3.53-3.34 (m, 4H), 3.20-3.05 (m, 1H), 1.61 (d, J = 6.3 Hz, 3H), 1.47 (d, J = 7.0 Hz, 3H). |
| IV-637 | 499.3 | 2.84 | 1H NMR (500 MHz, DMSO-d6) δ 10.30 (s, 1H), 9.69 (m, 1H), 9.34 (s, 1H), 9.01 (m, 1H), 8.71 (s, 1H), 7.84 (s, 2H), 4.69 (m, 1H), 4.10 (m, 3H), 3.30 (masked, 3H), 2.99 (m, 1H), 2.50 (masked, 1H), 2.30 (m, 2H), 1.43 (m, 3H), 1.15 (m, 3H). |
| IV-638 | 445.3 | 2.52 | 1H NMR (500 MHz, Methanol-d4) δ 10.35 (s, 1H), 9.20 (d, J = 1.4 Hz, 1H), 8.74 (s, 1H), 8.40 (d, J = 6.3 Hz, 1H), 7.71 (d, J = 1.3 Hz, 1H), 7.05 (s, 1H), 6.80 (d, J = 6.3 Hz, 1H), 5.49 (s, 1H), 4.88 (s, 1H), 4.47 (s, 1H), 3.91 (s, 1H), 3.03 (s, 1H), 1.41 (d, J = 6.1 Hz, 3H), 1.13-0.96 (m, 3H). |
| IV-639 | 445.2 | 2.52 | 1H NMR (500 MHz, Methanol-d4) δ 10.33 (s, 1H), 9.24-9.12 (m, 1H), 8.72 (s, 1H), 8.38 (d, J = 6.3 Hz, 1H), 7.71 (d, J = 1.3 Hz, 1H), 7.11-6.98 (m, 1H), 6.79 (d, J = 6.2 Hz, 1H), 5.33 (s, 1H), 4.91-4.86 (m, 1H), 4.47 (s, 1H), 3.90 (s, 1H), 3.02 (s, 1H), 1.41 (d, J = 6.1 Hz, 3H), 1.04 (d, J = 6.8 Hz, 3H). |
| IV-640 | 504.4 | 2.26 | |
| IV-641 | 416.45 | 2.09 | 1H NMR (400 MHz, DMSO-d6) δ 13.36 (s, 1H), 10.36 (s, 1H), 9.37-9.32 (m, 1H), 8.65 (s, 1H), 8.33 (d, J = 5.9 Hz, 1H), 6.52 (d, J = 7.4 Hz, 1H), 4.06 (s, 1H), 3.83 (s, 2H), 3.65 (s, 3H), 2.43 (d, J = 23.1 Hz, 2H), 2.32 (s, 2H). |
| IV-642 | 402.05 | 2.05 | 1H NMR (400 MHz, DMSO-d6) δ 13.82 (s, 1H), 10.34 (d, J = 17.5 Hz, 1H), 9.35 (s, 1H), 8.64 (d, J = 9.6 Hz, 1H), 8.34 (d, J = 6.0 Hz, 1H), 8.28 (s, 1H), 6.54 (s, 1H), 4.11 |

TABLE 7-continued

Analytical data for compounds of Formula IV

| IV- | LCMS_Plus | LCMS_RT | NMR |
|---|---|---|---|
| | | | (s, 1H), 3.95-3.51 (m, 3H), 2.49-2.05 (m, 3H). |
| IV-643 | 391.15 | 3.6 | 1H NMR (400 MHz, DMSO-d6) δ 10.31-10.20 (m, 1H), 9.36 (s, 1H), 8.71-8.64 (m, 1H), 8.38-8.26 (m, 1H), 6.89-6.72 (m, 1H), 3.85 (s, 1H), 2.10 (s, 1H), 1.95-1.50 (m, 1H), 1.48-1.30 (m, 1H), 1.29-1.13 (m, 2H), 1.17-1.00 (m, 3H), 1.01 (q, J = 3.5, 2.7 Hz, 2H), 1.01-0.88 (m, 4H), 0.76-0.63 (m, 1H). |
| IV-644 | 402.95 | 3.69 | 1H NMR (400 MHz, DMSO-d6) δ 10.38 (s, 1H), 9.34 (d, J = 1.3 Hz, 1H), 8.65 (s, 1H), 8.29 (d, J = 6.1 Hz, 1H), 6.52-6.43 (m, 1H), 3.91 (dd, J = 22.3, 12.6 Hz, 1H), 3.60-3.50 (m, 1H), 3.23-2.98 (m, 1H), 2.14 (s, 2H), 1.78 (s, 4H), 1.62 (s, 3H), 1.53 (s, 2H), 1.23 (s, 2H). |
| IV-645 | 434.1 | 2.17 | 1H NMR (400 MHz, DMSO-d6) δ 10.32 (s, 1H), 9.33 (d, J = 1.3 Hz, 1H), 8.64 (d, J = 10.0 Hz, 1H), 8.29 (d, J = 6.1 Hz, 1H), 6.48 (dd, J = 24.3, 6.2 Hz, 1H), 4.57 (d, J = 4.1 Hz, 1H), 3.93 (dt, J = 44.1, 9.3 Hz, 1H), 3.71-3.34 (m, 3H), 3.28-2.89 (m, 1H), 2.89-2.70 (m, 1H), 2.17 (td, J = 24.1, 20.4, 13.8 Hz, 3H), 1.86 (t, J = 10.0 Hz, 1H), 1.75 (d, J = 11.4 Hz, 3H), 1.42 (d, J = 11.9 Hz, 2H). 1 proton obscured by solvent peak |
| IV-646 | 411.85 | 2.59 | 1H NMR (400 MHz, DMSO-d6) δ 10.37 (d, J = 8.6 Hz, 1H), 9.35 (s, 1H), 8.72-8.60 (m, 3H), 8.50 (dd, J = 4.8, 1.6 Hz, 1H), 8.36 (d, J = 5.6 Hz, 1H), 7.83 (dt, J = 7.9, 2.0 Hz, 1H), 7.45-7.37 (m, 1H), 6.56 (d, J = 6.1 Hz, 1H), 4.28 (s, 1H), 3.98 (d, J = 9.7 Hz, 1H), 3.69 (d, J = 9.7 Hz, 1H), 3.61 (s, 1H), 3.58-3.40 (m, 1H), 2.21 (s, 1H). |
| IV-647 | 430.6 | 1.72 | 1H NMR (400 MHz, DMSO-d6) δ 10.35 (s, 1H), 9.33 (s, 1H), 8.64 (s, 1H), 8.30 (d, J = 6.1 Hz, 1H), 6.50 (dd, J = 14.1, 6.1 Hz, 1H), 5.27 (s, 1H), 4.04-3.72 (m, 1H), 3.66 (s, 1H), 3.55 (s, 1H), 3.39-3.14 (m, 5H), 2.33 (d, J = 14.2 Hz, 1H), 2.13 (s, 1H), 1.13 (dd, J = 6.5, 2.4 Hz, 1H). |
| IV-648 | 535.3 | 2.14 | 1H NMR (400 MHz, DMSO-d6) δ 12.68 (s, 1H), 10.32 (m, 1H), 9.34 (m, 1H), 8.66 (m, 1H), 7.70-7.48 (m, 2H), 5.97 (m, 1H), 5.01-4.71 (m, 1H), 4.05 (m, 2H), 3.45 (m, 6H), 2.85 (m, 1H), 2.50 (masked, 2H), 1.16 (m, 3H), 0.91 (m, 3H). |
| IV-649 | 444.3 | 2.2 | 1H NMR (500 MHz, Methanol-d4) δ 10.17 (s, 1H), 9.21 (s, 1H), 8.65 (s, 1H), 8.52 (s, 1H), 8.28 (s, 1H), 7.71 (s, 2H), 4.67 (m, 1H), 4.38 (m, 1H), 4.24 (m, 1H), 3.16 (m, 1H), 2.93 (m, 1H), 1.34 (d, 3H), 1.14 (d, 3H). |
| IV-650 | 444.3 | 2.2 | 1H NMR (500 MHz, Methanol-d4) δ 10.17 (s, 1H), 9.21 (s, 1H), 8.65 (s, 1H), 8.52 (s, 1H), 8.28 (s, 1H), 7.71 (s, 2H), 4.67 (m, 1H), 4.38 (m, 1H), 4.24 (m, 1H), 3.16 (m, 1H), 2.93 (m, 1H), 1.34 (d, 3H), 1.14 (d, 3H). |
| IV-651 | 464.2 | 2.48 | 1H NMR (400 MHz, DMSO-d6) δ 13.40 (s, 1H), 10.19 (s, 1H), 9.68-9.43 (m, 1H), 9.38 (s, 1H), 9.18-8.94 (m, 1H), 8.80 (s, 1H), 8.54 (d, J = 6.2 Hz, 1H), 8.12 (s, 1H), 7.08 (d, J = 6.3 Hz, 1H), 5.21-4.51 (m, 2H), 4.50-4.36 (m, 1H), 3.75-3.63 (m, 2H), 3.20-3.06 (m, 1H), 1.36 (d, J = 6.4 Hz, 3H). |
| IV-652 | 464.2 | 2.48 | |
| IV-653 | 483.1 | 3.08 | 1H NMR (400 MHz, DMSO-d6) δ 13.54 (d, J = 2.0 Hz, 1H), 10.18 (s, 1H), 9.34 (d, J = 1.3 Hz, 1H), 8.73 (s, 1H), 8.39 (d, J = 6.3 Hz, 1H), 6.95 (d, J = 6.4 Hz, 1H), 6.64 (d, J = 1.9 Hz, 1H), 4.59 (s, 2H), 3.26-3.06 (m, 2H), 2.98 (tt, J = 10.8, 3.8 Hz, 1H), 2.15 (d, |

TABLE 7-continued

Analytical data for compounds of Formula IV

| IV- | LCMS_Plus | LCMS_RT | NMR |
|---|---|---|---|
| | | | J = 12.4 Hz, 1H), 1.97-1.74 (m, 2H), 1.61 (q, J = 13.0, 12.4 Hz, 1H). |
| IV-654 | 497.1 | 2.98 | 1H NMR (400 MHz, DMSO-d6) δ 10.20 (s, 1H), 9.35 (d, J = 1.2 Hz, 1H), 8.70 (s, 1H), 8.38 (d, J = 6.3 Hz, 1H), 7.74 (d, J = 1.4 Hz, 1H), 6.94 (d, J = 6.3 Hz, 1H), 4.59 (s, 2H), 3.69 (s, 3H), 3.25 (d, J = 12.6 Hz, 1H masked by water), 3.22-2.94 (m, 2H), 2.18-1.99 (m, 1H), 1.87 (dd, J = 12.2, 9.2 Hz, 2H), 1.63 (q, J = 13.6, 12.8 Hz, 1H). |
| IV-655 | 429.2 | 2.75 | 1H NMR (400 MHz, DMSO-d6) δ 10.21 (s, 1H), 9.35 (d, J = 1.3 Hz, 1H), 8.68 (s, 1H), 8.39 (d, J = 6.3 Hz, 1H), 7.35 (d, J = 1.8 Hz, 1H), 6.95 (d, J = 6.4 Hz, 1H), 6.17 (d, J = 1.9 Hz, 1H), 4.54 (s, 2H), 3.81 (s, 3H), 3.13 (dt, J = 23.2, 12.4 Hz, 2H), 3.02-2.87 (m, 1H), 2.15-1.96 (m, 1H), 1.93-1.55 (m, 3H). |
| IV-656 | 417.1 | 2.44 | 1H NMR (400 MHz, DMSO-d6) δ 10.19 (d, J = 1.4 Hz, 1H), 9.35 (d, J = 1.1 Hz, 1H), 9.16 (s, 1H), 8.66 (s, 1H), 8.38 (d, J = 6.3 Hz, 1H), 6.91 (d, J = 6.4 Hz, 1H), 4.53 (s, 1H), 4, 14 (s, 1H), 3.71 (dd, J = 13.4, 9.0 Hz, 1H), 3.48 (t, J = 11.4 Hz, 1H), 3.43-3.33 (m, 1H masked by water), 2.32-2.12 (m, 1H), 2.07-1.93 (m, 1H), 1.90-1.79 (m, 1H), 1.77-1.57 (m, 1H). |
| IV-657 | 431.05 | 2.51 | 1H NMR (400 MHz, DMSO-d6) δ 12.51 (s, 1H), 10.21 (s, 1H), 9.35 (d, J = 1.3 Hz, 1H), 8.69 (s, 1H), 8.43 (d, J = 6.2 Hz, 1H), 7.46 (s, 1H), 6.94 (d, J = 6.3 Hz, 1H), 4.65 (d, J = 10.2 Hz, 1H), 4.42 (s, 2H), 4.09-4.01 (m, 1H), 3.75 (td, J = 11.6, 2.7 Hz, 1H), 3.31-3.19 (m, 1H), 2.08 (d, J = 0.7 Hz, 3H), 1.27 (dd, J = 6.6, 5.5 Hz, 1H). |
| IV-658 | 468.15 | 2.57 | 1H NMR (400 MHz, DMSO-d6) δ 10.23 (d, J = 1.4 Hz, 1H), 9.36 (s, 1H), 8.71 (d, J = 1.2 Hz, 1H), 8.41 (dd, J = 6.3, 1.2 Hz, 1H), 6.84 (d, J = 6.3 Hz, 1H), 3.43-3.34 (m, 4H), 3.25 (t, J = 7.6 Hz, 4H), 3.08 (s, 1H), 2.34-2.20 (m, 2H), 1.95 (s, 1H), 1.86 (ddd, J = 14.5, 8.7, 3.8 Hz, 2H), 1.57 (d, J = 12.8 Hz, 1H). |
| IV-659 | 498.11 | 2.86 | |
| IV-660 | 432.16 | 2.04 | 1H NMR (400 MHz, DMSO-d6) δ 11.22 (s, 1H), 10.26-10.20 (m, 1H), 9.36 (d, J = 1.3 Hz, 1H), 8.75 (s, 1H), 8.40 (d, J = 6.3 Hz, 1H), 6.92 (d, J = 6.4 Hz, 1H), 3.31 (s, 1H), 3.37-3.26 (m, 1H), 3.21 (t, J = 11.8 Hz, 1H), 2.77-2.65 (m, 1H), 2.12-2.02 (m, 1H), 1.95-1.74 (m, 2H), 1.57 (d, J = 12.3 Hz, 1H), 1.04-0.90 (m, 2H). |
| IV-661 | 432.16 | 2.02 | 1H NMR (400 MHz, DMSO-d6) δ 13.65 (s, 1H), 10.20 (s, 1H), 9.35 (d, J = 1.3 Hz, 1H), 8.69 (s, 1H), 8.43 (d, J = 6.2 Hz, 1H), 6.93 (d, J = 6.3 Hz, 1H), 4.69-4.61 (m, 1H), 4.33 (s, 1H), 4.06 (ddd, J = 11.5, 3.6, 1.9 Hz, 1H), 3.76 (td, J = 11.4, 2.8 Hz, 1H), 3.51 (q, J = 12.0, 9.9 Hz, 1H), 3.32-3.23 (m, 1H), 2.34 (s, 3H), 0.99-0.90 (m, 1H). |
| IV-662 | 473.28 | 2.47 | 1H NMR (400 MHz, DMSO-d6) δ 10.22 (s, 1H), 9.35 (d, J = 1.2 Hz, 1H), 8.65 (s, 1H), 8.36 (d, J = 6.3 Hz, 1H), 6.89 (d, J = 6.4 Hz, 1H), 6.01 (s, 1H), 4.77 (t, J = 5.3 Hz, 1H), 3.69 (s, 2H), 3.62 (td, J = 7.0, 5.3 Hz, 2H), 3.32 (s, 5H), 3.21-3.06 (m, 1H), 2.74 (t, J = 6.9 Hz, 2H), 2.05 (d, J = 12.6 Hz, 1H), 1.87-1.68 (m, 1H), 1.61 (s, 1H), 0.99-0.90 (m, 1H). |
| IV-663 | 432.1 | 2.42 | 1H NMR (400 MHz, DMSO-d6) δ 10.24 (s, 1H), 9.36 (d, J = 1.3 Hz, 1H), 8.67 (d, J = 3.5 Hz, 1H), 8.37 (dd, J = 6.4, 0.7 Hz, 1H), 7.58-7.53 (m, 1H), 7.08 (s, 1H), 6.88 (dd, J = 6.4, 3.3 Hz, 1H), 3.45 (t, J = 8.7 Hz, 1H), 3.17 (t, J = 11.7 Hz, 1H), 3.13-2.92 (m, |

TABLE 7-continued

Analytical data for compounds of Formula IV

| IV- | LCMS_Plus | LCMS_RT | NMR |
|---|---|---|---|
| | | | 3H), 2.34-1.94 (m, 4H), 1.78 (t, J = 11.3 Hz, 1H), 1.62-1.14 (m, 3H). |
| IV-664 | 483.3 | 3.48 | 1H NMR (400 MHz, DMSO-d6) δ 10.14 (s, 1H), 9.36 (s, 1H), 8.71 (s, 1H), 8.41 (d, J = 6.3 Hz, 1H), 8.18-8.01 (m, 1H), 6.98 (d, J = 6.4 Hz, 1H), 6.75 (d, J = 2.4 Hz, 1H), 4.79-4.60 (m, 1H), 4.59-4.47 (m, 1H), 4.47-4.18 (m, 1H), 3.67 (dd, J = 12.9, 9.9 Hz, 1H), 3.31 (ddd, J = 13.7, 11.1, 3.0 Hz, 1H), 2.28-2.15 (m, 2H), 1.98-1.86 (m, 1H), 1.76-1.60 (m, 1H). |
| IV-665 | 415.3 | 2.92 | 1H NMR (400 MHz, DMSO-d6) δ 10.15 (s, 1H), 9.36 (s, 1H), 8.69 (s, 1H), 8.40 (d, J = 6.4 Hz, 1H), 7.84 (d, J = 2.2 Hz, 1H), 7.49 (d, J = 1.8, 0.7 Hz, 1H), 6.96 (d, J = 6.5 Hz, 1H), 6.27 (t, J = 2.1 Hz, 1H), 4.81-4.51 (m, 1H), 4.50-4.21 (m, 2H), 3.57 (dd, J = 13.0, 10.0 Hz, 1H), 3.27 (ddd, J = 13.8, 11.3, 3.0 Hz, 1H), 2.26-2.14 (m, 2H), 1.98-1.85 (m, 1H), 1.76-1.59 (m, 1H). |
| IV-666 | 512.3 | 2.75 | 1H NMR (500 MHz, Methanol-d4) δ 10.29 (s, 1H), 9.23 (d, J = 1.3 Hz, 1H), 8.75 (s, 1H), 8.51 (d, J = 6.2 Hz, 1H), 7.54 (d, J = 0.7 Hz, 1H), 6.96 (d, J = 6.3 Hz, 1H), 4.92-4.86 (m, 1H), 3.62 (ddd, J = 10.8, 6.5, 3.8 Hz, 1H), 3.33 (d, J = 1.7 Hz, 1H), 1.56 (d, J = 6.6 Hz, 3H), 1.28 (d, J = 7.1 Hz, 3H). |
| IV-667 | 444.3 | 2.5 | 1H NMR (500 MHz, DMSO-d6) δ 10.23 (s, 1H), 9.36 (s, 1H), 8.72 (s, 1H), 8.41 (d, J = 6.2 Hz, 1H), 7.38 (s, 1H), 6.97 (d, J = 6.4 Hz, 1H), 6.31 (s, 1H), 4.01 (d, J = 11.8 Hz, 1H), 3.88 (s, 3H), 2.98-2.92 (m, 2H), 2.73-2.67 (m, 2H), 2.53-2.50 (m, 1H), 1.14 (d, J = 5.8 Hz, 3H). |
| IV-668 | 415.1 | 2.54 | 1H NMR (500 MHz, DMSO-d6) δ 12.6 (s, 1H), 10.45 (s, 1H), 9.34 (s, 1H), 8.64 (s, 1H), 7.74 (s, 1H), 7.48 (s, 1H), 6.41 (s, 1H), 4.15-3.80 (m, 1H), 3.73-3.65 (m, 1H), 3.45 (m, 2H), 2.38 (m, 3H), 2.03 (m, 1H), 1.24 (m, 1H), 0.98 (m, 1H). |
| IV-669 | 458.2 | 2.46 | 1H NMR (500 MHz, DMSO-d6) δ 12.6 (s, 1H), 10.32 (s, 1H), 9.34 (s, 1H), 8.67 (s, 1H), 7.61 (m, 2H), 6.80 (m, 1H), 4.95-4.60 (m, 1H), 4.25-3.80 (m, 2H), 2.85 (m, 1H), 2.70 (m, 1H), 2.37 (s, 3H), 1.24 (m, 3H), 0.98 (m, 3H). |
| IV-670 | 458.2 | 2.46 | 1H NMR (500 MHz, DMSO-d6) δ 12.6 (s, 1H), 10.32 (s, 1H), 9.34 (s, 1H), 8.67 (s, 1H), 7.61 (m, 2H), 6.80 (m, 1H), 4.95-4.60 (m, 1H), 4.25-3.80 (m, 2H), 2.85 (m, 1H), 2.70 (m, 1H), 2.37 (s, 3H), 1.24 (m, 3H), 0.98 (m, 3H). |
| IV-671 | 433.1 | 2.46 | 1H NMR (500 MHz, Methanol-d4) δ 10.33 (s, 1H), 9.40 (s, 1H), 9.20 (d, J = 1.4 Hz, 1H), 8.67 (s, 1H), 8.37 (d, J = 6.3 Hz, 1H), 6.85 (d, J = 6.4 Hz, 1H), 4.74 (s, 1H), 4.33 (s, 1H), 3.72 (dd, J = 13.3, 9.5 Hz, 1H), 3.61 (dd, J = 8.9, 5.1 Hz, 1H), 3.52-3.42 (m, 1H), 2.38 (dd, J = 13.1, 4.4 Hz, 1H), 2.16-2.05 (m, 1H), 1.98 (dt, J = 8.6, 4.4 Hz, 1H), 1.89-1.75 (m, 1H). |
| IV-672 | 444.1 | 2.16 | 1H NMR (500 MHz, DMSO-d6) δ 10.23 (s, 1H), 9.36 (s, 1H), 8.71 (s, 1H), 8.40 (d, J = 6.3 Hz, 1H), 7.57 (s, 1H), 6.95 (d, J = 6.4 Hz, 1H), 6.91 (s, 1H), 3.91 (dt, J = 11.3, 3.3 Hz, 1H), 3.69 (s, 3H), 3.00-2.86 (m, 2H), 2.67-2.60 (m, 2H), 2.53-2.50 (m, 1H), 1.13 (d, J = 6.2 Hz, 3H). |
| IV-673 | 512.2 | 2.52 | 1H NMR (500 MHz, Methanol-d4) δ 10.27 (s, 1H), 9.18 (d, J = 1.4 Hz, 1H), 8.67 (d, J = 5.9 Hz, 1H), 8.33 (d, J = 6.3 Hz, 1H), 7.27 (s, 1H), 6.88-6.74 (m, 1H), 5.31 (s, 1H), 4.52 (s, 1H), 4.24 (d, J = 3.9 Hz, 1H), 3.89 (s, 1H), 3.04 (ddd, J = 10.0, 6.1, 3.2 Hz, 1H), 2.86 (s, 1H), 1.31 (d, J = 6.2 Hz, 3H), 1.13-0.94 (m, 3H). |

TABLE 7-continued

Analytical data for compounds of Formula IV

| IV- | LCMS_Plus | LCMS_RT | NMR |
|---|---|---|---|
| IV-674 | 512.1 | 2.52 | 1H NMR (500 MHz, Methanol-d4) δ 10.27 (s, 1H), 9.18 (d, J = 1.4 Hz, 1H), 8.67 (d, J = 5.9 Hz, 1H), 8.33 (d, J = 6.3 Hz, 1H), 7.27 (s, 1H), 6.88-6.74 (m, 1H), 5.31 (s, 1H), 4.52 (s, 1H), 4.24 (d, J = 3.9 Hz, 1H), 3.89 (s, 1H), 3.04 (ddd, J = 10.0, 6.1, 3.2 Hz, 1H), 2.86 (s, 1H), 1.31 (d, J = 6.2 Hz, 3H), 1.13-0.94 (m, 3H). |
| IV-675 | 432.2 | 3.17 | 1H NMR (500 MHz, DMSO-d6) δ 10.16 (s, 1H), 9.37 (s, 1H), 8.68 (s, 1H), 8.40 (d, J = 6.4 Hz, 1H), 7.77 (d, J = 3.3 Hz, 1H), 7.66 (d, J = 3.3 Hz, 1H), 6.97 (d, J = 6.5 Hz, 1H), 4.88-4.51 (m, 2H), 3.51 (dd, J = 13.1, 10.1 Hz, 1H), 3.41-3.27 (m, 2H), 2.30-2.17 (m, 1H), 2.04-1.82 (m, 2H), 1.76-1.61 (m, 1H). |
| IV-676 | 471 | 2.15 | 1H NMR (500 MHz, Methanol-d4) δ 10.32 (s, 1H), 9.22 (s, 1H), 8.69 (s, 1H), 8.37 (d, 1H), 7.80 (m, 1H), 7.50 (m, 1H), 6.80 (m, 1H), 6.58 (m, 1H), 4.40 (m, 1H), 4.15-4.05 (m, 1H), 3.72 (m, 1H), 3.50 (m, 3H), 1.24 (m, 3H), 0.98 (m, 3H). |
| IV-677 | 471.2 | 2.23 | 1H NMR (500 MHz, Methanol-d4) δ 10.50-10.32 (m, 1H), 9.22 (s, 1H), 8.69 (s, 1H), 8.37 (d, 1H), 7.77 (m, 1H), 7.50 (m, 1H), 6.80 (m, 1H), 6.63 (m, 1H), 5.10 (m, 1H), 4.30 (m, 1H), 4.06 (m, 1H), 3.88 (m, 1H), 3.05 (m, 1H), 2.90 (m, 1H), 1.24 (m, 3H), 0.98 (m, 3H). |
| IV-678 | 416.1 | 2.58 | 1H NMR (500 MHz, DMSO-d6) δ 10.22 (s, 1H), 9.36 (s, 1H), 8.69 (s, 1H), 8.40 (d, J = 6.2 Hz, 1H), 8.26 (s, 1H), 7.02 (s, 1H), 6.92 (d, J = 6.3 Hz, 1H), 4.50 (s, 2H), 3.41 (dd, J = 13.2, 9.9 Hz, 1H), 3.34 (d, J = 11.2 Hz, 1H), 3.04 (d, J = 9.5 Hz, 1H), 2.13 (d, J = 9.8 Hz, 1H), 1.83 (d, J = 10.7 Hz, 2H), 1.64 (s, 1H). |
| IV-679 | 456.3 | 2.52 | 1H NMR (400 MHz, Methanol-d4) δ 10.31 (s, 1H), 9.20 (d, J = 1.3 Hz, 1H), 8.69 (s, 1H), 8.45 (d, J = 6.3 Hz, 1H), 7.86 (s, 2H), 6.91 (d, J = 6.3 Hz, 1H), 5.49 (d, J = 0.6 Hz, 1H), 3.22 (s, 1H), 2.29 (d, J = 11.4 Hz, 1H), 2.15 (d, J = 0.6 Hz, 1H), 1.86 (s, 1H), 1.42-1.19 (m, 5H). |
| IV-680 | 415.3 | 2.62 | 1H NMR (400 MHz, DMSO-d6) δ 12.53 (s, 1H), 10.24 (s, 1H), 9.35-9.34 (m, 1H), 8.67 (s, 1H), 8.35 (d, J = 6.3 Hz, 1H), 7.55 (br s, 1H), 7.39 (br s, 1H), 6.87 (d, J = 6.4 Hz, 1H), 4.52 (br s, 2H), 3.17-3.10 (m, 2H), 2.86 (tt, J = 11.5, 3.9 Hz, 1H), 1.98 (d, J = 15.0 Hz, 2H), 1.52 (qd, J = 12.7, 4.1 Hz, 2H). |
| IV-681 | 484.3 | 2.51 | 1H NMR (400 MHz, DMSO-d6) δ 12.63 (s, 1H), 10.21 (s, 1H), 9.36 (s, 1H), 8.68 (d, J = 8.5 Hz, 1H), 8.37 (dd, J = 17.0, 6.3 Hz, 1H), 7.57 (d, J = 71.2 Hz, 2H), 6.88 (d, J = 8.2 Hz, 1H), 3.51 (s, 1H), 3.19-2.56 (m, 7H), 2.45-2.17 (m, 2H), 2.13-1.52 (m, 5H), 1.33 (q, J = 12.2 Hz, 1H). |
| IV-682 | 473.1 | 2.31 | 1H NMR (500 MHz, Methanol-d4) δ 10.36 (d, J = 1.4 Hz, 1H), 9.22 (dd, J = 1.4, 0.7 Hz, 1H), 8.69 (d, J = 0.9 Hz, 1H), 8.38-8.24 (m, 1H), 7.51 (s, 2H), 6.73 (d, J = 6.4 Hz, 1H), 3.47-3.40 (m, 2H), 3.01 (t, J = 12.2 Hz, 1H), 2.32-2.15 (m, 1H), 2.04-1.80 (m, 2H), 1.30 (s, 6H). |
| IV-683 | 473.1 | 2.3 | 1H NMR (500 MHz, Methanol-d4) δ 10.35 (d, J = 0.9 Hz, 1H), 9.25-9.16 (m, 1H), 8.68 (s, 1H), 8.31 (d, J = 6.3 Hz, 1H), 7.49 (s, 2H), 6.72 (d, J = 6.4 Hz, 1H), 3.49-3.37 (m, 2H), 3.00 (t, J = 12.2 Hz, 1H), 2.21 (d, J = 12.8 Hz, 1H), 1.96 (td, J = 12.6, 4.6 Hz, 1H), 1.90-1.78 (m, 1H), 1.27 (s, 6H). |
| IV-684 | 473.1 | 2.26 | 1H NMR (500 MHz, Methanol-d4) δ 10.31 (s, 1H), 9.19 (d, J = 1.3 Hz, 1H), 8.64 (s, 1H), 8.34 (d, J = 6.3 Hz, 1H), 7.63 (s, 2H), |

TABLE 7-continued

Analytical data for compounds of Formula IV

| IV- | LCMS_Plus | LCMS_RT | NMR |
|---|---|---|---|
| | | | 6.79 (d, J = 6.4 Hz, 1H), 4.67 (s, 2H), 3.06-2.78 (m, 3H), 2.33-2.18 (m, 1H), 1.77-1.54 (m, 2H), 1.31 (d, J = 5.4 Hz, 7H). |
| IV-685 | 473.1 | 2.26 | 1H NMR (500 MHz, Methanol-d4) δ 10.30 (s, 1H), 9.19 (d, J = 1.3 Hz, 1H), 8.63 (s, 1H), 8.33 (d, J = 6.3 Hz, 1H), 7.62 (s, 2H), 6.78 (d, J = 6.4 Hz, 1H), 4.76 (s, 1H), 3.01-2.78 (m, 3H), 2.31-2.21 (m, 1H), 1.80-1.55 (m, 2H), 1.31 (d, J = 5.5 Hz, 6H). |
| IV-686 | 416.2 | 2.85 | 1H NMR (400 MHz, DMSO-d6) δ 10.22 (s, 1H), 9.37-9.36 (m, 1H), 8.67 (s, 1H), 8.38 (d, J = 6.3 Hz, 1H), 8.02 (s, 1H), 7.14 (d, J = 0.7 Hz, 1H), 6.91 (d, J = 6.4 Hz, 1H), 4.55 (br s, 1H), 4.20 (br s, 1H), 3.59 (dd, J = 13.3, 9.6 Hz, 1H), 3.44-3.37 (m, 1H), 3.18-3.11 (m, 1H), 2.20-2.14 (m, 1H), 1.99-1.82 (m, 2H), 1.69-1.60 (m, 1H). |
| IV-687 | 458.3 | 2.47 | 1H NMR (500 MHz, DMSO-d6) δ 10.25-10.12 (m, 1H), 9.34 (s, 1H), 8.70 (s, 1H), 8.38 (s, 1H), 7.65 (s, 1H), 7.42 (s, 1H), 6.88 (m, 1H), 4.98-4.75 (m, 0.5H), 4.25 (m, 0.5H), 4.02 (m, 1H), 3.83 (s, 3H), 2.90 (m, 1H), 2.80-2.70 (m, 1H), 2.60 (m, 0.5H), 1.17 (m, 3H), 1.00 (m, 3H); 1 proton not observed |
| IV-688 | 415.3 | 2.56 | 1H NMR (500 MHz, DMSO-d6) δ 12.71 (s, 1H), 10.34 (s, 1H), 9.36 (s, 1H), 8.68 (s, 1H), 8.35 (d, J = 6.4 Hz, 1H), 7.68 (s, 1H), 7.46 (s, 1H), 6.67-6.42 (m, 1H), 4.44 (d, J = 205.3 Hz, 1H), 3.78 (d, J = 89.4 Hz, 1H), 3.59-3.39 (m, 1H), 2.36 (d, J = 47.5 Hz, 2H), 1.26 (d, J = 11.7 Hz, 1H), 1.03-0.84 (m, 3H). |
| IV-689 | 415.3 | 2.66 | 1H NMR (500 MHz, DMSO-d6) δ 12.63 (s, 1H), 10.34 (s, 1H), 9.35 (d, J = 1.4 Hz, 1H), 8.67 (s, 1H), 8.35 (d, J = 6.0 Hz, 1H), 7.49 (d, J = 95.5 Hz, 2H), 6.53 (s, 1H), 4.22 (d, 1H) 3.59 (s, 2H), 2.16-1.92 (m, 1H), 1.34 (d, J = 95.4 Hz, 5H). |
| IV-690 | 461.3 | 2.72 | 1H NMR (500 MHz, Methanol-d4) δ 10.21 (s, 1H), 9.15 (d, 1H), 8.51 (s, 1H), 7.69 (s, 2H), 7.16-7.14 (dd, 1H), 6.64-6.62 (dd, 1H), 4.45 (m, 1H), 4.30 (m, 1H), 4.08 (m, 1H), 3.08-3.03 (m, 1H), 2.85-2.78 (m, 1H), 1.31 (m, 3H), 1.02 (m, 3H). |
| IV-691 | 432.2 | 3 | 1H NMR (500 MHz, DMSO-d6) δ 10.14 (s, 1H), 9.37 (d, J = 1.3 Hz, 1H), 9.01 (d, J = 0.8 Hz, 1H), 8.70 (s, 1H), 8.40 (d, J = 6.4 Hz, 1H), 7.85 (s, 1H), 6.99 (d, J = 6.5 Hz, 1H), 4.65-4.34 (m, 2H), 3.39-3.20 (m, 3H), 2.21-2.12 (m, 1H), 1.90-1.74 (m, 2H), 1.72-1.58 (m, 1H). |
| IV-692 | 390.1 | 2.07 | 1H NMR (500 MHz, DMSO-d6) δ 10.25 (s, 1H), 9.36 (s, 1H), 8.69 (s, 1H), 8.37 (d, J = 6.4 Hz, 1H), 6.88 (d, J = 6.3 Hz, 1H), 3.31 (br s, 4H)3.68 (d, J = 18.7 Hz, 4H), 1.80 (t, J = 5.7 Hz, 4H). |
| IV-693 | 505.3 | 2.06 | 1H NMR (500 MHz, Methanol-d4) δ 10.18 (s, 1H), 9.28 (s, 1H), 8.75 (s, 1H), 8.42 (d, J = 6.6 Hz, 1H), 7.71 (s, 2H), 7.05 (d, J = 6.7 Hz, 1H), 3.30-3.13 (m, 1H), 2.42-2.10 (m, 3H), 1.81-1.59 (m, 6H), 1.20 (d, J = 6.9 Hz, 3H). |
| IV-694 | 416.3 | 2.96 | 1H NMR (500 MHz, DMSO-d6) δ 10.18 (s, 1H), 9.37 (d, J = 1.3 Hz, 1H), 8.69 (s, 1H), 8.38 (d, J = 6.4 Hz, 1H), 8.32 (d, J = 0.9 Hz, 1H), 7.97 (s, 1H), 6.92 (d, J = 6.4 Hz, 1H), 4.68-4.30 (m, 2H), 3.35-3.20 (m, 2H), 2.87-2.77 (m, 1H), 2.16-2.04 (m, 1H), 1.90-1.74 (m, 2H), 1.72-1.56 (m, 1H). |
| IV-695 | 417.3 | 2.43 | 1H NMR (500 MHz, Methanol-d4) δ 10.44 (d, J = 5.2 Hz, 1H), 9.18 (s, 1H), 8.64 (d, J = 3.8 Hz, 1H), 8.34-8.21 (m, 1H), 7.40 (s, 2H), 6.50 (s, 1H), 4.93 (s, 1H), 4.56 (s, 1H), 3.91 (d, J = 9.2 Hz, 1H), 3.77-3.58 (m, |

TABLE 7-continued

Analytical data for compounds of Formula IV

| IV- | LCMS_Plus | LCMS_RT | NMR |
|---|---|---|---|
| | | | 1H), 2.43 (s, 1H), 2.32 (d, J = 16.0 Hz, 1H), 1.30 (d, J = 6.7 Hz, 1H). |
| IV-696 | 404.1 | 2.37 | 1H NMR (500 MHz, Methanol-d4) δ 10.33 (s, 1H), 9.20 (d, J = 1.3 Hz, 1H), 8.62 (s, 1H), 8.34-8.25 (m, 1H), 6.77-6.69 (m, 1H), 4.24 (s, 2H), 3.81 (dt, J = 20.2, 8.7 Hz, 2H), 3.72 (t, J = 8.3 Hz, 1H), 3.64 (q, J = 8.8 Hz, 1H), 3.28 (ddd, J = 13.7, 10.8, 3.3 Hz, 1H), 2.97 (tt, J = 23.1, 10.4 Hz, 1H), 2.73 (h, J = 8.0 Hz, 1H), 1.98-1.81 (m, 3H), 1.68-1.56 (m, 1H), 1.33 (ddd, J = 14.9, 11.5, 7.3 Hz, 1H). |
| IV-697 | 505.3 | 2.16 | 1H NMR (500 MHz, Methanol-d4) δ 10.18 (s, 1H), 9.28 (s, 1H), 8.75 (s, 1H), 8.42 (d, J = 6.6 Hz, 1H), 7.71 (s, 2H), 7.05 (d, J = 6.7 Hz, 1H), 3.30-3.13 (m, 1H), 2.42-2.10 (m, 3H), 1.81-1.59 (m, 6H), 1.20 (d, J = 6.9 Hz, 3H). |
| IV-698 | 468 | 2.48 | 1H NMR (500 MHz, DMSO-d6) δ 10.35 (dt, J = 1.5, 0.8 Hz, 1H), 9.37 (d, J = 1.3 Hz, 1H), 8.64 (s, 1H), 8.38 (d, J = 5.9 Hz, 1H), 6.41 (d, J = 6.0 Hz, 1H), 3.93 (s, 4H), 3.15 (s, 4H), 2.89 (s, 3H), 1.92 (t, J = 5.5 Hz, 4H). |
| IV-699 | 395.1 | 1.67 | 1H NMR (400 MHz, DMSO-d6) δ 10.46 (d, J = 1.5 Hz, 1H), 9.22 (d, J = 1.3 Hz, 1H), 8.66 (s, 1H), 8.42 (d, J = 6.1 Hz, 1H), 8.19 (d, J = 2.4 Hz, 1H), 7.86 (s, 1H), 6.53 (s, 1H), 4.18-3.47 (m, 6H), 2.05 (s, 3H), 1.49 (s, 6H). |
| IV-767 | 447.2 | 1.37 | (300 MHz, DMSO-d6) 12.27 (s, 1H), 10.20 (s, 1H), 9.36 (s, 1H), 8.67 (s, 1H), 8.38 (d, J = 6.2 Hz, 1H), 7.64 (s, 1H), 6.92 (d, J = 6.3 Hz, 1H), 4.55 (s, 2H), 2.84 (d, J = 12.9 Hz, 1H), 2.67 (q, J = 13.7, 13.0 Hz, 2H), 2.05 (d, J = 12.6 Hz, 1H), 1.73 (s, 1H), 1.39 (q, J = 12.4 Hz, 1H), 1.01 (d, J = 6.4 Hz, 3H). |

Purity and retention time of the compounds from this invention were measured by HPLC.

HPLC method: analytical reverse phase UPLC-MS was carried out on a Waters Acquity UPLC-MS system equipped with a waters BEH 1.7 mm C-18 reverse phase column (2.1 mm×50 mm, 1.7 μm). The mobile phases were acetonitrile and water/acetonitrile (95:5 with 10 mM ammonium formate, pH9). Run time 5 min

Example 107: 2-(1H-Pyrazol-4-yl)-4-[2-[2-(trifluoromethyl)imidazo[2,1-b]thiazol-5-yl]pyrimidin-4-yl]morpholine, V-15

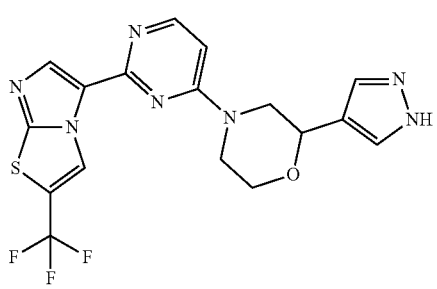 [SMILES: FC(F)(F)c1cn2c(-c3nccc(N4CCOC(c5cn[nH]c5)C4)n3)cnc2s1]

5-(4-Chloropyrimidin-2-yl)-2-(trifluoromethyl)imidazo[2,1-b]thiazole (11 mg, 0.036 mmol), 2-(1H-pyrazol-4-yl)morpholine (10 mg, 0.065 mmol) and DIPEA (30 μL, 0.172 mmol) were dissolved in NMP (1 mL) and heated in a sealed tube at 80° C. for 18 hours. The reaction mixture was cooled to ambient temperature and purified directly by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected and freeze-dried to give 2-(1H-pyrazol-4-yl)-4-[2-[2-(trifluoromethyl)imidazo[2,1-b]thiazol-5-yl]pyrimidin-4-yl]morpholine (trifluoroacetate salt) V-15 (7.8 mg, 40%) as a white solid; $^1$H NMR (500 MHz, DMSO-d$_6$) δ 9.10 (d, J=1.6 Hz, 1H), 8.35 (d, J=6.3 Hz, 1H), 8.14 (s, 1H), 7.69 (s, 2H), 6.87 (d, J=6.4 Hz, 1H), 4.58 (dd, J=10.7, 2.6 Hz, 1H), 4.05-4.03 (m, 1H), 3.70 (td, J=11.5, 2.6 Hz, 1H), 3.21-3.13 (m, 2H), 2.52-2.48 (m, 2H); $^{19}$F NMR (471 MHz, DMSO-d$_6$) δ −55.75, −74.34; ESVI-MS m/z 422.1 (M+1)$^+$.

The following compounds were prepared using a methodology similar to the one described in Example 107:

5-[4-[3-Dimethylphosphoryl-5-(1H-pyrazol-4-yl)-1-piperidyl]pyrimidin-2-yl]-2-(trifluoromethyl)imidazo[2,1-b]thiazole (racemic cis diastereomer), V-5;

5-[4-[3-Dimethylphosphoryl-5-(1H-pyrazol-4-yl)-1-piperidyl]pyrimidin-2-yl]-2-(trifluoromethyl)imidazo[2,1-b]thiazole (racemic trans diastereomer), V-6;

5-[4-[3-(1H-Pyrazol-4-yl)pyrrolidin-1-yl]pyrimidin-2-yl]-2-(trifluoromethyl)imidazo[2,1-b]thiazole, V-7;

1-[2-[2-(Trifluoromethyl)imidazo[2,1-b]thiazol-5-yl]pyrimidin-4-yl]-1,4-diazepan-5-one, V-8;

Dimethyl((1-(2-(2-(trifluoromethyl)imidazo[2,1-b]thiazol-5-yl)pyrimidin-4-yl)piperidin-3-yl)imino)-λ$^6$-sulfanone, V-9;

(3S)-1-[2-[2-(Trifluoromethyl)imidazo[2,1-b]thiazol-5-yl]
pyrimidin-4-yl]piperidine-3-carboxamide, V-10;
5-[4-[2,5-Dimethyl-3-(1H-pyrazol-4-yl)piperazin-1-yl]py-
rimidin-2-yl]-2-(trifluoromethyl)imidazo[2,1-b]thiazole,
V-13;
N-[[1-[2-[2-(Difluoromethyl)imidazo[2,1-b]thiazol-5-yl]
pyrimidin-4-yl]-4,4-difluoro-5-methyl-3-piperidyl]
methyl]methanesulfonamide, V-14

Example 108: N-((-1-(2-(2-(Difluoromethyl)imidazo
[2,1-b]thiazol-5-yl)pyrimidin-4-yl)-4,4-difluoro-5-
methylpiperidin-3-yl)methyl)methanesulfonamide
and N-((-1-(2-(2-(difluoromethyl)imidazo[2,1-b]
thiazol-5-yl)pyrimidin-4-yl)-4,4-difluoro-5-meth-
ylpiperidin-3-yl)methyl)methanesulfonamide, V-1
and V-2

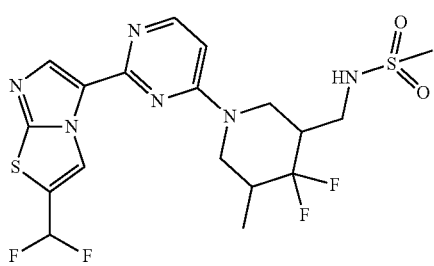

single stereoisomer

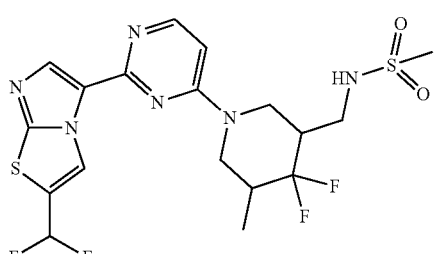

single stereoisomer

The racemic mixture of N-[[1-[2-[2-(difluoromethyl)imi-
dazo[2,1-b]thiazol-5-yl]pyrimidin-4-yl]-4,4-difluoro-5-
methyl-3-piperidyl]methyl]methanesulfonamide (prepared
using a methodology similar to the one described in
Example 121) was separated by chiral supercritical fluid
chromatography [Column: Chiralpak AS-H; Mobile phase:
CO2:methanol (+20 mM ammonia) 70:30] to give the
isolated single compounds, V-1 (8.4 mg, 77%, 99.1% ee)
and V-2 (7.5 mg, 69%, 99.5% ee) as a white solids.

Example 109: 2-(1H-Pyrazol-4-yl)-4-(2-(2-(trifluo-
romethyl)imidazo[2,1-b]thiazol-5-yl)pyrimidin-4-yl)
morpholine, V-3 and 2-(1H-pyrazol-4-yl)-4-(2-(2-
(trifluoromethyl)imidazo[2,1-b]thiazol-5-yl)
pyrimidin-4-yl)morpholine, V-4

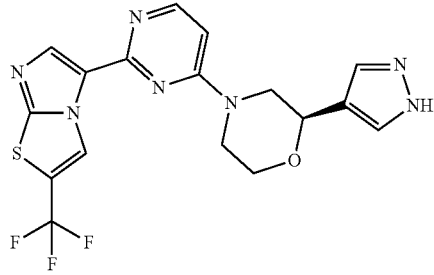

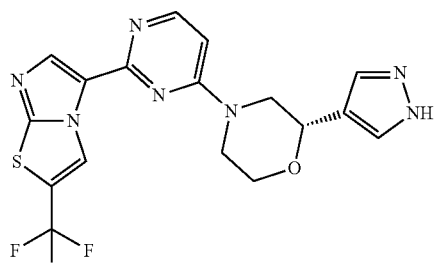

The racemic mixture of 2-(1H-pyrazol-4-yl)-4-(2-(2-(tri-
fluoromethyl)imidazo[2,1-b]thiazol-5-yl)pyrimidin-4-yl)
morpholine (prepared using a methodology similar to the
one described in Example 121 was separated by chiral
supercritical fluid chromatography [Column: Lux Cellulose-
2; Mobile phase: CO$_2$:isopropanol (+20 mM ammonia)
30:70] to give the isolated single compounds V-3 (16.8 mg,
38%, 96.9% ee) and V-4 (14.5 mg, 32%, 98.9% ee).

Example 110: 5-[4-[2,5-Dimethyl-3-(1H-pyrazol-4-
yl)piperazin-1-yl]pyrimidin-2-yl]-2-(trifluoromethyl)
imidazo[2,1-b]thiazole, V-11 and V-12

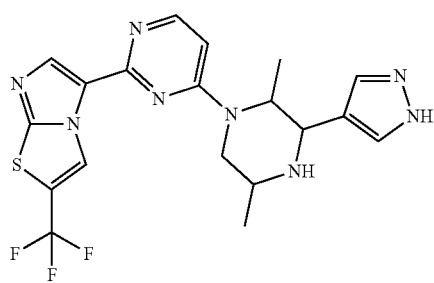

single stereoisomer

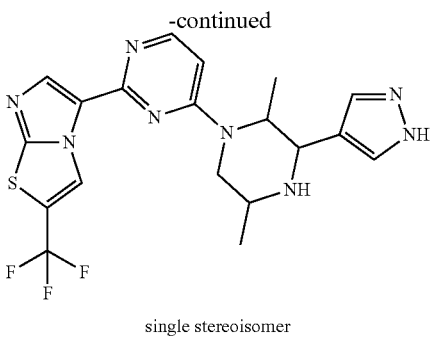

single stereoisomer

The racemic mixture of 5-[4-[2,5-dimethyl-3-(1H-pyrazol-4-yl)piperazin-1-yl]pyrimidin-2-yl]-2-(trifluoromethyl)imidazo[2,1-b]thiazole (prepared in a similar manner to Example 1) was separated by chiral supercritical fluid chromatography [Column: Chiralpak AD-H; Mobile phase: $CO_2$: methanol (+20 mM ammonia) 70:30] to give the isolated single enantiomers V-11 (6.0 mg, 41%, 99.5% ee) and V-12 (7.9 mg, 51%, 99.1% ee).

Example 111: Imino(methyl)((1-(2-(2-(trifluoromethyl)imidazo[2,1-b]thiazol-5-yl)pyrimidin-4-yl)piperidin-3-yl)methyl)-$\lambda^6$-sulfanone, V-18 and V-19

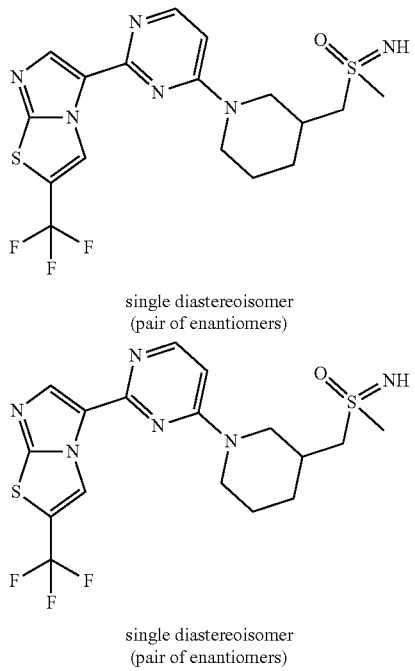

single diastereoisomer
(pair of enantiomers)

single diastereoisomer
(pair of enantiomers)

5-(4-Chloropyrimidin-2-yl)-2-(trifluoromethyl)imidazo[2,1-b]thiazole (25 mg, 0.082 mmol), 3-((methylsulfinyl)methyl)piperidine (62 mg, 0.123 mmol) and DIPEA (57 μL, 0.328 mmol) were dissolved in NMP (0.82 mL) and heated in a sealed tube at 100° C. for 16 hours. The reaction mixture was cooled to ambient temperature and purified directly by reverse phase preparative HPLC [Waters Sunfire C18, 10 μM, 100 Å column, gradient 10%-95% B (solvent A: 0.05% TFA in water; solvent B: $CH_3CN$) over 16 minutes at 25 mL/min]. The fractions were collected and freeze-dried to give 5-(4-(3-((methylsulfinyl)methyl)piperidin-1-yl)pyrimidin-2-yl)-2-(trifluoromethyl)imidazo[2,1-b]thiazole (as separated racemic diastereomers). Each diastereomer (15 mg, 0.035 mmol), ammonium carbamate (10.9 mg, 0.140 mmol) and (diacetoxyiodo)benzene (33.8 mg, 0.105 mmol) were combined in a round-bottomed flask before addition of MeOH/DCM (1:1 mixture 0.7 mL). The reaction was stirred at ambient temperature for 3 hours. The crude mixture was then purified by by reverse phase preparative HPLC [Waters Sunfire C18, 10 μM, 100 Å column, gradient 10%-95% B (solvent A: 0.1% ammonium hydroxide in water; solvent B: $CH_3CN$) over 16 minutes at 25 mL/min] to provide imino(methyl)((1-(2-(2-(trifluoromethyl)imidazo[2,1-b]thiazol-5-yl)pyrimidin-4-yl)piperidin-3-yl)methyl)-$\lambda^6$-sulfanone, V-18 and V-19.

The following compounds were prepared using a methodology similar to the one described in Example 111:

((2,5-Dimethyl-1-(2-(2-(trifluoromethyl)imidazo[2,1-b]thiazol-5-yl)pyrimidin-4-yl)piperidin-3-yl)methyl)(imino)(methyl)-$\lambda^6$-sulfanone, V-16 and V-17.

TABLE 8

Analytical data for compounds of Formula V

| V-# | LCMS (ES+) | LCMS (rt, min) | $^1$HNMR |
|---|---|---|---|
| V-1 | 493.8 | 2.77 | 1H NMR (500 MHz, DMSO-d6) δ 9.01 (s, 1H), 8.35 (d, 1H), 8.12 (s, 1H), 7.52 (t, 1H), 6.86 (d, 1H), 4.98 (br s, 1H), 4.47 (br s, 1H), 3.45 (dd, 1H), 3.02-2.97 (m, 1H), 2.97 (s, 3H), 2.87-2.79 (m, 2H), 2.21-2.15 (m, 2H), 1.05 (d, 3H). |
| V-2 | 493.9 | 2.76 | 1H NMR (500 MHz, DMSO-d6) δ 9.01 (s, 1H), 8.35 (d, 1H), 8.12 (s, 1H), 7.52 (t, 1H), 6.85 (d, 1H), 4.95 (br s, 1H), 4.43 (br s, 1H), 3.45 (dd, 1H), 3.02-2.97 (m, 1H), 2.97 (s, 3H), 2.87-2.79 (m, 2H), 2.20-2.13 (m, 2H), 1.05 (d, 3H). |
| V-3 | 422.1 | 2.50 | 1H NMR (500 MHz, Methanol-d4) δ 9.13 (q, 1H), 8.32 (d, 1H), 8.11 (s, 1H), 7.74 (br s, 2H), 6.75 (d, 1H), 4.71 (dd, 1H), 4.54 (br s, 1H), 4.31 (br s, 1H), 4.15-4.11 (m, 1H), 3.84 (td, 1H), 3.30-3.29 (m, 1H), 3.27-3.22 (m, 1H). |
| V-4 | 422.1 | 2.50 | 1H NMR (500 MHz, Methanol-d4) δ 9.13 (q, 1H), 8.32 (d, 1H), 8.11 (s, 1H), 7.74 (br d, 2H), 6.75 (d, 1H), 4.71 (dd, 1H), 4.54 (br s, 1H), 4.31 (br s, 1H), 4.15-4.11 (m, 1H), 3.84 (td, 1H), 3.30-3.27 (m, 1H), 3.25 (dd, 1H). |
| V-5 | 496.1 | 2.16 | 1H NMR (500 MHz, Methanol-d4) δ 9.13-9.08 (m, 1H), 8.32 (dd, J = 6.4, 1.5 Hz, 1H), 8.11 (d, J = 2.0 Hz, 1H), 7.67 (s, 2H), 6.82 (dd, J = 6.4, 1.5 Hz, 1H), 3.21-3.12 (m, 1H), 3.07 (t, J = 12.4 Hz, 1H), 2.94 (tt, J = 11.9, 4.2 Hz, 1H), 2.41-2.34 (m, 1H), 2.23 (dt, J = 12.2, 3.5 Hz, 1H), 1.89 (dq, J = 12.5, 6.0 Hz, 1H), 1.66 (ddd, J = 22.6, 12.9, 0.7 Hz, 6H), 1.15 (dd, J = 6.8, 2.8 Hz, 2H). |
| V-6 | 496.0 | 2.11 | 1H NMR (500 MHz, Methanol-d4) δ 9.11 (t, J = 1.4 Hz, 1H), 8.28 (d, J = 6.3 Hz, 1H), 8.12 (s, 1H), 7.57 (s, 2H), 6.74 (d, J = 6.4 Hz, 1H), 4.50 (d, J = 10.8 Hz, 1H), 4.45-4.38 (m, 1H), 3.69 (dd, J = 13.4, 3.8 Hz, 2H), 3.44 (t, J = 4.5 Hz, 1H), 2.30 (qt, J = 10.0, 5.0 Hz, 2H), 1.66 (d, J = 12.8 Hz, 3H), 1.62 (d, J = 12.8 Hz, 3H), 1.18 (d, J = 6.5 Hz, 2H). |

TABLE 8-continued

Analytical data for compounds of Formula V

| V-# | LCMS (ES+) | LCMS (rt, min) | ¹HNMR |
|---|---|---|---|
| V-7 | 406.1 | 2.64 | 1H NMR (500 MHz, Methanol-d4) δ 9.21-9.17 (m, 1H), 8.19 (d,7 = 6.1 Hz, 1H), 7.78 (s, 1H), 7.57 (s, 2H), 6.39 (d, J = 6.2 Hz, 1H), 4.22 (s, 1H), 3.98 (s, 1H), 3.60 (s, 3H), 2.52 (s, 1H), 2.17 (s, 1H). |
| V-8 | 383.0 | 2.28 | 1H NMR (400 MHz, DMSO-d6) δ 9.08 (q, J = 1.4 Hz, 1H), 8.32 (d, J = 6.3 Hz, 1H), 8.12 (s, 1H), 7.67 (t, J = 5.2 Hz, 1H), 6.79 (d, J = 6.3 Hz, 1H), 3.88 (s, 4H), 3.26 (d, J = 5.6 Hz, 1H), 2.62-2.53 (m, 2H), 2.46 (p, J = 1.8 Hz, 1H). |
| V-9 | 445.1 | 2.50 | 1H NMR (400 MHz, DMSO-d6) δ 9.11 (q, J = 1.4 Hz, 1H), 8.26 (d, J = 6.3 Hz, 1H), 8.05 (s, 1H), 6.70 (d, J = 6.3 Hz, 1H), 4.20 (s, 2H), 3.29 (s, 1H), 3.02 (dd, J = 11.3, 0.9 Hz, 7H), 2.85 (t, J = 11.7 Hz, 1H), 1.94-1.85 (m, 1H), 1.75 (q, J = 3.9 Hz, 1H), 1.57-1.44 (m, 2H). |
| V-10 | 397.1 | 2.42 | 1H NMR (400 MHz, DMSO-d6) δ 9.10 (q, J = 1.4 Hz, 1H), 8.27 (d, J = 6.3 Hz, 1H), 8.07 (s, 1H), 7.39 (s, 1H), 6.91 (s, 1H), 6.79 (d, J = 6.3 Hz, 1H), 4.34 (s, 2H), 3.21-2.97 (m, 2H), 2.36 (td, J = 10.9, 5.4 Hz, 1H), 1.97-1.87 (m, 1H), 1.82-1.63 (m, 2H), 1.45 (ddt, J = 16.2, 12.5, 6.5 Hz, 1H). |
| V-11 | 449.2 | 2.55 | 1H NMR (500 MHz, Methanol-d4) δ 9.04 (d, J = 9.9 Hz, 1H), 8.22 (d, J = 6.3 Hz, 1H), 8.04 (s, 1H), 7.68 (s, 2H), 6.69 (d, J = 6.3 Hz, 1H), 5.03 (s, 1H), 4.24 (d, J = 3.7 Hz, 1H), 3.81 (s, 1H), 3.00 (ddd, J = 9.5, 6.2, 3.1 Hz, 1H), 2.82 (s, 1H), 1.28 (d, J = 6.3 Hz, 3H), 1.08 (d, J = 6.8 Hz, 3H). |
| V-12 | 449.1 | 2.56 | 1H NMR (500 MHz, Methanol-d4) δ 9.04 (d, J = 9.9 Hz, 1H), 8.22 (d, J = 6.3 Hz, 1H), 8.04 (s, 1H), 7.68 (s, 2H), 6.69 (d, J = 6.3 Hz, 1H), 5.03 (s, 1H), 4.24 (d, J = 3.7 Hz, 1H), 3.81 (s, 1H), 3.00 (ddd, J = 9.5, 6.2, 3.1 Hz, 1H), 2.82 (s, 1H), 1.28 (d, J = 6.3 Hz, 3H), 1.08 (d, J = 6.8 Hz, 3H). |
| V-13 | 449.3 | 2.59 | 1H NMR (500 MHz, Methanol-d4) δ 9.11 (s, 1H), 8.42 (d, J = 6.3 Hz, 1H), 8.15 (s, 1H), 7.85 (s, 2H), 6.87 (d, J = 6.3 Hz, 1H), 4.88 (d, J = 4.2 Hz, 1H), 3.62 (ddd, J = 11.0, 6.4, 3.8 Hz, 1H), 3.19 (s, 1H), 2.67 (d, J = 5.4 Hz, 1H), 1.54 (d, J = 6.5 Hz, 3H), 1.31 (d, J = 7.1 Hz, 3H). |
| V-14 | 493.1 | 2.77 | 1H NMR (500 MHz, DMSO-d6) δ 8.99 (t, J = 2.6 Hz, 1H), 8.35 (d, J = 6.3 Hz, 1H), 8.15 (s, 1H), 7.51 (t, J = 53.7 Hz, 1H), 7.37 (t, J = 6.7 Hz, 1H), 6.88 (d, J = 6.3 Hz, 1H), 3.48-3.44 (m, 1H), 3.03-2.97 (m, 2H), 2.99 (s, 3H), 2.88-2.81 (m, 2H), 2.22-2.16 (m, 3H), 1.06 (d, J = 6.7 Hz, 3H). |
| V-15 | 422.1 | 2.49 | 1H NMR (500 MHz, DMSO-d6) δ 9.10 (d, J = 1.6 Hz, 1H), 8.35 (d, J = 6.3 Hz, 1H), 8.14 (s, 1H), 7.69 (s, 2H), 6.87 (d, J = 6.4 Hz, 1H), 4.58 (dd, J = 10.7, 2.6 Hz, 1H), 4.05-4.03 (m, 1H), 3.70 (td, J = 11.5, 2.6 Hz, 1H), 3.21-3.13 (m, 2H), 2.52-2.48 (m, 2H). |
| V-16 | 473.0 | 2.64 | — |
| V-17 | 473.0 | 2.65 | — |
| V-18 | 445.1 | 2.4 | 1H NMR (500 MHz, Methanol-d4) δ 9.15 (q, J = 1.4 Hz, 1H), 8.26 (d, J = 6.3 Hz, 1H), 8.12 (s, 1H), 6.70 (d, J = 6.4 Hz, 1H), 4.63 (s, 1H), 4.24 (s, 1H), 3.34-3.13 (m, 4H), 3.09 (d, J = 0.7 Hz, 3H), 2.32 (dtt, J = 12.6, 6.3, 3.0 Hz, 1H), 2.12 (dt, J = 12.7, 4.2 Hz, 1H), 1.90-1.80 (m, 1H), 1.75-1.56 (m, 2H). |
| V-19 | 445.1 | 2.41 | 1H NMR (500 MHz, Methanol-d4) δ 9.14 (q, J = 1.4 Hz, 1H), 8.25 (d, J = 6.3 Hz, 1H), 8.12 (s, 1H), 6.69 (d, J = 6.4 Hz, 1H), 4.69 (s, 1H), 4.27 (s, 1H), 3.34-3.21 (m, 2H), 3.20-3.13 (m, 2H), 3.10 (s, 3H), 2.37 (dddt, J = 13.9, 9.6, 8.0, 4.0 Hz, 1H), 2.12-2.03 (m, 1H), 1.93-1.81 (m, 1H), 1.76-1.55 (m, 2H). |

Purity and retention time of the compounds from this invention were measured by HPLC.

HPLC method: analytical reverse phase UPLC-MS was carried out on a waters Acquity UPLC-MS system equipped with a waters BEH 1.7 mm C-18 reverse phase column (2.1 mm×50 mm, 1.7 μm). The mobile phases were acetonitrile and water/acetonitrile (95:5 with 10 mM ammonium formate, pH9). Run time 5 min

Example 112: Additional Exemplary Compounds

Additional compounds of formula II were prepared using similar methodologies to those described in examples 1-111 above:

1-(4-(6-(6-(difluoromethyl)imidazo[1,2-b]pyridazin-3-yl)pyridin-2-yl)piperazin-1-yl)ethan-1-one, II-731

N-((4-(4-(imidazo[1,2-b]pyridazin-3-yl)pyridin-2-yl)morpholin-2-yl)methyl)methanesulfonamide, II-732

N-((1-(4-(6-(difluoromethyl)imidazo[1,2-b]pyridazin-3-yl)-5-methylpyridin-2-yl)piperidin-3-yl)methyl)methanesulfonamide, II-733

3-(2-(4-acetylpiperazin-1-yl)pyridin-4-yl)imidazo[1,2-b]pyridazine-6-carboxylic acid, II-734, N-(1-(4-(6-(pyridin-3-yl)imidazo[1,2-b]pyridazin-3-yl)pyridin-2-yl)piperidin-4-yl)acetamide, II-735

1-(4-(4-(6-(3-aminopyrrolidin-1-yl)imidazo[1,2-b]pyridazin-3-yl)pyridin-2-yl)piperazin-1-yl)ethan-1-one, II-736

1-(4-(4-(6-(pyridin-3-yl)imidazo[1,2-b]pyridazin-3-yl)pyridin-2-yl)piperazin-1-yl)ethan-1-one, II-737

1-(4-(4-(6-morpholinoimidazo[1,2-b]pyridazin-3-yl)pyridin-2-yl)piperazin-1-yl)ethan-1-one, II-738

N-(((2R,3S)-1-cyclopropyl-4-(6-(6-(difluoromethyl)imidazo[12-b]pyridazin-3-yl)pyrimidin-4-yl)-3-methylpiperazin-2-yl)methyl)methanesulfonamide, II-752

N-(((2S,3R)-1-cyclopropyl-4-(6-(6-(difluoromethyl)imidazo[1,2-b]pyridazin-3-yl)pyrimidin-4-yl)-3-methylpiperazin-2-yl)methyl)methanesulfonamide, II-753

N-(((2R,3S)-1-(6-(6-(difluoromethyl)imidazo[1,2-b]pyridazin-3-yl)pyrimidin-4-yl)-2-methylpiperidin-3-yl)methyl)methanesulfonamide, II-754

N-(((2S,3R)-1-(6-(6-(difluoromethyl)imidazo[1,2-b]pyridazin-3-yl)pyrimidin-4-yl)-2-methylpiperidin-3-yl)methyl)methanesulfonamide, II-755

N-(((2S,3S)-1-(6-(6-(difluoromethyl)imidazo[1,2-b]pyridazin-3-yl)pyrimidin-4-yl)-2-methylpiperidin-3-yl)methyl)methanesulfonamide, II-756 dimethyl((5-methyl-1-(6-(6-(trifluoromethyl)imidazo[1,2-b]pyridazin-3-yl)pyrimidin-4-yl)piperidin-3-yl)imino)-16-sulfanone, II-757

(2S,6S)-2-(1,3-dimethyl-1H-pyrazol-4-yl)-6-methyl-4-(6-(6-(trifluoromethyl)imidazo[1,2-b]pyridazin-3-yl)pyrimidin-4-yl)morpholine, II-758

(2R,6S)-2-(1,3-dimethyl-1H-pyrazol-4-yl)-6-methyl-4-(6-(6-(trifluoromethyl)imidazo[1,2-b]pyridazin-3-yl)pyrimidin-4-yl)morpholine, II-759

(2R,6R)-2-(1,3-dimethyl-1H-pyrazol-4-yl)-6-methyl-4-(6-(6-(trifluoromethyl)imidazo[1,2-b]pyridazin-3-yl)pyrimidin-4-yl)morpholine, II-760

(2S,6R)-2-(1,3-dimethyl-1H-pyrazol-4-yl)-6-methyl-4-(6-(6-(trifluoromethyl)imidazo[1,2-b]pyridazin-3-yl)pyrimidin-4-yl)morpholine, II-761

2-methyl-6-(5-methyl-1H-pyrazol-4-yl)-4-(6-(6-(trifluoromethyl)imidazo[1,2-b]pyridazin-3-yl)pyrimidin-4-yl)morpholine, II-762

N-(((2R,3R)-1-(6-(6-(difluoromethyl)imidazo[1,2-b]pyridazin-3-yl)pyrimidin-4-yl)-2-methylpiperidin-3-yl)methyl)methanesulfonamide, II-763

(((3S,5R)-1-(6-(6-(3-fluoroazetidin-1-yl)imidazo[1,2-b]pyridazin-3-yl)pyrimidin-4-yl)-5-methylpiperidin-3-yl)imino)dimethyl-16-sulfanone, II-764

(2S,6S)-2-methyl-6-(5-methyl-1H-pyrazol-4-yl)-4-(6-(6-(trifluoromethyl)imidazo[1,2-b]pyridazin-3-yl)pyrimidin-4-yl)morpholine, II-765

(2R,6R)-2-methyl-6-(5-methyl-1H-pyrazol-4-yl)-4-(6-(6-(trifluoromethyl)imidazo[1,2-b]pyridazin-3-yl)pyrimidin-4-yl)morpholine, II-766

(2S,6R)-2-methyl-6-(5-methyl-1H-pyrazol-4-yl)-4-(6-(6-(trifluoromethyl)imidazo[1,2-b]pyridazin-3-yl)pyrimidin-4-yl)morpholine, II-767

(2R,6S)-2-methyl-6-(5-methyl-1H-pyrazol-4-yl)-4-(6-(6-(trifluoromethyl)imidazo[1,2-b]pyridazin-3-yl)pyrimidin-4-yl)morpholine, II-768

N-(((2S,3S)-1-cyclopropyl-4-(6-(6-(difluoromethyl)imidazo[1,2-b]pyridazin-3-yl)pyrimidin-4-yl)-3-methylpiperazin-2-yl)methyl)methanesulfonamide, II-769

N-(((2R,3R)-1-cyclopropyl-4-(6-(6-(difluoromethyl)imidazo[1,2-b]pyridazin-3-yl)pyrimidin-4-yl)-3-methylpiperazin-2-yl)methyl)methanesulfonamide, II-770

N-(((2S,6R)-4-(6-(6-(difluoromethyl)imidazo[1,2-b]pyridazin-3-yl)pyrimidin-4-yl)-6-(trifluoromethyl)morpholin-2-yl)methyl)methanesulfonamide, II-771

N—(R)-1-((S)-4-(6-(6-(difluoromethyl)imidazo[1,2-b]pyridazin-3-yl)pyrimidin-4-yl)morpholin-2-yl)ethyl)methanesulfonamide, II-772

N-(((3S,5S)-1-(6-(6-(difluoromethyl)imidazo[1,2-b]pyridazin-3-yl)pyrimidin-4-yl)-4,4-difluoro-5-methylpiperidin-3-yl)methyl)methanesulfonamide, II-773

N-(((3S,5S)-5-cyclopropyl-1-(6-(6-(difluoromethyl)imidazo[12-b]pyridazin-3-yl)pyrimidin-4-yl)piperidin-3-yl)methyl)methanesulfonamide, II-774

N-((5-(6-(6-(difluoromethyl)imidazo[1,2-b]pyridazin-3-yl)pyrimidin-4-yl)-8,8-difluoro-5-azaspiro[2.5]octan-7-yl)methyl)methanesulfonamide, II-775

(S)—N-((4-(6-(6-(difluoromethyl)imidazo[1,2-b]pyridazin-3-yl)pyrimidin-4-yl)-6,6-dimethylmorpholin-2-yl)methyl)methanesulfonamide, II-776

N-((3R,5S)-1-(6-(6-(difluoromethyl)imidazo[1,2-b]pyridazin-3-yl)pyrimidin-4-yl)-5-methylpiperidin-3-yl)methanesulfonamide, II-777

N-(((3R,6S)-1-(6-(6-(difluoromethyl)imidazo[1,2-b]pyridazin-3-yl)pyrimidin-4-yl)-4,4-difluoro-6-methylpiperidin-3-yl)methyl)methanesulfonamide, II-778

N-((1-(6-(azetidin-3-yloxy)-4-(6-(difluoromethyl)imidazo[1,2-b]pyridazin-3-yl)pyridin-2-yl)piperidin-3-yl)methyl)methanesulfonamide, II-779

Additional compounds of formula III were prepared using similar methodologies to those described in examples 1-111 above:

3-(2-phenylpyridin-4-yl)pyrazolo[1,5-a]pyrimidine, III-15

2-(4-(pyrazolo[1,5-a]pyrimidin-3-yl)pyridin-2-yl)octahydro-6H-pyrido[1,2-a]pyrazin-6-one, III-16

Additional compounds of formula IV were prepared using similar methodologies to those described in examples 1-111 above:

3-(6-(4-acetylpiperazin-1-yl)-3-(trifluoromethyl)pyridin-2-yl)imidazo[1,2-a]pyrazine-6-carboxamide, IV-700

3-(2-(4-acetylpiperazin-1-yl)-5-methoxypyrimidin-4-yl)imidazo[1,2-a]pyrazine-6-carboxamide, IV-701

4-(3-(6-(difluoromethyl)imidazo[1,2-a]pyrazin-3-yl)-1,2,4-thiadiazol-5-yl)-2-(1H-pyrazol-4-yl)morpholine, IV-702

(S)—N-((4-(3-(6-(difluoromethyl)imidazo[1,2-a]pyrazin-3-yl)-1,2,4-thiadiazol-5-yl)morpholin-2-yl)methyl)methanesulfonamide, IV-703

2-(1H-pyrazol-4-yl)-4-(3-(6-(trifluoromethyl)imidazo[1,2-a]pyrazin-3-yl)-1,2,4-thiadiazol-5-yl)morpholine, IV-704

(S)—N-((4-(3-(6-(trifluoromethyl)imidazo[1,2-a]pyrazin-3-yl)-1,2,4-thiadiazol-5-yl)morpholin-2-yl)methyl)methanesulfonamide, IV-705

3-(4-(3-(4H-1,2,4-triazol-4-yl)piperidin-1-yl)pyrimidin-2-yl)-6-(trifluoromethyl)imidazo[1,2-a]pyrazine, IV-752

3-(2-((3R,5S)-3-(3-fluoro-1H-pyrazol-4-yl)-5-methylpiperidin-1-yl)pyrimidin-4-yl)-6-(trifluoromethyl)imidazo[1,2-a]pyrazine, IV-754

3-(2-((3S,5R)-3-methyl-5-(3-methyl-1H-pyrazol-4-yl)piperidin-1-yl)pyrimidin-4-yl)-6-(trifluoromethyl)imidazo[1,2-a]pyrazine, IV-755

-(2-((3R,5S)-3-methyl-5-(3-methyl-1H-pyrazol-4-yl)piperidin-1-yl)pyrimidin-4-yl)-6-(trifluoromethyl)imidazo[1,2-a]pyrazine, IV-756

3-(2-((3R,5S)-3-(3-fluoro-1H-pyrazol-4-yl)-5-methylpiperidin-1-yl)pyrimidin-4-yl)-6-(trifluoromethyl)imidazo[1,2-a]pyrazine, IV-757

3-(2-((3R,5R)-3-methyl-5-(3-methyl-1H-pyrazol-4-yl)piperidin-1-yl)pyrimidin-4-yl)-6-(trifluoromethyl)imidazo[1,2-a]pyrazine, IV-758

3-(2-((3S,5S)-3-methyl-5-(3-methyl-1H-pyrazol-4-yl)piperidin-1-yl)pyrimidin-4-yl)-6-(trifluoromethyl)imidazo[1,2-a]pyrazine, IV-759

(2R,6R)-2-methyl-6-(3-methyl-1H-pyrazol-4-yl)-4-(2-(6-(trifluoromethyl)imidazo[1,2-a]pyrazin-3-yl)pyrimidin-4-yl)morpholine, IV-760

(2S,6S)-2-methyl-6-(3-methyl-1H-pyrazol-4-yl)-4-(2-(6-(trifluoromethyl)imidazo[1,2-a]pyrazin-3-yl)pyrimidin-4-yl)morpholine, IV-761

(2R,6S)-2-methyl-6-(3-methyl-1H-pyrazol-4-yl)-4-(2-(6-(trifluoromethyl)imidazo[1,2-a]pyrazin-3-yl)pyrimidin-4-yl)morpholine, IV-762

(2S,6R)-2-methyl-6-(3-methyl-1H-pyrazol-4-yl)-4-(2-(6-(trifluoromethyl)imidazo[1,2-a]pyrazin-3-yl)pyrimidin-4-yl)morpholine, IV-763

3-(4-((3R,5S)-3-(3-fluoro-1H-pyrazol-4-yl)-5-methylpiperidin-1-yl)pyrimidin-2-yl)-6-(trifluoromethyl)imidazo[1,2-a]pyrazine, IV-764

3-(2-((3S,5R)-3-(3-fluoro-1H-pyrazol-4-yl)-5-methylpiperidin-1-yl)pyrimidin-4-yl)-6-(trifluoromethyl)imidazo[1,2-a]pyrazine, IV-765

3-(2-((3R,5R)-3-(3-fluoro-1H-pyrazol-4-yl)-5-methylpiperidin-1-yl)pyrimidin-2-yl)-6-(trifluoromethyl)imidazo[1,2-a]pyrazine, IV-766

3-(2-((3S,5S)-3-(3-fluoro-1H-pyrazol-4-yl)-5-methylpiperidin-1-yl)pyrimidin-2-yl)-6-(trifluoromethyl)imidazo[1,2-a]pyrazine, IV-767

3-(4-((3S,5R)-3-methyl-5-(1H-pyrazol-4-yl)piperidin-1-yl)pyrimidin-2-yl)-6-(trifluoromethyl)imidazo[1,2-a]pyrazine, IV-768

3-(4-((3R,5S)-3-methyl-5-(1H-pyrazol-4-yl)piperidin-1-yl)pyrimidin-2-yl)-6-(trifluoromethyl)imidazo[1,2-a]pyrazine, IV-769

3-(4-((3R,5R)-3-methyl-5-(1H-pyrazol-4-yl)piperidin-1-yl)pyrimidin-2-yl)-6-(trifluoromethyl)imidazo[1,2-a]pyrazine, IV-770

3-(4-((3S,5S)-3-methyl-5-(1H-pyrazol-4-yl)piperidin-1-yl)pyrimidin-2-yl)-6-(trifluoromethyl)imidazo[1,2-a]pyrazine, IV-771

(((3S,5R)-1-(2-(6-(difluoromethyl)imidazo[1,2-a]pyrazin-3-yl)pyrimidin-4-yl)-5-methylpiperidin-3-yl)imino)dimethyl-16-sulfanone, IV-772

(((3S,5R)-1-(2-(6-chloroimidazo[1,2-a]pyrazin-3-yl)pyrimidin-4-yl)-5-methylpiperidin-3-yl)imino)dimethyl-16-sulfanone, IV-773

(3S,5R)-5-(3-methyl-1H-pyrazol-4-yl)-1-(2-(6-(trifluoromethyl)imidazo[1,2-a]pyrazin-3-yl)pyrimidin-4-yl)piperidin-3-ol, IV-774

(3R,5S)-5-(3-methyl-1H-pyrazol-4-yl)-1-(2-(6-(trifluoromethyl)imidazo[1,2-a]pyrazin-3-yl)pyrimidin-4-yl)piperidin-3-ol, IV-775

(3R,5R)-5-(3-methyl-1H-pyrazol-4-yl)-1-(2-(6-(trifluoromethyl)imidazo[1,2-a]pyrazin-3-yl)pyrimidin-4-yl)piperidin-3-ol, IV-776

(3S,5S)-5-(3-methyl-1H-pyrazol-4-yl)-1-(2-(6-(trifluoromethyl)imidazo[1,2-a]pyrazin-3-yl)pyrimidin-4-yl)piperidin-3-ol, IV-777 cyclopropyl((2R,3S,6S)-3,6-dimethyl-2-(1H-pyrazol-4-yl)-4-(2-(6-(trifluoromethyl)imidazo[1,2-a]pyrazin-3-yl)pyrimidin-4-yl)piperazin-1-yl)methanone, IV-778

((2R,3S,6S)-3,6-dimethyl-2-(1H-pyrazol-4-yl)-4-(2-(6-(trifluoromethyl)imidazo[1,2-a]pyrazin-3-yl)pyrimidin-4-yl)piperazin-1-yl)(isoxazol-4-yl)methanone, IV-779

An additional compound of formula V was prepared using similar methodologies to those described in examples 1-111 above:

2-(1H-pyrazol-4-yl)-4-(2-(2-(trifluoromethyl)imidazo[2,1-b]thiazol-5-yl)pyrimidin-4-yl)morpholine, V-20

Example 113: GCN2 Enzyme Inhibition Assay

Compounds were screened for their ability to inhibit GCN2 kinase activity using a Transcreener® ADP$^2$ fluorescence polarization assay that detects ADP levels (BellBrook Labs, WI). Assays were carried out in a buffer consisting of 25 mM Tris-HCl (pH 7.5), 50 mM NaCl, 10 mM MgCl$_2$ and 1 mM DTT. Final substrate concentrations were 280 µM ATP and 200 µM peptidic substrate (H-Gly-Arg-Ser-Arg-Ser-Arg-Ser-Arg-Ser-Arg-Ser-Arg-Ser-Arg-OH [(RS)$_7$], Bachem, Switzerland). Assays were carried out at 25° C. in the presence of a (typical) final concentration of 4 nM GCN2 kinase.

An assay buffer containing GCN2 kinase and (RS)$_7$ was prepared. 4.7 µL of this stock solution was placed per well of a black, low volume, 384-well microtitre plate (e.g. catalogue number 3676, Corning Inc., NY). To this was added 0.65 µM of DMSO containing serial dilutions of the test compound (typical final concentrations of test compound were 0 to 8 µM). The plate was incubated for 10 minutes at 25° C. prior to the addition of 4.7 µL of ATP stock buffer to initiate the enzyme reaction. The reaction was allowed to proceed for 1 hour at 25° C., prior to the addition of 10 µL detection buffer (consisting of appropriate concentrations of ADP$^2$ antibody and ADP Alexa633 tracer in 1× stop and detect buffer as supplied by BellBrook Labs). The reaction was left to incubate for 1 hour at 25° C., prior to measuring the fluorescence polarisation signal (mP) in each well using a PHERAstar FS reader (BMG Labtech, Germany).

Fluorescence polarization values were normalized to an in plate standard curve consisting of various ratios of ATP to ADP in assay buffer to a final total concentration of 280 µM. 9.4 µL of each ATP:ADP ratio buffer was added to the plate along with 0.65 µL DMSO, prior to addition of detection buffer, to mimic assay volumes and conditions. The standard curve was used to convert mP values obtained from test wells into percentage ATP converted to ADP. Percentage inhibition of enzyme activity was then calculated at each compound dose. IC$_{50}$ and Ki$_{(app)}$ (using known assay and kinetic parameters) values were calculated from percentage inhibition data using a non-linear, tight-binding algorithm. All data analysis was undertaken using the Screener® software package (Genedata, Switzerland).

TABLE 9

Enzyme activity for compounds of Formula II

| Compound of formula II | GCN2 (Ki) |
|---|---|
| II-1 | ++ |
| II-2 | +++ |
| II-3 | +++ |
| II-4 | ++ |
| II-5 | ++ |
| II-6 | ++ |
| II-7 | + |
| II-8 | ++ |
| II-9 | ++ |
| II-10 | ++ |
| II-11 | ++ |
| II-12 | ++ |
| II-13 | +++ |
| II-14 | ++ |
| II-15 | ++ |
| II-16 | ++ |
| II-17 | ++ |
| II-18 | +++ |
| II-19 | ++ |
| II-20 | ++ |
| II-21 | ++ |
| II-22 | ++ |
| II-23 | ++ |
| II-24 | ++ |
| II-25 | ++ |
| II-26 | ++ |
| II-27 | ++ |
| II-28 | ++ |
| II-29 | ++ |
| II-30 | ++ |
| II-31 | +++ |
| II-32 | +++ |
| II-33 | +++ |
| II-34 | +++ |
| II-35 | ++ |
| II-36 | +++ |
| II-37 | ++ |
| II-38 | ++ |
| II-39 | ++ |
| II-40 | +++ |
| II-41 | ++ |
| II-42 | ++ |
| II-43 | + |
| II-44 | ++ |
| II-45 | +++ |
| II-46 | ++ |

TABLE 9-continued

Enzyme activity for compounds of Formula II

| Compound of formula II | GCN2 (Ki) |
|---|---|
| II-47 | ++ |
| II-48 | ++ |
| II-49 | ++ |
| II-50 | ++ |
| II-51 | ++ |
| II-52 | ++ |
| II-53 | +++ |
| II-54 | ++ |
| II-55 | +++ |
| II-56 | ++ |
| II-57 | +++ |
| II-58 | +++ |
| II-59 | +++ |
| II-60 | +++ |
| II-61 | +++ |
| II-62 | ++ |
| II-63 | +++ |
| II-64 | +++ |
| II-65 | +++ |
| II-66 | +++ |
| II-67 | +++ |
| II-68 | +++ |
| II-69 | +++ |
| II-70 | ++ |
| II-71 | +++ |
| II-72 | +++ |
| II-73 | ++ |
| II-74 | +++ |
| II-75 | +++ |
| II-76 | ++ |
| II-77 | ++ |
| II-78 | +++ |
| II-79 | ++ |
| II-80 | +++ |
| II-81 | ++ |
| II-82 | ++ |
| II-83 | +++ |
| II-84 | +++ |
| II-85 | +++ |
| II-86 | +++ |
| II-87 | +++ |
| II-88 | ++ |
| II-89 | +++ |
| II-90 | ++ |
| II-91 | +++ |
| II-92 | +++ |
| II-93 | +++ |
| II-94 | +++ |
| II-95 | ++ |
| II-96 | +++ |
| II-97 | ++ |
| II-98 | ++ |
| II-99 | +++ |
| II-100 | ++ |
| II-101 | +++ |
| II-102 | ++ |
| II-103 | +++ |
| II-104 | ++ |
| II-105 | +++ |
| II-106 | +++ |
| II-107 | ++ |
| II-108 | ++ |
| II-109 | ++ |
| II-110 | +++ |
| II-111 | +++ |
| II-112 | +++ |
| II-113 | ++ |
| II-114 | ++ |
| II-115 | ++ |
| II-116 | +++ |
| II-117 | ++ |
| II-118 | ++ |
| II-119 | +++ |
| II-120 | +++ |
| II-121 | +++ |
| II-122 | +++ |
| II-123 | ++ |
| II-124 | +++ |
| II-125 | +++ |
| II-126 | ++ |
| II-127 | ++ |
| II-128 | ++ |
| II-129 | +++ |
| II-130 | ++ |
| II-131 | +++ |
| II-132 | +++ |
| II-133 | +++ |
| II-134 | ++ |
| II-135 | ++ |
| II-136 | +++ |
| II-137 | ++ |
| II-138 | ++ |
| II-139 | ++ |
| II-140 | ++ |
| II-141 | +++ |
| II-142 | +++ |
| II-143 | +++ |
| II-144 | ++ |
| II-145 | ++ |
| II-146 | ++ |
| II-147 | ++ |
| II-148 | +++ |
| II-149 | +++ |
| II-150 | ++ |
| II-151 | ++ |
| II-152 | ++ |
| II-153 | +++ |
| II-154 | +++ |
| II-155 | ++ |
| II-156 | ++ |
| II-157 | +++ |
| II-158 | ++ |
| II-159 | ++ |
| II-160 | ++ |
| II-161 | ++ |
| II-162 | ++ |
| II-163 | ++ |
| II-164 | ++ |
| II-165 | ++ |
| II-166 | ++ |
| II-167 | ++ |
| II-168 | ++ |
| II-169 | ++ |
| II-170 | ++ |
| II-171 | ++ |
| II-172 | ++ |
| II-173 | ++ |
| II-174 | ++ |
| II-175 | ++ |
| II-176 | ++ |
| II-177 | +++ |
| II-178 | ++ |
| II-179 | ++ |
| II-180 | ++ |
| II-181 | + |
| II-182 | ++ |
| II-183 | ++ |
| II-184 | ++ |
| II-185 | ++ |
| II-186 | ++ |
| II-187 | ++ |
| II-188 | ++ |
| II-189 | ++ |
| II-190 | ++ |
| II-191 | ++ |
| II-192 | ++ |
| II-193 | ++ |
| II-194 | ++ |
| II-195 | ++ |
| II-196 | ++ |

TABLE 9-continued

Enzyme activity for compounds of Formula II

| Compound of formula II | GCN2 (Ki) |
|---|---|
| II-197 | +++ |
| II-198 | ++ |
| II-199 | ++ |
| II-200 | ++ |
| II-201 | ++ |
| II-202 | +++ |
| II-203 | ++ |
| II-204 | ++ |
| II-205 | ++ |
| II-206 | ++ |
| II-207 | ++ |
| II-208 | ++ |
| II-209 | ++ |
| II-210 | ++ |
| II-211 | ++ |
| II-212 | ++ |
| II-213 | +++ |
| II-214 | ++ |
| II-215 | ++ |
| II-216 | ++ |
| II-217 | ++ |
| II-218 | ++ |
| II-219 | +++ |
| II-220 | + |
| II-221 | +++ |
| II-222 | ++ |
| II-223 | ++ |
| II-224 | ++ |
| II-225 | +++ |
| II-226 | ++ |
| II-227 | ++ |
| II-228 | ++ |
| II-229 | +++ |
| II-230 | +++ |
| II-231 | ++ |
| II-232 | ++ |
| II-233 | +++ |
| II-234 | ++ |
| II-235 | ++ |
| II-236 | ++ |
| II-237 | +++ |
| II-238 | ++ |
| II-239 | +++ |
| II-240 | +++ |
| II-241 | + |
| II-242 | ++ |
| II-243 | ++ |
| II-244 | ++ |
| II-245 | ++ |
| II-246 | ++ |
| II-247 | +++ |
| II-248 | ++ |
| II-249 | ++ |
| II-250 | ++ |
| II-251 | ++ |
| II-252 | ++ |
| II-253 | ++ |
| II-254 | ++ |
| II-255 | ++ |
| II-256 | ++ |
| II-257 | ++ |
| II-258 | +++ |
| II-259 | +++ |
| II-260 | ++ |
| II-261 | ++ |
| II-262 | +++ |
| II-263 | ++ |
| II-264 | ++ |
| II-265 | ++ |
| II-266 | +++ |
| II-267 | ++ |
| II-268 | +++ |
| II-269 | ++ |
| II-270 | +++ |
| II-271 | ++ |
| II-272 | ++ |
| II-273 | ++ |
| II-274 | ++ |
| II-275 | ++ |
| II-276 | ++ |
| II-277 | +++ |
| II-278 | +++ |
| II-279 | ++ |
| II-280 | ++ |
| II-281 | +++ |
| II-282 | ++ |
| II-283 | ++ |
| II-284 | ++ |
| II-285 | ++ |
| II-286 | ++ |
| II-287 | ++ |
| II-288 | ++ |
| II-289 | ++ |
| II-290 | ++ |
| II-291 | +++ |
| II-292 | ++ |
| II-293 | ++ |
| II-294 | ++ |
| II-295 | + |
| II-296 | + |
| II-297 | ++ |
| II-298 | ++ |
| II-299 | ++ |
| II-300 | +++ |
| II-301 | ++ |
| II-302 | ++ |
| II-303 | ++ |
| II-304 | +++ |
| II-305 | ++ |
| II-306 | ++ |
| II-307 | ++ |
| II-308 | ++ |
| II-309 | + |
| II-310 | ++ |
| II-311 | +++ |
| II-312 | +++ |
| II-313 | +++ |
| II-314 | ++ |
| II-315 | ++ |
| II-316 | +++ |
| II-317 | ++ |
| II-318 | ++ |
| II-319 | ++ |
| II-320 | ++ |
| II-321 | ++ |
| II-322 | ++ |
| II-323 | ++ |
| II-324 | ++ |
| II-325 | ++ |
| II-326 | ++ |
| II-327 | ++ |
| II-328 | ++ |
| II-329 | +++ |
| II-330 | ++ |
| II-331 | +++ |
| II-332 | ++ |
| II-333 | ++ |
| II-334 | ++ |
| II-335 | ++ |
| II-336 | + |
| II-337 | ++ |
| II-338 | ++ |
| II-339 | ++ |
| II-340 | ++ |
| II-341 | ++ |
| II-342 | ++ |
| II-343 | ++ |
| II-344 | +++ |
| II-345 | +++ |
| II-346 | ++ |

TABLE 9-continued

Enzyme activity for compounds of Formula II

| Compound of formula II | GCN2 (Ki) |
|---|---|
| II-347 | +++ |
| II-348 | ++ |
| II-349 | ++ |
| II-350 | +++ |
| II-351 | ++ |
| II-352 | ++ |
| II-353 | ++ |
| II-354 | ++ |
| II-355 | ++ |
| II-356 | ++ |
| II-357 | ++ |
| II-358 | ++ |
| II-359 | ++ |
| II-360 | ++ |
| II-361 | +++ |
| II-362 | ++ |
| II-363 | ++ |
| II-364 | +++ |
| II-365 | ++ |
| II-366 | +++ |
| II-367 | ++ |
| II-368 | ++ |
| II-369 | ++ |
| II-370 | ++ |
| II-371 | +++ |
| II-372 | + |
| II-373 | +++ |
| II-374 | ++ |
| II-375 | +++ |
| II-376 | ++ |
| II-377 | ++ |
| II-378 | ++ |
| II-379 | ++ |
| II-380 | + |
| II-381 | +++ |
| II-382 | ++ |
| II-383 | ++ |
| II-384 | +++ |
| II-385 | +++ |
| II-386 | +++ |
| II-387 | ++ |
| II-388 | ++ |
| II-389 | ++ |
| II-390 | +++ |
| II-391 | +++ |
| II-392 | ++ |
| II-393 | ++ |
| II-394 | ++ |
| II-395 | ++ |
| II-396 | ++ |
| II-397 | +++ |
| II-398 | ++ |
| II-399 | ++ |
| II-400 | ++ |
| II-401 | ++ |
| II-402 | ++ |
| II-403 | +++ |
| II-404 | ++ |
| II-405 | ++ |
| II-406 | + |
| II-407 | ++ |
| II-408 | ++ |
| II-409 | ++ |
| II-410 | ++ |
| II-411 | ++ |
| II-412 | ++ |
| II-413 | + |
| II-414 | ++ |
| II-415 | ++ |
| II-416 | +++ |
| II-417 | ++ |
| II-418 | ++ |
| II-419 | ++ |
| II-420 | ++ |
| II-421 | ++ |
| II-422 | ++ |
| II-423 | ++ |
| II-424 | +++ |
| II-425 | ++ |
| II-426 | ++ |
| II-427 | +++ |
| II-428 | ++ |
| II-429 | ++ |
| II-430 | ++ |
| II-431 | +++ |
| II-432 | +++ |
| II-433 | +++ |
| II-434 | ++ |
| II-435 | ++ |
| II-436 | ++ |
| II-437 | +++ |
| II-438 | ++ |
| II-439 | ++ |
| II-440 | ++ |
| II-441 | ++ |
| II-442 | ++ |
| II-443 | +++ |
| II-444 | +++ |
| II-445 | ++ |
| II-446 | ++ |
| II-447 | ++ |
| II-448 | +++ |
| II-449 | +++ |
| II-450 | ++ |
| II-451 | ++ |
| II-452 | ++ |
| II-453 | ++ |
| II-454 | ++ |
| II-455 | ++ |
| II-456 | ++ |
| II-457 | ++ |
| II-458 | +++ |
| II-459 | + |
| II-460 | ++ |
| II-461 | +++ |
| II-462 | +++ |
| II-463 | +++ |
| II-464 | ++ |
| II-465 | ++ |
| II-466 | +++ |
| II-467 | +++ |
| II-468 | ++ |
| II-469 | ++ |
| II-470 | ++ |
| II-471 | ++ |
| II-472 | +++ |
| II-473 | ++ |
| II-474 | ++ |
| II-475 | ++ |
| II-476 | ++ |
| II-477 | ++ |
| II-478 | ++ |
| II-479 | +++ |
| II-480 | ++ |
| II-481 | ++ |
| II-482 | +++ |
| II-483 | ++ |
| II-484 | ++ |
| II-485 | +++ |
| II-486 | ++ |
| II-487 | ++ |
| II-488 | ++ |
| II-489 | + |
| II-490 | +++ |
| II-491 | +++ |
| II-492 | ++ |
| II-493 | ++ |
| II-494 | +++ |
| II-495 | +++ |
| II-496 | ++ |

TABLE 9-continued

Enzyme activity for compounds of Formula II

| Compound of formula II | GCN2 (Ki) |
|---|---|
| II-497 | ++ |
| II-498 | ++ |
| II-499 | ++ |
| II-500 | ++ |
| II-501 | ++ |
| II-502 | ++ |
| II-503 | ++ |
| II-504 | ++ |
| II-505 | ++ |
| II-506 | ++ |
| II-507 | +++ |
| II-508 | ++ |
| II-509 | +++ |
| II-510 | ++ |
| II-511 | +++ |
| II-512 | ++ |
| II-513 | ++ |
| II-514 | ++ |
| II-515 | +++ |
| II-516 | ++ |
| II-517 | ++ |
| II-518 | ++ |
| II-519 | ++ |
| II-520 | ++ |
| II-521 | ++ |
| II-522 | ++ |
| II-523 | +++ |
| II-524 | +++ |
| II-525 | +++ |
| II-526 | +++ |
| II-527 | +++ |
| II-528 | +++ |
| II-529 | ++ |
| II-530 | ++ |
| II-531 | ++ |
| II-532 | ++ |
| II-533 | ++ |
| II-534 | ++ |
| II-535 | ++ |
| II-536 | ++ |
| II-537 | +++ |
| II-538 | +++ |
| II-539 | ++ |
| II-540 | ++ |
| II-541 | +++ |
| II-542 | +++ |
| II-543 | ++ |
| II-544 | +++ |
| II-545 | ++ |
| II-546 | +++ |
| II-547 | ++ |
| II-548 | + |
| II-549 | ++ |
| II-550 | +++ |
| II-551 | ++ |
| II-552 | ++ |
| II-553 | ++ |
| II-554 | ++ |
| II-555 | ++ |
| II-556 | ++ |
| II-557 | ++ |
| II-558 | +++ |
| II-559 | ++ |
| II-560 | +++ |
| II-561 | ++ |
| II-562 | +++ |
| II-563 | ++ |
| II-564 | ++ |
| II-565 | ++ |
| II-566 | +++ |
| II-567 | ++ |
| II-568 | +++ |
| II-569 | ++ |
| II-570 | ++ |
| II-571 | ++ |
| II-572 | ++ |
| II-573 | ++ |
| II-574 | ++ |
| II-575 | ++ |
| II-576 | +++ |
| II-577 | +++ |
| II-578 | +++ |
| II-579 | ++ |
| II-580 | ++ |
| II-581 | ++ |
| II-582 | + |
| II-583 | + |
| II-584 | ++ |
| II-585 | +++ |
| II-586 | ++ |
| II-587 | +++ |
| II-588 | ++ |
| II-589 | ++ |
| II-590 | + |
| II-591 | +++ |
| II-592 | +++ |
| II-593 | +++ |
| II-594 | ++ |
| II-595 | ++ |
| II-596 | ++ |
| II-597 | ++ |
| II-598 | ++ |
| II-599 | ++ |
| II-600 | + |
| II-601 | +++ |
| II-602 | +++ |
| II-603 | ++ |
| II-604 | ++ |
| II-605 | ++ |
| II-606 | +++ |
| II-607 | +++ |
| II-608 | ++ |
| II-609 | +++ |
| II-610 | ++ |
| II-611 | ++ |
| II-612 | +++ |
| II-613 | ++ |
| II-614 | ++ |
| II-615 | ++ |
| II-616 | ++ |
| II-617 | ++ |
| II-618 | +++ |
| II-619 | ++ |
| II-620 | ++ |
| II-621 | ++ |
| II-622 | ++ |
| II-623 | +++ |
| II-624 | ++ |
| II-625 | ++ |
| II-626 | +++ |
| II-627 | ++ |
| II-628 | ++ |
| II-629 | ++ |
| II-630 | ++ |
| II-631 | +++ |
| II-632 | ++ |
| II-633 | ++ |
| II-634 | ++ |
| II-635 | ++ |
| II-636 | ++ |
| II-637 | ++ |
| II-638 | ++ |
| II-639 | ++ |
| II-640 | ++ |
| II-641 | ++ |
| II-642 | +++ |
| II-643 | +++ |
| II-644 | ++ |
| II-645 | ++ |
| II-646 | ++ |

TABLE 9-continued

Enzyme activity for compounds of Formula II

| Compound of formula II | GCN2 (Ki) |
|---|---|
| II-647 | ++ |
| II-648 | +++ |
| II-649 | ++ |
| II-650 | +++ |
| II-651 | ++ |
| II-652 | ++ |
| II-653 | ++ |
| II-654 | ++ |
| II-655 | ---- |
| II-656 | ---- |
| II-657 | ---- |
| II-658 | ---- |
| II-659 | ---- |
| II-660 | ---- |
| II-661 | ---- |
| II-662 | ---- |
| II-663 | ---- |
| II-664 | ---- |
| II-665 | ---- |
| II-666 | ---- |
| II-667 | ---- |
| II-668 | ---- |
| II-669 | ---- |
| II-670 | ---- |
| II-671 | ---- |
| II-672 | ---- |
| II-673 | ---- |
| II-674 | ---- |
| II-675 | ---- |
| II-676 | ++ |
| II-677 | ---- |
| II-678 | ---- |
| II-679 | ---- |
| II-680 | ---- |
| II-681 | ---- |
| II-682 | ---- |
| II-683 | ---- |
| II-684 | ---- |
| II-685 | ---- |
| II-686 | ---- |
| II-687 | ---- |
| II-688 | ---- |
| II-689 | ---- |
| II-690 | ---- |
| II-691 | ++ |
| II-692 | ++ |
| II-693 | ++ |
| II-694 | ++ |
| II-695 | +++ |
| II-696 | ++ |
| II-697 | + |
| II-698 | +++ |
| II-699 | ++ |
| II-700 | +++ |
| II-701 | ++ |
| II-702 | ++ |
| II-703 | +++ |
| II-704 | ++ |
| II-705 | +++ |
| II-706 | ++ |
| II-707 | ++ |
| II-708 | + |
| II-709 | ++ |
| II-710 | ++ |
| II-711 | ++ |
| II-712 | + |
| II-713 | ++ |
| II-714 | ---- |
| II-715 | ++ |
| II-716 | +++ |
| II-717 | +++ |
| II-718 | ++ |
| II-719 | ++ |
| II-720 | ++ |
| II-721 | ++ |
| II-722 | ++ |
| II-723 | ++ |
| II-724 | ++ |
| II-725 | +++ |
| II-726 | ++ |
| II-727 | ++ |
| II-728 | ++ |
| II-729 | +++ |
| II-730 | ++ |
| II-731 | + |
| II-732 | + |
| II-733 | + |
| II-734 | + |
| II-735 | + |
| II-736 | + |
| II-737 | + |
| II-738 | + |
| II-739 | ++ |
| II-740 | +++ |
| II-741 | +++ |
| II-742 | ++ |
| II-743 | ++ |
| II-744 | ++ |
| II-745 | ++ |
| II-746 | ++ |
| II-747 | ++ |
| II-748 | ++ |
| II-749 | ++ |
| II-750 | +++ |

+++ for Ki < 10 nM;
++ for Ki in 10 nM-1 μM range;
+ for Ki > 1 μM;
---- when no data available

TABLE 10

Enzyme activity for compounds of Formula II

| Compound II | GCN2 IC$_{50}$ |
|---|---|
| II-752 | +++ |
| II-753 | ++ |
| II-754 | + |
| II-755 | + |
| II-756 | + |
| II-757 | ++ |
| II-758 | + |
| II-759 | ++ |
| II-760 | ++ |
| II-761 | + |
| II-762 | ++ |
| II-763 | +++ |
| II-764 | ++ |
| II-765 | ++ |
| II-766 | ++ |
| II-767 | ++ |
| II-768 | +++ |
| II-769 | ++ |
| II-770 | ++ |
| II-771 | ++ |
| II-772 | ++ |

+++ for IC$_{50}$ < 10 nM;
++ for IC$_{50}$ in 10 nM-1 μM range;
+ for IC$_{50}$ > 1 μM

TABLE 11

Enzyme activity for compounds of Formula III

| Compound III | GCN2 (Ki) |
| --- | --- |
| III-1 | ++ |
| III-2 | +++ |
| III-3 | ++ |
| III-4 | +++ |
| III-5 | ++ |
| III-6 | +++ |
| III-7 | +++ |
| III-8 | ++ |
| III-9 | ++ |
| III-10 | +++ |
| III-11 | +++ |
| III-12 | +++ |
| III-13 | +++ |
| III-14 | ++ |
| III-15 | + |
| III-16 | + |

+++ for Ki < 10 nM;
++ for Ki in 10 nM-1 μM range;
+ for Ki > 1 μM;
---- when no data available

TABLE 12

Enzyme activity for compounds of Formula IV

| Compound of Formula IV- | GCN2 (Ki) |
| --- | --- |
| IV-1 | + |
| IV-2 | + |
| IV-3 | +++ |
| IV-4 | +++ |
| IV-5 | ++ |
| IV-6 | +++ |
| IV-7 | ++ |
| IV-8 | +++ |
| IV-9 | +++ |
| IV-10 | +++ |
| IV-11 | ++ |
| IV-12 | +++ |
| IV-13 | ++ |
| IV-14 | +++ |
| IV-15 | ++ |
| IV-16 | ++ |
| IV-17 | + |
| IV-18 | +++ |
| IV-19 | +++ |
| IV-20 | ++ |
| IV-21 | + |
| IV-22 | + |
| IV-23 | + |
| IV-24 | + |
| IV-25 | + |
| IV-26 | + |
| IV-27 | ++ |
| IV-28 | ++ |
| IV-29 | + |
| IV-30 | + |
| IV-31 | + |
| IV-32 | + |
| IV-33 | + |
| IV-34 | + |
| IV-35 | + |
| IV-36 | + |
| IV-37 | + |
| IV-38 | ++ |
| IV-39 | + |
| IV-40 | ++ |
| IV-41 | + |
| IV-42 | ++ |
| IV-43 | + |
| IV-44 | + |
| IV-45 | + |
| IV-46 | + |
| IV-47 | + |
| IV-48 | + |
| IV-49 | + |
| IV-50 | ++ |
| IV-51 | + |
| IV-52 | + |
| IV-53 | ++ |
| IV-54 | ++ |
| IV-55 | ++ |
| IV-56 | + |
| IV-57 | + |
| IV-58 | ++ |
| IV-59 | +++ |
| IV-60 | +++ |
| IV-61 | + |
| IV-62 | + |
| IV-63 | + |
| IV-64 | + |
| IV-65 | + |
| IV-66 | + |
| IV-67 | + |
| IV-68 | + |
| IV-69 | + |
| IV-70 | + |
| IV-71 | + |
| IV-72 | + |
| IV-73 | + |
| IV-74 | + |
| IV-75 | + |
| IV-76 | + |
| IV-77 | + |
| IV-78 | + |
| IV-79 | + |
| IV-80 | + |
| IV-81 | + |
| IV-82 | + |
| IV-83 | + |
| IV-84 | + |
| IV-85 | + |
| IV-86 | + |
| IV-87 | + |
| IV-88 | + |
| IV-89 | + |
| IV-90 | + |
| IV-91 | + |
| IV-92 | + |
| IV-93 | + |
| IV-94 | + |
| IV-95 | + |
| IV-96 | ++ |
| IV-97 | ++ |
| IV-98 | + |
| IV-99 | + |
| IV-100 | + |
| IV-101 | + |
| IV-102 | + |
| IV-103 | + |
| IV-104 | + |
| IV-105 | + |
| IV-106 | ++ |
| IV-107 | ++ |
| IV-108 | ++ |
| IV-109 | ++ |
| IV-110 | + |
| IV-111 | + |
| IV-112 | + |
| IV-113 | + |
| IV-114 | + |
| IV-115 | + |
| IV-116 | + |
| IV-117 | + |
| IV-118 | + |
| IV-119 | + |
| IV-120 | + |

TABLE 12-continued

Enzyme activity for compounds of Formula IV

| Compound of Formula IV- | GCN2 (Ki) |
|---|---|
| IV-121 | + |
| IV-122 | + |
| IV-123 | + |
| IV-124 | + |
| IV-125 | + |
| IV-126 | + |
| IV-127 | + |
| IV-128 | + |
| IV-129 | + |
| IV-130 | + |
| IV-131 | + |
| IV-132 | + |
| IV-133 | + |
| IV-134 | + |
| IV-135 | + |
| IV-136 | + |
| IV-137 | + |
| IV-138 | + |
| IV-139 | + |
| IV-140 | + |
| IV-141 | + |
| IV-142 | + |
| IV-143 | + |
| IV-144 | + |
| IV-145 | + |
| IV-146 | + |
| IV-147 | + |
| IV-148 | + |
| IV-149 | + |
| IV-150 | + |
| IV-151 | + |
| IV-152 | + |
| IV-153 | + |
| IV-154 | + |
| IV-155 | + |
| IV-156 | + |
| IV-157 | + |
| IV-158 | + |
| IV-159 | + |
| IV-160 | + |
| IV-161 | + |
| IV-162 | + |
| IV-163 | + |
| IV-164 | + |
| IV-165 | + |
| IV-166 | + |
| IV-167 | + |
| IV-168 | + |
| IV-169 | + |
| IV-170 | + |
| IV-171 | + |
| IV-172 | + |
| IV-173 | + |
| IV-174 | + |
| IV-175 | + |
| IV-176 | + |
| IV-177 | + |
| IV-178 | + |
| IV-179 | + |
| IV-180 | + |
| IV-181 | + |
| IV-182 | ++ |
| IV-183 | + |
| IV-184 | ++ |
| IV-185 | ++ |
| IV-186 | +++ |
| IV-187 | ++ |
| IV-188 | + |
| IV-189 | ++ |
| IV-190 | + |
| IV-191 | ++ |
| IV-192 | +++ |
| IV-193 | +++ |
| IV-194 | +++ |
| IV-195 | ++ |
| IV-196 | ++ |
| IV-197 | + |
| IV-198 | ++ |
| IV-199 | ++ |
| IV-200 | +++ |
| IV-201 | +++ |
| IV-202 | ++ |
| IV-203 | ++ |
| IV-204 | ++ |
| IV-205 | ++ |
| IV-206 | ++ |
| IV-207 | +++ |
| IV-208 | ++ |
| IV-209 | +++ |
| IV-210 | +++ |
| IV-211 | +++ |
| IV-212 | + |
| IV-213 | ++ |
| IV-214 | +++ |
| IV-215 | ++ |
| IV-216 | +++ |
| IV-217 | +++ |
| IV-218 | ++ |
| IV-219 | ++ |
| IV-220 | ++ |
| IV-221 | ++ |
| IV-222 | +++ |
| IV-223 | + |
| IV-224 | +++ |
| IV-225 | ++ |
| IV-226 | ++ |
| IV-227 | + |
| IV-228 | ++ |
| IV-229 | + |
| IV-230 | +++ |
| IV-231 | + |
| IV-232 | ++ |
| IV-233 | ++ |
| IV-234 | ++ |
| IV-235 | +++ |
| IV-236 | ++ |
| IV-237 | + |
| IV-238 | ++ |
| IV-239 | + |
| IV-240 | + |
| IV-241 | + |
| IV-242 | ++ |
| IV-243 | ++ |
| IV-244 | + |
| IV-245 | + |
| IV-246 | + |
| IV-247 | +++ |
| IV-248 | ++ |
| IV-249 | + |
| IV-250 | + |
| IV-251 | + |
| IV-252 | + |
| IV-253 | ++ |
| IV-254 | ++ |
| IV-255 | ++ |
| IV-256 | + |
| IV-257 | ++ |
| IV-258 | + |
| IV-259 | + |
| IV-260 | ++ |
| IV-261 | ++ |
| IV-262 | + |
| IV-263 | + |
| IV-264 | +++ |
| IV-265 | + |
| IV-266 | ++ |
| IV-267 | + |
| IV-268 | + |
| IV-269 | ++ |
| IV-270 | + |

TABLE 12-continued

Enzyme activity for compounds of Formula IV

| Compound of Formula IV- | GCN2 (Ki) |
|---|---|
| IV-271 | + |
| IV-272 | + |
| IV-273 | + |
| IV-274 | ++ |
| IV-275 | + |
| IV-276 | + |
| IV-277 | ++ |
| IV-278 | +++ |
| IV-279 | +++ |
| IV-280 | +++ |
| IV-281 | ++ |
| IV-282 | +++ |
| IV-283 | + |
| IV-284 | + |
| IV-285 | ++ |
| IV-286 | ++ |
| IV-287 | ++ |
| IV-288 | +++ |
| IV-289 | + |
| IV-290 | +++ |
| IV-291 | + |
| IV-292 | +++ |
| IV-293 | ++ |
| IV-294 | ++ |
| IV-295 | + |
| IV-296 | +++ |
| IV-297 | + |
| IV-298 | + |
| IV-299 | ++ |
| IV-300 | + |
| IV-301 | + |
| IV-302 | + |
| IV-303 | + |
| IV-304 | +++ |
| IV-305 | +++ |
| IV-306 | +++ |
| IV-307 | + |
| IV-308 | + |
| IV-309 | ++ |
| IV-310 | ++ |
| IV-311 | +++ |
| IV-312 | ++ |
| IV-313 | + |
| IV-314 | +++ |
| IV-315 | ++ |
| IV-316 | + |
| IV-317 | ++ |
| IV-318 | +++ |
| IV-319 | + |
| IV-320 | + |
| IV-321 | + |
| IV-322 | + |
| IV-323 | +++ |
| IV-324 | ++ |
| IV-325 | ++ |
| IV-326 | + |
| IV-327 | ++ |
| IV-328 | +++ |
| IV-329 | ++ |
| IV-330 | ++ |
| IV-331 | + |
| IV-332 | + |
| IV-333 | ++ |
| IV-334 | + |
| IV-335 | ++ |
| IV-336 | + |
| IV-337 | +++ |
| IV-338 | + |
| IV-339 | + |
| IV-340 | +++ |
| IV-341 | ++ |
| IV-342 | + |
| IV-343 | +++ |
| IV-344 | ++ |
| IV-345 | ++ |
| IV-346 | +++ |
| IV-347 | + |
| IV-348 | ++ |
| IV-349 | ++ |
| IV-350 | + |
| IV-351 | +++ |
| IV-352 | ++ |
| IV-353 | + |
| IV-354 | ++ |
| IV-355 | +++ |
| IV-356 | +++ |
| IV-357 | + |
| IV-358 | +++ |
| IV-359 | +++ |
| IV-360 | +++ |
| IV-361 | +++ |
| IV-362 | ++ |
| IV-363 | +++ |
| IV-364 | ++ |
| IV-365 | +++ |
| IV-366 | + |
| IV-367 | + |
| IV-368 | + |
| IV-369 | +++ |
| IV-370 | + |
| IV-371 | ++ |
| IV-372 | ++ |
| IV-373 | +++ |
| IV-374 | ++ |
| IV-375 | +++ |
| IV-376 | +++ |
| IV-377 | + |
| IV-378 | +++ |
| IV-379 | +++ |
| IV-380 | +++ |
| IV-381 | ++ |
| IV-382 | ++ |
| IV-383 | ++ |
| IV-384 | ++ |
| IV-385 | ++ |
| IV-386 | ++ |
| IV-387 | +++ |
| IV-388 | +++ |
| IV-389 | +++ |
| IV-390 | +++ |
| IV-391 | + |
| IV-392 | +++ |
| IV-393 | + |
| IV-394 | + |
| IV-395 | ++ |
| IV-396 | +++ |
| IV-397 | + |
| IV-398 | ++ |
| IV-399 | +++ |
| IV-400 | ++ |
| IV-401 | ++ |
| IV-402 | +++ |
| IV-403 | +++ |
| IV-404 | + |
| IV-405 | +++ |
| IV-406 | ++ |
| IV-407 | +++ |
| IV-408 | + |
| IV-409 | +++ |
| IV-410 | ++ |
| IV-411 | ++ |
| IV-412 | + |
| IV-413 | ++ |
| IV-414 | +++ |
| IV-415 | +++ |
| IV-416 | +++ |
| IV-417 | +++ |
| IV-418 | ++ |
| IV-419 | + |
| IV-420 | +++ |

TABLE 12-continued

Enzyme activity for compounds of Formula IV

| Compound of Formula IV- | GCN2 (Ki) |
|---|---|
| IV-421 | ++ |
| IV-422 | + |
| IV-423 | + |
| IV-424 | + |
| IV-425 | + |
| IV-426 | + |
| IV-427 | + |
| IV-428 | + |
| IV-429 | + |
| IV-430 | +++ |
| IV-431 | + |
| IV-432 | + |
| IV-433 | + |
| IV-434 | + |
| IV-435 | + |
| IV-436 | + |
| IV-437 | + |
| IV-438 | + |
| IV-439 | + |
| IV-440 | + |
| IV-441 | + |
| IV-442 | + |
| IV-443 | + |
| IV-444 | + |
| IV-445 | + |
| IV-446 | + |
| IV-447 | + |
| IV-448 | + |
| IV-449 | + |
| IV-450 | + |
| IV-451 | +++ |
| IV-452 | +++ |
| IV-453 | +++ |
| IV-454 | ++ |
| IV-455 | + |
| IV-456 | + |
| IV-457 | + |
| IV-458 | + |
| IV-459 | ++ |
| IV-460 | + |
| IV-461 | ++ |
| IV-462 | + |
| IV-463 | + |
| IV-464 | +++ |
| IV-465 | ++ |
| IV-466 | +++ |
| IV-467 | + |
| IV-468 | ++ |
| IV-469 | ++ |
| IV-470 | +++ |
| IV-471 | ++ |
| IV-472 | ++ |
| IV-473 | +++ |
| IV-474 | +++ |
| IV-475 | ++ |
| IV-476 | +++ |
| IV-477 | ++ |
| IV-478 | + |
| IV-479 | + |
| IV-480 | + |
| IV-481 | ++ |
| IV-482 | + |
| IV-483 | + |
| IV-484 | ++ |
| IV-485 | +++ |
| IV-486 | + |
| IV-487 | + |
| IV-488 | + |
| IV-489 | + |
| IV-490 | + |
| IV-491 | +++ |
| IV-492 | +++ |
| IV-493 | ++ |
| IV-494 | ++ |
| IV-495 | + |
| IV-496 | + |
| IV-497 | + |
| IV-498 | + |
| IV-499 | +++ |
| IV-500 | + |
| IV-501 | +++ |
| IV-502 | + |
| IV-503 | + |
| IV-504 | + |
| IV-505 | + |
| IV-506 | + |
| IV-507 | + |
| IV-508 | + |
| IV-509 | + |
| IV-510 | + |
| IV-511 | + |
| IV-512 | + |
| IV-513 | + |
| IV-514 | + |
| IV-515 | + |
| IV-516 | + |
| IV-517 | + |
| IV-518 | ++ |
| IV-519 | ++ |
| IV-520 | + |
| IV-521 | + |
| IV-522 | + |
| IV-523 | + |
| IV-524 | +++ |
| IV-525 | +++ |
| IV-526 | + |
| IV-527 | + |
| IV-528 | + |
| IV-529 | + |
| IV-530 | + |
| IV-531 | + |
| IV-532 | + |
| IV-533 | + |
| IV-534 | + |
| IV-535 | ++ |
| IV-536 | + |
| IV-537 | + |
| IV-538 | +++ |
| IV-539 | + |
| IV-540 | +++ |
| IV-541 | ++ |
| IV-542 | + |
| IV-543 | + |
| IV-544 | + |
| IV-545 | +++ |
| IV-546 | +++ |
| IV-547 | + |
| IV-548 | +++ |
| IV-549 | + |
| IV-550 | + |
| IV-551 | + |
| IV-552 | + |
| IV-553 | + |
| IV-554 | + |
| IV-555 | + |
| IV-556 | + |
| IV-557 | + |
| IV-558 | ++ |
| IV-559 | + |
| IV-560 | + |
| IV-561 | + |
| IV-562 | +++ |
| IV-563 | +++ |
| IV-564 | + |
| IV-565 | + |
| IV-566 | + |
| IV-567 | ++ |
| IV-568 | + |
| IV-569 | + |
| IV-570 | + |

TABLE 12-continued

Enzyme activity for compounds of Formula IV

| Compound of Formula IV- | GCN2 (Ki) |
|---|---|
| IV-571 | + |
| IV-572 | +++ |
| IV-573 | ++ |
| IV-574 | ++ |
| IV-575 | ++ |
| IV-576 | ++ |
| IV-577 | +++ |
| IV-578 | +++ |
| IV-579 | + |
| IV-580 | ++ |
| IV-581 | + |
| IV-582 | ++ |
| IV-583 | +++ |
| IV-584 | + |
| IV-585 | + |
| IV-586 | + |
| IV-587 | + |
| IV-588 | + |
| IV-589 | ++ |
| IV-590 | + |
| IV-591 | + |
| IV-592 | +++ |
| IV-593 | +++ |
| IV-594 | ++ |
| IV-595 | + |
| IV-596 | + |
| IV-597 | ++ |
| IV-598 | + |
| IV-599 | + |
| IV-600 | + |
| IV-601 | +++ |
| IV-602 | + |
| IV-603 | + |
| IV-604 | + |
| IV-605 | + |
| IV-606 | + |
| IV-607 | + |
| IV-608 | + |
| IV-609 | + |
| IV-610 | + |
| IV-611 | + |
| IV-612 | + |
| IV-613 | + |
| IV-614 | + |
| IV-615 | ++ |
| IV-616 | ++ |
| IV-617 | + |
| IV-618 | + |
| IV-619 | + |
| IV-620 | + |
| IV-621 | +++ |
| IV-622 | +++ |
| IV-623 | +++ |
| IV-624 | ++ |
| IV-625 | + |
| IV-626 | +++ |
| IV-627 | +++ |
| IV-628 | ++ |
| IV-629 | +++ |
| IV-630 | ++ |
| IV-631 | ++ |
| IV-632 | ++ |
| IV-633 | ++ |
| IV-634 | + |
| IV-635 | ++ |
| IV-636 | +++ |
| IV-637 | +++ |
| IV-638 | + |
| IV-639 | +++ |
| IV-640 | +++ |
| IV-641 | + |
| IV-642 | + |
| IV-643 | + |
| IV-644 | + |
| IV-645 | + |
| IV-646 | ++ |
| IV-647 | + |
| IV-648 | +++ |
| IV-649 | + |
| IV-650 | +++ |
| IV-651 | +++ |
| IV-652 | ++ |
| IV-653 | + |
| IV-654 | + |
| IV-655 | + |
| IV-656 | + |
| IV-657 | + |
| IV-658 | + |
| IV-659 | + |
| IV-660 | + |
| IV-661 | + |
| IV-662 | + |
| IV-663 | + |
| IV-664 | + |
| IV-665 | + |
| IV-666 | ++ |
| IV-667 | + |
| IV-668 | ++ |
| IV-669 | + |
| IV-670 | +++ |
| IV-671 | + |
| IV-672 | + |
| IV-673 | +++ |
| IV-674 | + |
| IV-675 | ++ |
| IV-676 | + |
| IV-677 | ++ |
| IV-678 | ++ |
| IV-679 | +++ |
| IV-680 | ++ |
| IV-681 | ++ |
| IV-682 | ++ |
| IV-683 | ++ |
| IV-684 | +++ |
| IV-685 | +++ |
| IV-686 | + |
| IV-687 | + |
| IV-688 | ++ |
| IV-689 | ++ |
| IV-690 | +++ |
| IV-691 | ++ |
| IV-692 | + |
| IV-693 | ++ |
| IV-694 | + |
| IV-695 | ++ |
| IV-696 | + |
| IV-697 | + |
| IV-698 | + |
| IV-699 | + |
| IV-700 | + |
| IV-701 | + |
| IV-702 | + |
| IV-703 | + |
| IV-704 | + |
| IV-705 | + |
| IV-706 | +++ |
| IV-707 | ++ |
| IV-708 | ++ |
| IV-709 | + |
| IV-710 | + |
| IV-711 | + |
| IV-712 | + |
| IV-713 | + |
| IV-714 | + |
| IV-715 | + |
| IV-716 | + |
| IV-717 | + |
| IV-718 | + |
| IV-719 | + |
| IV-720 | + |

TABLE 12-continued

Enzyme activity for compounds of Formula IV

| Compound of Formula IV- | GCN2 (Ki) |
|---|---|
| IV-721 | + |
| IV-722 | + |
| IV-723 | + |
| IV-724 | * |
| IV-725 | * |
| IV-726 | * |
| IV-727 | * |
| IV-728 | * |
| IV-729 | * |
| IV-730 | * |
| IV-731 | * |
| IV-732 | * |
| IV-733 | * |
| IV-734 | * |
| IV-735 | * |
| IV-736 | * |
| IV-737 | * |
| IV-738 | * |
| IV-739 | * |
| IV-740 | * |
| IV-741 | * |
| IV-742 | * |
| IV-743 | * |
| IV-744 | * |
| IV-745 | * |
| IV-746 | * |
| IV-747 | * |
| IV-748 | * |
| IV-749 | * |
| IV-750 | * |
| IV-751 | * |

+++ for Ki < 10 nM;
++ for Ki in 10 nM-100 nM range;
+ for Ki 100 nM-1 µM;
* for Ki > 1 µM;
--- when no data available

TABLE 13

Enzyme activity for compounds of Formula IV

| Compound IV | GCN2 IC$_{50}$ |
|---|---|
| IV-754 | ++ |
| IV-755 | ++ |
| IV-756 | ++ |
| IV-757 | ++ |
| IV-758 | ++ |
| IV-759 | ++ |
| IV-760 | ++ |
| IV-761 | ++ |
| IV-762 | ++ |
| IV-763 | +++ |
| IV-764 | ++ |
| IV-765 | ++ |
| IV-766 | ++ |
| IV-767 | +++ |
| IV-768 | ++ |
| IV-769 | ++ |
| IV-770 | ++ |
| IV-771 | +++ |
| IV-772 | ++ |
| IV-773 | ++ |
| IV-774 | ++ |
| IV-775 | ++ |
| IV-776 | +++ |
| IV-777 | ++ |
| IV-778 | ++ |
| IV-779 | ++ |

+++ for IC$_{50}$ < 10 nM;
++ for IC$_{50}$ in 10 nM-1 µM range;
+ for IC$_{50}$ > 1 µM

TABLE 14

Enzyme activity for compounds of Formula V

| Compound V | GCN2 (Ki) |
|---|---|
| V-1 | +++ |
| V-2 | + |
| V-3 | +++ |
| V-4 | ++ |
| V-5 | ++ |
| V-6 | + |
| V-7 | ++ |
| V-8 | + |
| V-9 | + |
| V-10 | +++ |
| V-11 | +++ |
| V-12 | + |
| V-13 | +++ |
| V-14 | ++ |
| V-15 | +++ |
| V-16 | + |
| V-17 | ++ |
| V-18 | + |
| V-19 | + |
| V-20 | +++ |

+++ for Ki < 10 nM;
++ for Ki in 10 nM-100 nM range;
+ for Ki 100 nM-1 µM;
--- when no data available Example 114: GCN2 Cellular Inhibition Assay Compounds can be screened for their ability to inhibit intracellular GCN2 using an AlphaScreen assay (Perkin Elmer) to detect phosphorylation of the GCN2 substrate eIF2α in borrelidin-treated cells. U2OS cells are plated at 5,000 cells per well in 384-well white polystyrene plates (Corning 3570) in McCoy's 5 A media (GIBCO 26600-023) supplemented with 10% foetal bovine serum (SAFC 12103C), Penicillin/Streptomycin solution diluted 1:100 (Sigma P0781), and 2 mM L-glutamine (Sigma G7513), and allowed to adhere overnight at 37° C. in 5% CO$_2$. Compounds are then added to the cell media from a final concentration of 40 µM in 4-fold serial dilutions. Borrelidin (FluoroChem M01440) is immediately added to the wells to a final concentration of 10 µM and the cells are incubated for 1 h at 37° C. in 5% CO$_2$. After 1 h of treatment with borrelidin, the media is removed, and the cells are lysed with lysis buffer (TGR BioSciences TGRLB) at ambient temperature.

An AlphaScreen SureFire P-eIF2α (Ser51) assay kit (Perkin Elmer TGREIF2S) was used to measure levels of eIF2α phosphorylated on Serine 51. Anti-phosphorylated eIF2α Ser51 antibody-linked acceptor beads (TGR BioScience 6760617) are added to the cell homogenate (diluted 1:250 into a mixture of activation (TGR BioScience TGRAB) and reaction buffer (TGR BioScience TGREIF2S) prepared immediately before use). The plate is then incubated for 2 h at ambient temperature in the dark. Anti-eIF2α antibody-linked donor beads (TGR BioScience 6760617) were then added (diluted 1:100 in dilution buffer (TGR BioScience TGRDB) prepared immediately before use). The plate is then incubated overnight at ambient temperature in the dark.

Plates are analyzed on an Alpha Technology-compatible PHERAstar FS plate reader (BMG Labtech Version 1.14) to quantify phosphorylated eIF2α Ser51 levels. The percentage inhibition of phosphorylated eIF2α is calculated by comparison to control wells stimulated with borrelidin alone. These data are plotted against concentration of compound and $IC_{50}$s are determined using Genedata Analyzer (Genedata AG Version 12.0.3).

TABLE 15

Cellular activity for compounds of Formula II (biomarker assay)

| Compound of formula II | GCN2 Biomarker ($IC_{50}$) |
|---|---|
| II-1 | ++ |
| II-2 | ++ |
| II-3 | ++ |
| II-4 | ++ |
| II-5 | + |
| II-6 | ++ |
| II-7 | + |
| II-8 | ++ |
| II-9 | ++ |
| II-10 | + |
| II-11 | + |
| II-12 | ++ |
| II-13 | ++ |
| II-14 | + |
| II-15 | + |
| II-16 | + |
| II-17 | ++ |
| II-18 | +++ |
| II-19 | ++ |
| II-20 | + |
| II-21 | + |
| II-22 | + |
| II-23 | --- |
| II-24 | + |
| II-25 | + |
| II-26 | + |
| II-27 | + |
| II-28 | +++ |
| II-29 | + |
| II-30 | ++ |
| II-31 | +++ |
| II-32 | +++ |
| II-33 | +++ |
| II-34 | +++ |
| II-35 | ++ |
| II-36 | +++ |
| II-37 | ++ |
| II-38 | + |
| II-39 | ++ |
| II-40 | +++ |
| II-41 | ++ |
| II-42 | + |
| II-43 | --- |
| II-44 | ++ |
| II-45 | +++ |
| II-46 | + |
| II-47 | ++ |
| II-48 | + |
| II-49 | ++ |
| II-50 | ++ |
| II-51 | ++ |
| II-52 | + |
| II-53 | ++ |
| II-54 | ++ |
| II-55 | +++ |
| II-56 | ++ |
| II-57 | ++ |
| II-58 | +++ |
| II-59 | +++ |
| II-60 | +++ |
| II-61 | ++ |
| II-62 | + |
| II-63 | + |
| II-64 | +++ |
| II-65 | ++ |
| II-66 | ++ |
| II-67 | +++ |
| II-68 | ++ |
| II-69 | +++ |
| II-70 | + |
| II-71 | ++ |
| II-72 | +++ |
| II-73 | + |
| II-74 | ++ |
| II-75 | +++ |
| II-76 | + |
| II-77 | + |
| II-78 | +++ |
| II-79 | + |
| II-80 | ++ |
| II-81 | + |
| II-82 | ++ |
| II-83 | ++ |
| II-84 | ++ |
| II-85 | ++ |
| II-86 | ++ |
| II-87 | ++ |
| II-88 | ++ |
| II-89 | ++ |
| II-90 | ++ |
| II-91 | --- |
| II-92 | ++ |
| II-93 | +++ |
| II-94 | +++ |
| II-95 | ++ |
| II-96 | ++ |
| II-97 | + |
| II-98 | ++ |
| II-99 | ++ |
| II-100 | ++ |
| II-101 | ++ |
| II-102 | + |
| II-103 | +++ |
| II-104 | + |
| II-105 | ++ |
| II-106 | ++ |
| II-107 | +++ |
| II-108 | ++ |
| II-109 | ++ |
| II-110 | +++ |
| II-111 | ++ |
| II-112 | ++ |
| II-113 | ++ |
| II-114 | + |
| II-115 | ++ |
| II-116 | ++ |
| II-117 | ++ |
| II-118 | ++ |
| II-119 | +++ |
| II-120 | + |
| II-121 | +++ |
| II-122 | ++ |
| II-123 | ++ |
| II-124 | ++ |
| II-125 | +++ |
| II-126 | + |
| II-127 | ++ |
| II-128 | ++ |
| II-129 | ++ |
| II-130 | + |
| II-131 | +++ |
| II-132 | ++ |
| II-133 | ++ |
| II-134 | ++ |
| II-135 | ++ |
| II-136 | +++ |
| II-137 | + |

TABLE 15-continued

Cellular activity for compounds of Formula II (biomarker assay)

| Compound of formula II | GCN2 Biomarker (IC$_{50}$) |
|---|---|
| II-138 | ++ |
| II-139 | ++ |
| II-140 | + |
| II-141 | ++ |
| II-142 | ++ |
| II-143 | +++ |
| II-144 | ++ |
| II-145 | ++ |
| II-146 | ++ |
| II-147 | +++ |
| II-148 | +++ |
| II-149 | +++ |
| II-150 | ++ |
| II-151 | ++ |
| II-152 | + |
| II-153 | +++ |
| II-154 | +++ |
| II-155 | ++ |
| II-156 | ++ |
| II-157 | +++ |
| II-158 | ++ |
| II-159 | ++ |
| II-160 | ++ |
| II-161 | + |
| II-162 | ++ |
| II-163 | ++ |
| II-164 | ++ |
| II-165 | --- |
| II-166 | --- |
| II-167 | + |
| II-168 | ++ |
| II-169 | + |
| II-170 | ++ |
| II-171 | ++ |
| II-172 | ++ |
| II-173 | ++ |
| II-174 | + |
| II-175 | ++ |
| II-176 | ++ |
| II-177 | +++ |
| II-178 | ++ |
| II-179 | ++ |
| II-180 | + |
| II-181 | + |
| II-182 | + |
| II-183 | ++ |
| II-184 | ++ |
| II-185 | + |
| II-186 | ++ |
| II-187 | + |
| II-188 | ++ |
| II-189 | ++ |
| II-190 | + |
| II-191 | + |
| II-192 | + |
| II-193 | + |
| II-194 | + |
| II-195 | + |
| II-196 | + |
| II-197 | +++ |
| II-198 | + |
| II-199 | + |
| II-200 | + |
| II-201 | + |
| II-202 | +++ |
| II-203 | + |
| II-204 | + |
| II-205 | ++ |
| II-206 | + |
| II-207 | + |
| II-208 | + |
| II-209 | + |
| II-210 | + |
| II-211 | ++ |
| II-212 | ++ |
| II-213 | ++ |
| II-214 | ++ |
| II-215 | ++ |
| II-216 | + |
| II-217 | ++ |
| II-218 | ++ |
| II-219 | +++ |
| II-220 | --- |
| II-221 | +++ |
| II-222 | ++ |
| II-223 | + |
| II-224 | ++ |
| II-225 | +++ |
| II-226 | ++ |
| II-227 | + |
| II-228 | + |
| II-229 | +++ |
| II-230 | +++ |
| II-231 | ++ |
| II-232 | ++ |
| II-233 | +++ |
| II-234 | ++ |
| II-235 | ++ |
| II-236 | --- |
| II-237 | ++ |
| II-238 | ++ |
| II-239 | ++ |
| II-240 | +++ |
| II-241 | + |
| II-242 | + |
| II-243 | ++ |
| II-244 | + |
| II-245 | + |
| II-246 | + |
| II-247 | +++ |
| II-248 | ++ |
| II-249 | ++ |
| II-250 | + |
| II-251 | + |
| II-252 | + |
| II-253 | + |
| II-254 | + |
| II-255 | + |
| II-256 | + |
| II-257 | ++ |
| II-258 | +++ |
| II-259 | +++ |
| II-260 | ++ |
| II-261 | ++ |
| II-262 | +++ |
| II-263 | ++ |
| II-264 | + |
| II-265 | + |
| II-266 | +++ |
| II-267 | ++ |
| II-268 | +++ |
| II-269 | --- |
| II-270 | ++ |
| II-271 | ++ |
| II-272 | + |
| II-273 | ++ |
| II-274 | + |
| II-275 | ++ |
| II-276 | ++ |
| II-277 | ++ |
| II-278 | +++ |
| II-279 | + |
| II-280 | + |
| II-281 | +++ |
| II-282 | + |
| II-283 | + |
| II-284 | + |
| II-285 | + |

TABLE 15-continued

Cellular activity for compounds of Formula II (biomarker assay)

| Compound of formula II | GCN2 Biomarker (IC$_{50}$) |
|---|---|
| II-286 | + |
| II-287 | + |
| II-288 | + |
| II-289 | ++ |
| II-290 | ++ |
| II-291 | +++ |
| II-292 | ++ |
| II-293 | ++ |
| II-294 | + |
| II-295 | + |
| II-296 | + |
| II-297 | ++ |
| II-298 | ++ |
| II-299 | ++ |
| II-300 | +++ |
| II-301 | ++ |
| II-302 | ++ |
| II-303 | ++ |
| II-304 | +++ |
| II-305 | + |
| II-306 | ++ |
| II-307 | ++ |
| II-308 | + |
| II-309 | + |
| II-310 | ++ |
| II-311 | +++ |
| II-312 | +++ |
| II-313 | +++ |
| II-314 | + |
| II-315 | + |
| II-316 | +++ |
| II-317 | ++ |
| II-318 | ++ |
| II-319 | + |
| II-320 | + |
| II-321 | + |
| II-322 | + |
| II-323 | ++ |
| II-324 | + |
| II-325 | ++ |
| II-326 | + |
| II-327 | + |
| II-328 | ++ |
| II-329 | +++ |
| II-330 | ++ |
| II-331 | +++ |
| II-332 | + |
| II-333 | ++ |
| II-334 | ++ |
| II-335 | + |
| II-336 | + |
| II-337 | + |
| II-338 | + |
| II-339 | ++ |
| II-340 | +++ |
| II-341 | + |
| II-342 | ++ |
| II-343 | + |
| II-344 | +++ |
| II-345 | +++ |
| II-346 | + |
| II-347 | +++ |
| II-348 | ++ |
| II-349 | ++ |
| II-350 | +++ |
| II-351 | + |
| II-352 | + |
| II-353 | + |
| II-354 | + |
| II-355 | + |
| II-356 | + |
| II-357 | + |
| II-358 | + |
| II-359 | + |
| II-360 | ++ |
| II-361 | +++ |
| II-362 | ++ |
| II-363 | + |
| II-364 | +++ |
| II-365 | + |
| II-366 | +++ |
| II-367 | ++ |
| II-368 | + |
| II-369 | + |
| II-370 | ++ |
| II-371 | --- |
| II-372 | + |
| II-373 | ++ |
| II-374 | ++ |
| II-375 | +++ |
| II-376 | ++ |
| II-377 | +++ |
| II-378 | ++ |
| II-379 | ++ |
| II-380 | + |
| II-381 | +++ |
| II-382 | ++ |
| II-383 | ++ |
| II-384 | +++ |
| II-385 | +++ |
| II-386 | +++ |
| II-387 | ++ |
| II-388 | ++ |
| II-389 | ++ |
| II-390 | +++ |
| II-391 | +++ |
| II-392 | ++ |
| II-393 | + |
| II-394 | ++ |
| II-395 | + |
| II-396 | ++ |
| II-397 | +++ |
| II-398 | ++ |
| II-399 | + |
| II-400 | + |
| II-401 | + |
| II-402 | + |
| II-403 | +++ |
| II-404 | ++ |
| II-405 | ++ |
| II-406 | + |
| II-407 | + |
| II-408 | ++ |
| II-409 | + |
| II-410 | ++ |
| II-411 | ++ |
| II-412 | ++ |
| II-413 | + |
| II-414 | + |
| II-415 | + |
| II-416 | +++ |
| II-417 | ++ |
| II-418 | ++ |
| II-419 | ++ |
| II-420 | ++ |
| II-421 | ++ |
| II-422 | +++ |
| II-423 | + |
| II-424 | +++ |
| II-425 | ++ |
| II-426 | ++ |
| II-427 | +++ |
| II-428 | + |
| II-429 | + |
| II-430 | ++ |
| II-431 | +++ |
| II-432 | +++ |
| II-433 | +++ |

TABLE 15-continued

Cellular activity for compounds of Formula II (biomarker assay)

| Compound of formula II | GCN2 Biomarker (IC$_{50}$) |
|---|---|
| II-434 | + |
| II-435 | + |
| II-436 | ++ |
| II-437 | +++ |
| II-438 | ++ |
| II-439 | ++ |
| II-440 | ++ |
| II-441 | ++ |
| II-442 | + |
| II-443 | +++ |
| II-444 | +++ |
| II-445 | + |
| II-446 | + |
| II-447 | ++ |
| II-448 | +++ |
| II-449 | +++ |
| II-450 | ++ |
| II-451 | ++ |
| II-452 | ++ |
| II-453 | + |
| II-454 | + |
| II-455 | ++ |
| II-456 | +++ |
| II-457 | ++ |
| II-458 | +++ |
| II-459 | + |
| II-460 | + |
| II-461 | ++ |
| II-462 | +++ |
| II-463 | +++ |
| II-464 | --- |
| II-465 | ++ |
| II-466 | +++ |
| II-467 | --- |
| II-468 | --- |
| II-469 | ++ |
| II-470 | ++ |
| II-471 | + |
| II-472 | +++ |
| II-473 | + |
| II-474 | ++ |
| II-475 | +++ |
| II-476 | ++ |
| II-477 | ++ |
| II-478 | ++ |
| II-479 | +++ |
| II-480 | + |
| II-481 | ++ |
| II-482 | +++ |
| II-483 | + |
| II-484 | ++ |
| II-485 | +++ |
| II-486 | ++ |
| II-487 | +++ |
| II-488 | + |
| II-489 | + |
| II-490 | +++ |
| II-491 | +++ |
| II-492 | ++ |
| II-493 | ++ |
| II-494 | --- |
| II-495 | +++ |
| II-496 | + |
| II-497 | ++ |
| II-498 | + |
| II-499 | ++ |
| II-500 | + |
| II-501 | --- |
| II-502 | +++ |
| II-503 | ++ |
| II-504 | + |
| II-505 | + |
| II-506 | + |
| II-507 | --- |
| II-508 | --- |
| II-509 | +++ |
| II-510 | ++ |
| II-511 | +++ |
| II-512 | --- |
| II-513 | --- |
| II-514 | --- |
| II-515 | --- |
| II-516 | ++ |
| II-517 | --- |
| II-518 | + |
| II-519 | ++ |
| II-520 | ++ |
| II-521 | ++ |
| II-522 | ++ |
| II-523 | +++ |
| II-524 | --- |
| II-525 | +++ |
| II-526 | +++ |
| II-527 | +++ |
| II-528 | +++ |
| II-529 | ++ |
| II-530 | --- |
| II-531 | --- |
| II-532 | --- |
| II-533 | --- |
| II-534 | --- |
| II-535 | ++ |
| II-536 | --- |
| II-537 | +++ |
| II-538 | +++ |
| II-539 | --- |
| II-540 | ++ |
| II-541 | +++ |
| II-542 | +++ |
| II-543 | ++ |
| II-544 | +++ |
| II-545 | ++ |
| II-546 | +++ |
| II-547 | ++ |
| II-548 | + |
| II-549 | --- |
| II-550 | --- |
| II-551 | --- |
| II-552 | --- |
| II-553 | --- |
| II-554 | --- |
| II-555 | --- |
| II-556 | --- |
| II-557 | --- |
| II-558 | --- |
| II-559 | --- |
| II-560 | --- |
| II-561 | --- |
| II-562 | --- |
| II-563 | --- |
| II-564 | --- |
| II-565 | --- |
| II-566 | --- |
| II-567 | --- |
| II-568 | --- |
| II-569 | --- |
| II-570 | --- |
| II-571 | --- |
| II-572 | --- |
| II-573 | --- |
| II-574 | --- |
| II-575 | --- |
| II-576 | --- |
| II-577 | --- |
| II-578 | --- |
| II-579 | --- |
| II-580 | --- |
| II-581 | --- |

TABLE 15-continued

Cellular activity for compounds of Formula II (biomarker assay)

| Compound of formula II | GCN2 Biomarker (IC$_{50}$) |
|---|---|
| II-582 | --- |
| II-583 | --- |
| II-584 | --- |
| II-585 | --- |
| II-586 | --- |
| II-587 | --- |
| II-588 | --- |
| II-589 | --- |
| II-590 | --- |
| II-591 | --- |
| II-592 | --- |
| II-593 | +++ |
| II-594 | --- |
| II-595 | --- |
| II-596 | --- |
| II-597 | --- |
| II-598 | --- |
| II-599 | --- |
| II-600 | --- |
| II-601 | --- |
| II-602 | +++ |
| II-603 | --- |
| II-604 | --- |
| II-605 | --- |
| II-606 | --- |
| II-607 | +++ |
| II-608 | --- |
| II-609 | --- |
| II-610 | --- |
| II-611 | --- |
| II-612 | --- |
| II-613 | --- |
| II-614 | --- |
| II-615 | --- |
| II-616 | --- |
| II-617 | --- |
| II-618 | +++ |
| II-619 | --- |
| II-620 | --- |
| II-621 | --- |
| II-622 | --- |
| II-623 | --- |
| II-624 | --- |
| II-625 | --- |
| II-626 | --- |
| II-627 | --- |
| II-628 | --- |
| II-629 | --- |
| II-630 | --- |
| II-631 | +++ |
| II-632 | --- |
| II-633 | --- |
| II-634 | --- |
| II-635 | --- |
| II-636 | --- |
| II-637 | --- |
| II-638 | --- |
| II-639 | --- |
| II-640 | --- |
| II-641 | --- |
| II-642 | --- |
| II-643 | --- |
| II-644 | --- |
| II-645 | --- |
| II-646 | --- |
| II-647 | --- |
| II-648 | --- |
| II-649 | --- |
| II-650 | +++ |
| II-651 | --- |
| II-652 | ++ |
| II-653 | --- |
| II-654 | --- |
| II-655 | --- |
| II-656 | --- |
| II-657 | --- |
| II-658 | --- |
| II-659 | --- |
| II-660 | --- |
| II-661 | --- |
| II-662 | --- |
| II-663 | --- |
| II-664 | --- |
| II-665 | --- |
| II-666 | --- |
| II-667 | --- |
| II-668 | --- |
| II-669 | --- |
| II-670 | --- |
| II-671 | --- |
| II-672 | --- |
| II-673 | --- |
| II-674 | --- |
| II-675 | --- |
| II-676 | + |
| II-677 | --- |
| II-678 | --- |
| II-679 | --- |
| II-680 | --- |
| II-681 | --- |
| II-682 | --- |
| II-683 | --- |
| II-684 | --- |
| II-685 | --- |
| II-686 | --- |
| II-687 | --- |
| II-688 | --- |
| II-689 | --- |
| II-690 | --- |
| II-691 | --- |
| II-692 | ++ |
| II-693 | ++ |
| II-694 | --- |
| II-695 | ++ |
| II-696 | + |
| II-697 | --- |
| II-698 | ++ |
| II-699 | + |
| II-700 | +++ |
| II-701 | + |
| II-702 | --- |
| II-703 | --- |
| II-704 | + |
| II-705 | +++ |
| II-706 | ++ |
| II-707 | + |
| II-708 | --- |
| II-709 | ++ |
| II-710 | ++ |
| II-711 | ++ |
| II-712 | --- |
| II-713 | --- |
| II-714 | --- |
| II-715 | ++ |
| II-716 | +++ |
| II-717 | +++ |
| II-718 | --- |
| II-719 | ++ |
| II-720 | ++ |
| II-721 | ++ |
| II-722 | --- |
| II-723 | ++ |
| II-724 | ++ |
| II-725 | +++ |
| II-726 | + |
| II-727 | + |
| II-728 | + |
| II-729 | ++ |

TABLE 15-continued

Cellular activity for compounds of Formula II (biomarker assay)

| Compound of formula II | GCN2 Biomarker ($IC_{50}$) |
| --- | --- |
| II-730 | ++ |
| II-731 | + |
| II-732 | + |
| II-733 | + |
| II-734 | --- |
| II-735 | + |
| II-736 | + |
| II-737 | + |
| II-738 | + |
| II-739 | +++ |
| II-740 | +++ |
| II-741 | +++ |
| II-752 | +++ |
| II-753 | ++ |
| II-757 | +++ |
| II-759 | + |
| II-762 | ++ |
| II-763 | +++ |
| II-765 | + |
| II-766 | + |
| II-767 | +++ |
| II-768 | +++ |
| II-769 | ++ |
| II-770 | ++ |

+++ for $IC_{50} < 0.5$ μM;
++ for $IC_{50}$ in 0.5 μM-5 μM range;
+ for $IC_{50} > 5$ μM;
---- when no data available

TABLE 16

Cellular activity for compounds of Formula III (biomarker assay)

| Compound III | GCN2 Biomarker ($IC_{50}$) |
| --- | --- |
| III-1 | + |
| III-2 | +++ |
| III-3 | + |
| III-4 | +++ |
| III-5 | + |
| III-6 | ++ |
| III-7 | ++ |
| III-8 | ++ |
| III-9 | + |
| III-10 | +++ |
| III-11 | +++ |
| III-12 | +++ |
| III-13 | --- |
| III-14 | --- |
| III-15 | --- |
| III-16 | + |

+++ for $IC_{50} < 0.5$ μM;
++ for $IC_{50}$ in 0.5 μM-5 μM range;
+ for $IC_{50} > 5$ μM;
--- when no data available

TABLE 17

Cellular activity for compounds of Formula IV (biomarker assay)

| Compound of Formula IV- | GCN2 Biomarker ($IC_{50}$) |
| --- | --- |
| IV-1 | --- |
| IV-2 | + |
| IV-3 | +++ |
| IV-4 | ++ |
| IV-5 | ++ |
| IV-6 | +++ |
| IV-7 | ++ |
| IV-8 | ++ |
| IV-9 | +++ |
| IV-10 | +++ |
| IV-11 | ++ |
| IV-12 | +++ |
| IV-13 | +++ |
| IV-14 | +++ |
| IV-15 | ++ |
| IV-16 | ++ |
| IV-17 | + |
| IV-18 | ++ |
| IV-19 | +++ |
| IV-20 | ++ |
| IV-21 | + |
| IV-22 | + |
| IV-23 | + |
| IV-24 | + |
| IV-25 | + |
| IV-26 | + |
| IV-27 | ++ |
| IV-28 | ++ |
| IV-29 | + |
| IV-30 | + |
| IV-31 | --- |
| IV-32 | ++ |
| IV-33 | + |
| IV-34 | + |
| IV-35 | + |
| IV-36 | + |
| IV-37 | + |
| IV-38 | + |
| IV-39 | + |
| IV-40 | +++ |
| IV-41 | + |
| IV-42 | ++ |
| IV-43 | + |
| IV-44 | + |
| IV-45 | + |
| IV-46 | + |
| IV-47 | --- |
| IV-48 | + |
| IV-49 | + |
| IV-50 | ++ |
| IV-51 | + |
| IV-52 | + |
| IV-53 | ++ |
| IV-54 | ++ |
| IV-55 | ++ |
| IV-56 | + |
| IV-57 | + |
| IV-58 | ++ |
| IV-59 | +++ |
| IV-60 | ++ |
| IV-61 | + |
| IV-62 | + |
| IV-63 | + |
| IV-64 | + |
| IV-65 | + |
| IV-66 | --- |
| IV-67 | + |
| IV-68 | + |
| IV-69 | + |
| IV-70 | + |
| IV-71 | + |
| IV-72 | + |
| IV-73 | + |
| IV-74 | + |
| IV-75 | + |
| IV-76 | + |
| IV-77 | + |

TABLE 17-continued

Cellular activity for compounds of Formula IV (biomarker assay)

| Compound of Formula IV- | GCN2 Biomarker (IC$_{50}$) |
|---|---|
| IV-78 | + |
| IV-79 | --- |
| IV-80 | --- |
| IV-81 | + |
| IV-82 | + |
| IV-83 | + |
| IV-84 | --- |
| IV-85 | + |
| IV-86 | + |
| IV-87 | + |
| IV-88 | + |
| IV-89 | + |
| IV-90 | + |
| IV-91 | + |
| IV-92 | + |
| IV-93 | + |
| IV-94 | + |
| IV-95 | + |
| IV-96 | ++ |
| IV-97 | + |
| IV-98 | + |
| IV-99 | + |
| IV-100 | + |
| IV-101 | + |
| IV-102 | + |
| IV-103 | + |
| IV-104 | + |
| IV-105 | + |
| IV-106 | ++ |
| IV-107 | --- |
| IV-108 | ++ |
| IV-109 | ++ |
| IV-110 | + |
| IV-111 | + |
| IV-112 | + |
| IV-113 | + |
| IV-114 | + |
| IV-115 | + |
| IV-116 | + |
| IV-117 | + |
| IV-118 | + |
| IV-119 | + |
| IV-120 | + |
| IV-121 | + |
| IV-122 | + |
| IV-123 | + |
| IV-124 | + |
| IV-125 | + |
| IV-126 | + |
| IV-127 | --- |
| IV-128 | + |
| IV-129 | + |
| IV-130 | + |
| IV-131 | + |
| IV-132 | + |
| IV-133 | --- |
| IV-134 | + |
| IV-135 | + |
| IV-136 | + |
| IV-137 | + |
| IV-138 | + |
| IV-139 | + |
| IV-140 | + |
| IV-141 | + |
| IV-142 | + |
| IV-143 | + |
| IV-144 | ++ |
| IV-145 | + |
| IV-146 | + |
| IV-147 | + |
| IV-148 | + |
| IV-149 | --- |
| IV-150 | + |
| IV-151 | --- |
| IV-152 | + |
| IV-153 | --- |
| IV-154 | + |
| IV-155 | + |
| IV-156 | + |
| IV-157 | + |
| IV-158 | --- |
| IV-159 | + |
| IV-160 | + |
| IV-161 | + |
| IV-162 | + |
| IV-163 | --- |
| IV-164 | + |
| IV-165 | + |
| IV-166 | + |
| IV-167 | + |
| IV-168 | + |
| IV-169 | + |
| IV-170 | + |
| IV-171 | + |
| IV-172 | + |
| IV-173 | --- |
| IV-174 | + |
| IV-175 | + |
| IV-176 | + |
| IV-177 | + |
| IV-178 | + |
| IV-179 | + |
| IV-180 | + |
| IV-181 | + |
| IV-182 | ++ |
| IV-183 | + |
| IV-184 | +++ |
| IV-185 | --- |
| IV-186 | --- |
| IV-187 | --- |
| IV-188 | --- |
| IV-189 | ++ |
| IV-190 | --- |
| IV-191 | ++ |
| IV-192 | ++ |
| IV-193 | +++ |
| IV-194 | +++ |
| IV-195 | ++ |
| IV-196 | --- |
| IV-197 | --- |
| IV-198 | --- |
| IV-199 | ++ |
| IV-200 | ++ |
| IV-201 | +++ |
| IV-202 | ++ |
| IV-203 | --- |
| IV-204 | + |
| IV-205 | --- |
| IV-206 | ++ |
| IV-207 | +++ |
| IV-208 | --- |
| IV-209 | ++ |
| IV-210 | ++ |
| IV-211 | ++ |
| IV-212 | --- |
| IV-213 | ++ |
| IV-214 | +++ |
| IV-215 | +++ |
| IV-216 | ++ |
| IV-217 | +++ |
| IV-218 | --- |
| IV-219 | --- |
| IV-220 | --- |
| IV-221 | --- |
| IV-222 | +++ |
| IV-223 | --- |
| IV-224 | +++ |
| IV-225 | ++ |

TABLE 17-continued

Cellular activity for compounds of Formula IV (biomarker assay)

| Compound of Formula IV- | GCN2 Biomarker (IC$_{50}$) |
|---|---|
| IV-226 | --- |
| IV-227 | --- |
| IV-228 | ++ |
| IV-229 | --- |
| IV-230 | ++ |
| IV-231 | --- |
| IV-232 | --- |
| IV-233 | --- |
| IV-234 | + |
| IV-235 | --- |
| IV-236 | --- |
| IV-237 | --- |
| IV-238 | --- |
| IV-239 | --- |
| IV-240 | --- |
| IV-241 | --- |
| IV-242 | --- |
| IV-243 | --- |
| IV-244 | --- |
| IV-245 | + |
| IV-246 | --- |
| IV-247 | +++ |
| IV-248 | --- |
| IV-249 | --- |
| IV-250 | --- |
| IV-251 | --- |
| IV-252 | --- |
| IV-253 | --- |
| IV-254 | --- |
| IV-255 | --- |
| IV-256 | --- |
| IV-257 | --- |
| IV-258 | --- |
| IV-259 | --- |
| IV-260 | --- |
| IV-261 | --- |
| IV-262 | --- |
| IV-263 | --- |
| IV-264 | --- |
| IV-265 | --- |
| IV-266 | --- |
| IV-267 | --- |
| IV-268 | --- |
| IV-269 | --- |
| IV-270 | --- |
| IV-271 | --- |
| IV-272 | --- |
| IV-273 | --- |
| IV-274 | --- |
| IV-275 | --- |
| IV-276 | --- |
| IV-277 | --- |
| IV-278 | --- |
| IV-279 | +++ |
| IV-280 | +++ |
| IV-281 | --- |
| IV-282 | --- |
| IV-283 | --- |
| IV-284 | --- |
| IV-285 | --- |
| IV-286 | --- |
| IV-287 | --- |
| IV-288 | +++ |
| IV-289 | --- |
| IV-290 | --- |
| IV-291 | --- |
| IV-292 | --- |
| IV-293 | --- |
| IV-294 | --- |
| IV-295 | --- |
| IV-296 | --- |
| IV-297 | --- |
| IV-298 | --- |
| IV-299 | --- |
| IV-300 | --- |
| IV-301 | --- |
| IV-302 | --- |
| IV-303 | --- |
| IV-304 | --- |
| IV-305 | ++ |
| IV-306 | --- |
| IV-307 | --- |
| IV-308 | --- |
| IV-309 | --- |
| IV-310 | --- |
| IV-311 | +++ |
| IV-312 | --- |
| IV-313 | --- |
| IV-314 | --- |
| IV-315 | --- |
| IV-316 | --- |
| IV-317 | --- |
| IV-318 | +++ |
| IV-319 | --- |
| IV-320 | --- |
| IV-321 | --- |
| IV-322 | --- |
| IV-323 | ++ |
| IV-324 | --- |
| IV-325 | --- |
| IV-326 | --- |
| IV-327 | --- |
| IV-328 | --- |
| IV-329 | --- |
| IV-330 | --- |
| IV-331 | --- |
| IV-332 | --- |
| IV-333 | --- |
| IV-334 | --- |
| IV-335 | --- |
| IV-336 | --- |
| IV-337 | --- |
| IV-338 | --- |
| IV-339 | --- |
| IV-340 | ++ |
| IV-341 | + |
| IV-342 | --- |
| IV-343 | +++ |
| IV-344 | ++ |
| IV-345 | ++ |
| IV-346 | +++ |
| IV-347 | + |
| IV-348 | --- |
| IV-349 | ++ |
| IV-350 | ++ |
| IV-351 | +++ |
| IV-352 | --- |
| IV-353 | ++ |
| IV-354 | + |
| IV-355 | ++ |
| IV-356 | --- |
| IV-357 | + |
| IV-358 | ++ |
| IV-359 | +++ |
| IV-360 | +++ |
| IV-361 | +++ |
| IV-362 | ++ |
| IV-363 | +++ |
| IV-364 | ++ |
| IV-365 | ++ |
| IV-366 | + |
| IV-367 | --- |
| IV-368 | + |
| IV-369 | ++ |
| IV-370 | --- |
| IV-371 | ++ |
| IV-372 | ++ |
| IV-373 | ++ |

TABLE 17-continued

Cellular activity for compounds of Formula IV (biomarker assay)

| Compound of Formula IV- | GCN2 Biomarker (IC$_{50}$) |
|---|---|
| IV-374 | ++ |
| IV-375 | +++ |
| IV-376 | ++ |
| IV-377 | ++ |
| IV-378 | +++ |
| IV-379 | ++ |
| IV-380 | --- |
| IV-381 | --- |
| IV-382 | --- |
| IV-383 | --- |
| IV-384 | ++ |
| IV-385 | ++ |
| IV-386 | ++ |
| IV-387 | +++ |
| IV-388 | +++ |
| IV-389 | ++ |
| IV-390 | --- |
| IV-391 | ++ |
| IV-392 | +++ |
| IV-393 | --- |
| IV-394 | + |
| IV-395 | --- |
| IV-396 | ++ |
| IV-397 | + |
| IV-398 | + |
| IV-399 | ++ |
| IV-400 | + |
| IV-401 | ++ |
| IV-402 | +++ |
| IV-403 | +++ |
| IV-404 | ++ |
| IV-405 | +++ |
| IV-406 | + |
| IV-407 | ++ |
| IV-408 | + |
| IV-409 | ++ |
| IV-410 | + |
| IV-411 | ++ |
| IV-412 | --- |
| IV-413 | ++ |
| IV-414 | +++ |
| IV-415 | +++ |
| IV-416 | ++ |
| IV-417 | --- |
| IV-418 | ++ |
| IV-419 | ++ |
| IV-420 | +++ |
| IV-421 | ++ |
| IV-422 | + |
| IV-423 | + |
| IV-424 | + |
| IV-425 | + |
| IV-426 | + |
| IV-427 | + |
| IV-428 | --- |
| IV-429 | --- |
| IV-430 | --- |
| IV-431 | --- |
| IV-432 | --- |
| IV-433 | --- |
| IV-434 | --- |
| IV-435 | ++ |
| IV-436 | + |
| IV-437 | + |
| IV-438 | --- |
| IV-439 | + |
| IV-440 | --- |
| IV-441 | --- |
| IV-442 | + |
| IV-443 | + |
| IV-444 | + |
| IV-445 | --- |
| IV-446 | --- |
| IV-447 | + |
| IV-448 | --- |
| IV-449 | + |
| IV-450 | ++ |
| IV-451 | +++ |
| IV-452 | ++ |
| IV-453 | --- |
| IV-454 | ++ |
| IV-455 | --- |
| IV-456 | --- |
| IV-457 | --- |
| IV-458 | + |
| IV-459 | ++ |
| IV-460 | ++ |
| IV-461 | ++ |
| IV-462 | + |
| IV-463 | + |
| IV-464 | --- |
| IV-465 | ++ |
| IV-466 | ++ |
| IV-467 | + |
| IV-468 | ++ |
| IV-469 | + |
| IV-470 | + |
| IV-471 | + |
| IV-472 | ++ |
| IV-473 | --- |
| IV-474 | +++ |
| IV-475 | --- |
| IV-476 | --- |
| IV-477 | --- |
| IV-478 | --- |
| IV-479 | --- |
| IV-480 | + |
| IV-481 | --- |
| IV-482 | --- |
| IV-483 | --- |
| IV-484 | --- |
| IV-485 | +++ |
| IV-486 | --- |
| IV-487 | --- |
| IV-488 | + |
| IV-489 | --- |
| IV-490 | --- |
| IV-491 | +++ |
| IV-492 | +++ |
| IV-493 | + |
| IV-494 | ++ |
| IV-495 | + |
| IV-496 | --- |
| IV-497 | --- |
| IV-498 | --- |
| IV-499 | ++ |
| IV-500 | --- |
| IV-501 | ++ |
| IV-502 | --- |
| IV-503 | --- |
| IV-504 | --- |
| IV-505 | --- |
| IV-506 | --- |
| IV-507 | --- |
| IV-508 | --- |
| IV-509 | --- |
| IV-510 | --- |
| IV-511 | --- |
| IV-512 | --- |
| IV-513 | --- |
| IV-514 | --- |
| IV-515 | --- |
| IV-516 | --- |
| IV-517 | --- |
| IV-518 | --- |
| IV-519 | --- |
| IV-520 | --- |
| IV-521 | --- |

TABLE 17-continued

Cellular activity for compounds of Formula IV (biomarker assay)

| Compound of Formula IV- | GCN2 Biomarker (IC$_{50}$) |
|---|---|
| IV-522 | --- |
| IV-523 | --- |
| IV-524 | +++ |
| IV-525 | ++ |
| IV-526 | --- |
| IV-527 | --- |
| IV-528 | --- |
| IV-529 | --- |
| IV-530 | --- |
| IV-531 | --- |
| IV-532 | --- |
| IV-533 | --- |
| IV-534 | --- |
| IV-535 | ++ |
| IV-536 | --- |
| IV-537 | --- |
| IV-538 | ++ |
| IV-539 | --- |
| IV-540 | ++ |
| IV-541 | --- |
| IV-542 | --- |
| IV-543 | --- |
| IV-544 | --- |
| IV-545 | ++ |
| IV-546 | +++ |
| IV-547 | --- |
| IV-548 | ++ |
| IV-549 | --- |
| IV-550 | --- |
| IV-551 | --- |
| IV-552 | --- |
| IV-553 | --- |
| IV-554 | --- |
| IV-555 | --- |
| IV-556 | --- |
| IV-557 | --- |
| IV-558 | + |
| IV-559 | --- |
| IV-560 | --- |
| IV-561 | --- |
| IV-562 | +++ |
| IV-563 | ++ |
| IV-564 | --- |
| IV-565 | --- |
| IV-566 | --- |
| IV-567 | ++ |
| IV-568 | --- |
| IV-569 | --- |
| IV-570 | --- |
| IV-571 | --- |
| IV-572 | ++ |
| IV-573 | ++ |
| IV-574 | + |
| IV-575 | ++ |
| IV-576 | ++ |
| IV-577 | ++ |
| IV-578 | ++ |
| IV-579 | --- |
| IV-580 | + |
| IV-581 | --- |
| IV-582 | ++ |
| IV-583 | ++ |
| IV-584 | --- |
| IV-585 | --- |
| IV-586 | --- |
| IV-587 | --- |
| IV-588 | --- |
| IV-589 | ++ |
| IV-590 | + |
| IV-591 | + |
| IV-592 | + |
| IV-593 | ++ |
| IV-594 | --- |
| IV-595 | --- |
| IV-596 | --- |
| IV-597 | --- |
| IV-598 | --- |
| IV-599 | --- |
| IV-600 | --- |
| IV-601 | +++ |
| IV-602 | --- |
| IV-603 | --- |
| IV-604 | --- |
| IV-605 | --- |
| IV-606 | --- |
| IV-607 | --- |
| IV-608 | ++ |
| IV-609 | + |
| IV-610 | --- |
| IV-611 | --- |
| IV-612 | --- |
| IV-613 | --- |
| IV-614 | + |
| IV-615 | ++ |
| IV-616 | --- |
| IV-617 | --- |
| IV-618 | --- |
| IV-619 | --- |
| IV-620 | --- |
| IV-621 | ++ |
| IV-622 | ++ |
| IV-623 | +++ |
| IV-624 | ++ |
| IV-625 | --- |
| IV-626 | ++ |
| IV-627 | ++ |
| IV-628 | ++ |
| IV-629 | ++ |
| IV-630 | + |
| IV-631 | ++ |
| IV-632 | + |
| IV-633 | + |
| IV-634 | --- |
| IV-635 | ++ |
| IV-636 | ++ |
| IV-637 | ++ |
| IV-638 | + |
| IV-639 | +++ |
| IV-640 | ++ |
| IV-641 | --- |
| IV-642 | --- |
| IV-643 | --- |
| IV-644 | --- |
| IV-645 | --- |
| IV-646 | --- |
| IV-647 | --- |
| IV-648 | ++ |
| IV-649 | + |
| IV-650 | ++ |
| IV-651 | +++ |
| IV-652 | ++ |
| IV-653 | --- |
| IV-654 | --- |
| IV-655 | --- |
| IV-656 | --- |
| IV-657 | --- |
| IV-658 | --- |
| IV-659 | --- |
| IV-660 | --- |
| IV-661 | --- |
| IV-662 | --- |
| IV-663 | --- |
| IV-664 | --- |
| IV-665 | --- |
| IV-666 | --- |
| IV-667 | --- |
| IV-668 | ++ |
| IV-669 | + |

TABLE 17-continued

Cellular activity for compounds of Formula IV (biomarker assay)

| Compound of Formula IV- | GCN2 Biomarker (IC$_{50}$) |
|---|---|
| IV-670 | ++ |
| IV-671 | --- |
| IV-672 | --- |
| IV-673 | ++ |
| IV-674 | --- |
| IV-675 | + |
| IV-676 | ++ |
| IV-677 | ++ |
| IV-678 | ++ |
| IV-679 | ++ |
| IV-680 | ++ |
| IV-681 | --- |
| IV-682 | ++ |
| IV-683 | ++ |
| IV-684 | +++ |
| IV-685 | +++ |
| IV-686 | ++ |
| IV-687 | ++ |
| IV-688 | ++ |
| IV-689 | + |
| IV-690 | ++ |
| IV-691 | ++ |
| IV-692 | + |
| IV-693 | + |
| IV-694 | + |
| IV-695 | + |
| IV-696 | + |
| IV-697 | --- |
| IV-698 | --- |
| IV-699 | --- |
| IV-700 | --- |
| IV-701 | --- |
| IV-702 | + |
| IV-703 | + |
| IV-704 | + |
| IV-705 | + |
| IV-712 | + |
| IV-716 | + |
| IV-724 | + |
| IV-733 | + |
| IV-741 | + |
| IV-743 | + |
| IV-754 | +++ |
| IV-757 | +++ |
| IV-758 | +++ |
| IV-763 | +++ |
| IV-764 | +++ |
| IV-765 | +++ |
| IV-766 | +++ |
| IV-767 | +++ |
| IV-769 | +++ |
| IV-770 | +++ |
| IV-771 | +++ |
| IV-772 | ++ |
| IV-774 | + |
| IV-775 | + |
| IV-776 | ++ |
| IV-777 | ++ |

+++ for IC$_{50}$ < 0.5 µM;
++ for IC$_{50}$ in 0.5 µM-5 µM range;
+ for IC$_{50}$ > 5 µM;
--- when no data available

TABLE 18

Cellular activity for compounds of Formula V (biomarker assay)

| Compound V | GCN2 Biomarker (IC$_{50}$) |
|---|---|
| V-1 | ++ |
| V-2 | --- |
| V-3 | +++ |
| V-4 | ++ |
| V-5 | + |
| V-6 | --- |
| V-7 | ++ |
| V-8 | --- |
| V-9 | --- |
| V-10 | +++ |
| V-11 | +++ |
| V-12 | ++ |
| V-13 | +++ |
| V-14 | ++ |
| V-15 | +++ |
| V-16 | + |
| V-17 | ++ |
| V-18 | + |
| V-19 | + |
| V-20 | +++ |

+++ for IC$_{50}$ < 0.5 µM;
++ for IC$_{50}$ in 0.5 µM-5 µM range;
+ for IC$_{50}$ > 5 µM;
--- when no data available

Example 115: Human IL-2 Assay for GCN2 Inhibition

Tumor microenvironment is profoundly immuno-suppressive. This may be attributed to the depletion of amino acids (like arginine and tryptophan) which triggers the activation of GCN2 in immune cells, including T cell and myeloid cells. In T cells, activation of GCN2 leads to reduce effector functions of CD8 T cells and induction and/or maintenance of immuno-suppressive T-regs. Inhibition of that immuno-suppressive response by GCN2 inhibitors enables an anti-cancer immune response by activating effector T-cells. Herein we describe an in-vitro system we established using human T-cells stimulated in low amino acid condition in order to engage the GCN2 biology. The method described involves the modulation of IL-2 levels secreted by human T cells in responses to the GCN2 inhibitors disclosed herein.

Amino acid-free RPMI was reconstituted with all but one of the amino acids found in standard RMPI (e.g. Arginine, Tryptophan), 10% charcoal-stripped fetal bovine serum, 100 Units/mL penicillin and 0.1 mg/mL streptomycin. Primary human pan T-cells were isolated using Pan T Cell Isolation Kit, human (MACS Miltenyi biotech Cat #Order no. 130-096-535) from apheresis cones and 5×104 pan T-cells per well. The purified T cells are seeded in Nunc™ 96-Well Polystyrene Round Bottom Microwell Plates (the cells are rested in No TRP media in a 15 ml falcon tube in the incubator for 30-45 minutes while titrations for tryptophan and the GCN2 inhibitor compound are made) A plate matrix was developed to titrate both a GCN2 inhibitor and the amino acid of interest ranging from "No Amino Acid" condition, up to the concentration found in the regular RPMI media (20 µM for TRP and 950 µM for Arginine). The cells were incubated for 30 min at 37° C. with the GCN2 inhibitor and then stimulated with 5×104 anti-CD3/CD28 Dynabeads® per well. After 96 hours of incubation the IL-2 level in the supernatant were measured using ELISA (R&D systems Cat #DY202 (Human IL-2 DuoSet ELISA). Data were plotted in GraphPad Prism software and $EC_{50}$ is calculated.

TABLE 19

$EC_{50}$ values based on IL-2 secretion from T cells

| Compound # | IL2/T-cell $EC_{50}$ (nM) |
|---|---|
| II-752 | +++, +++ |
| II-755 | ++ |
| II-768 | + |
| II-771 | ++ |
| II-772 | ++ |
| II-773 | +++ |
| II-774 | +++ |
| II-775 | ++ |
| II-776 | ++ |
| II-777 | ++ |
| II-778 | + |
| II-779 | + |
| IV-763 | ++ |
| IV-767 | ++ |
| IV-776 | + |

+++ for $EC_{50}$ < 100 nM;
++ for $EC_{50}$ in 100 μM 500 nM range;
+ for $EC_{50}$ > 500 nM;

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

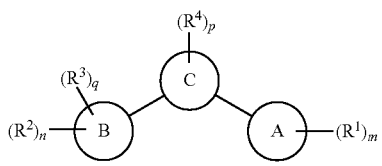

I or a pharmaceutically acceptable salt thereof, wherein:

Ring A is a 4-8 membered saturated monocyclic heterocyclic ring having 1-2 heteroatoms independently selected from nitrogen, oxygen, or sulfur;

Ring B is

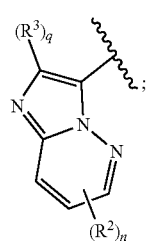

;

Ring C is

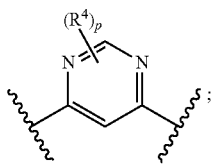

;

each of $R^1$ is independently fluoro, methyl, ethyl, —OH, methoxy, —CH$_2$OH,

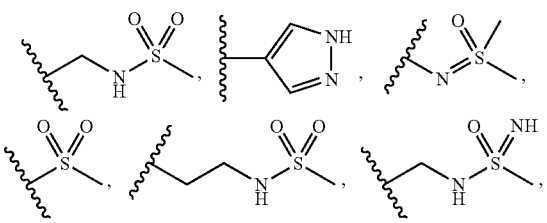

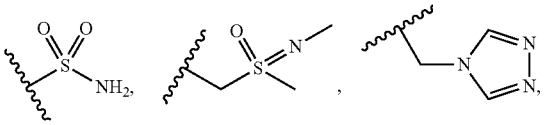

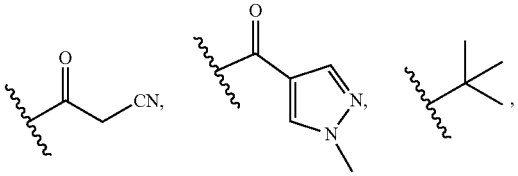

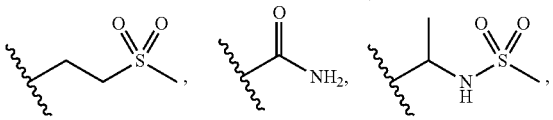

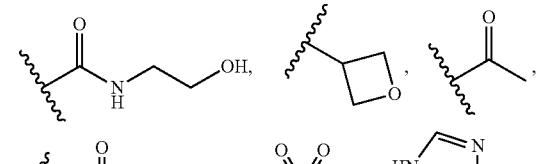

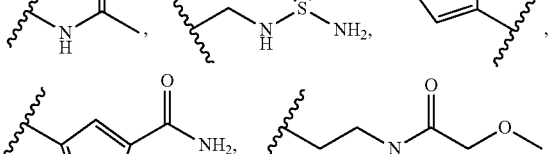

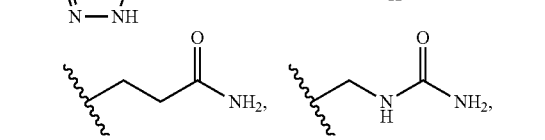

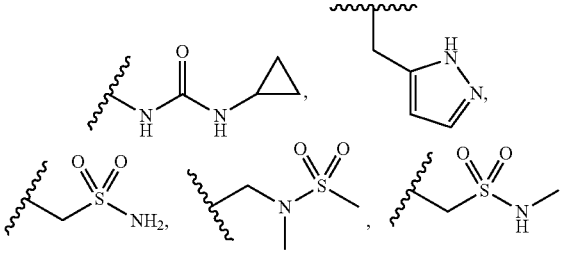

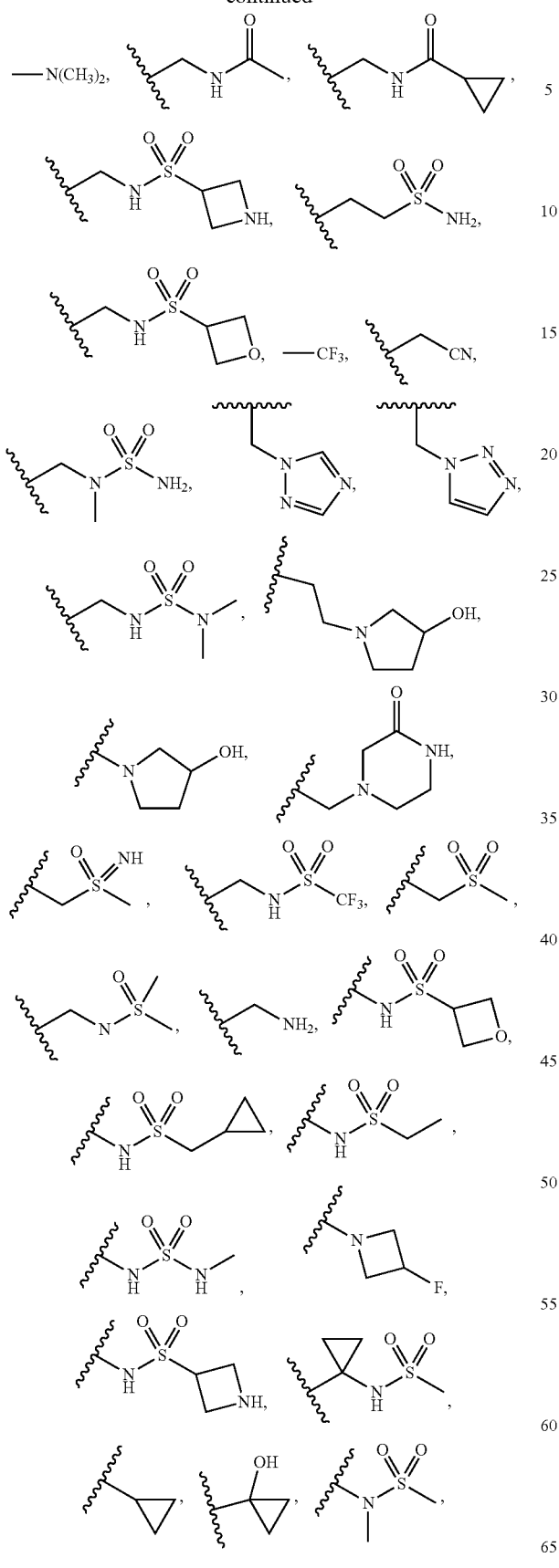
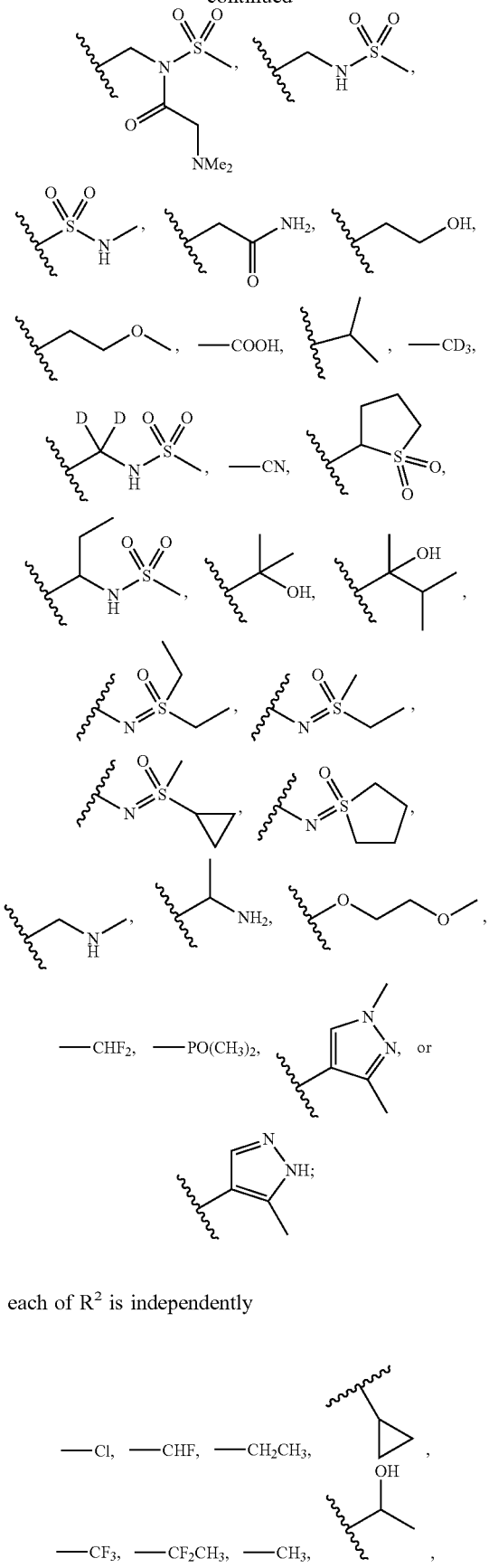
each of R² is independently

-continued

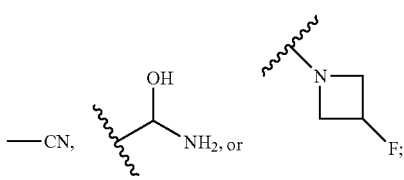

R³ is hydrogen;
R⁴ is hydrogen;
m is 0, 1, 2, 3, 4 or 5;
n is 0, 1, or 2;
p is 0 or 1; and
q is 0 or 1.

2. The compound of claim 1, of one of formula X-a, X-b, or X-c:

X-a
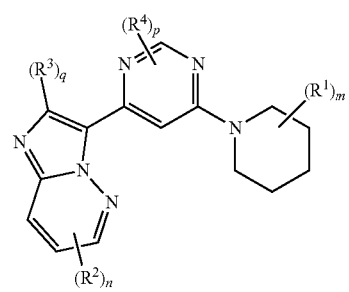

X-b
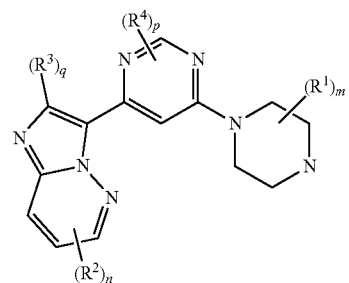

X-c
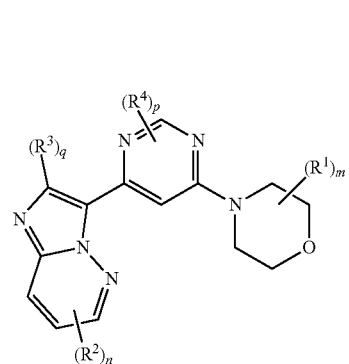

or a pharmaceutically acceptable salt thereof.

3. The compound of claim 1, wherein m is 1, 2, 3, or 4.

4. A pharmaceutical composition comprising a compound according to claim 1, and a pharmaceutically acceptable carrier, adjuvant, or vehicle.

5. The compound of claim 1, wherein Ring A is:

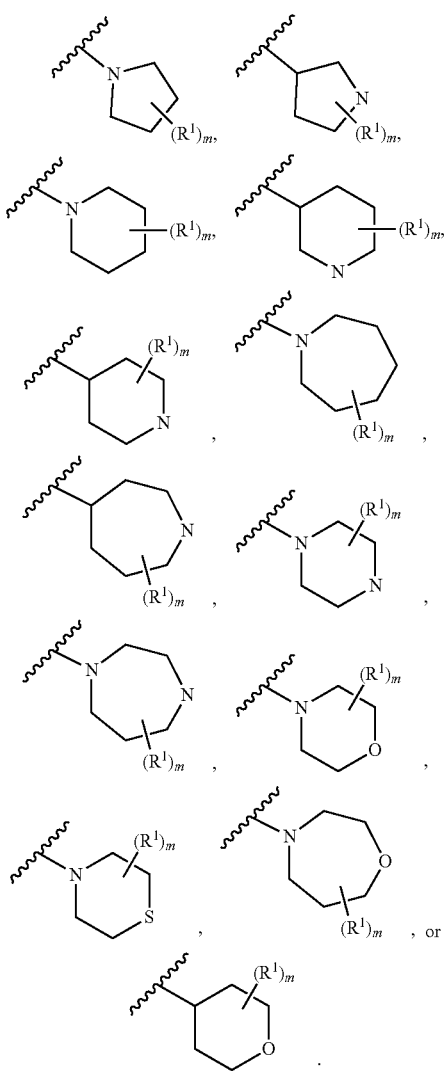

6. The compound of claim 1, wherein each of $R^1$ is independently fluoro, methyl, ethyl,

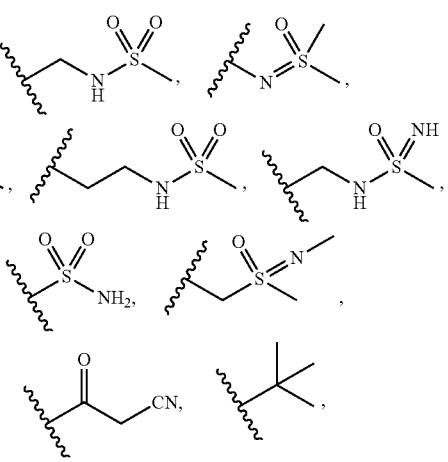

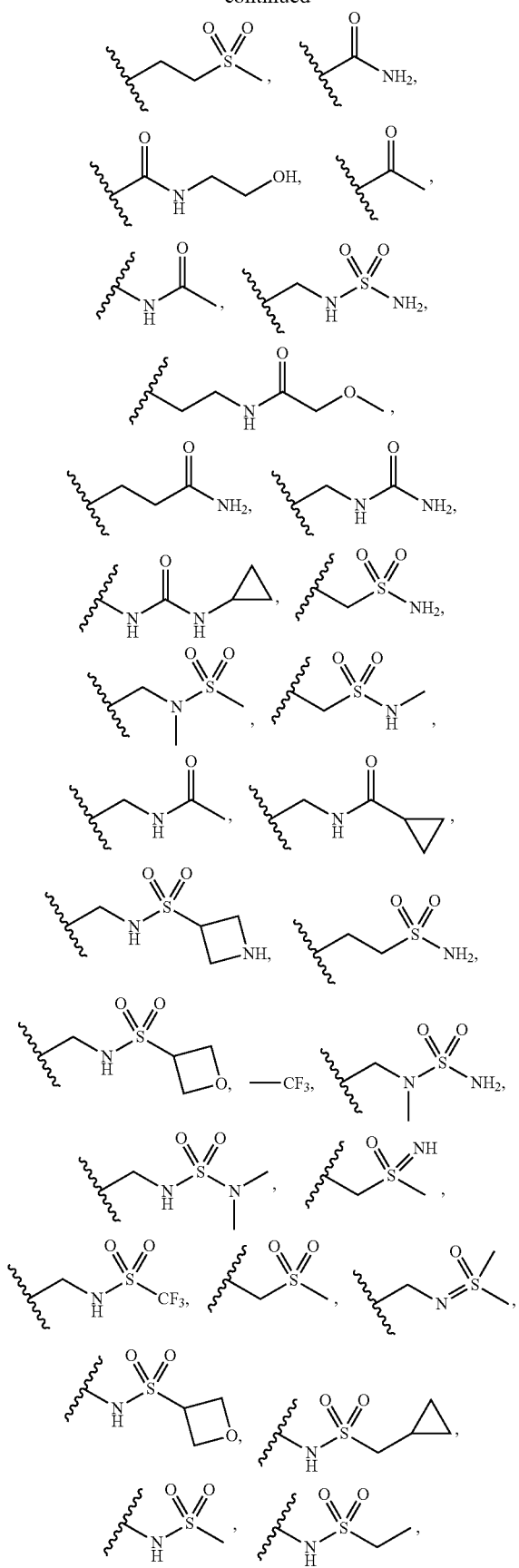
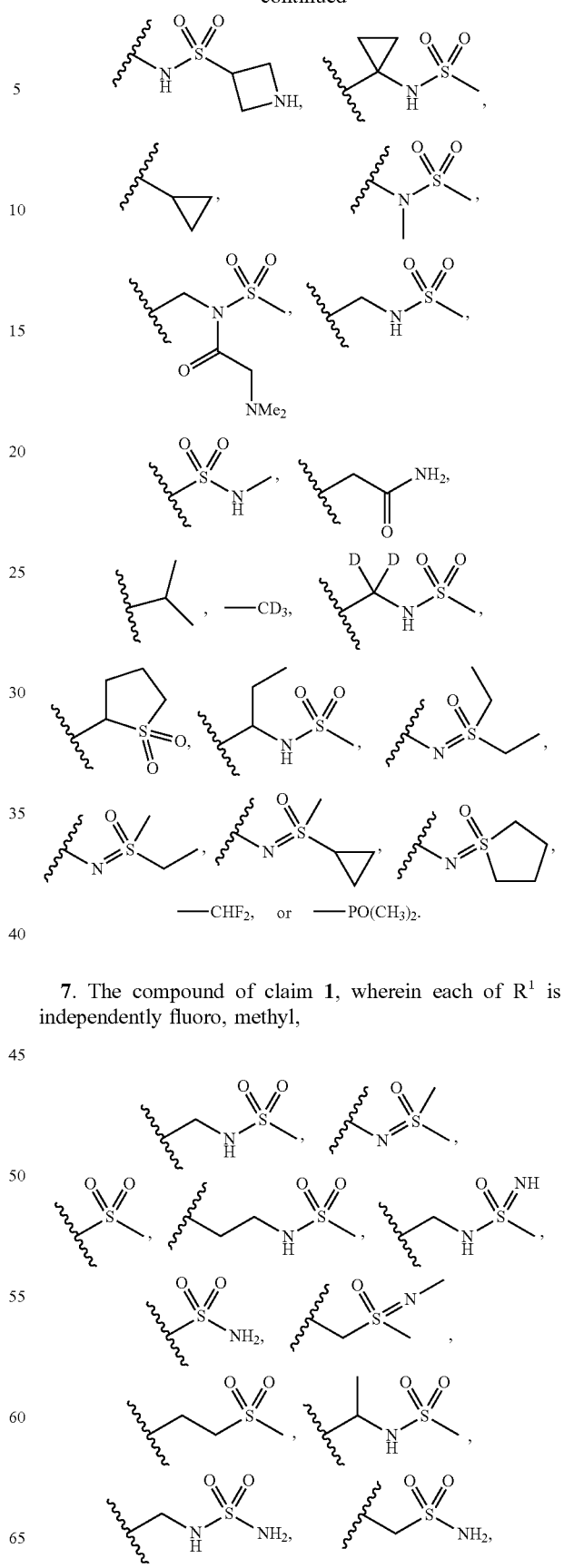
7. The compound of claim 1, wherein each of $R^1$ is independently fluoro, methyl, 1385
-continued
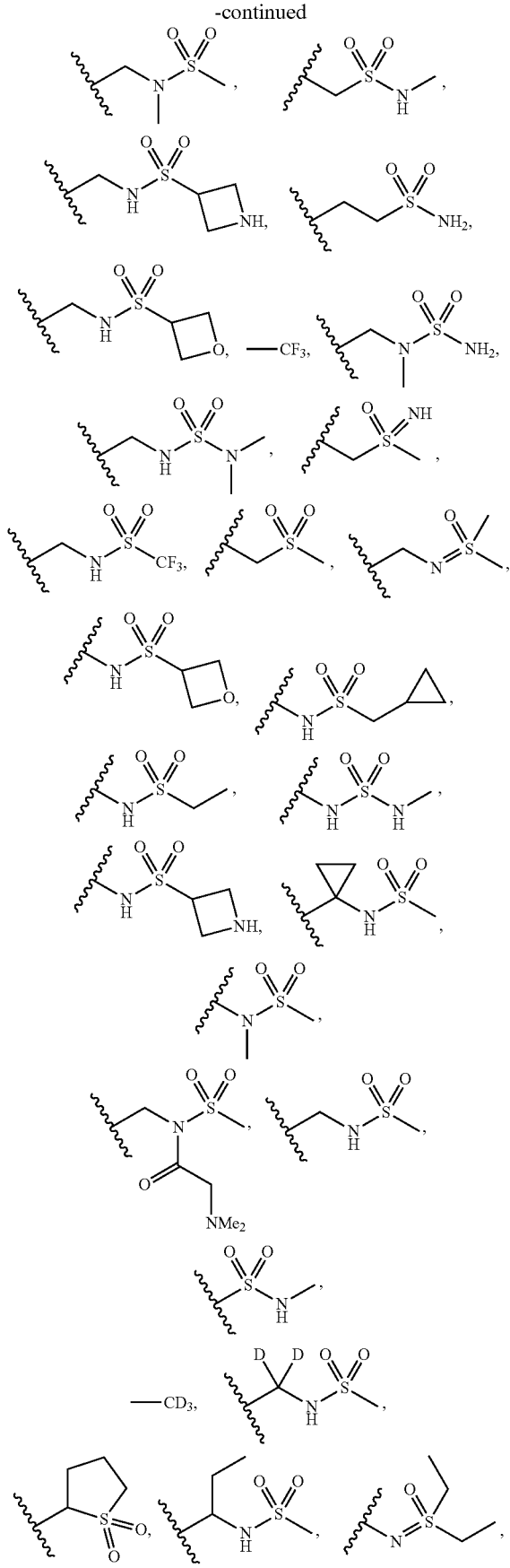
1386
-continued
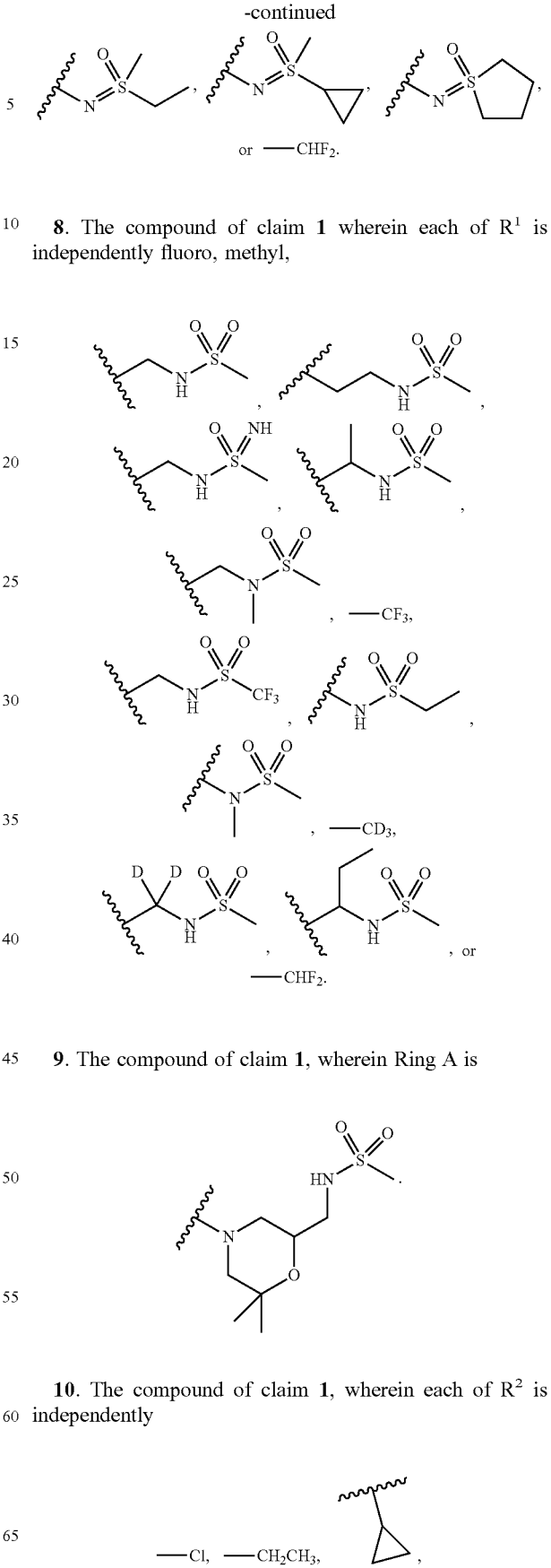
or —CHF$_2$.
8. The compound of claim 1 wherein each of R$^1$ is independently fluoro, methyl,
, or —CHF$_2$.
9. The compound of claim 1, wherein Ring A is
10. The compound of claim 1, wherein each of R$^2$ is independently
—Cl, —CH$_2$CH$_3$,

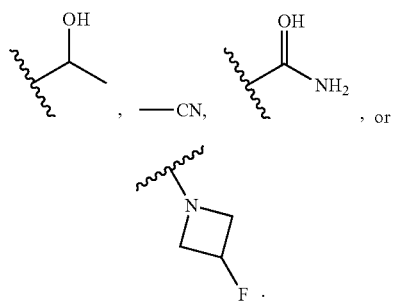
11. The compound of claim 1, wherein each of R² is independently —CHF₂, —CF₃, or —CF₂CH₃.
12. The compound of claim 1, wherein Ring B is
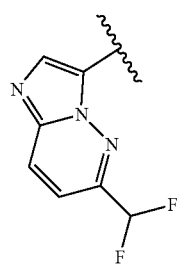
13. The compound of claim 1, wherein m is 3.
14. The compound of claim 1, wherein n is 1.
15. The compound of claim 1, wherein the compound is selected from the group consisting of:
II-3
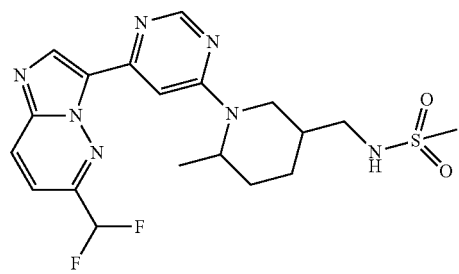
II-4
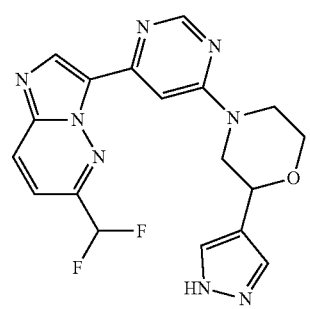
II-5
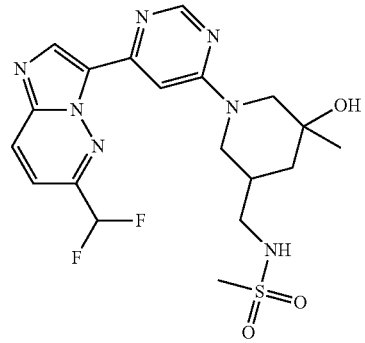
II-7
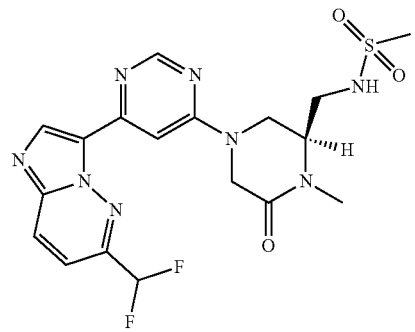
II-8
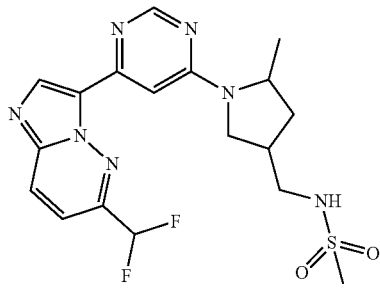
II-9
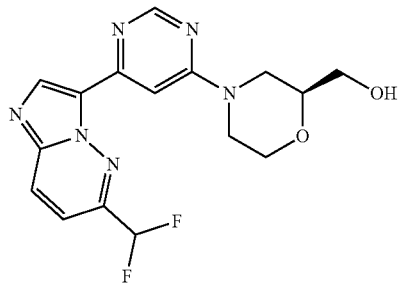
II-10
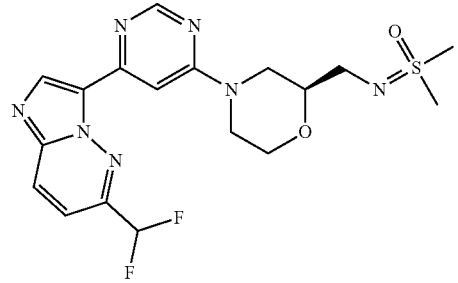

II-12
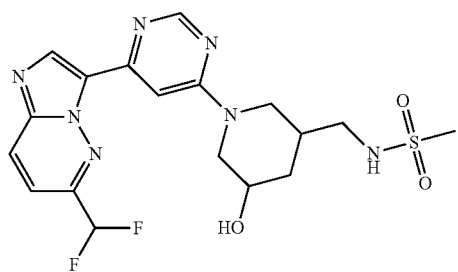
II-14
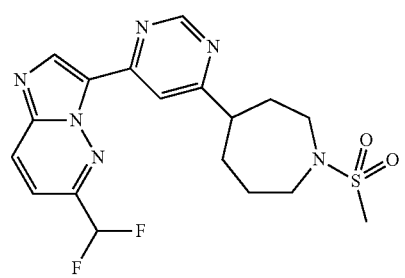
II-15
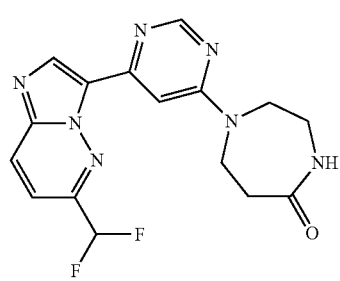
II-17
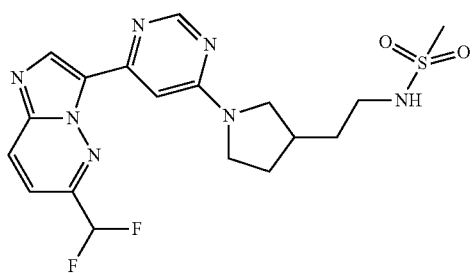
II-18
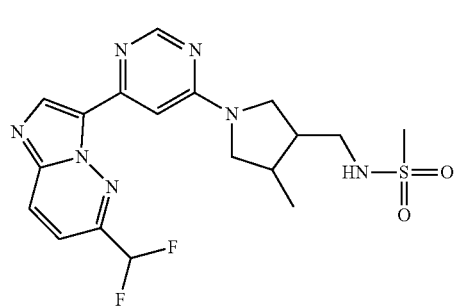
II-19
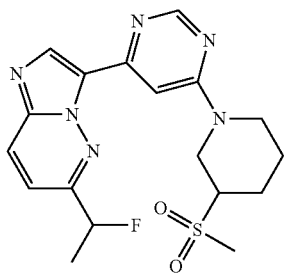
II-21
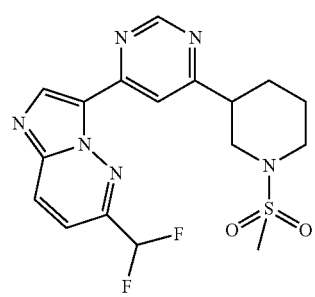
II-22
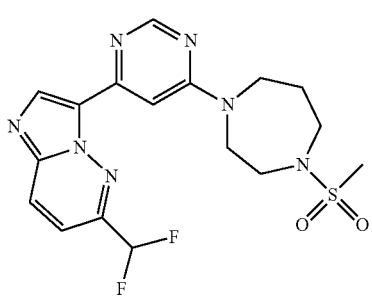
II-23
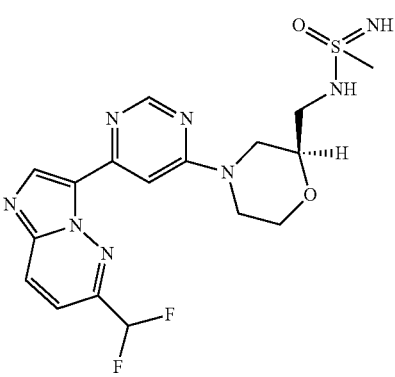
II-24
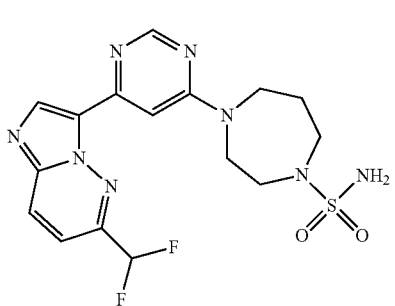

II-25
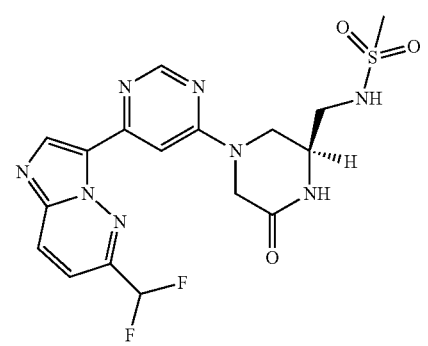
II-26
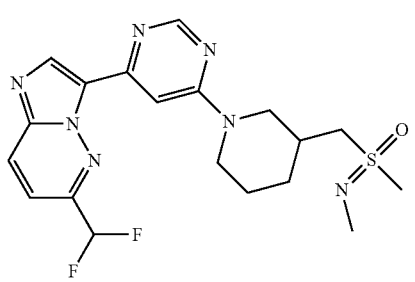
II-29
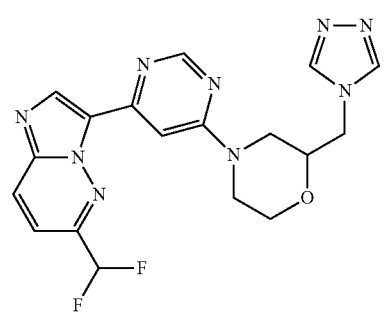
II-30
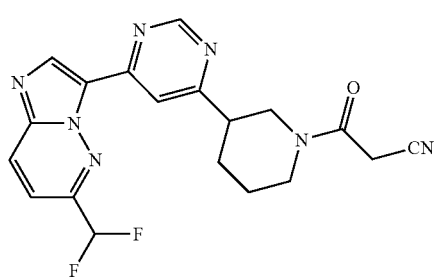
II-31
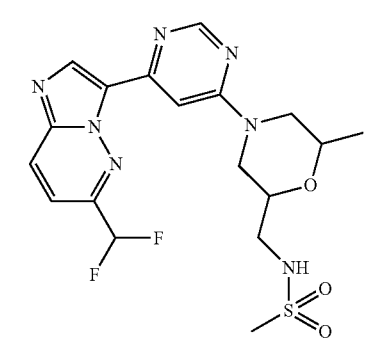
II-33
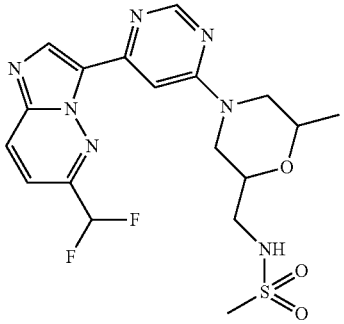
II-34
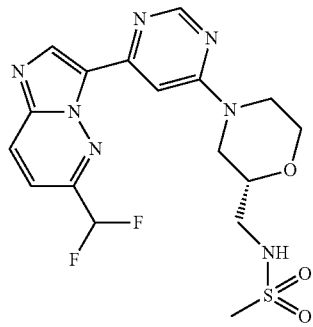
II-35
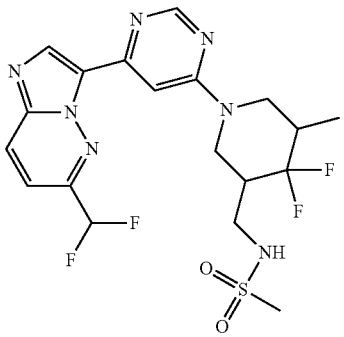
II-36
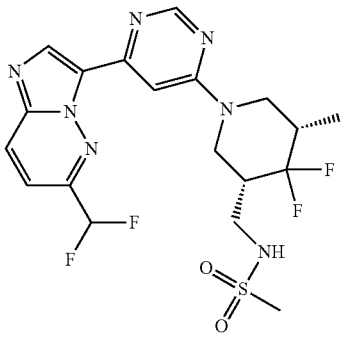
II-41
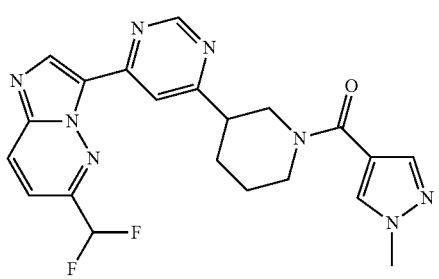

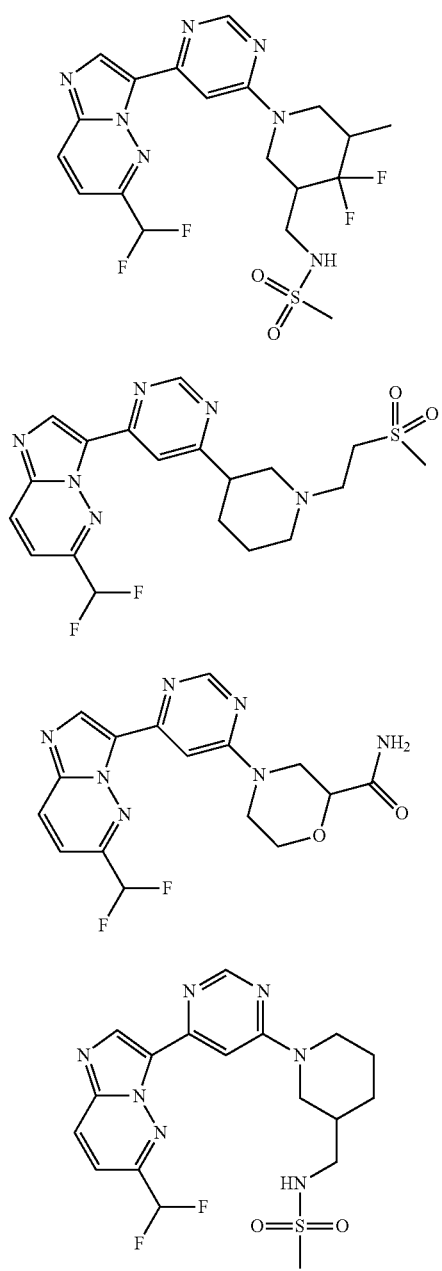
II-45
II-48
II-50
II-59
II-112
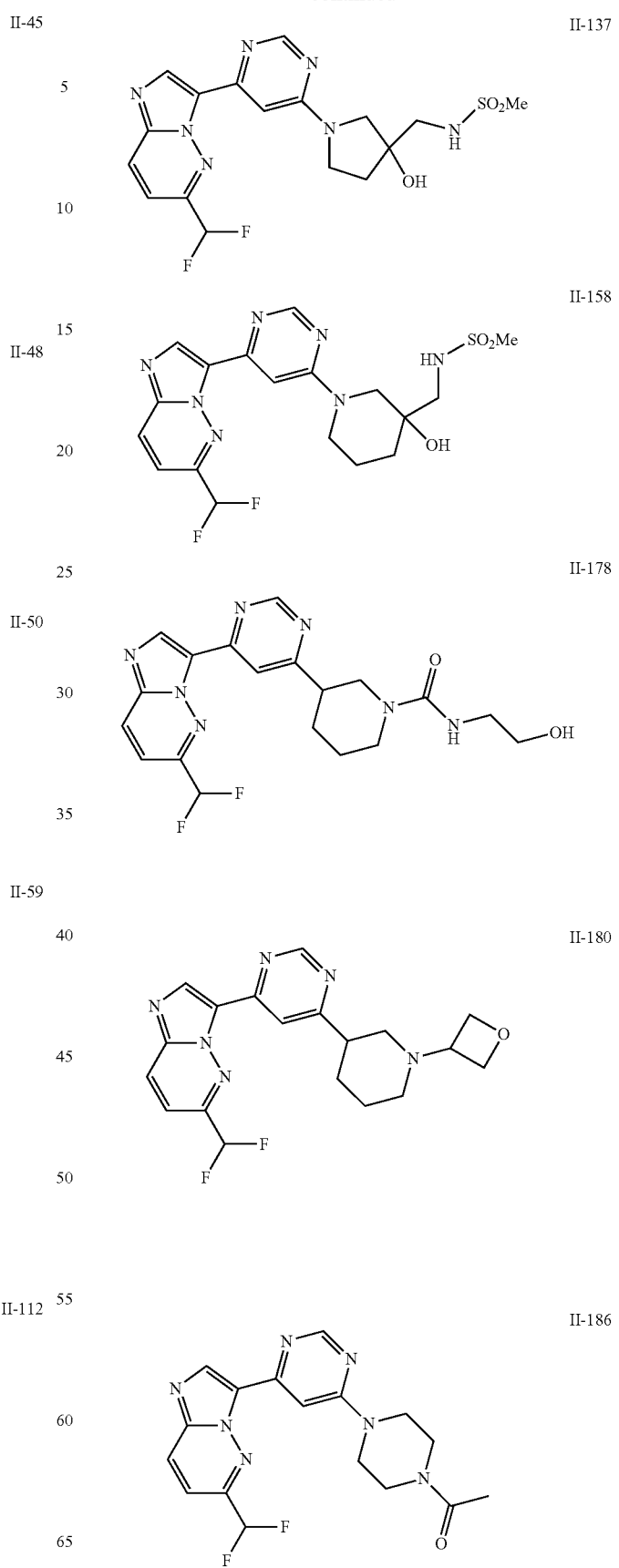
II-137
II-158
II-178
II-180
II-186

-continued
II-190
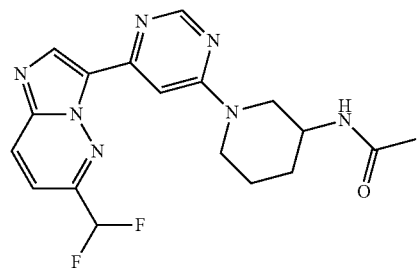
II-191
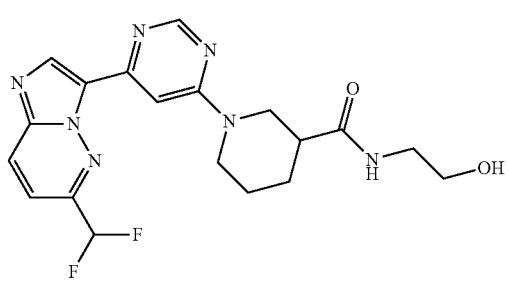
II-192
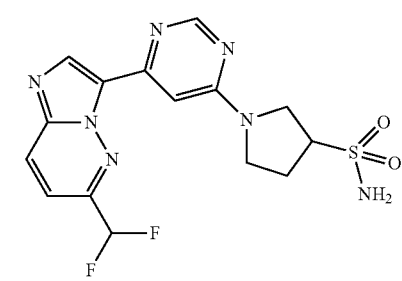
II-196
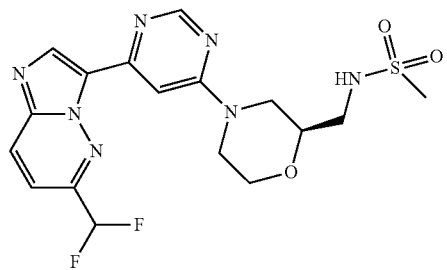
II-197
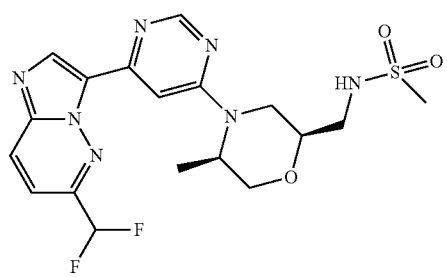
-continued
II-199
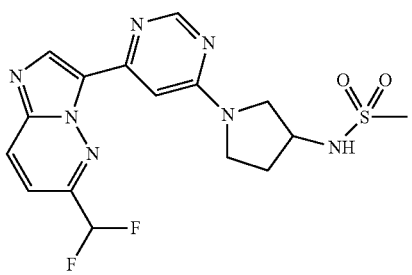
II-201
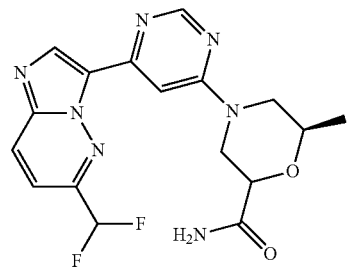
II-202
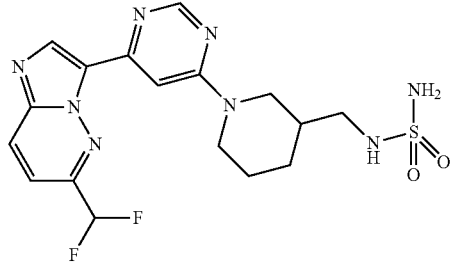
II-203
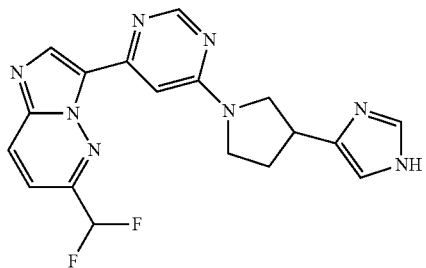
II-205
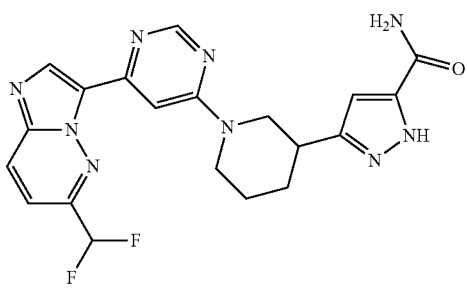

II-206
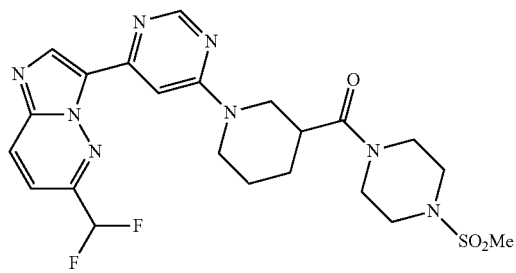
II-209
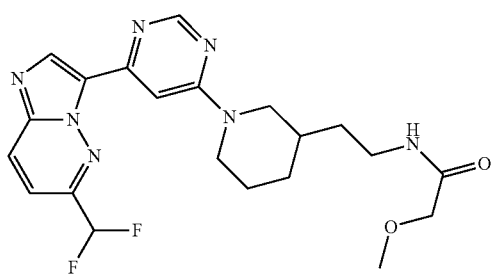
II-210
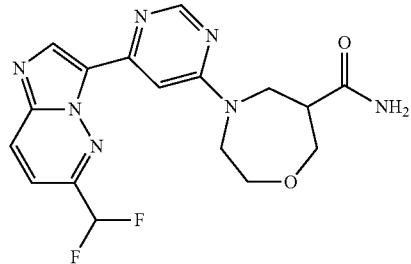
II-212
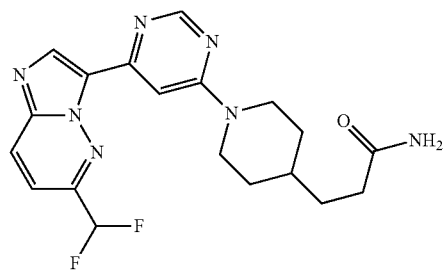
II-213
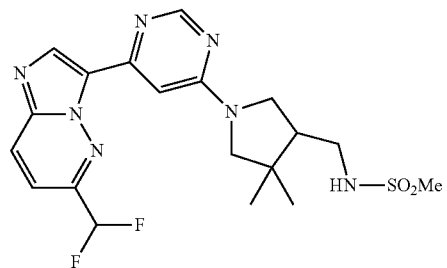
II-214
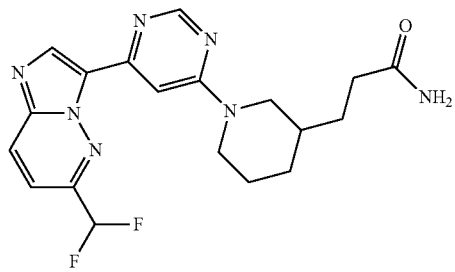
II-215
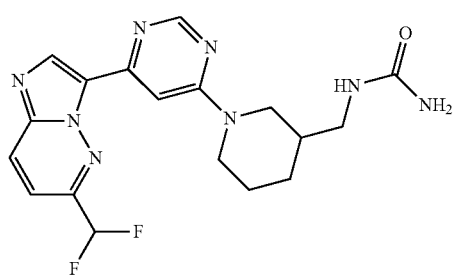
II-216
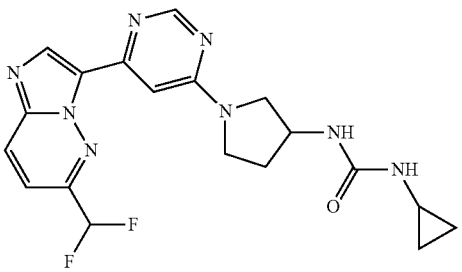
II-217
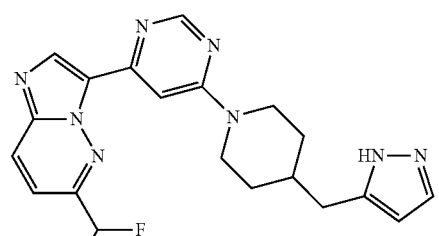
II-219
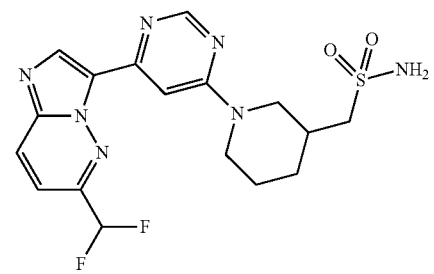

II-221 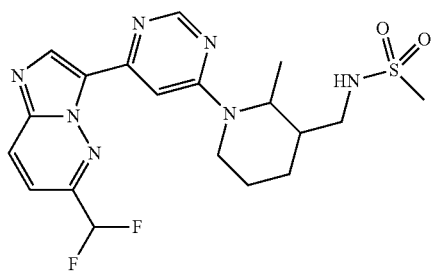
II-237 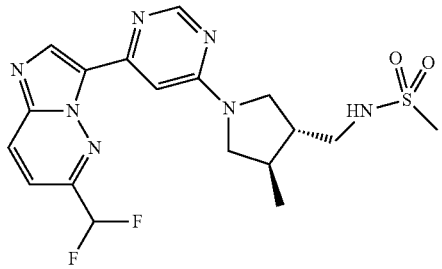
II-222 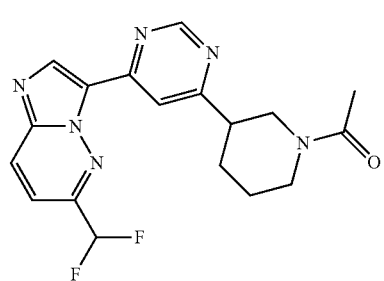
II-247 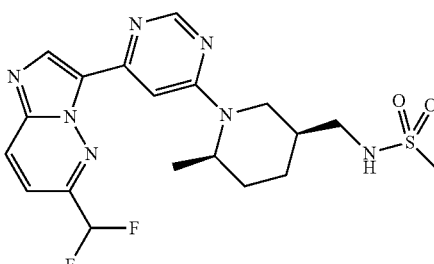
II-234 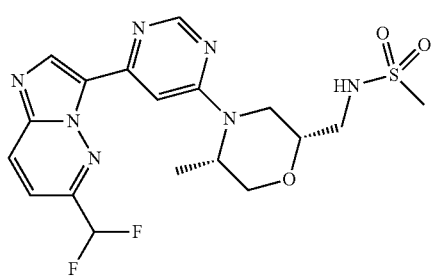
II-249 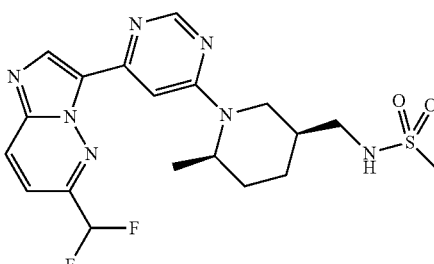
II-235 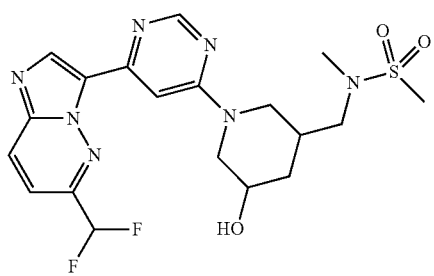
II-250 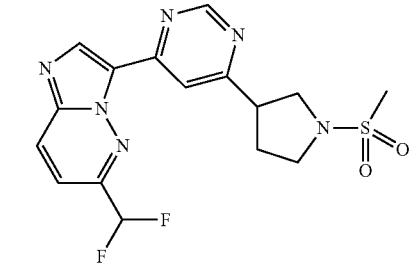
II-236 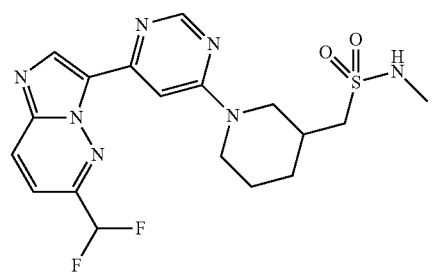
II-251 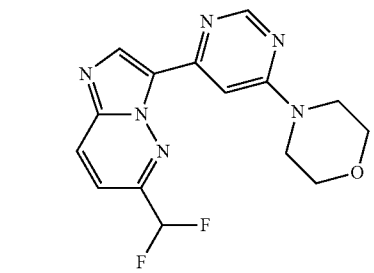

| 1401 -continued | 1402 -continued |
|---|---|
| II-253 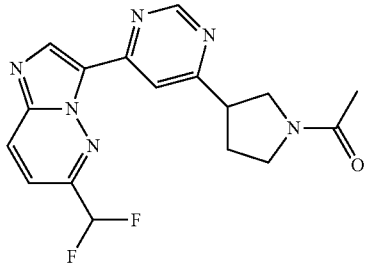 | II-261 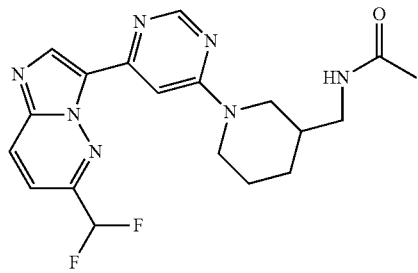 |
| II-254 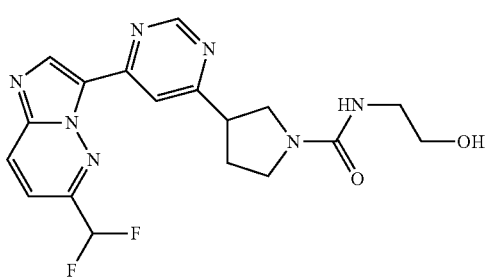 | II-262 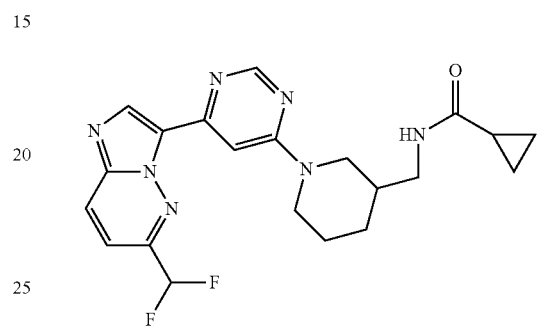 |
| II-255 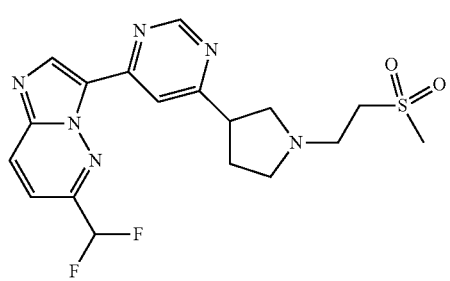 | II-268 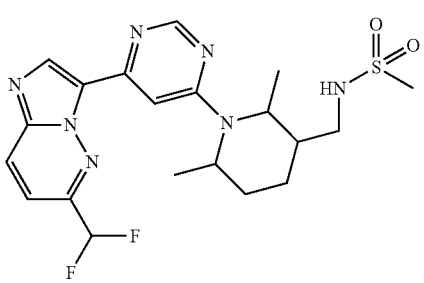 |
| II-257 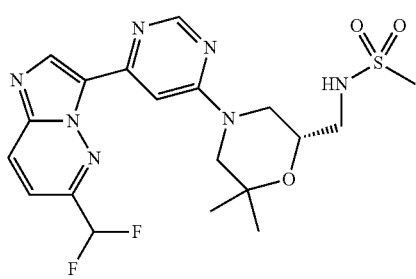 | II-272 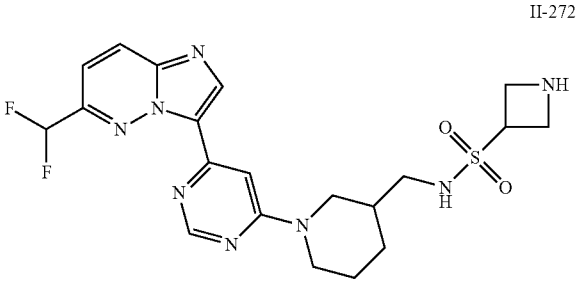 |
| II-258 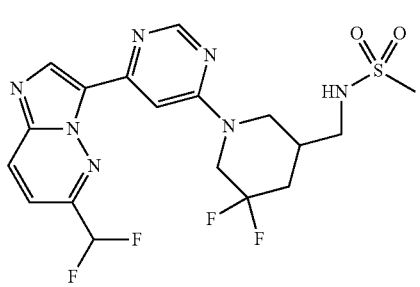 | II-283 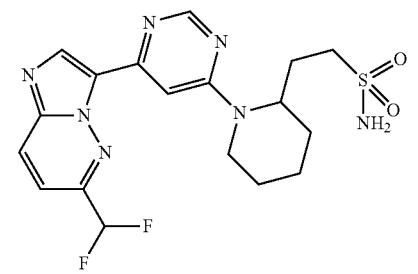 |

II-289
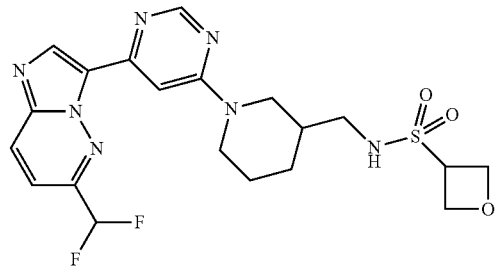
II-296
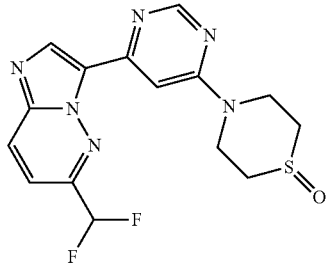
II-290
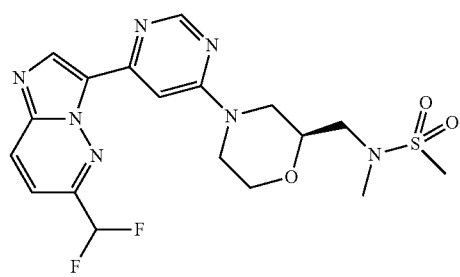
II-297
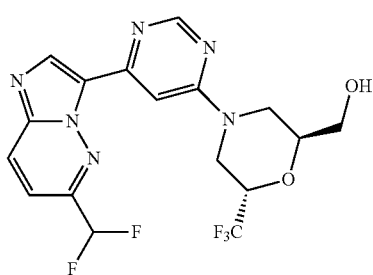
II-291
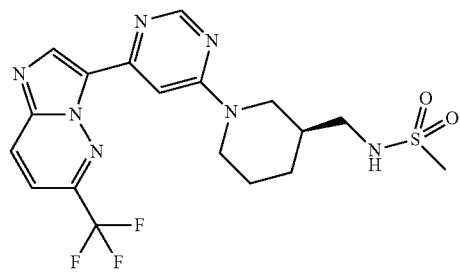
II-298
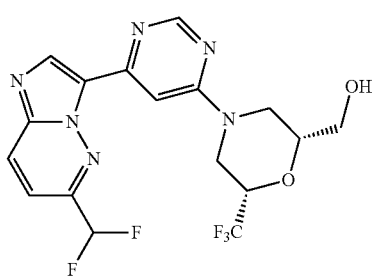
II-292
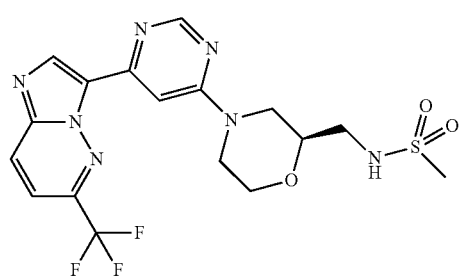
II-299
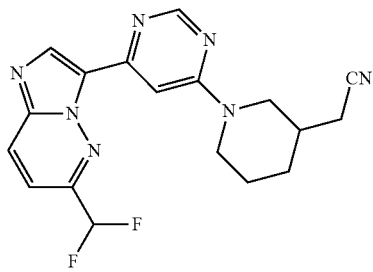
II-295
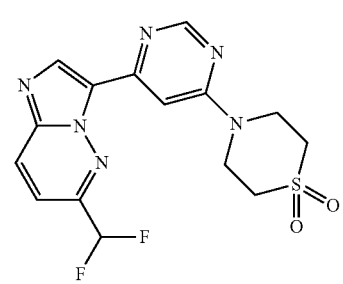
II-300
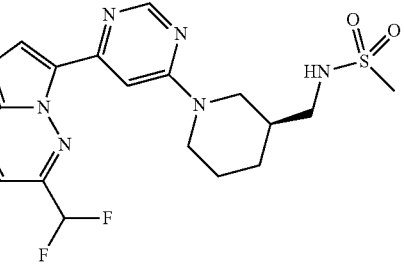

II-306 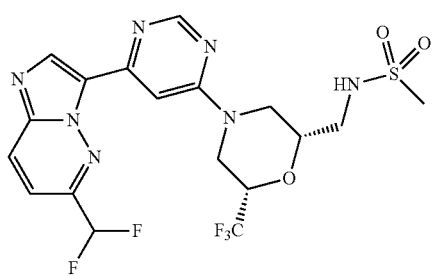
II-312 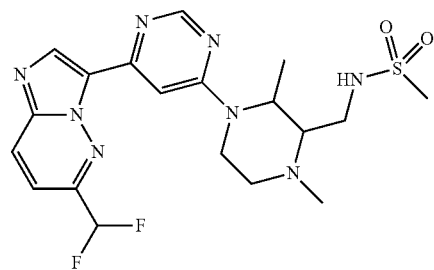
II-307 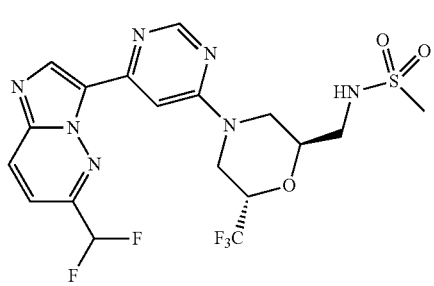
II-313 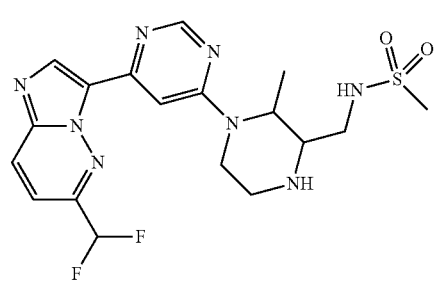
II-308 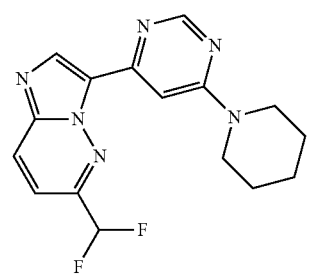
II-314 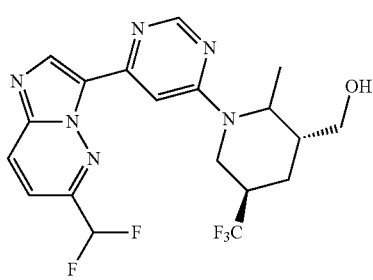
II-310 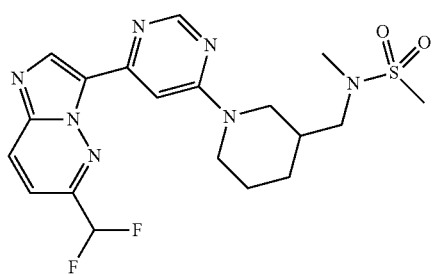
II-315 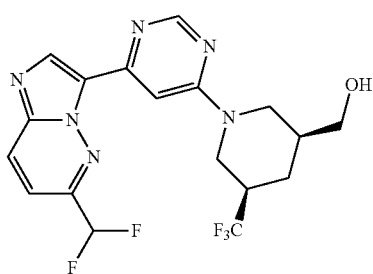
II-311 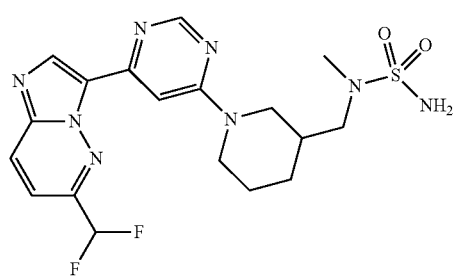
II-316 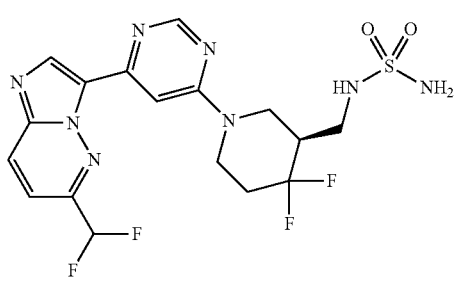

II-317
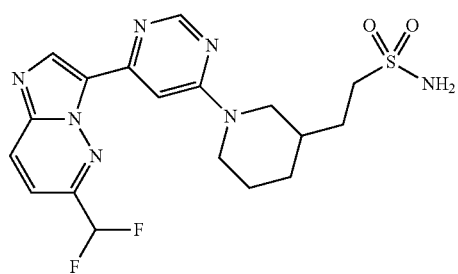
II-318
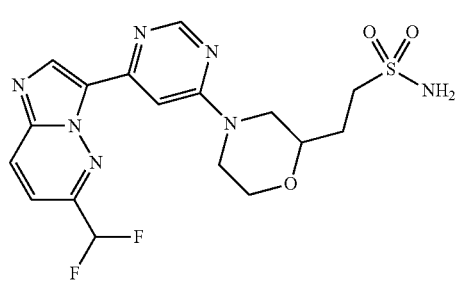
II-321
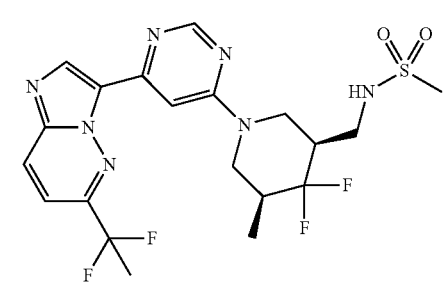
II-322
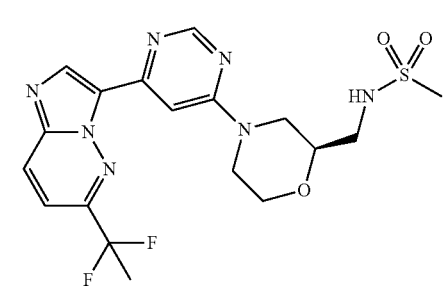
II-323
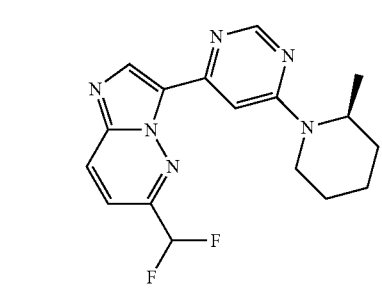
II-324
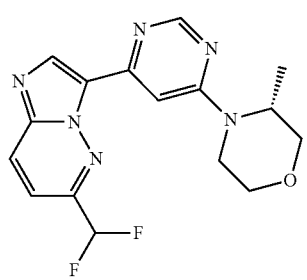
II-325
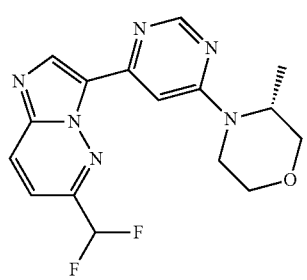
II-326
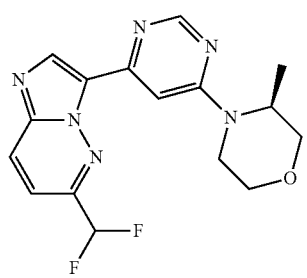
II-327
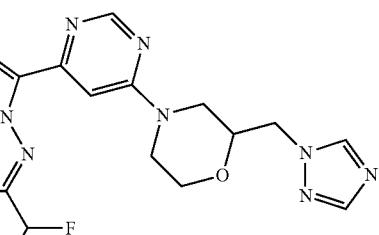
II-328
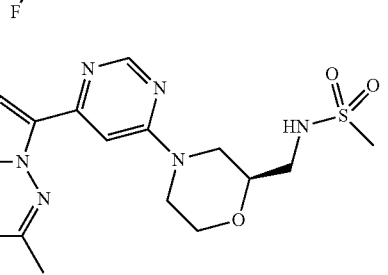
II-329
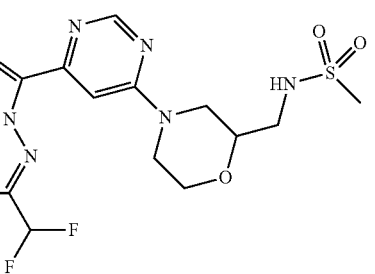

1409
-continued
II-330
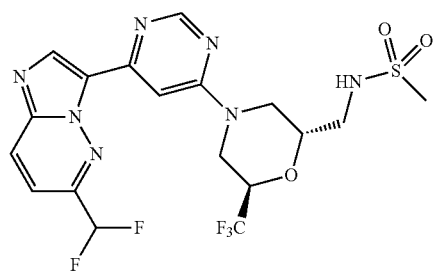
II-331
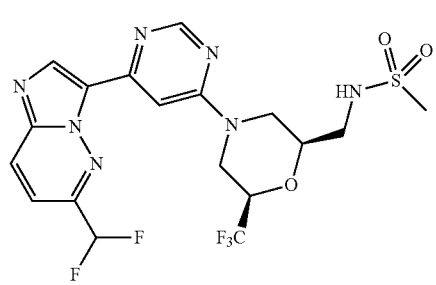
II-336
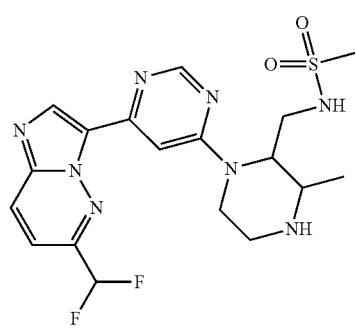
II-337
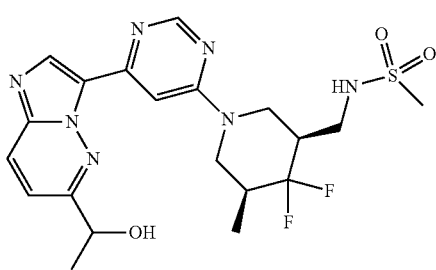
II-326
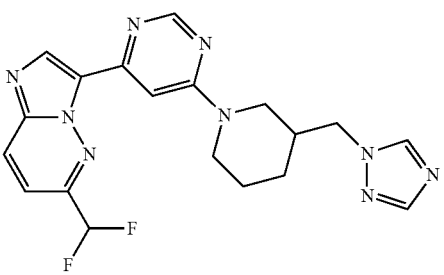
1410
-continued
II-327
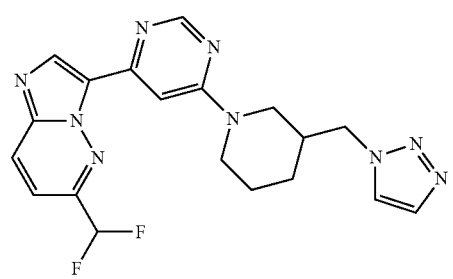
II-328
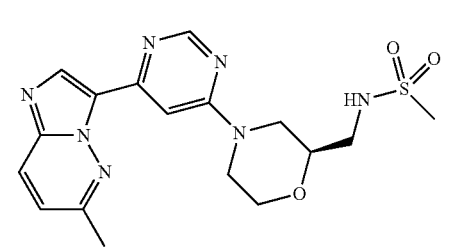
II-329
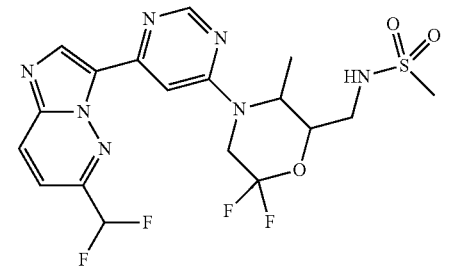
II-330
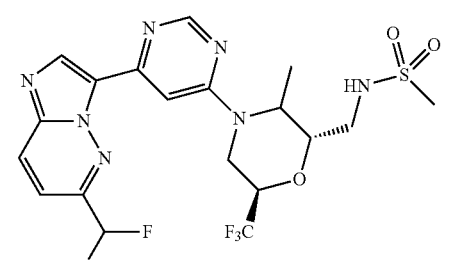
II-331
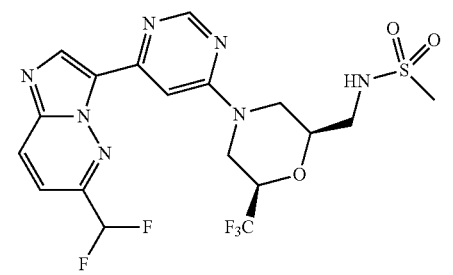

II-336 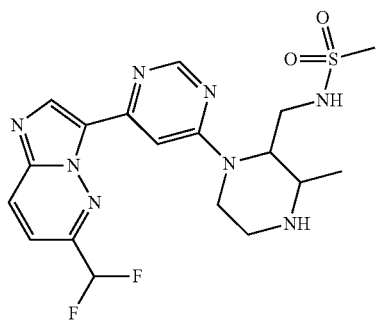
II-347 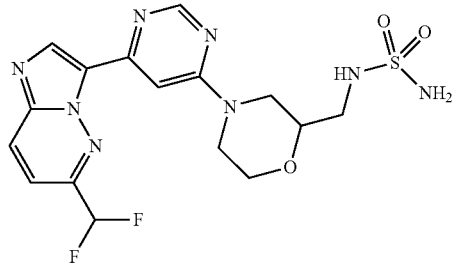
II-337 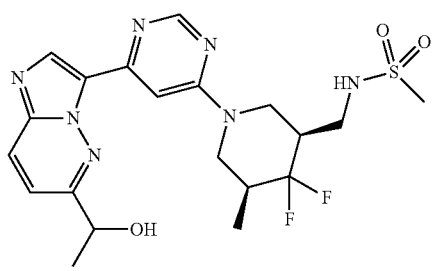
II-348 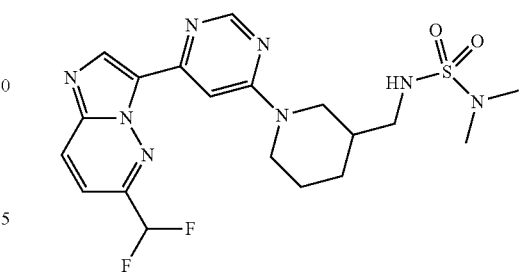
II-338 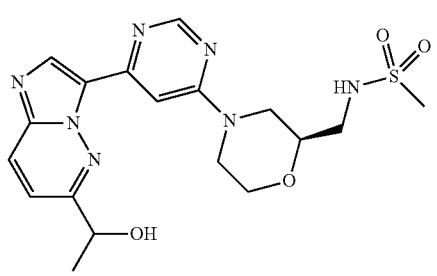
II-349 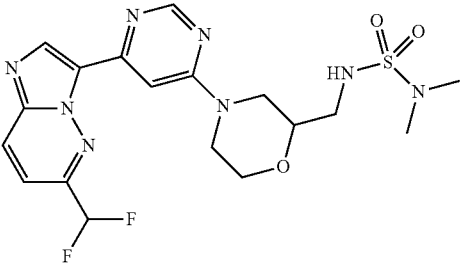
II-339 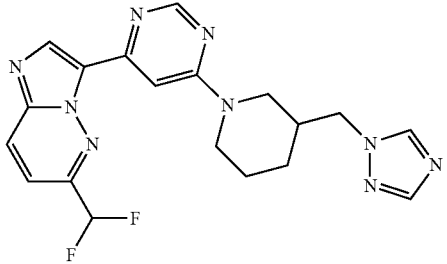
II-350 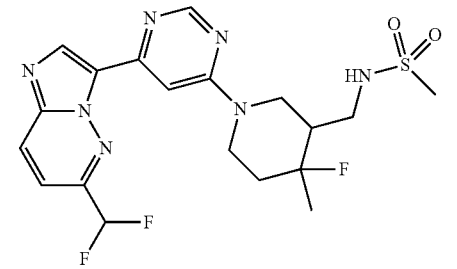
II-340 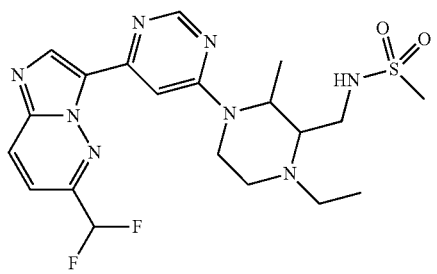
II-351 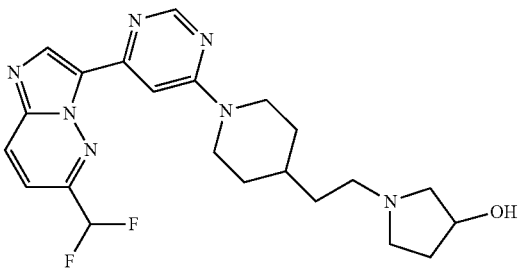

II-352 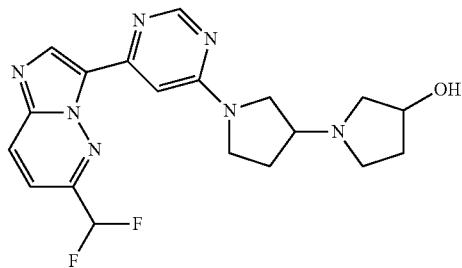
II-362 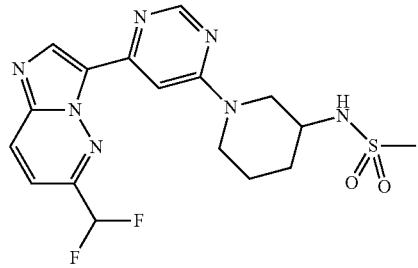
II-353 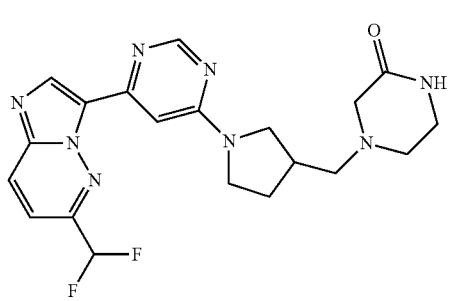
II-366 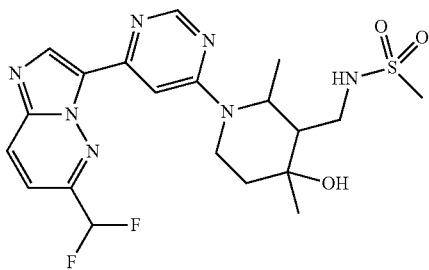
II-354 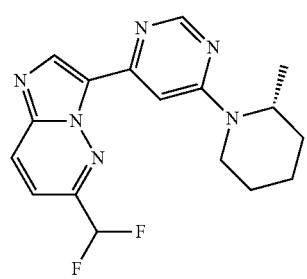
II-368 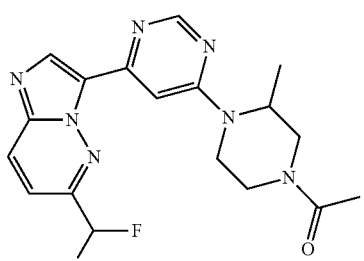
II-370 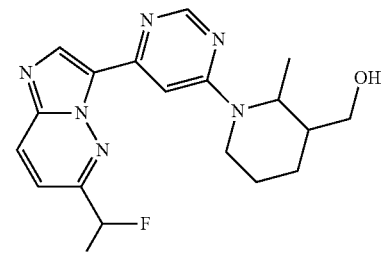
II-358 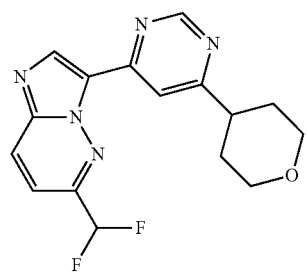
II-373 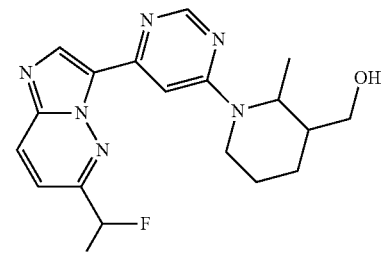
II-361 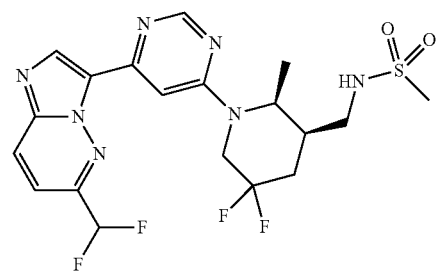
II-374 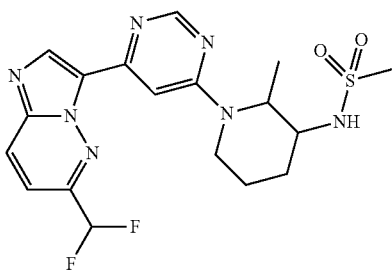

II-376
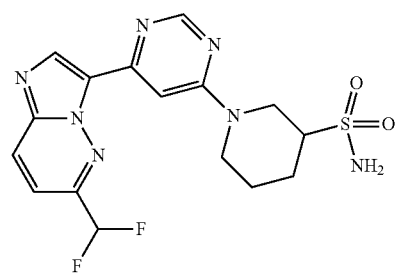
II-377
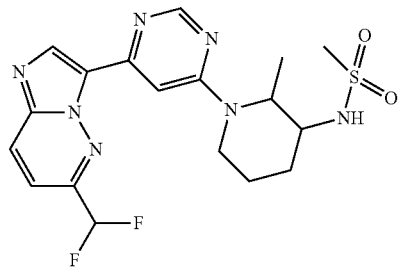
II-378
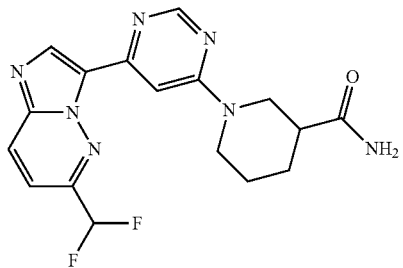
II-379
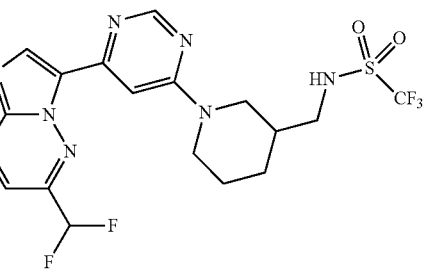
II-380
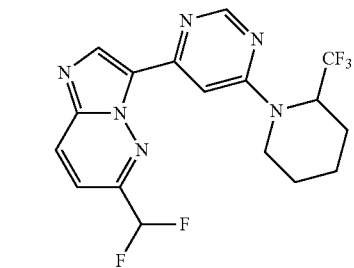
II-385
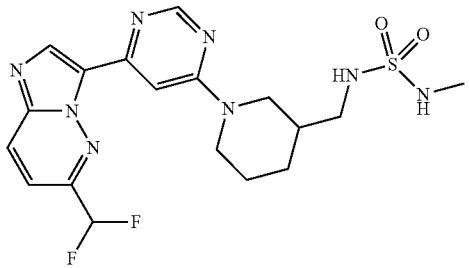
II-386
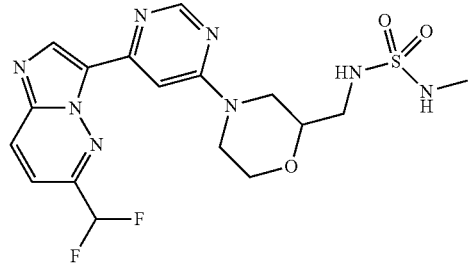
II-387
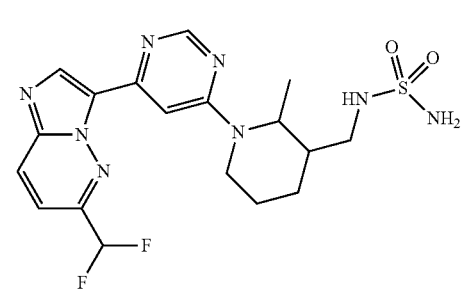
II-390
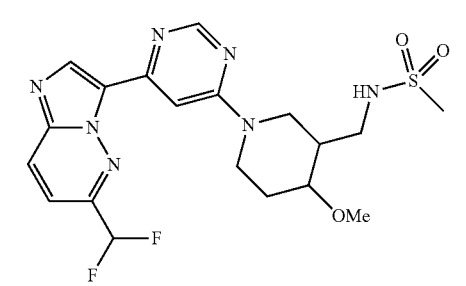
II-391
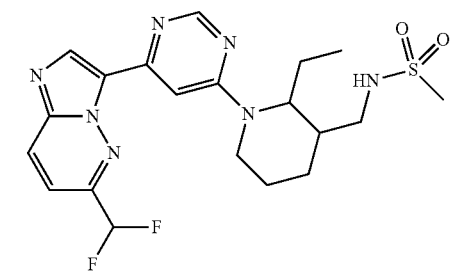
II-392
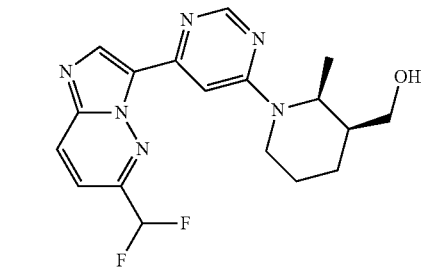

1417
-continued
II-394
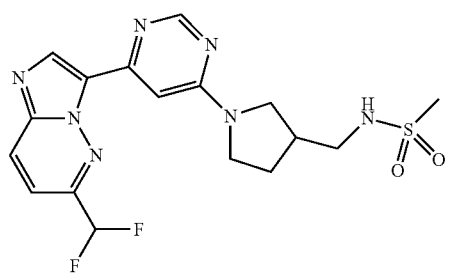
II-395
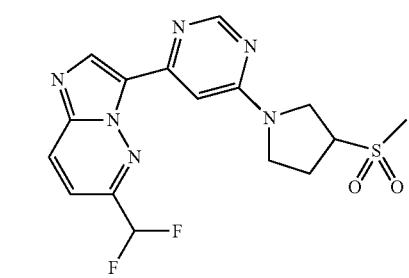
II-396
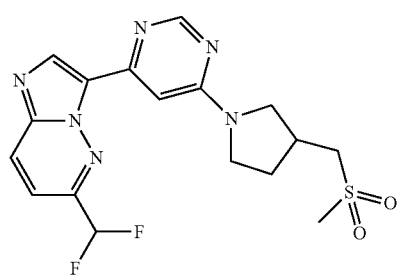
II-399
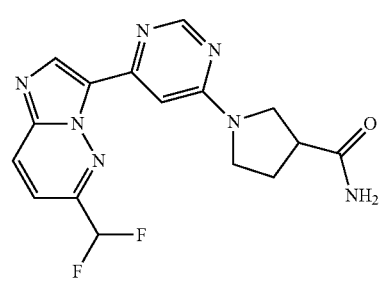
II-402
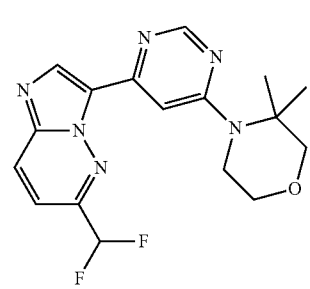
II-403
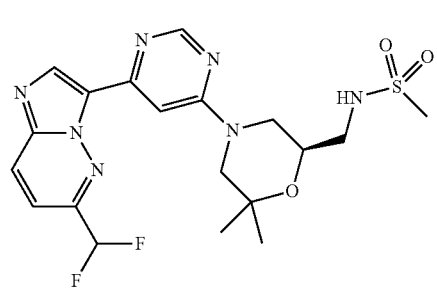
1418
-continued
II-404
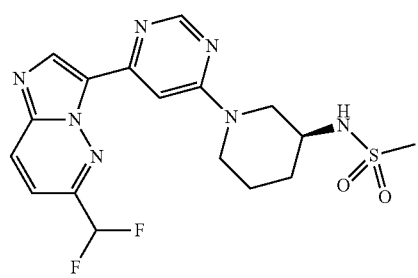
II-405
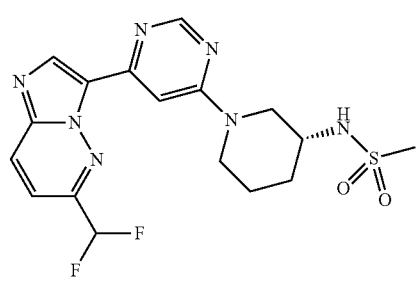
II-406
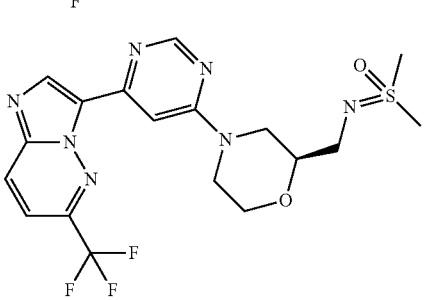
II-407
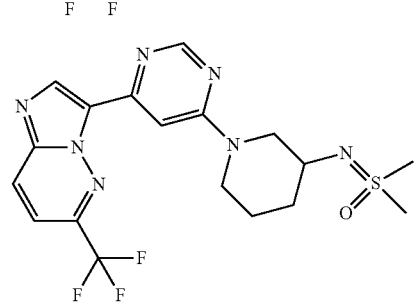
II-408
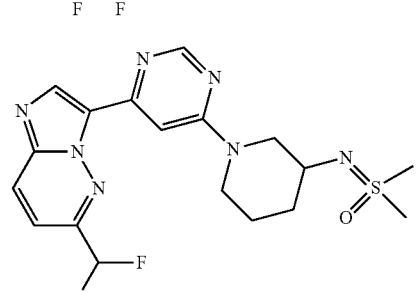
II409
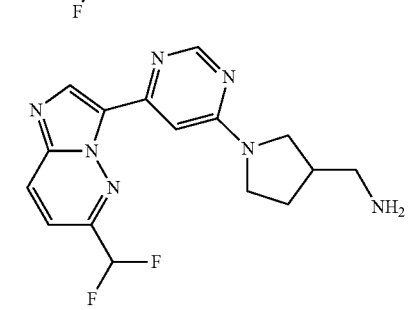

II-410 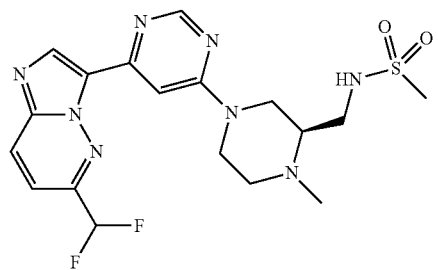
II-411 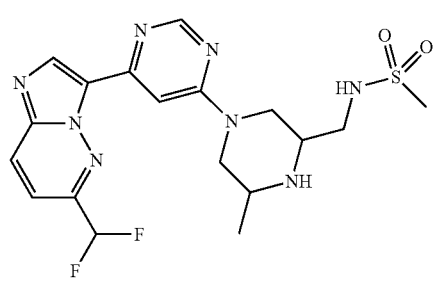
II-412 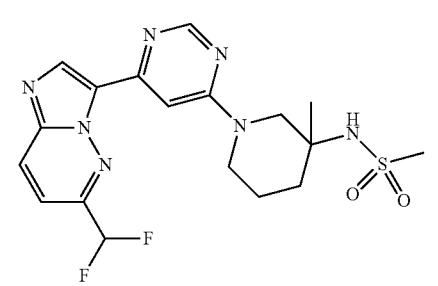
II-415 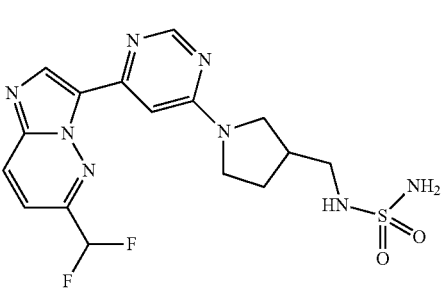
II-418 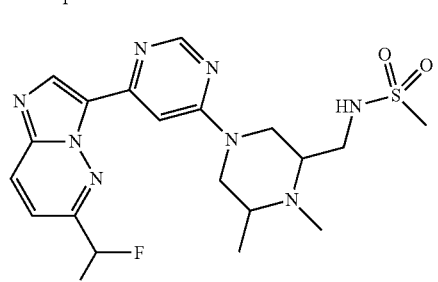
I-419 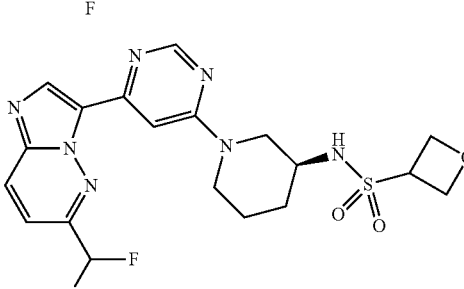
II-420 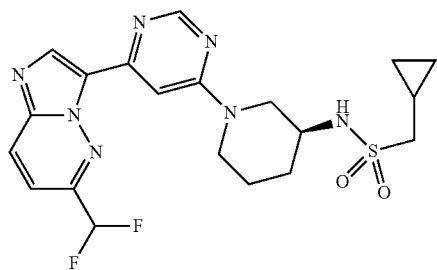
II-421 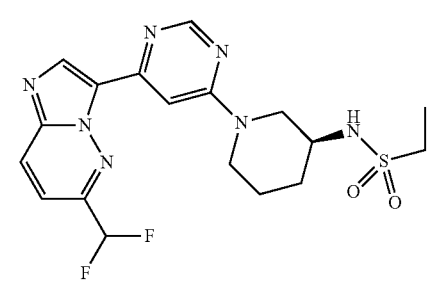
II-422 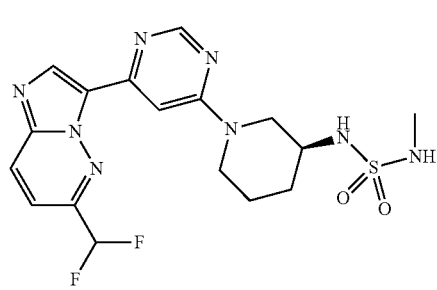
II-423 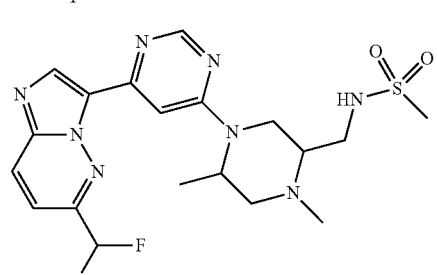
II-424 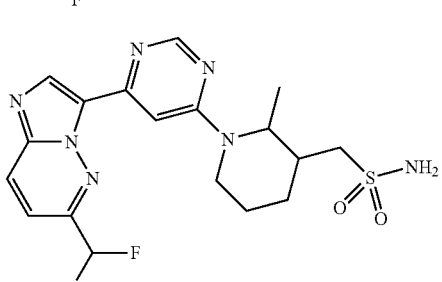
II-427 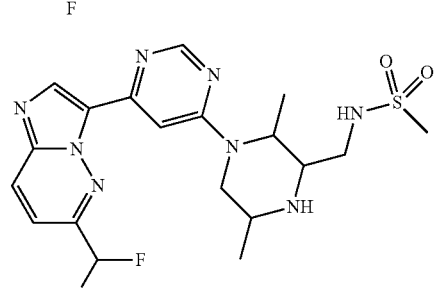

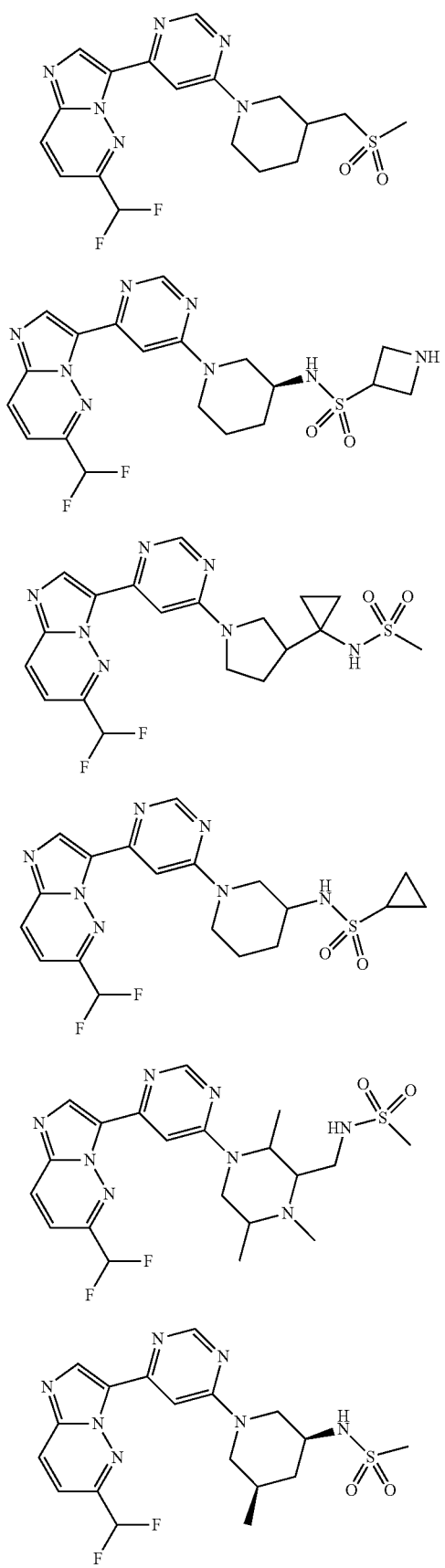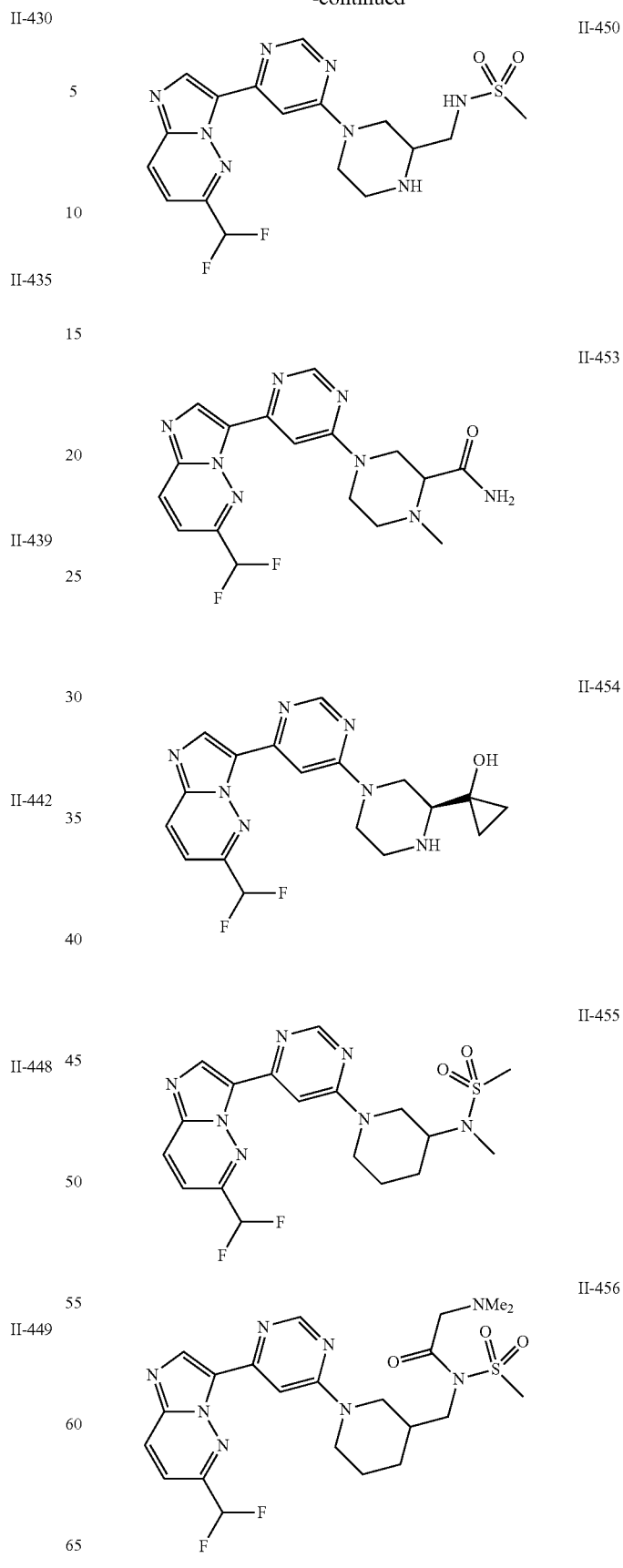

II-457
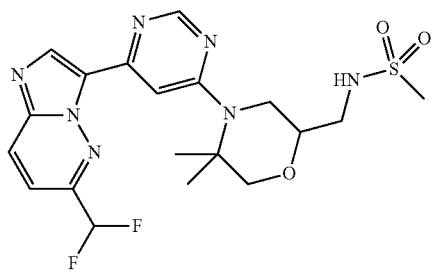
II-458
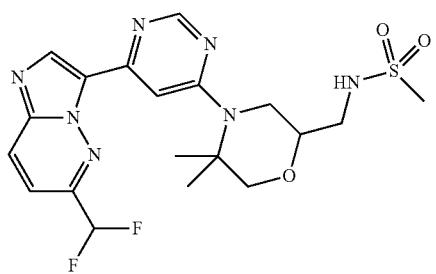
II-459
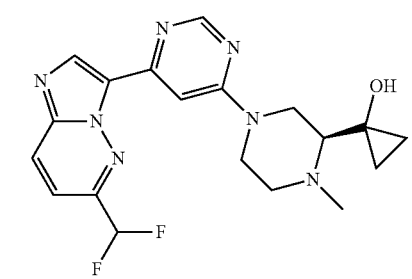
II-460
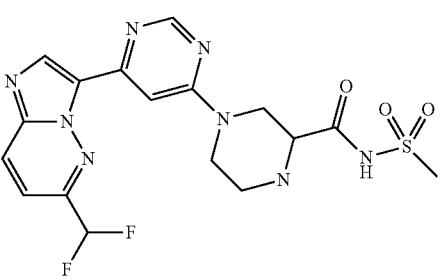
II-462
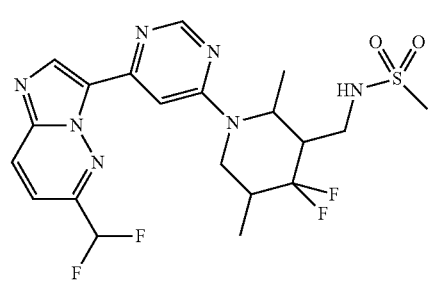
II-463
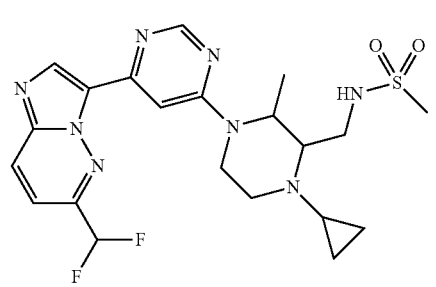
II464
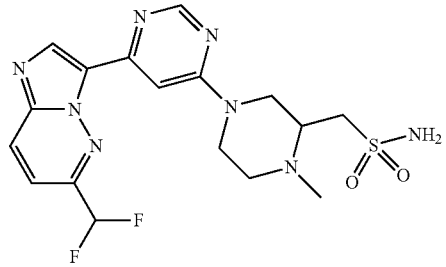
II-465
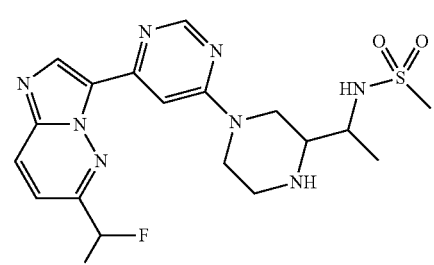
II-466
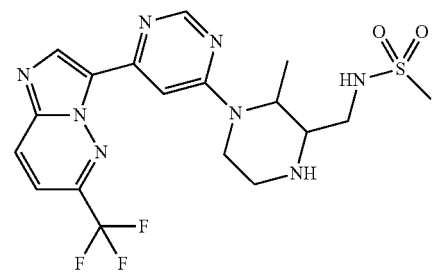
II-477
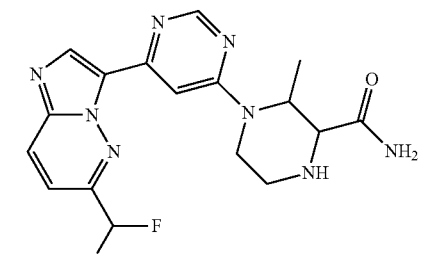
II-480
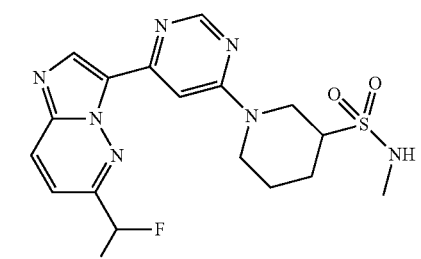

1425
-continued
II-481
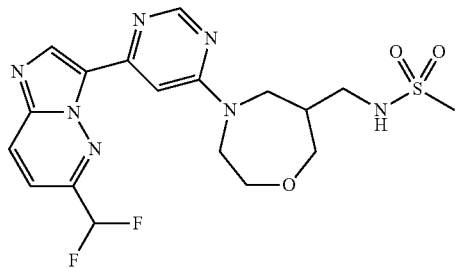
II-482
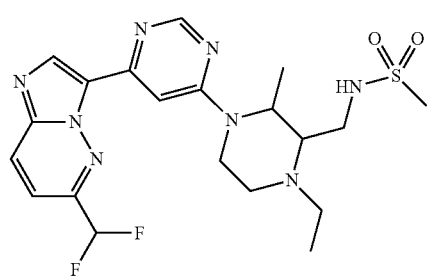
II-483
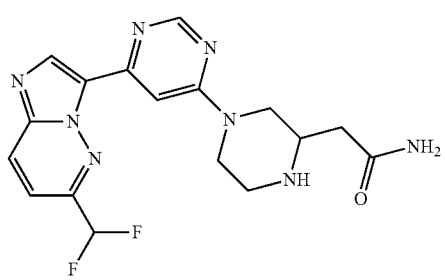
II-484
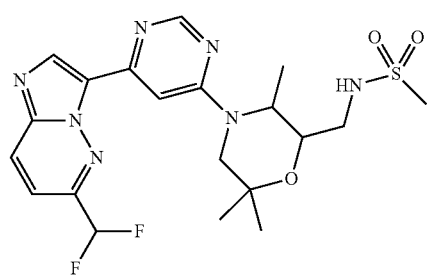
II-485
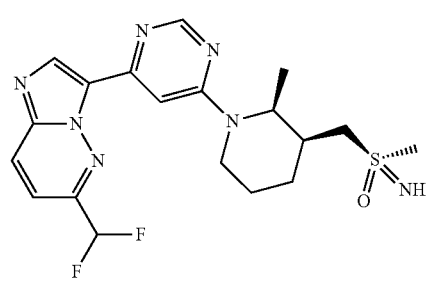
1426
-continued
II-490
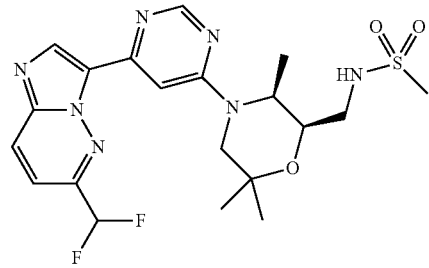
II-492
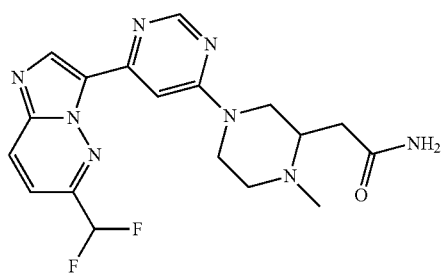
II-493
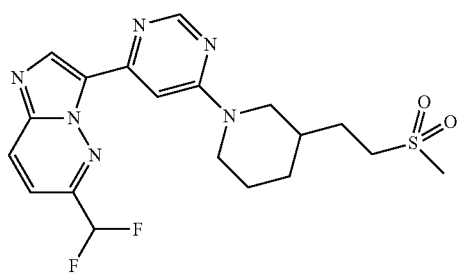
II-494
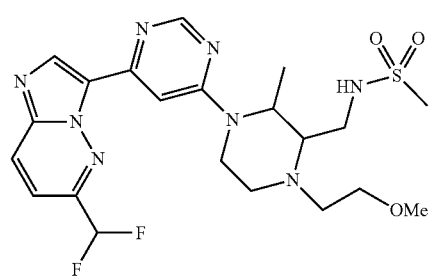
II-495
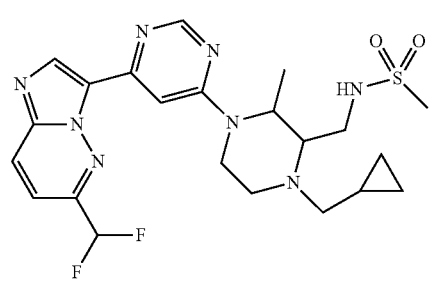

| 1427 -continued | 1428 -continued |
|---|---|
| 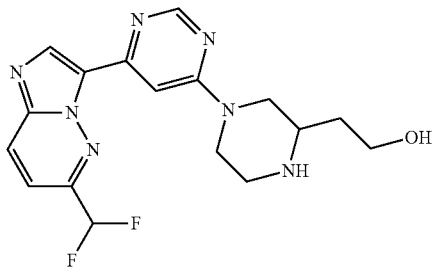 II-496 | 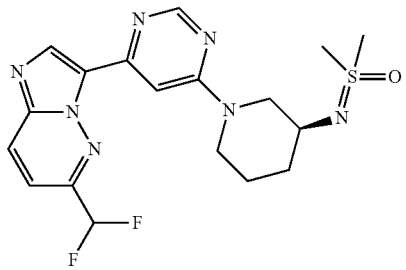 II-502 |
| 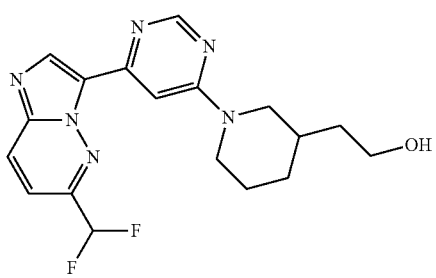 II-497 | 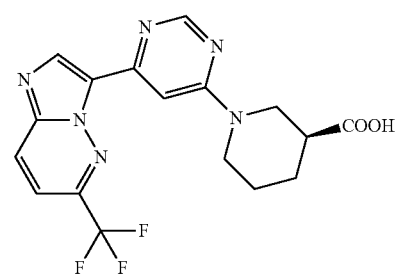 II-504 |
| 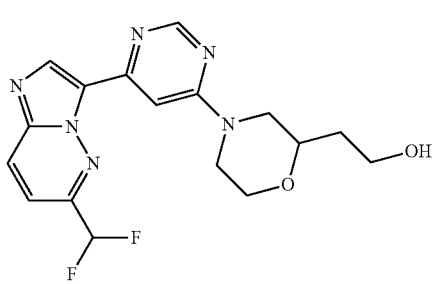 II-498 | 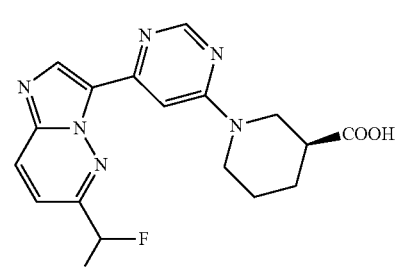 II-505 |
| 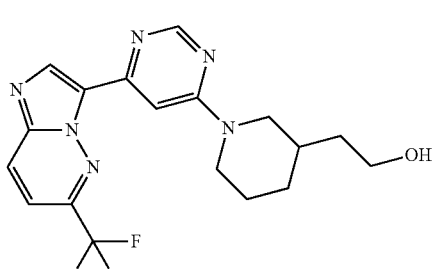 II-499 | 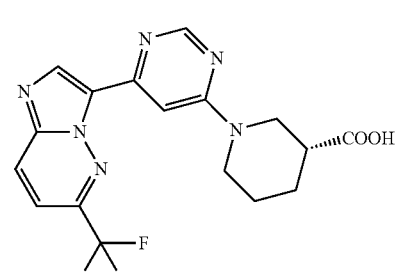 II-506 |
| 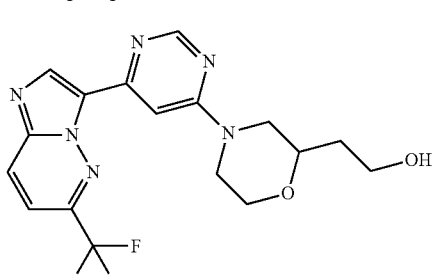 II-500 | 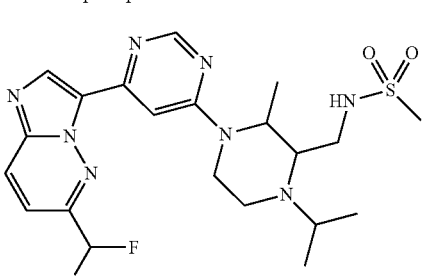 II-507 |
| 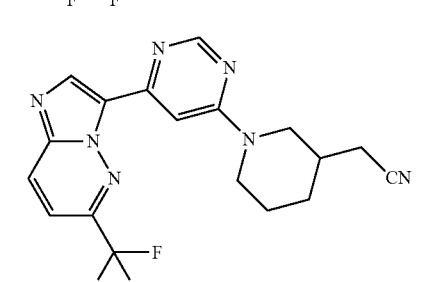 II-501 | 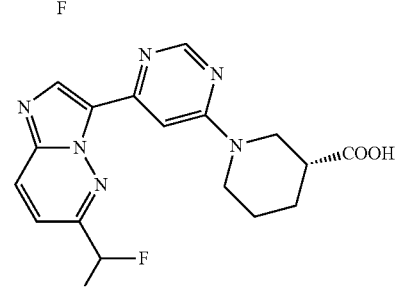 II-508 |

II-509
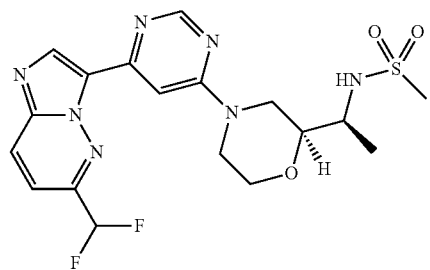
II-511
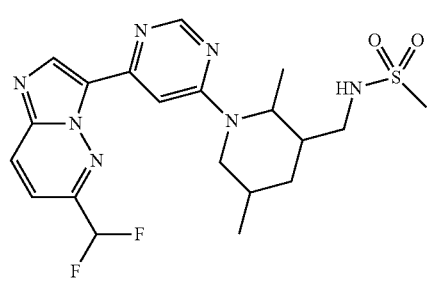
II-512
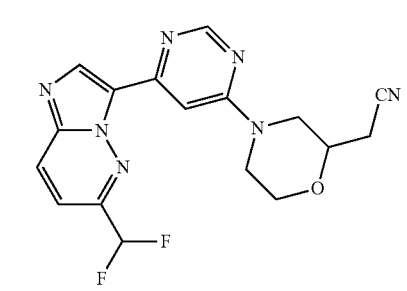
II-513
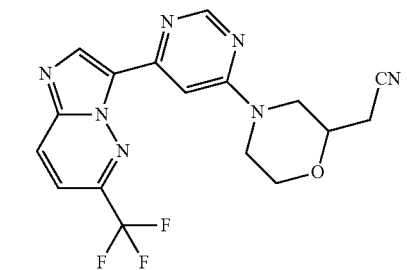
II-514
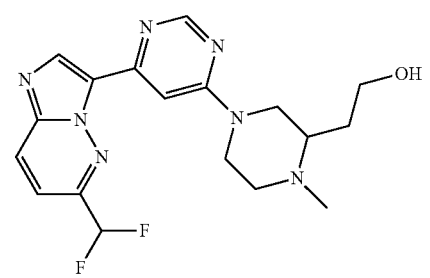
II-515
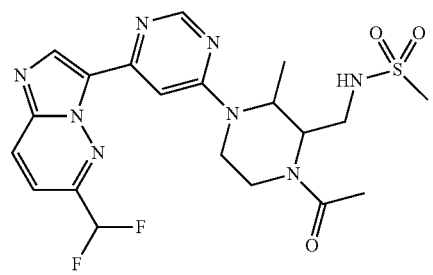
II-516
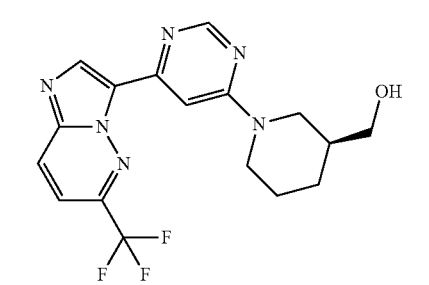
II-517
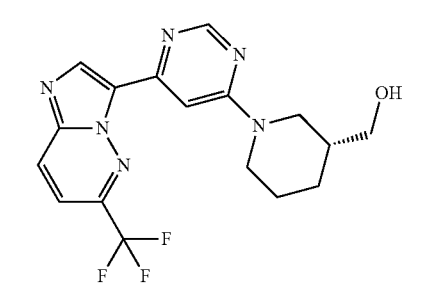
II-518
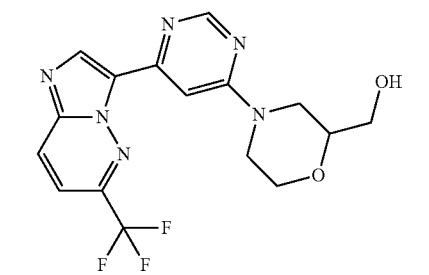
II-519
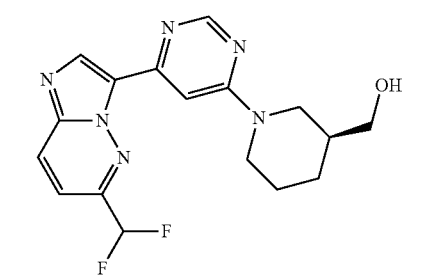

II-520 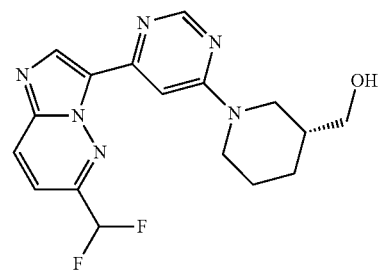
II-521 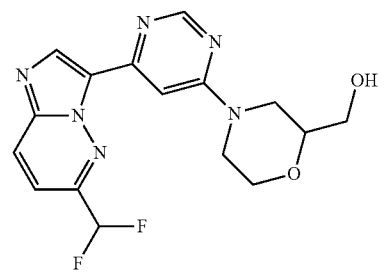
II-522 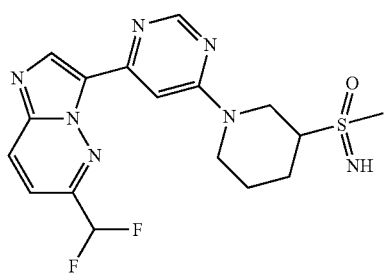
II-523 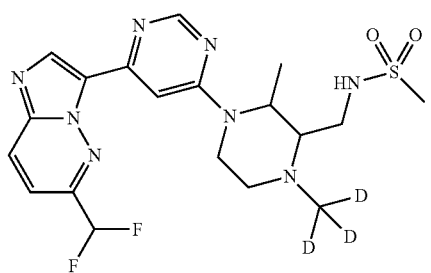
II-524 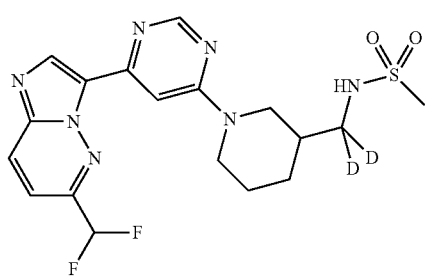
II-531 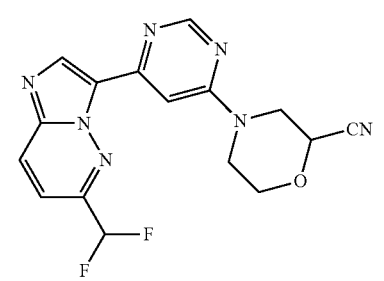
II-532 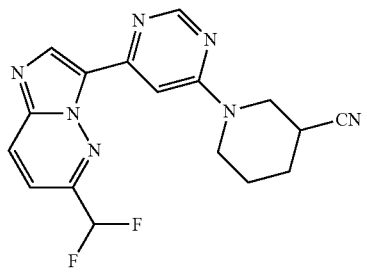
II-533 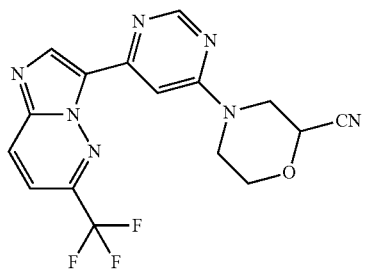
II-534 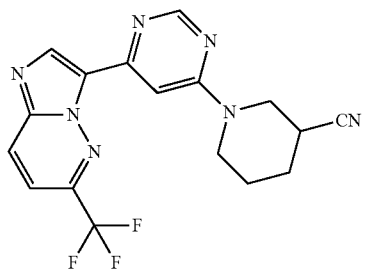
II-536 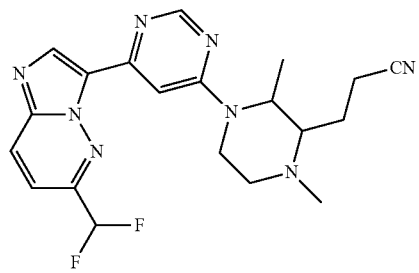
II-539 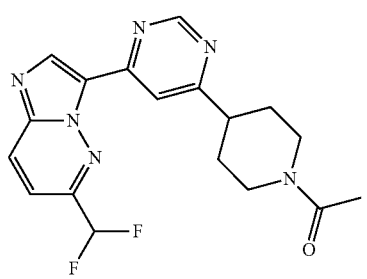
II-540 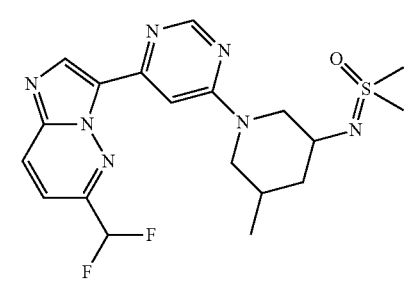

1433
-continued
II-541
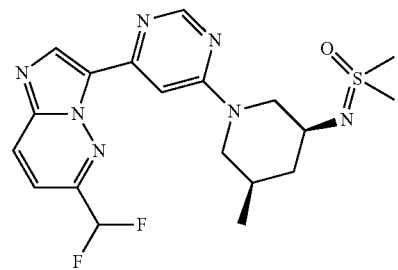
II-544
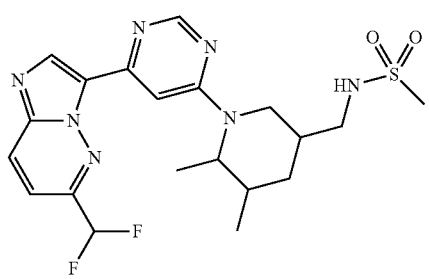
II-548
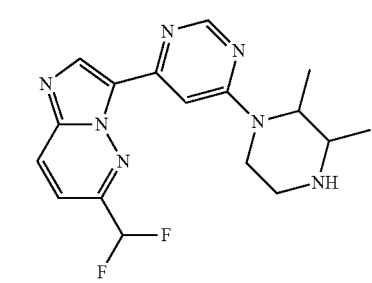
II-553
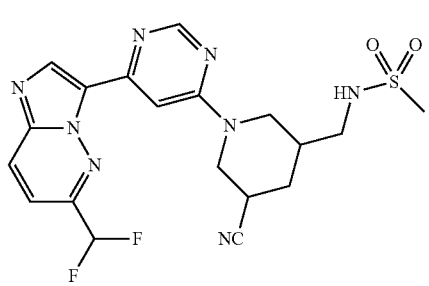
II-556
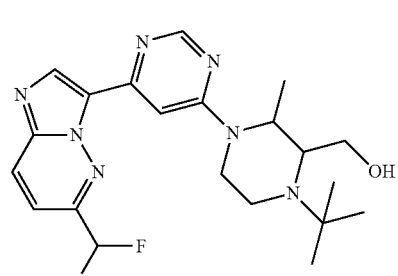
II-559
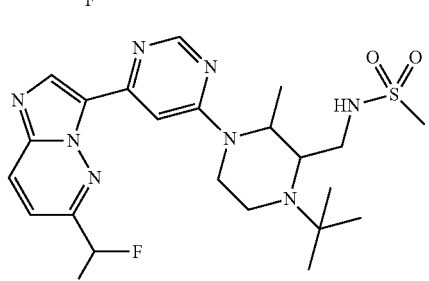
1434
-continued
II-563
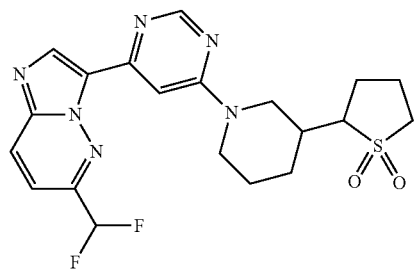
II-567
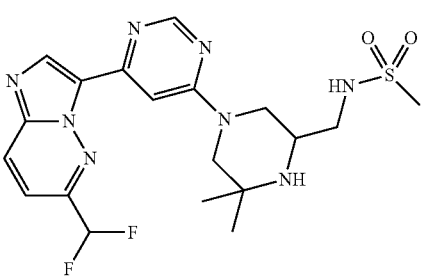
II-577
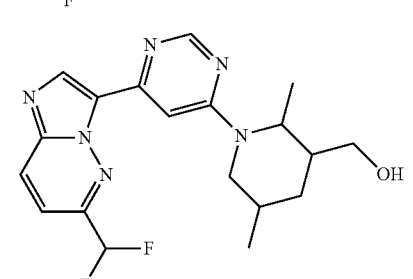
II-578
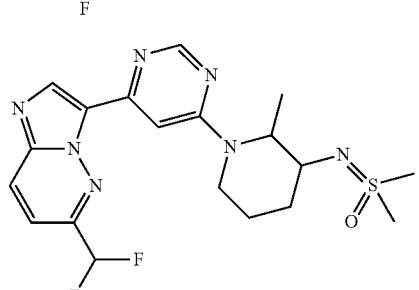
II-579
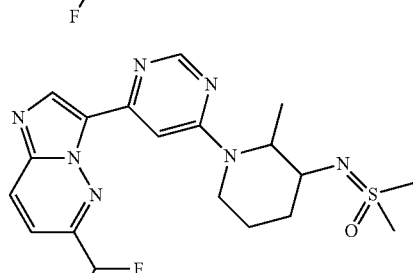
II-585
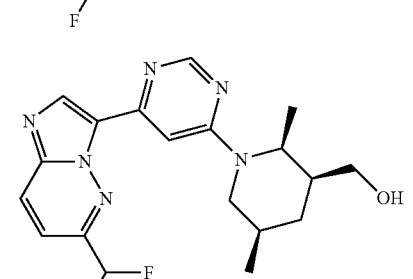

1435
-continued
II-589
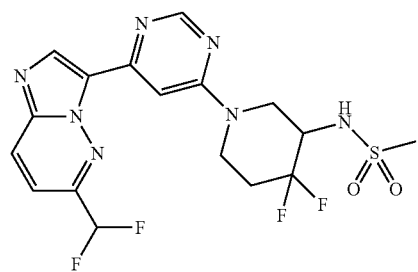
II-590
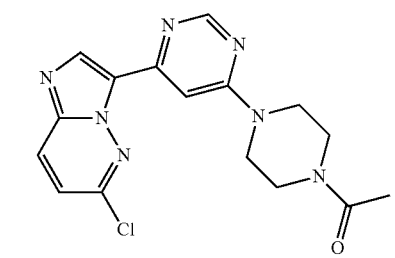
II-593
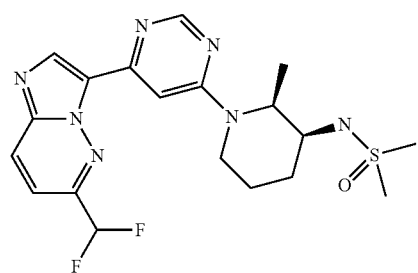
II-607
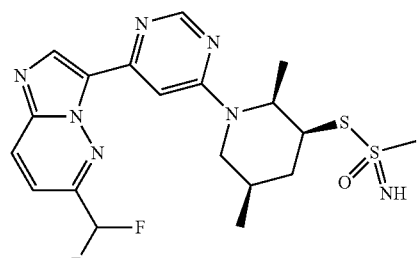
II-608
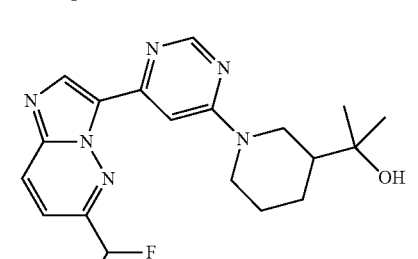
II-627
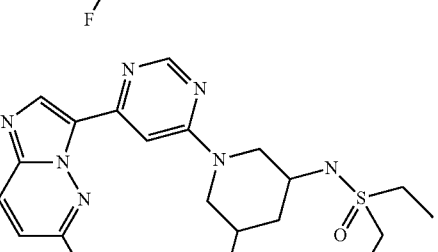
1436
-continued
II-629
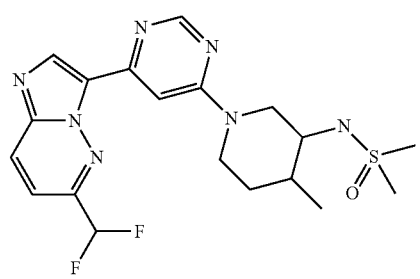
II-631
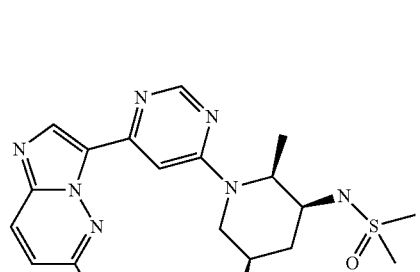
II-634
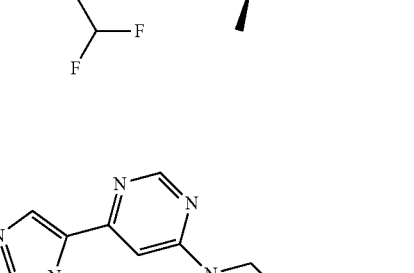
II-635
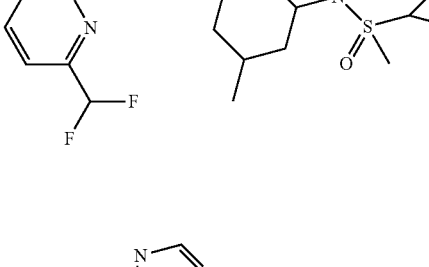
II-648
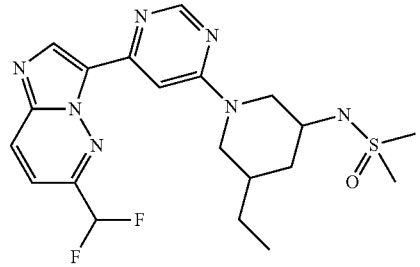

II-649
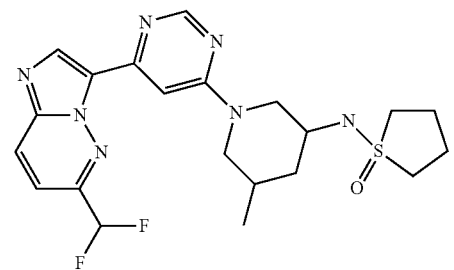
II-654
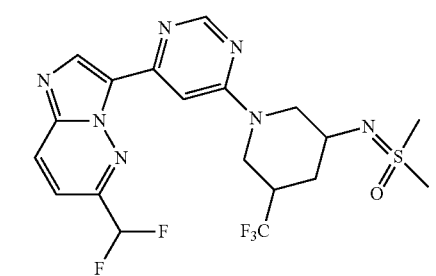
II-657
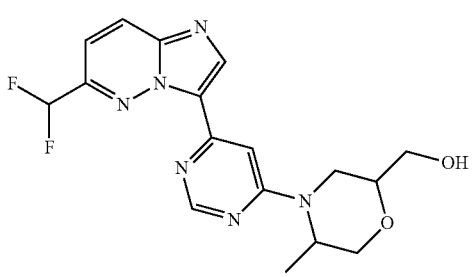
II-658
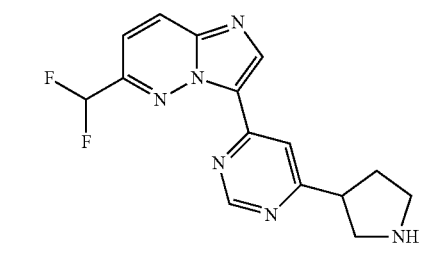
II-659
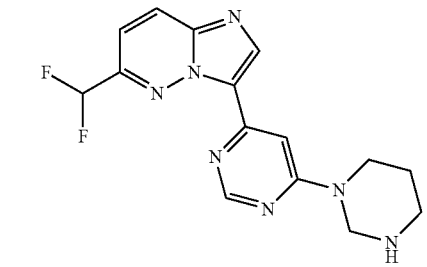
II-661
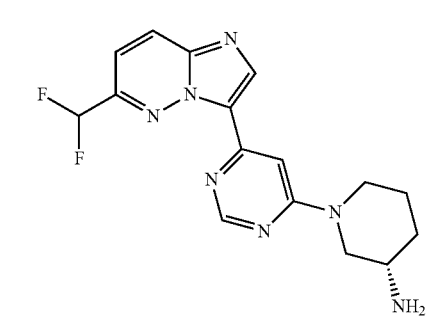
II-663
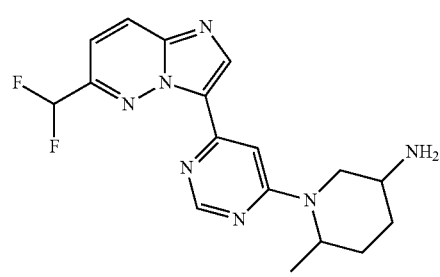
II-666
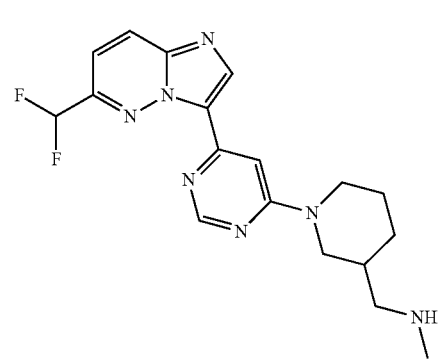
II-671
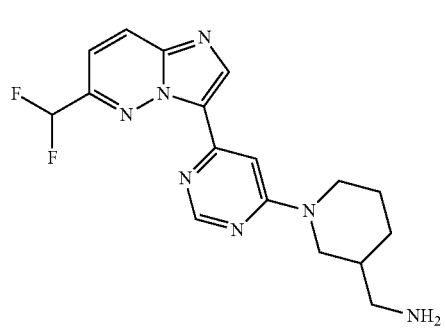
II-672
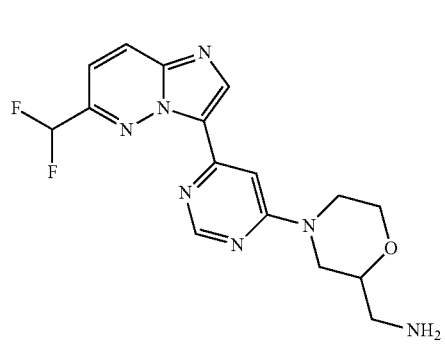
II-676
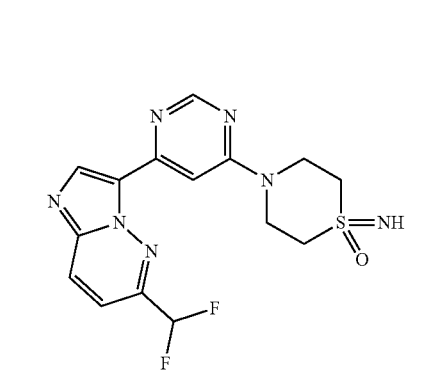

1439
-continued
II-678
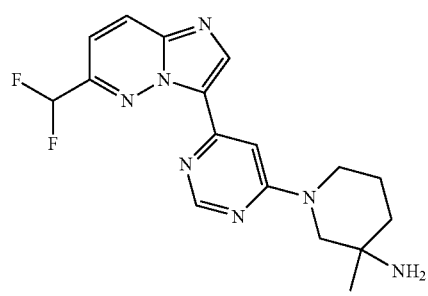
II-680
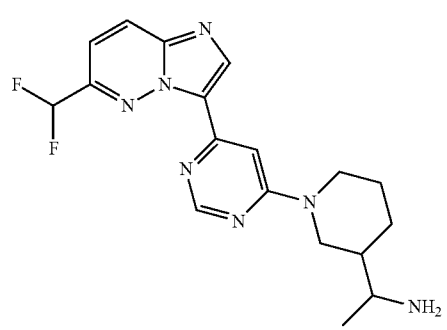
II-681
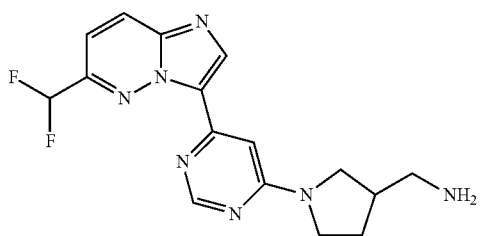
II-682
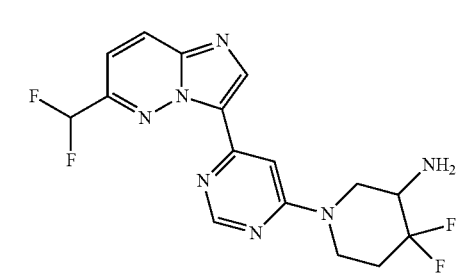
II-684
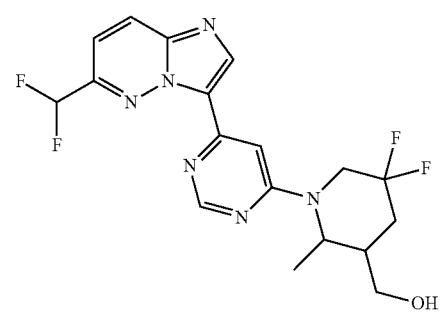
1440
-continued
II-685
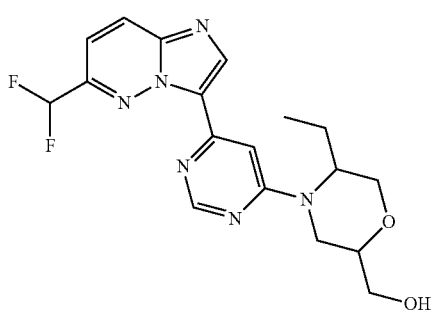
II-686
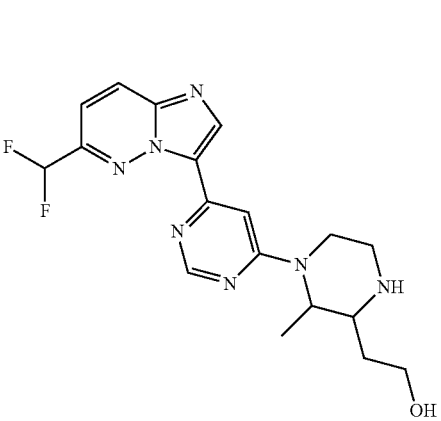
II-687
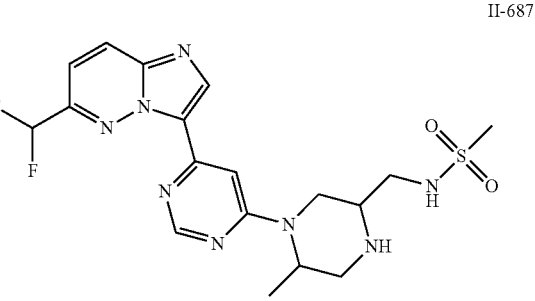
II-688
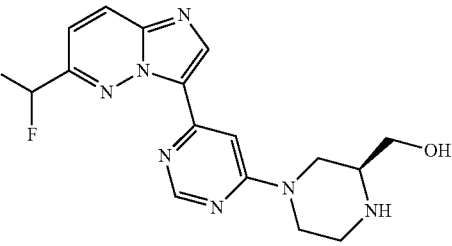
II-689
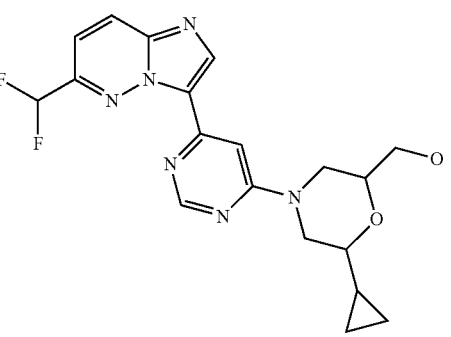

II-690
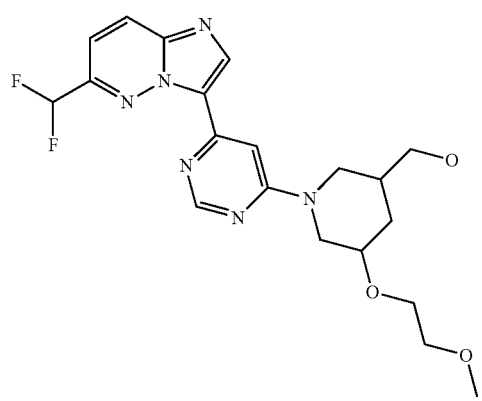
II-698
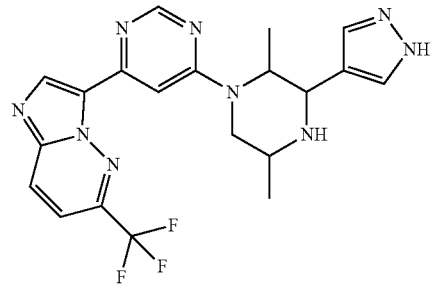
II-692
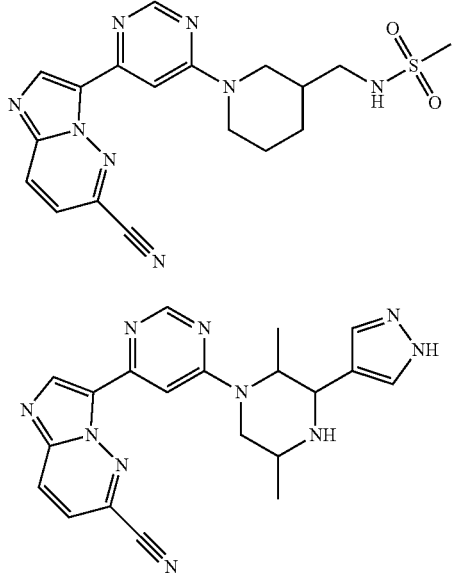
II-700
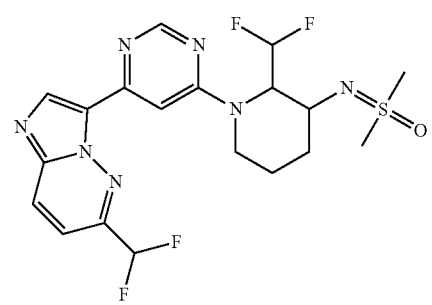
II-693
II-702
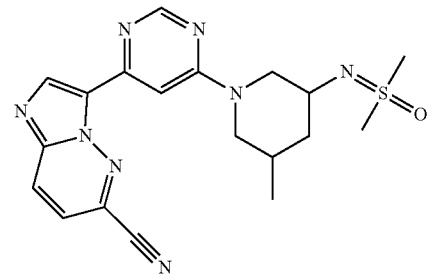
II-694
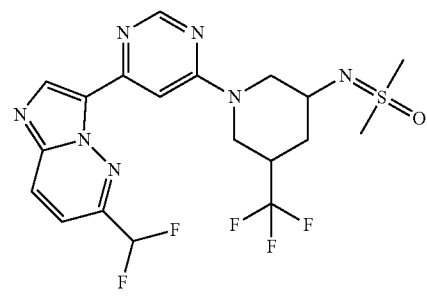
II-704
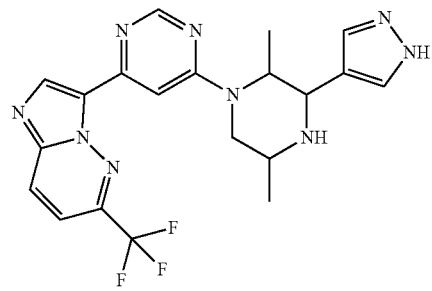
II-696
II-706
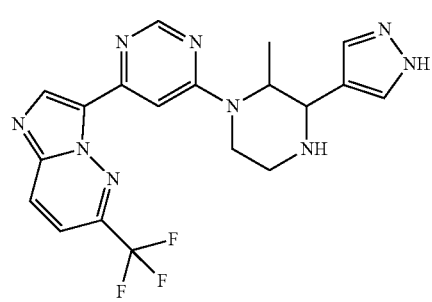

II-707
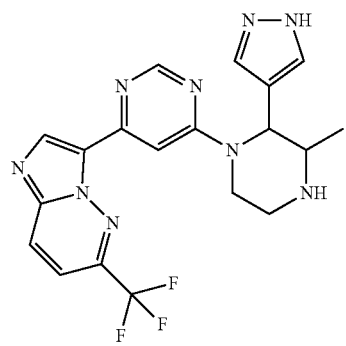
II-710
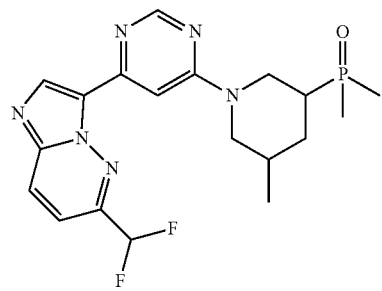
II-712
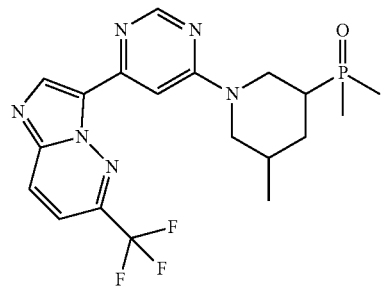
II-714
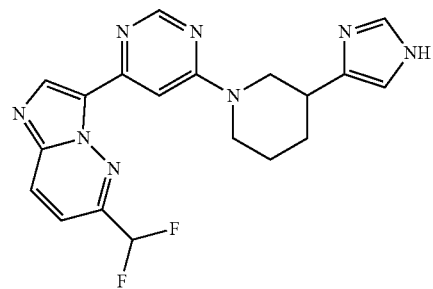
II-715
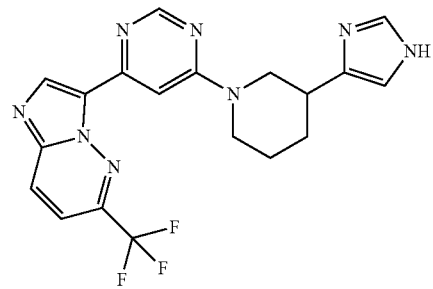
II-719
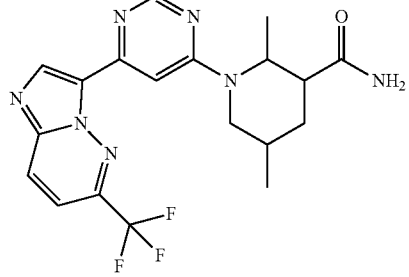
II-721
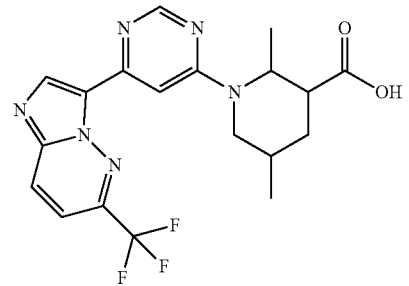
II-726
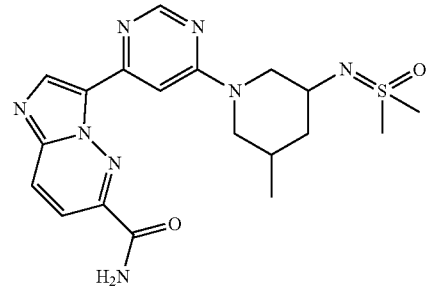
II-728
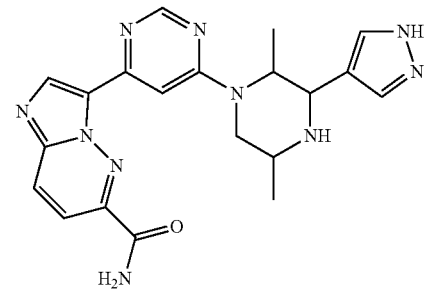
II-752
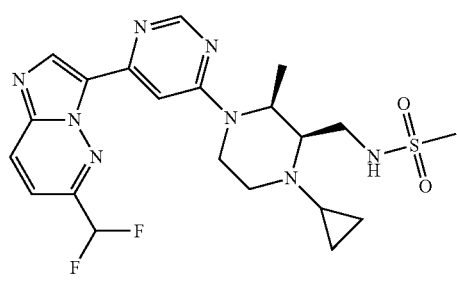

1445
-continued
II-753
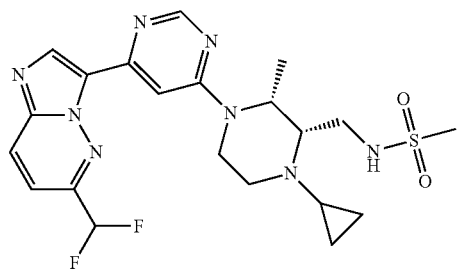
II-754
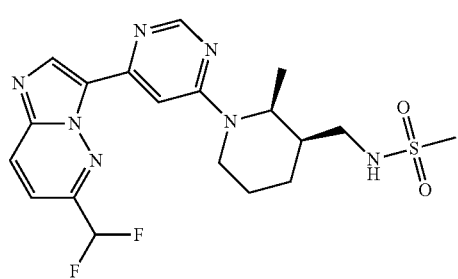
II-755
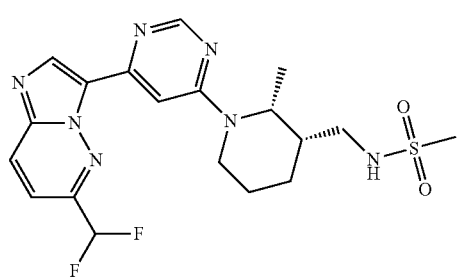
II-756
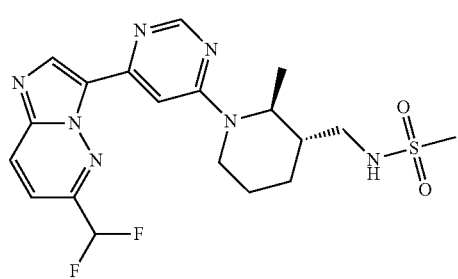
II-757
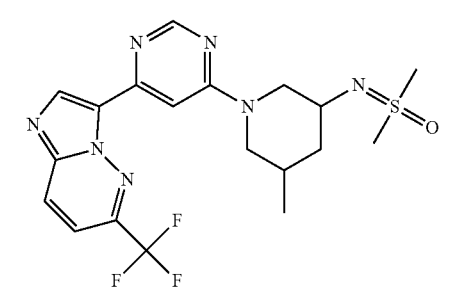
1446
-continued
II-758
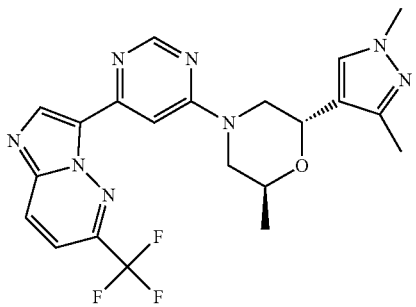
II-759
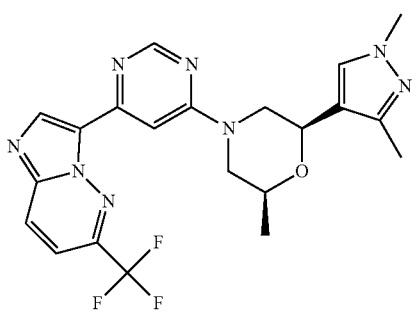
II-760
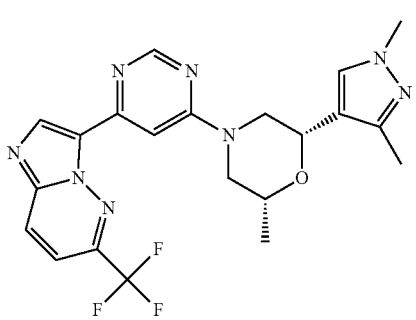
II-761
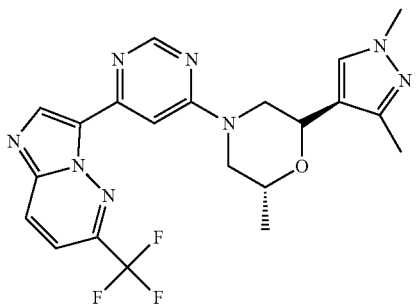
II-762
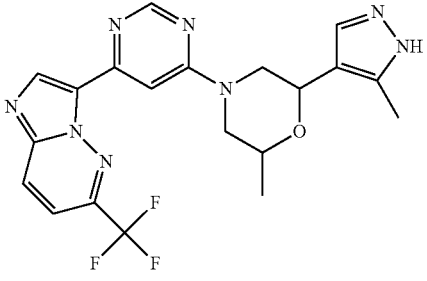

II-763 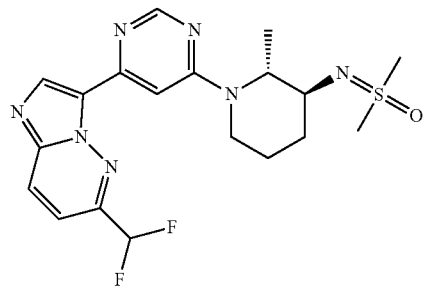
II-768 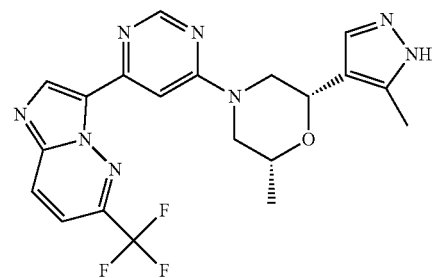
II-764 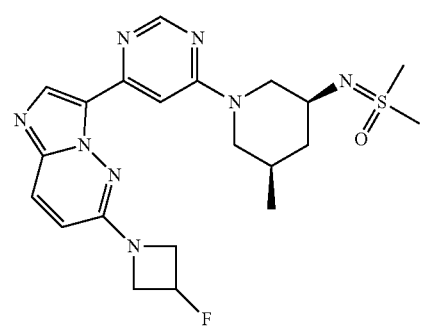
II-769 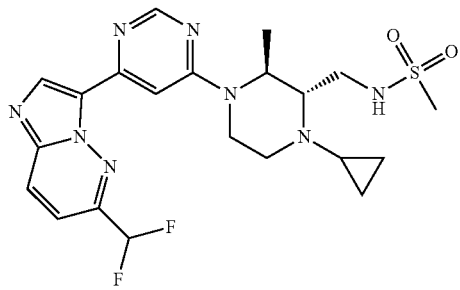
II-765 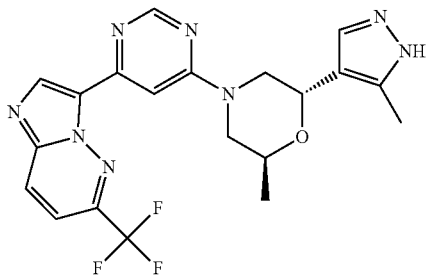
II-770 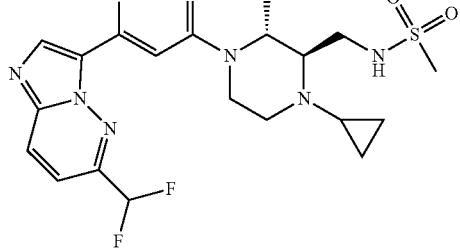
II-766 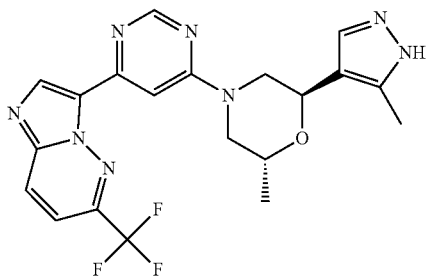
II-771 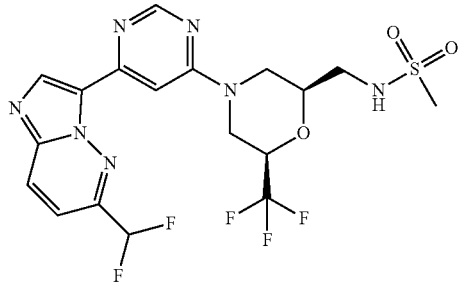
II-767 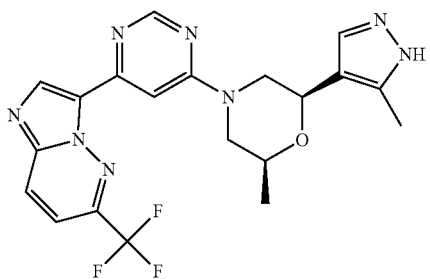
II-772 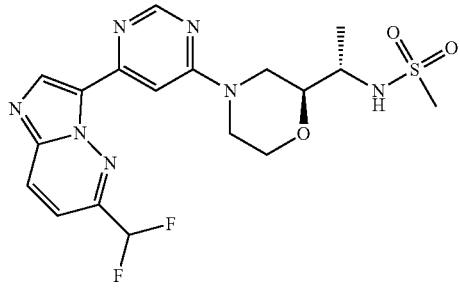

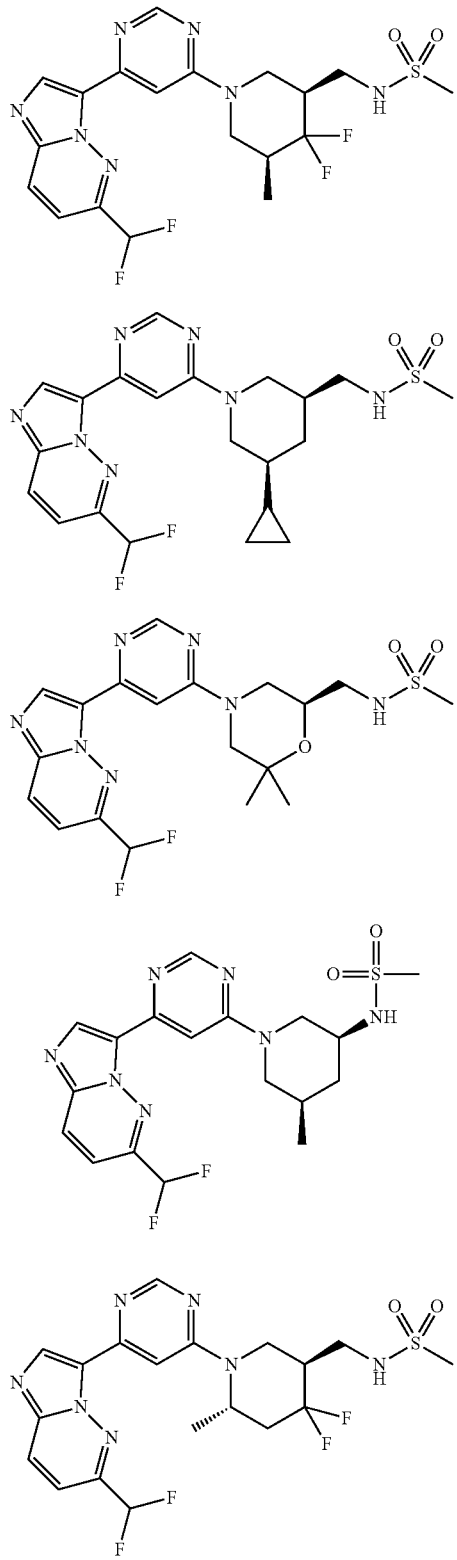

16. A pharmaceutical composition comprising a compound according to claim 15, and a pharmaceutically acceptable carrier, adjuvant, or vehicle.

17. The compound of claim 1, wherein Ring A is a 5-7 membered saturated monocyclic heterocyclic ring having 1-2 heteroatoms independently selected from nitrogen, oxygen, or sulfur.

18. The compound of claim 1, wherein Ring A is

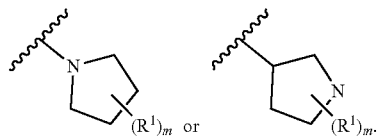

19. The compound of claim 1, wherein Ring A is:

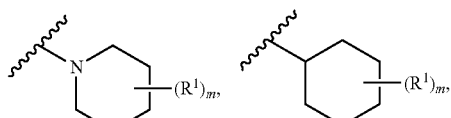

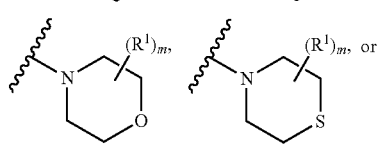

20. The compound of claim 1, wherein Ring A is:

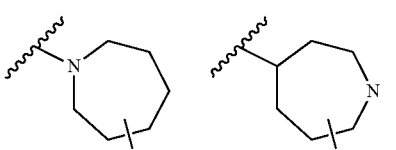

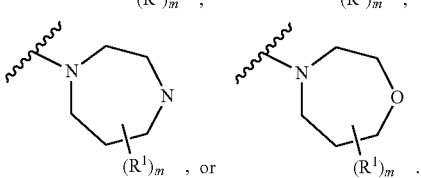

or a pharmaceutically acceptable salt thereof.

* * * * *

UNITED STATES PATENT AND TRADEMARK OFFICE
CERTIFICATE OF CORRECTION

PATENT NO. : 10,988,477 B2
APPLICATION NO. : 16/259979
DATED : April 27, 2021
INVENTOR(S) : Andrew Bayly et al.

It is certified that error appears in the above-identified patent and that said Letters Patent is hereby corrected as shown below:

On the Title Page

Item (72) 11th named Inventor "Shazia Kelly" should be "Shazia Keily".

Signed and Sealed this
Twelfth Day of November, 2024

Katherine Kelly Vidal
*Director of the United States Patent and Trademark Office*